US012091701B2

(12) United States Patent
Sato

(10) Patent No.: US 12,091,701 B2
(45) Date of Patent: Sep. 17, 2024

(54) SCREENING METHOD FOR CANDIDATE SUBSTANCES FOR ACTIVE COMPONENT TO PREVENT OR TREAT AT LEAST ONE DISEASE SELECTED FROM THE GROUP CONSISTING OF RENAL HYPOFUNCTION, CHRONIC KIDNEY DISEASE AND KIDNEY FAILURE

(71) Applicant: KARYDO THERAPEUTIX, INC., Tokyo (JP)

(72) Inventor: Narutoku Sato, Kyoto (JP)

(73) Assignee: KARYDO THERAPEUTIX, INC., Tokyo (JP)

( * ) Notice: Subject to any disclaimer, the term of this patent is extended or adjusted under 35 U.S.C. 154(b) by 1640 days.

(21) Appl. No.: 16/089,593

(22) PCT Filed: Mar. 28, 2017

(86) PCT No.: PCT/JP2017/012761
§ 371 (c)(1),
(2) Date: Mar. 22, 2019

(87) PCT Pub. No.: WO2017/170610
PCT Pub. Date: Oct. 5, 2017

(65) Prior Publication Data
US 2019/0218587 A1    Jul. 18, 2019

(30) Foreign Application Priority Data

Mar. 29, 2016 (JP) ................. 2016-066696
Jan. 31, 2017 (JP) ................. 2017-015821

(51) Int. Cl.
*G01N 33/48*    (2006.01)
*C12N 15/09*    (2006.01)
*C12Q 1/02*     (2006.01)
*C12Q 1/68*     (2018.01)
*G01N 33/50*    (2006.01)
*G01N 33/53*    (2006.01)
*G01N 33/68*    (2006.01)
*G16B 20/00*    (2019.01)

(52) U.S. Cl.
CPC ............. *C12Q 1/025* (2013.01); *C12N 15/09* (2013.01); *C12Q 1/68* (2013.01); *G01N 33/50* (2013.01); *G01N 33/5008* (2013.01); *G01N 33/53* (2013.01); *G01N 33/6845* (2013.01); *G01N 33/6893* (2013.01); *G01N 2500/04* (2013.01); *G01N 2500/10* (2013.01); *G01N 2800/347* (2013.01); *G01N 2800/52* (2013.01); *G01N 2800/56* (2013.01); *G01N 2800/60* (2013.01); *G01N 2800/70* (2013.01); *G16B 20/00* (2019.02)

(58) Field of Classification Search
CPC .......... G01N 33/6845; G01N 2500/04; G01N 2500/10; G01N 2800/347; G01N 2800/52; G01N 2800/60
See application file for complete search history.

(56) References Cited

U.S. PATENT DOCUMENTS

| 9,970,946 | B2 | 5/2018 | Uchiyama et al. |
|---|---|---|---|
| 2003/0017481 | A1 | 1/2003 | Golub et al. |
| 2004/0091498 | A1 | 5/2004 | Zhang et al. |
| 2004/0185503 | A1 | 9/2004 | Yamanouchi et al. |
| 2005/0079514 | A1 | 4/2005 | Liew |
| 2005/0112701 | A1 | 5/2005 | Arndt et al. |
| 2005/0159896 | A1 | 7/2005 | Ishikawa et al. |
| 2006/0008804 | A1 | 1/2006 | Chibout et al. |
| 2006/0088876 | A1 | 4/2006 | Bauer |
| 2007/0161125 | A1 | 7/2007 | Rosenfeld et al. |
| 2009/0061454 | A1 | 3/2009 | Brody et al. |
| 2009/0291434 | A1 | 11/2009 | Cowens et al. |
| 2010/0322850 | A1 | 12/2010 | Eizirik et al. |
| 2013/0023054 | A1 | 1/2013 | Meikle et al. |
| 2013/0045494 | A1 | 2/2013 | Anderberg et al. |
| 2013/0045873 | A1 | 2/2013 | Hood et al. |

(Continued)

FOREIGN PATENT DOCUMENTS

| CN | 101611319 | 12/2009 |
|---|---|---|
| CN | 102558336 | 7/2012 |
| CN | 102884205 | 1/2013 |
| CN | 103717620 | 4/2014 |
| CN | 103998937 | 8/2014 |
| CN | 105004864 | 10/2015 |
| DE | 44 00 745 | 7/1995 |
| EP | 1 124 572 | 8/2001 |
| EP | 1 466 925 | 10/2004 |
| EP | 2 479 572 | 7/2012 |
| EP | 3 316 159 | 5/2018 |
| EP | 3 438 282 | 2/2019 |
| JP | 2001-17171 | 1/2001 |
| JP | 2001-37486 | 2/2001 |

(Continued)

OTHER PUBLICATIONS

Partial Supplementary European Search Report dated Dec. 12, 2019 in corresponding European Patent Application No. 17775147.6.

(Continued)

*Primary Examiner* — Russell S Negin
(74) *Attorney, Agent, or Firm* — Wenderoth, Lind & Ponack, L.L.P.

(57) ABSTRACT

This invention provides a device for screening a candidate substance for an active ingredient to prevent or treat declined kidney function etc. A screening device 1 for screening a candidate substance for an active ingredient to prevent or treat declined kidney function etc. comprises a first measurement value obtaining unit 11 for obtaining a measurement value of a kidney function prediction marker protein and/or a measurement value of mRNA of the protein in a test-substance-treated specimen, and a candidate substance determination unit 14 for determining that the test substance is a candidate substance for the active ingredient based on the measurement value(s) obtained by the first measurement value obtaining unit 11.

10 Claims, 310 Drawing Sheets
Specification includes a Sequence Listing.

(56) References Cited

U.S. PATENT DOCUMENTS

| | | | |
|---|---|---|---|
| 2013/0157883 A1 | 6/2013 | Keller et al. | |
| 2013/0230871 A1 | 9/2013 | Anderberg et al. | |
| 2013/0259879 A1 | 10/2013 | Baumhof et al. | |
| 2014/0038203 A1 | 2/2014 | Arthur et al. | |
| 2014/0100125 A1 | 4/2014 | Vanburen et al. | |
| 2014/0170677 A1 | 6/2014 | Klinguer-Hamour et al. | |
| 2014/0286953 A1 | 9/2014 | Sasu et al. | |
| 2014/0323389 A1 | 10/2014 | Hohlbaum et al. | |
| 2015/0285821 A1 | 10/2015 | Uchiyama et al. | |
| 2017/0224770 A1 | 8/2017 | Hohlbaum et al. | |
| 2018/0311311 A1 | 11/2018 | Hohlbaum et al. | |
| 2019/0250170 A1 | 8/2019 | Anderberg et al. | |

FOREIGN PATENT DOCUMENTS

| | | | |
|---|---|---|---|
| JP | 2002-516107 | 6/2002 | |
| JP | 2004-187620 | 7/2004 | |
| JP | 2005-500803 | 1/2005 | |
| JP | 2005-508505 | 3/2005 | |
| JP | 2005-510240 | 4/2005 | |
| JP | 2005-518810 | 6/2005 | |
| JP | 2005-229834 | 9/2005 | |
| JP | 2005-323573 | 11/2005 | |
| JP | 2007-521799 | 8/2007 | |
| JP | 2008-512104 | 4/2008 | |
| JP | 2008-518626 | 6/2008 | |
| JP | 2011-50250 | 3/2011 | |
| JP | 2012-507012 | 3/2012 | |
| JP | 2013-126427 | 6/2013 | |
| JP | 2013-215201 | 10/2013 | |
| JP | 2013-538565 | 10/2013 | |
| JP | 2013-541323 | 11/2013 | |
| JP | 2014-122170 | 7/2014 | |
| WO | 99/61622 | 12/1999 | |
| WO | 00/23100 | 4/2000 | |
| WO | 02/20718 | 3/2002 | |
| WO | 03/040404 | 5/2003 | |
| WO | 03/046180 | 6/2003 | |
| WO | 03/057874 | 7/2003 | |
| WO | 03/074731 | 9/2003 | |
| WO | 03/085548 | 10/2003 | |
| WO | 2004/005934 | 1/2004 | |
| WO | 2005/045044 | 5/2005 | |
| WO | 2005/106493 | 11/2005 | |
| WO | 2005/114207 | 12/2005 | |
| WO | 2006/027265 | 3/2006 | |
| WO | 2007/011412 | 1/2007 | |
| WO | 2008/008430 | 1/2008 | |
| WO | 2010/048670 | 5/2010 | |
| WO | 2010/100633 | 9/2010 | |
| WO | 2012/012693 | 1/2012 | |
| WO | 2012/012725 | 1/2012 | |
| WO | WO-2012012704 A2 * | 1/2012 | ........... C12Q 1/6883 |
| WO | 2013/011059 | 1/2013 | |
| WO | 2013/011063 | 1/2013 | |
| WO | 2014/093622 | 6/2014 | |
| WO | 2015/069900 | 5/2015 | |
| WO | 2015/184011 | 12/2015 | |

OTHER PUBLICATIONS

Extended European Search Report dated Jan. 7, 2020 in European Patent Application No. 17775337.3.
Han et al., "Apelin: A novel inhibitor of vascular calcification in chronic kidney disease", Atherosclerosis, 2015, vol. 244, pp. 1-8.
Sagiroglu et al., "Effects of apelin and leptin on renal functions following renal ischemia/reperfusion: An experimental study", Experimental and Therapeutic Medicine, 2012, vol. 3, No. 5, pp. 908-914.
Chen et al., "Apelin protects against acute renal injury by inhibiting TGF-β1", Biochimica et Biophysica Acta, 2015, vol. 1852, No. 7, pp. 1278-1287.

Clarkson et al., "Serum and Urinary Fibrin/Fibrinogen Degradation Products in Glomerulonephritis", British Medical Journal, 1971, vol. 3, pp. 447-451.
Crotti et al., "Osteoimmunology: Major and Costimulatory Pathway Expression Associated with Chronic Inflammatory Induced Bone Loss", Journal of Immunology Research, 2015, vol. 2015, pp. 1-13.
Goettsch et al., "The Osteoclast-Associated Receptor (OSCAR) Is a Novel Receptor Regulated by Oxidized Low-Density Lipoprotein in Human Endothelial Cells", Endocrinology, 2011, vol. 152, No. 12, pp. 4915-4926.
Ndongo-Thiam et al., "Levels of soluble osteoclast-associated receptor (sOSCAR) in rheumatoid arthritis: link to disease severity and cardiovascular risk", Annals of the Rheumatic Diseases, 2014, vol. 73, No. 6, pp. 1276-1277.
Office Action dated Nov. 4, 2020 in U.S. Appl. No. 16/089,648.
Imel et al., "Fibroblast Growth Factor 23: Roles in Health and Disease", Journal of the American Society of Nephrology, 2005, vol. 16, pp. 2565-2575.
"C4b-binding protein alpha chain [*Homo sapiens*]", pp. 1 and 2, Apr. 27, 1993.
"C4BPA complement component 4 binding protein alpha [*Homo sapiens* (human)]", pp. 1-14, Jul. 3, 2022.
Extended European Search Report dated Apr. 26, 2022 in corresponding European Patent Application No. 21203319.5.
Beatriz Mattin-Antonio et al., "Genomic characterization and gene expression analysis of four hepcidin genes in the redbanded seabream (*Pagrus auriga*)", Fish & Shellfish Immunology, vol. 26, pp. 483-491, 2009.
Office Action dated May 25, 2021 in corresponding Chinese Patent Application No. 201680049081.1, with English Machine Translation.
International Search Report dated Sep. 27, 2016 in International (PCT) Application No. PCT/JP2016/069564.
Takeda, "Senescence-Accelerated Mouse (SAM): With Special Reference to Age-associated Pathologies and Their Modulation", vol. 51, Jpn. J. Hyp., 1996, pp. 569-578, with English abstract.
International Search Report dated Mar. 21, 2017 in International (PCT) Application No. PCT/JP2017/002406.
Oh et al., "Profile of Human β-Defensins 1,2 and Proinflammatory Cytokines (TNF-α, IL-6) in Patients with Chronic Kidney Disease", Kidney & Blood Pressure Research, vol. 37, 2013, pp. 602-610.
Koike et al., "Identification of α-HNP-3 defensin in diabetes mellitus patient's urine—Potential marker for early diagnosis of diabetic nephropathy-", Journal of Analytical Bio-science, vol. 30, No. 4, 2007, pp. 334-339, with English summary, cited in DC.
Orita, "Recent progress in protein restriction therapy for chronic renal insufficiency", Journal of Clinical and Experimental Medicine, vol. 171, No. 6, 1994, pp. 607-610, cited in DC.
Mikiko Funakoshi et al., "Proline-rich Protein (PRP) Levels In Inflammatory Diseases", The Journal Japan Atherosclerosis Society, vol. 14, No. 6, 1987, pp. 1249-1250, with English summary, cited in DC.
Lu et al., "Inductively coupled mass spectrometry analysis of biometals in conditional Hamp1 and Hamp1 and Hamp2 transgenic mouse models", Transgenic Res., vol. 24, 2015, pp. 765-773.
Lysaght, "Maintenance Dialysis Population Dynamics: Current Trends and Long-Term Implications", J Am Soc Nephrol, vol. 13, 2002, pp. S37-S40.
Sata et al., "New protein in human blood plasma, rich in proline, with lipid-binding properties", Proc. Nat. Acad. Sci. USA, vol. 73, No. 4, Apr. 1976, pp. 1063-1067.
Matsuguch et al., "Molecular Cloning of the cDNA Coding for Proline-Rich Protein (PRP): Identity of PRP as C4b-Binding Protein", Biochemical and Biophysical Research Communications, vol. 165, No. 1, Nov. 30, 1989, pp. 138-144.
International Search Report dated Jul. 4, 2017 in International (PCT) Application No. PCT/JP2017/012761.
Husain-Syed et al., "Cardio-Pulmonary-Renal Interactions", Journal of the American College of Cardiology, 2015, vol. 65, No. 22, pp. 2433-2448.
White et al., "Inflammatory Mechanisms of Organ Crosstalk during Ischemic Acute Kidney Injury", International Journal of Nephrology, 2012, Article ID 505197, pp. 1-8.

(56) References Cited

OTHER PUBLICATIONS

Zoccali et al., "Chronic Kidney Disease (CKD) as a Systemic Disease: Whole Body Autoregulation and Inter-Organ Cross-Talk", Kidney & Blood Pressure Research, 2014, vol. 39, pp. 134-141.
White et al., "Surgical Sepsis and Organ Crosstalk: The Role of the Kidney", Journal of Surgical Research, 2011, vol. 167, pp. 306-315.
Lysaght, "Maintenance Dialysis Population Dynamics: Current Trends and Long-Term Implications", Journal of the American Society of Nephrology, 2002, vol. 13, pp. S37-S40.
Hu et al., "Klotho Deficiency Causes Vascular Calcification in Chronic Kidney Disease", Journal of the American Society of Nephrology, 2011, vol. 22, pp. 124-136.
International Search Report dated May 9, 2017 in International (PCT) Application No. PCT/JP2017/013124.
Manconi et al., "The intriguing heterogeneity of human salivary proline-rich proteins; Short title: Salivary proline-rich protein species", Journal of Proteomics, 2015, vol. 134, pp. 47-56.
Hoffmann et al., "Fibrinogen Excretion in the Urine and Immunoreactivity in the Kidney Serves as a Translational Biomarker for Acute Kidney Injury", The American Journal of Pathology, 2012, vol. 181, No. 3, pp. 818-828.
Prinsen et al., "Increased albumin and fibrinogen synthesis rate in patients with chronic renal failure", Kidney International, 2003, vol. 64, pp. 1495-1504.
Zhang et al., "Urinary biomarkers track the progression of nephropathy in hypertensive and obese rats", Biomarkers in Medicine, 2014, vol. 8, No. 1, pp. 85-94.
Craciun et al., "Pharmacological and genetic depletion of fibrinogen protects from kidney fibrosis", American Journal of Physiology, 2014, vol. 307, pp. F471-F484.
International Preliminary Report on Patentability dated Apr. 6, 2017 in International (PCT) Application No. PCT/JP2017/002406, with English translation.
International Preliminary Report on Patentability dated Jun. 5, 2017 in International (PCT) Application No. PCT/JP2017/069564 with English translation.
Partial Supplementary European Search Report dated Mar. 13, 2019 in European Application No. 16814543.1.
Keen et al., "The Genotype-Tissue Expression (GTEx) Project: Linking Clinical Data with Molecular Analysis to Advance Personalized Medicine", Journal of Personalized Medicine, 2015, vol. 5, No. 1, pp. 22-29.
Uhlén et al., "Tissue-based map of the human proteome", Science, Jan. 2015, vol. 347, Issue No. 6220, pp. 1260419-1 to 1260419-9.
Kim et al., "A draft map of the human proteome", vol. 509, No. 7502, Nature, May 2014, pp. 575-581.
Uhlén et al., "Transcriptomics resources of human tissues and organs", Molecular Systems Biology, 2016, vol. 12:862, No. 4, pp. 1-12.
Kozawa et al., "The Body-Wide Transcriptome Landscape of Disease Models", iScience, vol. 2, 2018, pp. 238-268.
Supplementary Extended European Search Report dated Apr. 6, 2020 in European Patent Application No. 17775147.6.
Eulitz et al., "Inhibition of deoxyribonuclease I by actin is to protect cells from premature cell death", Apoptosis, 2007, vol. 12, No. 8, pp. 1511-1521.
Isern et al., "Functional analysis and androgen-regulated expression of mouse organic anion transporting polypeptide 1 (Oatp 1) in the kidney", Biochimica et Biophysica Acta, 2001, vol. 1518, No. 1-2, pp. 73-78.
Saraheimo et al., "Increased levels of α-defensin (-1, -2 and -3) in type 1 diabetic patients with nephropathy", Nephrology Dialysis Transplantation, 2008, vol. 23, No. 3, pp. 914-918.
Young et al., "Hepcidin for Clinicians", Clinical Journal of the American Society of Nephrology, 2009, vol. 4, No. 8, pp. 1384-1387.
Ruchala et al., "The pathophysiology and pharmacology of hepcidin", Trends in Pharmacological Sciences, 2014, vol. 35, No. 3, pp. 155-161.
Qisheng et al., "Gene Editing Tools Mediated by CRISPR-Cas", Biotechnology Bulletin, 2014, Issue No. 7, pp. 37-43.
Bing et al., "Significance of change of renal tubule markers before and after treatment in chronic glomerulonephritis", Lab Med Clin, 2012, vol. 9, No. 19, pp. 2436-2439.
Notice of First Office Action dated Sep. 3, 2020 in corresponding Chinese Patent Application No. 201780032992.8, with English Translation.
Karn et al., "Shared and Unique Proteins in Human, Mouse and Rat Saliva Proteomes: Footprints of Functional Adaptation", Proteomes, 2013, vol. 1, pp. 275-289.
Abstract of Isemura et al., "Tissue distribution and nucleotide sequence of bovine mRNA for salivary proline-rich protein P-B", Archives of Oral Biology, 2004, vol. 49, No. 11, pp. 881-887.
Hao et al., "Effects of Valsartan on Ventricular Hypertrophy and Expression of Proline-rich Tyrosine Kinase 2 in Myocardium of Re-novascular Hypertensive Rats", Chin J Hypertension, 2008, vol. 16, No. 3, pp. 249-252, with Abstract.
Tsuchiya, K, et al., Hepcidin is a Potential Regulator of Iron Status in Chronic Kidney Disease, Therapeutic Apheresis and Dialysis, 2013, vol. 17, No. 1, pp. 1-8.
Srai, S.K., et al., "Erythropoietin regulates intestinal iron absorption in a rat model of chronic renal failure", Kidney International, 2010, vol. 78, pp. 660-667.
Maleki, F. et al., "Size matters: how sample size affects the reproducibility and specificity of gene set analysis", Human Genomics, 2019, vol. 13 (Suppl. 1), No. 42, 12 pages.
Jafari, P. et al., "An assessment of recently published gene expression data analyses: reporting experimental design and statistical factors" BMC Medical Informatics and Decision Making, 2006, vol. 6, No. 27, 8 pages.
Office Action dated Apr. 12, 2023 in corresponding U.S. Appl. No. 16/072,708, 4 pages.
Office Action dated Jun. 23, 2023 in U.S. Appl. No. 17/396,084.
Office Action dated Jun. 23, 2023 in U.S. Appl. No. 17/396,165.
Office Action dated Sep. 22, 2023 in U.S. Appl. No. 16/072,708.
Manconi et al., "The intriguing heterogeneity of human salivary proline-rich proteins," Journal of Proteomics, vol. 134, pp. 47-56, Sep. 2015.
Office Action issued Nov. 28, 2023 in Chinese Patent Application No. 202210266914.7, with English-language translation.
Office Action issued Nov. 28, 2023 in Chinese Patent Application No. 202210267284.5, with English-language translation.
Office Action issued Apr. 3, 2024 in U.S. Appl. No. 17/396,084.
Office Action issued Apr. 3, 2024 in U.S. Appl. No. 17/396,165.
Office Action issued May 2, 2024 in U.S. Appl. No. 16/072,708.
Extended European Search Report issued Jul. 16, 2019 in European Application No. 16814543.1.
Tothill et al., "An Expression-Based Site of Origin Diagnostic Method Designed for Clinical Application to Cancer of Unknown Origin", Cancer Res., vol. 65, No. 10, May 15, 2005, pp. 4031-4040.
Talantov et al., "A Quantitive Reverse Transcriptase-Polymerase Chain Reaction Assay to Identify Metastatic Carcinoma Tissue of Origin", Journal of Molecular Diagnostic, vol. 8, No. 3, Jul. 2006, pp. 320-329.
Greene et al., "Understanding multicellular function and disease with human tissue-specific networks", Nat Genet., vol. 47, No. 6, Jun. 2015, pp. 569-576.

* cited by examiner

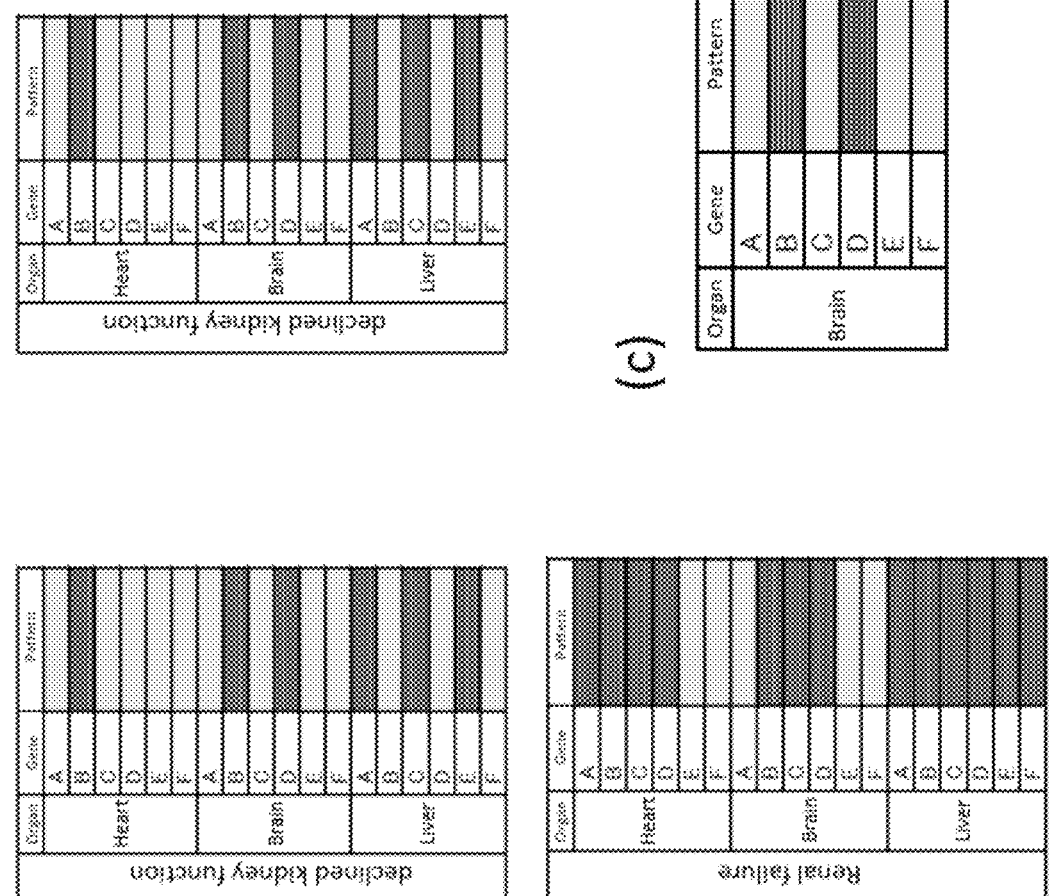
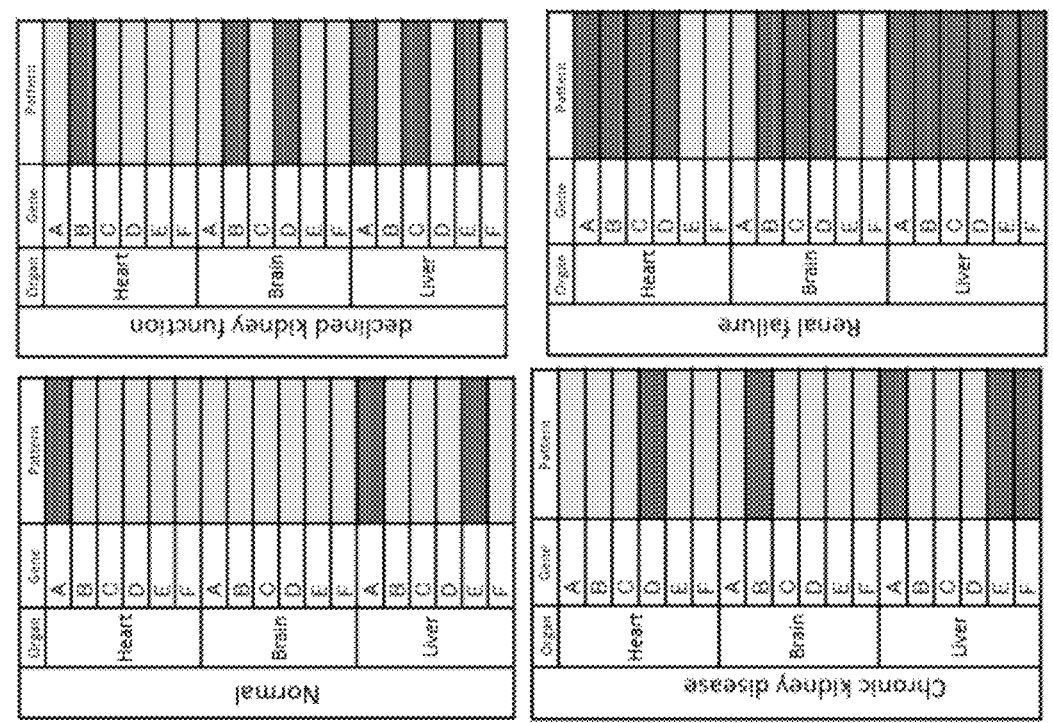
Fig.12

Fig.21 - 1

| Line No. | Gene Name | Reference Seq. ID | Chromosome Location |
|---|---|---|---|
| 1 | 0610005C13Rik | NR_038165.1 | chr7:45567794-45575176 |
| 2 | 0610007P14Rik | NM_021446.2 | chr12:85815454-85824545 |
| 3 | 0610009B22Rik | NM_025319.2 | chr11:51685384-51688634 |
| 4 | 0610009L18Rik | NR_038126.1 | chr11:120348677-120351190 |
| 5 | 0610009O20Rik | NM_024179.5 | chr18:38250248-38262629 |
| 6 | 0610010B08Rik | NM_001177543.1 | chr2:175965355-175981734 |
| 7 | 0610010F05Rik | NM_027860.2 | chr11:23573775-23633631 |
| 8 | 0610010K14Rik | NM_001177601.1 | chr11:70235203-70237914 |
| 9 | 0610011F06Rik | NM_026686.2 | chr17:25875499-25877163 |
| 10 | 0610012G03Rik | NR_027897.1 | chr16:31947050-31948521 |
| 11 | 0610030E20Rik | NM_026696.1 | chr6:72347316-72353160 |
| 12 | 0610031J06Rik | NM_020003.1 | chr3:88325022-88328631 |
| 13 | 0610031O16Rik | NR_045760.1 | chr3:138210716-138239663 |
| 14 | 0610037L13Rik | NM_028754.2 | chr4:107889898-107897802 |
| 15 | 0610038B21Rik | NR_028125.1 | chr8:77517055-77518578 |
| 16 | 0610039K10Rik | NR_028113.1 | chr2:163644849-163645800 |
| 17 | 0610040B10Rik | NR_027874.1 | chr5:143329307-143332704 |
| 18 | 0610040F04Rik | NR_040757.1 | chr6:108610217-108623167 |
| 19 | 0610040J01Rik | NM_029554.4 | chr5:63812494-63899619 |
| 20 | 0610043K17Rik | NR_040640.1 | chr4:101353782-101399185 |
| 21 | 1010001N08Rik | NR_105022.1 | chr18:11049928-11052567 |
| 22 | 1100001G20Rik | NM_183249.2 | chr11:83746939-83752646 |
| 23 | 1110001A03Rik | NM_025363.3 | chr6:38534860-38539449 |
| 24 | 1110002L01Rik | NR_030694.1 | chr12:3403882-3426747 |
| 25 | 1110004E09Rik | NM_026502.2 | chr16:90925810-90934849 |
| 26 | 1110004F10Rik | NM_019772.2 | chr7:116093379-116105210 |
| 27 | 1110006O24Rik | NR_027810.1 | chr5:115631048-115631816 |
| 28 | 1110007C09Rik | NM_026738.2 | chr13:49202950-49216026 |
| 29 | 1110008F13Rik | NM_026124.3 | chr2:156863121-156873562 |
| 30 | 1110008L16Rik | NM_025373.1 | chr12:55302636-55382491 |
| 31 | 1110008P14Rik | NM_198001.2 | chr2:32379106-32381915 |
| 32 | 1110012L19Rik | NM_026787.2 | chrX:70385912-70389416 |
| 33 | 1110015O18Rik | NR_045272.1 | chr3:4798707-4814911 |
| 34 | 1110017D15Rik | NM_001048005.1 | chr4:41505008-41517333 |
| 35 | 1110019D14Rik | NR_045995.1 | chr6:13871568-13896421 |
| 36 | 1110020A21Rik | NR_027897.1 | chr17:84917181-84957423 |
| 37 | 1110025L11Rik | NM_001276278.1 | chr16:89063409-89064002 |
| 38 | 1110028F11Rik | NR_045139.1 | chr13:87699523-87705327 |
| 39 | 1110028F18Rik | NR_045470.1 | chr8:106587142-106594820 |
| 40 | 1110032A03Rik | NM_023483.3 | chr9:50762827-50768152 |
| 41 | 1110032F04Rik | NM_001167996.1 | chr3:68869585-68872163 |
| 42 | 1110034G24Rik | NM_028637.3 | chr2:132690282-132751055 |
| 43 | 1110036E04Rik | NR_040713.1 | chr9:64049828-64054100 |
| 44 | 1110037F02Rik | NM_001081183.1 | chr4:11485957-11551143 |
| 45 | 1110038B12Rik | NR_015536.1 | chr17:34950235-34952471 |
| 46 | 1110038F14Rik | NM_054099.2 | chr15:76948543-76950731 |
| 47 | 1110046J04Rik | NR_040707.1 | chr13:33936031-33960181 |
| 48 | 1110051M20Rik | NM_175123.4 | chr2:91277827-91444642 |
| 49 | 1110054M08Rik | NR_037954.1 | chr16:24392555-24393655 |
| 50 | 1110057K04Rik | NM_001167767.1 | chr12:8208126-8285759 |
| 51 | 1110058L19Rik | NM_026503.3 | chr1:23995938-24005640 |
| 52 | 1110059E24Rik | NM_025423.2 | chr19:21597312-21652791 |
| 53 | 1110059G10Rik | NM_025419.4 | chr9:122945088-122951000 |
| 54 | 1110065P20Rik | NM_001142727.1 | chr4:124849484-124850730 |
| 55 | 1190002F15Rik | NR_037955.1 | chr6:134929091-134951718 |
| 56 | 1190002N15Rik | NM_001033145.2 | chr9:94517863-94538081 |
| 57 | 1190003K10Rik | NM_001119543.1 | chr13:64481245-64497792 |
| 58 | 1190005I06Rik | NM_197988.1 | chr8:120608601-120634382 |
| 59 | 1190007J07Rik | NM_001135567.1 | chr10:82619850-82623228 |
| 60 | 1200014J11Rik | NM_025818.3 | chr11:73047866-73083579 |
| 61 | 1300002E11Rik | NR_037957.1 | chr16:21794346-21806125 |
| 62 | 1300002K09Rik | NM_028788.4 | chr4:45848946-45887010 |
| 63 | 1300017J02Rik | NM_019782.2 | chr9:103250529-103288297 |
| 64 | 1500004A13Rik | NR_015498.2 | chr3:88822009-88832487 |
| 65 | 1500009C09Rik | NR_037697.1 | chr15:82252396-82260751 |
| 66 | 1500009L16Rik | NM_001145198.1 | chr10:83722864-83762762 |
| 67 | 1500011B03Rik | NR_027817.1 | chr5:114808195-114813976 |
| 68 | 1500011K16Rik | NR_015476.1 | chr2:127791176-127792488 |
| 69 | 1500012F01Rik | NM_001081005.1 | chr2:167062933-167065862 |
| 70 | 1500012K07Rik | NR_045821.1 | chr7:75308695-75318485 |
| 71 | 1500015A07Rik | NM_029432.1 | chr18:61726389-61728253 |
| 72 | 1500015L24Rik | NR_045817.2 | chr19:20405287-20422785 |
| 73 | 1500015O10Rik | NM_024283.3 | chr1:43730601-43742564 |
| 74 | 1500017E21Rik | NR_033510.1 | chr19:36619417-36689479 |
| 75 | 1600002D24Rik | NR_040484.1 | chr16:95841885-95929077 |
| 76 | 1600002H07Rik | NM_028676.1 | chr17:24215055-24220769 |
| 77 | 1600002K03Rik | NM_027207.2 | chr10:80172943-80175119 |
| 78 | 1600010M07Rik | NR_037959.1 | chr7:109998376-110006646 |
| 79 | 1600012H06Rik | NM_001083880.1 | chr17:14943183-14945939 |
| 80 | 1600014C10Rik | NM_001085385.1 | chr7:38183216-38197565 |
| 81 | 1600014C23Rik | NM_028164.1 | chr17:45732863-45733844 |
| 82 | 1600014K23Rik | NM_028046.1 | chrX:85249676-85270291 |
| 83 | 1600015I10Rik | NM_001081273.2 | chr6:48929895-48933687 |
| 84 | 1600016N20Rik | NM_028062.2 | chr7:141210042-141214080 |
| 85 | 1600019K03Rik | NR_040481.1 | chr6:35503169-35509419 |
| 86 | 1600020E01Rik | NR_037960.1 | chr6:86527329-86564449 |
| 87 | 1600023N17Rik | NR_073433.1 | chr5:45668700-45669708 |
| 88 | 1600025M17Rik | NR_038168.1 | chrX:56317607-56320664 |
| 89 | 1600027J07Rik | NR_036588.1 | chr8:103343877-103347534 |
| 90 | 1600029I14Rik | NR_028123.1 | chr9:99470420-99474751 |
| 91 | 1600029O15Rik | NR_033522.1 | chr9:58202896-58208808 |
| 92 | 1700001C02Rik | NR_045900.2 | chr5:30466076-30484087 |
| 93 | 1700001C19Rik | NM_001172091.1 | chr17:47412733-47414711 |
| 94 | 1700001D01Rik | NR_045475.1 | chr8:61281521-61288872 |
| 95 | 1700001F09Rik | NM_027940.2 | chr4:43342383-43347811 |
| 96 | 1700001G11Rik | NR_038077.1 | chr14:66295328-66297129 |
| 97 | 1700001G17Rik | NR_033199.1 | chr1:33669823-33670712 |
| 98 | 1700001J03Rik | NM_001008547.1 | chr5:146182449-146185304 |
| 99 | 1700001J11Rik | NR_033613.1 | chr9:40050557-40053025 |
| 100 | 1700001K19Rik | NM_025488.2 | chr12:110667688-110682619 |
| 101 | 1700001K23Rik | NR_036590.1 | chr19:53248735-53255205 |
| 102 | 1700001L05Rik | NR_027980.1 | chr15:83353846-83367297 |
| 103 | 1700001L19Rik | NM_027035.1 | chr13:68597438-68614231 |
| 104 | 1700001O22Rik | NM_198000.3 | chr2:30795562-30801737 |
| 105 | 1700001P01Rik | NM_028156.2 | chr11:97771480-97775918 |
| 106 | 1700003C15Rik | NR_045478.1 | chr5:11749832-11769308 |
| 107 | 1700003D09Rik | NR_045477.1 | chr11:98350717-98358283 |
| 108 | 1700003E16Rik | NM_027948.1 | chr6:83156403-83162975 |
| 109 | 1700003E24Rik | NR_103799.1 | chrX:93156220-93183944 |
| 110 | 1700003F12Rik | NM_029305.2 | chr2:154548903-154550048 |
| 111 | 1700003G13Rik | NR_040720.1 | chr9:45318265-45322079 |
| 112 | 1700003G18Rik | NM_029433.1 | chr7:116081761-116093149 |
| 113 | 1700003H04Rik | NR_015460.1 | chr3:124565890-124581091 |
| 114 | 1700003L19Rik | NR_040507.1 | chr16:12811389-12848653 |
| 115 | 1700003M02Rik | NM_027041.4 | chr4:34711331-34730206 |
| 116 | 1700003M07Rik | NR_040647.1 | chr4:129960373-129965138 |
| 117 | 1700003P14Rik | NR_045982.1 | chr13:118556167-118588629 |
| 118 | 1700006A11Rik | NM_027939.1 | chr3:124401154-124426028 |
| 119 | 1700006E09Rik | NM_029287.1 | chr11:101987055-101992264 |
| 120 | 1700006F04Rik | NR_045621.1 | chr14:119749226-119751564 |
| 121 | 1700006H21Rik | NR_045900.2 | chr13:107687396-107692168 |
| 122 | 1700007B14Rik | NM_001164235.1 | chr8:75448693-75984507 |
| 123 | 1700007F19Rik | NR_040538.1 | chr3:58141706-58163807 |
| 124 | 1700007G14Rik | NM_001024614.1 | chr5:98329303-98802019 |
| 125 | 1700007I10Rik | NR_045476.1 | chr11:59725916-59740154 |
| 126 | 1700007K09Rik | NM_027037.2 | chr7:131325930-131329499 |
| 127 | 1700007K13Rik | NM_027040.1 | chr2:28462000-28466324 |
| 128 | 1700007L15Rik | NR_045709.1 | chr16:33379853-33380736 |
| 129 | 1700007P06Rik | NR_040554.1 | chr1:187125137-187127852 |
| 130 | 1700008F21Rik | NM_001168369.1 | chr8:129067133-129183732 |
| 131 | 1700008I05Rik | NM_027952.3 | chrX:135654697-135693790 |
| 132 | 1700008J07Rik | NR_024331.1 | chr7:127510437-127512869 |
| 133 | 1700008K24Rik | NR_038141.1 | chr17:49112263-49113533 |
| 134 | 1700008O03Rik | NM_027049.3 | chr7:44360044-44375030 |
| 135 | 1700008P02Rik | NM_027048.1 | chr3:6615412-6620443 |
| 136 | 1700009C05Rik | NR_046040.1 | chr6:81900464-81910800 |
| 137 | 1700009J07Rik | NR_015547.1 | chr10:77893419-77896111 |
| 138 | 1700009N14Rik | NM_001081095.1 | chr4:39450292-39451778 |
| 139 | 1700009P17Rik | NM_001081275.1 | chr1:171121660-171126967 |
| 140 | 1700010B08Rik | NM_029308.1 | chr2:173719414-173722086 |
| 141 | 1700010D01Rik | NM_029590.3 | chrX:95732589-95733265 |
| 142 | 1700010I02Rik | NR_040587.1 | chr3:7925302-7954887 |
| 143 | 1700010I14Rik | NM_025851.3 | chr17:8988332-9008319 |
| 144 | 1700010I16Rik | NR_040579.1 | chr10:112726925-112785599 |
| 145 | 1700010K23Rik | NR_040512.1 | chr16:66657117-66664626 |
| 146 | 1700011A15Rik | NM_025487.3 | chr15:101447744-101453909 |
| 147 | 1700011B04Rik | NR_045616.1 | chr13:35181622-35188014 |
| 148 | 1700011E24Rik | NM_029298.1 | chr17:87389570-87427741 |
| 149 | 1700011H14Rik | NM_025956.4 | chr14:49226358-49245428 |
| 150 | 1700011I03Rik | NM_029290.1 | chr18:57533825-57731065 |
| 151 | 1700011L22Rik | NM_026315.1 | chr8:79210429-79248583 |
| 152 | 1700011M02Rik | NR_073044.1 | chrX:102908904-102909651 |
| 153 | 1700012A03Rik | NM_029587.2 | chr6:32050287-32058915 |
| 154 | 1700012B07Rik | NM_001162428.1 | chr11:109788290-109808046 |
| 155 | 1700012B09Rik | NM_029306.3 | chr9:14758193-14771030 |
| 156 | 1700012D01Rik | NR_045171.1 | chr10:127667122-127668861 |
| 157 | 1700012D14Rik | NR_015573.2 | chr7:111117672-111122675 |
| 158 | 1700012I11Rik | NR_045140.1 | chr15:67226768-67377094 |
| 159 | 1700012L04Rik | NM_029588.3 | chrX:9283763-9284288 |
| 160 | 1700012P22Rik | NR_027056.1 | chr4:144418190-144438772 |
| 161 | 1700013D24Rik | NM_001177502.1 | chr6:124347593-124357086 |
| 162 | 1700013F07Rik | NM_029314.1 | chr3:108537583-108544697 |
| 163 | 1700013G24Rik | NM_027063.2 | chr4:137453295-137455461 |
| 164 | 1700013H16Rik | NM_001209013.1 | chrX:53742900-53757831 |
| 165 | 1700015E13Rik | NM_001039593.1 | chr1:170308860-170312125 |
| 166 | 1700015F17Rik | NM_001200025.1 | chr5:5437826-5479143 |
| 167 | 1700015G11Rik | NM_001195601.1 | chr7:52011679-52015716 |
| 168 | 1700016C15Rik | NM_027077.2 | chr1:177729813-177753305 |
| 169 | 1700016D06Rik | NM_024271.1 | chr8:11654923-11678750 |
| 170 | 1700016G22Rik | NR_045891.1 | chr13:5855508-5858092 |
| 171 | 1700016H13Rik | NM_001163550.1 | chr5:103648586-103655732 |
| 172 | 1700016K19Rik | NM_198637.2 | chr11:75999911-76003569 |
| 173 | 1700016L04Rik | NR_045824.1 | chr10:147056608-147059019 |
| 174 | 1700016L21Rik | NR_040460.1 | chr1:80445931-80475660 |
| 175 | 1700016P04Rik | NR_038149.1 | chr6:13413336-13415996 |
| 176 | 1700017B05Rik | NM_028820.2 | chr9:57252321-57262599 |
| 177 | 1700017D01Rik | NM_027058.3 | chr19:111096815-111130878 |
| 178 | 1700017G19Rik | NR_040445.1 | chr3:40504864-40522912 |
| 179 | 1700017J07Rik | NR_040326.1 | chr2:168978268-168978906 |
| 180 | 1700017N19Rik | NM_001081246.1 | chr10:100592385-100618391 |
| 181 | 1700018A04Rik | NM_029439.1 | chr13:31565491-31582513 |
| 182 | 1700018B08Rik | NM_029597.3 | chr8:121530781-121541954 |
| 183 | 1700018B24Rik | NM_003617.1 | chr3:48605730-48609100 |
| 184 | 1700018C11Rik | NM_029324.2 | chr4:63607090-63622429 |
| 185 | 1700018E24Rik | NM_027069.3 | chr5:145042989-145045678 |
| 186 | 1700018G05Rik | NR_045422.1 | chrX:102928371-102929107 |
| 187 | 1700018L02Rik | NR_028360.1 | chr19:29047482-29048729 |
| 188 | 1700019A02Rik | NR_027070.1 | chr1:53158576-53187617 |
| 189 | 1700019B03Rik | NM_029598.1 | chr8:3470861-3487178 |
| 190 | 1700019B21Rik | NR_045442.1 | chrX:62510538-62527011 |
| 191 | 1700019D03Rik | NM_144953.2 | chr1:52925126-52952840 |
| 192 | 1700019E08Rik | NR_040497.1 | chr2:45696604-45698447 |
| 193 | 1700019G17Rik | NM_001145895.1 | chr6:85899050-85902533 |

Fig.21 - 2

| | | | | | | | | |
|---|---|---|---|---|---|---|---|---|
| 194 | 1700019G24Rik | NR_040255.1 | chr6:5963896-5977393 | | 291 | 1700041C23Rik | NR_033784.1 | chr9:57175274-57186110 |
| 195 | 1700019L03Rik | NM_025619.1 | chr2:32777412-32784405 | | 292 | 1700041M19Rik | NR_040573.1 | chr16:77004227-77010881 |
| 196 | 1700019M22Rik | NR_103800.1 | chr12:96046620-96047222 | | 293 | 1700042J14Rik | NM_001081671.1 | chrX:155124980-155147849 |
| 197 | 1700019N19Rik | NM_026208.2 | chr19:58785802-58794414 | | 294 | 1700042G07Rik | NM_001099295.2 | chr4:116173371-116174297 |
| 198 | 1700019O17Rik | NM_027966.1 | chr1:86426318-86428049 | | 295 | 1700042G15Rik | NR_038178.1 | chr4:57359791-57364292 |
| 199 | 1700020A23Rik | NM_001163483.1 | chr2:130405295-130406074 | | 296 | 1700042O19Rik | NR_045178.1 | chr11:11868122-11885321 |
| 200 | 1700020D05Rik | NM_023781.5 | chr19:5502768-5503787 | | 297 | 1700044C05Rik | NR_045624.1 | chr14:118365877-118398165 |
| 201 | 1700020G17Rik | NR_045979.1 | chr10:110801173-110896507 | | 298 | 1700044K03Rik | NR_033785.1 | chr18:49523288-49524441 |
| 202 | 1700020I14Rik | NR_015473.1 | chr2:119594295-119600744 | | 299 | 1700045H11Rik | NR_040649.1 | chr4:150828224-150854949 |
| 203 | 1700020L24Rik | NM_025492.3 | chr11:83437693-83441232 | | 300 | 1700046G09Rik | NR_045918.1 | chr11:14560335-14599225 |
| 204 | 1700020M21Rik | NR_040742.1 | chr3:120913773-120915250 | | 301 | 1700047A11Rik | NR_110583.1 | chr8:26082608-26096520 |
| 205 | 1700020N01Rik | NR_027968.1 | chr10:21593144-21622375 | | 302 | 1700047E10Rik | NR_073363.1 | chr14:44191606-44213237 |
| 206 | 1700020N15Rik | NM_029316.1 | chrX:69945280-69945980 | | 303 | 1700047G03Rik | NR_040447.1 | chr15:11967061-11970083 |
| 207 | 1700020N18Rik | NR_026924.1 | chr1:91404878-91406029 | | 304 | 1700047I17Rik2 | NM_001100116.1 | chr12:55124527-55217146 |
| 208 | 1700021F05Rik | NM_026411.1 | chr10:43525120-43540994 | | 305 | 1700047L14Rik | NR_046591.1 | chr5:108763841-108768917 |
| 209 | 1700021F07Rik | NM_028158.1 | chr2:173522591-173528502 | | 306 | 1700047M11Rik | NR_015458.1 | chr1:182300833-182303289 |
| 210 | 1700021L19Rik | NM_001200038.1 | chr16:32821701-32868366 | | 307 | 1700048M11Rik | NR_045300.1 | chr16:92308715-92312466 |
| 211 | 1700021N21Rik | NR_045800.1 | chr4:134467864-134450171 | | 308 | 1700048O20Rik | NR_033553.1 | chr9:121937274-121947016 |
| 212 | 1700022A21Rik | NR_003853.1 | chr5:24645452-24648860 | | 309 | 1700049I15Rik | NR_033636.1 | chr6:147690240-147702374 |
| 213 | 1700022A22Rik | NR_045509.1 | chr15:46324584-46373899 | | 310 | 1700049I22Rik | NR_040525.1 | chr6:100527399-100533426 |
| 214 | 1700022E09Rik | NR_040568.1 | chr16:59466871-59469238 | | 311 | 1700049N17Rik | NM_028538.1 | chr7:27907391-27929430 |
| 215 | 1700022I16Rik | NR_045488.1 | chr12:9565235-9570585 | | 312 | 1700049L16Rik | NR_003644.1 | chr10:71979884-71980690 |
| 216 | 1700022I11Rik | NM_026088.3 | chr4:42969945-42974325 | | 313 | 1700051A21Rik | NR_045922.1 | chr11:72266843-72268556 |
| 217 | 1700023C21Rik | NR_045909.1 | chr11:109845877-109848476 | | 314 | 1700052I22Rik | NR_033786.1 | chr12:80923431-80924447 |
| 218 | 1700023E05Rik | NM_027970.1 | chr5:77016022-77061522 | | 315 | 1700052N11Rik | NR_027956.1 | chr11:105179020-105181433 |
| 219 | 1700023F02Rik | NR_038039.1 | chr10:66120608-66124064 | | 316 | 1700052N19Rik | NM_024261.2 | chr10:4432604-4455140 |
| 220 | 1700023F06Rik | NM_001254724.2 | chr11:103198943-103208548 | | 317 | 1700054A03Rik | NR_045326.1 | chr19:53076251-53084392 |
| 221 | 1700023I04Rik | NR_040263.1 | chr6:29985328-29993531 | | 318 | 1700054I14Rik | NR_027865.1 | chr6:122120707-122125518 |
| 222 | 1700024B18Rik | NR_045479.1 | chr14:123987634-124015684 | | 319 | 1700054M17Rik | NR_045919.1 | chr2:118804913-118308166 |
| 223 | 1700024F13Rik | NR_045363.1 | chr13:34988049-35091393 | | 320 | 1700054O13Rik | NM_026096.1 | chrX:9846946-9847500 |
| 224 | 1700024G13Rik | NM_001034037.1 | chr14:32376501-32388373 | | 321 | 1700055C04Rik | NR_040726.1 | chr9:64038464-64041465 |
| 225 | 1700024P04Rik | NM_027064.1 | chr13:98984080-98984565 | | 322 | 1700055N04Rik | NM_028545.2 | chr19:3958807-3970438 |
| 226 | 1700024P16Rik | NM_001162980.1 | chr4:104913455-105016863 | | 323 | 1700056E22Rik | NM_028516.1 | chr1:184033033-184033998 |
| 227 | 1700025B11Rik | NR_040310.1 | chr15:77558239-77561892 | | 324 | 1700057G04Rik | NM_001033184.3 | chr9:92309376-92357876 |
| 228 | 1700025C18Rik | NR_033448.1 | chr2:165078692-165090750 | | 325 | 1700057H15Rik | NR_040774.1 | chr4:124449625-124485959 |
| 229 | 1700025F22Rik | NM_027074.3 | chr9:11139682-11165320 | | 326 | 1700060C16Rik | NR_045732.1 | chr6:143593352-143651288 |
| 230 | 1700025F24Rik | NR_040568.1 | chr10:119413443-119426864 | | 327 | 1700060C20Rik | NR_036606.2 | chr2:158192007-158195734 |
| 231 | 1700025G04Rik | NM_197990.3 | chr1:151884528-152090320 | | 328 | 1700061F12Rik | NR_038180.1 | chr2:9189514-9197484 |
| 232 | 1700025K24Rik | NR_045825.1 | chr17:54352582-54370074 | | 329 | 1700061G19Rik | NM_030141.1 | chr17:56875632-56888358 |
| 233 | 1700025M24Rik | NR_040687.1 | chr5:73268579-73284184 | | 330 | 1700061I17Rik | NR_038029.1 | chr3:117060521-117077765 |
| 234 | 1700025N23Rik | NR_040523.1 | chr6:39063878-39067586 | | 331 | 1700063A18Rik | NR_040467.1 | chr1:95990658-96021758 |
| 235 | 1700026O03Rik | NM_029335.3 | chr7:83779616-83794839 | | 332 | 1700063D05Rik | NR_040392.1 | chr9:41206154-41217627 |
| 236 | 1700026D11Rik | NR_028286.1 | chr2:132490727-132524057 | | 333 | 1700063O14Rik | NR_045383.1 | chr5:91766241-91767300 |
| 237 | 1700026F02Rik | NR_045487.1 | chr8:71006727-71026755 | | 334 | 1700064J06Rik | NR_045348.1 | chr10:119092904-119103107 |
| 238 | 1700026L06Rik | NM_027283.1 | chr2:28692079-28699651 | | 335 | 1700064M15Rik | NR_045288.1 | chr12:99626052-99627974 |
| 239 | 1700027A15Rik | NR_038001.1 | chr1:73015035-73025508 | | 336 | 1700065I16Rik | NM_001271569.1 | chr9:95855417-95857882 |
| 240 | 1700027F09Rik | NR_040681.1 | chr5:64454812-64467942 | | 337 | 1700065I18Rik | NR_040315.2 | chr15:63817187-63819540 |
| 241 | 1700027H10Rik | NR_040594.1 | chr3:45416583-45439309 | | 338 | 1700065J11Rik | NR_040526.1 | chr6:35330845-35336829 |
| 242 | 1700027J24Rik | NR_040741.1 | chr9:36668855-36693189 | | 339 | 1700065J18Rik | NR_040468.1 | chr1:192841704-192842739 |
| 243 | 1700027J07Rik | NR_040585.1 | chr10:43746187-43765336 | | 340 | 1700065L07Rik | NR_108032.1 | chr6:73436964-73471021 |
| 244 | 1700028B04Rik | NR_033605.1 | chr7:28495940-28497492 | | 341 | 1700065O20Rik | NR_045386.1 | chr18:49803331-49817956 |
| 245 | 1700028D13Rik | NR_045377.1 | chr5:112206762-112210002 | | 342 | 1700066B17Rik | NR_040465.1 | chr1:39842427-39847330 |
| 246 | 1700028E10Rik | NR_045699.1 | chr5:151368674-151396164 | | 343 | 1700066B19Rik | NM_001033168.2 | chr16:35726988-35730869 |
| 247 | 1700028I16Rik | NR_038042.1 | chr10:82812122-82824242 | | 344 | 1700066M21Rik | NM_028546.1 | chr15:57377619-57385422 |
| 248 | 1700028J19Rik | NR_042299.29-44236122 | chr7:45229929-44236122 | | 345 | 1700066O12Rik | NR_045924.1 | chr5:87908587-87979351 |
| 249 | 1700028K03Rik | NM_175241.1 | chr5:107534710-107551542 | | 346 | 1700066O22Rik | NR_015541.2 | chr18:57504421-57533752 |
| 250 | 1700028M03Rik | NR_036591.1 | chr3:83555366-83574118 | | 347 | 1700067G17Rik | NR_040471.1 | chr1:89016112-89022210 |
| 251 | 1700028P14Rik | NM_026188.2 | chr19:23558759-23652812 | | 348 | 1700067K07Rik | NM_183097.2 | chr8:84001705-84004770 |
| 252 | 1700028P15Rik | NR_040509.1 | chr2:171956878-171962799 | | 349 | 1700067P10Rik | NM_028626.2 | chr17:48089631-48090920 |
| 253 | 1700029B22Rik | NR_040531.1 | chr7:131146438-131150578 | | 350 | 1700069I16Rik | NR_033216.1 | chr5:113692423-113724772 |
| 254 | 1700029F12Rik | NM_001080777.2 | chr13:97021863-97034362 | | 351 | 1700069P05Rik | NR_040527.1 | chr6:118246694-118248454 |
| 255 | 1700029H14Rik | NM_001080781.2 | chr8:13550721-13562461 | | 352 | 1700071K01Rik | NM_001033765.2 | chr11:81572501-81573539 |
| 256 | 1700029I15Rik | NM_183112.3 | chr7:92383603-92383603 | | 353 | 1700071M16Rik | NR_045444.1 | chr17:43588339-43591509 |
| 257 | 1700029J03Rik | NR_040494.1 | chr16:93396814-93458872 | | 354 | 1700072B07Rik | NR_040727.1 | chr9:58370503-58374183 |
| 258 | 1700029J07Rik | NM_001033148.3 | chr8:45953605-45975252 | | 355 | 1700072O05Rik | NR_045733.1 | chr6:120554795-120574204 |
| 259 | 1700029M20Rik | NR_045626.1 | chr4:135626654-135630198 | | 356 | 1700073E17Rik | NR_003685.1 | chr6:145387624-145392223 |
| 260 | 1700029N11Rik | NR_045489.1 | chr13:44439726-44457567 | | 357 | 1700074H08Rik | NR_045296.1 | chr13:119680041-119681582 |
| 261 | 1700029P11Rik | NM_025503.4 | chr5:81980539-81981563 | | 358 | 1700074J13Rik | NM_028550.3 | chr6:40920459-40940557 |
| 262 | 1700030A11Rik | NR_045457.1 | chr7:28905264-28906771 | | 359 | 1700080E11Rik | NM_028562.3 | chr9:105143343-105145082 |
| 263 | 1700030C10Rik | NR_015521.1 | chr12:20804391-20815779 | | 360 | 1700080N15Rik | NR_040500.1 | chr2:4132664-4141141 |
| 264 | 1700030F04Rik | NR_045731.1 | chr6:117679206-117751769 | | 361 | 1700080O16Rik | NM_028851.1 | chrX:51968694-51972772 |
| 265 | 1700030F18Rik | NM_028180.3 | chr5:99918347-99931658 | | 362 | 1700081H04Rik | NR_040693.1 | chr5:119108235-119114543 |
| 266 | 1700030J22Rik | NM_027103.2 | chr8:116969598-116978943 | | 363 | 1700084C01Rik | NM_001033185.2 | chr3:169928938-169934653 |
| 267 | 1700030K09Rik | NR_040170.2 | chr8:72443879-72460541 | | 364 | 1700084E21Rik | NR_028299.1 | chr2:30237197-30237631 |
| 268 | 1700030L20Rik | NR_040592.1 | chr3:136435269-136449349 | | 365 | 1700084F23Rik | NR_045965.1 | chr13:70004049-70028348 |
| 269 | 1700030M09Rik | NR_045903.1 | chr8:121544387-121547652 | | 366 | 1700084I12Rik | NR_033608.1 | chr15:33405208-33405939 |
| 270 | 1700030N03Rik | NR_045304.1 | chr19:3153798-3197703 | | 367 | 1700085S21Rik | NR_046045.1 | chr12:82932519-82939155 |
| 271 | 1700030O20Rik | NR_045345.1 | chr15:116723066-116729177 | | 368 | 1700086L19Rik | NR_030733.1 | chr12:74284275-74295960 |
| 272 | 1700031A10Rik | NR_045493.1 | chr17:36923791-36933432 | | 369 | 1700088E04Rik | NR_046115.1 | chr18:38238404-38250198 |
| 273 | 1700031F05Rik | NM_028496.1 | chrX:102869186-102866353 | | 370 | 1700088E04Rik | NM_138581.2 | chr15:79134654-79141251 |
| 274 | 1700031M16Rik | NR_015496.1 | chr15:98398444-98416135 | | 371 | 1700091H14Rik | NR_073362.1 | chr14:42089749-42095277 |
| 275 | 1700031P21Rik | NR_045910.1 | chr12:52599983-52602322 | | 372 | 1700092C02Rik | NR_045467.1 | chr8:77624171-77628956 |
| 276 | 1700034E13Rik | NR_030097.1 | chr18:52646219-52663731 | | 373 | 1700092C10Rik | NR_045931.1 | chr14:69164798-69171843 |
| 277 | 1700034F02Rik | NM_001163521.1 | chr11:29547949-29578352 | | 374 | 1700092L19Rik | NR_045933.1 | chr13:26293158-26312406 |
| 278 | 1700034G24Rik | NR_045396.1 | chr15:112582935-112589996 | | 375 | 1700092L24Rik | NR_045930.1 | chr11:114198257-114199199 |
| 279 | 1700034H15Rik | NR_030669.1 | chr1:191894071-191907527 | | 376 | 1700092M07Rik | NM_001177347.1 | chr19:8740717-8741225 |
| 280 | 1700034I23Rik | NR_045380.1 | chr3:40990198-40902543 | | 377 | 1700093K21Rik | NM_001110133.1 | chr11:23516202-23519942 |
| 281 | 1700034J05Rik | NM_001164236.1 | chr6:146951300-146954421 | | 378 | 1700094D03Rik | NR_028567.1 | chr3:90062795-90068347 |
| 282 | 1700034K08Rik | NM_040756.1 | chr5:92979915-93005733 | | 379 | 1700094J05Rik | NR_040580.1 | chr10:76389014-76401507 |
| 283 | 1700034O15Rik | NM_028484.2 | chr6:41684430-41685717 | | 380 | 1700094M24Rik | NR_046049.1 | chr6:52492450-52500085 |
| 284 | 1700034P13Rik | NR_040462.1 | chr1:9747647-9771256 | | 381 | 1700095A21Rik | NR_045468.1 | chr4:146519038-146546878 |
| 285 | 1700036G14Rik | NR_045542.1 | chr5:85317518-85332027 | | 382 | 1700095B10Rik | NR_040675.1 | chr5:112793291-112801703 |
| 286 | 1700037C18Rik | NR_028484.2 | chr16:3905797-3908689 | | 383 | 1700096B18Rik | NR_027883.1 | chr11:109346866-109353651 |
| 287 | 1700037H04Rik | NM_026091.2 | chr2:131146324-131160020 | | 384 | 1700096J18Rik | NR_027388.1 | chr5:25530917-25531466 |
| 288 | 1700039G15Rik | NM_001033176.1 | chr7:45242879-45258993 | | 385 | 1700097N02Rik | NR_045287.1 | chr17:30622440-30626505 |
| 289 | 1700039J22Rik | NR_045315.1 | chr19:44828492-44835938 | | 386 | 1700098L14Rik | NR_045934.1 | chr13:70575240-70576104 |
| 290 | 1700040L02Rik | NM_028491.1 | chr10:68430955-68541875 | | 387 | 1700101E01Rik | NM_001166705.1 | chr2:28955480-29055066 |

| | | | | | | | | |
|---|---|---|---|---|---|---|---|---|
| 582 | 2410006H16Rik | NR_030736.1 | chr11:62602876-62604806 | | 679 | 2810410L24Rik | NR_030682.1 | chr11:120186649-120189856 |
| 583 | 2410007B07Rik | NR_040539.1 | chr3:75647440-75655731 | | 680 | 2810417H13Rik | NM_026515.2 | chr9:65890322-65903551 |
| 584 | 2410012E07Rik | NR_045939.1 | chr14:70852932-70873954 | | 681 | 2810428I15Rik | NM_025577.2 | chr8:70504295-70506739 |
| 585 | 2410012M07Rik | NM_028033.1 | chr9:98864766-98866580 | | 682 | 2810429I04Rik | NR_015522.1 | chr13:3478302-3492398 |
| 586 | 2410015M20Rik | NM_153152.3 | chr17:56607451-56609771 | | 683 | 2810433D01Rik | NR_033474.1 | chr11:102619506-102624416 |
| 587 | 2410016O06Rik | NM_023633.3 | chr12:83950607-83952953 | | 684 | 2810442I21Rik | NR_110421.1 | chr11:16934708-16951282 |
| 588 | 2410017I17Rik | NR_033517.1 | chr17:36145017-36162374 | | 685 | 2810442N19Rik | NR_040562.1 | chr1:162004968-162016485 |
| 589 | 2410018L13Rik | NR_015504.1 | chr12:22953996-23010243 | | 686 | 2810454H06Rik | NR_029441.1 | chr6:134897960-134900785 |
| 590 | 2410021H03Rik | NR_045428.1 | chr17:69275361-69277206 | | 687 | 2810459M11Rik | NM_001144992.1 | chr1:86045862-86055456 |
| 591 | 2410076I21Rik | NM_028598.1 | chr9:58652855-58741559 | | 688 | 2810468N07Rik | NR_045178.1 | chr17:25570810-25575043 |
| 592 | 2410088K16Rik | NR_040493.1 | chr1:88754889-88755733 | | 689 | 2810471M01Rik | NR_045906.1 | chr11:28681562-28693276 |
| 593 | 2410089E03Rik | NM_001162906.1 | chr15:8169105-8271158 | | 690 | 2810474O19Rik | NM_001298661.1 | chr6:149309413-149335663 |
| 594 | 2410114N07Rik | NR_040652.1 | chr4:34909788-34911481 | | 691 | 2900005I15Rik | NR_027851.1 | chr5:25100974-25103607 |
| 595 | 2410124H12Rik | NM_029740.1 | chr16:92478741-92497365 | | 692 | 2900008C10Rik | NR_045434.1 | chrX:12134483-12160346 |
| 596 | 2410127L17Rik | NM_026124.2 | chr19:18670779-18704792 | | 693 | 2900009J06Rik | NR_045298.1 | chr1:127753616-127774054 |
| 597 | 2410131K14Rik | NM_001081236.1 | chr5:118245226-118263114 | | 694 | 2900011O08Rik | NM_144518.3 | chr16:13986636-14101494 |
| 598 | 2410137M14Rik | NM_029747.3 | chr17:36977700-36981237 | | 695 | 2900026A02Rik | NM_172884.3 | chr5:113086322-113163313 |
| 599 | 2410141K09Rik | NM_001290396.1 | chr13:66431027-66441118 | | 696 | 2900041M22Rik | NR_015489.2 | chr11:117611246-117613417 |
| 600 | 2500004C02Rik | NR_040318.1 | chr2:153341156-153345810 | | 697 | 2900052N01Rik | NR_015605.1 | chr9:46913602-46927366 |
| 601 | 2510002D24Rik | NM_001033164.2 | chr16:18836579-18840113 | | 698 | 2900055J20Rik | NR_045177.1 | chr18:40256961-40257687 |
| 602 | 2510003E04Rik | NM_028197.2 | chr10:62558469-62578457 | | 699 | 2900056M20Rik | NR_040269.2 | chrX:152294823-152327493 |
| 603 | 2510009E07Rik | NM_001001881.2 | chr16:21649044-21694665 | | 700 | 2900057B20Rik | NR_045365.1 | chr18:76091556-76098471 |
| 604 | 2510039O18Rik | NM_029841.3 | chr4:147940894-147947314 | | 701 | 2900060B08Rik | NR_027901.1 | chr1:118458668-118459265 |
| 605 | 2510049J12Rik | NM_001101431.1 | chr6:115583546-115592576 | | 702 | 2900076A07Rik | NR_045299.1 | chr7:81523549-81531498 |
| 606 | 2610001J05Rik | NR_024619.1 | chr6:13869073-13871483 | | 703 | 2900079G21Rik | NR_015468.1 | chr9:112234380-112236018 |
| 607 | 2610002J02Rik | NM_001190465.1 | chr4:155249965-155256687 | | 704 | 2900092C05Rik | NM_028434.3 | chr7:12512550-12556321 |
| 608 | 2610002M06Rik | NM_025921.3 | chrX:107782751-107816334 | | 705 | 2900092L14Rik | NR_027891.1 | chr1:42700335-42703176 |
| 609 | 2610005L07Rik | NR_028428.1 | chr8:20385781-20424814 | | 706 | 2900097C17Rik | NR_024329.1 | chr2:156388062-156392979 |
| 610 | 2610008E11Rik | NM_001004362.2 | chr16:79064373-79097600 | | 707 | 3000002C10Rik | NR_033215.1 | chr9:109830153-109831431 |
| 611 | 2610015P09Rik | NM_027801.1 | chr16:43889901-43964314 | | 708 | 3010001F23Rik | NR_045451.1 | chrX:152368571-152416702 |
| 612 | 2610016A17Rik | NR_045483.1 | chr19:25671133-25672239 | | 709 | 3010012O09Rik | NM_026543.3 | chr11:50174850-50200115 |
| 613 | 2610018G03Rik | NM_133729.2 | chrX:50841370-50893098 | | 710 | 3010033K07Rik | NR_077224.1 | chr8:108553251-108584677 |
| 614 | 2610020C07Rik | NR_038156.1 | chr16:11203382-11225796 | | 711 | 3100003L05Rik | NR_045907.1 | chr7:124625669-124708935 |
| 615 | 2610020H08Rik | NM_001004187.1 | chr7:119794186-119848941 | | 712 | 3110001I22Rik | NM_026653.2 | chr16:13672019-13672385 |
| 616 | 2610027K06Rik | NR_077059.1 | chr11:85791659-85832388 | | 713 | 3110002H16Rik | NM_029623.2 | chr18:12168729-12189969 |
| 617 | 2610028E06Rik | NR_015560.1 | chr4:125887850-125922910 | | 714 | 3110007F17Rik | NM_028426.2 | chrX:123108522-123145654 |
| 618 | 2610028H24Rik | NM_029816.2 | chr10:76449080-76461218 | | 715 | 3110009E18Rik | NM_001172074.1 | chr1:120121186-120198189 |
| 619 | 2610034B18Rik | NM_027420.4 | chr7:79925358-79935264 | | 716 | 3110009F21Rik | NR_045466.1 | chr12:110151653-110158073 |
| 620 | 2610034M16Rik | NM_027071.1 | chr17:58878807-58991375 | | 717 | 3110015L04Rik | NR_045906.1 | chr13:111211468-111229431 |
| 621 | 2610035D17Rik | NR_015556.1 | chr11:113043905-113201838 | | 718 | 3110021A11Rik | NR_030776.1 | chr6:119848192-119849016 |
| 622 | 2610035F20Rik | NR_045046.1 | chr14:122470376-122475199 | | 719 | 3110021N24Rik | NM_001254730.1 | chr4:108719648-108781904 |
| 623 | 2610037D02Rik | NR_040423.1 | chr15:96190473-96197974 | | 720 | 3110035E14Rik | NM_178399.4 | chr1:9601266-9627142 |
| 624 | 2610044O15Rik | NM_153780.3 | chr8:129216353-129234046 | | 721 | 3110039O08Rik | NR_040725.2 | chr9:41376529-41432079 |
| 625 | 2610100L16Rik | NR_033490.1 | chr3:17789920-17800071 | | 722 | 3110039M20Rik | NR_026733.1 | chr12:49389651-49407346 |
| 626 | 2610203C20Rik | NR_015483.3 | chr9:41581252-41592829 | | 723 | 3110040N11Rik | NR_026077.3 | chr7:81782186-81789453 |
| 627 | 2610203C22Rik | NR_015470.1 | chr1:9580832-9631092 | | 724 | 3110043O21Rik | NM_001081343.1 | chr4:35191281-35225880 |
| 628 | 2610206C17Rik | NR_038175.1 | chr7:84689639-84776549 | | 725 | 3110045C21Rik | NR_040438.1 | chr1:169969408-169972396 |
| 629 | 2610207O16Rik | NR_110495.1 | chr1:42707062-42713454 | | 726 | 3110052M02Rik | NM_001166497.1 | chr17:21650610-21664966 |
| 630 | 2610301B20Rik | NM_026005.3 | chr4:10874497-10899423 | | 727 | 3110056K07Rik | NR_045055.1 | chr12:70991614-71015823 |
| 631 | 2610305D13Rik | NM_146078.2 | chr4:147611936-147642508 | | 728 | 3110057O12Rik | NM_026622.3 | chr3:40894276-40936307 |
| 632 | 2610306M01Rik | NR_028298.1 | chr6:86848406-86849440 | | 729 | 3110062M04Rik | NM_001135611.1 | chr6:34871770-34878065 |
| 633 | 2610307P16Rik | NR_045053.1 | chr13:28460033-28885422 | | 730 | 3110070M22Rik | NR_027974.1 | chr13:119487256-119488284 |
| 634 | 2610316D01Rik | NR_045172.1 | chr3:45280438-45378260 | | 731 | 3110079O15Rik | NM_028473.1 | chr1:87470263-87475459 |
| 635 | 2610318N02Rik | NM_183287.2 | chr16:17113897-17125106 | | 732 | 3110082I17Rik | NM_028469.3 | chr5:139359738-139460534 |
| 636 | 2610507B11Rik | NM_001020004.2 | chr11:78261753-78290625 | | 733 | 3110082J24Rik | NM_001256263.1 | chr5:30103583-30106088 |
| 637 | 2610507I01Rik | NR_037964.1 | chr15:59197792-59202431 | | 734 | 3110099E03Rik | NR_030712.1 | chr2:115493512-115512201 |
| 638 | 2610524H06Rik | NM_181075.3 | chr5:114821936-114823468 | | 735 | 3200001D21Rik | NR_045888.2 | chr12:88365313-88377323 |
| 639 | 2610528A11Rik | NM_001206684.1 | chr14:37102139-37110101 | | 736 | 3300002I08Rik | NM_027017.1 | chr2:150310936-150362765 |
| 640 | 2610528J11Rik | NM_025572.2 | chr4:118527274-118530217 | | 737 | 3300005B01Rik | NR_045079.1 | chr17:5799488-5803242 |
| 641 | 2700029M09Rik | NM_028299.1 | chr8:60890450-60907572 | | 738 | 3425401B19Rik | NM_001195097.1 | chr14:32659118-32685272 |
| 642 | 2700038G22Rik | NR_045040.1 | chr5:23506296-23855033 | | 739 | 3632451O06Rik | NR_026142.4 | chr14:49682016-49783367 |
| 643 | 2700046A07Rik | NR_037693.1 | chr18:62751673-62756347 | | 740 | 3632454L22Rik | NR_040281.1 | chrX:135022421-135036602 |
| 644 | 2700046G09Rik | NR_033198.1 | chr19:32389215-32391184 | | 741 | 3830400N18Rik | NM_027510.2 | chrX:56136571-56153496 |
| 645 | 2700049A03Rik | NM_001163378.1 | chr12:71136847-71243303 | | 742 | 3830406C13Rik | NM_001284383.1 | chr14:12284202-12303231 |
| 646 | 2700054A10Rik | NR_045436.1 | chr17:13487020-13554094 | | 743 | 3830408C21Rik | NR_015471.1 | chr13:107022569-107033518 |
| 647 | 2700060E02Rik | NM_026528.3 | chr14:19811401-19823823 | | 744 | 3830417A18Rik | NM_027512.2 | chrX:64173547-64176778 |
| 648 | 2700062C07Rik | NM_026529.4 | chr18:24470870-24477767 | | 745 | 3830402G23Rik | NR_030715.1 | chr6:109244426-10928457 |
| 649 | 2700069I18Rik | NR_045905.2 | chr3:5177823-5220823 | | 746 | 4430402I18Rik | NM_198651.2 | chr19:28923063-28964154 |
| 650 | 2700070H01Rik | NR_046019.1 | chr14:63065072-63058149 | | 747 | 4631405J19Rik | NR_110323.1 | chr2:93029347-93033445 |
| 651 | 2700081G15Rik | NM_175381.6 | chr19:7417624-7425904 | | 748 | 4632415L05Rik | NR_027985.1 | chr3:198948870-198898984 |
| 652 | 2700086A05Rik | NR_015611.3 | chr6:52201213-52213597 | | 749 | 4632427E13Rik | NR_015510.1 | chr7:92740705-92741459 |
| 653 | 2700089E24Rik | NM_001163445.2 | chr5:133105238-133107750 | | 750 | 4632428C04Rik | NR_033631.1 | chr16:30008666-30021430 |
| 654 | 2700089J24Rik | NR_045308.1 | chr19:59493135-59559391 | | 751 | 4632428N05Rik | NM_001159572.1 | chr10:60346850-60372684 |
| 655 | 2700094K13Rik | NM_001033166.2 | chr2:84669220-84670708 | | 752 | 4632434I11Rik | NM_001080995.1 | chr7:92857526-92874232 |
| 656 | 2700097O09Rik | NM_028314.2 | chr12:55045660-55080110 | | 753 | 4732416N19Rik | NR_015615.1 | chr6:148212287-148235663 |
| 657 | 2700099C18Rik | NR_024720.1 | chr17:94750099-94775129 | | 754 | 4732456N10Rik | NM_177717.4 | chr15:101552355-101552950 |
| 658 | 2810001G20Rik | NR_033780.1 | chr11:64079483-64083259 | | 755 | 4732471I01Rik | NR_015569.3 | chr7:25394712-25566417 |
| 659 | 2810002O19Rik | NR_027831.1 | chr2:94406706-94411680 | | 756 | 4732490I19Rik | NR_040276.1 | chr11:113203314-113209669 |
| 660 | 2810004N23Rik | NR_025615.3 | chr8:128439354-128463059 | | 757 | 4732493I18Rik | NR_045290.1 | chr17:12318852-12327250 |
| 661 | 2810006K23Rik | NM_011134717.2 | chr5:124328088-124341852 | | 758 | 4831440E17Rik | NR_030700.1 | chr5:25499796-25504473 |
| 662 | 2810007J24Rik | NM_001199306.1 | chr7:14410685-14438551 | | 759 | 4834403I15Rik | NM_029008.1 | chr18:46850098-46905446 |
| 663 | 2810008D09Rik | NR_027609.1 | chr11:117076782-117078955 | | 760 | 4833411C07Rik | NR_102285.1 | chr8:10899921-10902334 |
| 664 | 2810013P06Rik | NR_045268.1 | chr13:23042574-23044602 | | 761 | 4833412C05Rik | NR_045954.1 | chr7:67784537-67803496 |
| 665 | 2810021J22Rik | NM_172403.2 | chr11:58867239-58884338 | | 762 | 4833417C18Rik | NR_045187.1 | chr1:95858816-95861046 |
| 666 | 2810025M15Rik | NR_045983.2 | chr7:157141951-157420214 | | 763 | 4833418N02Rik | NR_015506.2 | chr17:87274885-87282814 |
| 667 | 2810029C07Rik | NR_045295.1 | chr2:111572316-111574402 | | 764 | 4833419F23Rik | NR_040328.1 | chr18:4353546-4368945 |
| 668 | 2810032G03Rik | NR_015709.1 | chr5:5416132 | | 765 | 4833420G17Rik | NM_001113550.1 | chr13:119462758-119486117 |
| 669 | 2810047C21Rik1 | NR_015598.1 | chr7:8086046-8093037 | | 766 | 4833422C13Rik | NR_015501.1 | chr13:91701664-91741872 |
| 670 | 2810049E08Rik | NR_036594.1 | chr13:83891207-83928710 | | 767 | 4833423E24Rik | NM_001081664.2 | chr2:85484091-85518935 |
| 671 | 2810055G20Rik | NR_015543.2 | chr6:77329127-77558428 | | 768 | 4833424O15Rik | NM_026425.3 | chr3:117575226-117689508 |
| 672 | 2810403A07Rik | NM_028814.3 | chr3:88685793-88712983 | | 769 | 4833427F10Rik | NR_045459.1 | chr17:35772449-35780687 |
| 673 | 2810403D21Rik | NR_015493.2 | chrX:108834477-108886896 | | 770 | 4833427G06Rik | NM_177702.3 | chr9:51081312-51102078 |
| 674 | 2810404M03Rik | NR_045497.1 | chr8:41827266-42046202 | | 771 | 4833428I15Rik | NR_040732.1 | chr9:45416625-45431232 |
| 675 | 2810405F15Rik | NR_033447.1 | chr2:116074547-116078096 | | 772 | 4833439I19Rik | NM_001252645.1 | chr3:54551217-54565382 |
| 676 | 2810408A11Rik | NM_027597.3 | chr17:69795987-69900986 | | 773 | 4921501E09Rik | NM_001009544.2 | chr17:33064142-33068058 |
| 677 | 2810408I11Rik | NR_038009.1 | chr1:64679868-64690659 | | 774 | 4921504A21Rik | NR_102341.1 | chr5:19202367-19226555 |
| 678 | 2810408M09Rik | NM_001007581.1 | chr2:165490111-165493314 | | 775 | 4921504E06Rik | NM_027600.4 | chr2:19462836-19553910 |

| | | | | | | | |
|---|---|---|---|---|---|---|---|
| 1164 | 4932438H23Rik | NM_001163695.1 | chr16:91053934-91069145 | 1261 | 4933432I09Rik | NR_015575.1 | chr16:18209685-18213863 |
| 1165 | 4932441J04Rik | NR_015588.2 | chr5:57570083-57717919 | 1262 | 4933432K03Rik | NR_102286.1 | chr7:121587385-121589836 |
| 1166 | 4932443I19Rik | NM_001101519.1 | chr8:13705888-13743066 | 1263 | 4933433C11Rik | NM_028961.1 | chr2:25212558-25214630 |
| 1167 | 4932702P03Rik | NR_045182.1 | chr13:24905599-24911780 | 1264 | 4933433F19Rik | NR_045856.1 | chr8:30568394-30575573 |
| 1168 | 4933400A11Rik | NR_003635.1 | chrX:169776377-169779635 | 1265 | 4933433G08Rik | NR_105026.1 | chr9:61103011-61105386 |
| 1169 | 4933400B14Rik | NR_045432.1 | chr17:89320226-89327333 | 1266 | 4933433G15Rik | NR_040719.1 | chr9:75410183-75415537 |
| 1170 | 4933400C23Rik | NR_040770.1 | chr9:92718715-92795711 | 1267 | 4933433G19Rik | NR_045851.1 | chr13:66996817-67032405 |
| 1171 | 4933400F21Rik | NR_015540.1 | chr1:89676506-89683892 | 1268 | 4933433H22Rik | NR_045458.1 | chr17:84078659-84089875 |
| 1172 | 4933400L20Rik | NR_045730.1 | chr8:103603798-103680382 | 1269 | 4933434E20Rik | NM_001287086.1 | chr3:90052801-90063341 |
| 1173 | 4933401B06Rik | NR_033580.1 | chrX:107542581-107543800 | 1270 | 4933434I20Rik | NM_026233.2 | chr8:83348471-83379402 |
| 1174 | 4933401D09Rik | NR_045431.1 | chr17:15631787-15641102 | 1271 | 4933436E23Rik | NR_040455.1 | chr1:139379451-139402852 |
| 1175 | 4933401H06Rik | NR_040540.1 | chr3:135833693-135840269 | 1272 | 4933436H12Rik | NR_046208.1 | chr7:68417423-68426133 |
| 1176 | 4933402C06Rik | NR_045504.1 | chr7:40674736-40691260 | 1273 | 4933436I01Rik | NM_025763.1 | chrX:67919863-67921450 |
| 1177 | 4933402D24Rik | NM_001256158.1 | chr1.63754908-63769267 | 1274 | 4933438B17Rik | NR_040685.1 | chr5:127030788-127088529 |
| 1178 | 4933402E13Rik | NM_001199996.1 | chrX:62287141-62292078 | 1275 | 4933438K21Rik | NR_045446.1 | chr4:147063365-147068436 |
| 1179 | 4933402J07Rik | NM_177901.3 | chr8.87563906-87589197 | 1276 | 4933439C10Rik | NR_015585.2 | chr11:59505684-59511067 |
| 1180 | 4933402J10Rik | NR_040682.1 | chr5:59963118-59986002 | 1277 | 4933439K11Rik | NR_040558.1 | chr1:172541619-172550806 |
| 1181 | 4933402J15Rik | NR_046059.1 | chr14:74355526-74369741 | 1278 | 4933440J02Rik | NR_045344.1 | chr10:111586718-111594273 |
| 1182 | 4933402N03Rik | NM_173409.4 | chr7:131138346-131146283 | 1279 | 4933440M02Rik | NR_045803.1 | chr7:125331781-125349786 |
| 1183 | 4933402N22Rik | NM_001177510.1 | chr5:11918042-11922804 | 1280 | 5031410I06Rik | NM_207657.3 | chr5:26098667-26105314 |
| 1184 | 4933402P03Rik | NM_175368.1 | chr11:69816565-69818440 | 1281 | 5031414D18Rik | NM_198642.2 | chr14:75016026-75052532 |
| 1185 | 4933403O08Rik | NM_001177389.1 | chrX:112239048-112243852 | 1282 | 5031425E22Rik | NR_040469.1 | chr5:23431807-23434353 |
| 1186 | 4933404G15Rik | NR_045920.1 | chr16:16707686-16718121 | 1283 | 5031425F14Rik | NR_015558.2 | chr2:166447450-166458770 |
| 1187 | 4933404K08Rik | NR_046038.1 | chr13:23278349-23282267 | 1284 | 5031426D15Rik | NR_027890.1 | chr2:6922701-6928722 |
| 1188 | 4933404O12Rik | NR_015555.1 | chr5:136919145-136937109 | 1285 | 5031434C07Rik | NR_045986.1 | chr6:112286793-112290319 |
| 1189 | 4933405D12Rik | NR_046036.1 | chr3:122882591-122924116 | 1286 | 5031434O11Rik | NR_033624.1 | chr3:51559756-51567116 |
| 1190 | 4933405E24Rik | NR_045506.1 | chr11:54177771-54213288 | 1287 | 5031439G07Rik | NM_001033273.2 | chr15:84945719-84987971 |
| 1191 | 4933405L10Rik | NM_027655.1 | chr8:105708302-105710168 | 1288 | 5033403H07Rik | NR_040413.1 | chr5:52973011-52992292 |
| 1192 | 4933405O20Rik | NM_172901.2 | chr7:50599189-50600528 | 1289 | 5033404E19Rik | NR_033600.1 | chr1:185497305-185498014 |
| 1193 | 4933406C10Rik | NR_044986.1 | chr12:32919383-32953789 | 1290 | 5033406O09Rik | NR_029464.1 | chr12:111941990-111944482 |
| 1194 | 4933406D12Rik | NR_040502.1 | chr2:146542930-146546108 | 1291 | 5133400J02Rik | NR_110444.1 | chr11:51189832-51220418 |
| 1195 | 4933406F09Rik | NR_015568.2 | chr14:7412472-7422685 | 1292 | 5330411J11Rik | NR_040510.1 | chr2:59382492-59386682 |
| 1196 | 4933406G16Rik | NR_046037.1 | chr11:19065274-19075740 | 1293 | 5330413P13Rik | NR_029381.1 | chr2:131820005-131847656 |
| 1197 | 4933406I18Rik | NR_029437.1 | chr7.114315478-114415161 | 1294 | 5330417C22Rik | NM_001033304.1 | chr3:108458068-108536522 |
| 1198 | 4933406J08Rik | NM_028914.1 | chr2:122186271-122206393 | 1295 | 5330426P16Rik | NR_028300.1 | chr16:50726750-50732773 |
| 1199 | 4933406J10Rik | NR_046004.1 | chr7:82743345-82755644 | 1296 | 5330434G04Rik | NR_015552.1 | chrX:105372993-105391754 |
| 1200 | 4933406K04Rik | NR_015512.2 | chr12:106685606-106716324 | 1297 | 5330439B14Rik | NR_037679.1 | chr6:142614594-142626462 |
| 1201 | 4933406M09Rik | NM_173771.4 | chr1:134385939-134390983 | 1298 | 5430401F13Rik | NM_001244628.1 | chr6:131543761-131553757 |
| 1202 | 4933407E24Rik | NR_045819.1 | chr4.124569178-124575538 | 1299 | 5430402E10Rik | NM_027768.3 | chrX:77919785-77925062 |
| 1203 | 4933407G14Rik | NR_045841.1 | chr10:75449509-75463104 | 1300 | 5430402O13Rik | NR_015581.1 | chr6:50566642-50594865 |
| 1204 | 4933407I05Rik | NR_040731.1 | chr9:51914428-51927003 | 1301 | 5430403N17Rik | NR_046181.1 | chr8:35864084-35882957 |
| 1205 | 4933407K13Rik | NR_029443.1 | chrX:75725457-75764699 | 1302 | 5430405H02Rik | NR_015591.1 | chr2:156852402-156862945 |
| 1206 | 4933407L21Rik | NR_037692.1 | chr1:85928482-85931756 | 1303 | 5430416N02Rik | NR_034038.1 | chr5:100420841-100429535 |
| 1207 | 4933408B17Rik | NM_177773.4 | chr18:34579845-34597468 | 1304 | 5430416O09Rik | NR_033355.1 | chr4:43730033-43734534 |
| 1208 | 4933408J17Rik | NR_045810.1 | chr10:93589412-93605245 | 1305 | 5430417L22Rik | NM_001301269.1 | chr2:118745758-118748810 |
| 1209 | 4933408N05Rik | NR_045831.2 | chr8.114341160-114351478 | 1306 | 5430419D17Rik | NM_175166.3 | chr7:131174401-131250945 |
| 1210 | 4933409G03Rik | NM_177651.3 | chr2.68582412-68616463 | 1307 | 5430421F17Rik | NR_040352.1 | chr8:25302649-25306270 |
| 1211 | 4933409K07Rik | NR_033123.1 | chr4:60800-42462993 | 1308 | 5430421N21Rik | NM_001201323.1 | chr15:101485129-101491512 |
| 1212 | 4933411E08Rik | NR_045342.1 | chr10:117925458-117948307 | 1309 | 5430425K12Rik | NR_103550.1 | chr13:80940402-80948597 |
| 1213 | 4933411G06Rik | NR_045158.1 | chr10:51756173-51757194 | 1310 | 5430427M07Rik | NR_045858.1 | chr12:91045847-91056635 |
| 1214 | 4933411G11Rik | NM_177880.4 | chr5:143181016-143205068 | 1311 | 5430427O19Rik | NM_001163539.1 | chrX:85870272-85891499 |
| 1215 | 4933411K16Rik | NM_025752.2 | chr19:42052227-42053628 | 1312 | 5430428K19Rik | NR_045426.1 | chrX:6452375-6574663 |
| 1216 | 4933411K20Rik | NM_025747.3 | chr8:46169555-46195590 | 1313 | 5430434I15Rik | NR_040541.1 | chr3:38203150-38208119 |
| 1217 | 4933412E12Rik | NR_038025.1 | chr10:116950561-116963279 | 1314 | 5430435G22Rik | NM_145509.3 | chr1:131688694-131715439 |
| 1218 | 4933412E24Rik | NM_027668.1 | chr15:60014865-60016618 | 1315 | 5430437J10Rik | NR_045274.1 | chr15:5496317-5594983 |
| 1219 | 4933412O06Rik | NR_045507.1 | chr13:15781663-15802630 | 1316 | 5430440P10Rik | NR_045859.1 | chr14:105427558-105437716 |
| 1220 | 4933413G19Rik | NM_027697.1 | chr6:128375509-128385144 | 1317 | 5530400C23Rik | NM_027784.1 | chr6:133292215-133295790 |
| 1221 | 4933413J09Rik | NR_038005.1 | chr14:26357546-26400456 | 1318 | 5530401A14Rik | NR_038010.1 | chr11:81860676-81894582 |
| 1222 | 4933413L06Rik | NR_045508.1 | chr13:117706763-117720011 | 1319 | 5530601H04Rik | NR_015467.1 | chrX:105040853-105070124 |
| 1223 | 4933415F23Rik | NM_025746.2 | chr1:23100473-23102253 | 1320 | 5730403I07Rik | NR_040378.1 | chr9:77366411-77399416 |
| 1224 | 4933416C03Rik | NM_001161855.1 | chr10:116111663-116113917 | 1321 | 5730405O15Rik | NR_038158.1 | chrX:13042014-13045295 |
| 1225 | 4933416E03Rik | NR_040498.1 | chr2:159947340-159981289 | 1322 | 5730408K05Rik | NR_027866.1 | chr19:8888386-8898770 |
| 1226 | 4933416I08Rik | NM_027700.1 | chrX:53686490-53691332 | 1323 | 5730409E04Rik | NM_001013755.3 | chr4:126609853-126614371 |
| 1227 | 4933416M06Rik | NR_045846.2 | chr13:101254318-101293396 | 1324 | 5730412P04Rik | NR_045424.1 | chrX:136104602-136115420 |
| 1228 | 4933416M07Rik | NR_045840.1 | chr8:27142909-27149706 | 1325 | 5730416F02Rik | NR_033596.1 | chrX:109001484-109002296 |
| 1229 | 4933417A18Rik | NM_025750.3 | chr13:34924408-34953196 | 1326 | 5730420D15Rik | NR_045338.1 | chr10:95417374-95428640 |
| 1230 | 4933417D19Rik | NR_045849.1 | chr8:123235090-123242359 | 1327 | 5730422E09Rik | NR_015478.2 | chr5:149119564-149182036 |
| 1231 | 4933417E11Rik | NR_040454.1 | chr1:71958997-72005195 | 1328 | 5730435O14Rik | NR_045341.1 | chr10:41568015-41576476 |
| 1232 | 4933417G07Rik | NR_033592.1 | chr3:55847104-55848065 | 1329 | 5730455P16Rik | NM_027472.3 | chr11:80360491-80378015 |
| 1233 | 4933417O13Rik | NR_045842.1 | chr7.143322771-143330650 | 1330 | 5730457N03Rik | NR_038163.1 | chr6:52308388-52314832 |
| 1234 | 4933421I07Rik | NM_027702.2 | chr7.42445461-42448080 | 1331 | 5730460C07Rik | NR_045801.1 | chr3:153789304-153792087 |
| 1235 | 4933421O10Rik | NR_036602.1 | chr4:33027138-33031323 | 1332 | 5730480H06Rik | NR_045500.1 | chr5:48395572-48414294 |
| 1236 | 4933422A05Rik | NR_040715.1 | chr9:35281104-35285423 | 1333 | 5730488B01Rik | NR_073462.1 | chr4:44702799-44705110 |
| 1237 | 4933422H20Rik | NM_001033775.3 | chr11:115440544-115448268 | 1334 | 5730507C01Rik | NM_001033157.4 | chr12:18514509-18535254 |
| 1238 | 4933424G05Rik | NR_045372.1 | chr18:14988994-15047987 | 1335 | 5730508B09Rik | NM_027482.3 | chr3:127869687-127896323 |
| 1239 | 4933424G06Rik | NR_040290.1 | chr1.36714537-36757960 | 1336 | 5730522E02Rik | NR_027973.1 | chr11:25616845-26210576 |
| 1240 | 4933425B07Rik | NR_046460.1 | chr14:46602805-46637423 | 1337 | 5730559C18Rik | NM_028872.3 | chr1:136213521-136234280 |
| 1241 | 4933425L06Rik | NM_025751.3 | chr13:105082121-105121782 | 1338 | 5830403L16Rik | NM_178243.3 | chr1:153849541-153851195 |
| 1242 | 4933426M11Rik | NM_001242419.1 | chr12:80790531-80880833 | 1339 | 5830411N06Rik | NM_001128145.1 | chr7:140247380-140299791 |
| 1243 | 4933427D06Rik | NM_175017.3 | chr6:89096114-89110037 | 1340 | 5830415F09Rik | NM_029086.2 | chr4:46376974-46389423 |
| 1244 | 4933427D14Rik | NM_028963.2 | chr11:72154096-72203371 | 1341 | 5830416I19Rik | NR_045384.1 | chr5:64044972-64050226 |
| 1245 | 4933427E11Rik | NR_033197.1 | chr15:74709160-74710374 | 1342 | 5830416P10Rik | NR_028427.1 | chr19:53441211-53464796 |
| 1246 | 4933427E13Rik | NR_045853.1 | chr11:25326106-25367137 | 1343 | 5830417I10Rik | NR_028359.1 | chr3:88777056-88829371 |
| 1247 | 4933427G17Rik | NM_028955.1 | chr7.120982508-121014787 | 1344 | 5830418K08Rik | NM_176976.4 | chr9:15316913-15357788 |
| 1248 | 4933427I22Rik | NR_045159.1 | chr4:139926110-139943519 | 1345 | 5830418P13Rik | NR_040466.1 | chr9:103423577-103461260 |
| 1249 | 4933428C19Rik | NR_040644.1 | chr4:40482839-40525548 | 1346 | 5830428M24Rik | NR_038060.1 | chr12:69464786-69475550 |
| 1250 | 4933428G20Rik | NM_001289118.1 | chr11:97490782-97500340 | 1347 | 5830432E09Rik | NR_015548.1 | chr7:135648456-135652314 |
| 1251 | 4933429K18Rik | NR_045307.1 | chr19:45726554-45730558 | 1348 | 5830444B04Rik | NR_102283.1 | chr4:155408308-155421704 |
| 1252 | 4933429O19Rik | NR_033783.1 | chr14:48878872-48887112 | 1349 | 5830454E08Rik | NR_073359.1 | chr9:120577330-120578073 |
| 1253 | 4933430H16Rik | NR_045855.1 | chr7.82937937-82971391 | 1350 | 5830473C10Rik | NM_001252661.1 | chr5:90561208-90597906 |
| 1254 | 4933430I17Rik | NM_177607.3 | chr4:62525368-62547993 | 1351 | 5930403L14Rik | NR_045643.1 | chr4:154630690-154636367 |
| 1255 | 4933430M04Rik | NR_045857.2 | chr11:24481908-24569951 | 1352 | 5930412G12Rik | NR_015517.2 | chr5:128579129-128600687 |
| 1256 | 4933430N04Rik | NR_045854.1 | chr8:9125411-9132288 | 1353 | 5930430L01Rik | NR_102383.1 | chr5:148990055-148995214 |
| 1257 | 4933431E20Rik | NR_015459.1 | chr3.107888849-107896213 | 1354 | 5930438M14Rik | NR_046158.1 | chr13:101232126-101247551 |
| 1258 | 4933431G14Rik | NR_045163.1 | chr6:72120212-72122940 | 1355 | 6030407O03Rik | NR_045311.1 | chr1:73618380-73864466 |
| 1259 | 4933432G23Rik | NR_040716.1 | chr9.118429838-118437048 | 1356 | 6030408B16Rik | NR_033803.1 | chr15:101293211-101297426 |
| 1260 | 4933432I03Rik | NR_045657.1 | chr14:102987411-103033803 | 1357 | 6030419C18Rik | NM_176921.3 | chr9:58488602-58499742 |

| | | | | | | |
|---|---|---|---|---|---|---|
| 1552 | A330048O09Rik | NR_045162.1 | chr13:48272417-48273884 | 1649 | A930019D19Rik | NR_040619.1 | chr2:146259285-146267160 |
| 1553 | A330049N07Rik | NR_040646.1 | chr10:72973302-73086705 | 1650 | A930024E05Rik | NR_045820.1 | chr5:122989353-122998341 |
| 1554 | A330050F15Rik | NM_001145192.1 | chr17:69439325-69489233 | 1651 | A930041C12Rik | NR_046195.1 | chr5:107630249-107633850 |
| 1555 | A330069E16Rik | NR_015464.1 | chr2:91237145-91238357 | 1652 | AA387883 | NR_030678.1 | chr19:52923180-52926931 |
| 1556 | A330070K13Rik | NM_198665.1 | chr5:130378850-130384631 | 1653 | AA388235 | NR_033265.1 | chr17:33981491-33985358 |
| 1557 | A330074K22Rik | NR_110496.1 | chr8:120204453-120228230 | 1654 | AA413626 | NR_102683.1 | chr11:4918515-4918918 |
| 1558 | A330076C08Rik | NR_045088.1 | chr13:44193588-44216487 | 1655 | AA414768 | NM_001272033.1 | chrX:12936872-12998541 |
| 1559 | A330076H08Rik | NR_015599.2 | chr7:61943900-61982303 | 1656 | AA415398 | NM_001004178.1 | chr4:119530314-119538769 |
| 1560 | A330093E20Rik | NR_040342.1 | chr18:45683486-46045260 | 1657 | AA465934 | NR_028363.1 | chr11:83291698-83294637 |
| 1561 | A330102H10Rik | NR_045073.1 | chr13:29016254-29040336 | 1658 | AA467197 | NM_001004174.1 | chr2:122637886-122641076 |
| 1562 | A3galt2 | NM_001009819.2 | chr4:128759925-128769298 | 1659 | AA474331 | NR_038628.1 | chr10:39892759-39899238 |
| 1563 | A430005L14Rik | NM_001163019.1 | chr4:153957236-153961924 | 1660 | AA536875 | NR_045143.1 | chr14:123169185-123176176 |
| 1564 | A430023K04Rik | NM_183025.2 | chr5:138622858-138648905 | 1661 | AA543186 | NR_027448.1 | chr2:25327449-25332571 |
| 1565 | A430035B10Rik | NR_040452.1 | chr6:85057058-85059161 | 1662 | AA543401 | NR_102273.1 | chr9:107192806-107194061 |
| 1566 | A430078G23Rik | NM_001033378.3 | chr8:3353414-3390299 | 1663 | AA545190 | NR_033776.1 | chr6:10971467-10974378 |
| 1567 | A430088P11Rik | NR_045309.1 | chr15:80691024-80697610 | 1664 | AA619741 | NR_033627.1 | chr1:34633534-34636210 |
| 1568 | A430089E19Rik | NM_177913.4 | chr5:5184-94955288 | 1665 | AA792892 | NM_178894.4 | chr5:94377339-94384334 |
| 1569 | A430090L17Rik | NR_045836.1 | chr13:114124347-114151592 | 1666 | AA986860 | NM_177604.3 | chr1:130731975-130744622 |
| 1570 | A430093F15Rik | NR_027805.1 | chr19:10740946-10786043 | 1667 | AA987161 | NM_001163246.2 | chr13:67589438-67609707 |
| 1571 | A430105J19Rik | NM_001001982.2 | chr2:118754144-118762661 | 1668 | Aaas | NM_153416.2 | chr15:102338246-102350759 |
| 1572 | A430107P09Rik | NM_001205242.1 | chr14:53666005-53666506 | 1669 | Aacs | NM_030210.1 | chr5:125475872-125517403 |
| 1573 | A4galt | NM_001004150.3 | chr15:83226721-83251774 | 1670 | Aadac | NM_023383.1 | chr3:60031787-60040157 |
| 1574 | A4gnt | NM_001077424.2 | chr9:99612501-99622367 | 1671 | Aadacl2 | NM_001128091.1 | chr3:60006742-60025420 |
| 1575 | A530006G24Rik | NR_046014.1 | chr2:147710692-147717632 | 1672 | Aadacl3 | NM_001085603.2 | chr4:144453770-144463756 |
| 1576 | A530013C23Rik | NR_015500.3 | chr2:167691176-167697413 | 1673 | Aadat | NM_011834.2 | chr8:60506123-60543677 |
| 1577 | A530016L24Rik | NM_177039.4 | chr12:112489447-112499927 | 1674 | Aaed1 | NM_025370.2 | chr13:64291855-64312710 |
| 1578 | A530032D15Rik | NM_213615.2 | chr1:85088138-85109853 | 1675 | Aagab | NM_025857.1 | chr9:63602654-63641889 |
| 1579 | A530046M15Rik | NR_046131.1 | chr13:15807224-15827537 | 1676 | Aak1 | NM_001040106.2 | chr6:86849516-87003227 |
| 1580 | A530050N04Rik | NR_045419.1 | chr18:61470224-61484607 | 1677 | Aamdc | NM_001177945.1 | chr7:97550330-97579497 |
| 1581 | A530053G22Rik | NR_015565.2 | chr6:60279042-60403707 | 1678 | Aamp | NM_001190444.1 | chr1:74279839-74284738 |
| 1582 | A530054K11Rik | NM_183146.3 | chr13:67617000-67637753 | 1679 | Aanat | NM_009591.3 | chr11:116593686-116597680 |
| 1583 | A530058N18Rik | NR_028423.1 | chr2:114013564-114032292 | 1680 | Aar2 | NM_001164818.1 | chr2:156547575-156568972 |
| 1584 | A530064D06Rik | NM_001113556.1 | chr17:48151895-48167257 | 1681 | Aard | NM_175503.3 | chr15:52040106-52045722 |
| 1585 | A530065N20Rik | NR_046142.1 | chr13:60029710-60116669 | 1682 | Aars | NM_146217.4 | chr8:111033841-111055569 |
| 1586 | A530072M11Rik | NR_045765.2 | chr4:16164109-16266225 | 1683 | Aars2 | NM_198608.2 | chr17:45506840-45520843 |
| 1587 | A530088E08Rik | NR_029458.1 | chr17:32403013-32404808 | 1684 | Aarsd1 | NM_144829.1 | chr11:101406839-101417433 |
| 1588 | A530099J19Rik | NM_175688.4 | chr13:19717416-19732951 | 1685 | Aasdh | NM_173785.3 | chr5:76875934-76908514 |
| 1589 | A630001G21Rik | NM_177055.3 | chr1:85717082-85736606 | 1686 | Aasdhppt | NM_026276.3 | chr9:4294792-4309484 |
| 1590 | A630007B08Rik | NM_170757.1 | chr19:56790962-56813683 | 1687 | Aass | NM_013930.4 | chr6:23072172-23132986 |
| 1591 | A630010A05Rik | NR_033556.1 | chr16:14562316-14621284 | 1688 | Aatf | NM_019816.1 | chr11:84422855-84513501 |
| 1592 | A630012P03Rik | NR_045367.2 | chrX:52575842-52619047 | 1689 | Aatk | NM_001198785.1 | chr11:120007315-120047145 |
| 1593 | A630019B02Rik | NR_046182.1 | chr13:93094832-93098968 | 1690 | AB041803 | NR_110469.1 | chr6:31165522-31218474 |
| 1594 | A630020A08 | NR_045740.1 | chr15:3996038-4015858 | 1691 | AB124611 | NM_001198794.1 | chr9:21526176-21545331 |
| 1595 | A630023A22Rik | NM_001251843.1 | chr14:34051129-34102754 | 1692 | Abat | NM_001170978.1 | chr16:8513428-8621567 |
| 1596 | A630029P12Rik | NR_102290.1 | chr5:110514922-110525979 | 1693 | Abca1 | NM_013454.3 | chr4:53030788-53159895 |
| 1597 | A630033H20Rik | NM_001122595.1 | chrX:107149453-107173661 | 1694 | Abca12 | NM_175210.3 | chr1:71243089-71414910 |
| 1598 | A630066F11Rik | NR_030699.1 | chr10:7663370-7864623 | 1695 | Abca13 | NM_178259.3 | chr11:9391941-9684259 |
| 1599 | A630072M13Rik | NR_030699.1 | chr5:20950988-20956398 | 1696 | Abca14 | NM_026458.4 | chr7:120203963-120325352 |
| 1600 | A630073D07Rik | NM_001142969.1 | chr6:132625110-132627511 | 1697 | Abca15 | NM_177213.3 | chr7:120328683-120407687 |
| 1601 | A630075F08Rik | NR_033682.1 | chr2:170061457-170070778 | 1698 | Abca16 | NM_001278943.1 | chr7:120409646-120544813 |
| 1602 | A630076J17Rik | NM_001256174.1 | chr3:107230613-107234031 | 1699 | Abca17 | NM_001031621.2 | chr17:24264278-24347252 |
| 1603 | A630077J23Rik | NR_040667.1 | chr4:43751858-43759464 | 1700 | Abca2 | NM_007379.2 | chr2:25428673-25448539 |
| 1604 | A630089N07Rik | NR_015491.1 | chr9:59062511-98082439 | 1701 | Abca3 | NM_001039581.2 | chr17:24352022-24410204 |
| 1605 | A630095E13Rik | NM_001033325.2 | chr9:36635753-36638602 | 1702 | Abca4 | NM_007378.1 | chr3:122044459-122180061 |
| 1606 | A630095N17Rik | NM_001203090.1 | chr1:75220694-75232093 | 1703 | Abca5 | NM_147219.2 | chr11:110269368-110337716 |
| 1607 | A730006G06Rik | NR_110485.1 | chr17:48064788-48090378 | 1704 | Abca6 | NM_001166556.1 | chr11:110236422-110251776 |
| 1608 | A730008B23Rik | NM_172505.4 | chr1:28264827-88277557 | 1705 | Abca7 | NM_013850.1 | chr10:79997614-80015572 |
| 1609 | A730017C20Rik | NM_001167925.2 | chr18:59062380-59076690 | 1706 | Abca8a | NM_153145.4 | chr11:110025633-110095937 |
| 1610 | A730017L22Rik | NR_015523.1 | chr2:130872540-130906396 | 1707 | Abca8b | NM_013851.2 | chr11:109933405-109995816 |
| 1611 | A730018C14Rik | NR_036459.1 | chr12:112411022-112423198 | 1708 | Abca9 | NM_147220.2 | chr11:110100821-110168153 |
| 1612 | A730020E08Rik | NR_040287.1 | chr6:61175603-61180810 | 1709 | Abcb10 | NM_019552.2 | chr8:123952458-123983122 |
| 1613 | A730020M07Rik | NR_036456.1 | chr12:121634935-121643485 | 1710 | Abcb11 | NM_021022.3 | chr2:69238281-69342616 |
| 1614 | A730036H17Rik | NR_045838.1 | chr12:129218968-129235606 | 1711 | Abcb1a | NM_011076.2 | chr5:8660091-8748570 |
| 1615 | A730043L09Rik | NR_040769.1 | chr9:62242595-62244100 | 1712 | Abcb1b | NM_011075.2 | chr5:8798146-8866314 |
| 1616 | A730046J19Rik | NR_040271.1 | chrX:144153694-144166274 | 1713 | Abcb4 | NM_008830.2 | chr5:8893720-8959226 |
| 1617 | A730056A06Rik | NR_040343.1 | chr7:73313805-73375774 | 1714 | Abcb5 | NM_029961.2 | chr12:118867823-118966421 |
| 1618 | A730082K24Rik | NR_040317.1 | chr7:114948649-114983967 | 1715 | Abcb6 | NM_023732.3 | chr1:75171640-75180392 |
| 1619 | A730085K09Rik | NR_045967.1 | chr9:122382021-122398801 | 1716 | Abcb7 | NM_009592.1 | chrX:104280564-104413846 |
| 1620 | A730090H04Rik | NR_040279.1 | chr11:95145052-95159047 | 1717 | Abcb8 | NM_029020.2 | chr5:24394155-24409947 |
| 1621 | A730090N16Rik | NR_040390.1 | chr6:65324019-65349429 | 1718 | Abcb9 | NM_019875.2 | chr5:124061856-124095798 |
| 1622 | A730098P11Rik | NR_038091.1 | chr16:24529313-24534472 | 1719 | Abcc1 | NM_008576.3 | chr16:14361557-14474878 |
| 1623 | A830009J08Rik | NR_045161.1 | chr13:91368989-91380085 | 1720 | Abcc10 | NM_145140.2 | chr17:46303229-46325766 |
| 1624 | A830010M20Rik | NM_001007574.2 | chr5:107497744-107512556 | 1721 | Abcc12 | NM_172912.4 | chr8:86504840-86566590 |
| 1625 | A830018L16Rik | NM_001160369.2 | chr1:11414104-11975962 | 1722 | Abcc2 | NM_013806.2 | chr19:43782307-43838218 |
| 1626 | A830019L24Rik | NR_040551.1 | chr3:143243054-143257996 | 1723 | Abcc3 | NM_029600.3 | chr11:94343294-94392976 |
| 1627 | A830052D11Rik | NR_045403.1 | chr18:32359056-32378284 | 1724 | Abcc4 | NM_001033336.3 | chr14:118482691-118706219 |
| 1628 | A830080D01Rik | NM_001033472.2 | chrX:159532667-159593081 | 1725 | Abcc5 | NM_013790.2 | chr16:20331303-20426394 |
| 1629 | A830082K12Rik | NR_045195.1 | chr13:78198016-78236564 | 1726 | Abcc6 | NM_018795.2 | chr7:45976379-46030286 |
| 1630 | A830082N09Rik | NR_015526.2 | chr19:38973215-33995055 | 1727 | Abcc8 | NM_015510.3 | chr7:46104522-46180033 |
| 1631 | A930001A20Rik | NR_040549.1 | chr3:14971200-15002727 | 1728 | Abcc9 | NM_001044720.1 | chr6:142587861-142702274 |
| 1632 | A930001C03Rik | NR_045989.1 | chr19:4439558-4448325 | 1729 | Abcd1 | NM_007435.1 | chrX:73716596-73738287 |
| 1633 | A930003A15Rik | NR_015648.1 | chr16:19876587-19884274 | 1730 | Abcd2 | NM_013994.2 | chr15:91145870-91191807 |
| 1634 | A930003O13Rik | NR_027362.1 | chr5:22738910-22746884 | 1731 | Abcd3 | NM_008991.2 | chr3:121758909-121815215 |
| 1635 | A930004D18Rik | NR_028376.1 | chr2:18025188-18037741 | 1732 | Abcd4 | NM_008992.2 | chr12:84602530-84617466 |
| 1636 | A930005H10Rik | NR_015573.1 | chr3:115881578-115888130 | 1733 | Abce1 | NM_015751.2 | chr8:79683441-79711740 |
| 1637 | A930006I01Rik | NR_040332.1 | chr2:103338600-103372764 | 1734 | Abcf1 | NM_013854.1 | chr17:35958818-35969750 |
| 1638 | A930006K02Rik | NR_077219.1 | chr16:91465103-91470123 | 1735 | Abcf2 | NM_001190443.1 | chr5:24565340-24577467 |
| 1639 | A930007J19Rik | NR_015567.2 | chr19:29503662-29521987 | 1736 | Abcf3 | NM_013852.2 | chr16:20548602-20561603 |
| 1640 | A930009A15Rik | NM_029982.1 | chr10:115569985-115582454 | 1737 | Abcg1 | NM_009593.2 | chr17:31057693-31117981 |
| 1641 | A930011G23Rik | NR_036924.1 | chr9:99297243-99729060 | 1738 | Abcg2 | NM_011920.3 | chr6:58596671-58692451 |
| 1642 | A930011O12Rik | NR_040709.1 | chr14:64588114-64593961 | 1739 | Abcg3 | NM_030219.2 | chr5:104935056-104982717 |
| 1643 | A930012L18Rik | NR_026853.1 | chr18:44661664-44676271 | 1740 | Abcg4 | NM_138955.3 | chr9:44273189-44288284 |
| 1644 | A930013F10Rik | NR_027886.1 | chr8:22634283-22636809 | 1741 | Abcg5 | NM_031884.1 | chr17:84658233-84682923 |
| 1645 | A930015D03Rik | NR_015618.2 | chr17:35994503-36038174 | 1742 | Abcg8 | NM_001286005.1 | chr17:84676301-84700333 |
| 1646 | A930016O22Rik | NR_073014.1 | chr7:19417465-19421417 | 1743 | Abhd1 | NR_021304.3 | chr5:30950105-30955091 |
| 1647 | A930017M01Rik | NR_033609.2 | chr15:44881393-44884743 | 1744 | Abhd10 | NM_001272070.1 | chr16:45729724-45742955 |
| 1648 | A930018P22Rik | NM_026634.2 | chr2:104122768-104124746 | 1745 | Abhd11 | NM_001190437.1 | chr5:135009151-135012175 |

Fig.21 - 10

| | | | | | | | | |
|---|---|---|---|---|---|---|---|---|
| 1746 | Abhd1os | NR_026686.1 | chr5:135012121-135013157 | 1843 | Acox2 | NM_001161667.1 | chr14:8225510-8258839 |
| 1747 | Abhd12 | NM_024465.3 | chr2:150832514-150904731 | 1844 | Acox3 | NM_030721.2 | chr5:35583059-35613801 |
| 1748 | Abhd12b | NM_001195033.1 | chr12:70154170-70183206 | 1845 | Acoxl | NM_028765.3 | chr2:127854627-128123892 |
| 1749 | Abhd13 | NM_001081119.1 | chr8:9977716-9992154 | 1846 | Acp1 | NM_001110239.1 | chr12:30893325-30911612 |
| 1750 | Abhd14a | NM_001110271.1 | chr9:106440050-106447678 | 1847 | Acp2 | NM_007387.2 | chr2:91202913-91214098 |
| 1751 | Abhd14b | NM_029631.3 | chr3:106448639-106452918 | 1848 | Acp5 | NM_001102404.1 | chr9:22126726-22131865 |
| 1752 | Abhd15 | NM_026185.4 | chr11:77515116-77520628 | 1849 | Acp6 | NM_019800.4 | chr3:97158776-97176576 |
| 1753 | Abhd16a | NM_178592.3 | chr17:35089290-35102987 | 1850 | Acpp | NM_019807.2 | chr9:104298999-104337722 |
| 1754 | Abhd16b | NM_183181.2 | chr2:181493205-181494980 | 1851 | Acpt | NM_001195034.1 | chr7:44253086-44257204 |
| 1755 | Abhd17a | NM_145421.2 | chr10:80583648-80590341 | 1852 | Acr | NM_001205049.1 | chr15:89568325-89574685 |
| 1756 | Abhd17b | NM_146096.3 | chr19:21653808-21688637 | 1853 | Acrbp | NM_001127340.1 | chr6:125049926-125054193 |
| 1757 | Abhd17c | NM_133722.2 | chr7:84109355-84151893 | 1854 | Acrv1 | NM_007391.2 | chr9:36693219-36698837 |
| 1758 | Abhd2 | NM_018811.6 | chr7:79273265-79361601 | 1855 | Acsbg1 | NM_053178.2 | chr9:54604996-54661885 |
| 1759 | Abhd3 | NM_134130.1 | chr18:10644410-10706696 | 1856 | Acsbg2 | NM_001039114.1 | chr17:56843103-56874447 |
| 1760 | Abhd4 | NM_001205181.1 | chr14:54254128-54269169 | 1857 | Acsf2 | NM_153807.2 | chr11:94557101-94601786 |
| 1761 | Abhd5 | NM_026179.2 | chr9:122351615-122381523 | 1858 | Acsf3 | NM_144932.3 | chr8:122775504-122817881 |
| 1762 | Abhd6 | NM_025341.3 | chr14:8002901-8056555 | 1859 | Acsl1 | NM_007981.4 | chr8:46471036-46536051 |
| 1763 | Abhd8 | NM_022419.3 | chr8:71456699-71463657 | 1860 | Acsl3 | NM_001033606.2 | chr1:78657824-78707743 |
| 1764 | Abi1 | NM_001077190.2 | chr2:22939986-23040241 | 1861 | Acsl4 | NM_001033600.1 | chrX:142317992-142390535 |
| 1765 | Abi2 | NM_001198570.1 | chr1:60409618-60481163 | 1862 | Acsl5 | NM_027976.2 | chr19:55253368-55296628 |
| 1766 | Abi3 | NM_001163464.1 | chr11:95830071-95842476 | 1863 | Acsl6 | NM_001203597.1 | chr11:54304203-54361539 |
| 1767 | Abi3bp | NM_001014399.2 | chr16:56477845-56690135 | 1864 | Acsm1 | NM_054094.5 | chr7:119617827-119662515 |
| 1768 | Abl1 | NM_001112703.2 | chr2:31688536-31804362 | 1865 | Acsm2 | NM_001177977.1 | chr7:119554339-119600694 |
| 1769 | Abl2 | NM_001136104.1 | chr1:156558786-156649619 | 1866 | Acsm3 | NM_016870.3 | chr7:119760922-119784896 |
| 1770 | Ablim1 | NM_001103177.2 | chr19:57033263-57197831 | 1867 | Acsm4 | NM_178414.3 | chr7:119690025-119714566 |
| 1771 | Ablim2 | NM_177696.1 | chr5:35757879-35884979 | 1868 | Acsm5 | NM_178758.3 | chr7:119526264-119543360 |
| 1772 | Ablim3 | NM_001164491.1 | chr18:61799392-61911852 | 1869 | Acss1 | NM_080575.2 | chr2:150618110-150668240 |
| 1773 | Abo | NM_001290444.1 | chr2:26842502-26864995 | 1870 | Acss2 | NM_019811.3 | chr2:155518042-155562743 |
| 1774 | Abr | NM_001291186.1 | chr11:76416731-76468465 | 1871 | Acss2os | NR_040613.1 | chr2:155547039-155556930 |
| 1775 | Abra | NM_175456.4 | chr15:41865292-41869720 | 1872 | Acss3 | NM_001142804.1 | chr10:106936163-107123664 |
| 1776 | Abracl | NM_028843.1 | chr19:18011259-18023252 | 1873 | Acta1 | NM_001272041.1 | chr8:123891757-123894775 |
| 1777 | Abt1 | NM_013924.3 | chr13:23418360-23423866 | 1874 | Acta2 | NM_007392.3 | chr19:34240335-34255373 |
| 1778 | Abtb1 | NM_030251.3 | chr6:88835913-88841935 | 1875 | Actb | NM_007393.5 | chr5:142903114-142906754 |
| 1779 | Abtb2 | NM_178890.3 | chr2:103566309-103718423 | 1876 | Actbl2 | NM_175497.3 | chr13:111255012-111257749 |
| 1780 | Acaa1a | NM_130864.3 | chr9:119341293-119350295 | 1877 | Actc1 | NM_009608.3 | chr2:114047283-114062875 |
| 1781 | Acaa1b | NM_146230.3 | chr9:119148042-119157093 | 1878 | Actg1 | NM_009609.3 | chr11:120348686-120348495 |
| 1782 | Acaa2 | NM_177470.3 | chr18:74779211-74806207 | 1879 | Actg2 | NM_009610.2 | chr6:83512908-83536251 |
| 1783 | Acaca | NM_133360.2 | chr11:84195437-84401651 | 1880 | Actl10 | NM_001171640.1 | chr2:154551775-154553276 |
| 1784 | Acacb | NM_133904.2 | chr5:114165517-114250758 | 1881 | Actl11 | NM_026338.3 | chr9:107928468-107932461 |
| 1785 | Acad10 | NM_028957.4 | chr5:121621028-121660510 | 1882 | Actl6a | NM_019673.2 | chr3:32708545-32726971 |
| 1786 | Acad11 | NM_175324.3 | chr9:104063702-104127646 | 1883 | Actl6b | NM_033404.4 | chr5:137653854-137669573 |
| 1787 | Acad12 | NM_178894.3 | chr5:121598280-121618938 | 1884 | Actl7a | NM_009611.3 | chr4:56743421-56744925 |
| 1788 | Acad8 | NM_025862.2 | chr9:26974138-26999549 | 1885 | Actl7b | NM_025271.2 | chr4:56740004-56741425 |
| 1789 | Acad9 | NM_172678.3 | chr3:36065999-36092857 | 1886 | Actl9 | NM_183282.2 | chr17:33432898-33434287 |
| 1790 | Acadl | NM_007381.4 | chr1:66830838-66863309 | 1887 | Actn1 | NM_134156.2 | chr12:80167541-80260371 |
| 1791 | Acadm | NM_007382.5 | chr3:153922352-153944643 | 1888 | Actn2 | NM_033268.4 | chr13:12269426-12340732 |
| 1792 | Acads | NM_007383.3 | chr5:115110298-115119346 | 1889 | Actn3 | NM_013456.2 | chr19:4861215-4877909 |
| 1793 | Acadsb | NM_025826.4 | chr7:131410600-131446211 | 1890 | Actn4 | NM_021895.2 | chr7:28893253-28962280 |
| 1794 | Acadvl | NM_017366.3 | chr11:70016182-70015428 | 1891 | Actr10 | NM_019785.2 | chr12:70937856-70964717 |
| 1795 | Acan | NM_007424.2 | chr7:79053482-79115099 | 1892 | Actr1a | NM_016860.1 | chr19:46376813-46395735 |
| 1796 | Acap1 | NM_153788.3 | chr11:69881566-69895539 | 1893 | Actr1b | NM_146107.2 | chr1:36699201-36709925 |
| 1797 | Acap2 | NM_030138.2 | chr16:31092412-31201238 | 1894 | Actr2 | NM_146243.2 | chr11:20062303-20112951 |
| 1798 | Acap3 | NM_207223.2 | chr4:155891874-155907251 | 1895 | Actr3 | NM_001205385.1 | chr1:125392904-125435727 |
| 1799 | Acat1 | NM_144784.3 | chr9:53580521-53610350 | 1896 | Actr3b | NM_001004365.2 | chr5:25759972-25850691 |
| 1800 | Acat2 | NM_009338.3 | chr17:12943041-12960725 | 1897 | Actr5 | NM_175419.4 | chr2:158624912-158639211 |
| 1801 | Acat3 | NM_153151.3 | chr17:12923958-12940396 | 1898 | Actr6 | NM_025914.2 | chr10:89711972-89732285 |
| 1802 | Acbd3 | NM_133225.3 | chr1:180726042-180754204 | 1899 | Actr8 | NM_027493.3 | chr14:29978336-29993221 |
| 1803 | Acbd4 | NM_025988.2 | chr11:103101687-103112199 | 1900 | Actr11 | NM_028514.3 | chrX:46329006-46330345 |
| 1804 | Acbd5 | NM_001102436.1 | chr2:23068200-23114512 | 1901 | Actrt2 | NM_028513.3 | chr4:154666427-154667867 |
| 1805 | Acbd6 | NM_001145781.1 | chr1:155558119-155587794 | 1902 | Actrt3 | NM_029690.2 | chr3:30597070-30599870 |
| 1806 | Acbd7 | NM_030063.2 | chr2:3336167-3340997 | 1903 | Acvr1 | NM_001110204.1 | chr2:58446437-58566828 |
| 1807 | Accs | NM_001290782.1 | chr2:93833466-93849943 | 1904 | Acvr1b | NM_007395.3 | chr15:101174124-101212601 |
| 1808 | Accsl | NM_001033445.4 | chr2:93855359-93869157 | 1905 | Acvr1c | NM_001033369.3 | chr2:58267452-58324807 |
| 1809 | Acd | NM_001012638.1 | chr8:105698152-105701095 | 1906 | Acvr2a | NM_007396.4 | chr2:48814108-48903264 |
| 1810 | Ace | NM_001281819.1 | chr11:105967944-105989964 | 1907 | Acvr2b | NM_007397.3 | chr9:119402177-119442148 |
| 1811 | Ace2 | NM_001130513.1 | chrX:164139341-164188418 | 1908 | Acvrl1 | NM_001277255.1 | chr15:101182521-101145336 |
| 1812 | Ace3 | NM_001101453.2 | chr11:105994674-106005443 | 1909 | Acy1 | NM_001276442.1 | chr9:106430980-106438236 |
| 1813 | Acer1 | NM_175731.4 | chr17:56953489-56982126 | 1910 | Acy3 | NM_001302479.1 | chr19:3986570-3990007 |
| 1814 | Acer2 | NM_001290541.1 | chr4:86874413-86920843 | 1911 | Acyp1 | NM_025421.2 | chr12:85272397-85280435 |
| 1815 | Acer3 | NM_025408.2 | chr7:98213659-98309527 | 1912 | Acyp2 | NM_029344.3 | chr11:30505991-30649396 |
| 1816 | Ache | NM_001290010.1 | chr5:137288253-137294466 | 1913 | Ada | NM_001272052.1 | chr2:163726570-163750239 |
| 1817 | Acin1 | NM_001085472.2 | chr14:54642160-54653701 | 1914 | Adad1 | NM_009350.3 | chr3:37063655-37111512 |
| 1818 | Ackr1 | NM_010045.2 | chr1:173331885-173333503 | 1915 | Adad2 | NM_029428.1 | chr8:119612746-119616926 |
| 1819 | Ackr2 | NM_001276719.1 | chr9:121898354-121911691 | 1916 | Adal | NM_001290811.1 | chr2:121140427-121156680 |
| 1820 | Ackr3 | NM_001271607.1 | chr1:90203979-90215722 | 1917 | Adam10 | NM_007399.3 | chr9:70679000-70780229 |
| 1821 | Ackr4 | NM_145700.2 | chr9:104098137-104126643 | 1918 | Adam11 | NM_001110778.1 | chr11:102761438-102780262 |
| 1822 | Acly | NM_001199296.1 | chr11:100476351-100528000 | 1919 | Adam12 | NM_007400.2 | chr7:133883198-134225097 |
| 1823 | Acmsd | NM_001033041.2 | chr1:127729412-127767564 | 1920 | Adam15 | NM_001037722.2 | chr3:89339639-89350010 |
| 1824 | Acn9 | NM_001077177.3 | chr6:6956017-7039220 | 1921 | Adam17 | NM_001277266.1 | chr12:21323508-21373632 |
| 1825 | Acnat1 | NM_001164565.1 | chr4:49443531-49451109 | 1922 | Adam18 | NM_010084.2 | chr8:24602245-24674755 |
| 1826 | Acnat2 | NM_145368.2 | chr4:49379844-49408151 | 1923 | Adam19 | NM_001291890.1 | chr11:46054501-46147347 |
| 1827 | Aco1 | NM_007386.2 | chr4:40143264-40199009 | 1924 | Adam1a | NM_172126.2 | chr5:121518803-121521695 |
| 1828 | Aco2 | NM_080633.2 | chr15:81872462-81915137 | 1925 | Adam1b | NM_172125.2 | chr5:121500096-121502980 |
| 1829 | Acot1 | NM_012006.2 | chr12:84009901-84017669 | 1926 | Adam2 | NM_009618.2 | chr14:66027328-66077733 |
| 1830 | Acot10 | NM_001112703.2 | chr15:20665523-20666750 | 1927 | Adam20 | NM_001009548.2 | chr8:40793272-40797303 |
| 1831 | Acot11 | NM_025590.4 | chr4:106744560-106799831 | 1928 | Adam21 | NM_020330.4 | chr12:81558583-81564874 |
| 1832 | Acot12 | NM_028790.3 | chr13:91741520-91786148 | 1929 | Adam22 | NM_001007220.3 | chr5:8092259-8368160 |
| 1833 | Acot13 | NM_025790.2 | chr13:24817954-24831489 | 1930 | Adam23 | NM_001177600.1 | chr1:63445903-63573219 |
| 1834 | Acot2 | NM_134188.3 | chr12:83987860-83993875 | 1931 | Adam24 | NM_010086.4 | chr8:40675093-40682199 |
| 1835 | Acot3 | NM_134246.3 | chr12:84050524-84059946 | 1932 | Adam25 | NM_011781.2 | chr8:40752207-40756176 |
| 1836 | Acot4 | NM_134247.3 | chr12:84038378-84044723 | 1933 | Adam26a | NM_010085.2 | chr8:43568275-43576707 |
| 1837 | Acot5 | NM_145444.3 | chr12:84069824-84076019 | 1934 | Adam26b | NM_001009547.2 | chr8:43519863-43528137 |
| 1838 | Acot6 | NM_172580.1 | chr12:84100653-84108783 | 1935 | Adam28 | NM_001048175.2 | chr14:68604997-68655842 |
| 1839 | Acot7 | NM_001146057.1 | chr4:152186133-152271855 | 1936 | Adam29 | NM_175939.3 | chr8:55870911-55908964 |
| 1840 | Acot8 | NM_133240.2 | chr2:164677233-24725825 | 1937 | Adam3 | NM_009619.4 | chr8:24677233-24725825 |
| 1841 | Acot9 | NM_019736.4 | chrX:155262442-155297654 | 1938 | Adam30 | NM_027665.1 | chr3:98160811-98163173 |
| 1842 | Acox1 | NM_001271898.1 | chr11:116171882-116199045 | 1939 | Adam32 | NM_153397.2 | chr8:24836142-24948804 |

Fig.21 - 11

| | | | | | | | | |
|---|---|---|---|---|---|---|---|---|
| 1940 | Adam33 | NM_001163529.1 | chr2:131050816-131063814 | 2037 | Adra2c | NM_007418.3 | chr5:35278565-35281763 |
| 1941 | Adam34 | NM_145745.2 | chr8:43650308-43665560 | 2038 | Adrb1 | NM_007419.2 | chr19:56722371-56724862 |
| 1942 | Adam39 | NM_001025380.3 | chr8:40823008-40826861 | 2039 | Adrb2 | NM_007420.3 | chr18:62177712-62179981 |
| 1943 | Adam4 | NM_009620.1 | chr12:81419548-81421878 | 2040 | Adrb3 | NM_013462.3 | chr8:27225775-27229588 |
| 1944 | Adam5 | NM_001272057.1 | chr8:24732983-24824369 | 2041 | Adrbk1 | NM_001290818.1 | chr19:4285998-4306222 |
| 1945 | Adam6a | NM_174885.3 | chr12:113543907-113546414 | 2042 | Adrbk2 | NM_001285806.1 | chr5:112910477-113015538 |
| 1946 | Adam6b | NM_001009545.1 | chr12:113489564-113491835 | 2043 | Adrm1 | NM_019822.3 | chr2:180171587-180176283 |
| 1947 | Adam7 | NM_007402.2 | chr14:68497336-68533689 | 2044 | Adsl | NM_009634.6 | chr15:80948489-80970947 |
| 1948 | Adam8 | NM_001291066.2 | chr7:139978931-139992562 | 2045 | Adss | NM_007422.3 | chr1:177763177-177796509 |
| 1949 | Adam9 | NM_001270996.1 | chr8:24949610-25016922 | 2046 | Adssl1 | NM_007421.2 | chr12:112620046-112641355 |
| 1950 | Adamdec1 | NM_021475.2 | chr14:68563386-68582072 | 2047 | Adtrp | NM_001141875.1 | chr13:41763147-41847618 |
| 1951 | Adamts1 | NM_009621.5 | chr16:85793827-85803113 | 2048 | Aebp1 | NM_001291857.2 | chr11:5861865-5872248 |
| 1952 | Adamts10 | NM_172619.3 | chr17:33524195-33553782 | 2049 | Aebp2 | NM_001005605.2 | chr6:140623501-140655481 |
| 1953 | Adamts12 | NM_175501.2 | chr15:11064789-11346867 | 2050 | Aen | NM_001162939.1 | chr7:78895926-78908833 |
| 1954 | Adamts13 | NM_001001322.2 | chr2:26972415-27009625 | 2051 | Aes | NM_001276288.1 | chr10:81559443-81566371 |
| 1955 | Adamts14 | NM_001081127.1 | chr10:61197111-61273438 | 2052 | AF067061 | NM_199060.2 | chr13:120263094-120264517 |
| 1956 | Adamts15 | NM_001024139.1 | chr9:30899154-30922452 | 2053 | AF067063 | NM_001001449.2 | chr13:119827960-119830217 |
| 1957 | Adamts16 | NM_172053.2 | chr13:70727807-70841810 | 2054 | AF251705 | NM_134158.1 | chr11:114996768-115001880 |
| 1958 | Adamts17 | NM_001033877.4 | chr7:66839734-87152625 | 2055 | AF357355 | NR_028433.2 | chr12:109654628-109654697 |
| 1959 | Adamts18 | NM_172466.2 | chr8:113698136-113848839 | 2056 | AF357359 | NR_028434.1 | chr12:109650708-109650738 |
| 1960 | Adamts19 | NM_175506.3 | chr8:58636763-59053678 | 2057 | AF357399 | NR_028129.1 | chr7:28351539-28351633 |
| 1961 | Adamts2 | NM_175643.3 | chr11:50602085-50807573 | 2058 | AF357425 | NR_046302.1 | chr12:109636011-109636080 |
| 1962 | Adamts20 | NM_001164785.1 | chr15:94320331-94404350 | 2059 | AF357426 | NR_046303.1 | chr12:109642837-109642904 |
| 1963 | Adamts3 | NM_001081401.2 | chr5:89673840-89883334 | 2060 | AF366264 | NM_153093.3 | chr5:13835230-13838089 |
| 1964 | Adamts4 | NM_172845.2 | chr1:171250421-171259922 | 2061 | AF529169 | NM_153509.2 | chr9:89590034-89622986 |
| 1965 | Adamts5 | NM_011782.2 | chr16:85858156-85901125 | 2062 | Afap1 | NM_027373.2 | chr5:35893318-36003922 |
| 1966 | Adamts6 | NM_001081020.1 | chr13:104287872-104494763 | 2063 | Afap1l1 | NM_178928.4 | chr18:61730261-61786662 |
| 1967 | Adamts7 | NM_001003911.2 | chr9:90162977-90200102 | 2064 | Afap1l2 | NM_001177796.1 | chr19:56912353-57008575 |
| 1968 | Adamts8 | NM_013906.2 | chr9:30942562-30962858 | 2065 | Aff1 | NM_001080798.2 | chr5:103754572-103955322 |
| 1969 | Adamts9 | NM_175314.3 | chr6:92772698-92901441 | 2066 | Aff2 | NM_008032.3 | chrX:69360930-69868037 |
| 1970 | Adamtsl1 | NM_029967.3 | chr4:86053914-86428382 | 2067 | Aff3 | NM_001290814.1 | chr1:38175990-38627244 |
| 1971 | Adamtsl2 | NM_029981.1 | chr2:27079380-27108613 | 2068 | Aff4 | NM_033565.2 | chr11:53350766-53421830 |
| 1972 | Adamtsl3 | NM_001190374.1 | chr7:82335693-82614448 | 2069 | Afg3l1 | NM_054070.3 | chr8:123477861-123503916 |
| 1973 | Adamtsl4 | NM_144899.3 | chr3:95676200-95687917 | 2070 | Afg3l2 | NM_027130.1 | chr18:67404763-67449136 |
| 1974 | Adamtsl5 | NM_001285435.1 | chr10:80339792-80348448 | 2071 | Afm | NM_145146.2 | chr5:90518948-90553544 |
| 1975 | Adap1 | NM_172729.4 | chr5:139271879-139325464 | 2072 | Afmid | NM_027827.3 | chr11:117825918-117839908 |
| 1976 | Adap2 | NM_172133.1 | chr11:80154161-80178827 | 2073 | Afp | NM_007423.4 | chr5:90490713-90508907 |
| 1977 | Adar | NM_001038587.4 | chr3:89715021-89753455 | 2074 | Aftph | NM_001252503.2 | chr11:20685084-20741556 |
| 1978 | Adarb1 | NM_001024237.2 | chr10:77290726-77418273 | 2075 | Aga | NM_001005847.2 | chr8:53511701-53523422 |
| 1979 | Adarb2 | NM_001289530.1 | chr13:8202865-8760442 | 2076 | Agap1 | NM_001037136.1 | chr1:89454810-89895282 |
| 1980 | Adat1 | NM_013925.4 | chr8:111966907-111992302 | 2077 | Agap2 | NM_001033263.5 | chr10:127078906-127093170 |
| 1981 | Adat2 | NM_025748.4 | chr10:13552906-13563378 | 2078 | Agap3 | NM_001256431.1 | chr5:24852176-24883184 |
| 1982 | Adat3 | NM_001100606.1 | chr10:80602879-80607654 | 2079 | Agbl1 | NM_001199224.1 | chr7:76229886-77124698 |
| 1983 | Adc | NM_172875.4 | chr4:128932016-128962455 | 2080 | Agbl2 | NM_178755.3 | chr2:90782743-90816231 |
| 1984 | Adck1 | NM_001277096.1 | chr12:88360513-88461726 | 2081 | Agbl3 | NM_001289656.1 | chr6:34780431-34859459 |
| 1985 | Adck2 | NM_178873.3 | chr6:39573875-39588769 | 2082 | Agbl4 | NM_001048189.4 | chr4:110397697-111657519 |
| 1986 | Adck3 | NM_001163290.1 | chr1:180165237-180193485 | 2083 | Agbl5 | NM_001048192.2 | chr5:30889005-30906666 |
| 1987 | Adck4 | NM_133770.2 | chr7:27233012-27257949 | 2084 | Ager | NM_001271422.1 | chr17:34597849-34600937 |
| 1988 | Adck5 | NM_172960.3 | chr15:76576358-76595811 | 2085 | Agfg1 | NM_010472.3 | chr1:82839459-82901001 |
| 1989 | Adcy1 | NM_009622.1 | chr11:7063488-7178505 | 2086 | Agfg2 | NM_001303266.1 | chr5:137650463-137684806 |
| 1990 | Adcy10 | NM_173029.3 | chr1:165485182-165576773 | 2087 | Aggf1 | NM_025630.3 | chr13:95350682-95375357 |
| 1991 | Adcy2 | NM_153534.2 | chr13:68620042-68999541 | 2088 | Agk | NM_023538.2 | chr6:40325477-40396762 |
| 1992 | Adcy3 | NM_001159536.1 | chr12:4133396-4213524 | 2089 | Agl | NM_001081326.1 | chr3:116739998-116808166 |
| 1993 | Adcy4 | NM_080435.1 | chr14:55769091-55784019 | 2090 | Agmat | NM_001081408.1 | chr4:141746674-141759263 |
| 1994 | Adcy5 | NM_001012765.4 | chr16:35155635-35304549 | 2091 | Agmo | NM_178767.5 | chr12:37243638-37581932 |
| 1995 | Adcy6 | NM_007405.2 | chr15:98589985-98607633 | 2092 | Ago1 | NM_153403.2 | chr4:126435012-126468421 |
| 1996 | Adcy7 | NM_001037723.2 | chr8:88289065-88329962 | 2093 | Ago2 | NM_153178.4 | chr15:73101624-73184947 |
| 1997 | Adcy8 | NM_001291503.1 | chr15:64699034-64922296 | 2094 | Ago3 | NM_153402.2 | chr4:126340877-126429542 |
| 1998 | Adcy9 | NM_001291910.1 | chr16:4284885-4420498 | 2095 | Ago4 | NM_153177.3 | chr4:126489642-126533458 |
| 1999 | Adcyap1 | NM_009625.3 | chr17:93199421-93205489 | 2096 | Agpat1 | NM_001163379.1 | chr17:34605860-34613443 |
| 2000 | Adcyap1r1 | NM_001025372.2 | chr6:55451977-55501435 | 2097 | Agpat2 | NM_026212.2 | chr2:26593056-26604417 |
| 2001 | Add1 | NM_001024458.3 | chr5:34579713-34632305 | 2098 | Agpat3 | NM_053014.3 | chr10:78271562-78315700 |
| 2002 | Add2 | NM_001275372.2 | chr6:86028680-86124409 | 2099 | Agpat4 | NM_026644.2 | chr17:12119283-12219640 |
| 2003 | Add3 | NM_001164099.2 | chr19:53146042-53247326 | 2100 | Agpat5 | NM_026792.3 | chr8:18846278-18884413 |
| 2004 | Adgb | NM_001273353.2 | chr10:10335762-10472314 | 2101 | Agpat6 | NM_018743.4 | chr8:23172945-23208453 |
| 2005 | Adh1 | NM_007409.3 | chr3:138277644-138290691 | 2102 | Agpat9 | NM_172715.3 | chr5:100846228-100889102 |
| 2006 | Adh4 | NM_011996.2 | chr3:138415496-138430892 | 2103 | Agps | NM_172666.3 | chr2:75832176-75931350 |
| 2007 | Adh5 | NM_001288578.1 | chr3:138437199-138455499 | 2104 | Agr2 | NM_011783.2 | chr12:35992924-36004081 |
| 2008 | Adh6a | NM_026945.1 | chr3:138313285-138331134 | 2105 | Agr3 | NM_207531.3 | chr12:35925620-35949730 |
| 2009 | Adh6-ps1 | NR_033581.1 | chr3:138374120-138388291 | 2106 | Agrn | NM_021604.3 | chr4:156165289-156197488 |
| 2010 | Adh7 | NM_009629.4 | chr3:138217772-138232042 | 2107 | Agrp | NM_001271806.1 | chr8:105566694-105579845 |
| 2011 | Adhfe1 | NM_175236.4 | chr1:9548045-9577968 | 2108 | Agt | NM_007428.3 | chr8:124556586-124569707 |
| 2012 | Adi1 | NM_134005.2 | chr12:28675206-28682174 | 2109 | Agtpbp1 | NM_001048008.2 | chr13:59493403-59557347 |
| 2013 | Adig | NM_145635.2 | chr2:158502611-158508198 | 2110 | Agtr1a | NM_177322.3 | chr13:30336355-30382867 |
| 2014 | Adipoq | NM_009605.4 | chr16:23146535-23157968 | 2111 | Agtr1b | NM_175086.3 | chr3:20314472-20367177 |
| 2015 | Adipor1 | NM_028320.4 | chr1:134415377-134433350 | 2112 | Agtr2 | NM_007429.5 | chrX:21484623-21488833 |
| 2016 | Adipor2 | NM_197985.3 | chr6:119353149-119417483 | 2113 | Agtrap | NM_009642.4 | chr4:148077060-148088064 |
| 2017 | Adk | NM_001243041.1 | chr14:21076151-21448569 | 2114 | Agxt | NM_001276710.1 | chr1:93135239-93145421 |
| 2018 | Adm | NM_009627.1 | chr7:110627668-110629819 | 2115 | Agxt2 | NM_001031851.1 | chr15:10358578-10409734 |
| 2019 | Adm2 | NM_182685.5 | chr15:89322719-89324730 | 2116 | Ahctf1 | NM_026375.2 | chr1:179744903-179804015 |
| 2020 | Adnp | NM_009628.3 | chr2:168180964-168207112 | 2117 | Ahcy | NM_016661.3 | chr2:155059311-155074497 |
| 2021 | Adnp2 | NM_175024.1 | chr18:80127134-80151482 | 2118 | Ahcyl1 | NM_145542.3 | chr3:107663119-107696548 |
| 2022 | Ado | NM_001095419.2 | chr10:67544510-67548955 | 2119 | Ahcyl2 | NM_001171000.2 | chr6:29768442-29912310 |
| 2023 | Adora1 | NM_001008533.3 | chr1:134199214-134235457 | 2120 | Ahdc1 | NM_146155.3 | chr4:133011505-133078110 |
| 2024 | Adora2a | NM_009630.2 | chr10:75316678-75334792 | 2121 | Ahi1 | NM_001177776.1 | chr10:21040819-21080429 |
| 2025 | Adora2b | NM_007413.4 | chr11:62248983-62266452 | 2122 | Ahnak | NM_001039959.2 | chr19:8989283-9076926 |
| 2026 | Adora3 | NM_001174169.2 | chr3:105870857-105908928 | 2123 | Ahi | NM_013464.4 | chr12:35497978-35534989 |
| 2027 | Adpgk | NM_028121.2 | chr9:59291571-59316200 | 2124 | Ahrr | NM_009644.2 | chr13:74211117-74292309 |
| 2028 | Adprh | NM_007414.3 | chr16:38445398-38452689 | 2125 | Ahsa1 | NM_146036.1 | chr12:87266727-87273952 |
| 2029 | Adprhl1 | NM_172750.3 | chr8:13235661-13254182 | 2126 | Ahsa2 | NM_001290654.1 | chr11:23487881-23498039 |
| 2030 | Adprhl2 | NM_138830.2 | chr4:126316350-126321703 | 2127 | Ahsg | NM_001276449.1 | chr16:22892014-22899451 |
| 2031 | Adprm | NM_025610.3 | chr11:67037879-67052618 | 2128 | AI115009 | NR_040386.1 | chr3:152666912-152681482 |
| 2032 | Adra1a | NM_001279759.1 | chr14:36650520-66733462 | 2129 | AI118078 | NM_172923.3 | chr9:55326948-55438344 |
| 2033 | Adra1b | NM_001284380.1 | chr11:43774604-43901237 | 2130 | AI182371 | NM_001243102.1 | chr2:35081860-35100685 |
| 2034 | Adra1d | NM_013460.4 | chr2:131545356-131562285 | 2131 | AI197445 | NR_045083.1 | chr13:107469821-107479188 |
| 2035 | Adra2a | NM_007417.4 | chr19:54045181-54048982 | 2132 | AI314180 | NM_172381.2 | chr4:58800030-58912725 |
| 2036 | Adra2b | NM_009633.3 | chr2:127363285-127367221 | 2133 | AI314278 | NR_102276.1 | chr7:89426305-89432077 |

Fig.21 - 12

| | | | | | | | | |
|---|---|---|---|---|---|---|---|---|
| 2134 | AI317395 | NM_144821.4 | chr10:40001572-40025268 | | 2231 | Akt1 | NM_001165894.1 | chr12:112653820-112674276 |
| 2135 | AI413582 | NM_001002895.2 | chr17:27563768-27565727 | | 2232 | Akt1s1 | NM_001253920.1 | chr7:44850006-44855421 |
| 2136 | AI414108 | NR_027907.1 | chr9:27352684-27357543 | | 2233 | Akt2 | NM_001110208.1 | chr7:27591559-27639453 |
| 2137 | AI427809 | NR_033139.1 | chr4:53261355-53270232 | | 2234 | Akt3 | NM_011785.3 | chr1:177022114-177248767 |
| 2138 | AI429214 | NM_001039220.3 | chr8:36993574-36995533 | | 2235 | Aktip | NM_010241.5 | chr8:91123498-91135494 |
| 2139 | AI450353 | NR_028364.1 | chr11:83293429-83294929 | | 2236 | Alad | NM_001276446.1 | chr4:62505983-62519909 |
| 2140 | AI462493 | NM_001160356.1 | chr19:8880013-8880933 | | 2237 | Alas1 | NM_001291835.1 | chr9:106233454-106247736 |
| 2141 | AI463170 | NR_046044.1 | chr12:76546971-76547925 | | 2238 | Alas2 | NM_001102446.1 | chrX:150547416-150576622 |
| 2142 | AI464131 | NM_001085515.2 | chr4:41495600-41503075 | | 2239 | Alb | NM_009654.4 | chr5:90460888-90476603 |
| 2143 | AI467606 | NM_178901.3 | chr7:127091435-127094049 | | 2240 | Alcam | NM_009655.2 | chr16:52248995-52452997 |
| 2144 | AI504432 | NR_033498.1 | chr3:107039503-107054322 | | 2241 | Aldh16a1 | NM_145954.1 | chr7:45141839-45154538 |
| 2145 | AI506816 | NR_015554.2 | chr5:23892260-23712667 | | 2242 | Aldh18a1 | NM_019698.2 | chr19:40550256-40588463 |
| 2146 | AI507597 | NR_033566.1 | chr4:141614369-141615604 | | 2243 | Aldh1a1 | NM_013467.3 | chr19:20601981-20643462 |
| 2147 | AI593442 | NM_001286641.1 | chr9:52673031-52679780 | | 2244 | Aldh1a2 | NM_009022.4 | chr9:71215788-71286243 |
| 2148 | AI597479 | NM_133818.1 | chr1:43098709-43115946 | | 2245 | Aldh1a3 | NM_053080.3 | chr7:66390892-66427477 |
| 2149 | AI606473 | NR_040387.1 | chr3:154330820-154334687 | | 2246 | Aldh1a7 | NM_011921.2 | chr19:20692952-20727556 |
| 2150 | AI607873 | NM_001204910.1 | chr1:173773427-173741809 | | 2247 | Aldh1b1 | NM_028270.4 | chr4:45799021-45804608 |
| 2151 | AI646519 | NR_040330.1 | chr2:147361542-147362793 | | 2248 | Aldh1l1 | NM_027406.1 | chr6:90550847-90598171 |
| 2152 | AI661453 | NM_145489.2 | chr17:47436638-47470638 | | 2249 | Aldh1l2 | NM_153543.2 | chr10:83487446-83534140 |
| 2153 | AI662270 | NR_015519.1 | chr11:83223575-83226584 | | 2250 | Aldh2 | NM_009656.4 | chr5:121566026-121593824 |
| 2154 | AI747448 | NM_001033199.3 | chr3:144910920-144932529 | | 2251 | Aldh3a1 | NM_001112725.1 | chr11:61208741-61218416 |
| 2155 | AI837181 | NM_001256515.1 | chr19:5425143-5427316 | | 2252 | Aldh3a2 | NM_007437.5 | chr11:61244751-61267186 |
| 2156 | AI839979 | NR_102275.1 | chr5:31565591-31571397 | | 2253 | Aldh3b1 | NM_026316.2 | chr19:3913490-3929716 |
| 2157 | AI846148 | NM_001033139.3 | chr19:7356463-7383026 | | 2254 | Aldh3b2 | NM_001177438.1 | chr19:3972327-3981665 |
| 2158 | AI847159 | NR_045264.1 | chr2:129178147-129180673 | | 2255 | Aldh4a1 | NM_175438.4 | chr4:139622893-139649691 |
| 2159 | AI848285 | NM_001207021.1 | chr15:82206951-82212815 | | 2256 | Aldh5a1 | NM_172532.3 | chr13:24907578-24937661 |
| 2160 | AI854517 | NR_040311.1 | chr7:79500025-79534403 | | 2257 | Aldh6a1 | NM_134042.3 | chr12:84430720-84451024 |
| 2161 | AI854703 | NR_027236.1 | chr6:48628166-48633688 | | 2258 | Aldh7a1 | NM_001127338.1 | chr18:56525735-56572939 |
| 2162 | AI987944 | NM_001199330.1 | chr7:41372929-41393379 | | 2259 | Aldh8a1 | NM_178713.4 | chr10:21377299-21396578 |
| 2163 | Aicda | NM_009645.2 | chr6:122553808-122564180 | | 2260 | Aldh9a1 | NM_019993.3 | chr1:167349990-167368530 |
| 2164 | Aida | NM_181732.4 | chr1:183297059-183324501 | | 2261 | Aldoa | NM_001177307.1 | chr7:126795233-126799176 |
| 2165 | Aif1 | NM_019467.2 | chr17:35170991-35176001 | | 2262 | Aldoart1 | NM_001199270.1 | chr4:72850582-72852634 |
| 2166 | Aifl1 | NM_145144.1 | chr2:31950303-31973442 | | 2263 | Aldoart2 | NM_001277340.1 | chr12:55565204-55566896 |
| 2167 | Aifm1 | NM_001290364.1 | chrX:48474943-48513563 | | 2264 | Aldob | NM_144903.3 | chr4:49535992-49549546 |
| 2168 | Aifm2 | NM_001039194.3 | chr10:61715262-61738652 | | 2265 | Aldoc | NM_009657.4 | chr11:78324197-78327778 |
| 2169 | Aifm3 | NM_001291070.1 | chr16:17491920-17507482 | | 2266 | Alg1 | NM_145362.2 | chr16:5233820-5244907 |
| 2170 | Aig1 | NM_025446.3 | chr10:13652708-13868830 | | 2267 | Alg10b | NM_001033441.3 | chr15:90224310-90230554 |
| 2171 | Aim1 | NM_172393.2 | chr10:43950306-44004846 | | 2268 | Alg11 | NM_001243161.1 | chr8:22060720-22071627 |
| 2172 | Aim1l | NM_001162976.1 | chr4:134084511-134092504 | | 2269 | Alg12 | NM_001142357.1 | chr15:88805242-88819318 |
| 2173 | Aim2 | NM_001013779.2 | chr1:173420603-173466036 | | 2270 | Alg13 | NM_026247.3 | chrX:144317965-144325197 |
| 2174 | Aimp1 | NM_007926.2 | chr3:132660497-132683879 | | 2271 | Alg14 | NM_024178.2 | chr3:121291816-121362011 |
| 2175 | Aimp2 | NM_001172346.1 | chr5:143902703-143909839 | | 2272 | Alg2 | NM_019998.3 | chr4:47469832-47474367 |
| 2176 | Aip | NM_001276284.1 | chr19:4313755-4321575 | | 2273 | Alg3 | NM_145919.2 | chr16:20609457-20610749 |
| 2177 | Aipl1 | NM_053245.2 | chr11:72018721-72037509 | | 2274 | Alg5 | NM_025442.3 | chr3:54735538-54749795 |
| 2178 | Aire | NM_001271549.1 | chr10:78030021-78043610 | | 2275 | Alg6 | NM_001081264.1 | chr4:99715629-99763460 |
| 2179 | Airn | NR_002853.2 | chr17:12741310-12815557 | | 2276 | Alg8 | NM_199035.2 | chr7:97371616-97392158 |
| 2180 | Ajap1 | NM_001099299.1 | chr4:153373220-153482830 | | 2277 | Alg9 | NM_133981.2 | chr9:50775224-50843639 |
| 2181 | Ajuba | NM_010590.5 | chr14:54567468-54577661 | | 2278 | Alk | NM_007439.2 | chr17:71868987-72604807 |
| 2182 | AK010878 | NM_001142938.1 | chr12:102753274-102757810 | | 2279 | Alkbh1 | NM_001102565.1 | chr12:87428077-87443839 |
| 2183 | Ak1 | NM_001198765.1 | chr2:32621757-32635058 | | 2280 | Alkbh2 | NM_175016.2 | chr5:114123933-114128176 |
| 2184 | AK129341 | NM_001045524.1 | chr8:8076632-8134294 | | 2281 | Alkbh3 | NM_026944.1 | chr2:93980633-94010730 |
| 2185 | Ak2 | NM_001033966.4 | chr4:128993223-129008723 | | 2282 | Alkbh4 | NM_028070.1 | chr5:136138780-136141614 |
| 2186 | Ak3 | NM_021299.1 | chr19:29020831-29047902 | | 2283 | Alkbh5 | NM_172943.4 | chr11:60537682-60558512 |
| 2187 | Ak4 | NM_001177602.1 | chr4:101419288-101467771 | | 2284 | Alkbh6 | NM_198027.2 | chr7:30308752-30314303 |
| 2188 | Ak5 | NM_001081277.1 | chr3:152462814-152668140 | | 2285 | Alkbh7 | NM_025638.3 | chr17:56997338-56999936 |
| 2189 | Ak6 | NM_027592.3 | chr13:100651942-100666415 | | 2286 | Alkbh8 | NM_026303.1 | chr9:3335230-3385846 |
| 2190 | Ak7 | NM_030187.1 | chr12:105705981-105782447 | | 2287 | Alk | NM_053156.2 | chr12:28553755-28582483 |
| 2191 | Ak8 | NM_001033874.2 | chr2:28700160-28813165 | | 2288 | Alms1 | NM_145223.2 | chr6:85587530-85702751 |
| 2192 | Akap1 | NM_001042541.1 | chr11:88830791-88864586 | | 2289 | Alms1-ps2 | NR_040440.2 | chr6:85792116-85840057 |
| 2193 | Akap10 | NM_019921.3 | chr11:61871306-61930257 | | 2290 | Alox12 | NM_007440.4 | chr11:70243454-70255341 |
| 2194 | Akap11 | NM_001164503.1 | chr14:78492245-78536860 | | 2291 | Alox12b | NM_009659.2 | chr11:69157071-69169791 |
| 2195 | Akap12 | NM_031185.3 | chr10:4266328-4359471 | | 2292 | Alox12e | NM_145684.1 | chr11:70315612-70322518 |
| 2196 | Akap13 | NM_029322.1 | chr7:75455533-75754609 | | 2293 | Alox15 | NM_009660.3 | chr11:70344146-70352031 |
| 2197 | Akap14 | NM_001033785.2 | chrX:37150697-37168842 | | 2294 | Alox5 | NM_009662.2 | chr6:116410070-116461178 |
| 2198 | Akap17b | NM_001081956.1 | chrX:36608182-36645414 | | 2295 | Alox5ap | NM_009663.2 | chr5:149265603-149288153 |
| 2199 | Akap2 | NM_001035532.2 | chr4:57845247-57896984 | | 2296 | Alox8 | NM_009661.4 | chr11:69183884-69197843 |
| 2200 | Akap3 | NM_009650.2 | chr6:126853097-126874308 | | 2297 | Aloxe3 | NM_011786.2 | chr11:69126376-69149115 |
| 2201 | Akap4 | NM_001042542.2 | chrX:7068209-7078606 | | 2298 | Alpi | NM_001081082.2 | chr1:87098001-87101806 |
| 2202 | Akap5 | NM_001101471.1 | chr12:76334151-76336860 | | 2299 | Alpk1 | NM_027808.1 | chr3:127670309-127780527 |
| 2203 | Akap6 | NM_198111.2 | chr12:52699382-53151015 | | 2300 | Alpk2 | NM_001037294.1 | chr18:65265530-65393888 |
| 2204 | Akap7 | NM_018747.4 | chr10:25169089-25299163 | | 2301 | Alpk3 | NM_054085.2 | chr7:81057599-81105612 |
| 2205 | Akap8 | NM_019774.5 | chr17:32303871-32321238 | | 2302 | Alpl | NM_001287172.1 | chr4:137741730-137766475 |
| 2206 | Akap8l | NM_017476.2 | chr17:32321423-32350577 | | 2303 | Alppl2 | NM_007433.3 | chr1:87086690-87089928 |
| 2207 | Akap9 | NM_194462.2 | chr5:3928185-4080204 | | 2304 | Als2 | NM_001159948.2 | chr1:59162755-59237093 |
| 2208 | Akip1 | NM_020618.1 | chr7:109703736-109712181 | | 2305 | Als2cl | NM_001146059.1 | chr9:110580173-110600530 |
| 2209 | Akirin1 | NM_023423.3 | chr4:123735194-123750299 | | 2306 | Als2cr11 | NM_175200.4 | chr1:59056505-59094900 |
| 2210 | Akirin2 | NM_001007589.3 | chr4:34350614-34566908 | | 2307 | Als2cr12 | NM_175370.5 | chr1:58658120-58695989 |
| 2211 | Akna | NM_001045514.3 | chr4:63367122-63403445 | | 2308 | Alx1 | NM_172553.4 | chr10:103007846-103028777 |
| 2212 | Aknad1 | NM_177859.3 | chr3:108739657-108782309 | | 2309 | Alx3 | NM_007441.3 | chr3:107595030-107605875 |
| 2213 | Akp3 | NM_007432.2 | chr1:87125007-87127912 | | 2310 | Alx4 | NM_007442.3 | chr2:93642433-93681339 |
| 2214 | Akr1a1 | NM_021473.3 | chr4:116636509-116651674 | | 2311 | Alyref | NM_011568.1 | chr11:120594515-120598365 |
| 2215 | Akr1b10 | NM_172398.3 | chr6:34384246-34396949 | | 2312 | Alyref2 | NM_019484.4 | chr1:171504377-171504750 |
| 2216 | Akr1b3 | NM_009658.3 | chr6:34303929-34317489 | | 2313 | Amacr | NM_008537.4 | chr15:10981755-10996624 |
| 2217 | Akr1b7 | NM_009731.2 | chr6:34412361-34423137 | | 2314 | Ambn | NM_009664.2 | chr5:88455990-88468529 |
| 2218 | Akr1b8 | NM_008012.1 | chr6:34354163-34368845 | | 2315 | Ambp | NM_007443.4 | chr4:63143278-63154142 |
| 2219 | Akr1c12 | NM_019777.2 | chr13:4261171-4279399 | | 2316 | Ambra1 | NM_001080754.1 | chr2:91730137-91918849 |
| 2220 | Akr1c13 | NM_013778.2 | chr13:4191186-4205603 | | 2317 | Amd1 | NM_009665.5 | chr10:40287457-40302188 |
| 2221 | Akr1c14 | NM_134072.1 | chr13:4059590-4090422 | | 2318 | Amd2 | NM_007444.3 | chr10:40287464-40302186 |
| 2222 | Akr1c18 | NM_134066.2 | chr13:4132626-4150631 | | 2319 | Amdhd1 | NM_027908.1 | chr10:93523337-93540033 |
| 2223 | Akr1c19 | NM_001013785.3 | chr13:4233739-4248359 | | 2320 | Amdhd2 | NM_172935.4 | chr17:24155832-24163733 |
| 2224 | Akr1c20 | NM_054080.1 | chr13:4507158-4523333 | | 2321 | Amelx | NM_001081978.2 | chrX:169176113-169187209 |
| 2225 | Akr1c21 | NM_029901.2 | chr13:4574074-4586543 | | 2322 | Amer1 | NM_175179.4 | chrX:95420313-95444840 |
| 2226 | Akr1c6 | NM_030611.3 | chr4:34434342-34458359 | | 2323 | Amer2 | NM_001164705.1 | chr14:60378285-60381903 |
| 2227 | Akr1d1 | NM_027582.4 | chr6:35013077-35032759 | | 2324 | Amer3 | NM_213727.2 | chr1:34579692-34590944 |
| 2228 | Akr1e1 | NM_145364.2 | chr6:37530172-37568815 | | 2325 | Amfr | NM_011787.2 | chr8:93971587-94012640 |
| 2229 | Akr1e1 | NM_018859.3 | chr13:4592489-4609164 | | 2326 | Amh | NM_007445.2 | chr10:80805247-80807648 |
| 2230 | Akr7a5 | NM_025337.3 | chr4:139310743-139318786 | | 2327 | Amhr2 | NM_144547.2 | chr15:102445366-102454639 |

Fig.21 - 13

| | | | | | | | | |
|---|---|---|---|---|---|---|---|---|
| 2328 | Amica1 | NM_001005421.4 | chr9:45079182-45108531 | | 2425 | Ankrd44 | NM_001081433.3 | chr1:54645339-54926387 |
| 2329 | Amigo1 | NM_001004293.2 | chr3:108186288-108192286 | | 2426 | Ankrd45 | NM_028664.1 | chr1:161142711-161170507 |
| 2330 | Amigo2 | NM_001164563.1 | chr15:97244073-97247287 | | 2427 | Ankrd46 | NM_175134.4 | chr15:36477667-36496791 |
| 2331 | Amigo3 | NM_177275.4 | chr9:108053158-108055701 | | 2428 | Ankrd49 | NM_019683.3 | chr9:14780197-14782964 |
| 2332 | Ammecr1 | NM_019496.3 | chrX:142853473-142966723 | | 2429 | Ankrd50 | NM_001167683.1 | chr3:38449260-38484816 |
| 2333 | Ammecr1l | NM_001242430.1 | chr18:31760615-31784083 | | 2430 | Ankrd52 | NM_172790.2 | chr10:128377123-128394006 |
| 2334 | Amn | NM_033603.3 | chr12:111271095-111276426 | | 2431 | Ankrd53 | NM_029245.3 | chr6:83762645-83768326 |
| 2335 | Amn1 | NM_011113424.1 | chr6:149157576-149188712 | | 2432 | Ankrd54 | NM_144849.1 | chr15:79053093-79062859 |
| 2336 | Amot | NM_001290274.1 | chrX:145451867-145487639 | | 2433 | Ankrd55 | NM_001168403.1 | chr13:112288450-112384002 |
| 2337 | Amotl1 | NM_001081395.1 | chr9:14541966-14615000 | | 2434 | Ankrd6 | NM_001012450.1 | chr4:32804034-32923505 |
| 2338 | Amotl2 | NM_019764.2 | chr3:102717803-102738417 | | 2435 | Ankrd60 | NM_001199955.1 | chr2:173572889-173578341 |
| 2339 | Ampd1 | NM_001033303.2 | chr3:103074013-103099720 | | 2436 | Ankrd61 | NM_025732.2 | chr5:143896740-143895067 |
| 2340 | Ampd2 | NM_001289719.1 | chr3:108074061-108086666 | | 2437 | Ankrd63 | NM_001081971.1 | chr2:118699102-118703963 |
| 2341 | Ampd3 | NM_001276301.1 | chr7:110768205-110812408 | | 2438 | Ankrd66 | NM_001254953.1 | chr17:43534173-43543639 |
| 2342 | Amph | NM_001289546.1 | chr13:18948350-19150919 | | 2439 | Ankrd7 | NM_001167757.1 | chr6:18866317-18879584 |
| 2343 | Amt | NM_001013814.1 | chr9:108296921-108301597 | | 2440 | Ankrd9 | NM_175207.1 | chr12:110975352-110979021 |
| 2344 | Amtn | NM_027793.1 | chr5:88376107-88389316 | | 2441 | Anks1 | NM_001286040.1 | chr17:27909305-28062779 |
| 2345 | Amy1 | NM_001110505.1 | chr3:113555951-113577750 | | 2442 | Anks1b | NM_001128086.2 | chr10:89673508-90972984 |
| 2346 | Amy2a2 | NM_001160192.1 | chr3:113278836-113356858 | | 2443 | Anks3 | NM_028301.4 | chr16:4943414-4964237 |
| 2347 | Amy2a5 | NM_001042711.2 | chr3:113249177-113356520 | | 2444 | Anks4b | NM_028085.2 | chr7:120173857-120183716 |
| 2348 | Amy2b | NM_001190403.1 | chr3:113147655-113156727 | | 2445 | Anks6 | NM_001024136.1 | chr4:47015688-47057305 |
| 2349 | Amz1 | NM_173405.2 | chr5:140724126-140753812 | | 2446 | Ankub1 | NM_001033349.2 | chr3:57667421-57692537 |
| 2350 | Amz2 | NM_001252393.1 | chr11:109426219-109438148 | | 2447 | Ankzf1 | NM_001267620.1 | chr1:75192159-75195538 |
| 2351 | Anapc1 | NM_008569.2 | chr2:128610082-128687395 | | 2448 | Anln | NM_028390.3 | chr9:22331213-22389206 |
| 2352 | Anapc10 | NM_026904.2 | chr8:79711819-79777321 | | 2449 | Ano1 | NM_001242349.1 | chr7:144588548-144738592 |
| 2353 | Anapc11 | NM_001098230.2 | chr11:120598531-120608198 | | 2450 | Ano10 | NM_001271873.1 | chr9:122175873-122294423 |
| 2354 | Anapc13 | NM_181394.3 | chr9:102626295-102634244 | | 2451 | Ano2 | NM_153589.2 | chr6:125690418-126040128 |
| 2355 | Anapc15 | NM_001291348.1 | chr7:101896330-101899545 | | 2452 | Ano3 | NM_001128103.2 | chr2:110655200-110950244 |
| 2356 | Anapc16 | NM_025514.2 | chr10:59987908-60003112 | | 2453 | Ano4 | NM_001024136.1 | chr10:88948993-89257790 |
| 2357 | Anapc2 | NM_175300.4 | chr2:25272465-25285916 | | 2454 | Ano5 | NM_001271879.1 | chr7:51511028-51598707 |
| 2358 | Anapc4 | NM_024213.2 | chr5:52842133-52866734 | | 2455 | Ano6 | NM_001253813.1 | chr15:95790842-95975472 |
| 2359 | Anapc5 | NM_001042491.2 | chr5:122787460-122821342 | | 2456 | Ano7 | NM_001271884.1 | chr1:93373895-93404304 |
| 2360 | Anapc7 | NM_019805.4 | chr5:122422443-122444911 | | 2457 | Ano8 | NM_001164679.1 | chr8:71476018-71486067 |
| 2361 | Ang | NM_001161731.2 | chr14:51091076-51102009 | | 2458 | Ano9 | NM_178361.3 | chr7:141101218-141117806 |
| 2362 | Ang2 | NM_007449.2 | chr14:51195485-51195923 | | 2459 | Anp32a | NM_009672.3 | chr9:62341342-62378805 |
| 2363 | Ang3 | NM_001123394.2 | chr14:43957068-43963080 | | 2460 | Anp32b | NM_130889.2 | chr4:46451116-46472523 |
| 2364 | Ang4 | NM_177448.1 | chr14:51763891-51773590 | | 2461 | Anp32e | NM_001253757.1 | chr3:95979256-95947387 |
| 2365 | Ang5 | NM_007448.3 | chr14:43957068-43963080 | | 2462 | Anpep | NM_008486.2 | chr7:79821802-79842352 |
| 2366 | Ang6 | NM_001011876.2 | chr14:44001663-44006418 | | 2463 | Antxr1 | NM_054041.2 | chr6:87133852-87335775 |
| 2367 | Angel1 | NM_144524.2 | chr12:86700501-86726460 | | 2464 | Antxr2 | NM_133738.1 | chr5:97884687-98030962 |
| 2368 | Angel2 | NM_001199020.1 | chr1:190925107-190946491 | | 2465 | Antxrl | NM_172808.2 | chr14:34053469-34075999 |
| 2369 | Angpt1 | NM_001286062.1 | chr15:42424666-42676977 | | 2466 | Anxa1 | NM_010730.2 | chr19:20373433-20390671 |
| 2370 | Angpt2 | NM_007426.4 | chr8:18690262-18741562 | | 2467 | Anxa10 | NM_001136089.2 | chr8:62057041-62123193 |
| 2371 | Angpt4 | NM_009641.1 | chr2:151911331-151944654 | | 2468 | Anxa11 | NM_013469.2 | chr14:25842154-25886804 |
| 2372 | Angptl2 | NM_028333.2 | chr1:156839022-156861079 | | 2469 | Anxa13 | NM_027211.2 | chr15:58341463-58389274 |
| 2373 | Angptl2 | NM_011923.4 | chr2:33215960-33247714 | | 2470 | Anxa2 | NM_007585.3 | chr9:69453682-69491785 |
| 2374 | Angptl3 | NM_013913.4 | chr4:99030953-99038102 | | 2471 | Anxa3 | NM_013470.2 | chr5:96793384-96845968 |
| 2375 | Angptl4 | NM_020581.2 | chr17:33774899-33781575 | | 2472 | Anxa4 | NM_013471.2 | chr6:86736839-86793584 |
| 2376 | Angptl6 | NM_145154.2 | chr9:20873808-20879710 | | 2473 | Anxa5 | NM_009673.2 | chr3:36448923-36475887 |
| 2377 | Angptl7 | NM_001039654.4 | chr4:148495279-148500462 | | 2474 | Anxa6 | NM_001110211.1 | chr11:54978961-55033471 |
| 2378 | Ank | NM_020332.4 | chr15:27466676-27594907 | | 2475 | Anxa7 | NM_001110794.1 | chr14:20455260-20486133 |
| 2379 | Ank1 | NM_001110783.1 | chr8:22974835-23150497 | | 2476 | Anxa8 | NM_001281845.1 | chr14:34085978-34100568 |
| 2380 | Ank2 | NM_001034168.1 | chr3:126921606-126943386 | | 2477 | Anxa9 | NM_001085383.1 | chr3:95296093-95306804 |
| 2381 | Ank3 | NM_009670.4 | chr10:69925531-70027436 | | 2478 | Aoah | NM_001281854.1 | chr13:20794112-20851967 |
| 2382 | Ankar | NM_176980.4 | chr1:72465979-72700564 | | 2479 | Auc1 | NM_001161621.1 | chr6:48904985-48909187 |
| 2383 | Ankdd1b | NM_001042714.1 | chr3:96416133-96471160 | | 2480 | Aoc2 | NM_178932.1 | chr11:101325062-101329694 |
| 2384 | Ankef1 | NM_175667.4 | chr2:136532320-136555854 | | 2481 | Aoc3 | NM_009675.2 | chr11:101330605-101339430 |
| 2385 | Ankfn1 | NM_001080933.1 | chr11:89421085-89538555 | | 2482 | Aox1 | NM_009676.2 | chr1:58029968-58106410 |
| 2386 | Ankfy1 | NM_009671.5 | chr11:72690001-72772146 | | 2483 | Aox2 | NM_001008419.2 | chr1:58278326-58379264 |
| 2387 | Ankhd1 | NM_175375.3 | chr18:36560602-36658908 | | 2484 | Aox3 | NM_023617.2 | chr1:58131135-58210452 |
| 2388 | Ankib1 | NM_001003909.4 | chr5:3689998-3803124 | | 2485 | Aox4 | NM_023631.2 | chr1:58210396-58268596 |
| 2389 | Ankk1 | NM_172922.3 | chr9:49415221-49427021 | | 2486 | Ap1ar | NM_145964.2 | chr3:127807264-127837492 |
| 2390 | Ankle1 | NM_172756.3 | chr8:71410331-71410542 | | 2487 | Ap1b1 | NM_001243043.1 | chr11:4947520-5042794 |
| 2391 | Ankle2 | NM_001253814.1 | chr5:110231003-110256651 | | 2488 | Ap1g1 | NM_009677.6 | chr8:109778582-109864209 |
| 2392 | Ankmy1 | NM_172850.3 | chr1:92870128-92902906 | | 2489 | Ap1g2 | NM_007455.5 | chr14:55098834-55106593 |
| 2393 | Ankmy2 | NM_146153.3 | chr12:36167123-36197291 | | 2490 | Ap1m1 | NM_007456.4 | chr8:72240131-72257379 |
| 2394 | Ankra2 | NM_001271388.1 | chr13:98263075-98273918 | | 2491 | Ap1m2 | NM_001130300.1 | chr9:21295456-21312333 |
| 2395 | Ankrd1 | NM_013468.3 | chr19:36111964-36119844 | | 2492 | Ap1s1 | NM_007457.2 | chr5:137034993-137046060 |
| 2396 | Ankrd10 | NM_001167967.2 | chr8:11613840-11635757 | | 2493 | Ap1s2 | NM_001290378.1 | chrX:163909016-163933666 |
| 2397 | Ankrd11 | NM_001081379.2 | chr8:122883821-123042284 | | 2494 | Ap1s3 | NM_183027.2 | chr1:79606875-79671972 |
| 2398 | Ankrd12 | NM_001025572.1 | chr17:65997500-66077046 | | 2495 | Ap2a1 | NM_001077264.1 | chr7:44900372-44929490 |
| 2399 | Ankrd13a | NM_026715.2 | chr5:114775139-114805820 | | 2496 | Ap2a2 | NM_007459.3 | chr7:141562179-141633011 |
| 2400 | Ankrd13b | NM_172945.2 | chr11:77470486-77489678 | | 2497 | Ap2b1 | NM_001035854.2 | chr11:83302696-83405033 |
| 2401 | Ankrd13c | NM_001013806.1 | chr3:157947465-158006637 | | 2498 | Ap2m1 | NM_009679.3 | chr16:20535479-20544909 |
| 2402 | Ankrd13d | NM_026720.2 | chr19:4270179-4283137 | | 2499 | Ap2s1 | NM_198613.2 | chr7:16738443-16749290 |
| 2403 | Ankrd16 | NM_177268.4 | chr2:11777752-11790323 | | 2500 | Ap3b1 | NM_009680.3 | chr13:94358959-94565316 |
| 2404 | Ankrd17 | NM_030826.3 | chr5:90227165-90366185 | | 2501 | Ap3b2 | NM_021492.3 | chr7:81460398-81493925 |
| 2405 | Ankrd2 | NM_020033.1 | chr19:42036037-42045110 | | 2502 | Ap3d1 | NM_007460.1 | chr10:80706977-80742211 |
| 2406 | Ankrd22 | NM_024204.2 | chr19:34322548-34166041 | | 2503 | Ap3m1 | NM_018829.4 | chr14:21033741-21052442 |
| 2407 | Ankrd23 | NM_153502.4 | chr1:36580192-36535739 | | 2504 | Ap3m2 | NM_001122820.1 | chr8:22787353-22805654 |
| 2408 | Ankrd24 | NM_027480.3 | chr10:81628539-81647612 | | 2505 | Ap3s1 | NM_009681.5 | chr18:46741875-46790826 |
| 2409 | Ankrd26 | NM_001081112.1 | chr6:118502563-118562256 | | 2506 | Ap3s2 | NM_009682.3 | chr7:79875324-79920640 |
| 2410 | Ankrd27 | NM_145633.3 | chr7:35586246-35639237 | | 2507 | Ap4b1 | NM_001163552.1 | chr3:103809516-103822025 |
| 2411 | Ankrd28 | NM_001024604.2 | chr14:31700014-31830415 | | 2508 | Ap4e1 | NM_175550.3 | chr2:127008710-127069814 |
| 2412 | Ankrd29 | NM_001190371.1 | chr18:12302356-12305720 | | 2509 | Ap4m1 | NM_012139.4 | chr5:138172020-138178685 |
| 2413 | Ankrd32 | NM_134071.3 | chr13:77043087-77135468 | | 2510 | Ap4s1 | NM_021710.3 | chr12:51690965-51738939 |
| 2414 | Ankrd33 | NM_144790.1 | chr15:101115754-101120024 | | 2511 | Ap5b1 | NM_001033448.2 | chr19:5568073-5571261 |
| 2415 | Ankrd33b | NM_001164441.1 | chr5:31291478-31367759 | | 2512 | Ap5m1 | NM_144535.4 | chr14:49066494-49087723 |
| 2416 | Ankrd34a | NM_001024851.3 | chr3:96596635-96599778 | | 2513 | Ap5s1 | NM_001291031.1 | chr2:131210359-131213514 |
| 2417 | Ankrd34b | NM_175455.4 | chr3:146925968-92441658 | | 2514 | Ap5z1 | NM_172725.2 | chr5:142463930-142478715 |
| 2418 | Ankrd34c | NM_207260.2 | chr9:89723248-89738475 | | 2515 | Apaf1 | NM_001042058.1 | chr10:90989310-91082743 |
| 2419 | Ankrd35 | NM_001081339.1 | chr3:96670130-96691034 | | 2516 | Apba1 | NM_177034.3 | chr19:23758875-23949597 |
| 2420 | Ankrd36 | NM_023816.2 | chr11:569683-5689337 | | 2517 | Apba2 | NM_001291166.1 | chr7:64502137-64753876 |
| 2421 | Ankrd37 | NM_001039562.1 | chr8:45996907-45999850 | | 2518 | Apba3 | NM_018758.2 | chr10:81268171-81273247 |
| 2422 | Ankrd39 | NM_026241.4 | chr1:36536190-36547252 | | 2519 | Apbb1 | NM_001253885.1 | chr7:105558464-105581491 |
| 2423 | Ankrd40 | NM_027799.2 | chr11:94328000-94341847 | | 2520 | Apbb1ip | NM_019456.2 | chr2:22774326-22875653 |
| 2424 | Ankrd42 | NM_028665.4 | chr7:92584182-92637142 | | 2521 | Apbb2 | NM_001201413.1 | chr5:66298724-66618817 |

Fig.21 - 14

| | | | | | | |
|---|---|---|---|---|---|---|
| 2522 | Apbb3 | NM_146085.1 | chr18:36671155-36679366 | 2619 | Arfgef2 | NM_001085495.2 | chr2:166805580-166898051 |
| 2523 | Apc | NM_007462.3 | chr18:34220983-34322190 | 2620 | Arfip1 | NM_001081093.2 | chr3:84496092-84582625 |
| 2524 | Apc2 | NM_011789.2 | chr10:80301819-80318256 | 2621 | Arfip2 | NM_029802.4 | chr7:105634200-105640416 |
| 2525 | Apcdd1 | NM_133237.3 | chr18:62922326-62953195 | 2622 | Arfrp1 | NM_001165991.1 | chr2:181357689-181365404 |
| 2526 | Apcs | NM_011318.2 | chr1:172893960-172895054 | 2623 | Arg1 | NM_007482.3 | chr10:24915206-24927476 |
| 2527 | Apeh | NM_146226.2 | chr9:108085413-108094480 | 2624 | Arg2 | NM_009705.3 | chr12:79130787-79156301 |
| 2528 | Apela | NM_001297554.1 | chr8:65028417-65037336 | 2625 | Arglu1 | NM_176849.3 | chr8:8666575-8690537 |
| 2529 | Apex1 | NM_009687.2 | chr14:50924948-50927188 | 2626 | Arhgap1 | NM_001145902.1 | chr2:91650117-91672320 |
| 2530 | Apex2 | NM_029943.2 | chrX:150571506-150588155 | 2627 | Arhgap10 | NM_030113.2 | chr8:77250365-77517907 |
| 2531 | Aph1a | NM_146104.3 | chr3:95893920-95898592 | 2628 | Arhgap11a | NM_183416.3 | chr2:113831491-113848661 |
| 2532 | Aph1b | NM_177583.4 | chr9:66775486-66795423 | 2629 | Arhgap12 | NM_001039692.1 | chr18:6024449-6136098 |
| 2533 | Aph1c | NM_026774.3 | chr9:66814993-66834706 | 2630 | Arhgap15 | NM_001301831.1 | chr2:43748783-44395953 |
| 2534 | Api5 | NM_097466.3 | chr2:94411726-94438186 | 2631 | Arhgap15os | NR_040622.1 | chr2:44059237-44065324 |
| 2535 | Apip | NM_019735.4 | chr2:103073674-103092649 | 2632 | Arhgap17 | NM_001122840.1 | chr7:123279148-123369915 |
| 2536 | Apitd1 | NM_027263.2 | chr4:149128348-149137600 | 2633 | Arhgap18 | NM_176837.2 | chr10:26772511-26918648 |
| 2537 | Aplf | NM_001170489.1 | chr6:87628428-87672168 | 2634 | Arhgap19 | NM_001163495.1 | chr19:41766587-41802084 |
| 2538 | Apln | NM_013912.3 | chrX:48025145-48034852 | 2635 | Arhgap20 | NM_175535.3 | chr9:51765351-51853059 |
| 2539 | Aplnr | NM_011784.3 | chr2:85136359-85139923 | 2636 | Arhgap20os | NR_033560.1 | chr9:51894492-51875885 |
| 2540 | Aplp1 | NM_007467.3 | chr7:30434979-30445582 | 2637 | Arhgap21 | NM_001081364.3 | chr2:20847918-20967721 |
| 2541 | Aplp2 | NM_001102455.1 | chr9:31149556-31211815 | 2638 | Arhgap22 | NM_153800.4 | chr14:33216822-33369936 |
| 2542 | Apmap | NM_027977.2 | chr2:150583080-150608523 | 2639 | Arhgap23 | NM_021493.2 | chr11:97450159-97502400 |
| 2543 | Apoa1 | NM_009692.4 | chr9:46228629-46230469 | 2640 | Arhgap24 | NM_001286468.1 | chr5:102768809-102897937 |
| 2544 | Apoa1bp | NM_144897.3 | chr3:88056522-88058495 | 2641 | Arhgap25 | NM_001037727.2 | chr6:87458544-87533259 |
| 2545 | Apoa2 | NM_013474.2 | chr1:171225053-171226379 | 2642 | Arhgap26 | NM_175164.4 | chr18:38993144-39376285 |
| 2546 | Apoa4 | NM_007468.2 | chr9:46240843-46243458 | 2643 | Arhgap27 | NM_001205236.1 | chr11:103331483-103363692 |
| 2547 | Apoa5 | NM_080434.3 | chr9:46268607-46271919 | 2644 | Arhgap27os3 | NR_045346.1 | chr11:103454752-103350126 |
| 2548 | Apob | NM_009693.2 | chr12:7977676-8016839 | 2645 | Arhgap28 | NM_172964.4 | chr17:67842707-68004108 |
| 2549 | Apobec1 | NM_031343891.1 | chr6:122577791-122602444 | 2646 | Arhgap29 | NM_172525.2 | chr3:121953325-122016153 |
| 2550 | Apobec2 | NM_009694.3 | chr17:48419230-48432518 | 2647 | Arhgap30 | NM_001005508.2 | chr1:171388959-171410239 |
| 2551 | Apobec3 | NM_001160415.1 | chr15:79892407-79908429 | 2648 | Arhgap31 | NM_020260.2 | chr16:38598842-38713035 |
| 2552 | Apobec4 | NM_001081197.1 | chr1:152750550-152757544 | 2649 | Arhgap32 | NM_001195932.1 | chr9:32116135-32265511 |
| 2553 | Apobr | NM_138310.1 | chr7:126585007-126589092 | 2650 | Arhgap33 | NM_001289670.1 | chr7:30522225-30535060 |
| 2554 | Apoc1 | NM_001110009.2 | chr7:19689479-19692659 | 2651 | Arhgap33os | NR_036630.1 | chr7:30515121-30522193 |
| 2555 | Apoc2 | NM_001277944.1 | chr7:19671578-19677941 | 2652 | Arhgap36 | NM_172739.4 | chr7:16494472-16614993 |
| 2556 | Apoc3 | NM_001289755.1 | chr9:46233049-46235299 | 2653 | Arhgap36 | NM_001081123.1 | chrX:49470449-49500250 |
| 2557 | Apoc4 | NM_007385.3 | chr7:19678089-19681460 | 2654 | Arhgap39 | NM_001168288.1 | chr15:76723984-76818170 |
| 2558 | Apod | NM_007470.4 | chr16:31296191-31314808 | 2655 | Arhgap4 | NM_001162423.1 | chrX:73894351-73911798 |
| 2559 | Apoe | NM_009696.4 | chr7:19696243-19699188 | 2656 | Arhgap40 | NM_001145915.1 | chr2:158512795-158550628 |
| 2560 | Apof | NM_133997.2 | chr10:128267996-128270151 | 2657 | Arhgap42 | NM_027823.1 | chr9:8994952-9239013 |
| 2561 | Apoh | NM_013475.4 | chr11:108395296-108414396 | 2658 | Arhgap44 | NM_001099288.1 | chr11:65002038-65162961 |
| 2562 | Apol10a | NM_177744.4 | chr15:77477046-77491069 | 2659 | Arhgap5 | NM_009706.2 | chr12:52516076-52567851 |
| 2563 | Apol10b | NM_175884.1 | chr15:77584157-77596125 | 2660 | Arhgap6 | NM_001287530.1 | chrX:169112877-169304440 |
| 2564 | Apol11a | NM_001177533.1 | chr15:77508270-77517319 | 2661 | Arhgap8 | NM_001164627.1 | chr15:84720051-84772207 |
| 2565 | Apol11b | NM_001143686.1 | chr15:77633950-77643286 | 2662 | Arhgap9 | NM_001285785.1 | chr10:127321963-127329343 |
| 2566 | Apol6 | NM_001163624.1 | chr15:77045074-77052351 | 2663 | Arhgdia | NM_133796.7 | chr10:120577234-120581620 |
| 2567 | Apol7a | NM_001164640.1 | chr15:77388216-77399110 | 2664 | Arhgdib | NM_007486.5 | chr6:136923660-136941756 |
| 2568 | Apol7b | NM_001024848.2 | chr15:77422028-77447460 | 2665 | Arhgdig | NM_008113.3 | chr17:26199182-26201350 |
| 2569 | Apol7c | NM_175914.4 | chr15:77524866-77533315 | 2666 | Arhgef1 | NM_001130150.1 | chr7:24902985-24926591 |
| 2570 | Apol7d | NR_040308.1 | chr1:71663334-71662843 | 2667 | Arhgef10 | NM_001037736.2 | chr8:14911662-15001085 |
| 2571 | Apol7e | NM_001348302.1 | chr15:77698888-77719288 | 2668 | Arhgef10l | NM_001112722.1 | chr4:140514484-140665905 |
| 2572 | Apol8 | NM_001081970.1 | chr15:77748612-77755229 | 2669 | Arhgef11 | NM_001003912.1 | chr3:87618750-87738033 |
| 2573 | Apol9a | NM_001162883.1 | chr15:77403788-77411080 | 2670 | Arhgef12 | NM_027144.2 | chr9:42963841-43105718 |
| 2574 | Apol9b | NM_001168660.1 | chr15:77729120-77736382 | 2671 | Arhgef15 | NM_175566.3 | chr11:68943153-68956858 |
| 2575 | Apold1 | NM_001109914.1 | chr6:134982000-134986836 | 2672 | Arhgef16 | NM_001112744.1 | chr4:154278469-154299895 |
| 2576 | Apom | NM_133892.3 | chr17:33928996-35131752 | 2673 | Arhgef17 | NM_001081116.1 | chr7:100869745-100932181 |
| 2577 | Apon | NM_133996.3 | chr10:128254130-128295901 | 2674 | Arhgef18 | NM_133962.3 | chr8:3393907-3456600 |
| 2578 | Apoo | NM_001199337.1 | chrX:94367153-94417092 | 2675 | Arhgef19 | NM_172520.2 | chr4:141242883-141257562 |
| 2579 | Apool | NM_026565.3 | chrX:112311351-112372755 | 2676 | Arhgef2 | NM_001198911.1 | chr3:88616206-88648052 |
| 2580 | Apool-ps | NR_004438.1 | chrX:94367123-94398202 | 2677 | Arhgef25 | NM_001166413.1 | chr10:127182520-127189823 |
| 2581 | Apopt1 | NM_001163388.1 | chr12:111713268-111755055 | 2678 | Arhgef26 | NM_001081295.1 | chr3:62338776-62462221 |
| 2582 | App | NM_001198463.1 | chr16:84954435-85173707 | 2679 | Arhgef28 | NM_012026.2 | chr13:97898594-98206165 |
| 2583 | Appbp2 | NM_025825.3 | chr11:85191309-85235120 | 2680 | Arhgef3 | NM_001289636.1 | chr14:27143992-27403911 |
| 2584 | Appl1 | NM_145218.7 | chr14:26918987-26970651 | 2681 | Arhgef33 | NM_001145452.1 | chr17:80307406-80388689 |
| 2585 | Appl2 | NM_145220.2 | chr10:83600033-83648664 | 2682 | Arhgef37 | NM_177828.4 | chr18:61493793-61536536 |
| 2586 | Aprt | NM_009698.2 | chr8:122574636-122576907 | 2683 | Arhgef38 | NM_029953.1 | chr3:133159530-133234889 |
| 2587 | Aptx | NM_001025444.3 | chr4:40682077-40703194 | 2684 | Arhgef39 | NM_001013377.2 | chr4:43496143-43499660 |
| 2588 | Aqp1 | NM_007472.2 | chr6:55336296-55348555 | 2685 | Arhgef4 | NM_183019.2 | chr1:34801721-34812754 |
| 2589 | Aqp11 | NM_175105.3 | chr7:97726378-97738247 | 2686 | Arhgef40 | NM_001145921.1 | chr14:51984832-52006247 |
| 2590 | Aqp12 | NM_001159626.1 | chr1:93006333-93012269 | 2687 | Arhgef5 | NM_133674.1 | chr6:43265643-43289320 |
| 2591 | Aqp2 | NM_009699.3 | chr15:99579055-99584545 | 2688 | Arhgef6 | NM_152801.2 | chrX:57231484-57338729 |
| 2592 | Aqp3 | NM_016689.2 | chr4:41092723-41098183 | 2689 | Arhgef7 | NM_001113517.1 | chr8:11728104-11827152 |
| 2593 | Aqp4 | NM_009700.2 | chr18:15389393-15403684 | 2690 | Arhgef9 | NM_001033293.9 | chrX:95048934-95166539 |
| 2594 | Aqp5 | NM_009701.4 | chr15:99591027-99594829 | 2691 | Arid1a | NM_001080819.1 | chr4:133679007-133753611 |
| 2595 | Aqp6 | NM_175096.2 | chr15:99601369-99605477 | 2692 | Arid1b | NM_001085355.1 | chr17:4995073-5347636 |
| 2596 | Aqp7 | NM_007473.4 | chr4:41033073-41048136 | 2693 | Arid2 | NM_175251.4 | chr15:96287521-96405463 |
| 2597 | Aqp8 | NM_001109045.1 | chr7:123462293-123468003 | 2694 | Arid3a | NM_001288625.1 | chr10:79927340-79955018 |
| 2598 | Aqp9 | NM_027218431 | chr9:71110658-71162633 | 2695 | Arid3b | NM_014689.2 | chr9:57790504-57834234 |
| 2599 | Aqr | NM_001290788.1 | chr2:114105161-114175339 | 2696 | Arid3c | NM_001017362.2 | chr4:41723836-41731142 |
| 2600 | Ar | NM_013476.3 | chrX:98148756-98323218 | 2697 | Arid4a | NM_001081195.1 | chr12:71015966-71099351 |
| 2601 | Araf | NM_001159645.1 | chrX:20848542-20852905 | 2698 | Arid4b | NM_194262.2 | chr13:14063783-14199603 |
| 2602 | Arap1 | NM_001040111.1 | chr7:101348068-101412586 | 2699 | Arid5a | NM_001172205.1 | chr1:36307732-36324029 |
| 2603 | Arap2 | NM_178407.3 | chr5:62602445-62766177 | 2700 | Arid5b | NM_023598.2 | chr10:68095592-68278726 |
| 2604 | Arap3 | NM_001205336.1 | chr18:37972622-37998969 | 2701 | Arih1 | NM_019927.2 | chr9:59388553-59486374 |
| 2605 | Arc | NM_001276684.1 | chr15:74669080-74672570 | 2702 | Arih2 | NM_013790.4 | chr9:108602942-108649380 |
| 2606 | Arcn1 | NM_145985.4 | chr9:44742143-44767808 | 2703 | Arl1 | NM_025859.3 | chr10:88731413-88743202 |
| 2607 | Areg | NM_009704.4 | chr5:91139598-91148432 | 2704 | Arl10 | NM_019968.2 | chr13:54575012-54581128 |
| 2608 | Areτ1 | NM_178065.4 | chr12:84918148-84970886 | 2705 | Arl11 | NM_177337.3 | chr14:61309752-61311936 |
| 2609 | Arf1 | NM_001130408.1 | chr11:59211411-59228162 | 2706 | Arl13a | NM_028947.1 | chrX:134187500-134208030 |
| 2610 | Arf2 | NM_007477.5 | chr11:103966870-103985350 | 2707 | Arl13b | NM_026573.3 | chr16:62793688-62847040 |
| 2611 | Arf3 | NM_007478.3 | chr15:97037625-98763118 | 2708 | Arl14 | NM_027843.1 | chr3:69222418-69223618 |
| 2612 | Arf4 | NM_007479.3 | chr14:26638196-26667258 | 2709 | Arl14ep | NM_001025102.1 | chr2:106962528-106974397 |
| 2613 | Arf5 | NM_007480.1 | chr6:28423639-28426499 | 2710 | Arl14epl | NM_001033446.2 | chr18:46921814-46934222 |
| 2614 | Arf6 | NM_007481.3 | chr12:69372149-69375980 | 2711 | Arl15 | NM_172595.4 | chr13:113794507-114157461 |
| 2615 | Arfgap1 | NM_001177706.1 | chr2:180967299-180982524 | 2712 | Arl16 | NM_197995.2 | chr11:120464325-120467600 |
| 2616 | Arfgap2 | NM_001166024.1 | chr2:91265114-91277371 | 2713 | Arl2 | NM_019722.3 | chr9:6134368-6141137 |
| 2617 | Arfgap3 | NM_025445.4 | chr15:83299739-83350247 | 2714 | Arl2bp | NM_024191.2 | chr8:94666599-94674457 |
| 2618 | Arfgef1 | NM_001192430.1 | chr1:10137506-10232670 | 2715 | Arl3 | NM_019718.2 | chr19:46531108-46573085 |

Fig.21 - 15

| | | | | | | | |
|---|---|---|---|---|---|---|---|
| 2716 | Arl4a | NM_001039515.1 | chr12:40033290-40037987 | 2813 | Ascc3 | NM_198007.2 | chr10:50592668-50851202 |
| 2717 | Arl4c | NM_177305.4 | chr1:88698225-88702191 | 2814 | Ascl1 | NM_008553.4 | chr10:87491040-87493660 |
| 2718 | Arl4d | NM_025404.3 | chr11:101665540-101667832 | 2815 | Ascl2 | NM_008554.3 | chr7:142966821-142969264 |
| 2719 | Arl5a | NM_182994.2 | chr2:52397950-52424874 | 2816 | Ascl3 | NM_020051.1 | chr7:109727464-109731732 |
| 2720 | Arl5b | NM_029466.4 | chr2:15055361-15079191 | 2817 | Ascl4 | NM_001163614.1 | chr10:85928490-85929647 |
| 2721 | Arl5c | NM_207231.1 | chr11:97989579-97996173 | 2818 | Ascl5 | NM_001270609.1 | chr1:136050803-136051370 |
| 2722 | Arl6 | NM_019665.3 | chr16:59613320-59639339 | 2819 | Asf1a | NM_025541.3 | chr10:53596960-53609215 |
| 2723 | Arl6ip1 | NM_019419.2 | chr7:118118889-118129625 | 2820 | Asf1b | NM_024184.2 | chr8:83855693-83970195 |
| 2724 | Arl6ip4 | NM_144509.2 | chr2:124116107-124118195 | 2821 | Asgr1 | NM_001291131.1 | chr11:70054123-70057895 |
| 2725 | Arl6ip5 | NM_022992.2 | chr6:97210791-97233315 | 2822 | Asgr2 | NM_007493.3 | chr11:70092643-70106186 |
| 2726 | Arl6ip6 | NM_022989.4 | chr2:53192083-53219221 | 2823 | Ash1l | NM_138679.5 | chr3:88965811-89079375 |
| 2727 | Arl8a | NM_026823.2 | chr1:135146833-135156268 | 2824 | Ash2l | NM_001080793.2 | chr8:25816000-25847694 |
| 2728 | Arl8b | NM_026011.3 | chr6:108783058-108823723 | 2825 | Asic1 | NM_001289791.1 | chr15:99691754-99701130 |
| 2729 | Arl9 | NM_208935.1 | chr5:77004054-77009478 | 2826 | Asic2 | NM_001034013.2 | chr11:80850164-81968396 |
| 2730 | Armc1 | NM_026840.2 | chr3:19132143-19163065 | 2827 | Asic3 | NM_183000.2 | chr5:24413450-24417634 |
| 2731 | Armc10 | NM_026034.4 | chr5:21645983-21662592 | 2828 | Asic4 | NM_183022.3 | chr1:75450509-75474340 |
| 2732 | Armc12 | NM_026290.3 | chr17:28530860-28538975 | 2829 | Asic5 | NM_021370.2 | chr3:81996921-82021233 |
| 2733 | Armc2 | NM_001034858.3 | chr10:41914989-42018382 | 2830 | Asl | NM_133768.4 | chr5:130011502-130024331 |
| 2734 | Armc3 | NM_001081083.2 | chr2:19199117-19310243 | 2831 | Asmt | NM_001199212.1 | chrX:170672844-170678054 |
| 2735 | Armc4 | NM_001081393.1 | chr18:7088232-7297901 | 2832 | Asna1 | NM_019652.1 | chr8:85017930-85025278 |
| 2736 | Armc5 | NM_146205.2 | chr7:128237356-128245100 | 2833 | Asns | NM_012055.3 | chr6:7675170-7693182 |
| 2737 | Armc6 | NM_133972.2 | chr8:70220192-70234422 | 2834 | Asnsd1 | NM_001290984.1 | chr1:53344616-53352752 |
| 2738 | Armc7 | NM_177778.4 | chr11:115475976-115490466 | 2835 | Aspa | NM_023113.5 | chr11:73304987-73324637 |
| 2739 | Armc8 | NM_001166138.1 | chr9:99518244-99568899 | 2836 | Aspdh | NM_026690.1 | chr7:44465434-44467751 |
| 2740 | Armc9 | NM_027456.2 | chr1:86154779-86252491 | 2837 | Aspg | NM_001081169.1 | chr12:112106682-112127573 |
| 2741 | Armcx1 | NM_001166377.1 | chrX:134721937-134721912 | 2838 | Asph | NM_001177849.1 | chr4:9449084-9669162 |
| 2742 | Armcx2 | NM_001166397.1 | chrX:134804141-134809221 | 2839 | Asphd1 | NM_001039645.1 | chr7:126946007-126949581 |
| 2743 | Armcx3 | NM_027870.3 | chrX:134756667-134761456 | 2840 | Asphd2 | NM_028386.1 | chr5:112385444-112392213 |
| 2744 | Armcx4 | NM_001202500.3 | chrX:134686518-134697772 | 2841 | Aspm | NM_009790.4 | chr1:139454772-139494088 |
| 2745 | Armcx5 | NM_001009575.5 | chrX:135742691-135747326 | 2842 | Aspn | NM_001172481.1 | chr13:49544442-49567562 |
| 2746 | Armcx6 | NM_001007578.2 | chrX:134748454-134751419 | 2843 | Asprv1 | NM_026414.2 | chr6:86628173-86629704 |
| 2747 | Armt | NM_001037737.2 | chr3:95434389-95497239 | 2844 | Aspsc1 | NM_001164224.1 | chr11:120676660-120709446 |
| 2748 | Arnt2 | NM_007488.3 | chr7:84246274-84410038 | 2845 | Asrgl1 | NM_025610.3 | chr19:9311718-9135586 |
| 2749 | Arnt | NM_001243064.1 | chr7:13207464-113314126 | 2846 | Ass1 | NM_007494.3 | chr2:31470769-31520670 |
| 2750 | Arnt2 | NM_001289679.1 | chr6:146805529-146833529 | 2847 | Aste1 | NM_001164828.1 | chr9:105400787-105405756 |
| 2751 | Arpc1a | NM_019767.2 | chr5:145083869-145108756 | 2848 | Astl | NM_001291303.1 | chr2:127341635-127357656 |
| 2752 | Arpc1b | NM_023142.2 | chr5:145114425-145128186 | 2849 | Astn1 | NM_001205204.1 | chr1:158362303-158691786 |
| 2753 | Arpc2 | NM_029711.1 | chr1:74236549-74268213 | 2850 | Astn2 | NM_019514.3 | chr4:65380802-66404483 |
| 2754 | Arpc3 | NM_019824.3 | chr5:122391927-122406178 | 2851 | Asun | NM_138757.1 | chr6:146549631-146557185 |
| 2755 | Arpc4 | NM_001170485.1 | chr6:113378117-113390447 | 2852 | Asxl1 | NM_001039939.1 | chr2:153346138-153404007 |
| 2756 | Arpc5 | NM_026369.2 | chr1:152766541-152775580 | 2853 | Asxl2 | NM_001270988.1 | chr12:3426856-3506849 |
| 2757 | Arpc5l | NM_028809.1 | chr2:39008138-39015872 | 2854 | Asxl3 | NM_001167777.1 | chr18:22343088-22530227 |
| 2758 | Arpp19 | NM_001142695.1 | chr9:75037619-75060313 | 2855 | Asz1 | NM_023729.3 | chr6:18050963-18109061 |
| 2759 | Arpp21 | NM_001177615.1 | chr9:112180031-112187926 | 2856 | Atad1 | NM_026487.3 | chr19:32672562-32712298 |
| 2760 | Arr3 | NM_133765.3 | chrX:100605496-100618493 | 2857 | Atad2 | NM_027435.2 | chr15:58094046-58135082 |
| 2761 | Arrb1 | NM_177231.2 | chr7:99535485-99606771 | 2858 | Atad2b | NM_001099628.1 | chr12:4917352-5047410 |
| 2762 | Arrb2 | NM_001271353.1 | chr11:70432579-70440828 | 2859 | Atad3a | NM_179203.3 | chr4:155740639-155761098 |
| 2763 | Arrdc1 | NM_001162485.1 | chr2:24925351-24935281 | 2860 | Atad3aos | NR_027971.1 | chr4:155776193-155782266 |
| 2764 | Arrdc2 | NM_027560.1 | chr8:70835137-70839720 | 2861 | Atad5 | NM_001029856.2 | chr11:80089399-80135791 |
| 2765 | Arrdc3 | NM_001042591.1 | chr3:88884421-80896043 | 2862 | Atat1 | NM_001142744.1 | chr17:35887597-35910068 |
| 2766 | Arrdc4 | NM_001042592.2 | chr7:68736993-68749238 | 2863 | Atcay | NM_178662.3 | chr10:81204512-81236779 |
| 2767 | Arrdc5 | NM_029799.1 | chr17:56294110-56300286 | 2864 | Atcayos | NR_015477.1 | chr10:81194690-81208370 |
| 2768 | Arsa | NM_009713.4 | chr15:89472475-89477424 | 2865 | Ate1 | NM_001029895.3 | chr7:130391493-130520369 |
| 2769 | Arsb | NM_009712.3 | chr13:93771678-93943016 | 2866 | Atf1 | NM_007497.3 | chr15:100227858-100261248 |
| 2770 | Arsg | NM_001164971.1 | chr11:109543710-109573329 | 2867 | Atf2 | NM_001025093.2 | chr2:73816508-73892639 |
| 2771 | Arsi | NM_001038499.1 | chr18:60912239-60917768 | 2868 | Atf3 | NM_007498.3 | chr1:191170296-191183333 |
| 2772 | Arsj | NM_173451.3 | chr3:126363851-126440374 | 2869 | Atf4 | NM_001287180.1 | chr15:80255183-80257545 |
| 2773 | Arsk | NM_029847.4 | chr13:76060421-76098660 | 2870 | Atf5 | NM_030693.2 | chr7:44812255-44815658 |
| 2774 | Art1 | NM_009710.4 | chr7:102101742-102111148 | 2871 | Atf6 | NM_001081304.1 | chr1:170704456-170867771 |
| 2775 | Art2a-ps | NM_007490.1 | chr7:101552775-101555802 | 2872 | Atf6b | NM_017406.4 | chr17:34647145-34655074 |
| 2776 | Art2b | NM_019915.2 | chr7:101578859-101581161 | 2873 | Atf7 | NM_001310066.1 | chr15:102536643-102625421 |
| 2777 | Art3 | NM_181728.3 | chr5:92388133-92414627 | 2874 | Atf7ip | NM_019426.2 | chr6:136518850-136607379 |
| 2778 | Art4 | NM_026629.2 | chr6:136848450-136857600 | 2875 | Atf7ip2 | NM_029253.1 | chr16:10192905-10237287 |
| 2779 | Art5 | NM_001291354.1 | chr7:102096878-102100229 | 2876 | Atg10 | NM_025770.3 | chr13:90935348-91223987 |
| 2780 | Artn | NM_001284191.1 | chr4:117926159-117929763 | 2877 | Atg101 | NM_026566.2 | chr15:101284300-101290934 |
| 2781 | Arv1 | NM_026855.4 | chr8:124722158-124734123 | 2878 | Atg12 | NM_026217.3 | chr18:46732416-46741579 |
| 2782 | Arvcf | NM_001272028.1 | chr16:18380732-18407074 | 2879 | Atg13 | NM_145528.3 | chr2:91674613-91710592 |
| 2783 | Arx | NM_007492.4 | chrX:93286506-93298355 | 2880 | Atg14 | NM_172599.4 | chr14:47540892-47568434 |
| 2784 | Arxes1 | NM_029541.3 | chrX:136033460-136034946 | 2881 | Atg16l1 | NM_001205391.1 | chr1:87756010-87792428 |
| 2785 | Arxes2 | NM_029823.2 | chrX:135993819-135995359 | 2882 | Atg16l2 | NM_001111191.1 | chr7:101289615-101302088 |
| 2786 | As3mt | NM_020577.2 | chr19:46707442-46741095 | 2883 | Atg2a | NM_194348.3 | chr19:6241667-6262304 |
| 2787 | Asah1 | NM_019734.3 | chr8:41340642-41374697 | 2884 | Atg2b | NM_029654.4 | chr12:105613539-105685241 |
| 2788 | Asah2 | NM_018830.1 | chr19:31984650-32103140 | 2885 | Atg3 | NM_026402.3 | chr16:45158828-45188538 |
| 2789 | Asap1 | NM_001276461.1 | chr15:64086839-64382919 | 2886 | Atg4a | NM_174875.3 | chr3:103643952-103646608 |
| 2790 | Asap2 | NM_001004264.2 | chr12:21111755-21270171 | 2887 | Atg4b | NM_174874.3 | chr1:93755032-93789529 |
| 2791 | Asap3 | NM_001008232.2 | chr4:136206364-136246573 | 2888 | Atg4c | NM_001145967.1 | chr4:99194146-99259787 |
| 2792 | Asb1 | NM_001053425.1 | chr1:91540564-91559590 | 2889 | Atg4d | NM_153583.10 | chr9:21265284-21274837 |
| 2793 | Asb10 | NM_080444.5 | chr5:24532696-24540457 | 2890 | Atg5 | NM_053069.6 | chr10:44268338-44364299 |
| 2794 | Asb11 | NM_001253717.1 | chrX:164436993-164459170 | 2891 | Atg7 | NM_001253717.1 | chr6:114643096-114866614 |
| 2795 | Asb12 | NM_080858.3 | chrX:95470198-95478129 | 2892 | Atg9a | NM_001003917.4 | chr1:75180860-75192010 |
| 2796 | Asb13 | NM_001267724.1 | chr13:3634031-3651779 | 2893 | Atg9b | NM_001002897.3 | chr5:24384180-24392143 |
| 2797 | Asb14 | NM_001170464.1 | chr14:26894603-26915257 | 2894 | Athl1 | NM_145387.4 | chr7:140941580-140947658 |
| 2798 | Asb15 | NM_080847.3 | chr6:24528143-24573164 | 2895 | Atic | NM_026195.3 | chr1:71557155-71579403 |
| 2799 | Asb16 | NM_148953.2 | chr11:102268822-102278061 | 2896 | Atl1 | NM_178628.5 | chr12:69893104-69964085 |
| 2800 | Asb17 | NM_025758.4 | chr3:153844246-153853615 | 2897 | Atl2 | NM_001286647.1 | chr17:79848389-79896123 |
| 2801 | Asb17os | NR_040373.1 | chr3:153850378-153882424 | 2898 | Atl3 | NM_001163505.1 | chr19:7494089-7538609 |
| 2802 | Asb18 | NM_139152.1 | chr1:89962677-90014577 | 2899 | Atm | NM_007499.2 | chr9:53437121-53536671 |
| 2803 | Asb2 | NM_023049.1 | chr12:103321141-103356001 | 2900 | Atmin | NM_177700.4 | chr8:116943392-116960445 |
| 2804 | Asb3 | NM_023906.3 | chr11:30954397-31102704 | 2901 | Atn1 | NM_007881.4 | chr6:124742543-124756487 |
| 2805 | Asb4 | NM_023048.5 | chr6:5383385-5433023 | 2902 | Atoh1 | NM_007500.4 | chr6:64729145-64731235 |
| 2806 | Asb5 | NM_029569.3 | chr8:54555330-54587836 | 2903 | Atoh7 | NM_016864.1 | chr10:63100155-63100605 |
| 2807 | Asb6 | NM_133346.2 | chr2:30823097-30828300 | 2904 | Atoh8 | NM_153778.3 | chr6:72206176-72235577 |
| 2808 | Asb7 | NM_080484.2 | chr7:66644566-66689561 | 2905 | Atox1 | NM_009720.2 | chr11:55446642-55461138 |
| 2809 | Asb8 | NM_001170710.1 | chr15:98134639-98145702 | 2906 | Atp10a | NM_009728.2 | chr7:58658201-58829426 |
| 2810 | Asb9 | NM_027027.2 | chrX:164497902-164509752 | 2907 | Atp10b | NM_176999.3 | chr11:43149876-43262286 |
| 2811 | Ascc1 | NM_001199187.1 | chr10:60003326-60099990 | 2908 | Atp10d | NM_153389.3 | chr5:72203342-72298758 |
| 2812 | Ascc2 | NM_029291.1 | chr11:4637792-4683286 | 2909 | Atp11a | NM_015804.3 | chr8:12757015-12868728 |

Fig.21 - 16

| | | | | | | | | |
|---|---|---|---|---|---|---|---|---|
| 2910 | Atp1b | NM_029570.3 | chr3:35794137-35896276 | 3007 | Atxn7l1 | NM_001033436.3 | chr12:33302514-33368277 |
| 2911 | Atp1c | NM_001001798.2 | chrX:60223289-60403981 | 3008 | Atxn7l2 | NM_001289545.1 | chr3:108202227-108210527 |
| 2912 | Atp12a | NM_138652.2 | chr14:56365067-56388551 | 3009 | Atxn7l3 | NM_001098836.1 | chr1:102289299-102296629 |
| 2913 | Atp13a1 | NM_133224.2 | chr8:69791162-69807748 | 3010 | Atxn7l3b | NM_001033474.2 | chr10:112925427-112929026 |
| 2914 | Atp13a2 | NM_001164366.1 | chr4:140986872-141007701 | 3011 | AU015228 | NM_001289265.1 | chr2:136100393-130101375 |
| 2915 | Atp13a3 | NM_001128094.1 | chr16:30312423-30388530 | 3012 | AU015791 | NR_102381.1 | chr12:105513432-105515248 |
| 2916 | Atp13a4 | NM_001164612.1 | chr16:29398037-29541483 | 3013 | AU015836 | NR_028320.1 | chrX:93968655-93975470 |
| 2917 | Atp13a5 | NM_001284375.1 | chr16:29231913-29378732 | 3014 | AU016765 | NR_045899.1 | chr17:64514088-64555590 |
| 2918 | Atp1a1 | NM_144900.2 | chr3:101576218-101604707 | 3015 | AU018091 | NM_001004153.2 | chr7:3154658-3169203 |
| 2919 | Atp1a2 | NM_178405.3 | chr1:172271708-172298064 | 3016 | AU018829 | NM_001200055.1 | chr5:82183-95195342 |
| 2920 | Atp1a3 | NM_001290469.1 | chr7:24978168-25005937 | 3017 | AU019823 | NM_001134902.1 | chr9:50605239-50617464 |
| 2921 | Atp1a4 | NM_013734.1 | chr1:172223507-172258424 | 3018 | AU019990 | NR_033468.1 | chr2:132598199-132653064 |
| 2922 | Atp1b1 | NM_009721.6 | chr1:164437098-164458355 | 3019 | AU021063 | NR_045936.1 | chr15:101221246-101222155 |
| 2923 | Atp1b2 | NM_013415.5 | chr11:69599749-69605960 | 3020 | AU021092 | NM_001032220.3 | chr16:5211818-5222299 |
| 2924 | Atp1b3 | NM_007502.4 | chr9:96332674-96364299 | 3021 | AU022252 | NM_001012400.2 | chr4:119225137-119232724 |
| 2925 | Atp1b4 | NM_001290389.1 | chrX:38316121-38336784 | 3022 | AU022751 | NM_001033211.3 | chrX:6081217-6083420 |
| 2926 | Atp2a1 | NM_007504.2 | chr7:126445859-126463073 | 3023 | AU022754 | NR_040433.1 | chr15:85581141-85593708 |
| 2927 | Atp2a2 | NM_001110140.3 | chr5:122456323-122502225 | 3024 | AU022793 | NR_045719.1 | chr15:39962648-39967515 |
| 2928 | Atp2a3 | NM_001163336.1 | chr11:72961168-72993043 | 3025 | AU023762 | NR_040760.1 | chr9:113496749-113587152 |
| 2929 | Atp2b1 | NM_026482.2 | chr10:98915151-99026143 | 3026 | AU040320 | NM_001035525.1 | chr4:126753554-126869694 |
| 2930 | Atp2b2 | NM_001036684.2 | chr6:113745667-113891376 | 3027 | AU040972 | NR_045305.1 | chr11:79481722-79484031 |
| 2931 | Atp2b3 | NM_177236.4 | chrX:73503085-73573270 | 3028 | AU041133 | NM_001163064.1 | chr10:82128012-82153086 |
| 2932 | Atp2b4 | NM_001167949.2 | chr1:133702673-133753747 | 3029 | Auh | NM_016709.2 | chr3:52835109-52929677 |
| 2933 | Atp2c1 | NM_001253831.1 | chr9:105411361-105521257 | 3030 | Aup1 | NM_007517.4 | chr6:83054520-83057682 |
| 2934 | Atp2c2 | NM_026922.1 | chr8:119700008-119757718 | 3031 | Aurka | NM_001291385.1 | chr2:172356189-172370570 |
| 2935 | Atp4a | NM_001290627.1 | chr7:30712208-30725534 | 3032 | Aurkaip1 | NM_025338.4 | chr4:155831268-155833098 |
| 2936 | Atp4b | NM_009724.2 | chr8:13386208-13396778 | 3033 | Aurkb | NM_011496.2 | chr11:69045642-69051662 |
| 2937 | Atp5a1 | NM_007505.2 | chr18:77773767-77782868 | 3034 | Aurkc | NM_001080965.1 | chr7:6995384-7003091 |
| 2938 | Atp5b | NM_016774.3 | chr10:128083306-128090388 | 3035 | Auts2 | NM_177047.3 | chr5:131437681-132542343 |
| 2939 | Atp5c1 | NM_001112738.1 | chr2:10056030-10080510 | 3036 | AV099307 | NR_038349.1 | chr3:120850855-120866690 |
| 2940 | Atp5d | NM_025313.2 | chr10:80142314-80145818 | 3037 | AV051173 | NR_040442.1 | chr4:116684964-116686022 |
| 2941 | Atp5e | NM_025983.3 | chr2:174461074-174464101 | 3038 | AV320801 | NM_177918.1 | chrX:135167623-135504594 |
| 2942 | Atp5f1 | NM_009725.4 | chr3:105942677-105960248 | 3039 | Aven | NM_001165935.1 | chr2:112559681-112631253 |
| 2943 | Atp5g1 | NM_001161419.1 | chr11:96072792-96075631 | 3040 | Avil | NM_009635.3 | chr10:127000708-127020994 |
| 2944 | Atp5g2 | NM_026468.2 | chr15:102662867-102671047 | 3041 | Avl9 | NM_030235.1 | chr6:56714904-56781911 |
| 2945 | Atp5g3 | NM_175015.3 | chr2:73908446-73911326 | 3042 | Avp | NM_009732.2 | chr2:130580619-130582588 |
| 2946 | Atp5h | NM_027862.1 | chr11:115415686-115419919 | 3043 | Avpi1 | NM_027106.4 | chr19:42123274-42128993 |
| 2947 | Atp5j | NM_016755.3 | chr16:84827870-84835625 | 3044 | Avpr1a | NM_016847.2 | chr10:122448498-122453453 |
| 2948 | Atp5j2 | NM_020582.2 | chr5:145183705-145191592 | 3045 | Avpr1b | NM_011924.2 | chr1:131599113-131612000 |
| 2949 | Atp5k | NM_007507.2 | chr5:108433252-108434378 | 3046 | Avpr2 | NM_001276298.1 | chrX:73892101-73894428 |
| 2950 | Atp5l | NM_013795.5 | chr9:44913247-44920742 | 3047 | AW011738 | NR_030671.1 | chr4:156203283-156206028 |
| 2951 | Atp5o | NM_138597.2 | chr16:91925222-91931630 | 3048 | AW046200 | NR_040698.1 | chr8:57651752-57663430 |
| 2952 | Atp5s | NM_026536.1 | chr12:69724961-69744658 | 3049 | AW112010 | NR_102366.1 | chr19:11047611-11050566 |
| 2953 | Atp5sl | NM_001290487.1 | chr7:25619413-25625550 | 3050 | AW146154 | NM_001033530.3 | chr7:41478873-41499890 |
| 2954 | Atp6ap1 | NM_018794.4 | chrX:74297096-74304721 | 3051 | AW209491 | NM_001104646.1 | chr13:14630244-14638202 |
| 2955 | Atp6ap1l | NM_001145879.1 | chr13:90883448-90905355 | 3052 | AW495222 | NR_045086.1 | chr13:93760699-93719175 |
| 2956 | Atp6ap2 | NM_027438.2 | chrX:12587758-12617051 | 3053 | AW549542 | NR_045702.1 | chr5:119570128-119580358 |
| 2957 | Atp6v0a1 | NM_001243049.1 | chr11:101009451-101063717 | 3054 | AW549877 | NM_145930.2 | chr15:3982034-3995752 |
| 2958 | Atp6v0a2 | NM_011596.5 | chr5:124629051-124724455 | 3055 | AW551984 | NM_001199556.1 | chr9:39587895-39608652 |
| 2959 | Atp6v0a4 | NM_080467.3 | chr6:38048482-38124586 | 3056 | AW554918 | NM_001083532.3 | chr18:25169019-25467321 |
| 2960 | Atp6v0b | NM_033617.3 | chr4:117884329-117887329 | 3057 | AW822252 | NR_110489.1 | chrX:53696921-53716578 |
| 2961 | Atp6v0c | NM_009729.3 | chr17:24163865-24169429 | 3058 | Awat1 | NM_001081136.1 | chrX:100572246-100578206 |
| 2962 | Atp6v0c-ps2 | NR_037854.1 | chr17:24163864-24169393 | 3059 | Awat2 | NM_001290395.1 | chrX:100402221-100442717 |
| 2963 | Atp6v0d1 | NM_013477.3 | chr8:105524469-105566040 | 3060 | Axin1 | NM_001159598.1 | chr17:26138685-26195811 |
| 2964 | Atp6v0d2 | NM_175406.3 | chr4:19876837-19922566 | 3061 | Axin2 | NM_015732.4 | chr11:108920348-108950781 |
| 2965 | Atp6v0e | NM_025272.2 | chr17:26676395-26699646 | 3062 | Axl | NM_001190974.1 | chr7:25756499-25788739 |
| 2966 | Atp6v0e2 | NM_133764.3 | chr6:48537568-48541800 | 3063 | AY074887 | NM_145229.2 | chr9:54950256-54950954 |
| 2967 | Atp6v1a | NM_001109757.2 | chr16:44085403-44139019 | 3064 | AY358078 | NM_194347.1 | chr14:51800045-51826359 |
| 2968 | Atp6v1b1 | NM_134157.2 | chr6:83743016-83758810 | 3065 | AY512915 | NR_033559.1 | chr6:95290573-95333993 |
| 2969 | Atp6v1b2 | NM_007509.3 | chr8:69088735-69113717 | 3066 | AY512931 | NR_033588.1 | chr8:45060701-45065418 |
| 2970 | Atp6v1c1 | NM_025494.3 | chr15:38661903-38692444 | 3067 | AY761184 | NM_001007582.3 | chr8:21702523-21703647 |
| 2971 | Atp6v1c2 | NM_001159632.1 | chr12:17284720-17324730 | 3068 | AY761185 | NM_001012640.2 | chr10:20943693-20944748 |
| 2972 | Atp6v1d | NM_023721.2 | chr12:78841483-78861638 | 3069 | Aym1 | NM_001012726.2 | chr5:113357293-113357821 |
| 2973 | Atp6v1e1 | NM_007510.2 | chr6:120795243-120822685 | 3070 | Azgp1 | NM_013478.2 | chr5:137981520-137990232 |
| 2974 | Atp6v1e2 | NM_029121.3 | chr17:86944108-86947887 | 3071 | Azi2 | NM_001048146.2 | chr9:118040521-118060484 |
| 2975 | Atp6v1f | NM_025381.2 | chr6:29467782-29470509 | 3072 | Azin1 | NM_001102458.1 | chr15:38487429-38519266 |
| 2976 | Atp6v1g1 | NM_024173.2 | chr4:63544764-63550761 | 3073 | B020004C17Rik | NM_001256260.1 | chr14:57015133-57018982 |
| 2977 | Atp6v1g2 | NM_023179.3 | chr17:35236595-35238768 | 3074 | B020004J07Rik | NM_001033780.3 | chr4:101834968-101844022 |
| 2978 | Atp6v1g3 | NM_177397.3 | chr1:138273737-138289462 | 3075 | B020014A21Rik | NR_045946.1 | chr10:3125090-3133193 |
| 2979 | Atp6v1h | NM_133826.5 | chr1:5083085-5162549 | 3076 | B020018J28Rik | NR_045950.1 | chr12:112428283-112435338 |
| 2980 | Atp7a | NM_001109757.2 | chrX:106027123-106128160 | 3077 | B020033M17Rik | NM_001033769.2 | chr13:119949356-119950806 |
| 2981 | Atp7b | NM_007511.2 | chr8:21994347-22060074 | 3078 | B130006D01Rik | NR_028263.1 | chr11:95723585-95726773 |
| 2982 | Atp8a1 | NM_001038999.2 | chr5:67618138-67847431 | 3079 | B130024E19Rik | NR_045850.1 | chr7:70365382-70411146 |
| 2983 | Atp8a2 | NM_015803.2 | chr14:59647740-60086334 | 3080 | B130034C11Rik | NR_040375.1 | chr16:87496072-87504038 |
| 2984 | Atp8b1 | NM_001001488.3 | chr18:64528978-64661000 | 3081 | B230112J18Rik | NR_110475.1 | chr5:116312359-116318274 |
| 2985 | Atp8b2 | NM_001081182.2 | chr3:89939480-89963332 | 3082 | B230118H07Rik | NM_026592.3 | chr2:101560780-101628986 |
| 2986 | Atp8b3 | NM_001080930.1 | chr10:80519584-80539124 | 3083 | B230118M05Rik | NR_045454.1 | chrX:134684561-134686642 |
| 2987 | Atp8b4 | NM_001080944.3 | chr2:126320972-126491553 | 3084 | B230208H07Rik | NR_033532.1 | chr7:141359177-141365110 |
| 2988 | Atp8b5 | NM_177195.3 | chr4:43627158-43373831 | 3085 | B230208H11Rik | NR_038027.1 | chr10:12916645-12923127 |
| 2989 | Atp9a | NM_001289445.1 | chr2:168634437-168734339 | 3086 | B230209F15Rik | NR_045727.1 | chr7:61529409-61615327 |
| 2990 | Atp9b | NM_001201569.1 | chr18:80734140-80934058 | 3087 | B230214G05Rik | NR_045281.1 | chr15:88314873-88372651 |
| 2991 | Atpaf1 | NM_181040.4 | chr4:115784813-115812314 | 3088 | B230216E23Rik | NM_001242345.1 | chr6:142413430-142419740 |
| 2992 | Atpaf2 | NM_145427.2 | chr11:60400623-60417099 | 3089 | B230216N24Rik | NR_037993.1 | chr1:98031122-98047793 |
| 2993 | Atpif1 | NM_007512.4 | chr4:132530554-132535414 | 3090 | B230217C12Rik | NM_001080935.1 | chr1:97840779-97843043 |
| 2994 | Atr | NM_019864.1 | chr9:95857596-95951644 | 3091 | B230217J21Rik | NR_040316.1 | chr19:57323196-57360899 |
| 2995 | Atraid | NM_027855.4 | chr5:31048639-31054633 | 3092 | B230219D22Rik | NR_181778.2 | chr5:85693123-85703500 |
| 2996 | Atrip | NM_172774.3 | chr9:109059746-109074124 | 3093 | B230232G24Rik | NR_040745.1 | chr2:180370857-180385585 |
| 2997 | Atrn | NM_009730.2 | chr2:130906495-131030326 | 3094 | B230319C09Rik | NR_028382.1 | chr6:83441754-83448322 |
| 2998 | Atrn1 | NM_181415.4 | chr19:57611033-58133340 | 3095 | B230323A14Rik | NR_040765.1 | chr9:69761145-69830199 |
| 2999 | Atrx | NM_009530.2 | chrX:105797614-105929372 | 3096 | B2m | NM_009735.3 | chr2:122147686-122153082 |
| 3000 | Atxn1 | NM_001199304.1 | chr13:45548735-45964991 | 3097 | B330016D10Rik | NR_030695.1 | chr4:141546163-141548313 |
| 3001 | Atxn10 | NM_016843.3 | chr15:85336380-85463836 | 3098 | B3galnt1 | NM_020026.4 | chr3:69573918-69598960 |
| 3002 | Atxn1l | NM_001080930.1 | chr8:109737530-109737739 | 3099 | B3galnt2 | NM_178640.2 | chr13:13954673-13999068 |
| 3003 | Atxn2 | NM_009125.3 | chr5:121711608-121811950 | 3100 | B3galt1 | NM_020283.4 | chr2:68104671-68122882 |
| 3004 | Atxn2l | NM_001083620.1 | chr7:126503302 | 3101 | B3galt2 | NM_020025.4 | chr1:143640696-143649937 |
| 3005 | Atxn3 | NM_001167914.1 | chr12:101952923-101958243 | 3102 | B3galt4 | NM_019420.2 | chr17:33949911-33951488 |
| 3006 | Atxn7 | NM_139227.4 | chr14:14012490-14107301 | 3103 | B3galt5 | NM_001122993.1 | chr16:96235800-96319858 |

Fig.21 - 17

| 3104 | B3galt6 | NM_080445.4 | chr4:155989465-155992678 | 3201 | Bbs1 | NM_001033128.3 | chr19:4886881-4906627 |
|---|---|---|---|---|---|---|---|
| 3105 | B3gat1 | NM_029792.1 | chr9:26751561-26761338 | 3202 | Bbs10 | NM_027914.1 | chr10:111298678-111301736 |
| 3106 | B3gat2 | NM_172124.2 | chr1:23761925-23847858 | 3203 | Bbs12 | NM_001008502.2 | chr3:37312553-37321451 |
| 3107 | B3gat3 | NM_024256.2 | chr19:8920392-8927236 | 3204 | Bbs2 | NM_026116.2 | chr8:94067953-94098811 |
| 3108 | B3glct | NM_001081204.1 | chr5:149678256-149762599 | 3205 | Bbs4 | NM_175325.3 | chr9:59321965-59363508 |
| 3109 | B3gnt1 | NM_175383.2 | chr19:5038825-5041134 | 3206 | Bbs5 | NM_028284.2 | chr2:69647254-69667569 |
| 3110 | B3gnt2 | NM_001169114.1 | chr11:22834738-22860336 | 3207 | Bbs7 | NM_027810.3 | chr3:36573142-36613389 |
| 3111 | B3gnt3 | NM_028189.3 | chr8:71691719-71701800 | 3208 | Bbs9 | NM_178415.1 | chr9:22475714-22888280 |
| 3112 | B3gnt4 | NM_198611.2 | chr5:123510459-123511882 | 3209 | Bbx | NM_027444.3 | chr16:50191843-50432389 |
| 3113 | B3gnt5 | NM_001159407.1 | chr16:19760233-19772753 | 3210 | BC002163 | NR_002445.2 | chr4:42955579-123718181 |
| 3114 | B3gnt6 | NM_001081167.1 | chr7:98192414-98199475 | 3211 | BC003331 | NM_001077237.1 | chr1:150361310-150393055 |
| 3115 | B3gnt7 | NM_145222.2 | chr1:86303220-86307305 | 3212 | BC003965 | NM_183150.2 | chr17:25184560-25187662 |
| 3116 | B3gnt8 | NM_001036740.2 | chr7:25627623-25629490 | 3213 | BC004004 | NM_030561.3 | chr17:29268787-29302887 |
| 3117 | B3gnt9 | NM_001271915.1 | chr2:105252637-105255153 | 3214 | BC005537 | NM_024473.3 | chr13:24801656-24812899 |
| 3118 | B3gntl1 | NM_178664.5 | chr11:121616207-121673151 | 3215 | BC005561 | NM_001166581.1 | chr5:104508351-104522383 |
| 3119 | B430010I23Rik | NR_015457.1 | chr8.41017467-41024216 | 3216 | BC005624 | NM_144885.2 | chr2:30972832-30981941 |
| 3120 | B430212C06Rik | NR_033214.1 | chr18:67321208-67344103 | 3217 | BC005764 | NM_001170935.1 | chr10:79860474-79874634 |
| 3121 | B430306N03Rik | NM_177083.4 | chr17:48316161-48326511 | 3218 | BC006965 | NR_024085.1 | chr11:112663926-112711356 |
| 3122 | B430319G19Rik | NR_029474.1 | chr9:92538800-92542869 | 3219 | BC016579 | NM_145389.2 | chr16:45626847-45654118 |
| 3123 | B4galnt1 | NM_001244617.1 | chr10:127165155-127168523 | 3220 | BC017158 | NM_145590.2 | chr7:128271378-128298131 |
| 3124 | B4galnt2 | NM_008081.3 | chr11:95863558-95914871 | 3221 | BC017643 | NM_001252548.1 | chr11:121222588-121229309 |
| 3125 | B4galnt3 | NM_198884.1 | chr6:120203809-120294659 | 3222 | BC018242 | NM_001290299.1 | chr3:21937009-21948907 |
| 3126 | B4galnt4 | NM_177897.3 | chr7:141061273-141072119 | 3223 | BC018473 | NR_033641 | chr11:116752166-116757883 |
| 3127 | B4galt1 | NM_022305.4 | chr4:40804581-40854537 | 3224 | BC018507 | NM_144837.3 | chr13:70588688-70637634 |
| 3128 | B4galt2 | NM_001253381.1 | chr4:117872999-117883476 | 3225 | BC020402 | NR_033219.1 | chr10:7678970-7681158 |
| 3129 | B4galt3 | NM_020579.2 | chr1:171270327-171276895 | 3226 | BC021614 | NM_144869.2 | chr19:4057486-4059294 |
| 3130 | B4galt4 | NM_001285793.1 | chr16:38742258-38769054 | 3227 | BC021767 | NR_033629.1 | chr3:94660588-94667152 |
| 3131 | B4galt5 | NM_019835.2 | chr2:167298444-167349178 | 3228 | BC021785 | NM_001001489.3 | chr10:39968152-39986646 |
| 3132 | B4galt6 | NM_019737.2 | chr18:20684598-20746404 | 3229 | BC021891 | NM_145608.2 | chr8:125910449-125947439 |
| 3133 | B4galt7 | NM_146045.2 | chr13:55599895-55610443 | 3230 | BC022687 | NM_145450.3 | chr12:112808974-112816245 |
| 3134 | B830005N14Rik | NM_175312.4 | chr6:136256674-136779966 | 3231 | BC023829 | NM_001033328.2 | chrX:70460055-70477043 |
| 3135 | B830019K06Rik | NR_045448.1 | chrX:8892352-8894964 | 3232 | BC024139 | NM_001142968.1 | chr15:76119517-76126558 |
| 3136 | B830017H08Rik | NR_027959.1 | chr16:17833118-17835019 | 3233 | BC024386 | NR_015583.1 | chr7:140906063-140907967 |
| 3137 | B930003M22Rik | NR_037588.1 | chr17:10319918-10321141 | 3234 | BC024978 | NM_001243888.1 | chr7:27195780-27204320 |
| 3138 | B930018H19Rik | NR_040706.1 | chr8.34589419-34640316 | 3235 | BC025920 | NR_030677.1 | chr10:81606307-81609836 |
| 3139 | B930025P03Rik | NR_040705.1 | chr8:10870421-10882464 | 3236 | BC026585 | NM_001033284.1 | chr1:157458531-157488733 |
| 3140 | B930041F14Rik | NM_178699.4 | chr4:155694361-155696483 | 3237 | BC027072 | NM_146082.3 | chr17:71743554-71752885 |
| 3141 | B930059L03Rik | NR_033340.1 | chr12:110591373-110592679 | 3238 | BC027231 | NM_145972.4 | chr16:44724300-44737284 |
| 3142 | B930092H01Rik | NR_045334.1 | chr9:61259459-61293809 | 3239 | BC028528 | NM_153513.2 | chr3:95884972-95891930 |
| 3143 | B9d1 | NM_013717.2 | chr11:61505171-61512927 | 3240 | BC029214 | NM_153557.1 | chr2:25459487-25461094 |
| 3144 | B9d2 | NM_172148.1 | chr7:25681157-25686558 | 3241 | BC029722 | NR_015628.1 | chr2:155817731-155819203 |
| 3145 | Baalc | NM_080640.5 | chr15:38933908-38952916 | 3242 | BC030307 | NM_001003910.2 | chr10:86770810-86776843 |
| 3146 | Baat | NM_007519.2 | chr4:49489417-49506558 | 3243 | BC030336 | NM_001164580.1 | chr7:120677819-120734854 |
| 3147 | Babam1 | NM_026636.1 | chr8:71396854-71404772 | 3244 | BC030499 | NM_001287206.1 | chr11:78290840-78296805 |
| 3148 | Bace1 | NM_001145947.1 | chr9:45838528-45862484 | 3245 | BC030500 | NM_173411.2 | chr8:58911754-58914298 |
| 3149 | Bace2 | NM_019517.4 | chr16:97356727-97439012 | 3246 | BC030867 | NM_153544.3 | chr11:102248881-102265183 |
| 3150 | Bach1 | NM_007520.2 | chr16:87698953-87733346 | 3247 | BC030870 | NM_033217.1 | chr8:65085614-65129537 |
| 3151 | Bach2 | NM_001109661.1 | chr4:32417434-32586108 | 3248 | BC031181 | NM_001001181.3 | chr18:75005899-75009933 |
| 3152 | Bach2os | NR_026843.1 | chr4:32519679-32571662 | 3249 | BC031361 | NR_033221.1 | chr16:38085063-38089260 |
| 3153 | Bad | NM_001285453.1 | chr19:6942561-6951905 | 3250 | BC033916 | NR_040470.1 | chr17:33905134-33906675 |
| 3154 | Bag1 | NM_001171739.1 | chr4:40936397-40948294 | 3251 | BC035044 | NM_001254946.1 | chr8:128848043-128891124 |
| 3155 | Bag2 | NM_145392.2 | chr1:33745483-33757750 | 3252 | BC037032 | NR_028266.1 | chr15:4020110-4027406 |
| 3156 | Bag3 | NM_001285382.1 | chr7:128523582-128546979 | 3253 | BC037034 | NM_153161.3 | chr5:138259657-138264052 |
| 3157 | Bag4 | NM_026121.3 | chr8:25764538-25785209 | 3254 | BC037704 | NR_045645.1 | chr19:43675177-43677170 |
| 3158 | Bag5 | NM_027404.2 | chr12:111709489-111713256 | 3255 | BC039771 | NR_033270.1 | chr2:145701194-145753672 |
| 3159 | Bag6 | NM_001252468.1 | chr17:35135177-35147322 | 3256 | BC039966 | NR_040670.1 | chr4:153948454-153950476 |
| 3160 | Bahcc1 | NM_198423.3 | chr11:120232946-120292297 | 3257 | BC048403 | NM_173022.2 | chr10:121739936-121752859 |
| 3161 | Bahd1 | NM_001045523.1 | chr2:118901614-118924524 | 3258 | BC048502 | NM_177631.3 | chr15:103438959-103448459 |
| 3162 | Bai1 | NM_174991.3 | chr15:74516196-74589464 | 3259 | BC048507 | NM_001001185.3 | chr13:67863325-87863923 |
| 3163 | Bai2 | NM_001199696.1 | chr4:129985077-130022633 | 3260 | BC048546 | NM_001001179.3 | chr6:128539821-128581606 |
| 3164 | Bai3 | NM_175642.4 | chr1:25267475-25829707 | 3261 | BC048562 | NM_001004192.1 | chr9:108436481-108446083 |
| 3165 | Baiap2 | NM_001037754.3 | chr11:119943091-120002618 | 3262 | BC048602 | NR_045280.1 | chr15:35307009-35328535 |
| 3166 | Baiap2l1 | NM_025833.3 | chr5:144264524-144358112 | 3263 | BC048609 | NM_001111317.1 | chr19:6080037-6080785 |
| 3167 | Baiap2l2 | NM_177580.3 | chr15:79258194-79285509 | 3264 | BC048644 | NM_001033485.2 | chr8:121907832-121918428 |
| 3168 | Baiap3 | NM_001163270.1 | chr17:25242658-25256364 | 3265 | BC048671 | NM_177738.2 | chr6:90301269-90305448 |
| 3169 | Bak1 | NM_007523.3 | chr17:27019811-27028626 | 3266 | BC048679 | NM_001193274.1 | chr7:81894273-81498330 |
| 3170 | Bambi | NM_026505.2 | chr18:3507956-3516404 | 3267 | BC049352 | NM_001198971.1 | chr9:45195765-45249985 |
| 3171 | Bambi-ps1 | NR_027919.1 | chr2:122466682-122467797 | 3268 | BC049635 | NM_177785.4 | chr4:42868002-42874203 |
| 3172 | Banf1 | NM_001038231.2 | chr19:5364632-5366363 | 3269 | BC049715 | NM_178776.3 | chr6:136828842-136840557 |
| 3173 | Banf2 | NM_001044750.1 | chr2:144093101-144073979 | 3270 | BC049730 | NM_199150.1 | chr7:24709258-24714535 |
| 3174 | Bank1 | NM_001033363.3 | chr3:136053363-136326066 | 3271 | BC049762 | NM_175567.3 | chr11:51253650-51262951 |
| 3175 | Banp | NM_001110100.2 | chr8:121950491-122029260 | 3272 | BC051019 | NM_001040700.2 | chr7:109712180-109723771 |
| 3176 | Bap1 | NM_027088.2 | chr14:31251488-31259929 | 3273 | BC051142 | NM_001001377.2 | chr7:34998819-34460734 |
| 3177 | Bard1 | NM_007525.3 | chr1:71027534-71102972 | 3274 | BC051226 | NR_045146.1 | chr17:33908181-33909178 |
| 3178 | Barhl1 | NM_001164186.1 | chr2:28907679-28916440 | 3275 | BC051537 | NR_046183.1 | chr17:34083842-34095309 |
| 3179 | Barhl2 | NM_001009477.1 | chr5:106452522-106458166 | 3276 | BC051628 | NM_199312.3 | chr2:181220015-181222851 |
| 3180 | Barx1 | NM_007526.4 | chr13:48663035-48666507 | 3277 | BC051665 | NM_199148.2 | chr13:67811886-67786864 |
| 3181 | Barx2 | NM_013800.2 | chr9:31846043-31913285 | 3278 | BC052040 | NM_001145898.1 | chr2:115581716-115778768 |
| 3182 | Basp1 | NM_027395.2 | chr15:25362876-25413764 | 3279 | BC052688 | NM_028430.1 | chr13:61771579-61787282 |
| 3183 | Batf | NM_016767.2 | chr12:85686719-85709087 | 3280 | BC053393 | NM_001025435.3 | chr11:46571512-46589232 |
| 3184 | Batf2 | NM_028967.1 | chr19:6164457-6172475 | 3281 | BC053749 | NM_183321.1 | chr7:30539133-30552272 |
| 3185 | Batf3 | NM_030646.2 | chr1:191098413-191108943 | 3282 | BC055111 | NM_183182.3 | chr4:106590908-106617238 |
| 3186 | Bax | NM_007527.3 | chr7:45461694-45466898 | 3283 | BC055324 | NM_203364.1 | chr1:163954007-163994781 |
| 3187 | Baz1a | NM_013815.2 | chr12:54892998-54986336 | 3284 | BC055402 | NR_037990.1 | chr1:57200644-57214998 |
| 3188 | Baz1b | NM_011714.2 | chr5:135187322-135246129 | 3285 | BC061194 | NM_001001334.2 | chr2:18699021-18749605 |
| 3189 | Baz2a | NM_054078.2 | chr10:128092782-128129303 | 3286 | BC061195 | NR_105038.1 | chrX:93156153-93183944 |
| 3190 | Baz2b | NM_001001182.3 | chr2:59899362-60125740 | 3287 | BC061212 | NM_198667.1 | chr5:94066454-94070545 |
| 3191 | BB014433 | NR_037972.1 | chr8:15041445-15046078 | 3288 | BC061237 | NM_198677.1 | chr14:44500121-44506345 |
| 3192 | BB019430 | NR_033565.1 | chr10:58696744-58704277 | 3289 | BC064078 | NR_015455.1 | chr6:128993019-129006649 |
| 3193 | BB031773 | NR_038391.1 | chr4:103004005-103011905 | 3290 | BC065397 | NR_033324.1 | chrX:136742956-136803361 |
| 3194 | BB123696 | NR_027893.1 | chr13:52729369-52757205 | 3291 | BC068157 | NM_207203.2 | chr8:4209542-4217312 |
| 3195 | BB283400 | NR_038124.1 | chr6:30176622-30178040 | 3292 | BC068281 | NM_001170858.1 | chr12:4843302-4856967 |
| 3196 | BB287469 | NM_001177573.1 | chr6:30180869-87820656 | 3293 | BC080695 | NM_001007579.3 | chr4:143567466-143573798 |
| 3197 | BB557941 | NR_040356.1 | chr2:57127476-57181754 | 3294 | BC089491 | NM_175035.3 | chr7:28284651-28291134 |
| 3198 | Bbc3 | NM_133234.2 | chr7:16309582-16318334 | 3295 | BC089597 | NM_145424.2 | chr10:127866475-127877319 |
| 3199 | Bbip1 | NM_001195338.1 | chr2:53929658-53944627 | 3296 | BC094916 | NM_001024721.2 | chr3:173521310-173535957 |
| 3200 | Bbox1 | NM_130452.1 | chr2:110265082-110305725 | 3297 | Bcl | NR_038028.1 | chrX:79697304-183352564 |

Fig.21 - 18

| | | | | | | | |
|---|---|---|---|---|---|---|---|
| 3298 | BC100451 | NM_021440.2 | chr11:118332359-118342534 | 3395 | Bicd1 | NM_001112796.2 | chr6:149408983-149563326 |
| 3299 | BC100530 | NM_001082546.1 | chr16:36359381-36367570 | 3396 | Bicd2 | NM_001039179.2 | chr13:49341548-49387026 |
| 3300 | BC107364 | NM_001256180.1 | chr3:96432787-96452306 | 3397 | Bid | NM_007544.3 | chr6:120893118-120916820 |
| 3301 | BC117090 | NM_001001312.1 | chr16:36321664-36334332 | 3398 | Bik | NM_007546.2 | chr15:83526861-83544835 |
| 3302 | BC147527 | NM_001037925.2 | chr13:120300391-120308841 | 3399 | Bin1 | NM_001083334.1 | chr18:32377216-32435740 |
| 3303 | Bcain | NM_020486.2 | chr7:19756137-19770532 | 3400 | Bin2 | NM_001270537.1 | chr15:100641081-100669500 |
| 3304 | Bcan | NM_001109758.1 | chr3:87992513-88000356 | 3401 | Bin3 | NM_021328.3 | chr14:70100144-70138206 |
| 3305 | Bcap29 | NM_001164090.1 | chr12:31595353-31634658 | 3402 | Birc2 | NM_007465.3 | chr9:7818225-7837057 |
| 3306 | Bcap31 | NM_012060.5 | chrX:73686177-73716204 | 3403 | Birc3 | NM_007464.3 | chr9:7848700-7873170 |
| 3307 | Bcar1 | NM_001198839.1 | chr8:111710474-111732136 | 3404 | Birc5 | NM_001012273.1 | chr11:117849236-117855743 |
| 3308 | Bcar3 | NM_013867.2 | chr3:122419779-122530182 | 3405 | Birc6 | NM_007566.3 | chr17:74528294-74703358 |
| 3309 | Bcas1 | NM_001164369.1 | chr2:170346990-170427845 | 3406 | Birc7 | NM_001163247.1 | chr2:180929022-180934010 |
| 3310 | Bcas1os2 | NR_040610.1 | chr2:170356360-170380435 | 3407 | Bivm | NM_144558.4 | chr14:119967-44144771 |
| 3311 | Bcas2 | NM_026602.3 | chr3:103171710-103179154 | 3408 | Bicap | NM_018916.3 | chr2:157556361-157566361 |
| 3312 | Bcas3 | NM_001166642.1 | chr11:85353163-85826058 | 3409 | Bik | NM_007549.2 | chr14:63372836-63417187 |
| 3313 | Bcas3os1 | NR_045875.1 | chr11:85702199-85719744 | 3410 | Bim | NM_001042527.2 | chr7:80454992-80535119 |
| 3314 | Bcas3os2 | NR_046194.1 | chr11:85766832-85775680 | 3411 | Blmh | NM_178645.4 | chr11:76945655-76987389 |
| 3315 | Bcat1 | NM_001024468.3 | chr6:144949884-145048812 | 3412 | Blnk | NM_008528.4 | chr19:40928926-40994535 |
| 3316 | Bcat2 | NM_001243092.1 | chr7:45571278-45589710 | 3413 | Bloc1s1 | NM_015740.3 | chr10:128919913-128923524 |
| 3317 | Bccip | NM_025392.2 | chr7:133709332-133721145 | 3414 | Bloc1s2 | NM_028607.1 | chr19:44139246-44146446 |
| 3318 | Bdkrn3d | NM_029236.2 | chr15:99470083-99474730 | 3415 | Bloc1s3 | NM_177692.3 | chr7:19505803-19508331 |
| 3319 | Bche | NM_009738.3 | chr3:73635808-73708415 | 3416 | Bloc1s4 | NM_133724.3 | chr5:36747373-36748679 |
| 3320 | Bckdha | NM_007533.5 | chr7:25629851-25658761 | 3417 | Bloc1s5 | NM_139063.1 | chr13:38602705-38635169 |
| 3321 | Bckdhb | NM_199195.1 | chr9:83948780-84124240 | 3418 | Bloc1s6 | NM_019788.3 | chr2:122738504-122748487 |
| 3322 | Bckdk | NM_009739.3 | chr7:127904072-127909664 | 3419 | Blvra | NM_026678.4 | chr2:127070656-127097084 |
| 3323 | Bcl10 | NM_009741.5 | chr3:145942261-145934364 | 3420 | Blvrb | NM_001290525.1 | chr7:27452417-27465981 |
| 3324 | Bcl11a | NM_001159289.1 | chr11:24078055-24173558 | 3421 | Bzf1 | NM_001160280.1 | chr1:164289799-164307484 |
| 3325 | Bcl11b | NM_001079883.1 | chr12:107910402-108003414 | 3422 | Bmi1 | NM_138313.3 | chr2:118528756-118549678 |
| 3326 | Bcl2 | NM_009741.5 | chr1:106538175-106714290 | 3423 | Bmi1 | NM_007552.4 | chr1:18677017-18696629 |
| 3327 | Bcl2a1a | NM_009742.3 | chr9:88956919-88962416 | 3424 | Bmp1 | NM_009755.3 | chr14:70474554-70520260 |
| 3328 | Bcl2a1b | NM_007534.3 | chr9:89139272-89207838 | 3425 | Bmp10 | NM_009756.3 | chr6:87428993-87434512 |
| 3329 | Bcl2a1c | NM_007535.2 | chr9:114330134-114330578 | 3426 | Bmp15 | NM_009757.4 | chrX:6314105-6320723 |
| 3330 | Bcl2a1d | NM_007536.2 | chr9:88723287-88731850 | 3427 | Bmp2 | NM_007553.3 | chr2:133552158-133562896 |
| 3331 | Bcl2l1 | NM_001289716.1 | chr2:152780663-152830717 | 3428 | Bmp2k | NM_080708.1 | chr5:96997888-97091048 |
| 3332 | Bcl2l10 | NM_013479.2 | chr9:75347757-75351640 | 3429 | Bmp3 | NM_173404.5 | chr5:98854414-98880960 |
| 3333 | Bcl2l11 | NM_001284430.2 | chr2:128127574-128131498 | 3430 | Bmp4 | NM_007554.3 | chr14:46383519-46390599 |
| 3334 | Bcl2l12 | NM_029530.3 | chr7:44991221-44997579 | 3431 | Bmp5 | NM_007555.4 | chr9:75775364-75899017 |
| 3335 | Bcl2l13 | NM_153516.2 | chr6:120836229-120892842 | 3432 | Bmp6 | NM_007556.3 | chr13:38345715-38499728 |
| 3336 | Bcl2l14 | NM_025778.3 | chr6:134036518-134438724 | 3433 | Bmp7 | NM_007557.3 | chr2:172868011-172940321 |
| 3337 | Bcl2l15 | NM_001142959.1 | chr3:103832695-103838648 | 3434 | Bmp8a | NM_001256019.1 | chr4:123312649-123343252 |
| 3338 | Bcl2l2 | NM_007537.1 | chr14:54883424-54888234 | 3435 | Bmp8b | NM_007559.4 | chr4:123105164-123126091 |
| 3339 | Bcl3 | NM_013601.3 | chr7:19808461-19822755 | 3436 | Bmper | NM_028472.2 | chr9:23223075-23488715 |
| 3340 | Bcl6 | NM_009744.3 | chr16:23965051-23988612 | 3437 | Bmpr1a | NM_009758.4 | chr14:34411067-34502546 |
| 3341 | Bcl6b | NM_007528.3 | chr11:70224126-70229798 | 3438 | Bmpr1b | NM_001277216.1 | chr3:141837135-142169228 |
| 3342 | Bcl7a | NM_029825.3 | chr5:123344447-123374083 | 3439 | Bmpr2 | NM_007561.4 | chr1:59764278-59878081 |
| 3343 | Bcl7b | NM_009745.2 | chr5:135168371-135181852 | 3440 | Bms1 | NM_194339.1 | chr6:118383380-118419417 |
| 3344 | Bcl7c | NM_009746.2 | chr7:127704977-127708766 | 3441 | Bmx | NM_009759.4 | chrX:164192841-164258193 |
| 3345 | Bcl9 | NM_029933.4 | chr3:97203661-97227364 | 3442 | Bmyc | NM_023326.2 | chr2:25706878-25707719 |
| 3346 | Bcl9l | NM_080256.2 | chr9:44489135-44510412 | 3443 | Bnc1 | NM_007562.2 | chr7:81966661-81992299 |
| 3347 | Bclaf1 | NM_001025392.1 | chr10:20312468-20342501 | 3444 | Bnc2 | NM_172870.4 | chr4:84772541-84675088 |
| 3348 | Bcmo1 | NM_001163028.1 | chr8:117095864-117133720 | 3445 | Bnip1 | NM_172149.5 | chr17:26781078-26792521 |
| 3349 | Bco2 | NM_133217.3 | chr9:50533086-50555138 | 3446 | Bnip2 | NM_001008238.3 | chr9:69989465-70011659 |
| 3350 | Bcor | NM_001168321.1 | chrX:12036737-12160355 | 3447 | Bnip3 | NM_009760.4 | chr7:138890835-138909506 |
| 3351 | Bcorl1 | NM_178782.4 | chrX:48341357-48406728 | 3448 | Bnip3l | NM_009761.3 | chr14:66985239-67008877 |
| 3352 | Bcr | NM_001081412.2 | chr10:75060895-75184923 | 3449 | Bnipl | NM_001168456.1 | chr3:95261292-95261193 |
| 3353 | Bcs1l | NM_025784.5 | chr1:74588288-74592443 | 3450 | Boc | NM_172506.2 | chr16:44485044-44558870 |
| 3354 | Bdh1 | NM_001122683.1 | chr16:31428752-31458901 | 3451 | Bod1 | NM_001024919.1 | chr11:31665149-31671852 |
| 3355 | Bdh2 | NM_001172055.1 | chr3:135281220-135304425 | 3452 | Bod1l | NM_001081422.3 | chr5:41787539-41844315 |
| 3356 | Bdkrb1 | NM_007539.2 | chr12:105604090-105605428 | 3453 | Bok | NM_016778.3 | chr1:93685574-93695770 |
| 3357 | Bdkrb2 | NM_009747.2 | chr12:105568171-105593071 | 3454 | Bola1 | NM_026975.2 | chr3:96196587-96197586 |
| 3358 | Bdnf | NM_001048139.1 | chr2:109676896-109727043 | 3455 | Bola2 | NM_175103.3 | chr7:126695999-126696693 |
| 3359 | Bdp1 | NM_001081061.1 | chr13:100017993-100104079 | 3456 | Bola3 | NM_175277.4 | chr6:83349483-83358392 |
| 3360 | Bean1 | NM_001141927.1 | chr8:104170512-104219097 | 3457 | Boll | NM_001113367.1 | chr1:55300068-55362707 |
| 3361 | Becn1 | NM_019584.3 | chr11:101288266-101302267 | 3458 | Bop1 | NM_013481.1 | chr15:76452995-76477269 |
| 3362 | Becn2 | NM_001290692.1 | chr1:175920328-175922225 | 3459 | Bora | NM_175265.4 | chr14:99046376-99074107 |
| 3363 | Begain | NM_001163751.1 | chr12:109082181-109068217 | 3460 | Bpgm | NM_007563.4 | chr6:34876355-34905610 |
| 3364 | Bend3 | NM_199028.2 | chr10:43479139-43515417 | 3461 | Bphl | NM_026512.1 | chr13:34017640-34074074 |
| 3365 | Bend4 | NM_001164806.1 | chr5:67392146-67427799 | 3462 | Bpi | NM_177850.3 | chr2:158258240-158294531 |
| 3366 | Bend5 | NM_026279.4 | chr4:111485005-111460298 | 3463 | Bpifa1 | NM_011126.3 | chr2:154142879-154149217 |
| 3367 | Bend6 | NM_177235.3 | chr1:33852051-33907621 | 3464 | Bpifa2 | NM_008953.2 | chr2:154068275-154016073 |
| 3368 | Bend7 | NM_001190400.1 | chr2:4717836-4802146 | 3465 | Bpifa3 | NM_001194079.1 | chr2:154130335-154138359 |
| 3369 | Best1 | NM_011913.2 | chr19:9985171-10001633 | 3466 | Bpifa5 | NM_025990.4 | chr2:154162606-154168446 |
| 3370 | Best2 | NM_001130394.1 | chr8:85007202-85014408 | 3467 | Bpifa6 | NM_001080811.1 | chr2:153974944-154000495 |
| 3371 | Best3 | NM_007583.1 | chr10:116986313-117025040 | 3468 | Bpifb1 | NM_001012992.1 | chr2:154190817-154220343 |
| 3372 | Bet1 | NM_009748.2 | chr6:4076903-4086927 | 3469 | Bpifb2 | NM_025631.3 | chr2:153875044-153895270 |
| 3373 | Bet1l | NM_018742.5 | chr7:140853383-140856383 | 3470 | Bpifb3 | NM_194357.1 | chr2:153918229-153932996 |
| 3374 | Bex1 | NM_009052.2 | chrX:136213971-136215513 | 3471 | Bpifb4 | NM_001034875.3 | chr2:153940861-153963852 |
| 3375 | Bex2 | NM_009749.2 | chrX:136066564-136068236 | 3472 | Bpifb5 | NM_144890.2 | chr2:154223741-154240902 |
| 3376 | Bex4 | NM_212457.2 | chrX:136139044-136140437 | 3473 | Bpifb6 | NM_199303.2 | chr2:153900387-153912793 |
| 3377 | Bex6 | NM_001033539.2 | chr16:32179799-32186944 | 3474 | Bpifb9a | NM_175187.3 | chr2:154257878-154271243 |
| 3378 | Bfar | NM_001177552.1 | chr16:13671857-13703612 | 3475 | Bpifb9b | NM_001025574.1 | chr2:154307243-154320642 |
| 3379 | Bfsp1 | NM_001291061.1 | chr2:143826527-143863173 | 3476 | Bpifc | NM_177772.4 | chr10:85956990-86011860 |
| 3380 | Bfsp2 | NM_001002896.2 | chr9:103424923-103480328 | 3477 | Bpnt1 | NM_011794.3 | chr1:185332158-185357769 |
| 3381 | Bglap | NM_001037939.2 | chr3:88381494-88384466 | 3478 | Bptf | NM_176850.2 | chr11:107033080-107131922 |
| 3382 | Bglap2 | NM_001032298.3 | chr3:88377735-88378701 | 3479 | Braf | NM_139294.5 | chr6:39603236-39725463 |
| 3383 | Bglap3 | NM_031368.5 | chr3:88368615-88369831 | 3480 | Brap | NM_001289643.1 | chr5:121660562-121687249 |
| 3384 | Bgn | NM_007549.3 | chrX:73463634-73495936 | 3481 | Brat1 | NM_001276287.1 | chr5:140705065-140719378 |
| 3385 | Bhlha15 | NM_010800.4 | chr5:144190285-144194441 | 3482 | Brca1 | NM_009764.3 | chr11:101488763-101551955 |
| 3386 | Bhlha9 | NM_177182.4 | chr11:76672469-76673676 | 3483 | Brca2 | NM_001081001.2 | chr5:150522620-150570146 |
| 3387 | Bhlhb9 | NM_001098392.1 | chr5:135885850-135891081 | 3484 | Brcc3 | NM_001166457.1 | chrX:75416627-75454001 |
| 3388 | Bhlhe22 | NM_021560.4 | chr3:18054324-18057514 | 3485 | Brd1 | NM_001033274.3 | chr15:88687084-88734219 |
| 3389 | Bhlhe23 | NM_080641.5 | chr2:180774380-180776900 | 3486 | Brd2 | NM_001204973.1 | chr17:34112018-34122607 |
| 3390 | Bhlhe40 | NM_011498.4 | chr6:108680628-108666925 | 3487 | Brd3 | NM_001113573.1 | chr2:27445580-27475673 |
| 3391 | Bhlhe41 | NM_001271768.1 | chr6:145858242-145865420 | 3488 | Brd4 | NM_001286630.1 | chr17:32196271-32284133 |
| 3392 | Bhmt | NM_016668.3 | chr13:93356098-93367758 | 3489 | Brd7 | NM_012047.2 | chr8:88332310-88362191 |
| 3393 | Bhmt2 | NM_022884.2 | chr13:93656096-93674302 | 3490 | Brd8 | NM_001289606.1 | chr18:34598614-34624863 |
| 3394 | Bicc1 | NM_031397.2 | chr10:70925095-71159634 | 3491 | Brd9 | NM_001024508.3 | chr13:73937810-73960889 |

Fig.21 - 19

| | | | | | | | |
|---|---|---|---|---|---|---|---|
| 3492 | Brdt | NM_001079873.1 | chr5:107331193-107360741 | 3589 | C130060C02Rik | NR_049355.1 | chr19:15985074-16010912 |
| 3493 | Bre | NM_144541.1 | chr5:31698049-32084739 | 3590 | C130060K24Rik | NM_175524.4 | chr6:65381293-65458150 |
| 3494 | Brf1 | NM_028193.3 | chr12:112959861-113000621 | 3591 | C130071C03Rik | NR_015561.2 | chr13:83728105-83735689 |
| 3495 | Brf2 | NM_025686.2 | chr8:27123831-27128632 | 3592 | C130074G19Rik | NM_178692.3 | chr1:184871925-184883036 |
| 3496 | Bri3 | NM_001163709.1 | chr5:144244436-144264873 | 3593 | C130079G13Rik | NM_177861.3 | chr3:59925213-59937949 |
| 3497 | Bri3bp | NM_029752.2 | chr5:125441567-125460885 | 3594 | C130080G10Rik | NM_028422.1 | chr2:114054395-114061502 |
| 3498 | Bricd5 | NM_175682.3 | chr17:24473883-24475469 | 3595 | C130083M11Rik | NR_040717.1 | chr5:52199983-52216433 |
| 3499 | Brinp1 | NM_019967.2 | chr4:68761371-68954397 | 3596 | C1d | NM_020559.3 | chr11:17257617-17269176 |
| 3500 | Brinp2 | NM_207583.2 | chr1:158245268-158356260 | 3597 | C1galt1 | NM_052993.3 | chr6:7845223-7872042 |
| 3501 | Brinp3 | NM_001145807.1 | chr1:146497686-146902472 | 3598 | C1galt1c1 | NM_023550.3 | chrX:38630782-38635143 |
| 3502 | Brip1 | NM_178309.2 | chr11:86058135-86201193 | 3599 | C1qa | NM_007572.2 | chr4:136895915-136898844 |
| 3503 | Brix1 | NM_026396.3 | chr15:10474778-10485937 | 3600 | C1qb | NM_009777.2 | chr4:136886144-136886177 |
| 3504 | Brk1 | NM_133937.1 | chr6:113604771-113616951 | 3601 | C1qbp | NM_007573.2 | chr11:70977845-70983026 |
| 3505 | Brms1 | NM_134155.1 | chr19:5041403-5049917 | 3602 | C1qc | NM_007574.2 | chr4:136898801-136892914 |
| 3506 | Brms1l | NM_001037756.2 | chr12:55830368-55869735 | 3603 | C1ql1 | NM_013795.2 | chr11:102939263-102946461 |
| 3507 | Brox | NM_027861.2 | chr1:183276341-183297008 | 3604 | C1ql2 | NM_207233.1 | chr1:120340581-120343174 |
| 3508 | Brpf1 | NM_001282126.1 | chr6:113307136-113324862 | 3605 | C1ql3 | NM_153155.2 | chr2:13001886-13010864 |
| 3509 | Brpf3 | NM_001081315.1 | chr17:28801125-28838789 | 3606 | C1ql4 | NM_001024702.1 | chr15:99084753-99087728 |
| 3510 | Brs3 | NM_009766.3 | chrX:57043073-57048758 | 3607 | C1qtnf1 | NM_001204129.1 | chr11:118428458-118451782 |
| 3511 | Brsk1 | NM_001003920.3 | chr7:4690927-4715997 | 3608 | C1qtnf2 | NM_026979.5 | chr11:43474305-43491525 |
| 3512 | Brsk2 | NM_001009929.3 | chr7:141949750-142004243 | 3609 | C1qtnf3 | NM_001204134.1 | chr15:10952356-10980162 |
| 3513 | Brwd1 | NM_001103179.1 | chr16:96001547-96082428 | 3610 | C1qtnf4 | NM_026161.3 | chr2:90885785-90890526 |
| 3514 | Brwd3 | NM_001081477.1 | chrX:108742207-108834355 | 3611 | C1qtnf5 | NM_001040631.2 | chr9:44107244-44109187 |
| 3515 | Btc | NM_011360.4 | chr19:8837466-8848683 | 3612 | C1qtnf6 | NM_001204152.1 | chr15:78523345-78529651 |
| 3516 | Bdc1 | NM_133889.2 | chr4:129461678-129488432 | 3613 | C1qtnf7 | NM_001139172.1 | chr5:43515866-43616586 |
| 3517 | Bsg | NM_001077184.1 | chr10:79704357-79711979 | 3614 | C1qtnf9 | NM_183175.4 | chr14:60768133-60780869 |
| 3518 | Bsn | NM_007567.2 | chr9:108096021-108190383 | 3615 | C1ra | NM_023143.3 | chr6:124512620-124523440 |
| 3519 | Bsnd | NM_080458.2 | chr4:106483457-106492243 | 3616 | C1rb | NM_001113356.1 | chr6:124570429-124581044 |
| 3520 | Bsph1 | NM_001033418.4 | chr7:13456840-13473450 | 3617 | C1rl | NM_181344.5 | chr6:124493112-124510643 |
| 3521 | Bsph2 | NM_001080942.2 | chr7:13554865-13571067 | 3618 | C1s1 | NM_001097617.1 | chr6:124530343-124542359 |
| 3522 | Bspry | NM_138653.1 | chr4:62480066-62497298 | 3619 | C1s2 | NM_178864.2 | chr6:124624624-124636085 |
| 3523 | Bst1 | NM_009763.3 | chr5:43818892-43843463 | 3620 | C2 | NM_013484.2 | chr17:34862601-34882100 |
| 3524 | Bst2 | NM_198095.2 | chr8:71534261-71537437 | 3621 | C230004F18Rik | NR_030706.1 | chrX:61116377-61139460 |
| 3525 | Bsx | NM_178245.3 | chr9:40874126-40877972 | 3622 | C230024C17Rik | NR_046171.1 | chr13:153721239-153737829 |
| 3526 | Btaf1 | NM_001080706.1 | chr19:36926078-37014057 | 3623 | C230029M16 | NR_110482.1 | chr10:118920380-118927143 |
| 3527 | Btbd1 | NM_146199.2 | chr7:81792079-81829431 | 3624 | C230035I16Rik | NR_015492.1 | chr13:23427975-23431017 |
| 3528 | Btbd10 | NM_133700.2 | chr7:113315663-113369339 | 3625 | C230037I18Rik | NR_077233.1 | chr15:89476251-89484850 |
| 3529 | Btbd11 | NM_001017525.1 | chr10:85598410-85660292 | 3626 | C230052I11Rik | NM_178643.5 | chr7:35392151-35396767 |
| 3530 | Btbd16 | NM_001081038.2 | chr7:136774068-130825899 | 3627 | C230079O03Rik | NR_040459.1 | chr7:136632215-136349415 |
| 3531 | Btbd17 | NM_028055.4 | chr11:114790668-114795892 | 3628 | C230091D08Rik | NR_015479.1 | chr7:59307923-59324149 |
| 3532 | Btbd18 | NM_001145100.1 | chr2:84659078-84668781 | 3629 | C2cd2 | NM_174847.2 | chr16:97855208-97922633 |
| 3533 | Btbd19 | NR_024078.1 | chr4:117119217-117125725 | 3630 | C2cd2l | NM_027909.2 | chr9:44309236-44320782 |
| 3534 | Btbd2 | NM_145361.2 | chr10:80642616-80670671 | 3631 | C2cd3 | NM_001017985.2 | chr7:100372232-100470159 |
| 3535 | Btbd3 | NM_001025431.1 | chr2:138256583-138287422 | 3632 | C2cd4a | NM_001163143.1 | chr9:67830531-67832330 |
| 3536 | Btbd6 | NM_001145900.1 | chr12:112976481-112978940 | 3633 | C2cd4b | NM_001081314.2 | chr9:67759436-67760933 |
| 3537 | Btbd7 | NM_172806.2 | chr12:102784647-102878406 | 3634 | C2cd4c | NM_001168624.1 | chr10:79606853-79614025 |
| 3538 | Btbd8 | NM_001255991.1 | chr5:107437996-107491596 | 3635 | C2cd4d | NM_001136117.1 | chr3:94362443-94364567 |
| 3539 | Btbd9 | NM_027060.1 | chr17:30215523-30576287 | 3636 | C2cd5 | NM_001109688.2 | chr6:143010919-143100152 |
| 3540 | Btc | NM_007568.5 | chr5:91387260-91402994 | 3637 | C3 | NM_009778.3 | chr17:57203966-57228136 |
| 3541 | Btd | NM_025294.4 | chr14:31641056-31668197 | 3638 | C330006A16Rik | NM_001256521.1 | chr2:26136807-26140506 |
| 3542 | Btf3 | NM_001170540.1 | chr13:98309896-98317006 | 3639 | C330007P06Rik | NR_029951.1 | chrX:36848543-36864246 |
| 3543 | Btf3l4 | NM_027453.2 | chr4:108634294-108833584 | 3640 | C330011F03Rik | NR_046166.1 | chr17:51425208-51448269 |
| 3544 | Btg1 | NM_007569.2 | chr10:96617000-96622811 | 3641 | C330013E15Rik | NR_045701.1 | chr15:100614139-100615110 |
| 3545 | Btg2 | NM_007570.2 | chr1:134074864-134079155 | 3642 | C330013F16Rik | NR_045455.1 | chrX:139240225-139356770 |
| 3546 | Btg3 | NM_009770.3 | chr16:78359859-78376810 | 3643 | C330018D20Rik | NM_029909.1 | chr18:56955830-56975379 |
| 3547 | Btg4 | NM_019493.3 | chr9:51116000-51119700 | 3644 | C330021F23Rik | NM_001024728.2 | chr8:3567997-3584776 |
| 3548 | Btk | NM_013482.2 | chrX:134542340-134583140 | 3645 | C330022C24Rik | NR_045717.1 | chr7:140837220-140845689 |
| 3549 | Btla | NM_001037719.2 | chr16:45224336-45252895 | 3646 | C330024D12Rik | NR_046161.1 | chr17:87192215-87194942 |
| 3550 | Btn1a1 | NM_013483.3 | chr13:23456992-23466901 | 3647 | C330024D21Rik | NR_015582.2 | chr5:67463897-67470831 |
| 3551 | Btn2a2 | NM_001289614.1 | chr13:23477062-23488357 | 3648 | C330027C09Rik | NM_172616.2 | chr16:48994187-49019705 |
| 3552 | Btnl1 | NM_001111094.1 | chr17:34377131-34386028 | 3649 | C330046N16Rik | NR_040658.1 | chr10:84547416-84553318 |
| 3553 | Btnl10 | NM_138678.2 | chr11:58918056-58926965 | 3650 | C3ar1 | NM_009779.2 | chr6:122847139-122856157 |
| 3554 | Btnl2 | NM_079834.1 | chr17:34354821-34369492 | 3651 | C430002E04Rik | NR_040385.1 | chr3:41487680-41493199 |
| 3555 | Btnl4 | NM_030746.1 | chr17:34469041-34475937 | 3652 | C430002N11Rik | NR_102293.1 | chr9:96765561-96774397 |
| 3556 | Btnl5-ps | NR_004651.1 | chr17:34487405-34497429 | 3653 | C430049B03Rik | NR_038184.1 | chrX:53053111-53057190 |
| 3557 | Btnl6 | NM_030747.1 | chr17:34507904-34517352 | 3654 | C4a | NM_011413.2 | chr17:34800091-34823454 |
| 3558 | Btnl9 | NM_172793.2 | chr11:49168324-49187089 | 3655 | C4b | NM_009780.2 | chr17:34728380-34743897 |
| 3559 | Btrc | NM_001037758.2 | chr19:45363733-45533343 | 3656 | C4bp | NM_007576.3 | chr1:130635920-130661618 |
| 3560 | Bub1 | NM_001113179.1 | chr2:127820199-127831859 | 3657 | C4bp-ps1 | NR_028304.1 | chr1:130670203-130681571 |
| 3561 | Bub1b | NM_009773.3 | chr2:118598210-118641592 | 3658 | C530005A16Rik | NR_029450.1 | chr4:116589732-116597630 |
| 3562 | Bub3 | NM_009774.3 | chr7:131560390-131571898 | 3659 | C530008M17Rik | NM_001163793.1 | chr5:76840598-76873554 |
| 3563 | Bud13 | NM_146000.2 | chr9:46283011-46298763 | 3660 | C530044C16Rik | NR_045984.1 | chr6:50776114-50814894 |
| 3564 | Bud31 | NM_001008705.2 | chr5:145140375-145148078 | 3661 | C5ar1 | NM_001173550.1 | chr7:16247744-16259338 |
| 3565 | Bves | NM_024285.2 | chr10:45335761-45369708 | 3662 | C5ar2 | NM_001146005.1 | chr7:16234584-16242931 |
| 3566 | Bysl | NM_016859.3 | chr17:47599330-47611492 | 3663 | C6 | NM_016704.2 | chr15:4727209-4804045 |
| 3567 | Bzrap1 | NM_172449.2 | chr11:87760540-87785928 | 3664 | C630028N04Rik | NR_040668.1 | chr4:51968033-52051110 |
| 3568 | Bzw1 | NM_025824.3 | chr1:58393135-58406548 | 3665 | C630036L19Rik | NR_046036.1 | chr12:29675629-29686445 |
| 3569 | Bzw2 | NM_025840.3 | chr12:36091834-36156825 | 3666 | C630043F03Rik | NR_027923.1 | chr4:72201243-72203930 |
| 3570 | C030006K11Rik | NM_145472.2 | chr15:76721464-76723845 | 3667 | C7 | NM_001234837.1 | chr15:4988761-5063773 |
| 3571 | C030007H22Rik | NR_040482.1 | chr1:89360343-89406133 | 3668 | C730002L08Rik | NR_045778.1 | chr19:20534526-20552330 |
| 3572 | C030013G03Rik | NR_077216.1 | chr17:12466843-12479577 | 3669 | C730027H18Rik | NR_038040.1 | chr10:71168796-71182040 |
| 3573 | C030016D13Rik | NR_027987.1 | chr19:27430036-27432631 | 3670 | C730036E19Rik | NR_038011.1 | chr5:151138033-151144095 |
| 3574 | C030018K13Rik | NR_045411.1 | chr5:64477007-64479746 | 3671 | C77080 | NM_001033189.3 | chr4:129219577-129248443 |
| 3575 | C030023E24Rik | NR_033502.1 | chrX:61191292-61194164 | 3672 | C77370 | NM_001077354.2 | chrX:104077434-104201117 |
| 3576 | C030029H02Rik | NR_102297.1 | chr7:136268323-136318551 | 3673 | C78339 | NM_001033192.2 | chr13:46669521-46675791 |
| 3577 | C030034I22Rik | NR_026848.1 | chr17:69416846-69419192 | 3674 | C86187 | NR_015609.1 | chr7:46967746-46975911 |
| 3578 | C030034L19Rik | NR_015494.2 | chr3:9403077-9413903 | 3675 | C86695 | NM_001081662.1 | chr8:21958713-21964303 |
| 3579 | C030037D09Rik | NR_038058.1 | chr11:88718642-88728572 | 3676 | C87198 | NR_046002.1 | chr12:56591058-56594554 |
| 3580 | C030039L03Rik | NM_001112731.1 | chr7:27689339-27706482 | 3677 | C87414 | NM_001164284.1 | chr15:93635184-93671463 |
| 3581 | C030046E11Rik | NR_046275.1 | chr19:29522281-29605921 | 3678 | C87436 | NM_001243741.1 | chr6:86438645-86470387 |
| 3582 | C130012O20Rik | NR_046275.1 | chr2:33641192-33649663 | 3679 | C87499 | NM_198663.3 | chr4:88627319-88634186 |
| 3583 | C130026I23Rik | NM_001037909.3 | chr1:85246343-85270566 | 3680 | C87977 | NM_001177542.1 | chr4:144206761-144213017 |
| 3584 | C130026L21Rik | NR_015546.2 | chr10:111581660-111587153 | 3681 | C8a | NM_001290645.1 | chr4:104815685-104876395 |
| 3585 | C130030K03Rik | NR_046212.1 | chr10:49093680-49095843 | 3682 | C8b | NM_133882.2 | chr4:104766316-104804548 |
| 3586 | C130036L24Rik | NR_015507.2 | chr3:86367694-86367694 | 3683 | C8g | NM_001271777.1 | chr2:25498649-25501719 |
| 3587 | C130046K22Rik | NR_102388.1 | chr1:103697723-103725573 | 3684 | C9 | NM_013485.1 | chr15:6445332-6498478 |
| 3588 | C130050O18Rik | NM_177000.3 | chr5:139406386-139416092 | 3685 | C920006O11Rik | NR_040401.1 | chr9:78175913-78178882 |

Fig.21 - 20

| | | | | | | | |
|---|---|---|---|---|---|---|---|
| 3686 | C920009818Rik | NR_015465.2 | chr10:22306719-22312942 | 3783 | Camsap3 | NM_001163749.1 | chr8:3587449-3609075 |
| 3687 | C920021L13Rik | NR_040446.1 | chr3:95871521-95889093 | 3784 | Camta1 | NM_001081557.3 | chr4:151059522-151861768 |
| 3688 | C920025E04Rik | NM_001271005.1 | chr17:36109029-36111676 | 3785 | Camta2 | NM_001190376.1 | chr11:70669462-70688105 |
| 3689 | Caap1 | NM_026368.2 | chr4:94500078-94556796 | 3786 | Cand1 | NM_027994.1 | chr10:119198811-119240055 |
| 3690 | Cab39 | NM_133781.4 | chr1:85793446-85851577 | 3787 | Cand2 | NM_025958.2 | chr6:115774556-115805555 |
| 3691 | Cab39l | NM_026908.3 | chr14:59440980-59548903 | 3788 | Cant1 | NM_001025617.2 | chr11:118406288-118419118 |
| 3692 | Cabin1 | NM_172549.3 | chr10:75646109-75764357 | 3789 | Canx | NM_001110499.1 | chr11:50293956-50325673 |
| 3693 | Cables1 | NM_001146287.1 | chr18:11839273-11945627 | 3790 | Cap1 | NM_007598.4 | chr4:122859047-122886057 |
| 3694 | Cables2 | NM_145851.2 | chr2:180258538-180273465 | 3791 | Cap2 | NM_026056.4 | chr13:46501902-46650281 |
| 3695 | Cabp1 | NM_013879.2 | chr5:115168690-115186121 | 3792 | Capg | NM_001942534.3 | chr6:72549272-72562983 |
| 3696 | Cabp2 | NM_001160252.1 | chr19:4083518-4087339 | 3793 | Capn1 | NM_001110504.1 | chr19:5988544-6015826 |
| 3697 | Cabp4 | NM_144532.2 | chr19:4135422-4139609 | 3794 | Capn10 | NM_011796.2 | chr1:92934407-92947948 |
| 3698 | Cabp5 | NM_013877.3 | chr7:13398154-13408878 | 3795 | Capn11 | NM_001013767.2 | chr17:45630203-45659309 |
| 3699 | Cabp7 | NM_138948.3 | chr11:4738820-4746778 | 3796 | Capn12 | NM_001110207.1 | chr7:28881656-28893585 |
| 3700 | Cabs1 | NM_027631.2 | chr5:87979450-87981541 | 3797 | Capn13 | NM_001033444.2 | chr17:73306463-73339296 |
| 3701 | Cabyr | NM_001042418.1 | chr18:12741354-12756142 | 3798 | Capn15 | NM_015830.1 | chr17:25959555-25965505 |
| 3702 | Cacfd1 | NM_001243239.1 | chr2:27009925-27016849 | 3799 | Capn2 | NM_009794.3 | chr1:182467258-182517483 |
| 3703 | Cachd1 | NM_198037.1 | chr4:100776678-101003748 | 3800 | Capn3 | NM_001109761.2 | chr2:120876908-120904919 |
| 3704 | Cacna1a | NM_001252059.1 | chr8:84415363-84640249 | 3801 | Capn5 | NM_007602.4 | chr7:98121558-98178274 |
| 3705 | Cacna1b | NM_001042528.2 | chr2:24603888-24763152 | 3802 | Capn6 | NM_007603.3 | chrX:143802236-143827412 |
| 3706 | Cacna1c | NM_001159533.2 | chr6:118587239-119108495 | 3803 | Capn7 | NM_009796.2 | chr14:31336723-31371983 |
| 3707 | Cacna1d | NM_001083616.2 | chr14:30039940-30353486 | 3804 | Capn8 | NM_001145806.1 | chr1:182565006-182605526 |
| 3708 | Cacna1e | NM_009782.3 | chr1:154392518-154725920 | 3805 | Capn9 | NM_023709.4 | chr8:124576110-124618731 |
| 3709 | Cacna1f | NM_019582.2 | chrX:7607102-7635196 | 3806 | Capns1 | NM_009795.3 | chr7:30186941-30195048 |
| 3710 | Cacna1g | NM_001112813.2 | chr11:94408390-94474198 | 3807 | Capns2 | NM_027112.1 | chr8:92901394-92902409 |
| 3711 | Cacna1h | NM_001163691.1 | chr17:25374286-25433783 | 3808 | Caprin1 | NM_001111289.1 | chr2:103762944-103797078 |
| 3712 | Cacna1i | NM_001044308.2 | chr15:80287237-80398292 | 3809 | Caprin2 | NM_181541.4 | chr6:148842491-148896237 |
| 3713 | Cacna1s | NM_001081023.1 | chr1:136052900-136119822 | 3810 | Caps2 | NM_178278.4 | chr10:112165675-112216555 |
| 3714 | Cacna2d1 | NM_001110843.1 | chr5:15934690-16374511 | 3811 | Capsl | NM_029341.1 | chr15:9416027-9466035 |
| 3715 | Cacna2d2 | NM_001740047.1 | chr9:107399879-107529343 | 3812 | Capza1 | NM_009797.2 | chr3:104822784-104864505 |
| 3716 | Cacna2d3 | NM_009785.1 | chr14:29404942-29721864 | 3813 | Capza2 | NM_007604.2 | chr6:17637097-17668538 |
| 3717 | Cacna2d4 | NM_001033382.2 | chr6:119236525-119352407 | 3814 | Capza3 | NM_007605.4 | chr6:140041524-140042786 |
| 3718 | Cacnb1 | NM_001159319.2 | chr11:98004924-98022627 | 3815 | Capzb | NM_001037761.2 | chr4:139192898-139291820 |
| 3719 | Cacnb2 | NM_001252533.1 | chr2:14824091-14987908 | 3816 | Car1 | NM_001083957.1 | chr3:14766213-14778460 |
| 3720 | Cacnb3 | NM_001044741.2 | chr15:98632327-98644536 | 3817 | Car10 | NM_028296.3 | chr11:93099289-93601751 |
| 3721 | Cacnb4 | NM_001037099.2 | chr2:52428319-52676609 | 3818 | Car11 | NM_009800.4 | chr7:45699966-45704661 |
| 3722 | Cacng1 | NM_007582.2 | chr11:107703217-107716476 | 3819 | Car12 | NM_178396.5 | chr9:66713685-66766845 |
| 3723 | Cacng2 | NM_007583.2 | chr15:77993622-78119280 | 3820 | Car13 | NM_024495.5 | chr3:14641726-14663002 |
| 3724 | Cacng3 | NM_019430.2 | chr7:122617143-122769394 | 3821 | Car14 | NM_011797.2 | chr3:95897799-95904639 |
| 3725 | Cacng4 | NM_019431.2 | chr11:107734779-107794464 | 3822 | Car15 | NM_030558.2 | chr16:17835275-17838186 |
| 3726 | Cacng5 | NM_001199301.1 | chr1:107874604-107915055 | 3823 | Car2 | NM_009801.4 | chr3:14886425-14900770 |
| 3727 | Cacng6 | NM_133183.1 | chr7:3424661-3434940 | 3824 | Car3 | NM_007606.3 | chr3:14863537-14872373 |
| 3728 | Cacng7 | NM_133189.3 | chr7:3336584-3366948 | 3825 | Car4 | NM_007607.2 | chr11:84957753-84966054 |
| 3729 | Cacng8 | NM_133190.1 | chr7:3394116-3415605 | 3826 | Car5a | NM_007608.2 | chr8:121916137-121944912 |
| 3730 | Cactin | NM_027381.2 | chr10:81321102-81326251 | 3827 | Car5b | NM_181315.4 | chrX:163976821-164028010 |
| 3731 | Cacul1 | NM_001172096.1 | chr19:60524695-60581023 | 3828 | Car6 | NM_009802.2 | chr4:150187015-150201135 |
| 3732 | Cacybp | NM_009789.2 | chr1:160202366-160212892 | 3829 | Car7 | NM_053070.3 | chr8:104540806-104550343 |
| 3733 | Cad | NM_001289522.1 | chr5:31054779-31078479 | 3830 | Car8 | NM_007592.3 | chr4:8141492-8239041 |
| 3734 | Cadm1 | NM_001025600.1 | chr9:47580351-47853385 | 3831 | Car9 | NM_139305.2 | chr4:43507025-43513725 |
| 3735 | Cadm2 | NM_001145977.1 | chr16:66655420-67620908 | 3832 | Card10 | NM_130859.2 | chr15:78775135-78803042 |
| 3736 | Cadm3 | NM_053199.3 | chr1:173334253-173367695 | 3833 | Card11 | NM_175362.2 | chr5:140872998-141000596 |
| 3737 | Cadm4 | NM_153112.3 | chr7:24482022-24504533 | 3834 | Card14 | NM_130886.3 | chr11:119314786-119345375 |
| 3738 | Cadps | NM_001042562.1 | chr14:13122562-12823079 | 3835 | Card6 | NM_001163338.1 | chr15:5097438-5108533 |
| 3739 | Cadps2 | NM_001252305.1 | chr6:23262773-23589421 | 3836 | Card9 | NM_001037747.1 | chr2:26352311-26359547 |
| 3740 | Cage1 | NM_027724.2 | chr13:38006051-38036937 | 3837 | Carf | NM_001285463.1 | chr1:60098246-60153953 |
| 3741 | Calb1 | NM_009788.4 | chr4:15881263-15906709 | 3838 | Carhsp1 | NM_025821.2 | chr16:8658586-8672153 |
| 3742 | Calb2 | NM_007586.1 | chr8:110142537-110168206 | 3839 | Carkd | NM_001190357.1 | chr8:11497505-11513286 |
| 3743 | Calca | NM_001033954.1 | chr7:114631477-114636357 | 3840 | Carm1 | NM_021531.6 | chr9:21546893-21589465 |
| 3744 | Calcb | NM_054084.2 | chr7:114718642-114723365 | 3841 | Carns1 | NM_134148.2 | chr19:4164323-4175479 |
| 3745 | Calcoco1 | NM_026192.3 | chr15:102706776-102722178 | 3842 | Cars | NM_001252593.1 | chr7:143557229-143600090 |
| 3746 | Calcoco2 | NM_001271018.1 | chr11:96098915-96111962 | 3843 | Cars2 | NM_024248.1 | chr8:11514016-11550771 |
| 3747 | Calcr | NM_001042725.1 | chr6:3685719-3763623 | 3844 | Cartpt | NM_001081493.2 | chr13:99898482-99900683 |
| 3748 | Calcrl | NM_018782.3 | chr2:84326626-84425266 | 3845 | Casc1 | NM_172222.4 | chr6:145174871-145210970 |
| 3749 | Cald1 | NM_145575.3 | chr6:34709443-34775469 | 3846 | Casc3 | NM_138660.2 | chr11:98809807-98833807 |
| 3750 | Calhm1 | NM_001081271.1 | chr19:47141034-47144174 | 3847 | Casc4 | NM_001205369.1 | chr2:121866969-121936207 |
| 3751 | Calhm2 | NM_133746.5 | chr19:47132231-47138294 | 3848 | Casc5 | NM_029617.2 | chr2:119047118-119104121 |
| 3752 | Calm1 | NM_009790.5 | chr12:100399434-100209824 | 3849 | Casd1 | NM_145398.2 | chr6:4601065-4643381 |
| 3753 | Calm2 | NM_007589.5 | chr17:87433400-87446935 | 3850 | Cask | NM_001284503.1 | chrX:13517080-13846556 |
| 3754 | Calm3 | NM_007590.3 | chr7:16915378-16924032 | 3851 | Caskin1 | NM_027937.2 | chr7:24488782-24508067 |
| 3755 | Calm4 | NM_020036.4 | chr13:3837756-3838671 | 3852 | Caskin2 | NM_080643.2 | chr11:115799351-115813592 |
| 3756 | Calm5 | NM_001008706.2 | chr13:3854472-3854761 | 3853 | Casp1 | NM_009807.2 | chr9:5298516-5307281 |
| 3757 | Calml3 | NM_027416.3 | chr13:3802892-3804318 | 3854 | Casp12 | NM_009808.4 | chr9:5345475-5373034 |
| 3758 | Calml4 | NM_001102468.1 | chr9:62858103-62875917 | 3855 | Casp14 | NM_009809.5 | chr10:78711994-78718293 |
| 3759 | Caln1 | NM_021471.3 | chr5:130448791-130840645 | 3856 | Casp2 | NM_007610.2 | chr6:42264984-42282508 |
| 3760 | Calr | NM_007591.3 | chr8:84842087-84846931 | 3857 | Casp3 | NM_001284409.1 | chr8:46617290-46639698 |
| 3761 | Calr3 | NM_028500.3 | chr8:72424182-72443778 | 3858 | Casp4 | NM_007609.3 | chr9:5308848-5336791 |
| 3762 | Calr4 | NM_001033226.4 | chr4:109235631-109254577 | 3859 | Casp6 | NM_009811.4 | chr3:129901414-129914112 |
| 3763 | Calu | NM_001285412.1 | chr6:29348105-29376675 | 3860 | Casp7 | NM_007611.2 | chr19:56397128-56442343 |
| 3764 | Caly | NM_011190385.1 | chr7:140082548-140082548 | 3861 | Casp8 | NM_009810.2 | chr1:58802501-58847503 |
| 3765 | Camk1 | NM_133926.2 | chr6:113334123-113343922 | 3862 | Casp8ap2 | NM_001122978.1 | chr4:32615472-32653265 |
| 3766 | Camk1d | NM_001290374.1 | chr2:5293456-5714762 | 3863 | Casp9 | NM_001277932.1 | chr4:141793611-141815978 |
| 3767 | Camk1g | NM_144817.2 | chr1:193346345-193370282 | 3864 | Casq1 | NM_009813.2 | chr1:172209893-172219895 |
| 3768 | Camk2a | NM_001286809.1 | chr18:60963553-60988152 | 3865 | Casq2 | NM_009814.3 | chr3:102086454-102146512 |
| 3769 | Camk2b | NM_001174053.1 | chr11:5969665-6085748 | 3866 | Casr | NM_013803.2 | chr16:36493695-36562134 |
| 3770 | Camk2d | NM_001025438.3 | chr3:126596950-126846326 | 3867 | Cass4 | NM_001080820.2 | chr2:172393793-172433757 |
| 3771 | Camk2g | NM_001039138.2 | chr14:20734872-20794088 | 3868 | Cast | NM_009817.4 | chr13:74693293-74807960 |
| 3772 | Camk2n1 | NM_025455.1 | chr4:138460326-138460326 | 3869 | Casz1 | NM_001159344.1 | chr4:148604391-148954892 |
| 3773 | Camk2n2 | NM_028420.2 | chr16:20619214-20621278 | 3870 | Cat | NM_009804.2 | chr2:103453903-103485153 |
| 3774 | Camk4 | NM_009793.3 | chr18:32939040-33195767 | 3871 | Catip | NM_001033345.2 | chr1:74362107-74369321 |
| 3775 | Camkk1 | NM_018883.2 | chr11:73019907-73042065 | 3872 | Catsper1 | NM_139301.2 | chr19:5335740-5344163 |
| 3776 | Camkk2 | NM_001199676.1 | chr5:122731169-122779410 | 3873 | Catsper2 | NM_153075.3 | chr2:121394354-121413792 |
| 3777 | Camkmt | NM_028676.2 | chr17:85090699-85458580 | 3874 | Catsper3 | NM_001252487.1 | chr13:55784978-55809000 |
| 3778 | Camkv | NM_145621.2 | chr9:107935919-107949691 | 3875 | Catsper4 | NM_001130030.1 | chr4:134211967-134227383 |
| 3779 | Caml | NM_007596.2 | chr15:55623004-55632416 | 3876 | Catsperb | NM_173025.2 | chr12:101404672-101626009 |
| 3780 | Camp | NM_009921.2 | chr9:109847376-109849456 | 3877 | Catsperd | NM_175350.3 | chr17:56628142-56664456 |
| 3781 | Camsap1 | NM_001276359.1 | chr2:25926837-25983282 | 3878 | Catsperg1 | NM_001164658.1 | chr7:29181531-29214033 |
| 3782 | Camsap2 | NM_001081360.1 | chr1:136268122-136346104 | 3879 | Catsperg2 | NM_029714.3 | chr7:29697218-29727015 |

Fig.21 - 21

| | | | | | | | |
|---|---|---|---|---|---|---|---|
| 3880 | Cav1 | NM_001243064.1 | chr6:17307639-17341328 | 3977 | Ccdc171 | NM_001081012.1 | chr4:83525544-83864670 |
| 3881 | Cav2 | NM_001277756.1 | chr6:17281184-17282684 | 3978 | Ccdc172 | NM_029372.2 | chr19:58512001-58553085 |
| 3882 | Cav3 | NM_007617.3 | chr6:112459504-112472872 | 3979 | Ccdc173 | NM_001077684.1 | chr2:69758056-69789486 |
| 3883 | Cbfa2t2 | NM_001285486.1 | chr2:154436483-154539356 | 3980 | Ccdc174 | NM_172730.2 | chr6:91878052-91899848 |
| 3884 | Cbfa2t3 | NM_001109873.1 | chr8:122625135-122678175 | 3981 | Ccdc175 | NM_028687.1 | chr12:72161291-72185029 |
| 3885 | Cbfb | NM_001161456.1 | chr8:105170673-105217988 | 3982 | Ccdc176 | NM_028377.3 | chr12:84409067-84433780 |
| 3886 | Cbl | NM_007619.2 | chr9:44149261-44234046 | 3983 | Ccdc177 | NM_001008423.2 | chr12:80755446-80760715 |
| 3887 | Cblb | NM_001033238.1 | chr16:52031548-52208046 | 3984 | Ccdc178 | NM_027616.3 | chr18:21810896-22171396 |
| 3888 | Cblc | NM_001161844.1 | chr7:19779717-19796809 | 3985 | Ccdc18 | NM_028481.1 | chr5:108132913-108232949 |
| 3889 | Cbll1 | NM_001253847.1 | chr12:31484828-31499616 | 3986 | Ccdc181 | NM_029115.3 | chr1:164275597-164287847 |
| 3890 | Cbln1 | NM_019626.3 | chr8:87468885.2-87472592 | 3987 | Ccdc183 | NM_029859.1 | chr2:25608628-25617678 |
| 3891 | Cbln2 | NM_172633.4 | chr18:86712064-86718283 | 3988 | Ccdc184 | NM_177716.3 | chr15:98167805-98170134 |
| 3892 | Cbln3 | NM_019820.3 | chr14:55878919-55884256 | 3989 | Ccdc185 | NM_001033547.2 | chr1:182747125-182749180 |
| 3893 | Cbln4 | NM_175631.3 | chr2:172036335-172043466 | 3990 | Ccdc19 | NM_027972.1 | chr1:172521129-172545870 |
| 3894 | Cbr1 | NM_007620.2 | chr16:93607836-93610349 | 3991 | Ccdc22 | NM_138603.3 | chrX:7593808-7605420 |
| 3895 | Cbr2 | NM_007621.2 | chr11:120729484-120732021 | 3992 | Ccdc23 | NM_001038998.2 | chr4:119195524-119201298 |
| 3896 | Cbr3 | NM_173047.3 | chr16:93683218-93690991 | 3993 | Ccdc24 | NM_001034876.1 | chr4:117869259-117872470 |
| 3897 | Cbr4 | NM_145596.2 | chr8:61487783-61503500 | 3994 | Ccdc25 | NM_145944.4 | chr14:65837301-65866604 |
| 3898 | Cbs | NM_001271353.1 | chr17:31612622-31637205 | 3995 | Ccdc27 | NM_001033455.2 | chr4:154026643-154042677 |
| 3899 | Cbwd1 | NM_146097.3 | chr19:24919915-24961616 | 3996 | Ccdc28a | NM_144820.3 | chr10:18213684-18234981 |
| 3900 | Cbx1 | NM_007622.3 | chr11:96789135-96808640 | 3997 | Ccdc28b | NM_025455.2 | chr4:129619273-129623908 |
| 3901 | Cbx2 | NM_007623.3 | chr11:119023020-119031275 | 3998 | Ccdc3 | NM_028804.1 | chr2:5137775-5230866 |
| 3902 | Cbx3 | NM_007624.3 | chr6:51470615-51483704 | 3999 | Ccdc30 | NM_001270435.1 | chr4:119322892-119415521 |
| 3903 | Cbx4 | NM_007625.2 | chr11:119077570-119086237 | 4000 | Ccdc32 | NM_199310.2 | chr2:119017778-119029393 |
| 3904 | Cbx5 | NM_001076789.1 | chr15:103191545-103239816 | 4001 | Ccdc33 | NM_001166282.1 | chr9:58028681-58118823 |
| 3905 | Cbx6 | NM_028763.3 | chr15:79823897-79834333 | 4002 | Ccdc34 | NM_026613.4 | chr2:110017816-110045325 |
| 3906 | Cbx7 | NM_144811.3 | chr15:79915806-79932646 | 4003 | Ccdc34os | NR_040508.1 | chr5:110031249-110050479 |
| 3907 | Cbx8 | NM_013926.1 | chr11:119038435-119040913 | 4004 | Ccdc36 | NM_001135198.1 | chr9:108403632-108428482 |
| 3908 | Cby1 | NM_026634.3 | chr15:79659226-79667660 | 4005 | Ccdc37 | NM_173775.3 | chr6:90403735-90428480 |
| 3909 | Cc2d1a | NM_145974.1 | chr8:84132827-84147753 | 4006 | Ccdc38 | NM_175488.6 | chr10:93540631-93584326 |
| 3910 | Cc2d1b | NM_177045.3 | chr4:108619955-108634122 | 4007 | Ccdc39 | NM_026222.2 | chr3:33812360-33844310 |
| 3911 | Cc2d2a | NM_172274.2 | chr5:43662378-43740970 | 4008 | Ccdc40 | NM_175430.4 | chr11:119228571-119265212 |
| 3912 | Ccar1 | NM_026201.3 | chr10:62743927-62792368 | 4009 | Ccdc42 | NM_177779.3 | chr11:68587036-68597951 |
| 3913 | Ccar2 | NM_146055.3 | chr14:70138168-70153791 | 4010 | Ccdc42b | NM_001195094.1 | chr5:120628334-120634235 |
| 3914 | Ccbe1 | NM_178793.4 | chr18:66056855-66291838 | 4011 | Ccdc43 | NM_025918.3 | chr11:102684687-102697725 |
| 3915 | Ccbl1 | NM_172404.2 | chr2:30185130-30205699 | 4012 | Ccdc47 | NM_026009.2 | chr11:106199355-106216367 |
| 3916 | Ccbl2 | NM_173763.4 | chr3:142701047-142744911 | 4013 | Ccdc50 | NM_001025615.3 | chr16:27388955-27452218 |
| 3917 | Ccdc101 | NM_029339.3 | chr7:126649308-126672779 | 4014 | Ccdc51 | NM_025689.4 | chr9:109082495-109091363 |
| 3918 | Ccdc102a | NM_001033533.3 | chr8:94902868-94918098 | 4015 | Ccdc53 | NM_001122960.1 | chr10:88201096-88246158 |
| 3919 | Ccdc103 | NM_028492.2 | chr11:102881243-102885215 | 4016 | Ccdc54 | NM_027046.3 | chr16:50589858-50591154 |
| 3920 | Ccdc104 | NM_025740.3 | chr11:29221535-29247272 | 4017 | Ccdc55 | NM_001012309.2 | chr11:77044291-77078437 |
| 3921 | Ccdc105 | NM_001034050.1 | chr10:78746923-78753067 | 4018 | Ccdc57 | NM_027745.1 | chr11:120826941-120932872 |
| 3922 | Ccdc106 | NM_001290429.1 | chr7:5056151-5060784 | 4019 | Ccdc58 | NM_001159421.1 | chr16:36071659-36092118 |
| 3923 | Ccdc107 | NM_001037913.2 | chr4:43493364-43495921 | 4020 | Ccdc59 | NM_025602.3 | chr10:105841478-105847510 |
| 3924 | Ccdc108 | NM_001039495.1 | chr1:74902079-74935599 | 4021 | Ccdc6 | NM_001111121.1 | chr10:70097120-70193200 |
| 3925 | Ccdc109b | NM_025779.3 | chr3:129914959-129970206 | 4022 | Ccdc60 | NM_177759.3 | chr5:116125580-116288985 |
| 3926 | Ccdc11 | NM_028948.2 | chr18:74283099-74359984 | 4023 | Ccdc61 | NM_001033314.3 | chr7:18890883-18910404 |
| 3927 | Ccdc110 | NM_001033246.2 | chr8:45934648-45944145 | 4024 | Ccdc62 | NM_001134767.1 | chr5:123930688-123969895 |
| 3928 | Ccdc112 | NM_001160399.1 | chr18:46282150-46311928 | 4025 | Ccdc63 | NM_001289829.1 | chr5:122108051-122134893 |
| 3929 | Ccdc113 | NM_172914.2 | chr8:95534099-95558888 | 4026 | Ccdc64 | NM_001080808.1 | chr5:116549285-115731559 |
| 3930 | Ccdc114 | NM_001033243.2 | chr7:45928397-45948956 | 4027 | Ccdc64b | NM_153784.2 | chr17:23660522-23668619 |
| 3931 | Ccdc115 | NM_027159.2 | chr1:34436669-34439672 | 4028 | Ccdc65 | NM_153518.1 | chr15:98708226-98723333 |
| 3932 | Ccdc116 | NM_001306169.1 | chr16:17136906-17147146 | 4029 | Ccdc66 | NM_177111.3 | chr14:27482404-27508480 |
| 3933 | Ccdc117 | NM_134033.2 | chr11:5528887-5542217 | 4030 | Ccdc67 | NM_181816.2 | chr9:15559863-15627933 |
| 3934 | Ccdc12 | NM_028312.3 | chr9:110656502-110711593 | 4031 | Ccdc68 | NM_203162.2 | chr18:69925558-69969484 |
| 3935 | Ccdc120 | NM_207202.2 | chrX:7741713-7741324 | 4032 | Ccdc69 | NM_177471.4 | chr11:55049737-55078131 |
| 3936 | Ccdc121 | NM_207280.3 | chr1:181509632-181511451 | 4033 | Ccdc7 | NM_001197041.1 | chr8:129045476-129065492 |
| 3937 | Ccdc122 | NM_175369.4 | chr14:77036771-77112263 | 4034 | Ccdc70 | NM_026459.3 | chr8:21970595-21974041 |
| 3938 | Ccdc124 | NM_026964.3 | chr8:70868226-70873490 | 4035 | Ccdc71 | NM_133744.4 | chr9:108460617-108465945 |
| 3939 | Ccdc126 | NM_001168386.2 | chr13:100669480-100697240 | 4036 | Ccdc71l | NM_001162903.1 | chr12:32378788-32382943 |
| 3940 | Ccdc126 | NM_175098.6 | chr6:49319273-49341586 | 4037 | Ccdc73 | NM_177600.4 | chr2:104886323-104999737 |
| 3941 | Ccdc127 | NM_001168658.1 | chr13:74350316-74365783 | 4038 | Ccdc74a | NM_001166164.1 | chr16:17646469-17650738 |
| 3942 | Ccdc129 | NM_001263166.1 | chr6:55830317-55978598 | 4039 | Ccdc77 | NM_026028.5 | chr6:120324321-120357469 |
| 3943 | Ccdc13 | NM_028384.1 | chr9:121797626-121839461 | 4040 | Ccdc78 | NM_001165929.1 | chr17:25786579-25790513 |
| 3944 | Ccdc130 | NM_026350.3 | chr8:84257766-84270402 | 4041 | Ccdc79 | NM_180958.3 | chr8:104446718-104509887 |
| 3945 | Ccdc132 | NM_001167750.1 | chr6:33498392-33603533 | 4042 | Ccdc8 | NM_001101535.1 | chr7:16994587-16996685 |
| 3946 | Ccdc134 | NM_172428.2 | chr15:82327923-82342202 | 4043 | Ccdc80 | NM_026439.2 | chr16:45094052-45127924 |
| 3947 | Ccdc135 | NM_001042715.3 | chr8:95055102-95078141 | 4044 | Ccdc81 | NM_001162979.1 | chr7:89866147-89903629 |
| 3948 | Ccdc136 | NM_001061378.1 | chr6:29396925-29426995 | 4045 | Ccdc82 | NM_025634.2 | chr9:13346978-13292353 |
| 3949 | Ccdc137 | NM_152807.3 | chr11:120458128-120464353 | 4046 | Ccdc83 | NM_029256.3 | chr7:90235760-90265432 |
| 3950 | Ccdc138 | NM_001162956.1 | chr10:58497936-58576244 | 4047 | Ccdc84 | NM_201372.3 | chr9:44410163-44418007 |
| 3951 | Ccdc14 | NM_172824.3 | chr16:34690615-34725194 | 4048 | Ccdc85a | NM_001166661.2 | chr11:28385683-28584324 |
| 3952 | Ccdc141 | NM_001025576.3 | chr2:770.9905-77170635 | 4049 | Ccdc85b | NM_001243307.1 | chr19:5453162-5457563 |
| 3953 | Ccdc142 | NM_001081266.3 | chr6:83101515-83109121 | 4050 | Ccdc85c | NM_001159910.1 | chr12:108206344-108275417 |
| 3954 | Ccdc144b | NM_178418.4 | chr3:36007246-36053547 | 4051 | Ccdc86 | NM_023731.3 | chr19:10941480-10949266 |
| 3955 | Ccdc146 | NM_029195.1 | chr5:21292960-21424677 | 4052 | Ccdc87 | NM_207268.3 | chr19:4839365-4842528 |
| 3956 | Ccdc147 | NM_001163267.1 | chr19:47937711-48035379 | 4053 | Ccdc88a | NM_176841.4 | chr11:29374171-29510808 |
| 3957 | Ccdc148 | NM_001001378.1 | chr2:58821697-59018606 | 4054 | Ccdc88b | NM_001081291.1 | chr19:6844622-6858211 |
| 3958 | Ccdc149 | NM_001256059.1 | chr5:52347650-52471543 | 4055 | Ccdc88c | NM_026681.4 | chr12:100912699-101028983 |
| 3959 | Ccdc15 | NM_001081429.1 | chr9:37275834-37348392 | 4056 | Ccdc89 | NM_027298.1 | chr7:90426811-90428664 |
| 3960 | Ccdc150 | NM_030025.2 | chr1:54250682-54368727 | 4057 | Ccdc9 | NM_001136471.1 | chr7:16274041-16286795 |
| 3961 | Ccdc151 | NM_001163785.1 | chr9:21989870-22002634 | 4058 | Ccdc90b | NM_001162918.1 | chr7:92561148-92582294 |
| 3962 | Ccdc152 | NM_001166063.2 | chr15:3280826-3303526 | 4059 | Ccdc91 | NM_025911.2 | chr6:147475870-147632612 |
| 3963 | Ccdc153 | NM_001081369.2 | chr9:44246076-44247306 | 4060 | Ccdc92 | NM_144819.2 | chr5:124834433-124862221 |
| 3964 | Ccdc154 | NM_001079929.2 | chr17:25162480-25171913 | 4061 | Ccdc93 | NM_001025156.2 | chr1:121431066-121506460 |
| 3965 | Ccdc155 | NM_201374.2 | chr7:45118675-45204892 | 4062 | Ccdc94 | NM_028381.3 | chr17:55959186-55967951 |
| 3966 | Ccdc157 | NM_001034041.1 | chr11:4141123-4160293 | 4063 | Ccdc96 | NM_025725.2 | chr5:36484587-36488171 |
| 3967 | Ccdc158 | NM_177230.3 | chr5:92608294-92675127 | 4064 | Ccdc97 | NM_028771.2 | chr7:25711116-25719053 |
| 3968 | Ccdc159 | NM_001164614.1 | chr9:21927470-21935872 | 4065 | Ccer1 | NM_025724.2 | chr10:97693058-97694926 |
| 3969 | Ccdc160 | NM_001034069.1 | chrX:52791199-52799468 | 4066 | Ccharl | NM_146248.2 | chr7:35517115-35531015 |
| 3970 | Ccdc162 | NM_001303469.1 | chr10:41538409-41716568 | 4067 | Ccin | NM_001002787.2 | chr4:43983503-43985533 |
| 3971 | Ccdc163 | NM_026714.2 | chr4:116708929-116715104 | 4068 | Cck | NM_001284508.2 | chr9:121489823-121495694 |
| 3972 | Ccdc166 | NM_001163518.1 | chr15:79871-75982285 | 4069 | Cckar | NM_009827.2 | chr5:53698484-53707704 |
| 3973 | Ccdc167 | NM_001163741.2 | chr17:29695976-29717017 | 4070 | Cckbr | NM_007627.5 | chr7:105425730-105436339 |
| 3974 | Ccdc169 | NM_001034069.1 | chr3:55172936-55172936 | 4071 | Ccl1 | NM_011329.3 | chr11:82176665-82179812 |
| 3975 | Ccdc17 | NM_001037916.3 | chr4:116596729-116600266 | 4072 | Ccl11 | NM_011330.3 | chr11:82097831-82062956 |
| 3976 | Ccdc170 | NM_001195672.1 | chr10:4509871-4561111 | 4073 | Ccl12 | NM_011331.2 | chr11:82101844-82103399 |

Fig.21 - 22

| | | | | | | | |
|---|---|---|---|---|---|---|---|
| 4074 | Ccl17 | NM_011332.3 | chr8:94810452-94812036 | 4171 | Cd200r1 | NM_021325.3 | chr16:44765735-44794977 |
| 4075 | Ccl19 | NM_011888.2 | chr4:102333-42756518 | 4172 | Cd200r2 | NM_206535.1 | chr16:44867096-44915840 |
| 4076 | Ccl2 | NM_011333.3 | chr11:82035576-82037452 | 4173 | Cd200r3 | NM_001128132.1 | chr16:44943677-44966290 |
| 4077 | Ccl20 | NM_001159738.1 | chr1:83118765-83119167 | 4174 | Cd200r4 | NM_207244.2 | chr16:44820727-44839150 |
| 4078 | Ccl21a | NM_011124.4 | chr4:120654-42773991 | 4175 | Cd207 | NM_144943.3 | chr6:83671206-83677857 |
| 4079 | Ccl21b | NM_011335.2 | chr4:0-42613253 | 4176 | Cd209a | NM_133238.5 | chr8:37433994-3748384 |
| 4080 | Ccl21c | NM_023052.2 | chr4:0-42613253 | 4177 | Cd209b | NM_001037800.3 | chr8:3917654-3926841 |
| 4081 | Ccl22 | NM_009137.2 | chr8:94745683-94751388 | 4178 | Cd209c | NM_130903.3 | chr8:3940221-3946863 |
| 4082 | Ccl24 | NM_019577.4 | chr5:135569936-135573043 | 4179 | Cd209d | NM_130904.2 | chr8:3871823-3878499 |
| 4083 | Ccl25 | NM_009138.3 | chr8:4349587-4360020 | 4180 | Cd209e | NM_130905.2 | chr8:3847972-3854286 |
| 4084 | Ccl26 | NM_001013412.2 | chr5:135560447-135563569 | 4181 | Cd209f | NM_026956.2 | chr8:4102792-4105764 |
| 4085 | Ccl27a | NM_001048179.1 | chr4:41769469-41774134 | 4182 | Cd209g | NM_027343.3 | chr8:4134735-4137707 |
| 4086 | Ccl27b | NM_001199959.1 | chr4:3059-42656005 | 4183 | Cd22 | NM_001043317.2 | chr7:30865403-30880342 |
| 4087 | Ccl28 | NM_020279.3 | chr13:119623818-119654358 | 4184 | Cd226 | NM_001039149.1 | chr18:89197426-89270327 |
| 4088 | Ccl3 | NM_011337.2 | chr11:83647842-83649378 | 4185 | Cd244 | NM_018729.2 | chr1:171559192-171585316 |
| 4089 | Ccl4 | NM_013652.2 | chr11:83662583-83664683 | 4186 | Cd247 | NM_001113391.2 | chr1:165788680-165862112 |
| 4090 | Ccl5 | NM_013653.3 | chr11:83525778-83530518 | 4187 | Cd248 | NM_054042.2 | chr19:5068077-5070639 |
| 4091 | Ccl6 | NM_009139.3 | chr11:83587685-83593087 | 4188 | Cd24a | NM_009846.2 | chr10:43579168-43584265 |
| 4092 | Ccl7 | NM_013654.3 | chr11:82045713-82047523 | 4189 | Cd27 | NM_001033126.2 | chr6:125232823-125237027 |
| 4093 | Ccl8 | NM_021443.3 | chr11:82115184-82116799 | 4190 | Cd274 | NM_021893.3 | chr19:29367437-29388094 |
| 4094 | Ccl9 | NM_011338.2 | chr11:83572916-83578636 | 4191 | Cd276 | NM_133983.4 | chr9:58524299-58540940 |
| 4095 | Ccm2 | NM_001190343.1 | chr11:6546886-6596761 | 4192 | Cd28 | NM_007642.4 | chr1:60746387-60773359 |
| 4096 | Ccm2l | NM_145536.3 | chr2:153065954-153081735 | 4193 | Cd2ap | NM_009847.3 | chr17:42792950-42876424 |
| 4097 | Ccna1 | NM_007628.3 | chr3:55045468-55059055 | 4194 | Cd2bp2 | NM_001285905.1 | chr7:127191659-127196077 |
| 4098 | Ccna2 | NM_009828.2 | chr3:36564864-36571996 | 4195 | Cd300a | NM_170758.3 | chr11:114890040-114904651 |
| 4099 | Ccnb1 | NM_172301.3 | chr13:100778738-100786486 | 4196 | Cd300c | NM_199225.1 | chr11:114956277-114960417 |
| 4100 | Ccnb1ip1 | NM_001111119.1 | chr14:50789248-50795728 | 4197 | Cd300e | NM_172050.2 | chr11:115051916-115062038 |
| 4101 | Ccnb2 | NM_007630.2 | chr9:70407688-70421554 | 4198 | Cd300lb | NM_199221.2 | chr11:114922780-114934386 |
| 4102 | Ccnb3 | NM_183015.3 | chrX:6979653-7041619 | 4199 | Cd300ld | NM_145437.2 | chr11:114982445-114998986 |
| 4103 | Ccnc | NM_001122982.2 | chr4:21727700-21747962 | 4200 | Cd300lf | NM_001169193.1 | chr11:115116213-115133992 |
| 4104 | Ccnd1 | NM_007631.2 | chr7:144929930-144939925 | 4201 | Cd300lg | NM_001160711.1 | chr11:102043510-102095617 |
| 4105 | Ccnd2 | NM_009829.3 | chr6:127125708-127151048 | 4202 | Cd300lh | NM_199201.1 | chr11:115031485-115048295 |
| 4106 | Ccnd3 | NM_001081635.1 | chr17:47505050-47599688 | 4203 | Cd302 | NM_001290660.1 | chr2:60251992-60284484 |
| 4107 | Ccndbp1 | NM_010761.2 | chr2:121008407-121016912 | 4204 | Cd320 | NM_019421.3 | chr17:33843090-33849774 |
| 4108 | Ccne1 | NM_007633.2 | chr7:38097983-38107490 | 4205 | Cd33 | NM_001111058.1 | chr7:43527456-43533171 |
| 4109 | Ccne2 | NM_001037134.2 | chr4:11191350-11204779 | 4206 | Cd34 | NM_001111059.1 | chr1:194938820-194961292 |
| 4110 | Ccnf | NM_007634.4 | chr17:24223231-24251409 | 4207 | Cd36 | NM_001159555.1 | chr5:17781689-17835896 |
| 4111 | Ccng1 | NM_009831.2 | chr11:40748551-40755286 | 4208 | Cd37 | NM_001290802.1 | chr7:45238631-45259115 |
| 4112 | Ccng2 | NM_007635.4 | chr5:93267572-93276231 | 4209 | Cd38 | NM_007646.5 | chr5:43868808-43912374 |
| 4113 | Ccnh | NM_023243.5 | chr13:85189476-85213723 | 4210 | Cd3d | NM_013487.3 | chr9:44981785-44987052 |
| 4114 | Ccni | NM_017367.3 | chr5:93181932-93206495 | 4211 | Cd3e | NM_007648.4 | chr9:44998742-45009590 |
| 4115 | Ccnj | NM_172839.4 | chr19:40831278-40848570 | 4212 | Cd3eap | NM_145322.2 | chr7:19356008-19358483 |
| 4116 | Ccnjl | NM_001045530.2 | chr11:43528748-43586999 | 4213 | Cd3g | NM_009850.2 | chr9:44969571-44980431 |
| 4117 | Ccnk | NM_009892.2 | chr12:108179737-108203359 | 4214 | Cd4 | NM_013488.2 | chr6:124864692-124888209 |
| 4118 | Ccnl1 | NM_019937.3 | chr3:65946150-65958225 | 4215 | Cd40 | NM_011611.2 | chr2:165055635-165071654 |
| 4119 | Ccnl2 | NM_207678.1 | chr4:155812488-155824643 | 4216 | Cd40lg | NM_011616.2 | chrX:57212142-57224642 |
| 4120 | Ccno | NM_001081062.1 | chr13:112987801-112990778 | 4217 | Cd44 | NM_001039150.1 | chr2:102811141-102901665 |
| 4121 | Ccnt1 | NM_009833.1 | chr15:98548210-98567636 | 4218 | Cd46 | NM_010778.4 | chr1:195041237-195092248 |
| 4122 | Ccnt2 | NM_028399.1 | chr1:127774163-127804837 | 4219 | Cd47 | NM_010581.3 | chr16:49855653-49911683 |
| 4123 | Ccny | NM_026484.3 | chr18:9314040-9450150 | 4220 | Cd48 | NM_007649.4 | chr1:171682054-171705257 |
| 4124 | Ccnyl1 | NM_001097644.1 | chr1:64691344-64725642 | 4221 | Cd5 | NM_007650.2 | chr19:10718142-10738974 |
| 4125 | Ccp110 | NM_182995.1 | chr7:118712610-118737018 | 4222 | Cd52 | NM_013706.2 | chr4:134093537-134095073 |
| 4126 | Ccpg1 | NM_001114328.2 | chr9:72985503-73013938 | 4223 | Cd53 | NM_007651.3 | chr3:106758860-106790149 |
| 4127 | Ccpg1os | NM_001198789.1 | chr9:72979724-72985376 | 4224 | Cd55 | NM_010016.2 | chr1:130489029-130462740 |
| 4128 | Ccr1 | NM_009912.4 | chr9:123915265-123968692 | 4225 | Cd59a | NM_001111960.2 | chr2:104098800-104115416 |
| 4129 | Ccr10 | NM_007721.4 | chr11:101172997-101175443 | 4226 | Cd59b | NM_181858.1 | chr2:104071909-104084957 |
| 4130 | Ccr1l1 | NM_007718.3 | chr9:123976948-123978408 | 4227 | Cd5l | NM_009690.2 | chr3:87357880-87371074 |
| 4131 | Ccr2 | NM_009915.2 | chr9:124102182-124109140 | 4228 | Cd6 | NM_001037801.2 | chr19:10789338-10830058 |
| 4132 | Ccr3 | NM_009914.4 | chr9:124021970-124031689 | 4229 | Cd63 | NM_001042580.1 | chr10:128908918-128912818 |
| 4133 | Ccr4 | NM_009916.2 | chr9:114490315-114496544 | 4230 | Cd68 | NM_001291058.1 | chr11:69664212-69666170 |
| 4134 | Ccr5 | NM_009917.5 | chr9:124121542-124127183 | 4231 | Cd69 | NM_001033122.3 | chr6:129276324-129275369 |
| 4135 | Ccr6 | NM_001190333.1 | chr17:8236042-8257129 | 4232 | Cd7 | NM_009854.2 | chr11:121036748-121039478 |
| 4136 | Ccr7 | NM_017466.5 | chr11:99145996-99155077 | 4233 | Cd70 | NM_011617.2 | chr17:57145996-57149777 |
| 4137 | Ccr8 | NM_007720.2 | chr9:120092132-120094906 | 4234 | Cd72 | NM_001110320.1 | chr4:43447723-43454626 |
| 4138 | Ccr9 | NM_001166625.1 | chr9:123767210-123783457 | 4235 | Cd74 | NM_001042605.1 | chr18:60803848-60812652 |
| 4139 | Ccrl2 | NM_017466.5 | chr9:111054833-111057270 | 4236 | Cd79a | NM_007655.3 | chr7:24897510-24902197 |
| 4140 | Ccm4l | NM_009834.2 | chr3:51224446-51251654 | 4237 | Cd79b | NM_008339.3 | chr11:106311340-106314562 |
| 4141 | Ccs | NM_016892.3 | chr19:4825365-4839322 | 4238 | Cd80 | NM_009855.2 | chr16:38458932-38486932 |
| 4142 | Ccsap | NM_027298.2 | chr4:234048-123860209 | 4239 | Cd81 | NM_133665.2 | chr7:143052749-143067930 |
| 4143 | Ccser1 | NM_001164316.1 | chr6:61180324-62382863 | 4240 | Cd82 | NM_001136056.2 | chr2:93419101-93462956 |
| 4144 | Ccser2 | NM_027645.1 | chr14:36874935-36968764 | 4241 | Cd83 | NM_001289915.1 | chr13:43785111-43803133 |
| 4145 | Cct2 | NM_007636.2 | chr10:117050997-117063814 | 4242 | Cd84 | NM_001252472.1 | chr1:171839696-171855097 |
| 4146 | Cct3 | NM_009836.1 | chr3:88297134-88321766 | 4243 | Cd86 | NM_019388.3 | chr16:36603868-36666077 |
| 4147 | Cct4 | NM_009837.1 | chr11:22990592-23003336 | 4244 | Cd8a | NM_001081110.2 | chr6:71379426-71379171 |
| 4148 | Cct5 | NM_007637.2 | chr15:31590883-31601804 | 4245 | Cd8b1 | NM_009858.2 | chr6:71322811-71337451 |
| 4149 | Cct6a | NM_009838.2 | chr5:129787355-129846443 | 4246 | Cd9 | NM_007657.3 | chr6:125460265-125494755 |
| 4150 | Cct6b | NM_001291242.1 | chr11:82719247-82764321 | 4247 | Cd93 | NM_010740.3 | chr2:148436650-148443535 |
| 4151 | Cct7 | NM_007638.4 | chr6:85481504-85468477 | 4248 | Cd96 | NM_032465.2 | chr16:46035656-46120248 |
| 4152 | Cct8 | NM_009512.4 | chr18:87483324-87495869 | 4249 | Cd97 | NM_001163029.1 | chr8:83723250-83741311 |
| 4153 | Cct8l1 | NM_198621.2 | chr5:25518066-25518027 | 4250 | Cd99l2 | NM_001199349.1 | chrX:71420059-71492849 |
| 4154 | Cct21 | NM_177682.3 | chr5:143987908-144014853 | 4251 | Cda | NM_028176.1 | chr4:138338527-138367955 |
| 4155 | Cd101 | NM_001167906.1 | chr3:100993529-101029495 | 4252 | Cdadc1 | NM_001168535.1 | chr14:59559387-59597959 |
| 4156 | Cd109 | NM_153098.3 | chr9:78615545-78716260 | 4253 | Cdan1 | NM_026891.3 | chr2:120716153-120731517 |
| 4157 | Cd14 | NM_009841.4 | chr18:36725063-36726815 | 4254 | Cdc123 | NM_133837.4 | chr2:5794293-5844960 |
| 4158 | Cd151 | NM_011110491.1 | chr14:146736T-141471481 | 4255 | Cdc14a | NM_001080818.2 | chr3:116272552-116424032 |
| 4159 | Cd160 | NM_001163496.1 | chr3:96798762-96829361 | 4256 | Cdc14b | NM_001129889.1 | chr13:64192544-64248533 |
| 4160 | Cd163 | NM_001170336.1 | chr6:124304650-124330527 | 4257 | Cdc16 | NM_027276.2 | chr8:13575689-13781882 |
| 4161 | Cd163l1 | NM_172909.4 | chr7:140218266-140231145 | 4258 | Cdc20 | NM_023223.2 | chr4:118432900-118437343 |
| 4162 | Cd164 | NM_016898.2 | chr10:41519499-41531042 | 4259 | Cdc20b | NM_001281487.1 | chr13:113035378-113091135 |
| 4163 | Cd164l2 | NM_027152.1 | chr4:133220808-133224554 | 4260 | Cdc23 | NM_178347.4 | chr18:34631682-34651736 |
| 4164 | Cd177 | NM_026862.3 | chr7:24743982-24760311 | 4261 | Cdc25a | NM_007658.3 | chr9:109875578-109893896 |
| 4165 | Cd180 | NM_008533.2 | chr13:102693557-102706631 | 4262 | Cdc25b | NM_001111075.4 | chr2:131186947-131198513 |
| 4166 | Cd19 | NM_009844.2 | chr7:126408647-126414870 | 4263 | Cdc25c | NM_009860.3 | chr18:34732994-34751533 |
| 4167 | Cd1d1 | NM_007639.3 | chr3:86995835-86999340 | 4264 | Cdc26 | NM_139291.3 | chr4:62394588-62408623 |
| 4168 | Cd1d2 | NM_001289449.1 | chr3:86985635-86989552 | 4265 | Cdc7 | NM_001285988.1 | chr11:104502525-104550620 |
| 4169 | Cd2 | NM_013486.2 | chr3:101275907-101287939 | 4266 | Cdc34 | NM_177613.2 | chr10:79682194-79688398 |
| 4170 | Cd200 | NM_010818.3 | chr16:45382134-45409053 | 4267 | Cdc37 | NM_016742.4 | chr9:21138540-21149906 |

Fig.21 - 23

| | | | | | | | | |
|---|---|---|---|---|---|---|---|---|
| 4268 | Cdc37l1 | NM_025950.3 | chr19:28990351-29020237 | 4365 | Cdkn2d | NM_009878.3 | chr9:21288463-21291209 |
| 4269 | Cdc40 | NM_027879.2 | chr10:40831621-40883143 | 4366 | Cdkn3 | NM_028222.1 | chr14:46760540-46771525 |
| 4270 | Cdc42 | NM_001243769.1 | chr4:137321762-137357759 | 4367 | Cdnf | NM_177647.4 | chr2:3513064-3526376 |
| 4271 | Cdc42bpa | NM_001033285.1 | chr1:179961088-180165602 | 4368 | Cdo1 | NM_033037.3 | chr18:46713204-46728342 |
| 4272 | Cdc42bpb | NM_183016.2 | chr12:111292971-111377718 | 4369 | Cdon | NM_021339.2 | chr9:35452075-35507652 |
| 4273 | Cdc42bpg | NM_001033342.1 | chr19:6306456-6325652 | 4370 | Cdpf1 | NM_001164625.1 | chr15:85860971-85811697 |
| 4274 | Cdc42ep1 | NM_027219.3 | chr15:78842646-78850902 | 4371 | Cdr1 | NM_001166258.1 | chrX:61183245-61185558 |
| 4275 | Cdc42ep2 | NM_026772.2 | chr19:5917555-5924816 | 4372 | Cdt2 | NM_007672.2 | chr1:120957036-120982312 |
| 4276 | Cdc42ep3 | NM_026514.2 | chr17:79334024-79356091 | 4373 | Cdr2l | NM_001080929.1 | chr11:115381915-115396132 |
| 4277 | Cdc42ep4 | NM_001163346.1 | chr11:113726849-113751815 | 4374 | Cdrt4 | NM_025496.1 | chr11:62951192-62993095 |
| 4278 | Cdc42ep5 | NM_021454.3 | chr7:4151259-4164699 | 4375 | Cds1 | NM_173370.3 | chr5:101765129-101823852 |
| 4279 | Cdc42se1 | NM_001038708.3 | chr3:95228942-95236424 | 4376 | Cds2 | NM_001291039.1 | chr2:132285938-132312050 |
| 4280 | Cdc42se2 | NM_178626.3 | chr1:54717414-54787703 | 4377 | Cdsn | NM_001008424.2 | chr17:35552127-35557180 |
| 4281 | Cdc45 | NM_001161623.1 | chr16:18780446-18811639 | 4378 | Cdt1 | NM_026014.3 | chr8:122568014-122573130 |
| 4282 | Cdc5l | NM_152810.2 | chr17:45391887-45433707 | 4379 | Cdv3 | NM_001134426.1 | chr9:103353101-103365780 |
| 4283 | Cdc6 | NM_001025779.1 | chr11:98907888-98923942 | 4380 | Cdx1 | NM_009880.3 | chr18:61018861-61036199 |
| 4284 | Cdc7 | NM_001271566.1 | chr5:106964560-106984439 | 4381 | Cdx2 | NM_007673.3 | chr5:147300899-147307249 |
| 4285 | Cdc73 | NM_145990.2 | chr1:143603275-143702893 | 4382 | Cdx4 | NM_007674.3 | chrX:103321397-103330224 |
| 4286 | Cdca2 | NM_001110162.1 | chr14:67676353-67715610 | 4383 | Cdyl | NM_001123386.1 | chr13:35743401-35874064 |
| 4287 | Cdca3 | NM_013538.5 | chr6:124830175-124833701 | 4384 | Cdyl2 | NM_029441.3 | chr8:116568723-116732991 |
| 4288 | Cdca4 | NM_028023.3 | chr12:112820234-112829389 | 4385 | Ceacam1 | NM_001039185.1 | chr7:25461701-25477625 |
| 4289 | Cdca5 | NM_026410.3 | chr19:6085096-6091773 | 4386 | Ceacam10 | NM_007675.4 | chr7:24777203-24784655 |
| 4290 | Cdca7 | NM_025866.3 | chr2:72476218-72486890 | 4387 | Ceacam11 | NM_023289.1 | chr7:17972166-17978556 |
| 4291 | Cdca7l | NM_146040.1 | chr12:117843860-117878706 | 4388 | Ceacam12 | NM_001162523 | chr7:18065928-18077988 |
| 4292 | Cdca8 | NM_026560.4 | chr4:124918464-124936917 | 4389 | Ceacam13 | NM_027210 | chr7:18009888-18019220 |
| 4293 | Cdcp1 | NM_133974.3 | chr9:123172284-123216038 | 4390 | Ceacam14 | NM_025957 | chr7:17812681-17815627 |
| 4294 | Cdcp2 | NM_172873.3 | chr4:107096890-107107748 | 4391 | Ceacam15 | NM_175315.1 | chr7:16671330-16675705 |
| 4295 | Cdh1 | NM_009864.2 | chr8:106603367-106670246 | 4392 | Ceacam16 | NM_001033419.1 | chr7:19852096-19861299 |
| 4296 | Cdh10 | NM_009867.2 | chr15:18820328-19014234 | 4393 | Ceacam18 | NM_028236.1 | chr7:43634738-43649294 |
| 4297 | Cdh11 | NM_009866.5 | chr8:102632094-102785111 | 4394 | Ceacam19 | NM_177036.5 | chr7:19875741-19887965 |
| 4298 | Cdh12 | NM_001008420.2 | chr15:21111451-21589633 | 4395 | Ceacam2 | NM_001133368.1 | chr7:25516041-25540004 |
| 4299 | Cdh13 | NM_019707.4 | chr8:118283754-119323448 | 4396 | Ceacam20 | NM_027839.2 | chr7:19965411-19991111 |
| 4300 | Cdh15 | NM_007662.2 | chr8:122848373-122867397 | 4397 | Ceacam3 | NM_054059.1 | chr7:17150399-17183231 |
| 4301 | Cdh16 | NM_001252627.1 | chr8:104614137-104624396 | 4398 | Ceacam5 | NM_028480.2 | chr7:17713251-17761121 |
| 4302 | Cdh17 | NM_019753.4 | chr4:11758156-11817908 | 4399 | Ceacam9 | NM_011927.4 | chr7:16721928-16726110 |
| 4303 | Cdh18 | NM_001081299.1 | chr15:23036462-23474418 | 4400 | Ceacam-ps1 | NR_003247.2 | chr7:16649029-16657478 |
| 4304 | Cdh19 | NM_001081386.1 | chr1:110889194-110977372 | 4401 | Cebpa | NM_001287514.1 | chr7:35119292-35121928 |
| 4305 | Cdh2 | NM_007664.4 | chr18:16588876-16809049 | 4402 | Cebpb | NM_009883.4 | chr2:167688914-167690432 |
| 4306 | Cdh20 | NM_011800.4 | chr1:104768188-104995481 | 4403 | Cebpd | NM_007679.4 | chr16:15887285-15889545 |
| 4307 | Cdh22 | NM_174988.3 | chr2:165111506-165234737 | 4404 | Cebpe | NM_207131.1 | chr14:54710362-54712174 |
| 4308 | Cdh23 | NM_001252635.1 | chr10:60302749-60696490 | 4405 | Cebpg | NM_009884.3 | chr7:35046421-35056566 |
| 4309 | Cdh24 | NM_199470.2 | chr14:54631991-54641364 | 4406 | Cebpz | NM_001024806.2 | chr17:78919002-78937070 |
| 4310 | Cdh26 | NM_001291189.1 | chr2:178430514-178487366 | 4407 | Cebpzos | NM_001177402.1 | chr17:78916498-78921048 |
| 4311 | Cdh3 | NM_001037809.5 | chr8:106510851-106556911 | 4408 | Cecr2 | NM_001128151.1 | chr6:120666420-120771191 |
| 4312 | Cdh4 | NM_009867.3 | chr2:179442477-179899375 | 4409 | Cecr5 | NM_144815.2 | chr6:120509493-120531299 |
| 4313 | Cdh5 | NM_009868.4 | chr8:104101624-104144602 | 4410 | Cecr6 | NM_033567.1 | chr6:120488938-120493807 |
| 4314 | Cdh6 | NM_007666.3 | chr15:13044199-13173639 | 4411 | Cel | NM_009885.2 | chr2:28555819-28563403 |
| 4315 | Cdh7 | NM_172853.2 | chr1:109983736-110139001 | 4412 | Cela1 | NM_033612.2 | chr15:100674421-100687920 |
| 4316 | Cdh8 | NM_001039154.2 | chr8:99028768-99416471 | 4413 | Cela2a | NM_007919.2 | chr4:141814962-141826003 |
| 4317 | Cdh9 | NM_009869.1 | chr15:16778100-16856777 | 4414 | Cela3b | NM_026419.2 | chr4:137421007-137430526 |
| 4318 | Cdhr1 | NM_130878.2 | chr14:37077848-37098311 | 4415 | Celf1 | NM_001244891.1 | chr2:90940396-91019497 |
| 4319 | Cdhr2 | NM_001033364.3 | chr13:54701462-54736662 | 4416 | Celf2 | NM_001110228.1 | chr2:6539608-6884996 |
| 4320 | Cdhr3 | NM_001024678.1 | chr12:33033795-33092875 | 4417 | Celf3 | NM_001289613.1 | chr3:94478548-94492198 |
| 4321 | Cdhr5 | NM_001114322.1 | chr7:141269084-141276786 | 4418 | Celf4 | NM_001146292.1 | chr18:25477619-25753983 |
| 4322 | Cdip1 | NM_025670.4 | chr16:4765460-4789935 | 4419 | Celf5 | NM_176954.4 | chr10:81459227-81482709 |
| 4323 | Cdipt | NM_026638.3 | chr7:126975913-126980501 | 4420 | Celf6 | NM_175235.3 | chr9:59578336-59607292 |
| 4324 | Cdk1 | NM_007659.3 | chr10:69336634-69352912 | 4421 | Celrr | NR_038008.1 | chr1:121087404-121120975 |
| 4325 | Cdk10 | NM_194444.2 | chr8:123224840-123232256 | 4422 | Celsr1 | NM_009886.2 | chr15:85898757-86033777 |
| 4326 | Cdk11b | NM_007661.3 | chr4:155624868-155649932 | 4423 | Celsr2 | NM_001004177.2 | chr3:108390847-108415494 |
| 4327 | Cdk12 | NM_001109626.1 | chr11:98203304-98253540 | 4424 | Celsr3 | NM_080437.2 | chr9:108826319-108852969 |
| 4328 | Cdk13 | NM_001081058.2 | chr13:17715961-17805097 | 4425 | Cemip | NM_030728.4 | chr7:83932856-84086505 |
| 4329 | Cdk14 | NM_011074.3 | chr5:4803383-5380251 | 4426 | Cend1 | NM_023316.4 | chr7:141426450-141429420 |
| 4330 | Cdk15 | NM_001033493.2 | chr1:59258090-59352369 | 4427 | Cenpa | NM_007681 | chr5:30666885-30674837 |
| 4331 | Cdk16 | NM_011049.5 | chrX:20688425-20699879 | 4428 | Cenpb | NM_007682 | chr2:131177288-131180012 |
| 4332 | Cdk17 | NM_146239.2 | chr10:93160875-93241342 | 4429 | Cenpc1 | NM_007683.3 | chr5:86012024-86065583 |
| 4333 | Cdk18 | NM_008795.2 | chr1:132113546-132139685 | 4430 | Cenpe | NM_173762 | chr3:135212562-135273540 |
| 4334 | Cdk19 | NM_001168304.1 | chr10:40349307-40483518 | 4431 | Cenpf | NM_001081363.2 | chr1:189640613-189680086 |
| 4335 | Cdk2 | NM_016756.4 | chr10:128697938-128705053 | 4432 | Cenph | NM_021886.1 | chr13:100759685-100775899 |
| 4336 | Cdk20 | NM_053180.1 | chr13:64432552-64439721 | 4433 | Cenpi | NM_145924.3 | chrX:134208083-134363104 |
| 4337 | Cdk2ap1 | NM_013812.2 | chr5:124345438-124354628 | 4434 | Cenpj | NM_001014996 | chr14:56526760-56571846 |
| 4338 | Cdk2ap2 | NM_026373 | chr19:4079350-4099017 | 4435 | Cenpk | NM_021790.2 | chr13:104229387-104249622 |
| 4339 | Cdk3-ps | NR_004853.1 | chr11:116216003-116220287 | 4436 | Cenpl | NM_001159930.2 | chr1:161070766-161086724 |
| 4340 | Cdk4 | NM_009870.3 | chr10:127063602-127067282 | 4437 | Cenpm | NM_001080358.1 | chr15:82233779-82244336 |
| 4341 | Cdk5 | NM_007668.3 | chr5:24421581-24423530 | 4438 | Cenpn | NM_028131.3 | chr8:116921739-116941503 |
| 4342 | Cdk5r1 | NM_009871.2 | chr11:80477045-80481179 | 4439 | Cenpo | NM_134046.5 | chr12:4211671-4234294 |
| 4343 | Cdk5r2 | NM_009872.3 | chr1:74859028-74857732 | 4440 | Cenpp | NM_025435.3 | chr13:49464058-49652731 |
| 4344 | Cdk5rap1 | NM_025876.2 | chr2:154335385-154372719 | 4441 | Cenpq | NM_031863.3 | chr17:40923054-40934651 |
| 4345 | Cdk5rap2 | NM_145990.4 | chr4:70218854-70410435 | 4442 | Cenpt | NM_177150.2 | chr8:165844677-105852008 |
| 4346 | Cdk5rap3 | NM_030243.2 | chr11:96907424-96916514 | 4443 | Cenpu | NM_027973.3 | chr8:46552068-46579584 |
| 4347 | Cdk6 | NM_009873.3 | chr5:3343892-3531009 | 4444 | Cenpv | NM_028448.1 | chr11:62524943-62539261 |
| 4348 | Cdk7 | NM_009874.3 | chr13:100697024-100730942 | 4445 | Cenpw | NM_001109747.1 | chr10:30196008-30200540 |
| 4349 | Cdk8 | NM_153799.3 | chr5:146231674-146302874 | 4446 | Cep104 | NM_177673.2 | chr4:153975560-154007225 |
| 4350 | Cdk9 | NM_130860.3 | chr2:32705781-32712784 | 4447 | Cep112 | NM_029586.2 | chr11:108582617-108860615 |
| 4351 | Cdkal1 | NM_144536.3 | chr13:29325300-29855673 | 4448 | Cep120 | NM_178686.3 | chr18:53681723-53744547 |
| 4352 | Cdkl1 | NM_183294.2 | chr12:69746847-69790707 | 4449 | Cep128 | NM_181815.3 | chr12:90998491-91384409 |
| 4353 | Cdkl2 | NM_001276315.1 | chr5:92006079-92042696 | 4450 | Cep131 | NM_009734.3 | chr11:120064429-120086827 |
| 4354 | Cdkl3 | NM_001166855.1 | chr11:52004220-52038165 | 4451 | Cep135 | NM_199032.2 | chr5:76591713-76646466 |
| 4355 | Cdkl4 | NM_001033443.4 | chr17:80523549-80563834 | 4452 | Cep152 | NM_001081091.1 | chr2:125563087-125625113 |
| 4356 | Cdkl5 | NM_001024624.2 | chrX:160784307-160994681 | 4453 | Cep162 | NM_199316.2 | chr9:87191962-87255532 |
| 4357 | Cdkn1a | NM_001111099.2 | chr17:29090978-29100722 | 4454 | Cep164 | NM_001081373.2 | chr9:45766945-45828638 |
| 4358 | Cdkn1b | NM_009875.4 | chr6:134920400-134925825 | 4455 | Cep170 | NM_001099637.2 | chr1:176733652-176807124 |
| 4359 | Cdkn1c | NM_001161624.1 | chr7:143458338-143461050 | 4456 | Cep170b | NM_001024602.3 | chr12:112722173-112746591 |
| 4360 | Cdkn2a | NM_001040654.1 | chr4:89274472-89282192 | 4457 | Cep19 | NM_025892.2 | chr16:32099801-32108054 |
| 4361 | Cdkn2aip | NM_172407.3 | chr8:47709343-47713931 | 4458 | Cep192 | NM_027556.1 | chr18:67800106-67885170 |
| 4362 | Cdkn2aipnl | NM_029976.3 | chr11:51967630-51977336 | 4459 | Cep250 | NM_001129999.1 | chr2:155956557-155998908 |
| 4363 | Cdkn2b | NM_007670.4 | chr4:89306288-89311032 | 4460 | Cep290 | NM_146009.2 | chr10:100488288-100573655 |
| 4364 | Cdkn2c | NM_007671.3 | chr4:109660875-109665372 | 4461 | Cep350 | NM_001039184.1 | chr1:155844963-155973255 |

Fig. 21 - 24

| | | | | | | | |
|---|---|---|---|---|---|---|---|
| 4462 | Cep41 | NM_031998.3 | chr6:30693456-30693749 | 4559 | Chd8 | NM_201637.2 | chr14:52198150-52237572 |
| 4463 | Cep44 | NM_001009951.1 | chr8:56531521-56550566 | 4560 | Chd9 | NM_177224.2 | chr8:90828834-91054508 |
| 4464 | Cep55 | NM_001164362.1 | chr19:38055041-38074425 | 4561 | Chdh | NM_001136240.1 | chr14:30008999-30040486 |
| 4465 | Cep57 | NM_026665.4 | chr9:13807787-13827107 | 4562 | Chek1 | NM_007691.5 | chr9:36708481-36726658 |
| 4466 | Cep57l1 | NM_001243074.1 | chr10:41718839-41809868 | 4563 | Chek2 | NM_016681.3 | chr5:110840016-110874133 |
| 4467 | Cep63 | NM_001081322.1 | chr3:102586577-102626124 | 4564 | Cherp | NM_138585.3 | chr8:72460482-72475233 |
| 4468 | Cep68 | NM_172260.3 | chr11:20227036-20249424 | 4565 | Chfr | NM_001289577.1 | chr5:110135829-110171973 |
| 4469 | Cep70 | NM_023873.3 | chr9:99243467-99300403 | 4566 | Chga | NM_007693.1 | chr12:102554968-102565027 |
| 4470 | Cep72 | NM_028959.3 | chr13:74036494-74062285 | 4567 | Chgb | NM_007694.4 | chr2:132781277-132795072 |
| 4471 | Cep76 | NM_001081073.1 | chr18:67617396-67641336 | 4568 | Chia1 | NM_023186.3 | chr3:106113381-106132116 |
| 4472 | Cep78 | NM_198019.2 | chr19:15955772-15984989 | 4569 | Chic1 | NM_009787.2 | chrX:103356475-103396118 |
| 4473 | Cep83 | NM_029852.2 | chr10:94688789-94790336 | 4570 | Chic2 | NM_028850.5 | chr5:75005003-75044641 |
| 4474 | Cep83os | NR_015524.1 | chr10:94673492-94688613 | 4571 | Chid1 | NM_001142681.1 | chr7:141493135-141539857 |
| 4475 | Cep85 | NM_144527.3 | chr4:134129857-134167085 | 4572 | Chil1 | NM_007695.3 | chr1:134182403-134190031 |
| 4476 | Cep85l | NM_001204983.1 | chr10:53278080-53379851 | 4573 | Chil3 | NM_009892.3 | chr3:106147553-106167564 |
| 4477 | Cep89 | NM_028120.2 | chr7:35397092-35438684 | 4574 | Chil4 | NM_145126.2 | chr3:106201490-106219479 |
| 4478 | Cep95 | NM_001166685.1 | chr11:106789251-106818861 | 4575 | Chil6 | NM_178412.2 | chr3:106387383-106406182 |
| 4479 | Cep97 | NM_001159364.1 | chr16:55923860-55934848 | 4576 | Chit1 | NM_001284524.1 | chr1:134111241-134151540 |
| 4480 | Cepti | NM_133869.4 | chr3:106502259-106547802 | 4577 | Chka | NM_001271496.1 | chr19:3851772-3894369 |
| 4481 | Cer1 | NM_009887.2 | chr4:82881750-82885151 | 4578 | Chkb | NM_007692.6 | chr15:89426348-89429927 |
| 4482 | Cercam | NM_207298.2 | chr2:29869493-29882840 | 4579 | ChkbCpt1b | NR_004843.2 | chr15:89416464-89429927 |
| 4483 | Cerk | NM_145475.4 | chr15:86139100-86186141 | 4580 | Chl1 | NM_007697.2 | chr6:103510875-103733035 |
| 4484 | Cerkl | NM_001048376.1 | chr2:79332490-79428988 | 4581 | Chm | NM_018818.2 | chrX:113040591-113185515 |
| 4485 | Cers1 | NM_138647.3 | chr8:70315774-70331588 | 4582 | Chml | NM_021350.2 | chr1:175682237-175683353 |
| 4486 | Cers2 | NM_029789.1 | chr3:95315251-95323568 | 4583 | Chmp1a | NM_145606.3 | chr8:123204260-123212788 |
| 4487 | Cers3 | NM_001164201.1 | chr7:66743503-66823692 | 4584 | Chmp1b | NM_024190.2 | chr18:67205358-67207887 |
| 4488 | Cers4 | NM_026058.4 | chr8:4493404-4526079 | 4585 | Chmp2a | NM_026885.3 | chr7:13032005-13034777 |
| 4489 | Cers5 | NM_028015.2 | chr15:99735591-99772515 | 4586 | Chmp2b | NM_026879.2 | chr16:65539132-65562697 |
| 4490 | Cers6 | NM_172856.3 | chr2:68861556-69111290 | 4587 | Chmp3 | NM_025783.3 | chr6:71543853-71581574 |
| 4491 | Ces1a | NM_001013764.2 | chr8:93020214-93048192 | 4588 | Chmp4b | NM_029362.3 | chr2:154657925-154684783 |
| 4492 | Ces1b | NM_001081312.1 | chr8:93056726-93080017 | 4589 | Chmp4c | NM_025519.2 | chr3:10366972-10391005 |
| 4493 | Ces1c | NM_007954.4 | chr8:93099015-93131283 | 4590 | Chmp5 | NM_029814.1 | chr4:40948552-40965302 |
| 4494 | Ces1d | NM_053200.2 | chr8:93166071-93197804 | 4591 | Chmp6 | NM_001085498.2 | chr11:119913809-119919552 |
| 4495 | Ces1e | NM_133660.3 | chr8:93201217-93229619 | 4592 | Chmp7 | NM_134078.4 | chr14:69716978-69732570 |
| 4496 | Ces1f | NM_144930.2 | chr8:93256235-93279736 | 4593 | Chn1 | NM_001113246.2 | chr2:73610659-73775346 |
| 4497 | Ces1g | NM_021456.4 | chr8:93302366-93337209 | 4594 | Chn1os3 | NR_040623.1 | chr2:73596525-73616012 |
| 4498 | Ces2a | NM_001063330.1 | chr8:104734002-104741834 | 4595 | Chn2 | NM_001163640.1 | chr6:54039931-54301812 |
| 4499 | Ces2b | NM_198171.2 | chr8:104831643-104838652 | 4596 | Chodl | NM_139134.3 | chr16:78930947-78951728 |
| 4500 | Ces2c | NM_145603.2 | chr8:104847067-104854482 | 4597 | Chordc1 | NM_025844.2 | chr9:18292266-18314600 |
| 4501 | Ces2d-ps | NR_033726.1 | chr8:104867423-104874082 | 4598 | Chp1 | NM_019769.3 | chr2:119547706-119587022 |
| 4502 | Ces2e | NM_001163756.1 | chr8:104926259-104934672 | 4599 | Chp2 | NM_027363.1 | chr7:122219495-122222539 |
| 4503 | Ces2f | NM_001079865.2 | chr8:104947155-104955962 | 4600 | Chpf | NM_001001565.2 | chr1:75874568-75879471 |
| 4504 | Ces2g | NM_197999.2 | chr8:104961717-104969637 | 4601 | Chpf2 | NM_133913.2 | chr5:24586749-24594486 |
| 4505 | Ces2h | NM_001272045.1 | chr8:105000852-105020410 | 4602 | Chpt1 | NM_001146690.1 | chr10:88472812-88503970 |
| 4506 | Ces3a | NM_001164621.1 | chr8:105048598-105058414 | 4603 | Chrac1 | NM_053068.3 | chr5:73090411-73094075 |
| 4507 | Ces3b | NM_001159415.1 | chr8:105083754-105093591 | 4604 | Chrd | NM_001278041.1 | chr16:20733126-20742384 |
| 4508 | Ces4a | NM_146213.2 | chr8:105131799-105150109 | 4605 | Chrdl1 | NM_001114385.1 | chrX:143285673-143394262 |
| 4509 | Ces5a | NM_001003951.2 | chr8:93499212-93535707 | 4606 | Chrdl2 | NM_001291320.1 | chr7:100009917-100034726 |
| 4510 | Cetn1 | NM_007593.5 | chr18:9618418-9619469 | 4607 | Chrm1 | NM_001112697.1 | chr19:8664004-8683602 |
| 4511 | Cetn2 | NM_026559.2 | chrX:72913564-72918344 | 4608 | Chrm2 | NM_203491.3 | chr6:36388083-36524774 |
| 4512 | Cetn3 | NM_007684.3 | chr13:81783291-81797157 | 4609 | Chrm3 | NM_033269.4 | chr13:9876612-10360803 |
| 4513 | Cetn4 | NM_145825.2 | chr3:37308626-37312446 | 4610 | Chrm4 | NM_007699.2 | chr2:91922188-91929829 |
| 4514 | Cfb | NM_001142706.1 | chr17:34856373-34862514 | 4611 | Chrm5 | NM_205783.2 | chr2:112479071-112480817 |
| 4515 | Cfc1 | NM_007685.2 | chr1:34535647-34544311 | 4612 | Chrna1 | NM_007389.5 | chr2:73563280-73580338 |
| 4516 | Cfd | NM_027827.1 | chr10:79892660-79892660 | 4613 | Chrna10 | NM_001081424.1 | chr7:102111265-102116719 |
| 4517 | Cfdp1 | NM_011801.1 | chr8:111768472-111854310 | 4614 | Chrna2 | NM_144803.2 | chr14:66140959-66152948 |
| 4518 | Cfh | NM_009888.3 | chr1:140085854-140183411 | 4615 | Chrna3 | NM_145129.2 | chr9:55011342-55026359 |
| 4519 | Cfhr1 | NM_015780.5 | chr1:139547063-139560222 | 4616 | Chrna4 | NM_015730.5 | chr2:181022310-181039177 |
| 4520 | Cfhr2 | NM_001025575.2 | chr1:139810291-139858699 | 4617 | Chrna5 | NM_176844.4 | chr9:54980879-55007779 |
| 4521 | Cfi | NM_007686.2 | chr3:129836738-129875328 | 4618 | Chrna6 | NM_021369.2 | chr8:27403211-27413944 |
| 4522 | Cfl1 | NM_007687.5 | chr9:5490454-5494031 | 4619 | Chrna7 | NM_007390.3 | chr7:63098691-63212526 |
| 4523 | Cfl2 | NM_007688 | chr12:54858818-54862877 | 4620 | Chrna9 | NM_001081104.1 | chr5:65967123-65977486 |
| 4524 | Cflar | NM_001289790.1 | chr1:58711490-58759209 | 4621 | Chrnb1 | NM_009601.4 | chr11:69784035-69795937 |
| 4525 | Cfp | NM_008823.4 | chrX:20925453-20931555 | 4622 | Chrnb2 | NM_009602.4 | chr3:89753447-89764632 |
| 4526 | Cftr | NM_021050.2 | chr6:18170686-18322769 | 4623 | Chrnb3 | NM_027454.4 | chr8:27368710-27399730 |
| 4527 | Cga | NM_009809.2 | chr4:34899573-34907374 | 4624 | Chrnb4 | NM_148944.4 | chr9:55028155-55048544 |
| 4528 | Cggbp1 | NM_178647.2 | chr16:64852084-64859491 | 4625 | Chrnd | NM_021600.3 | chr1:87190596-87200070 |
| 4529 | Cgn | NM_001037711.2 | chr3:94760069-94786515 | 4626 | Chrne | NM_009603.1 | chr11:70614882-70619194 |
| 4530 | Cgnl1 | NM_026599.5 | chr9:71626506-71771602 | 4627 | Chrng | NM_009604.3 | chr1:87205810-87211835 |
| 4531 | Cgref1 | NM_001160149.1 | chr5:30933142-30945427 | 4628 | Chst1 | NM_023850.2 | chr2:92599706-92615252 |
| 4532 | Cgrrf1 | NM_026832.3 | chr14:46854240-46854190 | 4629 | Chst10 | NM_145142.2 | chr1:38863872-38898160 |
| 4533 | Ch25h | NM_009890.1 | chr19:34473783-34475135 | 4630 | Chst11 | NM_021439.2 | chr10:82985496-83195891 |
| 4534 | Chac1 | NM_026929.4 | chr2:119351241-119354327 | 4631 | Chst12 | NM_021528.3 | chr5:140506608-140526238 |
| 4535 | Chac2 | NM_001290667.1 | chr11:30976706-30986365 | 4632 | Chst13 | NM_027928.1 | chr6:90308350-90325185 |
| 4536 | Chad | NM_007689.4 | chr11:94565073-94569127 | 4633 | Chst14 | NM_028117.3 | chr2:118926496-118928583 |
| 4537 | Chadl | NM_001164320.1 | chr15:81686166-81697287 | 4634 | Chst15 | NM_029935.5 | chr7:132236254-132317155 |
| 4538 | Chaf1a | NM_013733.3 | chr17:56063026-56068026 | 4635 | Chst2 | NM_018763.2 | chr9:95400925-95407270 |
| 4539 | Chaf1b | NM_028083.4 | chr16:93883900-93906106 | 4636 | Chst3 | NM_016803.3 | chr10:60181527-60219260 |
| 4540 | Champ1 | NM_181854.2 | chr8:13869640-13881639 | 4637 | Chst4 | NM_011998.4 | chr8:110029074-110039334 |
| 4541 | Chat | NM_009891.2 | chr14:32408202-32465909 | 4638 | Chst5 | NM_019950.2 | chr8:111889134-111910199 |
| 4542 | Chchd1 | NM_025366.3 | chr14:20703026-20704425 | 4639 | Chst7 | NM_021715.1 | chrX:20059568-20097520 |
| 4543 | Chchd10 | NM_175329.3 | chr10:75935572-75937734 | 4640 | Chst8 | NM_175140.4 | chr7:34674467-34812711 |
| 4544 | Chchd2 | NM_024166.6 | chr5:129881160-129887470 | 4641 | Chst9 | NM_199055.2 | chr18:15452174-15718046 |
| 4545 | Chchd3 | NM_025336.1 | chr6:32792226-33060192 | 4642 | Chsy1 | NM_001081163.1 | chr7:66109514-66173798 |
| 4546 | Chchd4 | NM_133824.5 | chr6:91464275-91473423 | 4643 | Chsy3 | NM_001081328.1 | chr18:59175339-59411336 |
| 4547 | Chchd5 | NM_025395.3 | chr2:129129669-129134111 | 4644 | Chtf18 | NM_145409.2 | chr17:25719029-25727415 |
| 4548 | Chchd6 | NM_001167736.1 | chr14:89995652-89995652 | 4645 | Chtf8 | NM_145412.3 | chr8:106883862-106893593 |
| 4549 | Chchd7 | NM_001190322.2 | chr4:3938887-3943525 | 4646 | Chtop | NM_023215.6 | chr3:90498538-90509498 |
| 4550 | Chd1 | NM_007690.3 | chr17:15704966-15772612 | 4647 | Chuk | NM_001162410.1 | chr19:44073333-44107477 |
| 4551 | Chd1l | NM_026539.2 | chr3:97560747-97610190 | 4648 | Churc1 | NM_206534.1 | chr12:76765572-76783178 |
| 4552 | Chd2 | NM_001081345.2 | chr7:73426651-73541746 | 4649 | Ciao1 | NM_025296.4 | chr2:127240937-127247816 |
| 4553 | Chd3 | NM_146019.4 | chr11:69343272-69369426 | 4650 | Ciapin1 | NM_134141.4 | chr8:94819817-94838340 |
| 4554 | Chd3os | NR_027827.1 | chr11:69338768-69342647 | 4651 | Ciart | NM_001033302.2 | chr3:95878504-95882228 |
| 4555 | Chd4 | NM_145979.2 | chr6:125096162-125130501 | 4652 | Cib1 | NM_001291275.1 | chr7:80227155-80232805 |
| 4556 | Chd5 | NM_001081376.1 | chr4:152335650-152390194 | 4653 | Cib2 | NM_019686.5 | chr9:54545353-54560079 |
| 4557 | Chd6 | NM_173368.1 | chr2:160946977-161109086 | 4654 | Cib3 | NM_001080812.1 | chr2:72204334-72212837 |
| 4558 | Chd7 | NM_001277149.1 | chr4:8690405-8868449 | 4655 | Cib4 | NM_028483.1 | chr5:30485583-30545836 |

Fig.21 - 25

| | | | | | | | |
|---|---|---|---|---|---|---|---|
| 4656 | Cic | NM_001302811.1 | chr7:25267657-25294159 | 4753 | Clec3a | NM_001007223.3 | chr8:114418033-114428133 |
| 4657 | Cidea | NM_007702.2 | chr18:67343563-67367794 | 4754 | Clec3b | NM_011606.2 | chr9:123150945-123157432 |
| 4658 | Cideb | NM_009894.3 | chr14:55754054-55758424 | 4755 | Clec4a1 | NM_199311.2 | chr6:122921847-122934619 |
| 4659 | Cidec | NM_178373.3 | chr6:113424635-113435755 | 4756 | Clec4a2 | NM_001170332.1 | chr6:123122689-123143999 |
| 4660 | Ciita | NM_001243760.2 | chr16:10480071-10527640 | 4757 | Clec4a3 | NM_001204241.1 | chr6:122952514-122969878 |
| 4661 | Cilp | NM_173385.2 | chr9:65265179-65280605 | 4758 | Clec4a4 | NM_001005860.2 | chr6:122990366-123024421 |
| 4662 | Cilp2 | NM_026818 | chr8:69880365-69887392 | 4759 | Clec4b1 | NM_001190310.1 | chr6:123049961-123071555 |
| 4663 | Cinp | NM_026048.4 | chr12:110872609-110889145 | 4760 | Clec4b2 | NM_001004159.2 | chr6:123173022-123204671 |
| 4664 | Cipc | NM_001289429.1 | chr12:86947040-86965366 | 4761 | Clec4d | NM_001163161.1 | chr6:123262106-123275268 |
| 4665 | Cir1 | NM_025854 | chr2:73283871-73312592 | 4762 | Clec4e | NM_019948.2 | chr6:123281788-123289871 |
| 4666 | Cirbp | NM_007705.2 | chr10:80167840-80171653 | 4763 | Clec4f | NM_016751.3 | chr8:3644541-83656116 |
| 4667 | Cirh1a | NM_011574.2 | chr8:106893639-106923094 | 4764 | Clec4g | NM_029465.3 | chr8:3716070-3720851 |
| 4668 | Cisd1 | NM_134007.4 | chr10:71330493-71344849 | 4765 | Clec4n | NM_001190320.1 | chr6:123229842-123247024 |
| 4669 | Cisd2 | NM_025902.3 | chr3:135406411-135423433 | 4766 | Clec5a | NM_001038604.1 | chr6:40574897-40585805 |
| 4670 | Cisd3 | NM_001085500.2 | chr11:97685951-97688625 | 4767 | Clec7a | NM_020008.3 | chr6:129461590-129472779 |
| 4671 | Cish | NM_009895.3 | chr9:107296688-107301961 | 4768 | Clec9a | NM_001205363.1 | chr6:129408861-129424764 |
| 4672 | Cistr-act | NR_104334.1 | chr15:102746440-102746909 | 4769 | Clgn | NM_009904.2 | chr8:83389890-83426829 |
| 4673 | Cit | NM_007708.3 | chr5:115845655-116006341 | 4770 | Clhc1 | NM_001081099.1 | chr4:134510998-134523922 |
| 4674 | Cited1 | NM_001276466.1 | chrX:102247377-102252181 | 4771 | Clic1 | NM_039444.2 | chr17:35050242-35058719 |
| 4675 | Cited2 | NM_010828.3 | chr10:17723227-17729674 | 4772 | Clic3 | NM_027085.3 | chr2:25456842-25458772 |
| 4676 | Cited4 | NM_019563.2 | chr4:120666562-120667820 | 4773 | Clic4 | NM_013885.2 | chr4:135213969-135272760 |
| 4677 | Cit1 | NM_001252534.1 | chr2:32363197-32378313 | 4774 | Clic5 | NM_172621.2 | chr17:44168571-44280168 |
| 4678 | CK137956 | NM_001134733.1 | chr4:127927591-127970841 | 4775 | Clic6 | NM_172469.3 | chr16:92498146-92541241 |
| 4679 | Ckap2 | NM_001004140.2 | chr8:22168151-22185819 | 4776 | Clint1 | NM_001045520.3 | chr11:45863963-45910625 |
| 4680 | Ckap2l | NM_181589.3 | chr2:129268209-129297212 | 4777 | Clip1 | NM_001291229.1 | chr5:123577793-123684361 |
| 4681 | Ckap4 | NM_175451.1 | chr10:84526304-84533888 | 4778 | Clip2 | NM_001089162.2 | chr5:134489382-134552434 |
| 4682 | Ckap5 | NM_001165989.1 | chr2:91546321-91620665 | 4779 | Clip3 | NM_001081114.1 | chr7:30291752-30308367 |
| 4683 | Ckb | NM_021273.4 | chr12:111669354-111672338 | 4780 | Clip4 | NM_001271483.1 | chr17:71781298-71864210 |
| 4684 | Cklf | NM_001037841.3 | chr8:104250860-104264936 | 4781 | Clk1 | NM_001042634.2 | chr1:58411987-58424088 |
| 4685 | Ckm | NM_007710.2 | chr7:19411093-19421583 | 4782 | Clk2 | NM_001163432.2 | chr3:89164794-89177087 |
| 4686 | Ckmt1 | NM_009897.2 | chr2:121358640-121363737 | 4783 | Clk3 | NM_007713.4 | chr9:57750710-57765860 |
| 4687 | Ckmt2 | NM_198415.2 | chr13:91853386-91876885 | 4784 | Clk4 | NM_007714.6 | chr11:51263113-51281770 |
| 4688 | Cks1b | NM_016904.1 | chr3:89415471-85418291 | 4785 | Clmn | NM_001040682.1 | chr12:104763113-104865076 |
| 4689 | Cks1brt | NM_001037922.3 | chr8:85151923-85173622 | 4786 | Clmp | NM_133733.4 | chr9:40685963-40784046 |
| 4690 | Cks2 | NM_025415.3 | chr13:51645231-51650662 | 4787 | Cln3 | NM_001146311.1 | chr7:126571399-126584280 |
| 4691 | Clasp1 | NM_001293300.1 | chr1:118389059-118609462 | 4788 | Cln5 | NM_001033242.1 | chr14:103070215-103077630 |
| 4692 | Clasp2 | NM_001081960.1 | chr9:113585-113919697 | 4789 | Cln6 | NM_001033175.2 | chr9:62838786-62852002 |
| 4693 | Clasrp | NM_016680.5 | chr7:19581037-19604486 | 4790 | Cln8 | NM_012000.3 | chr8:14888535-14901719 |
| 4694 | Clca1 | NM_009899.4 | chr3:144729876-144760977 | 4791 | Clnk | NM_013748.3 | chr5:38706456-38876693 |
| 4695 | Clca2 | NM_030601.3 | chr3:144796558-144819494 | 4792 | Clns1a | NM_023671.2 | chr7:97696656-97720793 |
| 4696 | Clca3 | NM_017474.2 | chr3:145004536-145032776 | 4793 | Clock | NM_001289826.1 | chr5:76209867-76304792 |
| 4697 | Clca4 | NM_139148.2 | chr3:144822623-144849302 | 4794 | Clpl | NM_133840.2 | chr2:84731421-84727768 |
| 4698 | Clca5 | NM_178697.4 | chr3:145070264-145099041 | 4795 | Clpb | NM_009191.3 | chr7:101663767-101790168 |
| 4699 | Clca6 | NM_207208.3 | chr3:144952485-144975045 | 4796 | Clpp | NM_017393.2 | chr17:56990263-56996371 |
| 4700 | Clcc1 | NM_001177770.1 | chr3:108653989-108678011 | 4797 | Clps | NM_025469.2 | chr17:28558213-28560714 |
| 4701 | Clcf1 | NM_019952.5 | chr19:4214237-4223505 | 4798 | Clpsl2 | NM_001034871.2 | chr17:28549486-28552618 |
| 4702 | Clcn1 | NM_013491.2 | chr6:42386684-42314656 | 4799 | Clptm1 | NM_019649.2 | chr7:19631579-19665030 |
| 4703 | Clcn2 | NM_009900.2 | chr16:20702965-20716636 | 4800 | Clptm1l | NM_146047.2 | chr13:73604001-73620639 |
| 4704 | Clcn3 | NM_007711.3 | chr8:60910388-60983311 | 4801 | Clpx | NM_001044389.2 | chr9:65294259-65330658 |
| 4705 | Clcn4-2 | NM_011334.4 | chr7:7282308-7299557 | 4802 | Clrn1 | NM_153384.3 | chr3:58844027-58885212 |
| 4706 | Clcn5 | NM_001243762.1 | chrX:7158411-7319858 | 4803 | Clrn2 | NM_001163317.1 | chr5:45453750-45464149 |
| 4707 | Clcn6 | NM_011929.3 | chr4:148004258-148038813 | 4804 | Clrn3 | NM_178669.5 | chr7:135511455-135528654 |
| 4708 | Clcn7 | NM_011334.4 | chr17:25133393-25162099 | 4805 | Clspn | NM_175554.4 | chr4:126156979-126193903 |
| 4709 | Clcnka | NM_001146307.1 | chr4:141384610-141398099 | 4806 | Clstn1 | NM_001290989.1 | chr4:149586467-149648899 |
| 4710 | Clcnkb | NM_019412.2 | chr4:141403584-141415988 | 4807 | Clstn2 | NM_022319.2 | chr9:97443394-98033167 |
| 4711 | Cldn1 | NM_016674.4 | chr16:26356645-26371839 | 4808 | Clstn3 | NM_153508.4 | chr6:124430755-124464784 |
| 4712 | Cldn10 | NM_001160096.1 | chr14:118787870-118874525 | 4809 | Clta | NM_001080384.1 | chr4:44012642-44032846 |
| 4713 | Cldn11 | NM_008770.3 | chr3:31149919-31164326 | 4810 | Cltb | NM_028870.3 | chr13:54592938-54611272 |
| 4714 | Cldn12 | NM_001193659.1 | chr5:5505014-5514849 | 4811 | Cltc | NM_001003908.1 | chr11:86694652-86757492 |
| 4715 | Cldn13 | NM_020504.4 | chr5:134914249-134915530 | 4812 | Clu | NM_013492.2 | chr14:65968482-65981545 |
| 4716 | Cldn14 | NM_001165925.1 | chr16:93919030-93929567 | 4813 | Cluap1 | NM_029738.2 | chr16:3909008-3941147 |
| 4717 | Cldn15 | NM_021719.4 | chr5:136967868-136975845 | 4814 | Cluh | NM_001081158.2 | chr11:74649494-74670847 |
| 4718 | Cldn16 | NM_053241.5 | chr16:26463134-26482764 | 4815 | Clvs1 | NM_028940.2 | chr4:9269316-9451691 |
| 4719 | Cldn17 | NM_181490.3 | chr16:88505806-88506978 | 4816 | Clvs2 | NM_175448.3 | chr10:33512333-33624600 |
| 4720 | Cldn18 | NM_001194921.1 | chr9:99690796-99717267 | 4817 | Clybl | NM_029556.3 | chr14:122181693-122402234 |
| 4721 | Cldn19 | NM_001038590.1 | chr4:119255648-119259855 | 4818 | Cma1 | NM_010780.2 | chr14:55941450-55944661 |
| 4722 | Cldn2 | NM_016675.4 | chrX:139580807-139811388 | 4819 | Cma2 | NM_001024714.2 | chr14:55971427-55973995 |
| 4723 | Cldn20 | NM_001101560.1 | chr17:3532553-3533213 | 4820 | Cmah | NM_001111310.2 | chr13:24327403-24477289 |
| 4724 | Cldn22 | NM_029383.1 | chr8:47824481-47825475 | 4821 | Cmas | NM_009908.2 | chr6:142756685-142775714 |
| 4725 | Cldn23 | NM_027998.4 | chr8:35824708-35826559 | 4822 | Cmbl | NM_181588.3 | chr15:31568911-31590119 |
| 4726 | Cldn24 | NM_001111318.1 | chr8:47822142-47822805 | 4823 | Cmc1 | NM_026442.3 | chr9:118064526-118150196 |
| 4727 | Cldn25 | NM_001252450.1 | chr16:58727909-58734247 | 4824 | Cmc2 | NM_026844.3 | chr8:116888684-116921436 |
| 4728 | Cldn26 | NM_029070.2 | chr16:8409275-8425136 | 4825 | Cmip | NM_001163262.1 | chr8:117257918-117461505 |
| 4729 | Cldn3 | NM_009902.4 | chr5:134986215-134987476 | 4826 | Cmklr1 | NM_008153.3 | chr5:113612354-113650390 |
| 4730 | Cldn4 | NM_009903.2 | chr5:134945123-134946934 | 4827 | Cml1 | NM_023160.2 | chr6:85910153-85915677 |
| 4731 | Cldn5 | NM_013805.4 | chr16:18776846-18778262 | 4828 | Cml2 | NM_053096.3 | chr6:85865421-85869137 |
| 4732 | Cldn6 | NM_018777.4 | chr17:23679634-23682446 | 4829 | Cml3 | NM_001037842.3 | chr6:85760630-85765744 |
| 4733 | Cldn7 | NM_001198619.1 | chr11:69964778-69967886 | 4830 | Cml5 | NM_023493.2 | chr6:85817217-85820972 |
| 4734 | Cldn8 | NM_018778.1 | chr16:88605205-88563183 | 4831 | Cmpk1 | NM_025647.3 | chr4:114960612-114987228 |
| 4735 | Cldn9 | NM_020293.3 | chr17:23682583-23684026 | 4832 | Cmpk2 | NM_020557.4 | chr12:26469214-26479837 |
| 4736 | Cldnd2 | NM_028849.1 | chr7:43440815-43443320 | 4833 | Cmss1 | NM_025599.3 | chr16:57301999-57606867 |
| 4737 | Clec10a | NM_001204252.1 | chr11:70166622-70170836 | 4834 | Cmtm1 | NM_183990.2 | chr8:104293541-104310145 |
| 4738 | Clec11a | NM_009131.3 | chr7:44303765-44306959 | 4835 | Cmtm2a | NM_027022.2 | chr8:104281041-104293181 |
| 4739 | Clec12a | NM_177686.4 | chr6:129350243-129365303 | 4836 | Cmtm2b | NM_028524.1 | chr8:104322226-104330784 |
| 4740 | Clec12b | NM_001204229.1 | chr6:129325162-129336874 | 4837 | Cmtm3 | NM_024217 | chr8:104340593-104347672 |
| 4741 | Clec14a | NM_025809.5 | chr12:58264719-58269258 | 4838 | Cmtm4 | NM_153582.5 | chr8:104348192-104395807 |
| 4742 | Clec16a | NM_001204229.1 | chr16:10545538-10744878 | 4839 | Cmtm5 | NM_026066.2 | chr14:54936469-54939277 |
| 4743 | Clec18a | NM_181549.3 | chr2:111069496-111081708 | 4840 | Cmtm6 | NM_026036.3 | chr9:114731202-114749343 |
| 4744 | Clec1a | NM_175526.3 | chr6:129426683-129452000 | 4841 | Cmtm7 | NM_001252479.1 | chr9:114756835-114781993 |
| 4745 | Clec1b | NM_001204239.1 | chr6:129399296-129405413 | 4842 | Cmtm8 | NM_147294.1 | chr9:114789344-114844152 |
| 4746 | Clec2d | NM_053109.3 | chr6:129180614-129186835 | 4843 | Cmtr1 | NM_028791.6 | chr17:29660594-29705979 |
| 4747 | Clec2e | NM_153506.4 | chr6:129091815-129100903 | 4844 | Cmtr2 | NM_146215.4 | chr8:110217959-110224489 |
| 4748 | Clec2f | NM_177202.1 | chr6:129020527 | 4845 | Cmya5 | NM_023821.3 | chr13:93040714-93144724 |
| 4749 | Clec2g | NM_001168223.1 | chr6:128971159-128984707 | 4846 | Cnbd2 | NM_027585.2 | chr2:156132472-156175638 |
| 4750 | Clec2h | NM_053165.5 | chr6:128662384-128677374 | 4847 | Cnbp | NM_001109745.1 | chr6:87842614-87851106 |
| 4751 | Clec2i | NM_001289706.1 | chr6:128887586-128898167 | 4848 | Cndp1 | NM_177450.4 | chr18:84610508-84650095 |
| 4752 | Clec2l | NM_001191507.1 | chr6:38663068-38680865 | 4849 | Cndp2 | NM_001289531.1 | chr18:84667464-84682059 |

Fig.21 - 26

| | | | | | | | |
|---|---|---|---|---|---|---|---|
| 4850 | Cnep1r1 | NM_029074.3 | chr8:88118758-88135197 | 4947 | Col26a1 | NM_024474.2 | chr5:136741763-136883107 |
| 4851 | Cnfn | NM_001081375.1 | chr7:25367615-25369724 | 4948 | Col27a1 | NM_025685.3 | chr4:63215411-63334990 |
| 4852 | Cnga1 | NM_007723.2 | chr5:72603696-72642752 | 4949 | Col28a1 | NM_001037865.1 | chr6:7997807-8192617 |
| 4853 | Cnga2 | NM_007724.3 | chrX:71991848-72010218 | 4950 | Col2a1 | NM_001113515.2 | chr15:97975601-98004724 |
| 4854 | Cnga3 | NM_001282010.1 | chr1:37218277-37263384 | 4951 | Col3a1 | NM_009930.2 | chr1:45311537-45349706 |
| 4855 | Cnga4 | NM_001033317.3 | chr7:105404567-105408738 | 4952 | Col4a1 | NM_009931.2 | chr8:11198422-11312826 |
| 4856 | Cngb1 | NM_001195413.1 | chr8:95239042-95306585 | 4953 | Col4a2 | NM_009932.4 | chr8:11312804-11449287 |
| 4857 | Cngb3 | NM_013927.2 | chr4:19280849-19510623 | 4954 | Col4a3 | NM_007734.2 | chr1:82586920-82722059 |
| 4858 | Cnih1 | NM_009919.2 | chr14:46775567-46788357 | 4955 | Col4a3bp | NM_001164222.1 | chr13:96542734-96640167 |
| 4859 | Cnih2 | NM_009920.4 | chr19:5092867-5098521 | 4956 | Col4a4 | NM_007735.2 | chr1:82450722-82568849 |
| 4860 | Cnih3 | NM_001160211.1 | chr1:181352627-181460641 | 4957 | Col4a5 | NM_001163155.1 | chrX:141475418-141689235 |
| 4861 | Cnih4 | NM_030131.3 | chr1:181150930-181168994 | 4958 | Col4a6 | NM_053185.2 | chrX:141165402-141474076 |
| 4862 | Cnksr1 | NM_001081047.1 | chr4:134228041-134238399 | 4959 | Col5a1 | NM_015734.2 | chr2:27886424-28039510 |
| 4863 | Cnksr2 | NM_177751.3 | chrX:157821572-158043197 | 4960 | Col5a2 | NM_007737.2 | chr1:45374330-45503282 |
| 4864 | Cnksr3 | NM_172546.2 | chr10:7119061-7212237 | 4961 | Col5a3 | NM_016919.2 | chr9:20770049-20815034 |
| 4865 | Cnn1 | NM_009922.4 | chr9:22099252-22109221 | 4962 | Col6a1 | NM_009933.4 | chr10:76708791-76726044 |
| 4866 | Cnn2 | NM_007725.2 | chr10:79988599-79995400 | 4963 | Col6a2 | NM_146007.2 | chr10:76595975-76623404 |
| 4867 | Cnn3 | NM_028044.2 | chr3:121426540-121458205 | 4964 | Col6a3 | NM_001243008.1 | chr1:90766859-90843971 |
| 4868 | Cnnm1 | NM_031396.2 | chr19:43440449-43497213 | 4965 | Col6a4 | NM_026763.2 | chr9:105990317-106096691 |
| 4869 | Cnnm2 | NM_001102471.1 | chr19:46761608-46878580 | 4966 | Col6a5 | NM_001167923.1 | chr9:105856069-105960643 |
| 4870 | Cnnm3 | NM_001039551.1 | chr1:36511875-36528237 | 4967 | Col6a6 | NM_001102607.1 | chr9:105689416-105828085 |
| 4871 | Cnnm4 | NM_033570.2 | chr1:36471596-36508776 | 4968 | Col7a1 | NM_007738.3 | chr9:108953744-108984875 |
| 4872 | Cnot1 | NM_001205226.1 | chr8:95719450-95807462 | 4969 | Col8a1 | NM_007739.2 | chr16:57624255-57754737 |
| 4873 | Cnot10 | NM_153585.5 | chr9:114585873-114640200 | 4970 | Col8a2 | NM_199473.2 | chr4:126286793-126314336 |
| 4874 | Cnot11 | NM_028043.2 | chr1:39535801-39546877 | 4971 | Col9a1 | NM_001290691.1 | chr1:24195202-24252738 |
| 4875 | Cnot2 | NM_001037846.3 | chr10:116485160-116581511 | 4972 | Col9a2 | NM_007741.2 | chr4:121039565-121055325 |
| 4876 | Cnot3 | NM_146176.3 | chr7:3645268-3661109 | 4973 | Col9a3 | NM_009936.2 | chr2:180598221-180622186 |
| 4877 | Cnot4 | NM_001164411.1 | chr6:35042706-35133737 | 4974 | Colec10 | NM_173422.3 | chr15:54410773-54466358 |
| 4878 | Cnot6 | NM_001290741.1 | chr11:49671496-49702654 | 4975 | Colec11 | NM_027866.2 | chr12:28594171-28623330 |
| 4879 | Cnot6l | NM_001285511.1 | chr5:96070332-96161547 | 4976 | Colec12 | NM_130449.2 | chr18:9707647-9877998 |
| 4880 | Cnot7 | NM_001271541.1 | chr8:40492537-40515847 | 4977 | Colgalt2 | NM_177756.4 | chr1:152399866-152510695 |
| 4881 | Cnot8 | NM_026949.3 | chr11:58104152-58118594 | 4978 | Colq | NM_009937.2 | chr14:31523083-31577383 |
| 4882 | Cnp | NM_001146318.1 | chr11:100575890-100581739 | 4979 | Commd1 | NM_144514.2 | chr11:22899727-22982284 |
| 4883 | Cnppd1 | NM_026977.2 | chr1:75135214-75142368 | 4980 | Commd10 | NM_178377.4 | chr18:46958875-47087994 |
| 4884 | Cnpy1 | NM_001310511.1 | chr5:28200826-28237873 | 4981 | Commd2 | NM_175095.4 | chr3:57644348-57651684 |
| 4885 | Cnpy2 | NM_019953.1 | chr10:128322498-128327187 | 4982 | Commd3 | NM_147778.3 | chr2:18672461-18676218 |
| 4886 | Cnpy3 | NM_028063.5 | chr17:46735710-46752214 | 4983 | Commd4 | NM_025417.2 | chr9:57155040-57158299 |
| 4887 | Cnpy4 | NM_178612.4 | chr5:138187534-138193894 | 4984 | Commd5 | NM_025536.2 | chr15:76899940-76901297 |
| 4888 | Cnr1 | NM_007726.3 | chr4:33924631-33948831 | 4985 | Commd6 | NM_001033132.3 | chr14:101633765-101640471 |
| 4889 | Cnr2 | NM_009924.4 | chr4:135895188-135920219 | 4986 | Commd7 | NM_001195390.1 | chr2:153616929-153632781 |
| 4890 | Cnrip1 | NM_029861.2 | chr11:17051933-17079372 | 4987 | Commd8 | NM_178599.4 | chr5:72156999-72168183 |
| 4891 | Cnst | NM_146105.3 | chr1:179546528-179627473 | 4988 | Commd9 | NM_029635.3 | chr2:101886261-101901639 |
| 4892 | Cntd1 | NM_026562.2 | chr11:101279202-101288701 | 4989 | Comp | NM_016685.2 | chr8:70373547-70382066 |
| 4893 | Cntf | NM_170786.2 | chr19:12763527-12765632 | 4990 | Comt | NM_001111062.1 | chr16:18406881-18426716 |
| 4894 | Cntfr | NM_001136056.2 | chr4:41657497-41695445 | 4991 | Comtd1 | NM_026965.2 | chr14:21845860-21848910 |
| 4895 | Cntln | NM_175275.4 | chr4:84884308-85131921 | 4992 | Copa | NM_009938.4 | chr1:172082528-172122332 |
| 4896 | Cntn1 | NM_001159647.1 | chr15:92161356-92341967 | 4993 | Copb1 | NM_033370.3 | chr7:114215558-114254680 |
| 4897 | Cntn2 | NM_177129.5 | chr1:132509424-132542940 | 4994 | Copb2 | NM_015827.2 | chr9:98563730-98598375 |
| 4898 | Cntn3 | NM_008779.2 | chr6:102163305-102464667 | 4995 | Cope | NM_021538.1 | chr8:70302784-70312990 |
| 4899 | Cntn4 | NM_001109749.1 | chr6:106677744-106699305 | 4996 | Copg1 | NM_017477.2 | chr6:87887939-87913594 |
| 4900 | Cntn5 | NM_001033359.2 | chr9:9660890-10904726 | 4997 | Copg2 | NM_017478.3 | chr6:30747553-30896794 |
| 4901 | Cntn6 | NM_017383.3 | chr6:104493043-104863405 | 4998 | Coprs | NM_025556.3 | chr8:13884787-13890271 |
| 4902 | Cntnap1 | NM_016782.2 | chr11:101176116-101190720 | 4999 | Cops2 | NM_001285507.1 | chr2:125830301-125859082 |
| 4903 | Cntnap2 | NM_001004357.2 | chr6:45060060-47301371 | 5000 | Cops3 | NM_011991.1 | chr11:59817803-59839767 |
| 4904 | Cntnap3 | NM_001081129.1 | chr13:64737590-64903888 | 5001 | Cops4 | NM_012001.2 | chr5:100518308-100547802 |
| 4905 | Cntnap4 | NM_130457.2 | chr8:112570042-112882707 | 5002 | Cops5 | NM_001277101.1 | chr1:10024599-10038159 |
| 4906 | Cntnap5a | NM_001077425.1 | chr1:115685136-116580674 | 5003 | Cops6 | NM_012002.3 | chr5:138161101-138163984 |
| 4907 | Cntnap5b | NM_001172764 | chr1:99772764-100485942 | 5004 | Cops7a | NM_001164089.1 | chr6:124958410-124965529 |
| 4908 | Cntnap5c | NM_001081653.1 | chr17:57769689-58410342 | 5005 | Cops7b | NM_172974.2 | chr1:86587099-86606500 |
| 4909 | Cntrl | NM_001290635.1 | chr2:35132238-35147671 | 5006 | Cops8 | NM_133805.3 | chr1:90603424-90613341 |
| 4910 | Cntrob | NM_172560.3 | chr11:69299485-69303873 | 5007 | Copz1 | NM_019817.1 | chr15:103272917-103299864 |
| 4911 | Coa3 | NM_026618.2 | chr11:101277969-101278948 | 5008 | Copz2 | NM_019877.2 | chr11:96849875-96861202 |
| 4912 | Coa4 | NM_183270.3 | chr7:100537099-100539812 | 5009 | Coq10a | NM_001081040.1 | chr10:128363096-128370037 |
| 4913 | Coa5 | NM_198006.4 | chr1:37417084-37430103 | 5010 | Coq10b | NM_001039710.1 | chr1:55052769-55072702 |
| 4914 | Coa6 | NM_174987.4 | chr4:126422500-126425435 | 5011 | Coq2 | NM_027978.2 | chr5:100654725-100674256 |
| 4915 | Coa7 | NM_027250.4 | chr4:108328151-108340718 | 5012 | Coq3 | NM_172687.1 | chr4:21879674-21912126 |
| 4916 | Coasy | NM_001305982.1 | chr11:101082562-101086619 | 5013 | Coq4 | NM_178693.4 | chr2:29788262-29797743 |
| 4917 | Cobl | NM_001282993.1 | chr11:12236675-12464960 | 5014 | Coq5 | NM_026504.2 | chr5:115279701-115296972 |
| 4918 | Cobll1 | NM_007725.2 | chr2:65088338-65238626 | 5015 | Coq6 | NM_172582.3 | chr12:84361967-84373796 |
| 4919 | Coch | NM_001198835.1 | chr12:51593340-51605773 | 5016 | Coq7 | NM_009940.3 | chr7:118525661-118553356 |
| 4920 | Cog1 | NM_013581.3 | chr11:113649528-113662401 | 5017 | Coq9 | NM_026452.2 | chr8:94838416-94854895 |
| 4921 | Cog2 | NM_029746.3 | chr1:124520766-124552007 | 5018 | Corin | NM_001122756.1 | chr5:72300024-72504540 |
| 4922 | Cog3 | NM_177381.3 | chr14:75702950-75754493 | 5019 | Coro1a | NM_009898.3 | chr7:126699773-126704816 |
| 4923 | Cog4 | NM_133973.2 | chr8:110847023-110882234 | 5020 | Coro1b | NM_013778.1 | chr19:4148662-4154035 |
| 4924 | Cog5 | NM_001163126.1 | chr12:31654868-31937680 | 5021 | Coro1c | NM_011779.3 | chr5:113842438-113908706 |
| 4925 | Cog6 | NM_026225.3 | chr3:52982122-53017223 | 5022 | Coro2a | NM_001164804.1 | chr4:46536936-46601929 |
| 4926 | Cog7 | NM_001033318.3 | chr7:121922838-121981693 | 5023 | Coro2b | NM_175484.3 | chr9:62419491-62537044 |
| 4927 | Cog8 | NM_139229.4 | chr8:107048708-107056737 | 5024 | Coro6 | NM_139128.1 | chr11:77463912-77469501 |
| 4928 | Coil | NM_009706.2 | chr11:88873934-88991613 | 5025 | Coro7 | NM_030205.4 | chr16:4626883-4679720 |
| 4929 | Col10a1 | NM_009925.4 | chr10:34389980-34397085 | 5026 | Corr | NM_007745.3 | chr4:149125190-149126741 |
| 4930 | Col11a1 | NM_007729.2 | chr3:114030539-114220326 | 5027 | Cotl1 | NM_028071.3 | chr8:119809213-119840579 |
| 4931 | Col11a2 | NM_009926.1 | chr17:34039436-34066242 | 5028 | Cox10 | NM_178379.3 | chr11:63962626-64079472 |
| 4932 | Col12a1 | NM_001290308.1 | chr9:79598986-79718722 | 5029 | Cox11 | NM_199008.2 | chr11:90638183-90645977 |
| 4933 | Col13a1 | NM_007731.3 | chr10:61838233-61979108 | 5030 | Cox14 | NM_183256.3 | chr15:99725617-99728136 |
| 4934 | Col14a1 | NM_181277.3 | chr15:55317744-55520803 | 5031 | Cox15 | NM_144874.4 | chr19:43733253-43753000 |
| 4935 | Col15a1 | NM_009928.3 | chr4:47208011-47313165 | 5032 | Cox16 | NM_025461.6 | chr12:81470602-81485137 |
| 4936 | Col16a1 | NM_028266.5 | chr4:130047859-130099277 | 5033 | Cox17 | NM_001017429.2 | chr16:38346998-38352763 |
| 4937 | Col17a1 | NM_001290825.1 | chr19:47646340-47692042 | 5034 | Cox18 | NM_001033310.3 | chr5:90214724-90223996 |
| 4938 | Col18a1 | NM_001109991.1 | chr10:77052178-77113705 | 5035 | Cox19 | NM_197980.1 | chr5:139337821-139345166 |
| 4939 | Col19a1 | NM_007733.2 | chr1:24257682-24587437 | 5036 | Cox20 | NM_025511.2 | chr1:178139152-178322693 |
| 4940 | Col1a1 | NM_007742.4 | chr11:94936223-94963042 | 5037 | Cox4i1 | NM_009941.3 | chr8:120668224-120674209 |
| 4941 | Col1a2 | NM_007743.2 | chr6:4505696-4541543 | 5038 | Cox4i2 | NM_053091.2 | chr2:152754172-152765037 |
| 4942 | Col20a1 | NM_028518.1 | chr2:180986534-181017540 | 5039 | Cox5a | NM_007747 | chr9:57521233-57532426 |
| 4943 | Col22a1 | NM_027174.1 | chr15:71798475-72034227 | 5040 | Cox5b | NM_009942.2 | chr1:36691486-36693388 |
| 4944 | Col23a1 | NM_153393.2 | chr11:51289919-51583325 | 5041 | Cox6a1 | NM_007748.2 | chr5:115345653-115348955 |
| 4945 | Col24a1 | NM_027770.2 | chr3:145292471-145552005 | 5042 | Cox6a2 | NM_009943.2 | chr7:128205434-128206366 |
| 4946 | Col25a1 | NM_001244952.1 | chr3:130180844-130599883 | 5043 | Cox6b1 | NM_025628.2 | chr7:30616973-30626151 |

Fig.21 - 27

| | | | | | | | | |
|---|---|---|---|---|---|---|---|---|
| 5044 | Cox6b2 | NM_001289848.1 | chr7:4751791-4753094 | 5141 | Crhr1 | NM_007762.5 | chr11:104132780-104175523 |
| 5045 | Cox6c | NM_053071.2 | chr15:35931975-35938246 | 5142 | Crhr2 | NM_001288618.1 | chr6:55090048-55133016 |
| 5046 | Cox7a1 | NM_009944.3 | chr7:30184170-30186030 | 5143 | Crim1 | NM_015800.3 | chr17:78200247-78376592 |
| 5047 | Cox7a2 | NM_009945.3 | chr9:79755240-79759853 | 5144 | Crip1 | NM_007763.3 | chr12:113152011-113153879 |
| 5048 | Cox7a2l | NM_001159529.1 | chr17:83501916-83514333 | 5145 | Crip2 | NM_024223.2 | chr12:113140235-113145906 |
| 5049 | Cox7b | NM_025379.2 | chrX:106015699-106022450 | 5146 | Crip3 | NM_053250.2 | chr17:46428941-46431771 |
| 5050 | Cox7b2 | NM_030052.3 | chr5:71442822-71548205 | 5147 | Cript | NM_019936.3 | chr17:87025560-87035808 |
| 5051 | Cox7c | NM_007749.3 | chr13:86044797-86046795 | 5148 | Crisp1 | NM_009638.3 | chr17:40293757-40319207 |
| 5052 | Cox8a | NM_007750.2 | chr19:7215157-7217616 | 5149 | Crisp2 | NM_001204071.1 | chr17:40764733-40794146 |
| 5053 | Cox8b | NM_007751.3 | chr7:140898941-140900446 | 5150 | Crisp3 | NM_009639.2 | chr17:40221776-40242258 |
| 5054 | Cox8c | NM_001039049.1 | chr12:102899305-102900534 | 5151 | Crisp4 | NM_030033.1 | chr1:18115190-18137051 |
| 5055 | Cp | NM_001276248.1 | chr3:19957053-20007609 | 5152 | Crispld1 | NM_031402.2 | chr1:177227416-17766207 |
| 5056 | Cpa1 | NM_025350.3 | chr6:30639220-30645361 | 5153 | Crispld2 | NM_030209.4 | chr8:119992437-120052794 |
| 5057 | Cpa2 | NM_001024698.2 | chr6:30541641-30564473 | 5154 | Crk | NM_001277219.1 | chr17:75679258-75708428 |
| 5058 | Cpa3 | NM_007753.2 | chr3:20215615-20242181 | 5155 | Crkl | NM_001277231.1 | chr16:17451984-17487440 |
| 5059 | Cpa4 | NM_027926.2 | chr6:30568375-30591747 | 5156 | Crif1 | NM_018827.2 | chr8:70493155-70504081 |
| 5060 | Cpa5 | NM_144537.3 | chr6:30611009-30631521 | 5157 | Crif2 | NM_001164735.1 | chr5:109554708-109558993 |
| 5061 | Cpa6 | NM_001289497.1 | chr1:10324718-10719945 | 5158 | Crif3 | NM_001277106.1 | chr11:80046492-80080991 |
| 5062 | Cpb1 | NM_029706.1 | chr3:20249463-20275729 | 5159 | Crls1 | NM_001024385.1 | chr2:132846665-132866768 |
| 5063 | Cpb2 | NM_019775.3 | chr14:75242286-75283553 | 5160 | Crmp1 | NM_001136058.2 | chr5:37242657-37292163 |
| 5064 | Cpd | NM_007754.2 | chr11:76777207-76847008 | 5161 | Crnde | NR_033641.3 | chr8:92326030-92356120 |
| 5065 | Cpe | NM_013494.3 | chr8:64592550-64693040 | 5162 | Crnkl1 | NM_025820.3 | chr2:145917481-145934700 |
| 5066 | Cpeb1 | NM_001252525.1 | chr7:81347025-81454758 | 5163 | Crnn | NM_001081200.1 | chr3:93144786-93149471 |
| 5067 | Cpeb2 | NM_001177379.1 | chr5:43233462-43289724 | 5164 | Crocc | NM_001145958.1 | chr4:141016636-141060545 |
| 5068 | Cpeb3 | NM_001290826.1 | chr19:37021290-37176063 | 5165 | Crot | NM_023733.3 | chr5:8966047-8997146 |
| 5069 | Cpeb4 | NM_001290676.1 | chr11:31870939-31935635 | 5166 | Crp | NM_007768.4 | chr1:172698055-172699966 |
| 5070 | Cped1 | NM_001081351.1 | chr6:21985909-22255606 | 5167 | Crtac1 | NM_145123.4 | chr19:42283036-42431783 |
| 5071 | Cphx1 | NM_175342.3 | chr14:25942543-26235735 | 5168 | Crtam | NM_001281954.1 | chr9:40972797-41004628 |
| 5072 | Cphx2 | NM_001270506.1 | chr14:25942539-26235740 | 5169 | Crtap | NM_019922.2 | chr9:114375130-114390713 |
| 5073 | Cplx1 | NM_007756.3 | chr5:108518553-108550027 | 5170 | Crtc1 | NM_001004062.2 | chr8:70382357-70439573 |
| 5074 | Cplx2 | NM_009946.3 | chr13:54371348-54383917 | 5171 | Crtc2 | NM_028871.2 | chr3:90254280-90264125 |
| 5075 | Cplx3 | NM_146223.3 | chr9:57569991-57606281 | 5172 | Crtc3 | NM_173863.2 | chr7:80586631-80688877 |
| 5076 | Cplx4 | NM_145493.1 | chr18:65955721-65970178 | 5173 | Crx | NM_001113330.1 | chr7:15865946-15872385 |
| 5077 | Cpm | NM_027468.1 | chr10:117629499-117687352 | 5174 | Crxos | NM_001033638.2 | chr7:15896123-15904030 |
| 5078 | Cpn1 | NM_030703.2 | chr19:43956307-43986520 | 5175 | Cry1 | NM_007771.3 | chr10:85131699-85185054 |
| 5079 | Cpn2 | NM_027904.3 | chr16:30256378-30267532 | 5176 | Cry2 | NM_009963.4 | chr2:92403646-92434069 |
| 5080 | Cpne1 | NM_170588.3 | chr2:156071840-156111965 | 5177 | Cryaa | NM_001278569.1 | chr17:31677930-31681730 |
| 5081 | Cpne2 | NM_153507.2 | chr8:94533027-94570529 | 5178 | Cryab | NM_001289782.1 | chr9:50751324-50756635 |
| 5082 | Cpne3 | NM_027769.2 | chr4:19519251-19570104 | 5179 | Crybal | NM_009965.3 | chr11:77718613-77725293 |
| 5083 | Cpne4 | NM_028719.1 | chr9:104569787-105034544 | 5180 | Cryba2 | NM_021541.3 | chr1:74889933-74893143 |
| 5084 | Cpne5 | NM_153166.2 | chr17:29156520-29237790 | 5181 | Cryba4 | NM_021351.2 | chr5:112246491-112252518 |
| 5085 | Cpne6 | NM_001136057.2 | chr14:55510447-55517431 | 5182 | Crybb1 | NM_023695.3 | chr5:112255819-112269585 |
| 5086 | Cpne7 | NM_170684.2 | chr8:123117373-123135185 | 5183 | Crybb2 | NM_007773.4 | chr5:113058257-113070117 |
| 5087 | Cpne8 | NM_001033851.1 | chr15:90643322-90679388 | 5184 | Crybb3 | NM_001159650.1 | chr5:113075838-113081584 |
| 5088 | Cpne9 | NM_170673.3 | chr6:113282306-113305571 | 5185 | Crybg3 | NM_174848.3 | chr16:59490774-59555752 |
| 5089 | Cpox | NM_007757.2 | chr16:58670207-58680389 | 5186 | Cryga | NM_007774.3 | chr1:65100388-65108363 |
| 5090 | Cpped1 | NM_146067.3 | chr16:11863720-11909423 | 5187 | Crygb | NM_144761.2 | chr1:65080221-65082290 |
| 5091 | Cpq | NM_018755.2 | chr15:33083128-33594552 | 5188 | Crygc | NM_001082573.2 | chr1:65071524-65073532 |
| 5092 | Cps1 | NM_001080809.2 | chr1:67123026-67231267 | 5189 | Crygd | NM_007776.2 | chr1:65061837-65063440 |
| 5093 | Cpsf1 | NM_001164173.1 | chr15:76595807-76607591 | 5190 | Cryge | NM_007777.3 | chr1:65048556-65051163 |
| 5094 | Cpsf2 | NM_016856.3 | chr12:101975973-102005993 | 5191 | Crygf | NM_070010.2 | chr1:65926521-65928304 |
| 5095 | Cpsf3 | NM_018813.3 | chr12:21286296-21315056 | 5192 | Crygn | NM_153076.2 | chr5:24751001-24757843 |
| 5096 | Cpsf3l | NM_028020.3 | chr4:155869566-155889103 | 5193 | Crygs | NM_009967.2 | chr16:22805202-22811410 |
| 5097 | Cpsf4 | NM_001291248.1 | chr5:145167212-145182041 | 5194 | Cryl1 | NM_030004.3 | chr14:57275033-57398483 |
| 5098 | Cpsf4l | NM_001164532.1 | chr11:113698170-113709526 | 5195 | Crym | NM_016669.1 | chr7:120186383-120201988 |
| 5099 | Cpsf6 | NM_001013391.2 | chr10:117344667-117376973 | 5196 | Cryz | NM_009968.3 | chr3:154596710-154623182 |
| 5100 | Cpsf7 | NM_001164221.1 | chr19:100525243-105477235 | 5197 | Cryzl1 | NM_026994.1 | chr16:91689321-91728802 |
| 5101 | Cpt1a | NM_013495.2 | chr19:3323300-3385733 | 5198 | Cs | NM_026444.3 | chr10:128337831-128362479 |
| 5102 | Cpt1b | NM_009948.2 | chr15:89416404-89425862 | 5199 | Csad | NM_144942.4 | chr15:102176997-102189043 |
| 5103 | Cpt1c | NM_001252470.1 | chr7:44969517-44974851 | 5200 | Csdc2 | NM_145473.3 | chr15:81936758-81950941 |
| 5104 | Cpt2 | NM_009949.2 | chr4:107903981-107923589 | 5201 | Csde1 | NM_001161854.2 | chr3:103020545-103058186 |
| 5105 | Cpvl | NM_001289713.1 | chr6:53873278-53978073 | 5202 | Cse1l | NM_023565.3 | chr2:166906095-166946389 |
| 5106 | Cpxcr1 | NM_001033471.3 | chrX:116448943-116478783 | 5203 | Csf1 | NM_001113529.1 | chr3:107741047-107760469 |
| 5107 | Cpxm1 | NM_019696.2 | chr2:130390774-130397629 | 5204 | Csf1r | NM_001037859.2 | chr18:61105571-61131139 |
| 5108 | Cpxm2 | NM_018867.5 | chr7:132042809-132154741 | 5205 | Csf2 | NM_009969.4 | chr11:54247269-54249809 |
| 5109 | Cpz | NM_153107.2 | chr5:35502217-35525826 | 5206 | Csf2ra | NM_009970.2 | chr19:61224401-61228418 |
| 5110 | Cr1l | NM_013499.2 | chr1:195103787-195131570 | 5207 | Csf2rb | NM_007780.4 | chr15:78325989-78351001 |
| 5111 | Cr2 | NM_007758.3 | chr1:195136810-195176715 | 5208 | Csf2rb2 | NM_001287389.1 | chr15:78282507-78309721 |
| 5112 | Crabp1 | NM_001284507.1 | chr9:54764747-54773110 | 5209 | Csf3 | NM_009971.1 | chr11:98701312-98703629 |
| 5113 | Crabp2 | NM_007759.2 | chr3:87948680-87953372 | 5210 | Csf3r | NM_001252651.1 | chr4:126024658-126044975 |
| 5114 | Cradd | NM_009950.2 | chr10:95174745-95324097 | 5211 | Csgalnact1 | NM_001252623.1 | chr8:68356780-68735146 |
| 5115 | Crampl1 | NM_020608.3 | chr17:24961225-25015230 | 5212 | Csgalnact2 | NM_030165.3 | chr6:118107431-118139140 |
| 5116 | Crat | NM_007760.3 | chr2:30400475-30415748 | 5213 | Csk | NM_007783.3 | chr9:57602645-57645653 |
| 5117 | Crb1 | NM_133239.2 | chr1:139198253-139377076 | 5214 | Csl | NM_027945.3 | chr10:99757704-99759658 |
| 5118 | Crb2 | NM_001163566.1 | chr2:37776248-37799103 | 5215 | Csmd1 | NM_053171.2 | chr8:15892544-17535385 |
| 5119 | Crb3 | NM_175706.2 | chr17:57062276-57065914 | 5216 | Csmd2 | NM_001281955.1 | chr4:127988043-128567656 |
| 5120 | Crbn | NM_021449.3 | chr6:106778244-106800087 | 5217 | Csmd2os | NM_029137.1 | chr4:128133522-128166597 |
| 5121 | Crcp | NM_007761.2 | chr5:130029905-130060783 | 5218 | Csmd3 | NM_001081391.2 | chr15:47580637-48791989 |
| 5122 | Crct1 | NM_028798.3 | chr3:93014204-93015686 | 5219 | Csn1s1 | NM_001286015.1 | chr5:87666207-87682577 |
| 5123 | Creb1 | NM_001037726.1 | chr1:64532803-64604548 | 5220 | Csn1s2a | NM_007785.2 | chr5:87774449-87788798 |
| 5124 | Creb3 | NM_497.3 | chr4:43562633-43567060 | 5221 | Csn1s2b | NM_009973.3 | chr5:87808120-87824421 |
| 5125 | Creb3l1 | NM_011957.2 | chr2:91982327-92024170 | 5222 | Csn2 | NM_001286020.1 | chr5:87682818-87699425 |
| 5126 | Creb3l2 | NM_178661.4 | chr6:37331020-37442148 | 5223 | Csn3 | NM_007786.4 | chr5:87925632-87932264 |
| 5127 | Creb3l3 | NM_145365.3 | chr10:81084332-81098672 | 5224 | Csnk1a1 | NM_146087.2 | chr18:61555581-61588299 |
| 5128 | Creb3l4 | NM_030080.3 | chr3:90237497-90243512 | 5225 | Csnk1d | NM_027874.2 | chr11:120961740-120991333 |
| 5129 | Creb5 | NM_172728.2 | chr6:53573374-53698832 | 5226 | Csnk1e | NM_001289898.1 | chr15:79417851-79442057 |
| 5130 | Crebbp | NM_001025432.1 | chr16:4084047-4213404 | 5227 | Csnk1g1 | NM_173185.2 | chr9:65909009-66045014 |
| 5131 | Crebl2 | NM_177687.3 | chr6:134830198-134857883 | 5228 | Csnk1g2 | NM_001159591.1 | chr10:80629655-80640771 |
| 5132 | Crebrf | NM_029870.2 | chr17:26715649-26776626 | 5229 | Csnk1g3 | NM_152809.2 | chr18:53862112-53956684 |
| 5133 | Crebzf | NM_145151.3 | chr7:90442780-90448043 | 5230 | Csnk2a1 | NM_007788.3 | chr2:152220839-152281851 |
| 5134 | Creg1 | NM_011804.2 | chr1:165763779-165775304 | 5231 | Csnk2a2 | NM_009974.3 | chr8:95446095-95488820 |
| 5135 | Creg2 | NM_029870.2 | chr1:39619405-39651182 | 5232 | Csnk2b | NM_009975.3 | chr17:35116194-35121292 |
| 5136 | Creld1 | NM_133930.1 | chr6:113483568-113493338 | 5233 | Csnka2ip | NM_173861.2 | chr16:64477810-64479134 |
| 5137 | Creld2 | NM_029826.4 | chr15:88645615-88826681 | 5234 | Cspg4 | NM_139001.2 | chr9:56865103-56899870 |
| 5138 | Crem | NM_001110850.2 | chr18:3266353-3327591 | 5235 | Cspg5 | NM_001166273.1 | chr9:110243782-110262576 |
| 5139 | Crh | NM_205769.3 | chr3:19693400-19695396 | 5236 | Cspp1 | NM_026493.3 | chr1:10038217-10136768 |
| 5140 | Crhbp | NM_198408.3 | chr13:95431375-95444831 | 5237 | Csprs | NM_033616.3 | chr1_GL456221_random:11157-163011 |

Fig. 21 - 28

| | | | | | | |
|---|---|---|---|---|---|---|
| 5238 | Csrp1 | NM_153287.3 | chr9:119971165-119984658 | 5335 | Cubn | NM_001081084.2 | chr2:13276337-13491876 |
| 5239 | Csrp2 | NM_153407.2 | chr15:100479569-100495239 | 5336 | Cuedc1 | NM_001172099.1 | chr11:88169564-88194140 |
| 5240 | Csrp3 | NM_001290665.1 | chr2:65931864-66031546 | 5337 | Cuedc2 | NM_001164290.1 | chr19:46329811-46338680 |
| 5241 | Csrp1 | NM_007791.5 | chr1:135729196-135752229 | 5338 | Cul1 | NM_012042.3 | chr6:47454323-47526139 |
| 5242 | Csrp2 | NM_007792.4 | chr10:110920175-110939514 | 5339 | Cul2 | NM_029402.3 | chr18:3383224-3436760 |
| 5243 | Csrp2bp | NM_001166640.1 | chr2:144369031-144407675 | 5340 | Cul3 | NM_016716.5 | chr1:80264922-80340690 |
| 5244 | Csrp3 | NM_001198841.1 | chr7:48830397-48848051 | 5341 | Cul4a | NM_146207.2 | chr8:13105720-13147939 |
| 5245 | Cst10 | NM_021405.2 | chr2:149405248-149410278 | 5342 | Cul4b | NM_001110142.1 | chrX:38531620-38576196 |
| 5246 | Cst11 | NM_030059.2 | chr2:148768617-148771497 | 5343 | Cul5 | NM_001161618.1 | chr9:53614581-53667507 |
| 5247 | Cst12 | NM_027054.1 | chr2:148789360-148793437 | 5344 | Cul7 | NM_025611.5 | chr17:46650337-46664364 |
| 5248 | Cst13 | NM_027024.3 | chr2:148820098-148830410 | 5345 | Cul9 | NM_001081335.2 | chr17:46500608-46546388 |
| 5249 | Cst3 | NM_009976.4 | chr2:148871221-148875512 | 5346 | Cuta | NM_026307.3 | chr17:26937971-26939938 |
| 5250 | Cst6 | NM_028623.5 | chr19:5344704-5349574 | 5347 | Cutal | NM_030021.3 | chr2:34874395-34892133 |
| 5251 | Cst7 | NM_009977.3 | chr2:150570414-150578944 | 5348 | Cutc | NM_001133562.1 | chr19:43753022-43768638 |
| 5252 | Cst8 | NM_009978.2 | chr2:148798838-148805684 | 5349 | Cux1 | NM_001291233.1 | chr5:136266409-136565981 |
| 5253 | Cst9 | NM_009979.1 | chr2:148835146-148838737 | 5350 | Cux2 | NM_007804.2 | chr5:121860215-122047825 |
| 5254 | Csta1 | NM_001033239.3 | chr16:36119945-36131189 | 5351 | Cuzd1 | NM_008411.3 | chr7:131308953-131322292 |
| 5255 | Cstad | NM_030137.2 | chr2:30595043-30608945 | 5352 | Cwc15 | NM_023153.3 | chr9:14500618-14510620 |
| 5256 | Cstb | NM_007793.3 | chr10:78425869-78427622 | 5353 | Cwc22 | NM_001290740.1 | chr2:77895652-77946358 |
| 5257 | Cstf1 | NM_024199.2 | chr2:172371002-172381086 | 5354 | Cwc25 | NM_026186.4 | chr11:97745469-97766613 |
| 5258 | Cstf2 | NM_001290396.1 | chrX:134059175-134086822 | 5355 | Cwc27 | NM_028072.1 | chr13:104631326-104816953 |
| 5259 | Cstf2t | NM_031249.2 | chr19:31082840-31086592 | 5356 | Cwf19l1 | NM_001081077.1 | chr19:44108636-44135876 |
| 5260 | Cstf3 | NM_001037326.2 | chr2:104590483-104609429 | 5357 | Cwf19l2 | NM_027545.2 | chr9:3404084-3479236 |
| 5261 | Cstl1 | NM_177655.3 | chr2:148750360-148755378 | 5358 | Cwh43 | NM_181323.2 | chr5:73406077-73453425 |
| 5262 | Ctag2 | NM_027302.2 | chrX:65047643-65049017 | 5359 | Cx3cl1 | NM_009142.3 | chr8:94772179-94782426 |
| 5263 | Ctage5 | NM_001165253.1 | chr12:59131452-59190220 | 5360 | Cx3cr1 | NM_009987.4 | chr9:120048682-120068296 |
| 5264 | Ctbp1 | NM_001198859.1 | chr5:33247722-33275004 | 5361 | Cxadr | NM_001025192.3 | chr16:78301670-78340759 |
| 5265 | Ctbp2 | NM_001170744.1 | chr7:132987010-133015247 | 5362 | Cxcl1 | NM_008176.3 | chr5:90891244-90893115 |
| 5266 | Ctbs | NM_028836.4 | chr3:146450466-146465848 | 5363 | Cxcl10 | NM_021274.2 | chr5:92346638-92348889 |
| 5267 | Ctc1 | NM_001013256.2 | chr11:69015910-69036473 | 5364 | Cxcl11 | NM_019494.1 | chr5:92359544-92363277 |
| 5268 | Ctcf | NM_181322.3 | chr8:105636537-105682922 | 5365 | Cxcl12 | NM_001012477.2 | chr6:117166534-117181368 |
| 5269 | Ctcfl | NM_001081387.2 | chr2:173093608-173119525 | 5366 | Cxcl13 | NM_018866.2 | chr5:95956938-95961068 |
| 5270 | Ctcflos | NR_040321.1 | chr2:173124748-173133204 | 5367 | Cxcl14 | NM_019568.2 | chr13:56288642-56296551 |
| 5271 | Ctdnep1 | NM_026017.2 | chr11:69981167-69990600 | 5368 | Cxcl15 | NM_011339.2 | chr5:90794533-90803067 |
| 5272 | Ctdp1 | NM_026295.2 | chr18:80407958-80469667 | 5369 | Cxcl16 | NM_023158.6 | chr11:70454233-70459984 |
| 5273 | Ctdsp1 | NM_153088.2 | chr1:74391608-74397285 | 5370 | Cxcl17 | NM_153576.2 | chr7:25400052-25412886 |
| 5274 | Ctdsp2 | NM_001113470.1 | chr10:126978716-126999975 | 5371 | Cxcl2 | NM_009140.2 | chr5:90903898-90905918 |
| 5275 | Ctdspl | NM_133710.3 | chr9:118926535-119044119 | 5372 | Cxcl3 | NM_203320.3 | chr5:90786100-90788093 |
| 5276 | Ctdspl2 | NM_001290991.1 | chr2:121956000-122015326 | 5373 | Cxcl5 | NM_009141.3 | chr5:90759297-90761625 |
| 5277 | Ctf1 | NM_007795.1 | chr7:127712735-127718185 | 5374 | Cxcl9 | NM_008599.4 | chr5:92321330-92328079 |
| 5278 | Ctf2 | NM_198858.1 | chr7:127718959-127725616 | 5375 | Cxcr1 | NM_178241.4 | chr1:74191785-74194631 |
| 5279 | Ctgf | NM_010217.2 | chr10:24595441-24598682 | 5376 | Cxcr2 | NM_009909.3 | chr1:74153993-74161746 |
| 5280 | Cth | NM_145953.2 | chr3:157894247-157925063 | 5377 | Cxcr3 | NM_009910.3 | chrX:101731534-101734147 |
| 5281 | Cthrc1 | NM_026778.2 | chr15:39076931-39087119 | 5378 | Cxcr4 | NM_009911.3 | chr1:128588198-128592299 |
| 5282 | Ctif | NM_175431.2 | chr18:75693220-75697696 | 5379 | Cxcr5 | NM_007551.2 | chr9:44511786-44526421 |
| 5283 | Ctla2a | NM_001145799.1 | chr13:60934154-60936566 | 5380 | Cxcr6 | NM_030712.4 | chr9:123806476-123811754 |
| 5284 | Ctla2b | NM_001145801.1 | chr13:60895350-60897447 | 5381 | Cxxla | NM_024170.2 | chrX:53642488-53643763 |
| 5285 | Ctla4 | NM_001281976.1 | chr1:60909024-60915832 | 5382 | Cxx1b | NM_001018063.1 | chrX:53669176-53670408 |
| 5286 | Ctnna1 | NM_009818.1 | chr18:35118911-35254775 | 5383 | Cxx1c | NM_028375.3 | chrX:53607921-53609134 |
| 5287 | Ctnna2 | NM_001109764.1 | chr6:76881636-77979667 | 5384 | Cxxc1 | NM_028868.3 | chr18:74216211-74221491 |
| 5288 | Ctnna3 | NM_001164376.1 | chr10:63457510-65003667 | 5385 | Cxxc4 | NM_001004367.4 | chr3:134236494-134262089 |
| 5289 | Ctnnal1 | NM_018761.3 | chr4:56810934-56865211 | 5386 | Cxxc5 | NM_133687.2 | chr18:35829817-35861688 |
| 5290 | Ctnnb1 | NM_001165902.1 | chr9:120933577-120960507 | 5387 | Cyb561 | NM_025797.3 | chr11:105933703-105944147 |
| 5291 | Ctnnbip1 | NM_001141930.1 | chr4:149545116-149566437 | 5388 | Cyb561a3 | NM_001282064.1 | chr19:10577158-10590041 |
| 5292 | Ctnnbl1 | NM_025696.4 | chr2:157737400-157891903 | 5389 | Cyb561d1 | NM_001081320.2 | chr3:108195770-108200834 |
| 5293 | Ctnnd1 | NM_001085448.1 | chr2:84600780-84650740 | 5390 | Cyb561d2 | NM_019720.4 | chr9:107539010-107541865 |
| 5294 | Ctnnd2 | NM_008729.2 | chr15:30172592-31029343 | 5391 | Cyb5b | NM_025558.5 | chr8:107105660-107187470 |
| 5295 | Ctns | NM_031251.4 | chr11:73183132-73199019 | 5392 | Cyb5d1 | NM_001045525.1 | chr11:69393611-88395346 |
| 5296 | Ctps | NM_016748.2 | chr4:120539867-120570276 | 5393 | Cyb5d2 | NM_001024926.3 | chr11:72777231-72795839 |
| 5297 | Ctps2 | NM_001168568.1 | chrX:162901559-163034541 | 5394 | Cyb5r1 | NM_028057.2 | chr1:134405989-134411738 |
| 5298 | Ctr9 | NM_009431.2 | chr7:111028950-111056371 | 5395 | Cyb5r2 | NM_001205227.1 | chr7:107748454-107758032 |
| 5299 | Ctrb1 | NM_025583.2 | chr8:111686509-111691910 | 5396 | Cyb5r3 | NM_029787.2 | chr15:83153500-83172208 |
| 5300 | Ctrc | NM_001033875.2 | chr4:141438239-141846359 | 5397 | Cyb5r4 | NM_024195.2 | chr9:87022028-87077774 |
| 5301 | Ctrcos | NR_040641.1 | chr4:141844320-141846990 | 5398 | Cyb5r1 | NM_175471.2 | chr4:107070167-107084805 |
| 5302 | Ctrl | NM_023182.2 | chr8:105931993-105933862 | 5399 | Cyba | NM_007806.3 | chr8:122424770-122432940 |
| 5303 | Cts3 | NM_026926.3 | chr13:61564629-61579127 | 5400 | Cybb | NM_007807.5 | chrX:9435253-9469324 |
| 5304 | Cts6 | NM_021445.1 | chr13:61395146-61263392 | 5401 | Cybrd1 | NM_028593.2 | chr2:71118053-71142926 |
| 5305 | Cts7 | NM_019539.3 | chr13:61352460-61358170 | 5402 | Cyc1 | NM_025567.2 | chr15:76343522-76345934 |
| 5306 | Cts8 | NM_019541.3 | chr13:61246746-61255348 | 5403 | Cyct | NM_007808.4 | chr6:50562562-50566474 |
| 5307 | Cts8-ps | NR_027871.2 | chr13:61281379-61288850 | 5404 | Cycs | NM_009989.3 | chr2:76353941-76380453 |
| 5308 | Ctsa | NM_001038492.2 | chr2:164832871-164841032 | 5405 | Cyfip1 | NM_001164661.1 | chr7:55842070-55932633 |
| 5309 | Ctsb | NM_007798.4 | chr14:63122461-63145923 | 5406 | Cyfip2 | NM_001252459.1 | chr11:46193848-46312859 |
| 5310 | Ctsc | NM_009982.5 | chr7:88278084-88315861 | 5407 | Cygb | NM_030206.4 | chr11:116645594-116654313 |
| 5311 | Ctsd | NM_009983.2 | chr7:142375915-142387870 | 5408 | Cyhr1 | NM_001276321.1 | chr15:76646926-76656901 |
| 5312 | Ctse | NM_007799.3 | chr1:131638313-131675507 | 5409 | Cylc1 | NM_026134.2 | chrX:111110417-111123874 |
| 5313 | Ctsf | NM_019861.1 | chr19:4855128-4860912 | 5410 | Cylc2 | NM_001162865.1 | chr4:51216677-51229928 |
| 5314 | Ctsg | NM_007800.2 | chr14:56099884-56102574 | 5411 | Cyld | NM_001128170.2 | chr8:88697027-88751946 |
| 5315 | Ctsh | NM_007801.3 | chr9:90054266-90076095 | 5412 | Cym | NM_001111143.1 | chr1:107211294-107221732 |
| 5316 | Ctsj | NM_010077.1 | chr13:61000277-61005911 | 5413 | Cyp11a1 | NM_019779.3 | chr9:58015016-58027023 |
| 5317 | Ctsk | NM_007802.4 | chr3:95499209-95509387 | 5414 | Cyp11b1 | NM_001033229.3 | chr15:74834891-74841643 |
| 5318 | Ctsl | NM_009984.4 | chr13:64361889-64370520 | 5415 | Cyp11b2 | NM_009991.3 | chr15:74851009-74856318 |
| 5319 | Ctsll3 | NM_027344.3 | chr13:60798249-60802844 | 5416 | Cyp17a1 | NM_007809.3 | chr19:46667164-46673000 |
| 5320 | Ctsm | NM_022326.3 | chr13:61538443-61541839 | 5417 | Cyp19a1 | NM_007810.3 | chr9:54165936-54193442 |
| 5321 | Ctso | NM_177662.2 | chr8:81932615-81956725 | 5418 | Cyp1a1 | NM_001136059.1 | chr9:57697612-57703624 |
| 5322 | Ctsq | NM_029636.3 | chr13:61035037-61046597 | 5419 | Cyp1a2 | NM_009993.3 | chr9:57677936-57683655 |
| 5323 | Ctsr | NM_028284.1 | chr13:61159214-61164188 | 5420 | Cyp1b1 | NM_009994.1 | chr17:79706952-79715041 |
| 5324 | Ctss | NM_001267695.2 | chr3:88725735-95556405 | 5421 | Cyp20a1 | NM_030013.3 | chr1:60343299-60388060 |
| 5325 | Ctsw | NM_009985.5 | chr19:5465042-5468507 | 5422 | Cyp21a1 | NM_009995.2 | chr17:34801347-34804426 |
| 5326 | Ctsz | NM_022325.5 | chr2:174427493-174439039 | 5423 | Cyp24a1 | NM_007811.2 | chr2:170482956-170497145 |
| 5327 | Cttn | NM_001252572.1 | chr7:144435723-144470935 | 5424 | Cyp26a1 | NM_007811.2 | chr19:37697807-37701936 |
| 5328 | Cttnbp2 | NM_080285.1 | chr6:18365476-18514825 | 5425 | Cyp26b1 | NM_001177713.1 | chr6:84571413-84593908 |
| 5329 | Cttnbp2nl | NM_001163332.1 | chr3:105001914-105052953 | 5426 | Cyp26c1 | NM_001105201.1 | chr19:37685679-37693307 |
| 5330 | Ctu1 | NM_145532.1 | chr7:43672030-43678297 | 5427 | Cyp27a1 | NM_024264.5 | chr1:74713534-74737697 |
| 5331 | Ctu2 | NM_153775.2 | chr8:122476142-122483092 | 5428 | Cyp27b1 | NM_010009.2 | chr10:127048245-127053006 |
| 5332 | Ctxn1 | NM_183315.2 | chr8:4257645-4259974 | 5429 | Cyp2a12 | NM_133657.1 | chr7:27029089-27038815 |
| 5333 | Ctxn2 | NM_001162934.1 | chr2:125136691-125147841 | 5430 | Cyp2a22 | NM_001101467.1 | chr7:26931630-26939386 |
| 5334 | Ctxn3 | NM_001134697.1 | chr18:57468485-57478134 | 5431 | | | |

Fig.21 - 29

| | | | | | | | |
|---|---|---|---|---|---|---|---|
| 5432 | Cyp2a4 | NM_009997.2 | chr7:26307191-26315088 | 5529 | Cys1 | NM_001004455.2 | chr12:24665837-24681795 |
| 5433 | Cyp2a5 | NM_007812.4 | chr7:26835338-26843264 | 5530 | Cysltr1 | NM_001281859.1 | chrX:106576508-106603679 |
| 5434 | Cyp2b1 | NM_183158.3 | chr16:20308386-20325404 | 5531 | Cysltr2 | NM_001162412.1 | chr14:73029127-73049114 |
| 5435 | Cyp2b10 | NM_009999.4 | chr7:25897657-25926624 | 5532 | Cystm1 | NM_001081365.1 | chr18:36348623-36393370 |
| 5436 | Cyp2b13 | NM_007813.2 | chr7:26061494-26096196 | 5533 | Cyth1 | NM_001112699.1 | chr11:118164165-118248592 |
| 5437 | Cyp2b19 | NM_007814.2 | chr7:26757141-26772630 | 5534 | Cyth2 | NM_001112701.1 | chr7:45806636-45814316 |
| 5438 | Cyp2b23 | NM_001081148.1 | chr7:26665226-26686430 | 5535 | Cyth3 | NM_001163548.1 | chr5:143661240-143710248 |
| 5439 | Cyp2b9 | NM_010000.2 | chr7:26173408-26210660 | 5536 | Cyth4 | NM_028195.3 | chr15:78597046-78622019 |
| 5440 | Cyp2c29 | NM_007815.3 | chr19:39287084-39330713 | 5537 | Cytip | NM_139200.4 | chr2:58129138-58180122 |
| 5441 | Cyp2c37 | NM_010001.2 | chr19:39992423-40012243 | 5538 | Cytl1 | NM_001081106.1 | chr5:37735518-37739820 |
| 5442 | Cyp2c38 | NM_010002.3 | chr19:39389555-39463075 | 5539 | Cyyr1 | NM_144853.3 | chr16:85456243-85550373 |
| 5443 | Cyp2c39 | NM_010003.2 | chr19:39510821-39568529 | 5540 | D030018L15Rik | NR_126492.1 | chr15:96051616-96079553 |
| 5444 | Cyp2c40 | NM_010004.2 | chr19:39767072-39812814 | 5541 | D030024E09Rik | NR_040350.1 | chr15:61699283-61774451 |
| 5445 | Cyp2c44 | NM_001004446.3 | chr19:44005021-44029247 | 5542 | D030025E07Rik | NR_045704.1 | chr3:128117014-128231605 |
| 5446 | Cyp2c50 | NM_001167875.1 | chr19:40089678-40113955 | 5543 | D030025P21Rik | NR_028577.1 | chr12:84875801-84879755 |
| 5447 | Cyp2c53-ps | NR_033614.1 | chr19:39229253-39274737 | 5544 | D030028A08Rik | NR_003293.3 | chr11:96944145-96965060 |
| 5448 | Cyp2c54 | NM_206537.2 | chr19:40037939-40073813 | 5545 | D030040B21Rik | NR_037998.1 | chr1:16657551-16662278 |
| 5449 | Cyp2c55 | NM_028089.3 | chr19:39007018-39042687 | 5546 | D030045P18Rik | NR_040624.1 | chr10:45807703-45852018 |
| 5450 | Cyp2c65 | NM_028191.2 | chr19:39061009-39093948 | 5547 | D030047H15Rik | NR_033548.1 | chr7:41216339-41349926 |
| 5451 | Cyp2c66 | NM_001011707.1 | chr19:39113897-39186756 | 5548 | D030056L22Rik | NM_177640.4 | chr19:18713235-18718428 |
| 5452 | Cyp2c67 | NM_001024719.2 | chr19:39608858-39649042 | 5549 | D10Bwg1379e | NM_001033258.4 | chr10:18588010-18743758 |
| 5453 | Cyp2c68 | NM_001039555.2 | chr19:39688835-39741101 | 5550 | D10Jhu81e | NM_138601.2 | chr10:78162066-78169788 |
| 5454 | Cyp2c69 | NM_001104525.1 | chr19:39842659-39886769 | 5551 | D10Wsu102e | NM_026679.3 | chr10:83360220-83368835 |
| 5455 | Cyp2c70 | NM_145499.2 | chr19:40153360-40187286 | 5552 | D11Wsu47e | NM_177777.5 | chr11:113684411-113694647 |
| 5456 | Cyp2d10 | NM_010005.3 | chr15:82402845-82407194 | 5553 | D130009I18Rik | NR_015593.2 | chr14:104639146-104966783 |
| 5457 | Cyp2d11 | NM_001104531.1 | chr15:82389153-82394022 | 5554 | D130017N08Rik | NR_015486.2 | chr5:143758353-143764942 |
| 5458 | Cyp2d12 | NM_201360.1 | chr15:82555097-82559413 | 5555 | D130020L05Rik | NR_038047.1 | chr12:101082450-101088927 |
| 5459 | Cyp2d13 | NR_003552.1 | chr15:82636749-82642045 | 5556 | D130040H23Rik | NM_172491.2 | chr8:69271079-69303375 |
| 5460 | Cyp2d22 | NM_001163472.1 | chr15:82370526-82380260 | 5557 | D130043K22Rik | NM_001081051.2 | chr13:24845150-24901439 |
| 5461 | Cyp2d26 | NM_029562.2 | chr15:82790106-82794245 | 5558 | D130058E03 | NR_073373.1 | chr6:127296185-127307967 |
| 5462 | Cyp2d34 | NM_145474.2 | chr15:82615964-82620907 | 5559 | D14Ertd670e | NR_105025.1 | chr14:19838924-19844677 |
| 5463 | Cyp2d37-ps | NR_033515.1 | chr15:82688749-82690058 | 5560 | D15Ertd621e | NM_145959.3 | chr15:58415467-58457801 |
| 5464 | Cyp2d40 | NM_023623.2 | chr15:82759832-82764122 | 5561 | D16Ertd472e | NM_001252438.1 | chr16:78540835-78576688 |
| 5465 | Cyp2d9 | NM_010008.2 | chr15:82452376-82456827 | 5562 | D16Ertd519e | NR_040474.1 | chr16:70616424-70624822 |
| 5466 | Cyp2e1 | NM_021282.2 | chr7:140763831-140774977 | 5563 | D17Ertd648e | NR_045808.1 | chr17:11863069-11883189 |
| 5467 | Cyp2f2 | NM_007817.2 | chr7:27119954-27133660 | 5564 | D17H6S53E | NM_033477.2 | chr17:35126401-35138855 |
| 5468 | Cyp2g1 | NM_033809.1 | chr7:28289026-28321197 | 5565 | D17Wsu104e | NM_080837.2 | chr17:56176540-56183920 |
| 5469 | Cyp2j11 | NM_001004141.2 | chr4:96294508-96348680 | 5566 | D17Wsu92e | NM_001033279.3 | chr17:27751291-27820542 |
| 5470 | Cyp2j12 | NM_001100182.2 | chr4:96093917-96141152 | 5567 | D198wg1357e | NM_177474.5 | chr19:27388697-27429908 |
| 5471 | Cyp2j13 | NM_145548.4 | chr4:96042659-96077540 | 5568 | D1Ertd622e | NM_133825.3 | chr1:97643901-97662018 |
| 5472 | Cyp2j5 | NM_010007.4 | chr4:96627431-96664119 | 5569 | D1Pas1 | NM_033077.3 | chr1:186967415-186979627 |
| 5473 | Cyp2j6 | NM_010006.4 | chr4:96516137-96553651 | 5570 | D230025D16Rik | NM_146604.2 | chr3:105225187-105253051 |
| 5474 | Cyp2j8 | NM_001104927.1 | chr4:96444587-96507386 | 5571 | D230010E09Rik | NR_045947.1 | chr12:118518296-118530193 |
| 5475 | Cyp2j9 | NM_028979.2 | chr4:96568428-96591485 | 5572 | D2hgdh | NM_178882.4 | chr1:93825239-93852361 |
| 5476 | Cyp2r1 | NM_177382.4 | chr7:114550162-114562972 | 5573 | D2Wsu81e | NM_172660.4 | chr2:30173446-30178459 |
| 5477 | Cyp2s1 | NM_028775.3 | chr7:25802475-25816530 | 5574 | D330023K18Rik | NR_040334.1 | chr2:31151048-31152291 |
| 5478 | Cyp2t4 | NM_001100184.1 | chr7:27153713-27158564 | 5575 | D330043H03Rik | NR_033554.1 | chr17:24409480-24414513 |
| 5479 | Cyp2u1 | NM_027816.3 | chr3:131290490-131303227 | 5576 | D330045A20Rik | NM_175326.5 | chrX:139480366-139554586 |
| 5480 | Cyp2w1 | NM_001160265.1 | chr5:139352616-139357033 | 5577 | D330050G23Rik | NR_040335.1 | chr3:116900151-116912791 |
| 5481 | Cyp39a1 | NM_001285947.1 | chr17:43667371-43751431 | 5578 | D330050I16Rik | NR_033224.1 | chr9:53988335-53990689 |
| 5482 | Cyp3a11 | NM_007818.3 | chr5:145854606-145879854 | 5579 | D3Bwg0562e | NM_177664.5 | chr3:117319145-117360876 |
| 5483 | Cyp3a13 | NM_007819.4 | chr5:137892932-137921619 | 5580 | D3Ertd254e | NM_001101478.1 | chr3:36151079-36170341 |
| 5484 | Cyp3a16 | NM_007820.2 | chr5:145436308-145469723 | 5581 | D3Ertd751e | NM_001099785.1 | chr3:41742617-41758939 |
| 5485 | Cyp3a25 | NM_019792.2 | chr5:145977193-146009617 | 5582 | D430019H16Rik | NM_001252508.1 | chr12:105453855-105493095 |
| 5486 | Cyp3a41a | NM_017396.3 | chr5:145694049-145720136 | 5583 | D430020I03Rik | NR_028421.1 | chr12:116401946-116405761 |
| 5487 | Cyp3a41b | NM_001105159.1 | chr5:145585663-145584730 | 5584 | D430036J16Rik | NR_040393.1 | chr9:81631929-81645156 |
| 5488 | Cyp3a44 | NM_177380.3 | chr5:145739982-145805874 | 5585 | D430041D05Rik | NM_001033347.2 | chr2:104143074-104410334 |
| 5489 | Cyp3a57 | NM_001100188.1 | chr5:145345269-145390512 | 5586 | D430042O09Rik | NM_001081022.1 | chr7:125707875-125874797 |
| 5490 | Cyp3a59 | NM_001105160.1 | chr5:146079257-146113283 | 5587 | D4Ertd817e | NR_029469.1 | chr4:118626403-118631915 |
| 5491 | Cyp46a1 | NM_010010.1 | chr12:108334380-108362234 | 5588 | D5300490J2Rik | NR_040605.1 | chr1:73398967-73430779 |
| 5492 | Cyp4a10 | NM_010011.3 | chr4:115518286-115533649 | 5589 | D5Ertd577e | NM_177187.4 | chr5:95456805-95485589 |
| 5493 | Cyp4a12a | NM_177406.3 | chr4:115429045-115332815 | 5590 | D5Ertd579e | NM_001081232.3 | chr5:36600485-36696021 |
| 5494 | Cyp4a12b | NM_172306.2 | chr4:115451452-115439034 | 5591 | D5Ertd605e | NR_033625.1 | chr5:147418619-147423044 |
| 5495 | Cyp4a14 | NM_007822.2 | chr4:115486199-115496141 | 5592 | D630003M21Rik | NM_001131021.2 | chr2:158182532-158229224 |
| 5496 | Cyp4a29 | NM_001100183.1 | chr4:115242083-115254557 | 5593 | D630010B17Rik | NR_045629.1 | chr15:94247201-94255606 |
| 5497 | Cyp4a30b | NM_001100185.1 | chr4:115452603-115471062 | 5594 | D630013N20Rik | NR_028269.1 | chr10:70601048-70651925 |
| 5498 | Cyp4a31 | NM_001252539.1 | chr4:115563648-115579015 | 5595 | D630023F18Rik | NM_001285881.1 | chr1:65107312-65123214 |
| 5499 | Cyp4a32 | NM_001100381.1 | chr4:115600937-115622366 | 5596 | D630024D03Rik | NR_102310.1 | chr11:31817983-31824547 |
| 5500 | Cyp4b1 | NM_007825.2 | chr4:115624727-115647705 | 5597 | D630029K05Rik | NR_027846.1 | chr10:116966273-116969107 |
| 5501 | Cyp4b1-ps2 | NR_033575.1 | chr4:115582037-115583127 | 5598 | D630032N06Rik | NR_028329.1 | chr11:85235165-85238304 |
| 5502 | Cyp4f13 | NM_130882.1 | chr17:32924687-32947361 | 5599 | D630033O11Rik | NM_001243261.1 | chr9:43259878-43280075 |
| 5503 | Cyp4f14 | NM_001204333.1 | chr17:32905069-32917329 | 5600 | D630039A03Rik | NM_178727.2 | chr4:57908383-57916264 |
| 5504 | Cyp4f15 | NM_134127.1 | chr17:32685658-32703349 | 5601 | D630041G03Rik | NR_028416.1 | chr7:44672244-44670884 |
| 5505 | Cyp4f16 | NM_024442.1 | chr17:32536628-32551797 | 5602 | D630043M12Rik | NM_194061.2 | chr6:38123173-38254009 |
| 5506 | Cyp4f17 | NM_001101445.1 | chr17:32506461-32528894 | 5603 | D630045M09Rik | NR_045293.1 | chr13:73344664-73347384 |
| 5507 | Cyp4f18 | NM_024444.2 | chr7:71988481-72009626 | 5604 | D6Ertd474e | NR_027803.1 | chr6:143245887-143297879 |
| 5508 | Cyp4f37 | NM_001100187.1 | chr17:32621318-32636184 | 5605 | D6Ertd527e | NM_001167937.1 | chr6:87104745-87113003 |
| 5509 | Cyp4f39 | NM_177307.3 | chr17:32452722-32493320 | 5606 | D6Wsu163e | NM_138594.3 | chr6:126959966-126975704 |
| 5510 | Cyp4f40 | NM_001101588.1 | chr17:32569482-32576480 | 5607 | D730005I28Rik | NR_027836.1 | chr15:74770907-74778859 |
| 5511 | Cyp4f41-ps | NR_033585.1 | chr17:32950960-32965716 | 5608 | D730005E14Rik | NR_030675.1 | chr15:79889531-79893138 |
| 5512 | Cyp4v3 | NM_133969.2 | chr8:45305801-45333196 | 5609 | D730045A05Rik | NR_045390.1 | chr18:74011906-74020088 |
| 5513 | Cyp4x1 | NM_001003947.1 | chr4:115108681-115133971 | 5610 | D730048I06Rik | NM_026593.3 | chr9:35788049-35790112 |
| 5514 | Cyp51 | NM_020010.2 | chr5:4080673-4104697 | 5611 | D730050B12Rik | NR_046196.1 | chr13:72809600-72816763 |
| 5515 | Cyp7a1 | NM_007824.2 | chr4:6265611-6275631 | 5612 | D7Ertd143e | NR_028425.1 | chr7:3218783-3221015 |
| 5516 | Cyp7b1 | NM_007825.4 | chr3:18071949-18243338 | 5613 | D7Ertd443e | NM_001083131.1 | chr7:134266261-134376828 |
| 5517 | Cypt1b1 | NM_009812.3 | chr3:121914355-121916305 | 5614 | D7Ertd715e | NR_015456.1 | chr7:59969676-59974431 |
| 5518 | Cypt1 | NM_025738.3 | chrX:16522868-16523691 | 5615 | D830005N08Rik | NR_040657.1 | chr10:33212344-33256357 |
| 5519 | Cypt12 | NM_029289.1 | chr3:17948443-17948952 | 5616 | D830013O20Rik | NR_046013.1 | chr12:73364074-73409563 |
| 5520 | Cypt14 | NM_001191082.1 | chrX:39862918-39863604 | 5617 | D830015G02Rik | NR_033497.1 | chr14:54968786-54974349 |
| 5521 | Cypt15 | NM_001177380.1 | chrX:39346265-39346961 | 5618 | D830026I12Rik | NM_102304.1 | chr6:17198106-17205695 |
| 5522 | Cypt2 | NM_178436.2 | chrX:105499771-105500637 | 5619 | D830030K20Rik | NM_177135.4 | chr13:3224439-3856080 |
| 5523 | Cypt3 | NM_173367.3 | chrX:153558592-153559435 | 5620 | D830031N03Rik | NM_001167918.1 | chr4:123403600-123411913 |
| 5524 | Cypt4 | NM_173412.2 | chrX:24625184-24625826 | 5621 | D830032E09Rik | NR_102306.1 | chr1:107917258-107950947 |
| 5525 | Cypt7 | NM_001039943.2 | chrX:16522880-16523615 | 5622 | D830046C22Rik | NR_033147.1 | chr5:139577696-139580053 |
| 5526 | Cypt8 | NM_001039945.2 | chrX:16522486-16523211 | 5623 | D8Ertd738e | NM_001052571.2 | chr8:84246234-84249761 |
| 5527 | Cypt9 | NM_001039942.1 | chr9:24625203-24625737 | 5624 | D8Ertd82e | NM_172911.3 | chr8:36094827-36147787 |
| 5528 | Cyr61 | NM_010516.2 | chr3:145646970-145649985 | 5625 | D930007P13Rik | NR_045743.1 | chr15:103123069-103148828 |

Fig.21 - 30

| | | | | | | | | |
|---|---|---|---|---|---|---|---|---|
| 5626 | D930015E06Rik | NM_172681.4 | chr3:83898286-84040161 | 5723 | Dctn2 | NM_001190453.1 | chr10:127266261-127281959 |
| 5627 | D930015M05Rik | NR_040621.1 | chr2:92408891-92432308 | 5724 | Dctn3 | NM_001159565.1 | chr4:41714797-41723163 |
| 5628 | D930016D06Rik | NR_030673.1 | chr5:104525734-104554211 | 5725 | Dctn4 | NM_026302.3 | chr18:60526220-60558762 |
| 5629 | D930020B18Rik | NM_177335.4 | chr10:121641700-121693914 | 5726 | Dctn5 | NM_023608.3 | chr7:122133040-122149044 |
| 5630 | D930028M14Rik | NR_045847.1 | chr7:25152456-25156630 | 5727 | Dctn6 | NM_011722.4 | chr8:34090420-34108712 |
| 5631 | D930032P07Rik | NR_045330.1 | chr19:28678223-28720027 | 5728 | Dctpp1 | NM_023203.1 | chr7:127266958-127260667 |
| 5632 | D930048N14Rik | NR_027958.1 | chr11:51650953-51657681 | 5729 | Dcun1d1 | NM_001205361.1 | chr3:35892104-35932966 |
| 5633 | Daam1 | NM_001286452.1 | chr12:71889542-71992376 | 5730 | Dcun1d2 | NM_001024504.2 | chr8:13255962-13288126 |
| 5634 | Daam2 | NM_001008231.2 | chr17:49456021-49564337 | 5731 | Dcun1d3 | NM_001163703.1 | chr7:119853162-119895745 |
| 5635 | Dab1 | NM_010014.3 | chr4:104387537-104680889 | 5732 | Dcun1d4 | NM_001190733.1 | chr5:73491025-73560794 |
| 5636 | Dab2 | NM_001008702.2 | chr15:6299788-6440709 | 5733 | Dcun1d5 | NM_029775.2 | chr9:7184565-7207031 |
| 5637 | Dab2ip | NM_001001602.2 | chr2:35691993-35730994 | 5734 | Dcx | NM_001110222.1 | chrX:143855841-143933124 |
| 5638 | Dach1 | NM_001038610.2 | chr14:97726845-98169765 | 5735 | Dcxr | NM_026428.2 | chr11:120725372-120727281 |
| 5639 | Dach2 | NM_001142570.1 | chrX:113298255-113895091 | 5736 | Dda1 | NM_025600.2 | chr8:71469193-71476097 |
| 5640 | Dact1 | NM_001110366.1 | chr12:71309883-71320107 | 5737 | Ddah1 | NM_026993.3 | chr3:145758691-145894277 |
| 5641 | Dact2 | NM_172826.3 | chr17:14195229-14203831 | 5738 | Ddah2 | NM_001190449.1 | chr17:35059034-35062099 |
| 5642 | Dact3 | NM_001081655.1 | chr7:16875316-16887301 | 5739 | Ddb1 | NM_015735.1 | chr19:10605624-10629821 |
| 5643 | Dad1 | NM_001113358.1 | chr14:54235484-54253929 | 5740 | Ddb2 | NM_028119.5 | chr2:91211581-91237066 |
| 5644 | Daf2 | NM_007827.2 | chr1:130388527-130422999 | 5741 | Ddc | NM_001190448.1 | chr11:11814100-11898144 |
| 5645 | Dag1 | NM_001276481.1 | chr9:108204860-108263815 | 5742 | Ddhd1 | NM_001039106.3 | chr14:45593176-45658143 |
| 5646 | Dagla | NM_198114.2 | chr19:10245264-10304877 | 5743 | Ddhd2 | NM_028102.1 | chr8:25725323-25754230 |
| 5647 | Daglb | NM_144915.3 | chr5:143464492-143504442 | 5744 | Ddi1 | NM_027942.1 | chr9:6265027-6286547 |
| 5648 | Dak | NM_145496.1 | chr19:10592196-10604258 | 5745 | Ddi2 | NM_001017966.2 | chr4:141683562-141723419 |
| 5649 | Dalrd3 | NM_026378.3 | chr9:108568891-108572771 | 5746 | Ddit3 | NM_001290183.1 | chr10:127290792-127296288 |
| 5650 | Dancr | NR_035531.1 | chr5:74093082-74094336 | 5747 | Ddit4 | NM_029083.2 | chr10:59949674-59951770 |
| 5651 | Dand5 | NM_201227.3 | chr8:84815404-84822823 | 5748 | Ddit4l | NM_030143.4 | chr3:137623671-137628932 |
| 5652 | Dao | NM_001286396.1 | chr5:114004807-114026675 | 5749 | Ddn | NM_001013741.1 | chr15:98803781-98807925 |
| 5653 | Dap | NM_146057.3 | chr15:31224384-31274338 | 5750 | Ddo | NM_027442.5 | chr10:40630010-40649931 |
| 5654 | Dap3 | NM_001164533.1 | chr3:88920802-88950282 | 5751 | Ddost | NM_007838.2 | chr4:138304737-138312611 |
| 5655 | Dapk1 | NM_001285917.1 | chr13:60601946-60763191 | 5752 | Ddr1 | NM_001198831.1 | chr17:35681566-35702044 |
| 5656 | Dapk2 | NM_010019.3 | chr9:66156225-66272242 | 5753 | Ddr2 | NM_022563.2 | chr1:169972306-170083944 |
| 5657 | Dapk3 | NM_001190473.1 | chr10:81183262-81193197 | 5754 | Ddrgk1 | NM_029832.2 | chr2:130654082-130664645 |
| 5658 | Dapl1 | NM_029723.3 | chr2:59484653-59505020 | 5755 | Dct | NM_010027.1 | chr10:75771232-75773374 |
| 5659 | Dapp1 | NM_011932.3 | chr3:137981006-137981549 | 5756 | Ddx1 | NM_134040.1 | chr12:13219306-13249174 |
| 5660 | Dars | NM_145507.2 | chr1:128412117-128417416 | 5757 | Ddx10 | NM_029936.2 | chr9:53098453-53248112 |
| 5661 | Dars2 | NM_172644.4 | chr1:161040600-161070660 | 5758 | Ddx11 | NM_001003919.1 | chr17:66123519-66152163 |
| 5662 | Daw1 | NM_027725.3 | chr1:83159761-83210572 | 5759 | Ddx17 | NM_001040187.1 | chr15:79527695-79546741 |
| 5663 | Daxx | NM_001199733.1 | chr17:33909600-33915590 | 5760 | Ddx18 | NM_025860.3 | chr1:121553834-121567980 |
| 5664 | Dazap1 | NM_001122604.1 | chr10:80264090-80288413 | 5761 | Ddx19a | NM_007916.2 | chr8:110974990-110997823 |
| 5665 | Dazap2 | NM_011873.2 | chr15:100615661-100620761 | 5762 | Ddx19b | NM_001190786.1 | chr8:111003185-111031751 |
| 5666 | Dazl | NM_001277863.1 | chr17:50279392-50293620 | 5763 | Ddx20 | NM_017397.3 | chr3:105678461-105687571 |
| 5667 | Dbf4 | NM_001190717.1 | chr5:8396698-8422718 | 5764 | Ddx21 | NM_019553.2 | chr10:62580246-62602298 |
| 5668 | Dbh | NM_138942.3 | chr2:27165506-27183204 | 5765 | Ddx23 | NM_001080981.1 | chr15:98645506-98662889 |
| 5669 | Dbhos | NR_040524.1 | chr2:27144897-27162703 | 5766 | Ddx24 | NM_001159502.1 | chr12:103407975-103425780 |
| 5670 | Dbi | NM_001037999.2 | chr1:120113279-120120919 | 5767 | Ddx25 | NM_013932.4 | chr9:35541847-35558470 |
| 5671 | Dbil5 | NM_021294.2 | chr11:76217612-76218665 | 5768 | Ddx26b | NM_172779.4 | chrX:56454838-56507843 |
| 5672 | Dbn1 | NM_001177371.1 | chr13:55473427-55488076 | 5769 | Ddx27 | NM_153065.3 | chr2:167015312-167034945 |
| 5673 | Dbndd1 | NM_001170975.2 | chr8:123505686-123515455 | 5770 | Ddx28 | NM_028038.3 | chr8:106009615-106011486 |
| 5674 | Dbndd2 | NM_001048227.1 | chr2:164486139-164493323 | 5771 | Ddx31 | NM_001033294.3 | chr2:28840405-28905575 |
| 5675 | Dbnl | NM_146308.1 | chr11:5788482-5800980 | 5772 | Ddx39 | NM_197982.3 | chr8:83715176-83723351 |
| 5676 | Dbp | NM_016974.3 | chr7:45705246-45710203 | 5773 | Ddx39b | NM_001252457.1 | chr17:35242816-35253707 |
| 5677 | Dbpht2 | NM_198866.2 | chr12:74297473-74300468 | 5774 | Ddx3x | NM_010028.3 | chrX:13281021-13293983 |
| 5678 | Dbr1 | NM_031423.3 | chr9:99575798-99584343 | 5775 | Ddx3y | NM_012008.2 | chrY:1260714-1286613 |
| 5679 | Dbt | NM_010022.3 | chr3:116513078-116549981 | 5776 | Ddx4 | NM_001145885.1 | chr13:112598332-112652310 |
| 5680 | Dbx1 | NM_001005232.1 | chr7:49631498-49636885 | 5777 | Ddx41 | NM_134059.2 | chr13:55530409-55536658 |
| 5681 | Dbx2 | NM_207533.2 | chr15:95623562-95654771 | 5778 | Ddx42 | NM_028074.4 | chr11:106216925-106249140 |
| 5682 | Dcaf10 | NM_153167.2 | chr4:45342100-45379722 | 5779 | Ddx43 | NM_001191044.1 | chr9:78395776-78423589 |
| 5683 | Dcaf11 | NM_001199009.1 | chr14:55560922-55570065 | 5780 | Ddx46 | NM_001282055.1 | chr13:55634998-55681267 |
| 5684 | Dcaf12 | NM_026893.3 | chr4:41291299-41314901 | 5781 | Ddx47 | NM_026360.3 | chr6:135011611-135023776 |
| 5685 | Dcaf12l1 | NM_001190718.1 | chrX:44786566-44790161 | 5782 | Ddx49 | NM_001024922.2 | chr8:70292865-70302452 |
| 5686 | Dcaf12l2 | NM_175539.3 | chrX:44336566-44368337 | 5783 | Ddx5 | NM_007840.3 | chr11:106780355-106788494 |
| 5687 | Dcaf13 | NM_198606.2 | chr15:39112873-39146855 | 5784 | Ddx50 | NM_053183.2 | chr10:62616022-62651198 |
| 5688 | Dcaf15 | NM_172502.3 | chr8:84097071-84104762 | 5785 | Ddx51 | NM_027156.3 | chr5:110653450-110660496 |
| 5689 | Dcaf17 | NM_001165980.1 | chr2:71055743-71095858 | 5786 | Ddx52 | NM_030096.2 | chr11:83942089-83963086 |
| 5690 | Dcaf4 | NM_001165256.1 | chr12:83526048-83541992 | 5787 | Ddx54 | NM_028041.2 | chr5:120613129-120628592 |
| 5691 | Dcaf5 | NM_172767.4 | chr12:80335646-80436601 | 5788 | Ddx55 | NM_001190795.1 | chr5:124552863-124569660 |
| 5692 | Dcaf6 | NM_026759.1 | chr1:165329500-165460463 | 5789 | Ddx56 | NM_026538.3 | chr11:6257544-6267729 |
| 5693 | Dcaf7 | NM_027946.3 | chr11:106036871-106059323 | 5790 | Ddx58 | NM_172689.3 | chr4:40203776-40239825 |
| 5694 | Dcaf8 | NM_153555.2 | chr1:172148014-172196393 | 5791 | Ddx59 | NM_026500.3 | chr1:136415270-136440220 |
| 5695 | Dcaf8l | NM_026553.3 | chr11:102994055-103017147 | 5792 | Ddx6 | NM_001110826.1 | chr9:44604891-44640731 |
| 5696 | Dcbld1 | NM_025877.3 | chr10:52233618-52321377 | 5793 | Ddx60 | NM_001293783.1 | chr8:61928066-62037704 |
| 5697 | Dcbld2 | NM_028523.3 | chr15:58408534-58469745 | 5794 | Dea1 | NM_001282072.1 | chr7:141297175-141327725 |
| 5698 | Dcc | NM_007831.3 | chr18:71253631-72351069 | 5795 | Dear1 | NM_001040461.2 | chr3:84965055-84968580 |
| 5699 | Dcdc2a | NM_001195617.1 | chr13:25056003-25121521 | 5796 | Deb1 | NM_026794.2 | chr9:121710388-121712921 |
| 5700 | Dcdc2b | NM_001195780.1 | chr4:129608330-129614257 | 5797 | Decr1 | NM_026172.3 | chr4:15917239-15945507 |
| 5701 | Dcdc2c | NM_001177964.2 | chr12:28437794-28548337 | 5798 | Decr2 | NM_011933.2 | chr17:26081210-26090164 |
| 5702 | Dchs1 | NM_001162988.1 | chr7:105752988-105787550 | 5799 | Dedd | NM_001128609.1 | chr1:171329144-171342501 |
| 5703 | Dck | NM_007832.4 | chr5:88765012-88783277 | 5800 | Dedd2 | NM_207677.3 | chr7:25202839-25219859 |
| 5704 | Dclk1 | NM_001111051.1 | chr3:55461757-55539068 | 5801 | Def6 | NM_027185.3 | chr17:28207777-28228608 |
| 5705 | Dclk2 | NM_001195496.1 | chr3:86786149-86920884 | 5802 | Def8 | NM_001253783.1 | chr8:123442955-123463899 |
| 5706 | Dclk3 | NM_172928.5 | chr9:111439080-111489611 | 5803 | Defa17 | NM_001167790.1 | chr8:21655766-21656736 |
| 5707 | Dclre1a | NM_018821.4 | chr19:56529160-56548222 | 5804 | Defa2 | NM_001195634.2 | chr8:21378516-21379495 |
| 5708 | Dclre1b | NM_001025312.1 | chr3:103800604-103809387 | 5805 | Defa20 | NM_183268.4 | chr8:21509257-21510237 |
| 5709 | Dclre1c | NM_001110214.1 | chr2:3424130-3461116 | 5806 | Defa21 | NM_183253.3 | chr8:21025544-21026517 |
| 5710 | Dcn | NM_001190465.1 | chr10:97479499-97518163 | 5807 | Defa22 | NM_207658.4 | chr8:21162276-21163249 |
| 5711 | Dcp1a | NM_133761.3 | chr14:30479564-30527056 | 5808 | Defa23 | NM_001012307.2 | chr8:21055039-21192549 |
| 5712 | Dcp1b | NM_001033379.3 | chr6:119152522-119221614 | 5809 | Defa24 | NM_001024225.2 | chr8:21734493-21735471 |
| 5713 | Dcp2 | NM_027490.1 | chr18:44380499-44424969 | 5810 | Defa25 | NM_007849.1 | chr8:21084441-21085285 |
| 5714 | Dcpp1 | NM_019910.2 | chr17:23880875-23882853 | 5811 | Defa26 | NM_001079933.2 | chr8:21618167-21618972 |
| 5715 | Dcpp2 | NM_001039238.2 | chr17:23900787-23902853 | 5812 | Defa3 | NM_207850.2 | chr8:21287408-21288377 |
| 5716 | Dcpp3 | NM_001077633.1 | chr17:23917437-23919441 | 5813 | Defa4 | NM_010039.2 | chr8:21065065-21065232 |
| 5717 | Dcps | NM_027030.2 | chr9:35124413-35175987 | 5814 | Defa5 | NM_007851.2 | chr8:21297393-21298375 |
| 5718 | Dcst1 | NM_029974.2 | chr3:89350218-89365253 | 5815 | Defa6 | NM_007852.1 | chr8:21734536-21735377 |
| 5719 | Dcstamp | NM_001289506.1 | chr15:39745929-39760938 | 5816 | Defa-ps1 | NR_003146.1 | chr8:21695611-21695853 |
| 5720 | Dct | NM_010024.3 | chr14:118012789-118052146 | 5817 | Defa-ps12 | NR_002881.2 | chr8:19210461-19212760 |
| 5721 | Dctd | NM_001161515.1 | chr8:48110012-48141667 | 5818 | Defa-ps13 | NR_002881.2 | chr8:19300676-19304794 |
| 5722 | Dctn1 | NM_001198866.1 | chr6:83165923-83200117 | 5819 | Defa-rs1 | NM_007844.2 | chr8:21325887-21327020 |

Fig. 21 - 31

| | | | | | | | | |
|---|---|---|---|---|---|---|---|---|
| 5820 | Defa-rs7 | NM_007848.2 | chr8:21055039-21192550 | | 5917 | Dgkz | NM_001166597.1 | chr2:91932826-91950348 |
| 5821 | Defb1 | NM_007843.3 | chr8:21776554-21795185 | | 5918 | Dguok | NM_001162521.1 | chr6:83480213-83506969 |
| 5822 | Defb10 | NM_139225.3 | chr8:21858900-21862010 | | 5919 | Dhcr24 | NM_053272.2 | chr4:106561037-106589133 |
| 5823 | Defb11 | NM_139221.2 | chr8:21905373-21906432 | | 5920 | Dhcr7 | NM_007856.2 | chr7:143823166-143848410 |
| 5824 | Defb12 | NM_152802.3 | chr8:19111930-19114833 | | 5921 | Dhdds | NM_026144.4 | chr4:133969056-134000864 |
| 5825 | Defb13 | NM_139223.3 | chr8:21946761-21948622 | | 5922 | Dhdh | NM_027903.3 | chr7:45473562-45488796 |
| 5826 | Defb14 | NM_183026.2 | chr8:19194327-19195309 | | 5923 | Dhfr | NM_010049.3 | chr13:92354782-92389053 |
| 5827 | Defb15 | NM_139222.3 | chr8:21929812-21932710 | | 5924 | Dhh | NM_007857.4 | chr15:98893026-98898540 |
| 5828 | Defb18 | NM_001039123.1 | chr1:18236472-18237443 | | 5925 | Dhodh | NM_020046.3 | chr8:109593247-109608673 |
| 5829 | Defb19 | NM_145157.3 | chr2:152576085-152580312 | | 5926 | Dhps | NM_001039514.1 | chr8:85071756-85075161 |
| 5830 | Defb2 | NM_010030.1 | chr8:21839925-21843481 | | 5927 | Dhrs1 | NM_026819.2 | chr14:55739019-55745684 |
| 5831 | Defb20 | NM_176950.3 | chr2:152477062-152479934 | | 5928 | Dhrs11 | NM_177564.5 | chr11:84820727-84829003 |
| 5832 | Defb21 | NM_207276.2 | chr2:152572743-152574943 | | 5929 | Dhrs13 | NM_183286.2 | chr11:78032312-78037864 |
| 5833 | Defb22 | NM_001002791.2 | chr2:152485685-152490138 | | 5930 | Dhrs2 | NM_027790.2 | chr14:55222006-55241440 |
| 5834 | Defb23 | NM_001037933.2 | chr2:152459054-152464620 | | 5931 | Dhrs3 | NM_001172424.1 | chr4:144892826-144927645 |
| 5835 | Defb25 | NM_001039122.1 | chr2:152622355-152623053 | | 5932 | Dhrs4 | NM_001037938.2 | chr14:55478757-55490340 |
| 5836 | Defb26 | NM_001039120.2 | chr2:152507755-152511736 | | 5933 | Dhrs7 | NM_025522.5 | chr12:72650352-72664828 |
| 5837 | Defb28 | NM_001037902.2 | chr2:152518254-152521447 | | 5934 | Dhrs7b | NM_001172112.1 | chr11:60830630-60858423 |
| 5838 | Defb29 | NM_001001444.2 | chr2:152538713-152540041 | | 5935 | Dhrs7c | NM_001013013.2 | chr11:67798270-67816002 |
| 5839 | Defb3 | NM_013756.2 | chr8:19293360-19295339 | | 5936 | Dhrs9 | NM_175512.2 | chr2:69380461-69403086 |
| 5840 | Defb30 | NM_001039566.2 | chr14:63034086-63037846 | | 5937 | Dhrsx | NM_001033326.2 | chr4_GL456216_random:15880-36213 |
| 5841 | Defb33 | NM_001039119.2 | chr8:20892666-20897723 | | 5938 | Dhtkd1 | NM_001081131.2 | chr2:5898059-5942792 |
| 5842 | Defb34 | NM_183035.1 | chr8:19123751-19126540 | | 5939 | Dhx15 | NM_001042620.2 | chr5:52153323-52190546 |
| 5843 | Defb35 | NM_139224.1 | chr8:21938351-21940878 | | 5940 | Dhx16 | NM_026987.2 | chr17:35879777-35892668 |
| 5844 | Defb36 | NM_001037247.4 | chr2:152604326-152612729 | | 5941 | Dhx29 | NM_172594.2 | chr13:112927792-112969187 |
| 5845 | Defb37 | NM_181683.2 | chr8:18986232-18991055 | | 5942 | Dhx30 | NM_001252682.1 | chr9:110084318-110117616 |
| 5846 | Defb38 | NM_183036.1 | chr8:19023463-19026529 | | 5943 | Dhx32 | NM_001286030.1 | chr7:133720934-133760269 |
| 5847 | Defb39 | NM_183038.2 | chr8:19052825-19064810 | | 5944 | Dhx33 | NM_178367.4 | chr11:70984090-71004832 |
| 5848 | Defb4 | NM_019728.4 | chr8:19198703-19201547 | | 5945 | Dhx34 | NM_001285931.1 | chr7:16197220-16221993 |
| 5849 | Defb40 | NM_183039.3 | chr8:18974939-18978116 | | 5946 | Dhx35 | NM_001291144.1 | chr2:158794806-158858220 |
| 5850 | Defb41 | NM_183124.3 | chr1:18250977-18265138 | | 5947 | Dhx36 | NM_028136.2 | chr3:62468641-62506988 |
| 5851 | Defb42 | NM_001034910.3 | chr14:63046990-63048606 | | 5948 | Dhx37 | NM_203319.1 | chr5:125414403-125434048 |
| 5852 | Defb43 | NM_001039121.1 | chr14:63011770-63018088 | | 5949 | Dhx38 | NM_178380.1 | chr8:109548023-109565601 |
| 5853 | Defb44-ps | NR_002879.2 | chr1:18210052-18223564 | | 5950 | Dhx40 | NM_026191.2 | chr11:86768848-86807660 |
| 5854 | Defb45 | NM_001037752.2 | chr2:152593190-152596485 | | 5951 | Dhx57 | NM_001183759.1 | chr17:80233303-80290478 |
| 5855 | Defb46 | NM_001025351.1 | chr8:19239915-19242143 | | 5952 | Dhx58 | NM_030150.2 | chr11:100694883-100704271 |
| 5856 | Defb47 | NM_001039125.2 | chr14:62998076-63001160 | | 5953 | Dhx8 | NM_144831.2 | chr11:101732955-101767357 |
| 5857 | Defb48 | NM_001037751.3 | chr14:62977523-62984510 | | 5954 | Dhx9 | NM_007842.2 | chr1:153455757-153487660 |
| 5858 | Defb5 | NM_030734.2 | chr8:19247591-19250828 | | 5955 | Diablo | NM_023232.3 | chr5:123511329-123524164 |
| 5859 | Defb50 | NM_199067.1 | chr8:21823538-21831296 | | 5956 | Diap1 | NM_007858.3 | chr18:37843600-37935423 |
| 5860 | Defb6 | NM_054074.1 | chr8:19225477-19228209 | | 5957 | Diap2 | NM_172493.2 | chrX:129749741-130465833 |
| 5861 | Defb7 | NM_139220.1 | chr8:19495096-19497775 | | 5958 | Diap3 | NM_019670.1 | chr14:86656322-87141114 |
| 5862 | Defb8 | NM_153108.4 | chr8:19445769-19447606 | | 5959 | Dicer1 | NM_148948.2 | chr12:104687741-104751952 |
| 5863 | Defb9 | NM_139219.2 | chr8:21881712-21885434 | | 5960 | Dido1 | NM_001291432.1 | chr2:180680953-180709999 |
| 5864 | Degs1 | NM_007853.4 | chr1:182275769-182282759 | | 5961 | Diexf | NM_145415.2 | chr1:193104402-193130251 |
| 5865 | Degs2 | NM_001171002.1 | chr12:108686791-108702306 | | 5962 | Dimt1 | NM_025447.4 | chr13:106947128-106960224 |
| 5866 | Dek | NM_025900.2 | chr13:47084766-47106221 | | 5963 | Dio1 | NM_007860.3 | chr4:107291464-107307143 |
| 5867 | Dennd1a | NM_146122.3 | chr2:37799989-38287364 | | 5964 | Dio2 | NM_010050.2 | chr12:90724551-90738438 |
| 5868 | Dennd1b | NM_001166501.1 | chr1:138963708-139176042 | | 5965 | Dio3 | NM_172119.2 | chr12:110279229-110281097 |
| 5869 | Dennd1c | NM_153351.1 | chr17:57066054-57076510 | | 5966 | Dio3os | NR_002866.2 | chr12:110275384-110278068 |
| 5870 | Dennd2a | NM_172477.4 | chr6:39462377-39557834 | | 5967 | Dip2a | NM_001081419.2 | chr10:76263048-76345291 |
| 5871 | Dennd2c | NM_177857.1 | chr3:103127555-103169733 | | 5968 | Dip2b | NM_001159361.1 | chr15:100038663-100219473 |
| 5872 | Dennd2d | NM_001093754.2 | chr3:106482430-106503030 | | 5969 | Dip2c | NM_001081426.2 | chr13:9276524-9688926 |
| 5873 | Dennd3 | NM_001081066.1 | chr15:73512559-73572247 | | 5970 | Diras1 | NM_145217.2 | chr10:81019589-81025377 |
| 5874 | Dennd4a | NM_001162917.1 | chr9:64811010-64919667 | | 5971 | Diras2 | NM_001024474.2 | chr13:52504374-52530836 |
| 5875 | Dennd4b | NM_201407.4 | chr3:90266513-90280665 | | 5972 | Dirc2 | NM_153556.3 | chr16:35694902-35769356 |
| 5876 | Dennd4c | NM_184084.4 | chr4:86748554-86850802 | | 5973 | Dis3 | NM_028315.2 | chr14:99076633-99099770 |
| 5877 | Dennd5a | NM_021494.1 | chr7:109893780-109960422 | | 5974 | Dis3l | NM_001001295.2 | chr9:64306759-64341257 |
| 5878 | Dennd5b | NM_177192.3 | chr6:148898068-149101680 | | 5975 | Dis3l2 | NM_001172157.1 | chr1:86703803-87050097 |
| 5879 | Dennd6a | NM_001134465.2 | chr14:26579549-26634322 | | 5976 | Disc1 | NM_174853.2 | chr8:125054194-125261151 |
| 5880 | Dennd6b | NM_027081.3 | chr15:89182212-89196474 | | 5977 | Disp1 | NM_001278218.1 | chr1:183086283-183221529 |
| 5881 | Denr | NM_026803.4 | chr5:123907274-123928832 | | 5978 | Disp2 | NM_170593.3 | chr2:118779718-118795175 |
| 5882 | Depdc1a | NM_001172092.1 | chr3:159495432-159529955 | | 5979 | Dixdc1 | NM_178118.2 | chr9:50662752-50727984 |
| 5883 | Depdc1b | NM_178683.4 | chr13:108316336-108389557 | | 5980 | Dkc1 | NM_001030307.2 | chrX:75095853-75109776 |
| 5884 | Depdc5 | NM_001025426.2 | chr5:32863720-32994233 | | 5981 | Dkk1 | NM_010051.3 | chr19:30545884-30549496 |
| 5885 | Depdc7 | NM_144804.3 | chr2:104721786-104742801 | | 5982 | Dkk2 | NM_020265.4 | chr3:132085291-132180304 |
| 5886 | Deptor | NM_001037937.3 | chr15:55133435-55259273 | | 5983 | Dkk3 | NM_015814.2 | chr7:112116018-112159057 |
| 5887 | Dera | NM_172733.1 | chr6:137754676-137827872 | | 5984 | Dkk4 | NM_145592.2 | chr8:22624042-22627546 |
| 5888 | Derl1 | NM_024207.4 | chr15:57869501-57892418 | | 5985 | Dkkl1 | NM_015789.3 | chr7:45207524-45211883 |
| 5889 | Derl2 | NM_001291146.1 | chr11:71007439-71019841 | | 5986 | Dlat | NM_145614.4 | chr9:50634632-50659780 |
| 5890 | Derl3 | NM_024440.2 | chr10:75893397-75895941 | | 5987 | Dlc1 | NM_001194940.2 | chr8:36567738-36952442 |
| 5891 | Des | NM_010043.2 | chr1:75360291-75368579 | | 5988 | Dld | NM_007861.5 | chr12:31331561-31351471 |
| 5892 | Desi1 | NM_134095.2 | chr15:81992522-82016140 | | 5989 | Dlec1 | NM_177117.3 | chr9:119102477-119147694 |
| 5893 | Desi2 | NM_024282.3 | chr1:178187416-178252597 | | 5990 | Dleu2 | NR_028264.1 | chr14:61602835-61682373 |
| 5894 | Det1 | NM_029585.3 | chr7:78827473-78847211 | | 5991 | Dleu7 | NM_173419.2 | chr14:62276228-62292979 |
| 5895 | Dexi | NM_021428.4 | chr16:10530206-10543054 | | 5992 | Dlg1 | NM_001252433.1 | chr16:31663934-31873356 |
| 5896 | Dffa | NM_001025296.2 | chr4:149104141-149120653 | | 5993 | Dlg2 | NM_001243046.1 | chr7:92062393-92449246 |
| 5897 | Dffb | NM_007869.3 | chr4:153964448-153975081 | | 5994 | Dlg3 | NM_001177778.2 | chrX:100767721-100818410 |
| 5898 | Dfna5 | NM_018769.3 | chr6:50207402-50261769 | | 5995 | Dlg4 | NM_001109752.1 | chr11:70018604-70045531 |
| 5899 | Dfnb59 | NM_001080711.2 | chr2:76650272-76658554 | | 5996 | Dlg5 | NM_001163513.1 | chr14:24133952-24245920 |
| 5900 | Dgat1 | NM_010046.2 | chr15:76502014-76511818 | | 5997 | Dlgap1 | NM_001128180.1 | chr17:70522109-70821413 |
| 5901 | Dgat2 | NM_026384.3 | chr7:99153662-99182713 | | 5998 | Dlgap2 | NM_001145965.3 | chr8:14095874-14847686 |
| 5902 | Dgat2l6 | NM_001114084.1 | chrX:100524837-100546108 | | 5999 | Dlgap3 | NM_198618.5 | chr4:127169203-127217022 |
| 5903 | Dgcr14 | NM_001081633.1 | chr16:17900708-17911348 | | 6000 | Dlgap4 | NM_001042487.1 | chr2:156721278-156764363 |
| 5904 | Dgcr2 | NM_001109750.1 | chr16:17840355-17891726 | | 6001 | Dlgap5 | NM_144553.2 | chr14:47387778-47418407 |
| 5905 | Dgcr6 | NM_001089813.1 | chr16:18066402-18073632 | | 6002 | Dlk1 | NM_001190703.1 | chr12:109453454-109463336 |
| 5906 | Dgcr8 | NM_033324.2 | chr16:18253964-18289168 | | 6003 | Dlk2 | NM_001286013.1 | chr17:46297927-46303271 |
| 5907 | Dgka | NM_016811.2 | chr10:128720135-128744056 | | 6004 | Dll1 | NM_007865.3 | chr17:15367359-15375823 |
| 5908 | Dgkb | NM_178681.4 | chr12:37880704-38633410 | | 6005 | Dll3 | NM_007866.2 | chr7:28293554-28301785 |
| 5909 | Dgkd | NM_177646.3 | chr1:87853286-87944489 | | 6006 | Dll4 | NM_019454.3 | chr2:119325783-119335666 |
| 5910 | Dgke | NM_019505.3 | chr11:89037581-89060748 | | 6007 | Dlst | NM_030225.4 | chr12:85110832-85134091 |
| 5911 | Dgkeos | NR_110318.1 | chr11:89060750-89067884 | | 6008 | Dlx1 | NM_010053.2 | chr2:71529444-71533981 |
| 5912 | Dgkg | NM_138650.2 | chr16:22466568-22657231 | | 6009 | Dlx1as | NR_002854.2 | chr2:71530637-71537891 |
| 5913 | Dgkh | NM_001081206.1 | chr14:78569608-78725089 | | 6010 | Dlx2 | NM_010054.2 | chr2:71543407-71546754 |
| 5914 | Dgki | NM_001081206.1 | chr6:36846021-37299976 | | 6011 | Dlx3 | NM_010055.3 | chr11:95120116-95125291 |
| 5915 | Dgkk | NM_177914.3 | chrX:6873483-6948361 | | 6012 | Dlx4 | NM_007867.4 | chr11:95140446-95145801 |
| 5916 | Dgkq | NM_199011.1 | chr5:108647043-108660769 | | 6013 | Dlx5 | NM_010056.3 | chr6:6877800-6882068 |

Fig.21 - 32

| | | | | | | | |
|---|---|---|---|---|---|---|---|
| 6014 | Dlx6 | NM_010057.2 | chr6:6863333-6867970 | 6111 | Dnase2a | NM_010062.3 | chr8:84908623-84911461 |
| 6015 | Dlx6as2 | NR_002839.2 | chr6:6863796-6865150 | 6112 | Dnase2b | NM_019957.4 | chr3:146581372-146615598 |
| 6016 | Dlx6os1 | NR_015388.1 | chr6:6820545-6869533 | 6113 | Dnd1 | NM_173383.2 | chr18:36763670-36766214 |
| 6017 | Dmap1 | NM_023128.2 | chr4:117674685-117682225 | 6114 | Dner | NM_152915.1 | chr1:84369838-84696221 |
| 6018 | Dmbt1 | NM_007769.2 | chr7:131032075-131121628 | 6115 | Dnlz | NM_001139503.1 | chr2:26348117-26352110 |
| 6019 | Dmbx1 | NM_001025567.1 | chr4:115915118-115939926 | 6116 | Dnm1 | NM_010065.3 | chr2:32308470-32353329 |
| 6020 | Dmc1 | NM_001278226.1 | chr15:79561497-79605109 | 6117 | Dnm1l | NM_001025947.2 | chr16:16312227-16359031 |
| 6021 | Dmd | NM_007868.6 | chrX:82948869-85205050 | 6118 | Dnm2 | NM_001039520.2 | chr9:21424907-21507146 |
| 6022 | Dmgdh | NM_028772.3 | chr13:93674435-93752823 | 6119 | Dnm3 | NM_001038619.1 | chr1:161987301-162478030 |
| 6023 | Dmkn | NM_001166173.1 | chr7:30763755-30781066 | 6120 | Dnm3os | NR_002870.2 | chr1:162217622-162225550 |
| 6024 | Dmp1 | NM_016779.2 | chr5:104220616-104214102 | 6121 | Dnmbp | NM_028029.4 | chr19:43846814-43930198 |
| 6025 | Dmpk | NM_001190490.1 | chr7:19083848-19093820 | 6122 | Dnmt1 | NM_001199431.1 | chr9:20907205-20952979 |
| 6026 | Dmr | NR_102372.1 | chr5:144358524-144361005 | 6123 | Dnmt3a | NM_001271753.1 | chr12:3807159-3914443 |
| 6027 | Dmrt1 | NM_015826.5 | chr19:25505705-25604328 | 6124 | Dnmt3aos | NR_045884.1 | chr12:3859292-3862244 |
| 6028 | Dmrt2 | NM_145831.3 | chr19:25672410-25678991 | 6125 | Dnmt3b | NM_001003960.4 | chr2:153649448-153687730 |
| 6029 | Dmrt3 | NM_177360.3 | chr19:25610536-25623921 | 6126 | Dnmt3l | NM_001081695.2 | chr10:78042286-78063622 |
| 6030 | Dmrta1 | NM_176647.3 | chr4:89688197-89694766 | 6127 | Dnpep | NM_001110831.1 | chr1:75308564-75317637 |
| 6031 | Dmrta2 | NM_172296.2 | chr4:109978024-109988684 | 6128 | Dnph1 | NM_207161.3 | chr17:48496788-46499618 |
| 6032 | Dmrtb1 | NM_019872.1 | chr4:107676289-107684182 | 6129 | Dntt | NM_001043228.1 | chr19:41029274-41059525 |
| 6033 | Dmrtc1a | NM_001038616.2 | chrX:102903220-102906557 | 6130 | Dnttip1 | NM_133763.1 | chr2:164746914-164768219 |
| 6034 | Dmrtc1b | NM_001039116.2 | chrX:102707880-102715209 | 6131 | Dnttip2 | NM_153806.1 | chr3:122274413-122285271 |
| 6035 | Dmrtc1c2 | NM_001142690.2 | chrX:102802962-102854616 | 6132 | Doc2a | NM_010069.1 | chr7:126847552-126852705 |
| 6036 | Dmrtc2 | NM_027732.2 | chr7:24870056-24877651 | 6133 | Doc2b | NM_007873.3 | chr11:75768270-75796060 |
| 6037 | Dmtf1 | NM_001110327.1 | chr5:9118867-9161776 | 6134 | Doc2g | NM_021791.3 | chr19:4063384-4007095 |
| 6038 | Dmtn | NM_001252662.1 | chr14:70602183-70627065 | 6135 | Dock1 | NM_001033420.2 | chr7:134670686-135173647 |
| 6039 | Dmwd | NM_010078.2 | chr7:19076199-19082775 | 6136 | Dock10 | NM_001285927.1 | chr1:80501067-80665352 |
| 6040 | Dmxl1 | NM_001081371.2 | chr18:49832996-49965473 | 6137 | Dock11 | NM_001009847.3 | chrX:35888831-36076562 |
| 6041 | Dmxl2 | NM_172771.2 | chr9:54365157-54501626 | 6138 | Dock2 | NM_033374.3 | chr11:34226820-34783905 |
| 6042 | Dna2 | NM_177372.3 | chr10:62947028-62974188 | 6139 | Dock3 | NM_153413.2 | chr9:106892824-107231909 |
| 6043 | Dnaaf1 | NM_026648.4 | chr8:119575234-119598454 | 6140 | Dock4 | NM_172803.2 | chr12:40446052-40846488 |
| 6044 | Dnaaf2 | NM_027269.4 | chr12:69189086-69198429 | 6141 | Dock5 | NM_177780.3 | chr14:67751927-67933972 |
| 6045 | Dnaaf3 | NM_001033548.2 | chr7:4522956-4532442 | 6142 | Dock6 | NM_177030.3 | chr9:21800179-21852635 |
| 6046 | Dnah1 | NM_001033668.1 | chr14:31260874-31323896 | 6143 | Dock7 | NM_001290636.1 | chr4:98996658-99120915 |
| 6047 | Dnah10 | NM_019536.1 | chr5:124725084-124834308 | 6144 | Dock8 | NM_028785.3 | chr19:24999528-25202432 |
| 6048 | Dnah11 | NM_010060.3 | chr12:117877881-118199043 | 6145 | Dock9 | NM_001081039.1 | chr14:121542038-121698417 |
| 6049 | Dnah17 | NM_001167746.1 | chr11:118021722-118129219 | 6146 | Dohh | NM_133964.2 | chr10:81384427-81388352 |
| 6050 | Dnah2 | NM_001081330.1 | chr11:69420808-69548108 | 6147 | Dok1 | NM_001291799.1 | chr6:83030935-83033471 |
| 6051 | Dnah5 | NM_133365.3 | chr15:28203765-28472045 | 6148 | Dok2 | NM_010071.2 | chr14:70774380-70778494 |
| 6052 | Dnah6 | NM_001164645.1 | chr6:73017606-73221631 | 6149 | Dok3 | NM_013739.2 | chr13:55523234-55528538 |
| 6053 | Dnah7a | NM_001252070.1 | chr1:53397001-53706784 | 6150 | Dok4 | NM_053246.3 | chr8:94863827-94876312 |
| 6054 | Dnah7b | NM_001160386.1 | chr1:46066737-46373550 | 6151 | Dok5 | NM_001163686.1 | chr2:170731806-170879775 |
| 6055 | Dnah8 | NM_013811.3 | chr17:30626935-30875264 | 6152 | Dok6 | NM_010039173.1 | chr18:89301134-89769136 |
| 6056 | Dnah9 | NM_001099633.1 | chr11:65831323-66168551 | 6153 | Dok7 | NM_172708.3 | chr5:35057083-35087831 |
| 6057 | Dnaic1 | NM_175138.4 | chr4:41569793-41638158 | 6154 | Dolk | NM_177648.3 | chr2:30284228-30286354 |
| 6058 | Dnaic2 | NM_001034878.2 | chr11:114727411-114757886 | 6155 | Dolpp1 | NM_001290508.1 | chr2:30392253-30400529 |
| 6059 | Dnaja1 | NM_001164671.2 | chr4:40722921-40734965 | 6156 | Donson | NM_021720.1 | chr16:91679264-91688728 |
| 6060 | Dnaja2 | NM_019794.4 | chr8:85537639-85555271 | 6157 | Dopey1 | NM_177208.3 | chr9:86467153-86555806 |
| 6061 | Dnaja3 | NM_001135132.1 | chr16:4684069-4707693 | 6158 | Dopey2 | NM_026700.2 | chr16:93713906-93740278 |
| 6062 | Dnaja4 | NM_021422.4 | chr9:54699558-54716317 | 6159 | Dos | NM_001195268.1 | chr10:80130433-80137387 |
| 6063 | Dnajb1 | NM_018808.3 | chr8:83608174-83612653 | 6160 | Dot1l | NM_199322.1 | chr10:80755205-80794347 |
| 6064 | Dnajb11 | NM_001190804.1 | chr16:22857844-22872465 | 6161 | Dox1 | NM_001029087.1 | chr6:48975142-48978745 |
| 6065 | Dnajb12 | NM_019965.2 | chr10:59879590-59898016 | 6162 | Dpagt1 | NM_007875.2 | chr9:44326844-44333600 |
| 6066 | Dnajb13 | NM_153527.2 | chr7:100503019-100514815 | 6163 | Dpcd | NM_172639.2 | chr19:45560614-45573287 |
| 6067 | Dnajb14 | NM_001033155.1 | chr3:137867674-137908931 | 6164 | Dpcr1 | NM_001033366.3 | chr17:35635754-35643695 |
| 6068 | Dnajb2 | NM_021317.2 | chr1:75236422-75245692 | 6165 | Dpep1 | NM_007876.2 | chr8:123186234-123201819 |
| 6069 | Dnajb3 | NM_008299.3 | chr1:88204731-88205748 | 6166 | Dpep2 | NM_176913.4 | chr8:105984945-105996423 |
| 6070 | Dnajb4 | NM_025926.4 | chr3:152183870-152193845 | 6167 | Dpep3 | NM_027960.2 | chr8:105973519-105979419 |
| 6071 | Dnajb5 | NM_019874.3 | chr4:42953093-42958732 | 6168 | Dpf1 | NM_013874.2 | chr7:29304004-29317586 |
| 6072 | Dnajb6 | NM_001037940.4 | chr5:29735897-29786478 | 6169 | Dpf2 | NM_001291078.1 | chr19:5896515-5912871 |
| 6073 | Dnajb7 | NM_021317.2 | chr15:81407087-81408273 | 6170 | Dpf3 | NM_001267625.1 | chr12:83213750-83487736 |
| 6074 | Dnajb8 | NM_001034583.1 | chr6:88222267-88223256 | 6171 | Dph1 | NM_144491.2 | chr11:75177642-75190483 |
| 6075 | Dnajb9 | NM_013760.4 | chr12:44205896-44210068 | 6172 | Dph2 | NM_026344.3 | chr4:117888642-117892003 |
| 6076 | Dnajc1 | NM_001190817.1 | chr2:18208332-18392830 | 6173 | Dph3 | NM_001047433.2 | chr14:32080516-32085692 |
| 6077 | Dnajc10 | NM_024181.2 | chr2:80315465-80354055 | 6174 | Dph5 | NM_027193.2 | chr3:115888182-115929323 |
| 6078 | Dnajc11 | NM_172704.1 | chr4:151933719-151981959 | 6175 | Dph6 | NM_025675.4 | chr2:114516417-114654928 |
| 6079 | Dnajc12 | NM_001253685.1 | chr10:63382442-63408840 | 6176 | Dph7 | NM_026043.3 | chr2:249624421-249734471 |
| 6080 | Dnajc13 | NM_001163026.1 | chr9:104151596-104262930 | 6177 | Dpm1 | NM_010072.4 | chr2:168209047-168230379 |
| 6081 | Dnajc14 | NM_028873.4 | chr10:128805675-128819446 | 6178 | Dpm2 | NM_010073.2 | chr2:32670857-32673571 |
| 6082 | Dnajc15 | NM_025384.4 | chr14:77874917 | 6179 | Dpm3 | NM_026767.4 | chr3:89266460-89267079 |
| 6083 | Dnajc16 | NM_172338.2 | chr4:141761997-141790644 | 6180 | Dpp10 | NM_199021.3 | chr1:123332137-124045559 |
| 6084 | Dnajc17 | NM_139139.2 | chr2:119172499-119208795 | 6181 | Dpp3 | NM_133803.2 | chr19:4907228-4928287 |
| 6085 | Dnajc18 | NM_029669.4 | chr18:35671104-35703144 | 6182 | Dpp4 | NM_001159543.1 | chr2:62333222-62412231 |
| 6086 | Dnajc19 | NM_001026211.2 | chr3:34057279-34081354 | 6183 | Dpp6 | NM_001130060.2 | chr5:27261934-27727500 |
| 6087 | Dnajc2 | NM_009634.3 | chr5:21757276-21785165 | 6184 | Dpp7 | NM_031843.2 | chr2:25352289-25356332 |
| 6088 | Dnajc21 | NM_030046.2 | chr15:10446762-10470516 | 6185 | Dpp8 | NM_028906.2 | chr9:65032457-65082651 |
| 6089 | Dnajc22 | NM_178835.2 | chr15:99099483-99104707 | 6186 | Dpp9 | NM_172624.3 | chr17:56186681-56218889 |
| 6090 | Dnajc24 | NM_026992.3 | chr2:105966707-106003549 | 6187 | Dppa1 | NM_001163358.1 | chr11:46607009-46622924 |
| 6091 | Dnajc25 | NM_001033165.3 | chr4:59003192-59023398 | 6188 | Dppa2 | NM_028615.1 | chr16:48310273-48319513 |
| 6092 | Dnajc27 | NM_153082.4 | chr6:42.4082573-4110612 | 6189 | Dppa3 | NM_139218.1 | chr6:122626423-122630271 |
| 6093 | Dnajc28 | NM_001099738.1 | chr16:91614256-91618999 | 6190 | Dppa4 | NM_001018002.1 | chr16:48283734-48294292 |
| 6094 | Dnajc3 | NM_008929.3 | chr14:118937931-118981702 | 6191 | Dppa5a | NM_025274.3 | chr9:78367053-78368199 |
| 6095 | Dnajc30 | NM_025362.3 | chr5:135064235-135065365 | 6192 | Dpt | NM_019759.2 | chr1:164796731-164824266 |
| 6096 | Dnajc4 | NM_020566.1 | chr19:6987910-6992272 | 6193 | Dpy19l1 | NM_172920.4 | chr9:24411778-24503140 |
| 6097 | Dnajc5 | NM_001271584.1 | chr2:181520484-181552880 | 6194 | Dpy19l2 | NM_001166207.1 | chr9:24557047-24696293 |
| 6098 | Dnajc5b | NM_001163536.1 | chr3:19508594-19610862 | 6195 | Dpy19l3 | NM_178704.3 | chr7:35685499-35754454 |
| 6099 | Dnajc5g | NM_177677.3 | chr5:31108318-31112524 | 6196 | Dpy19l4 | NM_001081201.1 | chr4:11265078-11322131 |
| 6100 | Dnajc6 | NM_001038603.1 | chr4:101550593-101642799 | 6197 | Dpy30 | NM_001146222.1 | chr17:74294473-74316394 |
| 6101 | Dnajc7 | NM_019795.4 | chr11:100582835-100620168 | 6198 | Dpyd | NM_170778.2 | chr3:118562177-119432918 |
| 6102 | Dnajc8 | NM_172400.3 | chr4:132535558-132553742 | 6199 | Dpys | NM_001164466.1 | chr15:39782696-39857470 |
| 6103 | Dnajc9 | NM_134081.5 | chr14:20384637-20388910 | 6200 | Dpysl2 | NM_009955.3 | chr14:66802863-66868600 |
| 6104 | Dnal1 | NM_028821.3 | chr12:84314327-84343510 | 6201 | Dpysl3 | NM_001136862.2 | chr18:43320978-43373272 |
| 6105 | Dnal4 | NM_017470.2 | chr15:79761448-79774467 | 6202 | Dpysl4 | NM_011993.4 | chr7:139086000-139101793 |
| 6106 | Dnase1l3 | NM_153223.4 | chr14:128065538-125065657 | 6203 | Dpysl5 | NM_001081201.1 | chr5:30711894-30799369 |
| 6107 | Dnase1 | NM_010061.5 | chr16:4037144-4040024 | 6204 | DQ267100 | NR_046304.1 | chr12:109649616-109649687 |
| 6108 | Dnase1l1 | NM_001172154.1 | chrX:74273216-74282333 | 6205 | DQ267101 | NR_046305.1 | chr12:109651423-109651495 |
| 6109 | Dnase1l2 | NM_025718.3 | chr7:24440767-24443101 | 6206 | DQ267102 | NR_046306.1 | chr12:109656344-109656415 |
| 6110 | Dnase1l3 | NM_007870.3 | chr14:7965189-7994182 | 6207 | Dqx1 | NM_033606.3 | chr6:83057843-83067219 |

Fig.21 - 33

| | | | | | | | |
|---|---|---|---|---|---|---|---|
| 6208 | Dr1 | NM_026106.4 | chr5:108268896-108280521 | 6305 | Dym | NM_027727.2 | chr18:75018771-75286966 |
| 6209 | Dram1 | NM_027878.2 | chr10:88322803-88357075 | 6306 | Dynap | NM_029346.1 | chr18:70240428-70244584 |
| 6210 | Dram2 | NM_001025582.2 | chr3:106547797-106575341 | 6307 | Dync1h1 | NM_030238.2 | chr12:110601394-110666944 |
| 6211 | Drap1 | NM_001291080.1 | chr19:5422803-5424979 | 6308 | Dync1i1 | NM_001191023.1 | chr6:5725638-6028039 |
| 6212 | Draxin | NM_027426.3 | chr4:148098436-148130698 | 6309 | Dync1i2 | NM_001198872.1 | chr2:71211705-71263302 |
| 6213 | Drc1 | NM_001033460.3 | chr5:30341662-30366708 | 6310 | Dync1li1 | NM_146229.2 | chr9:114688830-114723777 |
| 6214 | Drd1a | NM_001291801.1 | chr13:54051183-54054780 | 6311 | Dync1li2 | NM_001013380.2 | chr8:104417673-104443047 |
| 6215 | Drd2 | NM_010077.2 | chr9:49340661-49407214 | 6312 | Dync2h1 | NM_029851.2 | chr9:6928502-7177046 |
| 6216 | Drd3 | NM_007877.1 | chr16:43762241-43822839 | 6313 | Dync2li1 | NM_172256.1 | chr17:84626498-84655564 |
| 6217 | Drd4 | NM_007878.2 | chr7:141292008-141295001 | 6314 | Dynll1 | NM_019682.4 | chr5:115297109-115300990 |
| 6218 | Drd5 | NM_013503.3 | chr5:38319508-38322523 | 6315 | Dynll2 | NM_001168471.1 | chr11:87979524-87998298 |
| 6219 | Dreh | NR_105051.1 | chr17:64767110-64767931 | 6316 | Dynlrb1 | NM_001291108.1 | chr2:155236607-155250277 |
| 6220 | Drg1 | NM_007879.1 | chr11:3249921-3266386 | 6317 | Dynlrb2 | NM_029297.1 | chr8:116505014-116515915 |
| 6221 | Drg2 | NM_021354.1 | chr11:60454616-60468705 | 6318 | Dynlt1a | NM_001166629.2 | chr17:6306343-6317474 |
| 6222 | Drosha | NM_001130143.1 | chr15:12824814-12935291 | 6319 | Dynlt1b | NM_009342.2 | chr17:6430111-6436295 |
| 6223 | Drip2 | NM_010078.3 | chrX:134404779-134456573 | 6320 | Dynlt1c | NM_001166630.1 | chr17:6601778-6655831 |
| 6224 | Dsc1 | NM_001291804.1 | chr18:20083470-20114773 | 6321 | Dynlt1f | NM_001166627.1 | chr17:6601670-6655939 |
| 6225 | Dsc2 | NM_013505.3 | chr18:20030797-20059505 | 6322 | Dynlt3 | NM_025975.5 | chrX:9654269-9662983 |
| 6226 | Dsc3 | NM_001291809.1 | chr18:19960929-20002097 | 6323 | Dyrk1a | NM_001113389.1 | chr16:94570906-94695519 |
| 6227 | Dscam | NM_031174.4 | chr16:96592078-97170735 | 6324 | Dyrk1b | NM_001037957.3 | chr7:28179482-28187298 |
| 6228 | Dscaml1 | NM_001081170.1 | chr9:45430292-45753713 | 6325 | Dyrk2 | NM_001014390.2 | chr10:118859348-118868903 |
| 6229 | Dscc1 | NM_183089.2 | chr15:55076100-55090478 | 6326 | Dyrk3 | NM_145508.2 | chr1:131128440-131138234 |
| 6230 | Dscr3 | NM_007723.4 | chr16:94497723-94526629 | 6327 | Dyrk4 | NM_207210.2 | chr6:126876198-126921839 |
| 6231 | Dse | NM_172508.2 | chr10:34151392-34207551 | 6328 | Dysf | NM_001077694.2 | chr6:84008597-84211059 |
| 6232 | Dsel | NM_001081316.1 | chr1:111858701-111864918 | 6329 | Dytn | NM_001081658.1 | chr1:63622850-63686927 |
| 6233 | Dsg1a | NM_010079.2 | chr18:20130872-20343353 | 6330 | Dyx1c1 | NM_001163725.1 | chr9:72958784-72973067 |
| 6234 | Dsg1b | NM_181682.1 | chr18:20376834-20409741 | 6331 | Dzank1 | NM_172859.2 | chr2:144470556-144527398 |
| 6235 | Dsg1c | NM_181680.1 | chr18:20247339-20283923 | 6332 | Dzip1 | NM_025943.3 | chr14:118875519-118925470 |
| 6236 | Dsg2 | NM_007883.2 | chr18:20558115-20604526 | 6333 | Dzip1l | NM_028258.4 | chr9:99629530-99670075 |
| 6237 | Dsg3 | NM_030596.3 | chr18:20510303-20541310 | 6334 | Dzip3 | NM_001110017.1 | chr16:48924227-48994112 |
| 6238 | Dsg4 | NM_181564.2 | chr18:20436174-20471821 | 6335 | E030002O03Rik | NM_172905.2 | chr7:104153012-104164816 |
| 6239 | Dsn1 | NM_025853.3 | chr2:156995061-157007075 | 6336 | E030003E18Rik | NR_015502.1 | chr19:20492714-20556410 |
| 6240 | Dsp | NM_023842.2 | chr13:38151293-38198577 | 6337 | E030011O05Rik | NR_015511.2 | chr6:96731574-96752831 |
| 6241 | Dspp | NM_010080.2 | chr5:104170711-104180127 | 6338 | E030013I19Rik | NR_040353.1 | chr2:12301245-12312315 |
| 6242 | Dst | NM_001276764.1 | chr1:33908224-34308662 | 6339 | E030018I13Rik | NM_001256311.1 | chr7:63916856-63920539 |
| 6243 | Dstn | NM_019771.2 | chr2:143915330-143943324 | 6340 | E030019B06Rik | NM_001302546.1 | chr7:139600914-139683815 |
| 6244 | Dstyk | NM_172516.4 | chr1:132417452-132466959 | 6341 | E030019B06Rik | NR_045082.1 | chr12:56490427-56529420 |
| 6245 | Dtd1 | NM_025314.3 | chr2:144599952-144768747 | 6342 | E030024N20Rik | NR_033228.1 | chr19:16164097-16170458 |
| 6246 | Dtd2 | NM_025542.4 | chr12:51997506-52006501 | 6343 | E030025P04Rik | NR_037978.1 | chr11:109199290-109144369 |
| 6247 | Dthd1 | NM_001170705.1 | chr5:62813822-62888318 | 6344 | E030030I06Rik | NM_001254744.1 | chr10:22113049-22149270 |
| 6248 | Dtl | NM_029766.3 | chr1:191537355-191575544 | 6345 | E030044B06Rik | NR_045343.1 | chr19:40868315-40882639 |
| 6249 | Dtna | NM_001285807.1 | chr18:23415408-23659719 | 6346 | E130006O01Rik | NR_045832.1 | chr5:111734283-111761728 |
| 6250 | Dtnb | NM_001162465.1 | chr12:3572390-3781398 | 6347 | E130008D07Rik | NR_045153.1 | chr17:43149356-43158291 |
| 6251 | Dtnbp1 | NM_025772.4 | chr13:44922079-45002096 | 6348 | E130012A19Rik | NM_175332.3 | chr11:97627886-97629716 |
| 6252 | Dtwd1 | NM_026981.1 | chr2:126152140-126165277 | 6349 | E130018N17Rik | NR_040327.1 | chr2:168152602-168154513 |
| 6253 | Dtwd2 | NM_001170960.1 | chr18:49696144-49755601 | 6350 | E130102H24Rik | NR_040708.1 | chr4:101346923-101356248 |
| 6254 | Dtx1 | NM_008052.3 | chr5:120680263-120711669 | 6351 | E130104B19Rik | NR_015604.2 | chr6:125231275-125239934 |
| 6255 | Dtx2 | NM_001256096.1 | chr5:135984799-136032880 | 6352 | E130114P18Rik | NR_015513.2 | chr4:97567874-97584591 |
| 6256 | Dtx3 | NM_030714.2 | chr10:127190377-127196709 | 6353 | E130201H02Rik | NR_024324.1 | chr7:120597624-120598475 |
| 6257 | Dtx3l | NM_001013371.2 | chr16:35926814-35938027 | 6354 | E130215H24Rik | NR_040331.1 | chr2:150667493-150668932 |
| 6258 | Dtx4 | NM_172442.3 | chr19:12466335-12501996 | 6355 | E130218I03Rik | NR_040435.1 | chr4:134243762-134245873 |
| 6259 | Dtymk | NM_001105667.1 | chr1:93792575-93801934 | 6356 | E130304I02Rik | NR_033567.1 | chr7:35802591-35838074 |
| 6260 | Duox1 | NM_001099297.1 | chr2:122315671-122347972 | 6357 | E130307A14Rik | NR_038037.1 | chr10:39621410-39732007 |
| 6261 | Duox2 | NM_176610.2 | chr2:122280436-122298165 | 6358 | E130308A19Rik | NM_001015681.2 | chr4:59626210-59754303 |
| 6262 | Duoxa1 | NM_001305262.1 | chr2:122303540-122313744 | 6359 | E130309D14Rik | NM_172726.4 | chr5:143301071-143315960 |
| 6263 | Duoxa2 | NM_025777.2 | chr2:122298899-122302885 | 6360 | E130309D14Rik | NM_001013784.1 | chr11:74619604-74641516 |
| 6264 | Dupd1 | NM_001013826.2 | chr14:21676571-21714576 | 6361 | E130309F12Rik | NM_178756.4 | chr4:49059461-49340261 |
| 6265 | Dus1l | NM_026824.4 | chr11:120789201-120796395 | 6362 | E130310O04Rik | NR_045722.1 | chr16:34952025-34958864 |
| 6266 | Dus2 | NM_025518.2 | chr8:106011477-106053840 | 6363 | E130311K13Rik | NM_177856.4 | chr3:63914695-63929385 |
| 6267 | Dus3l | NM_144858.2 | chr17:56764750-56770098 | 6364 | E130317F20Rik | NR_029447.1 | chr10:79851376-79854971 |
| 6268 | Dus4l | NM_028002.2 | chr12:31640054-31654826 | 6365 | E230008N13Rik | NM_198660.2 | chr4:45890302-45950774 |
| 6269 | Dusp1 | NM_013642.3 | chr17:26505990-26508472 | 6366 | E230016K23Rik | NR_036452.1 | chr11:83582060-83623693 |
| 6270 | Dusp10 | NM_022019.2 | chr1:184034166-184075636 | 6367 | E230016M11Rik | NR_040278.1 | chr6:67036598-67080652 |
| 6271 | Dusp11 | NM_028099.4 | chr6:85942268-85961667 | 6368 | E230019M04Rik | NM_177921.3 | chrX:140062878-140106797 |
| 6272 | Dusp12 | NM_023173.2 | chr1:170874187-170885540 | 6369 | E230025N22Rik | NM_172831.2 | chr15:36684922-36695925 |
| 6273 | Dusp13 | NM_001007268.1 | chr14:21733394-21748622 | 6370 | E230029C05Rik | NR_110364.1 | chr7:90029158-90049071 |
| 6274 | Dusp14 | NM_019819.3 | chr11:64048044-64068357 | 6371 | E2f1 | NM_001291105.1 | chr2:154599399-154569426 |
| 6275 | Dusp15 | NM_001159376.1 | chr2:152940994-152951582 | 6372 | E2f2 | NM_177733.7 | chr4:136172273-136196056 |
| 6276 | Dusp16 | NM_001048054.2 | chr6:134715467-134792628 | 6373 | E2f3 | NM_001289920.1 | chr13:29906574-29984391 |
| 6277 | Dusp18 | NM_173745.5 | chr11:3895239-3901296 | 6374 | E2f4 | NM_148952.1 | chr8:105297662-105305370 |
| 6278 | Dusp19 | NM_024434.4 | chr2:80617213-80631661 | 6375 | E2f5 | NM_007892.2 | chr3:14578670-14606309 |
| 6279 | Dusp2 | NM_010090.2 | chr2:127336158-127338377 | 6376 | E2f6 | NM_033270.2 | chr12:16810964-16826752 |
| 6280 | Dusp21 | NM_028568.1 | chrX:18145869-18146692 | 6377 | E2f7 | NM_178609.4 | chr10:110745464-110787384 |
| 6281 | Dusp22 | NM_001037955.4 | chr13:30660058-30711232 | 6378 | E2f8 | NM_001013368.5 | chr7:48866428-48881041 |
| 6282 | Dusp23 | NM_026725.2 | chr1:172630768-172632974 | 6379 | E330009B07Rik | NR_045698.1 | chr6:40407497-40436133 |
| 6283 | Dusp26 | NM_025869.3 | chr8:31089661-31097401 | 6380 | E330011O21Rik | NR_045698.1 | chr16:78250862-78255454 |
| 6284 | Dusp27 | NM_001033344.3 | chr1:166098147-166127898 | 6381 | E330012B07Rik | NR_033640.1 | chr6:147180240-147208294 |
| 6285 | Dusp28 | NM_175118.3 | chr1:92906988-92908620 | 6382 | E330013P04Rik | NR_026942.1 | chr19:60146674-60162591 |
| 6286 | Dusp3 | NM_028207.3 | chr11:101971143-101984791 | 6383 | E330014E10Rik | NM_001122668.1 | chr5:82563-95804230 |
| 6287 | Dusp4 | NM_176933.4 | chr8:34807609-34819894 | 6384 | E330017A01Rik | NM_175011.2 | chr1:58635261-58638403 |
| 6288 | Dusp5 | NM_001085390.1 | chr19:53529317-53541322 | 6385 | E330017L17Rik | NR_045190.2 | chr4:129906225-129908996 |
| 6289 | Dusp6 | NM_026268.3 | chr10:99263230-99267489 | 6386 | E330020D12Rik | NR_033736.1 | chr1:153404185-153414233 |
| 6290 | Dusp7 | NM_153459.4 | chr9:106368631-106375723 | 6387 | E330021D16Rik | NM_001201390.1 | chr6:136400318-136415569 |
| 6291 | Dusp8 | NM_008748.2 | chr7:142079486-142095284 | 6388 | E330020J22Rik | NR_045332.1 | chr9:98748598-98820087 |
| 6292 | Dusp9 | NM_029352.3 | chrX:73639440-73643514 | 6389 | E330033B04Rik | NR_030690.1 | chr15:96268563-96275275 |
| 6293 | Dut | NM_001159646.1 | chr2:125247247-125259049 | 6390 | E330034G19Rik | NM_001032214.2 | chr14:24293363-24309959 |
| 6294 | Dux | NM_001081954.1 | chr10:58230659-58232675 | 6391 | E330026F18Rik | NR_015542.1 | chr7:78581065-78718220 |
| 6295 | Duxbl1 | NM_183389.1 | chr14:25983004-26269100 | 6392 | E430018J23Rik | NM_198011.2 | chr7:127390835-127393621 |
| 6296 | Duxbl2 | NM_001177538.1 | chr14:25983004-26269434 | 6393 | E430025E21Rik | NM_153548.2 | chr15:59331996-59374152 |
| 6297 | Duxbl3 | NM_001177538.1 | chr14:26258303-26269434 | 6394 | Eaf1 | NM_027893.4 | chr17:24445392 |
| 6298 | Dvl1 | NM_010091.4 | chr4:155847316-155859303 | 6395 | E530011F21Rik | NR_002167.2 | chrX:105164377-105165505 |
| 6299 | Dvl2 | NM_007888.3 | chr11:70000625-70010109 | 6396 | E530011L22Rik | NR_033533.1 | chr9:121756639-121759943 |
| 6300 | Dvl3 | NM_007889.2 | chr16:20517063-20532187 | 6397 | Eaf2 | NM_028932.4 | chr16:31495078-31509858 |
| 6301 | DXBay18 | NM_001025384.3 | chrX:73117046-73149450 | 6398 | Eaf2 | NM_001113401.1 | chr16:36792883-36828259 |
| 6302 | Dxo | NM_001163770.1 | chr17:34830710-34839186 | 6399 | Eapp | NM_025456.3 | chr12:54673466-54695865 |
| 6303 | Dydc1 | NM_027094.1 | chr17:41072910-41092197 | 6400 | Ear1 | NM_007894.3 | chr14:43818764-43819639 |
| 6304 | Dydc2 | NM_027717.1 | chr14:41049208-41069074 | 6401 | Ear10 | NM_053112.1 | chr14:43922897-43923368 |

Fig.21 - 34

| | | | | | | | |
|---|---|---|---|---|---|---|---|
| 6402 | Ear14 | NM_017389.2 | chr14:51203694-51204156 | 6499 | Eftud1 | NM_001159672.1 | chr7:82648613-82777852 |
| 6403 | Ear2 | NM_007895.2 | chr14:44102653-44103531 | 6500 | Eftud2 | NM_001109995.1 | chr11:102838471-102880975 |
| 6404 | Ear3 | NM_017388.1 | chr14:44102886-44103357 | 6501 | Egf | NM_010113.4 | chr3:129677576-129755322 |
| 6405 | Ear4 | NM_001017422.1 | chr14:51203689-51204156 | 6502 | Egfbp2 | NM_010115.6 | chr7:44012696-44016968 |
| 6406 | Ear6 | NM_053111.2 | chr14:51853767-51854642 | 6503 | Egfem1 | NM_001167748.1 | chr3:29082576-29691056 |
| 6407 | Ear7 | NM_017385.1 | chr14:51853997-51854465 | 6504 | Egfl6 | NM_019397.3 | chrX:166523006-166585716 |
| 6408 | Ears2 | NM_026140.3 | chr7:122034161-122067086 | 6505 | Egfl7 | NM_001164564.1 | chr2:26586629-26592682 |
| 6409 | Ebag9 | NM_019480.4 | chr15:44619640-44641026 | 6506 | Egfl8 | NM_152922.3 | chr17:34613349-34615971 |
| 6410 | Ebf1 | NM_001290709.1 | chr11:44618099-45008096 | 6507 | Egflam | NM_001289496.1 | chr15:7206119-7398390 |
| 6411 | Ebf2 | NM_001276387.1 | chr14:67233291-67430952 | 6508 | Egfr | NM_007912.4 | chr11:16752202-16887658 |
| 6412 | Ebf3 | NM_001113414.1 | chr7:137193670-137314445 | 6509 | Egln1 | NM_053207.2 | chr8:124908586-124949254 |
| 6413 | Ebf4 | NM_001110513.1 | chr2:130299938-130370424 | 6510 | Egln2 | NM_053208.4 | chr7:27158657-27166802 |
| 6414 | Ebi3 | NM_015766.2 | chr17:55952622-55957022 | 6511 | Egln3 | NM_028133.2 | chr12:54178980-54203874 |
| 6415 | Ebna1bp2 | NM_026932.4 | chr4:118620798-118627776 | 6512 | Egr1 | NM_007913.5 | chr18:34861206-34864956 |
| 6416 | Ebp | NM_007898.3 | chrX:8185328-8193512 | 6513 | Egr2 | NM_010118.3 | chr10:67537868-67542188 |
| 6417 | Ebpl | NM_026598.3 | chr14:61339762-61360445 | 6514 | Egr3 | NM_001289925.1 | chr14:70077444-70082613 |
| 6418 | Ecd | NM_027475.3 | chr14:20319858-20348121 | 6515 | Egr4 | NM_020596.2 | chr6:85511121-85513542 |
| 6419 | Ece1 | NM_199307.2 | chr4:137862236-137965229 | 6516 | Ehbp1 | NM_001252515.1 | chr11:22005825-22286795 |
| 6420 | Ece2 | NM_025462.2 | chr16:20611600-20618869 | 6517 | Ehbp1l1 | NM_001134595.1 | chr19:5707373-5726317 |
| 6421 | Ecel1 | NM_001277925.1 | chr1:87147654-87156136 | 6518 | Ehd1 | NM_010119.5 | chr19:6276895-6300096 |
| 6422 | Ech1 | NM_016772.1 | chr7:28825337-28832239 | 6519 | Ehd2 | NM_153068.3 | chr7:15948986-15967535 |
| 6423 | Echdc1 | NM_001110195.1 | chr10:29313165-29346661 | 6520 | Ehd3 | NM_020578.3 | chr17:73804840-73832093 |
| 6424 | Echdc2 | NM_001254754.1 | chr4:108165436-108179308 | 6521 | Ehd4 | NM_133838.4 | chr2:120089486-120154575 |
| 6425 | Echdc3 | NM_024208.4 | chr2:6184864-6212994 | 6522 | Ehf | NM_007914.3 | chr2:103263432-103303196 |
| 6426 | Echs1 | NM_053119.2 | chr7:140106722-140116423 | 6523 | Ehhadh | NM_023737.3 | chr16:21761284-21787834 |
| 6427 | Eci1 | NM_010023.4 | chr17:24428682-24439316 | 6524 | Ehmt1 | NM_001012518.3 | chr2:24790768-24919609 |
| 6428 | Eci2 | NM_001110331.1 | chr13:34977747-34994144 | 6525 | Ehmt2 | NM_001286673.1 | chr17:34898973-34914050 |
| 6429 | Eci3 | NM_026947.4 | chr13:34944613-34963809 | 6526 | Ei24 | NM_001199494.1 | chr9:36779152-36797393 |
| 6430 | Ecm1 | NM_001295653.1 | chr3:95734147-95739569 | 6527 | Eid1 | NM_025613.3 | chr2:125675099-125675642 |
| 6431 | Ecm2 | NM_001012324.2 | chr13:49504809-49532789 | 6528 | Eid2 | NM_198425.2 | chr7:28267880-28269168 |
| 6432 | Ecscr | NM_001033141.1 | chr18:35713088-35721491 | 6529 | Eid2b | NM_001177427.1 | chr7:28277705-28280129 |
| 6433 | Ecsit | NM_001253897.1 | chr9:22072245-22085427 | 6530 | Eid3 | NM_025499.2 | chr10:82866625-82867929 |
| 6434 | Ect2 | NM_001177625.1 | chr3:27097221-27153854 | 6531 | Eif1 | NM_011508.1 | chr11:100319995-100322096 |
| 6435 | Ect2l | NM_001195036.1 | chr10:18129021-18210890 | 6532 | Eif1a | NM_010120.5 | chr18:46597703-48610225 |
| 6436 | Eda | NM_001177937.1 | chrX:99975605-100400760 | 6533 | Eif1ad | NM_027236.2 | chr19:5366812-5371511 |
| 6437 | Eda2r | NM_001161432.1 | chrX:97333840-97377209 | 6534 | Eif1ax | NM_025437.4 | chrX:159372194-159385699 |
| 6438 | Edar | NM_010100.3 | chr10:58600787-58675696 | 6535 | Eif1b | NM_026892.3 | chr9:120492605-120495327 |
| 6439 | Edaradd | NM_133643.4 | chr13:12471208-12520450 | 6536 | Eif2a | NM_001005509.2 | chr3:58525820-58557501 |
| 6440 | Edc3 | NM_153799.3 | chr9:57730658-57750162 | 6537 | Eif2ak1 | NM_013557.2 | chr5:143871861-143902717 |
| 6441 | Edc4 | NM_181594.3 | chr8:105880880-106893225 | 6538 | Eif2ak2 | NM_011163.4 | chr17:78852549-78882572 |
| 6442 | Eddm36 | NM_203508.1 | chr14:51116552-51137791 | 6539 | Eif2ak3 | NM_010121.3 | chr6:70844514-70905241 |
| 6443 | Edem1 | NM_138677.1 | chr6:108828640-108859358 | 6540 | Eif2ak4 | NM_001177806.1 | chr2:118389111-118475234 |
| 6444 | Edem2 | NM_145537.2 | chr2:155701672-155729475 | 6541 | Eif2b1 | NM_145371.4 | chr5:124670213-124679131 |
| 6445 | Edem3 | NM_001039644.2 | chr1:151755373-151822328 | 6542 | Eif2b2 | NM_145445.4 | chr12:85219480-85226628 |
| 6446 | Edf1 | NM_021519.1 | chr2:25557899-25562082 | 6543 | Eif2b3 | NM_001111277.1 | chr4:117019407-117086852 |
| 6447 | Edil3 | NM_001037987.3 | chr13:88821471-89323225 | 6544 | Eif2b4 | NM_001127355.1 | chr5:31187557-31193139 |
| 6448 | Edn1 | NM_010104.3 | chr13:42301269-42307989 | 6545 | Eif2b5 | NM_172265.2 | chr16:20498816-20509325 |
| 6449 | Edn2 | NM_007902.2 | chr4:120161423-120167860 | 6546 | Eif2d | NM_001136070.1 | chr1:131153206-131173471 |
| 6450 | Edn3 | NM_007903.4 | chr2:174760757-174784042 | 6547 | Eif2s1 | NM_026114.3 | chr12:78862071-78887010 |
| 6451 | Ednra | NM_010332.2 | chr8:77663028-77724452 | 6548 | Eif2s2 | NM_026030.2 | chr2:154871409-154892906 |
| 6452 | Ednrb | NM_001136061.2 | chr14:103814614-103844476 | 6549 | Eif2s3␣ | NM_012010.3 | chrX:94188708-94212651 |
| 6453 | Edrf1 | NM_178115.4 | chr7:133637674-133673017 | 6550 | Eif2s3y | NM_012011.1 | chrY:1010611-1028598 |
| 6454 | Eea1 | NM_001001932.3 | chr10:95940662-96045618 | 6551 | Eif3a | NM_010123.3 | chr19:60761115-60790693 |
| 6455 | Eed | NM_021876.3 | chr7:89984653-89980976 | 6552 | Eif3b | NM_133916.2 | chr5:140419304-140443358 |
| 6456 | Eef1a1 | NM_010106.1 | chr9:78478453-78481724 | 6553 | Eif3c | NM_146200.1 | chr7:126546910-126566366 |
| 6457 | Eef1a2 | NM_007906.2 | chr2:181147691-181157015 | 6554 | Eif3d | NM_018749.2 | chr15:77958997-77970824 |
| 6458 | Eef1b2 | NM_018796.3 | chr1:63176830-63180486 | 6555 | Eif3e | NM_008388.2 | chr15:43250039-43282736 |
| 6459 | Eef1d | NM_001285429.1 | chr15:75894795-75909556 | 6556 | Eif3f | NM_025344.2 | chr7:108934414-108941942 |
| 6460 | Eef1e1 | NM_025380.2 | chr13:38645690-38659028 | 6557 | Eif3g | NM_018876.3 | chr9:20894348-20898590 |
| 6461 | Eef1g | NM_026007.4 | chr19:8967040-8978180 | 6558 | Eif3h | NM_080635.1 | chr15:51786662-51865461 |
| 6462 | Eef2 | NM_007907.2 | chr10:81176630-81182509 | 6559 | Eif3i | NM_018799.2 | chr4:129591973-129600648 |
| 6463 | Eef2k | NM_001267710.1 | chr7:120843599-120907219 | 6560 | Eif3j1 | NM_144545.4 | chr2:122028579-122053632 |
| 6464 | Eefsec | NM_023060.3 | chr6:88257333-88446539 | 6561 | Eif3j2 | NM_001256055.1 | chr2:122028582-122053631 |
| 6465 | Eepd1 | NM_026189.3 | chr9:25481596-25604110 | 6562 | Eif3k | NM_001285942.1 | chr7:28971371-28981888 |
| 6466 | Efcab1 | NM_025769.3 | chr16:14906645-14924527 | 6563 | Eif3l | NM_145139.2 | chr15:79075222-79094400 |
| 6467 | Efcab10 | NM_029152.1 | chr12:33463333-33401269 | 6564 | Eif3m | NM_145380.2 | chr2:104999656-105017027 |
| 6468 | Efcab11 | NM_030172.2 | chr12:99717530-99883442 | 6565 | Eif4a1 | NM_001159375.1 | chr11:69666985-69672423 |
| 6469 | Efcab12 | NM_001110506.1 | chr6:115810728-115838412 | 6566 | Eif4a2 | NM_001123037.2 | chr16:23107467-23114132 |
| 6470 | Efcab14 | NM_172698.2 | chr4:115738072-115777327 | 6567 | Eif4a3 | NM_138669.1 | chr11:119288362-119309043 |
| 6471 | Efcab2 | NM_026626.2 | chr1:178405880-178483249 | 6568 | Eif4b | NM_145625.3 | chr15:102073772-102097173 |
| 6472 | Efcab3 | NM_001031046.1 | chr11:105092218-105117531 | 6569 | Eif4e | NM_007917.4 | chr3:138526190-138559696 |
| 6473 | Efcab4a | NM_001025103.2 | chr7:141461093-141466602 | 6570 | Eif4e1b | NM_001033269.3 | chr13:54783997-54788458 |
| 6474 | Efcab4b | NM_001033464.3 | chr7:127577974-127629938 | 6571 | Eif4e2 | NM_001039169.1 | chr1:87213938-87228858 |
| 6475 | Efcab5 | NM_176965.3 | chr11:77080914-77188968 | 6572 | Eif4e3 | NM_025829.4 | chr6:99625136-99666771 |
| 6476 | Efcab6 | NM_001161628.1 | chr15:83866711-83936095 | 6573 | Eif4ebp1 | NM_007918.3 | chr8:27260326-27275656 |
| 6477 | Efcab7 | NM_145549.1 | chr4:99829499-99912783 | 6574 | Eif4ebp2 | NM_010124.2 | chr10:61432496-61452669 |
| 6478 | Efcab8 | NM_036629.1 | chr2:153780878-153795182 | 6575 | Eif4ebp3 | NM_201256.4 | chr18:36664059-36666324 |
| 6479 | Efcab9 | NM_027031.3 | chr11:32522732-32527574 | 6576 | Eif4enif1 | NM_001166547.1 | chr11:3202994-3244588 |
| 6480 | Efccl | NM_001159697.1 | chr6:87730868-87755911 | 6577 | Eif4g1 | NM_001304432.1 | chr16:20672720-20692883 |
| 6481 | Efemp1 | NM_146015.2 | chr11:28853204-28926748 | 6578 | Eif4g2 | NM_001040131.2 | chr7:111067984-111083080 |
| 6482 | Efemp2 | NM_001164352.1 | chr19:5474734-5481854 | 6579 | Eif4g3 | NM_001256195.1 | chr4:137993455-138207079 |
| 6483 | Efhb | NM_172497.3 | chr17:53399888-53463321 | 6580 | Eif4h | NM_033561.2 | chr5:134619871-134639409 |
| 6484 | Efhc1 | NM_027974.1 | chr1:20951625-20990841 | 6581 | Eif5 | NM_173363.5 | chr12:111538100-111546753 |
| 6485 | Efhc2 | NM_028916.4 | chrX:17132048-17319368 | 6582 | Eif5a | NM_001166589.1 | chr11:69916711-69921386 |
| 6486 | Efhd1 | NM_028117.3 | chr1:87264363-87310791 | 6583 | Eif5a2 | NM_177586.5 | chr3:28781310-28798846 |
| 6487 | Efhd2 | NM_025994.3 | chr4:141858141-141874920 | 6584 | Eif5b | NM_198303.2 | chr1:37998009-38085579 |
| 6488 | Efna1 | NM_010107.3 | chr3:89271729-89280951 | 6585 | Eif6 | NM_010579.2 | chr2:155819836-155826925 |
| 6489 | Efna2 | NM_007909.3 | chr10:80179481-80190010 | 6586 | Elac1 | NM_053255.3 | chr18:73735037-73754479 |
| 6490 | Efna3 | NM_010108.1 | chr3:89314950-89322873 | 6587 | Elac2 | NM_023479.2 | chr11:64979034-65002076 |
| 6491 | Efna4 | NM_007910.2 | chr3:89313392-89338028 | 6588 | Elane | NM_015779.2 | chr10:79886311-79888216 |
| 6492 | Efna5 | NM_010109.3 | chr17:62602956-62881317 | 6589 | Elavl1 | NM_010485.3 | chr8:4284783-4325100 |
| 6493 | Efnb1 | NM_010110.5 | chrX:99136060-99149022 | 6590 | Elavl2 | NM_001177883.1 | chr4:91250766-91376496 |
| 6494 | Efnb2 | NM_010111.5 | chr8:8617438-8660773 | 6591 | Elavl3 | NM_010487.2 | chr9:22015004-22052023 |
| 6495 | Efnb3 | NM_007911.5 | chr11:69554091-69560237 | 6592 | Elavl4 | NM_001038698.1 | chr4:110203736-110287511 |
| 6496 | Efr3a | NM_133766.3 | chr15:65787606-65873812 | 6593 | Elf1 | NM_133666.2 | chr14:79515673-79582491 |
| 6497 | Efr3b | NM_001082483.1 | chr12:3962553-4038915 | 6594 | Elf2 | NM_001291059.1 | chr3:51252719-51340644 |
| 6498 | Efs | NM_010112.4 | chr14:54916542-54926788 | 6595 | Elf3 | NM_001163131.1 | chr1:135253673-135258472 |

Fig.21 - 35

| | | | | | | | |
|---|---|---|---|---|---|---|---|
| 6596 | Elf4 | NM_019680.2 | chrX:48411048-48463132 | 6693 | Enthd2 | NM_183137.2 | chr11:120090521-120098731 |
| 6597 | Elf5 | NM_001145813.1 | chr2:103412097-103450988 | 6694 | Entpd1 | NM_009848.4 | chr19:40659769-40741602 |
| 6598 | Elfn1 | NM_175522.3 | chr5:139907942-139974724 | 6695 | Entpd2 | NM_009849.2 | chr2:25395873-25401323 |
| 6599 | Elfn2 | NM_183141.2 | chr15:78670006-78718113 | 6696 | Entpd3 | NM_178676.4 | chr9:120539817-120568326 |
| 6600 | Elk1 | NM_007922.5 | chrX:20933394-20950608 | 6697 | Entpd4 | NM_026174.3 | chr14:69337150-69584992 |
| 6601 | Elk3 | NM_001282967.1 | chr10:93247415-93311159 | 6698 | Entpd5 | NM_001026214.2 | chr12:84373875-84409029 |
| 6602 | Elk4 | NM_007923.2 | chr1:132007604-132025684 | 6699 | Entpd6 | NM_172117.5 | chr2:150749080-150771674 |
| 6603 | Ell | NM_007924.2 | chr8:70539674-70592858 | 6700 | Entpd7 | NM_053103.5 | chr19:43689688-43733853 |
| 6604 | Ell2 | NM_138953.2 | chr13:75707483-75772358 | 6701 | Entpd8 | NM_028093.1 | chr2:25080322-25085719 |
| 6605 | Ell3 | NM_145973.2 | chr2:121439026-121442601 | 6702 | Env2 | NM_175009.3 | chr15:44428110-44437685 |
| 6606 | Elmo1 | NM_080288.2 | chr13:20090506-20608353 | 6703 | Eogt | NM_175313.2 | chr6:97110943-97148883 |
| 6607 | Elmo2 | NM_080287.2 | chr2:165288030-165326479 | 6704 | Eomes | NM_001164789.1 | chr9:118478188-118486132 |
| 6608 | Elmo3 | NM_172760.3 | chr8:105305600-105310623 | 6705 | Ep300 | NM_177821.6 | chr15:81586213-81652077 |
| 6609 | Elmod1 | NM_177769.4 | chr9:53911459-53975361 | 6706 | Ep400 | NM_029337.2 | chr5:110664372-110770717 |
| 6610 | Elmod2 | NM_001170591.1 | chr8:83312631-83332486 | 6707 | Epas1 | NM_010137.3 | chr17:86753863-86833410 |
| 6611 | Elmod3 | NM_001253692.1 | chr6:72565921-72598413 | 6708 | Epb4.1 | NM_001128606.1 | chr4:131923428-132049078 |
| 6612 | Elmsan1 | NM_001163501.1 | chr12:84148173-84218881 | 6709 | Epb4.1l1 | NM_001006664.3 | chr2:156420487-156543214 |
| 6613 | Eln | NM_007925.4 | chr5:134702594-134747323 | 6710 | Epb4.1l2 | NM_001199265.1 | chr10:25350797-25525518 |
| 6614 | Elof1 | NM_170777.3 | chr9:22112986-22114169 | 6711 | Epb4.1l3 | NM_013813.1 | chr17:69156809-69289987 |
| 6615 | Elovl1 | NM_001039175.2 | chr4:118428092-118432952 | 6712 | Epb4.1l4a | NM_013512.2 | chr18:33796326-34007206 |
| 6616 | Elovl2 | NM_019423.2 | chr3:41182381-41220403 | 6713 | Epb4.1l4b | NM_019427.2 | chr4:57061725-57143155 |
| 6617 | Elovl3 | NM_007703.2 | chr19:46131898-46135694 | 6714 | Epb4.1l5 | NM_001113416.1 | chr1:119594823-119649000 |
| 6618 | Elovl4 | NM_148941.2 | chr9:83778691-83806305 | 6715 | Epb4.2 | NM_013513.3 | chr2:121017890-121036877 |
| 6619 | Elovl5 | NM_134255.3 | chr9:77917364-77984519 | 6716 | Epc1 | NM_001276350.1 | chr18:6438891-6490857 |
| 6620 | Elovl6 | NM_130450.2 | chr3:129532385-129638493 | 6717 | Epc2 | NM_172683.4 | chr2:49451485-49551609 |
| 6621 | Elovl7 | NM_029001.5 | chr13:108214403-108287107 | 6718 | Epcam | NM_008532.2 | chr17:87635978-87651127 |
| 6622 | Elp2 | NM_021448.2 | chr18:24603960-24638830 | 6719 | Epdr1 | NM_134065.4 | chr13:19591707-19619830 |
| 6623 | Elp3 | NM_001253812.1 | chr14:65530445-65593112 | 6720 | Epg5 | NM_001195633.1 | chr18:77938466-78035027 |
| 6624 | Elp4 | NM_023876.4 | chr2:105697319-105904564 | 6721 | Epgn | NM_053087.2 | chr5:91027516-91035212 |
| 6625 | Elp5 | NM_001253700.1 | chr11:69968225-69980330 | 6722 | Eps2 | NM_023580.4 | chr6:42358486-42373268 |
| 6626 | Elp6 | NM_001081381.1 | chr9:110305191-110322102 | 6723 | Epha1 | NM_001256432.1 | chr4:124881784-124917800 |
| 6627 | Eltd1 | NM_133222.3 | chr3:151437881-151545081 | 6724 | Epha2 | NM_010139.3 | chr4:141301220-141329384 |
| 6628 | Emb | NM_010330.4 | chr13:117220572-117274415 | 6725 | Epha3 | NM_010140.3 | chr16:63545217-63864157 |
| 6629 | Emc1 | NM_001039200.2 | chr4:139352586-139378735 | 6726 | Epha4 | NM_007936.3 | chr1:77367184-77515088 |
| 6630 | Emc10 | NM_197991.2 | chr7:44489987-44496513 | 6727 | Epha5 | NM_007937.3 | chr5:84054764-84417382 |
| 6631 | Emc2 | NM_025736.2 | chr15:43477228-43527777 | 6728 | Epha6 | NM_007938.2 | chr16:59653482-60605931 |
| 6632 | Emc3 | NM_175101.3 | chr6:113514886-113531838 | 6729 | Epha7 | NM_001122889.1 | chr4:28813144-28947453 |
| 6633 | Emc4 | NM_026519.3 | chr2:112363018-112368027 | 6730 | Epha8 | NM_007939.2 | chr4:136929418-136956816 |
| 6634 | Emc6 | NM_001168470.1 | chr11:73175502-73177008 | 6731 | Ephb1 | NM_001168236.1 | chr9:101922127-102354693 |
| 6635 | Emc7 | NM_133749.2 | chr2:112455024-112467436 | 6732 | Ephb2 | NM_001290753.2 | chr4:136647540-136836012 |
| 6636 | Emc8 | NM_010926.5 | chr8:120653913-120668112 | 6733 | Ephb3 | NM_010143.1 | chr16:21204794-21223304 |
| 6637 | Emc9 | NM_033146.1 | chr14:55581523-55585254 | 6734 | Ephb4 | NM_001159571.1 | chr5:137350108-137374522 |
| 6638 | Emcn | NM_001163522.1 | chr3:137941077-137981069 | 6735 | Ephb6 | NM_001146351.1 | chr6:41605481-41620507 |
| 6639 | Emd | NM_007927.3 | chrX:74254686-74257893 | 6736 | Ephx1 | NM_010145.3 | chr1:180989555-181017569 |
| 6640 | Eme1 | NM_177752.4 | chr11:94645001-94653754 | 6737 | Ephx2 | NM_001271402.1 | chr14:66084371-66124522 |
| 6641 | Eme2 | NM_001163102.1 | chr17:24892151-24895087 | 6738 | Ephx3 | NM_001033163.3 | chr17:32183769-32189483 |
| 6642 | Emg1 | NM_013516.2 | chr6:124704369-124712178 | 6739 | Ephx4 | NM_001001804.2 | chr5:107403512-107430031 |
| 6643 | Emid1 | NM_080595.2 | chr11:5106265-5152222 | 6740 | Epm2a | NM_010146.2 | chr10:11343444-11457477 |
| 6644 | Emilin1 | NM_133918.2 | chr5:30913785-30921273 | 6741 | Epm2aip1 | NM_175286.4 | chr9:111271844-111279091 |
| 6645 | Emilin2 | NM_145158.3 | chr17:71252175-71310965 | 6742 | Epn1 | NM_001252454.1 | chr7:5080234-5098178 |
| 6646 | Emilin3 | NM_001291145.1 | chr2:160906437-160912339 | 6743 | Epn2 | NM_001252188.1 | chr11:61517248-61579687 |
| 6647 | Eml1 | NM_001043335.1 | chr12:108422815-108539564 | 6744 | Epn3 | NM_027984.3 | chr11:94489598-94499974 |
| 6648 | Eml2 | NM_001168620.1 | chr7:19181169-19206482 | 6745 | Epo | NM_007942.2 | chr5:137483019-137485816 |
| 6649 | Eml3 | NM_144872.1 | chr19:8929693-8941582 | 6746 | Epor | NM_010149.3 | chr9:21958898-21963576 |
| 6650 | Eml4 | NM_001143461.1 | chr17:83350930-83480359 | 6747 | Eppin | NM_029325.2 | chr2:164588342-164593571 |
| 6651 | Eml5 | NM_010813911 | chr12:98786603-98901484 | 6748 | Eppk1 | NM_144848.2 | chr15:76101487-76120195 |
| 6652 | Eml6 | NM_146016.2 | chr11:29743050-30026033 | 6749 | Eprs | NM_029735.1 | chr1:185363094-185428355 |
| 6653 | Emp1 | NM_001288627.1 | chr6:135367492-135383173 | 6750 | Eps15 | NM_001159964.1 | chr4:109343055-109387816 |
| 6654 | Emp2 | NM_007929.2 | chr16:10281748-10313968 | 6751 | Eps15l1 | NM_001122832.1 | chr8:72377416-72421474 |
| 6655 | Emp3 | NM_001146346.1 | chr7:45915022-45920849 | 6752 | Eps8 | NM_001271587.1 | chr6:137477244-137571009 |
| 6656 | Emr1 | NM_010130.4 | chr17:57358685-57483529 | 6753 | Eps8l1 | NM_001290416.1 | chr7:4464848-4480487 |
| 6657 | Emr4 | NM_139138.3 | chr17:55749983-55853662 | 6754 | Eps8l2 | NM_133191.2 | chr7:141339001-141363016 |
| 6658 | Emx1 | NM_010131.3 | chr6:85487974-85204463 | 6755 | Eps8l3 | NM_133867.2 | chr3:107877229-107892900 |
| 6659 | Emx2 | NM_010132.2 | chr19:59458689-59465357 | 6756 | Epsti1 | NM_029495.2 | chr14:77904238-78002656 |
| 6660 | Emx2os | NR_002863.2 | chr19:59425169-59458635 | 6757 | Ept1 | NM_027652.2 | chr5:30232617-30272430 |
| 6661 | En1 | NM_010133.2 | chr1:120602486-120607991 | 6758 | Epx | NM_007946.2 | chr11:87863997-87875536 |
| 6662 | En2 | NM_010134.3 | chr5:28165695-28172166 | 6759 | Epyc | NM_007884.2 | chr10:97644067-97681900 |
| 6663 | Enah | NM_001083120.2 | chr1:181896385-182019980 | 6760 | Eqtn | NM_001290623.1 | chr4:94907266-94928843 |
| 6664 | Enam | NM_017468.3 | chr5:88487974-88506049 | 6761 | Eral1 | NM_022313.2 | chr11:78073375-78080383 |
| 6665 | Enc1 | NM_007930.4 | chr13:97241104-97253040 | 6762 | Erap1 | NM_030711.4 | chr13:74639871-74691875 |
| 6666 | Endod1 | NM_028013.3 | chr9:14353989-14381242 | 6763 | Eras | NM_181548.2 | chrX:7924275-7928607 |
| 6667 | Endog | NM_007931.1 | chr2:30171523-30174069 | 6764 | Erbb2 | NM_001003817.1 | chr11:98412483-98437716 |
| 6668 | Endou | NM_001168693.1 | chr15:97711018-97731405 | 6765 | Erbb2ip | NM_001005868.2 | chr13:103818788-103920586 |
| 6669 | Endov | NM_001164636.1 | chr11:119491346-119511446 | 6766 | Erbb3 | NM_010153.1 | chr10:128569367-128589501 |
| 6670 | Eng | NM_001146348.1 | chr2:32646594-32682669 | 6767 | Erbb4 | NM_010154.2 | chr1:68022186-69108059 |
| 6671 | Engase | NM_172573.2 | chr11:118476959-118489198 | 6768 | Erc1 | NM_053204.2 | chr6:119570795-119848150 |
| 6672 | Enho | NM_027147.1 | chr4:41638143-41640302 | 6769 | Erc2 | NM_177814.4 | chr14:27622441-28478537 |
| 6673 | Enkd1 | NM_198299.1 | chr8:105703651-105708168 | 6770 | Ercc1 | NM_001127324.1 | chr7:19345070-19354830 |
| 6674 | Enkur | NM_027728.2 | chr2:21180730-21205365 | 6771 | Ercc2 | NM_007949.4 | chr7:19382038-19395692 |
| 6675 | Eno1 | NM_023119.2 | chr4:150237196-150248873 | 6772 | Ercc3 | NM_133658.1 | chr18:32240330-32270147 |
| 6676 | Eno1b | NM_001025388.1 | chr4:48045334-150248873 | 6773 | Ercc4 | NM_015769.2 | chr16:13109736-13152009 |
| 6677 | Eno2 | NM_013509.3 | chr6:124760052-124769673 | 6774 | Ercc5 | NM_011729.2 | chr1:44147743-44181260 |
| 6678 | Eno3 | NM_001136062.2 | chr11:70657175-70662513 | 6775 | Ercc6 | NM_001081221.1 | chr14:32513520-32580989 |
| 6679 | Eno4 | NM_178689.4 | chr19:58943424-58971421 | 6776 | Ercc6l | NM_146235.3 | chrX:102142819-102157091 |
| 6680 | Enoph1 | NM_001009993-100068765 | | 6777 | Ercc6l2 | NM_001013608.2 | chr13:63815319-63900301 |
| 6681 | Enox1 | NM_001253759.1 | chr14:77136762-77721763 | 6778 | Ercc8 | NM_028042.3 | chr13:108158787-108194981 |
| 6682 | Enox2 | NM_001271447.1 | chrX:49009706-49288242 | 6779 | Erdr1 | NM_133362.2 | chrY:90785441-90816465 |
| 6683 | Enpep | NM_007934.3 | chr3:129269176-129332749 | 6780 | Ereg | NM_007950.2 | chr5:91074616-91093649 |
| 6684 | Enpp1 | NM_008813.4 | chr10:24637913-24712159 | 6781 | Erf | NM_010155.3 | chr7:25242559-25250758 |
| 6685 | Enpp2 | NM_001136077.3 | chr15:54838900-54920146 | 6782 | Erg | NM_133659.3 | chr16:95369168-95530365 |
| 6686 | Enpp3 | NM_134005.2 | chr10:24773813-24836195 | 6783 | Ergic1 | NM_026170.2 | chr17:26563511-26656933 |
| 6687 | Enpp4 | NM_199016.2 | chr17:44096309-44105808 | 6784 | Ergic2 | NM_001286560.1 | chr6:148179317-148212374 |
| 6688 | Enpp5 | NM_177847.4 | chr17:44086561 | 6785 | Ergic3 | NM_025516.4 | chr2:156008124-156018279 |
| 6689 | Enpp6 | NM_177304.3 | chr8:46986924-47094895 | 6786 | Erh | NM_007951.3 | chr12:80634022-80643861 |
| 6690 | Enpp7 | NM_001030291.1 | chr11:118968187-118992841 | 6787 | Eri1 | NM_026067.3 | chr8:35465264-35495593 |
| 6691 | Ensa | NM_001026212.1 | chr3:95624979-95630493 | 6788 | Eri2 | NM_027698.5 | chr7:119783825-119794058 |
| 6692 | Enthd1 | NM_001163189.1 | chr15:80452239-80560470 | 6789 | Eri3 | NM_001285899.1 | chr4:117550364-117674297 |

Fig. 21 - 36

| | | | | | | | | |
|---|---|---|---|---|---|---|---|---|
| 6790 | Erich1 | NM_001034862.2 | chr8:14027564-14090327 | 6887 | Exo1 | NM_012012.4 | chr1:175880777-175911396 |
| 6791 | Erich2 | NM_025744.2 | chr2:70508818-70540884 | 6888 | Exo5 | NM_001160043.1 | chr4:120921201-120925005 |
| 6792 | Erich3 | NM_175176.1 | chr3:154711132-154749012 | 6889 | Exoc1 | NM_001289770.1 | chr5:76529310-76570298 |
| 6793 | Erich4 | NM_001039243 | chr7:25614620-25615892 | 6890 | Exoc2 | NM_025588.2 | chr13:30813917-30974047 |
| 6794 | Erich5 | NM_173421 | chr15:34453311-34473892 | 6891 | Exoc3 | NM_177333.3 | chr13:74169804-74208700 |
| 6795 | Erich6 | NM_001081262.1 | chr3:58616299-58637207 | 6892 | Exoc3l | NM_177788.2 | chr8:105289923-105296098 |
| 6796 | Erlec1 | NM_025745.2 | chr11:30929783-30954131 | 6893 | Exoc3l4 | NM_001289487.1 | chr12:111417429-111431680 |
| 6797 | Erlin1 | NM_001164359.1 | chr19:44034942-44069775 | 6894 | Exoc4 | NM_009148 | chr6:33249149-33972930 |
| 6798 | Erlin2 | NM_153592 | chr8:27023798-27039435 | 6895 | Exoc5 | NM_207214 | chr14:49012143-49066867 |
| 6799 | Ermap | NM_013848.1 | chr4:119175456-119190011 | 6896 | Exoc6 | NM_175353.2 | chr19:37550417-37683249 |
| 6800 | Ermard | NM_001034891.3 | chr17:15053058-15064232 | 6897 | Exoc6b | NM_177077.2 | chr6:84618485-85069513 |
| 6801 | Ermn | NM_029972.3 | chr2:58045114-58052752 | 6898 | Exoc7 | NM_001162872.1 | chr11:116287997-116306738 |
| 6802 | Ermp1 | NM_001081213.1 | chr19:29609882-29648420 | 6899 | Exoc8 | NM_198103.2 | chr8:124890298-124897705 |
| 6803 | Ern1 | NM_023913.2 | chr11:106397619-106487796 | 6900 | Exog | NM_001172136.1 | chr9:119444922-119465518 |
| 6804 | Ern2 | NM_012016.2 | chr7:122169892-122186216 | 6901 | Exosc1 | NM_001164561.1 | chr19:41922979-41933314 |
| 6805 | Ero1l | NM_015774.3 | chr14:45283086-45318572 | 6902 | Exosc10 | NM_016699.2 | chr4:148558426-148582400 |
| 6806 | Ero1lb | NM_026184.2 | chr13:12565882-12609528 | 6903 | Exosc2 | NM_144886.2 | chr2:31670736-31681307 |
| 6807 | Erp27 | NM_026983.2 | chr6:136907386-136922180 | 6904 | Exosc3 | NM_025513.3 | chr4:45316629-45320603 |
| 6808 | Erp29 | NM_026129.2 | chr5:121444752-121452474 | 6905 | Exosc4 | NM_175399.4 | chr15:76327398-76330670 |
| 6809 | Erp44 | NM_029572.2 | chr4:48193330-48279583 | 6906 | Exosc5 | NM_138586.3 | chr7:25659152-25668032 |
| 6810 | Errfi1 | NM_133753.1 | chr4:150855090-150868880 | 6907 | Exosc6 | NM_028274.4 | chr8:111056338-111057664 |
| 6811 | Ertv3 | NM_001166206.1 | chr2:131853677-131859747 | 6908 | Exosc7 | NM_001081188.1 | chr9:123113230-123136129 |
| 6812 | Esam | NM_027102.3 | chr9:37528088-37538319 | 6909 | Exosc8 | NM_001163570.1 | chr3:54728678-54735364 |
| 6813 | Esco1 | NM_001081222.1 | chr18:10566513-10610352 | 6910 | Exosc9 | NM_019393.2 | chr3:36952605-36985727 |
| 6814 | Esco2 | NM_028039.2 | chr14:65819026-65833969 | 6911 | Exph5 | NM_176846.3 | chr9:53301689-53381158 |
| 6815 | Esd | NM_001285423.1 | chr14:74732296-74750765 | 6912 | Ext1 | NM_010162.2 | chr15:53068260-53346183 |
| 6816 | Esf1 | NM_001081090.1 | chr2:140119880-140170658 | 6913 | Ext2 | NM_010163.3 | chr2:93695630-93822568 |
| 6817 | Esm1 | NM_023612.3 | chr13:113209658-113218104 | 6914 | Extl1 | NM_019578.2 | chr4:134356872-134372547 |
| 6818 | Esp1 | NM_001038500.2 | chr17:40727119-40731782 | 6915 | Extl2 | NM_001165141 | chr3:116008296-116029016 |
| 6819 | Esp15 | NM_001244651.1 | chr17:39640956-39645667 | 6916 | Extl3 | NM_018788.3 | chr14:65052058-65098106 |
| 6820 | Esp16 | NM_001255977.1 | chr17:39536141-39540847 | 6917 | Eya1 | NM_001252192.1 | chr1:14168957-14310199 |
| 6821 | Esp18 | NM_001244763.1 | chr17:39406358-39410992 | 6918 | Eya2 | NM_001271962.1 | chr2:165630344-165771727 |
| 6822 | Esp23 | NM_001177582.1 | chr17:39073690-39077037 | 6919 | Eya3 | NM_010166.3 | chr4:132639045-132724765 |
| 6823 | Esp24 | NM_001265066.1 | chr17:39036694-39040227 | 6920 | Eya4 | NM_010167.4 | chr10:23104167-23349903 |
| 6824 | Esp3 | NM_001251916.1 | chr17:40632074-40637060 | 6921 | Ezh1 | NM_007970.3 | chr11:101191114-101226463 |
| 6825 | Esp31 | NM_001177586.1 | chr17:38639446-38645653 | 6922 | Ezh2 | NM_001146689.1 | chr6:47530273-47595030 |
| 6826 | Esp34 | NM_001177589.1 | chr17:38554191-38560621 | 6923 | Ezr | NM_009510.2 | chr17:67381130-67827780 |
| 6827 | Esp36 | NM_001177587.1 | chr17:38416473-38420185 | 6924 | F10 | NM_001242368.1 | chr8:130037307-130056676 |
| 6828 | Esp38 | NM_001256015.1 | chr17:39950519-39955287 | 6925 | F11 | NM_028066.2 | chr8:45241167-45262631 |
| 6829 | Esp4 | NM_001177583.1 | chr17:40598953-40602617 | 6926 | F11r | NM_172647.2 | chr1:171437560-171464593 |
| 6830 | Esp5 | NM_001287194.1 | chr17:40574710-40579549 | 6927 | F12 | NM_021489.3 | chr13:55417957-55426804 |
| 6831 | Esp6 | NM_001177579.1 | chr17:40561506-40565624 | 6928 | F13a1 | NM_001166391.1 | chr13:38867177-37050244 |
| 6832 | Esp6-esp5 | NM_001287195.1 | chr17:40561506-40579549 | 6929 | F13b | NM_031164.2 | chr1:139501706-139523756 |
| 6833 | Esp8 | NM_001177584.1 | chr17:40520021-40530702 | 6930 | F2 | NM_010168.3 | chr2:91625319-91636457 |
| 6834 | Espl1 | NM_001014976.2 | chr15:102296292-102324356 | 6931 | F2r | NM_010169.3 | chr13:95601788-95618433 |
| 6835 | Espn | NM_019585.3 | chr4:152120875-152128925 | 6932 | F2rl1 | NM_007974.4 | chr13:95511729-95525240 |
| 6836 | Espnl | NM_001033292 | chr1:91320474-91348303 | 6933 | F2rl2 | NM_010170.4 | chr13:95696919-95702768 |
| 6837 | Esr1 | NM_007956.5 | chr10:4611988-5005633 | 6934 | F2rl3 | NM_007975.3 | chr8:72761879-72763885 |
| 6838 | Esr2 | NM_010157.3 | chr12:76120418-76177259 | 6935 | F3 | NM_010171.3 | chr3:121723636-121735052 |
| 6839 | Esrp1 | NM_001290383.1 | chr4:11331932-11386781 | 6936 | F420014N23Rik | NR_045715.1 | chr10:127195248-127202643 |
| 6840 | Esrp2 | NM_176838.2 | chr8:106131182-106136974 | 6937 | F5 | NM_007976.3 | chr1:164151834-164220277 |
| 6841 | Esrra | NM_007953.2 | chr19:6910976-6921808 | 6938 | F630028O10Rik | NR_030718.1 | chrX:96239925-96243642 |
| 6842 | Esrrb | NM_001159500.1 | chr12:86361116-86521628 | 6939 | F630042O09Rik | NR_033540.1 | chr13:67278593-67283361 |
| 6843 | Esrrg | NM_011935.3 | chr1:187609005-188214884 | 6940 | F630111I10Rik | NR_045641.1 | chr9:59146295-59153628 |
| 6844 | Esx1 | NM_007156.4 | chrX:137115396-137120326 | 6941 | F630206G17Rik | NR_045876.1 | chr11:45880882-45842878 |
| 6845 | Esyt1 | NM_011843.2 | chr10:128510249-128525859 | 6942 | F7 | NM_010172.4 | chr8:13026033-13035805 |
| 6846 | Esyt2 | NM_028731.5 | chr12:116281221-116373098 | 6943 | F730035M05Rik | NR_045174.1 | chr12:70227840-70234165 |
| 6847 | Esyt3 | NM_177775.3 | chr9:99309966-99358530 | 6944 | F730043M19Rik | NR_015602.2 | chr12:33111710-33147586 |
| 6848 | Etaa1 | NM_026576.3 | chr11:17938748-17953875 | 6945 | F8 | NM_001161373.1 | chrX:75172714-75380041 |
| 6849 | Etd | NR_034074.1 | chrX:53434917-53443576 | 6946 | F830021J21Rik | NR_033558.1 | chr10:43593426-43630913 |
| 6850 | Etf1 | NM_144866.2 | chr18:34902784-34932003 | 6947 | F830160B08Rik | NM_001101475.2 | chr18:60293379-60303016 |
| 6851 | Etfa | NM_145615.4 | chr9:55454435-55512243 | 6948 | F830045P16Rik | NM_177653.3 | chr2:129458358-129536602 |
| 6852 | Etfb | NM_026695.4 | chr7:43444071-43457800 | 6949 | F8a | NM_007978.3 | chrX:73228305-73230795 |
| 6853 | Etfdh | NM_025794.2 | chr3:79603787-79628767 | 6950 | F9 | NM_007979.2 | chrX:59999463-60030760 |
| 6854 | Ethe1 | NM_023154.3 | chr7:24587542-24608926 | 6951 | F930015N05Rik | NR_028445.1 | chr1:64433134-64436674 |
| 6855 | Etl4 | NM_001081006.1 | chr2:20289912-20810535 | 6952 | Fa2h | NM_178086.3 | chr8:111345137-111393821 |
| 6856 | Etnk1 | NM_029250.2 | chr6:143167229-143208547 | 6953 | Faah | NM_010173.4 | chr4:115996655-116017902 |
| 6857 | Etnk2 | NM_175443.2 | chr1:133363871-133380319 | 6954 | Fabp1 | NM_017399.4 | chr6:71199887-71205023 |
| 6858 | Etnppl | NM_001163587.1 | chr3:130617447-130635750 | 6955 | Fabp12 | NM_029310.1 | chr3:10244208-10301183 |
| 6859 | Etohd2 | NR_015349.2 | chr13:59769965-59773680 | 6956 | Fabp2 | NM_007980.3 | chr3:122895671-121899506 |
| 6860 | Etohi1 | NM_001177083.2 | chr2:178023283-178035859 | 6957 | Fabp3 | NM_010174.1 | chr4:130308777-130315463 |
| 6861 | Ets1 | NM_001038642.1 | chr9:32696041-32757820 | 6958 | Fabp4 | NM_024406.2 | chr3:10204342-10208576 |
| 6862 | Ets2 | NM_011809.3 | chr16:95702406-95721049 | 6959 | Fabp5 | NM_001272097.1 | chr3:10012584-10016610 |
| 6863 | Etv1 | NM_001163154.1 | chr12:38783710-38868215 | 6960 | Fabp6 | NM_008375.2 | chr11:43596039-43601562 |
| 6864 | Etv2 | NM_007959.2 | chr7:30633615-30635852 | 6961 | Fabp7 | NM_021272.3 | chr10:57784922-57788450 |
| 6865 | Etv3 | NM_001083318.2 | chr3:87525577-87540158 | 6962 | Fabp9 | NM_011598.3 | chr3:10193623-10197283 |
| 6866 | Etv4 | NM_008815.3 | chr11:101769741-101785310 | 6963 | Fadd | NM_010175.5 | chr7:144578322-144582436 |
| 6867 | Etv5 | NM_023794.2 | chr16:22381312-22439570 | 6964 | Fads1 | NM_146094.2 | chr19:10182887-10196872 |
| 6868 | Etv6 | NM_007961.4 | chr6:134035699-134270147 | 6965 | Fads2 | NM_019699.1 | chr19:10064163-10101503 |
| 6869 | EU599041 | NM_001177525.1 | chr7:43214038-43226842 | 6966 | Fads3 | NM_021890.3 | chr19:10041547-10059671 |
| 6870 | Eva1a | NM_145570.2 | chr6:82041627-82093099 | 6967 | Fads6 | NM_178035.4 | chr11:115283386-115297546 |
| 6871 | Eva1b | NM_172145.3 | chr4:126148002-126149874 | 6968 | Faf1 | NM_007983.2 | chr4:109676626-109963960 |
| 6872 | Eva1c | NM_001199210.1 | chr16:90830858-90904885 | 6969 | Faf2 | NM_178397.3 | chr13:54621783-54664063 |
| 6873 | Evc | NM_021292.2 | chr5:37299170-37336881 | 6970 | Fah | NM_010176.4 | chr7:84585158-84605942 |
| 6874 | Evc2 | NM_145920.3 | chr5:37338477-37425054 | 6971 | Fahd1 | NM_023480.2 | chr17:24848895-24850302 |
| 6875 | Evi2a | NM_001033711.3 | chr11:79526560-79530609 | 6972 | Fahd2a | NM_029629.2 | chr2:127436214-127444565 |
| 6876 | Evi2a-evi2b | NM_146023.4 | chr11:79513384-79530609 | 6973 | Faim | NM_001122851.1 | chr9:98986372-99002019 |
| 6877 | Evi2b | NM_001077496.1 | chr11:79513384-79523762 | 6974 | Faim2 | NM_001038658.2 | chr15:99497004-99528165 |
| 6878 | Evi5 | NM_077964.2 | chr5:107744794-107875107 | 6975 | Faim3 | NM_026976.2 | chr1:130865776-130880790 |
| 6879 | Evi5l | NM_001039578.3 | chr8:4166566-4193701 | 6976 | Fam101a | NM_001038443.2 | chr5:125003474-125012547 |
| 6880 | Evl | NM_001163394.1 | chr12:108554719-108688515 | 6977 | Fam101b | NM_029688.1 | chr11:76019194-76027782 |
| 6881 | Evpl | NM_025276.3 | chr11:116220558-116238091 | 6978 | Fam102a | NM_153560.4 | chr2:32535858-32569750 |
| 6882 | Evx1 | NM_007966.4 | chr6:52313497-52318378 | 6979 | Fam102b | NM_001163567.1 | chr3:108970996-109027607 |
| 6883 | Evx2 | NM_007967.3 | chr2:74652990-74659557 | 6980 | Fam103a1 | NM_025997.2 | chr7:81762952-81769490 |
| 6884 | Ewsr1 | NM_001283061.1 | chr11:5069686-5099088 | 6981 | Fam104a | NM_138584.5 | chr11:113661318-113684151 |
| 6885 | Exd1 | NM_172857.2 | chr2:119519403-119547627 | 6982 | Fam104a23 | NM_001242423.1 | chr15:27655070-27681542 |
| 6886 | Exd2 | NM_133798.3 | chr12:80463094-80498135 | 6983 | Fam107a | NM_183187.3 | chr14:8296277-8309776 |

| | | | | | | | |
|---|---|---|---|---|---|---|---|
| 7178 | Fam69b | NM_019833.3 | chr2:26628456-26636497 | 7275 | Fbxl20 | NM_028149.1 | chr11:98082553-98149616 |
| 7179 | Fam69c | NM_173770.4 | chr18:84720241-84740436 | 7276 | Fbxl21 | NM_178674.4 | chr13:56522507-56537786 |
| 7180 | Fam71a | NM_001109759.1 | chr1:191162583-191164817 | 7277 | Fbxl22 | NM_175206.4 | chr9:66508458-66514593 |
| 7181 | Fam71b | NM_001013783.2 | chr1:46404727-46407985 | 7278 | Fbxl3 | NM_015822.2 | chr14:103080238-103099509 |
| 7182 | Fam71d | NM_027597.4 | chr12:78691534-78734519 | 7279 | Fbxl4 | NM_172988.4 | chr4:22357942-22434091 |
| 7183 | Fam71e1 | NM_028169.1 | chr7:44496587-44501134 | 7280 | Fbxl5 | NM_001159963.1 | chr5:43744617-43782149 |
| 7184 | Fam71e2 | NM_172895.3 | chr7:4753225-4771270 | 7281 | Fbxl6 | NM_013909.2 | chr15:76535727-76538746 |
| 7185 | Fam71f1 | NM_001289663.1 | chr6:29319139-29336022 | 7282 | Fbxl7 | NM_176959.3 | chr15:26540458-26895564 |
| 7186 | Fam71f2 | NM_001101486.1 | chr6:29281140-29290676 | 7283 | Fbxl8 | NM_015821.2 | chr8:105264647-105269326 |
| 7187 | Fam72a | NM_175382.3 | chr1:131527988-131539872 | 7284 | Fbxo10 | NM_001024142.1 | chr4:45034247-45084604 |
| 7188 | Fam73a | NM_001162375.1 | chr3:152273459-152340407 | 7285 | Fbxo11 | NM_001081034.1 | chr17:87990858-88066285 |
| 7189 | Fam73b | NM_001242698.1 | chr2:30364232-30385519 | 7286 | Fbxo15 | NM_015798.3 | chr18:84935024-84981392 |
| 7190 | Fam76a | NM_001163792.1 | chr4:132899212-132922551 | 7287 | Fbxo16 | NM_015795.1 | chr14:65266700-65321502 |
| 7191 | Fam76b | NM_176836.3 | chr9:13827726-13846522 | 7288 | Fbxo17 | NM_015796.2 | chr7:28716789-28738140 |
| 7192 | Fam78a | NM_175511.4 | chr2:32066884-32083705 | 7289 | Fbxo18 | NM_015792.1 | chr2:11742572-11777527 |
| 7193 | Fam78b | NM_001160261.1 | chr1:167001416-167091302 | 7290 | Fbxo2 | NM_176848.1 | chr4:148160667-148166417 |
| 7194 | Fam81a | NM_029784.2 | chr9:70089309-70141557 | 7291 | Fbxo21 | NM_145564.3 | chr5:117976769-118010191 |
| 7195 | Fam83a | NM_173862.2 | chr15:57985902-58010702 | 7292 | Fbxo22 | NM_028049.2 | chr9:55208934-55224433 |
| 7196 | Fam83b | NM_001045518.1 | chr9:76490704-76545804 | 7293 | Fbxo24 | NM_027708.1 | chr5:137612504-137625078 |
| 7197 | Fam83c | NM_027788.2 | chr2:155829182-155834854 | 7294 | Fbxo25 | NM_025785.2 | chr8:13907805-13940521 |
| 7198 | Fam83d | NM_027975.2 | chr2:158768098-158786637 | 7295 | Fbxo27 | NM_001163702.1 | chr7:28693143-28699337 |
| 7199 | Fam83e | NM_001033170.4 | chr7:45721219-45729492 | 7296 | Fbxo28 | NM_175127.2 | chr1:182313101-182341606 |
| 7200 | Fam83f | NM_145986.2 | chr15:80671846-80700425 | 7297 | Fbxo3 | NM_020593.2 | chr2:104027798-104055127 |
| 7201 | Fam83g | NM_178618.3 | chr11:61684409-61709950 | 7298 | Fbxo30 | NM_001168297.1 | chr10:11281586-11297969 |
| 7202 | Fam83h | NM_001162253.1 | chr15:76001091-76009498 | 7299 | Fbxo31 | NM_133785.4 | chr8:121549442-121578806 |
| 7203 | Fam84a | NM_029007.2 | chr12:14147597-14152038 | 7300 | Fbxo32 | NM_026346.3 | chr15:58175878-58214892 |
| 7204 | Fam84b | NM_001162926.1 | chr15:60818995-60825080 | 7301 | Fbxo33 | NM_001033156.4 | chr12:59200654-59219483 |
| 7205 | Fam86 | NM_027446.2 | chr16:5244154-5255956 | 7302 | Fbxo34 | NM_001146085.1 | chr14:47472560-47531962 |
| 7206 | Fam89a | NM_001081120.1 | chr8:124740256-124761809 | 7303 | Fbxo36 | NM_025386.3 | chr1:84839840-84900486 |
| 7207 | Fam89b | NM_023166.2 | chr19:5728086-5729666 | 7304 | Fbxo38 | NM_134136.3 | chr18:62504058-62548743 |
| 7208 | Fam92a | NM_026558.5 | chr4:12153141-12172015 | 7305 | Fbxo39 | NM_001009988.2 | chr11:72314443-72319419 |
| 7209 | Fam92b | NM_001033980.2 | chr8:120166396-120177469 | 7306 | Fbxo4 | NM_134099.2 | chr15:3963563-3979573 |
| 7210 | Fam96a | NM_026635.3 | chr9:66126610-66138988 | 7307 | Fbxo40 | NM_001073711.1 | chr16:36966072-36979136 |
| 7211 | Fam96b | NM_026753.2 | chr8:104639572-104641728 | 7308 | Fbxo41 | NM_001001160.3 | chr6:85469575-85502994 |
| 7212 | Fam98a | NM_133747.2 | chr17:75537086-75551946 | 7309 | Fbxo42 | NM_172518.3 | chr4:141147921-141204062 |
| 7213 | Fam98b | NM_026620.3 | chr2:117249736-117271540 | 7310 | Fbxo43 | NM_001108125.1 | chr15:36150059-36164884 |
| 7214 | Fam98c | NM_175478.023.1 | chr7:29152509-29156210 | 7311 | Fbxo44 | NM_001161853.1 | chr4:148152798-148169585 |
| 7215 | Fan1 | NM_177893.3 | chr7:64346757-64374095 | 7312 | Fbxo45 | NM_173439.2 | chr16:32230111-32247025 |
| 7216 | Fanca | NM_016925.3 | chr8:123268243-123318576 | 7313 | Fbxo46 | NM_175530.3 | chr7:19119858-19138261 |
| 7217 | Fancb | NM_001146081.1 | chrX:164980591-164997272 | 7314 | Fbxo47 | NM_001081435.1 | chr11:97854306-97884154 |
| 7218 | Fancc | NM_001042673.2 | chr13:63304708-63431745 | 7315 | Fbxo48 | NM_176982.2 | chr11:16951409-16954772 |
| 7219 | Fancd2 | NM_001033244.3 | chr6:113531681-113596285 | 7316 | Fbxo5 | NM_025995.2 | chr10:5799157-5805485 |
| 7220 | Fancd2os | NM_027633.3 | chr6:113596761-113600715 | 7317 | Fbxo6 | NM_001163704.1 | chr4:148149715-148151925 |
| 7221 | Fance | NM_001163819.1 | chr17:28313529-28326574 | 7318 | Fbxo7 | NM_153195.2 | chr10:86021928-86048328 |
| 7222 | Fancf | NM_001115087.1 | chr7:51860576-51862267 | 7319 | Fbxo8 | NM_015791.3 | chr8:56551133-56593939 |
| 7223 | Fancg | NM_001163233.1 | chr4:43002336-43010301 | 7320 | Fbxo9 | NM_001081490.2 | chr9:78081499-78109965 |
| 7224 | Fanci | NM_145946.2 | chr7:79392337-79450264 | 7321 | Fbxw10 | NM_001033669.2 | chr11:62847122-62877462 |
| 7225 | Fancl | NM_001277273.1 | chr11:26387083-26471683 | 7322 | Fbxw11 | NM_001271347.1 | chr11:32642554-32746814 |
| 7226 | Fancm | NM_178912.3 | chr12:65075605-65132058 | 7323 | Fbxw13 | NM_177598.3 | chr9:109179226-109195975 |
| 7227 | Fank1 | NM_025850.2 | chr7:133776899-133881532 | 7324 | Fbxw14 | NM_015793.2 | chr9:109271124-109287676 |
| 7228 | Fap | NM_007986.3 | chr2:62500935-62574021 | 7325 | Fbxw15 | NM_199036.2 | chr9:109552601-109568262 |
| 7229 | Far1 | NM_001285831.1 | chr7:113513833-113570888 | 7326 | Fbxw16 | NM_177070.3 | chr9:109432317-109449140 |
| 7230 | Far2 | NM_178797.3 | chr6:148047415-148182760 | 7327 | Fbxw17 | NM_175401.3 | chr13:50417876-50433769 |
| 7231 | Farp1 | NM_134082.3 | chr14:121035573-121283726 | 7328 | Fbxw18 | NM_001033794.3 | chr9:109676733-109702700 |
| 7232 | Farp2 | NM_145514.2 | chr1:93512103-93621976 | 7329 | Fbxw19 | NM_177703.3 | chr9:109478574-109495854 |
| 7233 | Fars2 | NM_001039189.2 | chr13:36117642-36537595 | 7330 | Fbxw2 | NM_001164768.1 | chr2:34804363-34823181 |
| 7234 | Farsa | NM_025648.3 | chr8:84856985-84869257 | 7331 | Fbxw20 | NM_001008428.3 | chr9:109217431-109234754 |
| 7235 | Farsb | NM_001258071.1 | chr1:78417957-78488897 | 7332 | Fbxw21 | NM_177069.3 | chr9:109139453-109162022 |
| 7236 | Fas | NM_001146708.1 | chr19:34290658-34309350 | 7333 | Fbxw22 | NM_001014395.2 | chr9:109378408-109404294 |
| 7237 | Fasl | NM_001205243.1 | chr1:161780691-161788493 | 7334 | Fbxw24 | NM_001013776.4 | chr9:109601115-109626059 |
| 7238 | Fasn | NM_007988.3 | chr11:120805957-120824547 | 7335 | Fbxw26 | NM_198674.2 | chr9:109717565-109746089 |
| 7239 | Fastk | NM_023229.2 | chr5:24441039-24445295 | 7336 | Fbxw28 | NM_001177419.1 | chr9:109322885-109339659 |
| 7240 | Fastkd1 | NM_177244.3 | chr2:69688823-69712606 | 7337 | Fbxw4 | NM_013907.2 | chr19:45378256-45660193 |
| 7241 | Fastkd2 | NM_172422.3 | chr1:63730624-63753385 | 7338 | Fbxw5 | NM_013908.4 | chr2:25500777-25505470 |
| 7242 | Fastkd3 | NM_027123.4 | chr13:68582247-68592279 | 7339 | Fbxw7 | NM_001177773.1 | chr3:84815576-84979198 |
| 7243 | Fastkd5 | NM_001146883.1 | chr2:130630027-130636027 | 7340 | Fbxw8 | NM_172721.2 | chr5:118064980-118155458 |
| 7244 | Fat1 | NM_001081286.2 | chr8:44950207-45052257 | 7341 | Fbxw9 | NM_026791.2 | chr8:85060118-85067120 |
| 7245 | Fat2 | NM_001029988.2 | chr11:55256809-55312257 | 7342 | Fcamr | NM_001170632.1 | chr1:130800901-130814740 |
| 7246 | Fat3 | NM_001080814.1 | chr9:15910192-16378231 | 7343 | Fcer1a | NM_019184.2 | chr1:173221270-173227229 |
| 7247 | Fat4 | NM_183221.3 | chr3:38886939-39011983 | 7344 | Fcer1g | NM_010185.4 | chr1:171229571-171234349 |
| 7248 | Fate1 | NR_003243.2 | chrX:52995085-71989046 | 7345 | Fcer2a | NM_001253737.1 | chr8:3681736-3690861 |
| 7249 | Fau | NM_001160239.2 | chr19:6057887-6059524 | 7346 | Fcf1 | NM_028632.2 | chr12:84970929-84983803 |
| 7250 | Faxc | NM_175234.4 | chr4:21931325-22001461 | 7347 | Fcgbp | NM_001122603.1 | chr7:28071236-28120864 |
| 7251 | Fbf1 | NM_172571.3 | chr11:116142284-116168178 | 7348 | Fcgr1 | NM_010186.5 | chr3:96282908-96293869 |
| 7252 | Fbf | NM_007991.3 | chr7:28169747-28179269 | 7349 | Fcgr2b | NM_001077157.1 | chr1:170960558-170976071 |
| 7253 | Fblm1 | NM_001163256.1 | chr4:141576061-141599924 | 7350 | Fcgr3 | NM_010188.5 | chr1:171051160-171059403 |
| 7254 | Fbll1 | NM_001004147.3 | chr11:35797379-35798884 | 7351 | Fcgr4 | NM_144559.2 | chr1:171018925-171029761 |
| 7255 | Fbln1 | NM_010180.2 | chr15:85260007-85286294 | 7352 | Fcgrt | NM_010189.3 | chr7:45092992-45103822 |
| 7256 | Fbln2 | NM_001081437.1 | chr6:91212763-91272540 | 7353 | Fcho1 | NM_028715.3 | chr8:71708386-71725681 |
| 7257 | Fbln5 | NM_011812.4 | chr12:101746564-101819119 | 7354 | Fcho2 | NM_172591.3 | chr13:98723405-98815449 |
| 7258 | Fbln7 | NM_024237.4 | chr2:128863931-128897034 | 7355 | Fchsd1 | NM_175684.4 | chr18:37957433-37969731 |
| 7259 | Fbn1 | NM_007993.2 | chr2:125300593-125506438 | 7356 | Fchsd2 | NM_001146010.1 | chr7:101108774-101284405 |
| 7260 | Fbn2 | NM_010181.2 | chr18:58008622-58209926 | 7357 | Fcna | NM_007995.3 | chr2:25624666-25627974 |
| 7261 | Fbp1 | NM_019395.3 | chr13:62864752-62888282 | 7358 | Fcnb | NM_010190.1 | chr2:28076478-28084878 |
| 7262 | Fbp2 | NM_007994.3 | chr13:62836884-62858370 | 7359 | Fcrl1 | NM_001136236.1 | chr3:87376386-87392133 |
| 7263 | Fbrs | NM_010183.1 | chr7:127485220-127491913 | 7360 | Fcrl5 | NM_001113238.1 | chr3:87435783-87500678 |
| 7264 | Fbrsl1 | NM_001142641.1 | chr5:110361753-110448503 | 7361 | Fcrl6 | NM_001164725.1 | chr1:172596639-172602553 |
| 7265 | Fbxl12 | NM_001002846.1 | chr9:20637748-20644767 | 7362 | Fcrla | NM_001160215.1 | chr1:170917593-170927583 |
| 7266 | Fbxl12os | NR_033729.1 | chr9:20607474-20617271 | 7363 | Fcrlb | NM_001029984.2 | chr1:170907272-170912941 |
| 7267 | Fbxl13 | NM_001199632.1 | chr5:21583486-21645605 | 7364 | Fcrls | NM_030707.3 | chr3:87250964-87263524 |
| 7268 | Fbxl14 | NM_133940.3 | chr6:119479667-119483886 | 7365 | Fdft1 | NM_010191.3 | chr14:63145150-63179978 |
| 7269 | Fbxl15 | NM_133694.2 | chr19:46328183-46330446 | 7366 | Fdps | NM_001253751.1 | chr3:89093587-89101967 |
| 7270 | Fbxl16 | NM_001164216.1 | chr17:25809084-25821265 | 7367 | Fdx1 | NM_007996.2 | chr9:51943024-51963602 |
| 7271 | Fbxl17 | NM_015794.1 | chr17:63045951-63500580 | 7368 | Fdxl1 | NM_001039824.2 | chr9:21067519-21073514 |
| 7272 | Fbxl18 | NM_001033312.3 | chr5:142871788-142895538 | 7369 | Fdxacb1 | NM_198675.2 | chr9:50768237-50772670 |
| 7273 | Fbxl19 | NM_172748.2 | chr7:127746774-127768928 | 7370 | Fdxr | NM_007997.1 | chr11:115268024-115276969 |
| 7274 | Fbxl2 | NM_178624.6 | chr9:113976957-114026751 | 7371 | Fech | NM_007998.6 | chr18:64456549-64489066 |

Fig.21 - 39

| | | | | | | | | |
|---|---|---|---|---|---|---|---|---|
| 7372 | Fem1a | NM_010192.4 | chr17:56256792-56263808 | 7469 | Fjx1 | NM_010218.2 | chr2:102449965-102451792 |
| 7373 | Fem1b | NM_010193.4 | chr9:62791829-62811648 | 7470 | Fkbp10 | NM_001163481.1 | chr11:100415693-100424840 |
| 7374 | Fem1c | NM_173423.4 | chr18:46504605-46525971 | 7471 | Fkbp11 | NM_024169.3 | chr15:98724367-98728198 |
| 7375 | Fen1 | NM_001271614.1 | chr19:10199131-10203943 | 7472 | Fkbp14 | NM_153573.1 | chr6:54577604-54593128 |
| 7376 | Fendrr | NR_045471.2 | chr8:121054881-121083110 | 7473 | Fkbp15 | NM_001045528.1 | chr4:62300341-62360548 |
| 7377 | Fer1l4 | NM_001136556.1 | chr2:156019139-156052947 | 7474 | Fkbp1a | NM_008019.3 | chr2:151542482-151561691 |
| 7378 | Fer1l5 | NM_001277076.1 | chr1:36372290-36422110 | 7475 | Fkbp1b | NM_016863.3 | chr12:4833173-4841595 |
| 7379 | Ferd3l | NM_033522.2 | chr12:33928424-33929309 | 7476 | Fkbp2 | NM_001166368.1 | chr19:6977738-6980461 |
| 7380 | Fermt1 | NM_198029.2 | chr2:132904178-132946036 | 7477 | Fkbp3 | NM_013902.4 | chr12:65062431-65073938 |
| 7381 | Fermt2 | NM_146054.2 | chr14:45438791-45530065 | 7478 | Fkbp4 | NM_010219.3 | chr6:128430106-128438631 |
| 7382 | Fermt3 | NM_153795.2 | chr19:6998957-7019469 | 7479 | Fkbp5 | NM_010220.4 | chr17:28398752-28486149 |
| 7383 | Fert2 | NM_001037997.3 | chr17:63863980-64199496 | 7480 | Fkbp6 | NM_001277891.1 | chr5:135337364-135350044 |
| 7384 | Fes | NM_010174.2 | chr7:80377757-80387946 | 7481 | Fkbp7 | NM_010222.2 | chr2:76663033-76673098 |
| 7385 | Fetub | NM_001083904.1 | chr16:22920221-22939768 | 7482 | Fkbp8 | NM_001111066.1 | chr8:70527742-70535328 |
| 7386 | Fev | NM_153113.2 | chr1:74881508-74885408 | 7483 | Fkbp9 | NM_012056.2 | chr6:56832658-56879360 |
| 7387 | Fez1 | NM_183171.4 | chr9:36843658-36878640 | 7484 | Fkbpl | NM_019873.2 | chr17:34644882-34646327 |
| 7388 | Fez2 | NM_001285940.1 | chr17:78377877-78418152 | 7485 | Fkrp | NM_173430.2 | chr7:16809266-16816732 |
| 7389 | Fezf1 | NM_028462.1 | chr6:23245046-23248264 | 7486 | Fktn | NM_139309.4 | chr4:53714181-53783271 |
| 7390 | Fezf2 | NM_080433.3 | chr14:12341891-12345865 | 7487 | Flad1 | NM_177041.3 | chr3:89402672-89411863 |
| 7391 | Ffar1 | NM_194057.2 | chr7:30860567-30861470 | 7488 | Flcn | NM_001271356.1 | chr11:59791407-59810039 |
| 7392 | Ffar2 | NM_001168509.1 | chr7:30818356-30821648 | 7489 | Flg2 | NM_001013804.1 | chr3:93197272-93221376 |
| 7393 | Ffar3 | NM_001033316.2 | chr7:30854329-30856178 | 7490 | Fli1 | NM_008026.5 | chr9:32422203-32541452 |
| 7394 | Ffar4 | NM_181748.2 | chr19:38070078-38114263 | 7491 | Flii | NM_022009.2 | chr11:60714145-60727263 |
| 7395 | Fga | NM_001111048.2 | chr3:83026152-83033617 | 7492 | Flna | NM_001290421.1 | chrX:74223460-74246534 |
| 7396 | Fgb | NM_181849.2 | chr3:83042304-83049790 | 7493 | Flnb | NM_001081427.1 | chr14:7817956-7951587 |
| 7397 | Fgd1 | NM_008001.4 | chrX:151047169-151089686 | 7494 | Flnc | NM_001081185.1 | chr6:29433152-29461888 |
| 7398 | Fgd2 | NM_001159538.1 | chr17:29360913-29379635 | 7495 | Flot1 | NM_008027.2 | chr17:35823356-35832787 |
| 7399 | Fgd3 | NM_015759.2 | chr13:49263109-49309208 | 7496 | Flot2 | NM_001040403.1 | chr11:78037940-78060432 |
| 7400 | Fgd4 | NM_139232.3 | chr16:16416914-16560219 | 7497 | Flrt1 | NM_201411.2 | chr19:7092010-7105729 |
| 7401 | Fgd5 | NM_172731.2 | chr6:91987109-92076005 | 7498 | Flrt2 | NM_203518.4 | chr12:95692225-95785213 |
| 7402 | Fgd6 | NM_053072.3 | chr10:94036000-94145339 | 7499 | Flrt3 | NM_001172160.1 | chr2:140658197-140671476 |
| 7403 | Fgf1 | NM_010197.3 | chr18:38838672-38918699 | 7500 | Flt1 | NM_010228.3 | chr5:147562195-147725988 |
| 7404 | Fgf10 | NM_008002.4 | chr13:118714698-118792573 | 7501 | Flt3 | NM_010229.2 | chr5:147730741-147804489 |
| 7405 | Fgf11 | NM_001291104.1 | chr11:69796067-69801716 | 7502 | Flt3l | NM_013520.3 | chr7:45131188-45136432 |
| 7406 | Fgf12 | NM_001276419.2 | chr16:28157782-28564951 | 7503 | Flt4 | NM_008029.3 | chr11:49609678-49652739 |
| 7407 | Fgf13 | NM_001290414.1 | chrX:59062145-59585572 | 7504 | Flywch1 | NM_153791.2 | chr17:23785422-23771991 |
| 7408 | Fgf14 | NM_010201.4 | chr14:123078290-124192546 | 7505 | Flywch2 | NM_029798.3 | chr17:23776917-23786077 |
| 7409 | Fgf15 | NM_008003.2 | chr7:144896531-144900951 | 7506 | Fmn1 | NM_001285458.1 | chr2:113327735-113716767 |
| 7410 | Fgf16 | NM_030614.2 | chrX:105764476-105776532 | 7507 | Fmn2 | NM_019445.2 | chr1:174561824-174822729 |
| 7411 | Fgf17 | NM_008004.4 | chr14:70636204-70642268 | 7508 | Fmnl1 | NM_001077698.1 | chr11:103171137-103198900 |
| 7412 | Fgf18 | NM_008005.2 | chr11:33116977-33147400 | 7509 | Fmnl2 | NM_172409.2 | chr2:52857867-53134202 |
| 7413 | Fgf2 | NM_008006.2 | chr3:37348652-37404830 | 7510 | Fmnl3 | NM_011711.2 | chr15:99317211-99370482 |
| 7414 | Fgf20 | NM_030610.2 | chr8:40279165-40286953 | 7511 | Fmo1 | NM_010231.2 | chr1:162829560-162866548 |
| 7415 | Fgf21 | NM_020013.4 | chr7:45613889-45615490 | 7512 | Fmo2 | NM_018881.3 | chr1:162875046-162898712 |
| 7416 | Fgf22 | NM_023024.1 | chr10:79755118-79756961 | 7513 | Fmo3 | NM_008030.2 | chr1:162953798-162984528 |
| 7417 | Fgf23 | NM_022657.4 | chr6:127072901-127082296 | 7514 | Fmo4 | NM_144878.1 | chr1:162793882-162812549 |
| 7418 | Fgf3 | NM_008007.2 | chr7:144838611-144843348 | 7515 | Fmo5 | NM_001161763.1 | chr3:97628803-97655287 |
| 7419 | Fgf4 | NM_010202.5 | chr7:144861385-144865243 | 7516 | Fmo6 | NM_001178038.1 | chr1:162916550-162937225 |
| 7420 | Fgf5 | NM_001277268.1 | chr5:98254183-98277033 | 7517 | Fmo9 | NM_172844.2 | chr1:166662054-166681845 |
| 7421 | Fgf6 | NM_010203.4 | chr6:127015541-127024718 | 7518 | Fmod | NM_021355.3 | chr1:134037514-134048277 |
| 7422 | Fgf7 | NM_008008.4 | chr2:126034657-126091185 | 7519 | Fmr1 | NM_001290424.1 | chrX:68678540-68717961 |
| 7423 | Fgf8 | NM_001166361.1 | chr19:45736797-45742884 | 7520 | Fmr1nb | NM_001166619.1 | chrX:68761838-68804560 |
| 7424 | Fgf9 | NM_013518.4 | chr14:58072685-58112720 | 7521 | Fn1 | NM_001276408.1 | chr1:71585472-71653234 |
| 7425 | Fgfbp1 | NM_001271616.1 | chr5:43978857-43981799 | 7522 | Fn3k | NM_010386.2 | chr11:121434952-121443505 |
| 7426 | Fgfbp3 | NM_028263.1 | chr19:36917549-36919599 | 7523 | Fn3krp | NM_183420.3 | chr11:121421372-121430768 |
| 7427 | Fgfr1 | NM_010079908.2 | chr8:25518758-25575718 | 7524 | Fnbp1 | NM_001038700.2 | chr2:31026205-31142008 |
| 7428 | Fgfr1op | NM_001197046.1 | chr17:8165517-8196470 | 7525 | Fnbp1l | NM_001114665.2 | chr3:122538718-122619714 |
| 7429 | Fgfr1op2 | NM_026172.2 | chr6:146577913-146599198 | 7526 | Fnbp4 | NM_188828.2 | chr2:90745369-90781020 |
| 7430 | Fgfr2 | NM_010207.2 | chr7:130162456-130266808 | 7527 | Fndc3c2 | NM_001033424.3 | chrX:106326245-106355372 |
| 7431 | Fgfr3 | NM_001163218.1 | chr5:33721729-33737068 | 7528 | Fndc1 | NM_001081416.1 | chr17:7738567-7804974 |
| 7432 | Fgfr4 | NM_008011.2 | chr5:55152617-55168759 | 7529 | Fndc3a | NM_207636.2 | chr14:72537952-72710003 |
| 7433 | Fgfrl1 | NM_001164259.1 | chr5:108694228-108706950 | 7530 | Fndc3b | NM_173182.2 | chr3:27416161-27710439 |
| 7434 | Fgg | NM_133862.1 | chr3:83030798-83015049 | 7531 | Fndc3c1 | NM_001007580.1 | chrX:106420042-106485229 |
| 7435 | Fggy | NM_001113412.1 | chr4:95557506-95926939 | 7532 | Fndc4 | NM_022424.5 | chr5:31292245-31295877 |
| 7436 | Fgl1 | NM_145594.2 | chr8:41191433-41215156 | 7533 | Fndc5 | NM_027402.3 | chr4:129137059-129144593 |
| 7437 | Fgl2 | NM_008013.4 | chr5:21372672-21378386 | 7534 | Fndc7 | NM_001165965.1 | chr3:108853677-108890008 |
| 7438 | Fgr | NM_010208.4 | chr4:132974094-133001882 | 7535 | Fndc8 | NM_030724.1 | chr11:82892144-82900737 |
| 7439 | Fh1 | NM_010209.2 | chr1:175601377-175625635 | 7536 | Fndc9 | NM_177075.4 | chr11:46235556-46239871 |
| 7440 | Fhad1 | NM_177868.4 | chr4:141890622-142011651 | 7537 | Fnip1 | NM_173753.4 | chr11:54438178-54518241 |
| 7441 | Fhadios1 | NR_040672.1 | chr4:141982991-141986797 | 7538 | Fnip2 | NM_001162999.2 | chr3:79455970-79567679 |
| 7442 | Fhdc1 | NM_001033314.5 | chr3:84442195-84480439 | 7539 | Fnta | NM_008033.3 | chr8:25998721-26015601 |
| 7443 | Fhit | NM_010210.3 | chr14:9550093-11162035 | 7540 | Fntb | NM_145927.2 | chr12:76817466-76921412 |
| 7444 | Fhl1 | NM_001077361.1 | chrX:56731956-56793346 | 7541 | Focad | NM_001081384.1 | chr4:88094629-88411011 |
| 7445 | Fhl2 | NM_001289533.1 | chr1:43123070-43196761 | 7542 | Foth1 | NM_001159706.1 | chr7:86718975-86775864 |
| 7446 | Fhl3 | NM_010213.3 | chr4:124700698-124708611 | 7543 | Folr1 | NM_001252552.1 | chr7:101858330-101870788 |
| 7447 | Fhl4 | NM_010214.4 | chr10:85097018-85102495 | 7544 | Folr2 | NM_008035.2 | chr7:101839987-101845331 |
| 7448 | Fhl5 | NM_021318.3 | chr4:25199908-25242876 | 7545 | Folr4 | NM_022888.2 | chr9:14900022-14903951 |
| 7449 | Fhod1 | NM_177699.4 | chr8:105329159-105347970 | 7546 | Fopnl | NM_025345.2 | chr16:14299243-14317332 |
| 7450 | Fhod3 | NM_001081243.1 | chr18:24708622-25133507 | 7547 | Fos | NM_010234.2 | chr12:85473900-85477270 |
| 7451 | Fibcd1 | NM_178887.4 | chr2:31813289-31846005 | 7548 | Fosb | NM_008036.2 | chr7:19302695-19310045 |
| 7452 | Fibin | NM_026271.1 | chr2:110360924-110362993 | 7549 | Fosl1 | NM_010235.2 | chr19:5447697-5456938 |
| 7453 | Fibp | NM_001253833.1 | chr19:5460606-5465052 | 7550 | Fosl2 | NM_008037.4 | chr5:32136471-32157839 |
| 7454 | Ficd | NM_001010825.3 | chr5:113737581-113740607 | 7551 | Foxa1 | NM_008259.3 | chr12:57540631-57546121 |
| 7455 | Fig4 | NM_133999.1 | chr10:41188171-41303241 | 7552 | Foxa2 | NM_001291065.1 | chr2:148042876-148045948 |
| 7456 | Figf | NM_010216.2 | chrX:164373521-164402650 | 7553 | Foxa3 | NM_008260.2 | chr7:19013282-19023539 |
| 7457 | Figla | NM_012013.1 | chr6:86017190-86020996 | 7554 | Foxb1 | NM_022378.3 | chr9:69757709-69760940 |
| 7458 | Fign | NM_001267846.1 | chr2:63971507-64098038 | 7555 | Foxb2 | NM_008023.1 | chr19:16872315-16873850 |
| 7459 | Fignl1 | NM_001163359.1 | chr11:11800287-11808962 | 7556 | Foxc1 | NM_008592.2 | chr13:31806645-31810635 |
| 7460 | Fignl2 | NM_001214911.2 | chr15:101050191-101054399 | 7557 | Foxc2 | NM_013519.2 | chr8:121116170-121118894 |
| 7461 | Filip1 | NM_001081243.1 | chr9:79815561-79977882 | 7558 | Foxd1 | NM_008242.2 | chr13:98354244-98356705 |
| 7462 | Filip1l | NM_001040397.4 | chr16:57352276-57572804 | 7559 | Foxd2 | NM_008593.3 | chr4:114906279-114908898 |
| 7463 | Fip1l1 | NM_001159573.1 | chr5:74585481-74597124 | 7560 | Foxd2os | NR_030721.1 | chr4:114909288-114921118 |
| 7464 | Firre | NR_015505.2 | chrX:50563119-50635321 | 7561 | Foxd3 | NM_010425.3 | chr4:99656298-99658673 |
| 7465 | Fis1 | NM_001163243.1 | chr5:136953274-136966234 | 7562 | Foxd4 | NM_008022.2 | chr19:24898964-24901309 |
| 7466 | Fitm1 | NM_026808.1 | chr14:55575561-55576952 | 7563 | Foxe1 | NM_183298.1 | chr4:46344193-46345309 |
| 7467 | Fitm2 | NM_173397.4 | chr2:163468702-163472629 | 7564 | Foxe3 | NM_015758.2 | chr4:114925146-114926013 |
| 7468 | Fiz1 | NM_001110328.1 | chr7:5007055-5014697 | 7565 | Foxf1 | NM_010426.2 | chr8:121084385-121088154 |

Fig.21 - 40

| | | | | | | | | |
|---|---|---|---|---|---|---|---|---|
| 7566 | Foxf2 | NM_010225.2 | chr13:31625815-31631406 | 7663 | Fuca1 | NM_024243.4 | chr4:135920725-135940300 |
| 7567 | Foxg1 | NM_001160112.1 | chr12:49382882-49386867 | 7664 | Fuca2 | NM_025799.4 | chr10:13501027-13517275 |
| 7568 | Foxh1 | NM_007989.4 | chr15:76668223-76669948 | 7665 | Fuk | NM_172283.3 | chr8:110882455-110902488 |
| 7569 | Foxi1 | NM_023907.4 | chr11:34204340-34208089 | 7666 | Fundc1 | NM_028058.4 | chrX:17555599-17572325 |
| 7570 | Foxi2 | NM_183193.2 | chr7:135410386-135413615 | 7667 | Fundc2 | NM_026126.4 | chrX:75382398-75397158 |
| 7571 | Foxi3 | NM_001101464.1 | chr6:70956605-70961086 | 7668 | Fuom | NM_001286217.1 | chr7:140097814-140102441 |
| 7572 | Foxj1 | NM_008240.3 | chr11:116336703-116335354 | 7669 | Furin | NM_001081454.2 | chr7:80389193-80405436 |
| 7573 | Foxj2 | NM_021899.3 | chr6:122820183-122845366 | 7670 | Fus | NM_139149.2 | chr7:127796747-127982031 |
| 7574 | Foxj3 | NM_001290696.1 | chr4:119539660-119629119 | 7671 | Fut1 | NM_001271981.1 | chr7:45617605-45621059 |
| 7575 | Foxk1 | NM_199068.2 | chr5:142401496-142462015 | 7672 | Fut10 | NM_001012517.5 | chr8:31187330-31261924 |
| 7576 | Foxk2 | NM_001080932.2 | chr11:121259986-121309896 | 7673 | Fut11 | NM_028428.2 | chr14:20694967-20700197 |
| 7577 | Foxl1 | NM_008024.2 | chr8:121127684-121130644 | 7674 | Fut2 | NM_001271993.1 | chr7:45648590-45666394 |
| 7578 | Foxl2 | NM_012020.2 | chr9:98955606-98958126 | 7675 | Fut4 | NM_010242.3 | chr9:14748845-14752122 |
| 7579 | Foxl2os | NR_003248.3 | chr9.98949154-98955310 | 7676 | Fut4-ps1 | NR_033644.1 | chr17:56734227-36739292 |
| 7580 | Foxm1 | NM_008021.4 | chr6.128362993-128375886 | 7677 | Fut7 | NM_001177366.1 | chr2:25423693-25428373 |
| 7581 | Foxn1 | NM_001277290.1 | chr11:78357576-78386608 | 7678 | Fut8 | NM_001252614.1 | chr12:77238103-77475996 |
| 7582 | Foxn2 | NM_180974.4 | chr17:88440711-88490533 | 7679 | Fut9 | NM_010243.3 | chr4:25609332-25800003 |
| 7583 | Foxn3 | NM_183186.2 | chr12:99195093-99450074 | 7680 | Fuz | NM_027176.3 | chr7:44896078-44900624 |
| 7584 | Foxn4 | NM_148935.2 | chr5:114254163-114273761 | 7681 | Fv1 | NM_010244.3 | chr4:147868978-147870358 |
| 7585 | Foxo1 | NM_019739.3 | chr3:52268336-52350103 | 7682 | Fxn | NM_008044.2 | chr19:24261452-24280586 |
| 7586 | Foxo3 | NM_019740.2 | chr10:42185785-42276742 | 7683 | Fxr1 | NM_001113188.1 | chr3:34020078-34089344 |
| 7587 | Foxo4 | NM_018789.2 | chrX:101254527-101260873 | 7684 | Fxr2 | NM_011814.2 | chr11:69632970-69653297 |
| 7588 | Foxo6 | NM_194060.1 | chr4:120267077-120287261 | 7685 | Fxyd1 | NM_019503.4 | chr7:31051677-31056656 |
| 7589 | Foxp1 | NM_001197321.1 | chr6:98925341-99266515 | 7686 | Fxyd2 | NM_007503.3 | chr9:45406076-45410278 |
| 7590 | Foxp2 | NM_001286607.1 | chr6:15185505-15441977 | 7687 | Fxyd3 | NM_008557.2 | chr7:31070534-31076697 |
| 7591 | Foxp3 | NM_001199347.1 | chrX:7579675-7595243 | 7688 | Fxyd4 | NM_001173372.1 | chr6:117933558-117937335 |
| 7592 | Foxp4 | NM_001110824.1 | chr17:47867132-47924632 | 7689 | Fxyd5 | NM_001111073.2 | chr7:31032722-31041839 |
| 7593 | Foxq1 | NM_008239.4 | chr13:31558189-31560974 | 7690 | Fxyd6 | NM_022004.6 | chr9:45370184-45396159 |
| 7594 | Foxr1 | NM_001033469.2 | chr9:44434233-44440868 | 7691 | Fxyd7 | NM_022007.1 | chr7:31042514-31051454 |
| 7595 | Foxr2 | NM_001034894.3 | chrX:153118787-153132861 | 7692 | Fyb | NM_001278269.1 | chr15:6579846-6665608 |
| 7596 | Foxred1 | NM_001291448.1 | chr9:35204220-35210055 | 7693 | Fycol | NM_001130253.2 | chr9:123789499-123851899 |
| 7597 | Foxred2 | NM_001017983.2 | chr15:77940521-77956722 | 7694 | Fyn | NM_001122892.1 | chr10:39369798-39565374 |
| 7598 | Foxs1 | NM_010226.2 | chr2:152931897-152933208 | 7695 | Fyttd1 | NM_001159349.1 | chr16:32877783-32908963 |
| 7599 | Fpgs | NM_010236.3 | chr2:32682608-32694175 | 7696 | Fzd1 | NM_021457.3 | chr5:4753838-4758216 |
| 7600 | Fpgt | NM_029330.2 | chr3:155084918-155093378 | 7697 | Fzd10 | NM_175284.3 | chr5:128601106-128664093 |
| 7601 | Fpr1 | NM_013521.2 | chr17:17876470-17883939 | 7698 | Fzd2 | NM_020510.2 | chr11:102604430-102608058 |
| 7602 | Fpr2 | NM_008039.2 | chr17:17887823-17893952 | 7699 | Fzd3 | NM_021458.2 | chr14:65192440-65262463 |
| 7603 | Fpr3 | NM_008042.2 | chr17:17970457-17971677 | 7700 | Fzd4 | NM_008055.4 | chr7:89404365-89410110 |
| 7604 | Fpr-rs3 | NM_008040.2 | chr17:20623845-20624877 | 7701 | Fzd5 | NM_001042659.1 | chr1:64730557-64737750 |
| 7605 | Fpr-rs4 | NM_008041.2 | chr17:18021732-18022704 | 7702 | Fzd6 | NM_001162494.1 | chr15:39006279-39038190 |
| 7606 | Fpr-rs6 | NM_177316.2 | chr17:20182077-20183097 | 7703 | Fzd7 | NM_008057.3 | chr1:59482146-59486955 |
| 7607 | Fra10ac1 | NM_001081075.1 | chr19:38188478-38224132 | 7704 | Fzd8 | NM_008058.2 | chr18:9212855-9216201 |
| 7608 | Fras1 | NM_175473.3 | chr5:96373954-96784728 | 7705 | Fzd9 | NM_010246.1 | chr5:135248937-135251047 |
| 7609 | Frat1 | NM_008043.3 | chr19:41829969-41832583 | 7706 | Fzr1 | NM_019757.1 | chr10:81366878-81378370 |
| 7610 | Frat2 | NM_177122.3 | chr19:41845975-41848132 | 7707 | G0s2 | NM_008059.3 | chr1:193272159-193273188 |
| 7611 | Frem1 | NM_001198811.1 | chr4:82897919-83052167 | 7708 | G2e3 | NM_001015099.2 | chr12:51348229-51376986 |
| 7612 | Frem2 | NM_172662.3 | chr3:53513937-53657355 | 7709 | G3bp1 | NM_013716.2 | chr11:55469751-55500887 |
| 7613 | Frem3 | NM_001167898.1 | chr8:80611038-80695557 | 7710 | G3bp2 | NM_001080794.2 | chr5:92052144-92093598 |
| 7614 | Frg1 | NM_013522.3 | chr8:41397453-41417118 | 7711 | G530011O06Rik | NR_029457.1 | chrX:169975842-169978917 |
| 7615 | Frk | NM_001159544.1 | chr10:34483399-34611230 | 7712 | G630020P09Rik | NR_027913.1 | chr1:69803668-69806038 |
| 7616 | Frmd3 | NM_001163792.1 | chr4:74013602-74202214 | 7713 | G630055G22Rik | NR_045404.1 | chr18:47922840-48107980 |
| 7617 | Frmd4a | NM_001177843.1 | chr2:4400975-4614043 | 7714 | G630071F17Rik | NR_045401.1 | chr18:60663409-60671624 |
| 7618 | Frmd4b | NM_145148.2 | chr9:97286866-97617657 | 7715 | G630080O17Rik | NM_001173500.2 | chr10:39946911-39960153 |
| 7619 | Frmd5 | NM_172673.3 | chr2:121545528-121807057 | 7716 | G630093K05Rik | NR_045156.1 | chr13:47910434-47934361 |
| 7620 | Frmd6 | NM_028127.1 | chr12:70825513-70902234 | 7717 | G6b | NM_001033221.3 | chr17:35062692-35066184 |
| 7621 | Frmd7 | NM_001190332.1 | chrX:50892644-50942710 | 7718 | G6bos | NM_001462.1 | chr17:35064436-35065596 |
| 7622 | Frmd8 | NM_026169.4 | chr19:5850973-5875208 | 7719 | G6pc | NM_008061.4 | chr11:101367715-101377903 |
| 7623 | Frmpd1 | NM_001081172.2 | chr4:45184965-45285936 | 7720 | G6pc2 | NM_001289856.1 | chr2:69211072-69227993 |
| 7624 | Frmpd1os | NR_040666.1 | chr4:45234722-45243990 | 7721 | G6pc3 | NM_175935.3 | chr11:102189698-102194081 |
| 7625 | Frmpd3 | NM_177750.6 | chrX:140367499-140394620 | 7722 | G6pd2 | NM_019468.2 | chr5:61808842-61810477 |
| 7626 | Frmpd4 | NM_001033330.3 | chrX:167471305-168577233 | 7723 | G6pdx | NM_008062.2 | chrX:74409485-74429161 |
| 7627 | Frra1 | NM_001134478.1 | chr3:116859966-116903750 | 7724 | G730013B05Rik | NR_040379.1 | chr16:50528501-50559459 |
| 7628 | Frs1l | NM_001142965.1 | chr4:56969135-56990391 | 7725 | Gaa | NM_001159324.1 | chr11:119267966-119285698 |
| 7629 | Frs2 | NM_177798.3 | chr10:117070126-117148474 | 7726 | Gab1 | NM_021356.2 | chr8:80764433-80880479 |
| 7630 | Frs3 | NM_144939.2 | chr17:47695206-47704286 | 7727 | Gab2 | NM_001162477.1 | chr7:97087150-97308951 |
| 7631 | Frs3os | NR_045912.1 | chr17:47699548-47701996 | 7728 | Gab3 | NM_181584.4 | chrX:74988544-75084905 |
| 7632 | Fry | NM_172887.2 | chr5:150259929-150497753 | 7729 | Gabarap | NM_019749.4 | chr11:69991369-69994949 |
| 7633 | Fryl | NM_028194.2 | chr5:73020190-73256618 | 7730 | Gabarapl1 | NM_020590.4 | chr6:129533191-129547331 |
| 7634 | Frzb | NM_011356.4 | chr2:80411969-80447396 | 7731 | Gabarapl2 | NM_026693.5 | chr8:111940702-111952915 |
| 7635 | Fsbp | NM_001256142.1 | chr4:115979661-115987802 | 7732 | Gabbr1 | NM_019439.3 | chr17:37045965-37074305 |
| 7636 | Fscb | NM_001163271.1 | chr12:64471332-64474898 | 7733 | Gabbr2 | NM_001081141.1 | chr4:46663897-46991714 |
| 7637 | Fscn1 | NM_007984.4 | chr5:142960354-142973189 | 7734 | Gabpa | NM_008065.2 | chr16:84835123-84863778 |
| 7638 | Fscn2 | NM_172802.4 | chr11:120361533-120368173 | 7735 | Gabph1 | NM_001271467.1 | chr2:126628906-126675592 |
| 7639 | Fscn3 | NM_019523.3 | chr6:28427900-28438622 | 7736 | Gabpb2 | NM_029835.1 | chr3:95181765-95217942 |
| 7640 | Fsd1 | NM_183178.2 | chr17:55988510-55998881 | 7737 | Gabra1 | NM_010250.5 | chr11:42130939-42182930 |
| 7641 | Fsd1l | NM_001195284.1 | chr4:53631470-53707009 | 7738 | Gabra2 | NM_008066.3 | chr5:70961056-71095849 |
| 7642 | Fsd2 | NM_172904.2 | chr7:81534353-81566981 | 7739 | Gabra3 | NM_008067.4 | chrX:72432675-72656246 |
| 7643 | Fshb | NM_008045.3 | chr2:107035985-107059651 | 7740 | Gabra4 | NM_010251.2 | chr5:71569733-71658308 |
| 7644 | Fshr | NM_013523.3 | chr17:88984951-89200675 | 7741 | Gabra5 | NM_176942.4 | chr7:57407668-57510009 |
| 7645 | Fsip1 | NM_027759.3 | chr2:118204887-118256966 | 7742 | Gabra6 | NM_001099641.2 | chr11:42306436-42321072 |
| 7646 | Fst | NM_008046.3 | chr13:114452261-114458951 | 7743 | Gabrb1 | NM_008069.4 | chr5:71700015-72137244 |
| 7647 | Fstl1 | NM_008047.5 | chr16:37777054-37836516 | 7744 | Gabrb2 | NM_008070.3 | chr11:42419756-42632591 |
| 7648 | Fstl3 | NM_031380.2 | chr10:79777273-79782630 | 7745 | Gabrb3 | NM_001038701.2 | chr7:57590517-57828801 |
| 7649 | Fstl4 | NM_177059.3 | chr11:52764705-53187347 | 7746 | Gabrd | NM_008072.2 | chr4:155384978-155398069 |
| 7650 | Fstl5 | NM_001285719.1 | chr3:76075582-76710005 | 7747 | Gabre | NM_017369.2 | chrX:72257431-72274721 |
| 7651 | Ftcd | NM_080845.2 | chr10:76575647-76590338 | 7748 | Gabrg1 | NM_010252.4 | chr5:70751046-70842617 |
| 7652 | Fth1 | NM_010239.2 | chr19:9982645-9985111 | 7749 | Gabrg2 | NM_008074.3 | chr11:41910189-42000714 |
| 7653 | Fth17 | NM_031261.2 | chrX:9033485-9034333 | 7750 | Gabrg3 | NM_008074.2 | chr7:56724241-57386871 |
| 7654 | Ftl1 | NM_010240.2 | chr7:45457943-45459886 | 7751 | Gabrp | NM_146017.3 | chr11:33550780-33578957 |
| 7655 | Ftmt | NM_026286.3 | chr18:52332996-52333996 | 7752 | Gabrq | NM_001290435.1 | chrX:72825177-72842602 |
| 7656 | Fto | NM_011936.2 | chr8:91313524-91668433 | 7753 | Gabrr1 | NM_008075.2 | chr4:33132555-33163588 |
| 7657 | Ftsj1 | NM_001290430.1 | chrX:8238667-8252406 | 7754 | Gabrr2 | NM_008076.3 | chr4:33063111-33095865 |
| 7658 | Ftsj2 | NM_026273.2 | chr5:140327673-140331298 | 7755 | Gabrr3 | NM_001081190.1 | chr16:59407381-59461739 |
| 7659 | Ftsj3 | NM_025310.2 | chr11:106249143-106255802 | 7756 | Gad1 | NM_008077.5 | chr2:70562128-70602014 |
| 7660 | Ftx | NR_028380.1 | chrX:103569504-103623754 | 7757 | Gad1os | NR_040496.1 | chr2:70489939-70563357 |
| 7661 | Fubp1 | NM_057172.3 | chr3:152210457-152236830 | 7758 | Gad2 | NM_008078.2 | chr2:22622326-22693877 |
| 7662 | Fubp3 | NM_001033389.4 | chr2:31572650-31617526 | 7759 | Gadd45a | NM_007836.1 | chr6:67035095-67037407 |

Fig.21 - 41

| | | | | | | | |
|---|---|---|---|---|---|---|---|
| 7760 | Gadd45b | NM_008655.1 | chr10:80930090-80932204 | 7857 | Gc | NM_008096.2 | chr5:89417910-89457898 |
| 7761 | Gadd45g | NM_011817.2 | chr13:51846674-51848474 | 7858 | Gca | NM_145523.3 | chr2:62664326-62694109 |
| 7762 | Gadd45gip1 | NM_183358.4 | chr8:84832281-84835482 | 7859 | Gcat | NM_001161712.1 | chr15:79030873-79042531 |
| 7763 | Gadl1 | NM_028638.1 | chr9:115909454-116076176 | 7860 | Gcc1 | NM_028900.4 | chr6:28416602-28421724 |
| 7764 | Gak | NM_001282051.1 | chr5:108568106-108629777 | 7861 | Gcc2 | NM_027375.2 | chr10:58255525-58305592 |
| 7765 | Gal | NM_010253.3 | chr19:3409916-3414457 | 7862 | Gcdh | NM_001044744.1 | chr8:84886386-84893921 |
| 7766 | Gal3st1 | NM_001177691.1 | chr11:3989932-3999328 | 7863 | Gcfc2 | NM_177884.2 | chr6:81923668-81959098 |
| 7767 | Gal3st2 | NM_199366.4 | chr1:93861343-93876494 | 7864 | Gcg | NM_008100.4 | chr2:62474529-62483653 |
| 7768 | Gal3st3 | NM_001024717.2 | chr19:5298330-5308739 | 7865 | Gcgr | NM_008101.2 | chr11:120530726-120538984 |
| 7769 | Gal3st4 | NM_001033446.2 | chr5:138264924-138272754 | 7866 | Gch1 | NM_008102.3 | chr14:47153894-47189402 |
| 7770 | Galc | NM_008079.4 | chr12:98202239-98259459 | 7867 | Gchfr | NM_177157.4 | chr2:119167787-119172389 |
| 7771 | Gale | NM_178389.3 | chr4:135965164-135968178 | 7868 | Gck | NM_001287386.1 | chr11:5900820-5915135 |
| 7772 | Galk1 | NM_016905.2 | chr11:116008356-116012719 | 7869 | Gckr | NM_144909.1 | chr5:31297580-31327302 |
| 7773 | Galk2 | NM_001291002.1 | chr2:125866222-125924298 | 7870 | Gclc | NM_010295.2 | chr9:77754534-77784489 |
| 7774 | Galm | NM_176963.4 | chr17:80127470-80185032 | 7871 | Gclm | NM_008129.4 | chr3:122245556-122267215 |
| 7775 | Galns | NM_001193645.1 | chr8:122578236-122611487 | 7872 | Gcm1 | NM_008103.3 | chr9:78051957-78065624 |
| 7776 | Galnt1 | NM_001160404.1 | chr18:24205993-24286816 | 7873 | Gcm2 | NM_008104.2 | chr13:41101426-41109988 |
| 7777 | Galnt10 | NM_134189.2 | chr11:57645441-57787500 | 7874 | Gcn1l1 | NM_172719.2 | chr5:115565262-115622654 |
| 7778 | Galnt11 | NM_144908.3 | chr5:25222892-25265918 | 7875 | Gcnt1 | NM_001136484.3 | chr19:17326140-17339505 |
| 7779 | Galnt12 | NM_172693.3 | chr4:47091952-47123042 | 7876 | Gcnt2 | NM_008105.3 | chr13:40886757-40960892 |
| 7780 | Galnt13 | NM_173030.2 | chr2:54436386-55117744 | 7877 | Gcnt3 | NM_028087.2 | chr9:70031495-70038088 |
| 7781 | Galnt14 | NM_027864.2 | chr17:73493750-73710451 | 7878 | Gcnt4 | NM_001166065.1 | chr13:96924688-96950914 |
| 7782 | Galnt15 | NM_030166.3 | chr14:32029102-32058326 | 7879 | Gcnt7 | NM_001039560.3 | chr2:172450312-172458596 |
| 7783 | Galnt16 | NM_001081421.1 | chr12:80518989-80603996 | 7880 | Gcsam | NM_001159297.1 | chr16:45610439-45622867 |
| 7784 | Galnt18 | NM_173739.3 | chr7:111471660-111779977 | 7881 | Gcsh | NM_026572.3 | chr8:116981827-116993449 |
| 7785 | Galnt2 | NM_139272.2 | chr8:124231393-124345723 | 7882 | Gda | NM_010266.2 | chr19:21391306-21472661 |
| 7786 | Galnt3 | NM_015736.2 | chr2:66082765-66124793 | 7883 | Gdap1 | NM_010267.3 | chr1:17145372-17164270 |
| 7787 | Galnt4 | NM_015737.4 | chr10:99108134-99113247 | 7884 | Gdap10 | NR_045032.1 | chr12:32824115-32826908 |
| 7788 | Galnt5 | NM_172855.3 | chr2:57998154-58039171 | 7885 | Gdap1l1 | NM_144891.2 | chr2:163438466-163455324 |
| 7789 | Galnt6 | NM_001161767.1 | chr15:100689914-100729376 | 7886 | Gdap2 | NM_010269.3 | chr3:100162462-100206989 |
| 7790 | Galnt7 | NM_001167981.1 | chr8:57523824-57653055 | 7887 | Gde1 | NM_019580.4 | chr7:118688557-118705798 |
| 7791 | Galnt9 | NM_001122639.2 | chr5:110603504-110621383 | 7888 | Gdf1 | NM_001163282.2 | chr8:70315774-70331592 |
| 7792 | Galnt15 | NM_026449.3 | chr2:25181479-25220289 | 7889 | Gdf10 | NM_145741.2 | chr14:33923586-33935282 |
| 7793 | Galntl6 | NM_175032.3 | chr8:57774051-58911627 | 7890 | Gdf11 | NM_010272.1 | chr10:128884545-128893718 |
| 7794 | Galp | NM_178028.2 | chr7:6197089-6216137 | 7891 | Gdf15 | NM_011819.2 | chr8:70629393-70631635 |
| 7795 | Galr1 | NM_008082.2 | chr18:82392495-82406777 | 7892 | Gdf2 | NM_019506.4 | chr14:33941088-33947198 |
| 7796 | Galr2 | NM_010254.4 | chr11:116280938-116283938 | 7893 | Gdf3 | NM_008108.4 | chr6:122605402-122610071 |
| 7797 | Galr3 | NM_015738.2 | chr15:79041884-79043558 | 7894 | Gdf5 | NM_008109.2 | chr2:155941024-155945364 |
| 7798 | Galt | NM_016658.3 | chr4:41755227-41759224 | 7895 | Gdf6 | NM_013526.1 | chr4:9844371-9862345 |
| 7799 | Gamt | NM_010255.3 | chr10:80258150-80260968 | 7896 | Gdf7 | NM_013527.1 | chr12:8297917-8301954 |
| 7800 | Gan | NM_001081151.1 | chr8:117158134-117205186 | 7897 | Gdf9 | NM_008110.2 | chr11:53433285-53437902 |
| 7801 | Ganab | NM_008060.2 | chr19:8898056-8916742 | 7898 | Gdi1 | NM_010273.4 | chrX:74305011-74311867 |
| 7802 | Ganc | NM_172672.2 | chr2:120403895-120460852 | 7899 | Gdi2 | NM_008112.4 | chr13:3538074-3566261 |
| 7803 | Gap43 | NM_008083.2 | chr16:42248560-42340651 | 7900 | Gdnf | NM_010275.3 | chr15:7810047-7837580 |
| 7804 | Gapdh | NM_001289726.1 | chr6:125161851-125166467 | 7901 | Gdpd1 | NM_025638.2 | chr11:87033793-87074137 |
| 7805 | Gapdhs | NM_001290631.1 | chr7:30729778-30743681 | 7902 | Gdpd2 | NM_023608.4 | chrX:100729846-100738901 |
| 7806 | Gapt | NM_177173.3 | chr13:110352614-110357172 | 7903 | Gdpd3 | NM_024228.2 | chr7:126766413-126775645 |
| 7807 | Gapvd1 | NM_025709.2 | chr2:34676982-34755232 | 7904 | Gdpd4 | NM_177696.3 | chr7:97919957-98049663 |
| 7808 | Gar1 | NM_026578.3 | chr3:129824911-129831396 | 7905 | Gdpd5 | NM_201352.2 | chr7:99381548-99460984 |
| 7809 | Garem | NM_001033445.3 | chr18:21127341-21300139 | 7906 | Gdpgp1 | NM_178752.3 | chr7:80232892-80241420 |
| 7810 | Gareml | NM_001167879.1 | chr5:30105195-30118380 | 7907 | Gem | NM_010276.4 | chr4:11704446-11714993 |
| 7811 | Garnl3 | NM_178888.4 | chr2:32986365-33087204 | 7908 | Gemin2 | NM_025656.5 | chr12:59013390-59028470 |
| 7812 | Gars | NM_180678.3 | chr6:55038000-55079504 | 7909 | Gemin4 | NM_177367.3 | chr11:76210670-76217572 |
| 7813 | Garl | NM_010256.2 | chr6:91621896-91646972 | 7910 | Gemin5 | NM_001166669.1 | chr11:58120000-58168539 |
| 7814 | Gas1 | NM_008086.2 | chr13:60174404-60177535 | 7911 | Gemin6 | NM_026653.3 | chr17:80224488-80228497 |
| 7815 | Gas2 | NM_008087.2 | chr7:51879144-51994458 | 7912 | Gemin7 | NM_027189.2 | chr7:19564948-19573343 |
| 7816 | Gas2l1 | NM_001190406.1 | chr11:5054130-5065327 | 7913 | Gemin8 | NM_146238.4 | chrX:166170453-166190512 |
| 7817 | Gas2l2 | NM_001013414.1 | chr11:83421634-83429521 | 7914 | Gen1 | NM_177331.4 | chr12:11240925-11265787 |
| 7818 | Gas2l3 | NM_001033331.2 | chr10:89408822-89443967 | 7915 | Get4 | NM_001163316.1 | chr5:139253496-139270050 |
| 7819 | Gas5 | NR_002840.2 | chr1:161035165-161038537 | 7916 | Gfap | NM_001131020.1 | chr11:102890165-102897200 |
| 7820 | Gas6 | NM_019521.2 | chr8:13464373-13494535 | 7917 | Gfer | NM_023040.3 | chr17:24693190-24696158 |
| 7821 | Gas7 | NM_001109657.2 | chr11:67588499-67688992 | 7918 | Gfi1 | NM_001267621.1 | chr5:107716654-107725805 |
| 7822 | Gas8 | NM_018555.2 | chr8:123518854-123536650 | 7919 | Gfi1b | NM_001160406.1 | chr2:28609449-28621982 |
| 7823 | Gast | NM_010257.1 | chr11:100334411-100336996 | 7920 | Gfm1 | NM_138591.2 | chr3:67430114-67475068 |
| 7824 | Gata1 | NM_008089.2 | chrX:7959259-7967910 | 7921 | Gfm2 | NM_001146043.2 | chr13:97137936-97181196 |
| 7825 | Gata2 | NM_008090.5 | chr6:88198663-88207032 | 7922 | Gfod1 | NM_001033399.4 | chr13:43195518-43304171 |
| 7826 | Gata3 | NM_008091.3 | chr2:9857077-9878600 | 7923 | Gfod2 | NM_027469.4 | chr8:105716112-105738607 |
| 7827 | Gata4 | NM_008092.4 | chr14:63198913-63246271 | 7924 | Gfpt1 | NM_013528.3 | chr6:87042845-87092207 |
| 7828 | Gata5 | NM_008093.2 | chr2:180329087-180334679 | 7925 | Gfpt2 | NM_013529.3 | chr11:49794154-49833620 |
| 7829 | Gata5os | NR_045877.1 | chr2:180332856-180340732 | 7926 | Gfra1 | NM_001285457.1 | chr19:58235604-58454594 |
| 7830 | Gata6 | NM_010258.3 | chr18:11052503-11085635 | 7927 | Gfra2 | NM_008115.3 | chr14:70850106-70979840 |
| 7831 | Gatad1 | NM_026033.2 | chr5:3639960-3647936 | 7928 | Gfra3 | NM_010280.4 | chr18:34689897-34720387 |
| 7832 | Gatad2a | NM_001119346.1 | chr8:69907068-69974383 | 7929 | Gfra4 | NM_001136063.2 | chr2:131039631-131043088 |
| 7833 | Gatad2b | NM_001033412.2 | chr3:90341659-90358120 | 7930 | Gfral | NM_205844.3 | chr9:76164101-76213657 |
| 7834 | Gatc | NM_029645.3 | chr5:115333241-115341161 | 7931 | Gfy | NM_001195255.1 | chr7:45176348-45179597 |
| 7835 | Gatm | NM_025961.5 | chr2:122594472-122611277 | 7932 | Gga1 | NM_145929.2 | chr15:78877189-78894585 |
| 7836 | Gatsl2 | NM_030719.2 | chr5:134099747-134141758 | 7933 | Gga2 | NM_028758.2 | chr7:121986721-122021198 |
| 7837 | Gatsl3 | NM_028022.1 | chr11:4218250-4222409 | 7934 | Gga3 | NM_001252067.1 | chr11:115584254-115603916 |
| 7838 | Gba | NM_001077411.2 | chr3:89205424-89208966 | 7935 | Ggact | NM_145466.2 | chr14:122890859-122913165 |
| 7839 | Gba2 | NM_172692.3 | chr4:43566927-43578864 | 7936 | Ggct | NM_026637.3 | chr6:54985094-54992867 |
| 7840 | Gbas | NM_008095.4 | chr5:129729074-129758325 | 7937 | Ggcx | NM_019802.5 | chr6:72414307-72431106 |
| 7841 | Gbe1 | NM_028803.4 | chr16:70313948-70569720 | 7938 | Ggh | NM_010281.2 | chr4:20042051-20066111 |
| 7842 | Gbf1 | NM_178930.3 | chr19:46152557-46286510 | 7939 | Ggn | NM_182694.2 | chr7:29170209-29173933 |
| 7843 | Gbgt1 | NM_139197.2 | chr2:28496890-28505415 | 7940 | Ggnbp1 | NM_001251881.1 | chr17:27018034-27036377 |
| 7844 | Gbp10 | NM_001039646.2 | chr5:105215698-105239533 | 7941 | Ggnbp2 | NM_153144.2 | chr11:84832360-84870738 |
| 7845 | Gbp11 | NM_001039647.3 | chr5:105323025-105346472 | 7942 | Ggps1 | NM_010282.2 | chr13:14052444-14063401 |
| 7846 | Gbp2 | NM_010260.1 | chr3:142562662-142638008 | 7943 | Ggt1 | NM_008116.3 | chr10:75573494-75586191 |
| 7847 | Gbp2b | NM_010259.2 | chr5:142594846-142619176 | 7944 | Ggt5 | NM_011820.4 | chr10:75589380-75616968 |
| 7848 | Gbp3 | NM_001289492.1 | chr3:142560051-142573212 | 7945 | Ggt6 | NM_027819.2 | chr11:72435525-72438404 |
| 7849 | Gbp4 | NM_001256005.1 | chr5:115765766-105139586 | 7946 | Ggt7 | NM_144786.2 | chr2:155490379-155514846 |
| 7850 | Gbp5 | NM_153564.3 | chr5:142496933-142522344 | 7947 | Ggta1 | NM_001145821.2 | chr2:35400178-35461449 |
| 7851 | Gbp6 | NM_194336.2 | chr5:105270701-105293699 | 7948 | Gh | NM_008117.3 | chr11:106300260-106301896 |
| 7852 | Gbp7 | NM_001083312.1 | chr5:142530035-142560151 | 7949 | Ghdc | NM_031871.1 | chr11:100766331-100770957 |
| 7853 | Gbp8 | NM_029509.4 | chr5:105014152-105053561 | 7950 | Ghitm | NM_001199122.1 | chr14:37120444-37135139 |
| 7854 | Gbp9 | NM_172777.3 | chr5:105078399-105110290 | 7951 | Ghr | NM_001048178.2 | chr15:3327524-3583352 |
| 7855 | Gbx1 | NM_015739.2 | chr5:24504425-24526848 | 7952 | Ghrh | NM_010285.2 | chr2:157349495-157346655 |
| 7856 | Gbx2 | NM_010262.3 | chr1:89927961-89931176 | 7953 | Ghrhr | NM_001003685.3 | chr6:55376294-55388530 |

Fig.21 - 42

| | | | | | | | | |
|---|---|---|---|---|---|---|---|---|
| 7954 | Ghrl | NM_001286404.1 | chr6:113716118-113719454 | | 8051 | Glt6d1 | NM_001039095.1 | chr2:25793966-25815836 |
| 7955 | Ghsr | NM_177330.4 | chr3:27371250-27378010 | | 8052 | Glt8d1 | NM_001165930.1 | chr14:31001392-31012441 |
| 7956 | Gid4 | NM_025757.4 | chr11:60417144-60445277 | | 8053 | Glt8d2 | NM_029102.3 | chr10:82650432-82690650 |
| 7957 | Gid8 | NM_001289651.1 | chr2:180710327-180721599 | | 8054 | Gltp | NM_019821.2 | chr5:114669499-114690935 |
| 7958 | Gif | NM_008118.3 | chr19:11747558-11763447 | | 8055 | Gltpd1 | NM_024472.4 | chr4:155864722-155869440 |
| 7959 | Gigyf1 | NM_031408.2 | chr5:137518879-137527935 | | 8056 | Gltpd2 | NM_146020.1 | chr11:70519208-70520736 |
| 7960 | Gigyf2 | NM_001110212.2 | chr1:87326997-87450810 | | 8057 | Gltscr1 | NM_001081418.1 | chr7:15971261-15999495 |
| 7961 | Gimap1 | NM_008376.3 | chr6:48739046-48743795 | | 8058 | Gltscr1l | NM_001100452.1 | chr17:46798115-46831413 |
| 7962 | Gimap3 | NM_031247.3 | chr6:48764463-48770851 | | 8059 | Gltscr2 | NM_133831.3 | chr7:15937835-15946108 |
| 7963 | Gimap4 | NM_001243199.1 | chr6:48684577-48692062 | | 8060 | Glud1 | NM_008133.4 | chr14:34310728-34349033 |
| 7964 | Gimap5 | NM_175035.5 | chr6:48746196-48754200 | | 8061 | Glul | NM_008131.4 | chr1:153899928-153909723 |
| 7965 | Gimap6 | NM_153175.3 | chr6:48701582-48708244 | | 8062 | Glyat | NM_145935.3 | chr19:12633307-12651737 |
| 7966 | Gimap7 | NM_146167.3 | chr6:48718620-48724636 | | 8063 | Glyatl3 | NM_001145060.1 | chr17:40904740-40914350 |
| 7967 | Gimap8 | NM_001077430.1 | chr6:48647233-48660875 | | 8064 | Glycam1 | NM_001289587.1 | chr15:103562759-103565081 |
| 7968 | Gimap9 | NM_174960.2 | chr6:48676134-48678704 | | 8065 | Glyctk | NM_001039586.1 | chr9:106152859-106158138 |
| 7969 | Gin1 | NM_026250.3 | chr1:97770171-97793708 | | 8066 | Glyr1 | NM_001079814.1 | chr16:5013901-5049910 |
| 7970 | Ginm1 | NM_145418.4 | chr10:7767946-7780917 | | 8067 | Gm10007 | NR_040449.1 | chr19:58296203-58300848 |
| 7971 | Gins1 | NM_001163476.1 | chr2:150909593-150926070 | | 8068 | Gm10012 | NR_028042.1 | chr7:25901855-25902227 |
| 7972 | Gins2 | NM_178856.1 | chr8:120581265-120589075 | | 8069 | Gm10024 | NM_001081452.2 | chr10:77713445-77712009 |
| 7973 | Gins3 | NM_030198.3 | chr5:95633558-95645059 | | 8070 | Gm10033 | NR_038043.1 | chr8:69371024-69395544 |
| 7974 | Gins4 | NM_024240.6 | chr8:23226609-23237668 | | 8071 | Gm10046 | NR_033484.1 | chr7:27765672-27770972 |
| 7975 | Gip | NM_008119.2 | chr11:96024544-96030828 | | 8072 | Gm10052 | NR_002885.3 | chr15:103240481-103244584 |
| 7976 | Gipc1 | NM_018771.3 | chr8:83652677-83664789 | | 8073 | Gm10057 | NM_001243016.1 | chrX:154001589-154005041 |
| 7977 | Gipc2 | NM_016867.1 | chr3:15209840-152165900 | | 8074 | Gm10058 | NM_001109969.2 | chrX:24948455-35427089 |
| 7978 | Gipc3 | NM_148951.1 | chr10:81337761-81343266 | | 8075 | Gm10069 | NR_028592.1 | chr6:128438756-128475845 |
| 7979 | Gipr | NM_001080815.1 | chr7:19157124-19166127 | | 8076 | Gm10081 | NM_001162940.1 | chr7:107105911-107106859 |
| 7980 | Git1 | NM_001004144.1 | chr11:77493411-77507774 | | 8077 | Gm10094 | NM_001142441.1 | chr14:57798217-57802330 |
| 7981 | Git2 | NM_001077359.1 | chr5:114727407-114773492 | | 8078 | Gm10096 | NM_001102678.2 | chrX:24948454-35427090 |
| 7982 | Gja1 | NM_010288.3 | chr10:56377299-56390419 | | 8079 | Gm101 | NM_001115074.1 | chr1:119923518-119995210 |
| 7983 | Gja10 | NM_010289.2 | chr4:32660864-32602382 | | 8080 | Gm10100 | NM_001205033.1 | chr10:77726485-77726848 |
| 7984 | Gja3 | NM_271623.1 | chr14:57034459-57057723 | | 8081 | Gm10104 | NM_001177481.1 | chr8:21065037-21066001 |
| 7985 | Gja4 | NM_008120.3 | chr4:127131419-127134039 | | 8082 | Gm10125 | NR_033552.1 | chr18:5491500-5592437 |
| 7986 | Gja5 | NM_001271628.1 | chr3:97032401-97053634 | | 8083 | Gm10142 | NM_001205035.1 | chr10:77715806-77716169 |
| 7987 | Gja6 | NM_001001496.2 | chrX:160902115-160907052 | | 8084 | Gm10147 | NM_001099919.2 | chrX:24948454-35427090 |
| 7988 | Gja8 | NM_008123.3 | chr3:96913565-96926051 | | 8085 | Gm10190 | NR_028385.1 | chr17:80371856-80373542 |
| 7989 | Gjb1 | NM_008124.3 | chrX:101377234-101385629 | | 8086 | Gm10220 | NM_001134289.1 | chr5:26114763-26121425 |
| 7990 | Gjb2 | NM_008125.3 | chr14:57098601-57104702 | | 8087 | Gm10228 | NM_001270487.1 | chr16:89040922-89041472 |
| 7991 | Gjb3 | NM_001160012.1 | chr4:127325234-127330836 | | 8088 | Gm10229 | NM_001199334.2 | chr16:89015276-89015846 |
| 7992 | Gjb4 | NM_008127.1 | chr4:127354081-127354081 | | 8089 | Gm10230 | NM_001099347.2 | chrX:24948450-35427093 |
| 7993 | Gjb5 | NM_010291.3 | chr4:127354808-127358164 | | 8090 | Gm10248 | NR_033550.1 | chr14:23038194-23094571 |
| 7994 | Gjb6 | NM_001010937.2 | chr14:57123300-57136611 | | 8091 | Gm10267 | NM_001281470.1 | chr18:44156402-44159885 |
| 7995 | Gjc1 | NM_001159382.1 | chr11:102799477-102819519 | | 8092 | Gm10272 | NR_028631.1 | chr10:77706586-77706966 |
| 7996 | Gjc2 | NM_080454.4 | chr11:59175563-59183213 | | 8093 | Gm10280 | NR_033584.1 | chr8:113067261-113093333 |
| 7997 | Gjc3 | NM_080450.4 | chr5:137953808-137962959 | | 8094 | Gm10318 | NM_001162944.1 | chr10:77852858-77853788 |
| 7998 | Gjd2 | NM_010290.2 | chr2:114009600-114013619 | | 8095 | Gm10319 | NR_003624.2 | chr6:122136627-122150958 |
| 7999 | Gjd3 | NM_178596.2 | chr11:98982179-98983016 | | 8096 | Gm10324 | NM_001177832.1 | chr13:66113452-66122836 |
| 8000 | Gjd4 | NM_153086.5 | chr18:9278606-9282809 | | 8097 | Gm10334 | NM_001103153.1 | chr6:41442213-41446097 |
| 8001 | Gje1 | NM_029722.1 | chr10:14715825-14718214 | | 8098 | Gm10336 | NR_045170.1 | chr13:12182716-12186488 |
| 8002 | Gk2 | NM_010294.1 | chr5:97465160-97457008 | | 8099 | Gm10354 | NM_001281514.1 | chr5:14974486-14978899 |
| 8003 | Gk5 | NM_177352.3 | chr9:96119428-96182953 | | 8100 | Gm10364 | NR_073535.1 | chr14:55038461-55042976 |
| 8004 | Gkap1 | NM_019832.3 | chr13:58233350-58274188 | | 8101 | Gm10373 | NR_046064.1 | chr15:43430942-43477036 |
| 8005 | Gkn1 | NM_025466.1 | chr6:87345652-87350915 | | 8102 | Gm10375 | NM_001098269.2 | chr14:43602626-43608013 |
| 8006 | Gkn2 | NM_025467.2 | chr6:87373364-87379494 | | 8103 | Gm10377 | NM_001244671.1 | chr14:41767171-43015576 |
| 8007 | Gkn3 | NM_026860.1 | chr6:87383318-87388935 | | 8104 | Gm10389 | NR_033541.1 | chr15:10600292-10611851 |
| 8008 | Gla | NM_013463.2 | chrX:134588168-134601005 | | 8105 | Gm10390 | NR_045793.1 | chr15:120121095-120139261 |
| 8009 | Glb1 | NM_009752.2 | chr9:114401077-114474379 | | 8106 | Gm10400 | NR_033555.1 | chr6:141340552-141344387 |
| 8010 | Glb1l | NM_029010.1 | chr1:75198234-75210778 | | 8107 | Gm10406 | NM_001164727.1 | chr14:7006114-7027449 |
| 8011 | Glb1l2 | NM_153803.1 | chr9:26763043-26806417 | | 8108 | Gm10408 | NM_001265601.1 | chr14:3449311-3698681 |
| 8012 | Glb1l3 | NM_001113323.1 | chr9:26817952-26860823 | | 8109 | Gm10409 | NR_033121.1 | chr14:3412613-3673272 |
| 8013 | Glcci1 | NM_001286728.1 | chr6:8520057-8597549 | | 8110 | Gm10413 | NM_029288.3 | chr14:3395092-3642992 |
| 8014 | Glce | NM_033320.4 | chr9:62057248-62070606 | | 8111 | Gm10415 | NR_045480.1 | chr6:126286648-126328686 |
| 8015 | Gldc | NM_138595.2 | chr19:30098440-30175441 | | 8112 | Gm10416 | NR_027964.1 | chr5:109833500-109834142 |
| 8016 | Gldn | NM_177595.3 | chr9:54288485-54341777 | | 8113 | Gm10421 | NR_033538.1 | chr12:117144522-117151269 |
| 8017 | Gldnos | NR_045805.1 | chr9:54268579-54301570 | | 8114 | Gm10432 | NR_045741.1 | chr2:100276608-100300908 |
| 8018 | Gle1 | NM_028923.3 | chr2:29935408-29959432 | | 8115 | Gm10433 | NR_045282.1 | chr12:100187967-100193538 |
| 8019 | Glg1 | NM_019749.2 | chr8:111157557-111259202 | | 8116 | Gm10436 | NM_001165254.1 | chr12:88175588-88183884 |
| 8020 | Gli1 | NM_010296.2 | chr10:127329881-127341579 | | 8117 | Gm10439 | NM_001037716.2 | chrX:149594600-149636621 |
| 8021 | Gli2 | NM_001081325.1 | chr1:118834060-119053619 | | 8118 | Gm10440 | NR_038045.1 | chr5:54349991-54358542 |
| 8022 | Gli3 | NM_008130.2 | chr13:15463722-15730025 | | 8119 | Gm10445 | NR_046063.1 | chr8:84412941-84423838 |
| 8023 | Glipr1 | NM_028608.3 | chr10:111985447-111997264 | | 8120 | Gm10456 | NM_001175577.1 | chr5:91987472-91995317 |
| 8024 | Glipr1l1 | NM_027061.1 | chr10:112060188-112078510 | | 8121 | Gm10461 | NR_028520.1 | chr12:76444496-76448698 |
| 8025 | Glipr1l2 | NM_026223.2 | chr10:112083353-112108098 | | 8122 | Gm10466 | NR_033491.1 | chr11:24723005-24730722 |
| 8026 | Glipr2 | NM_027450.3 | chr4:43957701-43979118 | | 8123 | Gm10471 | NM_001177579.1 | chr5:26082171-26089264 |
| 8027 | Gls | NM_147221.2 | chr1:99166379-99225001 | | 8124 | Gm10474 | NR_033481.1 | chrX:68667513-68678399 |
| 8028 | Gls2 | NM_031184.3 | chr10:4594712-4615957 | | 8125 | Gm10486 | NM_001109970.1 | chrX:24948451-35427093 |
| 8029 | Glrx3 | NM_175459.6 | chr19:28258850-28680077 | | 8126 | Gm10487 | NM_001100609.1 | chrX:30820542-30843469 |
| 8030 | Glmn | NM_001161738.1 | chr5:107540996-107597888 | | 8127 | Gm10488 | NM_001099325.2 | chrX:27472052-35427074 |
| 8031 | Glo1 | NM_001113560.1 | chr17:30592861-30612859 | | 8128 | Gm10494 | NR_033462.1 | chr17:79506048-79510486 |
| 8032 | Glod4 | NM_024620.2 | chr11:76220394-76243699 | | 8129 | Gm10509 | NR_045766.1 | chr17:21690211-21692213 |
| 8033 | Glod5 | NM_027227.2 | chrX:8004200-8018492 | | 8130 | Gm10510 | NR_033511.1 | chr17:15350812-15354461 |
| 8034 | Glp1r | NM_021332.2 | chr17:30901866-30936510 | | 8131 | Gm10512 | NR_033458.1 | chr17:13205041-13206211 |
| 8035 | Glp2r | NM_175681.3 | chr11:67706429-67771153 | | 8132 | Gm10516 | NR_033536.1 | chr1:192136897-192151025 |
| 8036 | Glra1 | NM_001290821.1 | chr11:55514238-55608198 | | 8133 | Gm10532 | NR_045879.1 | chr18:75514644-75522806 |
| 8037 | Glra2 | NM_183427.4 | chrX:165129016-165326981 | | 8134 | Gm10536 | NR_033455.1 | chr18:56936259-56940518 |
| 8038 | Glra3 | NM_010438.2 | chr8:55940824-56125352 | | 8135 | Gm10538 | NR_045892.1 | chr1:132729352-132732826 |
| 8039 | Glra4 | NM_010297.2 | chrX:136757679-136779721 | | 8136 | Gm10548 | NR_040834.1 | chr18:34207774-34221772 |
| 8040 | Glrb | NM_001281969.1 | chr3:80843598-80913634 | | 8137 | Gm10549 | NR_045415.1 | chr18:33464162-33474710 |
| 8041 | Glrp1 | NM_008132.2 | chr1:88499870-88510066 | | 8138 | Gm10556 | NR_045881.1 | chr18:4812485-4850959 |
| 8042 | Glrx | NM_053108.4 | chr13:75839885-75850151 | | 8139 | Gm10560 | NR_040563.1 | chr4:156021644-156023824 |
| 8043 | Glrx2 | NM_001038592.1 | chr1:143749567-143749678 | | 8140 | Gm10578 | NR_045885.1 | chr7:137242862-137242609 |
| 8044 | Glrx3 | NM_023140.4 | chr7:137437647-137468694 | | 8141 | Gm10584 | NR_028578.3 | chr7:132315663-132318291 |
| 8045 | Glrx5 | NM_028419.3 | chr12:105032617-105040911 | | 8142 | Gm10591 | NM_001193668.1 | chr4:42612123-42613253 |
| 8046 | Gls | NM_001081081.2 | chr1:52163449-52233232 | | 8143 | Gm10619 | NR_077222.1 | chr7:73808223-73816503 |
| 8047 | Gls2 | NM_001033264.3 | chr10:128194634-128210094 | | 8144 | Gm10635 | NR_045336.1 | chr9:79444036-79519302 |
| 8048 | Glt1d1 | NM_177005.4 | chr5:127632261-127707520 | | 8145 | Gm10636 | NR_033542.1 | chr3:146367152-146378944 |
| 8049 | Glt25d1 | NM_146211.3 | chr8:71611023-71624911 | | 8146 | Gm10637 | NR_040697.1 | chr8:87169746-87199850 |
| 8050 | Glt28d2 | NM_177130.3 | chr3:85869845-85887518 | | 8147 | Gm10638 | NR_027829.1 | chr8:86745698-86747060 |

Fig.21 - 43

| | | | | | | | | |
|---|---|---|---|---|---|---|---|---|
| 8148 | Gm10639 | NM_001122660.1 | chr9:78289927-78305525 | | 8245 | Gm11981 | NR_046025.1 | chr11:6716000-6720037 |
| 8149 | Gm10640 | NR_046062.1 | chr7:31162357-31170641 | | 8246 | Gm11985 | NR_045101.1 | chr11:7183156-7188569 |
| 8150 | Gm10649 | NR_028579.1 | chr8:76749086-76900173 | | 8247 | Gm11992 | NM_001037928.3 | chr11:9048591-9069354 |
| 8151 | Gm10653 | NR_003965.2 | chr9:62841476-62862024 | | 8248 | Gm12 | NM_001195544.1 | chr11:98598290-98599586 |
| 8152 | Gm10658 | NR_045886.1 | chr9:57056896-57071966 | | 8249 | Gm12060 | NR_004857.1 | chr11:23558059-23558842 |
| 8153 | Gm10662 | NM_001201364.1 | chr7:21909453-23144478 | | 8250 | Gm12070 | NR_002890.1 | chr11:26785107-26787859 |
| 8154 | Gm10665 | NM_001167160.1 | chr7:20473959-22464075 | | 8251 | Gm12130 | NR_040295.1 | chr11:38491547-38520045 |
| 8155 | Gm10666 | NM_001167573.1 | chr7:20138122-22134741 | | 8252 | Gm12159 | NR_045100.1 | chr11:45102865-45116928 |
| 8156 | Gm10670 | NM_001167361.1 | chr7:20473960-20474925 | | 8253 | Gm12169 | NM_001163357.1 | chr11:46524250-46538156 |
| 8157 | Gm10677 | NR_046048.1 | chr9:47799159-47818208 | | 8254 | Gm12171 | NM_001163353.1 | chr11:46548412-46556068 |
| 8158 | Gm10681 | NM_001270429.1 | chr3:98499070-98564009 | | 8255 | Gm12185 | NM_001045540.2 | chr11:48904655-48927182 |
| 8159 | Gm10684 | NR_033547.1 | chr9:45107175-45135606 | | 8256 | Gm12191 | NR_028101.1 | chr15:34440505-34443233 |
| 8160 | Gm10696 | NM_001146107.1 | chr3:94174411-94178193 | | 8257 | Gm12216 | NR_033332.1 | chr11:53785488-53859256 |
| 8161 | Gm10714 | NR_040530.1 | chr2:174129037-174123918 | | 8258 | Gm12238 | NR_028480.1 | chr11:55482705-55482829 |
| 8162 | Gm10731 | NR_045392.1 | chr3:40853475-40855285 | | 8259 | Gm12250 | NM_001135315.1 | chr11:58183842-58196198 |
| 8163 | Gm10745 | NR_040751.1 | chr3:11823228-11844359 | | 8260 | Gm12253 | NM_001045542.1 | chr11:58432558-58441622 |
| 8164 | Gm10754 | NR_033537.1 | chr10:97681413-97967090 | | 8261 | Gm12295 | NR_040280.1 | chr11:65277653-65287833 |
| 8165 | Gm10767 | NM_001177750.1 | chr13:66905414-66909166 | | 8262 | Gm12298 | NR_033539.1 | chr11:66905631-66947086 |
| 8166 | Gm10768 | NR_033472.1 | chr19:43838802-43840945 | | 8263 | Gm12338 | NR_110477.1 | chr11:75599645-75600231 |
| 8167 | Gm10778 | NM_001142963.1 | chr10:81649906-81826490 | | 8264 | Gm12359 | NR_033551.1 | chr11:98798308-98810089 |
| 8168 | Gm10782 | NR_046048.1 | chr3:56362899-56368857 | | 8265 | Gm12409 | NR_046068.1 | chr4:45762376-45764223 |
| 8169 | Gm10785 | NR_040389.1 | chr16:91688897-91715755 | | 8266 | Gm12429 | NM_001127167.1 | chr4:42848070-42853888 |
| 8170 | Gm10787 | NR_045882.1 | chr10:77011994-77022214 | | 8267 | Gm12504 | NR_040414.1 | chr4:44121892-44124123 |
| 8171 | Gm10789 | NR_033476.1 | chr16:90342236-90146527 | | 8268 | Gm12505 | NR_040674.1 | chr4:55410442-55418842 |
| 8172 | Gm10790 | NR_033545.1 | chr13:41865914-41933092 | | 8269 | Gm12522 | NR_040660.1 | chr9:108379276-108383741 |
| 8173 | Gm10791 | NR_045889.1 | chr16:84972210-84979451 | | 8270 | Gm12530 | NR_040669.1 | chr4:57172070-57176554 |
| 8174 | Gm10804 | NR_040532.1 | chr2:93452818-93469874 | | 8271 | Gm12603 | NR_033533.1 | chr4:89050306-89084610 |
| 8175 | Gm10814 | NR_045391.1 | chr19:6012619-6018459 | | 8272 | Gm12633 | NR_033610.1 | chr4:90359624-90361314 |
| 8176 | Gm10823 | NR_033475.1 | chr16:27849929-27926128 | | 8273 | Gm12657 | NM_001081019.1 | chr4:94593649-94600319 |
| 8177 | Gm10825 | NR_028580.1 | chr10:22402812-22407470 | | 8274 | Gm12669 | NR_033611.1 | chr7:137437873-137467980 |
| 8178 | Gm10845 | NR_033535.1 | chr14:79860520-79869176 | | 8275 | Gm12695 | NM_001081284.1 | chr4:96723886-96785160 |
| 8179 | Gm10857 | NR_033470.1 | chr2:6132868-6140570 | | 8276 | Gm12709 | NR_040444.1 | chr4:102967265-102989755 |
| 8180 | Gm10863 | NR_029470.1 | chr15:79166085-79216401 | | 8277 | Gm12718 | NR_040673.1 | chr4:103382499-103492188 |
| 8181 | Gm10865 | NR_045746.1 | chr15:78994854-79011041 | | 8278 | Gm12789 | NM_001085520.2 | chr4:101986839-101990213 |
| 8182 | Gm10872 | NR_045747.1 | chr15:76266786-76269839 | | 8279 | Gm12794 | NM_001085516.1 | chr4:101940406-101943183 |
| 8183 | Gm10921 | NM_001085553.1 | chrX:4289286-31383918 | | 8280 | Gm128 | NM_001024841.3 | chr3:95236919-95241109 |
| 8184 | Gm10922 | NM_001080635.1 | chrX:4370635-4372595 | | 8281 | Gm12830 | NR_033617.1 | chr4:114821719-114856166 |
| 8185 | Gm10941 | NR_026944.1 | chr10:77257772-77259223 | | 8282 | Gm12886 | NM_001144948.1 | chr4:121414734-121423099 |
| 8186 | Gm1110 | NM_001281475.1 | chr9:26879566-26928081 | | 8283 | Gm12887 | NM_001099309.1 | chr4:121614003-121622125 |
| 8187 | Gm11110 | NR_033508.1 | chr17:57092022-57106942 | | 8284 | Gm12888 | NM_001033791.3 | chr4:121316315-121324917 |
| 8188 | Gm11127 | NM_001199967.1 | chr17:36055815-36058371 | | 8285 | Gm12942 | NM_001099319.2 | chr4:127126042-127129660 |
| 8189 | Gm11128 | NM_001201389.1 | chr6:85808050-85809877 | | 8286 | Gm12992 | NR_102393.1 | chr4:131899477-131920029 |
| 8190 | Gm11149 | NR_029465.1 | chr9:49518287-49568025 | | 8287 | Gm13003 | NR_040443.1 | chr4:137159081-137165066 |
| 8191 | Gm11166 | NR_024558.1 | chr17:13096659-13098472 | | 8288 | Gm13011 | NM_001126318.1 | chr4:137740153-137409791 |
| 8192 | Gm11186 | NR_045746.1 | chr11:53111450-53120056 | | 8289 | Gm13023 | NM_001007077.2 | chr4:143789333-143795585 |
| 8193 | Gm11190 | NR_033549.1 | chr11:77912126-77929288 | | 8290 | Gm13031 | NR_045911.1 | chr4:140947665-140957902 |
| 8194 | Gm11201 | NR_045873.1 | chr11:79602659-79035005 | | 8291 | Gm13032 | NR_045944.1 | chr4:140810992-140817511 |
| 8195 | Gm11213 | NR_028583.1 | chr4:63596900-63605261 | | 8292 | Gm13034 | NR_030771.1 | chr4:146067523-146068718 |
| 8196 | Gm123 | NM_001080776.1 | chr9:99016964-99035890 | | 8293 | Gm13040 | NM_001113736.1 | chr4:143535954-143542471 |
| 8197 | Gm11237 | NM_001256461.1 | chr4:73605540-73672595 | | 8294 | Gm13043 | NM_001039595.2 | chr4:143511342-143517831 |
| 8198 | Gm11240 | NR_046041.1 | chr4:73791243-73798378 | | 8295 | Gm13051 | NM_001037926.2 | chr4:146097311-146126623 |
| 8199 | Gm11346 | NR_024599.1 | chr13:24598124-24604767 | | 8296 | Gm13057 | NM_001113735.1 | chr4:143511311-143558236 |
| 8200 | Gm11351 | NR_045962.1 | chr13:25921034-25966316 | | 8297 | Gm13078 | NM_001085412.2 | chr4:143719450-143729158 |
| 8201 | Gm1140 | NM_001126317.1 | chrX:67682899-67706350 | | 8298 | Gm13083 | NM_001126324.1 | chr4:143615002-143618595 |
| 8202 | Gm1141 | NR_027801.1 | chrX:71932437-71940871 | | 8299 | Gm13084 | NM_001005371.3 | chr4:143809990-143816093 |
| 8203 | Gm11413 | NR_045450.1 | chr4:83378316-83390668 | | 8300 | Gm13088 | NM_001126325.1 | chr4:143653759-143657246 |
| 8204 | Gm11426 | NR_033582.1 | chr11:82633352-82636309 | | 8301 | Gm13102 | NM_001085419.1 | chr4:144099879-144110101 |
| 8205 | Gm11437 | NM_001037692.1 | chr11:84148360-84167476 | | 8302 | Gm13103 | NM_177571.3 | chr4:143846496-143853637 |
| 8206 | Gm11468 | NR_033467.1 | chr2:166273907-166294831 | | 8303 | Gm13119 | NM_001034101.2 | chr4:144357963-144364419 |
| 8207 | Gm11487 | NM_001013393.1 | chr4:73401031-73405072 | | 8304 | Gm13124 | NM_001085542.1 | chr4:144554999-144565134 |
| 8208 | Gm11517 | NR_033523.1 | chr11:96791351-96798156 | | 8305 | Gm13125 | NM_001115077.1 | chr4:144372759-144377933 |
| 8209 | Gm11529 | NR_033524.1 | chr11:96446898-96464547 | | 8306 | Gm13128 | NM_001085541.1 | chr4:144430248-144433465 |
| 8210 | Gm11538 | NR_108029.1 | chr11:96203453-96205480 | | 8307 | Gm13139 | NM_001083918.1 | chr4:145783542-146468233 |
| 8211 | Gm11541 | NM_001007584.2 | chr11:94694497-94704499 | | 8308 | Gm13152 | NM_001039209.2 | chr4:147175865-147513420 |
| 8212 | Gm11544 | NM_001205037.1 | chr11:94844830-94849593 | | 8309 | Gm13154 | NM_001014397.4 | chr4:147553276-147585201 |
| 8213 | Gm11545 | NM_001105561.1 | chr11:94748305-94761182 | | 8310 | Gm13157 | NM_001177189.3 | chr4:147753973-147809788 |
| 8214 | Gm11548 | NR_040590.1 | chr3:36499803-36506809 | | 8311 | Gm13177 | NM_001081243.1 | chr4:144613706-144623398 |
| 8215 | Gm11549 | NR_040411.1 | chr3:36515056-36521445 | | 8312 | Gm13178 | NM_001085536.1 | chr4:144703190-144721404 |
| 8216 | Gm11554 | NM_001099313.2 | chr11:99798185-99809892 | | 8313 | Gm13212 | NM_001035101.1 | chr4:145617145-145624394 |
| 8217 | Gm11559 | NM_001177484.2 | chr11:99864475-99865571 | | 8314 | Gm1322 | NM_001033477.3 | chr2:67173833-67186212 |
| 8218 | Gm11562 | NM_001177537.2 | chr11:99619597-99620404 | | 8315 | Gm13238 | NR_033612.1 | chr4:145837218-145837992 |
| 8219 | Gm11563 | NM_001126320.2 | chr11:99657941-99658959 | | 8316 | Gm13242 | NM_001103158.2 | chr4:145670896-145704437 |
| 8220 | Gm11564 | NM_001100614.1 | chr11:99814975-99815866 | | 8317 | Gm13247 | NM_001243138.1 | chr4:146501999-146539395 |
| 8221 | Gm11565 | NM_001145750.1 | chr11:99914750-99915671 | | 8318 | Gm13251 | NM_001085522.2 | chr4:146449029-146469440 |
| 8222 | Gm11567 | NM_001101613.1 | chr11:99879186-99880229 | | 8319 | Gm13271 | NM_001085528.1 | chr4:88754867-88755416 |
| 8223 | Gm11568 | NM_001205030.1 | chr11:99857916-99859060 | | 8320 | Gm13272 | NM_001161608.1 | chr4:88779849-88780660 |
| 8224 | Gm11569 | NM_001099312.1 | chr11:99803547-99804446 | | 8321 | Gm13275 | NM_001085533.2 | chr4:88793741-88801130 |
| 8225 | Gm11570 | NM_001256057.1 | chr11:99984702-99986593 | | 8322 | Gm13276 | NM_001085532.3 | chr4:88785053-88786515 |
| 8226 | Gm11595 | NM_001126322.1 | chr11:99771713-99772913 | | 8323 | Gm13277 | NM_001098540.3 | chr4:88787976-88789438 |
| 8227 | Gm11596 | NM_001099311.2 | chr11:99792674-99793292 | | 8324 | Gm13278 | NM_001098841.3 | chr4:88790894-88798208 |
| 8228 | Gm11627 | NR_040286.1 | chr11:102576398-102579119 | | 8325 | Gm13279 | NM_001243166.1 | chr4:88791389-98798204 |
| 8229 | Gm11651 | NR_104047.1 | chr11:105965606-105985694 | | 8326 | Gm13283 | NM_001085531.2 | chr4:88760773-88761584 |
| 8230 | Gm11696 | NR_038097.1 | chr11:109354777-109363654 | | 8327 | Gm13285 | NM_001161609.1 | chr4:88773993-88806734 |
| 8231 | Gm11710 | NM_001101656.2 | chr11:115020688-115037690 | | 8328 | Gm13286 | NM_001243150.1 | chr4:88757843-88758392 |
| 8232 | Gm11744 | NM_001163318.1 | chr11:116657107-116668389 | | 8329 | Gm13288 | NM_001243167.1 | chr4:88805530-88808380 |
| 8233 | Gm11747 | NR_045902.1 | chr11:118454199-118454995 | | 8330 | Gm13290 | NM_001243155.1 | chr4:88775833-88806993 |
| 8234 | Gm11757 | NM_001085538.2 | chr4:73872219-73905921 | | 8331 | Gm13293 | NR_040369.1 | chr2:11339948-11344106 |
| 8235 | Gm11758 | NM_001097978.2 | chr4:73872218-73905953 | | 8332 | Gm13298 | NM_001085530.1 | chr4:144078-42528237 |
| 8236 | Gm11762 | NR_045099.1 | chr11:119548629-119569046 | | 8333 | Gm13304 | NM_001193666.1 | chr4:42114787-42115917 |
| 8237 | Gm11780 | NM_001277919.1 | chr4:4527773-4529458 | | 8334 | Gm13305 | NM_001099348.1 | chr4:3809-42665762 |
| 8238 | Gm11837 | NM_001243100.1 | chr4:14930640-14953030 | | 8335 | Gm13306 | NM_001164046.1 | chr4:3059-42666005 |
| 8239 | Gm11937 | NM_001099346.1 | chr11:99609793-99610189 | | 8336 | Gm13308 | NM_001177580.1 | chr4:173291-42440009 |
| 8240 | Gm11938 | NM_001127354.1 | chr11:99602645-99603308 | | 8337 | Gm13315 | NR_028497.1 | chr2:14720643-14722622 |
| 8241 | Gm11944 | NR_045708.1 | chr11:3308999-3320722 | | 8338 | Gm13363 | NR_002688.1 | chr1:30941591-30949710 |
| 8242 | Gm11961 | NR_027797.1 | chr11:4625375-4630011 | | 8339 | Gm13375 | NR_033225.1 | chr2:20968873-20970348 |
| 8243 | Gm11974 | NR_045893.1 | chr11:6525590-6528760 | | 8340 | Gm13446 | NR_045894.1 | chr2:35549533-35558702 |
| 8244 | Gm11978 | NR_028586.1 | chr11:6650147-6660236 | | 8341 | Gm13483 | NR_040361.1 | chr2:50296809-50365000 |

Fig.21 - 44

| | | | | | | | |
|---|---|---|---|---|---|---|---|
| 8342 | Gm13490 | NR_040639.1 | chr2:51656965-51732009 | 8439 | Gm15023 | NM_001099321.2 | chrX:135169304-135502913 |
| 8343 | Gm13497 | NR_040636.1 | chr2:51241830-51295945 | 8440 | Gm15055 | NR_110440.1 | chr6:52102948-52113684 |
| 8344 | Gm13498 | NR_033595.1 | chr2:50909683-50911846 | 8441 | Gm15056 | NM_001177471.1 | chr8:20900605-20901973 |
| 8345 | Gm13539 | NR_045340.1 | chr2:25784616-25787022 | 8442 | Gm15091 | NM_001122735.1 | chrX:149941654-149984982 |
| 8346 | Gm13544 | NR_040365.1 | chr2:58276778-58286902 | 8443 | Gm15093 | NM_001099920.1 | chrX:148322133-149487784 |
| 8347 | Gm13546 | NR_045895.1 | chr2:58163973-58177063 | 8444 | Gm15097 | NM_001198987.2 | chrX:149784503-149826694 |
| 8348 | Gm13547 | NM_001177392.1 | chr2:29761527-29764089 | 8445 | Gm15104 | NM_001101501.1 | chrX:150312950-150313364 |
| 8349 | Gm13580 | NR_046065.1 | chr2:60411524-60412574 | 8446 | Gm15107 | NM_001081648.1 | chrX:148180723-148224710 |
| 8350 | Gm13582 | NR_045335.1 | chr2:60964375-60975151 | 8447 | Gm15114 | NM_001082966.1 | chrX:148889948-148521446 |
| 8351 | Gm136 | NM_001033255.2 | chr4:34743787-34756259 | 8448 | Gm15127 | NM_001114400.2 | chrX:148663603-149984982 |
| 8352 | Gm13629 | NR_033495.1 | chr2:66440879-66547472 | 8449 | Gm15133 | NR_040749.1 | chr7:104315030-104324838 |
| 8353 | Gm13710 | NR_046046.1 | chr2:84500747-84506873 | 8450 | Gm15140 | NM_001243017.1 | chrX:154109633-154120688 |
| 8354 | Gm13749 | NR_027824.1 | chr1:63964726-63968999 | 8451 | Gm15179 | NR_037976.1 | chr1:75368209-75375015 |
| 8355 | Gm13752 | NR_040370.1 | chr2:80391363-80398216 | 8452 | Gm15217 | NR_027981.1 | chr14:46379523-46383806 |
| 8356 | Gm13763 | NM_001270423.1 | chr2:96322222-90325126 | 8453 | Gm1527 | NM_001033479.4 | chr3:28892616-28926724 |
| 8357 | Gm13807 | NR_040529.1 | chr2:93403546-93417830 | 8454 | Gm15284 | NM_001177485.1 | chr8:21134649-21135598 |
| 8358 | Gm13826 | NM_001271590.1 | chr5:115102921-115110268 | 8455 | Gm15292 | NM_001177487.1 | chr8:21249761-21250461 |
| 8359 | Gm13871 | NM_001177578.2 | chr4:73872218-73905921 | 8456 | Gm15293 | NM_001177486.1 | chr8:21201603-21202446 |
| 8360 | Gm13889 | NM_001145034.1 | chr2:93955809-93957100 | 8457 | Gm15299 | NM_001170955.1 | chr8:21315549-21316387 |
| 8361 | Gm13939 | NR_033473.1 | chr2:109902395-109913319 | 8458 | Gm15308 | NM_001177521.1 | chr8:21529029-21530012 |
| 8362 | Gm13944 | NR_040368.1 | chr2:77462643-77480938 | 8459 | Gm15315 | NM_001177528.1 | chr8:21665796-21666713 |
| 8363 | Gm14005 | NR_028589.1 | chr2:128298862-128429351 | 8460 | Gm15319 | NM_001177408.1 | chr2:20337663-20363202 |
| 8364 | Gm14015 | NR_040358.1 | chr2:106463822-106523103 | 8461 | Gm15328 | NR_045399.1 | chr18:16816406-16822783 |
| 8365 | Gm14023 | NR_040371.1 | chr2:129297369-129307826 | 8462 | Gm15348 | NR_033546.1 | chr8:12706943-12719127 |
| 8366 | Gm14057 | NR_024097.1 | chr2:130801965-130804101 | 8463 | Gm15350 | NR_045775.1 | chr8:12828337-12831919 |
| 8367 | Gm14085 | NM_001085515.1 | chr2:122484940-122528040 | 8464 | Gm15395 | NM_001040027.2 | chr1:18260523-18265138 |
| 8368 | Gm14092 | NM_001037929.2 | chr2:145549454-145554982 | 8465 | Gm15401 | NR_040421.1 | chr6:72629830-72637717 |
| 8369 | Gm14124 | NM_001142410.1 | chr2:150257516-150270300 | 8466 | Gm15408 | NR_040429.1 | chr5:149006961-149012776 |
| 8370 | Gm14137 | NM_001039223.3 | chr2:119174508-119177575 | 8467 | Gm15412 | NR_046043.1 | chr7:96339482-96341964 |
| 8371 | Gm14139 | NM_001145863.1 | chr2:150181754-150193279 | 8468 | Gm15413 | NR_045874.1 | chr7:96791432-96801549 |
| 8372 | Gm14151 | NM_001097977.1 | chr2:151086785-151103809 | 8469 | Gm15417 | NR_040403.1 | chr3:89391863-89398779 |
| 8373 | Gm14164 | NR_033505.1 | chr2:152345668-152375322 | 8470 | Gm15421 | NR_004442.1 | chr5:22528220-22529030 |
| 8374 | Gm14189 | NR_040372.1 | chr2:156609197-156613422 | 8471 | Gm15441 | NR_040409.1 | chr3:96555767-96566801 |
| 8375 | Gm14204 | NR_040358.1 | chr2:158598172-158610723 | 8472 | Gm15446 | NR_040366.1 | chr5:109933562-109941710 |
| 8376 | Gm14207 | NR_030683.1 | chr2:119321198-119326197 | 8473 | Gm15455 | NM_001161816.1 | chr1:33835898-33838914 |
| 8377 | Gm14288 | NM_001033123.3 | chr2:175275129-176432581 | 8474 | Gm15471 | NR_040412.1 | chr3:103803128-103808440 |
| 8378 | Gm14295 | NM_001205057.2 | chr2:176798599-176800704 | 8475 | Gm1553 | NM_001255990.1 | chr10:82486632-82492618 |
| 8379 | Gm14305 | NM_001099327.1 | chr2:176708352-176721813 | 8476 | Gm15545 | NR_045266.1 | chr7:44986899-44994601 |
| 8380 | Gm14306 | NM_001242944.1 | chr2:175470024-175480553 | 8477 | Gm156 | NM_001014997.1 | chr6:129766646-129775849 |
| 8381 | Gm14308 | NM_001099349.2 | chr2:175821833-176636319 | 8478 | Gm15612 | NR_045880.1 | chr6:88842853-88847274 |
| 8382 | Gm14322 | NM_001243903.1 | chr2:177759287-177773275 | 8479 | Gm1564 | NM_001175576.2 | chr1:102665584-102682238 |
| 8383 | Gm14325 | NM_001024849.2 | chr2:177828990-177840318 | 8480 | Gm15645 | NR_033578.1 | chr7:105861780-105863327 |
| 8384 | Gm14326 | NM_001190302.2 | chr2:177945490-177957288 | 8481 | Gm15663 | NR_038032.1 | chr10:105574550-105588870 |
| 8385 | Gm14327 | NR_038101.1 | chr2:177897162-177927850 | 8482 | Gm15679 | NR_110579.1 | chr8:99011886-99032741 |
| 8386 | Gm14345 | NM_001085545.1 | chrX:3700233-3702192 | 8483 | Gm15698 | NR_003564.1 | chr11:88964665-88965917 |
| 8387 | Gm14346 | NM_001085551.1 | chrX:3441731-3443690 | 8484 | Gm15706 | NR_045598.1 | chr6:145250551-145251856 |
| 8388 | Gm14347 | NM_001085543.1 | chrX:4196575-4198535 | 8485 | Gm15708 | NR_040432.1 | chr5:144277060-144280514 |
| 8389 | Gm14351 | NM_001085552.2 | chrX:3750931-3752885 | 8486 | Gm15713 | NR_046026.1 | chr16:43410517-43420196 |
| 8390 | Gm14374 | NM_001085523.1 | chrX:5690066-5671026 | 8487 | Gm15760 | NR_030670.1 | chr16:20546111-20548556 |
| 8391 | Gm14378 | NM_001195258.1 | chr8:4248213-4251423 | 8488 | Gm15772 | NR_003373.1 | chr11:68901588-68904534 |
| 8392 | Gm14379 | NR_026741.1 | chrX:7375924-7378042 | 8489 | Gm15787 | NR_040436.1 | chr5:110167507-110176504 |
| 8393 | Gm14391 | NM_001099308.1 | chr2:175194278-175881883 | 8490 | Gm15800 | NM_181421.4 | chr5:121226218-121368577 |
| 8394 | Gm14393 | NM_001085546.2 | chr2:175067769-175080569 | 8491 | Gm15816 | NM_001282148.1 | chr8:23138784-23149585 |
| 8395 | Gm14403 | NR_036450.1 | chr2:177498225-177512311 | 8492 | Gm15850 | NR_046167.1 | chr1:136127718-136131183 |
| 8396 | Gm14405 | NR_040256.1 | chr2:176829452-176864437 | 8493 | Gm1587 | NM_001033440.2 | chr14:77793944-77798953 |
| 8397 | Gm14420 | NM_001175568.1 | chr2:177464741-177479194 | 8494 | Gm15880 | NR_040343.1 | chr7:80636916-80644384 |
| 8398 | Gm14431 | NM_001177404.1 | chr2:176521004-176533821 | 8495 | Gm15881 | NM_001177534.2 | chr8:58692848-58700796 |
| 8399 | Gm14436 | NM_001242943.1 | chr2:175470059-175483322 | 8496 | Gm15910 | NR_038023.1 | chr10:120867628-129863328 |
| 8400 | Gm14440 | NM_001199308.1 | chr2:175275124-175801037 | 8497 | Gm15915 | NR_038017.1 | chr10:93674217-93683322 |
| 8401 | Gm14446 | NM_001101605.1 | chr19:34592887-34601968 | 8498 | Gm15941 | NR_045283.1 | chr15:37421132-37432664 |
| 8402 | Gm14458 | NM_001099326.2 | chrX:8985939-8986672 | 8499 | Gm15987 | NR_045009.2 | chr6:128952352-128975029 |
| 8403 | Gm14459 | NM_001126491.1 | chrX:8514051-8524954 | 8500 | Gm15997 | NR_045423.1 | chr5:149489055-149538030 |
| 8404 | Gm14461 | NM_177843.3 | chr2:78237546-78302230 | 8501 | Gm16023 | NR_040441.1 | chr4:155608296-155624755 |
| 8405 | Gm14474 | NM_001242947.1 | chrX:11302431-11302921 | 8502 | Gm16039 | NM_001302353.1 | chr6:8259288-8428767 |
| 8406 | Gm14475 | NM_001242954.1 | chrX:11324659-11324976 | 8503 | Gm16046 | NM_001033442.3 | chr17:7025542-8101228 |
| 8407 | Gm14476 | NM_001242950.1 | chrX:11299320-11324976 | 8504 | Gm16062 | NR_045686.1 | chr11:59810079-59818362 |
| 8408 | Gm14477 | NM_001242949.1 | chrX:11305655-11305972 | 8505 | Gm16063 | NR_046178.1 | chr5:119625941-119634462 |
| 8409 | Gm14478 | NM_001242953.1 | chrX:11318285-11321894 | 8506 | Gm16130 | NM_001243265.1 | chr9:58032273-58048997 |
| 8410 | Gm14479 | NM_001242958.1 | chrX:11315150-11315475 | 8507 | Gm16157 | NR_040340.1 | chr7:68266338-68276594 |
| 8411 | Gm14482 | NM_001242952.1 | chrX:11308754-11321931 | 8508 | Gm16287 | NR_033543.1 | chr4:139175406-139180655 |
| 8412 | Gm14483 | NM_001110017.1 | chrX:11299256-11309260 | 8509 | Gm16291 | NR_045788.1 | chr15:39797044-39812377 |
| 8413 | Gm14484 | NM_001025260.2 | chrX:11311933-11312427 | 8510 | Gm16294 | NR_046185.1 | chr15:40513321-40527277 |
| 8414 | Gm14496 | NM_001205282.1 | chr2:181991225-182001087 | 8511 | Gm1631 | NR_037979.1 | chr2:71719416-71730966 |
| 8415 | Gm14499 | NM_001277184.1 | chrX:8975717-9044410 | 8512 | Gm16325 | NR_045949.1 | chr3:146641933-146651715 |
| 8416 | Gm14501 | NM_001085537.2 | chrX:9350598-9351137 | 8513 | Gm16336 | NR_045267.1 | chr7:110904984-110905851 |
| 8417 | Gm14511 | NM_001085525.2 | chrX:8975717-8976559 | 8514 | Gm16367 | NM_001031622.2 | chr5:82194-95194489 |
| 8418 | Gm14525 | NM_001162544.1 | chr2:26672279-26702638 | 8515 | Gm16381 | NM_001166062.2 | chr12:87644119-87846716 |
| 8419 | Gm14548 | NM_001166672.1 | chr7:3884213-3898092 | 8516 | Gm16386 | NR_030709.2 | chr17:22776229-22817747 |
| 8420 | Gm14624 | NM_001230485.1 | chrX:55430234-55446892 | 8517 | Gm16390 | NM_001097980.1 | chrX:154886802-154890267 |
| 8421 | Gm14632 | NM_001006510.2 | chrX:30329715-30352646 | 8518 | Gm16404 | NM_001220497.1 | chrX:55551598-55568457 |
| 8422 | Gm14634 | NR_045852.1 | chrX:12762277-12821492 | 8519 | Gm16405 | NM_001166646.1 | chrX:54531207-54639016 |
| 8423 | Gm14635 | NR_045321.1 | chrX:12339778-12354996 | 8520 | Gm16430 | NM_001166601.1 | chrX:54622211-54639016 |
| 8424 | Gm14685 | NM_001025383.2 | chrX:73123067-73143424 | 8521 | Gm16432 | NM_001034899.3 | chr1:177991434-178048291 |
| 8425 | Gm14692 | NM_001163195.1 | chrX:67682991-67706258 | 8522 | Gm16445 | NM_001243032.1 | chrX:154152570-154156887 |
| 8426 | Gm14718 | NR_038463.1 | chrX:57200636-57204376 | 8523 | Gm16451 | NM_001177149.1 | chr7:20121655-22118245 |
| 8427 | Gm14725 | NM_001081476.1 | chrX:70546557-70546385 | 8524 | Gm1647 | NR_126833.3 | chr3:69131233-69157177 |
| 8428 | Gm14743 | NM_001126213.1 | chrX:78240461-78245921 | 8525 | Gm16497 | NR_045003.1 | chr2:142616533-142885684 |
| 8429 | Gm14744 | NM_001085544.1 | chrX:77864757-77870033 | 8526 | Gm16501 | NM_001113395.1 | chrY:2599098-2720674 |
| 8430 | Gm14781 | NM_001205268.1 | chrX:91632193-91635671 | 8527 | Gm16515 | NM_025294.5 | chr11:60902245-60913792 |
| 8431 | Gm14812 | NR_033544.2 | chrX:99405330-99443797 | 8528 | Gm16523 | NR_033526.1 | chr9:157485-39162235 |
| 8432 | Gm14819 | NM_001110250.2 | chrX:24948450-35427093 | 8529 | Gm1653 | NR_040691.1 | chr3:149274736-149279980 |
| 8433 | Gm14827 | NR_045329.1 | chrX:94442731-94447727 | 8530 | Gm1632 | NM_001134752.1 | chr7:6415174-6431086 |
| 8434 | Gm14850 | NM_001177522.1 | chr8:21427427-21566350 | 8531 | Gm16548 | NR_037987.1 | chr1:164148575-164152217 |
| 8435 | Gm14851 | NM_001177482.1 | chr2:21094970-21096050 | 8532 | Gm16551 | NR_045284.1 | chr9:74848436-74852672 |
| 8436 | Gm14858 | NM_001256650-102257689 | chrX:102252656-102257689 | 8533 | Gm16576 | NR_045069.1 | chr15:79742697-79757994 |
| 8437 | Gm14920 | NM_001102665.1 | chrX:117014756-117015104 | 8534 | Gm16596 | NR_045751.1 | chr12:108556401-108555618 |
| 8438 | Gm15008 | NR_045917.1 | chrX:36910833-38911985 | 8535 | Gm166 | NM_001033040.3 | chr7:127582382-127588595 |

| | | | | | | | |
|---|---|---|---|---|---|---|---|
| 8730 | Gm2694 | NR_033430.1 | chr8:87472811-87525954 | 8827 | Gm4719 | NR_045952.1 | chr17:89379240-89384993 |
| 8731 | Gm2696 | NM_001205009.1 | chr10:77814681-77815404 | 8828 | Gm4724 | NM_001256480.1 | chr2:175419391-175435777 |
| 8732 | Gm2721 | NR_045085.1 | chr12:105394855-105403760 | 8829 | Gm4736 | NM_053251.1 | chr6:132114220-132364135 |
| 8733 | Gm2762 | NR_037991.1 | chr13:53393688-53456630 | 8830 | Gm4745 | NM_001038676.1 | chr7:14659707-14665996 |
| 8734 | Gm2799 | NM_001168334.1 | chrX:32278393-32562004 | 8831 | Gm4759 | NR_003967.2 | chr7:106421549-106441073 |
| 8735 | Gm2825 | NM_001168337.1 | chrX:32973896-32975846 | 8832 | Gm4763 | NM_177593.1 | chr7:24722493-24724290 |
| 8736 | Gm2837 | NR_040388.1 | chrX:33056285-33057063 | 8833 | Gm4776 | NR_037690.1 | chr1:46020414-46030437 |
| 8737 | Gm2848 | NR_046069.1 | chr13:52569879-52573225 | 8834 | Gm4787 | NM_001038995.2 | chr12:81376990-81379486 |
| 8738 | Gm2863 | NM_001099333.3 | chrX:33313337-33315288 | 8835 | Gm4788 | NM_001029977.3 | chr1:139697918-139781239 |
| 8739 | Gm2897 | NM_001177715.2 | chr14:3049284-3076838 | 8836 | Gm4791 | NM_001243258.1 | chr9:46998740-47003860 |
| 8740 | Gm2913 | NM_001243015.1 | chrX:33750925-33577346 | 8837 | Gm4792 | NR_038209.1 | chr10:94293662-94298703 |
| 8741 | Gm2927 | NM_001282034.1 | chrX:33657139-33659082 | 8838 | Gm4794 | NM_001101452.1 | chr10:33766423-33782115 |
| 8742 | Gm2933 | NM_001145038.1 | chrX:33575613-33702349 | 8839 | Gm4814 | NR_036451.1 | chr13:93073203-93074755 |
| 8743 | Gm2a | NM_010299.3 | chr11:55097984-55113028 | 8840 | Gm4827 | NR_045935.1 | chr16:50019657-50072852 |
| 8744 | Gm3002 | NR_033388.1 | chr14:3814912-3830681 | 8841 | Gm4832 | NM_001190356.1 | chr17:88125511-88131116 |
| 8745 | Gm3020 | NR_033117.1 | chr14:3412613-3669589 | 8842 | Gm4836 | NM_009529.3 | chrX:27472050-35427076 |
| 8746 | Gm3086 | NR_036607.1 | chr12:69963408-69969744 | 8843 | Gm4841 | NM_001034859.3 | chr18:60268300-60273267 |
| 8747 | Gm3139 | NM_001243937.1 | chr5:40898-945338367 | 8844 | Gm4846 | NM_001164306.1 | chr1:166483612-166497588 |
| 8748 | Gm3143 | NR_038347.1 | chr3:34699639-34716662 | 8845 | Gm4847 | NM_001164312.1 | chr1:166628970-166647693 |
| 8749 | Gm3219 | NR_027380.1 | chr14:34345054-34345658 | 8846 | Gm4850 | NR_015347.1 | chr1:31264846-31268061 |
| 8750 | Gm3230 | NR_033642.1 | chr2:19655805-19657897 | 8847 | Gm4858 | NM_001034860.2 | chr3:93068822-93075505 |
| 8751 | Gm3238 | NM_001101630.1 | chr10:77770632-77771325 | 8848 | Gm4861 | NM_177665.3 | chr3:137550044-137552622 |
| 8752 | Gm3258 | NM_011509.2 | chr10:31413729-31414435 | 8849 | Gm4871 | NM_001101463.1 | chr5:145029599-145032764 |
| 8753 | Gm3259 | NM_001270456.1 | chr5:95309922-95343575 | 8850 | Gm4872 | NR_073371.1 | chr6:53221163-53224975 |
| 8754 | Gm3264 | NM_001242945.1 | chr14:4430991-4875851 | 8851 | Gm4884 | NM_183186.2 | chr7:41032718-41043302 |
| 8755 | Gm3279 | NR_046071.1 | chr6:55684570-55694574 | 8852 | Gm4890 | NR_045822.1 | chr8:79295077-79307774 |
| 8756 | Gm3285 | NM_001101631.1 | chr10:77861974-77862638 | 8853 | Gm4894 | NM_177701.3 | chr9:49250530-49280594 |
| 8757 | Gm3286 | NM_001122678.2 | chr5:82558-95804235 | 8854 | Gm4906 | NM_001114529.1 | chrX:11327821-11328151 |
| 8758 | Gm3317 | NM_001242941.2 | chr14:5163641-5522929 | 8855 | Gm4907 | NM_001034864.3 | chrX:23892762-23907550 |
| 8759 | Gm3336 | NM_001195253.1 | chr8:70718542-70722635 | 8856 | Gm4922 | NM_177706.4 | chr10:18779726-18786793 |
| 8760 | Gm3383 | NM_001291993.1 | chr14:5763194-5814642 | 8857 | Gm4925 | NM_001037166.2 | chr10:88729540-88731101 |
| 8761 | Gm3402 | NM_001243111.1 | chr5:146514122-146558915 | 8858 | Gm4926 | NR_028066.1 | chr11:46636505-46645006 |
| 8762 | Gm3404 | NM_001243109.1 | chr5:146529800-146528553 | 8859 | Gm4937 | NM_001013760.2 | chrX:76264305-76267673 |
| 8763 | Gm3409 | NM_001243113.1 | chr5:146537647-146540427 | 8860 | Gm4944 | NM_001205095.1 | chr17:22197264-22225614 |
| 8764 | Gm3414 | NR_027993.1 | chr5:45719666-45727578 | 8861 | Gm4951 | NM_001033767.3 | chr18:60212076-80247820 |
| 8765 | Gm3415 | NM_001243114.1 | chr5:146502376-146558915 | 8862 | Gm4952 | NM_001101762.2 | chr19:12600015-12627616 |
| 8766 | Gm3417 | NM_001123368.1 | chr17:14964188-15041559 | 8863 | Gm4956 | NR_002858.1 | chr1:21285245-21298312 |
| 8767 | Gm3428 | NR_030730.1 | chr9:35848544-35849880 | 8864 | Gm4961 | NR_045694.2 | chr5:30092939-30097686 |
| 8768 | Gm3434 | NR_030729.1 | chr9:36134286-36135630 | 8865 | Gm4971 | NR_033604.1 | chr7:73685491-73688563 |
| 8769 | Gm3435 | NM_001123372.1 | chr17:15009839-15022449 | 8866 | Gm4975 | NM_001195687.1 | chr8:63924693-63952170 |
| 8770 | Gm3458 | NR_110518.1 | chr9:71211912-71215386 | 8867 | Gm4980 | NM_001195291.1 | chr7:99624066-99627103 |
| 8771 | Gm3488 | NM_001256181.1 | chr14:5501623-5522929 | 8868 | Gm4981 | NM_001034869.2 | chr10:58234847-58236660 |
| 8772 | Gm3500 | NM_001256886.1 | chr14:5365791-5741602 | 8869 | Gm4984 | NM_001101484.1 | chrX:12651882-12652820 |
| 8773 | Gm3558 | NM_001270842.1 | chr14:7545150-7568568 | 8870 | Gm5 | NR_024513.1 | chr5:150499746-150502219 |
| 8774 | Gm3604 | NM_001162160.1 | chr13:62367715-62383174 | 8871 | Gm5039 | NR_003647.2 | chr12:88320121-88321792 |
| 8775 | Gm362 | NM_001195271.1 | chrX:43596988-43593530 | 8872 | Gm5065 | NR_003622.2 | chr7:5350541-5360682 |
| 8776 | Gm364 | NM_001128625.1 | chrX:57409148-57488771 | 8873 | Gm5069 | NR_003623.1 | chr1:180326968-180330549 |
| 8777 | Gm3646 | NM_001177348.1 | chr1:39804140-39805332 | 8874 | Gm5071 | NM_001256004.1 | chrX:91931945-91932980 |
| 8778 | Gm3696 | NM_001024712.2 | chr14:7083024-7105457 | 8875 | Gm5072 | NM_001144678.1 | chrX:91392499-91481160 |
| 8779 | Gm3701 | NM_001243011.1 | chrX:3955043-3957002 | 8876 | Gm5082 | NM_001145878.1 | chr13:41656761-41656777 |
| 8780 | Gm3706 | NM_001243001.1 | chrX:3441735-34161584 | 8877 | Gm5083 | NR_045285.1 | chr13:44121166-44125179 |
| 8781 | Gm3716 | NR_045078.1 | chr5:64593862-64610699 | 8878 | Gm5084 | NR_026449.1 | chr13:60205470-60216018 |
| 8782 | Gm3750 | NM_001099643.2 | chrX:4800411-4802359 | 8879 | Gm5086 | NR_046157.1 | chr3:97559999-97583994 |
| 8783 | Gm3763 | NM_001243024.1 | chrX:4952134-4954077 | 8880 | Gm5087 | NR_121588.1 | chr14:13157388-13284638 |
| 8784 | Gm3776 | NM_001243092.1 | chr9:78257128-78269166 | 8881 | Gm5088 | NR_002862.3 | chr14:89896223-89899447 |
| 8785 | Gm382 | NM_001033241.3 | chrX:127049971-127063986 | 8882 | Gm5089 | NR_033325.1 | chr14:122434853-122451115 |
| 8786 | Gm3893 | NR_033506.1 | chr4:41889794-42233950 | 8883 | Gm5091 | NR_046164.1 | chr17:15231584-15240783 |
| 8787 | Gm3985 | NM_001177589.1 | chr8:32888504-32950026 | 8884 | Gm5095 | NR_033454.1 | chr18:47537734-47718636 |
| 8788 | Gm4013 | NR_033452.1 | chr18:42274379-42275197 | 8885 | Gm5105 | NR_037975.1 | chr3:138048760-138067388 |
| 8789 | Gm4027 | NM_001177564.1 | chr12:87618908-87622143 | 8886 | Gm5108 | NM_001256184.1 | chr5:67941668-67977070 |
| 8790 | Gm4070 | NM_001243059.1 | chr7:105895118-106215337 | 8887 | Gm5111 | NM_183309.3 | chr6:48589444-48590584 |
| 8791 | Gm41 | NR_036689.1 | chrX:86345474-86354994 | 8888 | Gm5113 | NM_001033540.2 | chr7:30169921-30180209 |
| 8792 | Gm4133 | NM_001203141-22329717 | chr7:20393141-22329717 | 8889 | Gm5114 | NM_177890.3 | chr7:39407293-39413160 |
| 8793 | Gm4175 | NM_001167165.1 | chr7:21760531-21761475 | 8890 | Gm5122 | NR_040767.1 | chr9:61017068-61019797 |
| 8794 | Gm4201 | NM_001167162.1 | chr7:20575320-22565343 | 8891 | Gm5124 | NR_045668.1 | chrX:21360864-21364624 |
| 8795 | Gm4214 | NM_001167163.1 | chr7:22929729-22984673 | 8892 | Gm5126 | NR_026596.1 | chrX:102932046-102934223 |
| 8796 | Gm4216 | NM_001167166.1 | chr7:21795810-23019923 | 8893 | Gm5127 | NM_001035412.2 | chr5:106583185-106710557 |
| 8797 | Gm4224 | NR_046074.1 | chr7:12221315-12225807 | 8894 | Gm5129 | NR_028426.1 | chr5:29735833-29735936 |
| 8798 | Gm4251 | NR_046074.1 | chr14:71271059 | 8895 | Gm5132 | NM_001085517.2 | chrX:9571959-9572391 |
| 8799 | Gm4262 | NR_040518.1 | chr16:11008897-11015184 | 8896 | Gm5134 | NM_198635.3 | chr10:75954513-76009589 |
| 8800 | Gm4265 | NR_046077.1 | chr7:129962164-129978669 | 8897 | Gm5136 | NM_203660.2 | chr10:108699043-108700160 |
| 8801 | Gm4278 | NR_046081.1 | chr14:74975085-74987104 | 8898 | Gm5141 | NM_001256065.1 | chr13:62772199-62785868 |
| 8802 | Gm428 | NM_001081644.1 | chr4:73653245-73687559 | 8899 | Gm5142 | NM_001004358.2 | chr14:59158502-59178749 |
| 8803 | Gm4285 | NR_045294.1 | chr14:75842917-75844964 | 8900 | Gm5148 | NM_198657.2 | chr3:37714189-37724360 |
| 8804 | Gm4297 | NM_001100446.2 | chrX:24552249-24573305 | 8901 | Gm5150 | NM_001081687.1 | chr3:15948069-16006332 |
| 8805 | Gm4301 | NM_001166637.1 | chr10:100335675-100382560 | 8902 | Gm5166 | NR_027707.1 | chrX:102791135-102798389 |
| 8806 | Gm4302 | NM_001166634.1 | chr10:100345969-100362034 | 8903 | Gm5168 | NM_001025607.3 | chrX:26028213-26051941 |
| 8807 | Gm4303 | NM_001166638.1 | chr10:100345972-100346881 | 8904 | Gm5169 | NM_001040669.1 | chrX:25277482-25301455 |
| 8808 | Gm4307 | NM_001160837.1 | chr10:100340837-100346247 | 8905 | Gm5176 | NR_033603.1 | chr10:111500787-111501345 |
| 8809 | Gm4312 | NM_001166636.1 | chr10:100381647-100382560 | 8906 | Gm5177 | NR_038630.1 | chr10:106605944-10661631 |
| 8810 | Gm4340 | NM_001177535.1 | chr10:104142986-104188000 | 8907 | Gm525 | NM_001032266.2 | chr11:89073840-89093064 |
| 8811 | Gm4349 | NR_033637.1 | chr3:95427348-95431085 | 8908 | Gm527 | NM_001025605.1 | chr12:64917910-64924591 |
| 8812 | Gm436 | NM_001085504.1 | chr4:144669936-144686368 | 8909 | Gm5294 | NM_001195128.1 | chr5:138820079-138821619 |
| 8813 | Gm4371 | NR_028311.1 | chr15:96182799-96203470 | 8910 | Gm53 | NR_037977.1 | chr1:96251659-96264484 |
| 8814 | Gm4382 | NM_001166316.1 | chr14:144777203-144786593 | 8911 | Gm5334 | NR_038648.2 | chr7:68618455-68620009 |
| 8815 | Gm44 | NM_001101450.1 | chrX:90892141-90893134 | 8912 | Gm5346 | NM_001025240.1 | chr8:43624974-43627185 |
| 8816 | Gm4432 | NR_102329.1 | chr17:32421763-32442855 | 8913 | Gm5347 | NM_001079931.2 | chr8:43673657-43699491 |
| 8817 | Gm4461 | NM_001199062.1 | chr17:33215286-33216351 | 8914 | Gm5382 | NM_001034100.1 | chrX:14211147-14211657 |
| 8818 | Gm4477 | NM_001253910.2 | chr6:85706706-85708561 | 8915 | Gm5409 | NM_001003664.2 | chr6:41415306-41419593 |
| 8819 | Gm4489 | NR_027637.1 | chr17:122619696-122130558 | 8916 | Gm5414 | NM_001003670.1 | chr15:101624027-101628188 |
| 8820 | Gm4532 | NR_030674.1 | chr7:127232417-127233130 | 8917 | Gm5415 | NM_001164286.1 | chr1:32543545-32547293 |
| 8821 | Gm4541 | NR_033693.1 | chr7:20610883-23178761 | 8918 | Gm5416 | NM_001082542.1 | chr16:36210402-36217788 |
| 8822 | Gm4559 | NM_001199309.1 | chr7:142273763-142274363 | 8919 | Gm5420 | NR_045843.1 | chr10:21690844-21693978 |
| 8823 | Gm4566 | NR_028023.1 | chr7:71333200-71341804 | 8920 | Gm5424 | NR_002687.1 | chr2:31470307-31520629 |
| 8824 | Gm4598 | NM_001037643.3 | chr7:20724511-22719710 | 8921 | Gm5431 | NM_001024230.2 | chr11:48887421-48902152 |
| 8825 | Gm4598 | NR_030681.1 | chr7:24661293-24663109 | 8922 | Gm5434 | NR_003649.1 | chr12:36090378-36091829 |
| 8826 | Gm4710 | NR_033456.1 | chr17:75861022-75889039 | 8923 | Gm5441 | NR_044987.1 | chr12:117234520-117337012 |

Fig.21 - 47

| | | | | | | | | |
|---|---|---|---|---|---|---|---|---|
| 8924 | Gm5458 | NM_001024706.2 | chr14:19594137-19602587 | | 9021 | Gm6370 | NM_001243110.1 | chr5:146491362-146494132 |
| 8925 | Gm5460 | NM_001034880.2 | chr14:34041077-34046981 | | 9022 | Gm6377 | NM_001037917.2 | chrX:109196755-109200445 |
| 8926 | Gm5464 | NM_001034981.3 | chr14:66868849-66871005 | | 9023 | Gm6402 | NR_030688.1 | chr17:30394824-30396180 |
| 8927 | Gm5468 | NR_027376.1 | chr15:25414191-25452418 | | 9024 | Gm6406 | NM_001134661.1 | chr9:98856690-98857352 |
| 8928 | Gm5475 | NR_040351.1 | chr15:100423192-100428150 | | 9025 | Gm6408 | NM_001243104.1 | chr5:146481942-146484702 |
| 8929 | Gm5476 | NR_002868.1 | chr15:101587316-101588572 | | 9026 | Gm6416 | NR_046023.1 | chr13:117130024-117135884 |
| 8930 | Gm5477 | NR_002869.1 | chr15:101608873-101610479 | | 9027 | Gm6432 | NM_001244762.1 | chr9:99229375-99237239 |
| 8931 | Gm5478 | NR_003960.1 | chr15:101643019-101647380 | | 9028 | Gm6455 | NR_003596.2 | chr5:10865028-10870808 |
| 8932 | Gm5483 | NM_001082547.1 | chr16:36184211-36188110 | | 9029 | Gm6460 | NM_001037919.3 | chr5:11594955-11599480 |
| 8933 | Gm5485 | NR_015373.1 | chr16:48399452-48412416 | | 9030 | Gm648 | NM_001033372.2 | chrX:56543873-56549606 |
| 8934 | Gm5512 | NR_002891.1 | chr10:4403170-12906985 | | 9031 | Gm6484 | NM_001080940.1 | chr9:21835509-21837347 |
| 8935 | Gm5523 | NR_004447.1 | chr1:13785684-13786929 | | 9032 | Gm6498 | NR_003630.2 | chr14:48198715-48218413 |
| 8936 | Gm5531 | NM_001008426.3 | chr1:153874344-153876871 | | 9033 | Gm6524 | NR_028307.1 | chr8:11692981-11694514 |
| 8937 | Gm5535 | NM_001033778.1 | chr2:144173149-144189290 | | 9034 | Gm6525 | NR_036654.1 | chr3:84174637-84175193 |
| 8938 | Gm5538 | NM_001101531.1 | chr3:59729735-59752397 | | 9035 | Gm6537 | NM_001195031.1 | chr7:28756173-28758964 |
| 8939 | Gm5544 | NM_001033779.2 | chr3:97930172-97967018 | | 9036 | Gm6548 | NR_003363.1 | chr17:78850504-78852544 |
| 8940 | Gm5547 | NR_045845.1 | chr3:105815566-105817359 | | 9037 | Gm6559 | NR_110455.1 | chr6:51379709-51392791 |
| 8941 | Gm5549 | NM_001270430.1 | chr3:132630190-132644649 | | 9038 | Gm6567 | NR_046024.1 | chr7:73097751-73102068 |
| 8942 | Gm5577 | NR_028990.1 | chr6:87981682-87984180 | | 9039 | Gm6568 | NR_040420.2 | chrX:157540803-157541750 |
| 8943 | Gm5591 | NM_001013810.2 | chr7:38518138-38528193 | | 9040 | Gm6578 | NR_003631.2 | chr6:12099520-12109580 |
| 8944 | Gm5592 | NM_001033782.3 | chr7:41284326-41290183 | | 9041 | Gm6583 | NM_001039228.4 | chr5:112353772-112356033 |
| 8945 | Gm5595 | NM_001008427.1 | chr7:42660107-42692718 | | 9042 | Gm6588 | NM_001177504.1 | chr5:112448425-112451738 |
| 8946 | Gm5607 | NR_027975.2 | chr8:12385770-12436732 | | 9043 | Gm6592 | NM_001081564.1 | chrX:8843993-8849607 |
| 8947 | Gm561 | NM_001033297.2 | chr2:144594064-144595365 | | 9044 | Gm6602 | NR_045362.1 | chr3:111881902-112082001 |
| 8948 | Gm5615 | NM_001033783.2 | chr9:36532402-36541963 | | 9045 | Gm6607 | NR_033622.2 | chr9:22330138-22330690 |
| 8949 | Gm5617 | NM_001004191.3 | chr9:48495842-48495975 | | 9046 | Gm6614 | NM_001081318.1 | chr16:141972195-142008745 |
| 8950 | Gm5622 | NM_001013816.1 | chr14:51552789-51662953 | | 9047 | Gm6623 | NR_033619.1 | chr17:36178776-36181364 |
| 8951 | Gm5627 | NR_033301.1 | chr9:102739647-102756685 | | 9048 | Gm6634 | NR_040556.1 | chr3:70772378-70807291 |
| 8952 | Gm5634 | NM_001085524.1 | chrX:8962133-8962975 | | 9049 | Gm6639 | NR_040748.1 | chr3:35597151-35666163 |
| 8953 | Gm5635 | NM_001038697.2 | chrX:9063089-9063822 | | 9050 | Gm6642 | NR_033643.2 | chr19:30930385-30930962 |
| 8954 | Gm5640 | NM_001099302.1 | chrX:74639118-74645635 | | 9051 | Gm6644 | NR_037965.1 | chr6:34303933-34317443 |
| 8955 | Gm5643 | NR_002883.1 | chrX:103240453-142299237 | | 9052 | Gm6654 | NR_038089.1 | chr6:146647176-146647802 |
| 8956 | Gm5662 | NM_001013824.3 | chr12:88270634-88274497 | | 9053 | Gm6682 | NR_033599.1 | chr12:4782170-4783812 |
| 8957 | Gm5712 | NR_033594.1 | chr3:129433672-129434712 | | 9054 | Gm6696 | NM_001177523.1 | chr8:21583026-21583867 |
| 8958 | Gm572 | NM_001085505.1 | chr4:148643316-148671572 | | 9055 | Gm6710 | NM_001164689.1 | chr2:175192979-175883182 |
| 8959 | Gm5725 | NM_001166711.1 | chr7:21843343-23067456 | | 9056 | Gm6756 | NR_076393.1 | chr18:36920304-36922207 |
| 8960 | Gm5726 | NM_001167346.1 | chr7:20544834-20545757 | | 9057 | Gm6780 | NM_001177377.1 | chrX:64115404-64152198 |
| 8961 | Gm5728 | NM_001166713.1 | chr7:20374492-22371039 | | 9058 | Gm6763 | NM_001270899.1 | chr10:104142986-104196493 |
| 8962 | Gm5741 | NM_001195531.1 | chr8:85067567-85067982 | | 9059 | Gm6787 | NR_033632.2 | chrX:8097086-8106761 |
| 8963 | Gm5766 | NR_003628.1 | chr16:4229228-4231205 | | 9060 | Gm6792 | NM_001177416.1 | chr7:6252709-6281861 |
| 8964 | Gm5771 | NM_001038997.2 | chr6:41392355-41397256 | | 9061 | Gm6793 | NR_033513.1 | chr2:75659289-75665756 |
| 8965 | Gm5779 | NR_033602.1 | chr10:78352054-75352961 | | 9062 | Gm6812 | NM_001098842.2 | chrX:68892172-68893053 |
| 8966 | Gm5795 | NM_001270806.1 | chr14:3186283-3800987 | | 9063 | Gm6815 | NR_102685.1 | chr16:36194479-36197886 |
| 8967 | Gm5796 | NM_001029930.2 | chr14:4023940-4041368 | | 9064 | Gm684 | NM_001195681.1 | chr9:51270257-51278554 |
| 8968 | Gm5797 | NM_001025085.2 | chr14:7323987-7332395 | | 9065 | Gm6878 | NM_001037931.3 | chr14:67304887-67314711 |
| 8969 | Gm5800 | NM_001034102.2 | chr14:51711643-51717132 | | 9066 | Gm6880 | NM_001099305.1 | chrX:74480286-74481399 |
| 8970 | Gm5801 | NR_003628.1 | chr2:156010291-155957601 | | 9067 | Gm6890 | NM_001099306.1 | chrX:74740926-74742118 |
| 8971 | Gm5803 | NM_001165971.1 | chr15:22713819-22714984 | | 9068 | Gm6902 | NM_001270494.1 | chr7:20724513-23275243 |
| 8972 | Gm5820 | NM_001033789.2 | chr18:38892455-38971274 | | 9069 | Gm6904 | NM_001164329.1 | chr14:59244440-59260216 |
| 8973 | Gm5833 | NR_040304.1 | chr1:138640094-138682675 | | 9070 | Gm6927 | NM_001101585.1 | chrX:77674813-77675452 |
| 8974 | Gm5860 | NR_040659.1 | chr4:82065379-82102807 | | 9071 | Gm6936 | NR_045001.1 | chr16:49980459-49997475 |
| 8975 | Gm5862 | NM_001281525.1 | chr5:26018426-28022891 | | 9072 | Gm6938 | NR_033482.1 | chrX:21312209-21334727 |
| 8976 | Gm5868 | NM_001024147.2 | chr5:72581638-72587550 | | 9073 | Gm694 | NM_001033374.3 | chr4:141432671-141436105 |
| 8977 | Gm5878 | NM_001034902.2 | chr6:85111415-85126094 | | 9074 | Gm6981 | NR_023357.1 | chr9:52002060-52048705 |
| 8978 | Gm5885 | NM_001185040.1 | chr6:133529188-133532762 | | 9075 | Gm6994 | NR_033141.1 | chr14:77479482-77506868 |
| 8979 | Gm5886 | NM_001177652.2 | chr6:133763997-133767408 | | 9076 | Gm7008 | NR_045157.1 | chr12:40223363-40229183 |
| 8980 | Gm5891 | NM_001034904.2 | chr7:21909433-23144480 | | 9077 | Gm7030 | NM_001177467.1 | chr17:36127608-36129425 |
| 8981 | Gm5893 | NR_045096.1 | chr7:24818794-24840275 | | 9078 | Gm7056 | NR_035771.1 | chr5:89616435-89622611 |
| 8982 | Gm590 | NM_001195437.1 | chr9:110914738-110916861 | | 9079 | Gm7073 | NM_001039240.3 | chrX:60436051-60456195 |
| 8983 | Gm5901 | NM_001195271.1 | chr7:105375097-105378287 | | 9080 | Gm7102 | NM_001177513.1 | chr19:61174685-61176309 |
| 8984 | Gm5916 | NM_001167587.1 | chr9:36119933-36128770 | | 9081 | Gm7104 | NR_033570.1 | chr12:88282866-88287070 |
| 8985 | Gm5925 | NR_040410.1 | chrX:4515588-4517543 | | 9082 | Gm711 | NM_198628.2 | chr2:26934068-26953496 |
| 8986 | Gm5934 | NM_001100444.2 | chrX:24474302-24499163 | | 9083 | Gm7120 | NM_001039244.3 | chr13:119488038-119610459 |
| 8987 | Gm5935 | NM_001081657.1 | chrX:24753161-24775164 | | 9084 | Gm7134 | NR_033597.1 | chrX:110372752-110375156 |
| 8988 | Gm5936 | NM_001081670.2 | chrX:74837195-74843369 | | 9085 | Gm715 | NM_001271548.1 | chr5:60548007-60549216 |
| 8989 | Gm5938 | NM_001085534.2 | chrX:78125469-78130403 | | 9086 | Gm7157 | NM_001199311.1 | chrX:152563333-152563969 |
| 8990 | Gm5941 | NM_001034103.1 | chrX:92489948-92490679 | | 9087 | Gm7168 | NM_001229777.1 | chr17:139483372-139506678 |
| 8991 | Gm595 | NM_001085499.1 | chrX:48841465-48877713 | | 9088 | Gm7173 | NM_001099307.1 | chrX:79482567-79517285 |
| 8992 | Gm597 | NM_001176121.1 | chr12:28780252 | | 9089 | Gm7244 | NM_001101597.2 | chr9:31271400-31275385 |
| 8993 | Gm6026 | NM_001177569.1 | chrY:2599098-2720674 | | 9090 | Gm7257 | NM_001167586.1 | chr9:36431883-36434938 |
| 8994 | Gm6034 | NM_001034969.3 | chr7:36042960-36058645 | | 9091 | Gm7271 | NR_033501.1 | chr5:76484076-76516623 |
| 8995 | Gm6040 | NM_001025353.2 | chr8:20916489-20922071 | | 9092 | Gm732 | NM_001033252.2 | chrX:107945734-107948436 |
| 8996 | Gm6042 | NR_002872.1 | chr15:101503815-101506313 | | 9093 | Gm7325 | NM_001177468.1 | chr17:45660966-45602067 |
| 8997 | Gm608 | NM_001029889.2 | chr16:44173306-44227466 | | 9094 | Gm7334 | NR_042700.1 | chr16:78359862-78376757 |
| 8998 | Gm6083 | NR_102704.1 | chr5:29537948-29538624 | | 9095 | Gm7337 | NR_003652.2 | chr5:87850358-87853012 |
| 8999 | Gm6086 | NM_001039219.2 | chr1:93990508-94011539 | | 9096 | Gm7361 | NM_001281527.1 | chr5:26257761-26262188 |
| 9000 | Gm609 | NM_001005854.2 | chr15:45416754-45492969 | | 9097 | Gm7367 | NR_003376.2 | chr11:116434212-116439031 |
| 9001 | Gm6116 | NR_045866.1 | chr5:74949193-74966368 | | 9098 | Gm7444 | NR_033529.1 | chr9:56027635-56031573 |
| 9002 | Gm6121 | NM_001114754.1 | chrX:26952743-26935669 | | 9099 | Gm7457 | NR_045707.1 | chr6:142814230-142833494 |
| 9003 | Gm614 | NM_001033362.2 | chrX:101261376-101263992 | | 9100 | Gm7534 | NM_001080712.1 | chr4:134190803-134203004 |
| 9004 | Gm6150 | NR_038036.1 | chr10:9684721-9691909 | | 9101 | Gm7538 | NR_046033.1 | chr5:119194312-119200018 |
| 9005 | Gm6164 | NM_001167153.1 | chr7:20204683-22201264 | | 9102 | Gm7550 | NR_036839.1 | chr12:54387732-54391318 |
| 9006 | Gm6194 | NR_033512.1 | chr3:84613386-8463098 | | 9103 | Gm7609 | NM_001081746.1 | chr1:85199610-85213762 |
| 9007 | Gm6213 | NR_044988.1 | chr3:39297979-39368268 | | 9104 | Gm7616 | NM_001101600.1 | chr5:59951293-59959044 |
| 9008 | Gm6225 | NR_033457.1 | chr18:3336415-3366863 | | 9105 | Gm765 | NM_001128092.1 | chr6:98238013-98342754 |
| 9009 | Gm6249 | NR_046021.1 | chr7:136687954-136710604 | | 9106 | Gm766 | NM_001145390.1 | chr6:142785780-142804468 |
| 9010 | Gm6251 | NM_001161561.2 | chr10:20208435-20209030 | | 9107 | Gm7694 | NM_001198955.1 | chr1:370298192-170306392 |
| 9011 | Gm6260 | NR_040405.1 | chr3:143670891-143712143 | | 9108 | Gm7714 | NM_001110779.1 | chr5:88268918-88282835 |
| 9012 | Gm6268 | NR_044989.1 | chrX:36403476-36404654 | | 9109 | Gm773 | NM_001033423.2 | chrX:56189826-56212881 |
| 9013 | Gm6277 | NR_045421.1 | chr18:118211087-11839377 | | 9110 | Gm7788 | NR_110491.1 | chr18:23217595-23217818 |
| 9014 | Gm6289 | NR_126537.1 | chr3:148199322-144896011 | | 9111 | Gm7849 | NM_001177518.1 | chr5:21455426-21594465 |
| 9015 | Gm6297 | NR_077221.1 | chr4:40720153-40722317 | | 9112 | Gm7854 | NR_028417.1 | chr5:43151685-43235354 |
| 9016 | Gm6300 | NR_033591.1 | chr16:143774239 | | 9113 | Gm7861 | NM_001177526.1 | chr2:21455538-21594465 |
| 9017 | Gm6307 | NR_045331.1 | chr2:180385603-180401802 | | 9114 | Gm7903 | NM_001242937.1 | chrX:135373283-135383393 |
| 9018 | Gm6313 | NR_038036.1 | chr6:148606785-148614309 | | 9115 | Gm7904 | NR_033632.1 | chr21:21607083-21608329 |
| 9019 | Gm6329 | NR_040690.1 | chr8:45100493-45165145 | | 9116 | Gm7977 | NR_040408.1 | chr3:48026011-48026759 |
| 9020 | Gm6367 | NR_044992.1 | chr5:587624-95026538 | | 9117 | Gm7978 | NM_001270457.1 | chr5:95732092-95736173 |

Fig.21 - 48

| | | | | | | | | |
|---|---|---|---|---|---|---|---|---|
| 9118 | Gm805 | NR_046081.1 | chr12:86169340-86195102 | 9215 | Gna11 | NM_010301.3 | chr10:81528731-81545046 |
| 9119 | Gm806 | NM_001033400.2 | chr13:50467306-50475355 | 9216 | Gna12 | NM_010302.2 | chr5:140759943-140830431 |
| 9120 | Gm8096 | NR_033590.1 | chr8:28083193-28084853 | 9217 | Gna13 | NM_010303.3 | chr11:109362793-109401369 |
| 9121 | Gm813 | NM_001033404.2 | chr16:58613685-58616978 | 9218 | Gna14 | NM_008137.4 | chr19:18435666-16610818 |
| 9122 | Gm815 | NM_001033407.2 | chr19:26885924-26898647 | 9219 | Gna15 | NM_010304.3 | chr10:81502313-81524225 |
| 9123 | Gm8179 | NR_046039.1 | chr8:32151894-32181847 | 9220 | Gnai1 | NM_010305.1 | chr5:18265134-18360413 |
| 9124 | Gm8221 | NR_033577.1 | chr15:77618967-77627398 | 9221 | Gnai2 | NM_008138.4 | chr9:107614137-107635342 |
| 9125 | Gm8234 | NR_004433.3 | chr3:58652041-58654041 | 9222 | Gnai3 | NM_010306.3 | chr3:108107274-108146152 |
| 9126 | Gm826 | NM_001033411.2 | chr2:160311400-160327494 | 9223 | Gnal | NM_010307.3 | chr18:67133559-67226791 |
| 9127 | Gm8267 | NM_001162954.1 | chr14:44717166-44724987 | 9224 | Gnao1 | NM_001133384.1 | chr8:93810837-93960694 |
| 9128 | Gm829 | NM_001033412.2 | chr4:45683588-45723706 | 9225 | Gnaq | NM_008139.5 | chr19:16132830-16387453 |
| 9129 | Gm8298 | NM_001243003.1 | chr3:59861050-59877313 | 9226 | Gnas | NM_001077507.2 | chr2:174297858-174346742 |
| 9130 | Gm8300 | NM_001177565.1 | chr12:87514315-87518265 | 9227 | Gnat1 | NM_008140.2 | chr9:107674473-107679592 |
| 9131 | Gm833 | NR_033138.1 | chr4:152697539-152700922 | 9228 | Gnat2 | NM_008141.3 | chr3:108093065-108101430 |
| 9132 | Gm8363 | NR_073378.1 | chr17:5480088-5483069 | 9229 | Gnat3 | NM_001081143.1 | chr5:17962569-18019668 |
| 9133 | Gm8369 | NM_001164202.1 | chr19:11492037-11512577 | 9230 | Gnaz | NM_010311.3 | chr10:74967230-75015877 |
| 9134 | Gm839 | NR_033190.1 | chr6:89212196-89216179 | 9231 | Gnb1 | NM_001160016.1 | chr4:155491360-155558269 |
| 9135 | Gm8439 | NM_001101603.1 | chr4:120588744-120609672 | 9232 | Gnb1l | NM_001081682.2 | chr16:18498712-18566680 |
| 9136 | Gm853 | NM_001034872.2 | chr4:130209108-130222295 | 9233 | Gnb2 | NM_010312.4 | chr5:137528128-137533229 |
| 9137 | Gm8579 | NR_036696.1 | chr6:3288518-3317019 | 9234 | Gnb2l1 | NM_008143.3 | chr11:48800359-48806241 |
| 9138 | Gm8580 | NR_027478.1 | chr10:93665243-93665854 | 9235 | Gnb3 | NM_013530.1 | chr6:124834239-124840275 |
| 9139 | Gm8615 | NR_028061.1 | chr5:149154127-149156192 | 9236 | Gnb4 | NM_013531.4 | chr3:32583527-32618535 |
| 9140 | Gm8633 | NR_045179.1 | chr10:98299926-98351867 | 9237 | Gnb5 | NM_010313.2 | chr9:75306287-75345923 |
| 9141 | Gm867 | NM_001277132.1 | chr19:75937722-75940672 | 9238 | Gne | NM_001190414.1 | chr4:44036822-44072673 |
| 9142 | Gm8677 | NM_001167347.1 | chr7:22533964-22534887 | 9239 | Gng10 | NM_025277.3 | chr4:59035155-59041899 |
| 9143 | Gm8693 | NM_001167154.1 | chr7:22691329-22692317 | 9240 | Gng11 | NM_025331.2 | chr6:4003986-4008446 |
| 9144 | Gm8709 | NR_033633.1 | chr10:26673445-26674651 | 9241 | Gng12 | NM_001177556.1 | chr6:66896396-67021361 |
| 9145 | Gm8765 | NM_001244649.1 | chr13:50698328-50703409 | 9242 | Gng13 | NM_022422.5 | chr17:25717171-25719102 |
| 9146 | Gm8773 | NR_033499.1 | chr5:5573798-5576203 | 9243 | Gng2 | NM_001038637.1 | chr14:19872558-19977224 |
| 9147 | Gm8787 | NM_001099310.1 | chrX:79330512-79358068 | 9244 | Gng3 | NM_010316.3 | chr19:8836928-8839246 |
| 9148 | Gm8801 | NR_028278.1 | chr17:35947153-35953317 | 9245 | Gng4 | NM_010317.3 | chr13:13784306-13827895 |
| 9149 | Gm8817 | NM_001101606.1 | chrX:167063448-167070370 | 9246 | Gng5 | NM_010318.2 | chr3:146499835-146505543 |
| 9150 | Gm884 | NM_001033434.2 | chr11:103545476-103614739 | 9247 | Gng7 | NM_001038655.1 | chr10:80948623-81001365 |
| 9151 | Gm8882 | NM_001175586.1 | chr6:132361104-132364134 | 9248 | Gng8 | NM_010320.3 | chr7:16891785-16895435 |
| 9152 | Gm8883 | NR_027658.1 | chr1:71888111-71891204 | 9249 | Gngt1 | NM_010314.2 | chr6:3994011-3997436 |
| 9153 | Gm8884 | NR_026561.1 | chr9:48454343-48454727 | 9250 | Gngt2 | NM_001038664.2 | chr11:95842667-95845731 |
| 9154 | Gm8898 | NM_001177405.1 | chr2:175372461-176533821 | 9251 | Gnl1 | NM_008136.2 | chr17:35979954-35989462 |
| 9155 | Gm8909 | NM_001081032.2 | chr17:36164443-36168537 | 9252 | Gnl2 | NM_145552.2 | chr4:125030013-125055382 |
| 9156 | Gm8979 | NR_030719.1 | chr7:106075730-106079148 | 9253 | Gnl3 | NM_153547.6 | chr14:31012432-31019031 |
| 9157 | Gm8989 | NR_030720.1 | chr7:106075731-106324528 | 9254 | Gnl3l | NM_001168600.1 | chrX:150983132-151017293 |
| 9158 | Gm8994 | NM_001142734.1 | chr6:136327538-136329983 | 9255 | Gnmt | NM_010321.1 | chr17:46725663-46729165 |
| 9159 | Gm9 | NM_001033234.2 | chrX:37208501-37211041 | 9256 | Gnpat | NM_010322.3 | chr8:124863032-124890057 |
| 9160 | Gm904 | NM_001033770.1 | chr13:50643227-50645838 | 9257 | Gnpda1 | NM_011937.2 | chr18:38327536-38338993 |
| 9161 | Gm9047 | NM_001145360.1 | chr6:29471436-29473429 | 9258 | Gnpda2 | NM_001038015.1 | chr5:69575601-69592285 |
| 9162 | Gm9054 | NR_045827.1 | chr3:95985509-95986967 | 9259 | Gnpnat1 | NM_019425.2 | chr14:45376420-45388796 |
| 9163 | Gm906 | NM_001033438.2 | chr13:50245180-50250308 | 9260 | Gnptab | NM_001004164.2 | chr10:88379411-88447329 |
| 9164 | Gm9079 | NR_004052.1 | chr10:122078111-122079879 | 9261 | Gnptg | NM_172529.3 | chr17:25234317-25240116 |
| 9165 | Gm9112 | NM_001177365.1 | chrX:102706887-102707670 | 9262 | Gnrh1 | NM_008145.1 | chr14:67745228-67749436 |
| 9166 | Gm9126 | NM_001163730.2 | chr3:93986632-94054885 | 9263 | Gnrhr | NM_010323.2 | chr5:86180753-86197901 |
| 9167 | Gm9159 | NR_033584.1 | chrX:103545499-103547699 | 9264 | Gns | NM_029364.3 | chr10:121365089-121397245 |
| 9168 | Gm9199 | NR_027860.1 | chr14:73025602-73026890 | 9265 | Golga1 | NM_001290649.1 | chr2:39016155-39065541 |
| 9169 | Gm9268 | NM_001105061.1 | chr7:43018797-43048106 | 9266 | Golga2 | NM_001080968.1 | chr2:32288252-32307921 |
| 9170 | Gm933 | NM_001256309.1 | chr16:32804887-32810446 | 9267 | Golga3 | NM_008146.3 | chr5:110176700-110223155 |
| 9171 | Gm9376 | NM_001101609.1 | chr14:118267157-118267770 | 9268 | Golga4 | NM_018748.3 | chr9:118506317-118582519 |
| 9172 | Gm94 | NM_001033428.2 | chr18:43777195-43792878 | 9269 | Golga5 | NM_001199004.1 | chr12:102469133-102497907 |
| 9173 | Gm9513 | NM_001125510.1 | chr9:36475637-36477180 | 9270 | Golga7 | NM_001042484.1 | chr8:23241325-23257080 |
| 9174 | Gm9573 | NM_001244654.1 | chr17:35617922-35626637 | 9271 | Golga7b | NM_001141983.1 | chr19:42247577-42270348 |
| 9175 | Gm960 | NM_001033447.3 | chr19:46265840-46986658 | 9272 | Golgb1 | NM_030035.1 | chr16:36885010-36953085 |
| 9176 | Gm9696 | NR_037189.1 | chr3:59952308-59973594 | 9273 | Golim4 | NM_001291069.1 | chr3:75876182-75956949 |
| 9177 | Gm973 | NM_001013771.2 | chr1:59516263-59634509 | 9274 | Golm1 | NM_001035122.2 | chr13:59634995-59675784 |
| 9178 | Gm9731 | NR_033107.1 | chr8:27296044-27297200 | 9275 | Golph3 | NM_025673.2 | chr15:12321495-12351267 |
| 9179 | Gm9733 | NM_001076679.2 | chr3:15296550-15332362 | 9276 | Golph3l | NM_001177669.1 | chr3:95588933-95619247 |
| 9180 | Gm9758 | NM_198665.3 | chr5:14911363-14914889 | 9277 | Golt1a | NM_026680.4 | chr1:133309822-133323026 |
| 9181 | Gm9767 | NR_028030.2 | chr10:26078254-26079447 | 9278 | Golt1b | NM_025872.4 | chr6:142387242-142403858 |
| 9182 | Gm9776 | NR_045619.1 | chr13:94356748-94358923 | 9279 | Gon4l | NM_001242372.1 | chr3:88835230-88910099 |
| 9183 | Gm9833 | NR_045710.1 | chr3:10088276-10092562 | 9280 | Gopc | NM_001199272.1 | chr10:52337023-52382124 |
| 9184 | Gm9839 | NM_001199956.1 | chr1:32519562-32520999 | 9281 | Gorab | NM_178863.6 | chr1:163384902-163403669 |
| 9185 | Gm9856 | NR_037190.1 | chr10:82629841-82650277 | 9282 | Gorasp1 | NM_028976.2 | chr9:119925672-119937558 |
| 9186 | Gm9866 | NR_045686.1 | chr12:27140795-27160516 | 9283 | Gorasp2 | NM_027352.4 | chr2:70661508-70691725 |
| 9187 | Gm9871 | NR_027989.1 | chr6:101774248-101801982 | 9284 | Gosr1 | NM_016810.3 | chr11:76726601-76763555 |
| 9188 | Gm9895 | NR_045687.1 | chr19:29067300-29069503 | 9285 | Gosr2 | NM_199650.3 | chr11:103676848-103697710 |
| 9189 | Gm9899 | NR_040427.1 | chr5:30573986-30588619 | 9286 | Got1 | NM_010324.2 | chr19:43499752-43524605 |
| 9190 | Gm9920 | NR_045093.1 | chr15:55099916-55113582 | 9287 | Got1l1 | NM_029674.1 | chr8:27197458-27202547 |
| 9191 | Gm9926 | NR_040518.1 | chr18:66504177-66511737 | 9288 | Got2 | NM_010325.2 | chr8:95864136-95888365 |
| 9192 | Gm9958 | NR_045618.1 | chr5:90366996-90368488 | 9289 | Gp1ba | NM_010326.2 | chr11:70639121-70642055 |
| 9193 | Gm996 | NM_001005424.2 | chr2:25575415-25580099 | 9290 | Gp1bb | NM_001001999.1 | chr16:18620318-18622403 |
| 9194 | Gm9961 | NR_011901363.1 | chr11:11930594 | 9291 | Gp2 | NM_025989.3 | chr7:119442543-119459272 |
| 9195 | Gm9962 | NR_033504.1 | chr7:57387271-57409941 | 9292 | Gp49a | NM_001291892.1 | chr10:51480611-51486329 |
| 9196 | Gm9992 | NM_001142935.1 | chr17:73637113-7385305 | 9293 | Gp5 | NM_008148.4 | chr16:30307684-30310781 |
| 9197 | Gm9994 | NM_001205249.1 | chr1:93918436-93941239 | 9294 | Gp6 | NM_001163014.1 | chr7:4368712-4397744 |
| 9198 | Gm9999 | NR_033461.1 | chr7:46976631-46987803 | 9295 | Gp9 | NM_018762.1 | chr6:87778135-87779762 |
| 9199 | Gmcl1 | NM_011818.3 | chr6:86691767-86733378 | 9296 | Gpa33 | NM_021610.1 | chr1:166130459-166166510 |
| 9200 | Gmcl1l | NM_027955.3 | chrX:32560054-32562009 | 9297 | Gpaa1 | NM_010331.2 | chr15:76331293-76334899 |
| 9201 | Gmds | NM_146041.2 | chr13:31819585-32338544 | 9298 | Gpalpp1 | NM_026177.3 | chr14:76086231-76110815 |
| 9202 | Gmeb1 | NM_001122992.1 | chr4:132221014-132261549 | 9299 | Gpam | NM_008149.3 | chr19:55669733-55699447 |
| 9203 | Gmeb2 | NM_198169.2 | chr2:181251450-181287966 | 9300 | Gpank1 | NM_001128597.1 | chr17:35123495-35124815 |
| 9204 | Gmfb | NM_022023.1 | chr14:46808148-46822242 | 9301 | Gpat2 | NM_001081089.2 | chr2:127425198-127436092 |
| 9205 | Gmfg | NM_001039192.1 | chr7:28440936-28446895 | 9302 | Gpatch1 | NM_026181.1 | chr7:35276543-35318440 |
| 9206 | Gmip | NM_198101.1 | chr8:69808686-69821870 | 9303 | Gpatch11 | NM_181649.6 | chr17:78835515-78848308 |
| 9207 | Gml | NM_001177524.1 | chr15:74813454-74818815 | 9304 | Gpatch2 | NM_026367.4 | chr1:187215510-187351423 |
| 9208 | Gmnc | NM_001013761.2 | chr16:26957234-26961652 | 9305 | Gpatch2l | NM_027405.2 | chr12:86243877-86291368 |
| 9209 | Gmnn | NM_020567.2 | chr13:24751844-24761937 | 9306 | Gpatch3 | NM_172876.2 | chr4:133574744-133584242 |
| 9210 | Gmppa | NM_133708.3 | chr1:75435942-75443176 | 9307 | Gpatch4 | NM_001110809.2 | chr3:88043105-88055394 |
| 9211 | Gmppb | NM_177910.3 | chr9:108049289-108051936 | 9308 | Gpatch8 | NM_001159492.1 | chr11:102475915-102556158 |
| 9212 | Gmpr | NM_025508.5 | chr13:45507443-45546386 | 9309 | Gpbar1 | NM_174985.1 | chr1:74278599-74279589 |
| 9213 | Gmpr2 | NM_177992.2 | chr14:55672234-55678751 | 9310 | Gpbp1 | NM_001122963.1 | chr13:111425679-111490041 |
| 9214 | Gmps | NM_001033300.2 | chr3:63976142-64019078 | 9311 | Gpbp1l1 | NM_029868.2 | chr13:116557726-116593882 |

Fig.21 - 49

| | | | | | | | |
|---|---|---|---|---|---|---|---|
| 9312 | Gpc1 | NM_016696.4 | chr1:92831685-92860196 | 9409 | Gpr56 | NM_001198894.1 | chr8:94977108-95014208 |
| 9313 | Gpc2 | NM_172412.2 | chr5:138273659-138279937 | 9410 | Gpr6 | NM_199058.1 | chr10:41070492-41071584 |
| 9314 | Gpc3 | NM_016697.3 | chrX:52272426-52613974 | 9411 | Gpr61 | NM_001305461.1 | chr3:108148321-108154986 |
| 9315 | Gpc4 | NM_008150.2 | chrX:52053017-52164923 | 9412 | Gpr62 | NM_001159652.1 | chr9:106463959-106465940 |
| 9316 | Gpc5 | NM_175500.4 | chr14:115092214-116525192 | 9413 | Gpr63 | NM_030733.3 | chr4:24973418-25009233 |
| 9317 | Gpc6 | NM_001079844.2 | chr14:116925296-117979529 | 9414 | Gpr64 | NM_001079847.2 | chrX:160390689-160498076 |
| 9318 | Gpcpd1 | NM_001042672.1 | chr2:132529082-132578282 | 9415 | Gpr65 | NM_008152 | chr12:98268634-98276722 |
| 9319 | Gpd1 | NM_010271.2 | chr15:99717592-99725007 | 9416 | Gpr68 | NM_001177673.1 | chr12:100876681-100908198 |
| 9320 | Gpd1l | NM_175380.5 | chr9:114899338-114933987 | 9417 | Gpr75 | NM_175490.4 | chr11:30885357-30893725 |
| 9321 | Gpd2 | NM_001145820.1 | chr2:57237677-57370719 | 9418 | Gpr82 | NM_175869.3 | chrX:136613362-136677433 |
| 9322 | Gper1 | NM_029771.3 | chr5:139423178-139427800 | 9419 | Gpr83 | NM_010287.3 | chr9:14860209-14870789 |
| 9323 | Gphn2 | NM_130453.3 | chr19:6226400-6227768 | 9420 | Gpr84 | NM_030720.1 | chr15:103308234-103310438 |
| 9324 | Gphb5 | NM_175644.3 | chr12:75411719-75416781 | 9421 | Gpr85 | NM_145066.4 | chr6:13835073-13839848 |
| 9325 | Gphn | NM_145965.2 | chr12:78226854-78684769 | 9422 | Gpr87 | XM_006502394.2 | chr3:59178904-59185468 |
| 9326 | Gpi1 | NM_008155.4 | chr7:34201326-34230336 | 9423 | Gpr88 | NM_022427.2 | chr3:116249653-116253484 |
| 9327 | Gpihbp1 | NM_026730.1 | chr15:75596657-75598213 | 9424 | Gpr89 | NM_026229.4 | chr3:96871065-96906298 |
| 9328 | Gpkow | NM_173747.3 | chrX:7697133-7710259 | 9425 | Gpr97 | NM_173036.3 | chr8:95017691-95045249 |
| 9329 | Gpld1 | NM_008156.2 | chr13:24943151-24991936 | 9426 | Gpr98 | NM_054053.3 | chr13:81095067-81633144 |
| 9330 | Gpm6a | NM_001253794.1 | chr8:54779433-55060878 | 9427 | Gprasp1 | NM_001040459.2 | chrX:135742691-135803468 |
| 9331 | Gpm6b | NM_001177955.1 | chrX:166344552-166389033 | 9428 | Gprasp2 | NM_001163015.1 | chrX:135839033-135844780 |
| 9332 | Gpn1 | NM_133756.4 | chr5:31494760-31511627 | 9429 | Gprc5a | NM_181444.5 | chr6:135065561-135084708 |
| 9333 | Gpn2 | NM_001290742.1 | chr4:133584372-133591735 | 9430 | Gprc5b | NM_001195774.1 | chr7:118972039-118995211 |
| 9334 | Gpn3 | NM_024761.1 | chr5:122372507-122382769 | 9431 | Gprc5c | NM_001110337.1 | chr11:114851531-114872617 |
| 9335 | Gpnmb | NM_053110.4 | chr6:49036517-49058182 | 9432 | Gprc5d | NM_001205396.1 | chr6:135105990-135113283 |
| 9336 | Gpr1 | NM_146250.2 | chr1:63182570-63214281 | 9433 | Gprc6a | NM_153071.1 | chr10:51614822-51631458 |
| 9337 | Gpr101 | NM_001033660.3 | chrX:57496667-57503757 | 9434 | Gprin1 | NM_012014.3 | chr13:54736672-54749969 |
| 9338 | Gpr107 | NM_178760.4 | chr2:31152315-31216567 | 9435 | Gprin2 | NM_183209.2 | chr14:34194440-34201633 |
| 9339 | Gpr108 | NM_030084.4 | chr17:57234914-57247689 | 9436 | Gprin3 | NM_183183.2 | chr6:59352460-59426290 |
| 9340 | Gpr110 | NM_001177874.1 | chr7:43270346-43324406 | 9437 | Gps1 | NM_001177874.1 | chr11:120784271-120789102 |
| 9341 | Gpr111 | NM_001033493.2 | chr17:42708936-42742179 | 9438 | Gps2 | NM_019726.3 | chr11:69914191-69916591 |
| 9342 | Gpr113 | NM_001013494.2 | chr5:30193440-30205722 | 9439 | Gpsm1 | NM_001199146.1 | chr2:26315532-26348237 |
| 9343 | Gpr114 | NM_001033468.3 | chr8:94923693-94943290 | 9440 | Gpsm2 | NM_029522.2 | chr3:108678637-108722299 |
| 9344 | Gpr115 | NM_001289499.1 | chr17:42656886-42692284 | 9441 | Gpsm3 | NM_134116.5 | chr17:34589805-34591754 |
| 9345 | Gpr116 | NM_001081178.1 | chr17:43389465-43459557 | 9442 | Gpt | NM_182805.2 | chr15:76696763-76699675 |
| 9346 | Gpr119 | NM_181751.2 | chrX:48667978-48674478 | 9443 | Gpt2 | NM_173866.3 | chr8:85492616-85527558 |
| 9347 | Gpr12 | NM_001010941.2 | chr5:146582149-146585239 | 9444 | Gpx1 | NM_008160.1 | chr9:108339079-108340844 |
| 9348 | Gpr123 | NM_177469.3 | chr17:43979788-43978088 | 9445 | Gpx2 | NM_030677.2 | chr12:76792334-76795554 |
| 9349 | Gpr124 | NM_054044.2 | chr8:27085840-27123436 | 9446 | Gpx2-ps1 | NR_033563.1 | chr7:100264543-100265561 |
| 9350 | Gpr125 | NM_133911.1 | chr5:49959950-50058996 | 9447 | Gpx3 | NM_008161.3 | chr11:54902853-54910382 |
| 9351 | Gpr126 | NM_001002268.3 | chr10:14402584-14545036 | 9448 | Gpx4 | NM_001037741.3 | chr10:80054018-80056439 |
| 9352 | Gpr128 | NM_172825.3 | chr16:56724608-56795858 | 9449 | Gpx5 | NM_010343.2 | chr13:21286428-21292686 |
| 9353 | Gpr132 | NM_019925.4 | chr12:112850875-112860916 | 9450 | Gpx6 | NM_145451.3 | chr13:21312202-21319624 |
| 9354 | Gpr133 | NM_001081342.1 | chr5:129096749-129204599 | 9451 | Gpx7 | NM_024198.3 | chr4:108400216-108406713 |
| 9355 | Gpr135 | NM_181752.1 | chr12:72069617-72070991 | 9452 | Gpx8 | NM_027127.2 | chr13:113042762-113046388 |
| 9356 | Gpr137 | NM_001177360.1 | chr19:6938069-6941193 | 9453 | Gramd1a | NM_027898.3 | chr7:31130126-31151050 |
| 9357 | Gpr137b | NM_031999.2 | chr13:13357619-13393624 | 9454 | Gramd1b | NM_172768.1 | chr9:40297906-40455764 |
| 9358 | Gpr137b-ps | NR_003568.1 | chr13:12614064-12650395 | 9455 | Gramd1c | NM_001172107.1 | chr16:43980349-44027945 |
| 9359 | Gpr137c | NM_027518.2 | chr14:45219716-45280976 | 9456 | Gramd2 | NM_001033498.1 | chr9:59707763-59716424 |
| 9360 | Gpr139 | NM_001024338.1 | chr7:119144322-119184374 | 9457 | Gramd3 | NM_026240.2 | chr18:56432131-56503792 |
| 9361 | Gpr141 | NM_181754.4 | chr13:19749681-19824257 | 9458 | Gramd4 | NM_001205153.1 | chr15:86058726-86137636 |
| 9362 | Gpr142 | NM_181749.1 | chr11:114798923-114806745 | 9459 | Grap | NM_027817.3 | chr11:61653320-61672777 |
| 9363 | Gpr143 | NM_010951.3 | chrX:152781920-152808646 | 9460 | Grap2 | NM_001289442.1 | chr15:80572596-80652854 |
| 9364 | Gpr146 | NM_001038703.2 | chr5:139389903-139396414 | 9461 | Grasp | NM_019518.3 | chr15:101224206-101232756 |
| 9365 | Gpr149 | NM_177346.4 | chr3:62529962-62605140 | 9462 | Grb10 | NM_001177629.1 | chr11:11930498-12027971 |
| 9366 | Gpr15 | NM_001162615.1 | chr16:58717434-58718724 | 9463 | Grb14 | NM_016719.1 | chr2:64912481-65022768 |
| 9367 | Gpr150 | NM_175495.2 | chr13:76054850-76056996 | 9464 | Grb2 | NM_008163.4 | chr11:115644044-115708597 |
| 9368 | Gpr151 | NM_181543.1 | chr18:42578019-42579652 | 9465 | Grb7 | NM_010346.2 | chr11:98446833-98455373 |
| 9369 | Gpr152 | NM_206973.2 | chr19:4139798-4145780 | 9466 | Grcc10 | NM_013535.1 | chr6:124739183-124741079 |
| 9370 | Gpr153 | NM_178406.2 | chr4:152274361-152285337 | 9467 | Greb1 | NM_001252071.1 | chr12:16670614-16757239 |
| 9371 | Gpr155 | NM_001190297.2 | chr2:73341506-73386480 | 9468 | Greb1l | NM_001083628.1 | chr18:10325178-10562941 |
| 9372 | Gpr156 | NM_153394.2 | chr16:37916495-38007529 | 9469 | Grem1 | NM_011824.4 | chr2:113748674-113768648 |
| 9373 | Gpr157 | NM_177366.3 | chr4:150087502-150105927 | 9470 | Grem2 | NM_011825.1 | chr1:174833784-174921819 |
| 9374 | Gpr158 | NM_001004761.1 | chr2:21225686-21830542 | 9471 | Grhl1 | NM_001161406.1 | chr12:24372286-24617391 |
| 9375 | Gpr160 | NM_001134385.2 | chr3:30855949-30897194 | 9472 | Grhl2 | NM_026496.4 | chr15:37233035-37363568 |
| 9376 | Gpr161 | NM_001081126.2 | chr1:165295765-165326745 | 9473 | Grhl3 | NM_001013756.1 | chr4:135541887-135573620 |
| 9377 | Gpr162 | NM_033313.3 | chr6:124858444-124863917 | 9474 | Grhpr | NM_080289.2 | chr4:44981393-44990734 |
| 9378 | Gpr165 | NM_029536.3 | chrX:96713467-96719368 | 9475 | Gria1 | NM_001113325.2 | chr11:57013617-57330244 |
| 9379 | Gpr17 | NM_001025381.2 | chr18:31942998-31949636 | 9476 | Gria2 | NM_001039195.1 | chr3:80691491-80802791 |
| 9380 | Gpr171 | NM_173398.3 | chr3:59096447-59101821 | 9477 | Gria3 | NM_001281929.1 | chrX:41401300-41678601 |
| 9381 | Gpr173 | NM_027843.4 | chrX:152343598-152368704 | 9478 | Gria4 | NM_001113180.1 | chr9:4417892-4796234 |
| 9382 | Gpr174 | NM_001033251.4 | chrX:107256027-107296769 | 9479 | Grid1 | NM_008166.2 | chr14:34820135-35581115 |
| 9383 | Gpr176 | NM_201367.3 | chr2:118277097-118373419 | 9480 | Grid2 | NM_008167.2 | chr6:63256856-64666279 |
| 9384 | Gpr179 | NM_001081220.1 | chr11:97332108-97352073 | 9481 | Grid2ip | NM_001159321.1 | chr5:143357937-143391468 |
| 9385 | Gpr18 | NM_182806.1 | chr14:121911433-121915774 | 9482 | Griflin | NM_030022.1 | chr5:140563188-140565067 |
| 9386 | Gpr180 | NM_021434.5 | chr14:118137126-118164232 | 9483 | Grik1 | NM_010348.3 | chr16:87895896-88290258 |
| 9387 | Gpr182 | NM_007412.2 | chr10:127749601-127751798 | 9484 | Grik2 | NM_001111268.1 | chr10:49039462-49788754 |
| 9388 | Gpr183 | NM_183031.2 | chr14:121582330-121965193 | 9485 | Grik3 | NM_001081097.2 | chr4:125490830-125714173 |
| 9389 | Gpr19 | NM_001167894.2 | chr6:134869091-134897929 | 9486 | Grik4 | NM_175481.5 | chr9:42520411-42944371 |
| 9390 | Gpr20 | NM_177383.4 | chr15:73694606-73707505 | 9487 | Grik5 | NM_008168.2 | chr7:25009850-25072369 |
| 9391 | Gpr21 | NM_177383.4 | chr2:37518625-37519281 | 9488 | Grin1 | NM_001177656.2 | chr2:25291176-25319187 |
| 9392 | Gpr22 | NM_175191.4 | chr12:31708686-31713926 | 9489 | Grin1os | NM_001242940.1 | chr2:25291219-25298928 |
| 9393 | Gpr25 | NM_001101516.1 | chr1:136258913-136260873 | 9490 | Grin2a | NM_008170.2 | chr16:9577709-9392533 |
| 9394 | Gpr26 | NM_173410.3 | chr7:131964459-131985633 | 9491 | Grin2b | NM_008171.3 | chr6:135729804-136173511 |
| 9395 | Gpr27 | NM_008158.1 | chr6:99692678-99699318 | 9492 | Grin2c | NM_010350.2 | chr11:115249168-115267243 |
| 9396 | Gpr3 | NM_008154.3 | chr4:133209193-133212536 | 9493 | Grin2d | NM_008172.2 | chr7:45832482-45866681 |
| 9397 | Gpr31b | NM_001013832.2 | chr17:13051320-13052280 | 9494 | Grin3a | NM_001033351.2 | chr4:49861610-49845769 |
| 9398 | Gpr33 | NM_008159.3 | chr12:52023003-52028063 | 9495 | Grin3b | NM_130455.2 | chr10:79970723-79977190 |
| 9399 | Gpr34 | NM_011823.4 | chrX:13632768-13640858 | 9496 | Grina | NM_023168.3 | chr15:76246806-76249904 |
| 9400 | Gpr35 | NM_001104529.1 | chr1:92973118-92986391 | 9497 | Grip1 | NM_001277292.1 | chr10:119454033-120077161 |
| 9401 | Gpr37 | NM_010338.2 | chr6:25568522-25689980 | 9498 | Grip1os2 | NR_045359.1 | chr10:119746061-119761699 |
| 9402 | Gpr37l1 | NM_134438.3 | chr1:135160249-135187681 | 9499 | Grip2 | NM_001159607.1 | chr6:91761509-91807393 |
| 9403 | Gpr39 | NM_027677.2 | chr1:125676995-125873861 | 9500 | Gripap1 | NM_001290455.1 | chrX:7789992-7820567 |
| 9404 | Gpr4 | NM_175668.4 | chr7:19122537-19224176 | 9501 | Grk1 | NM_011881 | chr8:13405080-13421949 |
| 9405 | Gpr45 | NM_053107.4 | chr1:42952871-43035449 | 9502 | Grk4 | NM_001080743.1 | chr5:34660378-34701088 |
| 9406 | Gpr50 | NM_010340.2 | chrX:71663666-71669257 | 9503 | Grk5 | NM_018869.3 | chr19:60889748-61092555 |
| 9407 | Gpr52 | NM_001146330.1 | chr1:160576667-160577753 | 9504 | Grk6 | NM_001038018.4 | chr13:55455330-55460927 |
| 9408 | Gpr55 | NM_001033290.2 | chr1:85939536-85961055 | 9505 | Grm1 | NM_001114333.2 | chr10:10686058-11082331 |

Fig.21 - 50

| | | | | | | | | |
|---|---|---|---|---|---|---|---|---|
| 9506 | Grm2 | NM_001160353.1 | chr9:106644533-106656109 | | 9603 | Gtpbp3 | NM_032544.3 | chr8:71488102-71493400 |
| 9507 | Grm3 | NM_181850.2 | chr5:9485235-9725352 | | 9604 | Gtpbp4 | NM_027000.4 | chr13:8972477-8996012 |
| 9508 | Grm4 | NM_001013385.2 | chr17:27422387-27503533 | | 9605 | Gtpbp6 | NM_145147.5 | chr5:110103976-110108197 |
| 9509 | Grm5 | NM_001081414.2 | chr7:87584167-88135063 | | 9606 | Gtpbp8 | NM_001159329.1 | chr16:44738878-44746363 |
| 9510 | Grm6 | NM_173372.2 | chr11:50850684-50866208 | | 9607 | Grsel | NM_001168672.1 | chr15:85859706-85876573 |
| 9511 | Grm7 | NM_177328.3 | chr6:110645597-111567230 | | 9608 | Gtsf1 | NM_028797.1 | chr15:103402458-103430427 |
| 9512 | Grm8 | NM_008174.2 | chr6:27275120-28134369 | | 9609 | Gtsf1l | NM_026630.2 | chr2:163087030-163089601 |
| 9513 | Grn | NM_008175.4 | chr11:102430321-102436809 | | 9610 | Guca1a | NM_008189.2 | chr17:47394557-47400584 |
| 9514 | Grp | NM_175012.4 | chr18:65873485-65886596 | | 9611 | Guca1b | NM_146079.1 | chr17:47385392-47392967 |
| 9515 | Grpel1 | NM_024478.2 | chr5:36465184-36474077 | | 9612 | Guca2a | NM_008190.1 | chr4:119637731-119639468 |
| 9516 | Grpel2 | NM_021296.2 | chr18:61712423-61726331 | | 9613 | Guca2b | NM_008191.2 | chr4:119656602-119658945 |
| 9517 | Grpr | NM_008177.3 | chrX:163513903-163549736 | | 9614 | Gucd1 | NM_175133.1 | chr10:75506813-75517322 |
| 9518 | Grrp1 | NM_001099296.2 | chr4:134251109-134254106 | | 9615 | Gucy1a2 | NM_001033322.2 | chr9:353234S-3905787 |
| 9519 | Gtsf1 | NM_001098476.2 | chr5:88659232-88675580 | | 9616 | Gucy1a3 | NM_021896.5 | chr3:82092426-82145877 |
| 9520 | Grtp1 | NM_025768.2 | chr8:13176868-13200624 | | 9617 | Gucy1b2 | NM_001204340.1 | chr14:62392669-62456289 |
| 9521 | Grwd1 | NM_153419.2 | chr7:45825222-45830789 | | 9618 | Gucy1b3 | NM_001161796.1 | chr3:82032003-82074711 |
| 9522 | Grxcr1 | NM_001018019.2 | chr5:68031834-68166398 | | 9619 | Gucy2c | NM_001127318.1 | chr6:136697283-136781742 |
| 9523 | Grxcr2 | NM_001034426.2 | chr18:41986200-41990049 | | 9620 | Gucy2d | NM_001130693.3 | chr7:98440415-98477478 |
| 9524 | Gsap | NM_175437.3 | chr5:21186266-21291701 | | 9621 | Gucy2e | NM_008192.3 | chr11:69218118-69237022 |
| 9525 | Gsc | NM_010351.1 | chr12:104471208-104473236 | | 9622 | Gucy2f | NM_001007576.2 | chrX:142079288-142196936 |
| 9526 | Gsc2 | NM_029469.1 | chr16:17913553-17915059 | | 9623 | Gucy2g | NM_001081076.2 | chr19:55198097-55241236 |
| 9527 | Gsdma | NM_021347.4 | chr11:98664350-98677708 | | 9624 | Guf1 | NM_172711.3 | chr5:69556923-69574652 |
| 9528 | Gsdma2 | NM_029727.2 | chr11:98646758-98657957 | | 9625 | Guk1 | NM_001159410.1 | chr11:59183854-59187741 |
| 9529 | Gsdma3 | NM_001007461.1 | chr11:98626359-98638089 | | 9626 | Gulo | NM_178747.3 | chr14:65986786-66009210 |
| 9530 | Gsdmc2 | NM_031378.3 | chr15:63775970-63808739 | | 9627 | Gulp1 | NM_028450.3 | chr1:44556170-44796836 |
| 9531 | Gsdmc | NM_001168274.1 | chr15:63824345-63845176 | | 9628 | Gusb | NM_010368.1 | chr5:129989020-130002828 |
| 9532 | Gsdmc3 | NM_183194.3 | chr15:63857724-63878558 | | 9629 | Gvin1 | NM_001039160.2 | chr7:105895118-106215340 |
| 9533 | Gsdmc4 | NM_028992.1 | chr15:63891264-63912297 | | 9630 | Gxylt1 | NM_001033275.4 | chr15:93239741-93275084 |
| 9534 | Gsdmcl1 | NR_108651.1 | chr15:63847308-63850942 | | 9631 | Gxylt2 | NM_198612.2 | chr6:100704733-100905081 |
| 9535 | Gsdmcl2 | NR_108053.1 | chr15:63880706-63889073 | | 9632 | Gyg | NM_013755.3 | chr3:20122083-20155116 |
| 9536 | Gsdmcl-ps | NR_029434.1 | chr15:63914460-63925453 | | 9633 | Gyk | NM_008194.3 | chrX:85701936-85776819 |
| 9537 | Gsdmd | NM_026960.4 | chr15:75862338-75867404 | | 9634 | Gyk1l | NM_010293.3 | chr18:52693678-52695583 |
| 9538 | Gse1 | NM_001145896.1 | chr8:120557408-120581383 | | 9635 | Gvlt1b | NM_001166633.2 | chr2:92365045-92371057 |
| 9539 | Gsg1 | NM_001080552.1 | chr6:135237329-135247884 | | 9636 | Gypa | NM_010369.3 | chr8:80494044-80510785 |
| 9540 | Gsg1l | NM_001101488.1 | chr7:125878418-126082411 | | 9637 | Gypc | NM_001048207.1 | chr18:32528319-32560034 |
| 9541 | Gsg2 | NM_010359.2 | chr11:73135433-73138294 | | 9638 | Gys1 | NM_030678.3 | chr7:45434838-45456617 |
| 9542 | Gsk3a | NM_001031667.1 | chr7:25228258-25237851 | | 9639 | Gys2 | NM_145572.2 | chr6:142422612-142473109 |
| 9543 | Gsk3b | NM_019827.4 | chr16:38089000-38246079 | | 9640 | Gzf1 | NM_028986.3 | chr2:148681119-148692949 |
| 9544 | Gskip | NM_178613.3 | chr12:105685351-105705052 | | 9641 | Gzma | NM_010370.2 | chr13:113093826-113100981 |
| 9545 | Gsn | NM_001206367.1 | chr2:35256358-35307902 | | 9642 | Gzmb | NM_013542.2 | chr14:56258857-56262260 |
| 9546 | Gspt1 | NM_001130008.1 | chr16:11216240-11254325 | | 9643 | Gzmc | NM_010371.3 | chr14:56231400-56234657 |
| 9547 | Gspt2 | NM_001162068-94638961 | chrX:94638961 | | 9644 | Gzmd | NM_010372.2 | chr14:56129567-56132593 |
| 9548 | Gsr | NM_010344.4 | chr8:33653237-33698162 | | 9645 | Gzme | NM_010373.3 | chr14:56117618-56120625 |
| 9549 | Gss | NM_001291111.1 | chr2:155583180-155592810 | | 9646 | Gzmf | NM_010374.3 | chr14:56205262-56211407 |
| 9550 | Gsta1 | NM_008181.3 | chr9:78230668-78242683 | | 9647 | Gzmg | NM_010375.2 | chr14:56156580-56159579 |
| 9551 | Gsta2 | NM_008182.3 | chr9:78331019-78347145 | | 9648 | Gzmk | NM_008196.1 | chr13:113171873-113180897 |
| 9552 | Gsta3 | NM_001077353.2 | chr1:21240584-21265575 | | 9649 | Gzmm | NM_008504.3 | chr10:79689019-79695261 |
| 9553 | Gsta4 | NM_010357.3 | chr9:78191965-78209349 | | 9650 | Gzmn | NM_153052.2 | chr14:56165795-56174599 |
| 9554 | Gstcd | NM_026231.2 | chr3:132982550-133091740 | | 9651 | H13 | NM_001159581.1 | chr2:152669460-152708668 |
| 9555 | Gstk1 | NM_029555.3 | chr6:42245988-42250441 | | 9652 | H19 | NR_130973.1 | chr7:142575532-142578146 |
| 9556 | Gstm1 | NM_010358.5 | chr3:108012249-108017973 | | 9653 | H1f0 | NM_008197.3 | chr15:79028211-79030500 |
| 9557 | Gstm2 | NM_008183.3 | chr3:107981701-107986436 | | 9654 | H1fnt | NM_027304.2 | chr15:98255981-98257307 |
| 9558 | Gstm3 | NM_010359.3 | chr3:107963695-107969174 | | 9655 | H1foo | NM_138311.3 | chr6:115944930-115950242 |
| 9559 | Gstm4 | NM_001160411.1 | chr3:108040407-108044859 | | 9656 | H1fx | NM_198622.1 | chr6:87980420-87981482 |
| 9560 | Gstm5 | NM_010362.3 | chr3:107963853-107898685 | | 9657 | H2-Aa | NM_010378.2 | chr17:34263226-34269418 |
| 9561 | Gstm6 | NM_008184.3 | chr3:107948847-107943749 | | 9658 | H2-Ab1 | NM_207105.3 | chr17:34263226-34269418 |
| 9562 | Gstm7 | NM_026672.2 | chr3:107926333-107931745 | | 9659 | H2afb1 | NM_026627.2 | chr2:179964416-17996358 |
| 9563 | Gsto1 | NM_010362.2 | chr19:47854988-47864788 | | 9660 | H2afb2 | NM_001281530.1 | chrX:116681177-116681525 |
| 9564 | Gsto2 | NM_026619.2 | chr19:47865793-47886305 | | 9661 | H2afb3 | NM_001281531.1 | chrX:120312747-120313095 |
| 9565 | Gstp1 | NM_013541.1 | chr19:4035410-4037912 | | 9662 | H2afj | NM_177688.4 | chr6:136808247-136810074 |
| 9566 | Gstp2 | NM_181796.2 | chr19:4040287-4042221 | | 9663 | H2afv | NM_029938.1 | chr11:6427225-6444443 |
| 9567 | Gstt1 | NM_008185.3 | chr10:75788812-75798584 | | 9664 | H2afx | NM_010436.2 | chr9:44334714-44336073 |
| 9568 | Gstt2 | NM_010362.3 | chr10:75784481-75834881 | | 9665 | H2afy | NM_001159513.1 | chr13:56073621-56135550 |
| 9569 | Gstt3 | NM_133994.3 | chr10:75774121-75781414 | | 9666 | H2afy2 | NM_207000.2 | chr10:61738646-61783864 |
| 9570 | Gstt4 | NM_029472.3 | chr10:75814943-75822543 | | 9667 | H2afy3 | NR_003523.1 | chr15:62217540-62219451 |
| 9571 | Gstz1 | NM_001252555.1 | chr12:87147164-87164723 | | 9668 | H2afz | NM_016750.3 | chr3:137864486-137866922 |
| 9572 | Gsx1 | NM_008178.2 | chr5:147189695-147190946 | | 9669 | H2bfm | NM_027067.2 | chrX:136927324-136928375 |
| 9573 | Gsx2 | NM_133256.2 | chr5:75075600-75077893 | | 9670 | H2-Bl | NM_008199.2 | chr17:36080188-36084249 |
| 9574 | Gt(ROSA)26Sor | NR_027008.1 | chr6:113070398-113077244 | | 9671 | H2-D1 | NM_010380.3 | chr17:35263093-35267497 |
| 9575 | Gtdc1 | NM_172662.3 | chr2:44564411-44861622 | | 9672 | H2-DMa | NM_010386.4 | chr17:34122831-34139101 |
| 9576 | Gtf2a1 | NM_031391.2 | chr12:91555261-91589649 | | 9673 | H2-DMb1 | NM_010387.3 | chr17:34153190-34160229 |
| 9577 | Gtf2a1l | NM_023630.2 | chr17:88668859-88715150 | | 9674 | H2-DMb2 | NM_010388.4 | chr17:34145415-34151095 |
| 9578 | Gtf2a2 | NM_001039519.2 | chr9:70012547-70022866 | | 9675 | H2-Ea-ps | NM_010381.2 | chr17:34342211-34344645 |
| 9579 | Gtf2b | NM_145546.1 | chr3:142765246-142783605 | | 9676 | H2-Eb1 | NM_010382.2 | chr17:34305866-34316674 |
| 9580 | Gtf2e1 | NM_028812.3 | chr16:37509795-37539769 | | 9677 | H2-Eb2 | NM_001033978.3 | chr17:34325674-34341410 |
| 9581 | Gtf2e2 | NM_001167921.1 | chr8:33731913-33777173 | | 9678 | H2-K1 | NM_001001892.2 | chr17:33996011-34000333 |
| 9582 | Gtf2f1 | NM_133801.2 | chr17:57003401-57011288 | | 9679 | H2-K2 | NR_004446.1 | chr17:33974658-33978791 |
| 9583 | Gtf2f2 | NM_026816.3 | chr14:75896936-76010865 | | 9680 | H2-Ke2 | NM_001185182.1 | chr17:33938908-33940330 |
| 9584 | Gtf2h1 | NM_001291075.1 | chr7:46759670-46823800 | | 9681 | H2-Ke6 | NM_013542.4 | chr17:34026032-34028055 |
| 9585 | Gtf2h2 | NM_022011.4 | chr13:100468576-100492609 | | 9682 | H2-L | NM_001267808.1 | chr17:35263122-35266730 |
| 9586 | Gtf2h3 | NM_181410.3 | chr5:124579147-124597680 | | 9683 | H2-M1 | NM_177636.2 | chr17:36670007-36672197 |
| 9587 | Gtf2h4 | NM_010364.4 | chr17:35667727-35673743 | | 9684 | H2-M10.1 | NM_013544.3 | chr17:36322859-36326150 |
| 9588 | Gtf2h5 | NM_181392.3 | chr17:6079827-6085485 | | 9685 | H2-M10.3 | NM_177923.1 | chr17:36284280-36286421 |
| 9589 | Gtf2i | NM_001080746.2 | chr5:134237831-134314760 | | 9686 | H2-M10.3 | NM_203608.2 | chr17:36365003-36368417 |
| 9590 | Gtf2ird1 | NM_001081462.2 | chr5:134357660-134456716 | | 9687 | H2-M10.4 | NM_177634.1 | chr17:36460816-36462329 |
| 9591 | Gtf2ird2 | NM_053266.1 | chr5:134184037-134218143 | | 9688 | H2-M10.5 | NM_177637.1 | chr17:36772909-36776235 |
| 9592 | Gtf3a | NM_226523.3 | chr5:146944856-146955614 | | 9689 | H2-M10.6 | NM_201611.2 | chr17:36812174-36815566 |
| 9593 | Gtf3c1 | NM_207239.1 | chr7:125640953-125707688 | | 9690 | H2-M11 | NM_177635.1 | chr17:36547074-36549252 |
| 9594 | Gtf3c2 | NM_027901.2 | chr5:31156005-31180144 | | 9691 | H2-M2 | NM_008204.2 | chr17:37480850-37483529 |
| 9595 | Gtf3c3 | NM_001033194.3 | chr1:54395876-54439026 | | 9692 | H2-M3 | NM_013819.2 | chr17:37270733-37274485 |
| 9596 | Gtf3c4 | NM_001166033.1 | chr2:28822299-28840360 | | 9693 | H2-M5 | NM_001159075.1 | chr17:36986854-36989904 |
| 9597 | Gtf3c5 | NM_001290484.1 | chr2:28566244-28583279 | | 9694 | H2-M9 | NM_008205.1 | chr17:36640424-36642644 |
| 9598 | Gtf3c6 | NM_026726.2 | chr10:40249202-40257665 | | 9695 | H2-Oa | NM_008206.2 | chr17:34092378-34095234 |
| 9599 | Gtl3 | NM_008187.2 | chr9:95420249-95434869 | | 9696 | H2-Ob | NM_010389.3 | chr17:34238904-34245908 |
| 9600 | Gtpbp1 | NM_013818.2 | chr15:79690895-79721479 | | 9697 | H2-Q1 | NM_010390.3 | chr17:35320557-35325099 |
| 9601 | Gtpbp10 | NM_153116.1 | chr5:5537456-5559501 | | 9698 | H2-Q10 | NM_010391.4 | chr17:35470088-35474563 |
| 9602 | Gtpbp2 | NM_001145979.1 | chr17:46161031-46169370 | | 9699 | H2-Q2 | NM_010392.2 | chr17:35342332-35345722 |

Fig.21 - 51

| | | | | | | | |
|---|---|---|---|---|---|---|---|
| 9700 | H2-Q4 | NM_001143689.1 | chr17:35379616-35384674 | 9797 | Hdac7 | NM_001204275.1 | chr15:97792663-97844502 |
| 9701 | H2-Q5 | NR_051381.1 | chr17:35394098-35395630 | 9798 | Hdac8 | NM_027382.4 | chrX:102284637-102505158 |
| 9702 | H2-Q6 | NM_207648.1 | chr17:35424876-35428361 | 9799 | Hdac9 | NM_001271386.1 | chr12:34047581-34917095 |
| 9703 | H2-Q7 | NM_001198560.1 | chr17:35439154-35443773 | 9800 | Hdc | NM_008230.6 | chr2:126593659-126618678 |
| 9704 | H2-Q8 | NM_023124.5 | chr17:35424846-35428361 | 9801 | Hddc2 | NM_027168.2 | chr10:31313404-31328086 |
| 9705 | H2-Q9 | NM_001201460.1 | chr17:35439166-35443770 | 9802 | Hddc3 | NM_026812.2 | chr7:80343136-80346097 |
| 9706 | H2-T10 | NM_010395.7 | chr17:36115875-36121435 | 9803 | Hdgf | NM_008231.4 | chr3:87906320-87916132 |
| 9707 | H2-T22 | NM_010397.4 | chr17:36038408-36042702 | 9804 | Hdgfl1 | NM_008232.3 | chr13:26768171-26770165 |
| 9708 | H2-T23 | NM_010398.3 | chr17:36029976-36032701 | 9805 | Hdgfrp2 | NM_008233.3 | chr17:56079630-56100604 |
| 9709 | H2-T24 | NM_008207.3 | chr17:36005694-36020560 | 9806 | Hdgfrp3 | NM_013886.4 | chr7:81881255-81934459 |
| 9710 | H2-T3 | NM_008208.4 | chr17:36185570-36190151 | 9807 | Hdhd1a | NM_026108.3 | chrX:50567655-50568699 |
| 9711 | H2-T9 | NM_010399.2 | chr17:36038408-36042692 | 9808 | Hdhd2 | NM_001039201.1 | chr18:76944417-76972171 |
| 9712 | H3f3a | NM_008210.4 | chr1:180802567-180813603 | 9809 | Hdhd3 | NM_024257.1 | chr4:62499053-62502200 |
| 9713 | H3f3b | NM_008211.3 | chr11:116021960-116024504 | 9810 | Hdlbp | NM_133808.5 | chr1:93405939-93478917 |
| 9714 | H60b | NM_001177775.1 | chr10:22273473-22288848 | 9811 | Hdx | NM_001080549.2 | chrX:111575203-111697079 |
| 9715 | H60c | NM_001204916.2 | chr10:3256207-3257771 | 9812 | Heatr1 | NM_144835.4 | chr13:12395374-12438893 |
| 9716 | H6pd | NM_001291004.1 | chr4:149979473-150003236 | 9813 | Heatr2 | NM_001081265.1 | chr5:139130222-139186505 |
| 9717 | Hao | NM_025325.2 | chr17:83831353-83846790 | 9814 | Heatr3 | NM_172757.3 | chr8:88137884-88171983 |
| 9718 | Habp2 | NM_146101.1 | chr19:56287937-56320089 | 9815 | Heatr5a | NM_177171.4 | chr12:51875872-51971321 |
| 9719 | Habp4 | NM_019986 | chr3:64161865-64186537 | 9816 | Heatr5b | NM_001081379.1 | chr17:78752905-78835381 |
| 9720 | Hace1 | NM_172473.3 | chr10:45577828-45712345 | 9817 | Heatr6 | NM_145432.3 | chr11:83753636-83783754 |
| 9721 | Hacl1 | NM_019975.3 | chr14:31607225-31640965 | 9818 | Heatr9 | NM_001045543.2 | chr11:83518678-83522099 |
| 9722 | Hadh | NM_008212.4 | chr3:131233419-131272101 | 9819 | Hebp1 | NM_013546.2 | chr6:135137518-135168215 |
| 9723 | Hadha | NM_178878.2 | chr5:30118303-30154980 | 9820 | Hebp2 | NM_019487.3 | chr10:18540122-18546076 |
| 9724 | Hadhb | NM_001289798.1 | chr5:30155252-30184593 | 9821 | Heca | NM_001033432.3 | chr10:17900465-17948067 |
| 9725 | Hagh | NM_001159626.1 | chr17:24850666-24864450 | 9822 | Hectd1 | NM_144788.2 | chr12:51743721-51829536 |
| 9726 | Haghl | NM_001271433.1 | chr17:25782786-25785586 | 9823 | Hectd2 | NM_001163471.1 | chr19:36554638-36621135 |
| 9727 | Hal | NM_010401.3 | chr10:93488767-93516743 | 9824 | Hectd3 | NM_175244.3 | chr4:116995347-117005277 |
| 9728 | Hamp | NM_032541.1 | chr7:30942368-30944017 | 9825 | Hecw1 | NM_001081348.3 | chr13:14226437-14523226 |
| 9729 | Hamp2 | NM_183257.3 | chr7:30922371-30924181 | 9826 | Hecw2 | NM_001018833 | chr1:53806873-54198034 |
| 9730 | Hand1 | NM_008213.2 | chr11:57828712-57832147 | 9827 | Heg1 | NM_175256.5 | chr16:33834465-33768195 |
| 9731 | Hand2 | NM_010402.4 | chr8:57320982-57324517 | 9828 | Helb | NM_080446.2 | chr10:120083607-120112965 |
| 9732 | Hao1 | NM_010403.2 | chr2:134497360-134554352 | 9829 | Hells | NM_008234.3 | chr19:38930989-38968277 |
| 9733 | Hao2 | NM_019545.4 | chr3:98874518-98893230 | 9830 | Helq | NM_001081107.1 | chr5:100762147-100798600 |
| 9734 | Hap1 | NM_010404.3 | chr11:100347326-100366141 | 9831 | Helt | NM_173789.4 | chr8:46292047-46294671 |
| 9735 | Hapln1 | NM_013500.4 | chr13:89540635-89611832 | 9832 | Helz | NM_198798.1 | chr11:107547959-107686943 |
| 9736 | Hapln2 | NM_022031.1 | chr3:88021749-88027511 | 9833 | Helz2 | NM_183182.2 | chr2:181227614-181242027 |
| 9737 | Hapln3 | NM_178255.3 | chr7:79117026-79131018 | 9834 | Hemgn | NM_053149.2 | chr4:46393988-46404183 |
| 9738 | Hapln4 | NM_177900.4 | chr8:70083528-70090862 | 9835 | Hemk1 | NM_133984.2 | chr9:107327081-107338350 |
| 9739 | Harbi1 | NM_178724.4 | chr2:91710949-91721566 | 9836 | Hemt1 | NM_010416.2 | chr15:74819079-74824436 |
| 9740 | Hars | NM_008214.4 | chr18:36766527-36783205 | 9837 | Henmt1 | NM_001078646.1 | chr3:108940956-108960776 |
| 9741 | Hars2 | NM_080636.2 | chr18:36783208-36792560 | 9838 | Hepacam | NM_175189.4 | chr9:37387605-37386571 |
| 9742 | Has1 | NM_008215.2 | chr17:17843325-17855188 | 9839 | Hepacam2 | NM_178899.5 | chr6:3457088-3494498 |
| 9743 | Has2 | NM_008216.3 | chr15:56665626-56694546 | 9840 | Heph | NM_001159627.1 | chrX:96456345-96574484 |
| 9744 | Has2os | NR_002874.2 | chr15:56689943-56694460 | 9841 | Hephl1 | NM_001164797.1 | chr9:15051840-15112108 |
| 9745 | Has3 | NM_008217.4 | chr8:106870241-106882902 | 9842 | Herc1 | NM_145617.3 | chr9:66350449-66508775 |
| 9746 | Hat1 | NM_013259.2 | chr2:71389259-71441622 | 9843 | Herc2 | NM_010418.2 | chr7:56050154-56231798 |
| 9747 | Haus1 | NM_146089.2 | chr18:77757566-77767780 | 9844 | Herc3 | NM_028705.3 | chr6:58833699-58920396 |
| 9748 | Haus2 | NM_001290807.1 | chr2:120609594-120621559 | 9845 | Herc4 | NM_026101.4 | chr10:63243796-63317881 |
| 9749 | Haus3 | NM_146101.6 | chr5:34153896-34169424 | 9846 | Herc6 | NM_025992.2 | chr6:57580991-57665138 |
| 9750 | Haus4 | NM_145462.2 | chr14:54541784-54554361 | 9847 | Herpud1 | NM_022331.1 | chr8:94386499-94395358 |
| 9751 | Haus5 | NM_027999.1 | chr7:30663707-30664994 | 9848 | Herpud2 | NM_020586.2 | chr9:25108129-25151781 |
| 9752 | Haus6 | NM_173400.2 | chr4:86581284-86612022 | 9849 | Hes1 | NM_008235.2 | chr16:30065356-30067796 |
| 9753 | Haus7 | NM_028633.3 | chrX:73437314-73459029 | 9850 | Hes2 | NM_008236.4 | chr4:152158866-152162469 |
| 9754 | Haus8 | NM_001163042.1 | chr8:71251123-71272590 | 9851 | Hes3 | NM_008237.4 | chr4:152285971-152291862 |
| 9755 | Havcr1 | NM_001166631.1 | chr11:46750510-46799578 | 9852 | Hes5 | NM_010419.4 | chr4:154960922-154962371 |
| 9756 | Havcr2 | NM_134250.2 | chr11:46454936-46481254 | 9853 | Hes6 | NM_019479.3 | chr1:91411482-91413222 |
| 9757 | Hax1 | NM_001282032.1 | chr3:89995445-89998716 | 9854 | Hes7 | NM_033041.4 | chr11:69120452-69123259 |
| 9758 | Hba-a1 | NM_008218.2 | chr11:32283671-32297303 | 9855 | Hesx1 | NM_010420.2 | chr14:27000361-27002325 |
| 9759 | Hba-a2 | NM_001083955.1 | chr11:32283674-32297310 | 9856 | Hexa | NM_010421.4 | chr9:59539666-59565105 |
| 9760 | Hba-x | NM_010405.4 | chr11:32276599-32278115 | 9857 | Hexb | NM_010422.2 | chr13:97176330-97198357 |
| 9761 | Hbb-b1 | NM_001278161.1 | chr7:103826531-103827929 | 9858 | Hexdc | NM_001001333.2 | chr11:121204482-121222656 |
| 9762 | Hbb-bh1 | NM_008220.3 | chr7:103841637-103843162 | 9859 | Hexim1 | NM_138753.2 | chr11:103116324-103119724 |
| 9763 | Hbb-bh2 | NM_001127686.1 | chr7:103839123-103840521 | 9860 | Hexim2 | NM_001130515.1 | chr11:109133352-103139908 |
| 9764 | Hbb-bs | NM_001201391.1 | chr7:103826522-103827928 | 9861 | Hey1 | NM_010423.2 | chr3:8663358-8667028 |
| 9765 | Hbb-bt | NM_008229.5 | chr7:103812523-103813923 | 9862 | Hey2 | NM_013904.1 | chr10:30832358-30842783 |
| 9766 | Hbb-y | NM_008221.4 | chr7:103851753-103853207 | 9863 | Heyl | NM_013905.3 | chr4:123233555-123249870 |
| 9767 | Hbegf | NM_010415.2 | chr18:36504926-36515805 | 9864 | Hfe | NM_010424.4 | chr13:23703840-23710811 |
| 9768 | Hbp1 | NM_153106.3 | chr12:31926454-31950535 | 9865 | Hfe2 | NM_027126.4 | chr3:96525184-96529216 |
| 9769 | Hbq1a | NM_175000.2 | chr11:32300068-32300873 | 9866 | Hfm1 | NM_001252516.1 | chr5:106901888-106925890 |
| 9770 | Hbq1b | NM_001033983.1 | chr11:32288963-32287912 | 9867 | Hgd | NM_013547.3 | chr16:37580152-37632026 |
| 9771 | Hbs1l | NM_001042593.1 | chr10:21295978-21368689 | 9868 | Hgf | NM_001289458.1 | chr5:16553494-16619439 |
| 9772 | Hc | NM_010406.2 | chr2:34983330-35061441 | 9869 | Hgfac | NM_019447.3 | chr5:35041508-35048461 |
| 9773 | Hcar1 | NM_175220.4 | chr5:123863569-123880020 | 9870 | Hgs | NM_001159128.1 | chr11:120467634-120489984 |
| 9774 | Hcar2 | NM_030701.3 | chr5:123863569-123865516 | 9871 | Hgsnat | NM_029884.1 | chr8:25944458-25976744 |
| 9775 | Hccs | NM_008222.4 | chrX:169311530-169320343 | 9872 | Hhat | NM_144881.4 | chr1:192512827-192771219 |
| 9776 | Hcfc1 | NM_008224.2 | chrX:73942791-73966352 | 9873 | Hhatl | NM_029095.2 | chr9:121784015-121792507 |
| 9777 | Hcfc1r1 | NM_181821.1 | chr7:23673807-23678524 | 9874 | Hhex | NM_008245.3 | chr19:37434840-37440731 |
| 9778 | Hcfc2 | NM_001081218.1 | chr10:82699006-82741392 | 9875 | Hhip | NM_020259.4 | chr8:79965850-80058008 |
| 9779 | Hck | NM_010407.1 | chr2:153108467-153151441 | 9876 | Hhipl1 | NM_001044380.1 | chr12:108306269-108328300 |
| 9780 | Hcls1 | NM_008225.2 | chr16:36934982-36963214 | 9877 | Hhipl2 | NM_030175.5 | chr1:183418469-183437053 |
| 9781 | Hcn1 | NM_010408.3 | chr13:117602319-117981028 | 9878 | Hhla1 | NM_001145096.1 | chr15:65922442-65976804 |
| 9782 | Hcn2 | NM_008226.2 | chr10:79716633-79736108 | 9879 | Hiat1 | NM_008246.2 | chr3:116631166-116662677 |
| 9783 | Hcn3 | NM_008227.1 | chr3:89146774-89160157 | 9880 | Hiatl1 | NM_001083901.1 | chr13:65065029-65112982 |
| 9784 | Hcn4 | NM_001081192.1 | chr9:58823511-58860955 | 9881 | Hibadh | NM_145562.1 | chr6:52546229-52640300 |
| 9785 | Hcrt | NM_010410.2 | chr11:100761669-100762931 | 9882 | Hibch | NM_146108.2 | chr1:52845037-52920986 |
| 9786 | Hcrtr1 | NM_001163027.1 | chr4:130130216-130138551 | 9883 | Hic1 | NM_001098203.1 | chr11:75164564-75168152 |
| 9787 | Hcrtr2 | NM_198962.3 | chr9:76225879-76323578 | 9884 | Hic2 | NM_178922.3 | chr16:17233586-17263430 |
| 9788 | Hcst | NM_011827.3 | chr7:30417711-30419854 | 9885 | Hid1 | NM_175454.2 | chr11:115347708-115367719 |
| 9789 | Hdac1 | NM_008228.2 | chr4:129516103-129542646 | 9886 | Hif1a | NM_010431.2 | chr12:73907866-73947530 |
| 9790 | Hdac10 | NM_199198.2 | chr15:89123302-89128700 | 9887 | Hif1an | NM_176958.3 | chr19:44562853-44576274 |
| 9791 | Hdac11 | NM_144919.2 | chr6:91156814-91174683 | 9888 | Hif3a | NM_001162950.1 | chr7:17030992-17062427 |
| 9792 | Hdac2 | NM_008229.2 | chr10:36974542-37001888 | 9889 | Higd1a | NM_019814.4 | chr9:121848559-121858000 |
| 9793 | Hdac3 | NM_010411.2 | chr18:37936970-37954988 | 9890 | Higd1b | NM_080846.1 | chr11:102836295-102838039 |
| 9794 | Hdac4 | NM_207225.2 | chr1:91928778-92180341 | 9891 | Higd1c | NM_001002900.1 | chr15:100364584-100383955 |
| 9795 | Hdac5 | NM_001077696.1 | chr11:102195746-102230172 | 9892 | Higd2a | NM_025933.3 | chr13:54590230-54591147 |
| 9796 | Hdac6 | NM_001130416.1 | chrX:7930121-7947889 | 9893 | Hilpda | NM_001190461.1 | chr6:29272487-29275449 |

Fig.21 - 52

| | | | | | | | | |
|---|---|---|---|---|---|---|---|---|
| 9894 | Hlfs1 | NM_018792.2 | chr11:94967592-94968456 | | 9991 | Hmg20a | NM_025812.2 | chr9:56418845-56496936 |
| 9895 | Hinfp | NM_172162.3 | chr9:44295672-44305671 | | 9992 | Hmg20b | NM_001163165.1 | chr10:81346045-81350426 |
| 9896 | Hint1 | NM_008248.2 | chr11:54866437-54870496 | | 9993 | Hmga1 | NM_001025427.3 | chr17:27556573-27563672 |
| 9897 | Hint2 | NM_026871.1 | chr4:43654226-43656445 | | 9994 | Hmga1-rs1 | NM_001166476.1 | chr17:27556652-27563671 |
| 9898 | Hint3 | NM_025798.3 | chr10:30608206-30618366 | | 9995 | Hmga2 | NM_010441.2 | chr10:120361274-120476935 |
| 9899 | Hip1 | NM_146001.2 | chr5:135406518-135545122 | | 9996 | Hmga2-ps1 | NR_037996.1 | chr1:176834623-176836133 |
| 9900 | Hip1r | NM_145070.3 | chr5:123973627-124003215 | | 9997 | Hmgb1 | NM_010439.4 | chr5:149046701-149053057 |
| 9901 | Hipk1 | NM_010432.2 | chr3:103739814-103791275 | | 9998 | Hmgb1-rs17 | NR_033589.1 | chr8:33484310-33485757 |
| 9902 | Hipk2 | NM_001136065.2 | chr6:38697839-38837311 | | 9999 | Hmgb2 | NM_008252.3 | chr8:57511842-57515999 |
| 9903 | Hipk3 | NM_001145824.1 | chr2:104426481-104494489 | | 10000 | Hmgb3 | NM_008253.4 | chrX:71555918-71560673 |
| 9904 | Hipk4 | NM_001033315.2 | chr7:27523260-27531174 | | 10001 | Hmgb4 | NM_027036.3 | chr4:128260211-128260895 |
| 9905 | Hira | NM_010435.2 | chr16:18876749-18970308 | | 10002 | Hmgcl | NM_008254.2 | chr4:135946452-135962617 |
| 9906 | Hirip3 | NM_172746.3 | chr7:126861971-126865122 | | 10003 | Hmgcll1 | NM_173731.2 | chr9:76014976-76136350 |
| 9907 | Hist1h1a | NM_030609.3 | chr13:23763667-23764412 | | 10004 | Hmgcr | NM_008255.2 | chr13:96648961-96670936 |
| 9908 | Hist1h1b | NM_020034.2 | chr13:21779831-21780625 | | 10005 | Hmgcs1 | NM_001291439.1 | chr13:119690350-119708260 |
| 9909 | Hist1h1c | NM_015786.3 | chr13:23738806-23739531 | | 10006 | Hmgcs2 | NM_008256.4 | chr3:98280430-98310738 |
| 9910 | Hist1h1d | NM_145713.4 | chr13:23555031-23555807 | | 10007 | Hmgn1 | NM_008251.3 | chr16:96121587-96127725 |
| 9911 | Hist1h1e | NM_015787.4 | chr13:23621776-23622558 | | 10008 | Hmgn2 | NM_016957.3 | chr4:133964738-133967991 |
| 9912 | Hist1h1t | NM_010377.3 | chr13:23696810-23696545 | | 10009 | Hmgn3 | NM_026122.4 | chr9:83109941-83146607 |
| 9913 | Hist1h2aa | NM_175658.2 | chr13:23934461-23934913 | | 10010 | Hmgn5 | NM_016710.2 | chrX:109004536-109013380 |
| 9914 | Hist1h2ab | NM_175660.3 | chr13:23751087-23751592 | | 10011 | Hmgxb3 | NM_134134.2 | chr18:61131276-61177050 |
| 9915 | Hist1h2ac | NM_178189.5 | chr13:23683472-23683959 | | 10012 | Hmgxb4 | NM_178017.1 | chr2:74993702-75031972 |
| 9916 | Hist1h2ad | NM_178188.4 | chr13:23574380-23574915 | | 10013 | Hmha1 | NM_001142701.1 | chr10:80016671-80031471 |
| 9917 | Hist1h2ae | NM_178187.4 | chr13:23570662-23571220 | | 10014 | Hmmr | NM_013552.2 | chr11:40703387-40733437 |
| 9918 | Hist1h2af | NM_175661.2 | chr13:23533910-23534378 | | 10015 | Hmox1 | NM_010442.2 | chr8:75093617-75100593 |
| 9919 | Hist1h2ag | NM_178186.3 | chr13:22042477-22042949 | | 10016 | Hmox2 | NM_001136066.2 | chr16:4726360-4766249 |
| 9920 | Hist1h2ah | NM_175659.2 | chr13:22035121-22035643 | | 10017 | Hmx1 | NM_010445.2 | chr5:35389116-35392872 |
| 9921 | Hist1h2ai | NM_178182.3 | chr13:21716411-21716859 | | 10018 | Hmx2 | NM_145998.3 | chr7:131554061-131566582 |
| 9922 | Hist1h2ak | NM_178183.2 | chr13:21753376-21753912 | | 10019 | Hmx3 | NM_008257.3 | chr7:131542962-131544931 |
| 9923 | Hist1h2an | NM_178184.2 | chr13:21786791-21787218 | | 10020 | Hn1 | NM_008258.1 | chr11:115497352-115514370 |
| 9924 | Hist1h2ao | NM_001177544.2 | chr13:21810386-21810575 | | 10021 | Hn1l | NM_198937.2 | chr17:24942469-24960623 |
| 9925 | Hist1h2ap | NM_178185.2 | chr13:21810466-21833475 | | 10022 | Hnf1a | NM_009327.3 | chr5:114948979-114971062 |
| 9926 | Hist1h2ba | NM_175663.2 | chr13:23933724-23934156 | | 10023 | Hnf1b | NM_001291268.1 | chr11:83850868-83905917 |
| 9927 | Hist1h2bb | NM_175664.3 | chr13:23746733-23747223 | | 10024 | Hnf4a | NM_008261.3 | chr2:163547154-163572907 |
| 9928 | Hist1h2bc | NM_001290380.1 | chr13:23684198-23684667 | | 10025 | Hnf4aos | NR_027970.1 | chr2:163493803-163541721 |
| 9929 | Hist1h2be | NM_001177653.1 | chr13:23583669-23621094 | | 10026 | Hnf4g | NM_013920.2 | chr3:3508029-3659800 |
| 9930 | Hist1h2bf | NM_178195.2 | chr13:23573759-23574190 | | 10027 | Hnmt | NM_080462.2 | chr2:24002912-24049379 |
| 9931 | Hist1h2bg | NM_178196.4 | chr13:23571399-23571863 | | 10028 | Hnrnpa0 | NM_029872.1 | chr13:58125878-58128556 |
| 9932 | Hist1h2bh | NM_178197.2 | chr13:23542922-23543444 | | 10029 | Hnrnpa1 | NM_001039129.4 | chr15:103240396-103244962 |
| 9933 | Hist1h2bj | NM_178198.2 | chr13:22043229-22043658 | | 10030 | Hnrnpa2b1 | NM_016806.3 | chr6:51460434-51469894 |
| 9934 | Hist1h2bk | NM_175665.2 | chr13:22035820-22036320 | | 10031 | Hnrnpa3 | NM_053263.1 | chr2:75659258-75669407 |
| 9935 | Hist1h2bl | NM_178199.2 | chr13:21715712-21716143 | | 10032 | Hnrnpab | NM_001048061.1 | chr11:51600099-51606881 |
| 9936 | Hist1h2bm | NM_178200.2 | chr13:21722043-21722526 | | 10033 | Hnrnpc | NM_001170981.1 | chr14:52073379-52104028 |
| 9937 | Hist1h2bn | NM_178201.2 | chr13:21754212-21754653 | | 10034 | Hnrnpd | NM_001077265.2 | chr5:99955934-99978938 |
| 9938 | Hist1h2bp | NM_001290466.1 | chr13:21787487-21787943 | | 10035 | Hnrnpdl | NM_026890.4 | chr5:100033578-100039222 |
| 9939 | Hist1h2bq | NM_001097979.2 | chr13:21806411-21837530 | | 10036 | Hnrnpf | NM_001166427.1 | chr6:117917293-117925622 |
| 9940 | Hist1h3a | NM_013550.3 | chr13:23761884-23762386 | | 10037 | Hnrnph1 | NM_021510.2 | chr11:50377718-50386528 |
| 9941 | Hist1h3b | NM_178203.2 | chr13:23752379-23752840 | | 10038 | Hnrnph2 | NM_019868.4 | chrX:134601178-134607057 |
| 9942 | Hist1h3c | NM_175653.2 | chr13:23745041-23745521 | | 10039 | Hnrnph3 | NM_001079824.1 | chr10:63014663-63023849 |
| 9943 | Hist1h3d | NM_178204.2 | chr13:23575762-23576266 | | 10040 | Hnrnpk | NM_025279.3 | chr13:58391131-58402512 |
| 9944 | Hist1h3e | NM_178205.2 | chr13:23561895-23562365 | | 10041 | Hnrnpl | NM_177301.5 | chr7:28810889-28822266 |
| 9945 | Hist1h3f | NM_013548.4 | chr13:23544051-23544954 | | 10042 | Hnrnpll | NM_144802.4 | chr17:80029486-80062268 |
| 9946 | Hist1h3g | NM_145070.3 | chr13:23535417-23535909 | | 10043 | Hnrnpm | NM_001109913.1 | chr17:33646232-33685458 |
| 9947 | Hist1h3h | NM_178206.2 | chr13:21717627-21718115 | | 10044 | Hnrnpr | NM_001277221.1 | chr4:136310941-136345979 |
| 9948 | Hist1h3i | NM_178207.2 | chr13:21782074-21783397 | | 10045 | Hnrnpu | NM_016805.2 | chr1:178328299-178337784 |
| 9949 | Hist1h4a | NM_178192.2 | chr13:23760794-23761249 | | 10046 | Hnrnpul1 | NM_144922.2 | chr7:25722038-25754720 |
| 9950 | Hist1h4b | NM_178193.2 | chr13:23756936-23757386 | | 10047 | Hnrnpul2 | NM_001081196.1 | chr19:8819400-8834142 |
| 9951 | Hist1h4c | NM_178194.2 | chr13:23698083-23698458 | | 10048 | Hoga1 | NM_026152.1 | chr19:42045850-42070939 |
| 9952 | Hist1h4d | NM_175654.2 | chr13:23581601-23581969 | | 10049 | Homer1 | NM_001284189.1 | chr13:93304494-93408129 |
| 9953 | Hist1h4f | NM_175655.2 | chr13:23551285-23551643 | | 10050 | Homer2 | NM_001164086.1 | chr7:81600480-81706925 |
| 9954 | Hist1h4h | NM_153173.4 | chr13:23531043-23531478 | | 10051 | Homer3 | NM_011982.3 | chr8:70282998-70294361 |
| 9955 | Hist1h4i | NM_175656.3 | chr13:22040959-22041362 | | 10052 | Homez | NM_001177705.1 | chr14:54852786-54864158 |
| 9956 | Hist1h4j | NM_175657.2 | chr13:21735033-21735456 | | 10053 | Hook1 | NM_030014.2 | chr4:95967378-96024274 |
| 9957 | Hist1h4k | NM_178211.2 | chr13:21750144-21750553 | | 10054 | Hook2 | NM_001167991.1 | chr8:84990594-85003364 |
| 9958 | Hist1h4m | NM_001195421.1 | chr13:21811745-21812150 | | 10055 | Hook3 | NM_207659.3 | chr8:26021420-26119224 |
| 9959 | Hist1h4n | NM_175657.2 | chr13:21811783-21832158 | | 10056 | Hopx | NM_001159900.1 | chr5:77086985-77095267 |
| 9960 | Hist2h2aa1 | NM_013549.2 | chr3:96239778-96246052 | | 10057 | Hormad1 | NM_001289632.1 | chr3:95559676-95587860 |
| 9961 | Hist2h2aa2 | NM_178212.3 | chr3:96239778-96246052 | | 10058 | Hormad2 | NM_029458.1 | chr11:4346382-4441082 |
| 9962 | Hist2h2ab | NM_178213.4 | chr3:96269915-96220353 | | 10059 | Hotair | NR_047528.1 | chr15:102944061-102947946 |
| 9963 | Hist2h2ac | NM_175662.2 | chr3:96220412-96220880 | | 10060 | Hottip | NR_110441.1 | chr6:52262774-52267603 |
| 9964 | Hist2h2bb | NM_178215.2 | chr3:96269699-96270192 | | 10061 | Hoxa1 | NM_010449.4 | chr6:52155366-52158317 |
| 9965 | Hist2h2be | NM_178214.4 | chr3:96221071-96223738 | | 10062 | Hoxa10 | NM_001122950.2 | chr6:52231196-52240854 |
| 9966 | Hist2h3b | NM_178215.2 | chr3:96268653-96269155 | | 10063 | Hoxa11 | NM_010450.3 | chr6:52242104-52245810 |
| 9967 | Hist2h3c1 | NM_178216.3 | chr3:96238478-96247348 | | 10064 | Hoxa11os | NR_015348.1 | chr6:52245242-52249769 |
| 9968 | Hist2h3c2 | NM_054045.4 | chr3:96238478-96247348 | | 10065 | Hoxa13 | NM_008264.1 | chr6:52258852-52260880 |
| 9969 | Hist2h4 | NM_033596.3 | chr3:96262933-96263317 | | 10066 | Hoxa2 | NM_010451.2 | chr6:52162416-52164831 |
| 9970 | Hist3h2a | NM_178218.4 | chr11:58954684-58955192 | | 10067 | Hoxa3 | NM_010452.3 | chr6:52169061-52213067 |
| 9971 | Hist3h2ba | NM_030082.4 | chr11:58948910-58949372 | | 10068 | Hoxa4 | NM_008265.3 | chr6:52189686-52191703 |
| 9972 | Hist3h2bb-ps | NM_206882.1 | chr11:58954047-58954512 | | 10069 | Hoxa5 | NM_010453.4 | chr6:52201753-52204587 |
| 9973 | Hist4h4 | NM_175652.3 | chr6:136803992-136804431 | | 10070 | Hoxa6 | NM_010454.1 | chr6:52206864-52208624 |
| 9974 | Hivep1 | NM_007772.2 | chr13:42052020-42185026 | | 10071 | Hoxa7 | NM_010455.3 | chr6:52215623-52218573 |
| 9975 | Hivep2 | NM_010437.2 | chr10:13966378-14151378 | | 10072 | Hoxa9 | NM_001277238.1 | chr6:52223096-52227370 |
| 9976 | Hivep3 | NM_010657.3 | chr4:119814677-120135411 | | 10073 | Hoxb1 | NM_008266.5 | chr11:96365757-96368253 |
| 9977 | Hjurp | NM_198652.2 | chr1:88258855-88277579 | | 10074 | Hoxb13 | NM_008267.3 | chr11:96194360-96196599 |
| 9978 | Hk1 | NM_001146300.1 | chr10:62268854-62340421 | | 10075 | Hoxb2 | NM_134032.2 | chr11:96351631-96354014 |
| 9979 | Hk1os | NR_038038.1 | chr10:62340606-62349866 | | 10076 | Hoxb3 | NM_001079869.1 | chr11:96323125-96347930 |
| 9980 | Hk2 | NM_013820.3 | chr6:82725026-82774654 | | 10077 | Hoxb4 | NM_010459.2 | chr11:96318266-96321638 |
| 9981 | Hk3 | NM_001033245.4 | chr13:55005984-55021385 | | 10078 | Hoxb5 | NM_008268.2 | chr11:96305311-96306121 |
| 9982 | Hkdc1 | NM_145419.1 | chr10:62285136-62422457 | | 10079 | Hoxb6 | NM_008269.1 | chr11:96299170-96301589 |
| 9983 | Hlcs | NM_139145.4 | chr6:94129305-94287856 | | 10080 | Hoxb7 | NM_010460.2 | chr11:96286645-96290163 |
| 9984 | Hlf | NM_172563.3 | chr11:90338534-90390917 | | 10081 | Hoxb8 | NM_010461.2 | chr11:96283904-96285325 |
| 9985 | Hlx | NM_008250.2 | chr3:20057810-20118491 | | 10082 | Hoxb9 | NM_008270.2 | chr11:96271329-96276593 |
| 9986 | Hls | NM_008250.2 | chr14:184727144-184732493 | | 10083 | Hoxc10 | NM_010462.5 | chr15:102966795-102971897 |
| 9987 | Hmbox1 | NM_177338.5 | chr14:64822217-64940847 | | 10084 | Hoxc11 | NM_001024842.1 | chr15:102954525-102956701 |
| 9988 | Hmbs | NM_001110251.1 | chr9:44326347-44342351 | | 10085 | Hoxc12 | NM_010463.1 | chr15:102936852-102938517 |
| 9989 | Hmces | NM_173737.2 | chr6:87913975-87936613 | | 10086 | Hoxc13 | NM_010464.2 | chr15:102921130-102928814 |
| 9990 | Hmgn1 | NM_001024720.3 | chr1:150562501-150993435 | | 10087 | Hoxc4 | NM_013553.2 | chr15:103034394-103036852 |

Fig.21 - 53

| | | | | | | | |
|---|---|---|---|---|---|---|---|
| 10088 | Hoxc5 | NM_175730.5 | chr15:103014007-103017429 | 10185 | Hspa13 | NM_030201.3 | chr16:75795190-75766818 |
| 10089 | Hoxc6 | NM_010465.2 | chr15:103009561-103011881 | 10186 | Hspa14 | NM_015765.2 | chr2:3488853-3512814 |
| 10090 | Hoxc8 | NM_010466.2 | chr15:102990538-102994254 | 10187 | Hspa1a | NM_010479.2 | chr17:34969358-34972156 |
| 10091 | Hoxc9 | NM_008272.3 | chr15:102977031-102984444 | 10188 | Hspa1b | NM_010478.2 | chr17:34956428-34959238 |
| 10092 | Hoxd1 | NM_010467.2 | chr2:74762979-74765142 | 10189 | Hspa1l | NM_013558.2 | chr17:34972702-34979228 |
| 10093 | Hoxd10 | NM_013554.5 | chr2:74691890-74695106 | 10190 | Hspa2 | NM_001002012.1 | chr12:76404175-76406936 |
| 10094 | Hoxd11 | NM_008273.2 | chr2:74682322-74687016 | 10191 | Hspa4 | NM_008300.3 | chr11:53259813-53300479 |
| 10095 | Hoxd12 | NM_008274.3 | chr2:74675012-74677705 | 10192 | Hspa4l | NM_011020.3 | chr3:40745612-40790365 |
| 10096 | Hoxd13 | NM_008275.3 | chr2:74668309-74671599 | 10193 | Hspa5 | NM_001163434.1 | chr2:34772089-34776529 |
| 10097 | Hoxd3 | NM_010469.2 | chr2:74711992-74748271 | 10194 | Hspa8 | NM_031165.4 | chr9:40801272-40805199 |
| 10098 | Hoxd3os1 | NR_027899.1 | chr2:74710043-74716130 | 10195 | Hspa9 | NM_010481.2 | chr18:34937414-34954351 |
| 10099 | Hoxd4 | NM_010469.2 | chr2:74721977-74729159 | 10196 | Hspb1 | NM_013560.2 | chr5:135887918-135889563 |
| 10100 | Hoxd8 | NM_001290730.1 | chr2:74705488-74707932 | 10197 | Hspb11 | NM_028394.2 | chr4:107253933-107279888 |
| 10101 | Hoxd9 | NM_013555.4 | chr2:74697762-74700208 | 10198 | Hspb2 | NM_001164708.1 | chr5:50751071-50752354 |
| 10102 | Hp | NM_017370.2 | chr8:109575127-109579172 | 10199 | Hspb3 | NM_019960.2 | chr13:113662895-113663676 |
| 10103 | Hp1bp3 | NM_001122896.2 | chr4:138216611-138244682 | 10200 | Hspb6 | NM_001012401.2 | chr7:30553301-30555439 |
| 10104 | Hpca | NM_001130419.2 | chr4:129111569-129121747 | 10201 | Hspb7 | NM_013868.4 | chr4:141420778-141425310 |
| 10105 | Hpcal1 | NM_016677.4 | chr12:17690813-17791926 | 10202 | Hspb8 | NM_030704.3 | chr5:116408490-116422864 |
| 10106 | Hpcal4 | NM_174998.4 | chr4:123183503-123194699 | 10203 | Hspb9 | NM_029307.1 | chr11:100713849-100714575 |
| 10107 | Hpd | NM_008277.2 | chr5:123171806-123182686 | 10204 | Hspbap1 | NM_175111.3 | chr16:35770385-35828462 |
| 10108 | Hpdl | NM_146256.3 | chr4:116819906-116821508 | 10205 | Hspbp1 | NM_024172.3 | chr7:4660520-4684963 |
| 10109 | Hpgd | NM_008278.2 | chr8:56294551-56321046 | 10206 | Hspd1 | NM_010477.4 | chr1:55077833-55087932 |
| 10110 | Hpgds | NM_019455.4 | chr6:65117292-65144730 | 10207 | Hspe1 | NM_008303.4 | chr1:55088147-55091317 |
| 10111 | Hpn | NM_001110252.2 | chr7:31098724-31115326 | 10208 | Hspg2 | NM_008305.3 | chr4:137468802-137570636 |
| 10112 | Hprt | NM_013556.2 | chrX:52988077-53021660 | 10209 | Hsph1 | NM_013559.2 | chr5:149616844-149636315 |
| 10113 | Hps1 | NM_019424.2 | chr19:42755195-42779976 | 10210 | Htatip2 | NM_001146049.1 | chr7:49759105-49773999 |
| 10114 | Hps3 | NM_001146323.1 | chr3:19995944-20035310 | 10211 | Hratsf1 | NM_028242.2 | chrX:57053569-57067182 |
| 10115 | Hps4 | NM_138646.3 | chr5:112343094-112378424 | 10212 | Htr1a | NM_008308.4 | chr13:105443692-105448133 |
| 10116 | Hps5 | NM_001005247.2 | chr7:46760465-46795881 | 10213 | Htr1b | NM_010482.1 | chr9:81631391-81632552 |
| 10117 | Hps6 | NM_176785.3 | chr19:46003477-46006173 | 10214 | Htr1d | NM_001285482.1 | chr4:136423523-136444401 |
| 10118 | Hpse | NM_152808.4 | chr5:100679485-100719683 | 10215 | Htr1f | NM_008310.3 | chr16:64924728-65105784 |
| 10119 | Hpse2 | NM_001081257.2 | chr19:42788594-43388355 | 10216 | Htr2a | NM_172812.2 | chr14:74640839-74706859 |
| 10120 | Hpx | NM_017371.2 | chr7:105591610-105600116 | 10217 | Htr2b | NM_008311.2 | chr1:86099036-86111970 |
| 10121 | Hr | NM_021877.3 | chr14:70554055-70573548 | 10218 | Htr2c | NM_008312.4 | chrX:146962512-147197277 |
| 10122 | Hras | NM_001130443.1 | chr7:141189933-141194004 | 10219 | Htr3a | NM_001099644.1 | chr9:48899212-48911099 |
| 10123 | Hrasls | NM_019751.5 | chr16:29209694-29230530 | 10220 | Htr3b | NM_020774.4 | chr9:48935007-48964990 |
| 10124 | Hrasls5 | NM_025731.2 | chr19:7612568-7639238 | 10221 | Htr4 | NM_008313.4 | chr18:62324203-62467802 |
| 10125 | Hrc | NM_010473.2 | chr7:45335268-45338972 | 10222 | Htr5a | NM_008314.2 | chr5:27841946-27855086 |
| 10126 | Hrct1 | NM_025711.1 | chr4:43727197-43728110 | 10223 | Htr5b | NM_010483.3 | chr1:121509772-121528485 |
| 10127 | Hrg | NM_053176.2 | chr16:22951071-22961659 | 10224 | Htr7 | NM_021358.2 | chr4:139061408-139074789 |
| 10128 | Hrh1 | NM_001252642.1 | chr6:114403365-114483296 | 10225 | Htr7 | NM_008315.2 | chr19:35958728-36057360 |
| 10129 | Hrh2 | NM_001010973.2 | chr13:54192128-54222432 | 10226 | Htra1 | NM_019564.3 | chr7:130960202-130985658 |
| 10130 | Hrh3 | NM_133849.3 | chr2:180099464-180104407 | 10227 | Htra2 | NM_019752.3 | chr6:83051266-83054571 |
| 10131 | Hrh4 | NM_153087.2 | chr18:13006989-13022882 | 10228 | Htra3 | NM_001042615.2 | chr5:35661558-35679780 |
| 10132 | Hrk | NM_007545.2 | chr5:118169763-118129478 | 10229 | Htra4 | NM_001081187.3 | chr8:25024927-25038962 |
| 10133 | Hrnr | NM_133698.2 | chr3:93319748-93333572 | 10230 | Htt | NM_010414.3 | chr5:34761739-34912534 |
| 10134 | Hrsp12 | NM_026821.3 | chr15:34484021-34496246 | 10231 | Hunk | NM_015755.2 | chr16:90386396-90499553 |
| 10135 | Hs1bp3 | NM_021429.3 | chr12:8318432-8343824 | 10232 | Hus1 | NM_008316.5 | chr11:8993156-9011191 |
| 10136 | Hs2st1 | NM_011828.3 | chr3:144431106-144570216 | 10233 | Hus1b | NM_153072.2 | chr13:30946575-30947761 |
| 10137 | Hs3st1 | NM_010474.2 | chr5:39613934-39644631 | 10234 | Huwe1 | NM_023523.4 | chrX:151803281-151935417 |
| 10138 | Hs3st2 | NM_001081327.1 | chr7:121392295-121501768 | 10235 | Hvcn1 | NM_001042489.2 | chr5:122209728-122242297 |
| 10139 | Hs3st3a1 | NM_178870.5 | chr11:64435331-64522835 | 10236 | Hvat1 | NM_008317.4 | chr9:107576951-107580133 |
| 10140 | Hs3st3b1 | NM_018805.2 | chr11:63884692-63922284 | 10237 | Hvat2 | NM_010489.2 | chr9:107569162-107572778 |
| 10141 | Hs3st4 | NM_001252072.1 | chr7:123983180-124398989 | 10238 | Hyal3 | NM_178020.3 | chr9:107581295-107587359 |
| 10142 | Hs3st5 | NM_001081208.2 | chr19:36506806-36834394 | 10239 | Hyal4 | NM_029848.1 | chr6:24748366-24766519 |
| 10143 | Hs3st6 | NM_001012402.1 | chr17:24753002-24758684 | 10240 | Hyal5 | NM_028957.2 | chr6:24857996-24891958 |
| 10144 | Hs6st1 | NM_015818.2 | chr1:36068399-36106446 | 10241 | Hyal6 | NM_028920.2 | chr6:24733244-24745452 |
| 10145 | Hs6st2 | NM_001077202.2 | chrX:51386636-51681602 | 10242 | Hydin | NM_172916.2 | chr8:110266976-110610253 |
| 10146 | Hs6st3 | NM_015820.2 | chr14:119138264-119869815 | 10243 | Hyi | NM_026601.3 | chr4:118359998-118362744 |
| 10147 | Hsbp1 | NM_024219.1 | chr11:19944537-119348929 | 10244 | Hykk | NM_173351.4 | chr9:54917289-54949924 |
| 10148 | Hsbp1l1 | NM_001136381.1 | chr18:60229755-80247102 | 10245 | Hyls1 | NM_029782.1 | chr9:35560820-35570069 |
| 10149 | Hscb | NM_153571.2 | chr5:110829069-110899777 | 10246 | Hyou1 | NM_021395.4 | chr9:44379489-44392369 |
| 10150 | Hsd11b1 | NM_001044769.1 | chr1:193221640-193242360 | 10247 | Hypk | NM_026318.3 | chr2:121457087-121458440 |
| 10151 | Hsd11b2 | NM_008289.2 | chr8:105518745-105523988 | 10248 | 1700028E13Rik | NR_045705.1 | chr9:61138514-61145259 |
| 10152 | Hsd17b1 | NM_010475.1 | chr11:101078410-101080505 | 10249 | 1700030J21Rik | NR_045781.1 | chr15:100730504-100732737 |
| 10153 | Hsd17b10 | NM_016600.3 | chrX:152001895-152004442 | 10250 | I830012O16Rik | NM_001005858.3 | chr19:34607956-34613401 |
| 10154 | Hsd17b11 | NM_053262.3 | chr5:103989764-104021796 | 10251 | I830077J02Rik | NM_001033780.3 | chr3:105925890-105932664 |
| 10155 | Hsd17b12 | NM_019657.4 | chr2:94032696-94157909 | 10252 | Iah1 | NM_026347.3 | chr12:21316391-21323607 |
| 10156 | Hsd17b13 | NM_001163486.1 | chr5:103963464-103977388 | 10253 | Iapp | NM_010491.2 | chr6:142298424-142303819 |
| 10157 | Hsd17b14 | NM_025330.3 | chr7:45554927-45567321 | 10254 | Iars | NM_172015.3 | chr13:49682129-49734267 |
| 10158 | Hsd17b2 | NM_008290.2 | chr8:117701945-117759029 | 10255 | Iars2 | NM_198653.2 | chr1:185286661-185329401 |
| 10159 | Hsd17b3 | NM_008291.3 | chr13:64058273-64089201 | 10256 | Iba57 | NM_001270791.1 | chr11:59161118-59163745 |
| 10160 | Hsd17b4 | NM_008292.4 | chr18:50128200-50196270 | 10257 | Ibsp | NM_008318.3 | chr5:104299286-104311472 |
| 10161 | Hsd17b6 | NM_019786.2 | chr10:127990985-128007508 | 10258 | Ibtk | NM_001081282.2 | chr9:85687359-85749334 |
| 10162 | Hsd17b7 | NM_010476.3 | chr1:169949536-169969205 | 10259 | Ica1 | NM_001252266.1 | chr6:8630526-8758456 |
| 10163 | Hsd3b1 | NM_008293.4 | chr3:98852193-98859794 | 10260 | Ica1l | NM_027407.3 | chr1:59989067-60043087 |
| 10164 | Hsd3b2 | NM_153193.3 | chr3:98771106-98724543 | 10261 | Icam1 | NM_010493.2 | chr9:21015959-21028796 |
| 10165 | Hsd3b3 | NM_001012306.2 | chr3:98741475-98762410 | 10262 | Icam2 | NM_010494.1 | chr11:106377655-106382641 |
| 10166 | Hsd3b4 | NM_011336.1 | chr3:98445683-98563943 | 10263 | Icam4 | NM_023892.2 | chr9:21029372-21030531 |
| 10167 | Hsd3b5 | NM_008295.3 | chr3:98618635-98645934 | 10264 | Icam5 | NM_008319.2 | chr9:21032037-21039036 |
| 10168 | Hsd3b6 | NM_013821.3 | chr3:98805503-98814443 | 10265 | Ick | NM_001163780.1 | chr9:78109191-78172109 |
| 10169 | Hsd3b7 | NM_010406684.1 | chr7:127800668-127803802 | 10266 | Icmt | NM_133788.2 | chr4:152297213-152307126 |
| 10170 | Hsdl1 | NM_175185.4 | chr8:119561977-119575200 | 10267 | Icos | NM_017480.2 | chr1:60977913-61000321 |
| 10171 | Hsdl2 | NM_024255.3 | chr4:59581562-59618694 | 10268 | Icosl | NM_015790.3 | chr10:78069367-78079525 |
| 10172 | Hsf1 | NM_008296.2 | chr15:76477444-76506972 | 10269 | Ict1 | NM_026729.1 | chr11:115403765-115410913 |
| 10173 | Hsf2 | NM_008297.3 | chr15:57486384-57513143 | 10270 | Id1 | NM_010495.3 | chr2:152736250-152737410 |
| 10174 | Hsf2bp | NM_028092.1 | chr17:31944768-32034508 | 10271 | Id2 | NM_010496.3 | chr12:25093798-25096902 |
| 10175 | Hsf3 | NM_172931.4 | chr9:96306177-96456294 | 10272 | Id3 | NM_008321.2 | chr4:136143821-136145392 |
| 10176 | Hsf4 | NM_001256042.1 | chr8:105269800-105275845 | 10273 | Id4 | NM_031166.2 | chr13:48261426-48264036 |
| 10177 | Hsf5 | NM_001045527.1 | chr11:87617183-87659542 | 10274 | Ide | NM_031156.3 | chr19:37268740-37330613 |
| 10178 | Hsfy2 | NM_027661.2 | chr1:56636050-56637451 | 10275 | Idh1 | NM_001111320.1 | chr1:65158615-65186479 |
| 10179 | Hsh2d | NM_197944.1 | chr8:72189667-72200958 | 10276 | Idh2 | NM_173011.2 | chr7:80094846-80115350 |
| 10180 | Hsp90aa1 | NM_010480.5 | chr12:110691035-110696395 | 10277 | Idh3a | NM_029573.2 | chr9:54585610-54604662 |
| 10181 | Hsp90ab1 | NM_008302.3 | chr17:45567777-45573261 | 10278 | Idh3b | NM_130884.4 | chr2:130279308-130284451 |
| 10182 | Hsp90b1 | NM_011631.1 | chr10:86690840-86705444 | 10279 | Idh3g | NM_008323.1 | chrX:73778962-73786897 |
| 10183 | Hspa12a | NM_175199.3 | chr19:58795750-58860984 | 10280 | Idi1 | NM_145360.2 | chr13:8885605-8892396 |
| 10184 | Hspa12b | NM_028306.3 | chr2:131127411-131145983 | 10281 | Idi2 | NM_177197.4 | chr13:8952862-8960935 |

Fig.21 - 54

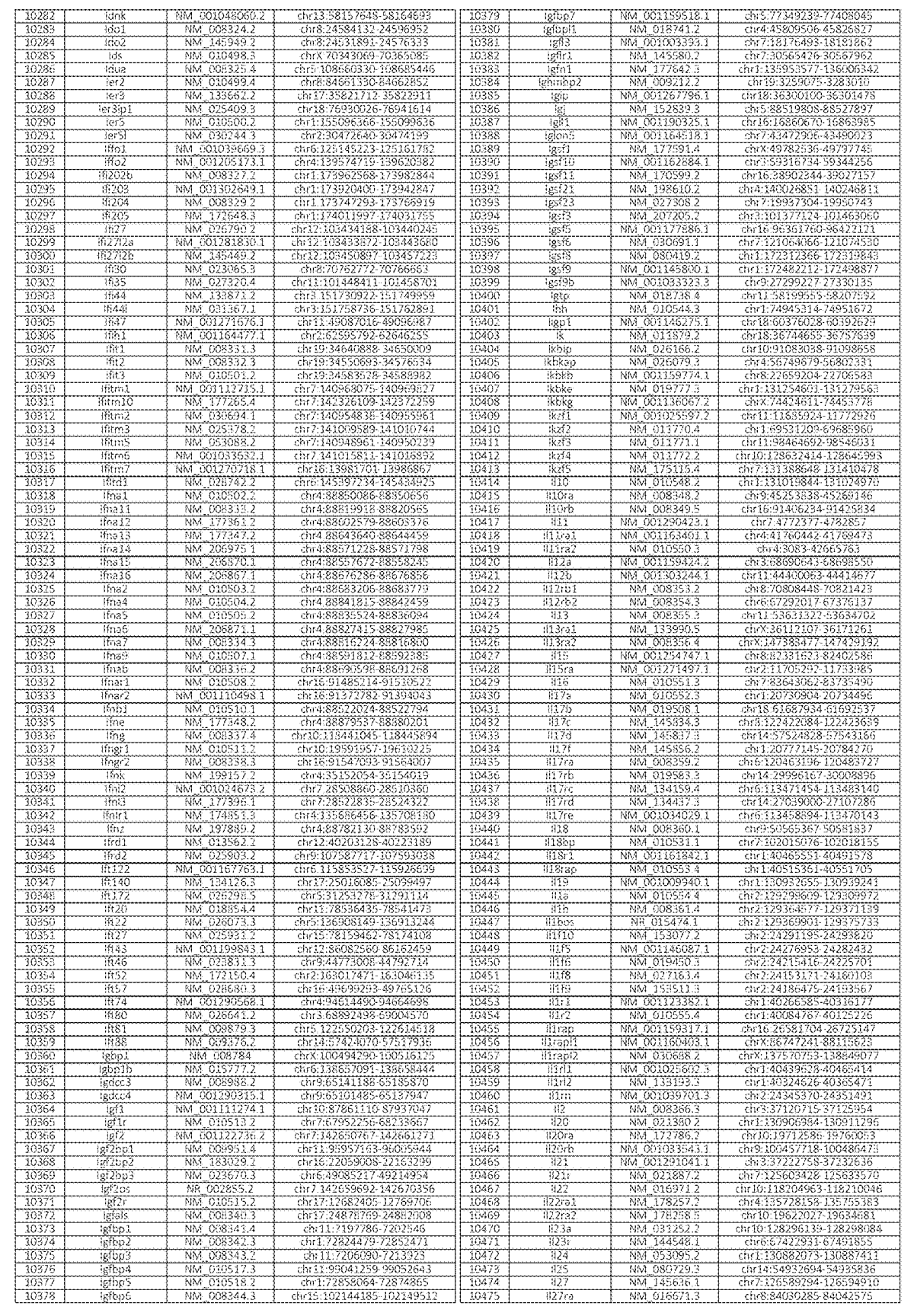

| | | | | | | | |
|---|---|---|---|---|---|---|---|
| 10282 | Idnk | NM_001048060.2 | chr13:58157648-58164693 | 10379 | Igfbp7 | NM_001159518.1 | chr5:77349239-77408045 |
| 10283 | Ido1 | NM_008324.2 | chr8:24584132-24596952 | 10380 | Igfbpl1 | NM_018741.2 | chr4:45809506-45826827 |
| 10284 | Ido2 | NM_145949.2 | chr8:24531891-24576333 | 10381 | Igfl3 | NM_001003393.1 | chr7:18176493-18181862 |
| 10285 | Ids | NM_010498.3 | chrX:70343069-70365085 | 10382 | Igflr1 | NM_145580.2 | chr7:30565426-30567962 |
| 10286 | Idua | NM_008325.4 | chr5:108660330-108685446 | 10383 | Igfn1 | NM_177642.3 | chr1:135953577-136006342 |
| 10287 | Ier2 | NM_010499.4 | chr8:84661330-84662852 | 10384 | Ighmbp2 | NM_009212.2 | chr19:3259075-3283010 |
| 10288 | Ier3 | NM_133662.2 | chr17:35821712-35822911 | 10385 | Igip | NM_001267796.1 | chr18:36300100-36301478 |
| 10289 | Ier3ip1 | NM_025409.3 | chr18:76930026-76941614 | 10386 | Igj | NM_152839.3 | chr5:88519808-88527897 |
| 10290 | Ier5 | NM_010500.2 | chr1:155096366-155099636 | 10387 | Igll1 | NM_001190325.1 | chr16:16860670-16863985 |
| 10291 | Ier5l | NM_030244.3 | chr2:30472640-30474199 | 10388 | Iglon5 | NM_001164518.1 | chr7:43472906-43490023 |
| 10292 | Iffo1 | NM_001039669.3 | chr6:125145223-125161782 | 10389 | Igsf1 | NM_177591.4 | chrX:49782536-49797745 |
| 10293 | Iffo2 | NM_001205173.1 | chr4:139574719-139620382 | 10390 | Igsf10 | NM_001162884.1 | chr3:59316734-59344256 |
| 10294 | Ifi202b | NM_008327.2 | chr1:173962568-173982844 | 10391 | Igsf11 | NM_170599.2 | chr16:38902344-39027157 |
| 10295 | Ifi203 | NM_001302649.1 | chr1:173920400-173942847 | 10392 | Igsf21 | NM_198610.2 | chr4:140026851-140246811 |
| 10296 | Ifi204 | NM_008329.2 | chr1:173747293-173766919 | 10393 | Igsf23 | NM_027308.2 | chr7:19937304-19950743 |
| 10297 | Ifi205 | NM_172648.3 | chr1:174011997-174031755 | 10394 | Igsf3 | NM_207205.2 | chr3:101377124-101463060 |
| 10298 | Ifi27 | NM_026790.2 | chr12:103434188-103440245 | 10395 | Igsf5 | NM_001177886.1 | chr16:96361760-96422121 |
| 10299 | Ifi27l2a | NM_001281830.1 | chr12:103433872-103443680 | 10396 | Igsf6 | NM_030691.1 | chr7:121064066-121074530 |
| 10300 | Ifi27l2b | NM_145449.2 | chr12:103450897-103457223 | 10397 | Igsf8 | NM_080419.2 | chr1:172312366-172319843 |
| 10301 | Ifi30 | NM_023065.3 | chr8:70762772-70766663 | 10398 | Igsf9 | NM_001145800.1 | chr1:172482212-172498877 |
| 10302 | Ifi35 | NM_027320.4 | chr11:101448411-101458701 | 10399 | Igsf9b | NM_001033323.3 | chr9:27299227-27330135 |
| 10303 | Ifi44 | NM_133871.2 | chr3:151730922-151749959 | 10400 | Igtp | NM_018738.4 | chr11:58199555-58207592 |
| 10304 | Ifi44l | NM_031367.1 | chr3:151758736-151762891 | 10401 | Ihh | NM_010544.3 | chr1:74945314-74951672 |
| 10305 | Ifi47 | NM_001271676.1 | chr11:49087016-49096987 | 10402 | Iigp1 | NM_001146275.1 | chr18:60376028-60392629 |
| 10306 | Ifih1 | NM_001164477.1 | chr2:62595792-62646255 | 10403 | Ik | NM_011879.2 | chr18:36744655-36757639 |
| 10307 | Ifit1 | NM_008331.3 | chr19:34640888-34650009 | 10404 | Ikbip | NM_026166.2 | chr10:91083038-91098658 |
| 10308 | Ifit2 | NM_008332.3 | chr19:34550693-34576534 | 10405 | Ikbkap | NM_026079.3 | chr4:56749679-56802331 |
| 10309 | Ifit3 | NM_010501.2 | chr19:34583528-34588982 | 10406 | Ikbkb | NM_001159774.1 | chr8:22659204-22706583 |
| 10310 | Ifitm1 | NM_001112715.1 | chr7:140968075-140969827 | 10407 | Ikbke | NM_019777.3 | chr1:131254601-131279563 |
| 10311 | Ifitm10 | NM_177265.4 | chr7:142326109-142372259 | 10408 | Ikbkg | NM_001136067.2 | chrX:74424611-74453778 |
| 10312 | Ifitm2 | NM_030694.1 | chr7:140954838-140955961 | 10409 | Ikzf1 | NM_001025597.2 | chr11:11685924-11772926 |
| 10313 | Ifitm3 | NM_025378.2 | chr7:141009589-141010744 | 10410 | Ikzf2 | NM_011770.4 | chr1:69531209-69685960 |
| 10314 | Ifitm5 | NM_053088.2 | chr7:140948961-140950239 | 10411 | Ikzf3 | NM_011771.1 | chr11:98464692-98546031 |
| 10315 | Ifitm6 | NM_001033632.1 | chr7:141015811-141016892 | 10412 | Ikzf4 | NM_011772.2 | chr10:128632414-128645993 |
| 10316 | Ifitm7 | NM_001270718.1 | chr16:13981701-13986867 | 10413 | Ikzf5 | NM_175115.4 | chr7:131388648-131410478 |
| 10317 | Ifltd1 | NM_028742.2 | chr6:145397234-145434925 | 10414 | Il10 | NM_010548.2 | chr1:131019844-131024970 |
| 10318 | Ifna1 | NM_010502.2 | chr4:88850086-88850656 | 10415 | Il10ra | NM_008348.2 | chr9:45253838-45269146 |
| 10319 | Ifna11 | NM_008333.2 | chr4:88819918-88820565 | 10416 | Il10rb | NM_008349.5 | chr16:91406234-91425834 |
| 10320 | Ifna12 | NM_177361.2 | chr4:88602579-88603376 | 10417 | Il11 | NM_001290423.1 | chr7:4772377-4782857 |
| 10321 | Ifna13 | NM_177347.2 | chr4:88643640-88644459 | 10418 | Il11ra1 | NM_001163401.1 | chr4:41760442-41769473 |
| 10322 | Ifna14 | NM_206975.1 | chr4:88571228-88571798 | 10419 | Il11ra2 | NM_010550.3 | chr4:3083-42665763 |
| 10323 | Ifna15 | NM_206870.1 | chr4:88557672-88558245 | 10420 | Il12a | NM_001159424.2 | chr3:68690643-68698550 |
| 10324 | Ifna16 | NM_206867.1 | chr4:88676286-88676856 | 10421 | Il12b | NM_001303244.1 | chr11:44400063-44414677 |
| 10325 | Ifna2 | NM_010503.2 | chr4:88683206-88683779 | 10422 | Il12rb1 | NM_008353.2 | chr8:70808448-70821423 |
| 10326 | Ifna4 | NM_010504.2 | chr4:88841815-88842459 | 10423 | Il12rb2 | NM_008354.3 | chr6:67292017-67376137 |
| 10327 | Ifna5 | NM_010505.2 | chr4:88835524-88836094 | 10424 | Il13 | NM_008355.3 | chr11:53631322-53634702 |
| 10328 | Ifna6 | NM_206871.1 | chr4:88827415-88827985 | 10425 | Il13ra1 | NM_133990.5 | chrX:36112107-36171261 |
| 10329 | Ifna7 | NM_008334.3 | chr4:88816224-88816800 | 10426 | Il13ra2 | NM_008356.4 | chrX:147383477-147429192 |
| 10330 | Ifna9 | NM_010507.1 | chr4:88591812-88592388 | 10427 | Il15 | NM_001254747.1 | chr8:82331623-82402586 |
| 10331 | Ifnab | NM_008336.2 | chr4:88690598-88691268 | 10428 | Il15ra | NM_001271497.1 | chr2:11705292-11733985 |
| 10332 | Ifnar1 | NM_010508.2 | chr16:91485214-91510522 | 10429 | Il16 | NM_010551.3 | chr7:83643062-83735490 |
| 10333 | Ifnar2 | NM_001110498.1 | chr16:91372782-91394043 | 10430 | Il17a | NM_010552.3 | chr1:20730904-20734496 |
| 10334 | Ifnb1 | NM_010510.1 | chr4:88522024-88522794 | 10431 | Il17b | NM_019508.1 | chr18:61687934-61692537 |
| 10335 | Ifne | NM_177348.2 | chr4:88879537-88880201 | 10432 | Il17c | NM_145834.3 | chr8:122422084-122423639 |
| 10336 | Ifng | NM_008337.4 | chr10:118441045-118445894 | 10433 | Il17d | NM_145837.3 | chr14:57524828-57543166 |
| 10337 | Ifngr1 | NM_010511.2 | chr10:19591957-19610225 | 10434 | Il17f | NM_145856.2 | chr1:20777145-20784270 |
| 10338 | Ifngr2 | NM_008338.3 | chr16:91547093-91564007 | 10435 | Il17ra | NM_008359.2 | chr6:120463196-120483727 |
| 10339 | Ifnk | NM_199157.2 | chr4:35152054-35154019 | 10436 | Il17rb | NM_019583.3 | chr14:29996167-30008896 |
| 10340 | Ifnl2 | NM_001024673.2 | chr7:28508860-28510360 | 10437 | Il17rc | NM_134159.4 | chr6:113471454-113483140 |
| 10341 | Ifnl3 | NM_177396.1 | chr7:28522835-28524322 | 10438 | Il17rd | NM_134437.3 | chr14:27039000-27107286 |
| 10342 | Ifnlr1 | NM_174851.3 | chr4:135686456-135708180 | 10439 | Il17re | NM_001034029.1 | chr6:113458894-113470143 |
| 10343 | Ifnz | NM_197889.2 | chr4:88782130-88783592 | 10440 | Il18 | NM_008360.1 | chr9:50565367-50581837 |
| 10344 | Ifrd1 | NM_013562.2 | chr12:40203128-40223189 | 10441 | Il18bp | NM_010531.1 | chr7:102015076-102018155 |
| 10345 | Ifrd2 | NM_025903.2 | chr9:107587717-107593038 | 10442 | Il18r1 | NM_001161842.1 | chr1:40465551-40491578 |
| 10346 | Ift122 | NM_001167763.1 | chr6:115853527-115926699 | 10443 | Il18rap | NM_010553.4 | chr1:40515361-40551705 |
| 10347 | Ift140 | NM_134126.3 | chr17:25016085-25099497 | 10444 | Il19 | NM_001009940.1 | chr1:130932655-130939241 |
| 10348 | Ift172 | NM_026298.5 | chr5:31253278-31291114 | 10445 | Il1a | NM_010554.4 | chr2:129299609-129309972 |
| 10349 | Ift20 | NM_018854.4 | chr11:78536435-78541473 | 10446 | Il1b | NM_008361.4 | chr2:129364577-129371139 |
| 10350 | Ift22 | NM_026073.3 | chr5:136908149-136913244 | 10447 | Il1bos | NR_015474.1 | chr2:129369901-129375733 |
| 10351 | Ift27 | NM_025931.2 | chr15:78159462-78174108 | 10448 | Il1f10 | NM_153077.2 | chr2:24291195-24293820 |
| 10352 | Ift43 | NM_001199843.1 | chr12:86082560-86162459 | 10449 | Il1f5 | NM_001146087.1 | chr2:24276953-24282432 |
| 10353 | Ift46 | NM_023831.3 | chr9:44773008-44792714 | 10450 | Il1f6 | NM_019450.3 | chr2:24215416-24225701 |
| 10354 | Ift52 | NM_172150.4 | chr2:163017471-163046135 | 10451 | Il1f8 | NM_027163.4 | chr2:24153171-24160103 |
| 10355 | Ift57 | NM_028680.3 | chr16:49699293-49765126 | 10452 | Il1f9 | NM_153511.3 | chr2:24186475-24193567 |
| 10356 | Ift74 | NM_001290568.1 | chr4:94614490-94664698 | 10453 | Il1r1 | NM_001123382.1 | chr1:40266585-40316177 |
| 10357 | Ift80 | NM_026641.2 | chr3:68892498-69004570 | 10454 | Il1r2 | NM_010555.4 | chr1:40084767-40125226 |
| 10358 | Ift81 | NM_009879.3 | chr5:122550203-122614618 | 10455 | Il1rap | NM_001159317.1 | chr16:26581704-26725147 |
| 10359 | Ift88 | NM_009376.2 | chr14:57424070-57517936 | 10456 | Il1rapl1 | NM_001160403.1 | chrX:86747241-88115623 |
| 10360 | Igbp1 | NM_008784 | chrX:100494290-100516125 | 10457 | Il1rapl2 | NM_030688.2 | chrX:137570753-138849077 |
| 10361 | Igbp1b | NM_015777.2 | chr6:138657091-138658444 | 10458 | Il1rl1 | NM_001025602.3 | chr1:40439628-40465414 |
| 10362 | Igdcc3 | NM_008988.2 | chr9:65141188-65185870 | 10459 | Il1rl2 | NM_133193.3 | chr1:40324626-40365471 |
| 10363 | Igdcc4 | NM_001290315.1 | chr9:65101485-65137947 | 10460 | Il1rn | NM_001039701.3 | chr2:24345370-24351491 |
| 10364 | Igf1 | NM_001111274.1 | chr10:87861110-87937047 | 10461 | Il2 | NM_008366.3 | chr3:37120715-37125954 |
| 10365 | Igf1r | NM_010513.2 | chr7:67952256-68233667 | 10462 | Il20 | NM_021380.2 | chr1:130906984-130911296 |
| 10366 | Igf2 | NM_001122736.2 | chr7:142650767-142661271 | 10463 | Il20ra | NM_172786.2 | chr10:19712586-19760053 |
| 10367 | Igf2bp1 | NM_009951.4 | chr11:95957163-96005944 | 10464 | Il20rb | NM_001033543.1 | chr9:100457718-100486473 |
| 10368 | Igf2bp2 | NM_183029.2 | chr16:22059008-22163299 | 10465 | Il21 | NM_001291041.1 | chr3:37222758-37232636 |
| 10369 | Igf2bp3 | NM_023670.3 | chr6:49085217-49214954 | 10466 | Il21r | NM_021887.2 | chr7:125603428-125633570 |
| 10370 | Igf2os | NR_002855.2 | chr7:142659692-142670356 | 10467 | Il22 | NM_016971.2 | chr10:118204963-118210046 |
| 10371 | Igf2r | NM_010515.2 | chr17:12682405-12769706 | 10468 | Il22ra1 | NM_178257.2 | chr4:135728158-135755383 |
| 10372 | Igfals | NM_008340.3 | chr17:24878769-24882008 | 10469 | Il22ra2 | NM_178258.5 | chr10:19622027-19634681 |
| 10373 | Igfbp1 | NM_008341.4 | chr11:7197786-7202546 | 10470 | Il23a | NM_031252.2 | chr10:128296139-128298084 |
| 10374 | Igfbp2 | NM_008342.3 | chr1:72824479-72852471 | 10471 | Il23r | NM_144548.1 | chr6:67422931-67491855 |
| 10375 | Igfbp3 | NM_008343.2 | chr11:7206090-7213923 | 10472 | Il24 | NM_053095.2 | chr1:130882073-130887411 |
| 10376 | Igfbp4 | NM_010517.3 | chr11:99041259-99052643 | 10473 | Il25 | NM_080729.3 | chr14:54932694-54935836 |
| 10377 | Igfbp5 | NM_010518.2 | chr1:72858064-72874865 | 10474 | Il27 | NM_145636.1 | chr7:126589294-126594910 |
| 10378 | Igfbp6 | NM_008344.3 | chr15:102144185-102149512 | 10475 | Il27ra | NM_016671.3 | chr8:84030285-84042575 |

Fig.21 - 55

| | | | | | | | |
|---|---|---|---|---|---|---|---|
| 10476 | Il2ra | NM_008367.3 | chr2:11642791-11693194 | 10573 | Ints8 | NM_001159595.1 | chr4:11202927-11254259 |
| 10477 | Il2rb | NM_008368.4 | chr15:78480548-78495066 | 10574 | Ints9 | NM_001253731.1 | chr14:64950044-65039835 |
| 10478 | Il2rg | NM_013563.4 | chrX:101264384-101268255 | 10575 | Intu | NM_175515.5 | chr3:40540766-40704774 |
| 10479 | Il3 | NM_010556.4 | chr11:54265084-54267279 | 10576 | Invs | NM_001281977.1 | chr4:48279759-48431953 |
| 10480 | Il3ra | NM_029594.1 | chr14:123480152-123482101 | 10577 | Ip6k1 | NM_013785.2 | chr9:108002647-108048782 |
| 10481 | Il31ra | NM_139299.2 | chr13:112522806-112580662 | 10578 | Ip6k2 | NM_029634.2 | chr9:108795993-108806333 |
| 10482 | Il33 | NM_001164724.1 | chr19:29945789-29960715 | 10579 | Ip6k3 | NM_173027.2 | chr17:27143970-27167764 |
| 10483 | Il34 | NM_001135100.2 | chr8:110741828-110805924 | 10580 | Ipcef1 | NM_001033391.2 | chr10:6911542-7023185 |
| 10484 | Il3ra | NM_008369.1 | chr14:14346494-14355490 | 10581 | Ipmk | NM_027184.1 | chr10:71347792-71385885 |
| 10485 | Il4 | NM_021283.2 | chr11:53612460-53618665 | 10582 | Ipo11 | NM_029665.3 | chr13:106794838-106936915 |
| 10486 | Il4i1 | NM_010215.3 | chr7:44838287-44840809 | 10583 | Ipo13 | NM_146152.3 | chr4:117894492-117914999 |
| 10487 | Il4ra | NM_001008700.3 | chr7:125552281-125579474 | 10584 | Ipo4 | NM_024267.6 | chr14:55625628-55635678 |
| 10488 | Il5 | NM_010558.1 | chr11:53720793-53725103 | 10585 | Ipo5 | NM_023579.4 | chr14:120911193-120948044 |
| 10489 | Il5ra | NM_008370.2 | chr6:106710378-106749037 | 10586 | Ipo7 | NM_181517.3 | chr7:110018424-110055114 |
| 10490 | Il6 | NM_031168.2 | chr5:30013113-30019975 | 10587 | Ipo8 | NM_001081113.1 | chr6:148770683-148831467 |
| 10491 | Il6ra | NM_010559.3 | chr3:89869323-89913196 | 10588 | Ipo9 | NM_153774.1 | chr1:135382314-135430493 |
| 10492 | Il6st | NM_010560.3 | chr13:112464069-112506860 | 10589 | Ipp | NM_008389.3 | chr4:116507948-116538235 |
| 10493 | Il7 | NM_008371.5 | chr3:7572027-7613760 | 10590 | Ippk | NM_001276399.1 | chr13:49421613-49463060 |
| 10494 | Il7r | NM_008372.4 | chr15:9506158-9529876 | 10591 | Ipw | NR_015351.1 | chr7:59619157-59678878 |
| 10495 | Il9 | NM_008373.1 | chr13:56479276-56482246 | 10592 | Iqca | NM_029122.2 | chr1:90042131-90153401 |
| 10496 | Il9r | NM_001134458.1 | chr11:32188996-32200279 | 10593 | Iqcb1 | NM_177128.4 | chr16:36828399-36872715 |
| 10497 | Ildr1 | NM_001285788.1 | chr16:36693977-36726804 | 10594 | Iqcc | NM_198026.2 | chr4:129615616-129619093 |
| 10498 | Ildr2 | NM_001164526.1 | chr1:166254138-166316832 | 10595 | Iqcd | NM_029408.2 | chr5:120589022-120607113 |
| 10499 | Ilf2 | NM_026374.3 | chr3:90476200-90488379 | 10596 | Iqce | NM_028833.3 | chr5:140663504-140702378 |
| 10500 | Ilf3 | NM_001042707.2 | chr9:21367870-21405363 | 10597 | Iqcf1 | NM_001146701.1 | chr9:106499966-106502250 |
| 10501 | Ilk | NM_001161724.1 | chr7:105736589-105742925 | 10598 | Iqcf3 | NM_026645.3 | chr9:106543388-106561625 |
| 10502 | Ilkap | NM_023343.2 | chr1:91375830-91398783 | 10599 | Iqcf4 | NM_026090.2 | chr9:106568318-106570967 |
| 10503 | Ilkfb | NM_054079.2 | chr10:118289629-118295038 | 10600 | Iqcf5 | NM_029300.1 | chr9:106514572-106516003 |
| 10504 | Ilvbl | NM_173751.4 | chr6:78574499-78584502 | 10601 | Iqcf6 | NM_001101628.1 | chr9:106626981-106627612 |
| 10505 | Immp1l | NM_028260.2 | chr2:105904637-105965558 | 10602 | Iqcg | NM_178378.3 | chr16:33014269-33056186 |
| 10506 | Immp2l | NM_053122.4 | chr12:41024089-41955588 | 10603 | Iqch | NM_030068.2 | chr9:63421448-63602493 |
| 10507 | Immt | NM_001253681.1 | chr6:71831319-71875266 | 10604 | Iqcj | NM_177585.3 | chr3:67892219-68056593 |
| 10508 | Imp3 | NM_133976.2 | chr9:56937499-58938398 | 10605 | Iqck | NM_001081446.1 | chr7:118855774-118972652 |
| 10509 | Imp4 | NM_178601.3 | chr1:34439828-34445747 | 10606 | Iqgap1 | NM_016721.2 | chr7:80711582-80803331 |
| 10510 | Impa1 | NM_018864.6 | chr3:10311955-10331439 | 10607 | Iqgap2 | NM_027711.1 | chr13:95627176-95891922 |
| 10511 | Impa2 | NM_053261.2 | chr18:67289222-67318341 | 10608 | Iqgap3 | NM_001033484.1 | chr3:88082050-88121048 |
| 10512 | Impact | NM_008378.2 | chr18:12972251-12992948 | 10609 | Iqsec1 | NM_001343383.1 | chr6:90659597-90716529 |
| 10513 | Impad1 | NM_177730.3 | chr4:4764350-4793306 | 10610 | Iqsec2 | NM_001005475.2 | chrX:152179008-152225237 |
| 10514 | Impdh1 | NM_011818.2 | chr6:29200436-29212297 | 10611 | Iqsec3 | NM_001033354.3 | chr6:121372927-121473678 |
| 10515 | Impdh2 | NM_011830.3 | chr9:108560500-108565566 | 10612 | Iqub | NM_172535.3 | chr6:24444864-24515067 |
| 10516 | Impg1 | NM_022016.3 | chr9:80313329-80465438 | 10613 | Irak1 | NM_001177973.1 | chrX:74013913-74023921 |
| 10517 | Impg2 | NM_174876.3 | chr16:56204312-56273753 | 10614 | Irak1bp1 | NM_001168240.1 | chr9:82829805-82847688 |
| 10518 | Ina | NM_146100.4 | chr19:47014697-47024346 | 10615 | Irak2 | NM_001135533.1 | chr6:113638466-113695027 |
| 10519 | Inadl | NM_001005784.1 | chr4:98395825-98497633 | 10616 | Irak3 | NM_028679.3 | chr10:120141653-120201537 |
| 10520 | Inca1 | NM_001252482.1 | chr11:70688360-70700155 | 10617 | Irak4 | NM_029926.5 | chr15:94543659-94568316 |
| 10521 | Incenp | NM_016692.3 | chr19:9872296-9899533 | 10618 | Ireb2 | NM_022655.3 | chr9:54863754-54912634 |
| 10522 | Inf2 | NM_198411.2 | chr12:112588783-112615557 | 10619 | Irf1 | NM_001159393.1 | chr11:53770013-53778374 |
| 10523 | Ing1 | NM_011919.5 | chr8:11556456-11563251 | 10620 | Irf2 | NM_008391.4 | chr8:46739744-46847458 |
| 10524 | Ing2 | NM_023503.3 | chr8:47667177-47675169 | 10621 | Irf2bp1 | NM_178757.3 | chr7:19004064-19006763 |
| 10525 | Ing3 | NM_023604.4 | chr6:21940614-21976017 | 10622 | Irf2bp2 | NM_001164598.1 | chr8:126588295-126593436 |
| 10526 | Ing4 | NM_133345.2 | chr6:125039847-125049264 | 10623 | Irf2bpl | NM_145836.2 | chr12:86880702-86884814 |
| 10527 | Ing5 | NM_025454.2 | chr1:93803964-93822100 | 10624 | Irf3 | NM_016849.4 | chr7:44997647-45002848 |
| 10528 | Inha | NM_010564.4 | chr1:75507076-75510354 | 10625 | Irf4 | NM_013674.1 | chr13:30749257-30766927 |
| 10529 | Inhba | NM_008380.1 | chr13:16014474-16027211 | 10626 | Irf5 | NM_001252382.1 | chr6:29529281-29537320 |
| 10530 | Inhbb | NM_008381.3 | chr1:119419446-119422248 | 10627 | Irf6 | NM_016851.2 | chr1:193153111-193172035 |
| 10531 | Inhbc | NM_010565.3 | chr10:127356325-127370544 | 10628 | Irf7 | NM_001252600.1 | chr7:141263182-141266424 |
| 10532 | Inhbe | NM_008382.2 | chr10:127349401-127351772 | 10629 | Irf8 | NM_008320.4 | chr8:120736357-120756692 |
| 10533 | Inip | NM_001035577.1 | chr4:59769646-59783855 | 10630 | Irf9 | NM_001159417.1 | chr14:55603984-55610030 |
| 10534 | Inmt | NM_009349.3 | chr6:55170626-55174990 | 10631 | Irg1 | NM_008392.1 | chr14:103047011-103056573 |
| 10535 | Ino80 | NM_026574.3 | chr2:119373041-119477629 | 10632 | Irgc1 | NM_199013.2 | chr7:24431925-24445682 |
| 10536 | Ino80b | NM_025473.1 | chr6:83121827-83125029 | 10633 | Irgm1 | NM_008326.1 | chr11:48865248-48871346 |
| 10537 | Ino80c | NM_172625.2 | chr18:24104760-24121819 | 10634 | Irgm2 | NM_019440.3 | chr11:58214976-58222783 |
| 10538 | Ino80d | NM_001081436.1 | chr1:63047800-63114267 | 10635 | Irq | NM_153134.3 | chr7:24538600-24538600 |
| 10539 | Ino80dos | NR_045914.1 | chr1:63114739-63158295 | 10636 | Irs1 | NM_010570.4 | chr1:82235104-82291439 |
| 10540 | Ino80e | NM_153580.1 | chr7:126852432-126861463 | 10637 | Irs2 | NM_001081212.1 | chr8:10986969-11008430 |
| 10541 | Inpp1 | NM_008384.1 | chr1:52789419-52817688 | 10638 | Irs3 | NM_010571.3 | chr5:137643031-137645714 |
| 10542 | Inpp4a | NM_001290797.1 | chr1:37299837-37410740 | 10639 | Irs4 | NM_010572.4 | chrX:141710997-141725217 |
| 10543 | Inpp4b | NM_001024617.3 | chr8:81342561-82122570 | 10640 | Irx1 | NM_010573.2 | chr13:71958231-71963723 |
| 10544 | Inpp5a | NM_001127363.1 | chr7:139389108-139579652 | 10641 | Irx2 | NM_010574.2 | chr13:72628977-72634194 |
| 10545 | Inpp5b | NM_008385.4 | chr4:124741849-124801511 | 10642 | Irx3 | NM_001253822.1 | chr8:91798510-91801654 |
| 10546 | Inpp5d | NM_001110192.1 | chr1:87620311-87720510 | 10643 | Irx4 | NM_018885.2 | chr13:73260496-73269620 |
| 10547 | Inpp5e | NM_001290437.1 | chr2:26396248-26409127 | 10644 | Irx5 | NM_018826.2 | chr8:92357795-92361456 |
| 10548 | Inpp5f | NM_178641.5 | chr7:128611364-128696436 | 10645 | Irx6 | NM_022428.3 | chr8:92674288-92680956 |
| 10549 | Inpp5j | NM_172439.3 | chr11:3494271-3504821 | 10646 | Isca1 | NM_026921.4 | chr13:59755414-59769789 |
| 10550 | Inpp5k | NM_008916.2 | chr11:75631019-75648865 | 10647 | Isca2 | NM_028863.1 | chr12:84773269-84775089 |
| 10551 | Inppl1 | NM_001127391.1 | chr7:101822631-101837324 | 10648 | Iscu | NM_025526.4 | chr5:113772811-113778282 |
| 10552 | Ins1 | NM_008386.4 | chr19:52264296-52265009 | 10649 | Isg15 | NM_015783.3 | chr4:156199423-156200818 |
| 10553 | Ins2 | NM_001185083.2 | chr7:142678665-142679726 | 10650 | Isg20 | NM_001113527.1 | chr7:78914234-78920396 |
| 10554 | Insc | NM_173767.3 | chr7:114745765-114850380 | 10651 | Isg20l2 | NM_177663.4 | chr3:87903013-87940686 |
| 10555 | Insig1 | NM_153526.5 | chr5:28071411-28078662 | 10652 | Isl1 | NM_021459.4 | chr13:116298269-116309688 |
| 10556 | Insig2 | NM_001271531.1 | chr1:121304352-121327678 | 10653 | Isl2 | NM_027397.3 | chr9:55541148-55546178 |
| 10557 | Insl3 | NM_013564.4 | chr8:71689251-71690577 | 10654 | Islr | NM_011954.1 | chr9:58156263-58158554 |
| 10558 | Insl5 | NM_001290648.1 | chr4:103017872-103026842 | 10655 | Islr2 | NM_001161535.1 | chr9:58196296-58201715 |
| 10559 | Insl6 | NM_013754.1 | chr19:29321353-29325318 | 10656 | Ism1 | NM_001276489.1 | chr2:139678177-139758581 |
| 10560 | Insm1 | NM_016889.3 | chr2:146221996-146225018 | 10657 | Ism2 | NM_001290302.1 | chr12:87278637-87299705 |
| 10561 | Insm2 | NM_020287.2 | chr12:55598916-55602017 | 10658 | Isoc1 | NM_025478.3 | chr18:58659481-58679570 |
| 10562 | Insr | NM_010568.2 | chr8:3150921-3279617 | 10659 | Isoc2a | NM_001101598.1 | chr7:4877052-4895716 |
| 10563 | Insrr | NM_011832.2 | chr3:87796950-87816101 | 10660 | Isoc2b | NM_026158.2 | chr7:4844959-4866976 |
| 10564 | Ints1 | NM_026748.2 | chr5:139751281-139755678 | 10661 | Ispd | NM_001289502.1 | chr12:36381449-36689503 |
| 10565 | Ints10 | NM_027590.4 | chr8:68793928-68829410 | 10662 | Ist1 | NM_028018.2 | chr8:109671320-109693294 |
| 10566 | Ints12 | NM_027927.3 | chr13:133091952-133110985 | 10663 | Isx | NM_027837.3 | chr8:74873173-74893506 |
| 10567 | Ints2 | NM_027421.2 | chr11:86210682-86257568 | 10664 | Isy1 | NM_133934.4 | chr6:87818447-87838759 |
| 10568 | Ints3 | NM_145540.3 | chr3:90433636-90433636 | 10665 | Isyna1 | NM_023627.1 | chr8:70594480-70597290 |
| 10569 | Ints4 | NM_027256.2 | chr7:97480955-97541398 | 10666 | Itch | NM_001243712.1 | chr2:155133480-155226855 |
| 10570 | Ints5 | NM_148843.3 | chr19:8692986-8897890 | 10667 | Itfg1 | NM_028007.3 | chr8:85717556-85840949 |
| 10571 | Ints6 | NM_008715.2 | chr14:62676324-62761112 | 10668 | Itfg2 | NM_133927.1 | chr6:128409443-128424910 |
| 10572 | Ints7 | NM_178632.6 | chr1:191575635-191623690 | 10669 | Itfg3 | NM_001206335.1 | chr17:26212691-26244242 |

Fig.21 - 56

| | | | | | | | | |
|---|---|---|---|---|---|---|---|---|
| 10670 | Itga1 | NM_001033228.3 | chr13:114958080-115101964 | | 10767 | Jsrp1 | NM_028001.3 | chr10:80208495-80813498 |
| 10671 | Itga10 | NM_001302471.1 | chr3:96645584-96664519 | | 10768 | Jtb | NM_206924.2 | chr3:90231596-90235840 |
| 10672 | Itga11 | NM_176922.5 | chr9:62677854-62783979 | | 10769 | Jun | NM_010591.2 | chr4:95049035-95052222 |
| 10673 | Itga2 | NM_008396.2 | chr13:114835911-114932041 | | 10770 | Junb | NM_008416.3 | chr8:84976908-84978748 |
| 10674 | Itga2b | NM_010575.2 | chr11:102453296-102469883 | | 10771 | Jund | NM_001286944.1 | chr8:70697738-70700616 |
| 10675 | Itga3 | NM_013565.3 | chr11:95044474-95076714 | | 10772 | Jup | NM_010593.2 | chr11:100368855-100397790 |
| 10676 | Itga4 | NM_010576.3 | chr2:79255425-79333114 | | 10773 | Kalrn | NM_001164268.1 | chr16:34152024-34514027 |
| 10677 | Itga5 | NM_010577.4 | chr15:103344285-103366791 | | 10774 | Kank1 | NM_181404.5 | chr19:25237201-25434496 |
| 10678 | Itga6 | NM_001277970.1 | chr2:71786938-71858427 | | 10775 | Kank2 | NM_145611.4 | chr9:21766772-21798546 |
| 10679 | Itga7 | NM_008398.2 | chr10:128933812-128958284 | | 10776 | Kank3 | NM_030697.2 | chr17:33810522-33822914 |
| 10680 | Itga8 | NM_001001309.2 | chr2:12106659-12301920 | | 10777 | Kank4 | NM_172872.3 | chr4:98754891-98817537 |
| 10681 | Itga9 | NM_001113514.1 | chr9:118711691-118901903 | | 10778 | Kank4os | NR_040437.1 | chr4:98793767-98799037 |
| 10682 | Itgad | NM_001029673.3 | chr7:128173945-128205503 | | 10779 | Kansl1 | NM_001081045.1 | chr11:104335228-104442291 |
| 10683 | Itgae | NM_008399.2 | chr11:73090894-73147449 | | 10780 | Kansl1l | NM_001122738.1 | chr1:66719242-66817595 |
| 10684 | Itgal | NM_001253872.1 | chr7:127296259-127335137 | | 10781 | Kansl2 | NM_001289437.1 | chr15:98517657-98534289 |
| 10685 | Itgam | NM_001082960.1 | chr7:128062639-128118491 | | 10782 | Kansl3 | NM_172652.3 | chr1:36335729-36369181 |
| 10686 | Itgav | NM_008402.3 | chr2:83724396-83806917 | | 10783 | Kap | NM_010594.2 | chr6:133849854-133853667 |
| 10687 | Itgax | NM_021334.2 | chr7:128128627-128150657 | | 10784 | Kars | NM_001130868.2 | chr8:111993438-112011354 |
| 10688 | Itgb1 | NM_010578.2 | chr8:128685653-128735579 | | 10785 | Kat2a | NM_008510.2 | chr11:100704745-100712467 |
| 10689 | Itgb1bp1 | NM_008403.4 | chr12:21269805-21286237 | | 10786 | Kat2b | NM_001190846.1 | chr17:53584125-53672721 |
| 10690 | Itgb1bp2 | NM_013712.2 | chrX:101449108-101453641 | | 10787 | Kat5 | NM_001199247.1 | chr19:5603013-5610094 |
| 10691 | Itgb2 | NM_008404.4 | chr10:77530347-77565674 | | 10788 | Kat6a | NM_001081149.1 | chr8:22859538-22943262 |
| 10692 | Itgb2l | NM_008405.3 | chr16:96422297-96443614 | | 10789 | Kat6b | NM_001205241.1 | chr14:21499769-21672478 |
| 10693 | Itgb3 | NM_016780.2 | chr11:104607999-104670471 | | 10790 | Kat7 | NM_001195103.1 | chr11:95271852-95310246 |
| 10694 | Itgb3bp | NM_026348.3 | chr4:99765401-99829118 | | 10791 | Kat8 | NM_026370.1 | chr7:127912616-127925762 |
| 10695 | Itgb4 | NM_001005608.2 | chr11:115974724-116008411 | | 10792 | Katna1 | NM_011835.2 | chr10:7725999-7763150 |
| 10696 | Itgb5 | NM_001145884.1 | chr16:33829664-33949338 | | 10793 | Katnal1 | NM_153572.2 | chr5:148871583-148928647 |
| 10697 | Itgb6 | NM_001159564.1 | chr2:60598291-60722603 | | 10794 | Katnal2 | NM_027721.2 | chr18:76993199-77047296 |
| 10698 | Itgb7 | NM_013566.2 | chr15:102215994-102231935 | | 10795 | Katnb1 | NM_028805.2 | chr8:95081200-95099874 |
| 10699 | Itgb8 | NM_177290.3 | chr12:119162802-119238276 | | 10796 | Katnbl1 | NM_024254.3 | chr2:112379210-112414237 |
| 10700 | Itgbl1 | NM_145467.2 | chr14:123660139-123974079 | | 10797 | Kazald1 | NM_178929.4 | chr19:45076138-45079289 |
| 10701 | Itih1 | NM_008406.3 | chr14:30929179-30943289 | | 10798 | Kazn | NM_001109684.1 | chr4:142139239-142210208 |
| 10702 | Itih2 | NM_010582.3 | chr2:10094590-10130683 | | 10799 | Kbtbd11 | NM_029116.2 | chr8:15011624-15033332 |
| 10703 | Itih3 | NM_008407.2 | chr14:30908573-30923587 | | 10800 | Kbtbd12 | NM_001278671.1 | chr6:88547721-88627448 |
| 10704 | Itih4 | NM_001159299.2 | chr14:30886475-30901986 | | 10801 | Kbtbd13 | NM_028974.1 | chr9:65388683-65391652 |
| 10705 | Itih5 | NM_172471.2 | chr2:10153542-10258529 | | 10802 | Kbtbd2 | NM_145958.2 | chr6:56777524-56797813 |
| 10706 | Itk | NM_001281965.1 | chr11:46325147-46389515 | | 10803 | Kbtbd3 | NM_001164574.1 | chr9:4309742-4331732 |
| 10707 | Itln1 | NM_010584.3 | chr1:171518123-171535294 | | 10804 | Kbtbd4 | NM_025991.3 | chr2:90904785-90910560 |
| 10708 | Itm2a | NM_008409.2 | chrX:107397194-107403360 | | 10805 | Kbtbd7 | NM_001024135.2 | chr14:79426510-79431038 |
| 10709 | Itm2b | NM_008410.2 | chr14:73362231-73386271 | | 10806 | Kbtbd8 | NM_001008785.5 | chr6:95117879-95129793 |
| 10710 | Itm2c | NM_022417.3 | chr1:85894509-85908698 | | 10807 | Kcnf1 | NM_019715.2 | chr6:72841113-72899979 |
| 10711 | Itpa | NM_025972.2 | chr2:130667840-130681614 | | 10808 | Kcna1 | NM_010595.3 | chr6:126636462-126645801 |
| 10712 | Itpk1 | NM_172584.3 | chr12:102568582-102704869 | | 10809 | Kcna10 | NM_001081140.1 | chr3:107183142-107195721 |
| 10713 | Itpka | NM_146125.2 | chr2:119742336-119751253 | | 10810 | Kcna2 | NM_008417.5 | chr3:107101566-107115005 |
| 10714 | Itpkb | NM_001081175.1 | chr1:180233075-180423659 | | 10811 | Kcna3 | NM_008418.2 | chr3:107036161-107038129 |
| 10715 | Itpkc | NM_181593.2 | chr7:27207169-27228597 | | 10812 | Kcna4 | NM_021275.4 | chr2:107290588-107298504 |
| 10716 | Itpr1 | NM_010585.5 | chr6:108213095-108551116 | | 10813 | Kcna5 | NM_145983.2 | chr6:126535550-126535555 |
| 10717 | Itpr2 | NM_010586.2 | chr6:146108298-146502223 | | 10814 | Kcna6 | NM_013568.6 | chr6:126708328-126740674 |
| 10718 | Itpr3 | NM_080553.3 | chr17:27057803-27122223 | | 10815 | Kcna7 | NM_010596.2 | chr7:45405959-45411382 |
| 10719 | Itprip | NM_001001738.2 | chr19:47894595-47919299 | | 10816 | Kcnab1 | NM_001289450.1 | chr3:65188102-65378225 |
| 10720 | Itpripl1 | NM_001163527.1 | chr2:127138768-127143457 | | 10817 | Kcnab2 | NM_001252654.1 | chr4:152390739-152477549 |
| 10721 | Itpripl2 | NM_001033380.3 | chr7:118485111-118491975 | | 10818 | Kcnab3 | NM_010599.4 | chr11:69326257-69333041 |
| 10722 | Itsn1 | NM_001110275.1 | chr16:91729370-91871655 | | 10819 | Kcnb1 | NM_008420.4 | chr2:167095968-167188818 |
| 10723 | Itsn2 | NM_001198968.2 | chr12:4593007-4713952 | | 10820 | Kcnb2 | NM_001098528.2 | chr1:15312451-15714214 |
| 10724 | Ivd | NM_013788.3 | chr2:118861999-118881357 | | 10821 | Kcnc1 | NM_001112739.2 | chr7:46396467-46438704 |
| 10725 | Ivl | NM_008412.3 | chr3:92570899-92573735 | | 10822 | Kcnc2 | NM_001025581.1 | chr10:112271122-112466304 |
| 10726 | Ivns1abp | NM_001039511.1 | chr1:151344497-151356798 | | 10823 | Kcnc3 | NM_001290682.1 | chr7:44590885-44604751 |
| 10727 | Iws1 | NM_173441.3 | chr18:32067733-32104331 | | 10824 | Kcnc4 | NM_145922.2 | chr3:107438302-107458898 |
| 10728 | Iyd | NM_027391.3 | chr10:3540278-3554877 | | 10825 | Kcnd1 | NM_008423.2 | chrX:7823758-7838278 |
| 10729 | Izumo1 | NM_001018013.1 | chr7:45621810-45627242 | | 10826 | Kcnd2 | NM_019697.3 | chr6:21216108-21729805 |
| 10730 | Izumo2 | NM_029317.1 | chr7:44708742-44719842 | | 10827 | Kcnd3 | NM_001039347.1 | chr3:105452329-105674002 |
| 10731 | Izumo3 | NM_027034.1 | chr4:92144317-92147221 | | 10828 | Kcnd3os | NR_040759.1 | chr3:105448189-105452955 |
| 10732 | Izumo4 | NM_027829.3 | chr10:80702692-80705382 | | 10829 | Kcne1 | NM_008424.3 | chr16:92346000-92359468 |
| 10733 | Jade1 | NM_001130184.1 | chr3:41555733-41616864 | | 10830 | Kcne1l | NM_021487.1 | chrX:142304752-142306198 |
| 10734 | Jade2 | NM_199299.3 | chr11:51813455-51857481 | | 10831 | Kcne2 | NM_134110.3 | chr16:92292388-92298133 |
| 10735 | Jade3 | NM_001289684.1 | chrX:20425687-20519939 | | 10832 | Kcne3 | NM_001190869.1 | chr7:100176669-100184869 |
| 10736 | Jag1 | NM_013822.5 | chr2:137081450-137116520 | | 10833 | Kcne4 | NM_021342.1 | chr1:78816948-78820025 |
| 10737 | Jag2 | NM_010588.2 | chr12:112908589-112929495 | | 10834 | Kcnf1 | NM_201531.3 | chr12:17172099-17176888 |
| 10738 | Jagn1 | NM_001080025.1 | chr6:113442516-113448229 | | 10835 | Kcng1 | NM_001081134.1 | chr2:168261697-168269331 |
| 10739 | Jak1 | NM_146145.2 | chr4:101151973-101265282 | | 10836 | Kcng2 | NM_001190873.1 | chr18:80294543-80364254 |
| 10740 | Jak2 | NM_001048217.2 | chr19:29251802-29313080 | | 10837 | Kcng3 | NM_153512.1 | chr17:83585956-83631895 |
| 10741 | Jak3 | NM_001190830.1 | chr8:71676382-71688313 | | 10838 | Kcng4 | NM_025734.2 | chr8:119628853-119635680 |
| 10742 | Jakmip1 | NM_178394.4 | chr5:37080856-37125298 | | 10839 | Kcnh1 | NM_001038607.2 | chr1:192190776-192510159 |
| 10743 | Jakmip2 | NM_001163637.1 | chr18:43531407-43687773 | | 10840 | Kcnh2 | NM_013569.2 | chr5:24319588-24351604 |
| 10744 | Jakmip3 | NM_028708.2 | chr7:138940729-139083976 | | 10841 | Kcnh3 | NM_010601.3 | chr15:99224975-99242817 |
| 10745 | Jam2 | NM_023844.5 | chr16:84774122-84826375 | | 10842 | Kcnh4 | NM_001081194.2 | chr11:100740377-100759778 |
| 10746 | Jam3 | NM_023277.4 | chr9:27097383-27155421 | | 10843 | Kcnh5 | NM_172805.3 | chr12:74897216-75177332 |
| 10747 | Jarid2 | NM_001205043.1 | chr13:44731270-44921643 | | 10844 | Kcnh6 | NM_001037712.1 | chr11:106008202-106034064 |
| 10748 | Jazf1 | NM_001168177.1 | chr6:52768067-52909620 | | 10845 | Kcnh7 | NM_133207.2 | chr2:62702945-63184287 |
| 10749 | Jdp2 | NM_001205052.1 | chr12:85599104-85639878 | | 10846 | Kcnh8 | NM_001031811.2 | chr17:52602708-52979194 |
| 10750 | Jkamp | NM_001205067.1 | chr12:72085838-72101527 | | 10847 | Kcnip1 | NM_001190885.1 | chr11:33829340-33843585 |
| 10751 | Jmjd1c | NM_001242369.1 | chr10:67185749-67256326 | | 10848 | Kcnip2 | NM_001276358.1 | chr19:45792345-45812291 |
| 10752 | Jmjd4 | NM_001205068.1 | chr11:59450044-59458567 | | 10849 | Kcnip3 | NM_001113311.1 | chr2:127456497-127482499 |
| 10753 | Jmjd6 | NM_033398.2 | chr11:116837431-116843449 | | 10850 | Kcnip4 | NM_001199242.1 | chr5:48389502-48509761 |
| 10754 | Jmjd7 | NM_001114637.1 | chr2:120027482-120032604 | | 10851 | Kcnj1 | NM_001168354.1 | chr9:32393984-32399194 |
| 10755 | Jmjd7-pla2g4b | NR_104353.1 | chr2:120029042-120032604 | | 10852 | Kcnj10 | NM_001039484.1 | chr1:172341269-172374085 |
| 10756 | Jmjd8 | NM_028180.2 | chr17:25329042-25831849 | | 10853 | Kcnj11 | NM_001204411.1 | chr7:46097122-46100764 |
| 10757 | Jmy | NM_021310.3 | chr13:93430096-93499808 | | 10854 | Kcnj12 | NM_001267693.1 | chr11:61022563-61073267 |
| 10758 | Josd1 | NM_028792.3 | chr15:79674249-79687872 | | 10855 | Kcnj13 | NM_001110227.2 | chr1:87364576-87394729 |
| 10759 | Josd2 | NM_001205070.1 | chr7:44467979-44471658 | | 10856 | Kcnj14 | NM_145963.2 | chr7:45816466-45824747 |
| 10760 | Jph1 | NM_020604.2 | chr1:16994939-17097789 | | 10857 | Kcnj15 | NM_001039056.2 | chr16:95257557-95300258 |
| 10761 | Jph2 | NM_001205076.1 | chr2:163336241-163397993 | | 10858 | Kcnj16 | NM_001252207.1 | chr11:110968032-111027967 |
| 10762 | Jph3 | NM_020605.3 | chr8:121730058-121791083 | | 10859 | Kcnj2 | NM_008425.4 | chr11:111066163-111076825 |
| 10763 | Jph4 | NM_177049.5 | chr14:55106825-55116935 | | 10860 | Kcnj3 | NM_008426.2 | chr2:55435969-55598145 |
| 10764 | Jpx | NR_015508.3 | chrX:103493557-103506425 | | 10861 | Kcnj4 | NM_008427.4 | chr15:79483713-79505241 |
| 10765 | Jrk | NM_008415.6 | chr15:74702411-74709322 | | 10862 | Kcnj5 | NM_010605.4 | chr9:32314782-32344237 |
| 10766 | Jrkl | NM_001033181.1 | chr9:13242789-13245741 | | 10863 | Kcnj6 | NM_001025584.2 | chr16:94748682-94997696 |

Fig.21 - 57

| | | | | | | | | |
|---|---|---|---|---|---|---|---|---|
| 10864 | Kcnj8 | NM_008428.4 | chr6:142564938-142571356 | 10961 | Khdc3 | NM_025890.3 | chr9:73102397-73104443 |
| 10865 | Kcnj9 | NM_008429.2 | chr1:172321032-172329263 | 10962 | Khdrbs1 | NM_011317.4 | chr4:129713814-129742303 |
| 10866 | Kcnk1 | NM_008430.2 | chr8:125995101-126030688 | 10963 | Khdrbs2 | NM_133235.2 | chr1:32172805-32657738 |
| 10867 | Kcnk10 | NM_029911.5 | chr12:98433993-98577940 | 10964 | Khdrbs3 | NM_010158.2 | chr15:68928419-69093518 |
| 10868 | Kcnk12 | NM_199251.1 | chr17:87745820-87797994 | 10965 | Khk | NM_008439.4 | chr5:30921558-30931248 |
| 10869 | Kcnk13 | NM_001164426.1 | chr12:99964498-100062682 | 10966 | Khnyn | NM_027143.2 | chr14:55884968-55896781 |
| 10870 | Kcnk15 | NM_001030292.1 | chr2:163853749-163858874 | 10967 | Khsrp | NM_010613.3 | chr17:57021048-57031507 |
| 10871 | Kcnk16 | NM_029006.1 | chr14:20262755-20269162 | 10968 | Kidins220 | NM_001081378.1 | chr12:24974931-25059697 |
| 10872 | Kcnk18 | NM_207261.3 | chr19:59219647-59237370 | 10969 | Kif11 | NM_010615.1 | chr19:37376402-37421859 |
| 10873 | Kcnk2 | NM_001159850.1 | chr1:189207929-189343353 | 10970 | Kif12 | NM_010616.2 | chr4:63165636-63172131 |
| 10874 | Kcnk3 | NM_010608.2 | chr5:30588169-30625270 | 10971 | Kif13a | NM_010617.2 | chr13:46749087-46929718 |
| 10875 | Kcnk4 | NM_008431.2 | chr19:6925689-6934515 | 10972 | Kif13b | NM_001081177.1 | chr14:64652530-64806296 |
| 10876 | Kcnk5 | NM_021542.4 | chr14:20140057-20181782 | 10973 | Kif14 | NM_001287179.2 | chr1:136467847-136530819 |
| 10877 | Kcnk6 | NM_001033525.3 | chr7:29221927-29232522 | 10974 | Kif15 | NM_010620.1 | chr9:122951080-123018733 |
| 10878 | Kcnk7 | NM_010609.2 | chr19:5704475-5707101 | 10975 | Kif16b | NM_001081133.2 | chr2:142618344-142901464 |
| 10879 | Kcnk9 | NM_001033876.1 | chr15:72512118-72546279 | 10976 | Kif17 | NM_001190978.1 | chr4:138262250-138301973 |
| 10880 | Kcnma1 | NM_001253358.1 | chr14:23298693-24004205 | 10977 | Kif18a | NM_139303.1 | chr2:109280737-109341746 |
| 10881 | Kcnmb1 | NM_031169.4 | chr11:33963012-33973638 | 10978 | Kif18b | NM_197959.2 | chr11:102905516-102925124 |
| 10882 | Kcnmb2 | NM_028231.2 | chr3:31902702-32200180 | 10979 | Kif19a | NM_001102615.1 | chr11:114765388-114790575 |
| 10883 | Kcnmb3 | NM_001195074.1 | chr3:32472320-32491969 | 10980 | Kif1a | NM_001110315.2 | chr1:93015454-93101874 |
| 10884 | Kcnmb4 | NM_021452.1 | chr11:116417867-116473523 | 10981 | Kif1b | NM_001290995.1 | chr4:149176318-149367733 |
| 10885 | Kcnmb4os1 | NR_028107.1 | chr10:116418120-116421235 | 10982 | Kif1c | NM_153103.2 | chr11:70700547-70731970 |
| 10886 | Kcnn1 | NM_032397.2 | chr8:70842048-70857008 | 10983 | Kif20a | NM_001166406.1 | chr18:34625032-34633277 |
| 10887 | Kcnn2 | NM_080465.2 | chr18:45560153-45885583 | 10984 | Kif20b | NM_183046.1 | chr19:34922357-34975731 |
| 10888 | Kcnn3 | NM_080466.2 | chr3:89520163-89672494 | 10985 | Kif21a | NM_001109040.2 | chr15:90933274-91049951 |
| 10889 | Kcnn4 | NM_001163516.1 | chr7:24370262-24385212 | 10986 | Kif21b | NM_010394972.1 | chr1:136131400-136178014 |
| 10890 | Kcnq1 | NM_008434.2 | chr7:143107253-143427042 | 10987 | Kif22 | NM_145588.1 | chr7:127027730-127042420 |
| 10891 | Kcnq1ot1 | NR_001461.5 | chr7:143213110-143296547 | 10988 | Kif23 | NM_024245.4 | chr9:61917277-61946799 |
| 10892 | Kcnq2 | NM_001003824.2 | chr2:181075578-181135289 | 10989 | Kif24 | NM_024241.2 | chr4:41390747-41464848 |
| 10893 | Kcnq3 | NM_152923.2 | chr15:65994914-66286224 | 10990 | Kif26a | NM_001097621.1 | chr12:112146207-112181747 |
| 10894 | Kcnq4 | NM_001081142.1 | chr4:120697472-120747176 | 10991 | Kif26b | NM_001161665.1 | chr1:178529124-178932857 |
| 10895 | Kcnq5 | NM_001160339.1 | chr1:21398402-21961942 | 10992 | Kif27 | NM_175214.3 | chr13:58287515-58354862 |
| 10896 | Kcnrg | NM_001039105.3 | chr14:61607456-61612833 | 10993 | Kif2a | NM_001145779.1 | chr13:106960584-107022114 |
| 10897 | Kcns1 | NM_008435.2 | chr2:164163618-164171113 | 10994 | Kif2b | NM_028547.2 | chr11:91575285-91577555 |
| 10898 | Kcns2 | NM_001271704.1 | chr15:34838048-34843407 | 10995 | Kif2c | NM_001290662.1 | chr4:117159632-117178772 |
| 10899 | Kcns3 | NM_001168664.1 | chr12:11090201-11150842 | 10996 | Kif3a | NM_001290805.1 | chr11:53567368-53604246 |
| 10900 | Kcnt1 | NM_001145402.1 | chr2:25863794-25918273 | 10997 | Kif3b | NM_008444.4 | chr2:153291415-153333389 |
| 10901 | Kcnt2 | NM_001081027.2 | chr1:140246256-140610261 | 10998 | Kif3c | NM_008445.2 | chr12:3365191-3406494 |
| 10902 | Kcnu1 | NM_008423.2 | chr8:25849622-25937934 | 10999 | Kif4 | NM_008446.2 | chrX:100626064-100727271 |
| 10903 | Kcnv1 | NM_026200.3 | chr15:45106283-45114934 | 11000 | Kif4-ps | NR_033653.1 | chr12:101145608-101149273 |
| 10904 | Kcnv2 | NM_183179.1 | chr19:27322618-27337179 | 11001 | Kif5a | NM_001039000.4 | chr10:127225694-127263363 |
| 10905 | Kcp | NM_001029985.4 | chr6:29482035-29507952 | 11002 | Kif5b | NM_008448.3 | chr18:6201004-6241524 |
| 10906 | Kctd1 | NM_001142731.1 | chr18:14968864-15063582 | 11003 | Kif5c | NM_008449.2 | chr2:49619313-49774778 |
| 10907 | Kctd10 | NM_001159941.1 | chr5:114383571-114380505 | 11004 | Kif6 | NM_177052.3 | chr17:49615171-49909847 |
| 10908 | Kctd11 | NM_153143.4 | chr11:69878263-69880985 | 11005 | Kif7 | NM_001291222.1 | chr7:79698097-79714186 |
| 10909 | Kctd12 | NM_177715.4 | chr14:102976580-102982637 | 11006 | Kif9 | NM_001163569.1 | chr9:110476993-110524440 |
| 10910 | Kctd12b | NM_175429.3 | chrX:153685153-153696280 | 11007 | Kifap3 | NM_010629.3 | chr1:163779582-163917107 |
| 10911 | Kctd13 | NM_172747.2 | chr7:126928878-126945609 | 11008 | Kifc1 | NM_001195298.1 | chr17:33875665-33890633 |
| 10912 | Kctd14 | NM_001010826.3 | chr7:97453203-97459557 | 11009 | Kifc2 | NM_010630.2 | chr15:76660640-76668196 |
| 10913 | Kctd15 | NM_146188.4 | chr7:34618780-34652841 | 11010 | Kifc3 | NM_001145831.1 | chr8:95099827-95142540 |
| 10914 | Kctd16 | NM_028135.1 | chr18:40258360-40531184 | 11011 | Kifc5b | NM_053173.2 | chr17:26917090-26932579 |
| 10915 | Kctd17 | NM_001289671.1 | chr15:78428563-78439303 | 11012 | Kin | NM_025280.2 | chr2:10080611-10092701 |
| 10916 | Kctd18 | NM_001159864.1 | chr1:57955100-57970084 | 11013 | Kir3dl1 | NM_177749.4 | chrX:136517998-136534306 |
| 10917 | Kctd19 | NM_177791.3 | chr8:105382806-105413502 | 11014 | Kir3dl2 | NM_177748.2 | chrX:136448106-136469041 |
| 10918 | Kctd2 | NM_183285.3 | chr11:115420125-115431274 | 11015 | Kirrel | NM_001170985.1 | chr3:87078591-87174747 |
| 10919 | Kctd20 | NM_025888.5 | chr17:28953215-28967937 | 11016 | Kirrel2 | NM_172898.3 | chr7:30447765-30457515 |
| 10920 | Kctd21 | NM_001039039.3 | chr7:97332322-97350216 | 11017 | Kirrel3 | NM_001190911.1 | chr9:34883730-35036307 |
| 10921 | Kctd3 | NM_172650.2 | chr1:188971097-189007840 | 11018 | Kis2 | NR_003188.1 | chrX:52742562-52744593 |
| 10922 | Kctd4 | NM_026214.3 | chr14:75965002-75965217 | 11019 | Kiss1 | NM_178260.3 | chr1:133327211-133329722 |
| 10923 | Kctd5 | NM_027008.2 | chr17:24047719-24073485 | 11020 | Kiss1r | NM_053244.5 | chr10:79916970-79922272 |
| 10924 | Kctd6 | NM_027782.3 | chr14:8214080-8223569 | 11021 | Kit | NM_001122733.1 | chr5:75574986-75656721 |
| 10925 | Kctd7 | NM_172509.3 | chr5:130144887-130155808 | 11022 | Kitl | NM_013598.2 | chr10:100015823-100100412 |
| 10926 | Kctd8 | NM_175519.5 | chr5:69916407-69527739 | 11023 | Kiz | NM_001033298.3 | chr2:146885288-146970089 |
| 10927 | Kctd9 | NM_001111028.1 | chr14:67718097-67742310 | 11024 | Kl | NM_013823.2 | chr5:150952606-150993817 |
| 10928 | Kdelc1 | NM_023645.3 | chr1:44106545-44118773 | 11025 | Klb | NM_031180.2 | chr5:65348410-65384603 |
| 10929 | Kdelc2 | NM_212445.2 | chr9:53384002-53401867 | 11026 | Klc1 | NM_001025358.2 | chr12:111758867-111794899 |
| 10930 | Kdelr1 | NM_139950.2 | chr7:45872839-45883726 | 11027 | Klc2 | NM_008451.2 | chr19:5107745-5118408 |
| 10931 | Kdelr2 | NM_025841.4 | chr5:143403819-143421904 | 11028 | Klc3 | NM_001286038.1 | chr7:19394439-19399921 |
| 10932 | Kdelr3 | NM_134090.3 | chr15:79516407-79527739 | 11029 | Klc4 | NM_029091.2 | chr17:46830630-46645144 |
| 10933 | Kdf1 | NM_001083916.1 | chr4:133518962-133530790 | 11030 | Klf1 | NM_010635.2 | chr8:84901927-84905295 |
| 10934 | Kdm1a | NM_133872.2 | chr4:136550532-136602723 | 11031 | Klf10 | NM_001289471.1 | chr15:38291463-38300711 |
| 10935 | Kdm1b | NM_172262.3 | chr13:47043498-47085279 | 11032 | Klf11 | NM_178357.3 | chr12:24651370-24662782 |
| 10936 | Kdm2a | NM_001019842.1 | chr19:4316146-4397077 | 11033 | Klf12 | NM_010636.3 | chr14:99870639-100149796 |
| 10937 | Kdm2b | NM_001003953.2 | chr5:122870675-122989099 | 11034 | Klf13 | NM_021366.3 | chr7:63886350-63938815 |
| 10938 | Kdm3a | NM_001038695.3 | chr6:71588969-71632937 | 11035 | Klf14 | NM_001135093.1 | chr6:30956020-30958990 |
| 10939 | Kdm3b | NM_001081256.1 | chr18:34777007-34839370 | 11036 | Klf15 | NM_023184.3 | chr6:90462625-90475209 |
| 10940 | Kdm4a | NM_001161823.1 | chr4:128117003-118180043 | 11037 | Klf16 | NM_078477.2 | chr10:80567120-80577296 |
| 10941 | Kdm4b | NM_172132.2 | chr17:56326049-56402873 | 11038 | Klf17 | NM_029416.2 | chr4:117756658-117765666 |
| 10942 | Kdm4c | NM_001172095.1 | chr4:74242496-74405864 | 11039 | Klf2 | NM_008452.2 | chr8:72319061-72321654 |
| 10943 | Kdm4d | NM_173433.2 | chr9:14462580-14500482 | 11040 | Klf3 | NM_008453.5 | chr5:64803522-64830129 |
| 10944 | Kdm5a | NM_145997.2 | chr6:120364098-120444574 | 11041 | Klf4 | NM_010637.3 | chr4:55527136-55532475 |
| 10945 | Kdm5b | NM_152895.2 | chr1:134560177-134632878 | 11042 | Klf5 | NM_009769.4 | chr14:99298690-99313409 |
| 10946 | Kdm5c | NM_013668.4 | chrX:152233226-152279099 | 11043 | Klf6 | NM_011803.2 | chr13:5861488-5870393 |
| 10947 | Kdm5d | NM_011419.3 | chrY:897787-943811 | 11044 | Klf7 | NM_033563.2 | chr1:64035670-64121389 |
| 10948 | Kdm6a | NM_18162574-18279936 | chrX:18162574-18279936 | 11045 | Klf8 | NM_173780.4 | chrX:153238044-153396134 |
| 10949 | Kdm6b | NM_001017426.3 | chr11:69398517-69413675 | 11046 | Klf9 | NM_010638.4 | chr19:23141225-23169911 |
| 10950 | Kdm7a | NM_001033430.4 | chr6:39193619-39206773 | 11047 | Klhdc1 | NM_178253.5 | chr12:69241831-69283981 |
| 10951 | Kdm8 | NM_029842.5 | chr7:125444619-125462268 | 11048 | Klhdc10 | NM_029742.3 | chr6:30401854-30455174 |
| 10952 | Kdr | NM_010612.2 | chr5:75933269-75978428 | 11049 | Klhdc2 | NM_027117.3 | chr12:69296680-69310687 |
| 10953 | Kdsr | NM_027554.3 | chr1:106720409-106759742 | 11050 | Klhdc3 | NM_001163729.2 | chr17:46674550-46680930 |
| 10954 | Keap1 | NM_001110305.1 | chr9:21229729-21239332 | 11051 | Klhdc4 | NM_146605.2 | chr8:121796307-121829569 |
| 10955 | Keg1 | NM_029550.4 | chr19:12695789-12719896 | 11052 | Klhdc7a | NM_173427.2 | chr4:139962172-139968026 |
| 10956 | Kel | NM_032540.3 | chr6:41686329-41704325 | 11053 | Klhdc7b | NM_001160178.1 | chr15:89386890-89388708 |
| 10957 | Kera | NM_008438.3 | chr10:97607204-97613688 | 11054 | Klhdc8a | NM_144810.4 | chr1:132298625-132307357 |
| 10958 | Khdc1a | NM_183322.2 | chr1:21349676-21352199 | 11055 | Klhdc8b | NM_030075.2 | chr9:108447638-108461581 |
| 10959 | Khdc1b | NM_001113187.1 | chr1:21383555-21386384 | 11056 | Klhdc9 | NM_023053039.2 | chr1:171358448-171360798 |
| 10960 | Khdc1c | NM_001033904.1 | chr1:21368330-21369743 | 11057 | Klhl1 | NM_053105.2 | chr14:96105264-96519034 |

Fig.21 - 58

| | | | | | | | |
|---|---|---|---|---|---|---|---|
| 11058 | Klhl10 | NM_025727.3 | chr11:100441923-100457024 | 11155 | Klrg2 | NM_001033171.2 | chr6:38626659-38637239 |
| 11059 | Klhl11 | NM_172565.2 | chr11:100462611-100472782 | 11156 | Klri1 | NM_001012520.2 | chr6:129697217-129717132 |
| 11060 | Klhl12 | NM_153128.3 | chr1:134455530-134490873 | 11157 | Klri2 | NM_177155.4 | chr6:129729040-129749484 |
| 11061 | Klhl13 | NM_001290476.2 | chrX:23219270-23285559 | 11158 | Klrk1 | NM_001083322.2 | chr6:129610322-129623864 |
| 11062 | Klhl14 | NM_001081403.1 | chr18:21550376-21652368 | 11159 | Kmo | NM_133809.1 | chr1:175632192-175660853 |
| 11063 | Klhl15 | NM_001039059.1 | chrX:94234929-94255968 | 11160 | Kmt2a | NM_001081049.1 | chr9:44803354-44881274 |
| 11064 | Klhl17 | NM_198305.2 | chr4:156229043-156234857 | 11161 | Kmt2b | NM_001290573.1 | chr7:30568854-30588726 |
| 11065 | Klhl18 | NM_177771.5 | chr9:110425925-110476694 | 11162 | Kmt2c | NM_001081383.1 | chr5:25271793-25498783 |
| 11066 | Klhl2 | NM_178633.3 | chr8:64739674-64849924 | 11163 | Kmt2d | NM_001033276.3 | chr15:98831668-98871205 |
| 11067 | Klhl20 | NM_001039482.1 | chr1:161088377-161131479 | 11164 | Kmt2e | NM_026984.1 | chr5:23434428-23504229 |
| 11068 | Klhl21 | NM_001033352.3 | chr4:152008890-152017677 | 11165 | Kncn | NM_001039124.3 | chr4:115884399-115887964 |
| 11069 | Klhl22 | NM_145479.4 | chr16:17759620-17793382 | 11166 | Kndc1 | NM_177261.4 | chr7:139894695-139941540 |
| 11070 | Klhl23 | NM_177784.4 | chr2:69822369-69836651 | 11167 | Kng1 | NM_001102411.1 | chr16:23058299-23080006 |
| 11071 | Klhl24 | NM_029436.3 | chr16:20097583-20127744 | 11168 | Kng2 | NM_001102409.1 | chr16:22985851-23029101 |
| 11072 | Klhl25 | NM_001122780.1 | chr7:75848337-75874130 | 11169 | Knop1 | NM_001168218.1 | chr7:118842217-118855998 |
| 11073 | Klhl26 | NM_001122850.1 | chr8:70450227-70476943 | 11170 | Knstrn | NM_026412.3 | chr2:118814002-118836212 |
| 11074 | Klhl28 | NM_025707.3 | chr12:64942439-64965536 | 11171 | Kntc1 | NM_001042421.1 | chr5:123749725-123821593 |
| 11075 | Klhl29 | NM_001164493.1 | chr12:5077465-5375682 | 11172 | Kpna1 | NM_008465.5 | chr16:35983362-36036162 |
| 11076 | Klhl3 | NM_001195075.1 | chr13:58004956-58102428 | 11173 | Kpna2 | NM_010655.3 | chr11:106988628-106999525 |
| 11077 | Klhl30 | NM_027551.2 | chr1:91351072-91362404 | 11174 | Kpna3 | NM_008466.5 | chr14:61365185-61439947 |
| 11078 | Klhl31 | NM_172925.2 | chr9:77636731-77660122 | 11175 | Kpna4 | NM_008467.4 | chr3:69072220-69127092 |
| 11079 | Klhl32 | NM_001035531.3 | chr4:24617272-24851086 | 11176 | Kpna6 | NM_008468.4 | chr4:129643978-129672767 |
| 11080 | Klhl33 | NM_001166651.1 | chr14:50891388-50893255 | 11177 | Kpna7 | NM_001013774.2 | chr5:144983743-145009636 |
| 11081 | Klhl34 | NM_001081667.2 | chrX:157618434-157821060 | 11178 | Kpnb1 | NM_008379.3 | chr11:97159709-97187892 |
| 11082 | Klhl35 | NM_028145.1 | chr7:99468003-99474020 | 11179 | Kprp | NM_028629.1 | chr3:92823073-92827247 |
| 11083 | Klhl36 | NM_146219.1 | chr8:119862204-119876989 | 11180 | Kptn | NM_133727.2 | chr7:16119875-16127516 |
| 11084 | Klhl38 | NM_177755.3 | chr15:58314572-58324169 | 11181 | Kras | NM_021284 | chr6:145216898-145250231 |
| 11085 | Klhl4 | NM_001290477.1 | chrX:114474332-114561129 | 11182 | Krba1 | NM_133922.3 | chr6:48395585-48419855 |
| 11086 | Klhl40 | NM_028202.3 | chr9:121777606-121783819 | 11183 | Krcc1 | NM_145568.3 | chr6:71272018-71295319 |
| 11087 | Klhl41 | NM_001081087.1 | chr2:69670119-69684239 | 11184 | Kremen1 | NM_032396.3 | chr11:5191552-5261610 |
| 11088 | Klhl42 | NM_026414.1 | chr6:147091074-147112778 | 11185 | Kremen2 | NM_026416.1 | chr17:23741198-23745829 |
| 11089 | Klhl5 | NM_175174.4 | chr5:65131230-65168142 | 11186 | Kri1 | NM_145416.3 | chr9:21273456-21287969 |
| 11090 | Klhl6 | NM_183390.3 | chr16:19946491-19983049 | 11187 | Krit1 | NM_001170552.1 | chr5:3803164-3844515 |
| 11091 | Klhl7 | NM_001161800.1 | chr5:24100589-24161231 | 11188 | Krr1 | NM_178610.4 | chr10:111972694-111988430 |
| 11092 | Klhl8 | NM_178741.3 | chr5:103862049-103911229 | 11189 | Krt1 | NM_008473.2 | chr15:101845425-101850786 |
| 11093 | Klhl9 | NM_172871.2 | chr4:88713291-88722508 | 11190 | Krt10 | NM_010660.2 | chr11:99385255-99389864 |
| 11094 | Klk1 | NM_010639.5 | chr7:44225436-44229617 | 11191 | Krt12 | NM_010661.2 | chr11:99415663-99422259 |
| 11095 | Klk10 | NM_133712.2 | chr7:43781053-43785410 | 11192 | Krt13 | NM_010662.2 | chr11:100117327-100121566 |
| 11096 | Klk11 | NM_011773.1 | chr7:43774616-43779262 | 11193 | Krt14 | NM_016958.2 | chr11:100203161-100207510 |
| 11097 | Klk12 | NM_027097.1 | chr7:43769099-43773481 | 11194 | Krt15 | NM_008469.2 | chr11:100131758-100135949 |
| 11098 | Klk13 | NM_001039042.2 | chr7:43712566-43726758 | 11195 | Krt16 | NM_008470.1 | chr11:100246090-100248902 |
| 11099 | Klk14 | NM_174866.3 | chr7:43690647-43695536 | 11196 | Krt17 | NM_010663.3 | chr11:100256214-100261029 |
| 11100 | Klk15 | NM_174865.1 | chr7:43933770-43939590 | 11197 | Krt18 | NM_010664.2 | chr15:102028215-102032026 |
| 11101 | Klk1b11 | NM_010645.2 | chr7:43966767-43971315 | 11198 | Krt19 | NM_008471.3 | chr11:100140810-100145926 |
| 11102 | Klk1b11 | NM_010640.1 | chr7:43995878-43999875 | 11199 | Krt2 | NM_010668.2 | chr15:101810688-101818169 |
| 11103 | Klk1b16 | NM_008454.2 | chr7:44136766-44141604 | 11200 | Krt20 | NM_023256.1 | chr11:99428402-99438153 |
| 11104 | Klk1b21 | NM_010643.2 | chr7:44102291-44106579 | 11201 | Krt222 | NM_172946.2 | chr11:99233097-99244067 |
| 11105 | Klk1b22 | NM_010114.1 | chr7:44112682-44116876 | 11202 | Krt23 | NM_033373.1 | chr11:99477972-99493110 |
| 11106 | Klk1b24 | NM_010643.1 | chr7:44188262-44192451 | 11203 | Krt24 | NM_029393.1 | chr11:99280092-99285238 |
| 11107 | Klk1b26 | NM_010644.7 | chr7:44161077-44016969 | 11204 | Krt25 | NM_133730.1 | chr11:99315843-99322941 |
| 11108 | Klk1b27 | NM_020268.3 | chr7:44052289-44056711 | 11205 | Krt26 | NM_001033397.5 | chr11:99328483-99337985 |
| 11109 | Klk1b3 | NM_008693.2 | chr7:44198196-44202351 | 11206 | Krt27 | NM_010666.2 | chr11:99345564-99351118 |
| 11110 | Klk1b4 | NM_010639.3 | chr7:44207464-44211754 | 11207 | Krt28 | NM_027574.1 | chr11:99365006-99374903 |
| 11111 | Klk1b5 | NM_008456.3 | chr7:44216474-44220703 | 11208 | Krt31 | NM_010659.2 | chr11:100046645-100050551 |
| 11112 | Klk1b7-ps | NR_033120.1 | chr7:43945011-43945927 | 11209 | Krt32 | NM_001080847-100088726 | chr11:100080847-100088726 |
| 11113 | Klk1b8 | NM_008457.2 | chr7:43950671-43954938 | 11210 | Krt33a | NM_027983.3 | chr11:100011198-100016212 |
| 11114 | Klk1b9 | NM_010116.1 | chr7:43976060-43980376 | 11211 | Krt33b | NM_013570.1 | chr11:100023633-100029868 |
| 11115 | Klk4 | NM_019928.1 | chr7:43881171-43885804 | 11212 | Krt34 | NM_027563.4 | chr11:100037347-100041554 |
| 11116 | Klk5 | NM_026806.2 | chr7:43842268-43851181 | 11213 | Krt35 | NM_016880.2 | chr11:100092191-100098224 |
| 11117 | Klk6 | NM_001164696.1 | chr7:43824543-43832027 | 11214 | Krt36 | NM_001174099.1 | chr11:100102012-100105626 |
| 11118 | Klk7 | NM_011872.2 | chr7:43811443-43816359 | 11215 | Krt39 | NM_213730.2 | chr11:99514623-99521258 |
| 11119 | Klk8 | NM_008940.2 | chr7:43795576-43803822 | 11216 | Krt4 | NM_008475.2 | chr15:101918594-101924735 |
| 11120 | Klk9 | NM_028660.3 | chr7:43789090-43796756 | 11217 | Krt40 | NM_001039666.1 | chr11:99537484-99543158 |
| 11121 | Klkb1 | NM_008455.2 | chr8:45269450-45294835 | 11218 | Krt42 | NM_212483.2 | chr11:100262881-100269871 |
| 11122 | Klra1 | NM_016659.3 | chr6:130363917-130386874 | 11219 | Krt5 | NM_027011.2 | chr15:101707069-101712891 |
| 11123 | Klra10 | NM_008459.1 | chr6:130281928-130281928 | 11220 | Krt6a | NM_008476.3 | chr15:101689927-101694305 |
| 11124 | Klra12 | NM_010646.1 | chr6:130044023-130306481 | 11221 | Krt6b | NM_010669.2 | chr15:101676022-101680259 |
| 11125 | Klra13-ps | NR_033451.1 | chr6:130291160-130306432 | 11222 | Krt7 | NM_033073.3 | chr15:101412402-101427806 |
| 11126 | Klra14-ps | NR_104105.1 | chr6:130149105-130160748 | 11223 | Krt71 | NM_019956.1 | chr15:101733948-101743097 |
| 11127 | Klra15 | NM_013793.2 | chr6:129972092-130380662 | 11224 | Krt72 | NM_213728.1 | chr15:101776559-101786458 |
| 11128 | Klra17 | NM_133203.5 | chr6:129853133-129876672 | 11225 | Krt73 | NM_212485.2 | chr15:101793307-101802332 |
| 11129 | Klra18 | NM_053159.2 | chr6:130043744-130067258 | 11226 | Krt74 | NR_033444.1 | chr15:101754258-101763504 |
| 11130 | Klra19 | NM_053154.2 | chr6:130013033-130026960 | 11227 | Krt75 | NM_133357.3 | chr15:101563842-101573904 |
| 11131 | Klra2 | NM_001170851.1 | chr6:131139234-131247362 | 11228 | Krt76 | NM_001033177.2 | chr15:101884350-101892920 |
| 11132 | Klra21 | NM_053151.1 | chr6:130315218-130129879 | 11229 | Krt77 | NM_001003667.1 | chr15:101859855-101869618 |
| 11133 | Klra22 | NM_053152.2 | chr6:129972081-130380808 | 11230 | Krt78 | NM_212487.4 | chr15:101946003-101954287 |
| 11134 | Klra23 | NM_024470.1 | chr6:129291160-130308361 | 11231 | Krt79 | NM_146063.1 | chr15:101929331-101940324 |
| 11135 | Klra3 | NM_001289604.1 | chr6:130323288-130337626 | 11232 | Krt8 | NM_031170.2 | chr15:101996710-102004342 |
| 11136 | Klra33 | NM_001039118.1 | chr6:130030995-130030995 | 11233 | Krt80 | NM_028770.2 | chr15:101349570-101376125 |
| 11137 | Klra4 | NM_001252577.1 | chr6:130044016-130067271 | 11234 | Krt81 | NM_001166157.1 | chr15:101459060-101463765 |
| 11138 | Klra5 | NM_008463.4 | chr6:129898991-129913224 | 11235 | Krt82 | NM_053249.3 | chr15:101541220-101550659 |
| 11139 | Klra6 | NM_008464.3 | chr6:130013032-130026954 | 11236 | Krt83 | NM_001003668.2 | chr15:101431489-101438804 |
| 11140 | Klra7 | NM_001110323.1 | chr6:130218830-130233322 | 11237 | Krt84 | NM_008474.2 | chr15:101525025-101532820 |
| 11141 | Klra8 | NM_001101620.1 | chr6:130115225-130129898 | 11238 | Krt85 | NM_016879.2 | chr15:101433013-101491303 |
| 11142 | Klra9 | NM_010651.3 | chr6:130178681-130193112 | 11239 | Krt86 | NM_010667.2 | chr15:101473477-101479983 |
| 11143 | Klrb1 | NM_001099918.1 | chr6:128706507-128723846 | 11240 | Krt9 | NM_201255.2 | chr11:100186780-100193246 |
| 11144 | Klrb1a | NM_008526.6 | chr6:128609256-128622934 | 11241 | Krtap10-10 | NM_001024709.3 | chr10:77835946-77837251 |
| 11145 | Klrb1b | NM_030599.4 | chr6:128813705-128826315 | 11242 | Krtap10-4 | NM_001135991.1 | chr10:77826168-77827070 |
| 11146 | Klrb1c | NM_001159904.1 | chr6:128784484-128788641 | 11243 | Krtap11-1 | NM_001113406.1 | chr16:89570175-89571183 |
| 11147 | Klrb1f | NM_153094.2 | chr6:129045900-129057471 | 11244 | Krtap12-1 | NM_010670.1 | chr10:77720585-77721256 |
| 11148 | Klrb1-ps1 | NR_073569.1 | chr6:129116517-129129446 | 11245 | Krtap13 | NM_010671.1 | chr16:88750743-88751628 |
| 11149 | Klrc1 | NM_001136068.2 | chr6:129666015-129678973 | 11246 | Krtap1-3 | NM_001085526.2 | chr11:99590460-99591377 |
| 11150 | Klrc2 | NM_001098669.1 | chr6:129660596-129660596 | 11247 | Krtap13-1 | NM_183189.1 | chr16:88728861-88729611 |
| 11151 | Klrc3 | NM_021378.5 | chr6:129639084-129643288 | 11248 | Krtap14 | NM_013707.2 | chr16:88825290-88826145 |
| 11152 | Klrd1 | NM_010654.3 | chr6:129591810-129593775 | 11249 | Krtap15 | NM_001039502.3 | chr16:99582548-99583677 |
| 11153 | Klre1 | NM_153590.3 | chr6:129578285-129585827 | 11250 | Krtap15 | NM_013713.1 | chr16:88829008-88829844 |
| 11154 | Klrg1 | NM_016970.1 | chr6:122270596-122282833 | 11251 | Krtap1-5 | NM_027157.3 | chr11:99579976-99581016 |

Fig.21 - 59

| | | | | | | | | |
|---|---|---|---|---|---|---|---|---|
| 11252 | Krtap16-1 | NM_130870.1 | chr16:88873664-88874269 | 11349 | Laptm5 | NM_010686.3 | chr4:130913333-130936148 |
| 11253 | Krtap16-3 | NM_183296.1 | chr16:88962303-88962873 | 11350 | large | NM_010687.1 | chr8:72814598-73352556 |
| 11254 | Krtap17-1 | NM_001099774.2 | chr11:99993231-99993994 | 11351 | Larp1 | NM_028451.1 | chr11:58009063-58062032 |
| 11255 | Krtap19-1 | NM_130876.3 | chr16:88868917-88869410 | 11352 | Larp1b | NM_001040399.1 | chr3:40950630-40977793 |
| 11256 | Krtap19-3 | NM_130875.2 | chr16:88877512-88878038 | 11353 | Larp4 | NM_001024626.2 | chr15:99972779-100016358 |
| 11257 | Krtap19-4 | NM_130873.1 | chr16:88884785-88885089 | 11354 | Larp4b | NM_172585.3 | chr9:9093880-9174451 |
| 11258 | Krtap19-5 | NM_010676.2 | chr16:88895967-88896449 | 11355 | Larp6 | NM_026235.4 | chr9:60713120-60738801 |
| 11259 | Krtap19-9b | NM_133359.2 | chr16:88931803-88932264 | 11356 | Larp7 | NM_138593.2 | chr3:127536713-127553349 |
| 11260 | Krtap20-2 | NM_001163615.1 | chr16:89205860-89206394 | 11357 | Lars | NM_134137.2 | chr18:42202348-42262071 |
| 11261 | Krtap21-1 | NM_028821.3 | chr16:89403026-89403774 | 11358 | Lars2 | NM_153168.2 | chr9:123366939-123462664 |
| 11262 | Krtap22-2 | NM_001191018.1 | chr16:89010379-89010759 | 11359 | Las1l | NM_152822.3 | chrX:95935312-95956974 |
| 11263 | Krtap2-4 | NM_027800.1 | chr11:99614016-99614846 | 11360 | Lasp1 | NM_010688.4 | chr11:97799671-97838764 |
| 11264 | Krtap24-1 | NM_001163141.1 | chr16:88861078-88612279 | 11361 | Lat | NM_010689.2 | chr7:126363827-126369534 |
| 11265 | Krtap26-1 | NM_027105.2 | chr16:88646823-88647796 | 11362 | Lat2 | NM_020044 | chr5:134600102-134615025 |
| 11266 | Krtap27-1 | NM_001163105.1 | chr16:88671045-88671654 | 11363 | Lats1 | NM_010690.1 | chr10:7681208-7716461 |
| 11267 | Krtap3-1 | NM_023511.1 | chr11:99566026-99566630 | 11364 | Lats2 | NM_015771.2 | chr14:57689661-57746123 |
| 11268 | Krtap31-1 | NM_027568.2 | chr11:99907919-99908390 | 11365 | Lax1 | NM_001159649.1 | chr1:133679028-133690108 |
| 11269 | Krtap31-2 | NM_001025244.3 | chr11:99936290-99937225 | 11366 | Layn | NM_001033534.1 | chr9:51056779-51077094 |
| 11270 | Krtap3-2 | NM_025720.3 | chr11:99555822-99556853 | 11367 | Lbh | NM_029999.4 | chr17:72918304-72941946 |
| 11271 | Krtap3-3 | NM_025524.2 | chr11:99550131-99550863 | 11368 | Lbp | NM_008489.2 | chr2:158306492-158332852 |
| 11272 | Krtap4-1 | NM_001048196.1 | chr11:99627228-99628239 | 11369 | Lbr | NM_133815.2 | chr1:181815314-181842401 |
| 11273 | Krtap4-13 | NM_027087.3 | chr11:99809077-99809896 | 11370 | Lbx1 | NM_010691.5 | chr19:45233727-45235236 |
| 11274 | Krtap4-16 | NM_001013823.1 | chr11:99850654-99851605 | 11371 | Lbx2 | NM_010692.3 | chr6:83086364-83088241 |
| 11275 | Krtap4-2 | NM_026807.2 | chr11:99634113-99635084 | 11372 | Lca5 | NM_027448.2 | chr9:83393415-83441099 |
| 11276 | Krtap4-6 | NM_026834.2 | chr11:99665042-99665960 | 11373 | Lca5l | NM_001001493.2 | chr16:96158405-96192257 |
| 11277 | Krtap4-7 | NM_029613.1 | chr11:99643111-99644089 | 11374 | Lcat | NM_008490.2 | chr8:105939550-105943402 |
| 11278 | Krtap4-8 | NM_001085547.2 | chr11:99780013-99780643 | 11375 | Lce1a1 | NM_025984.2 | chr3:92646531-92648307 |
| 11279 | Krtap4-9 | NM_001085548.2 | chr11:99785199-99786257 | 11376 | Lce1a2 | NM_028625.2 | chr3:92668612-92670315 |
| 11280 | Krtap5-1 | NM_015808.1 | chr7:142296376-142297069 | 11377 | Lce1b | NM_026822.1 | chr3:92665649-92666926 |
| 11281 | Krtap5-2 | NM_027844.4 | chr7:142174531-142176005 | 11378 | Lce1c | NM_028622.2 | chr3:92679246-92680918 |
| 11282 | Krtap5-3 | NM_028860.1 | chr7:142201363-142203015 | 11379 | Lce1d | NM_027137.2 | chr3:92685498-92687210 |
| 11283 | Krtap5-4 | NM_015809.2 | chr7:142303501-142304503 | 11380 | Lce1e | NM_026811.2 | chr3:92707399-92709074 |
| 11284 | Krtap5-5 | NM_001037822.1 | chr7:142228794-142229671 | 11381 | Lce1f | NM_028394.3 | chr3:92718695-92720350 |
| 11285 | Krtap6-1 | NM_010672.3 | chr16:89031698-89032292 | 11382 | Lce1g | NM_025413.2 | chr3:92750150-92752338 |
| 11286 | Krtap6-3 | NM_010673.2 | chr16:89419322-89420111 | 11383 | Lce1h | NM_028336.2 | chr3:92763214-92765065 |
| 11287 | Krtap6-5 | NM_138856.2 | chr16:89047288-89047899 | 11384 | Lce1i | NM_029667.2 | chr3:92777209-92778899 |
| 11288 | Krtap7-1 | NM_026570.2 | chr16:69507702-89508323 | 11385 | Lce1j | NM_001281489.1 | chr3:92788644-92790614 |
| 11289 | Krtap8-1 | NM_010675.1 | chr16:89487373-89487952 | 11386 | Lce1k | NM_001254760.1 | chr3:92806290-92807891 |
| 11290 | Krtap9-1 | NM_015741.2 | chr11:99873388-99874000 | 11387 | Lce1l | NM_028628.2 | chr3:92849948-92851286 |
| 11291 | Krtap9-5 | NM_029351.2 | chr11:99597347-99598106 | 11388 | Lce1m | NM_025420.2 | chr3:93017806-93019060 |
| 11292 | Krtap9-5 | NM_001085527.1 | chr11:99948474-99949551 | 11389 | Lce3a | NM_001039594.1 | chr3:92925286-92926230 |
| 11293 | Krtcap2 | NM_025327.3 | chr3:89246437-89249729 | 11390 | Lce3b | NM_025501.3 | chr3:92932978-92934096 |
| 11294 | Krtcap3 | NM_027221.3 | chr5:31251705-31253197 | 11391 | Lce3c | NM_033175.3 | chr3:92944489-92945730 |
| 11295 | Krtdap | NM_001033131.3 | chr7:30787904-30791083 | 11392 | Lce3d | NM_001270426.1 | chr3:92957389-92958574 |
| 11296 | Ksr1 | NM_013571.2 | chr11:79014800-79146354 | 11393 | Lce3e | NM_001254725.1 | chr3:92967060-92968281 |
| 11297 | Ksr2 | NM_001312914.1 | chr5:117413770-117775004 | 11394 | Lce3f | NM_001018079.1 | chr3:92992225-92993426 |
| 11298 | Ktl12 | NM_029571.2 | chr4:108847856-108849412 | 11395 | Lce6a | NM_001166172.1 | chr3:92620084-92621660 |
| 11299 | Ktn1 | NM_008477.2 | chr14:47668755-47736564 | 11396 | Lck | NM_001162432.1 | chr4:129548343-129558372 |
| 11300 | Kxd1 | NM_029366.2 | chr8:70513395-70523180 | 11397 | Lclat1 | NM_001081071.2 | chr17:73107984-73243366 |
| 11301 | Ky | NM_024791.3 | chr9:102506137-102546239 | 11398 | Lcmt1 | NM_025304.3 | chr7:123377981-123430358 |
| 11302 | Kynu | NM_001289593.1 | chr2:43555324-43680216 | 11399 | Lcmt2 | NM_177846.3 | chr2:121137291-121140698 |
| 11303 | L1cam | NM_008478.3 | chrX:73853779-73880834 | 11400 | Lcn10 | NM_178036.4 | chr2:25682725-25686080 |
| 11304 | L1td1 | NM_001100455.2 | chr4:98726753-98738486 | 11401 | Lcn11 | NM_001100455.2 | chr2:25777016-25780279 |
| 11305 | L2hgdh | NM_145443.2 | chr12:69690435-69724874 | 11402 | Lcn12 | NM_029958.2 | chr2:25490844-25493911 |
| 11306 | L3hypdh | NM_026038.2 | chr12:73074427-72085313 | 11403 | Lcn2 | NM_008491.1 | chr2:32384636-32387739 |
| 11307 | L3mbtl1 | NM_001081338.1 | chr2:162943464-162974522 | 11404 | Lcn3 | NM_010694.1 | chr2:25765568-25768099 |
| 11308 | L3mbtl2 | NM_001289711.1 | chr15:81663888-81688315 | 11405 | Lcn4 | NM_010695.1 | chr2:26667673-26671282 |
| 11309 | L3mbtl3 | NM_172787.2 | chr10:26275451-26375185 | 11406 | Lcn5 | NM_001042630.2 | chr2:25657951-25662230 |
| 11310 | L3mbtl4 | NM_177278.5 | chr17:68273796-68780086 | 11407 | Lcn6 | NM_001276448.1 | chr2:25676785-25681607 |
| 11311 | l7Rn6 | NM_001291286.1 | chr7:89913684-89941204 | 11408 | Lcn8 | NM_033145.1 | chr2:25653117-25656216 |
| 11312 | Lacc1 | NM_172488.2 | chr14:77024200-77036617 | 11409 | Lcn9 | NM_029959.2 | chr2:25823152-25825537 |
| 11313 | Lacc1 | NM_145743.2 | chr10:42312584-42478565 | 11410 | Lcor | NM_172154.4 | chr19:41549698-41559781 |
| 11314 | Lactb | NM_030717.1 | chr9:66955392-66975484 | 11411 | Lcorl | NM_001166073.1 | chr5:45730331-45857540 |
| 11315 | Lactb2 | NM_145381.2 | chr1:13625899-13660509 | 11412 | Lcp1 | NM_001247984.1 | chr14:75131122-75230842 |
| 11316 | Lactbl1 | NM_001243262.1 | chr4:136622620-136638110 | 11413 | Lcp2 | NM_010696.3 | chr11:34047200-34092280 |
| 11317 | Lad1 | NM_133664.3 | chr1:135814957-135833341 | 11414 | Lct | NM_001081078.2 | chr1:128284755-128328318 |
| 11318 | Lag3 | NM_008479.2 | chr6:124904358-124911705 | 11415 | Lctl | NM_145815.2 | chr9:64117146-64138118 |
| 11319 | Lage3 | NM_025410.2 | chrX:74352161-74353618 | 11416 | Ldb1 | NM_001113408.1 | chr19:46032600-46045211 |
| 11320 | Lair1 | NM_001113474.1 | chr7:4007072-4063204 | 11417 | Ldb2 | NM_001077398.2 | chr5:44472132-44799746 |
| 11321 | Lalba | NM_010679.1 | chr15:98480399-98482683 | 11418 | Ldb3 | NM_001039071.2 | chr14:34526698-34588681 |
| 11322 | Lama1 | NM_008480.2 | chr17:67697264-67822645 | 11419 | Ldha | NM_001136069.2 | chr7:46847081-46855627 |
| 11323 | Lama2 | NM_008481.2 | chr10:26981284-27616942 | 11420 | Ldhal6b | NM_175349.2 | chr17:5417322-5418767 |
| 11324 | Lama3 | NM_010680.1 | chr18:12334023-12583012 | 11421 | Ldhb | NM_008492.3 | chr6:142490248-142507957 |
| 11325 | Lama4 | NM_010777.1 | chr10:38965514-39110188 | 11422 | Ldhc | NM_013580.4 | chr7:46861262-46878142 |
| 11326 | Lama5 | NM_001081171.2 | chr2:180176372-180225859 | 11423 | Ldhd | NM_027570.3 | chr8:111626270-111630322 |
| 11327 | Lamb1 | NM_008482.2 | chr12:31265293-31329639 | 11424 | Ldlr | NM_001252658.1 | chr9:21723575-21749918 |
| 11328 | Lamb2 | NM_008483.3 | chr9:108479863-108490630 | 11425 | Ldlrad1 | NM_001081272.1 | chr4:107209179-107217914 |
| 11329 | Lamb3 | NM_001277928.1 | chr1:193302242-193343878 | 11426 | Ldlrad2 | NM_001033979.1 | chr4:137570875-137575180 |
| 11330 | Lamc1 | NM_010683.2 | chr1:153122755-153332786 | 11427 | Ldlrad3 | NM_001290784.1 | chr2:101950200-102186460 |
| 11331 | Lamc2 | NM_008485.3 | chr1:153122755-153186447 | 11428 | Ldlrad4 | NM_172631.3 | chr18:6793256-68255549 |
| 11332 | Lamc3 | NM_011836.3 | chr2:31887280-31946535 | 11429 | Ldlrap1 | NM_145554.2 | chr4:134745411-134768004 |
| 11333 | Lamp1 | NM_010684.2 | chr8:13159134-13175338 | 11430 | Ldoc1 | NM_001018087.1 | chrX:61709615-61710950 |
| 11334 | Lamp2 | NM_001017959.2 | chrX:38405048-38456460 | 11431 | Ldoc1l | NM_177630.3 | chr15:84553397-84557823 |
| 11335 | Lamp3 | NM_177356.3 | chr16:19653380-19706365 | 11432 | Leap2 | NM_153069.3 | chr11:53422180-53423136 |
| 11336 | Lamp5 | NM_029612.3 | chr2:136057926-136069971 | 11433 | Lect1 | NM_010701.3 | chr14:79637692-79662183 |
| 11337 | Lamtor1 | NM_026605.3 | chr7:101908836-101911903 | 11434 | Lect2 | NM_010702.2 | chr13:56542459-56548638 |
| 11338 | Lamtor2 | NM_023314.3 | chr3:88418898-88552927 | 11435 | Lef1 | NM_001276402.1 | chr3:131110296-131224357 |
| 11339 | Lamtor3 | NM_019920.2 | chr3:137918554-137928762 | 11436 | Lefty1 | NM_010094.3 | chr1:180935030-180938401 |
| 11340 | Lamtor4 | NM_001081108.2 | chr5:138255481-138259395 | 11437 | Lefty2 | NM_177099.4 | chr1:180893107-180899107 |
| 11341 | Lamtor5 | NM_026774.2 | chr3:107217857-107284081 | 11438 | Lekr1 | NM_001037923.4 | chr3:65666227-65686181 |
| 11342 | Lancl1 | NM_001190984.1 | chr1:67005516-67038834 | 11439 | Lelp1 | NM_027042.1 | chr3:92134993-92142754 |
| 11343 | Lancl2 | NM_133737.2 | chr6:57702454-57739449 | 11440 | Lemd1 | NM_001033250.4 | chr1:132191436-132257382 |
| 11344 | Lancl3 | NM_173414.3 | chrX:9199972-9268085 | 11441 | Lemd2 | NM_146075.2 | chr17:27189599-27204438 |
| 11345 | Lao1 | NM_133892.4 | chr4:118961966-118968910 | 11442 | Lemd3 | NM_001081193.2 | chr10:120923410-120979330 |
| 11346 | Lap3 | NM_024434.6 | chr5:45493378-45512691 | 11443 | Leng1 | NM_020517.4 | chr7:3660106-3665840 |
| 11347 | Laptm4a | NM_008640.2 | chr12:8921306-8938741 | 11444 | Leng8 | NM_027203.3 | chr7:4103955-4108173 |
| 11348 | Laptm4b | NM_033521.3 | chr15:34238025-34284295 | 11445 | Leng8 | NM_172736.3 | chr7:4137055-4148173 |

Fig.21 - 60

| | | | | | | | |
|---|---|---|---|---|---|---|---|
| 11446 | Leng9 | NM_175529.3 | chr7:4148182-4149872 | 11543 | Lipt1 | NM_001037918.3 | chr1:37872205-37876298 |
| 11447 | Leo1 | NM_001099522.1 | chr9:75441523-75466432 | 11544 | Lipt2 | NM_026010.2 | chr7:100159276-100160931 |
| 11448 | Lep | NM_008493.3 | chr6:29060220-29073876 | 11545 | Litaf | NM_019980.2 | chr16:10959272-10993121 |
| 11449 | Lepr | NM_001122899.1 | chr4:101717406-101813667 | 11546 | Lix1 | NM_025681.2 | chr17:17402685-17459388 |
| 11450 | Lepre1 | NM_001042411.1 | chr4:11923828-11924897 | 11547 | Lix1l | NM_001163170.1 | chr3:96601132-96625352 |
| 11451 | Leprel1 | NM_173379.2 | chr16:25960322-26105784 | 11548 | Lkaaear1 | NM_199023.3 | chr2:181696794-181698442 |
| 11452 | Leprel2 | NM_013534.4 | chr6:124841094-124857687 | 11549 | Lig1 | NM_001159404.1 | chr11:60699689-60714188 |
| 11453 | Leprel4 | NM_176820.2 | chr11:100408749-100414819 | 11550 | Lig2 | NM_001252532.1 | chr11:115824057-115855780 |
| 11454 | Leprot | NM_175036.4 | chr4:101647782-101659358 | 11551 | Liph | NM_025431.2 | chr10:120227059-120232070 |
| 11455 | Leprotl1 | NM_026078.2 | chr8:34135571-34146739 | 11552 | Lman1 | NM_001172062.1 | chr18:65983686-66002635 |
| 11456 | Letm1 | NM_019694.1 | chr5:33741351-33782704 | 11553 | Lman1l | NM_199222.3 | chr9:57607032-57620774 |
| 11457 | Letm2 | NM_173012.3 | chr8:25578489-25597487 | 11554 | Lman2 | NM_025828.3 | chr13:55343832-55362783 |
| 11458 | Letmd1 | NM_134093.2 | chr15:100469033-100479252 | 11555 | Lman2l | NM_001013374.2 | chr1:36423185-36445271 |
| 11459 | Lfng | NM_008494.3 | chr5:140607340-140615545 | 11556 | Lmbr1 | NM_020295.3 | chr5:29229801-29378390 |
| 11460 | Lgals1 | NM_008495.2 | chr15:78926724-78930465 | 11557 | Lmbr1l | NM_029098.3 | chr15:98903920-98918098 |
| 11461 | Lgals12 | NM_019516.3 | chr19:7596680-7607176 | 11558 | Lmbrd1 | NM_026719.2 | chr1:24678543-24766301 |
| 11462 | Lgals2 | NM_025622.3 | chr15:78830859-78855529 | 11559 | Lmbrd2 | NM_177178.3 | chr15:9140569-9197450 |
| 11463 | Lgals3 | NM_001145953.1 | chr14:47373859-47386167 | 11560 | Lmcd1 | NM_144799.2 | chr6:112273757-112330423 |
| 11464 | Lgals3bp | NM_011150.2 | chr11:118392751-118401931 | 11561 | Lmf1 | NM_029624.4 | chr17:25579173-25662826 |
| 11465 | Lgals4 | NM_010706.2 | chr7:28833793-28841703 | 11562 | Lmf2 | NM_178919.4 | chr15:89351003-89355659 |
| 11466 | Lgals6 | NM_010707.2 | chr7:28834181-28841633 | 11563 | Lmln | NM_172823.2 | chr16:33062520-33125659 |
| 11467 | Lgals7 | NM_008496.4 | chr7:28864385-28866284 | 11564 | Lmna | NM_001002011.3 | chr3:88481147-88503352 |
| 11468 | Lgals8 | NM_001199043.1 | chr13:12439414-12461738 | 11565 | Lmnb1 | NM_010721.2 | chr18:56707812-56755424 |
| 11469 | Lgals9 | NM_001159301.1 | chr11:78962978-78984924 | 11566 | Lmnb2 | NM_010722.5 | chr10:80901362-80918245 |
| 11470 | Lgalsl | NM_173752.4 | chr11:20823354-20831108 | 11567 | Lmo1 | NM_057173.3 | chr7:109138864-109170519 |
| 11471 | Lgi1 | NM_020278.2 | chr19:38264781-38308939 | 11568 | Lmo2 | NM_001142335.1 | chr2:103970286-103981878 |
| 11472 | Lgi2 | NM_144945.3 | chr5:52533516-52566306 | 11569 | Lmo3 | NM_207222.2 | chr6:138364480-138581968 |
| 11473 | Lgi3 | NM_145219.4 | chr14:70530820-70538324 | 11570 | Lmo4 | NM_001161769.1 | chr3:144188529-144202396 |
| 11474 | Lgi4 | NM_144556.2 | chr7:31059934-31070935 | 11571 | Lmo7 | NM_201529.2 | chr14:101729927-101934693 |
| 11475 | Lgmn | NM_011175.2 | chr12:102394097-102439697 | 11572 | Lmod1 | NM_053106.2 | chr1:135324812-135368065 |
| 11476 | Lgr4 | NM_172671.2 | chr2:109917646-110014257 | 11573 | Lmod2 | NM_053098.2 | chr6:24597770-24605414 |
| 11477 | Lgr5 | NM_010195.2 | chr10:115450313-115587780 | 11574 | Lmod3 | NM_001081157.1 | chr6:97238527-97252780 |
| 11478 | Lgr6 | NM_001033409.3 | chr1:134986352-135105276 | 11575 | Lmtk2 | NM_001081109.1 | chr5:144100435-144188204 |
| 11479 | Lgsn | NM_153601.1 | chr1:31176434-31204725 | 11576 | Lmtk3 | NM_001005511.3 | chr7:45783946-45804142 |
| 11480 | Lhb | NM_008497.2 | chr7:45420945-45421854 | 11577 | Lmx1a | NM_033652.5 | chr1:167689657-167848733 |
| 11481 | Lhcgr | NM_013582.2 | chr17:88741548-88791976 | 11578 | Lmx1b | NM_010725.2 | chr2:33564535-33640611 |
| 11482 | Lhfp | NM_175386.3 | chr3:53041546-53261679 | 11579 | Lnp | NM_001110209.1 | chr2:74514836-74578948 |
| 11483 | Lhfpl1 | NM_178358.3 | chrX:145290358-145348894 | 11580 | Lnpep | NM_172827.3 | chr17:17522722-17624489 |
| 11484 | Lhfpl2 | NM_172589.2 | chr13:94079775-94195409 | 11581 | Lnx1 | NM_001159577.1 | chr5:74597103-74702903 |
| 11485 | Lhfpl3 | NM_001081231.2 | chr5:22746192-23275597 | 11582 | Lnx2 | NM_080795.4 | chr5:147016654-147076572 |
| 11486 | Lhfpl4 | NM_177763.3 | chr6:113168086-113195384 | 11583 | LOC100038947 | NM_001173459.2 | chr3:15795146-15848487 |
| 11487 | Lhfpl5 | NM_026571.2 | chr17:28575718-28583593 | 11584 | LOC100040786 | NM_001160129.1 | chrY:54185856-66742170 |
| 11488 | Lhpp | NM_029609.1 | chr7:132610642-132706419 | 11585 | LOC100043315 | NR_015482.1 | chr5:95097621-95149318 |
| 11489 | Lhx1 | NM_008498.2 | chr11:84519378-84525534 | 11586 | LOC100048896 | NM_001199333.1 | chr4:61670177-61674094 |
| 11490 | Lhx1os | NR_038057.1 | chr11:84525659-84535831 | 11587 | LOC100502896 | NM_001277512.1 | chr4:73650909-73657292 |
| 11491 | Lhx2 | NM_001290646.1 | chr2:38339280-38369737 | 11588 | LOC100503280 | NM_001251890.1 | chrX:74966843-74969125 |
| 11492 | Lhx3 | NM_001039653.2 | chr2:26200211-26206575 | 11589 | LOC100503496 | NR_040680.1 | chr11:109440077-109453359 |
| 11493 | Lhx4 | NM_010712.2 | chr1:155701693-155742027 | 11590 | LOC100503676 | NR_103491.1 | chr5:84913334-84922915 |
| 11494 | Lhx5 | NM_008499.5 | chr5:120431885-120441457 | 11591 | LOC100504039 | NR_102724.1 | chrX:53686526-53691325 |
| 11495 | Lhx6 | NM_001083125.1 | chr2:36081952-36105468 | 11592 | LOC100504608 | NM_001205036.1 | chr10:127037904-127041394 |
| 11496 | Lhx8 | NM_010713.2 | chr3:154306293-154430560 | 11593 | LOC100504703 | NR_040660.1 | chr10:127070480-127071101 |
| 11497 | Lhx9 | NM_001025565.2 | chr1:138825185-138842444 | 11594 | LOC100505025 | NR_105062.1 | chr7:73310379-73315193 |
| 11498 | Lias | NM_024475.5 | chr5:65391496-65410423 | 11595 | LOC100508615 | NM_001270812.1 | chr14:6259746-6287250 |
| 11499 | Lif | NM_001039537.2 | chr11:4266795-4272514 | 11596 | LOC100861978 | NM_001267963.1 | chr4:168636-22237 |
| 11500 | Lifr | NM_001113385.1 | chr15:7129571-7185343 | 11597 | LOC100862011 | NM_001275531.1 | chr4:73635789-73642163 |
| 11501 | Lig1 | NM_001083188.1 | chr7:13279264-13311427 | 11598 | LOC100862268 | NR_105029.1 | chr3:127161304-127168290 |
| 11502 | Lig3 | NM_001291245.1 | chr11:82781108-82804274 | 11599 | LOC101055769 | NR_105031.1 | chr4:59260050-59269144 |
| 11503 | Lig4 | NM_176953.3 | chr8:9970019-9976323 | 11600 | LOC101055863 | NM_001277487.1 | chr4:73605543-73687560 |
| 11504 | Lilra5 | NM_001081239.2 | chr7:4237753-4243463 | 11601 | LOC101056043 | NR_105032.1 | chr5:110429874-110431955 |
| 11505 | Lilra6 | NM_011090.2 | chr7:3908279-3915501 | 11602 | LOC101056136 | NR_105055.1 | chr14:42254658-42260048 |
| 11506 | Lilrb4 | NM_001291894.1 | chr10:51490897-51496611 | 11603 | LOC101056149 | NR_105041.1 | chr13:34652922-34666774 |
| 11507 | Lim2 | NM_177693.3 | chr7:43430100-43435991 | 11604 | LOC101056236 | NR_105054.1 | chr16:92377070-92382683 |
| 11508 | Lima1 | NM_001113156.1 | chr15:99778487-99875456 | 11605 | LOC101243624 | NM_102297.1 | chr3:132842201-132878596 |
| 11509 | Limch1 | NM_001001980.2 | chr5:66745839-67057159 | 11606 | LOC101669761 | NR_103513.1 | chr16:31986830-31987791 |
| 11510 | Limd1 | NM_013860.2 | chr9:123478700-123521552 | 11607 | LOC102308570 | NM_001286303.1 | chr19:8883877-8890759 |
| 11511 | Limd2 | NM_172397.3 | chr11:106156255-106160142 | 11608 | LOC102631675 | NR_110502.1 | chr7:31152751-31163052 |
| 11512 | Lime1 | NM_026684.2 | chr2:181381234-181383628 | 11609 | LOC102632423 | NR_110507.1 | chr8:118300166-118308719 |
| 11513 | Limk1 | NM_010717.3 | chr5:134656038-134688590 | 11610 | LOC102632430 | NR_110508.1 | chr16:22874982-22894386 |
| 11514 | Limk2 | NM_010563.2 | chr11:3343296-3356141 | 11611 | LOC102633035 | NR_110509.1 | chr9:101342193-101348017 |
| 11515 | Lims1 | NM_001193303.1 | chr10:58394372-58424691 | 11612 | LOC102633315 | NR_110510.1 | chr8:25548672-25556083 |
| 11516 | Lims2 | NM_144862.3 | chr18:31931506-31958619 | 11613 | LOC102634101 | NR_110511.1 | chr10:67005074-67041326 |
| 11517 | Lin28a | NM_145833.1 | chr4:134003329-134018816 | 11614 | LOC102634401 | NR_110447.1 | chr2:74752683-74753742 |
| 11518 | Lin28b | NM_001031772.2 | chr10:45376618-45470201 | 11615 | LOC102634431 | NR_110513.1 | chr9:8644077-8740988 |
| 11519 | Lin37 | NM_001290569.1 | chr7:30555440-30559646 | 11616 | LOC102634705 | NR_110516.1 | chr3:99049823-99053742 |
| 11520 | Lin52 | NM_173756.4 | chr12:84451507-84531533 | 11617 | LOC102635087 | NR_110517.1 | chr9:71168775-71208122 |
| 11521 | Lin54 | NM_001115010.1 | chr5:100442034-100498573 | 11618 | LOC102636514 | NR_110474.1 | chr8:57304413-57320859 |
| 11522 | Lin7a | NM_001033223.2 | chr10:107271830-107425143 | 11619 | LOC106740 | NR_027905.1 | chr17:14947735-14948823 |
| 11523 | Lin7b | NM_011698.1 | chr7:45367890-45370564 | 11620 | LOC171588 | NR_036065.1 | chr2:144465175-144466732 |
| 11524 | Lin7c | NM_011699.1 | chr2:109900936 | 11621 | LOC381967 | NR_103487.1 | chr7:99260480-99267218 |
| 11525 | Lin9 | NM_001083382.2 | chr1:180641149-180690687 | 11622 | LOC666331 | NM_001256318.1 | chr1:101610699-101615956 |
| 11526 | Lincrna-cox2 | NR_110420.1 | chr1:150159042-150164948 | 11623 | Lohi2cr1 | NM_001170479.1 | chr6:134639611-134711184 |
| 11527 | Lingo1 | NM_181074.4 | chr9:56618474-56685253 | 11624 | Lonp1 | NM_028782.2 | chr17:56614297-56626993 |
| 11528 | Lingo2 | NM_001165999.1 | chr4:35706647-36951744 | 11625 | Lonp2 | NM_001168591.1 | chr8:86651568-86716638 |
| 11529 | Lingo3 | NM_001013758.2 | chr10:80832800-80844039 | 11626 | Lonrf1 | NM_001081150.1 | chr8:36216063-36249516 |
| 11530 | Lingo4 | NM_177250.2 | chr3:94399218-94404501 | 11627 | Lonrf2 | NM_001029878.1 | chr1:38794508-38821215 |
| 11531 | Lins | NM_001191001.3 | chr7:66689888-66717256 | 11628 | Lonrf3 | NM_028894.1 | chrX:36328408-36366856 |
| 11532 | Lipa | NM_001111100.1 | chr19:34492315-34527474 | 11629 | Lor | NM_008508.2 | chr3:92080270-92083142 |
| 11533 | Lipc | NM_008280.2 | chr9:70798127-70934808 | 11630 | Lox | NM_001286181.1 | chr18:52516059-52529721 |
| 11534 | Lipe | NM_001039507.2 | chr7:25379526-25390112 | 11631 | Loxhd1 | NM_172834.2 | chr18:77281957-77442257 |
| 11535 | Lipf | NM_026334.3 | chr19:33961247-33976813 | 11632 | Loxl1 | NM_010729.3 | chr9:58287722-58313212 |
| 11536 | Lipg | NM_010720.3 | chr18:74939321-74961263 | 11633 | Loxl2 | NM_033325.2 | chr14:69609475-69695834 |
| 11537 | Liph | NM_001083984.1 | chr16:21953817-21995642 | 11634 | Loxl3 | NM_013586.4 | chr6:83034223-83052564 |
| 11538 | Lipi | NM_001252513.1 | chr16:75540613-75586061 | 11635 | Loxl4 | NM_001164311.1 | chr9:42592278-42612806 |
| 11539 | Lipk | NM_001205349.1 | chr19:34008253-34047903 | 11636 | Lpar1 | NM_001290486.1 | chr4:58435251-58499403 |
| 11540 | Lipm | NM_023903.1 | chr19:33800400-34122687 | 11637 | Lpar2 | NM_020028.3 | chr8:69822564-69831102 |
| 11541 | Lipn | NM_027340.2 | chr19:34067357-34084918 | 11638 | Lpar3 | NM_022983.4 | chr3:146220960-146286214 |
| 11542 | Lipo1 | NM_001013770.2 | chr19:33555280-33590311 | 11639 | Lpar4 | NM_175271.4 | chrX:106920624-106933899 |

Fig.21 - 61

| | | | | | | | |
|---|---|---|---|---|---|---|---|
| 11640 | Lpar5 | NM_001163268.1 | chr6:125071276-125082472 | 11737 | Lrrc55 | NM_001033346.2 | chr2:85188070-85198699 |
| 11641 | Lpar6 | NM_175116.4 | chr14:73237890-73240358 | 11738 | Lrrc56 | NM_001172064.1 | chr7:141194129-141210055 |
| 11642 | Lpcat1 | NM_145376.5 | chr13:73467382-73514538 | 11739 | Lrrc57 | NM_001159609.1 | chr2:120604237-120609508 |
| 11643 | Lpcat2 | NM_173014.1 | chr8:92855349-92919279 | 11740 | Lrrc58 | NM_177093.3 | chr16:37868399-37888857 |
| 11644 | Lpcat2b | NM_027599.3 | chr5:107431548-107435039 | 11741 | Lrrc59 | NM_133807.1 | chr11:94629823-94645216 |
| 11645 | Lpcat3 | NM_145130.2 | chr6:124663103-124704716 | 11742 | Lrrc6 | NM_019457.2 | chr15:66379857-66500910 |
| 11646 | Lpcat4 | NM_207206.2 | chr2:112239840-112247111 | 11743 | Lrrc61 | NM_001110160.1 | chr6:48554798-48570722 |
| 11647 | Lpgat1 | NM_001134829.1 | chr1:191718394-191784257 | 11744 | Lrrc63 | NM_027581.1 | chr14:75084302-75130883 |
| 11648 | Lphn1 | NM_181039.2 | chr8:83900097-83941954 | 11745 | Lrrc66 | NM_153568.1 | chr5:73606641-73632421 |
| 11649 | Lphn2 | NM_001081298.1 | chr3:148815585-148954635 | 11746 | Lrrc69 | NM_028499.2 | chr4:14665753-14796052 |
| 11650 | Lphn3 | NM_198702.2 | chr5:81021592-81795730 | 11747 | Lrrc7 | NM_001081358.2 | chr3:158082894-158562221 |
| 11651 | Lpin1 | NM_001130412.1 | chr12:16535648-16589770 | 11748 | Lrrc71 | NM_028971.1 | chr3:87736922-87748623 |
| 11652 | Lpin2 | NM_001164885.1 | chr17:71204653-71249818 | 11749 | Lrrc72 | NM_001177877.1 | chr12:36209562-36253358 |
| 11653 | Lpin3 | NM_001199118.1 | chr2:160888167-160906000 | 11750 | Lrrc73 | NM_001111142.1 | chr17:46254164-46257316 |
| 11654 | Lpl | NM_008509.2 | chr8:68880514-68906932 | 11751 | Lrrc74 | NM_001195767.1 | chr12:86734368-86763795 |
| 11655 | Lpo | NM_080420.2 | chr11:87806427-87826114 | 11752 | Lrrc75a | NM_198861.1 | chr11:62604883-62648523 |
| 11656 | Lpp | NM_001145952.1 | chr16:24448090-24992578 | 11753 | Lrrc75b | NM_198860.2 | chr10:75560124-75560330 |
| 11657 | Lpxn | NM_134152.3 | chr19:12798608-12833808 | 11754 | Lrrc8a | NM_177725.4 | chr2:30237768-30263790 |
| 11658 | Lrat | NM_023624.4 | chr3:82892581-82903974 | 11755 | Lrrc8b | NM_001035550.2 | chr5:105419774-105486189 |
| 11659 | Lrba | NM_001077687.1 | chr3:86224689-86746710 | 11756 | Lrrc8c | NM_133897.2 | chr5:105519470-105608954 |
| 11660 | Lrch1 | NM_001033439.3 | chr14:74754672-74947877 | 11757 | Lrrc8d | NM_001122768.1 | chr5:105699968-105815215 |
| 11661 | Lrch2 | NM_001081173.1 | chrX:147471693-147554081 | 11758 | Lrrc8e | NM_028175.2 | chr8:4226826-4237470 |
| 11662 | Lrch3 | NM_001033439.1 | chr16:32914099-33016029 | 11759 | Lrrc9 | NM_001142728.1 | chr12:72441866-72510565 |
| 11663 | Lrch4 | NM_001168652.1 | chr5:137629122-137641699 | 11760 | Lrrcc1 | NM_001163579.1 | chr3:14533787-14568303 |
| 11664 | Lrcol1 | NM_001310709.1 | chr5:110344507-110356094 | 11761 | Lrrd1 | NM_172879.3 | chr5:3845172-3866596 |
| 11665 | Lrfn1 | NM_001141921.1 | chr7:28452237-28467548 | 11762 | Lrrfip1 | NM_001111311.1 | chr1:91053443-91117322 |
| 11666 | Lrfn2 | NM_027452.3 | chr17:48932581-49097590 | 11763 | Lrrfip2 | NM_001164838.1 | chr9:111118110-111225668 |
| 11667 | Lrfn3 | NM_175478.2 | chr7:30355513-30362772 | 11764 | Lrriq1 | NM_001163559.1 | chr10:103063197-103236322 |
| 11668 | Lrfn4 | NM_153188.3 | chr19:4615667 | 11765 | Lrriq3 | NM_028938.2 | chr3:155093433-155194276 |
| 11669 | Lrfn5 | NM_178714.5 | chr12:61523166-61845258 | 11766 | Lrriq4 | NM_001290510.1 | chr3:30647885-30672431 |
| 11670 | Lrg1 | NM_029796.2 | chr17:56119679-56121946 | 11767 | Lrrk1 | NM_146191.3 | chr7:66258746-66388341 |
| 11671 | Lrguk | NM_028886.1 | chr6:34029447-34134034 | 11768 | Lrrk2 | NM_025730.3 | chr15:91673223-91816124 |
| 11672 | Lrif1 | NM_001039478.1 | chr3:106684986-106736576 | 11769 | Lrrn1 | NM_008516.4 | chr6:107529725-107570228 |
| 11673 | Lrig1 | NM_008377.2 | chr6:94604528-94700145 | 11770 | Lrrn2 | NM_010732.4 | chr1:132880354-132940005 |
| 11674 | Lrig2 | NM_001025067.2 | chr3:104453982-104511918 | 11771 | Lrrn3 | NM_001271708.1 | chr12:41451667-41486057 |
| 11675 | Lrig3 | NM_177152.5 | chr10:125966218-126015359 | 11772 | Lrrn4 | NM_177303.4 | chr2:132868515-132880862 |
| 11676 | Lrit1 | NM_146245.3 | chr14:35064829-37064938 | 11773 | Lrrn4cl | NM_001013019.2 | chr19:8850784-8853909 |
| 11677 | Lrit2 | NM_173418.3 | chr14:37068048-37073735 | 11774 | Lrrtm1 | NM_028880.3 | chr6:77242716-77245517 |
| 11678 | Lrit3 | NM_001287224.1 | chr3:129784030-129804030 | 11775 | Lrrtm2 | NM_178005.4 | chr18:35209005-35215024 |
| 11679 | Lrmp | NM_001281980.1 | chr6:145115635-145174928 | 11776 | Lrrtm3 | NM_178678.4 | chr10:63928496-64090255 |
| 11680 | Lrp1 | NM_008512.2 | chr10:127538157-127621148 | 11777 | Lrrtm4 | NM_001134743.1 | chr6:80018876-80810143 |
| 11681 | Lrp10 | NM_022913.3 | chr14:54464146-54470291 | 11778 | Lrsam1 | NM_199302.2 | chr2:32925214-32961755 |
| 11682 | Lrp11 | NM_172784.3 | chr10:7589799-7625477 | 11779 | Lrtm1 | NM_176920.4 | chr14:29018207-29033642 |
| 11683 | Lrp12 | NM_172814.3 | chr15:39570802-39943757 | 11780 | Lrtm2 | NM_001172207.1 | chr6:119315132-119329204 |
| 11684 | Lrp1b | NM_053011.1 | chr2:40596772-42653598 | 11781 | Lrwd1 | NM_027891.4 | chr5:136123065-136136074 |
| 11685 | Lrp2 | NM_001081088.1 | chr2:69424334-69586067 | 11782 | Lsamp | NM_175548.3 | chr16:41533341-42146213 |
| 11686 | Lrp2bp | NM_026278.3 | chr8:46010601-46029476 | 11783 | Lsg1 | NM_178069.5 | chr16:30561368-30587589 |
| 11687 | Lrp3 | NM_001024707.2 | chr7:35200877-35215345 | 11784 | Lsm1 | NM_026032.1 | chr8:25785590-25803975 |
| 11688 | Lrp4 | NM_001145857.1 | chr2:91457530-91479287 | 11785 | Lsm10 | NM_001163266.1 | chr4:126096652-126098584 |
| 11689 | Lrp5 | NM_008514.3 | chr19:3584824-3686564 | 11786 | Lsm11 | NM_028185.2 | chr11:45928268-45944935 |
| 11690 | Lrp6 | NM_008514.4 | chr6:134446477-134566913 | 11787 | Lsm12 | NM_172947.3 | chr11:102185488-102185256 |
| 11691 | Lrp8 | NM_001080926.1 | chr4:107802258-107876840 | 11788 | Lsm14a | NM_025948.2 | chr7:34344719-34389540 |
| 11692 | Lrpap1 | NM_013587.2 | chr5:35091505-35105697 | 11789 | Lsm14b | NM_177227.4 | chr2:180024986-180035461 |
| 11693 | Lrppr | NM_028233.2 | chr17:84705246-84790786 | 11790 | Lsm2 | NM_001110101.2 | chr17:34981853-34985893 |
| 11694 | Lrr1 | NM_001081406.1 | chr12:69188513-69179010 | 11791 | Lsm3 | NM_026309.2 | chr6:91516034-91522620 |
| 11695 | Lrrc1 | NM_001146048.1 | chr9:77430822-77544852 | 11792 | Lsm4 | NM_015816.4 | chr8:70673230-70678752 |
| 11696 | Lrrc10 | NM_146242.2 | chr10:117045340-117046768 | 11793 | Lsm5 | NM_025520.3 | chr6:56701062-56704699 |
| 11697 | Lrrc10b | NM_001111140.2 | chr19:10455370-10457447 | 11794 | Lsm6 | NM_001191004.1 | chr8:78804867-78821152 |
| 11698 | Lrrc14 | NM_145471.2 | chr15:76710739-76715091 | 11795 | Lsm7 | NM_025349.2 | chr10:80852824-80855209 |
| 11699 | Lrrc14b | NM_001033042.3 | chr13:74359581-74364000 | 11796 | Lsm8 | NM_133931.1 | chr6:18848634-18854052 |
| 11700 | Lrrc15 | NM_001033437.2 | chr16:30269301-30283254 | 11797 | Lsmem1 | NM_001033437.2 | chr12:40176385-40199315 |
| 11701 | Lrrc16a | NM_026825.3 | chr13:24012483-24280790 | 11798 | Lsp1 | NM_001136971.2 | chr7:142460811-142494868 |
| 11702 | Lrrc16b | NM_001024645.1 | chr14:35491092-55508264 | 11799 | Lsr | NM_001164184.1 | chr7:30957769-30973469 |
| 11703 | Lrrc17 | NM_028977.1 | chr5:21543526-21575902 | 11800 | Lss | NM_146006.2 | chr10:76531604-76557139 |
| 11704 | Lrrc18 | NM_001146021.1 | chr14:32991381-33009398 | 11801 | Lst1 | NM_010734.2 | chr17:35185094-35188440 |
| 11705 | Lrrc19 | NM_175305.4 | chr4:94636659-94650144 | 11802 | Lta | NM_010735.2 | chr17:35203164-35205351 |
| 11706 | Lrrc2 | NM_028838.2 | chr9:110951544-110984064 | 11803 | Lta4h | NM_008517.2 | chr10:93453395-93484896 |
| 11707 | Lrrc20 | NM_153542.1 | chr10:61475832-61582228 | 11804 | Ltb | NM_008518.2 | chr17:35194506-35196305 |
| 11708 | Lrrc23 | NM_001302555.1 | chr6:124769869-124780341 | 11805 | Ltb4r1 | NM_008519.2 | chr14:55765961-55768491 |
| 11709 | Lrrc24 | NM_198119.2 | chr15:76715275-76722173 | 11806 | Ltb4r2 | NM_020490.2 | chr14:55761427-55763229 |
| 11710 | Lrrc25 | NM_153074.3 | chr8:70616843-70620850 | 11807 | Ltbp1 | NM_019919.3 | chr17:75005528-75392967 |
| 11711 | Lrrc26 | NM_146117.2 | chr2:25289910-25291193 | 11808 | Ltbp2 | NM_013589.3 | chr12:84783211-84876495 |
| 11712 | Lrrc27 | NM_001143755.1 | chr13:139213274-139229012 | 11809 | Ltbp3 | NM_008520.2 | chr19:5740909-5758532 |
| 11713 | Lrrc28 | NM_027321.3 | chr7:67594398-67645236 | 11810 | Ltbp4 | NM_001113549.1 | chr7:27305140-27333648 |
| 11714 | Lrrc29 | NM_177449.3 | chr8:105312339-105326276 | 11811 | Ltbr | NM_010736.3 | chr6:125306570-125313870 |
| 11715 | Lrrc3 | NM_145152.4 | chr10:77897575-77902536 | 11812 | Ltc4s | NM_008521.2 | chr11:50236460-50238532 |
| 11716 | Lrrc30 | NM_001033340.3 | chr17:30130964-67632723 | 11813 | Ltf | NM_008523.2 | chr9:111019291-111042766 |
| 11717 | Lrrc32 | NM_001113379.1 | chr7:98494221-98501830 | 11814 | Ltk | NM_008523.2 | chr2:119751325-119758525 |
| 11718 | Lrrc34 | NM_027941.1 | chr3:30624926-30647818 | 11815 | Ltn1 | NM_001081068.1 | chr16:87376650-87432606 |
| 11719 | Lrrc36 | NM_001033371.3 | chr8:105427639-105464096 | 11816 | Ltv1 | NM_181470.4 | chr10:13178637-13193137 |
| 11720 | Lrrc38 | NM_001162983.1 | chr4:143349749-143371028 | 11817 | Luc7l | NM_025881.3 | chr17:26252909-26280730 |
| 11721 | Lrrc39 | NM_001081068.1 | chr3:116562972-116573112 | 11818 | Luc7l2 | NM_001170848.1 | chr6:38551443-38609470 |
| 11722 | Lrrc3b | NM_146052.4 | chr14:15357515-15438987 | 11819 | Luc7l3 | NM_026313.1 | chr11:94291138-94311911 |
| 11723 | Lrrc4 | NM_138682.2 | chr6:28828125-28831747 | 11820 | Lum | NM_008524.2 | chr10:97565500-97572703 |
| 11724 | Lrrc40 | NM_001289524.1 | chr3:158036681-158067090 | 11821 | Lurap1 | NM_026547.1 | chr4:116136727-116144616 |
| 11725 | Lrrc41 | NM_153521.2 | chr4:116075268-116097109 | 11822 | Lurap1l | NM_026821.5 | chr4:80910685-80984301 |
| 11726 | Lrrc42 | NM_029985.2 | chr4:107253513-107253533 | 11823 | Luzp1 | NM_024452.2 | chr4:136469760-136549318 |
| 11727 | Lrrc43 | NM_001033461.3 | chr5:123489324-123508205 | 11824 | Luzp2 | NM_178705.5 | chr7:54835244-55268888 |
| 11728 | Lrrc45 | NM_153545.2 | chr11:120713952-120721127 | 11825 | Luzp4 | NM_001114383.1 | chrX:148882575-148924139 |
| 11729 | Lrrc46 | NM_027026.2 | chr11:97041369 | 11826 | Lxn | NM_016753.4 | chr3:67457998-67463907 |
| 11730 | Lrrc47 | NM_201226.1 | chr4:154011802-154021512 | 11827 | Ly6a | NM_001271416.1 | chr15:74994876-74998031 |
| 11731 | Lrrc48 | NM_029044.2 | chr11:60353379-60394333 | 11828 | Ly6c1 | NM_001252055.1 | chr15:75045014-75048837 |
| 11732 | Lrrc4b | NM_001146046.1 | chr9:30587234-60658134 | 11829 | Ly6c2 | NM_001099217.1 | chr15:75108160-75111949 |
| 11733 | Lrrc4b | NM_198250.1 | chr7:44442486-44463344 | 11830 | Ly6d | NM_010742.1 | chr15:74762055-74763567 |
| 11734 | Lrrc4c | NM_001289742.1 | chr6:96318168-97631664 | 11831 | Ly6e | NM_001164036.1 | chr15:74955070-74959605 |
| 11735 | Lrrc51 | NM_001162973.1 | chr7:101912988-101933857 | 11832 | Ly6f | NM_008530.2 | chr15:75268420-75272234 |
| 11736 | Lrrc52 | NM_001013382.2 | chr1:167448674-167466780 | 11833 | Ly6g5b | NM_148939.2 | chr17:35113945-35115400 |

Fig.21 - 62

| | | | | | | | |
|---|---|---|---|---|---|---|---|
| 11834 | Ly6g5c | NM_148947.1 | chr17:35108299-35111953 | 11931 | Maged2 | NM_001199246.1 | chrX:150806420-150813703 |
| 11835 | Ly6g6c | NM_023463.3 | chr17:35067324-35070048 | 11932 | Magee1 | NM_053201.4 | chrX:105120377-105123961 |
| 11836 | Ly6g6d | NM_033478.2 | chr17:35071347-35074464 | 11933 | Magee2 | NM_053206.2 | chrX:104854951-104857267 |
| 11837 | Ly6g6e | NM_027366.1 | chr17:35076941-35078804 | 11934 | Magch1 | NM_023788.3 | chrX:153036165-153037563 |
| 11838 | Ly6g6f | NM_001163192.1 | chr17:35080537-35085595 | 11935 | Magel2 | NM_013779.2 | chr7:62376978-62391640 |
| 11839 | Ly6h | NM_001135688.1 | chr15:75564744-75566856 | 11936 | Magi1 | NM_001029850.4 | chr6:93675452-94283917 |
| 11840 | Ly6i | NM_020498.2 | chr15:74979811-74983430 | 11937 | Magi2 | NM_001170745.1 | chr5:19907517-20704792 |
| 11841 | Ly6k | NM_029627.2 | chr15:74796873-74799968 | 11938 | Magi3 | NM_001159354.1 | chr3:104013264-104220406 |
| 11842 | Ly75 | NM_013825.3 | chr2:60293759-60383231 | 11939 | Magix | NM_018832.2 | chrX:7673166-7681089 |
| 11843 | Ly86 | NM_010745.2 | chr13:37345344-37419036 | 11940 | Magoh | NM_001282737.1 | chr4:107879754-107887424 |
| 11844 | Ly9 | NM_001277968.1 | chr1:171588612-171607410 | 11941 | Magohb | NM_025584.2 | chr6:131284888-131293244 |
| 11845 | Ly96 | NM_001159711.1 | chr1:16688455-16709605 | 11942 | Magt1 | NM_001190409.1 | chrX:105968084-106011899 |
| 11846 | Lyar | NM_025281.3 | chr5:38220481-38234306 | 11943 | Mak | NM_001145802.1 | chr13:41025119-41079706 |
| 11847 | Lyg1 | NM_027111.3 | chr1:37946737-37957759 | 11944 | Mak16 | NM_026453.3 | chr8:31159467-31168724 |
| 11848 | Lyg2 | NM_001033427.3 | chr1:37905922-37916493 | 11945 | Mal | NM_001171387.1 | chr2:127633225-127656695 |
| 11849 | Lyl1 | NM_008535.2 | chr8:84701456-84704716 | 11946 | Mal2 | NM_178920.4 | chr15:54571365-54602846 |
| 11850 | Lyn | NM_001111096.1 | chr4:3678120-3791612 | 11947 | Malat1 | NR_002847.2 | chr19:5795689-5802671 |
| 11851 | Lynx1 | NM_011838.4 | chr15:74747855-74752979 | 11948 | Mall | NM_145532.3 | chr2:127704189-127729897 |
| 11852 | Lypd1 | NM_145100.4 | chr1:125887621-125912214 | 11949 | Malsu1 | NM_029353.1 | chr6:49073794-49084717 |
| 11853 | Lypd2 | NM_026671.1 | chr15:74732251-74734313 | 11950 | Malt1 | NM_172833.2 | chr18:65430996-65478792 |
| 11854 | Lypd3 | NM_133743.1 | chr7:24636569-24641118 | 11951 | Mamdc2 | NM_148657.3 | chr19:23302608-23448322 |
| 11855 | Lypd4 | NM_182785.3 | chr7:24864619-24869691 | 11952 | Mamdc4 | NM_001081199.1 | chr2:25563114-25571316 |
| 11856 | Lypd5 | NM_029806.1 | chr7:24349223-24353833 | 11953 | Maml1 | NM_175334.3 | chr11:50255634-50292338 |
| 11857 | Lypd6 | NM_177139.5 | chr2:50066428-50193569 | 11954 | Maml2 | NM_001013811.3 | chr9:13619988-13709533 |
| 11858 | Lypd6b | NM_027990.3 | chr2:49787685-49948846 | 11955 | Maml3 | NM_001004176.2 | chr3:51687612-52109006 |
| 11859 | Lypd8 | NM_001083884.1 | chr11:58379031-58390541 | 11956 | Mamld1 | NM_001081354.2 | chrX:71050255-71154717 |
| 11860 | Lypla1 | NM_008866.2 | chr1:4807892-4846735 | 11957 | Mamstr | NM_172418.2 | chr7:45639976-45645768 |
| 11861 | Lypla2 | NM_011942.1 | chr4:135968224-135972594 | 11958 | Man1a | NM_008548.4 | chr10:53906032-54075796 |
| 11862 | Lypla1l | NM_146106.2 | chr1:186087731-186117310 | 11959 | Man1a2 | NM_010763.2 | chr3:100562204-100685473 |
| 11863 | Lyrm1 | NM_001285959.1 | chr7:119889860-119916756 | 11960 | Man1b1 | NM_001029983.2 | chr2:25332742-25352213 |
| 11864 | Lyrm2 | NM_175364.4 | chr4:32800258-32802254 | 11961 | Man1c1 | NM_207373.3 | chr4:134561889-134704290 |
| 11865 | Lyrm4 | NM_201358.2 | chr13:35978796-36177357 | 11962 | Man2a1 | NM_008549.2 | chr17:64601648-64755110 |
| 11866 | Lyrm5 | NM_001163628.1 | chr6:145211133-145216542 | 11963 | Man2a2 | NM_172903.4 | chr7:80349096-80371375 |
| 11867 | Lyrm7 | NM_029327.3 | chr11:54839288-54860591 | 11964 | Man2b1 | NM_010764.2 | chr8:85083268-85098739 |
| 11868 | Lyrm7os | NR_040284.1 | chr11:54819918-54824967 | 11965 | Man2b2 | NM_008550.2 | chr5:36806812-36830649 |
| 11869 | Lyrm9 | NM_001076681.2 | chr11:78826594-78843899 | 11966 | Man2c1 | NM_028636.2 | chr9:57130776-57142210 |
| 11870 | Lysmd1 | NM_153121.2 | chr3:95134087-95139525 | 11967 | Man2c1os | NR_102289.1 | chr9:57179981-57131290 |
| 11871 | Lysmd2 | NM_027309.2 | chr9:75625731-75637773 | 11968 | Manba | NM_027288.3 | chr3:135485610-135571403 |
| 11872 | Lysmd3 | NM_030257.1 | chr13:81657805-81671896 | 11969 | Manbal | NM_026968.3 | chr2:157367593-157396763 |
| 11873 | Lysmd4 | NM_001191061.1 | chr7:67222615-67228468 | 11970 | Manea | NM_172865.2 | chr4:26324505-26346652 |
| 11874 | Lyst | NM_010748.2 | chr13:13590408-13777440 | 11971 | Maneal | NM_001007673.2 | chr4:124855238-124862171 |
| 11875 | Lyve1 | NM_053247.4 | chr7:110830606-110862953 | 11972 | Manf | NM_029103.3 | chr9:106887414-106891938 |
| 11876 | Lyz1 | NM_013590.4 | chr10:117287794-117292868 | 11973 | Manr | NR_110437.1 | chr3:29891016-29924191 |
| 11877 | Lyz2 | NM_017372.3 | chr10:117277540-117282272 | 11974 | Mansc1 | NM_026345.4 | chr6:134609206-134632488 |
| 11878 | Lyzl1 | NM_026092.3 | chr18:4165831-4182236 | 11975 | Mansc4 | NM_001034903.3 | chr6:147075061-147087032 |
| 11879 | Lyzl4 | NM_026915.2 | chr9:121577842-121641566 | 11976 | Maoa | NM_173740.3 | chrX:16619697-16687812 |
| 11880 | Lyzl4os | NR_040740.1 | chr9:121592013-121614255 | 11977 | Maob | NM_172778.2 | chrX:16709280-16817366 |
| 11881 | Lyzl6 | NM_027083.1 | chr11:103631074-103638874 | 11978 | Map10 | NM_028908.3 | chr8:125669817-125673365 |
| 11882 | Lzic | NM_026963.5 | chr4:149485332-149496667 | 11979 | Map1a | NM_001173506.1 | chr2:121295453-121310832 |
| 11883 | Lzrfl1 | NM_033247.2 | chr9:123697592-123717557 | 11980 | Map1b | NM_008634.1 | chr13:99421463-99516602 |
| 11884 | Lztr1 | NM_025808.3 | chr16:17508970-17526330 | 11981 | Map1lc3a | NM_025735.3 | chr2:155276363-155278073 |
| 11885 | Lzts1 | NM_199364.2 | chr8:69135502-69140953 | 11982 | Map1lc3b | NM_026160.4 | chr8:121590467-121598047 |
| 11886 | Lzts2 | NM_001130525.1 | chr19:45015269-45027104 | 11983 | Map1s | NM_173013.3 | chr8:70905973-70917529 |
| 11887 | Lzts3 | NM_001291027.1 | chr2:130632764-130642844 | 11984 | Map2 | NM_001039934 | chr1:66175328-66442583 |
| 11888 | M1ap | NM_030079.2 | chr6:82846921-83030309 | 11985 | Map2k1 | NM_008927 | chr9:64185792-64253605 |
| 11889 | M6pr | NM_010749.6 | chr6:122309009-122317677 | 11986 | Map2k2 | NM_023138.1 | chr10:81105946-81124687 |
| 11890 | Maats1 | NM_001081025.1 | chr16:38297753-38341860 | 11987 | Map2k3 | NM_008928.4 | chr11:60932056-60952803 |
| 11891 | Mab21l1 | NM_010750.3 | chr3:55782509-55785287 | 11988 | Map2k3os | NR_027806.1 | chr11:60920940-60931887 |
| 11892 | Mab21l2 | NM_011839.3 | chr3:86545580-86548283 | 11989 | Map2k4 | NM_009157.5 | chr11:65688243-65788297 |
| 11893 | Mab21l3 | NM_172295.4 | chr3:101813079-101836223 | 11990 | Map2k5 | NM_011840.2 | chr9:63163769-63377852 |
| 11894 | Macc1 | NM_001163336.1 | chr11:19443409-19466932 | 11991 | Map2k6 | NM_011943.2 | chr11:110399121-110513637 |
| 11895 | Macf1 | NM_001199136.1 | chr4:123394632-123684360 | 11992 | Map2k7 | NM_001042957.2 | chr8:4238739-4247837 |
| 11896 | Macrod1 | NM_134147.4 | chr19:7056767-7198062 | 11993 | Map3k1 | NM_011945.2 | chr13:111746434-111808983 |
| 11897 | Macrod2 | NM_001038023 | chr2:140395429-142390050 | 11994 | Map3k10 | NM_001290528.1 | chr7:27656375-27674607 |
| 11898 | Mad1l1 | NM_010752.3 | chr5:140008688-140321552 | 11995 | Map3k11 | NM_022012.3 | chr19:5689130-5702864 |
| 11899 | Mad2l1 | NM_019499.4 | chr6:66535647-66540991 | 11996 | Map3k12 | NM_001163643.1 | chr15:102497646-102517004 |
| 11900 | Mad2l1bp | NM_026649.3 | chr17:46147334-46153551 | 11997 | Map3k13 | NM_172821.3 | chr16:21893968-21931877 |
| 11901 | Mad2l2 | NM_027985.3 | chr4:148140489-148145704 | 11998 | Map3k14 | NM_016896.3 | chr11:103219763-103267401 |
| 11902 | Madcam1 | NM_013591.2 | chr10:79664573-79668536 | 11999 | Map3k15 | NM_001163085.2 | chrX:159988432-160123351 |
| 11903 | Madd | NM_001177719.1 | chr2:91137359-91186047 | 12000 | Map3k19 | NM_011737.1 | chr1:127815270-127840290 |
| 11904 | Maea | NM_021500.2 | chr5:33335571-33373294 | 12001 | Map3k2 | NM_011946.3 | chr18:32163088-32236751 |
| 11905 | Mael | NM_175296.4 | chr1:166201384-166238744 | 12002 | Map3k3 | NM_011947.3 | chr11:106084901-106155434 |
| 11906 | Maf | NM_001025577.2 | chr8:115703252-115706894 | 12003 | Map3k4 | NM_011948.2 | chr17:12227620-12318660 |
| 11907 | Mafl1 | NM_001164607.1 | chr15:76351293-76354378 | 12004 | Map3k5 | NM_008580.4 | chr10:19934525-20142750 |
| 11908 | Mafa | NM_194350.1 | chr15:75746842-75747922 | 12005 | Map3k6 | NM_016693.5 | chr4:133240817-133252928 |
| 11909 | Mafb | NM_010658.3 | chr2:160363676-160367065 | 12006 | Map3k7 | NM_009316.1 | chr4:31964106-32023466 |
| 11910 | Maff | NM_010755.1 | chr15:79347519-79359076 | 12007 | Map3k7cl | NM_144854.2 | chr16:87555329-87595336 |
| 11911 | Mafg | NM_010756.3 | chr11:120628350-120633547 | 12008 | Map3k8 | NM_007746.2 | chr18:4331326-4352953 |
| 11912 | Mafk | NM_010757.3 | chr5:139791535-139802652 | 12009 | Map3k9 | NM_001174107.1 | chr12:81714949-81781170 |
| 11913 | Mag | NM_010758.2 | chr7:30899182-30914832 | 12010 | Map4 | NM_001205330.1 | chr9:109931773-110083954 |
| 11914 | Magea1 | NM_020015.2 | chrX:155088518-155089790 | 12011 | Map4k1 | NM_008279.2 | chr7:28982853-29003278 |
| 11915 | Magea10 | NM_001085106.1 | chrX:72381869-72386658 | 12012 | Map4k2 | NM_009221.7 | chr19:6341159-6355619 |
| 11916 | Magea2 | NM_020016.1 | chrX:155027200-155033292 | 12013 | Map4k3 | NM_001290345.1 | chr17:80580512-80728025 |
| 11917 | Magea3 | NM_020017.2 | chrX:154949462-154949569 | 12014 | Map4k4 | NM_001252200.1 | chr1:39900912-40026310 |
| 11918 | Magea4 | NM_020280.2 | chrX:72222064-72222964 | 12015 | Map4k5 | NM_201519.2 | chr12:69803756-69893163 |
| 11919 | Magea5 | NM_001080108.1 | chrX:155051060-155061853 | 12016 | Map6 | NM_001043555.2 | chr7:99268345-99387137 |
| 11920 | Magea6 | NM_020018.2 | chrX:154949013-154926315 | 12017 | Map6d1 | NM_198599.2 | chr16:20233308-20241358 |
| 11921 | Magea8 | NM_020020.4 | chrX:154985774-154995850 | 12018 | Map7 | NM_001198635.1 | chr10:20148919-20281590 |
| 11922 | Mageb1 | NM_010759.1 | chrX:91331754-92016333 | 12019 | Map7d1 | NM_001145970.1 | chr4:126232167-126256319 |
| 11923 | Mageb16 | NM_001081081.1 | chrX:91421571-91480757 | 12020 | Map7d2 | NM_001081124.2 | chrX:15941571-15949875 |
| 11924 | Mageb16-ps1 | NR_033647.1 | chrX:144552757-144556239 | 12021 | Map9 | NM_001081230.1 | chr3:82358073-82395268 |
| 11925 | Mageb18 | NM_173783.3 | chrX:92118878-92599572 | 12022 | Mapk1 | NM_001038663 | chr16:16983381-17039040 |
| 11926 | Mageb3 | NM_031171.1 | chrX:91331904-92016183 | 12023 | Mapk10 | NM_001081567.2 | chr5:102908548-103211334 |
| 11927 | Mageb3 | NM_008545.2 | chr2:121953770-121956092 | 12024 | Mapk11 | NM_011161.5 | chr15:89142483-89149606 |
| 11928 | Mageb4 | NM_001033492.2 | chrX:86250255-86256219 | 12025 | Mapk12 | NM_013871.3 | chr15:89130583-89140703 |
| 11929 | Mageb5 | NM_028847.1 | chrX:91729607-91782976 | 12026 | Mapk13 | NM_011950.2 | chr17:28769316-28778704 |
| 11930 | Maged1 | NM_019791.2 | chrX:94354373-94542074 | 12027 | Mapk14 | NM_001168508.1 | chr17:28691341-28748405 |

Fig.21 - 63

| | | | | | | | |
|---|---|---|---|---|---|---|---|
| 12028 | Mapk15 | NM_177922.2 | chr15:75993768-75999153 | 12125 | Mc2r | NM_001271716.1 | chr18:68406899-68429320 |
| 12029 | Mapk1ip1 | NM_001045483.1 | chr7:138835817-138846267 | 12126 | Mc3r | NM_008561.3 | chr2:172248491-172251114 |
| 12030 | Mapk1ip1l | NM_178684.5 | chr14:47298313-47323091 | 12127 | Mc4r | NM_016977.4 | chr18:66857704-66860487 |
| 12031 | Mapk3 | NM_011952.2 | chr7:126759625-126765816 | 12128 | Mc5r | NM_013596.2 | chr18:68337602-68339711 |
| 12032 | Mapk4 | NM_172632.2 | chr18:73928485-74064949 | 12129 | Mcam | NM_023061.2 | chr9:44134657-44142726 |
| 12033 | Mapk6 | NM_015806.5 | chr9:75386781-75410016 | 12130 | Mcat | NM_001030014.2 | chr15:83546796-83555711 |
| 12034 | Mapk7 | NM_001291033.1 | chr11:61486811-61494266 | 12131 | Mcc | NM_001085373.1 | chr18:44425059-44812182 |
| 12035 | Mapk8 | NM_016700.4 | chr14:33377898-33447158 | 12132 | Mccc1 | NM_023644.4 | chr3:35959305-36000678 |
| 12036 | Mapk8ip1 | NM_001202445.1 | chr2:92383675-92392683 | 12133 | Mccc1os | NR_029456.1 | chr3:35999912-36008828 |
| 12037 | Mapk8ip2 | NM_021921.3 | chr15:89453910-89462447 | 12134 | Mccc2 | NM_030026.2 | chr13:99948531-100015639 |
| 12038 | Mapk8ip3 | NM_001168447.1 | chr17:24897505-24936977 | 12135 | Mcee | NM_028626.1 | chr7:64392770-64412119 |
| 12039 | Mapk9 | NM_001163671.1 | chr11:49846750-49886421 | 12136 | Mcemp1 | NM_026985.1 | chr8:3665761-3668905 |
| 12040 | Mapkap1 | NM_001290625.1 | chr2:34406770-34624958 | 12137 | Mcf2 | NM_001289730.1 | chrX:60055955-60147700 |
| 12041 | Mapkapk2 | NM_008551.2 | chr1:131053700-131097843 | 12138 | Mcf2l | NM_001159485.1 | chr8:12949417-13020509 |
| 12042 | Mapkapk3 | NM_178907.3 | chr9:107254926-107289877 | 12139 | Mcfd2 | NM_139295.3 | chr17:87254442-87265947 |
| 12043 | Mapkapk5 | NM_010765.2 | chr5:121525050-121545892 | 12140 | Mchr1 | NM_145132.2 | chr15:81235498-81238964 |
| 12044 | Mapkbp1 | NM_011943.3 | chr2:119972698-120027403 | 12141 | Mcidas | NM_001037914.3 | chr13:112993867-113000394 |
| 12045 | Mapre1 | NM_007896.3 | chr2:153741286-153778314 | 12142 | Mcl1 | NM_008562.3 | chr3:95658720-95663178 |
| 12046 | Mapre2 | NM_001162941.1 | chr18:23753724-23893861 | 12143 | Mcm10 | NM_027290.3 | chr2:4990723-5012791 |
| 12047 | Mapre3 | NM_133350.2 | chr5:30814640-30866106 | 12144 | Mcm2 | NM_008564.2 | chr6:88883473-88898780 |
| 12048 | Mapt | NM_001038609.2 | chr11:104231435-104332089 | 12145 | Mcm3 | NM_008563.2 | chr1:20803013-20820213 |
| 12049 | Marc1 | NM_001290273.1 | chr1:184786766-184811300 | 12146 | Mcm3ap | NM_019434.2 | chr10:76468970-76515857 |
| 12050 | Marc2 | NM_133684.3 | chr1:184813067-184845847 | 12147 | Mcm4 | NM_008565.3 | chr16:15623896-15637400 |
| 12051 | March1 | NM_001166372.1 | chr8:66618039-66471637 | 12148 | Mcm5 | NM_008566.3 | chr8:75109508-75128439 |
| 12052 | March10 | NM_001039242.2 | chr11:105401653-105456735 | 12149 | Mcm6 | NM_008567.2 | chr1:128331574-128359705 |
| 12053 | March11 | NM_177597.6 | chr15:26309047-26409575 | 12150 | Mcm7 | NM_008568.2 | chr5:138164588-138171862 |
| 12054 | March2 | NM_001252480.1 | chr17:33691504-33718677 | 12151 | Mcm8 | NM_001291054.1 | chr2:132816140-132844188 |
| 12055 | March3 | NM_177115.2 | chr18:56761715-56925548 | 12152 | Mcm9 | NM_027830.2 | chr10:53537323-53630439 |
| 12056 | March4 | NM_001045633.1 | chr1:72427111-72536564 | 12153 | Mcmbp | NM_145955.3 | chr7:128696458-128740429 |
| 12057 | March5 | NM_001164336.1 | chr19:37207544-37221076 | 12154 | Mcmdc2 | NM_177722.3 | chr1:9908637-9940954 |
| 12058 | March6 | NM_172606.2 | chr15:31453898-31531037 | 12155 | Mcoln1 | NM_053177.1 | chr8:3500518-3515231 |
| 12059 | March7 | NM_020575.2 | chr2:60209935-60248385 | 12156 | Mcoln2 | NM_001005846.2 | chr3:146150173-146195512 |
| 12060 | March8 | NM_027920.5 | chr6:116338021-116409341 | 12157 | Mcoln3 | NM_134160.1 | chr3:146121790-146140646 |
| 12061 | March9 | NM_001033262.2 | chr10:127056049-127060184 | 12158 | Mcph1 | NM_173189.2 | chr8:18595172-18803188 |
| 12062 | Marcks | NM_008538.2 | chr10:37133242-37138926 | 12159 | Mcpt1 | NM_008570.1 | chr14:56017963-56020391 |
| 12063 | Marcksl1 | NM_010807.4 | chr4:129513580-129515981 | 12160 | Mcpt2 | NM_008571.1 | chr14:56042122-56044634 |
| 12064 | Marcksl1-ps4 | NR_026405.1 | chr3:4248734-4249707 | 12161 | Mcpt4 | NM_010779.2 | chr14:56059743-56062130 |
| 12065 | Marco | NM_010766.2 | chr1:120475437-120509084 | 12162 | Mcpt8 | NM_008572.1 | chr14:56082163-56085197 |
| 12066 | Marf1 | NM_001081154.2 | chr16:14109165-14159274 | 12163 | Mcpt9 | NM_010782.3 | chr14:56026863-56030495 |
| 12067 | Mark1 | NM_145515.2 | chr1:184896423-184999549 | 12164 | Mcpt-ps1 | NR_028284.1 | chr15:55849808-55952371 |
| 12068 | Mark2 | NM_001080388.2 | chr19:7275395-7341860 | 12165 | Mcrs1 | NM_001164156.1 | chr15:99242816-99251961 |
| 12069 | Mark3 | NM_021516.4 | chr12:111574309-111656227 | 12166 | Mctp1 | NM_030174.2 | chr13:76384960-77031810 |
| 12070 | Mark4 | NM_172279.1 | chr7:19426074-19458494 | 12167 | Mctp2 | NM_001024703.1 | chr7:72077829-72306595 |
| 12071 | Mars | NM_010003913.2 | chr10:127296220-127311786 | 12168 | Mcts1 | NM_026302.3 | chrX:38600857-38613522 |
| 12072 | Mars2 | NM_175439 | chr1:55237176-55240058 | 12169 | Mcts2 | NM_025543.2 | chr2:152687147-152687942 |
| 12073 | Marveld1 | NM_183195 | chr19:42147388-42151703 | 12170 | Mcu | NM_001033259.4 | chr10:59446983-59616692 |
| 12074 | Marveld2 | NM_001038602 | chr13:100595956-100616971 | 12171 | Mcur1 | NM_001081059.3 | chr13:43538405-43560191 |
| 12075 | Marveld3 | NM_028584.3 | chr8:109952908-109962205 | 12172 | Mdc1 | NM_010833.2 | chr17:35841497-35859670 |
| 12076 | Mas1 | NM_008552.4 | chr17:12841004-12868148 | 12173 | Mdfi | NM_001109973.2 | chr17:47815327-47834691 |
| 12077 | Masp1 | NM_008555.2 | chr16:23451784-23520590 | 12174 | Mdfic | NM_175088.5 | chr6:15720660-15802169 |
| 12078 | Masp2 | NM_001003893.2 | chr4:148602543-148615480 | 12175 | Mdga1 | NM_001081160.1 | chr17:29827957-29887882 |
| 12079 | Mast1 | NM_019945.2 | chr8:84911852-84937353 | 12176 | Mdga2 | NM_001193266.1 | chr12:66466058-67222549 |
| 12080 | Mast2 | NM_001042743.2 | chr4:116306759-116464181 | 12177 | Mdh1 | NM_008618.3 | chr11:21556691-21571934 |
| 12081 | Mast3 | NM_199308.2 | chr8:70778116-70792433 | 12178 | Mdh1b | NM_029696.4 | chr1:63698826-63730318 |
| 12082 | Mast4 | NM_001164336 | chr13:102732488-103134492 | 12179 | Mdh2 | NM_008617.2 | chr5:135778648-135790808 |
| 12083 | Mastl | NM_025979.4 | chr2:23116543-23156024 | 12180 | Mdk | NM_001012335.2 | chr2:91929604-91931702 |
| 12084 | Mat1a | NM_133653.3 | chr14:41105032-41124428 | 12181 | Mdm1 | NM_001162904.1 | chr10:118141786-118168999 |
| 12085 | Mat2a | NM_145569.4 | chr6:72432798-72439558 | 12182 | Mdm2 | NM_001288586.1 | chr10:117688874-117710758 |
| 12086 | Mat2b | NM_001199274.1 | chr11:40679313-40695203 | 12183 | Mdm4 | NM_008575.4 | chr1:132986104-133025416 |
| 12087 | Matk | NM_001285853.1 | chr10:81257298-81262981 | 12184 | Mdn1 | NM_001081392.1 | chr4:32657118-32775217 |
| 12088 | Matn1 | NM_010769.2 | chr4:130944384-130955476 | 12185 | Mdp1 | NM_023397.4 | chr14:55657876-55660508 |
| 12089 | Matn2 | NM_016762.2 | chr15:34306680-34436240 | 12186 | Me1 | NM_001198933.1 | chr9:86581362-86687277 |
| 12090 | Matn3 | NM_010770.4 | chr12:8947928-8972028 | 12187 | Me2 | NM_145494.2 | chr18:73770039-73815392 |
| 12091 | Matn4 | NM_001252563.1 | chr2:164389392-164405160 | 12188 | Me3 | NM_181407.4 | chr7:89632817-89854359 |
| 12092 | Matr3 | NM_010771.6 | chr18:35562157-35592045 | 12189 | Mea1 | NM_001277309.1 | chr17:46680985-46683126 |
| 12093 | Mau2 | NM_70016122-70042734 | chr8:70016122-70042734 | 12190 | Meaf6 | NM_001290701.1 | chr4:125085133-125110070 |
| 12094 | Mavs | NM_001206382.1 | chr2:131234062-131248024 | 12191 | Mecom | NM_007963.2 | chr3:29951295-30013204 |
| 12095 | Max | NM_001146376.1 | chr12:76937268-76962248 | 12192 | Mecp2 | NM_010081979.2 | chrX:74026691-74085690 |
| 12096 | Maz | NM_010772.1 | chr7:127022136-127026479 | 12193 | Mecr | NM_023297.2 | chr4:131843470-131867787 |
| 12097 | Mb | NM_001164047.1 | chr15:77015486-77022787 | 12194 | Med1 | NM_001080118.1 | chr11:98153660-98193293 |
| 12098 | Mb21d1 | NM_173386.5 | chr9:78430517-78443237 | 12195 | Med10 | NM_138596.2 | chr13:69809881-69816094 |
| 12099 | Mb21d2 | NM_177715.3 | chr16:28826175-28929698 | 12196 | Med11 | NM_025397.2 | chr11:70453930-70453726 |
| 12100 | Mbd1 | NM_013594.2 | chr18:74268287-74282684 | 12197 | Med12 | NM_021521.2 | chrX:101274090-101298984 |
| 12101 | Mbd2 | NM_010774.2 | chr18:70568291-70626131 | 12198 | Med13 | NM_177855.3 | chr11:59006977-59318412 |
| 12102 | Mbd3 | NM_013595.3 | chr10:80392538-80399531 | 12199 | Med13l | NM_001080931.1 | chr5:86265714-86357525 |
| 12103 | Mbd3l1 | NM_028557.2 | chr9:18478394-18485292 | 12200 | Med13l | NM_172424.4 | chr5:118560718-118765437 |
| 12104 | Mbd3l2 | NM_144934.3 | chr9:18460614-18446316 | 12201 | Med14 | NM_001048208.1 | chrX:12675370-12761973 |
| 12105 | Mbd4 | NM_010774.2 | chr6:115840696-115853341 | 12202 | Med15 | NM_001040683.2 | chr16:17691207-17722947 |
| 12106 | Mbd5 | NM_001290656.1 | chr2:49245899-49317069 | 12203 | Med16 | NM_001083276.1 | chr10:79894706-79908933 |
| 12107 | Mbd6 | NM_033072.2 | chr10:127281955-127288771 | 12204 | Med17 | NM_144933.1 | chr9:15260350-15279867 |
| 12108 | Mbip | NM_145442.2 | chr12:56328306-56345894 | 12205 | Med18 | NM_026039.3 | chr4:132458728-132463921 |
| 12109 | Mbl1 | NM_010775.2 | chr14:41151455-41158959 | 12206 | Med19 | NM_025885.3 | chr2:84678401-84688215 |
| 12110 | Mbl2 | NM_010776.1 | chr19:30232956-30239682 | 12207 | Med20 | NM_020048.3 | chr17:47611595-47624418 |
| 12111 | Mblac1 | NM_177878.3 | chr5:138194313-138195621 | 12208 | Med21 | NM_025315.3 | chr6:146642578-146650600 |
| 12112 | Mblac2 | NM_001167910.1 | chr13:81711416-817533275 | 12209 | Med22 | NM_001033908.1 | chr2:26905266-26910642 |
| 12113 | Mbnl1 | NM_001253708.2 | chr3:60501178-60629750 | 12210 | Med23 | NM_001164116.1 | chr10:24869985-24913529 |
| 12114 | Mbnl2 | NM_175343.4 | chr14:120275684-120346333 | 12211 | Med24 | NM_011869.2 | chr11:98704596-98729485 |
| 12115 | Mbnl3 | NM_134163.5 | chrX:51113493-51205990 | 12212 | Med25 | NM_029365.2 | chr7:44879385-44892366 |
| 12116 | Mboat1 | NM_153546.4 | chr13:30136489-30246694 | 12213 | Med26 | NM_027485.4 | chr8:72494558-72548310 |
| 12117 | Mboat2 | NM_001083348.1 | chr12:24985098-24960299 | 12214 | Med27 | NM_001290489.1 | chr2:29378513-29524790 |
| 12118 | Mboat4 | NM_001126314.2 | chr8:34115029-34129185 | 12215 | Med28 | NM_025895.4 | chr5:45520228-45529284 |
| 12119 | Mboat7 | NM_029934.3 | chr7:3677788-3693525 | 12216 | Med29 | NM_026042 | chr7:28385246-28392890 |
| 12120 | Mbp | NM_001025245.1 | chr18:82475122-82558703 | 12217 | Med30 | NM_027212.2 | chr15:52712444-52730431 |
| 12121 | Mbtd1 | NM_134012.3 | chr11:93886218-93946984 | 12218 | Med31 | NM_026068 | chr11:72211723-72215592 |
| 12122 | Mbtps1 | NM_001167910.1 | chr8:119508151-119558761 | 12219 | Med4 | NM_026119 | chr14:75010048-73518545 |
| 12123 | Mbtps2 | NM_172307.3 | chrX:157547821-157598715 | 12220 | Med6 | NM_027213.2 | chr12:81573563-81594958 |
| 12124 | Mc1r | NM_008559.2 | chr8:123407081-123410744 | 12221 | Med7 | NM_001104530.1 | chr11:46436946-46442721 |

Fig.21 - 64

| | | | | | | | | |
|---|---|---|---|---|---|---|---|---|
| 12222 | Med8 | NM_001290688.1 | chr4:118409336-118419824 | | 12319 | Mfsd3 | NM_027122.3 | chr15:76701941-76704239 |
| 12223 | Med9 | NM_138675.3 | chr11:59948213-59963306 | | 12320 | Mfsd4 | NM_001114662.1 | chr1:132036782-132068062 |
| 12224 | Med9os | NR_045273.1 | chr11:59946891-59948147 | | 12321 | Mfsd5 | NM_134100.4 | chr1:102279455-102281744 |
| 12225 | Medag | NM_027519.3 | chr5:149411805-149431703 | | 12322 | Mfsd6 | NM_133829.2 | chr1:52656304-52727318 |
| 12226 | Mef2a | NM_001033713.2 | chr7:67231162-67372858 | | 12323 | Mfsd6l | NM_146004.1 | chr11:68556185-68558245 |
| 12227 | Mef2b | NM_001045484.2 | chr8:70152760-70167488 | | 12324 | Mfsd7a | NM_172883.2 | chr5:108441053-108448891 |
| 12228 | Mef2c | NM_001170537.1 | chr13:83504033-83667079 | | 12325 | Mfsd7b | NM_001081259.1 | chr1:191005831-191026190 |
| 12229 | Mef2d | NM_133665.4 | chr3:88142371-88172091 | | 12326 | Mfsd7c | NM_145447.2 | chr12:85746538-85813585 |
| 12230 | Mefv | NM_001161790.1 | chr16:3707214-3718124 | | 12327 | Mfsd8 | NM_028140.4 | chr3:40818171-40846854 |
| 12231 | Meg3 | NR_003633.3 | chr12:109546397-109568650 | | 12328 | Mfsd9 | NM_172499.2 | chr1:40772039-40790657 |
| 12232 | Megf10 | NM_001001979.2 | chr18:57133089-57297467 | | 12329 | Mga | NM_001164274.1 | chr2:119897227-119969581 |
| 12233 | Megf11 | NM_001134985.1 | chr9:64385625-64709205 | | 12330 | Mgam | NM_001171903.1 | chr6:40628830-40769123 |
| 12234 | Megf6 | NM_001162977.1 | chr4:154170712-154275721 | | 12331 | Mgarp | NM_026358.3 | chr3:51388412-51396547 |
| 12235 | Megf8 | NM_001160400.1 | chr7:25317163-25365917 | | 12332 | Mgat1 | NM_001110348.1 | chr11:49244190-49263024 |
| 12236 | Megf9 | NM_172694.2 | chr4:70431926-70534928 | | 12333 | Mgat2 | NM_146035.2 | chr12:69184157-69186773 |
| 12237 | Mei1 | NM_028897.3 | chr15:82070116-82126814 | | 12334 | Mgat3 | NM_010795.4 | chr15:80173720-80215519 |
| 12238 | Mei4 | NM_175213.3 | chr9:81863743-82027491 | | 12335 | Mgat4a | NM_001290801.1 | chr1:37439339-37536404 |
| 12239 | Meig1 | NM_008579.4 | chr2:3409042-3422648 | | 12336 | Mgat4b | NM_145926.3 | chr11:50225334-50235103 |
| 12240 | Meiob | NM_029197.1 | chr17:24804381-24839787 | | 12337 | Mgat4c | NM_001162368.1 | chr10:102158857-102391468 |
| 12241 | Meis1 | NM_001193271.1 | chr11:18880427-19018969 | | 12338 | Mgat5 | NM_145128.3 | chr1:127204985-127482972 |
| 12242 | Meis2 | NM_001136072.2 | chr2:115861263-116065058 | | 12339 | Mgat5b | NM_172948.3 | chr11:116918862-116986944 |
| 12243 | Meis3 | NM_001277988.2 | chr7:16175394-16186508 | | 12340 | Mgea5 | NM_023799.3 | chr19:45750258-45783291 |
| 12244 | Melk | NM_010790.2 | chr4:44364916-44364675 | | 12341 | Mgl2 | NM_145137.2 | chr11:70130356-70137542 |
| 12245 | Memo1 | NM_133771.2 | chr17:74200699-74294863 | | 12342 | Mgll | NM_001166249.1 | chr6:85724411-58828360 |
| 12246 | Men1 | NM_001168488.1 | chr19:6334978-6340894 | | 12343 | Mgme1 | NM_001289630.1 | chr2:144270903-144281227 |
| 12247 | Meox1 | NM_010791.3 | chr11:101877509-101894354 | | 12344 | Mgmt | NM_008598.2 | chr7:136894610-137128188 |
| 12248 | Meox2 | NM_008584.3 | chr12:37108545-37179528 | | 12345 | Mgp | NM_008597.3 | chr6:136872434-136875806 |
| 12249 | Mep1a | NM_008585.2 | chr17:43474328-43502773 | | 12346 | Mgrn1 | NM_001252437.1 | chr16:4886909-4938296 |
| 12250 | Mep1b | NM_008586.3 | chr18:21072343-21100199 | | 12347 | Mgst1 | NM_019946.4 | chr6:138140536-138156752 |
| 12251 | Mepce | NM_144853.3 | chr5:137781905-137786701 | | 12348 | Mgst2 | NM_174995.3 | chr3:51661178-51682674 |
| 12252 | Mepe | NM_053172.2 | chr5:104325328-104338611 | | 12349 | Mgst3 | NM_025569.1 | chr1:167372383-167393797 |
| 12253 | Mertk | NM_008587.1 | chr2:128698996-128802188 | | 12350 | Mia | NM_019394.3 | chr7:27179740-27181149 |
| 12254 | Mesdc1 | NM_030705.4 | chr7:83880494-83884341 | | 12351 | Mia2 | NM_177321.2 | chr12:59095799-59109130 |
| 12255 | Mesdc2 | NM_023403.3 | chr7:83891999-83901532 | | 12352 | Mia3 | NM_177389.3 | chr1:183326235-183369565 |
| 12256 | Mesp1 | NM_008588.2 | chr7:79792240-79793590 | | 12353 | Miat | NR_003718.2 | chr5:112213227-112228948 |
| 12257 | Mesp2 | NM_008589.2 | chr7:79810726-79813431 | | 12354 | Mib1 | NM_144860.2 | chr18:10725624-10812217 |
| 12258 | Mest | NM_001252292.1 | chr6:30738052-30748466 | | 12355 | Mib2 | NM_001256107.1 | chr4:155654469-155669254 |
| 12259 | Met | NM_008591.2 | chr6:17453956-17573980 | | 12356 | Mical1 | NM_001164433.1 | chr10:41476313-41487030 |
| 12260 | Metap1 | NM_175224.4 | chr3:138458959-138489382 | | 12357 | Mical2 | NM_001193305.1 | chr7:112225835-112353975 |
| 12261 | Metap1d | NM_025633.3 | chr2:71453337-71525191 | | 12358 | Mical3 | NM_001270475.1 | chr6:120931545-121131022 |
| 12262 | Metap2 | NM_019648.3 | chr10:93858489-93891202 | | 12359 | Micalcl | NM_027587.2 | chr7:112368307-112413104 |
| 12263 | Metrn | NM_133719.2 | chr17:25794570-25797045 | | 12360 | Micall1 | NM_177461.1 | chr15:79108982-79136901 |
| 12264 | Metrnl | NM_144797.3 | chr11:121702426-121717389 | | 12361 | Micall2 | NM_174850.3 | chr5:139706892-139736333 |
| 12265 | Mettl1 | NM_010792.1 | chr10:127041931-127045463 | | 12362 | Micu1 | NM_001291442.1 | chr10:59702562-59864134 |
| 12266 | Mettl10 | NM_028095.1 | chr7:132827460-132852647 | | 12363 | Micu2 | NM_028643.3 | chr14:57916279-57999262 |
| 12267 | Mettl11b | NM_001143956.1 | chr1:163702992-163725232 | | 12364 | Micu3 | NM_030110.1 | chr8:40308050-40388304 |
| 12268 | Mettl13 | NM_144577.4 | chr1:162553671-162548345 | | 12365 | Mid1 | NM_001290504.1 | chrX:169828158-169990797 |
| 12269 | Mettl14 | NM_201638.2 | chr3:123388294-123385990 | | 12366 | Mid1ip1 | NM_001166635.1 | chrX:19717364-10719702 |
| 12270 | Mettl15 | NM_029790.3 | chr2:109082299-109278290 | | 12367 | Mid2 | NM_011845.2 | chrX:140678027-140767715 |
| 12271 | Mettl16 | NM_026171.2 | chr11:74770862-74818692 | | 12368 | Midn | NM_023565.2 | chr10:80148271-80158368 |
| 12272 | Mettl17 | NM_001029990.1 | chr14:51884841-51891868 | | 12369 | Mief1 | NM_178719.5 | chr15:80234079-80253371 |
| 12273 | Mettl18 | NM_027279.2 | chr1:163994944-163997244 | | 12370 | Mief2 | NM_001009927.2 | chr11:60728397-60732951 |
| 12274 | Mettl2 | NM_172567.3 | chr11:105126424-105141146 | | 12371 | Mien1 | NM_025559.2 | chr11:98437707-98438988 |
| 12275 | Mettl20 | NM_001252094.1 | chr6:349143512-149151170 | | 12372 | Mier1 | NM_001039081.2 | chr4:103119889-103165754 |
| 12276 | Mettl21a | NM_001013799.1 | chr1:64606479-64617168 | | 12373 | Mier2 | NM_027422.3 | chr10:79540244-79555091 |
| 12277 | Mettl21c | NM_001013799.1 | chr1:44009407-44020006 | | 12374 | Mier3 | NM_172593.3 | chr13:111686177-111718594 |
| 12278 | Mettl21e | NM_207281.3 | chr1:44204069-44218931 | | 12375 | Mif | NM_010798.2 | chr10:75859352-75860250 |
| 12279 | Mettl22 | NM_146247.1 | chr16:8470812-8490197 | | 12376 | Mif4gd | NM_001243584.1 | chr11:115607918-115612969 |
| 12280 | Mettl23 | NM_028865.3 | chr11:116843614-116849746 | | 12377 | Miip | NM_001025365.2 | chr4:147860777-147868719 |
| 12281 | Mettl24 | NM_177793.3 | chr10:40683281-40811083 | | 12378 | Mill1 | NM_153749.4 | chr7:18245346-18266092 |
| 12282 | Mettl25 | NM_028657.3 | chr10:105763184-105841380 | | 12379 | Mill2 | NM_153780.2 | chr7:18839965-18858653 |
| 12283 | Mettl3 | NM_019721.2 | chr14:52294841-52305124 | | 12380 | Milr1 | NM_001034435.3 | chr11:106751225-106767765 |
| 12284 | Mettl4 | NM_176917.4 | chr17:94721879-94749889 | | 12381 | Mina | NM_025910.3 | chr16:59471774-59492451 |
| 12285 | Mettl5 | NM_029280.4 | chr2:69871194-69885615 | | 12382 | Mink1 | NM_001045959.1 | chr11:70562880-70614482 |
| 12286 | Mettl6 | NM_025307.3 | chr14:31478797-31494977 | | 12383 | Minos1 | NM_001163006.2 | chr4:139101813-139131113 |
| 12287 | Mettl7a1 | NM_027384.5 | chr15:100304848-100314348 | | 12384 | Minpp1 | NM_100799.2 | chr19:32485768-32515370 |
| 12288 | Mettl7a2 | NM_199477.2 | chr15:100353199-100361819 | | 12385 | Mios | NM_145374.2 | chr6:8209226-8236273 |
| 12289 | Mettl7a2Higd1c | NM_001024672.3 | chr15:100353199-100384435 | | 12386 | Miox | NM_019977.2 | chr15:89334472-89337007 |
| 12290 | Mettl7a3 | NM_001081471.1 | chr15:100334928-100340169 | | 12387 | Mip | NM_008600.5 | chr10:128225809-128231812 |
| 12291 | Mettl7b | NM_027853.2 | chr10:128958276-128960988 | | 12388 | Mipep | NM_027436.3 | chr14:60784565-60903613 |
| 12292 | Mettl8 | NM_001110512.1 | chr2:70964561-71018374 | | 12389 | Mipol1 | NM_001164370.1 | chr12:57230424-57457241 |
| 12293 | Mettl9 | NM_021554.2 | chr7:121034444-121076835 | | 12390 | Mir100 | NR_029790.1 | chr9:41531424-41531504 |
| 12294 | Mex3a | NM_001029890.2 | chr3:88532394-88541394 | | 12391 | Mir101a | NR_029537.1 | chr4:101346944-101347027 |
| 12295 | Mex3b | NM_175366.3 | chr7:82867332-82871576 | | 12392 | Mir101b | NR_029778.1 | chr19:29135278-29135375 |
| 12296 | Mex3c | NM_001030214.4 | chr18:73572704-73592578 | | 12393 | Mir101c | NR_039646.1 | chr9:3038668-3038743 |
| 12297 | Mex3d | NM_198615.2 | chr10:80380354-80387651 | | 12394 | Mir103-1 | NR_029754.1 | chr11:35782395-35782481 |
| 12298 | Mfap1a | NM_026220.4 | chr2:122342680-121506656 | | 12395 | Mir103-2 | NR_029755.1 | chr2:131288051-131288137 |
| 12299 | Mfap1b | NM_001081975.3 | chr2:121461665-121474023 | | 12396 | Mir105 | NR_030546.1 | chrX:72591499-72591579 |
| 12300 | Mfap2 | NM_008546.3 | chr4:141010423-141015984 | | 12397 | Mir106a | NR_029742.1 | chrX:52742502-52742567 |
| 12301 | Mfap3 | NM_145426.2 | chr15:57518664-57533817 | | 12398 | Mir106b | NR_029658.1 | chr5:138165736-138165818 |
| 12302 | Mfap3l | NM_001177881.1 | chr8:60655109-60676791 | | 12399 | Mir107 | NR_029783.1 | chr19:34820686-34820773 |
| 12303 | Mfap4 | NM_001081279.3 | chr11:61485443-61488704 | | 12400 | Mir10a | NR_029784.1 | chr11:96317164-96317274 |
| 12304 | Mfap5 | NM_015776.2 | chr6:122513675-122529287 | | 12401 | Mir10b | NR_029566.1 | chr2:74726089-74726137 |
| 12305 | Mff | NM_029409.3 | chr1:82724889-82752389 | | 12402 | Mir1187 | NR_035415.1 | chr5:82798943-82799065 |
| 12306 | Mfge8 | NM_001045489.1 | chr7:79133767-79149060 | | 12403 | Mir1188 | NR_035419.1 | chr12:109611821-109611941 |
| 12307 | Mfhas1 | NM_001081279.3 | chr8:35587797-35679449 | | 12404 | Mir1190 | NR_035421 | chr12:101023672-101021768 |
| 12308 | Mfi2 | NM_013749.3 | chr16:31878809-31899019 | | 12405 | Mir1191 | NR_035422.1 | chr5:76206228-76469519 |
| 12309 | Mfn1 | NM_024200.4 | chr3:32529481-32579225 | | 12406 | Mir1191b | NR_106141.1 | chr10:81416239-81416297 |
| 12310 | Mfn2 | NM_001285920.1 | chr4:147873585-147904909 | | 12407 | Mir1192 | NR_035423.1 | chr19:23149430-23149551 |
| 12311 | Mfng | NM_008546.3 | chr15:78775882-78773445 | | 12408 | Mir1193 | NR_035424.1 | chr12:109715670-109715791 |
| 12312 | Mfrp | NM_001190314.1 | chr9:44101769-44109187 | | 12409 | Mir1195 | NR_035427 | chr16:30920953-31275697 |
| 12313 | Mfsd1 | NM_025813.3 | chr3:67582767-67604231 | | 12410 | Mir1197 | NR_035429.1 | chr12:109712316-109712436 |
| 12314 | Mfsd10 | NM_026660.2 | chr5:34633646-34637114 | | 12411 | Mir1198 | NR_035430.1 | chr12:55370694-55491306 |
| 12315 | Mfsd11 | NM_178620.3 | chr11:116854014-116875637 | | 12412 | Mir1199 | NR_035431.1 | chr8:84011514-84011633 |
| 12316 | Mfsd12 | NM_028657.3 | chr10:81357569-81364035 | | 12413 | Mir1224 | NR_035407.1 | chr18:20604451-20604536 |
| 12317 | Mfsd2a | NM_029662.2 | chr4:122846850-122961188 | | 12414 | Mir122a | NR_029600.1 | chr18:65248850-65248926 |
| 12318 | Mfsd2b | NM_001033428.2 | chr12:4862437-4874359 | | 12415 | Mir1231 | NR_049128.1 | chr1:135454602-135454683 |

Fig.21 - 65

| | | | | | | | | |
|---|---|---|---|---|---|---|---|---|
| 12416 | Mir1247 | NR_037204.1 | chr12:110278047-110278129 | 12513 | Mir1904 | NR_035442.1 | chr13:109903808-109903888 |
| 12417 | Mir1249 | NR_037206.1 | chr15:84951525-84951623 | 12514 | Mir1905 | NR_035434.1 | chr3:88536300-88536382 |
| 12418 | Mir124a-1 | NR_029813.1 | chr14:64590656-64590741 | 12515 | Mir1906-1 | NR_035440.1 | chrX:88759473-109544620 |
| 12419 | Mir124a-2 | NR_029814.1 | chr3:17795661-17795770 | 12516 | Mir1907 | NR_035444.1 | chr15:50889024-50889114 |
| 12420 | Mir124a-3 | NR_029538.1 | chr2:180894039-180894107 | 12517 | Mir1908 | NR_030543.1 | chr3:90070019-90070099 |
| 12421 | Mir1251 | NR_037219.1 | chr10:92137139-92137223 | 12518 | Mir191 | NR_029577.1 | chr9:108568318-108568392 |
| 12422 | Mir1258 | NR_106160.1 | chr18:56538138-56538198 | 12519 | Mir1912 | NR_037300.1 | chrX:147009440-147009527 |
| 12423 | Mir125a | NR_029539.1 | chr17:17830811-17830879 | 12520 | Mir192 | NR_029720.1 | chr19:6264843-6264932 |
| 12424 | Mir125b-1 | NR_029822.1 | chr9:41581925-41582002 | 12521 | Mir1928 | NR_035449.1 | chr1:74206553-74206620 |
| 12425 | Mir125b-2 | NR_029540.1 | chr19:77646272-77646343 | 12522 | Mir1929 | NR_035450.1 | chr10:44359675-44359768 |
| 12426 | Mir126 | NR_029541.1 | chr2:26591356-26591429 | 12523 | Mir193 | NR_029579.1 | chr11:79711968-79712034 |
| 12427 | Mir1264 | NR_037205.1 | chrX:147010600-147010686 | 12524 | Mir1930 | NR_035451.1 | chr10:77641223-77641307 |
| 12428 | Mir126b | NR_106155.1 | chr2:26591352-26591420 | 12525 | Mir1931 | NR_035452.1 | chr10:93162784-93162903 |
| 12429 | Mir127 | NR_029542.1 | chr12:109592845-109592915 | 12526 | Mir1932 | NR_035453.1 | chr11:119390471-119390561 |
| 12430 | Mir128-1 | NR_029543.1 | chr1:128202360-128202430 | 12527 | Mir1933 | NR_035454.1 | chr1:21344587-21344675 |
| 12431 | Mir128-2 | NR_029823.1 | chr9:112118635-112118711 | 12528 | Mir1934 | NR_035455.1 | chr11:69663042-69663125 |
| 12432 | Mir1291 | NR_106171.1 | chr15:98519761-98519878 | 12529 | Mir1936 | NR_035457.1 | chr12:102684927-102685020 |
| 12433 | Mir129-1 | NR_029567.1 | chr6:29022618-29022691 | 12530 | Mir1938 | NR_035459.1 | chr12:40222711-40222811 |
| 12434 | Mir129-2 | NR_029752.1 | chr2:94241363-94241453 | 12531 | Mir1939 | NR_030549.1 | chr16:13449522-13449601 |
| 12435 | Mir1298 | NR_037210.1 | chrX:147064904-147065002 | 12532 | Mir1940 | NR_035461.1 | chr13:95330586-95330683 |
| 12436 | Mir129b | NR_106139.1 | chr2:94241377-94241442 | 12533 | Mir1941 | NR_035462.1 | chr15:101369351-101369434 |
| 12437 | Mir1306 | NR_035467.2 | chr16:18284238-18284317 | 12534 | Mir194-1 | NR_029580.1 | chr1:185313318-185313385 |
| 12438 | Mir130a | NR_029544.1 | chr2:84741114-84741178 | 12535 | Mir1942 | NR_035463.1 | chr15:76215610-76215673 |
| 12439 | Mir130b | NR_029659.1 | chr16:17124060-17124142 | 12536 | Mir194-2 | NR_029830.1 | chr19:6264642-6264728 |
| 12440 | Mir130c | NR_105807.1 | chr9:53400804-53400886 | 12537 | Mir1943 | NR_035464.1 | chr15:79375227-79375300 |
| 12441 | Mir132 | NR_029546.1 | chr11:75173681-75173747 | 12538 | Mir1945 | NR_035466.1 | chr16:11254367-11254445 |
| 12442 | Mir133a-1 | NR_029547.1 | chr18:10782908-10782976 | 12539 | Mir1946a | NR_035468.1 | chr16:32267449-32267583 |
| 12443 | Mir133a-2 | NR_029901.1 | chr18:180398378-180398482 | 12540 | Mir1946b | NR_035496.1 | chr3:96080595-96148402 |
| 12444 | Mir133b | NR_029902.1 | chr1:20682768-20682887 | 12541 | Mir1947 | NR_035469.1 | chr16:33105360-33105445 |
| 12445 | Mir133c | NR_105793.1 | chr2:29475214-29475294 | 12542 | Mir1948 | NR_035471.1 | chr18:12714810-12714895 |
| 12446 | Mir134 | NR_029548.1 | chr12:109734108-109734209 | 12543 | Mir1949 | NR_035472.1 | chr18:35554568-35554636 |
| 12447 | Mir135a-1 | NR_029549.1 | chr3:106154123-106154213 | 12544 | Mir195 | NR_029581.1 | chr11:70235041-70235135 |
| 12448 | Mir135a-2 | NR_029812.1 | chr10:92072085-92072185 | 12545 | Mir1950 | NR_035473.1 | chr6:40529090-40910666 |
| 12449 | Mir135b | NR_029777.1 | chr1:132198087-132198184 | 12546 | Mir1951 | NR_035476.1 | chr2:115638724-115638813 |
| 12450 | Mir136 | NR_029550.1 | chr12:109595326-109595388 | 12547 | Mir1952 | NR_035477.1 | chr2:138819928-138820007 |
| 12451 | Mir137 | NR_029551.1 | chr3:118433856-118433929 | 12548 | Mir1953 | NR_035478.1 | chr2:151967528-151967617 |
| 12452 | Mir138-1 | NR_029819.1 | chr3:122682875-122682974 | 12549 | Mir1954 | NR_035479.1 | chr2:133220186-113423560 |
| 12453 | Mir138-2 | NR_029552.1 | chr8:94324310-94324381 | 12550 | Mir1955 | NR_035480.1 | chr2:92191976-92192074 |
| 12454 | Mir139 | NR_029791.1 | chr7:101475354-101475443 | 12551 | Mir1956 | NR_035481.1 | chr3:138526420-138526485 |
| 12455 | Mir140 | NR_029553.1 | chr8:107551243-107551313 | 12552 | Mir1957 | NR_035483.1 | chr6:24484966-94782876 |
| 12456 | Mir141 | NR_029554.1 | chr6:124717913-124717985 | 12553 | Mir1957b | NR_105819.1 | chr8:111450199-111450322 |
| 12457 | Mir142 | NR_029555.1 | chr11:87756863-87756927 | 12554 | Mir1958 | NR_035484.1 | chr1:83980972-83984483 |
| 12458 | Mir142b | NR_106176.1 | chr11:87756840-87756955 | 12555 | Mir1959 | NR_105751.1 | chr2:56785810-56785907 |
| 12459 | Mir143 | NR_029601.1 | chr11:61649195-61649258 | 12556 | Mir1960 | NR_035486.1 | chr5:30170738-30170816 |
| 12460 | Mir143hg | NR_045402.1 | chr18:61645877-61565538 | 12557 | Mir1961 | NR_035487.1 | chr5:92788450-92788562 |
| 12461 | Mir144 | NR_029556.1 | chr11:78073004-78073070 | 12558 | Mir1962 | NR_035488.1 | chr7:135566161-135566282 |
| 12462 | Mir145 | NR_029557.1 | chr18:61647824-61647894 | 12559 | Mir1963 | NR_035489.1 | chr7:29083635-29083694 |
| 12463 | Mir145b | NR_105780.1 | chr18:69022198-69022273 | 12560 | Mir1964 | NR_035490.1 | chr7:29773293-29773376 |
| 12464 | Mir146 | NR_029558.1 | chr11:43374396-43374461 | 12561 | Mir1966 | NR_035492 | chr8:105615465-105615573 |
| 12465 | Mir146b | NR_030461.1 | chr19:46342761-46342870 | 12562 | Mir1967 | NR_035493.1 | chr8:124022640-124022722 |
| 12466 | Mir147 | NR_030547.1 | chr2:122640802-122640881 | 12563 | Mir1968 | NR_035494.1 | chr8:13189030-13189098 |
| 12467 | Mir148a | NR_029719.1 | chr6:51269811-51269910 | 12564 | Mir1969 | NR_035495.1 | chr8:70925524-70925618 |
| 12468 | Mir148b | NR_029766.1 | chr1:103285124-103285221 | 12565 | Mir196a-1 | NR_029721.1 | chr11:96265163-96265265 |
| 12469 | Mir149 | NR_029559.1 | chr1:92850377-92850443 | 12566 | Mir196a-2 | NR_029722.1 | chr15:102973349-102973434 |
| 12470 | Mir150 | NR_029560.1 | chr7:45121756-45121821 | 12567 | Mir196b | NR_029912.1 | chr6:52230080-52230185 |
| 12471 | Mir152 | NR_029562.1 | chr11:96850392-96850465 | 12568 | Mir1970 | NR_035497.1 | chr7:107284774-107580276 |
| 12472 | Mir153 | NR_029563.1 | chr12:117250816-117250885 | 12569 | Mir1971 | NR_035499.1 | chr14:78191372-78191478 |
| 12473 | Mir154 | NR_029564.1 | chr12:109738432-109738498 | 12570 | Mir1981 | NR_035502.1 | chr1:184822406-184822428 |
| 12474 | Mir155 | NR_029565.1 | chr16:84714139-84714204 | 12571 | Mir1982 | NR_035503.1 | chr10:80828796-80828870 |
| 12475 | Mir15a | NR_029573.1 | chr14:61632026-61632110 | 12572 | Mir1983 | NR_035500.1 | chr13:21896917-21897049 |
| 12476 | Mir15b | NR_029519.1 | chr3:69009771-69009835 | 12573 | Mir199a-1 | NR_029585.1 | chr9:21496494-21496564 |
| 12477 | Mir16-1 | NR_029734.1 | chr14:61631879-61631972 | 12574 | Mir199a-2 | NR_029810.1 | chr1:162217813-162217929 |
| 12478 | Mir16-2 | NR_029568.1 | chr3:69009901-69009996 | 12575 | Mir199b | NR_029811.1 | chr2:32318459-32318569 |
| 12479 | Mir1668 | NR_106188.1 | chr8:83723877-83723984 | 12576 | Mir19a | NR_029786.1 | chr14:115043999-115044081 |
| 12480 | Mir17 | NR_029785.1 | chr14:115043670-115043754 | 12577 | Mir19b-1 | NR_029815.1 | chr14:115044304-115044391 |
| 12481 | Mir17hg | NR_028362.1 | chr14:115046648-115046728 | 12578 | Mir19b-2 | NR_029715.1 | chrX:52741982-52742066 |
| 12482 | Mir18 | NR_029736.1 | chr14:115043850-115043946 | 12579 | Mir1a-1 | NR_029528.1 | chr2:180389047-180389124 |
| 12483 | Mir181a-1 | NR_029795.1 | chr1:137966454-137966541 | 12580 | Mir1a-2 | NR_029781.1 | chr18:10785480-10785552 |
| 12484 | Mir181a-2 | NR_029568.1 | chr2:38852734-38852810 | 12581 | Mir1b | NR_035413.1 | chr18:10785445-10785557 |
| 12485 | Mir181b-1 | NR_029820.1 | chr1:137966638-137966718 | 12582 | Mir200a | NR_029723.1 | chr4:156054895-156054985 |
| 12486 | Mir181b-2 | NR_029769.1 | chr2:38853829-38853915 | 12583 | Mir200b | NR_029587.1 | chr4:156055680-156055750 |
| 12487 | Mir181c | NR_029821.1 | chr8:84178872-84178961 | 12584 | Mir200c | NR_029792.1 | chr6:124718321-124718390 |
| 12488 | Mir181d | NR_030534.1 | chr8:84178715-84178787 | 12585 | Mir201 | NR_029588.1 | chrX:67988095-67988161 |
| 12489 | Mir182 | NR_029569.1 | chr6:30165917-30165992 | 12586 | Mir202 | NR_029589.1 | chr7:139957688-139957760 |
| 12490 | Mir183 | NR_030713.1 | chr6:30169667-30169737 | 12587 | Mir203 | NR_029590.1 | chr12:112130879-112130955 |
| 12491 | Mir1839 | NR_035501.1 | chr7:81529915-81529988 | 12588 | Mir204 | NR_029591.1 | chr19:22750604-22750672 |
| 12492 | Mir184 | NR_029570.1 | chr9:89802259-89802328 | 12589 | Mir205 | NR_029592.1 | chr1:193507462-193507530 |
| 12493 | Mir1843 | NR_037207.1 | chr12:80391612-80391677 | 12590 | Mir206 | NR_029593.1 | chr1:20679909-20679982 |
| 12494 | Mir1843b | NR_029543.1 | chr1:159340423-159340423 | 12591 | Mir207 | NR_029594.1 | chr4:40722916-40722995 |
| 12495 | Mir185 | NR_029571.1 | chr16:18327400-18327465 | 12592 | Mir208a | NR_029724.1 | chr14:54949059-54949142 |
| 12496 | Mir186 | NR_029572.1 | chr16:157544278-157544349 | 12593 | Mir208b | NR_030607.1 | chr14:54975699-54975776 |
| 12497 | Mir187 | NR_029573.1 | chr18:24429109-24429170 | 12594 | Mir20a | NR_029573.1 | chr14:115044156-115044263 |
| 12498 | Mir188 | NR_029574.1 | chrX:72477988-72480056 | 12595 | Mir20b | NR_030273.1 | chrX:52742112-52742192 |
| 12499 | Mir1892 | NR_035439.1 | chr12:54645932-54646012 | 12596 | Mir21 | NR_029738.1 | chr1:86584066-86584158 |
| 12500 | Mir1893 | NR_035443.1 | chr16:6490563-6490646 | 12597 | Mir210 | NR_029739.1 | chr7:141221383-141221493 |
| 12501 | Mir1894 | NR_035445.1 | chr17:35917838-35917969 | 12598 | Mir211 | NR_029805.1 | chr7:64205805-64205911 |
| 12502 | Mir1895 | NR_035435.1 | chr3:134240564-134240583 | 12599 | Mir212 | NR_029741.1 | chr11:75173387-75173478 |
| 12503 | Mir1896 | NR_035441.1 | chr13:21445159-21445240 | 12600 | Mir213b | NR_035516.1 | chr9:104426112-104426187 |
| 12504 | Mir1897 | NR_035433.1 | chr3:34638463-34638542 | 12601 | Mir2137 | NR_035517.1 | chrX:72992078-72992144 |
| 12505 | Mir1898 | NR_035463.1 | chr15:12171491-12171574 | 12602 | Mir2139 | NR_035519.1 | chr4:139967525-139967620 |
| 12506 | Mir1899 | NR_035437.1 | chr9:8246785-8246881 | 12603 | Mir214 | NR_029796.1 | chr1:162223367-162223477 |
| 12507 | Mir18b | NR_030548.1 | chrX:52742330-52742413 | 12604 | Mir215 | NR_029908.1 | chr1:185313580-185313691 |
| 12508 | Mir190 | NR_029766.1 | chr9:67236659-67236726 | 12605 | Mir216a | NR_029764.1 | chr11:28757011-28757083 |
| 12509 | Mir1900 | NR_035438.1 | chr2:21032250-21032328 | 12606 | Mir216b | NR_030419.1 | chr11:28746190-28746276 |
| 12510 | Mir1901 | NR_035447.1 | chr18:11840046-11840438 | 12607 | Mir216c | NR_106152.1 | chr11:28746199-28746266 |
| 12511 | Mir1902 | NR_035441.1 | chr2:104428860-104428940 | 12608 | Mir217 | NR_029828.1 | chr11:28763727-28763835 |
| 12512 | Mir1903 | NR_035436.1 | chr8:128359240-128359320 | 12609 | Mir218-1 | NR_029798.1 | chr5:48223941-48224051 |

Fig.21 - 66

| | | | | | | | | |
|---|---|---|---|---|---|---|---|---|
| 12610 | Mir219-2 | NR_029799.1 | chr11:35616815-35616925 | 12707 | Mir3097 | NR_037280.1 | chr5:35021048-35021115 |
| 12611 | Mir219-1 | NR_029800.1 | chr17:34024982-34025092 | 12708 | Mir3098 | NR_037281.1 | chr2:131142468-131604824 |
| 12612 | Mir219-2 | NR_029838.1 | chr2:29845630-29845727 | 12709 | Mir3099 | NR_037213.1 | chr7:6803586-6803670 |
| 12613 | Mir219b | NR_106110.1 | chr2:29845646-29845711 | 12710 | Mir30a | NR_029533.1 | chr1:23272268-23272339 |
| 12614 | Mir219c | NR_106154.1 | chr17:34025011-34025071 | 12711 | Mir30b | NR_029634.1 | chr15:68337414-68337510 |
| 12615 | Mir21b | NR_105796.1 | chr3:29636743-29636851 | 12712 | Mir30c-1 | NR_029716.1 | chr4:120769533-120769622 |
| 12616 | Mir21c | NR_105822.1 | chr8:128278147-128278225 | 12713 | Mir30c-2 | NR_029717.1 | chr1:23291700-23291784 |
| 12617 | Mir22 | NR_029739.1 | chr11:75463715-75463810 | 12714 | Mir30d | NR_029718.1 | chr15:68341207-68341289 |
| 12618 | Mir221 | NR_029806.1 | chrX:19146293-19146388 | 12715 | Mir30f | NR_105851.1 | chr4:120772605-120772697 |
| 12619 | Mir222 | NR_029807.1 | chrX:19146892-19146971 | 12716 | Mir31 | NR_029747.1 | chr4:88910556-88910662 |
| 12620 | Mir223 | NR_029801.1 | chrX:96242816-96242926 | 12717 | Mir3100 | NR_037282.1 | chr7:19086827-19086892 |
| 12621 | Mir22hg | NR_030711.1 | chr11:75461538-75466690 | 12718 | Mir3101 | NR_037283.1 | chr7:27176005-27176093 |
| 12622 | Mir23a | NR_029746.1 | chr8:84208517-84208592 | 12719 | Mir3102 | NR_037285.1 | chr7:100082305-100882409 |
| 12623 | Mir23b | NR_029530.1 | chr13:63300483-63300557 | 12720 | Mir3103 | NR_037290.1 | chr7:128288368-128288435 |
| 12624 | Mir24-1 | NR_029575.1 | chr13:63301207-63301275 | 12721 | Mir3104 | NR_037291.1 | chr7:141992178-141992241 |
| 12625 | Mir24-2 | NR_029741.1 | chr8:84208814-84208921 | 12722 | Mir3106 | NR_037214.1 | chr8:16168756-16168838 |
| 12626 | Mir25 | NR_029787.1 | chr5:138165320-138165404 | 12723 | Mir3107 | NR_037293.1 | chr8:23142572-23142662 |
| 12627 | Mir26a-1 | NR_029742.1 | chr9:119031795-119031885 | 12724 | Mir3108 | NR_037295.1 | chr8:108936859-108936938 |
| 12628 | Mir26a-2 | NR_029803.1 | chr10:126995529-126995613 | 12725 | Mir3109 | NR_037296.1 | chr9:69456943-69457031 |
| 12629 | Mir26b | NR_029743.1 | chr1:74394309-74394394 | 12726 | Mir3110 | NR_037297.1 | chrX:38210440-38210520 |
| 12630 | Mir27a | NR_029744.1 | chr8:84208671-84208758 | 12727 | Mir3112 | NR_037299.1 | chrX:134075315-134075397 |
| 12631 | Mir27b | NR_029531.1 | chr13:63300711-63300784 | 12728 | Mir32 | NR_029789.1 | chr4:56895228-56895298 |
| 12632 | Mir28 | NR_029523.1 | chr18:52123624-52123546 | 12729 | Mir320 | NR_029802.1 | chr14:70443509-70443591 |
| 12633 | Mir2861 | NR_037217.1 | chr2:32712806-32712888 | 12730 | Mir322 | NR_029756.1 | chrX:53054254-53054349 |
| 12634 | Mir28b | NR_039551.1 | chr8:73016511-73016591 | 12731 | Mir323 | NR_029757.1 | chr12:109712507-109712593 |
| 12635 | Mir28c | NR_039538.1 | chr8:96545953-96545973 | 12732 | Mir324 | NR_029758.1 | chr11:70012042-70012131 |
| 12636 | Mir290 | NR_029640.1 | chr7:3218625-3218708 | 12733 | Mir325 | NR_029759.1 | chr13:107761060-107761087 |
| 12637 | Mir290b | NR_106158.1 | chr7:3218637-3218695 | 12734 | Mir326 | NR_029760.1 | chr7:99552268-99552363 |
| 12638 | Mir291a | NR_029641.1 | chr7:3218918-3219000 | 12735 | Mir328 | NR_029761.1 | chr8:105308363-105308460 |
| 12639 | Mir291b | NR_030276.1 | chr7:3219481-3219560 | 12736 | Mir329 | NR_029762.1 | chr12:109713480-109713577 |
| 12640 | Mir292 | NR_029642.1 | chr7:3219186-3219270 | 12737 | Mir33 | NR_029804.1 | chr15:82198121-82198190 |
| 12641 | Mir292b | NR_106140.1 | chr7:3219197-3219259 | 12738 | Mir330 | NR_029763.1 | chr7:19181464-19181562 |
| 12642 | Mir293 | NR_029643.1 | chr7:3220342-3220422 | 12739 | Mir331 | NR_029764.1 | chr10:93963767-93963863 |
| 12643 | Mir294 | NR_029644.1 | chr7:3220640-3220724 | 12740 | Mir335 | NR_029900.1 | chr6:30741298-30741396 |
| 12644 | Mir295 | NR_029645.1 | chr7:3220772-3220841 | 12741 | Mir337 | NR_029765.1 | chr12:109585788-109585886 |
| 12645 | Mir296 | NR_029646.1 | chr2:174267046-174267125 | 12742 | Mir338 | NR_029767.1 | chr11:120014764-120014862 |
| 12646 | Mir297-1 | NR_029647.1 | chr14:34645143-34653574 | 12743 | Mir339 | NR_029768.1 | chr5:139369649-139369745 |
| 12647 | Mir297-2 | NR_029648.2 | chr2:10472253-10472343 | 12744 | Mir340 | NR_029769.1 | chr11:50069701-50069799 |
| 12648 | Mir297a-3 | NR_030551.1 | chr2:10472253-10511772 | 12745 | Mir341 | NR_029770.1 | chr12:109611499-109611595 |
| 12649 | Mir297a-4 | NR_030552.1 | chr2:10472253-10472340 | 12746 | Mir343 | NR_030759.1 | chr7:19386642-19386717 |
| 12650 | Mir297b | NR_030474.1 | chr2:10511666-10511775 | 12747 | Mir344 | NR_029772.1 | chr7:61877769-61877864 |
| 12651 | Mir297c | NR_030555.1 | chr1:185537135-185988795 | 12748 | Mir344-2 | NR_030557.1 | chr7:61940026-61940106 |
| 12652 | Mir298 | NR_029649.1 | chr2:174267503-174267585 | 12749 | Mir344b | NR_037285.1 | chr7:61790518-61790581 |
| 12653 | Mir299 | NR_029650.1 | chr12:109710637-109710700 | 12750 | Mir344c | NR_037286.1 | chr7:61837310-61837402 |
| 12654 | Mir299b | NR_049185.1 | chr12:109710644-109710693 | 12751 | Mir344d-1 | NR_037215.1 | chr7:61683123-61683192 |
| 12655 | Mir29a | NR_029744.1 | chr6:31062659-31062747 | 12752 | Mir344d-2 | NR_037216.1 | chr7:61726248-61726323 |
| 12656 | Mir29b-1 | NR_029532.1 | chr6:31063032-31063093 | 12753 | Mir344d-3 | NR_037209.1 | chr7:61685271-61685351 |
| 12657 | Mir29b-2 | NR_029809.1 | chr1:195037039-195037120 | 12754 | Mir344e | NR_037284.1 | chr7:61735536-61735602 |
| 12658 | Mir29c | NR_029745.1 | chr1:195037546-195037634 | 12755 | Mir344f | NR_037288.1 | chr7:62046180-62046248 |
| 12659 | Mir300 | NR_029807.1 | chr12:109724312-109724391 | 12756 | Mir344g | NR_037287.1 | chr7:61982268-61982359 |
| 12660 | Mir301 | NR_029652.1 | chr11:87113003-87113089 | 12757 | Mir344h-1 | NR_049201.1 | chr7:61739349-61742425 |
| 12661 | Mir301b | NR_030415.1 | chr16:17124399-17124496 | 12758 | Mir344i | NR_049204.1 | chr7:62085222-62085310 |
| 12662 | Mir302a | NR_029653.1 | chr3:127545495-127545564 | 12759 | Mir345 | NR_029773.1 | chr12:108836972-108837068 |
| 12663 | Mir302b | NR_030403.1 | chr3:127545227-127545301 | 12760 | Mir346 | NR_029774.1 | chr14:34894608-34894706 |
| 12664 | Mir302c | NR_030404.1 | chr3:127545362-127545430 | 12761 | Mir3470a | NR_037301.1 | chr11:32390901-34462990 |
| 12665 | Mir302d | NR_030405.1 | chr3:127545623-127545689 | 12762 | Mir3470b | NR_037302.1 | chr7:143948404-144443433 |
| 12666 | Mir3057 | NR_037218.1 | chr10:81271596-81271687 | 12763 | Mir3471-1 | NR_037304.1 | chr5:23813937-24129968 |
| 12667 | Mir3058 | NR_037212.1 | chr10:95559230-95559321 | 12764 | Mir3473 | NR_037311.1 | chrX:13719852-162874995 |
| 12668 | Mir3059 | NR_037211.1 | chr10:101772691-101772772 | 12765 | Mir3473c | NR_039566.1 | chr1:191998553-191998634 |
| 12669 | Mir3060 | NR_037220.1 | chr11:4139363-4139446 | 12766 | Mir3473d | NR_039583.1 | chr8:111016449-111016530 |
| 12670 | Mir3061 | NR_037221.1 | chr11:52126745-52126836 | 12767 | Mir3473e | NR_105859.1 | chr5:31667230-31667340 |
| 12671 | Mir3062 | NR_037222.1 | chr11:68990673-68990678 | 12768 | Mir3473f | NR_106164.1 | chr1:106546495-106546631 |
| 12672 | Mir3063 | NR_037223.1 | chr11:95963291-95963383 | 12769 | Mir3473g | NR_106201.1 | chr2:126902249-126902385 |
| 12673 | Mir3064 | NR_037224.1 | chr11:106782692-106782759 | 12770 | Mir3474 | NR_037312.1 | chr2:158638582-158638640 |
| 12674 | Mir3065 | NR_037225.1 | chr11:120014766-120014853 | 12771 | Mir3475 | NR_037208.1 | chrX:140310947-140311012 |
| 12675 | Mir3066 | NR_037212.1 | chr12:17355391-17355474 | 12772 | Mir34a | NR_029655.1 | chr4:150068453-150068555 |
| 12676 | Mir3067 | NR_037227.1 | chr12:81166150-81166234 | 12773 | Mir34b | NR_029655.1 | chr9:51103561-51103645 |
| 12677 | Mir3068 | NR_037228.1 | chr12:87437678-87437757 | 12774 | Mir34c | NR_029654.1 | chr9:51103033-51103110 |
| 12678 | Mir3069 | NR_037229.1 | chr12:105031076-105031141 | 12775 | Mir350 | NR_029778.1 | chr1:176772324-176772423 |
| 12679 | Mir3070a | NR_037230.1 | chr12:109587942-109588091 | 12776 | Mir351 | NR_029776.1 | chrX:53053254-53053353 |
| 12680 | Mir3070b | NR_037231.1 | chr12:109588591-109588680 | 12777 | Mir3535 | NR_106184.1 | chr1:86351980-86352127 |
| 12681 | Mir3071 | NR_037232.1 | chr12:109595317-109595397 | 12778 | Mir3544 | NR_049184.1 | chr12:109585812-109585873 |
| 12682 | Mir3072 | NR_037233.1 | chr12:109747877-109747960 | 12779 | Mir3547 | NR_105931.1 | chr17:25245550-25245638 |
| 12683 | Mir3073 | NR_037234.1 | chr12:112109297-112109322 | 12780 | Mir3569 | NR_106134.1 | chr7:30589379-30589437 |
| 12684 | Mir3073b | NR_049197.1 | chr12:112109249-112109309 | 12781 | Mir3572 | NR_039587.1 | chr7:3655961-3656047 |
| 12685 | Mir3074-1 | NR_037235.1 | chr13:63301198-63301283 | 12782 | Mir362 | NR_029851.1 | chrX:7241982-7242046 |
| 12686 | Mir3074-2 | NR_037236.1 | chr8:84208824-84208907 | 12783 | Mir3620 | NR_106167.1 | chrX:150547384-150547445 |
| 12687 | Mir3075 | NR_037236.1 | chr14:25534438-25534523 | 12784 | Mir363 | NR_029853.1 | chrX:52741692-52741767 |
| 12688 | Mir3076 | NR_037237.1 | chr14:30572208-30572208 | 12785 | Mir365-1 | NR_029959.1 | chr16:13453839-13453926 |
| 12689 | Mir3077 | NR_037238.1 | chr14:57798423-57798487 | 12786 | Mir365-2 | NR_029959.1 | chr11:79726399-79726511 |
| 12690 | Mir3078 | NR_037239.1 | chr14:64591184-64591271 | 12787 | Mir367 | NR_030268.1 | chr3:127545732-127545807 |
| 12691 | Mir3079 | NR_037240.1 | chr1:5254697-5254622 | 12788 | Mir369 | NR_030272.1 | chr12:109743417-109743496 |
| 12692 | Mir3081 | NR_037242.1 | chr16:44558045-44558129 | 12789 | Mir370 | NR_029918.1 | chr12:109618257-109618336 |
| 12693 | Mir3082 | NR_037243.1 | chr17:25831364-25831428 | 12790 | Mir374 | NR_030418.1 | chrX:103573059-103573154 |
| 12694 | Mir3083 | NR_037244.1 | chr17:26948055-26948119 | 12791 | Mir374c | NR_037326.1 | chrX:103573084-103573133 |
| 12695 | Mir3084 | NR_037245.1 | chr17:24942235-24942303 | 12792 | Mir375 | NR_029876.1 | chr1:74900657-74900721 |
| 12696 | Mir3084-2 | NR_105743.1 | chr19:60774307-60774397 | 12793 | Mir376a | NR_029877.1 | chr12:109723780-109723848 |
| 12697 | Mir3085 | NR_037246.1 | chr19:42280081-42280170 | 12794 | Mir376b | NR_029915.1 | chr12:109723457-109723539 |
| 12698 | Mir3086 | NR_037247.1 | chr19:58911672-58911759 | 12795 | Mir376c | NR_030270.1 | chr12:109722717-109722802 |
| 12699 | Mir3087 | NR_037248.1 | chr2:25442878-25442834 | 12796 | Mir377 | NR_029878.1 | chr12:109740509-109740577 |
| 12700 | Mir3088 | NR_037271.1 | chr2:28733277-28733361 | 12797 | Mir378 | NR_029879.1 | chr9:71963440-71963460 |
| 12701 | Mir3089 | NR_037272.1 | chr2:30721209-30721293 | 12798 | Mir378b | NR_039545.1 | chr11:88352772-88352864 |
| 12702 | Mir3091 | NR_037274.1 | chr2:180257535-180257611 | 12799 | Mir378c | NR_105813.1 | chr3:97309255-97411316 |
| 12703 | Mir3092 | NR_037275.1 | chr3:27584899-27584995 | 12800 | Mir379 | NR_029880.1 | chr12:109709059-109709125 |
| 12704 | Mir3093 | NR_037276.1 | chr3:88215176-88215257 | 12801 | Mir380 | NR_029881.1 | chr12:109711802-109711863 |
| 12705 | Mir3094 | NR_037277.1 | chr4:40993694-40993758 | 12802 | Mir381 | NR_029882.1 | chr12:109726821-109726896 |
| 12706 | Mir3095 | NR_037278.1 | chr4:58441011-58441098 | 12803 | Mir382 | NR_029883.1 | chr12:109733770-109733846 |

Fig.21 - 67

| | | | | | | | | |
|---|---|---|---|---|---|---|---|---|
| 12804 | Mir383 | NR_029884.1 | chr8:38252132-38252202 | | 12901 | Mir5104 | NR_039563.1 | chr10:7836380-7836474 |
| 12805 | Mir384 | NR_029910.1 | chrX:105344281-105344369 | | 12902 | Mir5106 | NR_039565.1 | chr4:44221194-44221267 |
| 12806 | Mir3960 | NR_039536.1 | chr2:32712899-32712972 | | 12903 | Mir5107 | NR_039567.1 | chr18:60812075-60812183 |
| 12807 | Mir3962 | NR_039539.1 | chr7:144932115-144932135 | | 12904 | Mir5108 | NR_039568.1 | chr10:61774736-61774821 |
| 12808 | Mir3963 | NR_039540.1 | chr2:135405829-135405850 | | 12905 | Mir511 | NR_030609.1 | chr2:14261002-14261081 |
| 12809 | Mir3964 | NR_039542.1 | chr14:109460229-109490814 | | 12906 | Mir5112 | NR_039572.1 | chr18:82720280-82720340 |
| 12810 | Mir3965 | NR_039545.1 | chr7:99641529-99641549 | | 12907 | Mir5113 | NR_039573.1 | chr15:80940038-80940120 |
| 12811 | Mir3966 | NR_039547.1 | chr10:97423477-97423562 | | 12908 | Mir5114 | NR_039574.1 | chr19:44303170-44303231 |
| 12812 | Mir3967 | NR_039548.1 | chr2:22654282-22654350 | | 12909 | Mir5116 | NR_039576.1 | chrX:56587851-56587914 |
| 12813 | Mir3968 | NR_039549.1 | chr11:115447960-115448060 | | 12910 | Mir5119 | NR_039579.1 | chr11:98262605-98262682 |
| 12814 | Mir3969 | NR_039550.1 | chr5:87595901-87595993 | | 12911 | Mir5120 | NR_039580.1 | chr9:107486735-107486755 |
| 12815 | Mir3970 | NR_039552.1 | chr13:27010322-27010345 | | 12912 | Mir5121 | NR_039581.1 | chr7:45126917-45126991 |
| 12816 | Mir3971 | NR_039553.1 | chr1:75551428-75551511 | | 12913 | Mir5122 | NR_039582.1 | chr4:133369775-133369864 |
| 12817 | Mir409 | NR_029913.1 | chr12:109743187-109743236 | | 12914 | Mir5123 | NR_039584.1 | chr4:40850055-40850138 |
| 12818 | Mir410 | NR_029914.1 | chr12:109743715-109743795 | | 12915 | Mir5124 | NR_039585.1 | chr3:93428490-93428511 |
| 12819 | Mir411 | NR_029916.1 | chr12:109710174-109710256 | | 12916 | Mir5125 | NR_039586.1 | chr12:48219729-48301462 |
| 12820 | Mir412 | NR_029917.1 | chr12:109743288-109743368 | | 12917 | Mir5126 | NR_039588.1 | chr1:84695838-84695915 |
| 12821 | Mir421 | NR_030558.1 | chrX:103572920-103572996 | | 12918 | Mir5127 | NR_039589.1 | chr18:81992009-81992080 |
| 12822 | Mir423 | NR_030756.1 | chr11:77078083-77078172 | | 12919 | Mir5128 | NR_039590.1 | chr9:113951595-113993809 |
| 12823 | Mir425 | NR_029947.1 | chr9:108568776-108568861 | | 12920 | Mir5129 | NR_039591.1 | chr2:45023099-45023177 |
| 12824 | Mir429 | NR_029958.1 | chr4:156053904-156053987 | | 12921 | Mir5130 | NR_039592.1 | chr14:102982548-102982632 |
| 12825 | Mir431 | NR_029951.1 | chr12:109590446-109590537 | | 12922 | Mir5131 | NR_039593.1 | chr14:45657960-45658053 |
| 12826 | Mir432 | NR_035526.1 | chr12:109594955-109595030 | | 12923 | Mir5132 | NR_039594.1 | chrX:74023527-74023598 |
| 12827 | Mir433 | NR_029952.1 | chr12:109591714-109591836 | | 12924 | Mir5133 | NR_039595.1 | chr9:62122517-62122594 |
| 12828 | Mir434 | NR_029953.1 | chr12:109594509-109594599 | | 12925 | Mir5134 | NR_039596.1 | chr17:24234526-24234604 |
| 12829 | Mir448 | NR_029956.1 | chrX:147158209-147158321 | | 12926 | Mir5135 | NR_039597.1 | chr12:76533133-76533212 |
| 12830 | Mir449a | NR_029961.1 | chr13:113037533-113037624 | | 12927 | Mir5136 | NR_039598.1 | chr19:8888698-8888774 |
| 12831 | Mir449b | NR_030612.1 | chr13:113037418-113037498 | | 12928 | Mir532 | NR_030242.1 | chrX:7248401-7248497 |
| 12832 | Mir449c | NR_030452.1 | chr13:113035982-113036091 | | 12929 | Mir539 | NR_030262.1 | chr12:109728128-109729202 |
| 12833 | Mir450-1 | NR_029963.1 | chrX:53048153-53048244 | | 12930 | Mir540 | NR_030260.1 | chr12:109586079-109586146 |
| 12834 | Mir450-2 | NR_030498.1 | chrX:53048298-53048367 | | 12931 | Mir541 | NR_030263.1 | chr12:109742408-109742498 |
| 12835 | Mir450b | NR_030498.1 | chrX:53047996-53048078 | | 12932 | Mir542 | NR_030264.1 | chrX:53049402-53049487 |
| 12836 | Mir451 | NR_029971.1 | chr11:78073169-78073241 | | 12933 | Mir543 | NR_030261.1 | chr12:109717257-109717333 |
| 12837 | Mir452 | NR_029974.1 | chrX:72262223-72262308 | | 12934 | Mir544 | NR_030610.1 | chr12:109729324-109729402 |
| 12838 | Mir453 | NR_030559.1 | chr12:109735618-109735700 | | 12935 | Mir546 | NR_030259.1 | chr10:126998439-126998560 |
| 12839 | Mir455 | NR_030477.1 | chr4:63256850-63256932 | | 12936 | Mir547 | NR_030265.1 | chrX:67988373-67988451 |
| 12840 | Mir463 | NR_030147.1 | chrX:66799222-66799297 | | 12937 | Mir551b | NR_030422.1 | chr3:29416822-29416920 |
| 12841 | Mir465 | NR_030149.1 | chrX:66839051-66839125 | | 12938 | Mir5615-1 | NR_049186.1 | chr10:81104613-81104673 |
| 12842 | Mir465b-1 | NR_030560.1 | chrX:66835813-66835842 | | 12939 | Mir5615-2 | NR_049187.1 | chr10:81104615-81104675 |
| 12843 | Mir465c-1 | NR_030562.1 | chrX:66825954-66832597 | | 12940 | Mir5616 | NR_049189.1 | chr4:149537862-149537922 |
| 12844 | Mir465d | NR_106148.1 | chrX:66822655-66822713 | | 12941 | Mir5617 | NR_049190.1 | chrX:20863125-20863182 |
| 12845 | Mir466 | NR_030150.1 | chr12:112021429-112058438 | | 12942 | Mir5618 | NR_049191.1 | chr9:7784189-7784440 |
| 12846 | Mir466o | NR_037248.1 | chr12:70308504-70869399 | | 12943 | Mir5619 | NR_049192.1 | chr5:104048002-104048063 |
| 12847 | Mir466b-2 | NR_030564.1 | chr2:3523300-3523321 | | 12944 | Mir5620 | NR_049193.1 | chr7:7298890-7298946 |
| 12848 | Mir466b-3 | NR_030565.1 | chr2:10503564-10503645 | | 12945 | Mir5621 | NR_049194.1 | chr11:115795823-115795886 |
| 12849 | Mir466d | NR_030601.1 | chr2:5379389-5483389 | | 12946 | Mir5622 | NR_049195.1 | chr2:152865066-152865126 |
| 12850 | Mir466f-1 | NR_030566.1 | chr19:12071789-12413554 | | 12947 | Mir5623 | NR_049196.1 | chr19:58051166-58051236 |
| 12851 | Mir466f-2 | NR_030567.1 | chr7:28452226-28482345 | | 12948 | Mir5624 | NR_049198.1 | chr13:93790776-93790837 |
| 12852 | Mir466f-3 | NR_030568.1 | chr14:75004109-75388146 | | 12949 | Mir5625 | NR_049199.1 | chr5:30647935-30648015 |
| 12853 | Mir466g | NR_030569.1 | chr2:10514195-10514674 | | 12950 | Mir5626 | NR_049200.1 | chr9:70405693-70405753 |
| 12854 | Mir466h | NR_030570.1 | chr4:81476308-81487013 | | 12951 | Mir5627 | NR_049203.1 | chr12:44210312-44210373 |
| 12855 | Mir466i | NR_035412.1 | chr13:17747472-17747593 | | 12952 | Mir568 | NR_030576.1 | chr16:43640654-43640737 |
| 12856 | Mir466n | NR_037269.1 | chr11:114344525-114749749 | | 12953 | Mir5709 | NR_049205.1 | chr17:67026146-67026235 |
| 12857 | Mir466p | NR_105742.1 | chr18:65195452-66619615 | | 12954 | Mir5710 | NR_049206.1 | chr9:54708312-54708381 |
| 12858 | Mir467a-1 | NR_035406.1 | chr2:10476349-10503350 | | 12955 | Mir574 | NR_030577.1 | chr5:64970317-64970395 |
| 12859 | Mir467a-10 | NR_037267.1 | chr2:10503273-10503355 | | 12956 | Mir582 | NR_030644.1 | chr13:109324743-109324823 |
| 12860 | Mir467a-2 | NR_037249.1 | chr2:10478798-10478880 | | 12957 | Mir592 | NR_030420.1 | chr6:27986654-27986750 |
| 12861 | Mir467a-3 | NR_037252.1 | chr2:10483677-10503355 | | 12958 | Mir598 | NR_030611.1 | chr14:63727188-63727267 |
| 12862 | Mir467a-5 | NR_037256.1 | chr2:10476341-10500904 | | 12959 | Mir599 | NR_035527.1 | chr15:35660830-35660918 |
| 12863 | Mir467a-7 | NR_037261.1 | chr2:10493510-10493592 | | 12960 | Mir615 | NR_030626.1 | chr15:103014909-103015001 |
| 12864 | Mir467a-9 | NR_037265.1 | chr2:10498393-10498475 | | 12961 | Mir6236 | NR_105744.1 | chr9:110281286-110281409 |
| 12865 | Mir467b | NR_030472.1 | chr2:10481247-10481320 | | 12962 | Mir6237 | NR_105745.1 | chr9:9894430-9894521 |
| 12866 | Mir467c | NR_037571.1 | chr13:86416843-86520291 | | 12963 | Mir6238 | NR_105746.1 | chr7:53891760-53891889 |
| 12867 | Mir467d | NR_030572.1 | chr2:10507629-10507714 | | 12964 | Mir6239 | NR_105747.1 | chr14:117953742-117953847 |
| 12868 | Mir467e | NR_030645.1 | chr1:10708386-10865874 | | 12965 | Mir6241 | NR_105749.1 | chr14:118258633-118258736 |
| 12869 | Mir467f | NR_030646.1 | chr18:52922107-52902647 | | 12966 | Mir6244 | NR_105750.1 | chr9:52115622-52115739 |
| 12870 | Mir468 | NR_030151.1 | chr6:81896598-81896676 | | 12967 | Mir6335 | NR_105752.1 | chr2:67781042-67781140 |
| 12871 | Mir470 | NR_030153.1 | chrX:66813950-66814025 | | 12968 | Mir6336 | NR_105754.1 | chr2:42447438-42447568 |
| 12872 | Mir471 | NR_030154.1 | chrX:66792594-66792661 | | 12969 | Mir6337 | NR_105755.1 | chr2:65364295-65364400 |
| 12873 | Mir483 | NR_030251.1 | chr7:142654923-142654996 | | 12970 | Mir6338 | NR_105756.1 | chr11:72388755-72388864 |
| 12874 | Mir484 | NR_030252.1 | chr16:14159026-14159692 | | 12971 | Mir6339 | NR_105757.1 | chr2:130016291-130016408 |
| 12875 | Mir485 | NR_030253.1 | chr12:109734903-109734974 | | 12972 | Mir6340 | NR_105758.1 | chr2:173701029-173701148 |
| 12876 | Mir486 | NR_030254.1 | chr8:23142654-23142682 | | 12973 | Mir6341 | NR_105759.1 | chr1:12425985-12426106 |
| 12877 | Mir487b | NR_030271.1 | chr12:109727414-109727414 | | 12974 | Mir6342 | NR_105760.1 | chr1:29421487-29421612 |
| 12878 | Mir488 | NR_030441.1 | chr1:158505624-158505733 | | 12975 | Mir6343 | NR_105761.1 | chr1:76509559-76509643 |
| 12879 | Mir489 | NR_030250.1 | chr6:3721896-3722003 | | 12976 | Mir6344 | NR_105762.1 | chr1:82131915-82132019 |
| 12880 | Mir490 | NR_030524.1 | chr6:36421741-36421825 | | 12977 | Mir6345 | NR_105763.1 | chr1:93352157-93352285 |
| 12881 | Mir491 | NR_030478.1 | chr4:88122039-88122125 | | 12978 | Mir6348 | NR_105766.1 | chr1:168490642-168490762 |
| 12882 | Mir493 | NR_030535.1 | chr12:109580232-109580315 | | 12979 | Mir6349 | NR_105767.1 | chr1:39186895-39186992 |
| 12883 | Mir494 | NR_030269.1 | chr12:109715317-109715402 | | 12980 | Mir6350 | NR_105768.1 | chr1:47467020-47467125 |
| 12884 | Mir495 | NR_030446.1 | chr12:109718753-109718816 | | 12981 | Mir6352 | NR_105770.1 | chr1:77496652-77496768 |
| 12885 | Mir496 | NR_030437.1 | chr12:109739118-109739197 | | 12982 | Mir6353 | NR_105771.1 | chr1:84218848-84218961 |
| 12886 | Mir496b | NR_105852.1 | chr19:16314891-16315004 | | 12983 | Mir6354 | NR_105772.1 | chr11:62960060-63386069 |
| 12887 | Mir497 | NR_030444.1 | chr11:70234716-70234800 | | 12984 | Mir6355 | NR_105773.1 | chr18:59579629-59579735 |
| 12888 | Mir497b | NR_106149.1 | chr11:70234691-70234816 | | 12985 | Mir6356 | NR_105774.1 | chr18:68739399-68739501 |
| 12889 | Mir499 | NR_030757.1 | chr2:155622879-155622958 | | 12986 | Mir6357 | NR_105775.1 | chr18:70516785-70516889 |
| 12890 | Mir500 | NR_030495.1 | chrX:7237682-7237774 | | 12987 | Mir6358 | NR_105776.1 | chr18:76170551-76170652 |
| 12891 | Mir501 | NR_030496.1 | chrX:7241242-7241351 | | 12988 | Mir6359 | NR_105777.1 | chr18:88972029-88972110 |
| 12892 | Mir503 | NR_030275.1 | chrX:53053983-53054054 | | 12989 | Mir6360 | NR_105778.1 | chr18:23774863-23774989 |
| 12893 | Mir504 | NR_030574.1 | chrX:59097657-59097736 | | 12990 | Mir6361 | NR_105779.1 | chr18:32880572-32880673 |
| 12894 | Mir5046 | NR_039555.1 | chr19:68298835-68298944 | | 12991 | Mir6362 | NR_105781.1 | chr5:29789010-29970488 |
| 12895 | Mir505 | NR_030499.1 | chrX:60394402-60394492 | | 12992 | Mir6363 | NR_105782.1 | chr16:50727131-50727245 |
| 12896 | Mir509 | NR_030500.1 | chrX:68010104-68010179 | | 12993 | Mir6364 | NR_105783.1 | chr2:166672717-166722152 |
| 12897 | Mir509B | NR_039557.1 | chr2:28127350-119928917 | | 12994 | Mir6365 | NR_105784.1 | chr16:13471079-13471180 |
| 12898 | Mir5100 | NR_039559.1 | chr12:672682-60728726 | | 12995 | Mir6366 | NR_105785.1 | chr16:18165088-18165170 |
| 12899 | Mir5101 | NR_039560.1 | chr12:75909102-75909185 | | 12996 | Mir6367 | NR_105786.1 | chr19:9017903-9017931 |
| 12900 | Mir5103 | NR_039562.1 | chr1:34433120-34433199 | | 12997 | Mir6368 | NR_105787.1 | chr13:28710780-28710873 |

Fig.21 - 68

| | | | | | | | | |
|---|---|---|---|---|---|---|---|---|
| 12998 | Mir6369 | NR_105788.1 | chr13:58313043-58313149 | | 13095 | Mir684-1 | NR_030454.1 | chr2:7753088-129665839 |
| 12999 | Mir6370 | NR_105789.1 | chr6:19555341-19555461 | | 13096 | Mir684-2 | NR_030455.1 | chr4:11134096-111134182 |
| 13000 | Mir6372 | NR_105791.1 | chr11:26202239-26202348 | | 13097 | Mir686 | NR_030457.1 | chr14:54616676-54616785 |
| 13001 | Mir6373 | NR_105792.1 | chr6:102794383-102794485 | | 13098 | Mir687 | NR_030459.1 | chr14:73206762-73206851 |
| 13002 | Mir6374 | NR_105793.1 | chr6:83400995-83401102 | | 13099 | Mir688 | NR_030460.1 | chr15:102671791-102671866 |
| 13003 | Mir6375 | NR_105794.1 | chr6:85790139-85790234 | | 13100 | Mir6896 | NR_105861.1 | chr1:34117358-34117431 |
| 13004 | Mir6376 | NR_105795.1 | chr6:88104127-88104258 | | 13101 | Mir6897 | NR_105862.1 | chr1:36144251-36144313 |
| 13005 | Mir6378 | NR_105799.1 | chr3:34922544-34922651 | | 13102 | Mir6898 | NR_105863.1 | chr1:36348681-36348758 |
| 13006 | Mir6380 | NR_105801.1 | chr11:47739591-48074583 | | 13103 | Mir6899 | NR_105864.1 | chr1:64042437-64042501 |
| 13007 | Mir6381 | NR_105802.1 | chr3:142623859-142623946 | | 13104 | Mir690 | NR_030463.1 | chr16:28599934-28600043 |
| 13008 | Mir6382 | NR_105803.1 | chrX:106309825-106309935 | | 13105 | Mir6900 | NR_105865.1 | chr1:92464482-92464542 |
| 13009 | Mir6383 | NR_105804.1 | chrX:136183244-136183360 | | 13106 | Mir6901 | NR_105866.1 | chr1:93274548-93274610 |
| 13010 | Mir6384 | NR_105805.1 | chrX:52378120-52378181 | | 13107 | Mir6902 | NR_105867.1 | chr1:93346091-93346155 |
| 13011 | Mir6385 | NR_105806.1 | chr9:58221149-58221254 | | 13108 | Mir6903 | NR_105868.1 | chr1:137726557-137726645 |
| 13012 | Mir6386 | NR_105808.1 | chr9:92267257-92267361 | | 13109 | Mir6904 | NR_105869.1 | chr1:180587200-180587267 |
| 13013 | Mir6387 | NR_105809.1 | chr12:15800993-15801101 | | 13110 | Mir6905 | NR_105870.1 | chr10:24910663-24910733 |
| 13014 | Mir6388 | NR_105810.1 | chr12:115695719-115695794 | | 13111 | Mir6906 | NR_105871.1 | chr10:60126775-60126833 |
| 13015 | Mir6389 | NR_105812.1 | chr7:57581060-57581162 | | 13112 | Mir6907 | NR_105872.1 | chr10:78408474-78408545 |
| 13016 | Mir6390 | NR_105814.1 | chr14:105623643-105623770 | | 13113 | Mir6908 | NR_105873.1 | chr10:78445094-78445157 |
| 13017 | Mir6391 | NR_105815.1 | chr14:118592368-118592472 | | 13114 | Mir6909 | NR_105874.1 | chr10:79531028-79531090 |
| 13018 | Mir6392 | NR_105816.1 | chr15:84168269-84168377 | | 13115 | Mir691 | NR_030464.1 | chr16:74341989-74342067 |
| 13019 | Mir6393 | NR_105817.1 | chr15:87795849-87795943 | | 13116 | Mir6910 | NR_105875.1 | chr10:79862586-79862652 |
| 13020 | Mir6394 | NR_105818.1 | chr7:96305666-96305765 | | 13117 | Mir6911 | NR_105876.1 | chr10:80278163-80278232 |
| 13021 | Mir6395 | NR_105820.1 | chr8:34166621-34166712 | | 13118 | Mir6912 | NR_105877.1 | chr10:80609259-80609329 |
| 13022 | Mir6396 | NR_105821.1 | chr8:122622264-122622375 | | 13119 | Mir6913 | NR_105878.1 | chr10:81386346-81386412 |
| 13023 | Mir6397 | NR_105823.1 | chr4:108087356-108087449 | | 13120 | Mir6914 | NR_105879.1 | chr10:128382857-128382906 |
| 13024 | Mir6398 | NR_105824.1 | chr4:123616419-123616621 | | 13121 | Mir6915 | NR_105880.1 | chr10:128388831-128388900 |
| 13025 | Mir6399 | NR_105825.1 | chr4:138163208-138163292 | | 13122 | Mir6916 | NR_105881.1 | chr10:128511967-128512030 |
| 13026 | Mir6400 | NR_105826.1 | chr4:15942899-15942991 | | 13123 | Mir6917 | NR_105882.1 | chr10:128584486-128584497 |
| 13027 | Mir6401 | NR_105827.1 | chr7:139779017-139779126 | | 13124 | Mir6918 | NR_105883.1 | chr11:4891344-4891402 |
| 13028 | Mir6402 | NR_105828.1 | chr4:91373283-91373363 | | 13125 | Mir6919 | NR_105884.1 | chr11:50232244-50232306 |
| 13029 | Mir6403 | NR_105829.1 | chr4:134567722-134567851 | | 13126 | Mir6920 | NR_105885.1 | chr11:53409196-53409267 |
| 13030 | Mir6404 | NR_105830.1 | chr7:143933114-143933208 | | 13127 | Mir6921 | NR_105886.1 | chr11:60200637-60200617 |
| 13031 | Mir6405 | NR_105831.1 | chr19:44808525-44808529 | | 13128 | Mir692-1 | NR_030465.1 | chr17:6895228-6895337 |
| 13032 | Mir6406 | NR_105833.1 | chr11:68220891-68221011 | | 13129 | Mir6922 | NR_105887.1 | chr11:60202261-60202327 |
| 13033 | Mir6407 | NR_105834.1 | chr19:53010695-53010756 | | 13130 | Mir692-2b | NR_035409.1 | chr4:74407064-125504857 |
| 13034 | Mir6408 | NR_105835.1 | chr10:69023022-60923113 | | 13131 | Mir6923 | NR_105888.1 | chr11:67099803-67099875 |
| 13035 | Mir6409 | NR_105836.1 | chr10:76008925-76009017 | | 13132 | Mir6924 | NR_105889.1 | chr11:69882031-69882094 |
| 13036 | Mir6410 | NR_105837.1 | chr10:78434798-78434902 | | 13133 | Mir6925 | NR_105890.1 | chr11:70705989-70706059 |
| 13037 | Mir6411 | NR_105838.1 | chr10:104287268-104287376 | | 13134 | Mir6926 | NR_105891.1 | chr11:74868126-74868194 |
| 13038 | Mir6412 | NR_105839.1 | chr17:30256456-30256535 | | 13135 | Mir6927 | NR_105892.1 | chr11:97677059-97677130 |
| 13039 | Mir6413 | NR_105840.1 | chr10:20297580-20297688 | | 13136 | Mir6928 | NR_105893.1 | chr11:101030339-101030409 |
| 13040 | Mir6414 | NR_105842.1 | chr5:41891341-41891423 | | 13137 | Mir6929 | NR_105894.1 | chr11:101419186-101419253 |
| 13041 | Mir6415 | NR_105843.1 | chr5:92458556-92458656 | | 13138 | Mir693 | NR_030466.1 | chr17:46231530-46231619 |
| 13042 | Mir6416 | NR_105844.1 | chr7:64249982-64250099 | | 13139 | Mir6930 | NR_105895.1 | chr11:102404919-102404987 |
| 13043 | Mir6417 | NR_105845.1 | chr5:52135901-52136017 | | 13140 | Mir6931 | NR_105896.1 | chr11:102999847-102999921 |
| 13044 | Mir6418 | NR_105846.1 | chr5:137529479-137529594 | | 13141 | Mir6932 | NR_105897.1 | chr11:107637721-107637779 |
| 13045 | Mir6419 | NR_105847.1 | chr2:17563513-17563626 | | 13142 | Mir6933 | NR_105898.1 | chr11:118002269-118002350 |
| 13046 | Mir6420 | NR_105848.1 | chr17:64440806-64440907 | | 13143 | Mir6934 | NR_105899.1 | chr13:119154075-119154137 |
| 13047 | Mir6481 | NR_105852.1 | chr3:99199344-99199463 | | 13144 | Mir6935 | NR_105900.1 | chr11:120347349-120347413 |
| 13048 | Mir6516 | NR_105853.1 | chr11:117077347-117077457 | | 13145 | Mir6936 | NR_105901.1 | chr11:120624822-120624876 |
| 13049 | Mir653 | NR_030612.1 | chr6:3721300-3721385 | | 13146 | Mir6937 | NR_105902.1 | chr12:28679324-28679389 |
| 13050 | Mir6537 | NR_105855.1 | chr7:25097065-25097175 | | 13147 | Mir6938 | NR_105903.1 | chr12:85245922-85245985 |
| 13051 | Mir6538 | NR_105856.1 | chr12:26414900-26415010 | | 13148 | Mir6939 | NR_105904.1 | chr12:112659276-112659351 |
| 13052 | Mir6539 | NR_105857.1 | chr14:67859635-67859745 | | 13149 | Mir694 | NR_030467.1 | chr18:66219263-66219331 |
| 13053 | Mir654 | NR_030578.1 | chr12:109723217-109723301 | | 13150 | Mir6940 | NR_105905.1 | chr12:112733321-112733391 |
| 13054 | Mir6540 | NR_105858.1 | chr16:42303361-42303469 | | 13151 | Mir6941 | NR_105906.1 | chr12:112920482-112920541 |
| 13055 | Mir6541 | NR_105860.1 | chr14:62865541-62865651 | | 13152 | Mir6942 | NR_105907.1 | chr13:21396638-21396638 |
| 13056 | Mir6546 | NR_106103.1 | chr1:171064590-171064652 | | 13153 | Mir6943 | NR_105908.1 | chr13:55453105-55453171 |
| 13057 | Mir664 | NR_035529.1 | chr1:185242974-185243043 | | 13154 | Mir6944 | NR_105909.1 | chr13:55477680-55477776 |
| 13058 | Mir665 | NR_030435.1 | chr12:109586313-109586407 | | 13155 | Mir6945 | NR_105910.1 | chr13:55507624-55507692 |
| 13059 | Mir666 | NR_030435.1 | chr12:109717084-109717183 | | 13156 | Mir6946 | NR_105911.1 | chr14:20690694-20690703 |
| 13060 | Mir667 | NR_030424.1 | chr12:109720095-109720097 | | 13157 | Mir6947 | NR_105912.1 | chr14:29988887-29988952 |
| 13061 | Mir668 | NR_030424.1 | chr12:109734731-109734797 | | 13158 | Mir6948 | NR_105913.1 | chr14:54643048-54643110 |
| 13062 | Mir669a-1 | NR_035408.1 | chr2:10476852-10503883 | | 13159 | Mir6949 | NR_105914.1 | chr14:56082400-56082488 |
| 13063 | Mir669a-2 | NR_030470.1 | chr2:10476850-10510260 | | 13160 | Mir695 | NR_030475.1 | chr2:155356816-155356925 |
| 13064 | Mir669a-3 | NR_030471.1 | chr2:10474432-10474541 | | 13161 | Mir6950 | NR_105915.1 | chr14:69692247-69692320 |
| 13065 | Mir669a-4 | NR_037250.1 | chr17:51277987-51613053 | | 13162 | Mir6951 | NR_105916.1 | chr15:38490472-38490547 |
| 13066 | Mir669b | NR_030469.1 | chr8:114863252-115027151 | | 13163 | Mir6952 | NR_105917.1 | chr15:76064827-76064888 |
| 13067 | Mir669c | NR_030473.1 | chr12:91110228-91123337 | | 13164 | Mir6953 | NR_105918.1 | chr15:76248190-76248258 |
| 13068 | Mir669e | NR_035474.1 | chr8:39467447-40227787 | | 13165 | Mir6954 | NR_105919.1 | chr15:76433213-76433273 |
| 13069 | Mir669g | NR_035411.1 | chr2:10477149-10477272 | | 13166 | Mir6955 | NR_105920.1 | chr15:78891839-78891913 |
| 13070 | Mir669h | NR_035418.1 | chr19:113586577-113614774 | | 13167 | Mir6956 | NR_105921.1 | chr15:79002222-79002284 |
| 13071 | Mir669i | NR_035417.1 | chr2:10517603-10517730 | | 13168 | Mir6957 | NR_105922.1 | chr15:80646072-80646136 |
| 13072 | Mir669j | NR_035416.1 | chr2:10477909-10478030 | | 13169 | Mir6958 | NR_105923.1 | chr15:89185464-89185537 |
| 13073 | Mir669k | NR_035410.1 | chr2:10475299-10475426 | | 13170 | Mir6959 | NR_105924.1 | chr15:89305657-89305732 |
| 13074 | Mir669m-1 | NR_035412.1 | chr5:78929669-79515904 | | 13171 | Mir6960 | NR_105925.1 | chr15:99080804-99080885 |
| 13075 | Mir669m-2 | NR_035475.1 | chrX:77164402-77475936 | | 13172 | Mir6961 | NR_105926.1 | chr15:100649162-100649229 |
| 13076 | Mir669p-1 | NR_037257.1 | chr17:51277987-51613053 | | 13173 | Mir6962 | NR_105927.1 | chr15:101193868-101193931 |
| 13077 | Mir670 | NR_030431.1 | chr2:94261299-94261399 | | 13174 | Mir6963 | NR_105928.1 | chr15:103350454-103350525 |
| 13078 | Mir671 | NR_030423.1 | chr5:24592113-24592211 | | 13175 | Mir6964 | NR_105929.1 | chr16:97877232-97877291 |
| 13079 | Mir671S | NR_106116.1 | chr19:55192677-55192734 | | 13176 | Mir6965 | NR_105930.1 | chr17:24240882-24240947 |
| 13080 | Mir672 | NR_030430.1 | chrX:104116174-104116274 | | 13177 | Mir6966 | NR_105932.1 | chr17:25780807-25780879 |
| 13081 | Mir673 | NR_030438.1 | chr12:109571989-109572080 | | 13178 | Mir6968 | NR_105934.1 | chr17:26935471-26935539 |
| 13082 | Mir674 | NR_030440.1 | chr2:117185126-117185226 | | 13179 | Mir6969 | NR_105935.1 | chr17:28558440-28558501 |
| 13083 | Mir675 | NR_030416.1 | chr7:142577063-142577147 | | 13180 | Mir697 | NR_030479.1 | chr4:124731693-124731802 |
| 13084 | Mir676 | NR_030525.1 | chrX:100381096-100381185 | | 13181 | Mir6970 | NR_105936.1 | chr17:34845100-34845167 |
| 13085 | Mir6769b | NR_106035.1 | chr8:71631046-71631106 | | 13182 | Mir6971 | NR_105937.1 | chr17:34841808-34841871 |
| 13086 | Mir677 | NR_030442.2 | chr10:128085285-128085363 | | 13183 | Mir6972 | NR_105938.1 | chr17:34857568-34857632 |
| 13087 | Mir678 | NR_030443.1 | chr10:76207325-76207409 | | 13184 | Mir6973a | NR_105939.1 | chr15:194971-35195049 |
| 13088 | Mir679 | NR_030445.1 | chr12:109715576-109715650 | | 13185 | Mir6973b | NR_105969.1 | chr2:131040318-131040398 |
| 13089 | Mir680-2 | NR_030448.1 | chr9:22057712-22057923 | | 13186 | Mir6974 | NR_105940.1 | chr17:35204474-35204537 |
| 13090 | Mir680-3 | NR_030449.1 | chr10:25894599-25894505 | | 13187 | Mir6975 | NR_105941.1 | chr24:284074-35244135 |
| 13091 | Mir681 | NR_030450.1 | chr12:69763834-69763944 | | 13188 | Mir6976 | NR_105942.1 | chr17:46553826-46553889 |
| 13092 | Mir682 | NR_030452.1 | chr5:75645045-75645141 | | 13189 | Mir6977 | NR_105943.1 | chr17:56418845-56418909 |
| 13093 | Mir683-1 | NR_030453.1 | chr13:50544626-50544734 | | 13190 | Mir6978 | NR_105944.1 | chr17:57217171-57217228 |
| 13094 | Mir683-2 | NR_030647.1 | chr13:50600972-50601080 | | 13191 | Mir6979 | NR_105945.1 | chr18:37854604-37854660 |

Fig.21 - 69

| | | | | | | | |
|---|---|---|---|---|---|---|---|
| 13192 | Mir698 | NR_030480.1 | chr4:124743780-124743889 | 13289 | Mir7068 | NR_106036.1 | chr8:72470015-72470089 |
| 13193 | Mir6980 | NR_105946.1 | chr18:37990886-37990945 | 13290 | Mir7069 | NR_106037.1 | chr8:84867946-84868008 |
| 13194 | Mir6981 | NR_105947.1 | chr18:37974502-37974617 | 13291 | Mir707 | NR_030488.1 | chr7:44849698-44849771 |
| 13195 | Mir6982 | NR_105948.1 | chr18:60958072-60958140 | 13292 | Mir7070 | NR_106038.1 | chr8:85062085-85062171 |
| 13196 | Mir6983 | NR_105949.1 | chr18:61117467-61117531 | 13293 | Mir7071 | NR_106039.1 | chr8:88138205-88138274 |
| 13197 | Mir6984 | NR_105950.1 | chr19:3288919-3288983 | 13294 | Mir7072 | NR_106040.1 | chr8:94505045-94505105 |
| 13198 | Mir6985 | NR_105951.1 | chr19:4263817-4263878 | 13295 | Mir7073 | NR_106041.1 | chr8:95753150-95753214 |
| 13199 | Mir6986 | NR_105952.1 | chr19:4623897-4623955 | 13296 | Mir7074 | NR_106042.1 | chr8:105951636-105951699 |
| 13200 | Mir6987 | NR_105953.1 | chr19:5679003-5679076 | 13297 | Mir7075 | NR_106043.1 | chr8:107096024-107096106 |
| 13201 | Mir6988 | NR_105954.1 | chr19:6051333-6051392 | 13298 | Mir7076 | NR_106044.1 | chr8:111689600-111689674 |
| 13202 | Mir6989 | NR_105955.1 | chr11:46232134-46181905 | 13299 | Mir7077 | NR_106045.1 | chr8:117453022-117453079 |
| 13203 | Mir6990 | NR_105956.1 | chr19:6914195-6914286 | 13300 | Mir7078 | NR_106046.1 | chr8:117459264-117459328 |
| 13204 | Mir6991 | NR_105957.1 | chr19:7422572-7422642 | 13301 | Mir7079 | NR_106047.1 | chr8:123104974-123105043 |
| 13205 | Mir6992 | NR_105958.1 | chr19:8742970-8743079 | 13302 | Mir708 | NR_030489.1 | chr7:96249423-96249532 |
| 13206 | Mir6993 | NR_105959.1 | chr19:10191374-10191439 | 13303 | Mir7080 | NR_106048.1 | chr8:123130105-123136172 |
| 13207 | Mir6994 | NR_105960.1 | chr19:11923727-11923800 | 13304 | Mir7081 | NR_106049.1 | chr9:20914089-20914164 |
| 13208 | Mir6995 | NR_105961.1 | chr19:47273518-47273589 | 13305 | Mir7082 | NR_106050.1 | chr9:21075496-21075588 |
| 13209 | Mir6996 | NR_105962.1 | chr2:26470058-26470119 | 13306 | Mir7083 | NR_106051.1 | chr9:21809940-21810000 |
| 13210 | Mir6997 | NR_105963.1 | chr2:29995949-29996020 | 13307 | Mir7084 | NR_106052.1 | chr9:22113943-22114013 |
| 13211 | Mir6998 | NR_105964.1 | chr2:31612420-31612484 | 13308 | Mir7085 | NR_106053.1 | chr9:44400422-44400488 |
| 13212 | Mir6999 | NR_105965.1 | chr2:91944869-91944930 | 13309 | Mir7086 | NR_106054.1 | chr9:45266642-45266707 |
| 13213 | Mir700 | NR_030481.1 | chr4:135416554-135416633 | 13310 | Mir7087 | NR_106055.1 | chr9:45939520-45939590 |
| 13214 | Mir7000 | NR_105966.1 | chr2:92387383-92387446 | 13311 | Mir7088 | NR_106056.1 | chr9:108081497-108081583 |
| 13215 | Mir7001 | NR_105967.1 | chr2:93421928-93422007 | 13312 | Mir7089 | NR_106057.1 | chr9:109889642-109889716 |
| 13216 | Mir7002 | NR_105968.1 | chr2:114150515-114150570 | 13313 | Mir709 | NR_030490.1 | chr8:84086098-84086186 |
| 13217 | Mir7003 | NR_105970.1 | chr2:163068089-163068155 | 13314 | Mir7090 | NR_106058.1 | chr9:120955085-120955147 |
| 13218 | Mir7004 | NR_105971.1 | chr2:168640695-168640759 | 13315 | Mir7091 | NR_106059.1 | chrX:74274026-74274105 |
| 13219 | Mir7005 | NR_105972.1 | chr2:180179754-180179823 | 13316 | Mir7092 | NR_106060.1 | chrX:74317361-74317429 |
| 13220 | Mir7006 | NR_105973.1 | chr2:181587899-181587968 | 13317 | Mir7093 | NR_106061.1 | chr12:134757630-134757731 |
| 13221 | Mir7007 | NR_105974.1 | chr3:20222289-20222359 | 13318 | Mir7094-1 | NR_106062.1 | chr12:114469406-114469486 |
| 13222 | Mir7008 | NR_105975.1 | chr3:31039965-31039028 | 13319 | Mir7094-2 | NR_106063.1 | chr12:114513634-114513694 |
| 13223 | Mir7009 | NR_105976.1 | chr3:36475460-36475524 | 13320 | Mir7-1 | NR_029825.1 | chr13:58392778-58392886 |
| 13224 | Mir701 | NR_030482.1 | chr5:111004143-111004252 | 13321 | Mir710 | NR_030491.1 | chr5:64514333-64514441 |
| 13225 | Mir7010 | NR_105977.1 | chr3:82106246-82106309 | 13322 | Mir711 | NR_030492.1 | chr9:108969921-108970003 |
| 13226 | Mir7011 | NR_105978.1 | chr3:88440878-88440951 | 13323 | Mir7115 | NR_106064.1 | chr11:70438254-70438318 |
| 13227 | Mir7012 | NR_105979.1 | chr3:90270148-90270212 | 13324 | Mir7117 | NR_106065.1 | chr15:27571493-27571558 |
| 13228 | Mir7013 | NR_105980.1 | chr3:95004167-95004239 | 13325 | Mir7118 | NR_106066.1 | chr15:89162847-89162908 |
| 13229 | Mir7014 | NR_105981.1 | chr3:95734910-95734973 | 13326 | Mir7119 | NR_106067.1 | chr4:126559859-126559918 |
| 13230 | Mir7015 | NR_105982.1 | chr4:120973258-120973322 | 13327 | Mir713 | NR_030493.1 | chr13:62760738-62760846 |
| 13231 | Mir7016 | NR_105983.1 | chr4:129684499-129684571 | 13328 | Mir717 | NR_030497.1 | chrX:52422406-52422515 |
| 13232 | Mir7017 | NR_105984.1 | chr4:133195654-133195716 | 13329 | Mir718 | NR_030758.1 | chrX:74023848-74023936 |
| 13233 | Mir7018 | NR_105985.1 | chr4:137538285-137538370 | 13330 | Mir719 | NR_030454.1 | chr14:60228805-60228915 |
| 13234 | Mir7019 | NR_105986.1 | chr4:138316131-138316200 | 13331 | Mir7-2 | NR_029826.1 | chr7:78888276-78888373 |
| 13235 | Mir702 | NR_030483.1 | chr5:136991432-136991541 | 13332 | Mir721 | NR_030500.1 | chr5:136375715-136375803 |
| 13236 | Mir7020 | NR_105987.1 | chr4:139644041-139644111 | 13333 | Mir7210 | NR_106069.1 | chr14:24088876-24088930 |
| 13237 | Mir7021 | NR_105988.1 | chr4:143136099-143136162 | 13334 | Mir7211 | NR_106070.1 | chr10:94586136-94586199 |
| 13238 | Mir7022 | NR_105989.1 | chr4:148146935-148146996 | 13335 | Mir7212 | NR_106071.1 | chr15:25948226-25948287 |
| 13239 | Mir7023 | NR_105990.1 | chr4:149655503-149655567 | 13336 | Mir7213 | NR_106072.1 | chr15:79998969-79999026 |
| 13240 | Mir7024 | NR_105991.1 | chr5:33898909-33898971 | 13337 | Mir7214 | NR_106073.1 | chr17:27317034-27317095 |
| 13241 | Mir7025 | NR_105992.1 | chr5:75176830-75176904 | 13338 | Mir7215 | NR_106074.1 | chr10:62682507-62682558 |
| 13242 | Mir7026 | NR_105993.1 | chr5:110666074-110666141 | 13339 | Mir7216 | NR_106075.1 | chr17:27328384-27328460 |
| 13243 | Mir7027 | NR_105994.1 | chr5:114404467-114404539 | 13340 | Mir7217 | NR_106076.1 | chr17:27355737-27355799 |
| 13244 | Mir7028 | NR_105995.1 | chr5:114719514-114719578 | 13341 | Mir7218 | NR_106077.1 | chr17:27358096-27358155 |
| 13245 | Mir7029 | NR_105996.1 | chr5:115580948-115581009 | 13342 | Mir7219 | NR_106078.1 | chr18:68260919-68260973 |
| 13246 | Mir703 | NR_030484.1 | chr5:98475553-98475664 | 13343 | Mir7220 | NR_106079.1 | chr18:60953872-60953932 |
| 13247 | Mir7030 | NR_105997.1 | chr5:115645572-115645632 | 13344 | Mir7221 | NR_106080.1 | chr2:92592205-92592277 |
| 13248 | Mir7031 | NR_105998.1 | chr5:121819208-121819273 | 13345 | Mir7222 | NR_106081.1 | chr2:92594601-92594676 |
| 13249 | Mir7032 | NR_105999.1 | chr5:123996851-123996930 | 13346 | Mir7223 | NR_106082.1 | chr11:107996847-107996916 |
| 13250 | Mir7033 | NR_106000.1 | chr5:135383729-135383810 | 13347 | Mir7224 | NR_106083.1 | chr2:67675456-67675516 |
| 13251 | Mir7034 | NR_106001.1 | chr5:135735805-135735889 | 13348 | Mir7225 | NR_106084.1 | chr3:97690508-97690562 |
| 13252 | Mir7035 | NR_106002.1 | chr5:136105521-136105603 | 13349 | Mir7226 | NR_106085.1 | chr4:118210504-118210564 |
| 13253 | Mir7036 | NR_106003.1 | chr5:137296623-137296688 | 13350 | Mir7227 | NR_106086.1 | chr4:133717049-133717108 |
| 13254 | Mir7036b | NR_106111.1 | chr5:10340-34574213 | 13351 | Mir7228 | NR_106087.1 | chr5:134572075-134572114 |
| 13255 | Mir7037 | NR_106004.1 | chr5:139767878-139767943 | 13352 | Mir7229 | NR_106088.1 | chr5:113324492-113324545 |
| 13256 | Mir7038 | NR_106005.1 | chr5:140427338-140427409 | 13353 | Mir7230 | NR_106089.1 | chr5:113337589-113337645 |
| 13257 | Mir7039 | NR_106006.1 | chr5:144896816-144896816 | 13354 | Mir7231 | NR_106090.1 | chr6:122831376-122831437 |
| 13258 | Mir704 | NR_030485.1 | chr6:47803575-47803652 | 13355 | Mir7232 | NR_106091.1 | chr6:81895589-81895663 |
| 13259 | Mir7040 | NR_106007.1 | chr5:83049710-83049773 | 13356 | Mir7233 | NR_106092.1 | chr6:127788083-127788143 |
| 13260 | Mir7041 | NR_106008.1 | chr6:94606363-94606415 | 13357 | Mir7234 | NR_106093.1 | chr7:73819589-73819641 |
| 13261 | Mir7042 | NR_106009.1 | chr6:113707207-113707265 | 13358 | Mir7235 | NR_106094.1 | chr11:97146363-97146419 |
| 13262 | Mir7043 | NR_106010.1 | chr6:116646077-116646047 | 13359 | Mir7236 | NR_106095.1 | chr11:121387144-121387204 |
| 13263 | Mir7044 | NR_106011.1 | chr6:118085191-118085263 | 13360 | Mir7237 | NR_106096.1 | chr8:121976023-121973086 |
| 13264 | Mir7045 | NR_106012.1 | chr6:125097023-125097086 | 13361 | Mir7238 | NR_106097.1 | chr8:116635693-116635736 |
| 13265 | Mir7046 | NR_106013.1 | chr7:24970009-24970075 | 13362 | Mir7239 | NR_106098.1 | chr11:46170086-46170143 |
| 13266 | Mir7047 | NR_106014.1 | chr7:24987603-24987667 | 13363 | Mir7240 | NR_106099.1 | chr8:70798134-70798192 |
| 13267 | Mir7048 | NR_106015.1 | chr7:25217667-25217725 | 13364 | Mir7241 | NR_106100.1 | chr9:67727716-67727780 |
| 13268 | Mir7049 | NR_106016.1 | chr7:28560924-28560984 | 13365 | Mir7242 | NR_106101.1 | chr9:67729498-67729577 |
| 13269 | Mir705 | NR_030486.1 | chr6:85336291-85336373 | 13366 | Mir7243 | NR_106103.1 | chr9:102304923-102304975 |
| 13270 | Mir7050 | NR_106017.1 | chr7:31040257-31040317 | 13367 | Mir741 | NR_030501.1 | chrX:66796804-66796875 |
| 13271 | Mir7051 | NR_106018.1 | chr7:43457496-43457569 | 13368 | Mir742 | NR_030531.1 | chrX:66780372-66780437 |
| 13272 | Mir7052 | NR_106019.1 | chr7:44470346-44470411 | 13369 | Mir743 | NR_030532.1 | chrX:66776756-66776818 |
| 13273 | Mir7053 | NR_106020.1 | chr7:44538165-44538178 | 13370 | Mir743b | NR_030535.1 | chrX:66777255-66777332 |
| 13274 | Mir7054 | NR_106021.1 | chr7:45012425-45012487 | 13371 | Mir744 | NR_030417.1 | chr11:65734732-65734832 |
| 13275 | Mir7055 | NR_106022.1 | chr7:45173302-45173361 | 13372 | Mir7578 | NR_106102.1 | chr2:27450548-27450630 |
| 13276 | Mir7056 | NR_106023.1 | chr7:47083165-47083224 | 13373 | Mir758 | NR_030421.1 | chr12:109712809-109712890 |
| 13277 | Mir7057 | NR_106024.1 | chr7:66381666-66381724 | 13374 | Mir759 | NR_030436.1 | chr14:79738480-79738528 |
| 13278 | Mir7058 | NR_106025.1 | chr7:126368070-126368045 | 13375 | Mir760 | NR_030439.1 | chr3:122293584-122293703 |
| 13279 | Mir7059 | NR_106026.1 | chr7:126579473-126579532 | 13376 | Mir761 | NR_030432.1 | chr4:109017654-109017736 |
| 13280 | Mir706 | NR_030487.1 | chr7:120034227-120034311 | 13377 | Mir762 | NR_030428.1 | chr7:127708486-127708562 |
| 13281 | Mir7060 | NR_106027.1 | chr7:127489256-127489387 | 13378 | Mir764 | NR_030433.1 | chrX:147002258-147002366 |
| 13282 | Mir7061 | NR_106028.1 | chr7:130908267-130908335 | 13379 | Mir7646 | NR_106104.1 | chrX:135746715-135746769 |
| 13283 | Mir7062 | NR_106029.1 | chr7:139986808-139986874 | 13380 | Mir7647 | NR_106105.1 | chr5:123522636-123522695 |
| 13284 | Mir7063 | NR_106030.1 | chr7:141620700-141620791 | 13381 | Mir7648 | NR_106106.1 | chr15:90224359-90224412 |
| 13285 | Mir7064 | NR_106031.1 | chr7:143570670-143570759 | 13382 | Mir7649 | NR_106107.1 | chr6:128931792-128974895 |
| 13286 | Mir7065 | NR_106032.1 | chr8:13136011-13136132 | 13383 | Mir7650 | NR_106108.1 | chr9:15312610-15312669 |
| 13287 | Mir7066 | NR_106033.1 | chr8:70102523-70102586 | 13384 | Mir7652 | NR_106112.1 | chr1:150024760-150052202 |
| 13288 | Mir7067 | NR_106034.1 | chr8:70895507-70895570 | 13385 | Mir7653 | NR_106113.1 | chr11:78178826-78178887 |

Fig.21 - 70

| | | | | | | | | |
|---|---|---|---|---|---|---|---|---|
| 13386 | Mir7654 | NR_106114.1 | chr8:8690092-8690162 | | 13483 | Mirlet7d | NR_029656.1 | chr13:48536011-48536114 |
| 13387 | Mir7655 | NR_106115.1 | chr2:18057845-18057903 | | 13484 | Mirlet7e | NR_029730.1 | chr17:17830351-17830444 |
| 13388 | Mir7656 | NR_106116.1 | chr9:94751828-94751890 | | 13485 | Mirlet7f-1 | NR_029731.1 | chr13:48537828-48537917 |
| 13389 | Mir7657 | NR_106117.1 | chr3:122541624-122541681 | | 13486 | Mirlet7f-2 | NR_029732.1 | chrX:151912345-151912428 |
| 13390 | Mir7658 | NR_106118.1 | chr4:156230058-156230115 | | 13487 | Mirlet7g | NR_029526.1 | chr9:106178839-106178927 |
| 13391 | Mir7661 | NR_106121.1 | chr6:108489742-108489803 | | 13488 | Mirlet7i | NR_029527.1 | chr10:122985639-122985724 |
| 13392 | Mir7662 | NR_106122.1 | chr10:62194166-62194227 | | 13489 | Mirlet7j | NR_105798.1 | chr3:140028248-140028370 |
| 13393 | Mir7663 | NR_106123.1 | chr10:22729371-22729432 | | 13490 | Mirlet7k | NR_105854.1 | chr5:147283188-147283298 |
| 13394 | Mir7665 | NR_106125.1 | chr2:120017516-120017579 | | 13491 | Mis12 | NM_025993.2 | chr11:71019610-71027134 |
| 13395 | Mir7666 | NR_106126.1 | chr8:40307874-40307929 | | 13492 | Mis18a | NM_025642.1 | chr16:90719311-90727371 |
| 13396 | Mir7667 | NR_106127.1 | chr9:21168377-21226281 | | 13493 | Mis18bp1 | NM_172578.2 | chr12:65132734-65172580 |
| 13397 | Mir7668 | NR_106128.1 | chr7:29906508-29906567 | | 13494 | Misp | NM_030218.2 | chr10:79821020-79830452 |
| 13398 | Mir7669 | NR_106129.1 | chr3:90011152-90011210 | | 13495 | Mitd1 | NM_026913.2 | chr1:37878889-37890411 |
| 13399 | Mir767 | NR_035528.1 | chrX:72589987-72590094 | | 13496 | Mitf | NM_001113198.1 | chr6:97807087-98021358 |
| 13400 | Mir7670 | NR_106130.1 | chr6:38507324-38507393 | | 13497 | Mix1 | NM_013729.3 | chr1:180693047-180697034 |
| 13401 | Mir7671 | NR_106131.1 | chr7:53763996-53763654 | | 13498 | Mk67 | NM_001081117.2 | chr7:135689787-135716379 |
| 13402 | Mir7672 | NR_106132.1 | chr14:26669946-26669608 | | 13499 | Mkks | NM_001141946.1 | chr2:136873780-136891406 |
| 13403 | Mir7673 | NR_106133.1 | chr9:94274573-94274637 | | 13500 | Mkl1 | NM_001082536.1 | chr15:81012280-81190757 |
| 13404 | Mir7674 | NR_106135.1 | chr2:32050945-32051008 | | 13501 | Mkl2 | NM_001122667.2 | chr16:13256480-13417529 |
| 13405 | Mir7675 | NR_106136.1 | chr12:11299886-11299944 | | 13502 | Mkln1 | NM_013791.2 | chr6:31398827-31509477 |
| 13406 | Mir7676-2 | NR_106138.1 | chr15:78284787-78348660 | | 13503 | Mkln1os | NR_040300.1 | chr6:31366884-31398773 |
| 13407 | Mir7677 | NR_106142.1 | chr17:27091244-27091311 | | 13504 | Mknk1 | NM_001285487.1 | chr4:115839197-115879256 |
| 13408 | Mir7678 | NR_106143.1 | chr2:164354312-164354383 | | 13505 | Mknk2 | NM_021462.4 | chr10:80665317-80676293 |
| 13409 | Mir7679 | NR_106144.1 | chr11:82985002-82985065 | | 13506 | Mkrn1 | NM_018810.2 | chr6:39397820-39420369 |
| 13410 | Mir7680 | NR_106145.1 | chr16:21256012-21256066 | | 13507 | Mkrn2 | NM_023290.2 | chr6:115601937-115618670 |
| 13411 | Mir7681 | NR_106149.1 | chr1:53849423-53849495 | | 13508 | Mkrn3 | NM_011746.2 | chr7:62417592-62420139 |
| 13412 | Mir7682 | NR_106150.1 | chr1:151442392-151442450 | | 13509 | Mks1 | NM_001039684.2 | chr11:87853224-87863679 |
| 13413 | Mir7684 | NR_106153.1 | chr15:82393918-82393978 | | 13510 | Mkx | NM_177595.4 | chr18:6934965-7004779 |
| 13414 | Mir7685 | NR_106156.1 | chr2:158243503-158243565 | | 13511 | Mlana | NM_029993.1 | chr19:29697940-29708306 |
| 13415 | Mir7686 | NR_106157.1 | chr7:139957565-139957622 | | 13512 | Mlc1 | NM_133241.2 | chr15:88955883-88978553 |
| 13416 | Mir7687 | NR_106159.1 | chr8:120538695-120538754 | | 13513 | Mlec | NM_175403.3 | chr5:115142980-115158176 |
| 13417 | Mir770 | NR_030427.1 | chr12:109563691-109563785 | | 13514 | Mlf1 | NM_001039543.2 | chr3:67374096-67400000 |
| 13418 | Mir7b | NR_029827.1 | chr17:56242987-56243098 | | 13515 | Mlf2 | NM_001170341.1 | chr6:124931387-124936149 |
| 13419 | Mir802 | NR_030429.1 | chr16:93369719-93369816 | | 13516 | Mlh1 | NM_026810.2 | chr9:111228227-111271608 |
| 13420 | Mir804 | NR_030529.1 | chr11:50357784-50357879 | | 13517 | Mlh3 | NM_175337.2 | chr12:85234465-85270599 |
| 13421 | Mir8091 | NR_106166.1 | chr9:41588680-41588789 | | 13518 | Mlip | NM_027150.1 | chr9:77102083-77347870 |
| 13422 | Mir8092 | NR_106167.1 | chr9:40894702-40894789 | | 13519 | Mlki | NM_029005.3 | chr11:111797-1113.18205 |
| 13423 | Mir8093 | NR_106168.1 | chr2:32687629-32687766 | | 13520 | Mllt1 | NM_022328.2 | chr17:56892610-56935388 |
| 13424 | Mir8094 | NR_106169.1 | chr17:35251288-35251405 | | 13521 | Mllt10 | NM_001252560.1 | chr2:18064584-18212390 |
| 13425 | Mir8095 | NR_106170.1 | chr16:22532055-22532184 | | 13522 | Mllt11 | NM_019914.4 | chr3:95218643-95228677 |
| 13426 | Mir8096 | NR_106172.1 | chr1:85751947-85752074 | | 13523 | Mllt3 | NM_001286158.1 | chr4:87769924-87806323 |
| 13427 | Mir8097 | NR_106173.1 | chr5:36240045-36240164 | | 13524 | Mllt4 | NM_010306.1 | chr17:13760540-13905794 |
| 13428 | Mir8098 | NR_106174.1 | chr14:62837720-62837857 | | 13525 | Mllt6 | NM_139311.2 | chr11:97663411-97688458 |
| 13429 | Mir8099-1 | NR_106175.1 | chr3:93927337-95139186 | | 13526 | Mlph | NM_053015.3 | chr1:90915099-90951142 |
| 13430 | Mir8100 | NR_106177.1 | chr1:46102269-46102390 | | 13527 | Mlst8 | NM_001252463.1 | chr17:24473549-24479078 |
| 13431 | Mir8101 | NR_106179.1 | chr11:102230039-102230150 | | 13528 | Mlx | NM_001159384.1 | chr11:101087289-101092207 |
| 13432 | Mir8102 | NR_106180.1 | chr11:97744896-97745035 | | 13529 | Mlxip | NM_133917.3 | chr5:123394797-123457931 |
| 13433 | Mir8103 | NR_106181.1 | chr1:97063767-97063874 | | 13530 | Mlxipl | NM_021455.4 | chr5:135106890-135133382 |
| 13434 | Mir8104 | NR_106182.1 | chr12:122679314-122679415 | | 13531 | Mlycd | NM_019966.2 | chr8:119394891-119411088 |
| 13435 | Mir8105 | NR_106183.1 | chr10:128458679-128458768 | | 13532 | Mnaa | NM_133823.4 | chr8:79266423-79294858 |
| 13436 | Mir8106 | NR_106185.1 | chr9:122273889-122274028 | | 13533 | Mnab | NM_029956.3 | chr5:114431033-114444027 |
| 13437 | Mir8107 | NR_106186.1 | chr9:110635998-110636115 | | 13534 | Mmachc | NM_025962.3 | chr4:116702433-116708385 |
| 13438 | Mir8108 | NR_106187.1 | chr2:25159124-25159233 | | 13535 | Mmadhc | NM_133839.2 | chr2:50279880-50296677 |
| 13439 | Mir8109 | NR_106189.1 | chr8:85700904-85701021 | | 13536 | Mmd | NM_026178.2 | chr11:90249475-90278573 |
| 13440 | Mir8110 | NR_106190.1 | chr8:89024734-89024831 | | 13537 | Mmd2 | NM_175217.6 | chr5:142563480-142603752 |
| 13441 | Mir8111 | NR_106191.1 | chr8:84005627-84005764 | | 13538 | Mme | NM_001289462.1 | chr3:63295434-63383713 |
| 13442 | Mir8112 | NR_106192.1 | chr6:71271670-71271801 | | 13539 | Mmel1 | NM_013783.2 | chr4:154869584-154895530 |
| 13443 | Mir8113 | NR_106193.1 | chr6:125234683-125234812 | | 13540 | Mmrgt1 | NM_146234.3 | chrX:56585511-56597919 |
| 13444 | Mir8114 | NR_106194.1 | chr1:153899925-153900036 | | 13541 | Mmrgt2 | NM_175002.2 | chr11:62648663-82666359 |
| 13445 | Mir8115 | NR_106195.1 | chr11:86656070-87483748 | | 13542 | Mmp10 | NM_019471.3 | chr9:7502341-7510242 |
| 13446 | Mir8116 | NR_106198.1 | chr5:137293779-137293876 | | 13543 | Mmp11 | NM_008606.3 | chr10:75923221-75932502 |
| 13447 | Mir8118 | NR_106199.1 | chr4:33438080-33438209 | | 13544 | Mmp12 | NM_008605.3 | chr9:7347373-7360461 |
| 13448 | Mir8119 | NR_106199.1 | chr14:129557682-129557811 | | 13545 | Mmp13 | NM_008607.2 | chr9:7272513-7283333 |
| 13449 | Mir8120 | NR_106200.1 | chr3:65659287-65659426 | | 13546 | Mmp14 | NM_008608.3 | chr14:54431603-54441258 |
| 13450 | Mir871 | NR_030536.1 | chrX:66810427-66810504 | | 13547 | Mmp15 | NM_008609.3 | chr8:95352336-95374293 |
| 13451 | Mir872 | NR_030541.6 | chr4:94665156-94665237 | | 13548 | Mmp16 | NM_019724.3 | chr4:17853481-18118734 |
| 13452 | Mir873b | NR_105849.1 | chr4:36668509-36668586 | | 13549 | Mmp17 | NM_011846.4 | chr5:129584213-129608211 |
| 13453 | Mir874 | NR_030544.1 | chr13:58023124-58023200 | | 13550 | Mmp19 | NM_001164197.1 | chr10:128790909-128800824 |
| 13454 | Mir875 | NR_106609.1 | chr5:35661047-35661047 | | 13551 | Mmp1a | NM_032006.3 | chr9:7464140-7476869 |
| 13455 | Mir876 | NR_030545.1 | chr4:36645372-36645453 | | 13552 | Mmp1b | NM_032007.3 | chr9:7367869-7388026 |
| 13456 | Mir877 | NR_030603.1 | chr17:35960729-35960814 | | 13553 | Mrop2 | NM_008610.2 | chr8:92827327-92853420 |
| 13457 | Mir878 | NR_030603.1 | chrX:66801507-66801585 | | 13554 | Mmp20 | NM_013903.2 | chr9:7628230-7674968 |
| 13458 | Mir879 | NR_030537.1 | chr5:9375703-9375779 | | 13555 | Mmp21 | NM_152944.1 | chr7:133674269-133680061 |
| 13459 | Mir880 | NR_030538.1 | chrX:66806529-66806607 | | 13556 | Mmp23 | NM_019935.2 | chr4:155650654-155653384 |
| 13460 | Mir881 | NR_030539.1 | chrX:66801943-66802021 | | 13557 | Mmp24 | NM_010808.3 | chr2:155775343-155818366 |
| 13461 | Mir882 | NR_030540.1 | chr12:109682196-109682273 | | 13558 | Mmp25 | NM_001093339.3 | chr17:23629457-23645269 |
| 13462 | Mir883a | NR_030541.1 | chrX:66780757-66780833 | | 13559 | Mmp27 | NM_001083289.1 | chr9:7571457-7581393 |
| 13463 | Mir883b | NR_030542.1 | chrX:66789889-66789967 | | 13560 | Mmp28 | NM_080453.2 | chr11:83441875-83462961 |
| 13464 | Mir9-1 | NR_029817.1 | chr3:88215029-88215686 | | 13561 | Mmp3 | NM_010809.2 | chr9:7445821-7455974 |
| 13465 | Mir9-2 | NR_029545.1 | chr13:83738813-83738885 | | 13562 | Mmp7 | NM_010810.4 | chr9:7692110-7699416 |
| 13466 | Mir92-1 | NR_029816.1 | chr14:115044426-115044506 | | 13563 | Mmp8 | NM_008611.4 | chr9:7558428-7568486 |
| 13467 | Mir92-2 | NR_029748.1 | chrX:52741857-52741928 | | 13564 | Mmp9 | NM_013599.3 | chr2:164948218-164955849 |
| 13468 | Mir92b | NR_030579.1 | chr3:89227115-89227198 | | 13565 | Mmrn1 | NM_001163567.1 | chr6:60944316-60989378 |
| 13469 | Mir93 | NR_029749.1 | chr5:138165522-138165610 | | 13566 | Mmrn2 | NM_153127.3 | chr14:34375503-34404286 |
| 13470 | Mir9-3 | NR_029818.1 | chr7:79506353-79506353 | | 13567 | Mms19 | NM_028152.3 | chr19:41943706-41981136 |
| 13471 | Mir96 | NR_029750.1 | chr6:30169445-30169531 | | 13568 | Mms22l | NM_199467.2 | chr4:24496461-24602948 |
| 13472 | Mir98 | NR_029753.1 | chrX:151913213-151913321 | | 13569 | Mn1 | NM_001081235.1 | chr5:111418165-111457025 |
| 13473 | Mir99a | NR_029535.1 | chr16:77598935-77599000 | | 13570 | Mnat1 | NM_008612.2 | chr12:73123716-73273988 |
| 13474 | Mir99b | NR_029536.1 | chr17:17830187-17830257 | | 13571 | Mnd1 | NM_029797.3 | chr3:84087933-84155786 |
| 13475 | Mira | NR_045199.1 | chr6:52214491-52215288 | | 13572 | Mnd1-ps | NM_030680.1 | chr14:9884094-9886688 |
| 13476 | Mirg | NR_028265.1 | chr12:109734980-109749457 | | 13573 | Mnda | NM_001034450.4 | chr1:173896340-173913046 |
| 13477 | Mirlet7a-1 | NR_029725.1 | chr13:48538173-48538272 | | 13574 | Mndal | NM_001170853.1 | chr1:173857219-173880187 |
| 13478 | Mirlet7a-2 | NR_029726.1 | chr9:41536715-41536811 | | 13575 | Mns1 | NM_008613.3 | chr9:72438628-72458676 |
| 13479 | Mirlet7b | NR_029727.1 | chr15:85707318-85707403 | | 13576 | Mnt | NM_010813.3 | chr11:74830923-74845725 |
| 13480 | Mirlet7bhg | NR_110483.1 | chr15:85703772-85707524 | | 13577 | Mnx1 | NM_019944.2 | chr5:29473822-29478470 |
| 13481 | Mirlet7c-1 | NR_029728.1 | chr16:77599656-77599750 | | 13578 | Moap1 | NM_001142937.2 | chr12:102739829-102743661 |
| 13482 | Mirlet7c-2 | NR_029729.1 | chr15:85706602-85706697 | | 13579 | Mob1a | NM_145571.2 | chr6:83326038-83340949 |

Fig.21 - 71

| | | | | | | | | |
|---|---|---|---|---|---|---|---|---|
| 13580 | Mob1b | NM_026735.2 | chr5:88720870-88798455 | 13677 | Mrgprb5 | NM_207538.1 | chr7:48168016-48168985 |
| 13581 | Mob2 | NM_028308.2 | chr7:142008552-142061034 | 13678 | Mrgprb8 | NM_207539.2 | chr7:48388525-48389648 |
| 13582 | Mob3a | NM_172457.2 | chr10:80688252-80701820 | 13679 | Mrgprd | NM_203490.3 | chr7:145314834-145324059 |
| 13583 | Mob3b | NM_178061.5 | chr4:34949073-35157484 | 13680 | Mrgpre | NM_175534.3 | chr7:143778262-143784500 |
| 13584 | Mob3c | NM_175308.4 | chr4:115828091-115836183 | 13681 | Mrgprf | NM_145379.2 | chr7:145300908-145309557 |
| 13585 | Mob4 | NM_025283.3 | chr1:55131244-55154899 | 13682 | Mrgprg | NM_203492.2 | chr7:143763709-143766993 |
| 13586 | Mobp | NM_001039364.2 | chr9:120149741-120176091 | 13683 | Mrgprh | NM_030726.1 | chr17:12876033-12877842 |
| 13587 | Mocos | NM_026779.1 | chr18:24653690-24701556 | 13684 | Mrgprx1 | NM_207540.2 | chr7:48020970-48027597 |
| 13588 | Mocs1 | NM_020042.2 | chr17:49428363-49455430 | 13685 | Mrgprx2 | NM_001034868.3 | chr7:48478618-48499270 |
| 13589 | Mocs2 | NM_011133274.1 | chr13:114818236-114829420 | 13686 | Mr1 | NM_026423.4 | chr8:84250575-84257324 |
| 13590 | Mocs3 | NM_001160330.1 | chr2:168230621-168232303 | 13687 | Mrm1 | NM_145433.1 | chr11:84813060-84819515 |
| 13591 | Mog | NM_010814.2 | chr17:37010739-37023398 | 13688 | Mro | NM_027741.3 | chr18:73859384-73879134 |
| 13592 | Mogat1 | NM_026713.3 | chr1:78511059-78538173 | 13689 | Mroh1 | NM_001162489.1 | chr15:76390030-76439744 |
| 13593 | Mogat2 | NM_177448.4 | chr7:99219083-99238611 | 13690 | Mroh2a | NM_001281466.1 | chr1:88227019-88262289 |
| 13594 | Mogs | NM_020619.2 | chr6:83115505-83118898 | 13691 | Mroh2b | NM_001166066.1 | chr15:4898736-4962201 |
| 13595 | Mok | NM_011973.2 | chr12:110807797-110840939 | 13692 | Mroh4 | NM_001177437.1 | chr15:74606027-74636318 |
| 13596 | Mon1a | NM_028369.3 | chr9:107888128-107903139 | 13693 | Mroh5 | NM_001033365.2 | chr15:73786955-73839671 |
| 13597 | Mon1b | NM_001048343.2 | chr8:113635585-113645192 | 13694 | Mroh6 | NM_001282443.1 | chr15:75882933-75888723 |
| 13598 | Mon2 | NM_001163024.1 | chr10:122992060-123076505 | 13695 | Mroh7 | NM_001126487.1 | chr4:106680416-106727939 |
| 13599 | Morc1 | NM_010816.1 | chr16:48431236-48630905 | 13696 | Mroh8 | NM_001039557.4 | chr2:157208547-157279549 |
| 13600 | Morc2a | NM_001159288.1 | chr11:3649493-3690370 | 13697 | Mroh9 | NM_030071.1 | chr1:163024301-163085670 |
| 13601 | Morc2b | NM_177719.4 | chr17:33135589-33139683 | 13698 | Mrpl1 | NM_001039084.1 | chr5:96210114-96239684 |
| 13602 | Morc3 | NM_001045529.3 | chr16:93832120-93876073 | 13699 | Mrpl10 | NM_026154.1 | chr11:97041585-97049213 |
| 13603 | Morc4 | NM_001193309.1 | chrX:139821634-139871654 | 13700 | Mrpl11 | NM_025553.4 | chr19:4962305-4966995 |
| 13604 | Morf4l1 | NM_001039147.2 | chr9:90091668-90114820 | 13701 | Mrpl12 | NM_027204.2 | chr11:120484669-120488754 |
| 13605 | Morf4l2 | NM_001168225.1 | chrX:136732947-136741155 | 13702 | Mrpl13 | NM_026759.3 | chr15:55534094-55557312 |
| 13606 | Morn1 | NM_001081100.1 | chr4:155086576-155145507 | 13703 | Mrpl14 | NM_026732.2 | chr17:45686371-45698495 |
| 13607 | Morn2 | NM_194269.2 | chr17:80290211-80297476 | 13704 | Mrpl15 | NM_001177658.1 | chr1:4773199-4785726 |
| 13608 | Morn3 | NM_029112.1 | chr7:123037126-123046820 | 13705 | Mrpl16 | NM_025606.3 | chr19:11770414-11774946 |
| 13609 | Morn4 | NM_198108.2 | chr19:42074938-42086370 | 13706 | Mrpl17 | NM_025301.2 | chr7:105803781-105811087 |
| 13610 | Morn5 | NM_029309.2 | chr2:36049472-36079709 | 13707 | Mrpl18 | NM_026310.3 | chr17:12913354-12916091 |
| 13611 | Mos | NM_020121.2 | chr4:3870657-3872105 | 13708 | Mrpl19 | NM_026490.2 | chr6:81957841-81965949 |
| 13612 | Mospd1 | NM_001290514.1 | chrX:53344593-53370559 | 13709 | Mrpl2 | NM_025302.4 | chr17:48646247-48650132 |
| 13613 | Mospd2 | NM_001290523.1 | chrX:164936170-164980375 | 13710 | Mrpl20 | NM_025570.2 | chr4:155803617-155808829 |
| 13614 | Mospd3 | NM_001254762.1 | chr5:137596646-137600708 | 13711 | Mrpl21 | NM_172252.3 | chr19:3283046-3292837 |
| 13615 | Mospd4 | NR_045438.1 | chr18:46464933-46465316 | 13712 | Mrpl22 | NM_175001.3 | chr11:58171653-58179981 |
| 13616 | Mov10 | NM_001290514.1 | chr3:104794833-104818563 | 13713 | Mrpl23 | NM_011288.1 | chr7:142533116-142540742 |
| 13617 | Mov10l1 | NM_031260.2 | chr15:88982993-89055152 | 13714 | Mrpl24 | NM_026591.3 | chr3:87919543-87923433 |
| 13618 | Moxd1 | NM_021509.5 | chr10:24223516-24302783 | 13715 | Mrpl27 | NM_053161.2 | chr11:94653790-94660087 |
| 13619 | Moxd2 | NM_139296.2 | chr6:40878793-40887494 | 13716 | Mrpl28 | NM_024227.3 | chr17:26123502-26126613 |
| 13620 | Mpc1 | NM_018819.4 | chr17:8283812-8297661 | 13717 | Mrpl3 | NM_053159.3 | chr9:105053267-105077476 |
| 13621 | Mpc2 | NM_027430.2 | chr1:165461207-165481214 | 13718 | Mrpl30 | NM_027098.2 | chr1:37890552-37898313 |
| 13622 | Mpdu1 | NM_011900.4 | chr11:69656698-69662649 | 13719 | Mrpl32 | NM_029271.2 | chr13:14610300-14613037 |
| 13623 | Mpdz | NM_010820.3 | chr4:81278498-81442815 | 13720 | Mrpl33 | NM_025796.3 | chr5:31613950-31622644 |
| 13624 | Mpeg1 | NM_010821.1 | chr19:12460778-12465285 | 13721 | Mrpl34 | NM_053162.2 | chr8:71464925-71465753 |
| 13625 | Mpg | NM_010822.3 | chr11:32226504-32232702 | 13722 | Mrpl35 | NM_025430.3 | chr6:71812996-71823784 |
| 13626 | Mphosph10 | NM_026483.2 | chr7:64376540-64392236 | 13723 | Mrpl36 | NM_053163.1 | chr13:73331008-73332178 |
| 13627 | Mphosph6 | NM_026758.3 | chr8:117791644-117801929 | 13724 | Mrpl37 | NM_025500.2 | chr4:107055873-107066866 |
| 13628 | Mphosph8 | NM_023773.2 | chr14:56668247-56697429 | 13725 | Mrpl38 | NM_024177.3 | chr13:116131816-116138868 |
| 13629 | Mphosph9 | NM_001081083.1 | chr5:124250958-124327972 | 13726 | Mrpl39 | NM_017404.4 | chr16:84717579-84735802 |
| 13630 | Mpi | NM_025837.2 | chr9:57544267-57552752 | 13727 | Mrpl4 | NM_023167.2 | chr9:21002736-21008837 |
| 13631 | Mpl | NM_001122949.2 | chr4:118442414-118457513 | 13728 | Mrpl40 | NM_010922.2 | chr16:18872017-18876637 |
| 13632 | Mplkip | NM_024579.5 | chr13:17695412-17699105 | 13729 | Mrpl41 | NM_001031808.2 | chr2:24972469-24975098 |
| 13633 | Mpnd | NM_026530.5 | chr17:56009200-56016783 | 13730 | Mrpl42 | NM_026065.3 | chr10:95480805-95501927 |
| 13634 | Mpo | NM_010824.2 | chr11:87793783-87804412 | 13731 | Mrpl43 | NM_053164.3 | chr19:45005013-45006442 |
| 13635 | Mpp1 | NM_008621.3 | chrX:75109732-75131016 | 13732 | Mrpl44 | NM_001081210.1 | chr1:79776917-79781445 |
| 13636 | Mpp2 | NM_016695.3 | chr11:102057016-102088515 | 13733 | Mrpl45 | NM_025927.4 | chr11:97315715-97329920 |
| 13637 | Mpp3 | NM_027863.2 | chr11:101999862-102026905 | 13734 | Mrpl46 | NM_023331.2 | chr7:78775340-78783089 |
| 13638 | Mpp4 | NM_001164682.1 | chr1:59120934-59163389 | 13735 | Mrpl47 | NM_029017.2 | chr3:32727496-32736755 |
| 13639 | Mpp5 | NM_019579.3 | chr12:78748946-78840713 | 13736 | Mrpl48 | NM_198831.2 | chr7:100549116-100583130 |
| 13640 | Mpp6 | NM_146734.1 | chr6:50110240-50198593 | 13737 | Mrpl49 | NM_026246.3 | chr19:6053629-6057751 |
| 13641 | Mpp7 | NM_001081287.2 | chr18:7347961-7626863 | 13738 | Mrpl50 | NM_178603.4 | chr4:49512596-49521083 |
| 13642 | Mppe1 | NM_172127.2 | chr18:67229320-67245830 | 13739 | Mrpl51 | NM_025595.3 | chr6:125192199-125194392 |
| 13643 | Mpped1 | NM_172610.3 | chr15:83780022-83858474 | 13740 | Mrpl52 | NM_026851.2 | chr14:54426908-54429750 |
| 13644 | Mpped2 | NM_001143683.1 | chr2:106693458-106868360 | 13741 | Mrpl53 | NM_026744.3 | chr6:83109107-83109932 |
| 13645 | Mprip | NM_012027.2 | chr11:59662494-59780860 | 13742 | Mrpl54 | NM_025317.2 | chr10:81264721-81266928 |
| 13646 | Mpst | NM_001162492.1 | chr15:78406800-78414015 | 13743 | Mrpl55 | NM_026035.4 | chr11:59202485-59206135 |
| 13647 | Mptx1 | NM_025470.3 | chr1:174330617-174332877 | 13744 | Mrpl57 | NM_026401.2 | chr14:57826238-57828745 |
| 13648 | Mptx2 | NM_001265011.1 | chr1:173274460-173277756 | 13745 | Mrpl9 | NM_030116.2 | chr3:94443335-94448708 |
| 13649 | Mpv17 | NM_008622.6 | chr5:31140662-31154251 | 13746 | Mrps10 | NM_001146211.1 | chr17:47368886-47378679 |
| 13650 | Mpv17l | NM_001289561.1 | chr16:13940664-13949619 | 13747 | Mrps11 | NM_026498.2 | chr7:78783130-78792988 |
| 13651 | Mpv17l2 | NM_183170.2 | chr8:70758648-70760921 | 13748 | Mrps12 | NM_011885.4 | chr7:28739640-28741781 |
| 13652 | Mpz | NM_008623.5 | chr1:171150712-171161123 | 13749 | Mrps14 | NM_025474.3 | chr1:160195259-160201186 |
| 13653 | Mpzl1 | NM_001001880.2 | chr1:165592130-165634541 | 13750 | Mrps15 | NM_025442.2 | chr4:126046927-126055536 |
| 13654 | Mpzl2 | NM_007962.4 | chr9:45042343-45054043 | 13751 | Mrps16 | NM_025440.2 | chr14:20391230-20393555 |
| 13655 | Mpzl3 | NM_001093749.2 | chr9:45055180-45075042 | 13752 | Mrps17 | NM_025450.4 | chr5:129715527-129718691 |
| 13656 | Mr1 | NM_008029.4 | chr1:155127877-155146780 | 13753 | Mrps18a | NM_026768.3 | chr17:46111003-46128908 |
| 13657 | Mrap | NM_029844.3 | chr16:90738823-90749776 | 13754 | Mrps18b | NM_025878.1 | chr17:35910384-35916369 |
| 13658 | Mrap2 | NM_001101482.2 | chr9:87144505-87184045 | 13755 | Mrps18c | NM_026826.1 | chr5:100798758-100804467 |
| 13659 | Mras | NM_008624.3 | chr9:99185419-99436712 | 13756 | Mrps2 | NM_001166031.2 | chr2:28468055-28471177 |
| 13660 | Mrc1 | NM_008625.2 | chr2:14229413-14332035 | 13757 | Mrps21 | NM_078479.3 | chr3:95862651-95870619 |
| 13661 | Mrc2 | NM_008626.2 | chr11:105292645-105351145 | 13758 | Mrps22 | NM_025485.3 | chr9:98588729-98601679 |
| 13662 | Mre11a | NM_018736.3 | chr9:14784653-14837126 | 13759 | Mrps23 | NM_001291270.1 | chr11:88194105-88211507 |
| 13663 | Mreg | NM_001005423.2 | chr1:72159232-72212307 | 13760 | Mrps24 | NM_025080.2 | chr11:5703982-5707699 |
| 13664 | Mrfap1 | NM_026242.3 | chr5:36794866-36796754 | 13761 | Mrps25 | NM_025578.4 | chr6:92169522-92184023 |
| 13665 | Mrgbp | NM_028479.1 | chr2:180581308-180585634 | 13762 | Mrps26 | NM_207207.1 | chr2:130563756-130565394 |
| 13666 | Mrgpra1 | NM_153095.1 | chr7:47384874-47354040 | 13763 | Mrps27 | NM_173757.3 | chr13:99344785-99415561 |
| 13667 | Mrgpra2a | NM_001172588.1 | chr7:47426328-47452139 | 13764 | Mrps28 | NM_025434.3 | chr3:8802145-8923857 |
| 13668 | Mrgpra2b | NM_153101.3 | chr7:47463806-47489582 | 13765 | Mrps30 | NM_021556.3 | chr13:118380109-118387252 |
| 13669 | Mrgpra3 | NM_153523.2 | chr7:47588949-47601372 | 13766 | Mrps31 | NM_020560.2 | chr8:22411339-22429665 |
| 13670 | Mrgpra4 | NM_153524.2 | chr7:47980793-47982296 | 13767 | Mrps33 | NM_001010930.1 | chr6:39801806-39810936 |
| 13671 | Mrgpra6 | NM_001308537.1 | chr7:47185766-47189355 | 13768 | Mrps34 | NM_023260.1 | chr17:24895119-24896273 |
| 13672 | Mrgpra9 | NM_001288801.1 | chr7:47252848-47252848 | 13769 | Mrps35 | NM_145573.2 | chr6:147042769-147070902 |
| 13673 | Mrgprb1 | NM_205810.4 | chr7:48444112-48456342 | 13770 | Mrps36 | NM_001190264.1 | chr13:100735939-100744659 |
| 13674 | Mrgprb2 | NM_153151.4 | chr7:48550965-48558036 | 13771 | Mrps5 | NM_025963.2 | chr2:127587425-127603986 |
| 13675 | Mrgprb3 | NM_207537.1 | chr7:48642862-48643801 | 13772 | Mrps6 | NM_080456.1 | chr16:92058335-92112227 |
| 13676 | Mrgprb4 | NM_205795.1 | chr7:48198212-48199178 | 13773 | Mrps7 | NM_025305.2 | chr11:115604150-115607624 |

Fig.21 - 72

| | | | | | | | |
|---|---|---|---|---|---|---|---|
| 13774 | Mrps9 | NM_023514.4 | chr1:42891232-42905683 | 13871 | Mtss | NM_001039657.2 | chr19:3388856-3407823 |
| 13775 | Mrrf | NM_026422.2 | chr2:36136397-36190283 | 13872 | Mtm1 | NM_001164190.1 | chrX:71210766-71315295 |
| 13776 | Mrs2 | NM_001013389.2 | chr13:24992294-25020317 | 13873 | Mtmr1 | NM_016985.2 | chrX:71364759-71419196 |
| 13777 | Mrto4 | NM_001290810.1 | chr4:139347439-139352576 | 13874 | Mtmr10 | NM_172742.2 | chr7:64287669-64340806 |
| 13778 | Mrvi1 | NM_010826.5 | chr7:110868257-110946187 | 13875 | Mtmr11 | NM_181409.3 | chr3:96161969-96171718 |
| 13779 | Ms4a1 | NM_087641.5 | chr19:11250802-11266151 | 13876 | Mtmr12 | NM_172958.3 | chr15:12205093-12272240 |
| 13780 | Ms4a10 | NM_023529.2 | chr19:10962294-10974670 | 13877 | Mtmr14 | NM_026849.2 | chr6:113237842-113281392 |
| 13781 | Ms4a13 | NM_198224.3 | chr19:11169417-11196723 | 13878 | Mtmr2 | NM_023858.3 | chr9:13749180-13806481 |
| 13782 | Ms4a15 | NM_001034898.2 | chr19:10978306-10993250 | 13879 | Mtmr3 | NM_028860.2 | chr11:4480867-4594815 |
| 13783 | Ms4a18 | NM_001251849.1 | chr19:10997024-11017963 | 13880 | Mtmr4 | NM_133215.1 | chr11:87592218-87616296 |
| 13784 | Ms4a2 | NM_001276328.1 | chr19:11615520-11623719 | 13881 | Mtmr6 | NM_144843.4 | chr14:60265204-60302371 |
| 13785 | Ms4a3 | NM_133246.5 | chr19:11629498-11640851 | 13882 | Mtmr7 | NM_001040899.1 | chr8:40550158-40634792 |
| 13786 | Ms4a4b | NM_021718.2 | chr19:11443557-11463548 | 13883 | Mtmr9 | NM_177594.1 | chr14:63523609-63543953 |
| 13787 | Ms4a4c | NM_029499.3 | chr19:11407660-11427246 | 13884 | Mtnr1a | NM_008639.2 | chr8:45069209-45088506 |
| 13788 | Ms4a4d | NM_025658.4 | chr19:11536848-11558466 | 13885 | Mtnr1b | NM_145712.2 | chr9:15862613-15874556 |
| 13789 | Ms4a5 | NM_183190.2 | chr19:11273865-11283813 | 13886 | Mto1 | NM_026658.2 | chr9:78442209-78474152 |
| 13790 | Ms4a6b | NM_027209.3 | chr19:11515858-11530403 | 13887 | Mtor | NM_020009.2 | chr4:148448581-148557685 |
| 13791 | Ms4a6c | NM_001166376.1 | chr19:11469887-11472736 | 13888 | Mtpap | NM_026157.2 | chr18:4375591-4397330 |
| 13792 | Ms4a6d | NM_026835.2 | chr19:11588609-11604804 | 13889 | Mtpn | NM_008098.4 | chr6:35508823-35539888 |
| 13793 | Ms4a7 | NM_001025610.4 | chr19:11321035-11336146 | 13890 | Mtr | NM_001081128.3 | chr13:12186539-12258113 |
| 13794 | Ms4a8a | NM_022430.2 | chr19:11067479-11081103 | 13891 | Mtrf1 | NM_145960.4 | chr14:79397771-79423650 |
| 13795 | Msantd1 | NM_207277.1 | chr5:34915914-34923839 | 13892 | Mtrf1l | NM_175374.3 | chr10:5811886-5823943 |
| 13796 | Msantd2 | NM_146222.2 | chr9:37489320-37524150 | 13893 | Mtrr | NM_172480.3 | chr13:68560779-68582169 |
| 13797 | Msantd3 | NM_001145924.1 | chr4:48540080-48561920 | 13894 | Mtss1 | NM_001146180.1 | chr15:58941233-59082026 |
| 13798 | Msantd4 | NM_145609.1 | chr9:4383536-4386869 | 13895 | Mtss1l | NM_198625.2 | chr8:110721475-110741401 |
| 13799 | Msc | NM_010827.2 | chr1:14753345-14755966 | 13896 | Mttp | NM_001163457.1 | chr3:138089854-138143388 |
| 13800 | Msgn1 | NM_019544.1 | chr12:11208381-11208948 | 13897 | Mturn | NM_001289740.1 | chr6:54681623-54703855 |
| 13801 | Msh2 | NM_008628.2 | chr17:87672556-87723713 | 13898 | Mtus1 | NM_001005863.2 | chr8:40990911-41133726 |
| 13802 | Msh3 | NM_010807.3 | chr13:92211880-92355003 | 13899 | Mtus2 | NM_029920.7 | chr5:147957319-148316066 |
| 13803 | Msh4 | NM_001282054.1 | chr3:153887140-153904891 | 13900 | Mtx1 | NM_001161824.1 | chr3:89209080-89214335 |
| 13804 | Msh5 | NM_001146215.2 | chr17:35028604-35046745 | 13901 | Mtx2 | NM_016804.4 | chr2:74825811-74876748 |
| 13805 | Msh6 | NM_010830.2 | chr17:87975049-87990892 | 13902 | Mtx3 | NM_001162945.1 | chr13:92844786-92858230 |
| 13806 | Msi1 | NM_008629.1 | chr5:115429684-115454202 | 13903 | Muc1 | NM_013605.2 | chr3:89229055-89233381 |
| 13807 | Msi2 | NM_001201341.1 | chr11:88685953-88718267 | 13904 | Muc13 | NM_010739.2 | chr16:33794036-33819927 |
| 13808 | Msl1 | NM_028722.2 | chr11:98795788-98807859 | 13905 | Muc15 | NM_001290786.1 | chr2:110721493-110739537 |
| 13809 | Msl2 | NM_001100451.2 | chr9:101074761-101104799 | 13906 | Muc19 | NM_207243.2 | chr15:91838325-91934955 |
| 13810 | Msl3 | NM_010832.5 | chrX:1686:53098-168673902 | 13907 | Muc2 | NM_023566.3 | chr7:141690939-141754694 |
| 13811 | Msl3l2 | NM_001163833.1 | chr10:56106916-56116880 | 13908 | Muc20 | NM_001145874.1 | chr16:32777418-32797435 |
| 13812 | Msln | NM_018857.1 | chr17:25746612-25754327 | 13909 | Muc4 | NM_080457.3 | chr16:32735885-32782390 |
| 13813 | Mslnl | NM_177822.3 | chr17:25736039-25748330 | 13910 | Muc5ac | NM_010844.1 | chr7:141789010-141819135 |
| 13814 | Msmb | NM_020597.3 | chr14:32142022-32158126 | 13911 | Muc5b | NM_028801.2 | chr7:141839071-141873085 |
| 13815 | Msmo1 | NM_025436.2 | chr8:64718414-64733578 | 13912 | Muc6 | NM_181729.2 | chr7:141634048-141635308 |
| 13816 | Msmp | NM_001099314.1 | chr4:43583215-43584494 | 13913 | Mucl1 | NM_009268.1 | chr15:103751922-103899300 |
| 13817 | Msn | NM_010833.1 | chrX:96096044-96168553 | 13914 | Mug1 | NM_008645.3 | chr6:121838540-121889057 |
| 13818 | Msr1 | NM_001113326.1 | chr8:39581699-39642678 | 13915 | Mug2 | NM_008646.3 | chr6:122006797-122085967 |
| 13819 | Msra | NM_001253712.1 | chr14:64122620-64441040 | 13916 | Mug-ps1 | NR_027619.1 | chr6:122176052-122248566 |
| 13820 | Msrb1 | NM_013759.2 | chr17:24736641-24742778 | 13917 | Mul1 | NM_026689.3 | chr1:138434671-138442265 |
| 13821 | Msrb2 | NM_029619.2 | chr2:19371635-19394971 | 13918 | Mum1 | NM_028431.5 | chr10:80226697-80245144 |
| 13822 | Msrb3 | NM_177092.4 | chr10:120781100-120898971 | 13919 | Mum1l1 | NM_001164630.1 | chrX:139210843-139238335 |
| 13823 | Mss51 | NM_029104.1 | chr14:20482863-20496901 | 13920 | Mup1 | NM_001163910.1 | chr4:60498933-60501960 |
| 13824 | Mst1 | NM_008243.3 | chr9:108080435-108085027 | 13921 | Mup10 | NM_001122647.1 | chr4:60578260-60582155 |
| 13825 | Mst1r | NM_001287261.1 | chr9:107915002-107920383 | 13922 | Mup11 | NM_001164526.1 | chr4:60658465-60662395 |
| 13826 | Mstn | NM_010834.3 | chr1:53061639-53068079 | 13923 | Mup12 | NM_001199995.1 | chr4:60737380-60741281 |
| 13827 | Msto1 | NM_144898.2 | chr3:88909615-88913950 | 13924 | Mup13 | NM_001134674.1 | chr4:61243806-61228786 |
| 13828 | Msx1 | NM_010835.2 | chr5:37820490-37824585 | 13925 | Mup14 | NM_001300036-61303998 |
| 13829 | Msx1os | NR_027920.1 | chr5:37820563-37822751 | 13926 | Mup15 | NM_001200004.1 | chr4:60066468-61439704 |
| 13830 | Msx2 | NM_013601.2 | chr13:53466886-53472780 | 13927 | Mup16 | NM_001199036.1 | chr4:61515592-61519486 |
| 13831 | Msx3 | NM_001200006.1 | chr7:140046156-140049088 | 13928 | Mup17 | NM_001200006.1 | chr4:61591930-61595832 |
| 13832 | Mt1 | NM_013602.3 | chr8:94179088-94180327 | 13929 | Mup19 | NM_001135127.2 | chr4:61778327-61782224 |
| 13833 | Mt2 | NM_008630.2 | chr8:94172617-94173567 | 13930 | Mup2 | NM_001045550.2 | chr4:60136846-61439702 |
| 13834 | Mt3 | NM_013603.2 | chr8:94152606-94154148 | 13931 | Mup20 | NM_001012323.1 | chr4:62050234-62054117 |
| 13835 | Mt4 | NM_008631.2 | chr8:94137203-94139031 | 13932 | Mup21 | NM_001009950.2 | chr4:62147831-62150841 |
| 13836 | Mta1 | NM_054081.2 | chr12:113098277-113137206 | 13933 | Mup3 | NM_001039544.1 | chr4:62083475-62087312 |
| 13837 | Mta2 | NM_011842.3 | chr19:8941919-8952300 | 13934 | Mup4 | NM_008648.1 | chr4:59956805-59980665 |
| 13838 | Mta3 | NM_001171052.1 | chr17:83706152-83805422 | 13935 | Mup5 | NM_008649.2 | chr4:61831318-61835180 |
| 13839 | Mtag2 | NR_015480.1 | chr7:45366162-45367948 | 13936 | Mup6 | NM_001081285.1 | chr4:60003548-60006214 |
| 13840 | Mtap | NM_024433.2 | chr4:89137369-89181090 | 13937 | Mup7 | NM_001134675.1 | chr4:60066468-60070475 |
| 13841 | Mtap7d3 | NM_172293.3 | chr6:56797952-56822325 | 13938 | Mup8 | NM_001134676.1 | chr4:60218620-60222599 |
| 13842 | Mtbp | NM_001168250.1 | chr15:55557407-55610813 | 13939 | Mup9 | NM_001281979.1 | chr4:60418045-60421952 |
| 13843 | Mtch1 | NM_019880.3 | chr17:29332075-29347904 | 13940 | Murc | NM_026509.3 | chr4:48663515-48673492 |
| 13844 | Mtch2 | NM_019801.4 | chr2:90847154-90866634 | 13941 | Mus81 | NM_027877.3 | chr19:5482839-5488336 |
| 13845 | Mtcl1 | NM_001114098.1 | chr17:66336981-66449750 | 13942 | Musk | NM_001037127.2 | chr4:58285963-58374303 |
| 13846 | Mtcp1 | NM_001039373.5 | chrX:75410441-75416584 | 13943 | Mustn1 | NM_181390.3 | chr14:30879256-30881610 |
| 13847 | Mtdh | NM_054082.4 | chr15:34082718-34142385 | 13944 | Mut | NM_008650.3 | chr17:40934684-40961989 |
| 13848 | Mterf1a | NM_001013023.2 | chr5:3890580-3893933 | 13945 | Mutyh | NM_001159581.1 | chr4:116807733-116819431 |
| 13849 | Mterf1b | NM_001042670.1 | chr5:4192366-4197651 | 13946 | Mvb12a | NM_028617.2 | chr8:71542929-71548026 |
| 13850 | Mterfd1 | NM_025577.3 | chr13:66910297-66933072 | 13947 | Mvb12b | NM_175184.4 | chr2:33729955-33887946 |
| 13851 | Mterfd2 | NM_178051.4 | chr11:93301204-93305879 | 13948 | Mvd | NM_138656.2 | chr8:122433596-122443422 |
| 13852 | Mterfd3 | NM_028827.3 | chr10:85119433-85128027 | 13949 | Mvk | NM_023556.4 | chr5:114444268-114460590 |
| 13853 | Mtf1 | NM_008636.4 | chr4:124802548-124849800 | 13950 | Mvp | NM_080638.3 | chr7:126986859-127014594 |
| 13854 | Mtf2 | NM_001253877.1 | chr5:108065673-108109219 | 13951 | Mx1 | NM_010846.1 | chr16:97447096-97462905 |
| 13855 | Mtfmt | NM_027134.3 | chr9:65435781-65453054 | 13952 | Mx2 | NM_013606.1 | chr16:97536082-97560899 |
| 13856 | Mtfp1 | NM_026443.4 | chr11:4091480-4095431 | 13953 | Mxd1 | NM_010751.3 | chr6:86647044-86668159 |
| 13857 | Mtfr1 | NM_001253390.1 | chr3:19187328-19220817 | 13954 | Mxd3 | NM_016662.4 | chr13:55325167-55329730 |
| 13858 | Mtfr1l | NM_001256443.1 | chr4:134525554-134535268 | 13955 | Mxd4 | NM_010753.2 | chr5:34176579-34187710 |
| 13859 | Mtfr2 | NM_027930.3 | chr10:20347818-20361669 | 13956 | Mxi1 | NM_001008542.2 | chr19:53310505-53379810 |
| 13860 | Mtg1 | NM_001253863-140150786 | 13957 | Mxra7 | NM_026280.3 | chr11:116803399-116828046 |
| 13861 | Mtg2 | NM_001083328.1 | chr2:180070592-180085902 | 13958 | Mxra8 | NM_024263.4 | chr4:155839679-155844102 |
| 13862 | Mthfd1 | NM_138745.2 | chr12:76255231-76319820 | 13959 | Myadm | NM_001093764.1 | chr7:3289037-3299349 |
| 13863 | Mthfd1l | NM_001170785.1 | chr10:3973074-4167081 | 13960 | Myadml2 | NM_001204820.1 | chr11:120648030-120648337 |
| 13864 | Mthfd2 | NM_008638.2 | chr6:83085703-83117604 | 13961 | Myb | NM_001198914.1 | chr10:21124929-21160984 |
| 13865 | Mthfd2l | NM_026788.1 | chr5:90981195-91021370 | 13962 | Mybbp1a | NM_016776.2 | chr11:72441377-72451530 |
| 13866 | Mthfr | NM_001161798.1 | chr4:148041188-148059562 | 13963 | Mybl1 | NM_001290799.1 | chr1:9667410-9700209 |
| 13867 | Mthfs | NM_026829.2 | chr9:89211189-89240225 | 13964 | Mybl2 | NM_008652.2 | chr2:163064634-163084687 |
| 13868 | Mthfsd | NM_001166482.1 | chr8:121097556-121108379 | 13965 | Mybpc1 | NM_001252372.1 | chr10:88518278-88605152 |
| 13869 | Mtif2 | NM_001282118.1 | chr11:29526396-29545447 | 13966 | Mybpc2 | NM_146189.3 | chr7:44501698-44524669 |
| 13870 | Mtif3 | NM_001256100.1 | chr5:146915572-146963797 | 13967 | Mybpc3 | NM_008653.2 | chr2:91118143-91136516 |

Fig.21 - 73

| | | | | | | | |
|---|---|---|---|---|---|---|---|
| 13968 | Mybph | NM_016749.2 | chr1:134193447-134201232 | 14065 | N28178 | NM_172690.2 | chr4:42917250-42941607 |
| 13969 | Mybphl | NM_026831.1 | chr3:108364910-108380057 | 14066 | N4bp1 | NM_030563.2 | chr8:86841138-86885258 |
| 13970 | Myc | NM_001177354.1 | chr15:61985340-61990361 | 14067 | N4bp2 | NM_001024917.1 | chr5:65763520-65826784 |
| 13971 | Mycbp | NM_019660.3 | chr4:123905012-123912250 | 14068 | N4bp2l1 | NM_133898.4 | chr5:150571642-150594525 |
| 13972 | Mycbp2 | NM_207215.2 | chr14:103113410-103346800 | 14069 | N4bp2l2 | NM_201369.3 | chr5:150635972-150665612 |
| 13973 | Mycbpap | NM_170671.2 | chr11:94501346-94521502 | 14070 | N4bp3 | NM_145974.3 | chr11:51643088-51651073 |
| 13974 | Mycl | NM_008506.3 | chr4:122995930-123002480 | 14071 | N6amt1 | NM_001159331.1 | chr16:87354184-87368649 |
| 13975 | Mycn | NM_008709.3 | chr12:12936092-12941836 | 14072 | N6amt2 | NM_026526.2 | chr14:57549597-57571569 |
| 13976 | Mycs | NM_010850.2 | chrX:5466903-5469265 | 14073 | Naa10 | NM_001177965.1 | chrX:73916869-73921944 |
| 13977 | Myct1 | NM_026793.2 | chr10:6593727-5606791 | 14074 | Naa11 | NM_001033191.2 | chr5:97382208-97392330 |
| 13978 | Myd88 | NM_010851.2 | chr9:119335987-119340040 | 14075 | Naa15 | NM_053089.3 | chr3:51436015-51475985 |
| 13979 | Myef2 | NM_001162471.1 | chr2:125086270-125123660 | 14076 | Naa16 | NM_025832.2 | chr14:79334506-79390868 |
| 13980 | Myeov2 | NM_001163425.1 | chr1:192637144-92641985 | 14077 | Naa20 | NM_001141965.1 | chr2:145903240-145916425 |
| 13981 | Myf5 | NM_008656.5 | chr10:107482907-107486134 | 14078 | Naa25 | NM_172722.3 | chr5:121397981-121440113 |
| 13982 | Myf6 | NM_008657.2 | chr10:107492859-107494729 | 14079 | Naa30 | NM_001081430.1 | chr14:49172226-49191031 |
| 13983 | Myg1 | NM_021713.2 | chr15:102331708-102338138 | 14080 | Naa35 | NM_030153.2 | chr13:59585332-59634781 |
| 13984 | Myh1 | NM_030679.1 | chr11:67200113-67224575 | 14081 | Naa38 | NM_030083.2 | chr11:69395790-69396671 |
| 13985 | Myh10 | NM_175260.2 | chr11:68691914-68816624 | 14082 | Naa40 | NM_027643.1 | chr19:7225667-7241222 |
| 13986 | Myh11 | NM_001161775.1 | chr16:14194526-14291408 | 14083 | Naa50 | NM_028108.3 | chr16:44139808-44163364 |
| 13987 | Myh13 | NM_001081250.1 | chr11:67327102-67371502 | 14084 | Naa60 | NM_001290689.1 | chr16:3884618-3904781 |
| 13988 | Myh14 | NM_001271538.1 | chr7:44605802-44665503 | 14085 | Naa | NM_001163687.1 | chr5:92257659-92278181 |
| 13989 | Myh15 | NM_001166230.1 | chr16:49057485-49199104 | 14086 | Naalad2 | NM_028279.3 | chr9:18323020-18385928 |
| 13990 | Myh2 | NM_001039545.2 | chr11:67171026-67197517 | 14087 | Nsaladl1 | NM_001009546.1 | chr19:6105797-6115555 |
| 13991 | Myh3 | NM_001099635.1 | chr11:67078299-67102291 | 14088 | Nab1 | NM_008667.3 | chr1:52455848-52500448 |
| 13992 | Myh4 | NM_010855.3 | chr11:67237811-67260447 | 14089 | Nab2 | NM_001122895.1 | chr10:127660917-127666703 |
| 13993 | Myh6 | NM_001164171.1 | chr14:54941920-54966607 | 14090 | Nabp1 | NM_028696.3 | chr1:51469487-51478399 |
| 13994 | Myh7 | NM_080728.2 | chr14:54970687-54994649 | 14091 | Nabp2 | NM_027257.1 | chr10:128401394-128409796 |
| 13995 | Myh7b | NM_001085378.2 | chr2:155611242-155634307 | 14092 | Naca | NM_001113199.1 | chr10:128035345-128048637 |
| 13996 | Myh8 | NM_177369.3 | chr11:67277123-67308633 | 14093 | Nacad | NM_001081652.1 | chr11:6597822-6606054 |
| 13997 | Myh9 | NM_022410.3 | chr15:77760584-77842175 | 14094 | Nacc1 | NM_025788.3 | chr8:84670478-84687862 |
| 13998 | Myl1 | NM_001133687.1 | chr1:66924295-66935366 | 14095 | Nacc2 | NM_001037098.1 | chr2:26055535-26092398 |
| 13999 | Myl10 | NM_001085387.2 | chr5:136694176-136701094 | 14096 | Nadk | NM_001159637.1 | chr4:155563814-155591001 |
| 14000 | Myl12a | NM_026064.2 | chr17:70993792-71002533 | 14097 | Nadk2 | NM_001040395.4 | chr15:9071259-9110496 |
| 14001 | Myl12b | NM_023402.2 | chr17:70973962-70990516 | 14098 | Nadsyn1 | NM_030221.2 | chr7:143795590-143822652 |
| 14002 | Myl2 | NM_010861.3 | chr5:122100979-122106854 | 14099 | Nae1 | NM_144931.3 | chr8:104511027-104534637 |
| 14003 | Myl3 | NM_010859.2 | chr9:110763680-110769794 | 14100 | Naf1 | NM_001163564.1 | chr3:66860216-66890564 |
| 14004 | Myl4 | NM_010858.2 | chr11:104550662-104587219 | 14101 | Naga | NM_008669.4 | chr15:82329931-82338826 |
| 14005 | Myl6 | NM_010860.3 | chr10:128490860-128493825 | 14102 | Nagk | NM_001164187.1 | chr6:83795157-83802556 |
| 14006 | Myl6b | NM_172259.1 | chr10:128498685-128498685 | 14103 | Naglu | NM_013792.2 | chr11:101070093-101077671 |
| 14007 | Myl7 | NM_022879.2 | chr11:5896636-5898782 | 14104 | Nagpa | NM_013796.3 | chr16:5195279-5204012 |
| 14008 | Myl9 | NM_172118.1 | chr2:156775463-156781657 | 14105 | Nags | NM_145829.2 | chr11:102145512-102149528 |
| 14009 | Mylip | NM_153789.3 | chr13:45389741-45411940 | 14106 | Naif1 | NM_194335.2 | chr2:32450456-32455476 |
| 14010 | Mylk | NM_139300.3 | chr16:34784949-35002434 | 14107 | Naip1 | NM_008670.2 | chr13:100407769-100452864 |
| 14011 | Mylk2 | NM_001081044.2 | chr2:152911351-152923065 | 14108 | Naip2 | NM_001126182.2 | chr13:100144062-100202122 |
| 14012 | Mylk3 | NM_175441.5 | chr8:85324928-85365324 | 14109 | Naip5 | NM_010870.2 | chr13:100211739-100247336 |
| 14013 | Mylk4 | NM_001166030.1 | chr13:32700826-32781779 | 14110 | Naip6 | NM_010871.2 | chr13:100281120-100316616 |
| 14014 | Mylpf | NM_016754.5 | chr7:127211607-127214287 | 14111 | Naip7 | NM_021545.1 | chr13:100283114-100317688 |
| 14015 | Mynn | NM_001289621.1 | chr3:30602086-30619873 | 14112 | Nalcn | NM_177393.4 | chr14:123276640-123627144 |
| 14016 | Myo10 | NM_019472.2 | chr15:25622549-25813671 | 14113 | Nampt | NM_021524.2 | chr12:32820334-32853369 |
| 14017 | Myo15 | NM_001103171.1 | chr11:60469338-60528368 | 14114 | Nanog | NM_001289828.1 | chr6:122707564-122714633 |
| 14018 | Myo16 | NM_001081397.1 | chr8:10153922-10639950 | 14115 | Nanos1 | NM_178421.3 | chr19:60755986-60759914 |
| 14019 | Myo18a | NM_001291212.1 | chr11:77777234-77865988 | 14116 | Nanos2 | NM_194064.2 | chr7:18987523-18988962 |
| 14020 | Myo18b | NM_028208.2 | chr5:112688875-112896362 | 14117 | Nanos3 | NM_194059.2 | chr8:84173732-84176552 |
| 14021 | Myo19 | NM_025414.3 | chr11:84880219-84911131 | 14118 | Nanp | NM_026086.2 | chr2:151029684-151039379 |
| 14022 | Myo1a | NM_001081219.1 | chr10:127705255-127720940 | 14119 | Nans | NM_053179.3 | chr4:46489328-46503438 |
| 14023 | Myo1b | NM_001161817.2 | chr1:51749757-51915978 | 14120 | Napll1 | NM_001146707.1 | chr10:111480616-111498150 |
| 14024 | Myo1c | NM_001080774.1 | chr11:75652149-75674634 | 14121 | Napll2 | NM_008671.2 | chrX:103184858-103186664 |
| 14025 | Myo1d | NM_177390.3 | chr11:80482126-80780025 | 14122 | Napll3 | NM_138742.1 | chrX:122394560-122397385 |
| 14026 | Myo1e | NM_181072.3 | chr9:70207349-70400067 | 14123 | Napll4 | NM_001285489.1 | chr7:143513678-143549120 |
| 14027 | Myo1f | NM_053214.2 | chr17:33555706-33607764 | 14124 | Napll5 | NM_021432.2 | chr6:58905232-58907126 |
| 14028 | Myo1g | NM_146440.4 | chr11:6506547-6520958 | 14125 | Napa | NM_025898.3 | chr7:16098842-16117975 |
| 14029 | Myo1h | NM_001164573.1 | chr5:114314940-114364576 | 14126 | Napb | NM_019632.3 | chr2:148694656-148732420 |
| 14030 | Myo3a | NM_148413.3 | chr2:22227502-22423370 | 14127 | Napepld | NM_178728.5 | chr5:21662902-21701345 |
| 14031 | Myo3b | NM_177376.4 | chr2:70039125-70429195 | 14128 | Napg | NM_028017.1 | chr18:62977915-62999451 |
| 14032 | Myo5a | NM_010864.2 | chr9:75071205-75223687 | 14129 | Naprt1 | NM_172607.3 | chr15:75890963-75894481 |
| 14033 | Myo5b | NM_201600.2 | chr18:74442618-74771477 | 14130 | Napsa | NM_008437.1 | chr7:44572444-44586846 |
| 14034 | Myo5c | NM_001081322.1 | chr9:75232013-75305450 | 14131 | Narf | NM_026272.3 | chr11:121217235-121255856 |
| 14035 | Myo6 | NM_001039546.2 | chr9:80165033-80311729 | 14132 | Narfl | NM_026238.4 | chr17:25773775-25783332 |
| 14036 | Myo7a | NM_001256081.1 | chr7:96801053-98119493 | 14133 | Narg2 | NM_145618.3 | chr6:69397997-69433074 |
| 14037 | Myo7b | NM_032394.3 | chr18:31959233-32036931 | 14134 | Nars | NM_001142950.1 | chr18:64499646-64516557 |
| 14038 | Myo9a | NM_173018.2 | chr9:59751173-59928866 | 14135 | Nars2 | NM_153591.4 | chr7:96951526-97084757 |
| 14039 | Myo9b | NM_001142322.1 | chr8:71272713-71360712 | 14136 | Nasp | NM_001081475.1 | chr4:116601053-116627497 |
| 14040 | Myoc | NM_010865.3 | chr1:162639149-162649694 | 14137 | Nat1 | NM_008673.1 | chr8:67490757-67492103 |
| 14041 | Myocd | NM_145136.4 | chr11:65176570-65269989 | 14138 | Nat10 | NM_153126.2 | chr2:103721258-103761250 |
| 14042 | Myod1 | NM_010866.2 | chr7:46376473-46379092 | 14139 | Nat14 | NM_203355.3 | chr7:4922250-4925006 |
| 14043 | Myof | NM_001099634.1 | chr19:37899035-38043577 | 14140 | Nat2 | NM_001168577.1 | chr8:67494874-67502578 |
| 14044 | Myog | NM_031189.2 | chr1:134290003-134292548 | 14141 | Nat3 | NM_008674.2 | chr8:67523853-67548627 |
| 14045 | Myom1 | NM_001083934.1 | chr17:71019556-71126856 | 14142 | Nat6 | NM_019750.3 | chr9:107580169-107584048 |
| 14046 | Myom2 | NM_008664.2 | chr8:15057652-15133419 | 14143 | Nat8 | NM_023455.3 | chr6:85830356-85831890 |
| 14047 | Myom3 | NM_001085509.2 | chr4:135759714-135815967 | 14144 | Nat8l | NM_001001985.2 | chr5:33995983-34005915 |
| 14048 | Myot | NM_001033621.3 | chr18:44334073-44355722 | 14145 | Nat9 | NM_025400.3 | chr11:115182891-115187316 |
| 14049 | Myoz1 | NM_021508.3 | chr14:20649101-20656540 | 14146 | Nav1 | NM_173437.2 | chr1:135434579-135585355 |
| 14050 | Myoz2 | NM_021503.2 | chr3:123006205-123034987 | 14147 | Nav2 | NM_001111016.1 | chr7:48959072-49610088 |
| 14051 | Myoz3 | NM_133363.3 | chr18:60573716-60591716 | 14148 | Nav3 | NM_001081035.1 | chr10:109693438-110000219 |
| 14052 | Mypn | NM_182992.2 | chr10:63115794-63203952 | 14149 | Nbas | NM_027706.1 | chr12:13269126-13583811 |
| 14053 | Mypop | NM_145579.3 | chr7:18991284-19001766 | 14150 | Nbea | NM_030595.1 | chr3:55825197-56183701 |
| 14054 | Myrf | NM_001033481.9 | chr19:10120870-10240748 | 14151 | Nbeal1 | NM_173444.2 | chr1:60180598-60334705 |
| 14055 | Myrfl | NM_001033333.3 | chr10:116776544-116896879 | 14152 | Nbeal2 | NM_183276.2 | chr9:110624788-110654161 |
| 14056 | Myrip | NM_144557.5 | chr9:120304072-120474834 | 14153 | Nbl1 | NM_008675.3 | chr4:139082291-139092970 |
| 14057 | Mysm1 | NM_177239.2 | chr4:94942040-94979100 | 14154 | Nbn | NM_013752.3 | chr4:15975966-15992589 |
| 14058 | Myt1 | NM_001171615.1 | chr2:181763331-181827775 | 14155 | Nbr1 | NM_001252220.1 | chr11:101552106-101581951 |
| 14059 | Myt1l | NM_001093775.1 | chr12:29528383-29923209 | 14156 | Ncald | NM_001170866.1 | chr15:37866174-37792000 |
| 14060 | Myzap | NM_001033208.4 | chr9:71504346-71592360 | 14157 | Ncam1 | NM_001081445.1 | chr9:49502145-49799069 |
| 14061 | Mzb1 | NM_027222.3 | chr18:35647264-35649367 | 14158 | Ncam2 | NM_001113208.1 | chr16:81200696-81624287 |
| 14062 | Mzf1 | NM_001290452.1 | chr7:13042302-13054764 | 14159 | Ncan | NM_007789.3 | chr8:70093084-70120844 |
| 14063 | Mzt1 | NM_175245.4 | chr14:99034543-99046136 | 14160 | Ncapd2 | NM_146171.1 | chr6:125168006-125191586 |
| 14064 | Mzt2 | NM_029354.4 | chr16:15848440-15863322 | 14161 | Ncapd3 | NM_178113.3 | chr9:27039174-27095315 |

Fig.21 - 74

| | | | | | | | |
|---|---|---|---|---|---|---|---|
| 14162 | Ncapg | NM_019438.1 | chr5:45669924-45700547 | 14259 | Ndufv2 | NM_001278415.1 | chr17:66078794-66101559 |
| 14163 | Ncapg2 | NM_133762.3 | chr12:116405401-116463531 | 14260 | Ndufv3 | NM_001083891.1 | chr17:31520114-31531325 |
| 14164 | Ncaph | NM_144818.3 | chr2:127103809-127133954 | 14261 | Neat1 | NR_003513.3 | chr19:5842295-5845480 |
| 14165 | Ncaph2 | NM_001115132.2 | chr15:89355718-89372850 | 14262 | Neb | NM_010889.1 | chr2:52136646-52338798 |
| 14166 | Ncbp1 | NM_001033201.3 | chr4:46139510-46172402 | 14263 | Nebl | NM_028757.2 | chr2:17346733-17731068 |
| 14167 | Ncbp2 | NM_026854.4 | chr16:31948545-31958472 | 14264 | Necab1 | NM_178617.4 | chr4:14952244-15148131 |
| 14168 | Nccrp1 | NM_001081115.1 | chr7:28543595-28547254 | 14265 | Necab2 | NM_054095.2 | chr8:119446718-119472635 |
| 14169 | Ncdn | NM_011986.4 | chr4:126743749-126753429 | 14266 | Necab3 | NM_023546.3 | chr2:154544404-154558853 |
| 14170 | Nceh1 | NM_178772.3 | chr3:27183003-27244911 | 14267 | Nectan1 | NM_026267.2 | chr6:122874556-122888941 |
| 14171 | Ncf1 | NM_001286037.1 | chr5:134220258-134229625 | 14268 | Necap2 | NM_025383.3 | chr4:141066511-141078346 |
| 14172 | Ncf2 | NM_010877.5 | chr1:152800152-152836990 | 14269 | Nedd1 | NM_008682.2 | chr10:92684744-92722418 |
| 14173 | Ncf4 | NM_008677.2 | chr15:78244810-78262580 | 14270 | Nedd4 | NM_010890.3 | chr9:72662346-72749848 |
| 14174 | Nck1 | NM_010878.2 | chr9:100495002-100546053 | 14271 | Nedd4l | NM_001114386.1 | chr18:64887755-65217826 |
| 14175 | Nck2 | NM_010879.3 | chr1:43443750-43570518 | 14272 | Nedd8 | NM_008683.3 | chr14:55662266-55671906 |
| 14176 | Nckap1 | NM_001290745.1 | chr2:80500511-80581182 | 14273 | Nedd9 | NM_001111324.2 | chr13:41309915-41487360 |
| 14177 | Nckap1l | NM_153505.4 | chr15:103453824-103498200 | 14274 | Nefh | NM_010904.3 | chr11:4938755-4948064 |
| 14178 | Nckap5 | NM_001081756.1 | chr1:125913635-126880632 | 14275 | Nefl | NM_010910.1 | chr14:68083883-68087737 |
| 14179 | Nckap5l | NM_001001884.1 | chr15:99422033-99457748 | 14276 | Nefm | NM_008691.2 | chr14:68119544-68125004 |
| 14180 | Nckipsd | NM_030729.4 | chr9:108808379-108818366 | 14277 | Negr1 | NM_001039994.3 | chr3:156561793-157316464 |
| 14181 | Ncl | NM_010880.3 | chr1:86344718-86359455 | 14278 | Neil1 | NM_028347.2 | chr9:57143255-57147034 |
| 14182 | Ncln | NM_134004.5 | chr10:81486458-81496363 | 14279 | Neil2 | NM_201610.2 | chr14:63182444-63193525 |
| 14183 | Ncmap | NM_001168498.1 | chr4:135369576-135385672 | 14280 | Neil3 | NM_146208.2 | chr8:53586866-53639965 |
| 14184 | Ncoa1 | NM_010681.2 | chr12:4247361-4477182 | 14281 | Nek1 | NM_175089.4 | chr8:60993192-61131346 |
| 14185 | Ncoa2 | NM_001302702.1 | chr1:13139105-13374691 | 14282 | Nek10 | NM_001195229.1 | chr14:14820814-15006693 |
| 14186 | Ncoa3 | NM_008679.3 | chr2:165992636-166073242 | 14283 | Nek11 | NM_172481.3 | chr9:105162466-105395287 |
| 14187 | Ncoa4 | NM_001033989.2 | chr14:32159886-32179855 | 14284 | Nek2 | NM_010892.3 | chr1:191821472-191833049 |
| 14188 | Ncoa5 | NM_144892.1 | chr2:165000356-165034779 | 14285 | Nek3 | NM_001162947.1 | chr8:22128285-22162494 |
| 14189 | Ncoa6 | NM_001242558.1 | chr2:155390655-155440783 | 14286 | Nek4 | NM_011849.3 | chr14:30951376-30988821 |
| 14190 | Ncoa7 | NM_001111267.2 | chr10:30645581-30655867 | 14287 | Nek5 | NM_177898.4 | chr8:22073615-22125053 |
| 14191 | Ncor1 | NM_001252313.1 | chr11:62316425-62438515 | 14288 | Nek6 | NM_001159631.1 | chr2:38511875-38587490 |
| 14192 | Ncor2 | NM_001253904.1 | chr5:125017152-125179214 | 14289 | Nek7 | NM_021605.4 | chr1:138483836-138619757 |
| 14193 | Ncr1 | NM_010746.3 | chr7:4337723-4345164 | 14290 | Nek8 | NM_080849.3 | chr11:78166105-78176666 |
| 14194 | Ncs1 | NM_019681.3 | chr2:31245922-31295471 | 14291 | Nek9 | NM_145138.2 | chr12:85299513-85359362 |
| 14195 | Nestn | NM_021607.3 | chr1:172066012-172082749 | 14292 | Nelfa | NM_013914.2 | chr5:33898179-33936258 |
| 14196 | Nctc1 | NR_002452.2 | chr7:142544608-142558598 | 14293 | Nelfb | NM_021393.3 | chr2:25199711-25211489 |
| 14197 | Ndc1 | NM_028355.3 | chr4:107367783-107414338 | 14294 | Nelfcd | NM_020580.3 | chr2:174419803-174427502 |
| 14198 | Ndc80 | NM_023294.2 | chr17:71496098-71526857 | 14295 | Nelfe | NM_001045863.1 | chr17:34850390-34856372 |
| 14199 | Ndel1 | NM_001114085.1 | chr16:14163274-14192923 | 14296 | Nell1 | NM_001037906.2 | chr7:49975349-50863289 |
| 14200 | Ndel1 | NM_023682.2 | chr15:68821445-68853131 | 14297 | Nellos | NR_045928.1 | chr7:50517308-50575884 |
| 14201 | Ndfip1 | NM_022996.1 | chr18:38418974-38464406 | 14298 | Nell2 | NM_001289653.1 | chr15:95219439-95528252 |
| 14202 | Ndfip2 | NM_001190989.1 | chr14:105258672-105309298 | 14299 | Nemf | NM_025441.3 | chr12:69311542-69367176 |
| 14203 | Ndn | NM_010882.3 | chr7:62348276-62349927 | 14300 | Nenf | NM_025424.2 | chr1:191306796-191318118 |
| 14204 | Ndnf | NM_172399.3 | chr6:65671610-65706930 | 14301 | Neo1 | NM_001042752.1 | chr9:58874679-59036441 |
| 14205 | Ndnl2 | NM_023239.4 | chr7:64871649-64873040 | 14302 | Nepn | NM_025684.2 | chr10:52391607-52404604 |
| 14206 | Ndor1 | NM_001082476.2 | chr2:25244812-25255414 | 14303 | Nes | NM_016701.3 | chr3:87971092-87980451 |
| 14207 | Ndp | NM_010883.3 | chrX:16885520-16911774 | 14304 | Nespas | NR_002846.2 | chr2:174281236-174295436 |
| 14208 | Ndrg1 | NM_008681.2 | chr15:66923917-66969641 | 14305 | Net1 | NM_001047159.2 | chr13:3882017-3893581 |
| 14209 | Ndrg2 | NM_001145959.1 | chr14:51905270-51913488 | 14306 | Neto1 | NM_144946.4 | chr18:86394951-86501897 |
| 14210 | Ndrg3 | NM_013865.2 | chr2:156927341-156992111 | 14307 | Neto2 | NM_001081324.1 | chr8:85636587-85691009 |
| 14211 | Ndrg4 | NM_001195006.1 | chr8:95703036-95715119 | 14308 | Neu1 | NM_010893.3 | chr17:34931252-34937297 |
| 14212 | Ndst1 | NM_008306.4 | chr18:60685975-60733389 | 14309 | Neu2 | NM_001160363.1 | chr1:87574026-87597840 |
| 14213 | Ndst2 | NM_010811.2 | chr14:20723729-20734562 | 14310 | Neu3 | NM_016720.2 | chr7:99811438-99828417 |
| 14214 | Ndst3 | NM_031186.3 | chr3:123526165-123672477 | 14311 | Neu4 | NM_173772.3 | chr1:94020492-94028330 |
| 14215 | Ndst4 | NM_022565.2 | chr3:125404090-125724986 | 14312 | Neurl1a | NM_001168480.1 | chr19:47228842-47259441 |
| 14216 | Ndufa1 | NM_019443.2 | chrX:37187588-37191298 | 14313 | Neurl1b | NM_001081656.2 | chr17:26414964-26446842 |
| 14217 | Ndufa10 | NM_024197.1 | chr1:92439718-92473758 | 14314 | Neurl2 | NM_001082974.2 | chr2:164830729-164833596 |
| 14218 | Ndufa11 | NM_027244.1 | chr17:56717761-56724248 | 14315 | Neurl3 | NM_153408.2 | chr1:36264603-36273425 |
| 14219 | Ndufa12 | NM_025551.3 | chr10:94199008-94220948 | 14316 | Neurl4 | NM_001013414.3 | chr11:69901815-69913824 |
| 14220 | Ndufa13 | NM_023312.2 | chr8:69894181-69902558 | 14317 | Neurod1 | NM_010894.2 | chr2:79452640-79456636 |
| 14221 | Ndufa2 | NM_010885.5 | chr18:36742331-36744587 | 14318 | Neurod2 | NM_010895.3 | chr11:98325416-98329645 |
| 14222 | Ndufa3 | NM_025348.2 | chr7:3617372-3620161 | 14319 | Neurod4 | NM_007501.4 | chr10:130268151-130280240 |
| 14223 | Ndufa4 | NM_010886.2 | chr6:11900372-11907446 | 14320 | Neurod6 | NM_009717.2 | chr6:55677818-55681263 |
| 14224 | Ndufa4l2 | NM_001098789.1 | chr10:127514938-127517156 | 14321 | Neurog1 | NM_010896.3 | chr13:56250497-56252163 |
| 14225 | Ndufa5 | NM_026614.2 | chr6:24518665-24527687 | 14322 | Neurog2 | NM_009718.2 | chr3:127633144-127635631 |
| 14226 | Ndufa6 | NM_025987.3 | chr15:82350138-82354291 | 14323 | Neurog3 | NM_009719.6 | chr10:62133089-62134783 |
| 14227 | Ndufa7 | NM_023202.4 | chr17:33824571-33838316 | 14324 | Nexn | NM_199465.2 | chr3:152236983-152266320 |
| 14228 | Ndufa8 | NM_026703.2 | chr2:36036333-36049292 | 14325 | Nf1 | NM_010897.2 | chr11:79339891-79581609 |
| 14229 | Ndufa9 | NM_025358.3 | chr6:126821862-126849144 | 14326 | Nf2 | NM_010898.3 | chr11:4765844-4849544 |
| 14230 | Ndufab1 | NM_028058.3 | chr7:122085043-122101848 | 14327 | Nfam1 | NM_001252250.1 | chr15:82996735-83093397 |
| 14231 | Ndufaf1 | NM_027175.3 | chr2:119655450-119662798 | 14328 | Nfasc | NM_001274411.1 | chr1:132564689-132642858 |
| 14232 | Ndufaf2 | NM_001127346.1 | chr13:108052588-108158625 | 14329 | Nfat5 | NM_001286260.1 | chr8:107293469-107379517 |
| 14233 | Ndufaf3 | NM_023247.1 | chr9:108565864-108567342 | 14330 | Nfatc1 | NM_001164109.1 | chr18:80647434-80713071 |
| 14234 | Ndufaf4 | NM_026742.4 | chr4:24898082-24905001 | 14331 | Nfatc2 | NM_001037177.2 | chr2:168518198-168590365 |
| 14235 | Ndufaf5 | NM_027093.4 | chr2:140170645-140205252 | 14332 | Nfatc2ip | NM_010900.3 | chr7:126382853-126396737 |
| 14236 | Ndufaf6 | NM_001085493.2 | chr4:11051045-11076205 | 14333 | Nfatc3 | NM_010901.2 | chr8:106059802-106130537 |
| 14237 | Ndufaf7 | NM_028611.3 | chr17:78937134-78948052 | 14334 | Nfatc4 | NM_001168346.1 | chr14:55824794-55833943 |
| 14238 | Ndufb10 | NM_026684.2 | chr17:24722066-24724248 | 14335 | Nfe2 | NM_008685.3 | chr15:103248211-103255439 |
| 14239 | Ndufb11 | NM_019435.4 | chrX:20615325-20617564 | 14336 | Nfe2l1 | NM_001130450.1 | chr11:96817413-96829502 |
| 14240 | Ndufb2 | NM_026612.2 | chr6:39592582-39599471 | 14337 | Nfe2l2 | NM_010902.4 | chr2:75675512-75704663 |
| 14241 | Ndufb3 | NM_025597.3 | chr1:58586396-58595964 | 14338 | Nfe2l3 | NM_010903.1 | chr6:51432669-51458768 |
| 14242 | Ndufb4 | NM_026610.1 | chr16:37647601-37654368 | 14339 | Nfia | NM_001122952.1 | chr4:97581942-98118876 |
| 14243 | Ndufb5 | NM_025316.3 | chr3:32737062-32751559 | 14340 | Nfib | NM_001113209.2 | chr4:82290172-82505779 |
| 14244 | Ndufb6 | NM_001033305.3 | chr4:40276590-40279421 | 14341 | Nfic | NM_008688.3 | chr10:81396190-81407173 |
| 14245 | Ndufb7 | NM_025843.3 | chr8:83566757-83571623 | 14342 | Nfil3 | NM_017373.3 | chr13:52967208-52981039 |
| 14246 | Ndufb8 | NM_026684.2 | chr19:44550253-44556415 | 14343 | Nfix | NM_001081981.2 | chr8:84704711-84774369 |
| 14247 | Ndufb9 | NM_029172.3 | chr15:58933809-58939489 | 14344 | Nfkb1 | NM_008689.2 | chr3:135584654-135691547 |
| 14248 | Ndufc1 | NM_025523.1 | chr3:51418978-51408955 | 14345 | Nfkb2 | NM_001177369.1 | chr19:46304736-46312090 |
| 14249 | Ndufc2 | NM_024220.2 | chr7:97400002-97407800 | 14346 | Nfkbia | NM_010907.2 | chr12:55489408-55492647 |
| 14250 | Ndufs1 | NM_001160038.1 | chr1:63143591-63176822 | 14347 | Nfkbib | NM_010908.5 | chr7:28758250-28766644 |
| 14251 | Ndufs2 | NM_153064.5 | chr1:171234852-171247122 | 14348 | Nfkbid | NM_172142.3 | chr7:30423303-30428746 |
| 14252 | Ndufs3 | NM_026688.2 | chr2:90894635-90904721 | 14349 | Nfkbie | NM_008690.4 | chr17:45555699-45563168 |
| 14253 | Ndufs4 | NM_010887.2 | chr13:114287794-114388094 | 14350 | Nfkbil1 | NM_010909.4 | chr17:35220174-35235815 |
| 14254 | Ndufs5 | NM_001030274.1 | chr123712709-123718186 | 14351 | Nfkbiz | NM_001159394.1 | chr16:55811376-55822138 |
| 14255 | Ndufs6 | NM_010888.3 | chr13:73819875-73828482 | 14352 | Nfrkb | NM_172766.3 | chr9:31386191-31421334 |
| 14256 | Ndufs7 | NM_029272.3 | chr10:82094451-80256792 | 14353 | Nfs1 | NM_010911.2 | chr2:156123636-156144186 |
| 14257 | Ndufs8 | NM_027144.3 | chr19:3908862-3912774 | 14354 | Nfu1 | NM_001170591.1 | chr6:87009835-87028461 |
| 14258 | Ndufv1 | NM_133666.3 | chr19:4007438-4012755 | 14355 | Nfx1 | NM_001290448.1 | chr4:40979905-41013873 |

Fig.21 - 75

| | | | | | | | |
|---|---|---|---|---|---|---|---|
| 14356 | Nfxl1 | NM_133921.2 | chr5:72513303-72599645 | 14453 | Nlrp4c | NM_031389.2 | chr7:6045160-6105149 |
| 14357 | Nfya | NM_001110832.1 | chr17:48286884-48409820 | 14454 | Nlrp4e | NM_001004294.2 | chr7:23301191-23362277 |
| 14358 | Nfyb | NM_010914.2 | chr10:82748699-82764141 | 14455 | Nlrp4f | NM_175290.4 | chr13:65177110-65205716 |
| 14359 | Nfyc | NM_001048368.2 | chr4:120757434-120831579 | 14456 | Nlrp4g | NM_001004145.2 | chr9:124348830-124354483 |
| 14360 | Ngb | NM_022414.2 | chr12:87097530-87102539 | 14457 | Nlrp5 | NM_001039143.2 | chr7:23385888-23441923 |
| 14361 | Ngdn | NM_026890.2 | chr14:55015453-55024137 | 14458 | Nlrp5-ps | NR_045119.1 | chr7:14561170-14623066 |
| 14362 | Ngef | NM_001111314.1 | chr1:87476828-87573870 | 14459 | Nlrp6 | NM_133946.2 | chr7:140920901-140929192 |
| 14363 | Ngf | NM_001112698.2 | chr3:102469918-102521013 | 14460 | Nlrp9a | NM_001048219.2 | chr7:26535022-26574146 |
| 14364 | Ngfr | NM_033217.3 | chr11:95568826-95587698 | 14461 | Nlrp9b | NM_194058.2 | chr7:20008022-20082938 |
| 14365 | Ngfrap1 | NM_001110233.1 | chrX:136270252-136271978 | 14462 | Nlrp9c | NM_001942612.1 | chr7:26364886-26394243 |
| 14366 | Ngly1 | NM_021504.3 | chr14:16249813-16311926 | 14463 | Nlrx1 | NM_001163742.1 | chr9:44252712-44268599 |
| 14367 | Ngp | NM_008694.2 | chr9:110419807-110423012 | 14464 | Nmb | NM_001291280.1 | chr7:80902226-80905062 |
| 14368 | Ngrn | NM_031375.4 | chr7:80261214-80265378 | 14465 | Nmbr | NM_008703.2 | chr10:14760288-14770556 |
| 14369 | Nhej1 | NM_029342.4 | chr1:74967345-75046639 | 14466 | Nmd3 | NM_133787.2 | chr3:69722054-69749046 |
| 14370 | Nhlh1 | NM_010916.2 | chr1:172052291-172057596 | 14467 | Nme1 | NM_008704.2 | chr11:93958924-93968521 |
| 14371 | Nhlh2 | NM_178777.3 | chr3:102010144-102015492 | 14468 | Nme2 | NM_001077529.2 | chr11:93949813-93955783 |
| 14372 | Nhlrc1 | NM_175340.4 | chr13:47012556-47014850 | 14469 | Nme3 | NM_019730.2 | chr17:24896499-24899529 |
| 14373 | Nhlrc2 | NM_025811.3 | chr19:56548260-56598846 | 14470 | Nme4 | NM_019731.1 | chr17:26091744-26095470 |
| 14374 | Nhlrc3 | NM_172501.2 | chr3:53451995-53463258 | 14471 | Nme5 | NM_080637.3 | chr18:34562640-34579106 |
| 14375 | Nhlrc4 | NM_001039038.2 | chr17:25942232-25944931 | 14472 | Nme6 | NM_018757.1 | chr9:109832793-109842961 |
| 14376 | Nhp2 | NM_026631.3 | chr11:51619772-51623714 | 14473 | Nme7 | NM_138314.4 | chr1:164307671-164437300 |
| 14377 | Nhp2l1 | NM_011482.4 | chr15:82041344-82047598 | 14474 | Nme8 | NM_001167909.1 | chr13:19645078-19697780 |
| 14378 | Nhs | NM_001081052.2 | chrX:161836429-162159441 | 14475 | Nme9 | NM_001168957.1 | chr9:99456242-99479899 |
| 14379 | Nhsl1 | NM_001163592.1 | chr10:18469980-18533891 | 14476 | Nmi | NM_001141948.1 | chr2:51948498-51973208 |
| 14380 | Nhsl2 | NM_001163610.1 | chrX:101849384-102092055 | 14477 | Nmnat1 | NM_133435.1 | chr4:149468786-149485142 |
| 14381 | Nicn1 | NM_025449.3 | chr9:108290456-108296496 | 14478 | Nmnat2 | NM_175460.3 | chr1:152955100-153119261 |
| 14382 | Nid1 | NM_010917.2 | chr13:13437601-13512275 | 14479 | Nmnat3 | NM_144533.2 | chr9:98296582-98411428 |
| 14383 | Nid2 | NM_008695.2 | chr14:19751256-19811787 | 14480 | Nmral1 | NM_001290761.1 | chr16:4711317-4719356 |
| 14384 | NifSl1 | NM_025810.2 | chr2:58447632-58462276 | 14481 | Nmrk1 | NM_145497.2 | chr19:18632015-18652184 |
| 14385 | Nfk | NM_026472.4 | chr1:118321842-118333831 | 14482 | Nmrk2 | NM_027120.2 | chr10:81198169-81202037 |
| 14386 | Nim1k | NM_175583.3 | chr13:119710093-119755882 | 14483 | Nms | NM_001011684.2 | chr1:138939148-38950278 |
| 14387 | Nin | NM_001081453.1 | chr12:70011434-70102854 | 14484 | Nmt1 | NM_008707.3 | chr11:103028561-103066105 |
| 14388 | Ninj1 | NM_013610.2 | chr13:49187546-49196251 | 14485 | Nmt2 | NM_001290368.1 | chr2:3284211-3328877 |
| 14389 | Ninj2 | NM_016718.2 | chr6:120093379-120200338 | 14486 | Nmu | NM_019515.1 | chr5:76333494-76363777 |
| 14390 | Ninl | NM_207204.2 | chr2:150934618-151009398 | 14487 | Nmur1 | NM_010341.1 | chr1:86386324-86388141 |
| 14391 | Nip7 | NM_001164472.1 | chr8:107056876-107060928 | 14488 | Nmur2 | NM_153079.4 | chr11:56024989-56040987 |
| 14392 | Nipa1 | NM_153762.3 | chr7:55965483-56019573 | 14489 | Nnat | NM_001291128.1 | chr2:157560077-157562525 |
| 14393 | Nipa2 | NM_001256130.1 | chr7:55931265-55962493 | 14490 | Nnmt | NM_010924.3 | chr9:48591876-48605123 |
| 14394 | Nipal1 | NM_001081205.1 | chr5:72647795-72671078 | 14491 | Nnt | NM_008710.3 | chr13:119434316-119409011 |
| 14395 | Nipal2 | NM_145469.5 | chr15:34572798-34678706 | 14492 | Noa1 | NM_019836.3 | chr5:77294168-77310086 |
| 14396 | Nipal3 | NM_028995.3 | chr4:135448900-135494504 | 14493 | Nob1 | NM_026277.3 | chr8:107412488-107425038 |
| 14397 | Nipal4 | NM_172524.3 | chr11:46148154-46166339 | 14494 | Nobox | NM_130869.3 | chr6:43303673-43309554 |
| 14398 | Nipbl | NM_027707.3 | chr15:8289823-8444463 | 14495 | Noc2l | NM_023303.2 | chr4:156236009-156247616 |
| 14399 | Nipsnap1 | NM_008698.2 | chr11:4874002-4894200 | 14496 | Noc3l | NM_023315.2 | chr19:38788127-38819237 |
| 14400 | Nipsnap3a | NM_028529.3 | chr4:52989283-53000854 | 14497 | Noc4l | NM_153570.2 | chr5:110648418-110653382 |
| 14401 | Nipsnap3b | NM_025623.2 | chr4:53011923-53022059 | 14498 | Nod1 | NM_001171007.1 | chr6:54923941-54971661 |
| 14402 | Nisch | NM_022116.1 | chr14:31170927-31206826 | 14499 | Nod2 | NM_145857.2 | chr8:88647346-88688474 |
| 14403 | Nit1 | NM_001242580.1 | chr1:171342236-171345645 | 14500 | Nodal | NM_013611.4 | chr10:61417971-61425337 |
| 14404 | Nit2 | NM_023175.1 | chr16:57156664-57167332 | 14501 | Nog | NM_008711.2 | chr11:89300637-89302559 |
| 14405 | Nkain1 | NM_025993.3 | chr4:130530130-130574036 | 14502 | Nol10 | NM_001008421.1 | chr12:17348492-17430095 |
| 14406 | Nkain2 | NM_001013411.2 | chr10:31689318-32889915 | 14503 | Nol11 | NM_001161329.1 | chr11:107166660-107189381 |
| 14407 | Nkain3 | NM_001290410.1 | chr4:20118873-20778668 | 14504 | Nol12 | NM_133800.3 | chr15:78934932-78941910 |
| 14408 | Nkain4 | NM_001141933.1 | chr2:180934771-180954699 | 14505 | Nol3 | NM_030152.4 | chr8:105276446-105281939 |
| 14409 | Nkap | NM_025937.4 | chrX:37128762-37150746 | 14506 | Nol4 | NM_001161483.1 | chr18:22693154-23038663 |
| 14410 | Nkapl | NM_025719.3 | chr13:21467406-21468501 | 14507 | Nol6 | NM_139236.3 | chr4:41114426-41124339 |
| 14411 | Nkd1 | NM_001163660.1 | chr8:88527632-88594887 | 14508 | Nol7 | NM_023554.2 | chr13:43398375-43402858 |
| 14412 | Nkd2 | NM_028186.4 | chr13:73819327-73847631 | 14509 | Nol8 | NM_001271397.1 | chr13:49653077-49679016 |
| 14413 | Nkg7 | NM_024253.4 | chr7:43437137-43438246 | 14510 | Nol9 | NM_001159599.2 | chr4:152039320-152060038 |
| 14414 | Nkiras1 | NM_023526.4 | chr14:18271141-18284000 | 14511 | Nolc1 | NM_001039351.2 | chr19:46075846-46085543 |
| 14415 | Nkiras2 | NM_028024.2 | chr11:100622954-100627602 | 14512 | Nom1 | NM_001033457.2 | chr5:29434666-29452169 |
| 14416 | Nkpd1 | NM_027136.1 | chr7:19518730-19525050 | 14513 | Nomo1 | NM_153057.4 | chr7:46033695-46084212 |
| 14417 | Nkrf | NM_029891.2 | chrX:36887541-36902899 | 14514 | Nono | NM_001252518.1 | chrX:101429650-101448593 |
| 14418 | Nktr | NM_010918.1 | chr9:121719180-121756841 | 14515 | Nop10 | NM_025403.4 | chr2:112261925-112262898 |
| 14419 | Nkx1-1 | NM_011320.1 | chr5:33430733-33434090 | 14516 | Nop14 | NM_029278.2 | chr5:34638535-34660148 |
| 14420 | Nkx1-2 | NM_009123.2 | chr7:132596238-132599637 | 14517 | Nop16 | NM_178605.4 | chr13:54584190-54590074 |
| 14421 | Nkx2-1 | NM_001146398.1 | chr12:56535301-56535106 | 14518 | Nop2 | NM_138747.2 | chr6:125131582-125144753 |
| 14422 | Nkx2-2 | NM_001077632.1 | chr2:147177545-147186402 | 14519 | Nop56 | NM_024193.2 | chr2:130274411-130279315 |
| 14423 | Nkx2-2os | NR_030769.2 | chr2:147184082-147331681 | 14520 | Nop58 | NM_018868.2 | chr1:59685005-59711510 |
| 14424 | Nkx2-3 | NM_008690.2 | chr19:43615234-43616892 | 14521 | Nop9 | NM_026403.3 | chr14:85745692-55755634 |
| 14425 | Nkx2-4 | NM_023504.1 | chr2:147083875-147085345 | 14522 | Nos1 | NM_008712.3 | chr5:117866838-117958840 |
| 14426 | Nkx2-5 | NM_008700.1 | chr17:26838664-26841565 | 14523 | Nos1ap | NM_001109985.1 | chr1:170317495-170589849 |
| 14427 | Nkx2-6 | NM_010920.2 | chr14:69171803-69175540 | 14524 | Nos2 | NM_010927.4 | chr11:78920786-78960226 |
| 14428 | Nkx2-9 | NM_008701.2 | chr12:56611396-56613284 | 14525 | Nos3 | NM_008713.4 | chr5:24364818-24384474 |
| 14429 | Nkx3-1 | NM_010921.3 | chr14:69190691-69194658 | 14526 | Nosip | NM_001163684.1 | chr7:45062428-45078503 |
| 14430 | Nkx3-2 | NM_007524.3 | chr5:41761482-41764220 | 14527 | Nostrin | NM_181547.3 | chr2:69135799-69189329 |
| 14431 | Nkx6-1 | NM_144955.2 | chr5:101659196-101664711 | 14528 | Notch1 | NM_008714.3 | chr2:26457901-26503822 |
| 14432 | Nkx6-2 | NM_183288.3 | chr7:139581219-139582797 | 14529 | Notch2 | NM_010928.2 | chr3:98015357-98150367 |
| 14433 | Nkx6-3 | NM_029002.2 | chr8:23153270-23158948 | 14530 | Notch3 | NM_008716.2 | chr17:32120892-32166852 |
| 14434 | Nlel | NM_145431.2 | chr11:82900767-82908395 | 14531 | Notch4 | NM_010929.2 | chr17:34564294-34588543 |
| 14435 | Nlgn1 | NM_001163387.1 | chr3:25481840-26153307 | 14532 | Noto | NM_001007472.2 | chr6:85423885-85428877 |
| 14436 | Nlgn2 | NM_198862.2 | chr11:69823122-69834849 | 14533 | Notum | NM_175263.4 | chr11:120653788-120660837 |
| 14437 | Nlgn3 | NM_172932.4 | chrX:101299178-101321350 | 14534 | Nov | NM_010930.4 | chr15:54745927-54753761 |
| 14438 | Nlk | NM_008702.3 | chr11:78567167-78697425 | 14535 | Nova1 | NM_021361.1 | chr12:46694516-46818775 |
| 14439 | Nln | NM_029472.3 | chr13:104023438-104109614 | 14536 | Nova2 | NM_001029877.3 | chr7:18925867-18965319 |
| 14440 | Nlrc3 | NM_001081280.1 | chr16:3960682-3976692 | 14537 | Nox1 | NM_172203.2 | chrX:134086420-134111854 |
| 14441 | Nlrc4 | NM_001033867.3 | chr17:74426294-74459108 | 14538 | Nox3 | NM_198958.2 | chr17:3635289-3696261 |
| 14442 | Nlrc5 | NM_001033207.3 | chr8:94626742-94527272 | 14539 | Nox4 | NM_001285833.1 | chr7:87246648-87398708 |
| 14443 | Nlrp10 | NM_175532.3 | chr7:108921852-108930158 | 14540 | Noxa1 | NM_001163626.1 | chr2:25085669-25095205 |
| 14444 | Nlrp12 | NM_001033431.2 | chr7:3221509-3249740 | 14541 | Noxo1 | NM_027988.4 | chr17:24696233-24700529 |
| 14445 | Nlrp14 | NM_001002894.2 | chr7:107166989-107198103 | 14542 | Noxred1 | NM_027744.1 | chr12:87221122-87238601 |
| 14446 | Nlrp1a | NM_001004142.2 | chr11:71091196-71144704 | 14543 | Npas1 | NM_008718.2 | chr7:16455720-16476780 |
| 14447 | Nlrp1b | NM_001040696.1 | chr11:71153101-71230733 | 14544 | Npas2 | NM_008719.2 | chr1:39194271-39363240 |
| 14448 | Nlrp1c-ps | NR_027858.1 | chr11:71242429-71285232 | 14545 | Npas3 | NM_013780.2 | chr12:53248676-54072175 |
| 14449 | Nlrp2 | NM_177690.3 | chr7:5298546-5351035 | 14546 | Npas4 | NM_153553.4 | chr19:4984354-4989971 |
| 14450 | Nlrp3 | NM_145827.3 | chr11:59546285-59566956 | 14547 | Npat | NM_001081795.1 | chr9:53537046-53575627 |
| 14451 | Nlrp4a | NM_172896.2 | chr7:26435112-26475458 | 14548 | Npb | NM_153288.3 | chr11:120608476-120609100 |
| 14452 | Nlrp4b | NM_172481.2 | chr7:10687792-10730158 | 14549 | Npbwr1 | NM_010342.1 | chr5:5913706-5917398 |

Fig.21 - 76

| | | | | | | | | |
|---|---|---|---|---|---|---|---|---|
| 14550 | Npc1 | NM_008720.2 | chr18:12189693-12236386 | 14647 | Nrm1 | NM_153529.2 | chr13:36725621-36734477 |
| 14551 | Npc1l1 | NM_207242.2 | chr11:6211010-6230245 | 14648 | Nrn1l | NM_175024.4 | chr8:105893566-105895023 |
| 14552 | Npc2 | NM_023409.4 | chr12:84754558-84773112 | 14649 | Nron | NR_045729.1 | chr2:33805815-33813591 |
| 14553 | Npcd | NM_001013360.2 | chr15:79786350-79834333 | 14650 | Nrp | NM_001013372.2 | chr12:87442847-87444017 |
| 14554 | Npdc1 | NM_008721.4 | chr2:25403049-25409494 | 14651 | Nrp1 | NM_008737.2 | chr8:128359072-128505475 |
| 14555 | Npepl1 | NM_213733.2 | chr2:174110350-174122702 | 14652 | Nrp2 | NM_001077443.1 | chr1:62703316-62818692 |
| 14556 | Npepps | NM_008942.2 | chr11:97205855-97280576 | 14653 | Nrros | NM_146069.4 | chr16:32142824-32165476 |
| 14557 | Npff | NM_018787.1 | chr15:102523838-102524621 | 14654 | Nrsn1 | NM_009513.2 | chr13:25252038-25269996 |
| 14558 | Npffr1 | NM_001177511.1 | chr10:61595483-61626385 | 14655 | Nrsn2 | NM_001009948.1 | chr2:152368757-152376566 |
| 14559 | Npffr2 | NM_133192.3 | chr5:89527428-89583740 | 14656 | Nrtn | NM_008738.2 | chr17:56751324-56757530 |
| 14560 | Nphp1 | NM_001291012.1 | chr2:127740731-127788891 | 14657 | Nrxn1 | NM_020252.3 | chr17:90033648-91092802 |
| 14561 | Nphp3 | NM_028721.3 | chr9:104002543-104043811 | 14658 | Nrxn2 | NM_001205234.1 | chr19:6418737-6533217 |
| 14562 | Nphp4 | NM_153424.2 | chr4:152478141-152563184 | 14659 | Nrxn3 | NM_001198587.3 | chr12:88794503-90334933 |
| 14563 | Nphs1 | NM_019459.2 | chr7:30460057-30488609 | 14660 | Nsa2 | NM_021532.5 | chr13:97129426-97137926 |
| 14564 | Nphs1os | NR_004443.1 | chr7:30462163-30465591 | 14661 | Nsd1 | NM_008739.3 | chr13:55209781-55318325 |
| 14565 | Nphs2 | NM_130456.4 | chr1:156310718-156328035 | 14662 | Nsdhl | NM_010941.3 | chrX:72918520-72958528 |
| 14566 | Npl | NM_028749.1 | chr1:153503015-153549714 | 14663 | Nsf | NM_008740.4 | chr11:103821782-103954056 |
| 14567 | Nploc4 | NM_001195023.1 | chr11:120379797-120437700 | 14664 | Nsfl1c | NM_001291074.1 | chr2:151494181-151511310 |
| 14568 | Npm1 | NM_001252260.1 | chr11:33152497-33163206 | 14665 | Nsg1 | NM_010942.3 | chr5:38137192-38159467 |
| 14569 | Npm2 | NM_181345.3 | chr14:70647301-70653084 | 14666 | Nsg2 | NM_001290680.1 | chr11:32000699-32059211 |
| 14570 | Npm3 | NM_008723.1 | chr19:45747733-45749563 | 14667 | Nsl1 | NM_198654.3 | chr1:191063020-191084558 |
| 14571 | Npm3-ps1 | NR_002702.1 | chr6:85076140-85077126 | 14668 | Nsmaf | NM_010945.2 | chr4:6396207-6454271 |
| 14572 | Npnt | NM_001029836.2 | chr3:132881744-132950291 | 14669 | Nsmce1 | NM_026330.3 | chr7:125467639-125491542 |
| 14573 | Nppa | NM_008725.3 | chr4:148000745-148002067 | 14670 | Nsmce2 | NM_001164604.1 | chr15:59374197-59539666 |
| 14574 | Nppb | NM_001287348.1 | chr4:147985787-147987205 | 14671 | Nsmce4a | NM_001162855.1 | chr7:130532525-130547381 |
| 14575 | Nppc | NM_010933.5 | chr1:86666292-86670573 | 14672 | Nsmf | NM_001089386.1 | chr2:25054378-25062881 |
| 14576 | Npr1 | NM_008727.5 | chr3:90450591-90465866 | 14673 | Nsun2 | NM_145354.5 | chr13:69612015-69635779 |
| 14577 | Npr2 | NM_173788.3 | chr4:43631934-43651240 | 14674 | Nsun3 | NM_178925.3 | chr16:62734851-62786716 |
| 14578 | Npr3 | NM_001039181.1 | chr15:11839896-11905674 | 14675 | Nsun4 | NM_028142.4 | chr4:116031769-116053876 |
| 14579 | Nprl2 | NM_018879.2 | chr9:107542208-107545706 | 14676 | Nsun5 | NM_145414.2 | chr13:135369952-135376797 |
| 14580 | Nprl3 | NM_001284359.1 | chr11:32231962-32267707 | 14677 | Nsun6 | NM_001165941.1 | chr2:14995130-15054872 |
| 14581 | Nps | NM_001163611.1 | chr7:135268618-135272942 | 14678 | Nsun7 | NM_027602.2 | chr5:66260840-66298028 |
| 14582 | Npsr1 | NM_175678.3 | chr9:24098017-24316398 | 14679 | Nt5c | NM_015807.1 | chr11:115490425-115491814 |
| 14583 | Npto | NM_009145.2 | chr9:58582239-58652879 | 14680 | Nt5c1a | NM_001085602.1 | chr4:123201552-123216207 |
| 14584 | Nptx1 | NM_008730.2 | chr11:119538718-119547820 | 14681 | Nt5c1b | NM_027588.3 | chr12:10369970-10390174 |
| 14585 | Nptx2 | NM_016789.3 | chr5:144545886-144557478 | 14682 | Nt5c2 | NM_001164363.1 | chr19:46886830-47015189 |
| 14586 | Nptxr | NM_030689.4 | chr15:79786350-79804079 | 14683 | Nt5c3 | NM_001252374.1 | chr6:56882401-56901886 |
| 14587 | Npvf | NM_021892.1 | chr6:50650870-50654393 | 14684 | Nt5c3b | NM_001102650.1 | chr11:100429351-100441089 |
| 14588 | Npw | NM_001099664.1 | chr17:24529-24658425 | 14685 | Nt5dc1 | NM_176968.4 | chr10:34303611-34418528 |
| 14589 | Npy | NM_023456.3 | chr6:49822728-49829505 | 14686 | Nt5dc2 | NM_027289.1 | chr14:31134852-31139124 |
| 14590 | Npy1r | NM_010934.4 | chr8:66697421-66706798 | 14687 | Nt5dc3 | NM_175331.3 | chr10:86779004-86883389 |
| 14591 | Npy2r | NM_001205099.1 | chr3:82538382-82548085 | 14688 | Nt5e | NM_011851.4 | chr9:88027608-88372089 |
| 14592 | Npy4r | NM_008919.4 | chr14:34145645-34152419 | 14689 | Nt5m | NM_134029.2 | chr11:59848072-59876533 |
| 14593 | Npy5r | NM_016708.3 | chr8:66679964-66688094 | 14690 | Ntan1 | NM_010346.3 | chr16:13819276-13835431 |
| 14594 | Npy6r | NM_010935.3 | chr18:44270126-44277700 | 14691 | Ntf3 | NM_001164034.1 | chr6:126101411-126166744 |
| 14595 | Nqo1 | NM_008706.5 | chr8:107388224-107403205 | 14692 | Ntf5 | NM_198190.1 | chr7:45413694-45417179 |
| 14596 | Nqo2 | NM_001163299.1 | chr13:33964658-33988465 | 14693 | Nthl1 | NM_008743.2 | chr17:24632681-24638838 |
| 14597 | Nr0b1 | NM_007430.5 | chrX:86191774-86195946 | 14694 | Ntm | NM_172290.3 | chr9:28995963-29963129 |
| 14598 | Nr0b2 | NM_011850.3 | chr4:133553375-133556686 | 14695 | Ntmt1 | NM_170592.2 | chr2:30807976-30829014 |
| 14599 | Nr1d1 | NM_145434.4 | chr11:98767931-98775377 | 14696 | Ntn1 | NM_008744.2 | chr11:68209363-68386826 |
| 14600 | Nr1d2 | NM_011584.4 | chr14:18204055-18239106 | 14697 | Ntn3 | NM_010947.3 | chr17:24208842-24209387 |
| 14601 | Nr1h2 | NM_001285517.1 | chr7:44549615-44553965 | 14698 | Ntn4 | NM_021320.3 | chr10:93641048-93745972 |
| 14602 | Nr1h3 | NM_001184060.1 | chr2:91184060-91195116 | 14699 | Ntn5 | NM_001033356.3 | chr7:45684021-45694556 |
| 14603 | Nr1h4 | NM_001163504.1 | chr10:89454233-89533622 | 14700 | Ntng1 | NM_001163348.1 | chr3:109780049-110143472 |
| 14604 | Nr1h5 | NM_145998.2 | chr8:102939657-102964133 | 14701 | Ntng2 | NM_133500.2 | chr2:29194725-29248099 |
| 14605 | Nr1i2 | NM_010936.4 | chr16:38248348-38294824 | 14702 | Ntpcr | NM_025636.5 | chr8:125734202-125748235 |
| 14606 | Nr1i3 | NM_001243062.1 | chr1:171213969-171218845 | 14703 | Ntrk1 | NM_001033124.1 | chr3:87778243-87795162 |
| 14607 | Nr2c1 | NM_011629.3 | chr10:94147930-94197214 | 14704 | Ntrk2 | NM_001025074.2 | chr13:58807696-59133970 |
| 14608 | Nr2c2 | NM_011630.3 | chr6:92091417-92173058 | 14705 | Ntrk3 | NM_008746.5 | chr7:78192113-78577838 |
| 14609 | Nr2c2ap | NM_001025586.2 | chr8:70131326-70133751 | 14706 | Nts | NM_024435.2 | chr10:102481755-102490418 |
| 14610 | Nr2e1 | NM_152229.2 | chr10:42616970-42683588 | 14707 | Ntsr1 | NM_018766.2 | chr2:180499975-180544979 |
| 14611 | Nr2e3 | NM_013708.1 | chr9:59942770-59950079 | 14708 | Ntsr2 | NM_008747.2 | chr12:16553469-16660236 |
| 14612 | Nr2f1 | NM_010151.2 | chr13:78188972-78198982 | 14709 | Nuak1 | NM_001004363.1 | chr10:84371318-84440471 |
| 14613 | Nr2f2 | NM_009697.3 | chr7:70351949-70360593 | 14710 | Nuak2 | NM_001195025.1 | chr1:132316124-132333488 |
| 14614 | Nr2f6 | NM_010150.2 | chr8:71374118-71381952 | 14711 | Nubl | NM_016736.3 | chr5:24685814-24710378 |
| 14615 | Nr3c1 | NM_008173.3 | chr18:39410654-39487245 | 14712 | Nubpl | NM_011955.5 | chr16:10419937-10424425 |
| 14616 | Nr3c2 | NM_001083906.1 | chr8:76902507-77243639 | 14713 | Nubp2 | NM_011956.3 | chr17:24882610-24886350 |
| 14617 | Nr4a1 | NM_010444.2 | chr15:101266845-101274794 | 14714 | Nubpl | NM_029760.2 | chr12:52097745-52310959 |
| 14618 | Nr4a2 | NM_001139509.1 | chr2:57107225-57124003 | 14715 | Nucb1 | NM_001163662.1 | chr7:45492673-45510408 |
| 14619 | Nr4a3 | NM_015743.3 | chr4:48045304-48086446 | 14716 | Nucb2 | NM_001130479.2 | chr7:116504368-116540588 |
| 14620 | Nr5a1 | NM_139051.3 | chr2:38692659-38714592 | 14717 | Nucks1 | NM_001145804.1 | chr1:131910457-131936321 |
| 14621 | Nr5a2 | NM_001159769.2 | chr1:136845583-136953630 | 14718 | Nudc | NM_010948.3 | chr4:133532541-133546027 |
| 14622 | Nr6a1 | NM_001159548.1 | chr2:38723373-38784515 | 14719 | Nudcd1 | NM_001113554.1 | chr15:44375226-44428307 |
| 14623 | Nradd | NM_010621.3 | chr9:110621134-110624393 | 14720 | Nudcd2 | NM_001290697.1 | chr11:40733660-40740046 |
| 14624 | Nrap | NM_001286552.1 | chr19:56320040-56390058 | 14721 | Nudcd3 | NM_173748.4 | chr15:6105691-6200451 |
| 14625 | Nrarp | NM_025980.2 | chr2:25180757-25183332 | 14722 | Nudt1 | NM_008637.1 | chr5:140331921-140338135 |
| 14626 | Nras | NM_010937.2 | chr3:103058284-103067914 | 14723 | Nudt10 | NM_001031664.1 | chrX:6168695-6172991 |
| 14627 | Nrbf2 | NM_001036293.2 | chr10:67266688-67285281 | 14724 | Nudt11 | NM_021431.2 | chrX:6047506-6054751 |
| 14628 | Nrbp1 | NM_147012.2 | chr5:31240917-31251562 | 14725 | Nudt12 | NM_026497.2 | chr17:59001400-59013322 |
| 14629 | Nrbp2 | NM_144847.1 | chr15:76085593-76090013 | 14726 | Nudt13 | NM_026341.2 | chr14:20294689-20317575 |
| 14630 | Nrcam | NM_001146031.1 | chr12:44328884-44601846 | 14727 | Nudt14 | NM_025399.4 | chr12:112934792-112942118 |
| 14631 | Nrd1 | NM_146150.3 | chr4:109000804-109061771 | 14728 | Nudt15 | NM_172527.2 | chr14:73519863-73548242 |
| 14632 | Nrde2 | NM_001290303.1 | chr12:100125449-100159653 | 14729 | Nudt16 | NM_029385.2 | chr9:105129337-105131805 |
| 14633 | Nrep | NM_001109988.1 | chr18:33437018-33464029 | 14730 | Nudt16l1 | NM_025839.4 | chr16:4939110-4941020 |
| 14634 | Nrf1 | NM_001164226.1 | chr6:30047987-30153458 | 14731 | Nudt17 | NM_001162925.1 | chr3:96705891-96708560 |
| 14635 | Nrg1 | NM_178591.2 | chr8:31818027-31918263 | 14732 | Nudt18 | NM_153136.4 | chr14:70577846-70582671 |
| 14636 | Nrg2 | NM_001032002.2 | chr18:36017657-36197160 | 14733 | Nudt19 | NM_033080.2 | chr7:35547184-35555928 |
| 14637 | Nrg3 | NM_001190187.1 | chr14:38368956-39473088 | 14734 | Nudt2 | NM_025539.2 | chr4:41465147-41480926 |
| 14638 | Nrg3os | NR_045713.1 | chr14:38898301-38958794 | 14735 | Nudt21 | NM_026623.3 | chr8:94019402-94037639 |
| 14639 | Nrg4 | NM_032002.2 | chr9:55220221-55283625 | 14736 | Nudt22 | NM_026675.2 | chr19:6993018-6996037 |
| 14640 | Nrgn | NM_022029.2 | chr9:37544492-37559275 | 14737 | Nudt3 | NM_001291046.1 | chr17:27579381-27622984 |
| 14641 | Nrip1 | NM_173440.2 | chr16:76290861-76373049 | 14738 | Nudt4 | NM_027722.4 | chr10:95547006-95564167 |
| 14642 | Nrip2 | NM_001162855.1 | chr6:128408635-128408935 | 14739 | Nudt5 | NM_016918.3 | chr2:5845033-5868736 |
| 14643 | Nrip3 | NM_020610.1 | chr7:109758055-109781545 | 14740 | Nudt6 | NM_001291044.1 | chr3:37404981-37419596 |
| 14644 | Nrk | NM_013764.2 | chrX:138914429-139009090 | 14741 | Nudt7 | NM_001290180.1 | chr8:114133573-114152312 |
| 14645 | Nrl | NM_001136074.2 | chr14:55518977-55524981 | 14742 | Nudt8 | NM_025529.3 | chr19:4000579-4002102 |
| 14646 | Nrp | NM_134122.3 | chr17:35861317-35865400 | 14743 | Nudt9 | NM_028794.4 | chr5:104046863-104069378 |

Fig.21 - 77

| | | | | | | | |
|---|---|---|---|---|---|---|---|
| 14744 | Nuf2 | NM_023284.3 | chr1:169497933-169531464 | 14841 | Ociad2 | NM_026950.4 | chr5:73322197-73338947 |
| 14745 | Nufip1 | NM_013745.5 | chr14:76110890-76137379 | 14842 | Ocln | NM_008756.2 | chr13:100497366-100552498 |
| 14746 | Nufip2 | NM_001024205.2 | chr11:77686138-77717966 | 14843 | Ocm | NM_033039.3 | chr5:144019806-144050609 |
| 14747 | Nugge | NM_001195674.2 | chr14:65605266-65648443 | 14844 | Ocrl | NM_177215.3 | chrX:47912455-47965866 |
| 14748 | Numa1 | NM_133947.3 | chr7:101969842-102014959 | 14845 | Ocstamp | NM_029021.1 | chr2:165395449-165400394 |
| 14749 | Numb | NM_001136075.2 | chr12:83794033-83842358 | 14846 | Odam | NM_027128.2 | chr5:87856694-87892742 |
| 14750 | Numbl | NM_010950.2 | chr7:27258760-27282150 | 14847 | Odc1 | NM_013614.2 | chr12:17544872-17551502 |
| 14751 | Nup107 | NM_134010.2 | chr10:117750642-117792705 | 14848 | Odf1 | NM_008757.3 | chr15:38219202-38226735 |
| 14752 | Nup133 | NM_172288.2 | chr8:123897122-123949265 | 14849 | Odf2 | NM_001113213.1 | chr2:29889719-29931746 |
| 14753 | Nup153 | NM_175749.2 | chr13:46679901-46727849 | 14850 | Odf2l | NM_001162538.1 | chr3:145118568-145153915 |
| 14754 | Nup155 | NM_133227.3 | chr15:8109312-8159859 | 14851 | Odf3 | NM_027019.3 | chr7:140847915-140850925 |
| 14755 | Nup160 | NM_021512.2 | chr2:90677214-90736328 | 14852 | Odf3b | NM_001013022.1 | chr15:89377448-89379254 |
| 14756 | Nup188 | NM_198304.2 | chr2:30286432-30344262 | 14853 | Odf3l1 | NM_198673.2 | chr9:56848658-56851963 |
| 14757 | Nup205 | NM_027513.1 | chr6:35177615-35247598 | 14854 | Odf3l2 | NM_001033473.2 | chr10:79639525-79645738 |
| 14758 | Nup210 | NM_018815.2 | chr6:91013066-91116826 | 14855 | Odf4 | NM_145746.2 | chr11:68921834-68927081 |
| 14759 | Nup210l | NM_029937.1 | chr3:90104131-90212017 | 14856 | Ofcc1 | NM_172143.2 | chr13:40001881-40288011 |
| 14760 | Nup214 | NM_172268.2 | chr2:31974449-32053975 | 14857 | Ofd1 | NM_177429.3 | chrX:166390032-166446704 |
| 14761 | Nup35 | NM_001190379.1 | chr2:80639263-80660071 | 14858 | Ogdh | NM_001252282.1 | chr11:6291596-6359094 |
| 14762 | Nup37 | NM_027191.2 | chr10:88146991-88178395 | 14859 | Ogdhl | NM_001081130.1 | chr14:32322018-32347820 |
| 14763 | Nup43 | NM_145706.2 | chr10:7667503-7678886 | 14860 | Ogfod1 | NM_001093757.1 | chr8:94037197-94067922 |
| 14764 | Nup50 | NM_016714.2 | chr15:84923427-84942963 | 14861 | Ogfod2 | NM_025671.2 | chr5:124112337-124115476 |
| 14765 | Nup54 | NM_183392.2 | chr5:92415539-92435199 | 14862 | Ogfod3 | NM_025402.2 | chr11:121177592-121204648 |
| 14766 | Nup62 | NM_053074.2 | chr7:44816087-44831836 | 14863 | Ogfr | NM_031373.3 | chr2:180589406-180595837 |
| 14767 | Nup62cl | NM_001081668.1 | chrX:140007672-140062568 | 14864 | Ogfrl1 | NM_001081079.1 | chr1:23366423-23383175 |
| 14768 | Nup62-il4i1 | NM_001171024.1 | chr7:44816369-44840803 | 14865 | Ogg1 | NM_010957.4 | chr6:113326975-113334186 |
| 14769 | Nup85 | NM_001020929.4 | chr11:115564443-115583924 | 14866 | Ogn | NM_008760.4 | chr13:49608070-49624500 |
| 14770 | Nup88 | NM_001083381.2 | chr11:70943057-70969973 | 14867 | Ogt | NM_001290635.1 | chrX:101640217-101684351 |
| 14771 | Nup93 | NM_172410.2 | chr8:94214600-94315066 | 14868 | Oip5 | NM_001042653.1 | chr2:119609631-119618505 |
| 14772 | Nup98 | NM_001287164.1 | chr7:102119399-102210166 | 14869 | Oit1 | NM_146050.2 | chr14:8348947-8378763 |
| 14773 | Nuph1 | NM_170591.1 | chr14:60219467-60251378 | 14870 | Oit3 | NM_010959.2 | chr10:59422959-59441779 |
| 14774 | Nupl2 | NM_153002.4 | chr15:84969462-24184008 | 14871 | Ola1 | NM_025942.2 | chr2:73092800-73214447 |
| 14775 | Nupr1 | NM_019738.1 | chr7:126623245-126625470 | 14872 | Olah | NM_145921.1 | chr2:3341987-3366569 |
| 14776 | Nupr1l | NM_026916.3 | chr5:129908539-129911281 | 14873 | Olfm1 | NM_001038612.1 | chr2:28205688-28214431 |
| 14777 | Nus1 | NM_030250.2 | chr10:52417546-52440192 | 14874 | Olfm2 | NM_173777.3 | chr9:20667985-20728214 |
| 14778 | Nusap1 | NM_001042652.1 | chr2:119618297-119650160 | 14875 | Olfm3 | NM_001286750.1 | chr3:114904634-115125764 |
| 14779 | Nuff2 | NM_026532.3 | chr8:105860639-105880401 | 14876 | Olfm4 | NM_001030294.1 | chr14:80000301-80021930 |
| 14780 | Nutf2-ps1 | NR_033674.1 | chr8:105860659-105879337 | 14877 | Olfml1 | NM_172907.3 | chr7:107567432-107591365 |
| 14781 | Nutm1 | NM_172521.1 | chr2:112247947-112259291 | 14878 | Olfml2a | NM_172854.2 | chr2:38931979-38960585 |
| 14782 | Nvl | NM_026171.2 | chr1:181087137-181144204 | 14879 | Olfml2b | NM_177068.4 | chr1:170644531-170682784 |
| 14783 | Nwd1 | NM_176940.5 | chr8:72646710-72714748 | 14880 | Olfml3 | NM_133859.2 | chr3:103735393-103738001 |
| 14784 | Nwd2 | NM_177006.3 | chr5:63649102-63810643 | 14881 | Olfr1 | NM_146921.2 | chr11:73398075-73399495 |
| 14785 | Nxf1 | NM_001276704.1 | chr19:8757116-8770910 | 14882 | Olfr10 | NM_208322.1 | chr11:49317547-49318483 |
| 14786 | Nxf2 | NM_001289735.1 | chrX:134944525-134964754 | 14883 | Olfr100 | NM_207673.1 | chr17:37313455-37314382 |
| 14787 | Nxf3 | NM_001024141.4 | chrX:136072098-136085255 | 14884 | Olfr1000 | NM_001011695.1 | chr2:85607963-85608908 |
| 14788 | Nxf7 | NM_130884.1 | chrX:135579786-135593855 | 14885 | Olfr1002 | NM_146573.2 | chr2:85647362-85648319 |
| 14789 | Nxn | NM_008750.5 | chr11:76257225-76399141 | 14886 | Olfr1006 | NM_146570.2 | chr2:85674210-85678741 |
| 14790 | Nxnl1 | NM_145598.2 | chr8:71566546-71566649 | 14887 | Olfr1008 | NM_146866.1 | chr2:85689430-85690372 |
| 14791 | Nxnl2 | NM_029173.4 | chr13:51371024-51175187 | 14888 | Olfr1009 | NM_146572.2 | chr2:85721406-85722351 |
| 14792 | Nxpe2 | NM_030069.3 | chr9:48318003-48340898 | 14889 | Olfr101 | NM_146834.1 | chr17:37299493-37300420 |
| 14793 | Nxpe3 | NM_001134457.1 | chr16:55893629-55895279 | 14890 | Olfr1010 | NM_207149.2 | chr2:85753362-85754306 |
| 14794 | Nxpe4 | NM_172921.3 | chr9:48362040-48400025 | 14891 | Olfr1012 | NM_146568.2 | chr2:85759438-85760374 |
| 14795 | Nxpe5 | NM_001013773.3 | chr5:138225903-138251875 | 14892 | Olfr1013 | NM_146762.2 | chr2:85769802-85770720 |
| 14796 | Nxph1 | NM_008751.3 | chr6:8950018-9248678 | 14893 | Olfr1014 | NM_146569.2 | chr2:85776585-85777503 |
| 14797 | Nxph2 | NM_008752 | chr2:23321245-23401973 | 14894 | Olfr1015 | NM_146571.2 | chr2:85785473-85786489 |
| 14798 | Nxph3 | NM_130855 | chr11:95509845-95514565 | 14895 | Olfr1016 | NM_001011758.2 | chr2:85799358-85800268 |
| 14799 | Nxph4 | NM_183297 | chr10:127525472-127544559 | 14896 | Olfr1018 | NM_146586.2 | chr2:85822972-85823908 |
| 14800 | Nxt1 | NM_001110159.1 | chr2:148672640-148676026 | 14897 | Olfr1019 | NM_147015.1 | chr2:85840856-85841789 |
| 14801 | Nxt2 | NM_001161430.2 | chrX:142227918-142239700 | 14898 | Olfr102 | NM_001011721.2 | chr17:37313410-37314437 |
| 14802 | Nyap1 | NM_175521.3 | chr5:137730962-137739998 | 14899 | Olfr1020 | NM_146580.2 | chr2:85849419-85850498 |
| 14803 | Nyap2 | NM_172849.3 | chr1:81077316-81271651 | 14900 | Olfr1022 | NM_146565.2 | chr2:85868593-85869541 |
| 14804 | Nynrin | NM_001040072.1 | chr14:55854114-55874736 | 14901 | Olfr1023 | NM_146587.2 | chr2:85886801-85887737 |
| 14805 | Nyx | NM_173415.4 | chrX:13467671-13489313 | 14902 | Olfr1024 | NM_001005230.2 | chr2:85904068-85905052 |
| 14806 | Oacyl | NM_177028.3 | chr18:65698267-65751537 | 14903 | Olfr1026 | NM_146584.2 | chr2:85923269-85924193 |
| 14807 | Oaf | NM_178644.3 | chr9:43221277-43239816 | 14904 | Olfr1028 | NM_001011774.2 | chr2:85951064-85952039 |
| 14808 | Oard1 | NM_001289490.1 | chr17:48409999-48417276 | 14905 | Olfr1029 | NM_001011852.2 | chr2:85975212-85976273 |
| 14809 | Oas1a | NM_145211.2 | chr5:120896256-120907525 | 14906 | Olfr103 | NM_146833.1 | chr17:37336288-37337220 |
| 14810 | Oas1b | NM_001083925.1 | chr5:120812637-120824160 | 14907 | Olfr1030 | NM_146588.2 | chr2:85979311-85984798 |
| 14811 | Oas1c | NM_033541.4 | chr5:120800198-120812514 | 14908 | Olfr1031 | NM_001011759.2 | chr2:85991818-85992829 |
| 14812 | Oas1d | NM_133893.3 | chr5:120914817-120921647 | 14909 | Olfr1032 | NM_146579.2 | chr2:86007777-86008710 |
| 14813 | Oas1e | NM_145210.2 | chr5:120786311-120795530 | 14910 | Olfr1033 | NM_146578.2 | chr2:86020639-86044808 |
| 14814 | Oas1f | NM_145153.3 | chr5:120847366-120857986 | 14911 | Olfr1034 | NM_001011872.2 | chr2:86046443-86047466 |
| 14815 | Oas1g | NM_011852.3 | chr5:120876141-120887613 | 14912 | Olfr1036 | NM_207142.2 | chr2:86074703-86075718 |
| 14816 | Oas1h | NM_001159934.1 | chr5:120861421-120873505 | 14913 | Olfr1037 | NM_001011532.2 | chr2:86084729-86085854 |
| 14817 | Oas2 | NM_145227.3 | chr5:120671038-120749848 | 14914 | Olfr1038-ps | NM_147013.2 | chr2:86120223-86123037 |
| 14818 | Oas3 | NM_145226.2 | chr5:120753097-120777659 | 14915 | Olfr1039 | NM_001011784.2 | chr2:86130701-86131661 |
| 14819 | Oasl1 | NM_145209.3 | chr5:114923239-114937911 | 14916 | Olfr1040 | NM_207561.2 | chr2:86145790-86146732 |
| 14820 | Oasl2 | NM_011854.2 | chr5:114896933-114912245 | 14917 | Olfr1042 | NM_001011777.2 | chr2:86159344-86160441 |
| 14821 | Oat | NM_016978.2 | chr7:132557474-132576398 | 14918 | Olfr1043 | NM_146577.2 | chr2:86162002-86162947 |
| 14822 | Oaz1 | NM_008753.4 | chr10:80826655-80829290 | 14919 | Olfr1044 | NM_147011.1 | chr2:86170870-86171815 |
| 14823 | Oaz1-ps | NR_027656.1 | chr10:80826695-80829217 | 14920 | Olfr1045 | NM_147017.1 | chr2:86197802-86198750 |
| 14824 | Oaz2 | NM_010952.3 | chr9:65676547-65690300 | 14921 | Olfr1046 | NM_146582.2 | chr2:86216757-86217708 |
| 14825 | Oaz3 | NM_016901.3 | chr3:94433387-94436651 | 14922 | Olfr1047 | NM_147012.1 | chr2:86228009-86228969 |
| 14826 | Obfc1 | NM_175360.2 | chr19:47501047-47537020 | 14923 | Olfr1048 | NM_147014.1 | chr2:86235870-86236833 |
| 14827 | Obox1 | NM_027802.2 | chr7:15547256-15556846 | 14924 | Olfr1049 | NM_147016.2 | chr2:86254764-86255691 |
| 14828 | Obox2 | NM_145708.2 | chr7:15388850-15398543 | 14925 | Olfr1051 | NM_207152.1 | chr2:86275558-86276485 |
| 14829 | Obox3 | NM_145707.3 | chr7:15625306-15639777 | 14926 | Olfr1052 | NM_147010.2 | chr2:86297817-86298756 |
| 14830 | Obox5 | NM_145709.3 | chr7:15750369-15759274 | 14927 | Olfr1053 | NM_001177857.1 | chr2:86314342-86315285 |
| 14831 | Obox6 | NM_145710.2 | chr7:15833249-15839679 | 14928 | Olfr1054 | NM_147019.1 | chr2:86332415-86333354 |
| 14832 | Obp1a | NM_008754.2 | chrX:78085504-78091374 | 14929 | Olfr1055 | NM_147021.1 | chr2:86346825-86347764 |
| 14833 | Obp2a | NM_153558.1 | chr2:25700073-25703326 | 14930 | Olfr1056 | NM_147018.2 | chr2:86355358-86356437 |
| 14834 | Obp2b | NM_001099301.1 | chr2:25737008-25740097 | 14931 | Olfr1057 | NM_207563.2 | chr2:86374462-86375410 |
| 14835 | Obscn | NM_001171512.2 | chr11:58994255-59136375 | 14932 | Olfr1058 | NM_146391.2 | chr2:86385465-86386416 |
| 14836 | Obsl1 | NM_178884.5 | chr1:75485824-75506452 | 14933 | Olfr1061 | NM_207134.1 | chr2:86413108-86414050 |
| 14837 | Oc90 | NM_010953.2 | chr15:65876052-65912287 | 14934 | Olfr1062 | NM_147078.2 | chr2:86422718-86423674 |
| 14838 | Oca2 | NM_021879.2 | chr7:56239770-56536517 | 14935 | Olfr1065 | NM_146408.2 | chr2:86445012-86446004 |
| 14839 | Oca1 | NM_029865.2 | chr9:71371297-71373689 | 14936 | Olfr1066 | NM_001011735.2 | chr2:86455327-86456269 |
| 14840 | Ociad1 | NM_001159887.1 | chr5:73292793-73314077 | 14937 | Olfr107 | NM_146511.2 | chr17:37405476-37406509 |

Fig.21 - 78

| | | | | | | | |
|---|---|---|---|---|---|---|---|
| 14938 | Olfr1076 | NM_146406.2 | chr2:86508460-86509402 | 15035 | Olfr1195 | NM_146753.2 | chr2:88682803-88683730 |
| 14939 | Olfr1077-ps1 | NR_033507.1 | chr2:86525661-86528427 | 15036 | Olfr1196 | NM_146464.2 | chr2:88700382-88701327 |
| 14940 | Olfr1079 | NM_146407.1 | chr2:86537965-86538913 | 15037 | Olfr1197 | NM_001005225.1 | chr2:88728652-88729597 |
| 14941 | Olfr108 | NM_146465.2 | chr17:37445479-37446517 | 15038 | Olfr1198 | NM_207567.1 | chr2:88745959-88746886 |
| 14942 | Olfr1080 | NM_146409.2 | chr2:86553180-86558138 | 15039 | Olfr1199 | NM_146458.1 | chr2:88755740-88756673 |
| 14943 | Olfr1082 | NM_207674.2 | chr2:86593884-86598809 | 15040 | Olfr12 | NM_206896.2 | chr1:92619880-92621001 |
| 14944 | Olfr1084 | NM_207135.2 | chr2:86638764-86639718 | 15041 | Olfr120 | NM_146631.1 | chr17:37725998-37726991 |
| 14945 | Olfr1085 | NM_146590.2 | chr2:86657514-86658456 | 15042 | Olfr1200 | NM_001005227.2 | chr2:88767302-88768313 |
| 14946 | Olfr1086 | NM_146592.1 | chr2:86676398-86677331 | 15043 | Olfr1201 | NM_146895.1 | chr2:88794383-88795307 |
| 14947 | Olfr1087 | NM_146846.2 | chr2:86690031-86690973 | 15044 | Olfr1202 | NM_146462.1 | chr2:88817172-88818102 |
| 14948 | Olfr1089 | NM_001011771.1 | chr2:86732674-86733610 | 15045 | Olfr1204 | NM_146483.2 | chr2:88851951-88852881 |
| 14949 | Olfr109 | NM_146835.1 | chr17:37466207-37467152 | 15046 | Olfr1205 | NM_146896.3 | chr2:88829756-88832042 |
| 14950 | Olfr1090 | NM_146847.1 | chr2:86753794-86754736 | 15047 | Olfr1206 | NM_001001810.2 | chr2:88864606-88865536 |
| 14951 | Olfr1093 | NM_146366.1 | chr2:86785731-86786700 | 15048 | Olfr1208 | NM_146778.1 | chr2:88896668-88897595 |
| 14952 | Olfr1094 | NM_146365.2 | chr2:86828675-86829822 | 15049 | Olfr1209 | NM_146461.2 | chr2:88909458-88910391 |
| 14953 | Olfr1095 | NM_146730.2 | chr2:86850769-86851696 | 15050 | Olfr121 | NM_146629.2 | chr17:37748865-37753004 |
| 14954 | Olfr1097 | NM_146843.2 | chr2:86890225-86892163 | 15051 | Olfr1211 | NM_001011804.1 | chr2:88929377-88930313 |
| 14955 | Olfr1098 | NM_146845.2 | chr2:86922582-86923530 | 15052 | Olfr1212 | NM_207140.1 | chr2:88958467-88959403 |
| 14956 | Olfr1099 | NM_146768.1 | chr2:86958517-86959456 | 15053 | Olfr1213 | NM_146898.2 | chr2:88972953-88980267 |
| 14957 | Olfr11 | NM_146542.2 | chr13:21638579-21639521 | 15054 | Olfr1214 | NM_146897.2 | chr2:88987264-88988200 |
| 14958 | Olfr110 | NM_146328.2 | chr17:37492467-37499674 | 15055 | Olfr1215 | NM_146459.2 | chr2:89001347-89002290 |
| 14959 | Olfr1100 | NM_146594.1 | chr2:86977828-86978794 | 15056 | Olfr1216 | NM_146893.2 | chr2:89013126-89014062 |
| 14960 | Olfr1101 | NM_146598.2 | chr2:86988241-86989174 | 15057 | Olfr1217 | NM_146901.2 | chr2:89022994-89024099 |
| 14961 | Olfr1102 | NM_207154.2 | chr2:87001931-87002994 | 15058 | Olfr1218 | NM_146818.2 | chr2:89054488-89055424 |
| 14962 | Olfr1104 | NM_146767.2 | chr2:87021609-87022542 | 15059 | Olfr1219 | NM_146899.2 | chr2:89074153-89075089 |
| 14963 | Olfr1105 | NM_001011825.1 | chr2:87033208-87034219 | 15060 | Olfr122 | NM_146288.3 | chr17:37768641-37772620 |
| 14964 | Olfr1106 | NM_146752.2 | chr2:87048295-87049234 | 15061 | Olfr1220 | NM_146900.2 | chr2:89096937-89097963 |
| 14965 | Olfr1107 | NM_146844.2 | chr2:87071115-87072223 | 15062 | Olfr1221 | NM_146902.2 | chr2:89111574-89112510 |
| 14966 | Olfr1109 | NM_146766.2 | chr2:87092456-87093395 | 15063 | Olfr1222 | NM_001011860.1 | chr2:89124793-89125729 |
| 14967 | Olfr111 | NM_001005485.2 | chr17:37529956-37530997 | 15064 | Olfr1223 | NM_146892.2 | chr2:89144085-89151336 |
| 14968 | Olfr1110 | NM_146769.1 | chr2:87135380-87136319 | 15065 | Olfr1225 | NM_146891.2 | chr2:89170218-89171245 |
| 14969 | Olfr1111 | NM_146593.2 | chr2:87149719-87150659 | 15066 | Olfr1226 | NM_146967.1 | chr2:89193099-89194032 |
| 14970 | Olfr1112 | NM_146661.2 | chr2:87191638-87192645 | 15067 | Olfr1228 | NM_146971.1 | chr2:89248720-89249692 |
| 14971 | Olfr1113 | NM_207565.1 | chr2:87212893-87213874 | 15068 | Olfr1229 | NM_001011761.1 | chr2:89282195-89283131 |
| 14972 | Olfr1115 | NM_146297.2 | chr2:87251839-87252941 | 15069 | Olfr123 | NM_146630.1 | chr17:37795445-37796375 |
| 14973 | Olfr1116-ps | NM_001011734.1 | chr2:87263845-87269769 | 15070 | Olfr1230 | NM_146789.1 | chr2:89296350-89297268 |
| 14974 | Olfr1118 | NM_146332.2 | chr2:87308763-87309759 | 15071 | Olfr1231 | NM_146454.2 | chr2:89302648-89303590 |
| 14975 | Olfr112 | NM_001013575.4 | chr17:37563238-37569451 | 15072 | Olfr1232 | NM_146323.1 | chr2:89325242-89326178 |
| 14976 | Olfr1120 | NM_147029.1 | chr2:87357445-87358390 | 15073 | Olfr1233 | NM_146972.1 | chr2:89339382-89340300 |
| 14977 | Olfr1121 | NM_146348.2 | chr2:87371533-87372478 | 15074 | Olfr1234 | NM_146973.1 | chr2:89362482-89363427 |
| 14978 | Olfr1122 | NM_147031.1 | chr2:87387706-87388687 | 15075 | Olfr1238 | NM_146790.1 | chr2:89406129-89407077 |
| 14979 | Olfr1123 | NM_146350.2 | chr2:87411049-87419021 | 15076 | Olfr1239 | NM_146970.1 | chr2:89417493-89418411 |
| 14980 | Olfr1124 | NM_147028.2 | chr2:87434488-87435445 | 15077 | Olfr124 | NM_147062.2 | chr17:37805068-37806190 |
| 14981 | Olfr1126 | NM_146897.2 | chr2:87457166-87458111 | 15078 | Olfr1240 | NM_146808.2 | chr2:89439269-89440343 |
| 14982 | Olfr1128 | NM_146349.2 | chr2:87544606-87545542 | 15079 | Olfr1241 | NM_146455.1 | chr2:89482188-89483133 |
| 14983 | Olfr1129 | NM_001011836.2 | chr2:87575085-87576030 | 15080 | Olfr1242 | NM_146968.2 | chr2:89493293-89494346 |
| 14984 | Olfr113 | NM_146289.1 | chr17:37834482-37575421 | 15081 | Olfr1243 | NM_146969.1 | chr2:89527490-89528408 |
| 14985 | Olfr1130 | NM_146835.1 | chr2:87606211-87608334 | 15082 | Olfr1245 | NM_146788.2 | chr2:89574713-89575773 |
| 14986 | Olfr1131 | NM_146658.2 | chr2:87628464-87629394 | 15083 | Olfr1246 | NM_146792.2 | chr2:89590088-89591146 |
| 14987 | Olfr1132 | NM_146630.2 | chr2:87634818-87635745 | 15084 | Olfr1247 | NM_146966.2 | chr2:89609088-89610153 |
| 14988 | Olfr1133 | NM_146351.2 | chr2:87645179-87646121 | 15085 | Olfr1248 | NM_146791.2 | chr2:89617167-89618245 |
| 14989 | Olfr1134 | NM_147030.2 | chr2:87655924-87658457 | 15086 | Olfr1249 | NM_001011796.2 | chr2:89629939-89630896 |
| 14990 | Olfr1135 | NM_146660.2 | chr2:87671432-87672365 | 15087 | Olfr125 | NM_146290.2 | chr17:37834910-37836028 |
| 14991 | Olfr1136 | NM_146659.3 | chr2:87692380-87693947 | 15088 | Olfr1250 | NM_146965.1 | chr2:89656494-89657439 |
| 14992 | Olfr1137 | NM_001011833.1 | chr2:87710971-87711904 | 15089 | Olfr1251 | NM_001011529.1 | chr2:89666927-89667884 |
| 14993 | Olfr1138 | NM_146639.1 | chr2:87737386-87738322 | 15090 | Olfr1252 | NM_207568.1 | chr2:89721164-89722109 |
| 14994 | Olfr114 | NM_146287.1 | chr17:37589412-37590351 | 15091 | Olfr1253 | NM_146373.1 | chr2:89751869-89752826 |
| 14995 | Olfr1140 | NM_146642.2 | chr2:87746160-87747180 | 15092 | Olfr1254 | NM_146476.1 | chr2:89788405-89789350 |
| 14996 | Olfr1141 | NM_146637.1 | chr2:87753055-87753991 | 15093 | Olfr1255 | NM_146977.2 | chr2:89816327-89817260 |
| 14997 | Olfr1143 | NM_146293.2 | chr2:87802390-87803335 | 15094 | Olfr1256 | NM_146983.1 | chr2:89835022-89835943 |
| 14998 | Olfr1145 | NM_146320.2 | chr2:87809821-87810799 | 15095 | Olfr1257 | NM_146882.1 | chr2:89880827-89881757 |
| 14999 | Olfr1148 | NM_001011519.1 | chr2:87833040-87833985 | 15096 | Olfr1258 | NM_146978.1 | chr2:89929810-89930746 |
| 15000 | Olfr115 | NM_001011753.2 | chr17:37609784-37610779 | 15097 | Olfr1259 | NM_146341.1 | chr2:89943183-89944113 |
| 15001 | Olfr1151 | NM_146638.1 | chr2:87857176-87858103 | 15098 | Olfr126 | NM_146890.2 | chr17:37850593-37851553 |
| 15002 | Olfr1152 | NM_001011834.1 | chr2:87867992-87868925 | 15099 | Olfr1260 | NM_146981.1 | chr2:89977779-89978712 |
| 15003 | Olfr1153 | NM_146642.2 | chr2:87896176-87897133 | 15100 | Olfr1261 | NM_146474.1 | chr2:89993394-89994315 |
| 15004 | Olfr1154 | NM_146647.2 | chr2:87902741-87903674 | 15101 | Olfr1262 | NM_146974.1 | chr2:90002407-90003322 |
| 15005 | Olfr1155 | NM_146643.2 | chr2:87942681-87943626 | 15102 | Olfr1263 | NM_146794.1 | chr2:90014931-90015852 |
| 15006 | Olfr1156 | NM_146817.2 | chr2:87949189-87950285 | 15103 | Olfr1264 | NM_021368.1 | chr2:90021137-90022064 |
| 15007 | Olfr1157 | NM_146849.2 | chr2:87961951-87968257 | 15104 | Olfr1265 | NM_146343.1 | chr2:90036920-90037850 |
| 15008 | Olfr1158 | NM_146645.2 | chr2:87990112-87991054 | 15105 | Olfr1269 | NM_146342.1 | chr2:90118666-90119596 |
| 15009 | Olfr116 | NM_146632.1 | chr17:37623867-37624633 | 15106 | Olfr127 | NM_146377.1 | chr17:37903547-37904519 |
| 15010 | Olfr1160 | NM_146649.2 | chr2:88005816-88006776 | 15107 | Olfr1270 | NM_146885.2 | chr2:90149018-90150036 |
| 15011 | Olfr1161 | NM_146630.2 | chr2:88024701-88025713 | 15108 | Olfr1271 | NM_146793.1 | chr2:90265510-90266428 |
| 15012 | Olfr1162 | NM_001011835.1 | chr2:88049677-88050622 | 15109 | Olfr1272 | NM_146980.1 | chr2:90281646-90282573 |
| 15013 | Olfr1163 | NM_146644.2 | chr2:88070364-88071407 | 15110 | Olfr1273-ps | NM_146975.1 | chr2:90295935-90296859 |
| 15014 | Olfr1164 | NM_146641.2 | chr2:88092854-88093966 | 15111 | Olfr1274-ps | NM_146263.2 | chr2:90400639-90401674 |
| 15015 | Olfr1166 | NM_146650.2 | chr2:88123361-88124993 | 15112 | Olfr1275 | NM_001011795.1 | chr2:111230852-111231791 |
| 15016 | Olfr1167 | NM_146728.2 | chr2:88148983-88150083 | 15113 | Olfr1276 | NM_146395.1 | chr2:111257116-111258055 |
| 15017 | Olfr1168 | NM_146631.2 | chr2:88184878-88185817 | 15114 | Olfr1277 | NM_146396.1 | chr2:111269453-111270395 |
| 15018 | Olfr117 | NM_207155.2 | chr17:37659377-37660331 | 15115 | Olfr1278 | NM_146394.1 | chr2:111292269-111293211 |
| 15019 | Olfr1170 | NM_146632.1 | chr2:88224079-88225030 | 15116 | Olfr1279 | NM_146393.1 | chr2:111306200-111307142 |
| 15020 | Olfr1173 | NM_207566.1 | chr2:88274108-88275047 | 15117 | Olfr128 | NM_206816.1 | chr17:37923567-37924494 |
| 15021 | Olfr1176 | NM_146771.1 | chr2:88339566-88340514 | 15118 | Olfr1280 | NM_146908.1 | chr2:111315480-111316398 |
| 15022 | Olfr1178 | NM_001011868.1 | chr2:88391248-88392220 | 15119 | Olfr1281 | NM_001005568.1 | chr2:111328420-111329338 |
| 15023 | Olfr1179 | NM_146917.2 | chr2:88402008-88402982 | 15120 | Olfr1282 | NM_146907.2 | chr2:111335158-111336076 |
| 15024 | Olfr118 | NM_213723.2 | chr17:37672028-37672990 | 15121 | Olfr1283 | NM_207236.1 | chr2:111368633-111369551 |
| 15025 | Olfr1180 | NM_146918.2 | chr2:88411626-88412689 | 15122 | Olfr1284 | NM_146381.1 | chr2:111379001-111379937 |
| 15026 | Olfr1181 | NM_001011816.1 | chr2:88423087-88424023 | 15123 | Olfr1286 | NM_207254.1 | chr2:111420031-111420949 |
| 15027 | Olfr1182 | NM_001011535.2 | chr2:88446018-88449121 | 15124 | Olfr1287 | NM_001011773.1 | chr2:111449141-111450059 |
| 15028 | Olfr1183 | NM_146529.2 | chr2:88461341-88462263 | 15125 | Olfr1288 | NM_146400.2 | chr2:111478785-111479724 |
| 15029 | Olfr1184 | NM_146823.1 | chr2:88486733-88487669 | 15126 | Olfr1289 | NM_146404.1 | chr2:111483431-111484328 |
| 15030 | Olfr1186 | NM_146630.2 | chr2:88525500-88526590 | 15127 | Olfr129 | NM_146327.2 | chr17:38054598-38059784 |
| 15031 | Olfr1188 | NM_146919.2 | chr2:88559450-88560418 | 15128 | Olfr1290 | NM_001278787.1 | chr2:111489217-111493815 |
| 15032 | Olfr1189 | NM_146772.2 | chr2:88591805-88592726 | 15129 | Olfr1294 | NM_146885.1 | chr2:111537348-111538287 |
| 15033 | Olfr119 | NM_001011830.2 | chr17:37696684-37701637 | 15130 | Olfr1295 | NM_146403.1 | chr2:111564503-111565442 |
| 15034 | Olfr1193 | NM_001011517.2 | chr2:88677856-88678813 | 15131 | Olfr1297 | NM_146888.1 | chr2:111621133-111622072 |

Fig.21 - 79

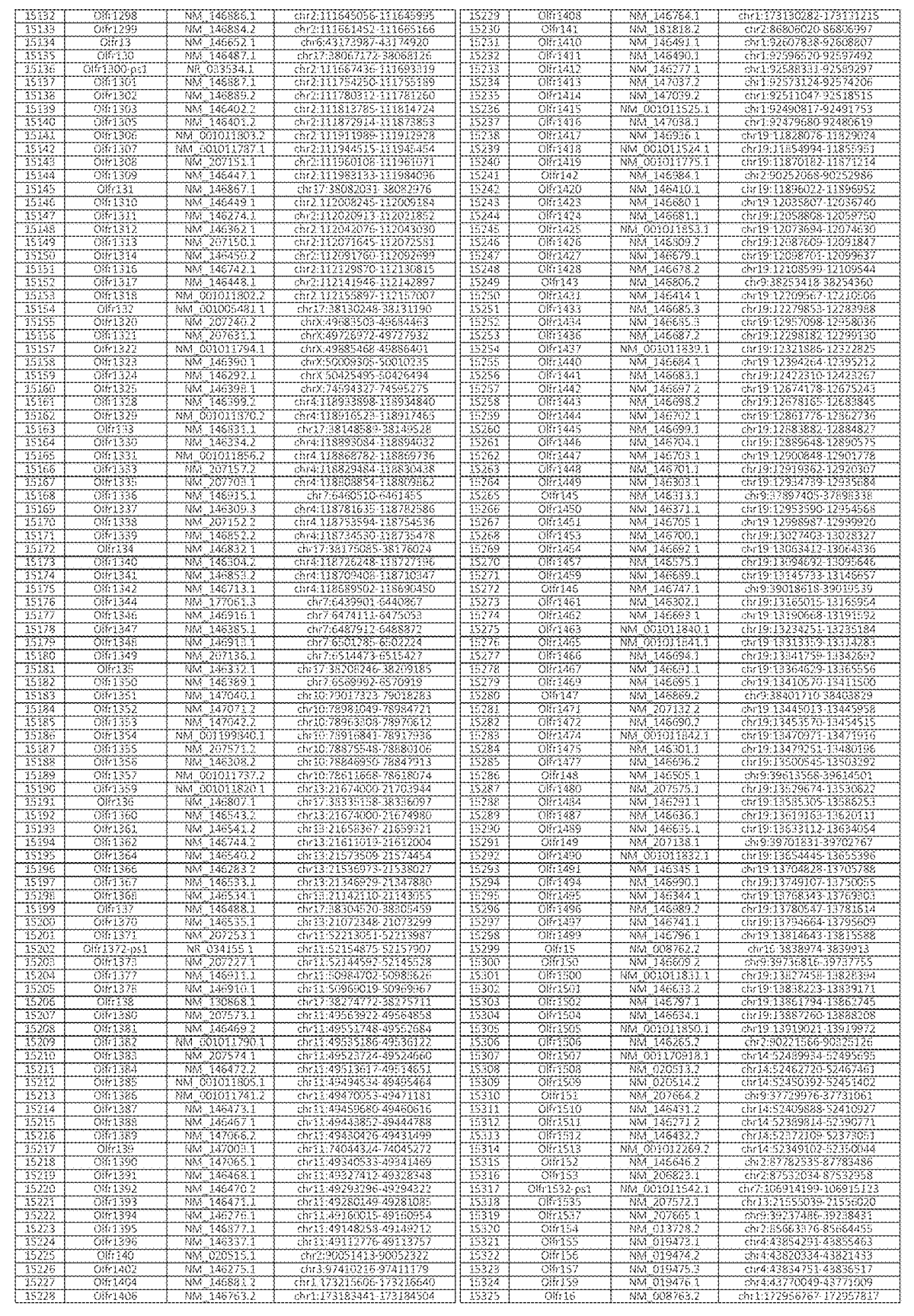

| | | | |
|---|---|---|---|
| 15132 | Olfr1298 | NM_146886.1 | chr2:111645056-111645995 |
| 15133 | Olfr1299 | NM_146884.2 | chr2:111661452-111665166 |
| 15134 | Olfr13 | NM_146652.1 | chr6:43173987-43174920 |
| 15135 | Olfr130 | NM_146487.1 | chr17:38067172-38068126 |
| 15136 | Olfr1300-ps1 | NR_033534.1 | chr2:111667436-111693319 |
| 15137 | Olfr1301 | NM_146887.1 | chr2:111754250-111755189 |
| 15138 | Olfr1302 | NM_146889.2 | chr2:111780312-111781260 |
| 15139 | Olfr1303 | NM_146402.2 | chr2:111813785-111814724 |
| 15140 | Olfr1305 | NM_146401.2 | chr2:111872914-111873853 |
| 15141 | Olfr1306 | NM_001011803.2 | chr2:111911989-111912928 |
| 15142 | Olfr1307 | NM_001011787.1 | chr2:111944515-111945454 |
| 15143 | Olfr1308 | NM_207151.1 | chr2:111960108-111961071 |
| 15144 | Olfr1309 | NM_146447.1 | chr2:111983133-111984096 |
| 15145 | Olfr131 | NM_146867.1 | chr17:38082031-38082976 |
| 15146 | Olfr1310 | NM_146449.1 | chr2:112008245-112009184 |
| 15147 | Olfr1311 | NM_146274.1 | chr2:112020913-112021852 |
| 15148 | Olfr1312 | NM_146362.1 | chr2:112042076-112043030 |
| 15149 | Olfr1313 | NM_207150.1 | chr2:112071645-112072581 |
| 15150 | Olfr1314 | NM_146450.2 | chr2:112091760-112092699 |
| 15151 | Olfr1316 | NM_146742.1 | chr2:112129870-112130815 |
| 15152 | Olfr1317 | NM_146448.1 | chr2:112141946-112142897 |
| 15153 | Olfr1318 | NM_001011802.2 | chr2:112155897-112157007 |
| 15154 | Olfr132 | NM_001005481.1 | chr17:38130248-38131190 |
| 15155 | Olfr1320 | NM_207240.2 | chrX:49683503-49684463 |
| 15156 | Olfr1321 | NM_207631.1 | chrX:49726972-49727932 |
| 15157 | Olfr1322 | NM_001011794.1 | chrX:49885468-49886401 |
| 15158 | Olfr1323 | NM_146390.1 | chrX:50009305-50010235 |
| 15159 | Olfr1324 | NM_146292.1 | chrX:50425495-50426494 |
| 15160 | Olfr1325 | NM_146398.1 | chrX:74594327-74595275 |
| 15161 | Olfr1328 | NM_146399.2 | chr4:118933898-118934840 |
| 15162 | Olfr1329 | NM_001011870.2 | chr4:118916523-118917465 |
| 15163 | Olfr133 | NM_146831.1 | chr17:38148589-38149528 |
| 15164 | Olfr1330 | NM_146334.2 | chr4:118893084-118894032 |
| 15165 | Olfr1331 | NM_001011856.2 | chr4:118868782-118869736 |
| 15166 | Olfr1333 | NM_207157.2 | chr4:118829484-118830438 |
| 15167 | Olfr1335 | NM_207703.1 | chr4:118808854-118809862 |
| 15168 | Olfr1336 | NM_146915.1 | chr7:6460510-6461455 |
| 15169 | Olfr1337 | NM_146309.3 | chr4:118781635-118782586 |
| 15170 | Olfr1338 | NM_207152.2 | chr4:118753594-118754536 |
| 15171 | Olfr1339 | NM_146852.2 | chr4:118734530-118735478 |
| 15172 | Olfr134 | NM_146832.1 | chr17:38175085-38176024 |
| 15173 | Olfr1340 | NM_146304.2 | chr4:118726248-118727196 |
| 15174 | Olfr1341 | NM_146853.2 | chr4:118709408-118710347 |
| 15175 | Olfr1342 | NM_146713.1 | chr4:118689502-118690450 |
| 15176 | Olfr1344 | NM_177061.3 | chr7:6439901-6440867 |
| 15177 | Olfr1346 | NM_146916.1 | chr7:6474111-6475053 |
| 15178 | Olfr1347 | NM_146385.1 | chr7:6487912-6488872 |
| 15179 | Olfr1348 | NM_146913.1 | chr7:6501285-6502224 |
| 15180 | Olfr1349 | NM_207136.1 | chr7:6514473-6515427 |
| 15181 | Olfr135 | NM_146332.1 | chr17:38208246-38209185 |
| 15182 | Olfr1350 | NM_146389.1 | chr7:6569992-6570919 |
| 15183 | Olfr1351 | NM_147040.1 | chr10:79017323-79018283 |
| 15184 | Olfr1352 | NM_147071.2 | chr10:78981049-78984721 |
| 15185 | Olfr1353 | NM_147042.2 | chr10:78963308-78970612 |
| 15186 | Olfr1354 | NM_001199840.1 | chr10:78916841-78917936 |
| 15187 | Olfr1355 | NM_207571.2 | chr10:78875548-78880106 |
| 15188 | Olfr1356 | NM_146308.2 | chr10:78846950-78847913 |
| 15189 | Olfr1357 | NM_001011737.2 | chr10:78611668-78618074 |
| 15190 | Olfr1359 | NM_001011820.1 | chr13:21674000-21703944 |
| 15191 | Olfr136 | NM_146807.1 | chr17:38335158-38336097 |
| 15192 | Olfr1360 | NM_146543.2 | chr13:21674000-21674980 |
| 15193 | Olfr1361 | NM_146541.2 | chr13:21658367-21659321 |
| 15194 | Olfr1362 | NM_146744.2 | chr13:21611019-21612004 |
| 15195 | Olfr1364 | NM_146540.2 | chr13:21573509-21574454 |
| 15196 | Olfr1366 | NM_146283.2 | chr13:21536973-21538027 |
| 15197 | Olfr1367 | NM_146533.1 | chr13:21346929-21347880 |
| 15198 | Olfr1368 | NM_146534.1 | chr13:21142110-21143055 |
| 15199 | Olfr137 | NM_146488.1 | chr17:38304520-38305459 |
| 15200 | Olfr1370 | NM_146535.1 | chr13:21072348-21073299 |
| 15201 | Olfr1371 | NM_207253.1 | chr11:52213051-52213987 |
| 15202 | Olfr1372-ps1 | NR_034155.1 | chr11:52154875-52157907 |
| 15203 | Olfr1373 | NM_207227.1 | chr11:52144592-52145528 |
| 15204 | Olfr1377 | NM_146911.1 | chr11:50984702-50985626 |
| 15205 | Olfr1378 | NM_146910.1 | chr11:50969019-50969967 |
| 15206 | Olfr138 | NM_130868.1 | chr17:38274772-38275711 |
| 15207 | Olfr1380 | NM_207573.1 | chr11:49563922-49564858 |
| 15208 | Olfr1381 | NM_146469.2 | chr11:49551748-49552684 |
| 15209 | Olfr1382 | NM_001011790.1 | chr11:49535186-49536122 |
| 15210 | Olfr1383 | NM_207574.1 | chr11:49523724-49524660 |
| 15211 | Olfr1384 | NM_146472.2 | chr11:49513617-49514651 |
| 15212 | Olfr1385 | NM_001011805.1 | chr11:49494534-49495464 |
| 15213 | Olfr1386 | NM_001011741.2 | chr11:49470053-49471181 |
| 15214 | Olfr1387 | NM_146473.1 | chr11:49459680-49460616 |
| 15215 | Olfr1388 | NM_146467.1 | chr11:49443852-49444788 |
| 15216 | Olfr1389 | NM_147066.2 | chr11:49430426-49431499 |
| 15217 | Olfr139 | NM_147003.1 | chr11:74044324-74045272 |
| 15218 | Olfr1390 | NM_147065.1 | chr11:49340533-49341469 |
| 15219 | Olfr1391 | NM_146468.1 | chr11:49327412-49328348 |
| 15220 | Olfr1392 | NM_146470.2 | chr11:49293296-49294322 |
| 15221 | Olfr1393 | NM_146471.1 | chr11:49280149-49281085 |
| 15222 | Olfr1394 | NM_146276.1 | chr11:49160015-49160954 |
| 15223 | Olfr1395 | NM_146877.1 | chr11:49148258-49149212 |
| 15224 | Olfr1396 | NM_146337.1 | chr11:49112776-49113757 |
| 15225 | Olfr140 | NM_020515.1 | chr2:90051413-90052322 |
| 15226 | Olfr1402 | NM_146275.1 | chr3:97410216-97411179 |
| 15227 | Olfr1404 | NM_146881.2 | chr1:173215606-173216640 |
| 15228 | Olfr1406 | NM_146763.2 | chr1:173183441-173184504 |
| 15229 | Olfr1408 | NM_146764.1 | chr1:173130282-173131215 |
| 15230 | Olfr141 | NM_181818.2 | chr2:86806020-86806997 |
| 15231 | Olfr1410 | NM_146491.1 | chr1:92607838-92608807 |
| 15232 | Olfr1411 | NM_146490.1 | chr1:92596520-92597492 |
| 15233 | Olfr1412 | NM_146277.1 | chr1:92588331-92589297 |
| 15234 | Olfr1413 | NM_147037.2 | chr1:92573124-92574206 |
| 15235 | Olfr1414 | NM_147039.2 | chr1:92511047-92518515 |
| 15236 | Olfr1415 | NM_001011525.1 | chr1:92490817-92491753 |
| 15237 | Olfr1416 | NM_147038.1 | chr1:92479680-92480619 |
| 15238 | Olfr1417 | NM_146936.1 | chr19:11828076-11829024 |
| 15239 | Olfr1418 | NM_001011524.1 | chr19:11854994-11855951 |
| 15240 | Olfr1419 | NM_001011775.1 | chr19:11870182-11871214 |
| 15241 | Olfr142 | NM_146984.1 | chr2:90252068-90252986 |
| 15242 | Olfr1420 | NM_146410.1 | chr19:11896022-11896952 |
| 15243 | Olfr1423 | NM_146680.1 | chr19:12035807-12036740 |
| 15244 | Olfr1424 | NM_146681.1 | chr19:12058808-12059750 |
| 15245 | Olfr1425 | NM_001011853.1 | chr19:12073694-12074630 |
| 15246 | Olfr1426 | NM_146809.2 | chr19:12087609-12091847 |
| 15247 | Olfr1427 | NM_146679.1 | chr19:12098701-12099637 |
| 15248 | Olfr1428 | NM_146678.2 | chr19:12108599-12109544 |
| 15249 | Olfr143 | NM_146806.2 | chr9:38253418-38254360 |
| 15250 | Olfr1431 | NM_146414.1 | chr19:12209567-12210506 |
| 15251 | Olfr1433 | NM_146685.3 | chr19:12279853-12283988 |
| 15252 | Olfr1434 | NM_146685.3 | chr19:12957098-12958036 |
| 15253 | Olfr1436 | NM_146687.2 | chr19:12298182-12299130 |
| 15254 | Olfr1437 | NM_001011839.1 | chr19:12321886-12322825 |
| 15255 | Olfr1440 | NM_146684.1 | chr19:12394264-12395212 |
| 15256 | Olfr1441 | NM_146683.1 | chr19:12422310-12423267 |
| 15257 | Olfr1442 | NM_146697.2 | chr19:12674178-12675243 |
| 15258 | Olfr1443 | NM_146698.2 | chr19:12678165-12683849 |
| 15259 | Olfr1444 | NM_146702.1 | chr19:12861776-12862736 |
| 15260 | Olfr1445 | NM_146699.1 | chr19:12883882-12884827 |
| 15261 | Olfr1446 | NM_146704.1 | chr19:12889648-12890575 |
| 15262 | Olfr1447 | NM_146703.1 | chr19:12900848-12901778 |
| 15263 | Olfr1448 | NM_146701.1 | chr19:12919362-12920307 |
| 15264 | Olfr1449 | NM_146303.1 | chr19:12934739-12935684 |
| 15265 | Olfr145 | NM_146313.1 | chr9:37897405-37898338 |
| 15266 | Olfr1450 | NM_146371.1 | chr19:12953590-12954568 |
| 15267 | Olfr1451 | NM_146705.1 | chr19:12998987-12999920 |
| 15268 | Olfr1453 | NM_146700.1 | chr19:13027403-13028327 |
| 15269 | Olfr1454 | NM_146692.1 | chr19:13063412-13064336 |
| 15270 | Olfr1457 | NM_146575.1 | chr19:13094692-13095646 |
| 15271 | Olfr1459 | NM_146689.1 | chr19:13145733-13146657 |
| 15272 | Olfr146 | NM_146747.1 | chr9:39018618-39019539 |
| 15273 | Olfr1461 | NM_146302.1 | chr19:13165015-13165954 |
| 15274 | Olfr1462 | NM_146693.1 | chr19:13190668-13191592 |
| 15275 | Olfr1463 | NM_001011840.1 | chr19:13234251-13235184 |
| 15276 | Olfr1465 | NM_001011841.1 | chr19:13313359-13314283 |
| 15277 | Olfr1466 | NM_146694.1 | chr19:13341759-13342692 |
| 15278 | Olfr1467 | NM_146691.1 | chr19:13364629-13365556 |
| 15279 | Olfr1469 | NM_146695.1 | chr19:13410570-13411500 |
| 15280 | Olfr147 | NM_146869.2 | chr9:38401710-38403829 |
| 15281 | Olfr1471 | NM_207132.2 | chr19:13445013-13445958 |
| 15282 | Olfr1472 | NM_146690.2 | chr19:13453570-13454515 |
| 15283 | Olfr1474 | NM_001011842.1 | chr19:13470971-13471916 |
| 15284 | Olfr1475 | NM_146301.1 | chr19:13479251-13480196 |
| 15285 | Olfr1477 | NM_146696.2 | chr19:13500545-13503292 |
| 15286 | Olfr148 | NM_146505.1 | chr9:39613568-39614501 |
| 15287 | Olfr1480 | NM_207575.1 | chr19:13529674-13530622 |
| 15288 | Olfr1484 | NM_146291.1 | chr19:13585305-13586253 |
| 15289 | Olfr1487 | NM_146636.1 | chr19:13619163-13620111 |
| 15290 | Olfr1489 | NM_146635.1 | chr19:13633112-13634054 |
| 15291 | Olfr149 | NM_207138.1 | chr9:39701831-39702767 |
| 15292 | Olfr1490 | NM_001011832.1 | chr19:13654445-13655396 |
| 15293 | Olfr1491 | NM_146345.1 | chr19:13704828-13705788 |
| 15294 | Olfr1494 | NM_146990.1 | chr19:13749107-13750055 |
| 15295 | Olfr1495 | NM_146344.1 | chr19:13768343-13769303 |
| 15296 | Olfr1496 | NM_146989.2 | chr19:13780547-13781614 |
| 15297 | Olfr1497 | NM_146741.1 | chr19:13794664-13795609 |
| 15298 | Olfr1499 | NM_146796.1 | chr19:13814643-13815588 |
| 15299 | Olfr15 | NM_008762.2 | chr16:3838974-3839913 |
| 15300 | Olfr150 | NM_146609.2 | chr9:39736816-39737755 |
| 15301 | Olfr1500 | NM_001011831.1 | chr19:13827458-13828394 |
| 15302 | Olfr1501 | NM_146633.2 | chr19:13838223-13839171 |
| 15303 | Olfr1502 | NM_146797.1 | chr19:13861794-13862745 |
| 15304 | Olfr1504 | NM_146634.1 | chr19:13887260-13888208 |
| 15305 | Olfr1505 | NM_001011850.1 | chr19:13919021-13919972 |
| 15306 | Olfr1506 | NM_146265.2 | chr2:90221566-90325126 |
| 15307 | Olfr1507 | NM_001170918.1 | chr14:52489934-52495695 |
| 15308 | Olfr1508 | NM_020513.2 | chr14:52462720-52467461 |
| 15309 | Olfr1509 | NM_020514.2 | chr14:52450392-52451402 |
| 15310 | Olfr151 | NM_207664.2 | chr9:37729976-37731061 |
| 15311 | Olfr1510 | NM_146431.2 | chr14:52409888-52410927 |
| 15312 | Olfr1511 | NM_146271.2 | chr14:52389814-52390771 |
| 15313 | Olfr1512 | NM_146432.2 | chr14:52372109-52373051 |
| 15314 | Olfr1513 | NM_001012269.2 | chr14:52349102-52350044 |
| 15315 | Olfr152 | NM_146646.2 | chr2:87782535-87783486 |
| 15316 | Olfr153 | NM_206823.1 | chr2:87532034-87532958 |
| 15317 | Olfr1532-ps1 | NM_001011542.1 | chr7:106914199-106915123 |
| 15318 | Olfr1535 | NM_207572.1 | chr13:21555039-21556020 |
| 15319 | Olfr1537 | NM_207665.1 | chr9:39237486-39238431 |
| 15320 | Olfr154 | NM_013728.2 | chr2:85663376-85664455 |
| 15321 | Olfr155 | NM_019473.1 | chr4:43854291-43855463 |
| 15322 | Olfr156 | NM_019474.2 | chr4:43820334-43821453 |
| 15323 | Olfr157 | NM_019475.3 | chr4:43834751-43836517 |
| 15324 | Olfr159 | NM_019476.1 | chr4:43770049-43771009 |
| 15325 | Olfr16 | NM_008763.2 | chr1:172956767-172957817 |

Fig.21 - 80

| | | | | | | | |
|---|---|---|---|---|---|---|---|
| 15326 | Olfr160 | NM_030553.2 | chr9:37711347-37712280 | 15423 | Olfr29-ps1 | NR_033638.1 | chr4:43781364-43782327 |
| 15327 | Olfr161 | NM_146860.1 | chr16:3592397-3593339 | 15424 | Olfr3 | NM_206903.1 | chr2:36812148-36813090 |
| 15328 | Olfr164 | NM_146451.1 | chr16:19285793-19286741 | 15425 | Olfr30 | NM_146878.2 | chr11:58454914-58455980 |
| 15329 | Olfr165 | NM_146466.1 | chr16:19407075-19408017 | 15426 | Olfr301 | NM_212436.2 | chr7:86403848-86413299 |
| 15330 | Olfr166 | NM_147068.1 | chr16:19486839-19487778 | 15427 | Olfr303 | NM_146819.1 | chr7:86394536-86395496 |
| 15331 | Olfr167 | NM_146935.1 | chr16:19514695-19515634 | 15428 | Olfr304 | NM_001011828.1 | chr7:86385656-86386658 |
| 15332 | Olfr168 | NM_146357.1 | chr16:19529979-19530918 | 15429 | Olfr305 | NM_146616.2 | chr7:86363375-86364335 |
| 15333 | Olfr169 | NM_001011855.1 | chr16:19565939-19566881 | 15430 | Olfr307 | NM_146617.1 | chr7:86335452-86336394 |
| 15334 | Olfr17 | NM_020598.2 | chr7:107097466-107098414 | 15431 | Olfr308 | NM_146621.1 | chr7:86321023-86321950 |
| 15335 | Olfr170 | NM_146957.1 | chr16:19605724-19606666 | 15432 | Olfr309 | NM_001011866.1 | chr7:86306184-86307111 |
| 15336 | Olfr171 | NM_146958.2 | chr16:19624156-19625101 | 15433 | Olfr31 | NM_147027.2 | chr14:14328112-14329068 |
| 15337 | Olfr172 | NM_147001.2 | chr16:58760152-58761240 | 15434 | Olfr310 | NM_001011520.2 | chr7:86268729-86269811 |
| 15338 | Olfr173 | NM_147000.2 | chr16:58796778-58797942 | 15435 | Olfr311 | NM_146537.2 | chr11:58841115-58842042 |
| 15339 | Olfr175-ps1 | NM_147002.2 | chr16:58823780-58826761 | 15436 | Olfr312 | NM_001011819.2 | chr11:58831155-58832082 |
| 15340 | Olfr176 | NM_146993.1 | chr16:58872214-58873148 | 15437 | Olfr313 | NM_146536.2 | chr11:58816927-58818001 |
| 15341 | Olfr177 | NM_146996.2 | chr16:58872218-58873148 | 15438 | Olfr314 | NM_001011760.2 | chr11:58786138-58787269 |
| 15342 | Olfr178 | NM_146997.2 | chr16:58889258-58890218 | 15439 | Olfr315 | NM_146538.2 | chr11:58778088-58779086 |
| 15343 | Olfr18 | NM_146563.1 | chr9:20313891-20336094 | 15440 | Olfr316 | NM_001011818.2 | chr11:58757666-58758587 |
| 15344 | Olfr180 | NM_001011662.2 | chr16:58915685-58918486 | 15441 | Olfr317 | NM_001011769.2 | chr11:58752095-58753223 |
| 15345 | Olfr181 | NM_146999.2 | chr16:58925556-58928644 | 15442 | Olfr318 | NM_146501.2 | chr11:58720068-58721094 |
| 15346 | Olfr183 | NM_146485.2 | chr16:58995403-59000616 | 15443 | Olfr319 | NM_146500.2 | chr11:58701702-58702623 |
| 15347 | Olfr186 | NM_146321.1 | chr16:59026975-59027905 | 15444 | Olfr32 | NM_010980.2 | chr2:90138179-90142293 |
| 15348 | Olfr187 | NM_146322.2 | chr16:59035779-59039749 | 15445 | Olfr320 | NM_207230.1 | chr11:58683874-58684795 |
| 15349 | Olfr19 | NM_146335.1 | chr16:16673049-16673979 | 15446 | Olfr322 | NM_207693.1 | chr11:58665560-58666544 |
| 15350 | Olfr190 | NM_146397.2 | chr16:59074154-59075078 | 15447 | Olfr323 | NM_146376.2 | chr11:58625072-58626044 |
| 15351 | Olfr191 | NM_001011807.2 | chr16:59085551-59086481 | 15448 | Olfr324 | NM_001011743.2 | chr11:58597344-58598466 |
| 15352 | Olfr192 | NM_207549.1 | chr16:59098065-59098990 | 15449 | Olfr325 | NM_207153.2 | chr11:58580836-58581877 |
| 15353 | Olfr193 | NM_001011711.1 | chr16:59109678-59110608 | 15450 | Olfr328 | NM_146502.2 | chr11:58551304-58552237 |
| 15354 | Olfr194 | NM_001005524.2 | chr16:59119147-59120068 | 15451 | Olfr329-ps | NM_001011531.1 | chr11:58542446-58543483 |
| 15355 | Olfr195 | NM_146998.1 | chr16:59148851-59149778 | 15452 | Olfr33 | NM_147073.1 | chr7:102713454-102714411 |
| 15356 | Olfr196 | NM_146770.2 | chr16:59167211-59168141 | 15453 | Olfr330 | NM_146879.2 | chr11:58528928-58534825 |
| 15357 | Olfr197 | NM_146484.1 | chr16:59185555-59186481 | 15454 | Olfr331 | NM_001011861.3 | chr11:58501597-58502572 |
| 15358 | Olfr198 | NM_001011808.1 | chr16:59201503-59202424 | 15455 | Olfr332 | NM_001011770.2 | chr11:58489718-58492499 |
| 15359 | Olfr199 | NM_207550.2 | chr16:59215684-59216611 | 15456 | Olfr338 | NM_146947.1 | chr2:36376777-36377698 |
| 15360 | Olfr2 | NM_010983.2 | chr7:107000874-107002605 | 15457 | Olfr339 | NM_146949.1 | chr2:36421399-36422329 |
| 15361 | Olfr20 | NM_146929.2 | chr11:73350808-73354699 | 15458 | Olfr340 | NM_146951.1 | chr2:36452586-36453525 |
| 15362 | Olfr201 | NM_146994.2 | chr16:59268738-59269665 | 15459 | Olfr341 | NM_146950.1 | chr2:36479186-36480128 |
| 15363 | Olfr202 | NM_146995.1 | chr16:59283571-59284495 | 15460 | Olfr342 | NM_146948.1 | chr2:36527413-36528352 |
| 15364 | Olfr203 | NM_146946.2 | chr16:59303154-59304075 | 15461 | Olfr344 | NM_146628.1 | chr2:36568599-36569529 |
| 15365 | Olfr204 | NM_146992.2 | chr16:59314487-59315405 | 15462 | Olfr345 | NM_146945.1 | chr2:36640040-36640976 |
| 15366 | Olfr205 | NM_001011736.1 | chr16:59328589-59329507 | 15463 | Olfr346 | NM_146938.1 | chr2:36688003-36688933 |
| 15367 | Olfr206 | NM_146991.1 | chr16:59344778-59345699 | 15464 | Olfr347 | NM_146843.1 | chr2:36734322-36735761 |
| 15368 | Olfr209 | NM_207551.2 | chr16:59361298-59362216 | 15465 | Olfr348 | NM_146944.1 | chr2:36786526-36787468 |
| 15369 | Olfr211 | NM_146912.1 | chr6:116493610-116494540 | 15466 | Olfr350 | NM_146627.1 | chr2:36850047-36850986 |
| 15370 | Olfr212 | NM_001011800.2 | chr6:116506515-116517965 | 15467 | Olfr351 | NM_146942.1 | chr2:36859413-36860346 |
| 15371 | Olfr213 | NM_001011801.1 | chr6:116540454-116541438 | 15468 | Olfr352 | NM_146940.1 | chr2:36869567-36870515 |
| 15372 | Olfr214 | NM_146759.1 | chr6:116556426-116557389 | 15469 | Olfr353 | NM_146941.1 | chr2:36889910-36890846 |
| 15373 | Olfr215 | NM_146446.1 | chr6:116582011-116582944 | 15470 | Olfr354 | NM_146939.1 | chr2:36906947-36907901 |
| 15374 | Olfr218 | NM_001001809.2 | chr1:173203357-173204299 | 15471 | Olfr355 | NM_146625.1 | chr2:36927179-36928112 |
| 15375 | Olfr220 | NM_207694.1 | chr1:174448570-174449602 | 15472 | Olfr356 | NM_146624.1 | chr2:36937120-36938068 |
| 15376 | Olfr221 | NM_001001808.2 | chr14:52035173-52036109 | 15473 | Olfr357 | NM_146623.1 | chr2:36996811-36997738 |
| 15377 | Olfr222 | NM_001011789.1 | chr11:59570781-59571738 | 15474 | Olfr358 | NM_207235.1 | chr2:37004619-37005612 |
| 15378 | Olfr223 | NM_146429.1 | chr11:59589127-59590087 | 15475 | Olfr360 | NM_146622.1 | chr2:37068306-37069260 |
| 15379 | Olfr224 | NM_207695.1 | chr11:58566898-58567343 | 15476 | Olfr361 | NM_146368.1 | chr2:37084777-37085746 |
| 15380 | Olfr225 | NM_001011760.2 | chr11:59612965-59614225 | 15477 | Olfr362 | NM_147061.1 | chr2:37104694-37105648 |
| 15381 | Olfr228 | NM_146405.2 | chr2:86482798-86483740 | 15478 | Olfr365 | NM_146662.1 | chr2:37201242-37202181 |
| 15382 | Olfr229 | NM_146613.1 | chr9:39909804-39910728 | 15479 | Olfr366 | NM_001005569.1 | chr2:37219490-37220420 |
| 15383 | Olfr23 | NM_010970.1 | chr11:73940247-73941225 | 15480 | Olfr367-ps | NM_001081010.2 | chr2:37266950-37271387 |
| 15384 | Olfr231 | NM_001005520.2 | chr1:174117090-174118014 | 15481 | Olfr368 | NM_146374.1 | chr2:37331748-37332732 |
| 15385 | Olfr235 | NM_146686.2 | chr19:12268231-12269170 | 15482 | Olfr370 | NM_146270.2 | chr8:83541092-83542188 |
| 15386 | Olfr237-ps1 | NM_146815.2 | chr6:43153106-43154239 | 15483 | Olfr371 | NM_146859.2 | chr8:85230496-85231435 |
| 15387 | Olfr239 | NM_207175.2 | chr17:33199061-33200009 | 15484 | Olfr372 | NM_207555.2 | chr8:72057659-72058675 |
| 15388 | Olfr24 | NM_146606.1 | chr9:18754691-18755633 | 15485 | Olfr373 | NM_146539.2 | chr8:72099761-72100706 |
| 15389 | Olfr242 | NM_010974.1 | chr9:39144101-39145018 | 15486 | Olfr374 | NM_146338.2 | chr8:72107039-72110509 |
| 15390 | Olfr243 | NM_001025386.1 | chr1:103716595-103717546 | 15487 | Olfr376 | NM_001172686.1 | chr11:73371245-73375784 |
| 15391 | Olfr247 | NM_146926.2 | chr10:129974604-129984424 | 15488 | Olfr378 | NM_147024.2 | chr11:73425036-73428477 |
| 15392 | Olfr248 | NM_146714.2 | chr1:174391045-174392055 | 15489 | Olfr38 | NM_146986.1 | chr6:42762053-42763007 |
| 15393 | Olfr25 | NM_146870.2 | chr9:38329491-38330559 | 15490 | Olfr380 | NM_147025.1 | chr11:73453274-73454210 |
| 15394 | Olfr259 | NM_146770.2 | chr2:87107446-87108385 | 15491 | Olfr381 | NM_147022.2 | chr11:73485886-73486822 |
| 15395 | Olfr26 | NM_146783.2 | chr9:38855059-38855990 | 15492 | Olfr382 | NM_146443.1 | chr11:73516258-73517197 |
| 15396 | Olfr262 | NM_146688.1 | chr9:12240702-12241659 | 15493 | Olfr384 | NM_207224.1 | chr11:73602581-73603520 |
| 15397 | Olfr263 | NM_010984.1 | chr13:21132776-21133730 | 15494 | Olfr385 | NM_147023.1 | chr11:73588797-73589736 |
| 15398 | Olfr266 | NM_146489.1 | chr3:106821606-106822557 | 15495 | Olfr389 | NM_147009.3 | chr11:73776386-73780589 |
| 15399 | Olfr267 | NM_146920.2 | chr4:58784778-58785720 | 15496 | Olfr39 | NM_146825.2 | chr9:20282350-20286648 |
| 15400 | Olfr27 | NM_146829.2 | chr9:39128166-39145070 | 15497 | Olfr390 | NM_146347.1 | chr11:73786939-73787875 |
| 15401 | Olfr270 | NM_146607.1 | chr4:52970628-52971567 | 15498 | Olfr391-ps | NM_001159775.1 | chr11:73798752-73802984 |
| 15402 | Olfr272 | NM_146839.1 | chr4:52910832-52911792 | 15499 | Olfr392 | NM_147006.2 | chr11:73814141-73816877 |
| 15403 | Olfr273 | NM_146824.1 | chr4:52855557-52856511 | 15500 | Olfr393 | NM_147008.2 | chr11:73847184-73848123 |
| 15404 | Olfr275 | NM_146858.2 | chr4:52825398-52826358 | 15501 | Olfr394 | NM_147007.1 | chr11:73887437-73888370 |
| 15405 | Olfr279 | NM_001001807.1 | chr15:98497473-98498406 | 15502 | Olfr395 | NM_147005.1 | chr11:73906651-73907490 |
| 15406 | Olfr281 | NM_146280.1 | chr15:98456311-98457247 | 15503 | Olfr397 | NM_146346.1 | chr11:73964609-73965557 |
| 15407 | Olfr282 | NM_146457.2 | chr15:98437469-98438397 | 15504 | Olfr398 | NM_146710.1 | chr11:73983661-73984606 |
| 15408 | Olfr283 | NM_147036.1 | chr15:98278178-98379108 | 15505 | Olfr399 | NM_147004.2 | chr11:74053775-74054778 |
| 15409 | Olfr284 | NM_146281.1 | chr15:98340021-98340939 | 15506 | Olfr401 | NM_146706.1 | chr11:74121290-74122238 |
| 15410 | Olfr285 | NM_001011778.1 | chr15:98312588-98313548 | 15507 | Olfr402 | NM_146708.1 | chr11:74155155-74156103 |
| 15411 | Olfr286 | NM_001011779.1 | chr15:98226674-98234450 | 15508 | Olfr403 | NM_207622.1 | chr11:74195504-74196446 |
| 15412 | Olfr287 | NM_001011760.2 | chr15:98206970-98221056 | 15509 | Olfr406 | NM_001011863.1 | chr11:74269390-74270362 |
| 15413 | Olfr288 | NM_001011733.2 | chr15:98186012-98195542 | 15510 | Olfr410 | NM_146707.1 | chr11:74334281-74335229 |
| 15414 | Olfr290 | NM_146416.2 | chr7:84915780-84916728 | 15511 | Olfr411 | NM_146709.2 | chr11:74346623-74347672 |
| 15415 | Olfr291 | NM_146415.2 | chr7:84855370-84857318 | 15512 | Olfr412 | NM_001011851.1 | chr11:74364670-74365609 |
| 15416 | Olfr292 | NM_146620.2 | chr7:86688340-86695384 | 15513 | Olfr414 | NM_146761.2 | chr1:174430429-174431384 |
| 15417 | Olfr293 | NM_001011752.1 | chr7:86663663-86664674 | 15514 | Olfr417 | NM_207137.1 | chr1:174368918-174369848 |
| 15418 | Olfr294 | NM_146618.2 | chr7:86615635-86616643 | 15515 | Olfr418-ps1 | NM_146651.2 | chr1:173270146-173271137 |
| 15419 | Olfr295 | NM_146851.2 | chr7:86585276-86586206 | 15516 | Olfr419 | NM_146715.2 | chr1:174249888-174250976 |
| 15420 | Olfr297 | NM_146618.2 | chr7:86526758-86527691 | 15517 | Olfr420 | NM_146305.2 | chr1:174158721-174159767 |
| 15421 | Olfr298 | NM_001011751.1 | chr7:86488550-86489549 | 15518 | Olfr421-ps1 | NR_047667.1 | chr1:174151480-174152530 |
| 15422 | Olfr299 | NM_001011767.1 | chr7:86465412-86466405 | 15519 | Olfr424 | NM_146721.2 | chr1:174136745-174137693 |

Fig.21 - 81

| | | | | | | | | |
|---|---|---|---|---|---|---|---|---|
| 15520 | Olfr426 | NM_001206926.1 | chr1:174099459-174100410 | | 15617 | Olfr539 | NM_146961.1 | chr7:140667288-140668248 |
| 15521 | Olfr427 | NM_207158.1 | chr1:174099459-174100407 | | 15618 | Olfr54 | NM_010997.1 | chr11:51027003-51027945 |
| 15522 | Olfr429 | NM_146722.2 | chr1:174089037-174089980 | | 15619 | Olfr541 | NM_146962.1 | chr7:140704252-140705191 |
| 15523 | Olfr43 | NM_146711.2 | chr11:74206197-74207289 | | 15620 | Olfr543 | NM_001011782.2 | chr7:102476772-102477902 |
| 15524 | Olfr430 | NM_146718.2 | chr1:174069299-174070253 | | 15621 | Olfr544 | NM_020289.2 | chr7:102484113-102488307 |
| 15525 | Olfr432 | NM_146716.2 | chr1:174050374-174051313 | | 15622 | Olfr545 | NM_146840.1 | chr7:102493822-102494773 |
| 15526 | Olfr433 | NM_146717.2 | chr1:174041932-174042936 | | 15623 | Olfr547 | NM_147079.2 | chr7:102534748-102535688 |
| 15527 | Olfr434 | NM_146369.1 | chr6:43216914-43217880 | | 15624 | Olfr549 | NM_147101.2 | chr7:102554285-102555236 |
| 15528 | Olfr435 | NM_146653.1 | chr6:43201645-43202587 | | 15625 | Olfr55 | NM_010998.2 | chr17:33176415-33177363 |
| 15529 | Olfr437 | NM_146296.1 | chr6:43167059-43167992 | | 15626 | Olfr550 | NM_147104.2 | chr7:102578468-102579506 |
| 15530 | Olfr44 | NM_146830.2 | chr9:39484203-39493988 | | 15627 | Olfr551 | NM_146755.2 | chr7:102587740-102588819 |
| 15531 | Olfr441 | NM_146655.1 | chr6:43115743-43116676 | | 15628 | Olfr552 | NM_147102.2 | chr7:102604355-102605309 |
| 15532 | Olfr444 | NM_146656.1 | chr6:42955499-42956432 | | 15629 | Olfr553 | NM_207621.1 | chr7:102614006-102614987 |
| 15533 | Olfr446 | NM_146295.1 | chr6:42927232-42928159 | | 15630 | Olfr554 | NM_146325.2 | chr7:102640247-102641201 |
| 15534 | Olfr447 | NM_146988.1 | chr6:42896162-42912457 | | 15631 | Olfr555 | NM_147103.2 | chr7:102658822-102659770 |
| 15535 | Olfr448 | NM_146273.1 | chr6:42896452-42897385 | | 15632 | Olfr556 | NM_146754.2 | chr7:102669900-102670923 |
| 15536 | Olfr449 | NM_147064.1 | chr6:42837882-42838818 | | 15633 | Olfr557 | NM_146361.2 | chr7:102698215-102699272 |
| 15537 | Olfr45 | NM_146963.1 | chr7:140690906-140691842 | | 15634 | Olfr558 | NM_147093.3 | chr7:102702322-102712054 |
| 15538 | Olfr450 | NM_146445.1 | chr6:42817472-42818405 | | 15635 | Olfr559 | NM_147112.1 | chr7:102723531-102724488 |
| 15539 | Olfr452 | NM_001011869.1 | chr6:42790040-42790994 | | 15636 | Olfr56 | NM_010999.2 | chr11:49050732-49135387 |
| 15540 | Olfr453 | NM_001011799.1 | chr6:42744038-42744992 | | 15637 | Olfr560 | NM_147113.2 | chr7:102752982-102753927 |
| 15541 | Olfr455 | NM_001081301.2 | chr6:42538066-42539020 | | 15638 | Olfr561 | NM_147092.1 | chr7:102774525-102775470 |
| 15542 | Olfr456 | NM_001011528.2 | chr6:42486162-42487214 | | 15639 | Olfr564 | NM_146359.2 | chr7:102803479-102804430 |
| 15543 | Olfr457 | NM_146987.1 | chr6:42471234-42472176 | | 15640 | Olfr566 | NM_001011536.1 | chr7:102856320-102857271 |
| 15544 | Olfr458 | NM_146444.1 | chr6:42460075-42461017 | | 15641 | Olfr568 | NM_147091.2 | chr7:102877121-102878063 |
| 15545 | Olfr459 | NM_147713.1 | chr6:41771352-41772297 | | 15642 | Olfr569 | NM_147088.1 | chr7:102887206-102888151 |
| 15546 | Olfr46 | NM_146934.2 | chr7:140601339-140611124 | | 15643 | Olfr57 | NM_147041.2 | chr10:79034722-79035802 |
| 15547 | Olfr460 | NM_146383.1 | chr6:40571387-40572332 | | 15644 | Olfr570 | NM_147110.1 | chr7:102900368-102901307 |
| 15548 | Olfr461 | NM_146382.1 | chr6:40544035-40544977 | | 15645 | Olfr571 | NM_147085.2 | chr7:102908868-102909837 |
| 15549 | Olfr462 | NM_146411.2 | chr11:87888958-87889894 | | 15646 | Olfr572 | NM_147089.2 | chr7:102927629-102928586 |
| 15550 | Olfr463 | NM_146413.2 | chr11:87892986-87893922 | | 15647 | Olfr574 | NM_146360.2 | chr7:102948466-102949507 |
| 15551 | Olfr464 | NM_146412.1 | chr11:87913919-87915003 | | 15648 | Olfr575 | NM_147114.2 | chr7:102954663-102955620 |
| 15552 | Olfr466 | NM_146819.2 | chr13:65152225-65153152 | | 15649 | Olfr576 | NM_001011805.2 | chr7:102965101-102966040 |
| 15553 | Olfr467 | NM_001005488.1 | chr7:107814585-107815506 | | 15650 | Olfr577 | NM_147109.1 | chr7:102973051-102973990 |
| 15554 | Olfr469 | NM_146426.1 | chr7:107822522-107823467 | | 15651 | Olfr578 | NM_147115.1 | chr7:102984220-102985162 |
| 15555 | Olfr47 | NM_146370.1 | chr6:43235609-43236575 | | 15652 | Olfr58 | NM_011001.2 | chr9:19780282-19784064 |
| 15556 | Olfr470 | NM_146425.1 | chr7:107844786-107845731 | | 15653 | Olfr582 | NM_147053.1 | chr7:103041480-103042440 |
| 15557 | Olfr472 | NM_146774.1 | chr7:107902718-107903651 | | 15654 | Olfr583 | NM_146757.1 | chr7:103051299-103052259 |
| 15558 | Olfr473 | NM_146773.1 | chr7:107933521-107934454 | | 15655 | Olfr584 | NM_147087.2 | chr7:103085519-103086479 |
| 15559 | Olfr474 | NM_146495.1 | chr7:107954642-107955575 | | 15656 | Olfr585 | NM_147087.2 | chr7:103097742-103098699 |
| 15560 | Olfr476 | NM_146924.1 | chr7:107967398-107968331 | | 15657 | Olfr586 | NM_147111.1 | chr7:103121828-103122782 |
| 15561 | Olfr477 | NM_146926.1 | chr7:107990366-107991299 | | 15658 | Olfr589 | NM_147052.1 | chr7:103154791-103155745 |
| 15562 | Olfr478 | NM_146734.1 | chr7:108031396-108032341 | | 15659 | Olfr59 | NM_011002.2 | chr11:74288808-74289646 |
| 15563 | Olfr479 | NM_001011742.1 | chr7:108054983-108055967 | | 15660 | Olfr591 | NM_001011847.1 | chr7:103172690-103173635 |
| 15564 | Olfr48 | NM_010990.1 | chr2:89844065-89844971 | | 15661 | Olfr592 | NM_207556.2 | chr7:103186602-103187541 |
| 15565 | Olfr480 | NM_020291.1 | chr7:108065767-108066796 | | 15662 | Olfr593 | NM_146380.1 | chr7:103211861-103212845 |
| 15566 | Olfr481 | NM_146929.1 | chr7:108080795-108081734 | | 15663 | Olfr594 | NM_207143.1 | chr7:103219719-103220655 |
| 15567 | Olfr482 | NM_146733.1 | chr7:108094596-108095568 | | 15664 | Olfr596 | NM_001190381.1 | chr7:103309722-103310661 |
| 15568 | Olfr483 | NM_146735.1 | chr7:108103310-108104258 | | 15665 | Olfr597 | NM_001011845.2 | chr7:103320412-103321360 |
| 15569 | Olfr484 | NM_146499.1 | chr7:108124295-108125261 | | 15666 | Olfr598 | NM_001011793.1 | chr7:103328487-103329447 |
| 15570 | Olfr485 | NM_001011810.2 | chr7:108158917-108159871 | | 15667 | Olfr599 | NM_146731.1 | chr7:103338055-103339003 |
| 15571 | Olfr486 | NM_146496.1 | chr7:108171797-108172742 | | 15668 | Olfr6 | NM_206897.2 | chr7:106955983-106956934 |
| 15572 | Olfr487 | NM_001011811.1 | chr7:108211582-108212527 | | 15669 | Olfr60 | NM_146955.1 | chr7:140345051-140345987 |
| 15573 | Olfr488 | NM_146732.1 | chr7:108255191-108256136 | | 15670 | Olfr600 | NM_147046.2 | chr7:103345981-103346926 |
| 15574 | Olfr49 | NM_010991.2 | chr14:54281895-54282925 | | 15671 | Olfr601 | NM_146314.2 | chr7:103358223-103359213 |
| 15575 | Olfr490 | NM_146498.1 | chr7:108286179-108287124 | | 15672 | Olfr603 | NM_147070.2 | chr7:103383061-103384000 |
| 15576 | Olfr491 | NM_146736.1 | chr7:108316895-108317828 | | 15673 | Olfr605 | NM_001011854.2 | chr7:103442139-103443150 |
| 15577 | Olfr492 | NM_146497.1 | chr7:108322729-108323674 | | 15674 | Olfr606 | NM_147054.1 | chr7:103451338-103452298 |
| 15578 | Olfr493 | NM_146310.1 | chr7:108346034-108346979 | | 15675 | Olfr608 | NM_146756.2 | chr7:103470040-103470991 |
| 15579 | Olfr494 | NM_146737.1 | chr7:108367491-108368436 | | 15676 | Olfr609 | NM_147082.2 | chr7:103491916-103492876 |
| 15580 | Olfr495 | NM_146364.1 | chr7:108395121-108396114 | | 15677 | Olfr61 | NM_146964.1 | chr7:140637702-140638638 |
| 15581 | Olfr497 | NM_146738.1 | chr7:108422572-108423517 | | 15678 | Olfr610 | NM_147081.2 | chr7:103505996-103506944 |
| 15582 | Olfr498 | NM_146307.2 | chr7:108465315-108466318 | | 15679 | Olfr611 | NM_146727.2 | chr7:103517410-103518382 |
| 15583 | Olfr5 | NM_146914.2 | chr7:6480215-6486813 | | 15680 | Olfr612 | NM_001200027.1 | chr7:103538260-103539232 |
| 15584 | Olfr50 | NM_146946.1 | chr2:36793237-36794176 | | 15681 | Olfr613 | NM_147100.3 | chr7:103550367-103555504 |
| 15585 | Olfr502 | NM_146902.1 | chr7:108523003-108523948 | | 15682 | Olfr615 | NM_147080.2 | chr7:103560478-103561420 |
| 15586 | Olfr503 | NM_001011527.1 | chr7:108544526-108545498 | | 15683 | Olfr616 | NM_147099.2 | chr7:103564323-103565277 |
| 15587 | Olfr504 | NM_001011858.1 | chr7:108564836-108565793 | | 15684 | Olfr617 | NM_146841.1 | chr7:103584023-103584980 |
| 15588 | Olfr506 | NM_001011871.1 | chr7:108612308-108613253 | | 15685 | Olfr618 | NM_147047.2 | chr7:103597317-103598274 |
| 15589 | Olfr507 | NM_146743.1 | chr7:108621813-108622764 | | 15686 | Olfr619 | NM_147076.2 | chr7:103603588-103604711 |
| 15590 | Olfr508 | NM_146729.1 | chr7:108629993-108630926 | | 15687 | Olfr62 | NM_146315.2 | chr4:118665518-118666466 |
| 15591 | Olfr509 | NM_146372.1 | chr7:108645608-108646574 | | 15688 | Olfr620 | NM_146812.2 | chr7:103611409-103612351 |
| 15592 | Olfr51 | NM_146909.1 | chr11:51006973-51007897 | | 15689 | Olfr622 | NM_147083.1 | chr7:103639184-103640138 |
| 15593 | Olfr510 | NM_146311.1 | chr7:108667417-108668362 | | 15690 | Olfr623 | NM_147122.2 | chr7:103660243-103661318 |
| 15594 | Olfr512 | NM_146724.1 | chr7:108713354-108714335 | | 15691 | Olfr624 | NM_001011865.2 | chr7:103670102-103671029 |
| 15595 | Olfr513 | NM_146723.1 | chr7:108754857-108755787 | | 15692 | Olfr628 | NM_147097.2 | chr7:103731927-103732878 |
| 15596 | Olfr514 | NM_146726.1 | chr7:108825064-108825997 | | 15693 | Olfr629 | NM_146821.2 | chr7:103740200-103741132 |
| 15597 | Olfr516 | NM_146725.1 | chr7:108845063-108846008 | | 15694 | Olfr63 | NM_146937.1 | chr17:33268725-33269676 |
| 15598 | Olfr517 | NM_001011846.1 | chr7:108868207-108869152 | | 15695 | Olfr630 | NM_147098.2 | chr7:103754149-103757550 |
| 15599 | Olfr518 | NM_146306.1 | chr7:108880602-108881604 | | 15696 | Olfr631 | NM_001271020.1 | chr7:103915061-103929811 |
| 15600 | Olfr519 | NM_207160.1 | chr7:108893460-108894405 | | 15697 | Olfr632 | NM_147119.1 | chr7:103937381-103938335 |
| 15601 | Olfr52 | NM_146583.1 | chr2:86181149-86182109 | | 15698 | Olfr633 | NM_146354.1 | chr7:103946567-103947506 |
| 15602 | Olfr520 | NM_147063.2 | chr7:99735144-99736095 | | 15699 | Olfr635 | NM_147118.2 | chr7:103979175-103980141 |
| 15603 | Olfr521 | NM_146362.1 | chr7:99767163-99768129 | | 15700 | Olfr638 | NM_147120.1 | chr7:104003258-104004224 |
| 15604 | Olfr522 | NM_146952.1 | chr7:140162009-140162948 | | 15701 | Olfr639 | NM_147084.1 | chr7:104011749-104012700 |
| 15605 | Olfr523 | NM_146518.1 | chr7:140176103-140177057 | | 15702 | Olfr64 | NM_013617.3 | chr7:103892809-103894471 |
| 15606 | Olfr524 | NM_001011814.1 | chr7:140201811-140202768 | | 15703 | Olfr640 | NM_146822.2 | chr7:104021371-104022316 |
| 15607 | Olfr525 | NM_146956.1 | chr7:140322700-140323630 | | 15704 | Olfr641 | NM_147073.2 | chr7:104039797-104040736 |
| 15608 | Olfr527 | NM_001011776.1 | chr7:140335863-140336781 | | 15705 | Olfr642 | NM_146329.1 | chr7:104049407-104050352 |
| 15609 | Olfr53 | NM_146960.2 | chr7:140652916-140652919 | | 15706 | Olfr643 | NM_147077.1 | chr7:104058655-104059600 |
| 15610 | Olfr530 | NM_146519.1 | chr7:140372684-140373608 | | 15707 | Olfr644 | NM_147121.1 | chr7:104068084-104069029 |
| 15611 | Olfr531 | NM_146953.1 | chr7:140390109-140401044 | | 15708 | Olfr645 | NM_207144.1 | chr7:104084130-104085078 |
| 15612 | Olfr532 | NM_147026.1 | chr7:140418841-140419771 | | 15709 | Olfr646 | NM_147056.1 | chr7:104106280-104107219 |
| 15613 | Olfr533 | NM_001011815.1 | chr7:140466202-140467165 | | 15710 | Olfr648 | NM_146751.1 | chr7:104179455-104180406 |
| 15614 | Olfr535 | NM_146954.1 | chr7:140493639-140493578 | | 15711 | Olfr649 | NM_146954.1 | chr7:104189266-104190205 |
| 15615 | Olfr536 | NM_146520.2 | chr7:140500852-140507318 | | 15712 | Olfr65 | NM_013616.4 | chr7:103906341-103907447 |
| 15616 | Olfr538 | NM_001011867.1 | chr7:140574154-140575087 | | 15713 | Olfr651 | NM_146813.2 | chr7:104552883-104553952 |

Fig.21 - 82

| | | | | | | | | |
|---|---|---|---|---|---|---|---|---|
| 15714 | Olfr652 | NM_147048.2 | chr7:104564151-104565212 | 15811 | Olfr769 | NM_146287.1 | chr10:129111484-129112423 |
| 15715 | Olfr653 | NM_147074.2 | chr7:104579623-104580669 | 15812 | Olfr77 | NM_146339.3 | chr9:19917228-19922510 |
| 15716 | Olfr654 | NM_146379.1 | chr7:104587754-104588780 | 15813 | Olfr770 | NM_146863.1 | chr10:129132830-129133766 |
| 15717 | Olfr655 | NM_146820.2 | chr7:104596252-104597179 | 15814 | Olfr771 | NM_146547.1 | chr10:129160026-129160982 |
| 15718 | Olfr656 | NM_147075.1 | chr7:104617656-104618646 | 15815 | Olfr772 | NM_146266.2 | chr10:129174050-129175054 |
| 15719 | Olfr657 | NM_146312.2 | chr7:104635675-104636635 | 15816 | Olfr773 | NM_207008.2 | chr10:129186483-129187419 |
| 15720 | Olfr658 | NM_147049.4 | chr7:104642879-104647305 | 15817 | Olfr774 | NM_207620.1 | chr10:129238150-129239089 |
| 15721 | Olfr659 | NM_147050.1 | chr7:104670703-104671672 | 15818 | Olfr775 | NM_146545.2 | chr10:129250535-129251474 |
| 15722 | Olfr66 | NM_013618.3 | chr7:103881305-103882241 | 15819 | Olfr776 | NM_207559.1 | chr10:129260962-129261901 |
| 15723 | Olfr661 | NM_146748.1 | chr7:104688016-104688976 | 15820 | Olfr777 | NM_146544.1 | chr10:129268385-129269321 |
| 15724 | Olfr663 | NM_001011757.1 | chr7:104703568-104704603 | 15821 | Olfr78 | NM_001168503.1 | chr7:102740720-102759471 |
| 15725 | Olfr665 | NM_146814.1 | chr7:104880708-104881659 | 15822 | Olfr780 | NM_146284.1 | chr10:129321624-129322563 |
| 15726 | Olfr666 | NM_147096.1 | chr7:104892669-104893626 | 15823 | Olfr781 | NM_146728.1 | chr10:129332882-129333818 |
| 15727 | Olfr667 | NM_147060.2 | chr7:104916313-104917294 | 15824 | Olfr782 | NM_001011797.1 | chr10:129350564-129351509 |
| 15728 | Olfr668 | NM_147059.1 | chr7:104924805-104925762 | 15825 | Olfr784 | NM_146729.1 | chr10:129387634-129388594 |
| 15729 | Olfr669 | NM_147043.1 | chr7:104938527-104939481 | 15826 | Olfr786 | NM_146549.1 | chr10:129436813-129437752 |
| 15730 | Olfr67 | NM_013619.3 | chr7:103787211-103791830 | 15827 | Olfr787 | NM_001011822.1 | chr10:129462677-129463616 |
| 15731 | Olfr670 | NM_207146.1 | chr7:104959791-104960730 | 15828 | Olfr788 | NM_146551.1 | chr10:129472693-129473629 |
| 15732 | Olfr671 | NM_001011795.1 | chr7:104975041-104975983 | 15829 | Olfr790 | NM_146913.1 | chr10:129500885-129501854 |
| 15733 | Olfr672 | NM_146760.1 | chr7:104995963-104996902 | 15830 | Olfr791 | NM_146930.1 | chr10:129526228-129527167 |
| 15734 | Olfr675 | NM_001011848.1 | chr7:105024024-105024966 | 15831 | Olfr792 | NM_001011849.1 | chr10:129540538-129541474 |
| 15735 | Olfr676 | NM_147095.1 | chr7:105035199-105036153 | 15832 | Olfr794 | NM_146378.1 | chr10:129570656-129571619 |
| 15736 | Olfr677 | NM_146358.1 | chr7:105056247-105057186 | 15833 | Olfr796 | NM_146931.1 | chr10:129607546-129608479 |
| 15737 | Olfr678 | NM_146756.1 | chr7:105069468-105070410 | 15834 | Olfr798 | NM_146556.2 | chr10:129625123-129626059 |
| 15738 | Olfr679 | NM_147044.1 | chr7:105085717-105086665 | 15835 | Olfr799 | NM_146927.1 | chr10:129647129-129648085 |
| 15739 | Olfr68 | NM_013620.2 | chr7:103777395-103778343 | 15836 | Olfr8 | NM_207201.1 | chr10:78955206-78956139 |
| 15740 | Olfr681 | NM_207557.2 | chr7:105121458-105122406 | 15837 | Olfr800 | NM_146548.1 | chr10:129659807-129660743 |
| 15741 | Olfr683 | NM_147045.1 | chr7:105143349-105144309 | 15838 | Olfr801 | NM_146285.1 | chr10:129669560-129670517 |
| 15742 | Olfr684 | NM_207249.2 | chr7:105156741-105157680 | 15839 | Olfr802 | NM_146932.1 | chr10:129681798-129682737 |
| 15743 | Olfr685 | NM_001011857.1 | chr7:105180360-105181311 | 15840 | Olfr803 | NM_146554.1 | chr10:129691112-129692039 |
| 15744 | Olfr686 | NM_147069.1 | chr7:105203387-105204341 | 15841 | Olfr804 | NM_001011821.1 | chr10:129704879-129705824 |
| 15745 | Olfr688 | NM_001011533.2 | chr7:105288094-105289060 | 15842 | Olfr805 | NM_146555.1 | chr10:129722582-129723542 |
| 15746 | Olfr689 | NM_146750.1 | chr7:105314005-105314968 | 15843 | Olfr806 | NM_146553.1 | chr10:129737973-129738915 |
| 15747 | Olfr69 | NM_013621.3 | chr7:103767276-103771594 | 15844 | Olfr807 | NM_146929.1 | chr10:129754512-129755448 |
| 15748 | Olfr690 | NM_020290.2 | chr7:105329216-105330278 | 15845 | Olfr808 | NM_146928.1 | chr10:129767497-129768436 |
| 15749 | Olfr691 | NM_147061.1 | chr7:105336748-105337714 | 15846 | Olfr809 | NM_146324.1 | chr10:129775870-129776857 |
| 15750 | Olfr692 | NM_146355.1 | chr7:105368327-105369317 | 15847 | Olfr810 | NM_146550.1 | chr10:129790648-129791587 |
| 15751 | Olfr693 | NM_146453.2 | chr7:106677533-106678485 | 15848 | Olfr811 | NM_146552.1 | chr10:129801563-129802523 |
| 15752 | Olfr694 | NM_146452.2 | chr7:106688781-106689729 | 15849 | Olfr812 | NM_146795.1 | chr10:129842107-129843040 |
| 15753 | Olfr695 | NM_146598.2 | chr7:106713731-106716345 | 15850 | Olfr813 | NM_207147.1 | chr10:129856519-129857452 |
| 15754 | Olfr697 | NM_146599.2 | chr7:106740907-106741956 | 15851 | Olfr814 | NM_207159.1 | chr10:129873822-129874755 |
| 15755 | Olfr698 | NM_146602.2 | chr7:106752450-106753386 | 15852 | Olfr815 | NM_146670.1 | chr10:129901775-129902726 |
| 15756 | Olfr699 | NM_001011862.1 | chr7:106790048-106790999 | 15853 | Olfr816 | NM_146672.1 | chr10:129911337-129912276 |
| 15757 | Olfr70 | NM_019486.1 | chr4:43694999-43700807 | 15854 | Olfr818 | NM_146777.1 | chr10:129945103-129946060 |
| 15758 | Olfr700 | NM_146600.1 | chr7:106805509-106806460 | 15855 | Olfr819 | NM_001165944.1 | chr10:129965735-129966658 |
| 15759 | Olfr701 | NM_028910.3 | chr7:106814143-106820709 | 15856 | Olfr820 | NM_146675.1 | chr10:130017362-130018301 |
| 15760 | Olfr702 | NM_146823.2 | chr7:106823488-106826763 | 15857 | Olfr821 | NM_146776.1 | chr10:130033627-130034560 |
| 15761 | Olfr703 | NM_146596.1 | chr7:106844612-106845572 | 15858 | Olfr822 | NM_146671.1 | chr10:130074411-130075350 |
| 15762 | Olfr704 | NM_001011749.1 | chr7:106864981-106865929 | 15859 | Olfr823 | NM_146673.2 | chr10:130111840-130112788 |
| 15763 | Olfr705 | NM_147032.2 | chr7:106873292-106874243 | 15860 | Olfr824 | NM_146674.1 | chr10:130126107-130127055 |
| 15764 | Olfr706 | NM_146353.2 | chr7:106885864-106886815 | 15861 | Olfr825 | NM_146677.1 | chr10:130162361-130163324 |
| 15765 | Olfr707 | NM_001095570.2 | chr7:106891183-106892107 | 15862 | Olfr826 | NM_146676.1 | chr10:130179936-130180878 |
| 15766 | Olfr71 | NM_019486.1 | chr4:43705627-43706566 | 15863 | Olfr827 | NM_146300.1 | chr10:130210159-130211128 |
| 15767 | Olfr710 | NM_146601.1 | chr7:106944066-106948312 | 15864 | Olfr828 | NM_146605.1 | chr9:18815353-18816292 |
| 15768 | Olfr711 | NM_147035.2 | chr7:106968372-106975451 | 15865 | Olfr829 | NM_147067.1 | chr9:18856626-18857552 |
| 15769 | Olfr713 | NM_147034.1 | chr7:107036135-107037110 | 15866 | Olfr830 | NM_146566.1 | chr9:18875328-18876276 |
| 15770 | Olfr714 | NM_147033.2 | chr7:107073829-107074783 | 15867 | Olfr832 | NM_001011824.1 | chr9:18944649-18945588 |
| 15771 | Olfr715 | NM_146780.2 | chr7:107128351-107129482 | 15868 | Olfr834 | NM_001011823.1 | chr9:18987989-18988928 |
| 15772 | Olfr716 | NM_146604.1 | chr7:107147317-107148262 | 15869 | Olfr835 | NM_001012266.1 | chr9:19035124-19036060 |
| 15773 | Olfr720 | NM_146392.1 | chr14:14175129-14176080 | 15870 | Olfr836 | NM_146564.2 | chr9:19120956-19121911 |
| 15774 | Olfr722 | NM_146494.2 | chr14:49894257-49901941 | 15871 | Olfr837 | NM_146565.2 | chr9:19136927-19137967 |
| 15775 | Olfr723 | NM_001011530.2 | chr14:49928562-49929568 | 15872 | Olfr843 | NM_146567.2 | chr9:19248356-19249463 |
| 15776 | Olfr724 | NM_146492.2 | chr14:49960090-49961096 | 15873 | Olfr845 | NM_147145.2 | chr9:19338458-19339400 |
| 15777 | Olfr725 | NM_146317.2 | chr14:50034396-50035500 | 15874 | Olfr846 | NM_146282.2 | chr9:19360414-19361356 |
| 15778 | Olfr726 | NM_146316.2 | chr14:50083713-50084679 | 15875 | Olfr847 | NM_146525.1 | chr9:19374940-19375879 |
| 15779 | Olfr727 | NM_146319.2 | chr14:50126552-50127587 | 15876 | Olfr849 | NM_146526.1 | chr9:19440914-19441853 |
| 15780 | Olfr728 | NM_001011809.1 | chr14:50139703-50140637 | 15877 | Olfr850 | NM_146523.1 | chr9:19477300-19478248 |
| 15781 | Olfr729 | NM_146278.1 | chr14:50147900-50148872 | 15878 | Olfr851 | NM_146905.2 | chr9:19496749-19497688 |
| 15782 | Olfr73 | NM_054090.1 | chr2:88034195-88035137 | 15879 | Olfr853 | NM_146906.1 | chr9:19537010-19537928 |
| 15783 | Olfr730 | NM_146493.2 | chr14:50186261-50187218 | 15880 | Olfr854 | NM_146522.1 | chr9:19566434-19567382 |
| 15784 | Olfr731 | NM_146363.2 | chr14:50237902-50238883 | 15881 | Olfr855 | NM_146524.2 | chr9:19584510-19585502 |
| 15785 | Olfr732 | NM_146665.2 | chr14:50281227-50282271 | 15882 | Olfr856-ps1 | NR_033621.1 | chr9:19657038-19658680 |
| 15786 | Olfr733 | NM_146663.2 | chr14:50298336-50299330 | 15883 | Olfr857 | NM_001012265.1 | chr9:19712828-19713758 |
| 15787 | Olfr734 | NM_146664.1 | chr14:50319891-50320333 | 15884 | Olfr859 | NM_146526.2 | chr9:19808319-19809249 |
| 15788 | Olfr735 | NM_001011754.2 | chr14:50345375-50346440 | 15885 | Olfr860 | NM_146528.2 | chr9:19845622-19849747 |
| 15789 | Olfr736 | NM_146666.1 | chr14:50392757-50393696 | 15886 | Olfr862 | NM_146562.1 | chr9:19883382-19884303 |
| 15790 | Olfr738 | NM_146420.2 | chr14:50413545-50414481 | 15887 | Olfr866 | NM_146558.2 | chr9:20026958-20028035 |
| 15791 | Olfr739 | NM_146668.2 | chr14:50424520-50425450 | 15888 | Olfr867 | NM_001011748.1 | chr9:20054465-20055461 |
| 15792 | Olfr74 | NM_054092.2 | chr2:87973706-87974663 | 15889 | Olfr868 | NM_146559.2 | chr9:20098625-20101696 |
| 15793 | Olfr740 | NM_146667.2 | chr14:50453053-50453989 | 15890 | Olfr869 | NM_146557.2 | chr9:20129119-20130089 |
| 15794 | Olfr741 | NM_207133.2 | chr14:50473056-50486395 | 15891 | Olfr870 | NM_146904.1 | chr9:20170633-20171569 |
| 15795 | Olfr742 | NM_146430.2 | chr14:50515120-50516240 | 15892 | Olfr871 | NM_146903.2 | chr9:20212206-20213353 |
| 15796 | Olfr743 | NM_001177508.1 | chr14:50533413-50534349 | 15893 | Olfr872 | NM_146560.2 | chr9:20237161-20280913 |
| 15797 | Olfr744 | NM_001011738.1 | chr14:50618223-50619195 | 15894 | Olfr873 | NM_146561.1 | chr9:20300210-20301170 |
| 15798 | Olfr745 | NM_146362.1 | chr14:50642194-50643369 | 15895 | Olfr874 | NM_146682.2 | chr9:37746135-37747068 |
| 15799 | Olfr746 | NM_146298.2 | chr14:50653238-50654183 | 15896 | Olfr875 | NM_146749.2 | chr9:37772636-37773640 |
| 15800 | Olfr747 | NM_207156.1 | chr14:50680690-50681645 | 15897 | Olfr876 | NM_146883.2 | chr9:37803888-37804936 |
| 15801 | Olfr748 | NM_001011837.1 | chr14:50710331-50711255 | 15898 | Olfr877 | NM_146417.1 | chr9:37854819-37855755 |
| 15802 | Olfr749 | NM_020288.2 | chr14:50736218-50744224 | 15899 | Olfr878 | NM_146798.2 | chr9:37918547-37919612 |
| 15803 | Olfr750 | NM_207558.2 | chr14:51070310-51071442 | 15900 | Olfr881 | NM_146418.2 | chr9:37992491-37993439 |
| 15804 | Olfr75-ps1 | NR_002859.2 | chr11:73405449-73409823 | 15901 | Olfr883 | NM_146419.2 | chr9:38025807-38026737 |
| 15805 | Olfr76 | NM_146682.1 | chr19:12119720-12120674 | 15902 | Olfr884 | NM_001011798.1 | chr9:38047223-38048153 |
| 15806 | Olfr761 | NM_001011829.1 | chr17:37952050-37953022 | 15903 | Olfr885 | NM_001011739.1 | chr9:38061323-38062251 |
| 15807 | Olfr763 | NM_146862.1 | chr10:129011286-129012216 | 15904 | Olfr887 | NM_146423.1 | chr9:38084837-38085767 |
| 15808 | Olfr765 | NM_001085477.1 | chr10:129046131-129047061 | 15905 | Olfr888 | NM_146424.1 | chr9:38108687-38109632 |
| 15809 | Olfr767 | NM_146318.2 | chr10:129079031-129079961 | 15906 | Olfr889 | NM_146482.1 | chr9:38115797-38116727 |
| 15810 | Olfr768 | NM_146864.1 | chr10:129093033-129093972 | 15907 | Olfr890 | NM_146481.2 | chr9:38143136-38144081 |

Fig.21 - 83

| | | | | | | | | |
|---|---|---|---|---|---|---|---|---|
| 15908 | Olfr891 | NM_146478.2 | chr9:38179870-38180821 | | 16005 | Omp | NM_011010.2 | chr7:98143358-98145447 |
| 15909 | Olfr893 | NM_146336.2 | chr9:38209051-38209993 | | 16006 | Omt2a | NM_001111286.1 | chr9:78311971-78314048 |
| 15910 | Olfr894 | NM_146868.2 | chr9:38218817-38219766 | | 16007 | Omt2b | NM_205822.2 | chr9:78328029-78329620 |
| 15911 | Olfr895 | NM_146875.2 | chr9:38268514-38269465 | | 16008 | Onecut1 | NM_008262.3 | chr9:74861920-74889647 |
| 15912 | Olfr898 | NM_146712.1 | chr9:38349084-38350035 | | 16009 | Onecut2 | NM_194268.2 | chr18:64340363-64398488 |
| 15913 | Olfr899 | NM_146479.1 | chr9:38367547-38368543 | | 16010 | Onecut3 | NM_139226.3 | chr10:80494905-80517260 |
| 15914 | Olfr9 | NM_146861.1 | chr10:128989913-128990852 | | 16011 | Ooep | NM_026480.3 | chr9:78376902-78378588 |
| 15915 | Olfr90 | NM_146477.2 | chr17:37086190-37086236 | | 16012 | Oog1 | NM_178657.5 | chr12:87602664-87608845 |
| 15916 | Olfr900 | NM_146874.1 | chr9:38377882-38378833 | | 16013 | Oog2 | NM_198661.3 | chr4:144190716-144196934 |
| 15917 | Olfr901 | NM_001011806.1 | chr9:38430283-38431219 | | 16014 | Oog3 | NM_201258.2 | chr4:144157555-144162651 |
| 15918 | Olfr902 | NM_146802.2 | chr9:38448791-38449847 | | 16015 | Oog4 | NM_173773.1 | chr4:143437163-143450302 |
| 15919 | Olfr904 | NM_146801.2 | chr9:38464042-38464975 | | 16016 | Oosp1 | NM_133353.3 | chr19:11667459-11691051 |
| 15920 | Olfr905 | NM_146804.2 | chr9:38472748-38473681 | | 16017 | Oosp2 | NM_001037634.3 | chr19:11647283-11660559 |
| 15921 | Olfr906 | NM_146803.2 | chr9:38488030-38488966 | | 16018 | Oosp3 | NM_001033283.2 | chr19:11697054-11711858 |
| 15922 | Olfr907 | NM_146805.2 | chr9:38498670-38499603 | | 16019 | Opa1 | NM_001199177.1 | chr16:29579333-29654602 |
| 15923 | Olfr908 | NM_146872.1 | chr9:38516033-38516965 | | 16020 | Opa3 | NM_207525.3 | chr7:19228388-19246817 |
| 15924 | Olfr91 | NM_182714.2 | chr17:37092933-37093872 | | 16021 | Opalin | NM_153520.1 | chr19:41063419-41077113 |
| 15925 | Olfr910 | NM_146811.2 | chr9:38537881-38538829 | | 16022 | Opcml | NM_177906.4 | chr9:27791268-28925048 |
| 15926 | Olfr911-ps1 | NM_146873.2 | chr9:38523729-38524669 | | 16023 | Optn1 | NM_052976.4 | chrX:98554279-98891025 |
| 15927 | Olfr912 | NM_146810.2 | chr9:38580243-38582211 | | 16024 | Oplah | NM_153122.2 | chr15:76296602-76307245 |
| 15928 | Olfr913 | NM_001011523.2 | chr9:38592802-38595161 | | 16025 | Opn1mw | NM_008106.2 | chrX:74127465-74150755 |
| 15929 | Olfr914 | NM_146786.2 | chr9:38606466-38607417 | | 16026 | Opn1sw | NM_007538.3 | chr6:29376670-29380513 |
| 15930 | Olfr915 | NM_146785.2 | chr9:38646689-38647522 | | 16027 | Opn3 | NM_010098.3 | chr1:175662420-175692632 |
| 15931 | Olfr916 | NM_146784.1 | chr9:38657457-38658390 | | 16028 | Opn4 | NM_001128599.1 | chr14:34590617-34600142 |
| 15932 | Olfr917 | NM_001011864.1 | chr9:38664912-38665842 | | 16029 | Opn5 | NM_181753.4 | chr17:42556782-42611313 |
| 15933 | Olfr918 | NM_146375.2 | chr9:38672503-38673481 | | 16030 | Oprd1 | NM_013622.3 | chr4:132110725-132144486 |
| 15934 | Olfr919 | NM_146440.1 | chr9:38697428-38698376 | | 16031 | Oprk1 | NM_001204371.1 | chr1:5584492-5606193 |
| 15935 | Olfr92 | NM_146467.2 | chr17:37111041-37111980 | | 16032 | Oprl1 | NM_001252565.1 | chr2:181715347-181720985 |
| 15936 | Olfr920 | NM_146787.2 | chr9:38752795-38756863 | | 16033 | Oprm1 | NM_001039652.2 | chr10:6788575-7038209 |
| 15937 | Olfr921 | NM_146782.2 | chr9:38773087-38776354 | | 16034 | Optc | NM_001160420.2 | chr1:133897193-133907999 |
| 15938 | Olfr922 | NM_146781.2 | chr9:38815407-38816539 | | 16035 | Optn | NM_181848.4 | chr2:5020641-5063938 |
| 15939 | Olfr923 | NM_146816.2 | chr9:38827614-38828682 | | 16036 | Orai1 | NM_175423.3 | chr5:123015673-123030452 |
| 15940 | Olfr924 | NM_207560.1 | chr9:38848115-38849042 | | 16037 | Orai2 | NM_178751.3 | chr5:136147460-136170656 |
| 15941 | Olfr926 | NM_146815.1 | chr9:38877177-38878104 | | 16038 | Orai3 | NM_198424.3 | chr7:127769814-127775150 |
| 15942 | Olfr93 | NM_146811813.1 | chr17:37151031-37151970 | | 16039 | Oraov1 | NM_028184.3 | chr7:144915193-144921137 |
| 15943 | Olfr930 | NM_146923.2 | chr9:38930219-38931099 | | 16040 | Orc1 | NM_011015.2 | chr4:108579453-108614831 |
| 15944 | Olfr933 | NM_146441.1 | chr9:38975677-38976604 | | 16041 | Orc2 | NM_001025378.2 | chr1:58462770-58501426 |
| 15945 | Olfr934 | NM_146442.1 | chr9:38982109-38983042 | | 16042 | Orc3 | NM_001159563.1 | chr4:34566780-34614942 |
| 15946 | Olfr935 | NM_146746.1 | chr9:38994506-38995433 | | 16043 | Orc4 | NM_001177313.1 | chr2:48931746-48949267 |
| 15947 | Olfr936 | NM_207139.1 | chr9:39046613-39047549 | | 16044 | Orc5 | NM_011959.2 | chr5:22486488-22550331 |
| 15948 | Olfr937 | NM_146439.1 | chr9:39059728-39060664 | | 16045 | Orc6 | NM_001163791.1 | chr8:85299631-85308279 |
| 15949 | Olfr938 | NM_146438.1 | chr9:39077795-39078743 | | 16046 | Orm1 | NM_008768.2 | chr4:63344555-63348163 |
| 15950 | Olfr94 | NM_001011518.1 | chr17:37196805-37197266 | | 16047 | Orm2 | NM_011016.2 | chr4:63362448-63365877 |
| 15951 | Olfr943 | NM_146336.2 | chr9:39166309-39185124 | | 16048 | Orm3 | NM_013623.2 | chr4:63356161-63359511 |
| 15952 | Olfr944 | NM_146507.1 | chr9:39217358-39218294 | | 16049 | Ormdl1 | NM_145517.4 | chr1:53297094-53310245 |
| 15953 | Olfr945 | NM_146506.1 | chr9:39257719-39258679 | | 16050 | Ormdl2 | NM_024180.5 | chr10:128817456-128821631 |
| 15954 | Olfr947-ps1 | NR_033820.1 | chr9:39287923-39299481 | | 16051 | Ormdl3 | NM_025661.4 | chr11:98581293-98587245 |
| 15955 | Olfr948 | NM_001011756.1 | chr9:39318646-39319612 | | 16052 | Os9 | NM_001171026.1 | chr10:127094258-127121160 |
| 15956 | Olfr95 | NM_146513.1 | chr17:37201912-37211851 | | 16053 | Osbp | NM_001033174.1 | chr19:11965843-11994114 |
| 15957 | Olfr951 | NM_001011812.1 | chr9:39393792-39394737 | | 16054 | Osbp2 | NM_152818.2 | chr11:3703730-3863903 |
| 15958 | Olfr952 | NM_146503.1 | chr9:39426124-39427069 | | 16055 | Osbpl10 | NM_148958.2 | chr9:115067279-115232223 |
| 15959 | Olfr954 | NM_146331.1 | chr9:39461432-39462377 | | 16056 | Osbpl11 | NM_176840.3 | chr16:33185070-33243312 |
| 15960 | Olfr955 | NM_207141.1 | chr9:39469779-39470724 | | 16057 | Osbpl1a | NM_001252489.1 | chr18:12755311-12879979 |
| 15961 | Olfr957 | NM_146745.2 | chr9:39510782-39511718 | | 16058 | Osbpl2 | NM_144500.3 | chr2:180119365-180162680 |
| 15962 | Olfr958 | NM_146330.1 | chr9:39549930-39550869 | | 16059 | Osbpl3 | NM_001163645.1 | chr6:50293326-50456170 |
| 15963 | Olfr959 | NM_146508.1 | chr9:39572321-39573257 | | 16060 | Osbpl5 | NM_001199227.1 | chr7:143688761-143740360 |
| 15964 | Olfr96 | NM_146514.1 | chr17:37225126-37226068 | | 16061 | Osbpl6 | NM_001290733.1 | chr2:76406507-76600647 |
| 15965 | Olfr960 | NM_146279.1 | chr9:39623124-39624075 | | 16062 | Osbpl7 | NM_001081434.1 | chr11:97050819-97068904 |
| 15966 | Olfr961 | NM_146504.1 | chr9:39646727-39647672 | | 16063 | Osbpl8 | NM_001003717.1 | chr10:111164801-111297247 |
| 15967 | Olfr963 | NM_001011827.1 | chr9:39669058-39669994 | | 16064 | Osbpl9 | NM_001134791.2 | chr4:109061144-109118036 |
| 15968 | Olfr965 | NM_001011859.1 | chr9:39719228-39720167 | | 16065 | Oscar | NM_001290377.1 | chr7:3609814-3616157 |
| 15969 | Olfr967 | NM_001011826.1 | chr9:39750387-39751320 | | 16066 | Oscp1 | NM_172701.2 | chr4:126058564-126089334 |
| 15970 | Olfr968 | NM_146612.2 | chr9:39771771-39772798 | | 16067 | Oser1 | NM_025699.2 | chr2:163405821-163419470 |
| 15971 | Olfr969 | NM_146826.1 | chr9:39795376-39796312 | | 16068 | Osgep | NM_133676.2 | chr14:50915373-50924893 |
| 15972 | Olfr97 | NM_146512.1 | chr17:37232145-37232368 | | 16069 | Osgepl1 | NM_001285839.1 | chr1:53313623-53326842 |
| 15973 | Olfr970 | NM_146611.1 | chr9:39819640-39820576 | | 16070 | Osgin1 | NM_027950.1 | chr8:119432161-119446256 |
| 15974 | Olfr971 | NM_146614.1 | chr9:39839435-39840359 | | 16071 | Osgin2 | NM_145950.4 | chr4:15997120-16013877 |
| 15975 | Olfr972 | NM_146613.1 | chr9:39873276-39874221 | | 16072 | Osm | NM_001013365.2 | chr11:4236784-4241026 |
| 15976 | Olfr974 | NM_147107.1 | chr9:39942261-39943194 | | 16073 | Osmr | NM_011019.3 | chr15:6813576-6874313 |
| 15977 | Olfr975 | NM_146538.1 | chr9:39949836-39950769 | | 16074 | Osr1 | NM_011859.3 | chr12:9574441-9581506 |
| 15978 | Olfr978 | NM_146367.2 | chr9:39954256-39957069 | | 16075 | Osr2 | NM_054049.2 | chr15:35296111-35303305 |
| 15979 | Olfr978 | NM_147105.2 | chr9:39993811-39994747 | | 16076 | Ost4 | NM_001134692.2 | chr5:30906815-30907788 |
| 15980 | Olfr979 | NM_147108.2 | chr9:40000205-40001250 | | 16077 | Ostc | NM_025909.3 | chr3:130695916-130709444 |
| 15981 | Olfr98 | NM_146510.1 | chr17:37262732-37263662 | | 16078 | Ostf1 | NM_017375.3 | chr19:18580363-18631813 |
| 15982 | Olfr980 | NM_147106.2 | chr9:40005993-40007029 | | 16079 | Ostm1 | NM_172416.3 | chr10:42678915-42702462 |
| 15983 | Olfr981 | NM_146023.2 | chr9:40022394-40023327 | | 16080 | Ostn | NM_198112.2 | chr16:27307640-27351209 |
| 15984 | Olfr982 | NM_146854.1 | chr9:40074296-40075262 | | 16081 | Otc | NM_008769.4 | chrX:10252304-10321024 |
| 15985 | Olfr983 | NM_146872.2 | chr9:40092016-40093558 | | 16082 | Otoa | NM_139310.1 | chr7:121083437-121163089 |
| 15986 | Olfr984 | NM_146602.1 | chr9:40100543-40101488 | | 16083 | Otof | NM_001100395.1 | chr5:30367065-30461932 |
| 15987 | Olfr985 | NM_146855.2 | chr9:40126923-40128039 | | 16084 | Otog | NM_013624.2 | chr7:46240986-46311434 |
| 15988 | Olfr986 | NM_146615.2 | chr9:40187074-40188094 | | 16085 | Otogl | NM_001177567.1 | chr10:107762309-107912134 |
| 15989 | Olfr987 | NM_001011785.1 | chr2:85330966-85331896 | | 16086 | Otol1 | NM_001018031.2 | chr3:70007612-70028708 |
| 15990 | Olfr988 | NM_001011534.1 | chr2:85352994-85353924 | | 16087 | Otop1 | NM_172709.3 | chr5:38277403-38304217 |
| 15991 | Olfr99 | NM_146515.2 | chr17:37279500-37280418 | | 16088 | Otop2 | NM_172801.2 | chr11:115307162-115332303 |
| 15992 | Olfr992 | NM_146865.1 | chr2:85399601-85400531 | | 16089 | Otop3 | NM_027132.2 | chr11:115334733-115346926 |
| 15993 | Olfr993 | NM_146513932-85414877 | chr2:85413932-85414877 | | 16090 | Otor | NM_020595.2 | chr2:143078491-143081699 |
| 15994 | Olfr994 | NM_146433.1 | chr2:85429882-85430827 | | 16091 | Otos | NM_153114.2 | chr1:92644217-92648841 |
| 15995 | Olfr995 | NM_146434.1 | chr2:85438208-85439156 | | 16092 | Otp | NM_011021.3 | chr13:94875626-94883681 |
| 15996 | Olfr996 | NM_146437.2 | chr2:85450754-85580282 | | 16093 | Ott | NM_011022.1 | chrX:147992992-149487784 |
| 15997 | Olfr998 | NM_146436.1 | chr2:85590509-85591521 | | 16094 | OTTMUSG00000016609 | NM_001100416.2 | chr2:175323786-176636311 |
| 15998 | Olig1 | NM_016968.4 | chr16:91269768-91271939 | | 16095 | Otub1 | NM_134150.2 | chr19:7198205-7206284 |
| 15999 | Olig2 | NM_016967.2 | chr16:91225549-91228677 | | 16096 | Otub2 | NM_001177841.1 | chr2:103388681-103406350 |
| 16000 | Olig3 | NM_053008.2 | chr10:19356538-19358604 | | 16097 | Otud1 | NM_027715.3 | chr2:19658061-19660590 |
| 16001 | Olr1 | NM_138648.2 | chr6:129485246-129507165 | | 16098 | Otud3 | NM_028453.1 | chr4:138895378-138913947 |
| 16002 | Oma1 | NM_025909.3 | chr4:103313845-103366428 | | 16099 | Otud4 | NM_001081164.1 | chr8:79639675-79677755 |
| 16003 | Omd | NM_012050.2 | chr13:49582746-49592609 | | 16100 | Otud5 | NM_001290536.1 | chrX:7841830-7878626 |
| 16004 | Omg | NM_019409.2 | chr11:79500981-79504082 | | 16101 | Otud6a | NM_001163191.1 | chrX:100429012-100429885 |

| | | | | | | | | |
|---|---|---|---|---|---|---|---|---|
| 16490 | Pds5a | NM_001081321.1 | chr5:65615259-65697856 | 16587 | Pgbd1 | NM_001012311.2 | chr13:21421274-21441053 |
| 16491 | Pds5b | NM_175310.6 | chr5:150673826-150810669 | 16588 | Pgbd5 | NM_171824.2 | chr8:124369048-124433936 |
| 16492 | Pdss1 | NM_019501.3 | chr2:22895521-22940259 | 16589 | Pgc | NM_025973.3 | chr17:47726841-47734478 |
| 16493 | Pdss2 | NM_001168289.1 | chr10:43221485-43464882 | 16590 | Pgd | NM_001081274.1 | chr4:149149984-149166707 |
| 16494 | Pdx1 | NM_008814.3 | chr5:147270130-147275149 | 16591 | Pgf | NM_001271705.1 | chr12:85166638-85175982 |
| 16495 | Pdxdc1 | NM_001039533.2 | chr16:13833572-13903145 | 16592 | Pggt1b | NM_172627.3 | chr18:46239948-46280850 |
| 16496 | Pdxk | NM_172134.2 | chr10:78436746-78464948 | 16593 | Pgk1 | NM_008828.3 | chrX:106187099-106203699 |
| 16497 | Pdxk-ps | NR_027316.1 | chr17:32076082-32091423 | 16594 | Pgk2 | NM_031190.2 | chr17:40207017-40208609 |
| 16498 | Pdxp | NM_020271.3 | chr15:78913918-78919517 | 16595 | Pgls | NM_025396.3 | chr7:8:71592183-71596267 |
| 16499 | Pdyn | NM_001286502.1 | chr2:129686548-129698658 | 16596 | Pglyrp1 | NM_009402.2 | chr7:18884689-18890438 |
| 16500 | Pdzd11 | NM_028303.3 | chrX:100622905-100625907 | 16597 | Pglyrp2 | NM_001271476.1 | chr17:32412460-32424167 |
| 16501 | Pdzd2 | NM_001081064.1 | chr15:12357053-12592556 | 16598 | Pglyrp3 | NM_207247.4 | chr3:92014582-92031584 |
| 16502 | Pdzd3 | NM_133226.2 | chr9:44247511-44251464 | 16599 | Pglyrp4 | NM_001165968.1 | chr3:90726905-90741517 |
| 16503 | Pdzd4 | NM_001029868.2 | chrX:73793356-73824969 | 16600 | Pgm1 | NM_025700.2 | chr5:64092949-64128158 |
| 16504 | Pdzd7 | NM_001195065.1 | chr19:45026906-45045772 | 16601 | Pgm2 | NM_028132.3 | chr4:99929450-99987294 |
| 16505 | Pdzd8 | NM_001033222.1 | chr19:59296083-59345780 | 16602 | Pgm2l1 | NM_027629.3 | chr7:100227606-100278872 |
| 16506 | Pdzd9 | NM_001040136.2 | chr7:120659295-120670343 | 16603 | Pgm3 | NM_001163746.1 | chr9:86552475-86571842 |
| 16507 | Pdzk1 | NM_001146001.1 | chr3:96832673-96870926 | 16604 | Pgm5 | NM_175013.2 | chr19:24678260-24861842 |
| 16508 | Pdzk1ip1 | NM_001164557.1 | chr4:115085707-115093894 | 16605 | Pgu | NM_025954.3 | chr17:24470472-24471596 |
| 16509 | Pdzrn3 | NM_018884.2 | chr6:101149606-101377897 | 16606 | Pgpep1 | NM_023217.4 | chr8:70646435-70659738 |
| 16510 | Pdzrn4 | NM_001164593.1 | chr15:92396809-92771819 | 16607 | Pgpep1l | NM_030101.1 | chr7:68236607-68264233 |
| 16511 | Pea15a | NM_011063.2 | chr1:172196728-172206781 | 16608 | Pgr | NM_008829.2 | chr9:8899832-8968611 |
| 16512 | Pea15b | NR_027806.1 | chr5:77510039-77511003 | 16609 | Pgr1s1 | NM_001033361.3 | chrX:97072595-97082104 |
| 16513 | Peak1 | NM_172924.3 | chr9:56201128-56418050 | 16610 | Pgrmc1 | NM_016783.4 | chrX:36598192-36606079 |
| 16514 | Pear1 | NM_001032413.1 | chr3:87749096-87768953 | 16611 | Pgrmc2 | NM_027558.1 | chr3:41066325-41083046 |
| 16515 | Pebp1 | NM_018858.2 | chr5:117282650-117287564 | 16612 | Pgs1 | NM_133757.2 | chr11:117986856-118024011 |
| 16516 | Pebp4 | NM_028526.4 | chr14:69840406-69851960 | 16613 | Phactr1 | NM_001005740.1 | chr13:42709580-43138512 |
| 16517 | Pecam1 | NM_001032378.2 | chr11:106654212-106715281 | 16614 | Phactr2 | NM_001033857.4 | chr10:13207716-13324160 |
| 16518 | Pecr | NM_023523.5 | chr1:72259172-72284314 | 16615 | Phactr3 | NM_001007154.3 | chr2:178193083-178338492 |
| 16519 | Pef1 | NM_026441.4 | chr4:130107555-130128134 | 16616 | Phactr4 | NM_001161797.1 | chr4:132355924-132422446 |
| 16520 | Peg10 | NM_130877.2 | chr6:4747305-4760615 | 16617 | Phax | NM_001162989.1 | chr18:56562568-56587712 |
| 16521 | Peg12 | NM_013788.2 | chr7:62461870-62464510 | 16618 | Phb | NM_008831.4 | chr11:95666956-95680773 |
| 16522 | Peg13 | NR_002864.1 | chr15:72805599-72810324 | 16619 | Phb2 | NM_007531.2 | chr6:124712288-124716945 |
| 16523 | Peg3 | NM_008817.2 | chr7:6705959-6730419 | 16620 | Phc1 | NM_001042623.2 | chr6:122317730-122339657 |
| 16524 | Peg3os | NR_028846.1 | chr7:6706759-6707624 | 16621 | Phc2 | NM_001195083.1 | chr4:128727570-128752881 |
| 16525 | Peli1 | NM_023324.2 | chr11:21091323-21150327 | 16622 | Phc3 | NM_001165954.1 | chr3:30899294-30969415 |
| 16526 | Peli2 | NM_033602.2 | chr14:48120868-48260883 | 16623 | Phex | NM_011077.2 | chrX:157162074-157415286 |
| 16527 | Peli3 | NM_172835.3 | chr19:4931854-4943092 | 16624 | Phf1 | NM_009343.3 | chr17:26933126-26937908 |
| 16528 | Pelo | NM_134058.3 | chr13:115088354-115090158 | 16625 | Phf10 | NM_024250.4 | chr17:14944994-14961280 |
| 16529 | Pelp1 | NM_029231.4 | chr11:70392880-70410031 | 16626 | Phf11a | NM_172603.3 | chr14:59276912-59297522 |
| 16530 | Pemt | NM_001290011.1 | chr11:59970613-60046489 | 16627 | Phf11b | NM_001164227.1 | chr14:59320963-59341330 |
| 16531 | Penk | NM_001002927.2 | chr4:4133535-4138445 | 16628 | Phf11c | NM_001164289.1 | chr14:59380832-59393512 |
| 16532 | Peo1 | NM_153796.3 | chr19:45006557-45012762 | 16629 | Phf11d | NM_199015.4 | chr14:59347406-59365490 |
| 16533 | Pepd | NM_008820.2 | chr7:34912406-35044708 | 16630 | Phf12 | NM_174852.3 | chr11:77982815-78030535 |
| 16534 | Per1 | NM_001159367.1 | chr11:69100157-69109957 | 16631 | Phf13 | NM_172705.2 | chr4:151989630-151996179 |
| 16535 | Per2 | NM_011066.3 | chr1:91415981-91459328 | 16632 | Phf14 | NM_001168282.1 | chr6:11925880-12081198 |
| 16536 | Per3 | NM_001289877.1 | chr4:151003654-151044665 | 16633 | Phf19 | NM_028716.4 | chr2:34893754-34913976 |
| 16537 | Peri1 | NR_110488.1 | chr3:34772074-34782346 | 16634 | Phf2 | NM_011078.3 | chr13:48801749-48870885 |
| 16538 | Perm1 | NM_172417.3 | chr4:156215926-156221307 | 16635 | Phf20 | NM_172674.2 | chr2:156196646-156309953 |
| 16539 | Perp | NM_022032.4 | chr10:18845070-18857072 | 16636 | Phf20l1 | NM_001081409.1 | chr15:66577571-66645255 |
| 16540 | Pes1 | NM_022869.3 | chr11:3963974-3980004 | 16637 | Phf21a | NM_001109690.1 | chr2:92221561-92364666 |
| 16541 | Pet100 | NM_001195244.1 | chr8:3621550-3624235 | 16638 | Phf21b | NM_001081166.2 | chr15:84785375-84856129 |
| 16542 | Pet112 | NM_144896.4 | chr3:85574128-85654470 | 16639 | Phf23 | NM_001291325.1 | chr11:69995765-70000011 |
| 16543 | Pet117 | NM_001164813.1 | chr2:144368982-144373337 | 16640 | Phf3 | NM_001081080.1 | chr1:30802941-30863256 |
| 16544 | Pet2 | NM_008821.1 | chrX:89403847-89409689 | 16641 | Phf5a | NM_026737.3 | chr15:81864515-81871892 |
| 16545 | Pex1 | NM_027777.2 | chr6:3596065-3637230 | 16642 | Phf6 | NM_001290546.1 | chrX:52912213-52956961 |
| 16546 | Pex10 | NM_001042407.1 | chr4:155067029-155072406 | 16643 | Phf7 | NM_027949.1 | chr14:31237695-31251218 |
| 16547 | Pex11a | NM_011068.1 | chr7:79737263-79748025 | 16644 | Phf8 | NM_001113354.1 | chrX:151520671-151633857 |
| 16548 | Pex11b | NM_001162387.1 | chr3:96635429-96645381 | 16645 | Phgdh | NM_016966.3 | chr3:98313170-98338969 |
| 16549 | Pex11g | NM_026951.2 | chr8:3458316-3467648 | 16646 | Phgr1 | NM_001145644.1 | chr2:118772768-118778164 |
| 16550 | Pex12 | NM_145305.3 | chr11:83294644-83298977 | 16647 | Phip | NM_001081216.1 | chr9:82866158-82975489 |
| 16551 | Pex13 | NM_023651.4 | chr11:23646478-23665935 | 16648 | Phka1 | NM_008832.2 | chrX:102513974-102644246 |
| 16552 | Pex14 | NM_019781.2 | chr4:148960534-149099812 | 16649 | Phka2 | NM_001177878.1 | chrX:160502433-160598878 |
| 16553 | Pex16 | NM_145122.2 | chr2:92375233-92381220 | 16650 | Phkb | NM_199446.1 | chr8:85841001-86080642 |
| 16554 | Pex19 | NM_001159525.1 | chr1:172126754-172136497 | 16651 | Phkg1 | NM_011079.2 | chr5:129863434-129879083 |
| 16555 | Pex2 | NM_001163031.1 | chr3:5560187-5576248 | 16652 | Phkg2 | NM_026888.3 | chr7:127573347-127583307 |
| 16556 | Pex26 | NM_028730.6 | chr6:121183666-121196192 | 16653 | Phlda1 | NM_009344.3 | chr10:111506285-111508649 |
| 16557 | Pex3 | NM_001164195.1 | chr10:13523841-13553142 | 16654 | Phlda2 | NM_009434.2 | chr7:143501547-143502524 |
| 16558 | Pex5 | NM_001277.2 | chr6:124396815-124414863 | 16655 | Phlda3 | NM_013750.2 | chr1:135768084-135769134 |
| 16559 | Pex5l | NM_001163516.3 | chr3:32947925-33143191 | 16656 | Phldb1 | NM_153537.4 | chr9:44686307-44735198 |
| 16560 | Pex6 | NM_145488.4 | chr17:46711462-46725514 | 16657 | Phldb2 | NM_001252442.1 | chr16:45746230-45844378 |
| 16561 | Pex7 | NM_001161825.1 | chr10:19860089-19907674 | 16658 | Phldb3 | NM_001102613.1 | chr7:24611327-24629297 |
| 16562 | Pf4 | NM_019932.4 | chr5:90772434-90773383 | 16659 | Phlpp1 | NM_133821.3 | chr1:106171868-106394245 |
| 16563 | Pfas | NM_001159519.1 | chr11:68985700-69008460 | 16660 | Phlpp2 | NM_001122594.2 | chr8:109869602-109944671 |
| 16564 | Pfdn1 | NM_026027.3 | chr18:36403678-36454495 | 16661 | Phospho1 | NM_153104.3 | chr11:95824499-95832140 |
| 16565 | Pfdn2 | NM_011070.3 | chr1:171345698-171358170 | 16662 | Phospho2 | NM_028521.2 | chr2:69789736-69797168 |
| 16566 | Pfdn4 | NM_001033692 | chr2:170496427-170519070 | 16663 | Phox2a | NM_008887.2 | chr7:101818312-101822726 |
| 16567 | Pfdn5 | NM_027044.3 | chr15:102326115-102331489 | 16664 | Phox2b | NM_008888.3 | chr5:67094396-67099126 |
| 16568 | Pfdn6 | NM_008824.3 | chrX:150589920-150643878 | 16665 | Phpt1 | NM_029293.2 | chr2:25573430-25574871 |
| 16569 | Pfkfb1 | NM_001162415.1 | chr1:130689042-130729253 | 16666 | Phrf1 | NM_001081118.1 | chr7:141228787-141262751 |
| 16570 | Pfkfb3 | NM_001177752.1 | chr2:11471430-11502090 | 16667 | Phtf1 | NM_001163467.1 | chr3:103968109-104007491 |
| 16571 | Pfkfb4 | NM_173019.5 | chr9:108991060-109032225 | 16668 | Phtf1os | NR_030676.1 | chr3:103964535-103968316 |
| 16572 | Pfkl | NM_008826.4 | chr10:77988948-78009796 | 16669 | Phtf2 | NM_172992.3 | chr5:20758663-20882124 |
| 16573 | Pfkm | NM_001163487.1 | chr15:98108470-98132447 | 16670 | Phxr4 | NR_028271.1 | chr9:13431360-13432740 |
| 16574 | Pfkp | NM_001163492.1 | chr13:6579873-6648771 | 16671 | Phyh | NM_010726.2 | chr2:4918995-4938743 |
| 16575 | Pfn1 | NM_011072.4 | chr11:70651846-70654650 | 16672 | Phyhd1 | NM_001252668.2 | chr2:30266202-30282149 |
| 16576 | Pfn2 | NM_019410.2 | chr3:57841894-57847757 | 16673 | Phyhip | NM_145981.3 | chr14:70457516-70468824 |
| 16577 | Pfn3 | NM_029303.2 | chr13:55414687-55415232 | 16674 | Phyhipl | NM_001162846.1 | chr10:70557685-70592812 |
| 16578 | Pfn4 | NM_028376.3 | chr12:4769294-4778266 | 16675 | Phykpl | NM_028398.2 | chr11:51584756-51603289 |
| 16579 | Pfpl | NM_019540.2 | chr12:47042494-12432110 | 16676 | Pi15 | NM_053191.2 | chr1:17601900-17630939 |
| 16580 | Pga5 | NM_021453.4 | chr19:10668956-10678071 | 16677 | Pi16 | NM_023734.3 | chr17:29318881-29328902 |
| 16581 | Pgam1 | NM_023418.2 | chr19:41911870-41918665 | 16678 | Pi4k2a | NM_145501.2 | chr19:42090434-42122218 |
| 16582 | Pgam2 | NM_018870.3 | chr11:5801636-5803796 | 16679 | Pi4k2b | NM_025951.3 | chr5:52741573-52769344 |
| 16583 | Pgam5 | NM_001163538.1 | chr5:110259134-110269899 | 16680 | Pi4ka | NM_001001983.2 | chr16:17280350-17406314 |
| 16584 | Pgap1 | NM_001163314.2 | chr1:54472999-54557684 | 16681 | Pi4kb | NM_175236.3 | chr3:94974730-95006937 |
| 16585 | Pgap2 | NM_001291358.1 | chr7:102120334-102238564 | 16682 | Pianp | NM_001145926.1 | chr6:124998609-125003097 |
| 16586 | Pgap3 | NM_001033537.2 | chr11:98388671-98400490 | 16683 | Pias1 | NM_019663.3 | chr9:62880076-62980879 |

Fig.21 - 87

| | | | | | | | | |
|---|---|---|---|---|---|---|---|---|
| 16684 | Pias2 | NM_001164167.1 | chr18:77065207-77155708 | | 16781 | Pitrm1 | NM_145131.1 | chr13:6548156-6580149 |
| 16685 | Pias3 | NM_001165949.1 | chr3:96697075-96706070 | | 16782 | Pitx1 | NM_011097.2 | chr13:55825053-55831425 |
| 16686 | Pias4 | NM_021501.4 | chr10:81153965-81167720 | | 16783 | Pitx2 | NM_001042502.2 | chr3:129213931-129239594 |
| 16687 | Pibf1 | NM_029320.3 | chr14:99099423-99254494 | | 16784 | Pitx3 | NM_008852.4 | chr19:46135685-46148325 |
| 16688 | Picalm | NM_001252520.1 | chr7:90130231-90209447 | | 16785 | Piwil1 | NM_021311.3 | chr5:128736245-128755474 |
| 16689 | Pick1 | NM_001045558.1 | chr15:79229381-79249466 | | 16786 | Piwil2 | NM_021308.1 | chr14:70372479-70429094 |
| 16690 | Pid1 | NM_001003948.2 | chr1:84036292-84284645 | | 16787 | Piwil4 | NM_177905.3 | chr9:14702357-14740733 |
| 16691 | Pidd1 | NM_022654.1 | chr7:141438514-141443355 | | 16788 | Pja1 | NM_001083110.2 | chrX:99465733-99470735 |
| 16692 | Piezo1 | NM_001037298.1 | chr8:122481697-122551329 | | 16789 | Pja2 | NM_001025309.1 | chr17:64281005-64331883 |
| 16693 | Piezo2 | NM_001039485.4 | chr18:63010212-63387183 | | 16790 | Pkd1 | NM_013630.2 | chr17:24549949-24596514 |
| 16694 | Pif1 | NM_172453.3 | chr9:65587204-65595962 | | 16791 | Pkd1l2 | NM_029686.4 | chr8:116995678-117082449 |
| 16695 | Pifo | NM_001200028.1 | chr3:105996956-106014646 | | 16792 | Pkd1l3 | NM_001039700.2 | chr8:109614816-109672592 |
| 16696 | Piga | NM_011081.2 | chrX:164419786-164433915 | | 16793 | Pkd2 | NM_008861.3 | chr5:104459456-104505819 |
| 16697 | Pigb | NM_018889.3 | chr9:73015695-73039699 | | 16794 | Pkd2l1 | NM_181422.3 | chr19:44147636-44192442 |
| 16698 | Pigc | NM_001039045.1 | chr1:161969187-161973435 | | 16795 | Pkd2l2 | NM_001163004.1 | chr18:34409422-34441794 |
| 16699 | Pigf | NM_008838.1 | chr17:86997258-87025401 | | 16796 | Pkdcc | NM_134117.2 | chr17:83215282-83225069 |
| 16700 | Pigg | NM_001081234.2 | chr5:108312924-108349355 | | 16797 | Pkdrej | NM_011105.2 | chr15:85814675-85821733 |
| 16701 | Pigh | NM_029988.2 | chr12:79080669-79089670 | | 16798 | Pkhd1 | NM_153179.3 | chr1:20057778-20618057 |
| 16702 | Pigk | NM_025662.5 | chr3:152714099-152789013 | | 16799 | Pkhd1l1 | NM_138674.2 | chr15:44457552-44597135 |
| 16703 | Pigl | NM_001039536.2 | chr11:62458459-62513900 | | 16800 | Pkia | NM_008862.3 | chr3:7366603-7445365 |
| 16704 | Pigm | NM_026234.4 | chr1:172376530-172384099 | | 16801 | Pkib | NM_001039050.1 | chr10:57650980-57741112 |
| 16705 | Pign | NM_013784.3 | chr1:105518421-105663676 | | 16802 | Pkig | NM_001039390.2 | chr2:163658385-163726158 |
| 16706 | Pigo | NM_020035.3 | chr4:43017625-43025774 | | 16803 | Pklr | NM_001099779.1 | chr3:89136622-89146594 |
| 16707 | Pigp | NM_001159616.1 | chr16:94364451-94370710 | | 16804 | Pkm | NM_001253883.1 | chr9:59656367-59679375 |
| 16708 | Pigq | NM_001291025.1 | chr17:25926419-25941989 | | 16805 | Pknyt1 | NM_023058.3 | chr17:23726335-23736729 |
| 16709 | Pigr | NM_011082.3 | chr1:130826683-130852249 | | 16806 | Pkn1 | NM_001199593.1 | chr8:83669761-83694061 |
| 16710 | Pigs | NM_201406.1 | chr11:78328421-78342776 | | 16807 | Pkn2 | NM_178654.4 | chr3:142790901-142882004 |
| 16711 | Pigt | NM_133779.2 | chr2:164497524-164508301 | | 16808 | Pkn3 | NM_153805.1 | chr2:30078765-30091019 |
| 16712 | Pigu | NM_001004721.1 | chr2:155278251-155357424 | | 16809 | Pknox1 | NM_016670.3 | chr17:31564772-31607693 |
| 16713 | Pigv | NM_001145955.1 | chr4:133661424-133672647 | | 16810 | Pknox2 | NM_001029838.2 | chr9:36890978-37147322 |
| 16714 | Pigw | NM_001077616.1 | chr11:84876312-84880285 | | 16811 | Pkp1 | NM_019645.3 | chr1:135871393-135919207 |
| 16715 | Pigx | NM_001111025.1 | chr16:32084415-32099727 | | 16812 | Pkp2 | NM_026163.2 | chr16:16213344-16272712 |
| 16716 | Pigyl | NM_001082532.1 | chr9:22156845-22158354 | | 16813 | Pkp3 | NM_001162924.1 | chr7:141078228-141090510 |
| 16717 | Pigz | NM_172822.3 | chr16:31933850-31946046 | | 16814 | Pkp4 | NM_026361.2 | chr2:59160849-59355205 |
| 16718 | Pih1d1 | NM_001278207.1 | chr7:45154302-45160064 | | 16815 | Pla1a | NM_134102.4 | chr16:38396116-38433145 |
| 16719 | Pih1d2 | NM_028300.2 | chr9:50617320-50625000 | | 16816 | Pla2g10 | NM_001291009.2 | chr16:13715056-13730484 |
| 16720 | Pih1d3 | NM_029062.2 | chr12:122838-31224287 | | 16817 | Pla2g10os | NR_040674.1 | chr16:13729835-13730471 |
| 16721 | Pik3ap1 | NM_031376.3 | chr19:41274217-41385070 | | 16818 | Pla2g12a | NM_001286948.1 | chr3:129878605-129895825 |
| 16722 | Pik3c2a | NM_011035.2 | chr7:116337275-116443458 | | 16819 | Pla2g12b | NM_023530.2 | chr10:59403684-59421976 |
| 16723 | Pik3c2b | NM_001099276.2 | chr1:133046011-133108688 | | 16820 | Pla2g15 | NM_133792.2 | chr8:106150398-106164715 |
| 16724 | Pik3c2g | NM_010084.2 | chr6:139841444-139969283 | | 16821 | Pla2g16 | NM_139269.2 | chr19:7557458-7588545 |
| 16725 | Pik3c3 | NM_181414.3 | chr18:30272895-30348120 | | 16822 | Pla2g1b | NM_011107.1 | chr5:115466265-115474717 |
| 16726 | Pik3ca | NM_008839.2 | chr3:32436150-32468486 | | 16823 | Pla2g2a | NM_001082531.1 | chr4:138831875-138835189 |
| 16727 | Pik3cb | NM_029094.3 | chr9:99038401-99140211 | | 16824 | Pla2g2c | NM_008868.3 | chr4:138725324-138744575 |
| 16728 | Pik3cd | NM_001029837.2 | chr4:149649167-149701629 | | 16825 | Pla2g2d | NM_011109.2 | chr4:138775734-138782143 |
| 16729 | Pik3cg | NM_001146200.1 | chr12:32173396-32208649 | | 16826 | Pla2g2e | NM_012044.2 | chr4:138877941-138882814 |
| 16730 | Pik3ip1 | NM_178144.4 | chr11:3330730-3342971 | | 16827 | Pla2g2f | NM_012045.4 | chr4:138750532-138757598 |
| 16731 | Pik3r1 | NM_001024955.2 | chr13:101680760-101692630 | | 16828 | Pla2g3 | NM_172791.2 | chr11:3488226-3494166 |
| 16732 | Pik3r2 | NM_008841.2 | chr8:70768180-70776712 | | 16829 | Pla2g4a | NM_008869.4 | chr1:149829618-149961290 |
| 16733 | Pik3r3 | NM_181585.5 | chr4:116218319-116303056 | | 16830 | Pla2g4b | NM_145378.4 | chr2:120033432-120043032 |
| 16734 | Pik3r4 | NM_001081309.1 | chr9:105642994-105687655 | | 16831 | Pla2g4c | NM_001004762.3 | chr7:13329321-13360668 |
| 16735 | Pik3r5 | NM_177320.2 | chr11:68432124-68497846 | | 16832 | Pla2g4d | NM_001024137.1 | chr2:120265868-120289069 |
| 16736 | Pik3r6 | NM_001004435.3 | chr11:68503018-68552695 | | 16833 | Pla2g4e | NM_177845.4 | chr2:120166411-120245535 |
| 16737 | Pikfyve | NM_011086.2 | chr1:65186684-65278696 | | 16834 | Pla2g4f | NM_001024145.2 | chr2:120299956-120314165 |
| 16738 | Pilra | NM_153510.3 | chr5:137821951-137836278 | | 16835 | Pla2g5 | NM_001122954.1 | chr4:138799246-138863489 |
| 16739 | Pilrb1 | NM_133209.2 | chr5:137852146-137858049 | | 16836 | Pla2g6 | NM_001199023.1 | chr15:79286227-79328371 |
| 16740 | Pilrb2 | NM_001024932.2 | chr5:137865828-137871758 | | 16837 | Pla2g7 | NM_013737.5 | chr17:43568450-43612201 |
| 16741 | Pim1 | NM_008842.3 | chr17:29491044-29495459 | | 16838 | Pla2r1 | NM_008867.2 | chr2:60417542-60553308 |
| 16742 | Pim2 | NM_138606.2 | chrX:7878305-7883432 | | 16839 | Plaa | NM_172695.2 | chr4:94565138-94603247 |
| 16743 | Pim3 | NM_145478.2 | chr15:88862193-88865726 | | 16840 | Plac1 | NM_019538.4 | chrX:53070001-53114405 |
| 16744 | Pin1 | NM_023371.3 | chr9:20652129-20666584 | | 16841 | Plac8 | NM_139198.2 | chr5:100553732-100572205 |
| 16745 | Pin1rt1 | NM_001083768.2 | chr2:104713925-104716290 | | 16842 | Plac8l1 | NM_027072.1 | chr18:42178674-42196709 |
| 16746 | Pin4 | NM_027184.1 | chrX:102119464-102127673 | | 16843 | Plac9a | NM_207229.1 | chr14:25888402-26182273 |
| 16747 | Pinc | NR_003202.1 | chr1:73391384-73407569 | | 16844 | Plac9b | NM_001270503.1 | chr14:25887933-26182351 |
| 16748 | Pink1 | NM_026880.2 | chr4:138313409-138326236 | | 16845 | Plag1 | NM_019969.3 | chr4:3901157-3938405 |
| 16749 | Pinlyp | NM_001037343.2 | chr7:24541615-24546005 | | 16846 | Plagl1 | NM_009538.2 | chr10:13090787-13131695 |
| 16750 | Pinx1 | NM_028228.3 | chr14:63860313-63919659 | | 16847 | Plagl2 | NM_018807.5 | chr2:153227768-153241358 |
| 16751 | Pip | NM_008843.3 | chr6:41847648-41852062 | | 16848 | Plat | NM_008872.3 | chr8:22757721-22782848 |
| 16752 | Pip4k2a | NM_008845.4 | chr2:18842255-18998121 | | 16849 | Plau | NM_008873.3 | chr14:20836661-20843388 |
| 16753 | Pip4k2b | NM_054051.1 | chr11:97715156-97744704 | | 16850 | Plaur | NM_011113.3 | chr7:24462499-24475873 |
| 16754 | Pip4k2c | NM_054097.3 | chr10:127197066-127211622 | | 16851 | Plb1 | NM_001081407.1 | chr5:32239083-32384356 |
| 16755 | Pip5k1a | NM_008847.3 | chr3:95058529-95106930 | | 16852 | Plbd1 | NM_025806.2 | chr6:136612070-136661893 |
| 16756 | Pip5k1b | NM_008846.2 | chr19:24294795-24555827 | | 16853 | Plbd2 | NM_023625.4 | chr5:120483892-120503623 |
| 16757 | Pip5k1c | NM_001146687.2 | chr10:81292992-81319974 | | 16854 | Plch1 | NM_001145830.1 | chr1:132786163-135475258 |
| 16758 | Pip5kl1 | NM_198191.2 | chr2:32575818-32583779 | | 16855 | Plcb2 | NM_001290790.1 | chr2:118707516-118728438 |
| 16759 | Pipox | NM_008952.2 | chr11:77880614-77892872 | | 16856 | Plcb3 | NM_001290349.1 | chr19:6953712-6969814 |
| 16760 | Pir | NM_027183.2 | chrX:164269430-164373013 | | 16857 | Plcb4 | NM_013829.2 | chr2:135741829-136013068 |
| 16761 | Pira1 | NM_011087.1 | chr7:3836814-3915484 | | 16858 | Plcd1 | NM_019676.3 | chr9:119071527-119093502 |
| 16762 | Pira11 | NM_011088.2 | chr7:3836530-3898093 | | 16859 | Plcd3 | NM_152813.3 | chr11:103070295-103101658 |
| 16763 | Pira2 | NM_011089.2 | chr7:3836809-3845051 | | 16860 | Plcd4 | NM_001081456.1 | chr1:74542688-74566977 |
| 16764 | Pira4 | NM_011091.1 | chr7:3838125-3898092 | | 16861 | Plce1 | NM_019588.2 | chr19:38524196-38785100 |
| 16765 | Pira6 | NM_001289428.1 | chr7:3731632-3898150 | | 16862 | Plcg1 | NM_021280.3 | chr2:160731309-160775760 |
| 16766 | Pira7 | NM_011094.1 | chr7:3838120-3898120 | | 16863 | Plcg2 | NM_172285.1 | chr8:117498290-117635142 |
| 16767 | Pirb | NM_011095.2 | chr7:3712504-3720382 | | 16864 | Plch1 | NM_001177732.1 | chr3:63696233-63850991 |
| 16768 | Pirt | NM_178656.3 | chr11:66911990-66928700 | | 16865 | Plch2 | NM_001113360.2 | chr4:154983114-155010984 |
| 16769 | Pisd | NM_177298.3 | chr5:32736319-32785626 | | 16866 | Plcl1 | NM_001114663.1 | chr1:55405945-55754285 |
| 16770 | Pisd-ps1 | NR_003517.1 | chr3:3124020-3131944 | | 16867 | Plcl2 | NM_013880.3 | chr17:50509546-50688454 |
| 16771 | Pisd-ps2 | NR_003519.3 | chr17:3064317-3084183 | | 16868 | Plcxd1 | NM_001281812.1 | chr5:110100558-110105952 |
| 16772 | Pisd-ps3 | NR_003518.2 | chrUn_JH584304:52673-59689 | | 16869 | Plcxd2 | NM_001134480.1 | chr16:45959260-46010413 |
| 16773 | Pithd1 | NM_025411.4 | chr4:135975601-135987244 | | 16870 | Plcxd3 | NM_177355.3 | chr5:4375490-4575579 |
| 16774 | Pitpna | NM_008850.2 | chr11:75586078-75628804 | | 16871 | Plcz1 | NM_054066.4 | chr6:139989723-140044117 |
| 16775 | Pitpnb | NM_019640.5 | chr5:111330696-111388359 | | 16872 | Pld1 | NM_001164056.1 | chr3:27938679-28133362 |
| 16776 | Pitpnc1 | NM_145823.2 | chr11:107207891-107470720 | | 16873 | Pld2 | NM_008876.3 | chr11:70540271-70558110 |
| 16777 | Pitpnm1 | NM_008851.4 | chr19:4100621-4133965 | | 16874 | Pld3 | NM_011116.1 | chr7:27532617-27553112 |
| 16778 | Pitpnm2 | NM_001289472.1 | chr5:124184687-124187182 | | 16875 | Pld4 | NM_178911.4 | chr12:112760654-112768986 |
| 16779 | Pitpnm2os1 | NR_045369.1 | chr5:124229724-124237137 | | 16876 | Pld5 | NM_001195816.1 | chr1:175962305-176213942 |
| 16780 | Pitpnm3 | NM_001024927.2 | chr11:72047527-72135889 | | 16877 | Pld6 | NM_001290283.1 | chr11:59783892-59787657 |

Fig.21 - 88

| | | | | | | |
|---|---|---|---|---|---|---|
| 16878 | Pld1 | NR_033616.1 | chr10:60928225-60938132 | 16975 | Pnck | NM_011993351.1 | chrX:73655991-73659854 |
| 16879 | Plec | NM_001163540.1 | chr15:76170973-76206321 | 16976 | Pnisr | NM_025669.1 | chr4:21847582-21876475 |
| 16880 | Plek | NM_019549.2 | chr11:16971205-17008718 | 16977 | Pnkd | NM_001030509.1 | chr1:74285033-74353692 |
| 16881 | Plek2 | NM_013738.3 | chr12:78888696-78906938 | 16978 | Pnkp | NM_001290764.1 | chr7:44857145-44862929 |
| 16882 | Plekha1 | NM_133942.2 | chr7:130865909-130913302 | 16979 | Pnldc1 | NM_001034866.1 | chr17:12888901-12910000 |
| 16883 | Plekha2 | NM_031257.3 | chr8:25039143-25101811 | 16980 | Pnlip | NM_026925.3 | chr19:58670364-58681788 |
| 16884 | Plekha3 | NM_031256.3 | chr2:76675314-76697335 | 16981 | Pnliprp1 | NM_018874.2 | chr19:58728886-58744169 |
| 16885 | Plekha4 | NM_148927.2 | chr7:45526329-45554229 | 16982 | Pnliprp2 | NM_011128.2 | chr19:58759722-58777534 |
| 16886 | Plekha5 | NM_144920.3 | chr6:140424098-140594906 | 16983 | Pnma1 | NM_027438.3 | chr12:84146130-84148489 |
| 16887 | Plekha6 | NM_001160268.1 | chr1:133246096-133303435 | 16984 | Pnma2 | NM_175498.4 | chr14:66911207-66920081 |
| 16888 | Plekha7 | NM_172743.3 | chr7:116123484-116189841 | 16985 | Pnma3 | NM_153189.2 | chrX:73064786-73068191 |
| 16889 | Plekha8 | NM_001001335.2 | chr6:54603146-54645822 | 16986 | Pnma5 | NM_001100461.3 | chrX:73033980-73037103 |
| 16890 | Plekhb1 | NM_001163586.1 | chr7:100643895-100662394 | 16987 | Pnmal1 | NM_001007569.1 | chr7:16959794-16962320 |
| 16891 | Plekhb2 | NM_145516.2 | chr1:34849958-34879585 | 16988 | Pnmal2 | NM_001099636.2 | chr7:16944681-16948828 |
| 16892 | Plekhd1 | NM_001177503.1 | chr12:80692600-80724216 | 16989 | Pnmt | NM_008890.1 | chr11:98386631-98388097 |
| 16893 | Plekhd1os | NR_037995.1 | chr12:80686374-80692466 | 16990 | Pnn | NM_008891.2 | chr12:59066918-59074017 |
| 16894 | Plekhf1 | NM_024413.2 | chr7:38220653-38227994 | 16991 | Pno1 | NM_025443.2 | chr11:17203199-17211589 |
| 16895 | Plekhf2 | NM_175175.4 | chr4:10988661-11007619 | 16992 | Pnoc | NM_001205075.1 | chr14:65400672-65425472 |
| 16896 | Plekhg1 | NM_001033253.3 | chr10:3872686-3967302 | 16993 | Pnp | NM_013632.4 | chr14:50944302-50954412 |
| 16897 | Plekhg2 | NM_001083912.1 | chr7:28359603-28372662 | 16994 | Pnp2 | NM_001123371.2 | chr14:50956146-50964749 |
| 16898 | Plekhg3 | NM_153804.4 | chr12:76535559-76579039 | 16995 | Pnpla1 | NM_001034885.3 | chr17:28858410-28890308 |
| 16899 | Plekhg4 | NM_001081333.1 | chr8:105375380-105382862 | 16996 | Pnpla2 | NM_001163689.1 | chr7:141455187-141460743 |
| 16900 | Plekhg5 | NM_001285999.1 | chr4:152096718-152115404 | 16997 | Pnpla3 | NM_054088.3 | chr15:84167815-84189521 |
| 16901 | Plekhg6 | NM_198604.2 | chr6:125362650-125380504 | 16998 | Pnpla5 | NM_029427.1 | chr15:84112620-84123175 |
| 16902 | Plekhh1 | NM_181073.3 | chr12:79029162-79081855 | 16999 | Pnpla6 | NM_001122818.2 | chr8:3515383-3544267 |
| 16903 | Plekhh2 | NM_177606.4 | chr17:84511894-84622142 | 17000 | Pnpla7 | NM_146251.4 | chr2:24976032-25054072 |
| 16904 | Plekhh3 | NM_146030.2 | chr11:101162679-101171302 | 17001 | Pnpla8 | NM_026164.2 | chr12:44269153-44313435 |
| 16905 | Plekhj1 | NM_023900.2 | chr10:80796098-80798626 | 17002 | Pnpo | NM_134021.2 | chr11:96937815-96944019 |
| 16906 | Plekhm1 | NM_183034.1 | chr11:103365091-103412664 | 17003 | Pnpt1 | NM_027869.1 | chr11:29130750-29161826 |
| 16907 | Plekhm2 | NM_001033150.1 | chr4:141625733-141664115 | 17004 | Pnrc1 | NM_001032225.2 | chr4:33245422-33248787 |
| 16908 | Plekhm3 | NM_001039493.1 | chr1:64789120-64956824 | 17005 | Pnrc2 | NM_026383.3 | chr4:135870925-135873846 |
| 16909 | Plekhn1 | NM_001008233.3 | chr4:156221455-156228542 | 17006 | Poc1a | NM_027354.2 | chr9:106281060-106349891 |
| 16910 | Plekho1 | NM_023320.2 | chr3:95988835-95995839 | 17007 | Poc1b | NM_027740.6 | chr10:99107170-99197988 |
| 16911 | Plekho2 | NM_153119.3 | chr9:65552576-65580087 | 17008 | Poc5 | NM_026173.3 | chr13:96388293-96415587 |
| 16912 | Plekhs1 | NM_001164263.1 | chr19:56461636-56486729 | 17009 | Podn | NM_001285956.1 | chr4:108014792-108030986 |
| 16913 | Plet1 | NM_029639.2 | chr9:50494524-50505639 | 17010 | Podnl1 | NM_001013384.2 | chr8:84125988-84132517 |
| 16914 | Pletlos | NR_040714.1 | chr9:50488798-50504805 | 17011 | Podxl | NM_013723.3 | chr6:31519492-31563917 |
| 16915 | Plg | NM_008877.3 | chr17:12378608-12419384 | 17012 | Podxl2 | NM_176973.4 | chr6:88842557-88874044 |
| 16916 | Plgrkt | NM_026362.2 | chr19:29348976-29361871 | 17013 | Pof1b | NM_181579.1 | chrX:112638426-112698651 |
| 16917 | Plin1 | NM_001113471.1 | chr7:79721163-79732776 | 17014 | Pofut1 | NM_080463.3 | chr2:153241531-153270249 |
| 16918 | Plin2 | NM_007408.3 | chr4:86656564-86670059 | 17015 | Pofut2 | NM_030262.3 | chr10:77259299-77269586 |
| 16919 | Plin3 | NM_025836.3 | chr17:56278641-56290511 | 17016 | Pogk | NM_001142948.1 | chr1:166393611-166409828 |
| 16920 | Plin4 | NM_020568.3 | chr17:56100590-56109802 | 17017 | Poglut1 | NM_172380.4 | chr16:38525057-38550256 |
| 16921 | Plin5 | NM_001077348.1 | chr17:56111600-56117298 | 17018 | Pogz | NM_001165948.1 | chr3:94837566-94883567 |
| 16922 | Plk1 | NM_011121.4 | chr7:122159434-122169884 | 17019 | Pola1 | NM_008892.2 | chrX:93304765-93632155 |
| 16923 | Plk2 | NM_152804.2 | chr13:110395043-110400843 | 17020 | Pola2 | NM_001164057.1 | chr19:5941104-5964306 |
| 16924 | Plk3 | NM_013807.3 | chr4:117128654-117133963 | 17021 | Polb | NM_011130.2 | chr8:22628118-22653437 |
| 16925 | Plk4 | NM_011495.2 | chr3:40799950-40816883 | 17022 | Pold1 | NM_011131.3 | chr7:44532743-44548815 |
| 16926 | Plk5 | NM_183152.3 | chr10:80356458-80365489 | 17023 | Pold2 | NM_008894.2 | chr11:5872179-5878256 |
| 16927 | Plp | NM_026385.4 | chr8:94674894-94696242 | 17024 | Pold3 | NM_133692.2 | chr7:100082112-100121506 |
| 16928 | Pln | NM_001141927.1 | chr10:53337685-53345999 | 17025 | Pold4 | NM_027196.4 | chr19:4231892-4233634 |
| 16929 | Plod1 | NM_011122.3 | chr4:147909752-147936776 | 17026 | Poldip2 | NM_026389.3 | chr11:78512295-78522736 |
| 16930 | Plod2 | NM_001142916.1 | chr9:92542222-92608427 | 17027 | Poldip3 | NM_178627.3 | chr15:83125977-83149336 |
| 16931 | Plod3 | NM_011962.3 | chr5:136987018-136996646 | 17028 | Pole | NM_011132.2 | chr5:110286318-110337483 |
| 16932 | Plp1 | NM_001290561.1 | chrX:136822745-136838682 | 17029 | Pole2 | NM_011133.2 | chr12:69201778-69228190 |
| 16933 | Plp2 | NM_019755.5 | chrX:7667940-7671390 | 17030 | Pole3 | NM_021498.2 | chr4:62523600-62525014 |
| 16934 | Plrg1 | NM_016784.3 | chr3:83055537-83072291 | 17031 | Pole4 | NM_025882.3 | chr6:82646711-82652865 |
| 16935 | Pls1 | NM_001033210.3 | chr9:95752641-95845279 | 17032 | Polg | NM_017462.2 | chr7:79449382-79466273 |
| 16936 | Pls3 | NM_001164453.1 | chrX:75785653-75875170 | 17033 | Polg2 | NM_015810.2 | chr11:106768203-106779637 |
| 16937 | Plscr1 | NM_011636.2 | chr9:92250199-92272561 | 17034 | Polh | NM_030715.3 | chr17:46171992-46202625 |
| 16938 | Plscr2 | NM_011195084.1 | chr9:92275601-92297752 | 17035 | Poli | NM_001136090.2 | chr18:70508679-70530321 |
| 16939 | Plscr3 | NM_001168497.1 | chr11:69846371-69852058 | 17036 | Polk | NM_012048.2 | chr13:96480688-96542485 |
| 16940 | Plscr4 | NM_178713.3 | chr9:92275977-92492516 | 17037 | Poll | NM_020032.2 | chr19:45552275-45560643 |
| 16941 | Plscr5 | NM_001195693.1 | chr9:92192935-92209698 | 17038 | Polm | NM_017401.2 | chr11:5827859-5838016 |
| 16942 | Pltp | NM_011125.2 | chr2:164839517-164857708 | 17039 | Poln | NM_001289803.1 | chr5:34007178-34169526 |
| 16943 | Plvap | NM_032398.2 | chr8:71497752-71511769 | 17040 | Polq | NM_001159369.1 | chr16:37011785-37095417 |
| 16944 | Plxdc1 | NM_001163608.1 | chr11:97923236-97986446 | 17041 | Polr1a | NM_009088.3 | chr6:71909052-71979360 |
| 16945 | Plxdc2 | NM_026162.6 | chr2:16356303-16755839 | 17042 | Polr1b | NM_009086.2 | chr2:129100995-129128595 |
| 16946 | Plxna1 | NM_008881.3 | chr6:89316313-89362613 | 17043 | Polr1c | NM_009085.2 | chr17:46243919-46248045 |
| 16947 | Plxna2 | NM_008882.2 | chr1:194619828-194816868 | 17044 | Polr1d | NM_009087.2 | chr5:147077345-147079086 |
| 16948 | Plxna3 | NM_008883.2 | chrX:74329065-74344689 | 17045 | Polr1e | NM_001285800.1 | chr4:45018608-45034279 |
| 16949 | Plxna4 | NM_175750.3 | chr6:32144556-32588192 | 17046 | Polr2a | NM_001291068.1 | chr11:69733998-69758633 |
| 16950 | Plxna4os1 | NR_040277.1 | chr6:32511140-32515576 | 17047 | Polr2b | NM_153798.2 | chr5:77310483-77349328 |
| 16951 | Plxnb1 | NM_172775.2 | chr9:109095435-109119915 | 17048 | Polr2c | NM_009090.5 | chr8:94857449-94864240 |
| 16952 | Plxnb2 | NM_001159521.2 | chr15:89155545-89173951 | 17049 | Polr2d | NM_027002.3 | chr18:31789158-31796642 |
| 16953 | Plxnb3 | NM_019587.2 | chrX:73757102-73772510 | 17050 | Polr2e | NM_025554.2 | chr10:80035952-80039659 |
| 16954 | Plxnc1 | NM_018754.3 | chr10:94790865-94944578 | 17051 | Polr2f | NM_027311.1 | chr15:79141366-79151767 |
| 16955 | Plxnd1 | NM_026376.3 | chr6:115984810-115995009 | 17052 | Polr2g | NM_026329.2 | chr19:8793128-8798557 |
| 16956 | Pm20d1 | NM_178079.3 | chr1:131797394-131818115 | 17053 | Polr2h | NM_145632.2 | chr16:20717825-20722285 |
| 16957 | Pm20d2 | NM_001034867.2 | chr4:33170405-33189737 | 17054 | Polr2i | NM_027259.1 | chr7:30232073-30233387 |
| 16958 | Pmaip1 | NM_021451.2 | chr18:66488603-66465558 | 17055 | Polr2j | NM_011293.2 | chr5:136116690-136122947 |
| 16959 | Pmch | NM_029971.2 | chr10:88091071-88092374 | 17056 | Polr2k | NM_001039368.2 | chr15:36174009-36177012 |
| 16960 | Pmel | NM_021882.4 | chr10:128706257-128720238 | 17057 | Polr2l | NM_025593.1 | chr7:141471859-141475153 |
| 16961 | Pmepa1 | NM_022995.3 | chr2:173224464-173276533 | 17058 | Polr2m | NM_001164793.1 | chr9:71478436-71484958 |
| 16962 | Pmf1 | NM_025769.4 | chr3:108394717-88410897 | 17059 | Polr3a | NM_001083247.1 | chr14:24448693-24487046 |
| 16963 | Pmfbp1 | NM_019938.3 | chr8:109494026-109542642 | 17060 | Polr3b | NM_027423.1 | chr10:84622436-84727178 |
| 16964 | Pmis2 | NR_027648.1 | chr7:30670721-30671605 | 17061 | Polr3c | NM_028925.1 | chr3:96711894-96727439 |
| 16965 | Pml | NM_008884.5 | chr9:58217179-58249786 | 17062 | Polr3d | NM_001164082.1 | chr14:70438747-70443227 |
| 16966 | Pmm1 | NM_001282040.1 | chr15:81951105-81960930 | 17063 | Polr3e | NM_001164096.1 | chr7:120917743-120947432 |
| 16967 | Pmm2 | NM_016881.2 | chr16:8637706-8657524 | 17064 | Polr3f | NM_029763.3 | chr2:144541779-144541779 |
| 16968 | Pmp2 | NM_001030305.2 | chr3:10179850-10188885 | 17065 | Polr3g | NM_001081176.1 | chr13:81673836-81711013 |
| 16969 | Pmp22 | NM_008885.3 | chr11:63181456-63159547 | 17066 | Polr3gl | NM_027241.4 | chr3:96577871-96594181 |
| 16970 | Pmpca | NM_173180.3 | chr2:26389247-26397121 | 17067 | Polr3h | NM_029029.4 | chr15:81915029-81926213 |
| 16971 | Pmpcb | NM_028431.2 | chr5:21737159-21757152 | 17068 | Polr3k | NM_025301.3 | chr2:181864359-181870826 |
| 16972 | Pms1 | NM_153556.2 | chr1:53188-53297028 | 17069 | Polrmt | NM_172531.3 | chr10:79736124-79746581 |
| 16973 | Pms2 | NM_008886.2 | chr5:143910000-143931756 | 17070 | Pom121 | NM_148932.2 | chr5:135376139-135394546 |
| 16974 | Pmvk | NM_026784.3 | chr3:89459117-89469009 | 17071 | Pom121l12 | NM_001164156.1 | chr11:14599239-14600316 |

Fig.21 - 89

| | | | | | | | |
|---|---|---|---|---|---|---|---|
| 17072 | Pom121l2 | NM_001162928.1 | chr13:21981180-21985903 | 17169 | Ppm1m | NM_026447.4 | chr9:106194952-106199233 |
| 17073 | Pomc | NM_001278581.1 | chr12:3954944-3960643 | 17170 | Ppm1n | NM_176691.3 | chr7:19276806-19280049 |
| 17074 | Pomgnt1 | NM_001290658.1 | chr4:116151430-116159844 | 17171 | Ppme1 | NM_028292.2 | chr7:100326736-100371896 |
| 17075 | Pomgnt2 | NM_001289558.1 | chr9:121981605-121996026 | 17172 | Ppox | NM_008911.2 | chr1:171276991-171281186 |
| 17076 | Pomk | NM_029037.4 | chr8:25980603-25994121 | 17173 | Pp1ca | NM_031868.2 | chr19:4192173-4195419 |
| 17077 | Pomp | NM_025624.2 | chr5:147860627-147875778 | 17174 | Pp1cb | NM_172707.3 | chr5:32458969-32493712 |
| 17078 | Pomt1 | NM_145145.1 | chr2:32236682-32255005 | 17175 | Pp1cc | NM_013636.3 | chr5:122158278-122175269 |
| 17079 | Pomt2 | NM_153415.4 | chr12:87106860-87147902 | 17176 | Ppp1r10 | NM_001163818.1 | chr17:35917195-35932283 |
| 17080 | Pon1 | NM_011134.3 | chr6:5168089-5193948 | 17177 | Ppp1r11 | NM_029632.3 | chr17:36948354-36951792 |
| 17081 | Pon2 | NM_183308.2 | chr6:5264623-5298373 | 17178 | Ppp1r12a | NM_027892.2 | chr10:108162399-108277575 |
| 17082 | Pon3 | NM_173006.1 | chr6:5220851-5256233 | 17179 | Ppp1r12b | NM_001081307.1 | chr1:134769842-134955940 |
| 17083 | Pop1 | NM_026340.3 | chr15:34495310-34530653 | 17180 | Ppp1r12c | NM_029834.3 | chr7:4481520-4501680 |
| 17084 | Pop4 | NM_025390.4 | chr7:38262819-38271348 | 17181 | Ppp1r13b | NM_011625.1 | chr12:111828457-111908055 |
| 17085 | Pop5 | NM_026398.4 | chr5:115235850-115240970 | 17182 | Ppp1r13l | NM_001010836.3 | chr7:19361215-19378533 |
| 17086 | Pop7 | NM_028753.2 | chr5:137501438-137502429 | 17183 | Ppp1r14a | NM_026731.3 | chr7:29289319-29293390 |
| 17087 | Popdc2 | NM_001081984.2 | chr16:38362189-38378216 | 17184 | Ppp1r14b | NM_008889.2 | chr19:6975047-6977324 |
| 17088 | Popdc3 | NM_024286.1 | chr10:45289304-45318450 | 17185 | Ppp1r14c | NM_133485.2 | chr10:3366149-3464975 |
| 17089 | Por | NM_008898.2 | chr5:135689144-135735326 | 17186 | Ppp1r14d | NM_001290796.1 | chr2:119218118-119229865 |
| 17090 | Porcn | NM_016913.4 | chrX:8193845-8206925 | 17187 | Ppp1r15a | NM_008654.2 | chr7:45522916-45526268 |
| 17091 | Postn | NM_001198765.1 | chr3:54361106-54391041 | 17188 | Ppp1r15b | NM_133819.3 | chr1:133131165-133139800 |
| 17092 | Pot1a | NM_133931.4 | chr6:25743734-25809226 | 17189 | Ppp1r16a | NM_033371.2 | chr15:76671679-76694915 |
| 17093 | Pot1b | NM_028370.1 | chr17:55652024-55712628 | 17190 | Ppp1r16b | NM_001159662.1 | chr2:158667134-158766334 |
| 17094 | Poteg | NM_026256.2 | chr8:27447669-27464112 | 17191 | Ppp1r17 | NM_011153.3 | chr6:56017514-56032688 |
| 17095 | Pou1f1 | NM_008849.4 | chr16:65520628-65533981 | 17192 | Ppp1r18 | NM_001146710.1 | chr17:35866127-35875596 |
| 17096 | Pou2af1 | NM_011136.2 | chr9:51213689-51240079 | 17193 | Ppp1r1a | NM_021391.3 | chr15:103530278-103537992 |
| 17097 | Pou2f1 | NM_011143.2 | chr1:165865153-166002634 | 17194 | Ppp1r1b | NM_144828.2 | chr11:98348405-98357796 |
| 17098 | Pou2f2 | NM_011135543 | chr7:25091114-25132460 | 17195 | Ppp1r1c | NM_001290743.1 | chr2:79707779-79818546 |
| 17099 | Pou2f3 | NM_011139.2 | chr9:43123938-43205755 | 17196 | Ppp1r2 | NM_025800.3 | chr16:31251540-31275277 |
| 17100 | Pou3f1 | NM_011141.2 | chr4:124657645-124660655 | 17197 | Ppp1r21 | NM_028658.4 | chr17:88530123-88588367 |
| 17101 | Pou3f2 | NM_008899.2 | chr4:22482094-22488366 | 17198 | Ppp1r26 | NM_001054420.1 | chr2:28447940-28455508 |
| 17102 | Pou3f3 | NM_008900.2 | chr1:42697145-42700209 | 17199 | Ppp1r27 | NM_026814.3 | chr11:120549974-120551132 |
| 17103 | Pou3f3os | NR_027826.1 | chr1:42648199-42694825 | 17200 | Ppp1r2-ps3 | NR_003650.1 | chr19:30538875-30539679 |
| 17104 | Pou3f4 | NM_008901.2 | chrX:110814378-110819108 | 17201 | Ppp1r2-ps7 | NR_033731.1 | chrX:22461595-22463543 |
| 17105 | Pou4f1 | NM_011143.4 | chr14:104462324-104467999 | 17202 | Ppp1r2-ps9 | NR_033171.1 | chrX:15110585-15111489 |
| 17106 | Pou4f2 | NM_138944.2 | chr8:78433008-78436652 | 17203 | Ppp1r32 | NM_133689.1 | chr19:10474256-10482897 |
| 17107 | Pou4f3 | NM_138945.2 | chr18:42394596-42396093 | 17204 | Ppp1r35 | NM_027242.4 | chr5:137778917-137780107 |
| 17108 | Pou5f1 | NM_001252452.1 | chr17:35508806-35510777 | 17205 | Ppp1r36 | NM_001163103.1 | chr12:76417598-76439491 |
| 17109 | Pou5f2 | NM_029315.1 | chr13:78024901-78026296 | 17206 | Ppp1r37 | NM_199149.3 | chr7:19530966-19562398 |
| 17110 | Pou6f1 | NM_001017.3 | chr15:100575317-100586365 | 17207 | Ppp1r3a | NM_080464.2 | chr6:14713821-14755274 |
| 17111 | Pou6f2 | NM_175006.2 | chr13:18124959-18382039 | 17208 | Ppp1r3b | NM_177741.3 | chr8:35375740-35388137 |
| 17112 | Ppzd1 | NM_173449.3 | chr17:53507459-53539451 | 17209 | Ppp1r3c | NM_016854.2 | chr19:36731730-36736604 |
| 17113 | Ppa1 | NM_023785.2 | chr10:61648620-61674165 | 17210 | Ppp1r3d | NM_001085601.2 | chr2:178411205-178414463 |
| 17114 | Ppa2 | NM_146141.2 | chr3:133310109-133378235 | 17211 | Ppp1r3e | NM_001167908.1 | chr14:54875596-54877538 |
| 17115 | Ppan | NM_145610.2 | chr9:20888174-20892179 | 17212 | Ppp1r3f | NM_001290574.1 | chrX:7558561-7574281 |
| 17116 | Ppap2a | NM_008247.3 | chr13:112800776-112867894 | 17213 | Ppp1r3fos | NR_029473.1 | chrX:7573599-7581016 |
| 17117 | Ppap2b | NM_080555.2 | chr4:105157346-105232767 | 17214 | Ppp1r3g | NM_029628.1 | chr13:35967905-35970388 |
| 17118 | Ppap2c | NM_028753.2 | chr10:79526423-79533787 | 17215 | Ppp1r42 | NM_145692.2 | chr1:9968622-10013541 |
| 17119 | Ppapdc1a | NM_001080963.1 | chr7:129257098-129391307 | 17216 | Ppp1r7 | NM_023200.2 | chr1:93343644-93367618 |
| 17120 | Ppapdc1b | NM_028000.1 | chr8:25720047-25724887 | 17217 | Ppp1r8 | NM_001290725.1 | chr4:132826923-132843169 |
| 17121 | Ppapdc2 | NM_028922.3 | chr19:28963919-28966301 | 17218 | Ppp1r9a | NM_181595.3 | chr6:4903319-5165661 |
| 17122 | Ppapdc3 | NM_145521.3 | chr2:32095650-32110820 | 17219 | Ppp1r9b | NM_172261.3 | chr11:94991211-95006898 |
| 17123 | Ppara | NM_001113418.1 | chr15:85735583-85806851 | 17220 | Ppp2ca | NM_019411.4 | chr11:52098823-52122749 |
| 17124 | Ppard | NM_011145.3 | chr17:28232753-28301469 | 17221 | Ppp2cb | NM_017374.3 | chr8:33599620-33619804 |
| 17125 | Pparg | NM_001127330.2 | chr6:115360950-115490401 | 17222 | Ppp2r1a | NM_016891.3 | chr17:20945453-20965905 |
| 17126 | Ppargc1a | NM_008904.2 | chr5:51454248-51553921 | 17223 | Ppp2r1b | NM_001004485.2 | chr9:50856923-50894229 |
| 17127 | Ppargc1b | NM_133249.2 | chr18:61298135-61400431 | 17224 | Ppp2r2a | NM_001205188.1 | chr14:67014055-67072471 |
| 17128 | Ppat | NM_172146.2 | chr5:76913248-78951578 | 17225 | Ppp2r2b | NM_028392.3 | chr18:42645220-43059471 |
| 17129 | Ppbp | NM_023785.2 | chr5:90768517-90770060 | 17226 | Ppp2r2c | NM_172994.2 | chr5:36868569-36955078 |
| 17130 | Ppcdc | NM_176831.4 | chr9:57417659-57440114 | 17227 | Ppp2r2cos | NR_045505.1 | chr5:36873594-36876879 |
| 17131 | Ppcs | NM_026494.3 | chr4:119418532-119422420 | 17228 | Ppp2r2d | NM_026391.2 | chr7:138846385-138883055 |
| 17132 | Ppdpf | NM_025598.2 | chr12:81187342-181188504 | 17229 | Ppp2r3a | NM_001161362.3 | chr9:101104988-101251832 |
| 17133 | Ppef1 | NM_011147.1 | chrX:160623093-160719972 | 17230 | Ppp2r3c | NM_021529.3 | chr12:55280813-55303000 |
| 17134 | Ppef2 | NM_011148.2 | chr5:92325373-92253159 | 17231 | Ppp2r3d | NM_001163415.1 | chr9:124474345-124476862 |
| 17135 | Ppfia1 | NM_001033319.2 | chr7:144476754-144553729 | 17232 | Ppp2r4 | NM_138748.5 | chr2:30416049-30447807 |
| 17136 | Ppfia2 | NM_001205341.1 | chr10:106470309-106933468 | 17233 | Ppp2r5a | NM_144880.4 | chr1:191351980-191397041 |
| 17137 | Ppfia3 | NM_001252411.1 | chr7:45339115-45367019 | 17234 | Ppp2r5b | NM_198168.3 | chr19:6227766-6235840 |
| 17138 | Ppfia4 | NM_001144855.1 | chr1:134296782-134382928 | 17235 | Ppp2r5c | NM_001081457.2 | chr12:110485738-110583074 |
| 17139 | Ppfibp1 | NM_001170433.1 | chr6:146888493-147032023 | 17236 | Ppp2r5d | NM_009358.3 | chr17:46682990-46705002 |
| 17140 | Ppfibp2 | NM_001163557.1 | chr7:107606843-107748583 | 17237 | Ppp2r5e | NM_012024.2 | chr12:75450880-75596200 |
| 17141 | Pphln1 | NM_001083114.1 | chr15:93398349-93491912 | 17238 | Ppp3ca | NM_008913.5 | chr3:136670065-136937727 |
| 17142 | Ppia | NM_008907.1 | chr11:6415869-6419810 | 17239 | Ppp3cb | NM_008914.3 | chr14:20499363-20546573 |
| 17143 | Ppib | NM_011149.2 | chr9:66060168-66066629 | 17240 | Ppp3cc | NM_008915.3 | chr14:70217864-70289497 |
| 17144 | Ppic | NM_008908.4 | chr18:53406840-53418007 | 17241 | Ppp3r1 | NM_024459.2 | chr11:17159297-17200380 |
| 17145 | Ppid | NM_026352.3 | chr3:79591388-79603650 | 17242 | Ppp3r2 | NM_001004025.4 | chr4:49678746-49681983 |
| 17146 | Ppie | NM_019489.5 | chr4:123127124-123139941 | 17243 | Ppp4c | NM_019674.3 | chr7:126728867-126792471 |
| 17147 | Ppif | NM_134084.1 | chr14:25694169-25700466 | 17244 | Ppp4r1 | NM_001114131.1 | chr17:65783354-65841926 |
| 17148 | Ppifos | NR_028021.1 | chr5:25695155-25701282 | 17245 | Ppp4r1l-ps | NR_027957.1 | chr2:173579319-173659539 |
| 17149 | Ppig | NM_001081086.1 | chr2:69723087-69754059 | 17246 | Ppp4r2 | NM_182939.4 | chr6:100833637-100868717 |
| 17150 | Pplh | NM_001110129.2 | chr4:119306289-119320623 | 17247 | Ppp4r4 | NM_028980.3 | chr12:103532564-103613832 |
| 17151 | Ppil1 | NM_026845.4 | chr17:29250834-29261971 | 17248 | Ppp5c | NM_011155.2 | chr7:17004640-17027914 |
| 17152 | Ppil2 | NM_001252444.1 | chr16:17086555-17111252 | 17249 | Ppp6c | NM_024209.2 | chr2:39196797-39226338 |
| 17153 | Ppil3 | NM_001285826.1 | chr1:58430392-58445486 | 17250 | Ppp6r1 | NM_172894.2 | chr7:4631494-4658950 |
| 17154 | Ppil4 | NM_026141.3 | chr10:7792893-7822563 | 17251 | Ppp6r2 | NM_026813.1 | chr15:89211558-89286261 |
| 17155 | Ppil6 | NM_028430.1 | chr10:41490438-41514288 | 17252 | Ppp6r3 | NM_001164159.1 | chr19:3454928-3575749 |
| 17156 | Ppip5k1 | NM_175246.3 | chr2:121310560-121351013 | 17253 | Pprc1 | NM_001081214.1 | chr19:46056538-46072909 |
| 17157 | Ppip5k2 | NM_179760.5 | chr1:97706082-97770092 | 17254 | Ppt1 | NM_008917.3 | chr4:122836226-122859175 |
| 17158 | Ppl | NM_008909.2 | chr16:5086290-5132481 | 17255 | Ppt2 | NM_019441.5 | chr17:34616661-34627148 |
| 17159 | Ppm1a | NM_008910.3 | chr12:72761210-72794940 | 17256 | Pptc7 | NM_177242.4 | chr5:122284397-122324281 |
| 17160 | Ppm1b | NM_001159496.1 | chr17:84958000-85014776 | 17257 | Ppwd1 | NM_172807.4 | chr13:104205121-104228844 |
| 17161 | Ppm1d | NM_016910.3 | chr11:85313153-85347071 | 17258 | Ppy | NM_008918.3 | chr11:102099930-102101300 |
| 17162 | Ppm1e | NM_177167.4 | chr11:87226905-87388994 | 17259 | Pqbp1 | NM_001252528.1 | chrX:7894518-7899000 |
| 17163 | Ppm1f | NM_176833.4 | chr16:16896468-16927375 | 17260 | Pqlc1 | NM_001164420.1 | chr18:80255244-80292724 |
| 17164 | Ppm1g | NM_008014.3 | chr5:31266507-31220545 | 17261 | Pqlc2 | NM_145374.2 | chr4:139298004-139310700 |
| 17165 | Ppm1h | NM_001110218.1 | chr10:122678761-122945793 | 17262 | Pqlc3 | NM_001161111.1 | chr12:16992960-17000118 |
| 17166 | Ppm1j | NM_027982.2 | chr3:104781055-104786017 | 17263 | Pradc1 | NM_001163427.1 | chr6:85466784-85451302 |
| 17167 | Ppm1k | NM_175523.4 | chr6:57506501-57535426 | 17264 | Praf2 | NM_138602.4 | chrX:7728570-7731063 |
| 17168 | Ppm1l | NM_178726.3 | chr3:69316917-69555396 | 17265 | Pram1 | NM_001002842.2 | chr17:33638055-33645706 |

Fig.21 - 90

| | | | | | | | |
|---|---|---|---|---|---|---|---|
| 17266 | Prame | NM_029459.2 | chrX:135613001-135627705 | 17363 | Prl2c1 | NM_001045533.2 | chr13:27649341-27657708 |
| 17267 | Pramef12 | NM_029948.2 | chr4:144391673-144408464 | 17364 | Prl2c2 | NM_031191.1 | chr13:12996123-13005330 |
| 17268 | Pramef17 | NM_001085540.2 | chr4:143991126-143994369 | 17365 | Prl2c3 | NM_011118.2 | chr13:12790820-12800079 |
| 17269 | Pramef25 | NM_001126315.2 | chr4:143948182-143951016 | 17366 | Prl2c4 | NM_011954.2 | chr13:12790817-12800058 |
| 17270 | Pramef6 | NM_001085414.2 | chr4:143894236-143900380 | 17367 | Prl2c5 | NM_181852.2 | chr13:13182715-13191925 |
| 17271 | Pramef8 | NM_172877.2 | chr4:143412425-143421087 | 17368 | Prl3a1 | NM_025896.2 | chr13:27259488-27276660 |
| 17272 | Pramel1 | NM_031377.2 | chr4:143394440-143399819 | 17369 | Prl3b1 | NM_008865.3 | chr13:27242429-27249740 |
| 17273 | Pramel3 | NM_031390.2 | chrX:135302315-135312636 | 17370 | Prl3c1 | NM_001163218.1 | chr13:27198902-27203750 |
| 17274 | Pramel4 | NM_001001319.3 | chr4:144059125-144069318 | 17371 | Prl3d1 | NM_001205322.1 | chr13:27094188-27100260 |
| 17275 | Pramel5 | NM_001085418.2 | chr4:144270632-144280466 | 17372 | Prl3d2 | NM_172155.1 | chr13:27121703-27127482 |
| 17276 | Pramel6 | NM_178249.2 | chr2:87508457-87510865 | 17373 | Prl3d3 | NM_172156.2 | chr13:27156798-27162520 |
| 17277 | Pramel7 | NM_178250.2 | chr2:87489087-87492418 | 17374 | Prl4a1 | NM_011165.3 | chr13:28016222-28023946 |
| 17278 | Prap1 | NM_009475.2 | chr7:140093395-140097203 | 17375 | Prl5a1 | NM_023746.4 | chr13:28142483-28151595 |
| 17279 | Prb1 | NM_198669.1 | chr6:132206794-132210521 | 17376 | Prl6a1 | NM_011166.2 | chr13:27312626-27319252 |
| 17280 | Prc1 | NM_001285997.1 | chr7:80294450-80316259 | 17377 | Prl7a1 | NM_001164058.1 | chr13:27633363-27642493 |
| 17281 | Prcc | NM_033573.2 | chr3:87858902-87885562 | 17378 | Prl7a2 | NM_011168.4 | chr13:27658583-27668036 |
| 17282 | Prcp | NM_028243.3 | chr7:92875252-92934581 | 17379 | Prl7b1 | NM_029355.2 | chr13:27601818-27610682 |
| 17283 | Prdm1 | NM_007548.4 | chr10:44437173-44458748 | 17380 | Prl7c1 | NM_028206.2 | chr13:27773494-27780804 |
| 17284 | Prdm10 | NM_001080817.1 | chr9:31315106-31378543 | 17381 | Prl7d1 | NM_011120.2 | chr13:27708997-27718737 |
| 17285 | Prdm11 | NM_001175536.1 | chr2:92974905-93046144 | 17382 | Prl8a1 | NM_028477.2 | chr13:27573921-27582171 |
| 17286 | Prdm12 | NM_001123362.1 | chr2:31640036-31655795 | 17383 | Prl8a2 | NM_001289919.1 | chr13:27345672-27354215 |
| 17287 | Prdm13 | NM_001080771.1 | chr4:21677479-21685963 | 17384 | Prl8a6 | NM_001271378.1 | chr13:27432680-27438688 |
| 17288 | Prdm14 | NM_001081209.2 | chr1:13113427-13127163 | 17385 | Prl8a8 | NM_023741.2 | chr13:27507071-27513213 |
| 17289 | Prdm15 | NM_144789.2 | chr16:97791466-97851227 | 17386 | Prl8a9 | NM_029332.4 | chr13:27558000-27564604 |
| 17290 | Prdm16 | NM_001177995.1 | chr4:154316124-154636873 | 17387 | Prlh | NM_001101647.1 | chr1:90953107-90954012 |
| 17291 | Prdm2 | NM_001081355.3 | chr4:143107290-143212709 | 17388 | Prlhr | NM_201615.2 | chr19:60466752-60468304 |
| 17292 | Prdm4 | NM_181650.3 | chr10:85891967-85916729 | 17389 | Prlr | NM_001253781.1 | chr15:10223905-10349180 |
| 17293 | Prdm5 | NM_027547.2 | chr6:65778961-65936377 | 17390 | Prm1 | NM_013637.4 | chr16:10796331-10796823 |
| 17294 | Prdm6 | NM_001033281.3 | chr18:53464545-53575857 | 17391 | Prm2 | NM_008933.2 | chr16:10791376-10792105 |
| 17295 | Prdm8 | NM_029947.2 | chr5:98180868-98187448 | 17392 | Prm3 | NM_013638.2 | chr16:10790507-10790914 |
| 17296 | Prdm9 | NM_144809.2 | chr17:15542876-15563323 | 17393 | Prmt1 | NM_001252476.1 | chr7:44976754-44986420 |
| 17297 | Prdx1 | NM_011034.4 | chr4:116685598-116700000 | 17394 | Prmt10 | NM_001081240.3 | chr8:77549396-77581338 |
| 17298 | Prdx2 | NM_011563.5 | chr8:84969647-84974313 | 17395 | Prmt2 | NM_001077638.2 | chr10:76207225-76237865 |
| 17299 | Prdx3 | NM_007452.2 | chr19:60864065-60874538 | 17396 | Prmt3 | NM_133740.2 | chr7:49778357-49858265 |
| 17300 | Prdx4 | NM_016764.5 | chrX:155323917-155338460 | 17397 | Prmt5 | NM_013768.3 | chr14:54507181-54517470 |
| 17301 | Prdx5 | NM_012021.2 | chr19:6906818-6909645 | 17398 | Prmt6 | NM_178891.5 | chr3:110248524-110250999 |
| 17302 | Prdx6 | NM_007453.4 | chr1:161240111-161251210 | 17399 | Prmt7 | NM_145404.1 | chr8:106211053-106251694 |
| 17303 | Prdx6b | NM_177256.5 | chr2:80292469-80295358 | 17400 | Prmt8 | NM_201371.2 | chr6:127689008-127769159 |
| 17304 | Preb | NM_030916.6 | chr5:30951666-30960327 | 17401 | Prn | NM_001278258.1 | chr2:131909927-131956131 |
| 17305 | Prelid1 | NM_025596.5 | chr13:55322054-55325272 | 17402 | Prnd | NM_001278256.1 | chr2:131950860-131956131 |
| 17306 | Prelid2 | NM_029942.1 | chr18:41875695-41951194 | 17403 | Prnp | NM_001278256.1 | chr2:131909927-131938436 |
| 17307 | Prelp | NM_054077.4 | chr1:133910303-133921401 | 17404 | Prob1 | NM_001270846.1 | chr18:35650350-35655199 |
| 17308 | Prep | NM_011156.2 | chr10:45067213-45158995 | 17405 | Proc | NM_001042767.3 | chr18:32132125-32139670 |
| 17309 | Prep1 | NM_001163622.1 | chr17:85063476-85090267 | 17406 | Proca1 | NM_001045516.2 | chr11:78193391-78205763 |
| 17310 | Prex1 | NM_177782.3 | chr2:166566344-166713832 | 17407 | Procr | NM_011171.2 | chr2:155751216-155755478 |
| 17311 | Prex2 | NM_001033636.4 | chr1:11263962-11303682 | 17408 | Prodh | NM_011172.2 | chr16:18071725-18089190 |
| 17312 | Prf1 | NM_011073.3 | chr10:61297835-61304263 | 17409 | Prodh2 | NM_019546.5 | chr7:30493657-30513402 |
| 17313 | Prg2 | NM_008920.4 | chr2:84980460-84983632 | 17410 | Prok1 | NM_001044382.1 | chr3:107235530-107239707 |
| 17314 | Prg3 | NM_016914.2 | chr2:84918214-84993886 | 17411 | Prok2 | NM_001037539.2 | chr6:99711298-99726392 |
| 17315 | Prg4 | NM_001110146.1 | chr1:150449411-150466165 | 17412 | Prokr1 | NM_023311.3 | chr6:87578591-87590701 |
| 17316 | Prh1 | NM_011174.4 | chr6:132569841-132572401 | 17413 | Prokr2 | NM_144944.3 | chr2:132370328-132385447 |
| 17317 | Prickle1 | NM_001033217.4 | chr15:93499113-93595891 | 17414 | Prol1 | NM_008644.2 | chr5:88317311-88328817 |
| 17318 | Prickle2 | NM_001081146.2 | chr6:92370891-92706184 | 17415 | Prom1 | NM_001163577.1 | chr5:43993621-44101736 |
| 17319 | Prickle3 | NM_001290624.1 | chrX:7657378-7668186 | 17416 | Prom2 | NM_138750.2 | chr2:127528952-127541417 |
| 17320 | Prickle4 | NM_001200337.1 | chr17:47688473-47694736 | 17417 | Prop1 | NM_008936.1 | chr11:50950805-50953632 |
| 17321 | Prim1 | NM_008921.2 | chr10:128015214-128030030 | 17418 | Prorsd1 | NM_001163454.2 | chr11:29511756-29515033 |
| 17322 | Prim2 | NM_008922.2 | chr1:33453807-33669794 | 17419 | Pros1 | NM_011173.3 | chr16:62854306-62929342 |
| 17323 | Prima1 | NM_133364.2 | chr12:103196907-103242146 | 17420 | Prosc | NM_001039077.2 | chr8:27042554-27060241 |
| 17324 | Primpol | NM_001001384.1 | chr8:46575593-46617200 | 17421 | Proser1 | NM_173382.1 | chr5:53463816-53481755 |
| 17325 | Prkaa1 | NM_001013367.3 | chr15:5143860-5181899 | 17422 | Proser2 | NM_001159657.1 | chr2:6098499-6130185 |
| 17326 | Prkaa2 | NM_178143.2 | chr4:105029649-105109898 | 17423 | Prox1 | NM_008937.2 | chr1:190121776-190170680 |
| 17327 | Prkab1 | NM_031869.2 | chr5:116013589-116024428 | 17424 | Prox2 | NM_175198.4 | chr12:85086813-85106431 |
| 17328 | Prkab2 | NM_182997.2 | chr3:97658211-97673067 | 17425 | Proz | NM_025834.3 | chr8:13060907-13075006 |
| 17329 | Prkaca | NM_001277898.1 | chr8:83976882-83996442 | 17426 | Prp2 | NM_031499.2 | chr6:132595945-132600702 |
| 17330 | Prkacb | NM_001164198.1 | chr3:146729578-146770238 | 17427 | Prpf18 | NM_026045.3 | chr2:4622166-4652086 |
| 17331 | Prkag1 | NM_016781.2 | chr15:98812796-98831508 | 17428 | Prpf19 | NM_001253843.1 | chr19:10895230-10909559 |
| 17332 | Prkag2 | NM_001170555.1 | chr5:24862734-24908509 | 17429 | Prpf3 | NM_027541.4 | chr3:95830621-95865753 |
| 17333 | Prkag2os1 | NR_040684.1 | chr5:24902568-24906849 | 17430 | Prpf31 | NM_001159714.1 | chr7:3629984-3642484 |
| 17334 | Prkag3 | NM_153744.3 | chr1:74738921-74748955 | 17431 | Prpf38a | NM_172697.3 | chr4:108564866-108579336 |
| 17335 | Prkar1a | NM_021880.3 | chr11:109650920-109669663 | 17432 | Prpf38b | NM_025845.2 | chr3:108902806-108911704 |
| 17336 | Prkar1b | NM_001253890.1 | chr5:139017303-139130386 | 17433 | Prpf39 | NM_177806.3 | chr12:65036333-65063386 |
| 17337 | Prkar2a | NM_008924.2 | chr9:108692142-108749511 | 17434 | Prpf4 | NM_027297.3 | chr4:62408782-62426990 |
| 17338 | Prkar2b | NM_011158.3 | chr12:31958478-32061279 | 17435 | Prpf40a | NM_018785.2 | chr2:53138475-53191187 |
| 17339 | Prkca | NM_011073.3 | chr11:107933186-108343888 | 17436 | Prpf40b | NM_018736.2 | chr15:99295408-99317007 |
| 17340 | Prkcb | NM_008855.3 | chr7:122289124-122634401 | 17437 | Prpf4b | NM_013830.2 | chr13:34875493-34902878 |
| 17341 | Prkcd | NM_011103.3 | chr14:30595353-30626208 | 17438 | Prpf6 | NM_133701.2 | chr2:181601318-181655661 |
| 17342 | Prkcdbp | NM_028444.1 | chr7:105480615-105482197 | 17439 | Prpf8 | NM_138659.2 | chr11:75486776-75509447 |
| 17343 | Prkce | NM_011104.3 | chr17:86167784-86657919 | 17440 | Prph | NM_001163588.1 | chr15:99055173-99058978 |
| 17344 | Prkcg | NM_001291434.1 | chr7:3303513-3331097 | 17441 | Prph2 | NM_008938.1 | chr17:46910484-46924926 |
| 17345 | Prkch | NM_008856.4 | chr12:73584795-73778184 | 17442 | Prpmep5 | NM_001024705.2 | chr6:132311589-132314743 |
| 17346 | Prkci | NM_008857.3 | chr3:30995770-31052740 | 17443 | Prps1 | NM_021463.4 | chrX:140456602-140476140 |
| 17347 | Prkcq | NM_008859.2 | chr2:11172381-11301226 | 17444 | Prps1l1 | NM_029294.2 | chr12:34984760-34986436 |
| 17348 | Prkcsh | NM_008925.2 | chr9:22002987-22014245 | 17445 | Prps1l3 | NM_001037746.3 | chr12:57230411-57242168 |
| 17349 | Prkcz | NM_001039079.2 | chr4:155280117-155345789 | 17446 | Prps2 | NM_026662.5 | chrX:167346319-167382749 |
| 17350 | Prkd1 | NM_008858.3 | chr12:50341231-50649223 | 17447 | Prpsap1 | NM_026384.3 | chr11:116470815-116490346 |
| 17351 | Prkd2 | NM_001252458.3 | chr7:16842901-16870461 | 17448 | Prpsap2 | NM_001164242.1 | chr11:61729649-61762083 |
| 17352 | Prkd3 | NM_001171004.1 | chr17:78949404-79020816 | 17449 | Prr11 | NM_175563.5 | chr11:87089155-87108714 |
| 17353 | Prkdc | NM_011159.2 | chr16:15637885-15842239 | 17450 | Prr12 | NM_175022.2 | chr7:45027706-45052881 |
| 17354 | Prkg1 | NM_001013833.3 | chr19:30564486-31765033 | 17451 | Prr13 | NM_001170911.1 | chr15:102459169-102462806 |
| 17355 | Prkg2 | NM_008926.4 | chr5:98929772-99037079 | 17452 | Prr14 | NM_145589.2 | chr7:127471613-127476758 |
| 17356 | Prkra | NM_011871.2 | chr2:76629936-76647984 | 17453 | Prr14l | NM_194340.2 | chr5:32789206-32854230 |
| 17357 | Prkrip1 | NM_025774.3 | chr5:136180356-136198954 | 17454 | Prr15 | NM_030024.2 | chr6:54327011-54330200 |
| 17358 | Prkrir | NM_198703862-198718081 | chr7:65827 | chr11:4876 | 17455 | Prr15l | NM_146026.1 | chr11:96929623-96935647 |
| 17359 | Prkx | NM_016979.1 | chrX:77762029-77795960 | 17456 | Prr16 | NM_001081224.2 | chr18:51117897-51304641 |
| 17360 | Prl | NM_001163536.1 | chr13:27057569-27065203 | 17457 | Prr18 | NM_178774.4 | chr17:8340738-8344113 |
| 17361 | Prl2a1 | NM_019911.1 | chr13:27801654-27808716 | 17458 | Prr19 | NM_001081294.1 | chr7:25301358-25304133 |
| 17362 | Prl2b1 | NM_025532.3 | chr13:27383344-27390846 | 17459 | Prr22 | NM_001195673.1 | chr17:56770275-56772134 |

Fig.21 - 91

| | | | | | | | |
|---|---|---|---|---|---|---|---|
| 17460 | Prr23a | NM_001134660.1 | chr9:98842586-98843645 | 17557 | Psma2 | NM_008944.2 | chr13:14613241-14625673 |
| 17461 | Prr24 | NM_001136270.1 | chr7:16272012-16273692 | 17558 | Psma3 | NM_011184.5 | chr12:70974622-70995877 |
| 17462 | Prr27 | NM_001163551.1 | chr5:87825696-87846386 | 17559 | Psma4 | NM_011966.3 | chr9:54950858-54958030 |
| 17463 | Prr3 | NM_001165892.1 | chr17:35977755-35979467 | 17560 | Psma5 | NM_011967.3 | chr3:108256925-108279952 |
| 17464 | Prr30 | NM_029680.1 | chr14:101397689-101200069 | 17561 | Psma6 | NM_011968.3 | chr12:55398824-55418459 |
| 17465 | Prr32 | NM_026841.1 | chrX:45090903-45092790 | 17562 | Psma7 | NM_001289476.1 | chr2:180036366-180042464 |
| 17466 | Prr33 | NR_033261.1 | chr7:142491079-142506771 | 17563 | Psma8 | NM_001163609.1 | chr18:14706150-14762299 |
| 17467 | Prr5 | NM_146061.4 | chr15:84680997-84703673 | 17564 | Psmb1 | NM_011185.3 | chr17:15475720-15498276 |
| 17468 | Prr5l | NM_001083810.2 | chr2:101714284-101797707 | 17565 | Psmb10 | NM_013640.3 | chr8:105935727-105938392 |
| 17469 | Prr7 | NM_001030296.4 | chr13:55464266-55473155 | 17566 | Psmb11 | NM_175204.4 | chr14:54625309-54629656 |
| 17470 | Prr9 | NM_175424.3 | chr3:92122203-92123947 | 17567 | Psmb2 | NM_011970.4 | chr4:126677642-126709715 |
| 17471 | Prrc1 | NM_028447.3 | chr18:57354732-57392719 | 17568 | Psmb3 | NM_011971.4 | chr11:97703433-97713900 |
| 17472 | Prrc2a | NM_001199044.1 | chr17:35149085-35164877 | 17569 | Psmb4 | NM_008945.3 | chr3:94884323-94886958 |
| 17473 | Prrc2b | NM_001159634.1 | chr2:32151147-32234537 | 17570 | Psmb5 | NM_011186.1 | chr14:54614119-54617995 |
| 17474 | Prrc2c | NM_001081290.1 | chr1:162671784-162740556 | 17571 | Psmb6 | NM_008946.4 | chr11:70525356-70527858 |
| 17475 | Prrg1 | NM_001164275.2 | chrX:78449609-78583805 | 17572 | Psmb7 | NM_011187.1 | chr2:38588045-38643906 |
| 17476 | Prrg2 | NM_022999.1 | chr7:45053606-45061652 | 17573 | Psmb8 | NM_010724.2 | chr17:34198194-34201454 |
| 17477 | Prrg3 | NM_001081335.2 | chrX:71962981-71972722 | 17574 | Psmb9 | NM_013585.2 | chr17:34182098-34187330 |
| 17478 | Prrg4 | NM_178695.5 | chr2:104830740-104849850 | 17575 | Psmc1 | NM_008947.3 | chr12:100113390-100123364 |
| 17479 | Prrt1 | NM_030890.1 | chr17:34629685-34632260 | 17576 | Psmc2 | NM_011188.3 | chr5:21785282-21803784 |
| 17480 | Prrt2 | NM_001102563.1 | chr7:127017541-127021211 | 17577 | Psmc3 | NM_008948.2 | chr2:91054015-91059438 |
| 17481 | Prrt3 | NM_001289699.1 | chr6:113493638-113501931 | 17578 | Psmc3ip | NM_008949.3 | chr11:101092140-101095435 |
| 17482 | Prrt4 | NM_001101443.1 | chr6:29169229-29179584 | 17579 | Psmc4 | NM_011874.2 | chr7:28041701-28050092 |
| 17483 | Prrx1 | NM_001025570.1 | chr1:163255276-163313650 | 17580 | Psmc5 | NM_008950.1 | chr11:106256184-106263112 |
| 17484 | Prrx2 | NM_009116.2 | chr2:30845366-30881247 | 17581 | Psmc6 | NM_025959.3 | chr14:45329823-45349071 |
| 17485 | Prrxl1 | NM_001001796.4 | chr14:32599926-32649246 | 17582 | Psrnd1 | NM_027357.2 | chr1:86064618-86139295 |
| 17486 | Prss1 | NM_053243.2 | chr6:41458929-41463786 | 17583 | Psmd10 | NM_001164177.1 | chrX:140948424-140956711 |
| 17487 | Prss12 | NM_008939.2 | chr3:123446912-123506602 | 17584 | Psmd11 | NM_178616.3 | chr11:80428614-80472133 |
| 17488 | Prss16 | NM_019412.2 | chr13:22002175-22009741 | 17585 | Psmd12 | NM_025894.2 | chr11:107479527-107499036 |
| 17489 | Prss2 | NM_099430.2 | chr6:41521775-41525079 | 17586 | Psmd13 | NM_011875.4 | chr7:140882393-140838642 |
| 17490 | Prss21 | NM_020487.4 | chr17:23868071-23873113 | 17587 | Psmd14 | NM_021528.2 | chr2:61711693-61800378 |
| 17491 | Prss22 | NM_133731.2 | chr17:23893533-23998100 | 17588 | Psmd2 | NM_134101.2 | chr16:20651651-20666414 |
| 17492 | Prss23 | NM_029614.3 | chr7:89507784-89517586 | 17589 | Psmd3 | NM_009439.1 | chr11:98682553-98695978 |
| 17493 | Prss27 | NM_175484.4 | chr17:24038242-24045949 | 17590 | Psmd4 | NM_001282017.1 | chr3:95032690-95042614 |
| 17494 | Prss28 | NM_053259.2 | chr17:25308646-25311876 | 17591 | Psmd5 | NM_080554.2 | chr2:34852088-34870962 |
| 17495 | Prss29 | NM_053260.3 | chr17:25318653-25322684 | 17592 | Psmd6 | NM_025590.2 | chr14:14112184-14120904 |
| 17496 | Prss3 | NM_011645.2 | chr6:41373758-41377613 | 17593 | Psmd7 | NM_010817.2 | chr8:107580379-107598482 |
| 17497 | Prss30 | NM_013921.3 | chr17:23972126-23975230 | 17594 | Psmd8 | NM_026545.3 | chr7:29174186-29180673 |
| 17498 | Prss32 | NM_027022.2 | chr17:23853771-23859776 | 17595 | Psmd9 | NM_026000.2 | chr5:123228189-123256125 |
| 17499 | Prss33 | NM_001081399.2 | chr17:23833360-23836767 | 17596 | Psme1 | NM_011189.1 | chr14:55578493-55581527 |
| 17500 | Prss34 | NM_178372.2 | chr17:25298393-25300161 | 17597 | Psme2 | NM_001029855.1 | chr14:55587439-55591101 |
| 17501 | Prss35 | NM_178738.3 | chr9:86743632-86757506 | 17598 | Psme2b | NM_001281472.1 | chr11:48945351-48946410 |
| 17502 | Prss36 | NM_001081374.1 | chr7:127932637-127946725 | 17599 | Psme3 | NM_011192.3 | chr11:101316250-101323530 |
| 17503 | Prss37 | NM_026317.2 | chr6:40514823-40519508 | 17600 | Psme4 | NM_134013.3 | chr11:30771774-30880361 |
| 17504 | Prss38 | NM_001045521.1 | chr11:59372668-59375653 | 17601 | Psmf1 | NM_212446.2 | chr2:151716061-151741310 |
| 17505 | Prss39 | NM_009355.2 | chr1:34498429-34503062 | 17602 | Psmg1 | NM_019537.2 | chr16:95979984-95990903 |
| 17506 | Prss40 | NM_009356.2 | chr1:34552330-34560943 | 17603 | Psmg2 | NM_134138.1 | chr18:67641598-67654152 |
| 17507 | Prss41 | NM_027644.1 | chr17:23836784-23844156 | 17604 | Psmg3 | NM_025604.3 | chr5:139823593-139826843 |
| 17508 | Prss42 | NM_153099.1 | chr9:110798184-110803744 | 17605 | Psmg4 | NM_001014130.2 | chr13:34162963-34178172 |
| 17509 | Prss43 | NM_199471.1 | chr9:110826689-110831504 | 17606 | Psors1c2 | NM_020576.2 | chr17:35533200-35534648 |
| 17510 | Prss44 | NM_148940.3 | chr9:110813993-110817999 | 17607 | Pspc1 | NM_025682.3 | chr14:56722448-56778316 |
| 17511 | Prss45 | NM_153172.1 | chr9:110834587-110841310 | 17608 | Psph | NM_133900.4 | chr5:129765557-129787253 |
| 17512 | Prss46 | NM_183103.2 | chr9:110844505-110856522 | 17609 | Pspn | NM_008954.2 | chr17:56999456-57000018 |
| 17513 | Prss48 | NM_001001650.1 | chr3:85993809-86002491 | 17610 | Psrc1 | NM_001190161.1 | chr3:108383803-108388231 |
| 17514 | Prss50 | NM_146227.4 | chr9:110857966-110864628 | 17611 | Psrk | NM_001039534.1 | chr3:131371145-131387838 |
| 17515 | Prss51 | NM_001193631.1 | chr14:64093695-64097672 | 17612 | Pstpip1 | NM_011193.2 | chr9:56089975-56128890 |
| 17516 | Prss52 | NM_028525.2 | chr14:64104322-64113751 | 17613 | Pstpip2 | NM_013831.4 | chr18:77794549-77882879 |
| 17517 | Prss53 | NM_001081268.1 | chr7:127885443-127890970 | 17614 | Ptafr | NM_001081211.2 | chr4:132564066-132582686 |
| 17518 | Prss54 | NM_027640.1 | chr8:95559291-95575197 | 17615 | Ptar1 | NM_028208.1 | chr19:23687399-23721129 |
| 17519 | Prss55 | NM_001081063.1 | chr14:64075442-64085389 | 17616 | Ptbp1 | NM_001077636.2 | chr10:79854431-79864435 |
| 17520 | Prss56 | NM_027084.2 | chr1:87183313-87188405 | 17617 | Ptbp2 | NM_019550.2 | chr3:119718741-119783188 |
| 17521 | Prss57 | NM_001042710.1 | chr10:79781473-79788985 | 17618 | Ptbp3 | NM_144904.2 | chr4:59471867-59549364 |
| 17522 | Prss58 | NM_175020.3 | chr6:40896261-40900387 | 17619 | Ptcd1 | NM_133735.2 | chr5:145147377-145167104 |
| 17523 | Prss8 | NM_133351.3 | chr7:127925716-127930113 | 17620 | Ptcd2 | NM_026873.2 | chr13:99319648-99344678 |
| 17524 | Prtg | NM_175485.4 | chr9:72807273-72917307 | 17621 | Ptcd3 | NM_027275.3 | chr6:71880637-71908762 |
| 17525 | Prtn3 | NM_177613.2 | chr10:79879666-79883172 | 17622 | Ptch1 | NM_008957.2 | chr13:63511532-63565520 |
| 17526 | Prune | NM_178347.2 | chr3:95253673-95282076 | 17623 | Ptch2 | NM_008958.3 | chr4:117096055-117116101 |
| 17527 | Prune2 | NM_181348.4 | chr19:16956117-17223932 | 17624 | Ptchd1 | NM_001093750.1 | chrX:155569735-155623327 |
| 17528 | Prx | NM_019412.2 | chr7:27499323-27520041 | 17625 | Ptchd2 | NM_001083342.1 | chr4:148236856-148287965 |
| 17529 | Psap | NM_001146120.1 | chr10:60277827-60302600 | 17626 | Ptchd3 | NM_029049.1 | chr11:121830217-121843436 |
| 17530 | Psapl1 | NM_175249.3 | chr5:36204020-36206567 | 17627 | Ptchd4 | NM_028474.1 | chr17:42315946-42507741 |
| 17531 | Psat1 | NM_001205339.1 | chr19:15905122-15924622 | 17628 | Ptcra | NM_011195.2 | chr17:46755662-46763712 |
| 17532 | Psca | NM_028216.2 | chr15:74714838-74717065 | 17629 | Ptdss1 | NM_008959.3 | chr13:66932829-66998401 |
| 17533 | Psd | NM_028627.2 | chr19:46312086-46327156 | 17630 | Ptdss2 | NM_019784.2 | chr7:141131285-141156154 |
| 17534 | Psd2 | NM_001289602.1 | chr18:35964829-36014716 | 17631 | Pten | NM_008960.1 | chr19:32757576-32826160 |
| 17535 | Psd3 | NM_027626.1 | chr8:67689081-67818295 | 17632 | Pter | NM_008961.3 | chr2:12924040-13003454 |
| 17536 | Psd4 | NM_001243396.2 | chr2:24385396-24408729 | 17633 | Ptf1a | NM_018809.2 | chr2:19445662-19447501 |
| 17537 | Pse1 | NM_008943.2 | chr12:83688662-83736199 | 17634 | Ptgdr | NM_008962.4 | chr14:44851234-44859375 |
| 17538 | Pse2 | NM_001128605.1 | chr1:180227003-180256300 | 17635 | Ptgdr2 | NM_009962.3 | chr19:10937159-10942511 |
| 17539 | Psenen | NM_025498.2 | chr7:30961865-30963184 | 17636 | Ptgds | NM_008963.2 | chr2:25466711-25469749 |
| 17540 | Psg16 | NM_007676.4 | chr7:17074039-17098971 | 17637 | Ptger1 | NM_013641.2 | chr8:83666639-83670103 |
| 17541 | Psg17 | NM_007677.2 | chr7:18813936-18821591 | 17638 | Ptger2 | NM_008964.4 | chr14:44988110-45003820 |
| 17542 | Psg18 | NM_001163685.1 | chr7:18348201-18354993 | 17639 | Ptger3 | NM_011196.2 | chr3:157566891-157644758 |
| 17543 | Psg19 | NM_011964.2 | chr7:18789124-18798510 | 17640 | Ptger4 | NM_001136079.2 | chr15:5233398-5244187 |
| 17544 | Psg20 | NM_054058.1 | chr7:18674365-18685992 | 17641 | Ptges | NM_022415.3 | chr2:30889470-30903297 |
| 17545 | Psg21 | NM_027403.4 | chr7:18646653-18656725 | 17642 | Ptges2 | NM_133783.2 | chr2:32395889-32402740 |
| 17546 | Psg22 | NM_001004152.2 | chr7:18718089-18727248 | 17643 | Ptges3 | NM_019766.4 | chr10:128058981-128077254 |
| 17547 | Psg23 | NM_020261.4 | chr7:18606342-18616501 | 17644 | Ptges3l | NM_026865.2 | chr11:101418813-101425333 |
| 17548 | Psg25 | NM_054060.1 | chr7:18519701-18532227 | 17645 | Ptgfr | NM_008966.3 | chr3:151798609-151837528 |
| 17549 | Psg26 | NM_001029893.1 | chr7:18474581-18484149 | 17646 | Ptgfrn | NM_011197.3 | chr3:101040235-101110166 |
| 17550 | Psg27 | NM_001037168.3 | chr7:18556513-18567305 | 17647 | Ptgir | NM_008967.3 | chr7:16906489-16910905 |
| 17551 | Psg28 | NM_054063.4 | chr7:18422535-18432055 | 17648 | Ptgis | NM_008968.3 | chr2:167203195-167240537 |
| 17552 | Psg29 | NM_002347.6 | chr7:17203476-17215756 | 17649 | Ptgr1 | NM_025968.3 | chr4:58965589-58987078 |
| 17553 | Psg-ps1 | NR_002857.1 | chr7:17672312-17682060 | 17650 | Ptgr2 | NM_001252625.1 | chr12:84285295-84315832 |
| 17554 | Psip1 | NM_001290527.1 | chr4:83461878-83486448 | 17651 | Ptgs1 | NM_008969.4 | chr2:36230425-36252271 |
| 17555 | Pskh1 | NM_173432.2 | chr8:105900473-105931802 | 17652 | Ptgs2 | NM_011198.4 | chr1:150100030-150108234 |
| 17556 | Psma1 | NM_011965.2 | chr7:114264549-114276116 | 17653 | Ptgs2os | NR_015466.3 | chr1:150074872-150099874 |

Fig.21 - 92

| | | | | | | | | |
|---|---|---|---|---|---|---|---|---|
| 17654 | Pth | NM_020623.2 | chr7:113385575-113388573 | | 17751 | Pxmp2 | NM_008993.2 | chr5:110274285-110286168 |
| 17655 | Pth1r | NM_001083935.1 | chr9:110722084-110743686 | | 17752 | Pxmp4 | NM_021534.3 | chr2:154587043-154603673 |
| 17656 | Pth2 | NM_053256.2 | chr7:45180994-45181838 | | 17753 | Pxn | NM_011223.3 | chr5:115506675-115555987 |
| 17657 | Pth2r | NM_139270.2 | chr1:65311256-65389244 | | 17754 | Pxt1 | NM_153390.1 | chr17:28933985-28942262 |
| 17658 | Pthlh | NM_008970.4 | chr6:147252108-147264013 | | 17755 | Pxylp1 | NM_001289645.1 | chr9:96823342-96899474 |
| 17659 | Ptk2 | NM_001130409.1 | chr15:73215556-73423191 | | 17756 | Pycard | NM_023258.4 | chr7:127991372-127993867 |
| 17660 | Ptk2b | NM_001162365.1 | chr14:66153256-66281052 | | 17757 | Pycr1 | NM_144795.3 | chr11:120635711-120643670 |
| 17661 | Ptk6 | NM_009184.2 | chr2:181195123-181202789 | | 17758 | Pycr2 | NM_133705.2 | chr1:180904273-180908088 |
| 17662 | Ptk7 | NM_175168.4 | chr17:46564450-46629504 | | 17759 | Pycrl | NM_025412.2 | chr15:75916462-75921560 |
| 17663 | Ptma | NM_008972.2 | chr1:86526735-86530698 | | 17760 | Pydc3 | NM_001162938.1 | chr1:173673679-173698392 |
| 17664 | Ptms | NM_026988.2 | chr6:124913674-124917946 | | 17761 | Pydc4 | NM_001177349.1 | chr1:173591956-173599274 |
| 17665 | Pth | NM_008973.2 | chr6:36715662-36811361 | | 17762 | Pygb | NM_153781.1 | chr2:150786795-150831748 |
| 17666 | Ptov1 | NM_133949.1 | chr7:44863067-44869788 | | 17763 | Pygl | NM_133198.2 | chr12:70190814-70227683 |
| 17667 | Ptp4a1 | NM_011200.2 | chr1:30940302-30949755 | | 17764 | Pygm | NM_011224.1 | chr19:6384428-6398459 |
| 17668 | Ptp4a2 | NM_001164745.1 | chr4:129820707-129850003 | | 17765 | Pygo1 | NM_028116.2 | chr9:72925649-72946615 |
| 17669 | Ptp4a3 | NM_001166388.1 | chr15:73724929-73758766 | | 17766 | Pygo2 | NM_026869.3 | chr3:89430836-89435130 |
| 17670 | Ptpdc1 | NM_207232.2 | chr13:48577868-48625672 | | 17767 | Pyhin1 | NM_175026.3 | chr1:173630858-173647928 |
| 17671 | Ptpla | NM_001012396.2 | chr2:14026830-14056035 | | 17768 | Pyroxd1 | NM_183165.3 | chr6:142345696-142367624 |
| 17672 | Ptplad1 | NM_021345.2 | chr9:64986982-85021717 | | 17769 | Pyroxd2 | NM_029011.2 | chr19:42752857-42752775 |
| 17673 | Ptplad2 | NM_025760.4 | chr4:88412929-88438926 | | 17770 | Pyurf | NM_025574.3 | chr6:57684738-57692078 |
| 17674 | Ptplb | NM_023587.2 | chr6:35022420-35109175 | | 17771 | Pvy | NM_145435.1 | chr11:102106675-102107776 |
| 17675 | Ptpmt1 | NM_025576.2 | chr2:90910712-90918050 | | 17772 | Pzp | NM_007376.4 | chr6:128483566-128526720 |
| 17676 | Ptpn1 | NM_011201.3 | chr2:167932326-167979385 | | 17773 | Qars | NM_001168270.1 | chr9:108509478-108515941 |
| 17677 | Ptpn11 | NM_001109992.1 | chr5:121130532-121191397 | | 17774 | Qdpr | NM_024236.2 | chr5:45434031-45450229 |
| 17678 | Ptpn12 | NM_011203.2 | chr5:20986644-21055797 | | 17775 | Qk | NM_001159516.1 | chr17:10210179-10319361 |
| 17679 | Ptpn13 | NM_011204.2 | chr5:103425191-103598361 | | 17776 | Qpct | NM_027455.3 | chr17:79051905-79090243 |
| 17680 | Ptpn14 | NM_008976.2 | chr1:189728267-189876693 | | 17777 | Qpctl | NM_026111.3 | chr7:19140216-19149196 |
| 17681 | Ptpn18 | NM_011206.2 | chr1:34459745-34473779 | | 17778 | Qprt | NM_133686.1 | chr7:127107769-127122029 |
| 17682 | Ptpn2 | NM_001127177.1 | chr18:67665500-67724621 | | 17779 | Qrfp | NM_183424.4 | chr2:31806167-31810580 |
| 17683 | Ptpn20 | NM_008978.2 | chr14:33589269-33640754 | | 17780 | Qrfpr | NM_198192.2 | chr3:36179425-36222775 |
| 17684 | Ptpn21 | NM_001146199.1 | chr12:98676760-98737405 | | 17781 | Qrich1 | NM_001114119.1 | chr9:108517086-108560167 |
| 17685 | Ptpn22 | NM_008979.2 | chr3:103860276-103912252 | | 17782 | Qrich2 | NM_001033267.2 | chr11:116441324-116454347 |
| 17686 | Ptpn23 | NM_001081043.1 | chr9:110389088-110408210 | | 17783 | Qsl1 | NM_001081054.2 | chr10:43874189-43901736 |
| 17687 | Ptpn3 | NM_011207.2 | chr4:57190840-57301837 | | 17784 | Qser1 | NM_001123327.2 | chr2:104754792-104816696 |
| 17688 | Ptpn4 | NM_019933.2 | chr1:119658092-119837071 | | 17785 | Qsox1 | NM_001024945.1 | chr1:155778154-155812899 |
| 17689 | Ptpn5 | NM_001163565.1 | chr7:47077799-47132598 | | 17786 | Qsox2 | NM_153539.3 | chr2:26209123-26237399 |
| 17690 | Ptpn6 | NM_001077620.1 | chr6:124720706-124738709 | | 17787 | Qtrt1 | NM_021888.2 | chr9:21411836-21420279 |
| 17691 | Ptpn7 | NM_177081.3 | chr1:135132724-135145320 | | 17788 | Qtrtd1 | NM_029128.2 | chr16:43861412-43889676 |
| 17692 | Ptpn9 | NM_019651.2 | chr9:56949697-57062807 | | 17789 | R3hcc1 | NM_001146012.2 | chr14:69697303-69707584 |
| 17693 | Ptpre | NM_001163688.1 | chr2:130450277-130554300 | | 17790 | R3hcc1l | NM_177464.4 | chr19:42518804-42592256 |
| 17694 | Ptprb | NM_029928.2 | chr10:116301373-116389538 | | 17791 | R3hdm1 | NM_181750.2 | chr1:128103305-128237735 |
| 17695 | Ptprc | NM_001111316.2 | chr1:138062858-138175126 | | 17792 | R3hdm2 | NM_001168292.1 | chr10:127390310-127499384 |
| 17696 | Ptprcap | NM_016933.3 | chr19:4154645-4156710 | | 17793 | R3hdm4 | NM_177994.4 | chr10:79910052-79916930 |
| 17697 | Ptprd | NM_011211.3 | chr4:75941236-78211895 | | 17794 | R3hdml | NM_001099331.2 | chr2:163492317-163502612 |
| 17698 | Ptpre | NM_011212.2 | chr7:135537823-135686294 | | 17795 | R74862 | NR_015529.2 | chr7:143032620-143053686 |
| 17699 | Ptprf | NM_011213.2 | chr4:118208212-118291397 | | 17796 | Rab1 | NM_008996.3 | chr11:20201601-20226856 |
| 17700 | Ptprg | NM_008979.3 | chr14:11553552-12242039 | | 17797 | Rab10 | NM_016676.5 | chr12:3247427-3309989 |
| 17701 | Ptprh | NM_207270.2 | chr7:4548613-4604041 | | 17798 | Rab10os | NR_015551.1 | chr12:3235790-3250374 |
| 17702 | Ptprj | NM_001136657.1 | chr2:90429755-90479174 | | 17799 | Rab11a | NM_017382.5 | chr9:64715299-64737756 |
| 17703 | Ptprk | NM_008984.2 | chr10:28074819-28597397 | | 17800 | Rab11b | NM_008997.3 | chr17:33742483-33760486 |
| 17704 | Ptprm | NM_008984.2 | chr17:66666847-67354459 | | 17801 | Rab11fip1 | NM_001080813.2 | chr8:27138772-27174646 |
| 17705 | Ptprn | NM_008985.2 | chr1:75247040-75264208 | | 17802 | Rab11fip2 | NM_001033172.3 | chr19:59902883-59943364 |
| 17706 | Ptprn2 | NM_011215.2 | chr1:116485719-117278167 | | 17803 | Rab11fip3 | NM_001162868.1 | chr17:25989035-28069177 |
| 17707 | Ptpro | NM_001164401.1 | chr6:137252298-137464633 | | 17804 | Rab11fip4 | NM_175543.3 | chr11:79591211-79694012 |
| 17708 | Ptprq | NM_001081432.1 | chr10:107517359-107720027 | | 17805 | Rab11fip4os1 | NR_003283.1 | chr11:79607078-79623163 |
| 17709 | Ptprq | NM_001161837.1 | chr10:116143897-116274929 | | 17806 | Rab11fip4os2 | NR_045898.2 | chr11:79670372-79675086 |
| 17710 | Ptprs | NM_001252453.1 | chr17:56412425-56476480 | | 17807 | Rab11fip5 | NM_001003955.2 | chr6:85354961-85374634 |
| 17711 | Ptprt | NM_001291149.1 | chr2:161521987-162661147 | | 17808 | Rab2 | NM_024448.2 | chr17:66494511-66519670 |
| 17712 | Ptprtos | NR_040617.1 | chr2:162390812-162393946 | | 17809 | Rab13 | NM_026677.4 | chr3:90220783-90226387 |
| 17713 | Ptpru | NM_001083139.2 | chr4:131768456-131838278 | | 17810 | Rab14 | NM_026697.3 | chr2:35180204-35201120 |
| 17714 | Ptprv | NM_007955.3 | chr1:135150497-135132575 | | 17811 | Rab15 | NM_134050.4 | chr12:76797962-76822524 |
| 17715 | Ptprz1 | NM_001081306.1 | chr6:22875501-23052916 | | 17812 | Rab17 | NM_001159725.2 | chr1:90958132-90967667 |
| 17716 | Ptrf | NM_008986.2 | chr16:100956735-100970617 | | 17813 | Rab18 | NM_001278447.1 | chr18:6765166-6791606 |
| 17717 | Ptrh1 | NM_178595.3 | chr2:32775820-32777593 | | 17814 | Rab19 | NM_011226.1 | chr6:39381427-39390379 |
| 17718 | Ptrh2 | NM_001098810.2 | chr11:86684080-86692457 | | 17815 | Rab1b | NM_029576.3 | chr19:5099206-5106998 |
| 17719 | Ptrhd1 | NM_001204912.1 | chr12:4234026-4240123 | | 17816 | Rab20 | NM_011227.1 | chr8:114539716-114578499 |
| 17720 | Pts | NM_011220.2 | chr9:50521616-50528641 | | 17817 | Rab21 | NM_024454.1 | chr10:115289861-115315591 |
| 17721 | Ptg1 | NM_001331054.1 | chr1:43420247-43426248 | | 17818 | Rab22a | NM_024436.3 | chr2:173659844-173702182 |
| 17722 | Ptg1ip | NM_145925.3 | chr10:77581766-77598732 | | 17819 | Rab23 | NM_001159729.1 | chr1:33720418-33742564 |
| 17723 | Ptx3 | NM_008987.3 | chr3:66219886-66225806 | | 17820 | Rab24 | NM_009000.3 | chr13:55319222-55321980 |
| 17724 | Ptx4 | NM_001120765.1 | chr17:25120759-25125268 | | 17821 | Rab25 | NM_016899.4 | chr3:88542028-88548279 |
| 17725 | Puf60 | NM_001164600.1 | chr15:76070181-76080870 | | 17822 | Rab26 | NM_177375.1 | chr17:24529053-24533747 |
| 17726 | Pum1 | NM_001159603.1 | chr4:130663358-130781565 | | 17823 | Rab26os | NR_045289.1 | chr17:24528250-24528744 |
| 17727 | Pum2 | NM_001160239.1 | chr12:8742258-8752583 | | 17824 | Rab27a | NM_023635.6 | chr9:73044809-73097614 |
| 17728 | Pura | NM_008989.3 | chr18:36281161-36288244 | | 17825 | Rab27b | NM_001082552.2 | chr18:69979130-70141605 |
| 17729 | Purb | NM_011221.3 | chr11:6467598-6476076 | | 17826 | Rab28 | NM_027295.3 | chr5:41624972-41708179 |
| 17730 | Purg | NM_001098253.1 | chr8:33386324-33417469 | | 17827 | Rab2a | NM_021518.3 | chr4:8535643-8607702 |
| 17731 | Pus1 | NM_025561.3 | chr5:110773666-110780596 | | 17828 | Rab2b | NM_172601.3 | chr14:52281758-52279395 |
| 17732 | Pus10 | NM_001033654.2 | chr11:23565673-23732876 | | 17829 | Rab30 | NM_029494.2 | chr7:92741713-92837117 |
| 17733 | Pus3 | NM_023292.4 | chr9:35589465-35567400 | | 17830 | Rab31 | NM_133685.2 | chr17:65651725-65772752 |
| 17734 | Pus7 | NM_001289780.1 | chr5:23740164-23783711 | | 17831 | Rab32 | NM_026405.3 | chr10:10545038-10558207 |
| 17735 | Pus7l | NM_172437.3 | chr15:94522639-94543507 | | 17832 | Rab33a | NM_011228.2 | chrX:48519284-48530240 |
| 17736 | Pusl1 | NM_001033490.1 | chr4:155888859-155891762 | | 17833 | Rab33b | NM_016858.2 | chr3:51483965-51496212 |
| 17737 | Pvalb | NM_013645.3 | chr15:78191117-78206351 | | 17834 | Rab34 | NM_001159482.1 | chr11:78198426-78192193 |
| 17738 | Pvr | NM_009368.2 | chr7:19903577-19921143 | | 17835 | Rab35 | NM_198163.1 | chr5:115615986-115647158 |
| 17739 | Pvrl1 | NM_021424.2 | chr9:43744575-43807461 | | 17836 | Rab36 | NM_029781.3 | chr10:75037088-75054100 |
| 17740 | Pvrl2 | NM_008990.4 | chr7:19724160-19749573 | | 17837 | Rab37 | NM_001163753.1 | chr11:115091430-115162240 |
| 17741 | Pvrl3 | NM_021495.4 | chr16:46447160-46496967 | | 17838 | Rab38 | NM_028238.7 | chr7:88430272-88491572 |
| 17742 | Pvrl4 | NM_001122680.1 | chr1:171370172-171388287 | | 17839 | Rab39 | NM_175562.3 | chr9:53684109-53706232 |
| 17743 | Pvt1 | NR_003368.2 | chr15:62037985-62250976 | | 17840 | Rab39b | NM_175122.6 | chrX:75572044-75576231 |
| 17744 | Pwp1 | NM_133993.3 | chr10:85871830-85889103 | | 17841 | Rab3a | NM_001166399.2 | chr8:70754678-70758686 |
| 17745 | Pwp2 | NM_029546.2 | chr10:78170909-78186149 | | 17842 | Rab3b | NM_023537.5 | chr4:108879069-108943324 |
| 17746 | Pwwp2a | NM_001164231.1 | chr11:43681997-43712653 | | 17843 | Rab3c | NM_023852.5 | chr13:100054186-110289206 |
| 17747 | Pwwp2b | NM_001033206.2 | chr7:139248481-139267253 | | 17844 | Rab3d | NM_031874.4 | chr9:21907510-21918121 |
| 17748 | Pxdc1 | NM_025831.3 | chr13:34627840-34652681 | | 17845 | Rab3gap1 | NM_178690.4 | chr1:127868772-127943876 |
| 17749 | Pxdn | NM_181395.2 | chr12:29938035-30017658 | | 17846 | Rab3gap2 | NM_001163754.1 | chr1:185204167-185286746 |
| 17750 | Pxk | NM_145458.3 | chr14:8098212-8165111 | | 17847 | Rab3il1 | NM_144538.2 | chr19:10018237-10035586 |

Fig.21-93

| | | | | | | | |
|---|---|---|---|---|---|---|---|
| 17848 | Rab3ip | NM_001003950.2 | chr10:116905783-116950380 | 17945 | Rap1gap2 | NM_001015046.2 | chr11:74383482-74590158 |
| 17849 | Rab40b | NM_139147.3 | chr11:121356120-121388251 | 17946 | Rap1gds1 | NM_001040690.2 | chr3:138925896-139075201 |
| 17850 | Rab40c | NM_139154.2 | chr17:25882113-25919714 | 17947 | Rap2a | NM_029519.3 | chr14:120478460-120567192 |
| 17851 | Rab42 | NM_001081651.1 | chr4:132302193-132303356 | 17948 | Rap2b | NM_028712.4 | chr3:61364506-61368703 |
| 17852 | Rab43 | NM_001039394.1 | chr6:87788852-87811779 | 17949 | Rap2c | NM_172413.2 | chrX:51003913-51018018 |
| 17853 | Rab44 | NM_001002786.2 | chr17:29135055-29148976 | 17950 | Rapgef1 | NM_001039086.1 | chr2:29619719-29740363 |
| 17854 | Rab4a | NM_009003.3 | chr8:123805995-123835291 | 17951 | Rapgef2 | NM_001009624.3 | chr3:79062510-79145875 |
| 17855 | Rab4b | NM_029391.2 | chr7:27168432-27178283 | 17952 | Rapgef3 | NM_001177810.1 | chr15:97744769-97767666 |
| 17856 | Rab5a | NM_025887.4 | chr17:53479233-53507678 | 17953 | Rapgef4 | NM_001204165.1 | chr2:71981214-72257474 |
| 17857 | Rab5b | NM_177411.4 | chr10:128677182-128696268 | 17954 | Rapgef5 | NM_175930.5 | chr12:117516478-117756978 |
| 17858 | Rab5c | NM_024456.5 | chr11:100715002-100738215 | 17955 | Rapgef6 | NM_001252494.1 | chr11:54522844-54699286 |
| 17859 | Rab6a | NM_001163663.1 | chr7:100607585-100641268 | 17956 | Rapgefl1 | NM_001080925.1 | chr11:98836784-98853005 |
| 17860 | Rab6b | NM_173781.4 | chr9:103112073-103185270 | 17957 | Raph1 | NM_001045513.3 | chr1:60483184-60566765 |
| 17861 | Rab7 | NM_009005.3 | chr6:87999105-88045270 | 17958 | Rapsn | NM_009023.3 | chr2:91035626-91045729 |
| 17862 | Rab7l1 | NM_144875.2 | chr1:131867276-131872889 | 17959 | Rara | NM_001176528.1 | chr11:98960470-98974942 |
| 17863 | Rab8a | NM_023126.2 | chr8:72161199-72181366 | 17960 | Rarb | NM_001289760.1 | chr14:16430839-17082331 |
| 17864 | Rab8b | NM_173413.3 | chr9:66843663-66919705 | 17961 | Rarg | NM_001042727.2 | chr15:102234937-102246500 |
| 17865 | Rab9 | NM_019773.2 | chrX:166457251-166479867 | 17962 | Rarres1 | NM_001164763.1 | chr3:67478885-67515523 |
| 17866 | Rab9b | NM_176971.2 | chrX:136858150-136868540 | 17963 | Rarres2 | NM_027852.2 | chr6:48569697-48572670 |
| 17867 | Rabac1 | NM_010261.2 | chr7:24969749-24972728 | 17964 | Rars | NM_025936.3 | chr11:35808380-35834528 |
| 17868 | Rabep1 | NM_001291141.1 | chr11:70844760-70943105 | 17965 | Rars2 | NM_181406.3 | chr4:34614957-34660167 |
| 17869 | Rabep2 | NM_030566.2 | chr7:126428766-126445907 | 17966 | Rasa1 | NM_145452.3 | chr13:85214698-85289486 |
| 17870 | Rabepk | NM_145522.4 | chr2:34778665-34799912 | 17967 | Rasa2 | NM_053268.2 | chr9:96539299-96631503 |
| 17871 | Rabgap1 | NM_001033960.1 | chr2:37452253-37544962 | 17968 | Rasa3 | NM_009025.2 | chr8:13567217-13677587 |
| 17872 | Rabgap1l | NM_001038621.2 | chr1:160219173-160351571 | 17969 | Rasa4 | NM_001039103.3 | chr5:136083915-136111861 |
| 17873 | Rabgef1 | NM_001199059.1 | chr5:130171818-130214337 | 17970 | Rasal1 | NM_001281999.1 | chr5:120649187-120679610 |
| 17874 | Rabggta | NM_019519.2 | chr14:55715876-55722176 | 17971 | Rasal2 | NM_177644.5 | chr1:157135182-157412595 |
| 17875 | Rabggtb | NM_001163478.1 | chr3:153907288-153912966 | 17972 | Rasal3 | NM_178785.3 | chr17:32390660-32403581 |
| 17876 | Rabif | NM_145510.1 | chr1:134494659-134507684 | 17973 | Rasd1 | NM_009026.5 | chr11:59963180-59964944 |
| 17877 | Rabl2 | NM_026817.3 | chr15:89582526-89591923 | 17974 | Rasd2 | NM_029182.1 | chr8:75213943-75224113 |
| 17878 | Rabl3 | NM_001042491.1 | chr16:37539893-37572385 | 17975 | Rasef | NM_001017427.1 | chr4:73714578-73790602 |
| 17879 | Rabl6 | NM_001024616.1 | chr2:25583017-25608446 | 17976 | Rasgef1a | NM_027526.1 | chr6:118066384-118091546 |
| 17880 | Rac1 | NM_009007.2 | chr5:143505480-143527993 | 17977 | Rasgef1b | NM_145839.2 | chr5:99217419-99252927 |
| 17881 | Rac2 | NM_009008.3 | chr15:78559158-78572783 | 17978 | Rasgef1c | NM_029004.1 | chr11:49901834-49980223 |
| 17882 | Rac3 | NM_133223.4 | chr11:120721467-120723969 | 17979 | Rasgrf1 | NM_001039655.1 | chr9:89909774-89915847 |
| 17883 | Racgap1 | NM_001253808.1 | chr15:99620495-99651656 | 17980 | Rasgrf2 | NM_009027.3 | chr13:91880406-91988042 |
| 17884 | Rad1 | NM_001289467.1 | chr15:10486037-10493695 | 17981 | Rasgrp1 | NM_011246.2 | chr2:117279992-117342877 |
| 17885 | Rad17 | NM_001044371.2 | chr13:100617163-100651061 | 17982 | Rasgrp2 | NM_011242.2 | chr19:6400582-6415216 |
| 17886 | Rad18 | NM_001167936.1 | chr6:112619850-112696670 | 17983 | Rasgrp3 | NM_001146493.1 | chr17:75435904-75529053 |
| 17887 | Rad21 | NM_009009.4 | chr15:51962603-51991760 | 17984 | Rasgrp4 | NM_001174155.1 | chr7:29134932-29153955 |
| 17888 | Rad23l | NM_001276400.1 | chr2:151645403-151668533 | 17985 | Rasip1 | NM_028544.1 | chr7:45627536-45639992 |
| 17889 | Rad23a | NM_009010.5 | chr8:84834651-84840685 | 17986 | Rasl10a | NM_145216.3 | chr11:5058127-5060383 |
| 17890 | Rad23b | NM_009011.4 | chr4:55350041-55392237 | 17987 | Rasl10b | NM_001013886.2 | chr11:83410071-83421038 |
| 17891 | Rad50 | NM_009012.2 | chr11:53649518-53707319 | 17988 | Rasl11a | NM_026864.1 | chr5:146845070-146847726 |
| 17892 | Rad51 | NM_011234.4 | chr2:119112816-119136070 | 17989 | Rasl11b | NM_026878.1 | chr5:74195325-74199477 |
| 17893 | Rad51ap1 | NM_009013.3 | chr6:126923418-126939655 | 17990 | Rasl12 | NM_001033158.2 | chr9:65398487-65412707 |
| 17894 | Rad51ap2 | NM_001111118.1 | chr12:11456076-11462928 | 17991 | Rasl2-9 | NM_009028.2 | chr7:5124941-5125950 |
| 17895 | Rad51b | NM_001252562.1 | chr12:79297350-79508654 | 17992 | Rassf1 | NM_001243748.1 | chr9:107551554-107562267 |
| 17896 | Rad51c | NM_001291440.1 | chr11:87377606-87404954 | 17993 | Rassf10 | NM_175279.3 | chr7:112953861-112957458 |
| 17897 | Rad51d | NM_001277938.1 | chr11:82873062-82890624 | 17994 | Rassf2 | NM_175445.4 | chr2:131992849-132029988 |
| 17898 | Rad52 | NM_001166381.1 | chr6:119902697-119922823 | 17995 | Rassf3 | NM_138956.3 | chr10:121410350-121476250 |
| 17899 | Rad54b | NM_001039556.3 | chr4:11558919-11615808 | 17996 | Rassf4 | NM_178045.4 | chr6:116633007-116673836 |
| 17900 | Rad54l | NM_001122958.1 | chr4:116096954-116123689 | 17997 | Rassf5 | NM_018750.4 | chr1:131176409-131245178 |
| 17901 | Rad54l2 | NM_030730.2 | chr9:106688079-106789213 | 17998 | Rassf6 | NM_028478.3 | chr5:90603075-90640527 |
| 17902 | Rad9a | NM_011237.2 | chr19:4196197-4201603 | 17999 | Rassf7 | NM_028886.3 | chr7:141215859-141218568 |
| 17903 | Rad9b | NM_144912.3 | chr5:122325507-122354195 | 18000 | Rassf8 | NM_027760.2 | chr6:145808182-145817584 |
| 17904 | Radil | NM_001289588.1 | chr5:142484838-142551098 | 18001 | Rassf9 | NM_146240.4 | chr10:102512221-102546560 |
| 17905 | Rael | NM_175112.5 | chr2:173000118-173015739 | 18002 | Raver1 | NM_027911.3 | chr9:21074163-21091988 |
| 17906 | Raet1a | NM_009016.1 | chr10:22158608-22374139 | 18003 | Raver1-ndx1l | NR_038081.2 | chr9:21067513-21092008 |
| 17907 | Raet1b | NM_009017.1 | chr10:22173874-22374113 | 18004 | Raver2 | NM_189024.1 | chr4:101069037-101152370 |
| 17908 | Raet1c | NM_020030.2 | chr10:22173901-22374139 | 18005 | Rax | NM_013833.2 | chr18:65934638-65939089 |
| 17909 | Raet1d | NM_020030.2 | chr10:22361893-22374139 | 18006 | Rb1 | NM_009029.2 | chr14:73195501-73325791 |
| 17910 | Raet1e | NM_198112.5 | chr10:22173520-22183914 | 18007 | Rb1cc1 | NM_009826.4 | chr1:6214661-6276104 |
| 17911 | Raf1 | NM_029780.3 | chr6:115618572-115676635 | 18008 | Rbak | NM_001045482.2 | chr5:143172185-143180775 |
| 17912 | Rag1 | NM_009019.2 | chr2:101638251-101649532 | 18009 | Rbakdn | NR_040424.1 | chr5:143164778-143165751 |
| 17913 | Rag2 | NM_009020.3 | chr2:101624747-101632528 | 18010 | Rbbp4 | NM_009030.3 | chr4:129307099-129335370 |
| 17914 | Rai1 | NM_001037764.1 | chr11:60340031-60399195 | 18011 | Rbbp5 | NM_172517.2 | chr1:132477366-132505665 |
| 17915 | Rai14 | NM_001166408.1 | chr15:10568977-10714631 | 18012 | Rbbp6 | NM_011247.2 | chr7:122970963-123002572 |
| 17916 | Rai2 | NM_001103367.1 | chrX:161717035-161779494 | 18013 | Rbbp7 | NM_009031.3 | chrX:162760371-162779090 |
| 17917 | Rala | NM_019491.5 | chr13:17820574-17944217 | 18014 | Rbbp8 | NM_001081223.2 | chr18:11657348-11743207 |
| 17918 | Ralb | NM_022227.5 | chr1:119470304-119504782 | 18015 | Rbbp8nl | NM_173031.3 | chr2:180277645-180289879 |
| 17919 | Ralbp1 | NM_001198949.1 | chr17:65848427-65864923 | 18016 | Rbbp9 | NM_015754.2 | chr2:144542264-144550859 |
| 17920 | Ralgapa1 | NM_001003719.2 | chr12:55602889-55821516 | 18017 | Rbck1 | NM_001083921.1 | chr2:152316833-152332425 |
| 17921 | Ralgapa2 | NM_001033348.3 | chr2:146241298-146512604 | 18018 | Rbfa | NM_199197.1 | chr18:80192263-80200619 |
| 17922 | Ralgapb | NM_001291137.1 | chr2:158409852-158490253 | 18019 | Rbfox1 | NM_021477.5 | chr16:5884792-7412486 |
| 17923 | Ralgds | NM_001145834.1 | chr2:28513166-28559082 | 18020 | Rbfox2 | NM_001110827.2 | chr15:77078989-77307053 |
| 17924 | Ralgps1 | NM_001290570.1 | chr2:33133418-33371494 | 18021 | Rbfox3 | NM_001024931.2 | chr11:118469759-118909572 |
| 17925 | Ralgps2 | NM_001159965.1 | chr1:156804165-156939626 | 18022 | Rbks | NM_153196.1 | chr5:31624438-31697610 |
| 17926 | Raly | NM_001139101.1 | chr2:154791109-154867261 | 18023 | Rbl1 | NM_001139516.1 | chr2:157174995-157204534 |
| 17927 | Ralyl | NM_001168328.1 | chr3:13471654-14182287 | 18024 | Rbl2 | NM_001282000.1 | chr8:91070056-91123844 |
| 17928 | Ramp1 | NM_001168392.1 | chr1:91179821-91206790 | 18025 | Rbm10 | NM_001167775.1 | chrX:20617502-20659305 |
| 17929 | Ramp2 | NM_019444.3 | chr11:101246333-101248250 | 18026 | Rbm11 | NM_198302.2 | chr16:75592890-75602825 |
| 17930 | Ramp3 | NM_019511.3 | chr11:6658532-6677475 | 18027 | Rbm12 | NM_029397.3 | chr2:156094881-156111965 |
| 17931 | Ran | NM_009391.3 | chr5:129020155-129024321 | 18028 | Rbm12b1 | NM_028226.2 | chr4:12140116-12146746 |
| 17932 | Ranbp1 | NM_011239.3 | chr16:18239978-18248694 | 18029 | Rbm12b2 | NM_198957.2 | chr4:12089369-12096271 |
| 17933 | Ranbp10 | NM_148824.4 | chr8:105768307-105827850 | 18030 | Rbm14 | NM_019869.3 | chr19:4800565-4811634 |
| 17934 | Ranbp17 | NM_023144.2 | chr11:33211793-33513746 | 18031 | Rbm14-rbm4 | NM_001290127.1 | chr19:4784292-4811634 |
| 17935 | Ranbp2 | NM_011240.3 | chr10:58446851-58494154 | 18032 | Rbm15 | NM_001045807.1 | chr3:107326109-107333289 |
| 17936 | Ranbp3 | NM_001252466.1 | chr17:56673224-56711769 | 18033 | Rbm15b | NM_175402.4 | chr9:106883984-106887000 |
| 17937 | Ranbp3l | NM_198024.2 | chr15:8967948-9067333 | 18034 | Rbm17 | NM_152824.1 | chr2:11583438-11603199 |
| 17938 | Ranbp6 | NM_177721.4 | chr19:29808107-29812974 | 18035 | Rbm18 | NM_001159635.1 | chr2:36136078-36136704 |
| 17939 | Ranbp9 | NM_019930.2 | chr13:43402672-43480973 | 18036 | Rbm19 | NM_028762.1 | chr5:120116512-120198973 |
| 17940 | Rangap1 | NM_001146174.1 | chr15:81704247-81729919 | 18037 | Rbm20 | NM_001170847.1 | chr19:53677305-53867080 |
| 17941 | Rangrf | NM_001285441.1 | chr11:68972483-68975185 | 18038 | Rbm22 | NM_025776.2 | chr18:60560785-60572729 |
| 17942 | Rap1a | NM_145541.5 | chr13:46418299-46431099 | 18039 | Rbm24 | NM_001081425.1 | chr13:46418299-46431099 |
| 17943 | Rap1b | NM_024457.2 | chr10:117843596-117884974 | 18040 | Rbm25 | NM_027349.3 | chr12:83632233-83683123 |
| 17944 | Rap1gap | NM_001081155.2 | chr4:137681666-137729861 | 18041 | Rbm26 | NM_134077.4 | chr14:105114518-105177327 |

Fig.21 - 94

| | | | | | | | | |
|---|---|---|---|---|---|---|---|---|
| 18042 | Rbm27 | NM_172626.2 | chr18:42275352-42341540 | 18139 | Reg3g | NM_011260.1 | chr6:78466267-78468874 |
| 18043 | Rbm28 | NM_133925.1 | chr6:29123572-29164724 | 18140 | Reg4 | NM_026328.2 | chr3:98222155-98236748 |
| 18044 | Rbm3 | NM_001166409.2 | chrX:8142355-8145880 | 18141 | Rel | NM_009044.2 | chr11:23741728-23770970 |
| 18045 | Rbm3ly | NM_028970.1 | chrY:12688109-17402718 | 18142 | Rela | NM_009045.4 | chr19:5637489-5648130 |
| 18046 | Rbm33 | NM_028234.1 | chr5:28317188-28419242 | 18143 | Relb | NM_001290457.1 | chr7:19606222-19629438 |
| 18047 | Rbm34 | NM_172762.2 | chr8:126947172-126971079 | 18144 | Rell1 | NM_145923.4 | chr5:63908897-63968897 |
| 18048 | Rbm38 | NM_019547.2 | chr2:173021901-173034731 | 18145 | Rell2 | NM_153793.2 | chr18:37955558-37959179 |
| 18049 | Rbm39 | NM_001291114.1 | chr2:156147240-156180238 | 18146 | Reln | NM_011261.2 | chr5:21884453-22344705 |
| 18050 | Rbm3os | NR_033561.1 | chrX:8145426-8147963 | 18147 | Relt | NM_177073.6 | chr7:100845847-100863413 |
| 18051 | Rbm4 | NM_001290122.1 | chr19:4784299-4794009 | 18148 | Rem1 | NM_009047.5 | chr2:152627007-152635191 |
| 18052 | Rbm41 | NM_001172347.1 | chrX:139941527-139998595 | 18149 | Rem2 | NM_080726.3 | chr14:54476099-54480434 |
| 18053 | Rbm42 | NM_133693.2 | chr7:30640994-30650228 | 18150 | Ren1 | NM_031192.3 | chr1:133350673-133360319 |
| 18054 | Rbm43 | NM_001141981.1 | chr2:51924448-51935009 | 18151 | Ren2 | NM_031193.2 | chr1:133350565-133360323 |
| 18055 | Rbm44 | NM_001033408.4 | chr1:91143102-91170795 | 18152 | Renbp | NM_001164704.1 | chrX:73922120-73930850 |
| 18056 | Rbm45 | NM_153405.2 | chr2:76369983-76383767 | 18153 | Rep15 | NM_026620.2 | chr6:147032536-147033518 |
| 18057 | Rbm46 | NM_001277170.1 | chr3:82836522-82876483 | 18154 | Repin1 | NM_001079901.1 | chr6:48593882-48599082 |
| 18058 | Rbm46os | NR_040381.1 | chr3:82904476-82943638 | 18155 | Reps1 | NM_001111065.1 | chr10:18055939-18125155 |
| 18059 | Rbm47 | NM_001127382.1 | chr5:66016548-66151954 | 18156 | Reps2 | NM_001290633.1 | chrX:162411951-162643658 |
| 18060 | Rbm48 | NM_172991.4 | chr5:3583977-3596547 | 18157 | Rer1 | NM_026395.1 | chr4:155074111-155086297 |
| 18061 | Rbm4b | NM_025717.3 | chr19:4756524-4765941 | 18158 | Rere | NM_001085492.1 | chr4:150281915-150621966 |
| 18062 | Rbm5 | NM_148930.3 | chr9:107740494-107771002 | 18159 | Rerg | NM_001164212.1 | chr6:137054824-137169718 |
| 18063 | Rbm6 | NM_011251.3 | chr9:107773558-107872819 | 18160 | Rergl | NM_001128090.1 | chr6:139493181-139501909 |
| 18064 | Rbm7 | NM_144948.5 | chr9:48468696-48495330 | 18161 | Resp18 | NM_009049.1 | chr1:75272201-75278380 |
| 18065 | Rbm8a | NM_011102407.1 | chr3:96629927-96633791 | 18162 | Rest | NM_011263.2 | chr5:77265493-77283697 |
| 18066 | Rbms1 | NM_001141931.1 | chr2:60751952-60881438 | 18163 | Ret | NM_001080780.1 | chr6:118151747-118197744 |
| 18067 | Rbms2 | NM_001099080.1 | chr10:128129469-128180297 | 18164 | Retn | NM_001204959.1 | chr8:3655769-3659818 |
| 18068 | Rbms3 | NM_001172121.1 | chr9:116572746-117629913 | 18165 | Retnla | NM_020509.3 | chr16:48842551-48844461 |
| 18069 | Rbmx | NM_001166623.1 | chrX:57388029-57393036 | 18166 | Retnlb | NM_023881.4 | chr16:48816855-48818892 |
| 18070 | Rbmx2 | NM_173376.3 | chrX:48695003-48710719 | 18167 | Retnlg | NM_181596.4 | chr16:48872607-48874498 |
| 18071 | Rbmxl1 | NM_001252089.1 | chr8:78505268-78508928 | 18168 | Retsat | NM_026159.4 | chr6:72598627-72607488 |
| 18072 | Rbmxl2 | NM_029660.2 | chr7:107209484-107210916 | 18169 | Rev1 | NM_019570.3 | chr1:38052785-38129662 |
| 18073 | Rbmy | NM_011253.2 | chrY:2830679-3783271 | 18170 | Rev3l | NM_011264.3 | chr10:39732159-39875205 |
| 18074 | Rbp1 | NM_011254.5 | chr9:98422960-98446550 | 18171 | Rex2 | NM_001177767.1 | chr4:147021849-147060799 |
| 18075 | Rbp2 | NM_009034.4 | chr9:98490536-98509771 | 18172 | Rexo1 | NM_025852.3 | chr10:80540925-80561560 |
| 18076 | Rbp3 | NM_015745.2 | chr14:33954021-33964216 | 18173 | Rexo2 | NM_024233.3 | chr9:48468513-48480611 |
| 18077 | Rbp4 | NM_011159487.1 | chr19:38118619-38125321 | 18174 | Rexo4 | NM_207234.2 | chr2:26893562-26964386 |
| 18078 | Rbp7 | NM_022020.2 | chr4:149449701-149454968 | 18175 | Rfc1 | NM_011258.2 | chr5:65261851-65336639 |
| 18079 | Rbpj | NM_001080927.2 | chr5:53590485-53657445 | 18176 | Rfc2 | NM_020022.2 | chr5:134582689-134598328 |
| 18080 | Rbpjl | NM_009034.1 | chr2:164403193-164415448 | 18177 | Rfc3 | NM_027009.2 | chr5:151642823-151651208 |
| 18081 | Rbpms | NM_001042674.2 | chr8:33782643-33929863 | 18178 | Rfc4 | NM_145480.1 | chr16:23113947-23127730 |
| 18082 | Rbpms2 | NM_028030.3 | chr9:65630581-65660518 | 18179 | Rfc5 | NM_028128.1 | chr5:117379144-117389023 |
| 18083 | Rbx1 | NM_019712.3 | chr15:81466315-81476369 | 18180 | Rfesd | NM_001131068.1 | chr13:76001534-76018606 |
| 18084 | Rc3h1 | NM_001024952.2 | chr1:160906410-160974976 | 18181 | Rfk | NM_001007465.3 | chr11:82803818-82871230 |
| 18085 | Rc3h2 | NM_001100591.1 | chr2:37370070-37422903 | 18182 | Rfk | NM_019437.3 | chr19:17394042-17401349 |
| 18086 | Rcan1 | NM_001081549.1 | chr16:92391950-92466169 | 18183 | Rfng | NM_009053.2 | chr11:120780744-120784204 |
| 18087 | Rcan2 | NM_001286653.1 | chr17:43804002-44039516 | 18184 | Rfpl3s | NM_183111.2 | chr5:55962588-55980932 |
| 18088 | Rcan3 | NM_022980.4 | chr4:135412308-135433805 | 18185 | Rfpl4 | NM_001145013.1 | chr7:5109786-5118911 |
| 18089 | Rcbtb1 | NM_027764.2 | chr14:59201227-59237265 | 18186 | Rfpl4b | NM_001177783.1 | chr10:38820540-38821779 |
| 18090 | Rcbtb2 | NM_001170694.1 | chr14:73142509-73184054 | 18187 | Rft1 | NM_177815.3 | chr14:30654874-30691313 |
| 18091 | Rcc1 | NM_001197082.1 | chr4:132331918-132345750 | 18188 | Rftn1 | NM_183397.2 | chr17:49993306-50190497 |
| 18092 | Rcc2 | NM_173867.5 | chr4:140701472-140723220 | 18189 | Rftn2 | NM_028713.1 | chr1:55170159-55226782 |
| 18093 | Rccd1 | NM_173445.4 | chr7:80316615-80324454 | 18190 | Rfwd2 | NM_011931.3 | chr1:159232325-159347580 |
| 18094 | Rce1 | NM_023131.1 | chr19:4622550-4625617 | 18191 | Rfwd3 | NM_146218.4 | chr8:111270943-111300222 |
| 18095 | Rchy1 | NM_001271797.1 | chr5:91948841-91963068 | 18192 | Rfx1 | NM_009555.4 | chr8:84066835-84096992 |
| 18096 | Rcl1 | NM_015525.2 | chr19:29101374-29143843 | 18193 | Rfx2 | NM_009056.2 | chr17:56775896-56831008 |
| 18097 | Rcn1 | NM_009037.2 | chr2:105385947-105399319 | 18194 | Rfx3 | NM_001166414.1 | chr19:27761720-27982948 |
| 18098 | Rcn2 | NM_001278274.1 | chr9:56041844-58043245 | 18195 | Rfx4 | NM_001024918.1 | chr10:84756047-84906536 |
| 18099 | Rcn3 | NM_026555.2 | chr7:45082913-45092213 | 18196 | Rfx5 | NM_017395.2 | chr3:94955014-94961561 |
| 18100 | Rcor1 | NM_198023.2 | chr12:111039797-111113386 | 18197 | Rfx6 | NM_001159389.1 | chr10:51677758-51730429 |
| 18101 | Rcor2 | NM_054048.3 | chr19:7269763-7275225 | 18198 | Rfx7 | NM_001033536.1 | chr9:72532239-72622949 |
| 18102 | Rcor3 | NM_029278.1 | chr1:192098545-192138040 | 18199 | Rfx8 | NM_001145660.1 | chr1:39665300-39720989 |
| 18103 | Rcsd1 | NM_001098846.1 | chr1:165648944-165708094 | 18200 | Rfxank | NM_001025589.1 | chr8:70130805-70139197 |
| 18104 | Rcvrn | NM_009038.1 | chr11:67695325-67703355 | 18201 | Rfxap | NM_133231.2 | chr3:54803114-54807791 |
| 18105 | Rd3 | NM_001177900.2 | chr1:191977369-191988282 | 18202 | Rgag1 | NM_001040434.2 | chrX:143099593-143104335 |
| 18106 | Rd3l | NM_001127685.1 | chr12:111979322-111980751 | 18203 | Rgag4 | NM_001278534.1 | chrX:102066941-102071307 |
| 18107 | Rdh1 | NM_080436.3 | chr10:127759762-127768299 | 18204 | Rgcc | NM_025427.2 | chr14:79288749-79301635 |
| 18108 | Rdh10 | NM_133832.3 | chr1:16105881-16132550 | 18205 | Rgl1 | NM_016846.3 | chr1:152517529-152625111 |
| 18109 | Rdh11 | NM_021557.5 | chr12:79175550-79191819 | 18206 | Rgl2 | NM_009059.2 | chr17:33929893-33937687 |
| 18110 | Rdh12 | NM_030017.4 | chr12:79208912-79222664 | 18207 | Rgl3 | NM_023622.4 | chr9:21971526-21989453 |
| 18111 | Rdh13 | NM_001290409.1 | chr7:4425664-4445657 | 18208 | Rgma | NM_177740.5 | chr7:73375519-73419899 |
| 18112 | Rdh14 | NM_023697.2 | chr12:10390679-10395562 | 18209 | Rgmb | NM_178615.3 | chr17:15806252-15826586 |
| 18113 | Rdh16 | NM_009040.3 | chr10:127801152-127815839 | 18210 | Rgn | NM_009060.2 | chrX:20549817-20562687 |
| 18114 | Rdh16-ps | NR_037604.1 | chr10:127824215-127846565 | 18211 | Rgp1 | NM_172866.3 | chr4:43578734-43587487 |
| 18115 | Rdh19 | NM_147222.2 | chr10:127849927-127861176 | 18212 | Rgr | NM_021340.4 | chr14:37034908-37049014 |
| 18116 | Rdh5 | NM_134006.4 | chr10:128913590-128919297 | 18213 | Rgs1 | NM_015811.2 | chr1:144244668-144249104 |
| 18117 | Rdh7 | NM_001150749.1 | chr10:127884026-127888733 | 18214 | Rgs10 | NM_026418.2 | chr7:128373624-128418172 |
| 18118 | Rdh8 | NM_008290.1 | chr9:20818503-20826163 | 18215 | Rgs11 | NM_001081069.1 | chr17:26202961-26211324 |
| 18119 | Rdh9 | NM_153133.2 | chr10:127776404-127792697 | 18216 | Rgs12 | NM_001163512.1 | chr5:34999077-35033593 |
| 18120 | Rdm1 | NM_026654.2 | chr11:101627948-101636081 | 18217 | Rgs13 | NM_153171.4 | chr1:144138666-144177372 |
| 18121 | Rdx | NM_001104616.1 | chr9:52047149-52088738 | 18218 | Rgs14 | NM_016758.3 | chr13:55369731-55384687 |
| 18122 | Rec8 | NM_020002.3 | chr14:55618185-55625395 | 18219 | Rgs16 | NM_011267.3 | chr1:153740352-153745468 |
| 18123 | Reck | NM_016678.2 | chr4:43875529-43944806 | 18220 | Rgs17 | NM_001161822.1 | chr10:5825663-5922400 |
| 18124 | Recql | NM_001204906.1 | chr6:142356946-142387087 | 18221 | Rgs18 | NM_022881.4 | chr1:144752840-144775421 |
| 18125 | Recql4 | NM_058214.3 | chr15:76703552-76710559 | 18222 | Rgs19 | NM_001291205.1 | chr2:181688418-181691817 |
| 18126 | Recql5 | NM_145542.2 | chr11:115934-115933492 | 18223 | Rgs2 | NM_009061.4 | chr1:143999337-144004149 |
| 18127 | Redrum | NR_040338.1 | chr18:54422294-54453294 | 18224 | Rgs20 | NM_001177795.1 | chr4:4909575-5076285 |
| 18128 | Reep1 | NM_178608.4 | chr6:71707680-71810705 | 18225 | Rgs21 | NM_001290269.1 | chr1:144519689-144567667 |
| 18129 | Reep2 | NM_001204914.1 | chr18:34840588-34847463 | 18226 | Rgs22 | NM_001195748.1 | chr15:36009476-36140400 |
| 18130 | Reep3 | NM_001204915.1 | chr10:67009188-67096988 | 18227 | Rgs3 | NM_001081650.2 | chr4:62619671-62659847 |
| 18131 | Reep4 | NM_180588.2 | chr14:70545250-70548935 | 18228 | Rgs4 | NM_009062.3 | chr1:169774476-169747642 |
| 18132 | Reep5 | NM_007874.3 | chr18:34344835-34373415 | 18229 | Rgs5 | NM_009063.4 | chr1:169655500-169695813 |
| 18133 | Reep6 | NM_001204931.1 | chr10:80330144-80336441 | 18230 | Rgs6 | NM_001282061.2 | chr12:82617498-83162036 |
| 18134 | Reg1 | NM_009042.1 | chr6:78425982-78428666 | 18231 | Rgs7 | NM_001199003.1 | chr1:175059075-175492545 |
| 18135 | Reg2 | NM_009043.1 | chr6:78405154-78408097 | 18232 | Rgs7bp | NM_029879.2 | chr13:104947152-105054330 |
| 18136 | Reg3a | NM_011259.2 | chr6:78380708-78383839 | 18233 | Rgs8 | NM_026380.3 | chr1:153653036-153697665 |
| 18137 | Reg3b | NM_011036.1 | chr6:78370884-78373466 | 18234 | Rgs9 | NM_001165934.1 | chr11:109229855-109298181 |
| 18138 | Reg3d | NM_001161741.1 | chr6:78375873-78378865 | 18235 | Rgs9bp | NM_145840.3 | chr7:35578995-35585582 |

Fig.21 - 95

| | | | | | | | | |
|---|---|---|---|---|---|---|---|---|
| 18236 | Rgs11 | NM_001243223.1 | chr1:153779386-153844141 | 18333 | Ripk3 | NM_001164107.1 | chr14:55784994-55788857 |
| 18237 | Rhag | NM_011269.2 | chr17:40811148-40840754 | 18334 | Ripk4 | NM_023663.6 | chr16:97741941-97763755 |
| 18238 | Rhbdd1 | NM_001122685.1 | chr1:82339048-82445367 | 18335 | Ripply1 | NM_001037915.2 | chrX:139779680-139782353 |
| 18239 | Rhbdd2 | NM_146002.2 | chr5:135632653-135646376 | 18336 | Ripply2 | NM_001037907.1 | chr9:87015536-87019916 |
| 18240 | Rhbdd3 | NM_001290491.1 | chr11:5099272-5106100 | 18337 | Ripply3 | NM_133229.2 | chr16:94328421-94336935 |
| 18241 | Rhbdf1 | NM_001291818.1 | chr11:32209584-32222293 | 18338 | Rit1 | NM_001163310.1 | chr3:88716853-88731048 |
| 18242 | Rhbdf2 | NM_001167680.1 | chr11:116596165-116624252 | 18339 | Rit2 | NM_009065.2 | chr18:30974313-31317128 |
| 18243 | Rhbdl1 | NM_144816.1 | chr17:25834464-25837127 | 18340 | Rita1 | NM_029096.3 | chr5:120609059-120612589 |
| 18244 | Rhbdl2 | NM_183163.2 | chr4:123787874-123829904 | 18341 | Rlbp1 | NM_001173483.1 | chr7:79374869-79387027 |
| 18245 | Rhbdl3 | NM_139228.3 | chr11:80300911-80355986 | 18342 | Rlf | NM_001081013.1 | chr4:121145372-121188534 |
| 18246 | Rhbg | NM_021375.3 | chr3:88242873-88254684 | 18343 | Rlim | NM_011276.3 | chrX:103957166-103981284 |
| 18247 | Rhcg | NM_019799.3 | chr7:79593362-79617657 | 18344 | Rln1 | NM_011272.2 | chr19:29331754-29334670 |
| 18248 | Rhd | NM_011270.3 | chr4:134864535-134896172 | 18345 | Rln3 | NM_173184.1 | chr8:84043066-84044979 |
| 18249 | Rheb | NM_053075.3 | chr5:24802822-24842361 | 18346 | Ritpr | NM_001033220.2 | chr8:105690905-105698165 |
| 18250 | Rhebl1 | NM_026967.4 | chr15:98877759-98881414 | 18347 | Rmdn1 | NM_025476.6 | chr4:19575665-19606932 |
| 18251 | Rhno1 | NR_027359.1 | chr6:128356999-128362897 | 18348 | Rmdn2 | NM_201361.2 | chr17:79614899-79682152 |
| 18252 | Rho | NM_145383.1 | chr6:115931926-115938830 | 18349 | Rmdn3 | NM_001033136.3 | chr2:119136997-119157034 |
| 18253 | Rhoa | NM_016802.5 | chr9:108306159-108337943 | 18350 | Rmi1 | NM_001168248.1 | chr13:58402596-58411149 |
| 18254 | Rhob | NM_007483.2 | chr12:8497758-8499985 | 18351 | Rmi2 | NM_001162932.1 | chr16:10835058-10843235 |
| 18255 | Rhobtb1 | NM_001081347.1 | chr10:69212656-69291784 | 18352 | Rmnd1 | NM_025343.5 | chr10:4403168-4432352 |
| 18256 | Rhobtb2 | NM_153514.5 | chr14:69784989-69805545 | 18353 | Rmnd5a | NM_024288.2 | chr6:71388633-71440637 |
| 18257 | Rhobtb3 | NM_028493.2 | chr13:75869536-75943824 | 18354 | Rmnd5b | NM_025346.1 | chr11:51623672-51635896 |
| 18258 | Rhoc | NM_001291859.1 | chr3:104789033-104794459 | 18355 | Rmrp | NR_001460.1 | chr4:43492784-43493059 |
| 18259 | Rhod | NM_007485.4 | chr19:4425456-4439424 | 18356 | Rmst | NR_028262.1 | chr10:92081745-92165178 |
| 18260 | Rhof | NM_175092.3 | chr5:123118179-123132629 | 18357 | Rn4.5s | NR_002841.1 | chr8:47654920-47752925 |
| 18261 | Rhog | NM_019566.3 | chr7:102239122-102250118 | 18358 | Rn45s | NR_046233.2 | chr17:39842996-39848829 |
| 18262 | Rhoh | NM_001081105.1 | chr5:65863568-65896700 | 18359 | Rnase1 | NM_011271.2 | chr14:51145001-51146787 |
| 18263 | Rhoj | NM_023275.2 | chr12:75308312-75401455 | 18360 | Rnase10 | NM_001162863.1 | chr14:51007750-51010758 |
| 18264 | Rhoq | NM_145452.2 | chr17:86963110-87000069 | 18361 | Rnase11 | NM_001011877.2 | chr14:51049450-51050183 |
| 18265 | Rhot1 | NM_001163354.1 | chr11:80209054-80267907 | 18362 | Rnase12 | NM_001011875.2 | chr14:51056697-51057242 |
| 18266 | Rhot2 | NM_145999.2 | chr17:25838837-25844851 | 18363 | Rnase13 | NM_001011687.2 | chr14:51922159-51922773 |
| 18267 | Rhou | NM_133955.4 | chr8:123653928-123663880 | 18364 | Rnase2a | NM_053113.2 | chr14:51255261-51256112 |
| 18268 | Rhov | NM_145530.2 | chr2:119269200-119271226 | 18365 | Rnase2b | NM_019398.2 | chr14:51162259-51163018 |
| 18269 | Rhox1 | NM_001025084.2 | chrX:37213804-37222258 | 18366 | Rnase4 | NM_021472.4 | chr14:51091076-51106151 |
| 18270 | Rhox10 | NM_001024850.2 | chrX:38066474-38071688 | 18367 | Rnase6 | NM_030098.2 | chr14:51129067-51131121 |
| 18271 | Rhox11 | NM_198598.2 | chrX:38076597-38085139 | 18368 | Rnase9 | NM_183032.2 | chr14:51038458-51041867 |
| 18272 | Rhox12 | NM_001025083.2 | chrX:38104061-38110907 | 18369 | Rnaseh1 | NM_001286865.1 | chr12:28649601-28659591 |
| 18273 | Rhox13 | NM_001185002.1 | chrX:38120839-38129966 | 18370 | Rnaseh2a | NM_027187.3 | chr8:84956609-84966011 |
| 18274 | Rhox2a | NM_029203.2 | chrX:37244991-37249690 | 18371 | Rnaseh2b | NM_026616.2 | chr14:62332104-62372992 |
| 18275 | Rhox2b | NM_001099316.1 | chrX:37412104-37416806 | 18372 | Rnaseh2c | NM_026616.2 | chr19:5601872-5602959 |
| 18276 | Rhox2c | NM_001099318.1 | chrX:37453658-37458375 | 18373 | Rnasek | NM_173742.3 | chr11:70238122-70239852 |
| 18277 | Rhox2d | NM_001081669.2 | chrX:37493409-37497715 | 18374 | Rnasel | NM_011882.2 | chr1:153749425-153764221 |
| 18278 | Rhox2e | NM_001085348.1 | chrX:37530467-37541809 | 18375 | Rnaset2a | NM_001083938.2 | chr17:8128597-8147788 |
| 18279 | Rhox2f | NM_001085356.1 | chrX:37571420-37576159 | 18376 | Rnaset2b | NM_026611.2 | chr17:6978859-8147832 |
| 18280 | Rhox2g | NM_001114153.1 | chrX:37639111-37643470 | 18377 | Rnd1 | NM_172612.3 | chr15:98669204-98677461 |
| 18281 | Rhox2h | NM_001100465.1 | chrX:37668996-37673277 | 18378 | Rnd2 | NM_009708.1 | chr11:101468337-101471306 |
| 18282 | Rhox3a | NM_194063.3 | chrX:37249918-37258978 | 18379 | Rnd3 | NM_028810.2 | chr2:51130438-51149111 |
| 18283 | Rhox3c | NM_001102457.4 | chrX:37469867-37473961 | 18380 | Rnf10 | NM_016698.2 | chr5:115241769-115272895 |
| 18284 | Rhox3e | NM_001184969.1 | chrX:37254877-37550897 | 18381 | Rnf103 | NM_009543.3 | chr6:71493876-71510880 |
| 18285 | Rhox3f | NM_001040089.3 | chrX:37581351-37585496 | 18382 | Rnf11 | NM_018876.3 | chr4:109452856-109476505 |
| 18286 | Rhox3g | NM_001145406.3 | chrX:37623430-37628139 | 18383 | Rnf111 | NM_033604.2 | chr9:70425428-70503725 |
| 18287 | Rhox3h | NM_001114157.1 | chrX:37657687-37668764 | 18384 | Rnf112 | NM_001291024.1 | chr11:61448416-61453992 |
| 18288 | Rhox4a | NM_001039688.3 | chrX:37265374-37395620 | 18385 | Rnf113a1 | NM_153503.2 | chrX:37191221-37192465 |
| 18289 | Rhox4b | NM_021300.2 | chrX:37432493-37437278 | 18386 | Rnf113a2 | NM_025525.2 | chr12:84417199-84418578 |
| 18290 | Rhox4c | NM_001039689.1 | chrX:37483630-37485124 | 18387 | Rnf114 | NM_030743.5 | chr2:167492644-167516186 |
| 18291 | Rhox4d | NM_001039695.1 | chrX:37514534-37519175 | 18388 | Rnf115 | NM_026406.3 | chr3:96727610-96791155 |
| 18292 | Rhox4e | NM_201236.3 | chrX:37557411-37562282 | 18389 | Rnf121 | NM_029211.2 | chr7:102019871-102065132 |
| 18293 | Rhox4f | NM_001039696.1 | chrX:37602894-37607686 | 18390 | Rnf122 | NM_175136.2 | chr8:31111845-31131473 |
| 18294 | Rhox4g | NM_001039698.1 | chrX:37646500-37651327 | 18391 | Rnf123 | NM_032543.2 | chr9:108051671-108079375 |
| 18295 | Rhox5 | NM_008818.2 | chrX:37754607-37808878 | 18392 | Rnf125 | NM_026301.2 | chr18:20946624-20983848 |
| 18296 | Rhox6 | NM_008955.1 | chrX:37827054-37829857 | 18393 | Rnf126 | NM_144528.3 | chr10:79758514-79766962 |
| 18297 | Rhox7 | NM_001025086.2 | chrX:37831685-37841171 | 18394 | Rnf128 | NM_001254761.1 | chrX:139563339-139679145 |
| 18298 | Rhox8 | NM_001004193.1 | chrX:37874775-37878944 | 18395 | Rnf13 | NM_001119413.2 | chr3:57736061-57835425 |
| 18299 | Rhox9 | NM_023894.1 | chrX:37899096-37901770 | 18396 | Rnf130 | NM_001290749.1 | chr11:50025330-50104759 |
| 18300 | Rhpn1 | NM_001163465.1 | chr15:75704287-75714419 | 18397 | Rnf133 | NM_198251.2 | chr6:23648868-23650305 |
| 18301 | Rhpn2 | NM_027747.3 | chr7:35384236-35392287 | 18398 | Rnf135 | NM_028019.3 | chr11:80183871-80199753 |
| 18302 | Rian | NR_028261.1 | chr12:109603944-109661711 | 18399 | Rnf138 | NM_019706.3 | chr18:21001299-21028224 |
| 18303 | Ribc1 | NM_025660.2 | chrX:152040683-152016295 | 18400 | Rnf138rt1 | NM_028842.3 | chrX:163760138-163761332 |
| 18304 | Ribc2 | NM_026357.2 | chr15:85132098-85144569 | 18401 | Rnf139 | NM_175226.4 | chr15:58889228-58902390 |
| 18305 | Ric3 | NM_001038624.1 | chr7:109034318-109083324 | 18402 | Rnf14 | NM_001164621.1 | chr18:38296804-38317849 |
| 18306 | Ric8 | NM_053194.4 | chr7:140857396-140863731 | 18403 | Rnf141 | NM_025999.3 | chr7:110816534-110844381 |
| 18307 | Ric8b | NM_001013441.2 | chr10:84917612-85018337 | 18404 | Rnf144a | NM_001081977.2 | chr12:26306793-26415262 |
| 18308 | Rictor | NM_030168.3 | chr15:6708380-6800400 | 18405 | Rnf144b | NM_001170843.1 | chr13:47194002-47247991 |
| 18309 | Rif1 | NM_175238.5 | chr2:52072836-52122381 | 18406 | Rnf145 | NM_001166553.1 | chr11:44519376-44554977 |
| 18310 | Rilpd1 | NM_025506.2 | chr3:94464984-94473591 | 18407 | Rnf146 | NM_001110196.1 | chr10:29344175-29362442 |
| 18311 | Rilp | NM_001029938.2 | chr11:75510093-75513166 | 18408 | Rnf148 | NM_027754.1 | chr6:23653894-23655136 |
| 18312 | Rilpl1 | NM_021342.2 | chr5:124493079-124531391 | 18409 | Rnf149 | NM_001033135.3 | chr1:39551295-39577347 |
| 18313 | Rilpl2 | NM_030259.1 | chr5:124463264-124478239 | 18410 | Rnf150 | NM_177378.4 | chr8:82863355-83091271 |
| 18314 | Rimbp2 | NM_001081388.2 | chr5:128757787-128953486 | 18411 | Rnf151 | NM_026205.3 | chr17:24715839-24718057 |
| 18315 | Rimbp3 | NM_001033338.3 | chr16:17208134-17213982 | 18412 | Rnf152 | NM_001160368.1 | chr1:105276916-105356710 |
| 18316 | Rimkla | NM_175572.4 | chr4:119465284-119492598 | 18413 | Rnf157 | NM_027258.1 | chr11:116336344-116413032 |
| 18317 | Rimklb | NM_027664.2 | chr6:122453608-122486305 | 18414 | Rnf165 | NM_001166504.1 | chr18:77456109-77565136 |
| 18318 | Rims1 | NM_001012623.1 | chr1:22288421-22805724 | 18415 | Rnf166 | NM_001033142.2 | chr8:122466146-122476064 |
| 18319 | Rims2 | NM_001256382.1 | chr15:39398285-39684372 | 18416 | Rnf167 | NM_027445.2 | chr11:70647588-70651414 |
| 18320 | Rims3 | NM_182929.1 | chr4:120877868-120891560 | 18417 | Rnf168 | NM_027355.2 | chr16:32277460-32301439 |
| 18321 | Rims4 | NM_183023.1 | chr2:163863880-163918683 | 18418 | Rnf169 | NM_175388.3 | chr7:99920253-99980458 |
| 18322 | Rin1 | NM_145495.2 | chr19:5050807-5057071 | 18419 | Rnf17 | NM_001033043.1 | chr14:56402696-56525031 |
| 18323 | Rin2 | NM_028724.4 | chr2:145286115-145887616 | 18420 | Rnf170 | NM_029965.2 | chr8:26119379-26143869 |
| 18324 | Rin3 | NM_001161365.1 | chr12:102283640-102390854 | 18421 | Rnf180 | NM_027934.2 | chr13:105147493-105293014 |
| 18325 | Ring1 | NM_009066.3 | chr17:34020791-34024680 | 18422 | Rnf181 | NM_025607.3 | chr6:72359713-72362381 |
| 18326 | Rin1 | NM_177158.5 | chr7:28783968-28798966 | 18423 | Rnf182 | NM_183204.4 | chr13:43615796-43670944 |
| 18327 | Rint1 | NM_177323.4 | chr5:23787710-23820369 | 18424 | Rnf183 | NM_153504.3 | chr4:62427541-62474726 |
| 18328 | Riok1 | NM_024242.3 | chr13:38036988-38061433 | 18425 | Rnf185 | NM_001290472.1 | chr11:3415972-3452956 |
| 18329 | Riok2 | NM_025934.2 | chr17:17374331-17394899 | 18426 | Rnf186 | NM_025786.3 | chr4:138967111-138968366 |
| 18330 | Riok3 | NM_024124.2 | chr18:12128849-12157367 | 18427 | Rnf187 | NM_024423.2 | chr11:58932287-58938506 |
| 18331 | Ripk1 | NM_009068.3 | chr13:34002873-34035170 | 18428 | Rnf19a | NM_013923.2 | chr15:36239933-36283147 |
| 18332 | Ripk2 | NM_138952.3 | chr4:16123374-16163498 | 18429 | Rnf19b | NM_029219.1 | chr4:129084526-129084526 |

Fig.21 - 96

| | | | | | | | |
|---|---|---|---|---|---|---|---|
| 18430 | Rnf2 | NM_011277.2 | chr1:151469405-151500823 | 18527 | Rpl19 | NM_001159483.1 | chr11:98026709-98030493 |
| 18431 | Rnf20 | NM_001163263.1 | chr4:49632059-49656886 | 18528 | Rpl21 | NM_019647.6 | chr5:146832889-146837032 |
| 18432 | Rnf207 | NM_001033489.2 | chr4:152307022-152318625 | 18529 | Rpl22 | NM_001277313.1 | chr4:152324435-152334082 |
| 18433 | Rnf208 | NM_176834.2 | chr2:25242928-25244261 | 18530 | Rpl22l1 | NM_026517.2 | chr3:28805510-28807415 |
| 18434 | Rnf214 | NM_178709.4 | chr9:45863690-45906877 | 18531 | Rpl23 | NM_022891.3 | chr11:97777525-97782439 |
| 18435 | Rnf215 | NM_027859.2 | chr11:4135159-4141192 | 18532 | Rpl23a | NM_207523.2 | chr11:78180935-78183584 |
| 18436 | Rnf216 | NM_080561.4 | chr5:142990892-143113020 | 18533 | Rpl24 | NM_024218.4 | chr16:55966274-55971437 |
| 18437 | Rnf217 | NM_001146349.1 | chr10:31501886-31609725 | 18534 | Rpl26 | NM_009080.2 | chr11:68901565-68904534 |
| 18438 | Rnf219 | NM_026047.4 | chr14:104477533-104522666 | 18535 | Rpl27 | NM_011289.3 | chr11:101442244-101445596 |
| 18439 | Rnf220 | NM_025739.3 | chr4:117271462-117497052 | 18536 | Rpl27a | NM_013975.3 | chr7:109519194-109522369 |
| 18440 | Rnf222 | NM_177060.3 | chr11:68888552-68895015 | 18537 | Rpl28 | NM_009081.2 | chr7:4792964-4794547 |
| 18441 | Rnf223 | NM_001220499.1 | chr4:156132169-156133419 | 18538 | Rpl29 | NM_009082.2 | chr9:106429538-106431567 |
| 18442 | Rnf224 | NM_001033410.2 | chr2:25234475-25236787 | 18539 | Rpl3 | NM_013762.2 | chr15:80077780-80083406 |
| 18443 | Rnf24 | NM_178607.4 | chr2:131298487-131352892 | 18540 | Rpl30 | NM_001163685.1 | chr15:34440507-34444276 |
| 18444 | Rnf25 | NM_021313.1 | chr1:74593747-74601397 | 18541 | Rpl31 | NM_001252218.1 | chr1:39367850-39371910 |
| 18445 | Rnf26 | NM_153762.3 | chr9:44110780-44113051 | 18542 | Rpl31-ps12 | NM_001258458.1 | chr16:16819712-16820196 |
| 18446 | Rnf31 | NM_194346.2 | chr14:55591789-55603671 | 18543 | Rpl32 | NM_172086.2 | chr6:115805513-115808743 |
| 18447 | Rnf32 | NM_001287057.1 | chr5:29195992-29225524 | 18544 | Rpl34 | NM_001005859.3 | chr3:130726826-130730398 |
| 18448 | Rnf34 | NM_030564.1 | chr5:122850187-122868945 | 18545 | Rpl34-ps1 | NM_001199350.1 | chr3:130726836-130730329 |
| 18449 | Rnf38 | NM_001038993.3 | chr4:44126211-44168283 | 18546 | Rpl35 | NM_025592.3 | chr2:39001580-39005131 |
| 18450 | Rnf39 | NM_001099632.1 | chr17:36943050-36947986 | 18547 | Rpl35a | NM_001130484.1 | chr16:33056481-33060188 |
| 18451 | Rnf4 | NM_011278.5 | chr5:34336249-34353445 | 18548 | Rpl36 | NM_018730.3 | chr17:56613394-58614246 |
| 18452 | Rnf40 | NM_172281.2 | chr7:127588697-127603605 | 18549 | Rpl36a | NM_019865.5 | chrX:134585653-134588062 |
| 18453 | Rnf41 | NM_001164237.1 | chr10:128411615-128441441 | 18550 | Rpl36al | NM_025589.4 | chr12:69152733-69184067 |
| 18454 | Rnf43 | NM_172448.3 | chr11:87663086-87735539 | 18551 | Rpl37 | NM_026069.3 | chr15:5116612-5119140 |
| 18455 | Rnf44 | NM_001146025.1 | chr13:54679398-54687808 | 18552 | Rpl37a | NM_009084.4 | chr1:72711259-72713813 |
| 18456 | Rnf5 | NM_019403.3 | chr17:34601098-34603561 | 18553 | Rpl38 | NM_001048057.1 | chr1:114668542-114672331 |
| 18457 | Rnf6 | NM_001256085.1 | chr5:146209193-146220971 | 18554 | Rpl39 | NM_026055.2 | chrX:37082517-37085222 |
| 18458 | Rnf7 | NM_011279.3 | chr9:96470936-96478675 | 18555 | Rpl39l | NM_026594.2 | chr16:10170227-10174911 |
| 18459 | Rnf8 | NM_021419.2 | chr17:29614788-29641664 | 18556 | Rpl3l | NM_001163945.1 | chr17:24727828-24736149 |
| 18460 | Rnft1 | NM_029788.5 | chr11:86484656-86499007 | 18557 | Rpl4 | NM_024212.4 | chr9:64173386-64178362 |
| 18461 | Rnft2 | NM_001109902.1 | chr5:118190735-118245025 | 18558 | Rpl41 | NM_018860.4 | chr10:128548109-128549168 |
| 18462 | Rngtt | NM_011884.3 | chr4:33310310-33502614 | 18559 | Rpl5 | NM_016980.2 | chr5:107900527-107909005 |
| 18463 | Rnh1 | NM_001172100.1 | chr7:141160325-141172851 | 18560 | Rpl6 | NM_011290.5 | chr5:121204500-121209241 |
| 18464 | Rnls | NM_001146342.2 | chr19:33137744-33392295 | 18561 | Rpl7 | NM_011291.5 | chr1:16101295-16104433 |
| 18465 | Rnmt | NM_001170953.1 | chr18:68300354-68324352 | 18562 | Rpl7a | NM_013721.3 | chr2:26910806-26913311 |
| 18466 | Rnmtl1 | NM_183263.5 | chr11:76243735-76250622 | 18563 | Rpl7l1 | NM_025433.3 | chr17:46773906-46782656 |
| 18467 | Rnpc3 | NM_001088696.1 | chr3:113605066-113630149 | 18564 | Rpl8 | NM_012053.2 | chr15:76904070-76906318 |
| 18468 | Rnpep | NM_001156295.1 | chr1:135262698-135284084 | 18565 | Rpl9 | NM_011292.2 | chr5:65388363-65391431 |
| 18469 | Rnpepl1 | NM_181405.4 | chr1:92910824-92920585 | 18566 | Rplp0 | NM_007475.5 | chr5:115559466-115563729 |
| 18470 | Rnps1 | NM_001080127.1 | chr17:24414674-24425897 | 18567 | Rplp1 | NM_018853.3 | chr9:61913282-61914510 |
| 18471 | Rnu11 | NR_002865.2 | chr4:132270078-132270186 | 18568 | Rplp2 | NM_026020.6 | chr7:141847649-141451342 |
| 18472 | Rnu12 | NR_004432.2 | chr15:83149644-83149794 | 18569 | Rplp2-ps1 | NR_038063.1 | chr12:75630924-75631749 |
| 18473 | Rnu6 | NR_003027.2 | chr19:14438479-14438506 | 18570 | Rpn1 | NM_133933.4 | chr6:88084472-88105304 |
| 18474 | Rnu7 | NR_024201.3 | chr5:53698563-53698588 | 18571 | Rpn2 | NM_019642.4 | chr2:157279097-157326318 |
| 18475 | Rnu73b | NR_004418.1 | chr3:86140616-86140687 | 18572 | Rpp14 | NM_025938.4 | chr14:8080312-8091846 |
| 18476 | Robo1 | NM_019413.2 | chr16:72663148-73046100 | 18573 | Rpp21 | NM_026308.2 | chr17:36255672-36257846 |
| 18477 | Robo2 | NM_175549.4 | chr16:73892305-74110912 | 18574 | Rpp25 | NM_133982.1 | chr9:57504103-57505447 |
| 18478 | Robo3 | NM_001164767.1 | chr9:37416044-37433175 | 18575 | Rpp25l | NM_027278.3 | chr4:41712032-41713517 |
| 18479 | Robo4 | NM_028783.3 | chr9:37401896-37414023 | 18576 | Rpp30 | NM_019428.3 | chr19:36083715-36104773 |
| 18480 | Rock1 | NM_009071.2 | chr18:10064400-10181792 | 18577 | Rpp38 | NM_001013376.2 | chr2:3328948-3332628 |
| 18481 | Rock2 | NM_009072.2 | chr12:16894977-16988274 | 18578 | Rpp40 | NM_145938.4 | chr13:35895103-35906347 |
| 18482 | Rogdi | NM_133185.2 | chr16:5008728-5013553 | 18579 | Rpph1 | NR_002142.2 | chr14:50807446-50807771 |
| 18483 | Rom1 | NM_009073.4 | chr19:8927381-8929356 | 18580 | Rprd1a | NM_144861.2 | chr18:24484961-24530264 |
| 18484 | Romo1 | NM_001164216.1 | chr2:156144152-156145794 | 18581 | Rprd1b | NM_001291134.1 | chr2:158026496-158078207 |
| 18485 | Ropn1 | NM_030744.2 | chr16:34651210-34678610 | 18582 | Rprd2 | NM_001081293.1 | chr3:95759872-95818959 |
| 18486 | Ropn1l | NM_145852.2 | chr15:31441209-31453689 | 18583 | Rpr11 | NR_004434.3 | chr6:69326936-69327174 |
| 18487 | Ror1 | NM_013845.5 | chr4:100095790-100444806 | 18584 | Rpr12 | NR_004439.2 | chr3:22251369-22251607 |
| 18488 | Ror2 | NM_013846.3 | chr13:53109316-53286109 | 18585 | Rpr13 | NR_024198.2 | chr8:3803124-3803361 |
| 18489 | Rora | NM_001289916.1 | chr9:69289840-69388246 | 18586 | Rprm | NM_023396.4 | chr2:54084092-54085552 |
| 18490 | Rorb | NM_001043534.2 | chr19:18930032-19111196 | 18587 | Rprml | NM_001033212.2 | chr11:103649508-103650580 |
| 18491 | Rorc | NM_011281.3 | chr3:94372793-94398274 | 18588 | Rps10 | NM_025963.3 | chr17:27630428-27635242 |
| 18492 | Ros1 | NM_011283.2 | chr10:52045925-52195244 | 18589 | Rps11 | NM_013725.4 | chr7:45122387-45124389 |
| 18493 | Rp1 | NM_011195662.1 | chr1:4290845-4409241 | 18590 | Rps12 | NM_011295.6 | chr10:23785182-23787209 |
| 18494 | Rp1l1 | NM_146246.3 | chr14:63992430-64033506 | 18591 | Rps13 | NM_026533.3 | chr7:116331506-116334190 |
| 18495 | Rp2h | NM_190643.1 | chrX:20364480-20400858 | 18592 | Rps14 | NM_020600.4 | chr18:60774595-60778546 |
| 18496 | Rp9 | NM_018739.2 | chr9:22448311-22468356 | 18593 | Rps15 | NM_009091.2 | chr10:80292480-80294114 |
| 18497 | Rpa1 | NM_001164223.1 | chr11:75300258-75348883 | 18594 | Rps15a | NM_170669.2 | chr7:118104375-118118147 |
| 18498 | Rpa2 | NM_011284.2 | chr4:132619359-132778746 | 18595 | Rps15a-ps4 | NR_036572.1 | chr14:132219892-132220589 |
| 18499 | Rpa3 | NM_026632.4 | chr6:8255935-8259141 | 18596 | Rps15a-ps6 | NR_029471.2 | chr11:6172507-6173331 |
| 18500 | Rpain | NM_001252413.1 | chr11:70970139-70977933 | 18597 | Rps16 | NM_013647.2 | chr7:28356688-28352698 |
| 18501 | Rpap1 | NM_001163701.1 | chr2:119763958-119787537 | 18598 | Rps17 | NM_009092.3 | chr7:81342732-81345234 |
| 18502 | Rpap2 | NM_001163461.2 | chr5:107587695-107642918 | 18599 | Rps18 | NM_011296.2 | chr17:33951998-33955641 |
| 18503 | Rpap3 | NM_025682.2 | chr15:97675104-97705822 | 18600 | Rps19 | NM_023133.1 | chr7:24884713-24889802 |
| 18504 | Rpe | NM_025683.3 | chr1:66700830-66719805 | 18601 | Rps19bp1 | NM_175109.3 | chr15:80260613-80264306 |
| 18505 | Rpe65 | NM_029987.2 | chr3:159599180-159625307 | 18602 | Rps19-ps3 | NR_033639.1 | chr4:147821776-147822202 |
| 18506 | Rpf1 | NM_027332.3 | chr3:146510794-146521423 | 18603 | Rps2 | NM_008503.5 | chr17:24720062-24721927 |
| 18507 | Rpf2 | NM_001042556.1 | chr10:40223245-40246979 | 18604 | Rps20 | NM_026147.5 | chr4:3834472-3835600 |
| 18508 | Rpgr | NM_001177950.1 | chrX:10158215-10216795 | 18605 | Rps21 | NM_025872.2 | chr12:180257378-180258444 |
| 18509 | Rpgrip1 | NM_001168515.1 | chr14:52110902-52161339 | 18606 | Rps23 | NM_024175.3 | chr13:90923121-90924732 |
| 18510 | Rpgrip1l | NM_173431.2 | chr8:91217029-91313222 | 18607 | Rps24 | NM_011297.2 | chr14:24490680-24496146 |
| 18511 | Rph3a | NM_001291295.1 | chr5:120940499-121009538 | 18608 | Rps25 | NM_024266.3 | chr9:44407713-44410406 |
| 18512 | Rph3al | NM_001291159.1 | chr11:75899724-75925891 | 18609 | Rps26 | NM_013765.2 | chr10:128624528-128626506 |
| 18513 | Rpia | NM_009075.2 | chr6:70765719-70792175 | 18610 | Rps27 | NM_027015.4 | chr3:90212666-90213648 |
| 18514 | Rpl10 | NM_052835.5 | chrX:74270815-74273135 | 18611 | Rps27a | NM_001033865.1 | chr11:29545841-29548040 |
| 18515 | Rpl10a | NM_011287.2 | chr17:28328470-28331033 | 18612 | Rps27l | NM_026467.4 | chr6:66946075-66949522 |
| 18516 | Rpl10l | NM_001162933.1 | chr12:66453879-66284401 | 18613 | Rps27rt | NM_001190258.1 | chr3:90212666-90213647 |
| 18517 | Rpl11 | NM_025919.2 | chr4:136049947-136053371 | 18614 | Rps28 | NM_016844.2 | chr17:33823036-33824498 |
| 18518 | Rpl12 | NM_009076.3 | chr2:32961711-32964045 | 18615 | Rps29 | NM_009093.2 | chr12:69157721-69159186 |
| 18519 | Rpl13 | NM_016738.5 | chr8:123102349-123105242 | 18616 | Rps3 | NM_012052.2 | chr7:99483709-99483709 |
| 18520 | Rpl13a | NM_009438.5 | chr7:45125562-45128745 | 18617 | Rps3a1 | NM_016959.4 | chr3:86137939-86142668 |
| 18521 | Rpl14 | NM_025974.2 | chr9:120571516-120574653 | 18618 | Rps4l | NR_036634.2 | chr6:148354655-148355596 |
| 18522 | Rpl14-ps1 | NR_110499.1 | chr7:45324957-45325651 | 18619 | Rps4x | NM_009094.2 | chrX:102184940-102189391 |
| 18523 | Rpl15 | NM_025586.3 | chr14:18267822-18270986 | 18620 | Rps5 | NM_009095.2 | chr7:12922310-12926686 |
| 18524 | Rpl17 | NM_001002239.3 | chr18:75000476-75003381 | 18621 | Rps6 | NM_009096.2 | chr4:86854098-86857367 |
| 18525 | Rpl18 | NM_009077.2 | chr7:45718070-45720835 | 18622 | Rps6ka1 | NM_001285505.1 | chr4:133847290-133887797 |
| 18526 | Rpl18a | NM_029751.4 | chr8:70894721-70897443 | 18623 | Rps6ka2 | NM_011299.4 | chr17:7170114-7303316 |

Fig.21 - 97

| | | | | | | | |
|---|---|---|---|---|---|---|---|
| 18624 | Rps6ka3 | NM_148945.2 | chrX:159255781-159368244 | 18721 | Rufy3 | NM_001289774.1 | chr5:88565039-88651417 |
| 18625 | Rps6ka4 | NM_019924.2 | chr19:6829083-6840627 | 18722 | Rufy4 | NM_001034060.3 | chr1:74125540-74148223 |
| 18626 | Rps6ka5 | NM_153587.2 | chr12:100549777-100725028 | 18723 | Rundc1 | NM_172566.4 | chr11:101425084-101435665 |
| 18627 | Rps6ka6 | NM_025949.3 | chrX:111387836-111537959 | 18724 | Rundc3a | NM_001252347.1 | chr11:102393402-102402939 |
| 18628 | Rps6kb1 | NM_001114334.1 | chr11:86499010-86544807 | 18725 | Rundc3b | NM_198620.1 | chr5:8490335-8622952 |
| 18629 | Rps6kb2 | NM_021485.2 | chr19:4156976-4163245 | 18726 | Runx1 | NM_001111021.2 | chr16:92601465-92826074 |
| 18630 | Rps6kc1 | NM_178775.4 | chr11:190772878-190911770 | 18727 | Runx1t1 | NM_001111026.2 | chr4:13743301-13895055 |
| 18631 | Rps6kl1 | NM_146244.4 | chr12:85135595-85151264 | 18728 | Runx2 | NM_001145920.2 | chr17:44603988-44736648 |
| 18632 | Rps7 | NM_011300.3 | chr12:28630846-28635953 | 18729 | Runx3 | NM_019732.2 | chr4:135120644-135177990 |
| 18633 | Rps8 | NM_009098.2 | chr4:117153835-117156132 | 18730 | Rusc1 | NM_001083807.1 | chr3:89083978-89093363 |
| 18634 | Rps9 | NM_029767.2 | chr7:3704040-3706897 | 18731 | Rusc2 | NM_001037709.2 | chr4:43381981-43427092 |
| 18635 | Rpsa | NM_011029.4 | chr9:120127765-120132369 | 18732 | Ruvbl1 | NM_019685.2 | chr6:88465422-88497566 |
| 18636 | Rptn | NM_009100.2 | chr3:93393698-93399442 | 18733 | Ruvbl2 | NM_011304.3 | chr7:45421897-45434464 |
| 18637 | Rptor | NM_028898.3 | chr11:119602904-119899591 | 18734 | Rwdd1 | NM_025614.3 | chr10:33996554-34019616 |
| 18638 | Rptoros | NR_045312.1 | chr11:119820810-119834365 | 18735 | Rwdd2a | NM_001145968.1 | chr9:86572052-86574899 |
| 18639 | Rpusd1 | NM_028009.3 | chr17:25727750-25731456 | 18736 | Rwdd2b | NM_016924.2 | chr16:87433330-87440592 |
| 18640 | Rpusd2 | NM_173450.3 | chr2:119034789-119042197 | 18737 | Rwdd3 | NM_025637.3 | chr3:121135401-121171695 |
| 18641 | Rpusd3 | NM_001033204.1 | chr6:113415318-113419340 | 18738 | Rwdd4a | NM_203507.3 | chr8:47533644-47552837 |
| 18642 | Rpusd4 | NM_028040.2 | chr9:35267880-35279957 | 18739 | Rxfp1 | NM_212452.1 | chr2:79644719-79737794 |
| 18643 | Rqcd1 | NM_021383.5 | chr1:74506059-74530842 | 18740 | Rxfp2 | NM_001289564.1 | chr5:150018674-150082186 |
| 18644 | Rrad | NM_019662.2 | chr8:104628065-104631321 | 18741 | Rxfp3 | NM_178717.3 | chr15:11033716-11037968 |
| 18645 | Rraga | NM_178376.3 | chr4:86575672-86577283 | 18742 | Rxfp4 | NM_181817.1 | chr3:88651897-88653142 |
| 18646 | Rragb | NM_001004154.2 | chrX:153139957-153171943 | 18743 | Rxra | NM_001290481.1 | chr2:27709291-27763319 |
| 18647 | Rragc | NM_017475.2 | chr4:123917432-123936997 | 18744 | Rxrb | NM_001205214.1 | chr17:34033811-34038403 |
| 18648 | Rragd | NM_027491.2 | chr4:32982997-33022180 | 18745 | Rxrg | NM_001159731.1 | chr1:167618264-167639623 |
| 18649 | Rras | NM_009101.2 | chr7:45018006-45021644 | 18746 | Rybp | NM_019743.3 | chr6:100228564-100287358 |
| 18650 | Rras2 | NM_025846.2 | chr7:114046781-114117781 | 18747 | Ryk | NM_001042607.1 | chr9:102834919-102906307 |
| 18651 | Rrbp1 | NM_024281.2 | chr2:143947394-144011263 | 18748 | Ryr1 | NM_009109.2 | chr7:29003339-29125151 |
| 18652 | Rreb1 | NM_001039188.1 | chr13:37827392-37935534 | 18749 | Ryr2 | NM_023868.2 | chr13:11553102-12106945 |
| 18653 | Rrh | NM_009102.3 | chr3:129808574-129822509 | 18750 | Ryr3 | NM_177652.2 | chr2:112631381-113030331 |
| 18654 | Rrm1 | NM_009103.4 | chr7:102441694-102469771 | 18751 | S100a1 | NM_011309.3 | chr3:90511033-90514130 |
| 18655 | Rrm2 | NM_009104.2 | chr12:24708253-24714146 | 18752 | S100a10 | NM_009112.2 | chr3:93555116-93564645 |
| 18656 | Rrm2b | NM_199476.1 | chr15:37923952-37961055 | 18753 | S100a11 | NM_016740.3 | chr3:93520495-93526288 |
| 18657 | Rrn3 | NM_001039521.1 | chr16:13780698-13814841 | 18754 | S100a13 | NM_009113.4 | chr3:90514434-90524581 |
| 18658 | Rrnad1 | NM_153562.4 | chr3:87922600-87930196 | 18755 | S100a14 | NM_001163525.2 | chr3:90526848-90528835 |
| 18659 | Rrp1 | NM_019925.2 | chr10:78400361-78413043 | 18756 | S100a16 | NM_026416.2 | chr3:90541222-90543151 |
| 18660 | Rrp12 | NM_199442.2 | chr19:41862850-41896153 | 18757 | S100a2 | NM_001195760.1 | chr3:90590246-90591508 |
| 18661 | Rrp15 | NM_026041.2 | chr1:186721086-186749358 | 18758 | S100a3 | NM_011310.2 | chr3:90600214-90602702 |
| 18662 | Rrp1b | NM_001163734.1 | chr17:32048284-32062862 | 18759 | S100a4 | NM_011311.2 | chr3:90603769-90606045 |
| 18663 | Rrp36 | NM_144857.3 | chr17:46667452-46674255 | 18760 | S100a5 | NM_011312.2 | chr3:90608521-90611780 |
| 18664 | Rrp7a | NM_029101.4 | chr15:83115845-83122801 | 18761 | S100a6 | NM_011313.2 | chr3:90612893-90614414 |
| 18665 | Rrp8 | NM_025897.2 | chr7:105731729-105736584 | 18762 | S100a7a | NM_199422.1 | chr3:90654301-90658130 |
| 18666 | Rrp9 | NM_145620.4 | chr9:106477308-106485415 | 18763 | S100a8 | NM_013650.2 | chr3:90669070-90670034 |
| 18667 | Rrs1 | NM_021511.2 | chr1:9545407-9547455 | 18764 | S100a9 | NM_001281852.1 | chr3:90692629-90695721 |
| 18668 | Rs1 | NM_011302.3 | chrX:160768012-160799863 | 18765 | S100b | NM_009115.3 | chr10:76253835-76261319 |
| 18669 | Rsad1 | NM_001013381.2 | chr11:94539797-94549207 | 18766 | S100g | NM_009789.1 | chrX:162961991-162964599 |
| 18670 | Rsad2 | NM_023386.4 | chr12:26442742-26456452 | 18767 | S100pbp | NM_029036.2 | chr4:129150824-129189482 |
| 18671 | Rsbn1 | NM_172684.2 | chr3:103914119-103966620 | 18768 | S100z | NM_001081159.1 | chr13:95477300-95478655 |
| 18672 | Rsbn1l | NM_001080977.1 | chr5:20893023-20951822 | 18769 | S1pr1 | NM_007901.5 | chr3:115710432-115715055 |
| 18673 | Rsc1a1 | NM_029544.5 | chr4:141683562-141685716 | 18770 | S1pr2 | NM_010333.4 | chr9:20965951-20976793 |
| 18674 | Rsf1 | NM_001081267.2 | chr7:97579895-97692782 | 18771 | S1pr3 | NM_010101.4 | chr13:51408617-51423797 |
| 18675 | Rsg1 | NM_001081174.2 | chr4:141213955-141220114 | 18772 | S1pr4 | NM_010102.2 | chr10:81497744-81500137 |
| 18676 | Rsl1 | NM_001013769.1 | chr13:67173181-67183498 | 18773 | S1pr5 | NM_053190.2 | chr9:21242916-21248443 |
| 18677 | Rsl1d1 | NM_025546.2 | chr16:11193036-11203292 | 18774 | Saa1 | NM_009117.3 | chr7:46740498-46742980 |
| 18678 | Rsl24d1 | NM_198004.2 | chr9:73113468-73123333 | 18775 | Saa2 | NM_011314.2 | chr7:46751832-46754314 |
| 18679 | Rslcan18 | NM_001256052.1 | chr3:67096612-67114028 | 18776 | Saa3 | NM_011315.3 | chr7:46711997-46715676 |
| 18680 | Rsph1 | NM_025290.3 | chr17:31255019-31277356 | 18777 | Saa4 | NM_011316.3 | chr7:46727998-46732543 |
| 18681 | Rsph3a | NM_025789.5 | chr17:7945613-7979556 | 18778 | Sac1l | NM_030233.1 | chr7:46686107-46710651 |
| 18682 | Rsph3b | NM_001083945.1 | chr17:6904715-6948356 | 18779 | Sac3d1 | NM_133678.3 | chr19:6116003-8118586 |
| 18683 | Rsph4a | NM_001162957.1 | chr10:33905110-33916021 | 18780 | Sacm1l | NM_030692.4 | chr9:123529853-123592598 |
| 18684 | Rsph6a | NM_011546686-19074447 | chr7:19054686-19074447 | 18781 | Sacs | NM_172809.3 | chr14:61138456-61240693 |
| 18685 | Rsph9 | NM_029338.3 | chr17:46125276-46144198 | 18782 | Sae1 | NM_001285891.1 | chr7:16820235-16387896 |
| 18686 | Rspo1 | NM_138683.3 | chr4:124986429-125009099 | 18783 | Safb | NM_001163300.1 | chr17:56584981-56606294 |
| 18687 | Rspo2 | NM_172815.3 | chr15:43020794-43170818 | 18784 | Safb2 | NM_001029979.2 | chr17:56562941-56584583 |
| 18688 | Rspo3 | NM_028351.3 | chr10:29453106-29535867 | 18785 | Sag | NM_009118.2 | chr1:87803679-87845157 |
| 18689 | Rspo4 | NM_001040689.1 | chr2:151842926-151874668 | 18786 | Sall1 | NM_021390.3 | chr8:89027242-89044162 |
| 18690 | Rspry1 | NM_026274.4 | chr8:94601940-94660276 | 18787 | Sall2 | NM_001244916.1 | chr14:52311176-52316823 |
| 18691 | Rsrc1 | NM_025822.3 | chr3:66985671-67358403 | 18788 | Sall3 | NM_178280.3 | chr18:80966373-80986578 |
| 18692 | Rsrc2 | NM_001005525.2 | chr5:123728425-123749414 | 18789 | Sall4 | NM_175303.4 | chr2:168748333-168767201 |
| 18693 | Rsrp1 | NM_023665.3 | chr4:134923624-134927370 | 18790 | Samd1 | NM_001081415.1 | chr8:83997671-84000386 |
| 18694 | Rsu1 | NM_009105.4 | chr2:13076066-13271415 | 18791 | Samd10 | NM_172676.2 | chr2:181595217-181599147 |
| 18695 | Rtbdn | NM_144929.2 | chr8:84946990-84956603 | 18792 | Samd11 | NM_001105161.1 | chr4:156246965-156255338 |
| 18696 | Rtcs | NM_025517.3 | chr3:116488963-116508375 | 18793 | Samd12 | NM_177225.4 | chr15:53461800-53902436 |
| 18697 | Rtcb | NM_145422.4 | chr10:85938636-85957793 | 18794 | Samd14 | NM_146025.2 | chr11:95009878-95026087 |
| 18698 | Rtdr1 | NM_001163533.1 | chr10:74957476-75032586 | 18795 | Samd15 | NM_001290288.1 | chr12:87200542-87213538 |
| 18699 | Rtel1 | NM_001001882.3 | chr2:181319723-181356616 | 18796 | Samd3 | NM_001013766.2 | chr10:26229706-26260804 |
| 18700 | Rtf1 | NM_030142.2 | chr2:119575067-119735407 | 18797 | Samd4 | NM_001037221.2 | chr14:46882964-47105817 |
| 18701 | Rtfdc1 | NM_025642.2 | chr2:172440577-172469899 | 18798 | Samd4b | NM_175021.3 | chr7:28399521-28436191 |
| 18702 | Rtkn | NM_001136271.1 | chr6:83067837-83152579 | 18799 | Samd5 | NM_177271.3 | chr10:9627258-9675208 |
| 18703 | Rtkn2 | NM_001081346.1 | chr10:67979597-68043864 | 18800 | Samd7 | NM_029489.3 | chr3:30746292-30767174 |
| 18704 | Rtl1 | NM_184109.1 | chr12:109590168-109585403 | 18801 | Samd8 | NM_026283.2 | chr14:21750590-21798725 |
| 18705 | Rtn1 | NM_001007696.2 | chr12:72211748-72236727 | 18802 | Samd9l | NM_010156.3 | chr6:3372257-3399571 |
| 18706 | Rtn2 | NM_001025364.3 | chr7:19291068-19296164 | 18803 | Samhd1 | NM_001139520.1 | chr2:157097528-157135222 |
| 18707 | Rtn3 | NM_001004933.2 | chr19:7425894-7483291 | 18804 | Samm50 | NM_178614.4 | chr15:84192232-84214303 |
| 18708 | Rtn4 | NM_024226.2 | chr11:29138562-29744414 | 18805 | Samsn1 | NM_023380.2 | chr16:75858793-75909266 |
| 18709 | Rtn4ip1 | NM_130892.4 | chr10:43901806-43947862 | 18806 | Samt2 | NM_001037167.1 | chrX:154575227-154679336 |
| 18710 | Rtn4r | NM_022982.2 | chr16:18177505-18152408 | 18807 | Samt3 | NM_028554.3 | chrX:86041198-86047313 |
| 18711 | Rtn4rl1 | NM_177708.5 | chr11:75199992-75267762 | 18808 | Samt4 | NM_029199.2 | chrX:154482001-154484682 |
| 18712 | Rtn4rl2 | NM_199223.1 | chr2:84871945-84886692 | 18809 | Sap130 | NM_172965.2 | chr18:31634382-31723061 |
| 18713 | Rtp1 | NM_001004351.2 | chr16:23429132-23433960 | 18810 | Sap18 | NM_009119.3 | chr14:57798188-57804980 |
| 18714 | Rtp2 | NM_001008230.3 | chr16:23925547-23930794 | 18811 | Sap25 | NM_001081962.2 | chr5:137641472-137642902 |
| 18715 | Rtp3 | NM_153100.2 | chr9:110984942-110989713 | 18812 | Sap30 | NM_021788.2 | chr8:57482701-57487860 |
| 18716 | Rtp4 | NM_023386.5 | chr16:23609918-23614222 | 18813 | Sap30bp | NM_020483 | chr11:115933658-115965534 |
| 18717 | Rttn | NM_175542.3 | chr18:88971789-89131014 | 18814 | Sap30l | NM_001081168 | chr11:57810636-57810615 |
| 18718 | Rubie | NR_046459.1 | chr14:46568330-46575651 | 18815 | Sapcd1 | NM_023893.4 | chr17:35025972-35028016 |
| 18719 | Rufy1 | NM_172557.3 | chr1:50389302-50431111 | 18816 | Sapcd2 | NM_001081085.2 | chr2:25372034-25378213 |
| 18720 | Rufy2 | NM_027425.3 | chr10:62980222-63018742 | 18817 | Sar1a | NM_009120.2 | chr10:61680320-61693297 |

| | | | | | | | | |
|---|---|---|---|---|---|---|---|---|
| 19012 | Sec24b | NM_207209.2 | chr3:129983184-130060907 | 19109 | Serpina1f | NM_001164742.1 | chr12:103688043-103694689 |
| 19013 | Sec24c | NM_001168273.1 | chr14:20674320-20694850 | 19110 | Serpina3a | NM_001167705.1 | chr12:104112723-104121896 |
| 19014 | Sec24d | NM_027135.2 | chr3:123267495-123356636 | 19111 | Serpina3b | NM_173024.3 | chr12:104127995-104139545 |
| 19015 | Sec31a | NM_026969.1 | chr5:100361648-100416234 | 19112 | Serpina3c | NM_008458.2 | chr12:104146906-104153872 |
| 19016 | Sec31b | NM_001033343.1 | chr19:44516956-44545848 | 19113 | Serpina3f | NM_001033335.3 | chr12:104214632-104221129 |
| 19017 | Sec61a1 | NM_016906.4 | chr6:88503606-88518800 | 19114 | Serpina3g | NM_009251.1 | chr12:104214543-104241934 |
| 19018 | Sec61a2 | NM_021305.3 | chr2:5870986-5895353 | 19115 | Serpina3i | NR_033450.1 | chr12:104247895-104254405 |
| 19019 | Sec61b | NM_024171.2 | chr4:47474660-47483233 | 19116 | Serpina3j | NM_001199940.1 | chr12:104263121-104269365 |
| 19020 | Sec61g | NM_001109971.1 | chr11:16501637-16508484 | 19117 | Serpina3j | NM_001101472.2 | chr12:104314569-104320586 |
| 19021 | Sec62 | NM_027016.2 | chr3:30792875-30821263 | 19118 | Serpina3k | NM_013458.2 | chr12:104338485-104345739 |
| 19022 | Sec63 | NM_153055.3 | chr10:42761495-42832514 | 19119 | Serpina3m | NM_009253.2 | chr12:104387163-104394257 |
| 19023 | Secisbp2l | NM_029279.2 | chr13:51651707-51684044 | 19120 | Serpina3n | NM_009252.2 | chr12:104406707-104414329 |
| 19024 | Secisbp2 | NM_177608.3 | chr2:125736985-125782870 | 19121 | Serpina4-ps1 | NR_002861.2 | chr12:104077958-104086920 |
| 19025 | Sectm1a | NM_145373.2 | chr11:121067402-121081139 | 19122 | Serpina5 | NM_172953.3 | chr12:104101112-104106137 |
| 19026 | Sectm1b | NM_026907.3 | chr11:121053422-121063569 | 19123 | Serpina6 | NM_007618.3 | chr12:103646630-103657218 |
| 19027 | Sech1l | NM_001039088.1 | chr18:67774875-67795487 | 19124 | Serpina7 | NM_177920.5 | chrX:139079249-139085236 |
| 19028 | Sel1l | NM_001039089.1 | chr12:91806042-91849157 | 19125 | Serpina9 | NM_027997.2 | chr12:103996619-104013652 |
| 19029 | Sel1l2 | NM_027296.2 | chr2:140229857-140389710 | 19126 | Serpinb10 | NM_001160307.1 | chr1:107529002-107549271 |
| 19030 | Sel1l3 | NM_172910.3 | chr5:53107082-53213452 | 19127 | Serpinb11 | NM_025867.2 | chr1:107362313-107380475 |
| 19031 | Sele | NM_011345.2 | chr1:164048233-164057677 | 19128 | Serpinb12 | NM_001199213.1 | chr1:106938956-106957080 |
| 19032 | Selenbp1 | NM_009150.3 | chr3:94933082-94944758 | 19129 | Serpinb13 | NM_172852.3 | chr1:106980983-107001195 |
| 19033 | Selenbp2 | NM_019414.2 | chr3:94693572-94704406 | 19130 | Serpinb1a | NM_025429.2 | chr13:32842091-32851185 |
| 19034 | Selk | NM_019979.2 | chr14:29968379-29975074 | 19131 | Serpinb1b | NM_173052.2 | chr13:33084102-33094380 |
| 19035 | Sell | NM_001164059.1 | chr1:164062075-164080785 | 19132 | Serpinb1c | NM_173051.2 | chr13:32881396-32898140 |
| 19036 | Selm | NM_053267.2 | chr11:3514701-3517351 | 19133 | Serpinb2 | NM_001174170.1 | chr1:107511422-107525600 |
| 19037 | Selo | NM_027905.2 | chr15:89089106-89100340 | 19134 | Serpinb3a | NM_009126.3 | chr1:107045586-107052303 |
| 19038 | Selp | NM_011347.2 | chr1:164115263-164150026 | 19135 | Serpinb3b | NM_198680.2 | chr1:107153960-107161114 |
| 19039 | Selpig | NM_009151.3 | chr5:113817797-113830501 | 19136 | Serpinb3c | NM_201363.2 | chr1:107271200-107278371 |
| 19040 | Selt | NM_001040396.2 | chr3:58576657-58593546 | 19137 | Serpinb3d | NM_201376.1 | chr1:107078192-107083480 |
| 19041 | Sema3a | NM_001243072.1 | chr5:13396783-13603485 | 19138 | Serpinb5 | NM_009257.3 | chr1:106861179-106883348 |
| 19042 | Sema3b | NM_001042779.2 | chr9:107597673-107609241 | 19139 | Serpinb6a | NM_001184117.1 | chr13:33917917-33936083 |
| 19043 | Sema3c | NM_013657.5 | chr5:17574815-17730267 | 19140 | Serpinb6b | NM_011454.1 | chr13:32965512-32979037 |
| 19044 | Sema3d | NM_028882.4 | chr5:12383165-12588943 | 19141 | Serpinb6c | NM_148942.2 | chr13:33879815-33905708 |
| 19045 | Sema3e | NM_011348.2 | chr5:140225275-14256689 | 19142 | Serpinb6d | NM_001078790.2 | chr13:33661404-33671585 |
| 19046 | Sema3f | NM_011349.3 | chr9:107681501-107710475 | 19143 | Serpinb6e | NM_001045535.2 | chr13:33832344-33843408 |
| 19047 | Sema3g | NM_001025379.1 | chr14:31217872-31229511 | 19144 | Serpinb7 | NM_027548.3 | chr1:107422688-107452689 |
| 19048 | Sema4a | NM_001163445.1 | chr3:88435961-88461182 | 19145 | Serpinb8 | NM_001159748.1 | chr1:107590005-107606150 |
| 19049 | Sema4b | NM_013659.4 | chr7:80186840-80226524 | 19146 | Serpinb9 | NM_009256.3 | chr13:33004540-33017955 |
| 19050 | Sema4c | NM_001126047.3 | chr1:36548638-36558381 | 19147 | Serpinb9b | NM_011452.2 | chr13:33027413-33046558 |
| 19051 | Sema4d | NM_001281880.1 | chr13:51701247-51793747 | 19148 | Serpinb9c | NM_001164524.1 | chr13:33149274-33159754 |
| 19052 | Sema4f | NM_001308374.1 | chr6:82911884-829897 | 19149 | Serpinb9d | NM_013460.2 | chr13:33192958-33203980 |
| 19053 | Sema4g | NM_011976.1 | chr19:44989943-45003395 | 19150 | Serpinb9e | NM_011456.2 | chr13:33249609-33260846 |
| 19054 | Sema5a | NM_009154.2 | chr15:32244812-32696341 | 19151 | Serpinb9f | NM_183197.1 | chr13:33324076-33335366 |
| 19055 | Sema5b | NM_013661.2 | chr16:35541361-35664258 | 19152 | Serpinb9g | NM_011455.3 | chr13:33484789-33496000 |
| 19056 | Sema6a | NM_018744.2 | chr18:47245253-47368868 | 19153 | Serpinc1 | NM_080844.4 | chr1:160978605-161003014 |
| 19057 | Sema6b | NM_001130456.1 | chr17:56123084-56140343 | 19154 | Serpind1 | NM_008223.3 | chr16:17331370-17343572 |
| 19058 | Sema6c | NM_001272024.1 | chr3:96506419-95174050 | 19155 | Serpine1 | NM_008871.2 | chr5:137061505-137072272 |
| 19059 | Sema6d | NM_001290997.1 | chr2:124089968-124667789 | 19156 | Serpine2 | NM_009255.4 | chr1:79794320-79858665 |
| 19060 | Sema7a | NM_011352.2 | chr9:57940134-57982865 | 19157 | Serpine3 | NM_001199945.1 | chr14:62663666-62692243 |
| 19061 | Senp1 | NM_144851.5 | chr15:98038743-98093569 | 19158 | Serpinf1 | NM_013340.3 | chr11:75410028-75422623 |
| 19062 | Senp2 | NM_029457.3 | chr16:22009483-22049269 | 19159 | Serpinf2 | NM_008878.2 | chr11:75431735-75439501 |
| 19063 | Senp3 | NM_001163571.1 | chr11:69673109-69682084 | 19160 | Serping1 | NM_009776.3 | chr2:84765359-84775429 |
| 19064 | Senp5 | NM_177103.4 | chr16:31959669-32003287 | 19161 | Serpinh1 | NM_001111043.1 | chr7:99345374-99353239 |
| 19065 | Senp6 | NM_146003.2 | chr9:80066902-80144780 | 19162 | Serpinl1 | NM_009250.2 | chr3:75557532-75642523 |
| 19066 | Senp7 | NM_001003972.2 | chr16:56072059-56190011 | 19163 | Serpini2 | NM_026460.3 | chr3:75242356-75270078 |
| 19067 | Senp8 | NM_001172068.1 | chr9:59734258-59750649 | 19164 | Sertad1 | NM_018820.4 | chr7:27486952-27490314 |
| 19068 | Sephs1 | NM_175400.6 | chr2:4881563-4910556 | 19165 | Sertad2 | NM_001038625.1 | chr11:20631976-20653023 |
| 19069 | Sephs2 | NM_009266.3 | chr7:127271878-127274059 | 19166 | Sertad3 | NM_133210.2 | chr7:27473839-27477364 |
| 19070 | Sepn1 | NM_029100.2 | chr4:134537891-134552166 | 19167 | Sertad4 | NM_001177794.1 | chr1:192844487-192851747 |
| 19071 | Sepp1 | NM_001042613.1 | chr15:3270766-3280508 | 19168 | Sertm1 | NM_177854.4 | chr3:54897068-54915887 |
| 19072 | Sepsecs | NM_172490.3 | chr5:52643406-52669701 | 19169 | Sesn1 | NM_001013370.2 | chr10:41887436-41908436 |
| 19073 | Sept1 | NM_017461.2 | chr7:127214441-127218445 | 19170 | Sesn2 | NM_144907.1 | chr4:132492806-132510456 |
| 19074 | Sept10 | NM_001024910.3 | chr10:59141626-59221847 | 19171 | Sesn3 | NM_030261.4 | chr9:14276300-14326134 |
| 19075 | Sept11 | NM_001009818.2 | chr5:93093415-93175075 | 19172 | Sestd1 | NM_175465.6 | chr2:77180339-77280592 |
| 19076 | Sept12 | NM_027669.3 | chr16:4986857-4997852 | 19173 | Set | NM_001204875.1 | chr2:30066473-30072577 |
| 19077 | Sept14 | NM_028826.1 | chr5:129683390-129708511 | 19174 | Setbp1 | NM_053099.2 | chr18:78750377-79109391 |
| 19078 | Sept15 | NM_053102.2 | chr3:144570426-144597676 | 19175 | Setd1a | NM_178029.3 | chr7:127777388-127800119 |
| 19079 | Sept2 | NM_001159717.1 | chr1:93478992-93509732 | 19176 | Setd1b | NM_001040398.2 | chr5:123142192-123168630 |
| 19080 | Sept3 | NM_011889.2 | chr15:82274934-82294442 | 19177 | Setd2 | NM_001081340.2 | chr9:110532596-110618633 |
| 19081 | Sept4 | NM_001284392.1 | chr11:87531060-87590539 | 19178 | Setd3 | NM_028262.3 | chr12:108106430-108179284 |
| 19082 | Sept5 | NM_213614.2 | chr16:18621810-18629938 | 19179 | Setd4 | NM_145482.3 | chr16:93583460-93603815 |
| 19083 | Sept6 | NM_001177323.2 | chrX:36911271-36989695 | 19180 | Setd5 | NM_028385.1 | chr6:113077638-113153424 |
| 19084 | Sept7 | NM_001205367.1 | chr9:25252438-25308571 | 19181 | Setd6 | NM_001035123.3 | chr8:95715912-95719004 |
| 19085 | Sept8 | NM_001252331.1 | chr11:53519735-53544096 | 19182 | Setd7 | NM_080793.5 | chr3:51515317-51560823 |
| 19086 | Sept9 | NM_001134486.1 | chr11:117199860-117362325 | 19183 | Setd8 | NM_030241.3 | chr5:124439929-124462311 |
| 19087 | Sepw1 | NM_009156.3 | chr7:15917207-15922371 | 19184 | Setdb1 | NM_001163641.1 | chr3:95323524-95357202 |
| 19088 | Serac1 | NM_001111017.1 | chr17:6040570-6079739 | 19185 | Setdb2 | NM_001081024.1 | chr14:59402010-59440877 |
| 19089 | Serbp1 | NM_001113564.1 | chr6:67266978-67289302 | 19186 | Setmar | NM_001276356.1 | chr6:108065944-108077127 |
| 19090 | Serf1 | NM_001081008-100114233 | | 19187 | Setx | NM_198033.2 | chr2:29124991-29182471 |
| 19091 | Serf2 | NM_001290837.1 | chr2:121449197-121453420 | 19188 | Sez6 | NM_001291225.1 | chr11:77930838-77979082 |
| 19092 | Sergef | NM_013789.2 | chr7:46443158-46639807 | 19189 | Sez6l | NM_001253916.1 | chr5:112419190-112577198 |
| 19093 | Serhl | NM_027435.3 | chr15:83100204-83116671 | 19190 | Sez6l2 | NM_001252566.1 | chr7:126950534-126970606 |
| 19094 | Serinc1 | NM_019760.3 | chr10:57515774-57532529 | 19191 | Sf1 | NM_001107791.1 | chr19:6363689-6378038 |
| 19095 | Serinc2 | NM_001253386.1 | chr4:130253496-130275220 | 19192 | Sf3a1 | NM_026175.5 | chr11:4160353-4182541 |
| 19096 | Serinc3 | NM_012032.4 | chr2:163623272-163645143 | 19193 | Sf3a2 | NM_013651.4 | chr10:80798734-80804922 |
| 19097 | Serinc4 | NM_001025371.2 | chr2:121451176-121466764 | 19194 | Sf3a3 | NM_029157.3 | chr4:124714860-124732422 |
| 19098 | Serinc5 | NM_172588.1 | chr13:92611137-92731946 | 19195 | Sf3b1 | NM_031179.2 | chr1:54985169-55027478 |
| 19099 | Serp1 | NM_030685.3 | chr3:58521970-58525884 | 19196 | Sf3b2 | NM_030109.2 | chr19:5273920-5295455 |
| 19100 | Serp2 | NM_001160326.1 | chr14:76532811-76556687 | 19197 | Sf3b3 | NM_133953.2 | chr8:110810491-110846803 |
| 19101 | Serpina10 | NM_144815.5 | chr12:103616674-103631444 | 19198 | Sf3b4 | NM_153053.4 | chr3:96172505-96177564 |
| 19102 | Serpina11 | NM_001166350.1 | chr12:103980242-103999957 | 19199 | Sf3b5 | NM_175102.4 | chr10:13008449-13009183 |
| 19103 | Serpina12 | NM_026535.2 | chr12:104028763-104044443 | 19200 | Sf3b6 | NM_025323.2 | chr12:4817607-4827659 |
| 19104 | Serpina1a | NM_001252569.1 | chr12:103853294-103863619 | 19201 | Sfi1 | NM_030207.2 | chr11:3131849-3193463 |
| 19105 | Serpina1b | NM_009244.4 | chr12:103728155-103738189 | 19202 | Sfmbt1 | NM_001166531.1 | chr14:30715166-30822721 |
| 19106 | Serpina1c | NM_009245.2 | chr12:103894925-103904950 | 19203 | Sfmbt2 | NM_001198808.1 | chr2:10370430-10595253 |
| 19107 | Serpina1d | NM_009246.3 | chr12:103763586-103773633 | 19204 | Sfn | NM_018754.2 | chr4:133600555-133602168 |
| 19108 | Serpina1e | NM_009247.2 | chr12:103946931-103956897 | 19205 | Sfpq | NM_023603.3 | chr4:127021300-127031236 |

Fig.21 - 100

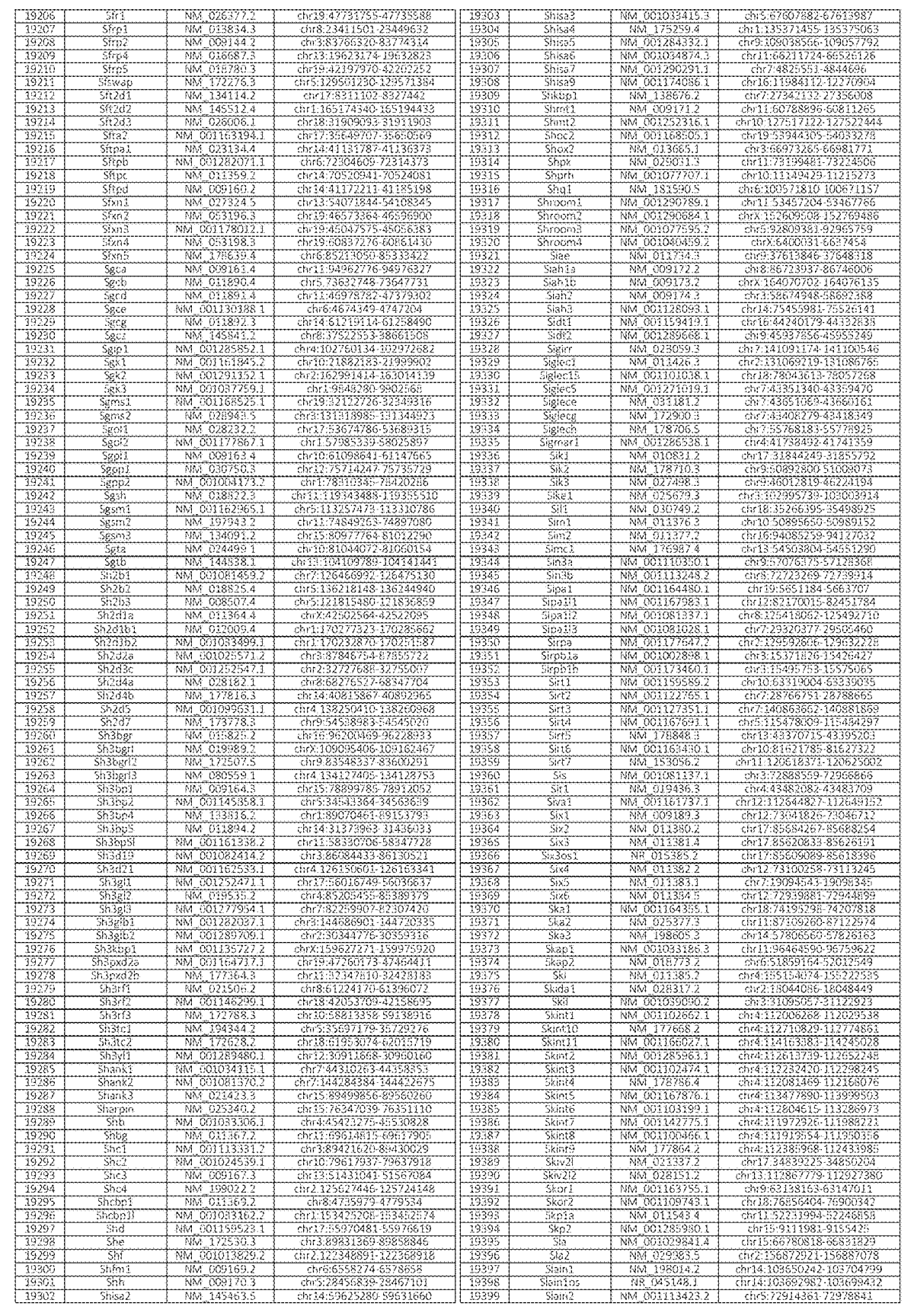

| | | | |
|---|---|---|---|
| 19206 | Sfr1 | NM_026377.2 | chr19:47731755-47735588 |
| 19207 | Sfrp1 | NM_013834.3 | chr8:23411501-23449632 |
| 19208 | Sfrp2 | NM_009144.2 | chr3:83766320-83774314 |
| 19209 | Sfrp4 | NM_016687.3 | chr13:19623174-19632823 |
| 19210 | Sfrp5 | NM_018780.3 | chr19:42197970-42202252 |
| 19211 | Sfswap | NM_172276.3 | chr5:129501230-129571384 |
| 19212 | Sft2d1 | NM_134114.2 | chr17:8311102-8327442 |
| 19213 | Sft2d2 | NM_145512.4 | chr1:165174340-165194433 |
| 19214 | Sft2d3 | NM_026006.1 | chr18:31909093-31911903 |
| 19215 | Sfta2 | NM_001163194.1 | chr17:35649707-35650569 |
| 19216 | Sftpa1 | NM_023134.4 | chr14:41131787-41136373 |
| 19217 | Sftpb | NM_001282071.1 | chr6:72304609-72314373 |
| 19218 | Sftpc | NM_011359.2 | chr14:70520941-70524081 |
| 19219 | Sftpd | NM_009160.2 | chr14:41172211-41185198 |
| 19220 | Sfxn1 | NM_027324.5 | chr13:54071844-54108345 |
| 19221 | Sfxn2 | NM_053196.3 | chr19:46573364-46596900 |
| 19222 | Sfxn3 | NM_001178012.1 | chr19:45047575-45056383 |
| 19223 | Sfxn4 | NM_053198.3 | chr19:60837276-60861430 |
| 19224 | Sfxn5 | NM_178639.4 | chr6:85213050-85333422 |
| 19225 | Sgca | NM_009161.4 | chr11:94962776-94976327 |
| 19226 | Sgcb | NM_011890.4 | chr5:73632748-73647731 |
| 19227 | Sgcd | NM_011891.4 | chr11:46978782-47379302 |
| 19228 | Sgce | NM_001130188.1 | chr6:4674349-4747204 |
| 19229 | Sgcg | NM_011892.3 | chr14:61219114-61258490 |
| 19230 | Sgcz | NM_145841.2 | chr8:37522553-38661508 |
| 19231 | Sgip1 | NM_001285852.1 | chr4:102760134-102972682 |
| 19232 | Sgk1 | NM_001161845.2 | chr10:21882183-21999902 |
| 19233 | Sgk2 | NM_001291152.1 | chr2:162991414-163014139 |
| 19234 | Sgk3 | NM_001037759.1 | chr1:9848280-9902568 |
| 19235 | Sgms1 | NM_001168525.1 | chr19:32122726-32349316 |
| 19236 | Sgms2 | NM_028943.5 | chr3:131318985-131344923 |
| 19237 | Sgol1 | NM_028232.2 | chr17:53674786-53689315 |
| 19238 | Sgol2 | NM_001177867.1 | chr1:57985339-58025897 |
| 19239 | Sgpl1 | NM_009163.4 | chr10:61098641-61147665 |
| 19240 | Sgpp1 | NM_030750.3 | chr12:75714247-75735729 |
| 19241 | Sgpp2 | NM_001004173.2 | chr1:78310345-78420286 |
| 19242 | Sgsh | NM_018822.3 | chr11:119343488-119355510 |
| 19243 | Sgsm1 | NM_001162965.1 | chr5:113257473-113310786 |
| 19244 | Sgsm2 | NM_197943.2 | chr11:74849263-74897080 |
| 19245 | Sgsm3 | NM_134091.2 | chr15:80977764-81012290 |
| 19246 | Sgta | NM_024499.1 | chr10:81044072-81060154 |
| 19247 | Sgtb | NM_144838.1 | chr13:104109789-104141441 |
| 19248 | Sh2b1 | NM_001081459.2 | chr7:126466992-126475130 |
| 19249 | Sh2b2 | NM_018825.4 | chr5:136218148-136244940 |
| 19250 | Sh2b3 | NM_008507.4 | chr5:121815480-121836859 |
| 19251 | Sh2d1a | NM_011364.4 | chrX:42502564-42522095 |
| 19252 | Sh2d1b1 | NM_012009.4 | chr1:170277323-170285662 |
| 19253 | Sh2d1b2 | NM_001033499.1 | chr1:170232870-170251587 |
| 19254 | Sh2d2a | NM_001025571.2 | chr3:87846754-87855722 |
| 19255 | Sh2d3c | NM_001252547.1 | chr2:32727688-32755007 |
| 19256 | Sh2d4a | NM_028182.1 | chr8:68276527-68347704 |
| 19257 | Sh2d4b | NM_177816.3 | chr14:40815867-40892965 |
| 19258 | Sh2d5 | NM_001099631.1 | chr4:138250410-138260968 |
| 19259 | Sh2d7 | NM_173778.3 | chr9:54538983-54545020 |
| 19260 | Sh3bgr | NM_015825.2 | chr16:96200469-96228933 |
| 19261 | Sh3bgrl | NM_019989.2 | chrX:109095406-109162467 |
| 19262 | Sh3bgrl2 | NM_172507.5 | chr9:83548337-83600291 |
| 19263 | Sh3bgrl3 | NM_080559.1 | chr4:134127405-134128753 |
| 19264 | Sh3bp1 | NM_009164.3 | chr15:78899785-78912052 |
| 19265 | Sh3bp2 | NM_001145858.1 | chr5:34543364-34563639 |
| 19266 | Sh3bp4 | NM_133816.2 | chr1:89070461-89153793 |
| 19267 | Sh3bp5 | NM_011894.2 | chr14:31373963-31436033 |
| 19268 | Sh3bp5l | NM_001161338.2 | chr11:58330706-58347728 |
| 19269 | Sh3d19 | NM_001082414.2 | chr3:86084433-86130521 |
| 19270 | Sh3d21 | NM_001162533.1 | chr4:126150601-126163341 |
| 19271 | Sh3gl1 | NM_001252471.1 | chr17:56016749-56036637 |
| 19272 | Sh3gl2 | NM_019535.2 | chr4:85205455-85389379 |
| 19273 | Sh3gl3 | NM_001277954.1 | chr7:82259907-82307420 |
| 19274 | Sh3glb1 | NM_001282037.1 | chr3:144686901-144720335 |
| 19275 | Sh3glb2 | NM_001289709.1 | chr2:30344776-30359316 |
| 19276 | Sh3kbp1 | NM_001135727.2 | chrX:159627271-159975920 |
| 19277 | Sh3pxd2a | NM_001164717.1 | chr19:47260173-47464411 |
| 19278 | Sh3pxd2b | NM_177364.3 | chr11:32347810-32428183 |
| 19279 | Sh3rf1 | NM_021506.2 | chr8:61224170-61396072 |
| 19280 | Sh3rf2 | NM_001146299.1 | chr18:42053709-42158695 |
| 19281 | Sh3rf3 | NM_172788.3 | chr10:58813358-59138916 |
| 19282 | Sh3tc1 | NM_194344.2 | chr5:35697179-35729276 |
| 19283 | Sh3tc2 | NM_172628.2 | chr18:61953074-62015719 |
| 19284 | Sh3yl1 | NM_001289480.1 | chr12:30911668-30960160 |
| 19285 | Shank1 | NM_001034115.1 | chr7:44310263-44358353 |
| 19286 | Shank2 | NM_001081370.2 | chr7:144284384-144422675 |
| 19287 | Shank3 | NM_021423.3 | chr15:89499856-89560260 |
| 19288 | Sharpin | NM_025340.2 | chr15:76347039-76351110 |
| 19289 | Shb | NM_001033306.1 | chr4:45423275-45530828 |
| 19290 | Shbg | NM_011367.2 | chr11:69614815-69617905 |
| 19291 | Shc1 | NM_001113331.2 | chr3:89421620-89430029 |
| 19292 | Shc2 | NM_001024539.1 | chr10:79617937-79637918 |
| 19293 | Shc3 | NM_009167.3 | chr13:51431041-51567084 |
| 19294 | Shc4 | NM_199022.2 | chr2:125627446-125724148 |
| 19295 | Shcbp1 | NM_011369.2 | chr8:4735979-4779534 |
| 19296 | Shcbp1l | NM_001033162.2 | chr1:153425208-153452574 |
| 19297 | Shd | NM_001159523.1 | chr17:55970481-55976619 |
| 19298 | She | NM_172530.3 | chr3:89831369-89858846 |
| 19299 | Shf | NM_001013829.2 | chr2:122348891-122368918 |
| 19300 | Shfm1 | NM_009169.2 | chr6:6558274-6578658 |
| 19301 | Shh | NM_009170.3 | chr5:28456839-28467101 |
| 19302 | Shisa2 | NM_145463.5 | chr14:59625280-59631660 |
| 19303 | Shisa3 | NM_001033415.3 | chr5:67607882-67613987 |
| 19304 | Shisa4 | NM_175259.4 | chr1:135371455-135375063 |
| 19305 | Shisa5 | NM_001284332.1 | chr9:109038566-109057792 |
| 19306 | Shisa6 | NM_001034874.3 | chr11:66211724-66526126 |
| 19307 | Shisa7 | NM_001290291.1 | chr7:4825551-4844696 |
| 19308 | Shisa9 | NM_001174086.1 | chr16:11984112-12270904 |
| 19309 | Shkbp1 | NM_138676.2 | chr7:27342132-27356008 |
| 19310 | Shmt1 | NM_009171.2 | chr11:60788896-60811265 |
| 19311 | Shmt2 | NM_001252316.1 | chr10:127517122-127522444 |
| 19312 | Shoc2 | NM_001168505.1 | chr19:53944305-54033278 |
| 19313 | Shox2 | NM_013665.1 | chr3:66973265-66981771 |
| 19314 | Shpk | NM_029031.3 | chr11:73199481-73224506 |
| 19315 | Shprh | NM_001077707.1 | chr10:11149429-11215273 |
| 19316 | Shq1 | NM_181590.5 | chr6:100571810-100671157 |
| 19317 | Shroom1 | NM_001290789.1 | chr11:53457204-53467766 |
| 19318 | Shroom2 | NM_001290684.1 | chrX:152609508-152769486 |
| 19319 | Shroom3 | NM_001077595.2 | chr5:92809381-92965759 |
| 19320 | Shroom4 | NM_001040459.2 | chrX:6400031-6637454 |
| 19321 | Siae | NM_011734.3 | chr9:37613846-37648318 |
| 19322 | Siah1a | NM_009172.2 | chr8:86723937-86746006 |
| 19323 | Siah1b | NM_009173.2 | chrX:164070702-164076135 |
| 19324 | Siah2 | NM_009174.3 | chr3:58674948-58692388 |
| 19325 | Siah3 | NM_001128093.1 | chr14:75455981-75526141 |
| 19326 | Sidt1 | NM_001159419.1 | chr16:44240179-44332838 |
| 19327 | Sidt2 | NM_001289668.1 | chr9:45937856-45955249 |
| 19328 | Sigirr | NM_023059.3 | chr7:141091174-141100546 |
| 19329 | Siglec1 | NM_011426.3 | chr2:131069219-131086765 |
| 19330 | Siglec15 | NM_001101038.1 | chr18:78043613-78057268 |
| 19331 | Siglec5 | NM_001271019.1 | chr7:43351340-43359470 |
| 19332 | Siglece | NM_031181.2 | chr7:43651069-43660161 |
| 19333 | Siglecg | NM_172900.3 | chr7:43408279-43418349 |
| 19334 | Siglech | NM_178706.5 | chr7:55768183-55778925 |
| 19335 | Sigmar1 | NM_001286538.1 | chr4:41738492-41741359 |
| 19336 | Sik1 | NM_010831.2 | chr17:31844249-31855792 |
| 19337 | Sik2 | NM_178710.3 | chr9:50892800-51009073 |
| 19338 | Sik3 | NM_027498.3 | chr9:46012819-46224194 |
| 19339 | Sike1 | NM_025679.3 | chr3:102995739-103003914 |
| 19340 | Sil1 | NM_030749.2 | chr18:35266395-35498925 |
| 19341 | Sim1 | NM_011376.3 | chr10:50895650-50989152 |
| 19342 | Sim2 | NM_011377.2 | chr16:94085259-94127032 |
| 19343 | Simc1 | NM_176987.4 | chr13:54503804-54551290 |
| 19344 | Sin3a | NM_001110350.1 | chr9:57076375-57128368 |
| 19345 | Sin3b | NM_001113248.2 | chr8:72723269-72739914 |
| 19346 | Sipa1 | NM_001164480.1 | chr19:5651184-5663707 |
| 19347 | Sipa1l1 | NM_001167983.1 | chr12:82170015-82451784 |
| 19348 | Sipa1l2 | NM_001081337.1 | chr8:125418062-125492710 |
| 19349 | Sipa1l3 | NM_001081028.1 | chr7:29320377-29505460 |
| 19350 | Sirpa | NM_001177647.2 | chr2:129592606-129632228 |
| 19351 | Sirpb1a | NM_001002898.1 | chr3:15371826-15426427 |
| 19352 | Sirpb1b | NM_001173460.1 | chr3:15495753-15575065 |
| 19353 | Sirt1 | NM_001159589.2 | chr10:63319004-63339035 |
| 19354 | Sirt2 | NM_001122765.1 | chr7:28766751-28788665 |
| 19355 | Sirt3 | NM_001127351.1 | chr7:140863662-140881869 |
| 19356 | Sirt4 | NM_001167691.1 | chr5:115478009-115484297 |
| 19357 | Sirt5 | NM_178848.3 | chr13:43370715-43395203 |
| 19358 | Sirt6 | NM_001163430.1 | chr10:81621785-81627322 |
| 19359 | Sirt7 | NM_153056.2 | chr11:120618371-120625002 |
| 19360 | Sis | NM_001081137.1 | chr3:72888559-72966866 |
| 19361 | Sit1 | NM_019436.3 | chr4:43482082-43483709 |
| 19362 | Siva1 | NM_001161737.1 | chr12:112644827-112649152 |
| 19363 | Six1 | NM_009189.3 | chr12:73041826-73046712 |
| 19364 | Six2 | NM_011380.2 | chr17:85684267-85688254 |
| 19365 | Six3 | NM_011381.4 | chr17:85620833-85626191 |
| 19366 | Six3os1 | NR_015385.2 | chr17:85609089-85618396 |
| 19367 | Six4 | NM_011382.2 | chr12:73100258-73113245 |
| 19368 | Six5 | NM_011383.1 | chr7:19094543-19098345 |
| 19369 | Six6 | NM_011384.5 | chr12:72939881-72944899 |
| 19370 | Ska1 | NM_001164355.1 | chr18:74195298-74207818 |
| 19371 | Ska2 | NM_025377.3 | chr11:87109260-87122974 |
| 19372 | Ska3 | NM_198605.3 | chr14:57806560-57826163 |
| 19373 | Skap1 | NM_001033186.3 | chr11:96464590-96759622 |
| 19374 | Skap2 | NM_018773.2 | chr6:51859164-52012549 |
| 19375 | Ski | NM_011385.2 | chr4:155154074-155222535 |
| 19376 | Skida1 | NM_028317.2 | chr2:18044086-18048449 |
| 19377 | Skil | NM_001039090.2 | chr3:31095057-31122923 |
| 19378 | Skint1 | NM_001102662.1 | chr4:112006268-112029538 |
| 19379 | Skint10 | NM_177668.2 | chr4:112710829-112774861 |
| 19380 | Skint11 | NM_001166027.1 | chr4:114163383-114245028 |
| 19381 | Skint2 | NM_001285963.1 | chr4:112613739-112652248 |
| 19382 | Skint3 | NM_001102474.1 | chr4:112232420-112298245 |
| 19383 | Skint4 | NM_178786.4 | chr4:112081469-112168076 |
| 19384 | Skint5 | NM_001167876.1 | chr4:113477890-113999503 |
| 19385 | Skint6 | NM_001103199.1 | chr4:112804615-113286973 |
| 19386 | Skint7 | NM_001142775.1 | chr4:111972926-111988221 |
| 19387 | Skint8 | NM_001100466.1 | chr4:111919554-111950356 |
| 19388 | Skint9 | NM_177864.2 | chr4:112385968-112433985 |
| 19389 | Skiv2l | NM_021337.2 | chr17:34839225-34850204 |
| 19390 | Skiv2l2 | NM_028151.2 | chr13:112867779-112927380 |
| 19391 | Skor1 | NM_001163755.1 | chr9:63138163-63147011 |
| 19392 | Skor2 | NM_001109743.1 | chr18:76856404-76900342 |
| 19393 | Skp1a | NM_011543.4 | chr11:52231994-52246858 |
| 19394 | Skp2 | NM_001285980.1 | chr15:9111981-9155425 |
| 19395 | Sla | NM_001029841.4 | chr15:66780818-66831829 |
| 19396 | Sla2 | NM_029383.5 | chr2:156872921-156887078 |
| 19397 | Slain1 | NM_198014.2 | chr14:103650242-103704799 |
| 19398 | Slain1os | NR_045148.1 | chr14:103692982-103699432 |
| 19399 | Slain2 | NM_001113423.2 | chr5:72914361-72978841 |

Fig.21 - 101

| | | | | | | | |
|---|---|---|---|---|---|---|---|
| 19400 | Slamf1 | NM_013730.4 | chr1:171767131-171801184 | 19497 | Slc22a30 | NM_177002.3 | chr19:8335622-8405105 |
| 19401 | Slamf6 | NM_030710.2 | chr1:171917536-171943868 | 19498 | Slc22a4 | NM_019687.3 | chr11:53983125-54028090 |
| 19402 | Slamf7 | NM_144539.5 | chr1:171632402-171653037 | 19499 | Slc22a5 | NM_011396.3 | chr11:53864541-53891703 |
| 19403 | Slamf8 | NM_029084.3 | chr1:172581376-172590568 | 19500 | Slc22a6 | NM_008766.3 | chr19:8617995-8628299 |
| 19404 | Slamf9 | NM_029612.4 | chr1:172475359-172478409 | 19501 | Slc22a7 | NM_144856.2 | chr17:46432184-46438477 |
| 19405 | Slbp | NM_001289724.1 | chr5:33640054-33652574 | 19502 | Slc22a8 | NM_001164634.1 | chr19:8591253-8611835 |
| 19406 | Slc10a1 | NM_001177561.1 | chr12:80953184-80968079 | 19503 | Slc23a1 | NM_011397.4 | chr18:35614603-35627227 |
| 19407 | Slc10a2 | NM_011388.2 | chr8:5085622-5105232 | 19504 | Slc23a2 | NM_018824.2 | chr2:132052495-132145108 |
| 19408 | Slc10a3 | NM_001256304.1 | chrX:74369218-74373349 | 19505 | Slc23a3 | NM_194333.3 | chr1:75125541-75133890 |
| 19409 | Slc10a3-ubl4 | NM_001278271.1 | chrX:74367446-74373349 | 19506 | Slc24a1 | NM_144813.1 | chr9:64922860-64951607 |
| 19410 | Slc10a4 | NM_173403.2 | chr5:73006903-73012955 | 19507 | Slc24a2 | NM_001110240.1 | chr4:86983125-87227963 |
| 19411 | Slc10a5 | NM_001010834.2 | chr3:10331733-10335656 | 19508 | Slc24a3 | NM_053195.2 | chr2:145242610-145641939 |
| 19412 | Slc10a6 | NM_029415.2 | chr5:103605710-103629403 | 19509 | Slc24a4 | NM_172152.2 | chr12:102129418-102266749 |
| 19413 | Slc10a7 | NM_001009981.2 | chr8:78509327-78734012 | 19510 | Slc24a5 | NM_175034.3 | chr2:125068126-125088677 |
| 19414 | Slc11a1 | NM_013612.2 | chr1:74375202-74386051 | 19511 | Slc25a1 | NM_153150.2 | chr16:17925210-17928219 |
| 19415 | Slc11a2 | NM_001146161.1 | chr15:100392657-100423055 | 19512 | Slc25a10 | NM_013770.2 | chr11:120491836-120501161 |
| 19416 | Slc12a1 | NM_001079690.1 | chr2:125152599-125230001 | 19513 | Slc25a11 | NM_024211.3 | chr11:70644026-70647039 |
| 19417 | Slc12a2 | NM_009194.3 | chr18:57878677-57946821 | 19514 | Slc25a12 | NM_172436.3 | chr2:71274294-71367554 |
| 19418 | Slc12a3 | NM_001205311.1 | chr8:94329207-94366221 | 19515 | Slc25a13 | NM_001177572.1 | chr6:6041217-6217173 |
| 19419 | Slc12a4 | NM_001253804.1 | chr8:105943589-105966115 | 19516 | Slc25a14 | NM_001166450.2 | chrX:48623673-48662298 |
| 19420 | Slc12a5 | NM_020333.2 | chr2:164967987-164999731 | 19517 | Slc25a15 | NM_181325.4 | chr8:22375549-22398621 |
| 19421 | Slc12a6 | NM_133648.2 | chr2:112284687-112363163 | 19518 | Slc25a16 | NM_175194.2 | chr10:62920632-62946494 |
| 19422 | Slc12a7 | NM_011390.2 | chr13:73763696-73816742 | 19519 | Slc25a17 | NM_011399.3 | chr15:81318920-81360765 |
| 19423 | Slc12a8 | NM_001083902.1 | chr16:33518594-33664135 | 19520 | Slc25a18 | NM_001081048.2 | chr6:120773767-120793982 |
| 19424 | Slc12a9 | NM_031406.3 | chr5:137314557-137333582 | 19521 | Slc25a19 | NM_001252384.1 | chr11:115614180-115628295 |
| 19425 | Slc13a1 | NM_019481.2 | chr6:24088282-24168092 | 19522 | Slc2a2 | NM_001159275.1 | chr18:37637377-37688723 |
| 19426 | Slc13a2 | NM_024411.3 | chr11:78397275-78422185 | 19523 | Slc25a20 | NM_020520.4 | chr9:108662097-108684641 |
| 19427 | Slc13a2os | NR_003282.2 | chr11:78394484-78405657 | 19524 | Slc25a21 | NM_001167976.1 | chr12:56712633-57160643 |
| 19428 | Slc13a3 | NM_054055.2 | chr2:165405294-165473197 | 19525 | Slc25a22 | NM_001175576.1 | chr7:141429748-141434594 |
| 19429 | Slc13a4 | NM_172392.3 | chr6:35287952-35308126 | 19526 | Slc25a23 | NM_025877.4 | chr17:57043710-57059863 |
| 19430 | Slc13a5 | NM_001004148.4 | chr11:72241993-72266604 | 19527 | Slc25a24 | NM_172685.3 | chr3:109123148-109168409 |
| 19431 | Slc14a1 | NM_001171010.1 | chr18:78100090-78123426 | 19528 | Slc25a25 | NM_001164357.1 | chr2:32414486-32451470 |
| 19432 | Slc14a2 | NM_001110273.1 | chr18:78146143-78179172 | 19529 | Slc25a26 | NM_026255.5 | chr6:94500313-94604652 |
| 19433 | Slc15a1 | NM_053079.2 | chr14:121459620-121505254 | 19530 | Slc25a27 | NM_028711.3 | chr17:43641899-43667015 |
| 19434 | Slc15a2 | NM_001145899.1 | chr16:36771876-36784962 | 19531 | Slc25a28 | NM_145156.1 | chr19:43663800-43674881 |
| 19435 | Slc15a3 | NM_023044.2 | chr19:10842543-10857915 | 19532 | Slc25a29 | NM_181328.3 | chr12:108825877-108835876 |
| 19436 | Slc15a4 | NM_133895.1 | chr5:127559665-127617392 | 19533 | Slc25a3 | NM_133668.3 | chr10:91116577-91123963 |
| 19437 | Slc15a5 | NM_177787.4 | chr6:137983589-138079916 | 19534 | Slc25a30 | NM_026232.3 | chr14:75761998-75787037 |
| 19438 | Slc16a1 | NM_009196.4 | chr3:104618663-104658462 | 19535 | Slc25a31 | NM_178386.3 | chr3:40708870-40726094 |
| 19439 | Slc16a10 | NM_001114332.1 | chr10:40033534-40142254 | 19536 | Slc25a32 | NM_172402.3 | chr15:39094190-39112716 |
| 19440 | Slc16a11 | NM_153081.3 | chr11:70213909-70216414 | 19537 | Slc25a33 | NM_027460.2 | chr4:149744035-149774267 |
| 19441 | Slc16a12 | NM_172838.3 | chr19:34660405-34747111 | 19538 | Slc25a34 | NM_001013780.1 | chr4:141618824-141623884 |
| 19442 | Slc16a13 | NM_172371.3 | chr11:70216791-70220994 | 19539 | Slc25a35 | NM_028048.2 | chr11:68968130-68972515 |
| 19443 | Slc16a14 | NM_027921.1 | chr1:84906704-84935083 | 19540 | Slc25a36 | NM_138756.4 | chr9:97077010-97111041 |
| 19444 | Slc16a2 | NM_009197.2 | chrX:103697413-103821988 | 19541 | Slc25a37 | NM_026331.3 | chr14:69241850-69285103 |
| 19445 | Slc16a3 | NM_001038653.1 | chr11:120949066-120959000 | 19542 | Slc25a38 | NM_144793.1 | chr9:120110398-120124319 |
| 19446 | Slc16a4 | NM_146136.1 | chr3:107291291-107312116 | 19543 | Slc25a39 | NM_026542.3 | chr11:102402975-102407517 |
| 19447 | Slc16a5 | NM_001080934.1 | chr11:115462472-115474398 | 19544 | Slc25a4 | NM_007450.4 | chr8:46207340-46211009 |
| 19448 | Slc16a6 | NM_001029842.1 | chr11:109450855-109473596 | 19545 | Slc25a40 | NM_001289595.1 | chr5:8422837-8454839 |
| 19449 | Slc16a7 | NM_011391.1 | chr10:125227484-125328535 | 19546 | Slc25a41 | NM_175333.3 | chr17:57037771-57041654 |
| 19450 | Slc16a8 | NM_020516.2 | chr15:79251015-79254748 | 19547 | Slc25a42 | NM_001007570.2 | chr8:70184339-70202281 |
| 19451 | Slc16a9 | NM_025807.3 | chr10:70245275-70285951 | 19548 | Slc25a43 | NM_001085497.2 | chrX:36743631-36773307 |
| 19452 | Slc17a1 | NM_001170638.1 | chr13:23870272-23895730 | 19549 | Slc25a44 | NM_001145876.2 | chr3:88410493-88425141 |
| 19453 | Slc17a2 | NM_172523.3 | chr13:23807026-23823525 | 19550 | Slc25a45 | NM_134154.3 | chr19:5878465-5885768 |
| 19454 | Slc17a3 | NM_001164743.1 | chr13:23839433-23860714 | 19551 | Slc25a46 | NM_026165.3 | chr18:31580167-31609902 |
| 19455 | Slc17a4 | NM_177016.3 | chr13:23897688-23915007 | 19552 | Slc25a47 | NM_001012310.2 | chr12:108851128-108856815 |
| 19456 | Slc17a5 | NM_001276452.1 | chr9:78536486-78588045 | 19553 | Slc25a48 | NM_177809.4 | chr13:56438354-56472363 |
| 19457 | Slc17a6 | NM_080853.3 | chr7:51621829-51671126 | 19554 | Slc25a5 | NM_007451.4 | chrX:36795596-36798808 |
| 19458 | Slc17a7 | NM_182993.2 | chr7:45163920-45176139 | 19555 | Slc25a51 | NM_001009949.3 | chr4:45395923-45408766 |
| 19459 | Slc17a8 | NM_182959.3 | chr10:89574019-89621249 | 19556 | Slc25a53 | NM_001082412.2 | chrX:136981115-137038302 |
| 19460 | Slc17a9 | NM_183161.3 | chr2:180725338-180742278 | 19557 | Slc25a54 | NM_029054.1 | chr3:109080498-109116582 |
| 19461 | Slc18a1 | NM_153054.2 | chr8:69037707-69089222 | 19558 | Slc26a1 | NM_174870.4 | chr5:108669880-108675365 |
| 19462 | Slc18a2 | NM_172523.3 | chr19:59260738-59296012 | 19559 | Slc26a10 | NM_177615.3 | chr10:127172425-127180645 |
| 19463 | Slc18a3 | NM_021712.2 | chr14:32462436-32464850 | 19560 | Slc26a11 | NM_178743.3 | chr11:119355556-119381076 |
| 19464 | Slc18b1 | NM_183116.2 | chr10:23796985-23827968 | 19561 | Slc26a2 | NM_007885.2 | chr18:61196853-61211596 |
| 19465 | Slc19a1 | NM_001199271.1 | chr10:77032738-77050432 | 19562 | Slc26a3 | NM_021353.3 | chr12:31438218-31473919 |
| 19466 | Slc19a2 | NM_001276455.1 | chr1:164249045-164265385 | 19563 | Slc26a4 | NM_011867.3 | chr12:31519818-31559969 |
| 19467 | Slc19a3 | NM_030556.2 | chr1:83012522-83038448 | 19564 | Slc26a5 | NM_001289787.1 | chr5:21809000-21862006 |
| 19468 | Slc1a1 | NM_009199.2 | chr19:23365185-28913960 | 19565 | Slc26a6 | NM_134420.4 | chr9:108854042-108862143 |
| 19469 | Slc1a2 | NM_001077514.3 | chr2:102658682-102790784 | 19566 | Slc26a7 | NM_145947.2 | chr4:14505196-14621778 |
| 19470 | Slc1a3 | NM_148938.3 | chr15:8634123-8710807 | 19567 | Slc26a8 | NM_001290320.1 | chr17:28637778-28689987 |
| 19471 | Slc1a4 | NM_018861.3 | chr11:20302179-20332713 | 19568 | Slc26a9 | NM_177243.4 | chr1:131744021-131770405 |
| 19472 | Slc1a5 | NM_009201.2 | chr7:16781345-16798274 | 19569 | Slc27a1 | NM_011977.3 | chr8:71568926-71586708 |
| 19473 | Slc1a6 | NM_009195.2 | chr10:78078495-78814825 | 19570 | Slc27a2 | NM_011978.2 | chr2:126553023-126588243 |
| 19474 | Slc1a7 | NM_146255.2 | chr4:107968333-108013532 | 19571 | Slc27a3 | NM_011988.3 | chr3:90385232-90389927 |
| 19475 | Slc20a1 | NM_001159593.1 | chr2:129198772-129205104 | 19572 | Slc27a4 | NM_011989.4 | chr2:29802679-29817522 |
| 19476 | Slc20a2 | NM_011394.3 | chr8:22476699-22569616 | 19573 | Slc27a5 | NM_009512.2 | chr7:12988345-12998192 |
| 19477 | Slc22a1 | NM_009202.5 | chr17:12648874-12675838 | 19574 | Slc27a6 | NM_001081072.1 | chr18:58556239-58612869 |
| 19478 | Slc22a12 | NM_009203.3 | chr19:6535855-6543070 | 19575 | Slc28a1 | NM_001004184.3 | chr7:81114798-81170416 |
| 19479 | Slc22a13 | NM_133868.3 | chr9:119192977-119209105 | 19576 | Slc28a2 | NM_172980.2 | chr2:122426476-122461180 |
| 19480 | Slc22a13b-ps | NR_033303.1 | chr9:119220490-119231692 | 19577 | Slc28a3 | NM_022317.3 | chr13:58553307-58610877 |
| 19481 | Slc22a14 | NM_001037749.2 | chr9:119169455-119190393 | 19578 | Slc29a1 | NM_001199313.1 | chr17:45585199-45593640 |
| 19482 | Slc22a15 | NM_001039371.2 | chr3:101855770-101924453 | 19579 | Slc29a2 | NM_007854.3 | chr19:5024005-5031972 |
| 19483 | Slc22a16 | NM_027572.1 | chr10:40570361-40604132 | 19580 | Slc29a3 | NM_023596.3 | chr10:60712071-60752782 |
| 19484 | Slc22a17 | NM_001042760.1 | chr14:54906726-54913132 | 19581 | Slc29a4 | NM_146257.2 | chr5:142702100-142722490 |
| 19485 | Slc22a18 | NM_001042760.1 | chr7:143475115-143499332 | 19582 | Slc2a1 | NM_011400.3 | chr4:119108744-119137329 |
| 19486 | Slc22a19 | NM_144785.1 | chr19:7673075-7711310 | 19583 | Slc2a10 | NM_130451.3 | chr2:165503896-165519917 |
| 19487 | Slc22a2 | NM_013667.2 | chr17:12584188-12628488 | 19584 | Slc2a12 | NM_178934.4 | chr10:22645010-22703880 |
| 19488 | Slc22a20 | NM_198650.2 | chr19:5970233-5986143 | 19585 | Slc2a13 | NM_001033633.3 | chr15:91267690-91573261 |
| 19489 | Slc22a21 | NM_019723.2 | chr11:53950823-53980027 | 19586 | Slc2a2 | NM_031197.2 | chr3:28697902-28726350 |
| 19490 | Slc22a22 | NM_172378.2 | chr15:57243770-57477625 | 19587 | Slc2a3 | NM_011401.4 | chr8:122727808-122742745 |
| 19491 | Slc22a23 | NM_001033167.3 | chr13:34179157-34345182 | 19588 | Slc2a4 | NM_009204.2 | chr11:69942285-69948190 |
| 19492 | Slc22a26 | NM_146232.1 | chr19:7781980-7802667 | 19589 | Slc2a4rg-ps | NR_045164.1 | chr2:181384249-181387596 |
| 19493 | Slc22a27 | NM_134256.1 | chr19:7864388-7966027 | 19590 | Slc2a5 | NM_019741.3 | chr4:150119343-150144168 |
| 19494 | Slc22a28 | NM_001013820.3 | chr19:8062208-8131982 | 19591 | Slc2a6 | NM_001177627.1 | chr2:27021366-27027998 |
| 19495 | Slc22a29 | NM_172776.2 | chr19:8160167-8218839 | 19592 | Slc2a7 | NM_001085529.1 | chr4:150148971-150168482 |
| 19496 | Slc22a3 | NM_011395.2 | chr17:12419973-12507704 | 19593 | Slc2a8 | NM_019488.4 | chr2:32972988-32982056 |

Fig.21 - 102

| | | | | | | | | |
|---|---|---|---|---|---|---|---|---|
| 19594 | Slc2a9 | NM_001012363.2 | chr5:38349272-38483385 | | 19691 | Slc46a1 | NM_026740.2 | chr11:78465700-78471945 |
| 19595 | Slc30a1 | NM_009579.3 | chr1:191906780-191913247 | | 19692 | Slc46a2 | NM_021033.4 | chr4:59905898-59915056 |
| 19596 | Slc30a10 | NM_001033286.2 | chr1:185454847-185468761 | | 19693 | Slc46a3 | NM_027872.3 | chr5:147878440-147894802 |
| 19597 | Slc30a2 | NM_001039677.2 | chr4:134343045-134354484 | | 19694 | Slc47a1 | NM_026183.5 | chr11:61343399-61378075 |
| 19598 | Slc30a3 | NM_011773.3 | chr5:31086105-31093527 | | 19695 | Slc47a2 | NM_001033542.2 | chr11:61301630-61342860 |
| 19599 | Slc30a4 | NM_001290993.1 | chr2:122681232-122702663 | | 19696 | Slc48a1 | NM_026353.4 | chr15:97784364-97792692 |
| 19600 | Slc30a5 | NM_022885.2 | chr13:100802647-100833427 | | 19697 | Slc4a1 | NM_011403.2 | chr11:102344819-102365281 |
| 19601 | Slc30a6 | NM_001252478.1 | chr17:74395607-74424229 | | 19698 | Slc4a10 | NM_001242378.1 | chr2:62046514-62326743 |
| 19602 | Slc30a7 | NM_023214.7 | chr3:115938972-116007406 | | 19699 | Slc4a11 | NM_001081162.1 | chr2:130684107-130697519 |
| 19603 | Slc30a8 | NM_172816.3 | chr15:52295552-52335733 | | 19700 | Slc4a1ap | NM_009206.2 | chr5:31526994-31584038 |
| 19604 | Slc30a9 | NM_178651.4 | chr5:67306954-67356142 | | 19701 | Slc4a2 | NM_001258892.1 | chr5:24427520-24440947 |
| 19605 | Slc31a1 | NM_175090.4 | chr4:62360700-62391769 | | 19702 | Slc4a3 | NM_009208.3 | chr1:75546265-75559431 |
| 19606 | Slc31a2 | NM_001290518.1 | chr4:62291546-62298412 | | 19703 | Slc4a4 | NM_001136260.1 | chr5:88887259-89239656 |
| 19607 | Slc32a1 | NM_009508.2 | chr2:158610757-158615747 | | 19704 | Slc4a5 | NM_001166067.1 | chr6:83237374-83304945 |
| 19608 | Slc33a1 | NM_001272035.1 | chr3:63942323-63964733 | | 19705 | Slc4a7 | NM_001033270.2 | chr14:14703024-14799943 |
| 19609 | Slc34a1 | NM_011392.2 | chr13:55399647-55414695 | | 19706 | Slc4a8 | NM_021530.2 | chr15:100761746-100823971 |
| 19610 | Slc34a2 | NM_011402.3 | chr5:53049352-53071663 | | 19707 | Slc4a9 | NM_001271544.1 | chr18:36528151-36544608 |
| 19611 | Slc34a3 | NM_080854.3 | chr2:25228896-25234234 | | 19708 | Slc50a1 | NM_009057.3 | chr3:89268245-89270570 |
| 19612 | Slc35a1 | NM_018895.3 | chr4:34663256-34687438 | | 19709 | Slc51a | NM_145932.3 | chr16:32475577-32487879 |
| 19613 | Slc35a2 | NM_001083937.1 | chrX:7884243-7894027 | | 19710 | Slc51b | NM_178933.2 | chr9:65412752-65422773 |
| 19614 | Slc35a3 | NM_144902.3 | chr3:116670797-116712280 | | 19711 | Slc52a2 | NM_029643.3 | chr15:76538942-76542130 |
| 19615 | Slc35a4 | NM_001083317.1 | chr18:36679214-36683862 | | 19712 | Slc52a3 | NM_001164819.1 | chr2:151999865-152009258 |
| 19616 | Slc35a5 | NM_028756.4 | chr16:45139572-45158673 | | 19713 | Slc5a1 | NM_019810.4 | chr5:33104218-33162699 |
| 19617 | Slc35b1 | NM_016752.1 | chr11:95384923-95391652 | | 19714 | Slc5a10 | NM_001033227.2 | chr11:61672781-61720799 |
| 19618 | Slc35b2 | NM_028662.2 | chr17:45564151-45567869 | | 19715 | Slc5a11 | NM_146198.2 | chr7:123214865-123273251 |
| 19619 | Slc35b3 | NM_001170403.1 | chr13:38932139-38960537 | | 19716 | Slc5a12 | NM_001003915.2 | chr2:110597298-110649345 |
| 19620 | Slc35b4 | NM_021435.3 | chr6:34155878-34177054 | | 19717 | Slc5a2 | NM_133254.3 | chr7:128265696-128272433 |
| 19621 | Slc35c1 | NM_145832.3 | chr2:92462764-92460518 | | 19718 | Slc5a3 | NM_017391.3 | chr16:92058321-92087473 |
| 19622 | Slc35c2 | NM_001252573.1 | chr2:165276521-165287787 | | 19719 | Slc5a4a | NM_133184.2 | chr10:76147450-76189265 |
| 19623 | Slc35d1 | NM_177732.4 | chr4:103171717-103214884 | | 19720 | Slc5a4b | NM_023219.2 | chr10:76958620-76111018 |
| 19624 | Slc35d2 | NM_001001321.3 | chr13:64090809-64129330 | | 19721 | Slc5a5 | NM_053248.2 | chr8:70882888-70892757 |
| 19625 | Slc35d3 | NM_029529.3 | chr10:19847916-19851459 | | 19722 | Slc5a6 | NM_001177621.1 | chr5:31036035-31048562 |
| 19626 | Slc35e1 | NM_177766.3 | chr8:72477994-72492614 | | 19723 | Slc5a7 | NM_022025.4 | chr17:54273589-54299034 |
| 19627 | Slc35e2 | NM_177186.4 | chr4:155601415-155623340 | | 19724 | Slc5a8 | NM_145423.2 | chr10:88885991-88929515 |
| 19628 | Slc35e3 | NM_029875.2 | chr10:117733677-117746358 | | 19725 | Slc5a9 | NM_145551.4 | chr4:111875376-111902796 |
| 19629 | Slc35e4 | NM_153142.3 | chr11:3907021-3914664 | | 19726 | Slc6a1 | NM_178703.4 | chr6:114282634-114317525 |
| 19630 | Slc35f1 | NM_178675.4 | chr10:52690500-53111622 | | 19727 | Slc6a11 | NM_172890.3 | chr6:114131240-114249886 |
| 19631 | Slc35f2 | NM_028060.3 | chr9:53771534-53818161 | | 19728 | Slc6a12 | NM_133661.3 | chr6:121346696-121365773 |
| 19632 | Slc35f3 | NM_175434.3 | chr8:126290578-126395977 | | 19729 | Slc6a13 | NM_144512.2 | chr6:121300295-121337718 |
| 19633 | Slc35f4 | NM_029238.2 | chr14:49298519-49525837 | | 19730 | Slc6a14 | NM_020049.4 | chrX:21714899-21742357 |
| 19634 | Slc35f5 | NM_028787.4 | chr1:125561015-125595684 | | 19731 | Slc6a15 | NM_001252330.1 | chr10:103367807-103419379 |
| 19635 | Slc35f6 | NM_175476.3 | chr5:30647938-30659729 | | 19732 | Slc6a17 | NM_172271.2 | chr3:107467547-107518018 |
| 19636 | Slc35g1 | NM_175507.3 | chr19:38395979-38405607 | | 19733 | Slc6a18 | NM_001040492.3 | chr13:73661749-73678023 |
| 19637 | Slc35g2 | NM_001101483.1 | chr9:100553187-100571085 | | 19734 | Slc6a19 | NM_028878.3 | chr13:73681156-73700695 |
| 19638 | Slc35g3 | NM_019871.2 | chr11:69759885-69761844 | | 19735 | Slc6a19os | NM_027780.1 | chr13:73699825-73709856 |
| 19639 | Slc36a1 | NM_153139.4 | chr11:55204339-55236330 | | 19736 | Slc6a2 | NM_009209.3 | chr8:92961046-93001667 |
| 19640 | Slc36a1os | NR_046034.1 | chr11:55191718-55197682 | | 19737 | Slc6a20a | NM_139142.2 | chr9:123636906-123678832 |
| 19641 | Slc36a2 | NM_153170.3 | chr11:55158467-55185077 | | 19738 | Slc6a20b | NM_011731.3 | chr9:123593819-123632565 |
| 19642 | Slc36a3 | NM_172258.3 | chr11:55124822-55151706 | | 19739 | Slc6a3 | NM_010020.3 | chr13:73536746-73578672 |
| 19643 | Slc36a4 | NM_172789.4 | chr9:15709768-15738789 | | 19740 | Slc6a4 | NM_010484.2 | chr11:76998596-77032843 |
| 19644 | Slc37a1 | NM_001242427.1 | chr17:31296223-31350698 | | 19741 | Slc6a5 | NM_001146013.1 | chr7:49910298-49959493 |
| 19645 | Slc37a2 | NM_001145960.1 | chr9:37229148-37255738 | | 19742 | Slc6a6 | NM_009320.4 | chr6:91684066-91759063 |
| 19646 | Slc37a3 | NM_028123.3 | chr6:39273770-39377707 | | 19743 | Slc6a7 | NM_201353.1 | chr18:60995379-61014199 |
| 19647 | Slc37a4 | NM_008063.2 | chr9:44398175-44402965 | | 19744 | Slc6a8 | NM_001142809.1 | chrX:73673132-73682500 |
| 19648 | Slc38a1 | NM_001166456.1 | chr15:96571417-96642343 | | 19745 | Slc6a9 | NM_008135.4 | chr4:117833257-117869305 |
| 19649 | Slc38a10 | NM_001164798.1 | chr11:120103950-120151351 | | 19746 | Slc7a1 | NM_007513.4 | chr5:148327409-148399904 |
| 19650 | Slc38a11 | NM_177074.2 | chr2:65316632-65364026 | | 19747 | Slc7a10 | NM_017394.4 | chr7:35186384-35201111 |
| 19651 | Slc38a2 | NM_175121.3 | chr15:96589737-96699698 | | 19748 | Slc7a11 | NM_011990.2 | chr3:50364935-50443613 |
| 19652 | Slc38a3 | NM_001199217.1 | chr9:107661154-107667399 | | 19749 | Slc7a12 | NM_080852.2 | chr3:14480698-14505818 |
| 19653 | Slc38a4 | NM_027052.3 | chr15:96994822-97055956 | | 19750 | Slc7a13 | NM_028746.3 | chr4:19818726-19842213 |
| 19654 | Slc38a5 | NM_172479.3 | chrX:8271380-8280176 | | 19751 | Slc7a14 | NM_172861.3 | chr3:31202855-31310319 |
| 19655 | Slc38a6 | NM_001077717.3 | chr12:73286847-73354045 | | 19752 | Slc7a15 | NM_001088660.2 | chr2:85228482-85239566 |
| 19656 | Slc38a7 | NM_172758.4 | chr8:95835922-95853491 | | 19753 | Slc7a2 | NM_001044740.2 | chr8:40862366-40922070 |
| 19657 | Slc38a8 | NM_001009950.1 | chr8:119479602-119501698 | | 19754 | Slc7a3 | NM_007515.3 | chrX:101079209-101085405 |
| 19658 | Slc38a9 | NM_178746.4 | chr13:112660765-112738752 | | 19755 | Slc7a4 | NM_144852.3 | chr16:17572017-17576671 |
| 19659 | Slc39a1 | NM_013901.2 | chr3:90248191-90253612 | | 19756 | Slc7a5 | NM_011404.3 | chr8:121881145-121907686 |
| 19660 | Slc39a10 | NM_172653.2 | chr1:46807543-46853509 | | 19757 | Slc7a6 | NM_178798.3 | chr8:106168874-106198704 |
| 19661 | Slc39a11 | NM_001166503.1 | chr11:113244854-113565815 | | 19758 | Slc7a6os | NM_001007567.2 | chr8:106200437-106210933 |
| 19662 | Slc39a12 | NM_001168397.1 | chr2:14494977 | | 19759 | Slc7a7 | NM_001253679.1 | chr14:54369441-54417679 |
| 19663 | Slc39a13 | NM_001290765.1 | chr2:91061780-91070315 | | 19760 | Slc7a8 | NM_016972.2 | chr14:54722214-54781886 |
| 19664 | Slc39a14 | NM_001135151.1 | chr14:70303461-70351424 | | 19761 | Slc7a9 | NM_001199015.1 | chr7:35449091-35466034 |
| 19665 | Slc39a2 | NM_001039676.2 | chr14:51893609-51896745 | | 19762 | Slc8a1 | NM_001112798.2 | chr17:81373104-81738387 |
| 19666 | Slc39a3 | NM_134135.1 | chr10:81028539-81033912 | | 19763 | Slc8a2 | NM_148946.2 | chr7:16130299-16160511 |
| 19667 | Slc39a4 | NM_028064.2 | chr15:76612382-76616352 | | 19764 | Slc8a3 | NM_001167920.1 | chr12:81197914-81333180 |
| 19668 | Slc39a5 | NM_001136237.1 | chr10:128395930-128401224 | | 19765 | Slc8b1 | NM_001177594.1 | chr5:120511191-120534024 |
| 19669 | Slc39a6 | NM_139143.3 | chr18:24579880-24602817 | | 19766 | Slc9a1 | NM_016981.2 | chr4:133369771-133423698 |
| 19670 | Slc39a7 | NM_001077709.1 | chr17:34028265-34031690 | | 19767 | Slc9a2 | NM_001033289.2 | chr1:40681711-40768815 |
| 19671 | Slc39a8 | NM_001135149.1 | chr3:135825656-135888572 | | 19768 | Slc9a3 | NM_001081060.1 | chr13:74121514-74166064 |
| 19672 | Slc39a9 | NM_026214.2 | chr12:80644214-80683342 | | 19769 | Slc9a3r1 | NM_012030.2 | chr11:115163340-115181178 |
| 19673 | Slc3a1 | NM_009205.2 | chr17:85028346-85064241 | | 19770 | Slc9a3r2 | NM_023055.2 | chr17:24639281-24650305 |
| 19674 | Slc3a2 | NM_001161413.1 | chr19:8706881-8723369 | | 19771 | Slc9a4 | NM_177084.3 | chr1:40580226-40630731 |
| 19675 | Slc40a1 | NM_016917.2 | chr1:45908069-45925594 | | 19772 | Slc9a5 | NM_001081332.1 | chr8:105348257-105369881 |
| 19676 | Slc41a1 | NM_173865.3 | chr1:131828011-131848864 | | 19773 | Slc9a6 | NM_172780.3 | chrX:56609834-56664230 |
| 19677 | Slc41a2 | NM_177388.3 | chr10:83231138-83337817 | | 19774 | Slc9a7 | NM_177353.3 | chrX:20105754-20291764 |
| 19678 | Slc41a3 | NM_001037493.2 | chr6:90619245-90646412 | | 19775 | Slc9a8 | NM_148929.3 | chr2:167421709-167477000 |
| 19679 | Slc43a1 | NM_001081349.2 | chr2:84863407-84863586 | | 19776 | Slc9a9 | NM_177909.5 | chr9:94669893-95280452 |
| 19680 | Slc43a2 | NM_001281.3 | chr11:75577572 | | 19777 | Slc9b1 | NM_028946.3 | chr3:135348036-135397827 |
| 19681 | Slc43a3 | NM_021398.3 | chr2:84936645-84958509 | | 19778 | Slc9b2 | NM_178877.6 | chr3:135307699-135342767 |
| 19682 | Slc44a1 | NM_001159633.1 | chr4:53440412-53550164 | | 19779 | Slc9c1 | NM_198106.4 | chr16:45535265-45607001 |
| 19683 | Slc44a2 | NM_001199386.1 | chr9:21355028 | | 19780 | Slco1a4 | NM_013797.5 | chr6:141192720-141946962 |
| 19684 | Slc44a3 | NM_146394.3 | chr3:121459527-121532344 | | 19781 | Slco1a5 | NM_030687.1 | chr6:141805439-141856171 |
| 19685 | Slc44a4 | NM_023557.3 | chr17:34914465-34930436 | | 19782 | Slco1a6 | NM_001267707.1 | chr6:142234226-142278874 |
| 19686 | Slc44a5 | NM_001081425.3 | chr3:153973435-154271720 | | 19783 | Slco1a8 | NM_023718.3 | chr6:142085767-142186149 |
| 19687 | Slc45a1 | NM_173774.3 | chr4:150629395-150652174 | | 19784 | Slco1b2 | NM_020495.1 | chr6:141629517-141686635 |
| 19688 | Slc45a2 | NM_053077.3 | chr15:11000720-11029233 | | 19785 | Slco1c1 | NM_001177772.1 | chr6:141524385-141570177 |
| 19689 | Slc45a3 | NM_001177628.2 | chr1:131962914-131982972 | | 19786 | Slco2a1 | NM_033314.3 | chr9:103008488-103087849 |
| 19690 | Slc45a4 | NM_001033219.3 | chr15:73580290-73624744 | | 19787 | Slco2b1 | NM_001252530.1 | chr7:99657803-99706842 |

Fig.21 - 103

| | | | | | | | | |
|---|---|---|---|---|---|---|---|---|
| 19788 | Slco3a1 | NM_001038643.1 | chr7:74279417-74594780 | 19885 | Smim14 | NM_133697.3 | chr5:65448754-65492835 |
| 19789 | Slco4a1 | NM_148933.1 | chr2:180460977-180474853 | 19886 | Smim15 | NM_001048250.2 | chr13:108044473-108049146 |
| 19790 | Slco4c1 | NM_172658.3 | chr1:96818783-96872171 | 19887 | Smim18 | NM_001206849.1 | chr8:33742111-33747770 |
| 19791 | Slco5a1 | NM_172841.2 | chr1:12866549-12991135 | 19888 | Smim19 | NM_001012667.2 | chr8:22462613-22476879 |
| 19792 | Slco6b1 | NR_120500.1 | chr1:96906176-96997560 | 19889 | Smim20 | NM_001145433.1 | chr5:53267105-53278540 |
| 19793 | Slco6c1 | NM_028942.4 | chr1:97059448-97128303 | 19890 | Smim22 | NM_001253796.1 | chr16:5007315-5008308 |
| 19794 | Slco6d1 | NM_001164233.1 | chr1:98421123-98509380 | 19891 | Smim23 | NM_027050.1 | chr11:32820375-32824594 |
| 19795 | Slfn1 | NM_011407.1 | chr11:83116844-83122659 | 19892 | Smim24 | NM_001099917.1 | chr10:81393063-81395079 |
| 19796 | Slfn10-ps | NR_073523.1 | chr11:83028125-83046042 | 19893 | Smim3 | NM_134133.2 | chr18:60474190-60501983 |
| 19797 | Slfn14 | NM_001166028.1 | chr11:83275111-83286726 | 19894 | Smim4 | NM_001308091.1 | chr14:31124505-31128930 |
| 19798 | Slfn2 | NM_011408.1 | chr11:83065111-83070678 | 19895 | Smim5 | NM_183259.3 | chr13:115900138-115906269 |
| 19799 | Slfn3 | NM_011409.1 | chr11:83191329-83215154 | 19896 | Smim6 | NM_001162998.1 | chr11:115912016-115913917 |
| 19800 | Slfn4 | NM_011410.3 | chr11:83175185-83190216 | 19897 | Smim7 | NM_172396.3 | chr8:72565197-72571048 |
| 19801 | Slfn5 | NM_183201.4 | chr11:82952101-82964850 | 19898 | Smim8 | NM_025471.2 | chr4:34768671-34778337 |
| 19802 | Slfn5os | NR_045932.1 | chr11:82942340-82960681 | 19899 | Smim9 | NM_001033786.2 | chrX:75146656-75163751 |
| 19803 | Slfn8 | NM_001167743.1 | chr11:83002157-83020722 | 19900 | Smlr1 | NM_001198596.1 | chr10:25527942-25536272 |
| 19804 | Slfn9 | NM_172796.2 | chr11:82980302-82991830 | 19901 | Smn1 | NM_001252629.1 | chr13:100123204-100137698 |
| 19805 | Slfnl1 | NM_177570.3 | chr4:120532230-120536861 | 19902 | Smndc1 | NM_172429.2 | chr19:53379213-53390573 |
| 19806 | Slirp | NM_029958.3 | chr12:87443899-87449924 | 19903 | Smo | NM_176996.4 | chr6:29735496-29761366 |
| 19807 | Slit1 | NM_015748.3 | chr19:41600256-41743856 | 19904 | Smoc1 | NM_001146217.1 | chr12:81026807-81186414 |
| 19808 | Slit2 | NM_001291227.2 | chr5:47983154-48307736 | 19905 | Smoc2 | NM_022315.2 | chr17:14279505-14404790 |
| 19809 | Slit3 | NM_011412.3 | chr11:35121455-35708507 | 19906 | Smok2a | NM_013741.1 | chr17:13221187-13227658 |
| 19810 | Slitrk1 | NM_199065.2 | chr14:108909988-108914239 | 19907 | Smok2b | NM_001167913.2 | chr17:13230262-13237189 |
| 19811 | Slitrk2 | NM_001161431.1 | chrX:66649317-66661402 | 19908 | Smok3a | NM_001126045.1 | chr5:138021428-138034665 |
| 19812 | Slitrk3 | NM_198864.2 | chr3:73048124-73056943 | 19909 | Smok3b | NM_001039889.3 | chr5:138037223-138050693 |
| 19813 | Slitrk4 | NM_178740.4 | chrX:64649843-64276996 | 19910 | Smok4a | NR_030763.1 | chr17:13521455-13528434 |
| 19814 | Slitrk5 | NM_198865.1 | chr14:111675114-111683135 | 19911 | Smox | NM_001177833.1 | chr2:131491861-131525183 |
| 19815 | Slitrk6 | NM_175499.4 | chr14:110748577-110755149 | 19912 | Smpd1 | NM_011421.2 | chr7:105554359-105558389 |
| 19816 | Slk | NM_001164639.1 | chr19:47580018-47645246 | 19913 | Smpd2 | NM_009213.2 | chr10:41487171-41490340 |
| 19817 | Slmap | NM_032008.4 | chr14:26413167-26534624 | 19914 | Smpd3 | NM_021491.3 | chr8:106252547-106337988 |
| 19818 | Slmo1 | NM_144867.2 | chr16:67474848-67480581 | 19915 | Smpd4 | NM_001164609.1 | chr16:17619353-17644830 |
| 19819 | Slmo2 | NM_025531.2 | chr2:174465090-174472941 | 19916 | Smpd5 | NM_001195937.1 | chr15:76294433-76296896 |
| 19820 | Sln | NM_025540.2 | chr9:53850250-53853849 | 19917 | Smpdl3a | NM_020561.2 | chr10:57794543-57811830 |
| 19821 | Slpi | NM_011414.3 | chr2:164354049-164356507 | 19918 | Smpdl3b | NM_133888.2 | chr4:132732965-132757171 |
| 19822 | Slirn | NM_025690.3 | chr9:70547869-70592232 | 19919 | Smpx | NM_001252591.2 | chrX:157698972-157752591 |
| 19823 | Slu7 | NM_148679.3 | chr11:43433730-43447981 | 19920 | Smr2 | NM_001252679.1 | chr5:88086555-88108053 |
| 19824 | Slurp1 | NM_020519.1 | chr15:74726643-74728026 | 19921 | Smr3a | NM_011422.3 | chr5:88002524-88008534 |
| 19825 | Slx | NM_001186476.1 | chrX:26522656-26545565 | 19922 | Sms | NM_009214.3 | chrX:157443953-157492046 |
| 19826 | Slx1b | NM_029420.2 | chr7:126626875-126695783 | 19923 | Smtn | NM_001159284.1 | chr11:3517521-3539292 |
| 19827 | Six4 | NM_177472.5 | chr16:3979105-4001678 | 19924 | Smtnl1 | NM_024230.2 | chr2:84811175-84812652 |
| 19828 | Slx4ip | NM_001038641.1 | chr2:136899350-137069778 | 19925 | Smtnl2 | NM_177776.3 | chr11:72390113-72411713 |
| 19829 | Slx1 | NM_029181.1 | chrX:55226875-55243736 | 19926 | Smu1 | NM_021335.4 | chr4:40735648-40757885 |
| 19830 | Sly | NM_201530.2 | chrY:55213719-75222053 | 19927 | Smug1 | NM_027885.3 | chr15:103153289-103163284 |
| 19831 | Smad1 | NM_008539.3 | chr6:79338397-79399468 | 19928 | Smurf1 | NM_001038627.1 | chr5:144876494-144965830 |
| 19832 | Smad2 | NM_001252481.1 | chr18:76261120-76311747 | 19929 | Smurf2 | NM_025481.2 | chr11:106820063-106920715 |
| 19833 | Smad3 | NM_016769.4 | chr9:63646766-63757994 | 19930 | Smyd1 | NM_001160127.1 | chr6:71213939-71262281 |
| 19834 | Smad4 | NM_008540.2 | chr18:73630012-73703741 | 19931 | Smyd2 | NM_026796.1 | chr1:189880491-189922288 |
| 19835 | Smad5 | NM_001164041.1 | chr13:56703051-56742378 | 19932 | Smyd3 | NM_027188.3 | chr1:178955038-179518003 |
| 19836 | Smad6 | NM_008542.3 | chr9:63953075-64022069 | 19933 | Smyd4 | NM_001102611.1 | chr11:75348432-75405705 |
| 19837 | Smad7 | NM_001042660.1 | chr18:75367364-75395934 | 19934 | Smyd5 | NM_144918.2 | chr6:85431975-85446429 |
| 19838 | Smad9 | NM_019483.5 | chr3:54755581-54801269 | 19935 | Snai1 | NM_011427.2 | chr2:167538226-167542813 |
| 19839 | Smagp | NM_001033872.2 | chr15:100621339-100626946 | 19936 | Snai2 | NM_011415.2 | chr16:14705858-14709382 |
| 19840 | Smap1 | NM_001290683.1 | chr1:23845624-23909736 | 19937 | Snai3 | NM_013914.2 | chr8:122454205-122460692 |
| 19841 | Smap2 | NM_133716.3 | chr4:120968316-121017247 | 19938 | Snap23 | NM_001177927.1 | chr2:120576670-120600722 |
| 19842 | Smarca1 | NM_029708.1 | chrX:47809369-47892552 | 19939 | Snap25 | NM_001291056.1 | chr2:136719449-136782428 |
| 19843 | Smarca2 | NM_011416.2 | chr19:26605159-26778321 | 19940 | Snap29 | NM_023348.4 | chr16:17405999-17430826 |
| 19844 | Smarca4 | NM_001174078.1 | chr9:21616168-21704230 | 19941 | Snap47 | NM_144521.2 | chr11:59407149-59449956 |
| 19845 | Smarca5 | NM_053124.2 | chr8:80659942-80739459 | 19942 | Snag91 | NM_001277982.1 | chr9:86765926-86880397 |
| 19846 | Smarca5-ps | NR_002888.2 | chr4:145464209-145467961 | 19943 | Snapc1 | NM_178392.4 | chr12:73964529-73984820 |
| 19847 | Smarcad1 | NM_001253392.1 | chr6:65043205-65116049 | 19944 | Snapc2 | NM_139968.1 | chr8:4258101-4258220 |
| 19848 | Smarcal1 | NM_018817.2 | chr1:72583250-72636790 | 19945 | Snapc3 | NM_029949.3 | chr4:83417743-83453340 |
| 19849 | Smarcb1 | NM_001161853.1 | chr10:75896768-75921614 | 19946 | Snapc4 | NM_172339.4 | chr2:26362764-26380653 |
| 19850 | Smarcc1 | NM_009211.2 | chr9:110313023-110240178 | 19947 | Snapc5 | NM_183316.2 | chr9:64179296-64182688 |
| 19851 | Smarcc2 | NM_001114096.1 | chr10:128459235-128490174 | 19948 | Snapin | NM_133854.3 | chr3:90488025-90491013 |
| 19852 | Smarcd1 | NM_031842.2 | chr15:99702286-99713995 | 19949 | Snca | NM_001042451.2 | chr6:60731572-60829004 |
| 19853 | Smarcd2 | NM_001130587.1 | chr11:106263170-106272972 | 19950 | Sncaip | NM_011999151.1 | chr18:52767810-52915981 |
| 19854 | Smarcd3 | NM_025891.3 | chr5:24592621-24602062 | 19951 | Sncb | NM_033610.2 | chr13:54758859-54766440 |
| 19855 | Smarce1 | NM_020618.4 | chr11:99209047-99231017 | 19952 | Sncg | NM_011430.3 | chr14:34370279-34374669 |
| 19856 | Smc1a | NM_019710.2 | chrX:152016427-152061973 | 19953 | Snd1 | NM_019776.2 | chr6:28480347-28888832 |
| 19857 | Smc1b | NM_080470.1 | chr15:85064688-85131957 | 19954 | Sned1 | NM_172463.4 | chr1:93235896-93296448 |
| 19858 | Smc2 | NM_008017.4 | chr4:52430220-52483365 | 19955 | Snf8 | NM_033568.2 | chr11:96034916-96047405 |
| 19859 | Smc2os | NR_045175.1 | chr4:52430283-52438964 | 19956 | Snhg1 | NR_002896.3 | chr19:8723486-8726326 |
| 19860 | Smc3 | NM_007790.3 | chr19:53600895-53648831 | 19957 | Snhg10 | NR_003145.3 | chr12:105030616-105032279 |
| 19861 | Smc4 | NM_133786.3 | chr3:69004971-69034623 | 19958 | Snhg11 | NM_175692.3 | chr2:158375637-158386145 |
| 19862 | Smc5 | NM_001252684.1 | chr19:23206440-23273897 | 19959 | Snhg12 | NR_029468.1 | chr4:132308677-132311024 |
| 19863 | Smc6 | NM_025695.4 | chr12:11265885-11319785 | 19960 | Snhg18 | NR_038186.1 | chr15:32240867-32244662 |
| 19864 | Smchd1 | NM_028873.2 | chr17:71344492-71475343 | 19961 | Snhg3 | NR_003276.2 | chr4:132351932-132353686 |
| 19865 | Smco1 | NM_183283.2 | chr16:32271808-32274779 | 19962 | Snhg4 | NR_036073.1 | chr18:35553409-35558318 |
| 19866 | Smco2 | NM_026709.1 | chr6:146825109-146871404 | 19963 | Snhg5 | NR_040721.1 | chr9:88521052-88522897 |
| 19867 | Smco3 | NM_001039558.2 | chr6:136829930-136835450 | 19964 | Snhg6 | NR_024067.2 | chr1:9942024-9944118 |
| 19868 | Smco4 | NM_133214.2 | chr9:15505494-15545259 | 19965 | Snhg7 | NR_024068.2 | chr2:26637175-26640244 |
| 19869 | Smcp | NM_008574.3 | chr3:92583865-92589024 | 19966 | Snhg8 | NR_028574.1 | chr3:123507551-123508336 |
| 19870 | Smcr8 | NM_001085440.1 | chr11:60777524-60788287 | 19967 | Snhg9 | NR_027900.2 | chr17:24719530-24719965 |
| 19871 | Smdt1 | NM_026914.1 | chr15:82346045-82349062 | 19968 | Snip1 | NM_175246.4 | chr4:125066692-125074043 |
| 19872 | Smek1 | NM_001106214.1 | chr10:109403-101083702 | 19969 | Snn | NM_009223.3 | chr16:11066297-11074986 |
| 19873 | Smek2 | NM_134034.2 | chr11:29172906-29220797 | 19970 | Snora15 | NR_003681.1 | chr5:129794560-129794676 |
| 19874 | Smg1 | NM_001031814.1 | chr7:118131311-118243637 | 19971 | Snora16a | NR_029412.1 | chr4:132309464-132309600 |
| 19875 | Smg5 | NM_178246.3 | chr3:88336259-88362337 | 19972 | Snora17 | NR_028571.1 | chr2:26639189-26639321 |
| 19876 | Smg6 | NM_001002764.1 | chr11:74925871-75164448 | 19973 | Snora19 | NR_034047.1 | chr19:24942235-60774385 |
| 19877 | Smg7 | NM_001005516.1 | chr1:152836994-152902646 | 19974 | Snora21 | NR_028549.1 | chr12:17922856-17922917 |
| 19878 | Smg8 | NM_024262.1 | chr11:87077731-87086777 | 19975 | Snora23 | NR_028078.1 | chr11:97783638-97781766 |
| 19879 | Smg9 | NM_028047.2 | chr7:24399627-24422777 | 19976 | Snora24 | NR_033336.1 | chr7:110046863-110046547 |
| 19880 | Smgc | NM_001918837.3 | chr15:91838327-91861435 | 19977 | Snora25 | NR_028573.1 | chr3:123507936-123508066 |
| 19881 | Smim1 | NM_001163721.1 | chr4:154020469-154026044 | 19978 | Snora26 | NR_031758.1 | chr5:74093529-74093650 |
| 19882 | Smim11 | NM_138743.2 | chr16:92301302-92313041 | 19979 | Snora28 | NR_033168.1 | chr12:111540945-111541066 |
| 19883 | Smim12 | NM_030252.2 | chr4:127243783-127247809 | 19980 | Snora2b | NR_034052.1 | chr15:98526347-98526459 |
| 19884 | Smim13 | NM_001135577.2 | chr13:41249843-41276577 | 19981 | Snora3 | NR_028079.1 | chr7:109520133-109520251 |

Fig.21 - 104

| | | | | | | | | |
|---|---|---|---|---|---|---|---|---|
| 19982 | Snora30 | NR_034045.1 | chr7:127527896-127528003 | 20079 | Snord99 | NR_028537.1 | chr4:132310702-132310758 |
| 19983 | Snora31 | NR_028481.1 | chr14:75847922-75848034 | 20080 | Snph | NM_001291076.1 | chr2:151590548-151632593 |
| 19984 | Snora33 | NR_037680.1 | chr10:23785346-23785451 | 20081 | Snrk | NM_001164572.1 | chr9:122117265-122169702 |
| 19985 | Snora34 | NR_034051.1 | chr15:98519716-98519834 | 20082 | Snrnp200 | NM_177214.4 | chr2:127208403-127240451 |
| 19986 | Snora35 | NR_028446.1 | chrX:146994389-146994508 | 20083 | Snrnp25 | NM_030093.3 | chr11:32265414-32208995 |
| 19987 | Snora36b | NR_034044.1 | chr1:185242925-185243038 | 20084 | Snrnp27 | NM_025665.2 | chr6:86675168-86684491 |
| 19988 | Snora41 | NR_028558.1 | chr1:63179022-63179135 | 20085 | Snrnp35 | NM_029532.2 | chr5:124483154-124491122 |
| 19989 | Snora43 | NR_028572.1 | chr2:26637846-26637985 | 20086 | Snrnp40 | NM_025645.2 | chr4:130360131-130390030 |
| 19990 | Snora44 | NR_034050.1 | chr4:132309952-132310069 | 20087 | Snrnp48 | NM_026382.2 | chr13:38204938-38227663 |
| 19991 | Snora47 | NR_034043.1 | chr13:95330616-95330736 | 20088 | Snrnp70 | NM_009224.3 | chr7:45376453-45395742 |
| 19992 | Snora52 | NR_034049.2 | chr7:141448802-141448936 | 20089 | Snrpa | NM_001104637.1 | chr7:27187005-27196760 |
| 19993 | Snora5c | NR_034042.1 | chr11:6620318-6620419 | 20090 | Snrpa1 | NM_021336.4 | chr7:66060335-66074587 |
| 19994 | Snora61 | NR_034046.1 | chr4:132310306-132310368 | 20091 | Snrpb | NM_009225.2 | chr2:130171635-130179364 |
| 19995 | Snora62 | NR_002902.2 | chr9:120130433-120130561 | 20092 | Snrpb2 | NM_021335.3 | chr2:143063068-143072052 |
| 19996 | Snora64 | NR_002897.1 | chr17:24720788-24720905 | 20093 | Snrpc | NM_011432.2 | chr17:27840086-27851987 |
| 19997 | Snora65 | NR_002898.2 | chr2:32963300-32963418 | 20094 | Snrpd1 | NM_009226.4 | chr18:10617795-10628230 |
| 19998 | Snora68 | NR_002901.1 | chr8:70895758-70895856 | 20095 | Snrpd2 | NM_026943.1 | chr7:19149837-19152728 |
| 19999 | Snora69 | NR_002900.1 | chrX:37082911-37083033 | 20096 | Snrpd3 | NM_026095.4 | chr10:75518041-75535440 |
| 20000 | Snora70 | NR_002899.1 | chrX:74272491-74272620 | 20097 | Snrpe | NM_009227.3 | chr1:133603870-133610289 |
| 20001 | Snora74a | NR_002905.3 | chr18:35557029-35557227 | 20098 | Snrpf | NM_027246.1 | chr10:93583028-93589658 |
| 20002 | Snora75 | NR_028478.1 | chr1:86351169-86351285 | 20099 | Snrpg | NM_028506.2 | chr6:86371539-86378902 |
| 20003 | Snora78 | NR_028515.1 | chr17:24719675-24719832 | 20100 | Snrpn | NM_001082961.1 | chr7:59982501-60097608 |
| 20004 | Snora7a | NR_028546.1 | chr6:115807974-115808103 | 20101 | Snta1 | NM_009228.2 | chr2:154376313-154408084 |
| 20005 | Snora81 | NR_034048.1 | chr16:23110769-23110933 | 20102 | Sntb1 | NM_016667.3 | chr15:55839153-55906949 |
| 20006 | Snord100 | NR_037681.1 | chr10:23785753-23785821 | 20103 | Sntb2 | NM_009229.4 | chr8:106935749-107014192 |
| 20007 | Snord104 | NR_030703.1 | chr1:106500990-106501063 | 20104 | Sntg1 | NM_001290390.1 | chr1:8359738-9299877 |
| 20008 | Snord11 | NR_028521.1 | chr1:59704807-59704870 | 20105 | Sntg2 | NM_172951.3 | chr12:30174556-30373375 |
| 20009 | Snord110 | NR_028547.1 | chr2:130275514-130275573 | 20106 | Sntn | NM_177624.3 | chr14:13670875-13683148 |
| 20010 | Snord111 | NR_028559.1 | chr8:110838534-110838598 | 20107 | Snupn | NM_178374.3 | chr9:56950923-56993199 |
| 20011 | Snord116 | NR_002895.2 | chr7:59675990-59676079 | 20108 | Snurf | NM_033174.3 | chr7:59982500-60005156 |
| 20012 | Snord116l1 | NR_033778.1 | chr7:59894622-59894711 | 20109 | Snw1 | NM_025607.2 | chr12:87449909-87472299 |
| 20013 | Snord116l2 | NR_033779.1 | chr7:59675989-59751580 | 20110 | Snx1 | NM_019727.2 | chr9:66088126-66124886 |
| 20014 | Snord118 | NR_028566.1 | chr19:7478517-7478561 | 20111 | Snx10 | NM_001127348.1 | chr6:51544522-51590670 |
| 20015 | Snord12 | NR_028540.1 | chr2:167065292-167065358 | 20112 | Snx11 | NM_001163389.1 | chr11:96767548-96777555 |
| 20016 | Snord123 | NR_028575.2 | chr15:32241844-32241932 | 20113 | Snx12 | NM_001103310.1 | chrX:101171960-101122563 |
| 20017 | Snord14a | NR_028273.1 | chr2:32777987-32778009 | 20114 | Snx13 | NM_001014973.2 | chr12:35047188-35147477 |
| 20018 | Snord14c | NR_028276.1 | chr10:46244748-46244770 | 20115 | Snx14 | NM_172926.3 | chr9:88376746-88438951 |
| 20019 | Snord14d | NR_028274.1 | chr10:46244747-46244770 | 20116 | Snx15 | NM_026912.1 | chr19:6119403-6128215 |
| 20020 | Snord15a | NR_002172.1 | chr7:99482784-99482932 | 20117 | Snx16 | NM_001127191.2 | chr3:10417816-10440130 |
| 20021 | Snord15b | NR_002173.1 | chr7:99479562-99479707 | 20118 | Snx17 | NM_153680.2 | chr5:31193303-31198900 |
| 20022 | Snord16a | NR_028548.1 | chr9:64175431-64175522 | 20119 | Snx18 | NM_130796.4 | chr13:113592178-113618564 |
| 20023 | Snord17 | NR_030762.1 | chr2:144265981-144266202 | 20120 | Snx19 | NM_028374.2 | chr9:30427328-30466726 |
| 20024 | Snord19 | NR_028523.1 | chr14:31016218-31016272 | 20121 | Snx2 | NM_026386.1 | chr18:53176364-53220860 |
| 20025 | Snord1a | NR_028570.1 | chr11:116674596-116674672 | 20122 | Snx20 | NM_027840.3 | chr8:88626827-88636128 |
| 20026 | Snord1b | NR_028567.1 | chr11:116674146-116674223 | 20123 | Snx21 | NM_133924.3 | chr2:164786020-164792770 |
| 20027 | Snord1c | NR_028569.1 | chr11:116672504-116672582 | 20124 | Snx22 | NM_001025612.2 | chr9:66065175-66069731 |
| 20028 | Snord2 | NR_002573.1 | chr18:23109020-23109020 | 20125 | Snx24 | NM_029394.3 | chr18:53245661-53390825 |
| 20029 | Snord22 | NR_004445.1 | chr19:8725865-8725991 | 20126 | Snx25 | NM_207213.2 | chr8:46033260-46124146 |
| 20030 | Snord23 | NR_028539.1 | chr7:15938761-15938860 | 20127 | Snx27 | NM_001082484.2 | chr3:94497941-94582716 |
| 20031 | Snord32a | NR_000002.8 | chr7:45127382-45127463 | 20128 | Snx29 | NM_001290148.1 | chr16:11405647-11755473 |
| 20032 | Snord33 | NR_001277.2 | chr7:45126863-45126945 | 20129 | Snx3 | NM_017472.4 | chr10:42502053-42535369 |
| 20033 | Snord34 | NR_002455.1 | chr7:45126602-45126668 | 20130 | Snx30 | NM_172468.2 | chr4:59805649-59904740 |
| 20034 | Snord35a | NR_000003.8 | chr7:45126346-45126435 | 20131 | Snx31 | NM_025712.4 | chr15:36504061-36555572 |
| 20035 | Snord35b | NR_000004.8 | chr7:45123025-45123111 | 20132 | Snx32 | NM_001024560.2 | chr19:5495277-5510489 |
| 20036 | Snord37 | NR_028549.1 | chr19:81178960-81179013 | 20133 | Snx33 | NM_175483.5 | chr9:56917199-56928371 |
| 20037 | Snord38a | NR_028524.1 | chr4:117154515-117154574 | 20134 | Snx4 | NM_080557.2 | chr16:33251455-33299562 |
| 20038 | Snord42a | NR_037682.1 | chr11:78181301-78181346 | 20135 | Snx5 | NM_001199188.1 | chr2:144250123-144270902 |
| 20039 | Snord42b | NR_037683.1 | chr11:78183058-78183113 | 20136 | Snx6 | NM_026998.3 | chr12:54746356-54795682 |
| 20040 | Snord43 | NR_028281.1 | chr15:80082858-80082906 | 20137 | Snx7 | NM_001190156.1 | chr3:117781496-117868936 |
| 20041 | Snord45b | NR_028561.1 | chr15:153910566-153910611 | 20138 | Snx8 | NM_172277.2 | chr5:140340302-140389247 |
| 20042 | Snord45c | NR_028525.1 | chr3:153391728-153391811 | 20139 | Snx9 | NM_025684.5 | chr17:5841379-5930711 |
| 20043 | Snord47 | NR_028543.1 | chr1:161038091-161038156 | 20140 | Soat1 | NM_009230.3 | chr1:156428107-156474328 |
| 20044 | Snord49a | NR_028550.1 | chr11:62603459-62603521 | 20141 | Soat2 | NM_146064.1 | chr15:102150574-102163436 |
| 20045 | Snord49b | NR_028526.1 | chr11:62603085-62603148 | 20142 | Sobp | NM_175407.3 | chr10:43002499-43174530 |
| 20046 | Snord4a | NR_030702.1 | chr11:78181686-78181756 | 20143 | Socs1 | NM_001271603.1 | chr16:10783808-10785536 |
| 20047 | Snord52 | NR_028571.1 | chr7:34950949-34951008 | 20144 | Socs2 | NM_001168655.1 | chr10:95411489-95416212 |
| 20048 | Snord53 | NR_028551.1 | chr7:71640888-110848315 | 20145 | Socs3 | NM_007707.3 | chr11:117966086-117969366 |
| 20049 | Snord55 | NR_030704.1 | chr4:117155770-117155848 | 20146 | Socs4 | NM_080843.2 | chr14:47277142-47291591 |
| 20050 | Snord57 | NR_028528.1 | chr2:130278025-130278088 | 20147 | Socs5 | NM_019654.2 | chr17:87107678-87137588 |
| 20051 | Snord58b | NR_028552.1 | chr14:52069314-75001122 | 20148 | Socs6 | NM_018821.4 | chr18:88867879-88894267 |
| 20052 | Snord61 | NR_002903.1 | chrX:57391447-57391509 | 20149 | Socs7 | NM_138657.3 | chr11:97362550-97398542 |
| 20053 | Snord64 | NR_028529.1 | chr7:59978810-59978856 | 20150 | Sod1 | NM_011434.1 | chr16:90220741-90226324 |
| 20054 | Snord65 | NR_028541.1 | chr11:62604529-62604586 | 20151 | Sod2 | NM_013671.3 | chr17:13007838-13018119 |
| 20055 | Snord66 | NR_028530.1 | chr16:20684285-20684313 | 20152 | Sod3 | NM_011435.3 | chr5:52363803-52369738 |
| 20056 | Snord67 | NR_028553.1 | chr2:91596080-91596178 | 20153 | Soga1 | NM_001164663.1 | chr2:157010441-157079265 |
| 20057 | Snord68 | NR_028128.1 | chr8:123103057-123103105 | 20154 | Soga3 | NM_026138.2 | chr10:29143995-29199628 |
| 20058 | Snord69 | NR_028533.1 | chr14:31014292-31014351 | 20155 | Sohlh1 | NM_001001714.1 | chr2:25842996-25847248 |
| 20059 | Snord7 | NR_028362.1 | chr11:83294303-83294399 | 20156 | Sohlh2 | NM_028937.3 | chr3:55182043-55269957 |
| 20060 | Snord70 | NR_028554.1 | chr6:59691957-59692010 | 20157 | Son | NM_019973.2 | chr16:91647823-91663318 |
| 20061 | Snord71 | NR_028525.1 | chr8:109839311-109839375 | 20158 | Sorbs1 | NM_001034962.1 | chr19:40292039-40451398 |
| 20062 | Snord72 | NR_028091.1 | chr15:5118420-5118480 | 20159 | Sorbs2 | NM_001205219.1 | chr8:45507787-45827906 |
| 20063 | Snord73a | NR_004417.1 | chr3:86138790-86138858 | 20160 | Sorbs2os | NR_045739.1 | chr8:45723324-45819297 |
| 20064 | Snord8 | NR_028542.1 | chr14:52209785-52209884 | 20161 | Sorbs3 | NM_001271407.1 | chr14:70180467-70206022 |
| 20065 | Snord82 | NR_002851.1 | chr1:86356259-86356327 | 20162 | Sorcs1 | NM_001252501.1 | chr19:50143300-50678646 |
| 20066 | Snord83b | NR_028558.1 | chr2:180978502-800785579 | 20163 | Sorcs2 | NM_030889.2 | chr5:36017180-36398139 |
| 20067 | Snord85 | NR_028565.1 | chr4:130749637-130749702 | 20164 | Sorcs3 | NM_025696.3 | chr19:48206024-48805505 |
| 20068 | Snord87 | NR_004410.1 | chr1:9942469-9942543 | 20165 | Sord | NM_146126.4 | chr2:122234838-122265337 |
| 20069 | Snord88a | NR_028533.1 | chr7:44250149-44250221 | 20166 | Sorl1 | NM_011436.3 | chr9:41968488-42124289 |
| 20070 | Snord88c | NR_028534.1 | chr7:44249854-44249938 | 20167 | Sort1 | NM_001271539.1 | chr3:108284063-108361519 |
| 20071 | Snord89 | NR_028555.2 | chr1:39548746-39548840 | 20168 | Sos1 | NM_009231.2 | chr17:80393751-80480453 |
| 20072 | Snord90 | NR_028535.1 | chr2:37400060-37400128 | 20169 | Sos2 | NM_001135559.1 | chr12:69583760-69681852 |
| 20073 | Snord91a | NR_028562.1 | chr11:74905445-74905505 | 20170 | Sost | NM_024449.6 | chr11:101962457-101967015 |
| 20074 | Snord92 | NR_028556.1 | chr17:71631278-71631361 | 20171 | Sostdc1 | NM_025312.3 | chr12:36314168-36318452 |
| 20075 | Snord93 | NR_028536.1 | chr5:23852232-23852277 | 20172 | Sowaha | NM_183173.2 | chr11:53476577-53480195 |
| 20076 | Snord95 | NR_028556.1 | chr1:48803318-48803206 | 20173 | Sowahb | NM_175203.4 | chr5:93041122-93045022 |
| 20077 | Snord96a | NR_028563.1 | chr11:48802032-48802109 | 20174 | Sowahc | NM_172939.3 | chr10:59221921-59226433 |
| 20078 | Snord98 | NR_028557.1 | chr10:62765578-62765606 | 20175 | Sowahd | NM_173779.3 | chrX:37048844-37050418 |

Fig.21 - 105

| | | | | | | | | |
|---|---|---|---|---|---|---|---|---|
| 20176 | Sox1 | NM_009233.3 | chr8:12395518-12399555 | | 20273 | Spdyb | NM_029048.3 | chr5:143216315-143225882 |
| 20177 | Sox10 | NM_011437.1 | chr15:79154912-79164490 | | 20274 | Specc1 | NM_001029936.3 | chr11:62077023-62223013 |
| 20178 | Sox11 | NM_009234.6 | chr12:27334267-27342718 | | 20275 | Specc1l | NM_001145826.1 | chr10:75212389-75312400 |
| 20179 | Sox12 | NM_011438.2 | chr2:152393611-152398046 | | 20276 | Speer1-ps1 | NR_001586.3 | chr5:11340407-11346273 |
| 20180 | Sox13 | NM_011439.2 | chr1:133382299-133424212 | | 20277 | Speer2 | NM_173069.3 | chr16:69856873-69863744 |
| 20181 | Sox14 | NM_011440.1 | chr9:99874105-99876170 | | 20278 | Speer3 | NM_027650.3 | chr5:13791618-13796819 |
| 20182 | Sox15 | NM_009235.2 | chr11:69655036-69656727 | | 20279 | Speer4a | NM_029376.2 | chr5:26034269-26039505 |
| 20183 | Sox17 | NM_001289464.1 | chr1:4490927-4497354 | | 20280 | Speer4b | NM_028561.2 | chr5:27495808-27501392 |
| 20184 | Sox18 | NM_009236.2 | chr2:181669836-181671640 | | 20281 | Speer4c | NM_001281511.1 | chr5:15709504-15714271 |
| 20185 | Sox2 | NM_011443.4 | chr3:34649994-34652460 | | 20282 | Speer4d | NM_025759.3 | chr5:15619098-15623864 |
| 20186 | Sox21 | NM_177753.3 | chr14:118233233-118237030 | | 20283 | Speer4e | NM_001122661.1 | chr5:14933630-14938475 |
| 20187 | Sox2ot | NR_015580.2 | chr3:34560380-34677993 | | 20284 | Speer4f | NM_027609.2 | chr5:17476121-17480936 |
| 20188 | Sox3 | NM_009237.2 | chrX:60891365-60893430 | | 20285 | Speer5-ps1 | NR_001582.2 | chr10:44170446-44219585 |
| 20189 | Sox30 | NM_173384.2 | chr11:45980309-46017992 | | 20286 | Speer6-ps1 | NR_001581.2 | chr13:3149474-3189678 |
| 20190 | Sox4 | NM_009238.2 | chr13:28950299-28953682 | | 20287 | Speer7-ps1 | NR_001585.3 | chr5:15680709-15714596 |
| 20191 | Sox5 | NM_001113559.2 | chr6:143828424-144209568 | | 20288 | Speer8-ps1 | NR_001584.3 | chr5:14945293-14978541 |
| 20192 | Sox5os3 | NR_040519.1 | chr6:144672867-144693832 | | 20289 | Speer9-ps1 | NR_001583.3 | chr7:3128145-3144992 |
| 20193 | Sox6 | NM_001025559.3 | chr7:115470871-116038744 | | 20290 | Spef1 | NM_027641.2 | chr2:131170260-131174810 |
| 20194 | Sox7 | NM_011446.1 | chr14:63943709-63950732 | | 20291 | Spef2 | NM_177123.4 | chr15:9661545-9748868 |
| 20195 | Sox8 | NM_011447.3 | chr17:25565892-25570686 | | 20292 | Speg | NM_001085370.1 | chr1:75385609-75432304 |
| 20196 | Sox9 | NM_011448.4 | chr11:112782209-112787757 | | 20293 | Spem1 | NM_028855.1 | chr11:69820870-69822165 |
| 20197 | Sp1 | NM_013672.2 | chr15:102406315-102436404 | | 20294 | Spen | NM_019763.2 | chr4:141467889-141538597 |
| 20198 | Sp100 | NM_013194.3 | chr1:85649987-85709997 | | 20295 | Spert | NM_001164139.1 | chr14:75582833-75593118 |
| 20199 | Sp110 | NM_030194.1 | chr1:85576898-85598810 | | 20296 | Spesp1 | NM_025721.2 | chr9:62270728-62282179 |
| 20200 | Sp140 | NM_001013817.2 | chr1:85600702-85645036 | | 20297 | Spg11 | NM_145531.2 | chr2:122053525-122118386 |
| 20201 | Sp2 | NM_001080964.1 | chr11:96953337-96977688 | | 20298 | Spg20 | NM_001144987.1 | chr3:55112165-55137332 |
| 20202 | Sp3 | NM_001018042.3 | chr2:72936431-72980446 | | 20299 | Spg21 | NM_138584.2 | chr9:65460936-65488470 |
| 20203 | Sp3os | NR_045269.2 | chr2:72979431-72989249 | | 20300 | Spg7 | NM_153176.4 | chr8:123065607-123097751 |
| 20204 | Sp4 | NM_001166385.2 | chr12:118231685-118301440 | | 20301 | Sphk1 | NM_001172472.1 | chr11:116532443-116536675 |
| 20205 | Sp5 | NM_022435.2 | chr2:70474922-70477726 | | 20302 | Sphk2 | NM_001172561.1 | chr7:45709462-45718002 |
| 20206 | Sp6 | NM_031183.2 | chr11:97013568-97024738 | | 20303 | Sphkap | NM_172430.3 | chr1:83255780-83408200 |
| 20207 | Sp7 | NM_130458.3 | chr15:102357176-102366271 | | 20304 | Spi1 | NM_011355.1 | chr2:91096796-91115756 |
| 20208 | Sp8 | NM_177082.4 | chr12:118846328-118852578 | | 20305 | Spib | NM_019866.1 | chr7:44525994-44532071 |
| 20209 | Sp9 | NM_001005343.2 | chr2:73271925-73275771 | | 20306 | Spic | NM_011463.1 | chr10:88675269-88683023 |
| 20210 | Spa17 | NM_011449.2 | chr9:37603293-37613720 | | 20307 | Spice1 | NM_144550.4 | chr16:44347400-44388492 |
| 20211 | Spaca1 | NM_001290443.1 | chr4:34024871-34030065 | | 20308 | Spidr | NM_146068.4 | chr16:15889224-16146851 |
| 20212 | Spaca3 | NM_029367.1 | chr11:80858388-80867814 | | 20309 | Spin1 | NM_001283028.1 | chr13:51100879-51152562 |
| 20213 | Spaca4 | NM_027055.3 | chr7:45725106-45725816 | | 20310 | Spin2c | NM_001005370.1 | chrX:153832292-153834240 |
| 20214 | Spaca5 | NM_001085393.2 | chrX:21068487-21077959 | | 20311 | Spin2d | NM_001243002.1 | chrX:73175301-73176989 |
| 20215 | Spaca6 | NM_001162909.1 | chr17:17830974-17839071 | | 20312 | Spin2-ps1 | NM_029106.2 | chrX:3835879-3836656 |
| 20216 | Spaca7 | NM_024279.2 | chr8:12573048-12600738 | | 20313 | Spin4 | NM_178753.4 | chrX:95022506-95026682 |
| 20217 | Spag1 | NM_001163629.1 | chr15:36179529-36235177 | | 20314 | Spink10 | NM_177829.3 | chr18:62548910-62661358 |
| 20218 | Spag11a | NM_153115.1 | chr8:19157886-19159578 | | 20315 | Spink11 | NM_001048217.3 | chr18:44190044-44196177 |
| 20219 | Spag11b | NM_001034905.2 | chr8:19140758-19143010 | | 20316 | Spink12 | NM_030061.3 | chr18:44104522-44108543 |
| 20220 | Spag16 | NM_001271533.1 | chr1:69826969-69926250 | | 20317 | Spink13 | NM_001168423.2 | chr18:62607539-62741387 |
| 20221 | Spag17 | NM_028892.4 | chr3:99885416-100143322 | | 20318 | Spink14 | NM_001039218.2 | chr18:44027868-44032208 |
| 20222 | Spag4 | NM_139511.4 | chr2:156065212-156069499 | | 20319 | Spink2 | NM_001289764.1 | chr5:77205106-77211259 |
| 20223 | Spag5 | NM_017407.2 | chr11:78301590-78322454 | | 20320 | Spink3 | NM_009258.5 | chr18:43728068-43737237 |
| 20224 | Spag6 | NM_015773.2 | chr16:16753015-16829363 | | 20321 | Spink4 | NM_011463.2 | chr4:40920055-40931395 |
| 20225 | Spag7 | NM_001167663.1 | chr11:70663768-70669416 | | 20322 | Spink5 | NM_001081180.1 | chr18:43963240-44022487 |
| 20226 | Spag8 | NM_001007463.1 | chr4:43651728-43653552 | | 20323 | Spink6 | NM_001013797.1 | chr18:44071392-44083610 |
| 20227 | Spag9 | NM_001025428.1 | chr11:94044204-94126082 | | 20324 | Spink7 | NM_001001803.2 | chr18:62592412-62596264 |
| 20228 | Spam1 | NM_001079875.2 | chr6:24791187-24801048 | | 20325 | Spink8 | NM_183136.2 | chr9:109816626-109826627 |
| 20229 | Sparc | NM_001290817.1 | chr11:55394158-55420080 | | 20326 | Spinkl | NM_183123.2 | chr18:44166357-44175073 |
| 20230 | Spard1 | NM_016907.3 | chr5:104079108-104114088 | | 20327 | Spint1 | NM_016907.3 | chr2:119237359-119249519 |
| 20231 | Spast | NM_001162870.1 | chr17:74338986-74391113 | | 20328 | Spint2 | NM_001082548.1 | chr7:29256329-29281977 |
| 20232 | Spata1 | NM_027617.3 | chr3:146457202-146499753 | | 20329 | Spint3 | NM_001177401.1 | chr2:164569694-164573456 |
| 20233 | Spata13 | NM_001033272.2 | chr14:60634704-60764556 | | 20330 | Spint4 | NM_030058.2 | chr2:164698500-164702448 |
| 20234 | Spata16 | NM_027583.3 | chr3:26637630-26927481 | | 20331 | Spint5 | NM_001040055.1 | chr2:164715304-164718068 |
| 20235 | Spata17 | NM_028848.3 | chr1:187048406-187215446 | | 20332 | Spire1 | NM_176832.2 | chr18:67488208-67549173 |
| 20236 | Spata18 | NM_028531.3 | chr5:73651379-73679484 | | 20333 | Spire2 | NM_172287.2 | chr8:123332712-123369518 |
| 20237 | Spata19 | NM_029299.3 | chr9:27396806-27401711 | | 20334 | Spn | NM_001037810.2 | chr7:127133463-127137823 |
| 20238 | Spata2 | NM_170756.3 | chr2:167485135-167492874 | | 20335 | Spn-ps | NR_033583.1 | chr5:90891395-90898476 |
| 20239 | Spata20 | NM_144827.4 | chr11:94478903-94485310 | | 20336 | Spns1 | NM_023712.3 | chr7:126370059-126377934 |
| 20240 | Spata21 | NM_178673.3 | chr4:141088344-141112759 | | 20337 | Spns2 | NM_001276383.1 | chr11:72451637-72475027 |
| 20241 | Spata22 | NM_001045531.1 | chr11:73240704-73346044 | | 20338 | Spns3 | NM_029932.3 | chr11:72498155-72550246 |
| 20242 | Spata24 | NM_027733.3 | chr18:35660015-35662186 | | 20339 | Spo11 | NM_001083959.1 | chr2:172979841-172993575 |
| 20243 | Spata25 | NM_029370.1 | chr2:164827381-164828534 | | 20340 | Spock1 | NM_001166463.1 | chr13:57426090-57908332 |
| 20244 | Spata2l | NM_030176.2 | chr8:123232257-123236209 | | 20341 | Spock2 | NM_052994.2 | chr10:60106256-60133913 |
| 20245 | Spata3 | NM_001122732.1 | chr1:86021941-86029958 | | 20342 | Spock3 | NM_001252620.1 | chr8:62951231-63357096 |
| 20246 | Spata31 | NM_030047.2 | chr13:64913405-64923195 | | 20343 | Spon1 | NM_145584.2 | chr7:113765997-114043375 |
| 20247 | Spata31d1a | NM_028157.2 | chr13:59700082-59706197 | | 20344 | Spon2 | NM_133903.3 | chr5:33213517-33218238 |
| 20248 | Spata31d1b | NM_001167593.1 | chr13:59712283-59719289 | | 20345 | Spop | NM_025287.2 | chr11:95414082-95493410 |
| 20249 | Spata31d1c | NM_001083890.2 | chr13:65033057-65038004 | | 20346 | Spopl | NM_001165997.1 | chr2:23510053-23572104 |
| 20250 | Spata31d1d | NM_177711.3 | chr13:59725924-59731752 | | 20347 | Spp1 | NM_001204201.1 | chr5:104435110-104441053 |
| 20251 | Spata32 | NM_177801.3 | chr11:103208126-103218432 | | 20348 | Spp2 | NM_029269.3 | chr1:88407009-88426438 |
| 20252 | Spata33 | NM_177794.4 | chr8:123212857-123222045 | | 20349 | Sppl2a | NM_023220.2 | chr2:126890394-126933235 |
| 20253 | Spata4 | NM_133711.3 | chr8:54600780-54610098 | | 20350 | Sppl2b | NM_175195.3 | chr10:80855274-80868708 |
| 20254 | Spata45 | NM_001162535.1 | chr1:191036521-191042941 | | 20351 | Sppl2c | NM_001082535.1 | chr11:104186326-104191166 |
| 20255 | Spata5 | NM_001163511.2 | chr3:37419949-37579096 | | 20352 | Sppl3 | NM_029012.2 | chr5:115011523-115098790 |
| 20256 | Spata5l1 | NM_001033256.3 | chr2:122630624-122632704 | | 20353 | Spr | NM_011467.2 | chr6:85133679-85137764 |
| 20257 | Spata6 | NM_001289572.1 | chr4:111720009-111829140 | | 20354 | Spred1 | NM_001277256.1 | chr2:117121070-117172853 |
| 20258 | Spata7 | NM_001289572.1 | chr12:98628141-98669819 | | 20355 | Spred2 | NM_033523.4 | chr11:19924441-20022597 |
| 20259 | Spata9 | NM_029343.3 | chr13:75967738-75998968 | | 20356 | Spred3 | NM_182927.3 | chr7:29158828-29168647 |
| 20260 | Spatc1 | NM_175060.3 | chr15:76268088-76292572 | | 20357 | Sprn | NM_183147.2 | chr7:140150627-140154659 |
| 20261 | Spatc1l | NM_029661.1 | chr15:76562271-76570200 | | 20358 | Sprr1a | NM_009264.2 | chr3:92483953-92485881 |
| 20262 | Spats1 | NM_027649.3 | chr17:45448978-45474938 | | 20359 | Sprr1b | NM_009265.3 | chr3:92436808-92438779 |
| 20263 | Spats2 | NM_139140.1 | chr15:99126844-99212466 | | 20360 | Sprr2a1 | NM_011468.4 | chr3:92215835-92222491 |
| 20264 | Spats2l | NM_001164566.1 | chr1:57845570-57948397 | | 20361 | Sprr2a2 | NM_001164787.1 | chr3:92215834-92257304 |
| 20265 | Spc24 | NM_026282.5 | chr15:5441-21760286 | | 20362 | Sprr2b | NM_011469.3 | chr3:92316704-92318085 |
| 20266 | Spc25 | NM_001199123.2 | chr2:69193894-69206213 | | 20363 | Sprr2d | NM_011470.2 | chr3:92339139-92340873 |
| 20267 | Spcs1 | NM_026911.3 | chr14:30999825-31001666 | | 20364 | Sprr2e | NM_011471.2 | chr3:92352142-92353449 |
| 20268 | Spcs2 | NM_025668.3 | chr7:99837658-99858843 | | 20365 | Sprr2f | NM_011472.2 | chr3:92365186-92366442 |
| 20269 | Spcs3 | NM_029701.1 | chr8:54520432-54529998 | | 20366 | Sprr2g | NR_003548.1 | chr3:92373914-92375229 |
| 20270 | Spdef | NM_013891.4 | chr17:27714446-27728951 | | 20367 | Sprr2h | NM_011474.3 | chr3:92385684-92387319 |
| 20271 | Spdl1 | NM_027411.2 | chr11:34809184-34833641 | | 20368 | Sprr2i | NM_011475.3 | chr3:92407990-92409271 |
| 20272 | Spdya | NM_001142831.1 | chr17:71552060-71578700 | | 20369 | Sprr2j-ps | NR_003185.1 | chr3:92418086-92419396 |

Fig.21 - 106

| | | | | | | | | |
|---|---|---|---|---|---|---|---|---|
| 20370 | Sprr2k | NM_011477.3 | chr3:92492581-92433927 | | 20467 | Ssc5d | NM_173008.2 | chr7:4925843-4944797 |
| 20371 | Sprr3 | NM_001204427.1 | chr3:92456501-92458720 | | 20468 | Ssfa2 | NM_080558.4 | chr2:79635424-79672964 |
| 20372 | Sprr4 | NM_173070.3 | chr3:92500262-92500493 | | 20469 | Ssh1 | NM_198109.4 | chr5:113942218-113993757 |
| 20373 | Sprtn | NM_001111141.1 | chr8:124897885-124903813 | | 20470 | Ssh2 | NM_001291190.1 | chr11:77348279-77460219 |
| 20374 | Sprv1 | NM_011896.3 | chr3:37639946-37644599 | | 20471 | Ssh3 | NM_198113.2 | chr19:4261668-4269172 |
| 20375 | Spry2 | NM_011897.3 | chr14:105891946-105896819 | | 20472 | Ssmem1 | NM_027073.1 | chr6:30509848-30520253 |
| 20376 | Spry3 | NM_001030293.2 | chrX_GL456233_random:10135 1-106192 | | 20473 | Ssna1 | NM_023464.2 | chr2:25271038-25272418 |
| | | | | | 20474 | Sspn | NM_010656.2 | chr6:145934146-145965225 |
| 20377 | Spry4 | NM_011898.2 | chr18:38586264-38601268 | | 20475 | Sspo | NM_173428.3 | chr6:48448228-48501250 |
| 20378 | Spryd3 | NM_001033277.3 | chr15:102116527-102136215 | | 20476 | Sst1 | NM_025965.3 | chr13:37971400-37994190 |
| 20379 | Spryd4 | NM_025716.2 | chr10:128209909-128211794 | | 20477 | Ssr2 | NM_025448.3 | chr3:88579670-88588413 |
| 20380 | Spryd7 | NM_025697.4 | chr14:61531850-61556886 | | 20478 | Ssr3 | NM_026155.3 | chr3:65379656-65392553 |
| 20381 | Spsb1 | NM_029035.2 | chr4:149896283-149955006 | | 20479 | Ssr4 | NM_001166480.1 | chrX:73787027-73790828 |
| 20382 | Spsb2 | NM_013539.2 | chr6:124808917-124810616 | | 20480 | Ssrp1 | NM_001136081.2 | chr2:85037450-85047114 |
| 20383 | Spsb3 | NM_001163750.1 | chr17:24886673-24892147 | | 20481 | Sssca1 | NM_020491.5 | chr19:5730305-5731732 |
| 20384 | Spsb4 | NM_145134.3 | chr9:96943481-97018355 | | 20482 | Sst | NM_009215.1 | chr16:23889580-23890844 |
| 20385 | Spt1 | NM_009267.2 | chr15:103895855-103899312 | | 20483 | Sstr1 | NM_009216.3 | chr12:58211803-58216036 |
| 20386 | Spta1 | NM_011465.4 | chr1:174172775-174248449 | | 20484 | Sstr2 | NM_001042606.2 | chr11:113619480-113625366 |
| 20387 | Sptan1 | NM_001177667.1 | chr2:29965553-30031451 | | 20485 | Sstr3 | NM_009218.3 | chr15:78537014-78544345 |
| 20388 | Sptb | NM_013675.3 | chr12:76580487-76710547 | | 20486 | Sstr4 | NM_009219.3 | chr2:148395376-148396764 |
| 20389 | Sptbn1 | NM_009260.2 | chr11:30106842-30198257 | | 20487 | Sstr5 | NM_001191008.1 | chr17:25489874-25497288 |
| 20390 | Sptbn2 | NM_021287.1 | chr19:4711222-4752352 | | 20488 | Ssty1 | NM_009220.2 | chrY:13376412-21097715 |
| 20391 | Sptbn4 | NM_001199234.1 | chr7:27356382-27396198 | | 20489 | Ssty2 | NM_023646.3 | chrY:22512350-80465434 |
| 20392 | Sptlc1 | NM_009269.2 | chr13:53332747-53377361 | | 20490 | Ssu2 | NM_175525.3 | chr6:112359323-112388023 |
| 20393 | Sptlc2 | NM_011479.4 | chr12:87305057-87388355 | | 20491 | Ssu72 | NM_026899.3 | chr4:155704814-155733873 |
| 20394 | Sptlc3 | NM_175467.3 | chr2:139493919-139637674 | | 20492 | Ssx2ip | NM_001253768.1 | chr3:146404641-146440137 |
| 20395 | Sptssa | NM_134054.2 | chr12:54645373-54656572 | | 20493 | Ssx9 | NM_199063.2 | chrX:8748429-8754587 |
| 20396 | Sptssb | NM_001164210.2 | chr3:69819538-69859894 | | 20494 | Ssxb1 | NM_026492.3 | chrX:8413304-8422157 |
| 20397 | Spty2d1 | NM_175818.4 | chr7:46990395-47008414 | | 20495 | Ssxb10 | NM_199064.1 | chrX:8327423-8336235 |
| 20398 | Spz1 | NM_030237.3 | chr13:92574631-92576232 | | 20496 | Ssxb2 | NM_001001450.4 | chrX:8454342-8461726 |
| 20399 | Sqle | NM_009270.3 | chr15:59315091-59331193 | | 20497 | Ssxb3 | NM_198898.2 | chrX:8583543-8589246 |
| 20400 | Sqrdl | NM_001162503.1 | chr2:122765358-122809551 | | 20498 | Ssxb5 | NM_199319.3 | chrX:8803690-8809386 |
| 20401 | Sqstm1 | NM_001290769.1 | chr11:50200151-50210820 | | 20499 | Ssxb6 | NM_001205108.1 | chrX:8542603-8548255 |
| 20402 | Sra1 | NM_001164406.1 | chr18:36567186-36670311 | | 20500 | Ssxb8 | NM_001081565.3 | chrX:8685330-8690844 |
| 20403 | Srbd1 | NM_030133.3 | chr17:85984664-86145175 | | 20501 | Ssxb9 | NM_199066.2 | chrX:8366977-8375388 |
| 20404 | Src | NM_001025395.2 | chr2:157419722-157471838 | | 20502 | St15 | NM_133726.2 | chr15:81365045-81399694 |
| 20405 | Srcin1 | NM_018873.2 | chr11:97509339-97575126 | | 20503 | St14 | NM_011176.4 | chr9:31088589-31131799 |
| 20406 | Srcrb4d | NM_001160366.1 | chr5:135960222-135974476 | | 20504 | St18 | NM_001244692.1 | chr1:6487230-6860940 |
| 20407 | Srd5a1 | NM_175283.3 | chr13:69573448-69611463 | | 20505 | St3gal1 | NM_009177.4 | chr15:67102874-67176882 |
| 20408 | Srd5a2 | NM_053188.2 | chr17:74017705-74047916 | | 20506 | St3gal2 | NM_009179.3 | chr8:110919864-110972497 |
| 20409 | Srd5a3 | NM_020611.4 | chr5:76140272-76155503 | | 20507 | St3gal3 | NM_001161774.2 | chr4:117932152-118134946 |
| 20410 | Srebf1 | NM_011480.4 | chr11:60199083-60220627 | | 20508 | St3gal4 | NM_009178.3 | chr9:35046578-35116810 |
| 20411 | Srebf2 | NM_033218.1 | chr15:82147268-82204960 | | 20509 | St3gal5 | NM_001035228.2 | chr6:72097607-72154570 |
| 20412 | Srek1 | NM_172592.2 | chr13:103741614-103764582 | | 20510 | St3gal6 | NM_018784.2 | chr16:58470540-58523212 |
| 20413 | Srek1ip1 | NM_026075.2 | chr13:104817238-104818659 | | 20511 | St5 | NM_001001326.3 | chr7:109523910-109617147 |
| 20414 | Srf | NM_020493.2 | chr17:46546838-46556162 | | 20512 | St6gal1 | NM_001252505.1 | chr16:23226020-23360350 |
| 20415 | Srfbp1 | NM_026040.3 | chr18:52465692-52490738 | | 20513 | St6gal2 | NM_172829.2 | chr17:55445716-55499226 |
| 20416 | Srgap1 | NM_001081037.2 | chr10:121780990-122047315 | | 20514 | St6galnac1 | NM_011371.2 | chr11:116765024-116775507 |
| 20417 | Srgap2 | NM_001081011.2 | chr1:131285250-131527361 | | 20515 | St6galnac2 | NM_009180.3 | chr11:116676704-116694658 |
| 20418 | Srgap3 | NM_080448.4 | chr6:112717971-112947266 | | 20516 | St6galnac3 | NM_011372.2 | chr3:153202508-153725133 |
| 20419 | Srgn | NM_011157.2 | chr10:62494427-62507755 | | 20517 | St6galnac4 | NM_001276425.1 | chr2:32587077-32598696 |
| 20420 | Sri | NM_020974.2 | chr5:8056541-8069314 | | 20518 | St6galnac5 | NM_012028.4 | chr3:152820709-152982207 |
| 20421 | Srl | NM_175347.4 | chr16:4480227-4523053 | | 20519 | St6galnac6 | NM_001025310.2 | chr2:32606984-32620809 |
| 20422 | Srm | NM_009272.4 | chr4:148591512-148594619 | | 20520 | St7 | NM_001083315.2 | chr6:17749169-17943023 |
| 20423 | Srms | NM_011481.3 | chr2:181205562-181213171 | | 20521 | St7l | NM_001253702.1 | chr3:104864505-104930063 |
| 20424 | Srp14 | NM_009273.4 | chr2:118475842-118479696 | | 20522 | St8sia1 | NM_011374.2 | chr6:142821540-142964452 |
| 20425 | Srp19 | NM_025527.3 | chr18:34331144-34336599 | | 20523 | St8sia2 | NM_009181.2 | chr7:73939119-74013682 |
| 20426 | Srp54a | NM_011899.4 | chr12:55080495-55115367 | | 20524 | St8sia3 | NM_009182.3 | chr18:64254358-64276144 |
| 20427 | Srp54b | NM_001100909.1 | chr12:55155103-55263480 | | 20525 | St8sia3os | NR_045366.1 | chr18:64157723-64277180 |
| 20428 | Srp54c | NM_001100110.1 | chr12:55230477-55263020 | | 20526 | St8sia4 | NM_001159745.1 | chr1:95627242-95667594 |
| 20429 | Srp68 | NM_146032.3 | chr11:116145165-116274217 | | 20527 | St8sia5 | NM_013666.2 | chr18:77185846-77255450 |
| 20430 | Srp72 | NM_025691.4 | chr5:76974700-76999935 | | 20528 | St8sia6 | NM_145838.1 | chr2:13654935-13793520 |
| 20431 | Srp9 | NM_012058.3 | chr1:182124736-182132415 | | 20529 | Stab1 | NM_138672.2 | chr14:31139016-31168641 |
| 20432 | Srpk1 | NM_016795.3 | chr17:28589591-28622454 | | 20530 | Stab2 | NM_138673.2 | chr10:86841209-87007942 |
| 20433 | Srpk2 | NM_009274.2 | chr5:23503355-23616571 | | 20531 | Stac | NM_016853.2 | chr9:111561433-111690216 |
| 20434 | Srpk3 | NM_019684.2 | chrX:73774404-73778924 | | 20532 | Stac2 | NM_146028.4 | chr11:98036623-98050462 |
| 20435 | Srpr | NM_026130.1 | chr9:35211202-35217003 | | 20533 | Stac3 | NM_177707.3 | chr10:127501716-127508815 |
| 20436 | Srprb | NM_009275.4 | chr9:103188032-103202065 | | 20534 | Stag1 | NM_009282.3 | chr9:100643622-100958544 |
| 20437 | Srpx | NM_016911.4 | chrX:10037976-10117861 | | 20535 | Stag2 | NM_001077712.2 | chrX:42149411-42277186 |
| 20438 | Srpx2 | NM_013908.5 | chrX:133908424-133932446 | | 20536 | Stag3 | NM_016964.2 | chr5:138280508-138312393 |
| 20439 | Srr | NM_001163311.1 | chr11:74906358-74925798 | | 20537 | Stam | NM_011484.2 | chr2:14074111-14148330 |
| 20440 | Srrd | NM_027323.2 | chr5:112337390-112343040 | | 20538 | Stam2 | NM_019667.2 | chr2:52692205-52742149 |
| 20441 | Srrm1 | NM_001130477.1 | chr4:135320483-135353214 | | 20539 | Stambp | NM_024239.2 | chr6:83543205-83572504 |
| 20442 | Srrm2 | NM_175229.3 | chr17:23803186-23824743 | | 20540 | Stambpl1 | NM_029682.4 | chr19:34192269-34240328 |
| 20443 | Srrm3 | NM_021403.3 | chr5:135818106-135874772 | | 20541 | Stames | NR_038162.1 | chr2:14070332-14073934 |
| 20444 | Srrm4 | NM_026886.3 | chr5:116439272-116591817 | | 20542 | Stap1 | NM_011992.4 | chr5:86071745-86104000 |
| 20445 | Srrm4os | NR_015595.2 | chr5:116438721-116465487 | | 20543 | Stap2 | NM_145934.2 | chr17:55997075-56005606 |
| 20446 | Srrt | NM_001166909.1 | chr5:137295703-137307674 | | 20544 | Star | NM_011485.4 | chr8:25808512-25815982 |
| 20447 | Srsf1 | NM_001078167.2 | chr11:88047372-88053757 | | 20545 | Stard10 | NM_019990.4 | chr7:101321318-101346312 |
| 20448 | Srsf10 | NM_001080387.2 | chr4:135856070-135865818 | | 20546 | Stard13 | NM_001163493.1 | chr5:151037514-151190193 |
| 20449 | Srsf11 | NM_001093752.1 | chr3:158010492-158036639 | | 20547 | Stard3 | NM_021547.3 | chr11:98058367-98381112 |
| 20450 | Srsf12 | NM_177774.4 | chr4:33208990-33233340 | | 20548 | Stard3nl | NM_024270.3 | chr13:19357675-19395813 |
| 20451 | Srsf2 | NM_011358.4 | chr11:116849896-116863094 | | 20549 | Stard4 | NM_133774.4 | chr18:33201420-33213816 |
| 20452 | Srsf3 | NM_013663.5 | chr17:29032659-29043372 | | 20550 | Stard5 | NM_023377.4 | chr7:83632016-83642328 |
| 20453 | Srsf4 | NM_020587.2 | chr4:131873638-131901725 | | 20551 | Stard6 | NM_001289648.1 | chr18:70472571-70501065 |
| 20454 | Srsf5 | NM_001079694.1 | chr12:80945503-80950507 | | 20552 | Stard7 | NM_139308.2 | chr2:127270228-127298434 |
| 20455 | Srsf6 | NM_026499.4 | chr2:162931507-162937120 | | 20553 | Stard8 | NM_199018.2 | chrX:99042580-99074728 |
| 20456 | Srsf7 | NM_001195485.1 | chr17:80200079-80207305 | | 20554 | Stat1 | NM_001205313.1 | chr1:52119621-52161865 |
| 20457 | Srsf9 | NM_025573.3 | chr5:115327176-115333080 | | 20555 | Stat2 | NM_019963.1 | chr10:128270575-128292849 |
| 20458 | Srxn1 | NM_029688.5 | chr2:152105523-152111376 | | 20556 | Stat3 | NM_011486.5 | chr11:100886805-100939540 |
| 20459 | Sry | NM_011564.1 | chrY:2662470-2663658 | | 20557 | Stat4 | NM_011487.5 | chr1:52008239-52107189 |
| 20460 | Ss18 | NM_001161369.1 | chr18:14625628-14682914 | | 20558 | Stat5a | NM_001164062.1 | chr11:100860483-100885169 |
| 20461 | Ss18l1 | NM_178750.5 | chr2:180042482-180070201 | | 20559 | Stat5b | NM_001113563.1 | chr11:100780730-100850585 |
| 20462 | Ssb | NM_009861.1 | chr2:69861586-69871846 | | 20560 | Stat6 | NM_009284.2 | chr10:127642985-127660987 |
| 20463 | Ssbp1 | NM_011286663.1 | chr6:40471467-40481823 | | 20561 | Stau1 | NM_001109905.2 | chr2:166947548-166996299 |
| 20464 | Ssbp2 | NM_024196.4 | chr13:91461096-91706175 | | 20562 | Stau2 | NM_001111272.1 | chr1:16228809-16519302 |
| 20465 | Ssbp3 | NM_023672.2 | chr4:106911469-107049694 | | 20563 | Stbd1 | NM_175096.3 | chr5:92603050-92606679 |
| 20466 | Ssbp4 | NM_133772.2 | chr8:70597489-70608314 | | | | | |

Fig.21 - 107

| | | | | | | | |
|---|---|---|---|---|---|---|---|
| 20564 | Stc1 | NM_009285.3 | chr14:69029285-69041401 | 20661 | Suclr1 | NM_032400.2 | chr3:60081868-60087566 |
| 20565 | Stc2 | NM_011491.3 | chr11:31359440-31370061 | 20662 | Suco | NM_172645.2 | chr1:161816111-161876661 |
| 20566 | Steap1 | NM_027399.3 | chr5:5736321-5749317 | 20663 | Suds3 | NM_001122666.2 | chr5:117091677-117115993 |
| 20567 | Steap2 | NM_001103156.2 | chr5:5664828-5694089 | 20664 | Sufu | NM_001025391.2 | chr19:46396895-46488804 |
| 20568 | Steap3 | NM_001085409.1 | chr1:120226415-120271082 | 20665 | Sugct | NM_138654.3 | chr13:16857474-17694765 |
| 20569 | Steap4 | NM_054098.3 | chr5:7980471-7982213 | 20666 | Sugp1 | NM_027481.2 | chr8:70042812-70071953 |
| 20570 | Stfa1 | NM_001082543.1 | chr16:36277147-36285371 | 20667 | Sugp2 | NM_001168290.1 | chr8:70234225-70261044 |
| 20571 | Stfa2 | NM_001082545.1 | chr16:36403945-36408363 | 20668 | Sugt1 | NM_026474.5 | chr14:79587690-79629755 |
| 20572 | Stfa2l1 | NM_173869.3 | chr16:36156810-36161948 | 20669 | Sulf1 | NM_001198565.1 | chr1:12692429-12860372 |
| 20573 | Stfa3 | NM_025288.2 | chr16:36450536-36455392 | 20670 | Sulf2 | NM_001252578.1 | chr2:166070898-166155285 |
| 20574 | Stil | NM_009185.3 | chr4:115000117-115043198 | 20671 | Sult1a1 | NM_133670.1 | chr7:126672869-126676357 |
| 20575 | Stim1 | NM_009287.4 | chr7:102267823-102436855 | 20672 | Sult1b1 | NM_019878.4 | chr5:87513338-87538195 |
| 20576 | Stim2 | NM_001081103.2 | chr5:53998522-54121057 | 20673 | Sult1c1 | NM_018751.2 | chr17:53961614-53990631 |
| 20577 | Stip1 | NM_016737.2 | chr19:7020695-7040026 | 20674 | Sult1c2 | NM_026935.4 | chr17:53829636-53845958 |
| 20578 | Stk10 | NM_009288.2 | chr11:32533265-32624595 | 20675 | Sult1d1 | NM_016771.3 | chr5:87554649-87569606 |
| 20579 | Stk11 | NM_011492.4 | chr10:80115802-80130685 | 20676 | Sult1e1 | NM_023135.2 | chr5:87575967-87591611 |
| 20580 | Stk11ip | NM_027886.3 | chr1:75521528-75537335 | 20677 | Sult2a1 | NM_001111296.2 | chr7:13796245-13837410 |
| 20581 | Stk16 | NM_001277992.1 | chr1:75210828-75215606 | 20678 | Sult2a2 | NM_009286.2 | chr7:13733505-13779637 |
| 20582 | Stk17b | NM_133810.3 | chr1:53755511-53785215 | 20679 | Sult2a3 | NM_001101586.2 | chr7:14067554-14122993 |
| 20583 | Stk19 | NM_019442.3 | chr17:34823992-34836903 | 20680 | Sult2a4 | NM_001101534.1 | chr7:13909676-13989588 |
| 20584 | Stk24 | NM_145465.2 | chr14:121286340-121379230 | 20681 | Sult2a5 | NM_001184980.1 | chr7:13623966-13670807 |
| 20585 | Stk25 | NM_021537.3 | chr1:93620750-93635727 | 20682 | Sult2a6 | NM_001081325.2 | chr7:14222402-14254870 |
| 20586 | Stk3 | NM_019635.2 | chr15:34875498-35155806 | 20683 | Sult2a7 | NM_001184981.1 | chr7:14465158-14492926 |
| 20587 | Stk31 | NM_029916.2 | chr6:49395603-49469502 | 20684 | Sult2b1 | NM_017465.2 | chr7:45729982-45759555 |
| 20588 | Stk32a | NM_178749.3 | chr18:43207696-43317481 | 20685 | Sult3a1 | NM_020565.2 | chr10:33857721-33879475 |
| 20589 | Stk32b | NM_022416.2 | chr5:37446824-37717153 | 20686 | Sult4a1 | NM_013873.3 | chr15:84076096-84105754 |
| 20590 | Stk32c | NM_001162540.1 | chr7:139103637-139213307 | 20687 | Sult5a1 | NM_020564.3 | chr8:123142846-123158280 |
| 20591 | Stk33 | NM_054103.1 | chr7:109279215-109439053 | 20688 | Sult6b1 | NM_001168625.1 | chr17:78883937-78906992 |
| 20592 | Stk35 | NM_001080635.2 | chr2:129800516-129832285 | 20689 | Sumf1 | NM_145937.3 | chr6:108107020-108185583 |
| 20593 | Stk36 | NM_175031.3 | chr1:74601454-74636893 | 20690 | Sumf2 | NM_026445.2 | chr5:129846989-129863951 |
| 20594 | Stk38 | NM_134115.2 | chr17:28970884-29007937 | 20691 | Sumo1 | NM_009460.2 | chr1:59639433-59670834 |
| 20595 | Stk38l | NM_172734.3 | chr6:146724929-146778814 | 20692 | Sumo2 | NM_133354.2 | chr11:115523108-115536230 |
| 20596 | Stk39 | NM_016866.2 | chr2:68210446-68471981 | 20693 | Sumo3 | NM_019929.4 | chr10:77606096-77618331 |
| 20597 | Stk4 | NM_021420.3 | chr2:164074177-164155521 | 20694 | Sun1 | NM_001256115.1 | chr5:139200836-139249839 |
| 20598 | Stk40 | NM_001145827.1 | chr4:126103956-126141029 | 20695 | Sun2 | NM_001205345.1 | chr15:79724067-79742536 |
| 20599 | Stmn1 | NM_019641.4 | chr4:134468319-134473843 | 20696 | Sun3 | NM_001290519.1 | chr11:9016053-9039591 |
| 20600 | Stmn1-rs1 | NR_029430.1 | chr5:315281091-315282070 | 20697 | Sun5 | NM_029499.2 | chr2:153856187-153871084 |
| 20601 | Stmn2 | NM_025285.2 | chr3:8509526-8561604 | 20698 | Suox | NM_173733.3 | chr10:128669886-128673918 |
| 20602 | Stmn3 | NM_009133.3 | chr2:181306458-181314500 | 20699 | Supt16 | NM_033618.3 | chr14:52160418-52197239 |
| 20603 | Stmn4 | NM_019675.3 | chr14:66344295-66361680 | 20700 | Supt20 | NM_019995.3 | chr3:54693104-54716837 |
| 20604 | Stmnd1 | NM_001005422.1 | chr13:46273720-46300115 | 20701 | Supt3 | NM_178652.2 | chr17:44777170-45119284 |
| 20605 | Stom | NM_013515.2 | chr2:35313989-35337009 | 20702 | Supt4a | NM_009296.1 | chr11:87737964-87743617 |
| 20606 | Stom11 | NM_026942.3 | chr9:58253163-58262524 | 20703 | Supt5 | NM_013676.1 | chr7:28314895-28338719 |
| 20607 | Stom12 | NM_023231.2 | chr4:43027689-43031384 | 20704 | Supt6 | NM_009297.2 | chr11:78206748-78245703 |
| 20608 | Stom13 | NM_153156.1 | chr3:53488792-53507652 | 20705 | Supt7l | NM_028150.2 | chr5:31514568-31526762 |
| 20609 | Ston1 | NM_029858.2 | chr17:88626554-88645724 | 20706 | Supv3l1 | NM_181423.2 | chr10:62429377-62449693 |
| 20610 | Ston2 | NM_175367.6 | chr12:91633008-91786436 | 20707 | Surf1 | NM_001271724.1 | chr2:26913377-26916530 |
| 20611 | Stox1 | NM_001033260.1 | chr10:62659421-62726099 | 20708 | Surf2 | NM_013678.2 | chr2:26916420-26920170 |
| 20612 | Stox2 | NM_001114311.1 | chr8:47718047-47289402 | 20709 | Surf4 | NM_011512.3 | chr2:26920840-26933511 |
| 20613 | Stpg1 | NM_030189.3 | chr4:135495986-135537803 | 20710 | Surf6 | NM_009298.3 | chr2:26890771-26902813 |
| 20614 | Stpg2 | NM_198659.2 | chr3:139205892-139710299 | 20711 | Susd1 | NM_001163286.2 | chr4:59314682-59438633 |
| 20615 | Stra13 | NM_016665.2 | chr11:120716940-120713767 | 20712 | Susd2 | NM_001162913.1 | chr10:75636618-75644008 |
| 20616 | Stra6 | NM_001162475.1 | chr9:58129087-58153997 | 20713 | Susd3 | NM_025491.3 | chr13:49230832-49248163 |
| 20617 | Stra8 | NM_009292.1 | chr6:34920959-34939342 | 20714 | Susd4 | NM_144796.4 | chr1:182764805-182895654 |
| 20618 | Strada | NM_001252448.1 | chr11:106162973-106193603 | 20715 | Susd5 | NM_001101510.1 | chr9:114057353-114099733 |
| 20619 | Stradb | NM_172656.5 | chr1:58973570-58995121 | 20716 | Suv39h1 | NM_001290716.1 | chrX:8061170-8074313 |
| 20620 | Strap | NM_011499.3 | chr6:137735081-137751930 | 20717 | Suv39h2 | NM_022724.4 | chr2:3455814-3474986 |
| 20621 | Strbp | NM_009261.3 | chr2:37569867-37647285 | 20718 | Suv420h1 | NM_001167884.1 | chr19:3767420-3806324 |
| 20622 | Strc | NM_080459.2 | chr2:121363726-121380940 | 20719 | Suv420h2 | NM_001115018.1 | chr7:4740126-4747514 |
| 20623 | Strip1 | NM_153569.2 | chr3:107612531-107631710 | 20720 | Suz12 | NM_001163018.1 | chr11:79993105-80034123 |
| 20624 | Strip2 | NM_001037740.1 | chr6:29917012-29959680 | 20721 | Sv2a | NM_022030.3 | chr3:96181226-96195180 |
| 20625 | Strn | NM_011500.2 | chr17:78653963-78736560 | 20722 | Sv2b | NM_001109753.1 | chr7:75114894-75308386 |
| 20626 | Strn3 | NM_001177098.1 | chr12:34008540-51691914 | 20723 | Sv2c | NM_029210.1 | chr13:95959442-96132577 |
| 20627 | Strn4 | NM_001039878.2 | chr7:16815888-16840931 | 20724 | Sva | NM_009299.2 | chr6:42032393-42042851 |
| 20628 | St3b | NM_008408.4 | chr9:36732412-36767578 | 20725 | Sval1 | NM_027822.3 | chr6:41951627-41956098 |
| 20629 | St3b | NM_024222.2 | chr9:36753228-115310421 | 20726 | Sval2 | NM_023542.1 | chr6:41860338-41864322 |
| 20630 | Stub1 | NM_019719.3 | chr17:25830635-25833361 | 20727 | Sval3 | NM_001003952.1 | chr6:41968139-41973090 |
| 20631 | Stx11 | NM_001163590.1 | chr10:12939982-12964259 | 20728 | Svep1 | NM_022814.2 | chr4:58042795-58206596 |
| 20632 | Stx12 | NM_133887.4 | chr4:135495063-132884458 | 20729 | Svil | NM_153153.3 | chr18:5046588-5119293 |
| 20633 | Stx16 | NM_001102423.1 | chr2:174077050-174099771 | 20730 | Svip | NM_001160345.1 | chr7:51997160-52006018 |
| 20634 | Stx17 | NM_026805.1 | chr4:48124918-48186656 | 20731 | Svop | NM_026805.1 | chr5:114026912-114091380 |
| 20635 | Stx18 | NM_001289535.1 | chr5:38039229-38137769 | 20732 | Svopl | NM_177200.4 | chr6:37983738-38046996 |
| 20636 | Stx19 | NM_026588.1 | chr16:62814675-62822722 | 20733 | Svs1 | NM_172888.3 | chr6:48986860-48991724 |
| 20637 | Stx1a | NM_016801.3 | chr5:135021371-135051699 | 20734 | Svs2 | NM_017390.4 | chr2:164235928-164238341 |
| 20638 | Stx1b | NM_024414.2 | chr7:127806843-127824531 | 20735 | Svs3a | NM_023163.2 | chr2:164289267-164291500 |
| 20639 | Stx2 | NM_001286033.1 | chr5:128984557-129008572 | 20736 | Svs3b | NM_173277.2 | chr2:164254362-164256643 |
| 20640 | Stx3 | NM_001025307.1 | chr5:128984557-129008572 | 20737 | Svs4 | NM_009300.3 | chr2:164275955-164278307 |
| 20641 | Stx4a | NM_009294.3 | chr7:127841807-127848965 | 20738 | Svs5 | NM_009301.2 | chr2:164352764-164334394 |
| 20642 | Stx5a | NM_016799.4 | chr19:8741423-8755642 | 20739 | Svs6 | NM_016750.2 | chr2:164316750-164318450 |
| 20643 | Stx6 | NM_021433.5 | chr1:155158702-155203517 | 20740 | Swap70 | NM_009302.3 | chr7:110221702-110283506 |
| 20644 | Stx7 | NM_016797.4 | chr10:24149316-24188959 | 20741 | Swi5 | NM_001290552.1 | chr2:32778804-32288069 |
| 20645 | Stx8 | NM_018768.2 | chr11:67966648-68207148 | 20742 | Swsap1 | NM_025870.1 | chr9:21955752-21958270 |
| 20646 | Stxbp1 | NM_001113569.1 | chr2:32787606-32847237 | 20743 | Swt1 | NM_025819.4 | chr1:151367698-151428435 |
| 20647 | Stxbp2 | NM_011503.4 | chr8:3631159-3643644 | 20744 | Syap1 | NM_025932.2 | chrX:162856842-162888462 |
| 20648 | Stxbp3a | NM_178793.179 | chr3:108440501- | 20745 | Sybu | NM_001032727.1 | chr15:44671855-44788063 |
| 20649 | Stxbp3b | NR_073859.1 | chr19:9557605-9559248 | 20746 | Syce1 | NM_134765.1 | chr7:140777228-140787854 |
| 20650 | Stxbp4 | NM_001113569.1 | chr11:90049892-90638108 | 20747 | Syce1l | NM_001048145.1 | chr8:113643212-113655533 |
| 20651 | Stxbp5 | NM_001081344.2 | chr10:9755546-9901040 | 20748 | Syce2 | NM_001168244.1 | chr8:84872257-84887446 |
| 20652 | Stxbp5l | NM_001114611.1 | chr16:37107309-37384958 | 20749 | Syce3 | NM_001162880.1 | chr15:89390173-89410503 |
| 20653 | Stxbp6 | NM_144552.3 | chr12:44652485-45074483 | 20750 | Sycn | NM_026716.3 | chr7:285408884-28542210 |
| 20654 | Styk1 | NM_172891.2 | chr6:131299148-131313827 | 20751 | Sycp1 | NM_011516.2 | chr3:102816498-102936100 |
| 20655 | Styx | NM_019637.3 | chr14:45351185-45376884 | 20752 | Sycp1-ps1 | NR_024208.1 | chr7:18786301-18789414 |
| 20656 | Styxl1 | NM_001289554.1 | chr5:135747219-135778301 | 20753 | Sycp2 | NM_177191.3 | chr2:178345295-178407668 |
| 20657 | Sub1 | NM_011294.5 | chr15:11981338-11996007 | 20754 | Sycp3 | NM_011517.2 | chr10:88459586-88473236 |
| 20658 | Suclg2 | NM_011506.3 | chr14:73552785-73596142 | 20755 | Syde1 | NM_027875.1 | chr10:78584502-78591964 |
| 20659 | Suclg1 | NM_019879.3 | chr6:73248504-73276907 | 20756 | Syde2 | NM_001166064.1 | chr3:145987869-146021720 |
| 20660 | Suclg2 | NM_011507.3 | chr6:95473008-95718846 | 20757 | Syf2 | NM_026780.3 | chr4:134930979-134937537 |

Fig.21 - 108

| | | | | | | | | |
|---|---|---|---|---|---|---|---|---|
| 20758 | Syk | NM_001198977.1 | chr13:52583436-52648792 | 20855 | Taf13 | NM_025444.2 | chr3:108571698-108582068 |
| 20759 | Sympk | NM_026605.2 | chr7:19024376-19054622 | 20856 | Taf15 | NM_027427.2 | chr11:83473107-83506740 |
| 20760 | Syn1 | NM_001110780.1 | chrX:20860510-20920918 | 20857 | Tafla | NM_001277957.1 | chr1:183388884-183410206 |
| 20761 | Syn2 | NM_001111015.1 | chr6:115134901-115282626 | 20858 | Taf1b | NM_020614.2 | chr12:24498580-24558571 |
| 20762 | Syn3 | NM_001164495.1 | chr10:86291592-86498896 | 20859 | Taf1c | NM_021441.2 | chr8:119597973-119605240 |
| 20763 | Syna | NM_001013751.2 | chr5:134557253-134560171 | 20860 | Taf1d | NM_027261.3 | chr9:15306213-15312105 |
| 20764 | Synb | NM_173420.3 | chr14:69290397-69512549 | 20861 | Taf2 | NM_001081288.1 | chr15:55015128-55072152 |
| 20765 | Sync | NM_023485.3 | chr4:129287620-129308559 | 20862 | Taf3 | NM_027748.3 | chr2:9914551-10048609 |
| 20766 | Syncrip | NM_001284328.1 | chr9:88449363-88482397 | 20863 | Taf4a | NM_001081092.1 | chr2:179912145-179976646 |
| 20767 | Syndig1 | NM_001085521.2 | chr2:149830782-150004392 | 20864 | Taf4b | NM_001100449.1 | chr18:14783244-14900359 |
| 20768 | Syndig1l | NM_001033334.2 | chr12:84677277-84698807 | 20865 | Taf5 | NM_177342.3 | chr19:47067747-47083479 |
| 20769 | Syne1 | NM_001079686.1 | chr10:5020195-5194707 | 20866 | Taf5l | NM_139966.2 | chr8:123998312-124021309 |
| 20770 | Syne2 | NM_001005510.2 | chr12:75818317-76110928 | 20867 | Taf6 | NM_009315.3 | chr5:138178616-138187186 |
| 20771 | Syne3 | NM_001042699.2 | chr12:104929932-104998677 | 20868 | Taf6l | NM_001177798.1 | chr19:8774353-8786417 |
| 20772 | Syne4 | NM_001290565.1 | chr7:36314815-30319045 | 20869 | Taf7 | NM_175770.4 | chr18:37640490-37644204 |
| 20773 | Syngap1 | NM_001281491.1 | chr17:26941451-26970645 | 20870 | Taf7l | NM_028958.4 | chrX:134460115-134476490 |
| 20774 | Syngr1 | NM_009303.2 | chr15:80091333-80113440 | 20871 | Taf8 | NM_022015.3 | chr17:47488049-47502287 |
| 20775 | Syngr2 | NM_009304.2 | chr11:117809666-117814286 | 20872 | Taf9 | NM_001015889.2 | chr13:100651606-100656060 |
| 20776 | Syngr3 | NM_015522.3 | chr17:24685091-24689949 | 20873 | Taf9b | NM_001001176.2 | chrX:106208873-106219842 |
| 20777 | Syngr4 | NM_001291064.1 | chr7:45886844-45896711 | 20874 | Tagap | NM_145968.2 | chr17:7925999-7934897 |
| 20778 | Synj1 | NM_001045515.1 | chr16:90936100-91011095 | 20875 | Tagap1 | NM_147155.2 | chr17:6954964-6961156 |
| 20779 | Synj2 | NM_001113351.1 | chr17:5975585-6044290 | 20876 | Tagln | NM_011526.5 | chr9:45929627-45936058 |
| 20780 | Synj2bp | NM_025292.7 | chr12:81492193-81532911 | 20877 | Tagln2 | NM_178598.2 | chr1:172500245-172507375 |
| 20781 | Synm | NM_183312.3 | chr7:67730160-67759742 | 20878 | Tagln3 | NM_019754.3 | chr16:45713229-45724531 |
| 20782 | Synpo | NM_001109975.1 | chr18:60600205-60630104 | 20879 | Tal1 | NM_001287388.1 | chr4:115057810-115071755 |
| 20783 | Synpo2 | NM_080451.2 | chr3:123076018-123236149 | 20880 | Tal2 | NM_009317.3 | chr4:53779704-53786885 |
| 20784 | Synpo2l | NM_175132.4 | chr14:20658947-20668354 | 20881 | Taldo1 | NM_015528.4 | chr7:141392159-141402976 |
| 20785 | Synpr | NM_001163032.1 | chr14:13453957-13615469 | 20882 | Tamm41 | NM_026894.1 | chr6:115004380-115037874 |
| 20786 | Synrg | NM_19434.2 | chr11:8964430-84044576 | 20883 | Tanc1 | NM_001290659.1 | chr2:59646768-59846213 |
| 20787 | Syp | NM_009305.2 | chrX:7638579-7653256 | 20884 | Tanc2 | NM_181071.3 | chr11:105589985-105929303 |
| 20788 | Sypl | NM_019635.3 | chr12:32953944-32979600 | 20885 | Tango2 | NM_138583.2 | chr16:18300824-18343932 |
| 20789 | Sypl2 | NM_018596.1 | chr3:108212265-108226599 | 20886 | Tango6 | NM_173037.1 | chr8:106683067-106851439 |
| 20790 | Sys1 | NM_025575.3 | chr2:164460970-164465510 | 20887 | Tank | NM_001164071.1 | chr2:61593096-61654169 |
| 20791 | Syt1 | NM_001252341.1 | chr10:108497649-109010975 | 20888 | Taok1 | NM_144825.2 | chr11:77529161-77607815 |
| 20792 | Syt10 | NM_018803.2 | chr15:89782392-89841860 | 20889 | Taok2 | NM_001163774.1 | chr7:126865676-126884967 |
| 20793 | Syt11 | NM_018804.1 | chr3:88744760-88772599 | 20890 | Taok3 | NM_001081308.2 | chr5:117133587-117275098 |
| 20794 | Syt12 | NM_134164.5 | chr19:4445907-4477143 | 20891 | Tap1 | NM_001161730.1 | chr17:34187555-34197225 |
| 20795 | Syt13 | NM_030725.4 | chr2:92915100-92956051 | 20892 | Tap2 | NM_011530.3 | chr17:34204478-34216321 |
| 20796 | Syt14 | NM_181395.2 | chr1:192891233-193035775 | 20893 | Tapbp | NM_001025313.1 | chr17:33919477-33929290 |
| 20797 | Syt15 | NM_176931.2 | chr14:34220045-34227740 | 20894 | Tapbpl | NM_145391.2 | chr6:125224211-125231860 |
| 20798 | Syt16 | NM_172804.2 | chr12:73997760-74267916 | 20895 | Tapt1 | NM_173764.3 | chr5:44175161-44226606 |
| 20799 | Syt17 | NM_118649.1 | chr7:118381555-118443552 | 20896 | Tarbp2 | NM_001253795.1 | chr15:102518191-102523676 |
| 20800 | Syt2 | NM_009307.3 | chr1:134646680-134749417 | 20897 | Tardbp | NM_001003898.3 | chr4:148612381-148626996 |
| 20801 | Syt3 | NM_001114116.1 | chr7:44384125-44400030 | 20898 | Tarm1 | NM_177363.3 | chr7:3489075-3502552 |
| 20802 | Syt4 | NM_009308.3 | chr18:31437807-31447415 | 20899 | Tars | NM_033074.3 | chr15:11383662-11399658 |
| 20803 | Syt5 | NM_016908.2 | chr7:4539764-4546567 | 20900 | Tars2 | NM_001163617.1 | chr3:95739973-95754977 |
| 20804 | Syt6 | NM_001275865.1 | chr3:103575281-103635179 | 20901 | Tarsl2 | NM_172310.2 | chr7:65644897-65692093 |
| 20805 | Syt7 | NM_018801.3 | chr19:10389089-10453181 | 20902 | Tas1r1 | NM_031867.2 | chr4:152027913-152038490 |
| 20806 | Syt8 | NM_001285857.1 | chr7:142434976-142440396 | 20903 | Tas1r2 | NM_031873.1 | chr4:139663537-139670279 |
| 20807 | Syt9 | NM_021889.4 | chr7:107370789-107548655 | 20904 | Tas1r3 | NM_031872.2 | chr4:155859269-155863353 |
| 20808 | Sytl1 | NM_031393.2 | chr4:133253089-133263087 | 20905 | Tas2r102 | NM_199153.2 | chr6:132762130-132763174 |
| 20809 | Sytl2 | NM_001040085.2 | chr7:90302354-90410719 | 20906 | Tas2r103 | NM_053211.1 | chr6:133036162-133037101 |
| 20810 | Sytl3 | NM_134395.2 | chr17:6673609-6738044 | 20907 | Tas2r104 | NM_207011.1 | chr6:131684835-131685744 |
| 20811 | Sytl4 | NM_001290717.1 | chrX:133986384-133981812 | 20908 | Tas2r105 | NM_020501.1 | chr6:131685560-131687463 |
| 20812 | Sytl5 | NM_001290728.1 | chrX:9885620-9998864 | 20909 | Tas2r106 | NM_207016.1 | chr6:131677959-131678886 |
| 20813 | Syvn1 | NM_001164709.1 | chr19:6047144-6053718 | 20910 | Tas2r107 | NM_199154.1 | chr6:131659157-131660084 |
| 20814 | Szrd1 | NM_001025608.2 | chr4:141112977-141139796 | 20911 | Tas2r108 | NM_020502.1 | chr6:40493593-40494485 |
| 20815 | Szt2 | NM_198170.4 | chr4:118362739-118409263 | 20912 | Tas2r109 | NM_207017.1 | chr6:132980014-132980965 |
| 20816 | T | NM_009309.2 | chr17:8434422-8442496 | 20913 | Tas2r110 | NM_199155.2 | chr6:132868007-132869009 |
| 20817 | T2 | NM_001161832.1 | chr17:8372395-8422726 | 20914 | Tas2r113 | NM_207018.1 | chr6:132893010-132893940 |
| 20818 | Taar1 | NM_053205.1 | chr10:23920405-23921404 | 20915 | Tas2r114 | NM_001168133.1 | chr6:131689133-131690063 |
| 20819 | Taar2 | NM_001007266.1 | chr10:23938571-23941583 | 20916 | Tas2r115 | NM_207020.1 | chr6:132737053-132737986 |
| 20820 | Taar3 | NM_001008429.1 | chr10:23949557-23950589 | 20917 | Tas2r116 | NM_053212.1 | chr6:132855437-132856355 |
| 20821 | Taar4 | NM_001008499.1 | chr10:23960493-23961537 | 20918 | Tas2r117 | NM_207021.1 | chr6:132802900-132803893 |
| 20822 | Taar5 | NM_001009574.1 | chr10:23970705-23971719 | 20919 | Tas2r118 | NM_207022.1 | chr6:23969160-23970060 |
| 20823 | Taar6 | NM_001010828.1 | chr10:23984608-23985646 | 20920 | Tas2r119 | NM_020503.2 | chr15:32177288-32178294 |
| 20824 | Taar7a | NM_001010829.1 | chr10:23992404-23993481 | 20921 | Tas2r120 | NM_207023.1 | chr6:132656956-132657844 |
| 20825 | Taar7b | NM_001010827.1 | chr10:23999938-24001015 | 20922 | Tas2r121 | NM_207024.1 | chr6:132700089-132701007 |
| 20826 | Taar7d | NM_001010838.1 | chr10:24027221-24028298 | 20923 | Tas2r122 | NM_001039128.1 | chr6:132710998-132711928 |
| 20827 | Taar7e | NM_001010835.1 | chr10:24037613-24038690 | 20924 | Tas2r123 | NM_207025.1 | chr6:132847141-131848143 |
| 20828 | Taar7f | NM_001010839.1 | chr10:24049509-24050586 | 20925 | Tas2r124 | NM_207026.1 | chr6:132754729-132755659 |
| 20829 | Taar8a | NM_001010830.1 | chr10:24076499-24077534 | 20926 | Tas2r125 | NM_207027.1 | chr6:132909650-132910586 |
| 20830 | Taar8b | NM_001010837.1 | chr10:24091259-24092294 | 20927 | Tas2r126 | NM_207028.1 | chr6:42434634-42435461 |
| 20831 | Taar8c | NM_001010842.2 | chr10:24100842-24101951 | 20928 | Tas2r129 | NM_207029.1 | chr6:132951103-132952064 |
| 20832 | Taar9 | NM_001010831.1 | chr10:24108487-24109534 | 20929 | Tas2r130 | NM_199156.1 | chr6:131629891-131630830 |
| 20833 | Tab1 | NM_025609.2 | chr15:80133153-80161702 | 20930 | Tas2r131 | NM_207030.1 | chr6:132956911-132957844 |
| 20834 | Tab2 | NM_138667.3 | chr10:7905647-7956123 | 20931 | Tas2r134 | NM_199158.1 | chr2:51627510-51628407 |
| 20835 | Tab3 | NM_025729.4 | chrX:85574021-85634469 | 20932 | Tas2r135 | NM_199159.1 | chr6:42405528-42406494 |
| 20836 | Tac1 | NM_009311.2 | chr6:7555070-7562973 | 20933 | Tas2r136 | NM_132776.1 | chr6:132777178-132778162 |
| 20837 | Tac2 | NM_009312.1 | chr10:127724477-127731768 | 20934 | Tas2r137 | NM_001025385.1 | chr6:40491237-40492239 |
| 20838 | Tac4 | NM_053093.1 | chr11:95261528-95269261 | 20935 | Tas2r138 | NM_001001451.1 | chr6:40612314-40613310 |
| 20839 | Tacc1 | NM_177089.5 | chr8:25154551-25201542 | 20936 | Tas2r139 | NM_181275.1 | chr6:42140935-42141895 |
| 20840 | Tacc2 | NM_001094468.2 | chr7:130577483-130764782 | 20937 | Tas2r140 | NM_021562.1 | chr6:133054854-133055793 |
| 20841 | Tacc3 | NM_001040435.3 | chr5:33658127-33672202 | 20938 | Tas2r143 | NM_001001452.1 | chr6:42400237-42401119 |
| 20842 | Taco1 | NM_027346.1 | chr11:106066106-106073612 | 20939 | Tas2r144 | NM_001001453.1 | chr6:42215327-42216287 |
| 20843 | Tacr1 | NM_009313.5 | chr6:82402474-82560104 | 20940 | Tasp1 | NM_001159840.2 | chr2:139833478-140066805 |
| 20844 | Tacr2 | NM_009314.4 | chr10:62622437-62265990 | 20941 | Tat | NM_146214.3 | chr8:109990435-109999804 |
| 20845 | Tacr3 | NM_021382.6 | chr3:134829006-134934581 | 20942 | Tatdn1 | NM_175151.4 | chr15:58890152-58933730 |
| 20846 | Tacstd2 | NM_020047.3 | chr6:67534058-67535822 | 20943 | Tatdn2 | NM_001033463.3 | chr6:113697498-113711068 |
| 20847 | Tada1 | NM_030245.3 | chr1:166379166-166393620 | 20944 | Tatdn3 | NM_001163421.1 | chr1:191045829-191062932 |
| 20848 | Tada2a | NM_172562.3 | chr11:84078919-84109568 | 20945 | Tax1bp1 | NM_025816.3 | chr6:52713728-52766779 |
| 20849 | Tada2b | NM_001170454.1 | chr5:36473669-36484285 | 20946 | Tax1bp3 | NM_029564.2 | chr11:73177082-73182046 |
| 20850 | Tada3 | NM_133932.2 | chr6:113366656-113377520 | 20947 | Tbata | NM_001173547.2 | chrX:74282717-74290151 |
| 20851 | Taf1 | NM_001290729.1 | chrX:101527574-101601789 | 20948 | Tbc1d1 | NM_001017407.1 | chr5:64230356-64351486 |
| 20852 | Taf10 | NM_020604.3 | chr7:105742093-105744338 | 20949 | Tbc1d10a | NM_001289514.1 | chr5:64230356-64351486 |
| 20853 | Taf11 | NM_026836.2 | chr17:27901127-27907724 | 20950 | Tbc1d10a | NM_134023.1 | chr11:4186832-4215505 |
| 20854 | Taf12 | NM_025579.3 | chr4:132274374-132293330 | 20951 | Tbc1d10b | NM_144522.5 | chr7:127197458-127208468 |

Fig.21 - 109

| | | | | | | | | |
|---|---|---|---|---|---|---|---|---|
| 20952 | Tbc1d10c | NM_178650.3 | chr19:4184356-4191047 | | 21049 | Tcf7l2 | NM_001142918.1 | chr19:55741809-55933655 |
| 20953 | Tbc1d12 | NM_145952.3 | chr19:38836578-38919923 | | 21050 | Tcfl5 | NM_178254.3 | chr2:180621956-180642691 |
| 20954 | Tbc1d13 | NM_146252.2 | chr2:30133870-30152013 | | 21051 | Tchh | NM_001163098.1 | chr3:93442329-93449077 |
| 20955 | Tbc1d14 | NM_001113362.1 | chr5:36490603-36586226 | | 21052 | Tchhl1 | NM_027762.3 | chr3:93468753-93471980 |
| 20956 | Tbc1d15 | NM_025706.3 | chr10:115197870-115251493 | | 21053 | Tchp | NM_029992.2 | chr5:114707778-114722327 |
| 20957 | Tbc1d16 | NM_172443.3 | chr11:119143042-119228499 | | 21054 | Tcirg1 | NM_001136091.2 | chr19:3896049-3907133 |
| 20958 | Tbc1d17 | NM_001042655.1 | chr7:44840775-44849079 | | 21055 | Tcl1 | NM_001289468.1 | chr12:105216754-105222737 |
| 20959 | Tbc1d19 | NM_144517.4 | chr5:53809626-53904380 | | 21056 | Tcl1b1 | NM_013773.2 | chr12:105159703-105166625 |
| 20960 | Tbc1d2 | NM_198664.3 | chr4:46604389-46650199 | | 21057 | Tcl1b2 | NM_013775.1 | chr12:105147032-105155225 |
| 20961 | Tbc1d20 | NM_024196.3 | chr2:152293871-152312590 | | 21058 | Tcl1b3 | NM_013772.2 | chr12:105191044-105195399 |
| 20962 | Tbc1d21 | NM_028854.3 | chr9:58359803-58370869 | | 21059 | Tcl1b4 | NM_013774.2 | chr12:105202421-105206993 |
| 20963 | Tbc1d22a | NM_145476.2 | chr15:86214458-86498503 | | 21060 | Tcl1b5 | NM_013776.1 | chr12:105176357-105181145 |
| 20964 | Tbc1d22b | NM_198647.1 | chr7:29549801-29606808 | | 21061 | Tcn2 | NM_001130458.1 | chr11:3917079-3932678 |
| 20965 | Tbc1d22bos | NR_045447.1 | chr17:29572815-29596305 | | 21062 | Tcof1 | NM_001198984.1 | chr18:60813755-60848964 |
| 20966 | Tbc1d23 | NM_026254.2 | chr16:57168863-57231466 | | 21063 | Tcp1 | NM_001290712.1 | chr17:12916328-12925087 |
| 20967 | Tbc1d24 | NM_001163847.1 | chr17:24175430-24205562 | | 21064 | Tcp10a | NM_011553.4 | chr17:7324659-7345860 |
| 20968 | Tbc1d25 | NM_001166437.1 | chrX:8154471-8176181 | | 21065 | Tcp10b | NM_009341.2 | chr17:13061110-13082226 |
| 20969 | Tbc1d2b | NM_194334.2 | chr9:90202048-90270769 | | 21066 | Tcp10c | NM_001167578.1 | chr17:13354571-13377223 |
| 20970 | Tbc1d30 | NM_029057.1 | chr10:121263819-121311189 | | 21067 | Tcp11 | NM_001085555.1 | chr17:28066746-28080639 |
| 20971 | Tbc1d31 | NM_001081396.2 | chr15:57912198-57970068 | | 21068 | Tcp11l1 | NM_177190.5 | chr2:104679979-104712162 |
| 20972 | Tbc1d32 | NM_001033385.3 | chr10:56014293-56228689 | | 21069 | Tcp11l2 | NM_148008.2 | chr10:84576946-84614355 |
| 20973 | Tbc1d4 | NM_001081278.2 | chr14:101422359-101609191 | | 21070 | Tcstv1 | NM_018756.3 | chr13:119893386-119894785 |
| 20974 | Tbc1d5 | NM_001285991.1 | chr17:50733126-51179352 | | 21071 | Tcstv3 | NM_153523.3 | chr13:120316861-120318281 |
| 20975 | Tbc1d7 | NM_001252639.1 | chr13:43151741-43171501 | | 21072 | Tcta | NM_139986.2 | chr9:108302954-108306159 |
| 20976 | Tbc1d8 | NM_018775.4 | chr1:39371495-39478747 | | 21073 | Tcte1 | NM_013688.2 | chr17:45523433-45542877 |
| 20977 | Tbc1d8b | NM_001081499.2 | chrX:139684995-139754218 | | 21074 | Tcte2 | NM_022311.2 | chr17:13716435-13761394 |
| 20978 | Tbc1d9 | NM_001111304.1 | chr8:83165351-83272940 | | 21075 | Tcte3 | NM_011560.3 | chr17:15027153-15041559 |
| 20979 | Tbc1d9b | NM_001290759.1 | chr11:50131359-50172785 | | 21076 | Tctex1d1 | NM_001163767.1 | chr4:102986378-103005594 |
| 20980 | Tbca | NM_009321.2 | chr13:94788942-94842899 | | 21077 | Tctex1d2 | NM_025329.3 | chr16:32419701-32428692 |
| 20981 | Tbcb | NM_025548.3 | chr7:30224130-30232029 | | 21078 | Tctex1d4 | NM_175030.2 | chr4:117126812-117128730 |
| 20982 | Tbcc | NM_178385.3 | chr17:46890620-46892463 | | 21079 | Tctn1 | NM_001039153.3 | chr5:122239494-122264460 |
| 20983 | Tbccd1 | NM_001081368.2 | chr16:22813214-22857569 | | 21080 | Tctn2 | NM_026486.3 | chr5:124598748-124627738 |
| 20984 | Tbcd | NM_029878.1 | chr11:121451948-121617170 | | 21081 | Tctn3 | NM_026260.2 | chr19:40596445-40612215 |
| 20985 | Tbce | NM_178337.3 | chr13:13997950-14039638 | | 21082 | Tdg | NM_011561.2 | chr10:82629837-82650494 |
| 20986 | Tbcel | NM_173038.3 | chr9:42412316-42472226 | | 21083 | Tdgf1 | NM_011562.2 | chr9:110936607-110946158 |
| 20987 | Tbck | NM_001163455.2 | chr3:132684142-132841688 | | 21084 | Tdh | NM_021480.5 | chr14:63492346-63509092 |
| 20988 | Tbk1 | NM_019786.4 | chr10:121546455-121586794 | | 21085 | Tdo2 | NM_019911.2 | chr3:81958411-81975728 |
| 20989 | Tbkbp1 | NM_198100.2 | chr11:97136170-97149712 | | 21086 | Tdp1 | NM_028354.4 | chr12:99884514-99955216 |
| 20990 | Tbl1x | NM_020601.2 | chrX:77511226-77660265 | | 21087 | Tdp2 | NM_019551.2 | chr13:24831658-24842153 |
| 20991 | Tbl1xr1 | NM_030732.3 | chr3:22076651-22216594 | | 21088 | Tdpoz1 | NM_148949.2 | chr3:93669332-93676283 |
| 20992 | Tbl2 | NM_013763.2 | chr5:135149710-135162662 | | 21089 | Tdpoz2 | NM_001007222.3 | chr3:93651541-93662686 |
| 20993 | Tbl3 | NM_175814.5 | chr17:24700652-24707653 | | 21090 | Tdpoz3 | NM_207271.2 | chr3:93826019-93827117 |
| 20994 | Tbp | NM_013684.3 | chr17:15499887-15517427 | | 21091 | Tdpoz4 | NM_207272.2 | chr3:93796397-93797510 |
| 20995 | Tbpl1 | NM_011603.5 | chr10:22703876-22731447 | | 21092 | Tdpoz5 | NM_207273.2 | chr3:93960291-94072644 |
| 20996 | Tbpl2 | NM_001289689.1 | chr2:24071365-24096595 | | 21093 | Tdrd1 | NM_001022238.2 | chr19:56826208-56870012 |
| 20997 | Tbr1 | NM_009322.3 | chr2:61804452-61814113 | | 21094 | Tdrd12 | NM_028034.2 | chr7:35493609-35537744 |
| 20998 | Tbrg1 | NM_025289.3 | chr9:37649181-37657312 | | 21095 | Tdrd3 | NM_001253755.1 | chr14:87416582-87515192 |
| 20999 | Tbrg3 | NR_027799.1 | chr5:82890482-82898461 | | 21096 | Tdrd5 | NM_001334741.1 | chr1:156155295-156303348 |
| 21000 | Tbrg4 | NM_001130457.1 | chr11:6615597-6626067 | | 21097 | Tdrd6 | NM_001161366.1 | chr17:43615334-43630299 |
| 21001 | Tbx1 | NM_001082976.2 | chr16:18581703-18590671 | | 21098 | Tdrd7 | NM_001290475.1 | chr4:45965334-46034765 |
| 21002 | Tbx10 | NM_001001320.1 | chr19:3992751-3999512 | | 21099 | Tdrd9 | NM_029056.1 | chr12:111971558-112068854 |
| 21003 | Tbx15 | NM_009323.2 | chr3:99253759-99354260 | | 21100 | Tdrkh | NM_028307.1 | chr3:94413317-94431499 |
| 21004 | Tbx18 | NM_023814.4 | chr9:87702799-87731260 | | 21101 | Tdrp | NM_173744.4 | chr8:13952007-13974777 |
| 21005 | Tbx19 | NM_032005.4 | chr1:165137852-165160773 | | 21102 | Tead1 | NM_001166584.1 | chr7:112679319-112908805 |
| 21006 | Tbx2 | NM_009324.2 | chr11:85832614-85841948 | | 21103 | Tead2 | NM_001285498.1 | chr7:45215752-45233619 |
| 21007 | Tbx20 | NM_001205085.1 | chr9:24740247-24774303 | | 21104 | Tead3 | NM_001098226.3 | chr17:28331672-28350600 |
| 21008 | Tbx21 | NM_019507.2 | chr11:97098006-97115331 | | 21105 | Tead4 | NM_001080979.1 | chr6:128227142-128300813 |
| 21009 | Tbx22 | NM_001290747.1 | chrX:107679014-107688980 | | 21106 | Tec | NM_001113460.2 | chr5:72755717-72868448 |
| 21010 | Tbx3 | NM_011535.3 | chr5:119671232-119684724 | | 21107 | Tecpr1 | NM_027410.1 | chr5:144195346-144223578 |
| 21011 | Tbx3os2 | NR_040416.1 | chr5:119685087-119691218 | | 21108 | Tecpr2 | NM_001081057.2 | chr12:110889263-110972394 |
| 21012 | Tbx4 | NM_011535.3 | chr11:85890062-85916097 | | 21109 | Tecr | NM_027179.1 | chr8:83571697-83594491 |
| 21013 | Tbx5 | NM_011537.3 | chr5:119834662-119885218 | | 21110 | Tecrl | NM_153801.3 | chr5:83278121-83355195 |
| 21014 | Tbx6 | NM_011538.2 | chr7:126781482-126785548 | | 21111 | Tecta | NM_009347.2 | chr9:42329621-42399929 |
| 21015 | Tbxa2r | NM_001277265.1 | chr10:81328702-81335174 | | 21112 | Tectb | NM_009348.3 | chr19:55180884-55196313 |
| 21016 | Tbxas1 | NM_011539.3 | chr6:38918985-39084579 | | 21113 | Teddm1 | NM_178244.3 | chr1:153891645-153893060 |
| 21017 | Tc2n | NM_001082976.1 | chr12:101645445-101718523 | | 21114 | Tef | NM_017376.3 | chr15:81811413-81826863 |
| 21018 | Tcaim | NM_001013405.2 | chr9:122505546-122886332 | | 21115 | Tefm | NM_183275.2 | chr11:80136677-80142153 |
| 21019 | Tcaml | NM_029467.3 | chr11:106276671-106288143 | | 21116 | Tek | NM_001290549.1 | chr4:94739288-94874976 |
| 21020 | Tcap | NM_011540.2 | chr11:98383810-98384953 | | 21117 | Tekt1 | NM_001282006.1 | chr11:72344716-72362442 |
| 21021 | Tcea1 | NM_001159750.1 | chr1:4857693-4897909 | | 21118 | Tekt2 | NM_011902.2 | chr4:126322120-126325199 |
| 21022 | Tcea2 | NM_009326.2 | chr2:181680309-181688051 | | 21119 | Tekt3 | NM_027660.1 | chr11:63061658-63094960 |
| 21023 | Tcea3 | NM_011542.2 | chr4:136247956-136274899 | | 21120 | Tekt4 | NM_027951.1 | chr17:25473589-25478594 |
| 21024 | Tceal1 | NM_146236.1 | chrX:136708064-136709866 | | 21121 | Tekt5 | NM_001099275.1 | chr16:10361253-10395448 |
| 21025 | Tceal3 | NM_001029978.2 | chrX:136666374-136668377 | | 21122 | Telo2 | NM_001163661.1 | chr17:25089568-25115967 |
| 21026 | Tceal5 | NM_177919.2 | chrX:136200950-136203851 | | 21123 | Ten1 | NM_027107.1 | chr11:116198854-116215318 |
| 21027 | Tceal6 | NM_025355.4 | chrX:135208685-135210687 | | 21124 | Tenc1 | NM_153533.2 | chr15:102102987-102116401 |
| 21028 | Tceal7 | NM_001127169.1 | chrX:136224040-136226100 | | 21125 | Tenm1 | NM_011855.4 | chrX:42532392-43274784 |
| 21029 | Tceal8 | NM_001168578.1 | chrX:136168983-136172251 | | 21126 | Tenm2 | NM_001290702.1 | chr11:36006655-36944241 |
| 21030 | Tceanc | NM_001007577.2 | chrX:166499814-166510478 | | 21127 | Tenm3 | NM_145937.1 | chr8:48225664-48674690 |
| 21031 | Tceanc2 | NM_025617.2 | chr4:107134161-107178366 | | 21128 | Tenm4 | NM_011858.4 | chr7:96210636-96911092 |
| 21032 | Tceb1 | NM_026456.3 | chr1:16442764-16556865 | | 21129 | Tep1 | NM_009351.2 | chr14:50824060-50870554 |
| 21033 | Tceb2 | NM_025395.2 | chr17:23824739-23829109 | | 21130 | Tepp | NM_028532.3 | chr8:95311597-95321329 |
| 21034 | Tceb3 | NM_013736.4 | chr4:136003369-136021649 | | 21131 | Terc | NR_001579.1 | chr3:96414436-96414833 |
| 21035 | Tcerg1 | NM_001039474.1 | chr18:42511486-42575785 | | 21132 | Terf1 | NM_001286628.1 | chr1:15805645-15844652 |
| 21036 | Tcerg1l | NM_183289.3 | chr7:138268971-138397730 | | 21133 | Terf2 | NM_001083118.2 | chr8:107075516-107096545 |
| 21037 | Tcf12 | NM_001253862.1 | chr9:71844251-72112281 | | 21134 | Terf2ip | NM_020584.2 | chr8:112011358-112020528 |
| 21038 | Tcf15 | NM_009328.3 | chr2:152143608-152149096 | | 21135 | Tert | NM_009354.1 | chr13:73627000-73649041 |
| 21039 | Tcf19 | NM_001163763.1 | chr17:35512734-35516824 | | 21136 | Tes | NM_207176.3 | chr6:17065148-17105825 |
| 21040 | Tcf20 | NM_001114140.1 | chr15:82808625-82912134 | | 21137 | Tesc | NM_021344.3 | chr5:118027823-118061870 |
| 21041 | Tcf21 | NM_011545.1 | chr10:22817274-22820128 | | 21138 | Tesk1 | NM_001163810.1 | chr4:43423079-24333965 |
| 21042 | Tcf23 | NM_053085.2 | chr5:30868676-30977018 | | 21139 | Tesk1 | NM_011571.3 | chr4:43442276-43448075 |
| 21043 | Tcf24 | NM_001285425.1 | chr1:9960162-9967485 | | 21140 | Tesk2 | NM_146151.4 | chr4:116720954-116804248 |
| 21044 | Tcf25 | NM_194334.2 | chr8:123373710-123404174 | | 21141 | Tespa1 | NM_183264.4 | chr10:130322851-130362642 |
| 21045 | Tcf3 | NM_001164147.1 | chr10:80409164-80433653 | | 21142 | Tet1 | NM_001253857.1 | chr10:62804569-62850014 |
| 21046 | Tcf4 | NM_013967.1 | chr18:69345726-69687967 | | 21143 | Tet2 | NM_001040400.2 | chr3:133463676-133544390 |
| 21047 | Tcf7 | NM_009331.4 | chr11:52252282-52282595 | | 21144 | Tet3 | NM_183138.2 | chr6:83362373-83441678 |
| 21048 | Tcf7l1 | NM_001079822.2 | chr6:72626370-72789045 | | 21145 | Tex10 | NM_172304.3 | chr4:48439956-48473422 |

Fig.21 - 110

| | | | | | | | | |
|---|---|---|---|---|---|---|---|---|
| 21146 | Tex101 | NM_019981.2 | chr7:24668011-24672050 | 21243 | Theg | NM_011583.3 | chr10:79576476-79587136 |
| 21147 | Tex11 | NM_001167997.1 | chrX:100877881-101059639 | 21244 | Them4 | NM_029431.1 | chr3:94310131-94332592 |
| 21148 | Tex12 | NM_025687.3 | chr9:50557147-50561268 | 21245 | Them5 | NM_025416.3 | chr3:94342098-94347352 |
| 21149 | Tex13 | NM_031381.2 | chrX:140808306-140813433 | 21246 | Them6 | NM_198607.1 | chr15:74721233-74724373 |
| 21150 | Tex13a | NM_026469.2 | chrX:138203164-138209580 | 21247 | Them7 | NM_001159638.1 | chr2:105224341-105379860 |
| 21151 | Tex14 | NM_001199293.1 | chr11:87427590-87555823 | 21248 | Themis | NM_178666.6 | chr10:28668359-28883818 |
| 21152 | Tex15 | NM_031374.2 | chr8:33550543-33585585 | 21249 | Themis2 | NM_001033308.2 | chr4:132782356-132796364 |
| 21153 | Tex16 | NM_031382.2 | chrX:112093519-112127326 | 21250 | Themis3 | NM_028998.1 | chr17:66555251-66594622 |
| 21154 | Tex19.1 | NM_028602.2 | chr11:121146142-121148313 | 21251 | Thg1l | NM_001080969.3 | chr11:45945305-45955503 |
| 21155 | Tex19.2 | NM_027822.3 | chr11:121116214-121118677 | 21252 | Thnsl1 | NM_001901297.2 | chr2:21205723-21215009 |
| 21156 | Tex2 | NM_198292.3 | chr11:106502138-106612980 | 21253 | Thnsl2 | NM_001038929.2 | chr6:71128165-71144380 |
| 21157 | Tex21 | NM_001159532.1 | chr12:76203984-76246746 | 21254 | Thoc1 | NM_153552.3 | chr18:9958179-9995484 |
| 21158 | Tex22 | NM_029381.1 | chr12:113074501-113088914 | 21255 | Thoc2 | NM_001033422.1 | chrX:41794993-41911901 |
| 21159 | Tex24 | NM_001013609.2 | chr8:27344393-27349188 | 21256 | Thoc3 | NM_028597.3 | chr13:54458836-54468840 |
| 21160 | Tex26 | NM_029464.2 | chr5:149439659-149470979 | 21257 | Thoc5 | NM_172438.3 | chr11:4895342-4928865 |
| 21161 | Tex261 | NM_009357.2 | chr6:83770413-83775812 | 21258 | Thoc6 | NM_001008425.1 | chr17:23668618-23673770 |
| 21162 | Tex264 | NM_001081654.2 | chr9:106658745-106685952 | 21259 | Thoc7 | NM_001285780.1 | chr14:13949011-13961313 |
| 21163 | Tex28 | NM_001126488.2 | chrX:74150943-74167838 | 21260 | Thop1 | NM_022653.4 | chr10:81070082-81082360 |
| 21164 | Tex29 | NM_029326.1 | chr8:118405520-11859761 | 21261 | Thpo | NM_001173505.1 | chr16:20724453-20730598 |
| 21165 | Tex30 | NM_029368.1 | chr1:44086616-44102388 | 21262 | Thra | NM_178060.4 | chr11:98741784-98765113 |
| 21166 | Tex33 | NM_001163612.2 | chr15:78378399-78395912 | 21263 | Thrap3 | NM_146153.3 | chr4:126164082-126202710 |
| 21167 | Tex35 | NM_028540.3 | chr1:157099146-157108650 | 21264 | Thrb | NM_001113417.1 | chr14:17660959-18038088 |
| 21168 | Tex36 | NM_001159396.1 | chr7:133587023-133602115 | 21265 | Thrsp | NM_009381.2 | chr7:97412956-97417510 |
| 21169 | Tex37 | NM_028825.3 | chr6:70913088-70918922 | 21266 | Thsd1 | NM_001205225.1 | chr8:22227302-22261332 |
| 21170 | Tex38 | NM_029196.1 | chr4:115779883-115781034 | 21267 | Thsd4 | NM_001040426.3 | chr9:59966930-60511035 |
| 21171 | Tex40 | NM_001099494.2 | chr19:6922425-6925380 | 21268 | Thsd7a | NM_001164805.1 | chr6:12311607-12749253 |
| 21172 | Tex43 | NM_026099.3 | chr18:56588347-56594779 | 21269 | Thsd7b | NM_172485.3 | chr1:129273303-130219278 |
| 21173 | Tex9 | NM_009359.4 | chr9:72458054-72491959 | 21270 | Thtpa | NM_153083.5 | chr14:55094783-55098995 |
| 21174 | Tfam | NM_009360.4 | chr10:71225476-71238044 | 21271 | Thumpd1 | NM_145585.2 | chr7:119715093-119720798 |
| 21175 | Tfap2a | NM_001122948.2 | chr13:40715302-40730457 | 21272 | Thumpd2 | NM_028138.1 | chr17:81026326-81065085 |
| 21176 | Tfap2b | NM_001025345.1 | chr1:19212053-19238845 | 21273 | Thumpd3 | NM_008188.2 | chr6:113046326-113068279 |
| 21177 | Tfap2c | NM_001159696.1 | chr2:172550990-172558621 | 21274 | Thy1 | NM_009382.3 | chr9:44043383-44048579 |
| 21178 | Tfap2d | NM_153154.2 | chr1:19103021-19166332 | 21275 | Thyn1 | NM_144543.2 | chr9:26999676-27007334 |
| 21179 | Tfap2e | NM_198960.2 | chr4:126102-126736269 | 21276 | Tia1 | NM_001164078.1 | chr6:86404218-86433405 |
| 21180 | Tfap4 | NM_031182.2 | chr16:4544660-4559720 | 21277 | Tial1 | NM_009383.2 | chr7:128439776-128461513 |
| 21181 | Tfb1m | NM_146074.1 | chr17:3519295-3557713 | 21278 | Tiam1 | NM_001145886.1 | chr16:89787110-89974699 |
| 21182 | Tfb2m | NM_008249.4 | chr1:179528055-179546267 | 21279 | Tiam2 | NM_001122998.1 | chr17:3326572-3519897 |
| 21183 | Tfcp2 | NM_001289603.1 | chr15:100502747-100552008 | 21280 | Ticam1 | NM_174989.4 | chr17:56269461-56276767 |
| 21184 | Tfcp2l1 | NM_023755.2 | chr1:118627944-118685168 | 21281 | Ticam2 | NM_173394.3 | chr18:46558230-46574533 |
| 21185 | Tfdp1 | NM_001291765.1 | chr8:13338750-13378448 | 21282 | Ticrr | NM_029835.1 | chr7:79660195-79698145 |
| 21186 | Tfdp2 | NM_001184706.1 | chr9:96196274-96323646 | 21283 | Tie1 | NM_013587.2 | chr4:118471190-118489849 |
| 21187 | Tfe3 | NM_001077319.1 | chrX:7762660-7775202 | 21284 | Tifa | NM_145133.3 | chr3:127789912-127798389 |
| 21188 | Tfeb | NM_001161722.1 | chr17:47737036-47792416 | 21285 | Tifab | NM_001168615.1 | chr13:56373702-56178885 |
| 21189 | Tfec | NM_031198.3 | chr6:16833380-16898441 | 21286 | Tigd2 | NM_001081145.1 | chr6:59208869-59212033 |
| 21190 | Tff1 | NM_009362.3 | chr17:31161395-31166053 | 21287 | Tigd3 | NM_198634.1 | chr19:5891137-5894107 |
| 21191 | Tff2 | NM_009363.3 | chr17:31141061-31144282 | 21288 | Tigd4 | NM_207278.2 | chr3:84593573-84597032 |
| 21192 | Tff3 | NM_011575.2 | chr17:31125305-31129611 | 21289 | Tigd5 | NM_178646.4 | chr15:75909734-75914535 |
| 21193 | Tfg | NM_001252443.1 | chr16:56690328-56717450 | 21290 | Tigit | NM_001146325.1 | chr16:43648860-43664184 |
| 21194 | Tfip11 | NM_018783.4 | chr5:112326368-112338073 | 21291 | Timd2 | NM_001161355.1 | chr11:46668989-46698830 |
| 21195 | Tfpi | NM_001177319.1 | chr2:84440722-84476759 | 21292 | Timd4 | NM_178759.4 | chr11:46810798-46844333 |
| 21196 | Tfpi2 | NM_009364.3 | chr6:3962594-3968354 | 21293 | Timeless | NM_001136082.2 | chr10:128232062-128252941 |
| 21197 | Tfpt | NM_001290382.1 | chr7:3620323-3629929 | 21294 | Timm10 | NM_013899.2 | chr2:84827020-84830213 |
| 21198 | Tfr2 | NM_001286507.1 | chr5:137570804-137588081 | 21295 | Timm10b | NM_019502.2 | chr7:105640539-105641845 |
| 21199 | Tfrc | NM_011638.4 | chr16:32608895-32632794 | 21296 | Timm13 | NM_013895.4 | chr10:80899449-80900969 |
| 21200 | Tg | NM_009375.2 | chr15:66670769-66850720 | 21297 | Timm17a | NM_013890.2 | chr1:135301534-135313737 |
| 21201 | Tgds | NM_029578.3 | chr14:118111910-118132765 | 21298 | Timm17b | NM_011591.5 | chrX:7899335-7907652 |
| 21202 | Tgfa | NM_031199.4 | chr6:86195226-86275743 | 21299 | Timm21 | NM_025969.4 | chr18:84947293-84951524 |
| 21203 | Tgfb1 | NM_011577.2 | chr7:25687001-25705077 | 21300 | Timm22 | NM_001291361.1 | chr11:76406924-76416313 |
| 21204 | Tgfb1i1 | NM_001289550.1 | chr7:128246811-128255699 | 21301 | Timm23 | NM_016897.3 | chr14:32180165-32201891 |
| 21205 | Tgfb2 | NM_009367.3 | chr1:186623185-186705992 | 21302 | Timm44 | NM_011595.2 | chr8:4259730-4275905 |
| 21206 | Tgfb3 | NM_009368.3 | chr12:86056742-86079041 | 21303 | Timm50 | NM_025616.3 | chr7:28305825-28312046 |
| 21207 | Tgfbi | NM_009369.4 | chr13:56609602-56639339 | 21304 | Timm8a1 | NM_013898.3 | chrX:11609223-134541670 |
| 21208 | Tgfbr1 | NM_009370.3 | chr4:47351221-47414924 | 21305 | Timm8a2 | NM_001037744.1 | chr14:122034673-122038422 |
| 21209 | Tgfbr2 | NM_009371.3 | chr9:116087694-116175363 | 21306 | Timm8b | NM_013897.2 | chr9:50603900-50605320 |
| 21210 | Tgfbr3 | NM_011578.5 | chr5:107106569-107289595 | 21307 | Timm9 | NM_001024853.1 | chr12:71123171-71136675 |
| 21211 | Tgfbrap1 | NM_001013025.2 | chr1:43047268-43098622 | 21308 | Timmdc1 | NM_024273.2 | chr16:38497842-38522863 |
| 21212 | Tgif1 | NM_001154074.1 | chr17:70844204-70853532 | 21309 | Timp1 | NM_001044384.1 | chrX:20870165-20874737 |
| 21213 | Tgif2 | NM_001291324.1 | chr2:156840006-156855569 | 21310 | Timp2 | NM_011594.3 | chr11:118301060-118355411 |
| 21214 | Tgif2lx1 | NM_153109.1 | chrX:118427234-118480729 | 21311 | Timp3 | NM_011595.2 | chr10:86300411-86349505 |
| 21215 | Tgif2lx2 | NM_001142750.1 | chrX:118427226-118480737 | 21312 | Timp4 | NM_080639.3 | chr6:115245615-115251849 |
| 21216 | Tgm1 | NM_001161714.1 | chr14:55700008-55713492 | 21313 | Tinag | NM_012033.3 | chr9:76951697-77045781 |
| 21217 | Tgm2 | NM_009373.3 | chr2:158116404-158146392 | 21314 | Tinagl1 | NM_001168333.1 | chr4:130165599-130174802 |
| 21218 | Tgm3 | NM_009374.3 | chr2:130012339-130050399 | 21315 | Tinf2 | NM_145705.3 | chr14:55679079-55681817 |
| 21219 | Tgm4 | NM_177911.4 | chr9:123074430-123067558 | 21316 | Tiparp | NM_178892.5 | chr3:65528446-65555518 |
| 21220 | Tgm5 | NM_028799.2 | chr2:121046110-121085759 | 21317 | Tipin | NM_025372.3 | chr9:64281606-64304792 |
| 21221 | Tgm6 | NM_001289747.1 | chr2:130123274-130154232 | 21318 | Tipr1 | NM_145513.4 | chr1:165212285-165236958 |
| 21222 | Tgm7 | NM_001164241.1 | chr2:121093588-121109791 | 21319 | Tiraj | NM_001177845.1 | chr9:35184390-35200291 |
| 21223 | Tgoln1 | NM_009443.3 | chr6:72608420-72617000 | 21320 | Tjap1 | NM_001252473.1 | chr17:46257850-46283026 |
| 21224 | Tgoln2 | NM_009444.1 | chr6:72615954-72616748 | 21321 | Tjp1 | NM_001163574.1 | chr7:65296164-65371244 |
| 21225 | Tgs1 | NM_054089.4 | chr4:3574878-3616623 | 21322 | Tjp2 | NM_001198985.1 | chr19:24094501-24174140 |
| 21226 | Tgtp1 | NM_011579.3 | chr11:48985328-48992246 | 21323 | Tjp3 | NM_001282095.1 | chr10:81273187-81291581 |
| 21227 | Tgtp2 | NM_001145164.1 | chr11:49057195-49064213 | 21324 | Tk1 | NM_001271729.1 | chr11:117815518-117826014 |
| 21228 | Th | NM_009377.1 | chr7:142892775-142899966 | 21325 | Tk2 | NM_021028.3 | chr8:104226690-104248558 |
| 21229 | Tha1 | NM_027919.4 | chr11:117867948-117873526 | 21326 | Tkt | NM_009388.6 | chr14:30549130-30574726 |
| 21230 | Thada | NM_184190055-84466208 | chr11:84190055-84466208 | 21327 | Tktl1 | NM_031379.2 | chrX:74177258-74208498 |
| 21231 | Thap1 | NM_199042.2 | chr8:26158168-26164151 | 21328 | Tktl2 | NM_001271574.1 | chr8:66517139-66519199 |
| 21232 | Thap11 | NM_001215.3 | chr8:105855102-105856950 | 21329 | Tlcd1 | NM_001271235.1 | chr11:78178148-78186819 |
| 21233 | Thap2 | NM_025780.3 | chr10:115369985-115384435 | 21330 | Tlcd2 | NM_001291156.1 | chr11:75468049-75470899 |
| 21234 | Thap3 | NM_001145929.1 | chr4:151982637-151988986 | 21331 | Tldc1 | NM_028883.2 | chr8:119760586-119778416 |
| 21235 | Thap4 | NM_025920.3 | chr1:93765390-93754838 | 21332 | Tldc2 | NM_001177439.1 | chr2:157087054-157096481 |
| 21236 | Thap6 | NR_028429.1 | chr5:91862881-91972137 | 21333 | Tle1 | NM_001285929.1 | chr4:72109944-72200893 |
| 21237 | Thap7 | NM_026909.2 | chr16:17527981-17531052 | 21334 | Tle2 | NM_001252401.1 | chr10:81575286-81590473 |
| 21238 | Thbd | NM_009378.3 | chr2:148408470-148408188 | 21335 | Tle3 | NM_001083927.1 | chr9:85372365-61418497 |
| 21239 | Thbs1 | NM_011580.4 | chr2:118111875-118127133 | 21336 | Tle4 | NM_011600.3 | chr19:14448071-14598183 |
| 21240 | Thbs2 | NM_011581.3 | chr17:14665499-14694262 | 21337 | Tle6 | NM_053254.2 | chr10:81590904-81600900 |
| 21241 | Thbs3 | NM_013691.2 | chr3:89215186-89226837 | 21338 | Tlk1 | NM_172664.3 | chr2:70712407-70825480 |
| 21242 | Thbs4 | NM_011582.3 | chr13:92751585-92794818 | 21339 | Tlk2 | NM_001112705.2 | chr11:105181526-105283959 |

Fig.21 - 111

| | | | | | | | | |
|---|---|---|---|---|---|---|---|---|
| 21340 | Tlr1 | NM_099390.2 | chr8:64014769-64205993 | | 21437 | Tmem129 | NM_026698.2 | chr5:33653215-33657832 |
| 21341 | Tlr2 | NM_011904.3 | chr19:41083980-41206774 | | 21438 | Tmem130 | NM_177735.4 | chr5:144735914-144761578 |
| 21342 | Tln1 | NM_011602.5 | chr4:43531512-43562583 | | 21439 | Tmem131 | NM_018872.2 | chr1:36792188-36939527 |
| 21343 | Tln2 | NM_001081242.2 | chr9:67217084-67559703 | | 21440 | Tmem132a | NM_133804.2 | chr19:10857828-10869779 |
| 21344 | Tlr1 | NM_001276445.1 | chr5:649246.79-64933558 | | 21441 | Tmem132b | NM_001190352.1 | chr5:125532417-125792583 |
| 21345 | Tlr11 | NM_205819.3 | chr14:50357913-50363663 | | 21442 | Tmem132c | NM_175432.3 | chr5:127241825-127565790 |
| 21346 | Tlr12 | NM_205823.2 | chr4:128615445-128618619 | | 21443 | Tmem132cos | NR_038127.1 | chr5:127256859-127281623 |
| 21347 | Tlr13 | NM_205820.1 | chrX:106143274-106160493 | | 21444 | Tmem132d | NM_172885.2 | chr5:127783490-128433077 |
| 21348 | Tlr2 | NM_011905.3 | chr3:83836271-83841608 | | 21445 | Tmem132e | NM_001304439.1 | chr11:82387446-82447618 |
| 21349 | Tlr3 | NM_126166.4 | chr8:45395664-45410539 | | 21446 | Tmem134 | NM_001078649.1 | chr19:4125959-4132307 |
| 21350 | Tlr4 | NM_021297.3 | chr4:66827550-66846681 | | 21447 | Tmem135 | NM_028343.4 | chr7:89139720-89338787 |
| 21351 | Tlr5 | NM_016928.3 | chr1:182954787-182976044 | | 21448 | Tmem136 | NM_001034861.3 | chr9:43108652-43116570 |
| 21352 | Tlr6 | NM_011604.3 | chr5:64953094-64960034 | | 21449 | Tmem138 | NM_028411.4 | chr19:10570477-10577386 |
| 21353 | Tlr7 | NM_001290755.1 | chrX:167304925-167330571 | | 21450 | Tmem139 | NM_175408.4 | chr6:42261969-42264555 |
| 21354 | Tlr8 | NM_133212.3 | chrX:167241122-167264329 | | 21451 | Tmem140 | NM_197986.2 | chr6:34863145-34874946 |
| 21355 | Tlr9 | NM_031178.2 | chr9:106222597-106226876 | | 21452 | Tmem141 | NM_001040130.3 | chr2:25620065-25622002 |
| 21356 | Tlx1 | NM_021901.3 | chr19:45136714-45156943 | | 21453 | Tmem143 | NM_144801.2 | chr7:45897068-45917413 |
| 21357 | Tlx2 | NM_009392.2 | chr6:83068324-83070225 | | 21454 | Tmem144 | NM_027495.4 | chr3:79813152-79842662 |
| 21358 | Tlx3 | NM_019916.2 | chr11:33200751-33203588 | | 21455 | Tmem145 | NM_183311.2 | chr7:25306107-25316195 |
| 21359 | Tm2d1 | NM_053157.2 | chr4:98355369-98383265 | | 21456 | Tmem147 | NM_027215.2 | chr7:30727700-30729534 |
| 21360 | Tm2d2 | NM_027194.3 | chr8:25017210-25023280 | | 21457 | Tmem14a | NM_001290679.1 | chr1:21218574-21230167 |
| 21361 | Tm2d3 | NM_026795.3 | chr7:65693416-65701913 | | 21458 | Tmem14c | NM_025387.3 | chr13:41016249-41022582 |
| 21362 | Tm4sf1 | NM_008536.3 | chr3:57287063-57301919 | | 21459 | Tmem150a | NM_144916.3 | chr6:72355482-72359762 |
| 21363 | Tm4sf19 | NM_001160402.1 | chr16:32400505-32408227 | | 21460 | Tmem150b | NM_001142792.1 | chr7:4716001-4725082 |
| 21364 | Tm4sf20 | NM_025453.3 | chr1:82756648-82768456 | | 21461 | Tmem150c | NM_182841.1 | chr5:100077872-100159808 |
| 21365 | Tm4sf4 | NM_145539.2 | chr3:57425409-57441675 | | 21462 | Tmem150cos | NR_045993.1 | chr5:100077961-100095273 |
| 21366 | Tm4sf5 | NM_029360.3 | chr11:70505273-70511183 | | 21463 | Tmem151a | NM_001001885.1 | chr19:5079336-5085477 |
| 21367 | Tm6sf1 | NM_001291282.1 | chr7:81862686-81884079 | | 21464 | Tmem151b | NM_001013749.2 | chr17:45541939-45549677 |
| 21368 | Tm6sf2 | NM_181540.4 | chr8:70072923-70080066 | | 21465 | Tmem154 | NM_177260.2 | chr3:84666191-84704575 |
| 21369 | Tm7sf1 | NM_028454.2 | chr19:6062820-6067850 | | 21466 | Tmem158 | NM_001002267.2 | chr9:123259956-123260789 |
| 21370 | Tm7sf3 | NM_026284.2 | chr6:146602275-146634692 | | 21467 | Tmem159 | NM_145586.1 | chr7:120102425-120120986 |
| 21371 | Tm9sf1 | NM_028780.3 | chr14:55635965-55643806 | | 21468 | Tmem160 | NM_026938.1 | chr7:16452778-16455490 |
| 21372 | Tm9sf2 | NM_080556.3 | chr14:122107081-122159603 | | 21469 | Tmem161a | NM_145597.4 | chr8:70172407-70183681 |
| 21373 | Tm9sf3 | NM_133352.2 | chr19:41210841-41264004 | | 21470 | Tmem161b | NM_175187.5 | chr13:84222295-84295966 |
| 21374 | Tm9sf4 | NM_133847.3 | chr2:153161300-153210463 | | 21471 | Tmem163 | NM_028136.2 | chr1:127490341-127678021 |
| 21375 | Tma16 | NM_025465.2 | chr8:66476346-66486507 | | 21472 | Tmem164 | NM_001199357.1 | chrX:142681399-142843494 |
| 21376 | Tma7 | NM_183250.2 | chr9:109077987-109082381 | | 21473 | Tmem165 | NM_011626.2 | chr5:76183879-76209244 |
| 21377 | Tmbim1 | NM_027154.5 | chr1:74288246-74304336 | | 21474 | Tmem167 | NM_025335.3 | chr13:90089666-90114921 |
| 21378 | Tmbim4 | NM_026617.3 | chr10:120208825-120224897 | | 21475 | Tmem167b | NM_026198.2 | chr3:108556424-108562486 |
| 21379 | Tmbim6 | NM_001171034.1 | chr15:99392946-99410049 | | 21476 | Tmem168 | NM_028990.4 | chr6:13580688-13608063 |
| 21380 | Tmbim7 | NM_029141.4 | chr5:3657003-3679544 | | 21477 | Tmem169 | NM_175564.4 | chr1:72284372-72362995 |
| 21381 | Tmc1 | NM_028853.2 | chr19:20783457-20954202 | | 21478 | Tmem17 | NM_153596.3 | chr1:22512282-22519233 |
| 21382 | Tmc2 | NM_138655.1 | chr2:130195193-130264445 | | 21479 | Tmem170 | NM_025781.2 | chr8:111864897-111876675 |
| 21383 | Tmc3 | NM_177695.4 | chr7:83584930-83623709 | | 21480 | Tmem170b | NM_001163572.1 | chr13:41606215-41641357 |
| 21384 | Tmc4 | NM_181820.2 | chr7:3665753-3677553 | | 21481 | Tmem171 | NM_001025606.1 | chr13:98686237-98694831 |
| 21385 | Tmc5 | NM_001105252.1 | chr7:118597296-118675085 | | 21482 | Tmem173 | NM_001289591.1 | chr18:35733677-35740654 |
| 21386 | Tmc6 | NM_145439.2 | chr11:117765984-117780683 | | 21483 | Tmem174 | NM_026685.2 | chr13:98634977-98637410 |
| 21387 | Tmc7 | NM_172476.4 | chr7:118535843-118584686 | | 21484 | Tmem175 | NM_001163531.1 | chr5:108629809-108647770 |
| 21388 | Tmc8 | NM_001195088.1 | chr11:117782657-117793137 | | 21485 | Tmem176a | NM_001098273.1 | chr6:48841655-48845364 |
| 21389 | Tmcc1 | NM_177412.1 | chr6:116018617-116193374 | | 21486 | Tmem176b | NM_001164207.1 | chr6:48833811-48841374 |
| 21390 | Tmcc2 | NM_178874.3 | chr1:132356314-132391386 | | 21487 | Tmem177 | NM_175106.3 | chr1:119907898-119913168 |
| 21391 | Tmcc3 | NM_001168684.1 | chr10:94575256-94590954 | | 21488 | Tmem178 | NM_026516.2 | chr17:80944631-81001816 |
| 21392 | Tmco1 | NM_001039483.1 | chr1:167308669-167333978 | | 21489 | Tmem178b | NM_001004182.3 | chr6:40110252-40248353 |
| 21393 | Tmco2 | NM_001081312.1 | chr4:121105650-121109226 | | 21490 | Tmem179 | NM_178915.3 | chr12:112500183-112511160 |
| 21394 | Tmco3 | NM_172724.2 | chr8:13320818-13322924 | | 21491 | Tmem179b | NM_026325.3 | chr19:8772521-8774467 |
| 21395 | Tmco4 | NM_029857.3 | chr4:138972904-139059171 | | 21492 | Tmem18 | NM_172049.2 | chr12:30584442-30591219 |
| 21396 | Tmco5 | NM_026104.4 | chr2:116878690-116892500 | | 21493 | Tmem180 | NM_029186.2 | chr19:48356879-46375254 |
| 21397 | Tmco5b | NM_029232.2 | chr2:113285731-113297190 | | 21494 | Tmem181a | NM_001033178.3 | chr17:6270469-6308314 |
| 21398 | Tmco6 | NM_028036.3 | chr18:36735089-36742391 | | 21495 | Tmem181b-ps | NR_033520.1 | chr17:6439001-6450994 |
| 21399 | Tmed1 | NM_019744.3 | chr9:21507379-21510186 | | 21496 | Tmem181c-ps | NR_028305.2 | chr17:6610102-6620925 |
| 21400 | Tmed10 | NM_026775.4 | chr12:85340613-85347717 | | 21497 | Tmem182 | NM_001081198.1 | chr1:40805600-40855267 |
| 21401 | Tmed11 | NM_026109.2 | chr5:108777234-108795363 | | 21498 | Tmem183a | NM_001042425.1 | chr1:134346096-134361999 |
| 21402 | Tmed2 | NM_019770.2 | chr5:124540790-124550503 | | 21499 | Tmem184a | NM_001161548.1 | chr5:139804951-139814283 |
| 21403 | Tmed3 | NM_025360.2 | chr9:89689202-89705043 | | 21500 | Tmem184b | NM_001253817.1 | chr15:79360683-79402919 |
| 21404 | Tmed4 | NM_134020.1 | chr11:6270713-6274837 | | 21501 | Tmem184c | NM_145599.4 | chr8:77959577-77610653 |
| 21405 | Tmed5 | NM_028876.2 | chr5:108121646-108132591 | | 21502 | Tmem185b | NM_146103.2 | chr1:119526153-119528983 |
| 21406 | Tmed6 | NM_025458.2 | chr8:107061483-107065644 | | 21503 | Tmem186 | NM_025708.4 | chr16:8633730-8637701 |
| 21407 | Tmed7 | NM_025698.1 | chr18:46585927-46597535 | | 21504 | Tmem189 | NM_145538.2 | chr2:167643224-167661544 |
| 21408 | Tmed8 | NM_001033475.3 | chr12:87166241-87200229 | | 21505 | Tmem19 | NM_133683.3 | chr10:115340739-115362262 |
| 21409 | Tmed9 | NM_026211.3 | chr13:55593134-55597694 | | 21506 | Tmem190 | NM_030028.1 | chr7:4782939-4784340 |
| 21410 | Tmeff1 | NM_021438.2 | chr4:48585192-48663131 | | 21507 | Tmem191c | NM_177473.3 | chr16:17276299-17278651 |
| 21411 | Tmeff2 | NM_019790.4 | chr1:50927522-51187270 | | 21508 | Tmem192 | NM_001163747.1 | chr8:64947184-64969037 |
| 21412 | Tmem100 | NM_026433.2 | chr11:90080347-90086505 | | 21509 | Tmem194 | NM_001113211.1 | chr10:127677064-127701047 |
| 21413 | Tmem101 | NM_001030483.4 | chr11:102152546-102156405 | | 21510 | Tmem194b | NM_142647.1 | chr1:52630704-52651919 |
| 21414 | Tmem102 | NM_001034483.4 | chr11:69803594-69805624 | | 21511 | Tmem196 | NM_001160385.2 | chr12:119945961-120021245 |
| 21415 | Tmem104 | NM_001033393.2 | chr11:115187486-115247025 | | 21512 | Tmem198 | NM_177056.4 | chr1:75479531-75485693 |
| 21416 | Tmem106a | NM_144830.3 | chr11:101582241-101591785 | | 21513 | Tmem198b | NM_178066.2 | chr10:128800035-128804370 |
| 21417 | Tmem106b | NM_027992.3 | chr6:13069758-13089269 | | 21514 | Tmem199 | NM_199199.3 | chr19:7850705-78512168 |
| 21418 | Tmem106c | NM_001252153.1 | chr15:97964228-97970286 | | 21515 | Tmem2 | NM_001033759.2 | chr19:21778339-21858360 |
| 21419 | Tmem107 | NM_025838.2 | chr11:69070808-69073293 | | 21516 | Tmem200a | NM_029881.3 | chr10:25991185-26079052 |
| 21420 | Tmem108 | NM_178638.4 | chr9:103482935-103761837 | | 21517 | Tmem200b | NM_001201367.1 | chr4:131921770-131923140 |
| 21421 | Tmem109 | NM_134142.1 | chr19:10870660-10881743 | | 21518 | Tmem200c | NM_001206661.1 | chr17:68837135-68843138 |
| 21422 | Tmem11 | NM_001168507.1 | chr11:60864451-60879038 | | 21519 | Tmem201 | NM_001284270.1 | chr4:149715374-149738068 |
| 21423 | Tmem110 | NM_028839.4 | chr14:30825593-30877210 | | 21520 | Tmem202 | NM_178368.2 | chr9:59518684-59525501 |
| 21424 | Tmem115 | NM_019790.4 | chr9:107533944-107538086 | | 21521 | Tmem203 | NM_177344.3 | chr2:25255438-25256352 |
| 21425 | Tmem116 | NM_001161626.1 | chr11:121483180-121495421 | | 21522 | Tmem204 | NM_001001183.1 | chr17:25057701-25081114 |
| 21426 | Tmem117 | NM_178789.4 | chr15:94618480-95098097 | | 21523 | Tmem205 | NM_001253867.1 | chr9:21921005-21927535 |
| 21427 | Tmem119 | NM_146162.2 | chr5:113793728-113800352 | | 21524 | Tmem206 | NM_025864.3 | chr1:191325964-191352925 |
| 21428 | Tmem120a | NM_172541.2 | chr5:135735489-135744172 | | 21525 | Tmem207 | NM_001101640.1 | chr16:26503792-26526771 |
| 21429 | Tmem120b | NM_001039723.2 | chr5:123076274-123117445 | | 21526 | Tmem208 | NM_025486.2 | chr8:105326363-105329057 |
| 21430 | Tmem121 | NM_153776.2 | chr12:113185902-113189522 | | 21527 | Tmem209 | NM_178625.4 | chr6:30481232-30509783 |
| 21431 | Tmem123 | NM_133739.2 | chr9:7764076-7794332 | | 21528 | Tmem210 | NM_030055.1 | chr2:25288144-25289187 |
| 21432 | Tmem125 | NM_172383.3 | chr4:118540940-118543726 | | 21529 | Tmem211 | NM_001033428.2 | chr5:113226908-113239263 |
| 21433 | Tmem126a | NM_025460.2 | chr7:90450711-90457208 | | 21530 | Tmem212 | NM_001164437.1 | chr3:27866664-27898368 |
| 21434 | Tmem126b | NM_026734.1 | chr7:90468828-90475995 | | 21531 | Tmem213 | NM_029921.1 | chr6:38109352-38115806 |
| 21435 | Tmem127 | NM_175145.3 | chr2:127247974-127260764 | | 21532 | Tmem214 | NM_144525.3 | chr5:30869646-30877467 |
| 21436 | Tmem128 | NM_025480.3 | chr5:38260374-38269618 | | 21533 | Tmem215 | NM_001166009.1 | chr4:40473129-40475653 |

Fig.21 - 112

| | | | | | | | | |
|---|---|---|---|---|---|---|---|---|
| 21534 | Tmem216 | NM_001277860.1 | chr19:10550460-10555763 | | 21631 | Tmem74b | NM_001160363.1 | chr2:151702007-151707310 |
| 21535 | Tmem217 | NM_001162901.1 | chr17:29526017-29549593 | | 21632 | Tmem79 | NM_024246.5 | chr3:88328652-88334433 |
| 21536 | Tmem218 | NM_025464.3 | chr9:37208222-37223228 | | 21633 | Tmem8 | NM_027193.2 | chr17:26113315-26123253 |
| 21537 | Tmem219 | NM_026827.1 | chr7:126886218-126896278 | | 21634 | Tmem80 | NM_001141950.1 | chr7:141328129-141337155 |
| 21538 | Tmem220 | NM_001291042.1 | chr11:67025153-67035312 | | 21635 | Tmem81 | NM_029025.3 | chr1:132506229-132508639 |
| 21539 | Tmem221 | NM_001100462.1 | chr8:71554302-71558871 | | 21636 | Tmem82 | NM_145987.2 | chr4:141614232-141618633 |
| 21540 | Tmem222 | NM_025667.3 | chr4:133266044-133277790 | | 21637 | Tmem86a | NM_026436.3 | chr7:47050639-47054776 |
| 21541 | Tmem223 | NM_025791.3 | chr19:8776995-8772475 | | 21638 | Tmem86b | NM_023440.2 | chr7:4628039-4630482 |
| 21542 | Tmem225 | NM_029379.1 | chr9:40148121-40150878 | | 21639 | Tmem87a | NM_001110496.1 | chr2:120355308-120404116 |
| 21543 | Tmem229a | NM_177013.3 | chr6:24951140-24956125 | | 21640 | Tmem87b | NM_028248.2 | chr2:128818302-128854261 |
| 21544 | Tmem229b | NM_001170401.1 | chr12:78961794-78983478 | | 21641 | Tmem88 | NM_025915.4 | chr11:69396515-69398234 |
| 21545 | Tmem230 | NM_001141971.1 | chr2:132239491-132247788 | | 21642 | Tmem88b | NM_001033394.3 | chr4:155781590-155785874 |
| 21546 | Tmem231 | NM_001033321.1 | chr8:111912017-111933791 | | 21643 | Tmem89 | NM_027066.1 | chr9:108914618-108915563 |
| 21547 | Tmem232 | NM_001008973.2 | chr17:65256004-65340782 | | 21644 | Tmem8b | NM_001085508.2 | chr4:43668970-43692667 |
| 21548 | Tmem233 | NM_001101546.1 | chr5:116040533-116083246 | | 21645 | Tmem8c | NM_001159602.1 | chr2:27061635-27067868 |
| 21549 | Tmem234 | NM_025748.2 | chr4:129600706-129607879 | | 21646 | Tmem9 | NM_001160145.1 | chr1:136008218-136035030 |
| 21550 | Tmem235 | NM_001085535.1 | chr11:117860751-117865543 | | 21647 | Tmem91 | NM_001290497.1 | chr7:25669139-25675166 |
| 21551 | Tmem236 | NM_001081310.2 | chr2:14174523-14221993 | | 21648 | Tmem92 | NM_001034896.2 | chr11:94777216-94782703 |
| 21552 | Tmem237 | NM_001033449.1 | chr1:59100592-59120096 | | 21649 | Tmem95 | NM_001195710.1 | chr11:69876683-69878018 |
| 21553 | Tmem238 | NM_029384.1 | chr7:4784784-4789560 | | 21650 | Tmem97 | NM_133706.2 | chr11:78541816-78550735 |
| 21554 | Tmem239 | NM_025753.3 | chr2:130406521-130407794 | | 21651 | Tmem98 | NM_029537.1 | chr11:80810414-80822033 |
| 21555 | Tmem240 | NM_001101506.1 | chr4:155734803-155740564 | | 21652 | Tmem9b | NM_020050.1 | chr7:109735835-109752263 |
| 21556 | Tmem241 | NM_001289666.1 | chr18:11981302-12121537 | | 21653 | Tmevpg1 | NR_104123.1 | chr10:118602034-118656625 |
| 21557 | Tmem242 | NM_027457.4 | chr17:5410863-5440260 | | 21654 | Tmf1 | NM_001081111.2 | chr6:97151949-97179124 |
| 21558 | Tmem243 | NM_001081029.1 | chr5:9100736-9118983 | | 21655 | Tmie | NM_146260.2 | chr9:110866045-110880083 |
| 21559 | Tmem245 | NM_175518.5 | chr4:56876012-56947429 | | 21656 | Tmigd1 | NM_025655.2 | chr11:76904544-76916586 |
| 21560 | Tmem246 | NM_025944.3 | chr4:49584505-49597870 | | 21657 | Tmlhe | NM_138758.1 | chrX_GL456233_random:15964 6-334187 |
| 21561 | Tmem247 | NM_001277980.1 | chr17:86917347-86922367 | | 21658 | Tmod1 | NM_021883.2 | chr4:46039221-46116032 |
| 21562 | Tmem248 | NM_001081394.1 | chr5:130219743-130243765 | | 21659 | Tmod2 | NM_001038710.1 | chr9:75565821-75599133 |
| 21563 | Tmem25 | NM_027865.2 | chr9:44793778-44799216 | | 21660 | Tmod3 | NM_016963.2 | chr9:75497783-75559657 |
| 21564 | Tmem251 | NM_177140.3 | chr12:102743759-102745397 | | 21661 | Tmod4 | NM_016712.3 | chr3:95124513-95129208 |
| 21565 | Tmem252 | NM_183160.3 | chr19:24874007-24879661 | | 21662 | Tmpo | NM_001080129.2 | chr10:91147570-91171619 |
| 21566 | Tmem253 | NM_001033805.3 | chr14:52016864-52019787 | | 21663 | Tmppe | NM_001200002.1 | chr9:114401094-114411201 |
| 21567 | Tmem254a | NM_025311.3 | chr14:25923297-26206619 | | 21664 | Tmprss11a | NM_001033233.2 | chr5:86410409-86468990 |
| 21568 | Tmem254b | NM_001270495.1 | chr14:25923996-26207025 | | 21665 | Tmprss11bnl | NM_177024.4 | chr5:86659521-86676298 |
| 21569 | Tmem254c | NM_001270498.1 | chr14:25923997-26207041 | | 21666 | Tmprss11c | NM_001080297.2 | chr5:86231480-86289308 |
| 21570 | Tmem255a | NM_001289727.1 | chrX:38196572-38252481 | | 21667 | Tmprss11d | NM_145561.2 | chr5:86302853-86373387 |
| 21571 | Tmem255b | NM_001143671.1 | chr8:13435458-13461451 | | 21668 | Tmprss11e | NM_172880.2 | chr5:86705185-86745807 |
| 21572 | Tmem256 | NM_026982.1 | chr11:69838524-69839558 | | 21669 | Tmprss11f | NM_178730.3 | chr5:86521225-86632424 |
| 21573 | Tmem258 | NM_001163431.1 | chr19:10206032-10207824 | | 21670 | Tmprss11g | NM_177162.4 | chr5:86485876-86518600 |
| 21574 | Tmem259 | NM_001003949.3 | chr10:79977119-79984330 | | 21671 | Tmprss12 | NM_183109.3 | chr15:100280836-100293053 |
| 21575 | Tmem26 | NM_177794.3 | chr10:68723745-68782654 | | 21672 | Tmprss13 | NM_001013673.2 | chr9:45319099-45347580 |
| 21576 | Tmem260 | NM_172600.4 | chr14:48446351-48515130 | | 21673 | Tmprss15 | NM_008941.3 | chr16:78953007-79091097 |
| 21577 | Tmem261 | NM_025849.3 | chr4:75277353-75278286 | | 21674 | Tmprss2 | NM_015775.2 | chr16:97564681-97611195 |
| 21578 | Tmem263 | NM_001013028.2 | chr10:85102626-85117747 | | 21675 | Tmprss3 | NM_001163776.1 | chr17:31179267-31198974 |
| 21579 | Tmem27 | NM_020626.2 | chrX:164090186-164118859 | | 21676 | Tmprss4 | NM_145403.2 | chr9:45172725-45204075 |
| 21580 | Tmem28 | NM_001081283.1 | chrX:98821068-99846345 | | 21677 | Tmprss5 | NM_030709.2 | chr9:49102778-49117587 |
| 21581 | Tmem29 | NM_001164683.1 | chrX:150397772-150459150 | | 21678 | Tmprss6 | NM_027902.2 | chr15:78439666-78468634 |
| 21582 | Tmem30a | NM_133718.4 | chr9:79768940-79793430 | | 21679 | Tmprss7 | NM_172455.3 | chr16:45658316-45693658 |
| 21583 | Tmem30b | NM_178715.3 | chr12:73543113-73546395 | | 21680 | Tmprss9 | NM_001081688.2 | chr10:80878815-80899494 |
| 21584 | Tmem30c | NM_027651.1 | chr16:57266138-57292851 | | 21681 | Tmsb10 | NM_001039392.2 | chr6:72957346-72958232 |
| 21585 | Tmem33 | NM_001285452.1 | chr5:67260564-67291461 | | 21682 | Tmsb15a | NM_030106.2 | chrX:135718666-135720673 |
| 21586 | Tmem35 | NM_026239.2 | chrX:134295224-134305969 | | 21683 | Tmsb15b1 | NM_001081883.1 | chrX:136974021-136976874 |
| 21587 | Tmem37 | NM_019432.2 | chr1:120067376-120073780 | | 21684 | Tmsb15b2 | NM_001080967.4 | chrX:136954987-136957979 |
| 21588 | Tmem38a | NM_145544.4 | chr8:72572102-72587284 | | 21685 | Tmsb15l | NM_267267.4 | chrX:136954987-136976874 |
| 21589 | Tmem38b | NM_028053.2 | chr4:53826044-53862018 | | 21686 | Tmsb4x | NM_021278.2 | chrX:167207093-167209218 |
| 21590 | Tmem39a | NM_001205286.1 | chr16:38558697-38592162 | | 21687 | Tmtc1 | NM_198967.5 | chr6:148232429-148444352 |
| 21591 | Tmem39b | NM_199305.1 | chr4:129676354-129696838 | | 21688 | Tmtc2 | NM_177368.4 | chr10:105187663-105574479 |
| 21592 | Tmem40 | NM_001168256.1 | chr6:115729136-115762466 | | 21689 | Tmtc3 | NM_001033332.2 | chr10:100448183-100487347 |
| 21593 | Tmem41a | NM_025693.4 | chr16:21934326-21947552 | | 21690 | Tmtc4 | NM_028651.2 | chr14:122918974-122983261 |
| 21594 | Tmem41b | NM_153525.5 | chr7:109972186-109986230 | | 21691 | Tmub1 | NM_022418.3 | chr5:24445462-24447846 |
| 21595 | Tmem42 | NM_001164823.1 | chr9:123021325-123023491 | | 21692 | Tmub2 | NM_028076.3 | chr11:102284938-102289427 |
| 21596 | Tmem43 | NM_028766.2 | chr6:91473750-91488458 | | 21693 | Tmx1 | NM_028339.1 | chr12:70453153-70467624 |
| 21597 | Tmem44 | NM_172464.3 | chr16:30511854-30550578 | | 21694 | Tmx2 | NM_001290751.1 | chr2:84671310-84678174 |
| 21598 | Tmem45a | NM_019631.3 | chr16:56805160-56886163 | | 21695 | Tmx3 | NM_198295.2 | chr18:90510159-90543267 |
| 21599 | Tmem45b | NM_144936.1 | chr9:31426195-31464238 | | 21696 | Tmx4 | NM_029148.1 | chr2:134544501-134644121 |
| 21600 | Tmem47 | NM_138751.2 | chrX:81070643-81097875 | | 21697 | Tnc | NM_011607.3 | chr4:63959784-64047015 |
| 21601 | Tmem5 | NM_153069.1259-122097102 | chr10:122081259-122097102 | | 21698 | Tnf | NM_001278601.1 | chr17:35199366-35202007 |
| 21602 | Tmem50a | NM_027935.2 | chr4:134897848-134914916 | | 21699 | Tnfaip1 | NM_001159392.1 | chr11:78522849-78536260 |
| 21603 | Tmem50b | NM_030308.3 | chr16:91574507-91597680 | | 21700 | Tnfaip2 | NM_009396.2 | chr12:111442660-111455018 |
| 21604 | Tmem51 | NM_145402.3 | chr4:142030992-142084304 | | 21701 | Tnfaip3 | NM_001166402.1 | chr10:19000909-19011963 |
| 21605 | Tmem51os1 | NR_027137.1 | chr4:142084297-142088101 | | 21702 | Tnfaip6 | NM_009398.2 | chr2:52038112-52056681 |
| 21606 | Tmem52 | NM_001253856.1 | chr4:155469113-155470858 | | 21703 | Tnfaip8 | NM_001177759.1 | chr18:49979426-50093229 |
| 21607 | Tmem52b | NM_001081186.1 | chr5:129512556-129519227 | | 21704 | Tnfaip8l1 | NM_025966.5 | chr17:56162490-56173955 |
| 21608 | Tmem53 | NM_001285812.1 | chr4:117251950-117266538 | | 21705 | Tnfaip8l2 | NM_027206.2 | chr3:95139520-95142360 |
| 21609 | Tmem54 | NM_001290706.1 | chr4:129105547-129111624 | | 21706 | Tnfaip8l3 | NM_001033535.3 | chr9:54025505-54068411 |
| 21610 | Tmem55a | NM_028264.4 | chr4:14864218-14915260 | | 21707 | Tnfrsf10b | NM_020275.4 | chr14:69767471-69784411 |
| 21611 | Tmem55b | NM_001033271.5 | chr14:50927214-50930849 | | 21708 | Tnfrsf11a | NM_009399.3 | chr1:105780722-105847981 |
| 21612 | Tmem56 | NM_178936.3 | chr3:121202009-121263316 | | 21709 | Tnfrsf11b | NM_008764.3 | chr15:54250618-54278484 |
| 21613 | Tmem57 | NM_025382.6 | chr4:134802759-134853345 | | 21710 | Tnfrsf12a | NM_001161746.1 | chr17:23675444-23677449 |
| 21614 | Tmem59 | NM_029565.3 | chr4:107178629-107200906 | | 21711 | Tnfrsf13b | NM_021349.1 | chr11:61140834-61147642 |
| 21615 | Tmem59l | NM_182991.2 | chr8:70433866-70487358 | | 21712 | Tnfrsf13c | NM_028075.2 | chr15:82221743-82224336 |
| 21616 | Tmem60 | NM_177601.3 | chr5:20882452-20886870 | | 21713 | Tnfrsf14 | NM_178931.2 | chr4:154922209-154928077 |
| 21617 | Tmem62 | NM_175285.3 | chr2:120977061-121007842 | | 21714 | Tnfrsf17 | NM_011608.1 | chr16:11313808-11320068 |
| 21618 | Tmem63a | NM_144794.2 | chr1:180942517-180975104 | | 21715 | Tnfrsf18 | NM_009400.2 | chr4:156026341-156028891 |
| 21619 | Tmem63b | NM_198167.3 | chr17:45660176-45686218 | | 21716 | Tnfrsf19 | NM_001164155.1 | chr14:60963833-61037987 |
| 21620 | Tmem63c | NM_172528.2 | chr12:87026563-87090039 | | 21717 | Tnfrsf1a | NM_011609.4 | chr6:125349722-125362483 |
| 21621 | Tmem64 | NM_181401.3 | chr4:15265819-15286753 | | 21718 | Tnfrsf1b | NM_011610.4 | chr4:145212367-145246870 |
| 21622 | Tmem65 | NM_175212.4 | chr15:58782268-58823427 | | 21719 | Tnfrsf21 | NM_178589.3 | chr17:43016554-43089188 |
| 21623 | Tmem66 | NM_026432.3 | chr8:34154562-34170847 | | 21720 | Tnfrsf22 | NM_023680.4 | chr7:143634807-143649664 |
| 21624 | Tmem67 | NM_177861.4 | chr4:12039355-12087957 | | 21721 | Tnfrsf23 | NM_024290.4 | chr7:143665806-143685875 |
| 21625 | Tmem68 | NM_028097.3 | chr4:3549040-3574768 | | 21722 | Tnfrsf25 | NM_001291010.1 | chr4:152119333-152126119 |
| 21626 | Tmem69 | NM_177870.4 | chr4:116551527-116555943 | | 21723 | Tnfrsf26 | NM_175649.5 | chr7:143607684-143627845 |
| 21627 | Tmem70 | NM_026392.1 | chr1:16590716-16676275 | | 21724 | Tnfrsf4 | NM_011659.2 | chr4:156013694-156016589 |
| 21628 | Tmem71 | NM_172514.3 | chr15:66526211-66561046 | | 21725 | Tnfrsf8 | NM_009401.2 | chr4:145268975-145315147 |
| 21629 | Tmem72 | NM_178768.4 | chr6:116692724-116716758 | | 21726 | Tnfrsf9 | NM_001077508.1 | chr4:150920154-150946102 |
| 21630 | Tmem74 | NM_175502.3 | chr15:43866694-43870029 | | 21727 | Tnfsf10 | NM_009425.2 | chr3:27317076-27339665 |

Fig.21 - 113

| | | | | | | | | |
|---|---|---|---|---|---|---|---|---|
| 21728 | Tnfsf11 | NM_011613.3 | chr14:78277449-78308043 | 21825 | Tpgs2 | NM_001004361.2 | chr18:25136039-25168877 |
| 21729 | Tnfsf12 | NM_011614.3 | chr11:69686239-69696098 | 21826 | Tph1 | NM_001136084.2 | chr7:46644640-46667377 |
| 21730 | Tnfsf12Tnfsf13 | NM_001034097.2 | chr11:69682576-69696098 | 21827 | Tph2 | NM_173391.3 | chr10:115078640-115185022 |
| 21731 | Tnfsf13 | NM_001159505.1 | chr11:69682576-69685554 | 21828 | Tpi1 | NM_009415.2 | chr6:124810591-124814296 |
| 21732 | Tnfsf13b | NM_033622.1 | chr8:10006632-10035999 | 21829 | Tpk1 | NM_013861.4 | chr6:43345000-43666278 |
| 21733 | Tnfsf14 | NM_019418.3 | chr17:57189473-57194181 | 21830 | Tpm1 | NM_001164248.1 | chr9:67027889-67049213 |
| 21734 | Tnfsf15 | NM_177371.3 | chr4:63724602-63745113 | 21831 | Tpm2 | NM_001277875.1 | chr4:43513725-43523554 |
| 21735 | Tnfsf18 | NM_183391.3 | chr1:161494656-161505290 | 21832 | Tpm3 | NM_001253738.1 | chr3:90079520-90100902 |
| 21736 | Tnfsf4 | NM_009452.2 | chr1:161395487-161418206 | 21833 | Tpm4 | NM_001001491.1 | chr8:72135291-72153129 |
| 21737 | Tnfsf8 | NM_009403.3 | chr4:63832823-63861284 | 21834 | Tpmt | NM_016785.2 | chr13:47023542-47043217 |
| 21738 | Tnfsf9 | NM_009404.3 | chr17:57105884-57107757 | 21835 | Tpo | NM_009417.3 | chr12:30054660-30132624 |
| 21739 | Tnik | NM_001163635.1 | chr3:28263213-28670585 | 21836 | Tpp1 | NM_009906.5 | chr7:105744846-105752207 |
| 21740 | Tnip1 | NM_001199275.2 | chr11:54910786-54962940 | 21837 | Tpp2 | NM_009418.3 | chr1:43923993-44003000 |
| 21741 | Tnip2 | NM_139064.2 | chr5:34496095-34513979 | 21838 | Tppp | NM_182839.2 | chr13:74009418-74035753 |
| 21742 | Tnip3 | NM_001001495.2 | chr6:65590397-65634040 | 21839 | Tppp2 | NM_001128634.1 | chr14:51918760-51920700 |
| 21743 | Tnk1 | NM_031880.3 | chr11:69850562-69858730 | 21840 | Tppp3 | NM_026481.3 | chr8:105467491-105471422 |
| 21744 | Tnk2 | NM_001110147.1 | chr16:32644642-32683493 | 21841 | Tpr | NM_133780.3 | chr1:150392837-150449935 |
| 21745 | Tnk2os | NR_033493.1 | chr16:32665222-32668197 | 21842 | Tpra1 | NM_011906.2 | chr6:88902250-88912740 |
| 21746 | Tnks | NM_175091.3 | chr8:34829178-34969690 | 21843 | Tprg | NM_175165.3 | chr16:25286818-25422344 |
| 21747 | Tnks1bp1 | NM_001081260.2 | chr2:85050459-85073048 | 21844 | Tprgl | NM_026388.2 | chr4:154157484-154160684 |
| 21748 | Tnks2 | NM_001163635.1 | chr19:36834231-36893477 | 21845 | Tprkb | NM_001170488.1 | chr6:85915718-85930284 |
| 21749 | Tnmd | NM_022322.2 | chrX:133851007-133865578 | 21846 | Tprn | NM_175286.4 | chr2:25262597-25269886 |
| 21750 | Tnn | NM_177839.3 | chr1:160085031-160153575 | 21847 | Tpsab1 | NM_031187.4 | chr17:25343244-25345562 |
| 21751 | Tnnc1 | NM_009393.2 | chr14:31208313-31211711 | 21848 | Tpsb2 | NM_010781.3 | chr17:25366332-25368092 |
| 21752 | Tnnc2 | NM_009394.2 | chr2:164777161-164779734 | 21849 | Tpsg1 | NM_012034.3 | chr17:25370552-25374442 |
| 21753 | Tnni1 | NM_001112702.1 | chr11:135795510-135810989 | 21850 | Tpst1 | NM_001130476.2 | chr5:130079369-130135733 |
| 21754 | Tnni2 | NM_009405.4 | chr7:142442467-142444405 | 21851 | Tpst2 | NM_009419.3 | chr5:112276706-112315356 |
| 21755 | Tnni3 | NM_009406.3 | chr7:4518307-4522443 | 21852 | Tpt1 | NM_009429.3 | chr14:75845255-75848303 |
| 21756 | Tnni3k | NM_177066.5 | chr3:154786290-155055407 | 21853 | Tpte | NM_199257.2 | chr8:22283440-22371418 |
| 21757 | Tnnt1 | NM_001277903.1 | chr7:4504569-4515975 | 21854 | Tpx2 | NM_001141975.1 | chr2:152847963-152885321 |
| 21758 | Tnnt2 | NM_001130174.2 | chr1:135836433-135852268 | 21855 | Tra2a | NM_198102.2 | chr6:49243920-49264052 |
| 21759 | Tnnt3 | NM_001163664.1 | chr7:142498835-142516009 | 21856 | Tra2b | NM_009186.4 | chr16:22245740-22265929 |
| 21760 | Tnp1 | NM_009407.2 | chr1:73015074-73015899 | 21857 | Trabd | NM_026485.2 | chr15:89076063-89087075 |
| 21761 | Tnp2 | NM_013694.4 | chr16:10793674-10788655 | 21858 | Trabd2b | NM_001085549.1 | chr4:114406723-114615098 |
| 21762 | Tnpo1 | NM_001048267.1 | chr13:98842080-98891042 | 21859 | Tradd | NM_001033161.2 | chr8:105258574-105264594 |
| 21763 | Tnpo2 | NM_001122843.1 | chr8:85037167-85057582 | 21860 | Traf1 | NM_009421.3 | chr2:34943257-34961772 |
| 21764 | Tnpo3 | NM_177296.4 | chr6:29040826-29609607 | 21861 | Traf2 | NM_001290413.1 | chr2:25517981-25546940 |
| 21765 | Tnr | NM_022312.3 | chr1:159523768-159924922 | 21862 | Traf3 | NM_001286122.1 | chr12:111166369-111267155 |
| 21766 | Tnrc18 | NM_001122730.2 | chr5:142724604-142817387 | 21863 | Traf3ip1 | NM_028718.2 | chr1:91494667-91529307 |
| 21767 | Tnrc6a | NM_144925.3 | chr7:123123884-123195296 | 21864 | Traf3ip2 | NM_134000.3 | chr10:39612933-39655307 |
| 21768 | Tnrc6b | NM_144812.2 | chr15:80711312-80941086 | 21865 | Traf3ip3 | NM_153137.4 | chr1:193175903-193201546 |
| 21769 | Tnrc6c | NM_198022.2 | chr11:117654288-117763441 | 21866 | Traf4 | NM_009423.4 | chr11:78158412-78165550 |
| 21770 | Tns1 | NM_001289895.1 | chr1:73910230-74124449 | 21867 | Traf5 | NM_011633.2 | chr1:191997202-192092599 |
| 21771 | Tns3 | NM_001083587.1 | chr11:8431651-8664535 | 21868 | Traf6 | NM_009424.3 | chr2:101678419-101701668 |
| 21772 | Tns4 | NM_172654.3 | chr11:99065677-99089306 | 21869 | Traf7 | NM_001172113.1 | chr17:24508849-24527938 |
| 21773 | Tnxb | NM_031176.2 | chr17:34670534-34719815 | 21870 | Trafd1 | NM_001163470.1 | chr5:121371724-121385615 |
| 21774 | Tob1 | NM_009427.2 | chr11:94211453-94215492 | 21871 | Traip | NM_011634.3 | chr9:107950962-107972268 |
| 21775 | Tob2 | NM_020507.3 | chr15:81848269-81858326 | 21872 | Trak1 | NM_175114.3 | chr9:121366957-121474918 |
| 21776 | Toe1 | NM_026654.2 | chr4:116804002-116807559 | 21873 | Trak2 | NM_172406.3 | chr1:58900449-58974482 |
| 21777 | Tollip | NM_023764.3 | chr7:141885684-141902406 | 21874 | Tram1 | NM_028173.5 | chr1:13564692-13589810 |
| 21778 | Tom1 | NM_001136259.1 | chr8:75033685-75070121 | 21875 | Tram1l1 | NM_146140.3 | chr3:124321036-124323260 |
| 21779 | Tom1l2 | NM_028011.2 | chr11:90645690-90687601 | 21876 | Tram2 | NM_177409.3 | chr1:21001336-21079225 |
| 21780 | Tomm20 | NM_001039092.3 | chr11:60226713-60352905 | 21877 | Trank1 | NM_001164659.1 | chr9:111311738-111395775 |
| 21781 | Tomm20l | NM_024234.2 | chr8:126930066-126946921 | 21878 | Trap1 | NM_026508.2 | chr16:4039976-4077810 |
| 21782 | Tomm20l | NM_029227.1 | chr12:71311427-71123222 | 21879 | Trap1a | NM_011635.1 | chrX:139338682-139338165 |
| 21783 | Tomm22 | NM_172609.3 | chr15:79670867-79672862 | 21880 | Trappc1 | NM_001024206.2 | chr11:69323985-69325793 |
| 21784 | Tomm34 | NM_001291155.1 | chr2:164065539-164071169 | 21881 | Trappc10 | NM_001081055.1 | chr10:78186725-78244642 |
| 21785 | Tomm40 | NM_001109748.1 | chr7:19701312-19715429 | 21882 | Trappc11 | NM_177240.3 | chr8:47490127-47533470 |
| 21786 | Tomm40l | NM_001037370.2 | chr1:171217802-171222514 | 21883 | Trappc12 | NM_001161410.1 | chr12:28690627-28750394 |
| 21787 | Tomm5 | NM_001099675.3 | chr4:45105209-45108113 | 21884 | Trappc13 | NM_001093759.1 | chr13:104142152-104178466 |
| 21788 | Tomm6 | NM_001164729.1 | chr17:47686644-47688386 | 21885 | Trappc2 | NM_025432.4 | chrX:166440754-166453140 |
| 21789 | Tomm6os | NR_045945.1 | chr17:47687609-47691092 | 21886 | Trappc2l | NM_025502.2 | chr8:122611626-122615591 |
| 21790 | Tomm7 | NM_025394.3 | chr5:23844943-23844145 | 21887 | Trappc3 | NM_013718.2 | chr4:126262404-126275883 |
| 21791 | Tomm70a | NM_138599.5 | chr16:57121713-57154530 | 21888 | Trappc3l | NM_001162937.1 | chr10:34037596-34109815 |
| 21792 | Tomt | NM_001081679.1 | chr7:101899807-101906359 | 21889 | Trappc4 | NM_021789.2 | chr9:44403758-44407548 |
| 21793 | Tonsl | NM_183091.3 | chr15:76626236-76639929 | 21890 | Trappc5 | NM_025701.4 | chr8:3676476-3680921 |
| 21794 | Top1 | NM_009408.2 | chr2:160645896-160722763 | 21891 | Trappc6a | NM_025960.3 | chr7:19508728-19516145 |
| 21795 | Top1mt | NM_028404.2 | chr15:75657032-75678790 | 21892 | Trappc6b | NM_030057.3 | chr12:59643091-59661472 |
| 21796 | Top2a | NM_011623.2 | chr11:98992946-99024189 | 21893 | Trappc8 | NM_029491.2 | chr18:20846144-20896078 |
| 21797 | Top2b | NM_009409.2 | chr14:16365205-16430787 | 21894 | Trappc9 | NM_001164641.1 | chr15:72799523-73061204 |
| 21798 | Top3a | NM_009410.3 | chr11:60740058-60777365 | 21895 | Trat1 | NM_198297.3 | chr16:48734689-48771956 |
| 21799 | Top3b | NM_011624.2 | chr16:16870890-16892986 | 21896 | Trcg1 | NM_001014398.2 | chr9:57236555-57249864 |
| 21800 | Topaz1 | NM_001199736.1 | chr9:122747345-122802074 | 21897 | Trdmt1 | NM_010067.4 | chr2:13510160-13546464 |
| 21801 | Tophp1 | NM_176979.5 | chr9:103305326-103350427 | 21898 | Trdn | NM_029726.2 | chr10:33083482-33476709 |
| 21802 | Topors | NM_134097.3 | chr4:40259605-40269841 | 21899 | Treh | NM_001277847.1 | chr9:44673232-44686305 |
| 21803 | Toporsl | NM_026652.2 | chr4:52596273-52612183 | 21900 | Trem1 | NM_021406.5 | chr17:48232738-48246924 |
| 21804 | Toporsos | NR_045945.1 | chr4:40269578-40270221 | 21901 | Trem2 | NM_001272078.1 | chr17:48346400-48352276 |
| 21805 | Tor1a | NM_144884.2 | chr2:30960560-30967918 | 21902 | Trem3 | NM_021407.3 | chr17:48247728-48258847 |
| 21806 | Tor1aip1 | NM_001160018.1 | chr1:156036098-156036480 | 21903 | Treml1 | NM_001289451.1 | chr17:48359915-48367176 |
| 21807 | Tor1aip2 | NM_001160380.1 | chr1:156035726-156058736 | 21904 | Treml2 | NM_001033405.2 | chr17:48300037-48312534 |
| 21808 | Tor1b | NM_138673.3 | chr2:30953000-30959015 | 21905 | Treml4 | NM_001033922.2 | chr17:48264294-48279358 |
| 21809 | Tor2a | NM_152800.3 | chr2:32757233-32762244 | 21906 | Trerf1 | NM_001097623.1 | chr17:47140941-47359458 |
| 21810 | Tor3a | NM_023141.2 | chr1:156655616-156674339 | 21907 | Trex1 | NM_001012236.1 | chr9:109057931-109059251 |
| 21811 | Tor4a | NM_146115.4 | chr2:25192719-25196813 | 21908 | Trex2 | NM_013907.4 | chrX:73433704-73435343 |
| 21812 | Tox | NM_145711.4 | chr4:6687385-6990723 | 21909 | Trf | NM_133977.2 | chr9:103208875-103230286 |
| 21813 | Tox2 | NM_001098799.3 | chr2:163225453-163323102 | 21910 | Trh | NM_009426.3 | chr6:92240060-92244650 |
| 21814 | Tox3 | NM_001098799.3 | chr8:90247111-90348252 | 21911 | Trhde | NM_146241.2 | chr10:114398820-114861370 |
| 21815 | Tox4 | NM_023434.3 | chr14:52279145-52295509 | 21912 | Trhr | NM_013696.2 | chr15:44396134-44235912 |
| 21816 | Tpbg | NM_001164792.1 | chr9:85842851-85847055 | 21913 | Trhr2 | NM_133202.2 | chr8:122356966-122360746 |
| 21817 | Tpbpa | NM_145711.4 | chr13:60938691-60941935 | 21914 | Triap1 | NM_026933.2 | chr15:341246-115343552 |
| 21818 | Tpbpb | NM_026429.4 | chr13:60901294-60904847 | 21915 | Trib1 | NM_144549.4 | chr15:59648653-59657099 |
| 21819 | Tpcn1 | NM_145853.2 | chr5:120534156-120588613 | 21916 | Trib2 | NM_144551.5 | chr12:15791726-15816785 |
| 21820 | Tpcn2 | NM_146206.5 | chr7:145259322-145284011 | 21917 | Trib3 | NM_175093.2 | chr2:152337424-152344060 |
| 21821 | Tpd52 | NM_001025261.1 | chr3:8929435-8964054 | 21918 | Tril | NM_025817.4 | chr6:53815467-53820825 |
| 21822 | Tpd52l1 | NM_009413.3 | chr17:36869573-36877833 | 21919 | Trim10 | NM_011636.2 | chr17:36869573-36877833 |
| 21823 | Tpd52l2 | NM_001291197.2 | chr2:181497141-181517962 | 21920 | Trim11 | NM_001290988.1 | chr11:58978092-58991462 |
| 21824 | Tpgs1 | NM_148934.2 | chr10:79669409-79676126 | 21921 | Trim12a | NM_001023835.2 | chr7:104299836-104315495 |

Fig.21 - 114

| | | | | | | | |
|---|---|---|---|---|---|---|---|
| 21922 | Trim12c | NM_001146007.1 | chr7:104338753-104353358 | 22019 | Trove2 | NM_013835.2 | chr1:143750790-143777051 |
| 21923 | Trim13 | NM_001164220.1 | chr14:61598225-61605945 | 22020 | Trp53 | NM_001127233.1 | chr11:69580358-69591873 |
| 21924 | Trim14 | NM_029077.4 | chr4:46505071-46536141 | 22021 | Trp53bp1 | NM_001290830.1 | chr2:121194834-121271407 |
| 21925 | Trim15 | NM_001024134.2 | chr17:36860690-36867187 | 22022 | Trp53bp2 | NM_173378.2 | chr1:182409166-182462436 |
| 21926 | Trim16 | NM_053169.2 | chr11:62820252-62842948 | 22023 | Trp53cor1 | NR_036469.2 | chr17:29057473-29079126 |
| 21927 | Trim17 | NM_031172.2 | chr11:58963780-58971729 | 22024 | Trp53i11 | NM_001025246.1 | chr2:93187583-93201757 |
| 21928 | Trim2 | NM_001271725.1 | chr3:84160438-84270783 | 22025 | Trp53i13 | NM_001024920.1 | chr11:77508098-77513273 |
| 21929 | Trim21 | NM_001082552.2 | chr7:102557919-102565482 | 22026 | Trp53inp1 | NM_001199105.1 | chr4:11156440-11174377 |
| 21930 | Trim23 | NM_030731.3 | chr13:104179097-104262048 | 22027 | Trp53inp2 | NM_178111.3 | chr2:155381855-155389847 |
| 21931 | Trim24 | NM_001272064.1 | chr6:37870810-37968445 | 22028 | Trp53rk | NM_023815.4 | chr2:166793766-166799492 |
| 21932 | Trim25 | NM_009546.2 | chr11:88999402-89020298 | 22029 | Trp53rg5 | NM_001271575.1 | chr2:164470303-164473724 |
| 21933 | Trim26 | NM_001025599.3 | chr17:36837145-36859398 | 22030 | Trp63 | NM_001127259.1 | chr16:25683764-25892088 |
| 21934 | Trim27 | NM_009052.4 | chr13:21179930-21194723 | 22031 | Trp73 | NM_001126330.1 | chr4:154056248-154097173 |
| 21935 | Trim28 | NM_011588.3 | chr7:13024151-13031032 | 22032 | Trpa1 | NM_177781.4 | chr1:14872647-14918862 |
| 21936 | Trim29 | NM_023655.2 | chr9:43310762-43336125 | 22033 | Trpc1 | NM_011643.3 | chr9:95705066-95750358 |
| 21937 | Trim3 | NM_001285870.1 | chr7:105610647-105633571 | 22034 | Trpc2 | NM_001109897.2 | chr7:102083115-102096864 |
| 21938 | Trim30a | NM_009099.2 | chr7:104409025-104465193 | 22035 | Trpc3 | NM_019510.2 | chr3:36620481-36680167 |
| 21939 | Trim30b | NM_175648.2 | chr7:104335397-104358646 | 22036 | Trpc4 | NM_001253682.1 | chr3:54156056-54318471 |
| 21940 | Trim30d | NM_001167828.1 | chr7:104470013-104507849 | 22037 | Trpc4ap | NM_001163452.1 | chr2:155634276-155692384 |
| 21941 | Trim30e-ps1 | NR_033673.1 | chr7:104532958-104535361 | 22038 | Trpc5 | NM_009428.3 | chrX:144377326-144688180 |
| 21942 | Trim31 | NM_146077.2 | chr17:36898129-36910217 | 22039 | Trpc5os | NM_001195579.1 | chrX:144456581-144477053 |
| 21943 | Trim32 | NM_001161782.1 | chr4:65604985-65616240 | 22040 | Trpc6 | NM_001282086.1 | chr9:8544141-8680741 |
| 21944 | Trim33 | NM_001079830.2 | chr3:103279292-103358770 | 22041 | Trpc7 | NM_012035.3 | chr13:56773097-56895789 |
| 21945 | Trim34a | NM_030684.3 | chr7:104244456-104262236 | 22042 | Trpd52l3 | NM_025741.2 | chr19:30003789-30006020 |
| 21946 | Trim34b | NM_001243916.1 | chr7:104329470-104336617 | 22043 | Trpm1 | NM_001039104.2 | chr7:64153834-64269759 |
| 21947 | Trim35 | NM_029679.3 | chr14:66297024-66311424 | 22044 | Trpm2 | NM_138301.2 | chr10:77907721-77969872 |
| 21948 | Trim36 | NM_001170855.1 | chr18:46165299-46198818 | 22045 | Trpm3 | NM_001035239.2 | chr19:22139116-22989882 |
| 21949 | Trim37 | NM_197987.2 | chr11:87127074-87220686 | 22046 | Trpm4 | NM_175130.4 | chr7:45303154-45333780 |
| 21950 | Trim38 | NM_001029935.2 | chr13:23782540-23791528 | 22047 | Trpm5 | NM_020277.2 | chr7:143071528-143094642 |
| 21951 | Trim39 | NM_024468.2 | chr17:36258872-36272004 | 22048 | Trpm6 | NM_153417.1 | chr19:18740982-18892511 |
| 21952 | Trim40 | NM_001033235.3 | chr17:36881597-36890125 | 22049 | Trpm7 | NM_001164325.1 | chr2:126791557-126876261 |
| 21953 | Trim41 | NM_145377.2 | chr11:48806403-48817391 | 22050 | Trpm8 | NM_134252.3 | chr1:88306711-88388851 |
| 21954 | Trim42 | NM_030219.2 | chr9:97349561-97369958 | 22051 | Trps1 | NM_032000.2 | chr15:50854758-50890041 |
| 21955 | Trim43a | NM_001034906.2 | chr9:88581035-88588819 | 22052 | Trpt1 | NM_153597.2 | chr19:6996130-6999046 |
| 21956 | Trim43b | NM_001170884.1 | chr9:89084623-89092835 | 22053 | Trpv1 | NM_001001445.2 | chr11:73234148-73261322 |
| 21957 | Trim43c | NM_001177858.1 | chr9:88839163-88848190 | 22054 | Trpv2 | NM_011706.2 | chr11:62574485-62600305 |
| 21958 | Trim44 | NM_030219.2 | chr2:102300118-102400900 | 22055 | Trpv3 | NM_145099.2 | chr11:73267619-73297200 |
| 21959 | Trim45 | NM_001165952.1 | chr3:100922492-100986925 | 22056 | Trpv4 | NM_022017.3 | chr5:114622153-114658421 |
| 21960 | Trim46 | NM_001034506.1 | chr3:89234175-89245199 | 22057 | Trpv5 | NM_001007572.2 | chr6:41652769-41680723 |
| 21961 | Trim47 | NM_001205081.1 | chr11:116105749-116110235 | 22058 | Trpv6 | NM_022413.4 | chr6:41620618-41636405 |
| 21962 | Trim50 | NM_178240.2 | chr5:135353295-135367654 | 22059 | Trrap | NM_001081362.1 | chr5:144768791-144859773 |
| 21963 | Trim52 | NM_198601.3 | chr14:106106197-106109280 | 22060 | Trub1 | NM_028115.3 | chr19:57452905-57491005 |
| 21964 | Trim54 | NM_021447.2 | chr5:31116611-31137626 | 22061 | Trub2 | NM_001290495.1 | chr2:29774683-29787671 |
| 21965 | Trim55 | NM_001081281.1 | chr3:19644459-19691593 | 22062 | Try10 | NM_001038996.2 | chr6:41354104-41357944 |
| 21966 | Trim56 | NM_201373.4 | chr5:137111285-137116207 | 22063 | Try4 | NM_011646.5 | chr6:41302271-41305533 |
| 21967 | Trim58 | NM_001039047.1 | chr11:58640464-58652404 | 22064 | Try5 | NM_001003405.4 | chr6:41311231-41314710 |
| 21968 | Trim59 | NM_025464.3 | chr3:69035293-69044742 | 22065 | Tsacc | NM_029801.2 | chr3:88282759-88296838 |
| 21969 | Trim6 | NM_001013616.2 | chr7:104218794-104235152 | 22066 | Tsc1 | NM_001289575.1 | chr2:28641232-28691172 |
| 21970 | Trim60 | NM_153097.2 | chr8:64998447-65018688 | 22067 | Tsc2 | NM_001039363.2 | chr17:24598815-24632627 |
| 21971 | Trim61 | NM_001177551.1 | chr8:65012975-65018688 | 22068 | Tsc22d1 | NM_001177751.2 | chr14:76488435-76507765 |
| 21972 | Trim62 | NM_178110.2 | chr4:128884139-128911326 | 22069 | Tsc22d2 | NM_001081229.1 | chr3:58415688-58466787 |
| 21973 | Trim63 | NM_001039048.2 | chr4:134315119-134329629 | 22070 | Tsc22d3 | NM_001077364.1 | chrX:140539528-140600522 |
| 21974 | Trim65 | NM_178802.4 | chr11:116124707-116131128 | 22071 | Tsc22d4 | NM_023910.6 | chr5:137745968-137759747 |
| 21975 | Trim66 | NM_001170912.1 | chr7:109449000-109508134 | 22072 | Tsen15 | NM_025677.3 | chr1:152370735-152386682 |
| 21976 | Trim67 | NM_198632.2 | chr8:124793018-124884704 | 22073 | Tsen2 | NM_199003.1 | chr6:115544703-115579338 |
| 21977 | Trim68 | NM_198123.3 | chr7:102677584-102687327 | 22074 | Tsen34 | NM_001164204.1 | chr7:3693609-3701035 |
| 21978 | Trim69 | NM_080510.2 | chr2:122160699-122179027 | 22075 | Tsen54 | NM_029557.1 | chr11:115814738-115823102 |
| 21979 | Trim7 | NM_053166.2 | chr11:48826137-48850195 | 22076 | Tsfm | NM_025537.3 | chr10:127022331-127030814 |
| 21980 | Trim71 | NM_001042503.2 | chr9:114511272-114564369 | 22077 | Tsg101 | NM_021884.3 | chr7:46889026-46919930 |
| 21981 | Trim72 | NM_001079932.3 | chr7:128104377-128011393 | 22078 | Tsga10 | NM_001290720.1 | chr1:37760823-37865298 |
| 21982 | Trim75 | NM_001034429.2 | chr8:64981650-64987644 | 22079 | Tsga13 | NM_054073.2 | chr6:30896980-30915573 |
| 21983 | Trim8 | NM_053100.2 | chr19:46501647-46516455 | 22080 | Tsga8 | NM_021898.2 | chrX:83486675-83487924 |
| 21984 | Trim9 | NM_053100.2 | chr12:70244534-70347614 | 22081 | Tshb | NM_001165939.1 | chr3:102777397-102782714 |
| 21985 | Triml1 | NM_177742.4 | chr8:43129806-43141486 | 22082 | Tshr | NM_001113404.1 | chr12:91400992-91522541 |
| 21986 | Triml2 | NM_001160412.1 | chr8:43183121-43193884 | 22083 | Tshz1 | NM_001081300.1 | chr18:84011626-84086582 |
| 21987 | Trio | NM_001081302.1 | chr15:27730648-28025848 | 22084 | Tshz2 | NM_080455.2 | chr2:169633645-169808504 |
| 21988 | Triobp | NM_001024716.1 | chr15:78983035-79005864 | 22085 | Tshz3 | NM_172398.2 | chr7:36698117-36773457 |
| 21989 | Trip10 | NM_001242389.1 | chr17:57249450-57263697 | 22086 | Tsix | NR_002844.2 | chrX:103431516-103484957 |
| 21990 | Trip11 | NM_028434.1 | chr12:101913371-101913371 | 22087 | Tsks | NM_001077591.1 | chr7:44943239-44958037 |
| 21991 | Trip12 | NM_133975.4 | chr1:84721188-84839304 | 22088 | Tsku | NM_001024619.3 | chr7:98350867-98361288 |
| 21992 | Trip13 | NM_027182.2 | chr13:73921461-73937767 | 22089 | Tslp | NM_021367.2 | chr18:32815382-32819799 |
| 21993 | Trip4 | NM_001170907.1 | chr9:65829925-65885173 | 22090 | Tsn | NM_011650.3 | chr1:118298517-118311132 |
| 21994 | Trip6 | NM_011639.3 | chr5:137309898-137314241 | 22091 | Tsnax | NM_016909.2 | chr1:125012996-125034192 |
| 21995 | Triqk | NM_001171801.1 | chr4:129016836-129081485 | 22092 | Tsnaxip1 | NM_024445.4 | chr8:105827743-105844676 |
| 21996 | Trit1 | NM_025873.2 | chr4:123016596-123054934 | 22093 | Tspan1 | NM_133681.4 | chr4:116161880-116167598 |
| 21997 | Trmt1 | NM_001164559.1 | chr8:84689246-84699808 | 22094 | Tspan10 | NM_145363.2 | chr11:120442630-120447321 |
| 21998 | Trmt10a | NM_153728.3 | chr3:138143537-138159820 | 22095 | Tspan11 | NM_026743.3 | chr6:127887621-127953031 |
| 21999 | Trmt10b | NM_027266.4 | chr4:45297167-45316131 | 22096 | Tspan12 | NM_173007.3 | chr6:21771394-21852515 |
| 22000 | Trmt10c | NM_029092.3 | chr16:56033710-56037774 | 22097 | Tspan13 | NM_025359.3 | chr12:36014554-36042478 |
| 22001 | Trmt11 | NM_028604.2 | chr10:30534224-30600749 | 22098 | Tspan14 | NM_145928.2 | chr14:40906443-40966807 |
| 22002 | Trmt112 | NM_001166370.1 | chr19:6909697-6911026 | 22099 | Tspan15 | NM_197996.2 | chr10:62185396-62231218 |
| 22003 | Trmt12 | NM_026642.2 | chr15:58572648-58876781 | 22100 | Tspan17 | NM_028841.3 | chr13:54789404-54796775 |
| 22004 | Trmt13 | NM_030016.2 | chr3:116581335-116614587 | 22101 | Tspan18 | NM_183180.2 | chr2:93201759-93334487 |
| 22005 | Trmt2 | NM_026876.3 | chr1:151428647-151458183 | 22102 | Tspan2 | NM_001243132.1 | chr3:102735214-102772310 |
| 22006 | Trmt2a | NM_001080999.2 | chr16:18248882-18254772 | 22103 | Tspan2os | NR_040588.1 | chr3:102720230-102735417 |
| 22007 | Trmt2b | NM_001167994.1 | chrX:134222954-134276984 | 22104 | Tspan3 | NM_019793.3 | chr9:56135883-56161070 |
| 22008 | Trmt44 | NM_030208.3 | chr5:35575070-35575070 | 22105 | Tspan31 | NM_025982.4 | chr10:127067289-127070261 |
| 22009 | Trmt5 | NM_029580.3 | chr12:73280409-73286711 | 22106 | Tspan32 | NM_001128080.2 | chr7:143005045-143019485 |
| 22010 | Trmt6 | NM_175113.3 | chr2:132804214-132816054 | 22107 | Tspan33 | NM_146173.3 | chr6:29694213-29718558 |
| 22011 | Trmt61a | NM_001099792.1 | chr2:111678104-111683902 | 22108 | Tspan4 | NM_001252588.1 | chr7:141876379-141493427 |
| 22012 | Trmt61b | NR_015549.1 | chr17:71557026-71598761 | 22109 | Tspan5 | NM_019571.5 | chr3:137742207-138904438 |
| 22013 | Trmu | NM_028063.2 | chr15:85879826-85897393 | 22110 | Tspan6 | NM_019656.3 | chrX:133891069-133898429 |
| 22014 | Trnau1ap | NM_027925.3 | chr14:132311762-132329558 | 22111 | Tspan7 | NM_019634.2 | chrX:104485115-10596604 |
| 22015 | Trnp1 | NM_001156.2 | chr4:133491099-133498550 | 22112 | Tspan8 | NM_001168679.1 | chr10:115817283-115849895 |
| 22016 | Trnt1 | NM_001242358.1 | chr6:106769137-106782474 | 22113 | Tspan9 | NM_127961399-128143578 | chr6:127961399-128143578 |
| 22017 | Tro | NM_001002272.3 | chrX:150644709-150657436 | 22114 | Tspear | NM_001287074.1 | chr10:77686656-77886789 |
| 22018 | Troap | NM_001162506.1 | chr15:99074972-99083409 | 22115 | Tspo | NM_009775.4 | chr15:83563572-83574203 |

Fig.21 - 115

| | | | | | | | | |
|---|---|---|---|---|---|---|---|---|
| 22116 | Tspo2 | NM_027292.2 | chr17:48448434-48451501 | 22213 | Tuba3a | NM_009446.2 | chr6:125278273-125286042 |
| 22117 | Tspyl1 | NM_009433.3 | chr10:34282189-34284885 | 22214 | Tuba3b | NM_009449.3 | chr6:145615962-145621477 |
| 22118 | Tspyl2 | NM_029836.3 | chrX:152336851-152342484 | 22215 | Tuba4a | NM_009447.4 | chr1:75214971-75219294 |
| 22119 | Tspyl3 | NM_198617.2 | chr2:153222369-153225441 | 22216 | Tuba8 | NM_017379.2 | chr6:121210733-121226098 |
| 22120 | Tspyl4 | NM_030203.2 | chr10:34297420-34301320 | 22217 | Tubal3 | NM_001033879.3 | chr13:3924694-3935277 |
| 22121 | Tspyl5 | NM_001085421.1 | chr15:33683874-33687883 | 22218 | Tubb1 | NM_001080971.2 | chr2:174450594-174458380 |
| 22122 | Tspy-ps | NR_027507.1 | chrY:1055763-1058868 | 22219 | Tubb2a | NM_009450.2 | chr13:34074279-34078008 |
| 22123 | Tsr1 | NM_177325.3 | chr11:74898079-74909340 | 22220 | Tubb2a-ps2 | NR_003964.2 | chr12:11882195-11882899 |
| 22124 | Tsr2 | NM_001164578.1 | chrX:151087093-151096543 | 22221 | Tubb2b | NM_023716.2 | chr13:34127007-34130354 |
| 22125 | Tsr3 | NM_001163718.1 | chr17:25240169-25242799 | 22222 | Tubb3 | NM_023279.2 | chr8:123411563-123422010 |
| 22126 | Tssc1 | NM_201357.2 | chr12:28751827-28867491 | 22223 | Tubb4a | NM_009451.3 | chr17:57080065-57087782 |
| 22127 | Tssc4 | NM_001115085.1 | chr7:143069367-143071987 | 22224 | Tubb4b | NM_146116.2 | chr2:25222157-25224702 |
| 22128 | Tssk1 | NM_009435.2 | chr16:17894202-17895653 | 22225 | Tubb5 | NM_011655.5 | chr17:35833919-35838301 |
| 22129 | Tssk2 | NM_009436.2 | chr16:17898636-17900024 | 22226 | Tubb6 | NM_026473.2 | chr18:67390730-67402749 |
| 22130 | Tssk3 | NM_080442.2 | chr4:129489007-129490770 | 22227 | Tubd1 | NM_001199045.1 | chr11:86544990-86567380 |
| 22131 | Tssk4 | NM_001253888.1 | chr14:55650183-55652539 | 22228 | Tube1 | NM_028006.2 | chr10:39138022-39151058 |
| 22132 | Tssk5 | NM_183099.2 | chr15:76371957-76374938 | 22229 | Tubg1 | NM_134024.2 | chr11:101120130-101126419 |
| 22133 | Tssk6 | NM_032004.1 | chr8:69902214-69903518 | 22230 | Tubg2 | NM_134028.2 | chr11:101155883-101161787 |
| 22134 | Tst | NM_009437.4 | chr15:78399555-78405859 | 22231 | Tubgcp2 | NM_001286007.1 | chr7:139995954-140036674 |
| 22135 | Tsta3 | NM_031201.1 | chr15:75924682-75929730 | 22232 | Tubgcp3 | NM_198031.1 | chr8:12614276-12672100 |
| 22136 | Tstd1 | NM_001164525.1 | chr1:171419032-171420352 | 22233 | Tubgcp4 | NM_001290824.1 | chr2:121171167-121198770 |
| 22137 | Tstd2 | NM_173033.3 | chr4:46114745-46138475 | 22234 | Tubgcp5 | NM_146190.2 | chr7:55794147-55831447 |
| 22138 | Tstd3 | NM_029840.1 | chr4:21757381-21767211 | 22235 | Tubgcp6 | NM_001163319.1 | chr15:89099097-89123150 |
| 22139 | Tsx | NM_009440.2 | chrX:103414466-103424583 | 22236 | Tufm | NM_001163713.1 | chr7:126487354-126490731 |
| 22140 | Ttbk1 | NM_001162864.1 | chr17:46442447-46487875 | 22237 | Tuft1 | NM_011656.3 | chr3:94612752-94658872 |
| 22141 | Ttbk2 | NM_001024856.2 | chr2:120732816-120850418 | 22238 | Tug1 | NR_002321.2 | chr11:3639784-3648814 |
| 22142 | Ttc1 | NM_133795.1 | chr11:43730005-43747973 | 22239 | Tulp1 | NM_021478.1 | chr17:28351518-28365143 |
| 22143 | Ttc12 | NM_172770.3 | chr9:49483960-49486225 | 22240 | Tulp2 | NM_001045555.2 | chr7:45513705-45522927 |
| 22144 | Ttc13 | NM_145607.3 | chr8:124671326-124721975 | 22241 | Tulp3 | NM_011657.2 | chr6:128321160-128355851 |
| 22145 | Ttc14 | NM_001290500.1 | chr3:33800182-33814860 | 22242 | Tulp4 | NM_001103181.1 | chr17:6106829-6240637 |
| 22146 | Ttc16 | NM_001290635.1 | chr2:32775203-32775633 | 22243 | Tunar | NR_045047.1 | chr2:105336593-105385932 |
| 22147 | Ttc17 | NM_183106.2 | chr2:94300765-94406689 | 22244 | Tusc1 | NM_026954.1 | chr4:93334147-93335511 |
| 22148 | Ttc18 | NM_001163638.1 | chr14:20394189-20452225 | 22245 | Tusc2 | NM_619742.4 | chr9:107563254-107566108 |
| 22149 | Ttc19 | NM_028360.2 | chr11:62281472-62316424 | 22246 | Tusc3 | NM_030254.3 | chr8:39005866-39130817 |
| 22150 | Ttc21a | NM_028735.3 | chr9:119937605-119967793 | 22247 | Tusc5 | NM_177709.3 | chr11:76679872-76698664 |
| 22151 | Ttc21b | NM_001047604.2 | chr2:66184326-66256617 | 22248 | Tuft1 | NM_197993.2 | chr19:8953849-8966210 |
| 22152 | Ttc22 | NM_177667.4 | chr4:106622448-106640187 | 22249 | Tvp23a | NM_001013778.1 | chr16:10420558-10447350 |
| 22153 | Ttc23 | NM_001168475.1 | chr7:67647409-67726576 | 22250 | Tvp23b | NM_026210.4 | chr11:62879489-62895184 |
| 22154 | Ttc23l | NM_029430.1 | chr15:10503946-10558668 | 22251 | Twf1 | NM_008971.4 | chr15:94577947-94589824 |
| 22155 | Ttc24 | NM_172526.3 | chr3.88069409-88078304 | 22252 | Twf2 | NM_011876.3 | chr9:106203107-106215387 |
| 22156 | Ttc25 | NM_028918.2 | chr11:100545831-100572566 | 22253 | Twist1 | NM_011658.2 | chr12:33957670-33959831 |
| 22157 | Ttc26 | NM_028341.4 | chr6:38381523-38427647 | 22254 | Twist2 | NM_007855.3 | chr1:91801460-91848034 |
| 22158 | Ttc27 | NM_152817.3 | chr17:74717749-74863570 | 22255 | Twistnb | NM_172253.2 | chr12:33429623-33439380 |
| 22159 | Ttc28 | NM_001267621.1 | chr5:110879802-111289779 | 22256 | Twsg1 | NM_023053.3 | chr17:65923064-65951187 |
| 22160 | Ttc29 | NM_183096.3 | chr8:78213341-78394326 | 22257 | Txk | NM_001122754.2 | chr5:72695977-72752777 |
| 22161 | Ttc3 | NM_009441.2 | chr16:94370738-94469221 | 22258 | Txlna | NM_001005506.3 | chr4:129626076-129640805 |
| 22162 | Ttc30a1 | NM_030188.3 | chr2.75979105-75981967 | 22259 | Txlnb | NM_138628.3 | chr10:17796218-17845663 |
| 22163 | Ttc30a2 | NM_001081228.1 | chr2:75976171-75978179 | 22260 | Txlng | NM_001290776.1 | chrX:162778916-162929454 |
| 22164 | Ttc30b | NM_028235.1 | chr2:75985849-75988462 | 22261 | Txn1 | NM_011660.3 | chr4:57943872-57956411 |
| 22165 | Ttc32 | NM_029321.2 | chr12:9029986-9036394 | 22262 | Txn2 | NM_019913.5 | chr15:77915050-77928994 |
| 22166 | Ttc33 | NM_026213.3 | chr15:5185559-5218332 | 22263 | Txndc11 | NM_029582.2 | chr16:11074916-11134532 |
| 22167 | Ttc34 | NM_172878.3 | chr4:154856199-154867127 | 22264 | Txndc12 | NM_025334.3 | chr4:108834677-108862119 |
| 22168 | Ttc36 | NM_138951.1 | chr9:44799399-44802951 | 22265 | Txndc15 | NM_175150.3 | chr13:55714649-55726228 |
| 22169 | Ttc37 | NM_001081352.1 | chr13:76098733-76187983 | 22266 | Txndc16 | NM_172597.3 | chr14:45134447-45219425 |
| 22170 | Ttc38 | NM_001033347.4 | chr15:85858822-85858822 | 22267 | Txndc17 | NM_026146.4 | chr11:72207553-72210487 |
| 22171 | Ttc39a | NM_001145948.1 | chr4:109415646-109444745 | 22268 | Txndc2 | NM_001146002.1 | chr17:65637504-65642204 |
| 22172 | Ttc39b | NM_027238.2 | chr4.83202300-83324189 | 22269 | Txndc5 | NM_001289598.1 | chr13:38500270-38528824 |
| 22173 | Ttc39c | NM_028341.4 | chr18:12643532-12737052 | 22270 | Txndc8 | NM_026132.2 | chr4:57984028-58009124 |
| 22174 | Ttc39d | NM_026351.2 | chr17:80215913-80217936 | 22271 | Txndc9 | NM_172954.4 | chr1:37983866-37997208 |
| 22175 | Ttc4 | NM_001172073.1 | chr4:106661807-106678686 | 22272 | Txnip | NM_001009935.2 | chr3:96557956-96561857 |
| 22176 | Ttc5 | NM_001080949.2 | chr14:50765408-50785520 | 22273 | Txnl1 | NM_016792.4 | chr18:63662800-63692359 |
| 22177 | Ttc7 | NM_028639.4 | chr17:87282885-87381770 | 22274 | Txnl4a | NM_001088608.2 | chr18:80206797-80212732 |
| 22178 | Ttc7b | NM_001013026.2 | chr12:100300763-100520822 | 22275 | Txnl4b | NM_175646.3 | chr8:109565985-109574053 |
| 22179 | Ttc8 | NM_029553.3 | chr12:98920573-98983238 | 22276 | Txnrd1 | NM_001042513.1 | chr10:82859205-82897724 |
| 22180 | Ttc9 | NM_001033149.3 | chr12:81631248-81667557 | 22277 | Txnrd2 | NM_013711.3 | chr16:18426416-18479073 |
| 22181 | Ttc9b | NM_027633023.3 | chr7:27653923-27656207 | 22278 | Txnrd3 | NM_001178058.1 | chr6:89643987-89675529 |
| 22182 | Ttc9c | NM_027412.3 | chr19:8809074-8819294 | 22279 | Tyk2 | NM_001205312.1 | chr9:21104067-21131275 |
| 22183 | Ttf1 | NM_009442.2 | chr2:29060262-29087650 | 22280 | Tymp | NM_138302.1 | chr15:89371930-89377037 |
| 22184 | Ttf2 | NM_001013026.2 | chr3:100958859-100969663 | 22281 | Tyms | NM_021288.4 | chr5:30058199-30073625 |
| 22185 | Tti1 | NM_029282.1 | chr2:157981802-158009360 | 22282 | Tyms-ps | NR_000040.2 | chr8:87966670-87968017 |
| 22186 | Tti2 | NM_001199988.1 | chr8:31165315-31164703 | 22283 | Tyr | NM_011661.4 | chr7:87427404-87493411 |
| 22187 | Ttk | NM_001110265.1 | chr9:83834688-83869493 | 22284 | Tyro3 | NM_001290800.1 | chr2:119797739-119818103 |
| 22188 | Ttl | NM_027192.2 | chr2:129065946-129096283 | 22285 | Tyrobp | NM_011662.2 | chr7:30413787-30417579 |
| 22189 | Ttll1 | NM_178869.4 | chr15:83483768-83510907 | 22286 | Tyrp1 | NM_001282014.1 | chr4:80834212-80851736 |
| 22190 | Ttll10 | NM_029264.2 | chr4:156034836-156050817 | 22287 | Tysnd1 | NM_001272090.1 | chr10:61695513-61702773 |
| 22191 | Ttll11 | NM_029774.2 | chr2:35751225-35979624 | 22288 | Tyw1 | NM_001015876.2 | chr5:130257036-130341567 |
| 22192 | Ttll12 | NM_183017.2 | chr15:83575093-83595157 | 22289 | Tyw3 | NM_001168358.1 | chr3:154576519-154597098 |
| 22193 | Ttll13 | NM_177765.3 | chr7:80246375-80260821 | 22290 | Tyw5 | NM_001037742.2 | chr1:57388243-57406874 |
| 22194 | Ttll2 | NM_001098267.3 | chr17:31647081-31658754 | 22291 | U2af1 | NM_001163769.1 | chr17:31647081-31658754 |
| 22195 | Ttll3 | NM_001142732.1 | chr6:113389259-113399448 | 22292 | U2af1l4 | NM_170760.3 | chr7:30563339-30565364 |
| 22196 | Ttll4 | NM_001014974.1 | chr1:74661753-74697973 | 22293 | U2af2 | NM_001205231.1 | chr7:5062142-5079945 |
| 22197 | Ttll5 | NM_001081423.1 | chr12:85824949-86053760 | 22294 | U2surp | NM_001114977.1 | chr9:95456893-95511996 |
| 22198 | Ttll6 | NM_172799.4 | chr11:96133785-96165452 | 22295 | U90926 | NR_033483.1 | chr5:92209894-92215408 |
| 22199 | Ttll7 | NM_001302957.1 | chr3:146852136-146984009 | 22296 | Uaca | NM_028283.2 | chr9:60794547-60880370 |
| 22200 | Ttll8 | NM_001083897.1 | chr15:88913897-88954418 | 22297 | Uap1 | NM_133806.5 | chr1:170141222-170174964 |
| 22201 | Ttll9 | NM_001083618.1 | chr2:152962484-153008482 | 22298 | Uap1l1 | NM_001032293.1 | chr2:25361491-25365626 |
| 22202 | Tln | NM_011652.3 | chr2:76703983-76982547 | 22299 | Ubal | NM_001136085.2 | chrX:20662895-20683179 |
| 22203 | Ttpa | NM_015767.3 | chr4:20008427-20030785 | 22300 | Ubaly | NM_011667.2 | chrY:818712-844224 |
| 22204 | Ttpal | NM_029512.2 | chr2:163602313-163619013 | 22301 | Uba2 | NM_016682.2 | chr7:34140696-34168529 |
| 22205 | Ttr | NM_013697.5 | chr18:20665249-20674326 | 22302 | Uba3 | NM_001111106.2 | chr6:97183631-97205647 |
| 22206 | Ttyh1 | NM_001001454.4 | chr7:4119529-4135407 | 22303 | Uba5 | NM_025692.3 | chr9:104046587-104063121 |
| 22207 | Ttyh2 | NM_053273.2 | chr11:114675467-114720984 | 22304 | Uba52 | NM_019883.3 | chr8:70508265-70510367 |
| 22208 | Ttyh3 | NM_175274.5 | chr5:140620576-140649031 | 22305 | Uba6 | NM_172712.2 | chr5:86110729-86172743 |
| 22209 | Tub | NM_021885.4 | chr7:109010879-109034459 | 22306 | Uba7 | NM_023738.4 | chr9:107975566-107984056 |
| 22210 | Tuba1a | NM_011653.2 | chr15:98929890-98953501 | 22307 | Ubac1 | NM_133835.2 | chr2:25996957-26021780 |
| 22211 | Tuba1b | NM_011654.2 | chr15:98931430-98934390 | 22308 | Ubac2 | NM_026861.2 | chr14:121878605-122021035 |
| 22212 | Tuba1c | NM_009448.4 | chr15:99029890-99038105 | 22309 | Ubald1 | NM_145359.2 | chr16:4874778-4879851 |

Fig.21 - 116

| | | | | | | | |
|---|---|---|---|---|---|---|---|
| 22310 | Ubald2 | NM_176902.3 | chr11:116434093-116439077 | 22407 | Ucma | NM_001113558.2 | chr2:4976121-4985748 |
| 22311 | Ubap1 | NM_001290454.1 | chr4:41348995-41389766 | 22408 | Ucn | NM_021290.2 | chr5:31137988-31138895 |
| 22312 | Ubap1l | NM_001111145.1 | chr9:65361059-65380377 | 22409 | Ucn2 | NM_145077.1 | chr9:108986162-108987164 |
| 22313 | Ubap2 | NM_026872.1 | chr4:41194314-41275135 | 22410 | Ucn3 | NM_031250.5 | chr13:3940687-3945349 |
| 22314 | Ubap2l | NM_001165983.1 | chr3:90000287-90052475 | 22411 | Ucp1 | NM_009463.3 | chr8:83290347-83298456 |
| 22315 | Ubash3a | NM_177823.4 | chr17:31208065-31242403 | 22412 | Ucp2 | NM_011671.5 | chr7:100493957-100499629 |
| 22316 | Ubash3b | NM_176860.5 | chr9:41013640-41157494 | 22413 | Ucp3 | NM_009464.3 | chr7:100472990-100486432 |
| 22317 | Ubb | NM_011664.4 | chr11:62551170-62553213 | 22414 | Uevld | NM_001040695.1 | chr7:46923215-46958518 |
| 22318 | Ubc | NM_019639.4 | chr5:125385964-125390017 | 22415 | Ufc1 | NM_025388.2 | chr1:171288563-171294982 |
| 22319 | Ubd | NM_023137.3 | chr17:37193891-37196101 | 22416 | Ufd1l | NM_011672.4 | chr16:18812293-18835261 |
| 22320 | Ube2a | NM_019668.4 | chrX:36874294-36884220 | 22417 | Ufl1 | NM_026194.4 | chr4:25248585-25281821 |
| 22321 | Ube2b | NM_009458.4 | chr11:51985145-52000466 | 22418 | Ufm1 | NM_026435.5 | chr3:53853375-53863807 |
| 22322 | Ube2c | NM_026785.2 | chr2:164769928-164772902 | 22419 | Ufsp1 | NM_027356.2 | chr5:137294668-137295664 |
| 22323 | Ube2cbp | NM_027394.2 | chr9:86307233-86464916 | 22420 | Ufsp2 | NM_138668.2 | chr4:45975527-45996956 |
| 22324 | Ube2d1 | NM_145420.2 | chr10:71254979-71285262 | 22421 | Ugcg | NM_011673.3 | chr4:59189549-59222833 |
| 22325 | Ube2d2a | NM_019912.2 | chr18:35771558-35807172 | 22422 | Ugdh | NM_009466.2 | chr5:65413221-65435842 |
| 22326 | Ube2d2b | NM_001276397.1 | chr5:107830161-107831777 | 22423 | Uggt1 | NM_198899.2 | chr1:36140027-36244302 |
| 22327 | Ube2d3 | NM_025356.4 | chr3:135438758-135467178 | 22424 | Uggt2 | NM_001081252.2 | chr14:118984984-119099434 |
| 22328 | Ube2dnl1 | NM_001276396.1 | chrX:114905011-114905941 | 22425 | Ugp2 | NM_001290434.1 | chr11:21323125-21371267 |
| 22329 | Ube2dnl2 | NM_001081661.1 | chrX:114907581-114908510 | 22426 | Ugt1a1 | NM_201645.2 | chr1:88211958-88220002 |
| 22330 | Ube2e1 | NM_009455.3 | chr14:18282728-18331844 | 22427 | Ugt1a10 | NM_201641.2 | chr1:88055410-88220002 |
| 22331 | Ube2e2 | NM_144839.1 | chr14:18573576-18893627 | 22428 | Ugt1a2 | NM_013701.3 | chr1:88200610-88220002 |
| 22332 | Ube2e3 | NM_009454.2 | chr2:78869046-78920583 | 22429 | Ugt1a5 | NM_201643.2 | chr1:88166011-88220002 |
| 22333 | Ube2f | NM_026454.3 | chr1:91259318-91286025 | 22430 | Ugt1a6a | NM_145079.3 | chr1:88134808-88220002 |
| 22334 | Ube2g1 | NM_025985.4 | chr11:72607260-72686481 | 22431 | Ugt1a6b | NM_201410.3 | chr1:88103256-88218998 |
| 22335 | Ube2g2 | NM_019803.3 | chr10:77622326-77645990 | 22432 | Ugt1a7c | NM_201642.4 | chr1:88095000-88220002 |
| 22336 | Ube2h | NM_001169576.1 | chr6:30211289-30304539 | 22433 | Ugt1a9 | NM_201644.2 | chr1:88070778-88220002 |
| 22337 | Ube2i | NM_001177609.1 | chr17:25260510-25273914 | 22434 | Ugt2a1 | NM_053184.2 | chr5:87459489-87490871 |
| 22338 | Ube2j1 | NM_019586.3 | chr4:33031424-33052364 | 22435 | Ugt2a2 | NM_001024148.1 | chr5:87459492-87492258 |
| 22339 | Ube2j2 | NM_001039157.2 | chr4:155943812-155959604 | 22436 | Ugt2a3 | NM_028094.3 | chr5:87324971-87337195 |
| 22340 | Ube2k | NM_016786.4 | chr5:65537244-65598989 | 22437 | Ugt2b1 | NM_152811.1 | chr5:86916638-86928503 |
| 22341 | Ube2l3 | NM_009456.2 | chr16:17152014-17201492 | 22438 | Ugt2b34 | NM_153598.2 | chr5:86889769-86906937 |
| 22342 | Ube2l6 | NM_019949.2 | chr2:84798827-84810003 | 22439 | Ugt2b35 | NM_172881.3 | chr5:87000859-87013274 |
| 22343 | Ube2m | NM_001168469.2 | chr7:13159319-13038275 | 22440 | Ugt2b36 | NM_001029867.1 | chr5:87065926-87092555 |
| 22344 | Ube2n | NM_080560.3 | chr10:95515161-95545658 | 22441 | Ugt2b37 | NM_053215.3 | chr5:87240491-87254788 |
| 22345 | Ube2o | NM_173755.3 | chr11:116537752-116581447 | 22442 | Ugt2b38 | NM_139894.2 | chr5:87409939-87424203 |
| 22346 | Ube2q1 | NM_027315.4 | chr3:89773608-89783997 | 22443 | Ugt2b5 | NM_009467.3 | chr5:87124946-87140340 |
| 22347 | Ube2q2 | NM_180600.3 | chr9:55149368-55207529 | 22444 | Ugt3a1 | NM_207216.2 | chr15:9279828-9315036 |
| 22348 | Ube2q1l | NM_001141820.1 | chr4:41136020-41193370 | 22445 | Ugt3a2 | NM_144845.3 | chr15:9335597-9370870 |
| 22349 | Ube2r2 | NM_026275.4 | chr4:41136020-41193370 | 22446 | Ugt8a | NM_011674.4 | chr3:125365342-125938550 |
| 22350 | Ube2s | NM_133777.2 | chr7:4808013-4812340 | 22447 | Uhmk1 | NM_010633.3 | chr1:170199255-170215393 |
| 22351 | Ube2t | NM_001276315.1 | chr1:134962564-134974179 | 22448 | Uhrf1 | NM_011110.78.1 | chr17:56304312-56323486 |
| 22352 | Ube2u | NM_001033773.4 | chr4:100478866-100550145 | 22449 | Uhrf1bp1 | NM_001080769.1 | chr17:27856506-27900040 |
| 22353 | Ube2v1 | NM_023230.2 | chr2:167640783-167632005 | 22450 | Uhrf1bp1l | NM_029166.2 | chr10:89744990-89819869 |
| 22354 | Ube2v2 | NM_001159351.1 | chr16:15550985-15594518 | 22451 | Uhrf2 | NM_144873.2 | chr19:30030612-30093724 |
| 22355 | Ube2w | NM_001271016.1 | chr1:16546787-16619338 | 22452 | Uimc1 | NM_013307.2 | chr13:55027879-55100295 |
| 22356 | Ube2z | NM_96047.03 | chr11:96065364 | 22453 | Ubp1 | NM_029975.2 | chr10:7444872-7473477 |
| 22357 | Ube3a | NM_001033962.1 | chr7:59223751-59306727 | 22454 | Ulk1 | NM_009469.3 | chr5:110784488-110810081 |
| 22358 | Ube3b | NM_054093.2 | chr5:114380606-114421166 | 22455 | Ulk2 | NM_013881.4 | chr11:61775597-61855092 |
| 22359 | Ube3c | NM_133967.2 | chr5:29569241-29676077 | 22456 | Ulk3 | NM_027895.1 | chr9:57589451-57596233 |
| 22360 | Ube4a | NM_145400.3 | chr9:44923126-44965600 | 22457 | Ulk4 | NM_175893.3 | chr9:120964453-121277172 |
| 22361 | Ube4b | NM_022022.3 | chr4:149328415-149426631 | 22458 | Umod | NM_001278605.1 | chr7:119462707-119479262 |
| 22362 | Ubfd1 | NM_138589.2 | chr17:122067197-122082199 | 22459 | Umodl1 | NM_177465.4 | chr17:30954682-31010710 |
| 22363 | Ubiad1 | NM_027873.2 | chr4:148434496-148444751 | 22460 | Umps | NM_009471.2 | chr16:33955011-33967003 |
| 22364 | Ubl3 | NM_011908.2 | chr5:148504630-148552788 | 22461 | Unc119 | NM_011676.3 | chr11:78343494-78349164 |
| 22365 | Ubl4 | NM_145405.2 | chrX:74365717-74368548 | 22462 | Unc119b | NM_175352.4 | chr5:115122565-115134975 |
| 22366 | Ubl4b | NM_026261.2 | chr3:107553697-107555073 | 22463 | Unc13a | NM_001029873.2 | chr8:71626711-71671757 |
| 22367 | Ubl5 | NM_024317.3 | chr9:20643317-20646789 | 22464 | Unc13b | NM_001081413.2 | chr4:43058952-43264873 |
| 22368 | Ubl7 | NM_001328873.1 | chr9:57910985-57929968 | 22465 | Unc13c | NM_001081153.1 | chr9:73479423-73933567 |
| 22369 | Ublcp1 | NM_024475.5 | chr11:44454570-44470548 | 22466 | Unc13d | NM_001009573.2 | chr11:116062095-116077961 |
| 22370 | Ubn1 | NM_026786.2 | chr16:5050067-5086285 | 22467 | Unc45a | NM_133952.2 | chr7:80325291-80340219 |
| 22371 | Ubn2 | NM_177185.4 | chr6:38433924-38512763 | 22468 | Unc45b | NM_178680.4 | chr11:82911252-82943406 |
| 22372 | Ubox5 | NM_001255993.1 | chr2:130589995-130630038 | 22469 | Unc50 | NM_026123.3 | chr1:37430171-37439124 |
| 22373 | Ubp1 | NM_001083319.1 | chr9:113930933-113977201 | 22470 | Unc5a | NM_153131.3 | chr13:54949431-55006018 |
| 22374 | Ubqln1 | NM_026842.4 | chr13:58176155-58215653 | 22471 | Unc5b | NM_029770.2 | chr10:60762594-60831581 |
| 22375 | Ubqln2 | NM_018798.2 | chrX:153498231-153501558 | 22472 | Unc5c | NM_009472.4 | chr3:141465563-141834924 |
| 22376 | Ubqln3 | NM_198623.2 | chr7:104140622-104143272 | 22473 | Unc5cl | NM_152823.4 | chr17:48454900-48468684 |
| 22377 | Ubqln4 | NM_033526.2 | chr3:88553715-88569725 | 22474 | Unc5d | NM_153135.3 | chr8:28646716-29219636 |
| 22378 | Ubqlnl | NM_198624.3 | chr7:104140458-104150556 | 22475 | Unc79 | NM_001081017.2 | chr12:102948858-103183997 |
| 22379 | Ubr1 | NM_009461.2 | chr2:120860275-120970715 | 22476 | Unc80 | NM_175510.3 | chr1:66468446-66699148 |
| 22380 | Ubr2 | NM_001177113.1 | chr17:13108616-13131791 | 22477 | Unc93a | NM_199252.2 | chr17:13108616-13131791 |
| 22381 | Ubr3 | NM_001303033.1 | chr2:69896969-70024010 | 22478 | Unc93b1 | NM_001161428.1 | chr19:3935185-3949340 |
| 22382 | Ubr4 | NM_001160319.1 | chr4:139380658-139489532 | 22479 | Uncx | NM_013702.3 | chr5:139543897-139548178 |
| 22383 | Ubr5 | NM_001081359.3 | chr15:37963727-38078354 | 22480 | Ung | NM_001040691.1 | chr5:114130434-114139321 |
| 22384 | Ubr7 | NM_025666.5 | chr12:102757974-102777703 | 22481 | Unk | NM_001286006.1 | chr11:116030315-116061214 |
| 22385 | Ubtd1 | NM_145500.3 | chr19:41981762-42034641 | 22482 | Unkl | NM_001197024.1 | chr17:25188399-25234442 |
| 22386 | Ubtd2 | NM_173784.1 | chr18:32455371-32518709 | 22483 | Uox | NM_009474.5 | chr3:146597148-146631483 |
| 22387 | Ubtf | NM_001044383.2 | chr11:102304562-102317287 | 22484 | Upb1 | NM_133995.4 | chr10:75406910-75431879 |
| 22388 | Ubtfl1 | NM_001033974.1 | chr9:18404417-18411502 | 22485 | Upf1 | NM_001122829.1 | chr8:70331521-70353273 |
| 22389 | Ubxn1 | NM_146093.1 | chr19:8871558-8875656 | 22486 | Upf2 | NM_001081132.1 | chr2:5951468-6056703 |
| 22390 | Ubxn10 | NM_001285928.1 | chr4:138718525-138737167 | 22487 | Upf3a | NM_025924.2 | chr8:13785614-13798537 |
| 22391 | Ubxn11 | NM_026257.3 | chr4:134102582-134126780 | 22488 | Upf3b | NM_026573.3 | chrX:37091677-37110322 |
| 22392 | Ubxn2a | NM_145441.3 | chr12:48790331-49072520 | 22489 | Upk1a | NM_026815.2 | chr7:30603093-30612734 |
| 22393 | Ubxn2b | NM_026534.2 | chr4:6191104-6219783 | 22490 | Upk1b | NM_178924.4 | chr16:38773183-38800203 |
| 22394 | Ubxn4 | NM_128244.168 | chr1:328244480-128279317 | 22491 | Upk2 | NM_009476.3 | chr9:44452714-44454767 |
| 22395 | Ubxn6 | NM_024432.2 | chr17:56068252-56074889 | 22492 | Upk3a | NM_029478.2 | chr15:85017140-85022860 |
| 22396 | Ubxn7 | NM_177063.1 | chr16:32332251-32393747 | 22493 | Upk3b | NM_175309.4 | chr5:136038495-136044953 |
| 22397 | Ubxn8 | NM_178648.2 | chr8:33619585-33641976 | 22494 | Upk3bl | NM_027158.1 | chr5:136057266-136064324 |
| 22398 | Uchl1 | NM_011670.2 | chr5:66676120-66687234 | 22495 | Upp1 | NM_001159401.1 | chr11:9118007-9136170 |
| 22399 | Uchl1os | NR_102714.1 | chr5:66626494-66676497 | 22496 | Upp2 | NM_001289659.1 | chr2:58755183-58791242 |
| 22400 | Uchl3 | NM_016723.2 | chr14:101663966-101696125 | 22497 | Uprt | NM_001081893.1 | chrX:104482783-104506262 |
| 22401 | Uchl4 | NM_033607.1 | chr9:64235200-64236362 | 22498 | Uqcc1 | NM_018888.4 | chr2:155846885-155930310 |
| 22402 | Uchl5 | NM_001159866.1 | chr1:143777277-143807466 | 22499 | Uqcc2 | NM_026063.2 | chr17:27122664-27133891 |
| 22403 | Uck1 | NM_011675.2 | chr2:32255001-32260105 | 22500 | Uqcr10 | NM_197979.2 | chr11:4701967-4704344 |
| 22404 | Uck2 | NM_030724.2 | chr1:167226083-167285127 | 22501 | Uqcr11 | NM_025650.2 | chr10:80402996-80406821 |
| 22405 | Uckl1 | NM_026765.3 | chr2:181598152-181581973 | 22502 | Uqcrb | NM_026219.1 | chr13:66900620-66905350 |
| 22406 | Uckl1os | NR_027289.1 | chr2:181578479-181585115 | 22503 | Uqcrc1 | NM_025407.2 | chr9:108936647-108949641 |

Fig.21 - 117

| | | | | | | | | |
|---|---|---|---|---|---|---|---|---|
| 22504 | Uqcrc2 | NM_025899.2 | chr7:120635188-120659523 | | 22601 | Uvrag | NM_178635.3 | chr7:98886742-99141144 |
| 22505 | Uqcrfs1 | NM_025710.2 | chr13:30540311-30945316 | | 22602 | Uvssa | NM_001081101.2 | chr5:33378695-33419754 |
| 22506 | Uqcrh | NM_025641.3 | chr4:116066964-116075070 | | 22603 | Uxs1 | NM_026480.3 | chr1:43750230-43827708 |
| 22507 | Uqcrq | NM_025352.2 | chr11:53428947-53430831 | | 22604 | Uxt | NM_013840.3 | chrX:20951664-20961978 |
| 22508 | Urad | NM_001039678.2 | chr5:147314983-147322440 | | 22605 | V1ra8 | NM_053223.1 | chr6:90202816-90209656 |
| 22509 | Urah | NM_029821.2 | chr7:140835495-140837968 | | 22606 | V1rd18 | NM_207618.2 | chr7:24003090-24004247 |
| 22510 | Urb1 | NM_029497.1 | chr16:90751526-90810413 | | 22607 | V1rd19 | NM_207619.2 | chr7:24003110-24004028 |
| 22511 | Urb2 | NM_001029876.1 | chr8:124023472-124048504 | | 22608 | Vac14 | NM_146216.2 | chr8:110618637-110720398 |
| 22512 | Urgcp | NM_001077661.1 | chr11:5713416-5762376 | | 22609 | Vamp1 | NM_001080557.1 | chr6:125215580-125222306 |
| 22513 | Uri1 | NM_011274.5 | chr7:37959991-38019552 | | 22610 | Vamp2 | NM_009497.3 | chr11:69088527-69092381 |
| 22514 | Urm1 | NM_026615.4 | chr2:29827388-29844996 | | 22611 | Vamp3 | NM_009498.4 | chr4:151047304-151057953 |
| 22515 | Uroc1 | NM_144940.2 | chr6:90333288-90364548 | | 22612 | Vamp4 | NM_016796.3 | chr1:162570827-162598078 |
| 22516 | Urod | NM_009478.4 | chr4:116989964-116994413 | | 22613 | Vamp5 | NM_001080742.2 | chr6:72368048-72380468 |
| 22517 | Uros | NM_009479.3 | chr7:133686354-133709295 | | 22614 | Vamp7 | NM_011515.5 | chrX_GL456233_random:10736-39191 |
| 22518 | Usb1 | NM_133954.2 | chr8:95332283-95347513 | | 22615 | Vamp8 | NM_016794.3 | chr6:72385220-72390667 |
| 22519 | Use1 | NM_001145780.1 | chr8:71366847-71369732 | | 22616 | Vangl1 | NM_177545.5 | chr3:102155899-102205011 |
| 22520 | Usf1 | NM_009480.3 | chr1:171411680-171418759 | | 22617 | Vangl2 | NM_033509.4 | chr1:172000959-172027295 |
| 22521 | Usf2 | NM_011680.2 | chr7:30945247-30956803 | | 22618 | Vapa | NM_013933.3 | chr17:65580052-65613555 |
| 22522 | Ush1c | NM_001163733.1 | chr7:46195350-46238490 | | 22619 | Vapb | NM_019806.5 | chr2:173737570-173784336 |
| 22523 | Ush1g | NM_176847.3 | chr11:115315191-115321918 | | 22620 | Vars | NM_011690.3 | chr17:35000906-35016329 |
| 22524 | Ush2a | NM_021408.3 | chr1:188262837-188965039 | | 22621 | Vars2 | NM_175137.4 | chr17:35655634-35667592 |
| 22525 | Ushbp1 | NM_181418.3 | chr8:71384273-71395801 | | 22622 | Vash1 | NM_177354.4 | chr12:86678699-86695681 |
| 22526 | Usmg5 | NM_023211.4 | chr19:47083470-47090625 | | 22623 | Vash2 | NM_144879.2 | chr1:190947645-190978998 |
| 22527 | Uso1 | NM_019490.1 | chr5:92137937-92202795 | | 22624 | Vasn | NM_139307.3 | chr16:4639944-4651166 |
| 22528 | Usp1 | NM_146144.4 | chr4:98923809-98935542 | | 22625 | Vasp | NM_001282021.1 | chr7:19256929-19271854 |
| 22529 | Usp10 | NM_009462.2 | chr8:119910359-119957559 | | 22626 | Vat1 | NM_012037.2 | chr11:101458747-101466199 |
| 22530 | Usp11 | NM_145628.4 | chrX:20703908-20720939 | | 22627 | Vat1l | NM_173016.3 | chr8:114205639-114374070 |
| 22531 | Usp12 | NM_011677.1 | chr5:146734811-146794956 | | 22628 | Vaultrc5 | NR_027885.1 | chr18:36801762-36802107 |
| 22532 | Usp13 | NM_001013024.2 | chr3:32817625-32935257 | | 22629 | Vav1 | NM_001163815.1 | chr17:57279099-57329236 |
| 22533 | Usp14 | NM_010388.2 | chr18:9993614-10030149 | | 22630 | Vav2 | NM_009500.3 | chr2:27263634-27426825 |
| 22534 | Usp15 | NM_027604.4 | chr10:123105005-123197019 | | 22631 | Vav3 | NM_020505.2 | chr3:109340682-109685694 |
| 22535 | Usp16 | NM_024258.2 | chr16:87454984-87483513 | | 22632 | Vax1 | NM_009501.1 | chr19:59166186-59170029 |
| 22536 | Usp17la | NM_087687.2 | chr7:104857015-104862667 | | 22633 | Vax2 | NM_011912.3 | chr6:83711263-83738304 |
| 22537 | Usp17lb | NM_201409.2 | chr7:104840311-104842606 | | 22634 | Vax2os | NR_002871.1 | chr6:83692805-83712201 |
| 22538 | Usp17lc | NM_010089.3 | chr7:103416695-103419174 | | 22635 | Vbp1 | NM_011692.2 | chrX:75514296-75534946 |
| 22539 | Usp17ld | NM_001001559.2 | chr7:103250085-103252505 | | 22636 | Vcam1 | NM_011693.3 | chr3:116110019-116129688 |
| 22540 | Usp17le | NM_001256973.1 | chr7:104768048-104777470 | | 22637 | Vcan | NM_001081249.1 | chr13:89655309-89742512 |
| 22541 | Usp18 | NM_011909.2 | chr6:121245905-121270917 | | 22638 | Vcl | NM_009502.4 | chr14:20929432-21033673 |
| 22542 | Usp19 | NM_001168371.2 | chr9:108490675-108502337 | | 22639 | Vcp | NM_009503.4 | chr4:42979963-43000507 |
| 22543 | Usp2 | NM_016808.2 | chr9:44069428-44095627 | | 22640 | Vcpip1 | NM_173443.2 | chr1:9718621-9748382 |
| 22544 | Usp20 | NM_028646.5 | chr2:30982278-31022665 | | 22641 | Vcpkmt | NM_001032236.2 | chr12:69577627-69583028 |
| 22545 | Usp21 | NM_013919.4 | chr1:171281952-171287961 | | 22642 | Vdac1 | NM_011694.5 | chr11:52360861-52389397 |
| 22546 | Usp22 | NM_001004143.4 | chr11:61151780-61175059 | | 22643 | Vdac2 | NM_011695.2 | chr14:21831560-21845879 |
| 22547 | Usp24 | NM_183225.2 | chr4:106316212-106441327 | | 22644 | Vdac3 | NM_001198998.1 | chr8:22577074-22593813 |
| 22548 | Usp25 | NM_013918.2 | chr16:77014068-77116780 | | 22645 | Vdr | NM_009504.4 | chr15:97854426-97908296 |
| 22549 | Usp26 | NM_031388.2 | chrX:51753958-51801233 | | 22646 | Vegfa | NM_001025250.3 | chr17:46016992-46032377 |
| 22550 | Usp27x | NM_019461.4 | chrX:7372590-7375830 | | 22647 | Vegfb | NM_001185164.1 | chr19:6982471-6987651 |
| 22551 | Usp28 | NM_175482.3 | chr9:48985384-49042517 | | 22648 | Vegfc | NM_009506.2 | chr8:54077531-54186454 |
| 22552 | Usp29 | NM_001290994.1 | chr7:6730582-6967219 | | 22649 | Vegph1 | NM_145820.3 | chr3:66053557-66296837 |
| 22553 | Usp3 | NM_144937.4 | chr9:66514638-66593115 | | 22650 | Vezf1 | NM_016686.4 | chr11:88068278-88084729 |
| 22554 | Usp30 | NM_001033202.3 | chr5:114100332-114122924 | | 22651 | Vezt | NM_172538.5 | chr10:93961521-94035799 |
| 22555 | Usp31 | NM_001033173.1 | chr7:121642020-121707253 | | 22652 | Vgf | NM_001039385.1 | chr5:137030294-137033351 |
| 22556 | Usp32 | NM_001029934.1 | chr11:84984487-85139955 | | 22653 | Vgll1 | NM_133251.2 | chrX:57088108-57106540 |
| 22557 | Usp33 | NM_001076676.2 | chr3:152346477-152393614 | | 22654 | Vgll2 | NM_153786.2 | chr10:52022501-52028471 |
| 22558 | Usp34 | NM_001190401.2 | chr11:23306894-23490560 | | 22655 | Vgll3 | NM_028572.1 | chr16:65815632-65863066 |
| 22559 | Usp35 | NM_001177412.1 | chr7:97309379-97325964 | | 22656 | Vgll4 | NM_177683.2 | chr6:114862091-114921752 |
| 22560 | Usp36 | NM_001033518.1 | chr11:118259652-118290244 | | 22657 | Vhl | NM_009507.3 | chr6:113624020-113631633 |
| 22561 | Usp37 | NM_176972.4 | chr1:74435509-74544286 | | 22658 | Vill | NM_009509.2 | chr1:74409383-74435560 |
| 22562 | Usp38 | NM_027554.2 | chr8:80980732-81014906 | | 22659 | Vill | NM_001164567.1 | chr9:119052777-119071525 |
| 22563 | Usp39 | NM_138592.4 | chr6:72318675-72345175 | | 22660 | Vim | NM_011701.4 | chr2:13574310-13582826 |
| 22564 | Usp4 | NM_011678.2 | chr9:108347830-108392529 | | 22661 | Vimp | NM_024439.3 | chr7:66079648-66089405 |
| 22565 | Usp40 | NM_001033291.2 | chr1:87945120-88008551 | | 22662 | Vip | NM_011702.3 | chr10:5639217-5647616 |
| 22566 | Usp42 | NM_029749.2 | chr5:143710925-143732280 | | 22663 | Vipas39 | NM_001142580.1 | chr12:87238874-87266286 |
| 22567 | Usp43 | NM_001291049.1 | chr11:67854522-67922153 | | 22664 | Vipr1 | NM_011703.4 | chr9:121642715-121672954 |
| 22568 | Usp44 | NM_001206851.1 | chr10:93831554-93858087 | | 22665 | Vipr2 | NM_009511.2 | chr12:116077725-116146261 |
| 22569 | Usp45 | NM_001290425.1 | chr4:21776269-21837872 | | 22666 | Vit | NM_001197028.1 | chr17:78580862-78627409 |
| 22570 | Usp46 | NM_177561.3 | chr5:74000037-74068411 | | 22667 | Vkorc1 | NM_178600.2 | chr7:127893062-127895617 |
| 22571 | Usp47 | NM_133764.3 | chr7:112023606-112111386 | | 22668 | Vkorc1l1 | NM_001001327.2 | chr5:129942108-129986692 |
| 22572 | Usp48 | NM_130879.2 | chr4:137594188-137658637 | | 22669 | Vldlr | NM_001161420.1 | chr19:27217019-27254231 |
| 22573 | Usp49 | NM_198421.1 | chr17:47630689-47684067 | | 22670 | Vma21 | NM_001081356.3 | chrX:71816757-71824706 |
| 22574 | Usp5 | NM_013700.3 | chr6:124815019-124829447 | | 22671 | Vmac | NM_001166474.1 | chr17:56713931-56717699 |
| 22575 | Usp50 | NM_029163.3 | chr2:126761049-126783460 | | 22672 | Vmn1r1 | NM_001166728.1 | chr1:182157177-182158098 |
| 22576 | Usp51 | NM_001137547.1 | chrX:153006468-153009459 | | 22673 | Vmn1r10 | NM_053231.2 | chr6:57113424-57114360 |
| 22577 | Usp53 | NM_133857.3 | chr3:122933600-122984447 | | 22674 | Vmn1r100 | NM_001166844.1 | chr7:20417941-22414306 |
| 22578 | Usp54 | NM_030180.2 | chr14:20548911-20613354 | | 22675 | Vmn1r101 | NM_001166836.1 | chr7:20441669-22438229 |
| 22579 | Usp6nl | NM_001080548.1 | chr2:6322756-6443620 | | 22676 | Vmn1r103 | NM_001166737.1 | chr7:20509616-20510534 |
| 22580 | Usp7 | NM_001003918.2 | chr16:8688721-8738342 | | 22677 | Vmn1r104 | NM_001166738.1 | chr7:20533836-22523890 |
| 22581 | Usp8 | NM_001252580.1 | chr2:126707327-126799314 | | 22678 | Vmn1r107 | NM_001166759.1 | chr7:20668917-23218255 |
| 22582 | Usp9x | NM_009481.2 | chrX:13071497-13173327 | | 22679 | Vmn1r11 | NM_053233.2 | chr6:57137352-57138252 |
| 22583 | Usp9y | NM_148943.2 | chrY:1298960-1459782 | | 22680 | Vmn1r112 | NM_001166847.1 | chr7:20771184-20772076 |
| 22584 | Uspl1 | NM_001013378.2 | chr5:149184959-149215434 | | 22681 | Vmn1r113 | NM_001166716.1 | chr7:20787284-20788208 |
| 22585 | Ust | NM_177387.3 | chr10:8204752-8518825 | | 22682 | Vmn1r114 | NM_001166837.1 | chr7:20811220-20812186 |
| 22586 | Utf1 | NM_009482.2 | chr7:139943855-139945112 | | 22683 | Vmn1r115 | NM_001166745.1 | chr7:20844097-20844985 |
| 22587 | Utp11l | NM_026031.3 | chr4:124678763-124693554 | | 22684 | Vmn1r116 | NM_001166744.1 | chr7:20872255-20873173 |
| 22588 | Utp14a | NM_028276.1 | chrX:48256933-48282449 | | 22685 | Vmn1r117 | NM_001166743.1 | chr7:20883197-20884121 |
| 22589 | Utp14b | NM_001001981.3 | chr1:78657824-78667601 | | 22686 | Vmn1r118 | NM_001166742.1 | chr7:20232907-22229484 |
| 22590 | Utp15 | NM_178912.3 | chr13:98246844-98262992 | | 22687 | Vmn1r119 | NM_001166708.1 | chr7:21011531-21012455 |
| 22591 | Utp18 | NM_001013375.1 | chr11:93859242-93885766 | | 22688 | Vmn1r12 | NM_001101579.1 | chr6:57158919-57159843 |
| 22592 | Utp20 | NM_175158.3 | chr10:88746606-88826814 | | 22689 | Vmn1r120 | NM_001166715.1 | chr7:21053866-21053784 |
| 22593 | Utp23 | NM_030132.5 | chr15:51877440-51884622 | | 22690 | Vmn1r121 | NM_001166741.1 | chr7:21097568-21098513 |
| 22594 | Utp3 | NM_023054.3 | chr5:88554482-88556083 | | 22691 | Vmn1r122 | NM_001166714.1 | chr7:21133219-21134128 |
| 22595 | Utp6 | NM_144826.3 | chr11:79933955-79962387 | | 22692 | Vmn1r123 | NM_001166707.1 | chr7:21162184-21163108 |
| 22596 | Utrn | NM_011682.4 | chr10:12382187-12861735 | | 22693 | Vmn1r124 | NM_001166757.1 | chr7:21259693-21260617 |
| 22597 | Uts2 | NM_011910.2 | chr4:150997096-151001810 | | 22694 | Vmn1r125 | NM_001166740.1 | chr7:21272178-21273102 |
| 22598 | Uts2b | NM_198166.3 | chr16:27353321-27370239 | | 22695 | Vmn1r126 | NM_001001983.3 | chr7:21300501-21301467 |
| 22599 | Uts2r | NM_145440.1 | chr11:121160270-121161975 | | 22696 | Vmn1r127 | NM_001166726.1 | chr7:21318943-21319861 |
| 22600 | Uty | NM_009484.2 | chrY:1097143-1245738 | | 22697 | Vmn1r128 | NM_001166739.1 | chr7:21349372-21350296 |

Fig.21 - 118

| | | | | | | | | |
|---|---|---|---|---|---|---|---|---|
| 22698 | Vmn1r129 | NM_001166725.1 | chr7:21360367-21361291 | | 22795 | Vmn1r236 | NM_134201.2 | chr17:21286532-21287653 |
| 22699 | Vmn1r13 | NM_053235.2 | chr6:57209857-57210760 | | 22796 | Vmn1r237 | NM_134200.1 | chr17:21314016-21314886 |
| 22700 | Vmn1r130 | NM_001166848.1 | chr7:21511780-21512703 | | 22797 | Vmn1r238 | NM_001167539.1 | chr18:3122491-3123412 |
| 22701 | Vmn1r132 | NM_001122682.1 | chr7:21612744-22097921 | | 22798 | Vmn1r24 | NM_134173.2 | chr6:57955640-57956531 |
| 22702 | Vmn1r135 | NM_001166747.1 | chr7:21832350-23056463 | | 22799 | Vmn1r25 | NM_053238.2 | chr6:57978393-57979302 |
| 22703 | Vmn1r137 | NM_001166849.1 | chr7:21994587-21995510 | | 22800 | Vmn1r26 | NM_134172.1 | chr6:58008182-58009202 |
| 22704 | Vmn1r138 | NM_001167169.1 | chr7:22027977-22028897 | | 22801 | Vmn1r27 | NM_134436.2 | chr6:58215105-58216017 |
| 22705 | Vmn1r139 | NM_001166748.1 | chr7:21614091-22097760 | | 22802 | Vmn1r28 | NM_134180.1 | chr6:58265173-58266082 |
| 22706 | Vmn1r14 | NM_053237.2 | chr6:57233438-57234350 | | 22803 | Vmn1r29 | NM_053232.1 | chr6:58307296-58308208 |
| 22707 | Vmn1r142 | NM_001166749.1 | chr7:20167459-22164035 | | 22804 | Vmn1r3 | NM_001167535.1 | chr4:3184384-3185305 |
| 22708 | Vmn1r148 | NM_030736.2 | chr7:22412230-22414668 | | 22805 | Vmn1r30 | NM_134177.1 | chr6:58434936-58435845 |
| 22709 | Vmn1r15 | NM_053236.2 | chr6:57258148-57259048 | | 22806 | Vmn1r31 | NM_001166729.1 | chr6:58471966-58472878 |
| 22710 | Vmn1r151 | NM_001166712.1 | chr7:22498760-22499678 | | 22807 | Vmn1r32 | NM_134170.3 | chr6:66525182-66559708 |
| 22711 | Vmn1r152 | NM_001166752.1 | chr7:20533836-22523890 | | 22808 | Vmn1r33 | NM_134169.1 | chr6:66611650-66612568 |
| 22712 | Vmn1r157 | NM_001166754.1 | chr7:22761696-22762590 | | 22809 | Vmn1r34 | NM_001166719.1 | chr6:66636822-66637752 |
| 22713 | Vmn1r158 | NM_001166841.1 | chr7:22789858-22790782 | | 22810 | Vmn1r35 | NM_134167.1 | chr6:66678793-66679684 |
| 22714 | Vmn1r159 | NM_001166758.1 | chr7:22842687-22843605 | | 22811 | Vmn1r36 | NM_134166.1 | chr6:66715971-66716889 |
| 22715 | Vmn1r16 | NM_134184.2 | chr6:57322723-57323635 | | 22812 | Vmn1r37 | NM_134165.1 | chr6:66731391-66732300 |
| 22716 | Vmn1r160 | NM_001166724.1 | chr7:22871223-22872147 | | 22813 | Vmn1r38 | NM_134168.1 | chr6:66776223-66777130 |
| 22717 | Vmn1r163 | NM_001166755.1 | chr7:23055540-23056463 | | 22814 | Vmn1r39 | NM_001166720.1 | chr6:66804414-66805332 |
| 22718 | Vmn1r165 | NM_001166850.1 | chr7:23217332-23218255 | | 22815 | Vmn1r4 | NM_134176.1 | chr6:56956512-56957405 |
| 22719 | Vmn1r166 | NM_001167168.1 | chr7:23250762-23251682 | | 22816 | Vmn1r40 | NM_053228.1 | chr6:89714202-89715135 |
| 22720 | Vmn1r167 | NM_001101562.1 | chr7:23504641-23505589 | | 22817 | Vmn1r41 | NM_053230.2 | chr6:89740687-89747414 |
| 22721 | Vmn1r168 | NM_001166842.1 | chr7:23540719-23541649 | | 22818 | Vmn1r42 | NM_053221.2 | chr6:89844517-89845615 |
| 22722 | Vmn1r169 | NM_001166843.1 | chr7:23577184-23578099 | | 22819 | Vmn1r43 | NM_053220.2 | chr6:89869460-89870529 |
| 22723 | Vmn1r17 | NM_134171.1 | chr6:57360466-57361378 | | 22820 | Vmn1r44 | NM_053227.2 | chr6:89893273-89894206 |
| 22724 | Vmn1r170 | NM_001166722.1 | chr7:23606174-23607089 | | 22821 | Vmn1r45 | NM_011684.2 | chr6:89931649-89940507 |
| 22725 | Vmn1r171 | NM_030737.2 | chr7:23631987-23633568 | | 22822 | Vmn1r46 | NM_053229.1 | chr6:89976170-89977100 |
| 22726 | Vmn1r172 | NM_030735.1 | chr7:23658315-23660663 | | 22823 | Vmn1r47 | NM_053219.2 | chr6:90021887-90022820 |
| 22727 | Vmn1r173 | NM_001166718.1 | chr7:23702341-23703283 | | 22824 | Vmn1r48 | NM_053218.1 | chr6:90035932-90036841 |
| 22728 | Vmn1r174 | NM_207548.2 | chr7:23753910-23754852 | | 22825 | Vmn1r49 | NM_011911.1 | chr6:90072085-90073018 |
| 22729 | Vmn1r175 | NM_001166727.1 | chr7:23808285-23809200 | | 22826 | Vmn1r5 | NM_134174.2 | chr6:56985341-56986289 |
| 22730 | Vmn1r176 | NM_001166721.1 | chr7:23834811-23835726 | | 22827 | Vmn1r50 | NM_053225.1 | chr6:80107274-90108207 |
| 22731 | Vmn1r177 | NM_206872.2 | chr7:23865519-23866449 | | 22828 | Vmn1r51 | NM_011683.2 | chr6:90122642-90130645 |
| 22732 | Vmn1r178 | NM_206868.1 | chr7:23893528-23894443 | | 22829 | Vmn1r52 | NM_053222.1 | chr6:90178715-90179643 |
| 22733 | Vmn1r179 | NM_207545.1 | chr7:23928386-23929357 | | 22830 | Vmn1r53 | NM_053226.2 | chr6:90223316-90224438 |
| 22734 | Vmn1r18 | NM_134181.1 | chr6:57389667-57390687 | | 22831 | Vmn1r54 | NM_053224.1 | chr6:90269105-90270053 |
| 22735 | Vmn1r180 | NM_206869.2 | chr7:23952386-23953356 | | 22832 | Vmn1r55 | NM_001166706.1 | chr7:5146489-5147422 |
| 22736 | Vmn1r181 | NM_207546.2 | chr7:23983960-23985048 | | 22833 | Vmn1r56 | NM_030740.1 | chr7:5194915-5196747 |
| 22737 | Vmn1r183 | NM_203489.1 | chr7:24054773-24055691 | | 22834 | Vmn1r57 | NM_001166734.1 | chr7:5220477-5221410 |
| 22738 | Vmn1r184 | NM_001167540.1 | chr7:26266830-26267775 | | 22835 | Vmn1r58 | NM_030739.2 | chr7:5408889-5413145 |
| 22739 | Vmn1r185 | NM_134231.1 | chr7:26611118-28612078 | | 22836 | Vmn1r59 | NM_207543.1 | chr7:5453826-5454759 |
| 22740 | Vmn1r186 | NM_001167567.1 | chr7:94185-5676224 | | 22837 | Vmn1r6 | NM_134175.1 | chr6:57002354-57003266 |
| 22741 | Vmn1r187 | NM_001167568.1 | chr7:149260-5803631 | | 22838 | Vmn1r60 | NM_001166732.1 | chr7:5544196-5545099 |
| 22742 | Vmn1r188 | NM_145850.1 | chr13:22087877-22088804 | | 22839 | Vmn1r61 | NM_001166733.1 | chr7:5610410-5611313 |
| 22743 | Vmn1r189 | NM_145844.1 | chr13:22101726-22102665 | | 22840 | Vmn1r62 | NM_030741.2 | chr7:93810-5678597 |
| 22744 | Vmn1r19 | NM_134182.1 | chr6:57404463-57405390 | | 22841 | Vmn1r63 | NM_030742.1 | chr7:148880-5805445 |
| 22745 | Vmn1r191 | NM_145849.1 | chr13:22178685-22179582 | | 22842 | Vmn1r64 | NM_207544.1 | chr7:5883579-5884542 |
| 22746 | Vmn1r192 | NM_145845.1 | chr13:22187145-22188048 | | 22843 | Vmn1r65 | NM_030738.2 | chr7:6007749-6011010 |
| 22747 | Vmn1r193 | NM_134225.1 | chr13:22218860-22219320 | | 22844 | Vmn1r66 | NM_134230.3 | chr7:10273827-10275351 |
| 22748 | Vmn1r194 | NM_001080972.1 | chr13:22244214-22245105 | | 22845 | Vmn1r67 | NM_134229.2 | chr7:10446788-10447787 |
| 22749 | Vmn1r195 | NM_134223.2 | chr13:22278316-22279404 | | 22846 | Vmn1r68 | NM_001172072.1 | chr7:10527209-10528169 |
| 22750 | Vmn1r196 | NM_001167565.1 | chr13:22293192-22294098 | | 22847 | Vmn1r69 | NM_145842.3 | chr7:10579755-10581487 |
| 22751 | Vmn1r197 | NM_134244.1 | chr13:22327910-22328807 | | 22848 | Vmn1r7 | NM_001166710.1 | chr6:57024837-57025273 |
| 22752 | Vmn1r198 | NM_134245.1 | chr13:22354345-22355248 | | 22849 | Vmn1r70 | NM_134228.1 | chr7:10633586-10634483 |
| 22753 | Vmn1r199 | NM_134213.1 | chr13:22382537-22383641 | | 22850 | Vmn1r71 | NM_145848.3 | chr7:10747501-10749538 |
| 22754 | Vmn1r2 | NM_001167534.1 | chr4:3172082-3173003 | | 22851 | Vmn1r72 | NM_145843.1 | chr7:11669598-11670519 |
| 22755 | Vmn1r20 | NM_001101533.1 | chr6:57431690-57432602 | | 22852 | Vmn1r73 | NM_134203.1 | chr7:11756256-11757168 |
| 22756 | Vmn1r200 | NM_134212.1 | chr13:22395028-22395967 | | 22853 | Vmn1r74 | NM_134206.1 | chr7:11846774-11847689 |
| 22757 | Vmn1r201 | NM_134221.1 | chr13:22474617-22475520 | | 22854 | Vmn1r75 | NM_134207.1 | chr7:11880342-11881260 |
| 22758 | Vmn1r202 | NM_134224.1 | chr13:22501336-22502245 | | 22855 | Vmn1r76 | NM_134205.2 | chr7:11930310-11931285 |
| 22759 | Vmn1r203 | NM_134236.1 | chr13:22524050-22524986 | | 22856 | Vmn1r77 | NM_001166731.1 | chr7:12041298-12042219 |
| 22760 | Vmn1r204 | NM_001045544.1 | chr13:22556200-22557109 | | 22857 | Vmn1r78 | NM_134208.2 | chr7:12152463-12153405 |
| 22761 | Vmn1r205 | NM_134217.1 | chr13:22591979-22592930 | | 22858 | Vmn1r79 | NM_001166835.1 | chr7:12176192-12177113 |
| 22762 | Vmn1r206 | NM_134216.1 | chr13:22620096-22621035 | | 22859 | Vmn1r8 | NM_134187.3 | chr6:57035912-57037125 |
| 22763 | Vmn1r207-ps | NM_001166709.1 | chr13:22725683-22726622 | | 22860 | Vmn1r80 | NM_134204.2 | chr7:12192964-12193891 |
| 22764 | Vmn1r208 | NM_134218.1 | chr13:22772398-22773325 | | 22861 | Vmn1r81 | NM_134210.1 | chr7:12259758-12260679 |
| 22765 | Vmn1r209 | NM_001013787.1 | chr13:22805579-22806518 | | 22862 | Vmn1r82 | NM_134234.1 | chr7:12304804-12305719 |
| 22766 | Vmn1r21 | NM_134185.1 | chr6:57843563-57844457 | | 22863 | Vmn1r83 | NM_134209.1 | chr7:12321207-12322128 |
| 22767 | Vmn1r210 | NM_134235.1 | chr13:22827193-22828114 | | 22864 | Vmn1r84 | NM_134233.1 | chr7:12361807-12362764 |
| 22768 | Vmn1r211 | NM_134243.1 | chr13:22851598-22852495 | | 22865 | Vmn1r85 | NM_145847.1 | chr7:13084288-13085215 |
| 22769 | Vmn1r212 | NM_134241.1 | chr13:22880087-22884161 | | 22866 | Vmn1r86 | NM_001167536.1 | chr7:13101996-13102947 |
| 22770 | Vmn1r213 | NM_134215.1 | chr13:23011248-23012403 | | 22867 | Vmn1r87 | NM_134227.1 | chr7:13131470-13132358 |
| 22771 | Vmn1r214 | NM_134214.1 | chr13:23034337-23035441 | | 22868 | Vmn1r88 | NM_001167537.1 | chr7:13177718-13178669 |
| 22772 | Vmn1r215 | NM_134219.1 | chr13:23075791-23076694 | | 22869 | Vmn1r89 | NM_134226.1 | chr7:13219338-13220289 |
| 22773 | Vmn1r216 | NM_134245.1 | chr13:23099148-23100045 | | 22870 | Vmn1r9 | NM_134185.2 | chr6:57070894-57071945 |
| 22774 | Vmn1r217 | NM_134239.1 | chr13:23111833-23114730 | | 22871 | Vmn1r90 | NM_001244031.1 | chr7:14561241-14562171 |
| 22775 | Vmn1r218 | NM_134222.1 | chr13:23136484-23137381 | | 22872 | Vmn1r91 | NM_001166736.1 | chr7:20101157-20102081 |
| 22776 | Vmn1r219 | NM_134238.1 | chr13:23162642-23163581 | | 22873 | Vmn1r94 | NM_001166723.1 | chr7:20167459-22164035 |
| 22777 | Vmn1r22 | NM_134178.1 | chr6:57900081-57900990 | | 22874 | Vmn1r95 | NM_001167538.1 | chr7:20193709-22190300 |
| 22778 | Vmn1r220 | NM_134237.1 | chr13:23183627-23184524 | | 22875 | Vmn1r-ps103 | NM_134211.2 | chr13:22441271-22442243 |
| 22779 | Vmn1r221 | NM_001167542.1 | chr13:23217372-23218311 | | 22876 | Vmn1r-ps79 | NR_030707.1 | chr7:20356625-22354555 |
| 22780 | Vmn1r222 | NM_134240.1 | chr13:23232114-23233041 | | 22877 | Vmn2r1 | NM_019918.2 | chr5:64081641-64105458 |
| 22781 | Vmn1r223 | NM_001083311.1 | chr13:23249237-23250323 | | 22878 | Vmn2r10 | NM_009491.3 | chr5:108995538-109006436 |
| 22782 | Vmn1r224 | NM_001166735.1 | chr13:20419162-20426059 | | 22879 | Vmn2r100 | NM_001104562.1 | chr17:19504810-19532060 |
| 22783 | Vmn1r225 | NM_134194.1 | chr17:20502298-20503195 | | 22880 | Vmn2r101 | NM_001104563.1 | chr17:19577230-19612317 |
| 22784 | Vmn1r226 | NM_134191.1 | chr17:20687507-20688404 | | 22881 | Vmn2r102 | NM_001104564.1 | chr17:19660398-19694748 |
| 22785 | Vmn1r227 | NM_134195.2 | chr17:20735099-20736126 | | 22882 | Vmn2r103 | NM_001104565.1 | chr17:19773362-19812536 |
| 22786 | Vmn1r228 | NM_134192.3 | chr17:20776058-20777501 | | 22883 | Vmn2r104 | NM_001104566.1 | chr17:20029424-20048205 |
| 22787 | Vmn1r229 | NM_134190.1 | chr17:20814494-20815415 | | 22884 | Vmn2r105 | NM_001104567.1 | chr17:20208229-20234872 |
| 22788 | Vmn1r23 | NM_134179.1 | chr6:57925882-57926791 | | 22885 | Vmn2r106 | NM_001104568.1 | chr17:20267546-20285430 |
| 22789 | Vmn1r230 | NM_134197.1 | chr17:20846650-20847501 | | 22886 | Vmn2r107 | NM_001104569.1 | chr17:20345424-20375772 |
| 22790 | Vmn1r231 | NM_134196.1 | chr17:20889715-20890651 | | 22887 | Vmn2r108 | NM_001104570.1 | chr17:20462372-20481236 |
| 22791 | Vmn1r232 | NM_134193.2 | chr17:20913204-20914363 | | 22888 | Vmn2r109 | NM_001104571.1 | chr17:20540516-20564756 |
| 22792 | Vmn1r233 | NM_001093726.1 | chr17:20993725-20994686 | | 22889 | Vmn2r11 | NM_001104571.1 | chr5:109046872-109059452 |
| 22793 | Vmn1r234 | NM_134198.1 | chr17:21228825-21229815 | | 22890 | Vmn2r110 | NM_001104572.1 | chr17:20573828-20596259 |
| 22794 | Vmn1r235 | NM_134199.3 | chr17:21260426-21262863 | | 22891 | Vmn2r111 | NM_001104573.1 | chr17:22547940-22573273 |

Fig.21 - 119

| | | | | | | | |
|---|---|---|---|---|---|---|---|
| 22892 | Vmn2r112 | NM_001104575.1 | chr17:22601147-22619133 | 22989 | Vmn2r90 | NM_001104539.1 | chr17:17703940-17734167 |
| 22893 | Vmn2r113 | NM_001104578.1 | chr17:22943183-22958814 | 22990 | Vmn2r91 | NM_001104540.1 | chr17:18085056-18136643 |
| 22894 | Vmn2r114 | NM_001102584.1 | chr17:23290933-23312313 | 22991 | Vmn2r92 | NM_001104541.1 | chr17:18151929-18185178 |
| 22895 | Vmn2r115 | NM_001104579.1 | chr17:23343976-23360128 | 22992 | Vmn2r93 | NM_001104542.1 | chr17:18298280-18326441 |
| 22896 | Vmn2r116 | NM_001104580.1 | chr17:23384802-23401864 | 22993 | Vmn2r94 | NM_001104543.1 | chr17:18243569-18277566 |
| 22897 | Vmn2r117 | NM_001104581.1 | chr17:23459674-23479597 | 22994 | Vmn2r95 | NM_001102581.1 | chr17:18424103-18452324 |
| 22898 | Vmn2r118 | NM_001104582.1 | chr17:55592340-55624672 | 22995 | Vmn2r96 | NM_001104547.1 | chr17:18581726-18598157 |
| 22899 | Vmn2r12 | NM_001104623.1 | chr5:109085848-109097864 | 22996 | Vmn2r97 | NM_001104549.1 | chr17:18914321-18948071 |
| 22900 | Vmn2r120 | NM_001104581.1 | chr17:57508782-57545314 | 22997 | Vmn2r98 | NM_001104550.1 | chr17:19053492-19081311 |
| 22901 | Vmn2r121 | NM_001100616.1 | chrX:124127338-124135910 | 22998 | Vmn2r99 | NM_001104551.2 | chr17:19362134-19394590 |
| 22902 | Vmn2r122 | NM_009488.2 | chr4_JH584292_random:3535-19355 | 22999 | Vmn2r-ps11 | NR_033962.1 | chr3:64632862-64844743 |
| 22903 | Vmn2r123 | NM_009485.1 | chr4:156331125-156339496 | 23000 | Vmn2r-ps129 | NR_033648.1 | chr17:23004970-23006659 |
| 22904 | Vmn2r124 | NM_001271863.1 | chr17:18049483-18074220 | 23001 | Vmn2r-ps159 | NR_028141.1 | chr4:156331102-156339499 |
| 22905 | Vmn2r13 | NM_001104624.1 | chr5:109195067-109192107 | 23002 | Vmn2r-ps54 | NR_004441.1 | chr7:41668013-41727193 |
| 22906 | Vmn2r14 | NM_001104625.1 | chr5:109215501-109224622 | 23003 | Vmn2r-ps60 | NR_028441.1 | chr7:42430104-42430369 |
| 22907 | Vmn2r15 | NM_001104626.1 | chr5:109286268-109297556 | 23004 | Vmo1 | NM_001013607.1 | chr11:70513515-70514616 |
| 22908 | Vmn2r16 | NM_001104627.1 | chr5:109330380-109364481 | 23005 | Vmp1 | NM_029478.3 | chr11:86583864-86683822 |
| 22909 | Vmn2r17 | NM_001104628.1 | chr5:109420012-109453387 | 23006 | Vnn1 | NM_011704.3 | chr10:23894687-23905343 |
| 22910 | Vmn2r18 | NM_001102582.1 | chr5:151561660-151586924 | 23007 | Vnn3 | NM_011979.2 | chr10:23851461-23869843 |
| 22911 | Vmn2r19 | NM_001104632.1 | chr5:123308332-123336537 | 23008 | Vopp1 | NM_146168.1 | chr6:57752263-57825125 |
| 22912 | Vmn2r2 | NM_001104592.1 | chr3:64116431-64137480 | 23009 | Vprbp | NM_001015507.2 | chr9:106821975-106880992 |
| 22913 | Vmn2r20 | NM_001104634.1 | chr6:123385261-123418061 | 23010 | Vpreb1 | NM_016982.2 | chr16:16868400-16869255 |
| 22914 | Vmn2r21 | NM_001104635.1 | chr6:123493507-123533406 | 23011 | Vpreb2 | NM_016983.1 | chr16:17980564-17981080 |
| 22915 | Vmn2r22 | NM_001104637.1 | chr6:123609757-123650635 | 23012 | Vpreb3 | NM_009514.4 | chr10:75948311-75949646 |
| 22916 | Vmn2r23 | NM_001104638.1 | chr6:123702820-123742239 | 23013 | Vps11 | NM_027889.1 | chr9:44348104-44361670 |
| 22917 | Vmn2r24 | NM_001104639.1 | chr6:123778970-123816280 | 23014 | Vps13a | NM_173028.4 | chr19:16615365-16780933 |
| 22918 | Vmn2r25 | NM_001104641.1 | chr6:123822813-123853190 | 23015 | Vps13b | NM_177151.3 | chr15:35371545-35931229 |
| 22919 | Vmn2r26 | NM_019917.2 | chr6:124024757-124062035 | 23016 | Vps13c | NM_177184.3 | chr9:67840395-67995634 |
| 22920 | Vmn2r27 | NM_001104642.1 | chr6:124191595-124231784 | 23017 | Vps13d | NM_001276465.1 | chr4:144972621-145195005 |
| 22921 | Vmn2r28 | NM_001081405.1 | chr7:5480455-5493851 | 23018 | Vps16 | NM_030559.3 | chr2:130424319-130444269 |
| 22922 | Vmn2r29 | NM_001113468.1 | chr7:7231326-7247328 | 23019 | Vps18 | NM_172269.3 | chr2:119288741-119298453 |
| 22923 | Vmn2r3 | NM_001104631.1 | chr3:64255960-64287417 | 23020 | Vps25 | NM_001284411.1 | chr11:101253706-101259547 |
| 22924 | Vmn2r30 | NM_009490.3 | chr7:7312273-7337493 | 23021 | Vps26a | NM_001113355.1 | chr10:62454842-62486598 |
| 22925 | Vmn2r31 | NM_001105062.1 | chr7:7383984-7399627 | 23022 | Vps26b | NM_178027.4 | chr9:27004501-27030094 |
| 22926 | Vmn2r32 | NM_001105063.1 | chr7:7463068-7479973 | 23023 | Vps28 | NM_025842.4 | chr15:76622085-76626084 |
| 22927 | Vmn2r33 | NM_001105065.2 | chr7:7550966-7566786 | 23024 | Vps29 | NM_019780.1 | chr5:122354412-122363287 |
| 22928 | Vmn2r34 | NM_001105066.1 | chr7:7671828-7689398 | 23025 | Vps33a | NM_029929.3 | chr5:123528759-123573015 |
| 22929 | Vmn2r35 | NM_001105067.1 | chr7:7786150-7819867 | 23026 | Vps33b | NM_178070.4 | chr7:80269654-80291579 |
| 22930 | Vmn2r36 | NM_001105068.1 | chr7:7876652-7902462 | 23027 | Vps35 | NM_022997.4 | chr8:85260391-85299497 |
| 22931 | Vmn2r37 | NM_009489.2 | chr7:8926548-9223653 | 23028 | Vps36 | NM_027338.1 | chr8:22192859-22218597 |
| 22932 | Vmn2r38 | NM_001105070.1 | chr7:9074795-9097765 | 23029 | Vps37a | NM_033560.3 | chr8:40611782-40651134 |
| 22933 | Vmn2r39 | NM_001105071.1 | chr7:9014749-9030682 | 23030 | Vps37b | NM_177876.4 | chr5:124004640-124032260 |
| 22934 | Vmn2r4 | NM_001104615.1 | chr3:64388620-64410057 | 23031 | Vps37c | NM_181403.2 | chr19:10688814-10714419 |
| 22935 | Vmn2r40 | NM_001105072.1 | chr7:8907733-8931402 | 23032 | Vps37d | NM_001199672.1 | chr5:135072899-135078266 |
| 22936 | Vmn2r41 | NM_001105073.1 | chr7:8137904-8161551 | 23033 | Vps39 | NM_147153.3 | chr2:120316460-120353133 |
| 22937 | Vmn2r42 | NM_009493.2 | chr7:8183268-8200320 | 23034 | Vps41 | NM_172120.4 | chr13:18717291-18866811 |
| 22938 | Vmn2r43 | NM_198961.2 | chr7:8244350-8260599 | 23035 | Vps45 | NM_013841.3 | chr3:95999831-96058455 |
| 22939 | Vmn2r44 | NM_001105074.1 | chr7:8367459-8383238 | 23036 | Vps4a | NM_126165.1 | chr8:107031325-107045756 |
| 22940 | Vmn2r45 | NM_001105075.1 | chr7:8471468-8488959 | 23037 | Vps4b | NM_009190.2 | chr1:106770787-106796725 |
| 22941 | Vmn2r46 | NM_001105150.1 | chr7:9485564-9770971 | 23038 | Vps51 | NM_001081041.1 | chr19:6067841-6077187 |
| 22942 | Vmn2r47 | NM_001105151.1 | chr7:8010338-9841325 | 23039 | Vps52 | NM_172620.3 | chr17:33955881-33966488 |
| 22943 | Vmn2r48 | NM_001105152.1 | chr7:9927623-9953585 | 23040 | Vps53 | NM_026664.3 | chr11:76046225-76179630 |
| 22944 | Vmn2r49 | NM_001105156.1 | chr7:9976244-9992139 | 23041 | Vps54 | NM_001290868.1 | chr11:21239031-21321133 |
| 22945 | Vmn2r5 | NM_001104618.1 | chr3:64490820-64507685 | 23042 | Vps72 | NM_009336.2 | chr3:95111041-95123051 |
| 22946 | Vmn2r50 | NM_001105178.1 | chr7:10037234-10053178 | 23043 | Vps8 | NM_001285893.1 | chr16:21423117-21644681 |
| 22947 | Vmn2r51 | NM_001105179.1 | chr7:10087197-10105659 | 23044 | Vps9d1 | NM_028200.2 | chr8:123242355-123254222 |
| 22948 | Vmn2r52 | NM_001105191.1 | chr7:10158651-10176286 | 23045 | Vrk1 | NM_001029843.1 | chr12:106010262-106077410 |
| 22949 | Vmn2r53 | NM_001104644.1 | chr7:12581469-12606544 | 23046 | Vrk2 | NM_001252447.1 | chr11:26471401-26593920 |
| 22950 | Vmn2r54 | NM_001081449.2 | chr7:12615232-12636134 | 23047 | Vrk3 | NM_133945.1 | chr7:44748628-44777514 |
| 22951 | Vmn2r55 | NM_001104645.1 | chr7:12651705-12684991 | 23048 | Vrtn | NM_001033776.2 | chr12:84642895-84651455 |
| 22952 | Vmn2r56 | NM_001104648.1 | chr7:12693997-12733105 | 23049 | Vsig1 | NM_026103.1 | chrX:140923188-140939472 |
| 22953 | Vmn2r57 | NM_177764.4 | chr7:41399731-41448641 | 23050 | Vsig10 | NM_001033311.3 | chr5:117319265-117355006 |
| 22954 | Vmn2r58 | NM_001105055.1 | chr7:41836880-41872670 | 23051 | Vsig10l | NM_001290316.1 | chr7:43463232-43472014 |
| 22955 | Vmn2r59 | NM_001101791.1 | chr7:42011791-42088981 | 23052 | Vsig2 | NM_020518.2 | chr9:37539254-37544205 |
| 22956 | Vmn2r6 | NM_001104619.1 | chr3:64537560-64559818 | 23053 | Vsig4 | NM_177789.4 | chrX:96247202-96293438 |
| 22957 | Vmn2r60 | NM_001105057.1 | chr7:42116470-42195776 | 23054 | Vsig8 | NM_177723.4 | chr1:172555937-172563717 |
| 22958 | Vmn2r61 | NM_001105058.1 | chr7:42260052-42300755 | 23055 | Vsnl1 | NM_012038.4 | chr12:11325244-11436649 |
| 22959 | Vmn2r62 | NM_001105059.1 | chr7:42764437-42793496 | 23056 | Vstm2a | NM_001290539.1 | chr11:16255723-16284551 |
| 22960 | Vmn2r63 | NM_001105060.1 | chr7:42903250-42933789 | 23057 | Vstm2b | NM_021387.3 | chr7:40899277-40929968 |
| 22961 | Vmn2r65 | NM_001105180.1 | chr7:84940168-84964009 | 23058 | Vstm2l | NM_198627.2 | chr2:157914652-157944719 |
| 22962 | Vmn2r66 | NM_001033878.3 | chr7:84994644-85012020 | 23059 | Vstm4 | NM_178791.4 | chr14:32856755-32939489 |
| 22963 | Vmn2r67 | NM_001102579.1 | chr7:85136239-85155902 | 23060 | Vstm5 | NM_026955.2 | chr9:15239044-15259413 |
| 22964 | Vmn2r68 | NM_001105181.1 | chr7:85221517-85237704 | 23061 | Vsx1 | NM_054068.2 | chr2:150680701-150689137 |
| 22965 | Vmn2r69 | NM_001105182.1 | chr7:85406375-85415676 | 23062 | Vsx2 | NM_007701.3 | chr12:84569827-84595457 |
| 22966 | Vmn2r7 | NM_175674.3 | chr3:64690659-64719602 | 23063 | Vta1 | NM_025418.3 | chr10:14655332-14705489 |
| 22967 | Vmn2r70 | NM_001105183.1 | chr7:85558702-85569088 | 23064 | Vtcn1 | NM_178594.3 | chr3:100825458-100896922 |
| 22968 | Vmn2r71 | NM_001105184.1 | chr7:85685811-85624547 | 23065 | Vti1a | NM_016862.4 | chr19:55316056-55627461 |
| 22969 | Vmn2r72 | NM_001105185.1 | chr7:85737783-85754981 | 23066 | Vti1b | NM_016800.3 | chr12:79156016-79172458 |
| 22970 | Vmn2r73 | NM_001105187.1 | chr7:85887546-85875938 | 23067 | Vtn | NM_011707.2 | chr11:78499119-78502325 |
| 22971 | Vmn2r74 | NM_001102578.1 | chr7:85951866-85961482 | 23068 | Vwa1 | NM_147776.4 | chr4:155768494-155774561 |
| 22972 | Vmn2r75 | NM_001105189.1 | chr7:86148041-86171724 | 23069 | Vwa2 | NM_172840.2 | chr19:56874415-56912078 |
| 22973 | Vmn2r76 | NM_001102580.1 | chr7:86225205-86246201 | 23070 | Vwa3a | NM_177697.3 | chr7:120739556-120805540 |
| 22974 | Vmn2r77 | NM_001105188.1 | chr7:86795140-86812032 | 23071 | Vwa5a | NM_001145957.1 | chr9:38718267-38743337 |
| 22975 | Vmn2r78 | NM_001105189.1 | chr7:86915348-86955177 | 23072 | Vwa5b1 | NM_029401.1 | chr4:138568968-138623992 |
| 22976 | Vmn2r79 | NM_001105190.1 | chr7:86996464-87037988 | 23073 | Vwa5b2 | NM_001144953.1 | chr16:20589581-20605377 |
| 22977 | Vmn2r8 | NM_001104620.1 | chr5:108797192-108808754 | 23074 | Vwa7 | NM_198582.3 | chr17:35016578-35026741 |
| 22978 | Vmn2r80 | NM_001105188.1 | chr10:79148815-79194933 | 23075 | Vwa8 | NM_027906.1 | chr14:78849177-79202310 |
| 22979 | Vmn2r81 | NM_175936.1 | chr10:79247776-79294535 | 23076 | Vwa9 | NM_001077631.2 | chr9:64960831-64986981 |
| 22980 | Vmn2r82 | NM_001101572.1 | chr10:79356590-79396766 | 23077 | Vwc2 | NM_177033.3 | chr11:11114015-11263526 |
| 22981 | Vmn2r83 | NM_001104537.1 | chr10:79468957-79492154 | 23078 | Vwc2l | NM_177164.3 | chr1:70725714-70885397 |
| 22982 | Vmn2r84 | NM_001081448.1 | chr10:130385799-130394241 | 23079 | Vwce | NM_027913.1 | chr19:10634232-10665210 |
| 22983 | Vmn2r85 | NM_001102602.1 | chr10:130418260-130429612 | 23080 | Vwde | NM_001013757.2 | chr6:13185610-13224965 |
| 22984 | Vmn2r86 | NM_001103366.1 | chr10:130446198-130455894 | 23081 | Vwf | NM_011708.4 | chr6:125552947-125686679 |
| 22985 | Vmn2r87 | NM_001103356.1 | chr10:130471820-130497379 | 23082 | Wac | NM_001146298.2 | chr18:7869196-7929028 |
| 22986 | Vmn2r88 | NM_011686.1 | chr14:51410060-51418882 | 23083 | Wap | NM_011709.5 | chr11:6635482-6638649 |
| 22987 | Vmn2r89 | NM_009486.3 | chr14:51451961-51461293 | 23084 | Wapal | NM_001004456.4 | chr14:34673927-34747983 |
| 22988 | Vmn2r9 | NM_001104621.1 | chr5:108842946-108852510 | 23085 | Wars | NM_001164314.1 | chr12:108860029-108894174 |

Fig.21 - 120

| | | | | | | | | |
|---|---|---|---|---|---|---|---|---|
| 23086 | Wars2 | NM_027462.4 | chr3:99141089-99220203 | | 23183 | Wee2 | NM_201370.2 | chr6:40442862-40466815 |
| 23087 | Was | NM_009515.2 | chrX:8081465-8090491 | | 23184 | Wfdc1 | NM_023395.2 | chr8:119666364-119688020 |
| 23088 | Wasf1 | NM_031877.3 | chr10:40883533-40938569 | | 23185 | Wfdc10 | NM_001039501.2 | chr2:164656045-164657368 |
| 23089 | Wasf2 | NM_153423.6 | chr4:133130632-133198330 | | 23186 | Wfdc11 | NM_001161806.1 | chr2:164662893-164674087 |
| 23090 | Wasf3 | NM_145155.3 | chr5:146385005-146471125 | | 23187 | Wfdc12 | NM_138684.2 | chr2:164189230-164190558 |
| 23091 | Wash | NM_001037757.1 | chr17:66111644-66120503 | | 23188 | Wfdc13 | NM_001012704.1 | chr2:164685106-164687706 |
| 23092 | Wasl | NM_001167745.1 | chr6:24632685-24664995 | | 23189 | Wfdc15a | NM_183271.2 | chr2:164198871-164200117 |
| 23093 | Wbp1 | NM_001083922.1 | chr6:83119043-83121461 | | 23190 | Wfdc15b | NM_001045554.1 | chr2:164221453-164221663 |
| 23094 | Wbp1l | NM_021714.4 | chr6:136813653-136828216 | | 23191 | Wfdc16 | NM_001012723.2 | chr2:164634707-164638802 |
| 23095 | Wbp1j | NM_001177812.1 | chr19:46599105-46667389 | | 23192 | Wfdc17 | NM_001081957.1 | chr11:83704055-83706269 |
| 23096 | Wbp2 | NM_016852.2 | chr11:116078572-116086964 | | 23193 | Wfdc18 | NM_007989.4 | chr11:83709003-83711360 |
| 23097 | Wbp2nl | NM_029066.1 | chr15:82298983-82314558 | | 23194 | Wfdc2 | NM_026323.2 | chr2:164562715-164568506 |
| 23098 | Wbp4 | NM_018765.3 | chr14:79459936-79481268 | | 23195 | Wfdc3 | NM_027961.1 | chr2:164731225-164743267 |
| 23099 | Wbp5 | NM_011712.2 | chrX:136248079-136247139 | | 23196 | Wfdc5 | NM_145369.3 | chr2:164176324-164182742 |
| 23100 | Wbscr16 | NM_033572.2 | chr5:134144057-134176767 | | 23197 | Wfdc6a | NM_001033240.4 | chr2:164579518-164585447 |
| 23101 | Wbscr17 | NM_145218.3 | chr5:130874950-131307522 | | 23198 | Wfdc6b | NM_001012725.2 | chr2:164613699-164618213 |
| 23102 | Wbscr22 | NM_025375.3 | chr5:135052956-135064666 | | 23199 | Wfdc8 | NM_001080550.2 | chr2:164596457-164613626 |
| 23103 | Wbscr25 | NR_026907.1 | chr5:134987432-135001350 | | 23200 | Wfdc9 | NM_001160414.1 | chr2:164649624-164654966 |
| 23104 | Wbscr27 | NM_024479.2 | chr5:134932372-134942637 | | 23201 | Wfikkn1 | NM_001100454.1 | chr17:25877627-25880858 |
| 23105 | Wbscr28 | NM_029681.3 | chr5:134901592-134906733 | | 23202 | Wfikkn2 | NM_181819.2 | chr11:94235951-94242579 |
| 23106 | Wdfy1 | NM_001111279.1 | chr1:79702261-79761769 | | 23203 | Wfs1 | NM_011716.2 | chr5:36966103-36988982 |
| 23107 | Wdfy2 | NM_175546.4 | chr14:62837689-62956886 | | 23204 | Whamm | NM_001004185.3 | chr7:81571291-81586836 |
| 23108 | Wdfy3 | NM_172682.3 | chr5:101832952-102069921 | | 23205 | Whrn | NM_001008791.2 | chr4:63414909-63495991 |
| 23109 | Wdfy4 | NM_001146022.2 | chr14:32959546-33185066 | | 23206 | Whsc1 | NM_001081102.2 | chr5:33843111-33857966 |
| 23110 | Wdhd1 | NM_172598.3 | chr14:47240943-47276857 | | 23207 | Whsc1l1 | NM_001001735.2 | chr8:25602283-25677972 |
| 23111 | Wdpcp | NM_145425.3 | chr11:21572280-21898686 | | 23208 | Wibg | NM_001170869.2 | chr10:128748454-128766568 |
| 23112 | Wdr1 | NM_011715.2 | chr5:38526812-38561595 | | 23209 | Wif1 | NM_011915.2 | chr10:121034003-121100642 |
| 23113 | Wdr11 | NM_172255.3 | chr7:129591862-129635738 | | 23210 | Wipf1 | NM_001289722.1 | chr2:73429609-73453889 |
| 23114 | Wdr12 | NM_001199060.1 | chr1:60076867-60098500 | | 23211 | Wipf2 | NM_197940.2 | chr11:98863597-98905578 |
| 23115 | Wdr13 | NM_001290783.1 | chrX:8123300-8132858 | | 23212 | Wipf3 | NM_001167860.1 | chr5:54852882-54903768 |
| 23116 | Wdr16 | NM_029768.2 | chr11:67924805-67965642 | | 23213 | Wipi1 | NM_145940.2 | chr11:109573520-109611389 |
| 23117 | Wdr17 | NM_001172352.1 | chr8:54629615-54724368 | | 23214 | Wipi2 | NM_178398.4 | chr5:142629583-142669370 |
| 23118 | Wdr18 | NM_175450.4 | chr10:79660151-79669246 | | 23215 | Wisp1 | NM_018865.2 | chr15:66891392-66923199 |
| 23119 | Wdr19 | NM_153391.2 | chr5:65199695-65260415 | | 23216 | Wisp2 | NM_016873.2 | chr2:163820833-163833147 |
| 23120 | Wdr20 | NM_027149.2 | chr12:110737948-110795028 | | 23217 | Wisp3 | NM_001127376.1 | chr10:39150970-39163794 |
| 23121 | Wdr20rt | NM_027614.1 | chr12:65225516-65228454 | | 23218 | Wiz | NM_011717.4 | chr17:32354049-32388950 |
| 23122 | Wdr24 | NM_173741.3 | chr17:25823626-25828730 | | 23219 | Wls | NM_026582.4 | chr3:159839694-159935175 |
| 23123 | Wdr25 | NM_177602.3 | chr12:108894271-109028452 | | 23220 | Wnk1 | NM_001185920.1 | chr6:119923968-120038655 |
| 23124 | Wdr26 | NM_145514.5 | chr1:181173225-181211978 | | 23221 | Wnk2 | NM_001290311.1 | chr3:49037600-49148328 |
| 23125 | Wdr27 | NM_175173.3 | chr17:14818671-14943124 | | 23222 | Wnk3 | NM_001271678.1 | chrX:151198077-151320192 |
| 23126 | Wdr3 | NM_175552.4 | chr3:100138179-100162403 | | 23223 | Wnk4 | NM_175638.3 | chr11:101260566-101277499 |
| 23127 | Wdr31 | NM_001290521.1 | chr4:62452631-62470895 | | 23224 | Wnt1 | NM_021279.4 | chr15:98789856-98793830 |
| 23128 | Wdr33 | NM_001170966.1 | chr18:31804056-31835435 | | 23225 | Wnt10a | NM_009518.2 | chr1:74792018-74804175 |
| 23129 | Wdr34 | NM_001008498.2 | chr2:30031557-30048279 | | 23226 | Wnt10b | NM_011718.2 | chr15:98771751-98778150 |
| 23130 | Wdr35 | NM_001159527.1 | chr12:8974000-9028847 | | 23227 | Wnt11 | NM_001285792.1 | chr7:98835111-98854747 |
| 23131 | Wdr36 | NM_001100015.1 | chr18:32837224-32866420 | | 23228 | Wnt16 | NM_053116.4 | chr6:22288226-22298522 |
| 23132 | Wdr37 | NM_001039388.2 | chr13:8802965-8871736 | | 23229 | Wnt2 | NM_023653.5 | chr6:17988939-18030445 |
| 23133 | Wdr38 | NM_029687.3 | chr2:38998308-39001584 | | 23230 | Wnt2b | NM_009520.3 | chr3:104944804-104961709 |
| 23134 | Wdr4 | NM_021322.2 | chr17:31494321-31512487 | | 23231 | Wnt3 | NM_009521.2 | chr11:103774174-103818021 |
| 23135 | Wdr41 | NM_172590.3 | chr13:94976343-95023016 | | 23232 | Wnt3a | NM_009522.2 | chr11:59248041-59290751 |
| 23136 | Wdr43 | NM_175639.1 | chr17:71616214-71659031 | | 23233 | Wnt4 | NM_009523.2 | chr4:137277634-137299501 |
| 23137 | Wdr44 | NM_175180.3 | chrX:23693050-23806061 | | 23234 | Wnt5a | NM_001256224.1 | chr14:28511404-28525515 |
| 23138 | Wdr45 | NM_001290792.1 | chrX:7722219-7728201 | | 23235 | Wnt6 | NM_001271757.1 | chr6:119432530-119449336 |
| 23139 | Wdr45b | NM_025793.3 | chr11:121327202-121354447 | | 23236 | Wnt7a | NM_009526.3 | chr6:91363982-91411369 |
| 23140 | Wdr46 | NM_026907.2 | chr17:33907227-33949695 | | 23237 | Wnt7b | NM_009527.3 | chr15:85535436-85580729 |
| 23141 | Wdr47 | NM_181400.3 | chr3:108591277-108645719 | | 23238 | Wnt7b | NM_001163633.1 | chr15:85535436-85580729 |
| 23142 | Wdr48 | NM_026236.3 | chr9:119884894-119926579 | | 23239 | Wnt8a | NM_009290.2 | chr18:34542327-34548061 |
| 23143 | Wdr5 | NM_080848.2 | chr2:27515146-27536538 | | 23240 | Wnt8b | NM_011720.3 | chr19:44493471-44514273 |
| 23144 | Wdr52 | NM_001033247.1 | chr16:44394798-44482428 | | 23241 | Wnt9a | NM_139298.2 | chr11:59306929-58333552 |
| 23145 | Wdr53 | NM_001185162.1 | chr16:32247226-32257083 | | 23242 | Wnt9b | NM_011719.4 | chr11:103727362-103749821 |
| 23146 | Wdr54 | NM_023790.2 | chr6:83152709-83156379 | | 23243 | Wrap53 | NM_144824.2 | chr11:69561753-69579324 |
| 23147 | Wdr55 | NM_026464.2 | chr18:36760238-36763708 | | 23244 | Wrb | NM_207301.2 | chr16:96145418-96167852 |
| 23148 | Wdr59 | NM_001170742.1 | chr8:111448783-111522101 | | 23245 | Wrn | NM_001122822.1 | chr8:33234372-33385527 |
| 23149 | Wdr5b | NM_027113.2 | chr16:36041189-36042974 | | 23246 | Wrnip1 | NM_030215.3 | chr13:32802029-32822610 |
| 23150 | Wdr6 | NM_031392.2 | chr9:108572312-108578670 | | 23247 | Wsb1 | NM_001042565.3 | chr11:79239382-79243024 |
| 23151 | Wdr60 | NM_146039.3 | chr12:116207049-116263025 | | 23248 | Wsb2 | NM_021539.4 | chr5:117357304-117378589 |
| 23152 | Wdr61 | NM_001025375.2 | chr9:54717152-54734549 | | 23249 | Wscd1 | NM_177618.4 | chr11:71750702-71789646 |
| 23153 | Wdr62 | NM_146186.3 | chr7:30240137-30280421 | | 23250 | Wscd2 | NM_172864.3 | chr5:113550419-113589725 |
| 23154 | Wdr63 | NM_172864.3 | chr3:146040525-146108036 | | 23251 | Wt1 | NM_144783.2 | chr2:105126528-105173614 |
| 23155 | Wdr64 | NM_029453.2 | chr1:175698592-175815733 | | 23252 | Wt1os | NR_015462.1 | chr2:105076537-105126510 |
| 23156 | Wdr65 | NM_026789.4 | chr4:118554550-118620405 | | 23253 | Wtap | NM_001113532.1 | chr17:12971019-12992259 |
| 23157 | Wdr7 | NM_001014981.1 | chr18:63708894-63969759 | | 23254 | Wtip | NM_207212.2 | chr7:34109549-34133268 |
| 23158 | Wdr70 | NM_001081402.1 | chr15:7873054-8099209 | | 23255 | Wwc1 | NM_170779.1 | chr11:35839177-35980089 |
| 23159 | Wdr72 | NM_001033500.3 | chr9:74110383-74283263 | | 23256 | Wwc2 | NM_133791.4 | chr8:47827605-47980551 |
| 23160 | Wdr73 | NM_028026.2 | chr7:80890722-80901269 | | 23257 | Wwcx | NM_019573.3 | chr8:114439851-115352712 |
| 23161 | Wdr74 | NM_134139.1 | chr19:8735838-8740624 | | 23258 | Wwp1 | NM_001276292.1 | chr4:19608239-19709004 |
| 23162 | Wdr75 | NM_028599.2 | chr1:45795500-45823613 | | 23259 | Wwp2 | NM_025830.3 | chr8:107436397-107558595 |
| 23163 | Wdr76 | NM_001290986.1 | chr2:121506722-121544859 | | 23260 | Wwtr1 | NM_001168281.1 | chr3:57455643-57575910 |
| 23164 | Wdr77 | NM_027432.3 | chr3:105959297-105969760 | | 23261 | Xab2 | NM_025162.2 | chr8:3610089-3621296 |
| 23165 | Wdr78 | NM_146254.4 | chr4:103038064-103114299 | | 23262 | Xaf1 | NM_001037713.4 | chr11:72301628-72313733 |
| 23166 | Wdr8 | NM_021499.2 | chr4:154142371-154156818 | | 23263 | Xbp1 | NM_001271730.1 | chr11:5520640-5525993 |
| 23167 | Wdr81 | NM_138950.2 | chr11:75440942-75454717 | | 23264 | Xcl1 | NM_008510.1 | chr1:164931647-164935510 |
| 23168 | Wdr82 | NM_029896.1 | chr9:106170928-106191706 | | 23265 | Xcr1 | NM_011798.4 | chr9:123852314-123862029 |
| 23169 | Wdr83 | NM_026399.2 | chr8:85075034-85080746 | | 23266 | Xdh | NM_011723.3 | chr17:73893894-73950196 |
| 23170 | Wdr83os | NM_001001493.2 | chr8:85080962-85082339 | | 23267 | Xiap | NM_009688.3 | chrX:42067836-42109664 |
| 23171 | Wdr86 | NM_001081441.1 | chr5:24712268-24730680 | | 23268 | Xirp1 | NM_011724.3 | chr9:120019754-120023598 |
| 23172 | Wdr89 | NM_178909.4 | chr12:75630593-75669537 | | 23269 | Xirp2 | NM_001024618.2 | chr2:67446001-67526606 |
| 23173 | Wdr90 | NM_001163766.1 | chr17:25844733-25861515 | | 23270 | Xist | NR_001463.3 | chrX:103460372-103483233 |
| 23174 | Wdr91 | NM_001013366.1 | chr6:34880425-34910831 | | 23271 | Xk | NM_023500.2 | chrX:9272783-9313245 |
| 23175 | Wdr92 | NM_178909.4 | chr11:17211892-17235200 | | 23272 | Xkr4 | NM_001011874.1 | chr1:3214481-3671498 |
| 23176 | Wdr93 | NM_001037927.1 | chr7:79743162-79789960 | | 23273 | Xkr5 | NM_001133502.2 | chr8:18932728-18950975 |
| 23177 | Wdr95 | NM_029440.3 | chr5:149528678-149611894 | | 23274 | Xkr6 | NM_173393.2 | chr14:63606529-63820410 |
| 23178 | Wdr96 | NM_027559.2 | chr19:47736856-47837361 | | 23275 | Xkr7 | NM_001011732.1 | chr2:153031853-153055775 |
| 23179 | Wdsub1 | NM_001159636.1 | chr2:59855193-59882606 | | 23276 | Xkr8 | NM_201368.1 | chr4:132724903-132752546 |
| 23180 | Wdtc1 | NM_001290489.1 | chr4:133292465-133339315 | | 23277 | Xkr9 | NM_001011873.2 | chr1:13668770-13701723 |
| 23181 | Wdyhv1 | NM_029734.1 | chr5:58141435-58158654 | | 23278 | Xkrx | NM_183319.2 | chrX:134149044-134161928 |
| 23182 | Wee1 | NM_009516.3 | chr7:110122058-110143299 | | 23279 | Xlr | NM_001291747.1 | chrX:53783734-53797706 |

Fig.21 - 121

| | | | | | | | | |
|---|---|---|---|---|---|---|---|---|
| 23280 | Xlr3a | NM_001110784.1 | chrX:73086292-73097095 | 23377 | Zbtb12 | NM_198886.3 | chr17:34894558-34896844 |
| 23281 | Xlr3b | NM_001081643.1 | chrX:73192178-73202930 | 23378 | Zbtb14 | NM_009547.2 | chr17:69383977-69390544 |
| 23282 | Xlr3c | NM_011727.2 | chrX:73254539-73265390 | 23379 | Zbtb16 | NM_001033324.2 | chr9:48654296-48835945 |
| 23283 | Xlr4a | NM_001081642.1 | chrX:73074344-73082507 | 23380 | Zbtb17 | NM_009541.2 | chr4:141844672-141467937 |
| 23284 | Xlr4b | NM_021365.3 | chrX:73214332-73222453 | 23381 | Zbtb18 | NM_001012330.1 | chr1:177444660-177450764 |
| 23285 | Xlr4c | NM_183094.3 | chrX:73234075-73243130 | 23382 | Zbtb2 | NM_001033466.3 | chr10:4367073-4388108 |
| 23286 | Xlr5a | NM_001045539.2 | chrX:73107634-73117702 | 23383 | Zbtb20 | NM_001285805.1 | chr16:42907644-43619123 |
| 23287 | Xlr5b | NM_001111293.1 | chrX:73148840-73158399 | 23384 | Zbtb21 | NM_001081684.1 | chr16:97947434-97962621 |
| 23288 | Xlr5c | NM_031493.1 | chrX:73285196-73290515 | 23385 | Zbtb22 | NM_020625.1 | chr17:33916175-33919325 |
| 23289 | Xndc1 | NM_001286689.1 | chr7:102065490-102083762 | 23386 | Zbtb24 | NM_001277229.1 | chr10:41450357-41465582 |
| 23290 | Xntrpc | NM_011644.3 | chr7:102071218-102096864 | 23387 | Zbtb25 | NM_001172104.1 | chr12:76348899-76369464 |
| 23291 | Xpa | NM_011728.2 | chr4:46175221-46196311 | 23388 | Zbtb26 | NM_199025.2 | chr2:37432167-37443121 |
| 23292 | Xpc | NM_009531.2 | chr6:91489306-91515888 | 23389 | Zbtb3 | NM_001098237.1 | chr19:8802529-8804854 |
| 23293 | Xpnpep1 | NM_133216.3 | chr19:52991179-53088654 | 23390 | Zbtb32 | NM_021397.2 | chr7:30589680-30592942 |
| 23294 | Xpnpep2 | NM_001289729.1 | chrX:48108724-48136981 | 23391 | Zbtb33 | NM_001079513.1 | chrX:38189792-38197646 |
| 23295 | Xpnpep3 | NM_177310.2 | chr15:81800187-81454888 | 23392 | Zbtb34 | NM_001085507.1 | chr2:33406107-33431324 |
| 23296 | Xpo1 | NM_001035226.1 | chr11:23256040-23297597 | 23393 | Zbtb37 | NM_173424.3 | chr1:161017755-161034259 |
| 23297 | Xpo4 | NM_020506.1 | chr14:57582270-57664956 | 23394 | Zbtb38 | NM_175537.3 | chr9:96685422-96731675 |
| 23298 | Xpo5 | NM_028198.2 | chr17:46202854-46242299 | 23395 | Zbtb39 | NM_198035.1 | chr10:127739537-127747339 |
| 23299 | Xpo6 | NM_028816.2 | chr7:126101718-126200408 | 23396 | Zbtb4 | NM_029348.2 | chr11:69765911-69784026 |
| 23300 | Xpo7 | NM_023045.2 | chr14:70654245-70766628 | 23397 | Zbtb40 | NM_198248.1 | chr4:136979731-137048695 |
| 23301 | Xpot | NM_001081056.1 | chr10:121587379-121626316 | 23398 | Zbtb41 | NM_172643.5 | chr1:139422382-139453007 |
| 23302 | Xpr1 | NM_011273.2 | chr1:155275656-155417444 | 23399 | Zbtb42 | NM_001100460.1 | chr12:112678839-112682747 |
| 23303 | Xrcc1 | NM_009532.4 | chr7:24547149-24573438 | 23400 | Zbtb43 | NM_001025594.1 | chr2:33450287-33468532 |
| 23304 | Xrcc2 | NM_020570.2 | chr5:25689815-25705797 | 23401 | Zbtb44 | NM_001115130.1 | chr9:31030643-31075885 |
| 23305 | Xrcc3 | NM_028875.3 | chr12:111803191-111813879 | 23402 | Zbtb45 | NM_001024699.1 | chr7:13005665-13009800 |
| 23306 | Xrcc4 | NM_028012.4 | chr13:89848913-90089608 | 23403 | Zbtb46 | NM_027656.2 | chr2:181390885-181424388 |
| 23307 | Xrcc5 | NM_009533.2 | chr1:72307420-72394953 | 23404 | Zbtb48 | NM_133879.2 | chr4:152019775-152027671 |
| 23308 | Xrcc6 | NM_010247.2 | chr15:82016368-82040084 | 23405 | Zbtb49 | NM_029162.2 | chr5:38200043-38220428 |
| 23309 | Xrcc6bp1 | NM_001159559.1 | chr10:126887247-126901373 | 23406 | Zbtb5 | NM_001169293.1 | chr4:44991242-45012412 |
| 23310 | Xrn1 | NM_011916.3 | chr9:95954759-96057806 | 23407 | Zbtb6 | NM_146295.5 | chr2:37425499-37430919 |
| 23311 | Xrn2 | NM_011917.2 | chr2:147013059-147077997 | 23408 | Zbtb7a | NM_010731.3 | chr10:81136270-81151657 |
| 23312 | Xrra1 | NM_001164258.1 | chr7:99859217-99917824 | 23409 | Zbtb7b | NM_009565.4 | chr3:89377645-89393203 |
| 23313 | Xxylt1 | NM_198626.2 | chr16:30955502-31081432 | 23410 | Zbtb7c | NM_145356.3 | chr18:75820177-76148564 |
| 23314 | Xylb | NM_001033209.3 | chr9:119357380-119393797 | 23411 | Zbtb8a | NM_028603.4 | chr4:129353631-129378028 |
| 23315 | Xylt1 | NM_175645.3 | chr7:117980978-117667630 | 23412 | Zbtb8b | NM_153541.3 | chr4:129425764-129440818 |
| 23316 | Xylt2 | NM_145828.3 | chr11:94663846-94677493 | 23413 | Zbtb8os | NM_025970.3 | chr4:129336025-129347029 |
| 23317 | Yaeld1 | NM_025904.3 | chr13:17986639-17993351 | 23414 | Zbtb9 | NM_001005916.2 | chr17:26973178-26976203 |
| 23318 | Yaf2 | NM_024189.6 | chr15:93284232-93336935 | 23415 | Zbtbd6 | NM_001034882.3 | chr14:79451834-79454816 |
| 23319 | Yap1 | NM_001171147.1 | chr9:7932000-8004596 | 23416 | Zc2hc1a | NM_173181.3 | chr3:7503425-7553848 |
| 23320 | Yars | NM_134151.4 | chr4:129189794-129219607 | 23417 | Zc2hc1b | NM_029172.1 | chr10:13149643-13178023 |
| 23321 | Yars2 | NM_146108.2 | chr16:16302964-16309640 | 23418 | Zc2hc1c | NM_172414.4 | chr12:85288590-85299358 |
| 23322 | Ybey | NM_172550.4 | chr10:76459566-76469114 | 23419 | Zc3h10 | NM_134003.1 | chr10:128543564-128547744 |
| 23323 | Ybx1 | NM_011732.2 | chr4:119277326-119294513 | 23420 | Zc3h11a | NM_001276767.1 | chr1:133619870-133661399 |
| 23324 | Ybx2 | NM_016875.2 | chr11:69935898-69941599 | 23421 | Zc3h12a | NM_153159.2 | chr4:125118413-125127881 |
| 23325 | Ybx3 | NM_011733.2 | chr6:131364857-131388450 | 23422 | Zc3h12b | NM_001034907.2 | chrX:95711677-95927970 |
| 23326 | Ydjc | NM_026940.4 | chr16:17148675-17148850 | 23423 | Zc3h12c | NM_001162921.1 | chr9:52111984-52188111 |
| 23327 | Yeats2 | NM_001033237.2 | chr16:20141062-20232573 | 23424 | Zc3h12d | NM_172785.3 | chr10:7832469-7870397 |
| 23328 | Yeats4 | NM_026870.4 | chr10:117215140-117224507 | 23425 | Zc3h13 | NM_026083.2 | chr14:75284372-75344426 |
| 23329 | Yes1 | NM_001205132.1 | chr5:32611170-32687066 | 23426 | Zc3h14 | NM_001008506.2 | chr12:98746967-98787774 |
| 23330 | Yif1a | NM_026553.4 | chr19:5088537-5092879 | 23427 | Zc3h15 | NM_026934.3 | chr2:83644577-83664616 |
| 23331 | Yif1b | NM_001110201.1 | chr7:29238322-29247532 | 23428 | Zc3h18 | NM_001029993.1 | chr8:122376615-122417360 |
| 23332 | Yipf1 | NM_001205156.1 | chr4:107314362-107359823 | 23429 | Zc3h3 | NM_172121.1 | chr15:75754446-75841908 |
| 23333 | Yipf2 | NM_001205357.1 | chr9:21518681-21592831 | 23430 | Zc3h4 | NM_198631.2 | chr7:16401195-16437696 |
| 23334 | Yipf3 | NM_153353.1 | chr17:46248079-46252253 | 23431 | Zc3h6 | NM_178404.3 | chr2:128967401-129018563 |
| 23335 | Yipf4 | NM_026417.4 | chr17:74489492-74500277 | 23432 | Zc3h7a | NM_145931.2 | chr16:11136593-11176383 |
| 23336 | Yipf5 | NM_023311.3 | chr18:40204864-40219399 | 23433 | Zc3h7b | NM_001081016.1 | chr15:81744847-81796269 |
| 23337 | Yipf6 | NM_207633.2 | chrX:98937780-98949020 | 23434 | Zc3h8 | NM_020594.2 | chr2:128926267-128944020 |
| 23338 | Yipf7 | NM_023784.5 | chr5:69518669-69542647 | 23435 | Zc3hav1 | NM_028421.1 | chr6:38310496-38354603 |
| 23339 | Ykt6 | NM_019661.4 | chr11:5955757-5967781 | 23436 | Zc3hav1l | NM_172467.3 | chr6:38287393-38299259 |
| 23340 | Ypm1 | NM_178363.3 | chr12:64996320-85070515 | 23437 | Zc3hc1 | NM_172735.2 | chr6:30366387-30391010 |
| 23341 | Yme1l1 | NM_013771.5 | chr2:23156504-23199260 | 23438 | Zc4h2 | NM_001003916.2 | chrX:95639193-95658509 |
| 23342 | Yod1 | NM_178643.2 | chr1:119571326-130722057 | 23439 | Zcchc10 | NM_026479.4 | chr11:53324688-53333301 |
| 23343 | Ypel1 | NM_001291047.1 | chr16:17070138-17086736 | 23440 | Zcchc11 | NM_175472.3 | chr4:108459425-108559415 |
| 23344 | Ypel2 | NM_001005341.3 | chr11:86936424-86993762 | 23441 | Zcchc12 | NM_028325.3 | chrX:36195903-36199158 |
| 23345 | Ypel3 | NM_025347.2 | chr7:126776914-126780514 | 23442 | Zcchc13 | NM_029158.2 | chrX:103630585-103631664 |
| 23346 | Ypel4 | NM_001005342.2 | chr2:84734203-84737877 | 23443 | Zcchc14 | NM_080855.2 | chr8:121598702-121651935 |
| 23347 | Ypel5 | NM_027166.5 | chr17:72836703-72851195 | 23444 | Zcchc16 | NM_001033795.4 | chrX:144688906-145122410 |
| 23348 | Yrdc | NM_153566.2 | chr4:124850758-124855242 | 23445 | Zcchc17 | NM_153160.4 | chr4:130318084-130359943 |
| 23349 | Ythdc1 | NM_177680.3 | chr5:86804489-86836657 | 23446 | Zcchc18 | NM_001035509.1 | chrX:136993154-136996923 |
| 23350 | Ythdc2 | NM_001286864.1 | chr18:44828664-44889720 | 23447 | Zcchc2 | NM_001122675.1 | chr1:105990405-106034079 |
| 23351 | Ythdf1 | NM_173761.3 | chr2:180940376-180920936 | 23448 | Zcchc24 | NM_001101433.1 | chr14:25713639-25768856 |
| 23352 | Ythdf2 | NM_145393.4 | chr4:132184915-132212256 | 23449 | Zcchc3 | NM_175126.4 | chr2:152411955-152415044 |
| 23353 | Ythdf3 | NM_001145919.1 | chr3:16183182-16217037 | 23450 | Zcchc4 | NM_030135.3 | chr5:52783054-52823571 |
| 23354 | Ywhab | NM_018753.6 | chr2:163995196-164018587 | 23451 | Zcchc5 | NM_199468.1 | chrX:106837081-106840643 |
| 23355 | Ywhae | NM_009536.4 | chr11:75732886-75765841 | 23452 | Zcchc6 | NM_153538.3 | chr13:59771878-59823147 |
| 23356 | Ywhag | NM_018871.3 | chr5:135908374-135934641 | 23453 | Zcchc7 | NM_138590.4 | chr4:44756558-44932214 |
| 23357 | Ywhah | NM_011738.2 | chr5:33018815-33027966 | 23454 | Zcchc8 | NM_027494.3 | chr5:123698301-123721044 |
| 23358 | Ywhaq | NM_011739.3 | chr12:21577180-21417436 | 23455 | Zcchc9 | NM_145453.2 | chr13:91796532-91807696 |
| 23359 | Ywhaz | NM_001253805.1 | chr15:36770261-36794538 | 23456 | Zcrb1 | NM_026025.2 | chr15:93386112-93398290 |
| 23360 | Yy1 | NM_009537.3 | chr12:108793310-108816632 | 23457 | Zcwpw1 | NM_001005426.2 | chr5:137887801-137822621 |
| 23361 | Yy2 | NM_001098723.1 | chrX:159758985-157568985 | 23458 | Zdbf2 | NM_001267872.1 | chr1:63273268-63314575 |
| 23362 | Zadh2 | NM_146090.5 | chr18:84088157-84097514 | 23459 | Zdhhc1 | NM_175160.3 | chr8:105472424-105496870 |
| 23363 | Zak | NM_001164791.1 | chr2:72285700-72407501 | 23460 | Zdhhc11 | NM_027704.2 | chr13:73963861-73992840 |
| 23364 | Zan | NM_011741.2 | chr5:137378636-137477064 | 23461 | Zdhhc12 | NM_001037762.1 | chr2:30090943-30093635 |
| 23365 | Zap70 | NM_001289612.3 | chr1:36778988-36782820 | 23462 | Zdhhc13 | NM_028031.3 | chr7:48789002-48827437 |
| 23366 | Zar1 | NM_174877.3 | chr5:72577813-72581084 | 23463 | Zdhhc14 | NM_146073.3 | chr17:5492599-5753891 |
| 23367 | Zar1l | NM_001159693.1 | chr5:150507068-150518159 | 23464 | Zdhhc15 | NM_175358.4 | chrX:104536989-104671064 |
| 23368 | Zbbx | NM_172515.3 | chr3:75037894-75143772 | 23465 | Zdhhc16 | NM_023740.2 | chr19:41933471-41944103 |
| 23369 | Zbed3 | NM_029521.4 | chr15:93624824-95337842 | 23466 | Zdhhc17 | NM_172554.2 | chr10:110494779-111010066 |
| 23370 | Zbed4 | NM_181412.3 | chr15:88751710-88784516 | 23467 | Zdhhc18 | NM_001017968.2 | chr4:133666993-133633429 |
| 23371 | Zbed5 | NM_183088.2 | chr5:129895722-129903622 | 23468 | Zdhhc19 | NM_199309.2 | chr16:32496280-32507214 |
| 23372 | Zbed6 | NM_001166552.1 | chr1:133695878-133660685 | 23469 | Zdhhc2 | NM_178395.3 | chr8:40423814-40484842 |
| 23373 | Zbp1 | NM_001135519.1 | chr2:173213735-173218922 | 23470 | Zdhhc20 | NM_029492.4 | chr14:57832701-57890262 |
| 23374 | Zbtb1 | NM_178744.2 | chr12:76376265-76388747 | 23471 | Zdhhc21 | NM_026647.3 | chr4:82792737-82859661 |
| 23375 | Zbtb10 | NM_177660.3 | chr3:9250566-9285332 | 23472 | Zdhhc22 | NM_001009943.2 | chr12:86983380-86988676 |
| 23376 | Zbtb11 | NM_173026.2 | chr16:55973803-56008912 | 23473 | Zdhhc23 | NM_001007460.1 | chr16:43969145-43979050 |

Fig.21 - 122

| | | | | | | | | |
|---|---|---|---|---|---|---|---|---|
| 23474 | Zdhhc24 | NM_001168516.1 | chr19:4878667-4885397 | | 23571 | Zfp30 | NM_013705.1 | chr7:29784789-29794540 |
| 23475 | Zdhhc25 | NM_027306.3 | chr15:88600301-88601669 | | 23572 | Zfp300 | NM_183185.3 | chrX:21079149-21089229 |
| 23476 | Zdhhc3 | NM_026917.5 | chr9:123072309-123113205 | | 23573 | Zfp316 | NM_017467.3 | chr5:143249694-143270022 |
| 23477 | Zdhhc4 | NM_028379.5 | chr5:143316468-143329238 | | 23574 | Zfp317 | NM_172918.4 | chr9:19622090-19649731 |
| 23478 | Zdhhc5 | NM_144887.4 | chr2:84687919-84715164 | | 23575 | Zfp318 | NM_021346.2 | chr17:46383765-46420918 |
| 23479 | Zdhhc6 | NM_001033573.1 | chr19:55298295-55316032 | | 23576 | Zfp319 | NM_024867.3 | chr8:95326135-95331950 |
| 23480 | Zdhhc7 | NM_133967.3 | chr8:120081094-120101472 | | 23577 | Zfp322a | NM_001111107.2 | chr13:23353102-23369208 |
| 23481 | Zdhhc8 | NM_172151.4 | chr16:18220752-18235136 | | 23578 | Zfp324 | NM_178732.3 | chr7:12965863-12973822 |
| 23482 | Zdhhc9 | NM_172465.4 | chrX:48171970-48208702 | | 23579 | Zfp326 | NM_018759.2 | chr5:105876567-105915820 |
| 23483 | Zeb1 | NM_011546.3 | chr18:5591859-5775468 | | 23580 | Zfp329 | NM_026046.3 | chr7:12803779-12818860 |
| 23484 | Zeb2 | NM_001289521.1 | chr2:44983511-45110277 | | 23581 | Zfp330 | NM_145600.1 | chr8:82763519-82774126 |
| 23485 | Zeb2os | NR_110571.1 | chr2:45112259-45114084 | | 23582 | Zfp334 | NM_178411.3 | chr2:165377435-165388259 |
| 23486 | Zer1 | NM_001290503.1 | chr2:30097282-30124611 | | 23583 | Zfp335 | NM_199027.2 | chr2:164891891-164911750 |
| 23487 | Zfl2 | NR_003547.2 | chrX_GL456233_random:2687982-2707075 | | 23584 | Zfp341 | NM_199304.1 | chr2:154613367-154648817 |
| 23488 | Zfand1 | NM_025512.2 | chr3:10339955-10351301 | | 23585 | Zfp345 | NM_001034900.3 | chr2:150470990-150485063 |
| 23489 | Zfand2a | NM_001159908.1 | chr5:139471215-139484491 | | 23586 | Zfp346 | NM_012017.2 | chr13:55105308-55135071 |
| 23490 | Zfand2b | NM_001159905.1 | chr1:75168643-75171626 | | 23587 | Zfp35 | NM_011755.2 | chr18:23989633-24005371 |
| 23491 | Zfand3 | NM_148926.2 | chr17:30005086-30210020 | | 23588 | Zfp352 | NM_153102.3 | chr4:90218819-90225687 |
| 23492 | Zfand4 | NM_001290338.1 | chr6:116264218-116330304 | | 23589 | Zfp354a | NM_009329.3 | chr11:51059256-51072799 |
| 23493 | Zfand5 | NM_009551.5 | chr19:21272277-21286840 | | 23590 | Zfp354b | NM_013744.3 | chr11:50921785-50931635 |
| 23494 | Zfand6 | NM_029985.6 | chr7:84615053-84679351 | | 23591 | Zfp354c | NM_013922.4 | chr11:50811084-50827731 |
| 23495 | Zfa-ps | NR_037920.1 | chr10:52542319-52545739 | | 23592 | Zfp358 | NM_080461.2 | chr8:3493137-3497208 |
| 23496 | Zfat | NM_001145888.1 | chr15:68083737-68258856 | | 23593 | Zfp36 | NM_011756.4 | chr7:28376783-28379228 |
| 23497 | Zfc3h1 | NM_001033261.2 | chr10:115384958-115432771 | | 23594 | Zfp362 | NM_001081098.1 | chr4:128773084-128806113 |
| 23498 | Zfhx2 | NM_001039198.1 | chr14:55061658-55092048 | | 23595 | Zfp365 | NM_178679.2 | chr10:67886104-67912662 |
| 23499 | Zfhx2os | NR_004444.2 | chr14:55073090-55075874 | | 23596 | Zfp366 | NM_001004149.1 | chr13:99184822-99247032 |
| 23500 | Zfhx3 | NM_007496.2 | chr8:108714643-108961636 | | 23597 | Zfp367 | NM_175494.4 | chr13:64133056-64153199 |
| 23501 | Zfhx4 | NM_030708.2 | chr3:5218553-5415855 | | 23598 | Zfp369 | NM_178364.5 | chr13:65278853-65297795 |
| 23502 | Zfmi | NM_001166371.1 | chr6:83914352-83986871 | | 23599 | Zfp36l1 | NM_007564.5 | chr12:80107759-80113013 |
| 23503 | Zfp1 | NM_010037665.2 | chr8:111643442-111671008 | | 23600 | Zfp36l2 | NM_001001806.2 | chr17:84183927-84187947 |
| 23504 | Zfp101 | NM_009542.2 | chr17:33380178-33394637 | | 23601 | Zfp36l3 | NM_001009549.2 | chrX:53772686-53776394 |
| 23505 | Zfp105 | NM_009954.2 | chr9:122923677-122931028 | | 23602 | Zfp37 | NM_001290350.1 | chr4:62189636-62208646 |
| 23506 | Zfp106 | NM_011743.2 | chr2:120506829-120563831 | | 23603 | Zfp382 | NM_001081007.1 | chr7:30121947-30135032 |
| 23507 | Zfp108 | NM_018791.2 | chr7:24254793-24262444 | | 23604 | Zfp383 | NM_001243908.1 | chr7:29908516-29916815 |
| 23508 | Zfp109 | NM_020262.3 | chr7:24227794-24237598 | | 23605 | Zfp384 | NM_001252083.1 | chr6:125009237-125037870 |
| 23509 | Zfp11 | NM_172462.4 | chr5:129654594-129670088 | | 23606 | Zfp385a | NM_013866.2 | chr15:103313894-103340086 |
| 23510 | Zfp110 | NM_022981.4 | chr7:12834809-12850584 | | 23607 | Zfp385b | NM_001113399.1 | chr2:77410626-77703272 |
| 23511 | Zfp111 | NM_019940.2 | chr7:24193214-24208149 | | 23608 | Zfp385c | NM_177790.4 | chr11:100626218-100650693 |
| 23512 | Zfp112 | NM_021307.2 | chr7:24112319-24127952 | | 23609 | Zfp386 | NM_001004066.3 | chr12:116047723-116063207 |
| 23513 | Zfp113 | NM_001146.3 | chr5:138187901-138155744 | | 23610 | Zfp389 | NR_026798.1 | chr13:21504315-21506524 |
| 23514 | Zfp114 | NM_001029933.2 | chr7:24175044-24182318 | | 23611 | Zfp39 | NM_011758.2 | chr11:58888152-58904225 |
| 23515 | Zfp119a | NM_144546.6 | chr17:55864891-55878953 | | 23612 | Zfp395 | NM_199029.2 | chr14:65358675-65398930 |
| 23516 | Zfp119b | NM_146249.4 | chr17:55938372-55945259 | | 23613 | Zfp397 | NM_027007.2 | chr18:23954687-23964670 |
| 23517 | Zfp12 | NM_001289889.1 | chr5:143235162-143248834 | | 23614 | Zfp398 | NM_027477.3 | chr6:47835660-47868257 |
| 23518 | Zfp120 | NM_023264.4 | chr2:150114406-150136678 | | 23615 | Zfp40 | NM_009555.2 | chr17:23173868-23193228 |
| 23519 | Zfp128 | NM_153802.4 | chr7:12881177-12893422 | | 23616 | Zfp407 | NM_001033341.2 | chr18:84207701-84589504 |
| 23520 | Zfp13 | NM_011747.2 | chr17:23579851-23599487 | | 23617 | Zfp408 | NM_001034512 | chr2:91643687-91649791 |
| 23521 | Zfp131 | NM_028245.4 | chr13:119765185-119790806 | | 23618 | Zfp41 | NM_001044718.2 | chr15:75616683-75625300 |
| 23522 | Zfp13b-ps | NR_033459.1 | chr2:144459279-144467794 | | 23619 | Zfp410 | NM_001252582.1 | chr12:84316858-84334119 |
| 23523 | Zfp14 | NM_011748.2 | chr7:30036358-30051396 | | 23620 | Zfp414 | NM_026712.3 | chr17:33629091-33631714 |
| 23524 | Zfp142 | NM_029888.3 | chr1:74566425-74588028 | | 23621 | Zfp418 | NM_146179.2 | chr7:7171352-7183660 |
| 23525 | Zfp143 | NM_009281.3 | chr7:110061701-110095392 | | 23622 | Zfp42 | NM_009556.2 | chr8:43295066-43307009 |
| 23526 | Zfp146 | NM_011980.3 | chr7:30161267-30169727 | | 23623 | Zfp420 | NM_172740.2 | chr7:29859979-29877302 |
| 23527 | Zfp148 | NM_011749.4 | chr16:33380774-33503903 | | 23624 | Zfp422 | NM_026057.3 | chr6:116624015-116628999 |
| 23528 | Zfp157 | NM_028130.3 | chr5:138441475-138460694 | | 23625 | Zfp423 | NM_033327.2 | chr8:87661809-87959595 |
| 23529 | Zfp160 | NM_145483.2 | chr17:21008940-21028856 | | 23626 | Zfp426 | NM_001110309.1 | chr2:20468546-20492746 |
| 23530 | Zfp169 | NM_001164575.1 | chr13:48487659-48513410 | | 23627 | Zfp428 | NM_001290461.1 | chr7:24507086-24515682 |
| 23531 | Zfp174 | NM_001081217.1 | chr16:3847222-3858880 | | 23628 | Zfp429 | NM_001080941.1 | chr13:67389327-67399767 |
| 23532 | Zfp180 | NM_001045486.2 | chr7:24081896-24107708 | | 23629 | Zfp433 | NM_001243067.1 | chr10:81704824-81881086 |
| 23533 | Zfp182 | NM_001013387.2 | chrX:21026183-21062038 | | 23630 | Zfp438 | NM_178722.5 | chr18:5210030-5334439 |
| 23534 | Zfp184 | NM_183014.1 | chr13:21945095-21960485 | | 23631 | Zfp442 | XM_006500041.2 | chr2:150406872-150451530 |
| 23535 | Zfp185 | NM_001109043.1 | chrX:72987338-73031543 | | 23632 | Zfp444 | NM_001146024.1 | chr7:6172512-6193164 |
| 23536 | Zfp189 | NM_001289901.1 | chr4:49521175-49531558 | | 23633 | Zfp445 | NM_173364.5 | chr9:122848909-122866006 |
| 23537 | Zfp191 | NM_021559.2 | chr18:20412286-24020771 | | 23634 | Zfp446 | NM_001168565.1 | chr7:12977847-12985716 |
| 23538 | Zfp2 | NM_001044697.2 | chr11:50898711-50916176 | | 23635 | Zfp449 | NM_030139.4 | chrX:56346399-56365674 |
| 23539 | Zfp202 | NM_030713.2 | chr9:40192315-40213604 | | 23636 | Zfp451 | NM_001290699.1 | chr1:33761540-33814595 |
| 23540 | Zfp207 | NM_001130189.1 | chr11:80383278-80396248 | | 23637 | Zfp454 | NM_172794.2 | chr11:50872722-50887449 |
| 23541 | Zfp212 | NM_001145881.1 | chr6:47920567-47932837 | | 23638 | Zfp455 | NM_001048204.1 | chr13:67194805-67209298 |
| 23542 | Zfp213 | NM_001033496.3 | chr17:23556766-23564226 | | 23639 | Zfp456 | NM_001001186.3 | chr13:67363583-67375763 |
| 23543 | Zfp217 | NM_001033299.3 | chr2:170108642-170131220 | | 23640 | Zfp457 | NM_001003666.2 | chr13:67292450-67306412 |
| 23544 | Zfp219 | NM_001253694.1 | chr14:52006085-52019713 | | 23641 | Zfp458 | NM_001001152.2 | chr13:67254917-67269068 |
| 23545 | Zfp229 | NM_001164676.1 | chr7:21733723-21748969 | | 23642 | Zfp459 | NM_177811.4 | chr13:67405712-67421418 |
| 23546 | Zfp235 | NM_019941.2 | chr7:24134162-24143241 | | 23643 | Zfp46 | NM_009557.3 | chr4:136286068-136293942 |
| 23547 | Zfp236 | NM_177832.3 | chr18:82593596-82692734 | | 23644 | Zfp462 | NM_172867.3 | chr4:54947944-55083563 |
| 23548 | Zfp239 | NM_001001792.1 | chr6:117863076-117872766 | | 23645 | Zfp467 | NM_001085413.1 | chr6:48436612-48445090 |
| 23549 | Zfp248 | NM_028335.2 | chr6:118427318-118455506 | | 23646 | Zfp472 | NM_153063.3 | chr17:32965830-32979211 |
| 23550 | Zfp251 | NM_001007648.2 | chr15:76852140-76871435 | | 23647 | Zfp473 | NM_001289836.1 | chr7:44731481-44748349 |
| 23551 | Zfp26 | NM_011753.3 | chr9:20428317-20460160 | | 23648 | Zfp474 | NM_025749.3 | chr18:52615914-52639830 |
| 23552 | Zfp260 | NM_011981.4 | chr7:30095075-30107614 | | 23649 | Zfp488 | NM_001013777.2 | chr14:33967069-33978764 |
| 23553 | Zfp263 | NM_148924.3 | chr16:3744098-3750788 | | 23650 | Zfp493 | NM_028402.2 | chr13:67779692-67789080 |
| 23554 | Zfp266 | NM_001082485.1 | chr9:20435068-20521419 | | 23651 | Zfp503 | NM_145459.3 | chr14:21983961-21989601 |
| 23555 | Zfp27 | NM_001037707.1 | chr7:29893338-29906104 | | 23652 | Zfp507 | NM_177739.3 | chr7:35772345-35802989 |
| 23556 | Zfp273 | NM_198022.3 | chr13:67813815-67827000 | | 23653 | Zfp51 | NM_009558.4 | chr17:21450373-21465589 |
| 23557 | Zfp275 | NM_001160229.1 | chrX:73342620-73359079 | | 23654 | Zfp511 | NM_027201.1 | chr7:140036390-140040605 |
| 23558 | Zfp276 | NM_020497.2 | chr8:123254194-123270551 | | 23655 | Zfp512 | NM_172993.3 | chr5:31452435-31481753 |
| 23559 | Zfp277 | NM_172575.3 | chr12:40315045-40445790 | | 23656 | Zfp513 | NM_001177901.1 | chr5:31198980-31202042 |
| 23560 | Zfp28 | NM_175247.3 | chr7:6383317-6396637 | | 23657 | Zfp516 | NM_001177464.1 | chr18:82914631-83005314 |
| 23561 | Zfp280b | NM_177475.3 | chr10:76032611-76042969 | | 23658 | Zfp518a | NM_028319.1 | chr19:40894704-40917947 |
| 23562 | Zfp280c | NM_001166648.1 | chrX:48541625-48594373 | | 23659 | Zfp518b | NM_001081144.2 | chr5:38668483-38684826 |
| 23563 | Zfp280d | NM_146224.5 | chr9:72274887-72363771 | | 23660 | Zfp52 | NM_144915.2 | chr17:21535538-21562601 |
| 23564 | Zfp281 | NM_001160251.1 | chr1:136624900-136630391 | | 23661 | Zfp521 | NM_145492.4 | chr18:13687013-13972733 |
| 23565 | Zfp282 | NM_146175.3 | chr6:47877554-47908484 | | 23662 | Zfp523 | NM_172617.3 | chr17:28177417-28205886 |
| 23566 | Zfp286 | NM_138949.3 | chr11:62711485-62729417 | | 23663 | Zfp524 | NM_025324.2 | chr7:5015507-5018488 |
| 23567 | Zfp287 | NM_133208.2 | chr11:62711485-62729093 | | 23664 | Zfp526 | NM_175436.5 | chr7:25221424-25227495 |
| 23568 | Zfp292 | NM_013889.2 | chr4:34803109-34882948 | | 23665 | Zfp53 | NM_013843.3 | chr17:21488987-21510477 |
| 23569 | Zfp296 | NM_022409.3 | chr7:19577286-19580656 | | 23666 | Zfp532 | NM_207255.2 | chr18:65580229-65689436 |
| 23570 | Zfp3 | NM_177565.3 | chr11:70764446-70772928 | | 23667 | Zfp534 | NM_001127188.2 | chr4:147674224-147702831 |

Fig.21 - 123

| | | | | | | | |
|---|---|---|---|---|---|---|---|
| 23668 | Zfp536 | NM_172385.2 | chr7:37479108-37769752 | 23765 | Zfp760 | NM_001008501.2 | chr17:21707740-21725636 |
| 23669 | Zfp54 | NM_011760.2 | chr17:21423226-21435384 | 23766 | Zfp763 | NM_028543.3 | chr17:33016863-33033381 |
| 23670 | Zfp541 | NM_001099277.1 | chr7:16071941-16096328 | 23767 | Zfp764 | NM_001167832.1 | chr7:127403667-127406822 |
| 23671 | Zfp551 | NM_001033820.3 | chr7:124125148-124422491 | 23768 | Zfp768 | NM_148202.1 | chr7:127342794-127345314 |
| 23672 | Zfp553 | NM_146201.1 | chr7:127233442-127237860 | 23769 | Zfp770 | NM_175466.4 | chr2:114193460-114201432 |
| 23673 | Zfp558 | NM_028935.1 | chr9:18454053-18473559 | 23770 | Zfp771 | NM_177362.3 | chr7:127244525-127254801 |
| 23674 | Zfp560 | NM_001004190.3 | chr9:20345135-20385158 | 23771 | Zfp772 | NM_145577.2 | chr7:7202121-7209998 |
| 23675 | Zfp563 | NM_001024950.2 | chr17:33089366-33110704 | 23772 | Zfp773 | NM_029584.1 | chr7:7130677-7136755 |
| 23676 | Zfp566 | NM_152814.2 | chr7:30077336-30090510 | 23773 | Zfp775 | NM_173429.2 | chr6:48613179-48623227 |
| 23677 | Zfp568 | NM_001033355.3 | chr7:29983954-30028282 | 23774 | Zfp777 | NM_001081382.1 | chr6:48024187-48048114 |
| 23678 | Zfp57 | NM_001013745.2 | chr17:37002524-37010729 | 23775 | Zfp78 | NM_001025163.1 | chr7:6363307-6382605 |
| 23679 | Zfp572 | NR_045613.1 | chr15:59306947-59312013 | 23776 | Zfp780b | NM_001081021.1 | chr7:27959799-27979157 |
| 23680 | Zfp574 | NM_001168506.1 | chr7:25077204-25083492 | 23777 | Zfp781 | NM_199062.1 | chr10:81742820-81930480 |
| 23681 | Zfp575 | NM_001033205.3 | chr7:24583837-24587641 | 23778 | Zfp783 | NR_027963.1 | chr6:47943174-47954549 |
| 23682 | Zfp579 | NM_026741.2 | chr7:4992851-4996101 | 23779 | Zfp784 | NM_001039532.2 | chr7:5034445-5038446 |
| 23683 | Zfp58 | NM_001007575.2 | chr13:67490166-67500522 | 23780 | Zfp786 | NM_177882.4 | chr6:47819265-47830505 |
| 23684 | Zfp580 | NM_026900.1 | chr7:5051531-5053723 | 23781 | Zfp787 | NM_001013012.1 | chr7:6131488-6155971 |
| 23685 | Zfp583 | NM_001033249.3 | chr7:6315664-6330434 | 23782 | Zfp788 | NM_023363.2 | chr7:41633530-41651532 |
| 23686 | Zfp59 | NM_011762.3 | chr7:27838583-27856774 | 23783 | Zfp790 | NM_001145880.1 | chr7:29816071-29832042 |
| 23687 | Zfp592 | NM_178707.4 | chr7:80993683-81045162 | 23784 | Zfp791 | NM_001037745.1 | chr8:85109166-85123095 |
| 23688 | Zfp593 | NM_024215.2 | chr4:134243305-134245591 | 23785 | Zfp799 | NM_177359.5 | chr17:32815452-32830261 |
| 23689 | Zfp595 | NM_177622.3 | chr13:67312997-67332560 | 23786 | Zfp800 | NM_001081678.1 | chr6:28239930-28261601 |
| 23690 | Zfp597 | NM_001033159.2 | chr16:3861543-3872374 | 23787 | Zfp804a | NM_175513.3 | chr2:82053657-82259878 |
| 23691 | Zfp598 | NM_183149.1 | chr17:24669751-24682016 | 23788 | Zfp804b | NM_001163223.1 | chr5:6769029-7344378 |
| 23692 | Zfp599 | NM_181419.3 | chr9:22247429-22259895 | 23789 | Zfp808 | NM_001039239.2 | chr13:62129889-62173936 |
| 23693 | Zfp6 | NM_009560.2 | chr7:27751472-27751689 | 23790 | Zfp809 | NM_001164624.1 | chr9:22225711-22239693 |
| 23694 | Zfp800 | NM_001177545.2 | chr4:146157689-146198756 | 23791 | Zfp81 | NM_207541.1 | chr17:33333727-33358878 |
| 23695 | Zfp605 | NM_001163996.1 | chr5:110110091-110129794 | 23792 | Zfp810 | NM_145612.2 | chr9:22276747-22307638 |
| 23696 | Zfp606 | NM_001039951.2 | chr7:124783304-124822714 | 23793 | Zfp811 | NM_001267583.1 | chr17:32795675-32809931 |
| 23697 | Zfp607 | NM_001024726.2 | chr7:27880584-27880825 | 23794 | Zfp819 | NM_028913.3 | chr7:43607168-43618279 |
| 23698 | Zfp608 | NM_175751.4 | chr18:54888044-54990180 | 23795 | Zfp82 | NM_001252519.1 | chr7:30056033-30072923 |
| 23699 | Zfp609 | NM_172536.3 | chr9:65691582-65827564 | 23796 | Zfp820 | NM_029281.2 | chr17:21816875-21845759 |
| 23700 | Zfp61 | NM_009561.2 | chr7:24291045-24299549 | 23797 | Zfp821 | NM_001167946.2 | chr8:109705545-109724932 |
| 23701 | Zfp612 | NM_175480.4 | chr8:110079334-110092752 | 23798 | Zfp825 | NM_146231.1 | chr13:74480056-74493950 |
| 23702 | Zfp616 | NM_001177570.1 | chr11:74070169-74087301 | 23799 | Zfp827 | NM_178267.3 | chr8:79028436-79193766 |
| 23703 | Zfp617 | NM_133358.3 | chr8:71922824-71934630 | 23800 | Zfp830 | NM_025834.4 | chr11:82764343-82767622 |
| 23704 | Zfp618 | NM_161618.1 | chr4:62965573-63134030 | 23801 | Zfp831 | NM_001099328.1 | chr2:174643533-174710830 |
| 23705 | Zfp619 | NM_001004139.2 | chr7:39517765-39540415 | 23802 | Zfp839 | NM_001199785.1 | chr12:110850278-110869998 |
| 23706 | Zfp62 | NM_001024846.1 | chr1:49203499-49218816 | 23803 | Zfp84 | NM_023750.2 | chr7:29768551-29781419 |
| 23707 | Zfp622 | NM_144523.2 | chr15:25984365-25998482 | 23804 | Zfp846 | NM_172919.1 | chr9:20581327-20595193 |
| 23708 | Zfp623 | NM_030199.3 | chr15:75940951-75949400 | 23805 | Zfp85 | NM_001001130.2 | chr13:67747799-67755134 |
| 23709 | Zfp628 | NM_170759.2 | chr7:4915216-4922003 | 23806 | Zfp850 | NM_001254951.1 | chr7:29984470-28014115 |
| 23710 | Zfp629 | NM_177226.5 | chr7:127607034-127614433 | 23807 | Zfp85os | NR_027969.1 | chr13:67729261-67756838 |
| 23711 | Zfp637 | NM_177684.2 | chr6:117841241-117845956 | 23808 | Zfp862-ps | NR_015597.1 | chr6:48504338-48534831 |
| 23712 | Zfp639 | NM_001161618.1 | chr3:32510549-32520833 | 23809 | Zfp865 | NM_001033383.2 | chr7:5020375-5033223 |
| 23713 | Zfp64 | NM_009564.2 | chr2:168925360-168955587 | 23810 | Zfp866 | NM_177899.3 | chr8:69761323-69774911 |
| 23714 | Zfp641 | NM_173793.3 | chr15:98286121-98296083 | 23811 | Zfp867 | NM_178417.3 | chr11:59461196-59472474 |
| 23715 | Zfp644 | NM_026856.2 | chr5:106616740-106696630 | 23812 | Zfp868 | NM_001045553.1 | chr8:69610653-69625175 |
| 23716 | Zfp646 | NM_172749.4 | chr7:127877700-127885996 | 23813 | Zfp869 | NM_001039965.1 | chr8:69705136-69716902 |
| 23717 | Zfp647 | NM_001168276.1 | chr15:76910049-76925448 | 23814 | Zfp87 | NM_133228.3 | chr13:67515781-67526231 |
| 23718 | Zfp648 | NM_001204908.1 | chr1:154201186-154205674 | 23815 | Zfp870 | NM_207245.2 | chr17:32879220-32891603 |
| 23719 | Zfp65 | NM_145622.2 | chr13:67705305-67729173 | 23816 | Zfp871 | NM_172458.3 | chr17:32765496-32788287 |
| 23720 | Zfp651 | NM_001166644.1 | chr9:121760032-121771742 | 23817 | Zfp872 | NM_001033813.4 | chr9:22188165-22202123 |
| 23721 | Zfp652 | NM_201609.2 | chr11:95749066-95764713 | 23818 | Zfp873 | NM_001024626.2 | chr10:82048126-82061586 |
| 23722 | Zfp65os | NR_045781.1 | chr13:95700005-95712754 | 23819 | Zfp874a | NM_177712.4 | chr13:67440430-67451624 |
| 23723 | Zfp653 | NM_177318.3 | chr9:22055410-22071376 | 23820 | Zfp874b | NM_001076791.2 | chr13:67471512-67484253 |
| 23724 | Zfp654 | NM_028059.2 | chr16:64780346-64786321 | 23821 | Zfp879 | NM_001290779.1 | chr11:50832030-50843552 |
| 23725 | Zfp655 | NM_001083958.1 | chr15:145231714-145238322 | 23822 | Zfp882 | NM_001166645.1 | chr8:71908605-71918851 |
| 23726 | Zfp658 | NM_001008549.2 | chr7:43562369-43575461 | 23823 | Zfp9 | NM_011763.2 | chr6:118461949-118479273 |
| 23727 | Zfp661 | NM_001111029.1 | chr2:127575534-127584677 | 23824 | Zfp90 | NM_011764.3 | chr8:106415338-106425889 |
| 23728 | Zfp663 | NM_001005425.1 | chr2:165351296-165362119 | 23825 | Zfp91 | NM_053009.3 | chr19:12766938-12796123 |
| 23729 | Zfp664 | NM_001081750.1 | chr5:124862704-124888630 | 23826 | Zfp91Cntf | NR_024093.1 | chr19:12763527-12796123 |
| 23730 | Zfp667 | NM_001024928.2 | chr7:6304879-6307883 | 23827 | Zfp92 | NM_009566.5 | chrX:73411095-73426998 |
| 23731 | Zfp668 | NM_146259.3 | chr7:127865358-127876823 | 23828 | Zfp93 | NM_009567.4 | chr7:24270417-24277794 |
| 23732 | Zfp672 | NM_001256516.1 | chr11:58315113-58323365 | 23829 | Zfp930 | NM_001013379.2 | chr8:69209045-69230539 |
| 23733 | Zfp677 | NM_172486.2 | chr17:21383747-21399265 | 23830 | Zfp931 | NM_001162922.1 | chr2:178065877-178078425 |
| 23734 | Zfp68 | NM_001044747.2 | chr5:138603651-138619743 | 23831 | Zfp932 | NM_145563.2 | chr5:109996526-110010411 |
| 23735 | Zfp687 | NM_030074.2 | chr3:95006701-95015238 | 23832 | Zfp933 | NM_198619.2 | chr4:147822985-147848375 |
| 23736 | Zfp688 | NM_026999.4 | chr7:127418965-127422034 | 23833 | Zfp934 | NM_001162911.1 | chr13:62516796-62558599 |
| 23737 | Zfp689 | NM_175163.3 | chr7:127442135-127449158 | 23834 | Zfp935 | NM_001138496.1 | chr13:62453015-62466812 |
| 23738 | Zfp69 | NM_001005788.3 | chr4:120930136-120951701 | 23835 | Zfp936 | NM_001034893.1 | chr7:43177587-43192109 |
| 23739 | Zfp691 | NM_001145935.1 | chr4:119169517-119173856 | 23836 | Zfp937 | NM_001142411.2 | chr2:150216098-150244874 |
| 23740 | Zfp692 | NM_001040686.1 | chr11:58309068-58314613 | 23837 | Zfp938 | NM_001105837.2 | chr10:82224855-82241275 |
| 23741 | Zfp697 | NM_172863.4 | chr3:98382480-98431949 | 23838 | Zfp939 | NM_001243621.1 | chr7:39449517-39477418 |
| 23742 | Zfp7 | NM_145916.2 | chr15:76879275-76892394 | 23839 | Zfp94 | NM_001199321.1 | chr7:24301705-24316666 |
| 23743 | Zfp703 | NM_001191502.1 | chr8:26977335-28981462 | 23840 | Zfp940 | NM_173738.2 | chr7:29843935-29853648 |
| 23744 | Zfp704 | NM_133218.2 | chr3:9427009-9610085 | 23841 | Zfp941 | NM_001001380.2 | chr7:140809676-140822178 |
| 23745 | Zfp706 | NM_026521.4 | chr15:36997026-37007402 | 23842 | Zfp942 | NM_001199048.1 | chr17:21926962-21962464 |
| 23746 | Zfp707 | NM_001081165.1 | chr15:75969944-75975865 | 23843 | Zfp943 | NM_001025373.2 | chr17:21962558-21994386 |
| 23747 | Zfp708 | NM_001012325.2 | chr15:67069397-67097976 | 23844 | Zfp944 | NM_176962.4 | chr17:22337988-22361460 |
| 23748 | Zfp709 | NM_145624.4 | chr8:71882067-71892565 | 23845 | Zfp945 | NM_001110254.1 | chr17:22846696-22867134 |
| 23749 | Zfp710 | NM_001145999.1 | chr7:80083429-80092751 | 23846 | Zfp946 | NM_198003.2 | chr17:22242267-22456689 |
| 23750 | Zfp711 | NM_177747.3 | chrX:112600525-112635062 | 23847 | Zfp947 | NM_177596.3 | chr17:22144358-22165977 |
| 23751 | Zfp712 | NM_001166218.1 | chr13:67038593-67061170 | 23848 | Zfp948 | NM_001002008.1 | chr17:21567045-21588682 |
| 23752 | Zfp715 | NM_027264.3 | chr7:43296522-43313261 | 23849 | Zfp949 | NM_001142943.1 | chr9:88548019-88571086 |
| 23753 | Zfp719 | NM_172482.1 | chr7:43579585-43593710 | 23850 | Zfp951 | NM_001039231.3 | chr5:104813167-104860068 |
| 23754 | Zfp72 | NM_001081086.1 | chr13:74371625-74376566 | 23851 | Zfp952 | NM_001045559.1 | chr17:32993138-33005437 |
| 23755 | Zfp735 | NM_001126489.2 | chr11:73688777-73713808 | 23852 | Zfp953 | NM_001038651.3 | chr13:67339308-67360572 |
| 23756 | Zfp738 | NM_001001187.3 | chr13:67667440-67683512 | 23853 | Zfp954 | NM_172738.3 | chr7:7114682-7121476 |
| 23757 | Zfp74 | NM_178384.3 | chr7:29992790-29951893 | 23854 | Zfp955a | NM_029952.3 | chr17:33239506-33255145 |
| 23758 | Zfp740 | NM_001289690.1 | chr15:102204570-102215610 | 23855 | Zfp955b | NM_001142957.1 | chr17:33289543-33304689 |
| 23759 | Zfp746 | NM_001163475.1 | chr6:48062394-48086593 | 23856 | Zfp956 | NM_178898.4 | chr6:47953189-47965299 |
| 23760 | Zfp747 | NM_175560.3 | chr7:127376050-127376050 | 23857 | Zfp957 | NM_001033215.3 | chr14:79212354-79247367 |
| 23761 | Zfp748 | NM_001035231.3 | chr7:67538640-67553152 | 23858 | Zfp958 | NM_145591.4 | chr8:4613169-4630231 |
| 23762 | Zfp750 | NM_178763.4 | chr11:121519705-121519342 | 23859 | Zfp959 | NM_001009535.2 | chr17:55892092-55898930 |
| 23763 | Zfp758 | NM_145484.2 | chr17:22361452-22377281 | 23860 | Zfp960 | NM_001005358.2 | chr17:17064102-17089631 |
| 23764 | Zfp759 | NM_172392.3 | chr13:67128227-67141787 | 23861 | Zfp961 | NM_001164581.1 | chr8:71951085-71970333 |

Fig.21 - 124

| | | | | | | | | |
|---|---|---|---|---|---|---|---|---|
| 23862 | Zfp963 | NM_001200023.1 | chr8:69741638-69749962 | 23959 | Zscan20 | NM_177758.4 | chr4:128583538-128610098 |
| 23863 | Zfp964 | NM_001177527.1 | chr8:69654555-69664453 | 23960 | Zscan21 | NM_001044703.2 | chr5:138116904-138134265 |
| 23864 | Zfp97 | NM_011765.5 | chr17:17121382-17146878 | 23961 | Zscan22 | NM_001001447.3 | chr7:12897808-12909083 |
| 23865 | Zfpl1 | NM_024231.2 | chr19:6080762-6084891 | 23962 | Zscan25 | NM_001081431.1 | chr5:145283342-145291469 |
| 23866 | Zfpm1 | NM_009569.3 | chr8:122282140-122337247 | 23963 | Zscan26 | NM_001013786.2 | chr13:21442174-21453727 |
| 23867 | Zfpm2 | NM_011766.5 | chr15:40655041-41104592 | 23964 | Zscan29 | NM_001290819.1 | chr2:121158272-121171125 |
| 23868 | Zfr | NM_011767.2 | chr15:12117850-12185449 | 23965 | Zscan4a | NR_033707.1 | chr7:10794240-10799065 |
| 23869 | Zfr2 | NM_001034895.3 | chr10:81233162-81252123 | 23966 | Zscan4b | NM_001185173.1 | chr7:10900739-10905050 |
| 23870 | Zfx | NM_001044386.1 | chrX:94074630-94123407 | 23967 | Zscan4c | NM_001013765.2 | chr7:11005744-11010547 |
| 23871 | Zfy1 | NM_009570.4 | chrY:725206-797409 | 23968 | Zscan4d | NM_001100186.1 | chr7:11161842-11166148 |
| 23872 | Zfy2 | NM_009571.2 | chrY:2106174-2170409 | 23969 | Zscan4e | NM_001161802.1 | chr7:11306369-11310682 |
| 23873 | Zfyve1 | NM_183154.3 | chr12:83546940-83597147 | 23970 | Zscan4f | NM_001110316.2 | chr7:11397914-11402318 |
| 23874 | Zfyve16 | NM_173392.4 | chr13:92487748-92530810 | 23971 | Zscan5b | NM_133204.2 | chr7:6222277-6239412 |
| 23875 | Zfyve19 | NM_001164827.1 | chr2:119208719-119217050 | 23972 | Zswim1 | NM_028028.2 | chr2:164822685-164826867 |
| 23876 | Zfyve20 | NM_030081.2 | chr6:92186711-92214811 | 23973 | Zswim2 | NM_027964.2 | chr2:83915078-83941226 |
| 23877 | Zfyve21 | NM_026752.4 | chr12:111814169-111828388 | 23974 | Zswim3 | NM_178375.2 | chr2:164805113-164822127 |
| 23878 | Zfyve26 | NM_001008550.1 | chr12:79232346-79296282 | 23975 | Zswim4 | NM_172503.3 | chr8:84210941-84237942 |
| 23879 | Zfyve27 | NM_001164531.1 | chr19:42170566-42194592 | 23976 | Zswim5 | NM_001029912.2 | chr4:116877401-116989105 |
| 23880 | Zfyve28 | NM_001015039.1 | chr5:34194893-34288324 | 23977 | Zswim6 | NM_145456.2 | chr13:107724618-107890064 |
| 23881 | Zfyve9 | NM_183300.2 | chr4:108639258-108723876 | 23978 | Zswim7 | NM_027198.1 | chr11:62267223-62281395 |
| 23882 | Zg16 | NM_026918.2 | chr7:127050155-127051977 | 23979 | Zswim8 | NM_001252081.1 | chr14:20707551-20723619 |
| 23883 | Zgpbl1 | NM_001103168.1 | chr9:21062392-21067093 | 23980 | Zufsp | NM_028287.2 | chr10:33926985-33951212 |
| 23884 | Zgpat | NM_001048348.1 | chr2:181365422-181380793 | 23981 | Zw10 | NM_012039.2 | chr9:49055580-49078773 |
| 23885 | Zgrf1 | NM_197997.2 | chr3:127553488-127618023 | 23982 | Zwilch | NM_026507.4 | chr9:64137143-64172931 |
| 23886 | Zhx1 | NM_001042438.2 | chr15:58047002-58076508 | 23983 | Zwint | NM_025635.4 | chr10:72654845-72669792 |
| 23887 | Zhx2 | NM_199449.2 | chr15:57694666-57839832 | 23984 | Zxda | NR_033292.1 | chrX:94791284-94798289 |
| 23888 | Zhx3 | NM_177263.3 | chr2:160770446-160872990 | 23985 | Zxdb | NM_001081473.1 | chrX:94724568-94730191 |
| 23889 | Zic1 | NM_009573.3 | chr9:91360344-91365799 | 23986 | Zxdc | NM_030260.3 | chr6:90369493-90385394 |
| 23890 | Zic2 | NM_009574.3 | chr14:122475383-122480828 | 23987 | Zyg11a | NM_001167936.1 | chr4:108181933-108217922 |
| 23891 | Zic3 | NM_009575.2 | chrX:58030627-58036630 | 23988 | Zyg11b | NM_001039634.3 | chr4:108227754-108301090 |
| 23892 | Zic4 | NM_009576.2 | chr9:91389671-91389348 | 23989 | Zyx | NM_001289617.1 | chr6:42349827-42360213 |
| 23893 | Zic5 | NM_022987.3 | chr14:122459159-122465658 | 23990 | Zzef1 | NM_001045536.2 | chr11:72796225-72927120 |
| 23894 | Zik1 | NM_009577.3 | chr7:10487223-10495381 | 23991 | Zzz3 | NM_001080755.2 | chr3:152396002-152462826 |
| 23895 | Zim1 | NM_011769.4 | chr7:6675442-6696432 | | | | |
| 23896 | Zim3 | NR_036631.2 | chr7:6955685-6976662 | | | | |
| 23897 | Zkscan1 | NM_029869.1 | chr5:138085083-138107822 | | | | |
| 23898 | Zkscan14 | NM_023422.2 | chr5:145194945-145201882 | | | | |
| 23899 | Zkscan16 | NM_001099323.2 | chr4:58943627-58958355 | | | | |
| 23900 | Zkscan17 | NM_001130529.2 | chr11:59485520-59506640 | | | | |
| 23901 | Zkscan2 | NM_001081329.1 | chr7:123478638-123500449 | | | | |
| 23902 | Zkscan3 | NM_001145778.1 | chr13:21387003-21402755 | | | | |
| 23903 | Zkscan4 | NM_001039315.2 | chr13:21478848-21485505 | | | | |
| 23904 | Zkscan5 | NM_001167944.1 | chr5:145204558-145221750 | | | | |
| 23905 | Zkscan6 | NM_026107.3 | chr11:65807174-65829239 | | | | |
| 23906 | Zkscan7 | NM_001177505.1 | chr9:122888470-122896124 | | | | |
| 23907 | Zkscan8 | NM_001251833.1 | chr13:21513220-21531114 | | | | |
| 23908 | Zmat1 | NM_175446.3 | chrX:134971372-135009209 | | | | |
| 23909 | Zmat2 | NM_025594.3 | chr18:36793922-36799660 | | | | |
| 23910 | Zmat3 | NM_009517.2 | chr3:32334793-32385865 | | | | |
| 23911 | Zmat4 | NM_001277239.1 | chr8:23669660-24063116 | | | | |
| 23912 | Zmat5 | NM_026015.2 | chr11:4704677-4737666 | | | | |
| 23913 | Zmiz1 | NM_183208.4 | chr14:25459184-25666743 | | | | |
| 23914 | Zmiz2 | NM_001058867.1 | chr11:6395124-6406162 | | | | |
| 23915 | Zmpste24 | NM_172700.2 | chr4:121059237-121098243 | | | | |
| 23916 | Zmym1 | NM_026670.4 | chr4:127047093-127061132 | | | | |
| 23917 | Zmym2 | NM_029498.3 | chr14:56887794-56962579 | | | | |
| 23918 | Zmym3 | NM_001177985.1 | chrX:101404383-101419914 | | | | |
| 23919 | Zmym4 | NM_001114399.1 | chr4:126861819-126967923 | | | | |
| 23920 | Zmym5 | NM_001253752.1 | chr14:56790684-56811716 | | | | |
| 23921 | Zmym6 | NM_001285385.1 | chr4:127077382-127124374 | | | | |
| 23922 | Zmynd10 | NM_053258.3 | chr9:107547309-107551319 | | | | |
| 23923 | Zmynd11 | NM_001199141.1 | chr13:9684835-9765314 | | | | |
| 23924 | Zmynd12 | NM_001014900.2 | chr4:119422683-119453899 | | | | |
| 23925 | Zmynd15 | NM_001029929.2 | chr11:70459621-70466199 | | | | |
| 23926 | Zmynd19 | NM_026021.4 | chr2:24949776-24960870 | | | | |
| 23927 | Zmynd8 | NM_001252584.2 | chr2:165784151-165884838 | | | | |
| 23928 | Znf41-ps | NR_040355.1 | chr4:145789514-145831978 | | | | |
| 23929 | Znf512b | NM_001164597.1 | chr2:181582102-181592461 | | | | |
| 23930 | Znfx1 | NM_001033196.2 | chr2:167035796-167063015 | | | | |
| 23931 | Znhit1 | NM_027318.4 | chr5:136982193-136987959 | | | | |
| 23932 | Znhit2 | NM_013859.2 | chr19:6061206-6062468 | | | | |
| 23933 | Znhit3 | NM_001005223.2 | chr11:84910954-84916356 | | | | |
| 23934 | Znhit6 | NM_001081094.1 | chr3:145576207-145605245 | | | | |
| 23935 | Znrd1 | NM_023162.4 | chr17:36954357-36958428 | | | | |
| 23936 | Znrd1as | NM_029602.1 | chr17:36958591-36965623 | | | | |
| 23937 | Znrf1 | NM_001168621.1 | chr8:111536639-111626030 | | | | |
| 23938 | Znrf2 | NM_199143.2 | chr6:54816915-54890224 | | | | |
| 23939 | Znrf3 | NM_001080924.2 | chr11:5276328-5444847 | | | | |
| 23940 | Znrf4 | NM_011483.2 | chr17:56511247-56512483 | | | | |
| 23941 | Zp1 | NM_009580.2 | chr19:10914295-10929601 | | | | |
| 23942 | Zp2 | NM_011775.6 | chr7:120132360-120145290 | | | | |
| 23943 | Zp3 | NM_011776.1 | chr5:135980104-135988624 | | | | |
| 23944 | Zp3r | NM_009581.2 | chr1:130576705-130629606 | | | | |
| 23945 | Zp4-ps | NR_027813.1 | chr13:11522051-11525682 | | | | |
| 23946 | Zpbp | NM_001185583.1 | chr11:11280039-11462419 | | | | |
| 23947 | Zpbp2 | NM_001166494.1 | chr11:98551096-98558665 | | | | |
| 23948 | Zpld1 | NM_178720.4 | chr16:55225174-55283237 | | | | |
| 23949 | Zpr1 | NM_011752.2 | chr9:46273063-46282642 | | | | |
| 23950 | Zranb1 | NM_207302.1 | chr7:132949621-132983951 | | | | |
| 23951 | Zranb2 | NM_017381.2 | chr3:157534396-157548339 | | | | |
| 23952 | Zranb3 | NM_001285945.1 | chr1:127954178-128103047 | | | | |
| 23953 | Zrsr1 | NM_011663.3 | chr11:22972004-22976496 | | | | |
| 23954 | Zrsr2 | NM_009453.2 | chrX:163935442-163958666 | | | | |
| 23955 | Zscan10 | NM_001033425.4 | chr17:23600825-23611019 | | | | |
| 23956 | Zscan12 | NM_016684.2 | chr13:21362819-21372302 | | | | |
| 23957 | Zscan18 | NM_001017955.1 | chr7:12768091-12775658 | | | | |
| 23958 | Zscan2 | NM_009553.2 | chr7:80862107-80876513 | | | | |

Fig.22 - 1

| Line No. | Groups | | | | Sub-Group | Gene Name | Human Gene ID | Updated |
|---|---|---|---|---|---|---|---|---|
| 303 | 2 | 3 | 4 | 5 | V-2 | 1700047G03Rik | | |
| 512 | 2 | 3 | 4 | 5 | V-2 | 2210409E12Rik | | |
| 563 | 2 | 3 | 4 | 5 | V-2 | 2310057J18Rik | | |
| 662 | 2 | 3 | 4 | 5 | V-2 | 2810007J24Rik | | |
| 680 | 2 | 3 | 4 | 5 | V-2 | 2810417H13Rik | | |
| 732 | 2 | 3 | 4 | 5 | V-2 | 3110082I17Rik | | |
| 1371 | 2 | 3 | 4 | 5 | V-2 | 6330410L21Rik | | |
| 1435 | 2 | 3 | 4 | 5 | V-2 | 9130204L05Rik | | |
| 1577 | 2 | 3 | 4 | 5 | V-2 | A530016L24Rik | | |
| 1953 | 2 | 3 | 4 | 5 | V-2 | Adamts12 | 81792 | 4-May-15 |
| 2009 | 2 | 3 | 4 | 5 | V-2 | Adh6-ps1 | | |
| 2163 | 2 | 3 | 4 | 5 | V-2 | Aicda | 57379 | 4-May-15 |
| 2221 | 2 | 3 | 4 | 5 | V-2 | Akr1c14 | | |
| 2222 | 2 | 3 | 4 | 5 | V-2 | Akr1c18 | | |
| 2238 | 2 | 3 | 4 | 5 | V-2 | Alas2 | 212 | 23-May-15 |
| 2249 | 2 | 3 | 4 | 5 | V-2 | Aldh1l2 | 160428 | 23-May-15 |
| 2310 | 2 | 3 | 4 | 5 | V-2 | Alx4 | 60529 | 23-May-15 |
| 2346 | 2 | 3 | 4 | 5 | V-2 | Amy2a2 | 279 | 7-Jun-15 |
| 2364 | 2 | 3 | 4 | 5 | V-2 | Ang4 | 51378 | 4-May-15 |
| 2377 | 2 | 3 | 4 | 5 | V-2 | Angptl7 | 10218 | 12-May-15 |
| 2539 | 2 | 3 | 4 | 5 | V-2 | Aplnr | 187 | 3-May-15 |
| 2543 | 2 | 3 | 4 | 5 | V-2 | Apoa1 | 335 | 31-May-15 |
| 2561 | 2 | 3 | 4 | 5 | V-2 | Apoh | 350 | 31-May-15 |
| 3027 | 2 | 3 | 4 | 5 | V-2 | AU040972 | | |
| 3063 | 2 | 3 | 4 | 5 | V-2 | AY074887 | | |
| 3260 | 2 | 3 | 4 | 5 | V-2 | BC048546 | | |
| 3340 | 2 | 3 | 4 | 5 | V-2 | Bcl6 | 604 | 17-May-15 |
| 3348 | 2 | 3 | 4 | 5 | V-2 | Bcmo1 | 53630 | 4-May-15 |
| 3463 | 2 | 3 | 4 | 5 | V-2 | Bpifa1 | 51297 | 10-May-15 |
| 3468 | 2 | 3 | 4 | 5 | V-2 | Bpifb1 | 92747 | 4-May-15 |
| 3612 | 2 | 3 | 4 | 5 | V-2 | C1qtnf6 | 114904 | 4-May-15 |
| 3663 | 2 | 3 | 4 | 5 | V-2 | C6 | 729 | 7-Jun-15 |
| 3682 | 2 | 3 | 4 | 5 | V-2 | C8b | 732 | 4-May-15 |
| 3816 | 2 | 3 | 4 | 5 | V-2 | Car1 | 759 | 2015/6/7 |
| 3825 | 2 | 3 | 4 | 5 | V-2 | Car4 | 762 | 23-May-15 |
| 3828 | 2 | 3 | 4 | 5 | V-2 | Car6 | | |
| 3886 | 2 | 3 | 4 | 5 | V-2 | Cbl | 867 | 12-May-15 |
| 4093 | 2 | 3 | 4 | 5 | V-2 | Ccl8 | 6355 | 4-May-15 |
| 4099 | 2 | 3 | 4 | 5 | V-2 | Ccnb1 | 891 | 24-May-15 |
| 4138 | 2 | 3 | 4 | 5 | V-2 | Ccr9 | 10803 | 4-May-15 |
| 4189 | 2 | 3 | 4 | 5 | V-2 | Cd27 | 939 | 4-May-15 |
| 4211 | 2 | 3 | 4 | 5 | V-2 | Cd3e | 916 | |
| 4214 | 2 | 3 | 4 | 5 | V-2 | Cd4 | 920 | 17-May-15 |
| 4227 | 2 | 3 | 4 | 5 | V-2 | Cd5l | 922 | 4-May-15 |
| 4244 | 2 | 3 | 4 | 5 | V-2 | Cd8a | 925 | 4-May-15 |
| 4245 | 2 | 3 | 4 | 5 | V-2 | Cd8b1 | 926 | 12-May-15 |
| 4347 | 2 | 3 | 4 | 5 | V-2 | Cdk6 | 1021 | 17-May-15 |
| 4506 | 2 | 3 | 4 | 5 | V-2 | Ces3a | | |
| 4507 | 2 | 3 | 4 | 5 | V-2 | Ces3b | | |
| 4531 | 2 | 3 | 4 | 5 | V-2 | Cgref1 | 10669 | |
| 4657 | 2 | 3 | 4 | 5 | V-2 | Cidea | 1149 | 4-May-15 |
| 4659 | 2 | 3 | 4 | 5 | V-2 | Cidec | 63924 | 4-May-15 |
| 4662 | 2 | 3 | 4 | 5 | V-2 | Cidp2 | 148113 | 4-May-15 |
| 4696 | 2 | 3 | 4 | 5 | V-2 | Clca3 | 9629 | 4-May-15 |
| 4738 | 2 | 3 | 4 | 5 | V-2 | Clec11a | 6320 | |
| 4750 | 2 | 3 | 4 | 5 | V-2 | Clec2h | | |
| 4830 | 2 | 3 | 4 | 5 | V-2 | Cmtl5 | | |
| 4935 | 2 | 3 | 4 | 5 | V-2 | Col15a1 | 1306 | |
| 4940 | 2 | 3 | 4 | 5 | V-2 | Col1a1 | 1277 | |
| 4941 | 2 | 3 | 4 | 5 | V-2 | Col1a2 | 1278 | |
| 4951 | 2 | 3 | 4 | 5 | V-2 | Col3a1 | 1281 | |
| 4959 | 2 | 3 | 4 | 5 | V-2 | Col5a1 | 1289 | |
| 4963 | 2 | 3 | 4 | 5 | V-2 | Col6a2 | 1292 | |
| 4964 | 2 | 3 | 4 | 5 | V-2 | Col6a3 | 1293 | |
| 5109 | 2 | 3 | 4 | 5 | V-2 | Cpz | 8532 | 4-May-15 |
| 5281 | 2 | 3 | 4 | 5 | V-2 | Cthrc1 | 115908 | |
| 5299 | 2 | 3 | 4 | 5 | V-2 | Ctrb1 | 1504 | 4-May-15 |
| 5334 | 2 | 3 | 4 | 5 | V-2 | Ctxn3 | 613212 | |
| 5448 | 2 | 3 | 4 | 5 | V-2 | Cyp2c54 | | |
| 5458 | 2 | 3 | 4 | 5 | V-2 | Cyp2d12 | | |
| 5465 | 2 | 3 | 4 | 5 | V-2 | Cyp2d9 | | |
| 5479 | 2 | 3 | 4 | 5 | V-2 | Cyp2g1 | 113612 | |
| 5493 | 2 | 3 | 4 | 5 | V-2 | Cyp4a12a | | |
| 5494 | 2 | 3 | 4 | 5 | V-2 | Cyp4a12b | | |
| 5516 | 2 | 3 | 4 | 5 | V-2 | Cyp7b1 | 9420 | 17-May-15 |
| 5517 | 2 | 3 | 4 | 5 | V-2 | Cyp8b1 | 1582 | 12-May-15 |
| 5582 | 2 | 3 | 4 | 5 | V-2 | D430019H16Rik | | |
| 5714 | 2 | 3 | 4 | 5 | V-2 | Dcpp1 | | |
| 5715 | 2 | 3 | 4 | 5 | V-2 | Dcpp2 | | |
| 5716 | 2 | 3 | 4 | 5 | V-2 | Dcpp3 | | |
| 5720 | 2 | 3 | 4 | 5 | V-2 | Dct | 1638 | 21-May-15 |
| 5807 | 2 | 3 | 4 | 5 | V-2 | Defa22 | | |
| 5862 | 2 | 3 | 4 | 5 | V-2 | Defb8 | | |
| 5963 | 2 | 3 | 4 | 5 | V-2 | Dio1 | 1733 | 10-Jun-15 |
| 6018 | 2 | 3 | 4 | 5 | V-2 | Dmbt1 | 1755 | 12-May-15 |
| 6129 | 2 | 3 | 4 | 5 | V-2 | Dntt | 1791 | 4-May-15 |
| 6264 | 2 | 3 | 4 | 5 | V-2 | Dupd1 | 338599 | 4-May-15 |
| 6508 | 2 | 3 | 4 | 5 | V-2 | Egfr | 1956 | 24-May-15 |
| 6617 | 2 | 3 | 4 | 5 | V-2 | Elovl3 | 83401 | |
| 6653 | 2 | 3 | 4 | 5 | V-2 | Emp1 | 2012 | 4-May-15 |
| 6814 | 2 | 3 | 4 | 5 | V-2 | Esco2 | 157570 | 23-May-15 |
| 6958 | 2 | 3 | 4 | 5 | V-2 | Fabp4 | 2167 | 24-May-15 |
| 6975 | 2 | 3 | 4 | 5 | V-2 | Faim3 | 9214 | 12-May-15 |
| 7173 | 2 | 3 | 4 | 5 | V-2 | Fam64a | 54478 | 4-May-15 |
| 7409 | 2 | 3 | 4 | 5 | V-2 | Fgf15 | | |
| 7583 | 2 | 3 | 4 | 5 | V-2 | Foxn3 | 1112 | 4-May-15 |
| 7704 | 2 | 3 | 4 | 5 | V-2 | Fzd8 | 8325 | 4-May-15 |
| 7845 | 2 | 3 | 4 | 5 | V-2 | Gbp11 | | |
| 7948 | 2 | 3 | 4 | 5 | V-2 | Gh | 2688 | 7-Jun-15 |
| 7990 | 2 | 3 | 4 | 5 | V-2 | Gjb2 | 2706 | 31-May-15 |
| 8125 | 2 | 3 | 4 | 5 | V-2 | Gm10486 | | |
| 8142 | 2 | 3 | 4 | 5 | V-2 | Gm10591 | | |
| 8158 | 2 | 3 | 4 | 5 | V-2 | Gm10681 | | |
| 8258 | 2 | 3 | 4 | 5 | V-2 | Gm12238 | | |
| 8335 | 2 | 3 | 4 | 5 | V-2 | Gm13304 | | |
| 8462 | 2 | 3 | 4 | 5 | V-2 | Gm15348 | | |
| 8532 | 2 | 3 | 4 | 5 | V-2 | Gm16551 | | |
| 8682 | 2 | 3 | 4 | 5 | V-2 | Gm2083 | | |
| 8709 | 2 | 3 | 4 | 5 | V-2 | Gm21498 | | |
| 8765 | 2 | 3 | 4 | 5 | V-2 | Gm3415 | | |
| 8863 | 2 | 3 | 4 | 5 | V-2 | Gm4956 | | |
| 8920 | 2 | 3 | 4 | 5 | V-2 | Gm5424 | | |
| 8941 | 2 | 3 | 4 | 5 | V-2 | Gm5549 | | |
| 9016 | 2 | 3 | 4 | 5 | V-2 | Gm6300 | | |
| 9111 | 2 | 3 | 4 | 5 | V-2 | Gm7849 | | |
| 9113 | 2 | 3 | 4 | 5 | V-2 | Gm7861 | | |
| 9136 | 2 | 3 | 4 | 5 | V-2 | Gm853 | | |
| 9277 | 2 | 3 | 4 | 5 | V-2 | Golt1a | 127845 | 4-May-15 |
| 9318 | 2 | 3 | 4 | 5 | V-2 | Gpcpd1 | 56261 | 4-May-15 |
| 9530 | 2 | 3 | 4 | 5 | V-2 | Gsdmc | 56169 | 4-May-15 |
| 9531 | 2 | 3 | 4 | 5 | V-2 | Gsdmc2 | | |
| 9532 | 2 | 3 | 4 | 5 | V-2 | Gsdmc3 | | |
| 9533 | 2 | 3 | 4 | 5 | V-2 | Gsdmc4 | | |
| 9732 | 2 | 3 | 4 | 5 | V-2 | Hao1 | 54363 | 12-May-15 |
| 9951 | 2 | 3 | 4 | 5 | V-2 | Hist1h4c | 8364 | 4-May-15 |
| 9954 | 2 | 3 | 4 | 5 | V-2 | Hist1h4h | 8365 | 12-May-15 |
| 9955 | 2 | 3 | 4 | 5 | V-2 | Hist1h4i | 8294 | 2-Jun-15 |
| 9956 | 2 | 3 | 4 | 5 | V-2 | Hist1h4j | 8363 | 12-May-15 |
| 9958 | 2 | 3 | 4 | 5 | V-2 | Hist1h4m | | |
| 10127 | 2 | 3 | 4 | 5 | V-2 | Hrg | 3273 | 7-Jun-15 |
| 10167 | 2 | 3 | 4 | 5 | V-2 | Hsd3b5 | | |
| 10316 | 2 | 3 | 4 | 5 | V-2 | Ifitm7 | | |
| 10707 | 2 | 3 | 4 | 5 | V-2 | Itln1 | 55600 | 17-May-15 |
| 10832 | 2 | 3 | 4 | 5 | V-2 | Kcne3 | 10008 | 23-May-15 |
| 10867 | 2 | 3 | 4 | 5 | V-2 | Kcnk10 | 54207 | 4-May-15 |
| 10984 | 2 | 3 | 4 | 5 | V-2 | Kif20b | 9585 | 21-May-15 |
| 11019 | 2 | 3 | 4 | 5 | V-2 | Kiss1 | 3814 | 7-Jun-15 |
| 11104 | 2 | 3 | 4 | 5 | V-2 | Klk1b21 | | |
| 11106 | 2 | 3 | 4 | 5 | V-2 | Klk1b24 | | |
| 11108 | 2 | 3 | 4 | 5 | V-2 | Klk1b27 | | |
| 11113 | 2 | 3 | 4 | 5 | V-2 | Klk1b8 | | |
| 11301 | 2 | 3 | 4 | 5 | V-2 | Ky | 339855 | 4-May-15 |
| 11396 | 2 | 3 | 4 | 5 | V-2 | Lck | 3932 | 4-May-15 |
| 11414 | 2 | 3 | 4 | 5 | V-2 | Lct | 3938 | 12-May-15 |
| 11433 | 2 | 3 | 4 | 5 | V-2 | Lect1 | 11061 | 4-May-15 |
| 11535 | 2 | 3 | 4 | 5 | V-2 | Lipf | 8513 | 4-May-15 |
| 11701 | 2 | 3 | 4 | 5 | V-2 | Lrrc16a | 55604 | 17-May-15 |
| 11711 | 2 | 3 | 4 | 5 | V-2 | Lrrc26 | 389816 | 12-May-15 |
| 11813 | 2 | 3 | 4 | 5 | V-2 | Ltf | 4057 | 23-May-15 |
| 11876 | 2 | 3 | 4 | 5 | V-2 | Lyz1 | | |
| 12007 | 2 | 3 | 4 | 5 | V-2 | Map3k7cl | 56911 | 4-May-15 |
| 12143 | 2 | 3 | 4 | 5 | V-2 | Mcm10 | 55388 | 4-May-15 |
| 12159 | 2 | 3 | 4 | 5 | V-2 | Mcpt1 | 1379 | 4-May-15 |
| 12160 | 2 | 3 | 4 | 5 | V-2 | Mcpt2 | | |
| 12227 | 2 | 3 | 4 | 5 | V-2 | Mef2b | 4207 | 7-Jun-15 |
| 12277 | 2 | 3 | 4 | 5 | V-2 | Mettl21c | 196541 | 4-May-15 |
| 12365 | 2 | 3 | 4 | 5 | V-2 | Mid1 | 4281 | 7-Jun-15 |
| 12412 | 2 | 3 | 4 | 5 | V-2 | Mir1199 | 102466515 | 4-May-15 |
| 12532 | 2 | 3 | 4 | 5 | V-2 | Mir1940 | | |
| 12827 | 2 | 3 | 4 | 5 | V-2 | Mir433 | 574034 | 21-May-15 |
| 12876 | 2 | 3 | 4 | 5 | V-2 | Mir486 | 619554 | 21-May-15 |
| 12935 | 2 | 3 | 4 | 5 | V-2 | Mir548 | | |
| 12961 | 2 | 3 | 4 | 5 | V-2 | Mir6236 | | |
| 12966 | 2 | 3 | 4 | 5 | V-2 | Mir6244 | | |
| 12989 | 2 | 3 | 4 | 5 | V-2 | Mir6360 | | |
| 13048 | 2 | 3 | 4 | 5 | V-2 | Mir6516 | 102466864 | 4-May-15 |
| 13194 | 2 | 3 | 4 | 5 | V-2 | Mir6981 | | |
| 13281 | 2 | 3 | 4 | 5 | V-2 | Mir7060 | | |
| 13421 | 2 | 3 | 4 | 5 | V-2 | Mir8091 | | |
| 13426 | 2 | 3 | 4 | 5 | V-2 | Mir8096 | | |
| 13432 | 2 | 3 | 4 | 5 | V-2 | Mir8102 | | |
| 13434 | 2 | 3 | 4 | 5 | V-2 | Mir8114 | | |
| 13647 | 2 | 3 | 4 | 5 | V-2 | Mptx1 | 649458 | 4-May-15 |
| 13648 | 2 | 3 | 4 | 5 | V-2 | Mptx2 | | |
| 13652 | 2 | 3 | 4 | 5 | V-2 | Mpz | 4359 | 23-May-15 |
| 13657 | 2 | 3 | 4 | 5 | V-2 | Mrap | 56246 | 7-Jun-15 |
| 13779 | 2 | 3 | 4 | 5 | V-2 | Ms4a1 | 931 | 7-Jun-15 |
| 13812 | 2 | 3 | 4 | 5 | V-2 | Msln | 10232 | 4-May-15 |
| 13920 | 2 | 3 | 4 | 5 | V-2 | Mup1 | 60386 | 23-May-15 |
| 13921 | 2 | 3 | 4 | 5 | V-2 | Mup10 | | |
| 13922 | 2 | 3 | 4 | 5 | V-2 | Mup11 | | |
| 13923 | 2 | 3 | 4 | 5 | V-2 | Mup12 | | |
| 13924 | 2 | 3 | 4 | 5 | V-2 | Mup13 | | |
| 13925 | 2 | 3 | 4 | 5 | V-2 | Mup14 | | |
| 13926 | 2 | 3 | 4 | 5 | V-2 | Mup15 | | |
| 13927 | 2 | 3 | 4 | 5 | V-2 | Mup16 | | |
| 13928 | 2 | 3 | 4 | 5 | V-2 | Mup17 | | |
| 13929 | 2 | 3 | 4 | 5 | V-2 | Mup19 | | |
| 13930 | 2 | 3 | 4 | 5 | V-2 | Mup2 | | |
| 13931 | 2 | 3 | 4 | 5 | V-2 | Mup20 | | |
| 13932 | 2 | 3 | 4 | 5 | V-2 | Mup21 | | |
| 13937 | 2 | 3 | 4 | 5 | V-2 | Mup7 | | |

Fig.22 - 2

| | | | | | | | | | | | | | | | |
|---|---|---|---|---|---|---|---|---|---|---|---|---|---|---|---|
| 13938 | 2 | 3 | 4 | 5 | V-2 | Mup8 | | | 1444 | 2 | 3 | 4 | 5 | V-1 | 9230102K24Rik | | |
| 13939 | 2 | 3 | 4 | 5 | V-2 | Mup9 | | | 1446 | 2 | 3 | 4 | 5 | V-1 | 9230104L09Rik | | |
| 13961 | 2 | 3 | 4 | 5 | V-2 | Myb | 4602 | 24-May-15 | 1449 | 2 | 3 | 4 | 5 | V-1 | 9230110F15Rik | | |
| 13963 | 2 | 3 | 4 | 5 | V-2 | Mybl1 | 4603 | 12-May-15 | 1608 | 2 | 3 | 4 | 5 | V-1 | A730008H23Rik | | |
| 14051 | 2 | 3 | 4 | 5 | V-2 | Myoz3 | 91977 | 4-May-15 | 1646 | 2 | 3 | 4 | 5 | V-1 | A930016O22Rik | | |
| 14143 | 2 | 3 | 4 | 5 | V-2 | Nat8 | 9027 | 4-May-15 | 1712 | 2 | 3 | 4 | 5 | V-1 | Abcb1b | | |
| 14429 | 2 | 3 | 4 | 5 | V-2 | Nkx3-1 | 4824 | 12-May-15 | 1740 | 2 | 3 | 4 | 5 | V-1 | Abcg4 | 64137 | 12-May-15 |
| 14482 | 2 | 3 | 4 | 5 | V-2 | Nmrk2 | 27231 | 4-May-15 | 1775 | 2 | 3 | 4 | 5 | V-1 | Abra | 137735 | 12-May-15 |
| 14633 | 2 | 3 | 4 | 5 | V-2 | Nrep | 9315 | 12-May-15 | 1795 | 2 | 3 | 4 | 5 | V-1 | Acan | 176 | 12-May-15 |
| 14747 | 2 | 3 | 4 | 5 | V-2 | Nugge | 389643 | 4-May-15 | 1806 | 2 | 3 | 4 | 5 | V-1 | Acbd7 | 414149 | 4-May-15 |
| 16008 | 2 | 3 | 4 | 5 | V-2 | Onecut1 | 3175 | 12-May-15 | 1826 | 2 | 3 | 4 | 5 | V-1 | Acnat2 | | |
| 16080 | 2 | 3 | 4 | 5 | V-2 | Osln | 344901 | 4-May-15 | 1835 | 2 | 3 | 4 | 5 | V-1 | Acot3 | | |
| 16126 | 2 | 3 | 4 | 5 | V-2 | Oxtr | 5021 | 31-May-15 | 1866 | 2 | 3 | 4 | 5 | V-1 | Acsm3 | 6296 | 12-May-15 |
| 16226 | 2 | 3 | 4 | 5 | V-2 | Paqr9 | 344838 | 4-May-15 | 1873 | 2 | 3 | 4 | 5 | V-1 | Acta1 | 58 | 23-May-15 |
| 16267 | 2 | 3 | 4 | 5 | V-2 | Pax5 | 5079 | 17-May-15 | 1877 | 2 | 3 | 4 | 5 | V-1 | Actc1 | 70 | 23-May-15 |
| 16444 | 2 | 3 | 4 | 5 | V-2 | Pde6a | 5145 | 23-May-15 | 1879 | 2 | 3 | 4 | 5 | V-1 | Actg2 | 72 | 12-May-15 |
| 16596 | 2 | 3 | 4 | 5 | V-2 | Pglyrp1 | 8993 | 4-May-15 | 1888 | 2 | 3 | 4 | 5 | V-1 | Actn2 | 88 | 23-May-15 |
| 16653 | 2 | 3 | 4 | 5 | V-2 | Phlda1 | 22822 | 4-May-15 | 1889 | 2 | 3 | 4 | 5 | V-1 | Actn3 | 89 | 29-May-15 |
| 16709 | 2 | 3 | 4 | 5 | V-2 | Pigi | 5284 | 12-May-15 | 1935 | 2 | 3 | 4 | 5 | V-1 | Adam28 | 10863 | 4-May-15 |
| 16831 | 2 | 3 | 4 | 5 | V-2 | Pla2g4c | 8605 | 4-May-15 | 1947 | 2 | 3 | 4 | 5 | V-1 | Adam7 | 8756 | 4-May-15 |
| 16843 | 2 | 3 | 4 | 5 | V-2 | Plac9a | | | 2002 | 2 | 3 | 4 | 5 | V-1 | Add2 | 119 | 12-May-15 |
| 16917 | 2 | 3 | 4 | 5 | V-2 | Plin1 | 5346 | 12-May-15 | 2005 | 2 | 3 | 4 | 5 | V-1 | Adh1 | 124 | 4-May-15 |
| 17465 | 2 | 3 | 4 | 5 | V-2 | Prr32 | 100130613 | 4-May-15 | 2010 | 2 | 3 | 4 | 5 | V-1 | Adh7 | 131 | 12-May-15 |
| 17696 | 2 | 3 | 4 | 5 | V-2 | Ptprcap | 5790 | 4-May-15 | 2013 | 2 | 3 | 4 | 5 | V-1 | Adig | 149685 | 4-May-15 |
| 17772 | 2 | 3 | 4 | 5 | V-2 | Pzp | 5858 | 12-May-15 | 2014 | 2 | 3 | 4 | 5 | V-1 | Adipoq | 9370 | 24-May-15 |
| 17912 | 2 | 3 | 4 | 5 | V-2 | Rag1 | 5896 | 23-May-15 | 2104 | 2 | 3 | 4 | 5 | V-1 | Agr2 | 10551 | 17-May-15 |
| 17962 | 2 | 3 | 4 | 5 | V-2 | Rarres1 | 5918 | 4-May-15 | 2127 | 2 | 3 | 4 | 5 | V-1 | Ahsg | 197 | 12-May-15 |
| 18137 | 2 | 3 | 4 | 5 | V-2 | Reg3b | | | 2213 | 2 | 3 | 4 | 5 | V-1 | Akp3 | | |
| 18139 | 2 | 3 | 4 | 5 | V-2 | Reg3g | 130120 | 4-May-15 | 2216 | 2 | 3 | 4 | 5 | V-1 | Akr1b3 | | |
| 18166 | 2 | 3 | 4 | 5 | V-2 | Retnlb | 84666 | 4-May-15 | 2217 | 2 | 3 | 4 | 5 | V-1 | Akr1b7 | | |
| 18217 | 2 | 3 | 4 | 5 | V-2 | Rgs13 | 6003 | 7-Jun-15 | 2218 | 2 | 3 | 4 | 5 | V-1 | Akr1b8 | | |
| 18358 | 2 | 3 | 4 | 5 | V-2 | Rn45s | 100861532 | 4-May-15 | 2239 | 2 | 3 | 4 | 5 | V-1 | Alb | 213 | 7-Jun-15 |
| 18472 | 2 | 3 | 4 | 5 | V-2 | Rnu12 | 267010 | 4-May-15 | 2243 | 2 | 3 | 4 | 5 | V-1 | Aldh1a1 | 216 | 23-May-15 |
| 18775 | 2 | 3 | 4 | 5 | V-2 | Saa2 | 6289 | 7-Jun-15 | 2245 | 2 | 3 | 4 | 5 | V-1 | Aldh1a3 | 220 | 12-May-15 |
| 18827 | 2 | 3 | 4 | 5 | V-2 | Sash3 | 54440 | 4-May-15 | 2251 | 2 | 3 | 4 | 5 | V-1 | Aldh3a1 | 218 | 23-May-15 |
| 18844 | 2 | 3 | 4 | 5 | V-2 | Sbp | | | 2264 | 2 | 3 | 4 | 5 | V-1 | Aldob | 229 | 12-May-15 |
| 18845 | 2 | 3 | 4 | 5 | V-2 | Sbpl | | | 2265 | 2 | 3 | 4 | 5 | V-1 | Aldoc | 230 | 17-May-15 |
| 18863 | 2 | 3 | 4 | 5 | V-2 | Scara5 | 286133 | 4-May-15 | 2301 | 2 | 3 | 4 | 5 | V-1 | Alpk3 | 57538 | 4-May-15 |
| 18874 | 2 | 3 | 4 | 5 | V-2 | Scarna3b | | | 2302 | 2 | 3 | 4 | 5 | V-1 | Alpl | 249 | 23-May-15 |
| 18876 | 2 | 3 | 4 | 5 | V-2 | Scarna8 | 677776 | 4-May-15 | 2317 | 2 | 3 | 4 | 5 | V-1 | Amd1 | 262 | 4-May-15 |
| 18880 | 2 | 3 | 4 | 5 | V-2 | Scd2 | 79966 | 4-May-15 | 2339 | 2 | 3 | 4 | 5 | V-1 | Ampd1 | 270 | 12-May-15 |
| 18881 | 2 | 3 | 4 | 5 | V-2 | Scd3 | | | 2345 | 2 | 3 | 4 | 5 | V-1 | Amy1 | 276, 277, 278 | 7-Jun-15 |
| 18882 | 2 | 3 | 4 | 5 | V-2 | Scd4 | 79966 | 4-May-15 | 2347 | 2 | 3 | 4 | 5 | V-1 | Amy2a5 | | |
| 18894 | 2 | 3 | 4 | 5 | V-2 | Scgb1b27 | | | 2348 | 2 | 3 | 4 | 5 | V-1 | Amy2b | 280 | 4-May-15 |
| 18900 | 2 | 3 | 4 | 5 | V-2 | Scgb2b12 | | | 2379 | 2 | 3 | 4 | 5 | V-1 | Ank1 | 286 | 12-May-15 |
| 18901 | 2 | 3 | 4 | 5 | V-2 | Scgb2b15 | | | 2395 | 2 | 3 | 4 | 5 | V-1 | Ankrd1 | 27063 | 23-May-15 |
| 18902 | 2 | 3 | 4 | 5 | V-2 | Scgb2b17 | | | 2405 | 2 | 3 | 4 | 5 | V-1 | Ankrd2 | 26287 | 4-May-15 |
| 19033 | 2 | 3 | 4 | 5 | V-2 | Selenbp2 | | | 2438 | 2 | 3 | 4 | 5 | V-1 | Ankrd66 | 100287718 | 21-May-15 |
| 19108 | 2 | 3 | 4 | 5 | V-2 | Serpina1e | | | 2462 | 2 | 3 | 4 | 5 | V-1 | Anpep | 290 | 12-May-15 |
| 19121 | 2 | 3 | 4 | 5 | V-2 | Serpina4-ps1 | | | 2491 | 2 | 3 | 4 | 5 | V-1 | Aplm2 | 10053 | 12-May-15 |
| 19210 | 2 | 3 | 4 | 5 | V-2 | Sfrp5 | 6425 | 10-May-15 | 2493 | 2 | 3 | 4 | 5 | V-1 | Ap1s2 | 8905 | 21-May-15 |
| 19501 | 2 | 3 | 4 | 5 | V-2 | Slc22a7 | 10864 | 17-May-15 | 2494 | 2 | 3 | 4 | 5 | V-1 | Ap1s3 | 130340 | 4-May-15 |
| 19786 | 2 | 3 | 4 | 5 | V-2 | Slco1a1 | | | 2545 | 2 | 3 | 4 | 5 | V-1 | Apoa2 | 336 | 7-Jun-15 |
| 19925 | 2 | 3 | 4 | 5 | V-2 | Smtnl2 | 342527 | 4-May-15 | 2546 | 2 | 3 | 4 | 5 | V-1 | Apoa4 | 337 | 4-May-15 |
| 19980 | 2 | 3 | 4 | 5 | V-2 | Snora2b | 677794 | 4-May-15 | 2547 | 2 | 3 | 4 | 5 | V-1 | Apoa5 | 116519 | 12-May-15 |
| 19982 | 2 | 3 | 4 | 5 | V-2 | Snora30 | 677813 | 4-May-15 | 2550 | 2 | 3 | 4 | 5 | V-1 | Apobec2 | 10930 | 4-May-15 |
| 19990 | 2 | 3 | 4 | 5 | V-2 | Snora44 | 677825 | 4-May-15 | 2556 | 2 | 3 | 4 | 5 | V-1 | Apoc3 | 345 | 12-May-15 |
| 20003 | 2 | 3 | 4 | 5 | V-2 | Snora78 | 677844 | 4-May-15 | 2557 | 2 | 3 | 4 | 5 | V-1 | Apoc4 | 346 | 12-May-15 |
| 20021 | 2 | 3 | 4 | 5 | V-2 | Snord15b | 114599 | 4-May-15 | 2559 | 2 | 3 | 4 | 5 | V-1 | Apoe | 348 | 24-May-15 |
| 20030 | 2 | 3 | 4 | 5 | V-2 | Snord23 | 692091 | 4-May-15 | 2572 | 2 | 3 | 4 | 5 | V-1 | Apol8 | | |
| 20385 | 2 | 3 | 4 | 5 | V-2 | Spt1 | 10558 | 23-May-15 | 2624 | 2 | 3 | 4 | 5 | V-1 | Arg2 | 384 | 4-May-15 |
| 20714 | 2 | 3 | 4 | 5 | V-2 | Susd4 | 55061 | 4-May-15 | 2746 | 2 | 3 | 4 | 5 | V-1 | Armcx6 | 54470 | 4-May-15 |
| 21117 | 2 | 3 | 4 | 5 | V-2 | Tekt1 | 83659 | 21-May-15 | 2748 | 2 | 3 | 4 | 5 | V-1 | Arnt2 | 9915 | 12-May-15 |
| 21265 | 2 | 3 | 4 | 5 | V-2 | Thrsp | 7069 | 4-May-15 | 2774 | 2 | 3 | 4 | 5 | V-1 | Art1 | 417 | 7-Jun-15 |
| 21288 | 2 | 3 | 4 | 5 | V-2 | Tigd4 | 201798 | 4-May-15 | 2794 | 2 | 3 | 4 | 5 | V-1 | Asb11 | 140456 | 4-May-15 |
| 21599 | 2 | 3 | 4 | 5 | V-2 | Tmem45b | 120224 | 4-May-15 | 2799 | 2 | 3 | 4 | 5 | V-1 | Asb16 | 92591 | 4-May-15 |
| 21712 | 2 | 3 | 4 | 5 | V-2 | Tnfrsf13c | 115650 | 12-May-15 | 2806 | 2 | 3 | 4 | 5 | V-1 | Asb5 | 140458 | 4-May-15 |
| 22205 | 2 | 3 | 4 | 5 | V-2 | Ttr | 7276 | 31-May-15 | 2817 | 2 | 3 | 4 | 5 | V-1 | Ascl4 | 121549 | 4-May-15 |
| 23012 | 2 | 3 | 4 | 5 | V-2 | Vpreb3 | 29802 | 13-May-15 | 2843 | 2 | 3 | 4 | 5 | V-1 | Asprv1 | 151516 | 4-May-15 |
| 23193 | 2 | 3 | 4 | 5 | V-2 | Wfdc18 | | | 2864 | 2 | 3 | 4 | 5 | V-1 | Atcayos | | |
| 23372 | 2 | 3 | 4 | 5 | V-2 | Zbed6 | 100381270 | 4-May-15 | 2907 | 2 | 3 | 4 | 5 | V-1 | Atp10b | 23120 | 4-May-15 |
| 23598 | 2 | 3 | 4 | 5 | V-2 | Zfp369 | | | 2926 | 2 | 3 | 4 | 5 | V-1 | Atp2a1 | 487 | 4-May-15 |
| 18 | 2 | 3 | 4 | 5 | V-1 | 0610040F04Rik | | | 2931 | 2 | 3 | 4 | 5 | V-1 | Atp2b3 | 492 | 4-May-15 |
| 138 | 2 | 3 | 4 | 5 | V-1 | 1700009N14Rik | | | 2962 | 2 | 3 | 4 | 5 | V-1 | Atp6v0c-ps2 | | |
| 239 | 2 | 3 | 4 | 5 | V-1 | 1700027A15Rik | | | 2964 | 2 | 3 | 4 | 5 | V-1 | Atp6v0d2 | 245973 | 4-May-15 |
| 440 | 2 | 3 | 4 | 5 | V-1 | 1810009J06Rik | | | 3012 | 2 | 3 | 4 | 5 | V-1 | AU015791 | | |
| 450 | 2 | 3 | 4 | 5 | V-1 | 1810019D21Rik | | | 3053 | 2 | 3 | 4 | 5 | V-1 | AW549542 | | |
| 466 | 2 | 3 | 4 | 5 | V-1 | 1810053B23Rik | | | 3068 | 2 | 3 | 4 | 5 | V-1 | AY761185 | | |
| 498 | 2 | 3 | 4 | 5 | V-1 | 2210010C04Rik | | | 3182 | 2 | 3 | 4 | 5 | V-1 | Basp1 | 10409 | 4-May-15 |
| 517 | 2 | 3 | 4 | 5 | V-1 | 2300002M23Rik | | | 3266 | 2 | 3 | 4 | 5 | V-1 | BC048679 | | |
| 526 | 2 | 3 | 4 | 5 | V-1 | 2310002L09Rik | | | 3299 | 2 | 3 | 4 | 5 | V-1 | BC100530 | | |
| 536 | 2 | 3 | 4 | 5 | V-1 | 2310010J17Rik | | | 3328 | 2 | 3 | 4 | 5 | V-1 | Bcl2a1b | | |
| 540 | 2 | 3 | 4 | 5 | V-1 | 2310015B20Rik | | | 3337 | 2 | 3 | 4 | 5 | V-1 | Bcl2l15 | 440603 | 4-May-15 |
| 568 | 2 | 3 | 4 | 5 | V-1 | 2310061N02Rik | | | 3374 | 2 | 3 | 4 | 5 | V-1 | Bex1 | 55859 | 7-Jun-15 |
| 639 | 2 | 3 | 4 | 5 | V-1 | 2610528A11Rik | | | 3375 | 2 | 3 | 4 | 5 | V-1 | Bex2 | 84707 | 7-Jun-15 |
| 687 | 2 | 3 | 4 | 5 | V-1 | 2810459M11Rik | | | 3376 | 2 | 3 | 4 | 5 | V-1 | Bex4 | 56271 | 4-May-15 |
| 705 | 2 | 3 | 4 | 5 | V-1 | 2900092D14Rik | | | 3383 | 2 | 3 | 4 | 5 | V-1 | Bglap3 | | |
| 738 | 2 | 3 | 4 | 5 | V-1 | 3425401B19Rik | | | 3392 | 2 | 3 | 4 | 5 | V-1 | Bhmt | 635 | 4-May-15 |
| 826 | 2 | 3 | 4 | 5 | V-1 | 4930412O13Rik | | | 3462 | 2 | 3 | 4 | 5 | V-1 | Bpi | 671 | 4-May-15 |
| 1088 | 2 | 3 | 4 | 5 | V-1 | 4930571K23Rik | | | 3520 | 2 | 3 | 4 | 5 | V-1 | Bsph1 | 100131137 | 4-May-15 |
| 1215 | 2 | 3 | 4 | 5 | V-1 | 4933411K16Rik | | | 3522 | 2 | 3 | 4 | 5 | V-1 | Bspry | 54836 | 4-May-15 |
| 1289 | 2 | 3 | 4 | 5 | V-1 | 5033404E19Rik | | | 3546 | 2 | 3 | 4 | 5 | V-1 | Btg3 | 10950 | 12-May-15 |
| 1338 | 2 | 3 | 4 | 5 | V-1 | 5830403L16Rik | | | 3553 | 2 | 3 | 4 | 5 | V-1 | Btnl10 | 100129094 | 4-May-15 |
| 1408 | 2 | 3 | 4 | 5 | V-1 | 8430408G22Rik | | | 3633 | 2 | 3 | 4 | 5 | V-1 | C2cd4b | 388125 | 4-May-15 |
| 1440 | 2 | 3 | 4 | 5 | V-1 | 9130230L23Rik | | | | | | | | | | | |

Fig.22 - 3

| | | | | | | | | | | | | | | | | |
|---|---|---|---|---|---|---|---|---|---|---|---|---|---|---|---|---|
| 3637 | 2 | 3 | 4 | 5 | V-1 | C3 | 718 | 23-May-15 | 5482 | 2 | 3 | 4 | 5 | V-1 | Cyp3a11 | | |
| 3656 | 2 | 3 | 4 | 5 | V-1 | C4bp | 722, 725 | 7-Jun-15 | 5488 | 2 | 3 | 4 | 5 | V-1 | Cyp3a44 | | |
| 3713 | 2 | 3 | 4 | 5 | V-1 | Cacna1s | 779 | 23-May-15 | 5490 | 2 | 3 | 4 | 5 | V-1 | Cyp3a59 | | |
| 3722 | 2 | 3 | 4 | 5 | V-1 | Cacng1 | 786 | 4-May-15 | 5495 | 2 | 3 | 4 | 5 | V-1 | Cyp4a14 | | |
| 3727 | 2 | 3 | 4 | 5 | V-1 | Cacng6 | 59285 | 4-May-15 | 5610 | 2 | 3 | 4 | 5 | V-1 | D730048I06Rik | | |
| 3755 | 2 | 3 | 4 | 5 | V-1 | Calm4 | | | 5671 | 2 | 3 | 4 | 5 | V-1 | Dbil5 | | |
| 3757 | 2 | 3 | 4 | 5 | V-1 | Calm3 | 810 | 4-May-15 | 5719 | 2 | 3 | 4 | 5 | V-1 | Dcstamp | 81501 | 12-May-15 |
| 3768 | 2 | 3 | 4 | 5 | V-1 | Camk2a | 815 | 12-May-15 | 5745 | 2 | 3 | 4 | 5 | V-1 | Ddi2 | 84301 | 4-May-15 |
| 3769 | 2 | 3 | 4 | 5 | V-1 | Camk2b | 816 | 4-May-15 | 5748 | 2 | 3 | 4 | 5 | V-1 | Ddit4l | 115265 | 4-May-15 |
| 3791 | 2 | 3 | 4 | 5 | V-1 | Cap2 | 10486 | 7-Jun-15 | 5809 | 2 | 3 | 4 | 5 | V-1 | Defa24 | | |
| 3801 | 2 | 3 | 4 | 5 | V-1 | Capn5 | 726 | | 5821 | 2 | 3 | 4 | 5 | V-1 | Defb1 | 1672 | 10-May-15 |
| 3823 | 2 | 3 | 4 | 5 | V-1 | Car2 | 760 | 2015/6/7 | 5822 | 2 | 3 | 4 | 5 | V-1 | Defb10 | 245813 | 4-May-15 |
| 3824 | 2 | 3 | 4 | 5 | V-1 | Car3 | 761 | 17-May-15 | 5824 | 2 | 3 | 4 | 5 | V-1 | Defb12 | 245915 | 4-May-15 |
| 3827 | 2 | 3 | 4 | 5 | V-1 | Car5b | | | 5826 | 2 | 3 | 4 | 5 | V-1 | Defb14 | 245928 | 4-May-15 |
| 3864 | 2 | 3 | 4 | 5 | V-1 | Casq1 | 844 | | 5827 | 2 | 3 | 4 | 5 | V-1 | Defb15 | 245929 | 4-May-15 |
| 3882 | 2 | 3 | 4 | 5 | V-1 | Cav3 | 859 | 23-May-15 | 5828 | 2 | 3 | 4 | 5 | V-1 | Defb18 | 117285 | 4-May-15 |
| 3894 | 2 | 3 | 4 | 5 | V-1 | Cbr1 | 873 | 4-May-15 | 5829 | 2 | 3 | 4 | 5 | V-1 | Defb19 | 245932 | 4-May-15 |
| 3896 | 2 | 3 | 4 | 5 | V-1 | Cbr3 | 874 | 4-May-15 | 5830 | 2 | 3 | 4 | 5 | V-1 | Defb2 | 1673 | 10-May-15 |
| 4074 | 2 | 3 | 4 | 5 | V-1 | Ccl17 | 6361 | | 5831 | 2 | 3 | 4 | 5 | V-1 | Defb20 | 245932 | 4-May-15 |
| 4076 | 2 | 3 | 4 | 5 | V-1 | Ccl2 | 6347 | | 5832 | 2 | 3 | 4 | 5 | V-1 | Defb21 | 245934 | 4-May-15 |
| 4077 | 2 | 3 | 4 | 5 | V-1 | Ccl20 | 6364 | 31-May-15 | 5833 | 2 | 3 | 4 | 5 | V-1 | Defb22 | 245935 | 12-May-15 |
| 4079 | 2 | 3 | 4 | 5 | V-1 | Ccl21b | | | 5834 | 2 | 3 | 4 | 5 | V-1 | Defb23 | 245936 | 4-May-15 |
| 4091 | 2 | 3 | 4 | 5 | V-1 | Ccl6 | | | 5835 | 2 | 3 | 4 | 5 | V-1 | Defb25 | 245938 | 4-May-15 |
| 4120 | 2 | 3 | 4 | 5 | V-1 | Ccno | 10309 | 4-May-15 | 5836 | 2 | 3 | 4 | 5 | V-1 | Defb26 | 81623 | 4-May-15 |
| 4222 | 2 | 3 | 4 | 5 | V-1 | Cd52 | 1043 | 12-May-15 | 5837 | 2 | 3 | 4 | 5 | V-1 | Defb28 | 245939 | 4-May-15 |
| 4293 | 2 | 3 | 4 | 5 | V-1 | Cdcp1 | 64866 | | 5838 | 2 | 3 | 4 | 5 | V-1 | Defb29 | 140881 | 4-May-15 |
| 4311 | 2 | 3 | 4 | 5 | V-1 | Cdh3 | 1001 | 2015/6/7 | 5840 | 2 | 3 | 4 | 5 | V-1 | Defb30 | 245940 | 4-May-15 |
| 4386 | 2 | 3 | 4 | 5 | V-1 | Ceacam10 | | | 5843 | 2 | 3 | 4 | 5 | V-1 | Defb35 | | |
| 4411 | 2 | 3 | 4 | 5 | V-1 | Cel | 1056 | 12-May-15 | 5845 | 2 | 3 | 4 | 5 | V-1 | Defb37 | | |
| 4412 | 2 | 3 | 4 | 5 | V-1 | Cela1 | 1990 | 4-May-15 | 5847 | 2 | 3 | 4 | 5 | V-1 | Defb39 | | |
| 4413 | 2 | 3 | 4 | 5 | V-1 | Cela2a | 63036 | 4-May-15 | 5848 | 2 | 3 | 4 | 5 | V-1 | Defb4 | 1673 | 7-Jun-15 |
| 4414 | 2 | 3 | 4 | 5 | V-1 | Cela3b | 23436 | 4-May-15 | 5850 | 2 | 3 | 4 | 5 | V-1 | Defb41 | | |
| 4493 | 2 | 3 | 4 | 5 | V-1 | Ces1c | | | 5851 | 2 | 3 | 4 | 5 | V-1 | Defb42 | | |
| 4509 | 2 | 3 | 4 | 5 | V-1 | Ces5a | 221223 | 4-May-15 | 5852 | 2 | 3 | 4 | 5 | V-1 | Defb43 | | |
| 4516 | 2 | 3 | 4 | 5 | V-1 | Cfd | 1675 | 7-Jun-15 | 5854 | 2 | 3 | 4 | 5 | V-1 | Defb45 | | |
| 4534 | 2 | 3 | 4 | 5 | V-1 | Chac1 | 79094 | 23-May-15 | 5856 | 2 | 3 | 4 | 5 | V-1 | Defb47 | | |
| 4566 | 2 | 3 | 4 | 5 | V-1 | Chga | 1113 | | 5857 | 2 | 3 | 4 | 5 | V-1 | Defb48 | | |
| 4674 | 2 | 3 | 4 | 5 | V-1 | Cited1 | 4435 | 4-May-15 | 5885 | 2 | 3 | 4 | 5 | V-1 | Depdc7 | 91614 | 4-May-15 |
| 4676 | 2 | 3 | 4 | 5 | V-1 | Cited4 | 163732 | | 5890 | 2 | 3 | 4 | 5 | V-1 | Derl3 | 91319 | 3-May-15 |
| 4685 | 2 | 3 | 4 | 5 | V-1 | Ckm | 1158 | 24-May-15 | 5891 | 2 | 3 | 4 | 5 | V-1 | Des | 1874 | 23-May-15 |
| 4687 | 2 | 3 | 4 | 5 | V-1 | Ckmt2 | 1160 | | 5935 | 2 | 3 | 4 | 5 | V-1 | Dhrs7c | 201140 | 4-May-15 |
| 4711 | 2 | 3 | 4 | 5 | V-1 | Cldn1 | 9076 | | 6023 | 2 | 3 | 4 | 5 | V-1 | Dmkn | 93099 | 21-May-15 |
| 4715 | 2 | 3 | 4 | 5 | V-1 | Cldn13 | | | 6035 | 2 | 3 | 4 | 5 | V-1 | Dmrtc1a | | |
| 4716 | 2 | 3 | 4 | 5 | V-1 | Cldn14 | 23562 | 4-May-15 | 6038 | 2 | 3 | 4 | 5 | V-1 | Dmrtn | 2039 | 7-Jun-15 |
| 4722 | 2 | 3 | 4 | 5 | V-1 | Cldn2 | 9075 | 24-May-15 | 6074 | 2 | 3 | 4 | 5 | V-1 | Dnajb8 | 165721 | 4-May-15 |
| 4724 | 2 | 3 | 4 | 5 | V-1 | Cldn22 | 53842 | 4-May-15 | 6107 | 2 | 3 | 4 | 5 | V-1 | Dnase1 | 1773 | 12-May-15 |
| 4726 | 2 | 3 | 4 | 5 | V-1 | Cldn24 | 100132463 | 4-May-15 | 6126 | 2 | 3 | 4 | 5 | V-1 | Dnmt3l | 29947 | 17-May-15 |
| 4729 | 2 | 3 | 4 | 5 | V-1 | Cldn3 | 1365 | 4-May-15 | 6158 | 2 | 3 | 4 | 5 | V-1 | Dopey2 | 9980 | 4-May-15 |
| 4730 | 2 | 3 | 4 | 5 | V-1 | Cldn4 | 1364 | 3-May-15 | 6263 | 2 | 3 | 4 | 5 | V-1 | Duoxa2 | 405753 | 4-May-15 |
| 4733 | 2 | 3 | 4 | 5 | V-1 | Cldn7 | 1366 | | 6273 | 2 | 3 | 4 | 5 | V-1 | Dusp13 | 51207 | 4-May-15 |
| 4734 | 2 | 3 | 4 | 5 | V-1 | Cldn8 | 9073 | 4-May-15 | 6275 | 2 | 3 | 4 | 5 | V-1 | Dusp15 | 128853 | 4-May-15 |
| 4752 | 2 | 3 | 4 | 5 | V-1 | Clec2l | 154790 | 4-May-15 | 6288 | 2 | 3 | 4 | 5 | V-1 | Dusp5 | 1847 | 4-May-15 |
| 4767 | 2 | 3 | 4 | 5 | V-1 | Clec7a | 64581 | | 6336 | 2 | 3 | 4 | 5 | V-1 | E030003E18Rik | | |
| 4797 | 2 | 3 | 4 | 5 | V-1 | Clps | 1208 | 4-May-15 | 6404 | 2 | 3 | 4 | 5 | V-1 | Ear3 | 7025 | 4-May-15 |
| 4798 | 2 | 3 | 4 | 5 | V-1 | Clpsl2 | 389383 | 4-May-15 | 6442 | 2 | 3 | 4 | 5 | V-1 | Eddm3b | 64184 | 4-May-15 |
| 4812 | 2 | 3 | 4 | 5 | V-1 | Clu | 1191 | 12-May-15 | 6457 | 2 | 3 | 4 | 5 | V-1 | Eef1a2 | 1917 | 4-May-15 |
| 4845 | 2 | 3 | 4 | 5 | V-1 | Cmya5 | 202333 | | 6513 | 2 | 3 | 4 | 5 | V-1 | Egr1 | 1958 | 23-May-15 |
| 4851 | 2 | 3 | 4 | 5 | V-1 | Cnfn | 84518 | 4-May-15 | 6560 | 2 | 3 | 4 | 5 | V-1 | Eif3j1 | | |
| 4865 | 2 | 3 | 4 | 5 | V-1 | Cnn1 | 1264 | | 6561 | 2 | 3 | 4 | 5 | V-1 | Eif3j2 | | |
| 4965 | 2 | 3 | 4 | 5 | V-1 | Col6a4 | 344875, 646300 | 7/5/4 | 6605 | 2 | 3 | 4 | 5 | V-1 | Elf3 | 80237 | 4-May-15 |
| 5042 | 2 | 3 | 4 | 5 | V-1 | Cox6a2 | 1339 | | 6616 | 2 | 3 | 4 | 5 | V-1 | Elovl2 | 54898 | 4-May-15 |
| 5046 | 2 | 3 | 4 | 5 | V-1 | Cox7a1 | 1346 | | 6618 | 2 | 3 | 4 | 5 | V-1 | Elovl4 | 6785 | 12-May-15 |
| 5056 | 2 | 3 | 4 | 5 | V-1 | Cpa1 | 1357 | 4-May-15 | 6643 | 2 | 3 | 4 | 5 | V-1 | Emid1 | 129080 | 4-May-15 |
| 5057 | 2 | 3 | 4 | 5 | V-1 | Cpa2 | 1358 | 4-May-15 | 6654 | 2 | 3 | 4 | 5 | V-1 | Emp2 | 2013 | 12-May-15 |
| 5062 | 2 | 3 | 4 | 5 | V-1 | Cpb1 | 1360 | | 6659 | 2 | 3 | 4 | 5 | V-1 | Emx2 | 2018 | 17-May-15 |
| 5119 | 2 | 3 | 4 | 5 | V-1 | Crb3 | 92359 | 4-May-15 | 6678 | 2 | 3 | 4 | 5 | V-1 | Eno3 | 2027 | 12-May-15 |
| 5122 | 2 | 3 | 4 | 5 | V-1 | Crct1 | 54544 | 4-May-15 | 6684 | 2 | 3 | 4 | 5 | V-1 | Enpp1 | 5167 | 23-May-15 |
| 5148 | 2 | 3 | 4 | 5 | V-1 | Crisp1 | 167 | | 6713 | 2 | 3 | 4 | 5 | V-1 | Epb41l4b | | |
| 5151 | 2 | 3 | 4 | 5 | V-1 | Crisp4 | | | 6715 | 2 | 3 | 4 | 5 | V-1 | Epb4.2 | | |
| 5177 | 2 | 3 | 4 | 5 | V-1 | Cryaa | 1409 | | 6718 | 2 | 3 | 4 | 5 | V-1 | Epcam | 4072 | 24-May-15 |
| 5180 | 2 | 3 | 4 | 5 | V-1 | Cryba2 | 1412 | 3-May-15 | 6747 | 2 | 3 | 4 | 5 | V-1 | Eppin | 57119 | 4-May-15 |
| 5181 | 2 | 3 | 4 | 5 | V-1 | Cryba4 | 1413 | 4-May-15 | 6799 | 2 | 3 | 4 | 5 | V-1 | Ermap | 114625 | 12-May-15 |
| 5188 | 2 | 3 | 4 | 5 | V-1 | Crygc | 1420 | | 6839 | 2 | 3 | 4 | 5 | V-1 | Esrp1 | 54845 | 4-May-15 |
| 5199 | 2 | 3 | 4 | 5 | V-1 | Csad | 51380 | 4-May-15 | 6840 | 2 | 3 | 4 | 5 | V-1 | Esrp2 | 80004 | 4-May-15 |
| 5244 | 2 | 3 | 4 | 5 | V-1 | Csrp3 | 8048 | 23-May-15 | 6866 | 2 | 3 | 4 | 5 | V-1 | Etv4 | 2118 | 28-May-15 |
| 5246 | 2 | 3 | 4 | 5 | V-1 | Cst11 | 140880 | 4-May-15 | 6867 | 2 | 3 | 4 | 5 | V-1 | Etv5 | 2119 | 24-May-15 |
| 5247 | 2 | 3 | 4 | 5 | V-1 | Cst12 | | | 6953 | 2 | 3 | 4 | 5 | V-1 | Faah | 2166 | 7-Jun-15 |
| 5252 | 2 | 3 | 4 | 5 | V-1 | Cst8 | 10047 | 4-May-15 | 6954 | 2 | 3 | 4 | 5 | V-1 | Fabp1 | 2168 | 12-May-15 |
| 5302 | 2 | 3 | 4 | 5 | V-1 | Ctrl | 1506 | 4-May-15 | 6967 | 2 | 3 | 4 | 5 | V-1 | Fads6 | 283985 | 7-Jun-15 |
| 5350 | 2 | 3 | 4 | 5 | V-1 | Cux2 | 23316 | 4-May-15 | 6974 | 2 | 3 | 4 | 5 | V-1 | Faim2 | 23017 | 4-May-15 |
| 5351 | 2 | 3 | 4 | 5 | V-1 | Cuzd1 | 50624 | 4-May-15 | 7111 | 2 | 3 | 4 | 5 | V-1 | Fam20a | 54757 | 30-Apr-15 |
| 5362 | 2 | 3 | 4 | 5 | V-1 | Cxcl1 | 2919 | | 7142 | 2 | 3 | 4 | 5 | V-1 | Fam25c | 644054 | 12-May-15 |
| 5366 | 2 | 3 | 4 | 5 | V-1 | Cxcl13 | 10563 | 3-May-15 | 7203 | 2 | 3 | 4 | 5 | V-1 | Fam84a | 151354 | 12-May-15 |
| 5388 | 2 | 3 | 4 | 5 | V-1 | Cyb561 | 1534 | 12-May-15 | 7367 | 2 | 3 | 4 | 5 | V-1 | Fbxo40 | 51725 | 4-May-15 |
| 5413 | 2 | 3 | 4 | 5 | V-1 | Cym | | | 7395 | 2 | 3 | 4 | 5 | V-1 | Fga | 2243 | 29-May-15 |
| 5419 | 2 | 3 | 4 | 5 | V-1 | Cyp1a1 | 1543 | 12-May-15 | 7396 | 2 | 3 | 4 | 5 | V-1 | Fgb | 2244 | 29-May-15 |
| 5426 | 2 | 3 | 4 | 5 | V-1 | Cyp26b1 | 56603 | | 7417 | 2 | 3 | 4 | 5 | V-1 | Fgf23 | 8074 | 17-May-15 |
| 5429 | 2 | 3 | 4 | 5 | V-1 | Cyp27b1 | 1594 | 12-May-15 | 7425 | 2 | 3 | 4 | 5 | V-1 | Fgfbp1 | 9982 | 4-May-15 |
| 5432 | 2 | 3 | 4 | 5 | V-1 | Cyp2a4 | | | 7434 | 2 | 3 | 4 | 5 | V-1 | Fgg | 2266 | 31-May-15 |
| 5433 | 2 | 3 | 4 | 5 | V-1 | Cyp2a5 | | | 7446 | 2 | 3 | 4 | 5 | V-1 | Fhl3 | 2275 | 7-Jun-15 |
| 5439 | 2 | 3 | 4 | 5 | V-1 | Cyp2b9 | 1555, 1556 | 7-Jun-15 | 7447 | 2 | 3 | 4 | 5 | V-1 | Fhl4 | 8676 | 23-May-15 |
| 5442 | 2 | 3 | 4 | 5 | V-1 | Cyp2c38 | | | 7466 | 2 | 3 | 4 | 5 | V-1 | Fitm1 | 161247 | 4-May-15 |
| 5466 | 2 | 3 | 4 | 5 | V-1 | Cyp2e1 | 1571 | 24-May-15 | 7494 | 2 | 3 | 4 | 5 | V-1 | Flnc | 2318 | 23-May-15 |
| 5467 | 2 | 3 | 4 | 5 | V-1 | Cyp2f2 | | | 7498 | 2 | 3 | 4 | 5 | V-1 | Flrt2 | 23768 | 4-May-15 |
| 5481 | 2 | 3 | 4 | 5 | V-1 | Cyp39a1 | 51302 | | 7512 | 2 | 3 | 4 | 5 | V-1 | Fmo2 | 2327 | 12-May-15 |
| | | | | | | | | | 7513 | 2 | 3 | 4 | 5 | V-1 | Fmo3 | 2328 | 24-May-15 |
| | | | | | | | | | 7522 | 2 | 3 | 4 | 5 | V-1 | Fn3k | 64122 | 4-May-15 |

Fig.22 - 4

| | | | | | | | | |
|---|---|---|---|---|---|---|---|---|
| 7569 | 2 | 3 | 4 | 5 | V-1 | Foxi1 | 2299 | 23-May-15 |
| 7572 | 2 | 3 | 4 | 5 | V-1 | Foxq1 | 2302 | 12-May-15 |
| 7671 | 2 | 3 | 4 | 5 | V-1 | Fut1 | 2523 | 12-May-15 |
| 7675 | 2 | 3 | 4 | 5 | V-1 | Fut4 | 2526 | 12-May-15 |
| 7688 | 2 | 3 | 4 | 5 | V-1 | Fxyd4 | 53828 | 4-May-15 |
| 7760 | 2 | 3 | 4 | 5 | V-1 | Gadd45b | 4616 | 4-May-15 |
| 7769 | 2 | 3 | 4 | 5 | V-1 | Gal3st4 | 79690 | 4-May-15 |
| 7779 | 2 | 3 | 4 | 5 | V-1 | Galnt12 | 79695 | 4-May-15 |
| 7803 | 2 | 3 | 4 | 5 | V-1 | Gap43 | 2596 | 12-May-15 |
| 7826 | 2 | 3 | 4 | 5 | V-1 | Gata3 | 2625 | 17-May-15 |
| 7857 | 2 | 3 | 4 | 5 | V-1 | Gc | 2638 | 17-May-15 |
| 7873 | 2 | 3 | 4 | 5 | V-1 | Gcm2 | 9247 | 12-May-15 |
| 7878 | 2 | 3 | 4 | 5 | V-1 | Gcm4 | 51301 | 4-May-15 |
| 7926 | 2 | 3 | 4 | 5 | V-1 | Gfra1 | 2674 | 12-May-15 |
| 8012 | 2 | 3 | 4 | 5 | V-1 | Glb1l3 | 112937 | 4-May-15 |
| 8015 | 2 | 3 | 4 | 5 | V-1 | Gldc | 2731 | 23-May-15 |
| 8041 | 2 | 3 | 4 | 5 | V-1 | Glrp1 | | |
| 8097 | 2 | 3 | 4 | 5 | V-1 | Gm10334 | | |
| 8126 | 2 | 3 | 4 | 5 | V-1 | Gm10487 | | |
| 8148 | 2 | 3 | 4 | 5 | V-1 | Gm10639 | | |
| 8186 | 2 | 3 | 4 | 5 | V-1 | Gm1110 | | |
| 8256 | 2 | 3 | 4 | 5 | V-1 | Gm12191 | | |
| 8338 | 2 | 3 | 4 | 5 | V-1 | Gm13363 | | |
| 8407 | 2 | 3 | 4 | 5 | V-1 | Gm14476 | | |
| 8441 | 2 | 3 | 4 | 5 | V-1 | Gm15056 | | |
| 8464 | 2 | 3 | 4 | 5 | V-1 | Gm15386 | | |
| 8491 | 2 | 3 | 4 | 5 | V-1 | Gm15818 | | |
| 8543 | 2 | 3 | 4 | 5 | V-1 | Gm1673 | | |
| 8564 | 2 | 3 | 4 | 5 | V-1 | Gm17252 | | |
| 8567 | 2 | 3 | 4 | 5 | V-1 | Gm17365 | | |
| 8571 | 2 | 3 | 4 | 5 | V-1 | Gm17677 | | |
| 8573 | 2 | 3 | 4 | 5 | V-1 | Gm17727 | | |
| 8636 | 2 | 3 | 4 | 5 | V-1 | Gm1987 | | |
| 8661 | 2 | 3 | 4 | 5 | V-1 | Gm2061 | | |
| 8728 | 2 | 3 | 4 | 5 | V-1 | Gm266 | | |
| 8729 | 2 | 3 | 4 | 5 | V-1 | Gm2663 | | |
| 8767 | 2 | 3 | 4 | 5 | V-1 | Gm3428 | | |
| 8784 | 2 | 3 | 4 | 5 | V-1 | Gm3776 | | |
| 8829 | 2 | 3 | 4 | 5 | V-1 | Gm4736 | | |
| 8844 | 2 | 3 | 4 | 5 | V-1 | Gm4846 | | |
| 8936 | 2 | 3 | 4 | 5 | V-1 | Gm5631 | | |
| 8962 | 2 | 3 | 4 | 5 | V-1 | Gm5741 | | |
| 8964 | 2 | 3 | 4 | 5 | V-1 | Gm5771 | | |
| 8984 | 2 | 3 | 4 | 5 | V-1 | Gm5916 | | |
| 8995 | 2 | 3 | 4 | 5 | V-1 | Gm6040 | | |
| 9051 | 2 | 3 | 4 | 5 | V-1 | Gm6644 | | |
| 9060 | 2 | 3 | 4 | 5 | V-1 | Gm6792 | | |
| 9093 | 2 | 3 | 4 | 5 | V-1 | Gm7325 | | |
| 9094 | 2 | 3 | 4 | 5 | V-1 | Gm7334 | | |
| 9141 | 2 | 3 | 4 | 5 | V-1 | Gm867 | | |
| 9161 | 2 | 3 | 4 | 5 | V-1 | Gm8882 | | |
| 9172 | 2 | 3 | 4 | 5 | V-1 | Gm94 | | |
| 9196 | 2 | 3 | 4 | 5 | V-1 | Gm9992 | | |
| 9207 | 2 | 3 | 4 | 5 | V-1 | Gml | 2765 | 4-May-15 |
| 9291 | 2 | 3 | 4 | 5 | V-1 | Gp2 | 2813 | 4-May-15 |
| 9335 | 2 | 3 | 4 | 5 | V-1 | Gpnmb | 10457 | 12-May-15 |
| 9418 | 2 | 3 | 4 | 5 | V-1 | Gpr82 | 27197 | 12-May-15 |
| 9449 | 2 | 3 | 4 | 5 | V-1 | Gpx5 | 2880 | 4-May-15 |
| 9456 | 2 | 3 | 4 | 5 | V-1 | Gpx6 | 257202 | 12-May-15 |
| 9472 | 2 | 3 | 4 | 5 | V-1 | Grhl2 | 79977 | 24-May-15 |
| 9539 | 2 | 3 | 4 | 5 | V-1 | Gsg1 | 83445 | 7-Jun-15 |
| 9550 | 2 | 3 | 4 | 5 | V-1 | Gsta1 | 2938 | 12-May-15 |
| 9551 | 2 | 3 | 4 | 5 | V-1 | Gsta2 | 2939 | 12-May-15 |
| 9553 | 2 | 3 | 4 | 5 | V-1 | Gsta4 | 2941 | 12-May-15 |
| 9556 | 2 | 3 | 4 | 5 | V-1 | Gstm1 | 2944 | 24-May-15 |
| 9558 | 2 | 3 | 4 | 5 | V-1 | Gstm3 | 2947 | 12-May-15 |
| 9626 | 2 | 3 | 4 | 5 | V-1 | Gulo | 2989 | 12-May-15 |
| 9636 | 2 | 3 | 4 | 5 | V-1 | Gypa | 2993 | 21-May-15 |
| 9652 | 2 | 3 | 4 | 5 | V-1 | H19 | 283120 | 23-May-15 |
| 9698 | 2 | 3 | 4 | 5 | V-1 | H2-Q10 | | |
| 9704 | 2 | 3 | 4 | 5 | V-1 | H2-Q8 | | |
| 9728 | 2 | 3 | 4 | 5 | V-1 | Hamp | 57817 | 24-May-15 |
| 9729 | 2 | 3 | 4 | 5 | V-1 | Hamp2 | | |
| 9734 | 2 | 3 | 4 | 5 | V-1 | Hap1 | 9001 | 7-Jun-15 |
| 9755 | 2 | 3 | 4 | 5 | V-1 | Havcr1 | 26762 | 13-May-15 |
| 9759 | 2 | 3 | 4 | 5 | V-1 | Hba-a2 | 3039 | 7-Jun-15 |
| 9764 | 2 | 3 | 4 | 5 | V-1 | Hbb-bs | 3044 | 9-Jun-16 |
| 9820 | 2 | 3 | 4 | 5 | V-1 | Hebp2 | 23593 | 4-May-15 |
| 9834 | 2 | 3 | 4 | 5 | V-1 | Hemgn | 55363 | 4-May-15 |
| 9836 | 2 | 3 | 4 | 5 | V-1 | Hemt1 | | |
| 9865 | 2 | 3 | 4 | 5 | V-1 | Hfe2 | 148738 | 23-May-15 |
| 9869 | 2 | 3 | 4 | 5 | V-1 | Hgfac | 3083 | 4-May-15 |
| 9902 | 2 | 3 | 4 | 5 | V-1 | Hipk2 | 28996 | 31-May-15 |
| 9961 | 2 | 3 | 4 | 5 | V-1 | Hist2h2aa2 | | |
| 9967 | 2 | 3 | 4 | 5 | V-1 | Hist2h3c1 | | |
| 9968 | 2 | 3 | 4 | 5 | V-1 | Hist2h3c2 | | |
| 10079 | 2 | 3 | 4 | 5 | V-1 | Hoxb6 | 3216 | 4-May-15 |
| 10081 | 2 | 3 | 4 | 5 | V-1 | Hoxb8 | 3218 | 4-May-15 |
| 10097 | 2 | 3 | 4 | 5 | V-1 | Hoxd3 | 3232 | 12-May-15 |
| 10108 | 2 | 3 | 4 | 5 | V-1 | Hpdl | 84842 | 7-Jun-15 |
| 10120 | 2 | 3 | 4 | 5 | V-1 | Hpx | 3263 | 4-May-15 |
| 10125 | 2 | 3 | 4 | 5 | V-1 | Hrc | 3270 | 12-May-15 |
| 10140 | 2 | 3 | 4 | 5 | V-1 | Hs3st3b1 | 9953 | 4-May-15 |
| 10161 | 2 | 3 | 4 | 5 | V-1 | Hsd17b6 | 8630 | 4-May-15 |
| 10199 | 2 | 3 | 4 | 5 | V-1 | Hspb3 | 8988 | 4-May-15 |
| 10200 | 2 | 3 | 4 | 5 | V-1 | Hspb6 | 126393 | 12-May-15 |
| 10201 | 2 | 3 | 4 | 5 | V-1 | Hspb7 | 27129 | 4-May-15 |
| 10203 | 2 | 3 | 4 | 5 | V-1 | Hspb9 | 94086 | 4-May-15 |
| 10263 | 2 | 3 | 4 | 5 | V-1 | Icam4 | 3386 | 12-May-15 |
| 10289 | 2 | 3 | 4 | 5 | V-1 | Ido1 | 3620 | 24-May-15 |
| 10373 | 2 | 3 | 4 | 5 | V-1 | Igfbp1 | 3484 | 17-May-15 |
| 10386 | 2 | 3 | 4 | 5 | V-1 | Igj | 3512 | 12-May-15 |
| 10468 | 2 | 3 | 4 | 5 | V-1 | Il22ra1 | 58985 | 4-May-15 |
| 10497 | 2 | 3 | 4 | 5 | V-1 | Ildr1 | 286676 | 4-May-15 |
| 10498 | 2 | 3 | 4 | 5 | V-1 | Ildr2 | 387597 | 12-May-15 |
| 10528 | 2 | 3 | 4 | 5 | V-1 | Inha | 3623 | 12-May-15 |
| 10579 | 2 | 3 | 4 | 5 | V-1 | Ip6k3 | 117283 | 12-May-15 |
| 10665 | 2 | 3 | 4 | 5 | V-1 | Isyna1 | 51477 | 12-May-15 |
| 10687 | 2 | 3 | 4 | 5 | V-1 | Itgax | 3687 | 4-May-15 |
| 10690 | 2 | 3 | 4 | 5 | V-1 | Itgb1bp2 | 26548 | 4-May-15 |
| 10761 | 2 | 3 | 4 | 5 | V-1 | Jph2 | 57158 | 4-May-15 |
| 10767 | 2 | 3 | 4 | 5 | V-1 | Jsrp1 | 126306 | 4-May-15 |
| 10815 | 2 | 3 | 4 | 5 | V-1 | Kcna7 | 3743 | 4-May-15 |
| 10824 | 2 | 3 | 4 | 5 | V-1 | Kcnc4 | 3749 | 4-May-15 |
| 10841 | 2 | 3 | 4 | 5 | V-1 | Kcnh3 | 23416 | 4-May-15 |
| 10853 | 2 | 3 | 4 | 5 | V-1 | Kcnj11 | 3767 | 31-May-15 |
| 10854 | 2 | 3 | 4 | 5 | V-1 | Kcnj12 | 3768 | 4-May-15 |
| 10857 | 2 | 3 | 4 | 5 | V-1 | Kcnj15 | 3772 | 21-May-15 |
| 10866 | 2 | 3 | 4 | 5 | V-1 | Kcnk1 | 3775 | 4-May-15 |
| 10879 | 2 | 3 | 4 | 5 | V-1 | Kcnk9 | 51305 | 4-May-15 |
| 10906 | 2 | 3 | 4 | 5 | V-1 | Kctd1 | 284252 | 4-May-15 |
| 10956 | 2 | 3 | 4 | 5 | V-1 | Kel | 3792 | 12-May-15 |
| 11030 | 2 | 3 | 4 | 5 | V-1 | Klf1 | 10661 | 12-May-15 |
| 11077 | 2 | 3 | 4 | 5 | V-1 | Klhl30 | 377007 | 4-May-15 |
| 11078 | 2 | 3 | 4 | 5 | V-1 | Klhl31 | 401265 | 4-May-15 |
| 11081 | 2 | 3 | 4 | 5 | V-1 | Klhl34 | 257240 | 4-May-15 |
| 11086 | 2 | 3 | 4 | 5 | V-1 | Klhl40 | 131377 | 4-May-15 |
| 11087 | 2 | 3 | 4 | 5 | V-1 | Klhl41 | 10324 | 4-May-15 |
| 11095 | 2 | 3 | 4 | 5 | V-1 | Klk10 | 5655 | 21-May-15 |
| 11099 | 2 | 3 | 4 | 5 | V-1 | Klk14 | 43847 | 4-May-15 |
| 11107 | 2 | 3 | 4 | 5 | V-1 | Klk1b26 | | |
| 11144 | 2 | 3 | 4 | 5 | V-1 | Klrb1a | | |
| 11146 | 2 | 3 | 4 | 5 | V-1 | Klrb1c | | |
| 11167 | 2 | 3 | 4 | 5 | V-1 | Kng1 | 3827 | 4-May-15 |
| 11192 | 2 | 3 | 4 | 5 | V-1 | Krt13 | 3860 | 7-Jun-15 |
| 11193 | 2 | 3 | 4 | 5 | V-1 | Krt14 | 3861 | 23-May-15 |
| 11195 | 2 | 3 | 4 | 5 | V-1 | Krt16 | 3868 | 23-May-15 |
| 11197 | 2 | 3 | 4 | 5 | V-1 | Krt18 | 3875 | 24-May-15 |
| 11202 | 2 | 3 | 4 | 5 | V-1 | Krt23 | 25984 | 4-May-15 |
| 11216 | 2 | 3 | 4 | 5 | V-1 | Krt4 | 3851 | 4-May-15 |
| 11219 | 2 | 3 | 4 | 5 | V-1 | Krt5 | 3852 | 23-May-15 |
| 11220 | 2 | 3 | 4 | 5 | V-1 | Krt6a | 3853 | 28-May-15 |
| 11230 | 2 | 3 | 4 | 5 | V-1 | Krt78 | 196374 | 4-May-15 |
| 11295 | 2 | 3 | 4 | 5 | V-1 | Krtdap | 388533 | 4-May-15 |
| 11302 | 2 | 3 | 4 | 5 | V-1 | Kynu | 8942 | 4-May-15 |
| 11317 | 2 | 3 | 4 | 5 | V-1 | Lad1 | 3898 | 7-Jun-15 |
| 11370 | 2 | 3 | 4 | 5 | V-1 | Lbx1 | 10660 | 4-May-15 |
| 11389 | 2 | 3 | 4 | 5 | V-1 | Lce3a | 353142 | 4-May-15 |
| 11390 | 2 | 3 | 4 | 5 | V-1 | Lce3b | 353143 | 4-May-15 |
| 11391 | 2 | 3 | 4 | 5 | V-1 | Lce3c | 353144 | 4-May-15 |
| 11393 | 2 | 3 | 4 | 5 | V-1 | Lce3e | 353145 | 4-May-15 |
| 11394 | 2 | 3 | 4 | 5 | V-1 | Lce3f | | |
| 11400 | 2 | 3 | 4 | 5 | V-1 | Lcn10 | 414332 | 4-May-15 |
| 11402 | 2 | 3 | 4 | 5 | V-1 | Lcn12 | 286256 | 4-May-15 |
| 11403 | 2 | 3 | 4 | 5 | V-1 | Lcn2 | 3934 | 17-May-15 |
| 11406 | 2 | 3 | 4 | 5 | V-1 | Lcn5 | 353176 | |
| 11407 | 2 | 3 | 4 | 5 | V-1 | Lcn6 | 158062 | 4-May-15 |
| 11408 | 2 | 3 | 4 | 5 | V-1 | Lcn8 | 138307 | 12-May-15 |
| 11409 | 2 | 3 | 4 | 5 | V-1 | Lcn9 | 392399 | 12-May-15 |
| 11418 | 2 | 3 | 4 | 5 | V-1 | Ldb3 | 11155 | 23-May-15 |
| 11435 | 2 | 3 | 4 | 5 | V-1 | Lef1 | 51176 | 12-May-15 |
| 11439 | 2 | 3 | 4 | 5 | V-1 | Lelp1 | 149018 | 4-May-15 |
| 11467 | 2 | 3 | 4 | 5 | V-1 | Lgals7 | 3963, 653499 | 7-Jun-15 |
| 11527 | 2 | 3 | 4 | 5 | V-1 | Lingo1 | 84894 | 12-May-15 |
| 11536 | 2 | 3 | 4 | 5 | V-1 | Lpg | 9388 | 12-May-15 |
| 11538 | 2 | 3 | 4 | 5 | V-1 | Lpi | 149998 | 4-May-15 |
| 11573 | 2 | 3 | 4 | 5 | V-1 | Lmod2 | 442721 | 12-May-15 |
| 11574 | 2 | 3 | 4 | 5 | V-1 | Lmod3 | 56203 | 12-May-15 |
| 11586 | 2 | 3 | 4 | 5 | V-1 | LOC100048884 | | |
| 11629 | 2 | 3 | 4 | 5 | V-1 | Lor | 4014 | 4-May-15 |
| 11664 | 2 | 3 | 4 | 5 | V-1 | Lrcol1 | 100507055 | 4-May-15 |
| 11716 | 2 | 3 | 4 | 5 | V-1 | Lrrc30 | 339291 | 4-May-15 |
| 11833 | 2 | 3 | 4 | 5 | V-1 | Ly6g5b | 58496 | 21-May-15 |
| 11834 | 2 | 3 | 4 | 5 | V-1 | Ly6g5c | 80741 | 4-May-15 |
| 11859 | 2 | 3 | 4 | 5 | V-1 | Lypd8 | 646627 | 4-May-15 |
| 11877 | 2 | 3 | 4 | 5 | V-1 | Lyz2 | | |
| 11908 | 2 | 3 | 4 | 5 | V-1 | Mafa | 389692 | 7-Jun-15 |
| 11945 | 2 | 3 | 4 | 5 | V-1 | Mal | 4118 | 7-Jun-15 |
| 12049 | 2 | 3 | 4 | 5 | V-1 | Marc1 | 64757 | 12-May-15 |
| 12084 | 2 | 3 | 4 | 5 | V-1 | Mat1a | 4143 | 12-May-15 |
| 12097 | 2 | 3 | 4 | 5 | V-1 | Mb | 4151 | 4-May-15 |
| 12115 | 2 | 3 | 4 | 5 | V-1 | Mbnl3 | 55796 | 4-May-15 |
| 12116 | 2 | 3 | 4 | 5 | V-1 | Mboat1 | 154141 | 4-May-15 |
| 12180 | 2 | 3 | 4 | 5 | V-1 | Mdk | 4192 | 7-Jun-15 |
| 12256 | 2 | 3 | 4 | 5 | V-1 | Mesp1 | 55897 | 28-May-15 |
| 12257 | 2 | 3 | 4 | 5 | V-1 | Mesp2 | 145873 | 23-May-15 |
| 12312 | 2 | 3 | 4 | 5 | V-1 | Mfrp | 83552 | 4-May-15 |
| 12317 | 2 | 3 | 4 | 5 | V-1 | Mfsd2a | 84879 | 4-May-15 |
| 12432 | 2 | 3 | 4 | 5 | V-1 | Mir1291 | 100302221 | 21-May-15 |
| 12443 | 2 | 3 | 4 | 5 | V-1 | Mir133a-2 | | |
| 12456 | 2 | 3 | 4 | 5 | V-1 | Mir142b | | |
| 12479 | 2 | 3 | 4 | 5 | V-1 | Mir1668 | | |

Fig.22 - 5

| | | | | | | | | |
|---|---|---|---|---|---|---|---|---|
| 12553 | 2 | 3 | 4 | 5 | V-1 | Mir1957b | | |
| 12604 | 2 | 3 | 4 | 5 | V-1 | Mir215 | 406997 | 21-May-15 |
| 12972 | 2 | 3 | 4 | 5 | V-1 | Mir6340 | | |
| 12986 | 2 | 3 | 4 | 5 | V-1 | Mir6357 | | |
| 12992 | 2 | 3 | 4 | 5 | V-1 | Mir6363 | | |
| 13011 | 2 | 3 | 4 | 5 | V-1 | Mir6385 | | |
| 13018 | 2 | 3 | 4 | 5 | V-1 | Mir6392 | | |
| 13022 | 2 | 3 | 4 | 5 | V-1 | Mir6396 | | |
| 13029 | 2 | 3 | 4 | 5 | V-1 | Mir6403 | | |
| 13044 | 2 | 3 | 4 | 5 | V-1 | Mir6418 | | |
| 13092 | 2 | 3 | 4 | 5 | V-1 | Mir682 | | |
| 13093 | 2 | 3 | 4 | 5 | V-1 | Mir683-1 | | |
| 13094 | 2 | 3 | 4 | 5 | V-1 | Mir683-2 | | |
| 13130 | 2 | 3 | 4 | 5 | V-1 | Mir692-2b | | |
| 13180 | 2 | 3 | 4 | 5 | V-1 | Mir697 | | |
| 13205 | 2 | 3 | 4 | 5 | V-1 | Mir6992 | | |
| 13246 | 2 | 3 | 4 | 5 | V-1 | Mir703 | | |
| 13320 | 2 | 3 | 4 | 5 | V-1 | Mir7-1 | 407043 | 24-May-15 |
| 13330 | 2 | 3 | 4 | 5 | V-1 | Mir719 | | |
| 13375 | 2 | 3 | 4 | 5 | V-1 | Mir760 | 100126348 | 21-May-15 |
| 13423 | 2 | 3 | 4 | 5 | V-1 | Mir8093 | | |
| 13424 | 2 | 3 | 4 | 5 | V-1 | Mir8094 | | |
| 13427 | 2 | 3 | 4 | 5 | V-1 | Mir8097 | | |
| 13428 | 2 | 3 | 4 | 5 | V-1 | Mir8098 | | |
| 13429 | 2 | 3 | 4 | 5 | V-1 | Mir8099-1 | | |
| 13433 | 2 | 3 | 4 | 5 | V-1 | Mir8103 | | |
| 13434 | 2 | 3 | 4 | 5 | V-1 | Mir8104 | | |
| 13438 | 2 | 3 | 4 | 5 | V-1 | Mir8108 | | |
| 13442 | 2 | 3 | 4 | 5 | V-1 | Mir8112 | | |
| 13448 | 2 | 3 | 4 | 5 | V-1 | Mir8119 | | |
| 13483 | 2 | 3 | 4 | 5 | V-1 | Mirlet7d | 406886 | 21-May-15 |
| 13514 | 2 | 3 | 4 | 5 | V-1 | Mlf1 | 4291 | 12-May-15 |
| 13544 | 2 | 3 | 4 | 5 | V-1 | Mmp12 | 4321 | 4-May-15 |
| 13563 | 2 | 3 | 4 | 5 | V-1 | Mmp7 | 4316 | 17-May-15 |
| 13823 | 2 | 3 | 4 | 5 | V-1 | Mss51 | 118490 | 4-May-15 |
| 13826 | 2 | 3 | 4 | 5 | V-1 | Mstn | 2660 | 23-May-15 |
| 13832 | 2 | 3 | 4 | 5 | V-1 | Mt1 | 4489, 4494, 4495 | 7-Jun-15 |
| 13833 | 2 | 3 | 4 | 5 | V-1 | Mt2 | 4502 | 7-Jun-15 |
| 13834 | 2 | 3 | 4 | 5 | V-1 | Mt3 | 4504 | 24-May-15 |
| 13835 | 2 | 3 | 4 | 5 | V-1 | Mt4 | 84560 | 4-May-15 |
| 13905 | 2 | 3 | 4 | 5 | V-1 | Muc15 | 143662 | 4-May-15 |
| 13911 | 2 | 3 | 4 | 5 | V-1 | Muc5b | 727897 | 23-May-15 |
| 13933 | 2 | 3 | 4 | 5 | V-1 | Mup3 | | |
| 13935 | 2 | 3 | 4 | 5 | V-1 | Mup5 | | |
| 13940 | 2 | 3 | 4 | 5 | V-1 | Murc | 347273 | 4-May-15 |
| 13960 | 2 | 3 | 4 | 5 | V-1 | Myadml2 | 255275 | 4-May-15 |
| 13965 | 2 | 3 | 4 | 5 | V-1 | Mybpc1 | 4604 | 4-May-15 |
| 13966 | 2 | 3 | 4 | 5 | V-1 | Mybpc2 | 4606 | 4-May-15 |
| 13982 | 2 | 3 | 4 | 5 | V-1 | Myf6 | 4618 | 28-May-15 |
| 13984 | 2 | 3 | 4 | 5 | V-1 | Myh1 | 4619 | 4-May-15 |
| 13990 | 2 | 3 | 4 | 5 | V-1 | Myh2 | 4620 | 4-May-15 |
| 13992 | 2 | 3 | 4 | 5 | V-1 | Myh4 | 4622 | 4-May-15 |
| 13994 | 2 | 3 | 4 | 5 | V-1 | Myh7 | 4625 | 23-May-15 |
| 13996 | 2 | 3 | 4 | 5 | V-1 | Myh8 | 4626 | 12-May-15 |
| 13998 | 2 | 3 | 4 | 5 | V-1 | Myl1 | 4632 | 4-May-15 |
| 14003 | 2 | 3 | 4 | 5 | V-1 | Myl3 | 4634 | 23-May-15 |
| 14006 | 2 | 3 | 4 | 5 | V-1 | Myl6b | 140465 | 4-May-15 |
| 14011 | 2 | 3 | 4 | 5 | V-1 | Mylk2 | 85366 | 23-May-15 |
| 14013 | 2 | 3 | 4 | 5 | V-1 | Mylk4 | 340156 | 4-May-15 |
| 14014 | 2 | 3 | 4 | 5 | V-1 | Mylpf | 29895 | 4-May-15 |
| 14020 | 2 | 3 | 4 | 5 | V-1 | Myo18b | 84700 | 4-May-15 |
| 14031 | 2 | 3 | 4 | 5 | V-1 | Myo3b | 140469 | 4-May-15 |
| 14033 | 2 | 3 | 4 | 5 | V-1 | Myo5b | 4645 | 4-May-15 |
| 14045 | 2 | 3 | 4 | 5 | V-1 | Myom1 | 8736 | 12-May-15 |
| 14046 | 2 | 3 | 4 | 5 | V-1 | Myom2 | 9172 | 4-May-15 |
| 14048 | 2 | 3 | 4 | 5 | V-1 | Myot | 9499 | 23-May-15 |
| 14049 | 2 | 3 | 4 | 5 | V-1 | Myoz1 | 58529 | 12-May-15 |
| 14050 | 2 | 3 | 4 | 5 | V-1 | Myoz2 | 51778 | 12-May-15 |
| 14052 | 2 | 3 | 4 | 5 | V-1 | Mypn | 84665 | 12-May-15 |
| 14111 | 2 | 3 | 4 | 5 | V-1 | Naip7 | | |
| 14147 | 2 | 3 | 4 | 5 | V-1 | Nav2 | 89797 | 4-May-15 |
| 14183 | 2 | 3 | 4 | 5 | V-1 | Ncmap | 400746 | 4-May-15 |
| 14196 | 2 | 3 | 4 | 5 | V-1 | Nctc1 | | |
| 14262 | 2 | 3 | 4 | 5 | V-1 | Neb | 4703 | 23-May-15 |
| 14296 | 2 | 3 | 4 | 5 | V-1 | Nell1 | 4745 | 12-May-15 |
| 14324 | 2 | 3 | 4 | 5 | V-1 | Nexn | 91624 | 23-May-15 |
| 14338 | 2 | 3 | 4 | 5 | V-1 | Nfe2l3 | 9603 | 4-May-15 |
| 14364 | 2 | 3 | 4 | 5 | V-1 | Ngfr | 4804 | 17-May-15 |
| 14379 | 2 | 3 | 4 | 5 | V-1 | Nhsl1 | 57224 | 4-May-15 |
| 14524 | 2 | 3 | 4 | 5 | V-1 | Nos2 | 4843 | 7-Jun-15 |
| 14586 | 2 | 3 | 4 | 5 | V-1 | Nptxr | 23467 | 4-May-15 |
| 14617 | 2 | 3 | 4 | 5 | V-1 | Nr4a1 | 3164 | 3-May-15 |
| 14624 | 2 | 3 | 4 | 5 | V-1 | Nrap | 4892 | 7-Jun-15 |
| 14680 | 2 | 3 | 4 | 5 | V-1 | Nt5c1a | 84618 | 4-May-15 |
| 14708 | 2 | 3 | 4 | 5 | V-1 | Ntsr2 | 23620 | 4-May-15 |
| 14776 | 2 | 3 | 4 | 5 | V-1 | Nupr1l | 389493 | 4-May-15 |
| 14787 | 2 | 3 | 4 | 5 | V-1 | Nxf3 | 56000 | 12-May-15 |
| 14792 | 2 | 3 | 4 | 5 | V-1 | Nxpe2 | 120406 | 4-May-15 |
| 14799 | 2 | 3 | 4 | 5 | V-1 | Nxph4 | 11247 | 4-May-15 |
| 14823 | 2 | 3 | 4 | 5 | V-1 | Oaz1-ps | | |
| 14825 | 2 | 3 | 4 | 5 | V-1 | Oaz3 | 51686 | 12-May-15 |
| 14841 | 2 | 3 | 4 | 5 | V-1 | Ociad2 | 132299 | 4-May-15 |
| 14848 | 2 | 3 | 4 | 5 | V-1 | Odf1 | 4956 | 4-May-15 |
| 14854 | 2 | 3 | 4 | 5 | V-1 | Odf3l2 | 284451 | 4-May-15 |
| 16005 | 2 | 3 | 4 | 5 | V-1 | Omp | 4975 | 4-May-15 |
| 16065 | 2 | 3 | 4 | 5 | V-1 | Oscar | 126014 | 17-May-15 |
| 16110 | 2 | 3 | 4 | 5 | V-1 | Ovch2 | 341277 | 4-May-15 |
| 16128 | 2 | 3 | 4 | 5 | V-1 | P2rx2 | 22953 | 21-May-15 |
| 16165 | 2 | 3 | 4 | 5 | V-1 | Padi2 | 11240 | 4-May-15 |
| 16256 | 2 | 3 | 4 | 5 | V-1 | Pate2 | 399967 | 4-May-15 |
| 16264 | 2 | 3 | 4 | 5 | V-1 | Pax2 | 5076 | 23-May-15 |
| 16271 | 2 | 3 | 4 | 5 | V-1 | Pax8 | 7849 | 24-May-15 |
| 16376 | 2 | 3 | 4 | 5 | V-1 | Pck1 | 5105 | 4-May-15 |
| 16393 | 2 | 3 | 4 | 5 | V-1 | Pcp4 | 5121 | 4-May-15 |
| 16394 | 2 | 3 | 4 | 5 | V-1 | Pcp4l1 | 654780 | 4-May-15 |
| 16404 | 2 | 3 | 4 | 5 | V-1 | Pcsk9 | 255738 | 23-May-15 |
| 16410 | 2 | 3 | 4 | 5 | V-1 | Pcyt1b | 9468 | 4-May-15 |
| 16477 | 2 | 3 | 4 | 5 | V-1 | Pdk4 | 5166 | 4-May-15 |
| 16480 | 2 | 3 | 4 | 5 | V-1 | Pdlim3 | 27295 | 4-May-15 |
| 16507 | 2 | 3 | 4 | 5 | V-1 | Pdzk1 | 5174 | 4-May-15 |
| 16508 | 2 | 3 | 4 | 5 | V-1 | Pdzk1ip1 | 10158 | 4-May-15 |
| 16582 | 2 | 3 | 4 | 5 | V-1 | Pgam2 | 5224 | 4-May-15 |
| 16589 | 2 | 3 | 4 | 5 | V-1 | Pgc | 5225 | 4-May-15 |
| 16594 | 2 | 3 | 4 | 5 | V-1 | Pgk2 | 5232 | 28-May-15 |
| 16756 | 2 | 3 | 4 | 5 | V-1 | Pip5k1b | 8395 | 12-May-15 |
| 16800 | 2 | 3 | 4 | 5 | V-1 | Pkia | 5569 | 4-May-15 |
| 16822 | 2 | 3 | 4 | 5 | V-1 | Pla2g1b | 5319 | 12-May-15 |
| 16835 | 2 | 3 | 4 | 5 | V-1 | Pla2g5 | 5322 | 4-May-15 |
| 16841 | 2 | 3 | 4 | 5 | V-1 | Plac8 | 51316 | 7-Jun-15 |
| 16881 | 2 | 3 | 4 | 5 | V-1 | Plek2 | 26499 | 4-May-15 |
| 16913 | 2 | 3 | 4 | 5 | V-1 | Plet1 | 349633 | 4-May-15 |
| 16920 | 2 | 3 | 4 | 5 | V-1 | Plin4 | 729359 | 4-May-15 |
| 16980 | 2 | 3 | 4 | 5 | V-1 | Pnlip | 5406 | 12-May-15 |
| 16981 | 2 | 3 | 4 | 5 | V-1 | Pnliprp1 | 5407 | 12-May-15 |
| 16983 | 2 | 3 | 4 | 5 | V-1 | Pnmt | 5409 | 7-Jun-15 |
| 17102 | 2 | 3 | 4 | 5 | V-1 | Pou3f3 | 5455 | 4-May-15 |
| 17103 | 2 | 3 | 4 | 5 | V-1 | Pou3f4 | | |
| 17122 | 2 | 3 | 4 | 5 | V-1 | Ppapdc3 | 84814 | 4-May-15 |
| 17158 | 2 | 3 | 4 | 5 | V-1 | Ppl | 5493 | 4-May-15 |
| 17185 | 2 | 3 | 4 | 5 | V-1 | Ppp1r14c | 81706 | 4-May-15 |
| 17199 | 2 | 3 | 4 | 5 | V-1 | Ppp1r27 | 116729 | 4-May-15 |
| 17207 | 2 | 3 | 4 | 5 | V-1 | Ppp1r3a | 5506 | 12-May-15 |
| 17279 | 2 | 3 | 4 | 5 | V-1 | Prb1 | 5542 | 7-Jun-15 |
| 17316 | 2 | 3 | 4 | 5 | V-1 | Prh1 | 5554 | 31-May-15 |
| 17347 | 2 | 3 | 4 | 5 | V-1 | Prkcq | 5588 | 3-May-15 |
| 17389 | 2 | 3 | 4 | 5 | V-1 | Prlr | 5618 | 7-Jun-15 |
| 17390 | 2 | 3 | 4 | 5 | V-1 | Prm1 | 5619 | 7-Jun-15 |
| 17391 | 2 | 3 | 4 | 5 | V-1 | Prm2 | 5620 | 12-May-15 |
| 17392 | 2 | 3 | 4 | 5 | V-1 | Prm3 | 58531 | 12-May-15 |
| 17414 | 2 | 3 | 4 | 5 | V-1 | Prol1 | 58503 | 4-May-15 |
| 17416 | 2 | 3 | 4 | 5 | V-1 | Prom2 | 150696 | 4-May-15 |
| 17426 | 2 | 3 | 4 | 5 | V-1 | Prp2 | | |
| 17440 | 2 | 3 | 4 | 5 | V-1 | Prph | 5630 | 7-Jun-15 |
| 17442 | 2 | 3 | 4 | 5 | V-1 | Prpmp5 | | |
| 17466 | 2 | 3 | 4 | 5 | V-1 | Prr33 | 102724536 | 17-Mar-15 |
| 17488 | 2 | 3 | 4 | 5 | V-1 | Prss1 | 5644 | 7-Jun-15 |
| 17489 | 2 | 3 | 4 | 5 | V-1 | Prss2 | 5645 | 23-May-15 |
| 17496 | 2 | 3 | 4 | 5 | V-1 | Prss3 | 5646 | 4-May-15 |
| 17523 | 2 | 3 | 4 | 5 | V-1 | Prss8 | 5652 | 12-May-15 |
| 17636 | 2 | 3 | 4 | 5 | V-1 | Ptgds | 5730 | 12-May-15 |
| 17652 | 2 | 3 | 4 | 5 | V-1 | Ptgs2 | 5743 | 24-May-15 |
| 17654 | 2 | 3 | 4 | 5 | V-1 | Pth | 5741 | 7-Jun-15 |
| 17689 | 2 | 3 | 4 | 5 | V-1 | Ptpn5 | 84867 | 12-May-15 |
| 17737 | 2 | 3 | 4 | 5 | V-1 | Pvalb | 5816 | 4-May-15 |
| 17742 | 2 | 3 | 4 | 5 | V-1 | Pvrl4 | 81607 | 4-May-15 |
| 17801 | 2 | 3 | 4 | 5 | V-1 | Rab11fip1 | 80223 | 4-May-15 |
| 17804 | 2 | 3 | 4 | 5 | V-1 | Rab11fip4 | 84440 | 12-May-15 |
| 17821 | 2 | 3 | 4 | 5 | V-1 | Rab25 | 57111 | 4-May-15 |
| 17822 | 2 | 3 | 4 | 5 | V-1 | Rab26 | 25837 | 12-May-15 |
| 17829 | 2 | 3 | 4 | 5 | V-1 | Rab30 | 27314 | 4-May-15 |
| 17895 | 2 | 3 | 4 | 5 | V-1 | Rad51b | 5890 | 4-May-15 |
| 17928 | 2 | 3 | 4 | 5 | V-1 | Ramp1 | 10267 | 21-May-15 |
| 17930 | 2 | 3 | 4 | 5 | V-1 | Ramp3 | 10268 | 12-May-15 |
| 17970 | 2 | 3 | 4 | 5 | V-1 | Rasal1 | 8437 | 4-May-15 |
| 17973 | 2 | 3 | 4 | 5 | V-1 | Rasd1 | 51655 | 4-May-15 |
| 17979 | 2 | 3 | 4 | 5 | V-1 | Rasgrf1 | 5923 | 4-May-15 |
| 17986 | 2 | 3 | 4 | 5 | V-1 | Rasl10a | 10633 | 4-May-15 |
| 18019 | 2 | 3 | 4 | 5 | V-1 | Rbfox1 | 54715 | 12-May-15 |
| 18026 | 2 | 3 | 4 | 5 | V-1 | Rbm11 | 54033 | 4-May-15 |
| 18039 | 2 | 3 | 4 | 5 | V-1 | Rbm24 | 221662 | 4-May-15 |
| 18134 | 2 | 3 | 4 | 5 | V-1 | Reg1 | | |
| 18135 | 2 | 3 | 4 | 5 | V-1 | Reg2 | | |
| 18234 | 2 | 3 | 4 | 5 | V-1 | Rgs9 | 8787 | 7-Jun-15 |
| 18237 | 2 | 3 | 4 | 5 | V-1 | Rhag | 6005 | 12-May-15 |
| 18247 | 2 | 3 | 4 | 5 | V-1 | Rhcg | 51458 | 12-May-15 |
| 18248 | 2 | 3 | 4 | 5 | V-1 | Rhd | 6007 | 21-May-15 |
| 18300 | 2 | 3 | 4 | 5 | V-1 | Rhpn1 | 114822 | 4-May-15 |
| 18355 | 2 | 3 | 4 | 5 | V-1 | Rmrp | 6023 | 23-May-15 |
| 18357 | 2 | 3 | 4 | 5 | V-1 | Rn4.5s | | |
| 18359 | 2 | 3 | 4 | 5 | V-1 | Rnase1 | 6035 | 4-May-15 |
| 18360 | 2 | 3 | 4 | 5 | V-1 | Rnase10 | 338879 | 4-May-15 |
| 18361 | 2 | 3 | 4 | 5 | V-1 | Rnase11 | 122651 | 4-May-15 |
| 18362 | 2 | 3 | 4 | 5 | V-1 | Rnase12 | 493901 | 4-May-15 |
| 18363 | 2 | 3 | 4 | 5 | V-1 | Rnase13 | 440163 | 4-May-15 |
| 18364 | 2 | 3 | 4 | 5 | V-1 | Rnase2a | | |
| 18368 | 2 | 3 | 4 | 5 | V-1 | Rnase9 | 390443 | 4-May-15 |
| 18394 | 2 | 3 | 4 | 5 | V-1 | Rnf128 | 79589 | 4-May-15 |
| 18409 | 2 | 3 | 4 | 5 | V-1 | Rnf149 | 284996 | 4-May-15 |
| 18421 | 2 | 3 | 4 | 5 | V-1 | Rnf180 | 285671 | 4-May-15 |
| 18426 | 2 | 3 | 4 | 5 | V-1 | Rnf186 | 54546 | 4-May-15 |
| 18454 | 2 | 3 | 4 | 5 | V-1 | Rnf43 | 54894 | 4-May-15 |
| 18553 | 2 | 3 | 4 | 5 | V-1 | Rpl38 | 6169 | 12-May-15 |

Fig.22 - 6

| | | | | | | | | | | | | | | | | |
|---|---|---|---|---|---|---|---|---|---|---|---|---|---|---|---|---|
| 18556 | 2 | 3 | 4 | 5 | V-1 | Rpl3l | 6123 | 4-May-15 | 20328 | 2 | 3 | 4 | 5 | V-1 | Spint2 | 10683 | 21-May-15 |
| 18579 | 2 | 3 | 4 | 5 | V-1 | Rpph1 | 85495 | 4-May-15 | 20330 | 2 | 3 | 4 | 5 | V-1 | Spint4 | 391253 | 4-May-15 |
| 18586 | 2 | 3 | 4 | 5 | V-1 | Rprm | 56475 | 4-May-15 | 20331 | 2 | 3 | 4 | 5 | V-1 | Spint5 | | |
| 18636 | 2 | 3 | 4 | 5 | V-1 | Rptn | 126638 | 4-May-15 | 20347 | 2 | 3 | 4 | 5 | V-1 | Spp1 | 6696 | 7-Jun-15 |
| 18706 | 2 | 3 | 4 | 5 | V-1 | Rtn2 | 6253 | 4-May-15 | 20358 | 2 | 3 | 4 | 5 | V-1 | Sprr1a | 6698 | 12-May-15 |
| 18728 | 2 | 3 | 4 | 5 | V-1 | Runx2 | 860 | 31-May-15 | 20367 | 2 | 3 | 4 | 5 | V-1 | Sprr2h | | |
| 18748 | 2 | 3 | 4 | 5 | V-1 | Ryr1 | 6261 | 24-May-15 | 20371 | 2 | 3 | 4 | 5 | V-1 | Sprr3 | 6707 | 4-May-15 |
| 18763 | 2 | 3 | 4 | 5 | V-1 | S100a8 | 6279 | 3-May-15 | 20386 | 2 | 3 | 4 | 5 | V-1 | Spta1 | 6708 | 12-May-15 |
| 18764 | 2 | 3 | 4 | 5 | V-1 | S100a9 | 6280 | 24-May-15 | 20388 | 2 | 3 | 4 | 5 | V-1 | Sptb | 6710 | 21-May-15 |
| 18766 | 2 | 3 | 4 | 5 | V-1 | S100g | 795 | 4-May-15 | 20398 | 2 | 3 | 4 | 5 | V-1 | Spz1 | 84654 | 4-May-15 |
| 18774 | 2 | 3 | 4 | 5 | V-1 | Saa1 | 6288 | 17-May-15 | 20408 | 2 | 3 | 4 | 5 | V-1 | Srd5a2 | 6716 | 4-May-15 |
| 18776 | 2 | 3 | 4 | 5 | V-1 | Saa3 | 5290 | 4-May-15 | 20421 | 2 | 3 | 4 | 5 | V-1 | Srl | 6345 | 4-May-15 |
| 18840 | 2 | 3 | 4 | 5 | V-1 | Sbk2 | 646643 | 4-May-15 | 20503 | 2 | 3 | 4 | 5 | V-1 | St14 | 6768 | 23-May-15 |
| 18889 | 2 | 3 | 4 | 5 | V-1 | Scgb1a1 | 7356 | 4-May-15 | 20512 | 2 | 3 | 4 | 5 | V-1 | St6gal1 | 6480 | 12-May-15 |
| 18909 | 2 | 3 | 4 | 5 | V-1 | Scgb2b27 | | | 20533 | 2 | 3 | 4 | 5 | V-1 | Stac3 | 246329 | 4-May-15 |
| 18913 | 2 | 3 | 4 | 5 | V-1 | Scgb3a2 | 117156 | 12-May-15 | 20565 | 2 | 3 | 4 | 5 | V-1 | Stc2 | 8614 | 4-May-15 |
| 18932 | 2 | 3 | 4 | 5 | V-1 | Scn4b | 6330 | 23-May-15 | 20570 | 2 | 3 | 4 | 5 | V-1 | Stfa1 | | |
| 18960 | 2 | 3 | 4 | 5 | V-1 | Scx | 642658 | 4-May-15 | 20572 | 2 | 3 | 4 | 5 | V-1 | Stfa2l1 | | |
| 19095 | 2 | 3 | 4 | 5 | V-1 | Serinc2 | 347735 | 4-May-15 | 20750 | 2 | 3 | 4 | 5 | V-1 | Sycn | 342898 | 4-May-15 |
| 19101 | 2 | 3 | 4 | 5 | V-1 | Serpina10 | 51156 | 12-May-15 | 20761 | 2 | 3 | 4 | 5 | V-1 | Syn2 | 6854 | 4-May-15 |
| 19104 | 2 | 3 | 4 | 5 | V-1 | Serpina1a | | | 20781 | 2 | 3 | 4 | 5 | V-1 | Synm | 23336 | 4-May-15 |
| 19105 | 2 | 3 | 4 | 5 | V-1 | Serpina1b | | | 20783 | 2 | 3 | 4 | 5 | V-1 | Synpo2 | 171024 | 4-May-15 |
| 19106 | 2 | 3 | 4 | 5 | V-1 | Serpina1c | | | 20784 | 2 | 3 | 4 | 5 | V-1 | Synpo2l | 79933 | 4-May-15 |
| 19107 | 2 | 3 | 4 | 5 | V-1 | Serpina1d | | | 20789 | 2 | 3 | 4 | 5 | V-1 | Sypl2 | 284612 | 4-May-15 |
| 19109 | 2 | 3 | 4 | 5 | V-1 | Serpina1f | | | 20811 | 2 | 3 | 4 | 5 | V-1 | Sytl4 | 94121 | 4-May-15 |
| 19118 | 2 | 3 | 4 | 5 | V-1 | Serpina3k | | | 20846 | 2 | 3 | 4 | 5 | V-1 | Tacstd2 | 4070 | 12-May-15 |
| 19134 | 2 | 3 | 4 | 5 | V-1 | Serpinb3a | | | 20976 | 2 | 3 | 4 | 5 | V-1 | Tbc1d8 | 11138 | 4-May-15 |
| 19143 | 2 | 3 | 4 | 5 | V-1 | Serpinb6e | | | 21001 | 2 | 3 | 4 | 5 | V-1 | Tbx1 | 6899 | 23-May-15 |
| 19153 | 2 | 3 | 4 | 5 | V-1 | Serpinc1 | 462 | 17-May-15 | 21003 | 2 | 3 | 4 | 5 | V-1 | Tbx15 | 6913 | 4-May-15 |
| 19159 | 2 | 3 | 4 | 5 | V-1 | Serpinf2 | 5345 | 20-May-15 | 21020 | 2 | 3 | 4 | 5 | V-1 | Tcap | 8557 | 23-May-15 |
| 19225 | 2 | 3 | 4 | 5 | V-1 | Sgca | 6442 | 12-May-15 | 21023 | 2 | 3 | 4 | 5 | V-1 | Tcea3 | 6920 | 4-May-15 |
| 19229 | 2 | 3 | 4 | 5 | V-1 | Sgcg | 6445 | 23-May-15 | 21025 | 2 | 3 | 4 | 5 | V-1 | Tceal3 | 85012 | 4-May-15 |
| 19272 | 2 | 3 | 4 | 5 | V-1 | Sh3gl2 | 6456 | 12-May-15 | 21047 | 2 | 3 | 4 | 5 | V-1 | Tcf7 | 6932 | 12-May-15 |
| 19294 | 2 | 3 | 4 | 5 | V-1 | Shc4 | 399694 | 4-May-15 | 21067 | 2 | 3 | 4 | 5 | V-1 | Tcp11 | 6954 | 4-May-15 |
| 19445 | 2 | 3 | 4 | 5 | V-1 | Slc16a3 | 9123 | 4-May-15 | 21113 | 2 | 3 | 4 | 5 | V-1 | Teddm1 | 127670 | 4-May-15 |
| 19451 | 2 | 3 | 4 | 5 | V-1 | Slc16a9 | 220963 | 4-May-15 | 21175 | 2 | 3 | 4 | 5 | V-1 | Tfap2a | 7020 | 23-May-15 |
| 19460 | 2 | 3 | 4 | 5 | V-1 | Slc17a9 | 63910 | 23-May-15 | 21176 | 2 | 3 | 4 | 5 | V-1 | Tfap2b | 7021 | 4-May-15 |
| 19468 | 2 | 3 | 4 | 5 | V-1 | Slc1a1 | 6505 | 12-May-15 | 21190 | 2 | 3 | 4 | 5 | V-1 | Tff1 | 7031 | 12-May-15 |
| 19492 | 2 | 3 | 4 | 5 | V-1 | Slc22a26 | | | 21191 | 2 | 3 | 4 | 5 | V-1 | Tff2 | 7032 | 12-May-15 |
| 19493 | 2 | 3 | 4 | 5 | V-1 | Slc22a27 | | | 21215 | 2 | 3 | 4 | 5 | V-1 | Tgif2lx2 | | |
| 19552 | 2 | 3 | 4 | 5 | V-1 | Slc25a47 | 283600 | 4-May-15 | 21218 | 2 | 3 | 4 | 5 | V-1 | Tgm3 | 7053 | 12-May-15 |
| 19596 | 2 | 3 | 4 | 5 | V-1 | Slc30a10 | 55532 | 23-May-15 | 21224 | 2 | 3 | 4 | 5 | V-1 | Tgoln2 | 10618 | 12-May-15 |
| 19610 | 2 | 3 | 4 | 5 | V-1 | Slc34a2 | 10568 | 17-May-15 | 21309 | 2 | 3 | 4 | 5 | V-1 | Timp1 | 7076 | 12-May-15 |
| 19631 | 2 | 3 | 4 | 5 | V-1 | Slc35f2 | 54733 | 4-May-15 | 21414 | 2 | 3 | 4 | 5 | V-1 | Tmem102 | 284114 | 14-May-15 |
| 19652 | 2 | 3 | 4 | 5 | V-1 | Slc38a3 | 10991 | 4-May-15 | 21450 | 2 | 3 | 4 | 5 | V-1 | Tmem139 | 135932 | 12-May-15 |
| 19664 | 2 | 3 | 4 | 5 | V-1 | Slc38a5 | 92745 | 4-May-15 | 21461 | 2 | 3 | 4 | 5 | V-1 | Tmem150c | 441027 | 4-May-15 |
| 19697 | 2 | 3 | 4 | 5 | V-1 | Slc4a1 | 6521 | 14-May-15 | 21497 | 2 | 3 | 4 | 5 | V-1 | Tmem182 | 130827 | 4-May-15 |
| 19710 | 2 | 3 | 4 | 5 | V-1 | Slc51b | 123264 | 4-May-15 | 21530 | 2 | 3 | 4 | 5 | V-1 | Tmem212 | 389177 | 4-May-15 |
| 19749 | 2 | 3 | 4 | 5 | V-1 | Slc7a12 | | | 21548 | 2 | 3 | 4 | 5 | V-1 | Tmem233 | 387890 | 4-May-15 |
| 19756 | 2 | 3 | 4 | 5 | V-1 | Slc7a5 | 8140 | 4-May-15 | 21565 | 2 | 3 | 4 | 5 | V-1 | Tmem252 | 169693 | 4-May-15 |
| 19760 | 2 | 3 | 4 | 5 | V-1 | Slc7a8 | 23428 | 4-May-15 | 21569 | 2 | 3 | 4 | 5 | V-1 | Tmem254c | | |
| 19781 | 2 | 3 | 4 | 5 | V-1 | Slco1a4 | | | 21583 | 2 | 3 | 4 | 5 | V-1 | Tmem30b | 161291 | 4-May-15 |
| 19820 | 2 | 3 | 4 | 5 | V-1 | Sln | 6588 | 12-May-15 | 21588 | 2 | 3 | 4 | 5 | V-1 | Tmem38a | 79041 | 4-May-15 |
| 19821 | 2 | 3 | 4 | 5 | V-1 | Slpi | 6590 | 4-May-15 | 23604 | 2 | 3 | 4 | 5 | V-1 | Tmem51 | 55092 | 4-May-15 |
| 19865 | 2 | 3 | 4 | 5 | V-1 | Smcol | 255798 | 4-May-15 | 21606 | 2 | 3 | 4 | 5 | V-1 | Tmem52 | 339456 | 4-May-15 |
| 19869 | 2 | 3 | 4 | 5 | V-1 | Smcp | 4184 | 4-May-15 | 21658 | 2 | 3 | 4 | 5 | V-1 | Tmod1 | 7111 | 12-May-15 |
| 19919 | 2 | 3 | 4 | 5 | V-1 | Smpx | 23676 | 23-May-15 | 21661 | 2 | 3 | 4 | 5 | V-1 | Tmod4 | 29765 | 4-May-15 |
| 19921 | 2 | 3 | 4 | 5 | V-1 | Smr3a | 26952 | 4-May-15 | 21673 | 2 | 3 | 4 | 5 | V-1 | Tmprss15 | 5651 | 7-Jun-15 |
| 19924 | 2 | 3 | 4 | 5 | V-1 | Smtnl1 | 219537 | 4-May-15 | 21752 | 2 | 3 | 4 | 5 | V-1 | Tnnc2 | 7125 | 12-May-15 |
| 19930 | 2 | 3 | 4 | 5 | V-1 | Smyd1 | 150572 | 4-May-15 | 21753 | 2 | 3 | 4 | 5 | V-1 | Tnni1 | 7135 | 12-May-15 |
| 19970 | 2 | 3 | 4 | 5 | V-1 | Snora15 | 677803 | 4-May-15 | 21754 | 2 | 3 | 4 | 5 | V-1 | Tnni2 | 7136 | 4-May-15 |
| 19971 | 2 | 3 | 4 | 5 | V-1 | Snora16a | 692073 | 4-May-15 | 21759 | 2 | 3 | 4 | 5 | V-1 | Tnnt3 | 7140 | 12-May-15 |
| 19972 | 2 | 3 | 4 | 5 | V-1 | Snora17 | 677804 | 4-May-15 | 21760 | 2 | 3 | 4 | 5 | V-1 | Tnp1 | 7141 | 12-May-15 |
| 19975 | 2 | 3 | 4 | 5 | V-1 | Snora21 | 619505 | 4-May-15 | 21761 | 2 | 3 | 4 | 5 | V-1 | Tnp2 | 7142 | 4-May-15 |
| 19979 | 2 | 3 | 4 | 5 | V-1 | Snora28 | 677811 | 4-May-15 | 21814 | 2 | 3 | 4 | 5 | V-1 | Tox3 | 27324 | 4-May-15 |
| 19981 | 2 | 3 | 4 | 5 | V-1 | Snora3 | 619562 | 4-May-15 | 21822 | 2 | 3 | 4 | 5 | V-1 | Tpd52l1 | 7164 | 4-May-15 |
| 19983 | 2 | 3 | 4 | 5 | V-1 | Snora31 | 677814 | 4-May-15 | 21831 | 2 | 3 | 4 | 5 | V-1 | Tpm2 | 7169 | 2-Jun-15 |
| 19984 | 2 | 3 | 4 | 5 | V-1 | Snora33 | 594839 | 4-May-15 | 21839 | 2 | 3 | 4 | 5 | V-1 | Tppp2 | 122664 | 21-May-15 |
| 19985 | 2 | 3 | 4 | 5 | V-1 | Snora34 | 677815 | 4-May-15 | 21877 | 2 | 3 | 4 | 5 | V-1 | Trank1 | 9881 | 4-May-15 |
| 19988 | 2 | 3 | 4 | 5 | V-1 | Snora41 | 619569 | 4-May-15 | 21898 | 2 | 3 | 4 | 5 | V-1 | Trdn | 10345 | 23-May-15 |
| 19989 | 2 | 3 | 4 | 5 | V-1 | Snora43 | 677824 | 4-May-15 | 21901 | 2 | 3 | 4 | 5 | V-1 | Trem2 | 54209 | 23-May-15 |
| 19992 | 2 | 3 | 4 | 5 | V-1 | Snora52 | 619565 | 4-May-15 | 21964 | 2 | 3 | 4 | 5 | V-1 | Trim54 | 57159 | 4-May-15 |
| 19996 | 2 | 3 | 4 | 5 | V-1 | Snora64 | 26784 | 4-May-15 | 21973 | 2 | 3 | 4 | 5 | V-1 | Trim63 | 84676 | 4-May-15 |
| 19997 | 2 | 3 | 4 | 5 | V-1 | Snora65 | 26783 | 4-May-15 | 21981 | 2 | 3 | 4 | 5 | V-1 | Trim72 | 493829 | 4-May-15 |
| 19998 | 2 | 3 | 4 | 5 | V-1 | Snora68 | 26780 | 4-May-15 | 22015 | 2 | 3 | 4 | 5 | V-1 | Trnp1 | 388610 | 4-May-15 |
| 19999 | 2 | 3 | 4 | 5 | V-1 | Snora69 | 26779 | 4-May-15 | 22058 | 2 | 3 | 4 | 5 | V-1 | Trpv6 | 55503 | 20-May-15 |
| 20000 | 2 | 3 | 4 | 5 | V-1 | Snora70 | 26778 | 4-May-15 | 22063 | 2 | 3 | 4 | 5 | V-1 | Try4 | 5647 | |
| 20002 | 2 | 3 | 4 | 5 | V-1 | Snora75 | 654321 | 4-May-15 | 22064 | 2 | 3 | 4 | 5 | V-1 | Try5 | 168330 | 4-May-15 |
| 20004 | 2 | 3 | 4 | 5 | V-1 | Snora7a | 619563 | 4-May-15 | 22093 | 2 | 3 | 4 | 5 | V-1 | Tspan1 | 10103 | 4-May-15 |
| 20005 | 2 | 3 | 4 | 5 | V-1 | Snora81 | 677847 | 4-May-15 | 22133 | 2 | 3 | 4 | 5 | V-1 | Tssk6 | 83983 | 4-May-15 |
| 20020 | 2 | 3 | 4 | 5 | V-1 | Snord15a | 6079 | 4-May-15 | 22168 | 2 | 3 | 4 | 5 | V-1 | Ttc36 | 143941 | 4-May-15 |
| 20029 | 2 | 3 | 4 | 5 | V-1 | Snord22 | 9304 | 4-May-15 | 22202 | 2 | 3 | 4 | 5 | V-1 | Ttn | 7273 | 23-May-15 |
| 20108 | 2 | 3 | 4 | 5 | V-1 | Snurf | 8926 | 7-Jun-15 | 22216 | 2 | 3 | 4 | 5 | V-1 | Tuba8 | 51807 | 4-May-15 |
| 20170 | 2 | 3 | 4 | 5 | V-1 | Sost | 50964 | 24-May-15 | 22220 | 2 | 3 | 4 | 5 | V-1 | Tubb2a-ps2 | | |
| 20193 | 2 | 3 | 4 | 5 | V-1 | Sox6 | 55553 | 12-May-15 | 22259 | 2 | 3 | 4 | 5 | V-1 | Txlnb | 167838 | 12-May-15 |
| 20218 | 2 | 3 | 4 | 5 | V-1 | Spag11a | 653423 | 4-May-15 | 22411 | 2 | 3 | 4 | 5 | V-1 | Ucp1 | 7350 | 12-May-15 |
| 20219 | 2 | 3 | 4 | 5 | V-1 | Spag11b | 10407 | 14-May-15 | 22426 | 2 | 3 | 4 | 5 | V-1 | Ugt1a3 | 54658 | 28-May-15 |
| 20245 | 2 | 3 | 4 | 5 | V-1 | Spata3 | 130560 | 4-May-15 | 22427 | 2 | 3 | 4 | 5 | V-1 | Ugt1a10 | 54575 | 28-May-15 |
| 20310 | 2 | 3 | 4 | 5 | V-1 | Spin2c | | | 22428 | 2 | 3 | 4 | 5 | V-1 | Ugt1a2 | | |
| 20314 | 2 | 3 | 4 | 5 | V-1 | Spink10 | | | 22483 | 2 | 3 | 4 | 5 | V-1 | Uox | 391051 | 12-May-15 |
| 20315 | 2 | 3 | 4 | 5 | V-1 | Spink11 | | | 22532 | 2 | 3 | 4 | 5 | V-1 | Usp13 | 8975 | 29-May-15 |
| 20316 | 2 | 3 | 4 | 5 | V-1 | Spink12 | | | 22623 | 2 | 3 | 4 | 5 | V-1 | Vash2 | 79805 | 4-May-15 |
| 20319 | 2 | 3 | 4 | 5 | V-1 | Spink2 | 6691 | 4-May-15 | 22654 | 2 | 3 | 4 | 5 | V-1 | Vgll2 | 245806 | 4-May-15 |
| 20320 | 2 | 3 | 4 | 5 | V-1 | Spink3 | 6690 | 23-May-15 | 23103 | 2 | 3 | 4 | 5 | V-1 | Wbscr25 | | |
| 20322 | 2 | 3 | 4 | 5 | V-1 | Spink5 | 11005 | 12-May-15 | 23185 | 2 | 3 | 4 | 5 | V-1 | Wfdc10 | | |
| 20325 | 2 | 3 | 4 | 5 | V-1 | Spink8 | 646424 | 4-May-15 | 23186 | 2 | 3 | 4 | 5 | V-1 | Wfdc11 | 259239 | 4-May-15 |
| 20327 | 2 | 3 | 4 | 5 | V-1 | Spint1 | 6692 | 4-May-15 | 23188 | 2 | 3 | 4 | 5 | V-1 | Wfdc13 | 164237 | 4-May-15 |

Fig.22 - 7

| | | | | | | | | | | | | | | | |
|---|---|---|---|---|---|---|---|---|---|---|---|---|---|---|---|
| 23190 | 2 | 3 | 4 | 5 | V-1 | Wfdc15b | | | 713 | 2 | 3 | 4 | | IV-2 | 3110002H16Rik | | |
| 23197 | 2 | 3 | 4 | 5 | V-1 | Wfdc6a | | | 716 | 2 | 3 | 4 | | IV-2 | 3110009F21Rik | | |
| 23198 | 2 | 3 | 4 | 5 | V-1 | Wfdc6b | | | 726 | 2 | 3 | 4 | | IV-2 | 3110052M02Rik | | |
| 23199 | 2 | 3 | 4 | 5 | V-1 | Wfdc8 | 90199 | 4-May-15 | 731 | 2 | 3 | 4 | | IV-2 | 3110079O15Rik | | |
| 23200 | 2 | 3 | 4 | 5 | V-1 | Wfdc9 | 259240 | 4-May-15 | 733 | 2 | 3 | 4 | | IV-2 | 3110082I24Rik | | |
| 23268 | 2 | 3 | 4 | 5 | V-1 | Xirp1 | 165904 | 17-May-15 | 739 | 2 | 3 | 4 | | IV-2 | 3632451O06Rik | | |
| 23269 | 2 | 3 | 4 | 5 | V-1 | Xirp2 | 129446 | 3-May-15 | 740 | 2 | 3 | 4 | | IV-2 | 3632454L22Rik | | |
| 23278 | 2 | 3 | 4 | 5 | V-1 | Xkrx | 402415 | 4-May-15 | 746 | 2 | 3 | 4 | | IV-2 | 4430402I18Rik | | |
| 23338 | 2 | 3 | 4 | 5 | V-1 | Yipf7 | 285525 | 4-May-15 | 752 | 2 | 3 | 4 | | IV-2 | 4632434I11Rik | | |
| 23346 | 2 | 3 | 4 | 5 | V-1 | Ypel4 | 219539 | 4-May-15 | 814 | 2 | 3 | 4 | | IV-2 | 4930404I05Rik | | |
| 23718 | 2 | 3 | 4 | 5 | V-1 | Zfp648 | | | 816 | 2 | 3 | 4 | | IV-2 | 4930405A10Rik | | |
| 23762 | 2 | 3 | 4 | 5 | V-1 | Zfp750 | 79755 | 28-May-15 | 843 | 2 | 3 | 4 | | IV-2 | 4930426L09Rik | | |
| 10 | 2 | 3 | 4 | | IV-2 | 0610012G03Rik | | | 845 | 2 | 3 | 4 | | IV-2 | 4930428D18Rik | | |
| 14 | 2 | 3 | 4 | | IV-2 | 0610037L13Rik | | | 853 | 2 | 3 | 4 | | IV-2 | 4930430A15Rik | | |
| 16 | 2 | 3 | 4 | | IV-2 | 0610039K10Rik | | | 887 | 2 | 3 | 4 | | IV-2 | 4930448I06Rik | | |
| 21 | 2 | 3 | 4 | | IV-2 | 1010001N08Rik | | | 905 | 2 | 3 | 4 | | IV-2 | 4930455I15Rik | | |
| 23 | 2 | 3 | 4 | | IV-2 | 1110001J03Rik | | | 956 | 2 | 3 | 4 | | IV-2 | 4930502E09Rik | | |
| 28 | 2 | 3 | 4 | | IV-2 | 1110007C09Rik | | | 977 | 2 | 3 | 4 | | IV-2 | 4930512B01Rik | | |
| 36 | 2 | 3 | 4 | | IV-2 | 1110020A21Rik | | | 1019 | 2 | 3 | 4 | | IV-2 | 4930529M08Rik | | |
| 37 | 2 | 3 | 4 | | IV-2 | 1110025L11Rik | | | 1027 | 2 | 3 | 4 | | IV-2 | 4930539M17Rik | | |
| 43 | 2 | 3 | 4 | | IV-2 | 1110038B04Rik | | | 1074 | 2 | 3 | 4 | | IV-2 | 4930563M20Rik | | |
| 48 | 2 | 3 | 4 | | IV-2 | 1110051M20Rik | | | 1076 | 2 | 3 | 4 | | IV-2 | 4930564C03Rik | | |
| 56 | 2 | 3 | 4 | | IV-2 | 1190002N15Rik | | | 1078 | 2 | 3 | 4 | | IV-2 | 4930565D16Rik | | |
| 57 | 2 | 3 | 4 | | IV-2 | 1190003K10Rik | | | 1081 | 2 | 3 | 4 | | IV-2 | 4930567H17Rik | | |
| 59 | 2 | 3 | 4 | | IV-2 | 1190007I07Rik | | | 1096 | 2 | 3 | 4 | | IV-2 | 4930578E11Rik | | |
| 75 | 2 | 3 | 4 | | IV-2 | 1600002O24Rik | | | 1099 | 2 | 3 | 4 | | IV-2 | 4930578N18Rik | | |
| 100 | 2 | 3 | 4 | | IV-2 | 1700001L19Rik | | | 1124 | 2 | 3 | 4 | | IV-2 | 4931403G20Rik | | |
| 105 | 2 | 3 | 4 | | IV-2 | 1700001P01Rik | | | 1131 | 2 | 3 | 4 | | IV-2 | 4931409K22Rik | | |
| 109 | 2 | 3 | 4 | | IV-2 | 1700003F24Rik | | | 1168 | 2 | 3 | 4 | | IV-2 | 4933400A11Rik | | |
| 169 | 2 | 3 | 4 | | IV-2 | 1700016D06Rik | | | 1287 | 2 | 3 | 4 | | IV-2 | 5031439G07Rik | | |
| 188 | 2 | 3 | 4 | | IV-2 | 1700019A02Rik | | | 1296 | 2 | 3 | 4 | | IV-2 | 5330434G04Rik | | |
| 201 | 2 | 3 | 4 | | IV-2 | 1700020G17Rik | | | 1304 | 2 | 3 | 4 | | IV-2 | 5430416O09Rik | | |
| 204 | 2 | 3 | 4 | | IV-2 | 1700020M21Rik | | | 1309 | 2 | 3 | 4 | | IV-2 | 5430425K12Rik | | |
| 225 | 2 | 3 | 4 | | IV-2 | 1700024P04Rik | | | 1323 | 2 | 3 | 4 | | IV-2 | 5730409E04Rik | | |
| 245 | 2 | 3 | 4 | | IV-2 | 1700028D13Rik | | | 1328 | 2 | 3 | 4 | | IV-2 | 5730435O14Rik | | |
| 257 | 2 | 3 | 4 | | IV-2 | 1700029I01Rik | | | 1336 | 2 | 3 | 4 | | IV-2 | 5730522E02Rik | | |
| 267 | 2 | 3 | 4 | | IV-2 | 1700030K09Rik | | | 1345 | 2 | 3 | 4 | | IV-2 | 5830418P13Rik | | |
| 308 | 2 | 3 | 4 | | IV-2 | 1700048O20Rik | | | 1354 | 2 | 3 | 4 | | IV-2 | 5930438M14Rik | | |
| 324 | 2 | 3 | 4 | | IV-2 | 1700057G04Rik | | | 1372 | 2 | 3 | 4 | | IV-2 | 6330415B21Rik | | |
| 354 | 2 | 3 | 4 | | IV-2 | 1700072B07Rik | | | 1375 | 2 | 3 | 4 | | IV-2 | 6330419J24Rik | | |
| 365 | 2 | 3 | 4 | | IV-2 | 1700084F23Rik | | | 1376 | 2 | 3 | 4 | | IV-2 | 6330549D23Rik | | |
| 369 | 2 | 3 | 4 | | IV-2 | 1700086O06Rik | | | 1378 | 2 | 3 | 4 | | IV-2 | 6430503K07Rik | | |
| 377 | 2 | 3 | 4 | | IV-2 | 1700093K21Rik | | | 1389 | 2 | 3 | 4 | | IV-2 | 6530411M01Rik | | |
| 384 | 2 | 3 | 4 | | IV-2 | 1700096K18Rik | | | 1413 | 2 | 3 | 4 | | IV-2 | 8430427H17Rik | | |
| 386 | 2 | 3 | 4 | | IV-2 | 1700100L14Rik | | | 1414 | 2 | 3 | 4 | | IV-2 | 8430429K09Rik | | |
| 391 | 2 | 3 | 4 | | IV-2 | 1700102P08Rik | | | 1424 | 2 | 3 | 4 | | IV-2 | 9030624G23Rik | | |
| 392 | 2 | 3 | 4 | | IV-2 | 1700104L18Rik | | | 1428 | 2 | 3 | 4 | | IV-2 | 9130011E15Rik | | |
| 405 | 2 | 3 | 4 | | IV-2 | 1700111N16Rik | | | 1434 | 2 | 3 | 4 | | IV-2 | 9130024F11Rik | | |
| 413 | 2 | 3 | 4 | | IV-2 | 1700120E14Rik | | | 1436 | 2 | 3 | 4 | | IV-2 | 9130209A04Rik | | |
| 416 | 2 | 3 | 4 | | IV-2 | 1700121L16Rik | | | 1463 | 2 | 3 | 4 | | IV-2 | 9330159M07Rik | | |
| 427 | 2 | 3 | 4 | | IV-2 | 1700125G02Rik | | | 1499 | 2 | 3 | 4 | | IV-2 | 9530059O14Rik | | |
| 430 | 2 | 3 | 4 | | IV-2 | 1700125H20Rik | | | 1503 | 2 | 3 | 4 | | IV-2 | 9530082P21Rik | | |
| 438 | 2 | 3 | 4 | | IV-2 | 1810008I18Rik | | | 1520 | 2 | 3 | 4 | | IV-2 | 9930111J21Rik2 | | |
| 439 | 2 | 3 | 4 | | IV-2 | 1810009A15Rik | | | 1522 | 2 | 3 | 4 | | IV-2 | A130010I15Rik | | |
| 447 | 2 | 3 | 4 | | IV-2 | 1810013L24Rik | | | 1534 | 2 | 3 | 4 | | IV-2 | A230057D06Rik | | |
| 454 | 2 | 3 | 4 | | IV-2 | 1810024B03Rik | | | 1545 | 2 | 3 | 4 | | IV-2 | A330021E22Rik | | |
| 459 | 2 | 3 | 4 | | IV-2 | 1810034E14Rik | | | 1572 | 2 | 3 | 4 | | IV-2 | A430107P09Rik | | |
| 462 | 2 | 3 | 4 | | IV-2 | 1810043G02Rik | | | 1575 | 2 | 3 | 4 | | IV-2 | A530006G24Rik | | |
| 470 | 2 | 3 | 4 | | IV-2 | 1810062O18Rik | | | 1578 | 2 | 3 | 4 | | IV-2 | A530032D15Rik | | |
| 476 | 2 | 3 | 4 | | IV-2 | 2010005H15Rik | | | 1582 | 2 | 3 | 4 | | IV-2 | A530054K11Rik | | |
| 479 | 2 | 3 | 4 | | IV-2 | 2010012O05Rik | | | 1590 | 2 | 3 | 4 | | IV-2 | A630007B06Rik | | |
| 489 | 2 | 3 | 4 | | IV-2 | 2010111I01Rik | | | 1591 | 2 | 3 | 4 | | IV-2 | A630010A05Rik | | |
| 497 | 2 | 3 | 4 | | IV-2 | 2200002J24Rik | | | 1603 | 2 | 3 | 4 | | IV-2 | A630077J23Rik | | |
| 499 | 2 | 3 | 4 | | IV-2 | 2210011C24Rik | | | 1605 | 2 | 3 | 4 | | IV-2 | A630095I13Rik | | |
| 500 | 2 | 3 | 4 | | IV-2 | 2210013O21Rik | | | 1610 | 2 | 3 | 4 | | IV-2 | A730017L22Rik | | |
| 507 | 2 | 3 | 4 | | IV-2 | 2210404O09Rik | | | 1621 | 2 | 3 | 4 | | IV-2 | A730090N16Rik | | |
| 510 | 2 | 3 | 4 | | IV-2 | 2210408I21Rik | | | 1633 | 2 | 3 | 4 | | IV-2 | A930003A15Rik | | |
| 513 | 2 | 3 | 4 | | IV-2 | 2210414B05Rik | | | 1639 | 2 | 3 | 4 | | IV-2 | A930007I19Rik | | |
| 515 | 2 | 3 | 4 | | IV-2 | 2210417A02Rik | | | 1647 | 2 | 3 | 4 | | IV-2 | A930017M01Rik | | |
| 521 | 2 | 3 | 4 | | IV-2 | 2310001H17Rik | | | 1660 | 2 | 3 | 4 | | IV-2 | AA536875 | | |
| 523 | 2 | 3 | 4 | | IV-2 | 2310002O06Rik | | | 1671 | 2 | 3 | 4 | | IV-2 | Aadacl2 | 344752 | 4-May-15 |
| 527 | 2 | 3 | 4 | | IV-2 | 2310003H01Rik | | | 1673 | 2 | 3 | 4 | | IV-2 | Aadat | 51166 | 4-May-15 |
| 537 | 2 | 3 | 4 | | IV-2 | 2310011J03Rik | | | 1674 | 2 | 3 | 4 | | IV-2 | Aaed1 | 195827 | 4-May-15 |
| 541 | 2 | 3 | 4 | | IV-2 | 2310015D24Rik | | | 1692 | 2 | 3 | 4 | | IV-2 | Abat | 18 | 4-May-15 |
| 552 | 2 | 3 | 4 | | IV-2 | 2310035C23Rik | | | 1693 | 2 | 3 | 4 | | IV-2 | Abca1 | 19 | 24-May-15 |
| 561 | 2 | 3 | 4 | | IV-2 | 2310047M10Rik | | | 1708 | 2 | 3 | 4 | | IV-2 | Abca9 | 10350 | 12-May-15 |
| 564 | 2 | 3 | 4 | | IV-2 | 2310057M21Rik | | | 1747 | 2 | 3 | 4 | | IV-2 | Abhd12 | 26090 | 4-May-15 |
| 570 | 2 | 3 | 4 | | IV-2 | 2310067B10Rik | | | 1759 | 2 | 3 | 4 | | IV-2 | Abhd3 | 171586 | 21-May-15 |
| 573 | 2 | 3 | 4 | | IV-2 | 2310069G16Rik | | | 1760 | 2 | 3 | 4 | | IV-2 | Abhd4 | 63874 | 4-May-15 |
| 574 | 2 | 3 | 4 | | IV-2 | 2310079G19Rik | | | 1768 | 2 | 3 | 4 | | IV-2 | Abi1 | 25 | 24-May-15 |
| 576 | 2 | 3 | 4 | | IV-2 | 2410002F23Rik | | | 1776 | 2 | 3 | 4 | | IV-2 | Abracl | 58527 | 12-May-15 |
| 583 | 2 | 3 | 4 | | IV-2 | 2410007B07Rik | | | 1797 | 2 | 3 | 4 | | IV-2 | Acap2 | 23527 | 4-May-15 |
| 592 | 2 | 3 | 4 | | IV-2 | 2410088K16Rik | | | 1811 | 2 | 3 | 4 | | IV-2 | Ace2 | 59272 | 17-May-15 |
| 623 | 2 | 3 | 4 | | IV-2 | 2510037D02Rik | | | 1812 | 2 | 3 | 4 | | IV-2 | Ace3 | 100129123 | 12-May-15 |
| 632 | 2 | 3 | 4 | | IV-2 | 2610306M01Rik | | | 1817 | 2 | 3 | 4 | | IV-2 | Acin1 | 22985 | 2-Jun-15 |
| 633 | 2 | 3 | 4 | | IV-2 | 2610307P16Rik | | | 1819 | 2 | 3 | 4 | | IV-2 | Ackr2 | 1238 | 4-May-15 |
| 641 | 2 | 3 | 4 | | IV-2 | 2700029M09Rik | | | 1821 | 2 | 3 | 4 | | IV-2 | Ackr4 | 51554 | 4-May-15 |
| 650 | 2 | 3 | 4 | | IV-2 | 2700070H01Rik | | | 1823 | 2 | 3 | 4 | | IV-2 | Acmsd | 130013 | 12-May-15 |
| 653 | 2 | 3 | 4 | | IV-2 | 2700089E24Rik | | | 1831 | 2 | 3 | 4 | | IV-2 | Acot11 | 26027 | 4-May-15 |
| 658 | 2 | 3 | 4 | | IV-2 | 2810001G20Rik | | | 1846 | 2 | 3 | 4 | | IV-2 | Acp1 | 52 | 12-May-15 |
| 668 | 2 | 3 | 4 | | IV-2 | 2810047C21Rik1 | | | 1849 | 2 | 3 | 4 | | IV-2 | Acp6 | 51205 | 4-May-15 |
| 678 | 2 | 3 | 4 | | IV-2 | 2810408M09Rik | | | 1851 | 2 | 3 | 4 | | IV-2 | Acpt | 93650 | 4-May-15 |
| 681 | 2 | 3 | 4 | | IV-2 | 2810428I15Rik | | | 1863 | 2 | 3 | 4 | | IV-2 | Acsl6 | 23305 | 4-May-15 |
| 684 | 2 | 3 | 4 | | IV-2 | 2810442J21Rik | | | 1865 | 2 | 3 | 4 | | IV-2 | Acsm2 | 123876 | 19-May-15 |
| 694 | 2 | 3 | 4 | | IV-2 | 2900011O08Rik | | | 1867 | 2 | 3 | 4 | | IV-2 | Acsm4 | 341392 | 4-May-15 |
| 697 | 2 | 3 | 4 | | IV-2 | 2900052N01Rik | | | 1870 | 2 | 3 | 4 | | IV-2 | Acss2 | 55902 | 4-May-15 |
| 711 | 2 | 3 | 4 | | IV-2 | 3100003L05Rik | | | 1871 | 2 | 3 | 4 | | IV-2 | Acss2os | | |

Fig.22 - 8

| | | | | | | | | | | | | | | | |
|---|---|---|---|---|---|---|---|---|---|---|---|---|---|---|---|
| 1875 | 2 | 3 | 4 | | IV-2 | Actb | 60 | 7-Jun-15 | 2530 | 2 | 3 | 4 | IV-2 | Apex2 | 27301 | 12-May-15 |
| 1878 | 2 | 3 | 4 | | IV-2 | Actg1 | 71 | 23-May-15 | 2537 | 2 | 3 | 4 | IV-2 | Aplf | 200558 | 4-May-15 |
| 1880 | 2 | 3 | 4 | | IV-2 | Actr10 | 170487 | 4-May-15 | 2540 | 2 | 3 | 4 | IV-2 | Aplp1 | 393 | 4-May-15 |
| 1890 | 2 | 3 | 4 | | IV-2 | Actn4 | 81 | 29-May-15 | 2544 | 2 | 3 | 4 | IV-2 | Apoa1bp | 128240 | 12-May-15 |
| 1904 | 2 | 3 | 4 | | IV-2 | Acvr1b | 91 | 4-May-15 | 2548 | 2 | 3 | 4 | IV-2 | Apob | 338 | 17-May-15 |
| 1911 | 2 | 3 | 4 | | IV-2 | Acyp1 | 97 | 12-May-15 | 2551 | 2 | 3 | 4 | IV-2 | Apobec3 | | |
| 1919 | 2 | 3 | 4 | | IV-2 | Adam12 | 8038 | 4-May-15 | 2562 | 2 | 3 | 4 | IV-2 | Apol10a | | |
| 1920 | 2 | 3 | 4 | | IV-2 | Adam15 | 8751 | 4-May-15 | 2563 | 2 | 3 | 4 | IV-2 | Apol10b | | |
| 1931 | 2 | 3 | 4 | | IV-2 | Adam24 | 646479 | 12-May-15 | 2564 | 2 | 3 | 4 | IV-2 | Apol11a | | |
| 1949 | 2 | 3 | 4 | | IV-2 | Adam9 | 8754 | 17-May-15 | 2567 | 2 | 3 | 4 | IV-2 | Apol7a | | |
| 1954 | 2 | 3 | 4 | | IV-2 | Adamts13 | 11093 | 31-May-15 | 2575 | 2 | 3 | 4 | IV-2 | Apold1 | 81575 | 4-May-15 |
| 1962 | 2 | 3 | 4 | | IV-2 | Adamts20 | 80070 | 12-May-15 | 2580 | 2 | 3 | 4 | IV-2 | Apoo-ps | | |
| 1965 | 2 | 3 | 4 | | IV-2 | Adamts5 | 11096 | 4-May-15 | 2589 | 2 | 3 | 4 | IV-2 | Aqp11 | 282679 | 4-May-15 |
| 1966 | 2 | 3 | 4 | | IV-2 | Adamts6 | 11174 | 4-May-15 | 2591 | 2 | 3 | 4 | IV-2 | Aqp2 | 359 | 23-May-15 |
| 1969 | 2 | 3 | 4 | | IV-2 | Adamts9 | 56999 | 4-May-15 | 2597 | 2 | 3 | 4 | IV-2 | Aqp8 | 343 | 17-May-15 |
| 1970 | 2 | 3 | 4 | | IV-2 | Adamtsl1 | 92949 | 4-May-15 | 2601 | 2 | 3 | 4 | IV-2 | Araf | 369 | 4-May-15 |
| 1976 | 2 | 3 | 4 | | IV-2 | Adap2 | 56803 | 4-May-15 | 2608 | 2 | 3 | 4 | IV-2 | Arel1 | 9870 | 4-May-15 |
| 1977 | 2 | 3 | 4 | | IV-2 | Adar | 103 | 12-May-15 | 2625 | 2 | 3 | 4 | IV-2 | Arglu1 | 55082 | 12-May-15 |
| 1983 | 2 | 3 | 4 | | IV-2 | Adc | | | 2629 | 2 | 3 | 4 | IV-2 | Arhgap12 | 94134 | 4-May-15 |
| 1990 | 2 | 3 | 4 | | IV-2 | Adcy10 | 55811 | 4-May-15 | 2631 | 2 | 3 | 4 | IV-2 | Arhgap15os | | |
| 1995 | 2 | 3 | 4 | | IV-2 | Adcy6 | 112 | 23-May-15 | 2636 | 2 | 3 | 4 | IV-2 | Arhgap20os | | |
| 2003 | 2 | 3 | 4 | | IV-2 | Add3 | 120 | 12-May-15 | 2643 | 2 | 3 | 4 | IV-2 | Arhgap27 | 201176 | 4-May-15 |
| 2008 | 2 | 3 | 4 | | IV-2 | Adh6a | | | 2648 | 2 | 3 | 4 | IV-2 | Arhgap31 | 57514 | 4-May-15 |
| 2015 | 2 | 3 | 4 | | IV-2 | Adipor1 | 51094 | 31-May-15 | 2656 | 2 | 3 | 4 | IV-2 | Arhgap40 | 343578 | 4-May-15 |
| 2020 | 2 | 3 | 4 | | IV-2 | Adnp | 23394 | 4-May-15 | 2676 | 2 | 3 | 4 | IV-2 | Arhgef2 | 9181 | 4-May-15 |
| 2030 | 2 | 3 | 4 | | IV-2 | Adprhl2 | 54936 | 4-May-15 | 2701 | 2 | 3 | 4 | IV-2 | Arih1 | 25820 | 31-May-15 |
| 2033 | 2 | 3 | 4 | | IV-2 | Adra1b | 147 | 14-May-15 | 2706 | 2 | 3 | 4 | IV-2 | Arl13a | 392509 | 4-May-15 |
| 2041 | 2 | 3 | 4 | | IV-2 | Adrbk1 | 156 | 12-May-15 | 2721 | 2 | 3 | 4 | IV-2 | Arl5c | 390790 | 4-May-15 |
| 2052 | 2 | 3 | 4 | | IV-2 | AF067061 | | | 2722 | 2 | 3 | 4 | IV-2 | Arl6 | 84100 | 7-Jun-15 |
| 2055 | 2 | 3 | 4 | | IV-2 | AF357355 | | | 2723 | 2 | 3 | 4 | IV-2 | Arl6ip1 | 23204 | 4-May-15 |
| 2072 | 2 | 3 | 4 | | IV-2 | Afmid | 125061 | 4-May-15 | 2743 | 2 | 3 | 4 | IV-2 | Arrdcx3 | 51566 | 4-May-15 |
| 2076 | 2 | 3 | 4 | | IV-2 | Agap1 | 116987 | 12-May-15 | 2747 | 2 | 3 | 4 | IV-2 | Arnt | 405 | 7-Jun-15 |
| 2094 | 2 | 3 | 4 | | IV-2 | Ago3 | 192669 | 4-May-15 | 2750 | 2 | 3 | 4 | IV-2 | Arntl2 | 56938 | 4-May-15 |
| 2098 | 2 | 3 | 4 | | IV-2 | Agpat3 | 56894 | 4-May-15 | 2760 | 2 | 3 | 4 | IV-2 | Arr3 | 407 | 4-May-15 |
| 2100 | 2 | 3 | 4 | | IV-2 | Agpat5 | 55326 | 4-May-15 | 2766 | 2 | 3 | 4 | IV-2 | Arrdc4 | 91947 | 4-May-15 |
| 2105 | 2 | 3 | 4 | | IV-2 | Agr3 | 155465 | 4-May-15 | 2771 | 2 | 3 | 4 | IV-2 | Arsi | 340075 | 23-May-15 |
| 2113 | 2 | 3 | 4 | | IV-2 | Agtrap | 57085 | 4-May-15 | 2772 | 2 | 3 | 4 | IV-2 | Arsj | 79642 | 4-May-15 |
| 2115 | 2 | 3 | 4 | | IV-2 | Agxt2 | 64902 | 12-May-15 | 2778 | 2 | 3 | 4 | IV-2 | Art4 | 420 | 7-Jun-15 |
| 2135 | 2 | 3 | 4 | | IV-2 | AI413582 | | | 2780 | 2 | 3 | 4 | IV-2 | Artn | 9048 | 4-May-15 |
| 2136 | 2 | 3 | 4 | | IV-2 | AI414108 | | | 2785 | 2 | 3 | 4 | IV-2 | Arxes2 | | |
| 2145 | 2 | 3 | 4 | | IV-2 | AI506816 | | | 2796 | 2 | 3 | 4 | IV-2 | Asb13 | 79754 | 4-May-15 |
| 2147 | 2 | 3 | 4 | | IV-2 | AI593442 | | | 2800 | 2 | 3 | 4 | IV-2 | Asb17 | 127247 | 4-May-15 |
| 2154 | 2 | 3 | 4 | | IV-2 | AI747448 | | | 2804 | 2 | 3 | 4 | IV-2 | Asb3 | 51130 | 10-May-15 |
| 2155 | 2 | 3 | 4 | | IV-2 | AI837181 | | | 2807 | 2 | 3 | 4 | IV-2 | Asb6 | 140459 | 4-May-15 |
| 2160 | 2 | 3 | 4 | | IV-2 | AI854517 | | | 2821 | 2 | 3 | 4 | IV-2 | Asgr1 | 432 | 4-May-15 |
| 2164 | 2 | 3 | 4 | | IV-2 | Aida | 64853 | 7-Jun-15 | 2834 | 2 | 3 | 4 | IV-2 | Asnsd1 | 54529 | 4-May-15 |
| 2166 | 2 | 3 | 4 | | IV-2 | Aif1l | 83543 | 4-May-15 | 2840 | 2 | 3 | 4 | IV-2 | Asphd2 | 57168 | 23-May-15 |
| 2170 | 2 | 3 | 4 | | IV-2 | Aig1 | 51390 | 12-May-15 | 2842 | 2 | 3 | 4 | IV-2 | Aspn | 54829 | 12-May-15 |
| 2171 | 2 | 3 | 4 | | IV-2 | Aim1 | 202 | 7-Jun-15 | 2844 | 2 | 3 | 4 | IV-2 | Aspscr1 | 79958 | 4-May-15 |
| 2174 | 2 | 3 | 4 | | IV-2 | Aimp1 | 9255 | 17-May-15 | 2847 | 2 | 3 | 4 | IV-2 | Aste1 | 28990 | 12-May-15 |
| 2180 | 2 | 3 | 4 | | IV-2 | Ajap1 | 55966 | 4-May-15 | 2858 | 2 | 3 | 4 | IV-2 | Atad2b | 54464 | 12-May-15 |
| 2185 | 2 | 3 | 4 | | IV-2 | Ak2 | 204 | 4-May-15 | 2861 | 2 | 3 | 4 | IV-2 | Atad5 | 79915 | 4-May-15 |
| 2229 | 2 | 3 | 4 | | IV-2 | Akr1e1 | | | 2862 | 2 | 3 | 4 | IV-2 | Atat1 | 79969 | 4-May-15 |
| 2231 | 2 | 3 | 4 | | IV-2 | Akt1 | 207 | 31-May-15 | 2865 | 2 | 3 | 4 | IV-2 | Ate1 | 11101 | 4-May-15 |
| 2240 | 2 | 3 | 4 | | IV-2 | Alcam | 214 | 4-May-15 | 2869 | 2 | 3 | 4 | IV-2 | Atf4 | 468 | 4-May-15 |
| 2247 | 2 | 3 | 4 | | IV-2 | Aldh1b1 | 219 | 23-May-15 | 2874 | 2 | 3 | 4 | IV-2 | Atf7ip | 55729 | 12-May-15 |
| 2250 | 2 | 3 | 4 | | IV-2 | Aldh2 | 217 | 24-May-15 | 2877 | 2 | 3 | 4 | IV-2 | Atg101 | 60673 | 21-May-15 |
| 2268 | 2 | 3 | 4 | | IV-2 | Alg11 | 440138 | 23-May-15 | 2894 | 2 | 3 | 4 | IV-2 | Athl1 | 80162 | 4-May-15 |
| 2289 | 2 | 3 | 4 | | IV-2 | Alms1-ps2 | | | 2910 | 2 | 3 | 4 | IV-2 | Atp11b | 23200 | 4-May-15 |
| 2290 | 2 | 3 | 4 | | IV-2 | Alox12 | 239 | 17-May-15 | 2927 | 2 | 3 | 4 | IV-2 | Atp2a2 | 468 | 24-May-15 |
| 2291 | 2 | 3 | 4 | | IV-2 | Alox12b | 242 | 4-May-15 | 2933 | 2 | 3 | 4 | IV-2 | Atp2c1 | 27032 | 4-May-15 |
| 2296 | 2 | 3 | 4 | | IV-2 | Alox8 | | | 2950 | 2 | 3 | 4 | IV-2 | Atp5l | 10632 | 4-May-15 |
| 2297 | 2 | 3 | 4 | | IV-2 | Aloxe3 | 59344 | 23-May-15 | 2963 | 2 | 3 | 4 | IV-2 | Atp6v0d1 | 9114 | 4-May-15 |
| 2308 | 2 | 3 | 4 | | IV-2 | Alx1 | 8092 | 12-May-15 | 2965 | 2 | 3 | 4 | IV-2 | Atp6v0e | 8992 | 4-May-15 |
| 2313 | 2 | 3 | 4 | | IV-2 | Amacr | 23600 | 12-May-15 | 2969 | 2 | 3 | 4 | IV-2 | Atp5v1b2 | 526 | 4-May-15 |
| 2314 | 2 | 3 | 4 | | IV-2 | Ambn | 258 | 4-May-15 | 3021 | 2 | 3 | 4 | IV-2 | AU022252 | | |
| 2316 | 2 | 3 | 4 | | IV-2 | Ambra1 | 55626 | 21-May-15 | 3028 | 2 | 3 | 4 | IV-2 | AU041133 | | |
| 2318 | 2 | 3 | 4 | | IV-2 | Amd2 | 263 | 4-May-15 | 3030 | 2 | 3 | 4 | IV-2 | Aup1 | 550 | 3-May-15 |
| 2319 | 2 | 3 | 4 | | IV-2 | Amdhd1 | 144193 | 4-May-15 | 3032 | 2 | 3 | 4 | IV-2 | Aurkaip1 | 54998 | 4-May-15 |
| 2320 | 2 | 3 | 4 | | IV-2 | Amdhd2 | 51005 | 4-May-15 | 3034 | 2 | 3 | 4 | IV-2 | Aurkc | 6795 | 21-May-15 |
| 2333 | 2 | 3 | 4 | | IV-2 | Ammecr1l | 83807 | 4-May-15 | 3037 | 2 | 3 | 4 | IV-2 | AV051173 | | |
| 2340 | 2 | 3 | 4 | | IV-2 | Ampd2 | 271 | 12-May-15 | 3038 | 2 | 3 | 4 | IV-2 | AV320801 | | |
| 2344 | 2 | 3 | 4 | | IV-2 | Amtn | 401138 | 4-May-15 | 3041 | 2 | 3 | 4 | IV-2 | Avil9 | 23080 | 12-May-15 |
| 2349 | 2 | 3 | 4 | | IV-2 | Amz1 | 155185 | 4-May-15 | 3045 | 2 | 3 | 4 | IV-2 | Avpr1b | 553 | 17-May-15 |
| 2362 | 2 | 3 | 4 | | IV-2 | Ang2 | | | 3050 | 2 | 3 | 4 | IV-2 | AW146154 | | |
| 2363 | 2 | 3 | 4 | | IV-2 | Ang3 | | | 3054 | 2 | 3 | 4 | IV-2 | AW549877 | | |
| 2365 | 2 | 3 | 4 | | IV-2 | Angl | 27329 | 4-May-15 | 3062 | 2 | 3 | 4 | IV-2 | Axl | 558 | 17-May-15 |
| 2372 | 2 | 3 | 4 | | IV-2 | Angptl1 | 9068 | 4-May-15 | 3064 | 2 | 3 | 4 | IV-2 | AY358078 | | |
| 2373 | 2 | 3 | 4 | | IV-2 | Angptl2 | 23452 | 4-May-15 | 3071 | 2 | 3 | 4 | IV-2 | Azi2 | 64343 | 7-Jun-15 |
| 2376 | 2 | 3 | 4 | | IV-2 | Angptl6 | 83854 | 4-May-15 | 3091 | 2 | 3 | 4 | IV-2 | B230217O12Rik | | |
| 2378 | 2 | 3 | 4 | | IV-2 | Ank | 56172 | 7-Jun-15 | 3094 | 2 | 3 | 4 | IV-2 | B230319C09Rik | | |
| 2380 | 2 | 3 | 4 | | IV-2 | Ank2 | 287 | 12-May-15 | 3101 | 2 | 3 | 4 | IV-2 | B3galt2 | 8707 | 23-May-15 |
| 2391 | 2 | 3 | 4 | | IV-2 | Ankle2 | 23141 | 4-May-15 | 3102 | 2 | 3 | 4 | IV-2 | B3galt4 | 8705 | 4-May-15 |
| 2408 | 2 | 3 | 4 | | IV-2 | Ankrd24 | 170961 | 4-May-15 | 3104 | 2 | 3 | 4 | IV-2 | B3galt6 | 126792 | 4-May-15 |
| 2412 | 2 | 3 | 4 | | IV-2 | Ankrd29 | 147463 | 12-May-15 | 3110 | 2 | 3 | 4 | IV-2 | B3gnt2 | 10678 | 4-May-15 |
| 2413 | 2 | 3 | 4 | | IV-2 | Ankrd32 | 84256 | 4-May-15 | 3114 | 2 | 3 | 4 | IV-2 | B3gnt6 | 192134 | 4-May-15 |
| 2422 | 2 | 3 | 4 | | IV-2 | Ankrd39 | 51299 | 4-May-15 | 3116 | 2 | 3 | 4 | IV-2 | B3gnt8 | 374907 | 4-May-15 |
| 2434 | 2 | 3 | 4 | | IV-2 | Ankrd6 | 22881 | 4-May-15 | 3121 | 2 | 3 | 4 | IV-2 | B430306N03Rik | | |
| 2449 | 2 | 3 | 4 | | IV-2 | Ano1 | 55107 | 29-May-15 | 3137 | 2 | 3 | 4 | IV-2 | B930003M22Rik | | |
| 2455 | 2 | 3 | 4 | | IV-2 | Ano6 | 196527 | 23-May-15 | 3138 | 2 | 3 | 4 | IV-2 | B930018H19Rik | | |
| 2470 | 2 | 3 | 4 | | IV-2 | Anxa2 | 302 | 17-May-15 | 3144 | 2 | 3 | 4 | IV-2 | B9d2 | 80776 | 4-May-15 |
| 2472 | 2 | 3 | 4 | | IV-2 | Anxa4 | 307 | 4-May-15 | 3152 | 2 | 3 | 4 | IV-2 | Bach2os | | |
| 2478 | 2 | 3 | 4 | | IV-2 | Aoah | 313 | 4-May-15 | 3156 | 2 | 3 | 4 | IV-2 | Bag3 | 9531 | 24-May-15 |
| 2486 | 2 | 3 | 4 | | IV-2 | Ap1ar | 55435 | 4-May-15 | 3171 | 2 | 3 | 4 | IV-2 | Bambi-ps1 | | |
| 2495 | 2 | 3 | 4 | | IV-2 | Ap2a1 | 160 | 4-May-15 | 3175 | 2 | 3 | 4 | IV-2 | Banp | 54971 | 12-May-15 |
| 2506 | 2 | 3 | 4 | | IV-2 | Ap3s2 | 10239 | 4-May-15 | 3178 | 2 | 3 | 4 | IV-2 | Barhl1 | 56751 | 28-May-15 |
| 2527 | 2 | 3 | 4 | | IV-2 | Apeh | 327 | 21-May-15 | 3184 | 2 | 3 | 4 | IV-2 | Batf2 | 116071 | 12-May-15 |

Fig.22 - 9

| | | | | | | | |
|---|---|---|---|---|---|---|---|
| 3186 | 2 | 3 | 4 | IV-2 | Bax | 581 | 24-May-15 |
| 3216 | 2 | 3 | 4 | IV-2 | BC005624 | | |
| 3227 | 2 | 3 | 4 | IV-2 | BC021767 | | |
| 3228 | 2 | 3 | 4 | IV-2 | BC021785 | | |
| 3237 | 2 | 3 | 4 | IV-2 | BC027072 | | |
| 3247 | 2 | 3 | 4 | IV-2 | BC030870 | | |
| 3261 | 2 | 3 | 4 | IV-2 | BC048562 | | |
| 3272 | 2 | 3 | 4 | IV-2 | BC051019 | | |
| 3275 | 2 | 3 | 4 | IV-2 | BC051537 | | |
| 3290 | 2 | 3 | 4 | IV-2 | BC065397 | | |
| 3296 | 2 | 3 | 4 | IV-2 | BC094916 | | |
| 3300 | 2 | 3 | 4 | IV-2 | BC107364 | | |
| 3310 | 2 | 3 | 4 | IV-2 | Bcaslos2 | | |
| 3325 | 2 | 3 | 4 | IV-2 | Bcl11b | 64919 | 28-May-15 |
| 3326 | 2 | 3 | 4 | IV-2 | Bcl2 | 596 | 31-May-15 |
| 3329 | 2 | 3 | 4 | IV-2 | Bcl2a1c | | |
| 3331 | 2 | 3 | 4 | IV-2 | Bcl2l1 | 598 | 24-May-15 |
| 3341 | 2 | 3 | 4 | IV-2 | Bcl6b | 255877 | 4-May-15 |
| 3342 | 2 | 3 | 4 | IV-2 | Bcl7a | 605 | 4-May-15 |
| 3349 | 2 | 3 | 4 | IV-2 | Bco2 | 83875 | 4-May-15 |
| 3350 | 2 | 3 | 4 | IV-2 | Bcor | 54880 | 23-May-15 |
| 3356 | 2 | 3 | 4 | IV-2 | Bdkrb1 | 623 | 12-May-15 |
| 3358 | 2 | 3 | 4 | IV-2 | Bdnf | 627 | 7-Jun-15 |
| 3360 | 2 | 3 | 4 | IV-2 | Bean1 | 146227 | 23-May-15 |
| 3372 | 2 | 3 | 4 | IV-2 | Bet1 | 10282 | 4-May-15 |
| 3377 | 2 | 3 | 4 | IV-2 | Bex6 | | |
| 3378 | 2 | 3 | 4 | IV-2 | Bfar | 51283 | 4-May-15 |
| 3385 | 2 | 3 | 4 | IV-2 | Bhlha15 | 168620 | 14-May-15 |
| 3393 | 2 | 3 | 4 | IV-2 | Bhmt2 | 23743 | 4-May-15 |
| 3395 | 2 | 3 | 4 | IV-2 | Bicd1 | 636 | 3-May-15 |
| 3401 | 2 | 3 | 4 | IV-2 | Bin3 | 55909 | 4-May-15 |
| 3405 | 2 | 3 | 4 | IV-2 | Birc6 | 57448 | 21-May-15 |
| 3411 | 2 | 3 | 4 | IV-2 | Blmh | 642 | 23-May-15 |
| 3421 | 2 | 3 | 4 | IV-2 | Blzf1 | 8548 | 4-May-15 |
| 3432 | 2 | 3 | 4 | IV-2 | Bmp6 | 654 | 17-May-15 |
| 3435 | 2 | 3 | 4 | IV-2 | Bmp8b | 656 | 4-May-15 |
| 3437 | 2 | 3 | 4 | IV-2 | Bmpr1a | 657 | 23-May-15 |
| 3443 | 2 | 3 | 4 | IV-2 | Bnc1 | 646 | 7-Jun-15 |
| 3444 | 2 | 3 | 4 | IV-2 | Bnc2 | 54796 | 4-May-15 |
| 3469 | 2 | 3 | 4 | IV-2 | Bpifb2 | 80341 | 4-May-15 |
| 3475 | 2 | 3 | 4 | IV-2 | Bpifb9b | | |
| 3483 | 2 | 3 | 4 | IV-2 | Brca2 | 675 | 25-May-15 |
| 3484 | 2 | 3 | 4 | IV-2 | Brcc3 | 79184 | 7-Jun-15 |
| 3503 | 2 | 3 | 4 | IV-2 | Brix1 | 55299 | 4-May-15 |
| 3515 | 2 | 3 | 4 | IV-2 | Bscl2 | 26580 | 23-May-15 |
| 3524 | 2 | 3 | 4 | IV-2 | Bst2 | 684 | 31-May-15 |
| 3525 | 2 | 3 | 4 | IV-2 | Bsx | 390259 | 4-May-15 |
| 3538 | 2 | 3 | 4 | IV-2 | Btbd8 | 284697 | 4-May-15 |
| 3541 | 2 | 3 | 4 | IV-2 | Btd | 686 | 7-Jun-15 |
| 3547 | 2 | 3 | 4 | IV-2 | Btg4 | 54766 | 14-May-15 |
| 3550 | 2 | 3 | 4 | IV-2 | Btnl1a1 | 696 | 20-May-15 |
| 3554 | 2 | 3 | 4 | IV-2 | Btnl2 | 56244 | 12-May-15 |
| 3559 | 2 | 3 | 4 | IV-2 | Btrc | 8945 | 4-May-15 |
| 3561 | 2 | 3 | 4 | IV-2 | Bub1b | 701 | 24-May-15 |
| 3562 | 2 | 3 | 4 | IV-2 | Bub3 | 9184 | 12-May-15 |
| 3566 | 2 | 3 | 4 | IV-2 | Bysl | 705 | 21-May-15 |
| 3615 | 2 | 3 | 4 | IV-2 | C1ra | | |
| 3627 | 2 | 3 | 4 | IV-2 | C230079O03Rik | | |
| 3634 | 2 | 3 | 4 | IV-2 | C2cd4c | 126567 | 4-May-15 |
| 3636 | 2 | 3 | 4 | IV-2 | C2cd5 | 9847 | 4-May-15 |
| 3642 | 2 | 3 | 4 | IV-2 | C330013F16Rik | | |
| 3649 | 2 | 3 | 4 | IV-2 | C330046G13Rik | | |
| 3664 | 2 | 3 | 4 | IV-2 | C630028M04Rik | | |
| 3668 | 2 | 3 | 4 | IV-2 | C730002L08Rik | | |
| 3674 | 2 | 3 | 4 | IV-2 | C86187 | | |
| 3684 | 2 | 3 | 4 | IV-2 | C9 | 735 | 7-Jun-15 |
| 3696 | 2 | 3 | 4 | IV-2 | Cabp2 | 51475 | 4-May-15 |
| 3704 | 2 | 3 | 4 | IV-2 | Cacna1a | 773 | 22-May-15 |
| 3705 | 2 | 3 | 4 | IV-2 | Cacna1b | 774 | 12-May-15 |
| 3709 | 2 | 3 | 4 | IV-2 | Cacna1f | 778 | 23-May-15 |
| 3711 | 2 | 3 | 4 | IV-2 | Cacna1h | 8912 | 4-May-15 |
| 3715 | 2 | 3 | 4 | IV-2 | Cacna2d2 | 9254 | 12-May-15 |
| 3716 | 2 | 3 | 4 | IV-2 | Cacna2d3 | 55799 | 4-May-15 |
| 3723 | 2 | 3 | 4 | IV-2 | Cacng2 | 10369 | 4-May-15 |
| 3730 | 2 | 3 | 4 | IV-2 | Cactin | 58509 | 4-May-15 |
| 3737 | 2 | 3 | 4 | IV-2 | Cadm4 | 199731 | 1-Jun-15 |
| 3745 | 2 | 3 | 4 | IV-2 | Calcoco1 | 57658 | 29-May-15 |
| 3759 | 2 | 3 | 4 | IV-2 | Cain1 | 83698 | 4-May-15 |
| 3771 | 2 | 3 | 4 | IV-2 | Camk2g | 818 | 4-May-15 |
| 3775 | 2 | 3 | 4 | IV-2 | Camkk1 | 84254 | 4-May-15 |
| 3781 | 2 | 3 | 4 | IV-2 | Camsap1 | 157922 | 4-May-15 |
| 3788 | 2 | 3 | 4 | IV-2 | Cant1 | 124583 | 4-May-15 |
| 3797 | 2 | 3 | 4 | IV-2 | Capn13 | 92291 | 4-May-15 |
| 3798 | 2 | 3 | 4 | IV-2 | Capn15 | 6650 | 12-May-15 |
| 3817 | 2 | 3 | 4 | IV-2 | Car10 | 8038 | 4-May-15 |
| 3820 | 2 | 3 | 4 | IV-2 | Car13 | | |
| 3822 | 2 | 3 | 4 | IV-2 | Car15 | | |
| 3826 | 2 | 3 | 4 | IV-2 | Car5a | | |
| 3829 | 2 | 3 | 4 | IV-2 | Car7 | | |
| 3834 | 2 | 3 | 4 | IV-2 | Card14 | 79092 | 4-May-15 |
| 3849 | 2 | 3 | 4 | IV-2 | Casd1 | 64921 | 4-May-15 |
| 3859 | 2 | 3 | 4 | IV-2 | Casp6 | 839 | 4-May-15 |
| 3860 | 2 | 3 | 4 | IV-2 | Casp7 | 840 | 12-May-15 |
| 3863 | 2 | 3 | 4 | IV-2 | Casp9 | 842 | 4-May-15 |
| 3881 | 2 | 3 | 4 | IV-2 | Cav2 | 858 | 4-May-15 |
| 3883 | 2 | 3 | 4 | IV-2 | Cbfa2t2 | 9139 | 12-May-15 |
| 3887 | 2 | 3 | 4 | IV-2 | Cblb | 868 | 7-Jun-15 |
| 3899 | 2 | 3 | 4 | IV-2 | Cbwd1 | 55871 | 4-May-15 |
| 3905 | 2 | 3 | 4 | IV-2 | Cbx6 | 23466 | 12-May-15 |
| 3916 | 2 | 3 | 4 | IV-2 | Ccbl2 | 56267 | 4-May-15 |
| 3923 | 2 | 3 | 4 | IV-2 | Ccdc107 | 203280 | 4-May-15 |
| 3960 | 2 | 3 | 4 | IV-2 | Ccdc150 | 284992 | 4-May-15 |
| 3964 | 2 | 3 | 4 | IV-2 | Ccdc154 | 649811 | 4-May-15 |
| 3986 | 2 | 3 | 4 | IV-2 | Ccdc181 | 57821 | 4-May-15 |
| 3999 | 2 | 3 | 4 | IV-2 | Ccdc30 | 728621 | 4-May-15 |
| 4024 | 2 | 3 | 4 | IV-2 | Ccdc62 | 84660 | 4-May-15 |
| 4033 | 2 | 3 | 4 | IV-2 | Ccdc7 | 79741 | 4-May-15 |
| 4039 | 2 | 3 | 4 | IV-2 | Ccdc77 | 84318 | |
| 4043 | 2 | 3 | 4 | IV-2 | Ccdc80 | 151837 | |
| 4044 | 2 | 3 | 4 | IV-2 | Ccdc81 | 60494 | 28-May-15 |
| 4049 | 2 | 3 | 4 | IV-2 | Ccdc85b | 11007 | 4-May-15 |
| 4051 | 2 | 3 | 4 | IV-2 | Ccdc86 | 79080 | 4-May-15 |
| 4061 | 2 | 3 | 4 | IV-2 | Ccdc93 | 54520 | 4-May-15 |
| 4069 | 2 | 3 | 4 | IV-2 | Cckar | 886 | 12-May-15 |
| 4073 | 2 | 3 | 4 | IV-2 | Ccl12 | | |
| 4082 | 2 | 3 | 4 | IV-2 | Ccl24 | 6369 | |
| 4083 | 2 | 3 | 4 | IV-2 | Ccl25 | 6370 | 4-May-15 |
| 4084 | 2 | 3 | 4 | IV-2 | Ccl26 | 10344 | 17-May-15 |
| 4088 | 2 | 3 | 4 | IV-2 | Ccl3 | 6348 | |
| 4089 | 2 | 3 | 4 | IV-2 | Ccl4 | 6351 | 3-May-15 |
| 4100 | 2 | 3 | 4 | IV-2 | Ccnb1ip1 | 57820 | |
| 4102 | 2 | 3 | 4 | IV-2 | Ccnb3 | 85417 | 4-May-15 |
| 4105 | 2 | 3 | 4 | IV-2 | Ccnd2 | 894 | 4-May-15 |
| 4110 | 2 | 3 | 4 | IV-2 | Ccnf | 899 | 4-May-15 |
| 4111 | 2 | 3 | 4 | IV-2 | Ccng1 | 900 | 4-May-15 |
| 4117 | 2 | 3 | 4 | IV-2 | Ccnk | 8812 | 4-May-15 |
| 4122 | 2 | 3 | 4 | IV-2 | Ccnt2 | 905 | 4-May-15 |
| 4130 | 2 | 3 | 4 | IV-2 | Ccr1l1 | | |
| 4137 | 2 | 3 | 4 | IV-2 | Ccr8 | 1237 | 4-May-15 |
| 4166 | 2 | 3 | 4 | IV-2 | Cd19 | 930 | 12-May-15 |
| 4168 | 2 | 3 | 4 | IV-2 | Cd1d2 | | |
| 4169 | 2 | 3 | 4 | IV-2 | Cd2 | 914 | 12-May-15 |
| 4170 | 2 | 3 | 4 | IV-2 | Cd200 | 4345 | |
| 4172 | 2 | 3 | 4 | IV-2 | Cd200r2 | 344807 | 4-May-15 |
| 4178 | 2 | 3 | 4 | IV-2 | Cd209e | | |
| 4180 | 2 | 3 | 4 | IV-2 | Cd209e | | |
| 4182 | 2 | 3 | 4 | IV-2 | Cd209g | | |
| 4184 | 2 | 3 | 4 | IV-2 | Cd226 | 10666 | 12-May-15 |
| 4187 | 2 | 3 | 4 | IV-2 | Cd248 | 57124 | |
| 4190 | 2 | 3 | 4 | IV-2 | Cd274 | 29126 | 24-May-15 |
| 4191 | 2 | 3 | 4 | IV-2 | Cd276 | 80381 | |
| 4192 | 2 | 3 | 4 | IV-2 | Cd28 | 940 | 12-May-15 |
| 4193 | 2 | 3 | 4 | IV-2 | Cd2ap | 23607 | 4-May-15 |
| 4199 | 2 | 3 | 4 | IV-2 | Cd300ld | 100131439 | 4-May-15 |
| 4203 | 2 | 3 | 4 | IV-2 | Cd302 | 9936 | 4-May-15 |
| 4206 | 2 | 3 | 4 | IV-2 | Cd34 | 947 | 17-May-15 |
| 4209 | 2 | 3 | 4 | IV-2 | Cd38 | 952 | |
| 4212 | 2 | 3 | 4 | IV-2 | Cd3eap | 10849 | 4-May-15 |
| 4215 | 2 | 3 | 4 | IV-2 | Cd40 | 958 | 12-May-15 |
| 4216 | 2 | 3 | 4 | IV-2 | Cd40lg | 959 | 31-May-15 |
| 4218 | 2 | 3 | 4 | IV-2 | Cd46 | 4179 | 23-May-15 |
| 4224 | 2 | 3 | 4 | IV-2 | Cd55 | 1604 | |
| 4232 | 2 | 3 | 4 | IV-2 | Cd7 | 924 | 4-May-15 |
| 4235 | 2 | 3 | 4 | IV-2 | Cd74 | 972 | |
| 4238 | 2 | 3 | 4 | IV-2 | Cd80 | 941 | |
| 4243 | 2 | 3 | 4 | IV-2 | Cd86 | 942 | 31-May-15 |
| 4252 | 2 | 3 | 4 | IV-2 | Cdadc1 | 81602 | 4-May-15 |
| 4259 | 2 | 3 | 4 | IV-2 | Cdc20b | 166979 | 4-May-15 |
| 4264 | 2 | 3 | 4 | IV-2 | Cdc26 | 246184 | 4-May-15 |
| 4279 | 2 | 3 | 4 | IV-2 | Cdc42se1 | 56882 | 21-May-15 |
| 4282 | 2 | 3 | 4 | IV-2 | Cdc5l | 988 | 24-May-15 |
| 4284 | 2 | 3 | 4 | IV-2 | Cdc7 | 8317 | |
| 4288 | 2 | 3 | 4 | IV-2 | Cdca4 | 55038 | |
| 4290 | 2 | 3 | 4 | IV-2 | Cdca7 | 83879 | |
| 4298 | 2 | 3 | 4 | IV-2 | Cdh12 | 1010 | 4-May-15 |
| 4302 | 2 | 3 | 4 | IV-2 | Cdh17 | 1015 | 17-May-15 |
| 4315 | 2 | 3 | 4 | IV-2 | Cdh7 | 1005 | 7-Jun-15 |
| 4325 | 2 | 3 | 4 | IV-2 | Cdk10 | 8558 | 12-May-15 |
| 4348 | 2 | 3 | 4 | IV-2 | Cdk7 | 1022 | 4-May-15 |
| 4373 | 2 | 3 | 4 | IV-2 | Cdt2l | 30850 | 12-May-15 |
| 4415 | 2 | 3 | 4 | IV-2 | Celf1 | 10658 | 2-Jun-15 |
| 4427 | 2 | 3 | 4 | IV-2 | Cenpa | 1058 | 17-May-15 |
| 4428 | 2 | 3 | 4 | IV-2 | Cenpb | 1059 | 4-May-15 |
| 4431 | 2 | 3 | 4 | IV-2 | Cenpf | 1063 | 21-May-15 |
| 4433 | 2 | 3 | 4 | IV-2 | Cenpi | 2491 | |
| 4434 | 2 | 3 | 4 | IV-2 | Cenpj | 55835 | 31-May-15 |
| 4436 | 2 | 3 | 4 | IV-2 | Cenpl | 91687 | |
| 4438 | 2 | 3 | 4 | IV-2 | Cenpo | 55839 | 4-May-15 |
| 4439 | 2 | 3 | 4 | IV-2 | Cenpp | 79172 | 4-May-15 |
| 4441 | 2 | 3 | 4 | IV-2 | Cenpq | 55166 | |
| 4444 | 2 | 3 | 4 | IV-2 | Cenpv | 201161 | 4-May-15 |
| 4459 | 2 | 3 | 4 | IV-2 | Cep250 | 11190 | 17-May-15 |
| 4465 | 2 | 3 | 4 | IV-2 | Cep57 | 9702 | 4-May-15 |
| 4477 | 2 | 3 | 4 | IV-2 | Cep89 | 84902 | 12-May-15 |
| 4483 | 2 | 3 | 4 | IV-2 | Cerk | 64781 | |
| 4486 | 2 | 3 | 4 | IV-2 | Cers2 | 29956 | 4-May-15 |
| 4491 | 2 | 3 | 4 | IV-2 | Ces1a | | |
| 4500 | 2 | 3 | 4 | IV-2 | Ces2c | | |
| 4501 | 2 | 3 | 4 | IV-2 | Ces2d-ps | | |
| 4503 | 2 | 3 | 4 | IV-2 | Ces2f | | |
| 4505 | 2 | 3 | 4 | IV-2 | Ces2h | | |
| 4517 | 2 | 3 | 4 | IV-2 | Cfdp1 | 10428 | 4-May-15 |
| 4532 | 2 | 3 | 4 | IV-2 | Cgrrf1 | 10668 | 21-May-15 |
| 4537 | 2 | 3 | 4 | IV-2 | Chad | 150356 | 12-May-15 |

Fig.22 - 10

| | | | | | | | |
|---|---|---|---|---|---|---|---|
| 4548 | 2 | 3 | 4 | IV-2 | Chchd6 | 84303 | 2-Jun-15 |
| 4563 | 2 | 3 | 4 | IV-2 | Chek2 | 11200 | |
| 4569 | 2 | 3 | 4 | IV-2 | Chic1 | 53344 | 4-May-15 |
| 4575 | 2 | 3 | 4 | IV-2 | Chil6 | | |
| 4583 | 2 | 3 | 4 | IV-2 | Chmp1a | 5119 | 4-May-15 |
| 4597 | 2 | 3 | 4 | IV-2 | Chordc1 | 26973 | 4-May-15 |
| 4606 | 2 | 3 | 4 | IV-2 | Chrdl2 | 25884 | 4-May-15 |
| 4617 | 2 | 3 | 4 | IV-2 | Chrna5 | 1138 | 24-May-15 |
| 4620 | 2 | 3 | 4 | IV-2 | Chrna9 | 55584 | 12-May-15 |
| 4631 | 2 | 3 | 4 | IV-2 | Chst12 | 55501 | |
| 4637 | 2 | 3 | 4 | IV-2 | Chst4 | 10164 | |
| 4640 | 2 | 3 | 4 | IV-2 | Chst8 | 64377 | 4-May-15 |
| 4654 | 2 | 3 | 4 | IV-2 | Cib3 | 117286 | |
| 4655 | 2 | 3 | 4 | IV-2 | Cib4 | 130106 | 4-May-15 |
| 4658 | 2 | 3 | 4 | IV-2 | Cideb | 27141 | 12-May-15 |
| 4660 | 2 | 3 | 4 | IV-2 | Ciita | 4261 | 12-May-15 |
| 4663 | 2 | 3 | 4 | IV-2 | Cinp | 51560 | 4-May-15 |
| 4677 | 2 | 3 | 4 | IV-2 | Ciz1 | 25792 | 12-May-15 |
| 4680 | 2 | 3 | 4 | IV-2 | Ckap2l | 150468 | 12-May-15 |
| 4681 | 2 | 3 | 4 | IV-2 | Ckap4 | 16970 | 4-May-15 |
| 4686 | 2 | 3 | 4 | IV-2 | Ckmt1 | 548596, 1159 | /6/7 |
| 4691 | 2 | 3 | 4 | IV-2 | Clasp1 | 23332 | 28-May-15 |
| 4697 | 2 | 3 | 4 | IV-2 | Clca4 | 22802 | 12-May-15 |
| 4703 | 2 | 3 | 4 | IV-2 | Clcn2 | 1181 | |
| 4713 | 2 | 3 | 4 | IV-2 | Cldn11 | 5010 | 12-May-15 |
| 4718 | 2 | 3 | 4 | IV-2 | Cldn16 | 10686 | 4-May-15 |
| 4723 | 2 | 3 | 4 | IV-2 | Cldn20 | 49861 | |
| 4732 | 2 | 3 | 4 | IV-2 | Cldn6 | 9074 | 4-May-15 |
| 4740 | 2 | 3 | 4 | IV-2 | Clec12b | 387837 | 4-May-15 |
| 4742 | 2 | 3 | 4 | IV-2 | Clec16a | 23274 | 10-May-15 |
| 4751 | 2 | 3 | 4 | IV-2 | Clec2i | | |
| 4756 | 2 | 3 | 4 | IV-2 | Clec4a2 | | |
| 4758 | 2 | 3 | 4 | IV-2 | Clec4a4 | | |
| 4768 | 2 | 3 | 4 | IV-2 | Clec9a | 283420 | 1-May-15 |
| 4771 | 2 | 3 | 4 | IV-2 | Clic1 | 1192 | |
| 4773 | 2 | 3 | 4 | IV-2 | Clic4 | 25932 | 4-May-15 |
| 4776 | 2 | 3 | 4 | IV-2 | Clint1 | 9685 | 12-May-15 |
| 4808 | 2 | 3 | 4 | IV-2 | Clstn3 | 9746 | 4-May-15 |
| 4809 | 2 | 3 | 4 | IV-2 | Clta | 1211 | 4-May-15 |
| 4813 | 2 | 3 | 4 | IV-2 | Cluap1 | 23059 | 4-May-15 |
| 4819 | 2 | 3 | 4 | IV-2 | Cma2 | | |
| 4820 | 2 | 3 | 4 | IV-2 | Cmah | 8418 | 3-May-15 |
| 4821 | 2 | 3 | 4 | IV-2 | Cmas | 55907 | 12-May-15 |
| 4828 | 2 | 3 | 4 | IV-2 | Cml2 | 51471 | 4-May-15 |
| 4829 | 2 | 3 | 4 | IV-2 | Cml3 | 339983 | 4-May-15 |
| 4831 | 2 | 3 | 4 | IV-2 | Cmpk1 | 51727 | 14-May-15 |
| 4834 | 2 | 3 | 4 | IV-2 | Cmtm1 | 113540 | 4-May-15 |
| 4846 | 2 | 3 | 4 | IV-2 | Cnbd2 | 140894 | 4-May-15 |
| 4850 | 2 | 3 | 4 | IV-2 | Cnepir1 | 255919 | 4-May-15 |
| 4866 | 2 | 3 | 4 | IV-2 | Cnn2 | 1265 | |
| 4891 | 2 | 3 | 4 | IV-2 | Cnst | 163882 | 4-May-15 |
| 4910 | 2 | 3 | 4 | IV-2 | Cntrob | 116840 | |
| 4931 | 2 | 3 | 4 | IV-2 | Col11a2 | 1302 | 28-May-15 |
| 4936 | 2 | 3 | 4 | IV-2 | Col16a1 | 1307 | |
| 4942 | 2 | 3 | 4 | IV-2 | Col20a1 | 57642 | 4-May-15 |
| 4945 | 2 | 3 | 4 | IV-2 | Col24a1 | 255631 | 21-May-15 |
| 4946 | 2 | 3 | 4 | IV-2 | Col25a1 | 84570 | 4-May-15 |
| 4949 | 2 | 3 | 4 | IV-2 | Col28a1 | 340267 | 4-May-15 |
| 4952 | 2 | 3 | 4 | IV-2 | Col4a1 | 1282 | |
| 4953 | 2 | 3 | 4 | IV-2 | Col4a2 | 1284 | |
| 4954 | 2 | 3 | 4 | IV-2 | Col4a3 | 1285 | |
| 4955 | 2 | 3 | 4 | IV-2 | Col4a3bp | 10087 | 21-May-15 |
| 4957 | 2 | 3 | 4 | IV-2 | Col4a5 | 1287 | 28-May-15 |
| 4958 | 2 | 3 | 4 | IV-2 | Col4a6 | 1288 | 4-May-15 |
| 4960 | 2 | 3 | 4 | IV-2 | Col5a2 | 1290 | |
| 4961 | 2 | 3 | 4 | IV-2 | Col5a3 | 50509 | |
| 4962 | 2 | 3 | 4 | IV-2 | Col6a1 | 1291 | |
| 4967 | 2 | 3 | 4 | IV-2 | Col6a6 | 131873 | 4-May-15 |
| 4968 | 2 | 3 | 4 | IV-2 | Col7a1 | 1294 | 31-May-15 |
| 4970 | 2 | 3 | 4 | IV-2 | Col8a2 | 1296 | 23-May-15 |
| 4976 | 2 | 3 | 4 | IV-2 | Colec12 | 81035 | 3-May-15 |
| 4979 | 2 | 3 | 4 | IV-2 | Commd1 | 150684 | 4-May-15 |
| 4986 | 2 | 3 | 4 | IV-2 | Commd7 | 149951 | 4-May-15 |
| 4990 | 2 | 3 | 4 | IV-2 | Comt | 1312 | 4-May-15 |
| 4999 | 2 | 3 | 4 | IV-2 | Cops2 | 9318 | 4-May-15 |
| 5009 | 2 | 3 | 4 | IV-2 | Coq10a | 93058 | 4-May-15 |
| 5019 | 2 | 3 | 4 | IV-2 | Coro1a | 11151 | 4-May-15 |
| 5020 | 2 | 3 | 4 | IV-2 | Coro1b | 57175 | 4-May-15 |
| 5025 | 2 | 3 | 4 | IV-2 | Coro7 | 79985 | |
| 5037 | 2 | 3 | 4 | IV-2 | Cox4i1 | 1327 | 4-May-15 |
| 5039 | 2 | 3 | 4 | IV-2 | Cox5a | 9377 | 4-May-15 |
| 5043 | 2 | 3 | 4 | IV-2 | Cox6b1 | 1340 | 4-May-15 |
| 5047 | 2 | 3 | 4 | IV-2 | Cox7a2 | 1347 | 4-May-15 |
| 5054 | 2 | 3 | 4 | IV-2 | Cox8c | 341947 | 4-May-15 |
| 5058 | 2 | 3 | 4 | IV-2 | Cpa3 | 1359 | /5/12 |
| 5059 | 2 | 3 | 4 | IV-2 | Cpa4 | 51200 | 4-May-15 |
| 5060 | 2 | 3 | 4 | IV-2 | Cpa5 | 93979 | 4-May-15 |
| 5063 | 2 | 3 | 4 | IV-2 | Cpb2 | 1361 | 4-May-15 |
| 5085 | 2 | 3 | 4 | IV-2 | Cpne6 | 9362 | 4-May-15 |
| 5093 | 2 | 3 | 4 | IV-2 | Cpsf1 | 29894 | 4-May-15 |
| 5108 | 2 | 3 | 4 | IV-2 | Cpxm2 | 119587 | 4-May-15 |
| 5110 | 2 | 3 | 4 | IV-2 | Cr1l | 1379 | |
| 5114 | 2 | 3 | 4 | IV-2 | Cradd | 8738 | 4-May-15 |
| 5126 | 2 | 3 | 4 | IV-2 | Creb3l2 | 64764 | |
| 5128 | 2 | 3 | 4 | IV-2 | Creb3l4 | 148305 | 28-May-15 |
| 5136 | 2 | 3 | 4 | IV-2 | Creld1 | 78987 | 4-May-15 |
| 5143 | 2 | 3 | 4 | IV-2 | Crim1 | 51232 | 12-May-15 |
| 5145 | 2 | 3 | 4 | IV-2 | Crip2 | 1397 | 4-May-15 |
| 5153 | 2 | 3 | 4 | IV-2 | Crispld2 | 83716 | |
| 5158 | 2 | 3 | 4 | IV-2 | Crlf3 | 51379 | 12-May-15 |
| 5162 | 2 | 3 | 4 | IV-2 | Crnkl1 | 51340 | 28-May-15 |
| 5164 | 2 | 3 | 4 | IV-2 | Crocc | 9696 | 4-May-15 |
| 5168 | 2 | 3 | 4 | IV-2 | Crtam | 56253 | 12-May-15 |
| 5179 | 2 | 3 | 4 | IV-2 | Cryba1 | 1411 | 17-May-15 |
| 5182 | 2 | 3 | 4 | IV-2 | Crybb1 | 1414 | |
| 5184 | 2 | 3 | 4 | IV-2 | Crybb3 | 1417 | 4-May-15 |
| 5185 | 2 | 3 | 4 | IV-2 | Crybg3 | 131544 | 4-May-15 |
| 5193 | 2 | 3 | 4 | IV-2 | Crygs | 1427 | 4-May-15 |
| 5196 | 2 | 3 | 4 | IV-2 | Cryz | 1429 | 12-May-15 |
| 5212 | 2 | 3 | 4 | IV-2 | Csgalnact2 | 55454 | 12-May-15 |
| 5251 | 2 | 3 | 4 | IV-2 | Cst7 | 8530 | 12-May-15 |
| 5257 | 2 | 3 | 4 | IV-2 | Cstf1 | 1477 | 12-May-15 |
| 5271 | 2 | 3 | 4 | IV-2 | Ctdnep1 | 23399 | 4-May-15 |
| 5282 | 2 | 3 | 4 | IV-2 | Ctif | 9811 | 4-May-15 |
| 5300 | 2 | 3 | 4 | IV-2 | Ctrc | 11330 | 23-May-15 |
| 5303 | 2 | 3 | 4 | IV-2 | Cts3 | | |
| 5318 | 2 | 3 | 4 | IV-2 | Ctsl | 1514 | |
| 5326 | 2 | 3 | 4 | IV-2 | Ctsz | 1522 | |
| 5335 | 2 | 3 | 4 | IV-2 | Cubn | 8029 | 12-May-15 |
| 5336 | 2 | 3 | 4 | IV-2 | Cuedc1 | 404093 | 12-May-15 |
| 5352 | 2 | 3 | 4 | IV-2 | Cwc15 | 51503 | 4-May-15 |
| 5364 | 2 | 3 | 4 | IV-2 | Cxcl11 | 6373 | 3-May-15 |
| 5372 | 2 | 3 | 4 | IV-2 | Cxcl3 | 2921 | 12-May-15 |
| 5374 | 2 | 3 | 4 | IV-2 | Cxcl9 | 4283 | |
| 5380 | 2 | 3 | 4 | IV-2 | Cxcr6 | 10663 | 14-May-15 |
| 5384 | 2 | 3 | 4 | IV-2 | Cxxc1 | 30827 | 4-May-15 |
| 5394 | 2 | 3 | 4 | IV-2 | Cyb5d2 | 124936 | 4-May-15 |
| 5403 | 2 | 3 | 4 | IV-2 | Cyc1 | 1537 | 7-Jun-15 |
| 5415 | 2 | 3 | 4 | IV-2 | Cyp11b1 | 1584 | 12-May-15 |
| 5418 | 2 | 3 | 4 | IV-2 | Cyp19a1 | 1588 | 21-May-15 |
| 5420 | 2 | 3 | 4 | IV-2 | Cyp1a2 | 1544 | 24-May-15 |
| 5430 | 2 | 3 | 4 | IV-2 | Cyp2s12 | | |
| 5434 | 2 | 3 | 4 | IV-2 | Cyp2ab1 | | |
| 5446 | 2 | 3 | 4 | IV-2 | Cyp2c50 | | |
| 5447 | 2 | 3 | 4 | IV-2 | Cyp2c53-ps | | |
| 5456 | 2 | 3 | 4 | IV-2 | Cyp2d10 | | |
| 5457 | 2 | 3 | 4 | IV-2 | Cyp2d11 | | |
| 5459 | 2 | 3 | 4 | IV-2 | Cyp2d13 | | |
| 5464 | 2 | 3 | 4 | IV-2 | Cyp2d40 | | |
| 5472 | 2 | 3 | 4 | IV-2 | Cyp2j5 | | |
| 5480 | 2 | 3 | 4 | IV-2 | Cyp2w1 | 54905 | 4-May-15 |
| 5502 | 2 | 3 | 4 | IV-2 | Cyp4f13 | | |
| 5504 | 2 | 3 | 4 | IV-2 | Cyp4f15 | | |
| 5508 | 2 | 3 | 4 | IV-2 | Cyp4f37 | | |
| 5513 | 2 | 3 | 4 | IV-2 | Cyp4x1 | 260293 | 4-May-15 |
| 5518 | 2 | 3 | 4 | IV-2 | Cypt1 | | |
| 5533 | 2 | 3 | 4 | IV-2 | Cyth1 | 9267 | 12-May-15 |
| 5537 | 2 | 3 | 4 | IV-2 | Cytip | 9595 | |
| 5540 | 2 | 3 | 4 | IV-2 | D030018L15Rik | | |
| 5545 | 2 | 3 | 4 | IV-2 | D030048B21Rik | | |
| 5555 | 2 | 3 | 4 | IV-2 | D130020L05Rik | | |
| 5556 | 2 | 3 | 4 | IV-2 | D130040H23Rik | | |
| 5558 | 2 | 3 | 4 | IV-2 | D130058E03 | | |
| 5576 | 2 | 3 | 4 | IV-2 | D330045A20Rik | | |
| 5583 | 2 | 3 | 4 | IV-2 | D430020J02Rik | | |
| 5584 | 2 | 3 | 4 | IV-2 | D430036J16Rik | | |
| 5593 | 2 | 3 | 4 | IV-2 | D630010B17Rik | | |
| 5597 | 2 | 3 | 4 | IV-2 | D630029K05Rik | | |
| 5608 | 2 | 3 | 4 | IV-2 | D730005E14Rik | | |
| 5621 | 2 | 3 | 4 | IV-2 | D830032E09Rik | | |
| 5648 | 2 | 3 | 4 | IV-2 | Dak | 26007 | 4-May-15 |
| 5656 | 2 | 3 | 4 | IV-2 | Dapk2 | 23804 | 21-May-15 |
| 5659 | 2 | 3 | 4 | IV-2 | Dapp1 | 27071 | 12-May-15 |
| 5669 | 2 | 3 | 4 | IV-2 | Dbhos | | |
| 5674 | 2 | 3 | 4 | IV-2 | Dbndd2 | 55861 | 4-May-15 |
| 5677 | 2 | 3 | 4 | IV-2 | Dbpht2 | | |
| 5700 | 2 | 3 | 4 | IV-2 | Dcdc2b | 149069 | 4-May-15 |
| 5704 | 2 | 3 | 4 | IV-2 | Dclk1 | 9201 | 21-May-15 |
| 5707 | 2 | 3 | 4 | IV-2 | Ddit4l | 9937 | 12-May-15 |
| 5717 | 2 | 3 | 4 | IV-2 | Dcps | 28960 | 4-May-15 |
| 5738 | 2 | 3 | 4 | IV-2 | Ddah2 | 23564 | 31-May-15 |
| 5739 | 2 | 3 | 4 | IV-2 | Ddb1 | 1642 | 4-May-15 |
| 5746 | 2 | 3 | 4 | IV-2 | Ddit3 | 1649 | 17-May-15 |
| 5751 | 2 | 3 | 4 | IV-2 | Ddost | 1650 | 23-May-15 |
| 5794 | 2 | 3 | 4 | IV-2 | Deaf1 | 10522 | 4-May-15 |
| 5802 | 2 | 3 | 4 | IV-2 | Def8 | 54849 | 4-May-15 |
| 5810 | 2 | 3 | 4 | IV-2 | Defa25 | | |
| 5813 | 2 | 3 | 4 | IV-2 | Defa4 | 1669 | 4-May-15 |
| 5839 | 2 | 3 | 4 | IV-2 | Defb3 | | |
| 5861 | 2 | 3 | 4 | IV-2 | Defb7 | 245910 | 4-May-15 |
| 5866 | 2 | 3 | 4 | IV-2 | Dek | 7913 | 4-May-15 |
| 5884 | 2 | 3 | 4 | IV-2 | Depdc5 | 9681 | 28-May-15 |
| 5892 | 2 | 3 | 4 | IV-2 | Desi1 | 27351 | 7-Jun-15 |
| 5909 | 2 | 3 | 4 | IV-2 | Dgkd | 8527 | 4-May-15 |
| 5920 | 2 | 3 | 4 | IV-2 | Dhcr7 | 1717 | 23-May-15 |
| 5921 | 2 | 3 | 4 | IV-2 | Dhdds | 79947 | 29-May-15 |
| 5925 | 2 | 3 | 4 | IV-2 | Dhodh | 1723 | 4-May-15 |
| 5934 | 2 | 3 | 4 | IV-2 | Dhrs7b | 25979 | 4-May-15 |
| 5936 | 2 | 3 | 4 | IV-2 | Dhrs9 | 10170 | 4-May-15 |
| 5937 | 2 | 3 | 4 | IV-2 | Dhrsx | 207063 | 4-May-15 |
| 5953 | 2 | 3 | 4 | IV-2 | Dhx8 | 1659 | 4-May-15 |
| 5964 | 2 | 3 | 4 | IV-2 | Dio2 | 1734 | 17-May-15 |
| 5965 | 2 | 3 | 4 | IV-2 | Dio3 | 1735 | 12-May-15 |
| 5979 | 2 | 3 | 4 | IV-2 | Dixdc1 | 85458 | 12-May-15 |

Fig.22 - 11

| | | | | | | | | | | | | | | | |
|---|---|---|---|---|---|---|---|---|---|---|---|---|---|---|---|
| 5991 | 2 | 3 | 4 | | IV-2 | Dleu7 | 220107 | 12-May-15 | 6760 | 2 | 3 | 4 | | IV-2 | Eqtn | 54586 | 4-May-15 |
| 5992 | 2 | 3 | 4 | | IV-2 | Dlg1 | 1739 | 12-May-15 | 6767 | 2 | 3 | 4 | | IV-2 | Erbb4 | 2066 | 23-May-15 |
| 6002 | 2 | 3 | 4 | | IV-2 | Dlk1 | 8788 | 31-May-15 | 6770 | 2 | 3 | 4 | | IV-2 | Ercc1 | 2067 | 23-May-15 |
| 6005 | 2 | 3 | 4 | | IV-2 | Dll3 | 10683 | 23-May-15 | 6777 | 2 | 3 | 4 | | IV-2 | Ercc6l2 | 375748 | 4-May-15 |
| 6010 | 2 | 3 | 4 | | IV-2 | Dlx2 | 1746 | 4-May-15 | 6780 | 2 | 3 | 4 | | IV-2 | Ereg | 2069 | 4-May-15 |
| 6011 | 2 | 3 | 4 | | IV-2 | Dlx3 | 1747 | 28-May-15 | 6789 | 2 | 3 | 4 | | IV-2 | Eri3 | 79033 | 2-Jun-15 |
| 6012 | 2 | 3 | 4 | | IV-2 | Dlx4 | 1748 | 4-May-15 | 6800 | 2 | 3 | 4 | | IV-2 | Ermard | 55780 | 12-May-15 |
| 6013 | 2 | 3 | 4 | | IV-2 | Dlx5 | 1749 | 28-May-15 | 6804 | 2 | 3 | 4 | | IV-2 | Ern2 | 10595 | 12-May-15 |
| 6019 | 2 | 3 | 4 | | IV-2 | Dmbx1 | 127343 | 4-May-15 | 6808 | 2 | 3 | 4 | | IV-2 | Erp29 | 10961 | 17-May-15 |
| 6021 | 2 | 3 | 4 | | IV-2 | Dmd | 1756 | 24-May-15 | 6813 | 2 | 3 | 4 | | IV-2 | Esco1 | 114799 | 4-May-15 |
| 6022 | 2 | 3 | 4 | | IV-2 | Dmgdh | 29958 | 4-May-15 | 6818 | 2 | 3 | 4 | | IV-2 | Esp1 | | |
| 6027 | 2 | 3 | 4 | | IV-2 | Dmrt1 | 1761 | 4-May-15 | 6858 | 2 | 3 | 4 | | IV-2 | Etnppl | 64850 | 3-May-15 |
| 6039 | 2 | 3 | 4 | | IV-2 | Dnrwd | 1762 | 4-May-15 | 6876 | 2 | 3 | 4 | | IV-2 | Evi2a-evi2b | | |
| 6067 | 2 | 3 | 4 | | IV-2 | Dnajb14 | 79982 | 4-May-15 | 6878 | 2 | 3 | 4 | | IV-2 | Evi5 | 7813 | 21-May-15 |
| 6090 | 2 | 3 | 4 | | IV-2 | Dnajc24 | 120526 | 4-May-15 | 6881 | 2 | 3 | 4 | | IV-2 | Evpl | 2125 | 12-May-15 |
| 6108 | 2 | 3 | 4 | | IV-2 | Dnase1l1 | 1774 | 12-May-15 | 6888 | 2 | 3 | 4 | | IV-2 | Exo5 | 64789 | 4-May-15 |
| 6115 | 2 | 3 | 4 | | IV-2 | Dnlz | 728489 | 4-May-15 | 6893 | 2 | 3 | 4 | | IV-2 | Exoc3l4 | 91828 | 4-May-15 |
| 6130 | 2 | 3 | 4 | | IV-2 | Dnmt1ip1 | 116092 | 4-May-15 | 6909 | 2 | 3 | 4 | | IV-2 | Exosc8 | 11340 | 4-May-15 |
| 6135 | 2 | 3 | 4 | | IV-2 | Dock1 | 1793 | 24-May-15 | 6915 | 2 | 3 | 4 | | IV-2 | Extl2 | 2135 | 4-May-15 |
| 6137 | 2 | 3 | 4 | | IV-2 | Dock11 | 139818 | 12-May-15 | 6926 | 2 | 3 | 4 | | IV-2 | F11r | 50848 | 4-May-15 |
| 6145 | 2 | 3 | 4 | | IV-2 | Dock9 | 23348 | 12-May-15 | 6931 | 2 | 3 | 3 | | IV-2 | F2r | 2149 | 17-May-15 |
| 6150 | 2 | 3 | 4 | | IV-2 | Dock4 | 55715 | 3-May-15 | 6948 | 2 | 3 | 4 | | IV-2 | F830045P16Rik | | |
| 6152 | 2 | 3 | 4 | | IV-2 | Dock6 | 220164 | 2-Jun-15 | 6955 | 2 | 3 | 4 | | IV-2 | Fabp12 | 646486 | 4-May-15 |
| 6167 | 2 | 3 | 4 | | IV-2 | Dpep3 | 64180 | 4-May-15 | 6968 | 2 | 3 | 4 | | IV-2 | Fgf1 | 11124 | 4-May-15 |
| 6171 | 2 | 3 | 4 | | IV-2 | Dph1 | 1801 | 4-May-15 | 6977 | 2 | 3 | 4 | | IV-2 | Fam101b | 359845 | 4-May-15 |
| 6185 | 2 | 3 | 4 | | IV-2 | Dpp8 | 54878 | 21-May-15 | 6978 | 2 | 3 | 4 | | IV-2 | Fam102a | 399665 | 4-May-15 |
| 6193 | 2 | 3 | 4 | | IV-2 | Dpy19l1 | 23333 | 4-May-15 | 6987 | 2 | 3 | 4 | | IV-2 | Fam110a | 83541 | 4-May-15 |
| 6196 | 2 | 3 | 4 | | IV-2 | Dpy19l4 | 286148 | 4-May-15 | 6988 | 2 | 3 | 4 | | IV-2 | Fam110b | 90362 | 4-May-15 |
| 6197 | 2 | 3 | 4 | | IV-2 | Dpy30 | 84661 | 24-May-15 | 6992 | 2 | 3 | 4 | | IV-2 | Fam114a2 | 10827 | 4-May-15 |
| 6207 | 2 | 3 | 4 | | IV-2 | Dqx1 | 165545 | 4-May-15 | 7014 | 2 | 3 | 4 | | IV-2 | Fam131a | 131408 | 12-May-15 |
| 6218 | 2 | 3 | 4 | | IV-2 | Drd5 | 1816 | 28-May-15 | 7019 | 2 | 3 | 4 | | IV-2 | Fam133b | 257415 | 4-May-15 |
| 6230 | 2 | 3 | 4 | | IV-2 | Dscr3 | 10311 | 12-May-15 | 7033 | 2 | 3 | 4 | | IV-2 | Fam151a | 338084 | 4-May-15 |
| 6243 | 2 | 3 | 4 | | IV-2 | Dstn | 11034 | 4-May-15 | 7034 | 2 | 3 | 4 | | IV-2 | Fam151b | 167555 | 4-May-15 |
| 6259 | 2 | 3 | 4 | | IV-2 | Dtymk | 1841 | 4-May-15 | 7035 | 2 | 3 | 4 | | IV-2 | Fam154a | 158297 | 4-May-15 |
| 6265 | 2 | 3 | 4 | | IV-2 | Dusl1 | 64118 | 4-May-15 | 7049 | 2 | 3 | 4 | | IV-2 | Fam163b | 642968 | 4-May-15 |
| 6271 | 2 | 3 | 4 | | IV-2 | Dusp11 | 8446 | 4-May-15 | 7050 | 2 | 3 | 4 | | IV-2 | Fam166a | 401565 | 4-May-15 |
| 6280 | 2 | 3 | 4 | | IV-2 | Dusp21 | 63904 | 4-May-15 | 7063 | 2 | 3 | 4 | | IV-2 | Fam172a | 83989 | 12-May-15 |
| 6293 | 2 | 3 | 4 | | IV-2 | Dut | 1854 | 12-May-15 | 7068 | 2 | 3 | 4 | | IV-2 | Fam175a | 84142 | 4-May-15 |
| 6297 | 2 | 3 | 4 | | IV-2 | Duxbl3 | | | 7072 | 2 | 3 | 4 | | IV-2 | Fam179a | 165186 | 4-May-15 |
| 6322 | 2 | 3 | 4 | | IV-2 | Dynlt3 | 6990 | 4-May-15 | 7078 | 2 | 3 | 4 | | IV-2 | Fam184a | 79632 | 4-May-15 |
| 6340 | 2 | 3 | 4 | | IV-2 | E030019B06Rik | | | 7095 | 2 | 3 | 4 | | IV-2 | Fam196b | 100131 897 | 4-May-15 |
| 6345 | 2 | 3 | 4 | | IV-2 | E030044B06Rik | | | 7114 | 2 | 3 | 4 | | IV-2 | Fam21 | | |
| 6352 | 2 | 3 | 4 | | IV-2 | E130114P18Rik | | | 7118 | 2 | 3 | 4 | | IV-2 | Fam212b | 95924 | 4-May-15 |
| 6361 | 2 | 3 | 4 | | IV-2 | E130309F12Rik | | | 7121 | 2 | 3 | 4 | | IV-2 | Fam214a | 56204 | 4-May-15 |
| 6363 | 2 | 3 | 4 | | IV-2 | E130311K13Rik | | | 7122 | 2 | 3 | 4 | | IV-2 | Fam214b | 80256 | 4-May-15 |
| 6372 | 2 | 3 | 4 | | IV-2 | E2f2 | 1870 | 4-May-15 | 7126 | 2 | 3 | 4 | | IV-2 | Fam217b | 63939 | 4-May-15 |
| 6373 | 2 | 3 | 4 | | IV-2 | E2f3 | 1871 | 17-May-15 | 7127 | 2 | 3 | 4 | | IV-2 | Fam219a | 203259 | 4-May-15 |
| 6379 | 2 | 3 | 4 | | IV-2 | E330009J07Rik | | | 7132 | 2 | 3 | 4 | | IV-2 | Fam219b | 392307 | 4-May-15 |
| 6380 | 2 | 3 | 4 | | IV-2 | E330011O21Rik | | | 7143 | 2 | 3 | 4 | | IV-2 | Fam26d | 221301 | 12-May-15 |
| 6402 | 2 | 3 | 4 | | IV-2 | Ear14 | | | 7144 | 2 | 3 | 4 | | IV-2 | Fam26e | 254228 | 4-May-15 |
| 6405 | 2 | 3 | 4 | | IV-2 | Ear4 | | | 7148 | 2 | 3 | 4 | | IV-2 | Fam32a | 26017 | 4-May-15 |
| 6415 | 2 | 3 | 4 | | IV-2 | Ebna1bp2 | 10969 | 4-May-15 | 7151 | 2 | 3 | 4 | | IV-2 | Fam43a | 131583 | 4-May-15 |
| 6424 | 2 | 3 | 4 | | IV-2 | Echdc2 | 55268 | 4-May-15 | 7157 | 2 | 3 | 4 | | IV-2 | Fam46d | 169966 | 4-May-15 |
| 6433 | 2 | 3 | 4 | | IV-2 | Ecsit | 51295 | 4-May-15 | 7168 | 2 | 3 | 4 | | IV-2 | Fam67b | 83723 | 4-May-15 |
| 6435 | 2 | 3 | 4 | | IV-2 | Ect2l | 345930 | 4-May-15 | 7169 | 2 | 3 | 4 | | IV-2 | Fam58b | 339521 | 4-May-15 |
| 6439 | 2 | 3 | 4 | | IV-2 | Edaradd | 128178 | 23-May-15 | 7174 | 2 | 3 | 4 | | IV-2 | Fam65a | 79567 | 4-May-15 |
| 6440 | 2 | 3 | 4 | | IV-2 | Edc3 | 80153 | 4-May-15 | 7176 | 2 | 3 | 4 | | IV-2 | Fam65c | 140876 | 12-May-15 |
| 6443 | 2 | 3 | 4 | | IV-2 | Edem1 | 9695 | 23-May-15 | 7177 | 2 | 3 | 4 | | IV-2 | Fam69a | 388650 | 4-May-15 |
| 6451 | 2 | 3 | 4 | | IV-2 | Edn1a | 1909 | 31-May-15 | 7179 | 2 | 3 | 4 | | IV-2 | Fam69c | 125704 | 4-May-15 |
| 6458 | 2 | 3 | 4 | | IV-2 | Eef1b2 | 1933 | 4-May-15 | 7193 | 2 | 3 | 4 | | IV-2 | Fam78b | 149297 | 4-May-15 |
| 6469 | 2 | 3 | 4 | | IV-2 | Efcab12 | 90288 | 4-May-15 | 7201 | 2 | 3 | 4 | | IV-2 | Fam83g | 644815 | 4-May-15 |
| 6475 | 2 | 3 | 4 | | IV-2 | Efcab5 | 374786 | 4-May-15 | 7207 | 2 | 3 | 4 | | IV-2 | Fam89b | 23625 | 4-May-15 |
| 6478 | 2 | 3 | 4 | | IV-2 | Efcab5 | 388795 | 4-May-15 | 7212 | 2 | 3 | 4 | | IV-2 | Fam98a | 25940 | 4-May-15 |
| 6483 | 2 | 3 | 4 | | IV-2 | Efhb | 151651 | 4-May-15 | 7220 | 2 | 3 | 4 | | IV-2 | Fancd2os | 115795 | 4-May-15 |
| 6487 | 2 | 3 | 4 | | IV-2 | Efhd2 | 79180 | 4-May-15 | 7221 | 2 | 3 | 4 | | IV-2 | Fance | 2178 | 23-May-15 |
| 6491 | 2 | 3 | 4 | | IV-2 | Efna4 | 1945 | 31-May-15 | 7226 | 2 | 3 | 4 | | IV-2 | Fancm | 57697 | 23-May-15 |
| 6493 | 2 | 3 | 4 | | IV-2 | Efna5 | 1946 | 24-May-15 | 7239 | 2 | 3 | 4 | | IV-2 | Fastk | 10922 | 4-May-15 |
| 6498 | 2 | 3 | 4 | | IV-2 | Efs | 10278 | 4-May-15 | 7258 | 2 | 3 | 4 | | IV-2 | Fbln7 | 129804 | 4-May-15 |
| 6503 | 2 | 3 | 4 | | IV-2 | Egfem1 | | | 7259 | 2 | 3 | 4 | | IV-2 | Fbn1 | 2200 | 23-May-15 |
| 6505 | 2 | 3 | 4 | | IV-2 | Egfl7 | 51162 | 4-May-15 | 7260 | 2 | 3 | 4 | | IV-2 | Fbn2 | 2201 | 23-May-15 |
| 6509 | 2 | 3 | 4 | | IV-2 | Egln1 | 54583 | 12-May-15 | 7263 | 2 | 3 | 4 | | IV-2 | Fbrs | 64319 | 12-May-15 |
| 6529 | 2 | 3 | 4 | | IV-2 | Eid2b | 126272 | 4-May-15 | 7270 | 2 | 3 | 4 | | IV-2 | Fbxl16 | 146330 | 4-May-15 |
| 6562 | 2 | 3 | 4 | | IV-2 | Eif3k | 27335 | 12-May-15 | 7273 | 2 | 3 | 4 | | IV-2 | Fbxl19 | 54620 | 4-May-15 |
| 6576 | 2 | 3 | 4 | | IV-2 | Eif4enif1 | 56478 | 4-May-15 | 7275 | 2 | 3 | 4 | | IV-2 | Fbxl20 | 84961 | 1-Jun-15 |
| 6589 | 2 | 3 | 4 | | IV-2 | Elavl1 | 1994 | 2-Jun-15 | 7308 | 2 | 3 | 4 | | IV-2 | Fbxo41 | 150726 | 4-May-15 |
| 6598 | 2 | 3 | 4 | | IV-2 | Elf1 | 392617 | 4-May-15 | 7316 | 2 | 3 | 4 | | IV-2 | Fbxo5 | 26271 | 23-May-15 |
| 6600 | 2 | 3 | 4 | | IV-2 | Elk1 | 2002 | 7-Jun-15 | 7317 | 2 | 3 | 4 | | IV-2 | Fbxo6 | 26270 | 4-May-15 |
| 6603 | 2 | 3 | 4 | | IV-2 | Ell | 8178 | 4-May-15 | 7343 | 2 | 3 | 4 | | IV-2 | Fcer1a | 2205 | 12-May-15 |
| 6606 | 2 | 3 | 4 | | IV-2 | Elmo1 | 9844 | 24-May-15 | 7349 | 2 | 3 | 4 | | IV-2 | Fcgr2b | 2213 | 17-May-15 |
| 6614 | 2 | 3 | 4 | | IV-2 | Elof1 | 84337 | 4-May-15 | 7352 | 2 | 3 | 4 | | IV-2 | Fcgrt | 2217 | 4-May-15 |
| 6621 | 2 | 3 | 4 | | IV-2 | Elovl7 | 79993 | 4-May-15 | 7358 | 2 | 3 | 4 | | IV-2 | Fcnb | | |
| 6641 | 2 | 3 | 4 | | IV-2 | Eme2 | 197342 | 4-May-15 | 7360 | 2 | 3 | 4 | | IV-2 | Fcrls | 83416 | 4-May-15 |
| 6644 | 2 | 3 | 4 | | IV-2 | Emilin1 | 11117 | 4-May-15 | 7363 | 2 | 3 | 4 | | IV-2 | Fcrlb | 127943 | 4-May-15 |
| 6657 | 2 | 3 | 4 | | IV-2 | Emr4 | 326342 | 4-May-15 | 7367 | 2 | 3 | 4 | | IV-2 | Fdx1 | 2230 | 12-May-15 |
| 6666 | 2 | 3 | 4 | | IV-2 | Endod1 | 23052 | 4-May-15 | 7368 | 2 | 3 | 4 | | IV-2 | Fdx1l | 112812 | 4-May-15 |
| 6669 | 2 | 3 | 4 | | IV-2 | Endov | 284131 | 14-May-15 | 7383 | 2 | 3 | 4 | | IV-2 | Fer1l2 | | |
| 6676 | 2 | 3 | 4 | | IV-2 | Eno1b | | | 7393 | 2 | 3 | 4 | | IV-2 | Ffar3 | 2865 | 4-May-15 |
| 6679 | 2 | 3 | 4 | | IV-2 | Eno4 | 387712 | 4-May-15 | 7403 | 2 | 3 | 4 | | IV-2 | Fgf1 | 2246 | 12-May-15 |
| 6690 | 2 | 3 | 4 | | IV-2 | Enpp7 | 339221 | 4-May-15 | 7410 | 2 | 3 | 4 | | IV-2 | Fgf16 | 8823 | 4-May-15 |
| 6702 | 2 | 3 | 4 | | IV-2 | Eny2 | 56943 | 12-May-15 | 7414 | 2 | 3 | 4 | | IV-2 | Fgf20 | 26281 | 4-May-15 |
| 6716 | 2 | 3 | 4 | | IV-2 | Epc1 | 80314 | 7-Jun-15 | 7421 | 2 | 3 | 4 | | IV-2 | Fgf6 | 2251 | 4-May-15 |
| 6726 | 2 | 3 | 4 | | IV-2 | Epha4 | 2043 | 12-May-15 | 7435 | 2 | 3 | 4 | | IV-2 | Fggy | 55277 | 4-May-15 |
| 6733 | 2 | 3 | 4 | | IV-2 | Ephb3 | 2049 | 4-May-15 | 7439 | 2 | 3 | 4 | | IV-2 | Fh1 | 2317 | 23-May-15 |
| 6738 | 2 | 3 | 4 | | IV-2 | Ephx3 | 79852 | 4-May-15 | 7445 | 2 | 3 | 4 | | IV-2 | Fhl2 | 2274 | 31-May-15 |
| 6739 | 2 | 3 | 4 | | IV-2 | Ephx4 | 253152 | 4-May-15 | 7449 | 2 | 3 | 4 | | IV-2 | Fhod1 | 29109 | 4-May-15 |
| 6741 | 2 | 3 | 4 | | IV-2 | Epm2aip1 | 9852 | 4-May-15 | 7460 | 2 | 3 | 4 | | IV-2 | Fignl2 | 401720 | 4-May-15 |
| 6754 | 2 | 3 | 4 | | IV-2 | Eps8l2 | 64787 | 4-May-15 | 7462 | 2 | 3 | 4 | | IV-2 | Filip1l | 11259 | 4-May-15 |

Fig.22 - 12

| | | | | | | | | | | | | | | | |
|---|---|---|---|---|---|---|---|---|---|---|---|---|---|---|---|
| 7467 | 2 | 3 | 4 | | IV-2 | Fitm2 | 128486 | 4-May-15 | 8070 | 2 | 3 | 4 | | IV-2 | Gm10033 |
| 7472 | 2 | 3 | 4 | | IV-2 | Fkbp14 | 56033 | 4-May-15 | 8072 | 2 | 3 | 4 | | IV-2 | Gm10052 |
| 7473 | 2 | 3 | 4 | | IV-2 | Fkbp15 | 23307 | 4-May-15 | 8076 | 2 | 3 | 4 | | IV-2 | Gm10081 |
| 7495 | 2 | 3 | 4 | | IV-2 | Flot1 | 10211 | 31-May-15 | 8081 | 2 | 3 | 4 | | IV-2 | Gm10104 |
| 7500 | 2 | 3 | 4 | | IV-2 | Flt1 | 2321 | 17-May-15 | 8084 | 2 | 3 | 4 | | IV-2 | Gm10147 |
| 7506 | 2 | 3 | 4 | | IV-2 | Fmn1 | 342184 | 12-May-15 | 8089 | 2 | 3 | 4 | | IV-2 | Gm10230 |
| 7509 | 2 | 3 | 4 | | IV-2 | Fmnl2 | 114793 | 4-May-15 | 8093 | 2 | 3 | 4 | | IV-2 | Gm10280 |
| 7514 | 2 | 3 | 4 | | IV-2 | Fmo4 | 2329 | 4-May-15 | 8095 | 2 | 3 | 4 | | IV-2 | Gm10319 |
| 7519 | 2 | 3 | 4 | | IV-2 | Fmr1 | 2332 | 7-Jun-15 | 8096 | 2 | 3 | 4 | | IV-2 | Gm10324 |
| 7520 | 2 | 3 | 4 | | IV-2 | Fmr1nb | 158521 | 4-May-15 | 8098 | 2 | 3 | 4 | | IV-2 | Gm10336 |
| 7529 | 2 | 3 | 4 | | IV-2 | Fndc3a | 22862 | 4-May-15 | 8113 | 2 | 3 | 4 | | IV-2 | Gm10421 |
| 7537 | 2 | 3 | 4 | | IV-2 | Fnip1 | 96459 | 4-May-15 | 8127 | 2 | 3 | 4 | | IV-2 | Gm10488 |
| 7541 | 2 | 3 | 4 | | IV-2 | Focad | 54914 | 4-May-15 | 8128 | 2 | 3 | 4 | | IV-2 | Gm10494 |
| 7545 | 2 | 3 | 4 | | IV-2 | Folr4 | 390243 | 4-May-15 | 8133 | 2 | 3 | 4 | | IV-2 | Gm10532 |
| 7549 | 2 | 3 | 4 | | IV-2 | Fosl1 | 8061 | 17-May-15 | 8143 | 2 | 3 | 4 | | IV-2 | Gm10619 |
| 7564 | 2 | 3 | 4 | | IV-2 | Foxe3 | 2301 | 12-May-15 | 8159 | 2 | 3 | 4 | | IV-2 | Gm10684 |
| 7565 | 2 | 3 | 4 | | IV-2 | Foxf1 | 2294 | 28-May-15 | 8171 | 2 | 3 | 4 | | IV-2 | Gm10789 |
| 7581 | 2 | 3 | 4 | | IV-2 | Foxn1 | 8456 | 4-May-15 | 8179 | 2 | 3 | 4 | | IV-2 | Gm10857 |
| 7584 | 2 | 3 | 4 | | IV-2 | Foxn4 | 121643 | 4-May-15 | 8183 | 2 | 3 | 4 | | IV-2 | Gm10921 |
| 7587 | 2 | 3 | 4 | | IV-2 | Foxo4 | 4303 | 12-May-15 | 8189 | 2 | 3 | 4 | | IV-2 | Gm11128 |
| 7589 | 2 | 3 | 4 | | IV-2 | Foxp1 | 27086 | 2-Jun-15 | 8190 | 2 | 3 | 4 | | IV-2 | Gm11149 |
| 7594 | 2 | 3 | 4 | | IV-2 | Foxr1 | 283150 | 28-May-15 | 8241 | 2 | 3 | 4 | | IV-2 | Gm11944 |
| 7611 | 2 | 3 | 4 | | IV-2 | Frem1 | 158326 | 23-May-15 | 8259 | 2 | 3 | 4 | | IV-2 | Gm12250 |
| 7612 | 2 | 3 | 4 | | IV-2 | Frem2 | 341640 | 4-May-15 | 8268 | 2 | 3 | 4 | | IV-2 | Gm12505 |
| 7635 | 2 | 3 | 4 | | IV-2 | Fsbp | 100861412 | 4-May-15 | 8277 | 2 | 3 | 4 | | IV-2 | Gm12718 |
| 7638 | 2 | 3 | 4 | | IV-2 | Fscn2 | 25794 | 23-May-15 | 8278 | 2 | 3 | 4 | | IV-2 | Gm12789 |
| 7643 | 2 | 3 | 4 | | IV-2 | Fshb | 2488 | 12-May-15 | 8286 | 2 | 3 | 4 | | IV-2 | Gm12992 |
| 7647 | 2 | 3 | 4 | | IV-2 | Fsl1 | 11167 | 4-May-15 | 8289 | 2 | 3 | 4 | | IV-2 | Gm13023 |
| 7648 | 2 | 3 | 4 | | IV-2 | Fstl3 | 10272 | 4-May-15 | 8309 | 2 | 3 | 4 | | IV-2 | Gm13154 |
| 7652 | 2 | 3 | 4 | | IV-2 | Fth1 | 2495 | 24-May-15 | 8314 | 2 | 3 | 4 | | IV-2 | Gm13322 |
| 7672 | 2 | 3 | 4 | | IV-2 | Fut10 | 84750 | 4-May-15 | 8334 | 2 | 3 | 4 | | IV-2 | Gm13305 |
| 7692 | 2 | 3 | 4 | | IV-2 | Fyb | 2533 | 12-May-15 | 8336 | 2 | 3 | 4 | | IV-2 | Gm13308 |
| 7693 | 2 | 3 | 4 | | IV-2 | Fyco1 | 79443 | 21-May-15 | 8337 | 2 | 3 | 4 | | IV-2 | Gm13315 |
| 7701 | 2 | 3 | 4 | | IV-2 | Fzd5 | 7855 | 12-May-15 | 8339 | 2 | 3 | 4 | | IV-2 | Gm13375 |
| 7705 | 2 | 3 | 4 | | IV-2 | Fzd9 | 8326 | 4-May-15 | 8343 | 2 | 3 | 4 | | IV-2 | Gm13497 |
| 7708 | 2 | 3 | 4 | | IV-2 | G2e3 | 55632 | 23-May-15 | 8354 | 2 | 3 | 4 | | IV-2 | Gm13749 |
| 7709 | 2 | 3 | 4 | | IV-2 | G3bp1 | 10146 | 31-May-15 | 8364 | 2 | 3 | 4 | | IV-2 | Gm14015 |
| 7716 | 2 | 3 | 4 | | IV-2 | G630093K05Rik | | | 8368 | 2 | 3 | 4 | | IV-2 | Gm14092 |
| 7718 | 2 | 3 | 4 | | IV-2 | G6bos | | | 8380 | 2 | 3 | 4 | | IV-2 | Gm14306 |
| 7720 | 2 | 3 | 4 | | IV-2 | G6pc2 | 57818 | 4-May-15 | 8400 | 2 | 3 | 4 | | IV-2 | Gm14440 |
| 7746 | 2 | 3 | 4 | | IV-2 | Gabrd | 2563 | 4-May-15 | 8402 | 2 | 3 | 4 | | IV-2 | Gm14458 |
| 7752 | 2 | 3 | 4 | | IV-2 | Gabrq | 55879 | 4-May-15 | 8420 | 2 | 3 | 4 | | IV-2 | Gm14625 |
| 7764 | 2 | 3 | 4 | | IV-2 | Gak | 2580 | 31-May-15 | 8438 | 2 | 3 | 4 | | IV-2 | Gm15008 |
| 7772 | 2 | 3 | 4 | | IV-2 | Galk1 | 2584 | 12-May-15 | 8442 | 2 | 3 | 4 | | IV-2 | Gm15091 |
| 7784 | 2 | 3 | 4 | | IV-2 | Galnt18 | 374378 | 14-May-15 | 8455 | 2 | 3 | 4 | | IV-2 | Gm15292 |
| 7801 | 2 | 3 | 4 | | IV-2 | Ganab | 23193 | 4-May-15 | 8456 | 2 | 3 | 4 | | IV-2 | Gm15293 |
| 7804 | 2 | 3 | 4 | | IV-2 | Gapdh | 2597 | 7-Jun-15 | 8459 | 2 | 3 | 4 | | IV-2 | Gm15315 |
| 7807 | 2 | 3 | 4 | | IV-2 | Gapvd1 | 26130 | 12-May-15 | 8463 | 2 | 3 | 4 | | IV-2 | Gm15350 |
| 7816 | 2 | 3 | 4 | | IV-2 | Gas2l1 | 10634 | 4-May-15 | 8467 | 2 | 3 | 4 | | IV-2 | Gm15412 |
| 7819 | 2 | 3 | 4 | | IV-2 | Gas5 | 60674 | 17-May-15 | 8472 | 2 | 3 | 4 | | IV-2 | Gm15446 |
| 7825 | 2 | 3 | 4 | | IV-2 | Gata2 | 2624 | 28-May-15 | 8481 | 2 | 3 | 4 | | IV-2 | Gm15663 |
| 7834 | 2 | 3 | 4 | | IV-2 | Gatc | 283459 | 23-May-15 | 8498 | 2 | 3 | 4 | | IV-2 | Gm15941 |
| 7836 | 2 | 3 | 4 | | IV-2 | Gatsl2 | 729438 | 14-May-15 | 8500 | 2 | 3 | 4 | | IV-2 | Gm15997 |
| 7838 | 2 | 3 | 4 | | IV-2 | Gba | 2629 | 31-May-15 | 8527 | 2 | 3 | 4 | | IV-2 | Gm16515 |
| 7844 | 2 | 3 | 4 | | IV-2 | Gbp10 | | | 8533 | 2 | 3 | 4 | | IV-2 | Gm16576 |
| 7846 | 2 | 3 | 4 | | IV-2 | Gbp2 | 2634 | 4-May-15 | 8544 | 2 | 3 | 4 | | IV-2 | Gm16740 |
| 7849 | 2 | 3 | 4 | | IV-2 | Gbp4 | 115361 | 4-May-15 | 8578 | 2 | 3 | 4 | | IV-2 | Gm17762 |
| 7850 | 2 | 3 | 4 | | IV-2 | Gbp5 | 115362 | 4-May-15 | 8593 | 2 | 3 | 4 | | IV-2 | Gm19424 |
| 7851 | 2 | 3 | 4 | | IV-2 | Gbp6 | 163351 | 4-May-15 | 8607 | 2 | 3 | 4 | | IV-2 | Gm1968 |
| 7852 | 2 | 3 | 4 | | IV-2 | Gbp7 | 388646 | 4-May-15 | 8617 | 2 | 3 | 4 | | IV-2 | Gm19897 |
| 7854 | 2 | 3 | 4 | | IV-2 | Gbp9 | | | 8618 | 2 | 3 | 4 | | IV-2 | Gm19993 |
| 7855 | 2 | 3 | 4 | | IV-2 | Gbx1 | 2636 | 4-May-15 | 8621 | 2 | 3 | 4 | | IV-2 | Gm2002 |
| 7858 | 2 | 3 | 4 | | IV-2 | Gca | 25801 | 4-May-15 | 8624 | 2 | 3 | 4 | | IV-2 | Gm2011 |
| 7868 | 2 | 3 | 4 | | IV-2 | Gck | 2645 | 7-Jun-15 | 8625 | 2 | 3 | 4 | | IV-2 | Gm20110 |
| 7869 | 2 | 3 | 4 | | IV-2 | Gckr | 2646 | 7-Jun-15 | 8635 | 2 | 3 | 4 | | IV-2 | Gm20268 |
| 7881 | 2 | 3 | 4 | | IV-2 | Gcsh | 2653 | 23-May-15 | 8640 | 2 | 3 | 4 | | IV-2 | Gm20324 |
| 7885 | 2 | 3 | 4 | | IV-2 | Gdap1l1 | 78997 | 4-May-15 | 8642 | 2 | 3 | 4 | | IV-2 | Gm20356 |
| 7890 | 2 | 3 | 4 | | IV-2 | Gdf11 | 10220 | 21-May-15 | 8650 | 2 | 3 | 4 | | IV-2 | Gm20605 |
| 7893 | 2 | 3 | 4 | | IV-2 | Gdf2 | 2658 | 4-May-15 | 8683 | 2 | 3 | 4 | | IV-2 | Gm20831 |
| 7896 | 2 | 3 | 4 | | IV-2 | Gdf7 | 151449 | 4-May-15 | 8696 | 2 | 3 | 4 | | IV-2 | Gm21057 |
| 7898 | 2 | 3 | 4 | | IV-2 | Gdi1 | 2664 | 12-May-15 | 8700 | 2 | 3 | 4 | | IV-2 | Gm21221 |
| 7915 | 2 | 3 | 4 | | IV-2 | Get4 | 51608 | 29-May-15 | 8710 | 2 | 3 | 4 | | IV-2 | Gm21541 |
| 7920 | 2 | 3 | 4 | | IV-2 | Gfm1 | 85476 | 12-May-15 | 8712 | 2 | 3 | 4 | | IV-2 | Gm21637 |
| 7928 | 2 | 3 | 4 | | IV-2 | Gfra3 | 2676 | 4-May-15 | 8731 | 2 | 3 | 4 | | IV-2 | Gm2696 |
| 7936 | 2 | 3 | 4 | | IV-2 | Ggct | 79017 | 4-May-15 | 8732 | 2 | 3 | 4 | | IV-2 | Gm2721 |
| 7937 | 2 | 3 | 4 | | IV-2 | Ggcx | 2677 | 31-May-15 | 8747 | 2 | 3 | 4 | | IV-2 | Gm3139 |
| 7944 | 2 | 3 | 4 | | IV-2 | Ggt5 | 2687 | 4-May-15 | 8752 | 2 | 3 | 4 | | IV-2 | Gm3258 |
| 7949 | 2 | 3 | 4 | | IV-2 | Ghdc | 84914 | 4-May-15 | 8755 | 2 | 3 | 4 | | IV-2 | Gm3279 |
| 7955 | 2 | 3 | 4 | | IV-2 | Ghsr | 2693 | 12-May-15 | 8757 | 2 | 3 | 4 | | IV-2 | Gm3286 |
| 7964 | 2 | 3 | 4 | | IV-2 | Gimap5 | 55340 | 4-May-15 | 8766 | 2 | 3 | 4 | | IV-2 | Gm3417 |
| 7967 | 2 | 3 | 4 | | IV-2 | Gimap8 | 155032 | 4-May-15 | 8775 | 2 | 3 | 4 | | IV-2 | Gm362 |
| 7973 | 2 | 3 | 4 | | IV-2 | Gins3 | 64785 | 4-May-15 | 8782 | 2 | 3 | 4 | | IV-2 | Gm3750 |
| 7985 | 2 | 3 | 4 | | IV-2 | Gja4 | 2701 | 12-May-15 | 8789 | 2 | 3 | 4 | | IV-2 | Gm4027 |
| 7997 | 2 | 3 | 4 | | IV-2 | Gjc3 | 349149 | 20-May-15 | 8791 | 2 | 3 | 4 | | IV-2 | Gm41 |
| 7999 | 2 | 3 | 4 | | IV-2 | Gjd3 | 125111 | 4-May-15 | 8804 | 2 | 3 | 4 | | IV-2 | Gm4297 |
| 8007 | 2 | 3 | 4 | | IV-2 | Gkn3 | | | 8812 | 2 | 3 | 4 | | IV-2 | Gm436 |
| 8008 | 2 | 3 | 4 | | IV-2 | Gla | 2717 | 7-Jun-15 | 8813 | 2 | 3 | 4 | | IV-2 | Gm4371 |
| 8017 | 2 | 3 | 4 | | IV-2 | Gldnos | | | 8819 | 2 | 3 | 4 | | IV-2 | Gm4489 |
| 8020 | 2 | 3 | 4 | | IV-2 | Gli1 | 2735 | 17-May-15 | 8853 | 2 | 3 | 4 | | IV-2 | Gm4894 |
| 8021 | 2 | 3 | 4 | | IV-2 | Gli2 | 2736 | 23-May-15 | 8862 | 2 | 3 | 4 | | IV-2 | Gm4952 |
| 8022 | 2 | 3 | 4 | | IV-2 | Gli3 | 2737 | 31-May-15 | 8864 | 2 | 3 | 4 | | IV-2 | Gm4961 |
| 8024 | 2 | 3 | 4 | | IV-2 | Glipr1l1 | 256710 | 12-May-15 | 8868 | 2 | 3 | 4 | | IV-2 | Gm4981 |
| 8027 | 2 | 3 | 4 | | IV-2 | Glis1 | 148979 | 4-May-15 | 8874 | 2 | 3 | 4 | | IV-2 | Gm5071 |
| 8028 | 2 | 3 | 4 | | IV-2 | Glis2 | 84662 | 28-May-15 | 8887 | 2 | 3 | 4 | | IV-2 | Gm5111 |
| 8030 | 2 | 3 | 4 | | IV-2 | Glmn | 11146 | 4-May-15 | 8897 | 2 | 3 | 4 | | IV-2 | Gm5136 |
| 8054 | 2 | 3 | 4 | | IV-2 | Gltp | 51228 | 12-May-15 | 8906 | 2 | 3 | 4 | | IV-2 | Gm5177 |
| 8066 | 2 | 3 | 4 | | IV-2 | Glyr1 | 84656 | 20-May-15 | 8908 | 2 | 3 | 4 | | IV-2 | Gm527 |

Fig.22 - 13

| | | | | | | | | | | | | | | | |
|---|---|---|---|---|---|---|---|---|---|---|---|---|---|---|---|
| 8911 | 2 | 3 | 4 | | IV-2 | Gm5334 | | | 9692 | 2 | 3 | 4 | | IV-2 | H2-M3 | | |
| 8921 | 2 | 3 | 4 | | IV-2 | Gm5431 | | | 9693 | 2 | 3 | 4 | | IV-2 | H2-M5 | | |
| 8942 | 2 | 3 | 4 | | IV-2 | Gm5577 | | | 9696 | 2 | 3 | 4 | | IV-2 | H2-Ob | | |
| 8952 | 2 | 3 | 4 | | IV-2 | Gm5634 | | | 9697 | 2 | 3 | 4 | | IV-2 | H2-Q1 | | |
| 8965 | 2 | 3 | 4 | | IV-2 | Gm5779 | | | 9699 | 2 | 3 | 4 | | IV-2 | H2-Q2 | | |
| 8966 | 2 | 3 | 4 | | IV-2 | Gm5795 | | | 9700 | 2 | 3 | 4 | | IV-2 | H2-Q4 | | |
| 8975 | 2 | 3 | 4 | | IV-2 | Gm5862 | | | 9702 | 2 | 3 | 4 | | IV-2 | H2-Q6 | | |
| 8983 | 2 | 3 | 4 | | IV-2 | Gm5901 | | | 9703 | 2 | 3 | 4 | | IV-2 | H2-Q7 | | |
| 8999 | 2 | 3 | 4 | | IV-2 | Gm6086 | | | 9706 | 2 | 3 | 4 | | IV-2 | H2-T10 | | |
| 9018 | 2 | 3 | 4 | | IV-2 | Gm6313 | | | 9708 | 2 | 3 | 4 | | IV-2 | H2-T23 | | |
| 9035 | 2 | 3 | 4 | | IV-2 | Gm6537 | | | 9733 | 2 | 3 | 4 | | IV-2 | Hao2 | 51179 | 12-May-15 |
| 9041 | 2 | 3 | 4 | | IV-2 | Gm6583 | | | 9739 | 2 | 3 | 4 | | IV-2 | Harbi1 | 283254 | 4-May-15 |
| 9052 | 2 | 3 | 4 | | IV-2 | Gm6654 | | | 9744 | 2 | 3 | 4 | | IV-2 | Has2os | | |
| 9090 | 2 | 3 | 4 | | IV-2 | Gm7257 | | | 9746 | 2 | 3 | 4 | | IV-2 | Hat1 | 8520 | 17-May-15 |
| 9095 | 2 | 3 | 4 | | IV-2 | Gm7337 | | | 9754 | 2 | 3 | 4 | | IV-2 | Haus8 | 93323 | 4-May-15 |
| 9104 | 2 | 3 | 4 | | IV-2 | Gm7616 | | | 9760 | 2 | 3 | 4 | | IV-2 | Hba-x | | |
| 9112 | 2 | 3 | 4 | | IV-2 | Gm7854 | | | 9763 | 2 | 3 | 4 | | IV-2 | Hbb-bh2 | | |
| 9114 | 2 | 3 | 4 | | IV-2 | Gm7903 | | | 9771 | 2 | 3 | 4 | | IV-2 | Hbs1l | 10767 | 4-May-15 |
| 9127 | 2 | 3 | 4 | | IV-2 | Gm8267 | | | 9774 | 2 | 3 | 4 | | IV-2 | Hcar2 | 338442 | 4-May-15 |
| 9134 | 2 | 3 | 4 | | IV-2 | Gm839 | | | 9775 | 2 | 3 | 4 | | IV-2 | Hccs | 3052 | 23-May-15 |
| 9137 | 2 | 3 | 4 | | IV-2 | Gm8579 | | | 9780 | 2 | 3 | 4 | | IV-2 | Hcls1 | 3059 | 12-May-15 |
| 9142 | 2 | 3 | 4 | | IV-2 | Gm8677 | | | 9781 | 2 | 3 | 4 | | IV-2 | Hcn1 | 348980 | 4-May-15 |
| 9146 | 2 | 3 | 4 | | IV-2 | Gm8773 | | | 9783 | 2 | 3 | 4 | | IV-2 | Hcn3 | 57657 | 12-May-15 |
| 9156 | 2 | 3 | 4 | | IV-2 | Gm8979 | | | 9784 | 2 | 3 | 4 | | IV-2 | Hcn4 | 10021 | 23-May-15 |
| 9158 | 2 | 3 | 4 | | IV-2 | Gm8994 | | | 9789 | 2 | 3 | 4 | | IV-2 | Hdac1 | 3065 | 28-May-15 |
| 9164 | 2 | 3 | 4 | | IV-2 | Gm9079 | | | 9792 | 2 | 3 | 4 | | IV-2 | Hdac2 | 3066 | 28-May-15 |
| 9169 | 2 | 3 | 4 | | IV-2 | Gm9268 | | | 9795 | 2 | 3 | 4 | | IV-2 | Hdac5 | 10014 | 31-May-15 |
| 9171 | 2 | 3 | 4 | | IV-2 | Gm9376 | | | 9799 | 2 | 3 | 4 | | IV-2 | Hdac9 | 9734 | 4-May-15 |
| 9184 | 2 | 3 | 4 | | IV-2 | Gm9839 | | | 9803 | 2 | 3 | 4 | | IV-2 | Hdgf | 3068 | 17-May-15 |
| 9186 | 2 | 3 | 4 | | IV-2 | Gm9866 | | | 9810 | 2 | 3 | 4 | | IV-2 | Hdlbp | 3069 | 12-May-15 |
| 9189 | 2 | 3 | 4 | | IV-2 | Gm9899 | | | 9821 | 2 | 3 | 4 | | IV-2 | Heca | 51696 | 4-May-15 |
| 9210 | 2 | 3 | 4 | | IV-2 | Gnppa | 29826 | 4-May-15 | 9828 | 2 | 3 | 4 | | IV-2 | Helb | 92797 | 4-May-15 |
| 9212 | 2 | 3 | 4 | | IV-2 | Gmpr | 2766 | 12-May-15 | 9830 | 2 | 3 | 4 | | IV-2 | Helq | 113510 | 4-May-15 |
| 9219 | 2 | 3 | 4 | | IV-2 | Gna15 | 2769 | 4-May-15 | 9835 | 2 | 3 | 4 | | IV-2 | Hemk1 | 51409 | 4-May-15 |
| 9225 | 2 | 3 | 4 | | IV-2 | Gnaq | 2776 | 4-May-15 | 9851 | 2 | 3 | 4 | | IV-2 | Hes3 | 390992 | 4-May-15 |
| 9237 | 2 | 3 | 4 | | IV-2 | Gnb5 | 10681 | 4-May-15 | 9866 | 2 | 3 | 4 | | IV-2 | Hfm1 | 164045 | 4-May-15 |
| 9241 | 2 | 3 | 4 | | IV-2 | Gng12 | 55970 | 4-May-15 | 9874 | 2 | 3 | 4 | | IV-2 | Hhex | 3087 | 12-May-15 |
| 9251 | 2 | 3 | 4 | | IV-2 | Gnl1 | 2794 | 12-May-15 | 9875 | 2 | 3 | 4 | | IV-2 | Hhip | 64399 | 12-May-15 |
| 9256 | 2 | 3 | 4 | | IV-2 | Gnpat | 8443 | 12-May-15 | 9876 | 2 | 3 | 4 | | IV-2 | Hhipl1 | 84439 | 14-May-15 |
| 9263 | 2 | 3 | 4 | | IV-2 | Gnrhr | 2798 | 23-May-15 | 9877 | 2 | 3 | 4 | | IV-2 | Hhipl2 | 79802 | 4-May-15 |
| 9272 | 2 | 3 | 4 | | IV-2 | Golgb1 | 2804 | 4-May-15 | 9887 | 2 | 3 | 4 | | IV-2 | Hiflan | 55662 | 4-May-15 |
| 9278 | 2 | 3 | 4 | | IV-2 | Golt1b | 51026 | 4-May-15 | 9891 | 2 | 3 | 4 | | IV-2 | Higd1c | 613227 | 4-May-15 |
| 9287 | 2 | 3 | 4 | | IV-2 | Got1l1 | 137362 | 4-May-15 | 9903 | 2 | 3 | 4 | | IV-2 | Hipk3 | 10114 | 4-May-15 |
| 9290 | 2 | 3 | 4 | | IV-2 | Gp1bb | 2812 | 12-May-15 | 9908 | 2 | 3 | 4 | | IV-2 | Hist1h1b | 3009 | 4-May-15 |
| 9294 | 2 | 3 | 4 | | IV-2 | Gp6 | 51206 | 4-May-15 | 9909 | 2 | 3 | 4 | | IV-2 | Hist1h1c | 3006 | 12-May-15 |
| 9295 | 2 | 3 | 4 | | IV-2 | Gp9 | 2815 | 12-May-15 | 9910 | 2 | 3 | 4 | | IV-2 | Hist1h1d | 3007 | 4-May-15 |
| 9296 | 2 | 3 | 4 | | IV-2 | Gpa33 | 10223 | 12-May-15 | 9911 | 2 | 3 | 4 | | IV-2 | Hist1h1e | 3008 | 12-May-15 |
| 9300 | 2 | 3 | 4 | | IV-2 | Gpank1 | 7918 | 4-May-15 | 9912 | 2 | 3 | 4 | | IV-2 | Hist1h1f | 3010 | 4-May-15 |
| 9324 | 2 | 3 | 4 | | IV-2 | Gphb5 | 122876 | 4-May-15 | 9916 | 2 | 3 | 4 | | IV-2 | Hist1h2ad | 3013 | 4-May-15 |
| 9328 | 2 | 3 | 4 | | IV-2 | Gpkow | 27238 | 4-May-15 | 9917 | 2 | 3 | 4 | | IV-2 | Hist1h2ae | 3012 | 14-May-15 |
| 9338 | 2 | 3 | 4 | | IV-2 | Gpr107 | 57720 | 12-May-15 | 9922 | 2 | 3 | 4 | | IV-2 | Hist1h2ak | 8330 | 4-May-15 |
| 9341 | 2 | 3 | 4 | | IV-2 | Gpr111 | 222811 | 4-May-15 | 9928 | 2 | 3 | 4 | | IV-2 | Hist1h2bc | 8347 | 12-May-15 |
| 9372 | 2 | 3 | 4 | | IV-2 | Gpr156 | 165829 | 12-May-15 | 9931 | 2 | 3 | 4 | | IV-2 | Hist1h2bg | 8339 | 4-May-15 |
| 9380 | 2 | 3 | 4 | | IV-2 | Gpr171 | 29909 | 4-May-15 | 9933 | 2 | 3 | 4 | | IV-2 | Hist1h2bj | 8970 | 4-May-15 |
| 9381 | 2 | 3 | 4 | | IV-2 | Gpr173 | 54328 | 12-May-15 | 9935 | 2 | 3 | 4 | | IV-2 | Hist1h2bf | 8340 | 4-May-15 |
| 9383 | 2 | 3 | 4 | | IV-2 | Gpr176 | 11245 | 4-May-15 | 9938 | 2 | 3 | 4 | | IV-2 | Hist1h2bp | | |
| 9386 | 2 | 3 | 4 | | IV-2 | Gpr180 | 160897 | 31-May-15 | 9939 | 2 | 3 | 4 | | IV-2 | Hist1h2bq | | |
| 9389 | 2 | 3 | 4 | | IV-2 | Gpr19 | 2842 | 4-May-15 | 9940 | 2 | 3 | 4 | | IV-2 | Hist1h3a | 8350 | 4-May-15 |
| 9396 | 2 | 3 | 4 | | IV-2 | Gpr3 | 2827 | 4-May-15 | 9941 | 2 | 3 | 4 | | IV-2 | Hist1h3b | 8358 | 4-May-15 |
| 9409 | 2 | 3 | 4 | | IV-2 | Gpr56 | 9289 | 23-May-15 | 9942 | 2 | 3 | 4 | | IV-2 | Hist1h3c | 8352 | 4-May-15 |
| 9433 | 2 | 3 | 4 | | IV-2 | Gprc6a | 222545 | 4-May-15 | 9944 | 2 | 3 | 4 | | IV-2 | Hist1h3e | 8353 | 4-May-15 |
| 9437 | 2 | 3 | 4 | | IV-2 | Gps1 | 2873 | 4-May-15 | 9945 | 2 | 3 | 4 | | IV-2 | Hist1h3f | 8968 | 4-May-15 |
| 9446 | 2 | 3 | 4 | | IV-2 | Gpx2-ps1 | | | 9948 | 2 | 3 | 4 | | IV-2 | Hist1h3i | 8354 | 4-May-15 |
| 9451 | 2 | 3 | 4 | | IV-2 | Gpx7 | 2882 | 4-May-15 | 9949 | 2 | 3 | 4 | | IV-2 | Hist1h4a | 8359 | 2-Jun-15 |
| 9452 | 2 | 3 | 4 | | IV-2 | Gpx8 | 493869 | 12-May-15 | 9950 | 2 | 3 | 4 | | IV-2 | Hist1h4b | 8366 | 4-May-15 |
| 9453 | 2 | 3 | 4 | | IV-2 | Gramd1a | 57655 | 12-May-15 | 9953 | 2 | 3 | 4 | | IV-2 | Hist1h4f | 8361 | 4-May-15 |
| 9460 | 2 | 3 | 4 | | IV-2 | Grap2 | 9402 | 12-May-15 | 9957 | 2 | 3 | 4 | | IV-2 | Hist1h4k | 8362 | 4-May-15 |
| 9461 | 2 | 3 | 4 | | IV-2 | Grasp | 160622 | 4-May-15 | 9962 | 2 | 3 | 4 | | IV-2 | Hist2h2ab | 317772 | 4-May-15 |
| 9464 | 2 | 3 | 4 | | IV-2 | Grb2 | 2885 | 31-May-15 | 9964 | 2 | 3 | 4 | | IV-2 | Hist2h2bb | 338391 | 4-May-15 |
| 9470 | 2 | 3 | 4 | | IV-2 | Grem2 | 54388 | 4-May-15 | 9970 | 2 | 3 | 4 | | IV-2 | Hist3h2a | 92815 | 4-May-15 |
| 9474 | 2 | 3 | 4 | | IV-2 | Grhpr | 9380 | 31-May-15 | 9972 | 2 | 3 | 4 | | IV-2 | Hist3h2bb-ps | | |
| 9475 | 2 | 3 | 4 | | IV-2 | Gria1 | 2890 | 3-May-15 | 9974 | 2 | 3 | 4 | | IV-2 | Hivep1 | 3096 | 12-May-15 |
| 9478 | 2 | 3 | 4 | | IV-2 | Gria4 | 2893 | 12-May-15 | 9976 | 2 | 3 | 4 | | IV-2 | Hivep3 | 59269 | 4-May-15 |
| 9492 | 2 | 3 | 4 | | IV-2 | Grin2c | 2905 | 4-May-15 | 9982 | 2 | 3 | 4 | | IV-2 | Hkdc1 | 80201 | 4-May-15 |
| 9494 | 2 | 3 | 4 | | IV-2 | Grin3a | 116443 | 4-May-15 | 9991 | 2 | 3 | 4 | | IV-2 | Hmg20a | 10363 | 12-May-15 |
| 9496 | 2 | 3 | 4 | | IV-2 | Grin3b | 116444 | 4-May-15 | 9997 | 2 | 3 | 4 | | IV-2 | Hmgb1 | 3146 | 7-Jun-15 |
| 9521 | 2 | 3 | 4 | | IV-2 | Grwd1 | 83743 | 12-May-15 | 9998 | 2 | 3 | 4 | | IV-2 | Hmgb1-rs17 | | |
| 9534 | 2 | 3 | 4 | | IV-2 | Gsdmcl1 | | | 10007 | 2 | 3 | 4 | | IV-2 | Hmgn1 | 3150 | 4-May-15 |
| 9536 | 2 | 3 | 4 | | IV-2 | Gsdmcl-ps | | | 10009 | 2 | 3 | 4 | | IV-2 | Hmgn3 | 9324 | 4-May-15 |
| 9577 | 2 | 3 | 4 | | IV-2 | Gtf2a1l | 11036 | 4-May-15 | 10010 | 2 | 3 | 4 | | IV-2 | Hmgn5 | 79366 | 4-May-15 |
| 9608 | 2 | 3 | 4 | | IV-2 | Gtsf1 | 121355 | 4-May-15 | 10014 | 2 | 3 | 4 | | IV-2 | Hmmr | 3161 | 23-May-15 |
| 9611 | 2 | 3 | 4 | | IV-2 | Guca1b | 2979 | 31-May-15 | 10030 | 2 | 3 | 4 | | IV-2 | Hnrnpa2b1 | 3181 | 31-May-15 |
| 9612 | 2 | 3 | 4 | | IV-2 | Guca2a | 2980 | 4-May-15 | 10050 | 2 | 3 | 4 | | IV-2 | Homer2 | 9455 | 14-May-15 |
| 9613 | 2 | 3 | 4 | | IV-2 | Guca2b | 2981 | 4-May-15 | 10071 | 2 | 3 | 4 | | IV-2 | Hoxa7 | 3204 | 28-May-15 |
| 9630 | 2 | 3 | 4 | | IV-2 | Gxylt1 | 283464 | 4-May-15 | 10103 | 2 | 3 | 4 | | IV-2 | Hpbp3 | 50809 | 12-May-15 |
| 9637 | 2 | 3 | 4 | | IV-2 | Gypc | 2995 | 12-May-15 | 10105 | 2 | 3 | 4 | | IV-2 | Hpcal1 | 3241 | 21-May-15 |
| 9640 | 2 | 3 | 4 | | IV-2 | Gzf1 | 64412 | 4-May-15 | 10107 | 2 | 3 | 4 | | IV-2 | Hpd | 3242 | 4-May-15 |
| 9653 | 2 | 3 | 4 | | IV-2 | H1f0 | 3005 | 4-May-15 | 10110 | 2 | 3 | 4 | | IV-2 | Hpgds | 27306 | 4-May-15 |
| 9657 | 2 | 3 | 4 | | IV-2 | H2-Aa | | | 10121 | 2 | 3 | 4 | | IV-2 | Hr | 55806 | 12-May-15 |
| 9658 | 2 | 3 | 4 | | IV-2 | H2-Ab1 | | | 10122 | 2 | 3 | 4 | | IV-2 | Hras | 3265 | 2-Jun-15 |
| 9659 | 2 | 3 | 4 | | IV-2 | H2afb1 | 474382 | 4-May-15 | 10128 | 2 | 3 | 4 | | IV-2 | Hrh1 | 3269 | 4-May-15 |
| 9660 | 2 | 3 | 4 | | IV-2 | H2afb2 | 474381 | 4-May-15 | 10144 | 2 | 3 | 4 | | IV-2 | Hs6st1 | 9394 | 14-May-15 |
| 9664 | 2 | 3 | 4 | | IV-2 | H2afk | 3014 | 4-May-15 | 10146 | 2 | 3 | 4 | | IV-2 | Hs6st3 | 266722 | 4-May-15 |
| 9669 | 2 | 3 | 4 | | IV-2 | H2bfm | 286436 | 4-May-15 | 10147 | 2 | 3 | 4 | | IV-2 | Hsbp1 | 3281 | 17-May-15 |
| 9671 | 2 | 3 | 4 | | IV-2 | H2-D1 | | | 10149 | 2 | 3 | 4 | | IV-2 | Hscb | 150274 | 4-May-15 |
| 9675 | 2 | 3 | 4 | | IV-2 | H2-Ea-ps | | | 10151 | 2 | 3 | 4 | | IV-2 | Hsd11b2 | 3291 | 12-May-15 |
| 9678 | 2 | 3 | 4 | | IV-2 | H2-K1 | | | 10152 | 2 | 3 | 4 | | IV-2 | Hsd17b1 | 3292 | 4-May-15 |

Fig.22 - 14

| | | | | | | | | | | | | | | | |
|---|---|---|---|---|---|---|---|---|---|---|---|---|---|---|---|
| 10155 | 2 | 3 | 4 | | IV-2 | Hsd17b12 | 51144 | 4-May-15 | 10885 | 2 | 3 | 4 | IV-2 | Kcnmb4os1 | |
| 10159 | 2 | 3 | 4 | | IV-2 | Hsd17b3 | 3293 | 4-May-15 | 10891 | 2 | 3 | 4 | IV-2 | Kcnq1ot1 | 10984 | 22-May-15 |
| 10165 | 2 | 3 | 4 | | IV-2 | Hsd3b3 | | | 10893 | 2 | 3 | 4 | IV-2 | Kcnq3 | 3786 | 23-May-15 |
| 10166 | 2 | 3 | 4 | | IV-2 | Hsd3b4 | | | 10898 | 2 | 3 | 4 | IV-2 | Kcns2 | 3788 | 4-May-15 |
| 10168 | 2 | 3 | 4 | | IV-2 | Hsd3b6 | | | 10916 | 2 | 3 | 4 | IV-2 | Kctd18 | 130535 | 4-May-15 |
| 10169 | 2 | 3 | 4 | | IV-2 | Hsd3b7 | 80270 | 4-May-15 | 10934 | 2 | 3 | 4 | IV-2 | Kdm1a | 23028 | 10-May-15 |
| 10170 | 2 | 3 | 4 | | IV-2 | Hsdl1 | 83693 | 4-May-15 | 10953 | 2 | 3 | 4 | IV-2 | Kdsr | 2531 | 4-May-15 |
| 10175 | 2 | 3 | 4 | | IV-2 | Hsf3 | | | 10957 | 2 | 3 | 4 | IV-2 | Kera | 11081 | 4-May-15 |
| 10180 | 2 | 3 | 4 | | IV-2 | Hsp90aa1 | 3320 | 17-May-15 | 10970 | 2 | 3 | 4 | IV-2 | Kif12 | 113220 | 4-May-15 |
| 10185 | 2 | 3 | 4 | | IV-2 | Hspa13 | 6782 | 4-May-15 | 10973 | 2 | 3 | 4 | IV-2 | Kif14 | 9928 | 17-May-15 |
| 10191 | 2 | 3 | 4 | | IV-2 | Hspa4 | 3308 | 7-Jun-15 | 10974 | 2 | 3 | 4 | IV-2 | Kif15 | 56992 | 17-May-15 |
| 10202 | 2 | 3 | 4 | | IV-2 | Hspb8 | 26353 | 23-May-15 | 10975 | 2 | 3 | 4 | IV-2 | Kif16b | 55614 | 4-May-15 |
| 10232 | 2 | 3 | 4 | | IV-2 | Hus1 | 3364 | 4-May-15 | 10978 | 2 | 3 | 4 | IV-2 | Kif18b | 146909 | 4-May-15 |
| 10237 | 2 | 3 | 4 | | IV-2 | Hyal2 | 8692 | 31-May-15 | 10979 | 2 | 3 | 4 | IV-2 | Kif19a | 124602 | 4-May-15 |
| 10244 | 2 | 3 | 4 | | IV-2 | Hvkk | 123688 | 4-May-15 | 10985 | 2 | 3 | 4 | IV-2 | Kif21a | 55605 | 23-May-15 |
| 10251 | 2 | 3 | 4 | | IV-2 | I830077J02Rik | | | 10987 | 2 | 3 | 4 | IV-2 | Kif22 | 3835 | 4-May-15 |
| 10264 | 2 | 3 | 4 | | IV-2 | Icam5 | 7087 | 4-May-15 | 10988 | 2 | 3 | 4 | IV-2 | Kif23 | 9493 | 4-May-15 |
| 10281 | 2 | 3 | 4 | | IV-2 | Id2 | 91734 | 12-May-15 | 10989 | 2 | 3 | 4 | IV-2 | Kif24 | 347240 | 4-May-15 |
| 10301 | 2 | 3 | 4 | | IV-2 | If30 | 10437 | 4-May-15 | 10996 | 2 | 3 | 4 | IV-2 | Kif3a | 11127 | 4-May-15 |
| 10304 | 2 | 3 | 4 | | IV-2 | Ifi44l | 10964 | 4-May-15 | 11000 | 2 | 3 | 4 | IV-2 | Kif4-ps | | |
| 10306 | 2 | 3 | 4 | | IV-2 | Ifih1 | 64135 | 17-May-15 | 11002 | 2 | 3 | 4 | IV-2 | Kif5b | 3799 | 4-May-15 |
| 10308 | 2 | 3 | 4 | | IV-2 | Ifit2 | 3433 | 12-May-15 | 11009 | 2 | 3 | 4 | IV-2 | Kifc2 | 90990 | 4-May-15 |
| 10317 | 2 | 3 | 4 | | IV-2 | Ifitd1 | 160492 | 4-May-15 | 11020 | 2 | 3 | 4 | IV-2 | Kiss1r | 84634 | 7-Jun-15 |
| 10364 | 2 | 3 | 4 | | IV-2 | Igf1 | 3479 | 24-May-15 | 11022 | 2 | 3 | 4 | IV-2 | Kit | 4254 | 24-May-15 |
| 10387 | 2 | 3 | 4 | | IV-2 | Igfl1 | 3543 | 12-May-15 | 11031 | 2 | 3 | 4 | IV-2 | Klf10 | 7071 | 3-May-15 |
| 10390 | 2 | 3 | 4 | | IV-2 | Igsf10 | 285313 | 4-May-15 | 11033 | 2 | 3 | 4 | IV-2 | Klf12 | 11278 | 2-Jun-15 |
| 10391 | 2 | 3 | 4 | | IV-2 | Igsf11 | 152404 | 12-May-15 | 11034 | 2 | 3 | 4 | IV-2 | Klf13 | 51621 | 4-May-15 |
| 10399 | 2 | 3 | 4 | | IV-2 | Igsf9b | 22997 | 4-May-15 | 11043 | 2 | 3 | 4 | IV-2 | Klf6 | 1316 | 4-May-15 |
| 10402 | 2 | 3 | 4 | | IV-2 | Ign1 | | | 11045 | 2 | 3 | 4 | IV-2 | Klf8 | 11279 | 4-May-15 |
| 10403 | 2 | 3 | 4 | | IV-2 | Ik | 3550 | 7-Jun-15 | 11053 | 2 | 3 | 4 | IV-2 | Klhdc7b | 113730 | 4-May-15 |
| 10410 | 2 | 3 | 4 | | IV-2 | Ikzf2 | 22807 | 10-May-15 | 11055 | 2 | 3 | 4 | IV-2 | Klhdc8b | 200942 | 4-May-15 |
| 10411 | 2 | 3 | 4 | | IV-2 | Ikzf3 | 22806 | 4-May-15 | 11056 | 2 | 3 | 4 | IV-2 | Klhdc9 | 126823 | 21-May-15 |
| 10412 | 2 | 3 | 4 | | IV-2 | Ikzf4 | 64375 | 4-May-15 | 11060 | 2 | 3 | 4 | IV-2 | Klhl12 | 59349 | 4-May-15 |
| 10416 | 2 | 3 | 4 | | IV-2 | Il10rb | 3588 | 12-May-15 | 11064 | 2 | 3 | 4 | IV-2 | Klhl17 | 339451 | 4-May-15 |
| 10436 | 2 | 3 | 4 | | IV-2 | Il17a | 3605 | 7-Jun-15 | 11079 | 2 | 3 | 4 | IV-2 | Klhl32 | 114792 | 4-May-15 |
| 10441 | 2 | 3 | 4 | | IV-2 | Il18bp | 10068 | 3-May-15 | 11082 | 2 | 3 | 4 | IV-2 | Klhl35 | 283212 | 7-Jun-15 |
| 10447 | 2 | 3 | 4 | | IV-2 | Il1bos | | | 11085 | 2 | 3 | 4 | IV-2 | Klhl4 | 56062 | 4-May-15 |
| 10467 | 2 | 3 | 4 | | IV-2 | Il22 | 50616 | 7-Jun-15 | 11088 | 2 | 3 | 4 | IV-2 | Klhl42 | 57542 | 4-May-15 |
| 10470 | 2 | 3 | 4 | | IV-2 | Il23a | 51561 | 17-May-15 | 11091 | 2 | 3 | 4 | IV-2 | Klhl7 | 55975 | 23-May-15 |
| 10479 | 2 | 3 | 4 | | IV-2 | Il3 | 3562 | 12-May-15 | 11102 | 2 | 3 | 4 | IV-2 | Klk1b11 | | |
| 10483 | 2 | 3 | 4 | | IV-2 | Il34 | 146433 | 4-May-15 | 11109 | 2 | 3 | 4 | IV-2 | Klk1b16 | | |
| 10490 | 2 | 3 | 4 | | IV-2 | Il6 | 3569 | 24-May-15 | 11105 | 2 | 3 | 4 | IV-2 | Klk1b22 | | |
| 10512 | 2 | 3 | 4 | | IV-2 | Impact | 55364 | 12-May-15 | 11112 | 2 | 3 | 4 | IV-2 | Klk1b7-ps | | |
| 10522 | 2 | 3 | 4 | | IV-2 | Inf2 | 64423 | 4-May-15 | 11115 | 2 | 3 | 4 | IV-2 | Klk4 | 9622 | 7-Jun-15 |
| 10531 | 2 | 3 | 4 | | IV-2 | Inhbc | 3626 | 4-May-15 | 11124 | 2 | 3 | 4 | IV-2 | Klra12 | | |
| 10533 | 2 | 3 | 4 | | IV-2 | Inip | 58493 | 4-May-15 | 11126 | 2 | 3 | 4 | IV-2 | Klra14-ps | | |
| 10535 | 2 | 3 | 4 | | IV-2 | Ino80 | 54811 | 4-May-15 | 11130 | 2 | 3 | 4 | IV-2 | Klra19 | | |
| 10547 | 2 | 3 | 4 | | IV-2 | Inpp5e | 56623 | 23-May-15 | 11132 | 2 | 3 | 4 | IV-2 | Klra21 | | |
| 10550 | 2 | 3 | 4 | | IV-2 | Inpp5k | 51763 | 4-May-15 | 11135 | 2 | 3 | 4 | IV-2 | Klra3 | | |
| 10553 | 2 | 3 | 4 | | IV-2 | Ins2 | | | 11136 | 2 | 3 | 4 | IV-2 | Klra33 | | |
| 10556 | 2 | 3 | 4 | | IV-2 | Insig2 | 51141 | 4-May-15 | 11143 | 2 | 3 | 4 | IV-2 | Klrb1 | 3820 | 4-May-15 |
| 10560 | 2 | 3 | 4 | | IV-2 | Insm1 | 3642 | 4-May-15 | 11153 | 2 | 3 | 4 | IV-2 | Klre1 | | |
| 10562 | 2 | 3 | 4 | | IV-2 | Insr | 3643 | 17-May-15 | 11154 | 2 | 3 | 4 | IV-2 | Klrg1 | 10219 | 4-May-15 |
| 10603 | 2 | 3 | 4 | | IV-2 | Iqch | 84799 | 7-Jun-15 | 11156 | 2 | 3 | 4 | IV-2 | Klri1 | | |
| 10609 | 2 | 3 | 4 | | IV-2 | Iqsec1 | 9922 | 12-May-15 | 11160 | 2 | 3 | 4 | IV-2 | Kmt2a | 4297 | 31-May-15 |
| 10615 | 2 | 3 | 4 | | IV-2 | Irak2 | 3656 | 4-May-15 | 11171 | 2 | 3 | 4 | IV-2 | Kntc1 | 9735 | 14-May-15 |
| 10626 | 2 | 3 | 4 | | IV-2 | Irf5 | 3663 | 24-May-15 | 11172 | 2 | 3 | 4 | IV-2 | Kpna1 | 3836 | 12-May-15 |
| 10629 | 2 | 3 | 4 | | IV-2 | Irf8 | 3394 | 24-May-15 | 11207 | 2 | 3 | 4 | IV-2 | Krt28 | 162605 | 4-May-15 |
| 10638 | 2 | 3 | 4 | | IV-2 | Irs3 | | | 11208 | 2 | 3 | 4 | IV-2 | Krt31 | 3881 | 4-May-15 |
| 10655 | 2 | 3 | 4 | | IV-2 | Isl1r2 | 57611 | 4-May-15 | 11209 | 2 | 3 | 4 | IV-2 | Krt32 | 3882 | 4-May-15 |
| 10661 | 2 | 3 | 4 | | IV-2 | Ispd | 729920 | 7-Jun-15 | 11211 | 2 | 3 | 4 | IV-2 | Krt33b | 3884 | 12-May-15 |
| 10680 | 2 | 3 | 4 | | IV-2 | Itga8 | 8516 | 4-May-15 | 11213 | 2 | 3 | 4 | IV-2 | Krt35 | 3886 | 4-May-15 |
| 10688 | 2 | 3 | 4 | | IV-2 | Itgb1 | 3888 | 31-May-15 | 11214 | 2 | 3 | 4 | IV-2 | Krt36 | 8689 | 4-May-15 |
| 10692 | 2 | 3 | 4 | | IV-2 | Itgb2l | | | 11225 | 2 | 3 | 4 | IV-2 | Krt73 | 319101 | 28-May-15 |
| 10698 | 2 | 3 | 4 | | IV-2 | Itgb7 | 3695 | 12-May-15 | 11235 | 2 | 3 | 4 | IV-2 | Krt82 | 3888 | 4-May-15 |
| 10701 | 2 | 3 | 4 | | IV-2 | Itih1 | 3697 | 4-May-15 | 11236 | 2 | 3 | 4 | IV-2 | Krt83 | 3889 | 4-May-15 |
| 10703 | 2 | 3 | 4 | | IV-2 | Itih3 | 3699 | 4-May-15 | 11237 | 2 | 3 | 4 | IV-2 | Krt84 | 3890 | 4-May-15 |
| 10706 | 2 | 3 | 4 | | IV-2 | Itk | 3702 | 24-May-15 | 11240 | 2 | 3 | 4 | IV-2 | Krt9 | 3857 | 4-May-15 |
| 10708 | 2 | 3 | 4 | | IV-2 | Itm2a | 9452 | 4-May-15 | 11241 | 2 | 3 | 4 | IV-2 | Krtap10-10 | 353333 | 4-May-15 |
| 10709 | 2 | 3 | 4 | | IV-2 | Itm2b | 9445 | 3-May-15 | 11242 | 2 | 3 | 4 | IV-2 | Krtap10-4 | 386672 | 4-May-15 |
| 10743 | 2 | 3 | 4 | | IV-2 | Jakmip2 | 9832 | 4-May-15 | 11244 | 2 | 3 | 4 | IV-2 | Krtap12-1 | 353332 | 4-May-15 |
| 10762 | 2 | 3 | 4 | | IV-2 | Jph3 | 57338 | 23-May-15 | 11245 | 2 | 3 | 4 | IV-2 | Krtap13 | 81860 | 4-May-15 |
| 10764 | 2 | 3 | 4 | | IV-2 | Jpx | 554203 | 22-May-15 | 11253 | 2 | 3 | 4 | IV-2 | Krtap16-3 | | |
| 10768 | 2 | 3 | 4 | | IV-2 | Jtb | 10899 | 4-May-15 | 11254 | 2 | 3 | 4 | IV-2 | Krtap17-1 | 83902 | 4-May-15 |
| 10784 | 2 | 3 | 4 | | IV-2 | Kars | 3735 | 4-May-15 | 11255 | 2 | 3 | 4 | IV-2 | Krtap19-1 | 337882 | 4-May-15 |
| 10796 | 2 | 3 | 4 | | IV-2 | Katnb11 | 79768 | 4-May-15 | 11257 | 2 | 3 | 4 | IV-2 | Krtap19-4 | 337971 | 4-May-15 |
| 10798 | 2 | 3 | 4 | | IV-2 | Kazn | 23254 | 2-Jun-15 | 11258 | 2 | 3 | 4 | IV-2 | Krtap19-5 | 337972 | 12-May-15 |
| 10812 | 2 | 3 | 4 | | IV-2 | Kcna4 | 3739 | 12-May-15 | 11260 | 2 | 3 | 4 | IV-2 | Krtap20-2 | 337976 | 4-May-15 |
| 10816 | 2 | 3 | 4 | | IV-2 | Kcnab1 | 7881 | 12-May-15 | 11261 | 2 | 3 | 4 | IV-2 | Krtap21-1 | 337977 | 4-May-15 |
| 10820 | 2 | 3 | 4 | | IV-2 | Kcnb2 | 9312 | 4-May-15 | 11264 | 2 | 3 | 4 | IV-2 | Krtap24-1 | 643803 | 4-May-15 |
| 10822 | 2 | 3 | 4 | | IV-2 | Kcnc2 | 3747 | 31-May-15 | 11268 | 2 | 3 | 4 | IV-2 | Krtap31-1 | | |
| 10828 | 2 | 3 | 4 | | IV-2 | Kcnd3os | | | 11281 | 2 | 3 | 4 | IV-2 | Krtap5-2 | 440021 | 4-May-15 |
| 10830 | 2 | 3 | 4 | | IV-2 | Kcne1l | 23830 | 4-May-15 | 11282 | 2 | 3 | 4 | IV-2 | Krtap5-3 | 387266 | 4-May-15 |
| 10831 | 2 | 3 | 4 | | IV-2 | Kcne2 | 9992 | 23-May-15 | 11284 | 2 | 3 | 4 | IV-2 | Krtap5-5 | 439915 | 4-May-15 |
| 10833 | 2 | 3 | 4 | | IV-2 | Kcne4 | 23704 | 4-May-15 | 11285 | 2 | 3 | 4 | IV-2 | Krtap6-1 | 337966 | 4-May-15 |
| 10836 | 2 | 3 | 4 | | IV-2 | Kcng2 | 26251 | 12-May-15 | 11292 | 2 | 3 | 4 | IV-2 | Krtap9-5 | 81870 | 4-May-15 |
| 10840 | 2 | 3 | 4 | | IV-2 | Kcnh2 | 3757 | 23-May-15 | 11293 | 2 | 3 | 4 | IV-2 | Krtcap2 | 200185 | 4-May-15 |
| 10846 | 2 | 3 | 4 | | IV-2 | Kcnh8 | 131096 | 4-May-15 | 11307 | 2 | 3 | 4 | IV-2 | L3mbtl1 | 26013 | 4-May-15 |
| 10856 | 2 | 3 | 4 | | IV-2 | Kcnj14 | 3770 | 4-May-15 | 11311 | 2 | 3 | 4 | IV-2 | l7Rn6 | 51501 | 4-May-15 |
| 10860 | 2 | 3 | 4 | | IV-2 | Kcnj3 | 3760 | 4-May-15 | 11319 | 2 | 3 | 4 | IV-2 | Lage3 | 8270 | 4-May-15 |
| 10861 | 2 | 3 | 4 | | IV-2 | Kcnj4 | 3761 | 4-May-15 | 11324 | 2 | 3 | 4 | IV-2 | Lama3 | 3909 | 7-Jun-15 |
| 10863 | 2 | 3 | 4 | | IV-2 | Kcnj6 | 3763 | 12-May-15 | 11333 | 2 | 3 | 4 | IV-2 | Lamp1 | 3916 | 29-May-15 |
| 10865 | 2 | 3 | 4 | | IV-2 | Kcnj9 | 3765 | 12-May-15 | 11350 | 2 | 3 | 4 | IV-2 | Large | 9215 | 23-May-15 |
| 10868 | 2 | 3 | 4 | | IV-2 | Kcnk12 | 56660 | 4-May-15 | 11359 | 2 | 3 | 4 | IV-2 | Las1l | 81887 | 4-May-15 |
| 10872 | 2 | 3 | 4 | | IV-2 | Kcnk18 | 338567 | 4-May-15 | 11363 | 2 | 3 | 4 | IV-2 | Lats1 | 9113 | 24-May-15 |
| 10875 | 2 | 3 | 4 | | IV-2 | Kcnk4 | 50801 | 12-May-15 | 11366 | 2 | 3 | 4 | IV-2 | Layn | 143903 | 4-May-15 |
| 10880 | 2 | 3 | 4 | | IV-2 | Kcnma1 | 3778 | 14-May-15 | 11397 | 2 | 3 | 4 | IV-2 | Lclat1 | 253558 | 12-May-15 |

Fig.22 - 15

| | | | | | | | | | | | | | | |
|---|---|---|---|---|---|---|---|---|---|---|---|---|---|---|
| 11404 | 2 | 3 | 4 | | IV-2 | Lcn3 | | | 12162 | 2 | 3 | 4 | IV-2 | Mcpt8 | | |
| 11412 | 2 | 3 | 4 | | IV-2 | Lcp1 | 3936 | 7-Jun-15 | 12176 | 2 | 3 | 4 | IV-2 | Mdga2 | 161357 | 4-May-15 |
| 11413 | 2 | 3 | 4 | | IV-2 | Lcp2 | 3937 | 4-May-15 | 12181 | 2 | 3 | 4 | IV-2 | Mdm1 | 56890 | 12-May-15 |
| 11415 | 2 | 3 | 4 | | IV-2 | Lctl | 197021 | 4-May-15 | 12184 | 2 | 3 | 4 | IV-2 | Mdn1 | 23195 | 21-May-15 |
| 11416 | 2 | 3 | 4 | | IV-2 | Ldb1 | 8861 | 7-Jun-15 | 12188 | 2 | 3 | 4 | IV-2 | Me3 | 10873 | 12-May-15 |
| 11419 | 2 | 3 | 4 | | IV-2 | Ldha | 3939 | 17-May-15 | 12209 | 2 | 3 | 4 | IV-2 | Med22 | 6837 | 28-May-15 |
| 11429 | 2 | 3 | 4 | | IV-2 | Ldlrap1 | 26119 | 12-May-15 | 12215 | 2 | 3 | 4 | IV-2 | Med28 | 80306 | 4-May-15 |
| 11434 | 2 | 3 | 4 | | IV-2 | Lect2 | 3950 | 17-May-15 | 12225 | 2 | 3 | 4 | IV-2 | Medag | 84935 | 4-May-15 |
| 11460 | 2 | 3 | 4 | | IV-2 | Lgals1 | 3956 | 24-May-15 | 12232 | 2 | 3 | 4 | IV-2 | Megf10 | 84466 | 7-Jun-15 |
| 11464 | 2 | 3 | 4 | | IV-2 | Lgals3bp | 3959 | 12-May-15 | 12237 | 2 | 3 | 4 | IV-2 | Mei1 | 150365 | 12-May-15 |
| 11485 | 2 | 3 | 4 | | IV-2 | Lhfpl3 | 375612 | 4-May-15 | 12240 | 2 | 3 | 4 | IV-2 | Meiob | 254528 | 4-May-15 |
| 11488 | 2 | 3 | 4 | | IV-2 | Lhpp | 64077 | 7-Jun-15 | 12245 | 2 | 3 | 4 | IV-2 | Memo1 | 51072 | 7-Jun-15 |
| 11500 | 2 | 3 | 4 | | IV-2 | Lifr | 3977 | 12-May-15 | 12248 | 2 | 3 | 4 | IV-2 | Meox2 | 4223 | 10-May-15 |
| 11501 | 2 | 3 | 4 | | IV-2 | Lig1 | 3978 | 7-Jun-15 | 12249 | 2 | 3 | 4 | IV-2 | Mep1a | 4224 | 12-May-15 |
| 11505 | 2 | 3 | 4 | | IV-2 | Lilra6 | 79168 | 20-May-15 | 12259 | 2 | 3 | 4 | IV-2 | Met | 4233 | 7-Jun-15 |
| 11512 | 2 | 3 | 4 | | IV-2 | Lime1 | 54923 | 4-May-15 | 12268 | 2 | 3 | 4 | IV-2 | Mettl13 | 51603 | 23-May-15 |
| 11524 | 2 | 3 | 4 | | IV-2 | Lin7c | 55327 | 4-May-15 | 12278 | 2 | 3 | 4 | IV-2 | Mettl21e | | |
| 11543 | 2 | 3 | 4 | | IV-2 | Lipt1 | 51601 | 13-May-15 | 12282 | 2 | 3 | 4 | IV-2 | Mettl25 | 84190 | 4-May-15 |
| 11554 | 2 | 3 | 4 | | IV-2 | Lman2 | 10960 | 4-May-15 | 12292 | 2 | 3 | 4 | IV-2 | Mettl8 | 79828 | 4-May-15 |
| 11564 | 2 | 3 | 4 | | IV-2 | Lmna | 4000 | 24-May-15 | 12295 | 2 | 3 | 4 | IV-2 | Mex3b | 84206 | 4-May-15 |
| 11566 | 2 | 3 | 4 | | IV-2 | Lmnb2 | 84823 | 4-May-15 | 12301 | 2 | 3 | 4 | IV-2 | Mfap3 | 4238 | 4-May-15 |
| 11575 | 2 | 3 | 4 | | IV-2 | Lmtk2 | 22853 | 12-May-15 | 12305 | 2 | 3 | 4 | IV-2 | Mff | 56947 | 4-May-15 |
| 11584 | 2 | 3 | 4 | | IV-2 | LOC100040786 | | | 12307 | 2 | 3 | 4 | IV-2 | Mfhas1 | 9258 | 4-May-15 |
| 11587 | 2 | 3 | 4 | | IV-2 | LOC100502896 | | | 12319 | 2 | 3 | 4 | IV-2 | Mfsd3 | 113655 | 4-May-15 |
| 11594 | 2 | 3 | 4 | | IV-2 | LOC100505025 | | | 12321 | 2 | 3 | 4 | IV-2 | Mfsd5 | 84975 | 4-May-15 |
| 11597 | 2 | 3 | 4 | | IV-2 | LOC100862015 | | | 12335 | 2 | 3 | 4 | IV-2 | Mgat4a | 11320 | 4-May-15 |
| 11609 | 2 | 3 | 4 | | IV-2 | LOC102632423 | | | 12351 | 2 | 3 | 4 | IV-2 | Mia2 | 117153 | 7-Jun-15 |
| 11627 | 2 | 3 | 4 | | IV-2 | Lonrf2 | 164832 | 12-May-15 | 12355 | 2 | 3 | 4 | IV-2 | Mib2 | 142678 | 4-May-15 |
| 11631 | 2 | 3 | 4 | | IV-2 | Loxhd1 | 125336 | 23-May-15 | 12362 | 2 | 3 | 4 | IV-2 | Micu1 | 10367 | 4-May-15 |
| 11634 | 2 | 3 | 4 | | IV-2 | Loxl3 | 84695 | 23-May-15 | 12413 | 2 | 3 | 4 | IV-2 | Mir1224 | 100187716 | 21-May-15 |
| 11636 | 2 | 3 | 4 | | IV-2 | Lpar1 | 1902 | 4-May-15 | 12435 | 2 | 3 | 4 | IV-2 | Mir1298 | 100302153 | 4-May-15 |
| 11639 | 2 | 3 | 4 | | IV-2 | Lpar4 | 2846 | 4-May-15 | 12459 | 2 | 3 | 4 | IV-2 | Mir143 | 406935 | 21-May-15 |
| 11648 | 2 | 3 | 4 | | IV-2 | Lphn1 | 22859 | 4-May-15 | 12480 | 2 | 3 | 4 | IV-2 | Mir17 | 406952 | 24-May-15 |
| 11652 | 2 | 3 | 4 | | IV-2 | Lpin2 | 9663 | 23-May-15 | 12533 | 2 | 3 | 4 | IV-2 | Mir1941 | 406969 | 21-May-15 |
| 11656 | 2 | 3 | 4 | | IV-2 | Lpp | 4026 | 12-May-15 | 12554 | 2 | 3 | 4 | IV-2 | Mir1958 | | |
| 11658 | 2 | 3 | 4 | | IV-2 | Lrat | 9227 | 23-May-15 | 12605 | 2 | 3 | 4 | IV-2 | Mir216a | 406998 | 21-May-15 |
| 11679 | 2 | 3 | 4 | | IV-2 | Lrmp | 4033 | 4-May-15 | 12828 | 2 | 3 | 4 | IV-2 | Mir434 | | |
| 11695 | 2 | 3 | 4 | | IV-2 | Lrrc1 | 55227 | 4-May-15 | 12877 | 2 | 3 | 4 | IV-2 | Mir487b | 664616 | 21-May-15 |
| 11697 | 2 | 3 | 4 | | IV-2 | Lrrc10b | 390205 | 4-May-15 | 12936 | 2 | 3 | 4 | IV-2 | Mir547 | | |
| 11700 | 2 | 3 | 4 | | IV-2 | Lrrc15 | 131578 | 4-May-15 | 12962 | 2 | 3 | 4 | IV-2 | Mir6237 | | |
| 11707 | 2 | 3 | 4 | | IV-2 | Lrrc20 | 55222 | 4-May-15 | 12967 | 2 | 3 | 4 | IV-2 | Mir6335 | | |
| 11708 | 2 | 3 | 4 | | IV-2 | Lrrc23 | 10233 | 4-May-15 | 12971 | 2 | 3 | 4 | IV-2 | Mir6339 | | |
| 11712 | 2 | 3 | 4 | | IV-2 | Lrrc27 | 80313 | 5-Jun-15 | 12973 | 2 | 3 | 4 | IV-2 | Mir6341 | | |
| 11713 | 2 | 3 | 4 | | IV-2 | Lrrc28 | 123355 | 4-May-15 | 12987 | 2 | 3 | 4 | IV-2 | Mir6358 | | |
| 11717 | 2 | 3 | 4 | | IV-2 | Lrrc32 | 2615 | 20-May-15 | 12990 | 2 | 3 | 4 | IV-2 | Mir6361 | | |
| 11718 | 2 | 3 | 4 | | IV-2 | Lrrc34 | 151827 | 4-May-15 | 12993 | 2 | 3 | 4 | IV-2 | Mir6364 | | |
| 11723 | 2 | 3 | 4 | | IV-2 | Lrrc4 | 64101 | 12-May-15 | 13019 | 2 | 3 | 4 | IV-2 | Mir6393 | | |
| 11724 | 2 | 3 | 4 | | IV-2 | Lrrc40 | 55631 | 4-May-15 | 13030 | 2 | 3 | 4 | IV-2 | Mir6404 | | |
| 11737 | 2 | 3 | 4 | | IV-2 | Lrrc55 | 219527 | 4-May-15 | 13049 | 2 | 3 | 4 | IV-2 | Mir653 | 724023 | 21-May-15 |
| 11754 | 2 | 3 | 4 | | IV-2 | Lrrc8a | 56262 | 1-Jun-15 | 13126 | 2 | 3 | 4 | IV-2 | Mir6920 | | |
| 11756 | 2 | 3 | 4 | | IV-2 | Lrrc8c | 84230 | 12-May-15 | 13195 | 2 | 3 | 4 | IV-2 | Mir6982 | | |
| 11770 | 2 | 3 | 4 | | IV-2 | Lrrn2 | 10446 | 4-May-15 | 13247 | 2 | 3 | 4 | IV-2 | Mir7030 | | |
| 11771 | 2 | 3 | 4 | | IV-2 | Lrrn3 | 54674 | 4-May-15 | 13282 | 2 | 3 | 4 | IV-2 | Mir7061 | | |
| 11780 | 2 | 3 | 4 | | IV-2 | Lrrtm2 | 654429 | 4-May-15 | 13331 | 2 | 3 | 4 | IV-2 | Mir7-2 | 407044 | 21-May-15 |
| 11792 | 2 | 3 | 4 | | IV-2 | Lsm4 | 25804 | 28-May-15 | 13332 | 2 | 3 | 4 | IV-2 | Mir721 | | |
| 11794 | 2 | 3 | 4 | | IV-2 | Lsm6 | 11157 | 4-May-15 | 13376 | 2 | 3 | 4 | IV-2 | Mir761 | 100313892 | 5-May-15 |
| 11798 | 2 | 3 | 4 | | IV-2 | Lsp1 | 4046 | 4-May-15 | 13422 | 2 | 3 | 4 | IV-2 | Mir8092 | | |
| 11802 | 2 | 3 | 4 | | IV-2 | Lta | 4049 | 12-May-15 | 13425 | 2 | 3 | 4 | IV-2 | Mir8095 | | |
| 11803 | 2 | 3 | 4 | | IV-2 | Lta4h | 4048 | 12-May-15 | 13430 | 2 | 3 | 4 | IV-2 | Mir8100 | | |
| 11806 | 2 | 3 | 4 | | IV-2 | Ltb4r2 | 56413 | 4-May-15 | 13435 | 2 | 3 | 4 | IV-2 | Mir8105 | | |
| 11807 | 2 | 3 | 4 | | IV-2 | Ltbp1 | 4052 | 12-May-15 | 13443 | 2 | 3 | 4 | IV-2 | Mir8113 | | |
| 11814 | 2 | 3 | 4 | | IV-2 | Ltk | 4058 | 4-May-15 | 13445 | 2 | 3 | 4 | IV-2 | Mir8115 | | |
| 11831 | 2 | 3 | 4 | | IV-2 | Ly6e | 4061 | 4-May-15 | 13476 | 2 | 3 | 4 | IV-2 | Mirg | | |
| 11837 | 2 | 3 | 4 | | IV-2 | Ly6g6e | 79136 | 4-May-15 | 13477 | 2 | 3 | 4 | IV-2 | Mirlet7a-1 | | |
| 11839 | 2 | 3 | 4 | | IV-2 | Ly6h | 4062 | 4-May-15 | 13484 | 2 | 3 | 4 | IV-2 | Mirlet7e | 406887 | 21-May-15 |
| 11840 | 2 | 3 | 4 | | IV-2 | Ly6i | | | 13494 | 2 | 3 | 4 | IV-2 | Misp | 126353 | 4-May-15 |
| 11842 | 2 | 3 | 4 | | IV-2 | Ly75 | 4065 | 31-May-15 | 13499 | 2 | 3 | 4 | IV-2 | Mkks | 8195 | 23-May-15 |
| 11846 | 2 | 3 | 4 | | IV-2 | Lyar | 55646 | 4-May-15 | 13501 | 2 | 3 | 4 | IV-2 | Mkl2 | 57496 | 21-May-15 |
| 11849 | 2 | 3 | 4 | | IV-2 | Lvl1 | 4066 | 12-May-15 | 13512 | 2 | 3 | 4 | IV-2 | Mki1 | 23209 | 31-May-15 |
| 11850 | 2 | 3 | 4 | | IV-2 | Lyn | 4067 | 12-May-15 | 13515 | 2 | 3 | 4 | IV-2 | Mlf2 | 8079 | 4-May-15 |
| 11864 | 2 | 3 | 4 | | IV-2 | Lyrm2 | 57226 | 4-May-15 | 13531 | 2 | 3 | 4 | IV-2 | Mlycd | 23417 | 4-May-15 |
| 11868 | 2 | 3 | 4 | | IV-2 | Lyrm7os | | | 13554 | 2 | 3 | 4 | IV-2 | Mmp20 | 9313 | 4-May-15 |
| 11876 | 2 | 3 | 4 | | IV-2 | Lyzl1 | 84569 | 4-May-15 | 13557 | 2 | 3 | 4 | IV-2 | Mmp24 | 10893 | 4-May-15 |
| 11886 | 2 | 3 | 4 | | IV-2 | Lzts2 | 84445 | 4-May-15 | 13558 | 2 | 3 | 4 | IV-2 | Mmp25 | 64386 | 7-Jun-15 |
| 11893 | 2 | 3 | 4 | | IV-2 | Mab21l3 | 126868 | 4-May-15 | 13576 | 2 | 3 | 4 | IV-2 | Mnt | 4335 | 12-May-15 |
| 11897 | 2 | 3 | 4 | | IV-2 | Macrod2 | 140733 | 3-May-15 | 13579 | 2 | 3 | 4 | IV-2 | Mob1a | 55233 | 4-May-15 |
| 11900 | 2 | 3 | 4 | | IV-2 | Mad2l1bp | 9587 | 4-May-15 | 13581 | 2 | 3 | 4 | IV-2 | Mob2 | 81532 | 4-May-15 |
| 11940 | 2 | 3 | 4 | | IV-2 | Magoh | 4116 | 7-Jun-15 | 13591 | 2 | 3 | 4 | IV-2 | Mog | 4340 | 21-May-15 |
| 11942 | 2 | 3 | 4 | | IV-2 | Magt1 | 84061 | 23-May-15 | 13594 | 2 | 3 | 4 | IV-2 | Mogs | 7841 | 23-May-15 |
| 11948 | 2 | 3 | 4 | | IV-2 | Mall | 7851 | 4-May-15 | 13608 | 2 | 3 | 4 | IV-2 | Morn3 | 283385 | 4-May-15 |
| 11949 | 2 | 3 | 4 | | IV-2 | Malsu1 | 115416 | 12-May-15 | 13619 | 2 | 3 | 4 | IV-2 | Moxd2 | 100289017 | 4-May-15 |
| 11957 | 2 | 3 | 4 | | IV-2 | Mamstr | 284358 | 4-May-15 | 13632 | 2 | 3 | 4 | IV-2 | Mpkip | 136647 | 7-Jun-15 |
| 11980 | 2 | 3 | 4 | | IV-2 | Map1b | 4131 | 4-May-15 | 13635 | 2 | 3 | 4 | IV-2 | Mpp1 | 4354 | 7-Jun-15 |
| 11981 | 2 | 3 | 4 | | IV-2 | Map1lc3a | 84557 | 21-May-15 | 13639 | 2 | 3 | 4 | IV-2 | Mpp5 | 64398 | 12-May-15 |
| 11992 | 2 | 3 | 4 | | IV-2 | Map2k7 | 5609 | 7-Jun-15 | 13643 | 2 | 3 | 4 | IV-2 | Mpped1 | 758 | 4-May-15 |
| 12008 | 2 | 3 | 4 | | IV-2 | Map3k8 | 1326 | 4-May-15 | 13644 | 2 | 3 | 4 | IV-2 | Mpped2 | 744 | 4-May-15 |
| 12037 | 2 | 3 | 4 | | IV-2 | Mapk8ip2 | 23542 | 7-Jun-15 | 13649 | 2 | 3 | 4 | IV-2 | Mpv17 | 4358 | 23-May-15 |
| 12052 | 2 | 3 | 4 | | IV-2 | March10 | 162333 | 4-May-15 | 13651 | 2 | 3 | 4 | IV-2 | Mpv17l2 | 84769 | 4-May-15 |
| 12063 | 2 | 3 | 4 | | IV-2 | Marcksl1 | 65108 | 4-May-15 | 13656 | 2 | 3 | 4 | IV-2 | Mr1 | 3140 | 7-Jun-15 |
| 12078 | 2 | 3 | 4 | | IV-2 | Masp2 | 10747 | 12-May-15 | 13662 | 2 | 3 | 4 | IV-2 | Mre11a | 4361 | 12-May-15 |
| 12085 | 2 | 3 | 4 | | IV-2 | Mat2a | 4144 | 12-May-15 | 13664 | 2 | 3 | 4 | IV-2 | Mrfap1 | 93621 | 4-May-15 |
| 12088 | 2 | 3 | 4 | | IV-2 | Matn1 | 4146 | 4-May-15 | 13712 | 2 | 3 | 4 | IV-2 | Mrpl22 | 29093 | 7-Jun-15 |
| 12092 | 2 | 3 | 4 | | IV-2 | Matr3 | 9782 | 10-May-15 | 13756 | 2 | 3 | 4 | IV-2 | Mrps2 | 51116 | 28-May-15 |
| 12098 | 2 | 3 | 4 | | IV-2 | Mb21d1 | 115004 | 4-May-15 | 13780 | 2 | 3 | 4 | IV-2 | Ms4a10 | 341116 | 4-May-15 |
| 12144 | 2 | 3 | 4 | | IV-2 | Mcm2 | 4171 | 7-Jun-15 | 13787 | 2 | 3 | 4 | IV-2 | Ms4a4c | | |
| 12145 | 2 | 3 | 4 | | IV-2 | Mcm3 | 4172 | 4-May-15 | | | | | | | | |
| 12149 | 2 | 3 | 4 | | IV-2 | Mcm6 | 4175 | 4-May-15 | | | | | | | | |

Fig.22 - 16

| | | | | | | | | | | | | | | |
|---|---|---|---|---|---|---|---|---|---|---|---|---|---|---|
| 13788 | 2 | 3 | 4 | | IV-2 | Ms4a4d | | | 14445 | 2 | 3 | 4 | IV-2 | Nlrp14 | 338323 | 4-May-15 |
| 13800 | 2 | 3 | 4 | | IV-2 | Msgn1 | 343930 | 28-May-15 | 14460 | 2 | 3 | 4 | IV-2 | Nlrp9a | | |
| 13807 | 2 | 3 | 4 | | IV-2 | Msi2 | 124540 | 17-May-15 | 14465 | 2 | 3 | 4 | IV-2 | Nmbr | 4829 | 4-May-15 |
| 13813 | 2 | 3 | 4 | | IV-2 | Mslnl | 401827 | 4-May-15 | 14470 | 2 | 3 | 4 | IV-2 | Nme4 | 4833 | 4-May-15 |
| 13822 | 2 | 3 | 4 | | IV-2 | Msrb3 | 253827 | 4-May-15 | 14472 | 2 | 3 | 4 | IV-2 | Nme6 | 10201 | 21-May-15 |
| 13824 | 2 | 3 | 4 | | IV-2 | Mst1 | 4485 | 16-Jun-15 | 14474 | 2 | 3 | 4 | IV-2 | Nme8 | 51314 | 28-May-15 |
| 13827 | 2 | 3 | 4 | | IV-2 | Msto1 | 55154 | 4-May-15 | 14478 | 2 | 3 | 4 | IV-2 | Nmnat2 | 23057 | 4-May-15 |
| 13829 | 2 | 3 | 4 | | IV-2 | Msx1os | | | 14483 | 2 | 3 | 4 | IV-2 | Nms | 129521 | 4-May-15 |
| 13831 | 2 | 3 | 4 | | IV-2 | Msx3 | | | 14491 | 2 | 3 | 4 | IV-2 | Nnt | 23530 | 13-May-15 |
| 13836 | 2 | 3 | 4 | | IV-2 | Mta1 | 9112 | 17-May-15 | 14502 | 2 | 3 | 4 | IV-2 | Nol10 | 79954 | 4-May-15 |
| 13853 | 2 | 3 | 4 | | IV-2 | Mrf1 | 4520 | 7-Jun-15 | 14525 | 2 | 3 | 4 | IV-2 | Nos3 | 4846 | 7-Jun-15 |
| 13860 | 2 | 3 | 4 | | IV-2 | Mtg1 | 92170 | 4-May-15 | 14535 | 2 | 3 | 4 | IV-2 | Nova1 | 4857 | 4-May-15 |
| 13883 | 2 | 3 | 4 | | IV-2 | Mtmr9 | 66036 | 4-May-15 | 14545 | 2 | 3 | 4 | IV-2 | Npas3 | 64067 | 28-May-15 |
| 13907 | 2 | 3 | 4 | | IV-2 | Muc2 | 4583 | 4-May-15 | 14547 | 2 | 3 | 4 | IV-2 | Npat | 4863 | 4-May-15 |
| 13910 | 2 | 3 | 4 | | IV-2 | Muc5ac | 4586 | 7-Jun-15 | 14554 | 2 | 3 | 4 | IV-2 | Npdc1 | 56654 | 4-May-15 |
| 13915 | 2 | 3 | 4 | | IV-2 | Mug2 | | | 14571 | 2 | 3 | 4 | IV-2 | Npm3-ps1 | | |
| 13941 | 2 | 3 | 4 | | IV-2 | Mus81 | 80198 | 17-May-15 | 14578 | 2 | 3 | 4 | IV-2 | Npr3 | 4883 | Jun-2015 |
| 13944 | 2 | 3 | 4 | | IV-2 | Mut | 4594 | 23-May-15 | 14579 | 2 | 3 | 4 | IV-2 | Nprl2 | 10641 | 29-May-15 |
| 13946 | 2 | 3 | 4 | | IV-2 | Mvb12a | 93343 | 4-May-15 | 14587 | 2 | 3 | 4 | IV-2 | Npvf | 64111 | 4-May-15 |
| 13952 | 2 | 3 | 4 | | IV-2 | Mx2 | 4600 | 12-May-15 | 14590 | 2 | 3 | 4 | IV-2 | Npy1r | 4886 | 4-May-15 |
| 13955 | 2 | 3 | 4 | | IV-2 | Mxd4 | 10608 | 4-May-15 | 14600 | 2 | 3 | 4 | IV-2 | Nr1d2 | 9975 | 4-May-15 |
| 13962 | 2 | 3 | 4 | | IV-2 | Mybbp1a | 10514 | 4-May-15 | 14609 | 2 | 3 | 4 | IV-2 | Nr2c2ap | 126382 | 4-May-15 |
| 13967 | 2 | 3 | 4 | | IV-2 | Mybpc3 | 4607 | 23-May-15 | 14625 | 2 | 3 | 4 | IV-2 | Nrarp | 441478 | 12-May-15 |
| 13971 | 2 | 3 | 4 | | IV-2 | Mycbp | 26292 | 4-May-15 | 14626 | 2 | 3 | 4 | IV-2 | Nras | 4893 | 24-May-15 |
| 13975 | 2 | 3 | 4 | | IV-2 | Mycn | 4613 | 23-May-15 | 14634 | 2 | 3 | 4 | IV-2 | Nrf1 | 4899 | 7-Jun-15 |
| 13976 | 2 | 3 | 4 | | IV-2 | Mycs | | | 14642 | 2 | 3 | 4 | IV-2 | Nrip2 | 83714 | 4-May-15 |
| 13978 | 2 | 3 | 4 | | IV-2 | Myd88 | 4615 | 4-May-15 | 14643 | 2 | 3 | 4 | IV-2 | Nrip3 | 56675 | 4-May-15 |
| 13983 | 2 | 3 | 4 | | IV-2 | Myg1 | 80314 | 4-May-15 | 14649 | 2 | 3 | 4 | IV-2 | Nron | 641373 | 4-May-15 |
| 13988 | 2 | 3 | 4 | | IV-2 | Myh14 | 79784 | 7-Jun-15 | 14654 | 2 | 3 | 4 | IV-2 | Nrsn1 | 140767 | 12-May-15 |
| 13991 | 2 | 3 | 4 | | IV-2 | Myh3 | 4621 | 12-May-15 | 14663 | 2 | 3 | 4 | IV-2 | Nsf | 4905 | 28-May-15 |
| 13993 | 2 | 3 | 4 | | IV-2 | Myh6 | 4624 | 23-May-15 | 14667 | 2 | 3 | 4 | IV-2 | Nsl1 | 25936 | 7-Jun-15 |
| 13995 | 2 | 3 | 4 | | IV-2 | Myh7b | 57644 | 4-May-15 | 14668 | 2 | 3 | 4 | IV-2 | Nsmaf | 8439 | 4-May-15 |
| 13997 | 2 | 3 | 4 | | IV-2 | Myh9 | 4627 | 23-May-15 | 14681 | 2 | 3 | 4 | IV-2 | Nt5c1b | 93034 | 4-May-15 |
| 13999 | 2 | 3 | 4 | | IV-2 | Myl10 | 93408 | 4-May-15 | 14689 | 2 | 3 | 4 | IV-2 | Nt5m | 56953 | 4-May-15 |
| 14004 | 2 | 3 | 4 | | IV-2 | Myl4 | 4635 | 12-May-15 | 14697 | 2 | 3 | 4 | IV-2 | Ntn3 | 4917 | 12-May-15 |
| 14005 | 2 | 3 | 4 | | IV-2 | Myl6 | 4637 | 4-May-15 | 14702 | 2 | 3 | 4 | IV-2 | Ntpcr | 84284 | 12-May-15 |
| 14007 | 2 | 3 | 4 | | IV-2 | Myl7 | 58498 | 4-May-15 | 14705 | 2 | 3 | 4 | IV-2 | Ntrk3 | 4916 | 12-May-15 |
| 14012 | 2 | 3 | 4 | | IV-2 | Mylk3 | 91807 | 12-May-15 | 14718 | 2 | 3 | 4 | IV-2 | Nudc | 10726 | 4-May-15 |
| 14015 | 2 | 3 | 4 | | IV-2 | Myom | 55892 | 12-May-15 | 14732 | 2 | 3 | 4 | IV-2 | Nudt18 | 79873 | 4-May-15 |
| 14021 | 2 | 3 | 4 | | IV-2 | Myo19 | 80179 | 12-May-15 | 14734 | 2 | 3 | 4 | IV-2 | Nudt2 | 318 | 12-May-15 |
| 14028 | 2 | 3 | 4 | | IV-2 | Myo1g | 64005 | 12-May-15 | 14735 | 2 | 3 | 4 | IV-2 | Nudt21 | 11051 | 4-May-15 |
| 14029 | 2 | 3 | 4 | | IV-2 | Myo1h | 283446 | 4-May-15 | 14742 | 2 | 3 | 4 | IV-2 | Nudt8 | 254552 | 4-May-15 |
| 14034 | 2 | 3 | 4 | | IV-2 | Myo5c | 55930 | 4-May-15 | 14743 | 2 | 3 | 4 | IV-2 | Nudt9 | 53343 | 4-May-15 |
| 14053 | 2 | 3 | 4 | | IV-2 | Myopop | 339344 | 4-May-15 | 14745 | 2 | 3 | 4 | IV-2 | Nufip1 | 26747 | 4-May-15 |
| 14062 | 2 | 3 | 4 | | IV-2 | Mzf1 | 7593 | 7-Jun-15 | 14748 | 2 | 3 | 4 | IV-2 | Numa1 | 4926 | 21-May-15 |
| 14068 | 2 | 3 | 4 | | IV-2 | N4bp2l1 | 90634 | 4-May-15 | 14763 | 2 | 3 | 4 | IV-2 | Nup43 | 348995 | 4-May-15 |
| 14087 | 2 | 3 | 4 | | IV-2 | Naaladl1 | 10004 | 4-May-15 | 14777 | 2 | 3 | 4 | IV-2 | Nus1 | 116150 | 28-May-15 |
| 14110 | 2 | 3 | 4 | | IV-2 | Naip6 | | | 14779 | 2 | 3 | 4 | IV-2 | Nutf2 | 10204 | 12-May-15 |
| 14112 | 2 | 3 | 4 | | IV-2 | Nalcn | 259232 | 17-May-15 | 14781 | 2 | 3 | 4 | IV-2 | Nutm1 | 256646 | 4-May-15 |
| 14125 | 2 | 3 | 4 | | IV-2 | Napa | 8775 | 7-Jun-15 | 14794 | 2 | 3 | 4 | IV-2 | Nxpe4 | 54827 | 4-May-15 |
| 14131 | 2 | 3 | 4 | | IV-2 | Narf | 26502 | n-2015 | 14796 | 2 | 3 | 4 | IV-2 | Nxph1 | 30010 | 4-May-15 |
| 14145 | 2 | 3 | 4 | | IV-2 | Nat9 | 26151 | 20-May-15 | 14800 | 2 | 3 | 4 | IV-2 | Nxt1 | 29107 | 4-May-15 |
| 14161 | 2 | 3 | 4 | | IV-2 | Ncapd3 | 23310 | 4-May-15 | 14805 | 2 | 3 | 4 | IV-2 | Nxx | 60506 | 23-May-15 |
| 14163 | 2 | 3 | 4 | | IV-2 | Ncapg2 | 54892 | 4-May-15 | 14806 | 2 | 3 | 4 | IV-2 | Oacyl | | |
| 14164 | 2 | 3 | 4 | | IV-2 | Ncaph | 23397 | 12-May-15 | 14808 | 2 | 3 | 4 | IV-2 | Oard1 | 221443 | 4-May-15 |
| 14165 | 2 | 3 | 4 | | IV-2 | Ncaph2 | 29781 | 4-May-15 | 14816 | 2 | 3 | 4 | IV-2 | Oas1h | | |
| 14169 | 2 | 3 | 4 | | IV-2 | Ncdn | 23154 | 12-May-15 | 14818 | 2 | 3 | 4 | IV-2 | Oas3 | 4940 | 10-May-15 |
| 14174 | 2 | 3 | 4 | | IV-2 | Nck1 | 4690 | 1-Jun-15 | 14819 | 2 | 3 | 4 | IV-2 | Oasl1 | | |
| 14178 | 2 | 3 | 4 | | IV-2 | Nckap5 | 344148 | 4-May-15 | 14820 | 2 | 3 | 4 | IV-2 | Oasl2 | | |
| 14194 | 2 | 3 | 4 | | IV-2 | Ncs1 | 23413 | 12-May-15 | 14821 | 2 | 3 | 4 | IV-2 | Oat | 4942 | 12-May-15 |
| 14197 | 2 | 3 | 4 | | IV-2 | Ndc1 | 55706 | 4-May-15 | 14822 | 2 | 3 | 4 | IV-2 | Oaz1 | 4946 | 12-May-15 |
| 14199 | 2 | 3 | 4 | | IV-2 | Nde1 | 54820 | 4-May-15 | 14824 | 2 | 3 | 4 | IV-2 | Oaz2 | 4947 | 4-May-15 |
| 14208 | 2 | 3 | 4 | | IV-2 | Ndrg1 | 10397 | 23-May-15 | 14826 | 2 | 3 | 4 | IV-2 | Obfc1 | 79991 | 12-May-15 |
| 14212 | 2 | 3 | 4 | | IV-2 | Ndst1 | 3340 | 4-May-15 | 14837 | 2 | 3 | 4 | IV-2 | Oc90 | 729330 | 4-May-15 |
| 14223 | 2 | 3 | 4 | | IV-2 | Ndufa6 | 4697 | 7-Jun-15 | 14853 | 2 | 3 | 4 | IV-2 | Odf3l1 | 161753 | 4-May-15 |
| 14225 | 2 | 3 | 4 | | IV-2 | Ndufa8 | 4698 | 12-May-15 | 14869 | 2 | 3 | 4 | IV-2 | Ol1 | 131177 | 4-May-15 |
| 14234 | 2 | 3 | 4 | | IV-2 | Ndufaf4 | 29078 | 4-May-15 | 14875 | 2 | 3 | 4 | IV-2 | Olfm3 | 118427 | 4-May-15 |
| 14263 | 2 | 3 | 4 | | IV-2 | Nebl | 10529 | 4-May-15 | 14876 | 2 | 3 | 4 | IV-2 | Olfm4 | 10562 | 4-May-15 |
| 14264 | 2 | 3 | 4 | | IV-2 | Necab1 | 64168 | 4-May-15 | 14879 | 2 | 3 | 4 | IV-2 | Olfml2b | 25903 | 4-May-15 |
| 14265 | 2 | 3 | 4 | | IV-2 | Necab2 | 54550 | 12-May-15 | 14880 | 2 | 3 | 4 | IV-2 | Olfml3 | 56944 | 4-May-15 |
| 14281 | 2 | 3 | 4 | | IV-2 | Nek1 | 4750 | 4-May-15 | 14881 | 2 | 3 | 4 | IV-2 | Olfr1 | 4991 | 4-May-15 |
| 14282 | 2 | 3 | 4 | | IV-2 | Nek10 | 152110 | 12-May-15 | 15225 | 2 | 3 | 4 | IV-2 | Olfr140 | | |
| 14285 | 2 | 3 | 4 | | IV-2 | Nek3 | 4752 | 4-May-15 | 15330 | 2 | 3 | 4 | IV-2 | Olfr166 | | |
| 14286 | 2 | 3 | 4 | | IV-2 | Nek4 | 6787 | 4-May-15 | 15380 | 2 | 3 | 4 | IV-2 | Olfr225 | | |
| 14287 | 2 | 3 | 4 | | IV-2 | Nek5 | 341676 | 4-May-15 | 15631 | 2 | 3 | 4 | IV-2 | Olfr555 | | |
| 14299 | 2 | 3 | 4 | | IV-2 | Nemf | 9147 | 12-May-15 | 15635 | 2 | 3 | 4 | IV-2 | Olfr559 | | |
| 14303 | 2 | 3 | 4 | | IV-2 | Nes | 10763 | 17-May-15 | 15982 | 2 | 3 | 4 | IV-2 | Olfr980 | | |
| 14304 | 2 | 3 | 4 | | IV-2 | Nespas | 149715 | 12-May-15 | 15999 | 2 | 3 | 4 | IV-2 | Olig2 | 10215 | 17-May-15 |
| 14308 | 2 | 3 | 4 | | IV-2 | Neu1 | 4758 | 7-Jun-15 | 16001 | 2 | 3 | 4 | IV-2 | Olr1 | 4973 | 12-May-15 |
| 14313 | 2 | 3 | 4 | | IV-2 | Neurl1b | 54492 | 21-May-15 | 16004 | 2 | 3 | 4 | IV-2 | Omg | 4974 | 4-May-15 |
| 14315 | 2 | 3 | 4 | | IV-2 | Neurl3 | 93082 | 7-Jun-15 | 16006 | 2 | 3 | 4 | IV-2 | Omt2a | | |
| 14323 | 2 | 3 | 4 | | IV-2 | Neurog3 | 50674 | 28-May-15 | 16009 | 2 | 3 | 4 | IV-2 | Onecut2 | 9480 | 28-May-15 |
| 14325 | 2 | 3 | 4 | | IV-2 | Nf1 | 4763 | 23-May-15 | 16038 | 2 | 3 | 4 | IV-2 | Orai3 | 93129 | 4-May-15 |
| 14328 | 2 | 3 | 4 | | IV-2 | Nfasc | 23114 | 4-May-15 | 16041 | 2 | 3 | 4 | IV-2 | Orc2 | 4999 | 7-Jun-15 |
| 14329 | 2 | 3 | 4 | | IV-2 | Nfat5 | 10725 | 12-May-15 | 16047 | 2 | 3 | 4 | IV-2 | Ormdl1 | 5095 | 3-May-15 |
| 14343 | 2 | 3 | 4 | | IV-2 | Nfix | 4784 | 4-May-15 | 16049 | 2 | 3 | 4 | IV-2 | Ormdl1 | 94101 | 4-May-15 |
| 14350 | 2 | 3 | 4 | | IV-2 | Nfkbil1 | 4795 | 12-May-15 | 16071 | 2 | 3 | 4 | IV-2 | Osgin2 | 734 | 4-May-15 |
| 14368 | 2 | 3 | 4 | | IV-2 | Ngrn | 51335 | 4-May-15 | 16076 | 2 | 3 | 4 | IV-2 | Ost4 | 100128731 | 4-May-15 |
| 14370 | 2 | 3 | 4 | | IV-2 | Nhlh1 | 4807 | 28-May-15 | 16081 | 2 | 3 | 4 | IV-2 | Otc | 5009 | 23-May-15 |
| 14373 | 2 | 3 | 4 | | IV-2 | Nhlrc2 | 374354 | 4-May-15 | 16088 | 2 | 3 | 4 | IV-2 | Otop2 | 92736 | 4-May-15 |
| 14376 | 2 | 3 | 4 | | IV-2 | Nhp2 | 55651 | 31-May-15 | 16114 | 2 | 3 | 4 | IV-2 | Ovol3 | 728361 | 28-May-15 |
| 14377 | 2 | 3 | 4 | | IV-2 | Nhp2l1 | 4809 | 2-Jun-15 | 16133 | 2 | 3 | 4 | IV-2 | P2rx7 | 5027 | 17-May-15 |
| 14384 | 2 | 3 | 4 | | IV-2 | Nif3l1 | 60491 | 3-May-15 | 16135 | 2 | 3 | 4 | IV-2 | P2ry10 | 27334 | 4-May-15 |
| 14390 | 2 | 3 | 4 | | IV-2 | Ninl | 22981 | 4-May-15 | 16136 | 2 | 3 | 4 | IV-2 | P2ry12 | 64805 | 17-May-15 |
| 14402 | 2 | 3 | 4 | | IV-2 | Nisch | 11188 | 17-May-15 | 16137 | 2 | 3 | 4 | IV-2 | P2ry13 | 53829 | 21-May-15 |
| 14430 | 2 | 3 | 4 | | IV-2 | Nkx3-2 | 579 | 4-May-15 | 16138 | 2 | 3 | 4 | IV-2 | P2ry14 | 9934 | 4-May-15 |
| 14433 | 2 | 3 | 4 | | IV-2 | Nkx6-3 | 157848 | 4-May-15 | 16142 | 2 | 3 | 4 | IV-2 | P4ha1 | 5033 | 12-May-15 |

Fig.22 - 17

| | | | | | | | | | | | | | | | |
|---|---|---|---|---|---|---|---|---|---|---|---|---|---|---|---|
| 16173 | 2 | 3 | 4 | | IV-2 | Pafah2 | 5051 | 4-May-15 | 17089 | 2 | 3 | 4 | IV-2 | Por | 5447 | 7-Jun-15 |
| 16177 | 2 | 3 | 4 | | IV-2 | Paics | 10606 | 4-May-15 | 17092 | 2 | 3 | 4 | IV-2 | Por1a | | |
| 16182 | 2 | 3 | 4 | | IV-2 | Pak1ip1 | 55003 | 4-May-15 | 17097 | 2 | 3 | 4 | IV-2 | Pou2f1 | 5451 | 28-May-15 |
| 16185 | 2 | 3 | 4 | | IV-2 | Pak4 | 10298 | 4-May-15 | 17124 | 2 | 3 | 4 | IV-2 | Ppard | 5467 | 17-May-15 |
| 16191 | 2 | 3 | 4 | | IV-2 | Palm | 5064 | 12-May-15 | 17130 | 2 | 3 | 4 | IV-2 | Ppcdc | 80490 | 12-May-15 |
| 16195 | 2 | 3 | 4 | | IV-2 | Pam | 5066 | 13-Jun-15 | 17132 | 2 | 3 | 4 | IV-2 | Ppdpf | 79144 | 12-May-15 |
| 16213 | 2 | 3 | 4 | | IV-2 | Papola | 10914 | 3-Jun-15 | 17145 | 2 | 3 | 4 | IV-2 | Ppid | 5481 | 17-May-15 |
| 16220 | 2 | 3 | 4 | | IV-2 | Paqr3 | 152559 | 4-May-15 | 17152 | 2 | 3 | 4 | IV-2 | Ppil2 | 23759 | 12-May-15 |
| 16221 | 2 | 3 | 4 | | IV-2 | Paqr4 | 124222 | 4-May-15 | 17159 | 2 | 3 | 4 | IV-2 | Ppm1a | 5494 | 4-May-15 |
| 16225 | 2 | 3 | 4 | | IV-2 | Paqr8 | 85315 | 4-May-15 | 17163 | 2 | 3 | 4 | IV-2 | Ppm1f | 9647 | 4-May-15 |
| 16237 | 2 | 3 | 4 | | IV-2 | Parn | 5073 | 4-Jun-15 | 17177 | 2 | 3 | 4 | IV-2 | Ppp1r11 | 6992 | 12-May-15 |
| 16251 | 2 | 3 | 4 | | IV-2 | Pars2 | 25973 | 4-May-15 | 17180 | 2 | 3 | 4 | IV-2 | Ppp1r12c | 54776 | 4-May-15 |
| 16254 | 2 | 3 | 4 | | IV-2 | Parvg | 64098 | 12-May-15 | 17184 | 2 | 3 | 4 | IV-2 | Ppp1r14b | 26472 | 4-May-15 |
| 16255 | 2 | 3 | 4 | | IV-2 | Pask | 23178 | 7-Jun-15 | 17186 | 2 | 3 | 4 | IV-2 | Ppp1r14d | 54866 | 4-May-15 |
| 16268 | 2 | 3 | 4 | | IV-2 | Pax6 | 5080 | 23-May-15 | 17195 | 2 | 3 | 4 | IV-2 | Ppp1r1c | 151242 | 12-May-15 |
| 16288 | 2 | 3 | 4 | | IV-2 | Pcbd2 | 84105 | 4-May-15 | 17203 | 2 | 3 | 4 | IV-2 | Ppp1r32 | 220004 | 4-May-15 |
| 16296 | 2 | 3 | 4 | | IV-2 | Pcdh10 | 57575 | 4-May-15 | 17212 | 2 | 3 | 4 | IV-2 | Ppp1r3f | 89801 | 4-May-15 |
| 16299 | 2 | 3 | 4 | | IV-2 | Pcdh15 | 65217 | 23-May-15 | 17218 | 2 | 3 | 4 | IV-2 | Ppp1r9a | 55607 | 12-May-15 |
| 16302 | 2 | 3 | 4 | | IV-2 | Pcdh19 | 57526 | 7-Jun-15 | 17263 | 2 | 3 | 4 | IV-2 | Pradc1 | 84279 | 4-May-15 |
| 16348 | 2 | 3 | 4 | | IV-2 | Pcdhga2 | 56113 | 4-May-15 | 17268 | 2 | 3 | 4 | IV-2 | Pramef17 | 391004 | 4-May-15 |
| 16396 | 2 | 3 | 4 | | IV-2 | Pcsk1n | 27344 | 4-May-15 | 17280 | 2 | 3 | 4 | IV-2 | Prc1 | 9055 | 4-May-15 |
| 16401 | 2 | 3 | 4 | | IV-2 | Pcsk5 | 5125 | 12-May-15 | 17281 | 2 | 3 | 4 | IV-2 | Prcc | 5546 | 4-May-15 |
| 16434 | 2 | 3 | 4 | | IV-2 | Pde1c | 5137 | 4-May-15 | 17294 | 2 | 3 | 4 | IV-2 | Prdm6 | 93166 | 12-May-15 |
| 16435 | 2 | 3 | 4 | | IV-2 | Pde2a | 5138 | 21-May-15 | 17308 | 2 | 3 | 4 | IV-2 | Prep | 5550 | 7-Jun-15 |
| 16443 | 2 | 3 | 4 | | IV-2 | Pde5a | 8654 | 4-May-15 | 17313 | 2 | 3 | 4 | IV-2 | Prg2 | 5553 | 7-Jun-15 |
| 16445 | 2 | 3 | 4 | | IV-2 | Pde6b | 5158 | 23-May-15 | 17324 | 2 | 3 | 4 | IV-2 | Primpol | 201973 | 23-May-15 |
| 16463 | 2 | 3 | 4 | | IV-2 | Pdha1 | 5160 | 21-May-15 | 17327 | 2 | 3 | 4 | IV-2 | Prkab1 | 5564 | 2-Jun-15 |
| 16468 | 2 | 3 | 4 | | IV-2 | Pdia3 | 2923 | 4-May-15 | 17329 | 2 | 3 | 4 | IV-2 | Prkaca | 5566 | 7-Jun-15 |
| 16481 | 2 | 3 | 4 | | IV-2 | Pdlim4 | 8572 | 4-May-15 | 17335 | 2 | 3 | 4 | IV-2 | Prkar1a | 5573 | 23-May-15 |
| 16482 | 2 | 3 | 4 | | IV-2 | Pdlim5 | 10611 | 12-May-15 | 17339 | 2 | 3 | 4 | IV-2 | Prkca | 5578 | 31-May-15 |
| 16489 | 2 | 3 | 4 | | IV-2 | Pdrg1 | 81572 | 12-May-15 | 17341 | 2 | 3 | 4 | IV-2 | Prkcd | 5580 | 17-May-15 |
| 16493 | 2 | 3 | 4 | | IV-2 | Pdss2 | 57107 | 31-May-15 | 17361 | 2 | 3 | 4 | IV-2 | Prl2a1 | | |
| 16509 | 2 | 3 | 4 | | IV-2 | Pdzrn3 | 23024 | 12-May-15 | 17403 | 2 | 3 | 4 | IV-2 | Prnp | 5621 | 23-May-15 |
| 16525 | 2 | 3 | 4 | | IV-2 | Peli1 | 57162 | 12-May-15 | 17405 | 2 | 3 | 4 | IV-2 | Proc | 5624 | 31-May-15 |
| 16532 | 2 | 3 | 4 | | IV-2 | Peo1 | 56652 | 23-May-15 | 17411 | 2 | 3 | 4 | IV-2 | Prok2 | 60675 | 23-May-15 |
| 16563 | 2 | 3 | 4 | | IV-2 | Pfas | 5198 | 21-May-15 | 17413 | 2 | 3 | 4 | IV-2 | Prokr2 | 128674 | 23-May-15 |
| 16571 | 2 | 3 | 4 | | IV-2 | Pfkfb4 | 5210 | 12-May-15 | 17424 | 2 | 3 | 4 | IV-2 | Prox2 | 283571 | 4-May-15 |
| 16574 | 2 | 3 | 4 | | IV-2 | Pfkp | 5214 | 4-May-15 | 17443 | 2 | 3 | 4 | IV-2 | Prps1 | 5631 | 7-Jun-15 |
| 16578 | 2 | 3 | 4 | | IV-2 | Pfn4 | 375189 | 4-May-15 | 17447 | 2 | 3 | 4 | IV-2 | Prpsap1 | 5635 | 21-May-15 |
| 16581 | 2 | 3 | 4 | | IV-2 | Pgam1 | 5223 | 7-Jun-15 | 17450 | 2 | 3 | 4 | IV-2 | Prr12 | 57479 | 4-May-15 |
| 16583 | 2 | 3 | 4 | | IV-2 | Pgam5 | 192111 | 24-May-15 | 17467 | 2 | 3 | 4 | IV-2 | Prr5 | 55615 | 4-May-15 |
| 16590 | 2 | 3 | 4 | | IV-2 | Pgd | 5226 | 7-Jun-15 | 17469 | 2 | 3 | 4 | IV-2 | Prr7 | 80758 | 4-May-15 |
| 16593 | 2 | 3 | 4 | | IV-2 | Pgk1 | 5230 | 12-May-15 | 17470 | 2 | 3 | 4 | IV-2 | Prr9 | 574414 | 4-May-15 |
| 16595 | 2 | 3 | 4 | | IV-2 | Pgls | 25796 | 4-May-15 | 17485 | 2 | 3 | 4 | IV-2 | Prrx1 | 644168 | 4-May-15 |
| 16597 | 2 | 3 | 4 | | IV-2 | Pglyrp2 | 114770 | 4-May-15 | 17490 | 2 | 3 | 4 | IV-2 | Prss21 | 10942 | 10-May-15 |
| 16605 | 2 | 3 | 4 | | IV-2 | Pgp | 283871 | 7-Jun-15 | 17494 | 2 | 3 | 4 | IV-2 | Prss28 | | |
| 16628 | 2 | 3 | 4 | | IV-2 | Phf11c | | | 17497 | 2 | 3 | 4 | IV-2 | Prss30 | | |
| 16634 | 2 | 3 | 4 | | IV-2 | Phf2 | 5253 | 7-Jun-15 | 17499 | 2 | 3 | 4 | IV-2 | Prss33 | 260429 | 4-May-15 |
| 16649 | 2 | 3 | 4 | | IV-2 | Phka2 | 5256 | 23-May-15 | 17502 | 2 | 3 | 4 | IV-2 | Prss36 | 146547 | 4-May-15 |
| 16652 | 2 | 3 | 4 | | IV-2 | Phkg2 | 5261 | 4-May-15 | 17518 | 2 | 3 | 4 | IV-2 | Prss54 | 221191 | 20-May-15 |
| 16654 | 2 | 3 | 4 | | IV-2 | Phlda2 | 7262 | 4-May-15 | 17526 | 2 | 3 | 4 | IV-2 | Prune | 58497 | 12-May-15 |
| 16655 | 2 | 3 | 4 | | IV-2 | Phlda3 | 23612 | 14-May-15 | 17528 | 2 | 3 | 4 | IV-2 | Prx | 57716 | 7-Jun-15 |
| 16674 | 2 | 3 | 4 | | IV-2 | Phyhipl | 84457 | 4-May-15 | 17533 | 2 | 3 | 4 | IV-2 | Psd | 5662 | 7-Jun-15 |
| 16677 | 2 | 3 | 4 | | IV-2 | Pi16 | 221476 | 1-May-15 | 17534 | 2 | 3 | 4 | IV-2 | Psd2 | 84249 | 4-May-15 |
| 16683 | 2 | 3 | 4 | | IV-2 | Pias1 | 8554 | 4-May-15 | 17555 | 2 | 3 | 4 | IV-2 | Psinc1 | 5700 | 21-May-15 |
| 16691 | 2 | 3 | 4 | | IV-2 | Pidd1 | 55367 | 12-May-15 | 17607 | 2 | 3 | 4 | IV-2 | Pspc1 | 55269 | 4-May-15 |
| 16708 | 2 | 3 | 4 | | IV-2 | Pigq | 9091 | 4-May-15 | 17616 | 2 | 3 | 4 | IV-2 | Ptbp1 | 5725 | 4-May-15 |
| 16710 | 2 | 3 | 4 | | IV-2 | Pigs | 94005 | 4-May-15 | 17623 | 2 | 3 | 4 | IV-2 | Ptch2 | 8643 | 23-May-15 |
| 16722 | 2 | 3 | 4 | | IV-2 | Pik3c2a | 5286 | 24-May-15 | 17624 | 2 | 3 | 4 | IV-2 | Ptchd1 | 139411 | 23-May-15 |
| 16729 | 2 | 3 | 4 | | IV-2 | Pik3cg | 5294 | 12-May-15 | 17635 | 2 | 3 | 4 | IV-2 | Ptgdr2 | 11251 | 4-May-15 |
| 16740 | 2 | 3 | 4 | | IV-2 | Pilrb2 | | | 17637 | 2 | 3 | 4 | IV-2 | Ptger1 | 5731 | 4-May-15 |
| 16747 | 2 | 3 | 4 | | IV-2 | Pinc | | | 17640 | 2 | 3 | 4 | IV-2 | Ptger4 | 5734 | 4-May-15 |
| 16752 | 2 | 3 | 4 | | IV-2 | Pip4k2a | 5305 | 4-May-15 | 17649 | 2 | 3 | 4 | IV-2 | Ptgr1 | 22949 | 4-May-15 |
| 16763 | 2 | 3 | 4 | | IV-2 | Pira2 | | | 17650 | 2 | 3 | 4 | IV-2 | Ptgr2 | 145482 | 4-May-15 |
| 16766 | 2 | 3 | 4 | | IV-2 | Pira7 | | | 17656 | 2 | 3 | 4 | IV-2 | Pth2 | 113091 | 4-May-15 |
| 16768 | 2 | 3 | 4 | | IV-2 | Pirt | 644139 | 12-May-15 | 17666 | 2 | 3 | 4 | IV-2 | Ptov1 | 53635 | 17-May-15 |
| 16784 | 2 | 3 | 4 | | IV-2 | Pitx3 | 5309 | 23-May-15 | 17674 | 2 | 3 | 4 | IV-2 | Ptplb | 201562 | 4-May-15 |
| 16804 | 2 | 3 | 4 | | IV-2 | Pkm | 5315 | 17-May-15 | 17692 | 2 | 3 | 4 | IV-2 | Ptpn9 | 5780 | 4-May-15 |
| 16816 | 2 | 3 | 4 | | IV-2 | Pla2g10 | 8399 | 12-May-15 | 17697 | 2 | 3 | 4 | IV-2 | Ptprd | 5789 | 4-May-15 |
| 16823 | 2 | 3 | 4 | | IV-2 | Pla2g2a | 5320 | 4-May-15 | 17703 | 2 | 3 | 4 | IV-2 | Ptprk | 5796 | 12-May-15 |
| 16826 | 2 | 3 | 4 | | IV-2 | Pla2g2e | 30814 | 4-May-15 | 17718 | 2 | 3 | 4 | IV-2 | Ptrh2 | 51651 | 21-May-15 |
| 16827 | 2 | 3 | 4 | | IV-2 | Pla2g2f | 64600 | 4-May-15 | 17725 | 2 | 3 | 4 | IV-2 | Puf60 | 22827 | 2-Jun-15 |
| 16832 | 2 | 3 | 4 | | IV-2 | Pla2g4d | 283748 | 4-May-15 | 17731 | 2 | 3 | 4 | IV-2 | Pus1 | 80324 | 4-May-15 |
| 16842 | 2 | 3 | 4 | | IV-2 | Plac8l1 | 153770 | 4-May-15 | 17738 | 2 | 3 | 4 | IV-2 | Pvr | 5817 | 17-May-15 |
| 16844 | 2 | 3 | 4 | | IV-2 | Plac9b | | | 17750 | 2 | 3 | 4 | IV-2 | Pxk | 54899 | 17-May-15 |
| 16852 | 2 | 3 | 4 | | IV-2 | Plbd1 | 79887 | 4-May-15 | 17752 | 2 | 3 | 4 | IV-2 | Pxmp4 | 11264 | 29-May-15 |
| 16858 | 2 | 3 | 4 | | IV-2 | Plcd1 | 5333 | 17-May-15 | 17758 | 2 | 3 | 4 | IV-2 | Pycr2 | 29920 | 4-May-15 |
| 16868 | 2 | 3 | 4 | | IV-2 | Plcxd1 | 55344 | 4-May-15 | 17760 | 2 | 3 | 4 | IV-2 | Pydc3 | | |
| 16870 | 2 | 3 | 4 | | IV-2 | Plcxd3 | 345557 | 4-May-15 | 17768 | 2 | 3 | 4 | IV-2 | Pyroxd1 | 79912 | 4-May-15 |
| 16889 | 2 | 3 | 4 | | IV-2 | Plekha8 | 84725 | 4-May-15 | 17773 | 2 | 3 | 4 | IV-2 | Qars | 5859 | 7-Jun-15 |
| 16919 | 2 | 3 | 4 | | IV-2 | Plin3 | 10226 | 4-May-15 | 17777 | 2 | 3 | 4 | IV-2 | Qpctl | 54814 | 4-May-15 |
| 16926 | 2 | 3 | 4 | | IV-2 | Plk5 | 126520 | 4-May-15 | 17802 | 2 | 3 | 4 | IV-2 | Rab11fip2 | 22841 | 4-May-15 |
| 16929 | 2 | 3 | 4 | | IV-2 | Plod1 | 5351 | 23-May-15 | 17824 | 2 | 3 | 4 | IV-2 | Rab27a | 5873 | 14-May-15 |
| 16943 | 2 | 3 | 4 | | IV-2 | Plvap | 83483 | 4-May-15 | 17830 | 2 | 3 | 4 | IV-2 | Rab31 | 11031 | 4-May-15 |
| 16955 | 2 | 3 | 4 | | IV-2 | Plxnd1 | 23129 | 4-May-15 | 17839 | 2 | 3 | 4 | IV-2 | Rab39 | 54734 | 7-Jun-15 |
| 16956 | 2 | 3 | 4 | | IV-2 | Pm20d1 | 148811 | 4-May-15 | 17852 | 2 | 3 | 4 | IV-2 | Rab43 | 339122 | 4-May-15 |
| 16961 | 2 | 3 | 4 | | IV-2 | Pmepa1 | 56937 | 4-May-15 | 17861 | 2 | 3 | 4 | IV-2 | Rab7 | 7879 | 7-Jun-15 |
| 16962 | 2 | 3 | 4 | | IV-2 | Pmf1 | 11243 | 7-Jun-15 | 17867 | 2 | 3 | 4 | IV-2 | Rabac1 | 10567 | 4-May-15 |
| 16975 | 2 | 3 | 4 | | IV-2 | Pnck | 139728 | 4-May-15 | 17878 | 2 | 3 | 4 | IV-2 | Rabl3 | 285282 | 4-May-15 |
| 16982 | 2 | 3 | 4 | | IV-2 | Phliprp2 | 5408 | 4-May-15 | 17882 | 2 | 3 | 4 | IV-2 | Rac3 | 5881 | 7-Jun-15 |
| 16983 | 2 | 3 | 4 | | IV-2 | Pnma1 | 9240 | 17-May-15 | 17884 | 2 | 3 | 4 | IV-2 | Rad1 | 5810 | 7-Jun-15 |
| 16999 | 2 | 3 | 4 | | IV-2 | Pnpla6 | 10908 | 4-May-15 | 17894 | 2 | 3 | 4 | IV-2 | Rad51ap2 | 729475 | 4-May-15 |
| 17029 | 2 | 3 | 4 | | IV-2 | Pole2 | 5427 | 12-May-15 | 17899 | 2 | 3 | 4 | IV-2 | Rad54b | 25788 | 4-May-15 |
| 17030 | 2 | 3 | 4 | | IV-2 | Pole3 | 54107 | 4-May-15 | 17900 | 2 | 3 | 4 | IV-2 | Rad54l | 8438 | 7-Jun-15 |
| 17041 | 2 | 3 | 4 | | IV-2 | Polr1a | 25885 | 4-Jun-15 | 17901 | 2 | 3 | 4 | IV-2 | Rad54l2 | 23132 | 4-May-15 |
| 17057 | 2 | 3 | 4 | | IV-2 | Polr2l | 5441 | 12-May-15 | 17910 | 2 | 3 | 4 | IV-2 | Raet1e | 135250 | 12-May-15 |
| 17074 | 2 | 3 | 4 | | IV-2 | Pomgnt1 | 55624 | 23-May-15 | 17911 | 2 | 3 | 4 | IV-2 | Raf1 | 5894 | 23-May-15 |

Fig.22 - 18

| | | | | | | | | | | | | | | | |
|---|---|---|---|---|---|---|---|---|---|---|---|---|---|---|---|
| 17913 | 2 | 3 | 4 | | IV-2 | Rag2 | 5897 | 12-May-15 | 18832 | 2 | 3 | 4 | IV-2 | Satb2 | 23314 | 4-May-15 |
| 17917 | 2 | 3 | 4 | | IV-2 | Rala | 5898 | 4-May-15 | 18847 | 2 | 3 | 4 | IV-2 | Sbspon | 157869 | 4-May-15 |
| 17957 | 2 | 3 | 4 | | IV-2 | Raph1 | 65059 | 4-May-15 | 18864 | 2 | 3 | 4 | IV-2 | Scarb1 | 949 | 24-May-15 |
| 17964 | 2 | 3 | 4 | | IV-2 | Rars | 5917 | 4-May-15 | 18871 | 2 | 3 | 4 | IV-2 | Scarna17 | 677769 | 12-May-15 |
| 17966 | 2 | 3 | 4 | | IV-2 | Rasa1 | 5921 | 7-Jun-15 | 18877 | 2 | 3 | 4 | IV-2 | Scarna9 | 619383 | 12-May-15 |
| 17978 | 2 | 3 | 4 | | IV-2 | Rasgef1c | 255426 | 4-May-15 | 18890 | 2 | 3 | 4 | IV-2 | Scgb1b19 | | |
| 17980 | 2 | 3 | 4 | | IV-2 | Rasgrf2 | 5924 | 4-May-15 | 18895 | 2 | 3 | 4 | IV-2 | Scgb1b29 | | |
| 17982 | 2 | 3 | 4 | | IV-2 | Rasgrp2 | 10235 | 4-May-15 | 18897 | 2 | 3 | 4 | IV-2 | Scgb1b30 | | |
| 17984 | 2 | 3 | 4 | | IV-2 | Rasgrp4 | 115727 | 12-May-15 | 18903 | 2 | 3 | 4 | IV-2 | Scgb2b19 | | |
| 17987 | 2 | 3 | 4 | | IV-2 | Rasl10b | 91608 | 4-May-15 | 18906 | 2 | 3 | 4 | IV-2 | Scgb2b23-ps | | |
| 17991 | 2 | 3 | 4 | | IV-2 | Rasl2-9 | | | 18910 | 2 | 3 | 4 | IV-2 | Scgb3b3 | | |
| 18020 | 2 | 3 | 4 | | IV-2 | Rbfox2 | 23543 | 2-Jun-15 | 18912 | 2 | 3 | 4 | IV-2 | Scgb3a1 | 92304 | 4-May-15 |
| 18032 | 2 | 3 | 4 | | IV-2 | Rbm15 | 64783 | 4-May-15 | 18914 | 2 | 3 | 4 | IV-2 | Scgn | 10590 | 4-May-15 |
| 18040 | 2 | 3 | 4 | | IV-2 | Rbm25 | 58517 | 12-May-15 | 18923 | 2 | 3 | 4 | IV-2 | Scn10a | 6336 | 4-May-15 |
| 18056 | 2 | 3 | 4 | | IV-2 | Rbm45 | 129831 | 4-May-15 | 18927 | 2 | 3 | 4 | IV-2 | Scn2a1 | 6326 | 17-May-15 |
| 18079 | 2 | 3 | 4 | | IV-2 | Rbpj | 3516 | 12-May-15 | 18933 | 2 | 3 | 4 | IV-2 | Scn5a | 6331 | 31-May-15 |
| 18081 | 2 | 3 | 4 | | IV-2 | Rbpms | 11030 | 4-May-15 | 18948 | 2 | 3 | 4 | IV-2 | Scrg1 | 11341 | 4-May-15 |
| 18118 | 2 | 3 | 4 | | IV-2 | Rdh8 | 50700 | 21-May-15 | 18951 | 2 | 3 | 4 | IV-2 | Scrn2 | 90507 | 4-May-15 |
| 18121 | 2 | 3 | 4 | | IV-2 | Rdx | 5962 | 3-Jun-15 | 18961 | 2 | 3 | 4 | IV-2 | Scyl1 | 57410 | 7-Jun-15 |
| 18140 | 2 | 3 | 4 | | IV-2 | Reg4 | 83998 | 4-May-15 | 18976 | 2 | 3 | 4 | IV-2 | Sdf4 | 51150 | 4-May-15 |
| 18141 | 2 | 3 | 4 | | IV-2 | Rel | 3968 | 28-May-15 | 18991 | 2 | 3 | 4 | IV-2 | Sds | 10993 | 21-May-15 |
| 18149 | 2 | 3 | 4 | | IV-2 | Rem2 | 161253 | 4-May-15 | 18999 | 2 | 3 | 4 | IV-2 | Sebox | 645832 | 12-May-15 |
| 18151 | 2 | 3 | 4 | | IV-2 | Ren2 | | | 19001 | 2 | 3 | 4 | IV-2 | Sec14l4 | 284904 | 4-May-15 |
| 18153 | 2 | 3 | 4 | | IV-2 | Rep15 | 387849 | 28-May-15 | 19002 | 2 | 3 | 4 | IV-2 | Sec14l5 | 9717 | 4-May-15 |
| 18163 | 2 | 3 | 4 | | IV-2 | Ret | 5979 | 22-May-15 | 19021 | 2 | 3 | 4 | IV-2 | Sec62 | 7095 | 12-May-15 |
| 18189 | 2 | 3 | 4 | | IV-2 | Rftn2 | 130132 | 12-May-15 | 19034 | 2 | 3 | 4 | IV-2 | Sek | 58515 | 4-May-15 |
| 18211 | 2 | 3 | 4 | | IV-2 | Rgp1 | 9827 | un-2015 | 19036 | 2 | 3 | 4 | IV-2 | Selm | 140606 | 4-May-15 |
| 18215 | 2 | 3 | 4 | | IV-2 | Rgs11 | 8786 | 21-May-15 | 19040 | 2 | 3 | 4 | IV-2 | Selt | 51714 | 4-May-15 |
| 18218 | 2 | 3 | 4 | | IV-2 | Rgs14 | 10636 | 4-May-15 | 19044 | 2 | 3 | 4 | IV-2 | Sema3d | 223117 | 21-May-15 |
| 18219 | 2 | 3 | 4 | | IV-2 | Rgs16 | 6004 | 4-May-15 | 19059 | 2 | 3 | 4 | IV-2 | Sema6d | 80031 | 4-May-15 |
| 18220 | 2 | 3 | 4 | | IV-2 | Rgs17 | 26575 | 4-May-15 | 19060 | 2 | 3 | 4 | IV-2 | Sema7a | 8482 | 4-May-15 |
| 18230 | 2 | 3 | 4 | | IV-2 | Rgs6 | 9628 | 17-May-15 | 19061 | 2 | 3 | 4 | IV-2 | Senp1 | 29843 | 4-May-15 |
| 18233 | 2 | 3 | 4 | | IV-2 | Rgs8 | 85397 | 4-May-15 | 19074 | 2 | 3 | 4 | IV-2 | Sept10 | 151011 | 4-May-15 |
| 18238 | 2 | 3 | 4 | | IV-2 | Rhbdd1 | 84236 | 29-May-15 | 19088 | 2 | 3 | 4 | IV-2 | Serac1 | 84947 | 23-May-15 |
| 18244 | 2 | 3 | 4 | | IV-2 | Rhbdl2 | 54933 | 4-May-15 | 19091 | 2 | 3 | 4 | IV-2 | Serf2 | 10169 | 4-May-15 |
| 18249 | 2 | 3 | 4 | | IV-2 | Rheb | 6009 | 7-Jun-15 | 19102 | 2 | 3 | 4 | IV-2 | Serpina11 | 256394 | 4-May-15 |
| 18251 | 2 | 3 | 4 | | IV-2 | Rhno1 | 83695 | 4-May-15 | 19115 | 2 | 3 | 4 | IV-2 | Serpina3h | | |
| 18253 | 2 | 3 | 4 | | IV-2 | Rhoa | 387 | 31-May-15 | 19122 | 2 | 3 | 4 | IV-2 | Serpina5 | 5104 | 12-May-15 |
| 18263 | 2 | 3 | 4 | | IV-2 | Rhoj | 57381 | 4-May-15 | 19131 | 2 | 3 | 4 | IV-2 | Serpinb1b | | |
| 18269 | 2 | 3 | 4 | | IV-2 | Rhoxf1 | | | 19135 | 2 | 3 | 4 | IV-2 | Serpinb3b | | |
| 18296 | 2 | 3 | 4 | | IV-2 | Rhox6 | | | 19140 | 2 | 3 | 4 | IV-2 | Serpinb6b | | |
| 18303 | 2 | 3 | 4 | | IV-2 | Ribc1 | 158787 | 4-May-15 | 19160 | 2 | 3 | 4 | IV-2 | Serping1 | 710 | 12-May-15 |
| 18310 | 2 | 3 | 4 | | IV-2 | Riiad1 | 284485 | 4-May-15 | 19162 | 2 | 3 | 4 | IV-2 | Serpini1 | 5274 | 12-May-15 |
| 18322 | 2 | 3 | 4 | | IV-2 | Rin1 | 9610 | 4-May-15 | 19164 | 2 | 3 | 4 | IV-2 | Sertad1 | 29950 | 4-May-15 |
| 18333 | 2 | 3 | 4 | | IV-2 | Ripk3 | 11035 | 17-May-15 | 19168 | 2 | 3 | 4 | IV-2 | Sertm1 | 400120 | 4-May-15 |
| 18346 | 2 | 3 | 4 | | IV-2 | Ritpr | 146206 | 4-May-15 | 19172 | 2 | 3 | 4 | IV-2 | Sestd1 | 91404 | 4-May-15 |
| 18347 | 2 | 3 | 4 | | IV-2 | Rmdn1 | 51115 | 12-May-15 | 19211 | 2 | 3 | 4 | IV-2 | Sfswap | 6433 | 12-May-15 |
| 18353 | 2 | 3 | 4 | | IV-2 | Rmnd5a | 64785 | 4-May-15 | 19219 | 2 | 3 | 4 | IV-2 | Sftpd | 6441 | 12-May-15 |
| 18356 | 2 | 3 | 4 | | IV-2 | Rmst | 196475 | 4-May-15 | 19223 | 2 | 3 | 4 | IV-2 | Sfxn4 | 119559 | 4-May-15 |
| 18377 | 2 | 3 | 4 | | IV-2 | Rnd1 | 27289 | 4-May-15 | 19230 | 2 | 3 | 4 | IV-2 | Sgcz | 137868 | 17-May-15 |
| 18379 | 2 | 3 | 4 | | IV-2 | Rnd3 | 390 | 12-May-15 | 19238 | 2 | 3 | 4 | IV-2 | Sgol2 | 151246 | 4-May-15 |
| 18391 | 2 | 3 | 4 | | IV-2 | Rnf123 | 63891 | 4-May-15 | 19239 | 2 | 3 | 4 | IV-2 | Sgpl1 | 8879 | 4-May-15 |
| 18393 | 2 | 3 | 4 | | IV-2 | Rnf126 | 55658 | 4-May-15 | 19248 | 2 | 3 | 4 | IV-2 | Sh2b1 | 25970 | 21-May-15 |
| 18404 | 2 | 3 | 4 | | IV-2 | Rnf144a | 9781 | 18-May-15 | 19250 | 2 | 3 | 4 | IV-2 | Sh2b3 | 10019 | 21-May-15 |
| 18424 | 2 | 3 | 4 | | IV-2 | Rnf183 | 138065 | 4-May-15 | 19252 | 2 | 3 | 4 | IV-2 | Sh2d1b1 | | |
| 18425 | 2 | 3 | 4 | | IV-2 | Rnf185 | 91445 | 28-May-15 | 19261 | 2 | 3 | 4 | IV-2 | Sh3bgrl | 6451 | 4-May-15 |
| 18444 | 2 | 3 | 4 | | IV-2 | Rnf25 | 64320 | 4-May-15 | 19266 | 2 | 3 | 4 | IV-2 | Sh3bp4 | 23677 | 4-May-15 |
| 18473 | 2 | 3 | 4 | | IV-2 | Rnu6 | | | 19277 | 2 | 3 | 4 | IV-2 | Sh3pxd2a | 9644 | 4-May-15 |
| 18485 | 2 | 3 | 4 | | IV-2 | Ropn1 | 54763 | 31-May-15 | 19278 | 2 | 3 | 4 | IV-2 | Sh3pxd2b | 285590 | 12-May-15 |
| 18500 | 2 | 3 | 4 | | IV-2 | Rpain | 84268 | 4-May-15 | 19296 | 2 | 3 | 4 | IV-2 | Shcbp1l | 81626 | 12-May-15 |
| 18509 | 2 | 3 | 4 | | IV-2 | Rpgrip1 | 57096 | 12-May-15 | 19303 | 2 | 3 | 4 | IV-2 | Shisa3 | 152573 | 4-May-15 |
| 18511 | 2 | 3 | 4 | | IV-2 | Rph3a | 22895 | 4-May-15 | 19321 | 2 | 3 | 4 | IV-2 | Siae | 54414 | 4-May-15 |
| 18538 | 2 | 3 | 4 | | IV-2 | Rpl29 | 6159 | 4-May-15 | 19334 | 2 | 3 | 4 | IV-2 | Siglech | | |
| 18541 | 2 | 3 | 4 | | IV-2 | Rpl31 | 6160 | 4-May-15 | 19335 | 2 | 3 | 4 | IV-2 | Sigmar1 | 10280 | 23-May-15 |
| 18546 | 2 | 3 | 4 | | IV-2 | Rpl35 | 11224 | 4-May-15 | 19338 | 2 | 3 | 4 | IV-2 | Sik3 | 23387 | 24-May-15 |
| 18554 | 2 | 3 | 4 | | IV-2 | Rpl39 | 6170 | 12-May-15 | 19357 | 2 | 3 | 4 | IV-2 | Sirt5 | 23408 | 31-May-15 |
| 18557 | 2 | 3 | 4 | | IV-2 | Rpl4 | 6124 | 4-May-15 | 19362 | 2 | 3 | 4 | IV-2 | Siva1 | 10572 | 31-May-15 |
| 18574 | 2 | 3 | 4 | | IV-2 | Rpp25 | 54913 | 4-May-15 | 19403 | 2 | 3 | 4 | IV-2 | Slamf8 | 56833 | 4-May-15 |
| 18592 | 2 | 3 | 4 | | IV-2 | Rps14 | 6208 | 2-Jun-15 | 19404 | 2 | 3 | 4 | IV-2 | Slamf9 | 89886 | 4-May-15 |
| 18616 | 2 | 3 | 4 | | IV-2 | Rps3 | 6188 | 4-May-15 | 19405 | 2 | 3 | 4 | IV-2 | Slbp | 7884 | 12-May-15 |
| 18632 | 2 | 3 | 4 | | IV-2 | Rps7 | 6201 | 7-Jun-15 | 19408 | 2 | 3 | 4 | IV-2 | Slc10a3 | 8273 | 4-May-15 |
| 18645 | 2 | 3 | 4 | | IV-2 | Rraga | 10670 | 29-May-15 | 19431 | 2 | 3 | 4 | IV-2 | Slc14a1 | 6563 | 21-May-15 |
| 18656 | 2 | 3 | 4 | | IV-2 | Rrm2b | 50484 | 17-May-15 | 19436 | 2 | 3 | 4 | IV-2 | Slc15a4 | 121260 | 12-May-15 |
| 18671 | 2 | 3 | 4 | | IV-2 | Rsbn1 | 54665 | 4-May-15 | 19438 | 2 | 3 | 4 | IV-2 | Slc16a1 | 6566 | 21-May-15 |
| 18703 | 2 | 3 | 4 | | IV-2 | Rtkn2 | 219790 | 4-May-15 | 19443 | 2 | 3 | 4 | IV-2 | Slc16a14 | 151473 | 4-May-15 |
| 18704 | 2 | 3 | 4 | | IV-2 | Rtl1 | 388015 | 4-May-15 | 19446 | 2 | 3 | 4 | IV-2 | Slc16a4 | 9122 | 4-May-15 |
| 18707 | 2 | 3 | 4 | | IV-2 | Rtn3 | 10313 | 12-May-15 | 19456 | 2 | 3 | 4 | IV-2 | Slc17a5 | 26503 | 23-May-15 |
| 18713 | 2 | 3 | 4 | | IV-2 | Rtp1 | 132112 | 9-May-15 | 19476 | 2 | 3 | 4 | IV-2 | Slc20a2 | 6575 | 23-May-15 |
| 18716 | 2 | 3 | 4 | | IV-2 | Rtp4 | 64108 | 9-May-15 | 19479 | 2 | 3 | 4 | IV-2 | Slc22a13 | 9390 | 4-May-15 |
| 18727 | 2 | 3 | 4 | | IV-2 | Runx1t1 | 862 | 21-May-15 | 19487 | 2 | 3 | 4 | IV-2 | Slc22a2 | 6582 | 4-May-15 |
| 18730 | 2 | 3 | 4 | | IV-2 | Rusc1 | 23623 | 4-May-15 | 19495 | 2 | 3 | 4 | IV-2 | Slc22a29 | | |
| 18737 | 2 | 3 | 4 | | IV-2 | Rwdd3 | 25950 | 4-May-15 | 19508 | 2 | 3 | 4 | IV-2 | Slc24a3 | 57439 | 4-May-15 |
| 18749 | 2 | 3 | 4 | | IV-2 | Ryr2 | 6262 | 23-May-15 | 19511 | 2 | 3 | 4 | IV-2 | Slc25a1 | 6576 | 17-May-15 |
| 18760 | 2 | 3 | 4 | | IV-2 | S100a5 | 6276 | 4-May-15 | 19512 | 2 | 3 | 4 | IV-2 | Slc25a10 | 1468 | 4-May-15 |
| 18765 | 2 | 3 | 4 | | IV-2 | S100b | 6285 | 24-May-15 | 19535 | 2 | 3 | 4 | IV-2 | Slc25a31 | 83447 | 12-May-15 |
| 18771 | 2 | 3 | 4 | | IV-2 | S1pr3 | 1903 | 4-May-15 | 19554 | 2 | 3 | 4 | IV-2 | Slc25a5 | 292 | 6-May-15 |
| 18772 | 2 | 3 | 4 | | IV-2 | S1pr4 | 8698 | 4-May-15 | 19562 | 2 | 3 | 4 | IV-2 | Slc26a3 | 1811 | 4-May-15 |
| 18777 | 2 | 3 | 4 | | IV-2 | Saa4 | 6291 | 7-Jun-15 | 19567 | 2 | 3 | 4 | IV-2 | Slc26a8 | 116369 | 4-May-15 |
| 18778 | 2 | 3 | 4 | | IV-2 | Saal1 | 113174 | 4-May-15 | 19571 | 2 | 3 | 4 | IV-2 | Slc27a3 | 11000 | 4-May-15 |
| 18793 | 2 | 3 | 4 | | IV-2 | Samd12 | 401474 | 4-May-15 | 19572 | 2 | 3 | 4 | IV-2 | Slc27a4 | 10999 | 17-May-15 |
| 18806 | 2 | 3 | 4 | | IV-2 | Samt2 | | | 19585 | 2 | 3 | 4 | IV-2 | Slc2a13 | 114134 | 4-May-15 |
| 18812 | 2 | 3 | 4 | | IV-2 | Sap30 | 8819 | 4-May-15 | 19586 | 2 | 3 | 4 | IV-2 | Slc2a2 | 6514 | 12-May-15 |
| 18813 | 2 | 3 | 4 | | IV-2 | Sap30bp | 29115 | 12-May-15 | 19589 | 2 | 3 | 4 | IV-2 | Slc2a4rg-ps | | |
| 18817 | 2 | 3 | 4 | | IV-2 | Sar1a | 56681 | 3-May-15 | 19591 | 2 | 3 | 4 | IV-2 | Slc2a6 | 11182 | 4-May-15 |
| 18820 | 2 | 3 | 4 | | IV-2 | Sarm1 | 23098 | 12-May-15 | 19599 | 2 | 3 | 4 | IV-2 | Slc30a4 | 7782 | 4-May-15 |
| 18821 | 2 | 3 | 4 | | IV-2 | Sarnp | 84324 | 4-May-15 | 19602 | 2 | 3 | 4 | IV-2 | Slc30a7 | 148867 | 4-May-15 |
| 18828 | 2 | 3 | 4 | | IV-2 | Sass6 | 163786 | 4-May-15 | 19611 | 2 | 3 | 4 | IV-2 | Slc34a3 | 142680 | 12-May-15 |

Fig.22 - 19

| | | | | | | | | | | | | | | | |
|---|---|---|---|---|---|---|---|---|---|---|---|---|---|---|---|
| 19612 | 2 | 3 | 4 | | IV-2 | Slc35a1 | 10559 | 23-May-15 | 20483 | 2 | 3 | 4 | | IV-2 | Sstr1 | 6751 | 4-May-15 |
| 19642 | 2 | 3 | 4 | | IV-2 | Slc36a3 | 285641 | 4-May-15 | 20485 | 2 | 3 | 4 | | IV-2 | Sstr3 | 6783 | 24-May-15 |
| 19650 | 2 | 3 | 4 | | IV-2 | Slc38a11 | 151258 | 4-May-15 | 20487 | 2 | 3 | 4 | | IV-2 | Sstr5 | 6755 | 12-May-15 |
| 19655 | 2 | 3 | 4 | | IV-2 | Slc38a6 | 145389 | 4-May-15 | 20507 | 2 | 3 | 4 | | IV-2 | St3gal3 | 6487 | 4-May-15 |
| 19661 | 2 | 3 | 4 | | IV-2 | Slc39a11 | 201266 | 4-May-15 | 20516 | 2 | 3 | 4 | | IV-2 | St6galnac3 | 256435 | 4-May-15 |
| 19676 | 2 | 3 | 4 | | IV-2 | Slc41a1 | 254428 | 4-May-15 | 20524 | 2 | 3 | 4 | | IV-2 | St8sia3 | 51046 | 23-May-15 |
| 19680 | 2 | 3 | 4 | | IV-2 | Slc43a2 | 124935 | 21-May-15 | 20534 | 2 | 3 | 4 | | IV-2 | Stag1 | 10274 | 16-Jun-15 |
| 19698 | 2 | 3 | 4 | | IV-2 | Slc4a10 | 57282 | 4-May-15 | 20550 | 2 | 3 | 4 | | IV-2 | Stard5 | 80765 | 4-May-15 |
| 19730 | 2 | 3 | 4 | | IV-2 | Slc6a14 | 11254 | 4-May-15 | 20574 | 2 | 3 | 4 | | IV-2 | Stil | 6491 | 23-May-15 |
| 19735 | 2 | 3 | 4 | | IV-2 | Slc6a19os | | | 20575 | 2 | 3 | 4 | | IV-2 | Stim1 | 6786 | 31-May-15 |
| 19741 | 2 | 3 | 4 | | IV-2 | Slc6a5 | 9152 | 7-Jun-15 | 20584 | 2 | 3 | 4 | | IV-2 | Stk24 | 8428 | 12-May-15 |
| 19751 | 2 | 3 | 4 | | IV-2 | Slc7a14 | 57709 | 4-May-15 | 20600 | 2 | 3 | 4 | | IV-2 | Stmn1-rs1 | | |
| 19769 | 2 | 3 | 4 | | IV-2 | Slc9a3r1 | 9368 | 31-May-15 | 20603 | 2 | 3 | 4 | | IV-2 | Stmn4 | 81551 | 4-May-15 |
| 19777 | 2 | 3 | 4 | | IV-2 | Slc9b1 | 150159 | 31-May-15 | 20610 | 2 | 3 | 4 | | IV-2 | Ston2 | 85439 | 12-May-15 |
| 19790 | 2 | 3 | 4 | | IV-2 | Slco4c1 | 353189 | 4-May-15 | 20617 | 2 | 3 | 4 | | IV-2 | Stra8 | 346673 | 4-May-15 |
| 19792 | 2 | 3 | 4 | | IV-2 | Slco6b1 | | | 20625 | 2 | 3 | 4 | | IV-2 | Strn | 6801 | 4-May-15 |
| 19796 | 2 | 3 | 4 | | IV-2 | Slfn10-ps | | | 20626 | 2 | 3 | 4 | | IV-2 | Strn3 | 29966 | 4-May-15 |
| 19799 | 2 | 3 | 4 | | IV-2 | Slfn3 | 55106 | 4-May-15 | 20632 | 2 | 3 | 4 | | IV-2 | Stx12 | 23673 | 4-May-15 |
| 19800 | 2 | 3 | 4 | | IV-2 | Slfn4 | | | 20647 | 2 | 3 | 4 | | IV-2 | Stxbp2 | 6813 | 22-May-15 |
| 19801 | 2 | 3 | 4 | | IV-2 | Slfn5 | 162394 | 4-May-15 | 20662 | 2 | 3 | 4 | | IV-2 | Suco | 51430 | 4-May-15 |
| 19802 | 2 | 3 | 4 | | IV-2 | Slfn5os | | | 20663 | 2 | 3 | 4 | | IV-2 | Suds3 | 64426 | 4-May-15 |
| 19805 | 2 | 3 | 4 | | IV-2 | Slirt1 | 200172 | 4-May-15 | 20673 | 2 | 3 | 4 | | IV-2 | Sult1c1 | 6819 | 7-Jun-15 |
| 19807 | 2 | 3 | 4 | | IV-2 | Slit1 | 6585 | 7-Jun-15 | 20675 | 2 | 3 | 4 | | IV-2 | Sult1d1 | 133150 | 4-May-15 |
| 19816 | 2 | 3 | 4 | | IV-2 | Slk | 9748 | 7-Jun-15 | 20676 | 2 | 3 | 4 | | IV-2 | Sult1e1 | 6783 | 12-May-15 |
| 19822 | 2 | 3 | 4 | | IV-2 | Slrn | 79811 | 4-May-15 | 20677 | 2 | 3 | 4 | | IV-2 | Sult2a1 | 6822 | 7-Jun-15 |
| 19844 | 2 | 3 | 4 | | IV-2 | Smarca4 | 6597 | 4-May-15 | 20688 | 2 | 3 | 4 | | IV-2 | Sult6b1 | 391365 | 4-May-15 |
| 19859 | 2 | 3 | 4 | | IV-2 | Smc2os | | | 20713 | 2 | 3 | 4 | | IV-2 | Susd3 | 203328 | 12-May-15 |
| 19862 | 2 | 3 | 4 | | IV-2 | Smc5 | 23137 | 4-May-15 | 20715 | 2 | 3 | 4 | | IV-2 | Susd5 | 26032 | 4-May-15 |
| 19866 | 2 | 3 | 4 | | IV-2 | Smco2 | 341346 | 4-May-15 | 20746 | 2 | 3 | 4 | | IV-2 | Syce1 | 93426 | 4-May-15 |
| 19870 | 2 | 3 | 4 | | IV-2 | Smcr8 | 140775 | 4-May-15 | 20749 | 2 | 3 | 4 | | IV-2 | Syce3 | 644186 | 4-May-15 |
| 19882 | 2 | 3 | 4 | | IV-2 | Smim11 | 54065 | 4-May-15 | 20751 | 2 | 3 | 4 | | IV-2 | Sycp1 | 6847 | 4-May-15 |
| 19888 | 2 | 3 | 4 | | IV-2 | Smim19 | 114926 | 4-May-15 | 20763 | 2 | 3 | 4 | | IV-2 | Syna | | |
| 19894 | 2 | 3 | 4 | | IV-2 | Smim4 | 440957 | 4-May-15 | 20766 | 2 | 3 | 4 | | IV-2 | Syncrip | 10492 | 1-Jun-15 |
| 19912 | 2 | 3 | 4 | | IV-2 | Smpd1 | 6609 | 23-May-15 | 20775 | 2 | 3 | 4 | | IV-2 | Syngr2 | 9144 | 4-May-15 |
| 19915 | 2 | 3 | 4 | | IV-2 | Smpd4 | 55627 | 12-May-15 | 20782 | 2 | 3 | 4 | | IV-2 | Synpo | 11346 | 4-May-15 |
| 19920 | 2 | 3 | 4 | | IV-2 | Smr2 | | | 20785 | 2 | 3 | 4 | | IV-2 | Synpr | 132204 | 4-May-15 |
| 19922 | 2 | 3 | 4 | | IV-2 | Sms | 6611 | 13-Jun-15 | 20788 | 2 | 3 | 4 | | IV-2 | Sypl | 6856 | 4-May-15 |
| 19926 | 2 | 3 | 4 | | IV-2 | Smu1 | 55234 | 4-May-15 | 20790 | 2 | 3 | 4 | | IV-2 | Sys1 | 90196 | 4-May-15 |
| 19931 | 2 | 3 | 4 | | IV-2 | Smyd2 | 56950 | 21-May-15 | 20792 | 2 | 3 | 4 | | IV-2 | Syt10 | 341359 | 4-May-15 |
| 19943 | 2 | 3 | 4 | | IV-2 | Snapc1 | 6617 | 4-May-15 | 20795 | 2 | 3 | 4 | | IV-2 | Syt13 | 57586 | 4-May-15 |
| 19946 | 2 | 3 | 4 | | IV-2 | Snapc4 | 6621 | 4-May-15 | 20797 | 2 | 3 | 4 | | IV-2 | Syt14 | 255928 | 12-May-15 |
| 19953 | 2 | 3 | 4 | | IV-2 | Snd1 | 27044 | 31-May-15 | 20799 | 2 | 3 | 4 | | IV-2 | Syt17 | 51760 | 12-May-15 |
| 19955 | 2 | 3 | 4 | | IV-2 | Snf8 | 11267 | 21-May-15 | 20803 | 2 | 3 | 4 | | IV-2 | Syt5 | 6861 | 4-May-15 |
| 19965 | 2 | 3 | 4 | | IV-2 | Snhg7 | 84973 | 12-May-15 | 20806 | 2 | 3 | 4 | | IV-2 | Syt8 | 90019 | 4-May-15 |
| 19966 | 2 | 3 | 4 | | IV-2 | Snhg8 | 100093630 | 12-May-15 | 20855 | 2 | 3 | 4 | | IV-2 | Taf13 | 6884 | 4-May-15 |
| 19973 | 2 | 3 | 4 | | IV-2 | Snora19 | 641451 | 4-May-15 | 20880 | 2 | 3 | 4 | | IV-2 | Tal2 | 6887 | 28-May-15 |
| 19977 | 2 | 3 | 4 | | IV-2 | Snora24 | 677809 | 21-May-15 | 20885 | 2 | 3 | 4 | | IV-2 | Tango2 | 128989 | 4-May-15 |
| 19986 | 2 | 3 | 4 | | IV-2 | Snora35 | 677816 | 4-May-15 | 20892 | 2 | 3 | 4 | | IV-2 | Tap2 | 6891 | 7-Jun-15 |
| 19991 | 2 | 3 | 4 | | IV-2 | Snora47 | 677828 | 4-May-15 | 20942 | 2 | 3 | 4 | | IV-2 | Tatdn1 | 83940 | 4-May-15 |
| 19993 | 2 | 3 | 4 | | IV-2 | Snora5c | 677796 | 4-May-15 | 20949 | 2 | 3 | 4 | | IV-2 | Tbc1d1 | 23216 | 4-May-15 |
| 20006 | 2 | 3 | 4 | | IV-2 | Snord100 | 594838 | 4-May-15 | 20953 | 2 | 3 | 4 | | IV-2 | Tbc1d12 | 23232 | 4-May-15 |
| 20022 | 2 | 3 | 4 | | IV-2 | Snord15a | | | 20991 | 2 | 3 | 4 | | IV-2 | Tbl1xr1 | 79718 | 12-May-15 |
| 20024 | 2 | 3 | 4 | | IV-2 | Snord19 | 692089 | 4-May-15 | 21002 | 2 | 3 | 4 | | IV-2 | Tbx10 | 347853 | 4-May-15 |
| 20031 | 2 | 3 | 4 | | IV-2 | Snord32a | 26819 | 4-May-15 | 21009 | 2 | 3 | 4 | | IV-2 | Tbx22 | 50945 | 17-May-15 |
| 20094 | 2 | 3 | 4 | | IV-2 | Snrpd1 | 6632 | 7-Jun-15 | 21016 | 2 | 3 | 4 | | IV-2 | Tbxas1 | 6916 | 12-May-15 |
| 20100 | 2 | 3 | 4 | | IV-2 | Snrpn | 6638 | 23-May-15 | 21018 | 2 | 3 | 4 | | IV-2 | Tcaim | 285848 | 4-May-15 |
| 20104 | 2 | 3 | 4 | | IV-2 | Sntg1 | 54212 | 28-May-15 | 21021 | 2 | 3 | 4 | | IV-2 | Tceal1 | 6917 | 4-May-15 |
| 20106 | 2 | 3 | 4 | | IV-2 | Sntn | 132203 | 4-May-15 | 21024 | 2 | 3 | 4 | | IV-2 | Tceal3 | 9338 | 4-May-15 |
| 20132 | 2 | 3 | 4 | | IV-2 | Snx32 | 254122 | 12-May-15 | 21026 | 2 | 3 | 4 | | IV-2 | Tceal5 | 340543 | 4-May-15 |
| 20147 | 2 | 3 | 4 | | IV-2 | Socs5 | 9655 | 12-May-15 | 21027 | 2 | 3 | 4 | | IV-2 | Tceal6 | 158931 | 4-May-15 |
| 20153 | 2 | 3 | 4 | | IV-2 | Soga1 | 140710 | 12-May-15 | 21028 | 2 | 3 | 4 | | IV-2 | Tceal7 | 56849 | 4-May-15 |
| 20162 | 2 | 3 | 4 | | IV-2 | Sorcs1 | 114815 | 4-May-15 | 21033 | 2 | 3 | 4 | | IV-2 | Tceal8 | 90843 | 4-May-15 |
| 20167 | 2 | 3 | 4 | | IV-2 | Sort1 | 6272 | 31-May-15 | 21039 | 2 | 3 | 4 | | IV-2 | Tcf19 | 6941 | 21-May-15 |
| 20178 | 2 | 3 | 4 | | IV-2 | Sox11 | 6664 | 28-May-15 | 21041 | 2 | 3 | 4 | | IV-2 | Tcf21 | 6943 | 28-May-15 |
| 20186 | 2 | 3 | 4 | | IV-2 | Sox21 | 11166 | 28-May-15 | 21048 | 2 | 3 | 4 | | IV-2 | Tcf7l1 | 83439 | 4-May-15 |
| 20194 | 2 | 3 | 4 | | IV-2 | Sox7 | 83595 | 4-May-15 | 21052 | 2 | 3 | 4 | | IV-2 | Tchhl1 | 126637 | 12-May-15 |
| 20195 | 2 | 3 | 4 | | IV-2 | Sox8 | 30812 | 4-May-15 | 21085 | 2 | 3 | 4 | | IV-2 | Tdo2 | 6999 | 4-May-15 |
| 20201 | 2 | 3 | 4 | | IV-2 | Sp2 | 6668 | 7-Jun-15 | 21097 | 2 | 3 | 4 | | IV-2 | Tdrd6 | 221400 | 4-May-15 |
| 20206 | 2 | 3 | 4 | | IV-2 | Sp6 | 80320 | 4-May-15 | 21106 | 2 | 3 | 4 | | IV-2 | Tec | 7006 | 7-Jun-15 |
| 20212 | 2 | 3 | 4 | | IV-2 | Spaca3 | 124912 | 4-May-15 | 21118 | 2 | 3 | 4 | | IV-2 | Tekt2 | 27285 | 12-May-15 |
| 20224 | 2 | 3 | 4 | | IV-2 | Spag6 | 9576 | 12-May-15 | 21129 | 2 | 3 | 4 | | IV-2 | Tep1 | 7011 | 7-Jun-15 |
| 20230 | 2 | 3 | 4 | | IV-2 | Sparcl1 | 8404 | 12-May-15 | 21136 | 2 | 3 | 4 | | IV-2 | Tes | 26136 | 4-May-15 |
| 20253 | 2 | 3 | 4 | | IV-2 | Spata4 | 132851 | 4-May-15 | 21138 | 2 | 3 | 4 | | IV-2 | Tescl | | |
| 20257 | 2 | 3 | 4 | | IV-2 | Spata6 | 54558 | 4-May-15 | 21166 | 2 | 3 | 4 | | IV-2 | Tex33 | 339669 | 4-May-15 |
| 20264 | 2 | 3 | 4 | | IV-2 | Spats2l | 26010 | 4-May-15 | 21171 | 2 | 3 | 4 | | IV-2 | Tex40 | 25858 | 4-May-15 |
| 20267 | 2 | 3 | 4 | | IV-2 | Spcs1 | 28972 | 4-May-15 | 21174 | 2 | 3 | 4 | | IV-2 | Tfam | 7019 | 31-May-15 |
| 20284 | 2 | 3 | 4 | | IV-2 | Speer4f | | | 21193 | 2 | 3 | 4 | | IV-2 | Tfg | 10342 | 17-May-15 |
| 20321 | 2 | 3 | 4 | | IV-2 | Spink4 | 27290 | 4-May-15 | 21197 | 2 | 3 | 4 | | IV-2 | Tfpt | 29844 | 4-May-15 |
| 20335 | 2 | 3 | 4 | | IV-2 | Spn-ps | | | 21201 | 2 | 3 | 4 | | IV-2 | Tgds | 23483 | 4-May-15 |
| 20338 | 2 | 3 | 4 | | IV-2 | Spns3 | 201305 | 4-May-15 | 21206 | 2 | 3 | 4 | | IV-2 | Tgfb3 | 7043 | 23-May-15 |
| 20344 | 2 | 3 | 4 | | IV-2 | Spon2 | 10417 | 4-May-15 | 21219 | 2 | 3 | 4 | | IV-2 | Tgm4 | 7047 | 21-May-15 |
| 20345 | 2 | 3 | 4 | | IV-2 | Spop | 8405 | 17-May-15 | 21221 | 2 | 3 | 4 | | IV-2 | Tgm6 | 343641 | 23-May-15 |
| 20348 | 2 | 3 | 4 | | IV-2 | Spp2 | 6694 | 4-May-15 | 21225 | 2 | 3 | 4 | | IV-2 | Tgs1 | 96764 | 7-Jun-15 |
| 20368 | 2 | 3 | 4 | | IV-2 | Sprr2i | | | 21227 | 2 | 3 | 4 | | IV-2 | Tgtp2 | | |
| 20378 | 2 | 3 | 4 | | IV-2 | Spryd3 | 84926 | 12-May-15 | 21228 | 2 | 3 | 4 | | IV-2 | Th | 7054 | 23-May-15 |
| 20387 | 2 | 3 | 4 | | IV-2 | Sptan1 | 6709 | 4-May-15 | 21243 | 2 | 3 | 4 | | IV-2 | Theg | 51298 | 4-May-15 |
| 20389 | 2 | 3 | 4 | | IV-2 | Sptbn1 | 6711 | 4-May-15 | 21248 | 2 | 3 | 4 | | IV-2 | Themis | 387357 | 12-May-15 |
| 20397 | 2 | 3 | 4 | | IV-2 | Spty2d1 | 144108 | 4-May-15 | 21249 | 2 | 3 | 4 | | IV-2 | Themis2 | 9473 | 4-May-15 |
| 20400 | 2 | 3 | 4 | | IV-2 | Sqrdl | 58472 | 4-May-15 | 21250 | 2 | 3 | 4 | | IV-2 | Themis3 | | |
| 20409 | 2 | 3 | 4 | | IV-2 | Srd5a3 | 79644 | 23-May-15 | 21279 | 2 | 3 | 4 | | IV-2 | Tiam2 | 26230 | 4-May-15 |
| 20411 | 2 | 3 | 4 | | IV-2 | Srebf2 | 6721 | 17-May-15 | 21282 | 2 | 3 | 4 | | IV-2 | Ticrr | 90381 | 12-May-15 |
| 20420 | 2 | 3 | 4 | | IV-2 | Sri | 6717 | 31-May-15 | 21289 | 2 | 3 | 4 | | IV-2 | Tigd5 | 84948 | 4-May-15 |
| 20422 | 2 | 3 | 4 | | IV-2 | Srm | 6723 | 7-Jun-15 | 21291 | 2 | 3 | 4 | | IV-2 | Timd2 | | |
| 20429 | 2 | 3 | 4 | | IV-2 | Srp68 | 6730 | 4-May-15 | 21310 | 2 | 3 | 4 | | IV-2 | Timp1 | 7077 | 24-May-15 |
| 20439 | 2 | 3 | 4 | | IV-2 | Srr | 63826 | 4-May-15 | 21325 | 2 | 3 | 4 | | IV-2 | Tk2 | 7084 | 23-May-15 |
| 20468 | 2 | 3 | 4 | | IV-2 | Ssfa2 | 6744 | 4-May-15 | 21327 | 2 | 3 | 4 | | IV-2 | Tkfl | 8277 | 4-May-15 |
| 20470 | 2 | 3 | 4 | | IV-2 | Ssh2 | 85464 | 12-May-15 | 21330 | 2 | 3 | 4 | | IV-2 | Tlcd2 | 727910 | 4-May-15 |

Fig.22 - 20

| | | | | | | | |
|---|---|---|---|---|---|---|---|
| 21331 | 2 | 3 | 4 | IV-2 | Tldc1 | 57707 | 4-May-15 |
| 21333 | 2 | 3 | 4 | IV-2 | Tle1 | 7088 | 4-May-15 |
| 21341 | 2 | 3 | 4 | IV-2 | Tlk2 | 7093 | 4-May-15 |
| 21345 | 2 | 3 | 4 | IV-2 | Tlr11 | | |
| 21355 | 2 | 3 | 4 | IV-2 | Tlr9 | 54106 | 17-May-15 |
| 21356 | 2 | 3 | 4 | IV-2 | Tlx1 | 3195 | 4-May-15 |
| 21366 | 2 | 3 | 4 | IV-2 | Tm4sf5 | 9032 | 4-May-15 |
| 21389 | 2 | 3 | 4 | IV-2 | Tmcc1 | 23023 | 4-May-15 |
| 21391 | 2 | 3 | 4 | IV-2 | Tmcc3 | 57458 | 4-May-15 |
| 21395 | 2 | 3 | 4 | IV-2 | Tmco4 | 255104 | 4-May-15 |
| 21427 | 2 | 3 | 4 | IV-2 | Tmem119 | 338773 | 4-May-15 |
| 21428 | 2 | 3 | 4 | IV-2 | Tmem120a | 83862 | 4-May-15 |
| 21430 | 2 | 3 | 4 | IV-2 | Tmem121 | 80757 | 4-May-15 |
| 21462 | 2 | 3 | 4 | IV-2 | Tmem150cos | | |
| 21472 | 2 | 3 | 4 | IV-2 | Tmem164 | 84187 | 12-May-15 |
| 21491 | 2 | 3 | 4 | IV-2 | Tmem179b | 374395 | 4-May-15 |
| 21498 | 2 | 3 | 4 | IV-2 | Tmem183a | 92703 | 4-May-15 |
| 21501 | 2 | 3 | 4 | IV-2 | Tmem184c | 55751 | 4-May-15 |
| 21512 | 2 | 3 | 4 | IV-2 | Tmem198 | 130612 | 12-May-15 |
| 21539 | 2 | 3 | 4 | IV-2 | Tmem221 | 100130519 | 4-May-15 |
| 21540 | 2 | 3 | 4 | IV-2 | Tmem222 | 84065 | 4-May-15 |
| 21545 | 2 | 3 | 4 | IV-2 | Tmem230 | 29058 | 4-May-15 |
| 21549 | 2 | 3 | 4 | IV-2 | Tmem234 | 56063 | 12-May-15 |
| 21553 | 2 | 3 | 4 | IV-2 | Tmem238 | 388564 | 4-May-15 |
| 21564 | 2 | 3 | 4 | IV-2 | Tmem251 | 26175 | 4-May-15 |
| 21570 | 2 | 3 | 4 | IV-2 | Tmem255a | 55026 | 4-May-15 |
| 21574 | 2 | 3 | 4 | IV-2 | Tmem259 | 91304 | 4-May-15 |
| 21581 | 2 | 3 | 4 | IV-2 | Tmem29 | 29057 | 4-May-15 |
| 21589 | 2 | 3 | 4 | IV-2 | Tmem38b | 55151 | 4-May-15 |
| 21598 | 2 | 3 | 4 | IV-2 | Tmem45a | 55076 | 12-May-15 |
| 21600 | 2 | 3 | 4 | IV-2 | Tmem47 | 83604 | 4-May-15 |
| 21607 | 2 | 3 | 4 | IV-2 | Tmem52b | 120939 | 4-May-15 |
| 21610 | 2 | 3 | 4 | IV-2 | Tmem55a | 55529 | 4-May-15 |
| 21623 | 2 | 3 | 4 | IV-2 | Tmem66 | 51669 | 12-May-15 |
| 21633 | 2 | 3 | 4 | IV-2 | Tmem8 | 58986 | 4-May-15 |
| 21638 | 2 | 3 | 4 | IV-2 | Tmem86b | 255043 | 4-May-15 |
| 21643 | 2 | 3 | 4 | IV-2 | Tmem89 | 440955 | 4-May-15 |
| 21659 | 2 | 3 | 4 | IV-2 | Tmod2 | 29767 | 12-May-15 |
| 21662 | 2 | 3 | 4 | IV-2 | Tmpo | 7112 | 23-May-15 |
| 21676 | 2 | 3 | 4 | IV-2 | Tmprss4 | 56649 | 12-May-15 |
| 21682 | 2 | 3 | 4 | IV-2 | Tmsb15a | 11013 | 4-May-15 |
| 21686 | 2 | 3 | 4 | IV-2 | Tmsb4x | 7114 | 12-May-15 |
| 21706 | 2 | 3 | 4 | IV-2 | Tnfaip8l3 | 388121 | 3-May-15 |
| 21713 | 2 | 3 | 4 | IV-2 | Tnfrsf14 | 8764 | 10-May-15 |
| 21714 | 2 | 3 | 4 | IV-2 | Tnfrsf17 | 608 | 4-May-15 |
| 21723 | 2 | 3 | 4 | IV-2 | Tnfrsf26 | | |
| 21733 | 2 | 3 | 4 | IV-2 | Tnfsf14 | 8740 | 24-May-15 |
| 21750 | 2 | 3 | 4 | IV-2 | Tnn | 63923 | 4-May-15 |
| 21762 | 2 | 3 | 4 | IV-2 | Tnpo1 | 3842 | 4-May-15 |
| 21763 | 2 | 3 | 4 | IV-2 | Tnpo2 | 30000 | 12-May-15 |
| 21767 | 2 | 3 | 4 | IV-2 | Tnrc6a | 27327 | 4-May-15 |
| 21774 | 2 | 3 | 4 | IV-2 | Tob1 | 10140 | 4-May-15 |
| 21793 | 2 | 3 | 4 | IV-2 | Tonsl | 4796 | 4-May-15 |
| 21797 | 2 | 3 | 4 | IV-2 | Top2b | 7155 | 17-May-15 |
| 21805 | 2 | 3 | 4 | IV-2 | Tor1a | 1861 | 23-May-15 |
| 21815 | 2 | 3 | 4 | IV-2 | Tox4 | 9878 | 4-May-15 |
| 21817 | 2 | 3 | 4 | IV-2 | Tpbpa | | |
| 21832 | 2 | 3 | 4 | IV-2 | Tpm3 | 7170 | 23-May-15 |
| 21835 | 2 | 3 | 4 | IV-2 | Tpo | 7173 | 12-May-15 |
| 21841 | 2 | 3 | 4 | IV-2 | Tpr | 7175 | 17-May-15 |
| 21855 | 2 | 3 | 4 | IV-2 | Tra2a | 29896 | 2-Jun-15 |
| 21859 | 2 | 3 | 4 | IV-2 | Tradd | 8717 | 4-May-15 |
| 21878 | 2 | 3 | 4 | IV-2 | Trap1 | 10131 | 7-Jun-15 |
| 21892 | 2 | 3 | 4 | IV-2 | Trappc6b | 122553 | 4-May-15 |
| 21899 | 2 | 3 | 4 | IV-2 | Treh | 11181 | 12-May-15 |
| 21904 | 2 | 3 | 4 | IV-2 | Treml2 | 79865 | 4-May-15 |
| 21905 | 2 | 3 | 4 | IV-2 | Treml4 | 285852 | 4-May-15 |
| 21920 | 2 | 3 | 4 | IV-2 | Trim11 | 81559 | 4-May-15 |
| 21924 | 2 | 3 | 4 | IV-2 | Trim14 | 9830 | 12-May-15 |
| 21925 | 2 | 3 | 4 | IV-2 | Trim15 | 89870 | 7-Jun-15 |
| 21947 | 2 | 3 | 4 | IV-2 | Trim35 | 23087 | 12-May-15 |
| 21951 | 2 | 3 | 4 | IV-2 | Trim39 | 56658 | 2-Jun-15 |
| 21953 | 2 | 3 | 4 | IV-2 | Trim41 | 90933 | 4-May-15 |
| 21968 | 2 | 3 | 4 | IV-2 | Trim59 | 286827 | 4-May-15 |
| 21969 | 2 | 3 | 4 | IV-2 | Trim6 | 117854 | 4-May-15 |
| 21974 | 2 | 3 | 4 | IV-2 | Trim65 | 201292 | 12-May-15 |
| 21977 | 2 | 3 | 4 | IV-2 | Trim68 | 55128 | 4-May-15 |
| 21980 | 2 | 3 | 4 | IV-2 | Trim71 | 131405 | 7-Jun-15 |
| 21982 | 2 | 3 | 4 | IV-2 | Trim75 | 391714 | 4-May-15 |
| 21991 | 2 | 3 | 4 | IV-2 | Trip12 | 9320 | 23-May-15 |
| 21993 | 2 | 3 | 4 | IV-2 | Trip4 | 9325 | 4-May-15 |
| 22013 | 2 | 3 | 4 | IV-2 | Trmu | 55687 | 23-May-15 |
| 22019 | 2 | 3 | 4 | IV-2 | Trove2 | 6738 | 4-May-15 |
| 22025 | 2 | 3 | 4 | IV-2 | Trp53i3 | | |
| 22028 | 2 | 3 | 4 | IV-2 | Trp53rk | | |
| 22041 | 2 | 3 | 4 | IV-2 | Trpc7 | 57113 | 7-Jun-15 |
| 22044 | 2 | 3 | 4 | IV-2 | Trpm2 | 7226 | 7-Jun-15 |
| 22053 | 2 | 3 | 4 | IV-2 | Trpv1 | 7442 | 17-May-15 |
| 22055 | 2 | 3 | 4 | IV-2 | Trpv3 | 162514 | 7-Jun-15 |
| 22066 | 2 | 3 | 4 | IV-2 | Tsc1 | 7248 | 13-Jun-15 |
| 22069 | 2 | 3 | 4 | IV-2 | Tsc22d2 | 9819 | 4-May-15 |
| 22083 | 2 | 3 | 4 | IV-2 | Tshz1 | 10194 | 12-May-15 |
| 22085 | 2 | 3 | 4 | IV-2 | Tshz3 | 57616 | 4-May-15 |
| 22090 | 2 | 3 | 4 | IV-2 | Tsn | 7247 | 3-May-15 |
| 22101 | 2 | 3 | 4 | IV-2 | Tspan18 | 90139 | 4-May-15 |
| 22111 | 2 | 3 | 4 | IV-2 | Tspan7 | 7102 | 23-May-15 |
| 22122 | 2 | 3 | 4 | IV-2 | Tspy-ps | | |
| 22139 | 2 | 3 | 4 | IV-2 | Tsx | | |
| 22157 | 2 | 3 | 4 | IV-2 | Ttc26 | 79989 | 12-May-15 |
| 22174 | 2 | 3 | 4 | IV-2 | Ttc39d | | |
| 22188 | 2 | 3 | 4 | IV-2 | Ttl | 150465 | 7-Jun-15 |
| 22197 | 2 | 3 | 4 | IV-2 | Ttll5 | 23093 | 7-Jun-15 |
| 22200 | 2 | 3 | 4 | IV-2 | Ttll8 | 164714 | 4-May-15 |
| 22211 | 2 | 3 | 4 | IV-2 | Tuba1b | 10376 | 4-May-15 |
| 22213 | 2 | 3 | 4 | IV-2 | Tuba3a | | |
| 22217 | 2 | 3 | 4 | IV-2 | Tubal3 | 79861 | 7-Jun-15 |
| 22238 | 2 | 3 | 4 | IV-2 | Tug1 | 55000 | 12-May-15 |
| 22247 | 2 | 3 | 4 | IV-2 | Tusc5 | 286753 | 4-May-15 |
| 22248 | 2 | 3 | 4 | IV-2 | Tut1 | 64852 | 4-May-15 |
| 22255 | 2 | 3 | 4 | IV-2 | Twistnb | 221830 | 12-May-15 |
| 22260 | 2 | 3 | 4 | IV-2 | Txlng | 55787 | 4-May-15 |
| 22281 | 2 | 3 | 4 | IV-2 | Tyms | 7298 | 17-May-15 |
| 22282 | 2 | 3 | 4 | IV-2 | Tyms-ps | | |
| 22283 | 2 | 3 | 4 | IV-2 | Tyr | 7299 | 7-Jun-15 |
| 22284 | 2 | 3 | 4 | IV-2 | Tyro3 | 7301 | 4-May-15 |
| 22286 | 2 | 3 | 4 | IV-2 | Tyrp1 | 7306 | 7-Jun-15 |
| 22287 | 2 | 3 | 4 | IV-2 | Tysnd1 | 219743 | 21-May-15 |
| 22290 | 2 | 3 | 4 | IV-2 | Tyw5 | 129450 | 4-May-15 |
| 22311 | 2 | 3 | 4 | IV-2 | Ubap1 | 51271 | 12-May-15 |
| 22320 | 2 | 3 | 4 | IV-2 | Ube2a | 7319 | 2-Jun-15 |
| 22323 | 2 | 3 | 4 | IV-2 | Ube2cbp | 90025 | 4-May-15 |
| 22356 | 2 | 3 | 4 | IV-2 | Ube3b | 89910 | 4-May-15 |
| 22364 | 2 | 3 | 4 | IV-2 | Ubl3 | 5412 | 4-May-15 |
| 22407 | 2 | 3 | 4 | IV-2 | Ucma | 221044 | 4-May-15 |
| 22412 | 2 | 3 | 4 | IV-2 | Ucp2 | 7351 | 12-May-15 |
| 22414 | 2 | 3 | 4 | IV-2 | Uevld | 55293 | 4-May-15 |
| 22437 | 2 | 3 | 4 | IV-2 | Ugt2b1 | | |
| 22444 | 2 | 3 | 4 | IV-2 | Ugt3a1 | 133688 | 28-May-15 |
| 22445 | 2 | 3 | 4 | IV-2 | Ugt3a2 | 167127 | 28-May-15 |
| 22449 | 2 | 3 | 4 | IV-2 | Uhrf1bp1 | 54887 | 4-May-15 |
| 22454 | 2 | 3 | 4 | IV-2 | Uhk1 | 8408 | 24-May-15 |
| 22462 | 2 | 3 | 4 | IV-2 | Unc119b | 84747 | 4-May-15 |
| 22469 | 2 | 3 | 4 | IV-2 | Unc50 | 25972 | 4-May-15 |
| 22481 | 2 | 3 | 4 | IV-2 | Unk | 85451 | 21-May-15 |
| 22484 | 2 | 3 | 4 | IV-2 | Upb1 | 51733 | 17-May-15 |
| 22494 | 2 | 3 | 4 | IV-2 | Upk3bl | 100134938 | 4-May-15 |
| 22496 | 2 | 3 | 4 | IV-2 | Upp2 | 151531 | 21-May-15 |
| 22498 | 2 | 3 | 4 | IV-2 | Uqcc1 | 55245 | 12-May-15 |
| 22527 | 2 | 3 | 4 | IV-2 | Uso1 | 8615 | 12-May-15 |
| 22533 | 2 | 3 | 4 | IV-2 | Usp14 | 9097 | 4-May-15 |
| 22590 | 2 | 3 | 4 | IV-2 | Utp15 | 84135 | 4-May-15 |
| 22618 | 2 | 3 | 4 | IV-2 | Vapa | 9218 | 4-May-15 |
| 22626 | 2 | 3 | 4 | IV-2 | Vat1 | 10493 | 13-Jun-15 |
| 22630 | 2 | 3 | 4 | IV-2 | Vav2 | 7410 | 4-May-15 |
| 22637 | 2 | 3 | 4 | IV-2 | Vcan | 1462 | 23-May-15 |
| 22638 | 2 | 3 | 4 | IV-2 | Vcl | 7414 | 28-May-15 |
| 22649 | 2 | 3 | 4 | IV-2 | Veph1 | 79674 | 4-May-15 |
| 22655 | 2 | 3 | 4 | IV-2 | Vgll3 | 389136 | 4-May-15 |
| 22656 | 2 | 3 | 4 | IV-2 | Vgll4 | 9686 | 12-May-15 |
| 22657 | 2 | 3 | 4 | IV-2 | Vhl | 7428 | 31-May-15 |
| 22660 | 2 | 3 | 4 | IV-2 | Vim | 7431 | 17-May-15 |
| 23013 | 2 | 3 | 4 | IV-2 | Vps11 | 55823 | 12-May-15 |
| 23044 | 2 | 3 | 4 | IV-2 | Vps9d1 | 9605 | 4-May-15 |
| 23055 | 2 | 3 | 4 | IV-2 | Vsnl1 | 7447 | 4-May-15 |
| 23068 | 2 | 3 | 4 | IV-2 | Vwa1 | 64856 | 4-May-15 |
| 23075 | 2 | 3 | 4 | IV-2 | Vwa8 | 23078 | 4-May-15 |
| 23088 | 2 | 3 | 4 | IV-2 | Wasf1 | 8936 | 4-May-15 |
| 23091 | 2 | 3 | 4 | IV-2 | Wash | 100287171 | 7-Jun-15 |
| 23108 | 2 | 3 | 4 | IV-2 | Wdfy3 | 23001 | 21-May-15 |
| 23159 | 2 | 3 | 4 | IV-2 | Wdr72 | 256764 | 4-May-15 |
| 23210 | 2 | 3 | 4 | IV-2 | Wipf1 | 7456 | 4-May-15 |
| 23217 | 2 | 3 | 4 | IV-2 | Wisp3 | 8838 | 4-May-15 |
| 23227 | 2 | 3 | 4 | IV-2 | Wnt11 | 7481 | 12-May-15 |
| 23231 | 2 | 3 | 4 | IV-2 | Wnt3 | 7473 | 23-May-15 |
| 23265 | 2 | 3 | 4 | IV-2 | Xcr1 | 2829 | 4-May-15 |
| 23270 | 2 | 3 | 4 | IV-2 | Xist | 7503 | 7-Jun-15 |
| 23274 | 2 | 3 | 4 | IV-2 | Xkr6 | 286046 | 4-May-15 |
| 23279 | 2 | 3 | 4 | IV-2 | Xlr | | |
| 23282 | 2 | 3 | 4 | IV-2 | Xlr3c | | |
| 23298 | 2 | 3 | 4 | IV-2 | Xpo5 | 57510 | 4-May-15 |
| 23311 | 2 | 3 | 4 | IV-2 | Xrn2 | 22803 | 4-May-15 |
| 23316 | 2 | 3 | 4 | IV-2 | Xylt2 | 64132 | 31-May-15 |
| 23339 | 2 | 3 | 4 | IV-2 | Ykt6 | 10652 | 23-May-15 |
| 23343 | 2 | 3 | 4 | IV-2 | Ypel1 | 29799 | 2-Jun-15 |
| 23347 | 2 | 3 | 4 | IV-2 | Ypel5 | 51646 | 12-May-15 |
| 23380 | 2 | 3 | 4 | IV-2 | Zbtb17 | 7709 | 3-May-15 |
| 23384 | 2 | 3 | 4 | IV-2 | Zbtb21 | 49854 | 28-May-15 |
| 23391 | 2 | 3 | 4 | IV-2 | Zbtb33 | 10009 | 12-May-15 |
| 23395 | 2 | 3 | 4 | IV-2 | Zbtb39 | 9880 | 4-May-15 |
| 23404 | 2 | 3 | 4 | IV-2 | Zbtb48 | 3104 | 4-May-15 |
| 23414 | 2 | 3 | 4 | IV-2 | Zbtb9 | 221504 | 4-May-15 |
| 23416 | 2 | 3 | 4 | IV-2 | Zc2hc1a | 51101 | 4-May-15 |
| 23425 | 2 | 3 | 4 | IV-2 | Zc3h13 | 23091 | 12-May-15 |
| 23459 | 2 | 3 | 4 | IV-2 | Zdhhc1 | 29800 | 4-May-15 |
| 23470 | 2 | 3 | 4 | IV-2 | Zdhhc20 | 253832 | 12-May-15 |
| 23474 | 2 | 3 | 4 | IV-2 | Zdhhc24 | 254359 | 4-May-15 |
| 23485 | 2 | 3 | 4 | IV-2 | Zeb2os | | |
| 23488 | 2 | 3 | 4 | IV-2 | Zfand1 | 79752 | 4-May-15 |
| 23523 | 2 | 3 | 4 | IV-2 | Zfp14 | 57677 | 4-May-15 |
| 23531 | 2 | 3 | 4 | IV-2 | Zfp174 | | |
| 23597 | 2 | 3 | 4 | IV-2 | Zfp367 | | |
| 23599 | 2 | 3 | 4 | IV-2 | Zfp36l1 | 677 | 4-May-15 |
| 23604 | 2 | 3 | 4 | IV-2 | Zfp383 | | |

Fig.22-21

| | | | | | | | | | | | | | | |
|---|---|---|---|---|---|---|---|---|---|---|---|---|---|---|
| 23608 | 2 | 3 | 4 | IV-2 | Zfp385c | | | | 453 | 2 | 3 | 4 | IV-1 | 1810022K09Rik |
| 23615 | 2 | 3 | 4 | IV-2 | Zfp40 | | | | 458 | 2 | 3 | 4 | IV-1 | 1810032O08Rik |
| 23620 | 2 | 3 | 4 | IV-2 | Zfp414 | 84330 | 4-May-15 | | 464 | 2 | 3 | 4 | IV-1 | 1810044D09Rik |
| 23652 | 2 | 3 | 4 | IV-2 | Zfp444 | | | | 465 | 2 | 3 | 4 | IV-1 | 1810046K07Rik |
| 23659 | 2 | 3 | 4 | IV-2 | Zfp518b | | | | 469 | 2 | 3 | 4 | IV-1 | 1810062G17Rik |
| 23660 | 2 | 3 | 4 | IV-2 | Zfp52 | | | | 471 | 2 | 3 | 4 | IV-1 | 1810064F22Rik |
| 23665 | 2 | 3 | 4 | IV-2 | Zfp53 | | | | 475 | 2 | 3 | 4 | IV-1 | 2010003K11Rik |
| 23669 | 2 | 3 | 4 | IV-2 | Zfp54 | | | | 478 | 2 | 3 | 4 | IV-1 | 2010010A06Rik |
| 23672 | 2 | 3 | 4 | IV-2 | Zfp553 | | | | 481 | 2 | 3 | 4 | IV-1 | 2010016J18Rik |
| 23686 | 2 | 3 | 4 | IV-2 | Zfp59 | | | | 485 | 2 | 3 | 4 | IV-1 | 2010107G12Rik |
| 23698 | 2 | 3 | 4 | IV-2 | Zfp608 | | | | 486 | 2 | 3 | 4 | IV-1 | 2010107G23Rik |
| 23715 | 2 | 3 | 4 | IV-2 | Zfp644 | | | | 488 | 2 | 3 | 4 | IV-1 | 2010109I03Rik |
| 23722 | 2 | 3 | 4 | IV-2 | Zfp652os | | | | 490 | 2 | 3 | 4 | IV-1 | 2010204K13Rik |
| 23737 | 2 | 3 | 4 | IV-2 | Zfp689 | | | | 491 | 2 | 3 | 4 | IV-1 | 2010300C02Rik |
| 23792 | 2 | 3 | 4 | IV-2 | Zfp810 | | | | 496 | 2 | 3 | 4 | IV-1 | 2200002D01Rik |
| 23797 | 2 | 3 | 4 | IV-2 | Zfp821 | | | | 506 | 2 | 3 | 4 | IV-1 | 2210039B01Rik |
| 23816 | 2 | 3 | 4 | IV-2 | Zfp871 | | | | 508 | 2 | 3 | 4 | IV-1 | 2210407C18Rik |
| 23818 | 2 | 3 | 4 | IV-2 | Zfp873 | | | | 509 | 2 | 3 | 4 | IV-1 | 2210408F21Rik |
| 23819 | 2 | 3 | 4 | IV-2 | Zfp874a | | | | 511 | 2 | 3 | 4 | IV-1 | 2210409D07Rik |
| 23830 | 2 | 3 | 4 | IV-2 | Zfp931 | | | | 519 | 2 | 3 | 4 | IV-1 | 2300006B03Rik |
| 23831 | 2 | 3 | 4 | IV-2 | Zfp932 | | | | 522 | 2 | 3 | 4 | IV-1 | 2310001K24Rik |
| 23837 | 2 | 3 | 4 | IV-2 | Zfp938 | | | | 525 | 2 | 3 | 4 | IV-1 | 2310002J15Rik |
| 23883 | 2 | 3 | 4 | IV-2 | Zglp1 | 100125288 | 4-May-15 | | 535 | 2 | 3 | 4 | IV-1 | 2310009B15Rik |
| 23886 | 2 | 3 | 4 | IV-2 | Zhx1 | 11244 | 4-May-15 | | 543 | 2 | 3 | 4 | IV-1 | 2310020H05Rik |
| 23907 | 2 | 3 | 4 | IV-2 | Zkscan8 | 7745 | 14-May-15 | | 547 | 2 | 3 | 4 | IV-1 | 2310030G06Rik |
| 23936 | 2 | 3 | 4 | IV-2 | Znrd1as | 80862 | 12-May-15 | | 550 | 2 | 3 | 4 | IV-1 | 2310034G01Rik |
| 23938 | 2 | 3 | 4 | IV-2 | Zorf2 | 223082 | 23-May-15 | | 551 | 2 | 3 | 4 | IV-1 | 2310034O05Rik |
| 23983 | 2 | 3 | 4 | IV-2 | Zwint | 11130 | 4-May-15 | | 556 | 2 | 3 | 4 | IV-1 | 2310040G24Rik |
| 1 | 2 | 3 | 4 | IV-1 | 0610005C13Rik | | | | 557 | 2 | 3 | 4 | IV-1 | 2310042E22Rik |
| 9 | 2 | 3 | 4 | IV-1 | 0610011F06Rik | | | | 569 | 2 | 3 | 4 | IV-1 | 2310065F04Rik |
| 17 | 2 | 3 | 4 | IV-1 | 0610040B10Rik | | | | 575 | 2 | 3 | 4 | IV-1 | 2310081J21Rik |
| 20 | 2 | 3 | 4 | IV-1 | 0610043K17Rik | | | | 580 | 2 | 3 | 4 | IV-1 | 2410004N09Rik |
| 22 | 2 | 3 | 4 | IV-1 | 1100001G20Rik | | | | 581 | 2 | 3 | 4 | IV-1 | 2410004P03Rik |
| 29 | 2 | 3 | 4 | IV-1 | 1110008F13Rik | | | | 582 | 2 | 3 | 4 | IV-1 | 2410006H16Rik |
| 45 | 2 | 3 | 4 | IV-1 | 1110038I12Rik | | | | 612 | 2 | 3 | 4 | IV-1 | 2610016A17Rik |
| 47 | 2 | 3 | 4 | IV-1 | 1110046L04Rik | | | | 626 | 2 | 3 | 4 | IV-1 | 2610203C20Rik |
| 55 | 2 | 3 | 4 | IV-1 | 1190002F15Rik | | | | 638 | 2 | 3 | 4 | IV-1 | 2610524H06Rik |
| 58 | 2 | 3 | 4 | IV-1 | 1190005I06Rik | | | | 640 | 2 | 3 | 4 | IV-1 | 2610528J11Rik |
| 62 | 2 | 3 | 4 | IV-1 | 1300002K09Rik | | | | 642 | 2 | 3 | 4 | IV-1 | 2700038G22Rik |
| 63 | 2 | 3 | 4 | IV-1 | 1300017J02Rik | | | | 656 | 2 | 3 | 4 | IV-1 | 2700097O09Rik |
| 66 | 2 | 3 | 4 | IV-1 | 1500009L16Rik | | | | 663 | 2 | 3 | 4 | IV-1 | 2810008D09Rik |
| 67 | 2 | 3 | 4 | IV-1 | 1500011B03Rik | | | | 668 | 2 | 3 | 4 | IV-1 | 2810032G03Rik |
| 74 | 2 | 3 | 4 | IV-1 | 1500017E21Rik | | | | 676 | 2 | 3 | 4 | IV-1 | 2810408A11Rik |
| 78 | 2 | 3 | 4 | IV-1 | 1600010M07Rik | | | | 688 | 2 | 3 | 4 | IV-1 | 2810468N07Rik |
| 81 | 2 | 3 | 4 | IV-1 | 1600014C23Rik | | | | 691 | 2 | 3 | 4 | IV-1 | 2900005J15Rik |
| 84 | 2 | 3 | 4 | IV-1 | 1600016N20Rik | | | | 696 | 2 | 3 | 4 | IV-1 | 2900041M22Rik |
| 86 | 2 | 3 | 4 | IV-1 | 1600020E01Rik | | | | 702 | 2 | 3 | 4 | IV-1 | 2900076A07Rik |
| 92 | 2 | 3 | 4 | IV-1 | 1700001C02Rik | | | | 707 | 2 | 3 | 4 | IV-1 | 3000002C10Rik |
| 97 | 2 | 3 | 4 | IV-1 | 1700001G17Rik | | | | 715 | 2 | 3 | 4 | IV-1 | 3110009E18Rik |
| 98 | 2 | 3 | 4 | IV-1 | 1700001J03Rik | | | | 719 | 2 | 3 | 4 | IV-1 | 3110021N24Rik |
| 104 | 2 | 3 | 4 | IV-1 | 1700001O22Rik | | | | 737 | 2 | 3 | 4 | IV-1 | 3300005D01Rik |
| 107 | 2 | 3 | 4 | IV-1 | 1700003D09Rik | | | | 760 | 2 | 3 | 4 | IV-1 | 4833411C07Rik |
| 108 | 2 | 3 | 4 | IV-1 | 1700003E16Rik | | | | 763 | 2 | 3 | 4 | IV-1 | 4833418N02Rik |
| 110 | 2 | 3 | 4 | IV-1 | 1700003F12Rik | | | | 764 | 2 | 3 | 4 | IV-1 | 4833419F23Rik |
| 127 | 2 | 3 | 4 | IV-1 | 1700007K13Rik | | | | 767 | 2 | 3 | 4 | IV-1 | 4833423E24Rik |
| 137 | 2 | 3 | 4 | IV-1 | 1700009J07Rik | | | | 785 | 2 | 3 | 4 | IV-1 | 4921511I17Rik |
| 139 | 2 | 3 | 4 | IV-1 | 1700009P17Rik | | | | 797 | 2 | 3 | 4 | IV-1 | 4921533L20Rik |
| 142 | 2 | 3 | 4 | IV-1 | 1700010I02Rik | | | | 815 | 2 | 3 | 4 | IV-1 | 4930404N11Rik |
| 149 | 2 | 3 | 4 | IV-1 | 1700011H14Rik | | | | 842 | 2 | 3 | 4 | IV-1 | 4930426D05Rik |
| 153 | 2 | 3 | 4 | IV-1 | 1700012A03Rik | | | | 852 | 2 | 3 | 4 | IV-1 | 4930429F24Rik |
| 155 | 2 | 3 | 4 | IV-1 | 1700012B09Rik | | | | 873 | 2 | 3 | 4 | IV-1 | 4930442L01Rik |
| 156 | 2 | 3 | 4 | IV-1 | 1700012D01Rik | | | | 881 | 2 | 3 | 4 | IV-1 | 4930447J18Rik |
| 157 | 2 | 3 | 4 | IV-1 | 1700012D14Rik | | | | 896 | 2 | 3 | 4 | IV-1 | 4930452A19Rik |
| 172 | 2 | 3 | 4 | IV-1 | 1700016L19Rik | | | | 904 | 2 | 3 | 4 | IV-1 | 4930455C13Rik |
| 174 | 2 | 3 | 4 | IV-1 | 1700016L21Rik | | | | 912 | 2 | 3 | 4 | IV-1 | 4930481G14Rik |
| 191 | 2 | 3 | 4 | IV-1 | 1700019D03Rik | | | | 930 | 2 | 3 | 4 | IV-1 | 4930474M22Rik |
| 203 | 2 | 3 | 4 | IV-1 | 1700020L24Rik | | | | 940 | 2 | 3 | 4 | IV-1 | 4930481A15Rik |
| 221 | 2 | 3 | 4 | IV-1 | 1700023L04Rik | | | | 948 | 2 | 3 | 4 | IV-1 | 4930487D11Rik |
| 226 | 2 | 3 | 4 | IV-1 | 1700024P16Rik | | | | 949 | 2 | 3 | 4 | IV-1 | 4930487H11Rik |
| 235 | 2 | 3 | 4 | IV-1 | 1700026O08Rik | | | | 958 | 2 | 3 | 4 | IV-1 | 4930503B20Rik |
| 238 | 2 | 3 | 4 | IV-1 | 1700026L06Rik | | | | 967 | 2 | 3 | 4 | IV-1 | 4930506C21Rik |
| 244 | 2 | 3 | 4 | IV-1 | 1700028B04Rik | | | | 968 | 2 | 3 | 4 | IV-1 | 4930506M07Rik |
| 258 | 2 | 3 | 4 | IV-1 | 1700029J07Rik | | | | 983 | 2 | 3 | 4 | IV-1 | 4930515G16Rik |
| 262 | 2 | 3 | 4 | IV-1 | 1700030A11Rik | | | | 994 | 2 | 3 | 4 | IV-1 | 4930520O04Rik |
| 263 | 2 | 3 | 4 | IV-1 | 1700030C10Rik | | | | 1018 | 2 | 3 | 4 | IV-1 | 4930529L06Rik |
| 286 | 2 | 3 | 4 | IV-1 | 1700037C18Rik | | | | 1026 | 2 | 3 | 4 | IV-1 | 4930539J05Rik |
| 291 | 2 | 3 | 4 | IV-1 | 1700041C23Rik | | | | 1068 | 2 | 3 | 4 | IV-1 | 4930562C15Rik |
| 304 | 2 | 3 | 4 | IV-1 | 1700047I17Rik2 | | | | 1070 | 2 | 3 | 4 | IV-1 | 4930562D23Rik |
| 348 | 2 | 3 | 4 | IV-1 | 1700067K01Rik | | | | 1104 | 2 | 3 | 4 | IV-1 | 4930581F22Rik |
| 353 | 2 | 3 | 4 | IV-1 | 1700071M16Rik | | | | 1145 | 2 | 3 | 4 | IV-1 | 4931431C16Rik |
| 363 | 2 | 3 | 4 | IV-1 | 1700084C01Rik | | | | 1164 | 2 | 3 | 4 | IV-1 | 4932438H23Rik |
| 364 | 2 | 3 | 4 | IV-1 | 1700084E18Rik | | | | 1184 | 2 | 3 | 4 | IV-1 | 4933402P03Rik |
| 372 | 2 | 3 | 4 | IV-1 | 1700092C02Rik | | | | 1188 | 2 | 3 | 4 | IV-1 | 4933404O12Rik |
| 376 | 2 | 3 | 4 | IV-1 | 1700092M07Rik | | | | 1193 | 2 | 3 | 4 | IV-1 | 4933406C10Rik |
| 388 | 2 | 3 | 4 | IV-1 | 1700101I11Rik | | | | 1223 | 2 | 3 | 4 | IV-1 | 4933415F23Rik |
| 404 | 2 | 3 | 4 | IV-1 | 1700110K17Rik | | | | 1230 | 2 | 3 | 4 | IV-1 | 4933417D19Rik |
| 406 | 2 | 3 | 4 | IV-1 | 1700112L06Rik | | | | 1248 | 2 | 3 | 4 | IV-1 | 4933427J22Rik |
| 411 | 2 | 3 | 4 | IV-1 | 1700119H24Rik | | | | 1288 | 2 | 3 | 4 | IV-1 | 5033403H07Rik |
| 412 | 2 | 3 | 4 | IV-1 | 1700120C14Rik | | | | 1297 | 2 | 3 | 4 | IV-1 | 5330439I14Rik |
| 415 | 2 | 3 | 4 | IV-1 | 1700120K04Rik | | | | 1302 | 2 | 3 | 4 | IV-1 | 5430405H02Rik |
| 426 | 2 | 3 | 4 | IV-1 | 1700124L16Rik | | | | 1303 | 2 | 3 | 4 | IV-1 | 5430416N02Rik |
| 441 | 2 | 3 | 4 | IV-1 | 1810010D01Rik | | | | 1308 | 2 | 3 | 4 | IV-1 | 5430421N21Rik |
| 442 | 2 | 3 | 4 | IV-1 | 1810010H24Rik | | | | 1310 | 2 | 3 | 4 | IV-1 | 5430427M07Rik |
| 443 | 2 | 3 | 4 | IV-1 | 1810011H11Rik | | | | 1314 | 2 | 3 | 4 | IV-1 | 5430435G22Rik |
| 444 | 2 | 3 | 4 | IV-1 | 1810011O10Rik | | | | 1322 | 2 | 3 | 4 | IV-1 | 5730408K05Rik |
| 445 | 2 | 3 | 4 | IV-1 | 1810012K16Rik | | | | 1325 | 2 | 3 | 4 | IV-1 | 5730416F02Rik |
| 452 | 2 | 3 | 4 | IV-1 | 1810021B22Rik | | | | 1334 | 2 | 3 | 4 | IV-1 | 5730507C01Rik |

Fig.22 - 22

| | | | | | | | | | | | | | | | |
|---|---|---|---|---|---|---|---|---|---|---|---|---|---|---|---|
| 1337 | 2 | 3 | 4 | | IV-1 | 5730559C18Rik | | | 1956 | 2 | 3 | 4 | IV-1 | Adamts15 | 170689 | 17-May-15 |
| 1346 | 2 | 3 | 4 | | IV-1 | 5830428M24Rik | | | 1967 | 2 | 3 | 4 | IV-1 | Adamts7 | 11173 | 4-May-15 |
| 1351 | 2 | 3 | 4 | | IV-1 | 5930403N14Rik | | | 1971 | 2 | 3 | 4 | IV-1 | Adamtsl2 | 9719 | 23-May-15 |
| 1357 | 2 | 3 | 4 | | IV-1 | 6030419C18Rik | | | 1973 | 2 | 3 | 4 | IV-1 | Adamtsl4 | 54507 | 23-May-15 |
| 1362 | 2 | 3 | 4 | | IV-1 | 6030468B19Rik | | | 1978 | 2 | 3 | 4 | IV-1 | Adarb1 | 104 | 12-May-15 |
| 1374 | 2 | 3 | 4 | | IV-1 | 6330418K02Rik | | | 1986 | 2 | 3 | 4 | IV-1 | Adck3 | 56997 | 4-May-15 |
| 1383 | 2 | 3 | 4 | | IV-1 | 6430571L13Rik | | | 1991 | 2 | 3 | 4 | IV-1 | Adcy2 | 108 | 4-May-15 |
| 1390 | 2 | 3 | 4 | | IV-1 | 6720418L17Rik | | | 1997 | 2 | 3 | 4 | IV-1 | Adcy8 | 114 | 12-May-15 |
| 1409 | 2 | 3 | 4 | | IV-1 | 8430419L09Rik | | | 2000 | 2 | 3 | 4 | IV-1 | Adcyap1r1 | 117 | 17-May-15 |
| 1445 | 2 | 3 | 4 | | IV-1 | 9230102O04Rik | | | 2011 | 2 | 3 | 4 | IV-1 | Adhfe1 | 137872 | 4-May-15 |
| 1447 | 2 | 3 | 4 | | IV-1 | 9230105E05Rik | | | 2018 | 2 | 3 | 4 | IV-1 | Adm | 133 | 17-May-15 |
| 1448 | 2 | 3 | 4 | | IV-1 | 9230110C19Rik | | | 2023 | 2 | 3 | 4 | IV-1 | Adora1 | 134 | 21-May-15 |
| 1453 | 2 | 3 | 4 | | IV-1 | 9230116L04Rik | | | 2026 | 2 | 3 | 4 | IV-1 | Adora3 | 140 | 12-May-15 |
| 1459 | 2 | 3 | 4 | | IV-1 | 9330133O14Rik | | | 2029 | 2 | 3 | 4 | IV-1 | Adprhl1 | 113622 | 4-May-15 |
| 1466 | 2 | 3 | 4 | | IV-1 | 9330175E14Rik | | | 2037 | 2 | 3 | 4 | IV-1 | Adra2c | 152 | 4-May-15 |
| 1490 | 2 | 3 | 4 | | IV-1 | 9530002B09Rik | | | 2039 | 2 | 3 | 4 | IV-1 | Adrb2 | 154 | 28-May-15 |
| 1493 | 2 | 3 | 4 | | IV-1 | 9530026P05Rik | | | 2040 | 2 | 3 | 4 | IV-1 | Adrb3 | 155 | 4-May-15 |
| 1497 | 2 | 3 | 4 | | IV-1 | 9530052E02Rik | | | 2046 | 2 | 3 | 4 | IV-1 | Adssl1 | 122622 | 12-May-15 |
| 1502 | 2 | 3 | 4 | | IV-1 | 9530080O11Rik | | | 2047 | 2 | 3 | 4 | IV-1 | Adtrp | 84830 | 4-May-15 |
| 1514 | 2 | 3 | 4 | | IV-1 | 9930012K11Rik | | | 2054 | 2 | 3 | 4 | IV-1 | AF251705 | | |
| 1541 | 2 | 3 | 4 | | IV-1 | A230103J11Rik | | | 2061 | 2 | 3 | 4 | IV-1 | AF529169 | | |
| 1558 | 2 | 3 | 4 | | IV-1 | A330076C08Rik | | | 2089 | 2 | 3 | 4 | IV-1 | Agl | 178 | 23-May-15 |
| 1573 | 2 | 3 | 4 | | IV-1 | A4galt | 53947 | 12-May-15 | 2091 | 2 | 3 | 4 | IV-1 | Agmo | 392636 | 4-May-15 |
| 1576 | 2 | 3 | 4 | | IV-1 | A530013C23Rik | | | 2093 | 2 | 3 | 4 | IV-1 | Ago2 | 27161 | 28-May-15 |
| 1595 | 2 | 3 | 4 | | IV-1 | A630023A22Rik | | | 2097 | 2 | 3 | 4 | IV-1 | Agpat2 | 10555 | 23-May-15 |
| 1598 | 2 | 3 | 4 | | IV-1 | A630066F11Rik | | | 2102 | 2 | 3 | 4 | IV-1 | Agpat9 | 84803 | 4-May-15 |
| 1600 | 2 | 3 | 4 | | IV-1 | A630073D07Rik | | | 2108 | 2 | 3 | 4 | IV-1 | Agt | 183 | 7-Jun-15 |
| 1609 | 2 | 3 | 4 | | IV-1 | A730017C20Rik | | | 2121 | 2 | 3 | 4 | IV-1 | Ahi1 | 54806 | 23-May-15 |
| 1613 | 2 | 3 | 4 | | IV-1 | A730020M07Rik | | | 2141 | 2 | 3 | 4 | IV-1 | AI463170 | | |
| 1614 | 2 | 3 | 4 | | IV-1 | A730036J17Rik | | | 2142 | 2 | 3 | 4 | IV-1 | AI464131 | | |
| 1645 | 2 | 3 | 4 | | IV-1 | A930015D03Rik | | | 2146 | 2 | 3 | 4 | IV-1 | AI507597 | | |
| 1654 | 2 | 3 | 4 | | IV-1 | AA413626 | | | 2151 | 2 | 3 | 4 | IV-1 | AI646519 | | |
| 1655 | 2 | 3 | 4 | | IV-1 | AA414768 | | | 2152 | 2 | 3 | 4 | IV-1 | AI661453 | | |
| 1657 | 2 | 3 | 4 | | IV-1 | AA465934 | | | 2153 | 2 | 3 | 4 | IV-1 | AI662270 | | |
| 1658 | 2 | 3 | 4 | | IV-1 | AA467197 | | | 2165 | 2 | 3 | 4 | IV-1 | Aif1 | 199 | 4-May-15 |
| 1659 | 2 | 3 | 4 | | IV-1 | AA474831 | | | 2168 | 2 | 3 | 4 | IV-1 | Aifm2 | 84884 | 4-May-15 |
| 1666 | 2 | 3 | 4 | | IV-1 | AA986860 | | | 2183 | 2 | 3 | 4 | IV-1 | Ak1 | 203 | 12-May-15 |
| 1670 | 2 | 3 | 4 | | IV-1 | Aadac | 13 | 4-May-15 | 2187 | 2 | 3 | 4 | IV-1 | Ak4 | 205 | 12-May-15 |
| 1687 | 2 | 3 | 4 | | IV-1 | Aass | 10157 | 4-May-15 | 2201 | 2 | 3 | 4 | IV-1 | Akap4 | 8852 | 4-May-15 |
| 1691 | 2 | 3 | 4 | | IV-1 | AB124611 | | | 2203 | 2 | 3 | 4 | IV-1 | Akap6 | 9472 | 4-May-15 |
| 1700 | 2 | 3 | 4 | | IV-1 | Abca2 | 20 | 12-May-15 | 2219 | 2 | 3 | 4 | IV-1 | Akr1c12 | | |
| 1704 | 2 | 3 | 4 | | IV-1 | Abca6 | 23460 | 12-May-15 | 2220 | 2 | 3 | 4 | IV-1 | Akr1c13 | | |
| 1706 | 2 | 3 | 4 | | IV-1 | Abca8a | | | 2223 | 2 | 3 | 4 | IV-1 | Akr1c19 | | |
| 1709 | 2 | 3 | 4 | | IV-1 | Abcb10 | 23456 | 12-May-15 | 2230 | 2 | 3 | 4 | IV-1 | Akr7a5 | | |
| 1711 | 2 | 3 | 4 | | IV-1 | Abcb1a | | | 2236 | 2 | 3 | 4 | IV-1 | Alad | 210 | 4-May-15 |
| 1713 | 2 | 3 | 4 | | IV-1 | Abcb4 | 5244 | 12-May-15 | 2244 | 2 | 3 | 4 | IV-1 | Aldh1a2 | 8854 | 23-May-15 |
| 1714 | 2 | 3 | 4 | | IV-1 | Abcb5 | 340273 | 4-May-15 | 2248 | 2 | 3 | 4 | IV-1 | Aldh1a7 | | |
| 1722 | 2 | 3 | 4 | | IV-1 | Abcc2 | 1244 | 17-May-15 | 2253 | 2 | 3 | 4 | IV-1 | Aldh3b1 | 221 | 23-May-15 |
| 1723 | 2 | 3 | 4 | | IV-1 | Abcc3 | 8714 | 17-May-15 | 2254 | 2 | 3 | 4 | IV-1 | Aldh3b2 | 222 | 23-May-15 |
| 1724 | 2 | 3 | 4 | | IV-1 | Abcc4 | 10257 | 12-May-15 | 2255 | 2 | 3 | 4 | IV-1 | Aldh4a1 | 8659 | 23-May-15 |
| 1728 | 2 | 3 | 4 | | IV-1 | Abcc9 | 10060 | 23-May-15 | 2256 | 2 | 3 | 4 | IV-1 | Aldh5a1 | 7915 | 23-May-15 |
| 1730 | 2 | 3 | 4 | | IV-1 | Abcd2 | 225 | 7-Jun-15 | 2257 | 2 | 3 | 4 | IV-1 | Aldh6a1 | 4329 | 23-May-15 |
| 1741 | 2 | 3 | 4 | | IV-1 | Abcg5 | 64240 | 23-May-15 | 2261 | 2 | 3 | 4 | IV-1 | Aldoa | 226 | 4-May-15 |
| 1746 | 2 | 3 | 4 | | IV-1 | Abhd1os | | | 2262 | 2 | 3 | 4 | IV-1 | Aldoart1 | | |
| 1748 | 2 | 3 | 4 | | IV-1 | Abhd12b | 145447 | 4-May-15 | 2263 | 2 | 3 | 4 | IV-1 | Aldoart2 | | |
| 1751 | 2 | 3 | 4 | | IV-1 | Abhd14b | 84836 | 4-May-15 | 2267 | 2 | 3 | 4 | IV-1 | Alg10b | 144245 | 12-May-15 |
| 1758 | 2 | 3 | 4 | | IV-1 | Abhd2 | 11057 | 23-May-15 | 2280 | 2 | 3 | 4 | IV-1 | Alkbh2 | 121642 | 12-May-15 |
| 1763 | 2 | 3 | 4 | | IV-1 | Abhd8 | 79575 | 4-May-15 | 2285 | 2 | 3 | 4 | IV-1 | Alkbh7 | 84266 | 4-May-15 |
| 1765 | 2 | 3 | 4 | | IV-1 | Abi2 | 10152 | 12-May-15 | 2293 | 2 | 3 | 4 | IV-1 | Alox15 | 246 | 4-May-15 |
| 1771 | 2 | 3 | 4 | | IV-1 | Ablim2 | 84448 | 12-May-15 | 2294 | 2 | 3 | 4 | IV-1 | Alox5 | 240 | 10-May-15 |
| 1772 | 2 | 3 | 4 | | IV-1 | Ablim3 | 22885 | 12-May-15 | 2295 | 2 | 3 | 4 | IV-1 | Alox5ap | 241 | 4-May-15 |
| 1773 | 2 | 3 | 4 | | IV-1 | Abo | 28 | 12-May-15 | 2300 | 2 | 3 | 4 | IV-1 | Alpk2 | 115701 | 4-May-15 |
| 1781 | 2 | 3 | 4 | | IV-1 | Acaa1b | | | 2307 | 2 | 3 | 4 | IV-1 | Als2cr12 | 130540 | 12-May-15 |
| 1783 | 2 | 3 | 4 | | IV-1 | Acaca | 31 | 4-May-15 | 2311 | 2 | 3 | 4 | IV-1 | Alyref | 10189 | 4-May-15 |
| 1784 | 2 | 3 | 4 | | IV-1 | Acacb | 32 | 12-May-15 | 2315 | 2 | 3 | 4 | IV-1 | Ambp | 259 | 12-May-15 |
| 1796 | 2 | 3 | 4 | | IV-1 | Acap1 | 9744 | 4-May-15 | 2328 | 2 | 3 | 4 | IV-1 | Amica1 | 120425 | 4-May-15 |
| 1810 | 2 | 3 | 4 | | IV-1 | Ace | 1636 | 24-May-15 | 2329 | 2 | 3 | 4 | IV-1 | Amigo1 | 57463 | 2-Jun-15 |
| 1816 | 2 | 3 | 4 | | IV-1 | Ache | 43 | 28-May-15 | 2330 | 2 | 3 | 4 | IV-1 | Amigo2 | 347902 | 4-May-15 |
| 1818 | 2 | 3 | 4 | | IV-1 | Ackr1 | 2532 | 21-May-15 | 2331 | 2 | 3 | 4 | IV-1 | Amigo3 | 386724 | 4-May-15 |
| 1820 | 2 | 3 | 4 | | IV-1 | Ackr3 | 57007 | 31-May-15 | 2335 | 2 | 3 | 4 | IV-1 | Amn | 196394 | 4-May-15 |
| 1822 | 2 | 3 | 4 | | IV-1 | Acly | 47 | 12-May-15 | 2336 | 2 | 3 | 4 | IV-1 | Amot | 154796 | 4-May-15 |
| 1824 | 2 | 3 | 4 | | IV-1 | Acn9 | 57001 | 4-May-15 | 2343 | 2 | 3 | 4 | IV-1 | Amt | 275 | 23-May-15 |
| 1825 | 2 | 3 | 4 | | IV-1 | Acnat1 | | | 2361 | 2 | 3 | 4 | IV-1 | Ang | 283 | 23-May-15 |
| 1829 | 2 | 3 | 4 | | IV-1 | Acot1 | 641371 | 4-May-15 | 2374 | 2 | 3 | 4 | IV-1 | Angptl3 | 27329 | 4-May-15 |
| 1832 | 2 | 3 | 4 | | IV-1 | Acot12 | 134526 | 4-May-15 | 2375 | 2 | 3 | 4 | IV-1 | Angptl4 | 51129 | 4-May-15 |
| 1834 | 2 | 3 | 4 | | IV-1 | Acot2 | 10965 | 4-May-15 | 2381 | 2 | 3 | 4 | IV-1 | Ank3 | 288 | 17-May-15 |
| 1836 | 2 | 3 | 4 | | IV-1 | Acot4 | 122970 | 4-May-15 | 2390 | 2 | 3 | 4 | IV-1 | Ankle1 | 126549 | 4-May-15 |
| 1843 | 2 | 3 | 4 | | IV-1 | Acox2 | 8309 | 4-May-15 | 2400 | 2 | 3 | 4 | IV-1 | Ankrd13b | 124930 | 4-May-15 |
| 1844 | 2 | 3 | 4 | | IV-1 | Acox3 | 8310 | 4-May-15 | 2407 | 2 | 3 | 4 | IV-1 | Ankrd23 | 200539 | 4-May-15 |
| 1848 | 2 | 3 | 4 | | IV-1 | Acp5 | 54 | 3-May-15 | 2419 | 2 | 3 | 4 | IV-1 | Ankrd35 | 148741 | 4-May-15 |
| 1850 | 2 | 3 | 4 | | IV-1 | Acpp | 55 | 12-May-15 | 2421 | 2 | 3 | 4 | IV-1 | Ankrd37 | 353322 | 21-May-15 |
| 1852 | 2 | 3 | 4 | | IV-1 | Acr | 49 | 12-May-15 | 2437 | 2 | 3 | 4 | IV-1 | Ankrd63 | 100131244 | 4-May-15 |
| 1853 | 2 | 3 | 4 | | IV-1 | Acrbp | 84519 | 4-May-15 | 2440 | 2 | 3 | 4 | IV-1 | Ankrd9 | 122416 | 4-May-15 |
| 1855 | 2 | 3 | 4 | | IV-1 | Acsbg1 | 23205 | 4-May-15 | 2448 | 2 | 3 | 4 | IV-1 | Anln | 54443 | 4-May-15 |
| 1857 | 2 | 3 | 4 | | IV-1 | Acsf2 | 80221 | 4-May-15 | 2454 | 2 | 3 | 4 | IV-1 | Ano5 | 203859 | 23-May-15 |
| 1859 | 2 | 3 | 4 | | IV-1 | Acsl1 | 2180 | 4-May-15 | 2463 | 2 | 3 | 4 | IV-1 | Antxr1 | 84168 | 4-May-15 |
| 1860 | 2 | 3 | 4 | | IV-1 | Acsl3 | 2181 | 4-May-15 | 2469 | 2 | 3 | 4 | IV-1 | Anxa13 | 312 | 4-May-15 |
| 1861 | 2 | 3 | 4 | | IV-1 | Acsl4 | 2182 | 23-May-15 | 2471 | 2 | 3 | 4 | IV-1 | Anxa3 | 306 | 12-May-15 |
| 1868 | 2 | 3 | 4 | | IV-1 | Acsm5 | 54988 | 4-May-15 | 2476 | 2 | 3 | 4 | IV-1 | Anxa8 | 653145 | 7-Jun-15 |
| 1869 | 2 | 3 | 4 | | IV-1 | Acss1 | 84532 | 4-May-15 | 2477 | 2 | 3 | 4 | IV-1 | Anxa9 | 8416 | 4-May-15 |
| 1872 | 2 | 3 | 4 | | IV-1 | Acss3 | 79611 | 4-May-15 | 2479 | 2 | 3 | 4 | IV-1 | Aoc1 | 26 | 4-May-15 |
| 1874 | 2 | 3 | 4 | | IV-1 | Acta2 | 59 | 23-May-15 | 2481 | 2 | 3 | 4 | IV-1 | Aoc3 | 8639 | 4-May-15 |
| 1912 | 2 | 3 | 4 | | IV-1 | Acyp2 | 98 | 3-May-15 | 2482 | 2 | 3 | 4 | IV-1 | Aox1 | 316 | 4-May-15 |
| 1913 | 2 | 3 | 4 | | IV-1 | Ada | 100 | 22-May-15 | 2501 | 2 | 3 | 4 | IV-1 | Ap3b2 | 8120 | 4-May-15 |
| 1948 | 2 | 3 | 4 | | IV-1 | Adam8 | 101 | 4-May-15 | 2520 | 2 | 3 | 4 | IV-1 | Apbb1ip | 54518 | 4-May-15 |
| 1950 | 2 | 3 | 4 | | IV-1 | Adamdec1 | 27299 | 24-May-15 | 2525 | 2 | 3 | 4 | IV-1 | Apcdd1 | 147495 | 4-May-15 |
| 1951 | 2 | 3 | 4 | | IV-1 | Adamts1 | 9510 | 4-May-15 | 2529 | 2 | 3 | 4 | IV-1 | Apex1 | 328 | 12-May-15 |

Fig.22 - 23

| | | | | | | | | | | | | | | | |
|---|---|---|---|---|---|---|---|---|---|---|---|---|---|---|---|
| 2549 | 2 | 3 | 4 | | IV-1 | Apobec1 | 339 | 23-May-15 | 3113 | 2 | 3 | 4 | IV-1 | B3gnt5 | 84002 | 4-May-15 |
| 2553 | 2 | 3 | 4 | | IV-1 | Apobr | 55911 | 4-May-15 | 3115 | 2 | 3 | 4 | IV-1 | B3gnt7 | 93010 | 4-May-15 |
| 2554 | 2 | 3 | 4 | | IV-1 | Apoc1 | 341 | 21-May-15 | 3123 | 2 | 3 | 4 | IV-1 | B4galnt1 | 2583 | 4-May-15 |
| 2555 | 2 | 3 | 4 | | IV-1 | Apoc2 | 344 | 4-May-15 | 3124 | 2 | 3 | 4 | IV-1 | B4galnt2 | 124872 | 4-May-15 |
| 2558 | 2 | 3 | 4 | | IV-1 | Apod | 347 | 12-May-15 | 3125 | 2 | 3 | 4 | IV-1 | B4galnt3 | 283358 | 4-May-15 |
| 2560 | 2 | 3 | 4 | | IV-1 | Apof | 319 | 4-May-15 | 3130 | 2 | 3 | 4 | IV-1 | B4galt4 | 8702 | 4-May-15 |
| 2565 | 2 | 3 | 4 | | IV-1 | Apol11b | | | 3132 | 2 | 3 | 4 | IV-1 | B4galt6 | 9331 | 4-May-15 |
| 2566 | 2 | 3 | 4 | | IV-1 | Apol6 | 80830 | 4-May-15 | 3150 | 2 | 3 | 4 | IV-1 | Bach1 | 571 | 13-Jun-15 |
| 2571 | 2 | 3 | 4 | | IV-1 | Apol7e | | | 3155 | 2 | 3 | 4 | IV-1 | Bag2 | 9532 | 4-May-15 |
| 2573 | 2 | 3 | 4 | | IV-1 | Apol9a | | | 3165 | 2 | 3 | 4 | IV-1 | Baiap2 | 10458 | 12-May-15 |
| 2574 | 2 | 3 | 4 | | IV-1 | Apol9b | | | 3166 | 2 | 3 | 4 | IV-1 | Baiap2l1 | 55971 | 4-May-15 |
| 2578 | 2 | 3 | 4 | | IV-1 | Apoo | 79135 | 4-May-15 | 3181 | 2 | 3 | 4 | IV-1 | Barx2 | 8538 | 28-May-15 |
| 2582 | 2 | 3 | 4 | | IV-1 | App | 351 | 31-May-15 | 3183 | 2 | 3 | 4 | IV-1 | Batf | 10538 | 7-Jun-15 |
| 2588 | 2 | 3 | 4 | | IV-1 | Aqp1 | 358 | 17-May-15 | 3185 | 2 | 3 | 4 | IV-1 | Batf3 | 55509 | 4-May-15 |
| 2592 | 2 | 3 | 4 | | IV-1 | Aqp3 | 360 | 12-May-15 | 3187 | 2 | 3 | 4 | IV-1 | Baz1a | 11177 | 4-May-15 |
| 2593 | 2 | 3 | 4 | | IV-1 | Aqp4 | 361 | 24-May-15 | 3191 | 2 | 3 | 4 | IV-1 | BB014433 | | |
| 2594 | 2 | 3 | 4 | | IV-1 | Aqp5 | 362 | 4-May-15 | 3194 | 2 | 3 | 4 | IV-1 | BB123696 | | |
| 2595 | 2 | 3 | 4 | | IV-1 | Aqp6 | 363 | 4-May-15 | 3203 | 2 | 3 | 4 | IV-1 | Bbs12 | 166379 | 23-May-15 |
| 2596 | 2 | 3 | 4 | | IV-1 | Aqp7 | 364 | 4-May-15 | 3215 | 2 | 3 | 4 | IV-1 | BC005561 | | |
| 2598 | 2 | 3 | 4 | | IV-1 | Aqp9 | 366 | 7-Jun-15 | 3222 | 2 | 3 | 4 | IV-1 | BC018242 | | |
| 2600 | 2 | 3 | 4 | | IV-1 | Ar | 367 | 7-Jun-15 | 3229 | 2 | 3 | 4 | IV-1 | BC021891 | | |
| 2607 | 2 | 3 | 4 | | IV-1 | Areg | 374 | 4-May-15 | 3230 | 2 | 3 | 4 | IV-1 | BC022687 | | |
| 2628 | 2 | 3 | 4 | | IV-1 | Arhgap11a | 9824 | 4-May-15 | 3236 | 2 | 3 | 4 | IV-1 | BC026585 | | |
| 2640 | 2 | 3 | 4 | | IV-1 | Arhgap24 | 83478 | 4-May-15 | 3239 | 2 | 3 | 4 | IV-1 | BC028528 | | |
| 2641 | 2 | 3 | 4 | | IV-1 | Arhgap25 | 9938 | 4-May-15 | 3240 | 2 | 3 | 4 | IV-1 | BC029214 | | |
| 2642 | 2 | 3 | 4 | | IV-1 | Arhgap26 | 23092 | 12-May-15 | 3250 | 2 | 3 | 4 | IV-1 | BC033916 | | |
| 2659 | 2 | 3 | 4 | | IV-1 | Arhgap5 | 394 | 12-May-15 | 3289 | 2 | 3 | 4 | IV-1 | BC064078 | | |
| 2661 | 2 | 3 | 4 | | IV-1 | Arhgap8 | 23779 | 4-May-15 | 3295 | 2 | 3 | 4 | IV-1 | BC089597 | | |
| 2662 | 2 | 3 | 4 | | IV-1 | Arhgap9 | 64333 | 4-May-15 | 3301 | 2 | 3 | 4 | IV-1 | BC117090 | | |
| 2665 | 2 | 3 | 4 | | IV-1 | Arhgdig | 398 | 4-May-15 | 3307 | 2 | 3 | 4 | IV-1 | Bcar1 | 9564 | 17-May-15 |
| 2672 | 2 | 3 | 4 | | IV-1 | Arhgef16 | 27237 | 12-May-15 | 3308 | 2 | 3 | 4 | IV-1 | Bcar3 | 8412 | 12-May-15 |
| 2673 | 2 | 3 | 4 | | IV-1 | Arhgef17 | 9828 | 4-May-15 | 3316 | 2 | 3 | 4 | IV-1 | Bcat2 | 587 | 4-May-15 |
| 2682 | 2 | 3 | 4 | | IV-1 | Arhgef37 | 389337 | 4-May-15 | 3319 | 2 | 3 | 4 | IV-1 | Bche | 590 | 17-May-15 |
| 2685 | 2 | 3 | 4 | | IV-1 | Arhgef4 | 50649 | 17-May-15 | 3327 | 2 | 3 | 4 | IV-1 | Bcl2a1a | | |
| 2699 | 2 | 3 | 4 | | IV-1 | Arid5a | 10865 | 4-May-15 | 3330 | 2 | 3 | 4 | IV-1 | Bcl2a1d | | |
| 2700 | 2 | 3 | 4 | | IV-1 | Arid5b | 84159 | 4-May-15 | 3333 | 2 | 3 | 4 | IV-1 | Bcl2l11 | 10018 | 17-May-15 |
| 2705 | 2 | 3 | 4 | | IV-1 | Arl11 | 115761 | 4-May-15 | 3336 | 2 | 3 | 4 | IV-1 | Bcl2l14 | 79370 | 4-May-15 |
| 2717 | 2 | 3 | 4 | | IV-1 | Arl4c | 10123 | 4-May-15 | 3339 | 2 | 3 | 4 | IV-1 | Bcl3 | 602 | 4-May-15 |
| 2718 | 2 | 3 | 4 | | IV-1 | Arl4d | 379 | 4-May-15 | 3354 | 2 | 3 | 4 | IV-1 | Bdh1 | 622 | 4-May-15 |
| 2720 | 2 | 3 | 4 | | IV-1 | Arl5b | 221079 | 4-May-15 | 3355 | 2 | 3 | 4 | IV-1 | Bdh2 | 56898 | 4-May-15 |
| 2732 | 2 | 3 | 4 | | IV-1 | Armc12 | 221481 | 4-May-15 | 3357 | 2 | 3 | 4 | IV-1 | Bdkrb2 | 624 | 7-Jun-15 |
| 2742 | 2 | 3 | 4 | | IV-1 | Armcx2 | 9823 | 4-May-15 | 3366 | 2 | 3 | 4 | IV-1 | Bend5 | 79656 | 4-May-15 |
| 2764 | 2 | 3 | 4 | | IV-1 | Arrdc2 | 27106 | 4-May-15 | 3370 | 2 | 3 | 4 | IV-1 | Best2 | 54831 | 4-May-15 |
| 2765 | 2 | 3 | 4 | | IV-1 | Arrdc3 | 57881 | 4-May-15 | 3381 | 2 | 3 | 4 | IV-1 | Bglap | 632 | 17-May-15 |
| 2767 | 2 | 3 | 4 | | IV-1 | Arrdc5 | 645432 | 21-May-15 | 3387 | 2 | 3 | 4 | IV-1 | Bhlhb9 | 80823 | 4-May-15 |
| 2775 | 2 | 3 | 4 | | IV-1 | Art2a-ps | | | 3391 | 2 | 3 | 4 | IV-1 | Bhlhe41 | 79365 | 4-May-15 |
| 2777 | 2 | 3 | 4 | | IV-1 | Art3 | 419 | 4-May-15 | 3399 | 2 | 3 | 4 | IV-1 | Bin1 | 274 | 12-May-15 |
| 2779 | 2 | 3 | 4 | | IV-1 | Art5 | 116969 | 4-May-15 | 3403 | 2 | 3 | 4 | IV-1 | Birc3 | 330 | 24-May-15 |
| 2781 | 2 | 3 | 4 | | IV-1 | Arv1 | 64801 | 4-May-15 | 3404 | 2 | 3 | 4 | IV-1 | Birc5 | 332 | 24-May-15 |
| 2784 | 2 | 3 | 4 | | IV-1 | Arxes1 | | | 3409 | 2 | 3 | 4 | IV-1 | Blk | 640 | 17-May-15 |
| 2791 | 2 | 3 | 4 | | IV-1 | Asap3 | 55616 | 4-May-15 | 3410 | 2 | 3 | 4 | IV-1 | Blm | 641 | 23-May-15 |
| 2793 | 2 | 3 | 4 | | IV-1 | Asb10 | 136371 | 4-May-15 | 3422 | 2 | 3 | 4 | IV-1 | Bmf | 90427 | 4-May-15 |
| 2795 | 2 | 3 | 4 | | IV-1 | Asb12 | 142689 | 4-May-15 | 3425 | 2 | 3 | 4 | IV-1 | Bmp10 | 27302 | 4-May-15 |
| 2797 | 2 | 3 | 4 | | IV-1 | Asb14 | 142686 | 4-May-15 | 3430 | 2 | 3 | 4 | IV-1 | Bmp4 | 652 | 31-May-15 |
| 2798 | 2 | 3 | 4 | | IV-1 | Asb15 | 142685 | 4-May-15 | 3433 | 2 | 3 | 4 | IV-1 | Bmp7 | 655 | 17-May-15 |
| 2801 | 2 | 3 | 4 | | IV-1 | Asb17os | | | 3434 | 2 | 3 | 4 | IV-1 | Bmp8a | 353500 | 4-May-15 |
| 2802 | 2 | 3 | 4 | | IV-1 | Asb18 | 401036 | 4-May-15 | 3438 | 2 | 3 | 4 | IV-1 | Bmpr1b | 658 | 3-May-15 |
| 2803 | 2 | 3 | 4 | | IV-1 | Asb2 | 51676 | 4-May-15 | 3442 | 2 | 3 | 4 | IV-1 | Bmyc | | |
| 2826 | 2 | 3 | 4 | | IV-1 | Asf1b | 55723 | 4-May-15 | 3447 | 2 | 3 | 4 | IV-1 | Bnip3 | 664 | 12-May-15 |
| 2830 | 2 | 3 | 4 | | IV-1 | Asl | 435 | 7-Jun-15 | 3450 | 2 | 3 | 4 | IV-1 | Boc | 91653 | 12-May-15 |
| 2833 | 2 | 3 | 4 | | IV-1 | Asns | 440 | 12-May-15 | 3456 | 2 | 3 | 4 | IV-1 | Bola3 | 388962 | 4-May-15 |
| 2835 | 2 | 3 | 4 | | IV-1 | Aspa | 443 | 23-May-15 | 3460 | 2 | 3 | 4 | IV-1 | Bpgm | 669 | 12-May-15 |
| 2837 | 2 | 3 | 4 | | IV-1 | Aspg | 374569 | 4-May-15 | 3461 | 2 | 3 | 4 | IV-1 | Bphl | 670 | 12-May-15 |
| 2838 | 2 | 3 | 4 | | IV-1 | Asph | 444 | 12-May-15 | 3464 | 2 | 3 | 4 | IV-1 | Bpifa2 | 140683 | 4-May-15 |
| 2846 | 2 | 3 | 4 | | IV-1 | Ass1 | 445 | 23-May-15 | 3497 | 2 | 3 | 4 | IV-1 | Bri3bp | 140707 | 4-May-15 |
| 2860 | 2 | 3 | 4 | | IV-1 | Atad3aos | | | 3521 | 2 | 3 | 4 | IV-1 | Bsph2 | | |
| 2863 | 2 | 3 | 4 | | IV-1 | Atcay | 85300 | 4-May-15 | 3537 | 2 | 3 | 4 | IV-1 | Btbd7 | 55727 | 4-May-15 |
| 2868 | 2 | 3 | 4 | | IV-1 | Atf3 | 467 | 12-May-15 | 3549 | 2 | 3 | 4 | IV-1 | Btla | 151888 | 4-May-15 |
| 2886 | 2 | 3 | 4 | | IV-1 | Atg4a | 115201 | 24-May-15 | 3555 | 2 | 3 | 4 | IV-1 | Bves | 11149 | 4-May-15 |
| 2904 | 2 | 3 | 4 | | IV-1 | Atoh8 | 84913 | 3-May-15 | 3567 | 2 | 3 | 4 | IV-1 | Bzrap1 | 9256 | 4-May-15 |
| 2912 | 2 | 3 | 4 | | IV-1 | Atp12a | 479 | 4-May-15 | 3572 | 2 | 3 | 4 | IV-1 | C030013G03Rik | | |
| 2916 | 2 | 3 | 4 | | IV-1 | Atp13a4 | 84239 | 4-May-15 | 3578 | 2 | 3 | 4 | IV-1 | C030034L19Rik | | |
| 2919 | 2 | 3 | 4 | | IV-1 | Atp1a2 | 477 | 23-May-15 | 3588 | 2 | 3 | 4 | IV-1 | C130050O18Rik | | |
| 2923 | 2 | 3 | 4 | | IV-1 | Atp1b2 | 482 | 4-May-15 | 3597 | 2 | 3 | 4 | IV-1 | C1galt1 | 56913 | 14-May-15 |
| 2929 | 2 | 3 | 4 | | IV-1 | Atp2b1 | 490 | 24-May-15 | 3599 | 2 | 3 | 4 | IV-1 | C1qa | 712 | 17-May-15 |
| 2930 | 2 | 3 | 4 | | IV-1 | Atp2b2 | 491 | 7-Jun-15 | 3600 | 2 | 3 | 4 | IV-1 | C1qb | 713 | 4-May-15 |
| 2935 | 2 | 3 | 4 | | IV-1 | Atp4a | 495 | 4-May-15 | 3602 | 2 | 3 | 4 | IV-1 | C1qc | 714 | 4-May-15 |
| 2946 | 2 | 3 | 4 | | IV-1 | Atp5h | 10476 | 4-May-15 | 3609 | 2 | 3 | 4 | IV-1 | C1qtnf3 | 114899 | 4-May-15 |
| 2949 | 2 | 3 | 4 | | IV-1 | Atp5k | 521 | 4-May-15 | 3610 | 2 | 3 | 4 | IV-1 | C1qtnf4 | 114900 | 4-May-15 |
| 2951 | 2 | 3 | 4 | | IV-1 | Atp5o | 539 | 23-May-15 | 3613 | 2 | 3 | 4 | IV-1 | C1qtnf7 | 114905 | 4-May-15 |
| 2956 | 2 | 3 | 4 | | IV-1 | Atp6ap2 | 10159 | 3-May-15 | 3624 | 2 | 3 | 4 | IV-1 | C230035I16Rik | | |
| 2966 | 2 | 3 | 4 | | IV-1 | Atp6v0e2 | 155060 | 4-May-15 | 3650 | 2 | 3 | 4 | IV-1 | C3ar1 | 719 | 4-May-15 |
| 2977 | 2 | 3 | 4 | | IV-1 | Atp6v1g2 | 534 | 4-May-15 | 3654 | 2 | 3 | 4 | IV-1 | C4a | 720 | 4-May-15 |
| 2978 | 2 | 3 | 4 | | IV-1 | Atp6v1g3 | 127124 | 4-May-15 | 3655 | 2 | 3 | 4 | IV-1 | C4b | 721 | 17-May-15 |
| 2988 | 2 | 3 | 4 | | IV-1 | Atp9a | 10079 | 4-May-15 | 3657 | 2 | 3 | 4 | IV-1 | C4bp-ps1 | | |
| 3033 | 2 | 3 | 4 | | IV-1 | Aurkb | 9212 | 17-May-15 | 3659 | 2 | 3 | 4 | IV-1 | C530008M17Rik | | |
| 3035 | 2 | 3 | 4 | | IV-1 | Auts2 | 26053 | 7-Jun-15 | 3667 | 2 | 3 | 4 | IV-1 | C7 | 730 | 7-Jun-15 |
| 3036 | 2 | 3 | 4 | | IV-1 | AV039307 | | | 3671 | 2 | 3 | 4 | IV-1 | C77080 | | |
| 3040 | 2 | 3 | 4 | | IV-1 | Avil | 10677 | 4-May-15 | 3673 | 2 | 3 | 4 | IV-1 | C78339 | | |
| 3042 | 2 | 3 | 4 | | IV-1 | Avp | 551 | 7-Jun-15 | 3683 | 2 | 3 | 4 | IV-1 | C8g | 733 | 4-May-15 |
| 3044 | 2 | 3 | 4 | | IV-1 | Avpr1a | 552 | 17-May-15 | 3693 | 2 | 3 | 4 | IV-1 | Cables1 | 91768 | 4-May-15 |
| 3047 | 2 | 3 | 4 | | IV-1 | AW011738 | | | 3697 | 2 | 3 | 4 | IV-1 | Cabp4 | 57010 | 14-May-15 |
| 3058 | 2 | 3 | 4 | | IV-1 | Awat1 | 158833 | 4-May-15 | 3698 | 2 | 3 | 4 | IV-1 | Cabp5 | 56344 | 12-May-15 |
| 3059 | 2 | 3 | 4 | | IV-1 | Awat2 | 158835 | 4-May-15 | 3700 | 2 | 3 | 4 | IV-1 | Cabs1 | 85438 | 4-May-15 |
| 3070 | 2 | 3 | 4 | | IV-1 | Azgp1 | 563 | 24-May-15 | 3707 | 2 | 3 | 4 | IV-1 | Cacna2d1 | 776 | 10-May-15 |
| 3085 | 2 | 3 | 4 | | IV-1 | B230208H11Rik | | | 3714 | 2 | 3 | 4 | IV-1 | Cacna2d1 | 781 | 12-May-15 |
| 3103 | 2 | 3 | 4 | | IV-1 | B3galt5 | 10317 | 23-May-15 | 3718 | 2 | 3 | 4 | IV-1 | Cacnb1 | 782 | 12-May-15 |

Fig.22 - 24

| | | | | | | | | | | | | | | | | |
|---|---|---|---|---|---|---|---|---|---|---|---|---|---|---|---|---|
| 3728 | 2 | 3 | 4 | | IV-1 | Cacng7 | 59284 | 4-May-15 | 4236 | 2 | 3 | 4 | | IV-1 | Cd79a | 973 | 12-May-15 |
| 3733 | 2 | 3 | 4 | | IV-1 | Cad | 790 | 7-Jun-15 | 4237 | 2 | 3 | 4 | | IV-1 | Cd79b | 974 | 4-May-15 |
| 3734 | 2 | 3 | 4 | | IV-1 | Cadm1 | 23705 | 12-May-15 | 4242 | 2 | 3 | 4 | | IV-1 | Cd84 | 8832 | |
| 3739 | 2 | 3 | 4 | | IV-1 | Cadps2 | 93664 | 12-May-15 | 4246 | 2 | 3 | 4 | | IV-1 | Cd9 | 928 | |
| 3741 | 2 | 3 | 4 | | IV-1 | Calb1 | 793 | 4-May-15 | 4251 | 2 | 3 | 4 | | IV-1 | Cda | 978 | 4-May-15 |
| 3743 | 2 | 3 | 4 | | IV-1 | Calca | 796 | 17-May-15 | 4261 | 2 | 3 | 4 | | IV-1 | Cdc25a | 993 | 31-May-15 |
| 3744 | 2 | 3 | 4 | | IV-1 | Calcb | 797 | 28-May-15 | 4278 | 2 | 3 | 4 | | IV-1 | Cdc42ep5 | 148170 | 4-May-15 |
| 3747 | 2 | 3 | 4 | | IV-1 | Calcr | 799 | 31-May-15 | 4283 | 2 | 3 | 4 | | IV-1 | Cdc6 | 990 | |
| 3758 | 2 | 3 | 4 | | IV-1 | Calml4 | 91860 | 4-May-15 | 4287 | 2 | 3 | 4 | | IV-1 | Cdca3 | 83461 | 12-May-15 |
| 3773 | 2 | 3 | 4 | | IV-1 | Camk2n2 | 94032 | 4-May-15 | 4291 | 2 | 3 | 4 | | IV-1 | Cdca7l | 55536 | |
| 3776 | 2 | 3 | 4 | | IV-1 | Camkk2 | 10645 | 12-May-15 | 4295 | 2 | 3 | 4 | | IV-1 | Cdh1 | 999 | 2015/6/7 |
| 3780 | 2 | 3 | 4 | | IV-1 | Camp | 820 | 7-Jun-15 | 4301 | 2 | 3 | 4 | | IV-1 | Cdh16 | 1014 | 7-Jun-15 |
| 3783 | 2 | 3 | 4 | | IV-1 | Camsap3 | 57662 | 4-May-15 | 4304 | 2 | 3 | 4 | | IV-1 | Cdh19 | 28513 | y-2015 |
| 3792 | 2 | 3 | 4 | | IV-1 | Capg | 822 | 2015/6/7 | 4307 | 2 | 3 | 4 | | IV-1 | Cdh22 | 64405 | 4-May-15 |
| 3794 | 2 | 3 | 4 | | IV-1 | Capn10 | 11132 | 23-May-15 | 4321 | 2 | 3 | 4 | | IV-1 | Cdhr5 | 53841 | 4-May-15 |
| 3800 | 2 | 3 | 4 | | IV-1 | Capn3 | 825 | 23-May-15 | 4324 | 2 | 3 | 4 | | IV-1 | Cdk1 | 983 | 24-May-15 |
| 3804 | 2 | 3 | 4 | | IV-1 | Capn8 | 388743 | 4-May-15 | 4333 | 2 | 3 | 4 | | IV-1 | Cdk18 | 5129 | 4-May-15 |
| 3807 | 2 | 3 | 4 | | IV-1 | Capns2 | 84290 | 4-May-15 | 4357 | 2 | 3 | 4 | | IV-1 | Cdkn1a | 1026 | 24-May-15 |
| 3819 | 2 | 3 | 4 | | IV-1 | Car12 | | | 4359 | 2 | 3 | 4 | | IV-1 | Cdkn1c | 1028 | |
| 3823 | 2 | 3 | 4 | | IV-1 | Car14 | | | 4363 | 2 | 3 | 4 | | IV-1 | Cdkn2b | 1030 | |
| 3830 | 2 | 3 | 4 | | IV-1 | Car8 | | | 4364 | 2 | 3 | 4 | | IV-1 | Cdkn2c | 1031 | |
| 3844 | 2 | 3 | 4 | | IV-1 | Cartpt | 9607 | | 4367 | 2 | 3 | 4 | | IV-1 | Cdnf | 441549 | 4-May-15 |
| 3854 | 2 | 3 | 4 | | IV-1 | Casp12 | 100506742 | 4-May-15 | 4368 | 2 | 3 | 4 | | IV-1 | Cdo1 | 1036 | |
| 3865 | 2 | 3 | 4 | | IV-1 | Casq2 | 845 | | 4370 | 2 | 3 | 4 | | IV-1 | Cdpf1 | 150383 | 4-May-15 |
| 3866 | 2 | 3 | 4 | | IV-1 | Casr | 846 | 24-May-15 | 4372 | 2 | 3 | 4 | | IV-1 | Cdr2 | 1039 | |
| 3875 | 2 | 3 | 4 | | IV-1 | Catsper4 | 378807 | 4-May-15 | 4375 | 2 | 3 | 4 | | IV-1 | Cds1 | 1040 | /6/7 |
| 3888 | 2 | 3 | 4 | | IV-1 | Cbfc | 23624 | 7-Jun-15 | 4377 | 2 | 3 | 4 | | IV-1 | Cdsn | 1041 | 30-May-15 |
| 3890 | 2 | 3 | 4 | | IV-1 | Cbln1 | 869 | 4-May-15 | 4378 | 2 | 3 | 4 | | IV-1 | Cdt1 | 81620 | |
| 3892 | 2 | 3 | 4 | | IV-1 | Cbln3 | 643866 | 4-May-15 | 4388 | 2 | 3 | 4 | | IV-1 | Ceacam12 | | |
| 3895 | 2 | 3 | 4 | | IV-1 | Cbr2 | | | 4401 | 2 | 3 | 4 | | IV-1 | Cebpa | 1050 | |
| 3898 | 2 | 3 | 4 | | IV-1 | Cbs | 875 | 23-May-15 | 4402 | 2 | 3 | 4 | | IV-1 | Cebpb | 1051 | |
| 3914 | 2 | 3 | 4 | | IV-1 | Ccbe1 | 147372 | | 4403 | 2 | 3 | 4 | | IV-1 | Cebpd | 1052 | 4-May-15 |
| 3915 | 2 | 3 | 4 | | IV-1 | Ccbl1 | 883 | 4-May-15 | 4420 | 2 | 3 | 4 | | IV-1 | Celf6 | 60677 | 4-May-15 |
| 3926 | 2 | 3 | 4 | | IV-1 | Ccdc11 | 220136 | 4-May-15 | 4426 | 2 | 3 | 4 | | IV-1 | Cend1 | 51286 | 4-May-15 |
| 3935 | 2 | 3 | 4 | | IV-1 | Ccdc120 | 90060 | 28-May-15 | 4432 | 2 | 3 | 4 | | IV-1 | Cenph | 64946 | 4-May-15 |
| 3937 | 2 | 3 | 4 | | IV-1 | Ccdc122 | 160857 | 4-May-15 | 4435 | 2 | 3 | 4 | | IV-1 | Cenpk | 64105 | |
| 3948 | 2 | 3 | 4 | | IV-1 | Ccdc136 | 64753 | | 4440 | 2 | 3 | 4 | | IV-1 | Cenpp | 401541 | |
| 3963 | 2 | 3 | 4 | | IV-1 | Ccdc153 | 283152 | 4-May-15 | 4442 | 2 | 3 | 4 | | IV-1 | Cenpt | 80152 | |
| 3990 | 2 | 3 | 4 | | IV-1 | Ccdc19 | 25790 | 4-May-15 | 4456 | 2 | 3 | 4 | | IV-1 | Cep170b | 283638 | 4-May-15 |
| 3992 | 2 | 3 | 4 | | IV-1 | Ccdc23 | 374969 | 4-May-15 | 4471 | 2 | 3 | 4 | | IV-1 | Cep76 | 79959 | |
| 3997 | 2 | 3 | 4 | | IV-1 | Ccdc28b | 79140 | 23-May-15 | 4472 | 2 | 3 | 4 | | IV-1 | Cep78 | 84131 | 4-May-15 |
| 4018 | 2 | 3 | 4 | | IV-1 | Ccdc57 | 284901 | | 4475 | 2 | 3 | 4 | | IV-1 | Cep85 | 64793 | 4-May-15 |
| 4019 | 2 | 3 | 4 | | IV-1 | Ccdc58 | 131076 | 21-May-15 | 4476 | 2 | 3 | 4 | | IV-1 | Cep85l | 387119 | |
| 4026 | 2 | 3 | 4 | | IV-1 | Ccdc64 | 92558 | | 4480 | 2 | 3 | 4 | | IV-1 | Cept1 | 10390 | 12-May-15 |
| 4028 | 2 | 3 | 4 | | IV-1 | Ccdc74a | 90557 | | 4485 | 2 | 3 | 4 | | IV-1 | Cers1 | 10715 | 21-May-15 |
| 4042 | 2 | 3 | 4 | | IV-1 | Ccdc8 | 83987 | 23-May-15 | 4489 | 2 | 3 | 4 | | IV-1 | Cers5 | 91012 | /5/21 |
| 4050 | 2 | 3 | 4 | | IV-1 | Ccdc85c | 317762 | 4-May-15 | 4490 | 2 | 3 | 4 | | IV-1 | Cers6 | 253782 | |
| 4055 | 2 | 3 | 4 | | IV-1 | Ccdc88c | 440193 | 12-May-15 | 4494 | 2 | 3 | 4 | | IV-1 | Ces1d | | |
| 4060 | 2 | 3 | 4 | | IV-1 | Ccdc92 | 80212 | 21-May-15 | 4495 | 2 | 3 | 4 | | IV-1 | Ces1e | | |
| 4068 | 2 | 3 | 4 | | IV-1 | Cck | 885 | 2015/6/7 | 4496 | 2 | 3 | 4 | | IV-1 | Ces1f | | |
| 4070 | 2 | 3 | 4 | | IV-1 | Cckbr | 887 | 12-May-15 | 4497 | 2 | 3 | 4 | | IV-1 | Ces1g | | |
| 4072 | 2 | 3 | 4 | | IV-1 | Ccl11 | 6356 | 10-May-15 | 4498 | 2 | 3 | 4 | | IV-1 | Ces2a | | |
| 4075 | 2 | 3 | 4 | | IV-1 | Ccl19 | 6363 | | 4499 | 2 | 3 | 4 | | IV-1 | Ces2b | | |
| 4078 | 2 | 3 | 4 | | IV-1 | Cd21a | | | 4502 | 2 | 3 | 4 | | IV-1 | Ces2e | | |
| 4080 | 2 | 3 | 4 | | IV-1 | Cd21c | | | 4504 | 2 | 3 | 4 | | IV-1 | Ces2g | | |
| 4081 | 2 | 3 | 4 | | IV-1 | Cd22 | 6367 | 4-May-15 | 4508 | 2 | 3 | 4 | | IV-1 | Ces4a | 283848 | |
| 4086 | 2 | 3 | 4 | | IV-1 | Cd27b | | | 4518 | 2 | 3 | 4 | | IV-1 | Cfh | 3075 | |
| 4087 | 2 | 3 | 4 | | IV-1 | Cd28 | 56477 | 7-Jun-15 | 4526 | 2 | 3 | 4 | | IV-1 | Cfi | 1080 | 24-May-15 |
| 4090 | 2 | 3 | 4 | | IV-1 | Cd5 | 6152 | 17-May-15 | 4529 | 2 | 3 | 4 | | IV-1 | Cgn | 57530 | |
| 4094 | 2 | 3 | 4 | | IV-1 | Cd9 | | | 4530 | 2 | 3 | 4 | | IV-1 | Cgnl1 | 84952 | 12-May-15 |
| 4104 | 2 | 3 | 4 | | IV-1 | Ccnd1 | 595 | 24-May-15 | 4535 | 2 | 3 | 4 | | IV-1 | Chac2 | 494143 | |
| 4108 | 2 | 3 | 4 | | IV-1 | Ccne1 | 898 | | 4543 | 2 | 3 | 4 | | IV-1 | Chchd10 | 400916 | |
| 4109 | 2 | 3 | 4 | | IV-1 | Ccne2 | 9134 | | 4549 | 2 | 3 | 4 | | IV-1 | Chchd7 | 79145 | 4-May-15 |
| 4128 | 2 | 3 | 4 | | IV-1 | Ccr1 | 1230 | | 4568 | 2 | 3 | 4 | | IV-1 | Chia1 | | |
| 4131 | 2 | 3 | 4 | | IV-1 | Ccr2 | 729230 | | 4572 | 2 | 3 | 4 | | IV-1 | Chil1 | | |
| 4132 | 2 | 3 | 4 | | IV-1 | Ccr3 | 1232 | 12-May-15 | 4573 | 2 | 3 | 4 | | IV-1 | Chil3 | | |
| 4135 | 2 | 3 | 4 | | IV-1 | Ccr6 | 1235 | | 4602 | 2 | 3 | 4 | | IV-1 | Chpt1 | 56994 | 4-May-15 |
| 4136 | 2 | 3 | 4 | | IV-1 | Ccr7 | 1236 | 17-May-15 | 4604 | 2 | 3 | 4 | | IV-1 | Chrd | 8646 | 12-May-15 |
| 4139 | 2 | 3 | 4 | | IV-1 | Ccrl2 | 9034 | 4-May-15 | 4605 | 2 | 3 | 4 | | IV-1 | Chrdl1 | 91851 | |
| 4140 | 2 | 3 | 4 | | IV-1 | Ccrn4l | 25819 | | 4608 | 2 | 3 | 4 | | IV-1 | Chrm2 | 1129 | 4-May-15 |
| 4155 | 2 | 3 | 4 | | IV-1 | Cd101 | 9398 | | 4610 | 2 | 3 | 4 | | IV-1 | Chrm4 | 1132 | 12-May-15 |
| 4157 | 2 | 3 | 4 | | IV-1 | Cd14 | 929 | 2015/6/7 | 4613 | 2 | 3 | 4 | | IV-1 | Chrna10 | 57053 | 4-May-15 |
| 4160 | 2 | 3 | 4 | | IV-1 | Cd163 | 9332 | | 4614 | 2 | 3 | 4 | | IV-1 | Chrna2 | 1135 | 23-May-15 |
| 4163 | 2 | 3 | 4 | | IV-1 | Cd163l2 | 388611 | 4-May-15 | 4615 | 2 | 3 | 4 | | IV-1 | Chrna3 | 1136 | 12-May-15 |
| 4164 | 2 | 3 | 4 | | IV-1 | Cd177 | 57126 | 4-May-15 | 4616 | 2 | 3 | 4 | | IV-1 | Chrna4 | 1137 | |
| 4167 | 2 | 3 | 4 | | IV-1 | Cd1d1 | | | 4628 | 2 | 3 | 4 | | IV-1 | Chst1 | 8534 | |
| 4175 | 2 | 3 | 4 | | IV-1 | Cd207 | 50489 | | 4629 | 2 | 3 | 4 | | IV-1 | Chst10 | 9486 | |
| 4177 | 2 | 3 | 4 | | IV-1 | Cd209b | | | 4639 | 2 | 3 | 4 | | IV-1 | Chst7 | 56548 | 12-May-15 |
| 4179 | 2 | 3 | 4 | | IV-1 | Cd209d | | | 4651 | 2 | 3 | 4 | | IV-1 | Ciart | 148523 | 12-May-15 |
| 4183 | 2 | 3 | 4 | | IV-1 | Cd22 | 933 | | 4653 | 2 | 3 | 4 | | IV-1 | Cib2 | 10518 | 4-May-15 |
| 4188 | 2 | 3 | 4 | | IV-1 | Cd24a | 100133941 | 21-May-15 | 4661 | 2 | 3 | 4 | | IV-1 | Cilp | 8483 | 12-May-15 |
| 4195 | 2 | 3 | 4 | | IV-1 | Cd300a | 11314 | | 4675 | 2 | 3 | 4 | | IV-1 | Cited2 | 10370 | 10-May-15 |
| 4198 | 2 | 3 | 4 | | IV-1 | Cd300lb | 124599 | | 4683 | 2 | 3 | 4 | | IV-1 | Ckb | 1152 | 7-Jun-15 |
| 4207 | 2 | 3 | 4 | | IV-1 | Cd36 | 948 | | 4684 | 2 | 3 | 4 | | IV-1 | Ckif | 51192 | /5/4 |
| 4210 | 2 | 3 | 4 | | IV-1 | Cd3d | 915 | 12-May-15 | 4688 | 2 | 3 | 4 | | IV-1 | Cks1b | 1163 | |
| 4217 | 2 | 3 | 4 | | IV-1 | Cd44 | 960 | | 4694 | 2 | 3 | 4 | | IV-1 | Clca1 | 1179 | |
| 4220 | 2 | 3 | 4 | | IV-1 | Cd48 | 962 | | 4695 | 2 | 3 | 4 | | IV-1 | Clca2 | 9635 | |
| 4221 | 2 | 3 | 4 | | IV-1 | Cd5 | 921 | 12-May-15 | 4698 | 2 | 3 | 4 | | IV-1 | Clca5 | | |
| 4223 | 2 | 3 | 4 | | IV-1 | Cd53 | 963 | | 4699 | 2 | 3 | 4 | | IV-1 | Clca6 | | |
| 4225 | 2 | 3 | 4 | | IV-1 | Cd59a | | | 4701 | 2 | 3 | 4 | | IV-1 | Clcf1 | 23529 | |
| 4228 | 2 | 3 | 4 | | IV-1 | Cd6 | 923 | 12-May-15 | 4702 | 2 | 3 | 4 | | IV-1 | Clcn1 | 1180 | 23-May-15 |
| 4229 | 2 | 3 | 4 | | IV-1 | Cd63 | 967 | 17-May-15 | 4706 | 2 | 3 | 4 | | IV-1 | Clcn5 | 1184 | |
| 4230 | 2 | 3 | 4 | | IV-1 | Cd68 | 968 | | 4712 | 2 | 3 | 4 | | IV-1 | Cldn10 | 9071 | 4-May-15 |
| 4231 | 2 | 3 | 4 | | IV-1 | Cd69 | 969 | 4-May-15 | 4719 | 2 | 3 | 4 | | IV-1 | Cldn17 | 26285 | 4-May-15 |
| 4233 | 2 | 3 | 4 | | IV-1 | Cd70 | 970 | 4-May-15 | 4725 | 2 | 3 | 4 | | IV-1 | Cldn23 | 137075 | |
| 4234 | 2 | 3 | 4 | | IV-1 | Cd72 | 971 | 4-May-15 | 4731 | 2 | 3 | 4 | | IV-1 | Cldn5 | 7122 | |
| | | | | | | | | | 4739 | 2 | 3 | 4 | | IV-1 | Clec12a | 160364 | |

Fig.22 - 25

| | | | | | | | | | | | | | | | |
|---|---|---|---|---|---|---|---|---|---|---|---|---|---|---|---|
| 4745 | 2 | 3 | 4 | | IV-1 | Clec1b | 51266 | 4-May-15 | 5387 | 2 | 3 | 4 | IV-1 | Cyb5 | 1528 | 12-May-15 |
| 4747 | 2 | 3 | 4 | | IV-1 | Clec2e | | | 5400 | 2 | 3 | 4 | IV-1 | Cyba | 1535 | |
| 4755 | 2 | 3 | 4 | | IV-1 | Clec4a1 | | | 5401 | 2 | 3 | 4 | IV-1 | Cybb | 1536 | |
| 4757 | 2 | 3 | 4 | | IV-1 | Clec4a3 | | | 5407 | 2 | 3 | 4 | IV-1 | Cyfip2 | 26999 | |
| 4759 | 2 | 3 | 4 | | IV-1 | Clec4b1 | | | 5408 | 2 | 3 | 4 | IV-1 | Cygb | 114757 | 12-May-15 |
| 4761 | 2 | 3 | 4 | | IV-1 | Clec4d | 338339 | | 5417 | 2 | 3 | 4 | IV-1 | Cyp17a1 | 1586 | 24-May-15 |
| 4766 | 2 | 3 | 4 | | IV-1 | Clec4n | 93978 | | 5424 | 2 | 3 | 4 | IV-1 | Cyp24a1 | 1591 | 4-May-15 |
| 4772 | 2 | 3 | 4 | | IV-1 | Clic3 | 9022 | | 5428 | 2 | 3 | 4 | IV-1 | Cyp27a1 | 1593 | 24-May-15 |
| 4774 | 2 | 3 | 4 | | IV-1 | Clic5 | 53405 | 4-May-15 | 5431 | 2 | 3 | 4 | IV-1 | Cyp2a22 | | |
| 4775 | 2 | 3 | 4 | | IV-1 | Clic6 | 54102 | | 5435 | 2 | 3 | 4 | IV-1 | Cyp2b10 | | |
| 4780 | 2 | 3 | 4 | | IV-1 | Clip4 | 79745 | 76/7 | 5436 | 2 | 3 | 4 | IV-1 | Cyp2b13 | | |
| 4786 | 2 | 3 | 4 | | IV-1 | Clmp | 79827 | | 5441 | 2 | 3 | 4 | IV-1 | Cyp2c37 | | |
| 4789 | 2 | 3 | 4 | | IV-1 | Cln6 | 54982 | 23-May-15 | 5443 | 2 | 3 | 4 | IV-1 | Cyp2c39 | | |
| 4806 | 2 | 3 | 4 | | IV-1 | Clstn1 | 22883 | 4-May-15 | 5444 | 2 | 3 | 4 | IV-1 | Cyp2c40 | | |
| 4818 | 2 | 3 | 4 | | IV-1 | Cma1 | 1215 | | 5445 | 2 | 3 | 4 | IV-1 | Cyp2c44 | | |
| 4822 | 2 | 3 | 4 | | IV-1 | Cmbl | 134147 | 4-May-15 | 5449 | 2 | 3 | 4 | IV-1 | Cyp2c55 | | |
| 4827 | 2 | 3 | 4 | | IV-1 | Cml1 | 9027 | 4-May-15 | 5453 | 2 | 3 | 4 | IV-1 | Cyp2c68 | | |
| 4857 | 2 | 3 | 4 | | IV-1 | Cngb3 | 54714 | 23-May-15 | 5454 | 2 | 3 | 4 | IV-1 | Cyp2c69 | | |
| 4862 | 2 | 3 | 4 | | IV-1 | Cnksr1 | 10256 | | 5460 | 2 | 3 | 4 | IV-1 | Cyp2d22 | | |
| 4863 | 2 | 3 | 4 | | IV-1 | Cnksr2 | 22886 | 13-May-15 | 5461 | 2 | 3 | 4 | IV-1 | Cyp2d26 | | |
| 4890 | 2 | 3 | 4 | | IV-1 | Cnrip1 | 25927 | 21-May-15 | 5468 | 2 | 3 | 4 | IV-1 | Cyp2g1 | 22952 | 12-May-15 |
| 4893 | 2 | 3 | 4 | | IV-1 | Cntf | 1270 | 4-May-15 | 5471 | 2 | 3 | 4 | IV-1 | Cyp2j13 | | |
| 4894 | 2 | 3 | 4 | | IV-1 | Cntfr | 1271 | | 5475 | 2 | 3 | 4 | IV-1 | Cyp2j9 | | |
| 4919 | 2 | 3 | 4 | | IV-1 | Coch | 1690 | | 5483 | 2 | 3 | 4 | IV-1 | Cyp3a13 | | |
| 4929 | 2 | 3 | 4 | | IV-1 | Col10a1 | 1300 | | 5485 | 2 | 3 | 4 | IV-1 | Cyp3a25 | | |
| 4932 | 2 | 3 | 4 | | IV-1 | Col12a1 | 1303 | 12-May-15 | 5486 | 2 | 3 | 4 | IV-1 | Cyp3a41a | | |
| 4944 | 2 | 3 | 4 | | IV-1 | Col23a1 | 91522 | 12-May-15 | 5487 | 2 | 3 | 4 | IV-1 | Cyp3a41b | | |
| 4969 | 2 | 3 | 4 | | IV-1 | Col8a1 | 1295 | 4-May-15 | 5492 | 2 | 3 | 4 | IV-1 | Cyp4a10 | | |
| 4973 | 2 | 3 | 4 | | IV-1 | Col9a3 | 1299 | 23-May-15 | 5498 | 2 | 3 | 4 | IV-1 | Cyp4a31 | | |
| 4998 | 2 | 3 | 4 | | IV-1 | Coprs | 55352 | 4-May-15 | 5500 | 2 | 3 | 4 | IV-1 | Cyp4b1 | 1580 | |
| 5000 | 2 | 3 | 4 | | IV-1 | Cops3 | 8533 | 4-May-15 | 5501 | 2 | 3 | 4 | IV-1 | Cyp4b1-ps2 | | |
| 5022 | 2 | 3 | 4 | | IV-1 | Coro2a | 7464 | | 5506 | 2 | 3 | 4 | IV-1 | Cyp4f17 | | |
| 5024 | 2 | 3 | 4 | | IV-1 | Coro6 | 84940 | | 5514 | 2 | 3 | 4 | IV-1 | Cyp51 | 1595 | |
| 5027 | 2 | 3 | 4 | | IV-1 | Cotl1 | 23406 | | 5528 | 2 | 3 | 4 | IV-1 | Cyr61 | 3491 | |
| 5038 | 2 | 3 | 4 | | IV-1 | Cox4i2 | 84701 | 4-May-15 | 5532 | 2 | 3 | 4 | IV-1 | Cystm1 | 84418 | 12-May-15 |
| 5044 | 2 | 3 | 4 | | IV-1 | Cox6b2 | 125965 | 4-May-15 | 5538 | 2 | 3 | 4 | IV-1 | Cyt1 | 54360 | |
| 5053 | 2 | 3 | 4 | | IV-1 | Cox8b | 404544 | | 5539 | 2 | 3 | 4 | IV-1 | Cyyr1 | 116159 | |
| 5055 | 2 | 3 | 4 | | IV-1 | Cp | 1356 | | 5549 | 2 | 3 | 4 | IV-1 | D10Bwg1379e | | |
| 5066 | 2 | 3 | 4 | | IV-1 | Cpeb1 | 64691 | 4-May-15 | 5554 | 2 | 3 | 4 | IV-1 | D130017N08Rik | | |
| 5067 | 2 | 3 | 4 | | IV-1 | Cpeb2 | 132864 | 4-May-15 | 5569 | 2 | 3 | 4 | IV-1 | D1Pas1 | | |
| 5071 | 2 | 3 | 4 | | IV-1 | Cphx1 | | | 5574 | 2 | 3 | 4 | IV-1 | D330023K18Rik | | |
| 5078 | 2 | 3 | 4 | | IV-1 | Cpn1 | 1369 | 7-Jun-15 | 5575 | 2 | 3 | 4 | IV-1 | D330041H03Rik | | |
| 5079 | 2 | 3 | 4 | | IV-1 | Cpn2 | 1370 | 7-Jun-15 | 5592 | 2 | 3 | 4 | IV-1 | D630003M21Rik | | |
| 5084 | 2 | 3 | 4 | | IV-1 | Cpne5 | 57609 | 4-May-15 | 5596 | 2 | 3 | 4 | IV-1 | D630024D03Rik | | |
| 5086 | 2 | 3 | 4 | | IV-1 | Cpne7 | 27132 | 12-May-15 | 5599 | 2 | 3 | 4 | IV-1 | D630033O11Rik | | |
| 5087 | 2 | 3 | 4 | | IV-1 | Cpne8 | 144402 | 4-May-15 | 5600 | 2 | 3 | 4 | IV-1 | D630039A03Rik | | |
| 5089 | 2 | 3 | 4 | | IV-1 | Cpox | 1371 | | 5602 | 2 | 3 | 4 | IV-1 | D630045J12Rik | | |
| 5092 | 2 | 3 | 4 | | IV-1 | Cps1 | 1373 | 7-Jun-15 | 5603 | 2 | 3 | 4 | IV-1 | D630045M09Rik | | |
| 5102 | 2 | 3 | 4 | | IV-1 | Cpt1b | 1375 | 76/7 | 5620 | 2 | 3 | 4 | IV-1 | D830031N03Rik | | |
| 5111 | 2 | 3 | 4 | | IV-1 | Cr2 | 1380 | 7-Jun-15 | 5627 | 2 | 3 | 4 | IV-1 | D930015M05Rik | | |
| 5112 | 2 | 3 | 4 | | IV-1 | Crabp1 | 1381 | 4-May-15 | 5632 | 2 | 3 | 4 | IV-1 | D930048N14Rik | | |
| 5113 | 2 | 3 | 4 | | IV-1 | Crabp2 | 1382 | | 5641 | 2 | 3 | 4 | IV-1 | Dact2 | 168002 | 17-May-15 |
| 5116 | 2 | 3 | 4 | | IV-1 | Crat | 1384 | 12-May-15 | 5642 | 2 | 3 | 4 | IV-1 | Dact3 | 147906 | 4-May-15 |
| 5124 | 2 | 3 | 4 | | IV-1 | Creb3 | 10488 | 7-Jun-15 | 5652 | 2 | 3 | 4 | IV-1 | Dao | 1610 | 7-Jun-15 |
| 5127 | 2 | 3 | 4 | | IV-1 | Creb3l3 | 84699 | 28-May-15 | 5658 | 2 | 3 | 4 | IV-1 | Dapl1 | 92196 | 12-May-15 |
| 5129 | 2 | 3 | 4 | | IV-1 | Creb5 | 9586 | 21-May-15 | 5667 | 2 | 3 | 4 | IV-1 | Dbf4 | 10926 | 4-May-15 |
| 5137 | 2 | 3 | 4 | | IV-1 | Creld2 | 79174 | | 5672 | 2 | 3 | 4 | IV-1 | Dbn1 | 1627 | 3-May-15 |
| 5138 | 2 | 3 | 4 | | IV-1 | Crem | 1390 | 12-May-15 | 5673 | 2 | 3 | 4 | IV-1 | Dbndd1 | 79007 | 21-May-15 |
| 5142 | 2 | 3 | 4 | | IV-1 | Crhr2 | 1395 | 4-May-15 | 5676 | 2 | 3 | 4 | IV-1 | Dbp | 1628 | 7-Jun-15 |
| 5144 | 2 | 3 | 4 | | IV-1 | Crip1 | 1396 | 76/7 | 5699 | 2 | 3 | 4 | IV-1 | Dcdc2a | 51473 | 24-May-15 |
| 5146 | 2 | 3 | 4 | | IV-1 | Crip3 | 401262 | 4-May-15 | 5701 | 2 | 3 | 4 | IV-1 | Dcdc2c | 728597 | 21-May-15 |
| 5149 | 2 | 3 | 4 | | IV-1 | Crisp2 | 7180 | 21-May-15 | 5710 | 2 | 3 | 4 | IV-1 | Dcn | 1634 | 23-May-15 |
| 5156 | 2 | 3 | 4 | | IV-1 | Crlf1 | 9244 | 23-May-15 | 5721 | 2 | 3 | 4 | IV-1 | Dctd | 1635 | 4-May-15 |
| 5175 | 2 | 3 | 4 | | IV-1 | Cry1 | 1407 | 4-May-15 | 5735 | 2 | 3 | 4 | IV-1 | Dcxr | 51181 | 4-May-15 |
| 5178 | 2 | 3 | 4 | | IV-1 | Cryab | 1410 | 23-May-15 | 5740 | 2 | 3 | 4 | IV-1 | Ddh2 | 1643 | 23-May-15 |
| 5183 | 2 | 3 | 4 | | IV-1 | Crybb2 | 1415 | 21-May-15 | 5747 | 2 | 3 | 4 | IV-1 | Ddit4 | 54541 | 4-May-15 |
| 5187 | 2 | 3 | 4 | | IV-1 | Crygb | 1419 | 4-May-15 | 5749 | 2 | 3 | 4 | IV-1 | Ddn | 23109 | 4-May-15 |
| 5192 | 2 | 3 | 4 | | IV-1 | Crygn | 155051 | 21-May-15 | 5750 | 2 | 3 | 4 | IV-1 | Ddo | 8528 | 4-May-15 |
| 5207 | 2 | 3 | 4 | | IV-1 | Csf2rb | 1439 | | 5768 | 2 | 3 | 4 | IV-1 | Ddx26b | 203522 | 4-May-15 |
| 5210 | 2 | 3 | 4 | | IV-1 | Csf3r | 1441 | | 5797 | 2 | 3 | 4 | IV-1 | Decr1 | 1666 | 12-May-15 |
| 5238 | 2 | 3 | 4 | | IV-1 | Csrnp1 | 64651 | | 5803 | 2 | 3 | 4 | IV-1 | Defa17 | | |
| 5245 | 2 | 3 | 4 | | IV-1 | Cst10 | | | 5804 | 2 | 3 | 4 | IV-1 | Defa2 | 1667 | 12-May-15 |
| 5250 | 2 | 3 | 4 | | IV-1 | Cst6 | 1474 | 7-Jun-15 | 5805 | 2 | 3 | 4 | IV-1 | Defa20 | | |
| 5279 | 2 | 3 | 4 | | IV-1 | Ctgf | 1490 | 12-May-15 | 5806 | 2 | 3 | 4 | IV-1 | Defa21 | | |
| 5280 | 2 | 3 | 4 | | IV-1 | Cth | 1491 | 7-Jun-15 | 5808 | 2 | 3 | 4 | IV-1 | Defa23 | | |
| 5283 | 2 | 3 | 4 | | IV-1 | Ctla2a | | | 5812 | 2 | 3 | 4 | IV-1 | Defa3 | 1668 | 4-May-15 |
| 5284 | 2 | 3 | 4 | | IV-1 | Ctla2b | | | 5816 | 2 | 3 | 4 | IV-1 | Defa-ps1 | | |
| 5285 | 2 | 3 | 4 | | IV-1 | Ctla4 | 1493 | 17-May-15 | 5823 | 2 | 3 | 4 | IV-1 | Defb11 | 245913 | 4-May-15 |
| 5301 | 2 | 3 | 4 | | IV-1 | Ctrcos | | | 5844 | 2 | 3 | 4 | IV-1 | Defb36 | | |
| 5310 | 2 | 3 | 4 | | IV-1 | Crsc | 1075 | | 5846 | 2 | 3 | 4 | IV-1 | Defb38 | | |
| 5312 | 2 | 3 | 4 | | IV-1 | Ctse | 1510 | 12-May-15 | 5849 | 2 | 3 | 4 | IV-1 | Defb40 | | |
| 5313 | 2 | 3 | 4 | | IV-1 | Ctsf | 8722 | 4-May-15 | 5860 | 2 | 3 | 4 | IV-1 | Defb6 | | |
| 5317 | 2 | 3 | 4 | | IV-1 | Ctsk | 1513 | | 5863 | 2 | 3 | 4 | IV-1 | Defb9 | 245912 | 4-May-15 |
| 5324 | 2 | 3 | 4 | | IV-1 | Ctss | 1520 | 24-May-15 | 5865 | 2 | 3 | 4 | IV-1 | Degs2 | 123099 | 4-May-15 |
| 5325 | 2 | 3 | 4 | | IV-1 | Ctsw | 1521 | 4-May-15 | 5870 | 2 | 3 | 4 | IV-1 | Dennd2a | 27147 | 4-May-15 |
| 5328 | 2 | 3 | 4 | | IV-1 | Cttnbp2 | 83992 | 17-May-15 | 5871 | 2 | 3 | 4 | IV-1 | Dennd2c | 163259 | 4-May-15 |
| 5332 | 2 | 3 | 4 | | IV-1 | Ctxn1 | 404217 | | 5883 | 2 | 3 | 4 | IV-1 | Depdc1b | 55789 | 4-May-15 |
| 5358 | 2 | 3 | 4 | | IV-1 | Cwh43 | 80157 | 4-May-15 | 5898 | 2 | 3 | 4 | IV-1 | Dfna5 | 1687 | 23-May-15 |
| 5359 | 2 | 3 | 4 | | IV-1 | Cx3cl1 | 6376 | | 5901 | 2 | 3 | 4 | IV-1 | Dgat2 | 84649 | 12-May-15 |
| 5360 | 2 | 3 | 4 | | IV-1 | Cx3cr1 | 1524 | | 5902 | 2 | 3 | 4 | IV-1 | Dgat2l6 | 347516 | 4-May-15 |
| 5361 | 2 | 3 | 4 | | IV-1 | Cxadr | 1525 | 17-May-15 | 5912 | 2 | 3 | 4 | IV-1 | Dgkg | 1608 | 12-May-15 |
| 5363 | 2 | 3 | 4 | | IV-1 | Cxcl10 | 3627 | | 5919 | 2 | 3 | 4 | IV-1 | Dhcr24 | 1718 | 12-May-15 |
| 5367 | 2 | 3 | 4 | | IV-1 | Cxcl14 | 9547 | | 5928 | 2 | 3 | 4 | IV-1 | Dhrs11 | 79154 | 4-May-15 |
| 5375 | 2 | 3 | 4 | | IV-1 | Cxcr1 | 3577 | | 5966 | 2 | 3 | 4 | IV-1 | Dio3os | 64150 | 12-May-15 |
| 5376 | 2 | 3 | 4 | | IV-1 | Cxcr2 | 3579 | 17-May-15 | 5983 | 2 | 3 | 4 | IV-1 | Dkk3 | 27122 | 4-May-15 |
| 5378 | 2 | 3 | 4 | | IV-1 | Cxcr4 | 7852 | 21-May-15 | 5985 | 2 | 3 | 4 | IV-1 | Dkk1 | 27120 | 4-May-15 |
| 5379 | 2 | 3 | 4 | | IV-1 | Cxcr5 | 643 | 17-May-15 | 5987 | 2 | 3 | 4 | IV-1 | Dkl1 | 10395 | 7-Jun-15 |

Fig.22 - 26

| | | | | | | | | | | | | | | | | |
|---|---|---|---|---|---|---|---|---|---|---|---|---|---|---|---|---|
| 5996 | 2 | 3 | 4 | | IV-1 | Dlg5 | 9231 | 12-May-15 | 6609 | 2 | 3 | 4 | | IV-1 | Elmod1 | 55531 | 12-May-15 |
| 5997 | 2 | 3 | 4 | | IV-1 | Dlgap1 | 9229 | 17-May-15 | 6613 | 2 | 3 | 4 | | IV-1 | Eln | 2006 | 23-May-15 |
| 6003 | 2 | 3 | 4 | | IV-1 | Dlk2 | 65989 | 4-May-15 | 6620 | 2 | 3 | 4 | | IV-1 | Elovl6 | 79071 | 4-May-15 |
| 6004 | 2 | 3 | 4 | | IV-1 | Dll1 | 28514 | 12-May-15 | 6627 | 2 | 3 | 4 | | IV-1 | Eltd1 | 64123 | 12-May-15 |
| 6024 | 2 | 3 | 4 | | IV-1 | Dmp1 | 1758 | 17-May-15 | 6628 | 2 | 3 | 4 | | IV-1 | Emb | 5463 | 4-May-15 |
| 6028 | 2 | 3 | 4 | | IV-1 | Dmrt2 | 10655 | 4-May-15 | 6637 | 2 | 3 | 4 | | IV-1 | Emc9 | 51016 | 4-May-15 |
| 6045 | 2 | 3 | 4 | | IV-1 | Dnaaf3 | 352909 | 23-May-15 | 6645 | 2 | 3 | 4 | | IV-1 | Emilin2 | 84034 | 4-May-15 |
| 6062 | 2 | 3 | 4 | | IV-1 | Dnaja4 | 55466 | 4-May-15 | 6655 | 2 | 3 | 4 | | IV-1 | Emp3 | 2014 | 4-May-15 |
| 6069 | 2 | 3 | 4 | | IV-1 | Dnajb3 | 414061 | 4-May-15 | 6656 | 2 | 3 | 4 | | IV-1 | Emr1 | 2015 | 4-May-15 |
| 6071 | 2 | 3 | 4 | | IV-1 | Dnajb5 | 25822 | 4-May-15 | 6665 | 2 | 3 | 4 | | IV-1 | Enc1 | 8507 | 4-May-15 |
| 6077 | 2 | 3 | 4 | | IV-1 | Dnajc10 | 54431 | 4-May-15 | 6672 | 2 | 3 | 4 | | IV-1 | Eno | 375704 | 4-May-15 |
| 6079 | 2 | 3 | 4 | | IV-1 | Dnajc12 | 56521 | 4-May-15 | 6674 | 2 | 3 | 4 | | IV-1 | Enkur | 219670 | 4-May-15 |
| 6082 | 2 | 3 | 4 | | IV-1 | Dnajc15 | 29103 | 21-May-15 | 6675 | 2 | 3 | 4 | | IV-1 | Eno1 | 2023 | 24-May-15 |
| 6106 | 2 | 3 | 4 | | IV-1 | Dnali1 | 7802 | 4-May-15 | 6685 | 2 | 3 | 4 | | IV-1 | Enpp2 | 5168 | 12-May-15 |
| 6109 | 2 | 3 | 4 | | IV-1 | Dnase1l2 | 1775 | 12-May-15 | 6688 | 2 | 3 | 4 | | IV-1 | Enpp5 | 59084 | 4-May-15 |
| 6113 | 2 | 3 | 4 | | IV-1 | Dnd1 | 373863 | 4-May-15 | 6696 | 2 | 3 | 4 | | IV-1 | Entpd3 | 956 | 4-May-15 |
| 6119 | 2 | 3 | 4 | | IV-1 | Dnm3 | 26052 | 12-May-15 | 6700 | 2 | 3 | 4 | | IV-1 | Entpd7 | 57089 | 4-May-15 |
| 6120 | 2 | 3 | 4 | | IV-1 | Dnm3os | 100628315 | 4-May-15 | 6709 | 2 | 3 | 4 | | IV-1 | Epb4.1l1 | | |
| | | | | | | | | | 6711 | 2 | 3 | 4 | | IV-1 | Epb4.1l3 | | |
| 6133 | 2 | 3 | 4 | | IV-1 | Doc2b | 8447 | 4-May-15 | 6719 | 2 | 3 | 4 | | IV-1 | Epdr1 | 54749 | 4-May-15 |
| 6134 | 2 | 3 | 4 | | IV-1 | Doc2g | | | 6721 | 2 | 3 | 4 | | IV-1 | Epgn | 255324 | 4-May-15 |
| 6142 | 2 | 3 | 4 | | IV-1 | Dock6 | 57972 | 21-May-15 | 6722 | 2 | 3 | 4 | | IV-1 | Epha1 | 2041 | 12-May-15 |
| 6149 | 2 | 3 | 4 | | IV-1 | Dok3 | 79930 | 21-May-15 | 6735 | 2 | 3 | 4 | | IV-1 | Ephb6 | 2051 | 17-May-15 |
| 6159 | 2 | 3 | 4 | | IV-1 | Dos | 255057 | 4-May-15 | 6736 | 2 | 3 | 4 | | IV-1 | Ephx1 | 2052 | 17-May-15 |
| 6165 | 2 | 3 | 4 | | IV-1 | Dpep1 | 1800 | 12-May-15 | 6737 | 2 | 3 | 4 | | IV-1 | Ephx2 | 2053 | 12-May-15 |
| 6193 | 2 | 3 | 4 | | IV-1 | Dppa5a | | | 6740 | 2 | 3 | 4 | | IV-1 | Epm2a | 7957 | 13-Jun-15 |
| 6198 | 2 | 3 | 4 | | IV-1 | Dpyd | 1806 | 31-May-15 | 6744 | 2 | 3 | 4 | | IV-1 | Epn3 | 55040 | 4-May-15 |
| 6199 | 2 | 3 | 4 | | IV-1 | Dpys | 1807 | 4-May-15 | 6746 | 2 | 3 | 4 | | IV-1 | Epor | 2057 | 12-May-15 |
| 6201 | 2 | 3 | 4 | | IV-1 | Dpysl3 | 1809 | 4-May-15 | 6748 | 2 | 3 | 4 | | IV-1 | Eppk1 | 83481 | 4-May-15 |
| 6219 | 2 | 3 | 4 | | IV-1 | Dreh | | | 6756 | 2 | 3 | 4 | | IV-1 | Epsti1 | 94240 | 4-May-15 |
| 6236 | 2 | 3 | 4 | | IV-1 | Dsg2 | 1829 | 23-May-15 | 6768 | 2 | 3 | 4 | | IV-1 | Erbb3 | 2065 | 17-May-15 |
| 6240 | 2 | 3 | 4 | | IV-1 | Dsp | 1832 | 7-Jun-15 | 6803 | 2 | 3 | 4 | | IV-1 | Erm1 | 2081 | 24-May-15 |
| 6249 | 2 | 3 | 4 | | IV-1 | Dtna | 1837 | 12-May-15 | 6810 | 2 | 3 | 4 | | IV-1 | Errfi1 | 54206 | 4-May-15 |
| 6250 | 2 | 3 | 4 | | IV-1 | Dtnb | 1838 | 4-May-15 | 6812 | 2 | 3 | 4 | | IV-1 | Esam | 90952 | 4-May-15 |
| 6254 | 2 | 3 | 4 | | IV-1 | Dtx1 | 1840 | 4-May-15 | 6815 | 2 | 3 | 4 | | IV-1 | Esd | 2098 | 4-May-15 |
| 6261 | 2 | 3 | 4 | | IV-1 | Duox2 | 50506 | 24-May-15 | 6835 | 2 | 3 | 4 | | IV-1 | Espn | 83715 | 23-May-15 |
| 6269 | 2 | 3 | 4 | | IV-1 | Dusp1 | 1843 | 7-Jun-15 | 6843 | 2 | 3 | 4 | | IV-1 | Esrrg | 2104 | 4-May-15 |
| 6270 | 2 | 3 | 4 | | IV-1 | Dusp10 | 11221 | 4-May-15 | 6847 | 2 | 3 | 4 | | IV-1 | Esyt3 | 83850 | 4-May-15 |
| 6274 | 2 | 3 | 4 | | IV-1 | Dusp14 | 11072 | 4-May-15 | 6863 | 2 | 3 | 4 | | IV-1 | Etv1 | 2115 | 24-May-15 |
| 6277 | 2 | 3 | 4 | | IV-1 | Dusp18 | 150290 | 12-May-15 | 6872 | 2 | 3 | 4 | | IV-1 | Eva1c | 59271 | 4-May-15 |
| 6279 | 2 | 3 | 4 | | IV-1 | Dusp2 | 1844 | 4-May-15 | 6873 | 2 | 3 | 4 | | IV-1 | Evc | 2121 | 12-May-15 |
| 6283 | 2 | 3 | 4 | | IV-1 | Dusp26 | 78986 | 7-Jun-15 | 6874 | 2 | 3 | 4 | | IV-1 | Evc2 | 132884 | 21-May-15 |
| 6284 | 2 | 3 | 4 | | IV-1 | Dusp27 | 92235 | 4-May-15 | 6875 | 2 | 3 | 4 | | IV-1 | Evi2a | 2123 | 12-May-15 |
| 6285 | 2 | 3 | 4 | | IV-1 | Dusp28 | 285193 | 4-May-15 | 6907 | 2 | 3 | 4 | | IV-1 | Exosc6 | 118460 | 23-May-15 |
| 6287 | 2 | 3 | 4 | | IV-1 | Dusp4 | 1846 | 4-May-15 | 6914 | 2 | 3 | 4 | | IV-1 | Extl1 | 2134 | 12-May-15 |
| 6290 | 2 | 3 | 4 | | IV-1 | Dusp7 | 1849 | 4-May-15 | 6917 | 2 | 3 | 4 | | IV-1 | Eya1 | 2138 | 23-May-15 |
| 6291 | 2 | 3 | 4 | | IV-1 | Dusp8 | 1850 | 4-May-15 | 6923 | 2 | 3 | 4 | | IV-1 | Ezr | 7430 | 24-May-15 |
| 6295 | 2 | 3 | 4 | | IV-1 | Duxbl1 | | | 6930 | 2 | 3 | 4 | | IV-1 | F2 | 2147 | 31-May-15 |
| 6304 | 2 | 3 | 4 | | IV-1 | Dydc2 | 84332 | 4-May-15 | 6932 | 2 | 3 | 4 | | IV-1 | F2rl1 | 2150 | 4-May-15 |
| 6314 | 2 | 3 | 4 | | IV-1 | Dynll1 | 8655 | 24-May-15 | 6935 | 2 | 3 | 4 | | IV-1 | F3 | 2152 | 7-Jun-15 |
| 6317 | 2 | 3 | 4 | | IV-1 | Dynlrb2 | 83657 | 12-May-15 | 6942 | 2 | 3 | 4 | | IV-1 | F7 | 2155 | 12-May-15 |
| 6321 | 2 | 3 | 4 | | IV-1 | Dynlt1f | | | 6946 | 2 | 3 | 4 | | IV-1 | F830002L21Rik | | |
| 6326 | 2 | 3 | 4 | | IV-1 | Dyrk3 | 8444 | 4-May-15 | 6947 | 2 | 3 | 4 | | IV-1 | F830016B08Rik | | |
| 6332 | 2 | 3 | 4 | | IV-1 | Dzip1 | 22873 | 4-May-15 | 6952 | 2 | 3 | 4 | | IV-1 | Fa2h | 79152 | 31-May-15 |
| 6333 | 2 | 3 | 4 | | IV-1 | Dzip1l | 199221 | 4-May-15 | 6957 | 2 | 3 | 4 | | IV-1 | Fabp3 | 2170 | 24-May-15 |
| 6337 | 2 | 3 | 4 | | IV-1 | E030011O05Rik | | | 6959 | 2 | 3 | 4 | | IV-1 | Fabp5 | 2171 | 7-Jun-15 |
| 6348 | 2 | 3 | 4 | | IV-1 | E130012A19Rik | | | 6960 | 2 | 3 | 4 | | IV-1 | Fabp6 | 2172 | 4-May-15 |
| 6351 | 2 | 3 | 4 | | IV-1 | E130112N10Rik | | | 6961 | 2 | 3 | 4 | | IV-1 | Fabp7 | 2173 | 12-May-15 |
| 6360 | 2 | 3 | 4 | | IV-1 | E130309D14Rik | | | 6962 | 2 | 3 | 4 | | IV-1 | Fabp9 | 646480 | 4-May-15 |
| 6362 | 2 | 3 | 4 | | IV-1 | E130310J04Rik | | | 6965 | 2 | 3 | 4 | | IV-1 | Fads2 | 9415 | 4-May-15 |
| 6370 | 2 | 3 | 4 | | IV-1 | E230029C05Rik | | | 6966 | 2 | 3 | 4 | | IV-1 | Fads3 | 3998 | 4-May-15 |
| 6371 | 2 | 3 | 4 | | IV-1 | E2f1 | 1869 | 7-Jun-15 | 6970 | 2 | 3 | 4 | | IV-1 | Fah | 2184 | 7-Jun-15 |
| 6378 | 2 | 3 | 4 | | IV-1 | E2f8 | 79733 | 12-May-15 | 6976 | 2 | 3 | 4 | | IV-1 | Fam101a | 144347 | 4-May-15 |
| 6382 | 2 | 3 | 4 | | IV-1 | E330013P04Rik | | | 6983 | 2 | 3 | 4 | | IV-1 | Fam107a | 11170 | 12-May-15 |
| 6396 | 2 | 3 | 4 | | IV-1 | E530011L22Rik | | | 6985 | 2 | 3 | 4 | | IV-1 | Fam109a | 144717 | 4-May-15 |
| 6403 | 2 | 3 | 4 | | IV-1 | Ear2 | 2063 | 4-May-15 | 6986 | 2 | 3 | 4 | | IV-1 | Fam109b | 150368 | 4-May-15 |
| 6423 | 2 | 3 | 4 | | IV-1 | Echdc1 | 55862 | 4-May-15 | 6989 | 2 | 3 | 4 | | IV-1 | Fam110c | 642273 | 4-May-15 |
| 6425 | 2 | 3 | 4 | | IV-1 | Echdc3 | 79746 | 4-May-15 | 6996 | 2 | 3 | 4 | | IV-1 | Fam117a | 81558 | 4-May-15 |
| 6429 | 2 | 3 | 4 | | IV-1 | Eci3 | | | 7009 | 2 | 3 | 4 | | IV-1 | Fam126a | 84668 | 23-May-15 |
| 6431 | 2 | 3 | 4 | | IV-1 | Ecm2 | 1842 | 4-May-15 | 7017 | 2 | 3 | 4 | | IV-1 | Fam132a | 388581 | 4-May-15 |
| 6432 | 2 | 3 | 4 | | IV-1 | Ecscr | 641700 | 4-May-15 | 7018 | 2 | 3 | 4 | | IV-1 | Fam132b | 151176 | 12-May-15 |
| 6436 | 2 | 3 | 4 | | IV-1 | Eda | 1896 | 24-May-15 | 7021 | 2 | 3 | 4 | | IV-1 | Fam134b | 54463 | 23-May-15 |
| 6448 | 2 | 3 | 4 | | IV-1 | Edn1 | 1906 | 24-May-15 | 7026 | 2 | 3 | 4 | | IV-1 | Fam13a | 10144 | 24-May-15 |
| 6450 | 2 | 3 | 4 | | IV-1 | Edn3 | 1908 | 23-May-15 | 7052 | 2 | 3 | 4 | | IV-1 | Fam167a | 83648 | 4-May-15 |
| 6455 | 2 | 3 | 4 | | IV-1 | Eed | 8726 | 2-Jun-15 | 7056 | 2 | 3 | 4 | | IV-1 | Fam169a | 26049 | 12-May-15 |
| 6463 | 2 | 3 | 4 | | IV-1 | Eef2k | 24904 | 4-May-15 | 7061 | 2 | 3 | 4 | | IV-1 | Fam171a2 | 284069 | 12-May-15 |
| 6465 | 2 | 3 | 4 | | IV-1 | Eepd1 | 80820 | 4-May-15 | 7077 | 2 | 3 | 4 | | IV-1 | Fam183b | 340286 | 21-May-15 |
| 6467 | 2 | 3 | 4 | | IV-1 | Efcab10 | 100130771 | 12-May-15 | 7079 | 2 | 3 | 4 | | IV-1 | Fam184b | 27146 | 4-May-15 |
| 6473 | 2 | 3 | 4 | | IV-1 | Efcab4a | 283229 | 4-May-15 | 7083 | 2 | 3 | 4 | | IV-1 | Fam187b | 148109 | 4-May-15 |
| 6474 | 2 | 3 | 4 | | IV-1 | Efcab4b | 84766 | 4-May-15 | 7092 | 2 | 3 | 4 | | IV-1 | Fam195a | 84331 | 4-May-15 |
| 6481 | 2 | 3 | 4 | | IV-1 | Efemp1 | 2202 | 29-May-15 | 7097 | 2 | 3 | 4 | | IV-1 | Fam198b | 51313 | 4-May-15 |
| 6482 | 2 | 3 | 4 | | IV-1 | Efemp2 | 30008 | 23-May-15 | 7103 | 2 | 3 | 4 | | IV-1 | Fam19a5 | 25817 | 4-May-15 |
| 6488 | 2 | 3 | 4 | | IV-1 | Efna1 | 1942 | 14-May-15 | 7113 | 2 | 3 | 4 | | IV-1 | Fam20c | 56975 | 17-May-15 |
| 6501 | 2 | 3 | 4 | | IV-1 | Egf | 1950 | 24-May-15 | 7119 | 2 | 3 | 4 | | IV-1 | Fam213a | 84293 | 4-May-15 |
| 6502 | 2 | 3 | 4 | | IV-1 | Egfbp2 | | | 7120 | 2 | 3 | 4 | | IV-1 | Fam213b | 127281 | 4-May-15 |
| 6504 | 2 | 3 | 4 | | IV-1 | Egfl6 | 25975 | 4-May-15 | 7133 | 2 | 3 | 4 | | IV-1 | Fam222a | 84915 | 4-May-15 |
| 6511 | 2 | 3 | 4 | | IV-1 | Egln3 | 112399 | 12-May-15 | 7150 | 2 | 3 | 4 | | IV-1 | Fam3c | 10447 | 4-May-15 |
| 6512 | 2 | 3 | 4 | | IV-1 | Egr1 | 1958 | 24-May-15 | 7154 | 2 | 3 | 4 | | IV-1 | Fam46a | 55603 | 12-May-15 |
| 6514 | 2 | 3 | 4 | | IV-1 | Egr3 | 1960 | 12-May-15 | 7155 | 2 | 3 | 4 | | IV-1 | Fam46b | 115572 | 4-May-15 |
| 6522 | 2 | 3 | 4 | | IV-1 | Ehf | 26298 | 4-May-15 | 7156 | 2 | 3 | 4 | | IV-1 | Fam46c | 54855 | 4-May-15 |
| 6523 | 2 | 3 | 4 | | IV-1 | Ehhadh | 1962 | 12-May-15 | 7167 | 2 | 3 | 4 | | IV-1 | Fam57a | 79850 | 4-May-15 |
| 6530 | 2 | 3 | 4 | | IV-1 | Eid3 | 493861 | 7-Jun-15 | 7178 | 2 | 3 | 4 | | IV-1 | Fam69b | 138311 | 4-May-15 |
| 6573 | 2 | 3 | 4 | | IV-1 | Eif4ebp1 | 1978 | 29-May-15 | 7181 | 2 | 3 | 4 | | IV-1 | Fam71b | 153745 | 4-May-15 |
| 6584 | 2 | 3 | 4 | | IV-1 | Eif5b | 9669 | 12-May-15 | 7183 | 2 | 3 | 4 | | IV-1 | Fam71e1 | 112703 | 12-May-15 |
| 6588 | 2 | 3 | 4 | | IV-1 | Elane | 1991 | 4-May-15 | 7186 | 2 | 3 | 4 | | IV-1 | Fam71f2 | 346653 | 4-May-15 |
| 6595 | 2 | 3 | 4 | | IV-1 | Elf3 | 1999 | 12-May-15 | 7188 | 2 | 3 | 4 | | IV-1 | Fam73a | 374986 | 4-May-15 |
| 6602 | 2 | 3 | 4 | | IV-1 | Elk4 | 2005 | 28-May-15 | 7192 | 2 | 3 | 4 | | IV-1 | Fam78a | 286336 | 4-May-15 |

Fig.22 - 27

| | | | | | | | | | | | | | | | |
|---|---|---|---|---|---|---|---|---|---|---|---|---|---|---|---|
| 7196 | 2 | 3 | 4 | | IV-1 | Fam83b | 222584 | 4-May-15 | 7707 | 2 | 3 | 4 | IV-1 | G0s2 | 50486 | 4-May-15 |
| 7202 | 2 | 3 | 4 | | IV-1 | Fam83h | 286077 | 21-May-15 | 7712 | 2 | 3 | 4 | IV-1 | G630025P09Rik | | 4-May-15 |
| 7204 | 2 | 3 | 4 | | IV-1 | Fam84b | 157638 | 4-May-15 | 7717 | 2 | 3 | 4 | IV-1 | G6b | 80739 | 4-May-15 |
| 7206 | 2 | 3 | 4 | | IV-1 | Fam89a | 375061 | 4-May-15 | 7719 | 2 | 3 | 4 | IV-1 | G6pc | 2538 | 23-May-15 |
| 7214 | 2 | 3 | 4 | | IV-1 | Fam98c | 147965 | 4-May-15 | 7726 | 2 | 3 | 4 | IV-1 | Gab1 | 2549 | 7-Jun-15 |
| 7230 | 2 | 3 | 4 | | IV-1 | Far2 | 55711 | 14-May-15 | 7759 | 2 | 3 | 4 | IV-1 | Gadd45a | 1647 | 24-May-15 |
| 7233 | 2 | 3 | 4 | | IV-1 | Fars2 | 10667 | 21-May-15 | 7761 | 2 | 3 | 4 | IV-1 | Gadd45g | 10912 | 4-May-15 |
| 7237 | 2 | 3 | 4 | | IV-1 | Fasl | 356 | 24-May-15 | 7766 | 2 | 3 | 4 | IV-1 | Gal3st1 | 9514 | 4-May-15 |
| 7238 | 2 | 3 | 4 | | IV-1 | Fasn | 7194 | 4-May-15 | 7781 | 2 | 3 | 4 | IV-1 | Galnt14 | 79623 | 14-May-15 |
| 7253 | 2 | 3 | 4 | | IV-1 | Fblim1 | 54751 | 4-May-15 | 7782 | 2 | 3 | 4 | IV-1 | Galnt15 | 117248 | 7-Jun-15 |
| 7257 | 2 | 3 | 4 | | IV-1 | Fbln5 | 10516 | 23-May-15 | 7786 | 2 | 3 | 4 | IV-1 | Galnt3 | 2591 | 4-May-15 |
| 7261 | 2 | 3 | 4 | | IV-1 | Fbp1 | 2203 | 12-May-15 | 7789 | 2 | 3 | 4 | IV-1 | Galnt6 | 11226 | 4-May-15 |
| 7262 | 2 | 3 | 4 | | IV-1 | Fbp2 | 8789 | 7-Jun-15 | 7800 | 2 | 3 | 4 | IV-1 | Gan | 8139 | 23-May-15 |
| 7272 | 2 | 3 | 4 | | IV-1 | Fbxl18 | 80028 | 4-May-15 | 7805 | 2 | 3 | 4 | IV-1 | Gapdhs | 26330 | 12-May-15 |
| 7284 | 2 | 3 | 4 | | IV-1 | Fbxo10 | 26267 | 4-May-15 | 7809 | 2 | 3 | 4 | IV-1 | Garem | 64762 | 4-May-15 |
| 7290 | 2 | 3 | 4 | | IV-1 | Fbxo2 | 26232 | 12-May-15 | 7814 | 2 | 3 | 4 | IV-1 | Gas1 | 2619 | 4-May-15 |
| 7298 | 2 | 3 | 4 | | IV-1 | Fbxo30 | 84085 | 7-Jun-15 | 7820 | 2 | 3 | 4 | IV-1 | Gas6 | 2621 | 18-May-15 |
| 7299 | 2 | 3 | 4 | | IV-1 | Fbxo31 | 79791 | 7-Jun-15 | 7824 | 2 | 3 | 4 | IV-1 | Gata1 | 2623 | 23-May-15 |
| 7300 | 2 | 3 | 4 | | IV-1 | Fbxo32 | 114907 | 12-May-15 | 7833 | 2 | 3 | 4 | IV-1 | Gatad2b | 57459 | 4-May-15 |
| 7303 | 2 | 3 | 4 | | IV-1 | Fbxo36 | 130888 | 4-May-15 | 7837 | 2 | 3 | 4 | IV-1 | Gatsl3 | 652968 | 4-May-15 |
| 7339 | 2 | 3 | 4 | | IV-1 | Fbxw7 | 55294 | 12-May-15 | 7859 | 2 | 3 | 4 | IV-1 | Gcat | 23464 | 4-May-15 |
| 7344 | 2 | 3 | 4 | | IV-1 | Fcer1g | 2207 | 12-May-15 | 7867 | 2 | 3 | 4 | IV-1 | Gchfr | 2644 | 4-May-15 |
| 7345 | 2 | 3 | 4 | | IV-1 | Fcer2a | | | 7871 | 2 | 3 | 4 | IV-1 | Gclm | 2730 | 21-May-15 |
| 7346 | 2 | 3 | 4 | | IV-1 | Fcf1 | 51077 | 12-May-15 | 7875 | 2 | 3 | 4 | IV-1 | Gcnt1 | 2650 | 4-May-15 |
| 7348 | 2 | 3 | 4 | | IV-1 | Fcgr1 | | | 7884 | 2 | 3 | 4 | IV-1 | Gdap10 | | |
| 7350 | 2 | 3 | 4 | | IV-1 | Fcgr3 | 2214, 2215 | 7-Jun-15 | 7889 | 2 | 3 | 4 | IV-1 | Gdf10 | 2662 | 4-May-15 |
| 7351 | 2 | 3 | 4 | | IV-1 | Fcgr4 | | | 7891 | 2 | 3 | 4 | IV-1 | Gdf15 | 9518 | 4-May-15 |
| 7357 | 2 | 3 | 4 | | IV-1 | Fcna | | | 7894 | 2 | 3 | 4 | IV-1 | Gdf5 | 8200 | 28-May-15 |
| 7359 | 2 | 3 | 4 | | IV-1 | Fcrl1 | 135350 | 4-May-15 | 7902 | 2 | 3 | 4 | IV-1 | Gdpd2 | 54857 | 4-May-15 |
| 7365 | 2 | 3 | 4 | | IV-1 | Fdft1 | 2222 | 12-May-15 | 7906 | 2 | 3 | 4 | IV-1 | Gdpgp1 | 390637 | 12-May-15 |
| 7366 | 2 | 3 | 4 | | IV-1 | Fdps | 2224 | 12-May-15 | 7907 | 2 | 3 | 4 | IV-1 | Gem | 2689 | 7-Jun-15 |
| 7371 | 2 | 3 | 4 | | IV-1 | Fech | 2235 | 23-May-15 | 7916 | 2 | 3 | 4 | IV-1 | Gfap | 2670 | 23-May-15 |
| 7372 | 2 | 3 | 4 | | IV-1 | Fem1a | 55527 | 7-Jun-15 | 7919 | 2 | 3 | 4 | IV-1 | Gfi1b | 8328 | 23-May-15 |
| 7384 | 2 | 3 | 4 | | IV-1 | Fes | 2242 | 12-May-15 | 7929 | 2 | 3 | 4 | IV-1 | Gfra4 | 64096 | 4-May-15 |
| 7385 | 2 | 3 | 4 | | IV-1 | Fetub | 26998 | 12-May-15 | 7938 | 2 | 3 | 4 | IV-1 | Ggh | 8836 | 12-May-15 |
| 7391 | 2 | 3 | 4 | | IV-1 | Ffar1 | 2864 | 17-May-15 | 7940 | 2 | 3 | 4 | IV-1 | Ggnbp1 | 449520 | 4-May-15 |
| 7394 | 2 | 3 | 4 | | IV-1 | Ffar4 | 338557 | 24-May-15 | 7942 | 2 | 3 | 4 | IV-1 | Ggps1 | 9453 | 4-May-15 |
| 7397 | 2 | 3 | 4 | | IV-1 | Fgd1 | 2245 | 31-May-15 | 7943 | 2 | 3 | 4 | IV-1 | Ggt1 | 2678 | 17-May-15 |
| 7400 | 2 | 3 | 4 | | IV-1 | Fgd4 | 121512 | 23-May-15 | 7946 | 2 | 3 | 4 | IV-1 | Ggt7 | 2686 | 4-May-15 |
| 7406 | 2 | 3 | 4 | | IV-1 | Fgf12 | 2257 | 4-May-15 | 7951 | 2 | 3 | 4 | IV-1 | Ghr | 2690 | 24-May-15 |
| 7407 | 2 | 3 | 4 | | IV-1 | Fgf13 | 2258 | 7-Jun-15 | 7962 | 2 | 3 | 4 | IV-1 | Gimap3 | 474345 | 4-May-15 |
| 7412 | 2 | 3 | 4 | | IV-1 | Fgf18 | 9817 | 4-May-15 | 7963 | 2 | 3 | 4 | IV-1 | Gimap4 | 55303 | 4-May-15 |
| 7413 | 2 | 3 | 4 | | IV-1 | Fgf2 | 2247 | 7-Jun-15 | 7966 | 2 | 3 | 4 | IV-1 | Gimap7 | 168537 | 4-May-15 |
| 7415 | 2 | 3 | 4 | | IV-1 | Fgf21 | 26291 | 17-May-15 | 7971 | 2 | 3 | 4 | IV-1 | Gins1 | 9837 | 12-May-15 |
| 7426 | 2 | 3 | 4 | | IV-1 | Fgfbp3 | 143282 | 4-May-15 | 7972 | 2 | 3 | 4 | IV-1 | Gins2 | 51659 | 4-May-15 |
| 7427 | 2 | 3 | 4 | | IV-1 | Fgfr1 | 2260 | 23-May-15 | 7977 | 2 | 3 | 4 | IV-1 | Gipc2 | 54810 | 4-May-15 |
| 7430 | 2 | 3 | 4 | | IV-1 | Fgfr2 | 2263 | 24-May-15 | 7978 | 2 | 3 | 4 | IV-1 | Gipc3 | 126326 | 4-May-15 |
| 7436 | 2 | 3 | 4 | | IV-1 | Fgl1 | 2267 | 4-May-15 | 7989 | 2 | 3 | 4 | IV-1 | Gjb1 | 2705 | 23-May-15 |
| 7442 | 2 | 3 | 4 | | IV-1 | Fhdc1 | 85462 | 21-May-15 | 7991 | 2 | 3 | 4 | IV-1 | Gjb3 | 2707 | 23-May-15 |
| 7443 | 2 | 3 | 4 | | IV-1 | Fhit | 2272 | 31-May-15 | 7992 | 2 | 3 | 4 | IV-1 | Gjb4 | 127534 | 4-May-15 |
| 7444 | 2 | 3 | 4 | | IV-1 | Fhl1 | 2273 | 7-Jun-15 | 7993 | 2 | 3 | 4 | IV-1 | Gjb5 | 2709 | 4-May-15 |
| 7452 | 2 | 3 | 4 | | IV-1 | Fibin | 387758 | 4-May-15 | 8002 | 2 | 3 | 4 | IV-1 | Gk2 | 2712 | 12-May-15 |
| 7456 | 2 | 3 | 4 | | IV-1 | Figf | 2277 | 17-May-15 | 8003 | 2 | 3 | 4 | IV-1 | Gk5 | 256356 | 4-May-15 |
| 7459 | 2 | 3 | 4 | | IV-1 | Fign1 | 63979 | 4-May-15 | 8004 | 2 | 3 | 4 | IV-1 | Gkap1 | 80318 | 12-May-15 |
| 7461 | 2 | 3 | 4 | | IV-1 | Filip1 | 27145 | 4-May-15 | 8006 | 2 | 3 | 4 | IV-1 | Gkn2 | 200504 | 4-May-15 |
| 7469 | 2 | 3 | 4 | | IV-1 | Fjx1 | 24147 | 4-May-15 | 8009 | 2 | 3 | 4 | IV-1 | Gkn1 | 2720 | 12-May-15 |
| 7471 | 2 | 3 | 4 | | IV-1 | Fkbp11 | 51303 | 21-May-15 | 8011 | 2 | 3 | 4 | IV-1 | Glb1l2 | 89944 | 4-May-15 |
| 7475 | 2 | 3 | 4 | | IV-1 | Fkbp1b | 2281 | 4-May-15 | 8023 | 2 | 3 | 4 | IV-1 | Glipr1 | 11010 | 4-May-15 |
| 7479 | 2 | 3 | 4 | | IV-1 | Fkbp5 | 2289 | 17-May-15 | 8026 | 2 | 3 | 4 | IV-1 | Glipr2 | 152007 | 4-May-15 |
| 7505 | 2 | 3 | 4 | | IV-1 | Flywch2 | 114984 | 4-May-15 | 8040 | 2 | 3 | 4 | IV-1 | Glrb | 2743 | 4-May-15 |
| 7511 | 2 | 3 | 4 | | IV-1 | Fmo1 | 2326 | 12-May-15 | 8045 | 2 | 3 | 4 | IV-1 | Glrx5 | 51218 | 4-May-15 |
| 7518 | 2 | 3 | 4 | | IV-1 | Fmod | 2331 | 12-May-15 | 8060 | 2 | 3 | 4 | IV-1 | Glud1 | 2746 | 7-Jun-15 |
| 7521 | 2 | 3 | 4 | | IV-1 | Fn1 | 2335 | 24-May-15 | 8061 | 2 | 3 | 4 | IV-1 | Glul | 2752 | 4-May-15 |
| 7523 | 2 | 3 | 4 | | IV-1 | Fn3krp | 79672 | 4-May-15 | 8064 | 2 | 3 | 4 | IV-1 | Glycam1 | 644076 | 4-May-15 |
| 7533 | 2 | 3 | 4 | | IV-1 | Fndc5 | 252995 | 17-May-15 | 8077 | 2 | 3 | 4 | IV-1 | Gm10094 | | |
| 7534 | 2 | 3 | 4 | | IV-1 | Fndc7 | 163479 | 4-May-15 | 8083 | 2 | 3 | 4 | IV-1 | Gm10142 | | |
| 7542 | 2 | 3 | 4 | | IV-1 | Foxh1 | 2346 | 14-May-15 | 8087 | 2 | 3 | 4 | IV-1 | Gm10228 | | |
| 7543 | 2 | 3 | 4 | | IV-1 | Foxl1 | 2348 | 24-May-15 | 8088 | 2 | 3 | 4 | IV-1 | Gm10229 | | |
| 7544 | 2 | 3 | 4 | | IV-1 | Foxl2 | 2350 | 12-May-15 | 8117 | 2 | 3 | 4 | IV-1 | Gm10439 | | |
| 7547 | 2 | 3 | 4 | | IV-1 | Fos | 2353 | 4-May-15 | 8121 | 2 | 3 | 4 | IV-1 | Gm10451 | | |
| 7548 | 2 | 3 | 4 | | IV-1 | Fosb | 2354 | 12-May-15 | 8139 | 2 | 3 | 4 | IV-1 | Gm10560 | | |
| 7550 | 2 | 3 | 4 | | IV-1 | Fosl2 | 2355 | 12-May-15 | 8147 | 2 | 3 | 4 | IV-1 | Gm10638 | | |
| 7556 | 2 | 3 | 4 | | IV-1 | Foxc1 | 2296 | 4-May-15 | 8151 | 2 | 3 | 4 | IV-1 | Gm10653 | | |
| 7561 | 2 | 3 | 4 | | IV-1 | Foxd3 | 27022 | 17-May-15 | 8172 | 2 | 3 | 4 | IV-1 | Gm10790 | | |
| 7567 | 2 | 3 | 4 | | IV-1 | Foxg1 | 2290 | 27-May-15 | 8176 | 2 | 3 | 4 | IV-1 | Gm10823 | | |
| 7578 | 2 | 3 | 4 | | IV-1 | Foxl2 | 668 | 28-May-15 | 8181 | 2 | 3 | 4 | IV-1 | Gm10865 | | |
| 7579 | 2 | 3 | 4 | | IV-1 | Foxl2os | | | 8182 | 2 | 3 | 4 | IV-1 | Gm10872 | | |
| 7586 | 2 | 3 | 4 | | IV-1 | Foxo3 | 2309 | 31-May-15 | 8188 | 2 | 3 | 4 | IV-1 | Gm11127 | | |
| 7593 | 2 | 3 | 4 | | IV-1 | Foxq1 | 94234 | 28-May-15 | 8208 | 2 | 3 | 4 | IV-1 | Gm11517 | | |
| 7597 | 2 | 3 | 4 | | IV-1 | Foxred2 | 80020 | 4-May-15 | 8216 | 2 | 3 | 4 | IV-1 | Gm11554 | | |
| 7599 | 2 | 3 | 4 | | IV-1 | Fpgs | 2356 | 12-May-15 | 8217 | 2 | 3 | 4 | IV-1 | Gm11559 | | |
| 7610 | 2 | 3 | 4 | | IV-1 | Frat2 | 23401 | 4-May-15 | 8218 | 2 | 3 | 4 | IV-1 | Gm11562 | | |
| 7613 | 2 | 3 | 4 | | IV-1 | Frem3 | 166752 | 12-May-15 | 8219 | 2 | 3 | 4 | IV-1 | Gm11563 | | |
| 7615 | 2 | 3 | 4 | | IV-1 | Frk | 2444 | 4-May-15 | 8220 | 2 | 3 | 4 | IV-1 | Gm11564 | | |
| 7619 | 2 | 3 | 4 | | IV-1 | Frmd5 | 84978 | 4-May-15 | 8222 | 2 | 3 | 4 | IV-1 | Gm11567 | | |
| 7623 | 2 | 3 | 4 | | IV-1 | Frmpd1 | 22844 | 4-May-15 | 8223 | 2 | 3 | 4 | IV-1 | Gm11568 | | |
| 7624 | 2 | 3 | 4 | | IV-1 | Frmpd1os | | | 8226 | 2 | 3 | 4 | IV-1 | Gm11595 | | |
| 7642 | 2 | 3 | 4 | | IV-1 | Fsd2 | 123722 | 4-May-15 | 8227 | 2 | 3 | 4 | IV-1 | Gm11596 | | |
| 7646 | 2 | 3 | 4 | | IV-1 | Fst | 10468 | 12-May-15 | 8231 | 2 | 3 | 4 | IV-1 | Gm11710 | | |
| 7667 | 2 | 3 | 4 | | IV-1 | Fundc2 | 65991 | 12-May-15 | 8232 | 2 | 3 | 4 | IV-1 | Gm11744 | | |
| 7674 | 2 | 3 | 4 | | IV-1 | Fut2 | 2524 | 31-May-15 | 8238 | 2 | 3 | 4 | IV-1 | Gm11837 | | |
| 7682 | 2 | 3 | 4 | | IV-1 | Fxn | 2395 | 28-May-15 | 8239 | 2 | 3 | 4 | IV-1 | Gm11937 | | |
| 7685 | 2 | 3 | 4 | | IV-1 | Fxyd1 | 5348 | 12-May-15 | 8240 | 2 | 3 | 4 | IV-1 | Gm11938 | | |
| 7686 | 2 | 3 | 4 | | IV-1 | Fxyd2 | 486 | 4-May-15 | 8243 | 2 | 3 | 4 | IV-1 | Gm11974 | | |
| 7687 | 2 | 3 | 4 | | IV-1 | Fxyd3 | 5349 | 4-May-15 | 8249 | 2 | 3 | 4 | IV-1 | Gm12060 | | |
| 7697 | 2 | 3 | 4 | | IV-1 | Fzd10 | 11211 | 4-May-15 | 8257 | 2 | 3 | 4 | IV-1 | Gm12216 | | |
| 7700 | 2 | 3 | 4 | | IV-1 | Fzd4 | 8322 | 23-May-15 | 8264 | 2 | 3 | 4 | IV-1 | Gm12359 | | |

Fig.22 - 28

| | | | | | | | | | | | | | | | | | |
|---|---|---|---|---|---|---|---|---|---|---|---|---|---|---|---|---|---|
| 8288 | 2 | 3 | 4 | | IV-1 | Gm13011 | | | 9220 | 2 | 3 | 4 | | IV-1 | Gnai1 | 2770 | 12-May-15 |
| 8304 | 2 | 3 | 4 | | IV-1 | Gm13124 | | | 9228 | 2 | 3 | 4 | | IV-1 | Gnat2 | 2780 | 23-May-15 |
| 8307 | 2 | 3 | 4 | | IV-1 | Gm13139 | | | 9229 | 2 | 3 | 4 | | IV-1 | Gnat3 | 346562 | 4-May-15 |
| 8308 | 2 | 3 | 4 | | IV-1 | Gm13152 | | | 9235 | 2 | 3 | 4 | | IV-1 | Gnb3 | 2784 | 12-May-15 |
| 8311 | 2 | 3 | 4 | | IV-1 | Gm13177 | | | 9242 | 2 | 3 | 4 | | IV-1 | Gng13 | 51764 | 4-May-15 |
| 8312 | 2 | 3 | 4 | | IV-1 | Gm13178 | | | 9243 | 2 | 3 | 4 | | IV-1 | Gng2 | 54331 | 12-May-15 |
| 8336 | 2 | 3 | 4 | | IV-1 | Gm13306 | | | 9245 | 2 | 3 | 4 | | IV-1 | Gng4 | 2786 | 4-May-15 |
| 8352 | 2 | 3 | 4 | | IV-1 | Gm13629 | | | 9248 | 2 | 3 | 4 | | IV-1 | Gng8 | 94235 | #NAME? |
| 8353 | 2 | 3 | 4 | | IV-1 | Gm13710 | | | 9250 | 2 | 3 | 4 | | IV-1 | Gngt2 | 2793 | 4-May-15 |
| 8357 | 2 | 3 | 4 | | IV-1 | Gm13807 | | | 9253 | 2 | 3 | 4 | | IV-1 | Gnl3 | 26354 | 4-May-15 |
| 8363 | 2 | 3 | 4 | | IV-1 | Gm14005 | | | 9255 | 2 | 3 | 4 | | IV-1 | Gnmt | 27232 | 12-May-15 |
| 8367 | 2 | 3 | 4 | | IV-1 | Gm14085 | | | 9286 | 2 | 3 | 4 | | IV-1 | Got1 | 2805 | 7-Jun-15 |
| 8370 | 2 | 3 | 4 | | IV-1 | Gm14137 | | | 9288 | 2 | 3 | 4 | | IV-1 | Got2 | 2806 | 4-May-15 |
| 8377 | 2 | 3 | 4 | | IV-1 | Gm14288 | | | 9292 | 2 | 3 | 4 | | IV-1 | Gp49a | | |
| 8378 | 2 | 3 | 4 | | IV-1 | Gm14295 | | | 9312 | 2 | 3 | 4 | | IV-1 | Gpc1 | 2817 | 3-May-15 |
| 8399 | 2 | 3 | 4 | | IV-1 | Gm14436 | | | 9313 | 2 | 3 | 4 | | IV-1 | Gpc2 | 221914 | 4-May-15 |
| 8401 | 2 | 3 | 4 | | IV-1 | Gm14446 | | | 9314 | 2 | 3 | 4 | | IV-1 | Gpc3 | 2719 | 23-May-15 |
| 8406 | 2 | 3 | 4 | | IV-1 | Gm14475 | | | 9319 | 2 | 3 | 4 | | IV-1 | Gpd1 | 2819 | 4-May-15 |
| 8419 | 2 | 3 | 4 | | IV-1 | Gm14548 | | | 9321 | 2 | 3 | 4 | | IV-1 | Gpd2 | 2820 | 12-May-15 |
| 8434 | 2 | 3 | 4 | | IV-1 | Gm14850 | | | 9322 | 2 | 3 | 4 | | IV-1 | Gper1 | 2852 | 31-May-15 |
| 8435 | 2 | 3 | 4 | | IV-1 | Gm14851 | | | 9323 | 2 | 3 | 4 | | IV-1 | Gpha2 | 170589 | 4-May-15 |
| 8443 | 2 | 3 | 4 | | IV-1 | Gm15093 | | | 9327 | 2 | 3 | 4 | | IV-1 | Gpihbp1 | 338328 | 4-May-15 |
| 8454 | 2 | 3 | 4 | | IV-1 | Gm15284 | | | 9336 | 2 | 3 | 4 | | IV-1 | Gpr1 | 2825 | 4-May-15 |
| 8458 | 2 | 3 | 4 | | IV-1 | Gm15308 | | | 9343 | 2 | 3 | 4 | | IV-1 | Gpr114 | 221188 | 12-May-15 |
| 8476 | 2 | 3 | 4 | | IV-1 | Gm15545 | | | 9345 | 2 | 3 | 4 | | IV-1 | Gpr116 | 221395 | 4-May-15 |
| 8478 | 2 | 3 | 4 | | IV-1 | Gm15612 | | | 9354 | 2 | 3 | 4 | | IV-1 | Gpr133 | 283383 | 4-May-15 |
| 8484 | 2 | 3 | 4 | | IV-1 | Gm15706 | | | 9357 | 2 | 3 | 4 | | IV-1 | Gpr137b | 7107 | 4-May-15 |
| 8487 | 2 | 3 | 4 | | IV-1 | Gm15760 | | | 9387 | 2 | 3 | 4 | | IV-1 | Gpr182 | 11338 | 4-May-15 |
| 8492 | 2 | 3 | 4 | | IV-1 | Gm15850 | | | 9395 | 2 | 3 | 4 | | IV-1 | Gpr27 | 2850 | 4-May-15 |
| 8497 | 2 | 3 | 4 | | IV-1 | Gm15915 | | | 9398 | 2 | 3 | 4 | | IV-1 | Gpr33 | 2856 | 2-Jun-15 |
| 8526 | 2 | 3 | 4 | | IV-1 | Gm16501 | | | 9403 | 2 | 3 | 4 | | IV-1 | Gpr39 | 2863 | 12-May-15 |
| 8537 | 2 | 3 | 4 | | IV-1 | Gm16617 | | | 9406 | 2 | 3 | 4 | | IV-1 | Gpr50 | 9248 | 21-May-15 |
| 8545 | 2 | 3 | 4 | | IV-1 | Gm16793 | | | 9414 | 2 | 3 | 4 | | IV-1 | Gpr64 | 10149 | 4-May-15 |
| 8548 | 2 | 3 | 4 | | IV-1 | Gm16845 | | | 9415 | 2 | 3 | 4 | | IV-1 | Gpr65 | 8477 | 4-May-15 |
| 8556 | 2 | 3 | 4 | | IV-1 | Gm16861 | | | 9416 | 2 | 3 | 4 | | IV-1 | Gpr68 | 8111 | 4-May-15 |
| 8559 | 2 | 3 | 4 | | IV-1 | Gm16998 | | | 9422 | 2 | 3 | 4 | | IV-1 | Gpr87 | 53836 | 4-May-15 |
| 8588 | 2 | 3 | 4 | | IV-1 | Gm19299 | | | 9428 | 2 | 3 | 4 | | IV-1 | Gprasp2 | 114928 | 4-May-15 |
| 8606 | 2 | 3 | 4 | | IV-1 | Gm19668 | | | 9429 | 2 | 3 | 4 | | IV-1 | Gprc5a | 9052 | 4-May-15 |
| 8609 | 2 | 3 | 4 | | IV-1 | Gm19705 | | | 9431 | 2 | 3 | 4 | | IV-1 | Gprc5c | 55890 | 12-May-15 |
| 8639 | 2 | 3 | 4 | | IV-1 | Gm20319 | | | 9432 | 2 | 3 | 4 | | IV-1 | Gprc5d | 55507 | 4-May-15 |
| 8662 | 2 | 3 | 4 | | IV-1 | Gm20748 | | | 9434 | 2 | 3 | 4 | | IV-1 | Gprin1 | 114787 | 4-May-15 |
| 8667 | 2 | 3 | 4 | | IV-1 | Gm20754 | | | 9436 | 2 | 3 | 4 | | IV-1 | Gprin3 | 285513 | 14-May-15 |
| 8694 | 2 | 3 | 4 | | IV-1 | Gm20939 | | | 9440 | 2 | 3 | 4 | | IV-1 | Gpsm2 | 29899 | 4-May-15 |
| 8695 | 2 | 3 | 4 | | IV-1 | Gm21002 | | | 9442 | 2 | 3 | 4 | | IV-1 | Gpt | 2875 | 7-Jun-15 |
| 8711 | 2 | 3 | 4 | | IV-1 | Gm21586 | | | 9443 | 2 | 3 | 4 | | IV-1 | Gpt2 | 84706 | 4-May-15 |
| 8722 | 2 | 3 | 4 | | IV-1 | Gm2373 | | | 9445 | 2 | 3 | 4 | | IV-1 | Gpx2 | 2877 | 4-May-15 |
| 8746 | 2 | 3 | 4 | | IV-1 | Gm3086 | | | 9447 | 2 | 3 | 4 | | IV-1 | Gpx3 | 2878 | 12-May-15 |
| 8749 | 2 | 3 | 4 | | IV-1 | Gm3219 | | | 9454 | 2 | 3 | 4 | | IV-1 | Gramd1b | 57476 | 21-May-15 |
| 8758 | 2 | 3 | 4 | | IV-1 | Gm3317 | | | 9458 | 2 | 3 | 4 | | IV-1 | Gramd4 | 23151 | 14-May-15 |
| 8768 | 2 | 3 | 4 | | IV-1 | Gm3434 | | | 9465 | 2 | 3 | 4 | | IV-1 | Grb7 | 2886 | 12-May-15 |
| 8788 | 2 | 3 | 4 | | IV-1 | Gm4013 | | | 9469 | 2 | 3 | 4 | | IV-1 | Grem1 | 26585 | 12-May-15 |
| 8803 | 2 | 3 | 4 | | IV-1 | Gm4285 | | | 9471 | 2 | 3 | 4 | | IV-1 | Grhl1 | 29841 | 28-May-15 |
| 8814 | 2 | 3 | 4 | | IV-1 | Gm438 | | | 9477 | 2 | 3 | 4 | | IV-1 | Gria3 | 2892 | 12-May-15 |
| 8820 | 2 | 3 | 4 | | IV-1 | Gm4532 | | | 9489 | 2 | 3 | 4 | | IV-1 | Grin1os | | |
| 8822 | 2 | 3 | 4 | | IV-1 | Gm4559 | | | 9516 | 2 | 3 | 4 | | IV-1 | Gripe12 | 134266 | 4-May-15 |
| 8842 | 2 | 3 | 4 | | IV-1 | Gm4836 | | | 9518 | 2 | 3 | 4 | | IV-1 | Grp1 | 79927 | 4-May-15 |
| 8848 | 2 | 3 | 4 | | IV-1 | Gm4861 | | | 9528 | 2 | 3 | 4 | | IV-1 | Gsdma2 | | |
| 8852 | 2 | 3 | 4 | | IV-1 | Gm4890 | | | 9541 | 2 | 3 | 4 | | IV-1 | Gsg2 | 83903 | 12-May-15 |
| 8858 | 2 | 3 | 4 | | IV-1 | Gm4926 | | | 9547 | 2 | 3 | 4 | | IV-1 | Gspt2 | 23708 | 21-May-15 |
| 8867 | 2 | 3 | 4 | | IV-1 | Gm4980 | | | 9548 | 2 | 3 | 4 | | IV-1 | Gsr | 2936 | 4-May-15 |
| 8882 | 2 | 3 | 4 | | IV-1 | Gm5089 | | | 9549 | 2 | 3 | 4 | | IV-1 | Gss | 2937 | 16-Jun-15 |
| 8886 | 2 | 3 | 4 | | IV-1 | Gm5108 | | | 9552 | 2 | 3 | 4 | | IV-1 | Gsta3 | 2940 | 12-May-15 |
| 8892 | 2 | 3 | 4 | | IV-1 | Gm5126 | | | 9555 | 2 | 3 | 4 | | IV-1 | Gstk1 | 373156 | 4-May-15 |
| 8905 | 2 | 3 | 4 | | IV-1 | Gm5176 | | | 9557 | 2 | 3 | 4 | | IV-1 | Gstm2 | 2946 | 17-May-15 |
| 8909 | 2 | 3 | 4 | | IV-1 | Gm5294 | | | 9559 | 2 | 3 | 4 | | IV-1 | Gstm4 | 2948 | 12-May-15 |
| 8910 | 2 | 3 | 4 | | IV-1 | Gm53 | | | 9560 | 2 | 3 | 4 | | IV-1 | Gstm5 | 2949 | 4-May-15 |
| 8922 | 2 | 3 | 4 | | IV-1 | Gm5434 | | | 9561 | 2 | 3 | 4 | | IV-1 | Gstm6 | | |
| 8932 | 2 | 3 | 4 | | IV-1 | Gm5483 | | | 9562 | 2 | 3 | 4 | | IV-1 | Gstm7 | | |
| 8933 | 2 | 3 | 4 | | IV-1 | Gm5485 | | | 9563 | 2 | 3 | 4 | | IV-1 | Gsto1 | 9446 | 4-May-15 |
| 8938 | 2 | 3 | 4 | | IV-1 | Gm5538 | | | 9566 | 2 | 3 | 4 | | IV-1 | Gstp2 | | |
| 8956 | 2 | 3 | 4 | | IV-1 | Gm5643 | | | 9567 | 2 | 3 | 4 | | IV-1 | Gstt1 | 2952 | 24-May-15 |
| 8968 | 2 | 3 | 4 | | IV-1 | Gm572 | | | 9568 | 2 | 3 | 4 | | IV-1 | Gstt2 | 2953 | 12-May-15 |
| 8982 | 2 | 3 | 4 | | IV-1 | Gm590 | | | 9604 | 2 | 3 | 4 | | IV-1 | Gtpbp4 | 23560 | 4-May-15 |
| 8998 | 2 | 3 | 4 | | IV-1 | Gm6083 | | | 9610 | 2 | 3 | 4 | | IV-1 | Guca1a | 2978 | 31-May-15 |
| 9000 | 2 | 3 | 4 | | IV-1 | Gm609 | | | 9616 | 2 | 3 | 4 | | IV-1 | Gucy1a3 | 2982 | 12-May-15 |
| 9012 | 2 | 3 | 4 | | IV-1 | Gm6268 | | | 9625 | 2 | 3 | 4 | | IV-1 | Guk1 | 2987 | 4-May-15 |
| 9014 | 2 | 3 | 4 | | IV-1 | Gm6289 | | | 9629 | 2 | 3 | 4 | | IV-1 | Gvin1 | 387751 | 4-May-15 |
| 9017 | 2 | 3 | 4 | | IV-1 | Gm6307 | | | 9632 | 2 | 3 | 4 | | IV-1 | Gyg | 2992 | 12-May-15 |
| 9022 | 2 | 3 | 4 | | IV-1 | Gm6377 | | | 9633 | 2 | 3 | 4 | | IV-1 | Gyk | | |
| 9031 | 2 | 3 | 4 | | IV-1 | Gm6484 | | | 9635 | 2 | 3 | 4 | | IV-1 | Gylt1b | 120071 | 23-May-15 |
| 9039 | 2 | 3 | 4 | | IV-1 | Gm6568 | | | 9641 | 2 | 3 | 4 | | IV-1 | Gzma | 3001 | 21-May-15 |
| 9046 | 2 | 3 | 4 | | IV-1 | Gm6614 | | | 9642 | 2 | 3 | 4 | | IV-1 | Gzmb | 3002 | 31-May-15 |
| 9050 | 2 | 3 | 4 | | IV-1 | Gm6642 | | | 9654 | 2 | 3 | 4 | | IV-1 | H1fnt | 341567 | 4-May-15 |
| 9054 | 2 | 3 | 4 | | IV-1 | Gm6696 | | | 9662 | 2 | 3 | 4 | | IV-1 | H2afj | 55766 | 7-Jun-15 |
| 9073 | 2 | 3 | 4 | | IV-1 | Gm694 | | | 9667 | 2 | 3 | 4 | | IV-1 | H2afy3 | | |
| 9085 | 2 | 3 | 4 | | IV-1 | Gm715 | | | 9670 | 2 | 3 | 4 | | IV-1 | H2-Bl | | |
| 9089 | 2 | 3 | 4 | | IV-1 | Gm7244 | | | 9674 | 2 | 3 | 4 | | IV-1 | H2-DMb2 | | |
| 9106 | 2 | 3 | 4 | | IV-1 | Gm766 | | | 9677 | 2 | 3 | 4 | | IV-1 | H2-Eb2 | | |
| 9107 | 2 | 3 | 4 | | IV-1 | Gm7694 | | | 9691 | 2 | 3 | 4 | | IV-1 | H2-M2 | | |
| 9133 | 2 | 3 | 4 | | IV-1 | Gm8369 | | | 9694 | 2 | 3 | 4 | | IV-1 | H2-M9 | | |
| 9148 | 2 | 3 | 4 | | IV-1 | Gm8801 | | | 9701 | 2 | 3 | 4 | | IV-1 | H2-Q5 | | |
| 9155 | 2 | 3 | 4 | | IV-1 | Gm8909 | | | 9705 | 2 | 3 | 4 | | IV-1 | H2-Q9 | | |
| 9170 | 2 | 3 | 4 | | IV-1 | Gm933 | | | 9707 | 2 | 3 | 4 | | IV-1 | H2-T22 | | |
| 9183 | 2 | 3 | 4 | | IV-1 | Gm9833 | | | 9711 | 2 | 3 | 4 | | IV-1 | H2-T9 | | |
| 9188 | 2 | 3 | 4 | | IV-1 | Gm9895 | | | 9721 | 2 | 3 | 4 | | IV-1 | Hacl1 | 26061 | 7-Jun-15 |
| 9194 | 2 | 3 | 4 | | IV-1 | Gm9961 | | | 9742 | 2 | 3 | 4 | | IV-1 | Has1 | 3036 | 4-May-15 |
| 9197 | 2 | 3 | 4 | | IV-1 | Gm9994 | | | 9750 | 2 | 3 | 4 | | IV-1 | Haus4 | 54930 | 4-May-15 |

Fig.22 - 29

| | | | | | | | | | | | | | | | |
|---|---|---|---|---|---|---|---|---|---|---|---|---|---|---|---|
| 9758 | 2 | 3 | 4 | | IV-1 | Hba-a1 | | | 10157 | 2 | 3 | 4 | IV-1 | Hsd17b14 | 51171 | 4-May-15 |
| 9761 | 2 | 3 | 4 | | IV-1 | Hbb-b1 | 3043 | 9-Jun-15 | 10162 | 2 | 3 | 4 | IV-1 | Hsd17b7 | 51478 | 7-Jun-15 |
| 9765 | 2 | 3 | 4 | | IV-1 | Hbb-bt | 3045 | 9-Jun-17 | 10183 | 2 | 3 | 4 | IV-1 | Hspa2a | 259217 | 12-May-15 |
| 9769 | 2 | 3 | 4 | | IV-1 | Hbq1a | | | 10187 | 2 | 3 | 4 | IV-1 | Hspa1a | 3303 | 20-May-15 |
| 9770 | 2 | 3 | 4 | | IV-1 | Hbq1b | | | 10188 | 2 | 3 | 4 | IV-1 | Hspa1b | 3304 | 20-May-15 |
| 9786 | 2 | 3 | 4 | | IV-1 | Hcrtr1 | 3061 | 17-May-15 | 10189 | 2 | 3 | 4 | IV-1 | Hspa1l | 3305 | 12-May-15 |
| 9791 | 2 | 3 | 4 | | IV-1 | Hdac11 | 79885 | 4-May-15 | 10190 | 2 | 3 | 4 | IV-1 | Hspa2 | 3306 | 4-May-15 |
| 9796 | 2 | 3 | 4 | | IV-1 | Hdac6 | 10013 | 10-May-15 | 10196 | 2 | 3 | 4 | IV-1 | Hspb1 | 3315 | 23-May-15 |
| 9800 | 2 | 3 | 4 | | IV-1 | Hdc | 3067 | 7-Jun-15 | 10197 | 2 | 3 | 4 | IV-1 | Hspb11 | 51668 | 4-May-15 |
| 9801 | 2 | 3 | 4 | | IV-1 | Hddc2 | 51020 | 4-May-15 | 10198 | 2 | 3 | 4 | IV-1 | Hspb2 | 3316 | 3-May-15 |
| 9802 | 2 | 3 | 4 | | IV-1 | Hddc3 | 374659 | 4-May-15 | 10207 | 2 | 3 | 4 | IV-1 | Hspe1 | 3336 | 4-May-15 |
| 9823 | 2 | 3 | 4 | | IV-1 | Hectd2 | 143279 | 12-May-15 | 10210 | 2 | 3 | 4 | IV-1 | Htatip2 | 10553 | 31-May-15 |
| 9827 | 2 | 3 | 4 | | IV-1 | Heg1 | 57493 | 12-May-15 | 10218 | 2 | 3 | 4 | IV-1 | Htr2c | 3358 | 31-May-15 |
| 9854 | 2 | 3 | 4 | | IV-1 | Hes7 | 84667 | 4-May-15 | 10223 | 2 | 3 | 4 | IV-1 | Htr5b | 645694 | 4-May-15 |
| 9857 | 2 | 3 | 4 | | IV-1 | Hexb | 3074 | 12-May-15 | 10226 | 2 | 3 | 4 | IV-1 | Htra1 | 5654 | 23-May-15 |
| 9863 | 2 | 3 | 4 | | IV-1 | Hey1 | 26508 | 4-May-15 | 10228 | 2 | 3 | 4 | IV-1 | Htra3 | 94031 | 4-May-15 |
| 9873 | 2 | 3 | 4 | | IV-1 | Hhat1 | 57467 | 4-May-15 | 10229 | 2 | 3 | 4 | IV-1 | Htra4 | 203100 | 4-May-15 |
| 9888 | 2 | 3 | 4 | | IV-1 | Hif3a | 64344 | 4-May-15 | 10235 | 2 | 3 | 4 | IV-1 | Hvcn1 | 84329 | 3-May-15 |
| 9890 | 2 | 3 | 4 | | IV-1 | Higd1b | 51751 | 4-May-15 | 10236 | 2 | 3 | 4 | IV-1 | Hyal1 | 3373 | 7-Jun-15 |
| 9894 | 2 | 3 | 4 | | IV-1 | Hils1 | 373861 | 12-May-15 | 10243 | 2 | 3 | 4 | IV-1 | Hyi | 81888 | 4-May-15 |
| 9897 | 2 | 3 | 4 | | IV-1 | Hint2 | 84681 | 12-May-15 | 10245 | 2 | 3 | 4 | IV-1 | Hyls1 | 219844 | 4-May-15 |
| 9900 | 2 | 3 | 4 | | IV-1 | Hip1r | 9026 | 4-May-15 | 10246 | 2 | 3 | 4 | IV-1 | Hyou1 | 10525 | 31-May-15 |
| 9907 | 2 | 3 | 4 | | IV-1 | Hist1h1a | 3024 | 4-May-15 | 10248 | 2 | 3 | 4 | IV-1 | I730028E13Rik | | |
| 9914 | 2 | 3 | 4 | | IV-1 | Hist1h2ab | 8335 | 4-May-15 | 10253 | 2 | 3 | 4 | IV-1 | Iapp | 3375 | 17-May-15 |
| 9915 | 2 | 3 | 4 | | IV-1 | Hist1h2ac | 8334 | 4-May-15 | 10257 | 2 | 3 | 4 | IV-1 | Ibsp | 3381 | 12-May-15 |
| 9918 | 2 | 3 | 4 | | IV-1 | Hist1h2af | | | 10270 | 2 | 3 | 4 | IV-1 | Id1 | 3397 | 31-May-15 |
| 9919 | 2 | 3 | 4 | | IV-1 | Hist1h2ag | 8969 | 4-May-15 | 10272 | 2 | 3 | 4 | IV-1 | Id3 | 3399 | 21-May-15 |
| 9920 | 2 | 3 | 4 | | IV-1 | Hist1h2ah | 85235 | 4-May-15 | 10276 | 2 | 3 | 4 | IV-1 | Idh2 | 3418 | 21-May-15 |
| 9921 | 2 | 3 | 4 | | IV-1 | Hist1h2ai | 8329 | 4-May-15 | 10280 | 2 | 3 | 4 | IV-1 | Idi1 | 3422 | 21-May-15 |
| 9924 | 2 | 3 | 4 | | IV-1 | Hist1h2ao | | | 10284 | 2 | 3 | 4 | IV-1 | Ido2 | 169355 | 4-May-15 |
| 9925 | 2 | 3 | 4 | | IV-1 | Hist1h2ap | | | 10288 | 2 | 3 | 4 | IV-1 | Ier3 | 8870 | 21-May-15 |
| 9926 | 2 | 3 | 4 | | IV-1 | Hist1h2ba | 255626 | 4-May-15 | 10299 | 2 | 3 | 4 | IV-1 | Ifi27l2a | | |
| 9927 | 2 | 3 | 4 | | IV-1 | Hist1h2bb | 3018 | 4-May-15 | 10300 | 2 | 3 | 4 | IV-1 | Ifi27l2b | | |
| 9930 | 2 | 3 | 4 | | IV-1 | Hist1h2bf | 8343 | 4-May-15 | 10310 | 2 | 3 | 4 | IV-1 | Ifitm1 | 8519 | 4-May-15 |
| 9932 | 2 | 3 | 4 | | IV-1 | Hist1h2bh | 8345 | 4-May-15 | 10314 | 2 | 3 | 4 | IV-1 | Ifitm5 | 387733 | 4-May-15 |
| 9934 | 2 | 3 | 4 | | IV-1 | Hist1h2bk | 85236 | 4-May-15 | 10315 | 2 | 3 | 4 | IV-1 | Ifitm6 | | |
| 9936 | 2 | 3 | 4 | | IV-1 | Hist1h2bm | 8342 | 4-May-15 | 10342 | 2 | 3 | 4 | IV-1 | Ifnlr1 | 163702 | 4-May-15 |
| 9937 | 2 | 3 | 4 | | IV-1 | Hist1h2bn | 8341 | 4-May-15 | 10345 | 2 | 3 | 4 | IV-1 | Ifrd2 | 7866 | 12-May-15 |
| 9943 | 2 | 3 | 4 | | IV-1 | Hist1h3d | 8351 | 4-May-15 | 10350 | 2 | 3 | 4 | IV-1 | Ift22 | 64792 | 12-May-15 |
| 9946 | 2 | 3 | 4 | | IV-1 | Hist1h3g | 8355 | 4-May-15 | 10356 | 2 | 3 | 4 | IV-1 | Ift74 | 80173 | 4-May-15 |
| 9947 | 2 | 3 | 4 | | IV-1 | Hist1h3h | 8357 | 4-May-15 | 10365 | 2 | 3 | 4 | IV-1 | Igf1r | 3480 | 7-Jun-15 |
| 9952 | 2 | 3 | 4 | | IV-1 | Hist1h4d | 8360 | 1-Jun-15 | 10374 | 2 | 3 | 4 | IV-1 | Igfbp2 | 3485 | 12-May-15 |
| 9959 | 2 | 3 | 4 | | IV-1 | Hist1h4n | | | 10375 | 2 | 3 | 4 | IV-1 | Igfbp3 | 3486 | 17-May-15 |
| 9960 | 2 | 3 | 4 | | IV-1 | Hist2h2aa1 | | | 10377 | 2 | 3 | 4 | IV-1 | Igfbp5 | 3488 | 12-May-15 |
| 9963 | 2 | 3 | 4 | | IV-1 | Hist2h2ac | 8338 | 4-May-15 | 10378 | 2 | 3 | 4 | IV-1 | Igfbp6 | 3489 | 4-May-15 |
| 9965 | 2 | 3 | 4 | | IV-1 | Hist2h2be | 8349 | 4-May-15 | 10381 | 2 | 3 | 4 | IV-1 | Igf3 | 388555 | 4-May-15 |
| 9966 | 2 | 3 | 4 | | IV-1 | Hist2h3b | | | 10383 | 2 | 3 | 4 | IV-1 | Igfn1 | 91156 | 4-May-15 |
| 9969 | 2 | 3 | 4 | | IV-1 | Hist2h4 | 8370 | 4-May-15 | 10393 | 2 | 3 | 4 | IV-1 | Igsf23 | 147710 | 4-May-15 |
| 9971 | 2 | 3 | 4 | | IV-1 | Hist3h2ba | 337872 | 4-May-15 | 10395 | 2 | 3 | 4 | IV-1 | Igsf5 | 150084 | 21-May-15 |
| 9977 | 2 | 3 | 4 | | IV-1 | Hjurp | 55355 | 17-May-15 | 10396 | 2 | 3 | 4 | IV-1 | Igsf6 | 10261 | 4-May-15 |
| 9980 | 2 | 3 | 4 | | IV-1 | Hk2 | 3099 | 7-Jun-15 | 10401 | 2 | 3 | 4 | IV-1 | Ihh | 3549 | 12-May-15 |
| 9984 | 2 | 3 | 4 | | IV-1 | Hlf | 3131 | 7-Jun-15 | 10421 | 2 | 3 | 4 | IV-1 | Il12b | 3593 | 23-May-15 |
| 9986 | 2 | 3 | 4 | | IV-1 | Hlx | 3142 | 4-May-15 | 10437 | 2 | 3 | 4 | IV-1 | Il17rc | 84818 | 4-May-15 |
| 9987 | 2 | 3 | 4 | | IV-1 | Hmbox1 | 79618 | 4-May-15 | 10440 | 2 | 3 | 4 | IV-1 | Il18 | 3606 | 17-May-15 |
| 9988 | 2 | 3 | 4 | | IV-1 | Hmbs | 3145 | 23-May-15 | 10443 | 2 | 3 | 4 | IV-1 | Il18rap | 8807 | 4-May-15 |
| 9993 | 2 | 3 | 4 | | IV-1 | Hmga1 | 3159 | 12-May-15 | 10446 | 2 | 3 | 4 | IV-1 | Il1b | 3553 | 24-May-15 |
| 9994 | 2 | 3 | 4 | | IV-1 | Hmga1-rs1 | | | 10451 | 2 | 3 | 4 | IV-1 | Il1f8 | 27177 | 4-May-15 |
| 10000 | 2 | 3 | 4 | | IV-1 | Hmgb3 | 3149 | 12-May-15 | 10452 | 2 | 3 | 4 | IV-1 | Il1f9 | 56300 | 4-May-15 |
| 10001 | 2 | 3 | 4 | | IV-1 | Hmgb4 | 127540 | 4-May-15 | 10454 | 2 | 3 | 4 | IV-1 | Il1r2 | 7850 | 4-May-15 |
| 10004 | 2 | 3 | 4 | | IV-1 | Hmgcr | 3156 | 12-May-15 | 10458 | 2 | 3 | 4 | IV-1 | Il1rl1 | 9173 | 12-May-15 |
| 10005 | 2 | 3 | 4 | | IV-1 | Hmgcs1 | 3157 | 12-May-15 | 10460 | 2 | 3 | 4 | IV-1 | Il1rn | 3557 | 23-May-15 |
| 10006 | 2 | 3 | 4 | | IV-1 | Hmgcs2 | 3158 | 12-May-15 | 10464 | 2 | 3 | 4 | IV-1 | Il20rb | 53833 | 4-May-15 |
| 10015 | 2 | 3 | 4 | | IV-1 | Hmox1 | 3162 | 17-May-15 | 10469 | 2 | 3 | 4 | IV-1 | Il22ra2 | 116379 | 4-May-15 |
| 10023 | 2 | 3 | 4 | | IV-1 | Hnf1b | 6928 | 31-May-15 | 10477 | 2 | 3 | 4 | IV-1 | Il2rb | 3560 | 12-May-15 |
| 10024 | 2 | 3 | 4 | | IV-1 | Hnf4a | 3172 | 23-May-15 | 10482 | 2 | 3 | 4 | IV-1 | Il33 | 90865 | 17-May-15 |
| 10029 | 2 | 3 | 4 | | IV-1 | Hnrnpa1 | 3178 | 23-May-15 | 10487 | 2 | 3 | 4 | IV-1 | Il4ra | 3566 | 17-May-15 |
| 10048 | 2 | 3 | 4 | | IV-1 | Hoga1 | 112817 | 12-May-15 | 10491 | 2 | 3 | 4 | IV-1 | Il6ra | 3570 | 17-May-15 |
| 10053 | 2 | 3 | 4 | | IV-1 | Hook1 | 51361 | 4-May-15 | 10494 | 2 | 3 | 4 | IV-1 | Il7r | 3575 | 12-May-15 |
| 10054 | 2 | 3 | 4 | | IV-1 | Hook2 | 29911 | 4-May-15 | 10505 | 2 | 3 | 4 | IV-1 | Imrnp1l | 196294 | 4-May-15 |
| 10056 | 2 | 3 | 4 | | IV-1 | Hopx | 84525 | 4-May-15 | 10506 | 2 | 3 | 4 | IV-1 | Imrnp2l | 83943 | 23-May-15 |
| 10066 | 2 | 3 | 4 | | IV-1 | Hoxa2 | 3199 | 12-May-15 | 10511 | 2 | 3 | 4 | IV-1 | Impa2 | 3613 | 12-May-15 |
| 10070 | 2 | 3 | 4 | | IV-1 | Hoxa6 | 3203 | 4-May-15 | 10514 | 2 | 3 | 4 | IV-1 | Impdh1 | 3614 | 7-Jun-15 |
| 10075 | 2 | 3 | 4 | | IV-1 | Hoxb2 | 3212 | 4-May-15 | 10519 | 2 | 3 | 4 | IV-1 | Inadl | 10207 | 4-May-15 |
| 10076 | 2 | 3 | 4 | | IV-1 | Hoxb3 | 3213 | 4-May-15 | 10520 | 2 | 3 | 4 | IV-1 | Inca1 | 388324 | 4-May-15 |
| 10077 | 2 | 3 | 4 | | IV-1 | Hoxb4 | 3214 | 4-May-15 | 10521 | 2 | 3 | 4 | IV-1 | Incenp | 3619 | 4-May-15 |
| 10080 | 2 | 3 | 4 | | IV-1 | Hoxb7 | 3217 | 4-May-15 | 10529 | 2 | 3 | 4 | IV-1 | Inhba | 3624 | 4-May-15 |
| 10082 | 2 | 3 | 4 | | IV-1 | Hoxb9 | 3219 | 24-May-15 | 10530 | 2 | 3 | 4 | IV-1 | Inhbb | 3625 | 4-May-15 |
| 10084 | 2 | 3 | 4 | | IV-1 | Hoxc11 | 3227 | 28-May-15 | 10534 | 2 | 3 | 4 | IV-1 | Inmt | 11185 | 4-May-15 |
| 10099 | 2 | 3 | 4 | | IV-1 | Hoxd4 | 3233 | 12-May-15 | 10546 | 2 | 3 | 4 | IV-1 | Inpp5d | 3635 | 12-May-15 |
| 10100 | 2 | 3 | 4 | | IV-1 | Hoxd8 | 3234 | 12-May-15 | 10551 | 2 | 3 | 4 | IV-1 | Inppl1 | 3636 | 17-May-15 |
| 10101 | 2 | 3 | 4 | | IV-1 | Hoxd9 | 3235 | 4-May-15 | 10555 | 2 | 3 | 4 | IV-1 | Insig1 | 3638 | 4-May-15 |
| 10102 | 2 | 3 | 4 | | IV-1 | Hp | 3240 | 7-Jun-15 | 10557 | 2 | 3 | 4 | IV-1 | Insl3 | 3640 | 4-May-15 |
| 10106 | 2 | 3 | 4 | | IV-1 | Hpcal4 | 51440 | 4-May-15 | 10559 | 2 | 3 | 4 | IV-1 | Insl6 | 11172 | 4-May-15 |
| 10109 | 2 | 3 | 4 | | IV-1 | Hpgd | 3248 | 17-May-15 | 10571 | 2 | 3 | 4 | IV-1 | Ints6 | 26512 | 12-May-15 |
| 10111 | 2 | 3 | 4 | | IV-1 | Hpn | 3249 | 12-May-15 | 10578 | 2 | 3 | 4 | IV-1 | Ip6k2 | 51447 | 4-May-15 |
| 10123 | 2 | 3 | 4 | | IV-1 | Hrasls | 57110 | 4-May-15 | 10581 | 2 | 3 | 4 | IV-1 | Ipmk | 253430 | 4-May-15 |
| 10124 | 2 | 3 | 4 | | IV-1 | Hrasls5 | 117245 | 4-May-15 | 10602 | 2 | 3 | 4 | IV-1 | Iqcg | 84223 | 4-May-15 |
| 10126 | 2 | 3 | 4 | | IV-1 | Hrct1 | 646962 | 4-May-15 | 10605 | 2 | 3 | 4 | IV-1 | Iqck | 124152 | 4-May-15 |
| 10131 | 2 | 3 | 4 | | IV-1 | Hrh4 | 59340 | 4-May-15 | 10625 | 2 | 3 | 4 | IV-1 | Irf4 | 3662 | 24-May-15 |
| 10133 | 2 | 3 | 4 | | IV-1 | Hrnr | 388697 | 17-May-15 | 10627 | 2 | 3 | 4 | IV-1 | Irf6 | 3664 | 23-May-15 |
| 10137 | 2 | 3 | 4 | | IV-1 | Hs3st1 | 9957 | 4-May-15 | 10632 | 2 | 3 | 4 | IV-1 | Irgc1 | 56269 | 4-May-15 |
| 10139 | 2 | 3 | 4 | | IV-1 | Hs3st3a1 | 9955 | 4-May-15 | 10637 | 2 | 3 | 4 | IV-1 | Irs2 | 8660 | 12-May-15 |
| 10143 | 2 | 3 | 4 | | IV-1 | Hs3st6 | 64711 | 4-May-15 | 10640 | 2 | 3 | 4 | IV-1 | Irx1 | 79192 | 7-Jun-15 |
| 10148 | 2 | 3 | 4 | | IV-1 | Hsbp1l | 440498 | 4-May-15 | 10641 | 2 | 3 | 4 | IV-1 | Irx2 | 153572 | 4-May-15 |
| 10150 | 2 | 3 | 4 | | IV-1 | Hsd11b1 | 3290 | 4-May-15 | 10648 | 2 | 3 | 4 | IV-1 | Iscu | 23479 | 23-May-15 |
| 10153 | 2 | 3 | 4 | | IV-1 | Hsd17b10 | 3028 | 12-May-15 | 10649 | 2 | 3 | 4 | IV-1 | Isg15 | 9636 | 12-May-15 |
| 10156 | 2 | 3 | 4 | | IV-1 | Hsd17b13 | 345275 | 4-May-15 | 10650 | 2 | 3 | 4 | IV-1 | Isg20 | 3669 | 12-May-15 |

Fig.22 - 30

| | | | | | | | | | | | | | | | |
|---|---|---|---|---|---|---|---|---|---|---|---|---|---|---|---|
| 10652 | 2 | 3 | 4 | | IV-1 | Isl1 | 3670 | 4-May-15 | 11212 | 2 | 3 | 4 | | IV-1 | Krt34 | 3885 | 12-May-15 |
| 10653 | 2 | 3 | 4 | | IV-1 | Isl2 | 64843 | 4-May-15 | 11215 | 2 | 3 | 4 | | IV-1 | Krt39 | 390792 | 4-May-15 |
| 10654 | 2 | 3 | 4 | | IV-1 | Islr | 3671 | 12-May-15 | 11218 | 2 | 3 | 4 | | IV-1 | Krt42 | | |
| 10656 | 2 | 3 | 4 | | IV-1 | Ism1 | 140862 | 4-May-15 | 11221 | 2 | 3 | 4 | | IV-1 | Krt6b | 3854 | 4-May-15 |
| 10657 | 2 | 3 | 4 | | IV-1 | Isro2 | 145501 | 4-May-15 | 11222 | 2 | 3 | 4 | | IV-1 | Krt7 | 3855 | 12-May-15 |
| 10659 | 2 | 3 | 4 | | IV-1 | Isoc2a | | | 11224 | 2 | 3 | 4 | | IV-1 | Krt72 | 140807 | 4-May-15 |
| 10664 | 2 | 3 | 4 | | IV-1 | Isy1 | 57461 | 12-May-15 | 11229 | 2 | 3 | 4 | | IV-1 | Krt77 | 374454 | 4-May-15 |
| 10669 | 2 | 3 | 4 | | IV-1 | Itfg3 | 83986 | 4-May-15 | 11231 | 2 | 3 | 4 | | IV-1 | Krt79 | 338785 | 4-May-15 |
| 10673 | 2 | 3 | 4 | | IV-1 | Itga2 | 3673 | 12-May-15 | 11232 | 2 | 3 | 4 | | IV-1 | krt8 | 3856 | 4-May-15 |
| 10675 | 2 | 3 | 4 | | IV-1 | Itga3 | 3675 | 30-May-15 | 11239 | 2 | 3 | 4 | | IV-1 | Krt86 | 3892 | 12-May-15 |
| 10682 | 2 | 3 | 4 | | IV-1 | Itgad | 3681 | 12-May-15 | 11243 | 2 | 3 | 4 | | IV-1 | Krtap11-1 | 337880 | 4-May-15 |
| 10685 | 2 | 3 | 4 | | IV-1 | Itgam | 3684 | 4-May-15 | 11246 | 2 | 3 | 4 | | IV-1 | Krtap1-3 | 81850 | 4-May-15 |
| 10691 | 2 | 3 | 4 | | IV-1 | Itgb2 | 3689 | 12-May-15 | 11247 | 2 | 3 | 4 | | IV-1 | Krtap13-1 | 140258 | 4-May-15 |
| 10702 | 2 | 3 | 4 | | IV-1 | Itih2 | 3698 | 4-May-15 | 11248 | 2 | 3 | 4 | | IV-1 | Krtap14 | 728255 | 4-May-15 |
| 10713 | 2 | 3 | 4 | | IV-1 | Itpka | 3706 | 4-May-15 | 11249 | 2 | 3 | 4 | | IV-1 | Krtap1-4 | 728255 | 4-May-15 |
| 10726 | 2 | 3 | 4 | | IV-1 | Ivns1abp | 10625 | 4-May-15 | 11250 | 2 | 3 | 4 | | IV-1 | Krtap15 | 83895 | 4-May-15 |
| 10728 | 2 | 3 | 4 | | IV-1 | Iyd | 389434 | 4-May-15 | 11252 | 2 | 3 | 4 | | IV-1 | Krtap16-1 | 100505 753 | 4-May-15 |
| 10735 | 2 | 3 | 4 | | IV-1 | Jade3 | 9767 | 4-May-15 | 11256 | 2 | 3 | 4 | | IV-1 | Krtap19-3 | 337970 | 4-May-15 |
| 10737 | 2 | 3 | 4 | | IV-1 | Jag2 | 3714 | 4-May-15 | 11259 | 2 | 3 | 4 | | IV-1 | Krtap19-9b | | |
| 10742 | 2 | 3 | 4 | | IV-1 | Jakmip1 | 152789 | 12-May-15 | 11262 | 2 | 3 | 4 | | IV-1 | Krtap22-2 | 100288 287 | 4-May-15 |
| 10780 | 2 | 3 | 4 | | IV-1 | Jph1 | 58704 | 17-May-15 | 11263 | 2 | 3 | 4 | | IV-1 | Krtap2-4 | 85294 | 4-May-15 |
| 10782 | 2 | 3 | 4 | | IV-1 | Kansl1l | 151050 | 12-May-15 | 11265 | 2 | 3 | 4 | | IV-1 | Krtap26-1 | 388818 | 4-May-15 |
| 10783 | 2 | 3 | 4 | | IV-1 | Kap | | | 11266 | 2 | 3 | 4 | | IV-1 | Krtap27-1 | 643812 | 4-May-15 |
| 10797 | 2 | 3 | 4 | | IV-1 | Kazald1 | 81621 | 4-May-15 | 11267 | 2 | 3 | 4 | | IV-1 | Krtap3-1 | 83896 | 4-May-15 |
| 10801 | 2 | 3 | 4 | | IV-1 | Kbtbd13 | 390594 | 23-May-15 | 11270 | 2 | 3 | 4 | | IV-1 | Krtap3-2 | 83897 | 4-May-15 |
| 10813 | 2 | 3 | 4 | | IV-1 | Kcns5 | 3741 | 17-May-15 | 11271 | 2 | 3 | 4 | | IV-1 | Krtap3-3 | 85293 | 4-May-15 |
| 10821 | 2 | 3 | 4 | | IV-1 | Kcnc1 | 3746 | 4-May-15 | 11272 | 2 | 3 | 4 | | IV-1 | Krtap4-1 | 85285 | 4-May-15 |
| 10823 | 2 | 3 | 4 | | IV-1 | Kcnc3 | 3748 | 23-May-15 | 11273 | 2 | 3 | 4 | | IV-1 | Krtap4-13 | 84616 | 4-May-15 |
| 10825 | 2 | 3 | 4 | | IV-1 | Kcnd1 | 3750 | 12-May-15 | 11274 | 2 | 3 | 4 | | IV-1 | Krtap4-16 | | |
| 10829 | 2 | 3 | 4 | | IV-1 | Kcne1 | 3753 | 23-May-15 | 11275 | 2 | 3 | 4 | | IV-1 | Krtap4-2 | 85291 | 4-May-15 |
| 10834 | 2 | 3 | 4 | | IV-1 | Kcnf1 | 3754 | 4-May-15 | 11276 | 2 | 3 | 4 | | IV-1 | Krtap4-6 | 81871 | 4-May-15 |
| 10838 | 2 | 3 | 4 | | IV-1 | Kcng4 | 93107 | 4-May-15 | 11277 | 2 | 3 | 4 | | IV-1 | Krtap4-7 | 100132 476 | 4-May-15 |
| 10839 | 2 | 3 | 4 | | IV-1 | Kcnh1 | 3756 | 17-May-15 | 11278 | 2 | 3 | 4 | | IV-1 | Krtap4-8 | 728224 | 4-May-15 |
| 10848 | 2 | 3 | 4 | | IV-1 | Kcnip2 | 30819 | 12-May-15 | 11279 | 2 | 3 | 4 | | IV-1 | Krtap4-9 | 100132 386 | 4-May-15 |
| 10849 | 2 | 3 | 4 | | IV-1 | Kcnip3 | 30818 | 12-May-15 | 11280 | 2 | 3 | 4 | | IV-1 | Krtap5-1 | 387264 | 4-May-15 |
| 10855 | 2 | 3 | 4 | | IV-1 | Kcnj13 | 3769 | 24-May-15 | 11283 | 2 | 3 | 4 | | IV-1 | Krtap5-4 | 387267 | 4-Apr-15 |
| 10858 | 2 | 3 | 4 | | IV-1 | Kcnj16 | 3773 | 12-May-15 | 11288 | 2 | 3 | 4 | | IV-1 | Krtap7-1 | 337878 | 4-May-15 |
| 10859 | 2 | 3 | 4 | | IV-1 | Kcnj2 | 3759 | 23-May-15 | 11289 | 2 | 3 | 4 | | IV-1 | Krtap8-1 | 337879 | 4-May-15 |
| 10864 | 2 | 3 | 4 | | IV-1 | Kcnj8 | 3764 | 4-May-15 | 11290 | 2 | 3 | 4 | | IV-1 | Krtap9-1 | 728318 | 4-May-15 |
| 10874 | 2 | 3 | 4 | | IV-1 | Kcnk3 | 3777 | 4-May-15 | 11291 | 2 | 3 | 4 | | IV-1 | Krtap9-3 | 83960 | 12-May-15 |
| 10876 | 2 | 3 | 4 | | IV-1 | Kcnk5 | 8645 | 4-May-15 | 11296 | 2 | 3 | 4 | | IV-1 | Ksr1 | 8844 | 4-May-15 |
| 10877 | 2 | 3 | 4 | | IV-1 | Kcnk6 | 9424 | 4-May-15 | 11306 | 2 | 3 | 4 | | IV-1 | L3hypdh | 112849 | 12-May-15 |
| 10884 | 2 | 3 | 4 | | IV-1 | Kcnmb4 | 27345 | 4-May-15 | 11318 | 2 | 3 | 4 | | IV-1 | Lag3 | 3902 | 4-May-15 |
| 10888 | 2 | 3 | 4 | | IV-1 | Kcnn3 | 3782 | 12-May-15 | 11325 | 2 | 3 | 4 | | IV-1 | Lama4 | 3910 | 4-May-15 |
| 10890 | 2 | 3 | 4 | | IV-1 | Kcnq1 | 3784 | 22-May-15 | 11327 | 2 | 3 | 4 | | IV-1 | Lamb1 | 3912 | 12-May-15 |
| 10899 | 2 | 3 | 4 | | IV-1 | Kcns3 | 3790 | 12-May-15 | 11329 | 2 | 3 | 4 | | IV-1 | Lamb3 | 3914 | 23-May-15 |
| 10900 | 2 | 3 | 4 | | IV-1 | Kcnt1 | 57582 | 7-Jun-15 | 11331 | 2 | 3 | 4 | | IV-1 | Lamc2 | 3918 | 23-May-15 |
| 10912 | 2 | 3 | 4 | | IV-1 | Kctd14 | 65987 | 4-May-15 | 11346 | 2 | 3 | 4 | | IV-1 | Lap3 | 51056 | 7-Jun-15 |
| 10913 | 2 | 3 | 4 | | IV-1 | Kctd15 | 79047 | 4-May-15 | 11349 | 2 | 3 | 4 | | IV-1 | Laptm5 | 7805 | 4-May-15 |
| 10933 | 2 | 3 | 4 | | IV-1 | Kdf1 | 126695 | 4-May-15 | 11355 | 2 | 3 | 4 | | IV-1 | Larp6 | 55323 | 4-May-15 |
| 10958 | 2 | 3 | 4 | | IV-1 | Khdc1a | | | 11358 | 2 | 3 | 4 | | IV-1 | Lars2 | 23395 | 4-May-15 |
| 10960 | 2 | 3 | 4 | | IV-1 | Khdc1c | | | 11362 | 2 | 3 | 4 | | IV-1 | Lat2 | 7462 | 7-Jun-15 |
| 10964 | 2 | 3 | 4 | | IV-1 | Khdrbs3 | 10656 | 12-May-15 | 11365 | 2 | 3 | 4 | | IV-1 | Lax1 | 54900 | 4-May-15 |
| 10965 | 2 | 3 | 4 | | IV-1 | Khk | 3795 | 3-May-15 | 11368 | 2 | 3 | 4 | | IV-1 | Lbp | 3929 | 7-Jun-15 |
| 10986 | 2 | 3 | 4 | | IV-1 | Kif21b | 23046 | 4-May-15 | 11369 | 2 | 3 | 4 | | IV-1 | Lbr | 3930 | 12-May-15 |
| 10990 | 2 | 3 | 4 | | IV-1 | Kif26a | 26153 | 4-May-15 | 11374 | 2 | 3 | 4 | | IV-1 | Lcat | 3931 | 4-May-15 |
| 11003 | 2 | 3 | 4 | | IV-1 | Kif5c | 3800 | 4-May-15 | 11375 | 2 | 3 | 4 | | IV-1 | Lce1a1 | | |
| 11017 | 2 | 3 | 4 | | IV-1 | Kisrel3 | 84623 | 4-May-15 | 11376 | 2 | 3 | 4 | | IV-1 | Lce1a2 | | |
| 11024 | 2 | 3 | 4 | | IV-1 | Kit | 9365 | 24-May-15 | 11377 | 2 | 3 | 4 | | IV-1 | Lce1b | 353132 | 4-May-15 |
| 11025 | 2 | 3 | 4 | | IV-1 | Kitlg | 152831 | 4-May-15 | 11378 | 2 | 3 | 4 | | IV-1 | Lce1c | 353133 | 4-May-15 |
| 11028 | 2 | 3 | 4 | | IV-1 | Klc3 | 147700 | 4-May-15 | 11379 | 2 | 3 | 4 | | IV-1 | Lce1d | 353134 | 4-May-15 |
| 11032 | 2 | 3 | 4 | | IV-1 | Klf11 | 8462 | 4-May-15 | 11380 | 2 | 3 | 4 | | IV-1 | Lce1e | 353135 | 4-May-15 |
| 11036 | 2 | 3 | 4 | | IV-1 | Klf15 | 28999 | 4-May-15 | 11381 | 2 | 3 | 4 | | IV-1 | Lce1f | 353137 | 4-May-15 |
| 11039 | 2 | 3 | 4 | | IV-1 | Klf2 | 10365 | 12-May-15 | 11382 | 2 | 3 | 4 | | IV-1 | Lce1g | | |
| 11042 | 2 | 3 | 4 | | IV-1 | Klf5 | 688 | 17-May-15 | 11383 | 2 | 3 | 4 | | IV-1 | Lce1h | | |
| 11044 | 2 | 3 | 4 | | IV-1 | Klf7 | 8609 | 4-May-15 | 11384 | 2 | 3 | 4 | | IV-1 | Lce1i | | |
| 11046 | 2 | 3 | 4 | | IV-1 | Klf9 | 687 | 31-May-15 | 11385 | 2 | 3 | 4 | | IV-1 | Lce1j | | |
| 11052 | 2 | 3 | 4 | | IV-1 | Klhdc7a | 127707 | 12-May-15 | 11386 | 2 | 3 | 4 | | IV-1 | Lce1k | | |
| 11058 | 2 | 3 | 4 | | IV-1 | Klhl10 | 317719 | 7-Jun-15 | 11387 | 2 | 3 | 4 | | IV-1 | Lce1l | | |
| 11059 | 2 | 3 | 4 | | IV-1 | Klhl11 | 55175 | 2-Jun-15 | 11392 | 2 | 3 | 4 | | IV-1 | Lce3d | 84648 | 4-May-15 |
| 11062 | 2 | 3 | 4 | | IV-1 | Klhl14 | 57565 | 4-May-15 | 11395 | 2 | 3 | 4 | | IV-1 | Lce6a | 448835 | 4-May-15 |
| 11063 | 2 | 3 | 4 | | IV-1 | Klhl15 | 80311 | 12-May-15 | 11410 | 2 | 3 | 4 | | IV-1 | Lcor | 84458 | 4-May-15 |
| 11070 | 2 | 3 | 4 | | IV-1 | Klhl23 | 151230 | 4-May-15 | 11411 | 2 | 3 | 4 | | IV-1 | Lcorl | 254251 | 4-May-15 |
| 11075 | 2 | 3 | 4 | | IV-1 | Klhl29 | 114818 | 4-May-15 | 11421 | 2 | 3 | 4 | | IV-1 | Ldhb | 3945 | 12-May-15 |
| 11080 | 2 | 3 | 4 | | IV-1 | Klhl33 | 123103 | 4-May-15 | 11423 | 2 | 3 | 4 | | IV-1 | Ldhd | 197257 | 4-May-15 |
| 11084 | 2 | 3 | 4 | | IV-1 | Klhl38 | 340359 | 4-May-15 | 11424 | 2 | 3 | 4 | | IV-1 | Ldlr | 3949 | 17-May-15 |
| 11094 | 2 | 3 | 4 | | IV-1 | Klk1 | 3816 | 12-May-15 | 11436 | 2 | 3 | 4 | | IV-1 | Lefty1 | 10637 | 4-May-15 |
| 11109 | 2 | 3 | 4 | | IV-1 | Klk1b3 | | | 11448 | 2 | 3 | 4 | | IV-1 | Lep | 3952 | 24-May-15 |
| 11110 | 2 | 3 | 4 | | IV-1 | Klk1b4 | | | 11449 | 2 | 3 | 4 | | IV-1 | Lepr | 3953 | 7-Jun-15 |
| 11111 | 2 | 3 | 4 | | IV-1 | Klk1b5 | | | 11459 | 2 | 3 | 4 | | IV-1 | Lfng | 3955 | 23-May-15 |
| 11114 | 2 | 3 | 4 | | IV-1 | Klk1b9 | | | 11461 | 2 | 3 | 4 | | IV-1 | Lgals12 | 85329 | 4-May-15 |
| 11117 | 2 | 3 | 4 | | IV-1 | Klk6 | 5653 | 7-Jun-15 | 11462 | 2 | 3 | 4 | | IV-1 | Lgals2 | 3957 | 7-Jun-15 |
| 11120 | 2 | 3 | 4 | | IV-1 | Klk9 | 284366 | 4-May-15 | 11463 | 2 | 3 | 4 | | IV-1 | Lgals3 | 3958 | 24-May-15 |
| 11134 | 2 | 3 | 4 | | IV-1 | Klra23 | | | 11465 | 2 | 3 | 4 | | IV-1 | Lgals4 | 3960 | 4-May-15 |
| 11140 | 2 | 3 | 4 | | IV-1 | Klra7 | | | 11466 | 2 | 3 | 4 | | IV-1 | Lgals6 | | |
| 11142 | 2 | 3 | 4 | | IV-1 | Klra9 | | | 11473 | 2 | 3 | 4 | | IV-1 | Lgi3 | 203190 | 4-May-15 |
| 11145 | 2 | 3 | 4 | | IV-1 | Klrb1b | | | 11475 | 2 | 3 | 4 | | IV-1 | Lgmn | 5641 | 4-May-15 |
| 11149 | 2 | 3 | 4 | | IV-1 | Klrc1 | 3821 | 12-May-15 | 11484 | 2 | 3 | 4 | | IV-1 | Lhfpl2 | 10184 | 4-May-15 |
| 11155 | 2 | 3 | 4 | | IV-1 | Klrg2 | 346689 | 4-May-15 | 11490 | 2 | 3 | 4 | | IV-1 | Lhx1os | | |
| 11168 | 2 | 3 | 4 | | IV-1 | Kng2 | | | 11495 | 2 | 3 | 4 | | IV-1 | Lhx6 | 26468 | 4-May-15 |
| 11179 | 2 | 3 | 4 | | IV-1 | Kprp | 448834 | 4-May-15 | 11499 | 2 | 3 | 4 | | IV-1 | Lif | 3976 | 28-May-15 |
| 11186 | 2 | 3 | 4 | | IV-1 | Krit1 | 66095 | 4-May-15 | 11506 | 2 | 3 | 4 | | IV-1 | Lilrb4 | 11006 | 12-May-15 |
| 11189 | 2 | 3 | 4 | | IV-1 | Krt1 | 3848 | 24-May-15 | 11516 | 2 | 3 | 4 | | IV-1 | Lims2 | 55679 | 17-May-15 |
| 11190 | 2 | 3 | 4 | | IV-1 | Krt10 | 3858 | 4-May-15 | 11523 | 2 | 3 | 4 | | IV-1 | Lin7b | 64130 | 12-May-15 |
| 11194 | 2 | 3 | 4 | | IV-1 | Krt15 | 3866 | 4-May-15 | 11534 | 2 | 3 | 4 | | IV-1 | Lipe | 3991 | 12-May-15 |
| 11198 | 2 | 3 | 4 | | IV-1 | Krt19 | 3880 | 12-May-15 | | | | | | | | | |
| 11200 | 2 | 3 | 4 | | IV-1 | Krt20 | 54474 | 4-May-15 | | | | | | | | | |

Fig.22 - 31

| | | | | | | | | | | | | | | |
|---|---|---|---|---|---|---|---|---|---|---|---|---|---|---|
| 11550 | 2 | 3 | 4 | | IV-1 | Ugl2 | 3993 | 31-May-15 | 12064 | 2 | 3 | 4 | IV-1 | Marcksl1-ps4 | | |
| 11559 | 2 | 3 | 4 | | IV-1 | Lmbrd2 | 92255 | 4-May-15 | 12065 | 2 | 3 | 4 | IV-1 | Marco | 8685 | 17-May-15 |
| 11560 | 2 | 3 | 4 | | IV-1 | Lmcd1 | 29995 | 4-May-15 | 12067 | 2 | 3 | 4 | IV-1 | Mark1 | 4139 | 4-May-15 |
| 11572 | 2 | 3 | 4 | | IV-1 | Lmod1 | 25802 | 12-May-15 | 12074 | 2 | 3 | 4 | IV-1 | Marveld2 | 153562 | 23-May-15 |
| 11580 | 2 | 3 | 4 | | IV-1 | Lnpep | 4012 | 12-May-15 | 12075 | 2 | 3 | 4 | IV-1 | Marveld3 | 91862 | 4-May-15 |
| 11581 | 2 | 3 | 4 | | IV-1 | Lnx1 | 84708 | 26-May-15 | 12077 | 2 | 3 | 4 | IV-1 | Masp1 | 5648 | 17-May-15 |
| 11589 | 2 | 3 | 4 | | IV-1 | LOC100503496 | | | 12087 | 2 | 3 | 4 | IV-1 | Matk | 4145 | 12-May-15 |
| 11590 | 2 | 3 | 4 | | IV-1 | LOC100503676 | | | 12110 | 2 | 3 | 4 | IV-1 | Mbl2 | 4153 | 7-Jun-15 |
| 11591 | 2 | 3 | 4 | | IV-1 | LOC100504039 | | | 12117 | 2 | 3 | 4 | IV-1 | Mboat2 | 129642 | 4-May-15 |
| 11593 | 2 | 3 | 4 | | IV-1 | LOC100504703 | | | 12125 | 2 | 3 | 4 | IV-1 | Mc2r | 4158 | 4-May-15 |
| 11605 | 2 | 3 | 4 | | IV-1 | LOC101243624 | | | 12128 | 2 | 3 | 4 | IV-1 | Mc5r | 4161 | 4-May-15 |
| 11619 | 2 | 3 | 4 | | IV-1 | LOC106740 | | | 12156 | 2 | 3 | 4 | IV-1 | Mcoln2 | 255231 | 12-May-15 |
| 11628 | 2 | 3 | 4 | | IV-1 | Lonrf3 | 79836 | 4-May-15 | 12157 | 2 | 3 | 4 | IV-1 | Mcoln3 | 55283 | 12-May-15 |
| 11630 | 2 | 3 | 4 | | IV-1 | Lox | 4015 | 12-May-15 | 12161 | 2 | 3 | 4 | IV-1 | Mcpt4 | | |
| 11633 | 2 | 3 | 4 | | IV-1 | Loxl2 | 4017 | 12-May-15 | 12169 | 2 | 3 | 4 | IV-1 | Mcts2 | 100190490 | 4-May-15 |
| 11638 | 2 | 3 | 4 | | IV-1 | Lpar3 | 23566 | 4-May-15 | 12175 | 2 | 3 | 4 | IV-1 | Mdga1 | 266727 | 4-May-15 |
| 11646 | 2 | 3 | 4 | | IV-1 | Lpcat4 | 254531 | 7-Jun-15 | 12183 | 2 | 3 | 4 | IV-1 | Mdm4 | 4194 | 4-May-15 |
| 11649 | 2 | 3 | 4 | | IV-1 | Lphn2 | 23266 | 12-May-15 | 12186 | 2 | 3 | 4 | IV-1 | Me1 | 4199 | 7-Jun-15 |
| 11651 | 2 | 3 | 4 | | IV-1 | Lpin1 | 23175 | 4-May-15 | 12224 | 2 | 3 | 4 | IV-1 | Med9os | | |
| 11653 | 2 | 3 | 4 | | IV-1 | Lpin3 | 64900 | 4-May-15 | 12228 | 2 | 3 | 4 | IV-1 | Mef2c | 4208 | 12-May-15 |
| 11654 | 2 | 3 | 4 | | IV-1 | Lpl | 4023 | 7-Jun-15 | 12234 | 2 | 3 | 4 | IV-1 | Megf6 | 1953 | 12-May-15 |
| 11665 | 2 | 3 | 4 | | IV-1 | Lpo | 4025 | 4-May-15 | 12235 | 2 | 3 | 4 | IV-1 | Megf8 | 1954 | 4-May-15 |
| 11668 | 2 | 3 | 4 | | IV-1 | Lrch4 | 4034 | 4-May-15 | 12236 | 2 | 3 | 4 | IV-1 | Megf9 | 1955 | 4-May-15 |
| 11670 | 2 | 3 | 4 | | IV-1 | Lrg1 | 116844 | 4-May-15 | 12242 | 2 | 3 | 4 | IV-1 | Meis2 | 4212 | 4-May-15 |
| 11675 | 2 | 3 | 4 | | IV-1 | Lrig3 | 121227 | 4-May-15 | 12263 | 2 | 3 | 4 | IV-1 | Metrn | 79006 | 4-May-15 |
| 11677 | 2 | 3 | 4 | | IV-1 | Lrit2 | 340745 | 4-May-15 | 12264 | 2 | 3 | 4 | IV-1 | Metrnl | 284207 | 4-May-15 |
| 11680 | 2 | 3 | 4 | | IV-1 | Lrp1 | 4035 | 7-Jun-15 | 12275 | 2 | 3 | 4 | IV-1 | Mettl20 | 254013 | 23-May-15 |
| 11688 | 2 | 3 | 4 | | IV-1 | Lrp4 | 4038 | 7-Jun-15 | 12279 | 2 | 3 | 4 | IV-1 | Mettl22 | 79091 | 4-May-15 |
| 11699 | 2 | 3 | 4 | | IV-1 | Lrrc14b | 389257 | 4-May-15 | 12300 | 2 | 3 | 4 | IV-1 | Mfap2 | 4237 | 4-May-15 |
| 11702 | 2 | 3 | 4 | | IV-1 | Lrrc16b | 90668 | 12-May-15 | 12302 | 2 | 3 | 4 | IV-1 | Mfap3l | 9848 | 12-May-15 |
| 11704 | 2 | 3 | 4 | | IV-1 | Lrrc18 | 474354 | 12-May-15 | 12303 | 2 | 3 | 4 | IV-1 | Mfap4 | 4239 | 4-May-15 |
| 11706 | 2 | 3 | 4 | | IV-1 | Lrrc2 | 79442 | 4-May-15 | 12304 | 2 | 3 | 4 | IV-1 | Mfap5 | 8076 | 21-May-15 |
| 11720 | 2 | 3 | 4 | | IV-1 | Lrrc38 | 126755 | 4-May-15 | 12306 | 2 | 3 | 4 | IV-1 | Mfge8 | 4240 | 4-May-15 |
| 11721 | 2 | 3 | 4 | | IV-1 | Lrrc39 | 127495 | 4-May-15 | 12323 | 2 | 3 | 4 | IV-1 | Mfsd6l | 162387 | 4-May-15 |
| 11728 | 2 | 3 | 4 | | IV-1 | Lrrc45 | 201255 | 4-May-15 | 12326 | 2 | 3 | 4 | IV-1 | Mfsd7c | 55640 | 4-May-15 |
| 11729 | 2 | 3 | 4 | | IV-1 | Lrrc46 | 90506 | 4-May-15 | 12331 | 2 | 3 | 4 | IV-1 | Mgarp | 84709 | 4-May-15 |
| 11735 | 2 | 3 | 4 | | IV-1 | Lrrc51 | 220074 | 23-May-15 | 12338 | 2 | 3 | 4 | IV-1 | Mgat5 | 4249 | 4-May-15 |
| 11736 | 2 | 3 | 4 | | IV-1 | Lrrc52 | 440699 | 4-May-15 | 12339 | 2 | 3 | 4 | IV-1 | Mgat5b | 146664 | 12-May-15 |
| 11753 | 2 | 3 | 4 | | IV-1 | Lrrc75b | 388486 | 4-May-15 | 12341 | 2 | 3 | 4 | IV-1 | Mgl2 | | |
| 11755 | 2 | 3 | 4 | | IV-1 | Lrrc8b | 23507 | 4-May-15 | 12345 | 2 | 3 | 4 | IV-1 | Mgp | 4256 | 12-May-15 |
| 11769 | 2 | 3 | 4 | | IV-1 | Lrrn1 | 57633 | 4-May-15 | 12347 | 2 | 3 | 4 | IV-1 | Mgst1 | 4257 | 21-May-15 |
| 11781 | 2 | 3 | 4 | | IV-1 | Lrwd1 | 222229 | 4-May-15 | 12349 | 2 | 3 | 4 | IV-1 | Mgst3 | 4259 | 4-May-15 |
| 11793 | 2 | 3 | 4 | | IV-1 | Lsm5 | 23658 | 4-May-15 | 12350 | 2 | 3 | 4 | IV-1 | Mia | 8190 | 4-May-15 |
| 11795 | 2 | 3 | 4 | | IV-1 | Lsm7 | 51690 | 4-May-15 | 12354 | 2 | 3 | 4 | IV-1 | Mib1 | 57534 | 7-Jun-15 |
| 11797 | 2 | 3 | 4 | | IV-1 | Lsmem1 | 286006 | 4-May-15 | 12366 | 2 | 3 | 4 | IV-1 | Mid1ip1 | 58526 | 4-May-15 |
| 11799 | 2 | 3 | 4 | | IV-1 | Lsr | 51599 | 4-May-15 | 12379 | 2 | 3 | 4 | IV-1 | Mill2 | | |
| 11800 | 2 | 3 | 4 | | IV-1 | Lss | 4047 | 7-Jun-15 | 12380 | 2 | 3 | 4 | IV-1 | Milr1 | 284021 | 12-May-15 |
| 11801 | 2 | 3 | 4 | | IV-1 | Lst1 | | | 12460 | 2 | 3 | 4 | IV-1 | Mir143hg | 728264 | 12-May-15 |
| 11804 | 2 | 3 | 4 | | IV-1 | Ltb | 4050 | 12-May-15 | 12621 | 2 | 3 | 4 | IV-1 | Mir22hg | 84981 | 12-May-15 |
| 11805 | 2 | 3 | 4 | | IV-1 | Ltb4r1 | 1241 | 17-May-15 | 13480 | 2 | 3 | 4 | IV-1 | Mirlet7bhg | 400931 | 12-May-15 |
| 11809 | 2 | 3 | 4 | | IV-1 | Ltbp3 | 4054 | 7-Jun-15 | 13518 | 2 | 3 | 4 | IV-1 | Mlip | 90523 | 4-May-15 |
| 11810 | 2 | 3 | 4 | | IV-1 | Ltbp4 | 8425 | 12-May-15 | 13526 | 2 | 3 | 4 | IV-1 | Mlph | 79083 | 7-Jun-15 |
| 11812 | 2 | 3 | 4 | | IV-1 | Lto4s | 4056 | 4-May-15 | 13530 | 2 | 3 | 4 | IV-1 | Mlxipl | 51085 | 23-May-15 |
| 11821 | 2 | 3 | 4 | | IV-1 | Lurap1 | 541468 | 4-May-15 | 13537 | 2 | 3 | 4 | IV-1 | Mmd2 | 221938 | 4-May-15 |
| 11826 | 2 | 3 | 4 | | IV-1 | Lxn | 56925 | 4-May-15 | 13538 | 2 | 3 | 4 | IV-1 | Mme | 4311 | 7-Jun-15 |
| 11830 | 2 | 3 | 4 | | IV-1 | Ly6d | 8581 | 7-Jun-15 | 13541 | 2 | 3 | 4 | IV-1 | Mmgt2 | | |
| 11832 | 2 | 3 | 4 | | IV-1 | Ly6f | | | 13543 | 2 | 3 | 4 | IV-1 | Mmp11 | 4320 | 4-May-15 |
| 11835 | 2 | 3 | 4 | | IV-1 | Ly6g6c | 80740 | 4-May-15 | 13545 | 2 | 3 | 4 | IV-1 | Mmp13 | 4322 | 24-May-15 |
| 11836 | 2 | 3 | 4 | | IV-1 | Ly6g6d | 58530 | 4-May-15 | 13546 | 2 | 3 | 4 | IV-1 | Mmp14 | 4323 | 10-May-15 |
| 11841 | 2 | 3 | 4 | | IV-1 | Ly6k | 54742 | 4-May-15 | 13560 | 2 | 3 | 4 | IV-1 | Mmp28 | 79148 | 12-May-15 |
| 11843 | 2 | 3 | 4 | | IV-1 | Ly86 | 9450 | 4-May-15 | 13561 | 2 | 3 | 4 | IV-1 | Mmp3 | 4314 | 17-May-15 |
| 11844 | 2 | 3 | 4 | | IV-1 | Ly9 | 4063 | 4-May-15 | 13563 | 2 | 3 | 4 | IV-1 | Mmp8 | 4317 | 24-May-15 |
| 11845 | 2 | 3 | 4 | | IV-1 | Ly96 | 23643 | 31-May-15 | 13564 | 2 | 3 | 4 | IV-1 | Mmp9 | 4318 | 24-May-15 |
| 11847 | 2 | 3 | 4 | | IV-1 | Lyg1 | 129530 | 4-May-15 | 13569 | 2 | 3 | 4 | IV-1 | Mn1 | 4330 | 12-May-15 |
| 11852 | 2 | 3 | 4 | | IV-1 | Lypd1 | 116372 | 4-May-15 | 13575 | 2 | 3 | 4 | IV-1 | Mns1 | 55329 | 4-May-15 |
| 11854 | 2 | 3 | 4 | | IV-1 | Lypd3 | 27076 | 4-May-15 | 13578 | 2 | 3 | 4 | IV-1 | Moap1 | 64112 | 4-May-15 |
| 11857 | 2 | 3 | 4 | | IV-1 | Lypd6 | 130574 | 4-May-15 | 13585 | 2 | 3 | 4 | IV-1 | Mob4 | 25843 | 4-May-15 |
| 11874 | 2 | 3 | 4 | | IV-1 | Lyst | 1130 | 23-May-15 | 13593 | 2 | 3 | 4 | IV-1 | Mogat2 | 80168 | 4-May-15 |
| 11875 | 2 | 3 | 4 | | IV-1 | Lyve1 | 10894 | 4-May-15 | 13603 | 2 | 3 | 4 | IV-1 | Morc4 | 79710 | 12-May-15 |
| 11896 | 2 | 3 | 4 | | IV-1 | Macrod1 | 28992 | 12-May-15 | 13624 | 2 | 3 | 4 | IV-1 | Mpeg1 | 219972 | 12-May-15 |
| 11901 | 2 | 3 | 4 | | IV-1 | Mad2l2 | 10459 | 4-May-15 | 13636 | 2 | 3 | 4 | IV-1 | Mpp2 | 4355 | 7-Jun-15 |
| 11902 | 2 | 3 | 4 | | IV-1 | Madcam1 | 8174 | 4-May-15 | 13637 | 2 | 3 | 4 | IV-1 | Mpp3 | 4356 | 4-May-15 |
| 11906 | 2 | 3 | 4 | | IV-1 | Maf | 4094 | 4-May-15 | 13640 | 2 | 3 | 4 | IV-1 | Mpp6 | 51678 | 7-Jun-15 |
| 11909 | 2 | 3 | 4 | | IV-1 | Mafb | 9935 | 2-Jun-15 | 13653 | 2 | 3 | 4 | IV-1 | Mpzl1 | 9019 | 4-May-15 |
| 11910 | 2 | 3 | 4 | | IV-1 | Maff | 23764 | 4-May-15 | 13654 | 2 | 3 | 4 | IV-1 | Mpzl2 | 10205 | 4-May-15 |
| 11926 | 2 | 3 | 4 | | IV-1 | Mageb2 | 4113 | 4-May-15 | 13655 | 2 | 3 | 4 | IV-1 | Mpzl3 | 196264 | 4-May-15 |
| 11939 | 2 | 3 | 4 | | IV-1 | Magix | 79917 | 4-May-15 | 13658 | 2 | 3 | 4 | IV-1 | Mrap2 | 112609 | 24-May-15 |
| 11946 | 2 | 3 | 4 | | IV-1 | Mal | 114569 | 4-May-15 | 13660 | 2 | 3 | 4 | IV-1 | Mrc1 | 4360 | 12-May-15 |
| 11955 | 2 | 3 | 4 | | IV-1 | Maml3 | 55534 | 4-May-15 | 13663 | 2 | 3 | 4 | IV-1 | Mreg | 55686 | 4-May-15 |
| 11958 | 2 | 3 | 4 | | IV-1 | Man1a | | | 13682 | 2 | 3 | 4 | IV-1 | Mrgprg | 386746 | 4-May-15 |
| 11967 | 2 | 3 | 4 | | IV-1 | Man2c1os | | | 13724 | 2 | 3 | 4 | IV-1 | Mrpl27 | 51253 | 4-May-15 |
| 11972 | 2 | 3 | 4 | | IV-1 | Manf | 7873 | 21-May-15 | 13755 | 2 | 3 | 4 | IV-1 | Mrps18c | 51023 | 12-May-15 |
| 11976 | 2 | 3 | 4 | | IV-1 | Maoa | 4128 | 31-May-15 | 13790 | 2 | 3 | 4 | IV-1 | Ms4a6b | | |
| 11977 | 2 | 3 | 4 | | IV-1 | Maob | 4129 | 17-May-15 | 13791 | 2 | 3 | 4 | IV-1 | Ms4a6c | | |
| 11997 | 2 | 3 | 4 | | IV-1 | Map3k13 | 9175 | 12-May-15 | 13792 | 2 | 3 | 4 | IV-1 | Ms4a6d | | |
| 11998 | 2 | 3 | 4 | | IV-1 | Map3k14 | 9020 | 14-May-15 | 13793 | 2 | 3 | 4 | IV-1 | Ms4a7 | 58475 | 7-Jun-15 |
| 12005 | 2 | 3 | 4 | | IV-1 | Map3k6 | 9064 | 12-May-15 | 13794 | 2 | 3 | 4 | IV-1 | Ms4a8a | | |
| 12017 | 2 | 3 | 4 | | IV-1 | Map6d1 | 79929 | 4-May-15 | 13815 | 2 | 3 | 4 | IV-1 | Msmo1 | 6307 | 4-May-15 |
| 12018 | 2 | 3 | 4 | | IV-1 | Map7 | 9053 | 4-May-15 | 13818 | 2 | 3 | 4 | IV-1 | Msr1 | 4481 | 17-May-15 |
| 12020 | 2 | 3 | 4 | | IV-1 | Map7d2 | 256714 | 4-May-15 | 13825 | 2 | 3 | 4 | IV-1 | Mst1r | 4486 | 12-May-15 |
| 12025 | 2 | 3 | 4 | | IV-1 | Mapk12 | 6300 | 12-May-15 | 13863 | 2 | 3 | 4 | IV-1 | Mthfd1l | 25902 | 4-May-15 |
| 12026 | 2 | 3 | 4 | | IV-1 | Mapk13 | 5603 | 4-May-15 | 13864 | 2 | 3 | 4 | IV-1 | Mthfd2 | 10797 | 4-May-15 |
| 12032 | 2 | 3 | 4 | | IV-1 | Mapk4 | 5596 | 4-May-15 | 13867 | 2 | 3 | 4 | IV-1 | Mthfs | 10588 | 4-May-15 |
| 12044 | 2 | 3 | 4 | | IV-1 | Mapkbp1 | 23005 | 4-May-15 | 13875 | 2 | 3 | 4 | IV-1 | Mtmr11 | 10903 | 17-May-15 |
| 12048 | 2 | 3 | 4 | | IV-1 | Mapt | 4137 | 23-May-15 | 13877 | 2 | 3 | 4 | IV-1 | Mtmr14 | 64419 | 12-May-15 |
| 12055 | 2 | 3 | 4 | | IV-1 | March3 | 115123 | 4-May-15 | 13898 | 2 | 3 | 4 | IV-1 | Mttus1 | 57509 | 12-May-15 |
| 12061 | 2 | 3 | 4 | | IV-1 | March9 | 92979 | 4-May-15 | 13903 | 2 | 3 | 4 | IV-1 | Muc1 | 4582 | 22-May-15 |

Fig.22 - 32

| | | | | | | | | | | | | | | | |
|---|---|---|---|---|---|---|---|---|---|---|---|---|---|---|---|
| 13906 | 2 | 3 | 4 | | IV-1 | Muc19 | 283463 | 12-May-15 | 14585 | 2 | 3 | 4 | | IV-1 | Nptx2 | 4885 | 12-May-15 |
| 13908 | 2 | 3 | 4 | | IV-1 | Muc20 | 200958 | 12-May-15 | 14588 | 2 | 3 | 4 | | IV-1 | Npw | 283869 | 12-May-15 |
| 13909 | 2 | 3 | 4 | | IV-1 | Muc4 | 4585 | 12-May-15 | 14589 | 2 | 3 | 4 | | IV-1 | Npy | 4852 | 17-May-15 |
| 13912 | 2 | 3 | 4 | | IV-1 | Muc6 | 4588 | 12-May-15 | 14595 | 2 | 3 | 4 | | IV-1 | Nqo1 | 1728 | 17-May-15 |
| 13919 | 2 | 3 | 4 | | IV-1 | Mum1l1 | 139221 | 4-May-15 | 14599 | 2 | 3 | 4 | | IV-1 | Nr1d1 | 9572 | 12-May-15 |
| 13934 | 2 | 3 | 4 | | IV-1 | Mup4 | | | 14603 | 2 | 3 | 4 | | IV-1 | Nr1h4 | 9971 | 31-May-15 |
| 13943 | 2 | 3 | 4 | | IV-1 | Mustn1 | 389125 | 12-May-15 | 14605 | 2 | 3 | 4 | | IV-1 | Nr1i2 | 8856 | 24-May-15 |
| 13948 | 2 | 3 | 4 | | IV-1 | Mvd | 4597 | 4-May-15 | 14606 | 2 | 3 | 4 | | IV-1 | Nr1i3 | 9970 | 4-May-15 |
| 13949 | 2 | 3 | 4 | | IV-1 | Mvk | 4598 | 17-May-15 | 14608 | 2 | 3 | 4 | | IV-1 | Nr2c2 | 7182 | 31-May-15 |
| 13950 | 2 | 3 | 4 | | IV-1 | Mvp | 9961 | 7-Jun-15 | 14612 | 2 | 3 | 4 | | IV-1 | Nr2f1 | 7025 | 7-Jun-15 |
| 13954 | 2 | 3 | 4 | | IV-1 | Mxd3 | 83463 | 4-May-15 | 14613 | 2 | 3 | 4 | | IV-1 | Nr2f2 | 7026 | 7-Jun-15 |
| 13958 | 2 | 3 | 4 | | IV-1 | Mxra8 | 54587 | 4-May-15 | 14619 | 2 | 3 | 4 | | IV-1 | Nr4a3 | 8013 | 4-May-15 |
| 13964 | 2 | 3 | 4 | | IV-1 | Mybl2 | 4605 | 4-May-15 | 14629 | 2 | 3 | 4 | | IV-1 | Nrbp2 | 340371 | 4-May-15 |
| 13968 | 2 | 3 | 4 | | IV-1 | Mybph | 4608 | 4-May-15 | 14640 | 2 | 3 | 4 | | IV-1 | Nrgn | 4900 | 4-May-15 |
| 13970 | 2 | 3 | 4 | | IV-1 | Myc | 4609 | 24-May-15 | 14641 | 2 | 3 | 4 | | IV-1 | Nrip1 | 8204 | 3-May-15 |
| 13973 | 2 | 3 | 4 | | IV-1 | Mycbpap | 84073 | 4-May-15 | 14647 | 2 | 3 | 4 | | IV-1 | Nrn1 | 51299 | 4-May-15 |
| 13974 | 2 | 3 | 4 | | IV-1 | Mycl | 4610 | 21-May-15 | 14656 | 2 | 3 | 4 | | IV-1 | Nrtn | 4902 | 23-May-15 |
| 13985 | 2 | 3 | 4 | | IV-1 | Myh10 | 4628 | 21-May-15 | 14672 | 2 | 3 | 4 | | IV-1 | Nsmf | 26012 | 4-May-15 |
| 13986 | 2 | 3 | 4 | | IV-1 | Myh11 | 4629 | 28-May-15 | 14678 | 2 | 3 | 4 | | IV-1 | Nsun7 | 79730 | 4-May-15 |
| 13987 | 2 | 3 | 4 | | IV-1 | Myh13 | 8735 | 4-May-15 | 14688 | 2 | 3 | 4 | | IV-1 | Nt5e | 4907 | 4-May-15 |
| 14002 | 2 | 3 | 4 | | IV-1 | Myl2 | 4633 | 23-May-15 | 14692 | 2 | 3 | 4 | | IV-1 | Ntf5 | 4909 | 4-May-15 |
| 14008 | 2 | 3 | 4 | | IV-1 | Myl9 | 10398 | 4-May-15 | 14701 | 2 | 3 | 4 | | IV-1 | Ntng2 | 84628 | 4-May-15 |
| 14010 | 2 | 3 | 4 | | IV-1 | Mylk | 4638 | 4-May-15 | 14707 | 2 | 3 | 4 | | IV-1 | Ntsr1 | 4923 | 4-May-15 |
| 14027 | 2 | 3 | 4 | | IV-1 | Myo1f | 4542 | 4-May-15 | 14716 | 2 | 3 | 4 | | IV-1 | Nudt2 | 4925 | 4-May-15 |
| 14040 | 2 | 3 | 4 | | IV-1 | Myoc | 4653 | 16-May-15 | 14723 | 2 | 3 | 4 | | IV-1 | Nudt10 | 170685 | 7-Jun-15 |
| 14041 | 2 | 3 | 4 | | IV-1 | Myocd | 93649 | 31-May-15 | 14724 | 2 | 3 | 4 | | IV-1 | Nudt11 | 55190 | 4-May-15 |
| 14042 | 2 | 3 | 4 | | IV-1 | Myod1 | 4654 | 28-May-15 | 14731 | 2 | 3 | 4 | | IV-1 | Nudt17 | 200035 | 23-May-15 |
| 14043 | 2 | 3 | 4 | | IV-1 | Myof | 26509 | 4-May-15 | 14736 | 2 | 3 | 4 | | IV-1 | Nudt22 | 84304 | 4-May-15 |
| 14044 | 2 | 3 | 4 | | IV-1 | Myog | 4656 | 4-May-15 | 14738 | 2 | 3 | 4 | | IV-1 | Nudt4 | 11163 | 12-May-15 |
| 14047 | 2 | 3 | 4 | | IV-1 | Myom3 | 127294 | 4-May-15 | 14758 | 2 | 3 | 4 | | IV-1 | Nup210 | 23225 | 4-May-15 |
| 14061 | 2 | 3 | 4 | | IV-1 | Mzb1 | 51237 | 4-May-15 | 14775 | 2 | 3 | 4 | | IV-1 | Nupr1 | 26471 | 4-May-15 |
| 14092 | 2 | 3 | 4 | | IV-1 | Naca | 4666 | 3-May-15 | 14780 | 2 | 3 | 4 | | IV-1 | Nutf2-ps1 | | |
| 14109 | 2 | 3 | 4 | | IV-1 | Naip5 | | | 14790 | 2 | 3 | 4 | | IV-1 | Nxn | 115861 | 4-May-15 |
| 14119 | 2 | 3 | 4 | | IV-1 | Nans | 54187 | 4-May-15 | 14791 | 2 | 3 | 4 | | IV-1 | Nxnl2 | 158046 | 4-May-15 |
| 14124 | 2 | 3 | 4 | | IV-1 | Nap1l5 | 266812 | 4-May-15 | 14793 | 2 | 3 | 4 | | IV-1 | Nxpe3 | 91775 | 4-May-15 |
| 14129 | 2 | 3 | 4 | | IV-1 | Naprt1 | 93100 | 4-May-15 | 14795 | 2 | 3 | 4 | | IV-1 | Nxpe5 | | |
| 14144 | 2 | 3 | 4 | | IV-1 | Nat8l | 339983 | 4-May-15 | 14810 | 2 | 3 | 4 | | IV-1 | Oas1b | | |
| 14152 | 2 | 3 | 4 | | IV-1 | Nbeal2 | 23218 | 4-May-15 | 14813 | 2 | 3 | 4 | | IV-1 | Oas1e | | |
| 14157 | 2 | 3 | 4 | | IV-1 | Ncoa1 | 4684 | 12-May-15 | 14833 | 2 | 3 | 4 | | IV-1 | Obp2a | 29991 | 12-May-15 |
| 14168 | 2 | 3 | 4 | | IV-1 | Nccrp1 | 342897 | 4-May-15 | 14835 | 2 | 3 | 4 | | IV-1 | Obscn | 84033 | 28-May-15 |
| 14171 | 2 | 3 | 4 | | IV-1 | Ncf1 | 653361 | 4-May-15 | 14836 | 2 | 3 | 4 | | IV-1 | Obsl1 | 23363 | 4-May-15 |
| 14172 | 2 | 3 | 4 | | IV-1 | Ncf2 | 4688 | 12-May-15 | 14842 | 2 | 3 | 4 | | IV-1 | Ocln | 100506658 | 12-May-15 |
| 14173 | 2 | 3 | 4 | | IV-1 | Ncf4 | 4689 | 4-May-15 | 14845 | 2 | 3 | 4 | | IV-1 | Ocstamp | 128506 | 4-May-15 |
| 14209 | 2 | 3 | 4 | | IV-1 | Ndrg2 | 57447 | 4-May-15 | 14852 | 2 | 3 | 4 | | IV-1 | Odf3b | 440836 | 4-May-15 |
| 14211 | 2 | 3 | 4 | | IV-1 | Ndrg4 | 65009 | 4-May-15 | 14870 | 2 | 3 | 4 | | IV-1 | Olf3 | 170392 | 4-May-15 |
| 14224 | 2 | 3 | 4 | | IV-1 | Ndufa4l2 | 56901 | 4-May-15 | 14874 | 2 | 3 | 4 | | IV-1 | Olfm2 | 93145 | 12-May-15 |
| 14240 | 2 | 3 | 4 | | IV-1 | Ndufb2 | 4708 | 12-May-15 | 14878 | 2 | 3 | 4 | | IV-1 | Olfml2a | 169611 | 4-May-15 |
| 14261 | 2 | 3 | 4 | | IV-1 | Neat1 | 283131 | 12-May-15 | 14910 | 2 | 3 | 4 | | IV-1 | Olfr1033 | | |
| 14273 | 2 | 3 | 4 | | IV-1 | Nedd9 | 4739 | 4-May-15 | 14911 | 2 | 3 | 4 | | IV-1 | Olfr1034 | | |
| 14275 | 2 | 3 | 4 | | IV-1 | Nefl | 4747 | 23-May-15 | 15202 | 2 | 3 | 4 | | IV-1 | Olfr1372-ps1 | | |
| 14276 | 2 | 3 | 4 | | IV-1 | Nefm | 4741 | 28-May-15 | 15210 | 2 | 3 | 4 | | IV-1 | Olfr1383 | | |
| 14279 | 2 | 3 | 4 | | IV-1 | Neil2 | 252969 | 4-May-15 | 15453 | 2 | 3 | 4 | | IV-1 | Olfr380 | | |
| 14280 | 2 | 3 | 4 | | IV-1 | Neil3 | 55247 | 4-May-15 | 15936 | 2 | 3 | 4 | | IV-1 | Olfr920 | | |
| 14284 | 2 | 3 | 4 | | IV-1 | Nek2 | 4751 | 4-May-15 | 15998 | 2 | 3 | 4 | | IV-1 | Olig1 | 116448 | 4-May-15 |
| 14290 | 2 | 3 | 4 | | IV-1 | Nek8 | 284086 | 7-Jun-15 | 16003 | 2 | 3 | 4 | | IV-1 | Omd | 4958 | 4-May-15 |
| 14305 | 2 | 3 | 4 | | IV-1 | Net1 | 10276 | n-2015 | 16034 | 2 | 3 | 4 | | IV-1 | Optc | 26254 | 4-May-15 |
| 14307 | 2 | 3 | 4 | | IV-1 | Neto2 | 81831 | 4-May-15 | 16040 | 2 | 3 | 4 | | IV-1 | Orc1 | 4998 | 7-Jun-15 |
| 14309 | 2 | 3 | 4 | | IV-1 | Neu2 | 4759 | 4-May-15 | 16054 | 2 | 3 | 4 | | IV-1 | Osbp2 | 23762 | 12-May-15 |
| 14310 | 2 | 3 | 4 | | IV-1 | Neu3 | 10825 | 3-May-15 | 16055 | 2 | 3 | 4 | | IV-1 | Osbpl10 | 114884 | 4-May-15 |
| 14312 | 2 | 3 | 4 | | IV-1 | Neurl1a | | | 16057 | 2 | 3 | 4 | | IV-1 | Osbpl1a | 114876 | 4-May-15 |
| 14314 | 2 | 3 | 4 | | IV-1 | Neurl2 | 140825 | 4-May-15 | 16062 | 2 | 3 | 4 | | IV-1 | Osbpl7 | 114881 | 21-May-15 |
| 14317 | 2 | 3 | 4 | | IV-1 | Neurod1 | 4760 | 28-May-15 | 16066 | 2 | 3 | 4 | | IV-1 | Oscp1 | 127700 | 4-May-15 |
| 14319 | 2 | 3 | 4 | | IV-1 | Neurod4 | 58158 | 7-Jun-15 | 16070 | 2 | 3 | 4 | | IV-1 | Osgin1 | 29948 | 4-May-15 |
| 14331 | 2 | 3 | 4 | | IV-1 | Nfatc2 | 4773 | 28-May-15 | 16073 | 2 | 3 | 4 | | IV-1 | Osmr | 9180 | 23-May-15 |
| 14335 | 2 | 3 | 4 | | IV-1 | Nfe2 | 4778 | 12-May-15 | 16074 | 2 | 3 | 4 | | IV-1 | Osr1 | 130497 | 7-Jun-15 |
| 14342 | 2 | 3 | 4 | | IV-1 | Nfil3 | 4783 | 4-May-15 | 16075 | 2 | 3 | 4 | | IV-1 | Osr2 | 116039 | 4-May-15 |
| 14349 | 2 | 3 | 4 | | IV-1 | Nfkb2 | 4791 | 28-May-15 | 16083 | 2 | 3 | 4 | | IV-1 | Otof | 9381 | 23-May-15 |
| 14346 | 2 | 3 | 4 | | IV-1 | Nfkbia | 4792 | 31-May-15 | 16113 | 2 | 3 | 4 | | IV-1 | Ovol2 | 58495 | 4-May-15 |
| 14351 | 2 | 3 | 4 | | IV-1 | Nfkbiz | 64332 | 4-May-15 | 16127 | 2 | 3 | 4 | | IV-1 | P2rx1 | 5023 | 17-May-15 |
| 14365 | 2 | 3 | 4 | | IV-1 | Ngfrap1 | 27018 | 12-May-15 | 16132 | 2 | 3 | 4 | | IV-1 | P2rx6 | 9127 | 4-May-15 |
| 14367 | 2 | 3 | 4 | | IV-1 | Ngp | | | 16139 | 2 | 3 | 4 | | IV-1 | P2ry2 | 5029 | 17-May-15 |
| 14369 | 2 | 3 | 4 | | IV-1 | Nhej1 | 79840 | 4-May-15 | 16140 | 2 | 3 | 4 | | IV-1 | P2ry4 | 5030 | 21-May-15 |
| 14375 | 2 | 3 | 4 | | IV-1 | Nhlrc4 | 283948 | 21-May-15 | 16143 | 2 | 3 | 4 | | IV-1 | P4ha2 | 8974 | 4-May-15 |
| 14383 | 2 | 3 | 4 | | IV-1 | Nid2 | 22795 | 12-May-15 | 16161 | 2 | 3 | 4 | | IV-1 | Pacsin1 | 29993 | 4-May-15 |
| 14392 | 2 | 3 | 4 | | IV-1 | Nipa1 | 123606 | 12-May-15 | 16163 | 2 | 3 | 4 | | IV-1 | Pacsin3 | 29763 | 4-May-15 |
| 14394 | 2 | 3 | 4 | | IV-1 | Nipal1 | 152519 | 4-May-15 | 16164 | 2 | 3 | 4 | | IV-1 | Padi1 | 29943 | 4-May-15 |
| 14395 | 2 | 3 | 4 | | IV-1 | Nipal2 | 79815 | 4-May-15 | 16172 | 2 | 3 | 4 | | IV-1 | Pafah1b3 | 5050 | 4-May-15 |
| 14435 | 2 | 3 | 4 | | IV-1 | Nlgn1 | 22871 | 28-May-15 | 16174 | 2 | 3 | 4 | | IV-1 | Pag1 | 55824 | 4-May-15 |
| 14447 | 2 | 3 | 4 | | IV-1 | Nkrp1b | | | 16176 | 2 | 3 | 4 | | IV-1 | Pah | 5053 | 23-May-15 |
| 14464 | 2 | 3 | 4 | | IV-1 | Nmb | 4828 | 7-Jun-15 | 16186 | 2 | 3 | 4 | | IV-1 | Pak6 | 56924 | 4-May-15 |
| 14471 | 2 | 3 | 4 | | IV-1 | Nme5 | 8382 | 4-May-15 | 16194 | 2 | 3 | 4 | | IV-1 | Palmd | 54873 | 4-May-15 |
| 14487 | 2 | 3 | 4 | | IV-1 | Nmur1 | 10316 | 12-May-15 | 16196 | 2 | 3 | 4 | | IV-1 | Pam16 | 51025 | 28-May-15 |
| 14489 | 2 | 3 | 4 | | IV-1 | Nnat | 4826 | 4-May-15 | 16197 | 2 | 3 | 4 | | IV-1 | Pamr1 | 25891 | 4-May-15 |
| 14490 | 2 | 3 | 4 | | IV-1 | Nnmt | 4837 | 17-May-15 | 16200 | 2 | 3 | 4 | | IV-1 | Pank1 | 53354 | 4-May-15 |
| 14533 | 2 | 3 | 4 | | IV-1 | Notum | 147111 | 9-May-15 | 16207 | 2 | 3 | 4 | | IV-1 | Paox | 196743 | 4-May-15 |
| 14534 | 2 | 3 | 4 | | IV-1 | Nov | 4856 | 7-Jun-15 | 16216 | 2 | 3 | 4 | | IV-1 | Pappa | 5069 | 17-May-15 |
| 14537 | 2 | 3 | 4 | | IV-1 | Nox1 | 27035 | 10-May-15 | 16217 | 2 | 3 | 4 | | IV-1 | Pappa2 | 60676 | 17-May-15 |
| 14540 | 2 | 3 | 4 | | IV-1 | Noxa1 | 10811 | 26-May-15 | 16227 | 2 | 3 | 4 | | IV-1 | Pard3 | 56288 | 4-May-15 |
| 14548 | 2 | 3 | 4 | | IV-1 | Nph | 256933 | 4-May-15 | 16230 | 2 | 3 | 4 | | IV-1 | Pard6b | 84612 | 4-May-15 |
| 14553 | 2 | 3 | 4 | | IV-1 | Npcd | | | 16231 | 2 | 3 | 4 | | IV-1 | Pard6g | 84552 | 4-May-15 |
| 14557 | 2 | 3 | 4 | | IV-1 | Npff | 8620 | 4-May-15 | 16236 | 2 | 3 | 4 | | IV-1 | Parm1 | 25849 | 4-May-15 |
| 14566 | 2 | 3 | 4 | | IV-1 | Npl | 80896 | 4-May-15 | 16248 | 2 | 3 | 4 | | IV-1 | Parp8 | 79668 | 12-May-15 |
| 14570 | 2 | 3 | 4 | | IV-1 | Npm3 | 10360 | 4-May-15 | 16252 | 2 | 3 | 4 | | IV-1 | Parva | 55742 | 4-May-15 |
| 14572 | 2 | 3 | 4 | | IV-1 | Npnt | 255743 | 4-May-15 | 16272 | 2 | 3 | 4 | | IV-1 | Pax9 | 5083 | 28-May-15 |
| 14573 | 2 | 3 | 4 | | IV-1 | Nppa | 4878 | 12-May-15 | 16277 | 2 | 3 | 4 | | IV-1 | Pbld1 | | |
| 14576 | 2 | 3 | 4 | | IV-1 | Npr1 | 4881 | 24-May-15 | 16291 | 2 | 3 | 4 | | IV-1 | Pcbp3 | 54039 | 4-May-15 |
| 14584 | 2 | 3 | 4 | | IV-1 | Nptx1 | 4884 | 3-May-15 | 16295 | 2 | 3 | 4 | | IV-1 | Pcdh1 | 5097 | 4-May-15 |

Fig.22 - 33

| | | | | | | | | | | | | | | | |
|---|---|---|---|---|---|---|---|---|---|---|---|---|---|---|---|
| 16360 | 2 | 3 | 4 | | IV-1 | Pcdhgb6 | 56100 | 4-May-15 | 16837 | 2 | 3 | 4 | IV-1 | Pla2g7 | 7941 | 12-May-15 |
| 16370 | 2 | 3 | 4 | | IV-1 | Pcgf2 | 7703 | 4-May-15 | 16851 | 2 | 3 | 4 | IV-1 | Plb1 | 151086 | 4-May-15 |
| 16377 | 2 | 3 | 4 | | IV-1 | Pck2 | 5106 | 12-May-15 | 16867 | 2 | 3 | 4 | IV-1 | Plcl2 | 23228 | 14-May-15 |
| 16391 | 2 | 3 | 4 | | IV-1 | Pcolce2 | 26577 | 12-May-15 | 16875 | 2 | 3 | 4 | IV-1 | Pld4 | 122618 | 12-May-15 |
| 16392 | 2 | 3 | 4 | | IV-1 | Pcp2 | 126006 | 7-Jun-15 | 16877 | 2 | 3 | 4 | IV-1 | Pld6 | 201164 | 29-May-15 |
| 16400 | 2 | 3 | 4 | | IV-1 | Pcsk4 | 54760 | 4-May-15 | 16880 | 2 | 3 | 4 | IV-1 | Plek | 5341 | 4-May-15 |
| 16402 | 2 | 3 | 4 | | IV-1 | Pcsk6 | 5046 | 4-May-15 | 16884 | 2 | 3 | 4 | IV-1 | Plekha3 | 65977 | 12-May-15 |
| 16405 | 2 | 3 | 4 | | IV-1 | Pctp | 58488 | 4-May-15 | 16887 | 2 | 3 | 4 | IV-1 | Plekha6 | 22874 | 4-May-15 |
| 16406 | 2 | 3 | 4 | | IV-1 | Pcx | | | 16890 | 2 | 3 | 4 | IV-1 | Plekhb1 | 58473 | 4-May-15 |
| 16408 | 2 | 3 | 4 | | IV-1 | Pcyox1l | 78991 | 4-May-15 | 16893 | 2 | 3 | 4 | IV-1 | Plekhd1os | | |
| 16421 | 2 | 3 | 4 | | IV-1 | Pdcd5 | 9141 | 4-May-15 | 16901 | 2 | 3 | 4 | IV-1 | Plekhg6 | 55200 | 4-May-15 |
| 16436 | 2 | 3 | 4 | | IV-1 | Pde3a | 5139 | 31-May-15 | 16902 | 2 | 3 | 4 | IV-1 | Plekhh1 | 57475 | 12-May-15 |
| 16437 | 2 | 3 | 4 | | IV-1 | Pde3b | 5140 | 4-May-15 | 16904 | 2 | 3 | 4 | IV-1 | Plekhh3 | 79990 | 12-May-15 |
| 16441 | 2 | 3 | 4 | | IV-1 | Pde4d | 5144 | 2-Jun-15 | 16912 | 2 | 3 | 4 | IV-1 | Plekhs1 | 79949 | 30-Apr-15 |
| 16442 | 2 | 3 | 4 | | IV-1 | Pde4dip | 9659 | 12-May-15 | 16914 | 2 | 3 | 4 | IV-1 | Pletlos | | |
| 16458 | 2 | 3 | 4 | | IV-1 | Pdgfc | 56034 | 17-May-15 | 16916 | 2 | 3 | 4 | IV-1 | Plgrkt | 55848 | 4-May-15 |
| 16460 | 2 | 3 | 4 | | IV-1 | Pdgfra | 5156 | 17-May-15 | 16918 | 2 | 3 | 4 | IV-1 | Plin2 | 123 | 4-May-15 |
| 16467 | 2 | 3 | 4 | | IV-1 | Pdia2 | 64714 | 12-May-15 | 16921 | 2 | 3 | 4 | IV-1 | Plin5 | 440503 | 4-May-15 |
| 16469 | 2 | 3 | 4 | | IV-1 | Pdia4 | 9601 | 4-May-15 | 16923 | 2 | 3 | 4 | IV-1 | Plk2 | 10769 | 17-May-15 |
| 16470 | 2 | 3 | 4 | | IV-1 | Pdia5 | 10954 | 4-May-15 | 16924 | 2 | 3 | 4 | IV-1 | Plk3 | 1263 | 4-May-15 |
| 16474 | 2 | 3 | 4 | | IV-1 | Pdk1 | 5163 | 7-Jun-15 | 16927 | 2 | 3 | 4 | IV-1 | Pllp | 51090 | 4-May-15 |
| 16475 | 2 | 3 | 4 | | IV-1 | Pdk2 | 5164 | 4-May-15 | 16936 | 2 | 3 | 4 | IV-1 | Pls3 | 5358 | 12-May-15 |
| 16479 | 2 | 3 | 4 | | IV-1 | Pdlim2 | 64236 | 4-May-15 | 16947 | 2 | 3 | 4 | IV-1 | Plxna2 | 5362 | 4-May-15 |
| 16483 | 2 | 3 | 4 | | IV-1 | Pdlim7 | 9260 | 24-May-15 | 16952 | 2 | 3 | 4 | IV-1 | Plxnb2 | 23654 | 4-May-15 |
| 16488 | 2 | 3 | 4 | | IV-1 | Pdpr | 55066 | 4-May-15 | 16957 | 2 | 3 | 4 | IV-1 | Pm20d2 | 135293 | 4-May-15 |
| 16490 | 2 | 3 | 4 | | IV-1 | Pds5a | 23244 | 4-May-15 | 16960 | 2 | 3 | 4 | IV-1 | Pmel | 6496 | 12-May-15 |
| 16494 | 2 | 3 | 4 | | IV-1 | Pdx1 | 3651 | 7-Jun-15 | 16974 | 2 | 3 | 4 | IV-1 | Pmvk | 10654 | 4-May-15 |
| 16496 | 2 | 3 | 4 | | IV-1 | Pdxk | 8566 | 4-May-15 | 16994 | 2 | 3 | 4 | IV-1 | Pnp2 | | |
| 16514 | 2 | 3 | 4 | | IV-1 | Pear1 | 375033 | 4-May-15 | 16995 | 2 | 3 | 4 | IV-1 | Pnpla2 | 57104 | 4-May-15 |
| 16515 | 2 | 3 | 4 | | IV-1 | Pebp1 | 5037 | 4-May-15 | 16998 | 2 | 3 | 4 | IV-1 | Pnpla5 | 150379 | 4-May-15 |
| 16520 | 2 | 3 | 4 | | IV-1 | Peg10 | 23089 | 4-May-15 | 17009 | 2 | 3 | 4 | IV-1 | Podn | 127435 | 4-May-15 |
| 16522 | 2 | 3 | 4 | | IV-1 | Peg13 | | | 17010 | 2 | 3 | 4 | IV-1 | Podnl1 | 79863 | 4-May-15 |
| 16523 | 2 | 3 | 4 | | IV-1 | Peg3 | 5178 | 12-May-15 | 17023 | 2 | 3 | 4 | IV-1 | Pold2 | 5425 | 12-May-15 |
| 16524 | 2 | 3 | 4 | | IV-1 | Peg3os | | | 17058 | 2 | 3 | 4 | IV-1 | Polr2k | 5440 | 4-May-15 |
| 16530 | 2 | 3 | 4 | | IV-1 | Pemt | 10400 | 7-Jun-15 | 17073 | 2 | 3 | 4 | IV-1 | Pomc | 5443 | 23-May-15 |
| 16531 | 2 | 3 | 4 | | IV-1 | Penk | 5179 | 12-May-15 | 17080 | 2 | 3 | 4 | IV-1 | Pon1 | 5444 | 4-May-15 |
| 16534 | 2 | 3 | 4 | | IV-1 | Per1 | 5187 | 12-May-15 | 17084 | 2 | 3 | 4 | IV-1 | Pop4 | 10775 | 4-May-15 |
| 16535 | 2 | 3 | 4 | | IV-1 | Per2 | 8864 | 17-May-15 | 17087 | 2 | 3 | 4 | IV-1 | Popdc2 | 64091 | 12-May-15 |
| 16536 | 2 | 3 | 4 | | IV-1 | Per3 | 8863 | 17-May-15 | 17088 | 2 | 3 | 4 | IV-1 | Popdc3 | 64208 | 4-May-15 |
| 16538 | 2 | 3 | 4 | | IV-1 | Perm1 | 84808 | 12-May-15 | 17090 | 2 | 3 | 4 | IV-1 | Porcn | 64840 | 23-May-15 |
| 16539 | 2 | 3 | 4 | | IV-1 | Perp | 64065 | 4-May-15 | 17091 | 2 | 3 | 4 | IV-1 | Postn | 10631 | 17-May-15 |
| 16543 | 2 | 3 | 4 | | IV-1 | Pet117 | 100303755 | 4-May-15 | 17096 | 2 | 3 | 4 | IV-1 | Pou2af1 | 5450 | 4-May-15 |
| 16547 | 2 | 3 | 4 | | IV-1 | Pex11a | 8800 | 4-May-15 | 17099 | 2 | 3 | 4 | IV-1 | Pou2f3 | 25833 | 28-May-15 |
| 16553 | 2 | 3 | 4 | | IV-1 | Pex16 | 9409 | 23-May-15 | 17100 | 2 | 3 | 4 | IV-1 | Pou3f1 | 5453 | 4-May-15 |
| 16565 | 2 | 3 | 4 | | IV-1 | Pfdn2 | 5202 | 4-May-15 | 17116 | 2 | 3 | 4 | IV-1 | Ppap2a | 8611 | 4-May-15 |
| 16568 | 2 | 3 | 4 | | IV-1 | Pfkfb1 | 5207 | 4-May-15 | 17118 | 2 | 3 | 4 | IV-1 | Ppap2c | 8612 | 4-May-15 |
| 16570 | 2 | 3 | 4 | | IV-1 | Pfkfb3 | 5209 | 12-May-15 | 17123 | 2 | 3 | 4 | IV-1 | Ppara | 5465 | 17-May-15 |
| 16573 | 2 | 3 | 4 | | IV-1 | Pfkm | 5213 | 4-May-15 | 17125 | 2 | 3 | 4 | IV-1 | Pparg | 5468 | 17-May-15 |
| 16576 | 2 | 3 | 4 | | IV-1 | Pfn2 | 5217 | 4-May-15 | 17127 | 2 | 3 | 4 | IV-1 | Ppargc1b | 133522 | 4-May-15 |
| 16584 | 2 | 3 | 4 | | IV-1 | Pgap1 | 80055 | 4-May-15 | 17129 | 2 | 3 | 4 | IV-1 | Ppbp | 5473 | 12-May-15 |
| 16585 | 2 | 3 | 4 | | IV-1 | Pgap2 | 27315 | 12-May-15 | 17166 | 2 | 3 | 4 | IV-1 | Ppm1j | 333926 | 12-May-15 |
| 16586 | 2 | 3 | 4 | | IV-1 | Pgap3 | 93210 | 12-May-15 | 17179 | 2 | 3 | 4 | IV-1 | Ppp1r12b | 4660 | 14-May-15 |
| 16591 | 2 | 3 | 4 | | IV-1 | Pgf | 5228 | 21-May-15 | 17187 | 2 | 3 | 4 | IV-1 | Ppp1r15a | 23645 | 12-May-15 |
| 16598 | 2 | 3 | 4 | | IV-1 | Pglyrp3 | 114771 | 4-May-15 | 17191 | 2 | 3 | 4 | IV-1 | Ppp1r17 | 10842 | 4-May-15 |
| 16602 | 2 | 3 | 4 | | IV-1 | Pgm2l1 | 283209 | 4-May-15 | 17193 | 2 | 3 | 4 | IV-1 | Ppp1r1a | 5502 | 4-May-15 |
| 16604 | 2 | 3 | 4 | | IV-1 | Pgm5 | 5239 | 17-May-15 | 17194 | 2 | 3 | 4 | IV-1 | Ppp1r1b | 84152 | 4-May-15 |
| 16608 | 2 | 3 | 4 | | IV-1 | Pgr | 5241 | 24-May-15 | 17198 | 2 | 3 | 4 | IV-1 | Ppp1r26 | 9858 | 4-May-15 |
| 16610 | 2 | 3 | 4 | | IV-1 | Pgrmc1 | 10857 | 3-May-15 | 17208 | 2 | 3 | 4 | IV-1 | Ppp1r3b | 79660 | 4-May-15 |
| 16633 | 2 | 3 | 4 | | IV-1 | Phf19 | 26147 | 4-May-15 | 17209 | 2 | 3 | 4 | IV-1 | Ppp1r3c | 5507 | 4-May-15 |
| 16642 | 2 | 3 | 4 | | IV-1 | Phf6 | 84295 | 24-May-15 | 17211 | 2 | 3 | 4 | IV-1 | Ppp1r3e | 90673 | 4-May-15 |
| 16643 | 2 | 3 | 4 | | IV-1 | Phf7 | 51533 | 4-May-15 | 17214 | 2 | 3 | 4 | IV-1 | Ppp1r3g | 648791 | 4-May-15 |
| 16645 | 2 | 3 | 4 | | IV-1 | Phgdh | 26227 | 13-May-15 | 17225 | 2 | 3 | 4 | IV-1 | Ppp2r2b | 5521 | 23-May-15 |
| 16646 | 2 | 3 | 4 | | IV-1 | Phgr1 | 644844 | 4-May-15 | 17229 | 2 | 3 | 4 | IV-1 | Ppp2r3a | 5523 | 4-May-15 |
| 16648 | 2 | 3 | 4 | | IV-1 | Phka1 | 5255 | 4-May-15 | 17258 | 2 | 3 | 4 | IV-1 | Ppy | 5539 | 4-May-15 |
| 16651 | 2 | 3 | 4 | | IV-1 | Phkg1 | 5260 | 12-May-15 | 17267 | 2 | 3 | 4 | IV-1 | Pramef12 | 390999 | 4-May-15 |
| 16656 | 2 | 3 | 4 | | IV-1 | Phldb1 | 23187 | 29-May-15 | 17278 | 2 | 3 | 4 | IV-1 | Prap1 | 118471 | 12-May-15 |
| 16661 | 2 | 3 | 4 | | IV-1 | Phospho1 | 162466 | 4-May-15 | 17298 | 2 | 3 | 4 | IV-1 | Prdx2 | 7001 | 4-May-15 |
| 16668 | 2 | 3 | 4 | | IV-1 | Phtf1os | | | 17307 | 2 | 3 | 4 | IV-1 | Prelp | 5549 | 12-May-15 |
| 16669 | 2 | 3 | 4 | | IV-1 | Phtf2 | 57157 | 4-May-15 | 17315 | 2 | 3 | 4 | IV-1 | Prg4 | 10216 | 7-Jun-15 |
| 16673 | 2 | 3 | 4 | | IV-1 | Phyhip | 9796 | 4-May-15 | 17328 | 2 | 3 | 4 | IV-1 | Prkaa2 | 5563 | 4-May-15 |
| 16696 | 2 | 3 | 4 | | IV-1 | Piga | 5277 | 12-May-15 | 17334 | 2 | 3 | 4 | IV-1 | Prkag3 | 53632 | 12-May-15 |
| 16697 | 2 | 3 | 4 | | IV-1 | Pigb | 9488 | 23-May-15 | 17338 | 2 | 3 | 4 | IV-1 | Prkar2b | 5577 | 12-May-15 |
| 16731 | 2 | 3 | 4 | | IV-1 | Pik3r1 | 5295 | 28-May-15 | 17360 | 2 | 3 | 4 | IV-1 | Prl | 5617 | 17-May-15 |
| 16742 | 2 | 3 | 4 | | IV-1 | Pim2 | 11040 | 4-May-15 | 17402 | 2 | 3 | 4 | IV-1 | Prnd | 23627 | 12-May-15 |
| 16746 | 2 | 3 | 4 | | IV-1 | Pin4 | 5303 | 12-May-15 | 17404 | 2 | 3 | 4 | IV-1 | Prob1 | 389333 | 4-May-15 |
| 16748 | 2 | 3 | 4 | | IV-1 | Pink1 | 65018 | 31-May-15 | 17406 | 2 | 3 | 4 | IV-1 | Proca1 | 147011 | 4-May-15 |
| 16751 | 2 | 3 | 4 | | IV-1 | Pip | 5304 | 7-Jun-15 | 17407 | 2 | 3 | 4 | IV-1 | Procr | 10544 | 4-May-15 |
| 16759 | 2 | 3 | 4 | | IV-1 | Pipox | 51268 | 4-May-15 | 17408 | 2 | 3 | 4 | IV-1 | Prodh | 5625 | 4-May-15 |
| 16760 | 2 | 3 | 4 | | IV-1 | Pir | 8544 | 3-May-15 | 17415 | 2 | 3 | 4 | IV-1 | Prom1 | 8842 | 23-May-15 |
| 16761 | 2 | 3 | 4 | | IV-1 | Pira1 | | | 17422 | 2 | 3 | 4 | IV-1 | Proser2 | 254427 | 4-May-15 |
| 16762 | 2 | 3 | 4 | | IV-1 | Pira11 | | | 17454 | 2 | 3 | 4 | IV-1 | Prr15 | 222171 | 4-May-15 |
| 16767 | 2 | 3 | 4 | | IV-1 | Pirb | 11025 | 4-May-15 | 17455 | 2 | 3 | 4 | IV-1 | Prr15l | 79170 | 4-May-15 |
| 16777 | 2 | 3 | 4 | | IV-1 | Pitpnm1 | 9600 | 4-May-15 | 17456 | 2 | 3 | 4 | IV-1 | Prr16 | 51334 | 12-May-15 |
| 16781 | 2 | 3 | 4 | | IV-1 | Pitrm1 | 10531 | 23-May-15 | 17462 | 2 | 3 | 4 | IV-1 | Prr27 | 401137 | 4-May-15 |
| 16783 | 2 | 3 | 4 | | IV-1 | Pitx2 | 5308 | 23-May-15 | 17464 | 2 | 3 | 4 | IV-1 | Prr30 | 339779 | 4-May-15 |
| 16788 | 2 | 3 | 4 | | IV-1 | Pja1 | 64219 | 4-May-15 | 17475 | 2 | 3 | 4 | IV-1 | Prrg1 | 5638 | 4-May-15 |
| 16795 | 2 | 3 | 4 | | IV-1 | Pkd2l2 | 27039 | 12-May-15 | 17479 | 2 | 3 | 4 | IV-1 | Prrt1 | 80863 | 4-May-15 |
| 16801 | 2 | 3 | 4 | | IV-1 | Pkib | 5570 | 4-May-15 | 17487 | 2 | 3 | 4 | IV-1 | Prss12 | 8492 | 4-May-15 |
| 16803 | 2 | 3 | 4 | | IV-1 | Pklr | 5313 | 17-May-15 | 17493 | 2 | 3 | 4 | IV-1 | Prss27 | 83886 | 4-May-15 |
| 16805 | 2 | 3 | 4 | | IV-1 | Pkmyt1 | 9088 | 4-May-15 | 17512 | 2 | 3 | 4 | IV-1 | Prss46 | 100287362 | 4-May-15 |
| 16810 | 2 | 3 | 4 | | IV-1 | Pknox2 | 63876 | 12-May-15 | 17517 | 2 | 3 | 4 | IV-1 | Prss53 | 339105 | 4-May-15 |
| 16811 | 2 | 3 | 4 | | IV-1 | Pkp3 | 8317 | 4-May-15 | 17530 | 2 | 3 | 4 | IV-1 | Psapl1 | 768239 | 4-May-15 |
| 16813 | 2 | 3 | 4 | | IV-1 | Pkp3 | 11187 | 4-May-15 | 17531 | 2 | 3 | 4 | IV-1 | Psat1 | 29968 | 12-May-15 |
| 16815 | 2 | 3 | 4 | | IV-1 | Pla1a | 51365 | 12-May-15 | 17532 | 2 | 3 | 4 | IV-1 | Psca | 8000 | 4-May-15 |
| 16817 | 2 | 3 | 4 | | IV-1 | Pla2g10os | | | 17548 | 2 | 3 | 4 | IV-1 | Psg25 | | |
| 16818 | 2 | 3 | 4 | | IV-1 | Pla2g12a | 81579 | 4-May-15 | 17595 | 2 | 3 | 4 | IV-1 | Psme1 | 5720 | 4-May-15 |
| 16825 | 2 | 3 | 4 | | IV-1 | Pla2g2d | 26279 | 12-May-15 | 17605 | 2 | 3 | 4 | IV-1 | Psmg4 | 389362 | 4-May-15 |

Fig.22 - 34

| | | | | | | | | | | | | | | | |
|---|---|---|---|---|---|---|---|---|---|---|---|---|---|---|---|
| 17612 | 2 | 3 | 4 | | IV-1 | Pstpip1 | 9051 | 12-May-15 | 18250 | 2 | 3 | 4 | | IV-1 | Rhebl1 | 121268 | 12-May-15 |
| 17620 | 2 | 3 | 4 | | IV-1 | Ptcd2 | 79810 | 4-May-15 | 18252 | 2 | 3 | 4 | | IV-1 | Rho | 6010 | 7-Jun-15 |
| 17622 | 2 | 3 | 4 | | IV-1 | Ptch1 | 5727 | 23-May-15 | 18259 | 2 | 3 | 4 | | IV-1 | Rhod | 29984 | 4-May-15 |
| 17630 | 2 | 3 | 4 | | IV-1 | Ptdss2 | 81490 | 12-May-15 | 18267 | 2 | 3 | 4 | | IV-1 | Rhou | 58480 | 4-May-15 |
| 17632 | 2 | 3 | 4 | | IV-1 | Pter | 9317 | 4-May-15 | 18268 | 2 | 3 | 4 | | IV-1 | Rhov | 171177 | 4-May-15 |
| 17639 | 2 | 3 | 4 | | IV-1 | Ptger3 | 5733 | 12-May-15 | 18301 | 2 | 3 | 4 | | IV-1 | Rhpn2 | 85415 | 4-May-15 |
| 17641 | 2 | 3 | 4 | | IV-1 | Ptges | 9536 | 12-May-15 | 18311 | 2 | 3 | 4 | | IV-1 | Rilp | 83547 | 7-Jun-15 |
| 17644 | 2 | 3 | 4 | | IV-1 | Ptges3l | 100885 848 | 4-May-15 | 18312 | 2 | 3 | 4 | | IV-1 | Rilpl1 | 353116 | 4-May-15 |
| 17648 | 2 | 3 | 4 | | IV-1 | Ptgis | 5740 | 12-May-15 | 18321 | 2 | 3 | 4 | | IV-1 | Rims4 | 140730 | 4-May-15 |
| 17655 | 2 | 3 | 4 | | IV-1 | Pth1r | 5745 | 12-May-15 | 18323 | 2 | 3 | 4 | | IV-1 | Rin2 | 54453 | 14-May-15 |
| 17658 | 2 | 3 | 4 | | IV-1 | Pthlh | 5744 | 12-May-15 | 18334 | 2 | 3 | 4 | | IV-1 | Ripk4 | 54101 | 10-May-15 |
| 17661 | 2 | 3 | 4 | | IV-1 | Ptk6 | 5753 | 12-May-15 | 18352 | 2 | 3 | 4 | | IV-1 | Rmnd1 | 55005 | 4-May-15 |
| 17669 | 2 | 3 | 4 | | IV-1 | Ptp4a3 | 11156 | 24-May-15 | 18365 | 2 | 3 | 4 | | IV-1 | Rnase2b | | |
| 17671 | 2 | 3 | 4 | | IV-1 | Ptpla | 9200 | 12-May-15 | 18366 | 2 | 3 | 4 | | IV-1 | Rnase4 | 6038 | 7-Jun-15 |
| 17679 | 2 | 3 | 4 | | IV-1 | Ptpn13 | 5783 | 12-May-15 | 18378 | 2 | 3 | 4 | | IV-1 | Rnd2 | 8153 | 4-May-15 |
| 17685 | 2 | 3 | 4 | | IV-1 | Ptpn22 | 26191 | 17-May-15 | 18392 | 2 | 3 | 4 | | IV-1 | Rnf125 | 54941 | 23-May-15 |
| 17687 | 2 | 3 | 4 | | IV-1 | Ptpn3 | 5774 | 4-May-15 | 18406 | 2 | 3 | 4 | | IV-1 | Rnf145 | 153830 | 4-May-15 |
| 17699 | 2 | 3 | 4 | | IV-1 | PtprF | 5792 | 4-May-15 | 18412 | 2 | 3 | 4 | | IV-1 | Rnf152 | 220441 | 4-May-15 |
| 17717 | 2 | 3 | 4 | | IV-1 | Ptrh1 | 138428 | 4-May-15 | 18413 | 2 | 3 | 4 | | IV-1 | Rnf157 | 114804 | 4-May-15 |
| 17740 | 2 | 3 | 4 | | IV-1 | Pvrl2 | 5819 | 12-May-15 | 18422 | 2 | 3 | 4 | | IV-1 | Rnf181 | 51255 | 23-May-15 |
| 17749 | 2 | 3 | 4 | | IV-1 | Pxdn | 7837 | 4-May-15 | 18423 | 2 | 3 | 4 | | IV-1 | Rnf182 | 221687 | 4-May-15 |
| 17751 | 2 | 3 | 4 | | IV-1 | Pxmp2 | 5827 | 12-May-15 | 18433 | 2 | 3 | 4 | | IV-1 | Rnf208 | 727800 | 4-May-15 |
| 17763 | 2 | 3 | 4 | | IV-1 | Pygl | 5836 | 23-May-15 | 18437 | 2 | 3 | 4 | | IV-1 | Rnf217 | 154214 | 4-May-15 |
| 17764 | 2 | 3 | 4 | | IV-1 | Pygm | 5837 | 23-May-15 | 18443 | 2 | 3 | 4 | | IV-1 | Rnf24 | 11237 | 2-Jun-15 |
| 17765 | 2 | 3 | 4 | | IV-1 | Pygo1 | 26108 | 4-May-15 | 18486 | 2 | 3 | 4 | | IV-1 | Ropn1l | 83853 | 4-May-15 |
| 17776 | 2 | 3 | 4 | | IV-1 | Qpct | 25797 | 4-May-15 | 18491 | 2 | 3 | 4 | | IV-1 | Rorc | 6097 | 4-May-15 |
| 17779 | 2 | 3 | 4 | | IV-1 | Qrfp | 347148 | 4-May-15 | 18492 | 2 | 3 | 4 | | IV-1 | Ros1 | 6098 | 12-May-15 |
| 17786 | 2 | 3 | 4 | | IV-1 | Qsox2 | 169714 | 4-May-15 | 18507 | 2 | 3 | 4 | | IV-1 | Rpf2 | 84154 | 4-May-15 |
| 17812 | 2 | 3 | 4 | | IV-1 | Rab17 | 64284 | 4-May-15 | 18518 | 2 | 3 | 4 | | IV-1 | Rpl12 | 6136 | 12-May-15 |
| 17816 | 2 | 3 | 4 | | IV-1 | Rab20 | 55647 | 4-May-15 | 18524 | 2 | 3 | 4 | | IV-1 | Rpl17 | 6139 | 7-Jun-15 |
| 17823 | 2 | 3 | 4 | | IV-1 | Rab26os | | | 18537 | 2 | 3 | 4 | | IV-1 | Rpl28 | 6158 | 3-May-15 |
| 17834 | 2 | 3 | 4 | | IV-1 | Rab34 | 83871 | 4-May-15 | 18540 | 2 | 3 | 4 | | IV-1 | Rpl30 | 6156 | 4-May-15 |
| 17838 | 2 | 3 | 4 | | IV-1 | Rab38 | 23682 | 4-May-15 | 18544 | 2 | 3 | 4 | | IV-1 | Rpl34 | 6164 | 4-May-15 |
| 17840 | 2 | 3 | 4 | | IV-1 | Rab39b | 116442 | 4-May-15 | 18545 | 2 | 3 | 4 | | IV-1 | Rpl34-ps1 | | |
| 17848 | 2 | 3 | 4 | | IV-1 | Rab3ip | 117177 | 4-May-15 | 18547 | 2 | 3 | 4 | | IV-1 | Rpl35a | 6165 | 2-Jun-15 |
| 17851 | 2 | 3 | 4 | | IV-1 | Rab42 | 115273 | 4-May-15 | 18548 | 2 | 3 | 4 | | IV-1 | Rpl36 | 25873 | 12-May-15 |
| 17884 | 2 | 3 | 4 | | IV-1 | Rab4a | 5867 | 21-May-15 | 18549 | 2 | 3 | 4 | | IV-1 | Rpl36a | 6173 | 7-Jun-15 |
| 17903 | 2 | 3 | 4 | | IV-1 | Rad9b | 144715 | 4-May-15 | 18551 | 2 | 3 | 4 | | IV-1 | Rpl37 | 6167 | 4-May-15 |
| 17916 | 2 | 3 | 4 | | IV-1 | Rai2 | 10742 | 4-May-15 | 18552 | 2 | 3 | 4 | | IV-1 | Rpl37a | 6168 | 4-May-15 |
| 17953 | 2 | 3 | 4 | | IV-1 | Rapgef4 | 11069 | 4-May-15 | 18568 | 2 | 3 | 4 | | IV-1 | Rplp2 | 6181 | 12-May-15 |
| 17954 | 2 | 3 | 4 | | IV-1 | Rapgef5 | 9771 | 4-May-15 | 18573 | 2 | 3 | 4 | | IV-1 | Rpp21 | 79897 | 4-May-15 |
| 17958 | 2 | 3 | 4 | | IV-1 | Rapsn | 5913 | 12-May-15 | 18576 | 2 | 3 | 4 | | IV-1 | Rps30 | 10556 | 4-May-15 |
| 17963 | 2 | 3 | 4 | | IV-1 | Rarres2 | 5919 | 4-May-15 | 18580 | 2 | 3 | 4 | | IV-1 | Rprd1a | 55197 | 12-May-15 |
| 17974 | 2 | 3 | 4 | | IV-1 | Rasd2 | 23551 | 4-May-15 | 18587 | 2 | 3 | 4 | | IV-1 | Rpml | 388394 | 4-May-15 |
| 17975 | 2 | 3 | 4 | | IV-1 | Rasef | 158158 | 14-May-15 | 18588 | 2 | 3 | 4 | | IV-1 | Rps10 | 6204 | 22-May-15 |
| 17977 | 2 | 3 | 4 | | IV-1 | Rasgef1b | 153020 | 4-May-15 | 18589 | 2 | 3 | 4 | | IV-1 | Rps11 | 6205 | 4-May-15 |
| 17988 | 2 | 3 | 4 | | IV-1 | Rasl11a | 387496 | 4-May-15 | 18590 | 2 | 3 | 4 | | IV-1 | Rps12 | 6206 | 7-Jun-15 |
| 17989 | 2 | 3 | 4 | | IV-1 | Rasl11b | 65997 | 4-May-15 | 18598 | 2 | 3 | 4 | | IV-1 | Rps17 | 6218 | 23-May-15 |
| 17993 | 2 | 3 | 4 | | IV-1 | Rassf10 | 644943 | 4-May-15 | 18599 | 2 | 3 | 4 | | IV-1 | Rps18 | 6222 | 7-Jun-15 |
| 17998 | 2 | 3 | 4 | | IV-1 | Rassf6 | 166824 | 4-May-15 | 18608 | 2 | 3 | 4 | | IV-1 | Rps25 | 6230 | 4-May-15 |
| 17999 | 2 | 3 | 4 | | IV-1 | Rassf7 | 8045 | 4-May-15 | 18609 | 2 | 3 | 4 | | IV-1 | Rps26 | 6231 | 7-Jun-15 |
| 18000 | 2 | 3 | 4 | | IV-1 | Rassf8 | 11228 | 4-May-15 | 18610 | 2 | 3 | 4 | | IV-1 | Rps27 | 6232 | 17-May-15 |
| 18001 | 2 | 3 | 4 | | IV-1 | Rassf9 | 9182 | 4-May-15 | 18614 | 2 | 3 | 4 | | IV-1 | Rps28 | 6234 | 28-May-15 |
| 18021 | 2 | 3 | 4 | | IV-1 | Rbfox3 | 146713 | 4-May-15 | 18615 | 2 | 3 | 4 | | IV-1 | Rps29 | 6235 | 4-May-15 |
| 18031 | 2 | 3 | 4 | | IV-1 | Rbm14-rbm4 | 100526 737 | 4-May-15 | 18633 | 2 | 3 | 4 | | IV-1 | Rps8 | 6202 | 4-May-15 |
| 18037 | 2 | 3 | 4 | | IV-1 | Rbm20 | 282996 | 23-May-15 | 18644 | 2 | 3 | 4 | | IV-1 | Rrad | 6236 | 4-May-15 |
| 18048 | 2 | 3 | 4 | | IV-1 | Rbm38 | 55544 | 4-May-15 | 18646 | 2 | 3 | 4 | | IV-1 | Rragb | 10325 | 4-May-15 |
| 18050 | 2 | 3 | 4 | | IV-1 | Rbm3os | | | 18648 | 2 | 3 | 4 | | IV-1 | Rragd | 58528 | 4-May-15 |
| 18074 | 2 | 3 | 4 | | IV-1 | Rbp1 | 5947 | 7-Jun-15 | 18655 | 2 | 3 | 4 | | IV-1 | Rrm2 | 6241 | 4-May-15 |
| 18075 | 2 | 3 | 4 | | IV-1 | Rbp2 | 5948 | 7-Jun-15 | 18670 | 2 | 3 | 4 | | IV-1 | Rsad2 | 91543 | 4-May-15 |
| 18077 | 2 | 3 | 4 | | IV-1 | Rbp4 | 5950 | 7-Jun-15 | 18685 | 2 | 3 | 4 | | IV-1 | Rsph9 | 221421 | 23-May-15 |
| 18078 | 2 | 3 | 4 | | IV-1 | Rbp7 | 116362 | 30-Apr-15 | 18711 | 2 | 3 | 4 | | IV-1 | Rtn4rl1 | 146760 | 4-May-15 |
| 18087 | 2 | 3 | 4 | | IV-1 | Rcan2 | 10231 | 4-May-15 | 18712 | 2 | 3 | 4 | | IV-1 | Rtn4rl2 | 349687 | 4-May-15 |
| 18097 | 2 | 3 | 4 | | IV-1 | Rcn1 | 5954 | 13-Jun-15 | 18722 | 2 | 3 | 4 | | IV-1 | Rufy4 | 285180 | 4-May-15 |
| 18100 | 2 | 3 | 4 | | IV-1 | Rcor1 | 23186 | 7-Jun-15 | 18723 | 2 | 3 | 4 | | IV-1 | Rundc1 | 146923 | 12-May-15 |
| 18103 | 2 | 3 | 4 | | IV-1 | Rcsd1 | 92241 | 23-May-15 | 18726 | 2 | 3 | 4 | | IV-1 | Runx1 | 861 | 21-May-15 |
| 18107 | 2 | 3 | 4 | | IV-1 | Rdh1 | 5959 | 4-May-15 | 18729 | 2 | 3 | 4 | | IV-1 | Runx3 | 864 | 21-May-15 |
| 18109 | 2 | 3 | 4 | | IV-1 | Rdh11 | 51109 | 4-May-15 | 18731 | 2 | 3 | 4 | | IV-1 | Rusc2 | 9853 | 4-May-15 |
| 18110 | 2 | 3 | 4 | | IV-1 | Rdh12 | 145226 | 23-May-15 | 18745 | 2 | 3 | 4 | | IV-1 | Rxrg | 6258 | 4-May-15 |
| 18113 | 2 | 3 | 4 | | IV-1 | Rdh16 | 8608 | 12-May-15 | 18752 | 2 | 3 | 4 | | IV-1 | S100a10 | 6281 | 12-May-15 |
| 18114 | 2 | 3 | 4 | | IV-1 | Rdh18-ps | | | 18755 | 2 | 3 | 4 | | IV-1 | S100a14 | 57402 | 7-Jun-15 |
| 18119 | 2 | 3 | 4 | | IV-1 | Rdh9 | | | 18759 | 2 | 3 | 4 | | IV-1 | S100a4 | 6275 | 17-May-15 |
| 18122 | 2 | 3 | 4 | | IV-1 | Rec8 | 9985 | 4-May-15 | 18767 | 2 | 3 | 4 | | IV-1 | S100pbp | 64766 | 4-May-15 |
| 18127 | 2 | 3 | 4 | | IV-1 | Redrum | | | 18785 | 2 | 3 | 4 | | IV-1 | Sag | 6295 | 7-Jun-15 |
| 18128 | 2 | 3 | 4 | | IV-1 | Reep1 | 65055 | 4-May-15 | 18786 | 2 | 3 | 4 | | IV-1 | Sall1 | 6299 | 23-May-15 |
| 18133 | 2 | 3 | 4 | | IV-1 | Reep6 | 92840 | 4-May-15 | 18791 | 2 | 3 | 4 | | IV-1 | Samd10 | 140700 | 4-May-15 |
| 18136 | 2 | 3 | 4 | | IV-1 | Reg3a | 5068 | 12-May-15 | 18792 | 2 | 3 | 4 | | IV-1 | Samd11 | | |
| 18138 | 2 | 3 | 4 | | IV-1 | Reg3d | | | 18794 | 2 | 3 | 4 | | IV-1 | Samd14 | 201191 | 4-May-15 |
| 18148 | 2 | 3 | 4 | | IV-1 | Rem1 | 28954 | 4-May-15 | 18797 | 2 | 3 | 4 | | IV-1 | Samd4 | 23034 | 4-May-15 |
| 18152 | 2 | 3 | 4 | | IV-1 | Renbp | 5973 | 4-May-15 | 18799 | 2 | 3 | 4 | | IV-1 | Samd5 | 389432 | 12-May-15 |
| 18159 | 2 | 3 | 4 | | IV-1 | Rerg | 85004 | 4-May-15 | 18811 | 2 | 3 | 4 | | IV-1 | Sap25 | 100316 904 | 4-May-15 |
| 18161 | 2 | 3 | 4 | | IV-1 | Resp18 | 389075 | 4-May-15 | 18815 | 2 | 3 | 4 | | IV-1 | Saprd1 | 401251 | 4-May-15 |
| 18164 | 2 | 3 | 4 | | IV-1 | Retn | 56729 | 17-May-15 | 18818 | 2 | 3 | 4 | | IV-1 | Sar1b | 51128 | 4-May-15 |
| 18165 | 2 | 3 | 4 | | IV-1 | Retnla | | | 18831 | 2 | 3 | 4 | | IV-1 | Satb1 | 6304 | 26-May-15 |
| 18167 | 2 | 3 | 4 | | IV-1 | Retnlg | | | 18841 | 2 | 3 | 4 | | IV-1 | Sbk3 | 100130 827 | 4-May-15 |
| 18168 | 2 | 3 | 4 | | IV-1 | Retsat | 54884 | 12-May-15 | 18846 | 2 | 3 | 4 | | IV-1 | Sbsn | 374897 | 4-May-15 |
| 18193 | 2 | 3 | 4 | | IV-1 | Rfx2 | 5990 | 4-May-15 | 18867 | 2 | 3 | 4 | | IV-1 | Scarf2 | 91179 | 21-May-15 |
| 18203 | 2 | 3 | 4 | | IV-1 | Rgag4 | 340526 | 4-May-15 | 18870 | 2 | 3 | 4 | | IV-1 | Scarna13 | 677768 | 4-May-15 |
| 18208 | 2 | 3 | 4 | | IV-1 | Rgma | 56963 | 4-May-15 | 18875 | 2 | 3 | 4 | | IV-1 | Scarna6 | 677772 | 4-May-15 |
| 18210 | 2 | 3 | 4 | | IV-1 | Rgn | 9104 | 4-May-15 | 18879 | 2 | 3 | 4 | | IV-1 | Scd1 | 6319 | 4-May-15 |
| 18213 | 2 | 3 | 4 | | IV-1 | Rgs1 | 5996 | 4-May-15 | 18883 | 2 | 3 | 4 | | IV-1 | Scel | 8796 | 4-May-15 |
| 18214 | 2 | 3 | 4 | | IV-1 | Rgs10 | 6001 | 4-May-15 | 18888 | 2 | 3 | 4 | | IV-1 | Scg5 | 6447 | 12-May-15 |
| 18223 | 2 | 3 | 4 | | IV-1 | Rgs2 | 5997 | 7-Jun-15 | 18899 | 2 | 3 | 4 | | IV-1 | Scgb1c1 | 147199 | 4-May-15 |
| 18229 | 2 | 3 | 4 | | IV-1 | Rgs5 | 8490 | 12-May-15 | 18907 | 2 | 3 | 4 | | IV-1 | Scgb2b24 | | |
| 18241 | 2 | 3 | 4 | | IV-1 | Rhbdf1 | 64285 | 4-May-15 | 18908 | 2 | 3 | 4 | | IV-1 | Scgb2b26 | | |
| 18246 | 2 | 3 | 4 | | IV-1 | Rhbg | 57127 | 12-May-15 | 18915 | 2 | 3 | 4 | | IV-1 | Schip1 | 29970 | 4-May-15 |

Fig.22 - 35

| | | | | | | | | | | | | | | | | |
|---|---|---|---|---|---|---|---|---|---|---|---|---|---|---|---|---|
| 18916 | 2 | 3 | 4 | | IV-1 | Scimp | 388325 | 4-May-15 | 19402 | 2 | 3 | 4 | | IV-1 | Slamf7 | 57823 | 4-May-15 |
| 18917 | 2 | 3 | 4 | | IV-1 | Scin | 85477 | 4-May-15 | 19406 | 2 | 3 | 4 | | IV-1 | Slc10a1 | 6554 | 17-May-15 |
| 18922 | 2 | 3 | 4 | | IV-1 | Scml4 | 256380 | 12-May-15 | 19407 | 2 | 3 | 4 | | IV-1 | Slc10a2 | 6555 | 12-May-15 |
| 18925 | 2 | 3 | 4 | | IV-1 | Scn1a | 6323 | 22-May-15 | 19411 | 2 | 3 | 4 | | IV-1 | Slc10a5 | 347051 | 4-May-15 |
| 18926 | 2 | 3 | 4 | | IV-1 | Scn1b | 6324 | 23-May-15 | 19412 | 2 | 3 | 4 | | IV-1 | Slc10a6 | 345274 | 4-May-15 |
| 18928 | 2 | 3 | 4 | | IV-1 | Scn2b | 6327 | 12-May-15 | 19414 | 2 | 3 | 4 | | IV-1 | Slc11a1 | 6556 | 12-May-15 |
| 18931 | 2 | 3 | 4 | | IV-1 | Scn4a | 6329 | 22-May-15 | 19425 | 2 | 3 | 4 | | IV-1 | Slc13a1 | 6561 | 4-May-15 |
| 18938 | 2 | 3 | 4 | | IV-1 | Scnn1a | 6337 | 12-May-15 | 19427 | 2 | 3 | 4 | | IV-1 | Slc13a2os | | |
| 18939 | 2 | 3 | 4 | | IV-1 | Scnn1b | 6338 | 12-May-15 | 19432 | 2 | 3 | 4 | | IV-1 | Slc14a2 | 8170 | 3-May-15 |
| 18940 | 2 | 3 | 4 | | IV-1 | Scnn1g | 6340 | 17-May-15 | 19433 | 2 | 3 | 4 | | IV-1 | Slc15a1 | 6564 | 12-May-15 |
| 18956 | 2 | 3 | 4 | | IV-1 | Sctr | 6344 | 4-May-15 | 19434 | 2 | 3 | 4 | | IV-1 | Slc15a2 | 6565 | 4-May-15 |
| 18957 | 2 | 3 | 4 | | IV-1 | Scube1 | 80274 | 4-May-15 | 19435 | 2 | 3 | 4 | | IV-1 | Slc15a3 | 51296 | 4-May-15 |
| 18965 | 2 | 3 | 4 | | IV-1 | Sdc1 | 6382 | 17-May-15 | 19439 | 2 | 3 | 4 | | IV-1 | Slc16a10 | 117247 | 4-May-15 |
| 18968 | 2 | 3 | 4 | | IV-1 | Sdc4 | 6385 | 3-May-15 | 19440 | 2 | 3 | 4 | | IV-1 | Slc16a11 | 162515 | 4-May-15 |
| 18970 | 2 | 3 | 4 | | IV-1 | Sdcbp2 | 27111 | 4-May-15 | 19441 | 2 | 3 | 4 | | IV-1 | Slc16a12 | 387700 | 4-May-15 |
| 18975 | 2 | 3 | 4 | | IV-1 | Sdf2l1 | 23753 | 4-May-15 | 19442 | 2 | 3 | 4 | | IV-1 | Slc16a13 | 201232 | 4-May-15 |
| 18987 | 2 | 3 | 4 | | IV-1 | Sdr16c6 | 442388 | 4-May-15 | 19444 | 2 | 3 | 4 | | IV-1 | Slc16a2 | 6567 | 23-May-15 |
| 18992 | 2 | 3 | 4 | | IV-1 | Sdsl | 113675 | 12-May-15 | 19447 | 2 | 3 | 4 | | IV-1 | Slc16a5 | 9121 | 4-May-15 |
| 18996 | 2 | 3 | 4 | | IV-1 | Sec11c | 90701 | 14-May-15 | 19448 | 2 | 3 | 4 | | IV-1 | Slc16a6 | 9120 | 20-May-15 |
| 18999 | 2 | 3 | 4 | | IV-1 | Sec14l2 | 23541 | 12-May-15 | 19449 | 2 | 3 | 4 | | IV-1 | Slc16a7 | 9194 | 4-May-15 |
| 19006 | 2 | 3 | 4 | | IV-1 | Sec14l3 | 266629 | 4-May-15 | 19452 | 2 | 3 | 4 | | IV-1 | Slc17a1 | 6568 | 12-May-15 |
| 19014 | 2 | 3 | 4 | | IV-1 | Sec24d | 9871 | 17-May-15 | 19455 | 2 | 3 | 4 | | IV-1 | Slc17a4 | 10050 | 4-May-15 |
| 19030 | 2 | 3 | 4 | | IV-1 | Sel1l3 | 23231 | 12-May-15 | 19465 | 2 | 3 | 4 | | IV-1 | Slc19a1 | 6573 | 4-May-15 |
| 19031 | 2 | 3 | 4 | | IV-1 | Sele | 6401 | 17-May-15 | 19467 | 2 | 3 | 4 | | IV-1 | Slc19a3 | 80704 | 23-May-15 |
| 19032 | 2 | 3 | 4 | | IV-1 | Selenbp1 | 8991 | 4-May-15 | 19470 | 2 | 3 | 4 | | IV-1 | Slc1a3 | 6507 | 23-May-15 |
| 19035 | 2 | 3 | 4 | | IV-1 | Sell | 6402 | 17-May-15 | 19471 | 2 | 3 | 4 | | IV-1 | Slc1a4 | 6509 | 28-May-15 |
| 19043 | 2 | 3 | 4 | | IV-1 | Sema3c | 10512 | 31-May-15 | 19472 | 2 | 3 | 4 | | IV-1 | Slc1a5 | 6510 | 4-May-15 |
| 19046 | 2 | 3 | 4 | | IV-1 | Sema3f | 6405 | 4-May-15 | 19475 | 2 | 3 | 4 | | IV-1 | Slc20a1 | 6574 | 4-May-15 |
| 19053 | 2 | 3 | 4 | | IV-1 | Sema4g | 57715 | 4-May-15 | 19484 | 2 | 3 | 4 | | IV-1 | Slc22a17 | 51310 | 1-Jun-15 |
| 19057 | 2 | 3 | 4 | | IV-1 | Sema6b | 10501 | 4-May-15 | 19498 | 2 | 3 | 4 | | IV-1 | Slc22a4 | 6583 | 12-May-15 |
| 19071 | 2 | 3 | 4 | | IV-1 | Sepp1 | 6414 | 3-May-15 | 19502 | 2 | 3 | 4 | | IV-1 | Slc22a8 | 9376 | 12-May-15 |
| 19072 | 2 | 3 | 4 | | IV-1 | Sepsecs | 51091 | 4-May-15 | 19505 | 2 | 3 | 4 | | IV-1 | Slc23a3 | 151295 | 4-May-15 |
| 19111 | 2 | 3 | 4 | | IV-1 | Serpina3b | | | 19509 | 2 | 3 | 4 | | IV-1 | Slc24a4 | 123041 | 4-May-15 |
| 19112 | 2 | 3 | 4 | | IV-1 | Serpina3c | | | 19510 | 2 | 3 | 4 | | IV-1 | Slc24a5 | 283652 | 4-May-15 |
| 19113 | 2 | 3 | 4 | | IV-1 | Serpina3f | | | 19514 | 2 | 3 | 4 | | IV-1 | Slc25a12 | 8604 | 4-May-15 |
| 19114 | 2 | 3 | 4 | | IV-1 | Serpina3g | | | 19515 | 2 | 3 | 4 | | IV-1 | Slc25a13 | 10165 | 23-May-15 |
| 19117 | 2 | 3 | 4 | | IV-1 | Serpina3j | | | 19524 | 2 | 3 | 4 | | IV-1 | Slc25a21 | 89874 | 4-May-15 |
| 19119 | 2 | 3 | 4 | | IV-1 | Serpina3m | | | 19527 | 2 | 3 | 4 | | IV-1 | Slc25a24 | 29957 | 4-May-15 |
| 19120 | 2 | 3 | 4 | | IV-1 | Serpina3n | | | 19528 | 2 | 3 | 4 | | IV-1 | Slc25a25 | 114789 | 4-May-15 |
| 19124 | 2 | 3 | 4 | | IV-1 | Serpina7 | 6906 | 4-May-15 | 19532 | 2 | 3 | 4 | | IV-1 | Slc25a29 | 123096 | 4-May-15 |
| 19127 | 2 | 3 | 4 | | IV-1 | Serpinb11 | 89778 | 12-May-15 | 19534 | 2 | 3 | 4 | | IV-1 | Slc25a30 | 253512 | 4-May-15 |
| 19128 | 2 | 3 | 4 | | IV-1 | Serpinb12 | 89777 | 20-May-15 | 19537 | 2 | 3 | 4 | | IV-1 | Slc25a33 | 84275 | 4-May-15 |
| 19130 | 2 | 3 | 4 | | IV-1 | Serpinb1a | | | 19541 | 2 | 3 | 4 | | IV-1 | Slc25a37 | 51312 | 4-May-15 |
| 19133 | 2 | 3 | 4 | | IV-1 | Serpinb2 | 5055 | 17-May-15 | 19544 | 2 | 3 | 4 | | IV-1 | Slc25a4 | 291 | 4-May-15 |
| 19136 | 2 | 3 | 4 | | IV-1 | Serpinb3c | | | 19553 | 2 | 3 | 4 | | IV-1 | Slc25a48 | 153328 | 4-May-15 |
| 19139 | 2 | 3 | 4 | | IV-1 | Serpinb6a | | | 19560 | 2 | 3 | 4 | | IV-1 | Slc26a11 | 284129 | 4-May-15 |
| 19154 | 2 | 3 | 4 | | IV-1 | Serpind1 | 3053 | 4-May-15 | 19561 | 2 | 3 | 4 | | IV-1 | Slc26a2 | 1836 | 23-May-15 |
| 19155 | 2 | 3 | 4 | | IV-1 | Serpine1 | 5054 | 24-May-15 | 19566 | 2 | 3 | 4 | | IV-1 | Slc26a9 | 115019 | 4-May-15 |
| 19156 | 2 | 3 | 4 | | IV-1 | Serpine2 | 5270 | 12-May-15 | 19569 | 2 | 3 | 4 | | IV-1 | Slc27a1 | 376497 | 4-May-15 |
| 19157 | 2 | 3 | 4 | | IV-1 | Serpine3 | 647174 | 4-May-15 | 19570 | 2 | 3 | 4 | | IV-1 | Slc27a2 | 11001 | 4-May-15 |
| 19163 | 2 | 3 | 4 | | IV-1 | Serpini2 | 5276 | 4-May-15 | 19576 | 2 | 3 | 4 | | IV-1 | Slc28a2 | 9153 | 4-May-15 |
| 19169 | 2 | 3 | 4 | | IV-1 | Sesn1 | 27244 | 4-May-15 | 19577 | 2 | 3 | 4 | | IV-1 | Slc28a3 | 64078 | 4-May-15 |
| 19171 | 2 | 3 | 4 | | IV-1 | Sesn3 | 143686 | 4-May-15 | 19584 | 2 | 3 | 4 | | IV-1 | Slc2a12 | 154091 | 17-May-15 |
| 19174 | 2 | 3 | 4 | | IV-1 | Setbp1 | 26040 | 17-May-15 | 19588 | 2 | 3 | 4 | | IV-1 | Slc2a4 | 6517 | 17-May-15 |
| 19179 | 2 | 3 | 4 | | IV-1 | Setd4 | 54093 | 4-May-15 | 19590 | 2 | 3 | 4 | | IV-1 | Slc2a5 | 6518 | 12-May-15 |
| 19204 | 2 | 3 | 4 | | IV-1 | Sfn | 2810 | 7-Jun-15 | 19592 | 2 | 3 | 4 | | IV-1 | Slc2a7 | 155184 | 4-May-15 |
| 19209 | 2 | 3 | 4 | | IV-1 | Sfrp4 | 6424 | 17-May-15 | 19597 | 2 | 3 | 4 | | IV-1 | Slc30a2 | 7780 | 4-May-15 |
| 19218 | 2 | 3 | 4 | | IV-1 | Sftpc | 6440 | 23-May-15 | 19598 | 2 | 3 | 4 | | IV-1 | Slc30a3 | 7781 | 4-May-15 |
| 19226 | 2 | 3 | 4 | | IV-1 | Sgcb | 6443 | 23-May-15 | 19628 | 2 | 3 | 4 | | IV-1 | Slc35e3 | 55508 | 4-May-15 |
| 19228 | 2 | 3 | 4 | | IV-1 | Sgce | 8910 | 23-May-15 | 19629 | 2 | 3 | 4 | | IV-1 | Slc35e4 | 339665 | 4-May-15 |
| 19232 | 2 | 3 | 4 | | IV-1 | Sgk1 | 6446 | 21-May-15 | 19636 | 2 | 3 | 4 | | IV-1 | Slc35g1 | 159371 | 4-May-15 |
| 19233 | 2 | 3 | 4 | | IV-1 | Sgk2 | 10110 | 7-Jun-15 | 19641 | 2 | 3 | 4 | | IV-1 | Slc36a2 | 153201 | 4-May-15 |
| 19236 | 2 | 3 | 4 | | IV-1 | Sgms2 | 166929 | 4-May-15 | 19643 | 2 | 3 | 4 | | IV-1 | Slc36a4 | 120103 | 28-May-15 |
| 19240 | 2 | 3 | 4 | | IV-1 | Sgpp1 | 81537 | 4-May-15 | 19644 | 2 | 3 | 4 | | IV-1 | Slc37a1 | 54020 | 4-May-15 |
| 19241 | 2 | 3 | 4 | | IV-1 | Sgpp2 | 130367 | 4-May-15 | 19645 | 2 | 3 | 4 | | IV-1 | Slc37a2 | 219855 | 12-May-15 |
| 19249 | 2 | 3 | 4 | | IV-1 | Sh2b2 | 10603 | 21-May-15 | 19653 | 2 | 3 | 4 | | IV-1 | Slc38a4 | 55089 | 4-May-15 |
| 19256 | 2 | 3 | 4 | | IV-1 | Sh2d4a | 63898 | 4-May-15 | 19669 | 2 | 3 | 4 | | IV-1 | Slc39a6 | 25800 | 12-May-15 |
| 19258 | 2 | 3 | 4 | | IV-1 | Sh2d5 | 400745 | 4-May-15 | 19671 | 2 | 3 | 4 | | IV-1 | Slc39a8 | 64116 | 4-May-15 |
| 19259 | 2 | 3 | 4 | | IV-1 | Sh2d7 | 646892 | 4-May-15 | 19677 | 2 | 3 | 4 | | IV-1 | Slc41a2 | 84102 | 4-May-15 |
| 19260 | 2 | 3 | 4 | | IV-1 | Sh3bgr | 6450 | 7-Jun-15 | 19678 | 2 | 3 | 4 | | IV-1 | Slc41a3 | 54946 | 4-May-15 |
| 19273 | 2 | 3 | 4 | | IV-1 | Sh3gl3 | 6457 | 4-May-15 | 19679 | 2 | 3 | 4 | | IV-1 | Slc43a1 | 8601 | 4-May-15 |
| 19280 | 2 | 3 | 4 | | IV-1 | Sh3rf2 | 153769 | 21-May-15 | 19685 | 2 | 3 | 4 | | IV-1 | Slc44a4 | 80736 | 4-May-15 |
| 19282 | 2 | 3 | 4 | | IV-1 | Sh3tc1 | 54436 | 4-May-15 | 19689 | 2 | 3 | 4 | | IV-1 | Slc45a3 | 85414 | 4-May-15 |
| 19283 | 2 | 3 | 4 | | IV-1 | Sh3tc2 | 79628 | 21-May-15 | 19691 | 2 | 3 | 4 | | IV-1 | Slc46a1 | 113235 | 23-May-15 |
| 19284 | 2 | 3 | 4 | | IV-1 | Sh3yl1 | 26751 | 12-May-15 | 19692 | 2 | 3 | 4 | | IV-1 | Slc46a2 | 57864 | 4-May-15 |
| 19286 | 2 | 3 | 4 | | IV-1 | Shank2 | 22941 | 23-May-15 | 19694 | 2 | 3 | 4 | | IV-1 | Slc47a1 | 55244 | 24-May-15 |
| 19289 | 2 | 3 | 4 | | IV-1 | Shb | 6461 | 4-May-15 | 19699 | 2 | 3 | 4 | | IV-1 | Slc4a11 | 83959 | 23-May-15 |
| 19299 | 2 | 3 | 4 | | IV-1 | Shf | 90525 | 21-May-15 | 19703 | 2 | 3 | 4 | | IV-1 | Slc4a4 | 8671 | 17-May-15 |
| 19301 | 2 | 3 | 4 | | IV-1 | Shh | 6469 | 24-May-15 | 19709 | 2 | 3 | 4 | | IV-1 | Slc51a | 200931 | 4-May-15 |
| 19302 | 2 | 3 | 4 | | IV-1 | Shisa2 | 387914 | 4-May-15 | 19712 | 2 | 3 | 4 | | IV-1 | Slc52a3 | 113278 | 4-May-15 |
| 19304 | 2 | 3 | 4 | | IV-1 | Shisa4 | 149345 | 4-May-15 | 19713 | 2 | 3 | 4 | | IV-1 | Slc5a1 | 6523 | 12-May-15 |
| 19316 | 2 | 3 | 4 | | IV-1 | Shq1 | 55164 | 3-May-15 | 19716 | 2 | 3 | 4 | | IV-1 | Slc5a12 | 159963 | 4-May-15 |
| 19317 | 2 | 3 | 4 | | IV-1 | Shroom1 | 134549 | 12-May-15 | 19718 | 2 | 3 | 4 | | IV-1 | Slc5a3 | 6526 | 12-May-15 |
| 19319 | 2 | 3 | 4 | | IV-1 | Shroom3 | 57619 | 21-May-15 | 19719 | 2 | 3 | 4 | | IV-1 | Slc5a4a | | |
| 19326 | 2 | 3 | 4 | | IV-1 | Sigirr | 59307 | 24-May-15 | 19722 | 2 | 3 | 4 | | IV-1 | Slc5a6 | 8884 | 12-May-15 |
| 19329 | 2 | 3 | 4 | | IV-1 | Siglec1 | 6614 | 4-May-15 | 19724 | 2 | 3 | 4 | | IV-1 | Slc5a8 | 160728 | 4-May-15 |
| 19330 | 2 | 3 | 4 | | IV-1 | Siglec15 | 284266 | 4-May-15 | 19731 | 2 | 3 | 4 | | IV-1 | Slc6a15 | 55117 | 14-May-15 |
| 19332 | 2 | 3 | 4 | | IV-1 | Siglece | | | 19732 | 2 | 3 | 4 | | IV-1 | Slc6a17 | 388662 | 17-May-15 |
| 19336 | 2 | 3 | 4 | | IV-1 | Sik1 | 150094 | 23-May-15 | 19733 | 2 | 3 | 4 | | IV-1 | Slc6a18 | 348932 | 4-May-15 |
| 19337 | 2 | 3 | 4 | | IV-1 | Sik2 | 23235 | 4-May-15 | 19734 | 2 | 3 | 4 | | IV-1 | Slc6a19 | 340024 | 4-May-15 |
| 19350 | 2 | 3 | 4 | | IV-1 | Sirpa | 140885 | 17-May-15 | 19736 | 2 | 3 | 4 | | IV-1 | Slc6a2 | 6530 | 12-May-15 |
| 19361 | 2 | 3 | 4 | | IV-1 | Sit3 | 27240 | 7-Jun-15 | 19740 | 2 | 3 | 4 | | IV-1 | Slc6a4 | 6532 | 17-May-15 |
| 19363 | 2 | 3 | 4 | | IV-1 | Six1 | 6495 | 31-May-15 | 19742 | 2 | 3 | 4 | | IV-1 | Slc6a6 | 6533 | 12-May-15 |
| 19368 | 2 | 3 | 4 | | IV-1 | Six5 | 147912 | 23-May-15 | 19744 | 2 | 3 | 4 | | IV-1 | Slc6a8 | 6535 | 23-May-15 |
| 19373 | 2 | 3 | 4 | | IV-1 | Skap1 | 8631 | 4-May-15 | 19745 | 2 | 3 | 4 | | IV-1 | Slc6a9 | 6536 | 4-May-15 |
| 19387 | 2 | 3 | 4 | | IV-1 | Skint8 | | | 19746 | 2 | 3 | 4 | | IV-1 | Slc7a1 | 6541 | 4-May-15 |
| 19395 | 2 | 3 | 4 | | IV-1 | Sla | 6503 | 7-Jun-15 | 19747 | 2 | 3 | 4 | | IV-1 | Slc7a10 | 56301 | 12-May-15 |

Fig.22 - 36

| | | | | | | | | | | | | | | |
|---|---|---|---|---|---|---|---|---|---|---|---|---|---|---|
| 19748 | 2 | 3 | 4 | | IV-1 | Slc7a11 | 23657 | 12-May-15 | 20374 | 2 | 3 | 4 | IV-1 | Spry1 | 10252 | 4-May-15 |
| 19753 | 2 | 3 | 4 | | IV-1 | Slc7a2 | 6542 | 4-May-15 | 20375 | 2 | 3 | 4 | IV-1 | Spry2 | 10253 | 17-May-15 |
| 19755 | 2 | 3 | 4 | | IV-1 | Slc7a4 | 6545 | 4-May-15 | 20396 | 2 | 3 | 4 | IV-1 | Sptssb | 165679 | 4-May-15 |
| 19764 | 2 | 3 | 4 | | IV-1 | Slc8a3 | 6547 | 4-May-15 | 20399 | 2 | 3 | 4 | IV-1 | Sqle | 6713 | 4-May-15 |
| 19767 | 2 | 3 | 4 | | IV-1 | Slc9a2 | 6549 | 12-May-15 | 20407 | 2 | 3 | 4 | IV-1 | Srd5a1 | 6715 | 12-May-15 |
| 19768 | 2 | 3 | 4 | | IV-1 | Slc9a3 | 6550 | 17-May-15 | 20417 | 2 | 3 | 4 | IV-1 | Srgap2 | 23380 | 7-Jun-15 |
| 19771 | 2 | 3 | 4 | | IV-1 | Slc9a4 | 389015 | 4-May-15 | 20428 | 2 | 3 | 4 | IV-1 | Srp54c | | |
| 19776 | 2 | 3 | 4 | | IV-1 | Slc9a9 | 285195 | 4-May-15 | 20434 | 2 | 3 | 4 | IV-1 | Srpk3 | 26576 | 4-May-15 |
| 19778 | 2 | 3 | 4 | | IV-1 | Slc9b2 | 133308 | 4-May-15 | 20461 | 2 | 3 | 4 | IV-1 | Ss18l1 | 26039 | 4-May-15 |
| 19782 | 2 | 3 | 4 | | IV-1 | Slco1a5 | | | 20482 | 2 | 3 | 4 | IV-1 | Sst | 6750 | 17-May-15 |
| 19788 | 2 | 3 | 4 | | IV-1 | Slco3a1 | 28232 | 12-May-15 | 20492 | 2 | 3 | 4 | IV-1 | Ssx2ip | 137178 | 4-May-15 |
| 19789 | 2 | 3 | 4 | | IV-1 | Slco4a1 | 28231 | 4-May-15 | 20496 | 2 | 3 | 4 | IV-1 | Ssxb2 | | |
| 19791 | 2 | 3 | 4 | | IV-1 | Slco5a1 | 81796 | 4-May-15 | 20505 | 2 | 3 | 4 | IV-1 | St3gal1 | 6482 | 12-May-15 |
| 19797 | 2 | 3 | 4 | | IV-1 | Slfn14 | 342618 | 4-May-15 | 20510 | 2 | 3 | 4 | IV-1 | St3gal6 | 10402 | 4-May-15 |
| 19798 | 2 | 3 | 4 | | IV-1 | Slfn2 | | | 20515 | 2 | 3 | 4 | IV-1 | St6galnac2 | 10610 | 4-May-15 |
| 19818 | 2 | 3 | 4 | | IV-1 | Slmo1 | 10650 | 12-May-15 | 20518 | 2 | 3 | 4 | IV-1 | St6galnac5 | 81849 | 4-May-15 |
| 19836 | 2 | 3 | 4 | | IV-1 | Smad6 | 4091 | 12-May-15 | 20527 | 2 | 3 | 4 | IV-1 | St8sia5 | 29906 | 12-May-15 |
| 19854 | 2 | 3 | 4 | | IV-1 | Smarcd3 | 6604 | 4-May-15 | 20528 | 2 | 3 | 4 | IV-1 | St8sia6 | 338586 | 4-May-15 |
| 19881 | 2 | 3 | 4 | | IV-1 | Smim1 | 388585 | 12-May-15 | 20530 | 2 | 3 | 4 | IV-1 | Stab2 | 55576 | 12-May-15 |
| 19890 | 2 | 3 | 4 | | IV-1 | Smim22 | 440335 | 12-May-15 | 20541 | 2 | 3 | 4 | IV-1 | Stamos | | |
| 19892 | 2 | 3 | 4 | | IV-1 | Smim24 | 284422 | 4-May-15 | 20542 | 2 | 3 | 4 | IV-1 | Stap1 | 26228 | 7-Jun-15 |
| 19893 | 2 | 3 | 4 | | IV-1 | Smim3 | 85027 | 4-May-15 | 20545 | 2 | 3 | 4 | IV-1 | Stard10 | 10809 | 12-May-15 |
| 19895 | 2 | 3 | 4 | | IV-1 | Smim5 | 643008 | 4-May-15 | 20564 | 2 | 3 | 4 | IV-1 | Stc1 | 6781 | 12-May-15 |
| 19914 | 2 | 3 | 4 | | IV-1 | Smpd3 | 55512 | 12-May-15 | 20567 | 2 | 3 | 4 | IV-1 | Steap2 | 261729 | 4-May-15 |
| 19918 | 2 | 3 | 4 | | IV-1 | Smpd3b | 27293 | 4-May-15 | 20568 | 2 | 3 | 4 | IV-1 | Steap3 | 55240 | 4-May-15 |
| 19936 | 2 | 3 | 4 | | IV-1 | Snai2 | 6591 | 1-Jun-15 | 20569 | 2 | 3 | 4 | IV-1 | Steap4 | 79689 | 4-May-15 |
| 19937 | 2 | 3 | 4 | | IV-1 | Snai3 | 333929 | 4-May-15 | 20571 | 2 | 3 | 4 | IV-1 | Stfa2 | | |
| 19942 | 2 | 3 | 4 | | IV-1 | Snap91 | 9892 | 4-May-15 | 20573 | 2 | 3 | 4 | IV-1 | Stfa3 | | |
| 19945 | 2 | 3 | 4 | | IV-1 | Snapc3 | 6619 | 4-May-15 | 20588 | 2 | 3 | 4 | IV-1 | Stk32a | 202374 | 28-May-15 |
| 19949 | 2 | 3 | 4 | | IV-1 | Snca | 6622 | 24-May-15 | 20601 | 2 | 3 | 4 | IV-1 | Stmn2 | 11075 | 4-May-15 |
| 19950 | 2 | 3 | 4 | | IV-1 | Sncaip | 9627 | 31-May-15 | 20609 | 2 | 3 | 4 | IV-1 | Ston1 | 11037 | 4-May-15 |
| 19952 | 2 | 3 | 4 | | IV-1 | Sncg | 6623 | 4-May-15 | 20624 | 2 | 3 | 4 | IV-1 | Strip2 | 57464 | 4-May-15 |
| 19957 | 2 | 3 | 4 | | IV-1 | Snhg10 | 283596 | 12-May-15 | 20671 | 2 | 3 | 4 | IV-1 | Sult1a1 | 6817 | 31-May-15 |
| 19958 | 2 | 3 | 4 | | IV-1 | Snhg11 | 128439 | 4-May-15 | 20674 | 2 | 3 | 4 | IV-1 | Sult1c2 | 6819 | 7-Jun-15 |
| 19959 | 2 | 3 | 4 | | IV-1 | Snhg12 | 85028 | 12-May-15 | 20684 | 2 | 3 | 4 | IV-1 | Sult2b1 | 6820 | 4-May-15 |
| 19961 | 2 | 3 | 4 | | IV-1 | Snhg3 | 8420 | 12-May-15 | 20698 | 2 | 3 | 4 | IV-1 | Suox | 6821 | 12-May-15 |
| 19963 | 2 | 3 | 4 | | IV-1 | Snhg5 | 387066 | 12-May-15 | 20711 | 2 | 3 | 4 | IV-1 | Susd1 | 64420 | 4-May-15 |
| 19964 | 2 | 3 | 4 | | IV-1 | Snhg6 | 641638 | 12-May-15 | 20712 | 2 | 3 | 4 | IV-1 | Susd2 | 56241 | 4-May-15 |
| 19967 | 2 | 3 | 4 | | IV-1 | Snhg9 | 735301 | 12-May-15 | 20730 | 2 | 3 | 4 | IV-1 | Svip | 258010 | 3-May-15 |
| 19969 | 2 | 3 | 4 | | IV-1 | Snn | 8303 | 4-May-15 | 20745 | 2 | 3 | 4 | IV-1 | Sybu | 55638 | 4-May-15 |
| 19976 | 2 | 3 | 4 | | IV-1 | Snora23 | 677808 | 4-May-15 | 20748 | 2 | 3 | 4 | IV-1 | Syce2 | 256126 | 4-May-15 |
| 20001 | 2 | 3 | 4 | | IV-1 | Snora74a | 26821 | 4-May-15 | 20765 | 2 | 3 | 4 | IV-1 | Sync | 81493 | 4-May-15 |
| 20023 | 2 | 3 | 4 | | IV-1 | Snord17 | 692086 | 4-May-15 | 20771 | 2 | 3 | 4 | IV-1 | Syne3 | 161176 | 4-May-15 |
| 20080 | 2 | 3 | 4 | | IV-1 | Snph | 9751 | 4-May-15 | 20772 | 2 | 3 | 4 | IV-1 | Syne4 | 163183 | 12-May-15 |
| 20085 | 2 | 3 | 4 | | IV-1 | Snrnp35 | 11066 | 4-May-15 | 20774 | 2 | 3 | 4 | IV-1 | Syngr1 | 9145 | 4-May-15 |
| 20090 | 2 | 3 | 4 | | IV-1 | Snrpa1 | 6627 | 2-Jun-15 | 20794 | 2 | 3 | 4 | IV-1 | Syt12 | 91683 | 7-Jun-15 |
| 20098 | 2 | 3 | 4 | | IV-1 | Snrpf | 6636 | 28-May-15 | 20801 | 2 | 3 | 4 | IV-1 | Syt3 | 84258 | 4-May-15 |
| 20099 | 2 | 3 | 4 | | IV-1 | Snrpg | 6637 | 4-May-15 | 20808 | 2 | 3 | 4 | IV-1 | Sytl1 | 84958 | 12-May-15 |
| 20101 | 2 | 3 | 4 | | IV-1 | Snta1 | 6640 | 23-May-15 | 20809 | 2 | 3 | 4 | IV-1 | Sytl2 | 54843 | 12-May-15 |
| 20102 | 2 | 3 | 4 | | IV-1 | Sntb1 | 6641 | 4-May-15 | 20810 | 2 | 3 | 4 | IV-1 | Sytl3 | 94120 | 4-May-15 |
| 20103 | 2 | 3 | 4 | | IV-1 | Sntb2 | 6645 | 4-May-15 | 20836 | 2 | 3 | 4 | IV-1 | Tac1 | 6863 | 4-May-15 |
| 20105 | 2 | 3 | 4 | | IV-1 | Sntg2 | 54221 | 4-May-15 | 20838 | 2 | 3 | 4 | IV-1 | Tac4 | 255061 | 7-Jun-15 |
| 20111 | 2 | 3 | 4 | | IV-1 | Snx10 | 29887 | 4-May-15 | 20876 | 2 | 3 | 4 | IV-1 | Tagln | 6876 | 12-May-15 |
| 20124 | 2 | 3 | 4 | | IV-1 | Snx22 | 79856 | 4-May-15 | 20879 | 2 | 3 | 4 | IV-1 | Tal1 | 6886 | 17-May-15 |
| 20141 | 2 | 3 | 4 | | IV-1 | Soat2 | 8435 | 12-May-15 | 20898 | 2 | 3 | 4 | IV-1 | Tarm1 | 441864 | 4-May-15 |
| 20142 | 2 | 3 | 4 | | IV-1 | Sobp | 55084 | 4-May-15 | 20941 | 2 | 3 | 4 | IV-1 | Tat | 6898 | 7-Jun-15 |
| 20143 | 2 | 3 | 4 | | IV-1 | Socs1 | 8651 | 4-May-15 | 20967 | 2 | 3 | 4 | IV-1 | Tbc1d24 | 57465 | 4-May-15 |
| 20144 | 2 | 3 | 4 | | IV-1 | Socs2 | 8835 | 14-May-15 | 20970 | 2 | 3 | 4 | IV-1 | Tbc1d30 | 23329 | 4-May-15 |
| 20145 | 2 | 3 | 4 | | IV-1 | Socs3 | 9021 | 23-May-15 | 20973 | 2 | 3 | 4 | IV-1 | Tbc1d4 | 9882 | 4-May-15 |
| 20146 | 2 | 3 | 4 | | IV-1 | Socs4 | 122809 | 7-Jun-15 | 20978 | 2 | 3 | 4 | IV-1 | Tbc1d9 | 23158 | 4-May-15 |
| 20155 | 2 | 3 | 4 | | IV-1 | Sohlh1 | 402381 | 4-May-15 | 21006 | 2 | 3 | 4 | IV-1 | Tbx2 | 6909 | 12-May-15 |
| 20163 | 2 | 3 | 4 | | IV-1 | Sorcs2 | 57537 | 4-May-15 | 21008 | 2 | 3 | 4 | IV-1 | Tbx21 | 30009 | 4-May-15 |
| 20172 | 2 | 3 | 4 | | IV-1 | Sowaha | 134548 | 4-May-15 | 21010 | 2 | 3 | 4 | IV-1 | Tbx3 | 6926 | 4-May-15 |
| 20173 | 2 | 3 | 4 | | IV-1 | Sowahb | 345079 | 4-May-15 | 21011 | 2 | 3 | 4 | IV-1 | Tbx3os2 | | |
| 20179 | 2 | 3 | 4 | | IV-1 | Sox12 | 6666 | 4-May-15 | 21022 | 2 | 3 | 4 | IV-1 | Tcea2 | 6919 | 12-May-15 |
| 20182 | 2 | 3 | 4 | | IV-1 | Sox15 | 6665 | 12-May-15 | 21032 | 2 | 3 | 4 | IV-1 | Tceb1 | 6921 | 4-May-15 |
| 20183 | 2 | 3 | 4 | | IV-1 | Sox17 | 64321 | 31-May-15 | 21038 | 2 | 3 | 4 | IV-1 | Tcf15 | 6939 | 10-May-15 |
| 20196 | 2 | 3 | 4 | | IV-1 | Sox9 | 6662 | 23-May-15 | 21042 | 2 | 3 | 4 | IV-1 | Tcf23 | 150921 | 4-May-15 |
| 20203 | 2 | 3 | 4 | | IV-1 | Sp3os | | | 21043 | 2 | 3 | 4 | IV-1 | Tcf24 | 100129654 | 4-May-15 |
| 20210 | 2 | 3 | 4 | | IV-1 | Spa17 | 53340 | 4-May-15 | 21051 | 2 | 3 | 4 | IV-1 | Tchh | 7062 | 12-May-15 |
| 20236 | 2 | 3 | 4 | | IV-1 | Spata18 | 132671 | 4-May-15 | 21061 | 2 | 3 | 4 | IV-1 | Tcn2 | 6948 | 4-May-15 |
| 20242 | 2 | 3 | 4 | | IV-1 | Spata24 | 202051 | 4-May-15 | 21075 | 2 | 3 | 4 | IV-1 | Tcte3 | 6991 | 12-May-15 |
| 20252 | 2 | 3 | 4 | | IV-1 | Spata33 | 124045 | 4-May-15 | 21077 | 2 | 3 | 4 | IV-1 | Tctex1d2 | 255758 | 4-May-15 |
| 20265 | 2 | 3 | 4 | | IV-1 | Spc24 | 147841 | 4-May-15 | 21078 | 2 | 3 | 4 | IV-1 | Tctex1d4 | 343521 | 4-May-15 |
| 20266 | 2 | 3 | 4 | | IV-1 | Spc25 | 57405 | 4-May-15 | 21082 | 2 | 3 | 4 | IV-1 | Tdg | 6996 | 12-May-15 |
| 20274 | 2 | 3 | 4 | | IV-1 | Sperc3 | 92521 | 4-May-15 | 21102 | 2 | 3 | 4 | IV-1 | Tead1 | 7003 | 4-May-15 |
| 20290 | 2 | 3 | 4 | | IV-1 | Spef3 | 25876 | 4-May-15 | 21111 | 2 | 3 | 4 | IV-1 | Tectz | 7007 | 23-May-15 |
| 20292 | 2 | 3 | 4 | | IV-1 | Speg | 10290 | 12-May-15 | 21114 | 2 | 3 | 4 | IV-1 | Tef | 7008 | 4-May-15 |
| 20293 | 2 | 3 | 4 | | IV-1 | Sperm1 | 374768 | 4-May-15 | 21124 | 2 | 3 | 4 | IV-1 | Tenc1 | 23371 | 17-May-15 |
| 20295 | 2 | 3 | 4 | | IV-1 | Spert | 220082 | 4-May-15 | 21131 | 2 | 3 | 4 | IV-1 | Terc | 7012 | 24-May-15 |
| 20301 | 2 | 3 | 4 | | IV-1 | Sphk1 | 8877 | 4-May-15 | 21170 | 2 | 3 | 4 | IV-1 | Tex38 | 374973 | 28-May-15 |
| 20305 | 2 | 3 | 4 | | IV-1 | Spib | 6689 | 12-May-15 | 21180 | 2 | 3 | 4 | IV-1 | Tfap4 | 7023 | 28-May-15 |
| 20306 | 2 | 3 | 4 | | IV-1 | Spic | 121599 | 28-May-15 | 21184 | 2 | 3 | 4 | IV-1 | Tfcp2l1 | 29842 | 4-May-15 |
| 20317 | 2 | 3 | 4 | | IV-1 | Spink13 | 153218 | 4-May-15 | 21185 | 2 | 3 | 4 | IV-1 | Tfdp1 | 7027 | 2-Jun-15 |
| 20326 | 2 | 3 | 4 | | IV-1 | Spinkl | | | 21186 | 2 | 3 | 4 | IV-1 | Tfdp2 | 7029 | 5-May-15 |
| 20329 | 2 | 3 | 4 | | IV-1 | Spint3 | 10816 | 7-Jun-15 | 21192 | 2 | 3 | 4 | IV-1 | Tff3 | 7033 | 24-May-15 |
| 20332 | 2 | 3 | 4 | | IV-1 | Spire1 | 56907 | 4-May-15 | 21198 | 2 | 3 | 4 | IV-1 | Tfr2 | 7036 | 23-May-15 |
| 20340 | 2 | 3 | 4 | | IV-1 | Spock1 | 6695 | 4-May-15 | 21199 | 2 | 3 | 4 | IV-1 | Tfrc | 7037 | 24-May-15 |
| 20341 | 2 | 3 | 4 | | IV-1 | Spock2 | 9806 | 12-May-15 | 21200 | 2 | 3 | 4 | IV-1 | Tg | 7038 | 31-May-15 |
| 20356 | 2 | 3 | 4 | | IV-1 | Spred3 | 399473 | 4-May-15 | 21212 | 2 | 3 | 4 | IV-1 | Tgif1 | 7050 | 23-May-15 |
| 20359 | 2 | 3 | 4 | | IV-1 | Spr1b | 6699 | 12-May-15 | 21216 | 2 | 3 | 4 | IV-1 | Tgm1 | 7051 | 23-May-15 |
| 20360 | 2 | 3 | 4 | | IV-1 | Sprr2a1 | | | 21239 | 2 | 3 | 4 | IV-1 | Thbs1 | 7057 | 12-May-15 |
| 20361 | 2 | 3 | 4 | | IV-1 | Sprr2a2 | | | 21240 | 2 | 3 | 4 | IV-1 | Thbs2 | 7058 | 17-May-15 |
| 20362 | 2 | 3 | 4 | | IV-1 | Sprr2b | 6701 | 4-May-15 | 21242 | 2 | 3 | 4 | IV-1 | Thbs4 | 7060 | 12-May-15 |
| 20363 | 2 | 3 | 4 | | IV-1 | Sprr2d | 6703 | 4-May-15 | 21245 | 2 | 3 | 4 | IV-1 | Them5 | 284486 | 4-May-15 |
| 20365 | 2 | 3 | 4 | | IV-1 | Sprr2f | 6705 | 4-May-15 | 21246 | 2 | 3 | 4 | IV-1 | Them6 | 51337 | 4-May-15 |
| 20366 | 2 | 3 | 4 | | IV-1 | Sprr2g | 6706 | 4-May-15 | 21247 | 2 | 3 | 4 | IV-1 | Them7 | | |

Fig.22 - 37

| | | | | | | | | | | | | | | | | |
|---|---|---|---|---|---|---|---|---|---|---|---|---|---|---|---|---|
| 21266 | 2 | 3 | 4 | | IV-1 | Thsd1 | 55901 | 4-May-15 | 21919 | 2 | 3 | 4 | | IV-1 | Trim10 | 10107 | 4-May-15 |
| 21267 | 2 | 3 | 4 | | IV-1 | Thsd4 | 79875 | 4-May-15 | 21931 | 2 | 3 | 4 | | IV-1 | Trim24 | 8805 | 4-May-15 |
| 21275 | 2 | 3 | 4 | | IV-1 | Thyn1 | 29087 | 4-May-15 | 21936 | 2 | 3 | 4 | | IV-1 | Trim29 | 23650 | 12-May-15 |
| 21283 | 2 | 3 | 4 | | IV-1 | Tie1 | 7075 | 4-May-15 | 21940 | 2 | 3 | 4 | | IV-1 | Trim30d | | |
| 21284 | 2 | 3 | 4 | | IV-1 | Tifa | 92610 | 7-Jun-15 | 21948 | 2 | 3 | 4 | | IV-1 | Trim36 | 55521 | 12-May-15 |
| 21292 | 2 | 3 | 4 | | IV-1 | Timd4 | 91937 | 4-May-15 | 21965 | 2 | 3 | 4 | | IV-1 | Trim55 | 84675 | 12-May-15 |
| 21312 | 2 | 3 | 4 | | IV-1 | Timp4 | 7079 | 12-May-15 | 21966 | 2 | 3 | 4 | | IV-1 | Trim56 | 81844 | 4-May-15 |
| 21322 | 2 | 3 | 4 | | IV-1 | Tjp2 | 9414 | 12-May-15 | 21967 | 2 | 3 | 4 | | IV-1 | Trim58 | 25893 | 4-May-15 |
| 21323 | 2 | 3 | 4 | | IV-1 | Tjp3 | 27134 | 4-May-15 | 21990 | 2 | 3 | 4 | | IV-1 | Trip11 | 9321 | 6-May-15 |
| 21326 | 2 | 3 | 4 | | IV-1 | Tkt | 7086 | 7-Jun-15 | 22030 | 2 | 3 | 4 | | IV-1 | Trp63 | | |
| 21329 | 2 | 3 | 4 | | IV-1 | Tlcd1 | 116238 | 4-May-15 | 22039 | 2 | 3 | 4 | | IV-1 | Trpc5os | 100329135 | 4-May-15 |
| 21334 | 2 | 3 | 4 | | IV-1 | Tle2 | 7089 | 4-May-15 | 22045 | 2 | 3 | 4 | | IV-1 | Trpm3 | 80036 | 4-May-15 |
| 21347 | 2 | 3 | 4 | | IV-1 | Tlr13 | | | 22046 | 2 | 3 | 4 | | IV-1 | Trpm4 | 54795 | 12-May-15 |
| 21348 | 2 | 3 | 4 | | IV-1 | Tlr2 | 7097 | 24-May-15 | 22047 | 2 | 3 | 4 | | IV-1 | Trpm5 | 29850 | 4-May-15 |
| 21351 | 2 | 3 | 4 | | IV-1 | Tlr5 | 7100 | 17-May-15 | 22056 | 2 | 3 | 4 | | IV-1 | Trpv4 | 59341 | 23-May-15 |
| 21353 | 2 | 3 | 4 | | IV-1 | Tlr7 | 51284 | 17-May-15 | 22057 | 2 | 3 | 4 | | IV-1 | Trpv5 | 56302 | 12-May-15 |
| 21363 | 2 | 3 | 4 | | IV-1 | Tm4sf19 | 116211 | 4-May-15 | 22062 | 2 | 3 | 4 | | IV-1 | Try10 | | |
| 21365 | 2 | 3 | 4 | | IV-1 | Tm4sf4 | 7104 | 4-May-15 | 22065 | 2 | 3 | 4 | | IV-1 | Tsacc | 128229 | 21-May-15 |
| 21368 | 2 | 3 | 4 | | IV-1 | Tm6sf2 | 53345 | 4-May-15 | 22068 | 2 | 3 | 4 | | IV-1 | Tsc22d1 | 8848 | 12-May-15 |
| 21369 | 2 | 3 | 4 | | IV-1 | Tm7sf2 | 7108 | 4-May-15 | 22070 | 2 | 3 | 4 | | IV-1 | Tsc22d3 | 1831 | 4-May-15 |
| 21384 | 2 | 3 | 4 | | IV-1 | Tmc4 | 147798 | 21-May-15 | 22079 | 2 | 3 | 4 | | IV-1 | Tsga13 | 114960 | 12-May-15 |
| 21385 | 2 | 3 | 4 | | IV-1 | Tmc5 | 79838 | 12-May-15 | 22088 | 2 | 3 | 4 | | IV-1 | Tsku | 25987 | 4-May-15 |
| 21387 | 2 | 3 | 4 | | IV-1 | Tmc7 | 79905 | 4-May-15 | 22089 | 2 | 3 | 4 | | IV-1 | Tslp | 85480 | 24-May-15 |
| 21390 | 2 | 3 | 4 | | IV-1 | Tmcc2 | 9911 | 12-May-15 | 22096 | 2 | 3 | 4 | | IV-1 | Tspan12 | 23554 | 23-May-15 |
| 21406 | 2 | 3 | 4 | | IV-1 | Tmed6 | 146456 | 4-May-15 | 22102 | 2 | 3 | 4 | | IV-1 | Tspan2 | 10100 | 21-May-15 |
| 21412 | 2 | 3 | 4 | | IV-1 | Tmem100 | 55273 | 3-May-15 | 22107 | 2 | 3 | 4 | | IV-1 | Tspan33 | 340348 | 4-May-15 |
| 21429 | 2 | 3 | 4 | | IV-1 | Tmem120b | 144404 | 4-May-15 | 22108 | 2 | 3 | 4 | | IV-1 | Tspan4 | 7106 | 4-May-15 |
| 21432 | 2 | 3 | 4 | | IV-1 | Tmem125 | 128218 | 4-May-15 | 22110 | 2 | 3 | 4 | | IV-1 | Tspan6 | 7105 | 4-May-15 |
| 21452 | 2 | 3 | 4 | | IV-1 | Tmem141 | 85014 | 4-May-15 | 22112 | 2 | 3 | 4 | | IV-1 | Tspan8 | 7103 | 17-May-15 |
| 21454 | 2 | 3 | 4 | | IV-1 | Tmem144 | 55314 | 4-May-15 | 22116 | 2 | 3 | 4 | | IV-1 | Tspo2 | 222642 | 4-May-15 |
| 21465 | 2 | 3 | 4 | | IV-1 | Tmem154 | 201799 | 4-May-15 | 22129 | 2 | 3 | 4 | | IV-1 | Tssk2 | 23617 | 4-May-15 |
| 21482 | 2 | 3 | 4 | | IV-1 | Tmem173 | 340061 | 4-May-15 | 22131 | 2 | 3 | 4 | | IV-1 | Tssk4 | 283629 | 7-Jun-15 |
| 21488 | 2 | 3 | 4 | | IV-1 | Tmem178 | 130733 | 2-Jun-15 | 22156 | 2 | 3 | 4 | | IV-1 | Ttc25 | 83538 | 4-May-15 |
| 21490 | 2 | 3 | 4 | | IV-1 | Tmem179 | 388021 | 4-May-15 | 22180 | 2 | 3 | 4 | | IV-1 | Ttc9 | 23508 | 4-May-15 |
| 21493 | 2 | 3 | 4 | | IV-1 | Tmem180 | 79847 | 21-May-15 | 22190 | 2 | 3 | 4 | | IV-1 | Tti10 | 254173 | 4-May-15 |
| 21499 | 2 | 3 | 4 | | IV-1 | Tmem184a | 202915 | 4-May-15 | 22194 | 2 | 3 | 4 | | IV-1 | Ttl2 | 83887 | 4-May-15 |
| 21507 | 2 | 3 | 4 | | IV-1 | Tmem191c | 645426 | 20-May-15 | 22196 | 2 | 3 | 4 | | IV-1 | Ttll4 | 9654 | 21-May-15 |
| 21517 | 2 | 3 | 4 | | IV-1 | Tmem200b | 399474 | 4-May-15 | 22203 | 2 | 3 | 4 | | IV-1 | Ttpa | 7274 | 23-May-15 |
| 21531 | 2 | 3 | 4 | | IV-1 | Tmem213 | 155006 | 4-May-15 | 22206 | 2 | 3 | 4 | | IV-1 | Ttyh1 | 57348 | 4-May-15 |
| 21538 | 2 | 3 | 4 | | IV-1 | Tmem220 | 388335 | 4-May-15 | 22215 | 2 | 3 | 4 | | IV-1 | Tuba4a | 7277 | 4-May-15 |
| 21559 | 2 | 3 | 4 | | IV-1 | Tmem245 | 23731 | 4-May-15 | 22219 | 2 | 3 | 4 | | IV-1 | Tubb2a | 7280 | 12-May-15 |
| 21568 | 2 | 3 | 4 | | IV-1 | Tmem254b | | | 22221 | 2 | 3 | 4 | | IV-1 | Tubb2b | 347733 | 4-May-15 |
| 21572 | 2 | 3 | 4 | | IV-1 | Tmem256 | 254863 | 4-May-15 | 22222 | 2 | 3 | 4 | | IV-1 | Tubb3 | 10381 | 23-May-15 |
| 21573 | 2 | 3 | 4 | | IV-1 | Tmem258 | 746 | 4-May-15 | 22239 | 2 | 3 | 4 | | IV-1 | Tulp1 | 7287 | 31-May-15 |
| 21587 | 2 | 3 | 4 | | IV-1 | Tmem37 | 140738 | 12-May-15 | 22244 | 2 | 3 | 4 | | IV-1 | Tusc1 | 286319 | 4-May-15 |
| 21592 | 2 | 3 | 4 | | IV-1 | Tmem40 | 55287 | 4-May-15 | 22246 | 2 | 3 | 4 | | IV-1 | Tusc3 | 7991 | 23-May-15 |
| 21608 | 2 | 3 | 4 | | IV-1 | Tmem53 | 79639 | 4-May-15 | 22268 | 2 | 3 | 4 | | IV-1 | Txndc2 | 84203 | 12-May-15 |
| 21612 | 2 | 3 | 4 | | IV-1 | Tmem56 | 148534 | 4-May-15 | 22285 | 2 | 3 | 4 | | IV-1 | Tyrobp | 7305 | 23-May-15 |
| 21621 | 2 | 3 | 4 | | IV-1 | Tmem64 | 169200 | 4-May-15 | 22298 | 2 | 3 | 4 | | IV-1 | Uap1l1 | 91373 | 24-May-15 |
| 21647 | 2 | 3 | 4 | | IV-1 | Tmem91 | 641649 | 4-May-15 | 22307 | 2 | 3 | 4 | | IV-1 | Ubac1 | 10422 | 4-May-15 |
| 21651 | 2 | 3 | 4 | | IV-1 | Tmem98 | 26022 | 12-May-15 | 22310 | 2 | 3 | 4 | | IV-1 | Ubald2 | 283991 | 4-May-15 |
| 21656 | 2 | 3 | 4 | | IV-1 | Tmigd1 | 388364 | 4-May-15 | 22319 | 2 | 3 | 4 | | IV-1 | Ubd | 10537 | 3-May-15 |
| 21664 | 2 | 3 | 4 | | IV-1 | Tmprss11a | 339967 | 12-May-15 | 22342 | 2 | 3 | 4 | | IV-1 | Ube2l6 | 9246 | 4-May-15 |
| 21670 | 2 | 3 | 4 | | IV-1 | Tmprss11g | | | 22348 | 2 | 3 | 4 | | IV-1 | Ube2ql1 | 134111 | 4-May-15 |
| 21674 | 2 | 3 | 4 | | IV-1 | Tmprss2 | 7113 | 21-May-15 | 22360 | 2 | 3 | 4 | | IV-1 | Ube4a | 9354 | 12-May-15 |
| 21683 | 2 | 3 | 4 | | IV-1 | Tmsb15b1 | | | 22366 | 2 | 3 | 4 | | IV-1 | Ubl4b | 164153 | 4-May-15 |
| 21684 | 2 | 3 | 4 | | IV-1 | Tmsb15b2 | | | 22390 | 2 | 3 | 4 | | IV-1 | Ubxn10 | 127733 | 4-May-15 |
| 21685 | 2 | 3 | 4 | | IV-1 | Tmsb15l | | | 22406 | 2 | 3 | 4 | | IV-1 | Ucklos | 100113386 | 4-May-15 |
| 21698 | 2 | 3 | 4 | | IV-1 | Tnf | 7124 | 31-May-15 | 22408 | 2 | 3 | 4 | | IV-1 | Ucn | 7349 | 4-May-15 |
| 21701 | 2 | 3 | 4 | | IV-1 | Tnfaip3 | 7128 | 12-May-15 | 22409 | 2 | 3 | 4 | | IV-1 | Ucn2 | 90226 | 7-Jun-15 |
| 21702 | 2 | 3 | 4 | | IV-1 | Tnfaip6 | 7130 | 23-May-15 | 22413 | 2 | 3 | 4 | | IV-1 | Ucp3 | 7352 | 17-May-15 |
| 21705 | 2 | 3 | 4 | | IV-1 | Tnfaip8l2 | 79626 | 4-May-15 | 22422 | 2 | 3 | 4 | | IV-1 | Ugdh | 7358 | 12-May-15 |
| 21710 | 2 | 3 | 4 | | IV-1 | Tnfrsf12a | 51330 | 4-May-15 | 22429 | 2 | 3 | 4 | | IV-1 | Ugt1a5 | 54579 | 12-May-15 |
| 21713 | 2 | 3 | 4 | | IV-1 | Tnfrsf13b | 23495 | 4-May-15 | 22430 | 2 | 3 | 4 | | IV-1 | Ugt1a6a | | |
| 21715 | 2 | 3 | 4 | | IV-1 | Tnfrsf18 | 8784 | 3-May-15 | 22431 | 2 | 3 | 4 | | IV-1 | Ugt1a6b | | |
| 21716 | 2 | 3 | 4 | | IV-1 | Tnfrsf19 | 55504 | 4-May-15 | 22432 | 2 | 3 | 4 | | IV-1 | Ugt1a7c | | |
| 21718 | 2 | 3 | 4 | | IV-1 | Tnfrsf1b | 7133 | 12-May-15 | 22433 | 2 | 3 | 4 | | IV-1 | Ugt1a9 | 54600 | 28-May-15 |
| 21719 | 2 | 3 | 4 | | IV-1 | Tnfrsf21 | 27242 | 4-May-15 | 22438 | 2 | 3 | 4 | | IV-1 | Ugt2b34 | | |
| 21722 | 2 | 3 | 4 | | IV-1 | Tnfrsf25 | 8718 | 24-May-15 | 22440 | 2 | 3 | 4 | | IV-1 | Ugt2b36 | | |
| 21724 | 2 | 3 | 4 | | IV-1 | Tnfrsf4 | 7293 | 4-May-15 | 22443 | 2 | 3 | 4 | | IV-1 | Ugt2b5 | | |
| 21726 | 2 | 3 | 4 | | IV-1 | Tnfrsf9 | 3604 | 24-May-15 | 22446 | 2 | 3 | 4 | | IV-1 | Ugt8a | | |
| 21731 | 2 | 3 | 4 | | IV-1 | Tnfsf13 | 8741 | 17-May-15 | 22447 | 2 | 3 | 4 | | IV-1 | Uhmk1 | 127933 | 4-May-15 |
| 21732 | 2 | 3 | 4 | | IV-1 | Tnfsf13b | 10673 | 17-May-15 | 22448 | 2 | 3 | 4 | | IV-1 | Uhrf1 | 29128 | 12-May-15 |
| 21743 | 2 | 3 | 4 | | IV-1 | Tnk1 | 8711 | 4-May-15 | 22458 | 2 | 3 | 4 | | IV-1 | Umod | 7369 | 23-May-15 |
| 21746 | 2 | 3 | 4 | | IV-1 | Tnks | 8658 | 4-May-15 | 22464 | 2 | 3 | 4 | | IV-1 | Unc13b | 10497 | 4-May-15 |
| 21747 | 2 | 3 | 4 | | IV-1 | Tnks1bp1 | 85456 | 4-May-15 | 22468 | 2 | 3 | 4 | | IV-1 | Unc45b | 146862 | 12-May-15 |
| 21749 | 2 | 3 | 4 | | IV-1 | Tnmd | 64102 | 4-May-15 | 22470 | 2 | 3 | 4 | | IV-1 | Unc5a | 90249 | 4-May-15 |
| 21751 | 2 | 3 | 4 | | IV-1 | Tnnc1 | 7134 | 7-Jun-15 | 22477 | 2 | 3 | 4 | | IV-1 | Unc93a | 54346 | 4-May-15 |
| 21755 | 2 | 3 | 4 | | IV-1 | Tnni3 | 7137 | 23-May-15 | 22480 | 2 | 3 | 4 | | IV-1 | Ung | 7374 | 4-May-15 |
| 21757 | 2 | 3 | 4 | | IV-1 | Tnnt1 | 7138 | 23-May-15 | 22489 | 2 | 3 | 4 | | IV-1 | Upk1a | 11045 | 4-May-15 |
| 21758 | 2 | 3 | 4 | | IV-1 | Tnnt2 | 7139 | 23-May-15 | 22490 | 2 | 3 | 4 | | IV-1 | Upk1b | 7348 | 4-May-15 |
| 21771 | 2 | 3 | 4 | | IV-1 | Tns3 | 64759 | 4-May-15 | 22492 | 2 | 3 | 4 | | IV-1 | Upk3a | 7380 | 4-May-15 |
| 21772 | 2 | 3 | 4 | | IV-1 | Tns4 | 84951 | 12-May-15 | 22493 | 2 | 3 | 4 | | IV-1 | Upk3b | 80761 | 19-Mar-15 |
| 21773 | 2 | 3 | 4 | | IV-1 | Tnxb | 7148 | 8-May-15 | 22497 | 2 | 3 | 4 | | IV-1 | Uprt | 139596 | 12-May-15 |
| 21779 | 2 | 3 | 4 | | IV-1 | Tom1l1 | 10040 | 4-May-15 | 22499 | 2 | 3 | 4 | | IV-1 | Uqcc2 | 84300 | 14-May-15 |
| 21804 | 2 | 3 | 4 | | IV-1 | Toporsos | | | 22516 | 2 | 3 | 4 | | IV-1 | Urod | 7389 | 23-May-15 |
| 21816 | 2 | 3 | 4 | | IV-1 | Tpbg | 7162 | 4-May-15 | 22526 | 2 | 3 | 4 | | IV-1 | Usmg5 | 84833 | 4-May-15 |
| 21821 | 2 | 3 | 4 | | IV-1 | Tpd52 | 7163 | 4-May-15 | 22543 | 2 | 3 | 4 | | IV-1 | Usp2 | 9099 | 12-May-15 |
| 21830 | 2 | 3 | 4 | | IV-1 | Tpm1 | 7168 | 31-May-15 | 22544 | 2 | 3 | 4 | | IV-1 | Usp20 | 10868 | 4-May-15 |
| 21834 | 2 | 3 | 4 | | IV-1 | Tpm3 | 7172 | 12-May-15 | 22558 | 2 | 3 | 4 | | IV-1 | Usp34 | 9736 | 4-May-15 |
| 21848 | 2 | 3 | 4 | | IV-1 | Tpsb2 | 64499 | 4-May-15 | 22559 | 2 | 3 | 4 | | IV-1 | Usp35 | 57558 | 4-May-15 |
| 21851 | 2 | 3 | 4 | | IV-1 | Tpst2 | 8459 | 4-May-15 | 22570 | 2 | 3 | 4 | | IV-1 | Usp46 | 64854 | 4-May-15 |
| 21876 | 2 | 3 | 4 | | IV-1 | Tram2 | 9697 | 21-May-15 | 22589 | 2 | 3 | 4 | | IV-1 | Utp14b | 9724 | 4-May-15 |
| 21902 | 2 | 3 | 4 | | IV-1 | Trem3 | | | 22599 | 2 | 3 | 4 | | IV-1 | Uts2r | 2837 | 7-Jun-15 |
| 21908 | 2 | 3 | 4 | | IV-1 | Trex2 | 11219 | 4-May-15 | 22627 | 2 | 3 | 4 | | IV-1 | Vat1l | 57687 | 4-May-15 |
| 21909 | 2 | 3 | 4 | | IV-1 | Trf | 7018 | 7-Jun-15 | 22636 | 2 | 3 | 4 | | IV-1 | Vcam1 | 7412 | 17-May-15 |
| 21917 | 2 | 3 | 4 | | IV-1 | Trib3 | 57761 | 12-May-15 | | | | | | | | | |

Fig.22 - 38

| | | | | | | | | | | | | | | | | |
|---|---|---|---|---|---|---|---|---|---|---|---|---|---|---|---|---|
| 22641 | 2 | 3 | 4 | | IV-1 | Vcpkmt | 79609 | 4-May-15 | 23911 | 2 | 3 | 4 | | IV-1 | Zmat4 | 79698 | 2-Jun-15 |
| 22642 | 2 | 3 | 4 | | IV-1 | Vdac1 | 7416 | 12-May-15 | 23940 | 2 | 3 | 4 | | IV-1 | Znrf4 | 148066 | 4-May-15 |
| 22645 | 2 | 3 | 4 | | IV-1 | Vdr | 7421 | 7-Jun-15 | 23957 | 2 | 3 | 4 | | IV-1 | Zscan18 | 65982 | 28-May-15 |
| 22652 | 2 | 3 | 4 | | IV-1 | Vgf | 7425 | 4-May-15 | 3 | 2 | 3 | | | III-2 | 0610009B22Rik | | |
| 22662 | 2 | 3 | 4 | | IV-1 | Vip | 7432 | 7-Jun-15 | 6 | 2 | 3 | | | III-2 | 0610010B08Rik | | |
| 22689 | 2 | 3 | 4 | | IV-1 | Vipr | 7436 | 23-May-15 | 8 | 2 | 3 | | | III-2 | 0610010K14Rik | | |
| 22996 | 2 | 3 | 4 | | IV-1 | Vmn2r97 | | | 11 | 2 | 3 | | | III-2 | 0610030E20Rik | | |
| 23006 | 2 | 3 | 4 | | IV-1 | Vnn1 | 8876 | 4-May-15 | 12 | 2 | 3 | | | III-2 | 0610031J06Rik | | |
| 23007 | 2 | 3 | 4 | | IV-1 | Vnn3 | 55350 | 23-May-15 | 15 | 2 | 3 | | | III-2 | 0610038B21Rik | | |
| 23016 | 2 | 3 | 4 | | IV-1 | Vps13c | 54832 | 4-May-15 | 26 | 2 | 3 | | | III-2 | 1110004F10Rik | | |
| 23023 | 2 | 3 | 4 | | IV-1 | Vps28 | 51160 | 4-May-15 | 33 | 2 | 3 | | | III-2 | 1110015O18Rik | | |
| 23030 | 2 | 3 | 4 | | IV-1 | Vps37b | 79720 | 4-May-15 | 34 | 2 | 3 | | | III-2 | 1110017D15Rik | | |
| 23032 | 2 | 3 | 4 | | IV-1 | Vps37d | 155382 | 4-May-15 | 39 | 2 | 3 | | | III-2 | 1110028F18Rik | | |
| 23050 | 2 | 3 | 4 | | IV-1 | Vsig10 | 54621 | 4-May-15 | 42 | 2 | 3 | | | III-2 | 1110034G24Rik | | |
| 23052 | 2 | 3 | 4 | | IV-1 | Vsig2 | 23584 | 4-May-15 | 44 | 2 | 3 | | | III-2 | 1110037F02Rik | | |
| 23054 | 2 | 3 | 4 | | IV-1 | Vsig8 | 391123 | 4-May-15 | 61 | 2 | 3 | | | III-2 | 1300002E11Rik | | |
| 23058 | 2 | 3 | 4 | | IV-1 | Vstm2l | 128434 | 4-May-15 | 71 | 2 | 3 | 4 | | III-2 | 1500019A07Rik | | |
| 23060 | 2 | 3 | 4 | | IV-1 | Vstm5 | 387804 | 4-May-15 | 73 | 2 | 3 | | | III-2 | 1500015O10Rik | | |
| 23067 | 2 | 3 | 4 | | IV-1 | Vtn | 7448 | 24-May-15 | 76 | 2 | 3 | | | III-2 | 1600002H07Rik | | |
| 23069 | 2 | 3 | 4 | | IV-1 | Vwa2 | 340706 | 4-May-15 | 80 | 2 | 3 | | | III-2 | 1600024C10Rik | | |
| 23085 | 2 | 3 | 4 | | IV-1 | Wars | 7453 | 12-May-15 | 94 | 2 | 3 | | | III-2 | 1700001D01Rik | | |
| 23107 | 2 | 3 | 4 | | IV-1 | Wdfy2 | 115825 | 12-May-15 | 95 | 2 | 3 | | | III-2 | 1700001F09Rik | | |
| 23123 | 2 | 3 | 4 | | IV-1 | Wdr25 | 79446 | 4-May-15 | 106 | 2 | 3 | | | III-2 | 1700003C15Rik | | |
| 23187 | 2 | 3 | 4 | | IV-1 | Wfdc12 | 128488 | 4-May-15 | 126 | 2 | 3 | | | III-2 | 1700007K09Rik | | |
| 23191 | 2 | 3 | 4 | | IV-1 | Wfdc16 | | | 130 | 2 | 3 | | | III-2 | 1700008F21Rik | | |
| 23192 | 2 | 3 | 4 | | IV-1 | Wfdc17 | | | 134 | 2 | 3 | | | III-2 | 1700008O03Rik | | |
| 23194 | 2 | 3 | 4 | | IV-1 | Wfdc2 | 10406 | 4-May-15 | 141 | 2 | 3 | | | III-2 | 1700010D01Rik | | |
| 23202 | 2 | 3 | 4 | | IV-1 | Wfikkn2 | 124857 | 12-May-15 | 145 | 2 | 3 | | | III-2 | 1700010K23Rik | | |
| 23205 | 2 | 3 | 4 | | IV-1 | Whrn | 25861 | 23-May-15 | 151 | 2 | 3 | | | III-2 | 1700011L22Rik | | |
| 23212 | 2 | 3 | 4 | | IV-1 | Wipf3 | 644150 | 4-May-15 | 159 | 2 | 3 | | | III-2 | 1700012L04Rik | | |
| 23213 | 2 | 3 | 4 | | IV-1 | Wipi1 | 55062 | 21-May-15 | 170 | 2 | 3 | | | III-2 | 1700016G22Rik | | |
| 23216 | 2 | 3 | 4 | | IV-1 | Wisp2 | 8839 | 21-May-15 | 189 | 2 | 3 | | | III-2 | 1700019B03Rik | | |
| 23221 | 2 | 3 | 4 | | IV-1 | Wnk2 | 65268 | 12-May-15 | 193 | 2 | 3 | | | III-2 | 1700019G17Rik | | |
| 23223 | 2 | 3 | 4 | | IV-1 | Wnk4 | 65266 | 23-May-15 | 197 | 2 | 3 | | | III-2 | 1700019N19Rik | | |
| 23225 | 2 | 3 | 4 | | IV-1 | Wnt10a | 80326 | 4-May-15 | 202 | 2 | 3 | | | III-2 | 1700020I14Rik | | |
| 23229 | 2 | 3 | 4 | | IV-1 | Wnt2 | 7472 | 12-May-15 | 205 | 2 | 3 | | | III-2 | 1700020N01Rik | | |
| 23230 | 2 | 3 | 4 | | IV-1 | Wnt2b | 7482 | 17-May-15 | 209 | 2 | 3 | | | III-2 | 1700021F07Rik | | |
| 23235 | 2 | 3 | 4 | | IV-1 | Wnt5b | 81029 | 12-May-15 | 231 | 2 | 3 | | | III-2 | 1700025G04Rik | | |
| 23236 | 2 | 3 | 4 | | IV-1 | Wnt6 | 7475 | 4-May-15 | 246 | 2 | 3 | | | III-2 | 1700028E10Rik | | |
| 23238 | 2 | 3 | 4 | | IV-1 | Wnt7b | 7477 | 4-May-15 | 265 | 2 | 3 | | | III-2 | 1700030F18Rik | | |
| 23247 | 2 | 3 | 4 | | IV-1 | Wsb1 | 26118 | 14-May-15 | 268 | 2 | 3 | | | III-2 | 1700030L20Rik | | |
| 23254 | 2 | 3 | 4 | | IV-1 | Wtip | 126374 | 4-May-15 | 269 | 2 | 3 | | | III-2 | 1700030M09Rik | | |
| 23255 | 2 | 3 | 4 | | IV-1 | Wwc1 | 23286 | 24-May-15 | 275 | 2 | 3 | | | III-2 | 1700031P21Rik | | |
| 23264 | 2 | 3 | 4 | | IV-1 | Xcl1 | 6375 | 4-May-15 | 289 | 2 | 3 | | | III-2 | 1700039E22Rik | | |
| 23266 | 2 | 3 | 4 | | IV-1 | Xdh | 7498 | 24-May-15 | 309 | 2 | 3 | | | III-2 | 1700049E15Rik | | |
| 23271 | 2 | 3 | 4 | | IV-1 | Xk | 7504 | 26-May-15 | 310 | 2 | 3 | | | III-2 | 1700049E22Rik | | |
| 23280 | 2 | 3 | 4 | | IV-1 | Xlr3a | | | 313 | 2 | 3 | | | III-2 | 1700051A21Rik | | |
| 23281 | 2 | 3 | 4 | | IV-1 | Xlr3b | | | 317 | 2 | 3 | | | III-2 | 1700054A03Rik | | |
| 23283 | 2 | 3 | 4 | | IV-1 | Xlr4a | | | 318 | 2 | 3 | | | III-2 | 1700054K19Rik | | |
| 23295 | 2 | 3 | 4 | | IV-1 | Xpnpep3 | 63929 | 4-May-15 | 320 | 2 | 3 | | | III-2 | 1700054O13Rik | | |
| 23307 | 2 | 3 | 4 | | IV-1 | Xrcc5 | 7520 | 23-May-15 | 325 | 2 | 3 | | | III-2 | 1700057H15Rik | | |
| 23309 | 2 | 3 | 4 | | IV-1 | Xrcc6bp1 | 91419 | 4-May-15 | 329 | 2 | 3 | | | III-2 | 1700061G19Rik | | |
| 23310 | 2 | 3 | 4 | | IV-1 | Xrn1 | 54464 | 4-May-15 | 338 | 2 | 3 | | | III-2 | 1700065J11Rik | | |
| 23314 | 2 | 3 | 4 | | IV-1 | Xylt | 9942 | 4-May-15 | 346 | 2 | 3 | | | III-2 | 1700066J22Rik | | |
| 23325 | 2 | 3 | 4 | | IV-1 | Ybx3 | 8531 | 12-May-15 | 357 | 2 | 3 | | | III-2 | 1700074H08Rik | | |
| 23342 | 2 | 3 | 4 | | IV-1 | Yod1 | 55432 | 29-May-15 | 366 | 2 | 3 | | | III-2 | 1700084J12Rik | | |
| 23344 | 2 | 3 | 4 | | IV-1 | Ypel2 | 388403 | 4-May-15 | 378 | 2 | 3 | | | III-2 | 1700094D03Rik | | |
| 23365 | 2 | 3 | 4 | | IV-1 | Zap70 | 7535 | 23-May-15 | 387 | 2 | 3 | | | III-2 | 1701101E01Rik | | |
| 23366 | 2 | 3 | 4 | | IV-1 | Zar1 | 326340 | 4-May-15 | 390 | 2 | 3 | | | III-2 | 1700102H20Rik | | |
| 23373 | 2 | 3 | 4 | | IV-1 | Zbp1 | 81030 | 7-Jun-15 | 393 | 2 | 3 | | | III-2 | 1700105P06Rik | | |
| 23379 | 2 | 3 | 4 | | IV-1 | Zbtb16 | 7704 | 4-May-15 | 408 | 2 | 3 | | | III-2 | 1700112J05Rik | | |
| 23390 | 2 | 3 | 4 | | IV-1 | Zbtb32 | 27033 | 4-May-15 | 414 | 2 | 3 | | | III-2 | 1700120G07Rik | | |
| 23399 | 2 | 3 | 4 | | IV-1 | Zbtb42 | 100128927 | 4-May-15 | 417 | 2 | 3 | | | III-2 | 1700121N20Rik | | |
| 23412 | 2 | 3 | 4 | | IV-1 | Zbtb8b | 728116 | 4-May-15 | 428 | 2 | 3 | | | III-2 | 1700126H18Rik | | |
| 23413 | 2 | 3 | 4 | | IV-1 | Zbtb8os | 339487 | 21-May-15 | 431 | 2 | 3 | | | III-2 | 1810014B01Rik | | |
| 23418 | 2 | 3 | 4 | | IV-1 | Zc2hc1c | 79696 | 4-May-15 | 448 | 2 | 3 | | | III-2 | 1810026B05Rik | | |
| 23421 | 2 | 3 | 4 | | IV-1 | Zc3h12a | 80149 | 4-May-15 | 455 | 2 | 3 | | | III-2 | 1810030O07Rik | | |
| 23423 | 2 | 3 | 4 | | IV-1 | Zc3h12c | 85463 | 4-May-15 | 457 | 2 | 3 | | | III-2 | 1810037I17Rik | | |
| 23434 | 2 | 3 | 4 | | IV-1 | Zc3h8 | 84524 | 4-May-15 | 460 | 2 | 3 | | | III-2 | 1810041L15Rik | | |
| 23443 | 2 | 3 | 4 | | IV-1 | Zcchc14 | 23174 | 4-May-15 | 461 | 2 | 3 | | | III-2 | 1810043H04Rik | | |
| 23446 | 2 | 3 | 4 | | IV-1 | Zcchc18 | 644353 | 4-May-15 | 463 | 2 | 3 | | | III-2 | 2010009K17Rik | | |
| 23473 | 2 | 3 | 4 | | IV-1 | Zdhhc23 | 254887 | 4-May-15 | 477 | 2 | 3 | | | III-2 | 2010015L04Rik | | |
| 23487 | 2 | 3 | 4 | | IV-1 | Zf12 | | | 480 | 2 | 3 | | | III-2 | 2010106J10Rik | | |
| 23507 | 2 | 3 | 4 | | IV-1 | Zfp108 | | | 483 | 2 | 3 | | | III-2 | 2210015D19Rik | | |
| 23516 | 2 | 3 | 4 | | IV-1 | Zfp119b | | | 501 | 2 | 3 | | | III-2 | 2210018L21Rik | | |
| 23520 | 2 | 3 | 4 | | IV-1 | Zfp13 | 7755 | 4-May-15 | 503 | 2 | 3 | | | III-2 | 2210416O15Rik | | |
| 23530 | 2 | 3 | 4 | | IV-1 | Zfp169 | | | 514 | 2 | 3 | | | III-2 | 2310005A03Rik | | |
| 23535 | 2 | 3 | 4 | | IV-1 | Zfp185 | | | 528 | 2 | 3 | | | III-2 | 2310005F17Rik | | |
| 23573 | 2 | 3 | 4 | | IV-1 | Zfp316 | | | 529 | 2 | 3 | | | III-2 | 2310014L17Rik | | |
| 23593 | 2 | 3 | 4 | | IV-1 | Zfp36 | 7538 | 21-May-15 | 538 | 2 | 3 | | | III-2 | 2310016D03Rik | | |
| 23596 | 2 | 3 | 4 | | IV-1 | Zfp366 | | | 542 | 2 | 3 | | | III-2 | 2310036O22Rik | | |
| 23600 | 2 | 3 | 4 | | IV-1 | Zfp382 | 678 | 4-May-15 | 553 | 2 | 3 | | | III-2 | 2310050C09Rik | | |
| 23606 | 2 | 3 | 4 | | IV-1 | Zfp385a | | | 562 | 2 | 3 | | | III-2 | 2310057N15Rik | | |
| 23607 | 2 | 3 | 4 | | IV-1 | Zfp385b | | | 565 | 2 | 3 | | | III-2 | 2310068J16Rik | | |
| 23628 | 2 | 3 | 4 | | IV-1 | Zfp429 | | | 571 | 2 | 3 | | | III-2 | 2410018L13Rik | | |
| 23651 | 2 | 3 | 4 | | IV-1 | Zfp503 | | | 584 | 2 | 3 | | | III-2 | 2410012E07Rik | | |
| 23676 | 2 | 3 | 4 | | IV-1 | Zfp566 | | | 589 | 2 | 3 | | | III-2 | 2410089E03Rik | | |
| 23678 | 2 | 3 | 4 | | IV-1 | Zfp57 | 346171 | 22-May-15 | 593 | 2 | 3 | | | III-2 | 2410013J14Rik | | |
| 23701 | 2 | 3 | 4 | | IV-1 | Zfp612 | 7571 | 12-May-15 | 597 | 2 | 3 | | | III-2 | 2510002D24Rik | | |
| 23720 | 2 | 3 | 4 | | IV-1 | Zfp651 | | | 601 | 2 | 3 | | | III-2 | 2510003E04Rik | | |
| 23721 | 2 | 3 | 4 | | IV-1 | Zfp652 | | | 602 | 2 | 3 | | | III-2 | 2510009E07Rik | | |
| 23740 | 2 | 3 | 4 | | IV-1 | Zfp692 | 55667 | 4-May-15 | 603 | 2 | 3 | | | III-2 | 2610015P09Rik | | |
| 23791 | 2 | 3 | 4 | | IV-1 | Zfp81 | | | 611 | 2 | 3 | | | III-2 | 2610020H08Rik | | |
| 23869 | 2 | 3 | 4 | | IV-1 | Zfr2 | 23217 | 4-May-15 | 615 | 2 | 3 | | | III-2 | 2610027K06Rik | | |
| 23882 | 2 | 3 | 4 | | IV-1 | Zg16 | 653808 | 4-May-15 | 616 | 2 | 3 | | | III-2 | 2610028H24Rik | | |
| 23888 | 2 | 3 | 4 | | IV-1 | Zhx3 | 23051 | 4-May-15 | 618 | 2 | 3 | | | III-2 | 2610035D17Rik | | |
| 23908 | 2 | 3 | 4 | | IV-1 | Zmat1 | 84460 | 4-May-15 | 621 | 2 | 3 | | | III-2 | 2610035D17Rik | | |

Fig.22 - 39

| | | | | | | | | | | | | | | |
|---|---|---|---|---|---|---|---|---|---|---|---|---|---|---|
| 624 | 2 | 3 | | III-2 | 2610044O15Rik | | | 1342 | 2 | 3 | | III-2 | 5830416P10Rik | |
| 634 | 2 | 3 | | III-2 | 2610316D01Rik | | | 1343 | 2 | 3 | | III-2 | 5830417I10Rik | |
| 637 | 2 | 3 | | III-2 | 2610507O11Rik | | | 1348 | 2 | 3 | | III-2 | 5830444B04Rik | |
| 644 | 2 | 3 | | III-2 | 2700046G09Rik | | | 1355 | 2 | 3 | | III-2 | 6030407O03Rik | |
| 646 | 2 | 3 | | III-2 | 2700054A10Rik | | | 1359 | 2 | 3 | | III-2 | 6030443J06Rik | |
| 651 | 2 | 3 | | III-2 | 2700081O15Rik | | | 1369 | 2 | 3 | | III-2 | 6330408A02Rik | |
| 654 | 2 | 3 | | III-2 | 2700089I24Rik | | | 1373 | 2 | 3 | | III-2 | 6330416G13Rik | |
| 655 | 2 | 3 | | III-2 | 2700094K13Rik | | | 1377 | 2 | 3 | | III-2 | 6430411K18Rik | |
| 661 | 2 | 3 | | III-2 | 2810006K23Rik | | | 1379 | 2 | 3 | | III-2 | 6430531B16Rik | |
| 665 | 2 | 3 | | III-2 | 2810021J22Rik | | | 1386 | 2 | 3 | | III-2 | 6430706D22Rik | |
| 670 | 2 | 3 | | III-2 | 2810049E08Rik | | | 1393 | 2 | 3 | | III-2 | 6720489N17Rik | |
| 675 | 2 | 3 | | III-2 | 2810405F15Rik | | | 1395 | 2 | 3 | | III-2 | 6820431F20Rik | |
| 679 | 2 | 3 | | III-2 | 2810410L24Rik | | | 1397 | 2 | 3 | | III-2 | 7420461P10Rik | |
| 682 | 2 | 3 | | III-2 | 2810429I04Rik | | | 1416 | 2 | 3 | | III-2 | 8430436N08Rik | |
| 685 | 2 | 3 | | III-2 | 2810442N19Rik | | | 1422 | 2 | 3 | | III-2 | 9030617O03Rik | |
| 686 | 2 | 3 | | III-2 | 2810454H06Rik | | | 1425 | 2 | 3 | | III-2 | 9030624J02Rik | |
| 690 | 2 | 3 | | III-2 | 2810474O19Rik | | | 1429 | 2 | 3 | | III-2 | 9130015A21Rik | |
| 695 | 2 | 3 | | III-2 | 2900026A02Rik | | | 1430 | 2 | 3 | | III-2 | 9130015L21Rik | |
| 704 | 2 | 3 | | III-2 | 2900092C05Rik | | | 1442 | 2 | 3 | | III-2 | 9130409I23Rik | |
| 709 | 2 | 3 | | III-2 | 3010026O09Rik | | | 1457 | 2 | 3 | | III-2 | 9330111N05Rik | |
| 712 | 2 | 3 | | III-2 | 3110001I22Rik | | | 1458 | 2 | 3 | | III-2 | 9330117O12Rik | |
| 717 | 2 | 3 | | III-2 | 3110015C05Rik | | | 1472 | 2 | 3 | | III-2 | 9330188P03Rik | |
| 721 | 2 | 3 | | III-2 | 3110039B08Rik | | | 1482 | 2 | 3 | | III-2 | 9430037G07Rik | |
| 727 | 2 | 3 | | III-2 | 3110056K07Rik | | | 1485 | 2 | 3 | | III-2 | 9430060I03Rik | |
| 730 | 2 | 3 | | III-2 | 3110070M22Rik | | | 1486 | 2 | 3 | | III-2 | 9430069I07Rik | |
| 734 | 2 | 3 | | III-2 | 3110099E03Rik | | | 1496 | 2 | 3 | | III-2 | 9530051G07Rik | |
| 741 | 2 | 3 | | III-2 | 3830403N18Rik | | | 1500 | 2 | 3 | | III-2 | 9530068E07Rik | |
| 749 | 2 | 3 | | III-2 | 4632427E13Rik | | | 1504 | 2 | 3 | | III-2 | 9530091C08Rik | |
| 751 | 2 | 3 | | III-2 | 4632428N05Rik | | | 1512 | 2 | 3 | | III-2 | 9830147E19Rik | |
| 753 | 2 | 3 | | III-2 | 4732416N19Rik | | | 1518 | 2 | 3 | | III-2 | 9930111H07Rik | |
| 755 | 2 | 3 | | III-2 | 4732471J01Rik | | | 1523 | 2 | 3 | | III-2 | A130077B15Rik | |
| 757 | 2 | 3 | | III-2 | 4732491K20Rik | | | 1527 | 2 | 3 | | III-2 | A230009B12Rik | |
| 766 | 2 | 3 | | III-2 | 4833422C13Rik | | | 1533 | 2 | 3 | | III-2 | A230056P14Rik | |
| 793 | 2 | 3 | | III-2 | 4921525O09Rik | | | 1538 | 2 | 3 | | III-2 | A230072E10Rik | |
| 799 | 2 | 3 | | III-2 | 4921536K21Rik | | | 1539 | 2 | 3 | | III-2 | A230073K19Rik | |
| 817 | 2 | 3 | | III-2 | 4930405A21Rik | | | 1543 | 2 | 3 | | III-2 | A2m | 2 | 23-May-15 |
| 818 | 2 | 3 | | III-2 | 4930405D11Rik | | | 1552 | 2 | 3 | | III-2 | A330048O09Rik | |
| 819 | 2 | 3 | | III-2 | 4930405O17Rik | | | 1554 | 2 | 3 | | III-2 | A330050F15Rik | |
| 828 | 2 | 3 | | III-2 | 4930413F20Rik | | | 1563 | 2 | 3 | | III-2 | A430050L14Rik | |
| 831 | 2 | 3 | | III-2 | 4930414L22Rik | | | 1567 | 2 | 3 | | III-2 | A430088P11Rik | |
| 833 | 2 | 3 | | III-2 | 4930415F15Rik | | | 1579 | 2 | 3 | | III-2 | A530046M15Rik | |
| 837 | 2 | 3 | | III-2 | 4930417O22Rik | | | 1586 | 2 | 3 | | III-2 | A530072M11Rik | |
| 846 | 2 | 3 | | III-2 | 4930428E07Rik | | | 1588 | 2 | 3 | | III-2 | A530099J19Rik | |
| 848 | 2 | 3 | | III-2 | 4930428I21Rik | | | 1592 | 2 | 3 | | III-2 | A630012P03Rik | |
| 850 | 2 | 3 | | III-2 | 4930429O17Rik | | | 1606 | 2 | 3 | | III-2 | A630095N17Rik | |
| 854 | 2 | 3 | | III-2 | 4930430I24Rik | | | 1607 | 2 | 3 | | III-2 | A730006G06Rik | |
| 857 | 2 | 3 | | III-2 | 4930430J02Rik | | | 1612 | 2 | 3 | | III-2 | A730020E08Rik | |
| 861 | 2 | 3 | | III-2 | 4930432K21Rik | | | 1618 | 2 | 3 | | III-2 | A730082K24Rik | |
| 875 | 2 | 3 | | III-2 | 4930444F02Rik | | | 1626 | 2 | 3 | | III-2 | A830019L24Rik | |
| 885 | 2 | 3 | | III-2 | 4930448F12Rik | | | 1627 | 2 | 3 | | III-2 | A830052D11Rik | |
| 898 | 2 | 3 | | III-2 | 4930452G13Rik | | | 1629 | 2 | 3 | | III-2 | A830082K12Rik | |
| 911 | 2 | 3 | | III-2 | 4930459L07Rik | | | 1630 | 2 | 3 | | III-2 | A830082N09Rik | |
| 932 | 2 | 3 | | III-2 | 4930474N09Rik | | | 1635 | 2 | 3 | | III-2 | A930004O18Rik | |
| 942 | 2 | 3 | | III-2 | 4930483J18Rik | | | 1638 | 2 | 3 | | III-2 | A930006K02Rik | |
| 957 | 2 | 3 | | III-2 | 4930502E18Rik | | | 1640 | 2 | 3 | | III-2 | A930009A15Rik | |
| 970 | 2 | 3 | | III-2 | 4930507D10Rik | | | 1648 | 2 | 3 | | III-2 | A930018P22Rik | |
| 978 | 2 | 3 | | III-2 | 4930513D17Rik | | | 1650 | 2 | 3 | | III-2 | A930024E05Rik | |
| 981 | 2 | 3 | | III-2 | 4930515B02Rik | | | 1661 | 2 | 3 | | III-2 | AA543186 | |
| 996 | 2 | 3 | | III-2 | 4930521E06Rik | | | 1663 | 2 | 3 | | III-2 | AA545190 | |
| 1006 | 2 | 3 | | III-2 | 4930525O18Rik | | | 1672 | 2 | 3 | | III-2 | Aadacl3 | 126767 | 12-May-15 |
| 1011 | 2 | 3 | | III-2 | 4930527F14Rik | | | 1679 | 2 | 3 | | III-2 | Aanat | 15 | 12-May-15 |
| 1020 | 2 | 3 | | III-2 | 4930532M18Rik | | | 1686 | 2 | 3 | | III-2 | Aasdhppt | 60496 | 4-May-15 |
| 1028 | 2 | 3 | | III-2 | 4930539N22Rik | | | 1690 | 2 | 3 | | III-2 | AB041803 | |
| 1032 | 2 | 3 | | III-2 | 4930543E12Rik | | | 1695 | 2 | 3 | | III-2 | Abca13 | 154684 | 12-May-15 |
| 1062 | 2 | 3 | | III-2 | 4930557A04Rik | | | 1703 | 2 | 3 | | III-2 | Abca5 | 23461 | 4-May-15 |
| 1075 | 2 | 3 | | III-2 | 4930564B18Rik | | | 1718 | 2 | 3 | | III-2 | Abcb9 | 23457 | 4-May-15 |
| 1077 | 2 | 3 | | III-2 | 4930564D02Rik | | | 1720 | 2 | 3 | | III-2 | Abcc10 | 89845 | 4-May-15 |
| 1079 | 2 | 3 | | III-2 | 4930565N06Rik | | | 1727 | 2 | 3 | | III-2 | Abcc8 | 6833 | 24-May-15 |
| 1083 | 2 | 3 | | III-2 | 4930567B20Rik | | | 1734 | 2 | 3 | | III-2 | Abcf1 | 23 | 21-May-15 |
| 1097 | 2 | 3 | | III-2 | 4930578E06Rik | | | 1754 | 2 | 3 | | III-2 | Abhd16b | 140701 | 4-May-15 |
| 1106 | 2 | 3 | | III-2 | 4930583P06Rik | | | 1769 | 2 | 3 | | III-2 | Abl2 | 27 | 12-May-15 |
| 1113 | 2 | 3 | | III-2 | 4930593A02Rik | | | 1778 | 2 | 3 | | III-2 | Abtb1 | 80325 | 4-May-15 |
| 1117 | 2 | 3 | | III-2 | 4930596O02Rik | | | 1780 | 2 | 3 | | III-2 | Acaa1a | |
| 1123 | 2 | 3 | | III-2 | 4931403E22Rik | | | 1789 | 2 | 3 | | III-2 | Acad9 | 28976 | 4-May-15 |
| 1125 | 2 | 3 | | III-2 | 4931406B18Rik | | | 1798 | 2 | 3 | | III-2 | Acap3 | 116983 | 4-May-15 |
| 1132 | 2 | 3 | | III-2 | 4931412M21 | | | 1805 | 2 | 3 | | III-2 | Acbd6 | 84320 | 14-May-15 |
| 1135 | 2 | 3 | | III-2 | 4931419H13Rik | | | 1813 | 2 | 3 | | III-2 | Acer1 | 125981 | 21-May-15 |
| 1137 | 2 | 3 | | III-2 | 4931423N10Rik | | | 1828 | 2 | 3 | | III-2 | Aco2 | 50 | 12-May-15 |
| 1140 | 2 | 3 | | III-2 | 4931429I11Rik | | | 1838 | 2 | 3 | | III-2 | Acot6 | 641372 | 4-May-15 |
| 1147 | 2 | 3 | | III-2 | 4931440F15Rik | | | 1876 | 2 | 3 | | III-2 | Actbl2 | 345651 | 4-May-15 |
| 1152 | 2 | 3 | | III-2 | 4932411N23Rik | | | 1881 | 2 | 3 | | III-2 | Actl11 | |
| 1166 | 2 | 3 | | III-2 | 4932443I19Rik | | | 1882 | 2 | 3 | | III-2 | Actl6a | 86 | 3-May-15 |
| 1169 | 2 | 3 | | III-2 | 4933408J14Rik | | | 1885 | 2 | 3 | | III-2 | Actl7b | 10880 | 12-May-15 |
| 1190 | 2 | 3 | | III-2 | 4933405E24Rik | | | 1891 | 2 | 3 | | III-2 | Actr10 | 55860 | 4-May-15 |
| 1209 | 2 | 3 | | III-2 | 4933408N05Rik | | | 1907 | 2 | 3 | | III-2 | Acvr2b | 93 | 12-May-15 |
| 1213 | 2 | 3 | | III-2 | 4933411G06Rik | | | 1917 | 2 | 3 | | III-2 | Adam10 | 102 | 24-May-15 |
| 1217 | 2 | 3 | | III-2 | 4933412K12Rik | | | 1918 | 2 | 3 | | III-2 | Adam11 | 4185 | 4-May-15 |
| 1219 | 2 | 3 | | III-2 | 4933412O06Rik | | | 1923 | 2 | 3 | | III-2 | Adam19 | 8728 | 4-May-15 |
| 1252 | 2 | 3 | | III-2 | 4933429O19Rik | | | 1926 | 2 | 3 | | III-2 | Adam2 | 2515 | 4-May-15 |
| 1259 | 2 | 3 | | III-2 | 4933432G23Rik | | | 1927 | 2 | 3 | | III-2 | Adam20 | 8748 | 4-May-15 |
| 1279 | 2 | 3 | | III-2 | 4933440M02Rik | | | 1932 | 2 | 3 | | III-2 | Adam25 | |
| 1292 | 2 | 3 | | III-2 | 5330411J13Rik | | | 1955 | 2 | 3 | | III-2 | Adamts14 | 140766 | 10-May-15 |
| 1294 | 2 | 3 | | III-2 | 5330417C22Rik | | | 1958 | 2 | 3 | | III-2 | Adamts17 | 170691 | 17-May-15 |
| 1305 | 2 | 3 | | III-2 | 5430417L22Rik | | | 1960 | 2 | 3 | | III-2 | Adamts19 | 171019 | 4-May-15 |
| 1321 | 2 | 3 | | III-2 | 5730405O15Rik | | | 1963 | 2 | 3 | | III-2 | Adamts3 | 9508 | May-15 |
| 1327 | 2 | 3 | | III-2 | 5730422E09Rik | | | 1985 | 2 | 3 | | III-2 | Adck2 | 90956 | 4-May-15 |
| 1329 | 2 | 3 | | III-2 | 5730455P16Rik | | | 2004 | 2 | 3 | | III-2 | Adgb | 79747 | 4-May-15 |

Fig.22 - 40

| | | | | | | | |
|---|---|---|---|---|---|---|---|
| 2016 | 2 | 3 | III-2 | Adipor2 | 79602 | 31-May-15 |
| 2021 | 2 | 3 | III-2 | Adnp2 | 22850 | 4-May-15 |
| 2025 | 2 | 3 | III-2 | Adora2b | 136 | 24-May-15 |
| 2028 | 2 | 3 | III-2 | Adprh | 141 | 12-May-15 |
| 2031 | 2 | 3 | III-2 | Adprm | 56985 | 4-May-15 |
| 2042 | 2 | 3 | III-2 | Adrbk2 | 157 | 14-May-15 |
| 2046 | 2 | 3 | III-2 | Adss | 159 | 4-May-15 |
| 2053 | 2 | 3 | III-2 | AF067063 | | |
| 2056 | 2 | 3 | III-2 | AF357359 | | |
| 2066 | 2 | 3 | III-2 | Aff2 | 2534 | 12-May-15 |
| 2069 | 2 | 3 | III-2 | Afg3l1 | 172 | 12-May-15 |
| 2074 | 2 | 3 | III-2 | Aftph | 54812 | 4-May-15 |
| 2075 | 2 | 3 | III-2 | Aga | 175 | 12-May-15 |
| 2079 | 2 | 3 | III-2 | Agbl1 | 123624 | 23-May-15 |
| 2083 | 2 | 3 | III-2 | Agbl5 | 60509 | 23-May-15 |
| 2085 | 2 | 3 | III-2 | Agfg1 | 3267 | 4-May-15 |
| 2095 | 2 | 3 | III-2 | Ago4 | 192670 | 4-May-15 |
| 2099 | 2 | 3 | III-2 | Agpat4 | 56895 | 4-May-15 |
| 2101 | 2 | 3 | III-2 | Agpat6 | 137964 | 4-May-15 |
| 2112 | 2 | 3 | III-2 | Agtr2 | 186 | 4-May-15 |
| 2114 | 2 | 3 | III-2 | Agxt | 189 | 23-May-15 |
| 2116 | 2 | 3 | III-2 | Ahctf1 | 25909 | 4-May-15 |
| 2119 | 2 | 3 | III-2 | Ahcyl2 | 23382 | 3-May-15 |
| 2124 | 2 | 3 | III-2 | Ahr | 57491 | 10-Jun-15 |
| 2125 | 2 | 3 | III-2 | Ahsa1 | 10598 | 4-May-15 |
| 2126 | 2 | 3 | III-2 | Ahsa2 | 130872 | 4-May-15 |
| 2132 | 2 | 3 | III-2 | AI314180 | | |
| 2137 | 2 | 3 | III-2 | AI427809 | | |
| 2144 | 2 | 3 | III-2 | AI504432 | | |
| 2148 | 2 | 3 | III-2 | AI597479 | | |
| 2156 | 2 | 3 | III-2 | AI839979 | | |
| 2158 | 2 | 3 | III-2 | AI847159 | | |
| 2161 | 2 | 3 | III-2 | AI854703 | | |
| 2172 | 2 | 3 | III-2 | Aim1l | 55057 | 4-May-15 |
| 2175 | 2 | 3 | III-2 | Aimp2 | 7965 | 4-May-15 |
| 2181 | 2 | 3 | III-2 | Ajuba | 84962 | 4-May-15 |
| 2186 | 2 | 3 | III-2 | Ak3 | 56808 | 7-Jun-15 |
| 2198 | 2 | 3 | III-2 | Akap17b | | |
| 2206 | 2 | 3 | III-2 | Akap8l | 26993 | 12-May-15 |
| 2210 | 2 | 3 | III-2 | Akirin2 | 55122 | 4-May-15 |
| 2227 | 2 | 3 | III-2 | Akr1c1 | | |
| 2228 | 2 | 3 | III-2 | Akr1d1 | 6718 | 4-May-15 |
| 2232 | 2 | 3 | III-2 | Akt1s1 | 84335 | 4-May-15 |
| 2242 | 2 | 3 | III-2 | Aldh18a1 | 5832 | 23-May-15 |
| 2260 | 2 | 3 | III-2 | Aldh9a1 | 223 | 23-May-15 |
| 2269 | 2 | 3 | III-2 | Alg12 | 79087 | 23-May-15 |
| 2271 | 2 | 3 | III-2 | Alg14 | 199857 | 5-May-15 |
| 2272 | 2 | 3 | III-2 | Alg2 | 85365 | 13-Jun-15 |
| 2273 | 2 | 3 | III-2 | Alg3 | 10195 | 22-May-15 |
| 2275 | 2 | 3 | III-2 | Alg6 | 29929 | 23-May-15 |
| 2278 | 2 | 3 | III-2 | Alk | 238 | 26-May-15 |
| 2282 | 2 | 3 | III-2 | Alkbh4 | 54784 | 4-May-15 |
| 2284 | 2 | 3 | III-2 | Alkbh6 | 84964 | 4-May-15 |
| 2287 | 2 | 3 | III-2 | Allc | 55821 | 20-May-15 |
| 2288 | 2 | 3 | III-2 | Alms1 | 7840 | 22-May-15 |
| 2292 | 2 | 3 | III-2 | Alox12e | 245 | 4-May-15 |
| 2309 | 2 | 3 | III-2 | Alx3 | 257 | 12-May-15 |
| 2321 | 2 | 3 | III-2 | Amelx | 265 | 12-May-15 |
| 2322 | 2 | 3 | III-2 | Amer1 | 139285 | 4-May-15 |
| 2324 | 2 | 3 | III-2 | Amer3 | 205147 | 4-May-15 |
| 2325 | 2 | 3 | III-2 | Amfr | 267 | 29-May-15 |
| 2334 | 2 | 3 | III-2 | Amn | 81693 | 7-Jun-15 |
| 2351 | 2 | 3 | III-2 | Anapc1 | 64682 | 12-May-15 |
| 2352 | 2 | 3 | III-2 | Anapc10 | 10393 | 4-May-15 |
| 2354 | 2 | 3 | III-2 | Anapc13 | 25847 | 4-May-15 |
| 2357 | 2 | 3 | III-2 | Anapc2 | 29882 | 4-May-15 |
| 2366 | 2 | 3 | III-2 | Ang6 | | |
| 2383 | 2 | 3 | III-2 | Ankdd1b | 728780 | 4-May-15 |
| 2385 | 2 | 3 | III-2 | Ankhl1 | 162282 | 4-May-15 |
| 2386 | 2 | 3 | III-2 | Ankfy1 | 51479 | 4-May-15 |
| 2392 | 2 | 3 | III-2 | Ankmy1 | 51281 | 21-May-15 |
| 2404 | 2 | 3 | III-2 | Ankrd17 | 26057 | 4-May-15 |
| 2410 | 2 | 3 | III-2 | Ankrd27 | 84079 | 4-May-15 |
| 2414 | 2 | 3 | III-2 | Ankrd33 | 341405 | 4-May-15 |
| 2415 | 2 | 3 | III-2 | Ankrd33b | 651746 | 4-May-15 |
| 2417 | 2 | 3 | III-2 | Ankrd34b | 340120 | 4-May-15 |
| 2418 | 2 | 3 | III-2 | Ankrd34c | 390616 | 4-May-15 |
| 2423 | 2 | 3 | III-2 | Ankrd40 | 91369 | 21-May-15 |
| 2424 | 2 | 3 | III-2 | Ankrd42 | 338699 | 4-May-15 |
| 2432 | 2 | 3 | III-2 | Ankrd54 | 129138 | 4-May-15 |
| 2435 | 2 | 3 | III-2 | Ankrd60 | 140731 | 12-May-15 |
| 2442 | 2 | 3 | III-2 | Anks1b | 56899 | 4-May-15 |
| 2443 | 2 | 3 | III-2 | Anks3 | 124401 | 12-May-15 |
| 2451 | 2 | 3 | III-2 | Ano2 | 57101 | 4-May-15 |
| 2452 | 2 | 3 | III-2 | Ano3 | 63982 | 21-May-15 |
| 2456 | 2 | 3 | III-2 | Ano7 | 50836 | 4-May-15 |
| 2466 | 2 | 3 | III-2 | Anxa1 | 301 | 24-May-15 |
| 2468 | 2 | 3 | III-2 | Anxa11 | 311 | 10-May-15 |
| 2475 | 2 | 3 | III-2 | Anxa7 | 310 | 4-May-15 |
| 2487 | 2 | 3 | III-2 | Ap1b1 | 162 | 4-May-15 |
| 2496 | 2 | 3 | III-2 | Ap2a2 | 161 | 4-May-15 |
| 2507 | 2 | 3 | III-2 | Ap4b1 | 10717 | 12-May-15 |
| 2509 | 2 | 3 | III-2 | Ap4m1 | 9179 | 4-May-15 |
| 2511 | 2 | 3 | III-2 | Ap5b1 | 91056 | 4-May-15 |
| 2513 | 2 | 3 | III-2 | Ap5s1 | 55317 | 4-May-15 |
| 2514 | 2 | 3 | III-2 | Ap5z1 | 9907 | 4-May-15 |
| 2515 | 2 | 3 | III-2 | Apaf1 | 317 | 12-May-15 |
| 2517 | 2 | 3 | III-2 | Apba2 | 321 | 12-May-15 |
| 2522 | 2 | 3 | III-2 | Apbb3 | 10307 | 4-May-15 |
| 2528 | 2 | 3 | III-2 | Apela | 109506013 | 12-May-15 |
| 2531 | 2 | 3 | III-2 | Aph1a | 51107 | 4-May-15 |
| 2532 | 2 | 3 | III-2 | Aph1b | 83464 | 4-May-15 |
| 2534 | 2 | 3 | III-2 | Api5 | 8539 | 4-May-15 |
| 2538 | 2 | 3 | III-2 | Apln | 8862 | 17-May-15 |
| 2542 | 2 | 3 | III-2 | Aplnr | 57136 | 4-May-15 |
| 2569 | 2 | 3 | III-2 | Apol7c | | |
| 2570 | 2 | 3 | III-2 | Apol7d | | |
| 2577 | 2 | 3 | III-2 | Apon | | |
| 2579 | 2 | 3 | III-2 | Apool | 139322 | 4-May-15 |
| 2585 | 2 | 3 | III-2 | Appl2 | 55198 | 7-Jun-15 |
| 2602 | 2 | 3 | III-2 | Arap1 | 116985 | 4-May-15 |
| 2609 | 2 | 3 | III-2 | Arf1 | 375 | 7-Jun-15 |
| 2626 | 2 | 3 | III-2 | Arhgap1 | 392 | 4-May-15 |
| 2630 | 2 | 3 | III-2 | Arhgap15 | 55843 | 4-May-15 |
| 2632 | 2 | 3 | III-2 | Arhgap17 | 55114 | 4-May-15 |
| 2638 | 2 | 3 | III-2 | Arhgap22 | 58504 | 14-May-15 |
| 2644 | 2 | 3 | III-2 | Arhgap27os3 | | |
| 2645 | 2 | 3 | III-2 | Arhgap28 | 79822 | 31-May-15 |
| 2647 | 2 | 3 | III-2 | Arhgap30 | 257106 | 12-May-15 |
| 2652 | 2 | 3 | III-2 | Arhgap35 | 2909 | 17-May-15 |
| 2654 | 2 | 3 | III-2 | Arhgap39 | 80728 | 21-May-15 |
| 2664 | 2 | 3 | III-2 | Arhgdib | 397 | 17-May-15 |
| 2667 | 2 | 3 | III-2 | Arhgef10 | 9639 | 12-May-15 |
| 2670 | 2 | 3 | III-2 | Arhgef12 | 23365 | 12-May-15 |
| 2675 | 2 | 3 | III-2 | Arhgef19 | 128272 | 4-May-15 |
| 2677 | 2 | 3 | III-2 | Arhgef25 | 115557 | 4-May-15 |
| 2678 | 2 | 3 | III-2 | Arhgef26 | 26084 | 4-May-15 |
| 2681 | 2 | 3 | III-2 | Arhgef33 | 100271715 | 12-May-15 |
| 2684 | 2 | 3 | III-2 | Arhgef39 | 84904 | 4-May-15 |
| 2690 | 2 | 3 | III-2 | Arhgef9 | 23229 | 23-May-15 |
| 2695 | 2 | 3 | III-2 | Arid3b | 10620 | 28-May-15 |
| 2702 | 2 | 3 | III-2 | Arih2 | 10425 | 4-May-15 |
| 2707 | 2 | 3 | III-2 | Arl13b | 200894 | 23-May-15 |
| 2713 | 2 | 3 | III-2 | Arl2 | 402 | 4-May-15 |
| 2725 | 2 | 3 | III-2 | Arl6ip5 | 10550 | 12-May-15 |
| 2735 | 2 | 3 | III-2 | Armc4 | 55130 | 28-May-15 |
| 2736 | 2 | 3 | III-2 | Armc5 | 79798 | 4-May-15 |
| 2739 | 2 | 3 | III-2 | Armc8 | 25852 | 4-May-15 |
| 2740 | 2 | 3 | III-2 | Armc9 | 80210 | 12-May-15 |
| 2744 | 2 | 3 | III-2 | Armcx4 | 100131755 | 12-May-15 |
| 2761 | 2 | 3 | III-2 | Arrb1 | 408 | 17-May-15 |
| 2773 | 2 | 3 | III-2 | Arsk | 153642 | 23-May-15 |
| 2788 | 2 | 3 | III-2 | Asah2 | 56624 | 4-May-15 |
| 2805 | 2 | 3 | III-2 | Asb4 | 51666 | 4-May-15 |
| 2808 | 2 | 3 | III-2 | Asb7 | 140460 | 4-May-15 |
| 2814 | 2 | 3 | III-2 | Ascl1 | 429 | 23-May-15 |
| 2818 | 2 | 3 | III-2 | Ascl3 | 56676 | 4-May-15 |
| 2819 | 2 | 3 | III-2 | Asf1a | 25842 | 4-May-15 |
| 2823 | 2 | 3 | III-2 | Ash1l | 55870 | 4-May-15 |
| 2841 | 2 | 3 | III-2 | Aspm | 259266 | 23-May-15 |
| 2845 | 2 | 3 | III-2 | Asrgl1 | 80150 | 12-May-15 |
| 2848 | 2 | 3 | III-2 | Ast1 | 431705 | 4-May-15 |
| 2851 | 2 | 3 | III-2 | Asun | 55726 | 4-May-15 |
| 2855 | 2 | 3 | III-2 | Asz1 | 136991 | 4-May-15 |
| 2859 | 2 | 3 | III-2 | Atad3a | 55210 | 4-May-15 |
| 2866 | 2 | 3 | III-2 | Atf1 | 466 | 7-Jun-15 |
| 2872 | 2 | 3 | III-2 | Atf6b | 1388 | 4-May-15 |
| 2876 | 2 | 3 | III-2 | Atg10 | 83734 | 4-May-15 |
| 2878 | 2 | 3 | III-2 | Atg12 | 9140 | 21-May-15 |
| 2879 | 2 | 3 | III-2 | Atg13 | 9776 | 28-May-15 |
| 2880 | 2 | 3 | III-2 | Atg14 | 22863 | 28-May-15 |
| 2884 | 2 | 3 | III-2 | Atg2b | 55102 | 21-May-15 |
| 2888 | 2 | 3 | III-2 | Atg4c | 84938 | 21-May-15 |
| 2895 | 2 | 3 | III-2 | Atic | 471 | 4-May-15 |
| 2896 | 2 | 3 | III-2 | Atl1 | 51062 | 7-Jun-15 |
| 2900 | 2 | 3 | III-2 | Atmin | 23300 | 4-May-15 |
| 2901 | 2 | 3 | III-2 | Atn1 | 1822 | 23-May-15 |
| 2903 | 2 | 3 | III-2 | Atoh7 | 220202 | 23-May-15 |
| 2909 | 2 | 3 | III-2 | Atp11a | 23250 | 4-May-15 |
| 2911 | 2 | 3 | III-2 | Atp11c | 286410 | 4-May-15 |
| 2914 | 2 | 3 | III-2 | Atp13a2 | 23400 | 4-May-15 |
| 2922 | 2 | 3 | III-2 | Atp1b1 | 481 | 12-May-15 |
| 2934 | 2 | 3 | III-2 | Atp2c2 | 9914 | 4-May-15 |
| 2937 | 2 | 3 | III-2 | Atp5a1 | 498 | 12-May-15 |
| 2943 | 2 | 3 | III-2 | Atp5g1 | 516 | 4-May-15 |
| 2953 | 2 | 3 | III-2 | Atp5sl | 55101 | 4-May-15 |
| 2975 | 2 | 3 | III-2 | Atp6v1f | 9296 | 4-May-15 |
| 2983 | 2 | 3 | III-2 | Atp8a2 | 51761 | 4-May-15 |
| 2984 | 2 | 3 | III-2 | Atp8b1 | 5205 | 23-May-15 |
| 2986 | 2 | 3 | III-2 | Atp8b3 | 148229 | 4-May-15 |
| 2991 | 2 | 3 | III-2 | Atpaf1 | 64756 | 4-May-15 |
| 2996 | 2 | 3 | III-2 | Atrip | 84126 | 4-May-15 |
| 2999 | 2 | 3 | III-2 | Atrx | 546 | 23-May-15 |
| 3000 | 2 | 3 | III-2 | Atxn1 | 6310 | 23-May-15 |
| 3004 | 2 | 3 | III-2 | Atxn2l | 11273 | 4-May-15 |
| 3009 | 2 | 3 | III-2 | Atxn7l3 | 56970 | 12-May-15 |
| 3010 | 2 | 3 | III-2 | Atxn7l3b | 552883 | 12-May-15 |
| 3031 | 2 | 3 | III-2 | Aurka | 6790 | 24-May-15 |
| 3051 | 2 | 3 | III-2 | AW209491 | | |
| 3055 | 2 | 3 | III-2 | AW551984 | | |
| 3056 | 2 | 3 | III-2 | AW554918 | | |
| 3066 | 2 | 3 | III-2 | AY512931 | | |

Fig.22 - 41

| | | | | | | | | | | | | | | | | |
|---|---|---|---|---|---|---|---|---|---|---|---|---|---|---|---|---|
| 3072 | 2 | 3 | | | III-2 | Azin1 | 51582 | 4-May-15 | 3563 | 2 | 3 | | | III-2 | Bud13 | 84811 | 12-May-15 |
| 3074 | 2 | 3 | | | III-2 | B020004J07Rik | | | 3569 | 2 | 3 | | | III-2 | Bzw2 | 28969 | 4-May-15 |
| 3088 | 2 | 3 | | | III-2 | B230216G23Rik | | | 3574 | 2 | 3 | | | III-2 | C030018K13Rik | | |
| 3090 | 2 | 3 | | | III-2 | B230217C12Rik | | | 3576 | 2 | 3 | | | III-2 | C030029H02Rik | | |
| 3092 | 2 | 3 | | | III-2 | B230219D22Rik | | | 3581 | 2 | 3 | | | III-2 | C030046E11Rik | | |
| 3093 | 2 | 3 | | | III-2 | B230312C02Rik | | | 3583 | 2 | 3 | | | III-2 | C130026L21Rik | | |
| 3095 | 2 | 3 | | | III-2 | B230323A14Rik | | | 3584 | 2 | 3 | | | III-2 | C130026L21Rik | | |
| 3107 | 2 | 3 | | | III-2 | B3gat3 | 26229 | 23-May-15 | 3590 | 2 | 3 | | | III-2 | C130060K24Rik | | |
| 3108 | 2 | 3 | | | III-2 | B3glct | 145173 | 23-May-15 | 3604 | 2 | 3 | | | III-2 | C1ql2 | 165257 | 4-May-15 |
| 3111 | 2 | 3 | | | III-2 | B3gnt3 | 10331 | 4-May-15 | 3606 | 2 | 3 | | | III-2 | C1ql4 | 338761 | 4-May-15 |
| 3118 | 2 | 3 | | | III-2 | B3gntl1 | 146712 | 4-May-15 | 3618 | 2 | 3 | | | III-2 | C1s1 | | |
| 3127 | 2 | 3 | | | III-2 | B4galt1 | 2683 | 23-May-15 | 3621 | 2 | 3 | | | III-2 | C230004F18Rik | | |
| 3134 | 2 | 3 | | | III-2 | B630005N14Rik | | | 3622 | 2 | 3 | | | III-2 | C230024C17Rik | | |
| 3139 | 2 | 3 | | | III-2 | B930025P03Rik | | | 3628 | 2 | 3 | | | III-2 | C230091D08Rik | | |
| 3143 | 2 | 3 | | | III-2 | B9d1 | 27077 | 4-May-15 | 3631 | 2 | 3 | | | III-2 | C2cd3 | 26005 | 12-May-15 |
| 3146 | 2 | 3 | | | III-2 | Baat | 570 | 4-May-15 | 3639 | 2 | 3 | | | III-2 | C330007P06Rik | | |
| 3153 | 2 | 3 | | | III-2 | Bad | 572 | 4-May-15 | 3643 | 2 | 3 | | | III-2 | C330018D20Rik | | |
| 3157 | 2 | 3 | | | III-2 | Bag4 | 9530 | 3-May-15 | 3644 | 2 | 3 | | | III-2 | C330021F23Rik | | |
| 3162 | 2 | 3 | | | III-2 | Bai1 | 575 | 4-May-15 | 3652 | 2 | 3 | | | III-2 | C430002N11Rik | | |
| 3173 | 2 | 3 | | | III-2 | Banf2 | 140836 | 4-May-15 | 3661 | 2 | 3 | | | III-2 | C5ar1 | 728 | 12-May-15 |
| 3174 | 2 | 3 | | | III-2 | Bank1 | 55024 | 4-May-15 | 3665 | 2 | 3 | | | III-2 | C630031E19Rik | | |
| 3176 | 2 | 3 | | | III-2 | Bap1 | 8314 | 7-Jun-15 | 3669 | 2 | 3 | | | III-2 | C730027H18Rik | | |
| 3179 | 2 | 3 | | | III-2 | Barhl2 | 343472 | 28-May-15 | 3675 | 2 | 3 | | | III-2 | C86695 | | |
| 3189 | 2 | 3 | | | III-2 | Baz2a | 11176 | 4-May-15 | 3685 | 2 | 3 | | | III-2 | C920006O11Rik | | |
| 3200 | 2 | 3 | | | III-2 | Bbox1 | 8424 | 12-May-15 | 3689 | 2 | 3 | | | III-2 | Casp1 | 79886 | 12-May-15 |
| 3202 | 2 | 3 | | | III-2 | Bbs10 | 79738 | 23-May-15 | 3691 | 2 | 3 | | | III-2 | Cab39l | 81617 | 4-May-15 |
| 3210 | 2 | 3 | | | III-2 | BC002163 | | | 3706 | 2 | 3 | | | III-2 | Cacna1c | 775 | 23-May-15 |
| 3212 | 2 | 3 | | | III-2 | BC003985 | | | 3710 | 2 | 3 | | | III-2 | Cacna1g | 8913 | 4-May-15 |
| 3217 | 2 | 3 | | | III-2 | BC005764 | | | 3717 | 2 | 3 | | | III-2 | Cacna2d4 | 93589 | 4-May-15 |
| 3238 | 2 | 3 | | | III-2 | BC027231 | | | 3720 | 2 | 3 | | | III-2 | Cacnb3 | 784 | 4-May-15 |
| 3242 | 2 | 3 | | | III-2 | BC030307 | | | 3724 | 2 | 3 | | | III-2 | Cacng3 | 10368 | 4-May-15 |
| 3253 | 2 | 3 | | | III-2 | BC037034 | | | 3726 | 2 | 3 | | | III-2 | Cacng5 | 27091 | 4-May-15 |
| 3256 | 2 | 3 | | | III-2 | BC039986 | | | 3731 | 2 | 3 | | | III-2 | Cacul1 | 143384 | 4-May-15 |
| 3262 | 2 | 3 | | | III-2 | BC048602 | | | 3738 | 2 | 3 | | | III-2 | Cadm3 | 57863 | 4-May-15 |
| 3271 | 2 | 3 | | | III-2 | BC049762 | | | 3751 | 2 | 3 | | | III-2 | Calhm2 | 51063 | 12-May-15 |
| 3273 | 2 | 3 | | | III-2 | BC051142 | | | 3753 | 2 | 3 | | | III-2 | Calm2 | 805 | 12-May-15 |
| 3276 | 2 | 3 | | | III-2 | BC051628 | | | 3765 | 2 | 3 | | | III-2 | Camk1 | 8536 | 7-Jun-15 |
| 3280 | 2 | 3 | | | III-2 | BC053393 | | | 3772 | 2 | 3 | | | III-2 | Camk2n1 | 55450 | 4-May-15 |
| 3283 | 2 | 3 | | | III-2 | BC055324 | | | 3779 | 2 | 3 | | | III-2 | Caml | 819 | 4-May-15 |
| 3285 | 2 | 3 | | | III-2 | BC061194 | | | 3782 | 2 | 3 | | | III-2 | Camsap2 | 23271 | 4-May-15 |
| 3286 | 2 | 3 | | | III-2 | BC061195 | | | 3786 | 2 | 3 | | | III-2 | Cand1 | 55832 | 4-May-15 |
| 3291 | 2 | 3 | | | III-2 | BC068157 | | | 3789 | 2 | 3 | | | III-2 | Canx | 821 | 17-May-15 |
| 3294 | 2 | 3 | | | III-2 | BC089491 | | | 3806 | 2 | 3 | | | III-2 | Capns1 | 826 | 12-May-15 |
| 3298 | 2 | 3 | | | III-2 | BC100461 | | | 3813 | 2 | 3 | | | III-2 | Capza2 | 830 | 4-May-15 |
| 3303 | 2 | 3 | | | III-2 | Bcam | 4059 | 7-Jun-15 | 3814 | 2 | 3 | | | III-2 | Capza3 | 93661 | 4-May-15 |
| 3311 | 2 | 3 | | | III-2 | Bcas2 | 10286 | 4-May-15 | 3818 | 2 | 3 | | | III-2 | Car11 | | |
| 3323 | 2 | 3 | | | III-2 | Bcl10 | 8915 | 12-May-15 | 3840 | 2 | 3 | | | III-2 | Carm1 | 10498 | 3-May-15 |
| 3332 | 2 | 3 | | | III-2 | Bcl2l10 | 10017 | 12-May-15 | 3850 | 2 | 3 | | | III-2 | Cask | 8573 | 4-May-15 |
| 3344 | 2 | 3 | | | III-2 | Bcl7c | 9274 | 4-May-15 | 3857 | 2 | 3 | | | III-2 | Casp3 | 836 | |
| 3346 | 2 | 3 | | | III-2 | Bcl9l | 283149 | 4-May-15 | 3858 | 2 | 3 | | | III-2 | Casp4 | 837 | |
| 3351 | 2 | 3 | | | III-2 | Bcorl1 | 63035 | 21-May-15 | 3861 | 2 | 3 | | | III-2 | Casp8 | 841 | 23-May-15 |
| 3353 | 2 | 3 | | | III-2 | Bcs1l | 617 | 23-May-15 | 3862 | 2 | 3 | | | III-2 | Casp8ap2 | 9994 | 12-May-15 |
| 3359 | 2 | 3 | | | III-2 | Bdp1 | 55814 | 7-Jun-15 | 3872 | 2 | 3 | | | III-2 | Catsper1 | 117144 | 23-May-15 |
| 3361 | 2 | 3 | | | III-2 | Becn1 | 8678 | 31-May-15 | 3873 | 2 | 3 | | | III-2 | Catsper2 | 117155 | 23-May-15 |
| 3362 | 2 | 3 | | | III-2 | Becn2 | 441925 | 4-May-15 | 3877 | 2 | 3 | | | III-2 | Catsperd | 257062 | 4-May-15 |
| 3365 | 2 | 3 | | | III-2 | Bend4 | 389206 | 4-May-15 | 3884 | 2 | 3 | | | III-2 | Cbfa2t3 | 863 | 4-May-15 |
| 3368 | 2 | 3 | | | III-2 | Bend7 | 222389 | 4-May-15 | 3901 | 2 | 3 | | | III-2 | Cbx1 | 84733 | 4-May-15 |
| 3373 | 2 | 3 | | | III-2 | Betl1 | 51272 | 4-May-15 | 3904 | 2 | 3 | | | III-2 | Cbx5 | 23468 | 4-May-15 |
| 3379 | 2 | 3 | | | III-2 | Bfsp1 | 631 | 4-May-15 | 3906 | 2 | 3 | | | III-2 | Cbx7 | 23492 | 21-May-15 |
| 3386 | 2 | 3 | | | III-2 | Bhlha9 | 727857 | 4-May-15 | 3909 | 2 | 3 | | | III-2 | Cc2d1a | 54862 | 31-May-15 |
| 3389 | 2 | 3 | | | III-2 | Bhlhe23 | 128408 | 4-May-15 | 3910 | 2 | 3 | | | III-2 | Cc2d1b | 200014 | 28-May-15 |
| 3390 | 2 | 3 | | | III-2 | Bhlhe40 | 8553 | 4-May-15 | 3913 | 2 | 3 | | | III-2 | Ccar2 | 57805 | 29-May-15 |
| 3394 | 2 | 3 | | | III-2 | Bicc1 | 80114 | 4-May-15 | 3930 | 2 | 3 | | | III-2 | Ccdc114 | 93233 | 4-May-15 |
| 3396 | 2 | 3 | | | III-2 | Bicd2 | 23299 | 4-May-15 | 3939 | 2 | 3 | | | III-2 | Ccdc125 | 202243 | 4-May-15 |
| 3397 | 2 | 3 | | | III-2 | Bid | 637 | 17-May-15 | 3940 | 2 | 3 | | | III-2 | Ccdc126 | 90693 | 4-May-15 |
| 3402 | 2 | 3 | | | III-2 | Birc2 | 329 | 24-May-15 | 3951 | 2 | 3 | | | III-2 | Ccdc14 | 64770 | 12-May-15 |
| 3406 | 2 | 3 | | | III-2 | Birc7 | 79444 | 23-May-15 | 3952 | 2 | 3 | | | III-2 | Ccdc141 | 285025 | 4-May-15 |
| 3407 | 2 | 3 | | | III-2 | Bivm | 54841 | 4-May-15 | 3957 | 2 | 3 | | | III-2 | Ccdc148 | 130940 | 12-May-15 |
| 3412 | 2 | 3 | | | III-2 | Blnk | 29760 | 17-May-15 | 3961 | 2 | 3 | | | III-2 | Ccdc151 | 115948 | 28-May-15 |
| 3414 | 2 | 3 | | | III-2 | Bloc1s2 | 282991 | 4-May-15 | 3965 | 2 | 3 | | | III-2 | Ccdc155 | 147872 | 14-May-15 |
| 3424 | 2 | 3 | | | III-2 | Bmp1 | 649 | 12-May-15 | 3971 | 2 | 3 | | | III-2 | Ccdc163 | | |
| 3429 | 2 | 3 | | | III-2 | Bmp3 | 651 | 12-May-15 | 3972 | 2 | 3 | | | III-2 | Ccdc166 | 100130274 | 4-May-15 |
| 3445 | 2 | 3 | | | III-2 | Bnip1 | 662 | 4-May-15 | 3973 | 2 | 3 | | | III-2 | Ccdc167 | 194467 | 4-May-15 |
| 3458 | 2 | 3 | | | III-2 | Bop1 | 23246 | 4-May-15 | 3975 | 2 | 3 | | | III-2 | Ccdc17 | 149483 | |
| 3470 | 2 | 3 | | | III-2 | Bpifb3 | 359710 | 4-May-15 | 3984 | 2 | 3 | | | III-2 | Ccdc178 | 374864 | 12-May-15 |
| 3474 | 2 | 3 | | | III-2 | Bpifb9a | | | 3987 | 2 | 3 | | | III-2 | Ccdc183 | 84960 | |
| 3476 | 2 | 3 | | | III-2 | Bpifc | 254240 | 4-May-15 | 4002 | 2 | 3 | | | III-2 | Ccdc34 | 91057 | |
| 3480 | 2 | 3 | | | III-2 | Brap | 8315 | 7-Jun-15 | 4013 | 2 | 3 | | | III-2 | Ccdc50 | 152137 | 23-May-15 |
| 3485 | 2 | 3 | | | III-2 | Brd1 | 23774 | 12-May-15 | 4017 | 2 | 3 | | | III-2 | Ccdc55 | 84081 | 4-May-15 |
| 3486 | 2 | 3 | | | III-2 | Brd2 | 6046 | 12-May-15 | 4023 | 2 | 3 | | | III-2 | Ccdc61 | 729440 | 4-May-15 |
| 3492 | 2 | 3 | | | III-2 | Brdt | 676 | 4-May-15 | 4028 | 2 | 3 | | | III-2 | Ccdc65 | 85478 | 4-May-15 |
| 3495 | 2 | 3 | | | III-2 | Brf2 | 55290 | 7-Jun-15 | 4034 | 2 | 3 | | | III-2 | Ccdc70 | 83446 | 4-May-15 |
| 3501 | 2 | 3 | | | III-2 | Brinp3 | 339479 | 4-May-15 | 4040 | 2 | 3 | | | III-2 | Ccdc78 | 124093 | 4-May-15 |
| 3504 | 2 | 3 | | | III-2 | Brk1 | 55845 | 4-May-15 | 4045 | 2 | 3 | | | III-2 | Ccdc82 | 79780 | 4-May-15 |
| 3516 | 2 | 3 | | | III-2 | Bsdc1 | 55108 | 4-May-15 | 4052 | 2 | 3 | | | III-2 | Ccdc87 | 55231 | 4-May-15 |
| 3518 | 2 | 3 | | | III-2 | Bsn | 8927 | 4-May-15 | 4057 | 2 | 3 | | | III-2 | Ccdc9 | 26093 | 4-May-15 |
| 3527 | 2 | 3 | | | III-2 | Btbd1 | 53339 | 4-May-15 | 4058 | 2 | 3 | | | III-2 | Ccdc90b | 60492 | 4-May-15 |
| 3531 | 2 | 3 | | | III-2 | Btbd17 | 388419 | 4-May-15 | 4062 | 2 | 3 | | | III-2 | Ccdc94 | 55702 | 4-May-15 |
| 3535 | 2 | 3 | | | III-2 | Btbd3 | 22903 | 4-May-15 | 4064 | 2 | 3 | | | III-2 | Ccdc97 | 90324 | 4-May-15 |
| 3539 | 2 | 3 | | | III-2 | Btbd9 | 134781 | 4-May-15 | 4085 | 2 | 3 | | | III-2 | Ccl27a | | |
| 3542 | 2 | 3 | | | III-2 | Btf3 | 689 | 7-Jun-15 | 4096 | 2 | 3 | | | III-2 | Ccm2l | 140706 | 4-May-15 |
| 3545 | 2 | 3 | | | III-2 | Btg2 | 7832 | 26-May-15 | 4098 | 2 | 3 | | | III-2 | Ccna2 | 890 | 24-May-15 |
| 3548 | 2 | 3 | | | III-2 | Btk | 695 | 27-May-15 | 4101 | 2 | 3 | | | III-2 | Ccnb2 | 9133 | 12-May-15 |
| 3551 | 2 | 3 | | | III-2 | Btn2a2 | 10385 | 4-May-15 | 4103 | 2 | 3 | | | III-2 | Ccnc | 892 | 17-May-15 |
| 3555 | 2 | 3 | | | III-2 | Btnl4 | | | 4107 | 2 | 3 | | | III-2 | Ccndbp1 | 23582 | 17-May-15 |
| 3557 | 2 | 3 | | | III-2 | Btnl6 | | | 4115 | 2 | 3 | | | III-2 | Ccnj | 54619 | 4-May-15 |
| 3560 | 2 | 3 | | | III-2 | Bub1 | 699 | 12-May-15 | 4123 | 2 | 3 | | | III-2 | Ccny | 219771 | 4-May-15 |

Fig.22 - 42

| | | | | | | | | | | | | | | | |
|---|---|---|---|---|---|---|---|---|---|---|---|---|---|---|---|
| 4127 | 2 | 3 | | | H-2 | Ccng1os | | | 4795 | 2 | 3 | | | H-2 | Clpb | 81570 | 31-May-15 |
| 4144 | 2 | 3 | | | H-2 | Ccser2 | 54462 | 4-May-15 | 4810 | 2 | 3 | | | H-2 | Cltb | 1212 | 4-May-15 |
| 4146 | 2 | 3 | | | H-2 | Cct3 | 7203 | 4-May-15 | 4817 | 2 | 3 | | | H-2 | Clybl | 171425 | |
| 4171 | 2 | 3 | | | H-2 | Cd200r1 | 131450 | | 4826 | 2 | 3 | | | H-2 | Cmklr1 | 1240 | |
| 4173 | 2 | 3 | | | H-2 | Cd200r3 | | | 4832 | 2 | 3 | | | H-2 | Cmpk2 | 129607 | |
| 4181 | 2 | 3 | | | H-2 | Cd209f | | | 4835 | 2 | 3 | | | H-2 | Cmtr2a | | |
| 4185 | 2 | 3 | | | H-2 | Cd244 | 51744 | | 4836 | 2 | 3 | | | H-2 | Cmtm2b | | |
| 4186 | 2 | 3 | | | H-2 | Cd247 | 919 | 21-May-15 | 4841 | 2 | 3 | | | H-2 | Cmtm7 | 112616 | 4-May-15 |
| 4239 | 2 | 3 | | | H-2 | Cd47 | 961 | 31-May-15 | 4842 | 2 | 3 | | | H-2 | Cmtm8 | 152189 | 4-May-15 |
| 4239 | 2 | 3 | | | H-2 | Cd81 | 975 | 31-May-15 | 4844 | 2 | 3 | | | H-2 | Cmtr2 | 55783 | 12-May-15 |
| 4249 | 2 | 3 | | | H-2 | Cd97 | 976 | | 4847 | 2 | 3 | | | H-2 | Cnbp | 7555 | 23-May-15 |
| 4253 | 2 | 3 | | | H-2 | Cdan1 | 145059 | 23-May-15 | 4856 | 2 | 3 | | | H-2 | Cngb1 | 1258 | 23-May-15 |
| 4258 | 2 | 3 | | | H-2 | Cdc20 | 991 | | 4861 | 2 | 3 | | | H-2 | Cnih4 | 29097 | 21-May-15 |
| 4260 | 2 | 3 | | | H-2 | Cdc23 | 8697 | 4-May-15 | 4867 | 2 | 3 | | | H-2 | Cnn3 | 1266 | 4-May-15 |
| 4277 | 2 | 3 | | | H-2 | Cdc42ep4 | 23580 | 12-May-15 | 4871 | 2 | 3 | | | H-2 | Cnnm4 | 26504 | 12-May-15 |
| 4280 | 2 | 3 | | | H-2 | Cdc42se2 | 56990 | 4-May-15 | 4874 | 2 | 3 | | | H-2 | Cnot11 | 55571 | 4-May-15 |
| 4285 | 2 | 3 | | | H-2 | Cdc73 | 79577 | 23-May-15 | 4877 | 2 | 3 | | | H-2 | Cnot4 | 4850 | 3-Jun-15 |
| 4289 | 2 | 3 | | | H-2 | Cdca5 | 113130 | 17-May-15 | 4879 | 2 | 3 | | | H-2 | Cnot6l | 246175 | 3-Jun-15 |
| 4299 | 2 | 3 | | | H-2 | Cdh13 | 1012 | 17-May-15 | 4880 | 2 | 3 | | | H-2 | Cnot7 | 29883 | 16-May-15 |
| 4309 | 2 | 3 | | | H-2 | Cdh24 | 54403 | 7-Jun-15 | 4881 | 2 | 3 | | | H-2 | Cnot8 | 9337 | 2-Jun-15 |
| 4314 | 2 | 3 | | | H-2 | Cdh6 | 1064 | 12-May-15 | 4883 | 2 | 3 | | | H-2 | Cnppd1 | 27083 | 12-May-15 |
| 4316 | 2 | 3 | | | H-2 | Cdh8 | 1006 | 12-May-15 | 4884 | 2 | 3 | | | H-2 | Cnpy1 | 285888 | 4-May-15 |
| 4317 | 2 | 3 | | | H-2 | Cdh9 | 1007 | 4-May-15 | 4887 | 2 | 3 | | | H-2 | Cnpy4 | 245812 | 4-May-15 |
| 4323 | 2 | 3 | | | H-2 | Cdipt | 10423 | 4-May-15 | 4888 | 2 | 3 | | | H-2 | Cnr1 | 1268 | 7-Jun-15 |
| 4326 | 2 | 3 | | | H-2 | Cdk11b | 984 | 12-May-15 | 4889 | 2 | 3 | | | H-2 | Cnr2 | 1269 | 17-May-15 |
| 4327 | 2 | 3 | | | H-2 | Cdk12 | 51755 | 21-May-15 | 4896 | 2 | 3 | | | H-2 | Cntn1 | 1272 | 4-May-15 |
| 4329 | 2 | 3 | | | H-2 | Cdk14 | 5218 | | 4904 | 2 | 3 | | | H-2 | Cntnap3 | 79987 | 4-May-15 |
| 4331 | 2 | 3 | | | H-2 | Cdk16 | 5127 | 31-May-15 | 4908 | 2 | 3 | | | H-2 | Cntnap5c | | |
| 4336 | 2 | 3 | | | H-2 | Cdk20 | 23552 | 4-May-15 | 4909 | 2 | 3 | | | H-2 | Cntrl | 11064 | 4-May-15 |
| 4337 | 2 | 3 | | | H-2 | Cdk2ap1 | 8099 | 4-May-15 | 4911 | 2 | 3 | | | H-2 | Coa3 | 28958 | 4-May-15 |
| 4341 | 2 | 3 | | | H-2 | Cdk5 | 1020 | 27-May-15 | 4912 | 2 | 3 | | | H-2 | Coa4 | 51287 | 4-May-15 |
| 4343 | 2 | 3 | | | H-2 | Cdk5r2 | 8941 | 4-May-15 | 4914 | 2 | 3 | | | H-2 | Coa6 | 388753 | 21-May-15 |
| 4344 | 2 | 3 | | | H-2 | Cdk5rap1 | 51654 | 4-May-15 | 4916 | 2 | 3 | | | H-2 | Coasy | 80347 | 4-May-15 |
| 4346 | 2 | 3 | | | H-2 | Cdk5rap3 | 80279 | 12-May-15 | 4921 | 2 | 3 | | | H-2 | Cog2 | 22796 | 4-May-15 |
| 4349 | 2 | 3 | | | H-2 | Cdk8 | 1024 | 17-May-15 | 4922 | 2 | 3 | | | H-2 | Cog3 | 83548 | 4-May-15 |
| 4354 | 2 | 3 | | | H-2 | Cdkl3 | 51265 | 4-May-15 | 4934 | 2 | 3 | | | H-2 | Col14a1 | 7373 | |
| 4380 | 2 | 3 | | | H-2 | Cdx1 | 1044 | 28-May-15 | 4937 | 2 | 3 | | | H-2 | Col17a1 | 1308 | 24-May-15 |
| 4397 | 2 | 3 | | | H-2 | Ceacam3 | 1084 | 4-May-15 | 4938 | 2 | 3 | | | H-2 | Col18a1 | 80781 | |
| 4406 | 2 | 3 | | | H-2 | Cebpz | 10153 | 7-Jun-15 | 4943 | 2 | 3 | | | H-2 | Col22a1 | 169044 | 12-May-15 |
| 4416 | 2 | 3 | | | H-2 | Celf2 | 10659 | | 4948 | 2 | 3 | | | H-2 | Col27a1 | 85301 | |
| 4418 | 2 | 3 | | | H-2 | Celf4 | 56853 | | 4956 | 2 | 3 | | | H-2 | Col4a4 | 1286 | 23-May-15 |
| 4425 | 2 | 3 | | | H-2 | Cemip | 57214 | 12-May-15 | 4972 | 2 | 3 | | | H-2 | Col9a2 | 1298 | 23-May-15 |
| 4429 | 2 | 3 | | | H-2 | Cenpc1 | 1060 | 4-May-15 | 4978 | 2 | 3 | | | H-2 | Colq | 8292 | |
| 4446 | 2 | 3 | | | H-2 | Cep104 | 9731 | 4-May-15 | 4980 | 2 | 3 | | | H-2 | Commd10 | 51397 | 12-May-15 |
| 4449 | 2 | 3 | | | H-2 | Cep128 | 145508 | 12-May-15 | 4985 | 2 | 3 | | | H-2 | Commd6 | 170622 | 4-May-15 |
| 4452 | 2 | 3 | | | H-2 | Cep152 | 22995 | | 4987 | 2 | 3 | | | H-2 | Commd8 | 54961 | 4-May-15 |
| 4453 | 2 | 3 | | | H-2 | Cep162 | 22882 | 4-May-15 | 4991 | 2 | 3 | | | H-2 | Comtd1 | 118881 | 4-May-15 |
| 4454 | 2 | 3 | | | H-2 | Cep164 | 22897 | 31-May-15 | 4993 | 2 | 3 | | | H-2 | Copb1 | 1315 | 4-May-15 |
| 4460 | 2 | 3 | | | H-2 | Cep290 | 80184 | 29-May-15 | 5002 | 2 | 3 | | | H-2 | Cops5 | 10987 | 4-May-15 |
| 4461 | 2 | 3 | | | H-2 | Cep350 | 9857 | 12-May-15 | 5015 | 2 | 3 | | | H-2 | Coq6 | 51004 | 23-May-15 |
| 4463 | 2 | 3 | | | H-2 | Cep44 | 80817 | 4-May-15 | 5016 | 2 | 3 | | | H-2 | Coq7 | 10229 | 28-May-15 |
| 4478 | 2 | 3 | | | H-2 | Cep95 | 90799 | 12-May-15 | 5021 | 2 | 3 | | | H-2 | Coro1c | 23603 | 4-May-15 |
| 4479 | 2 | 3 | | | H-2 | Cep97 | 79598 | 12-May-15 | 5026 | 2 | 3 | | | H-2 | Cort | 1325 | |
| 4484 | 2 | 3 | | | H-2 | Cerkl | 375298 | 23-May-15 | 5029 | 2 | 3 | | | H-2 | Cox11 | 1353 | 7-Jun-15 |
| 4487 | 2 | 3 | | | H-2 | Cers3 | 204219 | 4-May-15 | 5036 | 2 | 3 | | | H-2 | Cox20 | 116228 | 4-May-15 |
| 4492 | 2 | 3 | | | H-2 | Ces1b | | | 5049 | 2 | 3 | | | H-2 | Cox7b | 1349 | 15-May-15 |
| 4523 | 2 | 3 | | | H-2 | Cfl2 | 1073 | 23-May-15 | 5064 | 2 | 3 | | | H-2 | Cpd | 1362 | 7-Jun-15 |
| 4525 | 2 | 3 | | | H-2 | Cfp | 5199 | 17-May-15 | 5065 | 2 | 3 | | | H-2 | Cpe | 1363 | 12-May-15 |
| 4533 | 2 | 3 | | | H-2 | Ch25h | 9023 | 4-May-15 | 5073 | 2 | 3 | | | H-2 | Cplx1 | 10815 | 4-May-15 |
| 4538 | 2 | 3 | | | H-2 | Chaf1a | 10036 | | 5081 | 2 | 3 | | | H-2 | Cpne2 | 221184 | |
| 4539 | 2 | 3 | | | H-2 | Chaf1b | 8208 | | 5083 | 2 | 3 | | | H-2 | Cpne4 | 131034 | 4-May-15 |
| 4541 | 2 | 3 | | | H-2 | Chat | 1103 | 23-May-15 | 5091 | 2 | 3 | | | H-2 | Cpq | 10404 | 4-May-15 |
| 4547 | 2 | 3 | | | H-2 | Chchd5 | 84269 | 4-May-15 | 5094 | 2 | 3 | | | H-2 | Cpsf2 | 53981 | 4-May-15 |
| 4551 | 2 | 3 | | | H-2 | Chd1l | 9557 | 12-May-15 | 5101 | 2 | 3 | | | H-2 | Cpt1a | 1374 | 23-May-15 |
| 4552 | 2 | 3 | | | H-2 | Chd2 | 1106 | 7-Jun-15 | 5105 | 2 | 3 | | | H-2 | Cpvl | 54504 | 23-May-15 |
| 4555 | 2 | 3 | | | H-2 | Chd4 | 1108 | 12-May-15 | 5106 | 2 | 3 | | | H-2 | Cpxcr1 | 53336 | 4-May-15 |
| 4556 | 2 | 3 | | | H-2 | Chd5 | 26038 | 7-Jun-15 | 5118 | 2 | 3 | | | H-2 | Crb2 | 286204 | 12-May-15 |
| 4562 | 2 | 3 | | | H-2 | Chek1 | 1111 | | 5121 | 2 | 3 | | | H-2 | Crcp | 27297 | 4-May-15 |
| 4564 | 2 | 3 | | | H-2 | Cherp | 10523 | 4-May-15 | 5132 | 2 | 3 | | | H-2 | Crebrf | 153222 | 4-May-15 |
| 4565 | 2 | 3 | | | H-2 | Chfr | 55743 | 23-May-15 | 5155 | 2 | 3 | | | H-2 | Crkl | 1399 | 29-May-15 |
| 4570 | 2 | 3 | | | H-2 | Chic2 | 26511 | 4-May-15 | 5159 | 2 | 3 | | | H-2 | Crls1 | 54675 | 4-May-15 |
| 4576 | 2 | 3 | | | H-2 | Chit1 | 1118 | 4-May-15 | 5163 | 2 | 3 | | | H-2 | Crnn | 49860 | 4-May-15 |
| 4579 | 2 | 3 | | | H-2 | ChkbCpt1b | 386593 | 4-May-15 | 5166 | 2 | 3 | | | H-2 | Crp | 1401 | #NAME? |
| 4584 | 2 | 3 | | | H-2 | Chmp1b | 57132 | 4-May-15 | 5169 | 2 | 3 | | | H-2 | Crtap | 10491 | 4-May-15 |
| 4591 | 2 | 3 | | | H-2 | Chmp6 | 79643 | 3-May-15 | 5172 | 2 | 3 | | | H-2 | Crtc3 | 64784 | 12-May-15 |
| 4595 | 2 | 3 | | | H-2 | Chn2 | 1124 | 12-May-15 | 5186 | 2 | 3 | | | H-2 | Cryga | 1418 | 4-May-15 |
| 4598 | 2 | 3 | | | H-2 | Chp1 | 11261 | 7-Jun-15 | 5194 | 2 | 3 | | | H-2 | Cryl1 | 51084 | 4-May-15 |
| 4607 | 2 | 3 | | | H-2 | Chrm1 | 1128 | 4-May-15 | 5197 | 2 | 3 | | | H-2 | Cryzl1 | 9946 | 4-May-15 |
| 4618 | 2 | 3 | | | H-2 | Chrna6 | 8973 | | 5202 | 2 | 3 | | | H-2 | Cse1l | 1434 | 4-May-15 |
| 4621 | 2 | 3 | | | H-2 | Chrnb1 | 1140 | 7-May-15 | 5206 | 2 | 3 | | | H-2 | Csf2ra | 1438 | 4-May-15 |
| 4634 | 2 | 3 | | | H-2 | Chst15 | 51363 | 12-May-15 | 5213 | 2 | 3 | | | H-2 | Csk | 1445 | 3-May-15 |
| 4644 | 2 | 3 | | | H-2 | Chtf18 | 63922 | | 5225 | 2 | 3 | | | H-2 | Csnk1d | 1453 | 29-May-15 |
| 4646 | 2 | 3 | | | H-2 | Chtop | 26097 | 4-May-15 | 5236 | 2 | 3 | | | H-2 | Cspp1 | 79848 | 12-May-15 |
| 4664 | 2 | 3 | | | H-2 | Cipc | 85457 | 4-May-15 | 5237 | 2 | 3 | | | H-2 | Csprs | | |
| 4673 | 2 | 3 | | | H-2 | Cit | 11113 | 76/7 | 5258 | 2 | 3 | | | H-2 | Cstf2 | 1478 | 12-May-15 |
| 4679 | 2 | 3 | | | H-2 | Ckap2 | 26586 | 4-May-15 | 5260 | 2 | 3 | | | H-2 | Cstf3 | 1479 | 4-May-15 |
| 4682 | 2 | 3 | | | H-2 | Ckap5 | 9793 | 4-May-15 | 5269 | 2 | 3 | | | H-2 | Ctcfl | 140690 | 4-May-15 |
| 4690 | 2 | 3 | | | H-2 | Cks2 | 1164 | 12-May-15 | 5270 | 2 | 3 | | | H-2 | Ctcflos | | |
| 4692 | 2 | 3 | | | H-2 | Clasp2 | 23122 | 28-May-15 | 5272 | 2 | 3 | | | H-2 | Ctdp1 | 9150 | 23-May-15 |
| 4710 | 2 | 3 | | | H-2 | Clcnkb | 1188 | | 5277 | 2 | 3 | | | H-2 | Ctf1 | 1489 | 12-May-15 |
| 4721 | 2 | 3 | | | H-2 | Cldn19 | 149461 | 1-Jun-15 | 5291 | 2 | 3 | | | H-2 | Ctnnbip1 | 56998 | 14-May-15 |
| 4728 | 2 | 3 | | | H-2 | Cldn26 | | | 5298 | 2 | 3 | | | H-2 | Ctr9 | 9646 | 12-May-15 |
| 4743 | 2 | 3 | | | H-2 | Clec18a | 348174 | 4-May-15 | 5304 | 2 | 3 | | | H-2 | Cts6 | | |
| 4749 | 2 | 3 | | | H-2 | Clec2g | | | 5339 | 2 | 3 | | | H-2 | Cul2 | 8453 | 12-May-15 |
| 4764 | 2 | 3 | | | H-2 | Clec4g | 339390 | | 5344 | 2 | 3 | | | H-2 | Cul7 | 9820 | 23-May-15 |
| 4770 | 2 | 3 | | | H-2 | Clhc1 | 130162 | | 5347 | 2 | 3 | | | H-2 | Cutal | | |
| 4782 | 2 | 3 | | | H-2 | Clk2 | 1196 | 7-Jun-15 | 5369 | 2 | 3 | | | H-2 | Cxcl16 | 58191 | |

Fig.22 - 43

| | | | | | | | | | | | | | | | |
|---|---|---|---|---|---|---|---|---|---|---|---|---|---|---|---|
| 5371 | 2 | 3 | | III-2 | Cxcl2 | 2920 | 12-May-15 | 6040 | 2 | 3 | | III-2 | Dmxl1 | 1657 | 4-May-15 |
| 5373 | 2 | 3 | | III-2 | Cxcl5 | 6374 | | 6042 | 2 | 3 | | III-2 | Dna2 | 1783 | 3-May-15 |
| 5382 | 2 | 3 | | III-2 | Cxx1b | 26071 | 4-May-15 | 6044 | 2 | 3 | | III-2 | Dnaaf2 | 55172 | 28-May-15 |
| 5383 | 2 | 3 | | III-2 | Cxx1c | 441518 | 4-May-15 | 6057 | 2 | 3 | | III-2 | Dnact1 | | |
| 5385 | 2 | 3 | | III-2 | Cxxc4 | 80319 | 4-May-15 | 6061 | 2 | 3 | | III-2 | Dnaja3 | 9093 | 4-May-15 |
| 5399 | 2 | 3 | | III-2 | Cyb5rl | 606495 | 4-May-15 | 6064 | 2 | 3 | | III-2 | Dnajb11 | 51726 | 4-May-15 |
| 5406 | 2 | 3 | | III-2 | Cyfip1 | 23191 | 17-May-15 | 6065 | 2 | 3 | | III-2 | Dnajb12 | 54788 | 12-May-15 |
| 5463 | 2 | 3 | | III-2 | Cyp2d37-ps | | | 6073 | 2 | 3 | | III-2 | Dnajb7 | 150353 | 4-May-15 |
| 5473 | 2 | 3 | | III-2 | Cyp2j6 | | | 6081 | 2 | 3 | | III-2 | Dnajc14 | 85406 | 4-May-15 |
| 5511 | 2 | 3 | | III-2 | Cyp4f41-ps | | | 6084 | 2 | 3 | | III-2 | Dnajc17 | 55192 | 4-May-15 |
| 5519 | 2 | 3 | | III-2 | Cyth2 | | | 6092 | 2 | 3 | | III-2 | Dnajc27 | 51277 | 4-May-15 |
| 5534 | 2 | 3 | | III-2 | Cyth2 | 9266 | 31-May-15 | 6095 | 2 | 3 | | III-2 | Dnajc30 | 84277 | 4-May-15 |
| 5541 | 2 | 3 | | III-2 | D030024E09Rik | | | 6098 | 2 | 3 | | III-2 | Dnajc5b | 85479 | 4-May-15 |
| 5546 | 2 | 3 | | III-2 | D030045P18Rik | | | 6104 | 2 | 3 | | III-2 | Dnal1 | 83544 | 23-May-15 |
| 5548 | 2 | 3 | | III-2 | D030056L22Rik | | | 6116 | 2 | 3 | | III-2 | Dnm1 | 1759 | 21-May-15 |
| 5557 | 2 | 3 | | III-2 | D130043K22Rik | | | 6123 | 2 | 3 | | III-2 | Dnmt3a | 1788 | 21-May-15 |
| 5559 | 2 | 3 | | III-2 | D14Ertd670e | | | 6124 | 2 | 3 | | III-2 | Dnmt3aos | | |
| 5563 | 2 | 3 | | III-2 | D17Ertd648e | | | 6125 | 2 | 3 | | III-2 | Dnmt3b | 1789 | 24-May-15 |
| 5581 | 2 | 3 | | III-2 | D3Ertd751e | | | 6138 | 2 | 3 | | III-2 | Dock2 | 1794 | 4-May-15 |
| 5585 | 2 | 3 | | III-2 | D430041J06Rik | | | 6140 | 2 | 3 | | III-2 | Dock4 | 9732 | 4-May-15 |
| 5587 | 2 | 3 | | III-2 | D4Ertd617e | | | 6146 | 2 | 3 | | III-2 | Dohh | 83475 | 4-May-15 |
| 5594 | 2 | 3 | | III-2 | D630013N20Rik | | | 6153 | 2 | 3 | | III-2 | Dok7 | 285489 | 23-May-15 |
| 5598 | 2 | 3 | | III-2 | D630032N06Rik | | | 6155 | 2 | 3 | | III-2 | Dolpp1 | 57171 | 21-May-15 |
| 5607 | 2 | 3 | | III-2 | D730001G18Rik | | | 6156 | 2 | 3 | | III-2 | Donson | 29980 | 4-May-15 |
| 5614 | 2 | 3 | | III-2 | D7Ertd715e | | | 6162 | 2 | 3 | | III-2 | Dpagt1 | 1798 | 23-May-15 |
| 5617 | 2 | 3 | | III-2 | D830015G02Rik | | | 6168 | 2 | 3 | | III-2 | Dpf1 | 8193 | 2-Jun-15 |
| 5619 | 2 | 3 | | III-2 | D830030K20Rik | | | 6173 | 2 | 3 | | III-2 | Dph3 | 285381 | 4-May-15 |
| 5622 | 2 | 3 | | III-2 | D830046C22Rik | | | 6176 | 2 | 3 | | III-2 | Dph7 | 92715 | 12-May-15 |
| 5629 | 2 | 3 | | III-2 | D930020B18Rik | | | 6185 | 2 | 3 | | III-2 | Dpp9 | 91039 | 4-May-15 |
| 5635 | 2 | 3 | | III-2 | Dab1 | 1600 | 7-Jun-15 | 6194 | 2 | 3 | | III-2 | Dpy19l2 | 283417 | 4-May-15 |
| 5639 | 2 | 3 | | III-2 | Dach2 | 117154 | 4-May-15 | 6195 | 2 | 3 | | III-2 | Dpy19l3 | 147991 | 4-May-15 |
| 5640 | 2 | 3 | | III-2 | Dact1 | 51339 | 3-May-15 | 6205 | 2 | 3 | | III-2 | DQ267101 | | |
| 5647 | 2 | 3 | | III-2 | Daglb | 221955 | 21-May-15 | 6209 | 2 | 3 | | III-2 | Dram1 | 55332 | 4-May-15 |
| 5649 | 2 | 3 | | III-2 | Dalrd3 | 55152 | 4-May-15 | 6214 | 2 | 3 | | III-2 | Drd1a | 1812 | 28-May-15 |
| 5654 | 2 | 3 | | III-2 | Dap3 | 7818 | 7-Jun-15 | 6224 | 2 | 3 | | III-2 | Dsc1 | 1823 | 7-Jun-15 |
| 5655 | 2 | 3 | | III-2 | Dapk1 | 1612 | 4-May-15 | 6225 | 2 | 3 | | III-2 | Dsc2 | 1824 | 7-Jun-15 |
| 5661 | 2 | 3 | | III-2 | Dars2 | 55157 | 23-May-15 | 6231 | 2 | 3 | | III-2 | Dse | 29940 | 12-May-15 |
| 5662 | 2 | 3 | | III-2 | Daw1 | 164781 | 4-May-15 | 6234 | 2 | 3 | | III-2 | Dsg1b | | |
| 5675 | 2 | 3 | | III-2 | Dbnl | 28988 | 4-May-15 | 6244 | 2 | 3 | | III-2 | Dstyk | 25778 | 4-May-15 |
| 5679 | 2 | 3 | | III-2 | Dbt | 1629 | 23-May-15 | 6252 | 2 | 3 | | III-2 | Dtwd1 | 56986 | 14-May-15 |
| 5687 | 2 | 3 | | III-2 | Dcaf13 | 25879 | 4-May-15 | 6256 | 2 | 3 | | III-2 | Dtx3 | 196408 | 2-Jun-15 |
| 5691 | 2 | 3 | | III-2 | Dcaf5 | 8816 | 4-May-15 | 6257 | 2 | 3 | | III-2 | Dtx3l | 151636 | 12-May-15 |
| 5706 | 2 | 3 | | III-2 | Dclk3 | 85443 | 4-May-15 | 6260 | 2 | 3 | | III-2 | Duox1 | 53905 | 24-May-15 |
| 5708 | 2 | 3 | | III-2 | Dclre1b | 64858 | 4-May-15 | 6268 | 2 | 3 | | III-2 | Dus4l | 11062 | 4-May-15 |
| 5712 | 2 | 3 | | III-2 | Dcp1b | 196513 | 23-May-15 | 6272 | 2 | 3 | | III-2 | Dusp12 | 11266 | 4-May-15 |
| 5718 | 2 | 3 | | III-2 | Dcst1 | 149095 | 4-May-15 | 6281 | 2 | 3 | | III-2 | Dusp22 | 56940 | 4-May-15 |
| 5726 | 2 | 3 | | III-2 | Dctn5 | 84516 | 4-May-15 | 6294 | 2 | 3 | | III-2 | Dux | | |
| 5731 | 2 | 3 | | III-2 | Dcun1d3 | 123879 | 3-May-15 | 6298 | 2 | 3 | | III-2 | Dvl1 | 1855 | 7-Jun-15 |
| 5737 | 2 | 3 | | III-2 | Ddah1 | 23576 | 4-May-15 | 6303 | 2 | 3 | | III-2 | Dydc1 | 143241 | 4-May-15 |
| 5752 | 2 | 3 | | III-2 | Ddr1 | 780 | 4-May-15 | 6316 | 2 | 3 | | III-2 | Dynlrb1 | 83658 | 4-May-15 |
| 5755 | 2 | 3 | | III-2 | Ddr | 1652 | 4-May-15 | 6319 | 2 | 3 | | III-2 | Dynlt3b | | |
| 5760 | 2 | 3 | | III-2 | Ddx18 | 8886 | 4-May-15 | 6323 | 2 | 3 | | III-2 | Dyrk1a | 1859 | 12-May-15 |
| 5772 | 2 | 3 | | III-2 | Ddx39 | 10212 | 4-May-15 | 6328 | 2 | 3 | | III-2 | Dysf | 8291 | 31-May-15 |
| 5793 | 2 | 3 | | III-2 | Ddx60 | 55601 | 4-May-15 | 6339 | 2 | 3 | | III-2 | E030018B13Rik | | |
| 5795 | 2 | 3 | | III-2 | Dear1 | 55223 | 4-May-15 | 6341 | 2 | 3 | | III-2 | E030019B13Rik | | |
| 5799 | 2 | 3 | | III-2 | Dedd | 9191 | 4-May-15 | 6344 | 2 | 3 | | III-2 | E030030I06Rik | | |
| 5800 | 2 | 3 | | III-2 | Dedd2 | 162989 | 4-May-15 | 6346 | 2 | 3 | | III-2 | E130006D01Rik | | |
| 5801 | 2 | 3 | | III-2 | Def6 | 50619 | 76/7 | 6353 | 2 | 3 | | III-2 | E130201H02Rik | | |
| 5811 | 2 | 3 | | III-2 | Defa26 | | | 6364 | 2 | 3 | | III-2 | E130317F20Rik | | |
| 5814 | 2 | 3 | | III-2 | Defa5 | 1670 | 24-May-15 | 6366 | 2 | 3 | | III-2 | E230016K23Rik | | |
| 5867 | 2 | 3 | | III-2 | Dennd1a | 57706 | 4-May-15 | 6369 | 2 | 3 | | III-2 | E230025N22Rik | | |
| 5868 | 2 | 3 | | III-2 | Dennd1b | 163486 | 4-May-15 | 6387 | 2 | 3 | | III-2 | E330021D16Rik | | |
| 5869 | 2 | 3 | | III-2 | Dennd1c | 79958 | 12-May-15 | 6393 | 2 | 3 | | III-2 | E430025E21Rik | | |
| 5878 | 2 | 3 | | III-2 | Dennd5b | 160518 | 12-May-15 | 6394 | 2 | 3 | | III-2 | Eaf1 | 1877 | 23-May-15 |
| 5882 | 2 | 3 | | III-2 | Depdc1a | 55635 | 4-May-15 | 6395 | 2 | 3 | | III-2 | E530001F21Rik | | |
| 5888 | 2 | 3 | | III-2 | Derl1 | 79139 | 29-May-15 | 6397 | 2 | 3 | | III-2 | Eaf1 | 85403 | 7-Jun-15 |
| 5889 | 2 | 3 | | III-2 | Derl2 | 51009 | 12-May-15 | 6406 | 2 | 3 | | III-2 | Ear6 | | |
| 5896 | 2 | 3 | | III-2 | Dffa | 1676 | 4-May-15 | 6412 | 2 | 3 | | III-2 | Ebf3 | 253738 | 7-Jun-15 |
| 5910 | 2 | 3 | | III-2 | Dgke | 8526 | 24-May-15 | 6416 | 2 | 3 | | III-2 | Ebp | 10682 | 7-Jun-15 |
| 5911 | 2 | 3 | | III-2 | Dgkeos | | | 6419 | 2 | 3 | | III-2 | Ece1 | 1889 | 12-May-15 |
| 5914 | 2 | 3 | | III-2 | Dgki | 9162 | 4-May-15 | 6441 | 2 | 3 | | III-2 | Edc4 | 23644 | 4-May-15 |
| 5917 | 2 | 3 | | III-2 | Dgkz | 8525 | 4-May-15 | 6444 | 2 | 3 | | III-2 | Edem2 | 55741 | 4-May-15 |
| 5922 | 2 | 3 | | III-2 | Dhdh | 27294 | 4-May-15 | 6445 | 2 | 3 | | III-2 | Edem3 | 80267 | 4-May-15 |
| 5924 | 2 | 3 | | III-2 | Dhh | 50846 | 23-May-15 | 6446 | 2 | 3 | | III-2 | Edf1 | 8721 | 4-May-15 |
| 5926 | 2 | 3 | | III-2 | Dhps | 1725 | 12-May-15 | 6454 | 2 | 3 | | III-2 | Eea2 | 8411 | 4-May-15 |
| 5931 | 2 | 3 | | III-2 | Dhrs3 | 9249 | 21-May-15 | 6462 | 2 | 3 | | III-2 | Eef2 | 1938 | 23-May-15 |
| 5933 | 2 | 3 | | III-2 | Dhrs7 | 51635 | 4-May-15 | 6470 | 2 | 3 | | III-2 | Efcab14 | 9813 | 4-May-15 |
| 5938 | 2 | 3 | | III-2 | Dhtkd1 | 55526 | 4-May-15 | 6471 | 2 | 3 | | III-2 | Efcab2 | 84288 | 4-May-15 |
| 5940 | 2 | 3 | | III-2 | Dhx16 | 8449 | 4-May-15 | 6476 | 2 | 3 | | III-2 | Efcab6 | 64800 | 4-May-15 |
| 5941 | 2 | 3 | | III-2 | Dhx29 | 54505 | 4-May-15 | 6479 | 2 | 3 | | III-2 | Efcab9 | 285588 | 4-May-15 |
| 5943 | 2 | 3 | | III-2 | Dhx32 | 55760 | 4-May-15 | 6484 | 2 | 3 | | III-2 | Efhc1 | 114327 | 10-May-15 |
| 5945 | 2 | 3 | | III-2 | Dhx34 | 9704 | 4-May-15 | 6486 | 2 | 3 | | III-2 | Efhd1 | 80303 | 7-Jun-15 |
| 5947 | 2 | 3 | | III-2 | Dhx36 | 170506 | 21-May-15 | 6495 | 2 | 3 | | III-2 | Efnb3 | 1949 | 4-May-15 |
| 5948 | 2 | 3 | | III-2 | Dhx37 | 57647 | 4-May-15 | 6496 | 2 | 3 | | III-2 | Efr3a | 23167 | 4-May-15 |
| 5954 | 2 | 3 | | III-2 | Dhx9 | 1660 | 4-May-15 | 6500 | 2 | 3 | | III-2 | Eftud2 | 9343 | 23-May-15 |
| 5960 | 2 | 3 | | III-2 | Dido1 | 11083 | 4-May-15 | 6510 | 2 | 3 | | III-2 | Egln2 | 112398 | 4-May-15 |
| 5968 | 2 | 3 | | III-2 | Dip2b | 57609 | 4-May-15 | 6516 | 2 | 3 | | III-2 | Ehbp1 | 23301 | 4-May-15 |
| 5969 | 2 | 3 | | III-2 | Dip2c | 22982 | 4-May-15 | 6519 | 2 | 3 | | III-2 | Ehd2 | 30846 | 12-May-15 |
| 5975 | 2 | 3 | | III-2 | Dis3l2 | 129563 | 4-May-15 | 6525 | 2 | 3 | | III-2 | Ehmt2 | 10919 | 4-May-15 |
| 5977 | 2 | 3 | | III-2 | Disp1 | 84976 | 12-May-15 | 6538 | 2 | 3 | | III-2 | Eif2ak1 | 5610 | 31-May-15 |
| 5982 | 2 | 3 | | III-2 | Dkk2 | 27123 | 4-May-15 | 6540 | 2 | 3 | | III-2 | Eif2ak4 | 440275 | 4-May-15 |
| 5993 | 2 | 3 | | III-2 | Dlg2 | 1740 | 7-Jun-15 | 6542 | 2 | 3 | | III-2 | Eif2b2 | 8892 | 23-May-15 |
| 5995 | 2 | 3 | | III-2 | Dlg4 | 1742 | 7-Jun-15 | 6545 | 2 | 3 | | III-2 | Eif2b5 | 8893 | 23-May-15 |
| 6006 | 2 | 3 | | III-2 | Dlk4 | 54567 | 4-May-15 | 6546 | 2 | 3 | | III-2 | Eif2d | 1939 | 21-May-15 |
| 6008 | 2 | 3 | | III-2 | Dlx1 | 1745 | 4-May-15 | 6577 | 2 | 3 | | III-2 | Eif4g1 | 1981 | 29-May-15 |
| 6015 | 2 | 3 | | III-2 | Dlx6as2 | 100873 931 | 1-Feb-15 | 6581 | 2 | 3 | | III-2 | Eif5 | 1983 | 4-May-15 |
| 6020 | 2 | 3 | | III-2 | Dmc1 | 11144 | 7-Jun-15 | 6586 | 2 | 3 | | III-2 | Elac1 | 55520 | 4-May-15 |

Fig.22 - 44

| | | | | | | | | | | | | | | |
|---|---|---|---|---|---|---|---|---|---|---|---|---|---|---|
| 6590 | 2 | 3 | | | III-2 | Elavl2 | 1993 | 4-May-15 | 7094 | 2 | 3 | | III-2 | Fam196a | 642938 | 4-May-15 |
| 6597 | 2 | 3 | | | III-2 | Elf5 | 2001 | 4-May-15 | 7096 | 2 | 3 | | III-2 | Fam198a | 729085 | 4-May-15 |
| 6599 | 2 | 3 | | | III-2 | Elfn2 | 114794 | 4-May-15 | 7108 | 2 | 3 | | III-2 | Fam208a | 23272 | 4-May-15 |
| 6601 | 2 | 3 | | | III-2 | Elk3 | 2004 | 7-Jun-15 | 7110 | 2 | 3 | | III-2 | Fam209 | | |
| 6604 | 2 | 3 | | | III-2 | Elk2 | 22926 | 4-May-15 | 7115 | 2 | 3 | | III-2 | Fam210a | 125228 | 12-May-15 |
| 6607 | 2 | 3 | | | III-2 | Elmo2 | 63916 | 4-May-15 | 7125 | 2 | 3 | | III-2 | Fam217a | 222826 | 4-May-15 |
| 6615 | 2 | 3 | | | III-2 | Elovl1 | 64834 | 4-May-15 | 7128 | 2 | 3 | | III-2 | Fam219aos | | |
| 6623 | 2 | 3 | | | III-2 | Elp3 | 55140 | 4-May-15 | 7135 | 2 | 3 | | III-2 | Fam227a | 646851 | 4-May-15 |
| 6626 | 2 | 3 | | | III-2 | Elp6 | 54859 | 4-May-15 | 7139 | 2 | 3 | | III-2 | Fam229a | 100126071 | 21-May-15 |
| 6630 | 2 | 3 | | | III-2 | Emc10 | 284361 | 4-May-15 | 7147 | 2 | 3 | | III-2 | Fam35a | 54537 | 4-May-15 |
| 6633 | 2 | 3 | | | III-2 | Emc4 | 51234 | 4-May-15 | 7149 | 2 | 3 | | III-2 | Fam3b | 54097 | 12-May-15 |
| 6636 | 2 | 3 | | | III-2 | Emc8 | 10328 | 4-May-15 | 7153 | 2 | 3 | | III-2 | Fam45a | 404636 | 4-May-15 |
| 6640 | 2 | 3 | | | III-2 | Eme1 | 146956 | 4-May-15 | 7158 | 2 | 3 | | III-2 | Fam47c | 442434 | 4-May-15 |
| 6647 | 2 | 3 | | | III-2 | Eml1 | 2009 | 12-May-15 | 7163 | 2 | 3 | | III-2 | Fam50b | 26240 | 4-May-15 |
| 6649 | 2 | 3 | | | III-2 | Eml3 | 256364 | 12-May-15 | 7170 | 2 | 3 | | III-2 | Fam60a | 58516 | 12-May-15 |
| 6650 | 2 | 3 | | | III-2 | Eml4 | 27436 | 17-May-15 | 7175 | 2 | 3 | | III-2 | Fam65b | 9750 | 4-May-15 |
| 6658 | 2 | 3 | | | III-2 | Emx1 | 2016 | 4-May-15 | 7180 | 2 | 3 | | III-2 | Fam71a | 149647 | 12-May-15 |
| 6670 | 2 | 3 | | | III-2 | Eng | 2022 | 23-May-15 | 7185 | 2 | 3 | | III-2 | Fam71f1 | 84691 | 4-May-15 |
| 6680 | 2 | 3 | | | III-2 | Enoph1 | 58478 | 4-May-15 | 7191 | 2 | 3 | | III-2 | Fam76b | 143684 | 4-May-15 |
| 6683 | 2 | 3 | | | III-2 | Enpep | 2028 | 12-May-15 | 7194 | 2 | 3 | | III-2 | Fam81a | 145773 | 4-May-15 |
| 6703 | 2 | 3 | | | III-2 | Eogt | 285203 | 4-May-15 | 7195 | 2 | 3 | | III-2 | Fam83a | 84985 | 4-May-15 |
| 6707 | 2 | 3 | | | III-2 | Epas1 | 2034 | 17-May-15 | 7198 | 2 | 3 | | III-2 | Fam83d | 81610 | 12-May-15 |
| 6724 | 2 | 3 | | | III-2 | Epha2 | 1969 | 4-May-15 | 7200 | 2 | 3 | | III-2 | Fam83f | 133828 | 12-May-15 |
| 6727 | 2 | 3 | | | III-2 | Epha5 | 2044 | 29-May-15 | 7208 | 2 | 3 | | III-2 | Fam92a | | |
| 6730 | 2 | 3 | | | III-2 | Epha8 | 2046 | 3-May-15 | 7210 | 2 | 3 | | III-2 | Fam96a | 84191 | 4-May-15 |
| 6743 | 2 | 3 | | | III-2 | Epn2 | 22905 | 3-May-15 | 7213 | 2 | 3 | | III-2 | Fam98b | 283742 | 4-May-15 |
| 6750 | 2 | 3 | | | III-2 | Eps15 | 2060 | 12-May-15 | 7217 | 2 | 3 | | III-2 | Fancc | 2187 | 23-May-15 |
| 6752 | 2 | 3 | | | III-2 | Eps8 | 2059 | 4-May-15 | 7219 | 2 | 3 | | III-2 | Fancd2 | 2177 | 23-May-15 |
| 6758 | 2 | 3 | | | III-2 | Epx | 8288 | 12-May-15 | 7222 | 2 | 3 | | III-2 | Fancf | 2188 | 28-May-15 |
| 6759 | 2 | 3 | | | III-2 | Epyc | 1833 | 4-May-15 | 7224 | 2 | 3 | | III-2 | Fanci | 55215 | 23-May-15 |
| 6761 | 2 | 3 | | | III-2 | Erat1 | 26284 | 4-May-15 | 7227 | 2 | 3 | | III-2 | Fank1 | 92565 | 12-May-15 |
| 6763 | 2 | 3 | | | III-2 | Eras | 3266 | 10-May-15 | 7228 | 2 | 3 | | III-2 | Fap | 2191 | 7-Jun-15 |
| 6768 | 2 | 3 | | | III-2 | Ercc1 | 23085 | 12-May-15 | 7240 | 2 | 3 | | III-2 | Fastkd1 | 79675 | 4-May-15 |
| 6771 | 2 | 3 | | | III-2 | Ercc2 | 2068 | 4-Jun-15 | 7249 | 2 | 3 | | III-2 | Fau | 2197 | 12-May-15 |
| 6772 | 2 | 3 | | | III-2 | Ercc3 | 2071 | 4-Jun-15 | 7252 | 2 | 3 | | III-2 | Fbl | 2091 | 4-May-15 |
| 6773 | 2 | 3 | | | III-2 | Ercc4 | 2072 | 23-May-15 | 7264 | 2 | 3 | | III-2 | Fbrsl1 | 57666 | 4-May-15 |
| 6778 | 2 | 3 | | | III-2 | Ercc8 | 1161 | 23-May-15 | 7271 | 2 | 3 | | III-2 | Fbxl17 | 64839 | 4-May-15 |
| 6784 | 2 | 3 | | | III-2 | Ergic2 | 51290 | 4-May-15 | 7276 | 2 | 3 | | III-2 | Fbxl21 | 26223 | 4-May-15 |
| 6788 | 2 | 3 | | | III-2 | Eri2 | 112479 | 4-May-15 | 7279 | 2 | 3 | | III-2 | Fbxl4 | 26235 | 4-May-15 |
| 6791 | 2 | 3 | | | III-2 | Erich2 | 285141 | 12-May-15 | 7295 | 2 | 3 | | III-2 | Fbxo27 | 126433 | 4-May-15 |
| 6792 | 2 | 3 | | | III-2 | Erich3 | 127254 | 4-May-15 | 7296 | 2 | 3 | | III-2 | Fbxo28 | 23219 | 4-May-15 |
| 6795 | 2 | 3 | | | III-2 | Erich6 | 131831 | 12-May-15 | 7297 | 2 | 3 | | III-2 | Fbxo3 | 26273 | 31-May-15 |
| 6796 | 2 | 3 | | | III-2 | Erlec1 | 27248 | 3-May-15 | 7302 | 2 | 3 | | III-2 | Fbxo34 | 55030 | 4-May-15 |
| 6802 | 2 | 3 | | | III-2 | Ermp1 | 79956 | 4-May-15 | 7305 | 2 | 3 | | III-2 | Fbxo39 | 162517 | 4-May-15 |
| 6809 | 2 | 3 | | | III-2 | Erp44 | 23071 | 4-May-15 | 7309 | 2 | 3 | | III-2 | Fbxo42 | 54455 | 4-May-15 |
| 6817 | 2 | 3 | | | III-2 | Esm1 | 11082 | 12-May-15 | 7313 | 2 | 3 | | III-2 | Fbxo46 | 23403 | 4-May-15 |
| 6819 | 2 | 3 | | | III-2 | Esp15 | | | 7315 | 2 | 3 | | III-2 | Fbxo48 | 554251 | 4-May-15 |
| 6823 | 2 | 3 | | | III-2 | Esp24 | | | 7329 | 2 | 3 | | III-2 | Fbxw19 | | |
| 6837 | 2 | 3 | | | III-2 | Esr1 | 2099 | 31-May-15 | 7330 | 2 | 3 | | III-2 | Fbxw2 | 26190 | 4-May-15 |
| 6842 | 2 | 3 | | | III-2 | Esrrb | 2103 | 23-May-15 | 7341 | 2 | 3 | | III-2 | Fbxw9 | 84261 | 4-May-15 |
| 6845 | 2 | 3 | | | III-2 | Esyt1 | 23344 | 4-May-15 | 7354 | 2 | 3 | | III-2 | Fcho2 | 115548 | 4-May-15 |
| 6853 | 2 | 3 | | | III-2 | Etfdh | 2110 | 12-May-15 | 7355 | 2 | 3 | | III-2 | Fchsd1 | 89848 | 4-May-15 |
| 6870 | 2 | 3 | | | III-2 | Eva1a | 84141 | 4-May-15 | 7361 | 2 | 3 | | III-2 | Fcrl6 | 343419 | 4-May-15 |
| 6877 | 2 | 3 | | | III-2 | Evi2b | 2124 | 4-May-15 | 7364 | 2 | 3 | | III-2 | Fcrls | | |
| 6879 | 2 | 3 | | | III-2 | Evi5l | 115704 | 12-May-15 | 7370 | 2 | 3 | | III-2 | Fdx | 2232 | 4-May-15 |
| 6887 | 2 | 3 | | | III-2 | Exo1 | 9156 | 12-May-15 | 7374 | 2 | 3 | | III-2 | Fem1c | 56929 | 4-May-15 |
| 6889 | 2 | 3 | | | III-2 | Exoc1 | 55763 | 7-Jun-15 | 7377 | 2 | 3 | | III-2 | Fer1l4 | 80307 | 4-May-15 |
| 6890 | 2 | 3 | | | III-2 | Exoc2 | 55770 | 3-May-15 | 7378 | 2 | 3 | | III-2 | Fer1l5 | 90342 | 12-May-15 |
| 6894 | 2 | 3 | | | III-2 | Exoc4 | 60412 | 4-May-15 | 7390 | 2 | 3 | | III-2 | Fez2 | 55079 | 4-May-15 |
| 6896 | 2 | 3 | | | III-2 | Exoc6 | 54536 | 4-May-15 | 7404 | 2 | 3 | | III-2 | Fgf10 | 2255 | 12-May-15 |
| 6897 | 2 | 3 | | | III-2 | Exoc6b | 23233 | 4-May-15 | 7411 | 2 | 3 | | III-2 | Fgf17 | 8822 | 12-May-15 |
| 6898 | 2 | 3 | | | III-2 | Exoc7 | 23265 | 3-May-15 | 7429 | 2 | 3 | | III-2 | Fgfr1op2 | 26127 | 4-May-15 |
| 6900 | 2 | 3 | | | III-2 | Exog | 9941 | 3-May-15 | 7438 | 2 | 3 | | III-2 | Fgfrl1 | 53834 | 4-May-15 |
| 6904 | 2 | 3 | | | III-2 | Exosc3 | 51010 | 23-May-15 | 7440 | 2 | 3 | | III-2 | Fhad1 | 114827 | 4-May-15 |
| 6913 | 2 | 3 | | | III-2 | Ext2 | 2132 | 7-Jun-15 | 7450 | 2 | 3 | | III-2 | Fhod3 | 80206 | 7-Jun-15 |
| 6916 | 2 | 3 | | | III-2 | Extl3 | 2137 | 4-May-15 | 7455 | 2 | 3 | | III-2 | Fig4 | 9896 | 23-May-15 |
| 6920 | 2 | 3 | | | III-2 | Eya4 | 2070 | 23-May-15 | 7464 | 2 | 3 | | III-2 | Firre | 286467 | 22-May-15 |
| 6927 | 2 | 3 | | | III-2 | F12 | 2161 | 31-May-15 | 7474 | 2 | 3 | | III-2 | Fkbp1a | 2280 | 12-May-15 |
| 6938 | 2 | 3 | | | III-2 | F630028O10Rik | | | 7477 | 2 | 3 | | III-2 | Fkbp3 | 2287 | 4-May-15 |
| 6940 | 2 | 3 | | | III-2 | F630131L10Rik | | | 7483 | 2 | 3 | | III-2 | Fkbp9 | 11328 | 4-May-15 |
| 6949 | 2 | 3 | | | III-2 | F8a | 8263 | 4-May-15 | 7485 | 2 | 3 | | III-2 | Fkrp | 79147 | 23-May-15 |
| 6964 | 2 | 3 | | | III-2 | Fads1 | 3992 | 12-May-15 | 7486 | 2 | 3 | | III-2 | Fktn | 2218 | 23-May-15 |
| 6969 | 2 | 3 | | | III-2 | Faf2 | 23197 | 12-May-15 | 7488 | 2 | 3 | | III-2 | Flcn | 201163 | 24-May-15 |
| 6980 | 2 | 3 | | | III-2 | Fam103a1 | 83640 | 4-May-15 | 7492 | 2 | 3 | | III-2 | Flna | 2316 | 28-May-15 |
| 6981 | 2 | 3 | | | III-2 | Fam104a | 84923 | 4-May-15 | 7497 | 2 | 3 | | III-2 | Flrt1 | 23769 | 12-May-15 |
| 6993 | 2 | 3 | | | III-2 | Fam115a | 9747 | 4-May-15 | 7507 | 2 | 3 | | III-2 | Fmn2 | 56776 | 24-May-15 |
| 7001 | 2 | 3 | | | III-2 | Fam120aos | 158293 | 4-May-15 | 7510 | 2 | 3 | | III-2 | Fmnl3 | 91010 | 4-May-15 |
| 7003 | 2 | 3 | | | III-2 | Fam120c | 54954 | 4-May-15 | 7517 | 2 | 3 | | III-2 | Fmo9 | | |
| 7005 | 2 | 3 | | | III-2 | Fam122b | 159090 | 12-May-15 | 7525 | 2 | 3 | | III-2 | Fnbp1l | 54874 | 4-May-15 |
| 7007 | 2 | 3 | | | III-2 | Fam124a | 220108 | 4-May-15 | 7530 | 2 | 3 | | III-2 | Fndc3b | 64778 | 4-May-15 |
| 7029 | 2 | 3 | | | III-2 | Fam149a | 25854 | 4-May-15 | 7538 | 2 | 3 | | III-2 | Fnip2 | 57600 | 4-May-15 |
| 7031 | 2 | 3 | | | III-2 | Fam150a | 389658 | 4-May-15 | 7540 | 2 | 3 | | III-2 | Fntb | 2342 | 4-May-15 |
| 7032 | 2 | 3 | | | III-2 | Fam150b | 285016 | 4-May-15 | 7552 | 2 | 3 | | III-2 | Foxa2 | 3170 | 31-May-15 |
| 7036 | 2 | 3 | | | III-2 | Fam154b | 283726 | 4-May-15 | 7553 | 2 | 3 | | III-2 | Foxa3 | 3171 | 28-May-15 |
| 7039 | 2 | 3 | | | III-2 | Fam159b | 100133916 | 4-May-15 | 7554 | 2 | 3 | | III-2 | Foxb1 | 27023 | 28-May-15 |
| 7040 | 2 | 3 | | | III-2 | Fam160a1 | 729830 | 4-May-15 | 7559 | 2 | 3 | | III-2 | Foxd2 | 2306 | 28-May-15 |
| 7042 | 2 | 3 | | | III-2 | Fam160b1 | 57700 | 4-May-15 | 7560 | 2 | 3 | | III-2 | Foxd2os | | |
| 7051 | 2 | 3 | | | III-2 | Fam166b | 730112 | 4-May-15 | 7563 | 2 | 3 | | III-2 | Foxe1 | 2304 | 28-May-15 |
| 7055 | 2 | 3 | | | III-2 | Fam168b | 130074 | 21-May-15 | 7566 | 2 | 3 | | III-2 | Foxf2 | 2295 | 12-May-15 |
| 7059 | 2 | 3 | | | III-2 | Fam170b | 170370 | 4-May-15 | 7577 | 2 | 3 | | III-2 | Foxl1 | 2300 | 4-May-15 |
| 7064 | 2 | 3 | | | III-2 | Fam173a | 65990 | 21-May-15 | 7582 | 2 | 3 | | III-2 | Foxn2 | 3344 | 4-May-15 |
| 7069 | 2 | 3 | | | III-2 | Fam175b | 23172 | 4-May-15 | 7585 | 2 | 3 | | III-2 | Foxo1 | 2308 | 17-May-15 |
| 7070 | 2 | 3 | | | III-2 | Fam178a | 55719 | 12-May-15 | 7590 | 2 | 3 | | III-2 | Foxp2 | 93986 | 4-May-15 |
| 7076 | 2 | 3 | | | III-2 | Fam181b | 220382 | 4-May-15 | 7595 | 2 | 3 | | III-2 | Foxr2 | 139628 | 28-May-15 |
| 7085 | 2 | 3 | | | III-2 | Fam188b | 84182 | 4-May-15 | 7605 | 2 | 3 | | III-2 | Fpr-rs4 | | |
| 7087 | 2 | 3 | | | III-2 | Fam189a2 | 9413 | 4-May-15 | 7609 | 2 | 3 | | III-2 | Frat1 | 10023 | 4-May-15 |
| 7089 | 2 | 3 | | | III-2 | Fam192a | 80011 | 4-May-15 | 7617 | 2 | 3 | | III-2 | Frmd4a | 55691 | 14-May-15 |

Fig.22 - 45

| | | | | | | | | | | | | | | | |
|---|---|---|---|---|---|---|---|---|---|---|---|---|---|---|---|
| 7621 | 2 | 3 | | | H-2 | Frmd7 | 90167 | 23-May-15 | 8115 | 2 | 3 | | | H-2 | Gm10433 | |
| 7622 | 2 | 3 | | | H-2 | Frmd8 | 83786 | 12-May-15 | 8123 | 2 | 3 | | | H-2 | Gm10471 | |
| 7632 | 2 | 3 | | | H-2 | Fry | 10129 | 12-May-15 | 8129 | 2 | 3 | | | H-2 | Gm10509 | |
| 7633 | 2 | 3 | | | H-2 | Fryl | 285527 | 4-May-15 | 8131 | 2 | 3 | | | H-2 | Gm10512 | |
| 7634 | 2 | 3 | | | H-2 | Frzb | 2487 | 4-May-15 | 8134 | 2 | 3 | | | H-2 | Gm10536 | |
| 7636 | 2 | 3 | | | H-2 | Fscb | 84075 | 4-May-15 | 8137 | 2 | 3 | | | H-2 | Gm10549 | |
| 7637 | 2 | 3 | | | H-2 | Fscn1 | 5824 | 24-May-15 | 8138 | 2 | 3 | | | H-2 | Gm10556 | |
| 7639 | 2 | 3 | | | H-2 | Fscn3 | 29999 | 12-May-15 | 8141 | 2 | 3 | | | H-2 | Gm10584 | |
| 7640 | 2 | 3 | | | H-2 | Fsd1 | 79187 | 4-May-15 | 8144 | 2 | 3 | | | H-2 | Gm10635 | |
| 7644 | 2 | 3 | | | H-2 | Fshr | 2492 | 24-May-15 | 8146 | 2 | 3 | | | H-2 | Gm10637 | |
| 7645 | 2 | 3 | | | H-2 | Fsip3 | 161835 | 4-May-15 | 8154 | 2 | 3 | | | H-2 | Gm10665 | |
| 7650 | 2 | 3 | | | H-2 | Fst15 | 56884 | 4-May-15 | 8160 | 2 | 3 | | | H-2 | Gm10696 | |
| 7651 | 2 | 3 | | | H-2 | Ftcd | 10841 | 4-May-15 | 8169 | 2 | 3 | | | H-2 | Gm10785 | |
| 7653 | 2 | 3 | | | H-2 | Fthl17 | 53940 | 4-May-15 | 8180 | 2 | 3 | | | H-2 | Gm10863 | |
| 7656 | 2 | 3 | | | H-2 | Fto | 79068 | 31-May-15 | 8184 | 2 | 3 | | | H-2 | Gm10922 | |
| 7660 | 2 | 3 | | | H-2 | Ftx | 100302692 | 22-May-15 | 8191 | 2 | 3 | | | H-2 | Gm1166 | |
| 7662 | 2 | 3 | | | H-2 | Fubp3 | 8939 | 28-May-15 | 8207 | 2 | 3 | | | H-2 | Gm11487 | |
| 7666 | 2 | 3 | | | H-2 | Fundc1 | 139341 | 24-May-15 | 8210 | 2 | 3 | | | H-2 | Gm11538 | |
| 7670 | 2 | 3 | | | H-2 | Fus | 2521 | 31-May-15 | 8234 | 2 | 3 | | | H-2 | Gm11757 | |
| 7677 | 2 | 3 | | | H-2 | Fut7 | 2529 | 4-May-15 | 8242 | 2 | 3 | | | H-2 | Gm11961 | |
| 7679 | 2 | 3 | | | H-2 | Fut9 | 10690 | 12-May-15 | 8245 | 2 | 3 | | | H-2 | Gm11981 | |
| 7695 | 2 | 3 | | | H-2 | Fyttd1 | 84248 | 4-May-15 | 8252 | 2 | 3 | | | H-2 | Gm12159 | |
| 7702 | 2 | 3 | | | H-2 | Fzd6 | 8323 | 12-May-15 | 8261 | 2 | 3 | | | H-2 | Gm12295 | |
| 7706 | 2 | 3 | | | H-2 | Fzr1 | 51343 | 4-May-15 | 8267 | 2 | 3 | | | H-2 | Gm12504 | |
| 7710 | 2 | 3 | | | H-2 | G3bp2 | 9908 | 31-May-15 | 8269 | 2 | 3 | | | H-2 | Gm12522 | |
| 7714 | 2 | 3 | | | H-2 | G630071F17Rik | | | 8279 | 2 | 3 | | | H-2 | Gm12794 | |
| 7721 | 2 | 3 | | | H-2 | G6pc3 | 92579 | 4-May-15 | 8282 | 2 | 3 | | | H-2 | Gm12886 | |
| 7725 | 2 | 3 | | | H-2 | Gaa | 2548 | 23-May-15 | 8290 | 2 | 3 | | | H-2 | Gm13031 | |
| 7729 | 2 | 3 | | | H-2 | Gabarap | 11337 | 24-May-15 | 8292 | 2 | 3 | | | H-2 | Gm13034 | |
| 7735 | 2 | 3 | | | H-2 | Gabpb1 | 2553 | 7-Jun-15 | 8294 | 2 | 3 | | | H-2 | Gm13043 | |
| 7738 | 2 | 3 | | | H-2 | Gabra2 | 2555 | 4-May-15 | 8310 | 2 | 3 | | | H-2 | Gm13157 | |
| 7740 | 2 | 3 | | | H-2 | Gabra4 | 2557 | 4-May-15 | 8315 | 2 | 3 | | | H-2 | Gm13238 | |
| 7741 | 2 | 3 | | | H-2 | Gabra5 | 2558 | 28-May-15 | 8317 | 2 | 3 | | | H-2 | Gm13247 | |
| 7747 | 2 | 3 | | | H-2 | Gabre | 2564 | 12-May-15 | 8320 | 2 | 3 | | | H-2 | Gm13272 | |
| 7758 | 2 | 3 | | | H-2 | Gad2 | 2572 | 24-May-15 | 8341 | 2 | 3 | | | H-2 | Gm13483 | |
| 7765 | 2 | 3 | | | H-2 | Gal | 51083 | 17-May-15 | 8344 | 2 | 3 | | | H-2 | Gm13498 | |
| 7774 | 2 | 3 | | | H-2 | Galm | 130589 | 12-May-15 | 8349 | 2 | 3 | | | H-2 | Gm13580 | |
| 7775 | 2 | 3 | | | H-2 | Galns | 2588 | 23-May-15 | 8351 | 2 | 3 | | | H-2 | Gm136 | |
| 7777 | 2 | 3 | | | H-2 | Galnt10 | 55568 | 4-May-15 | 8355 | 2 | 3 | | | H-2 | Gm13752 | |
| 7778 | 2 | 3 | | | H-2 | Galnt11 | 63917 | 12-May-15 | 8362 | 2 | 3 | | | H-2 | Gm13944 | |
| 7798 | 2 | 3 | | | H-2 | Galt | 2592 | 7-Jun-15 | 8365 | 2 | 3 | | | H-2 | Gm14023 | |
| 7799 | 2 | 3 | | | H-2 | Gamt | 2593 | 23-May-15 | 8369 | 2 | 3 | | | H-2 | Gm14124 | |
| 7802 | 2 | 3 | | | H-2 | Ganc | 2595 | 12-May-15 | 8372 | 2 | 3 | | | H-2 | Gm14151 | |
| 7808 | 2 | 3 | | | H-2 | Gar1 | 54433 | 7-Jun-15 | 8381 | 2 | 3 | | | H-2 | Gm14308 | |
| 7811 | 2 | 3 | | | H-2 | Garnl3 | 84253 | 14-May-15 | 8393 | 2 | 3 | | | H-2 | Gm14391 | |
| 7812 | 2 | 3 | | | H-2 | Gas2l3 | 283431 | 12-May-15 | 8397 | 2 | 3 | | | H-2 | Gm14420 | |
| 7835 | 2 | 3 | | | H-2 | Gatm | 2628 | 23-May-15 | 8403 | 2 | 3 | | | H-2 | Gm14459 | |
| 7839 | 2 | 3 | | | H-2 | Gba2 | 57704 | 4-May-15 | 8421 | 2 | 3 | | | H-2 | Gm14632 | |
| 7843 | 2 | 3 | | | H-2 | Gbgt1 | 26301 | 12-May-15 | 8437 | 2 | 3 | | | H-2 | Gm14920 | |
| 7848 | 2 | 3 | | | H-2 | Gbp3 | 2635 | 7-Jun-15 | 8439 | 2 | 3 | | | H-2 | Gm15023 | |
| 7856 | 2 | 3 | | | H-2 | Gbx2 | 2637 | 12-May-15 | 8457 | 2 | 3 | | | H-2 | Gm15299 | |
| 7863 | 2 | 3 | | | H-2 | Gcfc2 | 6936 | 4-May-15 | 8460 | 2 | 3 | | | H-2 | Gm15319 | |
| 7864 | 2 | 3 | | | H-2 | Gcg | 2641 | 17-May-15 | 8461 | 2 | 3 | | | H-2 | Gm15328 | |
| 7882 | 2 | 3 | | | H-2 | Gda | 9615 | 7-Jun-15 | 8468 | 2 | 3 | | | H-2 | Gm15413 | |
| 7893 | 2 | 3 | | | H-2 | Gdf3 | 9573 | 4-May-15 | 8482 | 2 | 3 | | | H-2 | Gm15679 | |
| 7899 | 2 | 3 | | | H-2 | Gdi2 | 2665 | 4-May-15 | 8499 | 2 | 3 | | | H-2 | Gm15987 | |
| 7905 | 2 | 3 | | | H-2 | Gdpd5 | 81544 | 4-May-15 | 8501 | 2 | 3 | | | H-2 | Gm16023 | |
| 7910 | 2 | 3 | | | H-2 | Gemin5 | 25829 | 12-May-15 | 8503 | 2 | 3 | | | H-2 | Gm16046 | |
| 7921 | 2 | 3 | | | H-2 | Gfm2 | 84340 | 4-May-15 | 8506 | 2 | 3 | | | H-2 | Gm16130 | |
| 7924 | 2 | 3 | | | H-2 | Gfpt1 | 2673 | 23-May-15 | 8523 | 2 | 3 | | | H-2 | Gm16451 | |
| 7931 | 2 | 3 | | | H-2 | Gfy | 100507003 | 4-May-15 | 8528 | 2 | 3 | | | H-2 | Gm16523 | |
| | | | | | | | | | 8529 | 2 | 3 | | | H-2 | Gm1653 | |
| 7950 | 2 | 3 | | | H-2 | Ghitm | 27069 | 4-May-15 | 8531 | 2 | 3 | | | H-2 | Gm16548 | |
| 7953 | 2 | 3 | | | H-2 | Ghrhr | 2692 | 12-May-15 | 8536 | 2 | 3 | | | H-2 | Gm1561 | |
| 7956 | 2 | 3 | | | H-2 | Gid4 | 79018 | 12-May-15 | 8540 | 2 | 3 | | | H-2 | Gm16701 | |
| 7958 | 2 | 3 | | | H-2 | Gif | 2694 | 7-Jun-15 | 8541 | 2 | 3 | | | H-2 | Gm16702 | |
| 7975 | 2 | 3 | | | H-2 | Gip | 2695 | 7-Jun-15 | 8542 | 2 | 3 | | | H-2 | Gm16712 | |
| 7976 | 2 | 3 | | | H-2 | Gipc1 | 10755 | 4-May-15 | 8552 | 2 | 3 | | | H-2 | Gm16880 | |
| 7980 | 2 | 3 | | | H-2 | Git1 | 28964 | 12-May-15 | 8557 | 2 | 3 | | | H-2 | Gm16973 | |
| 7981 | 2 | 3 | | | H-2 | Git2 | 9815 | 31-May-15 | 8563 | 2 | 3 | | | H-2 | Gm1720 | |
| 7984 | 2 | 3 | | | H-2 | Gja3 | 2700 | 4-May-15 | 8570 | 2 | 3 | | | H-2 | Gm17660 | |
| 7988 | 2 | 3 | | | H-2 | Gja8 | 2701 | 12-May-15 | 8576 | 2 | 3 | | | H-2 | Gm17751 | |
| 7998 | 2 | 3 | | | H-2 | Gjd2 | 57369 | 12-May-15 | 8579 | 2 | 3 | | | H-2 | Gm17769 | |
| 8000 | 2 | 3 | | | H-2 | Gjd4 | 219770 | 4-May-15 | 8582 | 2 | 3 | | | H-2 | Gm17830 | |
| 8001 | 2 | 3 | | | H-2 | Gle1 | 100126572 | 4-May-15 | 8585 | 2 | 3 | | | H-2 | Gm18853 | |
| | | | | | | | | | 8594 | 2 | 3 | | | H-2 | Gm1943 | |
| 8018 | 2 | 3 | | | H-2 | Glipr1l2 | 144321 | 4-May-15 | 8596 | 2 | 3 | | | H-2 | Gm19461 | |
| 8025 | 2 | 3 | | | H-2 | Glis3 | 169792 | 14-May-15 | 8598 | 2 | 3 | | | H-2 | Gm19510 | |
| 8029 | 2 | 3 | | | H-2 | Glod4 | 51031 | 4-May-15 | 8602 | 2 | 3 | | | H-2 | Gm19589 | |
| 8032 | 2 | 3 | | | H-2 | Glra1 | 2741 | 23-May-15 | 8608 | 2 | 3 | | | H-2 | Gm19689 | |
| 8036 | 2 | 3 | | | H-2 | Glra3 | 8001 | 12-May-15 | 8614 | 2 | 3 | | | H-2 | Gm19784 | |
| 8038 | 2 | 3 | | | H-2 | Glrx3 | 10539 | 4-May-15 | 8619 | 2 | 3 | | | H-2 | Gm1995 | |
| 8044 | 2 | 3 | | | H-2 | Gt1d1 | 144423 | 12-May-15 | 8622 | 2 | 3 | | | H-2 | Gm20063 | |
| 8048 | 2 | 3 | | | H-2 | Gt8d1 | 55830 | 23-May-15 | 8626 | 2 | 3 | | | H-2 | Gm2012 | |
| 8052 | 2 | 3 | | | H-2 | Gltpd1 | 80772 | 4-May-15 | 8636 | 2 | 3 | | | H-2 | Gm2027 | |
| 8055 | 2 | 3 | | | H-2 | Gltpd2 | 388323 | 4-May-15 | 8638 | 2 | 3 | | | H-2 | Gm20300 | |
| 8056 | 2 | 3 | | | H-2 | Gm10007 | | | 8643 | 2 | 3 | | | H-2 | Gm20362 | |
| 8067 | 2 | 3 | | | H-2 | Gm10057 | | | 8649 | 2 | 3 | | | H-2 | Gm20604 | |
| 8073 | 2 | 3 | | | H-2 | Gm10126 | | | 8660 | 2 | 3 | | | H-2 | Gm20745 | |
| 8082 | 2 | 3 | | | H-2 | Gm10190 | | | 8684 | 2 | 3 | | | H-2 | Gm20854 | |
| 8085 | 2 | 3 | | | H-2 | Gm10220 | | | 8701 | 2 | 3 | | | H-2 | Gm21269 | |
| 8086 | 2 | 3 | | | H-2 | Gm10248 | | | 8713 | 2 | 3 | | | H-2 | Gm21671 | |
| 8090 | 2 | 3 | | | H-2 | Gm10318 | | | 8733 | 2 | 3 | | | H-2 | Gm2762 | |
| 8094 | 2 | 3 | | | H-2 | Gm10354 | | | 8739 | 2 | 3 | | | H-2 | Gm2897 | |
| 8099 | 2 | 3 | | | H-2 | Gm10373 | | | 8748 | 2 | 3 | | | H-2 | Gm3143 | |
| 8101 | 2 | 3 | | | H-2 | Gm10432 | | | 8753 | 2 | 3 | | | H-2 | Gm3259 | |
| 8114 | 2 | 3 | | | H-2 | Gm10432 | | | 8754 | 2 | 3 | | | H-2 | Gm3264 | |

Fig.22 - 46

| | | | | | | | | | | | | | | | |
|---|---|---|---|---|---|---|---|---|---|---|---|---|---|---|---|
| 8756 | 2 | 3 | | | III-2 | Gm3285 | | | 9382 | 2 | 3 | | III-2 | Gpr174 | 84636 | 4-May-15 |
| 8776 | 2 | 3 | | | III-2 | Gm364 | | | 9384 | 2 | 3 | | III-2 | Gpr179 | 440435 | 4-May-15 |
| 8783 | 2 | 3 | | | III-2 | Gm3763 | | | 9385 | 2 | 3 | | III-2 | Gpr18 | 2841 | 4-May-15 |
| 8786 | 2 | 3 | | | III-2 | Gm3893 | | | 9391 | 2 | 3 | | III-2 | Gpr21 | 2844 | 4-May-15 |
| 8792 | 2 | 3 | | | III-2 | Gm4133 | | | 9392 | 2 | 3 | | III-2 | Gpr22 | 2845 | 4-May-15 |
| 8793 | 2 | 3 | | | III-2 | Gm4175 | | | 9394 | 2 | 3 | | III-2 | Gpr26 | 2849 | 7-Jun-15 |
| 8805 | 2 | 3 | | | III-2 | Gm4301 | | | 9397 | 2 | 3 | | III-2 | Gpr31b | | |
| 8824 | 2 | 3 | | | III-2 | Gm4567 | | | 9401 | 2 | 3 | | III-2 | Gpr37 | 2861 | 28-May-15 |
| 8827 | 2 | 3 | | | III-2 | Gm4719 | | | 9402 | 2 | 3 | | III-2 | Gpr37l1 | 9283 | 4-May-15 |
| 8841 | 2 | 3 | | | III-2 | Gm4832 | | | 9410 | 2 | 3 | | III-2 | Gpr6 | 2830 | 4-May-15 |
| 8854 | 2 | 3 | | | III-2 | Gm4906 | | | 9421 | 2 | 3 | | III-2 | Gpr85 | 54329 | 4-May-15 |
| 8857 | 2 | 3 | | | III-2 | Gm4925 | | | 9438 | 2 | 3 | | III-2 | Gps2 | 2874 | 4-May-15 |
| 8865 | 2 | 3 | | | III-2 | Gm4971 | | | 9467 | 2 | 3 | | III-2 | Greb1 | 9687 | 18-May-15 |
| 8866 | 2 | 3 | | | III-2 | Gm4975 | | | 9479 | 2 | 3 | | III-2 | Grid1 | 2894 | 4-May-15 |
| 8869 | 2 | 3 | | | III-2 | Gm4984 | | | 9480 | 2 | 3 | | III-2 | Grid2 | 2895 | 4-May-15 |
| 8875 | 2 | 3 | | | III-2 | Gm5072 | | | 9481 | 2 | 3 | | III-2 | Grid2ip | 392862 | 4-May-15 |
| 8880 | 2 | 3 | | | III-2 | Gm5087 | | | 9496 | 2 | 3 | | III-2 | Grina | 2907 | 4-May-15 |
| 8890 | 2 | 3 | | | III-2 | Gm5122 | | | 9501 | 2 | 3 | | III-2 | Grk1 | 6011 | 12-May-15 |
| 8898 | 2 | 3 | | | III-2 | Gm5141 | | | 9504 | 2 | 3 | | III-2 | Grk6 | 2870 | 12-May-15 |
| 8900 | 2 | 3 | | | III-2 | Gm5148 | | | 9505 | 2 | 3 | | III-2 | Grm1 | 2911 | 4-May-15 |
| 8907 | 2 | 3 | | | III-2 | Gm525 | | | 9512 | 2 | 3 | | III-2 | Grm8 | 2918 | 12-May-15 |
| 8912 | 2 | 3 | | | III-2 | Gm5346 | | | 9520 | 2 | 3 | | III-2 | Grtp1 | 79774 | 4-May-15 |
| 8924 | 2 | 3 | | | III-2 | Gm5458 | | | 9526 | 2 | 3 | | III-2 | Gsc2 | 2928 | 4-May-15 |
| 8943 | 2 | 3 | | | III-2 | Gm5591 | | | 9527 | 2 | 3 | | III-2 | Gsdma | 284110 | 4-May-15 |
| 8944 | 2 | 3 | | | III-2 | Gm5592 | | | 9535 | 2 | 3 | | III-2 | Gsdmc2 | | |
| 8947 | 2 | 3 | | | III-2 | Gm561 | | | 9537 | 2 | 3 | | III-2 | Gsdmd | 79792 | 4-May-15 |
| 8951 | 2 | 3 | | | III-2 | Gm5627 | | | 9543 | 2 | 3 | | III-2 | Gsk3b | 2932 | 31-May-15 |
| 8957 | 2 | 3 | | | III-2 | Gm5712 | | | 9565 | 2 | 3 | | III-2 | Gstp1 | 2950 | 23-May-15 |
| 8967 | 2 | 3 | | | III-2 | Gm5796 | | | 9573 | 2 | 3 | | III-2 | Gsx2 | 170825 | 12-May-15 |
| 8973 | 2 | 3 | | | III-2 | Gm5833 | | | 9578 | 2 | 3 | | III-2 | Gtf2a2 | 2958 | 2-Jun-15 |
| 8977 | 2 | 3 | | | III-2 | Gm5878 | | | 9581 | 2 | 3 | | III-2 | Gtf2e2 | 2961 | 31-May-15 |
| 9002 | 2 | 3 | | | III-2 | Gm6121 | | | 9583 | 2 | 3 | | III-2 | Gtf2f2 | 2963 | 4-May-15 |
| 9008 | 2 | 3 | | | III-2 | Gm6225 | | | 9586 | 2 | 3 | | III-2 | Gtf2h3 | 2967 | 4-May-15 |
| 9019 | 2 | 3 | | | III-2 | Gm6329 | | | 9587 | 2 | 3 | | III-2 | Gtf2h4 | 2968 | 4-May-15 |
| 9025 | 2 | 3 | | | III-2 | Gm6408 | | | 9590 | 2 | 3 | | III-2 | Gtf2ird1 | 9569 | 28-May-15 |
| 9033 | 2 | 3 | | | III-2 | Gm6524 | | | 9594 | 2 | 3 | | III-2 | Gtf3c2 | 2976 | 4-May-15 |
| 9036 | 2 | 3 | | | III-2 | Gm6548 | | | 9597 | 2 | 3 | | III-2 | Gtf3c5 | 9328 | 4-May-15 |
| 9042 | 2 | 3 | | | III-2 | Gm6588 | | | 9599 | 2 | 3 | | III-2 | Gti3 | 29105 | 4-May-15 |
| 9066 | 2 | 3 | | | III-2 | Gm6880 | | | 9600 | 2 | 3 | | III-2 | Gtpbp1 | 9567 | 4-May-15 |
| 9075 | 2 | 3 | | | III-2 | Gm6994 | | | 9603 | 2 | 3 | | III-2 | Gtpbp3 | 84705 | 4-May-15 |
| 9076 | 2 | 3 | | | III-2 | Gm7008 | | | 9609 | 2 | 3 | | III-2 | Gtsf1l | 149699 | 4-May-15 |
| 9079 | 2 | 3 | | | III-2 | Gm7073 | | | 9618 | 2 | 3 | | III-2 | Gucy1b3 | 2983 | 12-May-15 |
| 9082 | 2 | 3 | | | III-2 | Gm711 | | | 9620 | 2 | 3 | | III-2 | Gucy2d | 3000 | 31-May-15 |
| 9087 | 2 | 3 | | | III-2 | Gm7168 | | | 9631 | 2 | 3 | | III-2 | Gxylt2 | 727936 | 4-May-15 |
| 9091 | 2 | 3 | | | III-2 | Gm7271 | | | 9651 | 2 | 3 | | III-2 | H13 | 81502 | 23-May-15 |
| 9096 | 2 | 3 | | | III-2 | Gm7361 | | | 9661 | 2 | 3 | | III-2 | H2afb3 | 83740 | 4-May-15 |
| 9099 | 2 | 3 | | | III-2 | Gm7457 | | | 9666 | 2 | 3 | | III-2 | H2afy2 | 55506 | 4-May-15 |
| 9105 | 2 | 3 | | | III-2 | Gm765 | | | 9676 | 2 | 3 | | III-2 | H2-Eb1 | | |
| 9109 | 2 | 3 | | | III-2 | Gm773 | | | 9681 | 2 | 3 | | III-2 | H2-Ke6 | 7929 | 4-May-15 |
| 9115 | 2 | 3 | | | III-2 | Gm7904 | | | 9683 | 2 | 3 | | III-2 | H2-M1 | | |
| 9135 | 2 | 3 | | | III-2 | Gm8439 | | | 9710 | 2 | 3 | | III-2 | H2-T3 | | |
| 9138 | 2 | 3 | | | III-2 | Gm8580 | | | 9714 | 2 | 3 | | III-2 | H60b | | |
| 9143 | 2 | 3 | | | III-2 | Gm8693 | | | 9715 | 2 | 3 | | III-2 | H60c | | |
| 9147 | 2 | 3 | | | III-2 | Gm8787 | | | 9720 | 2 | 3 | | III-2 | Hace1 | 57531 | 12-May-15 |
| 9150 | 2 | 3 | | | III-2 | Gm884 | | | 9723 | 2 | 3 | | III-2 | Hadha | 3030 | 31-May-15 |
| 9157 | 2 | 3 | | | III-2 | Gm8989 | | | 9731 | 2 | 3 | | III-2 | Hand2 | 9464 | 4-May-15 |
| 9162 | 2 | 3 | | | III-2 | Gm9054 | | | 9737 | 2 | 3 | | III-2 | Hapln3 | 145864 | 12-May-15 |
| 9165 | 2 | 3 | | | III-2 | Gm9112 | | | 9740 | 2 | 3 | | III-2 | Hars | 3035 | 12-May-15 |
| 9178 | 2 | 3 | | | III-2 | Gm9731 | | | 9745 | 2 | 3 | | III-2 | Has3 | 3038 | 4-May-15 |
| 9179 | 2 | 3 | | | III-2 | Gm9733 | | | 9749 | 2 | 3 | | III-2 | Haus3 | 79441 | 12-May-15 |
| 9185 | 2 | 3 | | | III-2 | Gm9855 | | | 9753 | 2 | 3 | | III-2 | Haus7 | 55559 | 4-May-15 |
| 9187 | 2 | 3 | | | III-2 | Gm9871 | | | 9772 | 2 | 3 | | III-2 | Hc | 727 | 7-Jun-15 |
| 9190 | 2 | 3 | | | III-2 | Gm9920 | | | 9776 | 2 | 3 | | III-2 | Hcfc1 | 3054 | 23-May-15 |
| 9191 | 2 | 3 | | | III-2 | Gm9926 | | | 9777 | 2 | 3 | | III-2 | Hcfc1r1 | 54985 | 12-May-15 |
| 9203 | 2 | 3 | | | III-2 | Gmeb2 | 26205 | 4-May-15 | 9782 | 2 | 3 | | III-2 | Hcn2 | 610 | 12-May-15 |
| 9211 | 2 | 3 | | | III-2 | Gmppb | 29925 | 4-May-15 | 9790 | 2 | 3 | | III-2 | Hdac10 | 83933 | 28-May-15 |
| 9214 | 2 | 3 | | | III-2 | Gmps | 8833 | 4-May-15 | 9793 | 2 | 3 | | III-2 | Hdac3 | 8841 | 31-May-15 |
| 9216 | 2 | 3 | | | III-2 | Gna12 | 2768 | 4-May-15 | 9804 | 2 | 3 | | III-2 | Hdgfl1 | 154150 | 12-May-15 |
| 9218 | 2 | 3 | | | III-2 | Gna14 | 9630 | 4-May-15 | 9811 | 2 | 3 | | III-2 | Hdx | 139324 | 4-May-15 |
| 9222 | 2 | 3 | | | III-2 | Gnai3 | 2773 | 12-May-15 | 9814 | 2 | 3 | | III-2 | Heatr3 | 55027 | 4-May-15 |
| 9226 | 2 | 3 | | | III-2 | Gnas | 2778 | 23-May-15 | 9818 | 2 | 3 | | III-2 | Heatr9 | 256957 | 4-May-15 |
| 9231 | 2 | 3 | | | III-2 | Gnb1 | 2782 | 3-May-15 | 9819 | 2 | 3 | | III-2 | Hebp1 | 50865 | 4-May-15 |
| 9232 | 2 | 3 | | | III-2 | Gnb1l | 54584 | 4-May-15 | 9825 | 2 | 3 | | III-2 | Hecw1 | 23072 | 4-May-15 |
| 9240 | 2 | 3 | | | III-2 | Gng13 | 2791 | 4-May-15 | 9829 | 2 | 3 | | III-2 | Hells | 3070 | 4-May-15 |
| 9252 | 2 | 3 | | | III-2 | Gnl2 | 29889 | 4-May-15 | 9832 | 2 | 3 | | III-2 | Helz | 9931 | 23-May-15 |
| 9257 | 2 | 3 | | | III-2 | Gnpda1 | 10007 | 12-May-15 | 9842 | 2 | 3 | | III-2 | Herc1 | 8925 | 12-May-15 |
| 9258 | 2 | 3 | | | III-2 | Gnpda2 | 132789 | 12-May-15 | 9847 | 2 | 3 | | III-2 | Herpud1 | 9709 | 12-May-15 |
| 9259 | 2 | 3 | | | III-2 | Gnpnat1 | 64841 | 4-May-15 | 9852 | 2 | 3 | | III-2 | Hes5 | 388585 | 4-May-15 |
| 9264 | 2 | 3 | | | III-2 | Gns | 2799 | 4-May-15 | 9859 | 2 | 3 | | III-2 | Hexim1 | 10614 | 4-May-15 |
| 9270 | 2 | 3 | | | III-2 | Golga7 | 51125 | 4-May-15 | 9867 | 2 | 3 | | III-2 | Hgd | 3081 | 23-May-15 |
| 9276 | 2 | 3 | | | III-2 | Golph3l | 55204 | 4-May-15 | 9878 | 2 | 3 | | III-2 | Hhla1 | 10086 | 4-May-15 |
| 9279 | 2 | 3 | | | III-2 | Gon4l | 54856 | 12-May-15 | 9879 | 2 | 3 | | III-2 | Hiat1 | 64645 | 4-May-15 |
| 9301 | 2 | 3 | | | III-2 | Gpat2 | 150763 | 4-May-15 | 9885 | 2 | 3 | | III-2 | Hid1 | 283987 | 12-May-15 |
| 9302 | 2 | 3 | | | III-2 | Gpatch1 | 55094 | 4-May-15 | 9886 | 2 | 3 | | III-2 | Hif1a | 3091 | 31-May-15 |
| 9310 | 2 | 3 | | | III-2 | Gpbp1 | 65056 | 4-May-15 | 9892 | 2 | 3 | | III-2 | Higd2a | 192286 | 4-May-15 |
| 9316 | 2 | 3 | | | III-2 | Gpc5 | 2262 | 24-May-15 | 9913 | 2 | 3 | | III-2 | Hist1h2aa | 221613 | 4-May-15 |
| 9325 | 2 | 3 | | | III-2 | Gphn | 10243 | 4-May-15 | 9923 | 2 | 3 | | III-2 | Hist1h2an | | |
| 9329 | 2 | 3 | | | III-2 | Gpld1 | 2822 | 4-May-15 | 9929 | 2 | 3 | | III-2 | Hist1h2be | 8344 | 4-May-15 |
| 9339 | 2 | 3 | | | III-2 | Gpr108 | 56927 | 4-May-15 | 9979 | 2 | 3 | | III-2 | Hkios | | |
| 9342 | 2 | 3 | | | III-2 | Gpr113 | 165082 | 4-May-15 | 9990 | 2 | 3 | | III-2 | Hmcn1 | 83872 | 4-May-15 |
| 9350 | 2 | 3 | | | III-2 | Gpr125 | 166647 | 14-May-15 | 9992 | 2 | 3 | | III-2 | Hmg20b | 10362 | 4-May-15 |
| 9351 | 2 | 3 | | | III-2 | Gpr126 | 57211 | 4-May-15 | 9999 | 2 | 3 | | III-2 | Hmgb2 | 3148 | 4-May-15 |
| 9361 | 2 | 3 | | | III-2 | Gpr141 | 353345 | 4-May-15 | 10011 | 2 | 3 | | III-2 | Hmgxb3 | 22993 | 4-May-15 |
| 9368 | 2 | 3 | | | III-2 | Gpr151 | 134391 | 4-May-15 | 10017 | 2 | 3 | | III-2 | Hmx1 | 3166 | 12-May-15 |
| 9373 | 2 | 3 | | | III-2 | Gpr157 | 80045 | 12-May-15 | 10019 | 2 | 3 | | III-2 | Hmx3 | 340784 | 4-May-15 |
| 9378 | 2 | 3 | | | III-2 | Gpr165 | | | 10021 | 2 | 3 | | III-2 | Hn1l | 90861 | 7-Jun-15 |
| 9379 | 2 | 3 | | | III-2 | Gpr17 | 2840 | 10-May-15 | 10027 | 2 | 3 | | III-2 | Hnmt | 3176 | 12-May-15 |

Fig.22 - 47

| | | | | | | | | | | | | | | | |
|---|---|---|---|---|---|---|---|---|---|---|---|---|---|---|---|
| 10031 | 2 | 3 | | III-2 | Hnrnpa3 | 220988 | 4-May-15 | 10646 | 2 | 3 | | III-2 | Isca1 | 81689 | 4-May-15 |
| 10041 | 2 | 3 | | III-2 | Hnrnpl | 3191 | 1-Jun-15 | 10662 | 2 | 3 | | III-2 | Ist1 | 9798 | 7-Jun-15 |
| 10052 | 2 | 3 | | III-2 | Homez | 57594 | 12-May-15 | 10668 | 2 | 3 | | III-2 | Isx | 91464 | 4-May-15 |
| 10058 | 2 | 3 | | III-2 | Hormad2 | 150280 | 4-May-15 | 10672 | 2 | 3 | | III-2 | Itga11 | 22801 | 21-May-15 |
| 10086 | 2 | 3 | | III-2 | Hoxc13 | 3229 | 7-Jun-15 | 10689 | 2 | 3 | | III-2 | Itgb1bp1 | 9270 | 8-May-15 |
| 10088 | 2 | 3 | | III-2 | Hoxc5 | 3222 | 4-May-15 | 10693 | 2 | 3 | | III-2 | Itgb3 | 3690 | 24-May-15 |
| 10090 | 2 | 3 | | III-2 | Hoxc8 | 3224 | 4-May-15 | 10695 | 2 | 3 | | III-2 | Itgb4 | 3691 | 23-May-15 |
| 10091 | 2 | 3 | | III-2 | Hoxc9 | 3225 | 4-May-15 | 10704 | 2 | 3 | | III-2 | Itih4 | 3700 | 17-May-15 |
| 10104 | 2 | 3 | | III-2 | Hpca | 3208 | 7-Jun-15 | 10716 | 2 | 3 | | III-2 | Itpr1 | 3708 | 4-May-15 |
| 10113 | 2 | 3 | | III-2 | Hps1 | 3257 | 23-May-15 | 10721 | 2 | 3 | | III-2 | Itpripl2 | 162073 | 4-May-15 |
| 10114 | 2 | 3 | | III-2 | Hps3 | 84343 | 23-May-15 | 10723 | 2 | 3 | | III-2 | Itsn2 | 50618 | 4-May-15 |
| 10117 | 2 | 3 | | III-2 | Hps6 | 79803 | 23-May-15 | 10730 | 2 | 3 | | III-2 | Izumo2 | 126123 | 4-May-15 |
| 10129 | 2 | 3 | | III-2 | Hrh2 | 3274 | 4-May-15 | 10734 | 2 | 3 | | III-2 | Jade2 | 23338 | 12-May-15 |
| 10142 | 2 | 3 | | III-2 | Hs3st5 | 222537 | 7-Jun-15 | 10739 | 2 | 3 | | III-2 | Jak1 | 3716 | 31-May-15 |
| 10145 | 2 | 3 | | III-2 | Hs6st2 | 90161 | 4-May-15 | 10744 | 2 | 3 | | III-2 | Jakmip3 | 282973 | 4-May-15 |
| 10160 | 2 | 3 | | III-2 | Hsd17b4 | 3295 | 12-May-15 | 10748 | 2 | 3 | | III-2 | Jazf1 | 221895 | 4-May-15 |
| 10171 | 2 | 3 | | III-2 | Hsdl2 | 84263 | 4-May-15 | 10763 | 2 | 3 | | III-2 | Jph4 | 84502 | 4-May-15 |
| 10173 | 2 | 3 | | III-2 | Hsf2 | 3298 | 12-May-15 | 10765 | 2 | 3 | | III-2 | Jrk | 8629 | 4-May-15 |
| 10174 | 2 | 3 | | III-2 | Hsf2bp | 11077 | 28-May-15 | 10766 | 2 | 3 | | III-2 | Jrkl | 8690 | 4-May-15 |
| 10176 | 2 | 3 | | III-2 | Hsf4 | 3299 | 4-May-15 | 10769 | 2 | 3 | | III-2 | Jun | 3725 | 31-May-15 |
| 10178 | 2 | 3 | | III-2 | Hsfy2 | 159119 | 4-May-15 | 10772 | 2 | 3 | | III-2 | Jup | 3728 | 22-May-15 |
| 10182 | 2 | 3 | | III-2 | Hsp90b1 | 7184 | 10-May-15 | 10779 | 2 | 3 | | III-2 | Kansl1 | 284058 | 23-May-15 |
| 10186 | 2 | 3 | | III-2 | Hspa14 | 51182 | 4-May-15 | 10782 | 2 | 3 | | III-2 | Kansl3 | 55683 | 4-May-15 |
| 10192 | 2 | 3 | | III-2 | Hspa4l | 22824 | 4-May-15 | 10785 | 2 | 3 | | III-2 | Kat2a | 2648 | 17-May-15 |
| 10205 | 2 | 3 | | III-2 | Hspbp1 | 23640 | 4-May-15 | 10791 | 2 | 3 | | III-2 | Kat8 | 84148 | 4-May-15 |
| 10212 | 2 | 3 | | III-2 | Htr1a | 3350 | 17-May-15 | 10794 | 2 | 3 | | III-2 | Katnal2 | 83473 | 4-May-15 |
| 10215 | 2 | 3 | | III-2 | Htr1f | 3355 | 4-May-15 | 10803 | 2 | 3 | | III-2 | Kbtbd3 | 143879 | 4-May-15 |
| 10231 | 2 | 3 | | III-2 | Hunk | 30811 | 4-May-15 | 10805 | 2 | 3 | | III-2 | Kbtbd7 | 84078 | 4-May-15 |
| 10233 | 2 | 3 | | III-2 | Hus1b | 135458 | 4-May-15 | 10810 | 2 | 3 | | III-2 | Kcna2 | 3737 | 22-May-15 |
| 10238 | 2 | 3 | | III-2 | Hyal3 | 8372 | 7-Jun-15 | 10819 | 2 | 3 | | III-2 | Kcnb1 | 3745 | 4-May-15 |
| 10240 | 2 | 3 | | III-2 | Hyal5 | 6677 | 12-May-15 | 10827 | 2 | 3 | | III-2 | Kcnd3 | 3752 | 22-May-15 |
| 10255 | 2 | 3 | | III-2 | Iars2 | 55699 | 12-May-15 | 10837 | 2 | 3 | | III-2 | Kcng3 | 170850 | 4-May-15 |
| 10265 | 2 | 3 | | III-2 | Ick | 22858 | 4-May-15 | 10847 | 2 | 3 | | III-2 | Kcnip1 | 30820 | 4-May-15 |
| 10266 | 2 | 3 | | III-2 | Icmt | 23463 | 4-May-15 | 10852 | 2 | 3 | | III-2 | Kcnj10 | 3766 | 23-May-15 |
| 10267 | 2 | 3 | | III-2 | Icos | 29851 | 17-May-15 | 10862 | 2 | 3 | | III-2 | Kcnj5 | 3762 | 23-May-15 |
| 10269 | 2 | 3 | | III-2 | Ict1 | 3996 | 4-May-15 | 10869 | 2 | 3 | | III-2 | Kcnk13 | 56659 | 4-May-15 |
| 10282 | 2 | 3 | | III-2 | Idnk | 414328 | 4-May-15 | 10873 | 2 | 3 | | III-2 | Kcnk2 | 3776 | 4-May-15 |
| 10286 | 2 | 3 | | III-2 | Idua | 3425 | 23-May-15 | 10882 | 2 | 3 | | III-2 | Kcnmb2 | 10242 | 7-Jun-15 |
| 10290 | 2 | 3 | | III-2 | Ier5 | 51278 | 12-May-15 | 10883 | 2 | 3 | | III-2 | Kcnmb3 | 27094 | 4-May-15 |
| 10293 | 2 | 3 | | III-2 | Ifo2 | 126917 | 4-May-15 | 10892 | 2 | 3 | | III-2 | Kcnq2 | 3785 | 23-May-15 |
| 10305 | 2 | 3 | | III-2 | Ifi47 | | | 10894 | 2 | 3 | | III-2 | Kcnq4 | 9132 | 23-May-15 |
| 10307 | 2 | 3 | | III-2 | Ifit1 | 3434 | 4-May-15 | 10897 | 2 | 3 | | III-2 | Kcns1 | 3787 | 4-May-15 |
| 10318 | 2 | 3 | | III-2 | Ifna1 | 3439 | 31-May-15 | 10908 | 2 | 3 | | III-2 | Kctd11 | 147040 | 4-May-15 |
| 10335 | 2 | 3 | | III-2 | Ifne | 338376 | 4-May-15 | 10911 | 2 | 3 | | III-2 | Kctd13 | 253980 | 4-May-15 |
| 10338 | 2 | 3 | | III-2 | Ifngr2 | 3460 | 24-May-15 | 10915 | 2 | 3 | | III-2 | Kctd17 | 79734 | 27-May-15 |
| 10340 | 2 | 3 | | III-2 | Ifnl2 | 282616 | 4-May-15 | 10917 | 2 | 3 | | III-2 | Kctd19 | 146212 | 4-May-15 |
| 10347 | 2 | 3 | | III-2 | Ift140 | 9742 | 4-May-15 | 10922 | 2 | 3 | | III-2 | Kctd4 | 386618 | 4-May-15 |
| 10354 | 2 | 3 | | III-2 | Ifr52 | 51098 | 12-May-15 | 10929 | 2 | 3 | | III-2 | Kdelc2 | 143888 | 4-May-15 |
| 10355 | 2 | 3 | | III-2 | Ifr57 | 55081 | 4-May-15 | 10935 | 2 | 3 | | III-2 | Kdm1b | 221656 | 31-May-15 |
| 10361 | 2 | 3 | | III-2 | igbp1b | | | 10946 | 2 | 3 | | III-2 | Kdm5c | 8242 | 23-May-15 |
| 10368 | 2 | 3 | | III-2 | Igf2bp2 | 10644 | 17-May-15 | 10947 | 2 | 3 | | III-2 | Kdm5d | 8284 | 23-May-15 |
| 10371 | 2 | 3 | | III-2 | Igf2r | 3482 | 21-May-15 | 10967 | 2 | 3 | | III-2 | Khsrp | 8570 | 31-May-15 |
| 10385 | 2 | 3 | | III-2 | Igip | 492311 | 4-May-15 | 10968 | 2 | 3 | | III-2 | Kidins220 | 57498 | 4-May-15 |
| 10388 | 2 | 3 | | III-2 | Iglon5 | 402665 | 4-May-15 | 10971 | 2 | 3 | | III-2 | Kif13a | 63971 | 4-May-15 |
| 10400 | 2 | 3 | | III-2 | Igtp | | | 10972 | 2 | 3 | | III-2 | Kif13b | 23303 | 4-May-15 |
| 10406 | 2 | 3 | | III-2 | Ikbkb | 3551 | 31-May-15 | 10980 | 2 | 3 | | III-2 | Kif1a | 547 | 23-May-15 |
| 10415 | 2 | 3 | | III-2 | Il10ra | 3587 | 4-May-15 | 10993 | 2 | 3 | | III-2 | Kif2a | 3796 | 3-May-15 |
| 10420 | 2 | 3 | | III-2 | Il12a | 3592 | 17-May-15 | 10995 | 2 | 3 | | III-2 | Kif2c | 11004 | 3-May-15 |
| 10423 | 2 | 3 | | III-2 | Il12rb2 | 3595 | 4-May-15 | 10997 | 2 | 3 | | III-2 | Kif3b | 9371 | 4-May-15 |
| 10427 | 2 | 3 | | III-2 | Il15 | 3600 | 17-May-15 | 10999 | 2 | 3 | | III-2 | Kif4 | 24137 | 4-May-15 |
| 10431 | 2 | 3 | | III-2 | Il17b | 27190 | 4-May-15 | 11001 | 2 | 3 | | III-2 | Kif5a | 3798 | 10-May-15 |
| 10435 | 2 | 3 | | III-2 | Il17ra | 23765 | 24-May-15 | 11005 | 2 | 3 | | III-2 | Kif7 | 374654 | 23-May-15 |
| 10448 | 2 | 3 | | III-2 | Il1f10 | 84639 | 4-May-15 | 11007 | 2 | 3 | | III-2 | Kifap3 | 22920 | 4-May-15 |
| 10456 | 2 | 3 | | III-2 | Il1rapl1 | 11141 | 23-May-15 | 11008 | 2 | 3 | | III-2 | Kifc1 | 3833 | 4-May-15 |
| 10462 | 2 | 3 | | III-2 | Il20 | 50604 | 4-May-15 | 11014 | 2 | 3 | | III-2 | Kir3dl2 | 3812 | 12-May-15 |
| 10466 | 2 | 3 | | III-2 | Il21r | 50615 | 4-May-15 | 11021 | 2 | 3 | | III-2 | Kit | 3815 | 24-May-15 |
| 10471 | 2 | 3 | | III-2 | Il23r | 149233 | 31-May-15 | 11049 | 2 | 3 | | III-2 | Klhdc2 | 23588 | 4-May-15 |
| 10480 | 2 | 3 | | III-2 | Il31 | 386653 | 7-Jun-15 | 11054 | 2 | 3 | | III-2 | Klhdc8a | 55220 | 4-May-15 |
| 10486 | 2 | 3 | | III-2 | Il4i1 | 259307 | 4-May-15 | 11061 | 2 | 3 | | III-2 | Klhl13 | 90293 | 4-May-15 |
| 10493 | 2 | 3 | | III-2 | Il7 | 3574 | 17-May-15 | 11065 | 2 | 3 | | III-2 | Klhl18 | 23276 | 4-May-15 |
| 10496 | 2 | 3 | | III-2 | Il9r | 3581 | 10-May-15 | 11068 | 2 | 3 | | III-2 | Klhl21 | 9903 | 4-May-15 |
| 10508 | 2 | 3 | | III-2 | Imp3 | 55272 | 7-Jun-15 | 11083 | 2 | 3 | | III-2 | Klhl36 | 79786 | 12-May-15 |
| 10526 | 2 | 3 | | III-2 | Ing4 | 51147 | 2-Jun-15 | 11089 | 2 | 3 | | III-2 | Klhl5 | 51088 | 12-May-15 |
| 10532 | 2 | 3 | | III-2 | Inhbe | 83729 | 12-May-15 | 11090 | 2 | 3 | | III-2 | Klhl6 | 89857 | 7-Jun-15 |
| 10536 | 2 | 3 | | III-2 | Ino80b | 83444 | 4-May-15 | 11092 | 2 | 3 | | III-2 | Klhl8 | 57563 | 12-May-15 |
| 10538 | 2 | 3 | | III-2 | Ino80d | 54891 | 12-May-15 | 11116 | 2 | 3 | | III-2 | Klk5 | 25818 | 4-May-15 |
| 10543 | 2 | 3 | | III-2 | Inpp4b | 8821 | 4-May-15 | 11125 | 2 | 3 | | III-2 | Klra13-ps | | |
| 10545 | 2 | 3 | | III-2 | Inpp5b | 3633 | 16-May-15 | 11127 | 2 | 3 | | III-2 | Klra15 | | |
| 10548 | 2 | 3 | | III-2 | Inpp5f | 22876 | 16-Jun-15 | 11128 | 2 | 3 | | III-2 | Klra17 | | |
| 10563 | 2 | 3 | | III-2 | Insrr | 3645 | 4-May-15 | 11131 | 2 | 3 | | III-2 | Klra2 | | |
| 10565 | 2 | 3 | | III-2 | Ints10 | 55174 | 4-May-15 | 11133 | 2 | 3 | | III-2 | Klra22 | | |
| 10566 | 2 | 3 | | III-2 | Ints12 | 57117 | 4-May-15 | 11137 | 2 | 3 | | III-2 | Klra4 | | |
| 10569 | 2 | 3 | | III-2 | Ints4 | 92105 | 4-May-15 | 11148 | 2 | 3 | | III-2 | Klrb1-ps1 | | |
| 10574 | 2 | 3 | | III-2 | Ints9 | 55756 | 4-May-15 | 11157 | 2 | 3 | | III-2 | Klri2 | | |
| 10577 | 2 | 3 | | III-2 | Ip6k1 | 9807 | 12-May-15 | 11166 | 2 | 3 | | III-2 | Kndc1 | 85442 | 4-May-15 |
| 10585 | 2 | 3 | | III-2 | Ipo8 | 3843 | 12-May-15 | 11173 | 2 | 3 | | III-2 | Kpna2 | 3838 | 17-May-15 |
| 10595 | 2 | 3 | | III-2 | Iqcd | 115811 | 4-May-15 | 11175 | 2 | 3 | | III-2 | Kpna4 | 3840 | 4-May-15 |
| 10604 | 2 | 3 | | III-2 | Iqcj | 654502 | 4-May-15 | 11182 | 2 | 3 | | III-2 | Krba1 | 84626 | 12-May-15 |
| 10612 | 2 | 3 | | III-2 | Iqub | 154865 | 4-May-15 | 11183 | 2 | 3 | | III-2 | Krcc1 | 51315 | 21-May-15 |
| 10613 | 2 | 3 | | III-2 | Irak1 | 3654 | 12-May-15 | 11184 | 2 | 3 | | III-2 | Kremen1 | 83999 | 4-May-15 |
| 10620 | 2 | 3 | | III-2 | Irf2 | 3660 | 31-May-15 | 11204 | 2 | 3 | | III-2 | Krt25 | 147183 | 4-May-15 |
| 10621 | 2 | 3 | | III-2 | Irf2bp1 | 26145 | 4-May-15 | 11210 | 2 | 3 | | III-2 | Krt33a | 3883 | 4-May-15 |
| 10622 | 2 | 3 | | III-2 | Irf2bp2 | 359948 | 4-May-15 | 11226 | 2 | 3 | | III-2 | Krt74 | 121391 | 7-Jun-15 |
| 10631 | 2 | 3 | | III-2 | Irg1 | 730249 | 4-May-15 | 11227 | 2 | 3 | | III-2 | Krt75 | 9119 | 4-May-15 |
| 10635 | 2 | 3 | | III-2 | Irgq | 126298 | 4-May-15 | 11228 | 2 | 3 | | III-2 | Krt76 | 51350 | 4-May-15 |
| 10636 | 2 | 3 | | III-2 | Irs1 | 3667 | 17-May-15 | 11269 | 2 | 3 | | III-2 | Krtap31-2 | | |
| 10645 | 2 | 3 | | III-2 | Irx6 | 79190 | 4-May-15 | 11298 | 2 | 3 | | III-2 | Ktl2 | 112970 | 4-May-15 |

Fig.22 - 48

| | | | | | | | | | | | | | | |
|---|---|---|---|---|---|---|---|---|---|---|---|---|---|---|
| 11299 | 2 | 3 | | | III-2 | Ktn1 | 3895 | 4-May-15 | 11898 | 2 | 3 | | III-2 | Mad1l1 | 8379 | 24-May-15 |
| 11308 | 2 | 3 | | | III-2 | L3mbtl2 | 83746 | 21-May-15 | 11905 | 2 | 3 | | III-2 | Mael | 84944 | 4-May-15 |
| 11314 | 2 | 3 | | | III-2 | Lactb | 114294 | 4-May-15 | 11932 | 2 | 3 | | III-2 | Magee1 | 57692 | 7-Jun-15 |
| 11316 | 2 | 3 | | | III-2 | Lactbl1 | 646262 | 4-May-15 | 11933 | 2 | 3 | | III-2 | Magee2 | 139599 | 4-May-15 |
| 11322 | 2 | 3 | | | III-2 | Lama1 | 284217 | 17-May-15 | 11934 | 2 | 3 | | III-2 | Mageh1 | 28986 | 4-May-15 |
| 11334 | 2 | 3 | | | III-2 | Lamp2 | 3920 | 12-May-15 | 11936 | 2 | 3 | | III-2 | Magi1 | 9223 | 7-Jun-15 |
| 11337 | 2 | 3 | | | III-2 | Lamtor1 | 55004 | 4-May-15 | 11941 | 2 | 3 | | III-2 | Magohb | 55110 | 12-May-15 |
| 11344 | 2 | 3 | | | III-2 | Lancl3 | 347404 | 4-May-15 | 11943 | 2 | 3 | | III-2 | Mak | 4117 | 7-Jun-15 |
| 11348 | 2 | 3 | | | III-2 | Laptm4b | 55353 | 17-May-15 | 11951 | 2 | 3 | | III-2 | Mamdc2 | 256691 | 4-May-15 |
| 11352 | 2 | 3 | | | III-2 | Larp1b | 55132 | 28-May-15 | 11953 | 2 | 3 | | III-2 | Maml1 | 9794 | 4-May-15 |
| 11354 | 2 | 3 | | | III-2 | Larp4b | 23185 | 24-May-15 | 11960 | 2 | 3 | | III-2 | Man1b1 | 11253 | 17-May-15 |
| 11357 | 2 | 3 | | | III-2 | Lars | 51520 | 4-May-15 | 11969 | 2 | 3 | | III-2 | Manba1 | 63905 | 4-May-15 |
| 11364 | 2 | 3 | | | III-2 | Lars2 | 26524 | 4-May-15 | 11974 | 2 | 3 | | III-2 | Mansc1 | 54682 | 4-May-15 |
| 11398 | 2 | 3 | | | III-2 | Lcmt1 | 51451 | 4-May-15 | 11979 | 2 | 3 | | III-2 | Map1a | 4130 | 7-Jun-15 |
| 11405 | 2 | 3 | | | III-2 | Lcn4 | | | 11983 | 2 | 3 | | III-2 | Map1s | 55201 | 21-May-15 |
| 11417 | 2 | 3 | | | III-2 | Ldb2 | 9079 | 12-May-15 | 11986 | 2 | 3 | | III-2 | Map2k2 | 5605 | 7-Jun-15 |
| 11426 | 2 | 3 | | | III-2 | Ldlrad2 | 401944 | 4-May-15 | 11990 | 2 | 3 | | III-2 | Map2k5 | 5607 | 3-May-15 |
| 11430 | 2 | 3 | | | III-2 | Ldoc1 | 23641 | 21-May-15 | 11993 | 2 | 3 | | III-2 | Map3k1 | 4214 | 12-May-15 |
| 11432 | 2 | 3 | | | III-2 | Leap2 | 116842 | 4-May-15 | 11995 | 2 | 3 | | III-2 | Map3k11 | 4296 | 4-May-15 |
| 11438 | 2 | 3 | | | III-2 | Lekr1 | 389170 | 4-May-15 | 12000 | 2 | 3 | | III-2 | Map3k19 | 80122 | 21-May-15 |
| 11445 | 2 | 3 | | | III-2 | Leng8 | 114823 | 4-May-15 | 12011 | 2 | 3 | | III-2 | Map4k1 | 11184 | 4-May-15 |
| 11452 | 2 | 3 | | | III-2 | Leprel2 | 10536 | 4-May-15 | 12012 | 2 | 3 | | III-2 | Map4k2 | 5871 | 3-May-15 |
| 11453 | 2 | 3 | | | III-2 | Leprel4 | 10609 | 12-May-15 | 12016 | 2 | 3 | | III-2 | Map6 | 4135 | 4-May-15 |
| 11469 | 2 | 3 | | | III-2 | Lgals9 | 3965 | 17-May-15 | 12028 | 2 | 3 | | III-2 | Mapk15 | 225689 | 3-May-15 |
| 11470 | 2 | 3 | | | III-2 | Lgalsl | 29094 | 12-May-15 | 12038 | 2 | 3 | | III-2 | Mapk8ip3 | 23162 | 4-May-15 |
| 11479 | 2 | 3 | | | III-2 | Lgsn | 51557 | 4-May-15 | 12039 | 2 | 3 | | III-2 | Mapk9 | 5601 | 4-May-15 |
| 11482 | 2 | 3 | | | III-2 | Lhfp | 10186 | 12-May-15 | 12051 | 2 | 3 | | III-2 | March1 | 55016 | 12-May-15 |
| 11483 | 2 | 3 | | | III-2 | Lhfpl1 | 340596 | 4-May-15 | 12053 | 2 | 3 | | III-2 | March11 | 441061 | 4-May-15 |
| 11486 | 2 | 3 | | | III-2 | Lhfpl4 | 375323 | 4-May-15 | 12057 | 2 | 3 | | III-2 | March5 | 54708 | 31-May-15 |
| 11502 | 2 | 3 | | | III-2 | Lig3 | 3980 | 16-Jun-15 | 12072 | 2 | 3 | | III-2 | Mars2 | 92935 | 4-May-15 |
| 11504 | 2 | 3 | | | III-2 | Lifra5 | 353514 | 4-May-15 | 12079 | 2 | 3 | | III-2 | Mast1 | 22983 | 7-Jun-15 |
| 11508 | 2 | 3 | | | III-2 | Lima1 | 51474 | 12-May-15 | 12089 | 2 | 3 | | III-2 | Matn2 | 4147 | 14-May-15 |
| 11511 | 2 | 3 | | | III-2 | Limd2 | 80774 | 4-May-15 | 12091 | 2 | 3 | | III-2 | Matn4 | 8785 | 4-May-15 |
| 11513 | 2 | 3 | | | III-2 | Limk1 | 3984 | 4-May-15 | 12093 | 2 | 3 | | III-2 | Mau2 | 23383 | 4-May-15 |
| 11515 | 2 | 3 | | | III-2 | Lims1 | 3987 | 24-May-15 | 12099 | 2 | 3 | | III-2 | Mb21d2 | 151963 | 4-May-15 |
| 11518 | 2 | 3 | | | III-2 | Lin28b | 389421 | 4-May-15 | 12101 | 2 | 3 | | III-2 | Mbd2 | 8932 | 7-Jun-15 |
| 11521 | 2 | 3 | | | III-2 | Lin54 | 132660 | 1-Jun-15 | 12123 | 2 | 3 | | III-2 | Mbtps2 | 51360 | 4-May-15 |
| 11525 | 2 | 3 | | | III-2 | Lin9 | 286826 | 4-May-15 | 12131 | 2 | 3 | | III-2 | Mcc | 4163 | 28-May-15 |
| 11529 | 2 | 3 | | | III-2 | Lingo3 | 645191 | 4-May-15 | 12134 | 2 | 3 | | III-2 | Mcce2 | 64087 | 23-May-15 |
| 11531 | 2 | 3 | | | III-2 | Lins | 55180 | 4-May-15 | 12136 | 2 | 3 | | III-2 | Mcemp1 | 199675 | 4-May-15 |
| 11549 | 2 | 3 | | | III-2 | Ligl1 | 3996 | 4-May-15 | 12137 | 2 | 3 | | III-2 | Mcf2 | 4168 | 4-May-15 |
| 11562 | 2 | 3 | | | III-2 | Lmf2 | 91289 | 4-May-15 | 12147 | 2 | 3 | | III-2 | Mcm4 | 4173 | 4-May-15 |
| 11567 | 2 | 3 | | | III-2 | Lmo1 | 4004 | 17-May-15 | 12153 | 2 | 3 | | III-2 | Mcmbp | 79892 | 4-May-15 |
| 11570 | 2 | 3 | | | III-2 | Lmo4 | 8543 | 7-Jun-15 | 12154 | 2 | 3 | | III-2 | Mcmdc2 | 157777 | 4-May-15 |
| 11578 | 2 | 3 | | | III-2 | Lmx1b | 4010 | 23-May-15 | 12163 | 2 | 3 | | III-2 | Mcpt9 | | |
| 11583 | 2 | 3 | | | III-2 | LOC100038947 | | | 12177 | 2 | 3 | | III-2 | Mdh1 | 4190 | 28-May-15 |
| 11585 | 2 | 3 | | | III-2 | LOC100043315 | | | 12185 | 2 | 3 | | III-2 | Mdp1 | 145553 | 7-Jun-15 |
| 11588 | 2 | 3 | | | III-2 | LOC100503280 | | | 12200 | 2 | 3 | | III-2 | Med13l | 23389 | 28-May-15 |
| 11595 | 2 | 3 | | | III-2 | LOC100861615 | | | 12203 | 2 | 3 | | III-2 | Med16 | 10025 | 12-May-15 |
| 11598 | 2 | 3 | | | III-2 | LOC100862268 | | | 12205 | 2 | 3 | | III-2 | Med18 | 54797 | 12-May-15 |
| 11601 | 2 | 3 | | | III-2 | LOC101056043 | | | 12210 | 2 | 3 | | III-2 | Med23 | 9439 | 21-May-15 |
| 11624 | 2 | 3 | | | III-2 | Lonp1 | 9361 | 23-May-15 | 12216 | 2 | 3 | | III-2 | Med29 | 55588 | 4-May-15 |
| 11632 | 2 | 3 | | | III-2 | Loxl1 | 4016 | 12-May-15 | 12220 | 2 | 3 | | III-2 | Med6 | 10001 | 4-May-15 |
| 11635 | 2 | 3 | | | III-2 | Loxl4 | 84171 | 4-May-15 | 12223 | 2 | 3 | | III-2 | Med9 | 55090 | 28-May-15 |
| 11640 | 2 | 3 | | | III-2 | Lpar5 | 57121 | 4-May-15 | 12226 | 2 | 3 | | III-2 | Mef2a | 4205 | 17-May-15 |
| 11642 | 2 | 3 | | | III-2 | Lpcat1 | 79888 | 4-May-15 | 12238 | 2 | 3 | | III-2 | Mei4 | 101928601 | 4-May-15 |
| 11643 | 2 | 3 | | | III-2 | Lpcat2 | 54947 | 12-May-15 | 12244 | 2 | 3 | | III-2 | Meik | 9833 | 4-May-15 |
| 11659 | 2 | 3 | | | III-2 | Lrba | 987 | 7-Jun-15 | 12247 | 2 | 3 | | III-2 | Meox1 | 4222 | 12-May-15 |
| 11667 | 2 | 3 | | | III-2 | Lrfn3 | 79414 | 4-May-15 | 12250 | 2 | 3 | | III-2 | Mep1b | 4225 | 12-May-15 |
| 11672 | 2 | 3 | | | III-2 | Lrif1 | 55791 | 4-May-15 | 12251 | 2 | 3 | | III-2 | Mepce | 56257 | 4-May-15 |
| 11674 | 2 | 3 | | | III-2 | Lrig2 | 9860 | 7-Jun-15 | 12252 | 2 | 3 | | III-2 | Mepe | 56955 | 12-May-15 |
| 11684 | 2 | 3 | | | III-2 | Lrp1b | 53353 | 12-May-15 | 12261 | 2 | 3 | | III-2 | Metap1d | 254042 | 4-May-15 |
| 11685 | 2 | 3 | | | III-2 | Lrp2 | 4036 | 23-May-15 | 12269 | 2 | 3 | | III-2 | Mettl14 | 57721 | 4-May-15 |
| 11691 | 2 | 3 | | | III-2 | Lrp8 | 7804 | 12-May-15 | 12272 | 2 | 3 | | III-2 | Mettl17 | 64745 | 4-May-15 |
| 11693 | 2 | 3 | | | III-2 | Lrpprc | 10128 | 7-Jun-15 | 12284 | 2 | 3 | | III-2 | Mettl4 | 64863 | 12-May-15 |
| 11696 | 2 | 3 | | | III-2 | Lrrc10 | 376132 | 4-May-15 | 12290 | 2 | 3 | | III-2 | Mettl7a3 | | |
| 11698 | 2 | 3 | | | III-2 | Lrrc14 | 9684 | 4-May-15 | 12293 | 2 | 3 | | III-2 | Mettl9 | 51108 | 21-May-15 |
| 11714 | 2 | 3 | | | III-2 | Lrrc29 | 26231 | 4-May-15 | 12296 | 2 | 3 | | III-2 | Mex3c | 51320 | 28-May-15 |
| 11719 | 2 | 3 | | | III-2 | Lrrc36 | 55282 | 4-May-15 | 12297 | 2 | 3 | | III-2 | Mex3d | 399664 | 4-May-15 |
| 11725 | 2 | 3 | | | III-2 | Lrrc41 | 10489 | 12-May-15 | 12299 | 2 | 3 | | III-2 | Mfap1b | | |
| 11726 | 2 | 3 | | | III-2 | Lrrc42 | 115353 | 4-May-15 | 12308 | 2 | 3 | | III-2 | Mfi2 | 4241 | 4-May-15 |
| 11738 | 2 | 3 | | | III-2 | Lrrc56 | 115399 | 4-May-15 | 12314 | 2 | 3 | | III-2 | Mfsd10 | 10227 | 4-May-15 |
| 11740 | 2 | 3 | | | III-2 | Lrrc58 | 116064 | 4-May-15 | 12316 | 2 | 3 | | III-2 | Mfsd12 | 126321 | 12-May-15 |
| 11747 | 2 | 3 | | | III-2 | Lrrc7 | 57554 | 14-May-15 | 12322 | 2 | 3 | | III-2 | Mfsd6 | 54842 | 4-May-15 |
| 11758 | 2 | 3 | | | III-2 | Lrrc8e | 80131 | 4-May-15 | 12330 | 2 | 3 | | III-2 | Mgam | 8972 | 4-May-15 |
| 11762 | 2 | 3 | | | III-2 | Lrrfip1 | 9208 | 4-May-15 | 12344 | 2 | 3 | | III-2 | Mgmt | 4255 | 17-May-15 |
| 11772 | 2 | 3 | | | III-2 | Lrrn4 | 164312 | 13-Jun-15 | 12356 | 2 | 3 | | III-2 | Mical1 | 64780 | 12-May-15 |
| 11773 | 2 | 3 | | | III-2 | Lrrn4cl | 221091 | 4-May-15 | 12357 | 2 | 3 | | III-2 | Mical2 | 9645 | 12-May-15 |
| 11775 | 2 | 3 | | | III-2 | Lrrtm2 | 26045 | 2-Jun-15 | 12359 | 2 | 3 | | III-2 | Micalcl | 84953 | 4-May-15 |
| 11779 | 2 | 3 | | | III-2 | Lrtm1 | 57408 | 12-May-15 | 12363 | 2 | 3 | | III-2 | Micu2 | 221154 | 4-May-15 |
| 11787 | 2 | 3 | | | III-2 | Lsm12 | 124801 | 21-May-15 | 12374 | 2 | 3 | | III-2 | Mier3 | 166968 | 12-May-15 |
| 11815 | 2 | 3 | | | III-2 | Ltn1 | 26046 | 23-May-15 | 12383 | 2 | 3 | | III-2 | Minos1 | 440574 | 2-Jun-15 |
| 11816 | 2 | 3 | | | III-2 | Ltv1 | 84946 | 12-May-15 | 12387 | 2 | 3 | | III-2 | Mip | 4284 | 7-Jun-15 |
| 11818 | 2 | 3 | | | III-2 | Luc7l2 | 51631 | 4-May-15 | 12388 | 2 | 3 | | III-2 | Mipep | 4285 | 12-May-15 |
| 11825 | 2 | 3 | | | III-2 | Luzp4 | 51213 | 4-May-15 | 12391 | 2 | 3 | | III-2 | Mir101a | | |
| 11828 | 2 | 3 | | | III-2 | Ly6c1 | | | 12414 | 2 | 3 | | III-2 | Mir122a | 406906 | 7-Jun-15 |
| 11829 | 2 | 3 | | | III-2 | Ly6c2 | | | 12436 | 2 | 3 | | III-2 | Mir129b | | |
| 11838 | 2 | 3 | | | III-2 | Ly6g6f | 259215 | 4-May-15 | 12462 | 2 | 3 | | III-2 | Mir145 | 406937 | 24-May-15 |
| 11861 | 2 | 3 | | | III-2 | Lypla2 | 11313 | 4-May-15 | 12481 | 2 | 3 | | III-2 | Mir17hg | 407975 | 17-May-15 |
| 11862 | 2 | 3 | | | III-2 | Lyplal1 | 127018 | 4-May-15 | 12483 | 2 | 3 | | III-2 | Mir181a-1 | | |
| 11865 | 2 | 3 | | | III-2 | Lyrm4 | 57128 | 12-May-15 | 12535 | 2 | 3 | | III-2 | Mir1942 | 406970 | 21-May-15 |
| 11867 | 2 | 3 | | | III-2 | Lyrm7 | 90824 | 12-May-15 | 12555 | 2 | 3 | | III-2 | Mir195b | | |
| 11869 | 2 | 3 | | | III-2 | Lyrm9 | 201229 | 4-May-15 | 12606 | 2 | 3 | | III-2 | Mir216b | 100126319 | 21-May-15 |
| 11871 | 2 | 3 | | | III-2 | Lysmd2 | 256586 | 4-May-15 | 12829 | 2 | 3 | | III-2 | Mir448 | 554212 | 21-May-15 |
| 11879 | 2 | 3 | | | III-2 | Lyzl4 | 131375 | 12-May-15 | 12878 | 2 | 3 | | III-2 | Mir488 | 574441 | 21-May-15 |
| 11890 | 2 | 3 | | | III-2 | Maats1 | 89876 | 4-May-15 | 12937 | 2 | 3 | | III-2 | Mir551b | 693136 | 21-May-15 |
| 11894 | 2 | 3 | | | III-2 | Macc1 | 346389 | 17-May-15 | | | | | | | | |

Fig.22 - 49

| | | | | | | | | | | | | | |
|---|---|---|---|---|---|---|---|---|---|---|---|---|---|
| 12963 | 2 | 3 | | III-2 | Mir6238 | | | 13879 | 2 | 3 | | III-2 | Mtmr3 | 8897 | 24-May-15 |
| 12968 | 2 | 3 | | III-2 | Mir6336 | | | 13889 | 2 | 3 | | III-2 | Mtpn | 136319 | 4-May-15 |
| 12974 | 2 | 3 | | III-2 | Mir6342 | | | 13890 | 2 | 3 | | III-2 | Mtr | 4548 | 23-May-15 |
| 12988 | 2 | 3 | | III-2 | Mir6359 | | | 13893 | 2 | 3 | | III-2 | Mtrr | 4552 | 23-May-15 |
| 12991 | 2 | 3 | | III-2 | Mir6362 | | | 13894 | 2 | 3 | | III-2 | Mtss1 | 9788 | 3-May-15 |
| 12994 | 2 | 3 | | III-2 | Mir6365 | | | 13914 | 2 | 3 | | III-2 | Mug1 | | |
| 13020 | 2 | 3 | | III-2 | Mir6394 | | | 13917 | 2 | 3 | | III-2 | Mul1 | 79594 | 23-May-15 |
| 13031 | 2 | 3 | | III-2 | Mir6405 | | | 13945 | 2 | 3 | | III-2 | Mutyh | 4595 | 23-May-15 |
| 13050 | 2 | 3 | | III-2 | Mir6537 | | | 13956 | 2 | 3 | | III-2 | Mxi1 | 4601 | 4-May-15 |
| 13127 | 2 | 3 | | III-2 | Mir6921 | | | 13957 | 2 | 3 | | III-2 | Mxra7 | 439921 | 12-May-15 |
| 13196 | 2 | 3 | | III-2 | Mir6983 | | | 13977 | 2 | 3 | | III-2 | Myct1 | 80177 | 4-May-15 |
| 13213 | 2 | 3 | | III-2 | Mir700 | | | 13989 | 2 | 3 | | III-2 | Myh15 | 22989 | 12-May-15 |
| 13248 | 2 | 3 | | III-2 | Mir7031 | | | 14000 | 2 | 3 | | III-2 | Myl12a | 10627 | 12-May-15 |
| 13283 | 2 | 3 | | III-2 | Mir7062 | | | 14015 | 2 | 3 | | III-2 | Myo10 | 4651 | 31-May-15 |
| 13333 | 2 | 3 | | III-2 | Mir7210 | | | 14018 | 2 | 3 | | III-2 | Myo16 | 23026 | 4-May-15 |
| 13377 | 2 | 3 | | III-2 | Mir762 | 100313837 | 4-May-15 | 14019 | 2 | 3 | | III-2 | Myo18a | 399687 | 4-May-15 |
| 13431 | 2 | 3 | | III-2 | Mir8101 | | | 14030 | 2 | 3 | | III-2 | Myo3a | 53904 | 23-May-15 |
| 13436 | 2 | 3 | | III-2 | Mir8106 | | | 14064 | 2 | 3 | | III-2 | Mzt2 | | |
| 13446 | 2 | 3 | | III-2 | Mir8116 | | | 14065 | 2 | 3 | | III-2 | N28178 | | |
| 13478 | 2 | 3 | | III-2 | Mirlet7a-2 | | | 14067 | 2 | 3 | | III-2 | N4bp2 | 55728 | 12-May-15 |
| 13482 | 2 | 3 | | III-2 | Mirlet7c-2 | | | 14071 | 2 | 3 | | III-2 | N6amt1 | 29104 | 4-May-15 |
| 13485 | 2 | 3 | | III-2 | Mirlet7f-1 | | | 14075 | 2 | 3 | | III-2 | Naa15 | 80155 | 4-May-15 |
| 13495 | 2 | 3 | | III-2 | Mitd1 | 129531 | 12-May-15 | 14078 | 2 | 3 | | III-2 | Naa25 | 80018 | 4-May-15 |
| 13500 | 2 | 3 | | III-2 | Mkl1 | 57591 | 17-May-15 | 14080 | 2 | 3 | | III-2 | Naa35 | 60560 | 4-May-15 |
| 13502 | 2 | 3 | | III-2 | Mkln1 | 4289 | 4-May-15 | 14083 | 2 | 3 | | III-2 | Naa50 | 80218 | 2-Jun-15 |
| 13503 | 2 | 3 | | III-2 | Mkln1os | | | 14085 | 2 | 3 | | III-2 | Naa | 27163 | 4-May-15 |
| 13505 | 2 | 3 | | III-2 | Mknk2 | 2872 | 4-May-15 | 14095 | 2 | 3 | | III-2 | Nacc2 | 138151 | 28-May-15 |
| 13508 | 2 | 3 | | III-2 | Mknk3 | 7681 | 23-May-15 | 14097 | 2 | 3 | | III-2 | Nadk2 | 133686 | 4-May-15 |
| 13513 | 2 | 3 | | III-2 | Mlec | 9761 | 12-May-15 | 14104 | 2 | 3 | | III-2 | Nagpa | 51172 | 4-May-15 |
| 13516 | 2 | 3 | | III-2 | Mlh1 | 4292 | 7-Jun-15 | 14105 | 2 | 3 | | III-2 | Nags | 162417 | 3-May-15 |
| 13521 | 2 | 3 | | III-2 | Mllt10 | 8028 | 4-May-15 | 14106 | 2 | 3 | | III-2 | Naif1 | 203245 | 4-May-15 |
| 13535 | 2 | 3 | | III-2 | Mmadhc | 27249 | 23-May-15 | 14108 | 2 | 3 | | III-2 | Naip2 | | |
| 13540 | 2 | 3 | | III-2 | Mmgt1 | 93380 | 4-May-15 | 14113 | 2 | 3 | | III-2 | Nampt | 10135 | 17-May-15 |
| 13548 | 2 | 3 | | III-2 | Mmp16 | 4325 | 17-May-15 | 14123 | 2 | 3 | | III-2 | Nap1l4 | 4676 | 12-May-15 |
| 13549 | 2 | 3 | | III-2 | Mmp17 | 4326 | 4-May-15 | 14126 | 2 | 3 | | III-2 | Napb | 63908 | 7-Jun-15 |
| 13552 | 2 | 3 | | III-2 | Mmp1b | | | 14132 | 2 | 3 | | III-2 | Narfl | 64428 | 12-May-15 |
| 13555 | 2 | 3 | | III-2 | Mmp21 | 118856 | 17-May-15 | 14133 | 2 | 3 | | III-2 | Narg2 | 79664 | 4-May-15 |
| 13559 | 2 | 3 | | III-2 | Mmp27 | 64066 | 4-May-15 | 14135 | 2 | 3 | | III-2 | Nars2 | 79731 | 3-May-15 |
| 13568 | 2 | 3 | | III-2 | Mns2l | 253714 | 4-May-15 | 14138 | 2 | 3 | | III-2 | Nat10 | 55226 | 4-May-15 |
| 13573 | 2 | 3 | | III-2 | Mndo | 4332 | 4-May-15 | 14139 | 2 | 3 | | III-2 | Nat14 | 57106 | 23-May-15 |
| 13577 | 2 | 3 | | III-2 | Mnx1 | 3110 | 12-May-15 | 14141 | 2 | 3 | | III-2 | Nat3 | | |
| 13582 | 2 | 3 | | III-2 | Mob3a | 126308 | 4-May-15 | 14149 | 2 | 3 | | III-2 | Nbas | 51594 | 29-May-15 |
| 13584 | 2 | 3 | | III-2 | Mob3c | 148932 | 4-May-15 | 14159 | 2 | 3 | | III-2 | Ncan | 1463 | 4-May-15 |
| 13592 | 2 | 3 | | III-2 | Mogat1 | 116255 | 4-May-15 | 14166 | 2 | 3 | | III-2 | Ncbp1 | 4686 | 4-May-15 |
| 13597 | 2 | 3 | | III-2 | Mon1b | 22879 | 4-May-15 | 14170 | 2 | 3 | | III-2 | Nceh1 | 57552 | 12-May-15 |
| 13605 | 2 | 3 | | III-2 | Morf4l2 | 9643 | 4-May-15 | 14175 | 2 | 3 | | III-2 | Nck2 | 8440 | 4-May-15 |
| 13611 | 2 | 3 | | III-2 | Mos | 4342 | 7-Jun-15 | 14180 | 2 | 3 | | III-2 | Nckipsd | 51517 | 4-May-15 |
| 13615 | 2 | 3 | | III-2 | Mospd4 | | | 14186 | 2 | 3 | | III-2 | Ncoa3 | 8202 | 17-May-15 |
| 13618 | 2 | 3 | | III-2 | Moxd1 | 26002 | 4-May-15 | 14201 | 2 | 3 | | III-2 | Ndfip1 | 80762 | 31-May-15 |
| 13620 | 2 | 3 | | III-2 | Mpc1 | 51660 | 7-Jun-15 | 14205 | 2 | 3 | | III-2 | Ndnl2 | 56160 | 4-May-15 |
| 13622 | 2 | 3 | | III-2 | Mpdu1 | 9526 | 4-May-15 | 14206 | 2 | 3 | | III-2 | Ndor1 | 27158 | 4-May-15 |
| 13623 | 2 | 3 | | III-2 | Mpdz | 8777 | 7-Jun-15 | 14214 | 2 | 3 | | III-2 | Ndst3 | 9348 | 4-May-15 |
| 13630 | 2 | 3 | | III-2 | Mpi | 4351 | 7-Jun-15 | 14218 | 2 | 3 | | III-2 | Ndufa11 | 126328 | 4-May-15 |
| 13633 | 2 | 3 | | III-2 | Mpnd | 84954 | 4-May-15 | 14232 | 2 | 3 | | III-2 | Ndufaf2 | 91942 | 23-May-15 |
| 13645 | 2 | 3 | | III-2 | Mprip | 23164 | 12-May-15 | 14235 | 2 | 3 | | III-2 | Ndufaf5 | 79133 | 23-May-15 |
| 13646 | 2 | 3 | | III-2 | Mpst | 4357 | 7-Jun-15 | 14238 | 2 | 3 | | III-2 | Ndufb10 | 4716 | 12-May-15 |
| 13650 | 2 | 3 | | III-2 | Mpv17l | 255027 | 4-May-15 | 14254 | 2 | 3 | | III-2 | Ndufs5 | 4725 | 4-May-15 |
| 13665 | 2 | 3 | | III-2 | Mrgbp | 55257 | 4-May-15 | 14255 | 2 | 3 | | III-2 | Ndufs6 | 4726 | 4-May-15 |
| 13685 | 2 | 3 | | III-2 | Mrgprx2 | 137194 | 12-May-15 | 14268 | 2 | 3 | | III-2 | Necap2 | 55707 | 4-May-15 |
| 13689 | 2 | 3 | | III-2 | Mroh1 | 727957 | 4-May-15 | 14271 | 2 | 3 | | III-2 | Nedd4l | 23327 | 17-May-15 |
| 13696 | 2 | 3 | | III-2 | Mroh8 | 140699 | 12-May-15 | 14283 | 2 | 3 | | III-2 | Nek11 | 79858 | 28-May-15 |
| 13700 | 2 | 3 | | III-2 | Mrpl11 | 65003 | 12-May-15 | 14288 | 2 | 3 | | III-2 | Nek6 | 10783 | 4-May-15 |
| 13705 | 2 | 3 | | III-2 | Mrpl16 | 54948 | 4-May-15 | 14292 | 2 | 3 | | III-2 | Nelfa | 7469 | 4-May-15 |
| 13709 | 2 | 3 | | III-2 | Mrpl2 | 51069 | 13-Jun-15 | 14321 | 2 | 3 | | III-2 | Neurog1 | 4762 | 12-May-15 |
| 13715 | 2 | 3 | | III-2 | Mrpl27 | 51264 | 7-Jun-15 | 14326 | 2 | 3 | | III-2 | Nf2 | 4771 | 1-Jun-15 |
| 13722 | 2 | 3 | | III-2 | Mrpl35 | 51318 | 4-May-15 | 14333 | 2 | 3 | | III-2 | Nfatc3 | 4775 | 24-May-15 |
| 13723 | 2 | 3 | | III-2 | Mrpl36 | 64979 | 4-May-15 | 14337 | 2 | 3 | | III-2 | Nfe2l2 | 4780 | 31-May-15 |
| 13730 | 2 | 3 | | III-2 | Mrpl42 | 28977 | 4-May-15 | 14359 | 2 | 3 | | III-2 | Nfyc | 4802 | 21-May-15 |
| 13735 | 2 | 3 | | III-2 | Mrpl47 | 57129 | 4-May-15 | 14360 | 2 | 3 | | III-2 | Ngb | 58157 | 7-Jun-15 |
| 13738 | 2 | 3 | | III-2 | Mrpl50 | 54534 | 14-May-15 | 14371 | 2 | 3 | | III-2 | Nhlh2 | 4808 | 23-May-15 |
| 13739 | 2 | 3 | | III-2 | Mrpl51 | 51258 | 28-May-15 | 14378 | 2 | 3 | | III-2 | Nhs | 4810 | 17-May-15 |
| 13742 | 2 | 3 | | III-2 | Mrpl54 | 116825 | 21-May-15 | 14381 | 2 | 3 | | III-2 | Nicn1 | 84276 | 4-May-15 |
| 13744 | 2 | 3 | | III-2 | Mrpl57 | 78988 | 28-May-15 | 14385 | 2 | 3 | | III-2 | Nifk | 84365 | 4-May-15 |
| 13745 | 2 | 3 | | III-2 | Mrpl9 | 65005 | 4-May-15 | 14387 | 2 | 3 | | III-2 | Nin | 51199 | 12-May-15 |
| 13746 | 2 | 3 | | III-2 | Mrps10 | 55173 | 28-May-15 | 14388 | 2 | 3 | | III-2 | Ninj1 | 4814 | 18-May-15 |
| 13749 | 2 | 3 | | III-2 | Mrps14 | 63931 | 12-May-15 | 14398 | 2 | 3 | | III-2 | Nipbl | 25836 | 23-May-15 |
| 13753 | 2 | 3 | | III-2 | Mrps18a | 55168 | 28-May-15 | 14401 | 2 | 3 | | III-2 | Nipsnap3b | 55335 | 12-May-15 |
| 13757 | 2 | 3 | | III-2 | Mrps21 | 54460 | 28-May-15 | 14403 | 2 | 3 | | III-2 | Nit1 | 4817 | 4-May-15 |
| 13760 | 2 | 3 | | III-2 | Mrps24 | 64951 | 28-May-15 | 14407 | 2 | 3 | | III-2 | Nkain3 | 286183 | 4-May-15 |
| 13765 | 2 | 3 | | III-2 | Mrps30 | 10884 | 12-May-15 | 14410 | 2 | 3 | | III-2 | Nkap | 222698 | 4-May-15 |
| 13772 | 2 | 3 | | III-2 | Mrps6 | 64968 | 28-May-15 | 14415 | 2 | 3 | | III-2 | Nkiras2 | 28511 | 4-May-15 |
| 13774 | 2 | 3 | | III-2 | Mrps9 | 64965 | 4-May-15 | 14424 | 2 | 3 | | III-2 | Nkx2-3 | 159296 | 4-May-15 |
| 13778 | 2 | 3 | | III-2 | Mrvi1 | 10335 | 12-May-15 | 14431 | 2 | 3 | | III-2 | Nkx6-1 | 4825 | 4-May-15 |
| 13781 | 2 | 3 | | III-2 | Ms4a13 | 503497 | 12-May-15 | 14434 | 2 | 3 | | III-2 | Nle1 | 54475 | 4-May-15 |
| 13797 | 2 | 3 | | III-2 | Msantd3 | 91283 | 4-May-15 | 14439 | 2 | 3 | | III-2 | Nln | 57486 | 4-May-15 |
| 13801 | 2 | 3 | | III-2 | Msh2 | 4436 | 23-May-15 | 14440 | 2 | 3 | | III-2 | Nlrc3 | 197358 | 4-May-15 |
| 13814 | 2 | 3 | | III-2 | Msmb | 4477 | 4-May-15 | 14443 | 2 | 3 | | III-2 | Nlrp10 | 338322 | 4-May-15 |
| 13817 | 2 | 3 | | III-2 | Msn | 4478 | 17-May-15 | 14444 | 2 | 3 | | III-2 | Nlrp12 | 91662 | 4-May-15 |
| 13820 | 2 | 3 | | III-2 | Msrb1 | 51734 | 12-May-15 | 14446 | 2 | 3 | | III-2 | Nlrp1a | | |
| 13830 | 2 | 3 | | III-2 | Msx2 | 4488 | 4-May-15 | 14455 | 2 | 3 | | III-2 | Nlrp4f | | |
| 13837 | 2 | 3 | | III-2 | Mta2 | 9219 | 4-May-15 | 14461 | 2 | 3 | | III-2 | Nlrp9b | | |
| 13841 | 2 | 3 | | III-2 | Mtap7d3 | | | 14466 | 2 | 3 | | III-2 | Nnd3 | 51068 | 4-May-15 |
| 13843 | 2 | 3 | | III-2 | Mtch1 | 23787 | 14-May-15 | 14468 | 2 | 3 | | III-2 | Nme2 | 4831 | 31-May-15 |
| 13851 | 2 | 3 | | III-2 | Mterfd2 | 130916 | 4-May-15 | 14469 | 2 | 3 | | III-2 | Nme3 | 4832 | 12-May-15 |
| 13854 | 2 | 3 | | III-2 | Mtf2 | 22823 | 4-May-15 | 14475 | 2 | 3 | | III-2 | Nme9 | 347736 | 4-May-15 |
| 13862 | 2 | 3 | | III-2 | Mthfd1 | 4522 | 21-May-15 | 14479 | 2 | 3 | | III-2 | Nmnat3 | 349565 | 4-May-15 |
| 13869 | 2 | 3 | | III-2 | Mtif2 | 4528 | 12-May-15 | 14484 | 2 | 3 | | III-2 | Nnt1 | 4836 | 4-May-15 |

Fig.22 - 50

| | | | | | | | | | | | | | | | |
|---|---|---|---|---|---|---|---|---|---|---|---|---|---|---|---|
| 14503 | 2 | 3 | | | III-2 | Nol11 | 25926 | 4-May-15 | 16169 | 2 | 3 | | | III-2 | Paf1 | 54623 | 7-Jun-15 |
| 14504 | 2 | 3 | | | III-2 | Nol12 | 79159 | 12-May-15 | 16178 | 2 | 3 | | | III-2 | Paip1 | 10605 | 12-May-15 |
| 14507 | 2 | 3 | | | III-2 | Nol6 | 65083 | 4-May-15 | 16183 | 2 | 3 | | | III-2 | Pak2 | 5062 | 7-Jun-15 |
| 14511 | 2 | 3 | | | III-2 | Nolc1 | 9221 | 12-May-15 | 16192 | 2 | 3 | | | III-2 | Palm2 | 114299 | 4-May-15 |
| 14522 | 2 | 3 | | | III-2 | Nos1 | 4842 | 7-Jun-15 | 16199 | 2 | 3 | | | III-2 | Pan3 | 255967 | 4-May-15 |
| 14532 | 2 | 3 | | | III-2 | Noto | 344022 | 4-May-15 | 16202 | 2 | 3 | | | III-2 | Pank3 | 79646 | 4-May-15 |
| 14536 | 2 | 3 | | | III-2 | Nova2 | 4858 | 4-May-15 | 16204 | 2 | 3 | | | III-2 | Panx1 | 24145 | 12-May-15 |
| 14539 | 2 | 3 | | | III-2 | Nox4 | 50507 | 10-May-15 | 16206 | 2 | 3 | | | III-2 | Panx3 | 116337 | 4-May-15 |
| 14543 | 2 | 3 | | | III-2 | Npas1 | 4861 | 28-May-15 | 16214 | 2 | 3 | | | III-2 | Papolb | 56903 | 12-May-15 |
| 14546 | 2 | 3 | | | III-2 | Npas4 | 266743 | 28-May-15 | 16219 | 2 | 3 | | | III-2 | Papss2 | 9060 | 4-May-15 |
| 14550 | 2 | 3 | | | III-2 | Npc1 | 4864 | 7-Jun-15 | 16222 | 2 | 3 | | | III-2 | Paqr5 | 54852 | 4-May-15 |
| 14556 | 2 | 3 | | | III-2 | Npepps | 9520 | 4-May-15 | 16223 | 2 | 3 | | | III-2 | Paqr6 | 79957 | 4-May-15 |
| 14561 | 2 | 3 | | | III-2 | Nphp3 | 27031 | 12-May-15 | 16235 | 2 | 3 | | | III-2 | Park | 55486 | 24-May-15 |
| 14568 | 2 | 3 | | | III-2 | Npm1 | 4869 | 17-May-15 | 16241 | 2 | 3 | | | III-2 | Parp12 | 64761 | 4-May-15 |
| 14581 | 2 | 3 | | | III-2 | Nps | 594857 | 4-May-15 | 16242 | 2 | 3 | | | III-2 | Parp14 | 54625 | 4-May-15 |
| 14592 | 2 | 3 | | | III-2 | Npy4r | 5540 | 4-May-15 | 16244 | 2 | 3 | | | III-2 | Parp2 | 10038 | 17-May-15 |
| 14601 | 2 | 3 | | | III-2 | Nr1h2 | 7376 | 29-May-15 | 16250 | 2 | 3 | | | III-2 | Parpbp | 55010 | 4-May-15 |
| 14611 | 2 | 3 | | | III-2 | Nr2e3 | 10002 | 23-May-15 | 16269 | 2 | 3 | | | III-2 | Pax6os1 | | |
| 14616 | 2 | 3 | | | III-2 | Nr3c2 | 4306 | 24-May-15 | 16274 | 2 | 3 | | | III-2 | Paxip1 | 22976 | 31-May-15 |
| 14627 | 2 | 3 | | | III-2 | Nrbf2 | 29982 | 4-May-15 | 16275 | 2 | 3 | | | III-2 | Pbdc1 | 51260 | 12-May-15 |
| 14635 | 2 | 3 | | | III-2 | Nrg1 | 3084 | 12-May-15 | 16280 | 2 | 3 | | | III-2 | Pbrm1 | 55193 | 4-May-15 |
| 14637 | 2 | 3 | | | III-2 | Nrg3 | 10718 | 4-May-15 | 16281 | 2 | 3 | | | III-2 | Pbsn | | |
| 14638 | 2 | 3 | | | III-2 | Nrg3os | | | 16282 | 2 | 3 | | | III-2 | Pbx1 | 5087 | 28-May-15 |
| 14650 | 2 | 3 | | | III-2 | Nrp | | | 16290 | 2 | 3 | | | III-2 | Pcbp2 | 5094 | 4-May-15 |
| 14651 | 2 | 3 | | | III-2 | Nrp1 | 8829 | 7-Jun-15 | 16297 | 2 | 3 | | | III-2 | Pcdh11x | 27328 | 12-May-15 |
| 14653 | 2 | 3 | | | III-2 | Nrros | 375387 | 4-May-15 | 16298 | 2 | 3 | | | III-2 | Pcdh12 | 51294 | 4-May-15 |
| 14655 | 2 | 3 | | | III-2 | Nrsn2 | 80023 | 4-May-15 | 16300 | 2 | 3 | | | III-2 | Pcdh17 | 27253 | 4-May-15 |
| 14658 | 2 | 3 | | | III-2 | Nrxn2 | 9379 | 4-May-15 | 16303 | 2 | 3 | | | III-2 | Pcdh20 | 64881 | 4-May-15 |
| 14660 | 2 | 3 | | | III-2 | Nsa2 | 10412 | 4-May-15 | 16304 | 2 | 3 | | | III-2 | Pcdh7 | 5099 | 4-May-15 |
| 14664 | 2 | 3 | | | III-2 | Nsfl1c | 55968 | 21-May-15 | 16306 | 2 | 3 | | | III-2 | Pcdh9 | 5101 | 4-May-15 |
| 14669 | 2 | 3 | | | III-2 | Nsmce1 | 197370 | 23-May-15 | 16308 | 2 | 3 | | | III-2 | Pcdha10 | 56139 | 4-May-15 |
| 14676 | 2 | 3 | | | III-2 | Nsun5 | 55695 | 4-May-15 | 16310 | 2 | 3 | | | III-2 | Pcdha12 | 56137 | 4-May-15 |
| 14686 | 2 | 3 | | | III-2 | Nt5dc2 | 64943 | 4-May-15 | 16321 | 2 | 3 | | | III-2 | Pcdhac2 | 56134 | 4-May-15 |
| 14690 | 2 | 3 | | | III-2 | Ntan1 | 123863 | 4-May-15 | 16327 | 2 | 3 | | | III-2 | Pcdhb14 | 56122 | 4-May-15 |
| 14695 | 2 | 3 | | | III-2 | Ntmt1 | 28989 | 4-May-15 | 16329 | 2 | 3 | | | III-2 | Pcdhb16 | 57717 | 12-May-15 |
| 14698 | 2 | 3 | | | III-2 | Ntn4 | 59277 | 7-Jun-15 | 16332 | 2 | 3 | | | III-2 | Pcdhb19 | 84054 | 4-May-15 |
| 14700 | 2 | 3 | | | III-2 | Ntng1 | 22854 | 7-Jun-15 | 16336 | 2 | 3 | | | III-2 | Pcdhb22 | | |
| 14703 | 2 | 3 | | | III-2 | Ntrk1 | 4914 | 23-May-15 | 16338 | 2 | 3 | | | III-2 | Pcdhb4 | 56131 | 12-May-15 |
| 14712 | 2 | 3 | | | III-2 | Nubp1 | 4682 | 10-Jun-15 | 16341 | 2 | 3 | | | III-2 | Pcdhb7 | 56129 | 4-May-15 |
| 14719 | 2 | 3 | | | III-2 | Nudcd1 | 84955 | 12-May-15 | 16345 | 2 | 3 | | | III-2 | Pcdhga10 | 56106 | 4-May-15 |
| 14722 | 2 | 3 | | | III-2 | Nudt1 | 4521 | 31-May-15 | 16347 | 2 | 3 | | | III-2 | Pcdhga12 | 26025 | 4-May-15 |
| 14727 | 2 | 3 | | | III-2 | Nudt14 | 256281 | 4-May-15 | 16351 | 2 | 3 | | | III-2 | Pcdhga5 | 56110 | 4-May-15 |
| 14749 | 2 | 3 | | | III-2 | Numb | 8650 | 4-May-15 | 16356 | 2 | 3 | | | III-2 | Pcdhgb1 | 56104 | 4-May-15 |
| 14750 | 2 | 3 | | | III-2 | Numbl | 9253 | 12-May-15 | 16363 | 2 | 3 | | | III-2 | Pcdhgc3 | 5098 | 4-May-15 |
| 14756 | 2 | 3 | | | III-2 | Nup188 | 23511 | 4-May-15 | 16367 | 2 | 3 | | | III-2 | Pced1b | 91523 | 4-May-15 |
| 14757 | 2 | 3 | | | III-2 | Nup205 | 23165 | 12-May-15 | 16369 | 2 | 3 | | | III-2 | Pcgf1 | 84759 | 4-May-15 |
| 14760 | 2 | 3 | | | III-2 | Nup214 | 8021 | 12-May-15 | 16373 | 2 | 3 | | | III-2 | Pcgf6 | 84108 | 4-May-15 |
| 14778 | 2 | 3 | | | III-2 | Nusap1 | 51203 | 4-May-15 | 16375 | 2 | 3 | | | III-2 | Pcif1 | 63935 | 4-May-15 |
| 14782 | 2 | 3 | | | III-2 | Nvl | 4931 | 4-May-15 | 16380 | 2 | 3 | | | III-2 | Pcmt1 | 5110 | 4-May-15 |
| 14797 | 2 | 3 | | | III-2 | Nxph2 | 11249 | 4-May-15 | 16381 | 2 | 3 | | | III-2 | Pcmtd1 | 115294 | 4-May-15 |
| 14801 | 2 | 3 | | | III-2 | Nxt2 | 55916 | 4-May-15 | 16385 | 2 | 3 | | | III-2 | Pcnt | 5116 | 4-May-15 |
| 14804 | 2 | 3 | | | III-2 | Nynrin | 57523 | 4-May-15 | 16388 | 2 | 3 | | | III-2 | Pcnxl3 | 399909 | 4-May-15 |
| 14817 | 2 | 3 | | | III-2 | Oas2 | 4939 | 4-May-15 | 16399 | 2 | 3 | | | III-2 | Pcsk2os2 | | |
| 14828 | 2 | 3 | | | III-2 | Obox2 | | | 16413 | 2 | 3 | | | III-2 | Pdc | 5132 | 7-Jun-15 |
| 14838 | 2 | 3 | | | III-2 | Oca2 | 4948 | 23-May-15 | 16416 | 2 | 3 | | | III-2 | Pdcd11 | 22984 | 4-May-15 |
| 14840 | 2 | 3 | | | III-2 | Ociad1 | 54940 | 4-May-15 | 16427 | 2 | 3 | | | III-2 | Pdcl3 | 79031 | 4-May-15 |
| 14856 | 2 | 3 | | | III-2 | Ofcc1 | 266553 | 7-Jun-15 | 16439 | 2 | 3 | | | III-2 | Pde4b | 5142 | 4-May-15 |
| 14861 | 2 | 3 | | | III-2 | Ogfod2 | 79676 | 23-May-15 | 16446 | 2 | 3 | | | III-2 | Pde6c | 5146 | 12-May-15 |
| 14864 | 2 | 3 | | | III-2 | Ogfrl1 | 79627 | 12-May-15 | 16450 | 2 | 3 | | | III-2 | Pde7a | 5150 | 4-May-15 |
| 14868 | 2 | 3 | | | III-2 | Oip5 | 11339 | 4-May-15 | 16453 | 2 | 3 | | | III-2 | Pde8b | 8622 | 4-May-15 |
| 14882 | 2 | 3 | | | III-2 | Olfr10 | | | 16456 | 2 | 3 | | | III-2 | Pdgfa | 5154 | 4-May-15 |
| 14913 | 2 | 3 | | | III-2 | Olfr1037 | | | 16487 | 2 | 3 | | | III-2 | Pdpn | 10630 | 17-May-15 |
| 15204 | 2 | 3 | | | III-2 | Olfr1377 | | | 16492 | 2 | 3 | | | III-2 | Pdss1 | 23590 | 4-May-15 |
| 15223 | 2 | 3 | | | III-2 | Olfr1395 | | | 16498 | 2 | 3 | | | III-2 | Pdxp | 57026 | 4-May-15 |
| 15226 | 2 | 3 | | | III-2 | Olfr1402 | | | 16500 | 2 | 3 | | | III-2 | Pdzd11 | 51248 | 4-May-15 |
| 15244 | 2 | 3 | | | III-2 | Olfr1424 | | | 16503 | 2 | 3 | | | III-2 | Pdzd4 | 57595 | 12-May-15 |
| 15331 | 2 | 3 | | | III-2 | Olfr187 | | | 16504 | 2 | 3 | | | III-2 | Pdzd7 | 79955 | 23-May-15 |
| 15381 | 2 | 3 | | | III-2 | Olfr228 | | | 16506 | 2 | 3 | | | III-2 | Pdzd9 | 255762 | 4-May-15 |
| 15632 | 2 | 3 | | | III-2 | Olfr556 | | | 16511 | 2 | 3 | | | III-2 | Pea15a | | |
| 15636 | 2 | 3 | | | III-2 | Olfr56 | | | 16513 | 2 | 3 | | | III-2 | Peak1 | 79834 | 4-May-15 |
| 15756 | 2 | 3 | | | III-2 | Olfr699 | | | 16526 | 2 | 3 | | | III-2 | Peli2 | 57161 | 4-May-15 |
| 15823 | 2 | 3 | | | III-2 | Olfr781 | | | 16539 | 2 | 3 | | | III-2 | Pepd | 5184 | 31-May-15 |
| 15979 | 2 | 3 | | | III-2 | Olfr978 | | | 16545 | 2 | 3 | | | III-2 | Pex1 | 5189 | 13-Jun-15 |
| 15983 | 2 | 3 | | | III-2 | Olfr981 | | | 16549 | 2 | 3 | | | III-2 | Pex11g | 92960 | 12-May-15 |
| 16000 | 2 | 3 | | | III-2 | Olig3 | 167826 | 4-May-15 | 16551 | 2 | 3 | | | III-2 | Pex13 | 5194 | 28-May-15 |
| 16002 | 2 | 3 | | | III-2 | Oma1 | 115209 | 3-May-15 | 16555 | 2 | 3 | | | III-2 | Pex2 | 5828 | 17-May-15 |
| 16007 | 2 | 3 | | | III-2 | Omt2b | | | 16561 | 2 | 3 | | | III-2 | Pex7 | 5191 | 23-May-15 |
| 16010 | 2 | 3 | | | III-2 | Onecut3 | 390874 | 28-May-15 | 16562 | 2 | 3 | | | III-2 | Pf4 | 5196 | 24-May-15 |
| 16012 | 2 | 3 | | | III-2 | Oog1 | | | 16575 | 2 | 3 | | | III-2 | Pfn3 | 5216 | 7-Jun-15 |
| 16018 | 2 | 3 | | | III-2 | Oosp3 | | | 16579 | 2 | 3 | | | III-2 | Pfpl | | |
| 16022 | 2 | 3 | | | III-2 | Opcml | 4978 | 4-May-15 | 16580 | 2 | 3 | | | III-2 | Pga5 | 5222 | 4-May-15 |
| 16026 | 2 | 3 | | | III-2 | Opn1sw | 611 | 12-May-15 | 16615 | 2 | 3 | | | III-2 | Phactr3 | 116154 | 4-May-15 |
| 16029 | 2 | 3 | | | III-2 | Opn5 | 221391 | 4-May-15 | 16624 | 2 | 3 | | | III-2 | Phf1 | 5252 | 4-May-15 |
| 16036 | 2 | 3 | | | III-2 | Orai1 | 84876 | 21-May-15 | 16630 | 2 | 3 | | | III-2 | Phf12 | 57649 | 12-May-15 |
| 16042 | 2 | 3 | | | III-2 | Orc3 | 23595 | 4-May-15 | 16633 | 2 | 3 | | | III-2 | Phf13 | 148479 | 4-May-15 |
| 16048 | 2 | 3 | | | III-2 | Orm3 | | | 16635 | 2 | 3 | | | III-2 | Phf20 | 51230 | 12-May-15 |
| 16050 | 2 | 3 | | | III-2 | Ormdl2 | 29095 | 4-May-15 | 16636 | 2 | 3 | | | III-2 | Phf20l1 | 51105 | 4-May-15 |
| 16068 | 2 | 3 | | | III-2 | Osgep | 55644 | 4-May-15 | 16638 | 2 | 3 | | | III-2 | Phf21b | 112885 | 12-May-15 |
| 16072 | 2 | 3 | | | III-2 | Osm | 5008 | 7-Jun-15 | 16650 | 2 | 3 | | | III-2 | Phkb | 5257 | 23-May-15 |
| 16082 | 2 | 3 | | | III-2 | Otoa | 146183 | 12-May-15 | 16660 | 2 | 3 | | | III-2 | Phlpp1 | 23239 | 4-May-15 |
| 16089 | 2 | 3 | | | III-2 | Otop3 | 347741 | 4-May-15 | 16663 | 2 | 3 | | | III-2 | Phlpp2 | 23035 | 4-May-15 |
| 16100 | 2 | 3 | | | III-2 | Otud5 | 55593 | 4-May-15 | 16665 | 2 | 3 | | | III-2 | Phox2a | 401 | 23-May-15 |
| 16101 | 2 | 3 | | | III-2 | Otud6a | 139562 | 4-May-15 | 16669 | 2 | 3 | | | III-2 | Phpt1 | 29085 | 4-May-15 |
| 16115 | 2 | 3 | | | III-2 | Oxa1l | 5018 | 4-May-15 | 16675 | 2 | 3 | | | III-2 | Phykpl | 85007 | 4-May-15 |
| 16125 | 2 | 3 | | | III-2 | Oxt | 5020 | 4-May-15 | 16679 | 2 | 3 | | | III-2 | Pi4k2b | 55300 | 4-May-15 |
| 16153 | 2 | 3 | | | III-2 | Pabpc5 | 140886 | 4-May-15 | 16682 | 2 | 3 | | | III-2 | Pianp | 196500 | 4-May-15 |
| 16160 | 2 | 3 | | | III-2 | Pacs2 | 23241 | 21-May-15 | 16684 | 2 | 3 | | | III-2 | Pias2 | 9063 | 4-May-15 |

Fig.22 - 51

| | | | | | | | | | | | | | | |
|---|---|---|---|---|---|---|---|---|---|---|---|---|---|---|
| 16688 | 2 | 3 | | H-2 | Picalm | 8301 | 12-May-15 | 17255 | 2 | 3 | | H-2 | Ppt2 | 9374 | 4-May-15 |
| 16689 | 2 | 3 | | H-2 | Pick1 | 9463 | 4-May-15 | 17257 | 2 | 3 | | H-2 | Ppwd1 | 23398 | 4-May-15 |
| 16694 | 2 | 3 | | H-2 | Pif1 | 80119 | 24-May-15 | 17269 | 2 | 3 | | H-2 | Pramef25 | 441873 | 4-May-15 |
| 16699 | 2 | 3 | | H-2 | Pigf | 5281 | 12-May-15 | 17282 | 2 | 3 | | H-2 | Prcp | 5547 | 4-May-15 |
| 16701 | 2 | 3 | | H-2 | Pigh | 5283 | 12-May-15 | 17286 | 2 | 3 | | H-2 | Prdm12 | 59335 | 28-May-15 |
| 16703 | 2 | 3 | | H-2 | Pigl | 9487 | 4-May-15 | 17292 | 2 | 3 | | H-2 | Prdm4 | 11108 | 4-May-15 |
| 16706 | 2 | 3 | | H-2 | Pigo | 84720 | 4-May-15 | 17295 | 2 | 3 | | H-2 | Prdm8 | 56978 | 4-May-15 |
| 16711 | 2 | 3 | | H-2 | Pigt | 51604 | 12-May-15 | 17296 | 2 | 3 | | H-2 | Prdm9 | 56979 | 12-May-15 |
| 16712 | 2 | 3 | | H-2 | Pigu | 128869 | 21-May-15 | 17302 | 2 | 3 | | H-2 | Prdx6 | 9588 | 7-Jun-15 |
| 16713 | 2 | 3 | | H-2 | Pigv | 55650 | 12-May-15 | 17319 | 2 | 3 | | H-2 | Prickle3 | 4007 | 12-May-15 |
| 16724 | 2 | 3 | | H-2 | Pik3c2g | 5288 | 3-May-15 | 17320 | 2 | 3 | | H-2 | Prickle4 | 29964 | 4-May-15 |
| 16725 | 2 | 3 | | H-2 | Pik3c3 | 5289 | 21-May-15 | 17330 | 2 | 3 | | H-2 | Prkacb | 5567 | 12-May-15 |
| 16727 | 2 | 3 | | H-2 | Pik3cb | 5291 | 31-May-15 | 17336 | 2 | 3 | | H-2 | Prkar1b | 5575 | 4-May-15 |
| 16735 | 2 | 3 | | H-2 | Pik3r5 | 23533 | 4-May-15 | 17344 | 2 | 3 | | H-2 | Prkcg | 5582 | 23-May-15 |
| 16737 | 2 | 3 | | H-2 | Pikfyve | 200576 | 12-May-15 | 17349 | 2 | 3 | | H-2 | Prkcz | 5590 | 4-May-15 |
| 16738 | 2 | 3 | | H-2 | Pilra | 29992 | 4-May-15 | 17351 | 2 | 3 | | H-2 | Prkd2 | 25865 | 4-May-15 |
| 16745 | 2 | 3 | | H-2 | Pin1rt1 | | | 17352 | 2 | 3 | | H-2 | Prkd3 | 23683 | 17-May-15 |
| 16753 | 2 | 3 | | H-2 | Pip4k2b | 8396 | 4-May-15 | 17353 | 2 | 3 | | H-2 | Prkdc | 5591 | 12-May-15 |
| 16758 | 2 | 3 | | H-2 | Pip5k1 | 138429 | 4-May-15 | 17354 | 2 | 3 | | H-2 | Prkg1 | 5592 | 28-May-15 |
| 16764 | 2 | 3 | | H-2 | Pira4 | | | 17356 | 2 | 3 | | H-2 | Prkra | 8575 | 12-May-15 |
| 16769 | 2 | 3 | | H-2 | Pisd | 23761 | 7-Jun-15 | 17357 | 2 | 3 | | H-2 | Prkrip1 | 79706 | 4-May-15 |
| 16770 | 2 | 3 | | H-2 | Pisd-ps1 | | | 17358 | 2 | 3 | | H-2 | Prkrir | 5612 | 4-May-15 |
| 16773 | 2 | 3 | | H-2 | Pithd1 | 57095 | 4-May-15 | 17362 | 2 | 3 | | H-2 | Prl2h1 | | |
| 16780 | 2 | 3 | | H-2 | Pitpnm3 | 83394 | 4-May-15 | 17397 | 2 | 3 | | H-2 | Prmt5 | 10419 | 4-May-15 |
| 16792 | 2 | 3 | | H-2 | Pkd1l3 | 342372 | 4-May-15 | 17398 | 2 | 3 | | H-2 | Prmt6 | 55170 | 4-May-15 |
| 16798 | 2 | 3 | | H-2 | Pkhd1 | 5314 | 23-May-15 | 17412 | 2 | 3 | | H-2 | Prokr1 | 10887 | 4-May-15 |
| 16808 | 2 | 3 | | H-2 | Pkn3 | 29941 | 21-May-15 | 17421 | 2 | 3 | | H-2 | Proser1 | 80209 | 4-May-15 |
| 16824 | 2 | 3 | | H-2 | Pla2g2c | 391013 | 4-May-15 | 17439 | 2 | 3 | | H-2 | Prpf8 | 10594 | 23-May-15 |
| 16828 | 2 | 3 | | H-2 | Pla2g3 | 50487 | 4-May-15 | 17445 | 2 | 3 | | H-2 | Prps1l3 | | |
| 16833 | 2 | 3 | | H-2 | Pla2g4e | 123745 | 4-May-15 | 17448 | 2 | 3 | | H-2 | Prpsap2 | 5636 | 4-May-15 |
| 16839 | 2 | 3 | | H-2 | Plaa | 9373 | 4-May-15 | 17451 | 2 | 3 | | H-2 | Prr13 | 54458 | 4-May-15 |
| 16840 | 2 | 3 | | H-2 | Plac1 | 10761 | 24-May-15 | 17453 | 2 | 3 | | H-2 | Prr14l | 253143 | 4-May-15 |
| 16846 | 2 | 3 | | H-2 | Plagl1 | 5325 | 28-May-15 | 17458 | 2 | 3 | | H-2 | Prr19 | 284338 | 20-May-15 |
| 16853 | 2 | 3 | | H-2 | Plbd2 | 196463 | 12-May-15 | 17461 | 2 | 3 | | H-2 | Prr24 | 255783 | 4-May-15 |
| 16854 | 2 | 3 | | H-2 | Plcb1 | 23236 | 4-May-15 | 17472 | 2 | 3 | | H-2 | Prrc2a | 7916 | 12-May-15 |
| 16856 | 2 | 3 | | H-2 | Plcb3 | 5331 | 4-May-15 | 17474 | 2 | 3 | | H-2 | Prrc2c | 23215 | 4-May-15 |
| 16857 | 2 | 3 | | H-2 | Plcb4 | 5332 | 12-May-15 | 17482 | 2 | 3 | | H-2 | Prrt4 | 401399 | 4-May-15 |
| 16865 | 2 | 3 | | H-2 | Plch2 | 9651 | 4-May-15 | 17484 | 2 | 3 | | H-2 | Prrx2 | 51450 | 4-May-15 |
| 16871 | 2 | 3 | | H-2 | Plcz1 | 89889 | 4-May-15 | 17491 | 2 | 3 | | H-2 | Prss22 | 64063 | 12-May-15 |
| 16872 | 2 | 3 | | H-2 | Pld1 | 5337 | 13-Jun-15 | 17495 | 2 | 3 | | H-2 | Prss29 | | |
| 16896 | 2 | 3 | | H-2 | Plekhg1 | 57480 | 4-May-15 | 17498 | 2 | 3 | | H-2 | Prss32 | | |
| 16900 | 2 | 3 | | H-2 | Plekhg5 | 57449 | 4-May-15 | 17500 | 2 | 3 | | H-2 | Prss34 | | |
| 16930 | 2 | 3 | | H-2 | Plod2 | 5352 | 28-May-15 | 17504 | 2 | 3 | | H-2 | Prss38 | 339501 | 4-May-15 |
| 16932 | 2 | 3 | | H-2 | Plp1 | 5354 | 23-May-15 | 17519 | 2 | 3 | | H-2 | Prss55 | 203074 | 4-May-15 |
| 16942 | 2 | 3 | | H-2 | Pltp | 5360 | 4-May-15 | 17535 | 2 | 3 | | H-2 | Psd3 | 23362 | 4-May-15 |
| 16946 | 2 | 3 | | H-2 | Plxna1 | 5361 | 4-May-15 | 17537 | 2 | 3 | | H-2 | Psen1 | 5663 | 31-May-15 |
| 16949 | 2 | 3 | | H-2 | Plxna4 | 91584 | 4-May-15 | 17538 | 2 | 3 | | H-2 | Psen2 | 5664 | 31-May-15 |
| 16964 | 2 | 3 | | H-2 | Pmis2 | | | 17556 | 2 | 3 | | H-2 | Psma1 | 5682 | 4-May-15 |
| 16971 | 2 | 3 | | H-2 | Pmpcb | 9512 | 4-May-15 | 17567 | 2 | 3 | | H-2 | Psmb2 | 5690 | 4-May-15 |
| 16973 | 2 | 3 | | H-2 | Pms2 | 5395 | 23-May-15 | 17574 | 2 | 3 | | H-2 | Psmb9 | 5698 | 12-May-15 |
| 16976 | 2 | 3 | | H-2 | Pnisr | 25957 | 12-May-15 | 17576 | 2 | 3 | | H-2 | Psmc2 | 5701 | 4-May-15 |
| 16977 | 2 | 3 | | H-2 | Pnkd | 25953 | 23-May-15 | 17580 | 2 | 3 | | H-2 | Psmc5 | 5705 | 4-May-15 |
| 16985 | 2 | 3 | | H-2 | Pnma3 | 29944 | 4-May-15 | 17581 | 2 | 3 | | H-2 | Psmc6 | 5706 | 4-May-15 |
| 17000 | 2 | 3 | | H-2 | Pnpla7 | 375775 | 4-May-15 | 17589 | 2 | 3 | | H-2 | Psmd3 | 5709 | 3-May-15 |
| 17002 | 2 | 3 | | H-2 | Pnpo | 55163 | 2-Jun-15 | 17599 | 2 | 3 | | H-2 | Psme3 | 10197 | 24-May-15 |
| 17008 | 2 | 3 | | H-2 | Poc5 | 134359 | 17-May-15 | 17611 | 2 | 3 | | H-2 | Pstk | 118672 | 12-May-15 |
| 17014 | 2 | 3 | | H-2 | Pofut1 | 23509 | 17-May-15 | 17617 | 2 | 3 | | H-2 | Ptbp2 | 58155 | 2-Jun-15 |
| 17021 | 2 | 3 | | H-2 | Polb | 5423 | 7-Jun-15 | 17625 | 2 | 3 | | H-2 | Ptchd2 | 57540 | 4-May-15 |
| 17026 | 2 | 3 | | H-2 | Poldip2 | 26073 | 12-May-15 | 17634 | 2 | 3 | | H-2 | Ptgdr | 5729 | 3-May-15 |
| 17032 | 2 | 3 | | H-2 | Polg | 5428 | 23-May-15 | 17638 | 2 | 3 | | H-2 | Ptger2 | 5732 | 12-May-15 |
| 17033 | 2 | 3 | | H-2 | Polg2 | 11232 | 12-May-15 | 17643 | 2 | 3 | | H-2 | Ptges3 | 10728 | 4-May-15 |
| 17036 | 2 | 3 | | H-2 | Polk | 51426 | 7-Jun-15 | 17651 | 2 | 3 | | H-2 | Ptgs1 | 5742 | 12-May-15 |
| 17038 | 2 | 3 | | H-2 | Polm | 27434 | 4-May-15 | 17657 | 2 | 3 | | H-2 | Pth2r | 5746 | 4-May-15 |
| 17040 | 2 | 3 | | H-2 | Polq | 10721 | 7-Jun-15 | 17660 | 2 | 3 | | H-2 | Ptk2b | 2185 | 4-May-15 |
| 17042 | 2 | 3 | | H-2 | Polr1b | 84172 | 4-May-15 | 17665 | 2 | 3 | | H-2 | Ptn | 5764 | 17-May-15 |
| 17047 | 2 | 3 | | H-2 | Polr2b | 5431 | 4-May-15 | 17667 | 2 | 3 | | H-2 | Ptp4a1 | 7803 | 17-May-15 |
| 17051 | 2 | 3 | | H-2 | Polr2f | 5435 | 12-May-15 | 17673 | 2 | 3 | | H-2 | Prplad2 | 401494 | 1-Jun-15 |
| 17058 | 2 | 3 | | H-2 | Polr2m | 81488 | 4-May-15 | 17694 | 2 | 3 | | H-2 | Ptprb | 5787 | 12-May-15 |
| 17059 | 2 | 3 | | H-2 | Polr3a | 11128 | 23-May-15 | 17701 | 2 | 3 | | H-2 | Ptprh | 5794 | 4-May-15 |
| 17067 | 2 | 3 | | H-2 | Polr3h | 171568 | 4-May-15 | 17708 | 2 | 3 | | H-2 | Ptprq | 374462 | 4-May-15 |
| 17068 | 2 | 3 | | H-2 | Polr3k | 51728 | 28-May-15 | 17709 | 2 | 3 | | H-2 | Ptprr | 5801 | 17-May-15 |
| 17075 | 2 | 3 | | H-2 | Pomgnt2 | 84892 | 4-May-15 | 17711 | 2 | 3 | | H-2 | Ptprt | 11122 | 4-May-15 |
| 17082 | 2 | 3 | | H-2 | Pon3 | 5446 | 4-May-15 | 17712 | 2 | 3 | | H-2 | Ptprtos | | |
| 17093 | 2 | 3 | | H-2 | Pot1b | | | 17719 | 2 | 3 | | H-2 | Ptrhd1 | 391356 | 4-May-15 |
| 17094 | 2 | 3 | | H-2 | Poteg | 404785 | 4-May-15 | 17723 | 2 | 3 | | H-2 | Ptx3 | 5806 | 24-May-15 |
| 17112 | 2 | 3 | | H-2 | Pp2d1 | 151849 | 4-May-15 | 17726 | 2 | 3 | | H-2 | Pum1 | 9698 | 29-May-15 |
| 17131 | 2 | 3 | | H-2 | Pcs | 79717 | 4-May-15 | 17730 | 2 | 3 | | H-2 | Purg | 29942 | 4-May-15 |
| 17134 | 2 | 3 | | H-2 | Ppef2 | 5470 | 4-May-15 | 17734 | 2 | 3 | | H-2 | Pus7 | 54517 | 12-May-15 |
| 17146 | 2 | 3 | | H-2 | Ppie | 10450 | 3-Jun-15 | 17745 | 2 | 3 | | H-2 | Pwp2 | 5822 | 4-May-15 |
| 17150 | 2 | 3 | | H-2 | Ppih | 10465 | 12-May-15 | 17759 | 2 | 3 | | H-2 | Pycr1 | 65263 | 4-May-15 |
| 17151 | 2 | 3 | | H-2 | Ppil1 | 51645 | 4-May-15 | 17761 | 2 | 3 | | H-2 | Pydc4 | | |
| 17153 | 2 | 3 | | H-2 | Ppil3 | 53938 | 4-May-15 | 17762 | 2 | 3 | | H-2 | Pygb | 5834 | 4-May-15 |
| 17160 | 2 | 3 | | H-2 | Ppm1b | 5495 | 31-May-15 | 17767 | 2 | 3 | | H-2 | Pyhin1 | 149628 | 4-May-15 |
| 17164 | 2 | 3 | | H-2 | Ppm1g | 5496 | 4-May-15 | 17771 | 2 | 3 | | H-2 | Pyy | 5697 | 23-May-15 |
| 17170 | 2 | 3 | | H-2 | Ppm1n | 147699 | 4-May-15 | 17774 | 2 | 3 | | H-2 | Qdpr | 5860 | 4-May-15 |
| 17172 | 2 | 3 | | H-2 | Ppox | 5498 | 13-Jun-15 | 17778 | 2 | 3 | | H-2 | Qprt | 23475 | 21-May-15 |
| 17173 | 2 | 3 | | H-2 | Ppp1ca | 5499 | 4-May-15 | 17782 | 2 | 3 | | H-2 | Qrich2 | 84074 | 4-May-15 |
| 17176 | 2 | 3 | | H-2 | Ppp1r10 | 5514 | 4-May-15 | 17789 | 2 | 3 | | H-2 | R3hcc1 | 203069 | 12-May-15 |
| 17178 | 2 | 3 | | H-2 | Ppp1r12a | 4659 | 12-May-15 | 17797 | 2 | 3 | | H-2 | Rab10 | 10890 | 4-May-15 |
| 17196 | 2 | 3 | | H-2 | Ppp1r2 | 5504 | 12-May-15 | 17803 | 2 | 3 | | H-2 | Rab11fip3 | 9727 | 21-May-15 |
| 17202 | 2 | 3 | | H-2 | Ppp1r2-ps9 | | | 17806 | 2 | 3 | | H-2 | Rab11fip4os2 | | |
| 17204 | 2 | 3 | | H-2 | Ppp1r35 | 221908 | 4-May-15 | 17809 | 2 | 3 | | H-2 | Rab13 | 5872 | 3-May-15 |
| 17220 | 2 | 3 | | H-2 | Ppp2ca | 5515 | 17-May-15 | 17811 | 2 | 3 | | H-2 | Rab15 | 376267 | 12-May-15 |
| 17235 | 2 | 3 | | H-2 | Ppp2r5c | 5527 | 4-May-15 | 17819 | 2 | 3 | | H-2 | Rab23 | 51715 | 21-May-15 |
| 17236 | 2 | 3 | | H-2 | Ppp2r5d | 5528 | 23-May-15 | 17827 | 2 | 3 | | H-2 | Rab2a | 5862 | 4-May-15 |
| 17241 | 2 | 3 | | H-2 | Ppp3r1 | 5534 | 4-May-15 | 17831 | 2 | 3 | | H-2 | Rab32 | 10981 | 4-May-15 |
| 17253 | 2 | 3 | | H-2 | Pprc1 | 23082 | 4-May-15 | 17832 | 2 | 3 | | H-2 | Rab33a | 9363 | 21-May-15 |

Fig.22 - 52

| | | | | | | | | | | | | | | |
|---|---|---|---|---|---|---|---|---|---|---|---|---|---|---|
| 17833 | 2 | 3 | | H-2 | Rab33b | 83452 | 21-May-15 | 18442 | 2 | 3 | | H-2 | Rnf224 | 643596 | 4-May-15 |
| 17853 | 2 | 3 | | H-2 | Rab44 | 401258 | 4-May-15 | 18447 | 2 | 3 | | H-2 | Rnf32 | 140546 | 21-May-15 |
| 17864 | 2 | 3 | | H-2 | Rab8b | 51762 | 4-May-15 | 18448 | 2 | 3 | | H-2 | Rnf34 | 80196 | 12-May-15 |
| 17879 | 2 | 3 | | H-2 | Rabl6 | 55884 | 4-May-15 | 18452 | 2 | 3 | | H-2 | Rnf40 | 9810 | 4-May-15 |
| 17885 | 2 | 3 | | H-2 | Rad17 | 5884 | 12-May-15 | 18466 | 2 | 3 | | H-2 | Rnmt1 | 55178 | 4-May-15 |
| 17888 | 2 | 3 | | H-2 | Rad21l | 642636 | 4-May-15 | 18471 | 2 | 3 | | H-2 | Rnu11 | 26824 | 7-Jun-15 |
| 17889 | 2 | 3 | | H-2 | Rad23a | 5886 | 4-May-15 | 18474 | 2 | 3 | | H-2 | Rnu7 | | |
| 17891 | 2 | 3 | | H-2 | Rad50 | 10111 | 4-May-15 | 18478 | 2 | 3 | | H-2 | Robo3 | 64221 | 4-May-15 |
| 17898 | 2 | 3 | | H-2 | Rad52 | 5893 | 12-May-15 | 18481 | 2 | 3 | | H-2 | Rock2 | 9475 | 31-May-15 |
| 17906 | 2 | 3 | | H-2 | Raet1a | | | 18482 | 2 | 3 | | H-2 | Rogdi | 79641 | 12-May-15 |
| 17914 | 2 | 3 | | H-2 | Rai1 | 10743 | 16-Jun-15 | 18483 | 2 | 3 | | H-2 | Rom1 | 6094 | 23-May-15 |
| 17918 | 2 | 3 | | H-2 | Ralb | 5899 | 21-May-15 | 18501 | 2 | 3 | | H-2 | Rpap1 | 26015 | 4-May-15 |
| 17919 | 2 | 3 | | H-2 | Ralbp1 | 10928 | 7-Jun-15 | 18502 | 2 | 3 | | H-2 | Rpap2 | 79871 | 4-May-15 |
| 17927 | 2 | 3 | | H-2 | Ralyl | 138046 | 2-Jun-15 | 18504 | 2 | 3 | | H-2 | Rpe | 6120 | 4-May-15 |
| 17932 | 2 | 3 | | H-2 | Ranbp1 | 5902 | 1-Jun-15 | 18505 | 2 | 3 | | H-2 | Rpe65 | 6121 | 23-May-15 |
| 17935 | 2 | 3 | | H-2 | Ranbp2 | 5903 | 23-May-15 | 18506 | 2 | 3 | | H-2 | Rpf1 | 80135 | 7-Jun-15 |
| 17937 | 2 | 3 | | H-2 | Ranbp3l | 202151 | 28-May-15 | 18510 | 2 | 3 | | H-2 | Rpgrip1l | 23322 | 23-May-15 |
| 17939 | 2 | 3 | | H-2 | Ranbp9 | 10048 | 4-May-15 | 18539 | 2 | 3 | | H-2 | Rpl3 | 6122 | 31-May-15 |
| 17943 | 2 | 3 | | H-2 | Rap1b | 5908 | 21-May-15 | 18542 | 2 | 3 | | H-2 | Rpl31-ps12 | | |
| 17947 | 2 | 3 | | H-2 | Rap2a | 5911 | 12-May-15 | 18578 | 2 | 3 | | H-2 | Rpp40 | 10799 | 12-May-15 |
| 17948 | 2 | 3 | | H-2 | Rap2b | 5912 | 4-May-15 | 18604 | 2 | 3 | | H-2 | Rps20 | 6224 | 4-May-15 |
| 17956 | 2 | 3 | | H-2 | Rapgef1 | 51195 | 12-May-15 | 18617 | 2 | 3 | | H-2 | Rps3a1 | | |
| 17960 | 2 | 3 | | H-2 | Rarb | 5915 | 12-May-15 | 18625 | 2 | 3 | | H-2 | Rps6ka4 | 8986 | 4-May-15 |
| 17967 | 2 | 3 | | H-2 | Rasa2 | 5922 | 4-May-15 | 18626 | 2 | 3 | | H-2 | Rps6ka5 | 9252 | 4-May-15 |
| 17983 | 2 | 3 | | H-2 | Rasgrp3 | 25780 | 12-May-15 | 18631 | 2 | 3 | | H-2 | Rps6kl1 | 83694 | 12-May-15 |
| 17985 | 2 | 3 | | H-2 | Rasip1 | 54922 | 4-May-15 | 18643 | 2 | 3 | | H-2 | Rqcd1 | 9125 | 12-May-15 |
| 18003 | 2 | 3 | | H-2 | Raver1-fdx1l | | | 18651 | 2 | 3 | | H-2 | Rrbp1 | 6238 | 4-May-15 |
| 18008 | 2 | 3 | | H-2 | Rbak | 57786 | 12-May-15 | 18657 | 2 | 3 | | H-2 | Rrn3 | 54700 | 4-May-15 |
| 18009 | 2 | 3 | | H-2 | Rbakdn | 389458 | 4-May-15 | 18662 | 2 | 3 | | H-2 | Rrp1b | 23076 | 4-May-15 |
| 18012 | 2 | 3 | | H-2 | Rbbp6 | 5930 | 12-May-15 | 18663 | 2 | 3 | | H-2 | Rrp36 | 88745 | 4-May-15 |
| 18016 | 2 | 3 | | H-2 | Rbbp9 | 10741 | 4-May-15 | 18665 | 2 | 3 | | H-2 | Rrp8 | 23378 | 28-May-15 |
| 18017 | 2 | 3 | | H-2 | Rbck1 | 10616 | 23-May-15 | 18673 | 2 | 3 | | H-2 | Rsc1a1 | 6248 | 4-May-15 |
| 18024 | 2 | 3 | | H-2 | Rbl2 | 5934 | 4-May-15 | 18675 | 2 | 3 | | H-2 | Rsg1 | 79363 | 4-May-15 |
| 18030 | 2 | 3 | | H-2 | Rbm14 | 10432 | 1-Jun-15 | 18678 | 2 | 3 | | H-2 | Rsl24d1 | 51187 | 4-May-15 |
| 18035 | 2 | 3 | | H-2 | Rbm18 | 92400 | 4-May-15 | 18682 | 2 | 3 | | H-2 | Rsph3b | | |
| 18036 | 2 | 3 | | H-2 | Rbm19 | 9904 | 4-May-15 | 18683 | 2 | 3 | | H-2 | Rsph4a | 345895 | 23-May-15 |
| 18041 | 2 | 3 | | H-2 | Rbm26 | 64062 | 4-May-15 | 18684 | 2 | 3 | | H-2 | Rsph6a | 81492 | 4-May-15 |
| 18046 | 2 | 3 | | H-2 | Rbm33 | 155435 | 4-May-15 | 18691 | 2 | 3 | | H-2 | Rsrc1 | 51319 | 4-May-15 |
| 18054 | 2 | 3 | | H-2 | Rbm43 | 375287 | 4-May-15 | 18705 | 2 | 3 | | H-2 | Rtn1 | 6252 | 12-May-15 |
| 18061 | 2 | 3 | | H-2 | Rbm4b | 83759 | 4-May-15 | 18708 | 2 | 3 | | H-2 | Rtn4 | 57142 | 10-May-15 |
| 18070 | 2 | 3 | | H-2 | Rbmx2 | 51634 | 4-May-15 | 18714 | 2 | 3 | | H-2 | Rtp2 | 344892 | 9-May-15 |
| 18080 | 2 | 3 | | H-2 | Rbpj | 11317 | 4-May-15 | 18715 | 2 | 3 | | H-2 | Rtp3 | 83597 | 9-May-15 |
| 18084 | 2 | 3 | | H-2 | Rc3h1 | 149041 | 4-May-15 | 18718 | 2 | 3 | | H-2 | Rubie | | |
| 18089 | 2 | 3 | | H-2 | Rcbtb1 | 55213 | 4-May-15 | 18719 | 2 | 3 | | H-2 | Rufy1 | 80230 | 4-May-15 |
| 18093 | 2 | 3 | | H-2 | Rccd1 | 91433 | 4-May-15 | 18739 | 2 | 3 | | H-2 | Rxfp1 | 59350 | 4-May-15 |
| 18099 | 2 | 3 | | H-2 | Rcn3 | 57333 | 7-Jun-15 | 18747 | 2 | 3 | | H-2 | Ryk | 6259 | 21-May-15 |
| 18102 | 2 | 3 | | H-2 | Rcor3 | 58758 | 14-May-15 | 18750 | 2 | 3 | | H-2 | Ryr3 | 6263 | 12-May-15 |
| 18124 | 2 | 3 | | H-2 | Recql | 5965 | 4-May-15 | 18757 | 2 | 3 | | H-2 | S100a2 | 6273 | 12-May-15 |
| 18125 | 2 | 3 | | H-2 | Recql4 | 9401 | 23-May-15 | 18761 | 2 | 3 | | H-2 | S100a6 | 6277 | 4-May-15 |
| 18131 | 2 | 3 | | H-2 | Reep4 | 80346 | 4-May-15 | 18773 | 2 | 3 | | H-2 | S1pr5 | 53637 | 4-May-15 |
| 18143 | 2 | 3 | | H-2 | Relb | 5971 | 28-May-15 | 18779 | 2 | 3 | | H-2 | Sac3d1 | 29901 | 4-May-15 |
| 18150 | 2 | 3 | | H-2 | Ren1 | | | 18781 | 2 | 3 | | H-2 | Sacs | 26278 | 23-May-15 |
| 18155 | 2 | 3 | | H-2 | Reps1 | 85021 | 4-May-15 | 18788 | 2 | 3 | | H-2 | Sall3 | 27164 | 4-May-15 |
| 18158 | 2 | 3 | | H-2 | Rere | 473 | 12-May-15 | 18790 | 2 | 3 | | H-2 | Samd1 | 90378 | 4-May-15 |
| 18172 | 2 | 3 | | H-2 | Rexo1 | 57455 | 4-May-15 | 18796 | 2 | 3 | | H-2 | Samd3 | 154075 | 7-Jun-15 |
| 18180 | 2 | 3 | | H-2 | Rfesd | 317671 | 4-May-15 | 18801 | 2 | 3 | | H-2 | Samd8 | 142891 | 4-May-15 |
| 18181 | 2 | 3 | | H-2 | Rfft | 117584 | 4-May-15 | 18804 | 2 | 3 | | H-2 | Sammo50 | 25813 | 4-May-15 |
| 18182 | 2 | 3 | | H-2 | Rfk | 55312 | 4-May-15 | 18807 | 2 | 3 | | H-2 | Samt3 | | |
| 18195 | 2 | 3 | | H-2 | Rfx4 | 5992 | 28-May-15 | 18814 | 2 | 3 | | H-2 | Sap30l | 79685 | 4-May-15 |
| 18196 | 2 | 3 | | H-2 | Rfx5 | 5993 | 4-May-15 | 18825 | 2 | 3 | | H-2 | Sart3 | 9733 | 12-May-15 |
| 18200 | 2 | 3 | | H-2 | Rfxank | 8625 | 4-May-15 | 18833 | 2 | 3 | | H-2 | Satl1 | 340562 | 4-May-15 |
| 18206 | 2 | 3 | | H-2 | Rgl2 | 5863 | 4-May-15 | 18834 | 2 | 3 | | H-2 | Sav1 | 60485 | 4-May-15 |
| 18207 | 2 | 3 | | H-2 | Rgl3 | 57139 | 4-May-15 | 18848 | 2 | 3 | | H-2 | Sc5d | 6309 | 12-May-15 |
| 18212 | 2 | 3 | | H-2 | Rgr | 5995 | 7-Jun-15 | 18849 | 2 | 3 | | H-2 | Scaf1 | 58506 | 4-May-15 |
| 18221 | 2 | 3 | | H-2 | Rgs18 | 64407 | 4-May-15 | 18850 | 2 | 3 | | H-2 | Scaf11 | 9169 | 12-May-15 |
| 18231 | 2 | 3 | | H-2 | Rgs7 | 6000 | 4-May-15 | 18852 | 2 | 3 | | H-2 | Scaf8 | 22828 | 4-May-15 |
| 18254 | 2 | 3 | | H-2 | Rhob | 388 | 12-May-15 | 18860 | 2 | 3 | | H-2 | Scap | 22937 | 7-Jun-15 |
| 18262 | 2 | 3 | | H-2 | Rhoh | 399 | 12-May-15 | 18861 | 2 | 3 | | H-2 | Scaper | 49855 | 4-May-15 |
| 18266 | 2 | 3 | | H-2 | Rhot2 | 89941 | 4-May-15 | 18862 | 2 | 3 | | H-2 | Scara3 | 51435 | 3-May-15 |
| 18270 | 2 | 3 | | H-2 | Rhox10 | | | 18869 | 2 | 3 | | H-2 | Scarna10 | 692148 | 4-May-15 |
| 18287 | 2 | 3 | | H-2 | Rhox3h | | | 18872 | 2 | 3 | | H-2 | Scarna2 | 677766 | 12-May-15 |
| 18297 | 2 | 3 | | H-2 | Rhox7 | | | 18878 | 2 | 3 | | H-2 | Sccpdh | 51097 | 4-May-15 |
| 18305 | 2 | 3 | | H-2 | Ric3 | 79608 | 14-May-15 | 18886 | 2 | 3 | | H-2 | Scg2 | 7857 | 7-Jun-15 |
| 18307 | 2 | 3 | | H-2 | Ric8b | 55188 | 4-May-15 | 18891 | 2 | 3 | | H-2 | Scgb1b2 | | |
| 18316 | 2 | 3 | | H-2 | Rimkla | 284716 | 4-May-15 | 18896 | 2 | 3 | | H-2 | Scgb1b3 | | |
| 18319 | 2 | 3 | | H-2 | Rims2 | 9899 | 12-May-15 | 18898 | 2 | 3 | | H-2 | Scgb1b7 | | |
| 18325 | 2 | 3 | | H-2 | Ring1 | 6015 | 4-May-15 | 18904 | 2 | 3 | | H-2 | Scgb2b2 | 284402 | 4-May-15 |
| 18326 | 2 | 3 | | H-2 | Rint | 126432 | 4-May-15 | 18905 | 2 | 3 | | H-2 | Scgb2b20 | | |
| 18328 | 2 | 3 | | H-2 | Riok1 | 83732 | 4-May-15 | 18911 | 2 | 3 | | H-2 | Scgb2b7 | | |
| 18339 | 2 | 3 | | H-2 | Rit2 | 6014 | 4-May-15 | 18924 | 2 | 3 | | H-2 | Scn1a | 11280 | 12-May-15 |
| 18344 | 2 | 3 | | H-2 | Rin1 | 6013 | 4-May-15 | 18930 | 2 | 3 | | H-2 | Scn3b | 55800 | 23-May-15 |
| 18345 | 2 | 3 | | H-2 | Rin3 | 117579 | 4-May-15 | 18942 | 2 | 3 | | H-2 | Sco2 | 9997 | 4-May-15 |
| 18348 | 2 | 3 | | H-2 | Rmdn2 | 151393 | 4-May-15 | 18944 | 2 | 3 | | H-2 | Scp2 | 6342 | 7-Jun-15 |
| 18350 | 2 | 3 | | H-2 | Rmi1 | 80010 | 4-May-15 | 18946 | 2 | 3 | | H-2 | Scpep1 | 59342 | 4-May-15 |
| 18351 | 2 | 3 | | H-2 | Rmi2 | 116028 | 4-May-15 | 18959 | 2 | 3 | | H-2 | Scube3 | 222663 | 4-May-15 |
| 18354 | 2 | 3 | | H-2 | Rmnd5b | 64777 | 4-May-15 | 18962 | 2 | 3 | | H-2 | Scyl2 | 55681 | 7-Jun-15 |
| 18381 | 2 | 3 | | H-2 | Rnf103 | 7844 | 4-May-15 | 18974 | 2 | 3 | | H-2 | Sdf4 | 6388 | 4-May-15 |
| 18384 | 2 | 3 | | H-2 | Rnf112 | 7732 | 4-May-15 | 18977 | 2 | 3 | | H-2 | Sdha | 6389 | 23-May-15 |
| 18386 | 2 | 3 | | H-2 | Rnf113a2 | | | 18982 | 2 | 3 | | H-2 | Sdhd | 6392 | 23-May-15 |
| 18390 | 2 | 3 | | H-2 | Rnf122 | 79845 | 4-May-15 | 18994 | 2 | 3 | | H-2 | Sec1 | 653677 | 4-May-15 |
| 18396 | 2 | 3 | | H-2 | Rnf130 | 55819 | 2-Jun-15 | 19009 | 2 | 3 | | H-2 | Sec23b | 10483 | 4-May-15 |
| 18402 | 2 | 3 | | H-2 | Rnf14 | 9604 | 4-May-15 | 19011 | 2 | 3 | | H-2 | Sec24a | 10802 | 4-May-15 |
| 18418 | 2 | 3 | | H-2 | Rnf169 | 254225 | 4-May-15 | 19016 | 2 | 3 | | H-2 | Sec31b | 25956 | 4-May-15 |
| 18419 | 2 | 3 | | H-2 | Rnf17 | 56163 | 14-May-15 | 19022 | 2 | 3 | | H-2 | Sec63 | 11231 | 4-May-15 |
| 18429 | 2 | 3 | | H-2 | Rnf19b | 127544 | 23-May-15 | 19032 | 2 | 3 | | H-2 | Sell | 6400 | 12-May-15 |
| 18436 | 2 | 3 | | H-2 | Rnf216 | 54476 | 4-May-15 | 19038 | 2 | 3 | | H-2 | Selp | 6403 | 7-Jun-15 |
| 18439 | 2 | 3 | | H-2 | Rnf220 | 55182 | 4-May-15 | 19041 | 2 | 3 | | H-2 | Sema3a | 10371 | 17-May-15 |

Fig.22 - 53

| | | | | | | | | | | | | | | |
|---|---|---|---|---|---|---|---|---|---|---|---|---|---|---|
| 19045 | 2 | 3 | | III-2 | Sema3e | 9723 | 23-May-15 | 19727 | 2 | 3 | | III-2 | Slc6a11 | 6538 | 4-May-15 |
| 19055 | 2 | 3 | | III-2 | Sema5b | 54437 | 4-May-15 | 19729 | 2 | 3 | | III-2 | Slc6a13 | 6540 | 4-May-15 |
| 19056 | 2 | 3 | | III-2 | Sema6a | 57556 | 12-May-15 | 19752 | 2 | 3 | | III-2 | Slc7a15 | | |
| 19062 | 2 | 3 | | III-2 | Senp2 | 59343 | 7-Jun-15 | 19762 | 2 | 3 | | III-2 | Slc8a1 | 6546 | 23-May-15 |
| 19068 | 2 | 3 | | III-2 | Sephs1 | 22929 | 2-Jun-15 | 19793 | 2 | 3 | | III-2 | Slco6c1 | | |
| 19076 | 2 | 3 | | III-2 | Sept12 | 124404 | 12-May-15 | 19803 | 2 | 3 | | III-2 | Slfn8 | | |
| 19082 | 2 | 3 | | III-2 | Sept5 | 5413 | 4-May-15 | 19806 | 2 | 3 | | III-2 | Slirp | 81892 | 4-May-15 |
| 19085 | 2 | 3 | | III-2 | Sept8 | 23176 | 4-May-15 | 19808 | 2 | 3 | | III-2 | Slit2 | 9353 | 7-Jun-15 |
| 19087 | 2 | 3 | | III-2 | Sepw1 | 6415 | 12-May-15 | 19811 | 2 | 3 | | III-2 | Slitrk2 | 84631 | 4-May-15 |
| 19092 | 2 | 3 | | III-2 | Sergef | 26297 | 4-May-15 | 19817 | 2 | 3 | | III-2 | Slmap | 7871 | 12-May-15 |
| 19103 | 2 | 3 | | III-2 | Serpina12 | 145264 | 12-May-15 | 19823 | 2 | 3 | | III-2 | Slu7 | 10569 | 4-May-15 |
| 19123 | 2 | 3 | | III-2 | Serpina6 | 866 | 31-May-15 | 19830 | 2 | 3 | | III-2 | Sly | 54440 | 4-May-15 |
| 19132 | 2 | 3 | | III-2 | Serpinb1c | | | 19841 | 2 | 3 | | III-2 | Smap2 | 64744 | 7-Jun-15 |
| 19142 | 2 | 3 | | III-2 | Serpinb6d | | | 19845 | 2 | 3 | | III-2 | Smarca5 | 8467 | 4-May-15 |
| 19148 | 2 | 3 | | III-2 | Serpinb9c | | | 19847 | 2 | 3 | | III-2 | Smarcad1 | 56916 | 4-May-15 |
| 19165 | 2 | 3 | | III-2 | Sertad2 | 9792 | 21-May-15 | 19848 | 2 | 3 | | III-2 | Smarcal1 | 50485 | 23-May-15 |
| 19173 | 2 | 3 | | III-2 | Ser | 6418 | 3-May-15 | 19849 | 2 | 3 | | III-2 | Smarcb1 | 6598 | 12-May-15 |
| 19181 | 2 | 3 | | III-2 | Setd6 | 79918 | 4-May-15 | 19856 | 2 | 3 | | III-2 | Smc1a | 8243 | 23-May-15 |
| 19185 | 2 | 3 | | III-2 | Setdb2 | 83852 | 4-May-15 | 19857 | 2 | 3 | | III-2 | Smc1b | 27127 | 4-May-15 |
| 19188 | 2 | 3 | | III-2 | Sez6 | 124925 | 4-May-15 | 19858 | 2 | 3 | | III-2 | Smc2 | 10592 | 7-Jun-15 |
| 19192 | 2 | 3 | | III-2 | Sf3a1 | 10291 | 4-May-15 | 19860 | 2 | 3 | | III-2 | Smc3 | 9126 | 23-May-15 |
| 19212 | 2 | 3 | | III-2 | Sft2d1 | 113402 | 4-May-15 | 19863 | 2 | 3 | | III-2 | Smc6 | 79677 | 4-May-15 |
| 19217 | 2 | 3 | | III-2 | Sftpb | 6439 | 12-May-15 | 19867 | 2 | 3 | | III-2 | Smco3 | 440087 | 4-May-15 |
| 19220 | 2 | 3 | | III-2 | Sfxn1 | 94081 | 4-May-15 | 19876 | 2 | 3 | | III-2 | Smg6 | 23293 | 4-May-15 |
| 19224 | 2 | 3 | | III-2 | Sfxn5 | 94097 | 4-May-15 | 19884 | 2 | 3 | | III-2 | Smim13 | 221710 | 12-May-15 |
| 19231 | 2 | 3 | | III-2 | Sgip1 | 84251 | 12-May-15 | 19898 | 2 | 3 | | III-2 | Smim8 | 57150 | 4-May-15 |
| 19267 | 2 | 3 | | III-2 | Sh3bp5 | 9467 | 4-May-15 | 19900 | 2 | 3 | | III-2 | Smlr1 | 100507203 | 4-May-15 |
| 19269 | 2 | 3 | | III-2 | Sh3d19 | 152503 | 4-May-15 | 19903 | 2 | 3 | | III-2 | Smo | 6608 | 7-Jun-15 |
| 19297 | 2 | 3 | | III-2 | Shd | 56961 | 4-May-15 | 19904 | 2 | 3 | | III-2 | Smoc1 | 64093 | 4-May-15 |
| 19306 | 2 | 3 | | III-2 | Shisa6 | 388336 | 14-May-15 | 19907 | 2 | 3 | | III-2 | Smok2b | | |
| 19309 | 2 | 3 | | III-2 | Shkbp1 | 92799 | 4-May-15 | 19913 | 2 | 3 | | III-2 | Smpd2 | 6610 | 4-May-15 |
| 19310 | 2 | 3 | | III-2 | Shrm1 | 6470 | 12-May-15 | 19916 | 2 | 3 | | III-2 | Smpd5 | 392275 | 4-May-15 |
| 19322 | 2 | 3 | | III-2 | Siah1a | 6477 | 24-May-15 | 19927 | 2 | 3 | | III-2 | Smug1 | 23583 | 4-May-15 |
| 19339 | 2 | 3 | | III-2 | Sike1 | 80143 | 4-May-15 | 19929 | 2 | 3 | | III-2 | Smurf2 | 64750 | 23-May-15 |
| 19348 | 2 | 3 | | III-2 | Sipa1l2 | 57568 | 4-May-15 | 19935 | 2 | 3 | | III-2 | Snai1 | 6615 | 17-May-15 |
| 19349 | 2 | 3 | | III-2 | Sipa1l3 | 23094 | 4-May-15 | 19939 | 2 | 3 | | III-2 | Snap25 | 6616 | 7-May-15 |
| 19352 | 2 | 3 | | III-2 | Sirpb1b | | | 19944 | 2 | 3 | | III-2 | Snapc2 | 6618 | 4-May-15 |
| 19354 | 2 | 3 | | III-2 | Sirt2 | 22933 | 17-May-15 | 19974 | 2 | 3 | | III-2 | Snora20 | 677806 | 4-May-15 |
| 19355 | 2 | 3 | | III-2 | Sirt3 | 23410 | 31-May-15 | 19978 | 2 | 3 | | III-2 | Snora26 | 677810 | 4-May-15 |
| 19359 | 2 | 3 | | III-2 | Sirt7 | 51547 | 23-May-15 | 19987 | 2 | 3 | | III-2 | Snora36b | 677818 | 4-May-15 |
| 19360 | 2 | 3 | | III-2 | Sis | 5155 | 7-Jun-15 | 19994 | 2 | 3 | | III-2 | Snora61 | 677838 | 4-May-15 |
| 19366 | 2 | 3 | | III-2 | Six3os1 | | | 20007 | 2 | 3 | | III-2 | Snord104 | 692227 | 12-May-15 |
| 19370 | 2 | 3 | | III-2 | Ska1 | 220134 | 4-May-15 | 20025 | 2 | 3 | | III-2 | Snord1a | 677848 | 4-May-15 |
| 19372 | 2 | 3 | | III-2 | Ska3 | 221150 | 4-May-15 | 20032 | 2 | 3 | | III-2 | Snord33 | 26818 | 4-May-15 |
| 19375 | 2 | 3 | | III-2 | Ski | 6497 | 23-May-15 | 20095 | 2 | 3 | | III-2 | Snrpd2 | 6633 | 4-May-15 |
| 19376 | 2 | 3 | | III-2 | Skida1 | 387640 | 4-May-15 | 20107 | 2 | 3 | | III-2 | Snupn | 10073 | 4-May-15 |
| 19378 | 2 | 3 | | III-2 | Skint1 | 391037 | 4-May-15 | 20110 | 2 | 3 | | III-2 | Snx1 | 6642 | 21-May-15 |
| 19384 | 2 | 3 | | III-2 | Skint5 | | | 20113 | 2 | 3 | | III-2 | Snx12 | 29934 | 2-Jun-15 |
| 19392 | 2 | 3 | | III-2 | Skor2 | 652991 | 21-May-15 | 20126 | 2 | 3 | | III-2 | Snx25 | 83891 | 4-May-15 |
| 19397 | 2 | 3 | | III-2 | Slain1 | 122060 | 4-May-15 | 20130 | 2 | 3 | | III-2 | Snx30 | 401548 | 7-Jun-15 |
| 19398 | 2 | 3 | | III-2 | Slain1os | | | 20135 | 2 | 3 | | III-2 | Snx5 | 27131 | 12-May-15 |
| 19399 | 2 | 3 | | III-2 | Slain2 | 57806 | 4-May-15 | 20154 | 2 | 3 | | III-2 | Soga3 | 387104 | 4-May-15 |
| 19401 | 2 | 3 | | III-2 | Slamf6 | 114836 | 4-May-15 | 20165 | 2 | 3 | | III-2 | Sord | 6652 | 12-May-15 |
| 19409 | 2 | 3 | | III-2 | Slc10a3-ubl4 | | | 20168 | 2 | 3 | | III-2 | Sos1 | 6654 | 23-May-15 |
| 19421 | 2 | 3 | | III-2 | Slc12a6 | 9990 | 23-May-15 | 20187 | 2 | 3 | | III-2 | Sox2ot | 347689 | 12-May-15 |
| 19422 | 2 | 3 | | III-2 | Slc12a7 | 10723 | 4-May-15 | 20189 | 2 | 3 | | III-2 | Sox30 | 11063 | 28-May-15 |
| 19423 | 2 | 3 | | III-2 | Slc12a8 | 84561 | 1-Jun-15 | 20190 | 2 | 3 | | III-2 | Sox4 | 6659 | 4-May-15 |
| 19429 | 2 | 3 | | III-2 | Slc13a4 | 26286 | 4-May-15 | 20192 | 2 | 3 | | III-2 | Sox5os3 | | |
| 19437 | 2 | 3 | | III-2 | Slc15a5 | 729025 | 4-May-15 | 20198 | 2 | 3 | | III-2 | Sp100 | 6672 | 4-May-15 |
| 19463 | 2 | 3 | | III-2 | Slc16a3 | 6572 | 4-May-15 | 20199 | 2 | 3 | | III-2 | Sp110 | 3431 | 7-Jun-15 |
| 19464 | 2 | 3 | | III-2 | Slc18b1 | 116843 | 4-May-15 | 20200 | 2 | 3 | | III-2 | Sp140 | 11262 | 4-May-15 |
| 19477 | 2 | 3 | | III-2 | Slc22a1 | 6580 | 17-May-15 | 20205 | 2 | 3 | | III-2 | Sp5 | 389058 | 4-May-15 |
| 19480 | 2 | 3 | | III-2 | Slc22a18b-ps | | | 20208 | 2 | 3 | | III-2 | Sp8 | 221833 | 4-May-15 |
| 19488 | 2 | 3 | | III-2 | Slc22a20 | 440044 | 4-May-15 | 20209 | 2 | 3 | | III-2 | Sp9 | 100131390 | 4-May-15 |
| 19489 | 2 | 3 | | III-2 | Slc22a21 | | | 20213 | 2 | 3 | | III-2 | Spaca4 | 171169 | 4-May-15 |
| 19497 | 2 | 3 | | III-2 | Slc22a30 | | | 20215 | 2 | 3 | | III-2 | Spaca6 | 147650 | 3-May-15 |
| 19513 | 2 | 3 | | III-2 | Slc25a11 | 8402 | 4-May-15 | 20217 | 2 | 3 | | III-2 | Spag1 | 6674 | 26-May-15 |
| 19518 | 2 | 3 | | III-2 | Slc25a16 | 8034 | 4-May-15 | 20225 | 2 | 3 | | III-2 | Spag7 | 9552 | 4-May-15 |
| 19526 | 2 | 3 | | III-2 | Slc25a23 | 79085 | 4-May-15 | 20232 | 2 | 3 | | III-2 | Spata1 | 100505741 | 4-May-15 |
| 19536 | 2 | 3 | | III-2 | Slc25a32 | 81034 | 4-May-15 | 20235 | 2 | 3 | | III-2 | Spata17 | 128153 | 4-May-15 |
| 19540 | 2 | 3 | | III-2 | Slc25a36 | 55186 | 4-May-15 | 20244 | 2 | 3 | | III-2 | Spata21 | 124044 | 4-May-15 |
| 19546 | 2 | 3 | | III-2 | Slc25a41 | 284427 | 4-May-15 | 20254 | 2 | 3 | | III-2 | Spata45 | 149643 | 4-May-15 |
| 19547 | 2 | 3 | | III-2 | Slc25a42 | 284439 | 4-May-15 | 20258 | 2 | 3 | | III-2 | Spata7 | 55812 | 23-May-15 |
| 19550 | 2 | 3 | | III-2 | Slc25a45 | 283130 | 12-May-15 | 20260 | 2 | 3 | | III-2 | Spatc1 | 375686 | 4-May-15 |
| 19565 | 2 | 3 | | III-2 | Slc26a6 | 65010 | 4-May-15 | 20261 | 2 | 3 | | III-2 | Spatc1l | 84221 | 4-May-15 |
| 19573 | 2 | 3 | | III-2 | Slc27a5 | 10998 | 4-May-15 | 20268 | 2 | 3 | | III-2 | Spcs2 | 9789 | 4-May-15 |
| 19587 | 2 | 3 | | III-2 | Slc2a3 | 6515 | 12-May-15 | 20285 | 2 | 3 | | III-2 | Speer5-ps1 | | |
| 19600 | 2 | 3 | | III-2 | Slc30a5 | 64924 | 4-May-15 | 20288 | 2 | 3 | | III-2 | Speer8-ps1 | | |
| 19603 | 2 | 3 | | III-2 | Slc30a8 | 169026 | 31-May-15 | 20299 | 2 | 3 | | III-2 | Spg21 | 51324 | 4-May-15 |
| 19613 | 2 | 3 | | III-2 | Slc35a2 | 7355 | 4-May-15 | 20308 | 2 | 3 | | III-2 | Spidr | 23514 | 12-May-15 |
| 19616 | 2 | 3 | | III-2 | Slc35a5 | 55032 | 4-May-15 | 20336 | 2 | 3 | | III-2 | Spns1 | 83985 | 4-May-15 |
| 19627 | 2 | 3 | | III-2 | Slc35e2 | 9906 | 7-Jun-15 | 20339 | 2 | 3 | | III-2 | Spo11 | 23626 | 31-May-15 |
| 19633 | 2 | 3 | | III-2 | Slc35f4 | 341880 | 12-May-15 | 20346 | 2 | 3 | | III-2 | Spopl | 339745 | 4-May-15 |
| 19635 | 2 | 3 | | III-2 | Slc35f6 | 54978 | 4-May-15 | 20349 | 2 | 3 | | III-2 | Sppl2a | 84888 | 29-May-15 |
| 19639 | 2 | 3 | | III-2 | Slc36a1 | 206358 | 12-May-15 | 20350 | 2 | 3 | | III-2 | Sppl2b | 56928 | 4-May-15 |
| 19647 | 2 | 3 | | III-2 | Slc37a4 | 2542 | 28-May-15 | 20352 | 2 | 3 | | III-2 | Sppl3 | 121665 | 29-May-15 |
| 19651 | 2 | 3 | | III-2 | Slc38a2 | 54407 | 12-May-15 | 20384 | 2 | 3 | | III-2 | Sptb4 | 92369 | 4-May-15 |
| 19660 | 2 | 3 | | III-2 | Slc39a10 | 57181 | 4-May-15 | 20390 | 2 | 3 | | III-2 | Sptbn2 | 6712 | 23-May-15 |
| 19662 | 2 | 3 | | III-2 | Slc39a12 | 221074 | 4-May-15 | 20393 | 2 | 3 | | III-2 | Sptlc2 | 9517 | 4-May-15 |
| 19663 | 2 | 3 | | III-2 | Slc39a13 | 91252 | 17-May-15 | 20410 | 2 | 3 | | III-2 | Srebf1 | 6720 | 24-May-15 |
| 19673 | 2 | 3 | | III-2 | Slc3a1 | 6519 | 12-May-15 | 20424 | 2 | 3 | | III-2 | Srp14 | 6727 | 3-Jun-15 |
| 19684 | 2 | 3 | | III-2 | Slc44a3 | 126969 | 4-May-15 | 20430 | 2 | 3 | | III-2 | Srp72 | 6731 | 12-May-15 |
| 19687 | 2 | 3 | | III-2 | Slc45a1 | 50651 | 21-May-15 | 20436 | 2 | 3 | | III-2 | Srprb | 58477 | 21-May-15 |
| 19696 | 2 | 3 | | III-2 | Slc48a1 | 55652 | 4-May-15 | 20440 | 2 | 3 | | III-2 | Srrd | 402055 | 4-May-15 |
| 19705 | 2 | 3 | | III-2 | Slc4a7 | 9497 | 4-May-15 | 20442 | 2 | 3 | | III-2 | Srrm2 | 23524 | 3-Jun-15 |
| 19707 | 2 | 3 | | III-2 | Slc4a9 | 83697 | 4-May-15 | | | | | | | | |
| 19708 | 2 | 3 | | III-2 | Slc50a1 | 55974 | 4-May-15 | | | | | | | | |

Fig.22 - 54

| | | | | | | | | | | | | | | | |
|---|---|---|---|---|---|---|---|---|---|---|---|---|---|---|---|
| 20444 | 2 | 3 | | | III-2 | Srrm4 | 84630 | 4-May-15 | 21108 | 2 | 3 | | III-2 | Tecpr2 | 9895 | 4-May-15 |
| 20449 | 2 | 3 | | | III-2 | Srsf11 | 9295 | 4-May-15 | 21130 | 2 | 3 | | III-2 | Tepp | 374739 | 4-May-15 |
| 20450 | 2 | 3 | | | III-2 | Srsf12 | 135295 | 4-May-15 | 21135 | 2 | 3 | | III-2 | Tert | 7015 | 4-Jun-15 |
| 20452 | 2 | 3 | | | III-2 | Srsf3 | 6428 | 21-May-15 | 21139 | 2 | 3 | | III-2 | Tesk1 | 7016 | 4-May-15 |
| 20454 | 2 | 3 | | | III-2 | Srsf5 | 6430 | 1-Jun-15 | 21143 | 2 | 3 | | III-2 | Tet2 | 54790 | 17-May-15 |
| 20460 | 2 | 3 | | | III-2 | Ss18 | 6760 | 12-May-15 | 21146 | 2 | 3 | | III-2 | Tex101 | 83639 | 4-May-15 |
| 20463 | 2 | 3 | | | III-2 | Ssbp1 | 6742 | 14-May-15 | 21147 | 2 | 3 | | III-2 | Tex11 | 56159 | 4-May-15 |
| 20464 | 2 | 3 | | | III-2 | Ssbp2 | 23635 | 12-May-15 | 21150 | 2 | 3 | | III-2 | Tex13a | 56157 | 21-May-15 |
| 20466 | 2 | 3 | | | III-2 | Ssbp4 | 170463 | 12-May-15 | 21154 | 2 | 3 | | III-2 | Tex19.1 | | |
| 20473 | 2 | 3 | | | III-2 | Ssna1 | 8636 | 4-May-15 | 21158 | 2 | 3 | | III-2 | Tex22 | 647310 | 4-May-15 |
| 20486 | 2 | 3 | | | III-2 | Sstr4 | 6754 | 12-May-15 | 21167 | 2 | 3 | | III-2 | Tex35 | 84066 | 4-May-15 |
| 20488 | 2 | 3 | | | III-2 | Ssty1 | | | 21173 | 2 | 3 | | III-2 | Tex9 | 374618 | 4-May-15 |
| 20489 | 2 | 3 | | | III-2 | Ssty2 | | | 21178 | 2 | 3 | | III-2 | Tfap2d | 83741 | 4-May-15 |
| 20494 | 2 | 3 | | | III-2 | Ssxb1 | | | 21182 | 2 | 3 | | III-2 | Tfb2m | 64216 | 4-May-15 |
| 20514 | 2 | 3 | | | III-2 | St6galnac1 | 55808 | 4-May-15 | 21226 | 2 | 3 | | III-2 | Tgtp1 | | |
| 20517 | 2 | 3 | | | III-2 | St6galnac4 | 27090 | 4-May-15 | 21229 | 2 | 3 | | III-2 | Tha1 | | |
| 20525 | 2 | 3 | | | III-2 | St8sia3os | | | 21238 | 2 | 3 | | III-2 | Thbd | 7056 | 23-May-15 |
| 20535 | 2 | 3 | | | III-2 | Stag2 | 10735 | 21-May-15 | 21244 | 2 | 3 | | III-2 | Them4 | 117145 | 4-May-15 |
| 20536 | 2 | 3 | | | III-2 | Stag3 | 10734 | 4-May-15 | 21251 | 2 | 3 | | III-2 | Thg1l | 54974 | 4-May-15 |
| 20537 | 2 | 3 | | | III-2 | Stam | 8027 | 4-May-15 | 21253 | 2 | 3 | | III-2 | Thnsl2 | 55258 | 4-May-15 |
| 20576 | 2 | 3 | | | III-2 | Stim2 | 57620 | 10-May-15 | 21256 | 2 | 3 | | III-2 | Thoc3 | 84321 | 4-May-15 |
| 20580 | 2 | 3 | | | III-2 | Stk11ip | 114790 | 1-Jun-15 | 21257 | 2 | 3 | | III-2 | Thoc5 | 8563 | 4-May-15 |
| 20582 | 2 | 3 | | | III-2 | Stk17b | 9262 | 4-May-15 | 21260 | 2 | 3 | | III-2 | Thop1 | 7064 | 12-May-15 |
| 20585 | 2 | 3 | | | III-2 | Stk25 | 10494 | 4-May-15 | 21263 | 2 | 3 | | III-2 | Thrap3 | 9967 | 12-May-15 |
| 20594 | 2 | 3 | | | III-2 | Stk38 | 11329 | 20-May-15 | 21264 | 2 | 3 | | III-2 | Thrb | 7068 | 14-May-15 |
| 20604 | 2 | 3 | | | III-2 | Stmnd1 | 461236 | 4-May-15 | 21269 | 2 | 3 | | III-2 | Thsd7b | 80731 | 4-May-15 |
| 20605 | 2 | 3 | | | III-2 | Stom | 2040 | 12-May-15 | 21270 | 2 | 3 | | III-2 | Thtpa | 79178 | 4-May-15 |
| 20614 | 2 | 3 | | | III-2 | Stpg2 | 285555 | 12-May-15 | 21274 | 2 | 3 | | III-2 | Thy1 | 7070 | 3-May-15 |
| 20615 | 2 | 3 | | | III-2 | Stra13 | 201254 | 7-Jun-15 | 21277 | 2 | 3 | | III-2 | Tial1 | 7073 | 2-Jun-15 |
| 20618 | 2 | 3 | | | III-2 | Strada | 92335 | 4-May-15 | 21281 | 2 | 3 | | III-2 | Ticam2 | 353376 | 4-May-15 |
| 20623 | 2 | 3 | | | III-2 | Strip1 | 85369 | 4-May-15 | 21287 | 2 | 3 | | III-2 | Tigd3 | 220359 | 21-May-15 |
| 20627 | 2 | 3 | | | III-2 | Strn4 | 29888 | 12-May-15 | 21290 | 2 | 3 | | III-2 | Tigit | 201633 | 3-May-15 |
| 20641 | 2 | 3 | | | III-2 | Stx4a | 6810 | 4-May-15 | 21294 | 2 | 3 | | III-2 | Timm10 | 26519 | 21-May-15 |
| 20648 | 2 | 3 | | | III-2 | Stxbp3a | | | 21298 | 2 | 3 | | III-2 | Timm13 | 26517 | 4-May-15 |
| 20652 | 2 | 3 | | | III-2 | Stxbp5l | 9515 | 12-May-15 | 21301 | 2 | 3 | | III-2 | Timm23 | 100287 932 | 7-Jun-15 |
| 20664 | 2 | 3 | | | III-2 | Sufu | 51684 | 23-May-15 | 21306 | 2 | 3 | | III-2 | Timm8b | 26521 | 4-May-15 |
| 20678 | 2 | 3 | | | III-2 | Sult2a2 | | | 21308 | 2 | 3 | | III-2 | Timmdc1 | 51300 | 4-May-15 |
| 20686 | 2 | 3 | | | III-2 | Sult4a1 | 25830 | 4-May-15 | 21311 | 2 | 3 | | III-2 | Timp3 | 7078 | 12-May-15 |
| 20689 | 2 | 3 | | | III-2 | Sumf1 | 285362 | 4-May-15 | 21314 | 2 | 3 | | III-2 | Tinagl1 | 64129 | 12-May-15 |
| 20692 | 2 | 3 | | | III-2 | Sumo2 | 6613 | 24-May-15 | 21319 | 2 | 3 | | III-2 | Tirap | 114609 | 12-May-15 |
| 20694 | 2 | 3 | | | III-2 | Sun1 | 23353 | 4-May-15 | 21328 | 2 | 3 | | III-2 | Tkt12 | 84076 | 4-May-15 |
| 20717 | 2 | 3 | | | III-2 | Suv39h2 | 79723 | 3-May-15 | 21332 | 2 | 3 | | III-2 | Tldc2 | 140711 | 4-May-15 |
| 20719 | 2 | 3 | | | III-2 | Suv420h2 | 84787 | 4-May-15 | 21336 | 2 | 3 | | III-2 | Tle4 | 7091 | 31-May-15 |
| 20721 | 2 | 3 | | | III-2 | Sv2a | 9900 | 12-May-15 | 21339 | 2 | 3 | | III-2 | Tlk2 | 11011 | 4-May-15 |
| 20725 | 2 | 3 | | | III-2 | Sval1 | | | 21342 | 2 | 3 | | III-2 | Tln1 | 7094 | 12-May-15 |
| 20727 | 2 | 3 | | | III-2 | Sval3 | | | 21357 | 2 | 3 | | III-2 | Tlx2 | 3196 | 7-Jun-15 |
| 20747 | 2 | 3 | | | III-2 | Syce1l | 100130 958 | 4-May-15 | 21359 | 2 | 3 | | III-2 | Tm2d1 | 83941 | 4-May-15 |
| 20752 | 2 | 3 | | | III-2 | Sycp1-ps1 | | | 21361 | 2 | 3 | | III-2 | Tm2d3 | 80213 | 12-May-15 |
| 20756 | 2 | 3 | | | III-2 | Syde2 | 84144 | 4-May-15 | 21371 | 2 | 3 | | III-2 | Tm9sf1 | 10548 | 21-May-15 |
| 20764 | 2 | 3 | | | III-2 | Synb | | | 21378 | 2 | 3 | | III-2 | Tm9sf2 | 9375 | 4-May-15 |
| 20767 | 2 | 3 | | | III-2 | Syndig1 | 79953 | 4-May-15 | 21393 | 2 | 3 | | III-2 | Tmbim4 | 51643 | 4-May-15 |
| 20776 | 2 | 3 | | | III-2 | Syngr3 | 9143 | 4-May-15 | 21396 | 2 | 3 | | III-2 | Tmco2 | 127391 | 4-May-15 |
| 20778 | 2 | 3 | | | III-2 | Synj1 | 8867 | 12-May-15 | 21401 | 2 | 3 | | III-2 | Tmco5 | 145942 | 12-May-15 |
| 20786 | 2 | 3 | | | III-2 | Synrg | 11276 | 4-May-15 | 21403 | 2 | 3 | | III-2 | Tmed11 | | |
| 20791 | 2 | 3 | | | III-2 | Syt1 | 6857 | 12-May-15 | 21405 | 2 | 3 | | III-2 | Tmed3 | 23423 | 4-May-15 |
| 20793 | 2 | 3 | | | III-2 | Syt11 | 23208 | 16-Jun-15 | 21410 | 2 | 3 | | III-2 | Tmed5 | 50999 | 4-May-15 |
| 20797 | 2 | 3 | | | III-2 | Syt15 | 83849 | 4-May-15 | 21422 | 2 | 3 | | III-2 | Tmeff1 | 8577 | 4-May-15 |
| 20800 | 2 | 3 | | | III-2 | Syt2 | 127833 | 5-May-15 | 21435 | 2 | 3 | | III-2 | Tmem11 | 8834 | 4-May-15 |
| 20804 | 2 | 3 | | | III-2 | Syt6 | 148281 | 4-May-15 | 21436 | 2 | 3 | | III-2 | Tmem127 | 55654 | 23-May-15 |
| 20807 | 2 | 3 | | | III-2 | Syt9 | 143425 | 4-May-15 | 21438 | 2 | 3 | | III-2 | Tmem128 | 86013 | 12-May-15 |
| 20813 | 2 | 3 | | | III-2 | Syvn1 | 84447 | 29-May-15 | 21440 | 2 | 3 | | III-2 | Tmem132a | 54972 | 4-May-15 |
| 20835 | 2 | 3 | | | III-2 | Tab3 | 257397 | 4-May-15 | 21442 | 2 | 3 | | III-2 | Tmem132c | 92293 | 4-May-15 |
| 20852 | 2 | 3 | | | III-2 | Taf10 | 6881 | 12-May-15 | 21443 | 2 | 3 | | III-2 | Tmem132cos | | |
| 20854 | 2 | 3 | | | III-2 | Taf12 | 6883 | 4-May-15 | 21444 | 2 | 3 | | III-2 | Tmem132d | 121256 | 4-May-15 |
| 20860 | 2 | 3 | | | III-2 | Taf1d | 79101 | 12-May-15 | 21448 | 2 | 3 | | III-2 | Tmem136 | 219902 | 4-May-15 |
| 20862 | 2 | 3 | | | III-2 | Taf3 | 83860 | 4-May-15 | 21459 | 2 | 3 | | III-2 | Tmem150a | 129303 | 4-May-15 |
| 20867 | 2 | 3 | | | III-2 | Taf6 | 6878 | 12-May-15 | 21463 | 2 | 3 | | III-2 | Tmem151a | 256472 | 4-May-15 |
| 20870 | 2 | 3 | | | III-2 | Taf7l | 54457 | 12-May-15 | 21467 | 2 | 3 | | III-2 | Tmem159 | 57146 | 12-May-15 |
| 20871 | 2 | 3 | | | III-2 | Taf8 | 129685 | 4-May-15 | 21469 | 2 | 3 | | III-2 | Tmem161a | 54929 | 4-May-15 |
| 20893 | 2 | 3 | | | III-2 | Tapbp | 6892 | 17-May-15 | 21470 | 2 | 3 | | III-2 | Tmem161b | 153396 | 4-May-15 |
| 20896 | 2 | 3 | | | III-2 | Tarbp2 | 6895 | 12-May-15 | 21476 | 2 | 3 | | III-2 | Tmem168 | 64418 | 4-May-15 |
| 20906 | 2 | 3 | | | III-2 | Tas2r103 | | | 21484 | 2 | 3 | | III-2 | Tmem175 | 84286 | 12-May-15 |
| 20943 | 2 | 3 | | | III-2 | Tatdn2 | 9797 | 12-May-15 | 21495 | 2 | 3 | | III-2 | Tmem181b-ps | | |
| 20948 | 2 | 3 | | | III-2 | Tbata | 219793 | 4-May-15 | 21502 | 2 | 3 | | III-2 | Tmem185b | 79134 | 12-May-15 |
| 20954 | 2 | 3 | | | III-2 | Tbc1d13 | 54662 | 4-May-15 | 21503 | 2 | 3 | | III-2 | Tmem186 | 25880 | 4-May-15 |
| 20959 | 2 | 3 | | | III-2 | Tbc1d19 | 55296 | 4-May-15 | 21504 | 2 | 3 | | III-2 | Tmem189 | 387521 | 4-May-15 |
| 20972 | 2 | 3 | | | III-2 | Tbc1d32 | 221322 | 4-May-15 | 21510 | 2 | 3 | | III-2 | Tmem194b | 100131 211 | 28-May-15 |
| 20984 | 2 | 3 | | | III-2 | Tbcd | 6904 | 4-May-15 | 21511 | 2 | 3 | | III-2 | Tmem196 | 256130 | 4-May-15 |
| 20989 | 2 | 3 | | | III-2 | Tbkbp1 | 9755 | 4-May-15 | 21514 | 2 | 3 | | III-2 | Tmem199 | 147007 | 4-May-15 |
| 20992 | 2 | 3 | | | III-2 | Tbl2 | 26608 | 4-May-15 | 21515 | 2 | 3 | | III-2 | Tmem2 | 23670 | 4-May-15 |
| 20994 | 2 | 3 | | | III-2 | Tbp | 6908 | 31-May-15 | 21526 | 2 | 3 | | III-2 | Tmem208 | 29100 | 4-May-15 |
| 20996 | 2 | 3 | | | III-2 | Tbpl2 | 387332 | 7-Jun-15 | 21528 | 2 | 3 | | III-2 | Tmem210 | 100505 993 | 4-May-15 |
| 21005 | 2 | 3 | | | III-2 | Tbx19 | 9095 | 4-May-15 | 21539 | 2 | 3 | | III-2 | Tmem211 | 295349 | 4-May-15 |
| 21019 | 2 | 3 | | | III-2 | Tcam1 | 146771 | 4-May-15 | 21533 | 2 | 3 | | III-2 | Tmem215 | 401498 | 4-May-15 |
| 21035 | 2 | 3 | | | III-2 | Tcerg1 | 10915 | 4-May-15 | 21536 | 2 | 3 | | III-2 | Tmem218 | 219854 | 4-May-15 |
| 21050 | 2 | 3 | | | III-2 | Tcf15 | 10732 | 24-May-15 | 21541 | 2 | 3 | | III-2 | Tmem223 | 79064 | 4-May-15 |
| 21063 | 2 | 3 | | | III-2 | Tcp1 | 6950 | 17-May-15 | 21543 | 2 | 3 | | III-2 | Tmem229a | 730130 | 12-May-15 |
| 21071 | 2 | 3 | | | III-2 | Tcstv3 | | | 21546 | 2 | 3 | | III-2 | Tmem231 | 79583 | 23-May-15 |
| 21074 | 2 | 3 | | | III-2 | Tcte2 | | | 21550 | 2 | 3 | | III-2 | Tmem235 | 283999 | 4-May-15 |
| 21081 | 2 | 3 | | | III-2 | Tctn3 | 26123 | 23-May-15 | 21551 | 2 | 3 | | III-2 | Tmem236 | 653567 | 4-May-15 |
| 21084 | 2 | 3 | | | III-2 | Tdh | 157739 | 7-Jun-15 | 21575 | 2 | 3 | | III-2 | Tmem26 | 219623 | 4-May-15 |
| 21086 | 2 | 3 | | | III-2 | Tdp1 | 55775 | 24-May-15 | 21577 | 2 | 3 | | III-2 | Tmem261 | 90871 | 21-May-15 |
| 21087 | 2 | 3 | | | III-2 | Tdp2 | 51567 | 3-May-15 | 21578 | 2 | 3 | | III-2 | Tmem263 | 90488 | 4-May-15 |
| 21098 | 2 | 3 | | | III-2 | Tdrd7 | 23424 | 4-May-15 | 21580 | 2 | 3 | | III-2 | Tmem28 | 27112 | 4-May-15 |
| 21100 | 2 | 3 | | | III-2 | Tdrkh | 11022 | 4-May-15 | 21582 | 2 | 3 | | III-2 | Tmem30a | 55754 | 3-May-15 |
| 21104 | 2 | 3 | | | III-2 | Tead3 | 7005 | 4-May-15 | | | | | | | | |
| 21107 | 2 | 3 | | | III-2 | Tecpr1 | 25851 | 21-May-15 | | | | | | | | |

Fig.22 - 55

| | | | | | | | | | | | | | | | | |
|---|---|---|---|---|---|---|---|---|---|---|---|---|---|---|---|---|
| 21585 | 2 | 3 | | | III-2 | Tmem33 | 55161 | 1-Jun-15 | 22138 | 2 | 3 | | | III-2 | Tstd3 | 100130890 | 12-May-15 |
| 21595 | 2 | 3 | | | III-2 | Tmem42 | 131616 | 4-May-15 | 22142 | 2 | 3 | | | III-2 | Ttc1 | 7265 | 4-May-15 |
| 21611 | 2 | 3 | | | III-2 | Tmem55b | 90809 | 4-May-15 | 22147 | 2 | 3 | | | III-2 | Ttc17 | 55761 | 12-May-15 |
| 21617 | 2 | 3 | | | III-2 | Tmem62 | 80021 | 4-May-15 | 22158 | 2 | 3 | | | III-2 | Ttc27 | 55622 | 12-May-15 |
| 21619 | 2 | 3 | | | III-2 | Tmem63b | 55362 | 4-May-15 | 22161 | 2 | 3 | | | III-2 | Ttc3 | 7267 | 12-May-15 |
| 21624 | 2 | 3 | | | III-2 | Tmem67 | 91147 | 23-May-15 | 22167 | 2 | 3 | | | III-2 | Ttc34 | 100287898 | 4-May-15 |
| 21628 | 2 | 3 | | | III-2 | Tmem71 | 137835 | 4-May-15 | 22171 | 2 | 3 | | | III-2 | Ttc39a | 22996 | 12-May-15 |
| 21630 | 2 | 3 | | | III-2 | Tmem74 | 157753 | 21-May-15 | 22173 | 2 | 3 | | | III-2 | Ttc39c | 125488 | 12-May-15 |
| 21635 | 2 | 3 | | | III-2 | Tmem81 | 388730 | 4-May-15 | 22175 | 2 | 3 | | | III-2 | Ttc4 | 7268 | 4-May-15 |
| 21640 | 2 | 3 | | | III-2 | Tmem87b | 84910 | 4-May-15 | 22184 | 2 | 3 | | | III-2 | Tti2 | 8458 | 7-Jun-15 |
| 21641 | 2 | 3 | | | III-2 | Tmem88 | 92162 | 4-May-15 | 22186 | 2 | 3 | | | III-2 | Tti2 | 80185 | 4-May-15 |
| 21653 | 2 | 3 | | | III-2 | Tmevpg1 | 100885789 | 1-May-15 | 22201 | 2 | 3 | | | III-2 | Ttll9 | 164395 | 4-May-15 |
| 21663 | 2 | 3 | | | III-2 | Tmppe | 643853 | 4-May-15 | 22210 | 2 | 3 | | | III-2 | Tuba1a | 7846 | 4-May-15 |
| 21677 | 2 | 3 | | | III-2 | Tmprss5 | 80975 | 12-May-15 | 22218 | 2 | 3 | | | III-2 | Tubb1 | 81027 | 7-Jun-15 |
| 21679 | 2 | 3 | | | III-2 | Tmprss7 | 344805 | 12-May-15 | 22225 | 2 | 3 | | | III-2 | Tubb5 | 203068 | 7-Jun-15 |
| 21681 | 2 | 3 | | | III-2 | Tmsb10 | 9168 | 21-May-15 | 22226 | 2 | 3 | | | III-2 | Tubb6 | 84617 | 12-May-15 |
| 21690 | 2 | 3 | | | III-2 | Tnfc4 | 84899 | 4-May-15 | 22228 | 2 | 3 | | | III-2 | Tube1 | 51175 | 4-May-15 |
| 21692 | 2 | 3 | | | III-2 | Tmub2 | 79089 | 4-May-15 | 22230 | 2 | 3 | | | III-2 | Tubg2 | 27175 | 14-May-15 |
| 21707 | 2 | 3 | | | III-2 | Tnfrsf10b | 8795 | 17-May-15 | 22233 | 2 | 3 | | | III-2 | Tubgcp4 | 27229 | 30-May-15 |
| 21708 | 2 | 3 | | | III-2 | Tnfrsf11a | 8792 | 31-May-15 | 22235 | 2 | 3 | | | III-2 | Tubgcp6 | 85378 | 4-May-15 |
| 21721 | 2 | 3 | | | III-2 | Tnfrsf23 | | | 22243 | 2 | 3 | | | III-2 | Tunar | 100507043 | 16-May-15 |
| 21735 | 2 | 3 | | | III-2 | Tnfsf18 | 8995 | 30-Apr-15 | 22249 | 2 | 3 | | | III-2 | Tvp23a | 780776 | 4-May-15 |
| 21737 | 2 | 3 | | | III-2 | Tnfsf8 | 944 | 17-May-15 | 22261 | 2 | 3 | | | III-2 | Txn1 | | |
| 21764 | 2 | 3 | | | III-2 | Tnpo3 | 23534 | 4-May-15 | 22280 | 2 | 3 | | | III-2 | Tymp | 1890 | 23-May-15 |
| 21770 | 2 | 3 | | | III-2 | Tns1 | 7145 | 12-May-15 | 22288 | 2 | 3 | | | III-2 | Tyw1 | 55253 | 4-May-15 |
| 21782 | 2 | 3 | | | III-2 | Tomm20l | 387990 | 4-May-15 | 22289 | 2 | 3 | | | III-2 | Tyw3 | 127253 | 21-May-15 |
| 21792 | 2 | 3 | | | III-2 | Tomt | | | 22293 | 2 | 3 | | | III-2 | U2af2 | 11338 | 21-May-15 |
| 21794 | 2 | 3 | | | III-2 | Top1 | 7150 | 12-May-15 | 22294 | 2 | 3 | | | III-2 | U2surp | 23350 | 4-May-15 |
| 21795 | 2 | 3 | | | III-2 | Top1mt | 116447 | 14-May-15 | 22296 | 2 | 3 | | | III-2 | Uaca | 55075 | 4-May-15 |
| 21798 | 2 | 3 | | | III-2 | Top3a | 7156 | 4-May-15 | 22297 | 2 | 3 | | | III-2 | Uap1 | 6675 | 4-May-15 |
| 21803 | 2 | 3 | | | III-2 | Toporsl | | | 22300 | 2 | 3 | | | III-2 | Uba1y | | |
| 21806 | 2 | 3 | | | III-2 | Tor1aip1 | 26092 | 4-May-15 | 22312 | 2 | 3 | | | III-2 | Ubap1l | 390595 | 4-May-15 |
| 21818 | 2 | 3 | | | III-2 | Tpbpb | | | 22314 | 2 | 3 | | | III-2 | Ubap2l | 9898 | 4-May-15 |
| 21824 | 2 | 3 | | | III-2 | Tpgs1 | 91978 | 12-May-15 | 22318 | 2 | 3 | | | III-2 | Ubc | 7316 | 7-Jun-15 |
| 21826 | 2 | 3 | | | III-2 | Tph1 | 7166 | 3-May-15 | 22321 | 2 | 3 | | | III-2 | ube2b | 7320 | 12-May-15 |
| 21828 | 2 | 3 | | | III-2 | Tpi1 | 7167 | 4-May-15 | 22326 | 2 | 3 | | | III-2 | Ube2d2b | | |
| 21833 | 2 | 3 | | | III-2 | Tpm4 | 7171 | 14-May-15 | 22333 | 2 | 3 | | | III-2 | Ube2f | 140739 | 2-Jun-15 |
| 21843 | 2 | 3 | | | III-2 | Tprg | | | 22341 | 2 | 3 | | | III-2 | Ube2l3 | 7332 | 3-May-15 |
| 21847 | 2 | 3 | | | III-2 | Tpsab1 | 7177 | 12-May-15 | 22353 | 2 | 3 | | | III-2 | Ube2v1 | 7335 | 3-Jun-15 |
| 21850 | 2 | 3 | | | III-2 | Tpst1 | 8460 | 21-May-15 | 22363 | 2 | 3 | | | III-2 | Ubiad1 | 29914 | 23-May-15 |
| 21856 | 2 | 3 | | | III-2 | Tra2b | 6434 | 17-May-15 | 22365 | 2 | 3 | | | III-2 | Ubl4 | 8266 | 29-May-15 |
| 21857 | 2 | 3 | | | III-2 | Trabd | 80305 | 4-May-15 | 22370 | 2 | 3 | | | III-2 | Ubn1 | 29855 | 12-May-15 |
| 21860 | 2 | 3 | | | III-2 | Traf1 | 7185 | 4-May-15 | 22373 | 2 | 3 | | | III-2 | Ubp1 | 7342 | 4-May-15 |
| 21862 | 2 | 3 | | | III-2 | Traf3 | 7187 | 29-May-15 | 22385 | 2 | 3 | | | III-2 | Ubtd1 | 80019 | 28-May-15 |
| 21864 | 2 | 3 | | | III-2 | Traf3ip2 | 10758 | 13-May-15 | 22387 | 2 | 3 | | | III-2 | Ubtf | 7343 | 12-May-15 |
| 21866 | 2 | 3 | | | III-2 | Traf4 | 9618 | 21-May-15 | 22388 | 2 | 3 | | | III-2 | Ubtfl1 | 642623 | 4-May-15 |
| 21869 | 2 | 3 | | | III-2 | Traf7 | 84231 | 4-May-15 | 22395 | 2 | 3 | | | III-2 | Ubxn6 | 80700 | 4-May-15 |
| 21870 | 2 | 3 | | | III-2 | Trafd1 | 10906 | 12-May-15 | 22398 | 2 | 3 | | | III-2 | Uchl1 | 7345 | 12-May-15 |
| 21873 | 2 | 3 | | | III-2 | Trak2 | 66008 | 4-May-15 | 22399 | 2 | 3 | | | III-2 | Uchl1os | | |
| 21879 | 2 | 3 | | | III-2 | Trap1a | | | 22400 | 2 | 3 | | | III-2 | Uchl3 | 7347 | 12-May-15 |
| 21888 | 2 | 3 | | | III-2 | Trappc3l | 100128327 | 7-Jun-15 | 22404 | 2 | 3 | | | III-2 | Uck2 | 7371 | 4-May-15 |
| 21891 | 2 | 3 | | | III-2 | Trappc6a | 79090 | 4-May-15 | 22405 | 2 | 3 | | | III-2 | uckl1 | 54963 | 4-May-15 |
| 21897 | 2 | 3 | | | III-2 | Trdmt1 | 1787 | 12-May-15 | 22415 | 2 | 3 | | | III-2 | Ufc1 | 51506 | 12-May-15 |
| 21906 | 2 | 3 | | | III-2 | Trerf1 | 55809 | 28-May-15 | 22421 | 2 | 3 | | | III-2 | Ugcg | 7357 | 4-May-15 |
| 21907 | 2 | 3 | | | III-2 | Trex1 | 11277 | 23-May-15 | 22424 | 2 | 3 | | | III-2 | Uggt2 | 55757 | 4-May-15 |
| 21913 | 2 | 3 | | | III-2 | Trhde | 29953 | 4-May-15 | 22442 | 2 | 3 | | | III-2 | Ugt2b38 | | |
| 21915 | 2 | 3 | | | III-2 | Trib1 | 10221 | | 22450 | 2 | 3 | | | III-2 | Uhrf1bp1l | 23074 | 4-May-15 |
| 21921 | 2 | 3 | | | III-2 | Trim12a | | | 22455 | 2 | 3 | | | III-2 | Ulk2 | 9706 | 21-May-15 |
| 21928 | 2 | 3 | | | III-2 | Trim2 | 23321 | 4-May-15 | 22457 | 2 | 3 | | | III-2 | Ulk4 | 54986 | 4-May-15 |
| 21933 | 2 | 3 | | | III-2 | Trim26 | 7726 | 4-May-15 | 22473 | 2 | 3 | | | III-2 | Unc5cl | 222643 | 4-May-15 |
| 21942 | 2 | 3 | | | III-2 | Trim31 | 11074 | 7-Jun-15 | 22482 | 2 | 3 | | | III-2 | Unkl | 64718 | 4-May-15 |
| 21950 | 2 | 3 | | | III-2 | Trim38 | 10475 | 12-May-15 | 22495 | 2 | 3 | | | III-2 | Upp1 | 7378 | 4-May-15 |
| 21952 | 2 | 3 | | | III-2 | Trim40 | 135644 | 7-Jun-15 | 22513 | 2 | 3 | | | III-2 | Uri1 | 8725 | 24-May-15 |
| 21954 | 2 | 3 | | | III-2 | Trim42 | 287015 | 4-May-15 | 22519 | 2 | 3 | | | III-2 | Use1 | 55850 | 7-Jun-15 |
| 21963 | 2 | 3 | | | III-2 | Trim52 | 84851 | 12-May-15 | 22524 | 2 | 3 | | | III-2 | Ush2a | 7399 | 23-May-15 |
| 21970 | 2 | 3 | | | III-2 | Trim60 | 166655 | 4-May-15 | 22525 | 2 | 3 | | | III-2 | Ushbp1 | 83878 | 12-May-15 |
| 21971 | 2 | 3 | | | III-2 | Trim61 | 391712 | 4-May-15 | 22528 | 2 | 3 | | | III-2 | Usp1 | 7398 | 4-May-15 |
| 21976 | 2 | 3 | | | III-2 | Trim67 | 440730 | 4-May-15 | 22530 | 2 | 3 | | | III-2 | Usp11 | 8237 | 21-May-15 |
| 21983 | 2 | 3 | | | III-2 | Trim8 | 81603 | 4-May-15 | 22534 | 2 | 3 | | | III-2 | Usp15 | 9958 | 2-Jun-15 |
| 21985 | 2 | 3 | | | III-2 | Triml1 | 339376 | 4-May-15 | 22546 | 2 | 3 | | | III-2 | Usp22 | 23326 | 21-May-15 |
| 21989 | 2 | 3 | | | III-2 | Trip10 | 9322 | 4-May-15 | 22557 | 2 | 3 | | | III-2 | Usp33 | 23032 | 21-May-15 |
| 21992 | 2 | 3 | | | III-2 | Trip13 | 9319 | 4-May-15 | 22561 | 2 | 3 | | | III-2 | Usp37 | 57695 | 4-May-15 |
| 21994 | 2 | 3 | | | III-2 | Trip6 | 7205 | 12-May-15 | 22575 | 2 | 3 | | | III-2 | Usp50 | 373509 | 12-May-15 |
| 22004 | 2 | 3 | | | III-2 | Trmt13 | 54482 | 4-May-15 | 22581 | 2 | 3 | | | III-2 | Usp8 | 9101 | 12-May-15 |
| 22006 | 2 | 3 | | | III-2 | Trmt2a | 27037 | 4-May-15 | 22591 | 2 | 3 | | | III-2 | Utp18 | 51096 | 4-May-15 |
| 22037 | 2 | 3 | | | III-2 | Trpc4ap | 26133 | 12-May-15 | 22605 | 2 | 3 | | | III-2 | V1ra8 | | |
| 22038 | 2 | 3 | | | III-2 | Trpc5 | 7224 | 4-May-15 | 22615 | 2 | 3 | | | III-2 | Vamp8 | 8673 | 28-May-15 |
| 22042 | 2 | 3 | | | III-2 | Trpd52l3 | | | 22616 | 2 | 3 | | | III-2 | Vangl1 | 81839 | 4-May-15 |
| 22049 | 2 | 3 | | | III-2 | Trpm7 | 54822 | 4-May-15 | 22619 | 2 | 3 | | | III-2 | Vapb | 9217 | 23-May-15 |
| 22051 | 2 | 3 | | | III-2 | Trps1 | 7227 | 4-May-15 | 22639 | 2 | 3 | | | III-2 | Vcp | 7415 | 29-May-15 |
| 22054 | 2 | 3 | | | III-2 | Trpv2 | 51393 | 4-May-15 | 22650 | 2 | 3 | | | III-2 | Vezf1 | 7716 | 4-May-15 |
| 22060 | 2 | 3 | | | III-2 | Trub1 | 142940 | 12-May-15 | 22651 | 2 | 3 | | | III-2 | Vezt | 55591 | 4-May-15 |
| 22075 | 2 | 3 | | | III-2 | Tsen54 | 283989 | 23-May-15 | 22658 | 2 | 3 | | | III-2 | Vill | 7429 | 12-May-15 |
| 22086 | 2 | 3 | | | III-2 | Tsix | 9383 | 12-May-15 | 22659 | 2 | 3 | | | III-2 | Vill | 50853 | 12-May-15 |
| 22087 | 2 | 3 | | | III-2 | Tsks | 60385 | 4-May-15 | 22661 | 2 | 3 | | | III-2 | Vimp | 55829 | 29-May-15 |
| 22091 | 2 | 3 | | | III-2 | Tsnax | 7257 | 12-May-15 | 22664 | 2 | 3 | | | III-2 | Vipr1 | 7433 | 12-May-15 |
| 22095 | 2 | 3 | | | III-2 | Tspan11 | 441631 | 12-May-15 | 22671 | 2 | 3 | | | III-2 | Vmac | 400673 | 4-May-15 |
| 22099 | 2 | 3 | | | III-2 | Tspan15 | 23555 | 4-May-15 | 22924 | 2 | 3 | | | III-2 | Vmn2r30 | | |
| 22104 | 2 | 3 | | | III-2 | Tspan3 | 10099 | 4-May-15 | 23014 | 2 | 3 | | | III-2 | Vps13a | 23230 | 23-May-15 |
| 22106 | 2 | 3 | | | III-2 | Tspan32 | 10077 | 4-May-15 | 23018 | 2 | 3 | | | III-2 | Vps16 | 64601 | 21-May-15 |
| 22115 | 2 | 3 | | | III-2 | Tspo | 706 | 12-May-15 | 23025 | 2 | 3 | | | III-2 | Vps33a | 65082 | 4-May-15 |
| 22117 | 2 | 3 | | | III-2 | Tspyl1 | 7259 | 4-May-15 | 23027 | 2 | 3 | | | III-2 | Vps35 | 55737 | 23-May-15 |
| 22123 | 2 | 3 | | | III-2 | Tsr1 | 55720 | 12-May-15 | 23034 | 2 | 3 | | | III-2 | Vps41 | 27072 | 7-Jun-15 |
| 22125 | 2 | 3 | | | III-2 | Tsr3 | 115939 | 4-May-15 | 23035 | 2 | 3 | | | III-2 | Vps45 | 11311 | 4-May-15 |
| 22127 | 2 | 3 | | | III-2 | Tssc4 | 10078 | 12-May-15 | 23037 | 2 | 3 | | | III-2 | Vps4b | 9525 | 31-May-15 |
| 22128 | 2 | 3 | | | III-2 | Tssk1 | 83942 | 7-Jun-15 | | | | | | | | | |

Fig.22 - 56

| | | | | | | | | | | | | | | | |
|---|---|---|---|---|---|---|---|---|---|---|---|---|---|---|---|
| 23045 | 2 | 3 | | III-2 | Vrk1 | 7443 | 4-May-15 | 23511 | 2 | 3 | | III-2 | Zfp111 | | |
| 23048 | 2 | 3 | | III-2 | Vrtn | 55237 | 4-May-15 | 23515 | 2 | 3 | | III-2 | Zfp119a | | |
| 23049 | 2 | 3 | | III-2 | Vsig1 | 340547 | 4-May-15 | 23519 | 2 | 3 | | III-2 | Zfp128 | 7554 | 4-May-15 |
| 23056 | 2 | 3 | | III-2 | Vstm2a | 222008 | 4-May-15 | 23524 | 2 | 3 | | III-2 | Zfp142 | | |
| 23073 | 2 | 3 | | III-2 | Vwa5b2 | 90113 | 4-May-15 | 23526 | 2 | 3 | | III-2 | Zfp146 | | |
| 23076 | 2 | 3 | | III-2 | Vwa9 | 81556 | 4-May-15 | 23532 | 2 | 3 | | III-2 | Zfp180 | | |
| 23077 | 2 | 3 | | III-2 | Vwc2 | 375567 | 4-May-15 | 23533 | 2 | 3 | | III-2 | Zfp182 | 7569 | 4-May-15 |
| 23083 | 2 | 3 | | III-2 | Wap | | | 23538 | 2 | 3 | | III-2 | Zfp2 | 80108 | 4-May-15 |
| 23089 | 2 | 3 | | III-2 | Wasf2 | 10163 | 4-May-15 | 23539 | 2 | 3 | | III-2 | Zfp202 | | |
| 23093 | 2 | 3 | | III-2 | Wbp1 | 23559 | 7-Jun-15 | 23543 | 2 | 3 | | III-2 | Zfp217 | | |
| 23095 | 2 | 3 | | III-2 | Wbp1l | 54838 | 4-May-15 | 23544 | 2 | 3 | | III-2 | Zfp219 | 51222 | 4-May-15 |
| 23116 | 2 | 3 | | III-2 | Wdr16 | 146845 | 4-May-15 | 23545 | 2 | 3 | | III-2 | Zfp229 | | |
| 23143 | 2 | 3 | | III-2 | Wdr5 | 11091 | 4-May-15 | 23547 | 2 | 3 | | III-2 | Zfp236 | | |
| 23151 | 2 | 3 | | III-2 | Wdr60 | 55112 | 4-May-15 | 23548 | 2 | 3 | | III-2 | Zfp239 | | |
| 23156 | 2 | 3 | | III-2 | Wdr65 | 149485 | 12-May-15 | 23552 | 2 | 3 | | III-2 | Zfp260 | 339324 | 4-May-15 |
| 23163 | 2 | 3 | | III-2 | Wdr76 | 79968 | 4-May-15 | 23553 | 2 | 3 | | III-2 | Zfp263 | | |
| 23165 | 2 | 3 | | III-2 | Wdr78 | 79819 | 4-May-15 | 23556 | 2 | 3 | | III-2 | Zfp273 | | |
| 23167 | 2 | 3 | | III-2 | Wdr81 | 124897 | 4-May-15 | 23560 | 2 | 3 | | III-2 | Zfp28 | 140612 | 12-May-15 |
| 23158 | 2 | 3 | | III-2 | Wdr82 | 80335 | 10-Jun-15 | 23564 | 2 | 3 | | III-2 | Zfp281 | | |
| 23159 | 2 | 3 | | III-2 | Wdr83 | 84292 | 4-May-15 | 23565 | 2 | 3 | | III-2 | Zfp282 | | |
| 23176 | 2 | 3 | | III-2 | Wdr93 | 56964 | 4-May-15 | 23566 | 2 | 3 | | III-2 | Zfp286 | | |
| 23178 | 2 | 3 | | III-2 | Wdr96 | 80217 | 4-May-15 | 23568 | 2 | 3 | | III-2 | Zfp292 | 23036 | 28-May-15 |
| 23207 | 2 | 3 | | III-2 | Whsc1l1 | 54904 | 7-May-15 | 23570 | 2 | 3 | | III-2 | Zfp3 | 124961 | 4-May-15 |
| 23208 | 2 | 3 | | III-2 | Wibg | 84305 | 4-May-15 | 23575 | 2 | 3 | | III-2 | Zfp318 | 24149 | 4-May-15 |
| 23211 | 2 | 3 | | III-2 | Wipf2 | 147179 | 10-May-15 | 23577 | 2 | 3 | | III-2 | Zfp322a | | |
| 23215 | 2 | 3 | | III-2 | Wisp1 | 8840 | 17-May-15 | 23578 | 2 | 3 | | III-2 | Zfp324 | | |
| 23218 | 2 | 3 | | III-2 | Wiz | 58825 | 4-May-15 | 23580 | 2 | 3 | | III-2 | Zfp329 | | |
| 23232 | 2 | 3 | | III-2 | Wnt3a | 89780 | 17-May-15 | 23582 | 2 | 3 | | III-2 | Zfp334 | | |
| 23240 | 2 | 3 | | III-2 | Wnt8b | 7479 | 4-May-15 | 23602 | 2 | 3 | | III-2 | Zfp37 | 7539 | 4-May-15 |
| 23243 | 2 | 3 | | III-2 | Wrap53 | 55135 | 23-May-15 | 23609 | 2 | 3 | | III-2 | Zfp386 | | |
| 23245 | 2 | 3 | | III-2 | Wrn | 7486 | 23-May-15 | 23614 | 2 | 3 | | III-2 | Zfp398 | | |
| 23249 | 2 | 3 | | III-2 | Wscd1 | 23302 | 4-May-15 | 23616 | 2 | 3 | | III-2 | Zfp407 | | |
| 23251 | 2 | 3 | | III-2 | Wt1 | 7490 | 24-May-15 | 23621 | 2 | 3 | | III-2 | Zfp418 | | |
| 23252 | 2 | 3 | | III-2 | Wt1os | | | 23622 | 2 | 3 | | III-2 | Zfp42 | 132825 | 12-May-15 |
| 23253 | 2 | 3 | | III-2 | Wtap | 9589 | 4-May-15 | 23623 | 2 | 3 | | III-2 | Zfp420 | | |
| 23259 | 2 | 3 | | III-2 | Wwp2 | 11060 | 23-May-15 | 23625 | 2 | 3 | | III-2 | Zfp423 | 23090 | 20-May-15 |
| 23262 | 2 | 3 | | III-2 | Xaf1 | 54739 | 4-May-15 | 23626 | 2 | 3 | | III-2 | Zfp426 | | |
| 23273 | 2 | 3 | | III-2 | Xkr5 | 389810 | 4-May-15 | 23627 | 2 | 3 | | III-2 | Zfp428 | 126299 | 4-May-15 |
| 23275 | 2 | 3 | | III-2 | Xkr7 | 343702 | 4-May-15 | 23630 | 2 | 3 | | III-2 | Zfp438 | | |
| 23276 | 2 | 3 | | III-2 | Xkr8 | 55113 | 4-May-15 | 23631 | 2 | 3 | | III-2 | Zfp442 | | |
| 23277 | 2 | 3 | | III-2 | Xkr9 | 389665 | 4-May-15 | 23633 | 2 | 3 | | III-2 | Zfp445 | | |
| 23285 | 2 | 3 | | III-2 | Xlr4c | | | 23635 | 2 | 3 | | III-2 | Zfp449 | | |
| 23286 | 2 | 3 | | III-2 | Xlr5a | | | 23639 | 2 | 3 | | III-2 | Zfp456 | | |
| 23297 | 2 | 3 | | III-2 | Xpo4 | 64328 | 4-May-15 | 23641 | 2 | 3 | | III-2 | Zfp458 | | |
| 23312 | 2 | 3 | | III-2 | Xrra1 | 143570 | 4-May-15 | 23644 | 2 | 3 | | III-2 | Zfp462 | 58499 | 4-May-15 |
| 23317 | 2 | 3 | | III-2 | Yae1d1 | 57602 | 12-May-15 | 23647 | 2 | 3 | | III-2 | Zfp473 | | |
| 23319 | 2 | 3 | | III-2 | Yap1 | 10413 | 31-May-15 | 23650 | 2 | 3 | | III-2 | Zfp493 | | |
| 23324 | 2 | 3 | | III-2 | Ybx2 | 51087 | 4-May-15 | 23653 | 2 | 3 | | III-2 | Zfp51 | | |
| 23328 | 2 | 3 | | III-2 | Yeats4 | 8089 | 4-May-15 | 23668 | 2 | 3 | | III-2 | Zfp536 | | |
| 23331 | 2 | 3 | | III-2 | Yif1b | 90522 | 4-May-15 | 23671 | 2 | 3 | | III-2 | Zfp551 | | |
| 23332 | 2 | 3 | | III-2 | Yipf1 | 54432 | 28-May-15 | 23680 | 2 | 3 | | III-2 | Zfp574 | | |
| 23340 | 2 | 3 | | III-2 | Yipm1 | 96262 | 12-May-15 | 23687 | 2 | 3 | | III-2 | Zfp592 | | |
| 23348 | 2 | 3 | | III-2 | Yrdc | 79693 | 4-May-15 | 23688 | 2 | 3 | | III-2 | Zfp593 | | |
| 23352 | 2 | 3 | | III-2 | Ythdf2 | 51441 | 4-May-15 | 23694 | 2 | 3 | | III-2 | Zfp600 | | |
| 23363 | 2 | 3 | | III-2 | Zak | 51776 | 4-May-15 | 23697 | 2 | 3 | | III-2 | Zfp607 | | |
| 23371 | 2 | 3 | | III-2 | Zbed5 | 58486 | 4-May-15 | 23703 | 2 | 3 | | III-2 | Zfp617 | | |
| 23375 | 2 | 3 | | III-2 | Zbtb10 | 65986 | 4-May-15 | 23706 | 2 | 3 | | III-2 | Zfp62 | 643836 | 4-May-15 |
| 23376 | 2 | 3 | | III-2 | Zbtb11 | 27107 | 12-May-15 | 23708 | 2 | 3 | | III-2 | Zfp623 | | |
| 23381 | 2 | 3 | | III-2 | Zbtb18 | 10472 | 4-May-15 | 23716 | 2 | 3 | | III-2 | Zfp646 | | |
| 23385 | 2 | 3 | | III-2 | Zbtb22 | 9278 | 4-May-15 | 23717 | 2 | 3 | | III-2 | Zfp647 | 58500 | 4-May-15 |
| 23389 | 2 | 3 | | III-2 | Zbtb3 | 79842 | 4-May-15 | 23726 | 2 | 3 | | III-2 | Zfp658 | | |
| 23392 | 2 | 3 | | III-2 | Zbtb34 | 403341 | 1-Jun-15 | 23727 | 2 | 3 | | III-2 | Zfp661 | 7549 | 12-May-15 |
| 23397 | 2 | 3 | | III-2 | Zbtb40 | 9923 | 4-May-15 | 23728 | 2 | 3 | | III-2 | Zfp663 | | |
| 23403 | 2 | 3 | | III-2 | Zbtb46 | 140685 | 28-May-15 | 23733 | 2 | 3 | | III-2 | Zfp677 | | |
| 23405 | 2 | 3 | | III-2 | Zbtb49 | 166793 | 28-May-15 | 23735 | 2 | 3 | | III-2 | Zfp687 | | |
| 23406 | 2 | 3 | | III-2 | Zbtb5 | 9925 | 4-May-15 | 23746 | 2 | 3 | | III-2 | Zfp707 | | |
| 23407 | 2 | 3 | | III-2 | Zbtb6 | 10773 | 4-May-15 | 23749 | 2 | 3 | | III-2 | Zfp710 | | |
| 23408 | 2 | 3 | | III-2 | Zbtb7a | 51341 | 4-May-15 | 23750 | 2 | 3 | | III-2 | Zfp711 | 7552 | 4-May-15 |
| 23415 | 2 | 3 | | III-2 | Zbtb6 | | | 23751 | 2 | 3 | | III-2 | Zfp712 | | |
| 23417 | 2 | 3 | | III-2 | Zc2hc1b | 153918 | 4-May-15 | 23753 | 2 | 3 | | III-2 | Zfp719 | | |
| 23420 | 2 | 3 | | III-2 | Zc3h11a | 9877 | 4-May-15 | 23758 | 2 | 3 | | III-2 | Zfp740 | 283337 | 4-May-15 |
| 23426 | 2 | 3 | | III-2 | Zc3h14 | 79882 | 4-May-15 | 23759 | 2 | 3 | | III-2 | Zfp746 | | |
| 23433 | 2 | 3 | | III-2 | Zc3h7b | 28264 | 4-May-15 | 23764 | 2 | 3 | | III-2 | Zfp759 | | |
| 23436 | 2 | 3 | | III-2 | Zc3hav1l | 92092 | 21-May-15 | 23765 | 2 | 3 | | III-2 | Zfp760 | | |
| 23437 | 2 | 3 | | III-2 | Zc3hc1 | 51530 | 4-May-15 | 23766 | 2 | 3 | | III-2 | Zfp763 | | |
| 23438 | 2 | 3 | | III-2 | Zc4h2 | 56906 | 4-May-15 | 23767 | 2 | 3 | | III-2 | Zfp764 | | |
| 23440 | 2 | 3 | | III-2 | Zcchc11 | 23318 | 4-May-15 | 23768 | 2 | 3 | | III-2 | Zfp768 | | |
| 23448 | 2 | 3 | | III-2 | Zcchc24 | 219654 | 4-May-15 | 23775 | 2 | 3 | | III-2 | Zfp78 | | |
| 23450 | 2 | 3 | | III-2 | Zcchc4 | 29063 | 4-May-15 | 23778 | 2 | 3 | | III-2 | Zfp783 | | |
| 23451 | 2 | 3 | | III-2 | Zcchc5 | 203430 | 4-May-15 | 23781 | 2 | 3 | | III-2 | Zfp787 | | |
| 23452 | 2 | 3 | | III-2 | Zcchc6 | 79670 | 12-May-15 | 23786 | 2 | 3 | | III-2 | Zfp800 | | |
| 23454 | 2 | 3 | | III-2 | Zcchc8 | 55596 | 27-May-15 | 23787 | 2 | 3 | | III-2 | Zfp804a | | |
| 23464 | 2 | 3 | | III-2 | Zdhhc15 | 158866 | 23-May-15 | 23788 | 2 | 3 | | III-2 | Zfp804b | | |
| 23465 | 2 | 3 | | III-2 | Zdhhc16 | 84287 | 12-May-15 | 23799 | 2 | 3 | | III-2 | Zfp825 | | |
| 23469 | 2 | 3 | | III-2 | Zdhhc2 | 51261 | 4-May-15 | 23802 | 2 | 3 | | III-2 | Zfp839 | | |
| 23475 | 2 | 3 | | III-2 | Zdhhc25 | | | 23807 | 2 | 3 | | III-2 | Zfp85os | | |
| 23476 | 2 | 3 | | III-2 | Zdhhc3 | 51304 | 4-May-15 | 23808 | 2 | 3 | | III-2 | Zfp862-ps | | |
| 23479 | 2 | 3 | | III-2 | Zdhhc6 | 64429 | 12-May-15 | 23810 | 2 | 3 | | III-2 | Zfp866 | | |
| 23490 | 2 | 3 | | III-2 | Zfand2b | 130617 | 4-May-15 | 23811 | 2 | 3 | | III-2 | Zfp867 | | |
| 23491 | 2 | 3 | | III-2 | Zfand3 | 60885 | 4-May-15 | 23817 | 2 | 3 | | III-2 | Zfp872 | | |
| 23492 | 2 | 3 | | III-2 | Zfand4 | 93850 | 4-May-15 | 23821 | 2 | 3 | | III-2 | Zfp879 | | |
| 23494 | 2 | 3 | | III-2 | Zfand6 | 54469 | 4-May-15 | 23822 | 2 | 3 | | III-2 | Zfp882 | | |
| 23498 | 2 | 3 | | III-2 | Zfhx2 | 85446 | 4-May-15 | 23832 | 2 | 3 | | III-2 | Zfp933 | | |
| 23502 | 2 | 3 | | III-2 | Zfml | 27332 | 4-May-15 | 23833 | 2 | 3 | | III-2 | Zfp934 | | |
| 23503 | 2 | 3 | | III-2 | Zfp1 | 162239 | 12-May-15 | 23835 | 2 | 3 | | III-2 | Zfp936 | | |
| 23509 | 2 | 3 | | III-2 | Zfp11 | | | 23836 | 2 | 3 | | III-2 | Zfp937 | | |
| 23510 | 2 | 3 | | III-2 | Zfp110 | | | 23838 | 2 | 3 | | III-2 | Zfp939 | | |

Fig.22 - 57

| | | | | | | | | | | | | | |
|---|---|---|---|---|---|---|---|---|---|---|---|---|---|
| 23840 | 2 | 3 | | III-2 | Zfp940 | | | 250 | 2 | 3 | | III-1 | 1700028M03Rik |
| 23844 | 2 | 3 | | III-2 | Zfp944 | | | 251 | 2 | 3 | | III-1 | 1700028P14Rik |
| 23848 | 2 | 3 | | III-2 | Zfp946 | | | 255 | 2 | 3 | | III-1 | 1700029H14Rik |
| 23852 | 2 | 3 | | III-2 | Zfp953 | | | 259 | 2 | 3 | | III-1 | 1700029M20Rik |
| 23855 | 2 | 3 | | III-2 | Zfp955b | | | 264 | 2 | 3 | | III-1 | 1700030F04Rik |
| 23856 | 2 | 3 | | III-2 | Zfp956 | | | 271 | 2 | 3 | | III-1 | 1700030O20Rik |
| 23858 | 2 | 3 | | III-2 | Zfp958 | | | 284 | 2 | 3 | | III-1 | 1700034P13Rik |
| 23868 | 2 | 3 | | III-2 | Zfr | 51663 | 12-May-15 | 287 | 2 | 3 | | III-1 | 1700037H04Rik |
| 23871 | 2 | 3 | | III-2 | Zfy1 | | | 288 | 2 | 3 | | III-1 | 1700039E15Rik |
| 23872 | 2 | 3 | | III-2 | Zfy2 | | | 292 | 2 | 3 | | III-1 | 1700041M19Rik |
| 23876 | 2 | 3 | | III-2 | Zfyve20 | 64145 | 12-May-15 | 297 | 2 | 3 | | III-1 | 1700044C05Rik |
| 23877 | 2 | 3 | | III-2 | Zfyve21 | 79038 | 21-May-15 | 300 | 2 | 3 | | III-1 | 1700046C09Rik |
| 23884 | 2 | 3 | | III-2 | Zgpat | 84619 | 12-May-15 | 305 | 2 | 3 | | III-1 | 1700047L14Rik |
| 23887 | 2 | 3 | | III-2 | Zhx2 | 22882 | 31-May-15 | 328 | 2 | 3 | | III-1 | 1700061F12Rik |
| 23890 | 2 | 3 | | III-2 | Zic2 | 7546 | 2-Jun-15 | 339 | 2 | 3 | | III-1 | 1700065J18Rik |
| 23891 | 2 | 3 | | III-2 | Zic3 | 7547 | 28-May-15 | 344 | 2 | 3 | | III-1 | 1700066M21Rik |
| 23893 | 2 | 3 | | III-2 | Zic5 | 85416 | 4-May-15 | 349 | 2 | 3 | | III-1 | 1700067P10Rik |
| 23897 | 2 | 3 | | III-2 | Zkscan1 | 7586 | 4-May-15 | 355 | 2 | 3 | | III-1 | 1700072O05Rik |
| 23903 | 2 | 3 | | III-2 | Zkscan4 | 387032 | 20-May-15 | 358 | 2 | 3 | | III-1 | 1700074P13Rik |
| 23904 | 2 | 3 | | III-2 | Zkscan5 | 23680 | 12-May-15 | 367 | 2 | 3 | | III-1 | 1700085C21Rik |
| 23906 | 2 | 3 | | III-2 | Zkscan7 | 55868 | 4-May-15 | 370 | 2 | 3 | | III-1 | 1700086E04Rik |
| 23915 | 2 | 3 | | III-2 | Zmpste24 | 10269 | 4-May-15 | 371 | 2 | 3 | | III-1 | 1700091H14Rik |
| 23918 | 2 | 3 | | III-2 | Zmym3 | 9203 | 12-May-15 | 373 | 2 | 3 | | III-1 | 1700092C10Rik |
| 23924 | 2 | 3 | | III-2 | Zmynd12 | 84217 | 4-May-15 | 379 | 2 | 3 | | III-1 | 1700094O05Rik |
| 23927 | 2 | 3 | | III-2 | Zmynd8 | 23613 | 12-May-15 | 383 | 2 | 3 | | III-1 | 1700096J18Rik |
| 23928 | 2 | 3 | | III-2 | Znf41-ps | | | 385 | 2 | 3 | | III-1 | 1700097N02Rik |
| 23929 | 2 | 3 | | III-2 | Znfl12b | 57473 | 4-May-15 | 389 | 2 | 3 | | III-1 | 1700101O22Rik |
| 23939 | 2 | 3 | | III-2 | Znrf3 | 84133 | 23-May-15 | 394 | 2 | 3 | | III-1 | 1700106J16Rik |
| 23942 | 2 | 3 | | III-2 | Zp2 | 7783 | 4-May-15 | 402 | 2 | 3 | | III-1 | 1700110C19Rik |
| 23952 | 2 | 3 | | III-2 | Zranb3 | 84083 | 4-May-15 | 407 | 2 | 3 | | III-1 | 1700112H15Rik |
| 23953 | 2 | 3 | | III-2 | Zrsr1 | 7310 | 4-May-15 | 410 | 2 | 3 | | III-1 | 1700113H08Rik |
| 23961 | 2 | 3 | | III-2 | Zscan22 | 342945 | 4-May-15 | 424 | 2 | 3 | | III-1 | 1700123O20Rik |
| 23976 | 2 | 3 | | III-2 | Zswim5 | 57643 | 4-May-15 | 436 | 2 | 3 | | III-1 | 1810007C17Rik |
| 23980 | 2 | 3 | | III-2 | Zufsp | 221302 | 4-May-15 | 446 | 2 | 3 | | III-1 | 1810013A23Rik |
| 23988 | 2 | 3 | | III-2 | Zyg11b | 79699 | 2-Jun-15 | 449 | 2 | 3 | | III-1 | 1810018F18Rik |
| 23990 | 2 | 3 | | III-2 | Zzef1 | 23140 | 12-May-15 | 451 | 2 | 3 | | III-1 | 1810020O05Rik |
| 2 | 2 | 3 | | III-1 | 0610007P14Rik | | | 467 | 2 | 3 | | III-1 | 1810055G02Rik |
| 5 | 2 | 3 | | III-1 | 0610009O20Rik | | | 468 | 2 | 3 | | III-1 | 1810058I24Rik |
| 7 | 2 | 3 | | III-1 | 0610010F05Rik | | | 472 | 2 | 3 | | III-1 | 1810066E05Rik |
| 19 | 2 | 3 | | III-1 | 0610040J01Rik | | | 473 | 2 | 3 | | III-1 | 2010001E11Rik |
| 24 | 2 | 3 | | III-1 | 1110002L01Rik | | | 482 | 2 | 3 | | III-1 | 2010106C02Rik |
| 25 | 2 | 3 | | III-1 | 1110004E09Rik | | | 484 | 2 | 3 | | III-1 | 2010107E04Rik |
| 30 | 2 | 3 | | III-1 | 1110008L16Rik | | | 487 | 2 | 3 | | III-1 | 2010109A12Rik |
| 31 | 2 | 3 | | III-1 | 1110008P14Rik | | | 492 | 2 | 3 | | III-1 | 2010308F09Rik |
| 32 | 2 | 3 | | III-1 | 1110012L19Rik | | | 493 | 2 | 3 | | III-1 | 2010310C07Rik |
| 35 | 2 | 3 | | III-1 | 1110019D14Rik | | | 502 | 2 | 3 | | III-1 | 2210016F16Rik |
| 38 | 2 | 3 | | III-1 | 1110028F11Rik | | | 516 | 2 | 3 | | III-1 | 2210420H20Rik |
| 41 | 2 | 3 | | III-1 | 1110032F04Rik | | | 518 | 2 | 3 | | III-1 | 2300003K06Rik |
| 46 | 2 | 3 | | III-1 | 1110038F14Rik | | | 520 | 2 | 3 | | III-1 | 2300009A05Rik |
| 49 | 2 | 3 | | III-1 | 1110054M08Rik | | | 524 | 2 | 3 | | III-1 | 2310002F09Rik |
| 50 | 2 | 3 | | III-1 | 1110057K04Rik | | | 532 | 2 | 3 | | III-1 | 2310007L24Rik |
| 51 | 2 | 3 | | III-1 | 1110058L19Rik | | | 533 | 2 | 3 | | III-1 | 2310008N11Rik |
| 54 | 2 | 3 | | III-1 | 1110065P20Rik | | | 534 | 2 | 3 | | III-1 | 2310009A05Rik |
| 60 | 2 | 3 | | III-1 | 1200014J11Rik | | | 544 | 2 | 3 | | III-1 | 2310022A10Rik |
| 64 | 2 | 3 | | III-1 | 1500004A13Rik | | | 548 | 2 | 3 | | III-1 | 2310033P09Rik |
| 65 | 2 | 3 | | III-1 | 1500009C09Rik | | | 549 | 2 | 3 | | III-1 | 2310034C09Rik |
| 68 | 2 | 3 | | III-1 | 1500011K16Rik | | | 555 | 2 | 3 | | III-1 | 2310039L15Rik |
| 69 | 2 | 3 | | III-1 | 1500012F01Rik | | | 558 | 2 | 3 | | III-1 | 2310043L19Rik |
| 70 | 2 | 3 | | III-1 | 1500012K07Rik | | | 567 | 2 | 3 | | III-1 | 2310061J03Rik |
| 72 | 2 | 3 | | III-1 | 1500015L24Rik | | | 572 | 2 | 3 | | III-1 | 2310069B03Rik |
| 77 | 2 | 3 | | III-1 | 1600002K03Rik | | | 577 | 2 | 3 | | III-1 | 2410003L11Rik |
| 79 | 2 | 3 | | III-1 | 1600012H06Rik | | | 587 | 2 | 3 | | III-1 | 2410016O06Rik |
| 82 | 2 | 3 | | III-1 | 1600014K23Rik | | | 588 | 2 | 3 | | III-1 | 2410017I17Rik |
| 85 | 2 | 3 | | III-1 | 1600019K03Rik | | | 599 | 2 | 3 | | III-1 | 2410141K09Rik |
| 87 | 2 | 3 | | III-1 | 1600023N17Rik | | | 606 | 2 | 3 | | III-1 | 2610001J05Rik |
| 88 | 2 | 3 | | III-1 | 1600025M17Rik | | | 610 | 2 | 3 | | III-1 | 2610008E11Rik |
| 89 | 2 | 3 | | III-1 | 1600027J07Rik | | | 613 | 2 | 3 | | III-1 | 2610018G03Rik |
| 93 | 2 | 3 | | III-1 | 1700001C19Rik | | | 614 | 2 | 3 | | III-1 | 2610020C07Rik |
| 96 | 2 | 3 | | III-1 | 1700001G11Rik | | | 620 | 2 | 3 | | III-1 | 2610034M16Rik |
| 99 | 2 | 3 | | III-1 | 1700001J11Rik | | | 622 | 2 | 3 | | III-1 | 2610035F20Rik |
| 101 | 2 | 3 | | III-1 | 1700001K23Rik | | | 625 | 2 | 3 | | III-1 | 2610100L16Rik |
| 103 | 2 | 3 | | III-1 | 1700003L19Rik | | | 627 | 2 | 3 | | III-1 | 2610203C22Rik |
| 111 | 2 | 3 | | III-1 | 1700003G13Rik | | | 629 | 2 | 3 | | III-1 | 2610207O16Rik |
| 128 | 2 | 3 | | III-1 | 1700007L15Rik | | | 631 | 2 | 3 | | III-1 | 2610305D13Rik |
| 129 | 2 | 3 | | III-1 | 1700007P06Rik | | | 636 | 2 | 3 | | III-1 | 2610507B11Rik |
| 133 | 2 | 3 | | III-1 | 1700008K24Rik | | | 643 | 2 | 3 | | III-1 | 2700046A07Rik |
| 140 | 2 | 3 | | III-1 | 1700010B08Rik | | | 645 | 2 | 3 | | III-1 | 2700049A03Rik |
| 143 | 2 | 3 | | III-1 | 1700010L14Rik | | | 648 | 2 | 3 | | III-1 | 2700062C07Rik |
| 150 | 2 | 3 | | III-1 | 1700011H03Rik | | | 657 | 2 | 3 | | III-1 | 2700099C18Rik |
| 154 | 2 | 3 | | III-1 | 1700012B07Rik | | | 659 | 2 | 3 | | III-1 | 2810002D19Rik |
| 158 | 2 | 3 | | III-1 | 1700012J11Rik | | | 664 | 2 | 3 | | III-1 | 2810013P06Rik |
| 164 | 2 | 3 | | III-1 | 1700013H16Rik | | | 666 | 2 | 3 | | III-1 | 2810025M15Rik |
| 173 | 2 | 3 | | III-1 | 1700016L04Rik | | | 667 | 2 | 3 | | III-1 | 2810029C07Rik |
| 175 | 2 | 3 | | III-1 | 1700016P04Rik | | | 671 | 2 | 3 | | III-1 | 2810055G20Rik |
| 177 | 2 | 3 | | III-1 | 1700017O01Rik | | | 674 | 2 | 3 | | III-1 | 2810404M03Rik |
| 187 | 2 | 3 | | III-1 | 1700018L02Rik | | | 677 | 2 | 3 | | III-1 | 2810408I11Rik |
| 192 | 2 | 3 | | III-1 | 1700019E08Rik | | | 689 | 2 | 3 | | III-1 | 2810471M01Rik |
| 194 | 2 | 3 | | III-1 | 1700019G24Rik | | | 692 | 2 | 3 | | III-1 | 2900008C10Rik |
| 206 | 2 | 3 | | III-1 | 1700020N15Rik | | | 693 | 2 | 3 | | III-1 | 2900009J06Rik |
| 215 | 2 | 3 | | III-1 | 1700022H16Rik | | | 698 | 2 | 3 | | III-1 | 2900055J20Rik |
| 222 | 2 | 3 | | III-1 | 1700024B18Rik | | | 700 | 2 | 3 | | III-1 | 2900057B20Rik |
| 227 | 2 | 3 | | III-1 | 1700025B11Rik | | | 701 | 2 | 3 | | III-1 | 2900060B14Rik |
| 232 | 2 | 3 | | III-1 | 1700025K24Rik | | | 703 | 2 | 3 | | III-1 | 2900079G21Rik |
| 236 | 2 | 3 | | III-1 | 1700026D11Rik | | | 706 | 2 | 3 | | III-1 | 2900097C17Rik |
| 240 | 2 | 3 | | III-1 | 1700027F09Rik | | | 708 | 2 | 3 | | III-1 | 3010001F23Rik |
| 247 | 2 | 3 | | III-1 | 1700028J16Rik | | | 710 | 2 | 3 | | III-1 | 3010033K07Rik |
| 249 | 2 | 3 | | III-1 | 1700028K03Rik | | | 714 | 2 | 3 | | III-1 | 3110007F17Rik |

Fig.22 - 58

| | | | | | | | | | | | | | |
|---|---|---|---|---|---|---|---|---|---|---|---|---|---|
| 718 | 2 | 3 | | | H-1 | 3110021A11Rik | | | 1216 | 2 | 3 | | H-1 | 4933411K20Rik |
| 720 | 2 | 3 | | | H-1 | 3110035E14Rik | | | 1218 | 2 | 3 | | H-1 | 4933412E24Rik |
| 724 | 2 | 3 | | | H-1 | 3110043O21Rik | | | 1221 | 2 | 3 | | H-1 | 4933413J09Rik |
| 725 | 2 | 3 | | | H-1 | 3110045C21Rik | | | 1224 | 2 | 3 | | H-1 | 4933416C03Rik |
| 728 | 2 | 3 | | | H-1 | 3110057O12Rik | | | 1227 | 2 | 3 | | H-1 | 4933416M06Rik |
| 729 | 2 | 3 | | | H-1 | 3110062M04Rik | | | 1231 | 2 | 3 | | H-1 | 4933417E11Rik |
| 742 | 2 | 3 | | | H-1 | 3830406C13Rik | | | 1232 | 2 | 3 | | H-1 | 4933417G07Rik |
| 744 | 2 | 3 | | | H-1 | 3830417A13Rik | | | 1233 | 2 | 3 | | H-1 | 4933417O13Rik |
| 747 | 2 | 3 | | | H-1 | 4631405J19Rik | | | 1236 | 2 | 3 | | H-1 | 4933422A05Rik |
| 750 | 2 | 3 | | | H-1 | 4632428C04Rik | | | 1238 | 2 | 3 | | H-1 | 4933424G05Rik |
| 754 | 2 | 3 | | | H-1 | 4732456N10Rik | | | 1249 | 2 | 3 | | H-1 | 4933428C19Rik |
| 756 | 2 | 3 | | | H-1 | 4732490B19Rik | | | 1253 | 2 | 3 | | H-1 | 4933430H16Rik |
| 758 | 2 | 3 | | | H-1 | 4831440E17Rik | | | 1258 | 2 | 3 | | H-1 | 4933431G14Rik |
| 759 | 2 | 3 | | | H-1 | 4833403J15Rik | | | 1277 | 2 | 3 | | H-1 | 4933439K11Rik |
| 761 | 2 | 3 | | | H-1 | 4833412C05Rik | | | 1278 | 2 | 3 | | H-1 | 4933440J02Rik |
| 765 | 2 | 3 | | | H-1 | 4833420G17Rik | | | 1283 | 2 | 3 | | H-1 | 5031425F14Rik |
| 768 | 2 | 3 | | | H-1 | 4833424O15Rik | | | 1290 | 2 | 3 | | H-1 | 5033406O09Rik |
| 770 | 2 | 3 | | | H-1 | 4834427G06Rik | | | 1291 | 2 | 3 | | H-1 | 5133400J02Rik |
| 779 | 2 | 3 | | | H-1 | 4921508D12Rik | | | 1298 | 2 | 3 | | H-1 | 5430401F13Rik |
| 786 | 2 | 3 | | | H-1 | 4921511M17Rik | | | 1301 | 2 | 3 | | H-1 | 5430403N17Rik |
| 796 | 2 | 3 | | | H-1 | 4921531P14Rik | | | 1311 | 2 | 3 | | H-1 | 5430427O19Rik |
| 798 | 2 | 3 | | | H-1 | 4921534H16Rik | | | 1315 | 2 | 3 | | H-1 | 5430437J10Rik |
| 800 | 2 | 3 | | | H-1 | 4921539E11Rik | | | 1316 | 2 | 3 | | H-1 | 5430440P10Rik |
| 802 | 2 | 3 | | | H-1 | 4922502H24Rik | | | 1324 | 2 | 3 | | H-1 | 5730412P04Rik |
| 803 | 2 | 3 | | | H-1 | 4922502N22Rik | | | 1326 | 2 | 3 | | H-1 | 5730420J15Rik |
| 810 | 2 | 3 | | | H-1 | 4930402K13Rik | | | 1333 | 2 | 3 | | H-1 | 5730488O18Rik |
| 821 | 2 | 3 | | | H-1 | 4930406D18Rik | | | 1335 | 2 | 3 | | H-1 | 5730508B09Rik |
| 825 | 2 | 3 | | | H-1 | 4930412D23Rik | | | 1339 | 2 | 3 | | H-1 | 5830411N06Rik |
| 827 | 2 | 3 | | | H-1 | 4930413E15Rik | | | 1340 | 2 | 3 | | H-1 | 5830415F09Rik |
| 829 | 2 | 3 | | | H-1 | 4930413G21Rik | | | 1341 | 2 | 3 | | H-1 | 5830416J19Rik |
| 830 | 2 | 3 | | | H-1 | 4930413M19Rik | | | 1347 | 2 | 3 | | H-1 | 5830432E09Rik |
| 838 | 2 | 3 | | | H-1 | 4930419G24Rik | | | 1349 | 2 | 3 | | H-1 | 5830454E08Rik |
| 841 | 2 | 3 | | | H-1 | 4930425O10Rik | | | 1350 | 2 | 3 | | H-1 | 5830473C10Rik |
| 844 | 2 | 3 | | | H-1 | 4930427A07Rik | | | 1352 | 2 | 3 | | H-1 | 5930412G12Rik |
| 856 | 2 | 3 | | | H-1 | 4930430F21Rik | | | 1353 | 2 | 3 | | H-1 | 5930430L01Rik |
| 870 | 2 | 3 | | | H-1 | 4930440J19Rik | | | 1358 | 2 | 3 | | H-1 | 6030440G07Rik |
| 872 | 2 | 3 | | | H-1 | 4930442J19Rik | | | 1363 | 2 | 3 | | H-1 | 6030469F06Rik |
| 874 | 2 | 3 | | | H-1 | 4930443O20Rik | | | 1366 | 2 | 3 | | H-1 | 6330403A02Rik |
| 882 | 2 | 3 | | | H-1 | 4930447K03Rik | | | 1367 | 2 | 3 | | H-1 | 6330403K07Rik |
| 888 | 2 | 3 | | | H-1 | 4930448J18Rik | | | 1368 | 2 | 3 | | H-1 | 6330407A03Rik |
| 897 | 2 | 3 | | | H-1 | 4930452B06Rik | | | 1384 | 2 | 3 | | H-1 | 6430573F11Rik |
| 903 | 2 | 3 | | | H-1 | 4930455B14Rik | | | 1385 | 2 | 3 | | H-1 | 6430584L05Rik |
| 906 | 2 | 3 | | | H-1 | 4930455F16Rik | | | 1391 | 2 | 3 | | H-1 | 6720468P15Rik |
| 910 | 2 | 3 | | | H-1 | 4930459C07Rik | | | 1396 | 2 | 3 | | H-1 | 7420426K07Rik |
| 913 | 2 | 3 | | | H-1 | 4930463O16Rik | | | 1403 | 2 | 3 | | H-1 | 8030423F21Rik |
| 915 | 2 | 3 | | | H-1 | 4930465M20Rik | | | 1410 | 2 | 3 | | H-1 | 8430422H06Rik |
| 931 | 2 | 3 | | | H-1 | 4930474N05Rik | | | 1415 | 2 | 3 | | H-1 | 8430431K14Rik |
| 936 | 2 | 3 | | | H-1 | 4930480E11Rik | | | 1423 | 2 | 3 | | H-1 | 9030619P08Rik |
| 938 | 2 | 3 | | | H-1 | 4930480K15Rik | | | 1427 | 2 | 3 | | H-1 | 9130008F23Rik |
| 941 | 2 | 3 | | | H-1 | 4930482G09Rik | | | 1437 | 2 | 3 | | H-1 | 9130221F21Rik |
| 950 | 2 | 3 | | | H-1 | 4930488B22Rik | | | 1441 | 2 | 3 | | H-1 | 9130401M01Rik |
| 959 | 2 | 3 | | | H-1 | 4930503E14Rik | | | 1443 | 2 | 3 | | H-1 | 9230009I02Rik |
| 964 | 2 | 3 | | | H-1 | 4930504O13Rik | | | 1450 | 2 | 3 | | H-1 | 9230112D13Rik |
| 969 | 2 | 3 | | | H-1 | 4930507D05Rik | | | 1454 | 2 | 3 | | H-1 | 9230116N13Rik |
| 972 | 2 | 3 | | | H-1 | 4930509J09Rik | | | 1455 | 2 | 3 | | H-1 | 9330020H09Rik |
| 984 | 2 | 3 | | | H-1 | 4930515L03Rik | | | 1460 | 2 | 3 | | H-1 | 9330151L19Rik |
| 990 | 2 | 3 | | | H-1 | 4930519F16Rik | | | 1461 | 2 | 3 | | H-1 | 9330158H04Rik |
| 991 | 2 | 3 | | | H-1 | 4930519F24Rik | | | 1464 | 2 | 3 | | H-1 | 9330162O12Rik |
| 995 | 2 | 3 | | | H-1 | 4930520P13Rik | | | 1465 | 2 | 3 | | H-1 | 9330162B11Rik |
| 1000 | 2 | 3 | | | H-1 | 4930523O13Rik | | | 1467 | 2 | 3 | | H-1 | 9330175M20Rik |
| 1010 | 2 | 3 | | | H-1 | 4930526L06Rik | | | 1470 | 2 | 3 | | H-1 | 9330182L06Rik |
| 1021 | 2 | 3 | | | H-1 | 4930533B01Rik | | | 1471 | 2 | 3 | | H-1 | 9330182G14Rik |
| 1024 | 2 | 3 | | | H-1 | 4930539J22Rik | | | 1475 | 2 | 3 | | H-1 | 9430014N10Rik |
| 1034 | 2 | 3 | | | H-1 | 4930544G11Rik | | | 1477 | 2 | 3 | | H-1 | 9430016H08Rik |
| 1037 | 2 | 3 | | | H-1 | 4930545H06Rik | | | 1481 | 2 | 3 | | H-1 | 9430021M05Rik |
| 1038 | 2 | 3 | | | H-1 | 4930545L23Rik | | | 1484 | 2 | 3 | | H-1 | 9430041J12Rik |
| 1044 | 2 | 3 | | | H-1 | 4930548H24Rik | | | 1489 | 2 | 3 | | H-1 | 9430091E24Rik |
| 1047 | 2 | 3 | | | H-1 | 4930549C01Rik | | | 1491 | 2 | 3 | | H-1 | 9530003J23Rik |
| 1050 | 2 | 3 | | | H-1 | 4930550L24Rik | | | 1494 | 2 | 3 | | H-1 | 9530027J09Rik |
| 1054 | 2 | 3 | | | H-1 | 4930554C24Rik | | | 1495 | 2 | 3 | | H-1 | 9530036O11Rik |
| 1057 | 2 | 3 | | | H-1 | 4930556C24Rik | | | 1498 | 2 | 3 | | H-1 | 9530053A07Rik |
| 1061 | 2 | 3 | | | H-1 | 4930556N09Rik | | | 1508 | 2 | 3 | | H-1 | 9630028H03Rik |
| 1069 | 2 | 3 | | | H-1 | 4930562F07Rik | | | 1510 | 2 | 3 | | H-1 | 9830107B12Rik |
| 1071 | 2 | 3 | | | H-1 | 4930563E18Rik | | | 1515 | 2 | 3 | | H-1 | 9930014A18Rik |
| 1089 | 2 | 3 | | | H-1 | 4930571O06Rik | | | 1516 | 2 | 3 | | H-1 | 9930021J03Rik |
| 1090 | 2 | 3 | | | H-1 | 4930572K03Rik | | | 1517 | 2 | 3 | | H-1 | 9930104L06Rik |
| 1095 | 2 | 3 | | | H-1 | 4930578C19Rik | 79742 | 4-May-15 | 1526 | 2 | 3 | | H-1 | A230001M10Rik |
| 1100 | 2 | 3 | | | H-1 | 4930579F01Rik | | | 1528 | 2 | 3 | | H-1 | A230020J21Rik |
| 1103 | 2 | 3 | | | H-1 | 4930579K19Rik | | | 1532 | 2 | 3 | | H-1 | A230056J06Rik |
| 1105 | 2 | 3 | | | H-1 | 4930583K01Rik | | | 1535 | 2 | 3 | | H-1 | A230065H16Rik |
| 1112 | 2 | 3 | | | H-1 | 4930592J03Rik | | | 1536 | 2 | 3 | | H-1 | A230070E04Rik |
| 1122 | 2 | 3 | | | H-1 | 4931402G19Rik | | | 1537 | 2 | 3 | | H-1 | A230072C01Rik |
| 1127 | 2 | 3 | | | H-1 | 4931406H21Rik | | | 1542 | 2 | 3 | | H-1 | A230108P19Rik |
| 1139 | 2 | 3 | | | H-1 | 4931428L19Rik | | | 1546 | 2 | 3 | | H-1 | A330023F24Rik |
| 1146 | 2 | 3 | | | H-1 | 4931431F19Rik | | | 1547 | 2 | 3 | | H-1 | A330032B11Rik |
| 1148 | 2 | 3 | | | H-1 | 4931440J10Rik | | | 1550 | 2 | 3 | | H-1 | A330040F15Rik |
| 1154 | 2 | 3 | | | H-1 | 4932413F04Rik | | | 1551 | 2 | 3 | | H-1 | A330041J22Rik |
| 1161 | 2 | 3 | | | H-1 | 4932429P05Rik | | | 1553 | 2 | 3 | | H-1 | A330049N07Rik |
| 1165 | 2 | 3 | | | H-1 | 4932441J04Rik | | | 1556 | 2 | 3 | | H-1 | A330070K13Rik |
| 1185 | 2 | 3 | | | H-1 | 4933403O08Rik | | | 1557 | 2 | 3 | | H-1 | A330074J22Rik |
| 1189 | 2 | 3 | | | H-1 | 4933405D12Rik | | | 1559 | 2 | 3 | | H-1 | A330076H08Rik |
| 1194 | 2 | 3 | | | H-1 | 4933406D12Rik | | | 1560 | 2 | 3 | | H-1 | A330093E20Rik |
| 1198 | 2 | 3 | | | H-1 | 4933406J08Rik | | | 1561 | 2 | 3 | | H-1 | A330102I10Rik |
| 1199 | 2 | 3 | | | H-1 | 4933406J10Rik | | | 1565 | 2 | 3 | | H-1 | A430035B10Rik |
| 1207 | 2 | 3 | | | H-1 | 4933408B17Rik | | | 1566 | 2 | 3 | | H-1 | A430078G23Rik |
| 1208 | 2 | 3 | | | H-1 | 4933408J17Rik | | | 1574 | 2 | 3 | | H-1 | A4gnt | 51146 | 4-May-15 |
| 1212 | 2 | 3 | | | H-1 | 4933411E08Rik | | | 1581 | 2 | 3 | | H-1 | A530053G22Rik |

Fig.22 - 59

| | | | | | | | | | | | | | | |
|---|---|---|---|---|---|---|---|---|---|---|---|---|---|---|
| 1583 | 2 | 3 | | III-1 | A530058N18Rik | | | 1936 | 2 | 3 | | III-1 | Adam29 | 11086 | 4-May-15 |
| 1584 | 2 | 3 | | III-1 | A530064D06Rik | | | 1944 | 2 | 3 | | III-1 | Adam5 | 255926 | 4-May-15 |
| 1589 | 2 | 3 | | III-1 | A630001G21Rik | | | 1952 | 2 | 3 | | III-1 | Adamts10 | 81794 | 23-May-15 |
| 1596 | 2 | 3 | | III-1 | A630023P12Rik | | | 1957 | 2 | 3 | | III-1 | Adamts16 | 170690 | 12-May-15 |
| 1597 | 2 | 3 | | III-1 | A630033H20Rik | | | 1968 | 2 | 3 | | III-1 | Adamts8 | 11095 | 4-May-15 |
| 1599 | 2 | 3 | | III-1 | A630072M18Rik | | | 1972 | 2 | 3 | | III-1 | Adamtsl3 | 57188 | 4-May-15 |
| 1601 | 2 | 3 | | III-1 | A630075F10Rik | | | 1974 | 2 | 3 | | III-1 | Adamtsl5 | 339366 | 4-May-15 |
| 1604 | 2 | 3 | | III-1 | A630089N07Rik | | | 1975 | 2 | 3 | | III-1 | Adap1 | 11033 | 4-May-15 |
| 1611 | 2 | 3 | | III-1 | A730018C14Rik | | | 1979 | 2 | 3 | | III-1 | Adarb2 | 105 | 4-May-15 |
| 1615 | 2 | 3 | | III-1 | A730043L09Rik | | | 1982 | 2 | 3 | | III-1 | Adat3 | 113179 | 4-May-15 |
| 1622 | 2 | 3 | | III-1 | A730098P11Rik | | | 1984 | 2 | 3 | | III-1 | Adck1 | 57143 | 4-May-15 |
| 1625 | 2 | 3 | | III-1 | A830018L16Rik | | | 1987 | 2 | 3 | | III-1 | Adck4 | 79934 | 23-May-15 |
| 1634 | 2 | 3 | | III-1 | A930003O13Rik | | | 1989 | 2 | 3 | | III-1 | Adcy1 | 107 | 4-May-15 |
| 1637 | 2 | 3 | | III-1 | A930006I01Rik | | | 1992 | 2 | 3 | | III-1 | Adcy3 | 109 | 7-Jun-15 |
| 1644 | 2 | 3 | | III-1 | A930018F10Rik | | | 1993 | 2 | 3 | | III-1 | Adcy4 | 196883 | 4-May-15 |
| 1649 | 2 | 3 | | III-1 | A930019D19Rik | | | 1994 | 2 | 3 | | III-1 | Adcy5 | 111 | 23-May-15 |
| 1651 | 2 | 3 | | III-1 | A930041C12Rik | | | 1996 | 2 | 3 | | III-1 | Adcy7 | 113 | 4-May-15 |
| 1652 | 2 | 3 | | III-1 | AA387883 | | | 1998 | 2 | 3 | | III-1 | Adcy9 | 115 | 24-May-15 |
| 1656 | 2 | 3 | | III-1 | AA415398 | | | 2001 | 2 | 3 | | III-1 | Add1 | 118 | 17-May-15 |
| 1667 | 2 | 3 | | III-1 | AA987161 | | | 2006 | 2 | 3 | | III-1 | Adh4 | 127 | 7-Jun-15 |
| 1668 | 2 | 3 | | III-1 | Aaas | 8086 | 12-May-15 | 2012 | 2 | 3 | | III-1 | Adi1 | 55256 | 12-May-15 |
| 1669 | 2 | 3 | | III-1 | Aacs | 65985 | 12-May-15 | 2019 | 2 | 3 | | III-1 | Adm2 | 79924 | 17-May-15 |
| 1675 | 2 | 3 | | III-1 | Aagab | 79719 | 17-May-15 | 2022 | 2 | 3 | | III-1 | Ado | 84890 | 4-May-15 |
| 1682 | 2 | 3 | | III-1 | Aars | 16 | 31-May-15 | 2024 | 2 | 3 | | III-1 | Adora2a | 135 | 12-May-15 |
| 1683 | 2 | 3 | | III-1 | Aars2 | 57505 | 4-May-15 | 2027 | 2 | 3 | | III-1 | Adpgk | 83440 | 14-May-15 |
| 1688 | 2 | 3 | | III-1 | Aatf | 26574 | 12-May-15 | 2034 | 2 | 3 | | III-1 | Adra1d | 146 | 4-May-15 |
| 1689 | 2 | 3 | | III-1 | Aatk | 9625 | 4-May-15 | 2035 | 2 | 3 | | III-1 | Adra2a | 150 | 4-May-15 |
| 1694 | 2 | 3 | | III-1 | Abca12 | 26154 | 23-May-15 | 2036 | 2 | 3 | | III-1 | Adra2b | 151 | 4-May-15 |
| 1701 | 2 | 3 | | III-1 | Abca3 | 21 | 12-May-15 | 2038 | 2 | 3 | | III-1 | Adrb1 | 153 | 24-May-15 |
| 1705 | 2 | 3 | | III-1 | Abca7 | 10347 | 12-May-15 | 2043 | 2 | 3 | | III-1 | Adrm1 | 11047 | 4-May-15 |
| 1707 | 2 | 3 | | III-1 | Abca8b | | | 2044 | 2 | 3 | | III-1 | Adsl | 158 | 12-May-15 |
| 1710 | 2 | 3 | | III-1 | Abcb11 | 8647 | 23-May-15 | 2048 | 2 | 3 | | III-1 | Aebp1 | 165 | 4-May-15 |
| 1715 | 2 | 3 | | III-1 | Abcb6 | 10058 | 12-May-15 | 2049 | 2 | 3 | | III-1 | Aebp2 | 121536 | 17-May-15 |
| 1716 | 2 | 3 | | III-1 | Abcb7 | 22 | 23-May-15 | 2051 | 2 | 3 | | III-1 | Aes | 166 | 12-May-15 |
| 1719 | 2 | 3 | | III-1 | Abcc1 | 4363 | 12-May-15 | 2064 | 2 | 3 | | III-1 | Afap1l2 | 84632 | 4-May-15 |
| 1721 | 2 | 3 | | III-1 | Abcc12 | 94160 | 4-May-15 | 2065 | 2 | 3 | | III-1 | Aff1 | 4299 | 12-May-15 |
| 1725 | 2 | 3 | | III-1 | Abcc5 | 10057 | 21-May-15 | 2068 | 2 | 3 | | III-1 | Aff4 | 27125 | 22-May-15 |
| 1729 | 2 | 3 | | III-1 | Abcd1 | 215 | 7-Jun-15 | 2073 | 2 | 3 | | III-1 | Afp | 174 | 7-Jun-15 |
| 1731 | 2 | 3 | | III-1 | Abcd3 | 5825 | 7-Jun-15 | 2077 | 2 | 3 | | III-1 | Agap2 | 116986 | 4-May-15 |
| 1732 | 2 | 3 | | III-1 | Abcd4 | 5826 | 23-May-15 | 2078 | 2 | 3 | | III-1 | Agap3 | 116988 | 12-May-15 |
| 1733 | 2 | 3 | | III-1 | Abce1 | 6059 | 21-May-15 | 2081 | 2 | 3 | | III-1 | Agbl3 | 340351 | 4-May-15 |
| 1738 | 2 | 3 | | III-1 | Abcg2 | 9429 | 24-May-15 | 2082 | 2 | 3 | | III-1 | Agbl4 | 84871 | 4-May-15 |
| 1739 | 2 | 3 | | III-1 | Abcg3 | | | 2084 | 2 | 3 | | III-1 | Ager | 177 | 17-May-15 |
| 1742 | 2 | 3 | | III-1 | Abcg8 | 64241 | 23-May-15 | 2087 | 2 | 3 | | III-1 | Aggf1 | 55109 | 4-May-15 |
| 1744 | 2 | 3 | | III-1 | Abhd10 | 55347 | 4-May-15 | 2090 | 2 | 3 | | III-1 | Agmat | 79814 | 4-May-15 |
| 1749 | 2 | 3 | | III-1 | Abhd13 | 84945 | 4-May-15 | 2092 | 2 | 3 | | III-1 | Ago1 | 26523 | 4-May-15 |
| 1752 | 2 | 3 | | III-1 | Abhd15 | 116236 | 4-May-15 | 2096 | 2 | 3 | | III-1 | Agpat1 | 10554 | 4-May-15 |
| 1753 | 2 | 3 | | III-1 | Abhd16a | 7920 | 4-May-15 | 2103 | 2 | 3 | | III-1 | Agps | 8540 | 4-May-15 |
| 1761 | 2 | 3 | | III-1 | Abhd5 | 51099 | 12-May-15 | 2106 | 2 | 3 | | III-1 | Agrn | 375790 | 12-May-15 |
| 1762 | 2 | 3 | | III-1 | Abhd8 | 57406 | 17-May-15 | 2107 | 2 | 3 | | III-1 | Agrp | 181 | 4-May-15 |
| 1764 | 2 | 3 | | III-1 | Abi1 | 10006 | 12-May-15 | 2109 | 2 | 3 | | III-1 | Agtphp1 | 23287 | 23-May-15 |
| 1766 | 2 | 3 | | III-1 | Abi3 | 51225 | 4-May-15 | 2110 | 2 | 3 | | III-1 | Agtr1a | | |
| 1767 | 2 | 3 | | III-1 | Abi3bp | 25890 | 4-May-15 | 2111 | 2 | 3 | | III-1 | Agtr1b | 185 | 24-May-15 |
| 1770 | 2 | 3 | | III-1 | Ablim1 | 3983 | 12-May-15 | 2117 | 2 | 3 | | III-1 | Ahcy | 191 | 12-May-15 |
| 1774 | 2 | 3 | | III-1 | Abr | 29 | 3-May-15 | 2118 | 2 | 3 | | III-1 | Ahcyl1 | 10768 | 3-May-15 |
| 1777 | 2 | 3 | | III-1 | Abt1 | 29777 | 4-May-15 | 2120 | 2 | 3 | | III-1 | Ahdc1 | 27245 | 4-May-15 |
| 1779 | 2 | 3 | | III-1 | Abtb2 | 25841 | 4-May-15 | 2122 | 2 | 3 | | III-1 | Ahnak | 79026 | 4-May-15 |
| 1782 | 2 | 3 | | III-1 | Acaa2 | 10449 | 4-May-15 | 2123 | 2 | 3 | | III-1 | Ahr | 196 | 17-May-15 |
| 1785 | 2 | 3 | | III-1 | Acad10 | 80724 | 4-May-15 | 2128 | 2 | 3 | | III-1 | AI115009 | | |
| 1786 | 2 | 3 | | III-1 | Acad11 | 84129 | 4-May-15 | 2130 | 2 | 3 | | III-1 | AI182371 | | |
| 1787 | 2 | 3 | | III-1 | Acad12 | | | 2131 | 2 | 3 | | III-1 | AI197445 | | |
| 1788 | 2 | 3 | | III-1 | Acad8 | 27034 | 12-May-15 | 2138 | 2 | 3 | | III-1 | AI429214 | | |
| 1791 | 2 | 3 | | III-1 | Acadm | 34 | 23-May-15 | 2139 | 2 | 3 | | III-1 | AI450353 | | |
| 1792 | 2 | 3 | | III-1 | Acads | 35 | 23-May-15 | 2140 | 2 | 3 | | III-1 | AI462493 | | |
| 1793 | 2 | 3 | | III-1 | Acadsb | 36 | 12-May-15 | 2143 | 2 | 3 | | III-1 | AI467606 | | |
| 1794 | 2 | 3 | | III-1 | Acadvl | 37 | 23-May-15 | 2157 | 2 | 3 | | III-1 | AI846148 | | |
| 1801 | 2 | 3 | | III-1 | Acat3 | | | 2159 | 2 | 3 | | III-1 | AI848285 | | |
| 1802 | 2 | 3 | | III-1 | Acbd3 | 64746 | 4-May-15 | 2167 | 2 | 3 | | III-1 | Aifm1 | 9131 | 19-May-15 |
| 1807 | 2 | 3 | | III-1 | Accs | 84680 | 20-May-15 | 2169 | 2 | 3 | | III-1 | Aifm3 | 150209 | 4-May-15 |
| 1808 | 2 | 3 | | III-1 | Accsl | 390110 | 12-May-15 | 2173 | 2 | 3 | | III-1 | Aim2 | 9447 | 17-May-15 |
| 1815 | 2 | 3 | | III-1 | Acer3 | 55331 | 4-May-15 | 2179 | 2 | 3 | | III-1 | Aim | 100271873 | 12-May-15 |
| 1827 | 2 | 3 | | III-1 | Aco1 | 48 | 31-May-15 | 2182 | 2 | 3 | | III-1 | AK010878 | | |
| 1830 | 2 | 3 | | III-1 | Acot10 | | | 2188 | 2 | 3 | | III-1 | Ak5 | 26289 | 4-May-15 |
| 1833 | 2 | 3 | | III-1 | Acot13 | 55856 | 24-May-15 | 2189 | 2 | 3 | | III-1 | Ak6 | 102157402 | 4-May-15 |
| 1837 | 2 | 3 | | III-1 | Acot5 | | | 2190 | 2 | 3 | | III-1 | Ak7 | 122481 | 4-May-15 |
| 1839 | 2 | 3 | | III-1 | Acot7 | 11332 | 4-May-15 | 2191 | 2 | 3 | | III-1 | Ak8 | 158067 | 4-May-15 |
| 1840 | 2 | 3 | | III-1 | Acot8 | 10005 | 12-May-15 | 2195 | 2 | 3 | | III-1 | Akap12 | 9590 | 4-May-15 |
| 1841 | 2 | 3 | | III-1 | Acot9 | 23597 | 4-May-15 | 2196 | 2 | 3 | | III-1 | Akap13 | 11214 | 26-May-15 |
| 1842 | 2 | 3 | | III-1 | Acox1 | 51 | 12-May-15 | 2197 | 2 | 3 | | III-1 | Akap14 | 158798 | 4-May-15 |
| 1845 | 2 | 3 | | III-1 | Acoxl | 55289 | 4-May-15 | 2202 | 2 | 3 | | III-1 | Akap5 | 9495 | 21-May-15 |
| 1847 | 2 | 3 | | III-1 | Acp2 | 53 | 12-May-15 | 2204 | 2 | 3 | | III-1 | Akap7 | 9465 | 4-May-15 |
| 1854 | 2 | 3 | | III-1 | Acrv1 | 56 | 4-May-15 | 2205 | 2 | 3 | | III-1 | Akap8 | 10270 | 4-May-15 |
| 1856 | 2 | 3 | | III-1 | Acsbg2 | 81616 | 4-May-15 | 2207 | 2 | 3 | | III-1 | Akap9 | 10142 | 29-May-15 |
| 1858 | 2 | 3 | | III-1 | Acsf3 | 197322 | 4-May-15 | 2208 | 2 | 3 | | III-1 | Akip1 | 56672 | 4-May-15 |
| 1862 | 2 | 3 | | III-1 | Acsl5 | 51703 | 4-May-15 | 2209 | 2 | 3 | | III-1 | Akirin1 | 79647 | 4-May-15 |
| 1864 | 2 | 3 | | III-1 | Acsm1 | 116285 | 4-May-15 | 2214 | 2 | 3 | | III-1 | Akr1a1 | 10327 | 12-May-15 |
| 1887 | 2 | 3 | | III-1 | Actn1 | 87 | 14-May-15 | 2224 | 2 | 3 | | III-1 | Akr1c20 | | |
| 1898 | 2 | 3 | | III-1 | Actr6 | 64431 | 4-May-15 | 2237 | 2 | 3 | | III-1 | Alas1 | 211 | 12-May-15 |
| 1899 | 2 | 3 | | III-1 | Actr8 | 93973 | 4-May-15 | 2241 | 2 | 3 | | III-1 | Aldh16a1 | 126133 | 23-May-15 |
| 1900 | 2 | 3 | | III-1 | Actrt1 | 139741 | 28-May-15 | 2248 | 2 | 3 | | III-1 | Aldh1l1 | 10840 | 23-May-15 |
| 1905 | 2 | 3 | | III-1 | Acvr1c | 130399 | 4-May-15 | 2252 | 2 | 3 | | III-1 | Aldh3a2 | 224 | 4-May-15 |
| 1906 | 2 | 3 | | III-1 | Acvr2a | 92 | 4-May-15 | 2258 | 2 | 3 | | III-1 | Aldh7a1 | 501 | 23-May-15 |
| 1909 | 2 | 3 | | III-1 | Acy1 | 95 | 4-May-15 | 2266 | 2 | 3 | | III-1 | Alg1 | 56052 | 23-May-15 |
| 1910 | 2 | 3 | | III-1 | Acy3 | 91703 | 4-May-15 | 2276 | 2 | 3 | | III-1 | Alg8 | 79053 | 4-May-15 |
| 1914 | 2 | 3 | | III-1 | Acad1 | 132612 | 4-May-15 | 2277 | 2 | 3 | | III-1 | Alg9 | 79796 | 23-May-15 |
| 1921 | 2 | 3 | | III-1 | Adam17 | 6868 | 24-May-15 | 2281 | 2 | 3 | | III-1 | Alkbh3 | 221120 | 4-May-15 |
| 1925 | 2 | 3 | | III-1 | Adam1b | 100420505 | 4-May-15 | | | | | | | | |

Fig.22 - 60

| | | | | | | | | | | | | | | | |
|---|---|---|---|---|---|---|---|---|---|---|---|---|---|---|---|
| 2286 | 2 | 3 | | | III-1 | Alkbh8 | 91801 | 4-May-15 | 2698 | 2 | 3 | | | III-1 | Arid4b | 51742 | 4-May-15 |
| 2298 | 2 | 3 | | | III-1 | Alpi | 248 | 4-May-15 | 2709 | 2 | 3 | | | III-1 | Arl4ep | 120534 | 4-May-15 |
| 2299 | 2 | 3 | | | III-1 | Alpk1 | 80216 | 28-May-15 | 2710 | 2 | 3 | | | III-1 | Arl4epl | 644100 | 4-May-15 |
| 2303 | 2 | 3 | | | III-1 | Alppl2 | 251 | 4-May-15 | 2714 | 2 | 3 | | | III-1 | Arl2bp | 23568 | 4-May-15 |
| 2304 | 2 | 3 | | | III-1 | Als2 | 57679 | 23-May-15 | 2716 | 2 | 3 | | | III-1 | Arl4a | 10124 | 4-May-15 |
| 2306 | 2 | 3 | | | III-1 | Als2cr11 | 151254 | 4-May-15 | 2719 | 2 | 3 | | | III-1 | Arl5a | 26225 | 4-May-15 |
| 2312 | 2 | 3 | | | III-1 | Alyref2 | | | 2724 | 2 | 3 | | | III-1 | Arl6ip4 | 51329 | 12-May-15 |
| 2323 | 2 | 3 | | | III-1 | Amer2 | 219287 | 4-May-15 | 2727 | 2 | 3 | | | III-1 | Arl8a | 127829 | 4-May-15 |
| 2327 | 2 | 3 | | | III-1 | Amhr2 | 269 | 12-May-15 | 2733 | 2 | 3 | | | III-1 | Armc2 | 84071 | 4-May-15 |
| 2332 | 2 | 3 | | | III-1 | Ammecr1 | 9949 | 12-May-15 | 2741 | 2 | 3 | | | III-1 | Armcx1 | 51309 | 12-May-15 |
| 2337 | 2 | 3 | | | III-1 | Amot1 | 154810 | 4-May-15 | 2749 | 2 | 3 | | | III-1 | Arnt1 | 406 | 12-May-15 |
| 2338 | 2 | 3 | | | III-1 | Amot2 | 51421 | 4-May-15 | 2751 | 2 | 3 | | | III-1 | Arpc1a | 10552 | 4-May-15 |
| 2341 | 2 | 3 | | | III-1 | Ampd3 | 272 | 12-May-15 | 2753 | 2 | 3 | | | III-1 | Arpc2 | 10109 | 31-May-15 |
| 2342 | 2 | 3 | | | III-1 | Amph | 273 | 12-May-15 | 2758 | 2 | 3 | | | III-1 | Arpp19 | 10776 | 12-May-15 |
| 2350 | 2 | 3 | | | III-1 | Amz2 | 51321 | 23-May-15 | 2759 | 2 | 3 | | | III-1 | Arpp21 | 10777 | 4-May-15 |
| 2355 | 2 | 3 | | | III-1 | Anapc15 | 25906 | 4-May-15 | 2763 | 2 | 3 | | | III-1 | Arrdc1 | 92714 | 4-May-15 |
| 2356 | 2 | 3 | | | III-1 | Anapc16 | 119504 | 31-May-15 | 2768 | 2 | 3 | | | III-1 | Arsa | 410 | 23-May-15 |
| 2370 | 2 | 3 | | | III-1 | Angpt2 | 285 | 24-May-15 | 2769 | 2 | 3 | | | III-1 | Arsb | 411 | 13-Jun-15 |
| 2371 | 2 | 3 | | | III-1 | Angpt4 | 51378 | 4-May-15 | 2770 | 2 | 3 | | | III-1 | Arsg | 22901 | 20-May-15 |
| 2382 | 2 | 3 | | | III-1 | Ankar | 150709 | 4-May-15 | 2776 | 2 | 3 | | | III-1 | Art2b | | |
| 2388 | 2 | 3 | | | III-1 | Ankib1 | 54467 | 4-May-15 | 2782 | 2 | 3 | | | III-1 | Arvcf | 421 | 12-May-15 |
| 2394 | 2 | 3 | | | III-1 | Ankra2 | 57763 | 4-May-15 | 2783 | 2 | 3 | | | III-1 | Arx | 170302 | 23-May-15 |
| 2396 | 2 | 3 | | | III-1 | Ankrd10 | 55608 | 12-May-15 | 2786 | 2 | 3 | | | III-1 | As3mt | 57412 | 4-May-15 |
| 2398 | 2 | 3 | | | III-1 | Ankrd12 | 23253 | 21-May-15 | 2787 | 2 | 3 | | | III-1 | Asah1 | 427 | 12-May-15 |
| 2399 | 2 | 3 | | | III-1 | Ankrd13a | 88455 | 12-May-15 | 2790 | 2 | 3 | | | III-1 | Asap2 | 8853 | 12-May-15 |
| 2401 | 2 | 3 | | | III-1 | Ankrd13c | 81573 | 4-May-15 | 2792 | 2 | 3 | | | III-1 | Asb1 | 51665 | 4-May-15 |
| 2403 | 2 | 3 | | | III-1 | Ankrd16 | 54822 | 4-May-15 | 2811 | 2 | 3 | | | III-1 | Ascc1 | 51008 | 12-May-15 |
| 2406 | 2 | 3 | | | III-1 | Ankrd22 | 118932 | 4-May-15 | 2812 | 2 | 3 | | | III-1 | Ascc2 | 84164 | 4-May-15 |
| 2409 | 2 | 3 | | | III-1 | Ankrd26 | 22852 | 4-May-15 | 2813 | 2 | 3 | | | III-1 | Ascc3 | 10973 | 4-May-15 |
| 2411 | 2 | 3 | | | III-1 | Ankrd28 | 23243 | 4-May-15 | 2815 | 2 | 3 | | | III-1 | Ascl2 | 430 | 4-May-15 |
| 2416 | 2 | 3 | | | III-1 | Ankrd34a | 284615 | 4-May-15 | 2818 | 2 | 3 | | | III-1 | Asd5 | 647219 | 4-May-15 |
| 2420 | 2 | 3 | | | III-1 | Ankrd36 | 375248 | 16-May-15 | 2822 | 2 | 3 | | | III-1 | Asgr2 | 433 | 12-May-15 |
| 2425 | 2 | 3 | | | III-1 | Ankrd44 | 91526 | 4-May-15 | 2824 | 2 | 3 | | | III-1 | Ash2l | 9070 | 4-May-15 |
| 2427 | 2 | 3 | | | III-1 | Ankrd46 | 157567 | 4-May-15 | 2826 | 2 | 3 | | | III-1 | Asic2 | 40 | 12-May-15 |
| 2431 | 2 | 3 | | | III-1 | Ankrd53 | 79998 | 4-May-15 | 2827 | 2 | 3 | | | III-1 | Asic3 | 9311 | 4-May-15 |
| 2439 | 2 | 3 | | | III-1 | Ankrd7 | 56311 | 4-May-15 | 2828 | 2 | 3 | | | III-1 | Asic4 | 55515 | 12-May-15 |
| 2441 | 2 | 3 | | | III-1 | Anks1 | 23294 | 21-May-15 | 2831 | 2 | 3 | | | III-1 | Asmt | | |
| 2445 | 2 | 3 | | | III-1 | Anks6 | 203286 | 4-May-15 | 2836 | 2 | 3 | | | III-1 | Aspdh | 554235 | 4-May-15 |
| 2450 | 2 | 3 | | | III-1 | Ano10 | 55129 | 4-May-15 | 2839 | 2 | 3 | | | III-1 | Asphd1 | 253982 | 4-May-15 |
| 2459 | 2 | 3 | | | III-1 | Anp32a | 8125 | 2-Jun-15 | 2854 | 2 | 3 | | | III-1 | Asxl3 | 80816 | 4-May-15 |
| 2464 | 2 | 3 | | | III-1 | Antxr2 | 118429 | 23-May-15 | 2856 | 2 | 3 | | | III-1 | Atad1 | 84896 | 4-May-15 |
| 2467 | 2 | 3 | | | III-1 | Anxa10 | 11199 | 4-May-15 | 2870 | 2 | 3 | | | III-1 | Atf5 | 22809 | 21-May-15 |
| 2473 | 2 | 3 | | | III-1 | Anxa5 | 308 | 28-May-15 | 2871 | 2 | 3 | | | III-1 | Atf6 | 22926 | 17-May-15 |
| 2474 | 2 | 3 | | | III-1 | Anxa6 | 309 | 4-May-15 | 2873 | 2 | 3 | | | III-1 | Atf7 | 11016 | 4-May-15 |
| 2480 | 2 | 3 | | | III-1 | Aoc2 | 314 | 21-May-15 | 2875 | 2 | 3 | | | III-1 | Atf7ip2 | 80063 | 4-May-15 |
| 2483 | 2 | 3 | | | III-1 | Aox2 | 344454 | 12-May-15 | 2883 | 2 | 3 | | | III-1 | Atg2a | 23130 | 21-May-15 |
| 2490 | 2 | 3 | | | III-1 | Ap1m1 | 8907 | 4-May-15 | 2887 | 2 | 3 | | | III-1 | Atg4b | 23192 | 23-May-15 |
| 2492 | 2 | 3 | | | III-1 | Ap1s1 | 1174 | 4-May-15 | 2889 | 2 | 3 | | | III-1 | Atg4d | 84971 | 21-May-15 |
| 2502 | 2 | 3 | | | III-1 | Ap3d1 | 8943 | 4-May-15 | 2893 | 2 | 3 | | | III-1 | Atg9b | 285973 | 21-May-15 |
| 2505 | 2 | 3 | | | III-1 | Ap3s1 | 1176 | 4-May-15 | 2897 | 2 | 3 | | | III-1 | Atl2 | 64225 | 23-May-15 |
| 2512 | 2 | 3 | | | III-1 | Ap5m1 | 55745 | 4-May-15 | 2898 | 2 | 3 | | | III-1 | Atl3 | 25923 | 4-May-15 |
| 2516 | 2 | 3 | | | III-1 | Apba1 | 320 | 4-May-15 | 2899 | 2 | 3 | | | III-1 | Atm | 472 | 31-May-15 |
| 2518 | 2 | 3 | | | III-1 | Apba3 | 9546 | 4-May-15 | 2902 | 2 | 3 | | | III-1 | Atoh1 | 474 | 4-May-15 |
| 2521 | 2 | 3 | | | III-1 | Apbb2 | 323 | 23-May-15 | 2905 | 2 | 3 | | | III-1 | Atox1 | 475 | 17-May-15 |
| 2523 | 2 | 3 | | | III-1 | Apc | 324 | 7-Jun-15 | 2906 | 2 | 3 | | | III-1 | Atp10a | 57194 | 21-May-15 |
| 2524 | 2 | 3 | | | III-1 | Apc2 | 10297 | 7-Jun-15 | 2908 | 2 | 3 | | | III-1 | Atp10d | 57205 | 4-May-15 |
| 2526 | 2 | 3 | | | III-1 | Apcs | 325 | 4-May-15 | 2913 | 2 | 3 | | | III-1 | Atp13a1 | 57130 | 4-May-15 |
| 2533 | 2 | 3 | | | III-1 | Aph1c | | | 2917 | 2 | 3 | | | III-1 | Atp13a5 | 344905 | 4-May-15 |
| 2536 | 2 | 3 | | | III-1 | Apitd1 | 378708 | 4-May-15 | 2918 | 2 | 3 | | | III-1 | Atp1a1 | 476 | 7-Jun-15 |
| 2541 | 2 | 3 | | | III-1 | Aplp2 | 334 | 12-May-15 | 2920 | 2 | 3 | | | III-1 | Atp1a3 | 478 | 23-May-15 |
| 2552 | 2 | 3 | | | III-1 | Apobec4 | 403314 | 4-May-15 | 2921 | 2 | 3 | | | III-1 | Atp1a4 | 480 | 12-May-15 |
| 2568 | 2 | 3 | | | III-1 | Apol7b | | | 2924 | 2 | 3 | | | III-1 | Atp1b3 | 483 | 12-May-15 |
| 2576 | 2 | 3 | | | III-1 | Apom | 55937 | 17-May-15 | 2925 | 2 | 3 | | | III-1 | Atp1b4 | 23439 | 4-May-15 |
| 2581 | 2 | 3 | | | III-1 | Apopt1 | 84334 | 4-May-15 | 2928 | 2 | 3 | | | III-1 | Atp2a3 | 489 | 12-May-15 |
| 2583 | 2 | 3 | | | III-1 | Apphp2 | 10513 | 4-May-15 | 2932 | 2 | 3 | | | III-1 | Atp2b4 | 493 | 17-May-15 |
| 2586 | 2 | 3 | | | III-1 | Aprt | 353 | 23-May-15 | 2936 | 2 | 3 | | | III-1 | Atp4b | 496 | 4-May-15 |
| 2587 | 2 | 3 | | | III-1 | Aptx | 54840 | 23-May-15 | 2938 | 2 | 3 | | | III-1 | Atp5b | 506 | 12-May-15 |
| 2590 | 2 | 3 | | | III-1 | Aqp12 | 375318 | 4-May-15 | 2939 | 2 | 3 | | | III-1 | Atp5c1 | 509 | 4-May-15 |
| 2599 | 2 | 3 | | | III-1 | Aqr | 9716 | 4-May-15 | 2940 | 2 | 3 | | | III-1 | Atp5d | 513 | 4-May-15 |
| 2604 | 2 | 3 | | | III-1 | Arap3 | 64411 | 4-May-15 | 2941 | 2 | 3 | | | III-1 | Atp5e | 514 | 4-May-15 |
| 2605 | 2 | 3 | | | III-1 | Arc | 23237 | 7-Jun-15 | 2942 | 2 | 3 | | | III-1 | Atp5f1 | 515 | 12-May-15 |
| 2606 | 2 | 3 | | | III-1 | Arcn1 | 372 | 4-May-15 | 2944 | 2 | 3 | | | III-1 | Atp5g2 | 517 | 4-May-15 |
| 2620 | 2 | 3 | | | III-1 | Arfip1 | 27236 | 4-May-15 | 2945 | 2 | 3 | | | III-1 | Atp5g3 | 518 | 4-May-15 |
| 2634 | 2 | 3 | | | III-1 | Arhgap19 | 84986 | 4-May-15 | 2947 | 2 | 3 | | | III-1 | Atp5j | 522 | 12-May-15 |
| 2635 | 2 | 3 | | | III-1 | Arhgap20 | 57569 | 4-May-15 | 2952 | 2 | 3 | | | III-1 | Atp5s | 27109 | 4-May-15 |
| 2637 | 2 | 3 | | | III-1 | Arhgap21 | 57584 | 4-May-15 | 2955 | 2 | 3 | | | III-1 | Atp6ap1l | 92270 | 4-May-15 |
| 2639 | 2 | 3 | | | III-1 | Arhgap23 | 57636 | 4-May-15 | 2957 | 2 | 3 | | | III-1 | Atp6v0a1 | 535 | 21-May-15 |
| 2646 | 2 | 3 | | | III-1 | Arhgap29 | 9411 | 24-May-15 | 2960 | 2 | 3 | | | III-1 | Atp6v0b | 533 | 3-Jun-15 |
| 2649 | 2 | 3 | | | III-1 | Arhgap32 | 9743 | 4-May-15 | 2967 | 2 | 3 | | | III-1 | Atp6v1a | 523 | 12-May-15 |
| 2650 | 2 | 3 | | | III-1 | Arhgap33 | 115703 | 4-May-15 | 2968 | 2 | 3 | | | III-1 | Atp6v1b1 | 525 | 24-May-15 |
| 2651 | 2 | 3 | | | III-1 | Arhgap33os | | | 2970 | 2 | 3 | | | III-1 | Atp6v1c1 | 528 | 2-Jun-15 |
| 2653 | 2 | 3 | | | III-1 | Arhgap36 | 158763 | 12-May-15 | 2971 | 2 | 3 | | | III-1 | Atp6v1c2 | 245973 | 4-May-15 |
| 2655 | 2 | 3 | | | III-1 | Arhgap4 | 393 | 4-May-15 | 2972 | 2 | 3 | | | III-1 | Atp6v1d | 51382 | 4-May-15 |
| 2657 | 2 | 3 | | | III-1 | Arhgap42 | 143872 | 4-May-15 | 2973 | 2 | 3 | | | III-1 | Atp6v1e1 | 529 | 4-May-15 |
| 2658 | 2 | 3 | | | III-1 | Arhgap44 | 9912 | 4-May-15 | 2974 | 2 | 3 | | | III-1 | Atp6v1e2 | 90423 | 4-May-15 |
| 2660 | 2 | 3 | | | III-1 | Arhgap6 | 395 | 4-May-15 | 2979 | 2 | 3 | | | III-1 | Atp6v1h | 51606 | 4-May-15 |
| 2663 | 2 | 3 | | | III-1 | Arhgdia | 396 | 12-May-15 | 2980 | 2 | 3 | | | III-1 | Atp7a | 538 | 23-May-15 |
| 2666 | 2 | 3 | | | III-1 | Arhgef1 | 9138 | 31-May-15 | 2981 | 2 | 3 | | | III-1 | Atp7b | 540 | 23-May-15 |
| 2668 | 2 | 3 | | | III-1 | Arhgef10l | 55160 | 4-May-15 | 2982 | 2 | 3 | | | III-1 | Atp8a1 | 10396 | 12-May-15 |
| 2669 | 2 | 3 | | | III-1 | Arhgef11 | 9826 | 4-May-15 | 2987 | 2 | 3 | | | III-1 | Atp8b4 | 79895 | 4-May-15 |
| 2674 | 2 | 3 | | | III-1 | Arhgef18 | 23370 | 4-May-15 | 2990 | 2 | 3 | | | III-1 | Atp9b | 374868 | 12-May-15 |
| 2679 | 2 | 3 | | | III-1 | Arhgef28 | 64283 | 4-May-15 | 2994 | 2 | 3 | | | III-1 | Atr | 545 | 13-Jun-15 |
| 2683 | 2 | 3 | | | III-1 | Arhgef38 | 54848 | 4-May-15 | 2995 | 2 | 3 | | | III-1 | Ataid | 51374 | 4-May-15 |
| 2686 | 2 | 3 | | | III-1 | Arhgef40 | 55701 | 4-May-15 | 3001 | 2 | 3 | | | III-1 | Atxn10 | 25814 | 23-May-15 |
| 2688 | 2 | 3 | | | III-1 | Arhgef6 | 9459 | 23-May-15 | 3005 | 2 | 3 | | | III-1 | Atxn3 | 4287 | 7-Jun-15 |
| 2694 | 2 | 3 | | | III-1 | Arid3a | 1820 | 28-May-15 | 3011 | 2 | 3 | | | III-1 | AU015228 | | |
| 2696 | 2 | 3 | | | III-1 | Arid3c | 138715 | 4-May-15 | 3013 | 2 | 3 | | | III-1 | AU015836 | | |

Fig.22 - 61

| | | | | | | | | | | | | | | |
|---|---|---|---|---|---|---|---|---|---|---|---|---|---|---|
| 3016 | 2 | 3 | | III-1 | AU018829 | | | 3371 | 2 | 3 | | III-1 | Best3 | 144453 | 4-May-15 |
| 3022 | 2 | 3 | | III-1 | AU022751 | | | 3380 | 2 | 3 | | III-1 | Bfsp2 | 8419 | 17-May-15 |
| 3039 | 2 | 3 | | III-1 | Aven | 57099 | 4-May-15 | 3382 | 2 | 3 | | III-1 | Bglap2 | | |
| 3043 | 2 | 3 | | III-1 | Avpi1 | 60370 | 21-May-15 | 3384 | 2 | 3 | | III-1 | Bgn | 633 | 17-May-15 |
| 3046 | 2 | 3 | | III-1 | Avpr2 | 554 | 23-May-15 | 3388 | 2 | 3 | | III-1 | Bhlhe22 | 27319 | 4-May-15 |
| 3048 | 2 | 3 | | III-1 | AW046200 | | | 3398 | 2 | 3 | | III-1 | Bik | 638 | 12-May-15 |
| 3049 | 2 | 3 | | III-1 | AW112010 | | | 3400 | 2 | 3 | | III-1 | Bin2 | 51413 | 12-May-15 |
| 3060 | 2 | 3 | | III-1 | Axin1 | 8312 | 4-May-15 | 3408 | 2 | 3 | | III-1 | Blcap | 10904 | 4-May-15 |
| 3061 | 2 | 3 | | III-1 | Axin2 | 8313 | 4-May-15 | 3413 | 2 | 3 | | III-1 | Bloc1s1 | 2647 | 28-May-15 |
| 3065 | 2 | 3 | | III-1 | AY512915 | | | 3415 | 2 | 3 | | III-1 | Bloc1s3 | 388552 | 23-May-15 |
| 3069 | 2 | 3 | | III-1 | Aym1 | | | 3416 | 2 | 3 | | III-1 | Bloc1s4 | 55330 | 4-May-15 |
| 3080 | 2 | 3 | | III-1 | B130034C11Rik | | | 3420 | 2 | 3 | | III-1 | Blvrb | 645 | 4-May-15 |
| 3081 | 2 | 3 | | III-1 | B230112J18Rik | | | 3423 | 2 | 3 | | III-1 | Bmi1 | 648 | 2-Jun-15 |
| 3084 | 2 | 3 | | III-1 | B230206H07Rik | | | 3425 | 2 | 3 | | III-1 | Bmp15 | 9210 | 3-May-15 |
| 3086 | 2 | 3 | | III-1 | B230209E15Rik | | | 3428 | 2 | 3 | | III-1 | Bmp2k | 55589 | 12-May-15 |
| 3089 | 2 | 3 | | III-1 | B230216N24Rik | | | 3431 | 2 | 3 | | III-1 | Bmp5 | 653 | 17-May-15 |
| 3097 | 2 | 3 | | III-1 | B330016D10Rik | | | 3436 | 2 | 3 | | III-1 | Bmper | 168667 | 4-May-15 |
| 3098 | 2 | 3 | | III-1 | B3galnt1 | 8706 | 14-May-15 | 3439 | 2 | 3 | | III-1 | Bmpr2 | 659 | 31-May-15 |
| 3099 | 2 | 3 | | III-1 | B3galnt2 | 148789 | 4-May-15 | 3446 | 2 | 3 | | III-1 | Bnip2 | 663 | 4-May-15 |
| 3105 | 2 | 3 | | III-1 | B3gat1 | 27087 | 4-May-15 | 3448 | 2 | 3 | | III-1 | Bnip3l | 665 | 4-May-15 |
| 3106 | 2 | 3 | | III-1 | B3gat2 | 135152 | 12-May-15 | 3449 | 2 | 3 | | III-1 | Bnipl | 149428 | 4-May-15 |
| 3112 | 2 | 3 | | III-1 | B3gnt4 | 79369 | 4-May-15 | 3451 | 2 | 3 | | III-1 | Bod1 | 91272 | 4-May-15 |
| 3117 | 2 | 3 | | III-1 | B3gnt9 | 84752 | 4-May-15 | 3453 | 2 | 3 | | III-1 | Bok | 666 | 4-May-15 |
| 3119 | 2 | 3 | | III-1 | B430010B23Rik | | | 3454 | 2 | 3 | | III-1 | Bola1 | 51027 | 4-May-15 |
| 3120 | 2 | 3 | | III-1 | B430212C06Rik | | | 3455 | 2 | 3 | | III-1 | Bola2 | 552900 | 7-Jun-15 |
| 3122 | 2 | 3 | | III-1 | B430319G15Rik | | | 3457 | 2 | 3 | | III-1 | Boll | 66037 | 4-May-15 |
| 3126 | 2 | 3 | | III-1 | B4galnt4 | 338707 | 4-May-15 | 3459 | 2 | 3 | | III-1 | Bora | 79886 | 4-May-15 |
| 3128 | 2 | 3 | | III-1 | B4galt2 | 8704 | 4-May-15 | 3465 | 2 | 3 | | III-1 | Bpifa3 | 128861 | 4-May-15 |
| 3129 | 2 | 3 | | III-1 | B4galt3 | 8703 | 7-Jun-15 | 3477 | 2 | 3 | | III-1 | Bpnt1 | 10380 | 4-May-15 |
| 3131 | 2 | 3 | | III-1 | B4galt5 | 9334 | 4-May-15 | 3494 | 2 | 3 | | III-1 | Brf1 | 2972 | 7-Jun-15 |
| 3133 | 2 | 3 | | III-1 | B4galt7 | 11285 | 4-May-15 | 3498 | 2 | 3 | | III-1 | Bricd5 | 283870 | 4-May-15 |
| 3136 | 2 | 3 | | III-1 | B830017H08Rik | | | 3506 | 2 | 3 | | III-1 | Brms1l | 84312 | 4-May-15 |
| 3141 | 2 | 3 | | III-1 | B930059L03Rik | | | 3507 | 2 | 3 | | III-1 | Brox | 148362 | 4-May-15 |
| 3142 | 2 | 3 | | III-1 | B930092H01Rik | | | 3510 | 2 | 3 | | III-1 | Brs3 | 680 | 4-May-15 |
| 3147 | 2 | 3 | | III-1 | Babam1 | 29086 | 4-May-15 | 3512 | 2 | 3 | | III-1 | Brsk2 | 9024 | 28-May-15 |
| 3149 | 2 | 3 | | III-1 | Bace2 | 25825 | 12-May-15 | 3513 | 2 | 3 | | III-1 | Brwd1 | 54014 | 12-May-15 |
| 3151 | 2 | 3 | | III-1 | Bach2 | 60468 | 12-May-15 | 3519 | 2 | 3 | | III-1 | Bsnd | 7809 | 12-May-15 |
| 3154 | 2 | 3 | | III-1 | Bag1 | 573 | 17-May-15 | 3523 | 2 | 3 | | III-1 | Bst1 | 683 | 7-Jun-15 |
| 3160 | 2 | 3 | | III-1 | Bahcc1 | 57597 | 4-May-15 | 3526 | 2 | 3 | | III-1 | Btaf1 | 9044 | 4-May-15 |
| 3161 | 2 | 3 | | III-1 | Bahd1 | 22893 | 4-May-15 | 3530 | 2 | 3 | | III-1 | Btbd16 | 118863 | 4-May-15 |
| 3163 | 2 | 3 | | III-1 | Bai2 | 576 | 4-May-15 | 3532 | 2 | 3 | | III-1 | Btbd18 | 643376 | 4-May-15 |
| 3167 | 2 | 3 | | III-1 | Baiap2l2 | 80115 | 4-May-15 | 3534 | 2 | 3 | | III-1 | Btbd2 | 55643 | 4-May-15 |
| 3168 | 2 | 3 | | III-1 | Baiap3 | 8938 | 4-May-15 | 3536 | 2 | 3 | | III-1 | Btbd6 | 90135 | 4-May-15 |
| 3170 | 2 | 3 | | III-1 | Bambi | 25805 | 12-May-15 | 3543 | 2 | 3 | | III-1 | Btf3l4 | 91408 | 4-May-15 |
| 3172 | 2 | 3 | | III-1 | Banf1 | 8815 | 4-May-15 | 3556 | 2 | 3 | | III-1 | Btnl5-ps | | |
| 3188 | 2 | 3 | | III-1 | Baz1b | 9031 | 4-May-15 | 3568 | 2 | 3 | | III-1 | Bzw1 | 9689 | 4-May-15 |
| 3192 | 2 | 3 | | III-1 | BB019430 | | | 3570 | 2 | 3 | | III-1 | C030006K11Rik | | |
| 3195 | 2 | 3 | | III-1 | BB283400 | | | 3571 | 2 | 3 | | III-1 | C030007H22Rik | | |
| 3197 | 2 | 3 | | III-1 | BB557941 | | | 3573 | 2 | 3 | | III-1 | C030016D13Rik | | |
| 3199 | 2 | 3 | | III-1 | Bbip1 | 92482 | 4-May-15 | 3579 | 2 | 3 | | III-1 | C030037D09Rik | | |
| 3201 | 2 | 3 | | III-1 | Bbs1 | 582 | 29-May-15 | 3580 | 2 | 3 | | III-1 | C030039L03Rik | | |
| 3204 | 2 | 3 | | III-1 | Bbs2 | 583 | 23-May-15 | 3586 | 2 | 3 | | III-1 | C130036L24Rik | | |
| 3205 | 2 | 3 | | III-1 | Bbs4 | 585 | 23-May-15 | 3587 | 2 | 3 | | III-1 | C130046K22Rik | | |
| 3207 | 2 | 3 | | III-1 | Bbs7 | 55212 | 23-May-15 | 3589 | 2 | 3 | | III-1 | C130060C02Rik | | |
| 3208 | 2 | 3 | | III-1 | Bbs9 | 27241 | 31-May-15 | 3594 | 2 | 3 | | III-1 | C150080G10Rik | | |
| 3218 | 2 | 3 | | III-1 | BC006965 | | | 3598 | 2 | 3 | | III-1 | C1galt1c1 | 29071 | 4-May-15 |
| 3219 | 2 | 3 | | III-1 | BC016579 | | | 3601 | 2 | 3 | | III-1 | C1qbp | 708 | 4-May-15 |
| 3223 | 2 | 3 | | III-1 | BC018473 | | | 3603 | 2 | 3 | | III-1 | C1ql1 | 10882 | 4-May-15 |
| 3225 | 2 | 3 | | III-1 | BC020402 | | | 3605 | 2 | 3 | | III-1 | C1ql3 | 389941 | 4-May-15 |
| 3226 | 2 | 3 | | III-1 | BC021614 | | | 3611 | 2 | 3 | | III-1 | C1qtnf5 | 114902 | 4-May-15 |
| 3231 | 2 | 3 | | III-1 | BC023829 | | | 3614 | 2 | 3 | | III-1 | C1qtnf9 | 338872 | 12-May-15 |
| 3232 | 2 | 3 | | III-1 | BC024139 | | | 3616 | 2 | 3 | | III-1 | C1rb | | |
| 3233 | 2 | 3 | | III-1 | BC024386 | | | 3617 | 2 | 3 | | III-1 | C1rl | 51279 | 12-May-15 |
| 3235 | 2 | 3 | | III-1 | BC025920 | | | 3619 | 2 | 3 | | III-1 | C1s2 | | |
| 3241 | 2 | 3 | | III-1 | BC029722 | | | 3620 | 2 | 3 | | III-1 | C2 | 717 | 7-Jun-15 |
| 3243 | 2 | 3 | | III-1 | BC030336 | | | 3625 | 2 | 3 | | III-1 | C230037L18Rik | | |
| 3248 | 2 | 3 | | III-1 | BC031181 | | | 3628 | 2 | 3 | | III-1 | C230052I12Rik | | |
| 3251 | 2 | 3 | | III-1 | BC035044 | | | 3630 | 2 | 3 | | III-1 | C2cd2l | 9854 | 4-May-15 |
| 3254 | 2 | 3 | | III-1 | BC037704 | | | 3635 | 2 | 3 | | III-1 | C2cd4d | 100191040 | 4-May-15 |
| 3255 | 2 | 3 | | III-1 | BC039771 | | | | | | | | | | |
| 3257 | 2 | 3 | | III-1 | BC048403 | | | 3638 | 2 | 3 | | III-1 | C330006A16Rik | | |
| 3263 | 2 | 3 | | III-1 | BC048609 | | | 3645 | 2 | 3 | | III-1 | C330022C24Rik | | |
| 3267 | 2 | 3 | | III-1 | BC049352 | | | 3646 | 2 | 3 | | III-1 | C330024C12Rik | | |
| 3270 | 2 | 3 | | III-1 | BC049730 | | | 3651 | 2 | 3 | | III-1 | C430002E04Rik | | |
| 3274 | 2 | 3 | | III-1 | BC051226 | | | 3658 | 2 | 3 | | III-1 | C530005A16Rik | | |
| 3279 | 2 | 3 | | III-1 | BC052668 | | | 3660 | 2 | 3 | | III-1 | C530044C16Rik | | |
| 3282 | 2 | 3 | | III-1 | BC055111 | | | 3662 | 2 | 3 | | III-1 | C5ar2 | 27202 | 4-May-15 |
| 3293 | 2 | 3 | | III-1 | BC080695 | | | 3672 | 2 | 3 | | III-1 | C77370 | | |
| 3297 | 2 | 3 | | III-1 | Bc1 | | | 3686 | 2 | 3 | | III-1 | C920009B18Rik | | |
| 3302 | 2 | 3 | | III-1 | BC147527 | | | 3688 | 2 | 3 | | III-1 | C920025E04Rik | | |
| 3304 | 2 | 3 | | III-1 | Bcan | 63827 | 12-May-15 | 3690 | 2 | 3 | | III-1 | Cab39 | 51719 | 4-May-15 |
| 3306 | 2 | 3 | | III-1 | Bcap31 | 10134 | 24-May-15 | 3694 | 2 | 3 | | III-1 | Cables2 | 81928 | 4-May-15 |
| 3309 | 2 | 3 | | III-1 | Bcas1 | 8537 | 4-May-15 | 3695 | 2 | 3 | | III-1 | Cabp1 | 9478 | 7-Jun-15 |
| 3315 | 2 | 3 | | III-1 | Bcat1 | 586 | 4-May-15 | 3699 | 2 | 3 | | III-1 | Cabp7 | 164633 | 4-May-15 |
| 3317 | 2 | 3 | | III-1 | Bccip | 56647 | 4-May-15 | 3701 | 2 | 3 | | III-1 | Cabyr | 26256 | 12-May-15 |
| 3320 | 2 | 3 | | III-1 | Bckdha | 593 | 29-May-15 | 3702 | 2 | 3 | | III-1 | Cacfd1 | 11094 | 4-May-15 |
| 3321 | 2 | 3 | | III-1 | Bckdhb | 594 | 23-May-15 | 3708 | 2 | 3 | | III-1 | Cacna1e | 777 | 12-May-15 |
| 3322 | 2 | 3 | | III-1 | Bckdk | 10295 | 4-May-15 | 3712 | 2 | 3 | | III-1 | Cacna1i | 8913 | 7-Jun-15 |
| 3334 | 2 | 3 | | III-1 | Bcl2l2 | 83596 | 4-May-15 | 3719 | 2 | 3 | | III-1 | Cacnb2 | 783 | 23-May-15 |
| 3335 | 2 | 3 | | III-1 | Bcl2l13 | 23786 | 4-May-15 | 3729 | 2 | 3 | | III-1 | Cacng8 | 59283 | 4-May-15 |
| 3338 | 2 | 3 | | III-1 | Bcl2l2 | 599 | 4-May-15 | 3735 | 2 | 3 | | III-1 | Cadm2 | 253559 | 2-Jun-15 |
| 3343 | 2 | 3 | | III-1 | Bcl7b | 9275 | 4-May-15 | 3738 | 2 | 3 | | III-1 | Cadps | 8618 | 4-May-15 |
| 3345 | 2 | 3 | | III-1 | Bcl9 | 607 | 4-May-15 | 3740 | 2 | 3 | | III-1 | Cage1 | 285782 | 4-May-15 |
| 3347 | 2 | 3 | | III-1 | Bclaf1 | 9774 | 4-May-15 | 3742 | 2 | 3 | | III-1 | Calb2 | 794 | 17-May-15 |
| 3352 | 2 | 3 | | III-1 | Bcr | 613 | 24-May-15 | 3746 | 2 | 3 | | III-1 | Calcoco2 | 10241 | 12-May-15 |
| 3364 | 2 | 3 | | III-1 | Bend3 | 57673 | 20-May-15 | 3748 | 2 | 3 | | III-1 | Calcrl | 10203 | 12-May-15 |
| 3367 | 2 | 3 | | III-1 | Bend6 | 221336 | 4-May-15 | 3750 | 2 | 3 | | III-1 | Calhm1 | 255022 | 4-May-15 |
| | | | | | | | | 3756 | 2 | 3 | | III-1 | Calm5 | | |

Fig.22 - 62

| | | | | | | | | | | | | | | | |
|---|---|---|---|---|---|---|---|---|---|---|---|---|---|---|---|
| 3760 | 2 | 3 | | | III-1 | Calr | 811 | 17-May-15 | 4112 | 2 | 3 | | III-1 | Ccng2 | 901 | |
| 3761 | 2 | 3 | | | III-1 | Calr3 | 125972 | 4-May-15 | 4113 | 2 | 3 | | III-1 | Ccnh | 902 | 4-May-15 |
| 3762 | 2 | 3 | | | III-1 | Calr4 | | | 4118 | 2 | 3 | | III-1 | Ccnl1 | 57018 | 7-Jun-15 |
| 3766 | 2 | 3 | | | III-1 | Camk1d | 57118 | 4-May-15 | 4121 | 2 | 3 | | III-1 | Ccnt1 | 904 | 4-May-15 |
| 3767 | 2 | 3 | | | III-1 | Camk1g | 57172 | 4-May-15 | 4129 | 2 | 3 | | III-1 | Ccr10 | 2826 | 7-Jun-15 |
| 3770 | 2 | 3 | | | III-1 | Camk2d | 817 | | 4133 | 2 | 3 | | III-1 | Ccr4 | 1233 | 7-Jun-15 |
| 3774 | 2 | 3 | | | III-1 | Camk4 | 814 | 4-May-15 | 4141 | 2 | 3 | | III-1 | Ccs | 9973 | 12-May-15 |
| 3777 | 2 | 3 | | | III-1 | Camkmt | 79823 | 12-May-15 | 4142 | 2 | 3 | | III-1 | Ccsap | 126731 | |
| 3778 | 2 | 3 | | | III-1 | Camkv | 79012 | 4-May-15 | 4143 | 2 | 3 | | III-1 | Ccser1 | 401145 | 4-May-15 |
| 3784 | 2 | 3 | | | III-1 | Camta1 | 23261 | 4-May-15 | 4156 | 2 | 3 | | III-1 | Cd109 | 135228 | |
| 3785 | 2 | 3 | | | III-1 | Camta2 | 23125 | 4-May-15 | 4158 | 2 | 3 | | III-1 | Cd151 | 977 | 4-May-15 |
| 3793 | 2 | 3 | | | III-1 | Capn1 | 823 | 17-May-15 | 4159 | 2 | 3 | | III-1 | Cd160 | 11126 | 31-May-15 |
| 3795 | 2 | 3 | | | III-1 | Capn11 | 11131 | 4-May-15 | 4161 | 2 | 3 | | III-1 | Cd163l1 | 283316 | 28-May-15 |
| 3799 | 2 | 3 | | | III-1 | Capn2 | 824 | 12-May-15 | 4162 | 2 | 3 | | III-1 | Cd164 | 8763 | 12-May-15 |
| 3802 | 2 | 3 | | | III-1 | Capn6 | 827 | | 4165 | 2 | 3 | | III-1 | Cd180 | 4064 | 4-May-15 |
| 3805 | 2 | 3 | | | III-1 | Capn9 | 10753 | 4-May-15 | 4176 | 2 | 3 | | III-1 | Cd209a | | |
| 3808 | 2 | 3 | | | III-1 | Caprin1 | 4076 | 4-May-15 | 4194 | 2 | 3 | | III-1 | Cd2bp2 | 10421 | 4-May-15 |
| 3810 | 2 | 3 | | | III-1 | Caps2 | 84698 | 4-May-15 | 4196 | 2 | 3 | | III-1 | Cd300c | 10871 | |
| 3831 | 2 | 3 | | | III-1 | Car9 | | | 4197 | 2 | 3 | | III-1 | Cd300e | 342510 | 4-May-15 |
| 3832 | 2 | 3 | | | III-1 | Card10 | 29775 | 4-May-15 | 4200 | 2 | 3 | | III-1 | Cd300lf | 146722 | 4-May-15 |
| 3833 | 2 | 3 | | | III-1 | Card11 | 84433 | 4-May-15 | 4201 | 2 | 3 | | III-1 | Cd300lg | 146894 | |
| 3835 | 2 | 3 | | | III-1 | Card6 | 84674 | 12-May-15 | 4202 | 2 | 3 | | III-1 | Cd300lh | | |
| 3836 | 2 | 3 | | | III-1 | Card9 | 64170 | 24-May-15 | 4204 | 2 | 3 | | III-1 | Cd320 | 51293 | 4-May-15 |
| 3839 | 2 | 3 | | | III-1 | Cark1 | 55739 | 4-May-15 | 4205 | 2 | 3 | | III-1 | Cd33 | 945 | |
| 3845 | 2 | 3 | | | III-1 | Casc1 | 55259 | 4-May-15 | 4208 | 2 | 3 | | III-1 | Cd37 | 951 | 4-May-15 |
| 3848 | 2 | 3 | | | III-1 | Casc5 | 57082 | | 4213 | 2 | 3 | | III-1 | Cd3g | 917 | 2015/6/7 |
| 3853 | 2 | 3 | | | III-1 | Casp1 | 834 | | 4226 | 2 | 3 | | III-1 | Cd59b | | |
| 3855 | 2 | 3 | | | III-1 | Casp14 | 23581 | 4-May-15 | 4241 | 2 | 3 | | III-1 | Cd83 | 9308 | |
| 3856 | 2 | 3 | | | III-1 | Casp2 | 835 | | 4247 | 2 | 3 | | III-1 | Cd93 | 22918 | |
| 3867 | 2 | 3 | | | III-1 | Cass4 | 57091 | | 4248 | 2 | 3 | | III-1 | Cd96 | 10225 | 12-May-15 |
| 3869 | 2 | 3 | | | III-1 | Casz1 | 54897 | 4-May-15 | 4250 | 2 | 3 | | III-1 | Cdc9l2 | 83692 | 4-May-15 |
| 3870 | 2 | 3 | | | III-1 | Cat | 847 | 7-Jun-15 | 4256 | 2 | 3 | | III-1 | Cdc14b | 8555 | 13-Jun-15 |
| 3871 | 2 | 3 | | | III-1 | Catip | 375307 | 21-May-15 | 4257 | 2 | 3 | | III-1 | Cdc16 | 8881 | 12-May-15 |
| 3874 | 2 | 3 | | | III-1 | Catsper3 | 347732 | 4-May-15 | 4262 | 2 | 3 | | III-1 | Cdc25b | 994 | |
| 3876 | 2 | 3 | | | III-1 | Catsperb | 79820 | 4-May-15 | 4263 | 2 | 3 | | III-1 | Cdc25c | 995 | |
| 3878 | 2 | 3 | | | III-1 | Catsperg1 | | | 4265 | 2 | 3 | | III-1 | Cdc27 | 996 | 31-May-15 |
| 3889 | 2 | 3 | | | III-1 | Cbll1 | 79872 | 12-May-15 | 4267 | 2 | 3 | | III-1 | Cdc37 | 11140 | 17-May-15 |
| 3891 | 2 | 3 | | | III-1 | Cbln2 | 147381 | 4-May-15 | 4272 | 2 | 3 | | III-1 | Cdc42bpb | 9578 | 4-May-15 |
| 3893 | 2 | 3 | | | III-1 | Cbln4 | 140689 | 4-May-15 | 4273 | 2 | 3 | | III-1 | Cdc42bpg | 55561 | 4-May-15 |
| 3897 | 2 | 3 | | | III-1 | Cbr4 | 84869 | 4-May-15 | 4274 | 2 | 3 | | III-1 | Cdc42ep1 | 11135 | 4-May-15 |
| 3900 | 2 | 3 | | | III-1 | Cbx1 | 10951 | | 4275 | 2 | 3 | | III-1 | Cdc42ep2 | 10435 | 4-May-15 |
| 3903 | 2 | 3 | | | III-1 | Cbx4 | 8535 | 17-May-15 | 4276 | 2 | 3 | | III-1 | Cdc42ep3 | 10602 | 4-May-15 |
| 3907 | 2 | 3 | | | III-1 | Cbx8 | 57332 | 4-May-15 | 4286 | 2 | 3 | | III-1 | Cdca2 | 157313 | |
| 3917 | 2 | 3 | | | III-1 | Ccdc101 | 112869 | 4-May-15 | 4292 | 2 | 3 | | III-1 | Cdca8 | 55143 | 4-May-15 |
| 3918 | 2 | 3 | | | III-1 | Ccdc102a | 92922 | 12-May-15 | 4294 | 2 | 3 | | III-1 | Cdcp2 | 200008 | 4-May-15 |
| 3919 | 2 | 3 | | | III-1 | Ccdc103 | 388389 | 23-May-15 | 4296 | 2 | 3 | | III-1 | Cdh10 | 1008 | 12-May-15 |
| 3921 | 2 | 3 | | | III-1 | Ccdc105 | 126402 | 4-May-15 | 4297 | 2 | 3 | | III-1 | Cdh11 | 1009 | |
| 3924 | 2 | 3 | | | III-1 | Ccdc108 | 255101 | 4-May-15 | 4300 | 2 | 3 | | III-1 | Cdh15 | 1013 | 12-May-15 |
| 3927 | 2 | 3 | | | III-1 | Ccdc110 | 256309 | 4-May-15 | 4303 | 2 | 3 | | III-1 | Cdh18 | 1016 | 12-May-15 |
| 3929 | 2 | 3 | | | III-1 | Ccdc113 | 29070 | 12-May-15 | 4305 | 2 | 3 | | III-1 | Cdh2 | 1000 | 24-May-15 |
| 3932 | 2 | 3 | | | III-1 | Ccdc116 | 164592 | 28-May-15 | 4306 | 2 | 3 | | III-1 | Cdh20 | 28316 | 12-May-15 |
| 3933 | 2 | 3 | | | III-1 | Ccdc117 | 150275 | 4-May-15 | 4308 | 2 | 3 | | III-1 | Cdh23 | 64072 | 23-May-15 |
| 3936 | 2 | 3 | | | III-1 | Ccdc121 | 79635 | 4-May-15 | 4312 | 2 | 3 | | III-1 | Cdh4 | 1002 | 4-May-15 |
| 3938 | 2 | 3 | | | III-1 | Ccdc124 | 115098 | 4-May-15 | 4319 | 2 | 3 | | III-1 | Cdhr2 | 54825 | 4-May-15 |
| 3941 | 2 | 3 | | | III-1 | Ccdc127 | 133957 | 4-May-15 | 4322 | 2 | 3 | | III-1 | Cdip1 | 29965 | 4-May-15 |
| 3947 | 2 | 3 | | | III-1 | Ccdc135 | 84229 | 4-May-15 | 4330 | 2 | 3 | | III-1 | Cdk15 | 65061 | 4-May-15 |
| 3949 | 2 | 3 | | | III-1 | Ccdc137 | 339230 | 4-May-15 | 4334 | 2 | 3 | | III-1 | Cdk19 | 23097 | 12-May-15 |
| 3950 | 2 | 3 | | | III-1 | Ccdc138 | 165056 | 12-May-15 | 4340 | 2 | 3 | | III-1 | Cdk4 | 1019 | 31-May-15 |
| 3953 | 2 | 3 | | | III-1 | Ccdc142 | 84865 | 4-May-15 | 4350 | 2 | 3 | | III-1 | Cdk9 | 1025 | 4-May-15 |
| 3954 | 2 | 3 | | | III-1 | Ccdc144b | 284047 | 4-May-15 | 4352 | 2 | 3 | | III-1 | Cdkl1 | 8814 | 21-May-15 |
| 3958 | 2 | 3 | | | III-1 | Ccdc149 | 91050 | 4-May-15 | 4353 | 2 | 3 | | III-1 | Cdkl2 | 8999 | 4-May-15 |
| 3969 | 2 | 3 | | | III-1 | Ccdc160 | 347475 | 12-May-15 | 4355 | 2 | 3 | | III-1 | Cdkl4 | 344387 | |
| 3970 | 2 | 3 | | | III-1 | Ccdc162 | 221262 | 4-May-15 | 4358 | 2 | 3 | | III-1 | Cdkn1b | 1027 | 31-May-15 |
| 3974 | 2 | 3 | | | III-1 | Ccdc169 | 728591 | 12-May-15 | 4360 | 2 | 3 | | III-1 | Cdkn2a | 1029 | 24-May-15 |
| 3976 | 2 | 3 | | | III-1 | Ccdc170 | 80129 | 4-May-15 | 4361 | 2 | 3 | | III-1 | Cdkn2aip | 55602 | 4-May-15 |
| 3977 | 2 | 3 | | | III-1 | Ccdc171 | 203238 | 4-May-15 | 4365 | 2 | 3 | | III-1 | Cdkn2d | 1032 | |
| 3980 | 2 | 3 | | | III-1 | Ccdc174 | 51244 | 4-May-15 | 4366 | 2 | 3 | | III-1 | Cdkn3 | 1033 | |
| 3981 | 2 | 3 | | | III-1 | Ccdc175 | 729665 | 4-May-15 | 4369 | 2 | 3 | | III-1 | Cdon | 50937 | |
| 3983 | 2 | 3 | | | III-1 | Ccdc177 | 56936 | 4-May-15 | 4371 | 2 | 3 | | III-1 | Cdr1 | 1038 | 4-May-15 |
| 3989 | 2 | 3 | | | III-1 | Ccdc185 | 164127 | 4-May-15 | 4374 | 2 | 3 | | III-1 | Cdr14 | 284040 | 4-May-15 |
| 3991 | 2 | 3 | | | III-1 | Ccdc22 | 28952 | 4-May-15 | 4376 | 2 | 3 | | III-1 | Cds2 | 8760 | 4-May-15 |
| 3993 | 2 | 3 | | | III-1 | Ccdc24 | 149473 | 12-May-15 | 4379 | 2 | 3 | | III-1 | Cdv3 | 55573 | 4-May-15 |
| 3994 | 2 | 3 | | | III-1 | Ccdc25 | 55246 | 12-May-15 | 4384 | 2 | 3 | | III-1 | Cdyl2 | 124359 | 4-May-15 |
| 3998 | 2 | 3 | | | III-1 | Ccdc3 | 83643 | 12-May-15 | 4387 | 2 | 3 | | III-1 | Ceacam11 | | |
| 4000 | 2 | 3 | | | III-1 | Ccdc32 | 90416 | 4-May-15 | 4389 | 2 | 3 | | III-1 | Ceacam13 | | |
| 4003 | 2 | 3 | | | III-1 | Ccdc34os | | | 4396 | 2 | 3 | | III-1 | Ceacam20 | 125931 | 4-May-15 |
| 4011 | 2 | 3 | | | III-1 | Ccdc43 | 124808 | 4-May-15 | 4400 | 2 | 3 | | III-1 | Ceacam-ps1 | | |
| 4012 | 2 | 3 | | | III-1 | Ccdc47 | 57003 | 4-May-15 | 4404 | 2 | 3 | | III-1 | Cebpe | 1053 | 4-May-15 |
| 4014 | 2 | 3 | | | III-1 | Ccdc51 | 79714 | 4-May-15 | 4405 | 2 | 3 | | III-1 | Cebpg | 1054 | 28-May-15 |
| 4016 | 2 | 3 | | | III-1 | Ccdc54 | 84692 | 4-May-15 | 4408 | 2 | 3 | | III-1 | Cecr2 | 27443 | |
| 4020 | 2 | 3 | | | III-1 | Ccdc59 | 29080 | 4-May-15 | 4409 | 2 | 3 | | III-1 | Cecr5 | 27440 | 4-May-15 |
| 4021 | 2 | 3 | | | III-1 | Ccdc6 | 8030 | | 4410 | 2 | 3 | | III-1 | Cecr6 | 27439 | 4-May-15 |
| 4025 | 2 | 3 | | | III-1 | Ccdc63 | 160762 | 12-May-15 | 4417 | 2 | 3 | | III-1 | Celf3 | 11189 | 4-May-15 |
| 4027 | 2 | 3 | | | III-1 | Ccdc64b | 146439 | 4-May-15 | 4419 | 2 | 3 | | III-1 | Celf5 | 60680 | 3-Jun-15 |
| 4030 | 2 | 3 | | | III-1 | Ccdc67 | 159989 | 4-May-15 | 4421 | 2 | 3 | | III-1 | Celrr | | |
| 4031 | 2 | 3 | | | III-1 | Ccdc68 | 80323 | | 4429 | 2 | 3 | | III-1 | Celsr2 | 1952 | 31-May-15 |
| 4032 | 2 | 3 | | | III-1 | Ccdc69 | 26112 | | 4434 | 2 | 3 | | III-1 | Celsr3 | 1951 | 12-May-15 |
| 4037 | 2 | 3 | | | III-1 | Ccdc73 | 493860 | 4-May-15 | 4437 | 2 | 3 | | III-1 | Cenpm | 79019 | |
| 4046 | 2 | 3 | | | III-1 | Ccdc83 | 220047 | 4-May-15 | 4443 | 2 | 3 | | III-1 | Cenpu | 79682 | |
| 4048 | 2 | 3 | | | III-1 | Ccdc85a | 114800 | 4-May-15 | 4445 | 2 | 3 | | III-1 | Cenpw | 387103 | |
| 4056 | 2 | 3 | | | III-1 | Ccdc89 | 220388 | 4-May-15 | 4447 | 2 | 3 | | III-1 | Cep112 | 201134 | 12-May-15 |
| 4063 | 2 | 3 | | | III-1 | Ccdc96 | 257236 | 28-May-15 | 4448 | 2 | 3 | | III-1 | Cep120 | 153241 | 4-May-15 |
| 4071 | 2 | 3 | | | III-1 | Ccl1 | 6346 | | 4451 | 2 | 3 | | III-1 | Cep135 | 9662 | 23-May-15 |
| 4092 | 2 | 3 | | | III-1 | Ccl7 | 6354 | | 4455 | 2 | 3 | | III-1 | Cep170 | 9859 | 12-May-15 |
| 4095 | 2 | 3 | | | III-1 | Ccm2 | 83605 | 23-May-15 | 4457 | 2 | 3 | | III-1 | Cep19 | 84984 | 4-May-15 |
| 4097 | 2 | 3 | | | III-1 | Ccna1 | 8900 | 12-May-15 | 4462 | 2 | 3 | | III-1 | Cep41 | 95681 | 23-May-15 |
| 4106 | 2 | 3 | | | III-1 | Ccnd3 | 896 | 12-May-15 | 4464 | 2 | 3 | | III-1 | Cep55 | 55165 | 4-May-15 |

Fig.22 - 63

| | | | | | | | |
|---|---|---|---|---|---|---|---|
| 4466 | 2 | 3 | III-1 | Cep57l1 | 285753 | 12-May-15 |
| 4467 | 2 | 3 | III-1 | Cep63 | 80254 | 4-May-15 |
| 4468 | 2 | 3 | III-1 | Cep68 | 23177 | 7-Jun-15 |
| 4470 | 2 | 3 | III-1 | Cep72 | 55722 | |
| 4473 | 2 | 3 | III-1 | Cep83 | 51134 | 12-May-15 |
| 4474 | 2 | 3 | III-1 | Cep83os | | |
| 4481 | 2 | 3 | III-1 | Cer1 | 9350 | 4-May-15 |
| 4488 | 2 | 3 | III-1 | Cers4 | 79603 | 4-May-15 |
| 4510 | 2 | 3 | III-1 | Cetn1 | 1068 | 4-May-15 |
| 4512 | 2 | 3 | III-1 | Cetn3 | 1070 | 12-May-15 |
| 4513 | 2 | 3 | III-1 | Cetn4 | | |
| 4514 | 2 | 3 | III-1 | Cfb | 629 | |
| 4515 | 2 | 3 | III-1 | Cfc1 | 55997 | 4-May-15 |
| 4519 | 2 | 3 | III-1 | Cfhr1 | 3078 | 23-May-15 |
| 4521 | 2 | 3 | III-1 | Cfi | 3426 | |
| 4522 | 2 | 3 | III-1 | Cfl1 | 1072 | 7-Jun-15 |
| 4524 | 2 | 3 | III-1 | Cflar | 8837 | 31-May-15 |
| 4527 | 2 | 3 | III-1 | Cga | 1081 | 7/6/7 |
| 4536 | 2 | 3 | III-1 | Chad | 1101 | 4-May-15 |
| 4540 | 2 | 3 | III-1 | Champ1 | 283489 | 4-May-15 |
| 4544 | 2 | 3 | III-1 | Chchd2 | 51142 | 21-May-15 |
| 4546 | 2 | 3 | III-1 | Chchd4 | 131474 | 4-May-15 |
| 4550 | 2 | 3 | III-1 | Chd1 | 1105 | 12-May-15 |
| 4553 | 2 | 3 | III-1 | Chd3 | 1107 | 4-May-15 |
| 4554 | 2 | 3 | III-1 | Chd3os | | |
| 4558 | 2 | 3 | III-1 | Chd7 | 55636 | 23-May-15 |
| 4559 | 2 | 3 | III-1 | Chd8 | 57680 | 12-May-15 |
| 4561 | 2 | 3 | III-1 | Chdh | 55349 | 21-May-15 |
| 4567 | 2 | 3 | III-1 | Chgb | 1114 | 21-May-15 |
| 4574 | 2 | 3 | III-1 | Chil4 | | |
| 4577 | 2 | 3 | III-1 | Chka | 1119 | |
| 4578 | 2 | 3 | III-1 | Chkb | 1120 | 22-May-15 |
| 4581 | 2 | 3 | III-1 | Chn1 | 1121 | 7-Jun-15 |
| 4590 | 2 | 3 | III-1 | Chmp5 | 51510 | 31-May-15 |
| 4599 | 2 | 3 | III-1 | Chp2 | 63928 | 4-May-15 |
| 4600 | 2 | 3 | III-1 | Chpf | 79586 | |
| 4601 | 2 | 3 | III-1 | Chpf2 | 54480 | 4-May-15 |
| 4603 | 2 | 3 | III-1 | Chrac1 | 54108 | 12-May-15 |
| 4609 | 2 | 3 | III-1 | Chrm3 | 1131 | 4-May-15 |
| 4611 | 2 | 3 | III-1 | Chrm5 | 1133 | 4-May-15 |
| 4619 | 2 | 3 | III-1 | Chrna7 | 1139 | 7-Jun-15 |
| 4622 | 2 | 3 | III-1 | Chrnb2 | 1141 | 23-May-15 |
| 4623 | 2 | 3 | III-1 | Chrnb3 | 1142 | 12-May-15 |
| 4625 | 2 | 3 | III-1 | Chrnd | 1144 | 7-May-15 |
| 4630 | 2 | 3 | III-1 | Chst11 | 50515 | 4-May-15 |
| 4632 | 2 | 3 | III-1 | Chst13 | 166012 | 4-May-15 |
| 4635 | 2 | 3 | III-1 | Chst2 | 9435 | |
| 4636 | 2 | 3 | III-1 | Chst3 | 9469 | |
| 4638 | 2 | 3 | III-1 | Chst5 | 23563 | 4-May-15 |
| 4641 | 2 | 3 | III-1 | Chst9 | 83539 | 4-May-15 |
| 4642 | 2 | 3 | III-1 | Chsy1 | 22856 | 4-May-15 |
| 4649 | 2 | 3 | III-1 | Ciao1 | 9391 | 4-May-15 |
| 4652 | 2 | 3 | III-1 | Cib1 | 10519 | 4-May-15 |
| 4656 | 2 | 3 | III-1 | Cic | 23152 | 17-May-15 |
| 4667 | 2 | 3 | III-1 | Cirh1a | 84916 | 12-May-15 |
| 4668 | 2 | 3 | III-1 | Cisd1 | 55847 | 4-May-15 |
| 4669 | 2 | 3 | III-1 | Cisd2 | 493856 | 2-Jun-15 |
| 4671 | 2 | 3 | III-1 | Cish | 1154 | 4-May-15 |
| 4672 | 2 | 3 | III-1 | Cistr-act | 102216 268 | 12-May-15 |
| 4678 | 2 | 3 | III-1 | CK137956 | | |
| 4689 | 2 | 3 | III-1 | Ckslbrt | | |
| 4700 | 2 | 3 | III-1 | Clcc1 | 23155 | 4-May-15 |
| 4704 | 2 | 3 | III-1 | Clcn3 | 1182 | 4-May-15 |
| 4705 | 2 | 3 | III-1 | Clcn4-2 | | |
| 4707 | 2 | 3 | III-1 | Clcn6 | 1185 | |
| 4708 | 2 | 3 | III-1 | Clcn7 | 1186 | 23-May-15 |
| 4709 | 2 | 3 | III-1 | Clcnka | 1187 | 4-May-15 |
| 4714 | 2 | 3 | III-1 | Cldn12 | 9069 | 4-May-15 |
| 4717 | 2 | 3 | III-1 | Cldn15 | 24146 | |
| 4720 | 2 | 3 | III-1 | Cldn18 | 51208 | 12-May-15 |
| 4727 | 2 | 3 | III-1 | Cldn25 | 644672 | 4-May-15 |
| 4735 | 2 | 3 | III-1 | Cldn9 | 9080 | 4-May-15 |
| 4736 | 2 | 3 | III-1 | Cldnd2 | 125875 | 4-May-15 |
| 4741 | 2 | 3 | III-1 | Clec4a | 161198 | 4-May-15 |
| 4744 | 2 | 3 | III-1 | Clec1a | 51267 | |
| 4746 | 2 | 3 | III-1 | Clec2d | 29121 | 4-May-15 |
| 4748 | 2 | 3 | III-1 | Clec2f | | |
| 4753 | 2 | 3 | III-1 | Clec3a | 10143 | 14-May-15 |
| 4760 | 2 | 3 | III-1 | Clec4b2 | | |
| 4762 | 2 | 3 | III-1 | Clec4e | 26253 | 4-May-15 |
| 4766 | 2 | 3 | III-1 | Clec5a | 23601 | |
| 4769 | 2 | 3 | III-1 | Clgn | 1047 | 13-Jun-15 |
| 4777 | 2 | 3 | III-1 | Clip1 | 6249 | 4-May-15 |
| 4778 | 2 | 3 | III-1 | Clip2 | 7461 | 7-Jun-15 |
| 4781 | 2 | 3 | III-1 | Clk1 | 1195 | 7-Jun-15 |
| 4787 | 2 | 3 | III-1 | Cln3 | 1201 | 23-May-15 |
| 4788 | 2 | 3 | III-1 | Cln5 | 1203 | 23-May-15 |
| 4790 | 2 | 3 | III-1 | Cln8 | 2055 | |
| 4799 | 2 | 3 | III-1 | Clptm1 | 1209 | 4-May-15 |
| 4807 | 2 | 3 | III-1 | Clstn2 | 64084 | 12-May-15 |
| 4814 | 2 | 3 | III-1 | Cluh | 23277 | 12-May-15 |
| 4823 | 2 | 3 | III-1 | Cmc1 | 152100 | 4-May-15 |
| 4824 | 2 | 3 | III-1 | Cmc2 | 56942 | |
| 4825 | 2 | 3 | III-1 | Cmip | 80790 | 12-May-15 |
| 4833 | 2 | 3 | III-1 | Cmss1 | 84319 | |
| 4839 | 2 | 3 | III-1 | Cmtm5 | 116173 | 4-May-15 |
| 4843 | 2 | 3 | III-1 | Cmtr1 | 23070 | 12-May-15 |

| | | | | | | | |
|---|---|---|---|---|---|---|---|
| 4848 | 2 | 3 | III-1 | Cndp1 | 84735 | 4-May-15 |
| 4849 | 2 | 3 | III-1 | Cndp2 | 55748 | 12-May-15 |
| 4852 | 2 | 3 | III-1 | Cnga1 | 1259 | 23-May-15 |
| 4854 | 2 | 3 | III-1 | Cnga3 | 1261 | 31-May-15 |
| 4855 | 2 | 3 | III-1 | Cnga4 | 1262 | 4-May-15 |
| 4858 | 2 | 3 | III-1 | Cnih1 | 10175 | 4-May-15 |
| 4859 | 2 | 3 | III-1 | Cnih2 | 254263 | 4-May-15 |
| 4860 | 2 | 3 | III-1 | Cnih3 | 149111 | 4-May-15 |
| 4864 | 2 | 3 | III-1 | Cnksr3 | 154043 | 4-May-15 |
| 4870 | 2 | 3 | III-1 | Cnnm3 | 26505 | 4-May-15 |
| 4873 | 2 | 3 | III-1 | Cnot10 | 25904 | 21-May-15 |
| 4875 | 2 | 3 | III-1 | Cnot2 | 4848 | 28-May-15 |
| 4892 | 2 | 3 | III-1 | Cntd1 | 124817 | 4-May-15 |
| 4895 | 2 | 3 | III-1 | Cntln | 54875 | 1-Jun-15 |
| 4897 | 2 | 3 | III-1 | Cntn2 | 6900 | 4-May-15 |
| 4903 | 2 | 3 | III-1 | Cntnap2 | 26047 | 12-May-15 |
| 4913 | 2 | 3 | III-1 | Coa5 | 493753 | 4-May-15 |
| 4918 | 2 | 3 | III-1 | Cobll1 | 22837 | 4-May-15 |
| 4920 | 2 | 3 | III-1 | Cog1 | 9382 | 23-May-15 |
| 4926 | 2 | 3 | III-1 | Cog7 | 91949 | 23-May-15 |
| 4930 | 2 | 3 | III-1 | Col11a1 | 1301 | 23-May-15 |
| 4933 | 2 | 3 | III-1 | Col13a1 | 1305 | 12-May-15 |
| 4939 | 2 | 3 | III-1 | Col19a1 | 1310 | 12-May-15 |
| 4947 | 2 | 3 | III-1 | Col26a1 | 136227 | 4-May-15 |
| 4950 | 2 | 3 | III-1 | Col2a1 | 1280 | |
| 4966 | 2 | 3 | III-1 | Col6a5 | 256076 | 4-May-15 |
| 4971 | 2 | 3 | III-1 | Col9a1 | 1297 | 23-May-15 |
| 4974 | 2 | 3 | III-1 | Colec10 | 10584 | 4-May-15 |
| 4977 | 2 | 3 | III-1 | Colgalt2 | 23127 | |
| 4981 | 2 | 3 | III-1 | Commd2 | 51122 | 4-May-15 |
| 4984 | 2 | 3 | III-1 | Commd5 | 28991 | 14-May-15 |
| 4988 | 2 | 3 | III-1 | Commd9 | 29099 | 12-May-15 |
| 4992 | 2 | 3 | III-1 | Copa | 1314 | 4-May-15 |
| 5001 | 2 | 3 | III-1 | Cops4 | 51138 | 4-May-15 |
| 5010 | 2 | 3 | III-1 | Coq10b | 80219 | 4-May-15 |
| 5011 | 2 | 3 | III-1 | Coq2 | 27235 | 12-May-15 |
| 5012 | 2 | 3 | III-1 | Coq3 | 51805 | 9-May-15 |
| 5013 | 2 | 3 | III-1 | Coq4 | 51117 | 3-Jun-15 |
| 5017 | 2 | 3 | III-1 | Coq9 | 57017 | 3-May-15 |
| 5018 | 2 | 3 | III-1 | Corin | 10699 | 10-May-15 |
| 5023 | 2 | 3 | III-1 | Coro2b | 10391 | 4-May-15 |
| 5028 | 2 | 3 | III-1 | Cox10 | 1352 | 22-May-15 |
| 5031 | 2 | 3 | III-1 | Cox15 | 1355 | 23-May-15 |
| 5032 | 2 | 3 | III-1 | Cox16 | 51241 | 4-May-15 |
| 5033 | 2 | 3 | III-1 | Cox17 | 10063 | 4-May-15 |
| 5034 | 2 | 3 | III-1 | Cox18 | 285521 | 4-May-15 |
| 5035 | 2 | 3 | III-1 | Cox19 | 90639 | 4-May-15 |
| 5040 | 2 | 3 | III-1 | Cox5b | 1329 | 21-May-15 |
| 5041 | 2 | 3 | III-1 | Cox6a1 | 1337 | 12-May-15 |
| 5045 | 2 | 3 | III-1 | Cox6c | 1345 | 4-May-15 |
| 5048 | 2 | 3 | III-1 | Cox7a2l | 9167 | 4-May-15 |
| 5050 | 2 | 3 | III-1 | Cox7b2 | 170712 | 4-May-15 |
| 5052 | 2 | 3 | III-1 | Cox8a | 1351 | 28-May-15 |
| 5061 | 2 | 3 | III-1 | Cpa6 | 57094 | 16-Jun-15 |
| 5068 | 2 | 3 | III-1 | Cpeb3 | 22849 | |
| 5069 | 2 | 3 | III-1 | Cpeb4 | 80315 | |
| 5070 | 2 | 3 | III-1 | Cped1 | 79974 | |
| 5072 | 2 | 3 | III-1 | Cplx2 | | |
| 5074 | 2 | 3 | III-1 | Cplx2 | 10814 | 12-May-15 |
| 5075 | 2 | 3 | III-1 | Cplx3 | 594855 | 4-May-15 |
| 5076 | 2 | 3 | III-1 | Cplx4 | 339302 | 4-May-15 |
| 5077 | 2 | 3 | III-1 | Cpm | 1368 | 12-May-15 |
| 5080 | 2 | 3 | III-1 | Cpne1 | 8904 | 3-May-15 |
| 5082 | 2 | 3 | III-1 | Cpne3 | 8895 | 3-May-15 |
| 5088 | 2 | 3 | III-1 | Cpne9 | 151835 | 12-May-15 |
| 5090 | 2 | 3 | III-1 | Cpped1 | 55313 | 4-May-15 |
| 5096 | 2 | 3 | III-1 | Cpsf3l | 54973 | 4-May-15 |
| 5099 | 2 | 3 | III-1 | Cpsf6 | 11052 | 1-Jun-15 |
| 5103 | 2 | 3 | III-1 | Cpt1c | 126129 | 28-May-15 |
| 5104 | 2 | 3 | III-1 | Cpt2 | 1376 | 23-May-15 |
| 5115 | 2 | 3 | III-1 | Cramp1l | 57585 | 4-May-15 |
| 5117 | 2 | 3 | III-1 | Crb1 | 23418 | 23-May-15 |
| 5120 | 2 | 3 | III-1 | Crbn | 51185 | 4-May-15 |
| 5123 | 2 | 3 | III-1 | Creb1 | 1385 | 2-Jun-15 |
| 5125 | 2 | 3 | III-1 | Creb3l1 | 90993 | |
| 5130 | 2 | 3 | III-1 | Crebbp | 1387 | 23-May-15 |
| 5131 | 2 | 3 | III-1 | Crebl2 | 1389 | 5-May-15 |
| 5133 | 2 | 3 | III-1 | Crebzf | 58487 | 4-May-15 |
| 5135 | 2 | 3 | III-1 | Creg2 | 200407 | 4-May-15 |
| 5139 | 2 | 3 | III-1 | Crh | 1392 | 4-May-15 |
| 5147 | 2 | 3 | III-1 | Cript | 9419 | 4-May-15 |
| 5150 | 2 | 3 | III-1 | Crisp3 | 10321 | |
| 5152 | 2 | 3 | III-1 | Crispld1 | 83690 | 4-May-15 |
| 5154 | 2 | 3 | III-1 | Crk | 1398 | 17-May-15 |
| 5157 | 2 | 3 | III-1 | Crlf2 | 64109 | 12-May-15 |
| 5160 | 2 | 3 | III-1 | Crmp1 | 1400 | 4-May-15 |
| 5161 | 2 | 3 | III-1 | Crnde | 643911 | 20-May-15 |
| 5165 | 2 | 3 | III-1 | Crot | 54677 | |
| 5167 | 2 | 3 | III-1 | Crtac1 | 55118 | 4-May-15 |
| 5170 | 2 | 3 | III-1 | Crtc1 | 23373 | 4-May-15 |
| 5171 | 2 | 3 | III-1 | Crtc2 | 200186 | 4-May-15 |
| 5176 | 2 | 3 | III-1 | Cry2 | 1408 | 20-May-15 |
| 5189 | 2 | 3 | III-1 | Crygd | 1421 | 4-May-15 |
| 5190 | 2 | 3 | III-1 | Cryge | | |
| 5195 | 2 | 3 | III-1 | Crym | 1428 | 23-May-15 |
| 5200 | 2 | 3 | III-1 | Csdc2 | 27254 | 4-May-15 |
| 5201 | 2 | 3 | III-1 | Csde1 | 7812 | 1-Jun-15 |

Fig.22 - 64

| | | | | | | | | | | | | | | |
|---|---|---|---|---|---|---|---|---|---|---|---|---|---|---|
| 5204 | 2 | 3 | | | III-1 | Csf1r | 1436 | 24-May-15 | 5579 | 2 | 3 | | III-1 | D38wg0562e | | |
| 5205 | 2 | 3 | | | III-1 | Csf2 | 1437 | 4-May-15 | 5580 | 2 | 3 | | III-1 | D8Ertd254e | 1601 | |
| 5208 | 2 | 3 | | | III-1 | Csf2rb2 | 23772 | | 5586 | 2 | 3 | | III-1 | D430042O09Rik | | |
| 5209 | 2 | 3 | | | III-1 | Csf3 | 1440 | 12-May-15 | 5601 | 2 | 3 | | III-1 | D630041G03Rik | | |
| 5211 | 2 | 3 | | | III-1 | Csgalnact1 | 55790 | | 5604 | 2 | 3 | | III-1 | D6Ertd474e | | |
| 5215 | 2 | 3 | | | III-1 | Csrnd1 | 54478 | 12-May-15 | 5606 | 2 | 3 | | III-1 | D6Wsu163e | | |
| 5232 | 2 | 3 | | | III-1 | Csnk2b | 1460 | 21-May-15 | 5609 | 2 | 3 | | III-1 | D730045A05Rik | | |
| 5239 | 2 | 3 | | | III-1 | Csrnp2 | 81566 | 28-May-15 | 5611 | 2 | 3 | | III-1 | D730050B12Rik | | |
| 5240 | 2 | 3 | | | III-1 | Csrnp3 | 80034 | 28-May-15 | 5615 | 2 | 3 | | III-1 | D830005E20Rik | | |
| 5243 | 2 | 3 | | | III-1 | Csrp2bp | 57325 | 7-Jun-15 | 5625 | 2 | 3 | | III-1 | D930007P13Rik | | |
| 5248 | 2 | 3 | | | III-1 | Cst13 | | | 5628 | 2 | 3 | | III-1 | D930016O06Rik | | |
| 5253 | 2 | 3 | | | III-1 | Cst9 | 128822 | 4-May-15 | 5630 | 2 | 3 | | III-1 | D930028M14Rik | | |
| 5256 | 2 | 3 | | | III-1 | Cstb | 1476 | 23-May-15 | 5631 | 2 | 3 | | III-1 | D930032P07Rik | | |
| 5261 | 2 | 3 | | | III-1 | Cstl1 | 128817 | 12-May-15 | 5634 | 2 | 3 | | III-1 | Daam2 | 23500 | 14-May-15 |
| 5266 | 2 | 3 | | | III-1 | Ctbs | 1486 | 12-May-15 | 5636 | 2 | 3 | | III-1 | Dab2 | 1601 | |
| 5267 | 2 | 3 | | | III-1 | Ctcl | 80169 | 22-May-15 | 5637 | 2 | 3 | | III-1 | Dab2ip | 153090 | 4-May-15 |
| 5278 | 2 | 3 | | | III-1 | Ctf2 | | | 5638 | 2 | 3 | | III-1 | Dach1 | 1602 | 23-May-15 |
| 5286 | 2 | 3 | | | III-1 | Ctnna1 | 1495 | 12-May-15 | 5643 | 2 | 3 | | III-1 | Dad1 | 1603 | 12-May-15 |
| 5290 | 2 | 3 | | | III-1 | Ctnnb1 | 1499 | 31-May-15 | 5644 | 2 | 3 | | III-1 | Dsf2 | | |
| 5292 | 2 | 3 | | | III-1 | Ctnnbl1 | 56259 | 12-May-15 | 5645 | 2 | 3 | | III-1 | Dag1 | 1605 | 28-May-15 |
| 5294 | 2 | 3 | | | III-1 | Ctnnd2 | 1501 | 29-May-15 | 5650 | 2 | 3 | | III-1 | Dancr | 57291 | |
| 5295 | 2 | 3 | | | III-1 | Ctns | 1497 | 23-May-15 | 5651 | 2 | 3 | | III-1 | Dand5 | 199699 | 4-May-15 |
| 5297 | 2 | 3 | | | III-1 | Ctps2 | 56474 | 4-May-15 | 5653 | 2 | 3 | | III-1 | Dap | 1611 | /6/7 |
| 5311 | 2 | 3 | | | III-1 | Ctsd | 1509 | 23-May-15 | 5657 | 2 | 3 | | III-1 | Dapk3 | 1613 | 4-May-15 |
| 5314 | 2 | 3 | | | III-1 | Ctsg | 1511 | 12-May-15 | 5660 | 2 | 3 | | III-1 | Dars | 1615 | 4-May-15 |
| 5315 | 2 | 3 | | | III-1 | Ctsh | 1512 | 12-May-15 | 5668 | 2 | 3 | | III-1 | Dbh | 1621 | 23-May-15 |
| 5316 | 2 | 3 | | | III-1 | Ctsj | | | 5670 | 2 | 3 | | III-1 | Dbi | 1622 | 7-Jun-15 |
| 5319 | 2 | 3 | | | III-1 | Crsl18 | 684021 | 4-May-15 | 5678 | 2 | 3 | | III-1 | Dbr1 | 51163 | 4-May-15 |
| 5327 | 2 | 3 | | | III-1 | Cttn | 2017 | 17-May-15 | 5680 | 2 | 3 | | III-1 | Dbx1 | 120237 | 4-May-15 |
| 5329 | 2 | 3 | | | III-1 | Cttnbp2nl | 55917 | 4-May-15 | 5686 | 2 | 3 | | III-1 | Dcaf12l2 | 340578 | 4-May-15 |
| 5330 | 2 | 3 | | | III-1 | Ctu1 | 90353 | 23-May-15 | 5688 | 2 | 3 | | III-1 | Dcaf15 | 90379 | 4-May-15 |
| 5331 | 2 | 3 | | | III-1 | Ctu2 | 348180 | 4-May-15 | 5696 | 2 | 3 | | III-1 | Dcbld1 | 285761 | 4-May-15 |
| 5333 | 2 | 3 | | | III-1 | Ctxn2 | 399697 | 4-May-15 | 5697 | 2 | 3 | | III-1 | Dcbld2 | 131566 | 4-May-15 |
| 5337 | 2 | 3 | | | III-1 | Cuedc2 | 79004 | 4-May-15 | 5698 | 2 | 3 | | III-1 | Dcc | 1630 | 17-May-15 |
| 5346 | 2 | 3 | | | III-1 | Cuta | 51596 | 12-May-15 | 5702 | 2 | 3 | | III-1 | Dchs1 | 8642 | 4-May-15 |
| 5348 | 2 | 3 | | | III-1 | Cutc | 51076 | 4-May-15 | 5705 | 2 | 3 | | III-1 | Dck2 | 166614 | 4-May-15 |
| 5349 | 2 | 3 | | | III-1 | Cux1 | 1523 | 28-May-15 | 5709 | 2 | 3 | | III-1 | Dclre1c | 64421 | 23-May-15 |
| 5353 | 2 | 3 | | | III-1 | Cwc22 | 57703 | 4-May-15 | 5711 | 2 | 3 | | III-1 | Dcp1a | 55802 | 4-May-15 |
| 5357 | 2 | 3 | | | III-1 | Cwf19l2 | 143884 | 4-May-15 | 5722 | 2 | 3 | | III-1 | Dctn1 | 1639 | 23-May-15 |
| 5365 | 2 | 3 | | | III-1 | Cxcl12 | 6387 | 17-May-15 | 5725 | 2 | 3 | | III-1 | Dctn4 | 51164 | 4-May-15 |
| 5368 | 2 | 3 | | | III-1 | Cxcl15 | | | 5729 | 2 | 3 | | III-1 | Dcun1d1 | 54165 | 2-Jun-15 |
| 5370 | 2 | 3 | | | III-1 | Cxcl17 | 284340 | 4-May-15 | 5732 | 2 | 3 | | III-1 | Dcun1d4 | 23142 | 4-May-15 |
| 5377 | 2 | 3 | | | III-1 | Cxcr3 | 2833 | 12-May-15 | 5736 | 2 | 3 | | III-1 | Dda1 | 79016 | 4-May-15 |
| 5381 | 2 | 3 | | | III-1 | Cxx1a | | | 5741 | 2 | 3 | | III-1 | Ddc | 1644 | 12-May-15 |
| 5389 | 2 | 3 | | | III-1 | Cyb561a3 | 220002 | 4-May-15 | 5742 | 2 | 3 | | III-1 | Ddhd1 | 80821 | 28-May-15 |
| 5392 | 2 | 3 | | | III-1 | Cyb5b | 80777 | 4-May-15 | 5743 | 2 | 3 | | III-1 | Ddhd2 | 23259 | 4-May-15 |
| 5395 | 2 | 3 | | | III-1 | Cyb5r1 | 51706 | 4-May-15 | 5744 | 2 | 3 | | III-1 | Ddi1 | 414301 | 4-May-15 |
| 5396 | 2 | 3 | | | III-1 | Cyb5r2 | 51700 | 12-May-15 | 5753 | 2 | 3 | | III-1 | Ddr2 | 4921 | 17-May-15 |
| 5397 | 2 | 3 | | | III-1 | Cyb5r3 | 1727 | 21-May-15 | 5756 | 2 | 3 | | III-1 | Ddx1 | 1653 | 4-May-15 |
| 5398 | 2 | 3 | | | III-1 | Cyb5r4 | 51167 | 4-May-15 | 5761 | 2 | 3 | | III-1 | Ddx19a | 55308 | 4-May-15 |
| 5402 | 2 | 3 | | | III-1 | Cybrd1 | 79901 | 12-May-15 | 5769 | 2 | 3 | | III-1 | Ddx27 | 55661 | 4-May-15 |
| 5404 | 2 | 3 | | | III-1 | Cycs | 54205 | 12-May-15 | 5770 | 2 | 3 | | III-1 | Ddx28 | 55794 | 4-May-15 |
| 5405 | 2 | 3 | | | III-1 | Cyct | | | 5776 | 2 | 3 | | III-1 | Ddx4 | 54514 | 4-May-15 |
| 5409 | 2 | 3 | | | III-1 | Cyhr1 | 50626 | 4-May-15 | 5783 | 2 | 3 | | III-1 | Ddx5 | 1655 | 4-May-15 |
| 5414 | 2 | 3 | | | III-1 | Cyp11a1 | 1583 | 12-May-15 | 5786 | 2 | 3 | | III-1 | Ddx52 | 11056 | 4-May-15 |
| 5416 | 2 | 3 | | | III-1 | Cyp11b2 | 1585 | 24-May-15 | 5790 | 2 | 3 | | III-1 | Ddx58 | 23586 | 24-May-15 |
| 5421 | 2 | 3 | | | III-1 | Cyp1b1 | 1545 | | 5791 | 2 | 3 | | III-1 | Ddx59 | 83479 | 4-May-15 |
| 5422 | 2 | 3 | | | III-1 | Cyp20a1 | 57404 | 4-May-15 | 5798 | 2 | 3 | | III-1 | Decr2 | 26063 | 4-May-15 |
| 5423 | 2 | 3 | | | III-1 | Cyp21a1 | | | 5815 | 2 | 3 | | III-1 | Defa6 | 1671 | 4-May-15 |
| 5425 | 2 | 3 | | | III-1 | Cyp26a1 | 1592 | 17-May-15 | 5817 | 2 | 3 | | III-1 | Defa-ps12 | | |
| 5427 | 2 | 3 | | | III-1 | Cyp26c1 | 340665 | 4-May-15 | 5825 | 2 | 3 | | III-1 | Defb13 | 245927 | 4-May-15 |
| 5437 | 2 | 3 | | | III-1 | Cyp2b19 | | | 5841 | 2 | 3 | | III-1 | Defb33 | | |
| 5438 | 2 | 3 | | | III-1 | Cyp2b23 | | | 5853 | 2 | 3 | | III-1 | Defb44-ps | | |
| 5440 | 2 | 3 | | | III-1 | Cyp2c29 | | | 5855 | 2 | 3 | | III-1 | Defb46 | | |
| 5450 | 2 | 3 | | | III-1 | Cyp2c65 | | | 5858 | 2 | 3 | | III-1 | Defb5 | | |
| 5451 | 2 | 3 | | | III-1 | Cyp2c66 | | | 5864 | 2 | 3 | | III-1 | Degs1 | 8560 | 12-May-15 |
| 5452 | 2 | 3 | | | III-1 | Cyp2c67 | | | 5872 | 2 | 3 | | III-1 | Dennd2d | 79961 | 4-May-15 |
| 5455 | 2 | 3 | | | III-1 | Cyp2c70 | | | 5873 | 2 | 3 | | III-1 | Dennd3 | 22898 | 12-May-15 |
| 5462 | 2 | 3 | | | III-1 | Cyp2d34 | | | 5874 | 2 | 3 | | III-1 | Dennd4a | 10260 | 12-May-15 |
| 5469 | 2 | 3 | | | III-1 | Cyp2j11 | | | 5876 | 2 | 3 | | III-1 | Dennd4c | 55667 | 4-May-15 |
| 5474 | 2 | 3 | | | III-1 | Cyp2j8 | | | 5877 | 2 | 3 | | III-1 | Dennd5a | 23258 | 4-May-15 |
| 5476 | 2 | 3 | | | III-1 | Cyp2r1 | 120227 | 31-May-15 | 5879 | 2 | 3 | | III-1 | Dennd6a | 201627 | 4-May-15 |
| 5477 | 2 | 3 | | | III-1 | Cyp2s1 | 29785 | | 5881 | 2 | 3 | | III-1 | Denr | 8562 | 4-May-15 |
| 5478 | 2 | 3 | | | III-1 | Cyp2t4 | | | 5886 | 2 | 3 | | III-1 | Deptor | 64798 | 31-May-15 |
| 5484 | 2 | 3 | | | III-1 | Cyp3a16 | | | 5887 | 2 | 3 | | III-1 | Dera | 51071 | 4-May-15 |
| 5489 | 2 | 3 | | | III-1 | Cyp3a57 | | | 5893 | 2 | 3 | | III-1 | Desi2 | 51029 | 7-Jun-15 |
| 5491 | 2 | 3 | | | III-1 | Cyp46a1 | 10858 | 4-May-15 | 5897 | 2 | 3 | | III-1 | Dffb | 1677 | 12-May-15 |
| 5496 | 2 | 3 | | | III-1 | Cyp4a29 | | | 5899 | 2 | 3 | | III-1 | Dfnb59 | 494513 | 23-May-15 |
| 5499 | 2 | 3 | | | III-1 | Cyp4a32 | | | 5903 | 2 | 3 | | III-1 | Dgcr14 | 8220 | 23-May-15 |
| 5503 | 2 | 3 | | | III-1 | Cyp4f14 | | | 5906 | 2 | 3 | | III-1 | Dgcr8 | 54487 | 23-May-15 |
| 5505 | 2 | 3 | | | III-1 | Cyp4f16 | | | 5907 | 2 | 3 | | III-1 | Dgka | 1606 | 12-May-15 |
| 5507 | 2 | 3 | | | III-1 | Cyp4f18 | | | 5913 | 2 | 3 | | III-1 | Dgkh | 160851 | 4-May-15 |
| 5509 | 2 | 3 | | | III-1 | Cyp4f39 | | | 5918 | 2 | 3 | | III-1 | Dguok | 1716 | 23-May-15 |
| 5515 | 2 | 3 | | | III-1 | Cyp7a1 | 1581 | 12-May-15 | 5923 | 2 | 3 | | III-1 | Dhfr | 1719 | 12-May-15 |
| 5520 | 2 | 3 | | | III-1 | Cypt14 | | | 5929 | 2 | 3 | | III-1 | Dhrs13 | 147015 | 4-May-15 |
| 5526 | 2 | 3 | | | III-1 | Cypt8 | | | 5930 | 2 | 3 | | III-1 | Dhrs2 | 10202 | 4-May-15 |
| 5527 | 2 | 3 | | | III-1 | Cypt9 | | | 5932 | 2 | 3 | | III-1 | Dhrs4 | 10901 | 12-May-15 |
| 5529 | 2 | 3 | | | III-1 | Cys1 | 192868 | 4-May-15 | 5939 | 2 | 3 | | III-1 | Dhx15 | 1665 | 3-May-15 |
| 5530 | 2 | 3 | | | III-1 | Cysltr1 | 10800 | 4-May-15 | 5942 | 2 | 3 | | III-1 | Dhx30 | 22907 | 4-May-15 |
| 5531 | 2 | 3 | | | III-1 | Cysltr2 | 57105 | 9-May-15 | 5955 | 2 | 3 | | III-1 | Diablo | 56616 | 17-May-15 |
| 5536 | 2 | 3 | | | III-1 | Cyth4 | 27128 | | 5957 | 2 | 3 | | III-1 | Diap2 | | |
| 5550 | 2 | 3 | | | III-1 | D10hu81e | | | 5959 | 2 | 3 | | III-1 | Dicer1 | 23405 | 24-May-15 |
| 5551 | 2 | 3 | | | III-1 | D10Wsu102e | | | 5961 | 2 | 3 | | III-1 | Dixxf | 27042 | 4-May-15 |
| 5570 | 2 | 3 | | | III-1 | D230025D16Rik | | | 5967 | 2 | 3 | | III-1 | Dip2a | 23181 | 4-May-15 |
| 5571 | 2 | 3 | | | III-1 | D230030D09Rik | | | 5970 | 2 | 3 | | III-1 | Dirc2 | 84925 | 4-May-15 |
| 5572 | 2 | 3 | | | III-1 | D2hgdh | 728294 | 4-May-15 | 5972 | 2 | 3 | | III-1 | Dis3 | 22894 | 17-May-15 |
| 5577 | 2 | 3 | | | III-1 | D330050G23Rik | | | 5974 | 2 | 3 | | III-1 | Dis3l | 115752 | 12-May-15 |

Fig.22 - 65

| | | | | | | | | | | | | | | |
|---|---|---|---|---|---|---|---|---|---|---|---|---|---|---|
| 5978 | 2 | 3 | | | III-1 | Disp2 | 85455 | 4-May-15 | 6334 | 2 | 3 | | III-1 | Dzip3 | 9666 | 21-May-15 |
| 5980 | 2 | 3 | | | III-1 | Dkc1 | 1736 | 31-May-15 | 6338 | 2 | 3 | | III-1 | E030013I19Rik | | |
| 5981 | 2 | 3 | | | III-1 | Dkk1 | 22943 | 31-May-15 | 6340 | 2 | 3 | | III-1 | E030025P04Rik | | |
| 5984 | 2 | 3 | | | III-1 | Dkk4 | 27121 | 4-May-15 | 6349 | 2 | 3 | | III-1 | E130018N17Rik | | |
| 5986 | 2 | 3 | | | III-1 | Dlat | 1737 | 29-May-15 | 6350 | 2 | 3 | | III-1 | E130102H24Rik | | |
| 5988 | 2 | 3 | | | III-1 | Dld | 1738 | 7-Jun-15 | 6354 | 2 | 3 | | III-1 | E130215H24Rik | | |
| 5994 | 2 | 3 | | | III-1 | Dlg3 | 1741 | 7-Jun-15 | 6355 | 2 | 3 | | III-1 | E130218I03Rik | | |
| 5998 | 2 | 3 | | | III-1 | Dlgap2 | 9228 | 4-May-15 | 6358 | 2 | 3 | | III-1 | E130308A19Rik | | |
| 6007 | 2 | 3 | | | III-1 | Dlst | 1743 | 4-May-15 | 6359 | 2 | 3 | | III-1 | E130309D02Rik | | |
| 6014 | 2 | 3 | | | III-1 | Dlx6 | 1750 | 4-May-15 | 6365 | 2 | 3 | | III-1 | E230008N13Rik | | |
| 6025 | 2 | 3 | | | III-1 | Dmpk | 1760 | 31-May-15 | 6367 | 2 | 3 | | III-1 | E230016M11Rik | | |
| 6026 | 2 | 3 | | | III-1 | Dmr | 91833 | 3-May-15 | 6368 | 2 | 3 | | III-1 | E230019M04Rik | | |
| 6029 | 2 | 3 | | | III-1 | Dmrt3 | 58524 | 4-May-15 | 6374 | 2 | 3 | | III-1 | E2f4 | 1874 | 4-May-15 |
| 6034 | 2 | 3 | | | III-1 | Dmrtc1b | 728656 | 4-May-15 | 6377 | 2 | 3 | | III-1 | E2f7 | 144455 | 4-May-15 |
| 6041 | 2 | 3 | | | III-1 | Dmxl2 | 23312 | 31-May-15 | 6381 | 2 | 3 | | III-1 | E330012B07Rik | | |
| 6043 | 2 | 3 | | | III-1 | Dnaaf1 | 123872 | 23-May-15 | 6383 | 2 | 3 | | III-1 | E330014E10Rik | | |
| 6046 | 2 | 3 | | | III-1 | Dnah3 | 25981 | 28-May-15 | 6386 | 2 | 3 | | III-1 | E330020D12Rik | | |
| 6063 | 2 | 3 | | | III-1 | Dnajb1 | 3337 | 12-May-15 | 6399 | 2 | 3 | | III-1 | Eapp | 55837 | 12-May-15 |
| 6068 | 2 | 3 | | | III-1 | Dnajb2 | 3300 | 23-May-15 | 6400 | 2 | 3 | | III-1 | Ear1 | 9572 | 12-May-15 |
| 6070 | 2 | 3 | | | III-1 | Dnajb4 | 11080 | 4-May-15 | 6401 | 2 | 3 | | III-1 | Ear10 | | |
| 6072 | 2 | 3 | | | III-1 | Dnajb6 | 10049 | 23-May-15 | 6407 | 2 | 3 | | III-1 | Ear7 | 7067 | 12-May-15 |
| 6075 | 2 | 3 | | | III-1 | Dnajb9 | 4189 | 4-May-15 | 6410 | 2 | 3 | | III-1 | Ebf1 | 1879 | 12-May-15 |
| 6076 | 2 | 3 | | | III-1 | Dnajc1 | 64215 | 4-May-15 | 6411 | 2 | 3 | | III-1 | Ebf2 | 64641 | 4-May-15 |
| 6078 | 2 | 3 | | | III-1 | Dnajc11 | 55735 | 4-May-15 | 6413 | 2 | 3 | | III-1 | Ebf4 | 57593 | 4-May-15 |
| 6080 | 2 | 3 | | | III-1 | Dnajc13 | 23317 | 23-May-15 | 6414 | 2 | 3 | | III-1 | Ebi3 | 10148 | 12-May-15 |
| 6083 | 2 | 3 | | | III-1 | Dnajc16 | 23341 | 4-May-15 | 6418 | 2 | 3 | | III-1 | Ecd | 11319 | 7-Jun-15 |
| 6086 | 2 | 3 | | | III-1 | Dnajc19 | 131118 | 4-May-15 | 6421 | 2 | 3 | | III-1 | Ecel1 | 9427 | 12-May-15 |
| 6088 | 2 | 3 | | | III-1 | Dnajc21 | 134218 | 4-May-15 | 6426 | 2 | 3 | | III-1 | Echs1 | 1892 | 31-May-15 |
| 6091 | 2 | 3 | | | III-1 | Dnajc25 | 548645 | 4-May-15 | 6427 | 2 | 3 | | III-1 | Eci1 | 1632 | 4-May-15 |
| 6093 | 2 | 3 | | | III-1 | Dnajc28 | 54943 | 4-May-15 | 6428 | 2 | 3 | | III-1 | Eci2 | 10455 | 4-May-15 |
| 6094 | 2 | 3 | | | III-1 | Dnajc3 | 5611 | 4-May-15 | 6430 | 2 | 3 | | III-1 | Ecm1 | 1893 | 12-May-15 |
| 6097 | 2 | 3 | | | III-1 | Dnajc5 | 80331 | 12-May-15 | 6434 | 2 | 3 | | III-1 | Ect2 | 1894 | 4-May-15 |
| 6102 | 2 | 3 | | | III-1 | Dnajc8 | 22826 | 4-May-15 | 6437 | 2 | 3 | | III-1 | Eda2r | 60401 | 4-May-15 |
| 6110 | 2 | 3 | | | III-1 | Dnase1l3 | 1776 | 4-May-15 | 6438 | 2 | 3 | | III-1 | Edar | 10913 | 23-May-15 |
| 6111 | 2 | 3 | | | III-1 | Dnase2a | 1777 | 12-May-15 | 6449 | 2 | 3 | | III-1 | Edn2 | 1907 | 4-May-15 |
| 6112 | 2 | 3 | | | III-1 | Dnase2b | 58511 | 4-May-15 | 6452 | 2 | 3 | | III-1 | Ednrb | 1910 | 24-May-15 |
| 6114 | 2 | 3 | | | III-1 | Dner | 92737 | 4-May-15 | 6453 | 2 | 3 | | III-1 | Edrf1 | 26098 | 4-May-15 |
| 6117 | 2 | 3 | | | III-1 | Dnmt1 | 10059 | 31-May-15 | 6456 | 2 | 3 | | III-1 | Eef1a1 | 1915 | 24-May-15 |
| 6121 | 2 | 3 | | | III-1 | Dnmbp | 23268 | 4-May-15 | 6459 | 2 | 3 | | III-1 | Eef1d | 1936 | 4-May-15 |
| 6122 | 2 | 3 | | | III-1 | Dnmt3l | 1786 | 22-May-15 | 6460 | 2 | 3 | | III-1 | Eef1e1 | 9521 | 4-May-15 |
| 6127 | 2 | 3 | | | III-1 | Dnpep | 23549 | 4-May-15 | 6461 | 2 | 3 | | III-1 | Eef1g | 1937 | 4-May-15 |
| 6131 | 2 | 3 | | | III-1 | Dnttip2 | 30836 | 4-May-15 | 6464 | 2 | 3 | | III-1 | Eefsec | 60628 | 4-May-15 |
| 6136 | 2 | 3 | | | III-1 | Dock10 | 55619 | 4-May-15 | 6466 | 2 | 3 | | III-1 | Efcab1 | 79645 | 4-May-15 |
| 6139 | 2 | 3 | | | III-1 | Dock3 | 1795 | 12-May-15 | 6468 | 2 | 3 | | III-1 | Efcab11 | 90141 | 4-May-15 |
| 6141 | 2 | 3 | | | III-1 | Dock5 | 80005 | 12-May-15 | 6472 | 2 | 3 | | III-1 | Efcab3 | 146779 | 4-May-15 |
| 6143 | 2 | 3 | | | III-1 | Dock7 | 85440 | 4-May-15 | 6489 | 2 | 3 | | III-1 | Efna2 | 1943 | 12-May-15 |
| 6144 | 2 | 3 | | | III-1 | Dock8 | 81704 | 4-May-15 | 6490 | 2 | 3 | | III-1 | Efna3 | 1944 | 4-May-15 |
| 6148 | 2 | 3 | | | III-1 | Dok2 | 9046 | 4-May-15 | 6493 | 2 | 3 | | III-1 | Efnb1 | 1947 | 12-May-15 |
| 6151 | 2 | 3 | | | III-1 | Dok5 | 55816 | 4-May-15 | 6494 | 2 | 3 | | III-1 | Efnb2 | 1948 | 4-May-15 |
| 6154 | 2 | 3 | | | III-1 | Dolk | 22845 | 23-May-15 | 6499 | 2 | 3 | | III-1 | Efrud1 | 79631 | 4-May-15 |
| 6157 | 2 | 3 | | | III-1 | Dopey1 | 23033 | 4-May-15 | 6506 | 2 | 3 | | III-1 | Egf8 | 80864 | 12-May-15 |
| 6160 | 2 | 3 | | | III-1 | Dor1l | 84444 | 4-May-15 | 6507 | 2 | 3 | | III-1 | Egflam | 133584 | 4-May-15 |
| 6161 | 2 | 3 | | | III-1 | Doxl2 | | | 6515 | 2 | 3 | | III-1 | Egr4 | 1961 | 4-May-15 |
| 6164 | 2 | 3 | | | III-1 | Dpcr1 | 135656 | 4-May-15 | 6517 | 2 | 3 | | III-1 | Ehbp1l1 | 254102 | 12-May-15 |
| 6166 | 2 | 3 | | | III-1 | Dpep2 | 64174 | 4-May-15 | 6518 | 2 | 3 | | III-1 | Ehd1 | 10938 | 10-May-15 |
| 6172 | 2 | 3 | | | III-1 | Dph2 | 1802 | 4-May-15 | 6520 | 2 | 3 | | III-1 | Ehd3 | 30845 | 4-May-15 |
| 6178 | 2 | 3 | | | III-1 | Dpm2 | 8818 | 23-May-15 | 6521 | 2 | 3 | | III-1 | Ehd4 | 30844 | 4-May-15 |
| 6183 | 2 | 3 | | | III-1 | Dpp6 | 1804 | 12-May-15 | 6524 | 2 | 3 | | III-1 | Ehmt1 | 79813 | 4-May-15 |
| 6184 | 2 | 3 | | | III-1 | Dpp7 | 29952 | 4-May-15 | 6531 | 2 | 3 | | III-1 | Eif1 | 10209 | 4-May-15 |
| 6190 | 2 | 3 | | | III-1 | Dppa4 | 55211 | 4-May-15 | 6532 | 2 | 3 | | III-1 | Eif1a | 1964 | 7-Jun-15 |
| 6192 | 2 | 3 | | | III-1 | Dpr | 1805 | 4-May-15 | 6537 | 2 | 3 | | III-1 | Eif2ak1 | 27102 | 7-Jun-15 |
| 6200 | 2 | 3 | | | III-1 | Dpysl2 | 1808 | 4-May-15 | 6539 | 2 | 3 | | III-1 | Eif2ak3 | 9451 | 31-May-15 |
| 6202 | 2 | 3 | | | III-1 | Dpysl4 | 10570 | 4-May-15 | 6541 | 2 | 3 | | III-1 | Eif2b1 | 1967 | 23-May-15 |
| 6203 | 2 | 3 | | | III-1 | Dpysl5 | 56896 | 4-May-15 | 6544 | 2 | 3 | | III-1 | Eif2b4 | 8890 | 23-May-15 |
| 6204 | 2 | 3 | | | III-1 | DQ267100 | | | 6556 | 2 | 3 | | III-1 | Eif3f | 8665 | 4-May-15 |
| 6208 | 2 | 3 | | | III-1 | Dr1 | 1810 | 24-May-15 | 6557 | 2 | 3 | | III-1 | Eif3g | 8666 | 12-May-15 |
| 6211 | 2 | 3 | | | III-1 | Drap1 | 10589 | 4-May-15 | 6563 | 2 | 3 | | III-1 | Eif3i | 51386 | 4-May-15 |
| 6212 | 2 | 3 | | | III-1 | Draxin | 374946 | 4-May-15 | 6565 | 2 | 3 | | III-1 | Eif4a1 | 1973 | 17-May-15 |
| 6220 | 2 | 3 | | | III-1 | Drg1 | 4733 | 7-Jun-15 | 6566 | 2 | 3 | | III-1 | Eif4a2 | 1974 | 4-May-15 |
| 6223 | 2 | 3 | | | III-1 | Drp2 | 1821 | 7-Jun-15 | 6574 | 2 | 3 | | III-1 | Eif4ebp2 | 1979 | 4-May-15 |
| 6226 | 2 | 3 | | | III-1 | Dsc3 | 1825 | 13-Jun-15 | 6575 | 2 | 3 | | III-1 | Eif4ebp3 | 8637 | 4-May-15 |
| 6227 | 2 | 3 | | | III-1 | Dscam | 1826 | 4-May-15 | 6585 | 2 | 3 | | III-1 | Eif6 | 3692 | 12-May-15 |
| 6233 | 2 | 3 | | | III-1 | Dsg1a | | | 6591 | 2 | 3 | | III-1 | Elavl3 | 1995 | 2-Jun-15 |
| 6237 | 2 | 3 | | | III-1 | Dsg3 | 1830 | 12-May-15 | 6594 | 2 | 3 | | III-1 | Elf2 | 1998 | 28-May-15 |
| 6241 | 2 | 3 | | | III-1 | Dspp | 1834 | 12-May-15 | 6596 | 2 | 3 | | III-1 | Elf4 | 2000 | 28-May-15 |
| 6246 | 2 | 3 | | | III-1 | Dtd2 | 112487 | 4-May-15 | 6610 | 2 | 3 | | III-1 | Elmod2 | 255520 | 4-May-15 |
| 6251 | 2 | 3 | | | III-1 | Dtnbp1 | 84062 | 31-May-15 | 6612 | 2 | 3 | | III-1 | Elmsan1 | 91748 | 9-May-15 |
| 6253 | 2 | 3 | | | III-1 | Dtwd2 | 285605 | 12-May-15 | 6619 | 2 | 3 | | III-1 | Elovl5 | 60481 | 21-May-15 |
| 6255 | 2 | 3 | | | III-1 | Dtx2 | 113878 | 4-May-15 | 6622 | 2 | 3 | | III-1 | Elp2 | 55250 | 4-May-15 |
| 6262 | 2 | 3 | | | III-1 | Duoxa1 | 90527 | 20-May-15 | 6625 | 2 | 3 | | III-1 | Elp5 | 23587 | 4-May-15 |
| 6266 | 2 | 3 | | | III-1 | Dus2 | 54920 | 4-May-15 | 6629 | 2 | 3 | | III-1 | Emc1 | 23065 | 4-May-15 |
| 6276 | 2 | 3 | | | III-1 | Dusp16 | 80824 | 4-May-15 | 6632 | 2 | 3 | | III-1 | Emc3 | 55831 | 21-May-15 |
| 6278 | 2 | 3 | | | III-1 | Dusp19 | 142679 | 4-May-15 | 6638 | 2 | 3 | | III-1 | Emcn | 51705 | 4-May-15 |
| 6282 | 2 | 3 | | | III-1 | Dusp23 | 54935 | 7-Jun-15 | 6639 | 2 | 3 | | III-1 | Emd | 2010 | 23-May-15 |
| 6286 | 2 | 3 | | | III-1 | Dusp3 | 1845 | 4-May-15 | 6642 | 2 | 3 | | III-1 | Emg1 | 10436 | 14-May-15 |
| 6289 | 2 | 3 | | | III-1 | Dusp6 | 1848 | 4-May-15 | 6646 | 2 | 3 | | III-1 | Emilin3 | 90187 | 7-Jun-15 |
| 6292 | 2 | 3 | | | III-1 | Dusp9 | 1852 | 4-May-15 | 6651 | 2 | 3 | | III-1 | Eml5 | 161436 | 12-May-15 |
| 6296 | 2 | 3 | | | III-1 | Duxbl2 | | | 6660 | 2 | 3 | | III-1 | Emx2os | 196047 | 12-May-15 |
| 6300 | 2 | 3 | | | III-1 | Dvl3 | 1857 | 12-May-15 | 6663 | 2 | 3 | | III-1 | Enah | 55740 | 31-May-15 |
| 6302 | 2 | 3 | | | III-1 | Dxo | 1797 | 12-May-15 | 6664 | 2 | 3 | | III-1 | Enam | 10117 | 12-May-15 |
| 6305 | 2 | 3 | | | III-1 | Dym | 54803 | 4-May-15 | 6667 | 2 | 3 | | III-1 | Endog | 2021 | 4-May-15 |
| 6308 | 2 | 3 | | | III-1 | Dync1l1 | 1780 | 12-May-15 | 6668 | 2 | 3 | | III-1 | Endou | 8909 | 23-May-15 |
| 6315 | 2 | 3 | | | III-1 | Dynll2 | 140735 | 4-May-15 | 6671 | 2 | 3 | | III-1 | Engase | 64772 | 12-May-15 |
| 6318 | 2 | 3 | | | III-1 | Dynlt1a | | | 6673 | 2 | 3 | | III-1 | Enkd1 | 84080 | 4-May-15 |
| 6320 | 2 | 3 | | | III-1 | Dynlt1c | | | 6677 | 2 | 3 | | III-1 | Eno2 | 2026 | 4-May-15 |
| 6327 | 2 | 3 | | | III-1 | Dyrk4 | 8798 | 4-May-15 | 6681 | 2 | 3 | | III-1 | Enox1 | 55068 | 4-May-15 |
| 6331 | 2 | 3 | | | III-1 | Dzank1 | 55184 | 28-May-15 | 6686 | 2 | 3 | | III-1 | Enpp3 | 5169 | 4-May-15 |

Fig.22 - 66

| | | | | | | | | | | | | | | | |
|---|---|---|---|---|---|---|---|---|---|---|---|---|---|---|---|
| 6687 | 2 | 3 | | | III-1 | Enpp4 | 22875 | 4-May-15 | 6997 | 2 | 3 | | | III-1 | Fam117b | 150864 | 4-May-15 |
| 6689 | 2 | 3 | | | III-1 | Enpp6 | 133121 | 12-May-15 | 6998 | 2 | 3 | | | III-1 | Fam118a | 55007 | 4-May-15 |
| 6691 | 2 | 3 | | | III-1 | Ensa | 2029 | 4-May-15 | 6999 | 2 | 3 | | | III-1 | Fam118b | 79607 | 4-May-15 |
| 6695 | 2 | 3 | | | III-1 | Entpd2 | 954 | 4-May-15 | 7008 | 2 | 3 | | | III-1 | Fam124b | 79843 | 4-May-15 |
| 6697 | 2 | 3 | | | III-1 | Entpd4 | 9583 | 21-May-15 | 7010 | 2 | 3 | | | III-1 | Fam126b | 285172 | 4-May-15 |
| 6698 | 2 | 3 | | | III-1 | Entpd5 | 957 | 12-May-15 | 7011 | 2 | 3 | | | III-1 | Fam129a | 116496 | 12-May-15 |
| 6699 | 2 | 3 | | | III-1 | Entpd6 | 955 | 4-May-15 | 7012 | 2 | 3 | | | III-1 | Fam129b | 64855 | 4-May-15 |
| 6701 | 2 | 3 | | | III-1 | Entpd8 | 377541 | 4-May-15 | 7013 | 2 | 3 | | | III-1 | Fam129c | 199786 | 4-May-15 |
| 6704 | 2 | 3 | | | III-1 | Eomes | 8320 | 12-May-15 | 7015 | 2 | 3 | | | III-1 | Fam131b | 9715 | 28-May-15 |
| 6705 | 2 | 3 | | | III-1 | Ep300 | 2033 | 29-May-15 | 7016 | 2 | 3 | | | III-1 | Fam131c | 348487 | 4-May-15 |
| 6706 | 2 | 3 | | | III-1 | Ep400 | 57634 | 4-May-15 | 7020 | 2 | 3 | | | III-1 | Fam134a | 79137 | 4-May-15 |
| 6708 | 2 | 3 | | | III-1 | Epb4.1 | | | 7022 | 2 | 3 | | | III-1 | Fam134c | 162427 | 12-May-15 |
| 6710 | 2 | 3 | | | III-1 | Epb4.1l2 | | | 7027 | 2 | 3 | | | III-1 | Fam13b | 51306 | 28-May-15 |
| 6712 | 2 | 3 | | | III-1 | Epb4.1l4a | | | 7028 | 2 | 3 | | | III-1 | Fam13c | 220965 | 4-May-15 |
| 6714 | 2 | 3 | | | III-1 | Epb4.1l5 | | | 7030 | 2 | 3 | | | III-1 | Fam149b | | |
| 6717 | 2 | 3 | | | III-1 | Epc2 | 26122 | 4-May-15 | 7041 | 2 | 3 | | | III-1 | Fam160a2 | 84067 | 4-May-15 |
| 6720 | 2 | 3 | | | III-1 | Epg5 | 57724 | 21-May-15 | 7045 | 2 | 3 | | | III-1 | Fam161b | 145483 | 12-May-15 |
| 6723 | 2 | 3 | | | III-1 | Epha10 | 284656 | 4-May-15 | 7046 | 2 | 3 | | | III-1 | Fam162a | 26355 | 4-May-15 |
| 6725 | 2 | 3 | | | III-1 | Epha3 | 2042 | 4-May-15 | 7047 | 2 | 3 | | | III-1 | Fam162b | 221303 | 4-May-15 |
| 6728 | 2 | 3 | | | III-1 | Epha6 | 285220 | 4-May-15 | 7053 | 2 | 3 | | | III-1 | Fam167b | 84734 | 4-May-15 |
| 6734 | 2 | 3 | | | III-1 | Ephb4 | 2050 | 31-May-15 | 7054 | 2 | 3 | | | III-1 | Fam168a | 23201 | 1-Jun-15 |
| 6742 | 2 | 3 | | | III-1 | Epn1 | 29924 | 3-May-15 | 7057 | 2 | 3 | | | III-1 | Fam169b | 283777 | 4-May-15 |
| 6745 | 2 | 3 | | | III-1 | Epo | 2056 | 7-Jun-15 | 7058 | 2 | 3 | | | III-1 | Fam170a | 340069 | 4-May-15 |
| 6749 | 2 | 3 | | | III-1 | Eprs | 2058 | 4-May-15 | 7062 | 2 | 3 | | | III-1 | Fam171b | 165215 | 4-May-15 |
| 6751 | 2 | 3 | | | III-1 | Eps15l1 | 58513 | 3-May-15 | 7066 | 2 | 3 | | | III-1 | Fam174a | 345757 | 4-May-15 |
| 6753 | 2 | 3 | | | III-1 | Eps8l1 | 54869 | 4-May-15 | 7071 | 2 | 3 | | | III-1 | Fam178b | 51252 | 4-May-15 |
| 6755 | 2 | 3 | | | III-1 | Eps8l3 | 79574 | 12-May-15 | 7073 | 2 | 3 | | | III-1 | Fam179b | 23116 | 12-May-15 |
| 6757 | 2 | 3 | | | III-1 | Ept1 | 85465 | 28-May-15 | 7074 | 2 | 3 | | | III-1 | Fam180a | 389558 | 4-May-15 |
| 6765 | 2 | 3 | | | III-1 | Erbb2ip | 55914 | 28-May-15 | 7075 | 2 | 3 | | | III-1 | Fam181a | 90050 | 4-May-15 |
| 6779 | 2 | 3 | | | III-1 | Erdr1 | | | 7080 | 2 | 3 | | | III-1 | Fam185a | 222234 | 4-May-15 |
| 6781 | 2 | 3 | | | III-1 | Erf | 2077 | 7-Jun-15 | 7084 | 2 | 3 | | | III-1 | Fam188a | 80013 | 4-May-15 |
| 6782 | 2 | 3 | | | III-1 | Erg | 2078 | 31-May-15 | 7086 | 2 | 3 | | | III-1 | Fam189a1 | 23359 | 4-May-15 |
| 6783 | 2 | 3 | | | III-1 | Ergic1 | 57222 | 28-May-15 | 7088 | 2 | 3 | | | III-1 | Fam189b | 10712 | 4-May-15 |
| 6787 | 2 | 3 | | | III-1 | Eri1 | 90459 | 4-May-15 | 7093 | 2 | 3 | | | III-1 | Fam195b | 348262 | 4-May-15 |
| 6790 | 2 | 3 | | | III-1 | Erich1 | 157697 | 14-May-15 | 7098 | 2 | 3 | | | III-1 | Fam199x | 139231 | 12-May-15 |
| 6793 | 2 | 3 | | | III-1 | Erich4 | 100170765 | 4-May-15 | 7099 | 2 | 3 | | | III-1 | Fam19a1 | 407738 | 4-May-15 |
| 6794 | 2 | 3 | | | III-1 | Erich5 | 203111 | 4-May-15 | 7104 | 2 | 3 | | | III-1 | Fam203a | 51296 | 4-May-15 |
| 6797 | 2 | 3 | | | III-1 | Erlin1 | 10613 | 28-May-15 | 7105 | 2 | 3 | | | III-1 | Fam204a | 63877 | 4-May-15 |
| 6801 | 2 | 3 | | | III-1 | Ermn | 57471 | 14-May-15 | 7112 | 2 | 3 | | | III-1 | Fam20b | 9917 | 23-May-15 |
| 6805 | 2 | 3 | | | III-1 | Ero1l | 30001 | 23-May-15 | 7116 | 2 | 3 | | | III-1 | Fam210b | 116151 | 4-May-15 |
| 6806 | 2 | 3 | | | III-1 | Ero1lb | 56695 | 4-May-15 | 7117 | 2 | 3 | | | III-1 | Fam212a | 389119 | 4-May-15 |
| 6807 | 2 | 3 | | | III-1 | Erp27 | 121506 | 4-May-15 | 7123 | 2 | 3 | | | III-1 | Fam216a | 29902 | 4-May-15 |
| 6811 | 2 | 3 | | | III-1 | Erv3 | 2086 | 21-May-15 | 7129 | 2 | 3 | | | III-1 | Fam219b | 57184 | 4-May-15 |
| 6816 | 2 | 3 | | | III-1 | Esf1 | 51575 | 4-May-15 | 7131 | 2 | 3 | | | III-1 | Fam221a | 340277 | 4-May-15 |
| 6834 | 2 | 3 | | | III-1 | Esp11 | 9700 | 4-May-15 | 7134 | 2 | 3 | | | III-1 | Fam222b | 55731 | 4-May-15 |
| 6836 | 2 | 3 | | | III-1 | Espnl | 339768 | 12-May-15 | 7140 | 2 | 3 | | | III-1 | Fam229b | 619208 | 4-May-15 |
| 6838 | 2 | 3 | | | III-1 | Esr2 | 2100 | 31-May-15 | 7141 | 2 | 3 | | | III-1 | Fam24a | 118670 | 4-May-15 |
| 6841 | 2 | 3 | | | III-1 | Esrra | 2101 | 10-May-15 | 7145 | 2 | 3 | | | III-1 | Fam26f | 441168 | 4-May-15 |
| 6844 | 2 | 3 | | | III-1 | Esx1 | 80712 | 12-May-15 | 7148 | 2 | 3 | | | III-1 | Fam3a | 60343 | 4-May-15 |
| 6848 | 2 | 3 | | | III-1 | Etaa1 | 54465 | 4-May-15 | 7152 | 2 | 3 | | | III-1 | Fam43b | 163933 | 4-May-15 |
| 6852 | 2 | 3 | | | III-1 | Etfb | 2109 | 12-May-15 | 7161 | 2 | 3 | | | III-1 | Fam49b | 51571 | 4-May-15 |
| 6855 | 2 | 3 | | | III-1 | Etl4 | 100144434 | 7-Dec-14 | 7162 | 2 | 3 | | | III-1 | Fam50a | 9130 | 21-May-15 |
| 6856 | 2 | 3 | | | III-1 | Etnk1 | 55500 | 4-May-15 | 7171 | 2 | 3 | | | III-1 | Fam63a | 55793 | 4-May-15 |
| 6857 | 2 | 3 | | | III-1 | Etnk2 | 55224 | 12-May-15 | 7172 | 2 | 3 | | | III-1 | Fam63b | 54629 | 4-May-15 |
| 6859 | 2 | 3 | | | III-1 | Etohd2 | | | 7182 | 2 | 3 | | | III-1 | Fam71d | 161142 | 4-May-15 |
| 6860 | 2 | 3 | | | III-1 | Etohi1 | | | 7184 | 2 | 3 | | | III-1 | Fam71e2 | 284418 | 4-May-15 |
| 6861 | 2 | 3 | | | III-1 | Ets1 | 2113 | 21-May-15 | 7187 | 2 | 3 | | | III-1 | Fam72a | 729533 | 4-May-15 |
| 6862 | 2 | 3 | | | III-1 | Ets2 | 2114 | 12-May-15 | 7189 | 2 | 3 | | | III-1 | Fam73b | 84895 | 4-May-15 |
| 6864 | 2 | 3 | | | III-1 | Etv2 | 2116 | 28-May-15 | 7197 | 2 | 3 | | | III-1 | Fam83c | 128876 | 4-May-15 |
| 6868 | 2 | 3 | | | III-1 | Etv6 | 2120 | 31-May-15 | 7199 | 2 | 3 | | | III-1 | Fam83e | 54854 | 4-May-15 |
| 6869 | 2 | 3 | | | III-1 | EU599041 | | | 7205 | 2 | 3 | | | III-1 | Fam86 | | |
| 6871 | 2 | 3 | | | III-1 | Evalb | 55194 | 28-May-15 | 7209 | 2 | 3 | | | III-1 | Fam92b | 339145 | 4-May-15 |
| 6880 | 2 | 3 | | | III-1 | Evi | 51466 | 12-May-15 | 7215 | 2 | 3 | | | III-1 | Fan1 | 22909 | 7-Jun-15 |
| 6882 | 2 | 3 | | | III-1 | Evx1 | 2128 | 4-May-15 | 7216 | 2 | 3 | | | III-1 | Fanca | 2175 | 23-May-15 |
| 6883 | 2 | 3 | | | III-1 | Evx2 | 344191 | 4-May-15 | 7223 | 2 | 3 | | | III-1 | Fancg | 2189 | 23-May-15 |
| 6895 | 2 | 3 | | | III-1 | Exoc5 | 10640 | 4-May-15 | 7229 | 2 | 3 | | | III-1 | Far1 | 84188 | 4-May-15 |
| 6902 | 2 | 3 | | | III-1 | Exosc10 | 5394 | 12-May-15 | 7231 | 2 | 3 | | | III-1 | Farp1 | 10160 | 4-May-15 |
| 6908 | 2 | 3 | | | III-1 | Exosc7 | 23016 | 4-May-15 | 7232 | 2 | 3 | | | III-1 | Farp2 | 9855 | 12-May-15 |
| 6910 | 2 | 3 | | | III-1 | Exosc9 | 5393 | 4-May-15 | 7234 | 2 | 3 | | | III-1 | Farsa | 2193 | 4-May-15 |
| 6911 | 2 | 3 | | | III-1 | Exph5 | 23086 | 12-May-15 | 7235 | 2 | 3 | | | III-1 | Farsb | 10056 | 4-May-15 |
| 6912 | 2 | 3 | | | III-1 | Ext1 | 2131 | 23-May-15 | 7244 | 2 | 3 | | | III-1 | Fat1 | 2195 | 12-May-15 |
| 6918 | 2 | 3 | | | III-1 | Eya2 | 2139 | 4-May-15 | 7245 | 2 | 3 | | | III-1 | Fat2 | 2196 | 12-May-15 |
| 6919 | 2 | 3 | | | III-1 | Eya3 | 2140 | 4-May-15 | 7246 | 2 | 3 | | | III-1 | Fat3 | 120114 | 4-May-15 |
| 6921 | 2 | 3 | | | III-1 | Ezh1 | 2145 | 13-Jun-15 | 7248 | 2 | 3 | | | III-1 | Fate1 | 89885 | 4-May-15 |
| 6922 | 2 | 3 | | | III-1 | Ezh2 | 2146 | 23-May-15 | 7250 | 2 | 3 | | | III-1 | Faxc | 84553 | 4-May-15 |
| 6924 | 2 | 3 | | | III-1 | F10 | 2159 | 7-Jun-15 | 7254 | 2 | 3 | | | III-1 | Fbln1 | 345630 | 3-May-15 |
| 6925 | 2 | 3 | | | III-1 | F11 | 2160 | 7-Jun-15 | 7256 | 2 | 3 | | | III-1 | Fbln2 | 2199 | 12-May-15 |
| 6929 | 2 | 3 | | | III-1 | F13b | 2165 | 12-May-15 | 7265 | 2 | 3 | | | III-1 | Fbxl12 | 54850 | 20-May-15 |
| 6933 | 2 | 3 | | | III-1 | F2rl2 | 2151 | 4-May-15 | 7267 | 2 | 3 | | | III-1 | Fbxl13 | 222235 | 4-May-15 |
| 6934 | 2 | 3 | | | III-1 | F2rl3 | 9002 | 17-May-15 | 7274 | 2 | 3 | | | III-1 | Fbxl2 | 25827 | 4-May-15 |
| 6936 | 2 | 3 | | | III-1 | F420014N23Rik | | | 7278 | 2 | 3 | | | III-1 | Fbxl3 | 26224 | 4-May-15 |
| 6937 | 2 | 3 | | | III-1 | F5 | 2153 | 23-May-15 | 7282 | 2 | 3 | | | III-1 | Fbxl7 | 23194 | 4-May-15 |
| 6939 | 2 | 3 | | | III-1 | F630042J09Rik | | | 7285 | 2 | 3 | | | III-1 | Fbxo11 | 80204 | 2-Jun-15 |
| 6943 | 2 | 3 | | | III-1 | F730035M05Rik | | | 7288 | 2 | 3 | | | III-1 | Fbxo17 | 115290 | 4-May-15 |
| 6945 | 2 | 3 | | | III-1 | F8 | 2157 | 28-May-15 | 7289 | 2 | 3 | | | III-1 | Fbxo18 | 84893 | 4-May-15 |
| 6956 | 2 | 3 | | | III-1 | Fabp2 | 2169 | 17-May-15 | 7291 | 2 | 3 | | | III-1 | Fbxo21 | 23014 | 4-May-15 |
| 6963 | 2 | 3 | | | III-1 | Fadd | 8772 | 31-May-15 | 7292 | 2 | 3 | | | III-1 | Fbxo22 | 26263 | 4-May-15 |
| 6971 | 2 | 3 | | | III-1 | Fahd1 | 81889 | 10-May-15 | 7301 | 2 | 3 | | | III-1 | Fbxo33 | 254170 | 4-May-15 |
| 6972 | 2 | 3 | | | III-1 | Fahd2a | 51011 | 4-May-15 | 7304 | 2 | 3 | | | III-1 | Fbxo38 | 81545 | 4-May-15 |
| 6973 | 2 | 3 | | | III-1 | Faim | 55179 | 4-May-15 | 7312 | 2 | 3 | | | III-1 | Fbxo45 | 200933 | 4-May-15 |
| 6979 | 2 | 3 | | | III-1 | Fam102b | 284611 | 4-May-15 | 7318 | 2 | 3 | | | III-1 | Fbxo7 | 25793 | 23-May-15 |
| 6984 | 2 | 3 | | | III-1 | Fam107b | 83641 | 4-May-15 | 7340 | 2 | 3 | | | III-1 | Fbxw8 | 26259 | 4-May-15 |
| 6990 | 2 | 3 | | | III-1 | Fam111a | 63901 | 4-May-15 | 7342 | 2 | 3 | | | III-1 | Fcamr | 83953 | 4-May-15 |
| 6991 | 2 | 3 | | | III-1 | Fam114a1 | 92689 | 4-May-15 | 7347 | 2 | 3 | | | III-1 | Fcgbp | 8857 | 4-May-15 |
| 6994 | 2 | 3 | | | III-1 | Fam115c | 285966 | 4-May-15 | 7353 | 2 | 3 | | | III-1 | Fcho1 | 23149 | 4-May-15 |
| 6995 | 2 | 3 | | | III-1 | Fam115e | | | 7356 | 2 | 3 | | | III-1 | Fchsd2 | 9873 | 4-May-15 |
| | | | | | | | | | 7369 | 2 | 3 | | | III-1 | Fdxacb1 | 91893 | 4-May-15 |

Fig.22 - 67

| | | | | | | | | | | | | | | |
|---|---|---|---|---|---|---|---|---|---|---|---|---|---|---|
| 7373 | 2 | 3 | | | III-1 | Fem1b | 10116 | 4-May-15 | 7734 | 2 | 3 | | III-1 | Gabpa | 2551 | 12-May-15 |
| 7375 | 2 | 3 | | | III-1 | Fen1 | 2237 | 3-May-15 | 7736 | 2 | 3 | | III-1 | Gabpb2 | 126626 | 7-Jun-15 |
| 7376 | 2 | 3 | | | III-1 | Ferdcr | 400550 | 16-May-15 | 7737 | 2 | 3 | | III-1 | Gabra1 | 2554 | 3-May-15 |
| 7381 | 2 | 3 | | | III-1 | Fermt2 | 10979 | 4-May-15 | 7748 | 2 | 3 | | III-1 | Gabrg1 | 2565 | 4-May-15 |
| 7382 | 2 | 3 | | | III-1 | Fermt3 | 83706 | 24-May-15 | 7753 | 2 | 3 | | III-1 | Gabrr1 | 2569 | 4-May-15 |
| 7386 | 2 | 3 | | | III-1 | Fev | 54738 | 12-May-15 | 7757 | 2 | 3 | | III-1 | Gad1os | | |
| 7387 | 2 | 3 | | | III-1 | Fez1 | 9638 | 7-Jun-15 | 7762 | 2 | 3 | | III-1 | Gadd45gip1 | 90480 | 4-May-15 |
| 7388 | 2 | 3 | | | III-1 | Fez2 | 9637 | 21-May-15 | 7763 | 2 | 3 | | III-1 | Gadl1 | 339896 | 4-May-15 |
| 7389 | 2 | 3 | | | III-1 | Fezf1 | 389549 | 4-May-15 | 7767 | 2 | 3 | | III-1 | Gal3st2 | 64090 | 7-Jun-15 |
| 7392 | 2 | 3 | | | III-1 | Ffar2 | 2867 | 7-Jun-15 | 7768 | 2 | 3 | | III-1 | Gal3st3 | 89792 | 4-May-15 |
| 7398 | 2 | 3 | | | III-1 | Fgd2 | 221472 | 7-Jun-15 | 7770 | 2 | 3 | | III-1 | Galc | 2581 | 23-May-15 |
| 7399 | 2 | 3 | | | III-1 | Fgd3 | 89846 | 7-Jun-15 | 7771 | 2 | 3 | | III-1 | Gale | 2582 | 23-May-15 |
| 7401 | 2 | 3 | | | III-1 | Fgd5 | 152273 | 12-May-15 | 7773 | 2 | 3 | | III-1 | Galk2 | 2585 | 4-May-15 |
| 7402 | 2 | 3 | | | III-1 | Fgd6 | 55785 | 4-May-15 | 7776 | 2 | 3 | | III-1 | Galnt1 | 2589 | 4-May-15 |
| 7405 | 2 | 3 | | | III-1 | Fgf11 | 2256 | 4-May-15 | 7780 | 2 | 3 | | III-1 | Galnt13 | 114805 | 7-Jun-15 |
| 7408 | 2 | 3 | | | III-1 | Fgf14 | 2259 | 23-May-15 | 7783 | 2 | 3 | | III-1 | Galnt16 | 57452 | 4-May-15 |
| 7416 | 2 | 3 | | | III-1 | Fgf22 | 27006 | 4-May-15 | 7785 | 2 | 3 | | III-1 | Galnt2 | 2590 | 12-May-15 |
| 7418 | 2 | 3 | | | III-1 | Fgf3 | 2248 | 4-May-15 | 7787 | 2 | 3 | | III-1 | Galnt4 | 8693 | 4-May-15 |
| 7422 | 2 | 3 | | | III-1 | Fgf7 | 2252 | 12-May-15 | 7788 | 2 | 3 | | III-1 | Galnt5 | 11227 | 4-May-15 |
| 7428 | 2 | 3 | | | III-1 | Fgfr1op | 11116 | 4-May-15 | 7790 | 2 | 3 | | III-1 | Galnt7 | 51809 | 7-Jun-15 |
| 7431 | 2 | 3 | | | III-1 | Fgfr3 | 2261 | 23-May-15 | 7791 | 2 | 3 | | III-1 | Galnt9 | 50614 | 4-May-15 |
| 7437 | 2 | 3 | | | III-1 | Fgl2 | 10875 | 12-May-15 | 7792 | 2 | 3 | | III-1 | Galntl5 | 168391 | 23-May-15 |
| 7438 | 2 | 3 | | | III-1 | Fgr | 2268 | 12-May-15 | 7797 | 2 | 3 | | III-1 | Galr3 | 8484 | 12-May-15 |
| 7448 | 2 | 3 | | | III-1 | Fhl5 | 9457 | 7-Jun-15 | 7806 | 2 | 3 | | III-1 | Gapt | 202309 | 12-May-15 |
| 7451 | 2 | 3 | | | III-1 | Fibcd1 | 84929 | 4-May-15 | 7810 | 2 | 3 | | III-1 | Garem1 | 150946 | 4-May-15 |
| 7453 | 2 | 3 | | | III-1 | Fibp | 9158 | 2-Jun-15 | 7815 | 2 | 3 | | III-1 | Gas2 | 2620 | 4-May-15 |
| 7454 | 2 | 3 | | | III-1 | Ficd | 11153 | 4-May-15 | 7817 | 2 | 3 | | III-1 | Gas2l2 | 246176 | 4-May-15 |
| 7457 | 2 | 3 | | | III-1 | Figla | 344018 | 4-May-15 | 7821 | 2 | 3 | | III-1 | Gas7 | 8522 | 4-May-15 |
| 7463 | 2 | 3 | | | III-1 | Fip1l1 | 81608 | 3-May-15 | 7822 | 2 | 3 | | III-1 | Gas8 | 2622 | 12-May-15 |
| 7465 | 2 | 3 | | | III-1 | Fis1 | 51024 | 4-May-15 | 7823 | 2 | 3 | | III-1 | Gast | 2520 | 12-May-15 |
| 7468 | 2 | 3 | | | III-1 | Fiz1 | 84922 | 4-May-15 | 7827 | 2 | 3 | | III-1 | Gata4 | 2626 | 31-May-15 |
| 7470 | 2 | 3 | | | III-1 | Fkbp10 | 60681 | 4-May-15 | 7828 | 2 | 3 | | III-1 | Gata5 | 140628 | 4-May-15 |
| 7476 | 2 | 3 | | | III-1 | Fkbp2 | 2286 | 4-May-15 | 7829 | 2 | 3 | | III-1 | Gata6os | | |
| 7478 | 2 | 3 | | | III-1 | Fkbp4 | 2288 | 7-Jun-15 | 7831 | 2 | 3 | | III-1 | Gatad1 | 57798 | 12-May-15 |
| 7480 | 2 | 3 | | | III-1 | Fkbp6 | 8468 | 4-May-15 | 7841 | 2 | 3 | | III-1 | Gbe1 | 2632 | 23-May-15 |
| 7484 | 2 | 3 | | | III-1 | Fkbpl | 63943 | 25-May-15 | 7842 | 2 | 3 | | III-1 | Gbf1 | 8729 | 16-Jun-15 |
| 7487 | 2 | 3 | | | III-1 | Flad1 | 80308 | 4-May-15 | 7847 | 2 | 3 | | III-1 | Gbp2b | | |
| 7490 | 2 | 3 | | | III-1 | Flt1 | 2313 | 7-Jun-15 | 7853 | 2 | 3 | | III-1 | Gbp8 | | |
| 7491 | 2 | 3 | | | III-1 | Flt | 2314 | 3-Jun-15 | 7860 | 2 | 3 | | III-1 | Gcc1 | 79571 | 4-May-15 |
| 7496 | 2 | 3 | | | III-1 | Flot2 | 2319 | 3-May-15 | 7861 | 2 | 3 | | III-1 | Gcc2 | 9648 | 4-May-15 |
| 7499 | 2 | 3 | | | III-1 | Flt3 | 23767 | 4-May-15 | 7865 | 2 | 3 | | III-1 | Gcgr | 2642 | 4-May-15 |
| 7501 | 2 | 3 | | | III-1 | Flt3 | 2322 | 31-May-15 | 7866 | 2 | 3 | | III-1 | Gch1 | 1643 | 23-May-15 |
| 7502 | 2 | 3 | | | III-1 | Flt3l | 2323 | 12-May-15 | 7870 | 2 | 3 | | III-1 | Gck | 2729 | 12-May-15 |
| 7503 | 2 | 3 | | | III-1 | Flt4 | 2324 | 23-May-15 | 7872 | 2 | 3 | | III-1 | Gcm1 | 8521 | 4-May-15 |
| 7504 | 2 | 3 | | | III-1 | Flywch1 | 84256 | 12-May-15 | 7874 | 2 | 3 | | III-1 | Gcnt1 | 10985 | 12-May-15 |
| 7515 | 2 | 3 | | | III-1 | Fmo5 | 2330 | 4-May-15 | 7876 | 2 | 3 | | III-1 | Gcnt2 | 2651 | 23-May-15 |
| 7516 | 2 | 3 | | | III-1 | Fmo6 | 388714 | 4-May-15 | 7877 | 2 | 3 | | III-1 | Gcnt3 | 9245 | 24-May-15 |
| 7524 | 2 | 3 | | | III-1 | Fnbp1 | 23048 | 4-May-15 | 7879 | 2 | 3 | | III-1 | Gcnt7 | 140687 | 4-May-15 |
| 7532 | 2 | 3 | | | III-1 | Fndc4 | 64838 | 4-May-15 | 7883 | 2 | 3 | | III-1 | Gdap1 | 54332 | 23-May-15 |
| 7535 | 2 | 3 | | | III-1 | Fndc8 | 54752 | 4-May-15 | 7886 | 2 | 3 | | III-1 | Gdap2 | 54834 | 12-May-15 |
| 7546 | 2 | 3 | | | III-1 | Fopnl | 123811 | 12-May-15 | 7888 | 2 | 3 | | III-1 | Gdf1 | 2657 | 4-May-15 |
| 7551 | 2 | 3 | | | III-1 | Foxa1 | 3169 | 17-May-15 | 7895 | 2 | 3 | | III-1 | Gdf6 | 392255 | 4-May-15 |
| 7557 | 2 | 3 | | | III-1 | Foxc2 | 2303 | 23-May-15 | 7897 | 2 | 3 | | III-1 | Gdf9 | 2661 | 4-May-15 |
| 7558 | 2 | 3 | | | III-1 | Foxd1 | 2297 | 28-May-15 | 7903 | 2 | 3 | | III-1 | Gdpd3 | 79153 | 21-May-15 |
| 7562 | 2 | 3 | | | III-1 | Foxd4 | 2298 | 28-May-15 | 7908 | 2 | 3 | | III-1 | Gemin2 | 8487 | 23-May-15 |
| 7568 | 2 | 3 | | | III-1 | Foxh1 | 8928 | 28-May-15 | 7909 | 2 | 3 | | III-1 | Gemin4 | 50628 | 4-May-15 |
| 7570 | 2 | 3 | | | III-1 | Foxi2 | 399823 | 28-May-15 | 7912 | 2 | 3 | | III-1 | Gemin7 | 79760 | 4-May-15 |
| 7573 | 2 | 3 | | | III-1 | Foxj2 | 55810 | 28-May-15 | 7914 | 2 | 3 | | III-1 | Gen1 | 348654 | 4-May-15 |
| 7580 | 2 | 3 | | | III-1 | Foxm1 | 2305 | 17-May-15 | 7917 | 2 | 3 | | III-1 | Gfer | 2671 | 12-May-15 |
| 7588 | 2 | 3 | | | III-1 | Foxo6 | 100132074 | 28-May-15 | 7923 | 2 | 3 | | III-1 | Gfod2 | 81577 | 4-May-15 |
| 7592 | 2 | 3 | | | III-1 | Foxp4 | 116113 | 4-May-15 | 7927 | 2 | 3 | | III-1 | Gfra2 | 2675 | 12-May-15 |
| 7598 | 2 | 3 | | | III-1 | Foxs1 | 2307 | 4-May-15 | 7930 | 2 | 3 | | III-1 | Gfral | 389400 | 4-May-15 |
| 7600 | 2 | 3 | | | III-1 | Fpgt | 8790 | 4-May-15 | 7934 | 2 | 3 | | III-1 | Gga3 | 23163 | 12-May-15 |
| 7603 | 2 | 3 | | | III-1 | Fpr3 | 2359 | 4-May-15 | 7939 | 2 | 3 | | III-1 | Ggn | 199720 | 4-May-15 |
| 7608 | 2 | 3 | | | III-1 | Fras1 | 80144 | 12-May-15 | 7941 | 2 | 3 | | III-1 | Ggnbp2 | 79893 | 4-May-15 |
| 7614 | 2 | 3 | | | III-1 | Frg1 | 2483 | 23-May-15 | 7945 | 2 | 3 | | III-1 | Ggt6 | 124975 | 4-May-15 |
| 7616 | 2 | 3 | | | III-1 | Frmd3 | 257019 | 4-May-15 | 7947 | 2 | 3 | | III-1 | Ggta1 | 2681 | 4-May-15 |
| 7618 | 2 | 3 | | | III-1 | Frmd4b | 23150 | 12-May-15 | 7952 | 2 | 3 | | III-1 | Ghrh | 2691 | 12-May-15 |
| 7620 | 2 | 3 | | | III-1 | Frmd8 | 122786 | 4-May-15 | 7960 | 2 | 3 | | III-1 | Gigyf2 | 26058 | 23-May-15 |
| 7625 | 2 | 3 | | | III-1 | Frmpd3 | 84443 | 4-May-15 | 7965 | 2 | 3 | | III-1 | Gimap6 | 474344 | 4-May-15 |
| 7628 | 2 | 3 | | | III-1 | Frrs1l | 23732 | 4-May-15 | 7968 | 2 | 3 | | III-1 | Gimap9 | | |
| 7630 | 2 | 3 | | | III-1 | Frs3 | 10817 | 3-May-15 | 7969 | 2 | 3 | | III-1 | Gin1 | 54826 | 4-May-15 |
| 7631 | 2 | 3 | | | III-1 | Frs3os | | | 7970 | 2 | 3 | | III-1 | Ginm1 | 116254 | 4-May-15 |
| 7649 | 2 | 3 | | | III-1 | Fstl4 | 23105 | 4-May-15 | 7974 | 2 | 3 | | III-1 | Gins4 | 84296 | 4-May-15 |
| 7655 | 2 | 3 | | | III-1 | Ftmt | 94033 | 28-May-15 | 7979 | 2 | 3 | | III-1 | Gipr | 2696 | 9-May-15 |
| 7658 | 2 | 3 | | | III-1 | Ftsj2 | 29960 | 30-May-15 | 7983 | 2 | 3 | | III-1 | Gja10 | 84694 | 4-May-15 |
| 7663 | 2 | 3 | | | III-1 | Fuca1 | 2517 | 21-May-15 | 7986 | 2 | 3 | | III-1 | Gja5 | 2702 | 31-May-15 |
| 7665 | 2 | 3 | | | III-1 | Fuk | 197258 | 4-May-15 | 7987 | 2 | 3 | | III-1 | Gja6 | | |
| 7668 | 2 | 3 | | | III-1 | Fuom | 282969 | 12-May-15 | 7994 | 2 | 3 | | III-1 | Gjb6 | 10804 | 23-May-15 |
| 7669 | 2 | 3 | | | III-1 | Furin | 5045 | 31-May-15 | 7995 | 2 | 3 | | III-1 | Gjc1 | 10052 | 7-Jun-15 |
| 7673 | 2 | 3 | | | III-1 | Fut11 | 170384 | 23-May-15 | 7996 | 2 | 3 | | III-1 | Gjc2 | 57165 | 12-May-15 |
| 7676 | 2 | 3 | | | III-1 | Fut4-ps1 | | | 8005 | 2 | 3 | | III-1 | Gkn1 | 56287 | 4-May-15 |
| 7681 | 2 | 3 | | | III-1 | Fv1 | | | 8010 | 2 | 3 | | III-1 | Glb1l | 79411 | 23-May-15 |
| 7683 | 2 | 3 | | | III-1 | Fxr1 | 8087 | 1-Jun-15 | 8013 | 2 | 3 | | III-1 | Glcci1 | 113263 | 12-May-15 |
| 7684 | 2 | 3 | | | III-1 | Fxr2 | 9513 | 12-May-15 | 8016 | 2 | 3 | | III-1 | Gldn | 342035 | 4-May-15 |
| 7689 | 2 | 3 | | | III-1 | Fxyd5 | 53827 | 4-May-15 | 8031 | 2 | 3 | | III-1 | Glo1 | 2739 | 17-May-15 |
| 7690 | 2 | 3 | | | III-1 | Fxyd6 | 53826 | 4-May-15 | 8035 | 2 | 3 | | III-1 | Glp2r | 9340 | 4-May-15 |
| 7691 | 2 | 3 | | | III-1 | Fxyd7 | 53822 | 12-May-15 | 8042 | 2 | 3 | | III-1 | Glrx | 2745 | 12-May-15 |
| 7694 | 2 | 3 | | | III-1 | Fyn | 2534 | 12-May-15 | 8043 | 2 | 3 | | III-1 | Glrx2 | 51022 | 4-May-15 |
| 7698 | 2 | 3 | | | III-1 | Fzd2 | 2535 | 4-May-15 | 8046 | 2 | 3 | | III-1 | Gls | 2744 | 13-Jun-15 |
| 7699 | 2 | 3 | | | III-1 | Fzd3 | 7976 | 7-Jun-15 | 8049 | 2 | 3 | | III-1 | Glt25d1 | 79709 | 4-May-15 |
| 7703 | 2 | 3 | | | III-1 | Fzd6 | 8324 | 4-May-15 | 8051 | 2 | 3 | | III-1 | Glt6d1 | 360203 | 4-May-15 |
| 7713 | 2 | 3 | | | III-1 | G630055G22Rik | | | 8053 | 2 | 3 | | III-1 | Glt8d2 | 83468 | 23-May-15 |
| 7723 | 2 | 3 | | | III-1 | G6pdx | | | 8057 | 2 | 3 | | III-1 | Gltscr1 | 29998 | 21-May-15 |
| 7724 | 2 | 3 | | | III-1 | G730013B05Rik | | | 8058 | 2 | 3 | | III-1 | Gltscr1l | 23506 | 12-May-15 |
| 7727 | 2 | 3 | | | III-1 | Gab2 | 9846 | 17-May-15 | 8059 | 2 | 3 | | III-1 | Gltscr2 | 29997 | 4-May-15 |
| 7728 | 2 | 3 | | | III-1 | Gab3 | 139716 | 12-May-15 | 8062 | 2 | 3 | | III-1 | Glyat | 10249 | 4-May-15 |

Fig.22 - 68

| | | | | | | | | | | | | | | |
|---|---|---|---|---|---|---|---|---|---|---|---|---|---|---|
| 8065 | 2 | 3 | | | III-1 | Glyctk | 132158 | 4-May-15 | 8572 | 2 | 3 | | | III-1 | Gm17689 |
| 8069 | 2 | 3 | | | III-1 | Gm10024 | | | 8574 | 2 | 3 | | | III-1 | Gm17745 |
| 8071 | 2 | 3 | | | III-1 | Gm10046 | | | 8589 | 2 | 3 | | | III-1 | Gm19303 |
| 8075 | 2 | 3 | | | III-1 | Gm10069 | | | 8600 | 2 | 3 | | | III-1 | Gm19557 |
| 8078 | 2 | 3 | | | III-1 | Gm10096 | | | 8601 | 2 | 3 | | | III-1 | Gm19583 |
| 8079 | 2 | 3 | | | III-1 | Gm101 | | | 8604 | 2 | 3 | | | III-1 | Gm1965 |
| 8110 | 2 | 3 | | | III-1 | Gm10413 | | | 8605 | 2 | 3 | | | III-1 | Gm1966 |
| 8118 | 2 | 3 | | | III-1 | Gm10440 | | | 8610 | 2 | 3 | | | III-1 | Gm19710 |
| 8122 | 2 | 3 | | | III-1 | Gm10466 | | | 8611 | 2 | 3 | | | III-1 | Gm19757 |
| 8130 | 2 | 3 | | | III-1 | Gm10510 | | | 8613 | 2 | 3 | | | III-1 | Gm19782 |
| 8140 | 2 | 3 | | | III-1 | Gm10578 | | | 8620 | 2 | 3 | | | III-1 | Gm19990 |
| 8149 | 2 | 3 | | | III-1 | Gm10640 | | | 8637 | 2 | 3 | | | III-1 | Gm2030 |
| 8152 | 2 | 3 | | | III-1 | Gm10658 | | | 8641 | 2 | 3 | | | III-1 | Gm20337 |
| 8153 | 2 | 3 | | | III-1 | Gm10662 | | | 8646 | 2 | 3 | | | III-1 | Gm20556 |
| 8166 | 2 | 3 | | | III-1 | Gm10768 | | | 8652 | 2 | 3 | | | III-1 | Gm20611 |
| 8167 | 2 | 3 | | | III-1 | Gm10778 | | | 8659 | 2 | 3 | | | III-1 | Gm20744 |
| 8173 | 2 | 3 | | | III-1 | Gm10791 | | | 8663 | 2 | 3 | | | III-1 | Gm20750 |
| 8177 | 2 | 3 | | | III-1 | Gm10825 | | | 8668 | 2 | 3 | | | III-1 | Gm20755 |
| 8187 | 2 | 3 | | | III-1 | Gm11110 | | | 8678 | 2 | 3 | | | III-1 | Gm20816 |
| 8192 | 2 | 3 | | | III-1 | Gm11186 | | | 8686 | 2 | 3 | | | III-1 | Gm20858 |
| 8199 | 2 | 3 | | | III-1 | Gm11346 | | | 8691 | 2 | 3 | | | III-1 | Gm20877 |
| 8200 | 2 | 3 | | | III-1 | Gm11351 | | | 8693 | 2 | 3 | | | III-1 | Gm20917 |
| 8201 | 2 | 3 | | | III-1 | Gm1140 | | | 8697 | 2 | 3 | | | III-1 | Gm2109 |
| 8206 | 2 | 3 | | | III-1 | Gm11468 | | | 8715 | 2 | 3 | | | III-1 | Gm21768 |
| 8209 | 2 | 3 | | | III-1 | Gm11529 | | | 8716 | 2 | 3 | | | III-1 | Gm2176 |
| 8221 | 2 | 3 | | | III-1 | Gm11565 | | | 8723 | 2 | 3 | | | III-1 | Gm2381 |
| 8224 | 2 | 3 | | | III-1 | Gm11569 | | | 8725 | 2 | 3 | | | III-1 | Gm2447 |
| 8225 | 2 | 3 | | | III-1 | Gm11570 | | | 8730 | 2 | 3 | | | III-1 | Gm2694 |
| 8228 | 2 | 3 | | | III-1 | Gm11627 | | | 8750 | 2 | 3 | | | III-1 | Gm3230 |
| 8229 | 2 | 3 | | | III-1 | Gm11651 | | | 8751 | 2 | 3 | | | III-1 | Gm3238 |
| 8230 | 2 | 3 | | | III-1 | Gm11696 | | | 8759 | 2 | 3 | | | III-1 | Gm3336 |
| 8233 | 2 | 3 | | | III-1 | Gm11747 | | | 8760 | 2 | 3 | | | III-1 | Gm3383 |
| 8237 | 2 | 3 | | | III-1 | Gm11780 | | | 8761 | 2 | 3 | | | III-1 | Gm3402 |
| 8244 | 2 | 3 | | | III-1 | Gm11978 | | | 8769 | 2 | 3 | | | III-1 | Gm3435 |
| 8250 | 2 | 3 | | | III-1 | Gm12070 | | | 8770 | 2 | 3 | | | III-1 | Gm3458 |
| 8251 | 2 | 3 | | | III-1 | Gm12130 | | | 8772 | 2 | 3 | | | III-1 | Gm3500 |
| 8260 | 2 | 3 | | | III-1 | Gm12253 | | | 8779 | 2 | 3 | | | III-1 | Gm3701 |
| 8265 | 2 | 3 | | | III-1 | Gm12409 | | | 8785 | 2 | 3 | | | III-1 | Gm382 |
| 8266 | 2 | 3 | | | III-1 | Gm12429 | | | 8790 | 2 | 3 | | | III-1 | Gm4070 |
| 8287 | 2 | 3 | | | III-1 | Gm13003 | | | 8800 | 2 | 3 | | | III-1 | Gm4265 |
| 8293 | 2 | 3 | | | III-1 | Gm13040 | | | 8815 | 2 | 3 | | | III-1 | Gm44 |
| 8305 | 2 | 3 | | | III-1 | Gm13125 | | | 8821 | 2 | 3 | | | III-1 | Gm4541 |
| 8313 | 2 | 3 | | | III-1 | Gm13212 | | | 8823 | 2 | 3 | | | III-1 | Gm4566 |
| 8319 | 2 | 3 | | | III-1 | Gm13271 | | | 8830 | 2 | 3 | | | III-1 | Gm4745 |
| 8340 | 2 | 3 | | | III-1 | Gm13446 | | | 8836 | 2 | 3 | | | III-1 | Gm4791 |
| 8345 | 2 | 3 | | | III-1 | Gm13539 | | | 8840 | 2 | 3 | | | III-1 | Gm4827 |
| 8348 | 2 | 3 | | | III-1 | Gm13547 | | | 8843 | 2 | 3 | | | III-1 | Gm4841 |
| 8353 | 2 | 3 | | | III-1 | Gm13826 | | | 8845 | 2 | 3 | | | III-1 | Gm4847 |
| 8359 | 2 | 3 | | | III-1 | Gm13871 | | | 8849 | 2 | 3 | | | III-1 | Gm4871 |
| 8371 | 2 | 3 | | | III-1 | Gm14139 | | | 8859 | 2 | 3 | | | III-1 | Gm4937 |
| 8379 | 2 | 3 | | | III-1 | Gm14305 | | | 8883 | 2 | 3 | | | III-1 | Gm5091 |
| 8384 | 2 | 3 | | | III-1 | Gm14326 | | | 8888 | 2 | 3 | | | III-1 | Gm5113 |
| 8385 | 2 | 3 | | | III-1 | Gm14327 | | | 8889 | 2 | 3 | | | III-1 | Gm5114 |
| 8386 | 2 | 3 | | | III-1 | Gm14345 | | | 8893 | 2 | 3 | | | III-1 | Gm5127 |
| 8392 | 2 | 3 | | | III-1 | Gm14379 | | | 8894 | 2 | 3 | | | III-1 | Gm5129 |
| 8394 | 2 | 3 | | | III-1 | Gm14393 | | | 8896 | 2 | 3 | | | III-1 | Gm5134 |
| 8395 | 2 | 3 | | | III-1 | Gm14403 | | | 8899 | 2 | 3 | | | III-1 | Gm5142 |
| 8396 | 2 | 3 | | | III-1 | Gm14405 | | | 8902 | 2 | 3 | | | III-1 | Gm5166 |
| 8398 | 2 | 3 | | | III-1 | Gm14431 | | | 8916 | 2 | 3 | | | III-1 | Gm5414 |
| 8408 | 2 | 3 | | | III-1 | Gm14477 | | | 8917 | 2 | 3 | | | III-1 | Gm5415 |
| 8416 | 2 | 3 | | | III-1 | Gm14501 | | | 8923 | 2 | 3 | | | III-1 | Gm5441 |
| 8427 | 2 | 3 | | | III-1 | Gm14725 | | | 8934 | 2 | 3 | | | III-1 | Gm5512 |
| 8436 | 2 | 3 | | | III-1 | Gm14858 | | | 8937 | 2 | 3 | | | III-1 | Gm5535 |
| 8444 | 2 | 3 | | | III-1 | Gm15097 | | | 8939 | 2 | 3 | | | III-1 | Gm5544 |
| 8450 | 2 | 3 | | | III-1 | Gm15140 | | | 8948 | 2 | 3 | | | III-1 | Gm5615 |
| 8452 | 2 | 3 | | | III-1 | Gm15217 | | | 8950 | 2 | 3 | | | III-1 | Gm5622 |
| 8465 | 2 | 3 | | | III-1 | Gm15401 | | | 8953 | 2 | 3 | | | III-1 | Gm5635 |
| 8466 | 2 | 3 | | | III-1 | Gm15408 | | | 8956 | 2 | 3 | | | III-1 | Gm5662 |
| 8470 | 2 | 3 | | | III-1 | Gm15421 | | | 8959 | 2 | 3 | | | III-1 | Gm5725 |
| 8473 | 2 | 3 | | | III-1 | Gm15455 | | | 8963 | 2 | 3 | | | III-1 | Gm5766 |
| 8474 | 2 | 3 | | | III-1 | Gm15471 | | | 8968 | 2 | 3 | | | III-1 | Gm5797 |
| 8477 | 2 | 3 | | | III-1 | Gm156 | | | 8972 | 2 | 3 | | | III-1 | Gm5820 |
| 8479 | 2 | 3 | | | III-1 | Gm1564 | | | 8976 | 2 | 3 | | | III-1 | Gm5868 |
| 8485 | 2 | 3 | | | III-1 | Gm15708 | | | 8985 | 2 | 3 | | | III-1 | Gm5925 |
| 8486 | 2 | 3 | | | III-1 | Gm15713 | | | 8989 | 2 | 3 | | | III-1 | Gm5938 |
| 8488 | 2 | 3 | | | III-1 | Gm15772 | | | 8996 | 2 | 3 | | | III-1 | Gm6042 |
| 8489 | 2 | 3 | | | III-1 | Gm15787 | | | 9001 | 2 | 3 | | | III-1 | Gm6116 |
| 8490 | 2 | 3 | | | III-1 | Gm15800 | | | 9004 | 2 | 3 | | | III-1 | Gm6150 |
| 8493 | 2 | 3 | | | III-1 | Gm1587 | | | 9011 | 2 | 3 | | | III-1 | Gm6260 |
| 8502 | 2 | 3 | | | III-1 | Gm16039 | | | 9013 | 2 | 3 | | | III-1 | Gm6277 |
| 8504 | 2 | 3 | | | III-1 | Gm16062 | | | 9015 | 2 | 3 | | | III-1 | Gm6297 |
| 8505 | 2 | 3 | | | III-1 | Gm16063 | | | 9020 | 2 | 3 | | | III-1 | Gm6367 |
| 8516 | 2 | 3 | | | III-1 | Gm16386 | | | 9023 | 2 | 3 | | | III-1 | Gm6402 |
| 8521 | 2 | 3 | | | III-1 | Gm16432 | | | 9032 | 2 | 3 | | | III-1 | Gm6498 |
| 8534 | 2 | 3 | | | III-1 | Gm16596 | | | 9040 | 2 | 3 | | | III-1 | Gm6578 |
| 8535 | 2 | 3 | | | III-1 | Gm166 | | | 9047 | 2 | 3 | | | III-1 | Gm6623 |
| 8538 | 2 | 3 | | | III-1 | Gm16675 | | | 9053 | 2 | 3 | | | III-1 | Gm6682 |
| 8539 | 2 | 3 | | | III-1 | Gm16677 | | | 9055 | 2 | 3 | | | III-1 | Gm6710 |
| 8546 | 2 | 3 | | | III-1 | Gm16796 | | | 9056 | 2 | 3 | | | III-1 | Gm6756 |
| 8549 | 2 | 3 | | | III-1 | Gm16853 | | | 9061 | 2 | 3 | | | III-1 | Gm6793 |
| 8551 | 2 | 3 | | | III-1 | Gm16863 | | | 9065 | 2 | 3 | | | III-1 | Gm6878 |
| 8556 | 2 | 3 | | | III-1 | Gm16938 | | | 9071 | 2 | 3 | | | III-1 | Gm6936 |
| 8558 | 2 | 3 | | | III-1 | Gm16982 | | | 9074 | 2 | 3 | | | III-1 | Gm6981 |
| 8560 | 2 | 3 | | | III-1 | Gm17019 | | | 9078 | 2 | 3 | | | III-1 | Gm7056 |
| 8562 | 2 | 3 | | | III-1 | Gm1715 | | | 9084 | 2 | 3 | | | III-1 | Gm7134 |
| 8565 | 2 | 3 | | | III-1 | Gm17296 | | | 9086 | 2 | 3 | | | III-1 | Gm7157 |
| 8568 | 2 | 3 | | | III-1 | Gm17455 | | | 9098 | 2 | 3 | | | III-1 | Gm7444 |

Fig.22 - 69

| | | | | | | | | | | | | | | | |
|---|---|---|---|---|---|---|---|---|---|---|---|---|---|---|---|
| 9108 | 2 | 3 | | III-1 | Gm7714 | | | 9499 | 2 | 3 | | III-1 | Grip2 | 80852 | 4-May-15 |
| 9110 | 2 | 3 | | III-1 | Gm7788 | | | 9500 | 2 | 3 | | III-1 | Gripap1 | 56850 | 4-May-15 |
| 9128 | 2 | 3 | | III-1 | Gm829 | | | 9507 | 2 | 3 | | III-1 | Grm3 | 2913 | 4-May-15 |
| 9149 | 2 | 3 | | III-1 | Gm8817 | | | 9514 | 2 | 3 | | III-1 | Grp | 2922 | 17-May-15 |
| 9152 | 2 | 3 | | III-1 | Gm8883 | | | 9517 | 2 | 3 | | III-1 | Grpr | 2925 | 17-May-15 |
| 9159 | 2 | 3 | | III-1 | Gm9 | | | 9519 | 2 | 3 | | III-1 | Grsf1 | 2926 | 31-May-15 |
| 9161 | 2 | 3 | | III-1 | Gm9047 | | | 9522 | 2 | 3 | | III-1 | Grxcr1 | 389207 | 4-May-15 |
| 9173 | 2 | 3 | | III-1 | Gm9513 | | | 9525 | 2 | 3 | | III-1 | Gsc | 145258 | 4-May-15 |
| 9193 | 2 | 3 | | III-1 | Gm996 | | | 9529 | 2 | 3 | | III-1 | Gsdma3 | | |
| 9195 | 2 | 3 | | III-1 | Gm9962 | | | 9540 | 2 | 3 | | III-1 | Gsg1l | 146395 | 4-May-15 |
| 9198 | 2 | 3 | | III-1 | Gm9999 | | | 9542 | 2 | 3 | | III-1 | Gsk3a | 2931 | 28-May-15 |
| 9202 | 2 | 3 | | III-1 | Gmeb1 | 10691 | 4-May-15 | 9545 | 2 | 3 | | III-1 | Gsn | 2934 | 12-May-15 |
| 9208 | 2 | 3 | | III-1 | Gmnc | 647309 | 4-May-15 | 9546 | 2 | 3 | | III-1 | Gspt1 | 2935 | 4-May-15 |
| 9209 | 2 | 3 | | III-1 | Gmnn | 51053 | 24-May-15 | 9554 | 2 | 3 | | III-1 | Gstcd | 79807 | 4-May-15 |
| 9213 | 2 | 3 | | III-1 | Gmpr2 | 51292 | 4-May-15 | 9564 | 2 | 3 | | III-1 | Gsto2 | 119391 | 12-May-15 |
| 9217 | 2 | 3 | | III-1 | Gna13 | 10672 | 17-May-15 | 9569 | 2 | 3 | | III-1 | Gstt3 | | |
| 9221 | 2 | 3 | | III-1 | Gnai2 | 2771 | 12-May-15 | 9570 | 2 | 3 | | III-1 | Gstt4 | 25774 | 4-May-15 |
| 9224 | 2 | 3 | | III-1 | Gnao1 | 2775 | 12-May-15 | 9572 | 2 | 3 | | III-1 | Gsx1 | 219409 | 28-May-15 |
| 9227 | 2 | 3 | | III-1 | Gnat1 | 2779 | 21-May-15 | 9575 | 2 | 3 | | III-1 | Gtdc1 | 79712 | 21-May-15 |
| 9230 | 2 | 3 | | III-1 | Gnaz | 2781 | 4-May-15 | 9579 | 2 | 3 | | III-1 | Gtf2b | 2959 | 4-May-15 |
| 9236 | 2 | 3 | | III-1 | Gnb4 | 59345 | 4-May-15 | 9584 | 2 | 3 | | III-1 | Gtf2h1 | 2965 | 4-May-15 |
| 9238 | 2 | 3 | | III-1 | Gne | 10020 | 23-May-15 | 9588 | 2 | 3 | | III-1 | Gtf2h5 | 404672 | 4-Jun-15 |
| 9239 | 2 | 3 | | III-1 | Gng10 | 2790 | 4-May-15 | 9589 | 2 | 3 | | III-1 | Gtf2i | 2969 | 7-Jun-15 |
| 9244 | 2 | 3 | | III-1 | Gng3 | 2785 | 4-May-15 | 9591 | 2 | 3 | | III-1 | Gtf2ird2 | 84163 | 4-May-15 |
| 9246 | 2 | 3 | | III-1 | Gng5 | 2787 | 12-May-15 | 9592 | 2 | 3 | | III-1 | Gtf3a | 2971 | 4-May-15 |
| 9247 | 2 | 3 | | III-1 | Gng7 | 2788 | 4-May-15 | 9602 | 2 | 3 | | III-1 | Gtpbp2 | 54676 | 2-Jun-15 |
| 9249 | 2 | 3 | | III-1 | Gngt1 | 2792 | 3-May-15 | 9605 | 2 | 3 | | III-1 | Gtpbp6 | 8225 | 21-May-15 |
| 9254 | 2 | 3 | | III-1 | Gnl3l | 54552 | 4-May-15 | 9607 | 2 | 3 | | III-1 | Gtse1 | 51512 | 12-May-15 |
| 9260 | 2 | 3 | | III-1 | Gnptab | 79158 | 23-May-15 | 9614 | 2 | 3 | | III-1 | Gucd1 | 83606 | 4-May-15 |
| 9261 | 2 | 3 | | III-1 | Gnptg | 84572 | 23-May-15 | 9615 | 2 | 3 | | III-1 | Gucy1a2 | 2977 | 4-May-15 |
| 9262 | 2 | 3 | | III-1 | Gnrh1 | 2796 | 31-May-15 | 9617 | 2 | 3 | | III-1 | Gucy1b2 | 2974 | 4-May-15 |
| 9268 | 2 | 3 | | III-1 | Golga4 | 2803 | 4-May-15 | 9627 | 2 | 3 | | III-1 | Gulp1 | 51454 | 12-May-15 |
| 9269 | 2 | 3 | | III-1 | Golga5 | 9950 | 7-Jun-15 | 9628 | 2 | 3 | | III-1 | Gusb | 2990 | 4-May-15 |
| 9273 | 2 | 3 | | III-1 | Golim4 | 27333 | 12-May-15 | 9634 | 2 | 3 | | III-1 | Gykl1 | | |
| 9274 | 2 | 3 | | III-1 | Golm1 | 51280 | 17-May-15 | 9638 | 2 | 3 | | III-1 | Gys1 | 2997 | 12-May-15 |
| 9275 | 2 | 3 | | III-1 | Golph3 | 64083 | 12-May-15 | 9639 | 2 | 3 | | III-1 | Gys2 | 2998 | 4-May-15 |
| 9281 | 2 | 3 | | III-1 | Gorab | 92344 | 4-May-15 | 9643 | 2 | 3 | | III-1 | Gzmc | | |
| 9282 | 2 | 3 | | III-1 | Gorasp1 | 64689 | 4-May-15 | 9644 | 2 | 3 | | III-1 | Gzmd | | |
| 9289 | 2 | 3 | | III-1 | Gp1ba | 2811 | 12-May-15 | 9650 | 2 | 3 | | III-1 | Gzmn | | |
| 9293 | 2 | 3 | | III-1 | Gp5 | 2814 | 4-May-15 | 9655 | 2 | 3 | | III-1 | H1foo | 132243 | 12-May-15 |
| 9297 | 2 | 3 | | III-1 | Gpaa1 | 8733 | 4-May-15 | 9663 | 2 | 3 | | III-1 | H2afv | 94239 | 2-Jun-15 |
| 9308 | 2 | 3 | | III-1 | Gpatch8 | 23131 | 4-May-15 | 9665 | 2 | 3 | | III-1 | H2afy | 9555 | 12-May-15 |
| 9315 | 2 | 3 | | III-1 | Gpc4 | 2239 | 23-May-15 | 9668 | 2 | 3 | | III-1 | H2afz | 3015 | 12-May-15 |
| 9317 | 2 | 3 | | III-1 | Gpc6 | 10082 | 4-May-15 | 9672 | 2 | 3 | | III-1 | H2-DMa | | |
| 9320 | 2 | 3 | | III-1 | Gpd1l | 23171 | 23-May-15 | 9673 | 2 | 3 | | III-1 | H2-DMb1 | | |
| 9331 | 2 | 3 | | III-1 | Gpm6b | 2824 | 12-May-15 | 9679 | 2 | 3 | | III-1 | H2-K2 | | |
| 9332 | 2 | 3 | | III-1 | Gpn1 | 11321 | 4-May-15 | 9680 | 2 | 3 | | III-1 | H2-Ke2 | 10471 | 4-May-15 |
| 9334 | 2 | 3 | | III-1 | Gpn3 | 51184 | 4-May-15 | 9682 | 2 | 3 | | III-1 | H2-L | | |
| 9337 | 2 | 3 | | III-1 | Gpr101 | 83550 | 4-May-15 | 9695 | 2 | 3 | | III-1 | H2-Oa | | |
| 9344 | 2 | 3 | | III-1 | Gpr115 | 221393 | 12-May-15 | 9709 | 2 | 3 | | III-1 | H2-T24 | | |
| 9346 | 2 | 3 | | III-1 | Gpr119 | 139760 | 4-May-15 | 9712 | 2 | 3 | | III-1 | H3f3a | 3020 | 12-May-15 |
| 9348 | 2 | 3 | | III-1 | Gpr123 | 84435 | 12-May-15 | 9716 | 2 | 3 | | III-1 | H6pd | 9563 | 13-May-15 |
| 9352 | 2 | 3 | | III-1 | Gpr128 | 84873 | 21-May-15 | 9717 | 2 | 3 | | III-1 | Haao | 23498 | 4-May-15 |
| 9355 | 2 | 3 | | III-1 | Gpr135 | 64582 | 21-May-15 | 9718 | 2 | 3 | | III-1 | Habp2 | 3026 | 23-May-15 |
| 9356 | 2 | 3 | | III-1 | Gpr137 | 56834 | 12-May-15 | 9719 | 2 | 3 | | III-1 | Habp4 | 22927 | 12-May-15 |
| 9358 | 2 | 3 | | III-1 | Gpr137b-ps | | | 9722 | 2 | 3 | | III-1 | Hadh | 3033 | 7-Jun-15 |
| 9359 | 2 | 3 | | III-1 | Gpr137c | 283564 | 4-May-15 | 9725 | 2 | 3 | | III-1 | Hagh | 3029 | 12-May-15 |
| 9360 | 2 | 3 | | III-1 | Gpr139 | 124274 | 12-May-15 | 9726 | 2 | 3 | | III-1 | Haghl | 84264 | 21-May-15 |
| 9365 | 2 | 3 | | III-1 | Gpr149 | 344758 | 4-May-15 | 9727 | 2 | 3 | | III-1 | Hal | 3034 | 12-May-15 |
| 9371 | 2 | 3 | | III-1 | Gpr155 | 151556 | 4-May-15 | 9730 | 2 | 3 | | III-1 | Hand1 | 9421 | 17-May-15 |
| 9374 | 2 | 3 | | III-1 | Gpr158 | 57512 | 31-May-15 | 9735 | 2 | 3 | | III-1 | Hapln1 | 1404 | 28-May-15 |
| 9376 | 2 | 3 | | III-1 | Gpr161 | 23432 | 12-May-15 | 9743 | 2 | 3 | | III-1 | Has2 | 3037 | 14-May-15 |
| 9388 | 2 | 3 | | III-1 | Gpr183 | 1880 | 4-May-15 | 9747 | 2 | 3 | | III-1 | Haus1 | 115106 | 4-May-15 |
| 9390 | 2 | 3 | | III-1 | Gpr20 | 2843 | 21-May-15 | 9748 | 2 | 3 | | III-1 | Haus2 | 55142 | 4-May-15 |
| 9393 | 2 | 3 | | III-1 | Gpr25 | 2848 | 4-May-15 | 9751 | 2 | 3 | | III-1 | Haus5 | 23354 | 4-May-15 |
| 9399 | 2 | 3 | | III-1 | Gpr34 | 2857 | 4-May-15 | 9752 | 2 | 3 | | III-1 | Haus6 | 54801 | 4-May-15 |
| 9400 | 2 | 3 | | III-1 | Gpr35 | 2859 | 4-May-15 | 9756 | 2 | 3 | | III-1 | Havcr2 | 84868 | 24-May-15 |
| 9404 | 2 | 3 | | III-1 | Gpr4 | 2828 | 4-May-15 | 9757 | 2 | 3 | | III-1 | Hax1 | 10456 | 4-May-15 |
| 9407 | 2 | 3 | | III-1 | Gpr52 | 9293 | 4-May-15 | 9762 | 2 | 3 | | III-1 | Hbb-bh1 | | |
| 9411 | 2 | 3 | | III-1 | Gpr61 | 83873 | 4-May-15 | 9766 | 2 | 3 | | III-1 | Hbb-y | | |
| 9417 | 2 | 3 | | III-1 | Gpr75 | 10936 | 4-May-15 | 9768 | 2 | 3 | | III-1 | Hbp1 | 26959 | 4-May-15 |
| 9419 | 2 | 3 | | III-1 | Gpr83 | 10888 | 12-May-15 | 9779 | 2 | 3 | | III-1 | Hck | 3055 | 12-May-15 |
| 9420 | 2 | 3 | | III-1 | Gpr84 | 53831 | 4-May-15 | 9785 | 2 | 3 | | III-1 | Hcrt | 3060 | 17-May-15 |
| 9423 | 2 | 3 | | III-1 | Gpr88 | 54112 | 4-May-15 | 9787 | 2 | 3 | | III-1 | Hcrtr2 | 3062 | 16-Jun-15 |
| 9424 | 2 | 3 | | III-1 | Gpr89 | 653519 51463 | 4-May-15 14-May-15 | 9797 | 2 | 3 | | III-1 | Hdac7 | 51564 | 7-Jun-15 |
| 9426 | 2 | 3 | | III-1 | Gpr98 | 84059 | 23-May-15 | 9807 | 2 | 3 | | III-1 | Hdhd1a | 8226 | 28-May-15 |
| 9430 | 2 | 3 | | III-1 | Gprc5b | 51704 | 12-May-15 | 9815 | 2 | 3 | | III-1 | Heatr5a | 25938 | 4-May-15 |
| 9435 | 2 | 3 | | III-1 | Gprin2 | 9721 | 4-May-15 | 9817 | 2 | 3 | | III-1 | Heatr6 | 63897 | 4-May-15 |
| 9439 | 2 | 3 | | III-1 | Gpsn1 | 26086 | 4-May-15 | 9822 | 2 | 3 | | III-1 | Hectd1 | 25831 | 12-May-15 |
| 9441 | 2 | 3 | | III-1 | Gpsm3 | 63940 | 4-May-15 | 9824 | 2 | 3 | | III-1 | Hectd3 | 79654 | 4-May-15 |
| 9444 | 2 | 3 | | III-1 | Gpx1 | 2876 | 12-May-15 | 9831 | 2 | 3 | | III-1 | Helt | 391723 | 4-May-15 |
| 9448 | 2 | 3 | | III-1 | Gpx4 | 2879 | 10-May-15 | 9833 | 2 | 3 | | III-1 | Helz2 | 85441 | 12-May-15 |
| 9455 | 2 | 3 | | III-1 | Gramd1c | 54762 | 4-May-15 | 9837 | 2 | 3 | | III-1 | Hemnt1 | 113802 | 4-May-15 |
| 9456 | 2 | 3 | | III-1 | Gramd2 | 196996 | 4-May-15 | 9839 | 2 | 3 | | III-1 | Hepacam2 | 253012 | 4-May-15 |
| 9457 | 2 | 3 | | III-1 | Gramd3 | 65983 | 12-May-15 | 9840 | 2 | 3 | | III-1 | Heph | 9843 | 4-May-15 |
| 9459 | 2 | 3 | | III-1 | Grap | 10750 | 4-May-15 | 9841 | 2 | 3 | | III-1 | Hephl1 | 341208 | 4-May-15 |
| 9462 | 2 | 3 | | III-1 | Grb10 | 2887 | 4-May-15 | 9843 | 2 | 3 | | III-1 | Herc2 | 8924 | 23-May-15 |
| 9463 | 2 | 3 | | III-1 | Grb14 | 2888 | 17-May-15 | 9844 | 2 | 3 | | III-1 | Herc3 | 8916 | 4-May-15 |
| 9466 | 2 | 3 | | III-1 | Grcc10 | 133246 | 12-May-15 | 9845 | 2 | 3 | | III-1 | Herc4 | 26091 | 4-May-15 |
| 9468 | 2 | 3 | | III-1 | Greb1l | 80000 | 4-May-15 | 9848 | 2 | 3 | | III-1 | Herpud2 | 64224 | 4-May-15 |
| 9473 | 2 | 3 | | III-1 | Grhl3 | 57822 | 4-May-15 | 9850 | 2 | 3 | | III-1 | Hes2 | 54626 | 4-May-15 |
| 9476 | 2 | 3 | | III-1 | Gria2 | 2891 | 4-May-15 | 9855 | 2 | 3 | | III-1 | Hesx1 | 8820 | 4-May-15 |
| 9484 | 2 | 3 | | III-1 | Grik2 | 2898 | 7-Jun-15 | 9856 | 2 | 3 | | III-1 | Hexa | 3073 | 23-May-15 |
| 9488 | 2 | 3 | | III-1 | Grin1 | 2902 | 7-Jun-15 | 9858 | 2 | 3 | | III-1 | Hexdc | 284004 | 4-May-15 |
| 9490 | 2 | 3 | | III-1 | Grin2a | 2903 | 31-May-15 | 9862 | 2 | 3 | | III-1 | Hey2 | 23493 | 4-May-15 |
| 9493 | 2 | 3 | | III-1 | Grin2d | 2906 | 4-May-15 | 9864 | 2 | 3 | | III-1 | Hfe | 3077 | 23-May-15 |
| 9497 | 2 | 3 | | III-1 | Grip1 | 23426 | 7-Jun-15 | 9870 | 2 | 3 | | III-1 | Hgs | 9146 | 4-May-15 |

Fig.22 - 70

| | | | | | | | | | | | | | | | |
|---|---|---|---|---|---|---|---|---|---|---|---|---|---|---|---|
| 9872 | 2 | 3 | | III-1 | Hhat | 55733 | 4-May-15 | 10312 | 2 | 3 | | III-1 | Ifitm2 | 10581 | 4-May-15 |
| 9882 | 2 | 3 | | III-1 | Hibch | 26275 | 12-May-15 | 10313 | 2 | 3 | | III-1 | Ifitm3 | 10410 | 31-May-15 |
| 9883 | 2 | 3 | | III-1 | Hic1 | 3090 | 4-May-15 | 10343 | 2 | 3 | | III-1 | Ifnz | | |
| 9884 | 2 | 3 | | III-1 | Hic2 | 23119 | 4-May-15 | 10346 | 2 | 3 | | III-1 | Ift122 | 55764 | 12-May-15 |
| 9889 | 2 | 3 | | III-1 | Higd1a | 25994 | 4-May-15 | 10348 | 2 | 3 | | III-1 | Ift172 | 26160 | 4-Jun-15 |
| 9895 | 2 | 3 | | III-1 | Hinfp | 25988 | 4-May-15 | 10351 | 2 | 3 | | III-1 | Ift27 | 11020 | 4-May-15 |
| 9898 | 2 | 3 | | III-1 | Hint3 | 135114 | 4-May-15 | 10352 | 2 | 3 | | III-1 | Ift43 | 112752 | 4-May-15 |
| 9899 | 2 | 3 | | III-1 | Hip1 | 3092 | 7-Jun-15 | 10353 | 2 | 3 | | III-1 | Ift46 | 56912 | 12-May-15 |
| 9901 | 2 | 3 | | III-1 | Hipk1 | 204851 | 4-May-15 | 10357 | 2 | 3 | | III-1 | Ift80 | 57560 | 4-May-15 |
| 9904 | 2 | 3 | | III-1 | Hipk4 | 147746 | 4-May-15 | 10359 | 2 | 3 | | III-1 | Ift88 | 8100 | 21-May-15 |
| 9905 | 2 | 3 | | III-1 | Hira | 7290 | 4-May-15 | 10363 | 2 | 3 | | III-1 | Igdcc4 | 57722 | 4-May-15 |
| 9973 | 2 | 3 | | III-1 | Hist4h4 | 121504 | 12-May-15 | 10366 | 2 | 3 | | III-1 | Igf2 | 3481 | 24-May-15 |
| 9975 | 2 | 3 | | III-1 | Hivep2 | 3097 | 12-May-15 | 10367 | 2 | 3 | | III-1 | Igf2bp1 | 10642 | 1-Jun-15 |
| 9978 | 2 | 3 | | III-1 | Hk1 | 3098 | 7-Jun-15 | 10376 | 2 | 3 | | III-1 | Igfbp4 | 3487 | 4-May-15 |
| 9981 | 2 | 3 | | III-1 | Hk3 | 3101 | 7-Jun-15 | 10379 | 2 | 3 | | III-1 | Igfbp7 | 3490 | 12-May-15 |
| 9983 | 2 | 3 | | III-1 | Hlcs | 3141 | 4-May-15 | 10380 | 2 | 3 | | III-1 | Igfbpl1 | 347252 | 4-May-15 |
| 9985 | 2 | 3 | | III-1 | Hltf | 6596 | 4-May-15 | 10382 | 2 | 3 | | III-1 | Igflr1 | 79713 | 4-May-15 |
| 9989 | 2 | 3 | | III-1 | Hmces | 56941 | 4-May-15 | 10384 | 2 | 3 | | III-1 | Ighmbp2 | 3508 | 23-May-15 |
| 9995 | 2 | 3 | | III-1 | Hmga2 | 8091 | 31-May-15 | 10389 | 2 | 3 | | III-1 | Igsf1 | 3547 | 4-May-15 |
| 9996 | 2 | 3 | | III-1 | Hmga2-ps1 | | | 10392 | 2 | 3 | | III-1 | Igsf21 | 84966 | 4-May-15 |
| 10002 | 2 | 3 | | III-1 | Hmgcl | 3155 | 23-May-15 | 10394 | 2 | 3 | | III-1 | Igsf3 | 3321 | 4-May-15 |
| 10008 | 2 | 3 | | III-1 | Hmgn2 | 3151 | 4-May-15 | 10397 | 2 | 3 | | III-1 | Igsf8 | 93185 | 4-May-15 |
| 10012 | 2 | 3 | | III-1 | Hmgxb4 | 10042 | 4-May-15 | 10398 | 2 | 3 | | III-1 | Igsf9 | 57549 | 4-May-15 |
| 10016 | 2 | 3 | | III-1 | Hmcx2 | 3163 | 4-May-15 | 10404 | 2 | 3 | | III-1 | Ikbip | 121457 | 4-May-15 |
| 10018 | 2 | 3 | | III-1 | Hmx2 | 3167 | 4-May-15 | 10405 | 2 | 3 | | III-1 | Ikbkap | 8518 | 23-May-15 |
| 10020 | 2 | 3 | | III-1 | Hn1 | 51155 | 7-Jun-15 | 10409 | 2 | 3 | | III-1 | Ikzf1 | 10320 | 12-May-15 |
| 10022 | 2 | 3 | | III-1 | Hnf1a | 6927 | 21-May-15 | 10413 | 2 | 3 | | III-1 | Ikzf5 | 64376 | 2-Jun-15 |
| 10025 | 2 | 3 | | III-1 | Hnf4aos | | | 10417 | 2 | 3 | | III-1 | Il11 | 3589 | 4-May-15 |
| 10036 | 2 | 3 | | III-1 | Hnrnpf | 3185 | 4-May-15 | 10419 | 2 | 3 | | III-1 | Il11ra2 | | |
| 10049 | 2 | 3 | | III-1 | Homer1 | 9456 | 4-May-15 | 10422 | 2 | 3 | | III-1 | Il12rb1 | 3594 | 4-May-15 |
| 10051 | 2 | 3 | | III-1 | Homer3 | 9454 | 4-May-15 | 10424 | 2 | 3 | | III-1 | Il13 | 3596 | 4-May-15 |
| 10055 | 2 | 3 | | III-1 | Hook3 | 84376 | 4-May-15 | 10425 | 2 | 3 | | III-1 | Il13ra1 | 3597 | 8-May-15 |
| 10057 | 2 | 3 | | III-1 | Hormad1 | 84072 | 4-May-15 | 10426 | 2 | 3 | | III-1 | Il13ra2 | 3598 | 12-May-15 |
| 10061 | 2 | 3 | | III-1 | Hoxa1 | 3198 | 7-Jun-15 | 10428 | 2 | 3 | | III-1 | Il15ra | 3601 | 4-May-15 |
| 10063 | 2 | 3 | | III-1 | Hoxa11 | 3207 | 4-May-15 | 10429 | 2 | 3 | | III-1 | Il16 | 3603 | 4-May-15 |
| 10065 | 2 | 3 | | III-1 | Hoxa13 | 3209 | 23-May-15 | 10433 | 2 | 3 | | III-1 | Il17d | 53342 | 4-May-15 |
| 10067 | 2 | 3 | | III-1 | Hoxa3 | 3200 | 21-May-15 | 10434 | 2 | 3 | | III-1 | Il17f | 112744 | 4-May-15 |
| 10068 | 2 | 3 | | III-1 | Hoxa4 | 3201 | 12-May-15 | 10438 | 2 | 3 | | III-1 | Il17rd | 54756 | 4-May-15 |
| 10069 | 2 | 3 | | III-1 | Hoxa5 | 3202 | 28-May-15 | 10442 | 2 | 3 | | III-1 | Il18r1 | 8809 | 24-May-15 |
| 10072 | 2 | 3 | | III-1 | Hoxa9 | 3205 | 31-May-15 | 10444 | 2 | 3 | | III-1 | Il19 | 29949 | 4-May-15 |
| 10073 | 2 | 3 | | III-1 | Hoxb1 | 3211 | 7-Jun-15 | 10449 | 2 | 3 | | III-1 | Il1f5 | 26525 | 7-Jun-15 |
| 10078 | 2 | 3 | | III-1 | Hoxb5 | 3215 | 28-May-15 | 10450 | 2 | 3 | | III-1 | Il1f6 | 27179 | 4-May-15 |
| 10083 | 2 | 3 | | III-1 | Hoxc10 | 3226 | 4-May-15 | 10453 | 2 | 3 | | III-1 | Il1r1 | 3554 | 12-May-15 |
| 10085 | 2 | 3 | | III-1 | Hoxc12 | 3228 | 4-May-15 | 10455 | 2 | 3 | | III-1 | Il1rap | 3556 | 12-May-15 |
| 10098 | 2 | 3 | | III-1 | Hoxd3os1 | | | 10459 | 2 | 3 | | III-1 | Il1rl2 | 8808 | 4-May-15 |
| 10112 | 2 | 3 | | III-1 | Hprt | 3251 | 23-May-15 | 10461 | 2 | 3 | | III-1 | Il2 | 3558 | 12-May-15 |
| 10115 | 2 | 3 | | III-1 | Hps4 | 89781 | 23-May-15 | 10465 | 2 | 3 | | III-1 | Il21 | 59067 | 7-Jun-15 |
| 10130 | 2 | 3 | | III-1 | Hrh3 | 11255 | 4-May-15 | 10472 | 2 | 3 | | III-1 | Il24 | 11009 | 4-May-15 |
| 10132 | 2 | 3 | | III-1 | Hrk | 8739 | 4-May-15 | 10476 | 2 | 3 | | III-1 | Il2ra | 3559 | 17-May-15 |
| 10134 | 2 | 3 | | III-1 | Hrsp12 | 10247 | 4-May-15 | 10478 | 2 | 3 | | III-1 | Il2rg | 3561 | 23-May-15 |
| 10135 | 2 | 3 | | III-1 | Hs1bp3 | 64342 | 4-May-15 | 10484 | 2 | 3 | | III-1 | Il3ra | 3563 | 4-May-15 |
| 10138 | 2 | 3 | | III-1 | Hs3st2 | 9956 | 31-May-15 | 10485 | 2 | 3 | | III-1 | Il4 | 3565 | 4-May-15 |
| 10141 | 2 | 3 | | III-1 | Hs3st4 | 9951 | 4-May-15 | 10488 | 2 | 3 | | III-1 | Il5 | 3567 | 28-May-15 |
| 10154 | 2 | 3 | | III-1 | Hsd17b11 | 51170 | 4-May-15 | 10489 | 2 | 3 | | III-1 | Il5ra | 3568 | 12-May-15 |
| 10158 | 2 | 3 | | III-1 | Hsd17b2 | 3294 | 12-May-15 | 10492 | 2 | 3 | | III-1 | Il6st | 3572 | 12-May-15 |
| 10163 | 2 | 3 | | III-1 | Hsd3b1 | 3283 | 12-May-15 | 10495 | 2 | 3 | | III-1 | Il9 | 3578 | 7-Jun-15 |
| 10164 | 2 | 3 | | III-1 | Hsd3b2 | 3284 | 4-May-15 | 10499 | 2 | 3 | | III-1 | Ilf2 | 3608 | 4-May-15 |
| 10172 | 2 | 3 | | III-1 | Hsf1 | 3297 | 24-May-15 | 10500 | 2 | 3 | | III-1 | Ilf3 | 3609 | 12-May-15 |
| 10177 | 2 | 3 | | III-1 | Hsf5 | 124535 | 4-May-15 | 10502 | 2 | 3 | | III-1 | Ilkap | 80895 | 7-Jun-15 |
| 10181 | 2 | 3 | | III-1 | Hsp90ab1 | 3326 | 21-May-15 | 10503 | 2 | 3 | | III-1 | Ilrfb | | |
| 10184 | 2 | 3 | | III-1 | Hspa12b | 116835 | 4-May-15 | 10507 | 2 | 3 | | III-1 | Imrnt | 10989 | 4-May-15 |
| 10194 | 2 | 3 | | III-1 | Hspa8 | 3312 | 4-May-15 | 10513 | 2 | 3 | | III-1 | Impad1 | 54928 | 4-May-15 |
| 10195 | 2 | 3 | | III-1 | Hspa9 | 3313 | 31-May-15 | 10515 | 2 | 3 | | III-1 | Impdh2 | 3615 | 31-May-15 |
| 10204 | 2 | 3 | | III-1 | Hspbap1 | 79663 | 7-Jun-15 | 10516 | 2 | 3 | | III-1 | Impg1 | 3617 | 12-May-15 |
| 10208 | 2 | 3 | | III-1 | Hspg2 | 3339 | 4-May-15 | 10518 | 2 | 3 | | III-1 | Ina | 9118 | 17-May-15 |
| 10209 | 2 | 3 | | III-1 | Hsph1 | 10808 | 12-May-15 | 10523 | 2 | 3 | | III-1 | Ing1 | 3621 | 17-May-15 |
| 10211 | 2 | 3 | | III-1 | Htatsf1 | 27336 | 4-May-15 | 10525 | 2 | 3 | | III-1 | Ing3 | 54556 | 4-May-15 |
| 10214 | 2 | 3 | | III-1 | Htr1d | 3352 | 24-May-15 | 10539 | 2 | 3 | | III-1 | Ino80dos | | |
| 10219 | 2 | 3 | | III-1 | Htr3a | 3359 | 12-May-15 | 10540 | 2 | 3 | | III-1 | Ino80e | 283899 | 12-May-15 |
| 10220 | 2 | 3 | | III-1 | Htr3b | 9177 | 4-May-15 | 10542 | 2 | 3 | | III-1 | Inpp4a | 3631 | 4-May-15 |
| 10221 | 2 | 3 | | III-1 | Htr4 | 3360 | 21-May-15 | 10552 | 2 | 3 | | III-1 | Ins1 | 2305 | 31-May-15 |
| 10224 | 2 | 3 | | III-1 | Htr6 | 3362 | 4-May-15 | 10554 | 2 | 3 | | III-1 | Insc | 387755 | 4-May-15 |
| 10227 | 2 | 3 | | III-1 | Htra2 | 27429 | 23-May-15 | 10558 | 2 | 3 | | III-1 | Insl5 | 10022 | 4-May-15 |
| 10230 | 2 | 3 | | III-1 | Htt | 3064 | 7-Jun-15 | 10561 | 2 | 3 | | III-1 | Insm2 | 84684 | 21-May-15 |
| 10247 | 2 | 3 | | III-1 | Hvpk | 25764 | 4-May-15 | 10564 | 2 | 3 | | III-1 | Ints1 | 26173 | 4-May-15 |
| 10249 | 2 | 3 | | III-1 | 1730030J21Rik | | | 10572 | 2 | 3 | | III-1 | Ints7 | 25896 | 4-May-15 |
| 10252 | 2 | 3 | | III-1 | Iah1 | 285148 | 14-May-15 | 10573 | 2 | 3 | | III-1 | Ints8 | 55656 | 4-May-15 |
| 10254 | 2 | 3 | | III-1 | Iars | 3376 | 4-May-15 | 10580 | 2 | 3 | | III-1 | Ipcef1 | 26034 | 4-May-15 |
| 10258 | 2 | 3 | | III-1 | Ibtk | 25998 | 4-May-15 | 10582 | 2 | 3 | | III-1 | Ipo11 | 51194 | 4-May-15 |
| 10262 | 2 | 3 | | III-1 | Icam2 | 3384 | 12-May-15 | 10584 | 2 | 3 | | III-1 | Ipo4 | 79711 | 4-May-15 |
| 10271 | 2 | 3 | | III-1 | Id2 | 3398 | 4-May-15 | 10587 | 2 | 3 | | III-1 | Ipo8 | 10526 | 4-May-15 |
| 10273 | 2 | 3 | | III-1 | Id4 | 3400 | 24-May-15 | 10591 | 2 | 3 | | III-1 | Ipw | 3653 | 23-May-15 |
| 10274 | 2 | 3 | | III-1 | Ide | 3416 | 24-May-15 | 10594 | 2 | 3 | | III-1 | Iqcc | 55721 | 4-May-15 |
| 10275 | 2 | 3 | | III-1 | Idh1 | 3417 | 7-Jun-15 | 10596 | 2 | 3 | | III-1 | Iqce | 23288 | 4-May-15 |
| 10277 | 2 | 3 | | III-1 | Idh3a | 3419 | 12-May-15 | 10599 | 2 | 3 | | III-1 | Iqcf4 | 100506840 | 4-May-15 |
| 10278 | 2 | 3 | | III-1 | Idh3b | 3420 | 28-May-15 | 10606 | 2 | 3 | | III-1 | Iqgap1 | 8826 | 17-May-15 |
| 10285 | 2 | 3 | | III-1 | Ids | 3423 | 23-May-15 | 10608 | 2 | 3 | | III-1 | Iqgap3 | 128239 | 17-May-15 |
| 10289 | 2 | 3 | | III-1 | Ier3ip1 | 51124 | 4-May-15 | 10610 | 2 | 3 | | III-1 | Iqsec2 | 23096 | 2-Jun-15 |
| 10291 | 2 | 3 | | III-1 | Ier5l | 389792 | 4-May-15 | 10611 | 2 | 3 | | III-1 | Iqsec3 | 440073 | 4-May-15 |
| 10292 | 2 | 3 | | III-1 | Iffo1 | 25900 | 4-May-15 | 10616 | 2 | 3 | | III-1 | Irak3 | 11213 | 17-May-15 |
| 10294 | 2 | 3 | | III-1 | Ifi202b | | | 10617 | 2 | 3 | | III-1 | Irak4 | 51135 | 3-May-15 |
| 10295 | 2 | 3 | | III-1 | Ifi203 | | | 10623 | 2 | 3 | | III-1 | Irf2bpl | 64207 | 12-May-15 |
| 10297 | 2 | 3 | | III-1 | Ifi205 | | | 10624 | 2 | 3 | | III-1 | Irf3 | 3661 | 7-Jun-15 |
| 10298 | 2 | 3 | | III-1 | Ifi27 | 3429 | 17-May-15 | 10628 | 2 | 3 | | III-1 | Irf7 | 3665 | 21-May-15 |
| 10302 | 2 | 3 | | III-1 | Ifi35 | 3430 | 12-May-15 | 10630 | 2 | 3 | | III-1 | Irf9 | 10379 | 4-May-15 |
| 10309 | 2 | 3 | | III-1 | Ifi83 | 3437 | 21-May-15 | 10633 | 2 | 3 | | III-1 | Irgm1 | 345611 | 21-May-15 |
| 10311 | 2 | 3 | | III-1 | Ifitm10 | 402778 | 4-May-15 | 10639 | 2 | 3 | | III-1 | Irs4 | 8471 | 14-May-15 |

Fig.22 - 71

| | | | | | | | | | | | | | | |
|---|---|---|---|---|---|---|---|---|---|---|---|---|---|---|
| 10642 | 2 | 3 | | III-1 | Irx3 | 79191 | 24-May-15 | 10959 | 2 | 3 | | III-1 | Khdc1b | | |
| 10643 | 2 | 3 | | III-1 | Irx4 | 50805 | 4-May-15 | 10961 | 2 | 3 | | III-1 | Khdc3 | | |
| 10644 | 2 | 3 | | III-1 | Irx5 | 10265 | 4-May-15 | 10962 | 2 | 3 | | III-1 | Khdrbs1 | 10657 | 31-May-15 |
| 10647 | 2 | 3 | | III-1 | Isca2 | 122961 | 31-May-15 | 10966 | 2 | 3 | | III-1 | Khnyn | 23351 | 12-May-15 |
| 10651 | 2 | 3 | | III-1 | Isg20l2 | 81875 | 4-May-15 | 10976 | 2 | 3 | | III-1 | Kif17 | 57576 | 4-May-15 |
| 10658 | 2 | 3 | | III-1 | Isoc1 | 51015 | 4-May-15 | 10977 | 2 | 3 | | III-1 | Kif18a | 81930 | 4-May-15 |
| 10660 | 2 | 3 | | III-1 | Isoc2b | | | 10982 | 2 | 3 | | III-1 | Kif1c | 10749 | 12-May-15 |
| 10666 | 2 | 3 | | III-1 | Itch | 83737 | 4-May-15 | 10983 | 2 | 3 | | III-1 | Kif20a | 10112 | 4-May-15 |
| 10670 | 2 | 3 | | III-1 | Itga1 | 3672 | 12-May-15 | 10991 | 2 | 3 | | III-1 | Kif26b | 55083 | 4-May-15 |
| 10671 | 2 | 3 | | III-1 | Itga10 | 8515 | 12-May-15 | 10992 | 2 | 3 | | III-1 | Kif27 | 55582 | 4-May-15 |
| 10674 | 2 | 3 | | III-1 | Itga2b | 3674 | 12-May-15 | 11004 | 2 | 3 | | III-1 | Kif6 | 221458 | 4-May-15 |
| 10676 | 2 | 3 | | III-1 | Itga4 | 3676 | 24-May-15 | 11006 | 2 | 3 | | III-1 | Kif9 | 64147 | 4-May-15 |
| 10677 | 2 | 3 | | III-1 | Itga5 | 3678 | 4-May-15 | 11010 | 2 | 3 | | III-1 | Kifc3 | 3801 | 4-May-15 |
| 10678 | 2 | 3 | | III-1 | Itga6 | 3655 | 23-May-15 | 11013 | 2 | 3 | | III-1 | Kir3dl1 | 3811 | 12-May-15 |
| 10679 | 2 | 3 | | III-1 | Itga7 | 3679 | 23-May-15 | 11016 | 2 | 3 | | III-1 | Kirrel2 | 84063 | 4-May-15 |
| 10681 | 2 | 3 | | III-1 | Itga9 | 3680 | 12-May-15 | 11018 | 2 | 3 | | III-1 | Kis2 | | |
| 10683 | 2 | 3 | | III-1 | Itgae | 3682 | 24-May-15 | 11023 | 2 | 3 | | III-1 | Kiz | 55857 | 21-May-15 |
| 10684 | 2 | 3 | | III-1 | Itgal | 3683 | 12-May-15 | 11026 | 2 | 3 | | III-1 | Klc1 | 3831 | 12-May-15 |
| 10686 | 2 | 3 | | III-1 | Itgav | 3685 | 31-May-15 | 11029 | 2 | 3 | | III-1 | Klc4 | 89953 | 4-May-15 |
| 10694 | 2 | 3 | | III-1 | Itgb3bp | 23421 | 4-May-15 | 11035 | 2 | 3 | | III-1 | Klf14 | 136259 | 4-May-15 |
| 10696 | 2 | 3 | | III-1 | Itgb5 | 3693 | 17-May-15 | 11037 | 2 | 3 | | III-1 | Klf16 | 83855 | 4-May-15 |
| 10697 | 2 | 3 | | III-1 | Itgb6 | 3694 | 4-May-15 | 11038 | 2 | 3 | | III-1 | Klf17 | 128209 | 24-May-15 |
| 10699 | 2 | 3 | | III-1 | Itgb8 | 3696 | 31-May-15 | 11040 | 2 | 3 | | III-1 | Klf3 | 51274 | 2-Jun-15 |
| 10700 | 2 | 3 | | III-1 | Itgbl1 | 9358 | 4-May-15 | 11041 | 2 | 3 | | III-1 | Klf4 | 9314 | 31-May-15 |
| 10705 | 2 | 3 | | III-1 | Itih5 | 80760 | 17-May-15 | 11047 | 2 | 3 | | III-1 | Klhdc1 | 122773 | 4-May-15 |
| 10710 | 2 | 3 | | III-1 | Itm2c | 81618 | 4-May-15 | 11048 | 2 | 3 | | III-1 | Klhdc10 | 23008 | 12-May-15 |
| 10711 | 2 | 3 | | III-1 | Itpa | 3704 | 31-May-15 | 11050 | 2 | 3 | | III-1 | Klhdc3 | 116138 | 12-May-15 |
| 10712 | 2 | 3 | | III-1 | Itpk1 | 3705 | 4-May-15 | 11051 | 2 | 3 | | III-1 | Klhdc4 | 54758 | 4-May-15 |
| 10714 | 2 | 3 | | III-1 | Itpkb | 3707 | 4-May-15 | 11057 | 2 | 3 | | III-1 | Klhl1 | 57626 | 4-May-15 |
| 10717 | 2 | 3 | | III-1 | Itpr2 | 3709 | 21-May-15 | 11067 | 2 | 3 | | III-1 | Klhl20 | 27252 | 4-May-15 |
| 10718 | 2 | 3 | | III-1 | Itpr3 | 3710 | 12-May-15 | 11069 | 2 | 3 | | III-1 | Klhl22 | 84861 | 4-May-15 |
| 10720 | 2 | 3 | | III-1 | Itprip1 | 150771 | 4-May-15 | 11071 | 2 | 3 | | III-1 | Klhl24 | 54800 | 4-May-15 |
| 10722 | 2 | 3 | | III-1 | Itsn1 | 6453 | 14-May-15 | 11072 | 2 | 3 | | III-1 | Klhl25 | 64410 | 4-May-15 |
| 10724 | 2 | 3 | | III-1 | Ivd | 3712 | 23-May-15 | 11073 | 2 | 3 | | III-1 | Klhl26 | 55295 | 4-May-15 |
| 10725 | 2 | 3 | | III-1 | Ivl | 3713 | 12-May-15 | 11076 | 2 | 3 | | III-1 | Klhl3 | 26249 | 4-May-15 |
| 10727 | 2 | 3 | | III-1 | Iws1 | 55677 | 14-May-15 | 11096 | 2 | 3 | | III-1 | Klk11 | 11012 | 4-May-15 |
| 10729 | 2 | 3 | | III-1 | Izumo1 | 284359 | 4-May-15 | 11097 | 2 | 3 | | III-1 | Klk12 | 43849 | 4-May-15 |
| 10733 | 2 | 3 | | III-1 | Jade1 | 79960 | 4-May-15 | 11098 | 2 | 3 | | III-1 | Klk13 | 26085 | 4-May-15 |
| 10736 | 2 | 3 | | III-1 | Jag1 | 182 | 31-May-15 | 11100 | 2 | 3 | | III-1 | Klk15 | 55554 | 12-May-15 |
| 10738 | 2 | 3 | | III-1 | Jagn1 | 84522 | 4-May-15 | 11118 | 2 | 3 | | III-1 | Klk7 | 5650 | 7-Jun-15 |
| 10746 | 2 | 3 | | III-1 | Jam3 | 83700 | 4-May-15 | 11119 | 2 | 3 | | III-1 | Klk8 | 11202 | 4-May-15 |
| 10749 | 2 | 3 | | III-1 | Jdp2 | 122953 | 4-May-15 | 11121 | 2 | 3 | | III-1 | Klkb1 | 3818 | 4-May-15 |
| 10750 | 2 | 3 | | III-1 | Jkamp | 51528 | 4-May-15 | 11129 | 2 | 3 | | III-1 | Klra18 | | |
| 10751 | 2 | 3 | | III-1 | Jmjd1c | 221037 | 4-May-15 | 11141 | 2 | 3 | | III-1 | Klra8 | | |
| 10753 | 2 | 3 | | III-1 | Jmjd6 | 23210 | 4-May-15 | 11147 | 2 | 3 | | III-1 | Klrb1f | | |
| 10754 | 2 | 3 | | III-1 | Jmjd7 | 100137047 | 4-May-15 | 11150 | 2 | 3 | | III-1 | Klrc2 | 3822 | 12-May-15 |
| 10755 | 2 | 3 | | III-1 | Jmjd7-pla2g4b | 8681 | 4-May-15 | 11159 | 2 | 3 | | III-1 | Kmo | 8564 | 4-May-15 |
| 10756 | 2 | 3 | | III-1 | Jmjd8 | 339123 | 21-May-15 | 11161 | 2 | 3 | | III-1 | Kmt2b | 9757 | 4-May-15 |
| 10770 | 2 | 3 | | III-1 | Junb | 3726 | 7-Jun-15 | 11162 | 2 | 3 | | III-1 | Kmt2c | 58508 | 4-May-15 |
| 10771 | 2 | 3 | | III-1 | Jund | 3727 | 4-May-15 | 11163 | 2 | 3 | | III-1 | Kmt2d | 8085 | 23-May-15 |
| 10774 | 2 | 3 | | III-1 | Kank1 | 23189 | 12-May-15 | 11164 | 2 | 3 | | III-1 | Kmt2e | 55904 | 4-May-15 |
| 10775 | 2 | 3 | | III-1 | Kank2 | 25959 | 4-May-15 | 11165 | 2 | 3 | | III-1 | Kncn | 148930 | 4-May-15 |
| 10776 | 2 | 3 | | III-1 | Kank3 | 256949 | 12-May-15 | 11169 | 2 | 3 | | III-1 | Knop1 | 400506 | 4-May-15 |
| 10777 | 2 | 3 | | III-1 | Kank4 | 163782 | 4-May-15 | 11174 | 2 | 3 | | III-1 | Kpna3 | 3839 | 4-May-15 |
| 10781 | 2 | 3 | | III-1 | Kansl2 | 54934 | 12-May-15 | 11180 | 2 | 3 | | III-1 | Kptn | 11133 | 4-May-15 |
| 10789 | 2 | 3 | | III-1 | Kat6b | 23522 | 4-May-15 | 11187 | 2 | 3 | | III-1 | Krit1 | 889 | 31-May-15 |
| 10790 | 2 | 3 | | III-1 | Kat7 | 11143 | 24-May-15 | 11191 | 2 | 3 | | III-1 | Krt12 | 3859 | 4-May-15 |
| 10792 | 2 | 3 | | III-1 | Katna1 | 11104 | 4-May-15 | 11196 | 2 | 3 | | III-1 | Krt17 | 3872 | 22-May-15 |
| 10793 | 2 | 3 | | III-1 | Katnal1 | 84056 | 4-May-15 | 11199 | 2 | 3 | | III-1 | Krt2 | 3849 | 4-May-15 |
| 10799 | 2 | 3 | | III-1 | Kbtbd11 | 9920 | 4-May-15 | 11201 | 2 | 3 | | III-1 | Krt222 | 125113 | 4-May-15 |
| 10800 | 2 | 3 | | III-1 | Kbtbd12 | 168348 | 4-May-15 | 11203 | 2 | 3 | | III-1 | Krt24 | 192666 | 4-May-15 |
| 10802 | 2 | 3 | | III-1 | Kbtbd2 | 25948 | 4-May-15 | 11206 | 2 | 3 | | III-1 | Krt27 | 342574 | 4-May-15 |
| 10804 | 2 | 3 | | III-1 | Kbtbd4 | 55709 | 4-May-15 | 11217 | 2 | 3 | | III-1 | Krt40 | 125115 | 4-May-15 |
| 10807 | 2 | 3 | | III-1 | Kcmf1 | 56882 | 4-May-15 | 11223 | 2 | 3 | | III-1 | Krt71 | 112802 | 4-May-15 |
| 10808 | 2 | 3 | | III-1 | Kcna1 | 3736 | 23-May-15 | 11233 | 2 | 3 | | III-1 | Krt80 | 144501 | 4-May-15 |
| 10809 | 2 | 3 | | III-1 | Kcna10 | 3744 | 4-May-15 | 11234 | 2 | 3 | | III-1 | Krt81 | 3887 | 12-May-15 |
| 10814 | 2 | 3 | | III-1 | Kcna6 | 3742 | 4-May-15 | 11238 | 2 | 3 | | III-1 | Krt85 | 3891 | 4-May-15 |
| 10817 | 2 | 3 | | III-1 | Kcnab2 | 8514 | 4-May-15 | 11251 | 2 | 3 | | III-1 | Krtap1-5 | 83895 | 4-May-15 |
| 10826 | 2 | 3 | | III-1 | Kcnd2 | 3751 | 12-May-15 | 11286 | 2 | 3 | | III-1 | Krtap6-2 | 337967 | 12-May-15 |
| 10835 | 2 | 3 | | III-1 | Kcng1 | 3755 | 3-May-15 | 11287 | 2 | 3 | | III-1 | Krtap6-5 | | |
| 10842 | 2 | 3 | | III-1 | Kcnh4 | 23415 | 4-May-15 | 11294 | 2 | 3 | | III-1 | Krtcap3 | 200634 | 4-May-15 |
| 10845 | 2 | 3 | | III-1 | Kcnh7 | 90134 | 4-May-15 | 11297 | 2 | 3 | | III-1 | Ksr2 | 283455 | 7-Jun-15 |
| 10850 | 2 | 3 | | III-1 | Kcnip4 | 80333 | 4-May-15 | 11303 | 2 | 3 | | III-1 | L1cam | 3897 | 23-May-15 |
| 10851 | 2 | 3 | | III-1 | Kcnj1 | 3758 | 4-May-15 | 11304 | 2 | 3 | | III-1 | L1td1 | 54596 | 4-May-15 |
| 10878 | 2 | 3 | | III-1 | Kcnk7 | 10089 | 4-May-15 | 11313 | 2 | 3 | | III-1 | Lace1 | 246269 | 4-May-15 |
| 10881 | 2 | 3 | | III-1 | Kcnmb1 | 3779 | 12-May-15 | 11315 | 2 | 3 | | III-1 | Lactb2 | 51110 | 4-May-15 |
| 10886 | 2 | 3 | | III-1 | Kcnn1 | 3780 | 12-May-15 | 11320 | 2 | 3 | | III-1 | Lair1 | 3903 | 3-May-15 |
| 10887 | 2 | 3 | | III-1 | Kcnn2 | 3781 | 4-May-15 | 11321 | 2 | 3 | | III-1 | Lalba | 3906 | 4-May-15 |
| 10889 | 2 | 3 | | III-1 | Kcnn4 | 3783 | 12-May-15 | 11326 | 2 | 3 | | III-1 | Lama5 | 3911 | 12-May-15 |
| 10895 | 2 | 3 | | III-1 | Kcnq5 | 56479 | 12-May-15 | 11328 | 2 | 3 | | III-1 | Lamb2 | 3913 | 7-Jun-15 |
| 10896 | 2 | 3 | | III-1 | Kcnrg | 283518 | 4-May-15 | 11330 | 2 | 3 | | III-1 | Lamc1 | 3915 | 12-May-15 |
| 10901 | 2 | 3 | | III-1 | Kcnt2 | 343450 | 4-May-15 | 11332 | 2 | 3 | | III-1 | Lamc3 | 10319 | 4-May-15 |
| 10905 | 2 | 3 | | III-1 | Kcp | 375616 | 4-May-15 | 11339 | 2 | 3 | | III-1 | Lamtor3 | 8649 | 4-May-15 |
| 10907 | 2 | 3 | | III-1 | Kctd10 | 83892 | 4-May-15 | 11340 | 2 | 3 | | III-1 | Lamtor4 | 389541 | 4-May-15 |
| 10909 | 2 | 3 | | III-1 | Kctd12 | 115207 | 4-May-15 | 11341 | 2 | 3 | | III-1 | Lamtor5 | 10542 | 17-May-15 |
| 10910 | 2 | 3 | | III-1 | Kctd12b | | | 11343 | 2 | 3 | | III-1 | Lancl2 | 55915 | 12-May-15 |
| 10914 | 2 | 3 | | III-1 | Kctd16 | 57628 | 4-May-15 | 11345 | 2 | 3 | | III-1 | Lao1 | | |
| 10919 | 2 | 3 | | III-1 | Kctd20 | 222658 | 4-May-15 | 11347 | 2 | 3 | | III-1 | Laptm4a | 9741 | 4-May-15 |
| 10923 | 2 | 3 | | III-1 | Kctd5 | 54442 | 4-May-15 | 11351 | 2 | 3 | | III-1 | Larp1 | 23367 | 4-May-15 |
| 10927 | 2 | 3 | | III-1 | Kctd9 | 54793 | 4-May-15 | 11353 | 2 | 3 | | III-1 | Larp4 | 113251 | 3-May-15 |
| 10928 | 2 | 3 | | III-1 | Kdelc1 | 79070 | 4-May-15 | 11356 | 2 | 3 | | III-1 | Larp7 | 51574 | 17-May-15 |
| 10939 | 2 | 3 | | III-1 | Kdm3b | 51780 | 4-May-15 | 11360 | 2 | 3 | | III-1 | Lasp1 | 3927 | 7-Jun-15 |
| 10949 | 2 | 3 | | III-1 | Kdm6b | 23135 | 4-May-15 | 11367 | 2 | 3 | | III-1 | Lbh | 81606 | 7-Jun-15 |
| 10950 | 2 | 3 | | III-1 | Kdm7a | 80853 | 23-May-15 | 11371 | 2 | 3 | | III-1 | Lbx2 | 85474 | 12-May-15 |
| 10951 | 2 | 3 | | III-1 | Kdm8 | 79831 | 4-May-15 | 11372 | 2 | 3 | | III-1 | Lca5 | 167691 | 23-May-15 |
| 10952 | 2 | 3 | | III-1 | Kdr | 3791 | 17-May-15 | 11388 | 2 | 3 | | III-1 | Lce1m | | |
| 10954 | 2 | 3 | | III-1 | Keap1 | 9817 | 31-May-15 | 11399 | 2 | 3 | | III-1 | Lcmt2 | 9836 | 4-May-15 |

Fig.22 - 72

| | | | | | | | | |
|---|---|---|---|---|---|---|---|---|
| 11401 | 2 | 3 | | III-1 | Lcn11 | | | |
| 11420 | 2 | 3 | | III-1 | Ldhal6b | 92483 | 12-May-15 |
| 11422 | 2 | 3 | | III-1 | Ldhc | 3948 | 21-May-15 |
| 11425 | 2 | 3 | | III-1 | Ldlrad1 | 388633 | 4-May-15 |
| 11428 | 2 | 3 | | III-1 | Ldlrad4 | 753 | 4-May-15 |
| 11437 | 2 | 3 | | III-1 | Lefty2 | 7044 | 4-May-15 |
| 11440 | 2 | 3 | | III-1 | Lemd1 | 93773 | 4-May-15 |
| 11444 | 2 | 3 | | III-1 | Leng1 | 79165 | 4-May-15 |
| 11447 | 2 | 3 | | III-1 | Leo1 | 123169 | 4-May-15 |
| 11450 | 2 | 3 | | III-1 | Leprel1 | 64175 | 4-May-15 |
| 11451 | 2 | 3 | | III-1 | Leprel1 | 55214 | 4-May-15 |
| 11454 | 2 | 3 | | III-1 | Leprot | 54741 | 4-May-15 |
| 11458 | 2 | 3 | | III-1 | Letmd1 | 25875 | 12-May-15 |
| 11468 | 2 | 3 | | III-1 | Lgals8 | 3964 | 17-May-15 |
| 11471 | 2 | 3 | | III-1 | Lgi1 | 9211 | 1-Jun-15 |
| 11474 | 2 | 3 | | III-1 | Lgi4 | 163175 | 4-May-15 |
| 11476 | 2 | 3 | | III-1 | Lgr4 | 55366 | 12-May-15 |
| 11477 | 2 | 3 | | III-1 | Lgr5 | 8549 | 17-May-15 |
| 11481 | 2 | 3 | | III-1 | Lhcgr | 3973 | 12-May-15 |
| 11489 | 2 | 3 | | III-1 | Lhx1 | 3975 | 4-May-15 |
| 11491 | 2 | 3 | | III-1 | Lhx2 | 9355 | 4-May-15 |
| 11492 | 2 | 3 | | III-1 | Lhx3 | 8022 | 12-May-15 |
| 11493 | 2 | 3 | | III-1 | Lhx4 | 89884 | 12-May-15 |
| 11496 | 2 | 3 | | III-1 | Lhx8 | 431707 | 4-May-15 |
| 11503 | 2 | 3 | | III-1 | Lig4 | 3981 | 4-May-15 |
| 11507 | 2 | 3 | | III-1 | Lim2 | 3982 | 4-May-15 |
| 11509 | 2 | 3 | | III-1 | Limch1 | 22998 | 12-May-15 |
| 11510 | 2 | 3 | | III-1 | Limd1 | 8994 | 24-May-15 |
| 11517 | 2 | 3 | | III-1 | Lin28a | 79727 | 4-May-15 |
| 11520 | 2 | 3 | | III-1 | Lin52 | 91750 | 4-May-15 |
| 11526 | 2 | 3 | | III-1 | Lincrna-cox2 | | |
| 11528 | 2 | 3 | | III-1 | Lingo2 | 158038 | 4-May-15 |
| 11530 | 2 | 3 | | III-1 | Lingo4 | 339398 | 4-May-15 |
| 11532 | 2 | 3 | | III-1 | Lipa | 3988 | 7-Jun-15 |
| 11533 | 2 | 3 | | III-1 | Lipc | 3990 | 24-May-15 |
| 11537 | 2 | 3 | | III-1 | Liph | 200879 | 13-Jun-15 |
| 11539 | 2 | 3 | | III-1 | Lipk | 643414 | 4-May-15 |
| 11542 | 2 | 3 | | III-1 | Lipo1 | | |
| 11544 | 2 | 3 | | III-1 | Lipt2 | 387787 | 4-May-15 |
| 11545 | 2 | 3 | | III-1 | Litaf | 9516 | 23-May-15 |
| 11546 | 2 | 3 | | III-1 | Lix1 | 167410 | 21-May-15 |
| 11547 | 2 | 3 | | III-1 | Lix1l | 128077 | 4-May-15 |
| 11548 | 2 | 3 | | III-1 | Lkaaear1 | 198437 | 4-May-15 |
| 11551 | 2 | 3 | | III-1 | Llph | 84298 | 4-May-15 |
| 11555 | 2 | 3 | | III-1 | Lman2l | 81562 | 17-May-15 |
| 11557 | 2 | 3 | | III-1 | Lmbr1l | 55716 | 4-May-15 |
| 11561 | 2 | 3 | | III-1 | Lmf1 | 64788 | 14-May-15 |
| 11565 | 2 | 3 | | III-1 | Lmnb1 | 4001 | 4-May-15 |
| 11568 | 2 | 3 | | III-1 | Lmo2 | 4005 | 21-May-15 |
| 11569 | 2 | 3 | | III-1 | Lmo3 | 55885 | 12-May-15 |
| 11571 | 2 | 3 | | III-1 | Lmo7 | 4008 | 12-May-15 |
| 11576 | 2 | 3 | | III-1 | Lmtk3 | 114783 | 4-May-15 |
| 11577 | 2 | 3 | | III-1 | Lmx1a | 4009 | 3-May-15 |
| 11582 | 2 | 3 | | III-1 | Lnx2 | 222484 | 4-May-15 |
| 11592 | 2 | 3 | | III-1 | LOC100504608 | | |
| 11596 | 2 | 3 | | III-1 | LOC100861978 | | |
| 11600 | 2 | 3 | | III-1 | LOC101055863 | | |
| 11602 | 2 | 3 | | III-1 | LOC101056136 | | |
| 11606 | 2 | 3 | | III-1 | LOC101669761 | | |
| 11607 | 2 | 3 | | III-1 | LOC102308570 | | |
| 11610 | 2 | 3 | | III-1 | LOC102632436 | | |
| 11613 | 2 | 3 | | III-1 | LOC102634101 | | |
| 11614 | 2 | 3 | | III-1 | LOC102634401 | | |
| 11620 | 2 | 3 | | III-1 | LOC171588 | | |
| 11623 | 2 | 3 | | III-1 | Loh12cr1 | 118426 | 4-May-15 |
| 11625 | 2 | 3 | | III-1 | Lonp2 | 83752 | 23-May-15 |
| 11637 | 2 | 3 | | III-1 | Lpar2 | 9170 | 12-May-15 |
| 11641 | 2 | 3 | | III-1 | Lpar6 | 10161 | 17-May-15 |
| 11644 | 2 | 3 | | III-1 | Lpcat2b | | |
| 11647 | 2 | 3 | | III-1 | Lpgat1 | 9926 | 4-May-15 |
| 11650 | 2 | 3 | | III-1 | Lphn3 | 23284 | 4-May-15 |
| 11657 | 2 | 3 | | III-1 | Lpxn | 9404 | 12-May-15 |
| 11660 | 2 | 3 | | III-1 | Lrch1 | 23143 | 4-May-15 |
| 11665 | 2 | 3 | | III-1 | Lrfn1 | 57622 | 12-May-15 |
| 11666 | 2 | 3 | | III-1 | Lrfn2 | 57497 | 4-May-15 |
| 11669 | 2 | 3 | | III-1 | Lrfn5 | 145581 | 4-May-15 |
| 11671 | 2 | 3 | | III-1 | Lrguk | 136332 | 4-May-15 |
| 11676 | 2 | 3 | | III-1 | Lrit1 | 26103 | 12-May-15 |
| 11678 | 2 | 3 | | III-1 | Lrit3 | 345193 | 7-Jun-15 |
| 11681 | 2 | 3 | | III-1 | Lrp10 | 26020 | 4-May-15 |
| 11687 | 2 | 3 | | III-1 | Lrp3 | 4037 | 4-May-15 |
| 11689 | 2 | 3 | | III-1 | Lrp5 | 4041 | 23-May-15 |
| 11690 | 2 | 3 | | III-1 | Lrp6 | 4040 | 4-May-15 |
| 11694 | 2 | 3 | | III-1 | Lrr1 | 122769 | 4-May-15 |
| 11703 | 2 | 3 | | III-1 | Lrrc17 | 10234 | 4-May-15 |
| 11705 | 2 | 3 | | III-1 | Lrrc19 | 64922 | 4-May-15 |
| 11709 | 2 | 3 | | III-1 | Lrrc24 | 441381 | 4-May-15 |
| 11710 | 2 | 3 | | III-1 | Lrrc25 | 126364 | 4-May-15 |
| 11715 | 2 | 3 | | III-1 | Lrrc3 | 81543 | 4-May-15 |
| 11722 | 2 | 3 | | III-1 | Lrrc3b | 116135 | 14-May-15 |
| 11730 | 2 | 3 | | III-1 | Lrrc47 | 57470 | 4-May-15 |
| 11732 | 2 | 3 | | III-1 | Lrrc49 | 54839 | 4-May-15 |
| 11733 | 2 | 3 | | III-1 | Lrrc4b | 94030 | 4-May-15 |
| 11734 | 2 | 3 | | III-1 | Lrrc4c | 57689 | 2-Jun-15 |
| 11739 | 2 | 3 | | III-1 | Lrrc57 | 255252 | 4-May-15 |
| 11741 | 2 | 3 | | III-1 | Lrrc59 | 55379 | 4-May-15 |
| 11743 | 2 | 3 | | III-1 | Lrrc61 | 65999 | 4-May-15 |
| 11749 | 2 | 3 | | III-1 | Lrrc72 | 100506049 | 4-May-15 |
| 11751 | 2 | 3 | | III-1 | Lrrc74 | 145497 | 4-May-15 |
| 11757 | 2 | 3 | | III-1 | Lrrc8d | 55144 | 4-May-15 |
| 11759 | 2 | 3 | | III-1 | Lrrc9 | 341883 | 4-May-15 |
| 11764 | 2 | 3 | | III-1 | Lrriq1 | 84125 | 4-May-15 |
| 11768 | 2 | 3 | | III-1 | Lrrk2 | 120892 | 23-May-15 |
| 11774 | 2 | 3 | | III-1 | Lrrtm1 | 347730 | 17-May-15 |
| 11777 | 2 | 3 | | III-1 | Lrrtm4 | 80059 | 4-May-15 |
| 11782 | 2 | 3 | | III-1 | Lsamp | 4045 | 21-May-15 |
| 11784 | 2 | 3 | | III-1 | Lsm1 | 27257 | 4-May-15 |
| 11786 | 2 | 3 | | III-1 | Lsm11 | 134353 | 4-May-15 |
| 11788 | 2 | 3 | | III-1 | Lsm14a | 26065 | 4-May-15 |
| 11791 | 2 | 3 | | III-1 | Lsm3 | 27258 | 4-May-15 |
| 11796 | 2 | 3 | | III-1 | Lsm8 | 51691 | 4-May-15 |
| 11808 | 2 | 3 | | III-1 | Ltbp2 | 4053 | 7-Jun-15 |
| 11811 | 2 | 3 | | III-1 | Ltbr | 4055 | 12-May-15 |
| 11817 | 2 | 3 | | III-1 | Luc7l | 55692 | 21-May-15 |
| 11822 | 2 | 3 | | III-1 | Lurap1l | 286343 | 4-May-15 |
| 11823 | 2 | 3 | | III-1 | Luzp1 | 7798 | 4-May-15 |
| 11824 | 2 | 3 | | III-1 | Luzp2 | 338645 | 4-May-15 |
| 11827 | 2 | 3 | | III-1 | Ly6a | | |
| 11848 | 2 | 3 | | III-1 | Lyg2 | 254773 | 4-May-15 |
| 11851 | 2 | 3 | | III-1 | Lynx1 | 66004 | 4-May-15 |
| 11853 | 2 | 3 | | III-1 | Lypd2 | 137797 | 4-May-15 |
| 11855 | 2 | 3 | | III-1 | Lypd4 | 147719 | 12-May-15 |
| 11858 | 2 | 3 | | III-1 | Lypd6b | 130576 | 4-May-15 |
| 11860 | 2 | 3 | | III-1 | Lypla1 | 10434 | 4-May-15 |
| 11863 | 2 | 3 | | III-1 | Lyrm1 | 57149 | 12-May-15 |
| 11866 | 2 | 3 | | III-1 | Lyrm5 | 144363 | 4-May-15 |
| 11870 | 2 | 3 | | III-1 | Lysmd1 | 388695 | 4-May-15 |
| 11872 | 2 | 3 | | III-1 | Lysmd3 | 116068 | 4-May-15 |
| 11873 | 2 | 3 | | III-1 | Lysmd4 | 145748 | 4-May-15 |
| 11887 | 2 | 3 | | III-1 | Lzts3 | 9762 | 4-May-15 |
| 11888 | 2 | 3 | | III-1 | M1ap | 130951 | 4-May-15 |
| 11899 | 2 | 3 | | III-1 | Mad2l1 | 4085 | 4-May-15 |
| 11903 | 2 | 3 | | III-1 | Madd | 8567 | 7-Jun-15 |
| 11904 | 2 | 3 | | III-1 | Maea | 10296 | 12-May-15 |
| 11907 | 2 | 3 | | III-1 | Maf1 | 84232 | 4-May-15 |
| 11911 | 2 | 3 | | III-1 | Mafg | 4097 | 2-Jun-15 |
| 11912 | 2 | 3 | | III-1 | Mafk | 7975 | 4-May-15 |
| 11913 | 2 | 3 | | III-1 | Mag | 4099 | 4-May-15 |
| 11927 | 2 | 3 | | III-1 | Mageb3 | 4114 | 4-May-15 |
| 11931 | 2 | 3 | | III-1 | Maged2 | 10916 | 4-May-15 |
| 11935 | 2 | 3 | | III-1 | Magel2 | 54551 | 23-May-15 |
| 11937 | 2 | 3 | | III-1 | Magi2 | 9863 | 10-May-15 |
| 11947 | 2 | 3 | | III-1 | Malat1 | 378938 | 21-May-15 |
| 11950 | 2 | 3 | | III-1 | Malt1 | 10892 | 4-May-15 |
| 11952 | 2 | 3 | | III-1 | Mamdc4 | 158056 | 4-May-15 |
| 11956 | 2 | 3 | | III-1 | Mamld1 | 10046 | 23-May-15 |
| 11959 | 2 | 3 | | III-1 | Man1a2 | 10905 | 12-May-15 |
| 11962 | 2 | 3 | | III-1 | Man2a1 | 4124 | 4-May-15 |
| 11963 | 2 | 3 | | III-1 | Man2a2 | 4122 | 12-May-15 |
| 11966 | 2 | 3 | | III-1 | Man2c1 | 4123 | 4-May-15 |
| 11968 | 2 | 3 | | III-1 | Manba | 4126 | 4-May-15 |
| 11973 | 2 | 3 | | III-1 | Manf | | |
| 11975 | 2 | 3 | | III-1 | Mansc4 | 100287284 | 4-May-15 |
| 11978 | 2 | 3 | | III-1 | Map10 | 54627 | 4-May-15 |
| 11982 | 2 | 3 | | III-1 | Map1lc3b | 81631 | 1-Jun-15 |
| 11985 | 2 | 3 | | III-1 | Map2k1 | 5604 | 28-May-15 |
| 11988 | 2 | 3 | | III-1 | Map3k3os | | |
| 11989 | 2 | 3 | | III-1 | Map2k4 | 6416 | 12-May-15 |
| 11999 | 2 | 3 | | III-1 | Map3k15 | 389840 | 4-May-15 |
| 12006 | 2 | 3 | | III-1 | Map3k7 | 6885 | 12-May-15 |
| 12009 | 2 | 3 | | III-1 | Map3k9 | 4293 | 4-May-15 |
| 12010 | 2 | 3 | | III-1 | Map4 | 4134 | 4-May-15 |
| 12015 | 2 | 3 | | III-1 | Map4k5 | 11183 | 4-May-15 |
| 12019 | 2 | 3 | | III-1 | Map7d1 | 55700 | 4-May-15 |
| 12021 | 2 | 3 | | III-1 | Map9 | 79884 | 4-May-15 |
| 12027 | 2 | 3 | | III-1 | Mapk14 | 1432 | 31-May-15 |
| 12029 | 2 | 3 | | III-1 | Mapk1ip1 | | |
| 12030 | 2 | 3 | | III-1 | Mapk1ip1l | 93487 | 4-May-15 |
| 12033 | 2 | 3 | | III-1 | Mapk6 | 5597 | 4-May-15 |
| 12034 | 2 | 3 | | III-1 | Mapk7 | 5598 | 4-May-15 |
| 12043 | 2 | 3 | | III-1 | Mapkapk5 | 8550 | 4-May-15 |
| 12045 | 2 | 3 | | III-1 | Mapre1 | 22919 | 31-May-15 |
| 12047 | 2 | 3 | | III-1 | Mapre3 | 22924 | 12-May-15 |
| 12050 | 2 | 3 | | III-1 | Marc2 | 54996 | 4-May-15 |
| 12056 | 2 | 3 | | III-1 | March4 | 57574 | 4-May-15 |
| 12060 | 2 | 3 | | III-1 | March8 | 220972 | 4-May-15 |
| 12062 | 2 | 3 | | III-1 | Marcks | 4082 | 10-May-15 |
| 12066 | 2 | 3 | | III-1 | Marf1 | 9665 | 4-May-15 |
| 12068 | 2 | 3 | | III-1 | Mark2 | 2011 | 21-May-15 |
| 12071 | 2 | 3 | | III-1 | Mars | 4141 | 7-Jun-15 |
| 12076 | 2 | 3 | | III-1 | Mas1 | 4142 | 4-May-15 |
| 12080 | 2 | 3 | | III-1 | Mast2 | 23139 | 4-May-15 |
| 12082 | 2 | 3 | | III-1 | Mast4 | 375449 | 12-May-15 |
| 12083 | 2 | 3 | | III-1 | Mastl | 84930 | 4-May-15 |
| 12086 | 2 | 3 | | III-1 | Mat2b | 27430 | 12-May-15 |
| 12100 | 2 | 3 | | III-1 | Mbd1 | 4152 | 7-Jun-15 |
| 12107 | 2 | 3 | | III-1 | Mbd6 | 114785 | 31-May-15 |
| 12109 | 2 | 3 | | III-1 | Mbl1 | | |
| 12111 | 2 | 3 | | III-1 | Mblac1 | 255374 | 4-May-15 |
| 12112 | 2 | 3 | | III-1 | Mblac2 | 153364 | 4-May-15 |
| 12113 | 2 | 3 | | III-1 | Mboi1 | 4154 | 4-May-15 |
| 12118 | 2 | 3 | | III-1 | Mboat4 | 619373 | 12-May-15 |
| 12119 | 2 | 3 | | III-1 | Mboat7 | 79143 | 4-May-15 |

Fig.22 - 73

| | | | | | | | | | | | | | | | |
|---|---|---|---|---|---|---|---|---|---|---|---|---|---|---|---|
| 12121 | 2 | 3 | | III-1 | Mbd1 | 54799 | 12-May-15 | 12385 | 2 | 3 | | III-1 | Mios | 54468 | 29-May-15 |
| 12124 | 2 | 3 | | III-1 | Mc1r | 4157 | 7-Jun-15 | 12389 | 2 | 3 | | III-1 | Mipol1 | 145282 | 12-May-15 |
| 12126 | 2 | 3 | | III-1 | Mc3r | 4159 | 24-May-15 | 12390 | 2 | 3 | | III-1 | Mir100 | 406892 | 21-May-15 |
| 12129 | 2 | 3 | | III-1 | Mcam | 4162 | 4-May-15 | 12444 | 2 | 3 | | III-1 | Mir133b | 442890 | 21-May-15 |
| 12132 | 2 | 3 | | III-1 | Mcc1 | 56922 | 23-May-15 | 12461 | 2 | 3 | | III-1 | Mir144 | 406936 | 21-May-15 |
| 12133 | 2 | 3 | | III-1 | Mccc1os | | | 12482 | 2 | 3 | | III-1 | Mir18 | 406953 | 21-May-15 |
| 12139 | 2 | 3 | | III-1 | Mcfd2 | 90411 | 1-Jun-15 | 12622 | 2 | 3 | | III-1 | Mir23a | 407010 | 24-May-15 |
| 12140 | 2 | 3 | | III-1 | Mchr1 | 2847 | 12-May-15 | 13012 | 2 | 3 | | III-1 | Mir6386 | | |
| 12141 | 2 | 3 | | III-1 | Mcidas | 385643 | 4-May-15 | 13023 | 2 | 3 | | III-1 | Mir6397 | | |
| 12146 | 2 | 3 | | III-1 | Mcm3ap | 8888 | 12-May-15 | 13045 | 2 | 3 | | III-1 | Mir6419 | | |
| 12148 | 2 | 3 | | III-1 | Mcm5 | 4174 | 4-May-15 | 13095 | 2 | 3 | | III-1 | Mir684-1 | | |
| 12150 | 2 | 3 | | III-1 | Mcm7 | 4176 | 10-May-15 | 13181 | 2 | 3 | | III-1 | Mir6970 | | |
| 12151 | 2 | 3 | | III-1 | Mcm8 | 84515 | 4-May-15 | 13206 | 2 | 3 | | III-1 | Mir6993 | | |
| 12152 | 2 | 3 | | III-1 | Mcm9 | 254394 | 4-May-15 | 13439 | 2 | 3 | | III-1 | Mir8109 | | |
| 12158 | 2 | 3 | | III-1 | Mcph1 | 79648 | 23-May-15 | 13449 | 2 | 3 | | III-1 | Mir8120 | | |
| 12164 | 2 | 3 | | III-1 | Mcpt-ps1 | | | 13481 | 2 | 3 | | III-1 | Mirlet7c-1 | | |
| 12166 | 2 | 3 | | III-1 | Mctp1 | 79772 | 12-May-15 | 13497 | 2 | 3 | | III-1 | Mixl1 | 83881 | 28-May-15 |
| 12167 | 2 | 3 | | III-1 | Mctp2 | 55784 | 4-May-15 | 13504 | 2 | 3 | | III-1 | Mknk1 | 8569 | 4-May-15 |
| 12168 | 2 | 3 | | III-1 | Mcts1 | 28985 | 4-May-15 | 13506 | 2 | 3 | | III-1 | Mkrn1 | 23608 | 12-May-15 |
| 12170 | 2 | 3 | | III-1 | Mcu | 90550 | 10-May-15 | 13507 | 2 | 3 | | III-1 | Mkrn2 | 23609 | 23-May-15 |
| 12174 | 2 | 3 | | III-1 | Mdfic | 29969 | 4-May-15 | 13510 | 2 | 3 | | III-1 | Mkx | 283078 | 4-May-15 |
| 12178 | 2 | 3 | | III-1 | Mdh1b | 130752 | 4-May-15 | 13511 | 2 | 3 | | III-1 | Mlana | 2315 | 4-May-15 |
| 12179 | 2 | 3 | | III-1 | Mdh2 | 4191 | 3-May-15 | 13519 | 2 | 3 | | III-1 | Mlki | 197259 | 4-May-15 |
| 12182 | 2 | 3 | | III-1 | Mdm2 | 4193 | 31-May-15 | 13520 | 2 | 3 | | III-1 | Mlt1 | 4298 | 21-May-15 |
| 12187 | 2 | 3 | | III-1 | Me2 | 4200 | 7-Jun-15 | 13524 | 2 | 3 | | III-1 | Mlt4 | 4301 | 21-May-15 |
| 12189 | 2 | 3 | | III-1 | Mea1 | 4201 | 4-May-15 | 13525 | 2 | 3 | | III-1 | Mlt6 | 4302 | 4-May-15 |
| 12192 | 2 | 3 | | III-1 | Mecp2 | 4204 | 23-May-15 | 13527 | 2 | 3 | | III-1 | Mlsr8 | 64223 | 4-May-15 |
| 12193 | 2 | 3 | | III-1 | Mecr | 51102 | 7-Jun-15 | 13532 | 2 | 3 | | III-1 | Mnaa | 166785 | 7-Jun-15 |
| 12194 | 2 | 3 | | III-1 | Med1 | 5469 | 7-Jun-15 | 13534 | 2 | 3 | | III-1 | Mmachc | 25974 | 23-May-15 |
| 12196 | 2 | 3 | | III-1 | Med11 | 400569 | 28-May-15 | 13539 | 2 | 3 | | III-1 | Mmel1 | 79258 | 4-May-15 |
| 12198 | 2 | 3 | | III-1 | Med12l | 116931 | 28-May-15 | 13542 | 2 | 3 | | III-1 | Mmp10 | 4319 | 12-May-15 |
| 12201 | 2 | 3 | | III-1 | Med14 | 9282 | 21-May-15 | 13547 | 2 | 3 | | III-1 | Mmp15 | 4324 | 31-May-15 |
| 12206 | 2 | 3 | | III-1 | Med19 | 219541 | 28-May-15 | 13551 | 2 | 3 | | III-1 | Mrpla | | |
| 12214 | 2 | 3 | | III-1 | Med27 | 9442 | 4-May-15 | 13565 | 2 | 3 | | III-1 | Mmrn1 | 22915 | 4-May-15 |
| 12218 | 2 | 3 | | III-1 | Med31 | 51003 | 2-Jun-15 | 13566 | 2 | 3 | | III-1 | Mmrn2 | 79812 | 4-May-15 |
| 12219 | 2 | 3 | | III-1 | Med4 | 29079 | 31-May-15 | 13567 | 2 | 3 | | III-1 | Mms19 | 64210 | 4-May-15 |
| 12221 | 2 | 3 | | III-1 | Med7 | 9443 | 4-May-15 | 13570 | 2 | 3 | | III-1 | Mnat1 | 4331 | 1-Jun-15 |
| 12222 | 2 | 3 | | III-1 | Med8 | 112950 | 12-May-15 | 13571 | 2 | 3 | | III-1 | Mnd1 | 84057 | 4-May-15 |
| 12229 | 2 | 3 | | III-1 | Mef2d | 4209 | 28-May-15 | 13572 | 2 | 3 | | III-1 | Mnd1-ps | | |
| 12230 | 2 | 3 | | III-1 | Mefv | 4210 | 23-May-15 | 13574 | 2 | 3 | | III-1 | Mndal | | |
| 12231 | 2 | 3 | | III-1 | Meg3 | 55384 | 7-Jun-15 | 13580 | 2 | 3 | | III-1 | Mob1b | 92597 | 4-May-15 |
| 12233 | 2 | 3 | | III-1 | Megf11 | 84465 | 4-May-15 | 13586 | 2 | 3 | | III-1 | Mobp | 4336 | 4-May-15 |
| 12241 | 2 | 3 | | III-1 | Meis1 | 4211 | 4-May-15 | 13588 | 2 | 3 | | III-1 | Mocs1 | 4337 | 12-May-15 |
| 12243 | 2 | 3 | | III-1 | Meis3 | 56917 | 7-Jun-15 | 13589 | 2 | 3 | | III-1 | Mocs2 | 4338 | 4-May-15 |
| 12246 | 2 | 3 | | III-1 | Men1 | 4221 | 23-May-15 | 13590 | 2 | 3 | | III-1 | Mocs3 | 27304 | 24-May-15 |
| 12254 | 2 | 3 | | III-1 | Mesdc1 | 59274 | 4-May-15 | 13595 | 2 | 3 | | III-1 | Mok | 5891 | 4-May-15 |
| 12258 | 2 | 3 | | III-1 | Mest | 4232 | 12-May-15 | 13601 | 2 | 3 | | III-1 | Morc2b | | |
| 12260 | 2 | 3 | | III-1 | Metap1 | 23173 | 4-May-15 | 13604 | 2 | 3 | | III-1 | Morf4l1 | 10933 | 4-May-15 |
| 12265 | 2 | 3 | | III-1 | Mettl1 | 4234 | 4-May-15 | 13606 | 2 | 3 | | III-1 | Morn1 | 79906 | 12-May-15 |
| 12266 | 2 | 3 | | III-1 | Mettl10 | 399818 | 4-May-15 | 13607 | 2 | 3 | | III-1 | Morn2 | 729967 | 4-May-15 |
| 12267 | 2 | 3 | | III-1 | Mettl11b | 149281 | 4-May-15 | 13609 | 2 | 3 | | III-1 | Morn4 | 118812 | 4-May-15 |
| 12270 | 2 | 3 | | III-1 | Mettl15 | 196074 | 4-May-15 | 13610 | 2 | 3 | | III-1 | Morn5 | 254956 | 4-May-15 |
| 12271 | 2 | 3 | | III-1 | Mettl16 | 79686 | 12-May-15 | 13613 | 2 | 3 | | III-1 | Mospd2 | 158747 | 4-May-15 |
| 12273 | 2 | 3 | | III-1 | Mettl18 | 92342 | 4-May-15 | 13614 | 2 | 3 | | III-1 | Mospd3 | 64598 | 4-May-15 |
| 12274 | 2 | 3 | | III-1 | Mettl2 | 339175 | 7-Jun-15 | 13617 | 2 | 3 | | III-1 | Mov10l1 | 54456 | 4-May-15 |
| 12276 | 2 | 3 | | III-1 | Mettl21a | 151194 | 23-May-15 | 13621 | 2 | 3 | | III-1 | Mpc2 | 25874 | 12-May-15 |
| 12280 | 2 | 3 | | III-1 | Mettl23 | 124512 | 12-May-15 | 13625 | 2 | 3 | | III-1 | Mpg | 4350 | 12-May-15 |
| 12283 | 2 | 3 | | III-1 | Mettl3 | 56339 | 29-May-15 | 13626 | 2 | 3 | | III-1 | Mphosph10 | 10199 | 4-May-15 |
| 12285 | 2 | 3 | | III-1 | Mettl5 | 29081 | 4-May-15 | 13627 | 2 | 3 | | III-1 | Mphosph6 | 10200 | 4-May-15 |
| 12286 | 2 | 3 | | III-1 | Mettl6 | 131965 | 12-May-15 | 13628 | 2 | 3 | | III-1 | Mphosph8 | 54737 | 17-May-15 |
| 12288 | 2 | 3 | | III-1 | Mettl7a2 | | | 13629 | 2 | 3 | | III-1 | Mphosph9 | 10198 | 4-May-15 |
| 12289 | 2 | 3 | | III-1 | Mettl7a2Higd1c | | | 13631 | 2 | 3 | | III-1 | Mpl | 4352 | 3-May-15 |
| 12291 | 2 | 3 | | III-1 | Mettl7b | 196410 | 4-May-15 | 13634 | 2 | 3 | | III-1 | Mpo | 4353 | 23-May-15 |
| 12298 | 2 | 3 | | III-1 | Mfap1a | | | 13638 | 2 | 3 | | III-1 | Mpp4 | 58538 | 7-Jun-15 |
| 12309 | 2 | 3 | | III-1 | Mfn1 | 55669 | 24-May-15 | 13641 | 2 | 3 | | III-1 | Mpp7 | 143098 | 7-Jun-15 |
| 12310 | 2 | 3 | | III-1 | Mfn2 | 9927 | 31-May-15 | 13659 | 2 | 3 | | III-1 | Mras | 22808 | 4-May-15 |
| 12311 | 2 | 3 | | III-1 | Mfng | 4242 | 4-May-15 | 13661 | 2 | 3 | | III-1 | Mrc2 | 9902 | 4-May-15 |
| 12313 | 2 | 3 | | III-1 | Mfsd1 | 64747 | 4-May-15 | 13666 | 2 | 3 | | III-1 | Mrgpra1 | | |
| 12315 | 2 | 3 | | III-1 | Mfsd11 | 79157 | 4-May-15 | 13674 | 2 | 3 | | III-1 | Mrgprb2 | | |
| 12318 | 2 | 3 | | III-1 | Mfsd2b | 388931 | 4-May-15 | 13676 | 2 | 3 | | III-1 | Mrgprb4 | | |
| 12320 | 2 | 3 | | III-1 | Mfsd4 | 148808 | 4-May-15 | 13681 | 2 | 3 | | III-1 | Mrgprf | 116835 | 4-May-15 |
| 12324 | 2 | 3 | | III-1 | Mfsd7a | | | 13683 | 2 | 3 | | III-1 | Mrgprh | | |
| 12325 | 2 | 3 | | III-1 | Mfsd7b | 28982 | 4-May-15 | 13688 | 2 | 3 | | III-1 | Mro | 83876 | 4-May-15 |
| 12327 | 2 | 3 | | III-1 | Mfsd8 | 256471 | 23-May-15 | 13690 | 2 | 3 | | III-1 | Mroh2a | 339766 | 3-May-15 |
| 12329 | 2 | 3 | | III-1 | Mga | 23269 | 7-Jun-15 | 13701 | 2 | 3 | | III-1 | Mrpl12 | 6182 | 4-May-15 |
| 12332 | 2 | 3 | | III-1 | Mgat1 | 4245 | 4-May-15 | 13703 | 2 | 3 | | III-1 | Mrpl14 | 64928 | 7-Jun-15 |
| 12334 | 2 | 3 | | III-1 | Mgat3 | 4248 | 7-Jun-15 | 13704 | 2 | 3 | | III-1 | Mrpl15 | 29088 | 7-Jun-15 |
| 12336 | 2 | 3 | | III-1 | Mgat4b | 11282 | 4-May-15 | 13710 | 2 | 3 | | III-1 | Mrpl20 | 55052 | 4-May-15 |
| 12337 | 2 | 3 | | III-1 | Mgat4c | 25834 | 12-May-15 | 13711 | 2 | 3 | | III-1 | Mrpl21 | 219927 | 4-May-15 |
| 12340 | 2 | 3 | | III-1 | Mgea5 | 10724 | 7-Jun-15 | 13713 | 2 | 3 | | III-1 | Mrpl23 | 6150 | 4-May-15 |
| 12342 | 2 | 3 | | III-1 | Mgll | 11343 | 17-May-15 | 13714 | 2 | 3 | | III-1 | Mrpl24 | 79590 | 4-May-15 |
| 12343 | 2 | 3 | | III-1 | Mgme1 | 92667 | 7-Jun-15 | 13716 | 2 | 3 | | III-1 | Mrpl28 | 10573 | 7-Jun-15 |
| 12346 | 2 | 3 | | III-1 | Mgrn1 | 23295 | 4-May-15 | 13719 | 2 | 3 | | III-1 | Mrpl32 | 64983 | 7-Jun-15 |
| 12348 | 2 | 3 | | III-1 | Mgst2 | 4258 | 4-May-15 | 13720 | 2 | 3 | | III-1 | Mrpl33 | 9553 | 4-May-15 |
| 12352 | 2 | 3 | | III-1 | Mia3 | 375056 | 4-May-15 | 13721 | 2 | 3 | | III-1 | Mrpl34 | 64981 | 4-May-15 |
| 12353 | 2 | 3 | | III-1 | Miat | 440823 | 12-May-15 | 13725 | 2 | 3 | | III-1 | Mrpl38 | 64978 | 4-May-15 |
| 12358 | 2 | 3 | | III-1 | Mical3 | 57553 | 23-May-15 | 13726 | 2 | 3 | | III-1 | Mrpl39 | 54148 | 12-May-15 |
| 12360 | 2 | 3 | | III-1 | Micall1 | 85377 | 24-May-15 | 13731 | 2 | 3 | | III-1 | Mrpl43 | 84545 | 12-May-15 |
| 12361 | 2 | 3 | | III-1 | Micall2 | 79778 | 4-May-15 | 13734 | 2 | 3 | | III-1 | Mrpl46 | 26589 | 4-May-15 |
| 12367 | 2 | 3 | | III-1 | Mid2 | 11043 | 4-May-15 | 13736 | 2 | 3 | | III-1 | Mrpl48 | 51642 | 4-May-15 |
| 12368 | 2 | 3 | | III-1 | Midn | 90007 | 4-May-15 | 13737 | 2 | 3 | | III-1 | Mrpl49 | 740 | 4-May-15 |
| 12371 | 2 | 3 | | III-1 | Mien1 | 84299 | 4-May-15 | 13741 | 2 | 3 | | III-1 | Mrpl53 | 116540 | 4-May-15 |
| 12372 | 2 | 3 | | III-1 | Mier1 | 57708 | 12-May-15 | 13745 | 2 | 3 | | III-1 | Mrps11 | 64963 | 28-May-15 |
| 12376 | 2 | 3 | | III-1 | Mif4gd | 57409 | 3-May-15 | 13752 | 2 | 3 | | III-1 | Mrps17 | 51373 | 28-May-15 |
| 12378 | 2 | 3 | | III-1 | Mill1 | | | 13754 | 2 | 3 | | III-1 | Mrps18b | 28973 | 28-May-15 |
| 12381 | 2 | 3 | | III-1 | Mina | 84864 | 12-May-15 | 13758 | 2 | 3 | | III-1 | Mrps22 | 56945 | 4-May-15 |
| 12382 | 2 | 3 | | III-1 | Mink1 | 50488 | 4-May-15 | 13759 | 2 | 3 | | III-1 | Mrps23 | 51649 | 4-May-15 |

Fig.22 - 74

| | | | | | | | | | | | | | | |
|---|---|---|---|---|---|---|---|---|---|---|---|---|---|---|
| 13761 | 2 | 3 | | III-1 | Mrps25 | 64432 | 4-May-15 | 14153 | 2 | 3 | | III-1 | Nbl1 | 4681 | 10-May-15 |
| 13762 | 2 | 3 | | III-1 | Mrps26 | 64949 | 4-May-15 | 14154 | 2 | 3 | | III-1 | Nbn | 4683 | 7-Jun-15 |
| 13763 | 2 | 3 | | III-1 | Mrps27 | 23107 | 4-May-15 | 14158 | 2 | 3 | | III-1 | Ncam2 | 4685 | 7-Jun-15 |
| 13768 | 2 | 3 | | III-1 | Mrps34 | 65993 | 21-May-15 | 14162 | 2 | 3 | | III-1 | Ncapg | 64151 | 4-May-15 |
| 13769 | 2 | 3 | | III-1 | Mrps35 | 60488 | 7-Jun-15 | 14167 | 2 | 3 | | III-1 | Ncbp2 | 22916 | 2-Jun-15 |
| 13770 | 2 | 3 | | III-1 | Mrps36 | 92259 | 4-May-15 | 14176 | 2 | 3 | | III-1 | Nckap1 | 10787 | 4-May-15 |
| 13775 | 2 | 3 | | III-1 | Mrrf | 92399 | 4-May-15 | 14179 | 2 | 3 | | III-1 | Nckap5l | 57701 | 4-May-15 |
| 13777 | 2 | 3 | | III-1 | Mrto4 | 51154 | 4-May-15 | 14181 | 2 | 3 | | III-1 | Ncl | 4691 | 13-Jun-15 |
| 13785 | 2 | 3 | | III-1 | Ms4a3 | 932 | 4-May-15 | 14184 | 2 | 3 | | III-1 | Ncoa1 | 8648 | 3-May-15 |
| 13789 | 2 | 3 | | III-1 | Ms4a5 | 64232 | 4-May-15 | 14190 | 2 | 3 | | III-1 | Ncoa7 | 135112 | 4-May-15 |
| 13795 | 2 | 3 | | III-1 | Msantd1 | 345222 | 4-May-15 | 14191 | 2 | 3 | | III-1 | Ncor1 | 9611 | 4-May-15 |
| 13796 | 2 | 3 | | III-1 | Msantd2 | 79684 | 12-May-15 | 14192 | 2 | 3 | | III-1 | Ncor2 | 9612 | 4-May-15 |
| 13805 | 2 | 3 | | III-1 | Msh6 | 2956 | 23-May-15 | 14195 | 2 | 3 | | III-1 | Ncstn | 23385 | 12-May-15 |
| 13806 | 2 | 3 | | III-1 | Msi1 | 4440 | 1-Jun-15 | 14198 | 2 | 3 | | III-1 | Ndc80 | 10403 | 4-May-15 |
| 13808 | 2 | 3 | | III-1 | Msi1 | 339287 | 7-Jun-15 | 14200 | 2 | 3 | | III-1 | Ndel1 | 81565 | 2-Jun-15 |
| 13816 | 2 | 3 | | III-1 | Msmp | 692094 | 4-May-15 | 14202 | 2 | 3 | | III-1 | Ndfip2 | 54602 | 4-May-15 |
| 13819 | 2 | 3 | | III-1 | Msra | 4482 | 12-May-15 | 14207 | 2 | 3 | | III-1 | Ndp | 4693 | 23-May-15 |
| 13821 | 2 | 3 | | III-1 | Msrb2 | 22921 | 23-May-15 | 14210 | 2 | 3 | | III-1 | Ndrg3 | 57446 | 4-May-15 |
| 13828 | 2 | 3 | | III-1 | Msx1 | 4487 | 17-May-15 | 14213 | 2 | 3 | | III-1 | Ndst2 | 8509 | 4-May-15 |
| 13845 | 2 | 3 | | III-1 | Mtcl1 | 23255 | 12-May-15 | 14217 | 2 | 3 | | III-1 | Ndufa10 | 4705 | 23-May-15 |
| 13847 | 2 | 3 | | III-1 | Mrdh | 92140 | 17-May-15 | 14219 | 2 | 3 | | III-1 | Ndufa12 | 55967 | 23-May-15 |
| 13848 | 2 | 3 | | III-1 | Mterf1a | | | 14220 | 2 | 3 | | III-1 | Ndufa13 | 51079 | 4-May-15 |
| 13856 | 2 | 3 | | III-1 | Mrerfd1 | 51001 | 4-May-15 | 14222 | 2 | 3 | | III-1 | Ndufa3 | 4696 | 23-May-15 |
| 13857 | 2 | 3 | | III-1 | Mtfr1 | 9650 | 20-May-15 | 14226 | 2 | 3 | | III-1 | Ndufa6 | 4700 | 23-May-15 |
| 13858 | 2 | 3 | | III-1 | Mtfr1l | 56181 | 4-May-15 | 14227 | 2 | 3 | | III-1 | Ndufa7 | 4701 | 29-May-15 |
| 13861 | 2 | 3 | | III-1 | Mtg2 | 26164 | 4-May-15 | 14228 | 2 | 3 | | III-1 | Ndufa8 | 4702 | 4-May-15 |
| 13865 | 2 | 3 | | III-1 | Mthfd2l | 441024 | 4-May-15 | 14229 | 2 | 3 | | III-1 | Ndufa9 | 4704 | 23-May-15 |
| 13866 | 2 | 3 | | III-1 | Mthfr | 4524 | 24-May-15 | 14231 | 2 | 3 | | III-1 | Ndufaf1 | 51103 | 4-May-15 |
| 13868 | 2 | 3 | | III-1 | Mthfsd | 64779 | 4-May-15 | 14233 | 2 | 3 | | III-1 | Ndufaf3 | 25915 | 4-May-15 |
| 13876 | 2 | 3 | | III-1 | Mtmr12 | 54545 | 12-May-15 | 14236 | 2 | 3 | | III-1 | Ndufaf6 | 137682 | 23-May-15 |
| 13878 | 2 | 3 | | III-1 | Mtmr2 | 8298 | 23-May-15 | 14237 | 2 | 3 | | III-1 | Ndufaf7 | 55471 | 31-May-15 |
| 13884 | 2 | 3 | | III-1 | Mtnr1a | 4543 | 4-May-15 | 14241 | 2 | 3 | | III-1 | Ndufb3 | 4709 | 23-May-15 |
| 13885 | 2 | 3 | | III-1 | Mtnr1b | 4544 | 21-May-15 | 14242 | 2 | 3 | | III-1 | Ndufb4 | 4710 | 4-May-15 |
| 13891 | 2 | 3 | | III-1 | Mtrf1 | 9617 | 4-May-15 | 14243 | 2 | 3 | | III-1 | Ndufb5 | 4711 | 4-May-15 |
| 13892 | 2 | 3 | | III-1 | Mrrf1l | 54516 | 4-May-15 | 14244 | 2 | 3 | | III-1 | Ndufb6 | 4712 | 4-May-15 |
| 13896 | 2 | 3 | | III-1 | Mttp | 4547 | 7-Jun-15 | 14247 | 2 | 3 | | III-1 | Ndufb9 | 4715 | 28-May-15 |
| 13897 | 2 | 3 | | III-1 | Mturn | 222166 | 4-May-15 | 14248 | 2 | 3 | | III-1 | Ndufc1 | 4717 | 4-May-15 |
| 13899 | 2 | 3 | | III-1 | Mtus2 | 23281 | 4-May-15 | 14249 | 2 | 3 | | III-1 | Ndufc2 | 4718 | 4-May-15 |
| 13900 | 2 | 3 | | III-1 | Mtx1 | 4580 | 4-May-15 | 14250 | 2 | 3 | | III-1 | Ndufs1 | 4719 | 4-May-15 |
| 13901 | 2 | 3 | | III-1 | Mtx2 | 10651 | 4-May-15 | 14251 | 2 | 3 | | III-1 | Ndufs2 | 4720 | 21-May-15 |
| 13902 | 2 | 3 | | III-1 | Mtx3 | 345778 | 4-May-15 | 14252 | 2 | 3 | | III-1 | Ndufs3 | 4722 | 23-May-15 |
| 13904 | 2 | 3 | | III-1 | Muc13 | 56667 | 4-May-15 | 14253 | 2 | 3 | | III-1 | Ndufs4 | 4724 | 23-May-15 |
| 13913 | 2 | 3 | | III-1 | Mucl1 | 118430 | 4-May-15 | 14256 | 2 | 3 | | III-1 | Ndufs7 | 374291 | 23-May-15 |
| 13916 | 2 | 3 | | III-1 | Mug-ps1 | | | 14257 | 2 | 3 | | III-1 | Ndufs8 | 4728 | 23-May-15 |
| 13936 | 2 | 3 | | III-1 | Mup6 | | | 14258 | 2 | 3 | | III-1 | Ndufv1 | 4723 | 12-May-15 |
| 13942 | 2 | 3 | | III-1 | Musk | 4593 | 7-May-15 | 14259 | 2 | 3 | | III-1 | Ndufv2 | 4729 | 4-May-15 |
| 13947 | 2 | 3 | | III-1 | Mvb12b | 89853 | 12-May-15 | 14260 | 2 | 3 | | III-1 | Ndufv3 | 4731 | 4-May-15 |
| 13951 | 2 | 3 | | III-1 | Mx1 | 4599 | 12-May-15 | 14266 | 2 | 3 | | III-1 | Necab3 | 63941 | 4-May-15 |
| 13953 | 2 | 3 | | III-1 | Mxd1 | 4084 | 24-May-15 | 14267 | 2 | 3 | | III-1 | Necap1 | 25977 | 4-May-15 |
| 13959 | 2 | 3 | | III-1 | Myadm | 91663 | 23-May-15 | 14272 | 2 | 3 | | III-1 | Nedd8 | 4738 | 4-May-15 |
| 13969 | 2 | 3 | | III-1 | Mybphl | 343263 | 4-May-15 | 14274 | 2 | 3 | | III-1 | Nefh | 4744 | 23-May-15 |
| 13972 | 2 | 3 | | III-1 | Mycbp2 | 23077 | 4-May-15 | 14277 | 2 | 3 | | III-1 | Negr1 | 257194 | 4-May-15 |
| 13979 | 2 | 3 | | III-1 | Myef2 | 50804 | 4-May-15 | 14278 | 2 | 3 | | III-1 | Neil1 | 79661 | 4-May-15 |
| 13980 | 2 | 3 | | III-1 | Myeov2 | 150678 | 4-May-15 | 14289 | 2 | 3 | | III-1 | Nek7 | 140609 | 4-May-15 |
| 13981 | 2 | 3 | | III-1 | Myf5 | 4617 | 28-May-15 | 14291 | 2 | 3 | | III-1 | Nek9 | 91754 | 4-May-15 |
| 14009 | 2 | 3 | | III-1 | Mylip | 29116 | 4-May-15 | 14293 | 2 | 3 | | III-1 | Nelfb | 25920 | 4-May-15 |
| 14017 | 2 | 3 | | III-1 | Myo15 | 51168 | 23-May-15 | 14297 | 2 | 3 | | III-1 | Nelllos | | |
| 14022 | 2 | 3 | | III-1 | Myo1a | 4640 | 23-May-15 | 14298 | 2 | 3 | | III-1 | Nell2 | 4753 | 12-May-15 |
| 14024 | 2 | 3 | | III-1 | Myo1c | 4641 | 7-Jun-15 | 14300 | 2 | 3 | | III-1 | Nenf | 29937 | 4-May-15 |
| 14025 | 2 | 3 | | III-1 | Myo1d | 4642 | 12-May-15 | 14302 | 2 | 3 | | III-1 | Nepn | 442253 | 4-May-15 |
| 14026 | 2 | 3 | | III-1 | Myo1e | 4643 | 12-May-15 | 14306 | 2 | 3 | | III-1 | Neto1 | 81832 | 4-May-15 |
| 14032 | 2 | 3 | | III-1 | Myo5a | 4644 | 4-May-15 | 14311 | 2 | 3 | | III-1 | Neu4 | 129807 | 4-May-15 |
| 14035 | 2 | 3 | | III-1 | Myo6 | 4646 | 23-May-15 | 14316 | 2 | 3 | | III-1 | Neurl4 | 84461 | 4-May-15 |
| 14036 | 2 | 3 | | III-1 | Myo7a | 4647 | 23-May-15 | 14318 | 2 | 3 | | III-1 | Neurod2 | 4761 | 28-May-15 |
| 14037 | 2 | 3 | | III-1 | Myo7b | 4648 | 4-May-15 | 14320 | 2 | 3 | | III-1 | Neurod6 | 63974 | 28-May-15 |
| 14054 | 2 | 3 | | III-1 | Myrf | 745 | 12-May-15 | 14330 | 2 | 3 | | III-1 | Nfatc1 | 4772 | 31-May-15 |
| 14057 | 2 | 3 | | III-1 | Mysm1 | 114803 | 4-May-15 | 14332 | 2 | 3 | | III-1 | Nfatc2ip | 84901 | 4-May-15 |
| 14063 | 2 | 3 | | III-1 | Mzt1 | 440145 | 4-May-15 | 14336 | 2 | 3 | | III-1 | Nfe2l1 | 4779 | 4-May-15 |
| 14066 | 2 | 3 | | III-1 | N4bp1 | 9683 | 4-May-15 | 14339 | 2 | 3 | | III-1 | Nfia | 4774 | 2-Jun-15 |
| 14069 | 2 | 3 | | III-1 | N4bp2l2 | 10443 | 4-May-15 | 14340 | 2 | 3 | | III-1 | Nfib | 4781 | 28-May-15 |
| 14072 | 2 | 3 | | III-1 | N6amt2 | 221143 | 4-May-15 | 14341 | 2 | 3 | | III-1 | Nfic | 4782 | 17-May-15 |
| 14074 | 2 | 3 | | III-1 | Naa11 | 84779 | 4-May-15 | 14344 | 2 | 3 | | III-1 | Nfkb1 | 4790 | 28-May-15 |
| 14077 | 2 | 3 | | III-1 | Naa20 | 51126 | 4-May-15 | 14347 | 2 | 3 | | III-1 | Nfkbib | 4793 | 31-May-15 |
| 14082 | 2 | 3 | | III-1 | Naa40 | 79829 | 4-May-15 | 14348 | 2 | 3 | | III-1 | Nfkbid | 84807 | 4-May-15 |
| 14088 | 2 | 3 | | III-1 | Nab1 | 4664 | 4-May-15 | 14349 | 2 | 3 | | III-1 | Nfkbie | 4794 | 12-May-15 |
| 14090 | 2 | 3 | | III-1 | Nabp1 | 64859 | 4-May-15 | 14352 | 2 | 3 | | III-1 | Nfrkb | 4798 | 4-May-15 |
| 14091 | 2 | 3 | | III-1 | Nabp2 | 79035 | 4-May-15 | 14355 | 2 | 3 | | III-1 | Nfx1 | 4799 | 4-May-15 |
| 14093 | 2 | 3 | | III-1 | Nacad | 23148 | 4-May-15 | 14361 | 2 | 3 | | III-1 | Ngdn | 25983 | 4-May-15 |
| 14094 | 2 | 3 | | III-1 | Nacc1 | 112939 | 4-May-15 | 14362 | 2 | 3 | | III-1 | Ngef | 25791 | 4-May-15 |
| 14096 | 2 | 3 | | III-1 | Nadk | 65220 | 4-May-15 | 14363 | 2 | 3 | | III-1 | Ngf | 4803 | 24-May-15 |
| 14098 | 2 | 3 | | III-1 | Nadsyn1 | 55191 | 12-May-15 | 14366 | 2 | 3 | | III-1 | Ngly1 | 55768 | 12-May-15 |
| 14100 | 2 | 3 | | III-1 | Naf1 | 92345 | 16-Jun-15 | 14374 | 2 | 3 | | III-1 | Nhlrc3 | 387921 | 4-May-15 |
| 14107 | 2 | 3 | | III-1 | Naip1 | | | 14380 | 2 | 3 | | III-1 | Nhsl2 | 340527 | 12-May-15 |
| 14114 | 2 | 3 | | III-1 | Nanog | 79923 | 7-Jun-15 | 14382 | 2 | 3 | | III-1 | Nid1 | 4811 | 12-May-15 |
| 14117 | 2 | 3 | | III-1 | Nanos3 | 342977 | 4-May-15 | 14389 | 2 | 3 | | III-1 | Ninj2 | 4815 | 4-May-15 |
| 14120 | 2 | 3 | | III-1 | Nap1l1 | 4673 | 12-May-15 | 14391 | 2 | 3 | | III-1 | Nip7 | 51388 | 4-May-15 |
| 14121 | 2 | 3 | | III-1 | Nap1l2 | 4674 | 12-May-15 | 14393 | 2 | 3 | | III-1 | Nipa2 | 81614 | 7-Jun-15 |
| 14122 | 2 | 3 | | III-1 | Nap1l3 | 4675 | 12-May-15 | 14396 | 2 | 3 | | III-1 | Nipal3 | 57185 | 4-May-15 |
| 14127 | 2 | 3 | | III-1 | Napepld | 222236 | 12-May-15 | 14399 | 2 | 3 | | III-1 | Nipsnap1 | 8508 | 17-May-15 |
| 14128 | 2 | 3 | | III-1 | Napg | 8774 | 4-May-15 | 14400 | 2 | 3 | | III-1 | Nipsnap3a | 25934 | 4-May-15 |
| 14130 | 2 | 3 | | III-1 | Napsa | 9476 | 4-May-15 | 14405 | 2 | 3 | | III-1 | Nkain1 | 79570 | 4-May-15 |
| 14136 | 2 | 3 | | III-1 | Nasp | 4678 | 21-May-15 | 14406 | 2 | 3 | | III-1 | Nkain2 | 154215 | 4-May-15 |
| 14140 | 2 | 3 | | III-1 | Nat2 | 10 | 16-Jun-15 | 14409 | 2 | 3 | | III-1 | Nkap | 79576 | 4-May-15 |
| 14146 | 2 | 3 | | III-1 | Nav1 | 89796 | 4-May-15 | 14411 | 2 | 3 | | III-1 | Nkd1 | 85407 | 12-May-15 |
| 14148 | 2 | 3 | | III-1 | Nav3 | 89795 | 4-May-15 | 14412 | 2 | 3 | | III-1 | Nkd2 | 85409 | 4-May-15 |
| 14150 | 2 | 3 | | III-1 | Nbea | 26960 | 4-May-15 | 14413 | 2 | 3 | | III-1 | Nkg7 | 4818 | 4-May-15 |
| 14151 | 2 | 3 | | III-1 | Nbeal1 | 65065 | 4-May-15 | 14414 | 2 | 3 | | III-1 | Nkiras1 | 28512 | 4-May-15 |

Fig.22 - 75

| | | | | | | | | | | | | | | | |
|---|---|---|---|---|---|---|---|---|---|---|---|---|---|---|---|
| 14417 | 2 | 3 | | | III-1 | Nkrf | 55922 | 4-May-15 | 14739 | 2 | 3 | | III-1 | Nudt5 | 11164 | 21-May-15 |
| 14418 | 2 | 3 | | | III-1 | Nktr | 4820 | 4-May-15 | 14741 | 2 | 3 | | III-1 | Nudt7 | 283927 | 4-May-15 |
| 14419 | 2 | 3 | | | III-1 | Nkx1-1 | 54729 | 4-May-15 | 14744 | 2 | 3 | | III-1 | Nuf2 | 83540 | 4-May-15 |
| 14423 | 2 | 3 | | | III-1 | Nkx2-2os | | | 14746 | 2 | 3 | | III-1 | Nufip2 | 57532 | 4-May-15 |
| 14425 | 2 | 3 | | | III-1 | Nkx2-4 | 644524 | 4-May-15 | 14751 | 2 | 3 | | III-1 | Nup107 | 57122 | 4-May-15 |
| 14426 | 2 | 3 | | | III-1 | Nkx2-5 | 1482 | 31-May-15 | 14759 | 2 | 3 | | III-1 | Nup210l | 91181 | 21-May-15 |
| 14436 | 2 | 3 | | | III-1 | Nlgn2 | 57555 | 28-May-15 | 14762 | 2 | 3 | | III-1 | Nup37 | 79023 | 2-Jun-15 |
| 14437 | 2 | 3 | | | III-1 | Nlgn3 | 54413 | 28-May-15 | 14764 | 2 | 3 | | III-1 | Nup50 | 10762 | 4-May-15 |
| 14438 | 2 | 3 | | | III-1 | Nlk | 51701 | 7-Jun-15 | 14769 | 2 | 3 | | III-1 | Nup85 | 79902 | 4-May-15 |
| 14448 | 2 | 3 | | | III-1 | Nlrp1c-ps | | | 14773 | 2 | 3 | | III-1 | Nupl1 | 9818 | 4-May-15 |
| 14451 | 2 | 3 | | | III-1 | Nlrp4a | | | 14774 | 2 | 3 | | III-1 | Nupl2 | 11097 | 12-May-15 |
| 14473 | 2 | 3 | | | III-1 | Nme7 | 29922 | 12-May-15 | 14784 | 2 | 3 | | III-1 | Nwd2 | 57495 | 4-May-15 |
| 14477 | 2 | 3 | | | III-1 | Nmnat1 | 64802 | 23-May-15 | 14788 | 2 | 3 | | III-1 | Nxf7 | | |
| 14480 | 2 | 3 | | | III-1 | Nmral1 | 57407 | 20-May-15 | 14807 | 2 | 3 | | III-1 | Oaf | 220323 | 4-May-15 |
| 14486 | 2 | 3 | | | III-1 | Nmu | 10874 | 12-May-15 | 14809 | 2 | 3 | | III-1 | Oas1a | | |
| 14488 | 2 | 3 | | | III-1 | Nmur2 | 56923 | 4-May-15 | 14811 | 2 | 3 | | III-1 | Oas1c | | |
| 14492 | 2 | 3 | | | III-1 | Noa1 | 84273 | 4-May-15 | 14812 | 2 | 3 | | III-1 | Oas1d | | |
| 14496 | 2 | 3 | | | III-1 | Noc3l | 64318 | 4-May-15 | 14814 | 2 | 3 | | III-1 | Oas1f | | |
| 14499 | 2 | 3 | | | III-1 | Nod2 | 64127 | 31-May-15 | 14827 | 2 | 3 | | III-1 | Obox1 | | |
| 14506 | 2 | 3 | | | III-1 | Nol4 | 8715 | 4-May-15 | 14834 | 2 | 3 | | III-1 | Obp2b | 29989 | 4-May-15 |
| 14510 | 2 | 3 | | | III-1 | Nol9 | 79707 | 4-May-15 | 14843 | 2 | 3 | | III-1 | Ocm | 654231 | 4-May-15 |
| 14512 | 2 | 3 | | | III-1 | Nom1 | 64434 | 4-May-15 | 14844 | 2 | 3 | | III-1 | Ocrl | 4952 | 23-May-15 |
| 14517 | 2 | 3 | | | III-1 | Nop16 | 51491 | 12-May-15 | 14846 | 2 | 3 | | III-1 | Odam | 54959 | 4-May-15 |
| 14518 | 2 | 3 | | | III-1 | Nop2 | 4839 | 12-May-15 | 14847 | 2 | 3 | | III-1 | Odc1 | 4953 | 7-Jun-15 |
| 14519 | 2 | 3 | | | III-1 | Nop56 | 10528 | 22-May-15 | 14849 | 2 | 3 | | III-1 | Odf2 | 4957 | 7-Jun-15 |
| 14520 | 2 | 3 | | | III-1 | Nop58 | 51602 | 21-May-15 | 14850 | 2 | 3 | | III-1 | Odf2l | 57489 | 4-May-15 |
| 14521 | 2 | 3 | | | III-1 | Nop9 | 161424 | 7-Jun-15 | 14851 | 2 | 3 | | III-1 | Odf3 | 113746 | 4-May-15 |
| 14523 | 2 | 3 | | | III-1 | Nos1ap | 9722 | 1-Jun-15 | 14855 | 2 | 3 | | III-1 | Odf4 | 146852 | 4-May-15 |
| 14526 | 2 | 3 | | | III-1 | Nosip | 51070 | 4-May-15 | 14858 | 2 | 3 | | III-1 | Ogdh | 4967 | 12-May-15 |
| 14528 | 2 | 3 | | | III-1 | Notch1 | 4851 | 31-May-15 | 14860 | 2 | 3 | | III-1 | Ogfod1 | 55239 | 12-May-15 |
| 14529 | 2 | 3 | | | III-1 | Notch2 | 4853 | 23-May-15 | 14862 | 2 | 3 | | III-1 | Ogfod3 | 79701 | 4-May-15 |
| 14530 | 2 | 3 | | | III-1 | Notch3 | 4854 | 23-May-15 | 14863 | 2 | 3 | | III-1 | Ogfr | 11054 | 4-May-15 |
| 14531 | 2 | 3 | | | III-1 | Notch4 | 4855 | 4-May-15 | 14865 | 2 | 3 | | III-1 | Ogg1 | 4968 | 4-May-15 |
| 14538 | 2 | 3 | | | III-1 | Nox3 | 50508 | 3-May-15 | 14867 | 2 | 3 | | III-1 | Ogt | 8473 | 17-May-15 |
| 14541 | 2 | 3 | | | III-1 | Noxo1 | 124056 | 4-May-15 | 14871 | 2 | 3 | | III-1 | Ola1 | 29789 | 23-May-15 |
| 14542 | 2 | 3 | | | III-1 | Noxred1 | 122945 | 4-May-15 | 14877 | 2 | 3 | | III-1 | Olfml1 | 283298 | 4-May-15 |
| 14549 | 2 | 3 | | | III-1 | Npbwr1 | 2831 | 4-May-15 | 14912 | 2 | 3 | | III-1 | Olfr1036 | | |
| 14551 | 2 | 3 | | | III-1 | Npc1l1 | 29881 | 17-May-15 | 15107 | 2 | 3 | | III-1 | Olfr1270 | | |
| 14555 | 2 | 3 | | | III-1 | Npepl1 | 79716 | 4-May-15 | 15177 | 2 | 3 | | III-1 | Olfr1346 | | |
| 14558 | 2 | 3 | | | III-1 | Npffr1 | 64106 | 4-May-15 | 15203 | 2 | 3 | | III-1 | Olfr1373 | | |
| 14562 | 2 | 3 | | | III-1 | Nphp4 | 261734 | 17-May-15 | 15211 | 2 | 3 | | III-1 | Olfr1384 | | |
| 14563 | 2 | 3 | | | III-1 | Nphs1 | 4868 | 4-May-15 | 15243 | 2 | 3 | | III-1 | Olfr1423 | | |
| 14567 | 2 | 3 | | | III-1 | Nploc4 | 55666 | 28-May-15 | 15308 | 2 | 3 | | III-1 | Olfr1508 | | |
| 14569 | 2 | 3 | | | III-1 | Npm2 | 10361 | 4-May-15 | 15454 | 2 | 3 | | III-1 | Olfr331 | | |
| 14574 | 2 | 3 | | | III-1 | Nppb | 4879 | 17-May-15 | 15619 | 2 | 3 | | III-1 | Olfr541 | | |
| 14575 | 2 | 3 | | | III-1 | Nppc | 4880 | 21-May-15 | 15937 | 2 | 3 | | III-1 | Olfr923 | | |
| 14577 | 2 | 3 | | | III-1 | Npr2 | 4882 | 7-Jun-15 | 15992 | 2 | 3 | | III-1 | Olfr992 | | |
| 14580 | 2 | 3 | | | III-1 | Npr3 | 8131 | 29-May-15 | 16021 | 2 | 3 | | III-1 | Opalin | 93377 | 4-May-15 |
| 14591 | 2 | 3 | | | III-1 | Npy2r | 4887 | 12-May-15 | 16024 | 2 | 3 | | III-1 | Oplah | 26873 | 4-May-15 |
| 14596 | 2 | 3 | | | III-1 | Nqo2 | 4835 | 28-May-15 | 16025 | 2 | 3 | | III-1 | Oprl1mw | 2652 | 23-May-15 |
| 14598 | 2 | 3 | | | III-1 | Nr0b2 | 8431 | 24-May-15 | 16028 | 2 | 3 | | III-1 | Opn4 | 94233 | 21-May-15 |
| 14604 | 2 | 3 | | | III-1 | Nr1h5 | 643609 | 4-May-15 | 16035 | 2 | 3 | | III-1 | Optn | 10133 | 23-May-15 |
| 14607 | 2 | 3 | | | III-1 | Nr2c1 | 7181 | 4-May-15 | 16037 | 2 | 3 | | III-1 | Orai2 | 80228 | 4-May-15 |
| 14610 | 2 | 3 | | | III-1 | Nr2e1 | 7101 | 4-May-15 | 16039 | 2 | 3 | | III-1 | Oraov1 | 220064 | 4-May-15 |
| 14614 | 2 | 3 | | | III-1 | Nr2f6 | 2063 | 4-May-15 | 16045 | 2 | 3 | | III-1 | Orc6 | 23594 | 4-May-15 |
| 14615 | 2 | 3 | | | III-1 | Nr3c1 | 2908 | 31-May-15 | 16046 | 2 | 3 | | III-1 | Orm1 | 5004 | 12-May-15 |
| 14618 | 2 | 3 | | | III-1 | Nr4a2 | 4929 | 31-May-15 | 16051 | 2 | 3 | | III-1 | Ormdl3 | 94103 | 4-May-15 |
| 14620 | 2 | 3 | | | III-1 | Nr5a1 | 2516 | 12-May-15 | 16052 | 2 | 3 | | III-1 | Os9 | 10956 | 3-May-15 |
| 14621 | 2 | 3 | | | III-1 | Nr5a2 | 2494 | 12-May-15 | 16056 | 2 | 3 | | III-1 | Osbpl11 | 114885 | 4-May-15 |
| 14623 | 2 | 3 | | | III-1 | Nradd | | | 16058 | 2 | 3 | | III-1 | Osbpl2 | 9885 | 22-May-15 |
| 14630 | 2 | 3 | | | III-1 | Nrcam | 4897 | 4-May-15 | 16059 | 2 | 3 | | III-1 | Osbpl3 | 26031 | 4-May-15 |
| 14632 | 2 | 3 | | | III-1 | Nrde2 | 55051 | 4-May-15 | 16060 | 2 | 3 | | III-1 | Osbpl5 | 114879 | 4-May-15 |
| 14636 | 2 | 3 | | | III-1 | Nrg2 | 9542 | 12-May-15 | 16061 | 2 | 3 | | III-1 | Osbpl6 | 114880 | 12-May-15 |
| 14639 | 2 | 3 | | | III-1 | Nrg4 | 145957 | 4-May-15 | 16063 | 2 | 3 | | III-1 | Osbpl8 | 114882 | 12-May-15 |
| 14644 | 2 | 3 | | | III-1 | Nrk | 203447 | 12-May-15 | 16067 | 2 | 3 | | III-1 | Oser1 | 51526 | 4-May-15 |
| 14648 | 2 | 3 | | | III-1 | Nrn1l | 123904 | 4-May-15 | 16069 | 2 | 3 | | III-1 | Osgepl1 | 64172 | 4-May-15 |
| 14657 | 2 | 3 | | | III-1 | Nrxn1 | 9378 | 4-May-15 | 16077 | 2 | 3 | | III-1 | Ostc | 58505 | 4-May-15 |
| 14659 | 2 | 3 | | | III-1 | Nrxn3 | 9369 | 4-May-15 | 16078 | 2 | 3 | | III-1 | Ostf1 | 26578 | 4-May-15 |
| 14661 | 2 | 3 | | | III-1 | Nsd1 | 64324 | 28-May-15 | 16079 | 2 | 3 | | III-1 | Ostm1 | 28962 | 4-May-15 |
| 14662 | 2 | 3 | | | III-1 | Nsdhl | 50814 | 23-May-15 | 16084 | 2 | 3 | | III-1 | Otog | 340990 | 7-Jun-15 |
| 14666 | 2 | 3 | | | III-1 | Nsg2 | | | 16090 | 2 | 3 | | III-1 | Otor | 56914 | 12-May-15 |
| 14671 | 2 | 3 | | | III-1 | Nsmce4a | 54780 | 4-May-15 | 16091 | 2 | 3 | | III-1 | Otos | 150677 | 4-May-15 |
| 14673 | 2 | 3 | | | III-1 | Nsun2 | 54888 | 4-May-15 | 16094 | 2 | 3 | | III-1 | OTTMUSG00000016609 | | |
| 14675 | 2 | 3 | | | III-1 | Nsun4 | 387338 | 4-May-15 | 16095 | 2 | 3 | | III-1 | Otub1 | 55611 | 4-May-15 |
| 14677 | 2 | 3 | | | III-1 | Nsun6 | 221078 | 12-May-15 | 16097 | 2 | 3 | | III-1 | Otud1 | 220213 | 4-May-15 |
| 14679 | 2 | 3 | | | III-1 | Nt5c | 30833 | 4-May-15 | 16098 | 2 | 3 | | III-1 | Otud3 | 23252 | 4-May-15 |
| 14682 | 2 | 3 | | | III-1 | Nt5c2 | 22978 | 2-Jun-15 | 16099 | 2 | 3 | | III-1 | Otud4 | 54726 | 4-May-15 |
| 14683 | 2 | 3 | | | III-1 | Nt5c3 | 51251 | 4-May-15 | 16104 | 2 | 3 | | III-1 | Otud7b | 56957 | 17-May-15 |
| 14684 | 2 | 3 | | | III-1 | Nt5c3b | 115024 | 10-May-15 | 16105 | 2 | 3 | | III-1 | Otulin | 90268 | 4-May-15 |
| 14687 | 2 | 3 | | | III-1 | Nt5dc3 | 51559 | 23-May-15 | 16106 | 2 | 3 | | III-1 | Otx1 | 5013 | 30-May-15 |
| 14691 | 2 | 3 | | | III-1 | Nth3 | 4908 | 3-May-15 | 16108 | 2 | 3 | | III-1 | Otx2os1 | 100309464 | 21-May-15 |
| 14693 | 2 | 3 | | | III-1 | Nthl1 | 4913 | 28-May-15 | 16111 | 2 | 3 | | III-1 | Ovgp1 | 5016 | 12-May-15 |
| 14694 | 2 | 3 | | | III-1 | Ntm | 50863 | 2-Jun-15 | 16112 | 2 | 3 | | III-1 | Ovol1 | 5017 | 4-May-15 |
| 14696 | 2 | 3 | | | III-1 | Ntn1 | 9423 | 17-May-15 | 16117 | 2 | 3 | | III-1 | Oxct2a | | |
| 14699 | 2 | 3 | | | III-1 | Ntn5 | 126147 | 4-May-15 | 16119 | 2 | 3 | | III-1 | Oxgr1 | 27199 | 4-May-15 |
| 14706 | 2 | 3 | | | III-1 | Nts | 4922 | 4-May-15 | 16121 | 2 | 3 | | III-1 | Oxnad1 | 92106 | 4-May-15 |
| 14709 | 2 | 3 | | | III-1 | Nuak1 | 9891 | 4-May-15 | 16122 | 2 | 3 | | III-1 | Oxr1 | 55074 | 12-May-15 |
| 14710 | 2 | 3 | | | III-1 | Nuak2 | 81788 | 4-May-15 | 16129 | 2 | 3 | | III-1 | P2rx3 | 5024 | 4-May-15 |
| 14711 | 2 | 3 | | | III-1 | Nubl | 51667 | 4-May-15 | 16131 | 2 | 3 | | III-1 | P2rx5 | 5026 | 24-May-15 |
| 14715 | 2 | 3 | | | III-1 | Nucb1 | 4924 | 4-May-15 | 16134 | 2 | 3 | | III-1 | P2ry1 | 5028 | 12-May-15 |
| 14717 | 2 | 3 | | | III-1 | Nucks1 | 64710 | 4-May-15 | 16141 | 2 | 3 | | III-1 | P2ry6 | 5031 | 4-May-15 |
| 14725 | 2 | 3 | | | III-1 | Nudt12 | 83594 | 4-May-15 | 16144 | 2 | 3 | | III-1 | P4ha3 | 283208 | 4-May-15 |
| 14726 | 2 | 3 | | | III-1 | Nudt13 | 25961 | 4-May-15 | 16145 | 2 | 3 | | III-1 | P4hb | 5034 | 17-May-15 |
| 14728 | 2 | 3 | | | III-1 | Nudt15 | 55270 | 4-May-15 | 16147 | 2 | 3 | | III-1 | Pa2g4 | 5036 | 4-May-15 |
| 14730 | 2 | 3 | | | III-1 | Nudt16l1 | 84309 | 4-May-15 | 16150 | 2 | 3 | | III-1 | Pabpc2 | 26986 | 12-May-15 |
| 14733 | 2 | 3 | | | III-1 | Nudt19 | 390916 | 21-May-15 | 16158 | 2 | 3 | | III-1 | Pacrgl | 133015 | 4-May-15 |
| 14737 | 2 | 3 | | | III-1 | Nudt3 | 11165 | 4-May-15 | | | | | | | | |

Fig.22 - 76

| | | | | | | | | | | | | | | |
|---|---|---|---|---|---|---|---|---|---|---|---|---|---|---|
| 16159 | 2 | 3 | | | III-1 | Pacs1 | 55690 | 4-May-15 | 16478 | 2 | 3 | | III-1 | Pdlim1 | 9124 | 21-May-15 |
| 16162 | 2 | 3 | | | III-1 | Pacsin2 | 11252 | 4-May-15 | 16484 | 2 | 3 | | III-1 | Pdp1 | 54704 | 7-Jun-15 |
| 16166 | 2 | 3 | | | III-1 | Padi3 | 51702 | 4-May-15 | 16485 | 2 | 3 | | III-1 | Pdp2 | 57546 | 4-May-15 |
| 16168 | 2 | 3 | | | III-1 | Padi6 | 353238 | 4-May-15 | 16488 | 2 | 3 | | III-1 | Pdpk1 | 5170 | 4-May-15 |
| 16175 | 2 | 3 | | | III-1 | Pagr1a | | | 16491 | 2 | 3 | | III-1 | Pds5b | 23047 | 4-May-15 |
| 16187 | 2 | 3 | | | III-1 | Pak7 | 57144 | 17-May-15 | 16495 | 2 | 3 | | III-1 | Pdxdc1 | 23042 | 23-May-15 |
| 16190 | 2 | 3 | | | III-1 | Pald | 23022 | 31-May-15 | 16497 | 2 | 3 | | III-1 | Pdxk-ps | | |
| 16193 | 2 | 3 | | | III-1 | Palm3 | 342979 | 4-May-15 | 16499 | 2 | 3 | | III-1 | Pdyn | 5173 | 23-May-15 |
| 16198 | 2 | 3 | | | III-1 | Pan2 | 9924 | 7-Jun-15 | 16501 | 2 | 3 | | III-1 | Pdzd2 | 23037 | 12-May-15 |
| 16201 | 2 | 3 | | | III-1 | Pank2 | 80025 | 28-May-15 | 16502 | 2 | 3 | | III-1 | Pdzd3 | 79849 | 4-May-15 |
| 16203 | 2 | 3 | | | III-1 | Pank4 | 55229 | 4-May-15 | 16510 | 2 | 3 | | III-1 | Pdzrn4 | 29951 | 4-May-15 |
| 16205 | 2 | 3 | | | III-1 | Panx2 | 56666 | 4-May-15 | 16512 | 2 | 3 | | III-1 | Pea15b | | |
| 16208 | 2 | 3 | | | III-1 | Papd4 | 167153 | 4-May-15 | 16516 | 2 | 3 | | III-1 | Pebp4 | 157310 | 4-May-15 |
| 16209 | 2 | 3 | | | III-1 | Papd5 | 64282 | 4-May-15 | 16519 | 2 | 3 | | III-1 | Pcf1 | 553115 | 4-May-15 |
| 16212 | 2 | 3 | | | III-1 | Papln | 89932 | 4-May-15 | 16521 | 2 | 3 | | III-1 | Peg12 | | |
| 16215 | 2 | 3 | | | III-1 | Papolg | 64895 | 4-May-15 | 16527 | 2 | 3 | | III-1 | Peli3 | 246330 | 3-May-15 |
| 16218 | 2 | 3 | | | III-1 | Papss1 | 9061 | 4-May-15 | 16529 | 2 | 3 | | III-1 | Pelp1 | 27043 | 12-May-15 |
| 16224 | 2 | 3 | | | III-1 | Paqr7 | 164091 | 4-May-15 | 16537 | 2 | 3 | | III-1 | Peril | | |
| 16228 | 2 | 3 | | | III-1 | Pard3b | 117583 | 12-May-15 | 16540 | 2 | 3 | | III-1 | Pes1 | 23481 | 7-Jun-15 |
| 16229 | 2 | 3 | | | III-1 | Pard6a | 50855 | 4-May-15 | 16541 | 2 | 3 | | III-1 | Pet100 | 100131801 | 4-May-15 |
| 16232 | 2 | 3 | | | III-1 | Parg | 8505 | 17-May-15 | 16542 | 2 | 3 | | III-1 | Pet112 | 5188 | 23-May-15 |
| 16234 | 2 | 3 | | | III-1 | Park7 | 11315 | 31-May-15 | 16544 | 2 | 3 | | III-1 | Pet2 | | |
| 16238 | 2 | 3 | | | III-1 | Parp1 | 142 | 31-May-15 | 16548 | 2 | 3 | | III-1 | Pex11b | 8799 | 4-May-15 |
| 16245 | 2 | 3 | | | III-1 | Parp3 | 10039 | 4-May-15 | 16550 | 2 | 3 | | III-1 | Pex12 | 5193 | 23-May-15 |
| 16249 | 2 | 3 | | | III-1 | Parp9 | 83666 | 4-May-15 | 16554 | 2 | 3 | | III-1 | Pex19 | 5824 | 4-May-15 |
| 16253 | 2 | 3 | | | III-1 | Parvb | 29780 | 4-May-15 | 16558 | 2 | 3 | | III-1 | Pex5 | 5830 | 23-May-15 |
| 16257 | 2 | 3 | | | III-1 | Pate4 | 399968 | 12-May-15 | 16564 | 2 | 3 | | III-1 | Pfdn1 | 5201 | 4-May-15 |
| 16261 | 2 | 3 | | | III-1 | Paupar | 103057000 | 4-May-15 | 16566 | 2 | 3 | | III-1 | Pfdn4 | 5203 | 4-May-15 |
| 16263 | 2 | 3 | | | III-1 | Pax1 | 5075 | 4-May-15 | 16567 | 2 | 3 | | III-1 | Pfdn5 | 5204 | 4-May-15 |
| 16265 | 2 | 3 | | | III-1 | Pax3 | 5077 | 23-May-15 | 16569 | 2 | 3 | | III-1 | Pfkfb2 | 5208 | 4-May-15 |
| 16273 | 2 | 3 | | | III-1 | Paxbp1 | 94104 | 12-May-15 | 16572 | 2 | 3 | | III-1 | Pfkl | 5211 | 4-May-15 |
| 16278 | 2 | 3 | | | III-1 | Pbld2 | | | 16577 | 2 | 3 | | III-1 | Pfn3 | 345456 | 4-May-15 |
| 16279 | 2 | 3 | | | III-1 | Pbp2 | | | 16587 | 2 | 3 | | III-1 | Pghd1 | 84547 | 4-May-15 |
| 16283 | 2 | 3 | | | III-1 | Pbx1 | 5089 | 7-Jun-15 | 16592 | 2 | 3 | | III-1 | Pggt1b | 5229 | 4-May-15 |
| 16285 | 2 | 3 | | | III-1 | Pbx4 | 80714 | 4-May-15 | 16599 | 2 | 3 | | III-1 | Pglyrp4 | 57115 | 4-May-15 |
| 16286 | 2 | 3 | | | III-1 | Pbxip1 | 57326 | 4-May-15 | 16600 | 2 | 3 | | III-1 | Pgm1 | 5236 | 23-May-15 |
| 16289 | 2 | 3 | | | III-1 | Pcbp1 | 5093 | 4-May-15 | 16601 | 2 | 3 | | III-1 | Pgm2 | 55276 | 4-May-15 |
| 16292 | 2 | 3 | | | III-1 | Pcbp4 | 57060 | 4-May-15 | 16603 | 2 | 3 | | III-1 | Pgm3 | 5238 | 4-May-15 |
| 16293 | 2 | 3 | | | III-1 | Pcca | 5095 | 23-May-15 | 16606 | 2 | 3 | | III-1 | Pgpep1 | 54858 | 12-May-15 |
| 16305 | 2 | 3 | | | III-1 | Pcdh8 | 5100 | 18-May-15 | 16607 | 2 | 3 | | III-1 | Pgpep1l | 145814 | 4-May-15 |
| 16307 | 2 | 3 | | | III-1 | Pcdha1 | 56147 | 4-May-15 | 16609 | 2 | 3 | | III-1 | Pgr15l | | |
| 16323 | 2 | 3 | | | III-1 | Pcdhb10 | 56126 | 12-May-15 | 16611 | 2 | 3 | | III-1 | Pgrmc2 | 10424 | 4-May-15 |
| 16328 | 2 | 3 | | | III-1 | Pcdhb15 | 56121 | 4-May-15 | 16613 | 2 | 3 | | III-1 | Phactr1 | 221692 | 4-May-15 |
| 16331 | 2 | 3 | | | III-1 | Pcdhb18 | 54660 | 4-May-15 | 16614 | 2 | 3 | | III-1 | Phactr2 | 9749 | 4-May-15 |
| 16346 | 2 | 3 | | | III-1 | Pcdhga11 | 56105 | 4-May-15 | 16616 | 2 | 3 | | III-1 | Phactr4 | 65979 | 4-May-15 |
| 16349 | 2 | 3 | | | III-1 | Pcdhga3 | 56112 | 12-May-15 | 16621 | 2 | 3 | | III-1 | Phc2 | 1912 | 14-May-15 |
| 16350 | 2 | 3 | | | III-1 | Pcdhga4 | 56111 | 4-May-15 | 16623 | 2 | 3 | | III-1 | Phex | 5251 | 23-May-15 |
| 16353 | 2 | 3 | | | III-1 | Pcdhga7 | 56108 | 4-May-15 | 16625 | 2 | 3 | | III-1 | Phf10 | 55274 | 4-May-15 |
| 16354 | 2 | 3 | | | III-1 | Pcdhga8 | 9708 | 4-May-15 | 16626 | 2 | 3 | | III-1 | Phf11a | | |
| 16357 | 2 | 3 | | | III-1 | Pcdhgb2 | 56103 | 4-May-15 | 16627 | 2 | 3 | | III-1 | Phf11b | | |
| 16358 | 2 | 3 | | | III-1 | Pcdhgb4 | 8641 | 4-May-15 | 16629 | 2 | 3 | | III-1 | Phf11d | | |
| 16359 | 2 | 3 | | | III-1 | Pcdhgb5 | 56101 | 4-May-15 | 16639 | 2 | 3 | | III-1 | Phf23 | 79142 | 4-May-15 |
| 16361 | 2 | 3 | | | III-1 | Pcdhgh7 | 56099 | 4-May-15 | 16640 | 2 | 3 | | III-1 | Phf3 | 23469 | 12-May-15 |
| 16362 | 2 | 3 | | | III-1 | Pcdhgb8 | | | 16641 | 2 | 3 | | III-1 | Phf5a | 84844 | 4-May-15 |
| 16364 | 2 | 3 | | | III-1 | Pcdhgc4 | 56098 | 12-May-15 | 16644 | 2 | 3 | | III-1 | Phf8 | 23133 | 4-May-15 |
| 16365 | 2 | 3 | | | III-1 | Pcdhgc5 | 56097 | 4-May-15 | 16647 | 2 | 3 | | III-1 | Phip | 55023 | 4-May-15 |
| 16366 | 2 | 3 | | | III-1 | Pced1a | 64773 | 4-May-15 | 16657 | 2 | 3 | | III-1 | Phldb2 | 90102 | 4-May-15 |
| 16368 | 2 | 3 | | | III-1 | Pcf11 | 51585 | 4-May-15 | 16658 | 2 | 3 | | III-1 | Phldb3 | 653583 | 4-May-15 |
| 16371 | 2 | 3 | | | III-1 | Pcgf3 | 10336 | 2-Jun-15 | 16662 | 2 | 3 | | III-1 | Phospho2 | 493911 | 4-May-15 |
| 16372 | 2 | 3 | | | III-1 | Pcgf5 | 84333 | 2-Jun-15 | 16666 | 2 | 3 | | III-1 | Phrf1 | 57661 | 4-May-15 |
| 16374 | 2 | 3 | | | III-1 | Pcid2 | 55795 | 4-May-15 | 16670 | 2 | 3 | | III-1 | Phxr4 | | |
| 16378 | 2 | 3 | | | III-1 | Pclo | 27445 | 4-May-15 | 16672 | 2 | 3 | | III-1 | Phyhd1 | 254295 | 4-May-15 |
| 16379 | 2 | 3 | | | III-1 | Pcmj | 5108 | 7-Jun-15 | 16676 | 2 | 3 | | III-1 | Pi15 | 51050 | 4-May-15 |
| 16383 | 2 | 3 | | | III-1 | Pcmtd2 | 55251 | 4-May-15 | 16678 | 2 | 3 | | III-1 | Pi4k2a | 55361 | 28-May-15 |
| 16386 | 2 | 3 | | | III-1 | Pcnx | 22990 | 21-May-15 | 16680 | 2 | 3 | | III-1 | Pi4ka | 5297 | 4-May-15 |
| 16387 | 2 | 3 | | | III-1 | Pcnxl2 | 80003 | 4-May-15 | 16681 | 2 | 3 | | III-1 | Pi4kb | 5298 | 4-May-15 |
| 16390 | 2 | 3 | | | III-1 | Pcolce | 5118 | 4-May-15 | 16686 | 2 | 3 | | III-1 | Pias4 | 51588 | 4-May-15 |
| 16395 | 2 | 3 | | | III-1 | Pcsk1 | 5122 | 4-May-15 | 16692 | 2 | 3 | | III-1 | Piezo1 | 9780 | 10-May-15 |
| 16397 | 2 | 3 | | | III-1 | Pcsk2 | 5126 | 12-May-15 | 16693 | 2 | 3 | | III-1 | Piezo2 | 63895 | 21-May-15 |
| 16398 | 2 | 3 | | | III-1 | Pcsk2os1 | | | 16698 | 2 | 3 | | III-1 | Pigc | 5279 | 4-May-15 |
| 16403 | 2 | 3 | | | III-1 | Pcsk7 | 9159 | 4-May-15 | 16700 | 2 | 3 | | III-1 | Pigg | 54872 | 4-May-15 |
| 16407 | 2 | 3 | | | III-1 | Pcyox1 | 51449 | 4-May-15 | 16702 | 2 | 3 | | III-1 | Pigk | 10026 | 4-May-15 |
| 16409 | 2 | 3 | | | III-1 | Pcyt1a | 5130 | 4-May-15 | 16707 | 2 | 3 | | III-1 | Pigp | 51227 | 4-May-15 |
| 16411 | 2 | 3 | | | III-1 | Pcyt2 | 5833 | 21-May-15 | 16716 | 2 | 3 | | III-1 | Pigyl | | |
| 16412 | 2 | 3 | | | III-1 | Pdap1 | 11333 | 4-May-15 | 16719 | 2 | 3 | | III-1 | Pih1d2 | 120379 | 4-May-15 |
| 16417 | 2 | 3 | | | III-1 | Pdcd1lg2 | 80380 | 4-May-15 | 16720 | 2 | 3 | | III-1 | Pih1d3 | 139212 | 4-May-15 |
| 16419 | 2 | 3 | | | III-1 | Pdcd2l | 84306 | 4-May-15 | 16723 | 2 | 3 | | III-1 | Pik3c2b | 5287 | 4-May-15 |
| 16422 | 2 | 3 | | | III-1 | Pdcd6 | 10016 | 4-May-15 | 16726 | 2 | 3 | | III-1 | Pik3ca | 5290 | 31-May-15 |
| 16423 | 2 | 3 | | | III-1 | Pdcd6ip | 10015 | 3-May-15 | 16730 | 2 | 3 | | III-1 | Pik3cg1 | 113791 | 4-May-15 |
| 16428 | 2 | 3 | | | III-1 | Pddc1 | 347862 | 12-May-15 | 16732 | 2 | 3 | | III-1 | Pik3r2 | 5296 | 28-May-15 |
| 16433 | 2 | 3 | | | III-1 | Pde1b | 5153 | 21-May-15 | 16734 | 2 | 3 | | III-1 | Pik3r4 | 30849 | 3-May-15 |
| 16438 | 2 | 3 | | | III-1 | Pde4a | 5141 | 12-May-15 | 16741 | 2 | 3 | | III-1 | Pim1 | 5292 | 7-Jun-15 |
| 16440 | 2 | 3 | | | III-1 | Pde4c | 5143 | 12-May-15 | 16743 | 2 | 3 | | III-1 | Pim3 | 415116 | 4-May-15 |
| 16449 | 2 | 3 | | | III-1 | Pde6h | 5149 | 23-May-15 | 16744 | 2 | 3 | | III-1 | Pin1 | 5300 | 7-Jun-15 |
| 16451 | 2 | 3 | | | III-1 | Pde7b | 27115 | 4-May-15 | 16749 | 2 | 3 | | III-1 | Pin1yp | 390940 | 4-May-15 |
| 16454 | 2 | 3 | | | III-1 | Pde9a | 5152 | 4-May-15 | 16750 | 2 | 3 | | III-1 | Pinx1 | 54984 | 31-May-15 |
| 16455 | 2 | 3 | | | III-1 | Pdf | 64146 | 4-May-15 | 16754 | 2 | 3 | | III-1 | Pip4k2c | 79837 | 4-May-15 |
| 16457 | 2 | 3 | | | III-1 | Pdgfb | 5155 | 31-May-15 | 16755 | 2 | 3 | | III-1 | Pip5k1a | 8394 | 4-May-15 |
| 16459 | 2 | 3 | | | III-1 | Pdgfd | 80310 | 4-May-15 | 16757 | 2 | 3 | | III-1 | Pip5k1c | 23396 | 4-May-15 |
| 16461 | 2 | 3 | | | III-1 | Pdgfrb | 5159 | 23-May-15 | 16771 | 2 | 3 | | III-1 | Pisd-ps2 | | |
| 16462 | 2 | 3 | | | III-1 | Pdgfrl | 5157 | 4-May-15 | 16778 | 2 | 3 | | III-1 | Pitpnm2 | 57605 | 12-May-15 |
| 16464 | 2 | 3 | | | III-1 | Pdha2 | 5161 | 4-May-15 | 16782 | 2 | 3 | | III-1 | Pitx1 | 5307 | 28-May-15 |
| 16466 | 2 | 3 | | | III-1 | Pdhx | 8050 | 29-May-15 | 16785 | 2 | 3 | | III-1 | Piwil1 | 9271 | 4-May-15 |
| 16471 | 2 | 3 | | | III-1 | Pdia6 | 10130 | 4-May-15 | 16789 | 2 | 3 | | III-1 | Pja2 | 9867 | 4-May-15 |
| 16472 | 2 | 3 | | | III-1 | Pdik1l | 149420 | 4-May-15 | 16791 | 2 | 3 | | III-1 | Pkd1l2 | 114780 | 12-May-15 |
| 16473 | 2 | 3 | | | III-1 | Pdilt | 204474 | 4-May-15 | 16794 | 2 | 3 | | III-1 | Pkd2l1 | 9033 | 12-May-15 |
| 16476 | 2 | 3 | | | III-1 | Pdk3 | 5165 | 4-May-15 | 16796 | 2 | 3 | | III-1 | Pkdcc | 91461 | 4-May-15 |

Fig.22 - 77

| | | | | | | | | | | | | | | | |
|---|---|---|---|---|---|---|---|---|---|---|---|---|---|---|---|
| 16797 | 2 | 3 | | | III-1 | Pkdrej | 10343 | 4-May-15 | 17083 | 2 | 3 | | III-1 | Pop1 | 10940 | 7-Jun-15 |
| 16802 | 2 | 3 | | | III-1 | Pkig | 11142 | 4-May-15 | 17085 | 2 | 3 | | III-1 | Pop5 | 51367 | 4-May-15 |
| 16806 | 2 | 3 | | | III-1 | Pkn1 | 5585 | 4-May-15 | 17086 | 2 | 3 | | III-1 | Pop7 | 10248 | 4-May-15 |
| 16807 | 2 | 3 | | | III-1 | Pkn2 | 5586 | 4-May-15 | 17098 | 2 | 3 | | III-1 | Pou2f2 | 5452 | 4-May-15 |
| 16812 | 2 | 3 | | | III-1 | Pkp2 | 5318 | 23-May-15 | 17101 | 2 | 3 | | III-1 | Pou3f2 | 5454 | 4-May-15 |
| 16814 | 2 | 3 | | | III-1 | Pkp4 | 8502 | 4-May-15 | 17104 | 2 | 3 | | III-1 | Pou3f4 | 5456 | 23-May-15 |
| 16819 | 2 | 3 | | | III-1 | Pla2g12b | 84647 | 4-May-15 | 17114 | 2 | 3 | | III-1 | Ppa2 | 27068 | 12-May-15 |
| 16829 | 2 | 3 | | | III-1 | Pla2g4a | 5321 | 12-May-15 | 17115 | 2 | 3 | | III-1 | Ppan | 56342 | 4-May-15 |
| 16830 | 2 | 3 | | | III-1 | Pla2g4b | 100137049 | 4-May-15 | 17117 | 2 | 3 | | III-1 | Ppap2h | 8613 | 21-May-15 |
| 16834 | 2 | 3 | | | III-1 | Pla2g4f | 255189 | 4-May-15 | 17119 | 2 | 3 | | III-1 | Ppapdc1a | 196051 | 4-May-15 |
| 16836 | 2 | 3 | | | III-1 | Pla2g6 | 8398 | 23-May-15 | 17120 | 2 | 3 | | III-1 | Ppapdc1b | 84513 | 4-May-15 |
| 16838 | 2 | 3 | | | III-1 | Pla2r1 | 22925 | 24-May-15 | 17121 | 2 | 3 | | III-1 | Ppapdc2 | 403313 | 23-May-15 |
| 16845 | 2 | 3 | | | III-1 | Plag1 | 5324 | 28-May-15 | 17126 | 2 | 3 | | III-1 | Ppargc1a | 10891 | 24-May-15 |
| 16847 | 2 | 3 | | | III-1 | Plagl2 | 5326 | 31-May-15 | 17128 | 2 | 3 | | III-1 | Ppat | 5471 | 7-Jun-15 |
| 16848 | 2 | 3 | | | III-1 | Plat | 5327 | 29-May-15 | 17133 | 2 | 3 | | III-1 | Ppef1 | 5475 | 4-May-15 |
| 16849 | 2 | 3 | | | III-1 | Plau | 5328 | 24-May-15 | 17138 | 2 | 3 | | III-1 | Ppfia4 | 8497 | 4-May-15 |
| 16850 | 2 | 3 | | | III-1 | Plaur | 5329 | 17-May-15 | 17140 | 2 | 3 | | III-1 | Ppfibp2 | 8495 | 4-May-15 |
| 16859 | 2 | 3 | | | III-1 | Plcd3 | 113026 | 4-May-15 | 17141 | 2 | 3 | | III-1 | Pphln1 | 51535 | 4-May-15 |
| 16860 | 2 | 3 | | | III-1 | Plcd4 | 84812 | 4-May-15 | 17144 | 2 | 3 | | III-1 | Ppic | 5480 | 4-May-15 |
| 16862 | 2 | 3 | | | III-1 | Plcg1 | 5335 | 31-May-15 | 17149 | 2 | 3 | | III-1 | Ppig | 9360 | 4-May-15 |
| 16863 | 2 | 3 | | | III-1 | Plcg2 | 5336 | 12-May-15 | 17157 | 2 | 3 | | III-1 | Ppip5k2 | 23262 | 4-May-15 |
| 16864 | 2 | 3 | | | III-1 | Plch1 | 23007 | 4-May-15 | 17167 | 2 | 3 | | III-1 | Ppm1k | 152926 | 4-May-15 |
| 16866 | 2 | 3 | | | III-1 | Plcl1 | 5334 | 4-May-15 | 17168 | 2 | 3 | | III-1 | Ppm1l | 151742 | 4-May-15 |
| 16869 | 2 | 3 | | | III-1 | Plcxd2 | 257068 | 4-May-15 | 17169 | 2 | 3 | | III-1 | Ppm1m | 132180 | 4-May-15 |
| 16873 | 2 | 3 | | | III-1 | Pld2 | 5338 | 31-May-15 | 17171 | 2 | 3 | | III-1 | Ppmel | 51400 | 4-May-15 |
| 16876 | 2 | 3 | | | III-1 | Pld5 | 200150 | 4-May-15 | 17181 | 2 | 3 | | III-1 | Ppp1r13b | 23368 | 17-May-15 |
| 16878 | 2 | 3 | | | III-1 | Pldi | | | 17183 | 2 | 3 | | III-1 | Ppp1r14a | 94274 | 4-May-15 |
| 16882 | 2 | 3 | | | III-1 | Plekha1 | 59338 | 17-May-15 | 17188 | 2 | 3 | | III-1 | Ppp1r15b | 84919 | 4-May-15 |
| 16883 | 2 | 3 | | | III-1 | Plekha2 | 59339 | 12-May-15 | 17192 | 2 | 3 | | III-1 | Ppp1r18 | 170954 | 4-May-15 |
| 16885 | 2 | 3 | | | III-1 | Plekha4 | 57664 | 4-May-15 | 17200 | 2 | 3 | | III-1 | Ppp1r2-ps3 | | |
| 16886 | 2 | 3 | | | III-1 | Plekha5 | 54477 | 12-May-15 | 17201 | 2 | 3 | | III-1 | Ppp1r2-ps7 | | |
| 16888 | 2 | 3 | | | III-1 | Plekha7 | 144100 | 4-May-15 | 17205 | 2 | 3 | | III-1 | Ppp1r36 | 145376 | 4-May-15 |
| 16891 | 2 | 3 | | | III-1 | Plekhb2 | 55041 | 12-May-15 | 17206 | 2 | 3 | | III-1 | Ppp1r37 | 284352 | 4-May-15 |
| 16894 | 2 | 3 | | | III-1 | Plekhf1 | 79156 | 21-May-15 | 17210 | 2 | 3 | | III-1 | Ppp1r3d | 5509 | 4-May-15 |
| 16895 | 2 | 3 | | | III-1 | Plekhf2 | 79666 | 4-May-15 | 17213 | 2 | 3 | | III-1 | Ppp1r3fos | | |
| 16898 | 2 | 3 | | | III-1 | Plekhg3 | 26030 | 21-May-15 | 17215 | 2 | 3 | | III-1 | Ppp1r42 | 286187 | 4-May-15 |
| 16903 | 2 | 3 | | | III-1 | Plekhh2 | 130271 | 4-May-15 | 17219 | 2 | 3 | | III-1 | Ppp1r9b | 84687 | 4-May-15 |
| 16905 | 2 | 3 | | | III-1 | Plekhj1 | 55111 | 4-May-15 | 17226 | 2 | 3 | | III-1 | Ppp2r2c | 5522 | 12-May-15 |
| 16906 | 2 | 3 | | | III-1 | Plekhm1 | 9842 | 12-May-15 | 17227 | 2 | 3 | | III-1 | Ppp2r2cos | | |
| 16910 | 2 | 3 | | | III-1 | Plekho1 | 51177 | 12-May-15 | 17230 | 2 | 3 | | III-1 | Ppp2r3c | 55012 | 20-May-15 |
| 16915 | 2 | 3 | | | III-1 | Plg | 5340 | 12-May-15 | 17231 | 2 | 3 | | III-1 | Ppp2r3d | | |
| 16922 | 2 | 3 | | | III-1 | Plk1 | 5347 | 24-May-15 | 17239 | 2 | 3 | | III-1 | Ppp3cb | 5532 | 4-May-15 |
| 16925 | 2 | 3 | | | III-1 | Plk4 | 10733 | 24-May-15 | 17246 | 2 | 3 | | III-1 | Ppp4r2 | 151987 | 4-May-15 |
| 16928 | 2 | 3 | | | III-1 | Pln | 5350 | 23-May-15 | 17250 | 2 | 3 | | III-1 | Ppp6c1 | 22870 | 4-May-15 |
| 16931 | 2 | 3 | | | III-1 | Plod3 | 8985 | 4-May-15 | 17252 | 2 | 3 | | III-1 | Ppp6r3 | 55291 | 4-May-15 |
| 16933 | 2 | 3 | | | III-1 | Plp2 | 5355 | 4-May-15 | 17254 | 2 | 3 | | III-1 | Ppt1 | 5538 | 23-May-15 |
| 16934 | 2 | 3 | | | III-1 | Prg1 | 5356 | 4-May-15 | 17259 | 2 | 3 | | III-1 | Pqbp1 | 10084 | 4-May-15 |
| 16935 | 2 | 3 | | | III-1 | Pls1 | 5357 | 4-May-15 | 17260 | 2 | 3 | | III-1 | Pqlc1 | 80148 | 4-May-15 |
| 16937 | 2 | 3 | | | III-1 | Plscr1 | 5359 | 28-May-15 | 17261 | 2 | 3 | | III-1 | Pqlc2 | 54896 | 4-May-15 |
| 16938 | 2 | 3 | | | III-1 | Plscr2 | 57047 | 4-May-15 | 17262 | 2 | 3 | | III-1 | Pqlc3 | 130814 | 4-May-15 |
| 16939 | 2 | 3 | | | III-1 | Plscr3 | 57048 | 4-May-15 | 17264 | 2 | 3 | | III-1 | Praf2 | 11230 | 12-May-15 |
| 16941 | 2 | 3 | | | III-1 | Plscr5 | 389158 | 12-May-15 | 17265 | 2 | 3 | | III-1 | Pram1 | 84106 | 24-May-15 |
| 16944 | 2 | 3 | | | III-1 | Plxdc1 | 57125 | 4-May-15 | 17266 | 2 | 3 | | III-1 | Prame | 23532 | 12-May-15 |
| 16948 | 2 | 3 | | | III-1 | Plxna3 | 55558 | 12-May-15 | 17283 | 2 | 3 | | III-1 | Prdm1 | 639 | 24-May-15 |
| 16950 | 2 | 3 | | | III-1 | Plxna4os1 | | | 17284 | 2 | 3 | | III-1 | Prdm10 | 56980 | 4-May-15 |
| 16953 | 2 | 3 | | | III-1 | Plxnb3 | 5365 | 4-May-15 | 17285 | 2 | 3 | | III-1 | Prdm11 | 56981 | 13-May-15 |
| 16958 | 2 | 3 | | | III-1 | Pmaip1 | 5366 | 4-May-15 | 17297 | 2 | 3 | | III-1 | Prdx1 | 5052 | 4-May-15 |
| 16959 | 2 | 3 | | | III-1 | Pmch | 5367 | 4-May-15 | 17299 | 2 | 3 | | III-1 | Prdx3 | 10935 | 4-May-15 |
| 16963 | 2 | 3 | | | III-1 | Pmfbp1 | 83449 | 4-May-15 | 17300 | 2 | 3 | | III-1 | Prdx4 | 10549 | 4-May-15 |
| 16967 | 2 | 3 | | | III-1 | Pmm2 | 5373 | 23-May-15 | 17301 | 2 | 3 | | III-1 | Prdx5 | 25824 | 4-May-15 |
| 16969 | 2 | 3 | | | III-1 | Pmp22 | 5376 | 7-Jun-15 | 17303 | 2 | 3 | | III-1 | Prdx6b | | |
| 16970 | 2 | 3 | | | III-1 | Pmpca | 23203 | 4-May-15 | 17304 | 2 | 3 | | III-1 | Preb | 10113 | 4-May-15 |
| 16984 | 2 | 3 | | | III-1 | Pnma2 | 10687 | 4-May-15 | 17309 | 2 | 3 | | III-1 | Prep1 | 9581 | 4-May-15 |
| 16986 | 2 | 3 | | | III-1 | Pnma5 | 114824 | 12-May-15 | 17310 | 2 | 3 | | III-1 | Prex1 | 57580 | 4-May-15 |
| 16990 | 2 | 3 | | | III-1 | Pnn | 5411 | 4-May-15 | 17312 | 2 | 3 | | III-1 | Prf1 | 5551 | 7-Jun-15 |
| 16992 | 2 | 3 | | | III-1 | Pnoc | 5368 | 12-May-15 | 17314 | 2 | 3 | | III-1 | Prg3 | 10394 | 4-May-15 |
| 16995 | 2 | 3 | | | III-1 | Pnpla1 | 285848 | 7-Jun-15 | 17317 | 2 | 3 | | III-1 | Prickle1 | 144165 | 23-May-15 |
| 16997 | 2 | 3 | | | III-1 | Pnpla3 | 80339 | 24-May-15 | 17321 | 2 | 3 | | III-1 | Prim1 | 5557 | 17-May-15 |
| 17001 | 2 | 3 | | | III-1 | Pnpla8 | 50640 | 31-May-15 | 17322 | 2 | 3 | | III-1 | Prim2 | 5558 | 17-May-15 |
| 17003 | 2 | 3 | | | III-1 | Pnpt1 | 87178 | 4-May-15 | 17323 | 2 | 3 | | III-1 | Prima1 | 145270 | 4-May-15 |
| 17004 | 2 | 3 | | | III-1 | Pnrc1 | 10957 | 12-May-15 | 17325 | 2 | 3 | | III-1 | Prkaa1 | 5562 | 31-May-15 |
| 17005 | 2 | 3 | | | III-1 | Pnrc2 | 55629 | 12-May-15 | 17328 | 2 | 3 | | III-1 | Prkab2 | 5565 | 12-May-15 |
| 17007 | 2 | 3 | | | III-1 | Poc1b | 282809 | 12-May-15 | 17333 | 2 | 3 | | III-1 | Prkag2os1 | | |
| 17011 | 2 | 3 | | | III-1 | Podx1 | 5420 | 12-May-15 | 17337 | 2 | 3 | | III-1 | Prkar2a | 5576 | 4-May-15 |
| 17012 | 2 | 3 | | | III-1 | Podxl2 | 50512 | 4-May-15 | 17340 | 2 | 3 | | III-1 | Prkch | 5579 | 24-May-15 |
| 17013 | 2 | 3 | | | III-1 | Pof1b | 79983 | 12-May-15 | 17342 | 2 | 3 | | III-1 | Prkcdbp | 112464 | 4-May-15 |
| 17017 | 2 | 3 | | | III-1 | Poglut1 | 56983 | 4-May-15 | 17343 | 2 | 3 | | III-1 | Prkce | 5581 | 10-May-15 |
| 17022 | 2 | 3 | | | III-1 | Pold1 | 5424 | 21-May-15 | 17345 | 2 | 3 | | III-1 | Prkch | 5583 | 4-May-15 |
| 17024 | 2 | 3 | | | III-1 | Pold3 | 10714 | 12-May-15 | 17346 | 2 | 3 | | III-1 | Prkci | 5584 | 17-May-15 |
| 17031 | 2 | 3 | | | III-1 | Pole4 | 56655 | 4-May-15 | 17348 | 2 | 3 | | III-1 | Prkcsh | 5589 | 12-May-15 |
| 17034 | 2 | 3 | | | III-1 | Polh | 5429 | 7-Jun-15 | 17350 | 2 | 3 | | III-1 | Prkd1 | 5587 | 4-May-15 |
| 17037 | 2 | 3 | | | III-1 | Poli | 27343 | 21-May-15 | 17393 | 2 | 3 | | III-1 | Prmt1 | 3276 | 12-May-15 |
| 17044 | 2 | 3 | | | III-1 | Polr1d | 51082 | 24-May-15 | 17396 | 2 | 3 | | III-1 | Prmt3 | 10196 | 4-May-15 |
| 17046 | 2 | 3 | | | III-1 | Polr2a | 5430 | 17-May-15 | 17401 | 2 | 3 | | III-1 | Prn | 64428 | 12-May-15 |
| 17052 | 2 | 3 | | | III-1 | Polr2g | 5436 | 4-May-15 | 17409 | 2 | 3 | | III-1 | Prodh2 | 58510 | 7-Jun-15 |
| 17053 | 2 | 3 | | | III-1 | Polr2h | 5437 | 7-Jun-15 | 17417 | 2 | 3 | | III-1 | Prop1 | 5626 | 23-May-15 |
| 17054 | 2 | 3 | | | III-1 | Polr2i | 5438 | 28-May-15 | 17419 | 2 | 3 | | III-1 | Pros1 | 5627 | 12-May-15 |
| 17055 | 2 | 3 | | | III-1 | Polr2j | 5439 | 4-May-15 | 17420 | 2 | 3 | | III-1 | Prosc | 11212 | 4-May-15 |
| 17062 | 2 | 3 | | | III-1 | Polr3d | 661 | 21-May-15 | 17423 | 2 | 3 | | III-1 | Prox1 | 5629 | 4-May-15 |
| 17063 | 2 | 3 | | | III-1 | Polr3e | 55718 | 4-May-15 | 17425 | 2 | 3 | | III-1 | Proz | 8858 | 4-May-15 |
| 17064 | 2 | 3 | | | III-1 | Polr3f | 10621 | 4-May-15 | 17427 | 2 | 3 | | III-1 | Prpf18 | 8559 | 12-May-15 |
| 17066 | 2 | 3 | | | III-1 | Polr3gl | 84265 | 4-May-15 | 17432 | 2 | 3 | | III-1 | Prpf38b | 55119 | 4-May-15 |
| 17070 | 2 | 3 | | | III-1 | Pom121 | 9883 | 7-Jun-15 | 17436 | 2 | 3 | | III-1 | Prpf40b | 25766 | 4-May-15 |
| 17071 | 2 | 3 | | | III-1 | Pom121l12 | 285877 | 12-May-15 | 17437 | 2 | 3 | | III-1 | Prpf4b | 8899 | 4-May-15 |
| 17076 | 2 | 3 | | | III-1 | Pomk | 84197 | 12-May-15 | 17438 | 2 | 3 | | III-1 | Prpf6 | 24148 | 23-May-15 |
| 17078 | 2 | 3 | | | III-1 | Pomt1 | 10585 | 23-May-15 | 17441 | 2 | 3 | | III-1 | Prph2 | 5961 | 23-May-15 |
| 17081 | 2 | 3 | | | III-1 | Pon2 | 5445 | 31-May-15 | 17444 | 2 | 3 | | III-1 | Prps1l1 | 221823 | 4-May-15 |

Fig.22 - 78

| | | | | | | | |
|---|---|---|---|---|---|---|---|
| 17452 | 2 | 3 | III-1 | Prr14 | 78994 | 4-May-15 |
| 17457 | 2 | 3 | III-1 | Prr18 | 285800 | 4-May-15 |
| 17463 | 2 | 3 | III-1 | Prr3 | 80742 | 7-Jun-15 |
| 17468 | 2 | 3 | III-1 | Prr5l | 79899 | 4-May-15 |
| 17471 | 2 | 3 | III-1 | Prrc1 | 133619 | 4-May-15 |
| 17476 | 2 | 3 | III-1 | Prrg2 | 5639 | 4-May-15 |
| 17477 | 2 | 3 | III-1 | Prrg3 | 79057 | 14-May-15 |
| 17478 | 2 | 3 | III-1 | Prrg4 | 79056 | 4-May-15 |
| 17480 | 2 | 3 | III-1 | Prrt2 | 112476 | 31-May-15 |
| 17481 | 2 | 3 | III-1 | Prrt3 | 285368 | 12-May-15 |
| 17483 | 2 | 3 | III-1 | Prrx1 | 5396 | 23-May-15 |
| 17488 | 2 | 3 | III-1 | Prss16 | 10279 | 4-May-15 |
| 17492 | 2 | 3 | III-1 | Prss23 | 11098 | 12-May-15 |
| 17503 | 2 | 3 | III-1 | Prss37 | 136242 | 4-May-15 |
| 17513 | 2 | 3 | III-1 | Prss48 | 345062 | 4-May-15 |
| 17515 | 2 | 3 | III-1 | Prss51 | 346702 | 17-Mar-15 |
| 17524 | 2 | 3 | III-1 | Prtg | 283659 | 4-May-15 |
| 17527 | 2 | 3 | III-1 | Prune2 | 158471 | 12-May-15 |
| 17529 | 2 | 3 | III-1 | Psap | 5660 | 7-Jun-15 |
| 17536 | 2 | 3 | III-1 | Psd4 | 23550 | 4-May-15 |
| 17539 | 2 | 3 | III-1 | Psenen | 55851 | 31-May-15 |
| 17541 | 2 | 3 | III-1 | Psg17 | | |
| 17549 | 2 | 3 | III-1 | Psg26 | | |
| 17553 | 2 | 3 | III-1 | Psg-ps1 | | |
| 17557 | 2 | 3 | III-1 | Psma2 | 5683 | 4-May-15 |
| 17559 | 2 | 3 | III-1 | Psma4 | 5685 | 4-May-15 |
| 17560 | 2 | 3 | III-1 | Psma5 | 5686 | 12-May-15 |
| 17561 | 2 | 3 | III-1 | Psma6 | 5687 | 4-May-15 |
| 17562 | 2 | 3 | III-1 | Psma7 | 5688 | 4-May-15 |
| 17566 | 2 | 3 | III-1 | Psmb11 | 122706 | 4-May-15 |
| 17568 | 2 | 3 | III-1 | Psmb3 | 5691 | 4-May-15 |
| 17569 | 2 | 3 | III-1 | Psmb4 | 5692 | 3-May-15 |
| 17570 | 2 | 3 | III-1 | Psmb5 | 5693 | 4-May-15 |
| 17571 | 2 | 3 | III-1 | Psmb6 | 5694 | 4-May-15 |
| 17572 | 2 | 3 | III-1 | Psmb7 | 5695 | 21-May-15 |
| 17573 | 2 | 3 | III-1 | Psmb8 | 5696 | 12-May-15 |
| 17577 | 2 | 3 | III-1 | Psmc3 | 5702 | 4-May-15 |
| 17579 | 2 | 3 | III-1 | Psmc4 | 5704 | 4-May-15 |
| 17582 | 2 | 3 | III-1 | Psmd1 | 5707 | 4-May-15 |
| 17585 | 2 | 3 | III-1 | Psmd12 | 5718 | 2-Jun-15 |
| 17587 | 2 | 3 | III-1 | Psmd14 | 10213 | 4-May-15 |
| 17588 | 2 | 3 | III-1 | Psmd2 | 5708 | 4-May-15 |
| 17597 | 2 | 3 | III-1 | Psme2 | 5721 | 4-May-15 |
| 17598 | 2 | 3 | III-1 | Psme2b | | |
| 17604 | 2 | 3 | III-1 | Psmg3 | 84262 | 4-May-15 |
| 17606 | 2 | 3 | III-1 | Psors1c2 | 170680 | 12-May-15 |
| 17608 | 2 | 3 | III-1 | Psph | 9723 | 4-May-15 |
| 17609 | 2 | 3 | III-1 | Pspn | 5623 | 12-May-15 |
| 17610 | 2 | 3 | III-1 | Psrc1 | 84722 | 4-May-15 |
| 17613 | 2 | 3 | III-1 | Pstpip2 | 9050 | 4-May-15 |
| 17614 | 2 | 3 | III-1 | Ptafr | 5724 | 4-May-15 |
| 17615 | 2 | 3 | III-1 | Ptar1 | 375743 | 4-May-15 |
| 17618 | 2 | 3 | III-1 | Ptbp3 | 9991 | 1-Jun-15 |
| 17621 | 2 | 3 | III-1 | Ptcd3 | 55037 | 4-May-15 |
| 17626 | 2 | 3 | III-1 | Ptchd3 | 374308 | 12-May-15 |
| 17631 | 2 | 3 | III-1 | Pten | 5728 | 2-Jun-15 |
| 17633 | 2 | 3 | III-1 | Ptf1a | 256297 | 28-May-15 |
| 17642 | 2 | 3 | III-1 | Ptges2 | 80142 | 4-May-15 |
| 17645 | 2 | 3 | III-1 | Ptgfr | 5737 | 4-May-15 |
| 17646 | 2 | 3 | III-1 | Ptgfrn | 5738 | 4-May-15 |
| 17653 | 2 | 3 | III-1 | Ptgs2os | | |
| 17659 | 2 | 3 | III-1 | Ptk2 | 5747 | 31-May-15 |
| 17662 | 2 | 3 | III-1 | Ptk7 | 5754 | 4-May-15 |
| 17663 | 2 | 3 | III-1 | Ptma | 5757 | 7-Jun-15 |
| 17668 | 2 | 3 | III-1 | Ptp4a2 | 8073 | 12-May-15 |
| 17670 | 2 | 3 | III-1 | Ptpdc1 | 198639 | 12-May-15 |
| 17673 | 2 | 3 | III-1 | Ptpla | 51495 | 4-May-15 |
| 17675 | 2 | 3 | III-1 | Ptpmt1 | 114971 | 4-May-15 |
| 17676 | 2 | 3 | III-1 | Ptpn1 | 5770 | 17-May-15 |
| 17680 | 2 | 3 | III-1 | Ptpn14 | 5784 | 4-May-15 |
| 17681 | 2 | 3 | III-1 | Ptpn18 | 26469 | 4-May-15 |
| 17682 | 2 | 3 | III-1 | Ptpn2 | 5771 | 24-May-15 |
| 17683 | 2 | 3 | III-1 | Ptpn20 | 26095 | 14-May-15 |
| 17686 | 2 | 3 | III-1 | Ptpn23 | 25930 | 4-May-15 |
| 17688 | 2 | 3 | III-1 | Ptpn4 | 5775 | 4-May-15 |
| 17690 | 2 | 3 | III-1 | Ptpn6 | 5777 | 24-May-15 |
| 17693 | 2 | 3 | III-1 | Ptpra | 5786 | 17-May-15 |
| 17695 | 2 | 3 | III-1 | Ptprc | 5788 | 4-May-15 |
| 17698 | 2 | 3 | III-1 | Ptpre | 5791 | 4-May-15 |
| 17700 | 2 | 3 | III-1 | Ptprg | 5793 | 12-May-15 |
| 17704 | 2 | 3 | III-1 | Ptprm | 5797 | 4-May-15 |
| 17705 | 2 | 3 | III-1 | Ptprn | 5798 | 4-May-15 |
| 17706 | 2 | 3 | III-1 | Ptprn2 | 5799 | 12-May-15 |
| 17710 | 2 | 3 | III-1 | Ptprs | 5802 | 12-May-15 |
| 17716 | 2 | 3 | III-1 | Ptrf | 284119 | 3-May-15 |
| 17721 | 2 | 3 | III-1 | Pttg1 | 9232 | 17-May-15 |
| 17722 | 2 | 3 | III-1 | Pttg1ip | 754 | 12-May-15 |
| 17724 | 2 | 3 | III-1 | Ptx4 | 390667 | 4-May-15 |
| 17729 | 2 | 3 | III-1 | Purb | 5814 | 4-May-15 |
| 17732 | 2 | 3 | III-1 | Pus10 | 150962 | 12-May-15 |
| 17736 | 2 | 3 | III-1 | Pus1l | 126789 | 23-May-15 |
| 17739 | 2 | 3 | III-1 | Pvrl1 | 5818 | 12-May-15 |
| 17741 | 2 | 3 | III-1 | Pvrl3 | 25945 | 4-May-15 |
| 17743 | 2 | 3 | III-1 | Pvt1 | 5820 | 17-May-15 |
| 17744 | 2 | 3 | III-1 | Pwp1 | 11137 | 4-May-15 |
| 17748 | 2 | 3 | III-1 | Pxdc1 | 221749 | 4-May-15 |
| 17753 | 2 | 3 | III-1 | Pxn | 5829 | 7-Jun-15 |
| 17756 | 2 | 3 | III-1 | Pycard | 29108 | 4-May-15 |
| 17757 | 2 | 3 | III-1 | Pycr1 | 5831 | 12-May-15 |
| 17766 | 2 | 3 | III-1 | Pygo2 | 90780 | 4-May-15 |
| 17769 | 2 | 3 | III-1 | Pyroxd2 | 84795 | 4-May-15 |
| 17770 | 2 | 3 | III-1 | Pyurf | 100996939 | 4-May-15 |
| 17775 | 2 | 3 | III-1 | Qk | 9444 | 28-May-15 |
| 17780 | 2 | 3 | III-1 | Qrfpr | 84109 | 4-May-15 |
| 17785 | 2 | 3 | III-1 | Qsox1 | 5768 | 4-May-15 |
| 17787 | 2 | 3 | III-1 | Qtrt1 | 81890 | 4-May-15 |
| 17788 | 2 | 3 | III-1 | Qtrtd1 | 79691 | 4-May-15 |
| 17799 | 2 | 3 | III-1 | Rab11a | 8766 | 29-May-15 |
| 17805 | 2 | 3 | III-1 | Rab11fip4os1 | | |
| 17808 | 2 | 3 | III-1 | Rab12 | 201475 | 21-May-15 |
| 17810 | 2 | 3 | III-1 | Rab14 | 51552 | 4-May-15 |
| 17813 | 2 | 3 | III-1 | Rab18 | 22931 | 24-May-15 |
| 17814 | 2 | 3 | III-1 | Rab19 | 401409 | 4-May-15 |
| 17815 | 2 | 3 | III-1 | Rab1b | 81876 | 21-May-15 |
| 17817 | 2 | 3 | III-1 | Rab21 | 23011 | 4-May-15 |
| 17825 | 2 | 3 | III-1 | Rab27b | 5874 | 4-May-15 |
| 17826 | 2 | 3 | III-1 | Rab28 | 9364 | 23-May-15 |
| 17828 | 2 | 3 | III-1 | Rab2b | 84932 | 4-May-15 |
| 17835 | 2 | 3 | III-1 | Rab35 | 11021 | 23-May-15 |
| 17841 | 2 | 3 | III-1 | Rab3a | 5864 | 12-May-15 |
| 17842 | 2 | 3 | III-1 | Rab3b | 5865 | 21-May-15 |
| 17844 | 2 | 3 | III-1 | Rab3d | 9545 | 4-May-15 |
| 17845 | 2 | 3 | III-1 | Rab3gap1 | 22930 | 4-May-15 |
| 17849 | 2 | 3 | III-1 | Rab40b | 10966 | 4-May-15 |
| 17850 | 2 | 3 | III-1 | Rab40c | 57799 | 4-May-15 |
| 17855 | 2 | 3 | III-1 | Rab4b | 53916 | 23-May-15 |
| 17862 | 2 | 3 | III-1 | Rab7l1 | 8934 | 4-May-15 |
| 17863 | 2 | 3 | III-1 | Rab8a | 4218 | 4-May-15 |
| 17866 | 2 | 3 | III-1 | Rab9b | 51209 | 4-May-15 |
| 17868 | 2 | 3 | III-1 | Rabep1 | 9135 | 4-May-15 |
| 17870 | 2 | 3 | III-1 | Rabepk | 10244 | 4-May-15 |
| 17873 | 2 | 3 | III-1 | Rabgef1 | 27342 | 31-May-15 |
| 17883 | 2 | 3 | III-1 | Racgap1 | 29127 | 3-May-15 |
| 17887 | 2 | 3 | III-1 | Rad21 | 5885 | 31-May-15 |
| 17893 | 2 | 3 | III-1 | Rad51ap1 | 10635 | 4-May-15 |
| 17896 | 2 | 3 | III-1 | Rad51c | 5889 | 23-May-15 |
| 17902 | 2 | 3 | III-1 | Rad9a | 5883 | 17-May-15 |
| 17904 | 2 | 3 | III-1 | Radil | 55698 | 4-May-15 |
| 17909 | 2 | 3 | III-1 | Raet1d | | |
| 17915 | 2 | 3 | III-1 | Rai14 | 26064 | 4-May-15 |
| 17922 | 2 | 3 | III-1 | Ralgapb | 57148 | 4-May-15 |
| 17924 | 2 | 3 | III-1 | Ralgps1 | 9649 | 4-May-15 |
| 17925 | 2 | 3 | III-1 | Ralgps2 | 55103 | 4-May-15 |
| 17926 | 2 | 3 | III-1 | Raly | 22913 | 12-May-15 |
| 17929 | 2 | 3 | III-1 | Ramp2 | 10266 | 4-May-15 |
| 17931 | 2 | 3 | III-1 | Ran | 5901 | 23-May-15 |
| 17934 | 2 | 3 | III-1 | Ranbp17 | 64901 | 12-May-15 |
| 17938 | 2 | 3 | III-1 | Ranbp3 | 8498 | 4-May-15 |
| 17942 | 2 | 3 | III-1 | Rap1a | 5906 | 10-May-15 |
| 17945 | 2 | 3 | III-1 | Rap1gap2 | 23108 | 4-May-15 |
| 17948 | 2 | 3 | III-1 | Rap1gds1 | 5910 | 4-May-15 |
| 17949 | 2 | 3 | III-1 | Rap2c | 57826 | 4-May-15 |
| 17952 | 2 | 3 | III-1 | Rapgef3 | 10411 | 31-May-15 |
| 17955 | 2 | 3 | III-1 | Rapgef6 | 51735 | 12-May-15 |
| 17959 | 2 | 3 | III-1 | Rara | 5914 | 17-May-15 |
| 17961 | 2 | 3 | III-1 | Rarg | 5916 | 4-May-15 |
| 17965 | 2 | 3 | III-1 | Rars2 | 57038 | 4-May-15 |
| 17969 | 2 | 3 | III-1 | Rasa4 | 10156 | 17-May-15 |
| 17971 | 2 | 3 | III-1 | Rasal2 | 9462 | 4-May-15 |
| 17972 | 2 | 3 | III-1 | Rasal3 | 64926 | 4-May-15 |
| 17976 | 2 | 3 | III-1 | Rasgef1a | 221002 | 4-May-15 |
| 17981 | 2 | 3 | III-1 | Rasgrp1 | 10125 | 12-May-15 |
| 17990 | 2 | 3 | III-1 | Rasl12 | 51285 | 12-May-15 |
| 17992 | 2 | 3 | III-1 | Rassf1 | 11186 | 17-May-15 |
| 17994 | 2 | 3 | III-1 | Rassf2 | 9770 | 28-May-15 |
| 17995 | 2 | 3 | III-1 | Rassf3 | 283349 | 7-Jun-15 |
| 17996 | 2 | 3 | III-1 | Rassf4 | 83937 | 13-Jun-15 |
| 17997 | 2 | 3 | III-1 | Rassf5 | 83593 | 13-Jun-15 |
| 18002 | 2 | 3 | III-1 | Raver1 | 125950 | 4-May-15 |
| 18005 | 2 | 3 | III-1 | Rax | 30062 | 7-Jun-15 |
| 18006 | 2 | 3 | III-1 | Rb1 | 5925 | 7-Jun-15 |
| 18013 | 2 | 3 | III-1 | Rbbp7 | 5931 | 4-May-15 |
| 18015 | 2 | 3 | III-1 | Rbbp8nl | 140893 | 4-May-15 |
| 18022 | 2 | 3 | III-1 | Rbks | 64080 | 4-May-15 |
| 18023 | 2 | 3 | III-1 | Rbl1 | 5933 | 4-May-15 |
| 18025 | 2 | 3 | III-1 | Rbm10 | 8241 | 12-May-15 |
| 18027 | 2 | 3 | III-1 | Rbm12 | 10137 | 4-May-15 |
| 18029 | 2 | 3 | III-1 | Rbm12b2 | | |
| 18033 | 2 | 3 | III-1 | Rbm15b | 29890 | 4-May-15 |
| 18034 | 2 | 3 | III-1 | Rbm17 | 84991 | 21-May-15 |
| 18038 | 2 | 3 | III-1 | Rbm22 | 55696 | 2-Jun-15 |
| 18042 | 2 | 3 | III-1 | Rbm27 | 54439 | 4-May-15 |
| 18044 | 2 | 3 | III-1 | Rbm3 | 5935 | 4-May-15 |
| 18045 | 2 | 3 | III-1 | Rbm31y | | |
| 18047 | 2 | 3 | III-1 | Rbm34 | 23029 | 4-May-15 |
| 18049 | 2 | 3 | III-1 | Rbm39 | 9584 | 4-May-15 |
| 18051 | 2 | 3 | III-1 | Rbm4 | 5936 | 17-May-15 |
| 18052 | 2 | 3 | III-1 | Rbm41 | 55285 | 4-May-15 |
| 18053 | 2 | 3 | III-1 | Rbm42 | 79171 | 4-May-15 |
| 18057 | 2 | 3 | III-1 | Rbm46 | 166863 | 4-May-15 |
| 18060 | 2 | 3 | III-1 | Rbm48 | 84060 | 4-May-15 |
| 18064 | 2 | 3 | III-1 | Rbm7 | 10179 | 4-May-15 |
| 18067 | 2 | 3 | III-1 | Rbms2 | 5939 | 4-May-15 |
| 18068 | 2 | 3 | III-1 | Rbms3 | 27303 | 4-May-15 |

Fig.22 - 79

| | | | | | | | | | | | | | | |
|---|---|---|---|---|---|---|---|---|---|---|---|---|---|---|
| 18069 | 2 | 3 | | III-1 | Rbmx | 27316 | 12-May-15 | 18416 | 2 | 3 | | III-1 | Rnf167 | 26001 | 4-May-15 |
| 18071 | 2 | 3 | | III-1 | Rbmxl1 | 494115 | 4-May-15 | 18427 | 2 | 3 | | III-1 | Rnf187 | 149603 | 12-May-15 |
| 18076 | 2 | 3 | | III-1 | Rbp3 | 5949 | 7-Jun-15 | 18431 | 2 | 3 | | III-1 | Rnf20 | 56254 | 2-Jun-15 |
| 18082 | 2 | 3 | | III-1 | Rbpms2 | 348093 | 4-May-15 | 18434 | 2 | 3 | | III-1 | Rnf214 | 257164 | 4-May-15 |
| 18083 | 2 | 3 | | III-1 | Rbx1 | 9978 | 2-Jun-15 | 18438 | 2 | 3 | | III-1 | Rnf219 | 79596 | 4-May-15 |
| 18088 | 2 | 3 | | III-1 | Rcan3 | 11123 | 12-May-15 | 18440 | 2 | 3 | | III-1 | Rnf222 | 643904 | 12-May-15 |
| 18090 | 2 | 3 | | III-1 | Rcbtb2 | 1102 | 4-May-15 | 18445 | 2 | 3 | | III-1 | Rnf25 | 79102 | 4-May-15 |
| 18095 | 2 | 3 | | III-1 | Rchy1 | 25898 | 2-Jun-15 | 18451 | 2 | 3 | | III-1 | Rnf4 | 6047 | 4-May-15 |
| 18098 | 2 | 3 | | III-1 | Rcn2 | 5955 | 7-Jun-15 | 18455 | 2 | 3 | | III-1 | Rnf44 | 22838 | 4-May-15 |
| 18101 | 2 | 3 | | III-1 | Rcor2 | 283248 | 4-May-15 | 18457 | 2 | 3 | | III-1 | Rnf6 | 6049 | 4-May-15 |
| 18104 | 2 | 3 | | III-1 | Rcvrn | 5957 | 12-May-15 | 18462 | 2 | 3 | | III-1 | Rngtt | 8732 | 12-May-15 |
| 18108 | 2 | 3 | | III-1 | Rdh10 | 157506 | 31-May-15 | 18465 | 2 | 3 | | III-1 | Rnmt | 8731 | 21-May-15 |
| 18111 | 2 | 3 | | III-1 | Rdh13 | 112724 | 4-May-15 | 18468 | 2 | 3 | | III-1 | Rnpep | 6051 | 4-May-15 |
| 18115 | 2 | 3 | | III-1 | Rdh19 | | | 18477 | 2 | 3 | | III-1 | Robo2 | 6092 | 12-May-15 |
| 18116 | 2 | 3 | | III-1 | Rdh5 | 5959 | 4-May-15 | 18480 | 2 | 3 | | III-1 | Rock1 | 6093 | 31-May-15 |
| 18117 | 2 | 3 | | III-1 | Rdh7 | | | 18484 | 2 | 3 | | III-1 | Romo1 | 140823 | 24-May-15 |
| 18120 | 2 | 3 | | III-1 | Rdm1 | 201299 | 4-May-15 | 18487 | 2 | 3 | | III-1 | Ror1 | 4919 | 7-Jun-15 |
| 18123 | 2 | 3 | | III-1 | Reck | 8434 | 31-May-15 | 18488 | 2 | 3 | | III-1 | Ror2 | 4920 | 7-Jun-15 |
| 18126 | 2 | 3 | | III-1 | Recql5 | 9400 | 21-May-15 | 18489 | 2 | 3 | | III-1 | Rora | 6095 | 12-May-15 |
| 18129 | 2 | 3 | | III-1 | Reep2 | 51308 | 4-May-15 | 18490 | 2 | 3 | | III-1 | Rorb | 6096 | 4-May-15 |
| 18130 | 2 | 3 | | III-1 | Reep3 | 221035 | 4-May-15 | 18493 | 2 | 3 | | III-1 | Rp1 | 6101 | 23-May-15 |
| 18132 | 2 | 3 | | III-1 | Reep5 | 7905 | 12-May-15 | 18497 | 2 | 3 | | III-1 | Rpa1 | 6117 | 7-Jun-15 |
| 18142 | 2 | 3 | | III-1 | Rela | 5970 | 29-May-15 | 18499 | 2 | 3 | | III-1 | Rpa3 | 6119 | 4-May-15 |
| 18144 | 2 | 3 | | III-1 | Rell1 | 768211 | 4-May-15 | 18508 | 2 | 3 | | III-1 | Rpgr | 6103 | 23-May-15 |
| 18145 | 2 | 3 | | III-1 | Rell2 | 285613 | 4-May-15 | 18512 | 2 | 3 | | III-1 | Rph3al | 9501 | 4-May-15 |
| 18147 | 2 | 3 | | III-1 | Relt | 84957 | 4-May-15 | 18513 | 2 | 3 | | III-1 | Rpia | 22934 | 4-May-15 |
| 18154 | 2 | 3 | | III-1 | Repin1 | 29803 | 17-May-15 | 18515 | 2 | 3 | | III-1 | Rpl10a | 4736 | 25-May-15 |
| 18156 | 2 | 3 | | III-1 | Reps2 | 9185 | 4-May-15 | 18516 | 2 | 3 | | III-1 | Rpl10l | 140801 | 4-May-15 |
| 18157 | 2 | 3 | | III-1 | Rer1 | 11079 | 20-May-15 | 18519 | 2 | 3 | | III-1 | Rpl13 | 6137 | 7-Jun-15 |
| 18160 | 2 | 3 | | III-1 | Rergl | 79785 | 4-May-15 | 18520 | 2 | 3 | | III-1 | Rpl13a | 23521 | 4-May-15 |
| 18162 | 2 | 3 | | III-1 | Rest | 5978 | 28-May-15 | 18521 | 2 | 3 | | III-1 | Rpl14 | 9045 | 12-May-15 |
| 18169 | 2 | 3 | | III-1 | Rev1 | 51455 | 23-May-15 | 18522 | 2 | 3 | | III-1 | Rpl14-ps1 | | |
| 18170 | 2 | 3 | | III-1 | Rev3l | 5980 | 12-May-15 | 18523 | 2 | 3 | | III-1 | Rpl15 | 6138 | 12-May-15 |
| 18171 | 2 | 3 | | III-1 | Rex2 | 25996 | 4-May-15 | 18525 | 2 | 3 | | III-1 | Rpl18 | 6141 | 21-May-15 |
| 18175 | 2 | 3 | | III-1 | Rfc1 | 5981 | 7-Jun-15 | 18527 | 2 | 3 | | III-1 | Rpl19 | 6143 | 21-May-15 |
| 18177 | 2 | 3 | | III-1 | Rfc3 | 5983 | 4-May-15 | 18528 | 2 | 3 | | III-1 | Rpl21 | 6144 | 7-Jun-15 |
| 18178 | 2 | 3 | | III-1 | Rfc4 | 5984 | 4-May-15 | 18529 | 2 | 3 | | III-1 | Rpl22 | 6146 | 4-May-15 |
| 18179 | 2 | 3 | | III-1 | Rfc5 | 5985 | 4-May-15 | 18531 | 2 | 3 | | III-1 | Rpl23 | 9349 | 7-Jun-15 |
| 18188 | 2 | 3 | | III-1 | Rftn1 | 23180 | 4-May-15 | 18532 | 2 | 3 | | III-1 | Rpl23a | 6147 | 12-May-15 |
| 18190 | 2 | 3 | | III-1 | Rfwd2 | 64326 | 4-May-15 | 18533 | 2 | 3 | | III-1 | Rpl24 | 6152 | 7-Jun-15 |
| 18194 | 2 | 3 | | III-1 | Rfx3 | 5991 | 28-May-15 | 18534 | 2 | 3 | | III-1 | Rpl26 | 6154 | 4-May-15 |
| 18204 | 2 | 3 | | III-1 | Rgcc | 28984 | 4-May-15 | 18536 | 2 | 3 | | III-1 | Rpl27a | 6157 | 4-May-15 |
| 18205 | 2 | 3 | | III-1 | Rgl1 | 23179 | 7-Jun-15 | 18543 | 2 | 3 | | III-1 | Rpl32 | 6161 | 4-May-15 |
| 18209 | 2 | 3 | | III-1 | Rgmb | 285704 | 4-May-15 | 18550 | 2 | 3 | | III-1 | Rpl36al | 6166 | 12-May-15 |
| 18216 | 2 | 3 | | III-1 | Rgs12 | 6002 | 21-May-15 | 18555 | 2 | 3 | | III-1 | Rpl39l | 116832 | 4-May-15 |
| 18222 | 2 | 3 | | III-1 | Rgs19 | 10287 | 4-May-15 | 18558 | 2 | 3 | | III-1 | Rpl41 | 6171 | 12-May-15 |
| 18224 | 2 | 3 | | III-1 | Rgs20 | 8601 | 4-May-15 | 18559 | 2 | 3 | | III-1 | Rpl5 | 6125 | 23-May-15 |
| 18225 | 2 | 3 | | III-1 | Rgs21 | 431704 | 4-May-15 | 18560 | 2 | 3 | | III-1 | Rpl6 | 6128 | 12-May-15 |
| 18227 | 2 | 3 | | III-1 | Rgs3 | 5998 | 12-May-15 | 18561 | 2 | 3 | | III-1 | Rpl7 | 6129 | 5-May-15 |
| 18228 | 2 | 3 | | III-1 | Rgs4 | 5999 | 4-May-15 | 18562 | 2 | 3 | | III-1 | Rpl7a | 6130 | 7-Jun-15 |
| 18232 | 2 | 3 | | III-1 | Rgs7bp | 401190 | 4-May-15 | 18563 | 2 | 3 | | III-1 | Rpl7l1 | 285855 | 12-May-15 |
| 18235 | 2 | 3 | | III-1 | Rgs9bp | 388531 | 4-May-15 | 18566 | 2 | 3 | | III-1 | Rplp0 | 6175 | 4-May-15 |
| 18239 | 2 | 3 | | III-1 | Rhbdd2 | 57414 | 4-May-15 | 18567 | 2 | 3 | | III-1 | Rplp1 | 6176 | 12-May-15 |
| 18240 | 2 | 3 | | III-1 | Rhbdd3 | 25807 | 4-May-15 | 18569 | 2 | 3 | | III-1 | Rplp2-ps1 | | |
| 18242 | 2 | 3 | | III-1 | Rhbdf2 | 79651 | 4-May-15 | 18570 | 2 | 3 | | III-1 | Rpn1 | 6184 | 7-Jun-15 |
| 18243 | 2 | 3 | | III-1 | Rhbdl1 | 9028 | 4-May-15 | 18575 | 2 | 3 | | III-1 | Rpp25l | 138716 | 4-May-15 |
| 18245 | 2 | 3 | | III-1 | Rhbdl3 | 162494 | 4-May-15 | 18577 | 2 | 3 | | III-1 | Rpp38 | 10557 | 4-May-15 |
| 18255 | 2 | 3 | | III-1 | Rhobtb1 | 9886 | 4-May-15 | 18581 | 2 | 3 | | III-1 | Rprd1b | 58490 | 3-Jun-15 |
| 18256 | 2 | 3 | | III-1 | Rhobtb2 | 23221 | 21-May-15 | 18591 | 2 | 3 | | III-1 | Rps13 | 6207 | 12-May-15 |
| 18258 | 2 | 3 | | III-1 | Rhoc | 389 | 3-May-15 | 18593 | 2 | 3 | | III-1 | Rps15 | 6209 | 12-May-15 |
| 18260 | 2 | 3 | | III-1 | Rhof | 54509 | 23-May-15 | 18595 | 2 | 3 | | III-1 | Rps15a-ps4 | | |
| 18261 | 2 | 3 | | III-1 | Rhog | 391 | 4-May-15 | 18596 | 2 | 3 | | III-1 | Rps15a-ps6 | | |
| 18264 | 2 | 3 | | III-1 | Rhoq | 23433 | 4-May-15 | 18597 | 2 | 3 | | III-1 | Rps16 | 6217 | 4-May-15 |
| 18265 | 2 | 3 | | III-1 | Rhot1 | 55288 | 23-May-15 | 18600 | 2 | 3 | | III-1 | Rps19 | 6223 | 21-May-15 |
| 18289 | 2 | 3 | | III-1 | Rhox4b | | | 18601 | 2 | 3 | | III-1 | Rps19bp1 | 91582 | 4-May-15 |
| 18290 | 2 | 3 | | III-1 | Rhox4c | | | 18602 | 2 | 3 | | III-1 | Rps19-ps3 | | |
| 18302 | 2 | 3 | | III-1 | Rian | 79104 | 12-May-15 | 18603 | 2 | 3 | | III-1 | Rps2 | 6187 | 4-May-15 |
| 18304 | 2 | 3 | | III-1 | Ribc2 | 26150 | 4-May-15 | 18605 | 2 | 3 | | III-1 | Rps21 | 6227 | 21-May-15 |
| 18309 | 2 | 3 | | III-1 | Rif1 | 55183 | 7-Jun-15 | 18607 | 2 | 3 | | III-1 | Rps24 | 6229 | 4-May-15 |
| 18313 | 2 | 3 | | III-1 | Rilpl2 | 196383 | 4-May-15 | 18611 | 2 | 3 | | III-1 | Rps27a | 6233 | 17-May-15 |
| 18314 | 2 | 3 | | III-1 | Rimbp2 | 23504 | 4-May-15 | 18612 | 2 | 3 | | III-1 | Rps27l | 51065 | 4-May-15 |
| 18317 | 2 | 3 | | III-1 | Rimklb | 57494 | 12-May-15 | 18613 | 2 | 3 | | III-1 | Rps27rt | | |
| 18318 | 2 | 3 | | III-1 | Rims1 | 22999 | 12-May-15 | 18618 | 2 | 3 | | III-1 | Rps4 | 128880 | 4-May-15 |
| 18320 | 2 | 3 | | III-1 | Rims3 | 9783 | 28-May-15 | 18619 | 2 | 3 | | III-1 | Rps4x | 6191 | 12-May-15 |
| 18324 | 2 | 3 | | III-1 | Rin3 | 79890 | 4-May-15 | 18620 | 2 | 3 | | III-1 | Rps5 | 6193 | 12-May-15 |
| 18335 | 2 | 3 | | III-1 | Ripply1 | 92129 | 4-May-15 | 18621 | 2 | 3 | | III-1 | Rps6 | 6194 | 4-May-15 |
| 18338 | 2 | 3 | | III-1 | Rit1 | 6016 | 7-Jun-15 | 18622 | 2 | 3 | | III-1 | Rps6ka1 | 6195 | 17-May-15 |
| 18341 | 2 | 3 | | III-1 | Rlbp1 | 6017 | 4-May-15 | 18624 | 2 | 3 | | III-1 | Rps6ka3 | 6197 | 23-May-15 |
| 18349 | 2 | 3 | | III-1 | Rmdn3 | 55177 | 12-May-15 | 18628 | 2 | 3 | | III-1 | Rps6kb1 | 6198 | 3-May-15 |
| 18367 | 2 | 3 | | III-1 | Rnase6 | 6039 | 4-May-15 | 18634 | 2 | 3 | | III-1 | Rps9 | 6203 | 4-May-15 |
| 18369 | 2 | 3 | | III-1 | Rnaseh1 | 246243 | 7-Jun-15 | 18635 | 2 | 3 | | III-1 | Rpsa | 3921 | 21-May-15 |
| 18371 | 2 | 3 | | III-1 | Rnaseh2b | 79621 | 23-May-15 | 18637 | 2 | 3 | | III-1 | Rptor | 57521 | 17-May-15 |
| 18372 | 2 | 3 | | III-1 | Rnaseh2c | 84153 | 23-May-15 | 18640 | 2 | 3 | | III-1 | Rpusd2 | 27079 | 4-May-15 |
| 18373 | 2 | 3 | | III-1 | Rnasek | 440400 | 21-May-15 | 18642 | 2 | 3 | | III-1 | Rpusd4 | 84881 | 4-May-15 |
| 18374 | 2 | 3 | | III-1 | Rnasel | 6041 | 4-May-15 | 18647 | 2 | 3 | | III-1 | Rragc | 64121 | 31-May-15 |
| 18375 | 2 | 3 | | III-1 | Rnaset2a | | | 18649 | 2 | 3 | | III-1 | Rras | 6237 | 12-May-15 |
| 18376 | 2 | 3 | | III-1 | Rnaset2b | | | 18650 | 2 | 3 | | III-1 | Rras2 | 22800 | 4-May-15 |
| 18380 | 2 | 3 | | III-1 | Rnf10 | 9921 | 4-May-15 | 18652 | 2 | 3 | | III-1 | Rreb1 | 6239 | 4-May-15 |
| 18385 | 2 | 3 | | III-1 | Rnf113a1 | | | 18660 | 2 | 3 | | III-1 | Rrp12 | 23223 | 4-May-15 |
| 18387 | 2 | 3 | | III-1 | Rnf114 | 55905 | 4-May-15 | 18661 | 2 | 3 | | III-1 | Rrp15 | 51018 | 4-May-15 |
| 18389 | 2 | 3 | | III-1 | Rnf121 | 55298 | 4-May-15 | 18667 | 2 | 3 | | III-1 | Rrs1 | 23212 | 4-May-15 |
| 18395 | 2 | 3 | | III-1 | Rnf13 | 11342 | 1-Jun-15 | 18672 | 2 | 3 | | III-1 | Rsbn1l | 222194 | 4-May-15 |
| 18405 | 2 | 3 | | III-1 | Rnf144b | 255488 | 4-May-15 | 18674 | 2 | 3 | | III-1 | Rsf1 | 51773 | 31-May-15 |
| 18407 | 2 | 3 | | III-1 | Rnf146 | 81847 | 4-Jun-15 | 18677 | 2 | 3 | | III-1 | Rsl1d1 | 26156 | 4-May-15 |
| 18410 | 2 | 3 | | III-1 | Rnf150 | 57484 | 4-May-15 | 18681 | 2 | 3 | | III-1 | Rsph3a | | |
| 18411 | 2 | 3 | | III-1 | Rnf151 | 146310 | 4-May-15 | 18686 | 2 | 3 | | III-1 | Rspo1 | 284654 | 4-May-15 |
| 18414 | 2 | 3 | | III-1 | Rnf165 | 494470 | 1-Jun-15 | 18687 | 2 | 3 | | III-1 | Rspo2 | 340419 | 4-May-15 |

Fig.22 - 80

| | | | | | | | | | | | | | | | |
|---|---|---|---|---|---|---|---|---|---|---|---|---|---|---|---|
| 18689 | 2 | 3 | | III-1 | Rspo4 | 343637 | 4-May-15 | 19075 | 2 | 3 | | III-1 | Sept11 | 55752 | 12-May-15 |
| 18690 | 2 | 3 | | III-1 | Rspry1 | 89970 | 20-May-15 | 19081 | 2 | 3 | | III-1 | Sept4 | 5414 | 12-May-15 |
| 18694 | 2 | 3 | | III-1 | Rsu1 | 6251 | 1-Jun-15 | 19083 | 2 | 3 | | III-1 | Sept6 | 23157 | 4-May-15 |
| 18696 | 2 | 3 | | III-1 | Rtca | 8634 | 12-May-15 | 19084 | 2 | 3 | | III-1 | Sept7 | 989 | 4-May-15 |
| 18698 | 2 | 3 | | III-1 | Rtdr1 | 27156 | 9-May-15 | 19086 | 2 | 3 | | III-1 | Sept9 | 10801 | 23-May-15 |
| 18709 | 2 | 3 | | III-1 | Rtn4ip1 | 84816 | 4-May-15 | 19089 | 2 | 3 | | III-1 | Serbp1 | 26135 | 4-May-15 |
| 18717 | 2 | 3 | | III-1 | Rttn | 25914 | 4-May-15 | 19094 | 2 | 3 | | III-1 | Serinc1 | 57515 | 28-May-15 |
| 18724 | 2 | 3 | | III-1 | Rundc3a | 10900 | 6-May-15 | 19096 | 2 | 3 | | III-1 | Serinc3 | 10955 | 12-May-15 |
| 18725 | 2 | 3 | | III-1 | Rundc3b | 154661 | 4-May-15 | 19097 | 2 | 3 | | III-1 | Serinc4 | 619189 | 14-May-15 |
| 18732 | 2 | 3 | | III-1 | Ruvbl1 | 8607 | 17-May-15 | 19099 | 2 | 3 | | III-1 | Serp1 | 27230 | 14-May-15 |
| 18733 | 2 | 3 | | III-1 | Ruvbl2 | 10856 | 17-May-15 | 19110 | 2 | 3 | | III-1 | Serpina3a | | |
| 18735 | 2 | 3 | | III-1 | Rwdd2a | 112811 | 4-May-15 | 19116 | 2 | 3 | | III-1 | Serpina3i | | |
| 18736 | 2 | 3 | | III-1 | Rwdd2b | 10069 | 4-May-15 | 19125 | 2 | 3 | | III-1 | Serpina9 | 327657 | 4-May-15 |
| 18738 | 2 | 3 | | III-1 | Rwdd4a | 201965 | 12-May-15 | 19126 | 2 | 3 | | III-1 | Serpinb10 | 5273 | 28-May-15 |
| 18744 | 2 | 3 | | III-1 | Rxrb | 6257 | 4-May-15 | 19129 | 2 | 3 | | III-1 | Serpinb13 | 5275 | 12-May-15 |
| 18746 | 2 | 3 | | III-1 | Rybp | 23429 | 2-Jun-15 | 19137 | 2 | 3 | | III-1 | Serpinb3d | | |
| 18753 | 2 | 3 | | III-1 | S100a11 | 6282 | 4-May-15 | 19141 | 2 | 3 | | III-1 | Serpinb6c | | |
| 18754 | 2 | 3 | | III-1 | S100a13 | 6284 | 12-May-15 | 19144 | 2 | 3 | | III-1 | Serpinb7 | 8710 | 4-May-15 |
| 18756 | 2 | 3 | | III-1 | S100a16 | 140576 | 7-Jun-15 | 19145 | 2 | 3 | | III-1 | Serpinb8 | 5271 | 4-May-15 |
| 18758 | 2 | 3 | | III-1 | S100a3 | 6274 | 4-May-15 | 19146 | 2 | 3 | | III-1 | Serpinb9 | 5272 | 4-May-15 |
| 18762 | 2 | 3 | | III-1 | S100a7a | 338324 | 4-May-15 | 19147 | 2 | 3 | | III-1 | Serpinb9b | | |
| 18768 | 2 | 3 | | III-1 | S100z | 170591 | 4-May-15 | 19158 | 2 | 3 | | III-1 | Serpinf1 | 5176 | 24-May-15 |
| 18769 | 2 | 3 | | III-1 | S1pr1 | 1901 | 12-May-15 | 19161 | 2 | 3 | | III-1 | Serpinh1 | 871 | 3-May-15 |
| 18770 | 2 | 3 | | III-1 | S1pr2 | 9294 | 21-May-15 | 19170 | 2 | 3 | | III-1 | Sesn2 | 83667 | 4-May-15 |
| 18787 | 2 | 3 | | III-1 | Sall2 | 6297 | 21-May-15 | 19175 | 2 | 3 | | III-1 | Setd1a | 9739 | 24-May-15 |
| 18795 | 2 | 3 | | III-1 | Samd15 | 161394 | 4-May-15 | 19176 | 2 | 3 | | III-1 | Setd1b | 23067 | 4-May-15 |
| 18798 | 2 | 3 | | III-1 | Samd4b | 56095 | 12-May-15 | 19177 | 2 | 3 | | III-1 | Setd2 | 29072 | 31-May-15 |
| 18800 | 2 | 3 | | III-1 | Samd7 | 344658 | 12-May-15 | 19178 | 2 | 3 | | III-1 | Setd3 | 84193 | 4-May-15 |
| 18802 | 2 | 3 | | III-1 | Samd9l | 219285 | 12-May-15 | 19180 | 2 | 3 | | III-1 | Setd5 | 55209 | 4-May-15 |
| 18805 | 2 | 3 | | III-1 | Samsn1 | 64092 | 4-May-15 | 19182 | 2 | 3 | | III-1 | Setd7 | 80854 | 12-May-15 |
| 18816 | 2 | 3 | | III-1 | Sapcd2 | 89958 | 4-May-15 | 19184 | 2 | 3 | | III-1 | Setdb1 | 9869 | 4-May-15 |
| 18819 | 2 | 3 | | III-1 | Sardh | 1757 | 12-May-15 | 19186 | 2 | 3 | | III-1 | Setmar | 6419 | 21-May-15 |
| 18822 | 2 | 3 | | III-1 | Sars | 6301 | 7-Jun-15 | 19187 | 2 | 3 | | III-1 | Setx | 23064 | 23-May-15 |
| 18829 | 2 | 3 | | III-1 | Sat1 | 6303 | 13-Jun-15 | 19191 | 2 | 3 | | III-1 | Sf1 | 7536 | 7-Jun-15 |
| 18830 | 2 | 3 | | III-1 | Sat2 | 112483 | 13-Jun-15 | 19195 | 2 | 3 | | III-1 | Sf3b1 | 23451 | 16-Jun-15 |
| 18835 | 2 | 3 | | III-1 | Saysd1 | 55776 | 12-May-15 | 19202 | 2 | 3 | | III-1 | Sfmbt1 | 51460 | 4-May-15 |
| 18842 | 2 | 3 | | III-1 | Sbno1 | 55206 | 4-May-15 | 19205 | 2 | 3 | | III-1 | Sfpq | 6421 | 7-Jun-15 |
| 18855 | 2 | 3 | | III-1 | Scamp2 | 10066 | 4-May-15 | 19206 | 2 | 3 | | III-1 | Sfr1 | 119392 | 4-May-15 |
| 18865 | 2 | 3 | | III-1 | Scarb2 | 950 | 17-May-15 | 19208 | 2 | 3 | | III-1 | Sfrp2 | 6423 | 4-May-15 |
| 18866 | 2 | 3 | | III-1 | Scarf1 | 8578 | 4-May-15 | 19213 | 2 | 3 | | III-1 | Sft2d2 | 375035 | 4-May-15 |
| 18868 | 2 | 3 | | III-1 | Scarletltr | | | 19216 | 2 | 3 | | III-1 | Sftpa1 | 653509 | 23-May-15 |
| 18884 | 2 | 3 | | III-1 | Scfd1 | 23256 | 21-May-15 | 19221 | 2 | 3 | | III-1 | Sfxn2 | 118980 | 4-May-15 |
| 18885 | 2 | 3 | | III-1 | Scfd2 | 152579 | 4-May-15 | 19222 | 2 | 3 | | III-1 | Sfxn3 | 81855 | 4-May-15 |
| 18918 | 2 | 3 | | III-1 | Scit1 | 132320 | 12-May-15 | 19227 | 2 | 3 | | III-1 | Sgcd | 6444 | 23-May-15 |
| 18919 | 2 | 3 | | III-1 | Scly | 51540 | 4-May-15 | 19234 | 2 | 3 | | III-1 | Sgk3 | 23678 | 4-May-15 |
| 18920 | 2 | 3 | | III-1 | Scmh1 | 22955 | 4-May-15 | 19235 | 2 | 3 | | III-1 | Sgms1 | 259230 | 12-May-15 |
| 18929 | 2 | 3 | | III-1 | Scn3a | 6328 | 12-May-15 | 19237 | 2 | 3 | | III-1 | Sgol1 | 151648 | 4-May-15 |
| 18934 | 2 | 3 | | III-1 | Scn7a | 6332 | 31-May-15 | 19242 | 2 | 3 | | III-1 | Sgsh | 6448 | 17-May-15 |
| 18935 | 2 | 3 | | III-1 | Scn8a | 6334 | 21-May-15 | 19244 | 2 | 3 | | III-1 | Sgsm2 | 9905 | 4-May-15 |
| 18941 | 2 | 3 | | III-1 | Sco1 | 6341 | 12-May-15 | 19246 | 2 | 3 | | III-1 | Sgta | 6449 | 12-May-15 |
| 18943 | 2 | 3 | | III-1 | Scoc | 60592 | 4-May-15 | 19251 | 2 | 3 | | III-1 | Sh2d1a | 4068 | 23-May-15 |
| 18947 | 2 | 3 | | III-1 | Scpep1os | | | 19253 | 2 | 3 | | III-1 | Sh2d1b2 | | |
| 18949 | 2 | 3 | | III-1 | Scrib | 23513 | 4-May-15 | 19255 | 2 | 3 | | III-1 | Sh2d3c | 10044 | 12-May-15 |
| 18950 | 2 | 3 | | III-1 | Scrn1 | 9805 | 4-May-15 | 19257 | 2 | 3 | | III-1 | Sh2d4b | 387694 | 4-May-15 |
| 18952 | 2 | 3 | | III-1 | Scrn3 | 79634 | 4-May-15 | 19262 | 2 | 3 | | III-1 | Sh3bgrl2 | 83699 | 4-May-15 |
| 18953 | 2 | 3 | | III-1 | Scrt1 | 83482 | 4-May-15 | 19263 | 2 | 3 | | III-1 | Sh3bgrl3 | 83442 | 4-May-15 |
| 18955 | 2 | 3 | | III-1 | Sct | 6343 | 7-Jun-15 | 19264 | 2 | 3 | | III-1 | Sh3bp1 | 23616 | 7-Jun-15 |
| 18958 | 2 | 3 | | III-1 | Scube2 | 57758 | 4-May-15 | 19265 | 2 | 3 | | III-1 | Sh3bp2 | 6452 | 23-May-15 |
| 18966 | 2 | 3 | | III-1 | Sdc2 | 6383 | 31-May-15 | 19270 | 2 | 3 | | III-1 | Sh3d21 | 79729 | 4-May-15 |
| 18967 | 2 | 3 | | III-1 | Sdc3 | 9672 | 4-May-15 | 19271 | 2 | 3 | | III-1 | Sh3gl1 | 6455 | 14-May-15 |
| 18969 | 2 | 3 | | III-1 | Sdcbp | 6386 | 10-May-15 | 19274 | 2 | 3 | | III-1 | Sh3glb1 | 51100 | 21-May-15 |
| 18971 | 2 | 3 | | III-1 | Sdccag3 | 10807 | 4-May-15 | 19276 | 2 | 3 | | III-1 | Sh3kbp1 | 30011 | 4-May-15 |
| 18978 | 2 | 3 | | III-1 | Sdhaf1 | 644096 | 4-May-15 | 19279 | 2 | 3 | | III-1 | Sh3rf1 | 57630 | 23-May-15 |
| 18979 | 2 | 3 | | III-1 | Sdhaf2 | 54949 | 23-May-15 | 19281 | 2 | 3 | | III-1 | Sh3rf3 | 344558 | 4-May-15 |
| 18980 | 2 | 3 | | III-1 | Sdhb | 6390 | 23-May-15 | 19285 | 2 | 3 | | III-1 | Shank1 | 50944 | 21-May-15 |
| 18981 | 2 | 3 | | III-1 | Sdhc | 6391 | 23-May-15 | 19287 | 2 | 3 | | III-1 | Shank3 | 85358 | 23-May-15 |
| 18986 | 2 | 3 | | III-1 | Sdr16c5 | 195814 | 4-May-15 | 19288 | 2 | 3 | | III-1 | Sharpin | 81858 | 21-May-15 |
| 18988 | 2 | 3 | | III-1 | Sdr39u1 | 56948 | 21-May-15 | 19290 | 2 | 3 | | III-1 | Shhg | 6462 | 4-May-15 |
| 18990 | 2 | 3 | | III-1 | Sdr9c7 | 121214 | 4-May-15 | 19295 | 2 | 3 | | III-1 | Shcbp1 | 79801 | 4-May-15 |
| 18995 | 2 | 3 | | III-1 | Sec11a | 23478 | 4-May-15 | 19298 | 2 | 3 | | III-1 | She | 126669 | 4-May-15 |
| 18997 | 2 | 3 | | III-1 | Sec13 | 6396 | 29-May-15 | 19300 | 2 | 3 | | III-1 | Shfm1 | 7979 | 21-May-15 |
| 19003 | 2 | 3 | | III-1 | Sec16a | 9919 | 12-May-15 | 19305 | 2 | 3 | | III-1 | Shisa5 | 51246 | 12-May-15 |
| 19004 | 2 | 3 | | III-1 | Sec16b | 89866 | 3-May-15 | 19311 | 2 | 3 | | III-1 | Shmt2 | 6472 | 4-May-15 |
| 19005 | 2 | 3 | | III-1 | Sec22a | 26984 | 4-May-15 | 19312 | 2 | 3 | | III-1 | Shoc2 | 8036 | 3-Jun-15 |
| 19006 | 2 | 3 | | III-1 | Sec22b | 9554 | 4-May-15 | 19315 | 2 | 3 | | III-1 | Shprh | 257218 | 4-May-15 |
| 19007 | 2 | 3 | | III-1 | Sec22c | 9117 | 4-May-15 | 19318 | 2 | 3 | | III-1 | Shroom2 | 357 | 4-May-15 |
| 19010 | 2 | 3 | | III-1 | Sec23ip | 11196 | 4-May-15 | 19320 | 2 | 3 | | III-1 | Shroom4 | 57477 | 4-May-15 |
| 19012 | 2 | 3 | | III-1 | Sec24b | 10427 | 4-May-15 | 19323 | 2 | 3 | | III-1 | Siah1b | | |
| 19015 | 2 | 3 | | III-1 | Sec31a | 22872 | 10-May-15 | 19324 | 2 | 3 | | III-1 | Siah2 | 6478 | 24-May-15 |
| 19017 | 2 | 3 | | III-1 | Sec61a1 | 29927 | 12-May-15 | 19325 | 2 | 3 | | III-1 | Siah3 | 283514 | 28-May-15 |
| 19018 | 2 | 3 | | III-1 | Sec61a2 | 55176 | 4-May-15 | 19326 | 2 | 3 | | III-1 | Sidt1 | 54847 | 12-May-15 |
| 19019 | 2 | 3 | | III-1 | Sec61b | 10952 | 4-May-15 | 19327 | 2 | 3 | | III-1 | Sidt2 | 51092 | 4-May-15 |
| 19020 | 2 | 3 | | III-1 | Sec61g | 23480 | 4-May-15 | 19331 | 2 | 3 | | III-1 | Siglec5 | 3778 | 4-May-15 |
| 19024 | 2 | 3 | | III-1 | Secisbp2l | 9728 | 4-May-15 | 19333 | 2 | 3 | | III-1 | Siglecg | | |
| 19025 | 2 | 3 | | III-1 | Sectm1a | | | 19343 | 2 | 3 | | III-1 | Simc1 | 375484 | 21-May-15 |
| 19026 | 2 | 3 | | III-1 | Sectm1b | | | 19344 | 2 | 3 | | III-1 | Sin3a | 25942 | 4-May-15 |
| 19027 | 2 | 3 | | III-1 | Setll | 81929 | 29-May-15 | 19346 | 2 | 3 | | III-1 | Sipa1 | 6494 | 12-May-15 |
| 19037 | 2 | 3 | | III-1 | Selo | 83642 | 4-May-15 | 19347 | 2 | 3 | | III-1 | Sipa1l1 | 26037 | 4-May-15 |
| 19039 | 2 | 3 | | III-1 | Selplg | 6404 | 12-May-15 | 19351 | 2 | 3 | | III-1 | Sirpb1a | | |
| 19047 | 2 | 3 | | III-1 | Sema3g | 56920 | 4-May-15 | 19358 | 2 | 3 | | III-1 | Sirt6 | 51548 | 31-May-15 |
| 19048 | 2 | 3 | | III-1 | Sema4a | 64218 | 23-May-15 | 19364 | 2 | 3 | | III-1 | Six2 | 10736 | 4-May-15 |
| 19049 | 2 | 3 | | III-1 | Sema4b | 10509 | 4-May-15 | 19365 | 2 | 3 | | III-1 | Six3 | 6496 | 22-May-15 |
| 19051 | 2 | 3 | | III-1 | Sema4d | 10507 | 4-May-15 | 19367 | 2 | 3 | | III-1 | Six4 | 51804 | 4-May-15 |
| 19054 | 2 | 3 | | III-1 | Sema5a | 9037 | 4-May-15 | 19369 | 2 | 3 | | III-1 | Six6 | 4990 | 28-May-15 |
| 19058 | 2 | 3 | | III-1 | Sema6c | 10500 | 4-May-15 | 19371 | 2 | 3 | | III-1 | Ska2 | 348235 | 24-May-15 |
| 19070 | 2 | 3 | | III-1 | Sepn1 | 57190 | 23-May-15 | 19374 | 2 | 3 | | III-1 | Skap2 | 8935 | 4-May-15 |
| 19073 | 2 | 3 | | III-1 | Sept1 | 1731 | 4-May-15 | 19377 | 2 | 3 | | III-1 | Skil | 6498 | 12-May-15 |

Fig.22 - 81

| | | | | | | | | | | | | | | | |
|---|---|---|---|---|---|---|---|---|---|---|---|---|---|---|---|
| 19379 | 2 | 3 | | | III-1 | Skint10 | | | 19700 | 2 | 3 | | III-1 | Slc4a1ap | 22950 | 4-May-15 |
| 19380 | 2 | 3 | | | III-1 | Skint11 | | | 19704 | 2 | 3 | | III-1 | Slc4a5 | 57835 | 4-May-15 |
| 19382 | 2 | 3 | | | III-1 | Skint3 | | | 19706 | 2 | 3 | | III-1 | Slc4a8 | 9498 | 4-May-15 |
| 19383 | 2 | 3 | | | III-1 | Skint4 | | | 19711 | 2 | 3 | | III-1 | Slc52a2 | 79581 | 4-May-15 |
| 19385 | 2 | 3 | | | III-1 | Skint6 | | | 19714 | 2 | 3 | | III-1 | Slc5a10 | 125206 | 4-May-15 |
| 19386 | 2 | 3 | | | III-1 | Skint7 | | | 19717 | 2 | 3 | | III-1 | Slc5a2 | 6524 | 20-May-15 |
| 19388 | 2 | 3 | | | III-1 | Skint9 | | | 19720 | 2 | 3 | | III-1 | Slc5a4b | | |
| 19389 | 2 | 3 | | | III-1 | Skiv2l | 6499 | 12-May-15 | 19723 | 2 | 3 | | III-1 | Slc5a7 | 60482 | 12-May-15 |
| 19394 | 2 | 3 | | | III-1 | Skp2 | 6502 | 17-May-15 | 19725 | 2 | 3 | | III-1 | Slc5a9 | 200010 | 4-May-15 |
| 19396 | 2 | 3 | | | III-1 | Sla2 | 84174 | 4-May-15 | 19726 | 2 | 3 | | III-1 | Slc6a1 | 6529 | 28-May-15 |
| 19413 | 2 | 3 | | | III-1 | Slc10a7 | 84068 | 4-May-15 | 19728 | 2 | 3 | | III-1 | Slc6a12 | 6539 | 4-May-15 |
| 19415 | 2 | 3 | | | III-1 | Slc11a2 | 4891 | 12-May-15 | 19737 | 2 | 3 | | III-1 | Slc6a20a | | |
| 19416 | 2 | 3 | | | III-1 | Slc12a1 | 6557 | 12-May-15 | 19738 | 2 | 3 | | III-1 | Slc6a20b | | |
| 19418 | 2 | 3 | | | III-1 | Slc12a3 | 6559 | 12-May-15 | 19739 | 2 | 3 | | III-1 | Slc6a3 | 6531 | 24-May-15 |
| 19419 | 2 | 3 | | | III-1 | Slc12a4 | 6560 | 4-May-15 | 19743 | 2 | 3 | | III-1 | Slc6a7 | 6534 | 4-May-15 |
| 19426 | 2 | 3 | | | III-1 | Slc13a2 | 9058 | 4-May-15 | 19750 | 2 | 3 | | III-1 | Slc7a13 | 157724 | 4-May-15 |
| 19428 | 2 | 3 | | | III-1 | Slc13a3 | 64849 | 4-May-15 | 19754 | 2 | 3 | | III-1 | Slc7a3 | 84889 | 4-May-15 |
| 19430 | 2 | 3 | | | III-1 | Slc13a5 | 284111 | 31-May-15 | 19757 | 2 | 3 | | III-1 | Slc7a6 | 9057 | 4-May-15 |
| 19450 | 2 | 3 | | | III-1 | Slc16a8 | 23539 | 4-May-15 | 19758 | 2 | 3 | | III-1 | Slc7a6os | 84138 | 4-May-15 |
| 19453 | 2 | 3 | | | III-1 | Slc17a2 | 10246 | 4-May-15 | 19761 | 2 | 3 | | III-1 | Slc7a9 | 11136 | 12-May-15 |
| 19454 | 2 | 3 | | | III-1 | Slc17a3 | 10786 | 4-May-15 | 19763 | 2 | 3 | | III-1 | Slc8a2 | 6543 | 4-May-15 |
| 19457 | 2 | 3 | | | III-1 | Slc17a6 | 57084 | 12-May-15 | 19765 | 2 | 3 | | III-1 | Slc8b1 | 80024 | 4-May-15 |
| 19458 | 2 | 3 | | | III-1 | Slc17a7 | 57030 | 4-May-15 | 19766 | 2 | 3 | | III-1 | Slc9a1 | 6548 | 4-May-15 |
| 19461 | 2 | 3 | | | III-1 | Slc18a1 | 6570 | 3-May-15 | 19770 | 2 | 3 | | III-1 | Slc9a3r2 | 9351 | 4-May-15 |
| 19462 | 2 | 3 | | | III-1 | Slc18a2 | 6571 | 4-May-15 | 19772 | 2 | 3 | | III-1 | Slc9a5 | 6553 | 4-May-15 |
| 19466 | 2 | 3 | | | III-1 | Slc19a2 | 10560 | 23-May-15 | 19775 | 2 | 3 | | III-1 | Slc9a8 | 23315 | 4-May-15 |
| 19469 | 2 | 3 | | | III-1 | Slc1a2 | 6506 | 21-May-15 | 19779 | 2 | 3 | | III-1 | Slc9c1 | 285335 | 4-May-15 |
| 19473 | 2 | 3 | | | III-1 | Slc1a6 | 6511 | 4-May-15 | 19783 | 2 | 3 | | III-1 | Slco1a6 | | |
| 19478 | 2 | 3 | | | III-1 | Slc22a12 | 116085 | 12-May-15 | 19786 | 2 | 3 | | III-1 | Slco2a1 | 6578 | 17-May-15 |
| 19485 | 2 | 3 | | | III-1 | Slc22a18 | 5002 | 23-May-15 | 19787 | 2 | 3 | | III-1 | Slco2b1 | 11309 | 12-May-15 |
| 19486 | 2 | 3 | | | III-1 | Slc22a19 | | | 19804 | 2 | 3 | | III-1 | Slfn9 | | |
| 19490 | 2 | 3 | | | III-1 | Slc22a22 | | | 19809 | 2 | 3 | | III-1 | Slit3 | 6586 | 7-Jun-15 |
| 19494 | 2 | 3 | | | III-1 | Slc22a28 | | | 19810 | 2 | 3 | | III-1 | Slitrk1 | 114798 | 23-May-15 |
| 19496 | 2 | 3 | | | III-1 | Slc22a3 | 6581 | 17-May-15 | 19819 | 2 | 3 | | III-1 | Simo2 | 51012 | 4-May-15 |
| 19499 | 2 | 3 | | | III-1 | Slc22a5 | 6584 | 23-May-15 | 19825 | 2 | 3 | | III-1 | Six | | |
| 19500 | 2 | 3 | | | III-1 | Slc22a6 | 9356 | 4-May-15 | 19827 | 2 | 3 | | III-1 | Six4 | 84464 | 23-May-15 |
| 19503 | 2 | 3 | | | III-1 | Slc23a1 | 9963 | 7-Jun-15 | 19828 | 2 | 3 | | III-1 | Six4ip | 128710 | 4-May-15 |
| 19504 | 2 | 3 | | | III-1 | Slc23a2 | 9962 | 7-Jun-15 | 19832 | 2 | 3 | | III-1 | Smad2 | 4087 | 24-May-15 |
| 19506 | 2 | 3 | | | III-1 | Slc24a1 | 9187 | 4-May-15 | 19837 | 2 | 3 | | III-1 | Smad7 | 4092 | 12-May-15 |
| 19516 | 2 | 3 | | | III-1 | Slc25a14 | 9018 | 4-May-15 | 19838 | 2 | 3 | | III-1 | Smad9 | 4093 | 4-May-15 |
| 19517 | 2 | 3 | | | III-1 | Slc25a15 | 10166 | 23-May-15 | 19839 | 2 | 3 | | III-1 | Smagp | 57228 | 4-May-15 |
| 19520 | 2 | 3 | | | III-1 | Slc25a18 | 83733 | 12-May-15 | 19840 | 2 | 3 | | III-1 | Smap1 | 60682 | 7-Jun-15 |
| 19525 | 2 | 3 | | | III-1 | Slc25a22 | 79751 | 4-May-15 | 19843 | 2 | 3 | | III-1 | Smarca2 | 6595 | 4-May-15 |
| 19529 | 2 | 3 | | | III-1 | Slc25a26 | 115286 | 12-May-15 | 19855 | 2 | 3 | | III-1 | Smarce1 | 6605 | 12-May-15 |
| 19530 | 2 | 3 | | | III-1 | Slc25a27 | 9481 | 4-May-15 | 19864 | 2 | 3 | | III-1 | Smchd1 | 23347 | 23-May-15 |
| 19531 | 2 | 3 | | | III-1 | Slc25a28 | 81894 | 12-May-15 | 19871 | 2 | 3 | | III-1 | Smdt1 | 91689 | 4-May-15 |
| 19533 | 2 | 3 | | | III-1 | Slc25a3 | 5250 | 21-May-15 | 19875 | 2 | 3 | | III-1 | Smg5 | 23381 | 12-May-15 |
| 19538 | 2 | 3 | | | III-1 | Slc25a34 | 284723 | 4-May-15 | 19880 | 2 | 3 | | III-1 | Smgc | | |
| 19539 | 2 | 3 | | | III-1 | Slc25a35 | 399512 | 21-May-15 | 19883 | 2 | 3 | | III-1 | Smim12 | 113444 | 4-May-15 |
| 19542 | 2 | 3 | | | III-1 | Slc25a38 | 54977 | 24-May-15 | 19889 | 2 | 3 | | III-1 | Smim20 | 389203 | 4-May-15 |
| 19543 | 2 | 3 | | | III-1 | Slc25a39 | 51629 | 4-May-15 | 19891 | 2 | 3 | | III-1 | Smim23 | 644994 | 21-May-15 |
| 19545 | 2 | 3 | | | III-1 | Slc25a40 | 55972 | 4-May-15 | 19896 | 2 | 3 | | III-1 | Smim6 | 100130933 | 4-May-15 |
| 19548 | 2 | 3 | | | III-1 | Slc25a43 | 203427 | 4-May-15 | 19897 | 2 | 3 | | III-1 | Smim7 | 79086 | 4-May-15 |
| 19551 | 2 | 3 | | | III-1 | Slc25a46 | 91137 | 3-Jun-15 | 19899 | 2 | 3 | | III-1 | Smim9 | 100132963 | 4-May-15 |
| 19555 | 2 | 3 | | | III-1 | Slc25a51 | 92014 | 4-May-15 | 19905 | 2 | 3 | | III-1 | Smoc2 | 64094 | 4-May-15 |
| 19557 | 2 | 3 | | | III-1 | Slc25a54 | | | 19906 | 2 | 3 | | III-1 | Smok2a | | |
| 19559 | 2 | 3 | | | III-1 | Slc26a10 | 65012 | 4-May-15 | 19917 | 2 | 3 | | III-1 | Smpdl3a | 10924 | 23-May-15 |
| 19563 | 2 | 3 | | | III-1 | Slc26a4 | 5172 | 22-May-15 | 19923 | 2 | 3 | | III-1 | Smtn | 6525 | 4-May-15 |
| 19574 | 2 | 3 | | | III-1 | Slc27a6 | 28965 | 4-May-15 | 19932 | 2 | 3 | | III-1 | Smyd3 | 64754 | 21-May-15 |
| 19578 | 2 | 3 | | | III-1 | Slc29a1 | 2030 | 17-May-15 | 19938 | 2 | 3 | | III-1 | Snap23 | 8773 | 4-May-15 |
| 19579 | 2 | 3 | | | III-1 | Slc29a2 | 3177 | 4-May-15 | 19940 | 2 | 3 | | III-1 | Snap29 | 9342 | 28-May-15 |
| 19580 | 2 | 3 | | | III-1 | Slc29a3 | 55315 | 4-May-15 | 19947 | 2 | 3 | | III-1 | Snapc5 | 10302 | 21-May-15 |
| 19581 | 2 | 3 | | | III-1 | Slc29a4 | 222962 | 4-May-15 | 19951 | 2 | 3 | | III-1 | Snch | 6620 | 4-May-15 |
| 19582 | 2 | 3 | | | III-1 | Slc2a1 | 6513 | 24-May-15 | 19954 | 2 | 3 | | III-1 | Sned1 | 25992 | 12-May-15 |
| 19583 | 2 | 3 | | | III-1 | Slc2a10 | 81031 | 23-May-15 | 19956 | 2 | 3 | | III-1 | Snhg1 | 23642 | 4-May-15 |
| 19593 | 2 | 3 | | | III-1 | Slc2a8 | 29988 | 4-May-15 | 19960 | 2 | 3 | | III-1 | Snhg18 | 100505806 | 4-May-15 |
| 19594 | 2 | 3 | | | III-1 | Slc2a9 | 56606 | 31-May-15 | 19962 | 2 | 3 | | III-1 | Snhg4 | 724102 | 4-May-15 |
| 19595 | 2 | 3 | | | III-1 | Slc30a1 | 7779 | 17-May-15 | 19968 | 2 | 3 | | III-1 | Snip1 | 79753 | 4-May-15 |
| 19606 | 2 | 3 | | | III-1 | Slc31a2 | 1318 | 4-May-15 | 20081 | 2 | 3 | | III-1 | Snrk | 54861 | 4-May-15 |
| 19614 | 2 | 3 | | | III-1 | Slc35a3 | 23443 | 4-May-15 | 20082 | 2 | 3 | | III-1 | Snrnp200 | 23020 | 23-May-15 |
| 19615 | 2 | 3 | | | III-1 | Slc35a4 | 113829 | 4-May-15 | 20083 | 2 | 3 | | III-1 | Snrnp25 | 79622 | 4-May-15 |
| 19620 | 2 | 3 | | | III-1 | Slc35b4 | 84912 | 4-May-15 | 20084 | 2 | 3 | | III-1 | Snrnp27 | 11017 | 4-May-15 |
| 19622 | 2 | 3 | | | III-1 | Slc35c2 | 51006 | 4-May-15 | 20086 | 2 | 3 | | III-1 | Snrnp40 | 9410 | 4-May-15 |
| 19624 | 2 | 3 | | | III-1 | Slc35d2 | 11046 | 4-May-15 | 20088 | 2 | 3 | | III-1 | Snrnp70 | 6625 | 12-May-15 |
| 19625 | 2 | 3 | | | III-1 | Slc35d3 | 340146 | 4-May-15 | 20089 | 2 | 3 | | III-1 | Snrpa | 6626 | 12-May-15 |
| 19630 | 2 | 3 | | | III-1 | Slc35f1 | 222553 | 4-May-15 | 20091 | 2 | 3 | | III-1 | Snrpb | 6628 | 28-May-15 |
| 19632 | 2 | 3 | | | III-1 | Slc35f3 | 148641 | 4-May-15 | 20092 | 2 | 3 | | III-1 | Snrpb2 | 6629 | 4-May-15 |
| 19637 | 2 | 3 | | | III-1 | Slc35g2 | 80723 | 4-May-15 | 20096 | 2 | 3 | | III-1 | Snrpd3 | 6634 | 4-May-15 |
| 19638 | 2 | 3 | | | III-1 | Slc35g3 | 146861 | 4-May-15 | 20109 | 2 | 3 | | III-1 | Snw1 | 22938 | 4-May-15 |
| 19640 | 2 | 3 | | | III-1 | Slc36a1os | | | 20112 | 2 | 3 | | III-1 | Snx11 | 29916 | 21-May-15 |
| 19646 | 2 | 3 | | | III-1 | Slc37a3 | 84255 | 4-May-15 | 20114 | 2 | 3 | | III-1 | Snx13 | 23161 | 12-May-15 |
| 19649 | 2 | 3 | | | III-1 | Slc38a10 | 124565 | 12-May-15 | 20125 | 2 | 3 | | III-1 | Snx24 | 28966 | 4-May-15 |
| 19656 | 2 | 3 | | | III-1 | Slc38a7 | 55238 | 12-May-15 | 20129 | 2 | 3 | | III-1 | Snx3 | 8724 | 2-Jun-15 |
| 19659 | 2 | 3 | | | III-1 | Slc39a1 | 27173 | 17-May-15 | 20131 | 2 | 3 | | III-1 | Snx31 | 169166 | 4-May-15 |
| 19665 | 2 | 3 | | | III-1 | Slc39a2 | 29986 | 4-May-15 | 20133 | 2 | 3 | | III-1 | Snx33 | 257364 | 12-May-15 |
| 19666 | 2 | 3 | | | III-1 | Slc39a3 | 29985 | 4-May-15 | 20136 | 2 | 3 | | III-1 | Snx6 | 58533 | 4-May-15 |
| 19668 | 2 | 3 | | | III-1 | Slc39a5 | 283375 | 4-May-15 | 20138 | 2 | 3 | | III-1 | Snx8 | 29886 | 4-May-15 |
| 19670 | 2 | 3 | | | III-1 | Slc39a7 | 7922 | 4-May-15 | 20148 | 2 | 3 | | III-1 | Socs6 | 9306 | 4-May-15 |
| 19672 | 2 | 3 | | | III-1 | Slc39a9 | 55334 | 12-May-15 | 20151 | 2 | 3 | | III-1 | Sod2 | 6648 | 17-May-15 |
| 19674 | 2 | 3 | | | III-1 | Slc3a2 | 6520 | 12-May-15 | 20152 | 2 | 3 | | III-1 | Sod3 | 6649 | 4-May-15 |
| 19675 | 2 | 3 | | | III-1 | Slc40a1 | 30061 | 28-May-15 | 20156 | 2 | 3 | | III-1 | Sohlh2 | 54937 | 4-May-15 |
| 19681 | 2 | 3 | | | III-1 | Slc43a3 | 29015 | 4-May-15 | 20158 | 2 | 3 | | III-1 | Sorbs1 | 10580 | 12-May-15 |
| 19682 | 2 | 3 | | | III-1 | Slc44a1 | 23446 | 4-May-15 | 20159 | 2 | 3 | | III-1 | Sorbs2 | 8470 | 20-May-15 |
| 19686 | 2 | 3 | | | III-1 | Slc44a5 | 204962 | 14-May-15 | 20160 | 2 | 3 | | III-1 | Sorbs2os | | |
| 19690 | 2 | 3 | | | III-1 | Slc45a4 | 57210 | 4-May-15 | 20164 | 2 | 3 | | III-1 | Socs3 | 22986 | 4-May-15 |
| 19693 | 2 | 3 | | | III-1 | Slc46a3 | 283537 | 12-May-15 | | | | | | | | |
| 19695 | 2 | 3 | | | III-1 | Slc47a2 | 146802 | 4-May-15 | | | | | | | | |

Fig.22 - 82

| | | | | | | | | | | | | | | |
|---|---|---|---|---|---|---|---|---|---|---|---|---|---|---|
| 20166 | 2 | 3 | | | III-1 | Sorl1 | 6653 | 23-May-15 | 20521 | 2 | 3 | | III-1 | St7l | 54879 | 21-May-15 |
| 20171 | 2 | 3 | | | III-1 | Sostdc1 | 25928 | 4-May-15 | 20526 | 2 | 3 | | III-1 | St8sia4 | 7903 | 4-May-15 |
| 20174 | 2 | 3 | | | III-1 | Sowahc | 65124 | 4-May-15 | 20529 | 2 | 3 | | III-1 | Stab1 | 23166 | 12-May-15 |
| 20175 | 2 | 3 | | | III-1 | Sowahd | 347454 | 4-May-15 | 20531 | 2 | 3 | | III-1 | Stac | 6769 | 12-May-15 |
| 20178 | 2 | 3 | | | III-1 | Sox1 | 6656 | 12-May-15 | 20532 | 2 | 3 | | III-1 | Stac2 | 342667 | 12-May-15 |
| 20180 | 2 | 3 | | | III-1 | Sox13 | 9580 | 4-May-15 | 20538 | 2 | 3 | | III-1 | Stam2 | 10254 | 4-May-15 |
| 20181 | 2 | 3 | | | III-1 | Sox14 | 8403 | 4-May-15 | 20540 | 2 | 3 | | III-1 | Stambp1 | 57559 | 4-May-15 |
| 20184 | 2 | 3 | | | III-1 | Sox18 | 54345 | 4-May-15 | 20543 | 2 | 3 | | III-1 | Stap2 | 55620 | 4-May-15 |
| 20185 | 2 | 3 | | | III-1 | Sox2 | 6657 | 24-May-15 | 20544 | 2 | 3 | | III-1 | Star | 6770 | 7-Jun-15 |
| 20197 | 2 | 3 | | | III-1 | Sp1 | 6667 | 13-Jun-15 | 20546 | 2 | 3 | | III-1 | Stard13 | 90627 | 17-May-15 |
| 20202 | 2 | 3 | | | III-1 | Sp3 | 6670 | 16-Jun-15 | 20547 | 2 | 3 | | III-1 | Stard3 | 10948 | 4-May-15 |
| 20204 | 2 | 3 | | | III-1 | Sp4 | 6671 | 28-May-15 | 20551 | 2 | 3 | | III-1 | Stard6 | 147323 | 4-May-15 |
| 20207 | 2 | 3 | | | III-1 | Sp7 | 121340 | 17-May-15 | 20554 | 2 | 3 | | III-1 | Stat1 | 6772 | 31-May-15 |
| 20211 | 2 | 3 | | | III-1 | Spaca1 | 81833 | 4-May-15 | 20556 | 2 | 3 | | III-1 | Stat3 | 6774 | 31-May-15 |
| 20216 | 2 | 3 | | | III-1 | Spaca7 | 122258 | 4-May-15 | 20557 | 2 | 3 | | III-1 | Stat4 | 6775 | 12-May-15 |
| 20220 | 2 | 3 | | | III-1 | Spag16 | 79582 | 12-May-15 | 20560 | 2 | 3 | | III-1 | Stat6 | 6778 | 24-May-15 |
| 20231 | 2 | 3 | | | III-1 | Spast | 6683 | 31-May-15 | 20563 | 2 | 3 | | III-1 | Stbd1 | 8987 | 4-May-15 |
| 20233 | 2 | 3 | | | III-1 | Spata13 | 221178 | 4-May-15 | 20566 | 2 | 3 | | III-1 | Steap1 | 26872 | 4-May-15 |
| 20234 | 2 | 3 | | | III-1 | Spata16 | 83893 | 12-May-15 | 20579 | 2 | 3 | | III-1 | Stk11 | 6794 | 24-May-15 |
| 20237 | 2 | 3 | | | III-1 | Spata19 | 219938 | 4-May-15 | 20583 | 2 | 3 | | III-1 | Stk19 | 8859 | 12-May-15 |
| 20243 | 2 | 3 | | | III-1 | Spata25 | 128497 | 4-May-15 | 20589 | 2 | 3 | | III-1 | Stk32b | 55351 | 14-May-15 |
| 20246 | 2 | 3 | | | III-1 | Spata31 | | | 20590 | 2 | 3 | | III-1 | Stk32c | 282974 | 4-May-15 |
| 20256 | 2 | 3 | | | III-1 | Spata5l1 | 79029 | 4-May-15 | 20591 | 2 | 3 | | III-1 | Stk33 | 65975 | 12-May-15 |
| 20259 | 2 | 3 | | | III-1 | Spata9 | 83890 | 4-May-15 | 20592 | 2 | 3 | | III-1 | Stk35 | 140901 | 4-May-15 |
| 20270 | 2 | 3 | | | III-1 | Spdef | 25803 | 20-May-15 | 20596 | 2 | 3 | | III-1 | Stk39 | 27347 | 4-May-15 |
| 20272 | 2 | 3 | | | III-1 | Spdya | 245711 | 4-May-15 | 20597 | 2 | 3 | | III-1 | Stk4 | 6789 | 4-May-15 |
| 20273 | 2 | 3 | | | III-1 | Spdyb | | | 20602 | 2 | 3 | | III-1 | Stmn4 | 50861 | 12-May-15 |
| 20275 | 2 | 3 | | | III-1 | Speccl1 | 23384 | 28-May-15 | 20606 | 2 | 3 | | III-1 | Stoml1 | 9399 | 12-May-15 |
| 20276 | 2 | 3 | | | III-1 | Speer1-ps1 | | | 20608 | 2 | 3 | | III-1 | Stoml3 | 161003 | 4-May-15 |
| 20291 | 2 | 3 | | | III-1 | Spef2 | 79925 | 4-May-15 | 20611 | 2 | 3 | | III-1 | Stox1 | 219736 | 3-May-15 |
| 20294 | 2 | 3 | | | III-1 | Spen | 23013 | 13-Jun-15 | 20612 | 2 | 3 | | III-1 | Stox2 | 56977 | 4-May-15 |
| 20296 | 2 | 3 | | | III-1 | Spesp1 | 246777 | 4-May-15 | 20613 | 2 | 3 | | III-1 | Stpg1 | 90529 | 4-May-15 |
| 20298 | 2 | 3 | | | III-1 | Spg20 | 23111 | 23-May-15 | 20616 | 2 | 3 | | III-1 | Stra6 | 64220 | 4-May-15 |
| 20302 | 2 | 3 | | | III-1 | Sphk2 | 56848 | 4-May-15 | 20620 | 2 | 3 | | III-1 | Strap | 11171 | 7-Jun-15 |
| 20303 | 2 | 3 | | | III-1 | Sphkap | 80309 | 12-May-15 | 20622 | 2 | 3 | | III-1 | Strc | 161497 | 23-May-15 |
| 20304 | 2 | 3 | | | III-1 | Spi1 | 6688 | 12-May-15 | 20631 | 2 | 3 | | III-1 | Stx11 | 8676 | 23-May-15 |
| 20307 | 2 | 3 | | | III-1 | Spice1 | 152185 | 4-May-15 | 20633 | 2 | 3 | | III-1 | Stx16 | 8675 | 4-May-15 |
| 20311 | 2 | 3 | | | III-1 | Spin2d | | | 20636 | 2 | 3 | | III-1 | Stx19 | 415117 | 4-May-15 |
| 20318 | 2 | 3 | | | III-1 | Spink14 | 408187 | 21-May-15 | 20637 | 2 | 3 | | III-1 | Stx1a | 6804 | 12-May-15 |
| 20323 | 2 | 3 | | | III-1 | Spink6 | 404203 | 4-May-15 | 20638 | 2 | 3 | | III-1 | Stx1b | 112755 | 12-May-15 |
| 20333 | 2 | 3 | | | III-1 | Spire2 | 84501 | 24-May-15 | 20639 | 2 | 3 | | III-1 | Stx2 | 2054 | 4-May-15 |
| 20334 | 2 | 3 | | | III-1 | Spn | 6693 | 7-Jun-15 | 20640 | 2 | 3 | | III-1 | Stx3 | 6809 | 3-May-15 |
| 20342 | 2 | 3 | | | III-1 | Spock3 | 50859 | 12-May-15 | 20646 | 2 | 3 | | III-1 | Stxbp1 | 6812 | 26-May-15 |
| 20343 | 2 | 3 | | | III-1 | Spon1 | 10418 | 4-May-15 | 20655 | 2 | 3 | | III-1 | Styx | 6815 | 4-May-15 |
| 20357 | 2 | 3 | | | III-1 | Sprn | 503542 | 4-May-15 | 20658 | 2 | 3 | | III-1 | Sucla2 | 8803 | 23-May-15 |
| 20364 | 2 | 3 | | | III-1 | Sprr2e | 6704 | 3-May-15 | 20659 | 2 | 3 | | III-1 | Suclg1 | 8802 | 4-May-15 |
| 20368 | 2 | 3 | | | III-1 | Sprr2j-ps | | | 20660 | 2 | 3 | | III-1 | Suclg2 | 8801 | 4-May-15 |
| 20372 | 2 | 3 | | | III-1 | Sprr4 | 163778 | 16-May-15 | 20661 | 2 | 3 | | III-1 | Sucnr1 | 56670 | 4-May-15 |
| 20373 | 2 | 3 | | | III-1 | Sprtn | 83932 | 12-May-15 | 20666 | 2 | 3 | | III-1 | Sugp1 | 57794 | 4-May-15 |
| 20376 | 2 | 3 | | | III-1 | Spry3 | 10251 | 12-May-15 | 20667 | 2 | 3 | | III-1 | Sugp2 | 10147 | 4-May-15 |
| 20379 | 2 | 3 | | | III-1 | Spryd4 | 283377 | 4-May-15 | 20669 | 2 | 3 | | III-1 | Sulf1 | 23213 | 17-May-15 |
| 20380 | 2 | 3 | | | III-1 | Spryd7 | 57213 | 4-May-15 | 20670 | 2 | 3 | | III-1 | Sulf2 | 55959 | 4-May-15 |
| 20381 | 2 | 3 | | | III-1 | Spsb1 | 80176 | 4-May-15 | 20672 | 2 | 3 | | III-1 | Sult1b1 | 27284 | 4-May-15 |
| 20382 | 2 | 3 | | | III-1 | Spsb2 | 84727 | 4-May-15 | 20685 | 2 | 3 | | III-1 | Sult3a1 | | |
| 20383 | 2 | 3 | | | III-1 | Spsb3 | 90864 | 4-May-15 | 20687 | 2 | 3 | | III-1 | Sult5a1 | | |
| 20391 | 2 | 3 | | | III-1 | Sptbn4 | 57731 | 4-May-15 | 20693 | 2 | 3 | | III-1 | Sumo3 | 6612 | 7-Jun-15 |
| 20395 | 2 | 3 | | | III-1 | Sptssa | 171546 | 4-May-15 | 20696 | 2 | 3 | | III-1 | Sun3 | 256979 | 4-May-15 |
| 20401 | 2 | 3 | | | III-1 | Sqstm1 | 8878 | 24-May-15 | 20699 | 2 | 3 | | III-1 | Supt16 | | |
| 20402 | 2 | 3 | | | III-1 | Sra1 | 10011 | 7-Jun-15 | 20701 | 2 | 3 | | III-1 | Supt3 | | |
| 20403 | 2 | 3 | | | III-1 | Srbd1 | 55133 | 4-May-15 | 20703 | 2 | 3 | | III-1 | Supt5 | | |
| 20405 | 2 | 3 | | | III-1 | Srcin1 | 80725 | 4-May-15 | 20715 | 2 | 3 | | III-1 | Suv39h1 | 6839 | 12-May-15 |
| 20412 | 2 | 3 | | | III-1 | Srek1 | 140890 | 3-Jun-15 | 20722 | 2 | 3 | | III-1 | Sv2b | 9899 | 4-May-15 |
| 20416 | 2 | 3 | | | III-1 | Srgap1 | 57522 | 4-May-15 | 20731 | 2 | 3 | | III-1 | Svop | 55530 | 4-May-15 |
| 20418 | 2 | 3 | | | III-1 | Srgap3 | 9901 | 7-Jun-15 | 20733 | 2 | 3 | | III-1 | Svs1 | | |
| 20419 | 2 | 3 | | | III-1 | Srgn | 5552 | 12-May-15 | 20744 | 2 | 3 | | III-1 | Syap1 | 94056 | 4-May-15 |
| 20423 | 2 | 3 | | | III-1 | Srms | 6725 | 4-May-15 | 20755 | 2 | 3 | | III-1 | Syde1 | 85360 | 4-May-15 |
| 20425 | 2 | 3 | | | III-1 | Srp19 | 6728 | 4-May-15 | 20757 | 2 | 3 | | III-1 | Syt2 | 25949 | 17-May-15 |
| 20426 | 2 | 3 | | | III-1 | Srp54a | | | 20759 | 2 | 3 | | III-1 | Sympk | 8189 | 4-May-15 |
| 20433 | 2 | 3 | | | III-1 | Srpk2 | 6733 | 4-May-15 | 20760 | 2 | 3 | | III-1 | Syn1 | 6853 | 7-Jun-15 |
| 20435 | 2 | 3 | | | III-1 | Srpr | 6734 | 4-May-15 | 20762 | 2 | 3 | | III-1 | Syn3 | 8224 | 4-May-15 |
| 20438 | 2 | 3 | | | III-1 | Srpx2 | 27286 | 23-May-15 | 20770 | 2 | 3 | | III-1 | Syne2 | 23224 | 4-May-15 |
| 20441 | 2 | 3 | | | III-1 | Srrm1 | 10250 | 4-May-15 | 20773 | 2 | 3 | | III-1 | Syngap1 | 8831 | 3-Jun-15 |
| 20443 | 2 | 3 | | | III-1 | Srrm3 | 222183 | 4-May-15 | 20777 | 2 | 3 | | III-1 | Syngr4 | 23546 | 4-May-15 |
| 20446 | 2 | 3 | | | III-1 | Srrt | 51593 | 4-May-15 | 20780 | 2 | 3 | | III-1 | Synj2bp | 55333 | 4-May-15 |
| 20447 | 2 | 3 | | | III-1 | Srsf1 | 6426 | 4-May-15 | 20798 | 2 | 3 | | III-1 | Syt16 | 83851 | 21-May-15 |
| 20455 | 2 | 3 | | | III-1 | Srsf6 | 6431 | 21-May-15 | 20802 | 2 | 3 | | III-1 | Syt4 | 6860 | 12-May-15 |
| 20459 | 2 | 3 | | | III-1 | Sry | 6736 | 28-May-15 | 20805 | 2 | 3 | | III-1 | Syt7 | 9066 | 4-May-15 |
| 20462 | 2 | 3 | | | III-1 | Ssh | 6741 | 21-May-15 | 20812 | 2 | 3 | | III-1 | Syt15 | 94122 | 21-May-15 |
| 20467 | 2 | 3 | | | III-1 | Ssc5d | 284297 | 4-May-15 | 20814 | 2 | 3 | | III-1 | Szrd1 | 26099 | 4-May-15 |
| 20469 | 2 | 3 | | | III-1 | Ssh1 | 54434 | 23-May-15 | 20837 | 2 | 3 | | III-1 | Tac2 | 6863 | 4-May-15 |
| 20471 | 2 | 3 | | | III-1 | Ssh3 | 54961 | 12-May-15 | 20839 | 2 | 3 | | III-1 | Tacc1 | 6867 | 4-May-15 |
| 20472 | 2 | 3 | | | III-1 | Ssmem1 | 136263 | 4-May-15 | 20841 | 2 | 3 | | III-1 | Tacc3 | 10460 | 23-May-15 |
| 20475 | 2 | 3 | | | III-1 | Sspo | 23145 | 4-May-15 | 20842 | 2 | 3 | | III-1 | Taco1 | 51204 | 4-May-15 |
| 20478 | 2 | 3 | | | III-1 | Ssr1 | 6745 | 12-May-15 | 20843 | 2 | 3 | | III-1 | Tacr1 | 6869 | 17-May-15 |
| 20479 | 2 | 3 | | | III-1 | Ssr3 | 6747 | 21-May-15 | 20845 | 2 | 3 | | III-1 | Tacr3 | 6870 | 12-May-15 |
| 20480 | 2 | 3 | | | III-1 | Ssrp1 | 6749 | 24-May-15 | 20847 | 2 | 3 | | III-1 | Tada1 | 117143 | 7-Jun-15 |
| 20484 | 2 | 3 | | | III-1 | Sstr2 | 6752 | 24-May-15 | 20849 | 2 | 3 | | III-1 | Tada2b | 93624 | 4-May-15 |
| 20493 | 2 | 3 | | | III-1 | Ssx9 | 280660 | 4-May-15 | 20856 | 2 | 3 | | III-1 | Taf15 | 8148 | 4-May-15 |
| 20497 | 2 | 3 | | | III-1 | Ssxb3 | | | 20857 | 2 | 3 | | III-1 | Taf1a | 9015 | 4-May-15 |
| 20504 | 2 | 3 | | | III-1 | St18 | 9705 | 12-May-15 | 20858 | 2 | 3 | | III-1 | Taf1b | 9014 | 4-May-15 |
| 20506 | 2 | 3 | | | III-1 | St3gal2 | 6483 | 12-May-15 | 20859 | 2 | 3 | | III-1 | Taf1c | 9013 | 4-May-15 |
| 20508 | 2 | 3 | | | III-1 | St3gal4 | 6484 | 21-May-15 | 20861 | 2 | 3 | | III-1 | Taf2 | 6873 | 12-May-15 |
| 20509 | 2 | 3 | | | III-1 | St3gal5 | 8869 | 4-May-15 | 20865 | 2 | 3 | | III-1 | Taf5 | 6877 | 4-May-15 |
| 20511 | 2 | 3 | | | III-1 | St5 | 6764 | 12-May-15 | 20869 | 2 | 3 | | III-1 | Taf7 | 6879 | 4-May-15 |
| 20513 | 2 | 3 | | | III-1 | St6gal2 | 84620 | 24-May-15 | 20872 | 2 | 3 | | III-1 | Taf9 | 6880 | 4-May-15 |
| 20519 | 2 | 3 | | | III-1 | St6galnac6 | 30815 | 4-May-15 | 20875 | 2 | 3 | | III-1 | Tagap1 | 117289 | 4-May-15 |
| 20520 | 2 | 3 | | | III-1 | St7 | 7982 | 7-Jun-15 | 20877 | 2 | 3 | | III-1 | Tagln2 | 8407 | 4-May-15 |

Fig.22 - 83

| | | | | | | | | | | | | | | | |
|---|---|---|---|---|---|---|---|---|---|---|---|---|---|---|---|
| 20878 | 2 | 3 | | | III-1 | Tagln3 | 29114 | 4-May-15 | 21254 | 2 | 3 | | III-1 | Thoc1 | 9984 | 4-May-15 |
| 20881 | 2 | 3 | | | III-1 | Taldo1 | 6888 | 12-May-15 | 21255 | 2 | 3 | | III-1 | Thoc2 | 57187 | 4-May-15 |
| 20882 | 2 | 3 | | | III-1 | Tamm41 | 132001 | 4-May-15 | 21259 | 2 | 3 | | III-1 | Thoc7 | 80145 | 4-May-15 |
| 20883 | 2 | 3 | | | III-1 | Tanc1 | 85461 | 4-May-15 | 21261 | 2 | 3 | | III-1 | Thpo | 7066 | 12-May-15 |
| 20884 | 2 | 3 | | | III-1 | Tanc2 | 26115 | 4-May-15 | 21262 | 2 | 3 | | III-1 | Thra | 7067 | 4-May-15 |
| 20886 | 2 | 3 | | | III-1 | Tango6 | 79613 | 12-May-15 | 21268 | 2 | 3 | | III-1 | Thsd7a | 221981 | 4-May-15 |
| 20888 | 2 | 3 | | | III-1 | Taok1 | 57551 | 4-May-15 | 21276 | 2 | 3 | | III-1 | Tia1 | 7072 | 4-May-15 |
| 20897 | 2 | 3 | | | III-1 | Tardbp | 23435 | 31-May-15 | 21280 | 2 | 3 | | III-1 | Ticam1 | 148022 | 17-May-15 |
| 20899 | 2 | 3 | | | III-1 | Tars | 6897 | 4-May-15 | 21285 | 2 | 3 | | III-1 | Tifab | 49718? | 4-May-15 |
| 20902 | 2 | 3 | | | III-1 | Tas1r1 | 80835 | 4-May-15 | 21286 | 2 | 3 | | III-1 | Tigd2 | 166815 | 4-May-15 |
| 20905 | 2 | 3 | | | III-1 | Tas2r102 | | | 21293 | 2 | 3 | | III-1 | Timeless | 8914 | 3-May-15 |
| 20944 | 2 | 3 | | | III-1 | Tatdn3 | 128387 | 4-May-15 | 21295 | 2 | 3 | | III-1 | Timm10b | 26515 | 4-May-15 |
| 20947 | 2 | 3 | | | III-1 | Taz | 6901 | 7-Jun-15 | 21299 | 2 | 3 | | III-1 | Timm21 | 29090 | 4-May-15 |
| 20950 | 2 | 3 | | | III-1 | Tbc1d10a | 83874 | 4-May-15 | 21300 | 2 | 3 | | III-1 | Timm22 | 29928 | 4-May-15 |
| 20958 | 2 | 3 | | | III-1 | Tbc1d17 | 79735 | 21-May-15 | 21302 | 2 | 3 | | III-1 | Timm44 | 10469 | 21-May-15 |
| 20961 | 2 | 3 | | | III-1 | Tbc1d20 | 128637 | 4-May-15 | 21304 | 2 | 3 | | III-1 | Timm8a1 | | |
| 20964 | 2 | 3 | | | III-1 | Tbc1d22b | 55633 | 4-May-15 | 21305 | 2 | 3 | | III-1 | Timm8a2 | | |
| 20968 | 2 | 3 | | | III-1 | Tbc1d25 | 4943 | 21-May-15 | 21313 | 2 | 3 | | III-1 | Tinag | 27283 | 4-May-15 |
| 20969 | 2 | 3 | | | III-1 | Tbc1d2b | 23102 | 4-May-15 | 21315 | 2 | 3 | | III-1 | Tinf2 | 26277 | 23-May-15 |
| 20971 | 2 | 3 | | | III-1 | Tbc1d31 | 93594 | 4-May-15 | 21318 | 2 | 3 | | III-1 | Tipd | 261726 | 31-May-15 |
| 20974 | 2 | 3 | | | III-1 | Tbc1d5 | 9779 | 28-May-15 | 21320 | 2 | 3 | | III-1 | Tjap1 | 93643 | 4-May-15 |
| 20977 | 2 | 3 | | | III-1 | Tbc1d8b | 54885 | 12-May-15 | 21324 | 2 | 3 | | III-1 | Tk1 | 7083 | 4-May-15 |
| 20979 | 2 | 3 | | | III-1 | Tbc1d9b | 23061 | 12-May-15 | 21335 | 2 | 3 | | III-1 | Tle3 | 7090 | 21-May-15 |
| 20981 | 2 | 3 | | | III-1 | Tbcb | 1155 | 10-May-15 | 21337 | 2 | 3 | | III-1 | Tle6 | 79816 | 4-May-15 |
| 20982 | 2 | 3 | | | III-1 | Tbcc | 6903 | 4-May-15 | 21338 | 2 | 3 | | III-1 | Tlk1 | 9874 | 4-May-15 |
| 20987 | 2 | 3 | | | III-1 | Tbck | 93627 | 4-May-15 | 21346 | 2 | 3 | | III-1 | Tlr12 | | |
| 20990 | 2 | 3 | | | III-1 | Tbl1x | 6907 | 4-May-15 | 21349 | 2 | 3 | | III-1 | Tlr3 | 7098 | 31-May-15 |
| 21004 | 2 | 3 | | | III-1 | Tbx18 | 9096 | 4-May-15 | 21350 | 2 | 3 | | III-1 | Tlr4 | 7099 | 31-May-15 |
| 21007 | 2 | 3 | | | III-1 | Tbx20 | 57057 | 12-May-15 | 21352 | 2 | 3 | | III-1 | Tlr6 | 10333 | 17-May-15 |
| 21012 | 2 | 3 | | | III-1 | Tbx4 | 9496 | 4-May-15 | 21354 | 2 | 3 | | III-1 | Tlr8 | 51311 | 17-May-15 |
| 21013 | 2 | 3 | | | III-1 | Tbx5 | 6910 | 31-May-15 | 21360 | 2 | 3 | | III-1 | Tm2d2 | 83877 | 4-May-15 |
| 21015 | 2 | 3 | | | III-1 | Tbxa2r | 6915 | 31-May-15 | 21362 | 2 | 3 | | III-1 | Tm4sf1 | 4071 | 4-May-15 |
| 21017 | 2 | 3 | | | III-1 | Tc2n | 123036 | 4-May-15 | 21364 | 2 | 3 | | III-1 | Tm4sf20 | 79853 | 4-May-15 |
| 21030 | 2 | 3 | | | III-1 | Tceanc | 170082 | 4-May-15 | 21367 | 2 | 3 | | III-1 | Tm6sf1 | 53346 | 17-May-15 |
| 21031 | 2 | 3 | | | III-1 | Tceanc2 | 127428 | 4-May-15 | 21370 | 2 | 3 | | III-1 | Tm7sf3 | 51768 | 12-May-15 |
| 21033 | 2 | 3 | | | III-1 | Tceb2 | 6923 | 2-Jun-15 | 21373 | 2 | 3 | | III-1 | Tm9sf3 | 56889 | 4-May-15 |
| 21040 | 2 | 3 | | | III-1 | Tcf20 | 6942 | 4-May-15 | 21376 | 2 | 3 | | III-1 | Tma7 | 51372 | 4-May-15 |
| 21044 | 2 | 3 | | | III-1 | Tcf25 | 22980 | 31-May-15 | 21377 | 2 | 3 | | III-1 | Tmbim1 | 64114 | 4-May-15 |
| 21049 | 2 | 3 | | | III-1 | Tcf7l2 | 6934 | 31-May-15 | 21379 | 2 | 3 | | III-1 | Tmbim6 | 7009 | 31-May-15 |
| 21053 | 2 | 3 | | | III-1 | Tchp | 84260 | 12-May-15 | 21386 | 2 | 3 | | III-1 | Tmc6 | 11322 | 4-May-15 |
| 21054 | 2 | 3 | | | III-1 | Tcirg1 | 10312 | 12-May-15 | 21388 | 2 | 3 | | III-1 | Tmc8 | 147138 | 4-May-15 |
| 21055 | 2 | 3 | | | III-1 | Tcl1 | 8115 | 7-Jun-15 | 21392 | 2 | 3 | | III-1 | Tmco1 | 54499 | 4-May-15 |
| 21062 | 2 | 3 | | | III-1 | Tcof1 | 6949 | 24-May-15 | 21399 | 2 | 3 | | III-1 | Tmed1 | 11018 | 4-May-15 |
| 21068 | 2 | 3 | | | III-1 | Tcp11l1 | 55346 | 4-May-15 | 21404 | 2 | 3 | | III-1 | Tmed4 | 222068 | 12-May-15 |
| 21069 | 2 | 3 | | | III-1 | Tcp11l2 | 255394 | 4-May-15 | 21407 | 2 | 3 | | III-1 | Tmed7 | 51014 | 4-May-15 |
| 21070 | 2 | 3 | | | III-1 | Tcsfv1 | | | 21411 | 2 | 3 | | III-1 | Tmeff2 | 23671 | 12-May-15 |
| 21076 | 2 | 3 | | | III-1 | Tctex1d1 | 200132 | 4-May-15 | 21413 | 2 | 3 | | III-1 | Tmem101 | 84336 | 4-May-15 |
| 21079 | 2 | 3 | | | III-1 | Tctn1 | 79600 | 23-May-15 | 21415 | 2 | 3 | | III-1 | Tmem104 | 54868 | 4-May-15 |
| 21083 | 2 | 3 | | | III-1 | Tdgf1 | 6997 | 13-Jun-15 | 21417 | 2 | 3 | | III-1 | Tmem106b | 54664 | 17-May-15 |
| 21088 | 2 | 3 | | | III-1 | Tdpoz1 | | | 21418 | 2 | 3 | | III-1 | Tmem106c | 79022 | 4-May-15 |
| 21096 | 2 | 3 | | | III-1 | Tdrd5 | 163589 | 4-May-15 | 21420 | 2 | 3 | | III-1 | Tmem108 | 66000 | 4-May-15 |
| 21101 | 2 | 3 | | | III-1 | Tdrp | 157895 | 4-May-15 | 21431 | 2 | 3 | | III-1 | Tmem123 | 114908 | 7-Jun-15 |
| 21103 | 2 | 3 | | | III-1 | Tead2 | 8463 | 4-May-15 | 21433 | 2 | 3 | | III-1 | Tmem126a | 84233 | 4-May-15 |
| 21105 | 2 | 3 | | | III-1 | Tead4 | 7004 | 4-May-15 | 21434 | 2 | 3 | | III-1 | Tmem126b | 55863 | 4-May-15 |
| 21109 | 2 | 3 | | | III-1 | Tecr | 9524 | 4-May-15 | 21441 | 2 | 3 | | III-1 | Tmem132b | 114795 | 4-May-15 |
| 21110 | 2 | 3 | | | III-1 | Tecrl | 253017 | 4-May-15 | 21447 | 2 | 3 | | III-1 | Tmem135 | 65084 | 15-May-15 |
| 21112 | 2 | 3 | | | III-1 | Tectb | 6975 | 4-May-15 | 21451 | 2 | 3 | | III-1 | Tmem140 | 55281 | 4-May-15 |
| 21115 | 2 | 3 | | | III-1 | Tefm | 79736 | 4-May-15 | 21453 | 2 | 3 | | III-1 | Tmem143 | 55260 | 12-May-15 |
| 21116 | 2 | 3 | | | III-1 | Tek | 7010 | 23-May-15 | 21455 | 2 | 3 | | III-1 | Tmem145 | 284339 | 4-May-15 |
| 21119 | 2 | 3 | | | III-1 | Tekt3 | 64518 | 4-May-15 | 21460 | 2 | 3 | | III-1 | Tmem150b | 284417 | 4-May-15 |
| 21125 | 2 | 3 | | | III-1 | Tenm1 | 10178 | 12-May-15 | 21464 | 2 | 3 | | III-1 | Tmem151b | 441151 | 4-May-15 |
| 21128 | 2 | 3 | | | III-1 | Tenm4 | 26011 | 12-May-15 | 21466 | 2 | 3 | | III-1 | Tmem158 | 25907 | 4-May-15 |
| 21132 | 2 | 3 | | | III-1 | Terf1 | 7013 | 4-May-15 | 21468 | 2 | 3 | | III-1 | Tmem160 | 54958 | 4-May-15 |
| 21133 | 2 | 3 | | | III-1 | Terf2 | 7014 | 4-May-15 | 21473 | 2 | 3 | | III-1 | Tmem165 | 55858 | 23-May-15 |
| 21134 | 2 | 3 | | | III-1 | Terf2ip | 54386 | 4-May-15 | 21479 | 2 | 3 | | III-1 | Tmem170 | 124491 | 12-May-15 |
| 21137 | 2 | 3 | | | III-1 | Tesc | 54997 | 17-May-15 | 21480 | 2 | 3 | | III-1 | Tmem170b | 100113407 | 4-May-15 |
| 21142 | 2 | 3 | | | III-1 | Tet1 | 80312 | 31-May-15 | 21481 | 2 | 3 | | III-1 | Tmem171 | 134285 | 4-May-15 |
| 21144 | 2 | 3 | | | III-1 | Tet3 | 200424 | 10-May-15 | 21483 | 2 | 3 | | III-1 | Tmem174 | 134288 | 4-May-15 |
| 21145 | 2 | 3 | | | III-1 | Tex10 | 54881 | 4-May-15 | 21486 | 2 | 3 | | III-1 | Tmem176b | 28959 | 4-May-15 |
| 21149 | 2 | 3 | | | III-1 | Tex13 | | | 21487 | 2 | 3 | | III-1 | Tmem177 | 80775 | 12-May-15 |
| 21161 | 2 | 3 | | | III-1 | Tex261 | 113419 | 4-May-15 | 21489 | 2 | 3 | | III-1 | Tmem178b | 100507421 | 4-May-15 |
| 21164 | 2 | 3 | | | III-1 | Tex29 | 121793 | 4-May-15 | 21492 | 2 | 3 | | III-1 | Tmem18 | 129787 | 4-May-15 |
| 21172 | 2 | 3 | | | III-1 | Tex43 | 389320 | 4-May-15 | 21494 | 2 | 3 | | III-1 | Tmem181a | | |
| 21177 | 2 | 3 | | | III-1 | Tfap2c | 7022 | 4-May-15 | 21500 | 2 | 3 | | III-1 | Tmem184b | 25829 | 21-May-15 |
| 21181 | 2 | 3 | | | III-1 | Tfb1m | 51106 | 4-May-15 | 21505 | 2 | 3 | | III-1 | Tmem19 | 55266 | 4-May-15 |
| 21187 | 2 | 3 | | | III-1 | Tie3 | 7030 | 28-May-15 | 21508 | 2 | 3 | | III-1 | Tmem192 | 201931 | 4-May-15 |
| 21189 | 2 | 3 | | | III-1 | Tfec | 22797 | 4-May-15 | 21509 | 2 | 3 | | III-1 | Tmem194 | 23306 | 28-May-15 |
| 21194 | 2 | 3 | | | III-1 | Tfip11 | 24144 | 4-May-15 | 21513 | 2 | 3 | | III-1 | Tmem198b | 440104 | 4-May-15 |
| 21202 | 2 | 3 | | | III-1 | Tgfa | 7039 | 12-May-15 | 21516 | 2 | 3 | | III-1 | Tmem200a | 114801 | 4-May-15 |
| 21203 | 2 | 3 | | | III-1 | Tgfb1 | 7040 | 24-May-15 | 21518 | 2 | 3 | | III-1 | Tmem200c | 645369 | 4-May-15 |
| 21204 | 2 | 3 | | | III-1 | Tgfb1i1 | 7041 | 4-May-15 | 21519 | 2 | 3 | | III-1 | Tmem201 | 199953 | 4-May-15 |
| 21205 | 2 | 3 | | | III-1 | Tgfb2 | 7042 | 23-May-15 | 21521 | 2 | 3 | | III-1 | Tmem203 | 94107 | 28-May-15 |
| 21207 | 2 | 3 | | | III-1 | Tgfbi | 7045 | 12-May-15 | 21523 | 2 | 3 | | III-1 | Tmem205 | 374882 | 4-May-15 |
| 21208 | 2 | 3 | | | III-1 | Tgfbr1 | 7046 | 24-May-15 | 21524 | 2 | 3 | | III-1 | Tmem206 | 55248 | 4-May-15 |
| 21209 | 2 | 3 | | | III-1 | Tgfbr2 | 7048 | 23-May-15 | 21527 | 2 | 3 | | III-1 | Tmem209 | 84928 | 21-May-15 |
| 21211 | 2 | 3 | | | III-1 | Tgfbrap1 | 9392 | 4-May-15 | 21532 | 2 | 3 | | III-1 | Tmem214 | 54867 | 4-May-15 |
| 21213 | 2 | 3 | | | III-1 | Tgif2 | 60436 | 4-May-15 | 21537 | 2 | 3 | | III-1 | Tmem219 | 124446 | 4-May-15 |
| 21214 | 2 | 3 | | | III-1 | Tgif2lx1 | | | 21547 | 2 | 3 | | III-1 | Tmem232 | 642987 | 4-May-15 |
| 21217 | 2 | 3 | | | III-1 | Tgm2 | 7052 | 12-May-15 | 21554 | 2 | 3 | | III-1 | Tmem239 | 100288797 | 4-May-15 |
| 21220 | 2 | 3 | | | III-1 | Tgm5 | 9333 | 4-May-15 | 21556 | 2 | 3 | | III-1 | Tmem241 | 85019 | 4-May-15 |
| 21222 | 2 | 3 | | | III-1 | Tgm7 | 116179 | 12-May-15 | 21557 | 2 | 3 | | III-1 | Tmem242 | 729515 | 4-May-15 |
| 21223 | 2 | 3 | | | III-1 | Tgoln1 | | | 21560 | 2 | 3 | | III-1 | Tmem246 | 84302 | 12-May-15 |
| 21230 | 2 | 3 | | | III-1 | Thada | 63892 | 4-May-15 | 21561 | 2 | 3 | | III-1 | Tmem247 | 388946 | 4-May-15 |
| 21234 | 2 | 3 | | | III-1 | Thap3 | 90326 | 4-May-15 | 21566 | 2 | 3 | | III-1 | Tmem253 | 643382 | 4-May-15 |
| 21235 | 2 | 3 | | | III-1 | Thap4 | 51078 | 4-May-15 | 21567 | 2 | 3 | | III-1 | Tmem254a | | |
| 21241 | 2 | 3 | | | III-1 | Thbs3 | 7059 | 12-May-15 | | | | | | | | |
| 21252 | 2 | 3 | | | III-1 | Thnsl1 | 79896 | 4-May-15 | | | | | | | | |

Fig.22 - 84

| | | | | | | | | | | | | | | |
|---|---|---|---|---|---|---|---|---|---|---|---|---|---|---|
| 21571 | 2 | 3 | | | III-1 | Tmem255b | 348013 | 4-May-15 | 21900 | 2 | 3 | | III-1 | Trem1 | 54210 | 28-May-15 |
| 21579 | 2 | 3 | | | III-1 | Tmem27 | 57393 | 17-May-15 | 21903 | 2 | 3 | | III-1 | Treml1 | 340205 | 4-May-15 |
| 21584 | 2 | 3 | | | III-1 | Tmem30c | 644444 | 4-May-15 | 21910 | 2 | 3 | | III-1 | Trh | 7200 | 4-May-15 |
| 21590 | 2 | 3 | | | III-1 | Tmem39a | 55254 | 28-May-15 | 21916 | 2 | 3 | | III-1 | Trib2 | 28951 | 4-May-15 |
| 21593 | 2 | 3 | | | III-1 | Tmem41a | 90407 | 4-May-15 | 21918 | 2 | 3 | | III-1 | Tril | 9865 | 12-May-15 |
| 21594 | 2 | 3 | | | III-1 | Tmem41b | 440026 | 4-May-15 | 21922 | 2 | 3 | | III-1 | Trim12c | | |
| 21601 | 2 | 3 | | | III-1 | Tmem5 | 10329 | 4-May-15 | 21926 | 2 | 3 | | III-1 | Trim16 | 10626 | 4-May-15 |
| 21602 | 2 | 3 | | | III-1 | Tmem50a | 23585 | 4-May-15 | 21927 | 2 | 3 | | III-1 | Trim17 | 51127 | 4-May-15 |
| 21603 | 2 | 3 | | | III-1 | Tmem50b | 757 | 4-May-15 | 21929 | 2 | 3 | | III-1 | Trim21 | 6737 | 24-May-15 |
| 21605 | 2 | 3 | | | III-1 | Tmem5los1 | | | 21932 | 2 | 3 | | III-1 | Trim25 | 7766 | 4-May-15 |
| 21609 | 2 | 3 | | | III-1 | Tmem54 | 113452 | 4-May-15 | 21937 | 2 | 3 | | III-1 | Trim3 | 10612 | 17-May-15 |
| 21613 | 2 | 3 | | | III-1 | Tmem57 | 55219 | 4-May-15 | 21938 | 2 | 3 | | III-1 | Trim30a | | |
| 21622 | 2 | 3 | | | III-1 | Tmem65 | 157378 | 12-May-15 | 21939 | 2 | 3 | | III-1 | Trim30b | | |
| 21626 | 2 | 3 | | | III-1 | Tmem69 | 51249 | 4-May-15 | 21941 | 2 | 3 | | III-1 | Trim30e-ps1 | | |
| 21629 | 2 | 3 | | | III-1 | Tmem72 | 643236 | 4-May-15 | 21949 | 2 | 3 | | III-1 | Trim37 | 4591 | 4-May-15 |
| 21632 | 2 | 3 | | | III-1 | Tmem79 | 84283 | 4-May-15 | 21961 | 2 | 3 | | III-1 | Trim47 | 91107 | 4-May-15 |
| 21634 | 2 | 3 | | | III-1 | Tmem80 | 283232 | 4-May-15 | 21962 | 2 | 3 | | III-1 | Trim50 | 135892 | 4-May-15 |
| 21637 | 2 | 3 | | | III-1 | Tmem86a | 144110 | 4-May-15 | 21975 | 2 | 3 | | III-1 | Trim66 | 9866 | 4-May-15 |
| 21639 | 2 | 3 | | | III-1 | Tmem87a | 25963 | 4-May-15 | 21978 | 2 | 3 | | III-1 | Trim69 | 140691 | 12-May-15 |
| 21644 | 2 | 3 | | | III-1 | Tmem8b | 51754 | 4-May-15 | 21984 | 2 | 3 | | III-1 | Trim9 | 114088 | 4-May-15 |
| 21645 | 2 | 3 | | | III-1 | Tmem8c | 389827 | 4-May-15 | 21995 | 2 | 3 | | III-1 | Triqk | 286144 | 4-May-15 |
| 21648 | 2 | 3 | | | III-1 | Tmem92 | 162461 | 7-Jun-15 | 21996 | 2 | 3 | | III-1 | Tril | 54802 | 4-May-15 |
| 21652 | 2 | 3 | | | III-1 | Tmem9b | 56674 | 12-May-15 | 21997 | 2 | 3 | | III-1 | Trmt1 | 55621 | 7-Jun-15 |
| 21657 | 2 | 3 | | | III-1 | Tmlhe | 55217 | 4-May-15 | 21998 | 2 | 3 | | III-1 | Trmt10a | 93587 | 4-May-15 |
| 21660 | 2 | 3 | | | III-1 | Tmod3 | 29766 | 4-May-15 | 21999 | 2 | 3 | | III-1 | Trmt10b | 158234 | 23-May-15 |
| 21665 | 2 | 3 | | | III-1 | Tmprss11bnl | 401136 | 4-May-15 | 22000 | 2 | 3 | | III-1 | Trmt10c | 54931 | 4-May-15 |
| 21666 | 2 | 3 | | | III-1 | Tmprss11c | | | 22001 | 2 | 3 | | III-1 | Trmt11 | 60487 | 4-May-15 |
| 21668 | 2 | 3 | | | III-1 | Tmprss11e | 28983 | 4-May-15 | 22002 | 2 | 3 | | III-1 | Trmt112 | 51504 | 4-May-15 |
| 21671 | 2 | 3 | | | III-1 | Tmprss12 | 283471 | 4-May-15 | 22003 | 2 | 3 | | III-1 | Trmt12 | 55039 | 4-May-15 |
| 21675 | 2 | 3 | | | III-1 | Tmprss3 | 64699 | 7-Jun-15 | 22005 | 2 | 3 | | III-1 | Trmt1l | 81627 | 4-May-15 |
| 21678 | 2 | 3 | | | III-1 | Tmprss6 | 164656 | 4-May-15 | 22007 | 2 | 3 | | III-1 | Trmt2b | 79979 | 4-May-15 |
| 21687 | 2 | 3 | | | III-1 | Tmtc1 | 83857 | 4-May-15 | 22011 | 2 | 3 | | III-1 | Trmt61a | 115768 | 4-May-15 |
| 21688 | 2 | 3 | | | III-1 | Tmtc2 | 160335 | 4-May-15 | 22014 | 2 | 3 | | III-1 | Trnau1ap | 54952 | 4-May-15 |
| 21689 | 2 | 3 | | | III-1 | Tmtc3 | 160418 | 4-May-15 | 22016 | 2 | 3 | | III-1 | Trnt1 | 51095 | 7-Jun-15 |
| 21691 | 2 | 3 | | | III-1 | Tmub1 | 83590 | 29-May-15 | 22017 | 2 | 3 | | III-1 | Tro | 7216 | 4-May-15 |
| 21694 | 2 | 3 | | | III-1 | Tmx2 | 51075 | 4-May-15 | 22020 | 2 | 3 | | III-1 | Trp53 | 7157 | 31-May-15 |
| 21696 | 2 | 3 | | | III-1 | Tmx4 | 56255 | 4-May-15 | 22023 | 2 | 3 | | III-1 | Trp53cor1 | 102800311 | 23-May-15 |
| 21699 | 2 | 3 | | | III-1 | Tnfaip1 | 7126 | 4-May-15 | 22026 | 2 | 3 | | III-1 | Trp53inp1 | | |
| 21703 | 2 | 3 | | | III-1 | Tnfaip8 | 25816 | 4-May-15 | 22027 | 2 | 3 | | III-1 | Trp53inp2 | | |
| 21709 | 2 | 3 | | | III-1 | Tnfrsf11b | 4982 | 7-Jun-15 | 22029 | 2 | 3 | | III-1 | Trp53tg5 | | |
| 21717 | 2 | 3 | | | III-1 | Tnfrsf1a | 7132 | 14-May-15 | 22031 | 2 | 3 | | III-1 | Trp73 | | |
| 21720 | 2 | 3 | | | III-1 | Tnfrsf22 | | | 22034 | 2 | 3 | | III-1 | Trpc2 | 7221 | 12-May-15 |
| 21725 | 2 | 3 | | | III-1 | Tnfrsf8 | 943 | 4-May-15 | 22035 | 2 | 3 | | III-1 | Trpc3 | 7222 | 10-May-15 |
| 21727 | 2 | 3 | | | III-1 | Tnfsf10 | 8743 | 24-May-15 | 22036 | 2 | 3 | | III-1 | Trpc4 | 7223 | 12-May-15 |
| 21728 | 2 | 3 | | | III-1 | Tnfsf11 | 8600 | 17-May-15 | 22040 | 2 | 3 | | III-1 | Trpc6 | 7225 | 24-May-15 |
| 21729 | 2 | 3 | | | III-1 | Tnfsf12 | 8742 | 4-May-15 | 22048 | 2 | 3 | | III-1 | Trpm6 | 140803 | 4-May-15 |
| 21730 | 2 | 3 | | | III-1 | Tnfsf12Tnfsf13 | 407977 | 4-May-15 | 22059 | 2 | 3 | | III-1 | Trrap | 8295 | 4-May-15 |
| 21734 | 2 | 3 | | | III-1 | Tnfsf15 | 9966 | 12-May-15 | 22067 | 2 | 3 | | III-1 | Tsc2 | 7249 | 12-May-15 |
| 21739 | 2 | 3 | | | III-1 | Tnik | 23043 | 4-May-15 | 22071 | 2 | 3 | | III-1 | Tsc22d4 | 81628 | 12-May-15 |
| 21740 | 2 | 3 | | | III-1 | Tnip1 | 10318 | 21-May-15 | 22073 | 2 | 3 | | III-1 | Tsen2 | 80746 | 23-May-15 |
| 21741 | 2 | 3 | | | III-1 | Tnip2 | 79155 | 4-May-15 | 22074 | 2 | 3 | | III-1 | Tsen34 | 79042 | 23-May-15 |
| 21742 | 2 | 3 | | | III-1 | Tnip3 | 79931 | 12-May-15 | 22078 | 2 | 3 | | III-1 | Tsga10 | 80705 | 21-May-15 |
| 21744 | 2 | 3 | | | III-1 | Tnk2 | 10188 | 21-May-15 | 22080 | 2 | 3 | | III-1 | Tsga8 | | |
| 21745 | 2 | 3 | | | III-1 | Tnk2os | | | 22084 | 2 | 3 | | III-1 | Tshz2 | 128553 | 4-May-15 |
| 21748 | 2 | 3 | | | III-1 | Tnks2 | 80351 | 12-May-15 | 22094 | 2 | 3 | | III-1 | Tspan10 | 83882 | 14-May-15 |
| 21756 | 2 | 3 | | | III-1 | Tnni3k | 51086 | 4-May-15 | 22097 | 2 | 3 | | III-1 | Tspan13 | 27075 | 12-May-15 |
| 21768 | 2 | 3 | | | III-1 | Tnrc6b | 23112 | 4-May-15 | 22098 | 2 | 3 | | III-1 | Tspan14 | 81619 | 4-May-15 |
| 21769 | 2 | 3 | | | III-1 | Tnrc6c | 57690 | 12-May-15 | 22100 | 2 | 3 | | III-1 | Tspan17 | 26262 | 4-May-15 |
| 21775 | 2 | 3 | | | III-1 | Tob2 | 10766 | 12-May-15 | 22103 | 2 | 3 | | III-1 | Tspan2os | | |
| 21776 | 2 | 3 | | | III-1 | Toe1 | 114034 | 4-May-15 | 22105 | 2 | 3 | | III-1 | Tspan31 | 6302 | 20-May-15 |
| 21777 | 2 | 3 | | | III-1 | Tollip | 54472 | 4-May-15 | 22109 | 2 | 3 | | III-1 | Tspan5 | 10098 | 4-May-15 |
| 21780 | 2 | 3 | | | III-1 | Tom1l2 | 146691 | 4-May-15 | 22113 | 2 | 3 | | III-1 | Tspan9 | 10867 | 4-May-15 |
| 21784 | 2 | 3 | | | III-1 | Tomm34 | 10953 | 4-May-15 | 22114 | 2 | 3 | | III-1 | Tspear | 54084 | 7-Jun-15 |
| 21787 | 2 | 3 | | | III-1 | Tomm5 | 401505 | 12-May-15 | 22119 | 2 | 3 | | III-1 | Tspyl3 | 128854 | 4-May-15 |
| 21788 | 2 | 3 | | | III-1 | Tomm6 | 100188893 | 4-May-15 | 22121 | 2 | 3 | | III-1 | Tspyl5 | 85453 | 4-May-15 |
| 21789 | 2 | 3 | | | III-1 | Tomm6os | | | 22124 | 2 | 3 | | III-1 | Tsr2 | 90121 | 4-May-15 |
| 21790 | 2 | 3 | | | III-1 | Tomm7 | 54543 | 4-May-15 | 22130 | 2 | 3 | | III-1 | Tssk3 | 81629 | 4-May-15 |
| 21791 | 2 | 3 | | | III-1 | Tomm70a | 9868 | 24-May-15 | 22132 | 2 | 3 | | III-1 | Tssk5 | 283629 | 12-May-15 |
| 21796 | 2 | 3 | | | III-1 | Top2a | 7153 | 12-May-15 | 22134 | 2 | 3 | | III-1 | Tst | 7263 | 4-May-15 |
| 21799 | 2 | 3 | | | III-1 | Top3b | 8940 | 4-May-15 | 22135 | 2 | 3 | | III-1 | Tsta3 | 7264 | 4-May-15 |
| 21802 | 2 | 3 | | | III-1 | Topors | 10210 | 23-May-15 | 22136 | 2 | 3 | | III-1 | Tstd1 | 100131187 | 4-May-15 |
| 21807 | 2 | 3 | | | III-1 | Torlaip2 | 163590 | 12-May-15 | 22137 | 2 | 3 | | III-1 | Tstd2 | 158427 | 4-May-15 |
| 21812 | 2 | 3 | | | III-1 | Tox | 9760 | 31-May-15 | 22140 | 2 | 3 | | III-1 | Ttbk1 | 84630 | 12-May-15 |
| 21813 | 2 | 3 | | | III-1 | Tox2 | 84969 | 4-May-15 | 22143 | 2 | 3 | | III-1 | Ttc12 | 54970 | 12-May-15 |
| 21820 | 2 | 3 | | | III-1 | Tpcn2 | 219931 | 29-May-15 | 22144 | 2 | 3 | | III-1 | Ttc13 | 79573 | 4-May-15 |
| 21823 | 2 | 3 | | | III-1 | Tpd52l2 | 7165 | 4-May-15 | 22149 | 2 | 3 | | III-1 | Ttc19 | 54902 | 4-May-15 |
| 21825 | 2 | 3 | | | III-1 | Tpgs2 | 25941 | 4-May-15 | 22151 | 2 | 3 | | III-1 | Ttc21b | 79809 | 22-May-15 |
| 21827 | 2 | 3 | | | III-1 | Tph2 | 121278 | 7-Jun-15 | 22153 | 2 | 3 | | III-1 | Ttc23 | 64927 | 4-May-15 |
| 21829 | 2 | 3 | | | III-1 | Tpk1 | 27010 | 4-May-15 | 22159 | 2 | 3 | | III-1 | Ttc28 | 23331 | 12-May-15 |
| 21836 | 2 | 3 | | | III-1 | Tpp1 | 1200 | 7-Jun-15 | 22160 | 2 | 3 | | III-1 | Ttc29 | 83894 | 4-May-15 |
| 21840 | 2 | 3 | | | III-1 | Tppp3 | 51673 | 4-May-15 | 22162 | 2 | 3 | | III-1 | Ttc30a1 | | |
| 21842 | 2 | 3 | | | III-1 | Tpra1 | 131601 | 4-May-15 | 22164 | 2 | 3 | | III-1 | Ttc30b | 150737 | 4-May-15 |
| 21844 | 2 | 3 | | | III-1 | Tprgl | | | 22165 | 2 | 3 | | III-1 | Ttc32 | 130502 | 12-May-15 |
| 21849 | 2 | 3 | | | III-1 | Tpsg1 | 25823 | 12-May-15 | 22166 | 2 | 3 | | III-1 | Ttc33 | 23548 | 4-May-15 |
| 21852 | 2 | 3 | | | III-1 | Tpt1 | 7178 | 4-May-15 | 22169 | 2 | 3 | | III-1 | Ttc37 | 9652 | 4-May-15 |
| 21853 | 2 | 3 | | | III-1 | Tpte | 7179 | 12-May-15 | 22170 | 2 | 3 | | III-1 | Ttc38 | 55020 | 4-May-15 |
| 21858 | 2 | 3 | | | III-1 | Trabd2b | 388630 | 4-May-15 | 22172 | 2 | 3 | | III-1 | Ttc39b | 158219 | 4-May-15 |
| 21861 | 2 | 3 | | | III-1 | Traf2 | 7186 | 7-Jun-15 | 22181 | 2 | 3 | | III-1 | Ttc9b | 148014 | 4-May-15 |
| 21865 | 2 | 3 | | | III-1 | Traf3ip3 | 80342 | 4-May-15 | 22189 | 2 | 3 | | III-1 | Ttll1 | 25809 | 4-May-15 |
| 21867 | 2 | 3 | | | III-1 | Traf5 | 7188 | 4-May-15 | 22191 | 2 | 3 | | III-1 | Ttll11 | 158135 | 4-May-15 |
| 21868 | 2 | 3 | | | III-1 | Traf6 | 7189 | 23-May-15 | 22192 | 2 | 3 | | III-1 | Ttll12 | 23170 | 4-May-15 |
| 21872 | 2 | 3 | | | III-1 | Trak1 | 22906 | 4-May-15 | 22193 | 2 | 3 | | III-1 | Ttll13 | 440307 | 4-May-15 |
| 21874 | 2 | 3 | | | III-1 | Tram1 | 23471 | 7-Jun-15 | 22195 | 2 | 3 | | III-1 | Ttll3 | 26140 | 23-May-15 |
| 21887 | 2 | 3 | | | III-1 | Trappc3 | 27095 | 2-Jun-15 | 22198 | 2 | 3 | | III-1 | Ttll6 | 284076 | 12-May-15 |
| 21890 | 2 | 3 | | | III-1 | Trappc5 | 126003 | 4-May-15 | 22204 | 2 | 3 | | III-1 | Ttpal | 79183 | 4-May-15 |
| 21893 | 2 | 3 | | | III-1 | Trappc8 | 22878 | 21-May-15 | 22207 | 2 | 3 | | III-1 | Ttyh2 | 94015 | 12-May-15 |
| 21896 | 2 | 3 | | | III-1 | Trcg1 | | | | | | | | | | |

Fig.22 - 85

| | | | | | | | | | | | | | | |
|---|---|---|---|---|---|---|---|---|---|---|---|---|---|---|
| 22208 | 2 | 3 | | III-1 | Tryh3 | 80727 | 4-May-15 | 22518 | 2 | 3 | | III-1 | Usb1 | 79650 | 23-May-15 |
| 22209 | 2 | 3 | | III-1 | Tub | 7275 | 28-May-15 | 22522 | 2 | 3 | | III-1 | Ush1c | 10083 | 23-May-15 |
| 22212 | 2 | 3 | | III-1 | Tuba1c | 84790 | 12-May-15 | 22531 | 2 | 3 | | III-1 | Usp12 | 219333 | 7-Jun-15 |
| 22214 | 2 | 3 | | III-1 | Tuba3b | | | 22542 | 2 | 3 | | III-1 | Usp19 | 10869 | 28-May-15 |
| 22223 | 2 | 3 | | III-1 | Tubb4a | 10382 | 12-May-15 | 22545 | 2 | 3 | | III-1 | Usp21 | 27005 | 7-Jun-15 |
| 22224 | 2 | 3 | | III-1 | Tubb4b | 10383 | 21-May-15 | 22552 | 2 | 3 | | III-1 | Usp29 | 57663 | 3-May-15 |
| 22227 | 2 | 3 | | III-1 | Tubd1 | 51174 | 4-May-15 | 22556 | 2 | 3 | | III-1 | Usp32 | 84669 | 4-May-15 |
| 22229 | 2 | 3 | | III-1 | Tubg1 | 7283 | 31-May-15 | 22560 | 2 | 3 | | III-1 | Usp36 | 57602 | 12-May-15 |
| 22231 | 2 | 3 | | III-1 | Tubgcp2 | 10844 | 4-May-15 | 22562 | 2 | 3 | | III-1 | Usp38 | 84640 | 12-May-15 |
| 22236 | 2 | 3 | | III-1 | Tufm | 7284 | 13-May-15 | 22571 | 2 | 3 | | III-1 | Usp47 | 55031 | 4-May-15 |
| 22240 | 2 | 3 | | III-1 | Tulp2 | 7288 | 28-May-15 | 22574 | 2 | 3 | | III-1 | Usp5 | 8078 | 29-May-15 |
| 22245 | 2 | 3 | | III-1 | Tusc2 | 11334 | 4-May-15 | 22578 | 2 | 3 | | III-1 | Usp54 | 159195 | 4-May-15 |
| 22251 | 2 | 3 | | III-1 | Twf1 | 5756 | 3-May-15 | 22579 | 2 | 3 | | III-1 | Usp6nl | 9712 | 12-May-15 |
| 22253 | 2 | 3 | | III-1 | Twist1 | 7291 | 28-May-15 | 22580 | 2 | 3 | | III-1 | Usp7 | 7874 | 31-May-15 |
| 22254 | 2 | 3 | | III-1 | Twist2 | 117581 | 4-May-15 | 22583 | 2 | 3 | | III-1 | Usp9y | 8287 | 23-May-15 |
| 22256 | 2 | 3 | | III-1 | Twsg1 | 57045 | 4-May-15 | 22586 | 2 | 3 | | III-1 | Utf1 | 8433 | 4-May-15 |
| 22258 | 2 | 3 | | III-1 | Txlna | 200081 | 28-May-15 | 22587 | 2 | 3 | | III-1 | Utp11l | 51118 | 4-May-15 |
| 22262 | 2 | 3 | | III-1 | Txn2 | 25828 | 12-May-15 | 22588 | 2 | 3 | | III-1 | Utp14a | 10813 | 4-May-15 |
| 22263 | 2 | 3 | | III-1 | Txndc11 | 51061 | 12-May-15 | 22600 | 2 | 3 | | III-1 | Uty | 7404 | 12-May-15 |
| 22264 | 2 | 3 | | III-1 | Txndc12 | 51060 | 4-May-15 | 22602 | 2 | 3 | | III-1 | Uvssa | 57654 | 21-May-15 |
| 22265 | 2 | 3 | | III-1 | Txndc15 | 79770 | 4-May-15 | 22603 | 2 | 3 | | III-1 | Uxs1 | 80146 | 12-May-15 |
| 22267 | 2 | 3 | | III-1 | Txndc17 | 84817 | 4-May-15 | 22604 | 2 | 3 | | III-1 | Uxt | 8409 | 4-May-15 |
| 22269 | 2 | 3 | | III-1 | Txndc5 | 81567 | 31-May-15 | 22610 | 2 | 3 | | III-1 | Vamp2 | 6844 | 4-May-15 |
| 22273 | 2 | 3 | | III-1 | Txnl1 | 9352 | 12-May-15 | 22613 | 2 | 3 | | III-1 | Vamp5 | 10791 | 4-May-15 |
| 22274 | 2 | 3 | | III-1 | Txnl4a | 10907 | 2-Jun-15 | 22614 | 2 | 3 | | III-1 | Vamp7 | 6845 | 21-May-15 |
| 22278 | 2 | 3 | | III-1 | Txnrd3 | 114112 | 12-May-15 | 22617 | 2 | 3 | | III-1 | Vangl2 | 57216 | 4-May-15 |
| 22279 | 2 | 3 | | III-1 | Tyk2 | 7297 | 4-May-15 | 22621 | 2 | 3 | | III-1 | Vars2 | 57176 | 7-Jun-15 |
| 22291 | 2 | 3 | | III-1 | U2af1 | 7307 | 2-Jun-15 | 22624 | 2 | 3 | | III-1 | Vasn | 114990 | 4-May-15 |
| 22292 | 2 | 3 | | III-1 | U2af1l4 | 199746 | 7-Jun-15 | 22625 | 2 | 3 | | III-1 | Vasp | 7408 | 17-May-15 |
| 22299 | 2 | 3 | | III-1 | Uba1 | 7317 | 31-May-15 | 22628 | 2 | 3 | | III-1 | Vaultrc5 | | |
| 22303 | 2 | 3 | | III-1 | Uba5 | 79876 | 4-May-15 | 22629 | 2 | 3 | | III-1 | Vav1 | 7409 | 12-May-15 |
| 22305 | 2 | 3 | | III-1 | Uba6 | 55236 | 4-May-15 | 22631 | 2 | 3 | | III-1 | Vav3 | 10451 | 4-May-15 |
| 22306 | 2 | 3 | | III-1 | Uba7 | 7318 | 4-May-15 | 22632 | 2 | 3 | | III-1 | Vax1 | 11023 | 23-May-15 |
| 22308 | 2 | 3 | | III-1 | Ubac2 | 337867 | 3-May-15 | 22643 | 2 | 3 | | III-1 | Vdac2 | 7417 | 12-May-15 |
| 22315 | 2 | 3 | | III-1 | Ubash3a | 53347 | 24-May-15 | 22646 | 2 | 3 | | III-1 | Vegfa | 7422 | 31-May-15 |
| 22322 | 2 | 3 | | III-1 | Ube2c | 11065 | 4-May-15 | 22647 | 2 | 3 | | III-1 | Vegfb | 7423 | 12-May-15 |
| 22324 | 2 | 3 | | III-1 | Ube2d1 | 7321 | 31-May-15 | 22648 | 2 | 3 | | III-1 | Vegfc | 7424 | 4-May-15 |
| 22325 | 2 | 3 | | III-1 | Ube2d2a | | | 22653 | 2 | 3 | | III-1 | Vgll1 | 51442 | 7-Jun-15 |
| 22339 | 2 | 3 | | III-1 | Ube2j2 | 118424 | 29-May-15 | 22663 | 2 | 3 | | III-1 | Vipas39 | 63894 | 4-May-15 |
| 22340 | 2 | 3 | | III-1 | Ube2k | 3093 | 2-Jun-15 | 22665 | 2 | 3 | | III-1 | Vipr2 | 7434 | 12-May-15 |
| 22343 | 2 | 3 | | III-1 | Ube2m | 9040 | 4-May-15 | 22666 | 2 | 3 | | III-1 | Vit | 5212 | 4-May-15 |
| 22346 | 2 | 3 | | III-1 | Ube2q1 | 55585 | 2-Jun-15 | 22667 | 2 | 3 | | III-1 | Vkorc1 | 79001 | 17-May-15 |
| 22347 | 2 | 3 | | III-1 | Ube2q2 | 92912 | 12-May-15 | 22668 | 2 | 3 | | III-1 | Vkorc1l1 | 154807 | 4-May-15 |
| 22349 | 2 | 3 | | III-1 | Ube2r2 | 54926 | 12-May-15 | 22670 | 2 | 3 | | III-1 | Vma21 | 203547 | 7-Jun-15 |
| 22350 | 2 | 3 | | III-1 | Ube2s | 27338 | 4-May-15 | 22737 | 2 | 3 | | III-1 | Vmn1r183 | | |
| 22352 | 2 | 3 | | III-1 | Ube2u | 148581 | 4-May-15 | 22923 | 2 | 3 | | III-1 | Vmn2r3 | | |
| 22357 | 2 | 3 | | III-1 | Ube3a | 7337 | 23-May-15 | 22997 | 2 | 3 | | III-1 | Vmn2r98 | | |
| 22359 | 2 | 3 | | III-1 | Ube3c | 9690 | 4-May-15 | 23000 | 2 | 3 | | III-1 | Vmn2r-ps129 | | |
| 22361 | 2 | 3 | | III-1 | Ube4b | 10277 | 4-May-15 | 23005 | 2 | 3 | | III-1 | Vmp1 | 81671 | 21-May-15 |
| 22367 | 2 | 3 | | III-1 | Ubl5 | 59286 | 7-Jun-15 | 23008 | 2 | 3 | | III-1 | Vopp1 | 81552 | 12-May-15 |
| 22368 | 2 | 3 | | III-1 | Ubl7 | 84993 | 12-May-15 | 23009 | 2 | 3 | | III-1 | Vprbp | 9730 | 4-May-15 |
| 22377 | 2 | 3 | | III-1 | Ubqln4 | 56893 | 13-May-15 | 23010 | 2 | 3 | | III-1 | Vpreb1 | 7441 | 12-May-15 |
| 22378 | 2 | 3 | | III-1 | Ubqlnl | 143630 | 4-May-15 | 23011 | 2 | 3 | | III-1 | Vpreb2 | 3543 | 12-May-15 |
| 22386 | 2 | 3 | | III-1 | Ubrd2 | 92181 | 4-May-15 | 23015 | 2 | 3 | | III-1 | Vps13b | 157680 | 23-May-15 |
| 22391 | 2 | 3 | | III-1 | Ubxn11 | 91544 | 4-May-15 | 23017 | 2 | 3 | | III-1 | Vps13d | 55187 | 12-May-15 |
| 22392 | 2 | 3 | | III-1 | Ubxn2a | 165324 | 21-May-15 | 23019 | 2 | 3 | | III-1 | Vps18 | 57617 | 4-May-15 |
| 22393 | 2 | 3 | | III-1 | Ubxn2b | 137886 | 21-May-15 | 23024 | 2 | 3 | | III-1 | Vps29 | 51699 | 4-May-15 |
| 22394 | 2 | 3 | | III-1 | Ubxn4 | 23190 | 4-May-15 | 23029 | 2 | 3 | | III-1 | Vps37a | 137492 | 4-May-15 |
| 22396 | 2 | 3 | | III-1 | Ubxn7 | 26043 | 4-May-15 | 23031 | 2 | 3 | | III-1 | Vps37c | 55048 | 4-May-15 |
| 22401 | 2 | 3 | | III-1 | Uchl4 | | | 23033 | 2 | 3 | | III-1 | Vps39 | 23339 | 21-May-15 |
| 22402 | 2 | 3 | | III-1 | Uchl5 | 51377 | 4-May-15 | 23047 | 2 | 3 | | III-1 | Vrk3 | 51231 | 21-May-15 |
| 22403 | 2 | 3 | | III-1 | Uck1 | 83549 | 13-Jun-15 | 23051 | 2 | 3 | | III-1 | Vsig10l | 147645 | 4-May-15 |
| 22410 | 2 | 3 | | III-1 | Ucn3 | 114131 | 7-Jun-15 | 23053 | 2 | 3 | | III-1 | Vsig4 | 11326 | 4-May-15 |
| 22416 | 2 | 3 | | III-1 | Ufd1l | 7353 | 28-May-15 | 23057 | 2 | 3 | | III-1 | Vstm2b | 342865 | 4-May-15 |
| 22417 | 2 | 3 | | III-1 | Ufl1 | 23376 | 23-May-15 | 23059 | 2 | 3 | | III-1 | Vstm4 | 196740 | 4-May-15 |
| 22420 | 2 | 3 | | III-1 | Ufsp2 | 55325 | 4-May-15 | 23061 | 2 | 3 | | III-1 | Vsx1 | 30813 | 12-May-15 |
| 22423 | 2 | 3 | | III-1 | Uggt1 | 56886 | 4-May-15 | 23070 | 2 | 3 | | III-1 | Vwa3a | 146177 | 4-May-15 |
| 22434 | 2 | 3 | | III-1 | Ugt2a1 | 10941 | 4-May-15 | 23071 | 2 | 3 | | III-1 | Vwa5a | 4013 | 4-May-15 |
| 22439 | 2 | 3 | | III-1 | Ugt2b35 | | | 23082 | 2 | 3 | | III-1 | Wac | 51322 | 12-May-15 |
| 22441 | 2 | 3 | | III-1 | Ugt2b37 | | | 23086 | 2 | 3 | | III-1 | Wars2 | 10352 | 12-May-15 |
| 22451 | 2 | 3 | | III-1 | Uhrf2 | 115426 | 4-May-15 | 23087 | 2 | 3 | | III-1 | Was | 7454 | 23-May-15 |
| 22459 | 2 | 3 | | III-1 | Umodl1 | 89766 | 4-May-15 | 23090 | 2 | 3 | | III-1 | Wasf3 | 10810 | 12-May-15 |
| 22461 | 2 | 3 | | III-1 | Unc119 | 9094 | 4-May-15 | 23092 | 2 | 3 | | III-1 | Wasl | 8976 | 4-May-15 |
| 22463 | 2 | 3 | | III-1 | Unc13a | 23025 | 17-May-15 | 23096 | 2 | 3 | | III-1 | Wbp2 | 23558 | 12-May-15 |
| 22465 | 2 | 3 | | III-1 | Unc13c | 440279 | 12-May-15 | 23100 | 2 | 3 | | III-1 | Wbscr16 | 81554 | 4-May-15 |
| 22471 | 2 | 3 | | III-1 | Unc5b | 219699 | 4-May-15 | 23101 | 2 | 3 | | III-1 | Wbscr17 | 64409 | 4-May-15 |
| 22472 | 2 | 3 | | III-1 | Unc5c | 8633 | 4-May-15 | 23102 | 2 | 3 | | III-1 | Wbscr22 | 114049 | 4-May-15 |
| 22478 | 2 | 3 | | III-1 | Unc5d | 137970 | 4-May-15 | 23104 | 2 | 3 | | III-1 | Wbscr27 | 155368 | 3-May-15 |
| 22479 | 2 | 3 | | III-1 | Unc93b1 | 81622 | 4-May-15 | 23105 | 2 | 3 | | III-1 | Wbscr28 | 135886 | 4-May-15 |
| 22485 | 2 | 3 | | III-1 | Uncx | 340260 | 21-May-15 | 23109 | 2 | 3 | | III-1 | Wdfy4 | 57705 | 4-May-15 |
| 22491 | 2 | 3 | | III-1 | Upf1 | 5976 | 2-Jun-15 | 23110 | 2 | 3 | | III-1 | Wdhd1 | 11169 | 4-May-15 |
| 22500 | 2 | 3 | | III-1 | Upk2 | 7379 | 4-May-15 | 23111 | 2 | 3 | | III-1 | Wdpcp | 51057 | 23-May-15 |
| 22501 | 2 | 3 | | III-1 | Uqcr10 | 29796 | 4-May-15 | 23112 | 2 | 3 | | III-1 | Wdr1 | 9948 | 14-May-15 |
| 22502 | 2 | 3 | | III-1 | Uqcr11 | 10975 | 4-May-15 | 23115 | 2 | 3 | | III-1 | Wdr13 | 64743 | 20-May-15 |
| 22503 | 2 | 3 | | III-1 | Uqcrb | 7381 | 12-May-15 | 23118 | 2 | 3 | | III-1 | Wdr18 | 57418 | 4-May-15 |
| 22504 | 2 | 3 | | III-1 | Uqcrc1 | 7384 | 4-May-15 | 23122 | 2 | 3 | | III-1 | Wdr24 | 84219 | 29-May-15 |
| 22505 | 2 | 3 | | III-1 | Uqcrc2 | 7385 | 4-May-15 | 23124 | 2 | 3 | | III-1 | Wdr26 | 80232 | 21-May-15 |
| 22506 | 2 | 3 | | III-1 | Uqcrfs1 | 7386 | 4-May-15 | 23127 | 2 | 3 | | III-1 | Wdr31 | 114987 | 4-May-15 |
| 22507 | 2 | 3 | | III-1 | Uqcrh | 7388 | 4-May-15 | 23130 | 2 | 3 | | III-1 | Wdr35 | 57539 | 28-May-15 |
| 22508 | 2 | 3 | | III-1 | Uqcrq | 27089 | 4-May-15 | 23131 | 2 | 3 | | III-1 | Wdr36 | 134430 | 4-May-15 |
| 22509 | 2 | 3 | | III-1 | Urad | 646625 | 4-May-15 | 23137 | 2 | 3 | | III-1 | Wdr44 | 54521 | 4-May-15 |
| 22510 | 2 | 3 | | III-1 | Urah | 100130015 | 4-May-15 | 23138 | 2 | 3 | | III-1 | Wdr45 | 11152 | 4-May-15 |
| 22511 | 2 | 3 | | III-1 | Urb1 | 9875 | 12-May-15 | 23139 | 2 | 3 | | III-1 | Wdr45b | 56270 | 21-May-15 |
| 22512 | 2 | 3 | | III-1 | Urb2 | 9816 | 4-May-15 | 23141 | 2 | 3 | | III-1 | Wdr47 | 22911 | 4-May-15 |
| 22514 | 2 | 3 | | III-1 | Urgcp | 55665 | 12-May-15 | 23145 | 2 | 3 | | III-1 | Wdr53 | 348793 | 4-May-15 |
| 22514 | 2 | 3 | | III-1 | Urm1 | 81605 | 24-May-15 | 23146 | 2 | 3 | | III-1 | Wdr54 | 84056 | 4-May-15 |
| 22517 | 2 | 3 | | III-1 | Uros | 7390 | 4-May-15 | 23147 | 2 | 3 | | III-1 | Wdr55 | 54853 | 4-May-15 |

Fig.22 - 86

| | | | | | | | | | | | | | |
|---|---|---|---|---|---|---|---|---|---|---|---|---|---|
| 23152 | 2 | 3 | | III-1 | Wdr61 | 80349 | 12-May-15 | 23529 | 2 | 3 | | III-1 | Zfp160 | | |
| 23160 | 2 | 3 | | III-1 | Wdr73 | 84942 | 20-May-15 | 23536 | 2 | 3 | | III-1 | Zfp189 | | |
| 23162 | 2 | 3 | | III-1 | Wdr75 | 84128 | 3-May-15 | 23537 | 2 | 3 | | III-1 | Zfp191 | 7572 | 12-May-15 |
| 23170 | 2 | 3 | | III-1 | Wdr83os | 51398 | 4-May-15 | 23540 | 2 | 3 | | III-1 | Zfp207 | | |
| 23171 | 2 | 3 | | III-1 | Wdr86 | 349136 | 21-May-15 | 23550 | 2 | 3 | | III-1 | Zfp251 | | |
| 23172 | 2 | 3 | | III-1 | Wdr89 | 112840 | 4-May-15 | 23558 | 2 | 3 | | III-1 | Zfp276 | 92822 | 4-May-15 |
| 23173 | 2 | 3 | | III-1 | Wdr90 | 197335 | 4-May-15 | 23561 | 2 | 3 | | III-1 | Zfp280b | | |
| 23174 | 2 | 3 | | III-1 | Wdr91 | 29062 | 12-May-15 | 23562 | 2 | 3 | | III-1 | Zfp280c | | |
| 23175 | 2 | 3 | | III-1 | Wdr92 | 116143 | 4-May-15 | 23563 | 2 | 3 | | III-1 | Zfp280d | | |
| 23183 | 2 | 3 | | III-1 | Wee2 | 494551 | 7-Jun-15 | 23569 | 2 | 3 | | III-1 | Zfp296 | 162979 | 4-May-15 |
| 23189 | 2 | 3 | | III-1 | Wfdc15a | | | 23571 | 2 | 3 | | III-1 | Zfp30 | 22835 | 4-May-15 |
| 23195 | 2 | 3 | | III-1 | Wfdc3 | 140886 | 4-May-15 | 23572 | 2 | 3 | | III-1 | Zfp300 | | |
| 23196 | 2 | 3 | | III-1 | Wfdc5 | 149708 | 4-May-15 | 23574 | 2 | 3 | | III-1 | Zfp317 | | |
| 23201 | 2 | 3 | | III-1 | Wfikkn1 | 117166 | 4-May-15 | 23576 | 2 | 3 | | III-1 | Zfp319 | 57567 | 4-May-15 |
| 23203 | 2 | 3 | | III-1 | Wfs1 | 7466 | 31-May-15 | 23579 | 2 | 3 | | III-1 | Zfp326 | 284695 | 4-May-15 |
| 23204 | 2 | 3 | | III-1 | Whamm | 128720 | 4-May-15 | 23583 | 2 | 3 | | III-1 | Zfp335 | | |
| 23206 | 2 | 3 | | III-1 | Whsc1 | 7468 | 23-May-15 | 23590 | 2 | 3 | | III-1 | Zfp354b | | |
| 23209 | 2 | 3 | | III-1 | Wif1 | 11197 | 4-May-15 | 23591 | 2 | 3 | | III-1 | Zfp354c | | |
| 23214 | 2 | 3 | | III-1 | Wipi2 | 26100 | 21-May-15 | 23594 | 2 | 3 | | III-1 | Zfp362 | | |
| 23222 | 2 | 3 | | III-1 | Wnk3 | 55287 | 4-May-15 | 23601 | 2 | 3 | | III-1 | Zfp383 | | |
| 23224 | 2 | 3 | | III-1 | Wnt1 | 7471 | 17-May-15 | 23605 | 2 | 3 | | III-1 | Zfp384 | | |
| 23226 | 2 | 3 | | III-1 | Wnt10b | 7480 | 4-May-15 | 23611 | 2 | 3 | | III-1 | Zfp39 | | |
| 23228 | 2 | 3 | | III-1 | Wnt16 | 51384 | 7-Jun-15 | 23613 | 2 | 3 | | III-1 | Zfp397 | | |
| 23234 | 2 | 3 | | III-1 | Wnt5a | 7474 | 31-May-15 | 23617 | 2 | 3 | | III-1 | Zfp408 | | |
| 23237 | 2 | 3 | | III-1 | Wnt7a | 7476 | 4-May-15 | 23618 | 2 | 3 | | III-1 | Zfp41 | 286128 | 12-May-15 |
| 23239 | 2 | 3 | | III-1 | Wnt8a | 7478 | 7-Jun-15 | 23624 | 2 | 3 | | III-1 | Zfp422 | 7570 | 4-May-15 |
| 23242 | 2 | 3 | | III-1 | Wnt9b | 7484 | 4-May-15 | 23629 | 2 | 3 | | III-1 | Zfp443 | | |
| 23248 | 2 | 3 | | III-1 | Wsb2 | 55884 | 2-Jun-15 | 23634 | 2 | 3 | | III-1 | Zfp446 | | |
| 23250 | 2 | 3 | | III-1 | Wscd2 | 9671 | 12-May-15 | 23637 | 2 | 3 | | III-1 | Zfp454 | | |
| 23256 | 2 | 3 | | III-1 | Wwc2 | 80014 | 4-May-15 | 23645 | 2 | 3 | | III-1 | Zfp467 | 168544 | 4-May-15 |
| 23257 | 2 | 3 | | III-1 | Wwox | 51741 | 12-May-15 | 23646 | 2 | 3 | | III-1 | Zfp472 | | |
| 23258 | 2 | 3 | | III-1 | Wwp1 | 11059 | 4-May-15 | 23649 | 2 | 3 | | III-1 | Zfp488 | | |
| 23261 | 2 | 3 | | III-1 | Xab2 | 56949 | 4-May-15 | 23652 | 2 | 3 | | III-1 | Zfp507 | | |
| 23267 | 2 | 3 | | III-1 | Xiap | 331 | 23-May-15 | 23658 | 2 | 3 | | III-1 | Zfp518a | | |
| 23272 | 2 | 3 | | III-1 | Xkr4 | 114786 | 4-May-15 | 23661 | 2 | 3 | | III-1 | Zfp521 | | |
| 23284 | 2 | 3 | | III-1 | Xkr4b | | | 23662 | 2 | 3 | | III-1 | Zfp523 | 7629 | 4-May-15 |
| 23292 | 2 | 3 | | III-1 | Xpc | 7508 | 23-May-15 | 23663 | 2 | 3 | | III-1 | Zfp524 | | |
| 23294 | 2 | 3 | | III-1 | Xpnpep2 | 7512 | 4-May-15 | 23664 | 2 | 3 | | III-1 | Zfp526 | | |
| 23296 | 2 | 3 | | III-1 | Xpo1 | 7514 | 24-May-15 | 23666 | 2 | 3 | | III-1 | Zfp532 | | |
| 23299 | 2 | 3 | | III-1 | Xpo6 | 23214 | 4-May-15 | 23667 | 2 | 3 | | III-1 | Zfp534 | | |
| 23301 | 2 | 3 | | III-1 | Xpot | 11260 | 4-May-15 | 23670 | 2 | 3 | | III-1 | Zfp541 | | |
| 23303 | 2 | 3 | | III-1 | Xrcc1 | 7515 | 31-May-15 | 23673 | 2 | 3 | | III-1 | Zfp558 | | |
| 23306 | 2 | 3 | | III-1 | Xrcc4 | 7518 | 17-May-15 | 23677 | 2 | 3 | | III-1 | Zfp568 | | |
| 23308 | 2 | 3 | | III-1 | Xrcc6 | 2547 | 24-May-15 | 23679 | 2 | 3 | | III-1 | Zfp572 | | |
| 23315 | 2 | 3 | | III-1 | Xylt1 | 64131 | 23-May-15 | 23685 | 2 | 3 | | III-1 | Zfp583 | | |
| 23320 | 2 | 3 | | III-1 | Yars | 8565 | 17-May-15 | 23689 | 2 | 3 | | III-1 | Zfp595 | | |
| 23326 | 2 | 3 | | III-1 | Ydjc | 150223 | 4-May-15 | 23699 | 2 | 3 | | III-1 | Zfp609 | | |
| 23327 | 2 | 3 | | III-1 | Yeats2 | 55689 | 4-May-15 | 23700 | 2 | 3 | | III-1 | Zfp61 | | |
| 23330 | 2 | 3 | | III-1 | Yif1a | 10897 | 12-May-15 | 23702 | 2 | 3 | | III-1 | Zfp616 | | |
| 23333 | 2 | 3 | | III-1 | Yipf2 | 78992 | 4-May-15 | 23705 | 2 | 3 | | III-1 | Zfp619 | | |
| 23334 | 2 | 3 | | III-1 | Yipf3 | 25844 | 4-May-15 | 23713 | 2 | 3 | | III-1 | Zfp64 | 55734 | 4-May-15 |
| 23341 | 2 | 3 | | III-1 | Yme1l1 | 10730 | 12-May-15 | 23719 | 2 | 3 | | III-1 | Zfp65 | | |
| 23345 | 2 | 3 | | III-1 | Ypel3 | 83719 | 4-May-15 | 23723 | 2 | 3 | | III-1 | Zfp653 | | |
| 23349 | 2 | 3 | | III-1 | Ythdc1 | 91746 | 12-May-15 | 23724 | 2 | 3 | | III-1 | Zfp654 | | |
| 23364 | 2 | 3 | | III-1 | Zan | 7455 | 12-May-15 | 23732 | 2 | 3 | | III-1 | Zfp672 | | |
| 23367 | 2 | 3 | | III-1 | Zar1l | 646799 | 4-May-15 | 23738 | 2 | 3 | | III-1 | Zfp69 | 339559 | 4-May-15 |
| 23370 | 2 | 3 | | III-1 | Zbed4 | 9889 | 4-May-15 | 23739 | 2 | 3 | | III-1 | Zfp691 | 51058 | 4-May-15 |
| 23374 | 2 | 3 | | III-1 | Zbtb1 | 22890 | 4-May-15 | 23741 | 2 | 3 | | III-1 | Zfp697 | | |
| 23378 | 2 | 3 | | III-1 | Zbtb14 | 7541 | 1-Jun-15 | 23742 | 2 | 3 | | III-1 | Zfp7 | | |
| 23382 | 2 | 3 | | III-1 | Zbtb2 | 57621 | 3-May-15 | 23743 | 2 | 3 | | III-1 | Zfp703 | | |
| 23393 | 2 | 3 | | III-1 | Zbtb37 | 84614 | 4-May-15 | 23745 | 2 | 3 | | III-1 | Zfp706 | | |
| 23396 | 2 | 3 | | III-1 | Zbtb4 | 57659 | 4-May-15 | 23755 | 2 | 3 | | III-1 | Zfp735 | | |
| 23398 | 2 | 3 | | III-1 | Zbtb41 | 360080 | 4-May-15 | 23761 | 2 | 3 | | III-1 | Zfp748 | | |
| 23400 | 2 | 3 | | III-1 | Zbtb43 | 23099 | 4-May-15 | 23763 | 2 | 3 | | III-1 | Zfp758 | | |
| 23401 | 2 | 3 | | III-1 | Zbtb44 | 29068 | 4-May-15 | 23769 | 2 | 3 | | III-1 | Zfp770 | | |
| 23410 | 2 | 3 | | III-1 | Zbtb7c | 201560 | 12-May-15 | 23771 | 2 | 3 | | III-1 | Zfp772 | | |
| 23411 | 2 | 3 | | III-1 | Zbtb8a | 653121 | 12-May-15 | 23772 | 2 | 3 | | III-1 | Zfp773 | | |
| 23419 | 2 | 3 | | III-1 | Zc3h10 | 84872 | 12-May-15 | 23774 | 2 | 3 | | III-1 | Zfp777 | | |
| 23422 | 2 | 3 | | III-1 | Zc3h12b | 340554 | 4-May-15 | 23779 | 2 | 3 | | III-1 | Zfp784 | | |
| 23424 | 2 | 3 | | III-1 | Zc3h12d | 340152 | 4-May-15 | 23780 | 2 | 3 | | III-1 | Zfp786 | | |
| 23427 | 2 | 3 | | III-1 | Zc3h15 | 55854 | 12-May-15 | 23783 | 2 | 3 | | III-1 | Zfp790 | | |
| 23430 | 2 | 3 | | III-1 | Zc3h4 | 23211 | 4-May-15 | 23785 | 2 | 3 | | III-1 | Zfp799 | | |
| 23432 | 2 | 3 | | III-1 | Zc3h7a | 29066 | 4-May-15 | 23790 | 2 | 3 | | III-1 | Zfp809 | | |
| 23435 | 2 | 3 | | III-1 | Zc3hav1 | 56829 | 4-May-15 | 23793 | 2 | 3 | | III-1 | Zfp811 | | |
| 23441 | 2 | 3 | | III-1 | Zcchc12 | 170261 | 4-May-15 | 23794 | 2 | 3 | | III-1 | Zfp819 | | |
| 23444 | 2 | 3 | | III-1 | Zcchc16 | 340595 | 4-May-15 | 23796 | 2 | 3 | | III-1 | Zfp820 | | |
| 23447 | 2 | 3 | | III-1 | Zcchc2 | 54877 | 4-May-15 | 23800 | 2 | 3 | | III-1 | Zfp830 | | |
| 23449 | 2 | 3 | | III-1 | Zcchc3 | 85364 | 4-May-15 | 23806 | 2 | 3 | | III-1 | Zfp850 | | |
| 23457 | 2 | 3 | | III-1 | Zcwpw1 | 55063 | 4-May-15 | 23809 | 2 | 3 | | III-1 | Zfp865 | | |
| 23460 | 2 | 3 | | III-1 | Zdhhc11 | 79844 | 14-May-15 | 23812 | 2 | 3 | | III-1 | Zfp868 | | |
| 23462 | 2 | 3 | | III-1 | Zdhhc13 | 54503 | 12-May-15 | 23820 | 2 | 3 | | III-1 | Zfp874b | | |
| 23463 | 2 | 3 | | III-1 | Zdhhc14 | 79683 | 4-May-15 | 23824 | 2 | 3 | | III-1 | Zfp90 | 146198 | 20-May-15 |
| 23466 | 2 | 3 | | III-1 | Zdhhc17 | 23390 | 1-Jun-15 | 23825 | 2 | 3 | | III-1 | Zfp91 | 80829 | 4-May-15 |
| 23471 | 2 | 3 | | III-1 | Zdhhc21 | 340481 | 4-May-15 | 23839 | 2 | 3 | | III-1 | Zfp94 | | |
| 23486 | 2 | 3 | | III-1 | Zer1 | 10444 | 4-May-15 | 23841 | 2 | 3 | | III-1 | Zfp947 | | |
| 23489 | 2 | 3 | | III-1 | Zfand2a | 90637 | 4-May-15 | 23847 | 2 | 3 | | III-1 | Zfp948 | | |
| 23495 | 2 | 3 | | III-1 | Zfa-ps | | | 23848 | 2 | 3 | | III-1 | Zfp949 | | |
| 23499 | 2 | 3 | | III-1 | Zfhx2os | | | 23849 | 2 | 3 | | III-1 | Zfp955a | | |
| 23500 | 2 | 3 | | III-1 | Zfhx3 | 463 | 12-May-15 | 23854 | 2 | 3 | | III-1 | Zfp957 | | |
| 23504 | 2 | 3 | | III-1 | Zfp101 | | | 23857 | 2 | 3 | | III-1 | Zfp959 | | |
| 23506 | 2 | 3 | | III-1 | Zfp106 | 64397 | 12-May-15 | 23859 | 2 | 3 | | III-1 | Zfp961 | | |
| 23508 | 2 | 3 | | III-1 | Zfp109 | | | 23861 | 2 | 3 | | III-1 | Zfp97 | | |
| 23513 | 2 | 3 | | III-1 | Zfp113 | 7551 | 12-May-15 | 23864 | 2 | 3 | | III-1 | Zfp97 | | |
| 23517 | 2 | 3 | | III-1 | Zfp12 | | | 23866 | 2 | 3 | | III-1 | Zfpm1 | 161882 | 17-May-15 |
| 23521 | 2 | 3 | | III-1 | Zfp131 | | | 23867 | 2 | 3 | | III-1 | Zfpm2 | 23414 | 4-May-15 |
| 23522 | 2 | 3 | | III-1 | Zfp133-ps | | | 23870 | 2 | 3 | | III-1 | Zfx | 7543 | 31-May-15 |
| 23525 | 2 | 3 | | III-1 | Zfp143 | | | 23874 | 2 | 3 | | III-1 | Zfyve16 | 9765 | 4-May-15 |

Fig.22 - 87

| | | | | | | | | | | | | | |
|---|---|---|---|---|---|---|---|---|---|---|---|---|---|
| 23875 | 2 | 3 | | | II-1 | Zfyve19 | 84936 | 21-May-15 | 1420 | 2 | | II-2 | 9030404E10Rik | | |
| 23878 | 2 | 3 | | | II-1 | Zfyve26 | 23503 | 4-May-15 | 1468 | 2 | | II-2 | 9330178D15Rik | | |
| 23881 | 2 | 3 | | | II-1 | Zfyve9 | 9372 | 24-May-15 | 1476 | 2 | | II-2 | 9430015G10Rik | | |
| 23889 | 2 | 3 | | | II-1 | Zic1 | 7545 | 2-Jun-15 | 1478 | 2 | | II-2 | 9430018G01Rik | | |
| 23896 | 2 | 3 | | | II-1 | Zim3 | 114026 | 12-May-15 | 1511 | 2 | | II-2 | 9830132P13Rik | | |
| 23909 | 2 | 3 | | | II-1 | Zmat2 | 153527 | 4-May-15 | 1513 | 2 | | II-2 | 9830166K06Rik | | |
| 23912 | 2 | 3 | | | II-1 | Zmat5 | 66954 | 2-Jun-15 | 1529 | 2 | | II-2 | A230028O05Rik | | |
| 23913 | 2 | 3 | | | II-1 | Zmiz1 | 57178 | 17-May-15 | 1571 | 2 | | II-2 | A430105I19Rik | | |
| 23914 | 2 | 3 | | | II-1 | Zmiz2 | 83637 | 4-May-15 | 1587 | 2 | | II-2 | A530088E08Rik | | |
| 23923 | 2 | 3 | | | II-1 | Zmynd11 | 10771 | 4-May-15 | 1642 | 2 | | II-2 | A930011O12Rik | | |
| 23926 | 2 | 3 | | | II-1 | Zmynd19 | 116225 | 2-Jun-15 | 1643 | 2 | | II-2 | A930012L21Rik | | |
| 23934 | 2 | 3 | | | II-1 | Znhit6 | 54880 | 4-May-15 | 1665 | 2 | | II-2 | AA792892 | | |
| 23937 | 2 | 3 | | | II-1 | Znrf1 | 84937 | 23-May-15 | 1676 | 2 | | II-2 | Aak1 | 22848 | 31-May-15 |
| 23941 | 2 | 3 | | | II-1 | Zp1 | 22917 | 12-May-15 | 1930 | 2 | | II-2 | Adam23 | 8745 | 4-May-15 |
| 23951 | 2 | 3 | | | II-1 | Zranb2 | 9406 | 2-Jun-15 | 2059 | 2 | | II-2 | AF357426 | | |
| 23954 | 2 | 3 | | | II-1 | Zrsr2 | 8233 | 4-May-15 | 2060 | 2 | | II-2 | AF366264 | | |
| 23958 | 2 | 3 | | | II-1 | Zscan2 | 54993 | 12-May-15 | 2134 | 2 | | II-2 | AI317395 | | |
| 23959 | 2 | 3 | | | II-1 | Zscan20 | 7579 | 12-May-15 | 2368 | 2 | | II-2 | Angel2 | 90806 | 12-May-15 |
| 23962 | 2 | 3 | | | II-1 | Zscan25 | 221785 | 4-May-15 | 2369 | 2 | | II-2 | Angpt1 | 284 | 17-May-15 |
| 23963 | 2 | 3 | | | II-1 | Zscan26 | 7741 | 12-May-15 | 2832 | 2 | | II-2 | Asna1 | 439 | 4-May-15 |
| 23979 | 2 | 3 | | | II-1 | Zswim8 | 23053 | 12-May-15 | 2857 | 2 | | II-2 | Atad2 | 29028 | 4-May-15 |
| 23984 | 2 | 3 | | | II-1 | Zxda | 7789 | 4-May-15 | 3017 | 2 | | II-2 | AU019823 | | |
| 23989 | 2 | 3 | | | II-1 | Zyx | 7791 | 4-May-15 | 3019 | 2 | | II-2 | AU021063 | | |
| 117 | 2 | | | | II-2 | 1700003P14Rik | | | 3026 | 2 | | II-2 | AU040320 | | |
| 124 | 2 | | | | II-2 | 1700007G11Rik | | | 3076 | 2 | | II-2 | B020018I22Rik | | |
| 161 | 2 | | | | II-2 | 1700013D24Rik | | | 3077 | 2 | | II-2 | B020031M17Rik | | |
| 176 | 2 | | | | II-2 | 1700017B05Rik | | | 3078 | 2 | | II-2 | B130006D01Rik | | |
| 182 | 2 | | | | II-2 | 1700018B08Rik | | | 3096 | 2 | | II-2 | B2m | 567 | 17-May-15 |
| 195 | 2 | | | | II-2 | 1700019L03Rik | | | 3258 | 2 | | II-2 | BC048502 | | |
| 218 | 2 | | | | II-2 | 1700023E05Rik | | | 3305 | 2 | | II-2 | Bcap29 | 55973 | 4-May-15 |
| 295 | 2 | | | | II-2 | 1700042G15Rik | | | 3472 | 2 | | II-2 | Bpifb5 | | |
| 334 | 2 | | | | II-2 | 1700064O06Rik | | | 3473 | 2 | | II-2 | Bpifb6 | 128859 | 4-May-15 |
| 336 | 2 | | | | II-2 | 1700065O16Rik | | | 3592 | 2 | | II-2 | C130074G19Rik | | |
| 337 | 2 | | | | II-2 | 1700066H16Rik | | | 3593 | 2 | | II-2 | C130079G13Rik | | |
| 343 | 2 | | | | II-2 | 1700066B19Rik | | | 3677 | 2 | | II-2 | C87414 | | |
| 345 | 2 | | | | II-2 | 1700066N21Rik | | | 3678 | 2 | | II-2 | C87436 | | |
| 374 | 2 | | | | II-2 | 1700092E19Rik | | | 3679 | 2 | | II-2 | C87499 | | |
| 395 | 2 | | | | II-2 | 1700108F19Rik | | | 3680 | 2 | | II-2 | C87977 | | |
| 403 | 2 | | | | II-2 | 1700110I01Rik | | | 3749 | 2 | | II-2 | Cald1 | 800 | 4-May-15 |
| 419 | 2 | | | | II-2 | 1700123O01Rik | | | 3967 | 2 | | II-2 | Ccdc158 | 339965 | 4-May-15 |
| 420 | 2 | | | | II-2 | 1700123K08Rik | | | 3968 | 2 | | II-2 | Ccdc159 | 126075 | 4-May-15 |
| 422 | 2 | | | | II-2 | 1700123M08Rik | | | 4006 | 2 | | II-2 | Ccdc38 | 120935 | 28-May-15 |
| 423 | 2 | | | | II-2 | 1700123O12Rik | | | 4390 | 2 | | II-2 | Ceacam14 | | |
| 434 | 2 | | | | II-2 | 1700123C05Rik | | | 4392 | 2 | | II-2 | Ceacam16 | 388551 | |
| 531 | 2 | | | | II-2 | 2310007B03Rik | | | 4393 | 2 | | II-2 | Ceacam18 | 729767 | 4-May-15 |
| 545 | 2 | | | | II-2 | 2310022B05Rik | | | 4582 | 2 | | II-2 | Chml | 1122 | 4-May-15 |
| 586 | 2 | | | | II-2 | 2410015M20Rik | | | 4665 | 2 | | II-2 | Cir1 | 9541 | 7-Jun-15 |
| 595 | 2 | | | | II-2 | 2410124H12Rik | | | 4794 | 2 | | II-2 | Clp1 | 10978 | 16-Jun-15 |
| 782 | 2 | | | | II-2 | 4921511C10Rik | | | 4837 | 2 | | II-2 | Cnitm3 | 123920 | 4-May-15 |
| 784 | 2 | | | | II-2 | 4921511H03Rik | | | 4901 | 2 | | II-2 | Cntn6 | 27255 | 21-May-15 |
| 791 | 2 | | | | II-2 | 4921524L21Rik | | | 5220 | 2 | | II-2 | Csn1s2a | 286828 | 4-May-15 |
| 806 | 2 | | | | II-2 | 4930401O12Rik | | | 5222 | 2 | | II-2 | Csn2 | 1447 | 7-Jun-15 |
| 807 | 2 | | | | II-2 | 4930402F06Rik | | | 5223 | 2 | | II-2 | Csn3 | 1448 | 7-Jun-15 |
| 859 | 2 | | | | II-2 | 4930431P03Rik | | | 5224 | 2 | | II-2 | Csnk1a1 | 1452 | 4-May-15 |
| 865 | 2 | | | | II-2 | 4930433N12Rik | | | 5306 | 2 | | II-2 | Cts8 | | |
| 867 | 2 | | | | II-2 | 4930435E12Rik | | | 5307 | 2 | | II-2 | Cts8-ps | | |
| 878 | 2 | | | | II-2 | 4930444P10Rik | | | 5308 | 2 | | II-2 | Ctsa | 5476 | 12-May-15 |
| 880 | 2 | | | | II-2 | 4930447C04Rik | | | 5309 | 2 | | II-2 | Ctsb | 1508 | 31-May-15 |
| 894 | 2 | | | | II-2 | 4930451G09Rik | | | 5322 | 2 | | II-2 | Ctsq | | |
| 944 | 2 | | | | II-2 | 4930483C08Rik | | | 5323 | 2 | | II-2 | Ctsr | | |
| 947 | 2 | | | | II-2 | 4930486L24Rik | | | 5544 | 2 | | II-2 | D030028A08Rik | | |
| 953 | 2 | | | | II-2 | 4930500J02Rik | | | 5561 | 2 | | II-2 | D16Ertd472e | | |
| 975 | 2 | | | | II-2 | 4930511E03Rik | | | 5562 | 2 | | II-2 | D16Ertd519e | | |
| 980 | 2 | | | | II-2 | 4930513O06Rik | | | 5565 | 2 | | II-2 | D17Wsu104e | | |
| 987 | 2 | | | | II-2 | 4930518P08Rik | | | 5566 | 2 | | II-2 | D17Wsu92e | | |
| 988 | 2 | | | | II-2 | 4930519O14Rik | | | 5591 | 2 | | II-2 | D5Ertd605e | | |
| 989 | 2 | | | | II-2 | 4930519F09Rik | | | 5618 | 2 | | II-2 | D830026I12Rik | | |
| 999 | 2 | | | | II-2 | 4930523K07Rik | | | 5633 | 2 | | II-2 | Daam1 | 23002 | 14-May-15 |
| 1025 | 2 | | | | II-2 | 4930539E08Rik | | | 5689 | 2 | | II-2 | Dcaf17 | 80067 | 23-May-15 |
| 1030 | 2 | | | | II-2 | 4930542C21Rik | | | 5820 | 2 | | II-2 | Defa-rs7 | | |
| 1031 | 2 | | | | II-2 | 4930542D17Rik | | | 6001 | 2 | | II-2 | Dlgap5 | 9787 | 4-May-15 |
| 1033 | 2 | | | | II-2 | 4930544D05Rik | | | 6030 | 2 | | II-2 | Dmrta1 | 63951 | 4-May-15 |
| 1042 | 2 | | | | II-2 | 4930547E14Rik | | | 6051 | 2 | | II-2 | Dnah5 | 1767 | 23-May-15 |
| 1080 | 2 | | | | II-2 | 4930567H12Rik | | | 6056 | 2 | | II-2 | Dnah9 | 1770 | 12-May-15 |
| 1085 | 2 | | | | II-2 | 4930568E12Rik | | | 6215 | 2 | | II-2 | Drd2 | 1813 | 31-May-15 |
| 1172 | 2 | | | | II-2 | 4933400L20Rik | | | 6301 | 2 | | II-2 | DX8ay18 | | |
| 1175 | 2 | | | | II-2 | 4933401H06Rik | | | 6309 | 2 | | II-2 | Dync1i2 | 1781 | 1-Jun-15 |
| 1228 | 2 | | | | II-2 | 4933416M07Rik | | | 6342 | 2 | | II-2 | E030024N20Rik | | |
| 1241 | 2 | | | | II-2 | 4933425L06Rik | | | 6384 | 2 | | II-2 | E330017A01Rik | | |
| 1244 | 2 | | | | II-2 | 4933427O14Rik | | | 6391 | 2 | | II-2 | E430016F16Rik | | |
| 1246 | 2 | | | | II-2 | 4933427E13Rik | | | 6408 | 2 | | II-2 | Ears2 | 124454 | 12-May-15 |
| 1256 | 2 | | | | II-2 | 4933430N04Rik | | | 6731 | 2 | | II-2 | Ephb1 | 2047 | 17-May-15 |
| 1262 | 2 | | | | II-2 | 4933432K03Rik | | | 6821 | 2 | | II-2 | Esp18 | | |
| 1263 | 2 | | | | II-2 | 4933433C11Rik | | | 6822 | 2 | | II-2 | Esp23 | | |
| 1265 | 2 | | | | II-2 | 4933433G08Rik | | | 6825 | 2 | | II-2 | Esp31 | | |
| 1267 | 2 | | | | II-2 | 4933433G19Rik | | | 6826 | 2 | | II-2 | Esp34 | | |
| 1274 | 2 | | | | II-2 | 4933438I17Rik | | | 6827 | 2 | | II-2 | Esp36 | | |
| 1331 | 2 | | | | II-2 | 5730460C07Rik | | | 6228 | 2 | | II-2 | Esp38 | | |
| 1361 | 2 | | | | II-2 | 6030466F02Rik | | | 6829 | 2 | | II-2 | Esp4 | | |
| 1381 | 2 | | | | II-2 | 6430550O23Rik | | | 6830 | 2 | | II-2 | Esp5 | | |
| 1392 | 2 | | | | II-2 | 6720483E21Rik | | | 6831 | 2 | | II-2 | Esp6 | | |
| 1399 | 2 | | | | II-2 | 7420701I03Rik | | | 6833 | 2 | | II-2 | Esp8 | | |
| 1402 | 2 | | | | II-2 | 8030411F24Rik | | | 6886 | 2 | | II-2 | Exd2 | 55218 | 4-May-15 |
| 1404 | 2 | | | | II-2 | 8030423J24Rik | | | 7251 | 2 | | II-2 | Pbf1 | 85302 | 4-May-15 |
| 1406 | 2 | | | | II-2 | 8030443G20Rik | | | 7326 | 2 | | II-2 | Fbxw16 | | |
| 1418 | 2 | | | | II-2 | 9030025P20Rik | | | 7327 | 2 | | II-2 | Fbxw17 | | |
| 1419 | 2 | | | | II-2 | 9030204H09Rik | | | 7328 | 2 | | II-2 | Fbxw18 | | |

Fig.22 - 88

| | | | | | | | | | | | | | |
|---|---|---|---|---|---|---|---|---|---|---|---|---|---|
| 7332 | 2 | | | II-2 | Fbxw21 | | | 8879 | 2 | | | II-2 | Gm5086 | | |
| 7334 | 2 | | | II-2 | Fbxw24 | | | 8881 | 2 | | | II-2 | Gm5088 | | |
| 7335 | 2 | | | II-2 | Fbxw26 | | | 8990 | 2 | | | II-2 | Gm5941 | | |
| 7336 | 2 | | | II-2 | Fbxw28 | | | 9005 | 2 | | | II-2 | Gm6164 | | |
| 7337 | 2 | | | II-2 | Fbxw4 | 6468 | 4-May-15 | 9007 | 2 | | | II-2 | Gm6213 | | |
| 7338 | 2 | | | II-2 | Fbxw5 | 54461 | 4-May-15 | 9021 | 2 | | | II-2 | Gm6170 | | |
| 7380 | 2 | | | II-2 | Fermt1 | 55612 | 12-May-15 | 9027 | 2 | | | II-2 | Gm6432 | | |
| 7571 | 2 | | | II-2 | Foxi3 | 344167 | 12-May-15 | 9029 | 2 | | | II-2 | Gm6460 | | |
| 7601 | 2 | | | II-2 | Fpr1 | 2357 | 12-May-15 | 9070 | 2 | | | II-2 | Gm6927 | | |
| 7654 | 2 | | | II-2 | Ftl1 | | | 9081 | 2 | | | II-2 | Gm7104 | | |
| 7813 | 2 | | | II-2 | Gart | 2618 | 4-May-15 | 9103 | 2 | | | II-2 | Gm7609 | | |
| 7961 | 2 | | | II-2 | Gimap1 | 170575 | 4-May-15 | 9119 | 2 | | | II-2 | Gm806 | | |
| 8039 | 2 | | | II-2 | Glra4 | 441509 | 4-May-15 | 9122 | 2 | | | II-2 | Gm815 | | |
| 8092 | 2 | | | II-2 | Gm10272 | | | 9124 | 2 | | | II-2 | Gm8221 | | |
| 8103 | 2 | | | II-2 | Gm10377 | | | 9125 | 2 | | | II-2 | Gm8234 | | |
| 8107 | 2 | | | II-2 | Gm10406 | | | 9126 | 2 | | | II-2 | Gm826 | | |
| 8108 | 2 | | | II-2 | Gm10408 | | | 9131 | 2 | | | II-2 | Gm833 | | |
| 8109 | 2 | | | II-2 | Gm10409 | | | 9132 | 2 | | | II-2 | Gm8363 | | |
| 8111 | 2 | | | II-2 | Gm10415 | | | 9139 | 2 | | | II-2 | Gm8615 | | |
| 8119 | 2 | | | II-2 | Gm10445 | | | 9266 | 2 | | | II-2 | Golga2 | 2801 | 4-May-15 |
| 8156 | 2 | | | II-2 | Gm10670 | | | 9349 | 2 | | | II-2 | Gpr124 | 25960 | 4-May-15 |
| 8157 | 2 | | | II-2 | Gm10677 | | | 9366 | 2 | | | II-2 | Gpr15 | 2838 | 4-May-15 |
| 8162 | 2 | | | II-2 | Gm10731 | | | 9408 | 2 | | | II-2 | Gpr55 | 9290 | 4-May-15 |
| 8163 | 2 | | | II-2 | Gm10745 | | | 9510 | 2 | | | II-2 | Grm6 | 2916 | 4-May-15 |
| 8164 | 2 | | | II-2 | Gm10754 | | | 9513 | 2 | | | II-2 | Grn | 2896 | 23-May-15 |
| 8174 | 2 | | | II-2 | Gm10804 | | | 9538 | 2 | | | II-2 | Gse1 | 23199 | 21-May-15 |
| 8195 | 2 | | | II-2 | Gm11213 | | | 9580 | 2 | | | II-2 | Gtf2e1 | 2960 | 4-May-15 |
| 8204 | 2 | | | II-2 | Gm11426 | | | 9623 | 2 | | | II-2 | Gucy2g | 390003 | 4-May-15 |
| 8214 | 2 | | | II-2 | Gm11548 | | | 9647 | 2 | | | II-2 | Gzmg | | |
| 8215 | 2 | | | II-2 | Gm11549 | | | 9649 | 2 | | | II-2 | Gzmm | 3004 | 4-May-15 |
| 8236 | 2 | | | II-2 | Gm11762 | | | 9685 | 2 | | | II-2 | H2-M10.2 | | |
| 8263 | 2 | | | II-2 | Gm12338 | | | 9686 | 2 | | | II-2 | H2-M10.3 | | |
| 8274 | 2 | | | II-2 | Gm12669 | | | 9687 | 2 | | | II-2 | H2-M10.4 | | |
| 8280 | 2 | | | II-2 | Gm128 | | | 9688 | 2 | | | II-2 | H2-M10.5 | | |
| 8281 | 2 | | | II-2 | Gm12830 | | | 9689 | 2 | | | II-2 | H2-M10.6 | | |
| 8285 | 2 | | | II-2 | Gm12942 | | | 9690 | 2 | | | II-2 | H2-M11 | | |
| 8296 | 2 | | | II-2 | Gm13057 | | | 9881 | 2 | | | II-2 | Hibadh | 11112 | 12-May-15 |
| 8297 | 2 | | | II-2 | Gm13078 | | | 10062 | 2 | | | II-2 | Hoxa10 | 3206 | 28-May-15 |
| 8299 | 2 | | | II-2 | Gm13084 | | | 10089 | 2 | | | II-2 | Hoxc6 | 3223 | 4-May-15 |
| 8300 | 2 | | | II-2 | Gm13088 | | | 10095 | 2 | | | II-2 | Hoxd12 | 3238 | 4-May-15 |
| 8301 | 2 | | | II-2 | Gm13102 | | | 10321 | 2 | | | II-2 | Ifna13 | 3447 | 4-May-15 |
| 8302 | 2 | | | II-2 | Gm13103 | | | 10322 | 2 | | | II-2 | Ifna14 | 3448 | 12-May-15 |
| 8303 | 2 | | | II-2 | Gm13119 | | | 10323 | 2 | | | II-2 | Ifna15 | | |
| 8318 | 2 | | | II-2 | Gm13251 | | | 10324 | 2 | | | II-2 | Ifna16 | 3449 | 12-May-15 |
| 8324 | 2 | | | II-2 | Gm13278 | | | 10325 | 2 | | | II-2 | Ifna2 | 3440 | 3-May-15 |
| 8329 | 2 | | | II-2 | Gm13288 | | | 10326 | 2 | | | II-2 | Ifna4 | 3441 | 4-May-15 |
| 8332 | 2 | | | II-2 | Gm13298 | | | 10327 | 2 | | | II-2 | Ifna5 | 3442 | 4-May-15 |
| 8346 | 2 | | | II-2 | Gm13544 | | | 10328 | 2 | | | II-2 | Ifna6 | 3443 | 4-May-15 |
| 8374 | 2 | | | II-2 | Gm14169 | | | 10329 | 2 | | | II-2 | Ifna7 | 3444 | 4-May-15 |
| 8383 | 2 | | | II-2 | Gm14325 | | | 10330 | 2 | | | II-2 | Ifna9 | | |
| 8389 | 2 | | | II-2 | Gm14351 | | | 10331 | 2 | | | II-2 | Ifnab | | |
| 8424 | 2 | | | II-2 | Gm14685 | | | 10332 | 2 | | | II-2 | Ifnar1 | 3454 | 12-May-15 |
| 8426 | 2 | | | II-2 | Gm14718 | | | 10333 | 2 | | | II-2 | Ifnar2 | 3455 | 12-May-15 |
| 8428 | 2 | | | II-2 | Gm14743 | | | 10337 | 2 | | | II-2 | Ifngr1 | 3459 | 12-May-15 |
| 8431 | 2 | | | II-2 | Gm14812 | | | 10344 | 2 | | | II-2 | Ifrd1 | 3475 | 26-May-15 |
| 8510 | 2 | | | II-2 | Gm16294 | | | 10370 | 2 | | | II-2 | Igf2os | | |
| 8511 | 2 | | | II-2 | Gm1631 | | | 10473 | 2 | | | II-2 | Il25 | 64806 | 7-Jun-15 |
| 8512 | 2 | | | II-2 | Gm16325 | | | 10475 | 2 | | | II-2 | Il27ra | 9466 | 4-May-15 |
| 8513 | 2 | | | II-2 | Gm16336 | | | 10607 | 2 | | | II-2 | Iqgap2 | 10788 | 17-May-15 |
| 8517 | 2 | | | II-2 | Gm16390 | | | 10634 | 2 | | | II-2 | Irgm2 | | |
| 8575 | 2 | | | II-2 | Gm17746 | | | 10904 | 2 | | | II-2 | Kcnv2 | 169522 | 4-May-15 |
| 8583 | 2 | | | II-2 | Gm1821 | | | 11139 | 2 | | | II-2 | Klra6 | | |
| 8584 | 2 | | | II-2 | Gm18409 | | | 11310 | 2 | | | II-2 | L3mbtl4 | 91133 | 14-May-15 |
| 8587 | 2 | | | II-2 | Gm19277 | | | 11312 | 2 | | | II-2 | Lacc1 | 144811 | 4-May-15 |
| 8590 | 2 | | | II-2 | Gm19345 | | | 11603 | 2 | | | II-2 | LOC101056149 | | |
| 8592 | 2 | | | II-2 | Gm19402 | | | 11618 | 2 | | | II-2 | LOC102636514 | | |
| 8628 | 2 | | | II-2 | Gm20139 | | | 11895 | 2 | | | II-2 | Macf1 | 23489 | 12-May-15 |
| 8632 | 2 | | | II-2 | Gm20199 | | | 11917 | 2 | | | II-2 | Magea3 | 4102 | 31-May-15 |
| 8633 | 2 | | | II-2 | Gm2022 | | | 11919 | 2 | | | II-2 | Magea5 | 4104 | 4-May-15 |
| 8645 | 2 | | | II-2 | Gm20554 | | | 11923 | 2 | | | II-2 | Mageb16 | 139604 | 4-May-15 |
| 8647 | 2 | | | II-2 | Gm20594 | | | 11925 | 2 | | | II-2 | Mageb18 | 286514 | 4-May-15 |
| 8655 | 2 | | | II-2 | Gm20738 | | | 11938 | 2 | | | II-2 | Magi3 | 260425 | 4-May-15 |
| 8656 | 2 | | | II-2 | Gm20740 | | | 12081 | 2 | | | II-2 | Mast3 | 23031 | 23-May-15 |
| 8666 | 2 | | | II-2 | Gm20753 | | | 12393 | 2 | | | II-2 | Mir101c | | |
| 8672 | 2 | | | II-2 | Gm20759 | | | 12394 | 2 | | | II-2 | Mir103-1 | 406895 | 21-May-15 |
| 8674 | 2 | | | II-2 | Gm20767 | | | 12395 | 2 | | | II-2 | Mir103-2 | 406896 | 21-May-15 |
| 8675 | 2 | | | II-2 | Gm20806 | | | 12396 | 2 | | | II-2 | Mir105 | | |
| 8676 | 2 | | | II-2 | Gm20809 | | | 12397 | 2 | | | II-2 | Mir106a | 406899 | 21-May-15 |
| 8677 | 2 | | | II-2 | Gm20815 | | | 12398 | 2 | | | II-2 | Mir106b | 406900 | 21-May-15 |
| 8681 | 2 | | | II-2 | Gm20826 | | | 12399 | 2 | | | II-2 | Mir107 | 406901 | 21-May-15 |
| 8708 | 2 | | | II-2 | Gm21319 | | | 12400 | 2 | | | II-2 | Mir10a | 406902 | 21-May-15 |
| 8721 | 2 | | | II-2 | Gm21951 | | | 12401 | 2 | | | II-2 | Mir10b | 406903 | 21-May-15 |
| 8726 | 2 | | | II-2 | Gm2516 | | | 12402 | 2 | | | II-2 | Mir1187 | | |
| 8735 | 2 | | | II-2 | Gm2825 | | | 12403 | 2 | | | II-2 | Mir1188 | | |
| 8796 | 2 | | | II-2 | Gm4216 | | | 12404 | 2 | | | II-2 | Mir1190 | | |
| 8798 | 2 | | | II-2 | Gm4251 | | | 12405 | 2 | | | II-2 | Mir1191 | | |
| 8807 | 2 | | | II-2 | Gm4303 | | | 12406 | 2 | | | II-2 | Mir1191b | | |
| 8808 | 2 | | | II-2 | Gm4307 | | | 12407 | 2 | | | II-2 | Mir1192 | | |
| 8809 | 2 | | | II-2 | Gm4312 | | | 12408 | 2 | | | II-2 | Mir1193 | 100424837 | 4-May-15 |
| 8810 | 2 | | | II-2 | Gm4340 | | | 12409 | 2 | | | II-2 | Mir1195 | | |
| 8811 | 2 | | | II-2 | Gm4349 | | | 12410 | 2 | | | II-2 | Mir1197 | 100302250 | 21-May-15 |
| 8816 | 2 | | | II-2 | Gm4432 | | | 12411 | 2 | | | II-2 | Mir1198 | | |
| 8818 | 2 | | | II-2 | Gm4477 | | | 12415 | 2 | | | II-2 | Mir1231 | 100302158 | 4-May-15 |
| 8826 | 2 | | | II-2 | Gm4710 | | | | | | | | | | |
| 8833 | 2 | | | II-2 | Gm4776 | | | 12416 | 2 | | | II-2 | Mir1247 | 100302145 | 21-May-15 |
| 8835 | 2 | | | II-2 | Gm4788 | | | | | | | | | | |
| 8877 | 2 | | | II-2 | Gm5083 | | | 12417 | 2 | | | II-2 | Mir1249 | 100302 | 4-May-15 |

Fig.22 - 89

| | | | | | | 149 | |
|---|---|---|---|---|---|---|---|
| 12418 | 2 | | | II-2 | Mir124a-1 | | |
| 12419 | 2 | | | II-2 | Mir124a-2 | | |
| 12420 | 2 | | | II-2 | Mir124a-3 | | |
| 12421 | 2 | | | II-2 | Mir1251 | 100302289 | 4-May-15 |
| 12422 | 2 | | | II-2 | Mir1258 | 100302172 | 21-May-15 |
| 12423 | 2 | | | II-2 | Mir125a | 406910 | 24-May-15 |
| 12424 | 2 | | | II-2 | Mir125b-1 | | |
| 12425 | 2 | | | II-2 | Mir125b-2 | | |
| 12426 | 2 | | | II-2 | Mir126 | 406913 | 21-May-15 |
| 12427 | 2 | | | II-2 | Mir1264 | 100302251 | 4-May-15 |
| 12428 | 2 | | | II-2 | Mir1266 | | |
| 12429 | 2 | | | II-2 | Mir127 | 406914 | 21-May-15 |
| 12430 | 2 | | | II-2 | Mir128-1 | 406915 | 21-May-15 |
| 12431 | 2 | | | II-2 | Mir128-2 | 406916 | 21-May-15 |
| 12433 | 2 | | | II-2 | Mir129-1 | 406917 | 21-May-15 |
| 12434 | 2 | | | II-2 | Mir129-2 | 406918 | 21-May-15 |
| 12438 | 2 | | | II-2 | Mir130a | 406919 | 24-May-15 |
| 12439 | 2 | | | II-2 | Mir130b | 406920 | 21-May-15 |
| 12440 | 2 | | | II-2 | Mir130c | | |
| 12441 | 2 | | | II-2 | Mir132 | 406921 | 21-May-15 |
| 12442 | 2 | | | II-2 | Mir133a-1 | | |
| 12445 | 2 | | | II-2 | Mir133c | | |
| 12447 | 2 | | | II-2 | Mir135a-1 | | |
| 12448 | 2 | | | II-2 | Mir135a-2 | | |
| 12449 | 2 | | | II-2 | Mir135b | 442891 | 21-May-15 |
| 12450 | 2 | | | II-2 | Mir136 | 406927 | 24-May-15 |
| 12451 | 2 | | | II-2 | Mir137 | 406928 | 21-May-15 |
| 12452 | 2 | | | II-2 | Mir138-1 | 406929 | 21-May-15 |
| 12453 | 2 | | | II-2 | Mir138-2 | 406930 | 21-May-15 |
| 12454 | 2 | | | II-2 | Mir139 | 406931 | 21-May-15 |
| 12455 | 2 | | | II-2 | Mir140 | 406932 | 21-May-15 |
| 12456 | 2 | | | II-2 | Mir141 | 406933 | 21-May-15 |
| 12457 | 2 | | | II-2 | Mir142 | 406934 | 21-May-15 |
| 12464 | 2 | | | II-2 | Mir146 | | |
| 12465 | 2 | | | II-2 | Mir146b | 574447 | 21-May-15 |
| 12466 | 2 | | | II-2 | Mir147 | 406939 | 4-May-15 |
| 12467 | 2 | | | II-2 | Mir148a | 406940 | 21-May-15 |
| 12468 | 2 | | | II-2 | Mir148b | 442892 | 21-May-15 |
| 12469 | 2 | | | II-2 | Mir149 | 406941 | 21-May-15 |
| 12470 | 2 | | | II-2 | Mir150 | 406942 | 21-May-15 |
| 12471 | 2 | | | II-2 | Mir152 | 406943 | 21-May-15 |
| 12472 | 2 | | | II-2 | Mir153 | | |
| 12473 | 2 | | | II-2 | Mir154 | 406946 | 21-May-15 |
| 12474 | 2 | | | II-2 | Mir155 | 406947 | 21-May-15 |
| 12475 | 2 | | | II-2 | Mir15a | 406948 | 21-May-15 |
| 12476 | 2 | | | II-2 | Mir15b | 406949 | 21-May-15 |
| 12477 | 2 | | | II-2 | Mir16-1 | 406950 | 21-May-15 |
| 12478 | 2 | | | II-2 | Mir16-2 | 406951 | 21-May-15 |
| 12485 | 2 | | | II-2 | Mir181b-1 | | |
| 12486 | 2 | | | II-2 | Mir181b-2 | | |
| 12487 | 2 | | | II-2 | Mir181c | 406957 | 21-May-15 |
| 12488 | 2 | | | II-2 | Mir181d | 574457 | 21-May-15 |
| 12489 | 2 | | | II-2 | Mir182 | 406958 | 7-Jun-15 |
| 12490 | 2 | | | II-2 | Mir183 | 406959 | 7-Jun-15 |
| 12491 | 2 | | | II-2 | Mir1839 | | |
| 12492 | 2 | | | II-2 | Mir184 | 406960 | 21-May-15 |
| 12493 | 2 | | | II-2 | Mir1843 | | |
| 12494 | 2 | | | II-2 | Mir1843b | | |
| 12495 | 2 | | | II-2 | Mir185 | 406961 | 24-May-15 |
| 12496 | 2 | | | II-2 | Mir186 | 406962 | 21-May-15 |
| 12497 | 2 | | | II-2 | Mir187 | 406963 | 21-May-15 |
| 12498 | 2 | | | II-2 | Mir188 | 406964 | 21-May-15 |
| 12499 | 2 | | | II-2 | Mir1892 | | |
| 12500 | 2 | | | II-2 | Mir1893 | | |
| 12501 | 2 | | | II-2 | Mir1894 | | |
| 12502 | 2 | | | II-2 | Mir1895 | | |
| 12503 | 2 | | | II-2 | Mir1896 | | |
| 12504 | 2 | | | II-2 | Mir1897 | | |
| 12505 | 2 | | | II-2 | Mir1898 | | |
| 12528 | 2 | | | II-2 | Mir1934 | | |
| 12550 | 2 | | | II-2 | Mir1955 | | |
| 12574 | 2 | | | II-2 | Mir199a-2 | | |
| 12576 | 2 | | | II-2 | Mir19a | 406979 | 24-May-15 |
| 12595 | 2 | | | II-2 | Mir20b | 574032 | 7-Jun-15 |
| 12597 | 2 | | | II-2 | Mir210 | 406992 | 24-May-15 |
| 12650 | 2 | | | II-2 | Mir2976 | | |
| 12669 | 2 | | | II-2 | Mir3060 | | |
| 12720 | 2 | | | II-2 | Mir3103 | | |
| 12737 | 2 | | | II-2 | Mir33 | 407039 | 21-May-15 |
| 12943 | 2 | | | II-2 | Mir5619 | | |
| 13051 | 2 | | | II-2 | Mir6538 | | |
| 13077 | 2 | | | II-2 | Mir670 | 100313777 | 4-May-15 |
| 13082 | 2 | | | II-2 | Mir674 | | |
| 13086 | 2 | | | II-2 | Mir677 | | |
| 13088 | 2 | | | II-2 | Mir679 | | |
| 13102 | 2 | | | II-2 | Mir6898 | | |
| 13105 | 2 | | | II-2 | Mir6900 | | |
| 13108 | 2 | | | II-2 | Mir6903 | | |
| 13134 | 2 | | | II-2 | Mir6926 | | |
| 13145 | 2 | | | II-2 | Mir6936 | | |
| 13164 | 2 | | | II-2 | Mir6953 | | |
| 13241 | 2 | | | II-2 | Mir7025 | | |
| 13308 | 2 | | | II-2 | Mir7085 | | |
| 13328 | 2 | | | II-2 | Mir717 | | |
| 13364 | 2 | | | II-2 | Mir7241 | | |
| 13399 | 2 | | | II-2 | Mir767 | 768215 | 21-May-15 |
| 13447 | 2 | | | II-2 | Mir8118 | | |
| 13491 | 2 | | | II-2 | Mis12 | 79003 | 4-May-15 |
| 13669 | 2 | | | II-2 | Mrgpra3 | | |
| 13672 | 2 | | | II-2 | Mrgpra9 | | |
| 13673 | 2 | | | II-2 | Mrgprb1 | | |
| 13675 | 2 | | | II-2 | Mrgprb3 | | |
| 13679 | 2 | | | II-2 | Mrgprd | 116512 | 4-May-15 |
| 13680 | 2 | | | II-2 | Mrgpre | 116534 | 12-May-15 |
| 13687 | 2 | | | II-2 | Mrm1 | 79922 | 4-May-15 |
| 13694 | 2 | | | II-2 | Mroh6 | 642475 | 4-May-15 |
| 13699 | 2 | | | II-2 | Mrpl10 | 124995 | 4-May-15 |
| 13803 | 2 | | | II-2 | Msh4 | 4438 | 4-May-15 |
| 13888 | 2 | | | II-2 | Mtpap | 55149 | 4-May-15 |
| 13918 | 2 | | | II-2 | Mum1 | 84939 | 7-Jun-15 |
| 14422 | 2 | | | II-2 | Nkx2-2 | 4821 | 17-May-15 |
| 14449 | 2 | | | II-2 | Nlrp2 | 55655 | 28-May-15 |
| 14452 | 2 | | | II-2 | Nlrp4b | | |
| 14454 | 2 | | | II-2 | Nlrp4e | | |
| 14457 | 2 | | | II-2 | Nlrp5 | 126206 | 4-May-15 |
| 14459 | 2 | | | II-2 | Nlrp6 | 171389 | 4-May-15 |
| 14463 | 2 | | | II-2 | Nlrx1 | 79671 | 4-May-15 |
| 14497 | 2 | | | II-2 | Noc4l | 79050 | 12-May-15 |
| 14552 | 2 | | | II-2 | Npc2 | 10577 | 23-May-15 |
| 14652 | 2 | | | II-2 | Nrp2 | 8828 | 7-Jun-15 |
| 14815 | 2 | | | II-2 | Oas1g | | |
| 14830 | 2 | | | II-2 | Obox5 | | |
| 14831 | 2 | | | II-2 | Obox6 | | |
| 14832 | 2 | | | II-2 | Obp1a | | |
| 14859 | 2 | | | II-2 | Ogdhl | 55753 | 4-May-15 |
| 14884 | 2 | | | II-2 | Olfr1000 | | |
| 14885 | 2 | | | II-2 | Olfr1002 | | |
| 14886 | 2 | | | II-2 | Olfr1006 | | |
| 14887 | 2 | | | II-2 | Olfr1008 | | |
| 14888 | 2 | | | II-2 | Olfr1009 | | |
| 14889 | 2 | | | II-2 | Olfr101 | | |
| 14890 | 2 | | | II-2 | Olfr1010 | | |
| 14891 | 2 | | | II-2 | Olfr1012 | | |
| 14892 | 2 | | | II-2 | Olfr1013 | | |
| 14893 | 2 | | | II-2 | Olfr1014 | | |
| 14894 | 2 | | | II-2 | Olfr1015 | | |
| 14895 | 2 | | | II-2 | Olfr1016 | | |
| 14896 | 2 | | | II-2 | Olfr1018 | | |
| 14897 | 2 | | | II-2 | Olfr1019 | | |
| 14898 | 2 | | | II-2 | Olfr102 | | |
| 14899 | 2 | | | II-2 | Olfr1020 | | |
| 14900 | 2 | | | II-2 | Olfr1022 | | |
| 14901 | 2 | | | II-2 | Olfr1023 | | |
| 14902 | 2 | | | II-2 | Olfr1024 | | |
| 14904 | 2 | | | II-2 | Olfr1028 | | |
| 14905 | 2 | | | II-2 | Olfr1029 | | |
| 14906 | 2 | | | II-2 | Olfr103 | | |
| 14907 | 2 | | | II-2 | Olfr1030 | | |
| 14908 | 2 | | | II-2 | Olfr1031 | | |
| 14909 | 2 | | | II-2 | Olfr1032 | | |
| 14915 | 2 | | | II-2 | Olfr1039 | | |
| 14916 | 2 | | | II-2 | Olfr1040 | | |
| 14917 | 2 | | | II-2 | Olfr1042 | | |
| 14918 | 2 | | | II-2 | Olfr1043 | | |
| 14919 | 2 | | | II-2 | Olfr1044 | | |
| 14920 | 2 | | | II-2 | Olfr1045 | | |
| 14921 | 2 | | | II-2 | Olfr1046 | | |
| 14922 | 2 | | | II-2 | Olfr1047 | | |
| 14923 | 2 | | | II-2 | Olfr1048 | | |
| 14924 | 2 | | | II-2 | Olfr1049 | | |
| 14925 | 2 | | | II-2 | Olfr1051 | | |
| 14926 | 2 | | | II-2 | Olfr1052 | | |
| 14927 | 2 | | | II-2 | Olfr1053 | | |
| 14931 | 2 | | | II-2 | Olfr1057 | | |
| 14933 | 2 | | | II-2 | Olfr1061 | | |
| 14934 | 2 | | | II-2 | Olfr1062 | | |
| 14935 | 2 | | | II-2 | Olfr1065 | | |
| 14936 | 2 | | | II-2 | Olfr1066 | | |
| 14937 | 2 | | | II-2 | Olfr107 | | |
| 14938 | 2 | | | II-2 | Olfr1076 | | |
| 14939 | 2 | | | II-2 | Olfr1077-ps1 | | |
| 14940 | 2 | | | II-2 | Olfr1079 | | |
| 14941 | 2 | | | II-2 | Olfr108 | | |
| 14942 | 2 | | | II-2 | Olfr1080 | | |
| 14951 | 2 | | | II-2 | Olfr1093 | | |
| 14952 | 2 | | | II-2 | Olfr1094 | | |
| 14954 | 2 | | | II-2 | Olfr1097 | | |
| 14955 | 2 | | | II-2 | Olfr1098 | | |
| 14956 | 2 | | | II-2 | Olfr1099 | | |
| 14957 | 2 | | | II-2 | Olfr11 | | |
| 14958 | 2 | | | II-2 | Olfr110 | | |
| 14959 | 2 | | | II-2 | Olfr1100 | | |
| 14960 | 2 | | | II-2 | Olfr1101 | | |
| 14961 | 2 | | | II-2 | Olfr1102 | | |
| 14963 | 2 | | | II-2 | Olfr1105 | | |
| 14964 | 2 | | | II-2 | Olfr1106 | | |
| 14965 | 2 | | | II-2 | Olfr1107 | | |
| 14966 | 2 | | | II-2 | Olfr1109 | | |
| 14967 | 2 | | | II-2 | Olfr111 | | |
| 14968 | 2 | | | II-2 | Olfr1110 | | |
| 14969 | 2 | | | II-2 | Olfr1111 | | |

Fig.22 - 90

| | | | | | | | | | | | | | |
|---|---|---|---|---|---|---|---|---|---|---|---|---|---|
| 14970 | 2 | | | II-2 | Olfr1112 | | | 17383 | 2 | | | II-2 | Prl8a2 | | |
| 14973 | 2 | | | II-2 | Olfr1116-ps | | | 17387 | 2 | | | II-2 | Prlh | 51052 | 4-May-15 |
| 14974 | 2 | | | II-2 | Olfr1118 | | | 17388 | 2 | | | II-2 | Prlhr | 2834 | 4-May-15 |
| 14975 | 2 | | | II-2 | Olfr112 | | | 17511 | 2 | | | II-2 | Prss45 | | |
| 14976 | 2 | | | II-2 | Olfr1120 | | | 17542 | 2 | | | II-2 | Psg18 | 377047 | 4-May-15 |
| 14977 | 2 | | | II-2 | Olfr1121 | | | 17544 | 2 | | | II-2 | Psg20 | | |
| 14979 | 2 | | | II-2 | Olfr1123 | | | 17545 | 2 | | | II-2 | Psg21 | | |
| 14980 | 2 | | | II-2 | Olfr1124 | | | 17547 | 2 | | | II-2 | Psg23 | | |
| 14981 | 2 | | | II-2 | Olfr1126 | | | 17550 | 2 | | | II-2 | Psg27 | | |
| 14982 | 2 | | | II-2 | Olfr1128 | | | 17552 | 2 | | | II-2 | Psg29 | | |
| 14983 | 2 | | | II-2 | Olfr1129 | | | 17554 | 2 | | | II-2 | Psip1 | 11168 | 21-May-15 |
| 14984 | 2 | | | II-2 | Olfr113 | | | 17555 | 2 | | | II-2 | Pskh1 | 5681 | 12-May-15 |
| 14985 | 2 | | | II-2 | Olfr1130 | | | 17715 | 2 | | | II-2 | Ptpra1 | 5803 | 17-May-15 |
| 14986 | 2 | | | II-2 | Olfr1131 | | | 17940 | 2 | | | II-2 | Rangap1 | 5905 | 4-May-15 |
| 14987 | 2 | | | II-2 | Olfr1132 | | | 18272 | 2 | | | II-2 | Rhox12 | | |
| 14989 | 2 | | | II-2 | Olfr1134 | | | 18273 | 2 | | | II-2 | Rhox13 | | |
| 14990 | 2 | | | II-2 | Olfr1135 | | | 18275 | 2 | | | II-2 | Rhox2b | | |
| 14991 | 2 | | | II-2 | Olfr1136 | | | 18277 | 2 | | | II-2 | Rhox2d | | |
| 14992 | 2 | | | II-2 | Olfr1137 | | | 18278 | 2 | | | II-2 | Rhox2e | | |
| 14993 | 2 | | | II-2 | Olfr1138 | | | 18279 | 2 | | | II-2 | Rhox2f | | |
| 14994 | 2 | | | II-2 | Olfr114 | | | 18280 | 2 | | | II-2 | Rhox2g | | |
| 14995 | 2 | | | II-2 | Olfr1140 | | | 18281 | 2 | | | II-2 | Rhox2h | | |
| 14996 | 2 | | | II-2 | Olfr1141 | | | 18282 | 2 | | | II-2 | Rhox3a | | |
| 15026 | 2 | | | II-2 | Olfr1181 | | | 18283 | 2 | | | II-2 | Rhox3c | | |
| 15027 | 2 | | | II-2 | Olfr1182 | | | 18284 | 2 | | | II-2 | Rhox3e | | |
| 15214 | 2 | | | II-2 | Olfr1387 | | | 18285 | 2 | | | II-2 | Rhox3f | | |
| 15222 | 2 | | | II-2 | Olfr1394 | | | 18286 | 2 | | | II-2 | Rhox3g | | |
| 15233 | 2 | | | II-2 | Olfr1412 | | | 18288 | 2 | | | II-2 | Rhox4a | | |
| 15292 | 2 | | | II-2 | Olfr1490 | | | 18294 | 2 | | | II-2 | Rhox4g | | |
| 15318 | 2 | | | II-2 | Olfr1535 | | | 18295 | 2 | | | II-2 | Rhox5 | | |
| 15326 | 2 | | | II-2 | Olfr160 | | | 18299 | 2 | | | II-2 | Rhox9 | | |
| 15336 | 2 | | | II-2 | Olfr171 | | | 18475 | 2 | | | II-2 | Rnu73b | 114665 | 4-May-15 |
| 15337 | 2 | | | II-2 | Olfr172 | | | 18476 | 2 | | | II-2 | Robo1 | 6091 | 17-May-15 |
| 15340 | 2 | | | II-2 | Olfr176 | | | 18742 | 2 | | | II-2 | Rxfp4 | 339403 | 4-May-15 |
| 15350 | 2 | | | II-2 | Olfr190 | | | 18780 | 2 | | | II-2 | Sacm1l | 22908 | 23-May-15 |
| 15354 | 2 | | | II-2 | Olfr194 | | | 18784 | 2 | | | II-2 | Safb2 | 9667 | 4-May-15 |
| 15358 | 2 | | | II-2 | Olfr198 | | | 18893 | 2 | | | II-2 | Scgb1b24 | | |
| 15375 | 2 | | | II-2 | Olfr220 | | | 19150 | 2 | | | II-2 | Serpinb9e | | |
| 15410 | 2 | | | II-2 | Olfr285 | | | 19151 | 2 | | | II-2 | Serpinb9f | | |
| 15424 | 2 | | | II-2 | Olfr3 | | | 19152 | 2 | | | II-2 | Serpinb9g | | |
| 15445 | 2 | | | II-2 | Olfr320 | | | 19491 | 2 | | | II-2 | Slc22a23 | 63027 | 10-May-15 |
| 15465 | 2 | | | II-2 | Olfr348 | | | 19549 | 2 | | | II-2 | Slc25a44 | 9673 | 14-May-15 |
| 15475 | 2 | | | II-2 | Olfr360 | | | 19795 | 2 | | | II-2 | Sltn1 | | |
| 15477 | 2 | | | II-2 | Olfr362 | | | 19902 | 2 | | | II-2 | Smndc1 | 10285 | 23-May-15 |
| 15486 | 2 | | | II-2 | Olfr374 | | | 20009 | 2 | | | II-2 | Snord110 | 692213 | 4-May-15 |
| 15495 | 2 | | | II-2 | Olfr389 | | | 20010 | 2 | | | II-2 | Snord111 | 692214 | 4-May-15 |
| 15521 | 2 | | | II-2 | Olfr427 | | | 20011 | 2 | | | II-2 | Snord116 | | |
| 15528 | 2 | | | II-2 | Olfr435 | | | 20012 | 2 | | | II-2 | Snord116l1 | | |
| 15549 | 2 | | | II-2 | Olfr462 | | | 20013 | 2 | | | II-2 | Snord116l2 | | |
| 15555 | 2 | | | II-2 | Olfr47 | | | 20014 | 2 | | | II-2 | Snord118 | | |
| 15556 | 2 | | | II-2 | Olfr470 | | | 20015 | 2 | | | II-2 | Snord12 | 692057 | 4-May-15 |
| 15557 | 2 | | | II-2 | Olfr472 | | | 20016 | 2 | | | II-2 | Snord123 | 100113384 | 4-May-15 |
| 15642 | 2 | | | II-2 | Olfr569 | | | 20017 | 2 | | | II-2 | Snord14a | | |
| 15736 | 2 | | | II-2 | Olfr677 | | | 20018 | 2 | | | II-2 | Snord14c | | |
| 15746 | 2 | | | II-2 | Olfr689 | | | 20019 | 2 | | | II-2 | Snord14d | | |
| 15750 | 2 | | | II-2 | Olfr692 | | | 20027 | 2 | | | II-2 | Snord1c | 677850 | 4-May-15 |
| 15870 | 2 | | | II-2 | Olfr836 | | | 20028 | 2 | | | II-2 | Snord2 | 619567 | 4-May-15 |
| 15875 | 2 | | | II-2 | Olfr847 | | | 20033 | 2 | | | II-2 | Snord34 | 26817 | 4-May-15 |
| 15901 | 2 | | | II-2 | Olfr883 | | | 20034 | 2 | | | II-2 | Snord35a | 26816 | 4-May-15 |
| 15920 | 2 | | | II-2 | Olfr905 | | | 20035 | 2 | | | II-2 | Snord35b | 84546 | 4-May-15 |
| 15922 | 2 | | | II-2 | Olfr907 | | | 20037 | 2 | | | II-2 | Snord38a | 94182 | 12-May-15 |
| 16155 | 2 | | | II-2 | Pabpn1 | 8106 | 23-May-15 | 20038 | 2 | | | II-2 | Snord42a | 26809 | 4-May-15 |
| 16156 | 2 | | | II-2 | Pabpn1l | 390748 | 4-May-15 | 20039 | 2 | | | II-2 | Snord42b | 26808 | 4-May-15 |
| 16262 | 2 | | | II-2 | Pawr | 5074 | 24-May-15 | 20040 | 2 | | | II-2 | Snord43 | 26807 | 4-May-15 |
| 16284 | 2 | | | II-2 | Pbx3 | 5090 | 17-May-15 | 20041 | 2 | | | II-2 | Snord45b | 26804 | 4-May-15 |
| 16317 | 2 | | | II-2 | Pcdha7 | 56141 | 4-May-15 | 20042 | 2 | | | II-2 | Snord45c | 692085 | 4-May-15 |
| 16323 | 2 | | | II-2 | Pcdhb1 | 29930 | 4-May-15 | 20043 | 2 | | | II-2 | Snord47 | 26802 | 4-May-15 |
| 16612 | 2 | | | II-2 | Pgs1 | 9489 | 4-May-15 | 20044 | 2 | | | II-2 | Snord49a | 26800 | 4-May-15 |
| 16774 | 2 | | | II-2 | Pitpna | 5306 | 21-May-15 | 20045 | 2 | | | II-2 | Snord49b | 692087 | 4-May-15 |
| 16790 | 2 | | | II-2 | Pkd1 | 5310 | 31-May-15 | 20046 | 2 | | | II-2 | Snord4a | 26773 | 4-May-15 |
| 17216 | 2 | | | II-2 | Ppp1r7 | 5510 | 12-May-15 | 20047 | 2 | | | II-2 | Snord52 | 26797 | 4-May-15 |
| 17271 | 2 | | | II-2 | Pramef8 | 391002 | 4-May-15 | 20048 | 2 | | | II-2 | Snord53 | 26796 | 4-May-15 |
| 17272 | 2 | | | II-2 | Pramel1 | | | 20049 | 2 | | | II-2 | Snord55 | 26811 | 4-May-15 |
| 17273 | 2 | | | II-2 | Pramel3 | | | 20050 | 2 | | | II-2 | Snord57 | 26792 | 4-May-15 |
| 17275 | 2 | | | II-2 | Pramel5 | | | 20051 | 2 | | | II-2 | Snord58b | 26790 | 4-May-15 |
| 17277 | 2 | | | II-2 | Pramel7 | | | 20052 | 2 | | | II-2 | Snord61 | 26787 | 4-May-15 |
| 17289 | 2 | | | II-2 | Prdm15 | 63977 | 21-May-15 | 20053 | 2 | | | II-2 | Snord64 | 347686 | 4-May-15 |
| 17290 | 2 | | | II-2 | Prdm16 | 63976 | 12-May-15 | 20054 | 2 | | | II-2 | Snord65 | 692106 | 4-May-15 |
| 17291 | 2 | | | II-2 | Prdm2 | 7799 | 4-May-15 | 20055 | 2 | | | II-2 | Snord66 | 692107 | 4-May-15 |
| 17364 | 2 | | | II-2 | Prl2c2 | | | 20056 | 2 | | | II-2 | Snord67 | 692108 | 4-May-15 |
| 17365 | 2 | | | II-2 | Prl2c3 | | | 20057 | 2 | | | II-2 | Snord68 | 606500 | 4-May-15 |
| 17366 | 2 | | | II-2 | Prl2c4 | | | 20058 | 2 | | | II-2 | Snord69 | 692109 | 4-May-15 |
| 17367 | 2 | | | II-2 | Prl2c5 | | | 20059 | 2 | | | II-2 | Snord7 | 692076 | 4-May-15 |
| 17368 | 2 | | | II-2 | Prl3a1 | | | 20060 | 2 | | | II-2 | Snord70 | 692110 | 4-May-15 |
| 17369 | 2 | | | II-2 | Prl3b1 | | | 20061 | 2 | | | II-2 | Snord71 | 692111 | 4-May-15 |
| 17370 | 2 | | | II-2 | Prl3c1 | | | 20062 | 2 | | | II-2 | Snord72 | 619564 | 4-May-15 |
| 17371 | 2 | | | II-2 | Prl3d1 | | | 20063 | 2 | | | II-2 | Snord73a | 8944 | 4-May-15 |
| 17372 | 2 | | | II-2 | Prl3d2 | | | 20064 | 2 | | | II-2 | Snord8 | 319103 | 4-May-15 |
| 17374 | 2 | | | II-2 | Prl4a1 | | | 20065 | 2 | | | II-2 | Snord82 | 25826 | 12-May-15 |
| 17375 | 2 | | | II-2 | Prl5a1 | | | 20066 | 2 | | | II-2 | Snord83b | 116938 | 4-May-15 |
| 17376 | 2 | | | II-2 | Prl6a1 | | | 20067 | 2 | | | II-2 | Snord85 | 692200 | 4-May-15 |
| 17377 | 2 | | | II-2 | Prl7a1 | | | 20068 | 2 | | | II-2 | Snord87 | 641648 | 4-May-15 |
| 17378 | 2 | | | II-2 | Prl7a2 | | | 20069 | 2 | | | II-2 | Snord88a | 692202 | 4-May-15 |
| 17379 | 2 | | | II-2 | Prl7b1 | | | 20070 | 2 | | | II-2 | Snord88c | 692204 | 4-May-15 |
| 17380 | 2 | | | II-2 | Prl7c1 | | | 20071 | 2 | | | II-2 | Snord89 | 692205 | 4-May-15 |
| 17381 | 2 | | | II-2 | Prl7d1 | | | 20073 | 2 | | | II-2 | Snord91a | 692207 | 12-May-15 |
| 17382 | 2 | | | II-2 | Prl8a1 | | | 20074 | 2 | | | II-2 | Snord92 | 692209 | 4-May-15 |

Fig.22 - 91

| | | | | | | | | | | | | | | |
|---|---|---|---|---|---|---|---|---|---|---|---|---|---|---|
| 20075 | 2 | | | II-2 | Snord93 | 692210 | 4-May-15 | 22689 | 2 | | | II-2 | Vmn1r120 | | |
| 20076 | 2 | | | II-2 | Snord95 | 619570 | 4-May-15 | 22690 | 2 | | | II-2 | Vmn1r121 | | |
| 20077 | 2 | | | II-2 | Snord96a | 619571 | 4-May-15 | 22691 | 2 | | | II-2 | Vmn1r122 | | |
| 20078 | 2 | | | II-2 | Snord98 | | | 22692 | 2 | | | II-2 | Vmn1r123 | | |
| 20079 | 2 | | | II-2 | Snord99 | 692212 | 4-May-15 | 22693 | 2 | | | II-2 | Vmn1r124 | | |
| 20249 | 2 | | | II-2 | Spata31d1c | | | 22694 | 2 | | | II-2 | Vmn1r125 | | |
| 20289 | 2 | | | II-2 | Speer9-ps1 | | | 22695 | 2 | | | II-2 | Vmn1r126 | | |
| 20490 | 2 | | | II-2 | Ssu2 | 51066 | 21-May-15 | 22696 | 2 | | | II-2 | Vmn1r127 | | |
| 20500 | 2 | | | II-2 | Ssxb8 | | | 22698 | 2 | | | II-2 | Vmn1r129 | | |
| 20501 | 2 | | | II-2 | Ssxb9 | | | 22699 | 2 | | | II-2 | Vmn1r13 | | |
| 20502 | 2 | | | II-2 | St13 | 6767 | 4-May-15 | 22700 | 2 | | | II-2 | Vmn1r130 | | |
| 20680 | 2 | | | II-2 | Sult2a4 | | | 22701 | 2 | | | II-2 | Vmn1r132 | | |
| 20681 | 2 | | | II-2 | Sult2a5 | | | 22702 | 2 | | | II-2 | Vmn1r135 | | |
| 20682 | 2 | | | II-2 | Sult2a6 | | | 22703 | 2 | | | II-2 | Vmn1r137 | | |
| 20683 | 2 | | | II-2 | Sult2a7 | | | 22704 | 2 | | | II-2 | Vmn1r138 | | |
| 20691 | 2 | | | II-2 | Sumo1 | 7341 | 17-May-15 | 22705 | 2 | | | II-2 | Vmn1r139 | | |
| 20729 | 2 | | | II-2 | Svil | 6840 | 12-May-15 | 22706 | 2 | | | II-2 | Vmn1r14 | | |
| 20736 | 2 | | | II-2 | Svs3b | | | 22707 | 2 | | | II-2 | Vmn1r142 | | |
| 20737 | 2 | | | II-2 | Svs4 | | | 22708 | 2 | | | II-2 | Vmn1r148 | | |
| 20739 | 2 | | | II-2 | Svs6 | | | 22709 | 2 | | | II-2 | Vmn1r15 | | |
| 20740 | 2 | | | II-2 | Swap70 | 23075 | 4-May-15 | 22710 | 2 | | | II-2 | Vmn1r151 | | |
| 20742 | 2 | | | II-2 | Swsap1 | 126074 | 4-May-15 | 22711 | 2 | | | II-2 | Vmn1r152 | | |
| 20819 | 2 | | | II-2 | Taar2 | 9287 | 7-Jun-15 | 22713 | 2 | | | II-2 | Vmn1r158 | | |
| 20821 | 2 | | | II-2 | Taar4 | | | 22714 | 2 | | | II-2 | Vmn1r159 | | |
| 20822 | 2 | | | II-2 | Taar5 | 9038 | 4-May-15 | 22715 | 2 | | | II-2 | Vmn1r16 | | |
| 20823 | 2 | | | II-2 | Taar6 | 319100 | 4-May-15 | 22716 | 2 | | | II-2 | Vmn1r160 | | |
| 20824 | 2 | | | II-2 | Taar7a | | | 22717 | 2 | | | II-2 | Vmn1r163 | | |
| 20825 | 2 | | | II-2 | Taar7b | | | 22718 | 2 | | | II-2 | Vmn1r165 | | |
| 20826 | 2 | | | II-2 | Taar7d | | | 22721 | 2 | | | II-2 | Vmn1r169 | | |
| 20827 | 2 | | | II-2 | Taar7e | | | 22723 | 2 | | | II-2 | Vmn1r17 | | |
| 20828 | 2 | | | II-2 | Taar7f | | | 22724 | 2 | | | II-2 | Vmn1r170 | | |
| 20829 | 2 | | | II-2 | Taar8a | | | 22725 | 2 | | | II-2 | Vmn1r171 | | |
| 20830 | 2 | | | II-2 | Taar8b | | | 22726 | 2 | | | II-2 | Vmn1r172 | | |
| 20831 | 2 | | | II-2 | Taar8c | | | 22727 | 2 | | | II-2 | Vmn1r173 | | |
| 20832 | 2 | | | II-2 | Taar9 | 134860 | 4-May-15 | 22728 | 2 | | | II-2 | Vmn1r174 | | |
| 20833 | 2 | | | II-2 | Tab1 | 10454 | 4-May-15 | 22729 | 2 | | | II-2 | Vmn1r175 | | |
| 20834 | 2 | | | II-2 | Tab2 | 23118 | 12-May-15 | 22730 | 2 | | | II-2 | Vmn1r176 | | |
| 20908 | 2 | | | II-2 | Tas2r105 | | | 22731 | 2 | | | II-2 | Vmn1r177 | | |
| 20909 | 2 | | | II-2 | Tas2r106 | | | 22732 | 2 | | | II-2 | Vmn1r178 | | |
| 20910 | 2 | | | II-2 | Tas2r107 | | | 22733 | 2 | | | II-2 | Vmn1r179 | | |
| 20911 | 2 | | | II-2 | Tas2r108 | | | 22734 | 2 | | | II-2 | Vmn1r18 | | |
| 20912 | 2 | | | II-2 | Tas2r109 | | | 22735 | 2 | | | II-2 | Vmn1r180 | | |
| 20913 | 2 | | | II-2 | Tas2r110 | | | 22736 | 2 | | | II-2 | Vmn1r181 | | |
| 20914 | 2 | | | II-2 | Tas2r113 | | | 22738 | 2 | | | II-2 | Vmn1r184 | | |
| 20915 | 2 | | | II-2 | Tas2r114 | | | 22740 | 2 | | | II-2 | Vmn1r186 | | |
| 20916 | 2 | | | II-2 | Tas2r115 | | | 22741 | 2 | | | II-2 | Vmn1r187 | | |
| 20917 | 2 | | | II-2 | Tas2r116 | | | 22742 | 2 | | | II-2 | Vmn1r188 | | |
| 20918 | 2 | | | II-2 | Tas2r117 | | | 22743 | 2 | | | II-2 | Vmn1r189 | | |
| 20919 | 2 | | | II-2 | Tas2r118 | | | 22744 | 2 | | | II-2 | Vmn1r19 | | |
| 20920 | 2 | | | II-2 | Tas2r119 | | | 22745 | 2 | | | II-2 | Vmn1r191 | | |
| 20922 | 2 | | | II-2 | Tas2r121 | | | 22746 | 2 | | | II-2 | Vmn1r192 | | |
| 20923 | 2 | | | II-2 | Tas2r122 | | | 22747 | 2 | | | II-2 | Vmn1r193 | | |
| 20924 | 2 | | | II-2 | Tas2r123 | | | 22748 | 2 | | | II-2 | Vmn1r194 | | |
| 20925 | 2 | | | II-2 | Tas2r124 | | | 22749 | 2 | | | II-2 | Vmn1r195 | | |
| 20926 | 2 | | | II-2 | Tas2r125 | | | 22750 | 2 | | | II-2 | Vmn1r196 | | |
| 20927 | 2 | | | II-2 | Tas2r126 | | | 22751 | 2 | | | II-2 | Vmn1r197 | | |
| 20928 | 2 | | | II-2 | Tas2r129 | | | 22752 | 2 | | | II-2 | Vmn1r198 | | |
| 20929 | 2 | | | II-2 | Tas2r130 | | | 22753 | 2 | | | II-2 | Vmn1r199 | | |
| 20930 | 2 | | | II-2 | Tas2r131 | | | 22754 | 2 | | | II-2 | Vmn1r2 | | |
| 20931 | 2 | | | II-2 | Tas2r134 | | | 22755 | 2 | | | II-2 | Vmn1r20 | | |
| 20999 | 2 | | | II-2 | Tbrg3 | | | 22756 | 2 | | | II-2 | Vmn1r200 | | |
| 21058 | 2 | | | II-2 | Tcl1b3 | | | 22757 | 2 | | | II-2 | Vmn1r201 | | |
| 21059 | 2 | | | II-2 | Tcl1b4 | | | 22758 | 2 | | | II-2 | Vmn1r202 | | |
| 21060 | 2 | | | II-2 | Tcl1b5 | | | 22759 | 2 | | | II-2 | Vmn1r203 | | |
| 21091 | 2 | | | II-2 | Tdpoz4 | | | 22760 | 2 | | | II-2 | Vmn1r204 | | |
| 21092 | 2 | | | II-2 | Tdpoz5 | | | 22761 | 2 | | | II-2 | Vmn1r205 | | |
| 21093 | 2 | | | II-2 | Tdrd1 | 56165 | 4-May-15 | 22762 | 2 | | | II-2 | Vmn1r206 | | |
| 21094 | 2 | | | II-2 | Tdrd12 | 91646 | 4-May-15 | 22763 | 2 | | | II-2 | Vmn1r207 ps | | |
| 21095 | 2 | | | II-2 | Tdrd3 | 81550 | 4-May-15 | 22764 | 2 | | | II-2 | Vmn1r208 | | |
| 21344 | 2 | | | II-2 | Tlr1 | 7096 | 17-May-15 | 22765 | 2 | | | II-2 | Vmn1r209 | | |
| 21669 | 2 | | | II-2 | Tmprss11f | 389208 | 4-May-15 | 22766 | 2 | | | II-2 | Vmn1r21 | | |
| 21785 | 2 | | | II-2 | Tomm40 | 10452 | 12-May-15 | 22767 | 2 | | | II-2 | Vmn1r210 | | |
| 21914 | 2 | | | II-2 | Trap1 | 51499 | 4-May-15 | 22768 | 2 | | | II-2 | Vmn1r211 | | |
| 21944 | 2 | | | II-2 | Trim33 | 51592 | 23-May-15 | 22770 | 2 | | | II-2 | Vmn1r213 | | |
| 21958 | 2 | | | II-2 | Trim44 | 54765 | 4-May-15 | 22771 | 2 | | | II-2 | Vmn1r214 | | |
| 21959 | 2 | | | II-2 | Trim45 | 80263 | 4-May-15 | 22772 | 2 | | | II-2 | Vmn1r215 | | |
| 22539 | 2 | | | II-2 | Usp17d | | | 22773 | 2 | | | II-2 | Vmn1r216 | | |
| 22540 | 2 | | | II-2 | Usp17e | | | 22774 | 2 | | | II-2 | Vmn1r217 | | |
| 22541 | 2 | | | II-2 | Usp18 | 11274 | 23-May-15 | 22775 | 2 | | | II-2 | Vmn1r218 | | |
| 22601 | 2 | | | II-2 | Uvrag | 7405 | 12-May-15 | 22776 | 2 | | | II-2 | Vmn1r219 | | |
| 22609 | 2 | | | II-2 | Vamp1 | 6843 | 23-May-15 | 22777 | 2 | | | II-2 | Vmn1r22 | | |
| 22673 | 2 | | | II-2 | Vmn1r10 | | | 22778 | 2 | | | II-2 | Vmn1r220 | | |
| 22674 | 2 | | | II-2 | Vmn1r100 | | | 22779 | 2 | | | II-2 | Vmn1r221 | | |
| 22675 | 2 | | | II-2 | Vmn1r101 | | | 22780 | 2 | | | II-2 | Vmn1r222 | | |
| 22676 | 2 | | | II-2 | Vmn1r103 | | | 22781 | 2 | | | II-2 | Vmn1r223 | | |
| 22677 | 2 | | | II-2 | Vmn1r104 | | | 22782 | 2 | | | II-2 | Vmn1r224 | | |
| 22678 | 2 | | | II-2 | Vmn1r107 | | | 22783 | 2 | | | II-2 | Vmn1r225 | | |
| 22679 | 2 | | | II-2 | Vmn1r11 | | | 22784 | 2 | | | II-2 | Vmn1r226 | | |
| 22680 | 2 | | | II-2 | Vmn1r112 | | | 22785 | 2 | | | II-2 | Vmn1r227 | | |
| 22681 | 2 | | | II-2 | Vmn1r113 | | | 22860 | 2 | | | II-2 | Vmn1r80 | | |
| 22682 | 2 | | | II-2 | Vmn1r114 | | | 22929 | 2 | | | II-2 | Vmn2r35 | | |
| 22683 | 2 | | | II-2 | Vmn1r115 | | | 22991 | 2 | | | II-2 | Vmn2r92 | | |
| 22684 | 2 | | | II-2 | Vmn1r116 | | | 23128 | 2 | | | II-2 | Wdr33 | 55339 | 4-May-15 |
| 22685 | 2 | | | II-2 | Vmn1r117 | | | 23289 | 2 | | | II-2 | Xndc1 | | |
| 22686 | 2 | | | II-2 | Vmn1r118 | | | 23290 | 2 | | | II-2 | Xntrpc | | |
| 22687 | 2 | | | II-2 | Vmn1r119 | | | 23291 | 2 | | | II-2 | Xpa | 7507 | 23-May-15 |
| 22688 | 2 | | | II-2 | Vmn1r12 | | | 23588 | 2 | | | II-2 | Zfp352 | | |

Fig.22 - 92

| | | | | | | | | | | | | | |
|---|---|---|---|---|---|---|---|---|---|---|---|---|---|
| 23643 | 2 | | | II-2 | Zfp46 | 80818 | 4-May-15 | 274 | 2 | | | II-1 | 1700031M16Rik |
| 23731 | 2 | | | II-2 | Zfp668 | | | 276 | 2 | | | II-1 | 1700034E13Rik |
| 23829 | 2 | | | II-2 | Zfp930 | | | 277 | 2 | | | II-1 | 1700034F02Rik |
| 23944 | 2 | | | II-2 | Zp3r | | | 278 | 2 | | | II-1 | 1700034G24Rik |
| 23945 | 2 | | | II-2 | Zp4-ps | | | 279 | 2 | | | II-1 | 1700034H15Rik |
| 23946 | 2 | | | II-2 | Zpbp | 11055 | 4-May-15 | 280 | 2 | | | II-1 | 1700034I23Rik |
| 23948 | 2 | | | II-2 | Zpld1 | 131368 | 4-May-15 | 281 | 2 | | | II-1 | 1700034J05Rik |
| 23968 | 2 | | | II-2 | Zscan4d | | | 282 | 2 | | | II-1 | 1700034K08Rik |
| 23969 | 2 | | | II-2 | Zscan4e | | | 283 | 2 | | | II-1 | 1700034O15Rik |
| 23970 | 2 | | | II-2 | Zscan4f | | | 285 | 2 | | | II-1 | 1700036G14Rik |
| 23971 | 2 | | | II-2 | Zscan5b | 342933 | 28-May-15 | 290 | 2 | | | II-1 | 1700040L02Rik |
| 23972 | 2 | | | II-2 | Zswim1 | 90204 | 4-May-15 | 293 | 2 | | | II-1 | 1700042B14Rik |
| 23973 | 2 | | | II-2 | Zswim2 | 151112 | 4-May-15 | 294 | 2 | | | II-1 | 1700042G07Rik |
| 4 | 2 | | | II-1 | 0610009L18Rik | | | 296 | 2 | | | II-1 | 1700042O10Rik |
| 13 | 2 | | | II-1 | 0610031O16Rik | | | 298 | 2 | | | II-1 | 1700044K03Rik |
| 27 | 2 | | | II-1 | 1110006O24Rik | | | 299 | 2 | | | II-1 | 1700045H11Rik |
| 40 | 2 | | | II-1 | 1110032A03Rik | | | 301 | 2 | | | II-1 | 1700047A11Rik |
| 52 | 2 | | | II-1 | 1110059E24Rik | | | 302 | 2 | | | II-1 | 1700047E10Rik |
| 53 | 2 | | | II-1 | 1110059G10Rik | | | 306 | 2 | | | II-1 | 1700047M11Rik |
| 83 | 2 | | | II-1 | 1600015I10Rik | | | 307 | 2 | | | II-1 | 1700048M11Rik |
| 90 | 2 | | | II-1 | 1600029I14Rik | | | 311 | 2 | | | II-1 | 1700049G17Rik |
| 91 | 2 | | | II-1 | 1600029O15Rik | | | 314 | 2 | | | II-1 | 1700052I22Rik |
| 102 | 2 | | | II-1 | 1700001L05Rik | | | 315 | 2 | | | II-1 | 1700052K11Rik |
| 112 | 2 | | | II-1 | 1700003G18Rik | | | 316 | 2 | | | II-1 | 1700052N19Rik |
| 113 | 2 | | | II-1 | 1700003H04Rik | | | 319 | 2 | | | II-1 | 1700054M17Rik |
| 114 | 2 | | | II-1 | 1700003L19Rik | | | 321 | 2 | | | II-1 | 1700055C04Rik |
| 115 | 2 | | | II-1 | 1700003M02Rik | | | 322 | 2 | | | II-1 | 1700055N04Rik |
| 116 | 2 | | | II-1 | 1700003M07Rik | | | 323 | 2 | | | II-1 | 1700056E22Rik |
| 118 | 2 | | | II-1 | 1700006A11Rik | | | 326 | 2 | | | II-1 | 1700060C16Rik |
| 119 | 2 | | | II-1 | 1700006E09Rik | | | 327 | 2 | | | II-1 | 1700060C20Rik |
| 120 | 2 | | | II-1 | 1700006F04Rik | | | 330 | 2 | | | II-1 | 1700061I17Rik |
| 121 | 2 | | | II-1 | 1700006H21Rik | | | 331 | 2 | | | II-1 | 1700063A18Rik |
| 122 | 2 | | | II-1 | 1700007B14Rik | | | 332 | 2 | | | II-1 | 1700063D05Rik |
| 123 | 2 | | | II-1 | 1700007F19Rik | | | 333 | 2 | | | II-1 | 1700063O14Rik |
| 125 | 2 | | | II-1 | 1700007J10Rik | | | 335 | 2 | | | II-1 | 1700064M15Rik |
| 131 | 2 | | | II-1 | 1700008I05Rik | | | 340 | 2 | | | II-1 | 1700065L07Rik |
| 132 | 2 | | | II-1 | 1700008J07Rik | | | 341 | 2 | | | II-1 | 1700065O20Rik |
| 135 | 2 | | | II-1 | 1700008P02Rik | | | 342 | 2 | | | II-1 | 1700066B17Rik |
| 136 | 2 | | | II-1 | 1700009C05Rik | | | 347 | 2 | | | II-1 | 1700067G17Rik |
| 144 | 2 | | | II-1 | 1700010J16Rik | | | 350 | 2 | | | II-1 | 1700069I16Rik |
| 146 | 2 | | | II-1 | 1700011A15Rik | | | 351 | 2 | | | II-1 | 1700069P05Rik |
| 147 | 2 | | | II-1 | 1700011B04Rik | | | 352 | 2 | | | II-1 | 1700071K01Rik |
| 148 | 2 | | | II-1 | 1700011E24Rik | | | 356 | 2 | | | II-1 | 1700073I17Rik |
| 152 | 2 | | | II-1 | 1700011M02Rik | | | 359 | 2 | | | II-1 | 1700080E11Rik |
| 160 | 2 | | | II-1 | 1700012P22Rik | | | 360 | 2 | | | II-1 | 1700080N15Rik |
| 162 | 2 | | | II-1 | 1700013F07Rik | | | 361 | 2 | | | II-1 | 1700080O36Rik |
| 163 | 2 | | | II-1 | 1700013G24Rik | | | 362 | 2 | | | II-1 | 1700081H04Rik |
| 165 | 2 | | | II-1 | 1700015E13Rik | | | 368 | 2 | | | II-1 | 1700086L19Rik |
| 166 | 2 | | | II-1 | 1700015F17Rik | | | 375 | 2 | | | II-1 | 1700092K14Rik |
| 167 | 2 | | | II-1 | 1700015G11Rik | | | 380 | 2 | | | II-1 | 1700094M24Rik |
| 168 | 2 | | | II-1 | 1700016C15Rik | | | 381 | 2 | | | II-1 | 1700095A21Rik |
| 171 | 2 | | | II-1 | 1700016H13Rik | | | 382 | 2 | | | II-1 | 1700095B10Rik |
| 178 | 2 | | | II-1 | 1700017G19Rik | | | 396 | 2 | | | II-1 | 1700108I01Rik |
| 179 | 2 | | | II-1 | 1700017I07Rik | | | 397 | 2 | | | II-1 | 1700109G14Rik |
| 180 | 2 | | | II-1 | 1700017N19Rik | | | 398 | 2 | | | II-1 | 1700109G15Rik |
| 181 | 2 | | | II-1 | 1700018A04Rik | | | 399 | 2 | | | II-1 | 1700109H08Rik |
| 183 | 2 | | | II-1 | 1700018B24Rik | | | 400 | 2 | | | II-1 | 1700109I08Rik |
| 184 | 2 | | | II-1 | 1700018C11Rik | | | 401 | 2 | | | II-1 | 1700109K24Rik |
| 185 | 2 | | | II-1 | 1700018F24Rik | | | 409 | 2 | | | II-1 | 1700113A16Rik |
| 186 | 2 | | | II-1 | 1700018G05Rik | | | 418 | 2 | | | II-1 | 1700122O11Rik |
| 190 | 2 | | | II-1 | 1700019B21Rik | | | 421 | 2 | | | II-1 | 1700123L14Rik |
| 196 | 2 | | | II-1 | 1700019M22Rik | | | 425 | 2 | | | II-1 | 1700123O21Rik |
| 198 | 2 | | | II-1 | 1700019O17Rik | | | 429 | 2 | | | II-1 | 1700125H03Rik |
| 199 | 2 | | | II-1 | 1700020A23Rik | | | 432 | 2 | | | II-1 | 1700128A07Rik |
| 200 | 2 | | | II-1 | 1700020D05Rik | | | 433 | 2 | | | II-1 | 1700128F08Rik |
| 208 | 2 | | | II-1 | 1700021F05Rik | | | 435 | 2 | | | II-1 | 1810006J02Rik |
| 210 | 2 | | | II-1 | 1700021K19Rik | | | 437 | 2 | | | II-1 | 1810007D17Rik |
| 211 | 2 | | | II-1 | 1700021N21Rik | | | 456 | 2 | | | II-1 | 1810026J23Rik |
| 212 | 2 | | | II-1 | 1700022A21Rik | | | 474 | 2 | | | II-1 | 2010002M12Rik |
| 213 | 2 | | | II-1 | 1700022A22Rik | | | 494 | 2 | | | II-1 | 2010315B03Rik |
| 214 | 2 | | | II-1 | 1700022E09Rik | | | 495 | 2 | | | II-1 | 2010320M18Rik |
| 216 | 2 | | | II-1 | 1700022I11Rik | | | 504 | 2 | | | II-1 | 2210018M11Rik |
| 217 | 2 | | | II-1 | 1700023C21Rik | | | 505 | 2 | | | II-1 | 2210019I11Rik |
| 219 | 2 | | | II-1 | 1700023F02Rik | | | 530 | 2 | | | II-1 | 2310005G13Rik |
| 220 | 2 | | | II-1 | 1700023F06Rik | | | 539 | 2 | | | II-1 | 2310015A10Rik |
| 223 | 2 | | | II-1 | 1700024F13Rik | | | 546 | 2 | | | II-1 | 2310030A07Rik |
| 224 | 2 | | | II-1 | 1700024G13Rik | | | 554 | 2 | | | II-1 | 2310039H08Rik |
| 228 | 2 | | | II-1 | 1700025C18Rik | | | 559 | 2 | | | II-1 | 2310043G21Rik |
| 229 | 2 | | | II-1 | 1700025F22Rik | | | 560 | 2 | | | II-1 | 2310045N01Rik |
| 230 | 2 | | | II-1 | 1700025F24Rik | | | 566 | 2 | | | II-1 | 2310061I04Rik |
| 233 | 2 | | | II-1 | 1700025M24Rik | | | 578 | 2 | | | II-1 | 2410004B18Rik |
| 234 | 2 | | | II-1 | 1700025N23Rik | | | 579 | 2 | | | II-1 | 2410004I01Rik |
| 237 | 2 | | | II-1 | 1700026F02Rik | | | 585 | 2 | | | II-1 | 2410012M07Rik |
| 241 | 2 | | | II-1 | 1700027H10Rik | | | 590 | 2 | | | II-1 | 2410021H03Rik |
| 242 | 2 | | | II-1 | 1700027I24Rik | | | 591 | 2 | | | II-1 | 2410076I21Rik |
| 243 | 2 | | | II-1 | 1700027J07Rik | | | 594 | 2 | | | II-1 | 2410114N07Rik |
| 248 | 2 | | | II-1 | 1700028J19Rik | | | 596 | 2 | | | II-1 | 2410127L13Rik |
| 252 | 2 | | | II-1 | 1700028P15Rik | | | 598 | 2 | | | II-1 | 2410137M14Rik |
| 253 | 2 | | | II-1 | 1700029B22Rik | | | 600 | 2 | | | II-1 | 2500004C02Rik |
| 254 | 2 | | | II-1 | 1700029F12Rik | | | 604 | 2 | | | II-1 | 2510039O18Rik |
| 256 | 2 | | | II-1 | 1700029I15Rik | | | 605 | 2 | | | II-1 | 2610049I12Rik |
| 260 | 2 | | | II-1 | 1700029N11Rik | | | 607 | 2 | | | II-1 | 2610002J02Rik |
| 261 | 2 | | | II-1 | 1700029P11Rik | | | 608 | 2 | | | II-1 | 2610002M06Rik |
| 266 | 2 | | | II-1 | 1700030J22Rik | | | 609 | 2 | | | II-1 | 2610005L07Rik |
| 270 | 2 | | | II-1 | 1700030N03Rik | | | 617 | 2 | | | II-1 | 2610028E06Rik |
| 272 | 2 | | | II-1 | 1700031A10Rik | | | 619 | 2 | | | II-1 | 2610034B18Rik |
| 273 | 2 | | | II-1 | 1700031F05Rik | | | 628 | 2 | | | II-1 | 2610206C17Rik |

Fig.22 - 93

| | | | | | | | | | | |
|---|---|---|---|---|---|---|---|---|---|---|
| 630 | 2 | | | H-1 | 2610301B20Rik | | 935 | 2 | H-1 | 4930479O17Rik |
| 635 | 2 | | | H-1 | 2610318N02Rik | | 937 | 2 | H-1 | 4930480G23Rik |
| 647 | 2 | | | H-1 | 2700060E02Rik | | 939 | 2 | H-1 | 4930480M12Rik |
| 649 | 2 | | | H-1 | 2700069J18Rik | | 943 | 2 | H-1 | 4930483K19Rik |
| 652 | 2 | | | H-1 | 2700086A05Rik | | 945 | 2 | H-1 | 4930486F22Rik |
| 660 | 2 | | | H-1 | 2810004N23Rik | | 946 | 2 | H-1 | 4930486I03Rik |
| 672 | 2 | | | H-1 | 2810403A07Rik | | 951 | 2 | H-1 | 4930488L21Rik |
| 673 | 2 | | | H-1 | 2810403D21Rik | | 952 | 2 | H-1 | 4930500F04Rik |
| 683 | 2 | | | H-1 | 2810433D01Rik | | 954 | 2 | H-1 | 4930500L23Rik |
| 699 | 2 | | | H-1 | 2900056M20Rik | | 955 | 2 | H-1 | 4930502A04Rik |
| 722 | 2 | | | H-1 | 3110039M20Rik | | 960 | 2 | H-1 | 4930503E24Rik |
| 723 | 2 | | | H-1 | 3110040N11Rik | | 961 | 2 | H-1 | 4930503H13Rik |
| 735 | 2 | | | H-1 | 3200001D21Rik | | 962 | 2 | H-1 | 4930503I19Rik |
| 736 | 2 | | | H-1 | 3300002I08Rik | | 963 | 2 | H-1 | 4930503O07Rik |
| 743 | 2 | | | H-1 | 3830408C21Rik | | 965 | 2 | H-1 | 4930505A04Rik |
| 745 | 2 | | | H-1 | 3930402G23Rik | | 966 | 2 | H-1 | 4930505G20Rik |
| 748 | 2 | | | H-1 | 4632415L05Rik | | 971 | 2 | H-1 | 4930509E16Rik |
| 762 | 2 | | | H-1 | 4833417C18Rik | | 973 | 2 | H-1 | 4930509K18Rik |
| 769 | 2 | | | H-1 | 4833427F10Rik | | 974 | 2 | H-1 | 4930511A02Rik |
| 771 | 2 | | | H-1 | 4833428L15Rik | | 979 | 2 | H-1 | 4930513N10Rik |
| 772 | 2 | | | H-1 | 4833439L19Rik | | 982 | 2 | H-1 | 4930515G01Rik |
| 773 | 2 | | | H-1 | 4921501E09Rik | | 985 | 2 | H-1 | 4930515I19Rik |
| 774 | 2 | | | H-1 | 4921504A21Rik | | 986 | 2 | H-1 | 4930517E11Rik |
| 775 | 2 | | | H-1 | 4921504E06Rik | | 992 | 2 | H-1 | 4930519G04Rik |
| 776 | 2 | | | H-1 | 4921506M07Rik | | 993 | 2 | H-1 | 4930519H02Rik |
| 777 | 2 | | | H-1 | 4921507L20Rik | | 997 | 2 | H-1 | 4930522H14Rik |
| 778 | 2 | | | H-1 | 4921507P07Rik | | 998 | 2 | H-1 | 4930522O17Rik |
| 780 | 2 | | | H-1 | 4921509C19Rik | | 1001 | 2 | H-1 | 4930524B15Rik |
| 781 | 2 | | | H-1 | 4921509O07Rik | | 1002 | 2 | H-1 | 4930524C18Rik |
| 783 | 2 | | | H-1 | 4921511C20Rik | | 1004 | 2 | H-1 | 4930524O05Rik |
| 787 | 2 | | | H-1 | 4921513I03Rik | | 1005 | 2 | H-1 | 4930524O08Rik |
| 788 | 2 | | | H-1 | 4921515E04Rik | | 1008 | 2 | H-1 | 4930525M21Rik |
| 789 | 2 | | | H-1 | 4921517O22Rik | | 1009 | 2 | H-1 | 4930526I15Rik |
| 790 | 2 | | | H-1 | 4921524J17Rik | | 1012 | 2 | H-1 | 4930527G23Rik |
| 793 | 2 | | | H-1 | 4921529L05Rik | | 1013 | 2 | H-1 | 4930528A17Rik |
| 794 | 2 | | | H-1 | 4921530L21Rik | | 1014 | 2 | H-1 | 4930528D03Rik |
| 795 | 2 | | | H-1 | 4921531C22Rik | | 1015 | 2 | H-1 | 4930528P14Rik |
| 801 | 2 | | | H-1 | 4922502D21Rik | | 1016 | 2 | H-1 | 4930529C04Rik |
| 804 | 2 | | | H-1 | 4930401C15Rik | | 1023 | 2 | H-1 | 4930538K18Rik |
| 805 | 2 | | | H-1 | 4930401O10Rik | | 1029 | 2 | H-1 | 4930540M03Rik |
| 808 | 2 | | | H-1 | 4930402F11Rik | | 1035 | 2 | H-1 | 4930544M13Rik |
| 809 | 2 | | | H-1 | 4930402H24Rik | | 1036 | 2 | H-1 | 4930545E07Rik |
| 811 | 2 | | | H-1 | 4930404A05Rik | | 1039 | 2 | H-1 | 4930546C10Rik |
| 812 | 2 | | | H-1 | 4930404A10Rik | | 1040 | 2 | H-1 | 4930546K05Rik |
| 813 | 2 | | | H-1 | 4930404H11Rik | | 1041 | 2 | H-1 | 4930547E08Rik |
| 820 | 2 | | | H-1 | 4930405L22Rik | | 1043 | 2 | H-1 | 4930548G14Rik |
| 822 | 2 | | | H-1 | 4930407I10Rik | | 1045 | 2 | H-1 | 4930548J01Rik |
| 823 | 2 | | | H-1 | 4930412B13Rik | | 1046 | 2 | H-1 | 4930548K13Rik |
| 824 | 2 | | | H-1 | 4930412C18Rik | | 1049 | 2 | H-1 | 4930550C14Rik |
| 832 | 2 | | | H-1 | 4930414N06Rik | | 1051 | 2 | H-1 | 4930552N02Rik |
| 834 | 2 | | | H-1 | 4930415L06Rik | | 1052 | 2 | H-1 | 4930552P12Rik |
| 835 | 2 | | | H-1 | 4930415O20Rik | | 1053 | 2 | H-1 | 4930553E22Rik |
| 836 | 2 | | | H-1 | 4930417O13Rik | | 1055 | 2 | H-1 | 4930555B11Rik |
| 839 | 2 | | | H-1 | 4930423M02Rik | | 1056 | 2 | H-1 | 4930555G01Rik |
| 840 | 2 | | | H-1 | 4930425K10Rik | | 1058 | 2 | H-1 | 4930556G01Rik |
| 847 | 2 | | | H-1 | 4930428G15Rik | | 1059 | 2 | H-1 | 4930556I02Rik |
| 851 | 2 | | | H-1 | 4930429F11Rik | | 1060 | 2 | H-1 | 4930556M19Rik |
| 855 | 2 | | | H-1 | 4930430F08Rik | | 1063 | 2 | H-1 | 4930557O02Rik |
| 858 | 2 | | | H-1 | 4930431F12Rik | | 1065 | 2 | H-1 | 4930558G05Rik |
| 860 | 2 | | | H-1 | 4930432J09Rik | | 1067 | 2 | H-1 | 4930558K02Rik |
| 862 | 2 | | | H-1 | 4930432M17Rik | | 1072 | 2 | H-1 | 4930563E22Rik |
| 863 | 2 | | | H-1 | 4930433B08Rik | | 1073 | 2 | H-1 | 4930563F08Rik |
| 864 | 2 | | | H-1 | 4930433I11Rik | | 1083 | 2 | H-1 | 4930567K20Rik |
| 866 | 2 | | | H-1 | 4930434J06Rik | | 1084 | 2 | H-1 | 4930568I16Rik |
| 868 | 2 | | | H-1 | 4930438E09Rik | | 1086 | 2 | H-1 | 4930568G15Rik |
| 869 | 2 | | | H-1 | 4930440C22Rik | | 1087 | 2 | H-1 | 4930570G19Rik |
| 871 | 2 | | | H-1 | 4930441J16Rik | | 1091 | 2 | H-1 | 4930572O03Rik |
| 876 | 2 | | | H-1 | 4930444G20Rik | | 1092 | 2 | H-1 | 4930572O13Rik |
| 877 | 2 | | | H-1 | 4930444M15Rik | | 1093 | 2 | H-1 | 4930573O16Rik |
| 879 | 2 | | | H-1 | 4930447A16Rik | | 1094 | 2 | H-1 | 4930577N17Rik |
| 883 | 2 | | | H-1 | 4930447N08Rik | | 1098 | 2 | H-1 | 4930578M01Rik |
| 884 | 2 | | | H-1 | 4930448C13Rik | | 1101 | 2 | H-1 | 4930579G18Rik |
| 886 | 2 | | | H-1 | 4930448H16Rik | | 1102 | 2 | H-1 | 4930579G24Rik |
| 889 | 2 | | | H-1 | 4930448K20Rik | | 1107 | 2 | H-1 | 4930584F24Rik |
| 890 | 2 | | | H-1 | 4930449E01Rik | | 1108 | 2 | H-1 | 4930590I08Rik |
| 892 | 2 | | | H-1 | 4930449I24Rik | | 1109 | 2 | H-1 | 4930590L20Rik |
| 893 | 2 | | | H-1 | 4930451C15Rik | | 1110 | 2 | H-1 | 4930591A17Rik |
| 899 | 2 | | | H-1 | 4930452N14Rik | | 1114 | 2 | H-1 | 4930593C16Rik |
| 900 | 2 | | | H-1 | 4930453H23Rik | | 1115 | 2 | H-1 | 4930594C11Rik |
| 901 | 2 | | | H-1 | 4930453I07Rik | | 1116 | 2 | H-1 | 4930595M18Rik |
| 907 | 2 | | | H-1 | 4930455B04Rik | | 1118 | 2 | H-1 | 4930596I21Rik |
| 908 | 2 | | | H-1 | 4930455J16Rik | | 1119 | 2 | H-1 | 4930597G03Rik |
| 909 | 2 | | | H-1 | 4930456L15Rik | | 1120 | 2 | H-1 | 4930598F16Rik |
| 916 | 2 | | | H-1 | 4930467D21Rik | | 1121 | 2 | H-1 | 4930599N23Rik |
| 917 | 2 | | | H-1 | 4930467E23Rik | | 1126 | 2 | H-1 | 4931406C07Rik |
| 918 | 2 | | | H-1 | 4930467K11Rik | | 1128 | 2 | H-1 | 4931406P16Rik |
| 920 | 2 | | | H-1 | 4930469G21Rik | | 1129 | 2 | H-1 | 4931408C20Rik |
| 922 | 2 | | | H-1 | 4930470P17Rik | | 1130 | 2 | H-1 | 4931408D14Rik |
| 923 | 2 | | | H-1 | 4930471C04Rik | | 1133 | 2 | H-1 | 4931414P19Rik |
| 924 | 2 | | | H-1 | 4930471G03Rik | | 1134 | 2 | H-1 | 4931417E11Rik |
| 925 | 2 | | | H-1 | 4930471M09Rik | | 1136 | 2 | H-1 | 4931420L22Rik |
| 926 | 2 | | | H-1 | 4930473A02Rik | | 1141 | 2 | H-1 | 4931429L15Rik |
| 927 | 2 | | | H-1 | 4930473O22Rik | | 1142 | 2 | H-1 | 4931429P17Rik |
| 928 | 2 | | | H-1 | 4930474G06Rik | | 1143 | 2 | H-1 | 4931430N09Rik |
| 929 | 2 | | | H-1 | 4930474H20Rik | | 1144 | 2 | H-1 | 4931431B13Rik |
| 933 | 2 | | | H-1 | 4930478L05Rik | | 1149 | 2 | H-1 | 4931440L10Rik |
| 934 | 2 | | | H-1 | 4930478P22Rik | | 1150 | 2 | H-1 | 4931440P22Rik |

Fig.22 - 94

| | | | | | | | | | | | |
|---|---|---|---|---|---|---|---|---|---|---|---|
| 1151 | 2 | | | II-1 | 4932411E22Rik | | 1426 | 2 | | II-1 | 9030625G05Rik | |
| 1153 | 2 | | | II-1 | 4932412D23Rik | | 1431 | 2 | | II-1 | 9130019G22Rik | |
| 1155 | 2 | | | II-1 | 4932414J04Rik | | 1438 | 2 | | II-1 | 9130221H12Rik | |
| 1156 | 2 | | | II-1 | 4932414N04Rik | | 1439 | 2 | | II-1 | 9130227L01Rik | |
| 1157 | 2 | | | II-1 | 4932415M13Rik | | 1451 | 2 | | II-1 | 9230112I17Rik | |
| 1159 | 2 | | | II-1 | 4932416K20Rik | | 1452 | 2 | | II-1 | 9230114K14Rik | |
| 1163 | 2 | | | II-1 | 4932438A13Rik | | 1456 | 2 | | II-1 | 9330102E08Rik | |
| 1167 | 2 | | | II-1 | 4932702P03Rik | | 1462 | 2 | | II-1 | 9330159F19Rik | |
| 1170 | 2 | | | II-1 | 4933400C23Rik | | 1469 | 2 | | II-1 | 9330179D12Rik | |
| 1171 | 2 | | | II-1 | 4933400F21Rik | | 1473 | 2 | | II-1 | 9430007A20Rik | |
| 1176 | 2 | | | II-1 | 4933402C08Rik | | 1479 | 2 | | II-1 | 9430019I16Rik | |
| 1177 | 2 | | | II-1 | 4933402D24Rik | | 1480 | 2 | | II-1 | 9430020K01Rik | |
| 1178 | 2 | | | II-1 | 4933402E13Rik | | 1483 | 2 | | II-1 | 9430038I01Rik | |
| 1179 | 2 | | | II-1 | 4933402J07Rik | | 1487 | 2 | | II-1 | 9430076C15Rik | |
| 1180 | 2 | | | II-1 | 4933402J10Rik | | 1488 | 2 | | II-1 | 9430083A17Rik | |
| 1181 | 2 | | | II-1 | 4933402J15Rik | | 1492 | 2 | | II-1 | 9530026F06Rik | |
| 1182 | 2 | | | II-1 | 4933402N03Rik | | 1501 | 2 | | II-1 | 9530077C05Rik | |
| 1183 | 2 | | | II-1 | 4933402N22Rik | | 1505 | 2 | | II-1 | 9630001P10Rik | |
| 1186 | 2 | | | II-1 | 4933404G15Rik | | 1506 | 2 | | II-1 | 9630013A20Rik | |
| 1187 | 2 | | | II-1 | 4933404K08Rik | | 1507 | 2 | | II-1 | 9630028B13Rik | |
| 1191 | 2 | | | II-1 | 4933405L10Rik | | 1509 | 2 | | II-1 | 9630033F20Rik | |
| 1195 | 2 | | | II-1 | 4933406F09Rik | | 1519 | 2 | | II-1 | 9930111J21Rik1 | |
| 1196 | 2 | | | II-1 | 4933406G16Rik | | 1521 | 2 | | II-1 | a | |
| 1197 | 2 | | | II-1 | 4933406I18Rik | | 1524 | 2 | | II-1 | A1bg | 1 | 4-May-15 |
| 1200 | 2 | | | II-1 | 4933406K04Rik | | 1525 | 2 | | II-1 | A1cf | 29974 | 4-May-15 |
| 1201 | 2 | | | II-1 | 4933406M09Rik | | 1530 | 2 | | II-1 | A230046K03Rik | |
| 1202 | 2 | | | II-1 | 4933407E24Rik | | 1531 | 2 | | II-1 | A230050P20Rik | |
| 1203 | 2 | | | II-1 | 4933407G14Rik | | 1540 | 2 | | II-1 | A230077H06Rik | |
| 1204 | 2 | | | II-1 | 4933407I05Rik | | 1544 | 2 | | II-1 | A330009N23Rik | |
| 1210 | 2 | | | II-1 | 4933409G03Rik | | 1548 | 2 | | II-1 | A330033J07Rik | |
| 1211 | 2 | | | II-1 | 4933409K07Rik | | 1549 | 2 | | II-1 | A330035P11Rik | |
| 1214 | 2 | | | II-1 | 4933411G11Rik | | 1555 | 2 | | II-1 | A330069E16Rik | |
| 1220 | 2 | | | II-1 | 4933413G19Rik | | 1562 | 2 | | II-1 | A3galt2 | 127550 | 4-May-15 |
| 1222 | 2 | | | II-1 | 4933413L06Rik | | 1564 | 2 | | II-1 | A430033K04Rik | |
| 1225 | 2 | | | II-1 | 4933416E03Rik | | 1568 | 2 | | II-1 | A430089I19Rik | |
| 1226 | 2 | | | II-1 | 4933416H08Rik | | 1569 | 2 | | II-1 | A430090L17Rik | |
| 1229 | 2 | | | II-1 | 4933417A18Rik | | 1570 | 2 | | II-1 | A430093F15Rik | |
| 1234 | 2 | | | II-1 | 4933421H07Rik | | 1580 | 2 | | II-1 | A530050N04Rik | |
| 1235 | 2 | | | II-1 | 4933421O10Rik | | 1585 | 2 | | II-1 | A530065N20Rik | |
| 1237 | 2 | | | II-1 | 4933422H20Rik | | 1593 | 2 | | II-1 | A630019A02Rik | |
| 1239 | 2 | | | II-1 | 4933424G06Rik | | 1594 | 2 | | II-1 | A630020A06 | |
| 1240 | 2 | | | II-1 | 4933425B07Rik | | 1602 | 2 | | II-1 | A630076J17Rik | |
| 1242 | 2 | | | II-1 | 4933426M11Rik | | 1616 | 2 | | II-1 | A730046J19Rik | |
| 1243 | 2 | | | II-1 | 4933427D06Rik | | 1617 | 2 | | II-1 | A730056A06Rik | |
| 1245 | 2 | | | II-1 | 4933427E11Rik | | 1619 | 2 | | II-1 | A730085K08Rik | |
| 1247 | 2 | | | II-1 | 4933427G17Rik | | 1620 | 2 | | II-1 | A730090H04Rik | |
| 1250 | 2 | | | II-1 | 4933428G20Rik | | 1623 | 2 | | II-1 | A830009L08Rik | |
| 1251 | 2 | | | II-1 | 4933429K18Rik | | 1624 | 2 | | II-1 | A830010M20Rik | |
| 1254 | 2 | | | II-1 | 4933430I17Rik | | 1628 | 2 | | II-1 | A830080D01Rik | |
| 1255 | 2 | | | II-1 | 4933430M04Rik | | 1631 | 2 | | II-1 | A930001A20Rik | |
| 1257 | 2 | | | II-1 | 4933431E20Rik | | 1632 | 2 | | II-1 | A930001C03Rik | |
| 1260 | 2 | | | II-1 | 4933432I03Rik | | 1636 | 2 | | II-1 | A930005H10Rik | |
| 1261 | 2 | | | II-1 | 4933432J09Rik | | 1641 | 2 | | II-1 | A930011G23Rik | |
| 1264 | 2 | | | II-1 | 4933433F19Rik | | 1653 | 2 | | II-1 | AA388235 | |
| 1266 | 2 | | | II-1 | 4933433G15Rik | | 1662 | 2 | | II-1 | AA543401 | |
| 1268 | 2 | | | II-1 | 4933433H22Rik | | 1664 | 2 | | II-1 | AA619741 | |
| 1269 | 2 | | | II-1 | 4933434E20Rik | | 1677 | 2 | | II-1 | Aamdc | 28971 | 4-May-15 |
| 1270 | 2 | | | II-1 | 4933434J20Rik | | 1678 | 2 | | II-1 | Aamp | 14 | 12-May-15 |
| 1271 | 2 | | | II-1 | 4933436E23Rik | | 1680 | 2 | | II-1 | Aar2 | 25980 | 4-May-15 |
| 1272 | 2 | | | II-1 | 4933436H12Rik | | 1681 | 2 | | II-1 | Aard | 441376 | 4-May-15 |
| 1273 | 2 | | | II-1 | 4933436I01Rik | | 1684 | 2 | | II-1 | Aarsd1 | 80755 | 4-May-15 |
| 1275 | 2 | | | II-1 | 4933438K21Rik | | 1685 | 2 | | II-1 | Aasdh | 132949 | 4-May-15 |
| 1278 | 2 | | | II-1 | 4933439C10Rik | | 1696 | 2 | | II-1 | Abca14 | |
| 1280 | 2 | | | II-1 | 5031410I06Rik | | 1697 | 2 | | II-1 | Abca15 | |
| 1282 | 2 | | | II-1 | 5031425E22Rik | | 1698 | 2 | | II-1 | Abca16 | |
| 1284 | 2 | | | II-1 | 5031426D15Rik | | 1699 | 2 | | II-1 | Abca17 | 650655 | 12-May-15 |
| 1285 | 2 | | | II-1 | 5031434C07Rik | | 1702 | 2 | | II-1 | Abca4 | 24 | 23-May-15 |
| 1286 | 2 | | | II-1 | 5031434O11Rik | | 1717 | 2 | | II-1 | Abcb8 | 11194 | 12-May-15 |
| 1293 | 2 | | | II-1 | 5330413P13Rik | | 1726 | 2 | | II-1 | Abcc6 | 368 | 23-May-15 |
| 1295 | 2 | | | II-1 | 5330426P16Rik | | 1735 | 2 | | II-1 | Abcf2 | 10061 | 12-May-15 |
| 1299 | 2 | | | II-1 | 5430402E10Rik | | 1736 | 2 | | II-1 | Abcf3 | 55324 | 4-May-15 |
| 1300 | 2 | | | II-1 | 5430402O13Rik | | 1737 | 2 | | II-1 | Abcg3 | 9619 | 24-May-15 |
| 1306 | 2 | | | II-1 | 5430419D17Rik | | 1743 | 2 | | II-1 | Abhd1 | 84696 | 4-May-15 |
| 1307 | 2 | | | II-1 | 5430421F17Rik | | 1745 | 2 | | II-1 | Abhd11 | 83451 | 4-May-15 |
| 1312 | 2 | | | II-1 | 5430428J19Rik | | 1750 | 2 | | II-1 | Abhd14a | 25864 | 4-May-15 |
| 1313 | 2 | | | II-1 | 5430434I15Rik | | 1755 | 2 | | II-1 | Abhd17a | 81926 | 4-May-15 |
| 1317 | 2 | | | II-1 | 5530400C23Rik | | 1756 | 2 | | II-1 | Abhd17b | 51104 | 4-May-15 |
| 1318 | 2 | | | II-1 | 5530401A14Rik | | 1757 | 2 | | II-1 | Abhd17c | 58489 | 4-May-15 |
| 1332 | 2 | | | II-1 | 5730480H06Rik | | 1790 | 2 | | II-1 | Acad | 33 | 4-May-15 |
| 1344 | 2 | | | II-1 | 5830418K08Rik | | 1799 | 2 | | II-1 | Acat1 | 38 | 7-Jun-15 |
| 1356 | 2 | | | II-1 | 6030408B16Rik | | 1800 | 2 | | II-1 | Acat2 | 39 | 7-Jun-15 |
| 1360 | 2 | | | II-1 | 6030458C11Rik | | 1803 | 2 | | II-1 | Acbd4 | 79777 | 4-May-15 |
| 1364 | 2 | | | II-1 | 6030498E09Rik | | 1804 | 2 | | II-1 | Acbd5 | 91452 | 12-May-15 |
| 1365 | 2 | | | II-1 | 6230400D17Rik | | 1809 | 2 | | II-1 | Acd | 65057 | 4-May-15 |
| 1376 | 2 | | | II-1 | 6330409D20Rik | | 1814 | 2 | | II-1 | Acer2 | 340485 | 4-May-15 |
| 1380 | 2 | | | II-1 | 6430548M08Rik | | 1883 | 2 | | II-1 | Actl6b | 51412 | 1-Jun-15 |
| 1382 | 2 | | | II-1 | 6430562O15Rik | | 1884 | 2 | | II-1 | Actl7a | 10881 | 4-May-15 |
| 1387 | 2 | | | II-1 | 6430710C18Rik | | 1886 | 2 | | II-1 | Actl9 | 284382 | 4-May-15 |
| 1388 | 2 | | | II-1 | 6530402F18Rik | | 1892 | 2 | | II-1 | Actr1a | 10121 | 4-May-15 |
| 1394 | 2 | | | II-1 | 6820408C15Rik | | 1893 | 2 | | II-1 | Actr1b | 10120 | 4-May-15 |
| 1398 | 2 | | | II-1 | 7420700N18Rik | | 1894 | 2 | | II-1 | Actr2 | 10097 | 4-May-15 |
| 1400 | 2 | | | II-1 | 7530416G11Rik | | 1895 | 2 | | II-1 | Actr3 | 10096 | 4-May-15 |
| 1405 | 2 | | | II-1 | 8030442B05Rik | | 1896 | 2 | | II-1 | Actr3b | 57180 | 4-May-15 |
| 1411 | 2 | | | II-1 | 8430423G03Rik | | 1897 | 2 | | II-1 | Actr5 | 79913 | 4-May-15 |
| 1412 | 2 | | | II-1 | 8430426J06Rik | | 1901 | 2 | | II-1 | Actrt2 | 140625 | 4-May-15 |
| 1417 | 2 | | | II-1 | 8430437L04Rik | | 1902 | 2 | | II-1 | Actrt3 | 84517 | 4-May-15 |
| 1421 | 2 | | | II-1 | 9030612E09Rik | | 1903 | 2 | | II-1 | Acvr1 | 90 | 12-May-15 |

Fig.22 - 95

| | | | | | | | | | | | | | |
|---|---|---|---|---|---|---|---|---|---|---|---|---|---|
| 1908 | 2 | | | II-1 | Acvrl1 | 94 | 23-May-15 | 2497 | 2 | | | II-1 | Ap2b1 | 163 | 4-May-15 |
| 1915 | 2 | | | II-1 | Adad2 | 161931 | 4-May-15 | 2498 | 2 | | | II-1 | Ap2m1 | 1173 | 4-May-15 |
| 1916 | 2 | | | II-1 | Adal | 161823 | 4-May-15 | 2499 | 2 | | | II-1 | Ap2s1 | 1175 | 12-May-15 |
| 1922 | 2 | | | II-1 | Adam18 | 8749 | May-15 | 2500 | 2 | | | II-1 | Ap3b1 | 8546 | 23-May-15 |
| 1924 | 2 | | | II-1 | Adam1a | 8759 | 4-May-15 | 2503 | 2 | | | II-1 | Ap3m1 | 26985 | 4-May-15 |
| 1928 | 2 | | | II-1 | Adam21 | 8747 | 4-May-15 | 2504 | 2 | | | II-1 | Ap3m2 | 10947 | 4-May-15 |
| 1929 | 2 | | | II-1 | Adam22 | 53616 | 4-May-15 | 2508 | 2 | | | II-1 | Ap4e1 | 23431 | 12-May-15 |
| 1933 | 2 | | | II-1 | Adam26a | | | 2510 | 2 | | | II-1 | Ap4s1 | 11154 | 4-May-15 |
| 1934 | 2 | | | II-1 | Adam26b | | | 2519 | 2 | | | II-1 | Apbb1 | 322 | 12-May-15 |
| 1937 | 2 | | | II-1 | Adam3 | 1587 | 4-May-15 | 2535 | 2 | | | II-1 | Apip | 51074 | 4-May-15 |
| 1938 | 2 | | | II-1 | Adam30 | 11085 | 4-May-15 | 2584 | 2 | | | II-1 | Appl1 | 26060 | 24-May-15 |
| 1939 | 2 | | | II-1 | Adam32 | 203102 | 4-May-15 | 2603 | 2 | | | II-1 | Arap2 | 116984 | 4-May-15 |
| 1940 | 2 | | | II-1 | Adam33 | 80332 | 4-May-15 | 2610 | 2 | | | II-1 | Arf2 | 378 | 31-May-15 |
| 1941 | 2 | | | II-1 | Adam34 | | | 2611 | 2 | | | II-1 | Arf3 | 377 | 4-May-15 |
| 1942 | 2 | | | II-1 | Adam39 | | | 2612 | 2 | | | II-1 | Arf4 | 378 | 31-May-15 |
| 1943 | 2 | | | II-1 | Adam4 | | | 2613 | 2 | | | II-1 | Arf5 | 381 | 23-May-15 |
| 1945 | 2 | | | II-1 | Adam6a | | | 2614 | 2 | | | II-1 | Arf6 | 382 | 23-May-15 |
| 1946 | 2 | | | II-1 | Adam6b | | | 2615 | 2 | | | II-1 | Arfgap1 | 55738 | 7-Jun-15 |
| 1959 | 2 | | | II-1 | Adamts18 | 170692 | 12-May-15 | 2616 | 2 | | | II-1 | Arfgap2 | 84364 | 4-May-15 |
| 1961 | 2 | | | II-1 | Adamts2 | 9509 | 7-Jun-15 | 2617 | 2 | | | II-1 | Arfgap3 | 26286 | 4-May-15 |
| 1964 | 2 | | | II-1 | Adamts4 | 9507 | 7-Jun-15 | 2618 | 2 | | | II-1 | Arfgef1 | 10565 | 4-May-15 |
| 1980 | 2 | | | II-1 | Adat1 | 23536 | 4-May-15 | 2619 | 2 | | | II-1 | Arfgef2 | 10564 | 4-May-15 |
| 1981 | 2 | | | II-1 | Adat2 | 134637 | 23-May-15 | 2621 | 2 | | | II-1 | Arfip2 | 23647 | 4-May-15 |
| 1988 | 2 | | | II-1 | Adck5 | 203054 | 4-May-15 | 2622 | 2 | | | II-1 | Arfrp1 | 10139 | 23-May-15 |
| 1999 | 2 | | | II-1 | Adcyap1 | 116 | 17-May-15 | 2623 | 2 | | | II-1 | Arg1 | 383 | 7-Jun-15 |
| 2007 | 2 | | | II-1 | Adh5 | 128 | 7-Jun-15 | 2627 | 2 | | | II-1 | Arhgap10 | 79658 | 7-Jun-15 |
| 2017 | 2 | | | II-1 | Adk | 132 | 4-May-15 | 2633 | 2 | | | II-1 | Arhgap18 | 93663 | 4-May-15 |
| 2032 | 2 | | | II-1 | Adra1a | 148 | 7-Jun-15 | 2671 | 2 | | | II-1 | Arhgef15 | 22899 | 4-May-15 |
| 2050 | 2 | | | II-1 | Aen | 64782 | 23-May-15 | 2680 | 2 | | | II-1 | Arhgef3 | 50650 | 4-May-15 |
| 2057 | 2 | | | II-1 | AF357399 | | | 2687 | 2 | | | II-1 | Arhgef5 | 79984 | 4-May-15 |
| 2062 | 2 | | | II-1 | Afap1 | 60312 | 4-May-15 | 2689 | 2 | | | II-1 | Arhgef7 | 8874 | 4-May-15 |
| 2063 | 2 | | | II-1 | Afap1l1 | 134265 | 4-May-15 | 2691 | 2 | | | II-1 | Arid1a | 8289 | 24-May-15 |
| 2067 | 2 | | | II-1 | Aff3 | 3899 | 4-May-15 | 2692 | 2 | | | II-1 | Arid1b | 57492 | 12-May-15 |
| 2070 | 2 | | | II-1 | Afg3l2 | 10939 | 23-May-15 | 2693 | 2 | | | II-1 | Arid2 | 196528 | 4-May-15 |
| 2071 | 2 | | | II-1 | Afm | 173 | 4-May-15 | 2697 | 2 | | | II-1 | Arid4a | 5926 | 4-May-15 |
| 2080 | 2 | | | II-1 | Agbl2 | 79841 | 23-May-15 | 2703 | 2 | | | II-1 | Arl1 | 400 | 7-Jun-15 |
| 2086 | 2 | | | II-1 | Agfg2 | 3268 | 4-May-15 | 2704 | 2 | | | II-1 | Arl10 | 285598 | 4-May-15 |
| 2088 | 2 | | | II-1 | Agk | 55750 | 4-May-15 | 2708 | 2 | | | II-1 | Arl14 | 80117 | 4-May-15 |
| 2129 | 2 | | | II-1 | AI118078 | | | 2711 | 2 | | | II-1 | Arl15 | 54622 | 4-May-15 |
| 2133 | 2 | | | II-1 | AI314278 | | | 2712 | 2 | | | II-1 | Arl16 | 339231 | 4-May-15 |
| 2149 | 2 | | | II-1 | AI606473 | | | 2715 | 2 | | | II-1 | Arl3 | 403 | 4-May-15 |
| 2150 | 2 | | | II-1 | AI607873 | | | 2726 | 2 | | | II-1 | Arl6ip6 | 151188 | 4-May-15 |
| 2162 | 2 | | | II-1 | AI987944 | | | 2728 | 2 | | | II-1 | Arl8b | 55207 | 4-May-15 |
| 2176 | 2 | | | II-1 | Aip | 9049 | 7-Jun-15 | 2729 | 2 | | | II-1 | Arl9 | 132946 | 4-May-15 |
| 2177 | 2 | | | II-1 | Aip1 | 23746 | 23-May-15 | 2730 | 2 | | | II-1 | Armc1 | 55156 | 4-May-15 |
| 2178 | 2 | | | II-1 | Aire | 326 | 28-May-15 | 2731 | 2 | | | II-1 | Armc10 | 83787 | 4-May-15 |
| 2184 | 2 | | | II-1 | AK129341 | | | 2734 | 2 | | | II-1 | Armc3 | 219681 | 4-May-15 |
| 2192 | 2 | | | II-1 | Akap1 | 8165 | 4-May-15 | 2737 | 2 | | | II-1 | Armc6 | 93436 | 4-May-15 |
| 2193 | 2 | | | II-1 | Akap10 | 11216 | 12-May-15 | 2738 | 2 | | | II-1 | Armc7 | 79637 | 12-May-15 |
| 2194 | 2 | | | II-1 | Akap11 | 11215 | 4-May-15 | 2745 | 2 | | | II-1 | Armcx5 | 64860 | 4-May-15 |
| 2199 | 2 | | | II-1 | Akap2 | 11217 | 7-Jun-15 | 2752 | 2 | | | II-1 | Arpc1b | 10095 | 4-May-15 |
| 2200 | 2 | | | II-1 | Akap3 | 10566 | 4-May-15 | 2754 | 2 | | | II-1 | Arpc3 | 10094 | 12-May-15 |
| 2211 | 2 | | | II-1 | Akna | 80709 | 4-May-15 | 2755 | 2 | | | II-1 | Arpc4 | 10093 | 4-May-15 |
| 2212 | 2 | | | II-1 | Aknad1 | 254268 | 4-May-15 | 2756 | 2 | | | II-1 | Arpc5 | 10092 | 4-May-15 |
| 2215 | 2 | | | II-1 | Akr1b10 | 57016 | 4-May-15 | 2757 | 2 | | | II-1 | Arpc5l | 81873 | 12-May-15 |
| 2225 | 2 | | | II-1 | Akr1c21 | | | 2762 | 2 | | | II-1 | Arrb2 | 409 | 17-May-15 |
| 2226 | 2 | | | II-1 | Akr1c6 | | | 2789 | 2 | | | II-1 | Asap1 | 50807 | 12-May-15 |
| 2233 | 2 | | | II-1 | Akt2 | 208 | 17-May-15 | 2809 | 2 | | | II-1 | Asb8 | 140461 | 4-May-15 |
| 2234 | 2 | | | II-1 | Akt3 | 10000 | 17-May-15 | 2810 | 2 | | | II-1 | Asb9 | 140462 | 3-May-15 |
| 2235 | 2 | | | II-1 | Aktip | 64400 | 12-May-15 | 2825 | 2 | | | II-1 | Asic1 | 41 | 4-May-15 |
| 2259 | 2 | | | II-1 | Aldh8a1 | 64577 | 23-May-15 | 2829 | 2 | | | II-1 | Asic5 | 51802 | 4-May-15 |
| 2270 | 2 | | | II-1 | Alg13 | 79868 | 23-May-15 | 2849 | 2 | | | II-1 | Astn1 | 460 | 4-May-15 |
| 2274 | 2 | | | II-1 | Alg5 | 29880 | 4-May-15 | 2850 | 2 | | | II-1 | Astn2 | 23245 | 4-May-15 |
| 2279 | 2 | | | II-1 | Alkbh1 | 8846 | 4-May-15 | 2852 | 2 | | | II-1 | Asxl1 | 171023 | 21-May-15 |
| 2283 | 2 | | | II-1 | Alkbh5 | 54890 | 4-May-15 | 2853 | 2 | | | II-1 | Asxl2 | 55252 | 4-May-15 |
| 2305 | 2 | | | II-1 | Als2cl | 259173 | 4-May-15 | 2867 | 2 | | | II-1 | Atf2 | 1386 | 7-Jun-15 |
| 2328 | 2 | | | II-1 | Amh | 268 | 17-May-15 | 2881 | 2 | | | II-1 | Atg16l1 | 55054 | 21-May-15 |
| 2353 | 2 | | | II-1 | Anapc11 | 51529 | 2-Jun-15 | 2882 | 2 | | | II-1 | Atg16l2 | 89849 | 21-May-15 |
| 2358 | 2 | | | II-1 | Anapc4 | 29945 | 4-May-15 | 2885 | 2 | | | II-1 | Atg3 | 64422 | 23-May-15 |
| 2359 | 2 | | | II-1 | Anapc5 | 51433 | 4-May-15 | 2890 | 2 | | | II-1 | Atg5 | 9474 | 21-May-15 |
| 2360 | 2 | | | II-1 | Anapc7 | 51434 | 4-May-15 | 2891 | 2 | | | II-1 | Atg7 | 10533 | 4-May-15 |
| 2367 | 2 | | | II-1 | Angel1 | 23357 | 29-May-15 | 2892 | 2 | | | II-1 | Atg9a | 79065 | 21-May-15 |
| 2384 | 2 | | | II-1 | Ankef1 | 63926 | 4-May-15 | 2915 | 2 | | | II-1 | Atp13a3 | 79572 | 4-May-15 |
| 2387 | 2 | | | II-1 | Ankhd1 | 54882 | 3-May-15 | 2948 | 2 | | | II-1 | Atp5j2 | 9551 | 4-May-15 |
| 2389 | 2 | | | II-1 | Ankk1 | 255239 | 24-May-15 | 2954 | 2 | | | II-1 | Atp6ap1 | 527 | 4-May-15 |
| 2393 | 2 | | | II-1 | Ankmy2 | 57037 | 4-May-15 | 2958 | 2 | | | II-1 | Atp6v0a2 | 23545 | 23-May-15 |
| 2397 | 2 | | | II-1 | Ankrd11 | 29123 | 12-May-15 | 2959 | 2 | | | II-1 | Atp6v0a4 | 50617 | 24-May-15 |
| 2402 | 2 | | | II-1 | Ankrd13d | 338692 | 4-May-15 | 2961 | 2 | | | II-1 | Atp6v0c | 527 | 4-May-15 |
| 2426 | 2 | | | II-1 | Ankrd45 | 339416 | 12-May-15 | 2976 | 2 | | | II-1 | Atp6v1g1 | 9550 | 4-May-15 |
| 2428 | 2 | | | II-1 | Ankrd49 | 54851 | 4-May-15 | 2985 | 2 | | | II-1 | Atp8b2 | 57198 | 21-May-15 |
| 2429 | 2 | | | II-1 | Ankrd50 | 57182 | 4-May-15 | 2988 | 2 | | | II-1 | Atp8b5 | | |
| 2430 | 2 | | | II-1 | Ankrd52 | 283373 | 4-May-15 | 2992 | 2 | | | II-1 | Atpaf2 | 91647 | 4-May-15 |
| 2433 | 2 | | | II-1 | Ankrd55 | 79722 | 4-May-15 | 2993 | 2 | | | II-1 | Atpif1 | 93974 | 24-May-15 |
| 2436 | 2 | | | II-1 | Ankrd61 | 100310 / 846 | 4-May-15 | 2997 | 2 | | | II-1 | Atrn | 8455 | 17-May-15 |
| 2444 | 2 | | | II-1 | Anks4b | 257629 | 4-May-15 | 2998 | 2 | | | II-1 | Atrnl1 | 26033 | 4-May-15 |
| 2446 | 2 | | | II-1 | Ankub1 | 389161 | 4-May-15 | 3002 | 2 | | | II-1 | Atxn1l | 342371 | 4-May-15 |
| 2447 | 2 | | | II-1 | Ankzf1 | 55139 | 4-May-15 | 3003 | 2 | | | II-1 | Atxn2 | 6311 | 23-May-15 |
| 2453 | 2 | | | II-1 | Ano4 | 121601 | 4-May-15 | 3006 | 2 | | | II-1 | Atxn7 | 6314 | 23-May-15 |
| 2457 | 2 | | | II-1 | Ano8 | 57719 | 4-May-15 | 3007 | 2 | | | II-1 | Atxn7l1 | 222255 | 12-May-15 |
| 2458 | 2 | | | II-1 | Ano9 | 338440 | 4-May-15 | 3008 | 2 | | | II-1 | Atxn7l2 | 127002 | 4-May-15 |
| 2460 | 2 | | | II-1 | Anp32b | 10541 | 4-May-15 | 3014 | 2 | | | II-1 | AU016765 | | |
| 2461 | 2 | | | II-1 | Anp32e | 81611 | 31-May-15 | 3015 | 2 | | | II-1 | AU018091 | | |
| 2465 | 2 | | | II-1 | Antxrl | 195977 | 4-May-15 | 3018 | 2 | | | II-1 | AU019990 | | |
| 2484 | 2 | | | II-1 | Aox3 | | | 3020 | 2 | | | II-1 | AU021092 | | |
| 2485 | 2 | | | II-1 | Aox4 | | | 3023 | 2 | | | II-1 | AU022754 | | |
| 2488 | 2 | | | II-1 | Ap1g1 | 164 | 4-May-15 | 3024 | 2 | | | II-1 | AU022793 | | |
| 2489 | 2 | | | II-1 | Ap1g2 | 8906 | 12-May-15 | 3025 | 2 | | | II-1 | AU023762 | | |

Fig.22 - 96

| | | | | | | | | | | | | | | |
|---|---|---|---|---|---|---|---|---|---|---|---|---|---|---|
| 3029 | 2 | | | II-1 | Auh | 549 | 21-May-15 | 3582 | 2 | | | II-1 | C130021J20Rik | | |
| 3052 | 2 | | | II-1 | AW495222 | | | 3585 | 2 | | | II-1 | C130030K03Rik | | |
| 3057 | 2 | | | II-1 | AW822252 | | | 3591 | 2 | | | II-1 | C130071C03Rik | | |
| 3067 | 2 | | | II-1 | AY761184 | | | 3595 | 2 | | | II-1 | C130083M11Rik | | |
| 3073 | 2 | | | II-1 | B020004C17Rik | | | 3596 | 2 | | | II-1 | C1d | 10438 | 4-May-15 |
| 3075 | 2 | | | II-1 | B020014A21Rik | | | 3607 | 2 | | | II-1 | C1qtnf1 | 114897 | 4-May-15 |
| 3082 | 2 | | | II-1 | B230118H07Rik | | | 3608 | 2 | | | II-1 | C1qtnf2 | 114898 | 12-May-15 |
| 3083 | 2 | | | II-1 | B230119M05Rik | | | 3623 | 2 | | | II-1 | C230029M16 | | |
| 3087 | 2 | | | II-1 | B230214G05Rik | | | 3629 | 2 | | | II-1 | C2cd2 | 25966 | 4-May-15 |
| 3100 | 2 | | | II-1 | B3galt1 | 8708 | 21-May-15 | 3632 | 2 | | | II-1 | C2cd4a | 145741 | 4-May-15 |
| 3109 | 2 | | | II-1 | B3gnt1 | 10678 | 7-Jun-15 | 3640 | 2 | | | II-1 | C330011F03Rik | | |
| 3135 | 2 | | | II-1 | B630019K06Rik | | | 3641 | 2 | | | II-1 | C330013E15Rik | | |
| 3140 | 2 | | | II-1 | B930041F14Rik | | | 3647 | 2 | | | II-1 | C330024D21Rik | | |
| 3145 | 2 | | | II-1 | Baalc | 79870 | 12-May-15 | 3648 | 2 | | | II-1 | C330027C09Rik | | |
| 3148 | 2 | | | II-1 | Bace1 | 23621 | 17-May-15 | 3653 | 2 | | | II-1 | C430049B03Rik | | |
| 3158 | 2 | | | II-1 | Bag5 | 9529 | 26-May-15 | 3666 | 2 | | | II-1 | C630043F03Rik | | |
| 3159 | 2 | | | II-1 | Bag6 | 7917 | 29-May-15 | 3670 | 2 | | | II-1 | C730036E19Rik | | |
| 3164 | 2 | | | II-1 | Bai3 | 577 | 4-May-15 | 3676 | 2 | | | II-1 | C87198 | | |
| 3169 | 2 | | | II-1 | Bak1 | 578 | 17-May-15 | 3681 | 2 | | | II-1 | C8a | 731 | 12-May-15 |
| 3177 | 2 | | | II-1 | Bard1 | 580 | 24-May-15 | 3692 | 2 | | | II-1 | Cabin1 | 23523 | 21-May-15 |
| 3180 | 2 | | | II-1 | Barx1 | 56033 | 4-May-15 | 3703 | 2 | | | II-1 | Cachd1 | 57685 | 12-May-15 |
| 3190 | 2 | | | II-1 | Barx2b | 29994 | 12-May-15 | 3721 | 2 | | | II-1 | Cacnb4 | 785 | 23-May-15 |
| 3193 | 2 | | | II-1 | BB031773 | | | 3725 | 2 | | | II-1 | Cacng4 | 27092 | 4-May-15 |
| 3196 | 2 | | | II-1 | BB287469 | | | 3732 | 2 | | | II-1 | Cacybp | 27101 | 26-May-15 |
| 3198 | 2 | | | II-1 | Bbc3 | 27113 | 24-May-15 | 3752 | 2 | | | II-1 | Calm1 | 801 | 17-May-15 |
| 3206 | 2 | | | II-1 | Bbs5 | 129880 | 23-May-15 | 3754 | 2 | | | II-1 | Calm3 | 808 | 12-May-15 |
| 3209 | 2 | | | II-1 | Bbx | 56987 | 4-May-15 | 3763 | 2 | | | II-1 | Calu | 813 | 2-Jun-15 |
| 3211 | 2 | | | II-1 | BC003331 | | | 3764 | 2 | | | II-1 | Caly | 50632 | 20-May-15 |
| 3213 | 2 | | | II-1 | BC094004 | | | 3787 | 2 | | | II-1 | Cand2 | 23066 | 4-May-15 |
| 3214 | 2 | | | II-1 | BC005537 | | | 3790 | 2 | | | II-1 | Cap1 | 10487 | 7-Jun-15 |
| 3220 | 2 | | | II-1 | BC017158 | | | 3796 | 2 | | | II-1 | Capn12 | 147988 | 4-May-15 |
| 3221 | 2 | | | II-1 | BC017643 | | | 3803 | 2 | | | II-1 | Capn7 | 23473 | 4-May-15 |
| 3224 | 2 | | | II-1 | BC018507 | | | 3809 | 2 | | | II-1 | Caprin2 | 65960 | 12-May-15 |
| 3234 | 2 | | | II-1 | BC024978 | | | 3811 | 2 | | | II-1 | Caps1 | 133690 | 4-May-15 |
| 3244 | 2 | | | II-1 | BC030499 | | | 3812 | 2 | | | II-1 | Capza1 | 829 | 4-May-15 |
| 3245 | 2 | | | II-1 | BC030500 | | | 3815 | 2 | | | II-1 | Capzb | 832 | 4-May-15 |
| 3246 | 2 | | | II-1 | BC030867 | | | 3837 | 2 | | | II-1 | Carf | 79800 | 7-Jun-15 |
| 3249 | 2 | | | II-1 | BC031361 | | | 3838 | 2 | | | II-1 | Carhsp1 | 23589 | |
| 3252 | 2 | | | II-1 | BC037032 | | | 3841 | 2 | | | II-1 | Cars1 | 57571 | 4-May-15 |
| 3259 | 2 | | | II-1 | BC048507 | | | 3842 | 2 | | | II-1 | Cars | 833 | 4-May-15 |
| 3264 | 2 | | | II-1 | BC048644 | | | 3843 | 2 | | | II-1 | Cars2 | 79587 | 4-May-15 |
| 3265 | 2 | | | II-1 | BC048671 | | | 3846 | 2 | | | II-1 | Casc3 | 22794 | 4-May-15 |
| 3268 | 2 | | | II-1 | BC049635 | | | 3847 | 2 | | | II-1 | Casc4 | 113201 | 4-May-15 |
| 3269 | 2 | | | II-1 | BC049715 | | | 3851 | 2 | | | II-1 | Caskin1 | 57524 | 4-May-15 |
| 3277 | 2 | | | II-1 | BC051665 | | | 3852 | 2 | | | II-1 | Caskin2 | 57513 | 4-May-15 |
| 3278 | 2 | | | II-1 | BC052040 | | | 3868 | 2 | | | II-1 | Cast | 831 | 7-Jun-15 |
| 3281 | 2 | | | II-1 | BC053749 | | | 3879 | 2 | | | II-1 | Catsperg2 | | |
| 3284 | 2 | | | II-1 | BC055402 | | | 3880 | 2 | | | II-1 | Cav1 | 857 | 31-May-15 |
| 3287 | 2 | | | II-1 | BC061212 | | | 3885 | 2 | | | II-1 | Cb8b | 865 | 7-Jun-15 |
| 3288 | 2 | | | II-1 | BC061237 | | | 3902 | 2 | | | II-1 | Cbx3 | 11335 | 12-May-15 |
| 3292 | 2 | | | II-1 | BC068281 | | | 3908 | 2 | | | II-1 | Cby1 | 25776 | 4-May-15 |
| 3312 | 2 | | | II-1 | Bcas3 | 54828 | 12-May-15 | 3911 | 2 | | | II-1 | Cc2d2a | 57545 | 12-May-15 |
| 3313 | 2 | | | II-1 | Bcas3os1 | | | 3912 | 2 | | | II-1 | Ccar1 | 55749 | 29-May-15 |
| 3314 | 2 | | | II-1 | Bcas3os2 | | | 3920 | 2 | | | II-1 | Ccdc104 | 112942 | 4-May-15 |
| 3318 | 2 | | | II-1 | Bcdin3d | 144233 | 4-May-15 | 3922 | 2 | | | II-1 | Ccdc106 | 29903 | 4-May-15 |
| 3324 | 2 | | | II-1 | Bcl11a | 53335 | 4-May-15 | 3925 | 2 | | | II-1 | Ccdc109b | 55013 | 4-May-15 |
| 3363 | 2 | | | II-1 | Begain | 57506 | 4-May-15 | 3928 | 2 | | | II-1 | Ccdc112 | 153733 | 12-May-15 |
| 3369 | 2 | | | II-1 | Best1 | 7439 | 23-May-15 | 3931 | 2 | | | II-1 | Ccdc115 | 84317 | 4-May-15 |
| 3417 | 2 | | | II-1 | Bloc1s5 | 63915 | 4-May-15 | 3934 | 2 | | | II-1 | Ccdc12 | 151903 | 4-May-15 |
| 3418 | 2 | | | II-1 | Bloc1s6 | 26258 | 23-May-15 | 3942 | 2 | | | II-1 | Ccdc129 | 223075 | 4-May-15 |
| 3419 | 2 | | | II-1 | Blvra | 644 | 4-May-15 | 3943 | 2 | | | II-1 | Ccdc13 | 152206 | 29-May-15 |
| 3427 | 2 | | | II-1 | Bmp2 | 650 | 24-May-15 | 3944 | 2 | | | II-1 | Ccdc130 | 81576 | 14-May-15 |
| 3440 | 2 | | | II-1 | Bms1 | 9790 | 4-May-15 | 3945 | 2 | | | II-1 | Ccdc132 | 55610 | 29-May-15 |
| 3441 | 2 | | | II-1 | Bmx | 660 | 4-May-15 | 3946 | 2 | | | II-1 | Ccdc134 | 79879 | 12-May-15 |
| 3452 | 2 | | | II-1 | Bod1l | 259282 | 4-May-15 | 3955 | 2 | | | II-1 | Ccdc146 | 57639 | 4-May-15 |
| 3466 | 2 | | | II-1 | Bpifa5 | | | 3956 | 2 | | | II-1 | Ccdc147 | 159686 | 4-May-15 |
| 3467 | 2 | | | II-1 | Bpifa6 | | | 3959 | 2 | | | II-1 | Ccdc15 | 80071 | 4-May-15 |
| 3471 | 2 | | | II-1 | Bpifb4 | 149354 | 4-May-15 | 3962 | 2 | | | II-1 | Ccdc152 | 100129792 | 4-May-15 |
| 3479 | 2 | | | II-1 | Braf | 673 | 7-Jun-15 | 3966 | 2 | | | II-1 | Ccdc157 | 550631 | |
| 3481 | 2 | | | II-1 | Brat1 | 221927 | 31-May-15 | 3978 | 2 | | | II-1 | Ccdc172 | 374355 | 4-May-15 |
| 3482 | 2 | | | II-1 | Brca1 | 672 | 25-May-15 | 3979 | 2 | | | II-1 | Ccdc173 | 129881 | 4-May-15 |
| 3487 | 2 | | | II-1 | Brd3 | 8019 | 4-May-15 | 3982 | 2 | | | II-1 | Ccdc176 | 80127 | 4-May-15 |
| 3488 | 2 | | | II-1 | Brd4 | 23476 | 24-May-15 | 3985 | 2 | | | II-1 | Ccdc18 | 343099 | |
| 3489 | 2 | | | II-1 | Brd7 | 29117 | 4-May-15 | 3988 | 2 | | | II-1 | Ccdc184 | 387856 | 4-May-15 |
| 3490 | 2 | | | II-1 | Brd8 | 10902 | 12-May-15 | 3995 | 2 | | | II-1 | Ccdc27 | 148870 | 4-May-15 |
| 3491 | 2 | | | II-1 | Brd9 | 65980 | 4-May-15 | 3996 | 2 | | | II-1 | Ccdc28a | 25901 | 4-May-15 |
| 3493 | 2 | | | II-1 | Bre | 9577 | 12-May-15 | 4001 | 2 | | | II-1 | Ccdc33 | 80125 | 12-May-15 |
| 3496 | 2 | | | II-1 | Bri3 | 25798 | 7-Jun-15 | 4004 | 2 | | | II-1 | Ccdc36 | 339834 | 4-May-15 |
| 3499 | 2 | | | II-1 | Brinp1 | 1620 | 4-May-15 | 4005 | 2 | | | II-1 | Ccdc37 | 348807 | 4-May-15 |
| 3500 | 2 | | | II-1 | Brinp2 | 57795 | 4-May-15 | 4007 | 2 | | | II-1 | Ccdc39 | 339829 | 23-May-15 |
| 3502 | 2 | | | II-1 | Brip1 | 83990 | 7-Jun-15 | 4008 | 2 | | | II-1 | Ccdc40 | 55036 | 23-May-15 |
| 3505 | 2 | | | II-1 | Brms1 | 25855 | 7-Jun-15 | 4009 | 2 | | | II-1 | Ccdc42 | 146849 | 4-May-15 |
| 3508 | 2 | | | II-1 | Brpf1 | 7862 | 7-Jun-15 | 4010 | 2 | | | II-1 | Ccdc42b | 387885 | 4-May-15 |
| 3509 | 2 | | | II-1 | Brpf3 | 27154 | 4-May-15 | 4015 | 2 | | | II-1 | Ccdc53 | 51019 | 4-May-15 |
| 3511 | 2 | | | II-1 | Brsk1 | 84446 | 4-May-15 | 4022 | 2 | | | II-1 | Ccdc60 | 160777 | 4-May-15 |
| 3514 | 2 | | | II-1 | Brwd3 | 254065 | 4-May-15 | 4029 | 2 | | | II-1 | Ccdc66 | 285331 | |
| 3517 | 2 | | | II-1 | Bsg | 682 | 17-May-15 | 4035 | 2 | | | II-1 | Ccdc71 | 64925 | 12-May-15 |
| 3528 | 2 | | | II-1 | Btbd10 | 84280 | 12-May-15 | 4036 | 2 | | | II-1 | Ccdc71l | 168455 | 4-May-15 |
| 3529 | 2 | | | II-1 | Btbd11 | 121551 | 4-May-15 | 4041 | 2 | | | II-1 | Ccdc79 | 283847 | 4-May-15 |
| 3533 | 2 | | | II-1 | Btbd19 | 149478 | 4-May-15 | 4047 | 2 | | | II-1 | Ccdc84 | 338657 | 4-May-15 |
| 3540 | 2 | | | II-1 | Btc | 685 | 4-May-15 | 4053 | 2 | | | II-1 | Ccdc88a | 55704 | 31-May-15 |
| 3544 | 2 | | | II-1 | Btg1 | 694 | 7-Jun-15 | 4054 | 2 | | | II-1 | Ccdc88b | 283234 | |
| 3552 | 2 | | | II-1 | Btnl1 | | | 4059 | 2 | | | II-1 | Ccdc91 | 55297 | 4-May-15 |
| 3558 | 2 | | | II-1 | Btnl9 | 153579 | 12-May-15 | 4065 | 2 | | | II-1 | Ccer1 | 196477 | 4-May-15 |
| 3564 | 2 | | | II-1 | Bud31 | 8896 | 4-May-15 | 4066 | 2 | | | II-1 | Cchcr1 | 54535 | 12-May-15 |
| 3575 | 2 | | | II-1 | C030023E24Rik | | | 4067 | 2 | | | II-1 | Cchcr1 | 881 | |
| 3577 | 2 | | | II-1 | C030034I22Rik | | | 4114 | 2 | | | II-1 | Ccni | 10983 | 4-May-15 |

Fig.22 - 97

| | | | | | | | |
|---|---|---|---|---|---|---|---|
| 4116 | 2 | | II-1 | Ccnjl | 79616 | | |
| 4119 | 2 | | II-1 | Ccnl2 | 81669 | 4-May-15 |
| 4124 | 2 | | II-1 | Ccnyl1 | 151195 | 4-May-15 |
| 4125 | 2 | | II-1 | Ccp110 | 9738 | 31-May-15 |
| 4126 | 2 | | II-1 | Ccpg1 | 9236 | 4-May-15 |
| 4134 | 2 | | II-1 | Ccr5 | 1234 | |
| 4145 | 2 | | II-1 | Cct2 | 10576 | 17-May-15 |
| 4147 | 2 | | II-1 | Cct4 | 10575 | 4-May-15 |
| 4148 | 2 | | II-1 | Cct5 | 22948 | 2-Jun-15 |
| 4149 | 2 | | II-1 | Cct6a | 908 | 4-May-15 |
| 4150 | 2 | | II-1 | Cct6b | 10693 | 4-May-15 |
| 4151 | 2 | | II-1 | Cct7 | 10574 | 4-May-15 |
| 4152 | 2 | | II-1 | Cct8 | 10694 | 12-May-15 |
| 4153 | 2 | | II-1 | Cct8l1 | 155100 | 4-May-15 |
| 4154 | 2 | | II-1 | Ccz1 | 51622 | 4-May-15 |
| 4174 | 2 | | II-1 | Cd200r4 | | |
| 4240 | 2 | | II-1 | Cd82 | 3732 | |
| 4254 | 2 | | II-1 | Cdc123 | 8872 | 4-May-15 |
| 4255 | 2 | | II-1 | Cdc14a | 8556 | 4-May-15 |
| 4266 | 2 | | II-1 | Cdc34 | 997 | 4-May-15 |
| 4268 | 2 | | II-1 | Cdc37l1 | 55664 | 4-May-15 |
| 4269 | 2 | | II-1 | Cdc40 | 51362 | 4-May-15 |
| 4270 | 2 | | II-1 | Cdc42 | 998 | 23-May-15 |
| 4271 | 2 | | II-1 | Cdc42bpa | 8476 | 4-May-15 |
| 4281 | 2 | | II-1 | Cdc45 | 8318 | 4-May-15 |
| 4310 | 2 | | II-1 | Cdh26 | 60437 | 4-May-15 |
| 4313 | 2 | | II-1 | Cdh5 | 1003 | 31-May-15 |
| 4318 | 2 | | II-1 | Cdhr1 | 92211 | 4-May-15 |
| 4320 | 2 | | II-1 | Cdhr3 | 222256 | |
| 4328 | 2 | | II-1 | Cdk13 | 8621 | 4-May-15 |
| 4332 | 2 | | II-1 | Cdk17 | 5128 | 4-May-15 |
| 4335 | 2 | | II-1 | Cdk2 | 1017 | 12-May-15 |
| 4338 | 2 | | II-1 | Cdk2ap2 | 10263 | 4-May-15 |
| 4339 | 2 | | II-1 | Cdk3-ps | | |
| 4342 | 2 | | II-1 | Cdk5r1 | 8851 | 4-May-15 |
| 4345 | 2 | | II-1 | Cdk5rap2 | 55755 | 23-May-15 |
| 4351 | 2 | | II-1 | Cdkal1 | 54901 | 31-May-15 |
| 4356 | 2 | | II-1 | Cdkl5 | 6792 | 23-May-15 |
| 4362 | 2 | | II-1 | Cdkn2aipnl | 91368 | 4-May-15 |
| 4381 | 2 | | II-1 | Cdx2 | 1045 | 31-May-15 |
| 4382 | 2 | | II-1 | Cdx4 | 1046 | 28-May-15 |
| 4383 | 2 | | II-1 | Cdyl | 9425 | 4-May-15 |
| 4385 | 2 | | II-1 | Ceacam1 | 634 | 12-May-15 |
| 4391 | 2 | | II-1 | Ceacam15 | | |
| 4394 | 2 | | II-1 | Ceacam19 | 56971 | 4-May-15 |
| 4395 | 2 | | II-1 | Ceacam2 | | |
| 4398 | 2 | | II-1 | Ceacam5 | 1048 | 21-May-15 |
| 4399 | 2 | | II-1 | Ceacam9 | | |
| 4407 | 2 | | II-1 | Cebpzos | 100509 876 | 12-May-15 |
| 4422 | 2 | | II-1 | Celsr1 | 9620 | 4-May-15 |
| 4430 | 2 | | II-1 | Cenpe | 1062 | 17-May-15 |
| 4450 | 2 | | II-1 | Cep131 | 22994 | 4-May-15 |
| 4458 | 2 | | II-1 | Cep192 | 55125 | 4-May-15 |
| 4469 | 2 | | II-1 | Cep70 | 80321 | 4-May-15 |
| 4482 | 2 | | II-1 | Cercam | 51148 | |
| 4511 | 2 | | II-1 | Cetn2 | 1069 | 31-May-15 |
| 4520 | 2 | | II-1 | Cfhr2 | 3080 | 4-May-15 |
| 4528 | 2 | | II-1 | Cggbp1 | 8545 | 4-May-15 |
| 4542 | 2 | | II-1 | Chchd1 | 138487 | 4-May-15 |
| 4545 | 2 | | II-1 | Chchd3 | 54927 | 4-May-15 |
| 4557 | 2 | | II-1 | Chd6 | 84181 | 4-May-15 |
| 4560 | 2 | | II-1 | Chd9 | 80205 | 12-May-15 |
| 4571 | 2 | | II-1 | Chid1 | 66005 | 4-May-15 |
| 4580 | 2 | | II-1 | Chl1 | 10752 | 7677 |
| 4585 | 2 | | II-1 | Chmp2a | 27243 | 4-May-15 |
| 4586 | 2 | | II-1 | Chmp2b | 25978 | 23-May-15 |
| 4587 | 2 | | II-1 | Chmp3 | 51652 | 4-May-15 |
| 4588 | 2 | | II-1 | Chmp4b | 128866 | 7-Jun-15 |
| 4589 | 2 | | II-1 | Chmp4c | 92421 | 4-May-15 |
| 4592 | 2 | | II-1 | Chmp7 | 91782 | 4-May-15 |
| 4593 | 2 | | II-1 | Chn1 | 1123 | 23-May-15 |
| 4594 | 2 | | II-1 | Chnlos3 | | |
| 4596 | 2 | | II-1 | Chodl | 140578 | 12-May-15 |
| 4612 | 2 | | II-1 | Chrna1 | 1134 | 23-May-15 |
| 4624 | 2 | | II-1 | Chrnb4 | 1143 | 12-May-15 |
| 4626 | 2 | | II-1 | Chrne | 1145 | 23-May-15 |
| 4627 | 2 | | II-1 | Chrng | 1146 | 4-May-15 |
| 4633 | 2 | | II-1 | Chst14 | 113189 | 4-May-15 |
| 4643 | 2 | | II-1 | Chsy3 | 337876 | #NAME? |
| 4645 | 2 | | II-1 | Chtf8 | 54921 | 4-May-15 |
| 4647 | 2 | | II-1 | Chuk | 1147 | 4-May-15 |
| 4648 | 2 | | II-1 | Churc1 | 91612 | 4-May-15 |
| 4650 | 2 | | II-1 | Ciapin1 | 57019 | 12-May-15 |
| 4666 | 2 | | II-1 | Cirbp | 1153 | 17-May-15 |
| 4670 | 2 | | II-1 | Cisd3 | 284106 | 4-May-15 |
| 4693 | 2 | | II-1 | Clasrp | 11129 | 12-May-15 |
| 4737 | 2 | | II-1 | Clec10a | 10462 | 4-May-15 |
| 4754 | 2 | | II-1 | Clec3b | 7123 | |
| 4763 | 2 | | II-1 | Clec4f | 165530 | 4-May-15 |
| 4779 | 2 | | II-1 | Clip3 | 25999 | |
| 4783 | 2 | | II-1 | Clk3 | 1198 | 4-May-15 |
| 4784 | 2 | | II-1 | Clk4 | 57396 | 12-May-15 |
| 4785 | 2 | | II-1 | Clmn | 79789 | 4-May-15 |
| 4791 | 2 | | II-1 | Clnk | 116449 | 4-May-15 |
| 4792 | 2 | | II-1 | Cns1a | 1207 | 12-May-15 |
| 4793 | 2 | | II-1 | Clock | 9575 | 12-May-15 |
| 4796 | 2 | | II-1 | Clpp | 8192 | 4-May-15 |

| | | | | | | | |
|---|---|---|---|---|---|---|---|
| 4800 | 2 | | II-1 | Clptm1l | 81037 | 17-May-15 |
| 4801 | 2 | | II-1 | Clpx | 10845 | |
| 4802 | 2 | | II-1 | Cln1 | 7401 | 23-May-15 |
| 4803 | 2 | | II-1 | Clrn2 | 645104 | 4-May-15 |
| 4804 | 2 | | II-1 | Clrn3 | 119467 | 4-May-15 |
| 4805 | 2 | | II-1 | Clspn | 63967 | |
| 4811 | 2 | | II-1 | Cltc | 1213 | 31-May-15 |
| 4815 | 2 | | II-1 | Clvs1 | 157807 | 28-May-15 |
| 4816 | 2 | | II-1 | Clvs2 | 134829 | 4-May-15 |
| 4838 | 2 | | II-1 | Cmtm4 | 146223 | 4-May-15 |
| 4840 | 2 | | II-1 | Cmtm6 | 54918 | 4-May-15 |
| 4853 | 2 | | II-1 | Cnga2 | 1260 | 6-May-15 |
| 4868 | 2 | | II-1 | Cnnm1 | 26507 | 4-May-15 |
| 4869 | 2 | | II-1 | Cnnm2 | 54805 | |
| 4872 | 2 | | II-1 | Cnot1 | 23019 | 21-May-15 |
| 4876 | 2 | | II-1 | Cnot3 | 4849 | 4-May-15 |
| 4878 | 2 | | II-1 | Cnot6 | 57472 | 4-May-15 |
| 4882 | 2 | | II-1 | Cnp | 1267 | 7-Jun-15 |
| 4885 | 2 | | II-1 | Cnpy2 | 10330 | 4-May-15 |
| 4886 | 2 | | II-1 | Cnpy3 | 10695 | 4-May-15 |
| 4898 | 2 | | II-1 | Cntn3 | 5067 | 4-May-15 |
| 4899 | 2 | | II-1 | Cntn4 | 152330 | 4-May-15 |
| 4900 | 2 | | II-1 | Cntn5 | 53942 | |
| 4902 | 2 | | II-1 | Cntnap1 | 8506 | 12-May-15 |
| 4905 | 2 | | II-1 | Cntnap4 | 85445 | 4-May-15 |
| 4906 | 2 | | II-1 | Cntnap5a | | |
| 4915 | 2 | | II-1 | Coa7 | 65260 | 4-May-15 |
| 4917 | 2 | | II-1 | Cobl | 23242 | 4-May-15 |
| 4923 | 2 | | II-1 | Cog4 | 25839 | 23-May-15 |
| 4924 | 2 | | II-1 | Cog5 | 10466 | 23-May-15 |
| 4925 | 2 | | II-1 | Cog6 | 57511 | 4-May-15 |
| 4927 | 2 | | II-1 | Cog8 | 84342 | 23-May-15 |
| 4928 | 2 | | II-1 | Coil | 8161 | 4-May-15 |
| 4975 | 2 | | II-1 | Colec11 | 78989 | 17-May-15 |
| 4982 | 2 | | II-1 | Commd3 | 23412 | 4-May-15 |
| 4983 | 2 | | II-1 | Commd4 | 54939 | 4-May-15 |
| 4989 | 2 | | II-1 | Comp | 1311 | 23-May-15 |
| 4994 | 2 | | II-1 | Copb2 | 9276 | 12-May-15 |
| 4995 | 2 | | II-1 | Cope | 11316 | 4-May-15 |
| 4996 | 2 | | II-1 | Copg1 | 22820 | 4-May-15 |
| 4997 | 2 | | II-1 | Copg2 | 26958 | 12-May-15 |
| 5003 | 2 | | II-1 | Cops6 | 10980 | 4-May-15 |
| 5004 | 2 | | II-1 | Cops7a | 50813 | 4-May-15 |
| 5005 | 2 | | II-1 | Cops7b | 64708 | 21-May-15 |
| 5006 | 2 | | II-1 | Cops8 | 10920 | 4-May-15 |
| 5007 | 2 | | II-1 | Copz1 | 22818 | 12-May-15 |
| 5008 | 2 | | II-1 | Copz2 | 51226 | 4-May-15 |
| 5014 | 2 | | II-1 | Coq5 | 84274 | 21-May-15 |
| 5030 | 2 | | II-1 | Cox14 | 84987 | 12-May-15 |
| 5051 | 2 | | II-1 | Cox7c | 1350 | 12-May-15 |
| 5095 | 2 | | II-1 | Cpsf3 | 51692 | 4-May-15 |
| 5097 | 2 | | II-1 | Cpsf4 | 10898 | 4-May-15 |
| 5098 | 2 | | II-1 | Cpsf4l | 642843 | 4-May-15 |
| 5100 | 2 | | II-1 | Cpsf7 | 79869 | 4-May-15 |
| 5107 | 2 | | II-1 | Cpxm1 | 56265 | |
| 5134 | 2 | | II-1 | Creg1 | 8804 | 4-May-15 |
| 5140 | 2 | | II-1 | Crhbp | 1393 | 4-May-15 |
| 5141 | 2 | | II-1 | Crhr1 | 1394 | 12-May-15 |
| 5173 | 2 | | II-1 | Crx | 1406 | 28-May-15 |
| 5174 | 2 | | II-1 | Crxos | | |
| 5191 | 2 | | II-1 | Crygf | | |
| 5198 | 2 | | II-1 | Cs | 1431 | 4-May-15 |
| 5203 | 2 | | II-1 | Csf1 | 1435 | 12-May-15 |
| 5214 | 2 | | II-1 | Csl | | |
| 5216 | 2 | | II-1 | Csmd2 | 114784 | 4-May-15 |
| 5217 | 2 | | II-1 | Csmd2os | | |
| 5218 | 2 | | II-1 | Csmd3 | 114788 | 4-May-15 |
| 5219 | 2 | | II-1 | Csn1s1 | 1446 | 12-May-15 |
| 5226 | 2 | | II-1 | Csnk1e | 1454 | 4-May-15 |
| 5227 | 2 | | II-1 | Csnk1g1 | 53944 | 21-May-15 |
| 5228 | 2 | | II-1 | Csnk1g2 | 1455 | 4-May-15 |
| 5229 | 2 | | II-1 | Csnk1g3 | 1456 | 4-May-15 |
| 5230 | 2 | | II-1 | Csnk2a1 | 1457 | 7-Jun-15 |
| 5231 | 2 | | II-1 | Csnk2a2 | 1459 | 2-Jun-15 |
| 5233 | 2 | | II-1 | Csnka2ip | | |
| 5234 | 2 | | II-1 | Cspg4 | 1464 | 4-May-15 |
| 5235 | 2 | | II-1 | Cspg5 | 10675 | 21-May-15 |
| 5241 | 2 | | II-1 | Csrp1 | 1465 | 12-May-15 |
| 5242 | 2 | | II-1 | Csrp2 | 1466 | |
| 5249 | 2 | | II-1 | Cst3 | 1471 | 24-May-15 |
| 5254 | 2 | | II-1 | Csta1 | | |
| 5255 | 2 | | II-1 | Cstad | | |
| 5259 | 2 | | II-1 | Cstf2t | 23283 | 4-May-15 |
| 5262 | 2 | | II-1 | Ctag2 | 30848 | 4-May-15 |
| 5263 | 2 | | II-1 | Ctages5 | 4253 | 4-May-15 |
| 5264 | 2 | | II-1 | Ctbp1 | 1487 | 4-May-15 |
| 5265 | 2 | | II-1 | Ctbp2 | 1488 | 12-May-15 |
| 5268 | 2 | | II-1 | Ctcf | 10664 | 12-May-15 |
| 5273 | 2 | | II-1 | Ctdsp1 | 58190 | 4-May-15 |
| 5274 | 2 | | II-1 | Ctdsp2 | 10106 | 12-May-15 |
| 5275 | 2 | | II-1 | Ctdspl | 10217 | 4-May-15 |
| 5276 | 2 | | II-1 | Ctdspl2 | 51496 | 12-May-15 |
| 5287 | 2 | | II-1 | Ctnna2 | 1496 | 12-May-15 |
| 5288 | 2 | | II-1 | Ctnna3 | 29119 | 4-May-15 |
| 5289 | 2 | | II-1 | Ctnnal1 | 8727 | 12-May-15 |
| 5293 | 2 | | II-1 | Ctnnd1 | 1500 | 3-May-15 |
| 5296 | 2 | | II-1 | Ctps | 1503 | |

Fig.22 - 98

| | | | | | | | | | | | | | | |
|---|---|---|---|---|---|---|---|---|---|---|---|---|---|---|
| 5305 | 2 | | | II-1 | Cts7 | | | 5792 | 2 | | | II-1 | Ddx6 | 1656 | 4-May-15 |
| 5320 | 2 | | | II-1 | Ctsm | | | 5796 | 2 | | | II-1 | Deb1 | | |
| 5321 | 2 | | | II-1 | Ctso | 1519 | 7-Jun-15 | 5818 | 2 | | | II-1 | Defa-ps13 | | |
| 5338 | 2 | | | II-1 | Cul1 | 8454 | 24-May-15 | 5819 | 2 | | | II-1 | Defa-rs1 | | |
| 5340 | 2 | | | II-1 | Cul3 | 8452 | 4-May-15 | 5842 | 2 | | | II-1 | Defb34 | | |
| 5341 | 2 | | | II-1 | Cul4a | 8451 | 21-May-15 | 5859 | 2 | | | II-1 | Defb50 | | |
| 5342 | 2 | | | II-1 | Cul4b | 8450 | 23-May-15 | 5875 | 2 | | | II-1 | Dennd4b | 9909 | 4-May-15 |
| 5343 | 2 | | | II-1 | Cul5 | 8065 | 4-May-15 | 5880 | 2 | | | II-1 | Dennd6b | 414918 | 4-May-15 |
| 5345 | 2 | | | II-1 | Cul9 | 23113 | 21-May-15 | 5894 | 2 | | | II-1 | Det1 | 55070 | 4-May-15 |
| 5354 | 2 | | | II-1 | Cwc25 | 54883 | 4-May-15 | 5895 | 2 | | | II-1 | Dexi | 28955 | 4-May-15 |
| 5355 | 2 | | | II-1 | Cwc27 | 10283 | 21-May-15 | 5900 | 2 | | | II-1 | Dgat1 | 8694 | 4-May-15 |
| 5356 | 2 | | | II-1 | Cwf19l1 | 56280 | 4-May-15 | 5904 | 2 | | | II-1 | Dgcr2 | 9993 | 7-Jun-15 |
| 5386 | 2 | | | II-1 | Cxxc5 | 51523 | | 5905 | 2 | | | II-1 | Dgcr6 | 8214 | 7-Jun-15 |
| 5390 | 2 | | | II-1 | Cyb561d1 | 284613 | 4-May-15 | 5908 | 2 | | | II-1 | Dgkb | 1607 | 4-May-15 |
| 5391 | 2 | | | II-1 | Cyb561d2 | 11068 | 4-May-15 | 5915 | 2 | | | II-1 | Dgkk | 139189 | 12-May-15 |
| 5393 | 2 | | | II-1 | Cyb5d1 | 124637 | 4-May-15 | 5916 | 2 | | | II-1 | Dgkq | 1609 | 21-May-15 |
| 5410 | 2 | | | II-1 | Cylc1 | 1538 | 4-May-15 | 5927 | 2 | | | II-1 | Dhrs1 | 115817 | 12-May-15 |
| 5411 | 2 | | | II-1 | Cylc2 | 1539 | 4-May-15 | 5944 | 2 | | | II-1 | Dhx33 | 56919 | 4-May-15 |
| 5412 | 2 | | | II-1 | Cyld | 1540 | 12-May-15 | 5946 | 2 | | | II-1 | Dhx35 | 60625 | 4-May-15 |
| 5470 | 2 | | | II-1 | Cyp2j12 | | | 5949 | 2 | | | II-1 | Dhx38 | 9785 | 4-May-15 |
| 5497 | 2 | | | II-1 | Cyp4a30b | | | 5950 | 2 | | | II-1 | Dhx40 | 79665 | 12-May-15 |
| 5510 | 2 | | | II-1 | Cyp4f40 | | | 5951 | 2 | | | II-1 | Dhx57 | 90957 | 12-May-15 |
| 5512 | 2 | | | II-1 | Cyp4v3 | | | 5952 | 2 | | | II-1 | Dhx58 | 79132 | 4-May-15 |
| 5521 | 2 | | | II-1 | Cypt1 | | | 5956 | 2 | | | II-1 | Diap1 | | |
| 5522 | 2 | | | II-1 | Cypt2 | | | 5958 | 2 | | | II-1 | Diap3 | 81624 | 12-May-15 |
| 5523 | 2 | | | II-1 | Cypt3 | | | 5962 | 2 | | | II-1 | Dimt1 | 27292 | 4-May-15 |
| 5524 | 2 | | | II-1 | Cypt4 | | | 5970 | 2 | | | II-1 | Diras1 | 148252 | 4-May-15 |
| 5525 | 2 | | | II-1 | Cypt7 | | | 5971 | 2 | | | II-1 | Diras2 | 54769 | 4-May-15 |
| 5535 | 2 | | | II-1 | Cyth3 | 9265 | 4-May-15 | 5976 | 2 | | | II-1 | Disc1 | 27185 | 31-May-15 |
| 5542 | 2 | | | II-1 | D030025E07Rik | | | 5989 | 2 | | | II-1 | Dlec1 | 9940 | 4-May-15 |
| 5543 | 2 | | | II-1 | D030025P21Rik | | | 5990 | 2 | | | II-1 | Dleu2 | 8847 | 12-May-15 |
| 5547 | 2 | | | II-1 | D030047H15Rik | | | 5999 | 2 | | | II-1 | Dlgap3 | 58512 | 4-May-15 |
| 5552 | 2 | | | II-1 | D11Wsu47e | | | 6000 | 2 | | | II-1 | Dlgap4 | 22839 | 4-May-15 |
| 5553 | 2 | | | II-1 | D13000091J8Rik | | | 6009 | 2 | | | II-1 | Dlx1as | | |
| 5560 | 2 | | | II-1 | D15Ertd621e | | | 6016 | 2 | | | II-1 | Dlx6os1 | | |
| 5564 | 2 | | | II-1 | D17H6S53E | | | 6017 | 2 | | | II-1 | Dmap1 | 55929 | 4-May-15 |
| 5567 | 2 | | | II-1 | D19Bwg1357e | | | 6031 | 2 | | | II-1 | Dmrta2 | 63950 | 4-May-15 |
| 5568 | 2 | | | II-1 | D1Ertd622e | | | 6032 | 2 | | | II-1 | Dmrtb1 | 63948 | 4-May-15 |
| 5573 | 2 | | | II-1 | D2Wsu81e | | | 6035 | 2 | | | II-1 | Dmrtc1c2 | | |
| 5578 | 2 | | | II-1 | D330050B16Rik | | | 6036 | 2 | | | II-1 | Dmrtc2 | 63946 | 4-May-15 |
| 5588 | 2 | | | II-1 | D530049B02Rik | | | 6037 | 2 | | | II-1 | Dmtf1 | 9988 | 4-May-15 |
| 5589 | 2 | | | II-1 | D5Ertd577e | | | 6047 | 2 | | | II-1 | Dnah10 | 196386 | 4-May-15 |
| 5595 | 2 | | | II-1 | D630023F18Rik | | | 6048 | 2 | | | II-1 | Dnah11 | 8701 | 23-May-15 |
| 5605 | 2 | | | II-1 | D6Ertd527e | | | 6049 | 2 | | | II-1 | Dnah17 | 8632 | 4-May-15 |
| 5613 | 2 | | | II-1 | D7Ertd443e | | | 6050 | 2 | | | II-1 | Dnah2 | 146754 | 12-May-15 |
| 5616 | 2 | | | II-1 | D830013O20Rik | | | 6052 | 2 | | | II-1 | Dnah6 | 1768 | 4-May-15 |
| 5623 | 2 | | | II-1 | D8Ertd738e | | | 6053 | 2 | | | II-1 | Dnah7a | | |
| 5624 | 2 | | | II-1 | D8Ertd82e | | | 6054 | 2 | | | II-1 | Dnah7b | | |
| 5626 | 2 | | | II-1 | D930015E06Rik | | | 6055 | 2 | | | II-1 | Dnah8 | 1769 | 4-May-15 |
| 5646 | 2 | | | II-1 | Dagla | 747 | 4-May-15 | | | | | | | | |
| 5663 | 2 | | | II-1 | Daxx | 1616 | 17-May-15 | 6058 | 2 | | | II-1 | Dnaic2 | | |
| 5664 | 2 | | | II-1 | Dazap1 | 26528 | 2-Jun-15 | 6059 | 2 | | | II-1 | Dnaja1 | 3301 | 4-May-15 |
| 5665 | 2 | | | II-1 | Dazap2 | 9802 | 12-May-15 | 6060 | 2 | | | II-1 | Dnaja2 | 10294 | 4-May-15 |
| 5666 | 2 | | | II-1 | Dazl | 1618 | 12-May-15 | 6066 | 2 | | | II-1 | Dnajb13 | 374407 | 12-May-15 |
| 5681 | 2 | | | II-1 | Dbx2 | 440097 | 4-May-15 | 6085 | 2 | | | II-1 | Dnajc18 | 202052 | 4-May-15 |
| 5682 | 2 | | | II-1 | Dcaf10 | 79269 | 4-May-15 | 6087 | 2 | | | II-1 | Dnajc2 | 27000 | 4-May-15 |
| 5684 | 2 | | | II-1 | Dcaf12 | 25853 | 4-May-15 | 6089 | 2 | | | II-1 | Dnajc22 | 79962 | 12-May-15 |
| 5685 | 2 | | | II-1 | Dcaf12l1 | 139170 | 30-Apr-15 | 6096 | 2 | | | II-1 | Dnajc4 | 3338 | 21-May-15 |
| 5690 | 2 | | | II-1 | Dcaf4 | 26094 | 21-May-15 | 6099 | 2 | | | II-1 | Dnajc5g | 285126 | 14-May-15 |
| 5692 | 2 | | | II-1 | Dcaf6 | 55827 | 4-May-15 | 6100 | 2 | | | II-1 | Dnajc6 | 9829 | 12-May-15 |
| 5693 | 2 | | | II-1 | Dcaf7 | 10238 | 4-May-15 | 6101 | 2 | | | II-1 | Dnajc7 | 7266 | 4-May-15 |
| 5694 | 2 | | | II-1 | Dcaf8 | 50717 | 4-May-15 | 6103 | 2 | | | II-1 | Dnajc9 | 23234 | 4-May-15 |
| 5695 | 2 | | | II-1 | Dcakd | 79977 | 4-May-15 | 6105 | 2 | | | II-1 | Dnal4 | 10126 | 4-May-15 |
| 5703 | 2 | | | II-1 | Dck | 1633 | 12-May-15 | 6118 | 2 | | | II-1 | Dnm2 | 1785 | 23-May-15 |
| 5713 | 2 | | | II-1 | Dcp2 | 167227 | 4-May-15 | 6128 | 2 | | | II-1 | Dnph1 | 10591 | 23-May-15 |
| 5723 | 2 | | | II-1 | Dctn2 | 10540 | 29-May-15 | 6132 | 2 | | | II-1 | Doc2a | 8448 | 4-May-15 |
| 5724 | 2 | | | II-1 | Dctn3 | 11258 | 4-May-15 | 6147 | 2 | | | II-1 | Dok1 | 1796 | 7-Jun-15 |
| 5727 | 2 | | | II-1 | Dctn6 | 10671 | 4-May-15 | 6163 | 2 | | | II-1 | Dpcd | 25911 | 4-May-15 |
| 5728 | 2 | | | II-1 | Dctpp1 | 79077 | 4-May-15 | 6169 | 2 | | | II-1 | Dpf2 | 5977 | 2-Jun-15 |
| 5730 | 2 | | | II-1 | Dcun1d2 | 55208 | 4-May-15 | 6170 | 2 | | | II-1 | Dpf3 | 8110 | 17-May-15 |
| 5733 | 2 | | | II-1 | Dcun1d5 | 84259 | 4-May-15 | 6174 | 2 | | | II-1 | Dph5 | 51611 | 4-May-15 |
| 5734 | 2 | | | II-1 | Dcx | 1641 | 31-May-15 | 6175 | 2 | | | II-1 | Dph6 | 89978 | 4-May-15 |
| 5754 | 2 | | | II-1 | Ddrgk1 | 65992 | 4-May-15 | 6177 | 2 | | | II-1 | Dpm1 | 8813 | 4-May-15 |
| 5757 | 2 | | | II-1 | Ddx10 | 1662 | 4-May-15 | 6179 | 2 | | | II-1 | Dpm3 | 54344 | 23-May-15 |
| 5758 | 2 | | | II-1 | Ddx11 | 1663 | 21-May-15 | 6180 | 2 | | | II-1 | Dpp10 | 57628 | 4-May-15 |
| 5759 | 2 | | | II-1 | Ddx17 | 10521 | 4-May-15 | 6181 | 2 | | | II-1 | Dpp3 | 10072 | 12-May-15 |
| 5762 | 2 | | | II-1 | Ddx19b | 11269 | 4-May-15 | 6182 | 2 | | | II-1 | Dpp4 | 1803 | 17-May-15 |
| 5763 | 2 | | | II-1 | Ddx20 | 11218 | 28-May-15 | 6187 | 2 | | | II-1 | Dppa1 | | |
| 5764 | 2 | | | II-1 | Ddx21 | 9188 | 7-Jun-15 | 6188 | 2 | | | II-1 | Dppa2 | 151871 | 4-May-15 |
| 5765 | 2 | | | II-1 | Ddx23 | 9416 | 4-May-15 | 6189 | 2 | | | II-1 | Dppa3 | 359787 | 4-May-15 |
| 5766 | 2 | | | II-1 | Ddx24 | 57062 | 4-May-15 | 6206 | 2 | | | II-1 | DQ267102 | | |
| 5767 | 2 | | | II-1 | Ddx25 | 29118 | 12-May-15 | 6210 | 2 | | | II-1 | Dram2 | 128338 | 4-May-15 |
| 5771 | 2 | | | II-1 | Ddx31 | 64794 | 7-Jun-15 | 6213 | 2 | | | II-1 | Drc1 | 92749 | 7-Jun-15 |
| 5773 | 2 | | | II-1 | Ddx39b | 7919 | 4-May-15 | 6216 | 2 | | | II-1 | Drd3 | 1814 | 17-May-15 |
| 5774 | 2 | | | II-1 | Ddx3x | 1654 | 12-May-15 | 6217 | 2 | | | II-1 | Drd4 | 1815 | 29-May-15 |
| 5775 | 2 | | | II-1 | Ddx3y | 8653 | 29-May-15 | 6221 | 2 | | | II-1 | Drg2 | 1819 | 4-May-15 |
| 5777 | 2 | | | II-1 | Ddx41 | 51428 | 4-May-15 | 6222 | 2 | | | II-1 | Drosha | 29102 | 4-May-15 |
| 5778 | 2 | | | II-1 | Ddx42 | 11325 | 4-May-15 | 6228 | 2 | | | II-1 | Dscam1 | 57453 | 4-May-15 |
| 5779 | 2 | | | II-1 | Ddx43 | 55510 | 17-May-15 | 6229 | 2 | | | II-1 | Dscc1 | 79075 | 4-May-15 |
| 5780 | 2 | | | II-1 | Ddx46 | 9879 | 3-May-15 | 6232 | 2 | | | II-1 | Dsel | 92126 | 4-May-15 |
| 5781 | 2 | | | II-1 | Ddx47 | 51202 | 4-May-15 | 6235 | 2 | | | II-1 | Dsg1c | | |
| 5782 | 2 | | | II-1 | Ddx49 | 54555 | 4-May-15 | 6238 | 2 | | | II-1 | Dsg4 | 147409 | 4-May-15 |
| 5784 | 2 | | | II-1 | Ddx50 | 79009 | 4-May-15 | 6239 | 2 | | | II-1 | Dsn1 | 79980 | 4-May-15 |
| 5785 | 2 | | | II-1 | Ddx51 | 317781 | 4-May-15 | 6242 | 2 | | | II-1 | Dst | 667 | 12-May-15 |
| 5787 | 2 | | | II-1 | Ddx54 | 79039 | 4-May-15 | 6245 | 2 | | | II-1 | Dtd1 | 92675 | 4-May-15 |
| 5788 | 2 | | | II-1 | Ddx55 | 57696 | 4-May-15 | 6247 | 2 | | | II-1 | Dthd1 | 401124 | 4-May-15 |
| 5789 | 2 | | | II-1 | Ddx56 | 54606 | 4-May-15 | | | | | | | | |

Fig.22 - 99

| | | | | | | | | | | | | | | |
|---|---|---|---|---|---|---|---|---|---|---|---|---|---|---|
| 6248 | 2 | | | H-1 | Dtl | 51514 | 7-Jun-15 | 6846 | 2 | | | H-1 | Esyt2 | 57488 | 4-May-15 |
| 6258 | 2 | | | H-1 | Dtx4 | 23220 | 12-May-15 | 6849 | 2 | | | H-1 | Etd | | |
| 6267 | 2 | | | H-1 | Dus3l | 56331 | 23-May-15 | 6850 | 2 | | | H-1 | Etf1 | 2107 | 2-Jun-15 |
| 6299 | 2 | | | H-1 | Dvl2 | 1856 | 3-May-15 | 6851 | 2 | | | H-1 | Etfa | 2108 | 21-May-15 |
| 6306 | 2 | | | H-1 | Dynap | 284254 | 12-May-15 | 6854 | 2 | | | H-1 | Ethe1 | 23474 | 4-May-15 |
| 6307 | 2 | | | H-1 | Dync1h1 | 1778 | 23-May-15 | 6865 | 2 | | | H-1 | Etv3 | 2117 | 28-May-15 |
| 6310 | 2 | | | H-1 | Dync1li1 | 51143 | 4-May-15 | 6884 | 2 | | | H-1 | Ewsr1 | 2130 | 21-May-15 |
| 6311 | 2 | | | H-1 | Dync1li2 | 1783 | 4-May-15 | 6885 | 2 | | | H-1 | Exd1 | 161829 | 4-May-15 |
| 6312 | 2 | | | H-1 | Dync2h1 | 79659 | 23-May-15 | 6891 | 2 | | | H-1 | Exoc3 | 11336 | 4-May-15 |
| 6313 | 2 | | | H-1 | Dync2li1 | 51626 | 4-May-15 | 6892 | 2 | | | H-1 | Exoc3l | 283849 | 4-May-15 |
| 6324 | 2 | | | H-1 | Dyrk1b | 9149 | 4-May-15 | 6899 | 2 | | | H-1 | Exoc8 | 149371 | 4-May-15 |
| 6325 | 2 | | | H-1 | Dyrk2 | 8445 | 12-May-15 | 6901 | 2 | | | H-1 | Exosc1 | 51013 | 2-Jun-15 |
| 6329 | 2 | | | H-1 | Dyth | 391475 | 4-May-15 | 6903 | 2 | | | H-1 | Exosc2 | 23404 | 20-May-15 |
| 6330 | 2 | | | H-1 | Dyx1c1 | 161582 | 4-May-15 | 6905 | 2 | | | H-1 | Exosc4 | 54512 | 4-May-15 |
| 6335 | 2 | | | H-1 | E030062O03Rik | | | 6906 | 2 | | | H-1 | Exosc5 | 56915 | 4-May-15 |
| 6347 | 2 | | | H-1 | E130008D07Rik | | | 6928 | 2 | | | H-1 | F13a1 | 2162 | 23-May-15 |
| 6356 | 2 | | | H-1 | E130304I02Rik | | | 6941 | 2 | | | H-1 | F630206G17Rik | | |
| 6357 | 2 | | | H-1 | E130307A14Rik | | | 6950 | 2 | | | H-1 | F9 | 2158 | 23-May-15 |
| 6375 | 2 | | | H-1 | E2f5 | 1875 | 4-May-15 | 6951 | 2 | | | H-1 | F930015N05Rik | | |
| 6376 | 2 | | | H-1 | E2f6 | 1876 | 4-May-15 | 6982 | 2 | | | H-1 | Fam105a | 54491 | 4-May-15 |
| 6385 | 2 | | | H-1 | E330017L17Rik | | | 7000 | 2 | | | H-1 | Fam120a | 23196 | 4-May-15 |
| 6388 | 2 | | | H-1 | E330023G01Rik | | | 7002 | 2 | | | H-1 | Fam120b | 84498 | 12-May-15 |
| 6389 | 2 | | | H-1 | E330033B04Rik | | | 7004 | 2 | | | H-1 | Fam122a | 116224 | 4-May-15 |
| 6390 | 2 | | | H-1 | E330034G19Rik | | | 7006 | 2 | | | H-1 | Fam122c | 159091 | 12-May-15 |
| 6392 | 2 | | | H-1 | E430018J23Rik | | | 7023 | 2 | | | H-1 | Fam135a | 57579 | 4-May-15 |
| 6398 | 2 | | | H-1 | Eaf2 | 55840 | 7-Jun-15 | 7024 | 2 | | | H-1 | Fam135b | 51059 | 14-May-15 |
| 6409 | 2 | | | H-1 | Ebag9 | 9166 | 17-May-15 | 7025 | 2 | | | H-1 | Fam136a | 84908 | 4-May-15 |
| 6417 | 2 | | | H-1 | Ebpl | 84650 | 4-May-15 | 7037 | 2 | | | H-1 | Fam155a | 728215 | 4-May-15 |
| 6420 | 2 | | | H-1 | Ece2 | 9718 | 4-May-15 | 7038 | 2 | | | H-1 | Fam159a | 348378 | 4-May-15 |
| 6422 | 2 | | | H-1 | Ech1 | 1891 | 23-May-15 | 7043 | 2 | | | H-1 | Fam160b2 | 64760 | 4-May-15 |
| 6447 | 2 | | | H-1 | Ed3 | 10085 | 4-May-15 | 7044 | 2 | | | H-1 | Fam161a | 84140 | 23-May-15 |
| 6477 | 2 | | | H-1 | Efcab7 | 84455 | 4-May-15 | 7048 | 2 | | | H-1 | Fam163a | 148753 | 14-May-15 |
| 6480 | 2 | | | H-1 | Efcc1 | 79825 | 4-May-15 | 7060 | 2 | | | H-1 | Fam171a1 | 221061 | 12-May-15 |
| 6485 | 2 | | | H-1 | Efhc2 | 80258 | 4-May-15 | 7065 | 2 | | | H-1 | Fam173b | 134146 | 4-May-15 |
| 6497 | 2 | | | H-1 | Efr3b | 22979 | 4-May-15 | 7067 | 2 | | | H-1 | Fam174b | 400451 | 4-May-15 |
| 6526 | 2 | | | H-1 | Ei24 | 9538 | 21-May-15 | 7081 | 2 | | | H-1 | Fam186b | 84070 | 4-May-15 |
| 6527 | 2 | | | H-1 | Eid1 | 23741 | 4-May-15 | 7082 | 2 | | | H-1 | Fam187a | 100528020 | 7-Dec-14 |
| 6528 | 2 | | | H-1 | Eid2 | 163126 | 4-May-15 | 7090 | 2 | | | H-1 | Fam193a | 8603 | 4-May-15 |
| 6533 | 2 | | | H-1 | Eif1ad | 84285 | 4-May-15 | 7091 | 2 | | | H-1 | Fam193b | 54540 | 4-May-15 |
| 6534 | 2 | | | H-1 | Eif1ax | 1964 | 4-May-15 | 7100 | 2 | | | H-1 | Fam19a2 | 338811 | 21-May-15 |
| 6535 | 2 | | | H-1 | Eif1b | 10289 | 4-May-15 | 7101 | 2 | | | H-1 | Fam19a3 | 284467 | 4-May-15 |
| 6536 | 2 | | | H-1 | Eif2a | 83939 | 7-Jun-15 | 7102 | 2 | | | H-1 | Fam19a4 | 151647 | 4-May-15 |
| 6543 | 2 | | | H-1 | Eif2b3 | 8891 | 23-May-15 | 7106 | 2 | | | H-1 | Fam206a | 54942 | 3-May-15 |
| 6547 | 2 | | | H-1 | Eif2s1 | 1965 | 28-May-15 | 7107 | 2 | | | H-1 | Fam207a | 85395 | 4-May-15 |
| 6548 | 2 | | | H-1 | Eif2s2 | 8894 | 4-May-15 | 7109 | 2 | | | H-1 | Fam208b | 54906 | 4-May-15 |
| 6549 | 2 | | | H-1 | Eif2s3x | | | 7124 | 2 | | | H-1 | Fam216b | 144809 | 4-May-15 |
| 6550 | 2 | | | H-1 | Eif2s3y | | | 7130 | 2 | | | H-1 | Fam220a | 84792 | 4-May-15 |
| 6551 | 2 | | | H-1 | Eif3a | 8661 | 13-Jun-15 | 7136 | 2 | | | H-1 | Fam227b | 196951 | 4-May-15 |
| 6552 | 2 | | | H-1 | Eif3b | 8662 | 12-May-15 | 7137 | 2 | | | H-1 | Fam228a | 853140 | 4-May-15 |
| 6553 | 2 | | | H-1 | Eif3c | 8663 | 4-May-15 | 7138 | 2 | | | H-1 | Fam228b | 375190 | 12-May-15 |
| 6554 | 2 | | | H-1 | Eif3d | 8664 | 4-May-15 | 7159 | 2 | | | H-1 | Fam47e | 100126583 | 4-May-15 |
| 6555 | 2 | | | H-1 | Eif3e | 3646 | 12-May-15 | 7160 | 2 | | | H-1 | Fam49a | 81553 | 4-May-15 |
| 6558 | 2 | | | H-1 | Eif3h | 8667 | 12-May-15 | 7164 | 2 | | | H-1 | Fam53a | 152877 | 21-May-15 |
| 6559 | 2 | | | H-1 | Eif3l | 8668 | 4-May-15 | 7165 | 2 | | | H-1 | Fam53b | 9679 | 4-May-15 |
| 6564 | 2 | | | H-1 | Eif2m | 10480 | 12-May-15 | 7166 | 2 | | | H-1 | Fam53c | 51307 | 12-May-15 |
| 6567 | 2 | | | H-1 | Eif4a3 | 9775 | 4-May-15 | 7190 | 2 | | | H-1 | Fam76a | 199870 | 4-May-15 |
| 6568 | 2 | | | H-1 | Eif4b | 1975 | 17-May-15 | 7211 | 2 | | | H-1 | Fam96b | 51647 | 4-May-15 |
| 6569 | 2 | | | H-1 | Eif4e | 1977 | 31-May-15 | 7218 | 2 | | | H-1 | Fancc | 2176 | 28-May-15 |
| 6570 | 2 | | | H-1 | Eif4e1b | 253314 | 4-May-15 | 7225 | 2 | | | H-1 | Fancl | 55120 | 23-May-15 |
| 6571 | 2 | | | H-1 | Eif4e2 | 9470 | 31-May-15 | 7236 | 2 | | | H-1 | Fas | 355 | 13-Jun-15 |
| 6572 | 2 | | | H-1 | Eif4e3 | 317649 | 4-May-15 | 7241 | 2 | | | H-1 | Fastkd2 | 22868 | 4-May-15 |
| 6578 | 2 | | | H-1 | Eif4g2 | 1982 | 4-May-15 | 7242 | 2 | | | H-1 | Fastkd3 | 79072 | 4-May-15 |
| 6579 | 2 | | | H-1 | Eif4g3 | 8672 | 4-May-15 | 7243 | 2 | | | H-1 | Fastkd5 | 60493 | 4-May-15 |
| 6580 | 2 | | | H-1 | Eif4h | 7458 | 12-May-15 | 7247 | 2 | | | H-1 | Fat4 | 79633 | 4-May-15 |
| 6582 | 2 | | | H-1 | Eif5a | 1984 | 7-Jun-15 | 7255 | 2 | | | H-1 | Fbln1 | 2192 | 12-May-15 |
| 6583 | 2 | | | H-1 | Eif5a2 | 56648 | 4-May-15 | 7266 | 2 | | | H-1 | Fbxl2os | | |
| 6587 | 2 | | | H-1 | Elac2 | 60528 | 4-May-15 | 7268 | 2 | | | H-1 | Fbxl14 | 144699 | 2-Jun-15 |
| 6592 | 2 | | | H-1 | Elavl4 | 1996 | 12-May-15 | 7269 | 2 | | | H-1 | Fbxl15 | 79176 | 4-May-15 |
| 6593 | 2 | | | H-1 | Elf1 | 1997 | 7-Jun-15 | 7277 | 2 | | | H-1 | Fbxl22 | 283807 | 4-May-15 |
| 6608 | 2 | | | H-1 | Elmo3 | 79767 | 4-May-15 | 7280 | 2 | | | H-1 | Fbxl5 | 26234 | 4-May-15 |
| 6611 | 2 | | | H-1 | Elmod3 | 84173 | 4-May-15 | 7281 | 2 | | | H-1 | Fbxl6 | 26233 | 4-May-15 |
| 6624 | 2 | | | H-1 | Elp4 | 26610 | 23-May-15 | 7283 | 2 | | | H-1 | Fbxl8 | 55336 | 4-May-15 |
| 6631 | 2 | | | H-1 | Emc2 | 9694 | 12-May-15 | 7286 | 2 | | | H-1 | Fbxo15 | 201456 | 4-May-15 |
| 6634 | 2 | | | H-1 | Emc6 | 83460 | 21-May-15 | 7287 | 2 | | | H-1 | Fbxo16 | 157574 | 4-May-15 |
| 6635 | 2 | | | H-1 | Emc7 | 56851 | 4-May-15 | 7293 | 2 | | | H-1 | Fbxo24 | 26261 | 4-May-15 |
| 6648 | 2 | | | H-1 | Eml2 | 24139 | 12-May-15 | 7294 | 2 | | | H-1 | Fbxo25 | 26260 | 4-May-15 |
| 6652 | 2 | | | H-1 | Eml6 | 400954 | 12-May-15 | 7306 | 2 | | | H-1 | Fbxo4 | 26272 | 4-May-15 |
| 6661 | 2 | | | H-1 | En1 | 2019 | 4-May-15 | 7310 | 2 | | | H-1 | Fbxo43 | 286151 | 4-May-15 |
| 6662 | 2 | | | H-1 | En2 | 2020 | 4-May-15 | 7311 | 2 | | | H-1 | Fbxo44 | 93611 | 12-May-15 |
| 6682 | 2 | | | H-1 | Enox2 | 10495 | 17-May-15 | 7314 | 2 | | | H-1 | Fbxo47 | 494188 | 4-May-15 |
| 6692 | 2 | | | H-1 | Enthd1 | 150350 | 4-May-15 | 7319 | 2 | | | H-1 | Fbxo8 | 26269 | 4-May-15 |
| 6693 | 2 | | | H-1 | Enthd2 | 146705 | 4-May-15 | 7320 | 2 | | | H-1 | Fbxo9 | 26268 | 4-May-15 |
| 6694 | 2 | | | H-1 | Entpd1 | 953 | 12-May-15 | 7321 | 2 | | | H-1 | Fbxw10 | 10517 | 4-May-15 |
| 6729 | 2 | | | H-1 | Epha7 | 2045 | 17-May-15 | 7322 | 2 | | | H-1 | Fbxw11 | 23291 | 4-May-15 |
| 6732 | 2 | | | H-1 | Ephb2 | 2048 | 23-May-15 | 7323 | 2 | | | H-1 | Fbxw13 | | |
| 6762 | 2 | | | H-1 | Erap1 | 51752 | 21-May-15 | 7324 | 2 | | | H-1 | Fbxw14 | | |
| 6764 | 2 | | | H-1 | Erbb2 | 2064 | 31-May-15 | 7325 | 2 | | | H-1 | Fbxw15 | | |
| 6769 | 2 | | | H-1 | Erc2 | 26059 | 12-May-15 | 7331 | 2 | | | H-1 | Fbxw20 | | |
| 6774 | 2 | | | H-1 | Ercc5 | 2073 | 4-May-15 | 7333 | 2 | | | H-1 | Fbxw22 | | |
| 6775 | 2 | | | H-1 | Ercc6 | 2074 | 23-May-15 | 7362 | 2 | | | H-1 | Fcrla | 84824 | 4-May-15 |
| 6776 | 2 | | | H-1 | Ercc6l | 54821 | 10-May-15 | 7379 | 2 | | | H-1 | Ferd3l | 222894 | 4-May-15 |
| 6785 | 2 | | | H-1 | Ergic3 | 51814 | 2-Jun-15 | 7419 | 2 | | | H-1 | Fgf4 | 2249 | 4-May-15 |
| 6786 | 2 | | | H-1 | Erh | 2079 | 4-May-15 | 7420 | 2 | | | H-1 | Fgf5 | 2250 | 12-May-15 |
| 6798 | 2 | | | H-1 | Erlin2 | 11160 | 29-May-15 | 7423 | 2 | | | H-1 | Fgf8 | 2253 | 23-May-15 |
| 6820 | 2 | | | H-1 | Esp16 | | | 7424 | 2 | | | H-1 | Fgf9 | 2254 | 4-May-15 |
| 6824 | 2 | | | H-1 | Esp3 | | | 7432 | 2 | | | H-1 | Fgfr4 | 2264 | 18-May-15 |
| 6832 | 2 | | | H-1 | Esp6-esp5 | | | | | | | | | | |

Fig.22 - 100

| | | | | | | | | | | | |
|---|---|---|---|---|---|---|---|---|---|---|---|
| 7441 | 2 | | | II-1 | Fhad1os1 | | | 8136 | 2 | | | II-1 | Gm10548 | |
| 7458 | 2 | | | II-1 | Fign | 55137 | 4-May-15 | 8145 | 2 | | | II-1 | Gm10636 | |
| 7481 | 2 | | | II-1 | Fkbp7 | 51661 | 4-May-15 | 8150 | 2 | | | II-1 | Gm10649 | |
| 7482 | 2 | | | II-1 | Fkbp8 | 23770 | 12-May-15 | 8155 | 2 | | | II-1 | Gm10666 | |
| 7489 | 2 | | | II-1 | Flg2 | 388698 | 12-May-15 | 8161 | 2 | | | II-1 | Gm10714 | |
| 7493 | 2 | | | II-1 | Flnb | 2317 | 23-May-15 | 8165 | 2 | | | II-1 | Gm10767 | |
| 7508 | 2 | | | II-1 | Fmn1 | 752 | 14-May-15 | 8168 | 2 | | | II-1 | Gm10782 | |
| 7526 | 2 | | | II-1 | Fnbp4 | 23360 | 21-May-15 | 8170 | 2 | | | II-1 | Gm10787 | |
| 7527 | 2 | | | II-1 | Fnd3c2 | | | 8175 | 2 | | | II-1 | Gm10814 | |
| 7528 | 2 | | | II-1 | Fndc1 | 84624 | 4-May-15 | 8178 | 2 | | | II-1 | Gm10845 | |
| 7531 | 2 | | | II-1 | Fndc3c1 | | | 8185 | 2 | | | II-1 | Gm10941 | |
| 7536 | 2 | | | II-1 | Fndc9 | 408263 | 4-May-15 | 8193 | 2 | | | II-1 | Gm11190 | |
| 7539 | 2 | | | II-1 | Fnta | 2339 | 4-May-15 | 8194 | 2 | | | II-1 | Gm11985 | |
| 7555 | 2 | | | II-1 | Foxb2 | 442425 | 28-May-15 | 8196 | 2 | | | II-1 | Gm1123 | |
| 7574 | 2 | | | II-1 | Foxj3 | 22887 | 28-May-15 | 8197 | 2 | | | II-1 | Gm11237 | |
| 7575 | 2 | | | II-1 | Foxk1 | 221937 | 4-May-15 | 8198 | 2 | | | II-1 | Gm11240 | |
| 7576 | 2 | | | II-1 | Foxk2 | 3607 | 28-May-15 | 8202 | 2 | | | II-1 | Gm1141 | |
| 7591 | 2 | | | II-1 | Foxp3 | 50943 | 31-May-15 | 8203 | 2 | | | II-1 | Gm11413 | |
| 7596 | 2 | | | II-1 | Foxred1 | 55572 | 23-May-15 | 8205 | 2 | | | II-1 | Gm11437 | |
| 7604 | 2 | | | II-1 | Fpr-rs3 | | | 8211 | 2 | | | II-1 | Gm11541 | |
| 7606 | 2 | | | II-1 | Fpr-rs6 | | | 8213 | 2 | | | II-1 | Gm11545 | |
| 7607 | 2 | | | II-1 | Fra10ac1 | 118924 | 12-May-15 | 8235 | 2 | | | II-1 | Gm11758 | |
| 7626 | 2 | | | II-1 | Frmpd4 | 9758 | 4-May-15 | 8246 | 2 | | | II-1 | Gm11985 | |
| 7627 | 2 | | | II-1 | Frs1 | 391059 | 4-May-15 | 8247 | 2 | | | II-1 | Gm11992 | |
| 7629 | 2 | | | II-1 | Frs2 | 10818 | 4-May-15 | 8248 | 2 | | | II-1 | Gm12 | |
| 7641 | 2 | | | II-1 | Fsd1l | 83856 | 12-May-15 | 8253 | 2 | | | II-1 | Gm12169 | |
| 7657 | 2 | | | II-1 | Ftsj1 | 24140 | 23-May-15 | 8255 | 2 | | | II-1 | Gm12185 | |
| 7659 | 2 | | | II-1 | Ftsj3 | 117246 | 4-May-15 | 8262 | 2 | | | II-1 | Gm12298 | |
| 7661 | 2 | | | II-1 | Fubp1 | 8880 | 12-May-15 | 8270 | 2 | | | II-1 | Gm12530 | |
| 7664 | 2 | | | II-1 | Fuca2 | 2519 | 4-May-15 | 8271 | 2 | | | II-1 | Gm12603 | |
| 7678 | 2 | | | II-1 | Fut8 | 2530 | 17-May-15 | 8272 | 2 | | | II-1 | Gm12633 | |
| 7680 | 2 | | | II-1 | Fuz | 80199 | 4-May-15 | 8276 | 2 | | | II-1 | Gm12709 | |
| 7696 | 2 | | | II-1 | Fzd1 | 8321 | 4-May-15 | 8283 | 2 | | | II-1 | Gm12887 | |
| 7711 | 2 | | | II-1 | G530011I006Rik | | | 8291 | 2 | | | II-1 | Gm13032 | |
| 7715 | 2 | | | II-1 | G630090E17Rik | | | 8295 | 2 | | | II-1 | Gm13051 | |
| 7722 | 2 | | | II-1 | G6pd2 | | | 8298 | 2 | | | II-1 | Gm13083 | |
| 7730 | 2 | | | II-1 | Gabarapl1 | 23710 | 21-May-15 | 8316 | 2 | | | II-1 | Gm13242 | |
| 7731 | 2 | | | II-1 | Gabarapl2 | 11345 | 21-May-15 | 8321 | 2 | | | II-1 | Gm13275 | |
| 7732 | 2 | | | II-1 | Gabbr1 | 2550 | 7-Jun-15 | 8342 | 2 | | | II-1 | Gm13490 | |
| 7733 | 2 | | | II-1 | Gabbr2 | 9568 | 4-May-15 | 8347 | 2 | | | II-1 | Gm13546 | |
| 7739 | 2 | | | II-1 | Gabra3 | 2556 | 12-May-15 | 8350 | 2 | | | II-1 | Gm13582 | |
| 7742 | 2 | | | II-1 | Gabra6 | 2559 | 4-May-15 | 8356 | 2 | | | II-1 | Gm13769 | |
| 7743 | 2 | | | II-1 | Gabrb1 | 2560 | 12-May-15 | 8360 | 2 | | | II-1 | Gm13889 | |
| 7744 | 2 | | | II-1 | Gabrb2 | 2561 | 12-May-15 | 8361 | 2 | | | II-1 | Gm13939 | |
| 7745 | 2 | | | II-1 | Gabrb3 | 2562 | 4-May-15 | 8366 | 2 | | | II-1 | Gm14057 | |
| 7749 | 2 | | | II-1 | Gabrg2 | 2566 | 2-Jun-15 | 8373 | 2 | | | II-1 | Gm14164 | |
| 7750 | 2 | | | II-1 | Gabrg3 | 2567 | 12-May-15 | 8375 | 2 | | | II-1 | Gm14204 | |
| 7751 | 2 | | | II-1 | Gabrp | 2568 | 4-May-15 | 8382 | 2 | | | II-1 | Gm14322 | |
| 7754 | 2 | | | II-1 | Gabrr2 | 2570 | 4-May-15 | 8387 | 2 | | | II-1 | Gm14346 | |
| 7755 | 2 | | | II-1 | Gabrr3 | 200959 | 13-May-15 | 8388 | 2 | | | II-1 | Gm14347 | |
| 7756 | 2 | | | II-1 | Gad1 | 2571 | 24-May-15 | 8391 | 2 | | | II-1 | Gm14378 | |
| 7793 | 2 | | | II-1 | Galntl6 | 442117 | 12-May-15 | 8404 | 2 | | | II-1 | Gm14461 | |
| 7794 | 2 | | | II-1 | Galp | 85569 | 4-May-15 | 8405 | 2 | | | II-1 | Gm14474 | |
| 7795 | 2 | | | II-1 | Galr1 | 2587 | 12-May-15 | 8409 | 2 | | | II-1 | Gm14478 | |
| 7796 | 2 | | | II-1 | Galr2 | 8811 | 4-May-15 | 8410 | 2 | | | II-1 | Gm14479 | |
| 7812 | 2 | | | II-1 | Gars | 2617 | 7-Jun-15 | 8411 | 2 | | | II-1 | Gm14482 | |
| 7830 | 2 | | | II-1 | Gata6 | 2627 | 24-May-15 | 8413 | 2 | | | II-1 | Gm14484 | |
| 7832 | 2 | | | II-1 | Gatad2a | 54815 | 12-May-15 | 8414 | 2 | | | II-1 | Gm14496 | |
| 7840 | 2 | | | II-1 | Gbas | 2631 | 4-May-15 | 8418 | 2 | | | II-1 | Gm14525 | |
| 7862 | 2 | | | II-1 | Gcdh | 2639 | 31-May-15 | 8422 | 2 | | | II-1 | Gm14634 | |
| 7880 | 2 | | | II-1 | Gcsam | 257144 | 4-May-15 | 8423 | 2 | | | II-1 | Gm14635 | |
| 7887 | 2 | | | II-1 | Gde1 | 51573 | 4-May-15 | 8425 | 2 | | | II-1 | Gm14692 | |
| 7900 | 2 | | | II-1 | Gdnf | 2668 | 23-May-15 | 8429 | 2 | | | II-1 | Gm14744 | |
| 7901 | 2 | | | II-1 | Gdpd1 | 284161 | 4-May-15 | 8430 | 2 | | | II-1 | Gm14781 | |
| 7904 | 2 | | | II-1 | Gdpd4 | 220032 | 4-May-15 | 8433 | 2 | | | II-1 | Gm14827 | |
| 7911 | 2 | | | II-1 | Gemin6 | 79833 | 4-May-15 | 8440 | 2 | | | II-1 | Gm15055 | |
| 7913 | 2 | | | II-1 | Gemin8 | 54960 | 4-May-15 | 8446 | 2 | | | II-1 | Gm15107 | |
| 7918 | 2 | | | II-1 | Gfi1 | 2672 | 4-May-15 | 8447 | 2 | | | II-1 | Gm15114 | |
| 7922 | 2 | | | II-1 | Gfod1 | 54438 | 14-May-15 | 8448 | 2 | | | II-1 | Gm15127 | |
| 7925 | 2 | | | II-1 | Gfpt2 | 9945 | 4-May-15 | 8449 | 2 | | | II-1 | Gm15133 | |
| 7932 | 2 | | | II-1 | Gga1 | 26088 | 21-May-15 | 8451 | 2 | | | II-1 | Gm15179 | |
| 7935 | 2 | | | II-1 | Ggact | 87769 | 4-May-15 | 8453 | 2 | | | II-1 | Gm1527 | |
| 7954 | 2 | | | II-1 | Ghrl | 51738 | 21-May-15 | 8469 | 2 | | | II-1 | Gm15417 | |
| 7957 | 2 | | | II-1 | Gid8 | 54994 | 4-May-15 | 8475 | 2 | | | II-1 | Gm1553 | |
| 7959 | 2 | | | II-1 | Gigyf1 | 64599 | 4-May-15 | 8483 | 2 | | | II-1 | Gm15698 | |
| 7982 | 2 | | | II-1 | Gja1 | 2697 | 24-May-15 | 8494 | 2 | | | II-1 | Gm15880 | |
| 8014 | 2 | | | II-1 | Glce | 26035 | 4-May-15 | 8495 | 2 | | | II-1 | Gm15881 | |
| 8019 | 2 | | | II-1 | Glg1 | 2734 | 4-May-15 | 8507 | 2 | | | II-1 | Gm16157 | |
| 8033 | 2 | | | II-1 | Glod5 | 392465 | 4-May-15 | 8508 | 2 | | | II-1 | Gm16287 | |
| 8034 | 2 | | | II-1 | Glp1r | 2740 | 17-May-15 | 8509 | 2 | | | II-1 | Gm16291 | |
| 8037 | 2 | | | II-1 | Glra2 | 2742 | 12-May-15 | 8514 | 2 | | | II-1 | Gm16367 | |
| 8047 | 2 | | | II-1 | Gls2 | 27165 | 24-May-15 | 8515 | 2 | | | II-1 | Gm16381 | |
| 8050 | 2 | | | II-1 | Glt28d2 | | | 8518 | 2 | | | II-1 | Gm16404 | |
| 8063 | 2 | | | II-1 | Glyatl3 | 389396 | 4-May-15 | 8519 | 2 | | | II-1 | Gm16405 | |
| 8068 | 2 | | | II-1 | Gm10012 | | | 8522 | 2 | | | II-1 | Gm16445 | |
| 8074 | 2 | | | II-1 | Gm10058 | | | 8524 | 2 | | | II-1 | Gm1647 | |
| 8080 | 2 | | | II-1 | Gm10100 | | | 8525 | 2 | | | II-1 | Gm16497 | |
| 8091 | 2 | | | II-1 | Gm10267 | | | 8530 | 2 | | | II-1 | Gm16532 | |
| 8100 | 2 | | | II-1 | Gm10364 | | | 8547 | 2 | | | II-1 | Gm16833 | |
| 8102 | 2 | | | II-1 | Gm10375 | | | 8553 | 2 | | | II-1 | Gm16894 | |
| 8105 | 2 | | | II-1 | Gm10390 | | | 8555 | 2 | | | II-1 | Gm16907 | |
| 8106 | 2 | | | II-1 | Gm10400 | | | 8561 | 2 | | | II-1 | Gm17066 | |
| 8112 | 2 | | | II-1 | Gm10416 | | | 8566 | 2 | | | II-1 | Gm17359 | |
| 8120 | 2 | | | II-1 | Gm1045 | | | 8569 | 2 | | | II-1 | Gm17644 | |
| 8124 | 2 | | | II-1 | Gm10474 | | | 8577 | 2 | | | II-1 | Gm17757 | |
| 8132 | 2 | | | II-1 | Gm10516 | | | 8580 | 2 | | | II-1 | Gm17801 | |
| 8135 | 2 | | | II-1 | Gm10538 | | | 8581 | 2 | | | II-1 | Gm17821 | |

Fig.22 - 101

| | | | | | | | | | | | | | | |
|---|---|---|---|---|---|---|---|---|---|---|---|---|---|---|
| 8586 | 2 | | | II-1 | Gm19276 | | | 8915 | 2 | | | II-1 | Gm5409 | | |
| 8591 | 2 | | | II-1 | Gm19395 | | | 8918 | 2 | | | II-1 | Gm5416 | | |
| 8595 | 2 | | | II-1 | Gm19434 | | | 8919 | 2 | | | II-1 | Gm5420 | | |
| 8597 | 2 | | | II-1 | Gm19466 | | | 8925 | 2 | | | II-1 | Gm5460 | | |
| 8599 | 2 | | | II-1 | Gm19522 | | | 8927 | 2 | | | II-1 | Gm5468 | | |
| 8603 | 2 | | | II-1 | Gm19619 | | | 8928 | 2 | | | II-1 | Gm5475 | | |
| 8612 | 2 | | | II-1 | Gm1976 | | | 8929 | 2 | | | II-1 | Gm5476 | | |
| 8615 | 2 | | | II-1 | Gm1979 | | | 8930 | 2 | | | II-1 | Gm5477 | | |
| 8623 | 2 | | | II-1 | Gm20098 | | | 8935 | 2 | | | II-1 | Gm5523 | | |
| 8627 | 2 | | | II-1 | Gm20125 | | | 8945 | 2 | | | II-1 | Gm5595 | | |
| 8629 | 2 | | | II-1 | Gm2016 | | | 8949 | 2 | | | II-1 | Gm5617 | | |
| 8631 | 2 | | | II-1 | Gm20187 | | | 8954 | 2 | | | II-1 | Gm5640 | | |
| 8644 | 2 | | | II-1 | Gm2042 | | | 8960 | 2 | | | II-1 | Gm5726 | | |
| 8648 | 2 | | | II-1 | Gm20597 | | | 8961 | 2 | | | II-1 | Gm5728 | | |
| 8653 | 2 | | | II-1 | Gm20735 | | | 8969 | 2 | | | II-1 | Gm5860 | | |
| 8654 | 2 | | | II-1 | Gm20736 | | | 8970 | 2 | | | II-1 | Gm5801 | | |
| 8657 | 2 | | | II-1 | Gm20741 | | | 8971 | 2 | | | II-1 | Gm5803 | | |
| 8658 | 2 | | | II-1 | Gm20743 | | | 8974 | 2 | | | II-1 | Gm5860 | | |
| 8661 | 2 | | | II-1 | Gm20747 | | | 8978 | 2 | | | II-1 | Gm5885 | | |
| 8664 | 2 | | | II-1 | Gm20751 | | | 8979 | 2 | | | II-1 | Gm5886 | | |
| 8665 | 2 | | | II-1 | Gm20752 | | | 8980 | 2 | | | II-1 | Gm5891 | | |
| 8669 | 2 | | | II-1 | Gm20756 | | | 8986 | 2 | | | II-1 | Gm5934 | | |
| 8670 | 2 | | | II-1 | Gm20757 | | | 8987 | 2 | | | II-1 | Gm5935 | | |
| 8671 | 2 | | | II-1 | Gm20758 | | | 8988 | 2 | | | II-1 | Gm5936 | | |
| 8673 | 2 | | | II-1 | Gm20765 | | | 8991 | 2 | | | II-1 | Gm595 | | |
| 8679 | 2 | | | II-1 | Gm20822 | | | 8993 | 2 | | | II-1 | Gm6026 | | |
| 8680 | 2 | | | II-1 | Gm20823 | | | 8994 | 2 | | | II-1 | Gm6034 | | |
| 8685 | 2 | | | II-1 | Gm20857 | | | 8997 | 2 | | | II-1 | Gm608 | | |
| 8687 | 2 | | | II-1 | Gm20865 | | | 9003 | 2 | | | II-1 | Gm614 | | |
| 8688 | 2 | | | II-1 | Gm20867 | | | 9006 | 2 | | | II-1 | Gm6194 | | |
| 8689 | 2 | | | II-1 | Gm2087 | | | 9009 | 2 | | | II-1 | Gm6249 | | |
| 8690 | 2 | | | II-1 | Gm20871 | | | 9010 | 2 | | | II-1 | Gm6251 | | |
| 8698 | 2 | | | II-1 | Gm21119 | | | 9024 | 2 | | | II-1 | Gm6406 | | |
| 8699 | 2 | | | II-1 | Gm2115 | | | 9026 | 2 | | | II-1 | Gm6416 | | |
| 8702 | 2 | | | II-1 | Gm21276 | | | 9030 | 2 | | | II-1 | Gm648 | | |
| 8703 | 2 | | | II-1 | Gm21283 | | | 9034 | 2 | | | II-1 | Gm6525 | | |
| 8704 | 2 | | | II-1 | Gm21284 | | | 9037 | 2 | | | II-1 | Gm6559 | | |
| 8705 | 2 | | | II-1 | Gm21293 | | | 9038 | 2 | | | II-1 | Gm6567 | | |
| 8706 | 2 | | | II-1 | Gm21304 | | | 9043 | 2 | | | II-1 | Gm6592 | | |
| 8707 | 2 | | | II-1 | Gm21312 | | | 9044 | 2 | | | II-1 | Gm6602 | | |
| 8714 | 2 | | | II-1 | Gm21693 | | | 9045 | 2 | | | II-1 | Gm6607 | | |
| 8717 | 2 | | | II-1 | Gm21943 | | | 9048 | 2 | | | II-1 | Gm6634 | | |
| 8718 | 2 | | | II-1 | Gm21944 | | | 9049 | 2 | | | II-1 | Gm6639 | | |
| 8719 | 2 | | | II-1 | Gm21949 | | | 9057 | 2 | | | II-1 | Gm6760 | | |
| 8720 | 2 | | | II-1 | Gm21950 | | | 9058 | 2 | | | II-1 | Gm6763 | | |
| 8724 | 2 | | | II-1 | Gm2382 | | | 9059 | 2 | | | II-1 | Gm6787 | | |
| 8727 | 2 | | | II-1 | Gm2518 | | | 9062 | 2 | | | II-1 | Gm6812 | | |
| 8734 | 2 | | | II-1 | Gm2799 | | | 9063 | 2 | | | II-1 | Gm6815 | | |
| 8736 | 2 | | | II-1 | Gm2837 | | | 9067 | 2 | | | II-1 | Gm6890 | | |
| 8737 | 2 | | | II-1 | Gm2848 | | | 9069 | 2 | | | II-1 | Gm6904 | | |
| 8738 | 2 | | | II-1 | Gm2863 | | | 9072 | 2 | | | II-1 | Gm6938 | | |
| 8740 | 2 | | | II-1 | Gm2913 | | | 9077 | 2 | | | II-1 | Gm7030 | | |
| 8741 | 2 | | | II-1 | Gm2927 | | | 9080 | 2 | | | II-1 | Gm7102 | | |
| 8742 | 2 | | | II-1 | Gm2933 | | | 9083 | 2 | | | II-1 | Gm7120 | | |
| 8744 | 2 | | | II-1 | Gm3002 | | | 9088 | 2 | | | II-1 | Gm7173 | | |
| 8745 | 2 | | | II-1 | Gm3020 | | | 9092 | 2 | | | II-1 | Gm732 | | |
| 8762 | 2 | | | II-1 | Gm3404 | | | 9097 | 2 | | | II-1 | Gm7367 | | |
| 8763 | 2 | | | II-1 | Gm3409 | | | 9100 | 2 | | | II-1 | Gm7534 | | |
| 8764 | 2 | | | II-1 | Gm3414 | | | 9101 | 2 | | | II-1 | Gm7538 | | |
| 8771 | 2 | | | II-1 | Gm3488 | | | 9102 | 2 | | | II-1 | Gm7550 | | |
| 8773 | 2 | | | II-1 | Gm3558 | | | 9115 | 2 | | | II-1 | Gm7977 | | |
| 8774 | 2 | | | II-1 | Gm3604 | | | 9117 | 2 | | | II-1 | Gm7978 | | |
| 8777 | 2 | | | II-1 | Gm3646 | | | 9118 | 2 | | | II-1 | Gm805 | | |
| 8778 | 2 | | | II-1 | Gm3696 | | | 9123 | 2 | | | II-1 | Gm8179 | | |
| 8780 | 2 | | | II-1 | Gm3706 | | | 9129 | 2 | | | II-1 | Gm8298 | | |
| 8781 | 2 | | | II-1 | Gm3716 | | | 9130 | 2 | | | II-1 | Gm8300 | | |
| 8787 | 2 | | | II-1 | Gm3985 | | | 9144 | 2 | | | II-1 | Gm8709 | | |
| 8794 | 2 | | | II-1 | Gm4201 | | | 9154 | 2 | | | II-1 | Gm8898 | | |
| 8801 | 2 | | | II-1 | Gm4278 | | | 9160 | 2 | | | II-1 | Gm904 | | |
| 8802 | 2 | | | II-1 | Gm428 | | | 9163 | 2 | | | II-1 | Gm906 | | |
| 8806 | 2 | | | II-1 | Gm4302 | | | 9166 | 2 | | | II-1 | Gm9125 | | |
| 8817 | 2 | | | II-1 | Gm4461 | | | 9167 | 2 | | | II-1 | Gm9139 | | |
| 8825 | 2 | | | II-1 | Gm4598 | | | 9168 | 2 | | | II-1 | Gm9199 | | |
| 8828 | 2 | | | II-1 | Gm4724 | | | 9175 | 2 | | | II-1 | Gm960 | | |
| 8831 | 2 | | | II-1 | Gm4759 | | | 9177 | 2 | | | II-1 | Gm973 | | |
| 8832 | 2 | | | II-1 | Gm4763 | | | 9180 | 2 | | | II-1 | Gm9758 | | |
| 8837 | 2 | | | II-1 | Gm4792 | | | 9182 | 2 | | | II-1 | Gm9776 | | |
| 8838 | 2 | | | II-1 | Gm4794 | | | 9192 | 2 | | | II-1 | Gm9958 | | |
| 8846 | 2 | | | II-1 | Gm4850 | | | 9199 | 2 | | | II-1 | Gmcl1 | 64395 | 4-May-15 |
| 8847 | 2 | | | II-1 | Gm4858 | | | 9200 | 2 | | | II-1 | Gmcl1 | 64396 | 4-May-15 |
| 8851 | 2 | | | II-1 | Gm4884 | | | 9201 | 2 | | | II-1 | Gmds | 2762 | 4-May-15 |
| 8855 | 2 | | | II-1 | Gm4907 | | | 9204 | 2 | | | II-1 | Gmfb | 2764 | 4-May-15 |
| 8860 | 2 | | | II-1 | Gm4944 | | | 9205 | 2 | | | II-1 | Gmfg | 9535 | 12-May-15 |
| 8861 | 2 | | | II-1 | Gm4951 | | | 9206 | 2 | | | II-1 | Gmip | 51291 | 28-May-15 |
| 8870 | 2 | | | II-1 | Gm5 | | | 9215 | 2 | | | II-1 | Gnai1 | 2767 | 4-May-15 |
| 8872 | 2 | | | II-1 | Gm5065 | | | 9229 | 2 | | | II-1 | Gnat | 2774 | 12-May-15 |
| 8876 | 2 | | | II-1 | Gm5082 | | | 9233 | 2 | | | II-1 | Gnb2 | 2783 | 4-May-15 |
| 8878 | 2 | | | II-1 | Gm5084 | | | 9234 | 2 | | | II-1 | Gnb2l1 | 10399 | 31-May-15 |
| 8884 | 2 | | | II-1 | Gm5095 | | | 9265 | 2 | | | II-1 | Golga1 | 2800 | 4-May-15 |
| 8888 | 2 | | | II-1 | Gm5105 | | | 9267 | 2 | | | II-1 | Golga3 | 2802 | 4-May-15 |
| 8891 | 2 | | | II-1 | Gm5124 | | | 9271 | 2 | | | II-1 | Golga7b | 401647 | 4-May-15 |
| 8895 | 2 | | | II-1 | Gm5132 | | | 9280 | 2 | | | II-1 | Gopc | 57120 | 24-May-15 |
| 8901 | 2 | | | II-1 | Gm5150 | | | 9283 | 2 | | | II-1 | Gorasp2 | 26003 | 4-May-15 |
| 8903 | 2 | | | II-1 | Gm5168 | | | 9284 | 2 | | | II-1 | Gosr1 | 9527 | 4-May-15 |
| 8904 | 2 | | | II-1 | Gm5169 | | | 9285 | 2 | | | II-1 | Gosr2 | 9570 | 4-May-15 |
| 8913 | 2 | | | II-1 | Gm5347 | | | 9298 | 2 | | | II-1 | Gpalpp1 | 55425 | 12-May-15 |
| 8914 | 2 | | | II-1 | Gm5382 | | | 9299 | 2 | | | II-1 | Gpam | 57678 | 12-May-15 |

Fig.22 - 102

| | | | | | | | | | | | | | | |
|---|---|---|---|---|---|---|---|---|---|---|---|---|---|---|
| 9303 | 2 | | | H-1 | Gpatch11 | 253635 | 4-May-15 | 10033 | 2 | | | H-1 | Hnrnpc | 3183 | 4-May-15 |
| 9304 | 2 | | | H-1 | Gpatch2 | 56105 | 4-May-15 | 10034 | 2 | | | H-1 | Hnrnpd | 3184 | 2-Jun-15 |
| 9305 | 2 | | | H-1 | Gpatch2l | 55668 | 12-May-15 | 10035 | 2 | | | H-1 | Hnrnpdl | 9987 | 4-May-15 |
| 9306 | 2 | | | H-1 | Gpatch3 | 63906 | 4-May-15 | 10037 | 2 | | | H-1 | Hnrnph1 | 3187 | 4-May-15 |
| 9307 | 2 | | | H-1 | Gpatch4 | 54865 | 4-May-15 | 10038 | 2 | | | H-1 | Hnrnph2 | 3188 | 4-May-15 |
| 9309 | 2 | | | H-1 | Gpbar1 | 151306 | 4-May-15 | 10039 | 2 | | | H-1 | Hnrnph3 | 3189 | 4-May-15 |
| 9311 | 2 | | | H-1 | Gpbp1l1 | 60313 | 4-May-15 | 10040 | 2 | | | H-1 | Hnrnpk | 3190 | 28-May-15 |
| 9326 | 2 | | | H-1 | Gpi1 | 9091 | 4-May-15 | 10042 | 2 | | | H-1 | Hnrnpll | 92906 | 12-May-15 |
| 9330 | 2 | | | H-1 | Gpm6a | 2823 | 4-May-15 | 10043 | 2 | | | H-1 | Hnrnpm | 4670 | 3-Jun-15 |
| 9333 | 2 | | | H-1 | Gpn2 | 54707 | 4-May-15 | 10044 | 2 | | | H-1 | Hnrnpr | 10236 | 2-Jun-15 |
| 9340 | 2 | | | H-1 | Gpr110 | 266977 | 4-May-15 | 10045 | 2 | | | H-1 | Hnrnpu | 3192 | 4-May-15 |
| 9347 | 2 | | | H-1 | Gpr12 | 2835 | 4-May-15 | 10046 | 2 | | | H-1 | Hnrnpul1 | 11100 | 12-May-15 |
| 9353 | 2 | | | H-1 | Gpr132 | 29933 | 4-May-15 | 10047 | 2 | | | H-1 | Hnrnpul2 | 221092 | 12-May-15 |
| 9362 | 2 | | | H-1 | Gpr142 | 350383 | 4-May-15 | 10059 | 2 | | | H-1 | Hotair | 100124700 | 31-May-15 |
| 9363 | 2 | | | H-1 | Gpr143 | 4935 | 23-May-15 | 10060 | 2 | | | H-1 | Hottip | 100316868 | 12-May-15 |
| 9364 | 2 | | | H-1 | Gpr146 | 115330 | 12-May-15 | 10064 | 2 | | | H-1 | Hoxa11os | | |
| 9367 | 2 | | | H-1 | Gpr150 | 285601 | 4-May-15 | 10074 | 2 | | | H-1 | Hoxb13 | 10481 | 31-May-15 |
| 9369 | 2 | | | H-1 | Gpr152 | 390212 | 4-May-15 | 10087 | 2 | | | H-1 | Hoxc4 | 3221 | 4-May-15 |
| 9370 | 2 | | | H-1 | Gpr153 | 387509 | 4-May-15 | 10092 | 2 | | | H-1 | Hoxd1 | 3231 | 12-May-15 |
| 9375 | 2 | | | H-1 | Gpr160 | 26996 | 4-May-15 | 10093 | 2 | | | H-1 | Hoxd10 | 3236 | 12-May-15 |
| 9377 | 2 | | | H-1 | Gpr162 | 27239 | 4-May-15 | 10094 | 2 | | | H-1 | Hoxd11 | 3237 | 12-May-15 |
| 9405 | 2 | | | H-1 | Gpr45 | 11250 | 4-May-15 | 10096 | 2 | | | H-1 | Hoxd13 | 3239 | 12-May-15 |
| 9412 | 2 | | | H-1 | Gpr62 | 118442 | 12-May-15 | 10116 | 2 | | | H-1 | Hps5 | 11234 | 23-May-15 |
| 9413 | 2 | | | H-1 | Gpr63 | 81491 | 4-May-15 | 10118 | 2 | | | H-1 | Hps6 | 10855 | 24-May-15 |
| 9425 | 2 | | | H-1 | Gpr97 | 222487 | 4-May-15 | 10119 | 2 | | | H-1 | Hpse2 | 60495 | 12-May-15 |
| 9427 | 2 | | | H-1 | Gprasp1 | 9737 | 4-May-15 | 10136 | 2 | | | H-1 | Hs2st1 | 9653 | 4-May-15 |
| 9482 | 2 | | | H-1 | Grifin | 402635 | 3-May-15 | 10179 | 2 | | | H-1 | Hsh2d | 84941 | 4-May-15 |
| 9485 | 2 | | | H-1 | Grik3 | 2899 | 4-May-15 | 10193 | 2 | | | H-1 | Hspa5 | 3309 | 31-May-15 |
| 9486 | 2 | | | H-1 | Grik4 | 2900 | 4-May-15 | 10206 | 2 | | | H-1 | Hspd1 | 3329 | 17-May-15 |
| 9487 | 2 | | | H-1 | Grik5 | 2901 | 12-May-15 | 10213 | 2 | | | H-1 | Htr1b | 3351 | 24-May-15 |
| 9491 | 2 | | | H-1 | Grin2b | 2904 | 17-May-15 | 10216 | 2 | | | H-1 | Htr2a | 3356 | 7-Jun-15 |
| 9498 | 2 | | | H-1 | Grip1os2 | | | 10217 | 2 | | | H-1 | Htr2b | 3357 | 12-May-15 |
| 9502 | 2 | | | H-1 | Grk4 | 2868 | 12-May-15 | 10222 | 2 | | | H-1 | Htr5a | 3361 | 12-May-15 |
| 9503 | 2 | | | H-1 | Grk5 | 2869 | 4-May-15 | 10225 | 2 | | | H-1 | Htr7 | 3363 | 12-May-15 |
| 9506 | 2 | | | H-1 | Grm2 | 2912 | 12-May-15 | 10234 | 2 | | | H-1 | Huwe1 | 10075 | 12-May-15 |
| 9508 | 2 | | | H-1 | Grm4 | 2914 | 7-Jun-15 | 10239 | 2 | | | H-1 | Hyal4 | 23553 | 4-May-15 |
| 9509 | 2 | | | H-1 | Grm5 | 2915 | 7-Jun-15 | 10241 | 2 | | | H-1 | Hyal6 | 26062 | 12-May-15 |
| 9511 | 2 | | | H-1 | Grm7 | 2917 | 12-May-15 | 10242 | 2 | | | H-1 | Hydin | 54768 | 23-May-15 |
| 9515 | 2 | | | H-1 | Grpel1 | 80273 | 4-May-15 | 10250 | 2 | | | H-1 | I830012O16Rik | | |
| 9523 | 2 | | | H-1 | Grxcr2 | 643226 | 4-May-15 | 10256 | 2 | | | H-1 | Iba57 | 200205 | 4-May-15 |
| 9524 | 2 | | | H-1 | Gsap | 54103 | 4-May-15 | 10259 | 2 | | | H-1 | Ica1 | 3382 | 12-May-15 |
| 9544 | 2 | | | H-1 | Gskip | 51527 | 4-May-15 | 10260 | 2 | | | H-1 | Ica1l | 130026 | 4-May-15 |
| 9571 | 2 | | | H-1 | Gstz1 | 2954 | 12-May-15 | 10261 | 2 | | | H-1 | Icam1 | 3383 | 17-May-15 |
| 9574 | 2 | | | H-1 | Gt(ROSA)26Sor | | | 10268 | 2 | | | H-1 | Icos1 | 23308 | 17-May-15 |
| 9576 | 2 | | | H-1 | Gtf2a1 | 2957 | 4-May-15 | 10279 | 2 | | | H-1 | Idh3g | 3421 | 4-May-15 |
| 9582 | 2 | | | H-1 | Gtf2h1 | 2962 | 4-May-15 | 10287 | 2 | | | H-1 | Ier2 | 9592 | 21-May-15 |
| 9585 | 2 | | | H-1 | Gtf2h2 | 2966 | 4-May-15 | 10296 | 2 | | | H-1 | Ifi204 | | |
| 9593 | 2 | | | H-1 | Gtf3c1 | 2975 | 4-May-15 | 10303 | 2 | | | H-1 | Ifi44 | 10561 | 4-May-15 |
| 9595 | 2 | | | H-1 | Gtf3c3 | 9330 | 4-May-15 | 10319 | 2 | | | H-1 | Ifna11 | | |
| 9596 | 2 | | | H-1 | Gtf3c4 | 9329 | 4-May-15 | 10320 | 2 | | | H-1 | Ifna12 | | |
| 9598 | 2 | | | H-1 | Gtf3c6 | 112495 | 4-May-15 | 10334 | 2 | | | H-1 | Ifnb1 | 3456 | 31-May-15 |
| 9603 | 2 | | | H-1 | Gtpbp10 | 85865 | 4-May-15 | 10336 | 2 | | | H-1 | Ifng | 3458 | 31-May-15 |
| 9606 | 2 | | | H-1 | Gtpbp8 | 29083 | 4-May-15 | 10341 | 2 | | | H-1 | Ifnl3 | 282617 | 7-Jun-15 |
| 9619 | 2 | | | H-1 | Gucy2c | 2984 | 12-May-15 | 10349 | 2 | | | H-1 | Ift20 | 90410 | 29-May-15 |
| 9621 | 2 | | | H-1 | Gucy2e | 390248 | 4-May-15 | 10358 | 2 | | | H-1 | Ifi81 | 78981 | 4-May-15 |
| 9622 | 2 | | | H-1 | Gucy2f | 2986 | 4-May-15 | 10360 | 2 | | | H-1 | Igbp1 | 3476 | 4-May-15 |
| 9624 | 2 | | | H-1 | Gz1 | 60558 | 4-May-15 | 10362 | 2 | | | H-1 | Igdcc3 | 9543 | 4-May-15 |
| 9645 | 2 | | | H-1 | Gzme | | | 10369 | 2 | | | H-1 | Igf2bp3 | 10643 | 4-May-15 |
| 9646 | 2 | | | H-1 | Gzmf | | | 10372 | 2 | | | H-1 | Igfals | 3483 | 12-May-15 |
| 9648 | 2 | | | H-1 | Gzmk | 3003 | 4-May-15 | 10407 | 2 | | | H-1 | Ikbke | 9641 | 12-May-15 |
| 9656 | 2 | | | H-1 | H1fx | 8971 | 4-May-15 | 10408 | 2 | | | H-1 | Ikbkg | 8517 | 23-May-15 |
| 9684 | 2 | | | H-1 | H2-M10.1 | | | 10414 | 2 | | | H-1 | Il10 | 3586 | 31-May-15 |
| 9713 | 2 | | | H-1 | H3f3b | 3021 | 4-May-15 | 10418 | 2 | | | H-1 | Il11ra1 | | |
| 9724 | 2 | | | H-1 | Hadhb | 3032 | 4-May-15 | 10432 | 2 | | | H-1 | Il17c | 27189 | 12-May-15 |
| 9736 | 2 | | | H-1 | Hapln2 | 60484 | 4-May-15 | 10436 | 2 | | | H-1 | Il17rb | 55540 | 4-May-15 |
| 9741 | 2 | | | H-1 | Hars2 | 23428 | 7-Jun-15 | 10439 | 2 | | | H-1 | Il17re | 132014 | 12-May-15 |
| 9767 | 2 | | | H-1 | Hbegf | 1839 | 12-May-15 | 10445 | 2 | | | H-1 | Il1a | 3552 | 31-May-15 |
| 9773 | 2 | | | H-1 | Hcar1 | 27198 | 21-May-15 | 10457 | 2 | | | H-1 | Il1rapl2 | 26280 | 12-May-15 |
| 9778 | 2 | | | H-1 | Hcfc2 | 29915 | 4-May-15 | 10463 | 2 | | | H-1 | Il20ra | 53832 | 12-May-15 |
| 9788 | 2 | | | H-1 | Hcst | 10870 | 7-Jun-15 | 10474 | 2 | | | H-1 | Il27 | 246778 | 4-May-15 |
| 9794 | 2 | | | H-1 | Hdac4 | 9759 | 28-May-15 | 10481 | 2 | | | H-1 | Il31ra | 133396 | 7-Jun-15 |
| 9798 | 2 | | | H-1 | Hdac8 | 55869 | 28-May-15 | 10501 | 2 | | | H-1 | Ilk | 3611 | 4-May-15 |
| 9805 | 2 | | | H-1 | Hdgfrp2 | 84717 | 30-May-15 | 10504 | 2 | | | H-1 | Ilvbl | 10994 | 4-May-15 |
| 9806 | 2 | | | H-1 | Hdgfrp3 | 50810 | 4-May-15 | 10509 | 2 | | | H-1 | Imp4 | 92856 | 7-Jun-15 |
| 9808 | 2 | | | H-1 | Hdhd2 | 84064 | 12-May-15 | 10510 | 2 | | | H-1 | Impa1 | 3612 | 12-May-15 |
| 9809 | 2 | | | H-1 | Hdhd3 | 81932 | 12-May-15 | 10517 | 2 | | | H-1 | Impg2 | 50939 | 23-May-15 |
| 9812 | 2 | | | H-1 | Heatr1 | 55127 | 21-May-15 | 10524 | 2 | | | H-1 | Ing2 | 3622 | 7-Jun-15 |
| 9813 | 2 | | | H-1 | Heatr2 | 54919 | 7-Jun-15 | 10527 | 2 | | | H-1 | Ing5 | 84289 | 4-May-15 |
| 9816 | 2 | | | H-1 | Heatr5b | 54497 | 12-May-15 | 10537 | 2 | | | H-1 | Ino80c | 125476 | 12-May-15 |
| 9826 | 2 | | | H-1 | Hecw2 | 57520 | 12-May-15 | 10541 | 2 | | | H-1 | Inpp1 | 3628 | 4-May-15 |
| 9838 | 2 | | | H-1 | Hepacam | 220296 | 23-May-15 | 10544 | 2 | | | H-1 | Inpp5a | 3632 | 4-May-15 |
| 9846 | 2 | | | H-1 | Herc6 | 55008 | 4-May-15 | 10549 | 2 | | | H-1 | Inpp5j | 27124 | 4-May-15 |
| 9849 | 2 | | | H-1 | Hes1 | 3280 | 7-Jun-15 | 10567 | 2 | | | H-1 | Ints2 | 57508 | 4-May-15 |
| 9853 | 2 | | | H-1 | Hes6 | 55502 | 24-May-15 | 10568 | 2 | | | H-1 | Ints3 | 65123 | 4-May-15 |
| 9860 | 2 | | | H-1 | Hexim2 | 124790 | 12-May-15 | 10570 | 2 | | | H-1 | Ints5 | 80789 | 4-May-15 |
| 9861 | 2 | | | H-1 | Hey1 | 23462 | 28-May-15 | 10575 | 2 | | | H-1 | Intu | 27152 | 12-May-15 |
| 9868 | 2 | | | H-1 | Hgf | 3082 | 7-Jun-15 | 10576 | 2 | | | H-1 | Invs | 27130 | 14-May-15 |
| 9871 | 2 | | | H-1 | Hgsnat | 138050 | 4-May-15 | 10583 | 2 | | | H-1 | Ipo13 | 9670 | 4-May-15 |
| 9820 | 2 | | | H-1 | Hiatl1 | 84641 | 4-May-15 | 10586 | 2 | | | H-1 | Ipo7 | 10527 | 4-May-15 |
| 9893 | 2 | | | H-1 | Hilpda | 29923 | 4-May-15 | 10588 | 2 | | | H-1 | Ipo9 | 55705 | 4-May-15 |
| 9896 | 2 | | | H-1 | Hint1 | 3094 | 7-Jun-15 | 10589 | 2 | | | H-1 | Ipp | 3652 | 4-May-15 |
| 9906 | 2 | | | H-1 | Hirip3 | 8479 | 4-May-15 | 10590 | 2 | | | H-1 | Ippk | 64768 | 28-May-15 |
| 10003 | 2 | | | H-1 | Hmgcl1 | 54511 | 4-May-15 | 10592 | 2 | | | H-1 | Iqca | 79781 | 4-May-15 |
| 10013 | 2 | | | H-1 | Hmha1 | 23526 | 4-May-15 | 10593 | 2 | | | H-1 | Iqcb1 | 9657 | 4-May-15 |
| 10026 | 2 | | | H-1 | Hnf4g | 3174 | 12-May-15 | 10597 | 2 | | | H-1 | Iqcf1 | 132141 | 4-May-15 |
| 10028 | 2 | | | H-1 | Hnrnpa0 | 10949 | 4-May-15 | 10598 | 2 | | | H-1 | Iqcf3 | 401067 | 4-May-15 |
| 10032 | 2 | | | H-1 | Hnrnpab | 3182 | 4-May-15 | | | | | | | | |

Fig.22 - 103

| | | | | | | | | | | | | | |
|---|---|---|---|---|---|---|---|---|---|---|---|---|---|
| 10600 | 2 | | | II-1 | Iqcf5 | 389124 | 4-May-15 | 11455 | 2 | | | II-1 | Leprot11 | 23484 | 4-May-15 |
| 10601 | 2 | | | II-1 | Iqcf6 | 440956 | 4-May-15 | 11456 | 2 | | | II-1 | Letm1 | 3954 | 17-May-15 |
| 10614 | 2 | | | II-1 | Irak1bp1 | 134728 | 4-May-15 | 11457 | 2 | | | II-1 | Letm2 | 137994 | 4-May-15 |
| 10618 | 2 | | | II-1 | Ireb2 | 3658 | 12-May-15 | 11472 | 2 | | | II-1 | Lgi2 | 55203 | 12-May-15 |
| 10619 | 2 | | | II-1 | Irf1 | 3659 | 12-May-15 | 11478 | 2 | | | II-1 | Lgr6 | 59352 | 4-May-15 |
| 10667 | 2 | | | II-1 | Itfg1 | 81533 | 12-May-15 | 11480 | 2 | | | II-1 | Lhb | 3972 | 12-May-15 |
| 10668 | 2 | | | II-1 | Itfg2 | 55846 | 4-May-15 | 11487 | 2 | | | II-1 | Lhfpl5 | 222662 | 23-May-15 |
| 10715 | 2 | | | II-1 | Itpkc | 80271 | 31-May-15 | 11494 | 2 | | | II-1 | Lhx5 | 64211 | 4-May-15 |
| 10719 | 2 | | | II-1 | Itprip | 85450 | 12-May-15 | 11497 | 2 | | | II-1 | Lhx9 | 56956 | 12-May-15 |
| 10731 | 2 | | | II-1 | Izumo3 | 100129669 | 4-May-15 | 11498 | 2 | | | II-1 | Lias | 11019 | 4-May-15 |
| 10732 | 2 | | | II-1 | Izumo4 | 133177 | 4-May-15 | 11514 | 2 | | | II-1 | Limk2 | 3985 | 12-May-15 |
| 10740 | 2 | | | II-1 | Jak2 | 3717 | 7-Jun-15 | 11519 | 2 | | | II-1 | Lin37 | 55957 | 4-May-15 |
| 10741 | 2 | | | II-1 | Jak3 | 3718 | 10-May-15 | 11522 | 2 | | | II-1 | Lin7a | 8825 | 4-May-15 |
| 10745 | 2 | | | II-1 | Jam2 | 58494 | 7-Jun-15 | 11540 | 2 | | | II-1 | Lipm | 340654 | 4-May-15 |
| 10747 | 2 | | | II-1 | Jarid2 | 3720 | 31-May-15 | 11541 | 2 | | | II-1 | Lipn | 643418 | 4-May-15 |
| 10752 | 2 | | | II-1 | Jmjd4 | 65094 | 12-May-15 | 11552 | 2 | | | II-1 | Lman1 | 3998 | 12-May-15 |
| 10757 | 2 | | | II-1 | Jrny | 133746 | 4-May-15 | 11553 | 2 | | | II-1 | Lman1l | 79748 | 4-May-15 |
| 10758 | 2 | | | II-1 | Josd1 | 9929 | 12-May-15 | 11556 | 2 | | | II-1 | Lmbr1 | 64327 | 4-May-15 |
| 10759 | 2 | | | II-1 | Josd2 | 126119 | 4-May-15 | 11558 | 2 | | | II-1 | Lmbrd1 | 55788 | 23-May-15 |
| 10773 | 2 | | | II-1 | Kalrn | 8997 | 4-May-15 | 11563 | 2 | | | II-1 | Lmln | 89782 | 4-May-15 |
| 10778 | 2 | | | II-1 | Kank4os | | | 11579 | 2 | | | II-1 | Lnp | 80856 | 13-Jun-15 |
| 10786 | 2 | | | II-1 | Kat2b | 8850 | 4-May-15 | 11599 | 2 | | | II-1 | LOC101055769 | | |
| 10787 | 2 | | | II-1 | Kat5 | 10524 | 31-May-15 | 11604 | 2 | | | II-1 | LOC101056236 | | |
| 10788 | 2 | | | II-1 | Kat6a | 7994 | 3-Jun-15 | 11608 | 2 | | | II-1 | LOC102631757 | | |
| 10795 | 2 | | | II-1 | Katnb1 | 10300 | 12-May-15 | 11611 | 2 | | | II-1 | LOC102633085 | | |
| 10806 | 2 | | | II-1 | Kbtbd8 | 84541 | 4-May-15 | 11612 | 2 | | | II-1 | LOC102633315 | | |
| 10811 | 2 | | | II-1 | Kcna3 | 3738 | 4-May-15 | 11615 | 2 | | | II-1 | LOC102634431 | | |
| 10818 | 2 | | | II-1 | Kcnab3 | 9196 | 4-May-15 | 11616 | 2 | | | II-1 | LOC102634793 | | |
| 10843 | 2 | | | II-1 | Kcnh5 | 27133 | 2-Jun-15 | 11617 | 2 | | | II-1 | LOC102635087 | | |
| 10844 | 2 | | | II-1 | Kcnh6 | 81033 | 4-May-15 | 11621 | 2 | | | II-1 | LOC381967 | | |
| 10870 | 2 | | | II-1 | Kcnk15 | 60598 | 4-May-15 | 11622 | 2 | | | II-1 | LOC666331 | | |
| 10871 | 2 | | | II-1 | Kcnk16 | 83795 | 4-May-15 | 11626 | 2 | | | II-1 | Lonrf1 | 91694 | 4-May-15 |
| 10902 | 2 | | | II-1 | Kcnu1 | 157855 | 4-May-15 | 11645 | 2 | | | II-1 | Lpcat3 | 10162 | 12-May-15 |
| 10903 | 2 | | | II-1 | Kcnv1 | 27012 | 1-Jun-15 | 11661 | 2 | | | II-1 | Lrch2 | 57631 | 4-May-15 |
| 10918 | 2 | | | II-1 | Kctd2 | 23510 | 4-May-15 | 11662 | 2 | | | II-1 | Lrch3 | 84859 | 4-May-15 |
| 10920 | 2 | | | II-1 | Kctd21 | 283219 | 4-May-15 | 11668 | 2 | | | II-1 | Lrfn4 | 78999 | 4-May-15 |
| 10921 | 2 | | | II-1 | Kctd3 | 51133 | 12-May-15 | 11673 | 2 | | | II-1 | Lrig1 | 26018 | 4-May-15 |
| 10924 | 2 | | | II-1 | Kctd6 | 200845 | 2-Jun-15 | 11682 | 2 | | | II-1 | Lrp11 | 84918 | 29-May-15 |
| 10925 | 2 | | | II-1 | Kctd7 | 154881 | 4-May-15 | 11683 | 2 | | | II-1 | Lrp12 | 29967 | 12-May-15 |
| 10926 | 2 | | | II-1 | Kctd8 | 386617 | 4-May-15 | 11686 | 2 | | | II-1 | Lrp2bp | 55805 | 7-Jun-15 |
| 10930 | 2 | | | II-1 | Kdelr1 | 10945 | 4-May-15 | 11692 | 2 | | | II-1 | Lrpap1 | 4043 | 12-May-15 |
| 10931 | 2 | | | II-1 | Kdelr2 | 11014 | 4-May-15 | 11727 | 2 | | | II-1 | Lrrc43 | 254050 | 4-May-15 |
| 10932 | 2 | | | II-1 | Kdelr3 | 11015 | 4-May-15 | 11731 | 2 | | | II-1 | Lrrc48 | 83450 | 4-May-15 |
| 10936 | 2 | | | II-1 | Kdm2a | 22992 | 17-May-15 | 11742 | 2 | | | II-1 | Lrrc6 | 23639 | 7-Jun-15 |
| 10937 | 2 | | | II-1 | Kdm2b | 84678 | 17-May-15 | 11744 | 2 | | | II-1 | Lrrc63 | 220416 | 4-May-15 |
| 10938 | 2 | | | II-1 | Kdm3a | 55818 | 3-May-15 | 11745 | 2 | | | II-1 | Lrrc6 | 339977 | 4-May-15 |
| 10940 | 2 | | | II-1 | Kdm4a | 9682 | 12-May-15 | 11746 | 2 | | | II-1 | Lrrc69 | 100130742 | 12-May-15 |
| 10941 | 2 | | | II-1 | Kdm4b | 23030 | 24-May-15 | 11748 | 2 | | | II-1 | Lrrc71 | 149499 | 4-May-15 |
| 10942 | 2 | | | II-1 | Kdm4c | 23081 | 17-May-15 | 11750 | 2 | | | II-1 | Lrrc73 | 221424 | 2-Jun-15 |
| 10943 | 2 | | | II-1 | Kdm4d | 55693 | 4-May-15 | 11752 | 2 | | | II-1 | Lrrc75a | 388341 | 4-May-15 |
| 10944 | 2 | | | II-1 | Kdm5a | 5927 | 4-May-15 | 11760 | 2 | | | II-1 | Lrrcc1 | 85444 | 4-May-15 |
| 10945 | 2 | | | II-1 | Kdm5b | 10765 | 12-May-15 | 11761 | 2 | | | II-1 | Lrrd1 | 401387 | 4-May-15 |
| 10948 | 2 | | | II-1 | Kdm6a | 7403 | 23-May-15 | 11763 | 2 | | | II-1 | Lrrfip2 | 9209 | 4-May-15 |
| 10955 | 2 | | | II-1 | Keg1 | | | 11765 | 2 | | | II-1 | Lrrig3 | 127255 | 4-May-15 |
| 10963 | 2 | | | II-1 | Khdrbs2 | 202559 | 12-May-15 | 11766 | 2 | | | II-1 | Lrriq4 | 344657 | 4-May-15 |
| 10969 | 2 | | | II-1 | Kif11 | 3832 | 4-May-15 | 11767 | 2 | | | II-1 | Lrrk1 | 79705 | 4-May-15 |
| 10981 | 2 | | | II-1 | Kif1b | 23095 | 23-May-15 | 11776 | 2 | | | II-1 | Lrrtm3 | 347731 | 1-Jun-15 |
| 10994 | 2 | | | II-1 | Kif2b | 84643 | 12-May-15 | 11778 | 2 | | | II-1 | Lrsam1 | 90678 | 7-Jun-15 |
| 10998 | 2 | | | II-1 | Kif3c | 3797 | 4-May-15 | 11783 | 2 | | | II-1 | Lsg1 | 55341 | 23-May-15 |
| 11011 | 2 | | | II-1 | Kifc5b | | | 11785 | 2 | | | II-1 | Lsm10 | 84967 | 4-May-15 |
| 11012 | 2 | | | II-1 | Kin | 22944 | 4-May-15 | 11789 | 2 | | | II-1 | Lsm14b | 149986 | 4-May-15 |
| 11015 | 2 | | | II-1 | Kirrel | 55243 | 4-May-15 | 11790 | 2 | | | II-1 | Lsm2 | 57819 | 4-May-15 |
| 11027 | 2 | | | II-1 | Klc2 | 64837 | 7-Jun-15 | 11819 | 2 | | | II-1 | Luc7l3 | 51747 | 4-May-15 |
| 11066 | 2 | | | II-1 | Klhl2 | 11275 | 4-May-15 | 11820 | 2 | | | II-1 | Lum | 4060 | 12-May-15 |
| 11074 | 2 | | | II-1 | Klhl28 | 54813 | 12-May-15 | 11856 | 2 | | | II-1 | Lypd5 | 284348 | 14-May-15 |
| 11093 | 2 | | | II-1 | Klhl9 | 55958 | 4-May-15 | 11880 | 2 | | | II-1 | Lyz14os | | |
| 11101 | 2 | | | II-1 | Klk1b1 | | | 11881 | 2 | | | II-1 | Lyzl6 | 57151 | 4-May-15 |
| 11122 | 2 | | | II-1 | Klra1 | 10748 | 12-May-15 | 11882 | 2 | | | II-1 | Lzic | 84328 | 12-May-15 |
| 11123 | 2 | | | II-1 | Klra10 | | | 11883 | 2 | | | II-1 | Lztfl1 | 54585 | 4-May-15 |
| 11138 | 2 | | | II-1 | Klra5 | | | 11884 | 2 | | | II-1 | Lztr1 | 8216 | 12-May-15 |
| 11151 | 2 | | | II-1 | Klrc3 | 3823 | 12-May-15 | 11885 | 2 | | | II-1 | Lzts1 | 11178 | 4-May-15 |
| 11152 | 2 | | | II-1 | Klrd1 | 3824 | 12-May-15 | 11889 | 2 | | | II-1 | M6pr | 4074 | 7-Jun-15 |
| 11158 | 2 | | | II-1 | Klrk1 | 22914 | 24-May-15 | 11891 | 2 | | | II-1 | Mab21l1 | 4081 | 4-May-15 |
| 11170 | 2 | | | II-1 | Knstrn | 90417 | 4-May-15 | 11892 | 2 | | | II-1 | Mab21l2 | 10586 | 4-May-15 |
| 11176 | 2 | | | II-1 | Kpna6 | 23633 | 4-May-15 | 11914 | 2 | | | II-1 | Magea1 | 4100 | 4-May-15 |
| 11177 | 2 | | | II-1 | Kpna7 | 402569 | 7-Jun-15 | 11915 | 2 | | | II-1 | Magea10 | 4109 | 4-May-15 |
| 11178 | 2 | | | II-1 | Kpnb1 | 3837 | 4-May-15 | 11916 | 2 | | | II-1 | Magea2 | 4101 | 7-Jun-15 |
| 11181 | 2 | | | II-1 | Kras | 3845 | 7-Jun-15 | 11918 | 2 | | | II-1 | Magea4 | 4103 | 7-Jun-15 |
| 11185 | 2 | | | II-1 | Kremen2 | 79412 | 4-May-15 | 11920 | 2 | | | II-1 | Magea6 | 4105 | 7-Jun-15 |
| 11188 | 2 | | | II-1 | Krr1 | 11103 | 4-May-15 | 11921 | 2 | | | II-1 | Magea8 | 4107 | 12-May-15 |
| 11205 | 2 | | | II-1 | Krt26 | 353288 | 4-May-15 | 11922 | 2 | | | II-1 | Mageb1 | 4112 | 12-May-15 |
| 11300 | 2 | | | II-1 | Kxd1 | 79036 | 4-May-15 | 11924 | 2 | | | II-1 | Mageb16-ps1 | | |
| 11305 | 2 | | | II-1 | L2hgdh | 79944 | 4-May-15 | 11928 | 2 | | | II-1 | Mageb4 | 4115 | 4-May-15 |
| 11309 | 2 | | | II-1 | L3mbtl3 | 84456 | 4-May-15 | 11929 | 2 | | | II-1 | Mageb5 | 347541 | 4-May-15 |
| 11323 | 2 | | | II-1 | Lama2 | 3908 | 4-May-15 | 11930 | 2 | | | II-1 | Maged1 | 9500 | 4-May-15 |
| 11335 | 2 | | | II-1 | Lamp3 | 27074 | 7-Jun-15 | 11944 | 2 | | | II-1 | Mak16 | 84549 | 4-May-15 |
| 11336 | 2 | | | II-1 | Lamp5 | 24141 | 4-May-15 | 11954 | 2 | | | II-1 | Maml2 | 84441 | 4-May-15 |
| 11338 | 2 | | | II-1 | Lamtor2 | 28956 | 4-May-15 | 11961 | 2 | | | II-1 | Man1c1 | 57134 | 4-May-15 |
| 11342 | 2 | | | II-1 | Landl1 | 10314 | 12-May-15 | 11964 | 2 | | | II-1 | Man2b1 | 4125 | 23-May-15 |
| 11361 | 2 | | | II-1 | Lat | 27040 | 7-Jun-15 | 11965 | 2 | | | II-1 | Man2b2 | 23324 | 12-May-15 |
| 11373 | 2 | | | II-1 | Lca5l | 150082 | 12-May-15 | 11970 | 2 | | | II-1 | Manea | 79694 | 4-May-15 |
| 11427 | 2 | | | II-1 | Ldlrad3 | 143458 | 12-May-15 | 11971 | 2 | | | II-1 | Maneal | 149175 | 4-May-15 |
| 11431 | 2 | | | II-1 | Ldoc1l | 84247 | 4-May-15 | 11984 | 2 | | | II-1 | Map2 | 4133 | 4-May-15 |
| 11441 | 2 | | | II-1 | Lemd2 | 221496 | 29-May-15 | 11987 | 2 | | | II-1 | Map2k3 | 5606 | 4-May-15 |
| 11442 | 2 | | | II-1 | Lemd3 | 23592 | 12-May-15 | 11991 | 2 | | | II-1 | Map3k6 | 5608 | 4-May-15 |
| 11443 | 2 | | | II-1 | Lenep | 55891 | 12-May-15 | 11994 | 2 | | | II-1 | Map3k10 | 4294 | 4-May-15 |
| 11446 | 2 | | | II-1 | Leng9 | 94059 | 28-May-15 | 11996 | 2 | | | II-1 | Map3k12 | 7786 | 28-May-15 |

Fig.22 - 104

| | | | | | | | | | | | | | |
|---|---|---|---|---|---|---|---|---|---|---|---|---|---|
| 12001 | 2 | | | II-1 | Map3k2 | 10746 | 4-May-15 | 13249 | 2 | | | II-1 | Mir7032 | | |
| 12002 | 2 | | | II-1 | Map3k3 | 4215 | 24-May-15 | 13334 | 2 | | | II-1 | Mir7211 | | |
| 12003 | 2 | | | II-1 | Map3k4 | 4216 | 4-May-15 | 13378 | 2 | | | II-1 | Mir764 | 100313838 | 4-May-15 |
| 12004 | 2 | | | II-1 | Map3k5 | 4217 | 7-Jun-15 | 13437 | 2 | | | II-1 | Mir8107 | | |
| 12013 | 2 | | | II-1 | Map4k3 | 8491 | 12-May-15 | 13441 | 2 | | | II-1 | Mir8111 | | |
| 12014 | 2 | | | II-1 | Map4k4 | 9448 | 4-May-15 | 13451 | 2 | | | II-1 | Mir872 | | |
| 12022 | 2 | | | II-1 | Mapk1 | 5594 | 7-Jun-15 | 13479 | 2 | | | II-1 | Mirlet7b | 406884 | 21-May-15 |
| 12023 | 2 | | | II-1 | Mapk10 | 5602 | 3-May-15 | 13486 | 2 | | | II-1 | Mirlet7f-2 | | |
| 12024 | 2 | | | II-1 | Mapk11 | 5600 | 4-May-15 | 13496 | 2 | | | II-1 | Mitf | 4286 | 31-May-15 |
| 12031 | 2 | | | II-1 | Mapk3 | 5595 | 7-Jun-15 | 13498 | 2 | | | II-1 | Mki67 | 4288 | 24-May-15 |
| 12035 | 2 | | | II-1 | Mapk8 | 5599 | 7-Jun-15 | 13509 | 2 | | | II-1 | Mks1 | 54903 | 23-May-15 |
| 12036 | 2 | | | II-1 | Mapk8ip1 | 9479 | 4-May-15 | 13517 | 2 | | | II-1 | Mlh3 | 27030 | 4-May-15 |
| 12040 | 2 | | | II-1 | Mapkap1 | 79109 | 2-Jun-15 | 13522 | 2 | | | II-1 | Mllt11 | 10962 | 4-May-15 |
| 12041 | 2 | | | II-1 | Mapkapk2 | 9261 | 3-May-15 | 13523 | 2 | | | II-1 | Mllt3 | 4300 | 12-May-15 |
| 12042 | 2 | | | II-1 | Mapkapk3 | 7867 | 4-May-15 | 13528 | 2 | | | II-1 | Mlx | 6945 | 4-May-15 |
| 12046 | 2 | | | II-1 | Mapre2 | 10982 | 12-May-15 | 13529 | 2 | | | II-1 | Mlxip | 22877 | 4-May-15 |
| 12054 | 2 | | | II-1 | March2 | 51257 | 4-May-15 | 13533 | 2 | | | II-1 | Mmab | 326625 | 23-May-15 |
| 12058 | 2 | | | II-1 | March6 | 10299 | 4-May-15 | 13536 | 2 | | | II-1 | Mmd | 23531 | 4-May-15 |
| 12059 | 2 | | | II-1 | March7 | 64844 | 23-May-15 | 13550 | 2 | | | II-1 | Mmp19 | 4327 | 12-May-15 |
| 12069 | 2 | | | II-1 | Mark3 | 4140 | 21-May-15 | 13553 | 2 | | | II-1 | Mmp2 | 4313 | 24-May-15 |
| 12070 | 2 | | | II-1 | Mark4 | 57787 | 4-May-15 | 13556 | 2 | | | II-1 | Mmp23 | | |
| 12073 | 2 | | | II-1 | Marveld1 | 83742 | 4-May-15 | 13583 | 2 | | | II-1 | Mob3b | 79817 | 4-May-15 |
| 12090 | 2 | | | II-1 | Matn3 | 4148 | 23-May-15 | 13587 | 2 | | | II-1 | Mocos | 55034 | 4-May-15 |
| 12094 | 2 | | | II-1 | Mavs | 57506 | 24-May-15 | 13596 | 2 | | | II-1 | Mon1a | 84315 | 4-May-15 |
| 12095 | 2 | | | II-1 | Max | 4149 | 22-May-15 | 13598 | 2 | | | II-1 | Mon2 | 23041 | 4-May-15 |
| 12096 | 2 | | | II-1 | Maz | 4150 | 4-May-15 | 13599 | 2 | | | II-1 | Morc1 | 27136 | 4-May-15 |
| 12102 | 2 | | | II-1 | Mbd3 | 53615 | 7-Jun-15 | 13600 | 2 | | | II-1 | Morc2a | | |
| 12103 | 2 | | | II-1 | Mbd3l1 | 85509 | 4-May-15 | 13612 | 2 | | | II-1 | Mospd1 | 96180 | 12-May-15 |
| 12104 | 2 | | | II-1 | Mbd3l2 | 125997 | 21-May-15 | 13616 | 2 | | | II-1 | Mov10 | 4343 | 4-May-15 |
| 12105 | 2 | | | II-1 | Mbd4 | 8930 | 12-May-15 | 13642 | 2 | | | II-1 | Mppe1 | 65258 | 12-May-15 |
| 12106 | 2 | | | II-1 | Mbd5 | 55777 | 31-May-15 | 13667 | 2 | | | II-1 | Mrgpra2a | | |
| 12108 | 2 | | | II-1 | Mbip | 51562 | 12-May-15 | 13668 | 2 | | | II-1 | Mrgpra2b | | |
| 12114 | 2 | | | II-1 | Mbnl2 | 10150 | 12-May-15 | 13670 | 2 | | | II-1 | Mrgpra4 | | |
| 12120 | 2 | | | II-1 | Mbp | 4155 | 7-Jun-15 | 13671 | 2 | | | II-1 | Mrgpra6 | | |
| 12122 | 2 | | | II-1 | Mbtps1 | 8720 | 17-May-15 | 13677 | 2 | | | II-1 | Mrgprb5 | | |
| 12127 | 2 | | | II-1 | Mc4r | 4160 | 31-May-15 | 13678 | 2 | | | II-1 | Mrgprb8 | | |
| 12130 | 2 | | | II-1 | Mcat | 27349 | 4-May-15 | 13684 | 2 | | | II-1 | Mrgprx1 | 259249 | 4-May-15 |
| 12135 | 2 | | | II-1 | Mcee | 84693 | 23-May-15 | 13686 | 2 | | | II-1 | Mri1 | 84245 | 4-May-15 |
| 12138 | 2 | | | II-1 | Mcf2l | 23263 | 4-May-15 | 13691 | 2 | | | II-1 | Mroh2b | 133558 | 4-May-15 |
| 12142 | 2 | | | II-1 | Mcl1 | 4170 | 7-Jun-15 | 13692 | 2 | | | II-1 | Mroh4 | | |
| 12155 | 2 | | | II-1 | Mcoln1 | 57192 | 7-Jun-15 | 13693 | 2 | | | II-1 | Mroh5 | 389690 | 4-May-15 |
| 12165 | 2 | | | II-1 | Mcrs1 | 10445 | 12-May-15 | 13695 | 2 | | | II-1 | Mroh7 | 374977 | 4-May-15 |
| 12171 | 2 | | | II-1 | Mcur1 | 63933 | 4-May-15 | 13697 | 2 | | | II-1 | Mroh9 | 80133 | 4-May-15 |
| 12172 | 2 | | | II-1 | Mdc1 | 9656 | 31-May-15 | 13698 | 2 | | | II-1 | Mrpl1 | 65008 | 4-May-15 |
| 12173 | 2 | | | II-1 | Mdh | 4188 | 12-May-15 | 13702 | 2 | | | II-1 | Mrpl13 | 28998 | 21-May-15 |
| 12190 | 2 | | | II-1 | Meaf6 | 64769 | 2-Jun-15 | 13706 | 2 | | | II-1 | Mrpl17 | 63875 | 4-May-15 |
| 12191 | 2 | | | II-1 | Mecom | 2122 | 4-May-15 | 13707 | 2 | | | II-1 | Mrpl18 | 29074 | 7-Jun-15 |
| 12195 | 2 | | | II-1 | Med10 | 84246 | 4-May-15 | 13708 | 2 | | | II-1 | Mrpl19 | 9801 | 4-May-15 |
| 12197 | 2 | | | II-1 | Med12 | 9968 | 24-May-15 | 13717 | 2 | | | II-1 | Mrpl3 | 11222 | 7-Jun-15 |
| 12199 | 2 | | | II-1 | Med13 | 9969 | 4-May-15 | 13718 | 2 | | | II-1 | Mrpl30 | 51263 | 4-May-15 |
| 12202 | 2 | | | II-1 | Med15 | 51586 | 12-May-15 | 13727 | 2 | | | II-1 | Mrpl4 | 51073 | 4-May-15 |
| 12204 | 2 | | | II-1 | Med17 | 9440 | 4-May-15 | 13728 | 2 | | | II-1 | Mrpl40 | 64976 | 4-May-15 |
| 12207 | 2 | | | II-1 | Med20 | 9477 | 2-Jun-15 | 13729 | 2 | | | II-1 | Mrpl43 | 64975 | 4-May-15 |
| 12208 | 2 | | | II-1 | Med21 | 9412 | 4-May-15 | 13732 | 2 | | | II-1 | Mrpl44 | 65080 | 21-May-15 |
| 12211 | 2 | | | II-1 | Med24 | 9862 | 7-Jun-15 | 13733 | 2 | | | II-1 | Mrpl45 | 84311 | 4-May-15 |
| 12212 | 2 | | | II-1 | Med25 | 81857 | 7-Jun-15 | 13740 | 2 | | | II-1 | Mrpl52 | 122704 | 4-May-15 |
| 12213 | 2 | | | II-1 | Med26 | 9441 | 4-May-15 | 13743 | 2 | | | II-1 | Mrpl55 | 128308 | 4-May-15 |
| 12217 | 2 | | | II-1 | Med30 | 90390 | 4-May-15 | 13748 | 2 | | | II-1 | Mrps12 | 6183 | 7-Jun-15 |
| 12239 | 2 | | | II-1 | Meig1 | 644890 | 4-May-15 | 13750 | 2 | | | II-1 | Mrps15 | 64960 | 28-May-15 |
| 12253 | 2 | | | II-1 | Mertk | 10461 | 23-May-15 | 13751 | 2 | | | II-1 | Mrps16 | 51021 | 28-May-15 |
| 12255 | 2 | | | II-1 | Mesdc2 | 23184 | 4-May-15 | 13764 | 2 | | | II-1 | Mrps28 | 28957 | 7-Jun-15 |
| 12262 | 2 | | | II-1 | Metap2 | 10988 | 12-May-15 | 13766 | 2 | | | II-1 | Mrps31 | 10240 | 4-May-15 |
| 12281 | 2 | | | II-1 | Mettl24 | 728464 | 4-May-15 | 13767 | 2 | | | II-1 | Mrps33 | 51650 | 4-May-15 |
| 12287 | 2 | | | II-1 | Mettl7a1 | | | 13771 | 2 | | | II-1 | Mrps5 | 64969 | 12-May-15 |
| 12294 | 2 | | | II-1 | Mex3a | 92312 | 4-May-15 | 13773 | 2 | | | II-1 | Mrps7 | 51081 | 28-May-15 |
| 12328 | 2 | | | II-1 | Mfsd9 | 84804 | 4-May-15 | 13776 | 2 | | | II-1 | Mrs2 | 57380 | 4-May-15 |
| 12333 | 2 | | | II-1 | Mgat2 | 4247 | 23-May-15 | 13782 | 2 | | | II-1 | Ms4a15 | 219995 | 4-May-15 |
| 12364 | 2 | | | II-1 | Micu3 | 286003 | 4-May-15 | 13783 | 2 | | | II-1 | Ms4a18 | 728586 | 4-May-15 |
| 12369 | 2 | | | II-1 | Mief1 | 54471 | 12-May-15 | 13784 | 2 | | | II-1 | Ms4a2 | 2206 | 7-Jun-15 |
| 12370 | 2 | | | II-1 | Mief2 | 125170 | 12-May-15 | 13786 | 2 | | | II-1 | Ms4a4b | | |
| 12373 | 2 | | | II-1 | Mier2 | 54531 | 4-May-15 | 13798 | 2 | | | II-1 | Msantd4 | 84437 | 4-May-15 |
| 12375 | 2 | | | II-1 | Mif | 4282 | 7-Jun-15 | 13799 | 2 | | | II-1 | Msc | 9242 | 7-Jun-15 |
| 12377 | 2 | | | II-1 | Mip | 60672 | 4-May-15 | 13802 | 2 | | | II-1 | Msh3 | 4437 | 4-May-15 |
| 12384 | 2 | | | II-1 | Minpp1 | 9562 | 4-May-15 | 13804 | 2 | | | II-1 | Msh5 | 4439 | 12-May-15 |
| 12386 | 2 | | | II-1 | Miox | 55586 | 4-May-15 | 13809 | 2 | | | II-1 | Msl2 | 55167 | 4-May-15 |
| 12392 | 2 | | | II-1 | Mir1018 | | | 13810 | 2 | | | II-1 | Msl3 | 10943 | 4-May-15 |
| 12437 | 2 | | | II-1 | Mir1306 | 100302197 | 21-May-15 | 13811 | 2 | | | II-1 | Msl3l2 | 151507 | 4-May-15 |
| 12446 | 2 | | | II-1 | Mir134 | 406924 | 21-May-15 | 13838 | 2 | | | II-1 | Mta3 | 57504 | 4-May-15 |
| 12463 | 2 | | | II-1 | Mir145b | | | 13839 | 2 | | | II-1 | Mtag2 | 84677 | 4-May-15 |
| 12484 | 2 | | | II-1 | Mir181a-2 | | | 13840 | 2 | | | II-1 | Mtap | 4507 | 12-May-15 |
| 12556 | 2 | | | II-1 | Mir1960 | | | 13842 | 2 | | | II-1 | Mtbp | 27085 | 4-May-15 |
| 12607 | 2 | | | II-1 | Mir216c | | | 13844 | 2 | | | II-1 | Mtch2 | 23788 | 4-May-15 |
| 12624 | 2 | | | II-1 | Mir24-1 | 407012 | 21-May-15 | 13846 | 2 | | | II-1 | Mtcp1 | 4515 | 7-Jun-15 |
| 12964 | 2 | | | II-1 | Mir6239 | | | 13849 | 2 | | | II-1 | Mterf1b | | |
| 12975 | 2 | | | II-1 | Mir6343 | | | 13852 | 2 | | | II-1 | Mterfd3 | 80298 | 4-May-15 |
| 12995 | 2 | | | II-1 | Mir6366 | | | 13855 | 2 | | | II-1 | Mtfmt | 123263 | 4-May-15 |
| 13014 | 2 | | | II-1 | Mir6388 | | | 13856 | 2 | | | II-1 | Mtfp1 | 51537 | 12-May-15 |
| 13021 | 2 | | | II-1 | Mir6395 | | | 13859 | 2 | | | II-1 | Mtfr2 | 113115 | 4-May-15 |
| 13025 | 2 | | | II-1 | Mir6399 | | | 13870 | 2 | | | II-1 | Mtif3 | 219402 | 4-May-15 |
| 13032 | 2 | | | II-1 | Mir6406 | | | 13871 | 2 | | | II-1 | Mtl5 | 9633 | 12-May-15 |
| 13047 | 2 | | | II-1 | Mir6481 | | | 13872 | 2 | | | II-1 | Mtm1 | 4534 | 23-May-15 |
| 13096 | 2 | | | II-1 | Mir684-2 | | | 13873 | 2 | | | II-1 | Mtmr1 | 8776 | 12-May-15 |
| 13097 | 2 | | | II-1 | Mir686 | | | 13874 | 2 | | | II-1 | Mtmr10 | 54893 | 4-May-15 |
| 13129 | 2 | | | II-1 | Mir6922 | | | 13880 | 2 | | | II-1 | Mtmr4 | 9110 | 24-May-15 |
| 13183 | 2 | | | II-1 | Mir6972 | | | 13881 | 2 | | | II-1 | Mtmr6 | 9107 | 4-May-15 |
| 13208 | 2 | | | II-1 | Mir6995 | | | 13882 | 2 | | | II-1 | Mtmr7 | 9108 | 12-May-15 |
| 13214 | 2 | | | II-1 | Mir7000 | | | 13886 | 2 | | | II-1 | Mto1 | 25821 | 12-May-15 |

Fig.22 - 105

| | | | | | | | | | | | | | | |
|---|---|---|---|---|---|---|---|---|---|---|---|---|---|---|
| 13887 | 2 | | | II-1 | Mtor | 2475 | 31-May-15 | 14544 | 2 | | | II-1 | Npas2 | 4862 | 4-May-15 |
| 13895 | 2 | | | II-1 | Mtss1l | 92154 | 4-May-15 | 14559 | 2 | | | II-1 | Npffr2 | 10886 | 4-May-15 |
| 14001 | 2 | | | II-1 | Myl12b | 103910 | 4-May-15 | 14560 | 2 | | | II-1 | Nphp1 | 4867 | 23-May-15 |
| 14023 | 2 | | | II-1 | Myo1b | 4430 | 4-May-15 | 14564 | 2 | | | II-1 | Nphs1os | | |
| 14038 | 2 | | | II-1 | Myo9a | 4649 | 4-May-15 | 14565 | 2 | | | II-1 | Nphs2 | 7827 | 12-May-15 |
| 14039 | 2 | | | II-1 | Myo9b | 4650 | 4-May-15 | 14582 | 2 | | | II-1 | Npsr1 | 387129 | 31-May-15 |
| 14055 | 2 | | | II-1 | Myrf | 196446 | 12-May-15 | 14583 | 2 | | | II-1 | Nptn | 27020 | 4-May-15 |
| 14056 | 2 | | | II-1 | Myrip | 25924 | 4-May-15 | 14593 | 2 | | | II-1 | Npy5r | 4889 | 4-May-15 |
| 14058 | 2 | | | II-1 | Myt1 | 4661 | 7-Jun-15 | 14594 | 2 | | | II-1 | Npy6r | 4888 | 4-May-15 |
| 14059 | 2 | | | II-1 | Myt1l | 23040 | 12-May-15 | 14597 | 2 | | | II-1 | Nr0b1 | 190 | 23-May-15 |
| 14060 | 2 | | | II-1 | Myzap | 100820829 | 4-May-15 | 14602 | 2 | | | II-1 | Nr1h3 | 10062 | 31-May-15 |
| 14070 | 2 | | | II-1 | N4bp3 | 23138 | 4-May-15 | 14622 | 2 | | | II-1 | Nr6a1 | 2649 | 4-May-15 |
| 14073 | 2 | | | II-1 | Naa10 | 8260 | 23-May-15 | 14628 | 2 | | | II-1 | Nrbp1 | 29959 | 4-May-15 |
| 14076 | 2 | | | II-1 | Naa16 | 79612 | 12-May-15 | 14631 | 2 | | | II-1 | Nrd1 | 4898 | 12-May-15 |
| 14079 | 2 | | | II-1 | Naa30 | 122830 | 4-May-15 | 14645 | 2 | | | II-1 | Nrl | 4901 | 23-May-15 |
| 14081 | 2 | | | II-1 | Naa38 | 84316 | 7-Jun-15 | 14646 | 2 | | | II-1 | Nrm | 11270 | 4-May-15 |
| 14084 | 2 | | | II-1 | Naa60 | 79903 | 4-May-15 | 14665 | 2 | | | II-1 | Nsg1 | 27065 | 4-May-15 |
| 14086 | 2 | | | II-1 | Naalad2 | 10003 | 4-May-15 | 14670 | 2 | | | II-1 | Nsmce2 | 286053 | 17-May-15 |
| 14089 | 2 | | | II-1 | Nab2 | 4665 | 24-May-15 | 14674 | 2 | | | II-1 | Nsun3 | 63899 | 4-May-15 |
| 14099 | 2 | | | II-1 | Nae1 | 8883 | 12-May-15 | 14685 | 2 | | | II-1 | Nt5dc1 | 221294 | 4-May-15 |
| 14101 | 2 | | | II-1 | Naga | 4668 | 4-May-15 | 14704 | 2 | | | II-1 | Ntrk2 | 4915 | 4-May-15 |
| 14102 | 2 | | | II-1 | Nagk | 55577 | 4-May-15 | 14713 | 2 | | | II-1 | Nubp2 | 10101 | 4-May-15 |
| 14103 | 2 | | | II-1 | Naglu | 4669 | 4-May-15 | 14714 | 2 | | | II-1 | Nubpl | 80224 | 4-May-15 |
| 14115 | 2 | | | II-1 | Nanos1 | 340719 | 4-May-15 | 14720 | 2 | | | II-1 | Nudcd2 | 134492 | 4-May-15 |
| 14116 | 2 | | | II-1 | Nanos2 | 339345 | 4-May-15 | 14721 | 2 | | | II-1 | Nudcd3 | 23386 | 4-May-15 |
| 14118 | 2 | | | II-1 | Nanp | 140838 | 4-May-15 | 14729 | 2 | | | II-1 | Nudt16 | 131870 | 4-May-15 |
| 14134 | 2 | | | II-1 | Nars | 4677 | 4-May-15 | 14740 | 2 | | | II-1 | Nudt6 | 11162 | 12-May-15 |
| 14137 | 2 | | | II-1 | Nat1 | 9 | 7-Jun-15 | 14752 | 2 | | | II-1 | Nup133 | 55746 | 4-May-15 |
| 14142 | 2 | | | II-1 | Nat6 | 24142 | 7-Jun-15 | 14753 | 2 | | | II-1 | Nup153 | 9972 | 4-May-15 |
| 14155 | 2 | | | II-1 | Nbr1 | 4077 | 24-May-15 | 14754 | 2 | | | II-1 | Nup155 | 9631 | 4-May-15 |
| 14156 | 2 | | | II-1 | Ncald | 83988 | 4-May-15 | 14755 | 2 | | | II-1 | Nup160 | 23279 | 4-May-15 |
| 14160 | 2 | | | II-1 | Ncapd2 | 9918 | 21-May-15 | 14761 | 2 | | | II-1 | Nup35 | 129401 | 4-May-15 |
| 14177 | 2 | | | II-1 | Nckap1l | 3071 | 4-May-15 | 14765 | 2 | | | II-1 | Nup54 | 53371 | 4-May-15 |
| 14183 | 2 | | | II-1 | Ncln | 56926 | 3-May-15 | 14766 | 2 | | | II-1 | Nup62 | 23636 | 4-May-15 |
| 14185 | 2 | | | II-1 | Ncoa2 | 10499 | 17-May-15 | 14767 | 2 | | | II-1 | Nup62cl | 54830 | 4-May-15 |
| 14187 | 2 | | | II-1 | Ncoa4 | 8031 | 4-May-15 | 14768 | 2 | | | II-1 | Nup62-il4i1 | | |
| 14188 | 2 | | | II-1 | Ncoa5 | 57727 | 4-May-15 | 14770 | 2 | | | II-1 | Nup88 | 4927 | 4-May-15 |
| 14189 | 2 | | | II-1 | Ncoa6 | 23054 | 4-May-15 | 14771 | 2 | | | II-1 | Nup93 | 9688 | 28-May-15 |
| 14193 | 2 | | | II-1 | Ncr1 | 9437 | 4-May-15 | 14772 | 2 | | | II-1 | Nup98 | 4928 | 4-May-15 |
| 14203 | 2 | | | II-1 | Ndc | 4692 | 23-May-15 | 14783 | 2 | | | II-1 | Nwd1 | 284434 | 9-May-15 |
| 14204 | 2 | | | II-1 | Ndnf | 79625 | 4-May-15 | 14785 | 2 | | | II-1 | Nxf1 | 10482 | 1-Jun-15 |
| 14215 | 2 | | | II-1 | Ndst4 | 64579 | 4-May-15 | 14786 | 2 | | | II-1 | Nxf2 | 56001 | 14-May-15 |
| 14216 | 2 | | | II-1 | Ndufa1 | 4694 | 3-May-15 | 14789 | 2 | | | II-1 | Nxn | 64359 | 4-May-15 |
| 14221 | 2 | | | II-1 | Ndufa2 | 4695 | 23-May-15 | 14798 | 2 | | | II-1 | Nxph3 | 11248 | 12-May-15 |
| 14230 | 2 | | | II-1 | Ndufab1 | 4706 | 4-May-15 | 14802 | 2 | | | II-1 | Nyap1 | 222950 | 4-May-15 |
| 14239 | 2 | | | II-1 | Ndufb11 | 54539 | 31-May-15 | 14803 | 2 | | | II-1 | Nyap2 | 57624 | 4-May-15 |
| 14245 | 2 | | | II-1 | Ndufb7 | 4713 | 4-May-15 | 14829 | 2 | | | II-1 | Obox3 | | |
| 14246 | 2 | | | II-1 | Ndufb8 | 4714 | 23-May-15 | 14839 | 2 | | | II-1 | Ocel1 | 79629 | 4-May-15 |
| 14269 | 2 | | | II-1 | Nedd1 | 121441 | 4-May-15 | 14857 | 2 | | | II-1 | Ofd1 | 8481 | 31-May-15 |
| 14270 | 2 | | | II-1 | Nedd4 | 4734 | 4-May-15 | 14866 | 2 | | | II-1 | Ogn | 4969 | 12-May-15 |
| 14294 | 2 | | | II-1 | Nelfcd | 51497 | 4-May-15 | 14872 | 2 | | | II-1 | Olah | 55301 | 4-May-15 |
| 14295 | 2 | | | II-1 | Nelfe | 7936 | 12-May-15 | 14873 | 2 | | | II-1 | Olfm1 | 10439 | 4-May-15 |
| 14301 | 2 | | | II-1 | Neo1 | 4756 | 4-May-15 | 14883 | 2 | | | II-1 | Olfr100 | | |
| 14322 | 2 | | | II-1 | Neurog2 | 63973 | 4-May-15 | 14914 | 2 | | | II-1 | Olfr1038-ps | | |
| 14327 | 2 | | | II-1 | Nfam1 | 150372 | 4-May-15 | 14978 | 2 | | | II-1 | Olfr1122 | | |
| 14334 | 2 | | | II-1 | Nfatc4 | 4776 | 24-May-15 | 15109 | 2 | | | II-1 | Olfr1272 | | |
| 14353 | 2 | | | II-1 | Nfs1 | 9054 | 4-May-15 | 15119 | 2 | | | II-1 | Olfr1281 | | |
| 14354 | 2 | | | II-1 | Nfu1 | 27247 | 2-Jun-15 | 15120 | 2 | | | II-1 | Olfr1282 | | |
| 14356 | 2 | | | II-1 | Nfxl1 | 152518 | 12-May-15 | 15137 | 2 | | | II-1 | Olfr1301 | | |
| 14357 | 2 | | | II-1 | Nfya | 4800 | 4-May-15 | 15173 | 2 | | | II-1 | Olfr1340 | | |
| 14358 | 2 | | | II-1 | Nfyb | 4801 | 4-May-15 | 15179 | 2 | | | II-1 | Olfr1348 | | |
| 14372 | 2 | | | II-1 | Nhlrc1 | 378884 | 23-May-15 | 15205 | 2 | | | II-1 | Olfr1378 | | |
| 14386 | 2 | | | II-1 | Nim1k | 167359 | 4-May-15 | 15213 | 2 | | | II-1 | Olfr1386 | | |
| 14397 | 2 | | | II-1 | Nipal4 | 348938 | 23-May-15 | 15224 | 2 | | | II-1 | Olfr1396 | | |
| 14404 | 2 | | | II-1 | Nit2 | 56954 | 12-May-15 | 15227 | 2 | | | II-1 | Olfr1404 | | |
| 14408 | 2 | | | II-1 | Nkain4 | 128414 | 4-May-15 | 15241 | 2 | | | II-1 | Olfr142 | | |
| 14416 | 2 | | | II-1 | Nkpd1 | 284353 | 4-May-15 | 15245 | 2 | | | II-1 | Olfr1425 | | |
| 13420 | 2 | | | II-1 | Nkx1-2 | 390010 | 4-May-15 | 15310 | 2 | | | II-1 | Olfr151 | | |
| 14421 | 2 | | | II-1 | Nkx2-1 | 7080 | 23-May-15 | 15332 | 2 | | | II-1 | Olfr168 | | |
| 14427 | 2 | | | II-1 | Nkx2-6 | 137814 | 4-May-15 | 15349 | 2 | | | II-1 | Olfr19 | | |
| 14428 | 2 | | | II-1 | Nkx2-8 | 26257 | 12-May-15 | 15352 | 2 | | | II-1 | Olfr192 | | |
| 14432 | 2 | | | II-1 | Nkx6-2 | 84504 | 4-May-15 | 15362 | 2 | | | II-1 | Olfr201 | | |
| 14441 | 2 | | | II-1 | Nlrc4 | 58484 | 12-May-15 | 15373 | 2 | | | II-1 | Olfr215 | | |
| 14442 | 2 | | | II-1 | Nlrc5 | 84166 | 10-May-15 | 15376 | 2 | | | II-1 | Olfr221 | | |
| 14450 | 2 | | | II-1 | Nlrp3 | 114548 | 24-May-15 | 15386 | 2 | | | II-1 | Olfr237-ps1 | | |
| 14453 | 2 | | | II-1 | Nlrp4c | | | 15414 | 2 | | | II-1 | Olfr290 | | |
| 14456 | 2 | | | II-1 | Nlrp4g | | | 15430 | 2 | | | II-1 | Olfr307 | | |
| 14458 | 2 | | | II-1 | Nlrp5-ps | | | 15436 | 2 | | | II-1 | Olfr312 | | |
| 14462 | 2 | | | II-1 | Nlrp9c | | | 15443 | 2 | | | II-1 | Olfr319 | | |
| 14467 | 2 | | | II-1 | Nme1 | 4830 | 7-Jun-15 | 15444 | 2 | | | II-1 | Olfr32 | | |
| 14476 | 2 | | | II-1 | Nmi | 9111 | 7-Jun-15 | 15456 | 2 | | | II-1 | Olfr338 | | |
| 14481 | 2 | | | II-1 | Nmrk1 | 54981 | 4-May-15 | 15520 | 2 | | | II-1 | Olfr426 | | |
| 14485 | 2 | | | II-1 | Nmt2 | 9397 | 12-May-15 | 15529 | 2 | | | II-1 | Olfr437 | | |
| 14493 | 2 | | | II-1 | Nob1 | 28987 | 17-May-15 | 15621 | 2 | | | II-1 | Olfr544 | | |
| 14494 | 2 | | | II-1 | Nobox | 135935 | 28-May-15 | 15623 | 2 | | | II-1 | Olfr547 | | |
| 14495 | 2 | | | II-1 | Noc2l | | | 15625 | 2 | | | II-1 | Olfr55 | | |
| 14498 | 2 | | | II-1 | Nod1 | 10392 | 29-May-15 | 15629 | 2 | | | II-1 | Olfr553 | | |
| 14500 | 2 | | | II-1 | Nodal | 4838 | 29-May-15 | 15633 | 2 | | | II-1 | Olfr557 | | |
| 14501 | 2 | | | II-1 | Nog | 9241 | 13-May-15 | 15637 | 2 | | | II-1 | Olfr560 | | |
| 14505 | 2 | | | II-1 | Nol3 | 8996 | 24-May-15 | 15762 | 2 | | | II-1 | Olfr704 | | |
| 14508 | 2 | | | II-1 | Nol7 | 51406 | 4-May-15 | 15787 | 2 | | | II-1 | Olfr734 | | |
| 14509 | 2 | | | II-1 | Nol8 | 55035 | 4-May-15 | 15789 | 2 | | | II-1 | Olfr736 | | |
| 14513 | 2 | | | II-1 | Nomo1 | 23420 | 4-May-15 | 15824 | 2 | | | II-1 | Olfr782 | | |
| 14514 | 2 | | | II-1 | Nono | 4841 | 1-Jun-15 | 15939 | 2 | | | II-1 | Olfr923 | | |
| 14515 | 2 | | | II-1 | Nop10 | 55505 | 31-May-15 | 15980 | 2 | | | II-1 | Olfr979 | | |
| 14516 | 2 | | | II-1 | Nop14 | 8602 | 12-May-15 | 15994 | 2 | | | II-1 | Olfr994 | | |
| 14527 | 2 | | | II-1 | Nostrin | 115677 | 4-May-15 | 16011 | 2 | | | II-1 | Ooep | 441161 | 4-May-15 |

Fig.22 - 106

| | | | | | | | | | | | | | |
|---|---|---|---|---|---|---|---|---|---|---|---|---|---|
| 16013 | 2 | | | II-1 | Oog2 | | | 16448 | 2 | | | II-1 | Pde6g | 5148 | 23-May-15 |
| 16014 | 2 | | | II-1 | Oog3 | | | 16452 | 2 | | | II-1 | Pde8a | 5151 | 4-May-15 |
| 16023 | 2 | | | II-1 | Ophn1 | 4983 | 12-May-15 | 16465 | 2 | | | II-1 | Pdhb | 5162 | 12-May-15 |
| 16027 | 2 | | | II-1 | Opn3 | 23596 | 12-May-15 | 16505 | 2 | | | II-1 | Pdzd8 | 118987 | 4-May-15 |
| 16030 | 2 | | | II-1 | Oprd1 | 4985 | 4-May-15 | 16517 | 2 | | | II-1 | Pecam1 | 5175 | 17-May-15 |
| 16031 | 2 | | | II-1 | Oprk1 | 4986 | 12-May-15 | 16518 | 2 | | | II-1 | Pecr | 55825 | 4-May-15 |
| 16033 | 2 | | | II-1 | Oprm1 | 4988 | 31-May-15 | 16528 | 2 | | | II-1 | Pelo | 53918 | 4-May-15 |
| 16043 | 2 | | | II-1 | Orc4 | 5000 | 4-May-15 | 16546 | 2 | | | II-1 | Pex10 | 5192 | 4-May-15 |
| 16044 | 2 | | | II-1 | Orc5 | 5001 | 4-May-15 | 16552 | 2 | | | II-1 | Pex14 | 5195 | 4-May-15 |
| 16053 | 2 | | | II-1 | Osbp | 5007 | 28-May-15 | 16556 | 2 | | | II-1 | Pex26 | 55670 | 4-May-15 |
| 16064 | 2 | | | II-1 | Osbpl9 | 114883 | 12-May-15 | 16557 | 2 | | | II-1 | Pex3 | 8504 | 28-May-15 |
| 16086 | 2 | | | II-1 | Otdd1 | 131149 | 4-May-15 | 16559 | 2 | | | II-1 | Pex5l | 51555 | 3-Jun-15 |
| 16092 | 2 | | | II-1 | Otp | 23440 | 4-May-15 | 16560 | 2 | | | II-1 | Pex6 | 5190 | 23-May-15 |
| 16093 | 2 | | | II-1 | Ott | 64783 | 4-May-15 | 16588 | 2 | | | II-1 | Pgbd5 | 79605 | 4-May-15 |
| 16102 | 2 | | | II-1 | Otud6b | 51633 | 4-May-15 | 16617 | 2 | | | II-1 | Phax | 51808 | 4-May-15 |
| 16103 | 2 | | | II-1 | Otud7a | 161725 | 4-May-15 | 16618 | 2 | | | II-1 | Phb | 5245 | 23-May-15 |
| 16107 | 2 | | | II-1 | Otx2 | 5015 | 28-May-15 | 16619 | 2 | | | II-1 | Phb2 | 11331 | 1-Jun-15 |
| 16109 | 2 | | | II-1 | Ovca2 | 124641 | 4-May-15 | 16620 | 2 | | | II-1 | Phc1 | 1911 | 4-May-15 |
| 16116 | 2 | | | II-1 | Oxct1 | 5019 | 12-May-15 | 16622 | 2 | | | II-1 | Phc3 | 80012 | 12-May-15 |
| 16118 | 2 | | | II-1 | Oxct2b | | | 16632 | 2 | | | II-1 | Phf14 | 9678 | 12-May-15 |
| 16120 | 2 | | | II-1 | Oxld1 | 339229 | 12-May-15 | 16637 | 2 | | | II-1 | Phf21a | 51317 | 4-May-15 |
| 16123 | 2 | | | II-1 | Oxsm | 54995 | 4-May-15 | 16664 | 2 | | | II-1 | Phox2b | 8929 | 28-May-15 |
| 16124 | 2 | | | II-1 | Oxsr1 | 9943 | 12-May-15 | 16667 | 2 | | | II-1 | Phtf1 | 10745 | 4-May-15 |
| 16130 | 2 | | | II-1 | P2rx4 | 5025 | 12-May-15 | 16671 | 2 | | | II-1 | Phyh | 5264 | 23-May-15 |
| 16146 | 2 | | | II-1 | P4htm | 54681 | 12-May-15 | 16685 | 2 | | | II-1 | Pias3 | 10401 | 4-May-15 |
| 16148 | 2 | | | II-1 | Pabpc1 | 26986 | 12-May-15 | 16687 | 2 | | | II-1 | Pibf1 | 10464 | 4-May-15 |
| 16149 | 2 | | | II-1 | Pabpc1l | 80336 | 4-May-15 | 16690 | 2 | | | II-1 | Pid1 | 55022 | 3-May-15 |
| 16151 | 2 | | | II-1 | Pabpc4 | 8761 | 4-May-15 | 16695 | 2 | | | II-1 | Pifo | 128344 | 4-May-15 |
| 16152 | 2 | | | II-1 | Pabpc4l | 132430 | 12-May-15 | 16704 | 2 | | | II-1 | Pigm | 93183 | 4-May-15 |
| 16154 | 2 | | | II-1 | Pabpc6 | | | 16705 | 2 | | | II-1 | Pign | 23556 | 31-May-15 |
| 16157 | 2 | | | II-1 | Pacrg | 135138 | 4-May-15 | 16714 | 2 | | | II-1 | Pigw | 284098 | 4-May-15 |
| 16167 | 2 | | | II-1 | Padi4 | 23569 | 21-May-15 | 16715 | 2 | | | II-1 | Pigx | 54965 | 4-May-15 |
| 16170 | 2 | | | II-1 | Pafah1b1 | 5048 | 23-May-15 | 16717 | 2 | | | II-1 | Pigz | 80235 | 4-May-15 |
| 16171 | 2 | | | II-1 | Pafah1b2 | 5049 | 2-Jun-15 | 16718 | 2 | | | II-1 | Pih1d1 | 55011 | 4-May-15 |
| 16179 | 2 | | | II-1 | Paip2 | 51247 | 4-May-15 | 16721 | 2 | | | II-1 | Pik3ap1 | 118788 | 4-May-15 |
| 16180 | 2 | | | II-1 | Paip2b | 400961 | 4-May-15 | 16728 | 2 | | | II-1 | Pik3cd | 5293 | 7-Jun-15 |
| 16181 | 2 | | | II-1 | Pak1 | 5058 | 7-Jun-15 | 16733 | 2 | | | II-1 | Pik3r3 | 8503 | 28-May-15 |
| 16184 | 2 | | | II-1 | Pak3 | 5063 | 7-Jun-15 | 16736 | 2 | | | II-1 | Pik3r6 | 146850 | 4-May-15 |
| 16188 | 2 | | | II-1 | Palb2 | 79728 | 24-May-15 | 16739 | 2 | | | II-1 | Pilrb1 | | |
| 16189 | 2 | | | II-1 | Pald1 | 27143 | 4-May-15 | 16765 | 2 | | | II-1 | Pira6 | | |
| 16210 | 2 | | | II-1 | Papd7 | 11044 | 4-May-15 | 16772 | 2 | | | II-1 | Pisd-ps3 | | |
| 16211 | 2 | | | II-1 | Papl | 390928 | 4-May-15 | 16775 | 2 | | | II-1 | Pitpnb | 23760 | 4-May-15 |
| 16233 | 2 | | | II-1 | Park2 | 5071 | 31-May-15 | 16776 | 2 | | | II-1 | Pitpnc1 | 26207 | 4-May-15 |
| 16239 | 2 | | | II-1 | Parp10 | 84875 | 4-May-15 | 16779 | 2 | | | II-1 | Pitpnm2os1 | | |
| 16240 | 2 | | | II-1 | Parp11 | 57097 | 2-Jun-15 | 16786 | 2 | | | II-1 | Piwil2 | 55124 | 4-May-15 |
| 16243 | 2 | | | II-1 | Parp16 | 54956 | 4-May-15 | 16787 | 2 | | | II-1 | Piwil4 | 143689 | 4-May-15 |
| 16246 | 2 | | | II-1 | Parp4 | 143 | 4-May-15 | 16793 | 2 | | | II-1 | Pkd2 | 5311 | 7-Jun-15 |
| 16247 | 2 | | | II-1 | Parp6 | 56965 | 12-May-15 | 16799 | 2 | | | II-1 | Pkhd1l1 | 93035 | 12-May-15 |
| 16258 | 2 | | | II-1 | Patl1 | 219988 | 4-May-15 | 16809 | 2 | | | II-1 | Pknox1 | 5316 | 4-May-15 |
| 16259 | 2 | | | II-1 | Patl2 | 197135 | 4-May-15 | 16820 | 2 | | | II-1 | Pla2g15 | 23659 | 4-May-15 |
| 16260 | 2 | | | II-1 | Patz1 | 23598 | 4-May-15 | 16821 | 2 | | | II-1 | Pla2g16 | 11145 | 4-May-15 |
| 16266 | 2 | | | II-1 | Pax4 | 5078 | 4-May-15 | 16855 | 2 | | | II-1 | Plcb2 | 5330 | 4-May-15 |
| 16270 | 2 | | | II-1 | Pax7 | 5081 | 12-May-15 | 16861 | 2 | | | II-1 | Plce1 | 51196 | 31-May-15 |
| 16276 | 2 | | | II-1 | Pbk | 55872 | 24-May-15 | 16874 | 2 | | | II-1 | Pld3 | 23646 | 12-May-15 |
| 16287 | 2 | | | II-1 | Pcbd1 | 5092 | 4-May-15 | 16879 | 2 | | | II-1 | Plec | 5339 | 23-May-15 |
| 16294 | 2 | | | II-1 | Pccb | 5096 | 23-May-15 | 16892 | 2 | | | II-1 | Plekhd1 | 400224 | 4-May-15 |
| 16301 | 2 | | | II-1 | Pcdh18 | 54510 | 12-May-15 | 16897 | 2 | | | II-1 | Plekhg2 | 64857 | 4-May-15 |
| 16309 | 2 | | | II-1 | Pcdha11 | 56138 | 4-May-15 | 16899 | 2 | | | II-1 | Plekhg4 | 25894 | 17-May-15 |
| 16311 | 2 | | | II-1 | Pcdha2 | 56146 | 4-May-15 | 16907 | 2 | | | II-1 | Plekhm2 | 23207 | 29-May-15 |
| 16312 | 2 | | | II-1 | Pcdha3 | 56145 | 4-May-15 | 16908 | 2 | | | II-1 | Plekhm3 | 389072 | 21-May-15 |
| 16313 | 2 | | | II-1 | Pcdha4 | 56144 | 4-May-15 | 16909 | 2 | | | II-1 | Plekhn1 | 84069 | 4-May-15 |
| 16314 | 2 | | | II-1 | Pcdha4-g | | | 16911 | 2 | | | II-1 | Plekho2 | 80301 | 12-May-15 |
| 16315 | 2 | | | II-1 | Pcdha5 | 56143 | 4-May-15 | 16940 | 2 | | | II-1 | Plscr4 | 57088 | 4-May-15 |
| 16316 | 2 | | | II-1 | Pcdha6 | 56142 | 4-May-15 | 16945 | 2 | | | II-1 | Plxdc2 | 84898 | 4-May-15 |
| 16318 | 2 | | | II-1 | Pcdha8 | 56140 | 4-May-15 | 16951 | 2 | | | II-1 | Plxnb1 | 5364 | 4-May-15 |
| 16319 | 2 | | | II-1 | Pcdha9 | 9752 | 4-May-15 | 16954 | 2 | | | II-1 | Plxnc1 | 10154 | 4-May-15 |
| 16320 | 2 | | | II-1 | Pcdhac1 | 56135 | 4-May-15 | 16965 | 2 | | | II-1 | Pml | 5371 | 21-May-15 |
| 16324 | 2 | | | II-1 | Pcdhb11 | 56125 | 4-May-15 | 16966 | 2 | | | II-1 | Pmm1 | 5372 | 4-May-15 |
| 16325 | 2 | | | II-1 | Pcdhb12 | 56124 | 4-May-15 | 16968 | 2 | | | II-1 | Pmp2 | 5375 | 4-May-15 |
| 16326 | 2 | | | II-1 | Pcdhb13 | 56123 | 4-May-15 | 16972 | 2 | | | II-1 | Pms1 | 5378 | 23-May-15 |
| 16330 | 2 | | | II-1 | Pcdhb17 | 54861 | 12-May-15 | 16978 | 2 | | | II-1 | Pnkp | 11284 | 17-May-15 |
| 16333 | 2 | | | II-1 | Pcdhb2 | 56133 | 12-May-15 | 16979 | 2 | | | II-1 | Pnldc1 | 154197 | 4-May-15 |
| 16334 | 2 | | | II-1 | Pcdhb20 | | | 16987 | 2 | | | II-1 | Pnmal1 | 55228 | 4-May-15 |
| 16335 | 2 | | | II-1 | Pcdhb21 | | | 16988 | 2 | | | II-1 | Pnmal2 | 57469 | 4-May-15 |
| 16337 | 2 | | | II-1 | Pcdhb3 | 56132 | 4-May-15 | 16991 | 2 | | | II-1 | Pno1 | 56902 | 12-May-15 |
| 16339 | 2 | | | II-1 | Pcdhb5 | 25197 | 4-May-15 | 16993 | 2 | | | II-1 | Pnp | 4860 | 7-Jun-15 |
| 16340 | 2 | | | II-1 | Pcdhb6 | 56130 | 21-May-15 | 17006 | 2 | | | II-1 | Poc1a | 25886 | 4-May-15 |
| 16342 | 2 | | | II-1 | Pcdhb8 | 56128 | 4-May-15 | 17015 | 2 | | | II-1 | Pofut2 | 23275 | 12-May-15 |
| 16343 | 2 | | | II-1 | Pcdhb9 | 56127 | 4-May-15 | 17016 | 2 | | | II-1 | Pogk | 57645 | 4-May-15 |
| 16344 | 2 | | | II-1 | Pcdhga1 | 56114 | 4-May-15 | 17018 | 2 | | | II-1 | Pogz | 23126 | 23-May-15 |
| 16352 | 2 | | | II-1 | Pcdhga6 | 56109 | 4-May-15 | 17019 | 2 | | | II-1 | Pola1 | 5422 | 12-May-15 |
| 16355 | 2 | | | II-1 | Pcdhga9 | 56107 | 4-May-15 | 17020 | 2 | | | II-1 | Pola2 | 23649 | 4-May-15 |
| 16383 | 2 | | | II-1 | Pcna | 5111 | 17-May-15 | 17025 | 2 | | | II-1 | Pold4 | 57804 | 7-Jun-15 |
| 16384 | 2 | | | II-1 | Pcnp | 57092 | 4-May-15 | 17027 | 2 | | | II-1 | Poldip3 | 84271 | 4-May-15 |
| 16389 | 2 | | | II-1 | Pcnxl4 | 64430 | 4-May-15 | 17028 | 2 | | | II-1 | Pole | 5426 | 17-May-15 |
| 16414 | 2 | | | II-1 | Pdcd1 | 5133 | 24-May-15 | 17035 | 2 | | | II-1 | Poli | 11201 | 4-May-15 |
| 16415 | 2 | | | II-1 | Pdcd10 | 11235 | 23-May-15 | 17039 | 2 | | | II-1 | Poln | 353497 | 4-May-15 |
| 16418 | 2 | | | II-1 | Pdcd2 | 5134 | 4-May-15 | 17043 | 2 | | | II-1 | Polr1c | 9533 | 7-Jun-15 |
| 16420 | 2 | | | II-1 | Pdcd4 | 27250 | 31-May-15 | 17045 | 2 | | | II-1 | Polr1e | 64425 | 4-May-15 |
| 16424 | 2 | | | II-1 | Pdcd7 | 10081 | 4-May-15 | 17048 | 2 | | | II-1 | Polr2c | 5432 | 4-May-15 |
| 16425 | 2 | | | II-1 | Pdcl | 5082 | 3-May-15 | 17049 | 2 | | | II-1 | Polr2d | 5433 | 4-May-15 |
| 16426 | 2 | | | II-1 | Pdcl2 | 132954 | 4-May-15 | 17050 | 2 | | | II-1 | Polr2e | 5434 | 4-May-15 |
| 16429 | 2 | | | II-1 | Pde10a | 10846 | 4-May-15 | 17060 | 2 | | | II-1 | Polr3b | 55703 | 2-Jun-15 |
| 16430 | 2 | | | II-1 | Pde11a | 50940 | 12-May-15 | 17061 | 2 | | | II-1 | Polr3c | 10623 | 12-May-15 |
| 16431 | 2 | | | II-1 | Pde12 | 201626 | 4-May-15 | 17065 | 2 | | | II-1 | Polr3g | 10622 | 12-May-15 |
| 16432 | 2 | | | II-1 | Pde1a | 5136 | 14-May-15 | 17069 | 2 | | | II-1 | Polrmt | 5442 | 4-May-15 |
| 16447 | 2 | | | II-1 | Pde6d | 5147 | 12-May-15 | 17072 | 2 | | | II-1 | Pom121l2 | 94026 | 4-May-15 |

Fig.22 - 107

| | | | | | | | | | | | | | |
|---|---|---|---|---|---|---|---|---|---|---|---|---|---|
| 17077 | 2 | | | II-1 | Pomp | 51371 | 7-Jun-15 | 17522 | 2 | | | II-1 | Prss58 | 136541 | 4-May-15 |
| 17079 | 2 | | | II-1 | Pomt2 | 29954 | 23-May-15 | 17525 | 2 | | | II-1 | Prtn3 | 5657 | 17-May-15 |
| 17095 | 2 | | | II-1 | Pou1f1 | 5449 | 4-May-15 | 17540 | 2 | | | II-1 | Psg16 | | |
| 17105 | 2 | | | II-1 | Pou4f1 | 5457 | 28-May-15 | 17543 | 2 | | | II-1 | Psg19 | | |
| 17106 | 2 | | | II-1 | Pou4f2 | 5458 | 28-May-15 | 17546 | 2 | | | II-1 | Psg22 | | |
| 17107 | 2 | | | II-1 | Pou4f3 | 5459 | 28-May-15 | 17551 | 2 | | | II-1 | Psg28 | | |
| 17108 | 2 | | | II-1 | Pou5f1 | 5460 | 24-May-15 | 17558 | 2 | | | II-1 | Psma3 | 5684 | 4-May-15 |
| 17109 | 2 | | | II-1 | Pou5f2 | 134187 | 4-May-15 | 17563 | 2 | | | II-1 | Psma8 | 143471 | 12-May-15 |
| 17110 | 2 | | | II-1 | Pou6f1 | 5463 | 4-May-15 | 17564 | 2 | | | II-1 | Psmb1 | 5689 | 4-May-15 |
| 17111 | 2 | | | II-1 | Pou6f2 | 11281 | 4-May-15 | 17565 | 2 | | | II-1 | Psmb10 | 5699 | 4-May-15 |
| 17113 | 2 | | | II-1 | Ppa1 | 5464 | 4-May-15 | 17578 | 2 | | | II-1 | Psmc3ip | 29893 | 4-May-15 |
| 17135 | 2 | | | II-1 | Ppfia1 | 8500 | 4-May-15 | 17583 | 2 | | | II-1 | Psmd10 | 5716 | 4-May-15 |
| 17136 | 2 | | | II-1 | Ppfia2 | 8499 | 4-May-15 | 17584 | 2 | | | II-1 | Psmd11 | 5717 | 4-May-15 |
| 17137 | 2 | | | II-1 | Ppfia3 | 8541 | 4-May-15 | 17586 | 2 | | | II-1 | Psmd13 | 5719 | 4-May-15 |
| 17139 | 2 | | | II-1 | Ppfibp1 | 8496 | 4-May-15 | 17590 | 2 | | | II-1 | Psmd4 | 5710 | 4-May-15 |
| 17142 | 2 | | | II-1 | Ppia | 5478 | 12-May-15 | 17591 | 2 | | | II-1 | Psmd5 | 5711 | 4-May-15 |
| 17143 | 2 | | | II-1 | Ppib | 5479 | 12-May-15 | 17592 | 2 | | | II-1 | Psmd6 | 9861 | 4-May-15 |
| 17147 | 2 | | | II-1 | Ppif | 10105 | 4-May-15 | 17593 | 2 | | | II-1 | Psmd7 | 5713 | 4-May-15 |
| 17148 | 2 | | | II-1 | Ppifos | | | 17594 | 2 | | | II-1 | Psmd8 | 5714 | 4-May-15 |
| 17154 | 2 | | | II-1 | Ppil4 | 85313 | 4-May-15 | 17595 | 2 | | | II-1 | Psmd9 | 5715 | 4-May-15 |
| 17155 | 2 | | | II-1 | Ppil6 | 285755 | 4-May-15 | 17600 | 2 | | | II-1 | Psme4 | 23198 | 4-May-15 |
| 17156 | 2 | | | II-1 | Ppip5k1 | 9677 | 4-May-15 | 17601 | 2 | | | II-1 | Psmf1 | 9491 | 4-May-15 |
| 17161 | 2 | | | II-1 | Ppm1d | 8493 | 31-May-15 | 17602 | 2 | | | II-1 | Psmg1 | 8624 | 4-May-15 |
| 17162 | 2 | | | II-1 | Ppm1e | 22843 | 4-May-15 | 17603 | 2 | | | II-1 | Psmg2 | 56984 | 4-May-15 |
| 17165 | 2 | | | II-1 | Ppm1h | 57460 | 4-May-15 | 17619 | 2 | | | II-1 | Ptcd1 | 26024 | 17-May-15 |
| 17174 | 2 | | | II-1 | Ppp1cb | 5500 | 12-May-15 | 17627 | 2 | | | II-1 | Ptchd4 | 442213 | 4-May-15 |
| 17175 | 2 | | | II-1 | Ppp1cc | 5501 | 21-May-15 | 17628 | 2 | | | II-1 | Ptcra | 171558 | 12-May-15 |
| 17182 | 2 | | | II-1 | Ppp1r13l | 10848 | 4-May-15 | 17629 | 2 | | | II-1 | Ptdss1 | 9791 | 4-May-15 |
| 17189 | 2 | | | II-1 | Ppp1r16a | 84988 | 4-May-15 | 17647 | 2 | | | II-1 | Ptgir | 5739 | 4-May-15 |
| 17190 | 2 | | | II-1 | Ppp1r16b | 26051 | 12-May-15 | 17664 | 2 | | | II-1 | Ptms | 5763 | 4-May-15 |
| 17197 | 2 | | | II-1 | Ppp1r21 | 129285 | 4-May-15 | 17677 | 2 | | | II-1 | Ptpn11 | 5781 | 31-May-15 |
| 17217 | 2 | | | II-1 | Ppp1r8 | 5511 | 4-May-15 | 17678 | 2 | | | II-1 | Ptpn12 | 5782 | 4-May-15 |
| 17221 | 2 | | | II-1 | Ppp2cb | 5516 | 4-May-15 | 17684 | 2 | | | II-1 | Ptpn21 | 11099 | 4-May-15 |
| 17222 | 2 | | | II-1 | Ppp2r1a | 5518 | 23-May-15 | 17691 | 2 | | | II-1 | Ptpn7 | 5778 | 4-May-15 |
| 17223 | 2 | | | II-1 | Ppp2r1b | 5519 | 12-May-15 | 17702 | 2 | | | II-1 | Ptprj | 5795 | 12-May-15 |
| 17224 | 2 | | | II-1 | Ppp2r2a | 5520 | 4-May-15 | 17707 | 2 | | | II-1 | Ptpro | 5800 | 7-Jun-15 |
| 17228 | 2 | | | II-1 | Ppp2r2d | 55844 | 4-May-15 | 17713 | 2 | | | II-1 | Ptpru | 10076 | 12-May-15 |
| 17232 | 2 | | | II-1 | Ppp2r4 | 5524 | 12-May-15 | 17714 | 2 | | | II-1 | Ptprv | 148713 | 4-May-15 |
| 17233 | 2 | | | II-1 | Ppp2r5a | 5525 | 4-May-15 | 17720 | 2 | | | II-1 | Pts | 5805 | 12-May-15 |
| 17234 | 2 | | | II-1 | Ppp2r5b | 5526 | 4-May-15 | 17727 | 2 | | | II-1 | Pum2 | 23369 | 29-May-15 |
| 17237 | 2 | | | II-1 | Ppp2r5e | 5529 | 28-May-15 | 17728 | 2 | | | II-1 | Pura | 5813 | 28-May-15 |
| 17238 | 2 | | | II-1 | Ppp3ca | 5530 | 17-May-15 | 17733 | 2 | | | II-1 | Pus3 | 83480 | 4-May-15 |
| 17240 | 2 | | | II-1 | Ppp3cc | 5533 | 12-May-15 | 17735 | 2 | | | II-1 | Pus7l | 83448 | 4-May-15 |
| 17242 | 2 | | | II-1 | Ppp3r2 | 5535 | 4-May-15 | 17746 | 2 | | | II-1 | Pwwp2a | 114825 | 4-May-15 |
| 17243 | 2 | | | II-1 | Ppp4c | 5531 | 1-Jun-15 | 17747 | 2 | | | II-1 | Pwwp2b | 170394 | 12-May-15 |
| 17244 | 2 | | | II-1 | Ppp4r1 | 9989 | 4-May-15 | 17754 | 2 | | | II-1 | Pxt1 | 222659 | 4-May-15 |
| 17245 | 2 | | | II-1 | Ppp4r1l-ps | | | 17755 | 2 | | | II-1 | Pxylp1 | 92370 | 4-May-15 |
| 17247 | 2 | | | II-1 | Ppp4r4 | 57718 | 4-May-15 | 17781 | 2 | | | II-1 | Qrich1 | 54278 | 12-May-15 |
| 17248 | 2 | | | II-1 | Ppp5c | 5536 | 4-May-15 | 17783 | 2 | | | II-1 | Qrsl1 | 55278 | 4-May-15 |
| 17249 | 2 | | | II-1 | Ppp6c | 5537 | 4-May-15 | 17784 | 2 | | | II-1 | Qser1 | 79832 | 4-May-15 |
| 17251 | 2 | | | II-1 | Ppp6r2 | 9701 | 4-May-15 | 17790 | 2 | | | II-1 | R3hcc1l | 27291 | 4-May-15 |
| 17256 | 2 | | | II-1 | Pptc7 | 160760 | 4-May-15 | 17791 | 2 | | | II-1 | R3hdm1 | 23518 | 4-May-15 |
| 17270 | 2 | | | II-1 | Pramef6 | 440561 | 4-May-15 | 17792 | 2 | | | II-1 | R3hdm2 | 22864 | 21-May-15 |
| 17274 | 2 | | | II-1 | Pramef4 | | | 17793 | 2 | | | II-1 | R3hdm4 | 91300 | 4-May-15 |
| 17276 | 2 | | | II-1 | Prameft | | | 17794 | 2 | | | II-1 | R3hdml | 140902 | 4-May-15 |
| 17287 | 2 | | | II-1 | Prdm13 | 59336 | 28-May-15 | 17795 | 2 | | | II-1 | R74862 | | |
| 17288 | 2 | | | II-1 | Prdm14 | 63979 | 4-May-15 | 17796 | 2 | | | II-1 | Rab1 | 5861 | 7-Jun-15 |
| 17293 | 2 | | | II-1 | Prdm5 | 11107 | 12-May-15 | 17798 | 2 | | | II-1 | Rab10os | | |
| 17305 | 2 | | | II-1 | Prelid1 | 27166 | 4-May-15 | 17800 | 2 | | | II-1 | Rab11b | 9230 | 7-Jun-15 |
| 17306 | 2 | | | II-1 | Prelid2 | 153768 | 4-May-15 | 17807 | 2 | | | II-1 | Rab11fip5 | 26056 | 4-May-15 |
| 17311 | 2 | | | II-1 | Prex2 | 80243 | 4-May-15 | 17818 | 2 | | | II-1 | Rab22a | 57403 | 4-May-15 |
| 17318 | 2 | | | II-1 | Prickle2 | 166336 | 4-May-15 | 17820 | 2 | | | II-1 | Rab24 | 53917 | 21-May-15 |
| 17331 | 2 | | | II-1 | Prkag1 | 5571 | 31-May-15 | 17836 | 2 | | | II-1 | Rab36 | 9609 | 23-May-15 |
| 17332 | 2 | | | II-1 | Prkag2 | 51422 | 31-May-15 | 17837 | 2 | | | II-1 | Rab37 | 326624 | 12-May-15 |
| 17355 | 2 | | | II-1 | Prkg2 | 5593 | 17-May-15 | 17843 | 2 | | | II-1 | Rab3c | 115827 | 12-May-15 |
| 17359 | 2 | | | II-1 | Prkx | 5613 | 4-May-15 | 17846 | 2 | | | II-1 | Rab3gap2 | 25782 | 4-May-15 |
| 17363 | 2 | | | II-1 | Prl2c1 | | | 17847 | 2 | | | II-1 | Rab3il1 | 5886 | 4-May-15 |
| 17373 | 2 | | | II-1 | Prl3d3 | | | 17856 | 2 | | | II-1 | Rab5a | 5868 | 31-May-15 |
| 17394 | 2 | | | II-1 | Prmt10 | 90826 | 4-May-15 | 17857 | 2 | | | II-1 | Rab5b | 5869 | 2-Jun-15 |
| 17395 | 2 | | | II-1 | Prmt2 | 3275 | 4-May-15 | 17858 | 2 | | | II-1 | Rab5c | 5878 | 4-May-15 |
| 17399 | 2 | | | II-1 | Prmt7 | 54496 | 4-May-15 | 17859 | 2 | | | II-1 | Rab6a | 5870 | 29-May-15 |
| 17400 | 2 | | | II-1 | Prmt8 | 56341 | 4-May-15 | 17860 | 2 | | | II-1 | Rab6b | 51560 | 23-May-15 |
| 17410 | 2 | | | II-1 | Prok1 | 84432 | 4-May-15 | 17865 | 2 | | | II-1 | Rab9 | 9367 | 29-May-15 |
| 17418 | 2 | | | II-1 | Prorsd1 | | | 17869 | 2 | | | II-1 | Rabep2 | 79874 | 4-May-15 |
| 17428 | 2 | | | II-1 | Prpf19 | 27339 | 4-May-15 | 17871 | 2 | | | II-1 | Rabgap1 | 23637 | 4-May-15 |
| 17429 | 2 | | | II-1 | Prpf3 | 9129 | 23-May-15 | 17872 | 2 | | | II-1 | Rabgap1l | 9910 | 3-May-15 |
| 17430 | 2 | | | II-1 | Prpf31 | 26121 | 23-May-15 | 17874 | 2 | | | II-1 | Rabggta | 5875 | 12-May-15 |
| 17431 | 2 | | | II-1 | Prpf38a | 84950 | 4-May-15 | 17875 | 2 | | | II-1 | Rabggtb | 5876 | 4-May-15 |
| 17433 | 2 | | | II-1 | Prpf39 | 55015 | 4-May-15 | 17876 | 2 | | | II-1 | Rabif | 5877 | 4-May-15 |
| 17434 | 2 | | | II-1 | Prpf4 | 9128 | 4-May-15 | 17877 | 2 | | | II-1 | Rabl2 | | |
| 17435 | 2 | | | II-1 | Prpf40a | 55660 | 4-May-15 | 17880 | 2 | | | II-1 | Rac1 | 5879 | 7-Jun-15 |
| 17446 | 2 | | | II-1 | Prps2 | 5634 | 4-May-15 | 17881 | 2 | | | II-1 | Rac2 | 5880 | 4-May-15 |
| 17449 | 2 | | | II-1 | Prr11 | 55771 | 17-May-15 | 17886 | 2 | | | II-1 | Rad18 | 56852 | 12-May-15 |
| 17459 | 2 | | | II-1 | Prr22 | 163154 | 4-May-15 | 17890 | 2 | | | II-1 | Rad23b | 5887 | 4-May-15 |
| 17460 | 2 | | | II-1 | Prr23a | 729627 | 4-May-15 | 17892 | 2 | | | II-1 | Rad51 | 5888 | 24-May-15 |
| 17473 | 2 | | | II-1 | Prrc2b | 84726 | 4-May-15 | 17897 | 2 | | | II-1 | Rad51d | 5892 | 4-May-15 |
| 17501 | 2 | | | II-1 | Prss35 | 167681 | 4-May-15 | 17905 | 2 | | | II-1 | Rae1 | 8480 | 12-May-15 |
| 17505 | 2 | | | II-1 | Prss39 | | | 17907 | 2 | | | II-1 | Raet1b | | |
| 17506 | 2 | | | II-1 | Prss40 | | | 17908 | 2 | | | II-1 | Raet1c | | |
| 17507 | 2 | | | II-1 | Prss41 | 360226 | 4-May-15 | 17920 | 2 | | | II-1 | Ralgapa1 | 253860 | 12-May-15 |
| 17508 | 2 | | | II-1 | Prss42 | 339906 | 4-May-15 | 17921 | 2 | | | II-1 | Ralgapa2 | 57186 | 4-May-15 |
| 17509 | 2 | | | II-1 | Prss43 | 100288 960 | | 17923 | 2 | | | II-1 | Ralgds | 5900 | 12-May-15 |
| 17510 | 2 | | | II-1 | Prss44 | 729756 | 17-Mar-15 | 17933 | 2 | | | II-1 | Ranbp10 | 57610 | 4-May-15 |
| 17514 | 2 | | | II-1 | Prss50 | 29122 | 4-May-15 | 17938 | 2 | | | II-1 | Ranbp6 | 26953 | 4-May-15 |
| 17516 | 2 | | | II-1 | Prss52 | | | 17941 | 2 | | | II-1 | Rangrf | 29098 | 4-May-15 |
| 17520 | 2 | | | II-1 | Prss56 | 648960 | 4-May-15 | 17944 | 2 | | | II-1 | Rap1gap | 5909 | 4-May-15 |
| 17521 | 2 | | | II-1 | Prss57 | 400668 | 23-May-15 | 17950 | 2 | | | II-1 | Rapgef1 | 2889 | 12-May-15 |

Fig.22 - 108

| | | | | | | | | | | | | | | |
|---|---|---|---|---|---|---|---|---|---|---|---|---|---|---|
| 17951 | 2 | | | II-1 | Rapgef2 | 9693 | 4-May-15 | 18467 | 2 | | | II-1 | Rnpc3 | 55599 | 4-May-15 |
| 17968 | 2 | | | II-1 | Rasa3 | 22821 | 12-May-15 | 18469 | 2 | | | II-1 | Rnpepl1 | 57140 | 4-May-15 |
| 18004 | 2 | | | II-1 | Raver2 | 55225 | 4-May-15 | 18470 | 2 | | | II-1 | Rnps1 | 10921 | 12-May-15 |
| 18007 | 2 | | | II-1 | Rb1cc1 | 9821 | 23-May-15 | 18479 | 2 | | | II-1 | Robo4 | 54538 | 4-May-15 |
| 18010 | 2 | | | II-1 | Rbbp4 | 5928 | 24-May-15 | 18494 | 2 | | | II-1 | Rpl11 | 94137 | 12-May-15 |
| 18011 | 2 | | | II-1 | Rbbp5 | 5929 | 4-May-15 | 18495 | 2 | | | II-1 | Rp2h | | |
| 18014 | 2 | | | II-1 | Rbbp8 | 5932 | 17-May-15 | 18496 | 2 | | | II-1 | Rp9 | 6100 | 4-May-15 |
| 18018 | 2 | | | II-1 | Rbfa | 79863 | 4-May-15 | 18498 | 2 | | | II-1 | Rpa2 | 6118 | 7-Jun-15 |
| 18028 | 2 | | | II-1 | Rbm12l1 | | | 18503 | 2 | | | II-1 | Rpap3 | 79657 | 4-May-15 |
| 18043 | 2 | | | II-1 | Rbm28 | 55131 | 12-May-15 | 18514 | 2 | | | II-1 | Rpl10 | 6134 | 7-Jun-15 |
| 18055 | 2 | | | II-1 | Rbm44 | 375316 | 4-May-15 | 18517 | 2 | | | II-1 | Rpl11 | 6135 | 23-May-15 |
| 18058 | 2 | | | II-1 | Rbm46os | | | 18526 | 2 | | | II-1 | Rpl18a | 6142 | 12-May-15 |
| 18059 | 2 | | | II-1 | Rbm47 | 54502 | 21-May-15 | 18530 | 2 | | | II-1 | Rpl22l1 | 200916 | 4-May-15 |
| 18062 | 2 | | | II-1 | Rbm5 | 10181 | 4-May-15 | 18535 | 2 | | | II-1 | Rpl27 | 6155 | 21-May-15 |
| 18063 | 2 | | | II-1 | Rbm6 | 10180 | 4-May-15 | 18564 | 2 | | | II-1 | Rpl8 | 6132 | 4-May-15 |
| 18065 | 2 | | | II-1 | Rbm8a | 9939 | 23-May-15 | 18565 | 2 | | | II-1 | Rpl9 | 6133 | 4-May-15 |
| 18066 | 2 | | | II-1 | Rbms1 | 5937 | 4-May-15 | 18571 | 2 | | | II-1 | Rpn2 | 6185 | 7-Jun-15 |
| 18072 | 2 | | | II-1 | Rbmxl2 | 27288 | 4-May-15 | 18572 | 2 | | | II-1 | Rps14 | 11102 | 4-May-15 |
| 18073 | 2 | | | II-1 | Rbmy | 5940 | 23-May-15 | 18582 | 2 | | | II-1 | Rprd2 | 23248 | 4-May-15 |
| 18085 | 2 | | | II-1 | Rc3h2 | 54542 | 4-May-15 | 18583 | 2 | | | II-1 | Rprl1 | | |
| 18086 | 2 | | | II-1 | Rcan1 | 1827 | 17-May-15 | 18584 | 2 | | | II-1 | Rprl2 | | |
| 18091 | 2 | | | II-1 | Rcc1 | 1104 | 4-May-15 | 18585 | 2 | | | II-1 | Rprl3 | | |
| 18092 | 2 | | | II-1 | Rcc2 | 55920 | 12-May-15 | 18594 | 2 | | | II-1 | Rps15a | 6210 | 4-May-15 |
| 18094 | 2 | | | II-1 | Rce1 | 9986 | 4-May-15 | 18606 | 2 | | | II-1 | Rps23 | 6228 | 12-May-15 |
| 18096 | 2 | | | II-1 | Rcl1 | 10171 | 1-Jun-15 | 18623 | 2 | | | II-1 | Rps6ka2 | 6196 | 21-May-15 |
| 18105 | 2 | | | II-1 | Rd5 | 343035 | 23-May-15 | 18627 | 2 | | | II-1 | Rps6ka6 | 27330 | 4-May-15 |
| 18106 | 2 | | | II-1 | Rd3l | 647286 | 4-May-15 | 18629 | 2 | | | II-1 | Rps6kb2 | 6199 | 4-May-15 |
| 18112 | 2 | | | II-1 | Rdh14 | 57665 | 4-May-15 | 18630 | 2 | | | II-1 | Rps6kc1 | 26750 | 21-May-15 |
| 18146 | 2 | | | II-1 | Reln | 5649 | 17-May-15 | 18638 | 2 | | | II-1 | Rptoros | | |
| 18173 | 2 | | | II-1 | Rexo2 | 25996 | 4-May-15 | 18639 | 2 | | | II-1 | Rpusd1 | 113000 | 4-May-15 |
| 18174 | 2 | | | II-1 | Rexo4 | 57109 | 4-May-15 | 18641 | 2 | | | II-1 | Rpusd3 | 285367 | 4-May-15 |
| 18176 | 2 | | | II-1 | Rfc2 | 5982 | 4-May-15 | 18653 | 2 | | | II-1 | Rrh | 10692 | 4-May-15 |
| 18183 | 2 | | | II-1 | Rfng | 5986 | 4-May-15 | 18654 | 2 | | | II-1 | Rrm1 | 6240 | 4-May-15 |
| 18184 | 2 | | | II-1 | Rfpl3s | 10737 | 4-May-15 | 18658 | 2 | | | II-1 | Rrnad1 | 51093 | 4-May-15 |
| 18185 | 2 | | | II-1 | Rfpl4 | 342931 | 24-May-15 | 18659 | 2 | | | II-1 | Rrp1 | 8568 | 7-Jun-15 |
| 18186 | 2 | | | II-1 | Rfpl4b | 442247 | 4-May-15 | 18664 | 2 | | | II-1 | Rrp7a | 27341 | 4-May-15 |
| 18187 | 2 | | | II-1 | Rft1 | 91869 | 13-Jun-15 | 18666 | 2 | | | II-1 | Rrp9 | 9136 | 4-May-15 |
| 18191 | 2 | | | II-1 | Rfwd3 | 55159 | 28-May-15 | 18668 | 2 | | | II-1 | Rs1 | 6247 | 24-May-15 |
| 18192 | 2 | | | II-1 | Rfx1 | 5989 | 4-May-15 | 18669 | 2 | | | II-1 | Rsad1 | 55316 | 4-May-15 |
| 18197 | 2 | | | II-1 | Rfx6 | 222546 | 28-May-15 | 18676 | 2 | | | II-1 | Rsl1 | | |
| 18198 | 2 | | | II-1 | Rfx7 | 64864 | 4-May-15 | 18679 | 2 | | | II-1 | Rslcan18 | | |
| 18199 | 2 | | | II-1 | Rfx8 | 731220 | 4-May-15 | 18680 | 2 | | | II-1 | Rsph1 | 89765 | 4-May-15 |
| 18201 | 2 | | | II-1 | Rfxap | 5994 | 4-May-15 | 18688 | 2 | | | II-1 | Rspo3 | 84870 | 4-May-15 |
| 18202 | 2 | | | II-1 | Rgag1 | 57529 | 4-May-15 | 18692 | 2 | | | II-1 | Rsrc2 | 65117 | 4-May-15 |
| 18226 | 2 | | | II-1 | Rgs22 | 26166 | 4-May-15 | 18693 | 2 | | | II-1 | Rsrp1 | 57035 | 4-May-15 |
| 18236 | 2 | | | II-1 | Rgsl1 | 353299 | 4-May-15 | 18695 | 2 | | | II-1 | Rtbdn | 83546 | 10-May-15 |
| 18257 | 2 | | | II-1 | Rhobtb3 | 22836 | 4-May-15 | 18697 | 2 | | | II-1 | Rtcb | 51493 | 12-May-15 |
| 18271 | 2 | | | II-1 | Rhox11 | | | 18699 | 2 | | | II-1 | Rtel1 | 51750 | 4-Jun-15 |
| 18274 | 2 | | | II-1 | Rhox2a | | | 18700 | 2 | | | II-1 | Rtf1 | 23168 | 4-May-15 |
| 18276 | 2 | | | II-1 | Rhox2c | | | 18701 | 2 | | | II-1 | Rtfdc1 | 51507 | 4-May-15 |
| 18291 | 2 | | | II-1 | Rhox4d | | | 18702 | 2 | | | II-1 | Rtkn | 6242 | 12-May-15 |
| 18292 | 2 | | | II-1 | Rhox4e | | | 18710 | 2 | | | II-1 | Rtn4r | 65078 | 4-May-15 |
| 18293 | 2 | | | II-1 | Rhox4f | | | 18720 | 2 | | | II-1 | Rufy2 | 55680 | 1-Jun-15 |
| 18298 | 2 | | | II-1 | Rhox8 | | | 18721 | 2 | | | II-1 | Rufy3 | 22902 | 7-Jun-15 |
| 18306 | 2 | | | II-1 | Ric8 | 60626 | 7-Jun-15 | 18734 | 2 | | | II-1 | Rwdd1 | 51389 | 4-May-15 |
| 18308 | 2 | | | II-1 | Rictor | 253260 | 4-May-15 | 18740 | 2 | | | II-1 | Rxfp2 | 122042 | 4-May-15 |
| 18315 | 2 | | | II-1 | Rimbp3 | 85376 | 4-May-15 | 18741 | 2 | | | II-1 | Rxfp3 | 51289 | 4-May-15 |
| 18327 | 2 | | | II-1 | Rint1 | 60561 | 29-May-15 | 18743 | 2 | | | II-1 | Rxra | 6256 | 4-May-15 |
| 18329 | 2 | | | II-1 | Riok2 | 55781 | 4-May-15 | 18751 | 2 | | | II-1 | S100a1 | 6271 | 4-May-15 |
| 18330 | 2 | | | II-1 | Riok3 | 8780 | 4-May-15 | 18782 | 2 | | | II-1 | Sae1 | 10055 | 4-May-15 |
| 18331 | 2 | | | II-1 | Ripk1 | 8737 | 4-May-15 | 18783 | 2 | | | II-1 | Safb | 6294 | 4-May-15 |
| 18332 | 2 | | | II-1 | Ripk2 | 8767 | 29-May-15 | 18789 | 2 | | | II-1 | Sall4 | 57167 | 23-May-15 |
| 18336 | 2 | | | II-1 | Ripply1 | 134701 | 12-May-15 | 18803 | 2 | | | II-1 | Samhd1 | 25939 | 23-May-15 |
| 18337 | 2 | | | II-1 | Ripply3 | 53820 | 4-May-15 | 18808 | 2 | | | II-1 | Samt4 | | |
| 18340 | 2 | | | II-1 | Rita1 | 84934 | 4-May-15 | 18809 | 2 | | | II-1 | Sap130 | 79595 | 7-Jun-15 |
| 18342 | 2 | | | II-1 | Rif | 6018 | 7-Jun-15 | 18810 | 2 | | | II-1 | Sap18 | 10284 | 4-May-15 |
| 18343 | 2 | | | II-1 | Rlim | 51132 | 4-May-15 | 18823 | 2 | | | II-1 | Sars2 | 54938 | 4-May-15 |
| 18370 | 2 | | | II-1 | Rnaseh2a | 10535 | 23-May-15 | 18824 | 2 | | | II-1 | Sart1 | 9092 | 12-May-15 |
| 18382 | 2 | | | II-1 | Rnf11 | 26994 | 2-Jun-15 | 18826 | 2 | | | II-1 | Sash1 | 23328 | 12-May-15 |
| 18383 | 2 | | | II-1 | Rnf111 | 54778 | 4-May-15 | 18836 | 2 | | | II-1 | Sbds | 51119 | 23-May-15 |
| 18388 | 2 | | | II-1 | Rnf115 | 27246 | 4-May-15 | 18837 | 2 | | | II-1 | Sbf1 | 6305 | 23-May-15 |
| 18397 | 2 | | | II-1 | Rnf133 | 168433 | 4-May-15 | 18838 | 2 | | | II-1 | Sbf2 | 81846 | 23-May-15 |
| 18398 | 2 | | | II-1 | Rnf135 | 84282 | 4-May-15 | 18839 | 2 | | | II-1 | Sbk1 | 388228 | 4-May-15 |
| 18399 | 2 | | | II-1 | Rnf138 | 51444 | 4-May-15 | 18843 | 2 | | | II-1 | Sbno2 | 22904 | 4-May-15 |
| 18400 | 2 | | | II-1 | Rnf138rt1 | | | 18851 | 2 | | | II-1 | Scaf4 | 57466 | 12-May-15 |
| 18401 | 2 | | | II-1 | Rnf139 | 11236 | 4-May-15 | 18853 | 2 | | | II-1 | Scai | 286205 | 4-May-15 |
| 18403 | 2 | | | II-1 | Rnf141 | 50862 | 1-Jun-15 | 18854 | 2 | | | II-1 | Scamp1 | 9522 | 12-May-15 |
| 18408 | 2 | | | II-1 | Rnf148 | 378925 | 4-May-15 | 18856 | 2 | | | II-1 | Scamp3 | 10067 | 4-May-15 |
| 18415 | 2 | | | II-1 | Rnf166 | 115992 | 4-May-15 | 18857 | 2 | | | II-1 | Scamp4 | 113178 | 4-May-15 |
| 18417 | 2 | | | II-1 | Rnf168 | 165918 | 23-May-15 | 18858 | 2 | | | II-1 | Scamp5 | 192683 | 4-May-15 |
| 18420 | 2 | | | II-1 | Rnf170 | 81790 | 23-May-15 | 18859 | 2 | | | II-1 | Scand1 | 51282 | 28-May-15 |
| 18428 | 2 | | | II-1 | Rnf19a | 25987 | 12-May-15 | 18873 | 2 | | | II-1 | Scarna3a | | |
| 18430 | 2 | | | II-1 | Rnf2 | 6045 | 2-Jun-15 | 18887 | 2 | | | II-1 | Scg3 | 29106 | 7-Jun-15 |
| 18432 | 2 | | | II-1 | Rnf207 | 388591 | 4-May-15 | 18892 | 2 | | | II-1 | Scgb1b29 | | |
| 18435 | 2 | | | II-1 | Rnf215 | 200312 | 4-May-15 | 18921 | 2 | | | II-1 | Scml2 | 10389 | 31-May-15 |
| 18441 | 2 | | | II-1 | Rnf223 | 401934 | 4-May-15 | 18936 | 2 | | | II-1 | Scn9a | 6335 | 24-May-15 |
| 18446 | 2 | | | II-1 | Rnf31 | 55072 | 4-May-15 | 18937 | 2 | | | II-1 | Scnm1 | 79005 | 4-May-15 |
| 18449 | 2 | | | II-1 | Rnf38 | 152006 | 2-Jun-15 | 18945 | 2 | | | II-1 | Scp2d1 | 140856 | 4-May-15 |
| 18450 | 2 | | | II-1 | Rnf39 | 80352 | 4-May-15 | 18954 | 2 | | | II-1 | Scrt2 | 85508 | 4-May-15 |
| 18453 | 2 | | | II-1 | Rnf41 | 10193 | 2-Jun-15 | 18963 | 2 | | | II-1 | Scyl3 | 57147 | 7-Jun-15 |
| 18456 | 2 | | | II-1 | Rnf5 | 6048 | 2-Jun-15 | 18964 | 2 | | | II-1 | Sdad1 | 55183 | 4-May-15 |
| 18458 | 2 | | | II-1 | Rnf7 | 9616 | 2-Jun-15 | 18972 | 2 | | | II-1 | Sdccag8 | 10806 | 23-May-15 |
| 18459 | 2 | | | II-1 | Rnf8 | 9025 | 4-May-15 | 18973 | 2 | | | II-1 | Sde2 | 163859 | 4-May-15 |
| 18460 | 2 | | | II-1 | Rnft1 | 51136 | 4-May-15 | 18983 | 2 | | | II-1 | Sdk1 | 221935 | 4-May-15 |
| 18461 | 2 | | | II-1 | Rnft2 | 84900 | 12-May-15 | 18984 | 2 | | | II-1 | Sdk2 | 54549 | 4-May-15 |
| 18463 | 2 | | | II-1 | Rnh1 | 6050 | 13-Jun-15 | 18985 | 2 | | | II-1 | Sdpr | 8436 | 12-May-15 |
| 18464 | 2 | | | II-1 | Rnls | 55328 | 12-May-15 | 18989 | 2 | | | II-1 | Sdr42e1 | 93517 | 4-May-15 |

Fig.22 - 109

| | | | | | | | | | | | | | |
|---|---|---|---|---|---|---|---|---|---|---|---|---|---|
| 18998 | 2 | | | II-1 | Sec14l1 | 6397 | 31-May-15 | 19648 | 2 | | | II-1 | Slc38a1 | 81539 | 4-May-15 |
| 19008 | 2 | | | II-1 | Sec23a | 10484 | 12-May-15 | 19657 | 2 | | | II-1 | Slc38a8 | 146167 | 4-May-15 |
| 19013 | 2 | | | II-1 | Sec24c | 9632 | 12-May-15 | 19658 | 2 | | | II-1 | Slc38a9 | 153129 | 14-May-15 |
| 19023 | 2 | | | II-1 | Secisbp2 | 79048 | 4-May-15 | 19664 | 2 | | | II-1 | Slc39a14 | 23516 | 4-May-15 |
| 19029 | 2 | | | II-1 | Sell12 | 80343 | 4-May-15 | 19667 | 2 | | | II-1 | Slc39a4 | 55630 | 10-May-15 |
| 19042 | 2 | | | II-1 | Sema3b | 7869 | 12-May-15 | 19683 | 2 | | | II-1 | Slc44a2 | 57153 | 12-May-15 |
| 19050 | 2 | | | II-1 | Sema4c | 54910 | 4-May-15 | 19688 | 2 | | | II-1 | Slc45a2 | 51151 | 23-May-15 |
| 19052 | 2 | | | II-1 | Sema4f | 10505 | 4-May-15 | 19701 | 2 | | | II-1 | Slc4a2 | 6522 | 21-May-15 |
| 19063 | 2 | | | II-1 | Senp3 | 26168 | 4-May-15 | 19702 | 2 | | | II-1 | Slc4a3 | 6508 | 12-May-15 |
| 19064 | 2 | | | II-1 | Senp5 | 205564 | 12-May-15 | 19715 | 2 | | | II-1 | Slc5a11 | 115584 | 4-May-15 |
| 19065 | 2 | | | II-1 | Senp6 | 26054 | 12-May-15 | 19721 | 2 | | | II-1 | Slc5a5 | 6528 | 12-May-15 |
| 19066 | 2 | | | II-1 | Senp7 | 57337 | 4-May-15 | 19759 | 2 | | | II-1 | Slc7a7 | 9056 | 23-May-15 |
| 19067 | 2 | | | II-1 | Senp8 | 123228 | 4-May-15 | 19773 | 2 | | | II-1 | Slc9a6 | 10479 | 7-Jun-15 |
| 19069 | 2 | | | II-1 | Sephs2 | 22928 | 4-May-15 | 19774 | 2 | | | II-1 | Slc9a7 | 84679 | 4-May-15 |
| 19077 | 2 | | | II-1 | Sept14 | 346288 | 4-May-15 | 19784 | 2 | | | II-1 | Slco1b2 | | |
| 19078 | 2 | | | II-1 | Sept15 | | | 19785 | 2 | | | II-1 | Slco1c1 | 53919 | 4-May-15 |
| 19079 | 2 | | | II-1 | Sept2 | 4735 | 7-Jun-15 | 19794 | 2 | | | II-1 | Slco6d1 | | |
| 19080 | 2 | | | II-1 | Sept3 | 55964 | 4-May-15 | 19812 | 2 | | | II-1 | Slitrk3 | 22865 | 4-May-15 |
| 19090 | 2 | | | II-1 | Serf1 | 8293 | 4-May-15 | 19813 | 2 | | | II-1 | Slitrk4 | 139065 | 4-May-15 |
| 19093 | 2 | | | II-1 | Serhl | 94009 | 4-May-15 | 19814 | 2 | | | II-1 | Slitrk5 | 26060 | 4-May-15 |
| 19098 | 2 | | | II-1 | Serinc5 | 256987 | 28-May-15 | 19815 | 2 | | | II-1 | Slitrk6 | 84189 | 23-May-15 |
| 19100 | 2 | | | II-1 | Serp2 | 387923 | 21-May-15 | 19824 | 2 | | | II-1 | Sturp1 | 57152 | 4-May-15 |
| 19138 | 2 | | | II-1 | Serpinb5 | 5268 | 4-May-15 | 19826 | 2 | | | II-1 | Six1b | 79008 | 4-May-15 |
| 19149 | 2 | | | II-1 | Serpinb9d | | | 19829 | 2 | | | II-1 | Six1 | | |
| 19166 | 2 | | | II-1 | Sertad3 | 29946 | 4-May-15 | 19831 | 2 | | | II-1 | Smad1 | 4086 | 7-Jun-15 |
| 19167 | 2 | | | II-1 | Sertad4 | 56256 | 4-May-15 | 19833 | 2 | | | II-1 | Smad3 | 4088 | 24-May-15 |
| 19183 | 2 | | | II-1 | Setd8 | 387893 | 4-May-15 | 19834 | 2 | | | II-1 | Smad4 | 4089 | 23-May-15 |
| 19189 | 2 | | | II-1 | Sez6l | 23544 | 12-May-15 | 19835 | 2 | | | II-1 | Smad5 | 4090 | 12-May-15 |
| 19190 | 2 | | | II-1 | Sez6l2 | 26470 | 4-May-15 | 19842 | 2 | | | II-1 | Smarca1 | 6594 | 2-Jun-15 |
| 19193 | 2 | | | II-1 | Sf3a2 | 8175 | 4-May-15 | 19846 | 2 | | | II-1 | Smarca5-ps | | |
| 19194 | 2 | | | II-1 | Sf3a3 | 10946 | 4-May-15 | 19850 | 2 | | | II-1 | Smarcc1 | 6599 | 4-May-15 |
| 19196 | 2 | | | II-1 | Sf3b2 | 10992 | 12-May-15 | 19851 | 2 | | | II-1 | Smarcc2 | 6601 | 4-May-15 |
| 19197 | 2 | | | II-1 | Sf3b3 | 23450 | 4-May-15 | 19852 | 2 | | | II-1 | Smarcd1 | 6602 | 4-May-15 |
| 19198 | 2 | | | II-1 | Sf3b4 | 10262 | 1-Jun-15 | 19853 | 2 | | | II-1 | Smarcd2 | 6603 | 4-May-15 |
| 19199 | 2 | | | II-1 | Sf3b5 | 83443 | 4-May-15 | 19861 | 2 | | | II-1 | Smc4 | 10051 | 4-May-15 |
| 19200 | 2 | | | II-1 | Sf3b6 | 51639 | 4-May-15 | 19868 | 2 | | | II-1 | Smco4 | 56935 | 4-May-15 |
| 19201 | 2 | | | II-1 | Sfi1 | 9814 | 4-May-15 | 19872 | 2 | | | II-1 | Smek1 | 55671 | 1-Jun-15 |
| 19203 | 2 | | | II-1 | Sfmbt2 | 57713 | 4-May-15 | 19873 | 2 | | | II-1 | Smek2 | 57223 | 4-May-15 |
| 19207 | 2 | | | II-1 | Sfrp1 | 6422 | 12-May-15 | 19874 | 2 | | | II-1 | Smg1 | 23049 | 4-May-15 |
| 19214 | 2 | | | II-1 | Sft2d3 | 84826 | 4-May-15 | 19877 | 2 | | | II-1 | Smg7 | 9887 | 4-May-15 |
| 19215 | 2 | | | II-1 | Sfta2 | 389376 | 4-May-15 | 19878 | 2 | | | II-1 | Smg8 | 55181 | 4-May-15 |
| 19243 | 2 | | | II-1 | Sgsm1 | 129049 | 4-May-15 | 19879 | 2 | | | II-1 | Smg9 | 56006 | 4-May-15 |
| 19245 | 2 | | | II-1 | Sgsm3 | 27352 | 4-May-15 | 19885 | 2 | | | II-1 | Smim14 | 201895 | 4-May-15 |
| 19247 | 2 | | | II-1 | Sgtb | 54557 | 14-May-15 | 19886 | 2 | | | II-1 | Smim15 | 643155 | 4-May-15 |
| 19254 | 2 | | | II-1 | Sh2d2a | 9047 | 4-May-15 | 19887 | 2 | | | II-1 | Smim18 | 100507341 | 4-May-15 |
| 19268 | 2 | | | II-1 | Sh3bp5l | 80851 | 4-May-15 | 19901 | 2 | | | II-1 | Smn1 | 6606 | 23-May-15 |
| 19275 | 2 | | | II-1 | Sh3glb2 | 56904 | 4-May-15 | 19908 | 2 | | | II-1 | Smok3a | | |
| 19291 | 2 | | | II-1 | Shc1 | 6464 | 31-May-15 | 19909 | 2 | | | II-1 | Smok3b | | |
| 19292 | 2 | | | II-1 | Shc2 | 25759 | 4-May-15 | 19910 | 2 | | | II-1 | Smok4a | | |
| 19293 | 2 | | | II-1 | Shc3 | 53358 | 12-May-15 | 19911 | 2 | | | II-1 | Smox | 54498 | 4-May-15 |
| 19307 | 2 | | | II-1 | Shisa7 | 729956 | 4-May-15 | 19928 | 2 | | | II-1 | Smurf1 | 57154 | 31-May-15 |
| 19308 | 2 | | | II-1 | Shisa9 | 729993 | 12-May-15 | 19933 | 2 | | | II-1 | Smyd4 | 114826 | 4-May-15 |
| 19313 | 2 | | | II-1 | Shox2 | 6474 | 17-May-15 | 19934 | 2 | | | II-1 | Smyd5 | 10322 | 4-May-15 |
| 19314 | 2 | | | II-1 | Shpk | 23729 | 4-May-15 | 19941 | 2 | | | II-1 | Snap47 | 116841 | 21-May-15 |
| 19340 | 2 | | | II-1 | Sil1 | 64374 | 21-May-15 | 19948 | 2 | | | II-1 | Snapin | 23557 | 21-May-15 |
| 19341 | 2 | | | II-1 | Sim1 | 6492 | 28-May-15 | 19995 | 2 | | | II-1 | Snora62 | 6044 | 4-May-15 |
| 19342 | 2 | | | II-1 | Sim2 | 6493 | 28-May-15 | 20008 | 2 | | | II-1 | Snord11 | 692058 | 4-May-15 |
| 19345 | 2 | | | II-1 | Sin3b | 23309 | 12-May-15 | 20026 | 2 | | | II-1 | Snord1b | 677849 | 4-May-15 |
| 19353 | 2 | | | II-1 | Sirt1 | 23411 | 31-May-15 | 20087 | 2 | | | II-1 | Snmp48 | 154007 | 4-May-15 |
| 19356 | 2 | | | II-1 | Sirt4 | 23409 | 31-May-15 | 20093 | 2 | | | II-1 | Snrpc | 6631 | 7-Jun-15 |
| 19381 | 2 | | | II-1 | Skint2 | | | 20097 | 2 | | | II-1 | Snrpe | 6635 | 12-May-15 |
| 19390 | 2 | | | II-1 | Skiv2l2 | 23517 | 21-May-15 | 20115 | 2 | | | II-1 | Snx14 | 57231 | 29-May-15 |
| 19391 | 2 | | | II-1 | Skor1 | 390598 | 4-May-15 | 20116 | 2 | | | II-1 | Snx15 | 29907 | 4-May-15 |
| 19393 | 2 | | | II-1 | Skp1a | 6500 | 4-May-15 | 20117 | 2 | | | II-1 | Snx16 | 64089 | 4-May-15 |
| 19400 | 2 | | | II-1 | Slamf1 | 6504 | 12-May-15 | 20118 | 2 | | | II-1 | Snx17 | 9784 | 12-May-15 |
| 19410 | 2 | | | II-1 | Slc10a4 | 201780 | 4-May-15 | 20119 | 2 | | | II-1 | Snx18 | 112574 | 4-May-15 |
| 19417 | 2 | | | II-1 | Slc12a2 | 6558 | 4-May-15 | 20120 | 2 | | | II-1 | Snx19 | 399979 | 12-May-15 |
| 19420 | 2 | | | II-1 | Slc12a5 | 57468 | 12-May-15 | 20121 | 2 | | | II-1 | Snx2 | 6643 | 4-May-15 |
| 19424 | 2 | | | II-1 | Slc12a9 | 56996 | 4-May-15 | 20122 | 2 | | | II-1 | Snx20 | 124460 | 4-May-15 |
| 19459 | 2 | | | II-1 | Slc17a8 | 246213 | 23-May-15 | 20123 | 2 | | | II-1 | Snx21 | 90203 | 4-May-15 |
| 19474 | 2 | | | II-1 | Slc1a7 | 6512 | 4-May-15 | 20127 | 2 | | | II-1 | Snx27 | 81609 | 4-May-15 |
| 19481 | 2 | | | II-1 | Slc22a14 | 9389 | 4-May-15 | 20128 | 2 | | | II-1 | Snx29 | 92017 | 4-May-15 |
| 19482 | 2 | | | II-1 | Slc22a15 | 55356 | 4-May-15 | 20134 | 2 | | | II-1 | Snx4 | 8723 | 4-May-15 |
| 19483 | 2 | | | II-1 | Slc22a16 | 85413 | 4-May-15 | 20137 | 2 | | | II-1 | Snx7 | 51375 | 4-May-15 |
| 19507 | 2 | | | II-1 | Slc24a2 | 25769 | 4-May-15 | 20139 | 2 | | | II-1 | Snx9 | 51429 | 4-May-15 |
| 19519 | 2 | | | II-1 | Slc25a17 | 10478 | 4-May-15 | 20140 | 2 | | | II-1 | Soat1 | 6646 | 4-May-15 |
| 19521 | 2 | | | II-1 | Slc25a19 | 60386 | 23-May-15 | 20149 | 2 | | | II-1 | Socs7 | 30837 | 7-Jun-15 |
| 19522 | 2 | | | II-1 | Slc25a42 | 83884 | 4-May-15 | 20150 | 2 | | | II-1 | Sod1 | 6647 | 31-May-15 |
| 19523 | 2 | | | II-1 | Slc25a26 | 788 | 12-May-15 | 20163 | 2 | | | II-1 | Sorbs3 | 10174 | 12-May-15 |
| 19556 | 2 | | | II-1 | Slc25a53 | 401612 | 4-May-15 | 20169 | 2 | | | II-1 | Sos2 | 6655 | 4-May-15 |
| 19558 | 2 | | | II-1 | Slc26a1 | 10861 | 4-May-15 | 20177 | 2 | | | II-1 | Sox10 | 6663 | 31-May-15 |
| 19564 | 2 | | | II-1 | Slc26a5 | 375611 | 4-May-15 | 20188 | 2 | | | II-1 | Sox3 | 6658 | 23-May-15 |
| 19566 | 2 | | | II-1 | Slc26a7 | 115111 | 4-May-15 | 20191 | 2 | | | II-1 | Sox5 | 6660 | 12-May-15 |
| 19575 | 2 | | | II-1 | Slc28a1 | 9154 | 12-May-15 | 20214 | 2 | | | II-1 | Spaca5 | 389852 | 4-May-15 |
| 19601 | 2 | | | II-1 | Slc30a6 | 55676 | 4-May-15 | 20221 | 2 | | | II-1 | Spag17 | 200162 | 12-May-15 |
| 19604 | 2 | | | II-1 | Slc30a9 | 10463 | 4-May-15 | 20222 | 2 | | | II-1 | Spag4 | 6676 | 4-May-15 |
| 19605 | 2 | | | II-1 | Slc31a1 | 1317 | 17-May-15 | 20223 | 2 | | | II-1 | Spag5 | 10615 | 4-May-15 |
| 19607 | 2 | | | II-1 | Slc32a1 | 140679 | 4-May-15 | 20226 | 2 | | | II-1 | Spag8 | 26206 | 4-May-15 |
| 19608 | 2 | | | II-1 | Slc33a1 | 9197 | 4-May-15 | 20227 | 2 | | | II-1 | Spag9 | 9043 | 4-May-15 |
| 19609 | 2 | | | II-1 | Slc34a1 | 6569 | 24-May-15 | 20228 | 2 | | | II-1 | Spam1 | 6677 | 12-May-15 |
| 19617 | 2 | | | II-1 | Slc35b1 | 10237 | 21-May-15 | 20229 | 2 | | | II-1 | Sparc | 6678 | 17-May-15 |
| 19618 | 2 | | | II-1 | Slc35b2 | 347734 | 4-May-15 | 20238 | 2 | | | II-1 | Spata2 | 9825 | 12-May-15 |
| 19619 | 2 | | | II-1 | Slc35b3 | 51000 | 28-May-15 | 20239 | 2 | | | II-1 | Spata20 | 64847 | 4-May-15 |
| 19621 | 2 | | | II-1 | Slc35c1 | 55343 | 28-May-15 | 20240 | 2 | | | II-1 | Spata21 | 374955 | 4-May-15 |
| 19623 | 2 | | | II-1 | Slc35d1 | 23169 | 12-May-15 | 20241 | 2 | | | II-1 | Spata22 | 84690 | 4-May-15 |
| 19626 | 2 | | | II-1 | Slc35e1 | 79939 | 4-May-15 | 20247 | 2 | | | II-1 | Spata31d1a | | |
| 19634 | 2 | | | II-1 | Slc35f5 | 80255 | 4-May-15 | 20248 | 2 | | | II-1 | Spata31d1b | | |

Fig.22 - 110

| | | | | | | | | | | | | | |
|---|---|---|---|---|---|---|---|---|---|---|---|---|---|
| 20250 | 2 | | | II-1 | Spata31d1d | | | 20668 | 2 | | | II-1 | Sugt1 | 10910 | 28-May-15 |
| 20251 | 2 | | | II-1 | Spata32 | 124783 | 21-May-15 | 20679 | 2 | | | II-1 | Sult2a3 | | |
| 20255 | 2 | | | II-1 | Spata5 | 166378 | 4-May-15 | 20690 | 2 | | | II-1 | Sumf2 | 25870 | 4-May-15 |
| 20262 | 2 | | | II-1 | Spats1 | 221409 | 4-May-15 | 20695 | 2 | | | II-1 | Sun2 | 25777 | 17-May-15 |
| 20263 | 2 | | | II-1 | Spats2 | 65244 | 12-May-15 | 20697 | 2 | | | II-1 | Sun5 | 140732 | 4-May-15 |
| 20269 | 2 | | | II-1 | Spcs3 | 60559 | 4-May-15 | 20700 | 2 | | | II-1 | Supt20 | | |
| 20271 | 2 | | | II-1 | Spdl1 | 54908 | 4-May-15 | 20702 | 2 | | | II-1 | Supt4a | | |
| 20277 | 2 | | | II-1 | Speer2 | | | 20704 | 2 | | | II-1 | Supt6 | | |
| 20278 | 2 | | | II-1 | Speer3 | | | 20705 | 2 | | | II-1 | Supt7l | 9913 | 4-May-15 |
| 20279 | 2 | | | II-1 | Speer4a | | | 20706 | 2 | | | II-1 | Supv3l1 | 6832 | 4-May-15 |
| 20280 | 2 | | | II-1 | Speer4b | | | 20707 | 2 | | | II-1 | Surf1 | 6834 | 23-May-15 |
| 20281 | 2 | | | II-1 | Speer4c | | | 20708 | 2 | | | II-1 | Surf2 | 6835 | 4-May-15 |
| 20282 | 2 | | | II-1 | Speer4d | | | 20709 | 2 | | | II-1 | Surf4 | 6836 | 4-May-15 |
| 20283 | 2 | | | II-1 | Speer4e | | | 20710 | 2 | | | II-1 | Surf6 | 6838 | 31-May-15 |
| 20286 | 2 | | | II-1 | Speer6-ps1 | | | 20718 | 2 | | | II-1 | Suv420h1 | 51111 | 12-May-15 |
| 20287 | 2 | | | II-1 | Speer7-ps1 | | | 20720 | 2 | | | II-1 | Suz12 | 23512 | 4-May-15 |
| 20297 | 2 | | | II-1 | Spg11 | 80208 | 23-May-15 | 20723 | 2 | | | II-1 | Sv2c | 22987 | 4-May-15 |
| 20300 | 2 | | | II-1 | Spg7 | 6687 | 23-May-15 | 20724 | 2 | | | II-1 | Sva | | |
| 20309 | 2 | | | II-1 | Spin1 | 10927 | 7-Jun-15 | 20726 | 2 | | | II-1 | Sval2 | | |
| 20312 | 2 | | | II-1 | Spin2-ps1 | | | 20728 | 2 | | | II-1 | Svep1 | 79987 | 12-May-15 |
| 20313 | 2 | | | II-1 | Spin4 | 139888 | 4-May-15 | 20732 | 2 | | | II-1 | Svopl | 136306 | 4-May-15 |
| 20324 | 2 | | | II-1 | Spink7 | 84651 | 12-May-15 | 20734 | 2 | | | II-1 | Svs2 | | |
| 20337 | 2 | | | II-1 | Spns2 | 124976 | 4-May-15 | 20735 | 2 | | | II-1 | Svs3a | | |
| 20351 | 2 | | | II-1 | Sppl2c | 162340 | 12-May-15 | 20741 | 2 | | | II-1 | Swi5 | 375757 | 4-May-15 |
| 20353 | 2 | | | II-1 | Spr | 6697 | 7-Jun-15 | 20743 | 2 | | | II-1 | Swt1 | 54823 | 4-May-15 |
| 20354 | 2 | | | II-1 | Spred1 | 161742 | 23-May-15 | 20753 | 2 | | | II-1 | Sycp2 | 10388 | 4-May-15 |
| 20355 | 2 | | | II-1 | Spred2 | 200734 | 2-Jun-15 | 20754 | 2 | | | II-1 | Sycp3 | 50511 | 4-May-15 |
| 20376 | 2 | | | II-1 | Spir2k | | | 20758 | 2 | | | II-1 | Syk | 6850 | 10-May-15 |
| 20377 | 2 | | | II-1 | Spry4 | 81848 | 4-May-15 | 20768 | 2 | | | II-1 | Syndig1l | 646658 | 4-May-15 |
| 20392 | 2 | | | II-1 | Sptlc1 | 10558 | 23-May-15 | 20769 | 2 | | | II-1 | Syne1 | 23345 | 23-May-15 |
| 20394 | 2 | | | II-1 | Sptlc3 | 55304 | 4-May-15 | 20779 | 2 | | | II-1 | Synj2 | 8871 | 4-May-15 |
| 20404 | 2 | | | II-1 | Src | 6714 | 17-May-15 | 20787 | 2 | | | II-1 | Syp | 6855 | 4-May-15 |
| 20406 | 2 | | | II-1 | Srcrb4d | 136853 | 12-May-15 | 20815 | 2 | | | II-1 | Szt2 | 23334 | 12-May-15 |
| 20413 | 2 | | | II-1 | Srek1ip1 | 285672 | 12-May-15 | 20816 | 2 | | | II-1 | T | 6862 | 4-May-15 |
| 20414 | 2 | | | II-1 | Srf | 6722 | 4-May-15 | 20817 | 2 | | | II-1 | T2 | | |
| 20415 | 2 | | | II-1 | Srfbp1 | 153443 | 4-May-15 | 20818 | 2 | | | II-1 | Taar1 | 134864 | 7-Jun-15 |
| 20427 | 2 | | | II-1 | Srp54b | | | 20820 | 2 | | | II-1 | Taar3 | 9288 | 4-May-15 |
| 20431 | 2 | | | II-1 | Srp9 | 6726 | 12-May-15 | 20840 | 2 | | | II-1 | Tacr2 | 10579 | 12-May-15 |
| 20432 | 2 | | | II-1 | Srpk1 | 6732 | 17-May-15 | 20844 | 2 | | | II-1 | Tacr2 | 6865 | 12-May-15 |
| 20437 | 2 | | | II-1 | Srpx | 8406 | 21-May-15 | 20848 | 2 | | | II-1 | Tada2a | 6871 | 1-Jun-15 |
| 20445 | 2 | | | II-1 | Srrm4os | | | 20850 | 2 | | | II-1 | Tada3 | 10474 | 4-May-15 |
| 20448 | 2 | | | II-1 | Srsf10 | 10772 | 1-Jun-15 | 20851 | 2 | | | II-1 | Taf1 | 6872 | 23-May-15 |
| 20451 | 2 | | | II-1 | Srsf2 | 6427 | 31-May-15 | 20853 | 2 | | | II-1 | Taf11 | 6882 | 4-May-15 |
| 20453 | 2 | | | II-1 | Srsf4 | 6429 | 4-May-15 | 20863 | 2 | | | II-1 | Taf4a | 6874 | 12-May-15 |
| 20456 | 2 | | | II-1 | Srsf7 | 6432 | 1-Jun-15 | 20864 | 2 | | | II-1 | Taf4b | 6875 | 16-Jun-15 |
| 20457 | 2 | | | II-1 | Srsf9 | 8683 | 31-May-15 | 20866 | 2 | | | II-1 | Taf5l | 27097 | 4-May-15 |
| 20458 | 2 | | | II-1 | Srxn1 | 140809 | 4-May-15 | 20868 | 2 | | | II-1 | Taf6l | 10629 | 4-May-15 |
| 20465 | 2 | | | II-1 | Ssbp3 | 23648 | 12-May-15 | 20873 | 2 | | | II-1 | Taf9b | 51616 | 4-May-15 |
| 20474 | 2 | | | II-1 | Sspn | 8082 | 14-May-15 | 20874 | 2 | | | II-1 | Tagap | 117289 | 4-May-15 |
| 20477 | 2 | | | II-1 | Ssr2 | 6746 | 4-May-15 | 20887 | 2 | | | II-1 | Tank | 10010 | 4-May-15 |
| 20479 | 2 | | | II-1 | Ssr4 | 6748 | 23-May-15 | 20889 | 2 | | | II-1 | Taok2 | 9344 | 4-May-15 |
| 20481 | 2 | | | II-1 | Ssscal | 10534 | 12-May-15 | 20890 | 2 | | | II-1 | Taok3 | 51347 | 12-May-15 |
| 20491 | 2 | | | II-1 | Ssu72 | 29101 | 4-May-15 | 20891 | 2 | | | II-1 | Tap1 | 6890 | 13-Jun-15 |
| 20495 | 2 | | | II-1 | Ssxb10 | | | 20894 | 2 | | | II-1 | Tapbpl | 55080 | 4-May-15 |
| 20498 | 2 | | | II-1 | Ssxb5 | | | 20895 | 2 | | | II-1 | Tapt1 | 202018 | 4-May-15 |
| 20499 | 2 | | | II-1 | Ssxb6 | | | 20900 | 2 | | | II-1 | Tars2 | 80222 | 4-May-15 |
| 20522 | 2 | | | II-1 | St8sia1 | 6489 | 4-May-15 | 20901 | 2 | | | II-1 | Tarsl2 | 123283 | 4-May-15 |
| 20523 | 2 | | | II-1 | St8sia2 | 8128 | 4-May-15 | 20903 | 2 | | | II-1 | Tas1r2 | 80834 | 7-Jun-15 |
| 20539 | 2 | | | II-1 | Stambp | 10617 | 23-May-15 | 20904 | 2 | | | II-1 | Tas1r3 | 83756 | 4-May-15 |
| 20548 | 2 | | | II-1 | Stard3nl | 83930 | 4-May-15 | 20907 | 2 | | | II-1 | Tas2r104 | | |
| 20549 | 2 | | | II-1 | Stard4 | 134429 | 12-May-15 | 20921 | 2 | | | II-1 | Tas2r120 | | |
| 20552 | 2 | | | II-1 | Stard7 | 56910 | 4-May-15 | 20945 | 2 | | | II-1 | Tax1bp1 | 8887 | 12-May-15 |
| 20553 | 2 | | | II-1 | Stard8 | 9754 | 4-May-15 | 20946 | 2 | | | II-1 | Tax1bp3 | 30851 | 1-Jun-15 |
| 20555 | 2 | | | II-1 | Stat2 | 6773 | 28-May-15 | 20951 | 2 | | | II-1 | Tbc1d10b | 26000 | 4-May-15 |
| 20558 | 2 | | | II-1 | Stat5a | 6776 | 31-May-15 | 20952 | 2 | | | II-1 | Tbc1d10c | 374403 | 12-May-15 |
| 20559 | 2 | | | II-1 | Stat5b | 6777 | 24-May-15 | 20955 | 2 | | | II-1 | Tbc1d14 | 57533 | 21-May-15 |
| 20561 | 2 | | | II-1 | Stau1 | 6780 | 4-May-15 | 20956 | 2 | | | II-1 | Tbc1d15 | 64786 | 4-May-15 |
| 20562 | 2 | | | II-1 | Stau2 | 27067 | 4-May-15 | 20957 | 2 | | | II-1 | Tbc1d16 | 125058 | 4-May-15 |
| 20577 | 2 | | | II-1 | Stip1 | 10963 | 7-Jun-15 | 20960 | 2 | | | II-1 | Tbc1d2 | 55357 | 4-May-15 |
| 20578 | 2 | | | II-1 | Stk10 | 6793 | 4-May-15 | 20962 | 2 | | | II-1 | Tbc1d21 | 161514 | 12-May-15 |
| 20581 | 2 | | | II-1 | Stk16 | 8576 | 28-May-15 | 20963 | 2 | | | II-1 | Tbc1d22a | 25771 | 12-May-15 |
| 20586 | 2 | | | II-1 | Stk3 | 6788 | 7-Jun-15 | 20965 | 2 | | | II-1 | Tbc1d22bos | | |
| 20587 | 2 | | | II-1 | Stk31 | 56164 | 4-May-15 | 20966 | 2 | | | II-1 | Tbc1d23 | 55773 | 4-May-15 |
| 20593 | 2 | | | II-1 | Stk36 | 27148 | 4-May-15 | 20975 | 2 | | | II-1 | Tbc1d7 | 51256 | 4-May-15 |
| 20595 | 2 | | | II-1 | Stk38l | 23012 | 4-May-15 | 20980 | 2 | | | II-1 | Tbca | 6902 | 12-May-15 |
| 20598 | 2 | | | II-1 | Stk40 | 83931 | 4-May-15 | 20983 | 2 | | | II-1 | Tbccd1 | 55171 | 4-May-15 |
| 20599 | 2 | | | II-1 | Stmn1 | 3925 | 24-May-15 | 20985 | 2 | | | II-1 | Tbce | 6905 | 4-May-15 |
| 20607 | 2 | | | II-1 | Stoml2 | 30968 | 4-May-15 | 20986 | 2 | | | II-1 | Tbcel | 219899 | 4-May-15 |
| 20619 | 2 | | | II-1 | Stradb | 55437 | 4-May-15 | 20988 | 2 | | | II-1 | Tbk1 | 29110 | 4-May-15 |
| 20621 | 2 | | | II-1 | Strbp | 55342 | 4-May-15 | 20993 | 2 | | | II-1 | Tbl3 | 10607 | 4-May-15 |
| 20628 | 2 | | | II-1 | Stt3a | 3703 | 4-May-15 | 20995 | 2 | | | II-1 | Tbpl1 | 9519 | 4-May-15 |
| 20629 | 2 | | | II-1 | Stt3b | 201595 | 4-May-15 | 20997 | 2 | | | II-1 | Tbr1 | 10716 | 12-May-15 |
| 20630 | 2 | | | II-1 | Stub1 | 10273 | 12-May-15 | 20998 | 2 | | | II-1 | Tbrg1 | 84897 | 4-May-15 |
| 20634 | 2 | | | II-1 | Stx17 | 55014 | 21-May-15 | 21000 | 2 | | | II-1 | Tbrg4 | 9238 | 4-May-15 |
| 20635 | 2 | | | II-1 | Stx18 | 53407 | 4-May-15 | 21014 | 2 | | | II-1 | Tbx6 | 6911 | 12-May-15 |
| 20642 | 2 | | | II-1 | Stx5a | 6811 | 4-May-15 | 21034 | 2 | | | II-1 | Tceb3 | 6924 | 4-May-15 |
| 20643 | 2 | | | II-1 | Stx6 | 10228 | 12-May-15 | 21036 | 2 | | | II-1 | Tcerg1l | 256536 | 4-May-15 |
| 20644 | 2 | | | II-1 | Stx7 | 8417 | 4-May-15 | 21037 | 2 | | | II-1 | Tcf12 | 6938 | 28-May-15 |
| 20645 | 2 | | | II-1 | Stx8 | 9482 | 10-May-15 | 21045 | 2 | | | II-1 | Tcf3 | 6929 | 7-Jun-15 |
| 20649 | 2 | | | II-1 | Stxbp3b | | | 21046 | 2 | | | II-1 | Tcf4 | 6925 | 7-Jun-15 |
| 20650 | 2 | | | II-1 | Stxbp4 | 252983 | 4-May-15 | 21056 | 2 | | | II-1 | Tcl1b1 | | |
| 20651 | 2 | | | II-1 | Stxbp5 | 134957 | 4-May-15 | 21057 | 2 | | | II-1 | Tcl1b2 | | |
| 20653 | 2 | | | II-1 | Stxbp6 | 29091 | 12-May-15 | 21064 | 2 | | | II-1 | Tcp10a | 6953 | 4-May-15 |
| 20654 | 2 | | | II-1 | Styk1 | 55359 | 31-May-15 | 21065 | 2 | | | II-1 | Tcp10b | | |
| 20656 | 2 | | | II-1 | Styxl1 | 51657 | 12-May-15 | 21066 | 2 | | | II-1 | Tcp10c | | |
| 20657 | 2 | | | II-1 | Sub1 | 10923 | 28-May-15 | 21072 | 2 | | | II-1 | Tcta | 6988 | 4-May-15 |
| 20665 | 2 | | | II-1 | Sugct | 79783 | 12-May-15 | 21073 | 2 | | | II-1 | Tcte1 | 202500 | 4-May-15 |

Fig.22 - 111

| | | | | | | | | | | | | | |
|---|---|---|---|---|---|---|---|---|---|---|---|---|---|
| 21080 | 2 | | | H-1 | Tctn2 | 79867 | 23-May-15 | 21552 | 2 | | | H-1 | Tmem237 | 65062 | 23-May-15 |
| 21089 | 2 | | | H-1 | Tdpoz2 | | | 21555 | 2 | | | H-1 | Tmem240 | 339453 | 23-May-15 |
| 21090 | 2 | | | H-1 | Tdpoz3 | | | 21558 | 2 | | | H-1 | Tmem243 | 79161 | 4-May-15 |
| 21099 | 2 | | | H-1 | Tdrd9 | 122402 | 4-May-15 | 21562 | 2 | | | H-1 | Tmem248 | 55069 | 4-May-15 |
| 21120 | 2 | | | H-1 | Tekt4 | 150483 | 4-May-15 | 21563 | 2 | | | H-1 | Tmem25 | 84866 | 4-May-15 |
| 21121 | 2 | | | H-1 | Tekt5 | 146279 | 4-May-15 | 21576 | 2 | | | H-1 | Tmem260 | 54916 | 4-May-15 |
| 21122 | 2 | | | H-1 | Telo2 | 9894 | 4-May-15 | 21586 | 2 | | | H-1 | Tmem35 | 59353 | 4-May-15 |
| 21123 | 2 | | | H-1 | Ten1 | 100134 934 | 4-May-15 | 21591 | 2 | | | H-1 | Tmem39b | 55116 | 28-May-15 |
| 21126 | 2 | | | H-1 | Tenm2 | 57451 | 12-May-15 | 21596 | 2 | | | H-1 | Tmem43 | 79188 | 23-May-15 |
| 21127 | 2 | | | H-1 | Tenm3 | 55714 | 4-May-15 | 21597 | 2 | | | H-1 | Tmem44 | 93109 | 4-May-15 |
| 21140 | 2 | | | H-1 | Tesk2 | 10420 | 4-May-15 | 21614 | 2 | | | H-1 | Tmem59 | 9528 | 4-May-15 |
| 21141 | 2 | | | H-1 | Tespa1 | 9840 | 4-May-15 | 21615 | 2 | | | H-1 | Tmem59l | 25789 | 4-May-15 |
| 21148 | 2 | | | H-1 | Tex12 | 56158 | 4-May-15 | 21616 | 2 | | | H-1 | Tmem60 | 85025 | 21-May-15 |
| 21151 | 2 | | | H-1 | Tex14 | 56155 | 4-May-15 | 21618 | 2 | | | H-1 | Tmem63a | 9725 | 12-May-15 |
| 21152 | 2 | | | H-1 | Tex15 | 56154 | 4-May-15 | 21620 | 2 | | | H-1 | Tmem63c | 57156 | 4-May-15 |
| 21153 | 2 | | | H-1 | Tex16 | | | 21625 | 2 | | | H-1 | Tmem68 | 137695 | 4-May-15 |
| 21155 | 2 | | | H-1 | Tex19.2 | | | 21627 | 2 | | | H-1 | Tmem70 | 54968 | 12-May-15 |
| 21156 | 2 | | | H-1 | Tex2 | 55852 | 4-May-15 | 21631 | 2 | | | H-1 | Tmem74b | 55321 | 12-May-15 |
| 21157 | 2 | | | H-1 | Tex21 | | | 21636 | 2 | | | H-1 | Tmem82 | 388595 | 4-May-15 |
| 21159 | 2 | | | H-1 | Tex24 | | | 21642 | 2 | | | H-1 | Tmem88b | 643965 | 4-May-15 |
| 21160 | 2 | | | H-1 | Tex28 | 122046 | 4-May-15 | 21646 | 2 | | | H-1 | Tmem9 | 252839 | 4-May-15 |
| 21162 | 2 | | | H-1 | Tex264 | 51368 | 4-May-15 | 21649 | 2 | | | H-1 | Tmem95 | 339168 | 4-May-15 |
| 21163 | 2 | | | H-1 | Tex28 | 1527 | 4-May-15 | 21650 | 2 | | | H-1 | Tmem97 | 27346 | 31-May-15 |
| 21165 | 2 | | | H-1 | Tex30 | 93081 | 4-May-15 | 21654 | 2 | | | H-1 | Tmf1 | 7110 | 4-May-15 |
| 21168 | 2 | | | H-1 | Tex36 | 387718 | 4-May-15 | 21655 | 2 | | | H-1 | Tmie | 259236 | 23-May-15 |
| 21169 | 2 | | | H-1 | Tex37 | 200523 | 20-May-15 | 21667 | 2 | | | H-1 | Tmprss11d | 9407 | 4-May-15 |
| 21179 | 2 | | | H-1 | Tfap2e | 339488 | 28-May-15 | 21672 | 2 | | | H-1 | Tmprss13 | 84000 | 4-May-15 |
| 21183 | 2 | | | H-1 | Tfcp2 | 7024 | 4-May-15 | 21680 | 2 | | | H-1 | Tmprss9 | 360200 | 4-May-15 |
| 21188 | 2 | | | H-1 | Tfeb | 7942 | 28-May-15 | 21693 | 2 | | | H-1 | Tmx1 | 81542 | 4-May-15 |
| 21195 | 2 | | | H-1 | Tfpi | 7035 | 12-May-15 | 21695 | 2 | | | H-1 | Tmx3 | 54495 | 4-May-15 |
| 21196 | 2 | | | H-1 | Tfpi2 | 7980 | 12-May-15 | 21697 | 2 | | | H-1 | Tnc | 3371 | 7-Jun-15 |
| 21210 | 2 | | | H-1 | Tgfbr3 | 7049 | 12-May-15 | 21700 | 2 | | | H-1 | Tnfaip2 | 7127 | 4-May-15 |
| 21231 | 2 | | | H-1 | Thap1 | 56145 | 17-May-15 | 21704 | 2 | | | H-1 | Tnfaip8l1 | 126282 | 12-May-15 |
| 21232 | 2 | | | H-1 | Thap11 | 57215 | 12-May-15 | 21736 | 2 | | | H-1 | Tnfsf4 | 7292 | 4-May-15 |
| 21233 | 2 | | | H-1 | Thap2 | 83591 | 4-May-15 | 21738 | 2 | | | H-1 | Tnfsf9 | 8744 | 4-May-15 |
| 21236 | 2 | | | H-1 | Thap6 | 152815 | 4-May-15 | 21765 | 2 | | | H-1 | Thr | 7143 | 4-May-15 |
| 21237 | 2 | | | H-1 | Thap7 | 80764 | 4-May-15 | 21766 | 2 | | | H-1 | Tnrc18 | 84629 | 7-Jun-15 |
| 21258 | 2 | | | H-1 | Thoc6 | 79228 | 4-May-15 | 21778 | 2 | | | H-1 | Tom1 | 10043 | 4-May-15 |
| 21271 | 2 | | | H-1 | Thumpd1 | 55623 | 12-May-15 | 21781 | 2 | | | H-1 | Tomm20 | 9804 | 12-May-15 |
| 21272 | 2 | | | H-1 | Thumpd2 | 80745 | 4-May-15 | 21783 | 2 | | | H-1 | Tomm22 | 56993 | 4-May-15 |
| 21273 | 2 | | | H-1 | Thumpd3 | 25917 | 12-May-15 | 21786 | 2 | | | H-1 | Tomm40 | 84134 | 4-May-15 |
| 21278 | 2 | | | H-1 | Tiam1 | 7074 | 17-May-15 | 21800 | 2 | | | H-1 | Topaz1 | 375337 | 4-May-15 |
| 21297 | 2 | | | H-1 | Timm17a | 10440 | 4-May-15 | 21801 | 2 | | | H-1 | Topbp1 | 11073 | 4-May-15 |
| 21298 | 2 | | | H-1 | Timm17b | 10245 | 4-May-15 | 21808 | 2 | | | H-1 | Tor1b | 27348 | 4-May-15 |
| 21303 | 2 | | | H-1 | Timm50 | 92609 | 4-May-15 | 21809 | 2 | | | H-1 | Tor2a | 27433 | 31-May-15 |
| 21307 | 2 | | | H-1 | Timm9 | 26520 | 12-May-15 | 21810 | 2 | | | H-1 | Tor3a | 64222 | 12-May-15 |
| 21316 | 2 | | | H-1 | Tiparp | 25976 | 4-May-15 | 21811 | 2 | | | H-1 | Tor4a | 54863 | 4-May-15 |
| 21317 | 2 | | | H-1 | Tipin | 54962 | 4-May-15 | 21819 | 2 | | | H-1 | Tpcn1 | 53373 | 12-May-15 |
| 21323 | 2 | | | H-1 | Tjp1 | 7082 | 31-May-15 | 21837 | 2 | | | H-1 | Tpp2 | 7174 | 4-May-15 |
| 21340 | 2 | | | H-1 | Tll1 | 7092 | 4-May-15 | 21838 | 2 | | | H-1 | Tppp | 11076 | 4-May-15 |
| 21343 | 2 | | | H-1 | Tln2 | 83660 | 4-May-15 | 21845 | 2 | | | H-1 | Tprkb | 51002 | 4-May-15 |
| 21358 | 2 | | | H-1 | Tlx3 | 30012 | 12-May-15 | 21846 | 2 | | | H-1 | Tprn | 286262 | 4-May-15 |
| 21374 | 2 | | | H-1 | Tm9sf4 | 9777 | 4-May-15 | 21854 | 2 | | | H-1 | Tpx2 | 22974 | 4-May-15 |
| 21375 | 2 | | | H-1 | Tma16 | 55319 | 4-May-15 | 21863 | 2 | | | H-1 | Traf3ip1 | 26146 | 4-May-15 |
| 21380 | 2 | | | H-1 | Tmbim7 | | | 21871 | 2 | | | H-1 | Traip | 10293 | 4-May-15 |
| 21381 | 2 | | | H-1 | Tmc1 | 117531 | 23-May-15 | 21875 | 2 | | | H-1 | Tram1l1 | 133022 | 4-May-15 |
| 21382 | 2 | | | H-1 | Tmc2 | 117532 | 4-May-15 | 21880 | 2 | | | H-1 | Trappc1 | 58485 | 4-May-15 |
| 21383 | 2 | | | H-1 | Tmc3 | 342125 | 4-May-15 | 21881 | 2 | | | H-1 | Trappc10 | 7109 | 4-May-15 |
| 21394 | 2 | | | H-1 | Tmco3 | 55002 | 12-May-15 | 21882 | 2 | | | H-1 | Trappc11 | 60684 | 12-May-15 |
| 21397 | 2 | | | H-1 | Tmco5b | 100652 857 | 4-May-15 | 21883 | 2 | | | H-1 | Trappc12 | 51112 | 14-May-15 |
| 21398 | 2 | | | H-1 | Tmco6 | 55374 | 4-May-15 | 21884 | 2 | | | H-1 | Trappc13 | 80006 | 4-May-15 |
| 21400 | 2 | | | H-1 | Tmed10 | 10972 | 12-May-15 | 21885 | 2 | | | H-1 | Trappc2 | 6399 | 23-May-15 |
| 21402 | 2 | | | H-1 | Tmed2 | 10959 | 4-May-15 | 21886 | 2 | | | H-1 | Trappc2l | 51693 | 4-May-15 |
| 21408 | 2 | | | H-1 | Tmed8 | 283578 | 12-May-15 | 21889 | 2 | | | H-1 | Trappc4 | 51399 | 4-May-15 |
| 21409 | 2 | | | H-1 | Tmed9 | 54732 | 4-May-15 | 21894 | 2 | | | H-1 | Trappc9 | 83696 | 4-May-15 |
| 21416 | 2 | | | H-1 | Tmem106a | 113277 | 12-May-15 | 21895 | 2 | | | H-1 | Trat1 | 50852 | 4-May-15 |
| 21419 | 2 | | | H-1 | Tmem107 | 84314 | 12-May-15 | 21912 | 2 | | | H-1 | Trhr | 7201 | 12-May-15 |
| 21421 | 2 | | | H-1 | Tmem109 | 79073 | 4-May-15 | 21913 | 2 | | | H-1 | Trhr2 | | |
| 21423 | 2 | | | H-1 | Tmem110 | 375346 | 4-May-15 | 21923 | 2 | | | H-1 | Trim13 | 10206 | 12-May-15 |
| 21424 | 2 | | | H-1 | Tmem115 | 11070 | 4-May-15 | 21930 | 2 | | | H-1 | Trim23 | 373 | 2-Jun-15 |
| 21425 | 2 | | | H-1 | Tmem116 | 89894 | 4-May-15 | 21934 | 2 | | | H-1 | Trim27 | 5987 | 2-Jun-15 |
| 21426 | 2 | | | H-1 | Tmem117 | 84216 | 4-May-15 | 21935 | 2 | | | H-1 | Trim28 | 10155 | 4-May-15 |
| 21437 | 2 | | | H-1 | Tmem129 | 92305 | 23-May-15 | 21943 | 2 | | | H-1 | Trim32 | 22954 | 23-May-15 |
| 21438 | 2 | | | H-1 | Tmem130 | 222865 | 4-May-15 | 21945 | 2 | | | H-1 | Trim34a | | |
| 21439 | 2 | | | H-1 | Tmem131 | 23505 | 4-May-15 | 21946 | 2 | | | H-1 | Trim34b | | |
| 21445 | 2 | | | H-1 | Tmem132e | 124842 | 4-May-15 | 21955 | 2 | | | H-1 | Trim43a | 129868 | 4-May-15 |
| 21446 | 2 | | | H-1 | Tmem134 | 80194 | 4-May-15 | 21956 | 2 | | | H-1 | Trim43b | 653192 | 4-May-15 |
| 21449 | 2 | | | H-1 | Tmem138 | 51524 | 23-May-15 | 21957 | 2 | | | H-1 | Trim43c | | |
| 21456 | 2 | | | H-1 | Tmem147 | 10430 | 4-May-15 | 21960 | 2 | | | H-1 | Trim46 | 80128 | 4-May-15 |
| 21457 | 2 | | | H-1 | Tmem14a | 28978 | 4-May-15 | 21972 | 2 | | | H-1 | Trim62 | 55223 | 4-May-15 |
| 21458 | 2 | | | H-1 | Tmem14c | 51522 | 4-May-15 | 21979 | 2 | | | H-1 | Trim7 | 81786 | 4-May-15 |
| 21471 | 2 | | | H-1 | Tmem163 | 81615 | 4-May-15 | 21986 | 2 | | | H-1 | Triml2 | 205860 | 7-Jun-15 |
| 21474 | 2 | | | H-1 | Tmem167 | 153339 | 4-May-15 | 21987 | 2 | | | H-1 | Trio | 7204 | 12-May-15 |
| 21475 | 2 | | | H-1 | Tmem167b | 56900 | 4-May-15 | 21988 | 2 | | | H-1 | Triobp | 11078 | 23-May-15 |
| 21477 | 2 | | | H-1 | Tmem169 | 92691 | 4-May-15 | 22008 | 2 | | | H-1 | Trmt44 | 152992 | 12-May-15 |
| 21478 | 2 | | | H-1 | Tmem176 | 200728 | 4-May-15 | 22009 | 2 | | | H-1 | Trmt5 | 57570 | 4-May-15 |
| 21485 | 2 | | | H-1 | Tmem176a | 55365 | 4-May-15 | 22010 | 2 | | | H-1 | Trmt6 | 51605 | 4-May-15 |
| 21496 | 2 | | | H-1 | Tmem181c-ps | | | 22012 | 2 | | | H-1 | Trmt61b | 55006 | 4-May-15 |
| 21506 | 2 | | | H-1 | Tmem190 | 147744 | 4-May-15 | 22021 | 2 | | | H-1 | Troap | 10024 | 4-May-15 |
| 21520 | 2 | | | H-1 | Tmem202 | 338849 | 4-May-15 | 22022 | 2 | | | H-1 | Trp53bp1 | | |
| 21522 | 2 | | | H-1 | Tmem204 | 79652 | 4-May-15 | 22024 | 2 | | | H-1 | Trp53bp2 | | |
| 21525 | 2 | | | H-1 | Tmem207 | 131920 | 4-May-15 | 22032 | 2 | | | H-1 | Trp53i11 | | |
| 21534 | 2 | | | H-1 | Tmem216 | 51259 | 23-May-15 | 22033 | 2 | | | H-1 | Trpa1 | 8989 | 7-Jun-15 |
| 21535 | 2 | | | H-1 | Tmem217 | 221468 | 4-May-15 | 22043 | 2 | | | H-1 | Trpc1 | 7220 | 10-May-15 |
| 21542 | 2 | | | H-1 | Tmem225 | 338661 | 4-May-15 | 22050 | 2 | | | H-1 | Trpm1 | 4308 | 12-May-15 |
| 21544 | 2 | | | H-1 | Tmem229b | 161145 | 4-May-15 | 22052 | 2 | | | H-1 | Trpm8 | 79054 | 24-May-15 |
| | | | | | | | | 22052 | 2 | | | H-1 | Trpt1 | 83707 | 4-May-15 |

Fig.22 - 112

| | | | | | | | | | | | | |
|---|---|---|---|---|---|---|---|---|---|---|---|---|
| 22061 | 2 | | | II-1 | Trub2 | 26995 | 12-May-15 | 22487 | 2 | | II-1 | Upf3a | 65110 | 4-May-15 |
| 22072 | 2 | | | II-1 | Tsen15 | 116461 | 4-May-15 | 22488 | 2 | | II-1 | Upf3b | 65109 | 23-May-15 |
| 22076 | 2 | | | II-1 | Tsfm | 10102 | 4-May-15 | 22515 | 2 | | II-1 | Urod1 | 131669 | 14-May-15 |
| 22077 | 2 | | | II-1 | Tsg101 | 7251 | 1-Jun-15 | 22520 | 2 | | II-1 | Usf1 | 7391 | 4-May-15 |
| 22081 | 2 | | | II-1 | Tshb | 7252 | 31-May-15 | 22521 | 2 | | II-1 | Usf2 | 7392 | 17-May-15 |
| 22082 | 2 | | | II-1 | Tshr | 7253 | 12-May-15 | 22523 | 2 | | II-1 | Ush1g | 124590 | 23-May-15 |
| 22092 | 2 | | | II-1 | Tsnaxip1 | 55815 | 4-May-15 | 22529 | 2 | | II-1 | Usp10 | 9100 | 7-Jun-15 |
| 22118 | 2 | | | II-1 | Tspy12 | 64061 | 4-May-15 | 22535 | 2 | | II-1 | Usp16 | 10600 | 7-Jun-15 |
| 22126 | 2 | | | II-1 | Tspyl4 | 23270 | 12-May-15 | 22536 | 2 | | II-1 | Usp17la | | |
| 22128 | 2 | | | II-1 | Tssc1 | 7260 | 4-May-15 | 22537 | 2 | | II-1 | Usp17lb | | |
| 22141 | 2 | | | II-1 | Ttbk2 | 146057 | 31-May-15 | 22538 | 2 | | II-1 | Usp17lc | | |
| 22145 | 2 | | | II-1 | Ttc14 | 151813 | 4-May-15 | 22547 | 2 | | II-1 | Usp24 | 23358 | 4-May-15 |
| 22146 | 2 | | | II-1 | Ttc16 | 158248 | 4-May-15 | 22548 | 2 | | II-1 | Usp25 | 29761 | 12-May-15 |
| 22148 | 2 | | | II-1 | Ttc18 | 118491 | 4-May-15 | 22549 | 2 | | II-1 | Usp26 | 83844 | 4-May-15 |
| 22150 | 2 | | | II-1 | Ttc21a | 199223 | 4-May-15 | 22550 | 2 | | II-1 | Usp27x | 389856 | 4-May-15 |
| 22152 | 2 | | | II-1 | Ttc22 | 55003 | 4-May-15 | 22551 | 2 | | II-1 | Usp28 | 57646 | 12-May-15 |
| 22154 | 2 | | | II-1 | Ttc23 | 153657 | 22-May-15 | 22553 | 2 | | II-1 | Usp3 | 9960 | 4-May-15 |
| 22155 | 2 | | | II-1 | Ttc24 | 164118 | 4-May-15 | 22554 | 2 | | II-1 | Usp30 | 84749 | 12-May-15 |
| 22163 | 2 | | | II-1 | Ttc30a2 | | | 22555 | 2 | | II-1 | Usp31 | 57478 | 7-Jun-15 |
| 22176 | 2 | | | II-1 | Ttc5 | 91875 | 4-May-15 | 22563 | 2 | | II-1 | Usp39 | 10713 | 4-May-15 |
| 22177 | 2 | | | II-1 | Ttc7 | 57217 | 21-May-15 | 22564 | 2 | | II-1 | Usp4 | 7375 | 12-May-15 |
| 22178 | 2 | | | II-1 | Ttc7b | 145567 | 4-May-15 | 22565 | 2 | | II-1 | Usp40 | 55230 | 12-May-15 |
| 22179 | 2 | | | II-1 | Ttc8 | 123016 | 23-May-15 | 22566 | 2 | | II-1 | Usp42 | 84132 | 12-May-15 |
| 22182 | 2 | | | II-1 | Ttc9c | 283237 | 4-May-15 | 22567 | 2 | | II-1 | Usp43 | 124739 | 4-May-15 |
| 22183 | 2 | | | II-1 | Ttf1 | 7270 | 7-Jun-15 | 22568 | 2 | | II-1 | Usp44 | 84101 | 4-May-15 |
| 22186 | 2 | | | II-1 | Ttll | 9675 | 12-May-15 | 22569 | 2 | | II-1 | Usp45 | 85015 | 4-May-15 |
| 22187 | 2 | | | II-1 | Ttk | 7272 | 4-May-15 | 22572 | 2 | | II-1 | Usp48 | 84196 | 4-May-15 |
| 22199 | 2 | | | II-1 | Ttll7 | 79799 | 4-May-15 | 22573 | 2 | | II-1 | Usp49 | 25862 | 4-May-15 |
| 22232 | 2 | | | II-1 | Tubgcp3 | 10426 | 4-May-15 | 22576 | 2 | | II-1 | Usp51 | 158880 | 4-May-15 |
| 22234 | 2 | | | II-1 | Tubgcp5 | 114791 | 4-May-15 | 22577 | 2 | | II-1 | Usp53 | 54532 | 12-May-15 |
| 22237 | 2 | | | II-1 | Tuft1 | 7286 | 12-May-15 | 22582 | 2 | | II-1 | Usp9x | 8239 | 4-May-15 |
| 22241 | 2 | | | II-1 | Tulp3 | 7289 | 28-May-15 | 22584 | 2 | | II-1 | Uspl1 | 10208 | 23-May-15 |
| 22242 | 2 | | | II-1 | Tulp4 | 56995 | 28-May-15 | 22585 | 2 | | II-1 | Ust | 10090 | 4-May-15 |
| 22250 | 2 | | | II-1 | Tvp23b | 51030 | 4-May-15 | 22592 | 2 | | II-1 | Utp20 | 27340 | 4-May-15 |
| 22252 | 2 | | | II-1 | Twf2 | 11344 | 3-May-15 | 22593 | 2 | | II-1 | Utp23 | 84294 | 4-May-15 |
| 22257 | 2 | | | II-1 | Txk | 7294 | 28-May-15 | 22594 | 2 | | II-1 | Utp3 | 57050 | 4-May-15 |
| 22266 | 2 | | | II-1 | Txndc16 | 57544 | 4-May-15 | 22595 | 2 | | II-1 | Utp6 | 55813 | 4-May-15 |
| 22270 | 2 | | | II-1 | Txndc8 | 255220 | 4-May-15 | 22596 | 2 | | II-1 | Utrn | 7402 | 12-May-15 |
| 22271 | 2 | | | II-1 | Txndc9 | 10190 | 4-May-15 | 22597 | 2 | | II-1 | Uts2 | 10911 | 17-May-15 |
| 22272 | 2 | | | II-1 | Txnip | 10628 | 12-May-15 | 22598 | 2 | | II-1 | Uts2b | 257313 | 4-May-15 |
| 22275 | 2 | | | II-1 | Txnl4b | 54957 | 4-May-15 | 22606 | 2 | | II-1 | V1rd18 | | |
| 22276 | 2 | | | II-1 | Txnrd1 | 7296 | 14-May-15 | 22607 | 2 | | II-1 | V1rd19 | | |
| 22277 | 2 | | | II-1 | Txnrd2 | 10587 | 4-May-15 | 22608 | 2 | | II-1 | Vac14 | 55697 | 4-May-15 |
| 22295 | 2 | | | II-1 | U90926 | | | 22611 | 2 | | II-1 | Vamp3 | 9341 | 4-May-15 |
| 22301 | 2 | | | II-1 | Uba2 | 10054 | 23-May-15 | 22612 | 2 | | II-1 | Vamp4 | 8674 | 4-May-15 |
| 22302 | 2 | | | II-1 | Uba3 | 9039 | 23-May-15 | 22620 | 2 | | II-1 | Vars | 7407 | 21-May-15 |
| 22304 | 2 | | | II-1 | Uba52 | 7311 | 1-Jun-15 | 22622 | 2 | | II-1 | Vash1 | 22846 | 21-May-15 |
| 22309 | 2 | | | II-1 | Uhaid1 | 124402 | 4-May-15 | 22633 | 2 | | II-1 | Vax2 | 25806 | 4-May-15 |
| 22313 | 2 | | | II-1 | Ubap2 | 55833 | 4-May-15 | 22634 | 2 | | II-1 | Vax2os | | |
| 22316 | 2 | | | II-1 | Ubash3b | 84959 | 4-May-15 | 22635 | 2 | | II-1 | Vbp1 | 7411 | 1-Jun-15 |
| 22317 | 2 | | | II-1 | Ubb | 7314 | 29-May-15 | 22640 | 2 | | II-1 | Vcpip1 | 80124 | 4-May-15 |
| 22327 | 2 | | | II-1 | Ube2d3 | 7323 | 4-May-15 | 22644 | 2 | | II-1 | Vdac3 | 7419 | 7-Jun-15 |
| 22328 | 2 | | | II-1 | Ube2dnl1 | | | 22672 | 2 | | II-1 | Vmn1r1 | | |
| 22329 | 2 | | | II-1 | Ube2dnl2 | | | 22739 | 2 | | II-1 | Vmn1r185 | | |
| 22330 | 2 | | | II-1 | Ube2e1 | 7324 | 4-May-15 | 22769 | 2 | | II-1 | Vmn1r212 | | |
| 22331 | 2 | | | II-1 | Ube2e2 | 7325 | 12-May-15 | 22875 | 2 | | II-1 | Vmn1r-ps103 | | |
| 22332 | 2 | | | II-1 | Ube2e3 | 10477 | 4-May-15 | 22876 | 2 | | II-1 | Vmn1r-ps79 | | |
| 22334 | 2 | | | II-1 | Ube2g1 | 7326 | 29-May-15 | 22878 | 2 | | II-1 | Vmn2r10 | | |
| 22335 | 2 | | | II-1 | Ube2g2 | 7327 | 12-May-15 | 22925 | 2 | | II-1 | Vmn2r31 | | |
| 22336 | 2 | | | II-1 | Ube2h | 7328 | 12-May-15 | 22937 | 2 | | II-1 | Vmn2r42 | | |
| 22337 | 2 | | | II-1 | Ube2i | 7329 | 17-May-15 | 22969 | 2 | | II-1 | Vmn2r72 | | |
| 22338 | 2 | | | II-1 | Ube2j1 | 51465 | 3-May-15 | 22985 | 2 | | II-1 | Vmn2r87 | | |
| 22344 | 2 | | | II-1 | Ube2n | 7334 | 4-May-15 | 22989 | 2 | | II-1 | Vmn2r90 | | |
| 22345 | 2 | | | II-1 | Ube2o | 63893 | 4-May-15 | 22999 | 2 | | II-1 | Vmn2r-ps11 | | |
| 22351 | 2 | | | II-1 | Ube2t | 29089 | 4-May-15 | 23002 | 2 | | II-1 | Vmn2r-ps54 | | |
| 22354 | 2 | | | II-1 | Ube2v2 | 7336 | 4-May-15 | 23004 | 2 | | II-1 | Vmo1 | 284013 | 4-May-15 |
| 22355 | 2 | | | II-1 | Ube2w | 55284 | 4-May-15 | 23020 | 2 | | II-1 | Vps25 | 84313 | 4-May-15 |
| 22356 | 2 | | | II-1 | Ube2z | 65264 | 4-May-15 | 23021 | 2 | | II-1 | Vps26a | 9559 | 4-May-15 |
| 22362 | 2 | | | II-1 | Ubfd1 | 56061 | 12-May-15 | 23022 | 2 | | II-1 | Vps26b | 112936 | 4-May-15 |
| 22369 | 2 | | | II-1 | Ubkp1 | 134510 | 28-May-15 | 23026 | 2 | | II-1 | Vps33b | 26276 | 4-May-15 |
| 22371 | 2 | | | II-1 | Ubn2 | 254048 | 4-May-15 | 23028 | 2 | | II-1 | Vps36 | 51028 | 4-May-15 |
| 22372 | 2 | | | II-1 | Ubox5 | 22888 | 4-May-15 | 23036 | 2 | | II-1 | Vps4a | 27183 | 4-May-15 |
| 22374 | 2 | | | II-1 | Ubqln1 | 29979 | 21-May-15 | 23038 | 2 | | II-1 | Vps51 | 738 | 29-May-15 |
| 22375 | 2 | | | II-1 | Ubqln2 | 29978 | 23-May-15 | 23039 | 2 | | II-1 | Vps52 | 6293 | 29-May-15 |
| 22376 | 2 | | | II-1 | Ubqln3 | 50613 | 4-May-15 | 23040 | 2 | | II-1 | Vps53 | 55275 | 29-May-15 |
| 22379 | 2 | | | II-1 | Ubr1 | 197131 | 12-May-15 | 23041 | 2 | | II-1 | Vps54 | 51542 | 29-May-15 |
| 22380 | 2 | | | II-1 | Ubr2 | 23304 | 4-May-15 | 23042 | 2 | | II-1 | Vps72 | 6944 | 4-May-15 |
| 22381 | 2 | | | II-1 | Ubr3 | 130507 | 4-May-15 | 23043 | 2 | | II-1 | Vps8 | 23355 | 21-May-15 |
| 22382 | 2 | | | II-1 | Ubr4 | 23352 | 4-May-15 | 23046 | 2 | | II-1 | Vrk2 | 7444 | 4-May-15 |
| 22383 | 2 | | | II-1 | Ubr5 | 51366 | 12-May-15 | 23062 | 2 | | II-1 | Vsx2 | 338917 | 7-Jun-15 |
| 22384 | 2 | | | II-1 | Ubr7 | 55148 | 4-May-15 | 23063 | 2 | | II-1 | Vta1 | 51534 | 31-May-15 |
| 22389 | 2 | | | II-1 | Ubxn1 | 51035 | 31-May-15 | 23064 | 2 | | II-1 | Vtcn1 | 79679 | 24-May-15 |
| 22397 | 2 | | | II-1 | Ubxn8 | 7993 | 4-May-15 | 23065 | 2 | | II-1 | Vti1a | 143187 | 21-May-15 |
| 22418 | 2 | | | II-1 | Ufm1 | 51569 | 4-May-15 | 23066 | 2 | | II-1 | Vti1b | 10490 | 21-May-15 |
| 22419 | 2 | | | II-1 | Ufsp1 | 402682 | 4-May-15 | 23072 | 2 | | II-1 | Vwa5b1 | 127731 | 4-May-15 |
| 22425 | 2 | | | II-1 | Ugp2 | 7360 | 4-May-15 | 23074 | 2 | | II-1 | Vwa7 | 80737 | 4-May-15 |
| 22435 | 2 | | | II-1 | Ugt2a2 | 574537 | 12-May-15 | 23078 | 2 | | II-1 | Vwc2l | 402117 | 2-Jun-15 |
| 22436 | 2 | | | II-1 | Ugt2a3 | 79799 | 28-May-15 | 23079 | 2 | | II-1 | Vwce | 220001 | 4-May-15 |
| 22452 | 2 | | | II-1 | Uimc1 | 51720 | 4-May-15 | 23080 | 2 | | II-1 | Vwde | 221806 | 7-Jun-15 |
| 22453 | 2 | | | II-1 | Uhbp1 | 80329 | 4-May-15 | 23081 | 2 | | II-1 | Vwf | 7450 | 31-May-15 |
| 22456 | 2 | | | II-1 | Ulk3 | 25989 | 21-May-15 | 23084 | 2 | | II-1 | Wapal | 23063 | 4-May-15 |
| 22460 | 2 | | | II-1 | Umps | 7372 | 12-May-15 | 23094 | 2 | | II-1 | Wbp11 | 51729 | 3-May-15 |
| 22466 | 2 | | | II-1 | Unc13d | 201294 | 12-May-15 | 23097 | 2 | | II-1 | Wbp2nl | 164684 | 12-May-15 |
| 22467 | 2 | | | II-1 | Unc45a | 55898 | 4-May-15 | 23098 | 2 | | II-1 | Wbp4 | 11193 | 4-May-15 |
| 22475 | 2 | | | II-1 | Unc79 | 57578 | 4-May-15 | 23099 | 2 | | II-1 | Wbp5 | 51186 | 4-May-15 |
| 22476 | 2 | | | II-1 | Unc80 | 285175 | 4-May-15 | 23106 | 2 | | II-1 | Wdfy1 | 57590 | 12-May-15 |
| 22486 | 2 | | | II-1 | Upf2 | 26019 | 12-May-15 | 23113 | 2 | | II-1 | Wdr11 | 55717 | 7-Jun-15 |

Fig.22 - 113

| | | | | | | | | | | | | | |
|---|---|---|---|---|---|---|---|---|---|---|---|---|---|
| 23114 | 2 | | | II-1 | Wdr12 | 55759 | 4-May-15 | 23483 | 2 | | | II-1 | Zeb1 | 6935 | 31-May-15 |
| 23117 | 2 | | | II-1 | Wdr17 | 116966 | 4-May-15 | 23484 | 2 | | | II-1 | Zeb2 | 9839 | 31-May-15 |
| 23119 | 2 | | | II-1 | Wdr19 | 57728 | 4-May-15 | 23493 | 2 | | | II-1 | Zfand5 | 7763 | 4-May-15 |
| 23120 | 2 | | | II-1 | Wdr20 | 91833 | 3-May-15 | 23496 | 2 | | | II-1 | Zfat | 57623 | 28-May-15 |
| 23121 | 2 | | | II-1 | Wdr20rt | | | 23497 | 2 | | | II-1 | Zfc3h1 | 196441 | 4-May-15 |
| 23125 | 2 | | | II-1 | Wdr27 | 253769 | 4-May-15 | 23501 | 2 | | | II-1 | Zfhx4 | 79776 | 12-May-15 |
| 23126 | 2 | | | II-1 | Wdr3 | 10885 | 12-May-15 | 23505 | 2 | | | II-1 | Zfp106 | 7584 | 12-May-15 |
| 23129 | 2 | | | II-1 | Wdr34 | 89891 | 4-May-15 | 23512 | 2 | | | II-1 | Zfp112 | 7771 | 4-May-15 |
| 23132 | 2 | | | II-1 | Wdr37 | 22884 | 4-May-15 | 23514 | 2 | | | II-1 | Zfp114 | | |
| 23133 | 2 | | | II-1 | Wdr38 | 401551 | 4-May-15 | 23518 | 2 | | | II-1 | Zfp120 | | |
| 23134 | 2 | | | II-1 | Wdr4 | 10785 | 4-May-15 | 23527 | 2 | | | II-1 | Zfp148 | 7707 | 2-Jun-15 |
| 23135 | 2 | | | II-1 | Wdr41 | 55255 | 4-May-15 | 23528 | 2 | | | II-1 | Zfp157 | | |
| 23136 | 2 | | | II-1 | Wdr43 | 23160 | 4-May-15 | 23534 | 2 | | | II-1 | Zfp184 | | |
| 23140 | 2 | | | II-1 | Wdr46 | 9277 | 4-May-15 | 23541 | 2 | | | II-1 | Zfp212 | | |
| 23142 | 2 | | | II-1 | Wdr48 | 57599 | 12-May-15 | 23542 | 2 | | | II-1 | Zfp213 | | |
| 23144 | 2 | | | II-1 | Wdr52 | 55779 | 4-May-15 | 23546 | 2 | | | II-1 | Zfp235 | | |
| 23148 | 2 | | | II-1 | Wdr59 | 79726 | 29-May-15 | 23549 | 2 | | | II-1 | Zfp248 | | |
| 23149 | 2 | | | II-1 | Wdr5b | 54554 | 4-May-15 | 23551 | 2 | | | II-1 | Zfp26 | 50862 | 1-Jun-15 |
| 23150 | 2 | | | II-1 | Wdr6 | 11180 | 4-May-15 | 23554 | 2 | | | II-1 | Zfp266 | | |
| 23153 | 2 | | | II-1 | Wdr62 | 284403 | 23-May-15 | 23555 | 2 | | | II-1 | Zfp27 | | |
| 23154 | 2 | | | II-1 | Wdr63 | 126820 | 12-May-15 | 23557 | 2 | | | II-1 | Zfp275 | | |
| 23155 | 2 | | | II-1 | Wdr64 | 128025 | 4-May-15 | 23559 | 2 | | | II-1 | Zfp277 | | |
| 23157 | 2 | | | II-1 | Wdr7 | 23335 | 4-May-15 | 23567 | 2 | | | II-1 | Zfp287 | | |
| 23158 | 2 | | | II-1 | Wdr70 | 55100 | 4-May-15 | 23581 | 2 | | | II-1 | Zfp330 | | |
| 23161 | 2 | | | II-1 | Wdr74 | 54663 | 12-May-15 | 23584 | 2 | | | II-1 | Zfp341 | | |
| 23164 | 2 | | | II-1 | Wdr77 | 79084 | 4-May-15 | 23585 | 2 | | | II-1 | Zfp345 | | |
| 23166 | 2 | | | II-1 | Wdr8 | 49856 | 12-May-15 | 23586 | 2 | | | II-1 | Zfp346 | 23567 | 21-May-15 |
| 23177 | 2 | | | II-1 | Wdr95 | | | 23587 | 2 | | | II-1 | Zfp35 | | |
| 23179 | 2 | | | II-1 | Wdsub1 | 151525 | 12-May-15 | 23589 | 2 | | | II-1 | Zfp354a | | |
| 23180 | 2 | | | II-1 | Wdtc1 | 23038 | 21-May-15 | 23592 | 2 | | | II-1 | Zfp358 | | |
| 23181 | 2 | | | II-1 | Wdyhv1 | 55093 | 23-May-15 | 23595 | 2 | | | II-1 | Zfp365 | | |
| 23182 | 2 | | | II-1 | Wee1 | 7465 | 4-May-15 | 23603 | 2 | | | II-1 | Zfp382 | | |
| 23184 | 2 | | | II-1 | Wfdc1 | 58189 | 4-May-15 | 23610 | 2 | | | II-1 | Zfp389 | | |
| 23219 | 2 | | | II-1 | Wls | 79971 | 17-May-15 | 23612 | 2 | | | II-1 | Zfp395 | | |
| 23226 | 2 | | | II-1 | Wnk1 | 85125 | 31-May-15 | 23619 | 2 | | | II-1 | Zfp410 | | |
| 23233 | 2 | | | II-1 | Wnt4 | 54361 | 4-May-15 | 23636 | 2 | | | II-1 | Zfp451 | | |
| 23241 | 2 | | | II-1 | Wnt9a | 7483 | 4-May-15 | 23638 | 2 | | | II-1 | Zfp455 | | |
| 23244 | 2 | | | II-1 | Wrb | 7485 | 4-May-15 | 23640 | 2 | | | II-1 | Zfp457 | | |
| 23246 | 2 | | | II-1 | Wrnip1 | 56897 | 4-May-15 | 23642 | 2 | | | II-1 | Zfp459 | | |
| 23260 | 2 | | | II-1 | Wwtr1 | 25937 | 4-May-15 | 23648 | 2 | | | II-1 | Zfp474 | | |
| 23263 | 2 | | | II-1 | Xbp1 | 7494 | 7-Jun-15 | 23654 | 2 | | | II-1 | Zfp511 | | |
| 23287 | 2 | | | II-1 | Xkr5b | | | 23655 | 2 | | | II-1 | Zfp512 | | |
| 23288 | 2 | | | II-1 | Xkr5c | | | 23656 | 2 | | | II-1 | Zfp513 | | |
| 23300 | 2 | | | II-1 | Xpo7 | 23039 | 4-May-15 | 23657 | 2 | | | II-1 | Zfp516 | | |
| 23302 | 2 | | | II-1 | Xpr1 | 9213 | 4-May-15 | 23674 | 2 | | | II-1 | Zfp560 | | |
| 23304 | 2 | | | II-1 | Xrcc2 | 7516 | 17-May-15 | 23675 | 2 | | | II-1 | Zfp563 | | |
| 23305 | 2 | | | II-1 | Xrcc3 | 7517 | 22-May-15 | 23681 | 2 | | | II-1 | Zfp575 | | |
| 23313 | 2 | | | II-1 | Xylt1 | 152002 | 12-May-15 | 23682 | 2 | | | II-1 | Zfp579 | | |
| 23318 | 2 | | | II-1 | Yaf2 | 10138 | 4-May-15 | 23683 | 2 | | | II-1 | Zfp58 | | |
| 23321 | 2 | | | II-1 | Yars2 | 51067 | 4-May-15 | 23684 | 2 | | | II-1 | Zfp580 | | |
| 23322 | 2 | | | II-1 | Ybey | 54059 | 4-May-15 | 23690 | 2 | | | II-1 | Zfp597 | | |
| 23323 | 2 | | | II-1 | Ybx1 | 4904 | 2-Jun-15 | 23691 | 2 | | | II-1 | Zfp598 | | |
| 23329 | 2 | | | II-1 | Yes1 | 7525 | 12-May-15 | 23692 | 2 | | | II-1 | Zfp599 | | |
| 23335 | 2 | | | II-1 | Yipf4 | 84272 | 4-May-15 | 23693 | 2 | | | II-1 | Zfp60 | | |
| 23336 | 2 | | | II-1 | Yipf5 | 81555 | 4-May-15 | 23695 | 2 | | | II-1 | Zfp606 | | |
| 23337 | 2 | | | II-1 | Yipf6 | 286451 | 4-May-15 | 23696 | 2 | | | II-1 | Zfp606 | | |
| 23350 | 2 | | | II-1 | Ythdc2 | 64848 | 4-May-15 | 23704 | 2 | | | II-1 | Zfp618 | | |
| 23351 | 2 | | | II-1 | Ythdf1 | 54915 | 12-May-15 | 23707 | 2 | | | II-1 | Zfp622 | | |
| 23353 | 2 | | | II-1 | Ythdf3 | 253943 | 4-May-15 | 23709 | 2 | | | II-1 | Zfp628 | 89887 | 4-May-15 |
| 23354 | 2 | | | II-1 | Ywhab | 7529 | 4-May-15 | 23710 | 2 | | | II-1 | Zfp629 | | |
| 23355 | 2 | | | II-1 | Ywhae | 7531 | 4-May-15 | 23711 | 2 | | | II-1 | Zfp637 | | |
| 23356 | 2 | | | II-1 | Ywhag | 7532 | 4-May-15 | 23712 | 2 | | | II-1 | Zfp639 | | |
| 23357 | 2 | | | II-1 | Ywhah | 7533 | 12-May-15 | 23714 | 2 | | | II-1 | Zfp641 | | |
| 23358 | 2 | | | II-1 | Ywhaq | 10971 | 31-May-15 | 23725 | 2 | | | II-1 | Zfp655 | | |
| 23359 | 2 | | | II-1 | Ywhaz | 7534 | 31-May-15 | 23729 | 2 | | | II-1 | Zfp664 | | |
| 23360 | 2 | | | II-1 | Yy1 | 7528 | 17-May-15 | 23730 | 2 | | | II-1 | Zfp667 | | |
| 23361 | 2 | | | II-1 | Yy2 | 404281 | 4-May-15 | 23734 | 2 | | | II-1 | Zfp68 | | |
| 23362 | 2 | | | II-1 | Zadh2 | 284273 | 12-May-15 | 23736 | 2 | | | II-1 | Zfp688 | | |
| 23368 | 2 | | | II-1 | Zbbx | 79740 | 4-May-15 | 23744 | 2 | | | II-1 | Zfp704 | | |
| 23369 | 2 | | | II-1 | Zbed3 | 84327 | 4-May-15 | 23747 | 2 | | | II-1 | Zfp708 | | |
| 23377 | 2 | | | II-1 | Zbtb12 | 221527 | 4-May-15 | 23748 | 2 | | | II-1 | Zfp709 | | |
| 23383 | 2 | | | II-1 | Zbtb20 | 26137 | 4-May-15 | 23752 | 2 | | | II-1 | Zfp715 | | |
| 23386 | 2 | | | II-1 | Zbtb24 | 9841 | 4-May-15 | 23754 | 2 | | | II-1 | Zfp72 | | |
| 23387 | 2 | | | II-1 | Zbtb25 | 7597 | 28-May-15 | 23756 | 2 | | | II-1 | Zfp738 | | |
| 23388 | 2 | | | II-1 | Zbtb26 | 57684 | 2-Jun-15 | 23757 | 2 | | | II-1 | Zfp74 | | |
| 23394 | 2 | | | II-1 | Zbtb38 | 253461 | 12-May-15 | 23760 | 2 | | | II-1 | Zfp747 | | |
| 23402 | 2 | | | II-1 | Zbtb45 | 84878 | 12-May-15 | 23770 | 2 | | | II-1 | Zfp771 | | |
| 23409 | 2 | | | II-1 | Zbtb7b | 51043 | 4-May-15 | 23773 | 2 | | | II-1 | Zfp775 | | |
| 23428 | 2 | | | II-1 | Zc3h18 | 124245 | 7-Jun-15 | 23776 | 2 | | | II-1 | Zfp780b | | |
| 23429 | 2 | | | II-1 | Zc3h3 | 23144 | 21-May-15 | 23777 | 2 | | | II-1 | Zfp781 | | |
| 23431 | 2 | | | II-1 | Zc3h6 | 376940 | 4-May-15 | 23782 | 2 | | | II-1 | Zfp788 | | |
| 23439 | 2 | | | II-1 | Zcchc10 | 54819 | 12-May-15 | 23784 | 2 | | | II-1 | Zfp791 | | |
| 23442 | 2 | | | II-1 | Zcchc13 | 389874 | 4-May-15 | 23789 | 2 | | | II-1 | Zfp808 | | |
| 23445 | 2 | | | II-1 | Zcchc17 | 51538 | 28-May-15 | 23795 | 2 | | | II-1 | Zfp82 | 284406 | 4-May-15 |
| 23453 | 2 | | | II-1 | Zcchc7 | 84186 | 4-May-15 | 23799 | 2 | | | II-1 | Zfp827 | | |
| 23455 | 2 | | | II-1 | Zcchc9 | 84240 | 4-May-15 | 23801 | 2 | | | II-1 | Zfp831 | | |
| 23456 | 2 | | | II-1 | Zcrb1 | 85437 | 4-May-15 | 23803 | 2 | | | II-1 | Zfp84 | | |
| 23458 | 2 | | | II-1 | Zdbf2 | 57683 | 4-May-15 | 23804 | 2 | | | II-1 | Zfp846 | | |
| 23461 | 2 | | | II-1 | Zdhhc12 | 84885 | 4-May-15 | 23805 | 2 | | | II-1 | Zfp85 | | |
| 23467 | 2 | | | II-1 | Zdhhc18 | 84243 | 4-May-15 | 23813 | 2 | | | II-1 | Zfp869 | | |
| 23468 | 2 | | | II-1 | Zdhhc19 | 131840 | 4-May-15 | 23814 | 2 | | | II-1 | Zfp87 | | |
| 23472 | 2 | | | II-1 | Zdhhc22 | 283576 | 4-May-15 | 23815 | 2 | | | II-1 | Zfp870 | | |
| 23477 | 2 | | | II-1 | Zdhhc4 | 55146 | 4-May-15 | 23823 | 2 | | | II-1 | Zfp9 | 219749 | 4-May-15 |
| 23478 | 2 | | | II-1 | Zdhhc5 | 25921 | 4-May-15 | 23826 | 2 | | | II-1 | Zfp91Cntf | 386607 | 7-Jun-15 |
| 23480 | 2 | | | II-1 | Zdhhc7 | 55625 | 4-May-15 | 23827 | 2 | | | II-1 | Zfp92 | 139735 | 4-May-15 |
| 23481 | 2 | | | II-1 | Zdhhc8 | 29801 | 3-May-15 | 23828 | 2 | | | II-1 | Zfp93 | 9310 | 12-May-15 |
| 23482 | 2 | | | II-1 | Zdhhc9 | 51114 | 4-May-15 | 23834 | 2 | | | II-1 | Zfp935 | | |

Fig.22 - 114

| | | | | | | | | | | | | | |
|---|---|---|---|---|---|---|---|---|---|---|---|---|---|
| 23842 | 2 | | | II-1 | Zfp942 | | | 4907 | | | | Cntnap5b | | |
| 23843 | 2 | | | II-1 | Zfp943 | | | 5221 | | | | Csnk2b | 100337 616 | 4-May-15 |
| 23845 | 2 | | | II-1 | Zfp945 | | | 5590 | | | | D5Ertd579e | | |
| 23850 | 2 | | | II-1 | Zfp951 | | | 5612 | | | | D7Ertd143e | | |
| 23851 | 2 | | | II-1 | Zfp952 | | | 5683 | | | | Dcaf11 | 80344 | 12-May-15 |
| 23853 | 2 | | | II-1 | Zfp954 | | | 6944 | | | | F730043M19Rik | | |
| 23860 | 2 | | | II-1 | Zfp960 | | | 7602 | | | | Fpr2 | 2358 | 4-May-15 |
| 23862 | 2 | | | II-1 | Zfp963 | | | 7933 | | | | Gga2 | 23062 | 4-May-15 |
| 23863 | 2 | | | II-1 | Zfp964 | | | 8104 | | | | Gm10389 | | |
| 23865 | 2 | | | II-1 | Zfpl1 | 7542 | 4-May-15 | 8116 | | | | Gm10436 | | |
| 23873 | 2 | | | II-1 | Zfyve1 | 53349 | 21-May-15 | 8212 | | | | Gm11544 | | |
| 23879 | 2 | | | II-1 | Zfyve27 | 118813 | 12-May-15 | 8254 | | | | Gm12171 | | |
| 23880 | 2 | | | II-1 | Zfyve28 | 57732 | 4-May-15 | 8273 | | | | Gm12657 | | |
| 23885 | 2 | | | II-1 | Zgrf1 | 55345 | 4-May-15 | 8275 | | | | Gm12695 | | |
| 23892 | 2 | | | II-1 | Zic4 | 84107 | 4-May-15 | 8284 | | | | Gm12888 | | |
| 23894 | 2 | | | II-1 | Zik1 | 284307 | 4-May-15 | 8306 | | | | Gm13128 | | |
| 23895 | 2 | | | II-1 | Zim1 | | | 8322 | | | | Gm13276 | | |
| 23898 | 2 | | | II-1 | Zkscan14 | 84124 | 21-May-15 | 8323 | | | | Gm13277 | | |
| 23899 | 2 | | | II-1 | Zkscan16 | 158399 | 4-May-15 | 8325 | | | | Gm13279 | | |
| 23900 | 2 | | | II-1 | Zkscan17 | 84838 | 28-May-15 | 8326 | | | | Gm13283 | | |
| 23901 | 2 | | | II-1 | Zkscan2 | 342357 | 28-May-15 | 8327 | | | | Gm13285 | | |
| 23902 | 2 | | | II-1 | Zkscan3 | 80317 | 4-May-15 | 8328 | | | | Gm13286 | | |
| 23905 | 2 | | | II-1 | Zkscan6 | 7566 | 28-May-15 | 8330 | | | | Gm13290 | | |
| 23910 | 2 | | | II-1 | Zmat3 | 64393 | 4-May-15 | 8331 | | | | Gm13293 | | |
| 23916 | 2 | | | II-1 | Zmym1 | 79830 | 20-May-15 | 8376 | | | | Gm14207 | | |
| 23917 | 2 | | | II-1 | Zmym2 | 7750 | 12-May-15 | 8390 | | | | Gm14374 | | |
| 23919 | 2 | | | II-1 | Zmym4 | 9202 | 4-May-15 | 8412 | | | | Gm14483 | | |
| 23920 | 2 | | | II-1 | Zmym5 | 9205 | 4-May-15 | 8415 | | | | Gm14499 | | |
| 23921 | 2 | | | II-1 | Zmym6 | 9204 | 12-May-15 | 8417 | | | | Gm14611 | | |
| 23922 | 2 | | | II-1 | Zmynd10 | 51364 | 21-May-15 | 8432 | | | | Gm14819 | | |
| 23925 | 2 | | | II-1 | Zmynd15 | 84225 | 4-May-15 | 8445 | | | | Gm15104 | | |
| 23930 | 2 | | | II-1 | Znfx1 | 57169 | 4-May-15 | 8471 | | | | Gm15441 | | |
| 23931 | 2 | | | II-1 | Znhit1 | 10467 | 4-May-15 | 8480 | | | | Gm15645 | | |
| 23932 | 2 | | | II-1 | Znhit2 | 741 | 4-May-15 | 8496 | | | | Gm15910 | | |
| 23933 | 2 | | | II-1 | Znhit3 | 9326 | 4-May-15 | 8520 | | | | Gm16430 | | |
| 23935 | 2 | | | II-1 | Znrd1 | 30834 | 12-May-15 | 8554 | | | | Gm16897 | | |
| 23943 | 2 | | | II-1 | Zp3 | 7784 | 7-Jun-15 | 8630 | | | | Gm20172 | | |
| 23947 | 2 | | | II-1 | Zpbp2 | 124626 | 4-May-15 | 8634 | | | | Gm20257 | | |
| 23949 | 2 | | | II-1 | Zpr1 | 8882 | 12-May-15 | 8692 | | | | Gm20878 | | |
| 23950 | 2 | | | II-1 | Zranb1 | 54764 | 2-Jun-15 | 8743 | | | | Gm2a | 2760 | 21-May-15 |
| 23955 | 2 | | | II-1 | Zscan10 | 84891 | 4-May-15 | 8795 | | | | Gm4214 | | |
| 23956 | 2 | | | II-1 | Zscan12 | 9753 | 4-May-15 | 8797 | | | | Gm4224 | | |
| 23960 | 2 | | | II-1 | Zscan21 | 7589 | 28-May-15 | 8799 | | | | Gm4262 | | |
| 23964 | 2 | | | II-1 | Zscan29 | 146050 | 28-May-15 | 8834 | | | | Gm4787 | | |
| 23965 | 2 | | | II-1 | Zscan4a | | | 8839 | | | | Gm4814 | | |
| 23966 | 2 | | | II-1 | Zscan4b | | | 8850 | | | | Gm4872 | | |
| 23967 | 2 | | | II-1 | Zscan4c | | | 8856 | | | | Gm4922 | | |
| 23974 | 2 | | | II-1 | Zswim3 | 140831 | 4-May-15 | 8871 | | | | Gm5039 | | |
| 23975 | 2 | | | II-1 | Zswim4 | 65249 | 4-May-15 | 8873 | | | | Gm5069 | | |
| 23977 | 2 | | | II-1 | Zswim6 | 57688 | 4-May-15 | 8926 | | | | Gm5464 | | |
| 23978 | 2 | | | II-1 | Zswim7 | 125150 | 4-May-15 | 8931 | | | | Gm5478 | | |
| 23981 | 2 | | | II-1 | Zw10 | 9183 | 29-May-15 | 8940 | | | | Gm5547 | | |
| 23982 | 2 | | | II-1 | Zwilch | 55055 | 29-May-15 | 8946 | | | | Gm5607 | | |
| 23985 | 2 | | | II-1 | Zxdb | 158586 | 4-May-15 | 8981 | | | | Gm5893 | | |
| 23986 | 2 | | | II-1 | Zxdc | 79364 | 4-May-15 | 8992 | | | | Gm597 | | |
| 23987 | 2 | | | II-1 | Zyg11a | 440590 | 12-May-15 | 9028 | | | | Gm6455 | | |
| 23991 | 2 | | | II-1 | Zzz3 | 26009 | 21-May-15 | 9064 | | | | Gm684 | | |
| 207 | | | | | 1700020N18Rik | | | 9068 | | | | Gm6902 | | |
| 312 | | | | | 1700049L16Rik | | | 9120 | | | | Gm8096 | | |
| 849 | | | | | 4930429B21Rik | | | 9121 | | | | Gm813 | | |
| 891 | | | | | 4930449E18Rik | | | 9140 | | | | Gm8633 | | |
| 895 | | | | | 4930451I11Rik | | | 9145 | | | | Gm8765 | | |
| 902 | | | | | 4930453N24Rik | | | 9153 | | | | Gm8884 | | |
| 914 | | | | | 4930465K10Rik | | | 9174 | | | | Gm9573 | | |
| 919 | | | | | 4930468A15Rik | | | 9176 | | | | Gm9696 | | |
| 921 | | | | | 4930470H14Rik | | | 9181 | | | | Gm9767 | | |
| 976 | | | | | 4930511M06Rik | | | 9483 | | | | Grik1 | 2897 | 31-May-15 |
| 1003 | | | | | 4930524N10Rik | | | 9738 | | | | Hapln4 | 404037 | 4-May-15 |
| 1007 | | | | | 4930525G20Rik | | | 10339 | | | | Ifnk | 56832 | 4-May-15 |
| 1017 | | | | | 4930529K09Rik | | | 12506 | | | | Mir1899 | | |
| 1022 | | | | | 4930533P14Rik | | | 12507 | | | | Mir18b | 574033 | 21-May-15 |
| 1048 | | | | | 4930549G23Rik | | | 12508 | | | | Mir190 | 406965 | 21-May-15 |
| 1064 | | | | | 4930558C23Rik | | | 12509 | | | | Mir1900 | | |
| 1086 | | | | | 4930558J18Rik | | | 12510 | | | | Mir1901 | | |
| 1111 | | | | | 4930592A05Rik | | | 12511 | | | | Mir1902 | | |
| 1138 | | | | | 4931428F04Rik | | | 12512 | | | | Mir1903 | | |
| 1158 | | | | | 4932416H05Rik | | | 12513 | | | | Mir1904 | | |
| 1160 | | | | | 4932418E24Rik | | | 12514 | | | | Mir1905 | | |
| 1162 | | | | | 4932435O22Rik | | | 12515 | | | | Mir1906-1 | | |
| 1173 | | | | | 4933401D18Rik | | | 12516 | | | | Mir1907 | | |
| 1174 | | | | | 4933401D09Rik | | | 12517 | | | | Mir190b | 100126 346 | 21-May-15 |
| 1192 | | | | | 4933405O20Rik | | | 12518 | | | | Mir191 | 406966 | 21-May-15 |
| 1205 | | | | | 4933407K13Rik | | | 12519 | | | | Mir1912 | 100302 144 | 21-May-15 |
| 1206 | | | | | 4933407L21Rik | | | 12520 | | | | Mir192 | 406967 | 21-May-15 |
| 1281 | | | | | 5031414D18Rik | | | 12521 | | | | Mir1928 | | |
| 1319 | | | | | 5530601H04Rik | | | 12522 | | | | Mir1929 | | |
| 1320 | | | | | 5730403I07Rik | | | 12523 | | | | Mir193 | | |
| 1330 | | | | | 5730457N03Rik | | | 12524 | | | | Mir1930 | | |
| 1401 | | | | | 7630403G23Rik | | | 12525 | | | | Mir1931 | | |
| 1407 | | | | | 8030462N17Rik | | | 12526 | | | | Mir1932 | | |
| 1432 | | | | | 9130019P16Rik | | | 12527 | | | | Mir1933 | | |
| 1433 | | | | | 9130023H24Rik | | | 12529 | | | | Mir1936 | | |
| 1474 | | | | | 9430008C03Rik | | | 12530 | | | | Mir1938 | | |
| 2058 | | | | | AF357425 | | | 12531 | | | | Mir193b | 574455 | 21-May-15 |
| 3079 | | | | | B130024G19Rik | | | 12534 | | | | Mir194-1 | 406969 | 21-May-15 |
| 3478 | | | | | Bptf | 2186 | 4-May-15 | | | | | | | |
| 3687 | | | | | C920021L13Rik | | | | | | | | | |

Fig.22 - 115

| | | | | Mir | | |
|---|---|---|---|---|---|---|
| 12536 | | | | Mir194-2 | 406970 | 21-May-15 |
| 12537 | | | | Mir1943 | | |
| 12538 | | | | Mir1945 | | |
| 12539 | | | | Mir1946a | | |
| 12540 | | | | Mir1946b | | |
| 12541 | | | | Mir1947 | | |
| 12542 | | | | Mir1948 | | |
| 12543 | | | | Mir1949 | | |
| 12544 | | | | Mir195 | 406971 | 21-May-15 |
| 12545 | | | | Mir1950 | | |
| 12546 | | | | Mir1951 | | |
| 12547 | | | | Mir1952 | | |
| 12548 | | | | Mir1953 | | |
| 12549 | | | | Mir1954 | | |
| 12551 | | | | Mir1956 | | |
| 12552 | | | | Mir1957 | | |
| 12557 | | | | Mir1961 | | |
| 12558 | | | | Mir1962 | | |
| 12559 | | | | Mir1963 | | |
| 12560 | | | | Mir1964 | | |
| 12561 | | | | Mir1966 | | |
| 12562 | | | | Mir1967 | | |
| 12563 | | | | Mir1968 | | |
| 12564 | | | | Mir1969 | | |
| 12565 | | | | Mir196a-1 | | |
| 12566 | | | | Mir196a-2 | | |
| 12567 | | | | Mir196b | 442920 | 21-May-15 |
| 12568 | | | | Mir1970 | | |
| 12569 | | | | Mir1971 | | |
| 12570 | | | | Mir1981 | | |
| 12571 | | | | Mir1982 | | |
| 12572 | | | | Mir1983 | | |
| 12573 | | | | Mir199a-1 | | |
| 12575 | | | | Mir199b | 406978 | 21-May-15 |
| 12577 | | | | Mir19b-1 | | |
| 12578 | | | | Mir19b-2 | | |
| 12579 | | | | Mir1a-1 | | |
| 12580 | | | | Mir1a-2 | | |
| 12581 | | | | Mir1b | | |
| 12582 | | | | Mir200a | 406983 | 21-May-15 |
| 12583 | | | | Mir200b | 406984 | 21-May-15 |
| 12584 | | | | Mir200c | 406985 | 21-May-15 |
| 12585 | | | | Mir201 | | |
| 12586 | | | | Mir202 | 574448 | 21-May-15 |
| 12587 | | | | Mir203 | 406986 | 21-May-15 |
| 12588 | | | | Mir204 | 406987 | 31-May-15 |
| 12589 | | | | Mir205 | 406988 | 21-May-15 |
| 12590 | | | | Mir206 | 406989 | 21-May-15 |
| 12591 | | | | Mir207 | | |
| 12592 | | | | Mir208a | 406990 | 4-May-15 |
| 12593 | | | | Mir208b | 100126336 | 21-May-15 |
| 12994 | | | | Mir20a | 406982 | 21-May-15 |
| 12596 | | | | Mir21 | 406991 | 7-Jun-15 |
| 12598 | | | | Mir211 | 406993 | 21-May-15 |
| 12599 | | | | Mir212 | 406994 | 21-May-15 |
| 12600 | | | | Mir2136 | | |
| 12601 | | | | Mir2137 | | |
| 12602 | | | | Mir2139 | | |
| 12603 | | | | Mir214 | 406996 | 21-May-15 |
| 12608 | | | | Mir217 | 406999 | 21-May-15 |
| 12609 | | | | Mir218-1 | 407000 | 21-May-15 |
| 12610 | | | | Mir218-2 | 407001 | 21-May-15 |
| 12611 | | | | Mir219-1 | 407002 | 21-May-15 |
| 12612 | | | | Mir219-2 | 407003 | 21-May-15 |
| 12613 | | | | Mir219b | 100616335 | 21-May-15 |
| 12614 | | | | Mir219c | | |
| 12615 | | | | Mir21b | | |
| 12616 | | | | Mir21c | | |
| 12617 | | | | Mir22 | 407004 | 24-May-15 |
| 12618 | | | | Mir221 | 407006 | 21-May-15 |
| 12619 | | | | Mir222 | 407007 | 21-May-15 |
| 12620 | | | | Mir223 | 407008 | 21-May-15 |
| 12623 | | | | Mir23b | 407011 | 21-May-15 |
| 12624 | | | | Mir24-2 | 407013 | 21-May-15 |
| 12625 | | | | Mir25 | 407014 | 21-May-15 |
| 12627 | | | | Mir26a-1 | | |
| 12628 | | | | Mir26a-2 | | |
| 12629 | | | | Mir26b | 407017 | 21-May-15 |
| 12630 | | | | Mir27a | 407018 | 21-May-15 |
| 12631 | | | | Mir27b | 407019 | 21-May-15 |
| 12632 | | | | Mir28 | | |
| 12633 | | | | Mir2861 | 100422910 | 9-May-15 |
| 12634 | | | | Mir28b | | |
| 12635 | | | | Mir28c | | |
| 12636 | | | | Mir290 | | |
| 12637 | | | | Mir290b | | |
| 12638 | | | | Mir291a | | |
| 12639 | | | | Mir291b | | |
| 12640 | | | | Mir292 | | |
| 12641 | | | | Mir292b | | |
| 12642 | | | | Mir293 | | |
| 12643 | | | | Mir294 | | |
| 12644 | | | | Mir295 | | |
| 12645 | | | | Mir296 | 407022 | 21-May-15 |
| 12646 | | | | Mir297-1 | | |
| 12647 | | | | Mir297-2 | | |
| 12648 | | | | Mir297a-3 | | |
| 12649 | | | | Mir297a-4 | | |
| 12651 | | | | Mir297c | | |
| 12652 | | | | Mir298 | 100126296 | 4-May-15 |
| 12653 | | | | Mir299 | 407023 | 21-May-15 |
| 12654 | | | | Mir299b | | |
| 12655 | | | | Mir29a | 407021 | 21-May-15 |
| 12656 | | | | Mir29b-1 | | |
| 12657 | | | | Mir29b-2 | | |
| 12658 | | | | Mir29c | 407026 | 21-May-15 |
| 12659 | | | | Mir300 | 100126297 | 4-May-15 |
| 12660 | | | | Mir301 | 407027 | 21-May-15 |
| 12661 | | | | Mir301b | 100126318 | 21-May-15 |
| 12662 | | | | Mir302a | 407028 | 21-May-15 |
| 12663 | | | | Mir302b | 442894 | 21-May-15 |
| 12664 | | | | Mir302c | 442895 | 21-May-15 |
| 12665 | | | | Mir302d | 442896 | 21-May-15 |
| 12666 | | | | Mir3057 | | |
| 12667 | | | | Mir3058 | | |
| 12668 | | | | Mir3059 | | |
| 12670 | | | | Mir3061 | | |
| 12671 | | | | Mir3062 | | |
| 12672 | | | | Mir3063 | | |
| 12673 | | | | Mir3064 | 100616387 | 4-May-15 |
| 12674 | | | | Mir3065 | 100422915 | 21-May-15 |
| 12675 | | | | Mir3066 | | |
| 12676 | | | | Mir3067 | | |
| 12677 | | | | Mir3068 | | |
| 12678 | | | | Mir3069 | | |
| 12679 | | | | Mir3070a | | |
| 12680 | | | | Mir3070b | | |
| 12681 | | | | Mir3071 | | |
| 12682 | | | | Mir3072 | | |
| 12683 | | | | Mir3073 | | |
| 12684 | | | | Mir3073b | | |
| 12685 | | | | Mir3074-1 | | |
| 12686 | | | | Mir3074-2 | | |
| 12687 | | | | Mir3075 | | |
| 12688 | | | | Mir3076 | | |
| 12689 | | | | Mir3077 | | |
| 12690 | | | | Mir3078 | | |
| 12691 | | | | Mir3079 | | |
| 12692 | | | | Mir3081 | | |
| 12693 | | | | Mir3082 | | |
| 12694 | | | | Mir3083 | | |
| 12695 | | | | Mir3084 | | |
| 12696 | | | | Mir3084-2 | | |
| 12697 | | | | Mir3085 | | |
| 12698 | | | | Mir3086 | | |
| 12699 | | | | Mir3087 | | |
| 12700 | | | | Mir3088 | | |
| 12701 | | | | Mir3089 | | |
| 12702 | | | | Mir3091 | | |
| 12703 | | | | Mir3092 | | |
| 12704 | | | | Mir3093 | | |
| 12705 | | | | Mir3094 | | |
| 12706 | | | | Mir3095 | | |
| 12707 | | | | Mir3097 | | |
| 12708 | | | | Mir3098 | | |
| 12709 | | | | Mir3099 | | |
| 12710 | | | | Mir30a | 407029 | 7-Jun-15 |
| 12711 | | | | Mir30b | 407030 | 21-May-15 |
| 12712 | | | | Mir30c-1 | | |
| 12713 | | | | Mir30c-2 | | |
| 12714 | | | | Mir30d | 407033 | 21-May-15 |
| 12715 | | | | Mir30f | | |
| 12716 | | | | Mir31 | 407035 | 21-May-15 |
| 12717 | | | | Mir3100 | | |
| 12718 | | | | Mir3101 | | |
| 12719 | | | | Mir3102 | | |
| 12721 | | | | Mir3104 | | |
| 12722 | | | | Mir3106 | | |
| 12723 | | | | Mir3107 | | |
| 12724 | | | | Mir3108 | | |
| 12725 | | | | Mir3109 | | |
| 12726 | | | | Mir3110 | | |
| 12727 | | | | Mir3112 | | |
| 12728 | | | | Mir32 | 407036 | 21-May-15 |
| 12729 | | | | Mir320 | | |
| 12730 | | | | Mir322 | 494336 | 21-May-15 |
| 12731 | | | | Mir323 | 442897 | 21-May-15 |
| 12732 | | | | Mir324 | 442898 | 21-May-15 |
| 12733 | | | | Mir325 | | |
| 12734 | | | | Mir326 | 442900 | 21-May-15 |
| 12735 | | | | Mir328 | 442901 | 21-May-15 |
| 12736 | | | | Mir329 | | |
| 12738 | | | | Mir330 | 442902 | 21-May-15 |
| 12739 | | | | Mir331 | 442903 | 21-May-15 |
| 12740 | | | | Mir335 | 442904 | 21-May-15 |
| 12741 | | | | Mir337 | 442905 | 21-May-15 |
| 12742 | | | | Mir338 | 442906 | 21-May-15 |
| 12743 | | | | Mir339 | 442907 | 21-May-15 |
| 12744 | | | | Mir340 | 442908 | 21-May-15 |

Fig.22 - 116

| | | | | | | | | | | | |
|---|---|---|---|---|---|---|---|---|---|---|---|
| 12745 | | | | Mir341 | | | 12840 | | | Mir463 | | |
| 12746 | | | | Mir343 | | | 12841 | | | Mir465 | | |
| 12747 | | | | Mir344 | | | 12842 | | | Mir465b-1 | | |
| 12748 | | | | Mir344-2 | | | 12843 | | | Mir465c-1 | | |
| 12749 | | | | Mir344b | | | 12844 | | | Mir465d | | |
| 12750 | | | | Mir344c | | | 12845 | | | Mir466 | 100423 038 | 4-May-15 |
| 12751 | | | | Mir344d-1 | | | 12846 | | | Mir466b | 100616 350 | 4-May-15 |
| 12752 | | | | Mir344d-2 | | | 12847 | | | Mir466b-2 | | |
| 12753 | | | | Mir344d-3 | | | 12848 | | | Mir466b-3 | | |
| 12754 | | | | Mir344e | | | 12849 | | | Mir466d | | |
| 12755 | | | | Mir344f | | | 12850 | | | Mir466f-1 | | |
| 12756 | | | | Mir344g | | | 12851 | | | Mir466f-2 | | |
| 12757 | | | | Mir344h-1 | | | 12852 | | | Mir466f-3 | | |
| 12758 | | | | Mir344i | | | 12853 | | | Mir466g | | |
| 12759 | | | | Mir345 | 442910 | 21-May-15 | 12854 | | | Mir466h | | |
| 12760 | | | | Mir346 | 442911 | 21-May-15 | 12855 | | | Mir466i | | |
| 12761 | | | | Mir3470a | | | 12856 | | | Mir466n | | |
| 12762 | | | | Mir3470b | | | 12857 | | | Mir466o | | |
| 12763 | | | | Mir3471-1 | | | 12858 | | | Mir467a-1 | | |
| 12764 | | | | Mir3473 | | | 12859 | | | Mir467a-10 | | |
| 12765 | | | | Mir3473c | | | 12860 | | | Mir467a-2 | | |
| 12766 | | | | Mir3473d | | | 12861 | | | Mir467a-3 | | |
| 12767 | | | | Mir3473e | | | 12862 | | | Mir467a-5 | | |
| 12768 | | | | Mir3473f | | | 12863 | | | Mir467a-7 | | |
| 12769 | | | | Mir3473g | | | 12864 | | | Mir467a-9 | | |
| 12770 | | | | Mir3474 | | | 12865 | | | Mir467b | | |
| 12771 | | | | Mir3475 | | | 12866 | | | Mir467c | | |
| 12772 | | | | Mir34a | 407040 | 21-May-15 | 12867 | | | Mir467d | | |
| 12773 | | | | Mir34b | 407041 | 21-May-15 | 12868 | | | Mir467e | | |
| 12774 | | | | Mir34c | 407042 | 21-May-15 | 12869 | | | Mir467f | | |
| 12775 | | | | Mir350 | | | 12870 | | | Mir468 | | |
| 12776 | | | | Mir351 | | | 12871 | | | Mir470 | | |
| 12777 | | | | Mir3535 | | | 12872 | | | Mir471 | | |
| 12778 | | | | Mir3544 | | | 12873 | | | Mir483 | 619552 | 24-May-15 |
| 12779 | | | | Mir3547 | | | 12874 | | | Mir484 | 619553 | 21-May-15 |
| 12780 | | | | Mir3569 | | | 12875 | | | Mir485 | 574436 | 21-May-15 |
| 12781 | | | | Mir3572 | | | 12879 | | | Mir489 | 574442 | 21-May-15 |
| 12782 | | | | Mir362 | 574030 | 21-May-15 | 12880 | | | Mir490 | 574443 | 24-May-15 |
| 12783 | | | | Mir3620 | 100500 810 | 21-May-15 | 12881 | | | Mir491 | 574444 | 24-May-15 |
| 12784 | | | | Mir363 | 574031 | 21-May-15 | 12882 | | | Mir493 | 574450 | 21-May-15 |
| 12785 | | | | Mir365-1 | 100126 355 | 21-May-15 | 12883 | | | Mir494 | 574452 | 7-Jun-15 |
| 12786 | | | | Mir365-2 | 100126 356 | 21-May-15 | 12884 | | | Mir495 | 574453 | 21-May-15 |
| 12787 | | | | Mir367 | 442912 | 17-May-15 | 12885 | | | Mir496 | 574454 | 21-May-15 |
| 12788 | | | | Mir369 | 442914 | 21-May-15 | 12886 | | | Mir496b | | |
| 12789 | | | | Mir370 | 442915 | 21-May-15 | 12887 | | | Mir497 | 574456 | 7-Jun-15 |
| 12790 | | | | Mir374 | | | 12888 | | | Mir497b | | |
| 12791 | | | | Mir374c | 100500 807 | 21-May-15 | 12889 | | | Mir499 | 574501 | 21-May-15 |
| 12792 | | | | Mir375 | 494324 | 31-May-15 | 12890 | | | Mir500 | 574502 | 21-May-15 |
| 12793 | | | | Mir376a | | | 12891 | | | Mir501 | 574503 | 21-May-15 |
| 12794 | | | | Mir376b | 574435 | 21-May-15 | 12892 | | | Mir503 | 574506 | 21-May-15 |
| 12795 | | | | Mir376c | 442913 | 21-May-15 | 12893 | | | Mir504 | 574507 | 21-May-15 |
| 12796 | | | | Mir377 | 494326 | 21-May-15 | 12894 | | | Mir5046 | | |
| 12797 | | | | Mir378 | | | 12895 | | | Mir505 | 574508 | 21-May-15 |
| 12798 | | | | Mir378b | 100422 933 | 4-May-15 | 12896 | | | Mir509 | | |
| 12799 | | | | Mir378c | | | 12897 | | | Mir5098 | | |
| 12800 | | | | Mir379 | 494328 | 21-May-15 | 12898 | | | Mir5100 | 100847 014 | 4-May-15 |
| 12801 | | | | Mir380 | 494329 | 21-May-15 | 12899 | | | Mir5101 | | |
| 12802 | | | | Mir381 | 494330 | 21-May-15 | 12900 | | | Mir5103 | | |
| 12803 | | | | Mir382 | 494331 | 21-May-15 | 12901 | | | Mir5104 | | |
| 12804 | | | | Mir383 | 494332 | 21-May-15 | 12902 | | | Mir5106 | | |
| 12805 | | | | Mir384 | 494333 | 4-May-15 | 12903 | | | Mir5107 | | |
| 12806 | | | | Mir3960 | 100616 250 | 5-May-15 | 12904 | | | Mir5108 | | |
| 12807 | | | | Mir3962 | | | 12905 | | | Mir511 | 574445 | 21-May-15 |
| 12808 | | | | Mir3963 | | | 12906 | | | Mir5112 | 574446 | 21-May-15 |
| 12809 | | | | Mir3964 | | | 12907 | | | Mir5113 | | |
| 12810 | | | | Mir3965 | | | 12908 | | | Mir5114 | | |
| 12811 | | | | Mir3966 | | | 12909 | | | Mir5118 | | |
| 12812 | | | | Mir3967 | | | 12910 | | | Mir5119 | | |
| 12813 | | | | Mir3968 | | | 12911 | | | Mir5120 | | |
| 12814 | | | | Mir3969 | | | 12912 | | | Mir5121 | 574458 | 21-May-15 |
| 12815 | | | | Mir3970 | | | 12913 | | | Mir5122 | 574459 | 21-May-15 |
| 12816 | | | | Mir3971 | | | 12914 | | | Mir5123 | | |
| 12817 | | | | Mir409 | 574413 | 21-May-15 | 12915 | | | Mir5124 | | |
| 12818 | | | | Mir410 | 574434 | 21-May-15 | 12916 | | | Mir5125 | | |
| 12819 | | | | Mir411 | 693121 | 21-May-15 | 12917 | | | Mir5126 | | |
| 12820 | | | | Mir412 | 574433 | 21-May-15 | 12918 | | | Mir5127 | | |
| 12821 | | | | Mir421 | 693122 | 4-May-15 | 12919 | | | Mir5128 | | |
| 12822 | | | | Mir423 | 494335 | 21-May-15 | 12920 | | | Mir5129 | | |
| 12823 | | | | Mir425 | 494337 | 21-May-15 | 12921 | | | Mir5130 | | |
| 12824 | | | | Mir429 | 554210 | 21-May-15 | 12922 | | | Mir5131 | | |
| 12825 | | | | Mir431 | 574038 | 21-May-15 | 12923 | | | Mir5132 | | |
| 12826 | | | | Mir432 | 574451 | 21-May-15 | 12924 | | | Mir5133 | | |
| 12830 | | | | Mir449a | 554213 | 21-May-15 | 12925 | | | Mir5134 | | |
| 12831 | | | | Mir449b | 693123 | 21-May-15 | 12926 | | | Mir5135 | | |
| 12832 | | | | Mir449c | 100313 923 | 21-May-15 | 12927 | | | Mir5136 | | |
| 12833 | | | | Mir450-1 | | | 12928 | | | Mir532 | 693124 | 21-May-15 |
| 12834 | | | | Mir450-2 | | | 12929 | | | Mir539 | 664612 | 21-May-15 |
| 12835 | | | | Mir450b | 100126 302 | 21-May-15 | 12930 | | | Mir540 | | |
| 12836 | | | | Mir451 | 574411 | 21-May-15 | 12931 | | | Mir541 | 100126 308 | 21-May-15 |
| 12837 | | | | Mir452 | 574412 | 21-May-15 | 12932 | | | Mir542 | 664617 | 21-May-15 |
| 12838 | | | | Mir453 | 574410 | 21-May-15 | 12933 | | | Mir543 | 100126 335 | 21-May-15 |
| 12839 | | | | Mir455 | 619556 | 21-May-15 | 12934 | | | Mir544 | | |
| | | | | | | | 12938 | | | Mir5615-1 | | |
| | | | | | | | 12939 | | | Mir5615-2 | | |

Fig.22 - 117

| | | | | Mir | | |
|---|---|---|---|---|---|---|
| 12940 | | | | Mir5616 | | |
| 12941 | | | | Mir5617 | | |
| 12942 | | | | Mir5618 | | |
| 12944 | | | | Mir5620 | | |
| 12945 | | | | Mir5621 | | |
| 12946 | | | | Mir5622 | | |
| 12947 | | | | Mir5623 | | |
| 12948 | | | | Mir5624 | | |
| 12949 | | | | Mir5625 | | |
| 12950 | | | | Mir5626 | | |
| 12951 | | | | Mir5627 | | |
| 12952 | | | | Mir568 | 693153 | 4-May-15 |
| 12953 | | | | Mir5709 | | |
| 12954 | | | | Mir5710 | | |
| 12955 | | | | Mir574 | 693159 | 21-May-15 |
| 12956 | | | | Mir582 | 693167 | 5-May-15 |
| 12957 | | | | Mir592 | 693177 | 21-May-15 |
| 12958 | | | | Mir598 | 693183 | 21-May-15 |
| 12959 | | | | Mir599 | 693184 | 4-May-15 |
| 12960 | | | | Mir615 | 693200 | 21-May-15 |
| 12965 | | | | Mir6241 | | |
| 12969 | | | | Mir6337 | | |
| 12970 | | | | Mir6338 | | |
| 12976 | | | | Mir6344 | | |
| 12977 | | | | Mir6345 | | |
| 12978 | | | | Mir6348 | | |
| 12979 | | | | Mir6349 | | |
| 12980 | | | | Mir6350 | | |
| 12981 | | | | Mir6352 | | |
| 12982 | | | | Mir6353 | | |
| 12983 | | | | Mir6354 | | |
| 12984 | | | | Mir6355 | | |
| 12985 | | | | Mir6356 | | |
| 12996 | | | | Mir6367 | | |
| 12997 | | | | Mir6368 | | |
| 12998 | | | | Mir6369 | | |
| 12999 | | | | Mir6370 | | |
| 13000 | | | | Mir6372 | | |
| 13001 | | | | Mir6373 | | |
| 13002 | | | | Mir6374 | | |
| 13003 | | | | Mir6375 | | |
| 13004 | | | | Mir6376 | | |
| 13005 | | | | Mir6378 | | |
| 13006 | | | | Mir6380 | | |
| 13007 | | | | Mir6381 | | |
| 13008 | | | | Mir6382 | | |
| 13009 | | | | Mir6383 | | |
| 13010 | | | | Mir6384 | | |
| 13013 | | | | Mir6387 | | |
| 13015 | | | | Mir6389 | | |
| 13016 | | | | Mir6390 | | |
| 13017 | | | | Mir6391 | | |
| 13024 | | | | Mir6398 | | |
| 13026 | | | | Mir6400 | | |
| 13027 | | | | Mir6401 | | |
| 13028 | | | | Mir6402 | | |
| 13033 | | | | Mir6407 | | |
| 13034 | | | | Mir6408 | | |
| 13035 | | | | Mir6409 | | |
| 13036 | | | | Mir6410 | | |
| 13037 | | | | Mir6411 | | |
| 13038 | | | | Mir6412 | | |
| 13039 | | | | Mir6413 | | |
| 13040 | | | | Mir6414 | | |
| 13041 | | | | Mir6415 | | |
| 13042 | | | | Mir6416 | | |
| 13043 | | | | Mir6417 | | |
| 13046 | | | | Mir6420 | | |
| 13052 | | | | Mir6539 | | |
| 13053 | | | | Mir654 | 724024 | 21-May-15 |
| 13054 | | | | Mir6540 | | |
| 13055 | | | | Mir6541 | | |
| 13056 | | | | Mir6546 | | |
| 13057 | | | | Mir664 | 100302234 | 21-May-15 |
| 13058 | | | | Mir665 | 100126315 | 21-May-15 |
| 13059 | | | | Mir666 | | |
| 13060 | | | | Mir667 | | |
| 13061 | | | | Mir668 | 768214 | 4-May-15 |
| 13062 | | | | Mir669a-1 | | |
| 13063 | | | | Mir669a-2 | | |
| 13064 | | | | Mir669a-3 | | |
| 13065 | | | | Mir669a-4 | | |
| 13066 | | | | Mir669b | | |
| 13067 | | | | Mir669c | | |
| 13068 | | | | Mir669e | | |
| 13069 | | | | Mir669g | | |
| 13070 | | | | Mir669h | | |
| 13071 | | | | Mir669i | | |
| 13072 | | | | Mir669j | | |
| 13073 | | | | Mir669k | | |
| 13074 | | | | Mir669m-1 | | |
| 13075 | | | | Mir669m-2 | | |
| 13076 | | | | Mir669p-1 | | |
| 13078 | | | | Mir671 | 768213 | 21-May-15 |
| 13079 | | | | Mir6715 | | |
| 13080 | | | | Mir672 | | |
| 13081 | | | | Mir673 | | |
| 13083 | | | | Mir675 | 100033819 | 4-May-15 |
| 13084 | | | | Mir676 | 100500887 | 21-May-15 |
| 13085 | | | | Mir6769b | 102466202 | 4-May-15 |
| 13087 | | | | Mir678 | | |
| 13089 | | | | Mir680-2 | | |
| 13090 | | | | Mir680-3 | | |
| 13091 | | | | Mir681 | | |
| 13098 | | | | Mir687 | | |
| 13099 | | | | Mir688 | | |
| 13100 | | | | Mir6896 | | |
| 13101 | | | | Mir6897 | | |
| 13103 | | | | Mir6899 | | |
| 13104 | | | | Mir690 | | |
| 13106 | | | | Mir6901 | | |
| 13107 | | | | Mir6902 | | |
| 13109 | | | | Mir6904 | | |
| 13110 | | | | Mir6905 | | |
| 13111 | | | | Mir6906 | | |
| 13112 | | | | Mir6907 | | |
| 13113 | | | | Mir6908 | | |
| 13114 | | | | Mir6909 | | |
| 13115 | | | | Mir691 | | |
| 13116 | | | | Mir6910 | | |
| 13117 | | | | Mir6911 | | |
| 13118 | | | | Mir6912 | | |
| 13119 | | | | Mir6913 | | |
| 13120 | | | | Mir6914 | | |
| 13121 | | | | Mir6915 | | |
| 13122 | | | | Mir6916 | | |
| 13123 | | | | Mir6917 | | |
| 13124 | | | | Mir6918 | | |
| 13125 | | | | Mir6919 | | |
| 13128 | | | | Mir692-1 | | |
| 13131 | | | | Mir6923 | | |
| 13132 | | | | Mir6924 | | |
| 13133 | | | | Mir6925 | | |
| 13135 | | | | Mir6927 | | |
| 13136 | | | | Mir6928 | | |
| 13137 | | | | Mir6929 | | |
| 13138 | | | | Mir693 | | |
| 13139 | | | | Mir6930 | | |
| 13140 | | | | Mir6931 | | |
| 13141 | | | | Mir6932 | | |
| 13142 | | | | Mir6933 | | |
| 13143 | | | | Mir6934 | | |
| 13144 | | | | Mir6935 | | |
| 13146 | | | | Mir6937 | | |
| 13147 | | | | Mir6938 | | |
| 13148 | | | | Mir6939 | | |
| 13149 | | | | Mir694 | | |
| 13150 | | | | Mir6940 | | |
| 13151 | | | | Mir6941 | | |
| 13152 | | | | Mir6942 | | |
| 13153 | | | | Mir6943 | | |
| 13154 | | | | Mir6944 | | |
| 13155 | | | | Mir6945 | | |
| 13156 | | | | Mir6946 | | |
| 13157 | | | | Mir6947 | | |
| 13158 | | | | Mir6948 | | |
| 13159 | | | | Mir6949 | | |
| 13160 | | | | Mir695 | | |
| 13161 | | | | Mir6950 | | |
| 13162 | | | | Mir6951 | | |
| 13163 | | | | Mir6952 | | |
| 13165 | | | | Mir6954 | | |
| 13166 | | | | Mir6955 | | |
| 13167 | | | | Mir6956 | | |
| 13168 | | | | Mir6957 | | |
| 13169 | | | | Mir6958 | | |
| 13170 | | | | Mir6959 | | |
| 13171 | | | | Mir6960 | | |
| 13172 | | | | Mir6961 | | |
| 13173 | | | | Mir6962 | | |
| 13174 | | | | Mir6963 | | |
| 13175 | | | | Mir6964 | | |
| 13176 | | | | Mir6965 | | |
| 13177 | | | | Mir6966 | | |
| 13178 | | | | Mir6968 | | |
| 13179 | | | | Mir6969 | | |
| 13182 | | | | Mir6971 | | |
| 13184 | | | | Mir6973a | | |
| 13185 | | | | Mir6973b | | |
| 13186 | | | | Mir6974 | | |
| 13187 | | | | Mir6975 | | |
| 13188 | | | | Mir6976 | | |
| 13189 | | | | Mir6977 | | |
| 13190 | | | | Mir6978 | | |
| 13191 | | | | Mir6979 | | |
| 13192 | | | | Mir698 | | |
| 13193 | | | | Mir6980 | | |
| 13197 | | | | Mir6984 | | |
| 13198 | | | | Mir6985 | | |
| 13199 | | | | Mir6986 | | |
| 13200 | | | | Mir6987 | | |

Fig.22 - 118

| | | | | | | | | | | | | |
|---|---|---|---|---|---|---|---|---|---|---|---|---|
| 13201 | | | | Mir6988 | | | 13312 | | | | Mir7089 | | |
| 13202 | | | | Mir6989 | | | 13313 | | | | Mir709 | | |
| 13203 | | | | Mir6990 | | | 13314 | | | | Mir7090 | | |
| 13204 | | | | Mir6991 | | | 13315 | | | | Mir7091 | | |
| 13207 | | | | Mir6994 | | | 13316 | | | | Mir7092 | | |
| 13209 | | | | Mir6996 | | | 13317 | | | | Mir7093 | | |
| 13210 | | | | Mir6997 | | | 13318 | | | | Mir7094-1 | | |
| 13211 | | | | Mir6998 | | | 13319 | | | | Mir7094-2 | | |
| 13212 | | | | Mir6999 | | | 13321 | | | | Mir710 | | |
| 13215 | | | | Mir7001 | | | 13322 | | | | Mir711 | 100313 843 | 4-May-15 |
| 13216 | | | | Mir7002 | | | 13323 | | | | Mir7115 | | |
| 13217 | | | | Mir7003 | | | 13324 | | | | Mir7117 | | |
| 13218 | | | | Mir7004 | | | 13325 | | | | Mir7118 | | |
| 13219 | | | | Mir7005 | | | 13326 | | | | Mir7119 | | |
| 13220 | | | | Mir7006 | | | 13327 | | | | Mir713 | | |
| 13221 | | | | Mir7007 | | | 13329 | | | | Mir718 | 100313 781 | 4-May-15 |
| 13222 | | | | Mir7008 | | | 13335 | | | | Mir7212 | | |
| 13223 | | | | Mir7009 | | | 13336 | | | | Mir7213 | | |
| 13224 | | | | Mir701 | | | 13337 | | | | Mir7214 | | |
| 13225 | | | | Mir7010 | | | 13338 | | | | Mir7215 | | |
| 13226 | | | | Mir7011 | | | 13339 | | | | Mir7216 | | |
| 13227 | | | | Mir7012 | | | 13340 | | | | Mir7217 | | |
| 13228 | | | | Mir7013 | | | 13341 | | | | Mir7218 | | |
| 13229 | | | | Mir7014 | | | 13342 | | | | Mir7219 | | |
| 13230 | | | | Mir7015 | | | 13343 | | | | Mir7220 | | |
| 13231 | | | | Mir7016 | | | 13344 | | | | Mir7221 | | |
| 13232 | | | | Mir7017 | | | 13345 | | | | Mir7222 | | |
| 13233 | | | | Mir7018 | | | 13346 | | | | Mir7223 | | |
| 13234 | | | | Mir7019 | | | 13347 | | | | Mir7224 | | |
| 13235 | | | | Mir702 | | | 13348 | | | | Mir7225 | | |
| 13236 | | | | Mir7020 | | | 13349 | | | | Mir7226 | | |
| 13237 | | | | Mir7021 | | | 13350 | | | | Mir7227 | | |
| 13238 | | | | Mir7022 | | | 13351 | | | | Mir7228 | | |
| 13239 | | | | Mir7023 | | | 13352 | | | | Mir7229 | | |
| 13240 | | | | Mir7024 | | | 13353 | | | | Mir7230 | | |
| 13242 | | | | Mir7026 | | | 13354 | | | | Mir7231 | | |
| 13243 | | | | Mir7027 | | | 13355 | | | | Mir7232 | | |
| 13244 | | | | Mir7028 | | | 13356 | | | | Mir7233 | | |
| 13245 | | | | Mir7029 | | | 13357 | | | | Mir7234 | | |
| 13250 | | | | Mir7033 | | | 13358 | | | | Mir7235 | | |
| 13251 | | | | Mir7034 | | | 13359 | | | | Mir7236 | | |
| 13252 | | | | Mir7035 | | | 13360 | | | | Mir7237 | | |
| 13253 | | | | Mir7036 | | | 13361 | | | | Mir7238 | | |
| 13254 | | | | Mir7036b | | | 13362 | | | | Mir7239 | | |
| 13255 | | | | Mir7037 | | | 13363 | | | | Mir7240 | | |
| 13256 | | | | Mir7038 | | | 13365 | | | | Mir7242 | | |
| 13257 | | | | Mir7039 | | | 13366 | | | | Mir7243 | | |
| 13258 | | | | Mir704 | | | 13367 | | | | Mir741 | | |
| 13259 | | | | Mir7040 | | | 13368 | | | | Mir742 | | |
| 13260 | | | | Mir7041 | | | 13369 | | | | Mir743 | | |
| 13261 | | | | Mir7042 | | | 13370 | | | | Mir743b | | |
| 13262 | | | | Mir7043 | | | 13371 | | | | Mir744 | 100126 313 | 21-May-15 |
| 13263 | | | | Mir7044 | | | 13372 | | | | Mir7578 | | |
| 13264 | | | | Mir7045 | | | 13373 | | | | Mir758 | 768212 | 21-May-15 |
| 13265 | | | | Mir7046 | | | 13374 | | | | Mir759 | 100313 778 | 4-May-15 |
| 13266 | | | | Mir7047 | | | 13379 | | | | Mir7646 | | |
| 13267 | | | | Mir7048 | | | 13380 | | | | Mir7647 | | |
| 13268 | | | | Mir7049 | | | 13381 | | | | Mir7648 | | |
| 13269 | | | | Mir705 | | | 13382 | | | | Mir7649 | | |
| 13270 | | | | Mir7050 | | | 13383 | | | | Mir7650 | | |
| 13271 | | | | Mir7051 | | | 13384 | | | | Mir7652 | | |
| 13272 | | | | Mir7052 | | | 13385 | | | | Mir7653 | | |
| 13273 | | | | Mir7053 | | | 13386 | | | | Mir7654 | | |
| 13274 | | | | Mir7054 | | | 13387 | | | | Mir7655 | | |
| 13275 | | | | Mir7055 | | | 13388 | | | | Mir7656 | | |
| 13276 | | | | Mir7056 | | | 13389 | | | | Mir7657 | | |
| 13277 | | | | Mir7057 | | | 13390 | | | | Mir7658 | | |
| 13278 | | | | Mir7058 | | | 13391 | | | | Mir7661 | | |
| 13279 | | | | Mir7059 | | | 13392 | | | | Mir7662 | | |
| 13280 | | | | Mir706 | | | 13393 | | | | Mir7663 | | |
| 13284 | | | | Mir7063 | | | 13394 | | | | Mir7665 | | |
| 13285 | | | | Mir7064 | | | 13395 | | | | Mir7666 | | |
| 13286 | | | | Mir7065 | | | 13396 | | | | Mir7667 | | |
| 13287 | | | | Mir7066 | | | 13397 | | | | Mir7668 | | |
| 13288 | | | | Mir7067 | | | 13398 | | | | Mir7669 | | |
| 13289 | | | | Mir7068 | | | 13400 | | | | Mir7670 | | |
| 13290 | | | | Mir7069 | | | 13401 | | | | Mir7671 | | |
| 13291 | | | | Mir707 | | | 13402 | | | | Mir7672 | | |
| 13292 | | | | Mir7070 | | | 13403 | | | | Mir7673 | | |
| 13293 | | | | Mir7071 | | | 13404 | | | | Mir7674 | | |
| 13294 | | | | Mir7072 | | | 13405 | | | | Mir7675 | | |
| 13295 | | | | Mir7073 | | | 13406 | | | | Mir7676-2 | | |
| 13296 | | | | Mir7074 | | | 13407 | | | | Mir7677 | | |
| 13297 | | | | Mir7075 | | | 13408 | | | | Mir7678 | | |
| 13298 | | | | Mir7076 | | | 13409 | | | | Mir7679 | | |
| 13299 | | | | Mir7077 | | | 13410 | | | | Mir7680 | | |
| 13300 | | | | Mir7078 | | | 13411 | | | | Mir7681 | | |
| 13301 | | | | Mir7079 | | | 13412 | | | | Mir7682 | | |
| 13302 | | | | Mir708 | 100126 333 | 4-May-15 | 13413 | | | | Mir7684 | | |
| 13303 | | | | Mir7080 | | | 13414 | | | | Mir7685 | | |
| 13304 | | | | Mir7081 | | | 13415 | | | | Mir7686 | | |
| 13305 | | | | Mir7082 | | | 13416 | | | | Mir7687 | | |
| 13306 | | | | Mir7083 | | | 13417 | | | | Mir770 | 768222 | 4-May-15 |
| 13307 | | | | Mir7084 | | | 13418 | | | | Mir7b | | |
| 13309 | | | | Mir7086 | | | 13419 | | | | Mir802 | 768219 | 17-May-15 |
| 13310 | | | | Mir7087 | | | | | | | | | |
| 13331 | | | | Mir7088 | | | | | | | | | |

Fig.22 - 119

| | | | | | | | | | | |
|---|---|---|---|---|---|---|---|---|---|---|
| 13420 | | | Mir804 | | | 15041 | | | Olfr120 | |
| 13440 | | | Mir8110 | | | 15042 | | | Olfr1200 | |
| 13450 | | | Mir871 | | | 15043 | | | Olfr1201 | |
| 13452 | | | Mir873b | 100126316 | 21-May-15 | 15044 | | | Olfr1202 | |
| 13453 | | | Mir874 | 100126343 | 21-May-15 | 15045 | | | Olfr1204 | |
| 13454 | | | Mir875 | 100126309 | 4-May-15 | 15046 | | | Olfr1205 | |
| | | | | | | 15047 | | | Olfr1206 | |
| 13455 | | | Mir876 | 100126310 | 21-May-15 | 15048 | | | Olfr1208 | |
| 13456 | | | Mir877 | 100126314 | 21-May-15 | 15049 | | | Olfr1209 | |
| | | | | | | 15050 | | | Olfr121 | |
| 13457 | | | Mir878 | | | 15051 | | | Olfr1211 | |
| 13458 | | | Mir879 | | | 15052 | | | Olfr1212 | |
| 13459 | | | Mir880 | | | 15053 | | | Olfr1213 | |
| 13460 | | | Mir881 | | | 15054 | | | Olfr1214 | |
| 13461 | | | Mir882 | | | 15055 | | | Olfr1215 | |
| 13462 | | | Mir883a | | | 15056 | | | Olfr1216 | |
| 13463 | | | Mir883b | | | 15057 | | | Olfr1217 | |
| 13464 | | | Mir9-1 | 407046 | 21-May-15 | 15058 | | | Olfr1218 | |
| 13465 | | | Mir9-2 | 407047 | 21-May-15 | 15059 | | | Olfr1219 | |
| 13466 | | | Mir92-1 | 407048 | 21-May-15 | 15060 | | | Olfr122 | |
| 13467 | | | Mir92-2 | | | 15061 | | | Olfr1220 | |
| 13468 | | | Mir92b | 693235 | 21-May-15 | 15062 | | | Olfr1221 | |
| 13469 | | | Mir93 | 407050 | 21-May-15 | 15063 | | | Olfr1222 | |
| 13470 | | | Mir9-3 | 407051 | 21-May-15 | 15064 | | | Olfr1223 | |
| 13471 | | | Mir96 | 407053 | 7-Jun-15 | 15065 | | | Olfr1225 | |
| 13472 | | | Mir98 | 407054 | 21-May-15 | 15066 | | | Olfr1226 | |
| 13473 | | | Mir99a | 407055 | 21-May-15 | 15067 | | | Olfr1228 | |
| 13474 | | | Mir99b | 407056 | 21-May-15 | 15068 | | | Olfr1229 | |
| 13475 | | | Mira | | | 15069 | | | Olfr123 | |
| | | | | | | 15070 | | | Olfr1230 | |
| 13487 | | | Mirlet7g | 406890 | 21-May-15 | 15071 | | | Olfr1231 | |
| 13488 | | | Mirlet7i | 406891 | 21-May-15 | 15072 | | | Olfr1232 | |
| 13489 | | | Mirlet7j | | | 15073 | | | Olfr1233 | |
| 13490 | | | Mirlet7k | | | 15074 | | | Olfr1234 | |
| 13492 | | | Mis18a | 54069 | 12-May-15 | 15075 | | | Olfr1238 | |
| 13493 | | | Mis18bp1 | 55320 | 4-May-15 | 15076 | | | Olfr1239 | |
| 13602 | | | Morc3 | 23515 | 4-May-15 | 15077 | | | Olfr124 | |
| 14903 | | | Olfr1026 | | | 15078 | | | Olfr1240 | |
| 14928 | | | Olfr1054 | | | 15079 | | | Olfr1241 | |
| 14929 | | | Olfr1055 | | | 15080 | | | Olfr1242 | |
| 14930 | | | Olfr1056 | | | 15081 | | | Olfr1243 | |
| 14932 | | | Olfr1058 | | | 15082 | | | Olfr1245 | |
| 14943 | | | Olfr1082 | | | 15083 | | | Olfr1246 | |
| 14944 | | | Olfr1084 | | | 15084 | | | Olfr1247 | |
| 14945 | | | Olfr1085 | | | 15085 | | | Olfr1248 | |
| 14946 | | | Olfr1086 | | | 15086 | | | Olfr1249 | |
| 14947 | | | Olfr1087 | | | 15087 | | | Olfr125 | |
| 14948 | | | Olfr1089 | | | 15088 | | | Olfr1250 | |
| 14949 | | | Olfr109 | | | 15089 | | | Olfr1251 | |
| 14950 | | | Olfr1090 | | | 15090 | | | Olfr1252 | |
| 14953 | | | Olfr1095 | | | 15091 | | | Olfr1253 | |
| 14962 | | | Olfr1104 | | | 15092 | | | Olfr1254 | |
| 14971 | | | Olfr1113 | | | 15093 | | | Olfr1255 | |
| 14972 | | | Olfr1115 | | | 15094 | | | Olfr1256 | |
| 14988 | | | Olfr1133 | | | 15095 | | | Olfr1257 | |
| 14997 | | | Olfr1143 | | | 15096 | | | Olfr1258 | |
| 14998 | | | Olfr1145 | | | 15097 | | | Olfr1259 | |
| 14999 | | | Olfr1148 | | | 15098 | | | Olfr126 | |
| 15000 | | | Olfr115 | | | 15099 | | | Olfr1260 | |
| 15001 | | | Olfr1151 | | | 15100 | | | Olfr1261 | |
| 15002 | | | Olfr1152 | | | 15101 | | | Olfr1262 | |
| 15003 | | | Olfr1153 | | | 15102 | | | Olfr1263 | |
| 15004 | | | Olfr1154 | | | 15103 | | | Olfr1264 | |
| 15005 | | | Olfr1155 | | | 15104 | | | Olfr1265 | |
| 15006 | | | Olfr1156 | | | 15105 | | | Olfr1269 | |
| 15007 | | | Olfr1157 | | | 15106 | | | Olfr127 | |
| 15008 | | | Olfr1158 | | | 15108 | | | Olfr1271 | |
| 15009 | | | Olfr116 | | | 15110 | | | Olfr1273-ps | |
| 15010 | | | Olfr1160 | | | 15111 | | | Olfr1274-ps | |
| 15011 | | | Olfr1161 | | | 15112 | | | Olfr1275 | |
| 15012 | | | Olfr1162 | | | 15113 | | | Olfr1276 | |
| 15013 | | | Olfr1163 | | | 15114 | | | Olfr1277 | |
| 15014 | | | Olfr1164 | | | 15115 | | | Olfr1278 | |
| 15015 | | | Olfr1166 | | | 15116 | | | Olfr1279 | |
| 15016 | | | Olfr1167 | | | 15117 | | | Olfr128 | |
| 15017 | | | Olfr1168 | | | 15118 | | | Olfr1280 | |
| 15018 | | | Olfr117 | | | 15121 | | | Olfr1283 | |
| 15019 | | | Olfr1170 | | | 15122 | | | Olfr1284 | |
| 15020 | | | Olfr1173 | | | 15123 | | | Olfr1286 | |
| 15021 | | | Olfr1176 | | | 15124 | | | Olfr1287 | |
| 15022 | | | Olfr1178 | | | 15125 | | | Olfr1288 | |
| 15023 | | | Olfr1179 | | | 15126 | | | Olfr1289 | |
| 15024 | | | Olfr118 | | | 15127 | | | Olfr129 | |
| 15025 | | | Olfr1180 | | | 15128 | | | Olfr1290 | |
| 15028 | | | Olfr1183 | | | 15129 | | | Olfr1294 | |
| 15029 | | | Olfr1184 | | | 15130 | | | Olfr1295 | |
| 15030 | | | Olfr1186 | | | 15131 | | | Olfr1297 | |
| 15031 | | | Olfr1188 | | | 15132 | | | Olfr1298 | |
| 15032 | | | Olfr1189 | | | 15133 | | | Olfr1299 | |
| 15033 | | | Olfr119 | | | 15134 | | | Olfr13 | |
| 15034 | | | Olfr1193 | | | 15135 | | | Olfr130 | |
| 15035 | | | Olfr1195 | | | 15136 | | | Olfr1300-ps1 | |
| 15036 | | | Olfr1196 | | | 15138 | | | Olfr1302 | |
| 15037 | | | Olfr1197 | | | 15139 | | | Olfr1303 | |
| 15038 | | | Olfr1198 | | | 15140 | | | Olfr1305 | |
| 15039 | | | Olfr1199 | | | 15141 | | | Olfr1306 | |
| 15040 | | | Olfr12 | | | 15142 | | | Olfr1307 | |

Fig.22 - 120

| | | | | | | | | | | |
|---|---|---|---|---|---|---|---|---|---|---|
| 15143 | | | Olfr1308 | | | 15262 | | | Olfr1447 | | |
| 15144 | | | Olfr1309 | | | 15263 | | | Olfr1448 | | |
| 15145 | | | Olfr131 | | | 15264 | | | Olfr1449 | | |
| 15146 | | | Olfr1310 | | | 15265 | | | Olfr145 | | |
| 15147 | | | Olfr1311 | | | 15266 | | | Olfr1450 | | |
| 15148 | | | Olfr1312 | | | 15267 | | | Olfr1451 | | |
| 15149 | | | Olfr1313 | | | 15268 | | | Olfr1453 | | |
| 15150 | | | Olfr1314 | | | 15269 | | | Olfr1454 | | |
| 15151 | | | Olfr1316 | | | 15270 | | | Olfr1457 | | |
| 15152 | | | Olfr1317 | | | 15271 | | | Olfr1459 | | |
| 15153 | | | Olfr1318 | | | 15272 | | | Olfr146 | | |
| 15154 | | | Olfr132 | | | 15273 | | | Olfr1461 | | |
| 15155 | | | Olfr1320 | | | 15274 | | | Olfr1462 | | |
| 15156 | | | Olfr1321 | | | 15275 | | | Olfr1463 | | |
| 15157 | | | Olfr1322 | | | 15276 | | | Olfr1465 | | |
| 15158 | | | Olfr1323 | | | 15277 | | | Olfr1466 | | |
| 15159 | | | Olfr1324 | | | 15278 | | | Olfr1467 | | |
| 15160 | | | Olfr1325 | | | 15279 | | | Olfr1469 | | |
| 15161 | | | Olfr1328 | | | 15280 | | | Olfr147 | | |
| 15162 | | | Olfr1329 | | | 15281 | | | Olfr1471 | | |
| 15163 | | | Olfr133 | | | 15282 | | | Olfr1472 | | |
| 15164 | | | Olfr1330 | | | 15283 | | | Olfr1474 | | |
| 15165 | | | Olfr1331 | | | 15284 | | | Olfr1475 | | |
| 15166 | | | Olfr1333 | | | 15285 | | | Olfr1477 | | |
| 15167 | | | Olfr1335 | | | 15286 | | | Olfr148 | | |
| 15168 | | | Olfr1336 | | | 15287 | | | Olfr1480 | | |
| 15169 | | | Olfr1337 | | | 15288 | | | Olfr1484 | | |
| 15170 | | | Olfr1338 | | | 15289 | | | Olfr1487 | | |
| 15171 | | | Olfr1339 | | | 15290 | | | Olfr1489 | | |
| 15172 | | | Olfr134 | | | 15291 | | | Olfr149 | | |
| 15174 | | | Olfr1341 | | | 15293 | | | Olfr1491 | | |
| 15175 | | | Olfr1342 | | | 15294 | | | Olfr1494 | | |
| 15176 | | | Olfr1344 | | | 15295 | | | Olfr1495 | | |
| 15178 | | | Olfr1347 | | | 15296 | | | Olfr1496 | | |
| 15180 | | | Olfr1349 | | | 15297 | | | Olfr1497 | | |
| 15181 | | | Olfr135 | | | 15298 | | | Olfr1499 | | |
| 15182 | | | Olfr1350 | | | 15299 | | | Olfr15 | | |
| 15183 | | | Olfr1351 | | | 15300 | | | Olfr150 | | |
| 15184 | | | Olfr1352 | | | 15301 | | | Olfr1500 | | |
| 15185 | | | Olfr1353 | | | 15302 | | | Olfr1501 | | |
| 15186 | | | Olfr1354 | | | 15303 | | | Olfr1502 | | |
| 15187 | | | Olfr1355 | | | 15304 | | | Olfr1504 | | |
| 15188 | | | Olfr1356 | | | 15305 | | | Olfr1505 | | |
| 15189 | | | Olfr1357 | | | 15306 | | | Olfr1506 | | |
| 15190 | | | Olfr1359 | | | 15307 | | | Olfr1507 | | |
| 15191 | | | Olfr136 | | | 15309 | | | Olfr1509 | | |
| 15192 | | | Olfr1360 | | | 15311 | | | Olfr1510 | | |
| 15193 | | | Olfr1361 | | | 15312 | | | Olfr1511 | | |
| 15194 | | | Olfr1362 | | | 15313 | | | Olfr1512 | | |
| 15195 | | | Olfr1364 | | | 15314 | | | Olfr1513 | | |
| 15196 | | | Olfr1366 | | | 15315 | | | Olfr152 | | |
| 15197 | | | Olfr1367 | | | 15316 | | | Olfr153 | | |
| 15198 | | | Olfr1368 | | | 15317 | | | Olfr1532-ps1 | | |
| 15199 | | | Olfr137 | | | 15319 | | | Olfr1537 | | |
| 15200 | | | Olfr1370 | | | 15320 | | | Olfr154 | | |
| 15201 | | | Olfr1371 | | | 15321 | | | Olfr155 | | |
| 15206 | | | Olfr138 | | | 15322 | | | Olfr156 | | |
| 15207 | | | Olfr1380 | | | 15323 | | | Olfr157 | | |
| 15208 | | | Olfr1381 | | | 15324 | | | Olfr159 | | |
| 15209 | | | Olfr1382 | | | 15325 | | | Olfr16 | | |
| 15212 | | | Olfr1385 | | | 15327 | | | Olfr161 | | |
| 15215 | | | Olfr1388 | | | 15328 | | | Olfr164 | | |
| 15216 | | | Olfr1389 | | | 15329 | | | Olfr165 | | |
| 15217 | | | Olfr139 | | | 15333 | | | Olfr169 | | |
| 15218 | | | Olfr1390 | | | 15334 | | | Olfr17 | | |
| 15219 | | | Olfr1391 | | | 15335 | | | Olfr170 | | |
| 15220 | | | Olfr1392 | | | 15338 | | | Olfr173 | | |
| 15221 | | | Olfr1393 | | | 15339 | | | Olfr175-ps1 | | |
| 15228 | | | Olfr1406 | | | 15341 | | | Olfr177 | | |
| 15229 | | | Olfr1408 | | | 15342 | | | Olfr178 | | |
| 15230 | | | Olfr141 | | | 15343 | | | Olfr18 | | |
| 15231 | | | Olfr1410 | | | 15344 | | | Olfr180 | | |
| 15232 | | | Olfr1411 | | | 15345 | | | Olfr181 | | |
| 15234 | | | Olfr1413 | | | 15346 | | | Olfr183 | | |
| 15235 | | | Olfr1414 | | | 15347 | | | Olfr186 | | |
| 15236 | | | Olfr1415 | | | 15348 | | | Olfr187 | | |
| 15237 | | | Olfr1416 | | | 15351 | | | Olfr191 | | |
| 15238 | | | Olfr1417 | | | 15353 | | | Olfr193 | | |
| 15239 | | | Olfr1418 | | | 15355 | | | Olfr195 | | |
| 15240 | | | Olfr1419 | | | 15356 | | | Olfr196 | | |
| 15242 | | | Olfr1420 | | | 15357 | | | Olfr197 | | |
| 15246 | | | Olfr1426 | | | 15359 | | | Olfr199 | | |
| 15247 | | | Olfr1427 | | | 15360 | | | Olfr2 | 7932 | 4-May-15 |
| 15248 | | | Olfr1428 | | | 15361 | | | Olfr20 | | |
| 15249 | | | Olfr143 | | | 15363 | | | Olfr202 | | |
| 15250 | | | Olfr1431 | | | 15364 | | | Olfr203 | | |
| 15251 | | | Olfr1433 | | | 15365 | | | Olfr204 | | |
| 15252 | | | Olfr1434 | | | 15366 | | | Olfr205 | | |
| 15253 | | | Olfr1436 | | | 15367 | | | Olfr206 | | |
| 15254 | | | Olfr1437 | | | 15368 | | | Olfr209 | | |
| 15255 | | | Olfr1440 | | | 15369 | | | Olfr211 | | |
| 15256 | | | Olfr1441 | | | 15370 | | | Olfr212 | | |
| 15257 | | | Olfr1442 | | | 15371 | | | Olfr213 | | |
| 15258 | | | Olfr1443 | | | 15372 | | | Olfr214 | | |
| 15259 | | | Olfr1444 | | | 15374 | | | Olfr218 | | |
| 15260 | | | Olfr1445 | | | 15377 | | | Olfr222 | | |
| 15261 | | | Olfr1446 | | | 15378 | | | Olfr223 | | |

Fig.22 - 121

| | | | | | | | | | | |
|---|---|---|---|---|---|---|---|---|---|---|
| 15379 | | | | Olfr224 | | | 15494 | | Olfr385 | |
| 15382 | | | | Olfr229 | | | 15496 | | Olfr39 | |
| 15383 | | | | Olfr23 | | | 15497 | | Olfr390 | |
| 15384 | | | | Olfr231 | | | 15498 | | Olfr391-ps | |
| 15385 | | | | Olfr235 | | | 15499 | | Olfr392 | |
| 15387 | | | | Olfr239 | | | 15500 | | Olfr393 | |
| 15388 | | | | Olfr24 | | | 15501 | | Olfr394 | |
| 15389 | | | | Olfr242 | | | 15502 | | Olfr395 | |
| 15390 | | | | Olfr243 | | | 15503 | | Olfr397 | |
| 15391 | | | | Olfr247 | | | 15504 | | Olfr398 | |
| 15392 | | | | Olfr248 | | | 15505 | | Olfr399 | |
| 15393 | | | | Olfr25 | | | 15506 | | Olfr401 | |
| 15394 | | | | Olfr259 | | | 15507 | | Olfr402 | |
| 15395 | | | | Olfr26 | | | 15508 | | Olfr403 | |
| 15396 | | | | Olfr262 | | | 15509 | | Olfr406 | |
| 15397 | | | | Olfr263 | | | 15510 | | Olfr410 | |
| 15398 | | | | Olfr266 | | | 15511 | | Olfr411 | |
| 15399 | | | | Olfr267 | | | 15512 | | Olfr412 | |
| 15400 | | | | Olfr27 | | | 15513 | | Olfr414 | |
| 15401 | | | | Olfr270 | | | 15514 | | Olfr417 | |
| 15402 | | | | Olfr272 | | | 15515 | | Olfr418-ps1 | |
| 15403 | | | | Olfr273 | | | 15516 | | Olfr419 | |
| 15404 | | | | Olfr275 | | | 15517 | | Olfr420 | |
| 15405 | | | | Olfr279 | | | 15518 | | Olfr421-ps1 | |
| 15406 | | | | Olfr281 | | | 15519 | | Olfr424 | |
| 15407 | | | | Olfr282 | | | 15522 | | Olfr429 | |
| 15408 | | | | Olfr283 | | | 15523 | | Olfr43 | |
| 15409 | | | | Olfr284 | | | 15524 | | Olfr430 | |
| 15411 | | | | Olfr286 | | | 15525 | | Olfr432 | |
| 15412 | | | | Olfr287 | | | 15526 | | Olfr433 | |
| 15413 | | | | Olfr288 | | | 15527 | | Olfr434 | |
| 15415 | | | | Olfr291 | | | 15530 | | Olfr44 | |
| 15416 | | | | Olfr292 | | | 15531 | | Olfr441 | |
| 15417 | | | | Olfr293 | | | 15532 | | Olfr444 | |
| 15418 | | | | Olfr294 | | | 15533 | | Olfr446 | |
| 15419 | | | | Olfr295 | | | 15534 | | Olfr447 | |
| 15420 | | | | Olfr297 | | | 15535 | | Olfr448 | |
| 15421 | | | | Olfr298 | | | 15536 | | Olfr449 | |
| 15422 | | | | Olfr299 | | | 15537 | | Olfr45 | |
| 15423 | | | | Olfr29-ps1 | | | 15538 | | Olfr450 | |
| 15425 | | | | Olfr30 | | | 15539 | | Olfr452 | |
| 15426 | | | | Olfr301 | | | 15540 | | Olfr453 | |
| 15427 | | | | Olfr303 | | | 15541 | | Olfr455 | |
| 15428 | | | | Olfr304 | | | 15542 | | Olfr456 | |
| 15429 | | | | Olfr305 | | | 15543 | | Olfr457 | |
| 15431 | | | | Olfr308 | | | 15544 | | Olfr458 | |
| 15432 | | | | Olfr309 | | | 15545 | | Olfr459 | |
| 15433 | | | | Olfr31 | | | 15546 | | Olfr46 | |
| 15434 | | | | Olfr310 | | | 15547 | | Olfr460 | |
| 15435 | | | | Olfr311 | | | 15548 | | Olfr461 | |
| 15437 | | | | Olfr313 | | | 15550 | | Olfr463 | |
| 15438 | | | | Olfr314 | | | 15551 | | Olfr464 | |
| 15439 | | | | Olfr315 | | | 15552 | | Olfr466 | |
| 15440 | | | | Olfr316 | | | 15553 | | Olfr467 | |
| 15441 | | | | Olfr317 | | | 15554 | | Olfr469 | |
| 15442 | | | | Olfr318 | | | 15558 | | Olfr473 | |
| 15446 | | | | Olfr322 | | | 15559 | | Olfr474 | |
| 15447 | | | | Olfr323 | | | 15560 | | Olfr476 | |
| 15448 | | | | Olfr324 | | | 15561 | | Olfr477 | |
| 15449 | | | | Olfr325 | | | 15562 | | Olfr478 | |
| 15450 | | | | Olfr328 | | | 15563 | | Olfr479 | |
| 15451 | | | | Olfr329-ps | | | 15564 | | Olfr48 | |
| 15452 | | | | Olfr33 | | | 15565 | | Olfr480 | |
| 15455 | | | | Olfr332 | | | 15566 | | Olfr481 | |
| 15457 | | | | Olfr339 | | | 15567 | | Olfr482 | |
| 15458 | | | | Olfr340 | | | 15568 | | Olfr483 | |
| 15459 | | | | Olfr341 | | | 15569 | | Olfr484 | |
| 15460 | | | | Olfr342 | | | 15570 | | Olfr485 | |
| 15461 | | | | Olfr344 | | | 15571 | | Olfr486 | |
| 15462 | | | | Olfr345 | | | 15572 | | Olfr487 | |
| 15463 | | | | Olfr346 | | | 15573 | | Olfr488 | |
| 15464 | | | | Olfr347 | | | 15574 | | Olfr49 | |
| 15466 | | | | Olfr350 | | | 15575 | | Olfr490 | |
| 15467 | | | | Olfr351 | | | 15576 | | Olfr491 | |
| 15468 | | | | Olfr352 | | | 15577 | | Olfr492 | |
| 15469 | | | | Olfr353 | | | 15578 | | Olfr493 | |
| 15470 | | | | Olfr354 | | | 15579 | | Olfr494 | |
| 15471 | | | | Olfr355 | | | 15580 | | Olfr495 | |
| 15472 | | | | Olfr356 | | | 15581 | | Olfr497 | |
| 15473 | | | | Olfr357 | | | 15582 | | Olfr498 | |
| 15474 | | | | Olfr358 | | | 15583 | | Olfr5 | |
| 15476 | | | | Olfr361 | | | 15584 | | Olfr50 | |
| 15478 | | | | Olfr365 | | | 15585 | | Olfr502 | |
| 15479 | | | | Olfr366 | | | 15586 | | Olfr503 | |
| 15480 | | | | Olfr367-ps | | | 15587 | | Olfr504 | |
| 15481 | | | | Olfr368 | | | 15588 | | Olfr506 | |
| 15482 | | | | Olfr370 | | | 15589 | | Olfr507 | |
| 15483 | | | | Olfr371 | | | 15590 | | Olfr508 | |
| 15484 | | | | Olfr372 | | | 15591 | | Olfr509 | |
| 15485 | | | | Olfr373 | | | 15592 | | Olfr51 | |
| 15487 | | | | Olfr376 | | | 15593 | | Olfr510 | |
| 15488 | | | | Olfr378 | | | 15594 | | Olfr512 | |
| 15489 | | | | Olfr38 | | | 15595 | | Olfr513 | |
| 15490 | | | | Olfr380 | | | 15596 | | Olfr514 | |
| 15491 | | | | Olfr381 | | | 15597 | | Olfr516 | |
| 15492 | | | | Olfr382 | | | 15598 | | Olfr517 | |
| 15493 | | | | Olfr384 | | | 15599 | | Olfr518 | |

Fig.22 - 122

| | | | | | | | | | | |
|---|---|---|---|---|---|---|---|---|---|---|
| 15600 | | | | Olfr519 | | | 15709 | | | Olfr646 |
| 15601 | | | | Olfr52 | | | 15710 | | | Olfr648 |
| 15602 | | | | Olfr520 | | | 15711 | | | Olfr649 |
| 15603 | | | | Olfr521 | | | 15712 | | | Olfr65 |
| 15604 | | | | Olfr522 | | | 15713 | | | Olfr651 |
| 15605 | | | | Olfr523 | | | 15714 | | | Olfr652 |
| 15606 | | | | Olfr524 | | | 15715 | | | Olfr653 |
| 15607 | | | | Olfr525 | | | 15716 | | | Olfr654 |
| 15608 | | | | Olfr527 | | | 15717 | | | Olfr655 |
| 15609 | | | | Olfr53 | | | 15718 | | | Olfr656 |
| 15610 | | | | Olfr530 | | | 15719 | | | Olfr657 |
| 15611 | | | | Olfr531 | | | 15720 | | | Olfr658 |
| 15612 | | | | Olfr532 | | | 15721 | | | Olfr659 |
| 15613 | | | | Olfr533 | | | 15722 | | | Olfr66 |
| 15614 | | | | Olfr535 | | | 15723 | | | Olfr661 |
| 15615 | | | | Olfr536 | | | 15724 | | | Olfr663 |
| 15616 | | | | Olfr538 | | | 15725 | | | Olfr665 |
| 15617 | | | | Olfr539 | | | 15726 | | | Olfr666 |
| 15618 | | | | Olfr54 | | | 15727 | | | Olfr667 |
| 15620 | | | | Olfr543 | | | 15728 | | | Olfr668 |
| 15622 | | | | Olfr545 | | | 15729 | | | Olfr669 |
| 15624 | | | | Olfr549 | | | 15730 | | | Olfr67 |
| 15626 | | | | Olfr550 | | | 15731 | | | Olfr670 |
| 15627 | | | | Olfr551 | | | 15732 | | | Olfr671 |
| 15628 | | | | Olfr552 | | | 15733 | | | Olfr672 |
| 15630 | | | | Olfr554 | | | 15734 | | | Olfr675 |
| 15634 | | | | Olfr558 | | | 15735 | | | Olfr676 |
| 15638 | | | | Olfr561 | | | 15737 | | | Olfr678 |
| 15639 | | | | Olfr564 | | | 15738 | | | Olfr679 |
| 15640 | | | | Olfr566 | | | 15739 | | | Olfr68 |
| 15641 | | | | Olfr568 | | | 15740 | | | Olfr681 |
| 15643 | | | | Olfr57 | | | 15741 | | | Olfr683 |
| 15644 | | | | Olfr570 | | | 15742 | | | Olfr684 |
| 15645 | | | | Olfr571 | | | 15743 | | | Olfr685 |
| 15646 | | | | Olfr572 | | | 15744 | | | Olfr686 |
| 15647 | | | | Olfr574 | | | 15745 | | | Olfr688 |
| 15648 | | | | Olfr575 | | | 15747 | | | Olfr69 |
| 15649 | | | | Olfr576 | | | 15748 | | | Olfr690 |
| 15650 | | | | Olfr577 | | | 15749 | | | Olfr691 |
| 15651 | | | | Olfr578 | | | 15751 | | | Olfr693 |
| 15652 | | | | Olfr58 | | | 15752 | | | Olfr694 |
| 15653 | | | | Olfr582 | | | 15753 | | | Olfr695 |
| 15654 | | | | Olfr583 | | | 15754 | | | Olfr697 |
| 15655 | | | | Olfr584 | | | 15755 | | | Olfr698 |
| 15656 | | | | Olfr585 | | | 15757 | | | Olfr70 |
| 15657 | | | | Olfr586 | | | 15758 | | | Olfr700 |
| 15658 | | | | Olfr589 | | | 15759 | | | Olfr701 |
| 15659 | | | | Olfr59 | | | 15760 | | | Olfr702 |
| 15660 | | | | Olfr591 | | | 15761 | | | Olfr703 |
| 15661 | | | | Olfr592 | | | 15763 | | | Olfr705 |
| 15662 | | | | Olfr593 | | | 15764 | | | Olfr706 |
| 15663 | | | | Olfr594 | | | 15765 | | | Olfr707 |
| 15664 | | | | Olfr596 | | | 15766 | | | Olfr71 |
| 15665 | | | | Olfr597 | | | 15767 | | | Olfr710 |
| 15666 | | | | Olfr598 | | | 15768 | | | Olfr711 |
| 15667 | | | | Olfr599 | | | 15769 | | | Olfr713 |
| 15668 | | | | Olfr6 | | | 15770 | | | Olfr714 |
| 15669 | | | | Olfr60 | | | 15771 | | | Olfr715 |
| 15670 | | | | Olfr600 | | | 15772 | | | Olfr716 |
| 15671 | | | | Olfr601 | | | 15773 | | | Olfr720 |
| 15672 | | | | Olfr603 | | | 15774 | | | Olfr722 |
| 15673 | | | | Olfr605 | | | 15775 | | | Olfr723 |
| 15674 | | | | Olfr606 | | | 15776 | | | Olfr724 |
| 15675 | | | | Olfr608 | | | 15777 | | | Olfr725 |
| 15676 | | | | Olfr609 | | | 15778 | | | Olfr726 |
| 15677 | | | | Olfr61 | | | 15779 | | | Olfr727 |
| 15678 | | | | Olfr610 | | | 15780 | | | Olfr728 |
| 15679 | | | | Olfr611 | | | 15781 | | | Olfr729 |
| 15680 | | | | Olfr612 | | | 15782 | | | Olfr73 |
| 15681 | | | | Olfr613 | | | 15783 | | | Olfr730 |
| 15682 | | | | Olfr615 | | | 15784 | | | Olfr731 |
| 15683 | | | | Olfr616 | | | 15785 | | | Olfr732 |
| 15684 | | | | Olfr617 | | | 15786 | | | Olfr733 |
| 15685 | | | | Olfr618 | | | 15788 | | | Olfr735 |
| 15686 | | | | Olfr619 | | | 15790 | | | Olfr738 |
| 15687 | | | | Olfr62 | | | 15791 | | | Olfr739 |
| 15688 | | | | Olfr620 | | | 15792 | | | Olfr74 |
| 15689 | | | | Olfr622 | | | 15793 | | | Olfr740 |
| 15690 | | | | Olfr623 | | | 15794 | | | Olfr741 |
| 15691 | | | | Olfr624 | | | 15795 | | | Olfr742 |
| 15692 | | | | Olfr628 | | | 15796 | | | Olfr743 |
| 15693 | | | | Olfr629 | | | 15797 | | | Olfr744 |
| 15694 | | | | Olfr63 | | | 15798 | | | Olfr745 |
| 15695 | | | | Olfr630 | | | 15799 | | | Olfr746 |
| 15696 | | | | Olfr631 | | | 15800 | | | Olfr747 |
| 15697 | | | | Olfr632 | | | 15801 | | | Olfr748 |
| 15698 | | | | Olfr633 | | | 15802 | | | Olfr749 |
| 15699 | | | | Olfr635 | | | 15803 | | | Olfr750 |
| 15700 | | | | Olfr638 | | | 15804 | | | Olfr75-ps1 |
| 15701 | | | | Olfr639 | | | 15805 | | | Olfr76 |
| 15702 | | | | Olfr64 | | | 15806 | | | Olfr761 |
| 15703 | | | | Olfr640 | | | 15807 | | | Olfr763 |
| 15704 | | | | Olfr641 | | | 15808 | | | Olfr765 |
| 15705 | | | | Olfr642 | | | 15809 | | | Olfr767 |
| 15706 | | | | Olfr643 | | | 15810 | | | Olfr768 |
| 15707 | | | | Olfr644 | | | 15811 | | | Olfr769 |
| 15708 | | | | Olfr645 | | | 15812 | | | Olfr77 |

Fig.22 - 123

| | | | | | | | | | | | |
|---|---|---|---|---|---|---|---|---|---|---|---|
| 15813 | | | | Olfr770 | | | 15915 | | | Olfr90 | |
| 15814 | | | | Olfr771 | | | 15916 | | | Olfr900 | |
| 15815 | | | | Olfr772 | | | 15917 | | | Olfr901 | |
| 15816 | | | | Olfr773 | | | 15918 | | | Olfr902 | |
| 15817 | | | | Olfr774 | | | 15919 | | | Olfr904 | |
| 15818 | | | | Olfr775 | | | 15921 | | | Olfr906 | |
| 15819 | | | | Olfr776 | | | 15923 | | | Olfr908 | |
| 15820 | | | | Olfr777 | | | 15924 | | | Olfr91 | |
| 15821 | | | | Olfr78 | | | 15925 | | | Olfr910 | |
| 15822 | | | | Olfr780 | | | 15926 | | | Olfr911-ps1 | |
| 15825 | | | | Olfr784 | | | 15927 | | | Olfr912 | |
| 15826 | | | | Olfr786 | | | 15928 | | | Olfr913 | |
| 15827 | | | | Olfr787 | | | 15929 | | | Olfr914 | |
| 15828 | | | | Olfr788 | | | 15930 | | | Olfr915 | |
| 15829 | | | | Olfr790 | | | 15931 | | | Olfr916 | |
| 15830 | | | | Olfr791 | | | 15932 | | | Olfr917 | |
| 15831 | | | | Olfr792 | | | 15933 | | | Olfr918 | |
| 15832 | | | | Olfr794 | | | 15934 | | | Olfr919 | |
| 15833 | | | | Olfr796 | | | 15935 | | | Olfr92 | |
| 15834 | | | | Olfr798 | | | 15938 | | | Olfr922 | |
| 15835 | | | | Olfr799 | | | 15940 | | | Olfr924 | |
| 15836 | | | | Olfr8 | | | 15941 | | | Olfr926 | |
| 15837 | | | | Olfr800 | | | 15942 | | | Olfr93 | |
| 15838 | | | | Olfr801 | | | 15943 | | | Olfr930 | |
| 15839 | | | | Olfr802 | | | 15944 | | | Olfr933 | |
| 15840 | | | | Olfr803 | | | 15945 | | | Olfr934 | |
| 15841 | | | | Olfr804 | | | 15946 | | | Olfr935 | |
| 15842 | | | | Olfr805 | | | 15947 | | | Olfr936 | |
| 15843 | | | | Olfr806 | | | 15948 | | | Olfr937 | |
| 15844 | | | | Olfr807 | | | 15949 | | | Olfr938 | |
| 15845 | | | | Olfr808 | | | 15950 | | | Olfr94 | |
| 15846 | | | | Olfr809 | | | 15951 | | | Olfr943 | |
| 15847 | | | | Olfr810 | | | 15952 | | | Olfr944 | |
| 15848 | | | | Olfr811 | | | 15953 | | | Olfr945 | |
| 15849 | | | | Olfr812 | | | 15954 | | | Olfr947-ps1 | |
| 15850 | | | | Olfr813 | | | 15955 | | | Olfr948 | |
| 15851 | | | | Olfr814 | | | 15956 | | | Olfr95 | |
| 15852 | | | | Olfr815 | | | 15957 | | | Olfr951 | |
| 15853 | | | | Olfr816 | | | 15958 | | | Olfr952 | |
| 15854 | | | | Olfr818 | | | 15959 | | | Olfr954 | |
| 15855 | | | | Olfr819 | | | 15960 | | | Olfr955 | |
| 15856 | | | | Olfr820 | | | 15961 | | | Olfr957 | |
| 15857 | | | | Olfr821 | | | 15962 | | | Olfr958 | |
| 15858 | | | | Olfr822 | | | 15963 | | | Olfr959 | |
| 15859 | | | | Olfr823 | | | 15964 | | | Olfr96 | |
| 15860 | | | | Olfr824 | | | 15965 | | | Olfr960 | |
| 15861 | | | | Olfr825 | | | 15966 | | | Olfr961 | |
| 15862 | | | | Olfr826 | | | 15967 | | | Olfr963 | |
| 15863 | | | | Olfr827 | | | 15968 | | | Olfr965 | |
| 15864 | | | | Olfr828 | | | 15969 | | | Olfr967 | |
| 15865 | | | | Olfr829 | | | 15970 | | | Olfr968 | |
| 15866 | | | | Olfr830 | | | 15971 | | | Olfr969 | |
| 15867 | | | | Olfr832 | | | 15972 | | | Olfr97 | |
| 15868 | | | | Olfr834 | | | 15973 | | | Olfr970 | |
| 15869 | | | | Olfr835 | | | 15974 | | | Olfr971 | |
| 15871 | | | | Olfr837 | | | 15975 | | | Olfr972 | |
| 15872 | | | | Olfr843 | | | 15976 | | | Olfr974 | |
| 15873 | | | | Olfr845 | | | 15977 | | | Olfr975 | |
| 15874 | | | | Olfr846 | | | 15978 | | | Olfr976 | |
| 15876 | | | | Olfr849 | | | 15981 | | | Olfr98 | |
| 15877 | | | | Olfr850 | | | 15984 | | | Olfr982 | |
| 15878 | | | | Olfr851 | | | 15985 | | | Olfr983 | |
| 15879 | | | | Olfr853 | | | 15986 | | | Olfr984 | |
| 15880 | | | | Olfr854 | | | 15987 | | | Olfr985 | |
| 15881 | | | | Olfr855 | | | 15988 | | | Olfr986 | |
| 15882 | | | | Olfr856-ps1 | | | 15989 | | | Olfr987 | |
| 15883 | | | | Olfr857 | | | 15990 | | | Olfr988 | |
| 15884 | | | | Olfr859 | | | 15991 | | | Olfr99 | |
| 15885 | | | | Olfr860 | | | 15993 | | | Olfr993 | |
| 15886 | | | | Olfr862 | | | 15995 | | | Olfr995 | |
| 15887 | | | | Olfr866 | | | 15996 | | | Olfr996 | |
| 15888 | | | | Olfr867 | | | 15997 | | | Olfr998 | |
| 15889 | | | | Olfr868 | | | 16015 | | | Oog4 | |
| 15890 | | | | Olfr869 | | | 16016 | | | Oosp1 | 255649 | 4-May-15 |
| 15891 | | | | Olfr870 | | | 16017 | | | Oosp2 | 219990 | 4-May-15 |
| 15892 | | | | Olfr871 | | | 16019 | | | Opa1 | 4976 | 7-Jun-15 |
| 15893 | | | | Olfr872 | | | 16020 | | | Opa3 | 80207 | 23-May-15 |
| 15894 | | | | Olfr873 | | | 16032 | | | Oprl1 | 4987 | 4-May-15 |
| 15895 | | | | Olfr874 | | | 16085 | | | Otog1 | 283310 | 7-Jun-15 |
| 15896 | | | | Olfr875 | | | 16087 | | | Otop1 | 133060 | 4-May-15 |
| 15897 | | | | Olfr876 | | | 16096 | | | Otub2 | 78990 | 4-May-15 |
| 15898 | | | | Olfr877 | | | 17384 | | | Prl8a6 | | |
| 15899 | | | | Olfr878 | | | 17385 | | | Prl8a8 | | |
| 15900 | | | | Olfr881 | | | 17386 | | | Prl8a9 | | |
| 15902 | | | | Olfr884 | | | 20036 | | | Snord37 | 26812 | 4-May-15 |
| 15903 | | | | Olfr885 | | | 20072 | | | Snord90 | 692206 | 4-May-15 |
| 15904 | | | | Olfr887 | | | 20157 | | | Son | 6651 | 12-May-15 |
| 15905 | | | | Olfr888 | | | 20738 | | | Svs5 | | |
| 15906 | | | | Olfr889 | | | 20932 | | | Tas2r135 | | |
| 15907 | | | | Olfr890 | | | 20933 | | | Tas2r136 | | |
| 15908 | | | | Olfr891 | | | 20934 | | | Tas2r137 | | |
| 15909 | | | | Olfr893 | | | 20935 | | | Tas2r138 | | |
| 15910 | | | | Olfr894 | | | 20936 | | | Tas2r139 | | |
| 15911 | | | | Olfr895 | | | 20937 | | | Tas2r140 | | |
| 15912 | | | | Olfr898 | | | 20938 | | | Tas2r143 | | |
| 15913 | | | | Olfr899 | | | 20939 | | | Tas2r144 | | |
| 15914 | | | | Olfr9 | | | 20940 | | | Tasp1 | 55617 | 4-May-15 |

Fig.22 - 124

| | | | | | | | | | | |
|---|---|---|---|---|---|---|---|---|---|---|
| 22697 | | | Vmn1r128 | | | 22882 | | | Vmn2r103 | |
| 22712 | | | Vmn1r157 | | | 22883 | | | Vmn2r104 | |
| 22719 | | | Vmn1r166 | | | 22884 | | | Vmn2r105 | |
| 22720 | | | Vmn1r167 | | | 22885 | | | Vmn2r106 | |
| 22721 | | | Vmn1r168 | | | 22886 | | | Vmn2r107 | |
| 22786 | | | Vmn1r228 | | | 22887 | | | Vmn2r108 | |
| 22787 | | | Vmn1r229 | | | 22888 | | | Vmn2r109 | |
| 22788 | | | Vmn1r23 | | | 22889 | | | Vmn2r11 | |
| 22789 | | | Vmn1r230 | | | 22890 | | | Vmn2r110 | |
| 22790 | | | Vmn1r231 | | | 22891 | | | Vmn2r111 | |
| 22791 | | | Vmn1r232 | | | 22892 | | | Vmn2r112 | |
| 22792 | | | Vmn1r233 | | | 22893 | | | Vmn2r113 | |
| 22793 | | | Vmn1r234 | | | 22894 | | | Vmn2r114 | |
| 22794 | | | Vmn1r235 | | | 22895 | | | Vmn2r115 | |
| 22795 | | | Vmn1r236 | | | 22896 | | | Vmn2r116 | |
| 22796 | | | Vmn1r237 | | | 22897 | | | Vmn2r117 | |
| 22797 | | | Vmn1r238 | | | 22898 | | | Vmn2r118 | |
| 22798 | | | Vmn1r24 | | | 22899 | | | Vmn2r12 | |
| 22799 | | | Vmn1r25 | | | 22900 | | | Vmn2r120 | |
| 22800 | | | Vmn1r26 | | | 22901 | | | Vmn2r121 | |
| 22801 | | | Vmn1r27 | | | 22902 | | | Vmn2r122 | |
| 22802 | | | Vmn1r28 | | | 22903 | | | Vmn2r123 | |
| 22803 | | | Vmn1r29 | | | 22904 | | | Vmn2r124 | |
| 22804 | | | Vmn1r3 | | | 22905 | | | Vmn2r13 | |
| 22805 | | | Vmn1r30 | | | 22906 | | | Vmn2r14 | |
| 22806 | | | Vmn1r31 | | | 22907 | | | Vmn2r15 | |
| 22807 | | | Vmn1r32 | | | 22908 | | | Vmn2r16 | |
| 22808 | | | Vmn1r33 | | | 22909 | | | Vmn2r17 | |
| 22809 | | | Vmn1r34 | | | 22910 | | | Vmn2r18 | |
| 22810 | | | Vmn1r35 | | | 22911 | | | Vmn2r19 | |
| 22811 | | | Vmn1r36 | | | 22912 | | | Vmn2r2 | |
| 22812 | | | Vmn1r37 | | | 22913 | | | Vmn2r20 | |
| 22813 | | | Vmn1r38 | | | 22914 | | | Vmn2r21 | |
| 22814 | | | Vmn1r39 | | | 22915 | | | Vmn2r22 | |
| 22815 | | | Vmn1r4 | | | 22916 | | | Vmn2r23 | |
| 22816 | | | Vmn1r40 | | | 22917 | | | Vmn2r24 | |
| 22817 | | | Vmn1r41 | | | 22918 | | | Vmn2r25 | |
| 22818 | | | Vmn1r42 | | | 22919 | | | Vmn2r26 | |
| 22819 | | | Vmn1r43 | | | 22920 | | | Vmn2r27 | |
| 22820 | | | Vmn1r44 | | | 22921 | | | Vmn2r28 | |
| 22821 | | | Vmn1r45 | | | 22922 | | | Vmn2r29 | |
| 22822 | | | Vmn1r46 | | | 22926 | | | Vmn2r32 | |
| 22823 | | | Vmn1r47 | | | 22927 | | | Vmn2r33 | |
| 22824 | | | Vmn1r48 | | | 22928 | | | Vmn2r34 | |
| 22825 | | | Vmn1r49 | | | 22930 | | | Vmn2r36 | |
| 22826 | | | Vmn1r5 | | | 22931 | | | Vmn2r37 | |
| 22827 | | | Vmn1r50 | | | 22932 | | | Vmn2r38 | |
| 22828 | | | Vmn1r51 | | | 22933 | | | Vmn2r39 | |
| 22829 | | | Vmn1r52 | | | 22934 | | | Vmn2r4 | |
| 22830 | | | Vmn1r53 | | | 22935 | | | Vmn2r40 | |
| 22831 | | | Vmn1r54 | | | 22936 | | | Vmn2r41 | |
| 22832 | | | Vmn1r55 | | | 22938 | | | Vmn2r43 | |
| 22833 | | | Vmn1r56 | | | 22939 | | | Vmn2r44 | |
| 22834 | | | Vmn1r57 | | | 22940 | | | Vmn2r45 | |
| 22835 | | | Vmn1r58 | | | 22941 | | | Vmn2r46 | |
| 22836 | | | Vmn1r59 | | | 22942 | | | Vmn2r47 | |
| 22837 | | | Vmn1r6 | | | 22943 | | | Vmn2r48 | |
| 22838 | | | Vmn1r60 | | | 22944 | | | Vmn2r49 | |
| 22839 | | | Vmn1r61 | | | 22945 | | | Vmn2r5 | |
| 22840 | | | Vmn1r62 | | | 22946 | | | Vmn2r50 | |
| 22841 | | | Vmn1r63 | | | 22947 | | | Vmn2r51 | |
| 22842 | | | Vmn1r64 | | | 22948 | | | Vmn2r52 | |
| 22843 | | | Vmn1r65 | | | 22949 | | | Vmn2r53 | |
| 22844 | | | Vmn1r66 | | | 22950 | | | Vmn2r54 | |
| 22845 | | | Vmn1r67 | | | 22951 | | | Vmn2r55 | |
| 22846 | | | Vmn1r68 | | | 22952 | | | Vmn2r56 | |
| 22847 | | | Vmn1r69 | | | 22953 | | | Vmn2r57 | |
| 22848 | | | Vmn1r7 | | | 22954 | | | Vmn2r58 | |
| 22849 | | | Vmn1r70 | | | 22955 | | | Vmn2r59 | |
| 22850 | | | Vmn1r71 | | | 22956 | | | Vmn2r6 | |
| 22851 | | | Vmn1r72 | | | 22957 | | | Vmn2r60 | |
| 22852 | | | Vmn1r73 | | | 22958 | | | Vmn2r61 | |
| 22853 | | | Vmn1r74 | | | 22959 | | | Vmn2r62 | |
| 22854 | | | Vmn1r75 | | | 22960 | | | Vmn2r63 | |
| 22855 | | | Vmn1r76 | | | 22961 | | | Vmn2r65 | |
| 22856 | | | Vmn1r77 | | | 22962 | | | Vmn2r66 | |
| 22857 | | | Vmn1r78 | | | 22963 | | | Vmn2r67 | |
| 22858 | | | Vmn1r79 | | | 22964 | | | Vmn2r68 | |
| 22859 | | | Vmn1r8 | | | 22965 | | | Vmn2r69 | |
| 22861 | | | Vmn1r81 | | | 22966 | | | Vmn2r7 | |
| 22862 | | | Vmn1r82 | | | 22967 | | | Vmn2r70 | |
| 22863 | | | Vmn1r83 | | | 22968 | | | Vmn2r71 | |
| 22864 | | | Vmn1r84 | | | 22970 | | | Vmn2r73 | |
| 22865 | | | Vmn1r85 | | | 22971 | | | Vmn2r74 | |
| 22866 | | | Vmn1r86 | | | 22972 | | | Vmn2r75 | |
| 22867 | | | Vmn1r87 | | | 22973 | | | Vmn2r76 | |
| 22868 | | | Vmn1r88 | | | 22974 | | | Vmn2r77 | |
| 22869 | | | Vmn1r89 | | | 22975 | | | Vmn2r78 | |
| 22870 | | | Vmn1r9 | | | 22976 | | | Vmn2r79 | |
| 22871 | | | Vmn1r90 | | | 22977 | | | Vmn2r8 | |
| 22872 | | | Vmn1r91 | | | 22978 | | | Vmn2r80 | |
| 22873 | | | Vmn1r94 | | | 22979 | | | Vmn2r81 | |
| 22874 | | | Vmn1r95 | | | 22980 | | | Vmn2r82 | |
| 22877 | | | Vmn2r1 | | | 22981 | | | Vmn2r83 | |
| 22879 | | | Vmn2r100 | | | 22982 | | | Vmn2r84 | |
| 22880 | | | Vmn2r101 | | | 22983 | | | Vmn2r85 | |
| 22881 | | | Vmn2r102 | | | 22984 | | | Vmn2r86 | |

Fig.22 - 125

| 22986 | | | | | Vmn2r88 | | |
| --- | --- | --- | --- | --- | --- | --- | --- |
| 22987 | | | | | Vmn2r89 | | |
| 22988 | | | | | Vmn2r9 | | |
| 22990 | | | | | Vmn2r91 | | |
| 22992 | | | | | Vmn2r93 | | |
| 22993 | | | | | Vmn2r94 | | |
| 22994 | | | | | Vmn2r95 | | |
| 22995 | | | | | Vmn2r96 | | |
| 22998 | | | | | Vmn2r99 | | |
| 23001 | | | | | Vmn2r-ps159 | | |
| 23003 | | | | | Vmn2r-ps60 | | |
| 23293 | | | | | Xpnpep1 | 7511 | 12-May-15 |

[Fig. 23-1]

| | AG | | Aorta | | Brain | | Lung | | Pancreas | | PG | | Skin | | Skull | | SM | | Spleen | | Testis | | TG | |
|---|---|---|---|---|---|---|---|---|---|---|---|---|---|---|---|---|---|---|---|---|---|---|---|---|
| | E | M | E | M | E | M | E | M | E | M | E | M | E | M | E | M | E | M | E | M | E | M | E | M |
| Abcb1b | 0.9 | 1.3 | 1.1 | 1.4 | 1.0 | 1.0 | 0.9 | 0.8 | 1.0 | 1.0 | 1.0 | 1.2 | 1.2 | 1.2 | 1.3 | 0.6 | 2.0 | 2.7 | 1.0 | 1.2 | 1.0 | 1.0 | 1.0 | 1.0 |
| Abcg4 | 1.0 | 1.3 | 1.0 | 0.9 | 1.0 | 0.9 | 1.0 | 1.0 | 1.0 | 1.0 | 1.7 | 1.1 | 1.3 | 1.1 | 1.5 | 1.2 | 1.0 | 1.0 | 10.2 | 0.4 | 1.0 | 1.0 | 1.0 | 1.0 |
| Abra | 1.0 | 1.0 | 1.4 | 0.9 | 1.0 | 1.0 | 1.2 | 0.9 | 1.0 | 1.0 | 1.0 | 1.0 | 2.3 | 0.8 | 2.6 | 0.2 | 0.9 | 1.6 | 1.0 | 1.0 | 1.0 | 1.0 | 1.2 | 6.0 |
| Acad7 | 1.0 | 1.0 | 1.0 | 1.0 | 1.0 | 1.0 | 1.0 | 1.0 | 1.0 | 1.0 | 2.0 | 0.7 | 1.0 | 1.0 | 1.0 | 1.0 | 1.0 | 1.2 | 1.0 | 1.0 | 1.0 | 1.0 | 1.0 | 1.0 |
| Acmsd | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Acot3 | 1.0 | 1.0 | 1.0 | 1.0 | 0.7 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Acsm3 | 4.4 | 3.9 | 2.0 | 2.1 | 1.0 | 1.0 | 1.0 | 1.0 | 1.0 | 1.0 | 1.0 | 1.0 | 1.3 | 0.9 | 1.0 | 1.0 | 1.7 | 1.4 | 1.0 | 1.0 | 1.0 | 1.0 | 2.8 | 2.3 |
| Acta1 | 6.2 | 1.0 | 0.6 | 0.3 | 1.1 | 1.4 | 0.7 | 1.4 | 1.0 | 1.0 | 1.0 | 1.0 | 1.7 | 0.8 | 4.2 | 0.3 | 1.0 | 1.1 | 0.8 | 1.0 | 0.9 | 1.2 | 3.1 | 23.8 |
| Actc1 | 2.1 | 1.0 | 0.9 | 0.8 | 1.0 | 1.0 | 0.7 | 0.8 | 1.0 | 1.0 | 1.0 | 1.0 | 0.9 | 0.2 | 0.9 | 0.3 | 0.5 | 0.6 | 1.0 | 1.0 | 0.8 | 1.0 | 25.4 | 0.6 |
| Actg2 | 1.0 | 1.0 | 1.2 | 1.2 | 1.0 | 1.0 | 0.8 | 1.0 | 1.4 | 1.5 | 1.0 | 1.0 | 1.4 | 1.1 | 0.9 | 0.9 | 1.0 | 1.0 | 1.4 | 1.1 | 1.0 | 1.0 | 1.0 | 1.2 |
| Actn2 | 1.0 | 1.0 | 1.2 | 0.9 | 0.8 | 1.0 | 0.7 | 0.8 | 1.0 | 1.0 | 0.9 | 0.8 | 1.9 | 0.8 | 8.3 | 0.3 | 0.8 | 1.3 | 1.0 | 1.0 | 1.0 | 1.0 | 1.7 | 7.9 |
| Actn3 | 1.0 | 1.0 | 1.0 | 1.0 | 1.0 | 1.0 | 1.0 | 1.0 | 1.0 | 1.0 | 1.0 | 1.0 | 4.5 | 1.2 | 7.9 | 0.3 | 1.7 | 1.6 | 1.0 | 1.0 | 1.2 | 0.6 | 1.2 | 34.5 |
| Adam28 | 1.0 | 1.0 | 1.0 | 1.0 | 1.0 | 1.0 | 0.9 | 1.0 | 1.0 | 1.0 | 1.2 | 1.0 | 1.0 | 1.0 | 1.0 | 1.0 | 1.0 | 1.0 | 1.0 | 1.0 | 1.0 | 1.0 | 0.8 | 1.0 |
| Adam7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.3 | 1.0 | 1.0 |
| Adcl2 | 1.0 | 1.5 | 1.0 | 1.0 | 1.0 | 0.9 | 1.0 | 1.0 | 1.0 | 1.0 | 1.0 | 1.0 | 1.0 | 0.8 | 1.7 | 1.6 | 1.0 | 1.0 | 9.6 | 0.3 | 1.1 | 0.9 | 1.0 | 1.0 |
| Adh1 | 4.4 | 9.5 | 1.3 | 1.3 | 1.1 | 1.0 | 1.0 | 1.0 | 1.0 | 1.2 | 1.0 | 1.0 | 1.7 | 1.3 | 3.5 | 1.9 | 1.6 | 1.3 | 1.1 | 1.1 | 1.1 | 1.8 | 1.3 | 0.9 | 1.2 | 1.5 |
| Adh6-ps1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Adh7 | 3.0 | 5.3 | 0.7 | 1.3 | 1.0 | 1.0 | 0.9 | 1.1 | 1.0 | 1.0 | 1.0 | 1.0 | 3.3 | 1.4 | 0.6 | 1.3 | 1.0 | 1.0 | 1.0 | 1.0 | 1.0 | 1.1 | 1.0 | 1.0 |
| Adig | 1.7 | 1.5 | 0.8 | 1.2 | 1.0 | 1.0 | 1.5 | 0.4 | 1.0 | 1.0 | 1.0 | 1.0 | 1.1 | 2.3 | 1.0 | 1.0 | 1.2 | 0.7 | 1.0 | 1.0 | 1.0 | 0.9 | 1.4 | 1.4 |
| Adipoq | 1.9 | 1.8 | 1.2 | 1.6 | 1.0 | 1.0 | 0.9 | 0.2 | 0.3 | 0.3 | 1.0 | 1.0 | 1.0 | 1.6 | 1.4 | 2.9 | 0.9 | 0.7 | 3.4 | 1.4 | 1.0 | 0.9 | 1.6 | 1.4 |
| Agps | 1.0 | 0.9 | 1.0 | 1.3 | 1.0 | 0.9 | 1.0 | 1.1 | 0.8 | 1.0 | 0.9 | 1.1 | 0.9 | 0.9 | 0.9 | 0.9 | 1.0 | 1.0 | 1.0 | 1.0 | 0.9 | 1.1 | 1.0 | 1.0 |
| Agr2 | 1.0 | 1.0 | 1.0 | 1.0 | 1.0 | 1.0 | 1.0 | 1.4 | 1.6 | 2.0 | 1.0 | 1.0 | 1.0 | 1.0 | 1.0 | 1.0 | 1.0 | 1.0 | 1.0 | 1.0 | 1.0 | 1.0 | 0.5 | 0.4 |
| Ahsg | 1.4 | 1.0 | 1.6 | 0.2 | 1.9 | 0.9 | 1.6 | 1.0 | 1.7 | 1.1 | 0.9 | 0.6 | 1.0 | 1.0 | 2.5 | 1.1 | 1.0 | 1.0 | 1.0 | 1.0 | 1.0 | 1.0 | 1.0 | 1.2 |
| Aicda | 1.0 | 1.0 | 1.0 | 1.0 | 1.0 | 1.0 | 1.0 | 1.0 | 1.0 | 1.0 | 1.0 | 1.0 | 1.0 | 0.6 | 1.0 | 1.0 | 0.5 | 0.2 | 1.0 | 1.0 | 1.0 | 1.0 | 1.0 | 1.0 |
| Aim | 1.1 | 0.7 | 1.4 | 0.9 | 0.6 | 0.8 | 1.1 | 0.9 | 1.0 | 1.0 | 0.9 | 1.0 | 0.9 | 0.7 | 1.0 | 0.9 | 1.0 | 0.5 | 1.4 | 0.9 | 1.0 | 1.0 | 0.8 | 1.1 |
| Akp3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Akr1b3 | 0.5 | 1.1 | 1.6 | 0.6 | 1.0 | 0.7 | 1.2 | 0.5 | 1.0 | 1.0 | 1.0 | 0.9 | 0.5 | 0.2 | 0.3 | 1.2 | 2.2 | 1.1 | 1.3 | 2.1 | 0.3 | 0.4 | 2.4 | 2.0 |
| Akr1b7 | 1.4 | 1.6 | 1.0 | 1.0 | 1.0 | 1.0 | 1.0 | 1.0 | 1.0 | 1.0 | 1.0 | 1.0 | 1.0 | 1.0 | 1.0 | 1.0 | 0.8 | 0.9 | 1.0 | 1.0 | 1.0 | 1.0 | 1.0 | 1.0 |
| Akr1b8 | 1.7 | 1.6 | 0.8 | 0.9 | 1.0 | 1.0 | 1.1 | 1.1 | 1.0 | 1.0 | 0.8 | 0.9 | 0.8 | 1.4 | 2.9 | 2.0 | 1.0 | 0.7 | 1.6 | 1.0 | 1.1 | 1.2 | 1.0 | 1.1 |
| Akr1c14 | 1.0 | 0.7 | 0.7 | 0.6 | 1.0 | 1.0 | 2.0 | 1.8 | 1.6 | 1.0 | 0.2 | 0.1 | 0.7 | 0.9 | 1.2 | 1.0 | 0.8 | 0.6 | 0.8 | 1.2 | 1.0 | 1.0 | 0.9 | 0.7 |
| Akr1c19 | 1.0 | 1.0 | 1.0 | 1.0 | 1.0 | 1.0 | 1.0 | 1.0 | 1.0 | 1.0 | 1.0 | 1.0 | 0.9 | 0.9 | 1.0 | 1.0 | 1.0 | 1.0 | 1.0 | 1.0 | 1.0 | 1.0 | 1.0 | 1.0 |
| Alas2 | 2.3 | 2.0 | 2.5 | 1.6 | 1.3 | 1.3 | 2.5 | 1.6 | 1.0 | 1.4 | 1.2 | 0.7 | 1.3 | 1.2 | 1.6 | 2.3 | 1.7 | 2.4 | 1.9 | 0.7 | 0.9 | 1.1 | 3.8 | 2.5 |
| Alb | 1.9 | 0.6 | 1.0 | 0.2 | 1.0 | 0.7 | 1.6 | 1.0 | 1.1 | 1.2 | 0.8 | 0.9 | 1.0 | 1.5 | 5.0 | 1.0 | 1.0 | 0.8 | 1.6 | 1.0 | 1.0 | 1.2 | 1.0 | 1.0 |
| Aldh1a1 | 0.5 | 0.1 | 1.3 | 1.0 | 1.0 | 1.0 | 1.1 | 1.0 | 1.2 | 0.9 | 0.9 | 1.5 | 1.4 | 1.0 | 2.0 | 1.5 | 1.5 | 1.4 | 2.3 | 0.7 | 0.7 | 0.9 | 0.8 | 4.3 |
| Aldh1a3 | 1.0 | 0.9 | 1.2 | 1.3 | 1.0 | 1.0 | 1.1 | 1.2 | 1.0 | 1.0 | 1.0 | 1.0 | 0.6 | 0.9 | 0.4 | 0.6 | 1.0 | 1.2 | 0.9 | 0.7 | 1.0 | 1.1 | 33.7 | 3.8 |
| Aldh3a1 | 1.0 | 1.0 | 1.2 | 1.0 | 1.0 | 1.0 | 1.1 | 1.2 | 1.0 | 1.0 | 0.7 | 0.7 | 1.7 | 1.5 | 1.2 | 1.0 | 1.0 | 1.0 | 1.0 | 1.0 | 0.8 | 0.5 | 16.3 | 1.0 |
| Aldob | 2.1 | 0.8 | 1.0 | 0.2 | 1.3 | 1.1 | 1.3 | 1.0 | 1.9 | 1.9 | 0.7 | 1.0 | 1.0 | 1.2 | 1.6 | 1.6 | 1.0 | 1.0 | 1.7 | 1.0 | 2.2 | 1.1 | 1.0 | 1.0 |
| Aldoc | 1.1 | 1.3 | 1.7 | 1.2 | 1.1 | 1.0 | 1.4 | 1.1 | 1.0 | 1.0 | 1.3 | 1.1 | 1.0 | 0.8 | 1.6 | 1.1 | 1.0 | 0.8 | 1.0 | 0.6 | 0.7 | 0.8 | 0.9 |
| Alpk3 | 1.0 | 1.0 | 1.0 | 0.9 | 1.0 | 1.0 | 0.9 | 1.0 | 1.0 | 1.0 | 1.0 | 1.0 | 2.3 | 0.9 | 3.1 | 0.3 | 1.0 | 1.2 | 1.0 | 1.0 | 1.0 | 1.0 | 1.6 | 7.3 |
| Alpl | 0.5 | 0.5 | 0.5 | 0.6 | 0.9 | 0.9 | 0.9 | 1.0 | 1.0 | 1.0 | 0.7 | 0.9 | 0.9 | 1.2 | 0.9 | 1.1 | 0.6 | 0.8 | 1.0 | 1.3 | 1.0 | 0.6 | 1.0 | 0.7 |
| Ambn | 1.0 | 0.9 | 1.0 | 0.4 | 1.0 | 1.0 | 1.0 | 1.0 | 1.0 | 1.8 | 1.0 | 1.0 | 1.0 | 1.0 | 1.0 | 1.0 | 1.0 | 1.0 | 1.0 | 1.0 | 1.0 | 1.0 | 1.0 | 1.0 |
| Amd1 | 1.0 | 0.1 | 1.0 | 1.0 | 1.0 | 1.0 | 1.0 | 0.2 | 1.0 | 1.0 | 1.0 | 1.0 | 1.0 | 0.1 | 1.0 | 5.5 | 0.0 | 0.3 | 1.0 | 1.0 | 1.0 | 1.0 | 1.0 | 1.0 |
| Ampd1 | 1.0 | 1.0 | 1.0 | 1.0 | 1.0 | 1.0 | 1.0 | 1.0 | 1.0 | 1.0 | 1.0 | 1.0 | 2.1 | 0.7 | 2.9 | 0.3 | 0.8 | 0.9 | 1.0 | 1.0 | 1.0 | 1.0 | 0.5 | 12.9 |
| Amy1 | 1.3 | 1.4 | 1.2 | 1.5 | 1.2 | 1.0 | 1.2 | 0.8 | 0.9 | 1.0 | 2.3 | 2.1 | 1.1 | 1.6 | 1.8 | 1.2 | 1.5 | 1.4 | 1.0 | 1.3 | 1.0 | 1.1 | 1.5 | 2.1 |
| Amy2a2 | 1.0 | 1.0 | 1.0 | 1.0 | 1.0 | 1.0 | 1.0 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Prol1 | 0.1 | 0.9 | 1.0 | 1.0 | 0.9 | 0.9 | 0.9 | 1.0 | 0.9 | 1.0 | 0.6 | 0.7 | 10.1 | 1.0 | 14.5 | 1.0 | 1.4 | 1.0 | 0.7 | 0.9 | 1.1 | 0.6 | 1.1 | 1.0 |
| Amy2b | 1.0 | 0.8 | 1.0 | 1.0 | 0.9 | 1.3 | 1.0 | 1.0 | 0.9 | 1.0 | 0.8 | 1.0 | 2.3 | 1.0 | 1.3 | 1.1 | 1.0 | 1.0 | 1.0 | 0.8 | 1.0 | 1.0 | 1.0 | 1.0 |
| Ang6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Angptl7 | 1.0 | 1.0 | 1.4 | 1.3 | 1.0 | 1.0 | 1.0 | 1.0 | 0.6 | 0.7 | 1.0 | 1.0 | 1.0 | 1.0 | 1.5 | 0.9 | 0.7 | 0.4 | 0.6 | 1.3 | 1.0 | 1.5 | 1.0 | 1.9 | 2.4 |
| Ank1 | 0.8 | 0.7 | 1.0 | 0.9 | 1.0 | 0.9 | 1.0 | 1.0 | 1.0 | 1.0 | 0.5 | 1.0 | 1.2 | 0.8 | 1.5 | 1.3 | 0.8 | 1.0 | 9.0 | 0.3 | 1.0 | 1.0 | 3.0 | 4.6 |
| Ankrd1 | 1.0 | 1.0 | 1.1 | 1.1 | 1.0 | 1.0 | 1.0 | 0.7 | 1.0 | 1.0 | 1.0 | 1.0 | 2.3 | 0.7 | 2.0 | 0.8 | 0.2 | 2.7 | 1.0 | 1.0 | 1.0 | 1.0 | 6.4 | 1.2 |
| Ankrd2 | 1.0 | 1.0 | 1.0 | 1.0 | 1.0 | 1.0 | 1.0 | 1.0 | 1.0 | 1.0 | 1.6 | 0.7 | 4.5 | 1.6 | 0.6 | 1.3 | 1.6 | 2.0 | 1.0 | 1.0 | 1.4 | 5.1 |
| Ankrd23 | 1.1 | 1.0 | 1.1 | 0.7 | 0.7 | 1.2 | 1.1 | 0.9 | 0.8 | 1.1 | 1.1 | 1.4 | 2.8 | 0.9 | 2.9 | 0.2 | 1.0 | 1.1 | 1.8 | 1.3 | 1.4 | 0.9 | 1.2 | 3.6 |
| Ankrd66 | 1.0 | 1.0 | 1.0 | 1.0 | 1.0 | 1.0 | 1.3 | 0.7 | 1.0 | 1.0 | 1.0 | 1.0 | 0.8 | 1.3 | 1.0 | 1.0 | 1.8 | 1.2 | 1.0 | 1.0 | 6.7 | 14.3 |
| Anpep | 0.9 | 0.6 | 1.0 | 0.8 | 1.1 | 1.1 | 1.0 | 1.1 | 1.2 | 1.1 | 1.0 | 1.2 | 1.2 | 1.1 | 1.2 | 1.0 | 1.0 | 0.7 | 0.6 | 1.0 | 1.0 | 28.3 | 4.0 |
| Ap1m2 | 1.0 | 1.0 | 1.0 | 1.0 | 1.0 | 1.0 | 0.9 | 1.0 | 1.1 | 1.1 | 0.9 | 1.0 | 1.3 | 0.8 | 1.0 | 1.0 | 0.7 | 0.6 | 1.0 | 1.0 | 1.0 | 0.9 |
| Ap1s2 | 1.1 | 0.9 | 1.0 | 0.9 | 1.0 | 1.0 | 1.1 | 0.9 | 1.0 | 1.0 | 1.0 | 1.0 | 0.9 | 1.1 | 0.9 | 0.9 | 0.9 | 0.9 | 0.9 | 0.9 | 0.9 | 1.3 | 1.0 | 1.0 |
| Ap1s3 | 1.0 | 1.0 | 1.0 | 1.0 | 1.4 | 1.1 | 0.2 | 1.0 | 0.5 | 0.9 | 1.0 | 1.0 | 0.9 | 0.9 | 0.7 | 1.1 | 1.0 | 1.0 | 0.9 | 0.9 | 1.0 | 1.0 | 1.3 | 1.0 |
| Apln | 0.3 | 0.2 | 0.5 | 0.6 | 0.8 | 0.8 | 0.6 | 0.7 | 1.0 | 1.0 | 1.1 | 1.1 | 0.5 | 0.9 | 0.2 | 0.6 | 0.6 | 0.6 | 1.0 | 1.0 | 0.6 | 1.0 | 1.3 | 0.6 |
| Aplnr | 0.4 | 0.7 | 0.3 | 0.5 | 1.0 | 1.0 | 0.4 | 0.4 | 1.0 | 1.0 | 0.9 | 0.1 | 0.6 | 0.5 | 0.7 | 0.5 | 1.0 | 0.2 | 0.5 | 0.5 | 1.0 | 1.0 | 0.4 | 0.3 |
| Apoa1 | 2.8 | 1.1 | 1.0 | 1.0 | 1.3 | 0.7 | 1.6 | 1.0 | 1.2 | 1.0 | 0.7 | 1.0 | 1.9 | 2.0 | 2.0 | 0.8 | 1.0 | 2.0 | 0.7 | 2.2 | 1.0 | 3.2 | 1.0 | 1.0 |
| Apoa2 | 5.3 | 1.5 | 0.8 | 0.1 | 0.6 | 0.9 | 2.7 | 1.0 | 0.8 | 1.6 | 1.3 | 0.6 | 1.0 | 1.0 | 1.1 | 1.2 | 1.0 | 1.0 | 0.5 | 1.2 | 1.0 | 1.7 | 1.2 | 1.1 |
| Apoa4 | 1.0 | 1.0 | 1.0 | 1.0 | 1.0 | 1.0 | 1.0 | 1.0 | 1.0 | 1.0 | 1.1 | 1.0 | 1.0 | 3.2 | 1.0 | 1.0 | 1.0 | 1.0 | 1.0 | 1.5 | 1.0 | 7.7 | 1.0 | 1.0 |
| Apoa5 | 1.0 | 0.9 | 1.0 | 0.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Apobec2 | 1.0 | 0.8 | 1.1 | 0.6 | 1.0 | 1.0 | 0.6 | 0.8 | 1.0 | 1.0 | 1.1 | 1.2 | 1.6 | 0.8 | 2.7 | 0.4 | 1.1 | 0.9 | 0.9 | 0.3 | 1.4 | 1.0 | 1.9 | 17.9 |
| Apoc3 | 4.4 | 1.6 | 1.0 | 0.2 | 0.6 | 0.7 | 0.8 | 1.0 | 1.0 | 1.0 | 1.7 | 2.5 | 1.0 | 1.0 | 1.0 | 1.0 | 1.0 | 1.0 | 1.0 | 0.8 | 1.0 | 1.0 | 1.0 | 0.9 |
| Apoc4 | 1.3 | 1.5 | 1.0 | 0.3 | 1.0 | 1.0 | 1.0 | 1.0 | 1.0 | 1.0 | 1.0 | 1.0 | 3.7 | 0.8 | 1.0 | 1.0 | 1.0 | 1.0 | 1.0 | 1.0 | 1.0 | 1.0 | 1.0 | 1.0 |
| Apoe | 0.8 | 0.7 | 1.6 | 1.6 | 1.1 | 1.2 | 1.0 | 0.8 | 0.2 | 1.1 | 1.3 | 1.0 | 1.4 | 1.1 | 1.1 | 1.5 | 1.1 | 0.7 | 1.1 | 1.3 | 1.2 | 0.8 | 1.2 | 1.2 |
| Apoh | 1.1 | 1.3 | 1.0 | 0.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Apol10b | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Apol11b | 1.0 | 1.0 | 1.0 | 1.0 | 1.0 | 1.0 | 1.0 | 1.0 | 1.0 | 1.0 | 1.0 | 1.0 | 1.1 | 1.2 | 1.0 | 1.0 | 2.2 | 0.3 | 1.0 | 1.0 | 1.0 | 1.0 | 1.0 | 1.0 |
| Apol8 | 1.0 | 1.0 | 1.0 | 1.0 | 1.2 | 1.2 | 1.0 | 1.0 | 1.0 | 1.0 | 1.0 | 1.0 | 1.0 | 1.6 | 1.0 | 1.0 | 8.6 | 0.3 | 1.0 | 1.0 | 1.0 | 1.0 | 1.0 | 1.0 |
| Arg2 | 1.0 | 1.0 | 1.0 | 1.0 | 1.5 | 1.7 | 2.0 | 2.0 | 2.7 | 4.1 | 1.0 | 1.0 | 0.4 | 0.7 | 0.8 | 0.8 | 1.0 | 1.0 | 1.5 | 1.0 | 1.0 | 1.0 | 0.9 | 1.0 |
| Armcx6 | 1.1 | 0.9 | 1.0 | 1.0 | 0.8 | 0.9 | 0.8 | 0.9 | 1.0 | 1.0 | 1.2 | 1.0 | 0.4 | 0.4 | 0.7 | 1.2 | 0.7 | 0.6 | 0.8 | 1.0 | 1.0 | 0.9 | 0.7 | 0.7 |
| Arnt2 | 0.7 | 0.6 | 1.0 | 0.2 | 1.0 | 0.9 | 1.0 | 1.0 | 1.0 | 1.0 | 1.4 | 1.1 | 0.8 | 0.3 | 0.7 | 0.9 | 1.0 | 1.0 | 1.0 | 1.0 | 1.0 | 1.0 | 1.0 | 1.0 |
| Art1 | 1.0 | 1.0 | 1.0 | 0.9 | 1.0 | 1.0 | 0.5 | 0.9 | 1.0 | 1.0 | 1.0 | 1.0 | 2.2 | 0.9 | 4.7 | 0.3 | 1.1 | 0.9 | 1.0 | 1.0 | 1.1 | 1.3 | 9.6 |
| Asb11 | 1.0 | 1.0 | 1.0 | 1.7 | 0.9 | 1.7 | 1.0 | 0.8 | 2.8 | 2.9 | 1.0 | 1.0 | 4.5 | 1.4 | 7.8 | 0.4 | 1.8 | 1.7 | 1.0 | 1.0 | 1.0 | 1.0 | 1.8 | 13.2 |
| Asb16 | 1.0 | 1.0 | 1.0 | 1.0 | 1.1 | 0.7 | 1.0 | 1.0 | 1.3 | 1.6 | 1.0 | 1.0 | 2.0 | 1.2 | 3.5 | 0.3 | 1.2 | 1.6 | 1.0 | 1.0 | 1.0 | 1.0 | 1.6 | 5.7 |
| Asb2 | 1.0 | 1.0 | 1.0 | 0.7 | 1.0 | 1.2 | 0.8 | 0.8 | 1.0 | 1.0 | 1.0 | 1.0 | 3.5 | 1.0 | 3.2 | 0.3 | 1.3 | 0.9 | 0.9 | 1.1 | 1.1 | 0.8 | 1.4 | 3.8 |
| Asb5 | 1.0 | 1.0 | 1.0 | 1.0 | 1.0 | 1.0 | 1.0 | 1.0 | 1.0 | 1.0 | 1.0 | 1.0 | 2.3 | 1.0 | 3.6 | 0.4 | 1.0 | 1.0 | 1.0 | 1.0 | 1.0 | 1.0 | 1.0 | 11.4 |
| Asb14 | 1.0 | 1.0 | 1.0 | 1.0 | 1.0 | 1.0 | 1.0 | 1.0 | 1.0 | 1.0 | 1.2 | 0.6 | 0.7 | 0.6 | 1.0 | 1.0 | 1.0 | 1.0 | 1.0 | 1.0 | 1.0 | 1.0 | 1.1 | 1.1 |
| Asprv1 | 1.0 | 1.0 | 1.0 | 1.0 | 1.4 | 1.4 | 2.8 | 2.6 | 1.0 | 1.0 | 1.0 | 1.1 | 1.3 | 3.5 | 1.8 | 2.0 | 1.0 | 1.0 | 1.2 | 1.3 | 0.5 | 1.3 | 39.1 | 1.0 |

| | | | | | | | | | | | | | | | | | | | | | | | | |
|---|---|---|---|---|---|---|---|---|---|---|---|---|---|---|---|---|---|---|---|---|---|---|---|---|
| Cxcl1 | 1.0 | 1.0 | 1.0 | 1.0 | 1.0 | 1.0 | 0.9 | 0.7 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 |
| Cxcl3 | 8.5 | 4.5 | 3.6 | 3.8 | 1.0 | 1.0 | 1.6 | 0.4 | 1.1 | 0.8 | 1.2 | 1.5 | 4.6 | 2.4 | 2.0 | 1.5 | 5.1 | 1.8 | 1.0 | 1.2 | 1.0 | 1.0 | 0.4 | 0.5 |
| Cxcr5 | 1.0 | 1.0 | 1.2 | 1.0 | 1.0 | 1.0 | 0.4 | 0.5 | 1.0 | 1.0 | 1.0 | 1.0 | 1.0 | 1.0 | 1.8 | 2.1 | 1.0 | 1.0 | 0.9 | 0.9 | 1.2 | 0.8 | 1.0 | 1.0 |
| Cyb561 | 0.8 | 0.7 | 1.2 | 1.3 | 1.1 | 1.1 | 1.1 | 1.1 | 1.1 | 1.4 | 0.9 | 0.9 | 0.8 | 1.0 | 1.3 | 1.4 | 0.7 | 1.0 | 1.4 | 1.4 | 1.0 | 1.2 | 0.9 | 0.9 |
| Cyr | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp1a1 | 1.0 | 1.0 | 2.1 | 3.9 | 1.0 | 1.0 | 3.1 | 6.0 | 1.0 | 1.0 | 1.0 | 1.0 | 1.0 | 1.8 | 1.0 | 1.0 | 1.2 | 1.0 | 1.0 | 1.0 | 1.0 | 1.0 | 1.4 | 2.1 |
| Cyp26b1 | 2.1 | 1.8 | 1.7 | 1.3 | 1.0 | 1.0 | 3.5 | 2.0 | 1.0 | 1.0 | 2.7 | 2.9 | 1.3 | 1.2 | 1.6 | 1.7 | 1.2 | 1.5 | 1.9 | 3.0 | 1.1 | 0.9 | 2.7 | 1.0 |
| Cyp27b1 | 1.0 | 1.0 | 1.0 | 1.0 | 1.0 | 1.0 | 1.0 | 1.0 | 1.0 | 1.0 | 1.0 | 0.4 | 0.5 | 1.0 | 1.0 | 1.0 | 1.0 | 1.0 | 1.0 | 1.0 | 1.0 | 1.0 | 1.6 | 0.7 |
| Cyp2b4 | 1.0 | 1.0 | 1.0 | 1.0 | 1.0 | 1.0 | 1.0 | 2.1 | 1.0 | 1.0 | 1.0 | 1.0 | 1.0 | 1.0 | 1.0 | 1.0 | 1.0 | 1.0 | 1.0 | 1.0 | 1.0 | 1.0 | 0.3 | 1.0 |
| Cyp2b5 | 1.0 | 1.0 | 1.0 | 1.0 | 1.0 | 1.0 | 0.8 | 1.6 | 1.0 | 1.0 | 1.5 | 2.4 | 1.0 | 1.0 | 1.0 | 1.0 | 1.0 | 1.0 | 1.0 | 1.0 | 1.0 | 1.0 | 0.0 | 6.9 |
| Cyp2b9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2c38 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2c54 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2d12 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2d40 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2d9 | 1.0 | 1.0 | 0.4 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp2e1 | 2.8 | 2.5 | 1.8 | 2.0 | 1.0 | 1.0 | 0.9 | 0.3 | 0.6 | 0.6 | 0.9 | 1.0 | 1.4 | 3.1 | 1.2 | 3.2 | 2.0 | 1.4 | 5.0 | 1.5 | 1.2 | 1.0 | 1.6 | 1.9 |
| Cyp2f2 | 5.3 | 2.5 | 2.7 | 1.7 | 1.0 | 1.0 | 1.1 | 1.0 | 1.0 | 1.0 | 1.3 | 1.4 | 1.4 | 1.5 | 0.8 | 1.2 | 1.3 | 1.9 | 1.0 | 1.0 | 1.0 | 1.0 | 0.4 | 1.0 |
| Cyp2u1 | 1.0 | 0.7 | 0.8 | 0.9 | 0.8 | 0.8 | 1.0 | 1.0 | 1.0 | 1.0 | 1.2 | 0.8 | 1.0 | 1.0 | 1.0 | 0.9 | 0.9 | 0.9 | 1.1 | 1.1 | 1.2 | 1.1 | 0.9 | 0.8 |
| Cyp39a1 | 0.9 | 0.9 | 0.8 | 0.9 | 1.2 | 0.8 | 1.0 | 0.9 | 1.2 | 1.5 | 1.1 | 1.0 | 1.0 | 1.0 | 0.7 | 0.9 | 0.8 | 1.1 | 0.6 | 0.8 | 1.2 | 1.3 | 0.9 | 1.2 |
| Cyp3a11 | 1.0 | 1.0 | 1.0 | 0.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp3a44 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp3a59 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp4a12a | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp4a12b | 1.0 | 1.0 | 1.0 | 1.0 | 1.0 | 1.0 | 1.0 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 0.4 | 1.0 |
| Cyp4a3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp4b1-ps2 | 1.0 | 1.0 | 1.0 | 1.0 | 1.0 | 1.0 | 1.0 | 0.7 | 1.0 | 1.0 | 1.0 | 1.0 | 1.0 | 1.0 | 1.2 | 2.2 | 1.0 | 1.0 | 1.5 | 0.4 | 1.1 | 1.0 | 0.7 | 1.0 |
| Cyp7b1 | 1.1 | 0.7 | 1.0 | 1.0 | 1.0 | 1.0 | 1.1 | 0.8 | 1.0 | 1.0 | 1.1 | 1.0 | 0.5 | 1.1 | 0.6 | 1.1 | 1.0 | 1.0 | 1.1 | 1.7 | 1.0 | 1.0 | 0.7 | 0.7 |
| Cyp8b1 | 1.0 | 1.0 | 1.0 | 1.0 | 1.0 | 1.0 | 1.1 | 1.2 | 1.0 | 1.0 | 1.0 | 1.0 | 0.8 | 1.0 | 1.0 | 1.0 | 1.0 | 0.9 | 1.3 | 1.0 | 1.0 | 1.0 | 1.0 | 1.0 |
| Cystm1 | 0.9 | 1.7 | 0.4 | 0.3 | 1.2 | 1.1 | 1.3 | 1.4 | 1.5 | 1.3 | 1.0 | 0.8 | 2.2 | 1.0 | 1.8 | 0.5 | 1.1 | 1.2 | 1.3 | 2.0 | 1.0 | 0.9 | 0.8 | 1.1 |
| D6R5 | 1.0 | 1.0 | 1.0 | 1.2 | 1.4 | 0.7 | 1.0 | 1.0 | 1.0 | 1.0 | 1.0 | 0.8 | 1.0 | 0.7 | 1.0 | 1.3 | 1.0 | 1.0 | 1.0 | 1.0 | 1.1 | 1.2 | 1.8 | 1.0 |
| Dcpp2 | 1.0 | 1.0 | 1.0 | 0.7 | 1.0 | 1.0 | 1.0 | 0.7 | 0.5 | 1.0 | 1.2 | 1.0 | 1.0 | 1.0 | 1.0 | 1.0 | 0.5 | 1.0 | 1.0 | 1.0 | 1.0 | 1.0 | 0.2 | 0.2 |
| Dcpp3 | 1.0 | 1.0 | 1.0 | 1.1 | 1.0 | 1.0 | 1.0 | 0.6 | 0.6 | 1.0 | 0.7 | 1.0 | 1.0 | 1.0 | 1.0 | 1.0 | 0.5 | 1.0 | 1.0 | 1.0 | 1.0 | 1.0 | 0.3 | 0.3 |
| Dcstamp | 1.0 | 1.0 | 1.0 | 1.0 | 1.0 | 1.0 | 1.0 | 1.0 | 1.0 | 1.0 | 1.0 | 1.0 | 1.0 | 1.0 | 3.4 | 6.3 | 1.0 | 1.0 | 1.0 | 1.0 | 1.0 | 1.0 | 1.0 | 1.0 |
| Dct | 1.0 | 1.0 | 1.0 | 1.0 | 1.0 | 1.0 | 1.0 | 1.0 | 1.0 | 1.0 | 1.6 | 1.0 | 0.2 | 0.4 | 1.0 | 1.0 | 1.0 | 1.0 | 1.0 | 1.0 | 1.1 | 0.9 | 1.0 | 1.0 |
| Scgb1b27 | 0.1 | 0.8 | 1.7 | 1.6 | 0.8 | 0.9 | 1.0 | 1.7 | 1.2 | 1.0 | 1.1 | 1.0 | 0.8 | 1.1 | 1.5 | 0.7 | 2.3 | 1.9 | 0.9 | 0.9 | 0.8 | 1.0 | 0.9 | 1.0 |
| Ddb1 | 1.0 | 1.0 | 1.0 | 1.0 | 1.1 | 1.0 | 0.8 | 1.0 | 1.0 | 1.0 | 1.5 | 1.0 | 1.7 | 0.8 | 1.9 | 0.5 | 1.1 | 1.0 | 1.0 | 1.0 | 1.0 | 1.0 | 0.8 | 3.8 |
| Defa24 | 1.0 | 1.0 | 1.0 | 1.0 | 1.0 | 1.0 | 1.0 | 1.0 | 1.0 | 1.0 | 1.0 | 1.2 | 0.8 | 0.2 | 1.0 | 1.0 | 5.3 | 1.0 | 1.0 | 1.0 | 4.5 | 1.0 | 1.0 | 1.0 |
| Defb1 | 1.0 | 1.0 | 1.0 | 1.0 | 1.0 | 1.0 | 1.0 | 1.0 | 1.0 | 1.0 | 1.0 | 1.4 | 1.4 | 1.0 | 1.0 | 1.0 | 1.0 | 1.0 | 1.0 | 1.0 | 1.0 | 1.0 | 1.0 | 1.0 |
| Defb10 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb12 | 1.0 | 1.0 | 1.0 | 1.0 | 1.0 | 1.0 | 1.0 | 1.0 | 1.0 | 1.0 | 1.6 | 1.0 | 1.0 | 1.0 | 1.0 | 1.0 | 1.0 | 1.0 | 1.0 | 1.0 | 1.0 | 1.0 | 1.0 | 1.0 |
| Defb14 | 1.0 | 1.0 | 1.0 | 1.0 | 1.0 | 1.0 | 1.0 | 1.0 | 1.0 | 1.0 | 1.0 | 1.0 | 2.9 | 5.3 | 1.0 | 1.0 | 1.0 | 1.0 | 1.0 | 1.0 | 1.6 | 2.8 | 1.0 | 1.0 |
| Defb15 | 1.0 | 1.0 | 1.0 | 1.0 | 1.0 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.8 | 1.9 | 1.0 | 1.0 |
| Defb18 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb19 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.9 | 1.0 | 1.0 |
| | AG | | Aorta | | Brain | | Lung | | Pancreas | | PG | | Skin | | Skull | | SM | | Spleen | | Testis | | TG | |
| | E | M | E | M | E | M | E | M | E | M | E | M | E | M | E | M | E | M | E | M | E | M | E | M |
| Defb2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb20 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb21 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.4 | 1.2 | 1.0 | 1.0 |
| Defb22 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.1 | 12.0 | 1.0 | 1.0 |
| Defb23 | 1.0 | 1.0 | 1.0 | 1.0 | 1.0 | 1.0 | 0.6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb25 | 1.0 | 0.6 | 1.0 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 |
| Defb26 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.9 | 1.0 | 1.0 |
| Defb28 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.8 | 2.9 | 7.3 | 1.0 | 1.0 |
| Defb29 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb30 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.2 | 1.6 | 1.0 | 1.0 |
| Defb35 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb37 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.3 | 5.2 | 1.0 | 1.0 |
| Defb39 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.4 | 1.0 | 1.0 |
| Defb4 | 1.0 | 1.0 | 1.0 | 1.0 | 1.0 | 1.0 | 1.0 | 1.0 | 1.0 | 1.0 | 1.0 | 1.0 | 3.8 | 1.0 | 1.0 | 1.0 | 1.0 | 1.0 | 1.0 | 1.0 | 1.0 | 1.0 | 13.4 | 1.0 |
| Defb41 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.3 | 1.0 |
| Defb42 | 1.0 | 1.0 | 0.3 | 0.6 | 1.0 | 1.0 | 1.0 | 1.0 | 1.0 | 1.0 | 1.0 | 1.0 | 1.0 | 1.0 | 1.0 | 1.0 | 0.8 | 0.8 | 1.0 | 1.0 | 1.0 | 1.2 | 0.8 | 0.7 |
| Defb43 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.2 | 3.2 | 1.0 |
| Defb45 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.6 | 1.3 | 1.0 | 1.0 |
| Defb47 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb48 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Defb8 | 1.0 | 1.0 | 1.0 | 1.0 | 1.0 | 1.0 | 1.0 | 1.0 | 1.0 | 1.0 | 1.0 | 1.0 | 0.2 | 0.9 | 1.0 | 1.0 | 1.0 | 1.0 | 1.0 | 1.0 | 1.0 | 1.0 | 1.0 | 1.0 |
| Degcr7 | 1.0 | 1.0 | 1.0 | 1.0 | 1.0 | 0.9 | 1.0 | 1.0 | 1.2 | 1.0 | 0.9 | 1.7 | 1.6 | 1.0 | 0.8 | 0.8 | 1.0 | 1.0 | 1.2 | 1.7 | 1.0 | 1.0 | 1.0 | 1.0 |
| Derl3 | 1.3 | 1.0 | 1.0 | 0.9 | 1.0 | 0.8 | 0.8 | 1.2 | 1.4 | 1.0 | 0.7 | 1.0 | 0.6 | 0.9 | 0.9 | 1.0 | 1.0 | 0.7 | 1.1 | 1.0 | 0.8 | 1.0 | 0.8 | 0.7 |
| Des | 1.0 | 0.9 | 0.9 | 1.0 | 1.0 | 0.9 | 0.6 | 0.9 | 1.5 | 1.3 | 0.9 | 0.8 | 2.8 | 0.9 | 4.6 | 0.4 | 1.4 | 1.2 | 0.9 | 1.0 | 1.0 | 0.8 | 1.5 | 15.1 |
| Dhrs7c | 1.0 | 1.0 | 1.0 | 1.1 | 1.0 | 1.0 | 0.9 | 0.4 | 1.0 | 1.0 | 1.0 | 1.0 | 2.4 | 1.3 | 6.8 | 0.5 | 1.3 | 1.4 | 1.0 | 1.0 | 1.0 | 1.0 | 3.4 | 10.8 |
| Dio1 | 1.0 | 1.0 | 1.0 | 1.0 | 1.0 | 1.0 | 1.0 | 1.0 | 0.4 | 0.6 | 1.0 | 1.3 | 1.0 | 1.0 | 1.0 | 1.0 | 1.0 | 1.0 | 1.0 | 1.0 | 1.6 | 1.3 | 0.7 | 0.8 |
| Dmbt1 | 1.0 | 1.0 | 1.0 | 1.0 | 1.0 | 1.0 | 1.0 | 1.0 | 2.0 | 1.3 | 1.0 | 1.0 | 1.0 | 1.0 | 1.0 | 1.0 | 1.6 | 1.0 | 1.0 | 1.0 | 1.0 | 1.0 | 0.0 | 0.0 |
| Drakn | 1.2 | 0.7 | 1.0 | 1.1 | 1.2 | 0.8 | 1.2 | 0.8 | 1.0 | 1.0 | 1.0 | 1.0 | 1.3 | 1.5 | 0.7 | 1.1 | 1.0 | 1.0 | 1.0 | 1.0 | 1.2 | 0.8 | 10.0 | 1.0 |
| Dmrtc1a | 1.0 | 1.0 | 1.0 | 1.0 | 0.7 | 1.3 | 1.0 | 1.0 | 1.0 | 0.8 | 1.0 | 1.0 | 1.0 | 1.0 | 1.0 | 1.0 | 1.0 | 1.0 | 1.0 | 1.0 | 1.3 | 3.3 | 4.6 | |
| Dntt | 1.0 | 1.0 | 1.0 | 1.0 | 1.0 | 1.0 | 1.0 | 0.4 | 0.9 | 1.0 | 1.0 | 1.0 | 0.7 | 1.0 | 1.4 | 1.4 | 1.0 | 0.8 | 7.0 | 0.4 | 1.0 | 0.8 | 0.6 | |
| Dnajb8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Dnase1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Dnrc3l | 2.3 | 5.7 | 1.0 | 1.0 | 1.0 | 1.0 | 1.0 | 1.0 | 1.0 | 1.0 | 1.0 | 1.0 | 0.8 | 1.1 | 1.0 | 1.0 | 1.0 | 1.0 | 1.0 | 1.0 | 0.9 | 1.0 | 1.0 | 1.0 |
| Dot1 | 1.0 | 1.0 | 1.0 | 1.0 | 1.0 | 1.0 | 1.0 | 1.0 | 1.0 | 1.0 | 1.0 | 1.0 | 0.6 | 1.1 | 1.0 | 0.7 | 1.4 | 1.0 | 1.0 | 0.0 | 1.0 | 1.0 | 1.0 | 1.0 |
| Douev2 | 0.7 | 0.7 | 1.2 | 0.9 | 0.5 | 0.8 | 1.0 | 1.0 | 1.0 | 1.0 | 0.9 | 1.0 | 1.2 | 1.0 | 0.8 | 0.9 | 1.3 | 1.2 | 1.0 | 1.1 | 0.8 | 9.7 | 4.4 | |
| Ddx4 | 0.5 | 0.3 | 1.0 | 1.0 | 1.0 | 1.0 | 1.0 | 1.0 | 1.0 | 0.7 | 0.5 | 1.0 | 1.0 | 1.0 | 1.0 | 1.0 | 1.0 | 1.0 | 1.0 | 1.0 | 0.8 | 0.0 | 1.0 | |
| Duoxa2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.8 | 0.6 |

[Fig. 23-S]

Due to the extremely dense tabular data with hundreds of cells of small numerical values that cannot be reliably transcribed at this resolution, a faithful reproduction is not possible.

| | | | | | | | | | | | | | | | | | | | | | | | |
|---|---|---|---|---|---|---|---|---|---|---|---|---|---|---|---|---|---|---|---|---|---|---|---|
| Msln | 0.7 | 0.8 | 0.9 | 1.4 | 1.0 | 1.0 | 1.0 | 1.1 | 1.1 | 1.0 | 1.0 | 1.0 | 1.0 | 1.0 | 1.3 | 1.8 | 1.0 | 1.0 | 1.0 | 0.9 | 1.0 | 1.0 | 0.2 | 0.6 |
| Mss51 | 1.0 | 1.0 | 1.0 | 1.0 | 1.0 | 1.0 | 0.9 | 1.0 | 1.0 | 1.0 | 1.0 | 0.7 | 1.0 | 3.5 | 0.2 | 0.6 | 0.4 | 1.4 | 1.1 | 1.4 | 1.3 | 0.6 | 9.6 |
| Mstn | 1.0 | 1.0 | 1.0 | 1.0 | 1.0 | 1.0 | 1.0 | 1.0 | 1.0 | 1.0 | 1.0 | 1.8 | 0.7 | 2.7 | 0.4 | 1.3 | 1.0 | 1.0 | 1.0 | 1.0 | 1.0 | 1.6 | 5.3 |
| Msx1 | 0.6 | 1.1 | 0.8 | 0.9 | 1.3 | 0.9 | 0.7 | 0.7 | 1.0 | 1.0 | 1.2 | 1.0 | 0.3 | 0.5 | 0.9 | 0.9 | 0.8 | 0.5 | 1.3 | 0.9 | 1.0 | 1.0 | 0.8 | 0.7 |
| Mt1 | 1.2 | 1.1 | 1.0 | 1.4 | 1.4 | 1.4 | 1.7 | 1.5 | 0.5 | 0.7 | 1.2 | 1.2 | 1.0 | 1.3 | 1.9 | 1.3 | 2.1 | 1.3 | 1.1 | 1.1 | 0.7 | 0.9 | 0.9 |
| Mt2 | 1.2 | 0.8 | 0.8 | 2.1 | 1.2 | 1.4 | 2.1 | 2.2 | 0.4 | 0.7 | 1.2 | 1.8 | 1.0 | 0.5 | 1.2 | 2.3 | 1.2 | 2.8 | 2.6 | 0.5 | 1.1 | 1.0 | 0.9 | 0.9 |
| Mt3 | 1.0 | 2.2 | 1.0 | 1.3 | 1.1 | 1.2 | 1.0 | 1.0 | 1.0 | 1.0 | 1.2 | 1.1 | 1.0 | 1.0 | 5.3 | 2.4 | 1.0 | 1.1 | 1.0 | 1.0 | 0.8 | 0.6 | 3.6 | 2.6 |
| Mt4 | 1.0 | 1.0 | 1.0 | 1.0 | 1.0 | 1.0 | 1.0 | 1.0 | 1.0 | 1.0 | 1.0 | 0.8 | 0.4 | 1.0 | 1.0 | 1.0 | 1.0 | 1.0 | 1.0 | 1.0 | 1.0 | 8.1 | 1.0 |
| Muc15 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Muc5b | 1.0 | 1.0 | 1.0 | 1.0 | 1.0 | 1.0 | 0.8 | 1.3 | 1.0 | 1.0 | 1.0 | 1.0 | 1.0 | 1.0 | 1.0 | 1.0 | 1.0 | 1.0 | 1.0 | 1.0 | 1.0 | 0.1 | 0.2 |
| Mug1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup1 | 1.0 | 0.3 | 1.0 | 0.2 | 1.0 | 1.0 | 1.0 | 1.0 | 1.0 | 1.0 | 1.0 | 0.7 | 1.1 | 1.0 | 1.0 | 1.0 | 1.0 | 1.0 | 1.0 | 1.0 | 1.0 | 1.0 | 1.0 |
| Mup10 | 1.0 | 0.6 | 0.6 | 0.1 | 1.0 | 1.0 | 1.0 | 1.0 | 1.0 | 1.0 | 1.0 | 0.8 | 1.0 | 1.0 | 1.0 | 1.2 | 0.6 | 1.0 | 1.0 | 1.0 | 1.0 | 1.0 | 1.0 |
| Mup11 | 1.0 | 1.2 | 1.0 | 1.0 | 1.0 | 1.0 | 1.0 | 1.0 | 1.0 | 1.0 | 1.0 | 2.1 | 1.0 | 1.0 | 1.0 | 1.0 | 1.0 | 1.0 | 1.0 | 1.0 | 1.0 | 1.0 | 1.0 |
| Mup12 | 1.0 | 0.3 | 0.9 | 0.1 | 1.0 | 1.0 | 1.0 | 1.0 | 1.0 | 1.0 | 1.0 | 0.7 | 0.9 | 1.0 | 1.0 | 0.7 | 1.0 | 1.0 | 1.0 | 1.0 | 1.0 | 1.0 | 1.0 |
| Mup13 | 1.0 | 0.4 | 0.8 | 0.1 | 1.0 | 1.0 | 1.2 | 1.0 | 1.0 | 1.0 | 1.0 | 1.0 | 0.8 | 1.0 | 1.0 | 0.5 | 1.0 | 1.0 | 1.0 | 1.0 | 1.0 | 1.0 | 1.0 |
| Mup14 | 1.0 | 0.3 | 0.9 | 1.0 | 1.0 | 2.0 | 1.0 | 1.0 | 1.0 | 1.0 | 1.0 | 0.3 | 0.5 | 1.0 | 1.0 | 1.0 | 1.0 | 1.0 | 1.0 | 1.0 | 1.0 | 1.0 | 1.0 |
| Mup15 | 1.0 | 0.3 | 0.6 | 0.2 | 1.0 | 1.0 | 1.7 | 1.0 | 1.0 | 1.0 | 1.0 | 0.7 | 1.4 | 1.0 | 1.0 | 0.6 | 0.9 | 1.0 | 1.0 | 1.0 | 1.0 | 1.0 | 1.0 |
| Mup16 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup17 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup18 | 1.0 | 0.5 | 0.8 | 1.0 | 1.0 | 1.0 | 1.0 | 1.0 | 1.0 | 1.0 | 1.0 | 0.9 | 0.8 | 1.0 | 1.0 | 0.5 | 0.6 | 1.0 | 1.0 | 1.0 | 1.0 | 1.0 | 1.0 |

| | AG | | Acuta | | Brain | | Lung | | Pancreas | | PG | | Skin | | Skull | | SM | | Spleen | | Testis | | TG | |
|---|---|---|---|---|---|---|---|---|---|---|---|---|---|---|---|---|---|---|---|---|---|---|---|---|
| | E | M | E | M | E | M | E | M | E | M | E | M | E | M | E | M | E | M | E | M | E | M | E | M |
| Mup2 | 1.0 | 0.2 | 0.4 | 0.2 | 1.0 | 0.9 | 1.7 | 1.0 | 1.0 | 2.0 | 1.0 | 1.0 | 0.5 | 1.0 | 0.9 | 0.7 | 0.7 | 0.8 | 1.0 | 1.0 | 1.0 | 1.0 | 0.8 | 1.0 |
| Mup20 | 1.0 | 0.2 | 1.0 | 0.2 | 1.0 | 1.0 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup21 | 1.0 | 1.0 | 1.0 | 0.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup3 | 1.0 | 0.2 | 1.0 | 0.2 | 1.0 | 1.0 | 1.0 | 1.0 | 1.0 | 1.3 | 1.0 | 1.0 | 0.6 | 1.0 | 1.0 | 1.0 | 1.0 | 1.0 | 1.0 | 1.0 | 1.0 | 1.0 | 1.0 | 1.0 |
| Mup5 | 1.0 | 1.0 | 1.0 | 0.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mup7 | 1.0 | 0.1 | 1.0 | 0.1 | 1.0 | 1.1 | 2.4 | 1.0 | 1.0 | 1.6 | 1.0 | 1.0 | 0.5 | 0.2 | 1.0 | 1.0 | 1.0 | 1.0 | 1.0 | 1.0 | 1.0 | 1.0 | 1.0 | 1.0 |
| Mup8 | 1.0 | 1.0 | 1.0 | 0.1 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 |
| Mup9 | 1.0 | 0.8 | 1.0 | 0.1 | 1.0 | 1.0 | 1.0 | 1.0 | 1.0 | 1.0 | 1.0 | 0.7 | 1.0 | 1.0 | 1.0 | 0.8 | 1.0 | 1.0 | 1.0 | 1.0 | 1.0 | 1.0 | 1.0 | 1.0 |
| Murc | 1.0 | 1.0 | 0.6 | 0.8 | 1.0 | 1.0 | 0.7 | 1.4 | 1.0 | 1.0 | 1.0 | 1.0 | 2.4 | 0.7 | 4.0 | 0.4 | 1.0 | 1.1 | 1.0 | 1.0 | 1.0 | 1.3 | 1.4 | 7.2 |
| Myadm2 | 1.0 | 1.0 | 1.1 | 0.8 | 0.8 | 0.9 | 0.5 | 1.0 | 1.0 | 1.0 | 0.8 | 0.8 | 1.9 | 0.7 | 2.9 | 0.3 | 0.8 | 1.0 | 0.7 | 1.0 | 1.0 | 1.0 | 1.1 | 7.0 |
| Myb | 1.0 | 1.0 | 1.0 | 1.0 | 1.0 | 1.0 | 0.8 | 0.9 | 1.0 | 1.0 | 0.4 | 1.0 | 0.7 | 0.8 | 0.8 | 0.8 | 1.0 | 1.0 | 1.0 | 0.7 | 1.0 | 1.0 | 0.1 | 1.0 |
| Mybl1 | 0.8 | 0.7 | 1.0 | 1.0 | 1.0 | 0.6 | 1.0 | 1.0 | 1.0 | 1.0 | 1.1 | 1.0 | 0.8 | 1.0 | 0.8 | 0.9 | 1.0 | 1.0 | 0.8 | 0.1 | 0.9 | 1.2 | 1.0 | 1.0 |
| Mybpc1 | 0.8 | 0.9 | 1.0 | 0.8 | 1.1 | 1.4 | 1.0 | 1.0 | 1.0 | 1.0 | 1.0 | 1.0 | 1.5 | 0.9 | 5.0 | 0.3 | 0.9 | 1.1 | 1.1 | 1.2 | 1.0 | 1.0 | 0.9 | 14.6 |
| Mybpc2 | 1.0 | 1.0 | 1.0 | 0.8 | 1.0 | 1.0 | 1.0 | 1.0 | 1.0 | 1.0 | 1.0 | 1.0 | 3.1 | 1.1 | 3.8 | 0.2 | 1.1 | 1.2 | 1.0 | 1.0 | 1.0 | 1.0 | 0.9 | 17.1 |
| Myf6 | 1.0 | 1.0 | 1.0 | 1.0 | 1.0 | 1.0 | 1.0 | 1.0 | 1.0 | 1.0 | 1.0 | 1.0 | 1.8 | 1.0 | 2.3 | 0.2 | 1.1 | 1.0 | 1.0 | 1.0 | 1.2 | 1.1 | 1.4 | 11.7 |
| Myh1 | 1.0 | 1.0 | 1.0 | 0.4 | 1.0 | 1.0 | 1.0 | 1.0 | 1.0 | 1.0 | 1.0 | 1.0 | 2.2 | 1.0 | 4.7 | 0.3 | 0.9 | 1.1 | 1.0 | 1.0 | 1.0 | 1.0 | 1.6 | 14.3 |
| Myh2 | 1.0 | 1.0 | 1.0 | 0.3 | 1.0 | 1.0 | 1.0 | 1.0 | 1.0 | 1.0 | 1.0 | 1.0 | 1.7 | 1.2 | 5.3 | 0.4 | 0.7 | 1.3 | 1.0 | 1.0 | 1.0 | 1.0 | 1.0 | 42.8 |
| Myh4 | 1.0 | 1.0 | 1.0 | 0.3 | 1.0 | 1.0 | 1.0 | 1.0 | 1.0 | 1.0 | 1.0 | 1.0 | 2.5 | 0.9 | 3.5 | 0.2 | 0.8 | 1.2 | 1.0 | 1.0 | 1.0 | 1.0 | 1.2 | 10.5 |
| Myh7 | 1.0 | 1.0 | 1.0 | 1.0 | 0.9 | 1.4 | 1.1 | 1.0 | 1.0 | 1.0 | 1.0 | 1.0 | 0.3 | 1.2 | 5.2 | 0.9 | 1.2 | 3.8 | 1.0 | 1.0 | 1.0 | 1.0 | 1.0 | 1.0 |
| Myh8 | 1.0 | 1.0 | 1.0 | 1.0 | 1.0 | 1.0 | 1.0 | 1.0 | 1.0 | 1.0 | 1.0 | 1.0 | 2.2 | 1.0 | 3.7 | 0.4 | 0.8 | 1.4 | 1.0 | 1.0 | 1.0 | 1.0 | 7.0 | 6.6 |
| Myl1 | 1.1 | 1.3 | 0.6 | 0.7 | 1.0 | 1.0 | 0.8 | 0.5 | 1.0 | 1.0 | 1.0 | 1.0 | 1.1 | 0.4 | 2.6 | 0.2 | 0.6 | 0.6 | 1.0 | 1.0 | 1.0 | 1.0 | 0.9 | 6.4 |
| Myl3 | 1.0 | 1.0 | 1.0 | 0.6 | 1.0 | 1.0 | 0.4 | 0.6 | 1.0 | 1.0 | 1.0 | 1.0 | 0.3 | 1.0 | 4.8 | 1.0 | 0.8 | 2.3 | 1.0 | 1.0 | 1.0 | 1.0 | 18.4 | 1.0 |
| Myl6b | 0.6 | 0.8 | 0.5 | 0.5 | 0.6 | 1.0 | 1.0 | 1.0 | 1.0 | 1.0 | 1.0 | 0.8 | 0.7 | 0.5 | 5.4 | 0.6 | 0.8 | 0.8 | 1.0 | 0.7 | 1.2 | 1.2 | 1.0 | 1.1 |
| Mylk2 | 1.0 | 1.0 | 1.5 | 1.1 | 1.0 | 1.0 | 1.0 | 1.0 | 1.0 | 1.0 | 1.0 | 1.0 | 3.2 | 1.1 | 4.3 | 0.3 | 1.5 | 1.2 | 1.0 | 1.0 | 1.0 | 1.0 | 1.6 | 32.7 |
| Mylk4 | 1.0 | 1.0 | 0.9 | 0.8 | 1.0 | 1.0 | 0.6 | 1.0 | 1.0 | 1.0 | 1.0 | 1.0 | 2.0 | 0.5 | 3.6 | 0.2 | 1.0 | 1.1 | 1.0 | 1.0 | 1.0 | 1.0 | 1.0 | 17.4 |
| Mylpf | 1.0 | 1.0 | 1.0 | 0.3 | 1.0 | 1.0 | 1.0 | 0.8 | 1.0 | 1.0 | 1.0 | 1.0 | 2.1 | 0.9 | 3.3 | 0.3 | 1.0 | 1.1 | 0.6 | 0.7 | 1.0 | 1.0 | 1.1 | 13.6 |
| Myo18b | 1.0 | 1.0 | 1.0 | 0.9 | 1.0 | 1.0 | 1.0 | 1.0 | 1.0 | 1.0 | 1.0 | 1.0 | 2.5 | 1.0 | 3.8 | 0.3 | 1.2 | 1.5 | 1.0 | 1.0 | 1.0 | 0.9 | 1.4 | 7.2 |
| Myo3b | 1.0 | 1.0 | 1.0 | 1.0 | 1.0 | 1.0 | 1.0 | 1.0 | 1.0 | 1.0 | 0.7 | 0.8 | 1.0 | 1.0 | 1.0 | 1.0 | 1.0 | 1.0 | 1.0 | 1.0 | 1.0 | 1.0 | 0.7 | 0.8 |
| Myo5b | 0.8 | 0.8 | 0.5 | 0.7 | 1.1 | 0.9 | 1.2 | 1.3 | 1.0 | 0.8 | 1.1 | 1.1 | 1.0 | 1.2 | 1.0 | 1.0 | 1.0 | 1.0 | 1.0 | 1.0 | 1.0 | 1.0 | 0.9 | 0.7 |
| Myom1 | 1.0 | 1.0 | 1.5 | 1.1 | 1.0 | 1.0 | 0.9 | 1.0 | 1.0 | 1.0 | 1.0 | 1.0 | 2.4 | 1.1 | 3.1 | 0.4 | 1.5 | 1.4 | 0.8 | 1.2 | 1.0 | 1.0 | 1.9 | 7.7 |
| Myom2 | 1.0 | 1.0 | 1.0 | 1.5 | 1.0 | 1.0 | 1.1 | 0.9 | 1.0 | 1.0 | 1.0 | 1.0 | 2.1 | 0.9 | 3.3 | 0.3 | 1.0 | 1.0 | 1.0 | 1.0 | 1.0 | 1.0 | 1.1 | 17.0 |
| Myot | 1.2 | 1.2 | 1.0 | 0.5 | 1.0 | 1.0 | 1.0 | 1.0 | 1.0 | 1.0 | 1.0 | 1.0 | 2.5 | 1.1 | 4.7 | 0.3 | 1.2 | 1.2 | 1.0 | 1.0 | 1.0 | 1.0 | 1.5 | 17.1 |
| Myoz1 | 1.2 | 1.0 | 1.0 | 0.5 | 1.0 | 1.0 | 1.0 | 1.0 | 1.0 | 1.0 | 1.0 | 1.0 | 2.9 | 1.0 | 4.0 | 0.3 | 1.2 | 1.1 | 1.0 | 1.0 | 1.0 | 1.0 | 1.3 | 19.8 |
| Myoz2 | 1.0 | 1.0 | 1.1 | 1.2 | 1.0 | 1.0 | 0.7 | 0.7 | 1.0 | 1.0 | 1.0 | 1.0 | 1.7 | 1.1 | 5.2 | 0.5 | 1.2 | 1.5 | 1.0 | 1.0 | 1.2 | 1.0 | 1.6 | 11.2 |
| Myoz3 | 1.0 | 1.0 | 1.0 | 1.0 | 1.0 | 1.0 | 1.0 | 1.0 | 1.0 | 1.0 | 1.0 | 1.0 | 1.4 | 0.6 | 3.5 | 0.2 | 0.7 | 0.7 | 1.0 | 1.0 | 1.0 | 1.0 | 1.3 | 3.9 |
| Myon | 1.0 | 1.0 | 1.0 | 1.0 | 1.0 | 1.0 | 1.0 | 1.0 | 1.0 | 1.0 | 1.0 | 1.0 | 2.5 | 1.1 | 3.9 | 0.3 | 1.2 | 1.3 | 1.0 | 1.0 | 1.0 | 1.0 | 1.4 | 8.3 |
| Mzb1 | 2.4 | 1.8 | 1.0 | 1.0 | 1.0 | 1.0 | 0.5 | 0.4 | 1.0 | 1.0 | 1.0 | 1.0 | 1.0 | 1.0 | 0.6 | 0.8 | 1.3 | 1.0 | 0.9 | 0.6 | 0.5 | 0.9 | 0.7 | 1.1 |
| Nktip2 | 1.0 | 1.0 | 1.1 | 1.0 | 0.7 | 1.0 | 0.2 | 1.0 | 1.0 | 1.0 | 0.9 | 0.8 | 0.6 | 0.8 | 1.0 | 0.6 | 1.0 | 1.0 | 0.9 | 0.8 | 1.0 | 1.1 | 1.1 | 0.7 |
| Nalp7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Nat8 | 0.9 | 0.9 | 1.0 | 1.0 | 0.8 | 1.0 | 1.0 | 0.6 | 1.0 | 0.4 | 1.2 | 1.0 | 0.8 | 1.5 | 1.0 | 1.0 | 1.0 | 1.0 | 1.0 | 0.6 | 0.5 | 1.0 | 1.0 |
| Nav2 | 0.9 | 1.0 | 1.3 | 0.8 | 1.0 | 0.9 | 0.9 | 1.2 | 1.0 | 1.0 | 1.0 | 0.9 | 0.3 | 0.8 | 1.1 | 0.7 | 0.7 | 1.1 | 1.1 | 1.0 | 0.9 | 0.8 | 0.9 | 0.7 |
| Ncmap | 1.0 | 1.0 | 1.0 | 1.0 | 1.1 | 1.2 | 1.4 | 1.2 | 1.0 | 1.0 | 0.8 | 1.5 | 1.6 | 1.8 | 0.7 | 1.0 | 0.9 | 0.8 | 1.0 | 0.9 | 1.1 | 0.9 | 1.4 | 1.0 |
| Nctc1 | 1.0 | 1.0 | 1.0 | 1.0 | 1.0 | 1.0 | 1.0 | 1.0 | 1.0 | 1.0 | 1.0 | 1.0 | 2.2 | 1.0 | 5.1 | 0.4 | 1.3 | 1.0 | 1.0 | 1.0 | 1.0 | 1.0 | 1.4 | 9.8 |
| Neat1 | 0.9 | 1.0 | 1.0 | 1.1 | 1.1 | 0.8 | 1.2 | 1.0 | 0.6 | 0.6 | 1.3 | 1.1 | 1.3 | 1.0 | 0.9 | 1.0 | 1.0 | 0.7 | 1.0 | 1.0 | 1.1 | 0.8 | 1.1 | 1.2 |
| Neb | 1.0 | 1.0 | 1.0 | 1.0 | 1.0 | 1.0 | 1.0 | 1.0 | 1.0 | 1.0 | 1.0 | 1.0 | 2.2 | 1.0 | 3.6 | 0.3 | 1.1 | 1.2 | 1.0 | 1.0 | 1.0 | 1.0 | 1.2 | 8.7 |
| Nebl | 1.0 | 1.0 | 1.0 | 1.0 | 1.0 | 1.0 | 1.0 | 0.9 | 1.1 | 1.0 | 1.0 | 1.0 | 1.4 | 1.5 | 1.2 | 1.0 | 1.0 | 1.0 | 1.0 | 1.0 | 1.0 | 1.0 | 5.7 | 5.3 |
| Nexn | 1.0 | 0.9 | 1.0 | 0.9 | 0.2 | 1.3 | 0.9 | 1.1 | 1.0 | 1.0 | 1.1 | 1.1 | 1.7 | 1.0 | 2.7 | 0.4 | 0.8 | 1.0 | 1.3 | 1.0 | 1.4 | 1.0 | 4.9 | 5.8 |
| Nfe2l3 | 1.0 | 1.0 | 0.8 | 1.1 | 0.9 | 1.1 | 1.1 | 0.8 | 1.0 | 1.0 | 1.0 | 1.0 | 1.2 | 1.0 | 1.0 | 1.0 | 0.7 | 0.7 | 0.8 | 0.9 | 1.5 | 0.9 |
| Ngfr | 0.8 | 4.2 | 0.8 | 0.5 | 0.8 | 0.7 | 1.0 | 1.0 | 1.0 | 1.0 | 1.3 | 1.7 | 1.1 | 1.4 | 0.8 | 0.7 | 1.0 | 1.3 | 0.9 | 1.3 | 1.1 | 1.0 | 6.9 | 26.1 |
| Nhsl1 | 0.7 | 0.8 | 1.3 | 0.7 | 0.8 | 0.9 | 0.8 | 1.1 | 1.4 | 1.1 | 1.0 | 1.0 | 0.9 | 1.0 | 0.7 | 0.8 | 0.9 | 1.4 | 0.8 | 0.9 | 0.9 | 0.9 | 0.8 | 0.8 |
| Nkx3-1 | 1.3 | 1.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.6 | 1.0 | 1.0 | 0.9 | 1.2 | 0.1 | 0.7 |
| Nmrk2 | 1.0 | 1.0 | 1.0 | 1.0 | 1.0 | 1.0 | 1.0 | 1.0 | 1.0 | 1.0 | 1.0 | 1.0 | 0.7 | 1.0 | 1.2 | 1.0 | 0.6 | 0.2 | 1.0 | 1.0 | 1.0 | 1.0 | 1.0 |
| Nnat | 1.2 | 1.1 | 2.4 | 2.6 | 1.0 | 1.2 | 0.8 | 0.8 | 0.5 | 0.5 | 0.8 | 0.8 | 0.5 | 1.5 | 0.2 | 1.7 | 0.5 | 0.7 | 1.8 | 1.2 | 1.0 | 0.8 | 0.8 | 0.9 |
| Nos2 | 1.0 | 1.0 | 0.9 | 0.7 | 1.0 | 1.0 | 1.0 | 1.0 | 1.0 | 1.6 | 1.0 | 1.0 | 1.0 | 1.0 | 1.0 | 1.0 | 1.0 | 1.0 | 1.0 | 2.6 | 1.3 | 1.0 | 1.0 | 1.0 |
| Nos3 | 0.2 | 0.9 | 1.5 | 1.8 | 0.9 | 0.7 | 0.9 | 0.8 | 0.8 | 0.8 | 1.3 | 0.8 | 0.4 | 1.2 | 0.8 | 1.5 | 0.9 | 1.0 | 1.0 | 0.8 |
| Nrtd1 | 0.5 | 1.4 | 0.5 | 0.9 | 1.0 | 1.0 | 0.5 | 1.2 | 0.3 | 0.8 | 0.8 | 1.2 | 0.7 | 1.4 | 0.6 | 0.7 | 0.6 | 1.3 | 1.1 | 0.9 | 1.5 | 0.9 | 0.8 | 1.3 |
| Nr6a1 | 1.4 | 1.2 | 1.8 | 1.0 | 1.2 | 0.8 | 1.2 | 0.7 | 1.0 | 1.3 | 1.6 | 1.7 | 0.8 | 1.0 | 0.7 | 1.0 | 1.1 | 1.1 | 1.0 | 1.0 | 0.7 | 1.0 | 1.4 |
| Nrap | 1.0 | 1.0 | 1.0 | 0.8 | 1.0 | 1.0 | 1.0 | 1.0 | 1.0 | 1.0 | 1.0 | 1.0 | 2.9 | 1.0 | 4.0 | 0.3 | 1.1 | 1.4 | 1.0 | 1.0 | 1.0 | 1.0 | 1.7 | 13.3 |
| Nreb | 0.8 | 1.0 | 0.8 | 0.6 | 0.9 | 0.9 | 0.6 | 0.7 | 0.7 | 0.8 | 0.8 | 0.7 | 0.9 | 0.9 | 0.5 | 0.3 | 0.3 | 0.7 | 0.8 | 1.3 | 1.3 | 0.4 | 1.2 |
| Nrip1 | 0.5 | 0.7 | 1.2 | 1.3 | 0.9 | 0.7 | 0.8 | 1.0 | 1.0 | 1.2 | 1.3 | 0.8 | 1.0 | 1.3 | 0.6 | 0.9 | 1.9 | 1.0 | 1.1 | 0.9 | 1.0 | 1.0 | 0.6 |
| Ntsr2 | 1.0 | 1.0 | 0.7 | 0.8 | 1.0 | 1.0 | 1.0 | 1.0 | 1.0 | 1.0 | 1.0 | 1.5 | 1.0 | 1.0 | 1.0 | 0.7 | 1.2 | 1.0 | 1.0 | 1.0 | 1.0 | 1.1 | 1.0 |

[Fig. 23-10]

| | | | | | | | | | | | | | | | | | | | | | | | |
|---|---|---|---|---|---|---|---|---|---|---|---|---|---|---|---|---|---|---|---|---|---|---|---|
| Nudt7 | 1.1 | 1.2 | 0.6 | 0.8 | 1.1 | 1.3 | 0.9 | 0.8 | 1.1 | 0.9 | 0.7 | 1.2 | 1.0 | 1.4 | 1.0 | 0.9 | 0.6 | 0.6 | 1.0 | 1.1 | 0.7 | 1.2 | 1.1 | 1.4 |
| Nupgc | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.6 | 0.2 | 1.4 | 0.9 | 1.0 | 0.9 |
| Nubr1l | 1.1 | 1.3 | 1.4 | 1.4 | 1.0 | 1.9 | 1.0 | 0.9 | 1.0 | 1.0 | 0.9 | 1.0 | 1.3 | 1.6 | 1.0 | 1.1 | 1.0 | 1.0 | 0.5 | 1.9 | 1.1 | 0.7 | 1.2 | 1.1 |
| Nxtf2-ps1 | 1.6 | 4.3 | 1.0 | 1.1 | 1.0 | 1.0 | 1.3 | 2.0 | 0.8 | 1.3 | 0.5 | 1.0 | 1.2 | 0.3 | 1.4 | 1.4 | 1.0 | 1.0 | 0.8 | 1.1 | 0.8 | 1.0 | 0.7 | 1.7 |
| Nxf3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.9 | 1.3 | 1.0 | 1.0 | 1.0 |
| Nxpe2 | 1.0 | 1.0 | 1.0 | 1.0 | 1.0 | 1.0 | 1.0 | 0.9 | 1.0 | 1.0 | 1.0 | 1.0 | 1.0 | 1.0 | 1.5 | 1.2 | 1.0 | 1.0 | 2.1 | 0.6 | 1.0 | 1.0 | 1.0 | 0.8 |
| Nxph4 | 0.8 | 0.7 | 1.0 | 1.0 | 1.2 | 1.2 | 1.0 | 1.0 | 1.0 | 1.0 | 0.9 | 0.6 | 1.2 | 1.0 | 1.0 | 1.0 | 1.0 | 1.0 | 1.0 | 1.0 | 1.0 | 1.0 | 1.0 | 1.0 |
| Oaz1-ps | 1.0 | 1.3 | 1.2 | 1.2 | 1.0 | 1.0 | 0.0 | 1.0 | 1.0 | 1.4 | 18.5 | 2.3 | 1.0 | 0.3 | 1.0 | 10.6 | 1.0 | 1.0 | 0.9 | 8.1 | 0.2 | 1.2 | 11.7 | 1.0 |
| Oaz3 | 1.4 | 1.0 | 1.0 | 1.0 | 1.0 | 1.1 | 1.0 | 1.0 | 1.0 | 1.0 | 1.3 | 0.7 | 1.0 | 1.0 | 1.0 | 1.0 | 1.0 | 1.0 | 1.0 | 1.0 | 1.1 | 1.1 | 1.0 | 1.0 |
| Obscn | 1.0 | 1.0 | 1.0 | 0.8 | 1.0 | 1.0 | 1.0 | 1.0 | 1.0 | 1.0 | 1.0 | 1.0 | 1.9 | 0.9 | 3.6 | 0.2 | 1.1 | 1.3 | 1.0 | 1.0 | 1.0 | 1.0 | 3.4 | 4.0 |
| Oclad2 | 1.3 | 1.3 | 1.0 | 0.9 | 1.2 | 1.3 | 1.0 | 0.8 | 0.9 | 0.9 | 1.3 | 1.1 | 1.5 | 1.4 | 1.4 | 1.0 | 0.9 | 0.5 | 1.0 | 1.0 | 0.7 | 0.9 | 0.9 | 1.1 |
| Odf1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.1 | 0.9 | 1.0 | 1.0 |
| Odf3l2 | 1.0 | 1.0 | 1.0 | 1.0 | 1.0 | 1.0 | 1.0 | 1.0 | 1.0 | 1.0 | 1.0 | 1.0 | 2.4 | 1.5 | 4.2 | 0.5 | 1.8 | 1.7 | 1.0 | 1.0 | 1.0 | 1.0 | 1.7 | 26.1 |
| Olfr165 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Orop | 1.0 | 5.4 | 1.1 | 1.0 | 1.0 | 0.9 | 1.0 | 1.0 | 1.0 | 1.0 | 1.0 | 1.0 | 1.5 | 0.4 | 1.6 | 1.1 | 1.0 | 1.0 | 1.0 | 0.9 | 1.0 | 1.0 | 1.0 | 1.0 |
| Onecut1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Oscar | 1.0 | 1.0 | 1.0 | 1.0 | 1.0 | 1.0 | 1.7 | 1.1 | 1.0 | 1.0 | 1.0 | 1.0 | 1.0 | 1.0 | 4.7 | 5.4 | 1.0 | 1.0 | 1.0 | 1.0 | 1.7 | 1.1 | 1.0 | 1.0 |
| Ostn | 1.0 | 1.0 | 1.0 | 1.0 | 1.0 | 1.0 | 1.0 | 1.0 | 1.0 | 1.0 | 1.0 | 1.0 | 1.0 | 1.0 | 0.1 | 0.3 | 0.6 | 0.8 | 1.0 | 1.0 | 1.0 | 1.0 | 1.0 | 1.0 |
| Ovch2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Oxtr | 1.8 | 4.0 | 1.0 | 1.0 | 1.0 | 1.0 | 1.0 | 1.0 | 1.0 | 1.0 | 1.0 | 1.0 | 1.0 | 0.8 | 1.0 | 1.0 | 1.0 | 1.0 | 1.0 | 0.6 | 0.7 | 1.0 | 1.0 | 1.0 |
| P2rx2 | 1.0 | 1.0 | 1.0 | 1.0 | 1.0 | 1.0 | 1.0 | 1.0 | 1.0 | 1.0 | 1.0 | 1.2 | 1.7 | 1.3 | 0.8 | 1.3 | 1.0 | 1.0 | 1.0 | 1.0 | 0.9 | 1.0 | 1.0 | 1.0 |
| Padi2 | 0.5 | 0.7 | 0.9 | 1.0 | 0.9 | 0.8 | 0.7 | 0.9 | 1.0 | 0.8 | 1.5 | 1.2 | 2.0 | 1.4 | 1.5 | 1.0 | 1.1 | 1.4 | 1.0 | 1.2 | 1.2 | 1.1 | 0.9 | 1.3 |
| Paqr9 | 0.8 | 0.8 | 0.7 | 0.8 | 0.5 | 0.9 | 1.0 | 0.8 | 1.0 | 1.0 | 1.0 | 0.9 | 0.8 | 0.7 | 1.5 | 1.1 | 0.6 | 0.6 | 1.4 | 0.9 | 1.0 | 0.8 | 0.9 | 0.9 |
| Pate2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Pax2 | 1.0 | 1.0 | 1.0 | 1.0 | 0.9 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.7 | 1.0 | 1.0 |
| Pax6 | 1.0 | 1.0 | 1.0 | 1.0 | 1.0 | 1.0 | 0.7 | 0.6 | 1.0 | 1.0 | 1.0 | 1.0 | 1.0 | 1.0 | 0.1 | 1.1 | 1.0 | 1.0 | 0.8 | 0.8 | 1.2 | 0.9 | 1.0 | 1.0 |
| Pax8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.9 | 0.6 |
| Pck1 | 1.9 | 1.5 | 1.2 | 1.3 | 1.0 | 1.0 | 0.6 | 0.1 | 1.0 | 1.0 | 1.0 | 0.2 | 1.8 | 1.5 | 1.0 | 1.1 | 0.4 | 1.0 | 1.0 | 1.0 | 1.0 | 1.5 | 1.4 |  |
| Pcp4 | 1.2 | 0.9 | 1.0 | 1.0 | 1.1 | 1.0 | 1.0 | 0.4 | 0.7 | 1.0 | 0.6 | 0.5 | 1.3 | 1.9 | 2.6 | 0.5 | 1.0 | 0.5 | 1.0 | 1.0 | 1.0 | 1.0 | 0.9 | 0.9 |
| Pcp4l1 | 1.1 | 1.0 | 0.9 | 0.8 | 1.1 | 1.1 | 1.0 | 0.9 | 1.0 | 1.0 | 1.1 | 0.8 | 1.4 | 1.0 | 1.2 | 0.8 | 0.6 | 0.6 | 0.9 | 1.3 | 0.8 | 0.7 | 0.8 | 0.7 |
| Pcsk9 | 1.0 | 1.0 | 1.0 | 1.0 | 0.9 | 0.9 | 1.0 | 1.0 | 1.0 | 1.0 | 1.0 | 1.0 | 0.7 | 1.0 | 1.0 | 1.0 | 1.0 | 1.0 | 1.0 | 1.0 | 1.0 | 1.0 | 1.0 | 1.0 |
| Pcyt1b | 1.0 | 1.0 | 1.0 | 1.0 | 0.8 | 0.9 | 1.1 | 1.2 | 1.0 | 1.0 | 1.0 | 1.0 | 0.9 | 1.0 | 1.3 | 1.2 | 1.0 | 1.0 | 2.5 | 0.6 | 0.8 | 1.0 | 6.8 | 6.0 |
| Pde6a | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Pdgfrl | 0.7 | 0.5 | 0.9 | 0.8 | 1.0 | 1.0 | 0.7 | 0.6 | 1.0 | 1.0 | 0.4 | 1.2 | 0.3 | 0.6 | 0.5 | 0.8 | 0.4 | 0.3 | 0.5 | 1.4 | 1.0 | 1.0 | 0.8 | 1.0 |
| Pdx4 | 1.4 | 1.0 | 0.9 | 0.9 | 1.2 | 1.0 | 1.3 | 1.4 | 2.5 | 1.0 | 1.5 | 1.0 | 1.3 | 0.7 | 1.1 | 1.2 | 1.8 | 2.3 | 0.9 | 1.0 | 1.2 | 2.0 |  |  |
| Pdlim3 | 1.0 | 0.8 | 1.3 | 1.0 | 1.3 | 1.2 | 0.9 | 0.9 | 0.8 | 1.0 | 1.7 | 1.2 | 2.1 | 0.8 | 2.5 | 0.3 | 1.9 | 1.0 | 1.4 | 1.7 | 0.9 | 1.4 | 1.2 | 12.7 |

| | AG | | Aorta | | Brain | | Lung | | Pancreas | | PG | | Skin | | Skull | | SM | | Spleen | | Testis | | TG | |
|---|---|---|---|---|---|---|---|---|---|---|---|---|---|---|---|---|---|---|---|---|---|---|---|---|
| | F | M | F | M | F | M | F | M | F | M | F | M | F | M | F | M | F | M | F | M | F | M | F | M |
| Pdzk1 | 0.8 | 0.9 | 1.3 | 0.7 | 0.7 | 0.9 | 0.9 | 1.1 | 1.0 | 1.0 | 0.7 | 0.9 | 1.1 | 1.2 | 0.9 | 1.5 | 1.0 | 1.0 | 1.0 | 1.0 | 1.1 | 1.2 | 1.2 | 0.8 |
| Pdzk1ip1 | 1.0 | 1.0 | 1.0 | 1.0 | 1.0 | 1.0 | 1.1 | 1.0 | 1.2 | 1.2 | 0.9 | 0.8 | 1.5 | 1.3 | 1.1 | 1.5 | 1.0 | 1.0 | 2.3 | 0.3 | 1.0 | 0.9 | 0.8 | 0.9 |
| Pgam2 | 1.1 | 1.9 | 1.1 | 0.7 | 1.2 | 1.1 | 0.6 | 0.7 | 1.0 | 1.0 | 1.6 | 0.9 | 1.4 | 0.7 | 2.6 | 0.2 | 0.7 | 0.7 | 0.7 | 1.2 | 1.1 | 0.9 | 0.8 | 8.1 |
| Pgc | 1.0 | 1.0 | 1.0 | 0.8 | 1.0 | 1.0 | 1.0 | 0.9 | 1.1 | 1.0 | 1.0 | 1.0 | 1.0 | 1.0 | 1.0 | 1.0 | 1.0 | 0.1 | 0.3 | 1.0 | 1.0 | 1.0 | 1.0 | 0.6 |
| Pgk2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.3 | 1.0 | 1.0 |
| Pglyrp1 | 1.0 | 2.3 | 1.4 | 0.8 | 1.1 | 1.0 | 0.9 | 1.1 | 1.0 | 1.0 | 1.0 | 1.0 | 0.7 | 3.4 | 9.8 | 1.2 | 1.0 | 0.9 | 0.3 | 1.0 | 1.0 | 0.1 | 0.4 |  |
| Phkg1 | 1.1 | 1.2 | 1.3 | 1.0 | 0.8 | 0.8 | 0.9 | 0.6 | 1.0 | 1.0 | 1.0 | 1.0 | 2.0 | 0.8 | 3.6 | 0.2 | 0.9 | 0.9 | 1.0 | 1.0 | 1.0 | 1.0 | 1.1 | 3.5 |
| Phldal | 1.1 | 1.1 | 0.8 | 0.9 | 1.1 | 1.0 | 1.2 | 0.9 | 0.8 | 1.0 | 1.0 | 1.0 | 0.9 | 0.8 | 9.8 | 1.0 | 1.0 | 0.7 | 0.7 | 0.6 | 1.0 | 1.0 | 1.0 | 1.7 |
| Pi15 | 1.0 | 1.0 | 1.3 | 0.9 | 1.0 | 1.0 | 0.7 | 0.8 | 1.0 | 1.0 | 1.0 | 1.0 | 0.3 | 0.5 | 1.0 | 1.0 | 1.0 | 1.0 | 1.2 | 1.0 | 1.0 | 1.0 | 1.0 | 1.0 |
| Pigr | 1.0 | 1.0 | 1.0 | 0.6 | 1.0 | 1.0 | 1.1 | 1.1 | 0.5 | 1.0 | 1.0 | 1.0 | 1.0 | 1.1 | 1.0 | 1.0 | 1.8 | 0.8 | 1.0 | 1.0 | 1.4 | 0.1 | 0.3 |  |
| Pip5k1b | 1.1 | 1.3 | 1.0 | 1.0 | 1.1 | 1.0 | 1.4 | 1.3 | 1.3 | 1.0 | 1.0 | 0.8 | 1.0 | 0.8 | 1.4 | 1.4 | 1.0 | 1.0 | 2.1 | 0.8 | 1.3 | 1.1 | 0.7 | 0.7 |
| Pi16 | 0.8 | 1.1 | 0.9 | 0.9 | 1.0 | 1.1 | 0.8 | 0.9 | 1.0 | 1.0 | 1.1 | 1.1 | 1.2 | 0.9 | 3.0 | 0.4 | 1.1 | 1.0 | 0.9 | 1.1 | 1.0 | 1.1 | 6.7 |  |
| Pla2g1b | 1.0 | 1.0 | 1.0 | 1.0 | 1.2 | 1.0 | 1.5 | 0.8 | 1.3 | 1.0 | 1.0 | 1.0 | 1.0 | 1.6 | 1.0 | 1.0 | 0.2 | 1.0 | 1.0 | 1.0 | 1.0 | 0.4 |  |  |
| Pla2g4c | 1.0 | 1.0 | 1.0 | 1.0 | 1.0 | 1.0 | 1.0 | 1.0 | 1.0 | 1.0 | 1.0 | 1.0 | 1.0 | 1.0 | 1.5 | 1.5 | 1.0 | 1.0 | 3.5 | 1.0 | 1.0 | 1.0 | 1.0 | 1.0 |
| Pla2g5 | 0.8 | 0.7 | 1.0 | 1.0 | 1.2 | 1.0 | 1.0 | 1.0 | 1.0 | 1.0 | 1.4 | 1.4 | 0.6 | 0.7 | 0.7 | 1.2 | 1.0 | 1.3 | 3.0 | 1.0 | 1.1 | 1.0 | 0.8 | 0.8 |
| Plac8 | 1.3 | 0.9 | 0.9 | 0.8 | 1.1 | 0.6 | 0.6 | 0.5 | 1.0 | 1.0 | 1.1 | 0.9 | 0.7 | 1.2 | 0.8 | 0.9 | 1.1 | 0.8 | 0.9 | 1.0 | 1.7 | 1.0 | 1.8 |  |
| Plac9a | 0.4 | 0.6 | 0.8 | 1.0 | 2.5 | 3.5 | 0.9 | 0.4 | 2.2 | 0.9 | 0.4 | 1.2 | 1.0 | 0.4 | 2.5 | 3.4 | 0.5 | 0.4 | 1.5 | 1.6 | 0.4 | 1.4 | 3.2 | 0.3 |
| Plek2 | 1.0 | 1.0 | 1.0 | 1.0 | 1.0 | 1.0 | 1.0 | 1.0 | 0.7 | 1.5 | 1.0 | 1.0 | 0.9 | 1.1 | 3.0 | 1.3 | 1.0 | 1.0 | 2.8 | 1.0 | 1.0 | 1.0 | 0.8 | 0.9 |
| Plet1 | 1.0 | 1.0 | 1.7 | 1.0 | 1.0 | 1.0 | 1.2 | 1.1 | 1.8 | 1.3 | 1.0 | 1.0 | 1.3 | 1.5 | 1.0 | 1.0 | 1.0 | 1.0 | 1.0 | 1.0 | 1.0 | 1.0 | 0.8 | 0.7 |
| Pln3 | 0.9 | 1.0 | 0.2 | 0.7 | 1.0 | 1.0 | 0.8 | 0.1 | 0.9 | 0.8 | 1.0 | 1.0 | 0.7 | 1.0 | 0.9 | 0.9 | 0.6 | 0.5 | 1.0 | 1.0 | 1.0 | 0.8 | 1.3 | 1.1 |
| Pln4 | 0.9 | 0.9 | 1.2 | 0.8 | 1.2 | 1.7 | 0.8 | 0.5 | 0.5 | 0.6 | 1.1 | 1.0 | 1.6 | 1.3 | 3.2 | 0.5 | 1.6 | 1.9 | 1.5 | 1.0 | 1.0 | 1.0 | 1.6 | 1.2 |
| Pnlip | 1.0 | 0.8 | 1.0 | 1.0 | 1.3 | 0.9 | 1.0 | 1.0 | 0.9 | 1.2 | 0.8 | 0.7 | 1.8 | 1.0 | 1.6 | 0.8 | 1.0 | 1.0 | 1.2 | 1.0 | 1.0 | 0.6 | 1.0 |  |
| Pnliprp1 | 1.0 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Pnmt | 1.0 | 0.8 | 1.0 | 1.0 | 1.8 | 1.0 | 1.0 | 1.1 | 1.5 | 1.0 | 1.0 | 1.3 | 1.9 | 1.0 | 1.0 | 1.0 | 5.2 | 2.3 | 1.0 | 1.0 | 1.0 | 1.0 | 1.2 |  |
| Pou2af1 | 1.4 | 1.0 | 1.0 | 1.2 | 1.0 | 1.0 | 0.6 | 0.5 | 1.0 | 1.0 | 1.0 | 1.0 | 1.0 | 1.0 | 0.6 | 0.8 | 1.0 | 1.0 | 0.8 | 0.5 | 1.0 | 1.0 | 1.0 | 1.0 |
| Pou3f3 | 1.0 | 1.0 | 1.0 | 1.0 | 1.0 | 0.9 | 1.0 | 1.0 | 1.0 | 1.0 | 1.0 | 1.0 | 1.3 | 0.7 | 1.0 | 1.0 | 1.0 | 1.0 | 1.0 | 1.0 | 1.0 | 1.0 | 1.0 | 1.0 |
| Pou3f3os | 1.0 | 1.0 | 1.0 | 1.0 | 1.2 | 1.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.4 | 1.0 | 1.0 |
| Ppapdc3 | 1.1 | 1.0 | 0.8 | 0.7 | 0.6 | 1.2 | 0.9 | 1.4 | 0.7 | 1.1 | 0.9 | 0.9 | 1.4 | 0.8 | 1.8 | 0.4 | 0.8 | 0.9 | 1.1 | 1.1 | 0.8 | 0.7 | 0.8 | 6.3 |
| Ppl | 0.4 | 0.3 | 1.2 | 1.4 | 1.0 | 1.0 | 1.2 | 1.3 | 1.0 | 1.0 | 0.8 | 1.1 | 1.3 | 1.0 | 9.8 | 0.7 | 1.1 | 1.0 | 1.3 | 1.0 | 1.0 | 1.0 | 0.9 |  |
| Ppp1r14c | 3.0 | 5.5 | 1.0 | 0.8 | 1.0 | 1.0 | 0.9 | 0.6 | 1.0 | 1.0 | 1.0 | 1.1 | 1.2 | 2.6 | 0.3 | 0.6 | 0.9 | 1.0 | 1.0 | 1.0 | 1.0 | 0.7 | 5.2 |  |
| Ppp1r27 | 1.0 | 1.0 | 1.0 | 1.0 | 1.0 | 1.0 | 1.0 | 1.0 | 1.0 | 1.0 | 1.0 | 1.0 | 1.5 | 0.8 | 4.2 | 0.3 | 0.6 | 0.7 | 1.0 | 1.0 | 1.1 | 1.0 | 0.5 | 7.2 |
| Ppp1r3a | 1.0 | 1.0 | 1.0 | 1.0 | 1.0 | 1.0 | 1.0 | 1.5 | 1.0 | 1.0 | 1.0 | 1.0 | 2.1 | 1.1 | 4.6 | 0.2 | 1.3 | 1.2 | 1.0 | 1.0 | 1.0 | 1.0 | 1.2 | 7.1 |
| Prb1 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 0.1 | 1.0 |
| Prb1 | 1.0 | 1.0 | 1.0 | 1.0 | 1.2 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 3.0 | 0.7 |  |
| Prkcq | 1.0 | 1.0 | 1.0 | 1.0 | 0.8 | 0.8 | 0.9 | 0.9 | 1.0 | 1.0 | 0.7 | 0.7 | 1.9 | 0.9 | 1.5 | 0.9 | 1.2 | 1.4 | 1.1 | 0.9 | 1.0 | 1.1 | 2.0 | 5.2 |
| Prlr | 1.2 | 1.5 | 1.0 | 1.0 | 0.7 | 0.8 | 1.0 | 1.0 | 1.0 | 1.0 | 0.7 | 0.7 | 0.9 | 1.4 | 1.0 | 0.8 | 1.0 | 1.0 | 1.6 | 0.9 | 0.8 | 0.9 | 0.7 | 0.8 |
| Prm1 | 1.0 | 1.0 | 0.7 | 1.0 | 1.0 | 1.0 | 1.0 | 1.0 | 1.0 | 1.0 | 0.7 | 1.2 | 0.9 | 0.5 | 1.0 | 1.0 | 0.9 | 1.7 | 2.5 | 1.0 | 1.1 | 1.0 | 1.0 | 1.0 |
| Prm2 | 1.0 | 1.0 | 0.5 | 1.0 | 1.0 | 1.0 | 1.0 | 1.0 | 1.0 | 1.0 | 1.0 | 1.0 | 2.5 | 1.0 | 1.0 | 1.0 | 0.6 | 2.5 | 0.7 | 1.0 | 1.1 | 0.9 | 1.0 | 1.0 |
| Prm3 | 1.0 | 1.0 | 1.0 | 1.0 | 1.0 | 1.0 | 1.0 | 1.0 | 1.0 | 1.0 | 1.6 | 1.0 | 1.0 | 1.0 | 1.0 | 1.0 | 1.0 | 1.0 | 1.0 | 1.0 | 1.1 | 1.0 | 1.0 | 1.0 |
| Prnd | 0.7 | 1.0 | 0.6 | 0.5 | 0.3 | 1.0 | 0.9 | 1.0 | 1.0 | 1.0 | 1.0 | 1.0 | 1.0 | 3.4 | 1.0 | 1.0 | 0.8 | 0.8 | 0.9 | 1.0 | 0.9 | 1.0 |  |  |
| Prss1a | 0.2 | 1.0 | 1.0 | 1.1 | 0.9 | 1.0 | 1.2 | 0.6 | 1.0 | 0.9 | 1.0 | 1.0 | 1.0 | 12.5 | 1.0 | 1.0 | 0.9 | 1.0 | 1.0 | 1.0 | 1.1 | 0.9 |  |  |
| Prom2 | 1.0 | 1.0 | 1.0 | 1.0 | 1.0 | 1.0 | 1.0 | 1.0 | 1.0 | 1.3 | 1.2 | 1.0 | 1.1 | 0.9 | 1.0 | 1.0 | 1.0 | 1.0 | 1.0 | 1.0 | 1.0 | 1.5 | 0.8 | 0.7 |
| Pnp2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Prph | 1.5 | 7.8 | 1.0 | 0.8 | 0.7 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Prpmp5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 1.0 |
| Prr32 | 1.0 | 1.0 | 1.7 | 1.2 | 0.7 | 0.8 | 1.0 | 1.0 | 1.0 | 1.0 | 1.0 | 1.0 | 1.0 | 1.0 | 2.1 | 1.1 | 1.0 | 1.0 | 1.0 | 0.9 | 1.3 | 1.2 | 1.0 |  |

[Fig. 23-11]

[Fig. 23-12]

| | | | | | | | | | | | | | | | | | | | | | | | |
|---|---|---|---|---|---|---|---|---|---|---|---|---|---|---|---|---|---|---|---|---|---|---|---|
| Saa1 | 1.0 | 1.0 | 1.0 | 0.8 | 1.0 | 1.0 | 1.0 | 1.0 | 1.0 | 1.0 | 1.0 | 1.0 | 1.0 | 0.6 | 1.0 | 1.0 | 1.0 | 1.0 | 1.0 | 1.0 | 0.6 | 0.9 | 1.0 | 1.0 |
| Saa2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Saa3 | 1.0 | 1.0 | 2.6 | 2.0 | 1.0 | 1.0 | 1.1 | 1.4 | 1.0 | 1.0 | 1.0 | 1.0 | 0.7 | 2.8 | 1.7 | 1.8 | 1.0 | 1.0 | 1.0 | 1.0 | 1.0 | 1.0 | 1.0 | 1.0 |
| Sash3 | 1.1 | 0.9 | 1.3 | 1.2 | 1.0 | 1.0 | 0.7 | 0.7 | 1.0 | 1.0 | 1.0 | 1.0 | 0.9 | 1.3 | 0.9 | 0.9 | 1.0 | 1.0 | 0.9 | 0.9 | 1.0 | 1.0 | 0.7 | 0.9 |
| Sbk2 | 1.0 | 1.0 | 0.7 | 1.0 | 1.0 | 1.0 | 1.0 | 0.5 | 1.0 | 1.0 | 1.1 | 1.3 | 0.7 | 0.4 | 1.5 | 0.3 | 0.6 | 0.4 | 1.5 | 1.0 | 1.0 | 1.0 | 0.5 | 15.4 |
| Sbp | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 0.1 |
| Sbpl | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.7 | 0.9 |
| Scara5 | 1.1 | 1.5 | 0.9 | 1.0 | 1.0 | 1.0 | 0.9 | 0.8 | 0.9 | 0.8 | 0.8 | 1.0 | 0.9 | 0.5 | 0.8 | 0.8 | 0.9 | 0.7 | 1.0 | 1.4 | 1.0 | 1.1 | 1.0 | 0.8 |
| Scarna3b | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Scarna8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Scd1 | 0.4 | 0.6 | 0.2 | 0.3 | 0.9 | 0.8 | 1.1 | 0.9 | 0.3 | 0.4 | 0.9 | 0.8 | 1.0 | 2.0 | 1.6 | 1.6 | 0.5 | 0.4 | 1.0 | 1.1 | 0.8 | 0.9 | 1.1 | 1.0 |
| Scd2 | 0.9 | 1.1 | 0.4 | 0.2 | 0.9 | 0.9 | 1.1 | 1.2 | 1.0 | 1.0 | 1.0 | 0.9 | 0.7 | 0.6 | 1.0 | 0.8 | 0.5 | 0.4 | 1.1 | 1.1 | 0.9 | 0.9 | 1.0 | 0.8 |
| Slc15a2 | 0.2 | 0.6 | 0.2 | 0.3 | 1.0 | 1.0 | 1.0 | 1.0 | 1.0 | 1.0 | 1.1 | 0.9 | 1.3 | 1.9 | 1.3 | 1.0 | 0.6 | 0.5 | 0.9 | 1.0 | 1.0 | 1.1 | 1.3 | 1.0 |
| Scd4 | 0.3 | 0.6 | 0.2 | 0.2 | 1.0 | 1.0 | 0.9 | 1.5 | 1.0 | 1.0 | 1.0 | 0.8 | 0.8 | 1.7 | 1.0 | 1.0 | 1.0 | 1.0 | 1.0 | 1.0 | 1.0 | 1.0 | 1.2 | 1.1 |
| Snora64 | 0.2 | 1.0 | 1.2 | 1.2 | 0.2 | 1.0 | 1.3 | 0.9 | 1.0 | 1.0 | 0.8 | 1.0 | 1.9 | 1.6 | 3.9 | 1.0 | 1.0 | 0.1 | 1.4 | 1.0 | 1.0 | 1.0 | 0.9 | 5.8 |
| Acot1 | 0.2 | 1.0 | 1.0 | 1.2 | 0.6 | 1.0 | 1.4 | 0.7 | 0.8 | 1.0 | 1.3 | 1.0 | 1.0 | 1.5 | 4.8 | 1.0 | 0.1 | 1.0 | 1.0 | 1.0 | 1.0 | 1.0 | 2.0 | 1.1 |
| Scgb2b12 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 1.0 |
| Scgb2b15 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 1.0 |
| Scgb2b17 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 0.5 |
| Scgb2b20 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 1.0 |
| Scgb2b27 | 0.3 | 1.0 | 1.0 | 0.8 | 0.6 | 1.0 | 1.6 | 0.5 | 0.9 | 1.0 | 0.8 | 1.0 | 1.0 | 1.0 | 3.1 | 1.0 | 1.0 | 0.1 | 1.0 | 1.0 | 1.0 | 1.0 | 0.7 | 0.7 |
| Scgb3a1 | 1.0 | 1.0 | 1.0 | 1.0 | 1.0 | 1.0 | 1.1 | 1.3 | 1.0 | 1.0 | 1.0 | 1.0 | 1.0 | 1.0 | 1.0 | 1.0 | 1.0 | 1.0 | 1.0 | 1.0 | 1.0 | 1.0 | 0.2 | 0.4 |
| Scgb3a2 | 1.0 | 1.0 | 1.0 | 1.0 | 1.0 | 1.0 | 1.0 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 0.3 | 5.2 |
| Scn4b | 1.0 | 1.0 | 0.7 | 1.0 | 1.0 | 1.0 | 0.9 | 1.0 | 0.7 | 1.0 | 1.7 | 1.0 | 0.9 | 0.7 | 3.7 | 0.3 | 0.9 | 1.1 | 0.9 | 0.9 | 1.0 | 1.0 | 1.2 | 5.5 |
| Scx | 1.0 | 1.0 | 1.5 | 1.0 | 1.0 | 1.3 | 1.1 | 0.9 | 1.2 | 2.7 | 1.4 | 1.1 | 1.8 | 0.8 | 0.9 | 0.5 | 1.3 | 1.2 | 2.0 | 1.1 | 1.2 | 0.7 | 0.8 | 0.7 |
| Sectm1b | 1.0 | 1.0 | 1.0 | 1.0 | 1.0 | 1.0 | 1.1 | 1.1 | 1.0 | 1.0 | 0.7 | 1.0 | 1.0 | 1.0 | 1.0 | 1.0 | 1.0 | 1.0 | 1.0 | 1.0 | 1.0 | 1.0 | 0.4 | 2.2 |
| Selenbp2 | 0.8 | 1.1 | 2.0 | 1.2 | 1.0 | 1.0 | 1.3 | 1.2 | 1.0 | 1.1 | 1.1 | 1.7 | 1.7 | 0.5 | 1.2 | 1.3 | 1.5 | 2.0 | 1.2 | 1.7 | 1.0 | 0.9 | 1.3 | 1.6 |
| Sell | 1.0 | 1.0 | 1.1 | 1.0 | 1.0 | 1.0 | 0.7 | 0.9 | 1.0 | 1.0 | 1.0 | 1.0 | 1.0 | 1.0 | 1.0 | 1.2 | 1.0 | 1.0 | 1.0 | 0.8 | 1.2 | 0.6 | 1.0 | |
| Serinc2 | 1.2 | 0.7 | 1.0 | 1.0 | 0.9 | 0.8 | 1.5 | 1.2 | 0.9 | 0.9 | 0.5 | 0.9 | 1.3 | 0.8 | 3.1 | 0.6 | 0.9 | 0.8 | 1.0 | 1.0 | 1.1 | 1.0 | 0.8 | 1.2 |
| Serpina10 | 1.0 | 1.0 | 1.0 | 1.0 | 1.0 | 1.0 | 1.0 | 1.0 | 0.9 | 0.4 | 1.0 | 1.0 | 1.0 | 1.0 | 1.0 | 1.0 | 1.0 | 1.0 | 0.7 | 1.3 | 1.0 | 1.0 | 1.0 | 1.0 |
| Serpina12 | 1.0 | 1.0 | 1.0 | 1.0 | 1.0 | 1.0 | 1.0 | 1.0 | 1.0 | 1.0 | 1.0 | 1.0 | 1.3 | 1.5 | 1.0 | 1.0 | 1.0 | 1.0 | 1.0 | 1.0 | 1.0 | 1.0 | 1.0 | 1.0 |
| Serpina1a | 0.8 | 0.4 | 1.0 | 0.1 | 1.0 | 1.0 | 1.3 | 1.0 | 1.0 | 1.0 | 0.8 | 1.0 | 1.0 | 1.0 | 1.0 | 1.0 | 0.6 | 1.2 | 1.0 | 1.0 | 1.0 | 1.0 | 1.2 | 1.0 |
| Serpina1b | 1.2 | 0.5 | 1.0 | 0.1 | 1.0 | 1.0 | 2.4 | 1.0 | 0.7 | 1.0 | 0.9 | 1.0 | 1.0 | 1.0 | 1.1 | 1.0 | 1.0 | 0.8 | 1.2 | 1.0 | 1.0 | 1.0 | 1.4 | 1.0 |
| Serpina1c | 0.6 | 0.3 | 1.0 | 0.1 | 1.0 | 1.0 | 2.1 | 1.0 | 0.7 | 1.3 | 1.0 | 1.0 | 1.0 | 1.0 | 1.3 | 1.0 | 1.0 | 1.0 | 0.9 | 0.7 | 1.0 | 1.0 | 0.8 | 1.0 |
| Serpina1d | 0.9 | 0.3 | 1.0 | 0.1 | 1.0 | 1.0 | 1.5 | 1.0 | 1.0 | 1.0 | 1.6 | 1.0 | 1.0 | 1.0 | 1.0 | 1.0 | 1.0 | 1.0 | 0.8 | 0.9 | 1.0 | 1.0 | 1.5 | 1.0 |
| Serpina1e | 1.0 | 0.1 | 1.0 | 0.2 | 0.5 | 1.0 | 1.9 | 1.0 | 1.1 | 1.0 | 1.0 | 1.0 | 1.4 | 0.7 | 1.0 | 1.0 | 1.0 | 1.0 | 1.1 | 1.7 | 1.0 | 1.0 | 1.0 | 1.0 |
| Serpina1f | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.2 | 1.0 | 1.0 |
| Serpina3c | 1.8 | 1.2 | 1.2 | 1.0 | 1.0 | 1.0 | 0.9 | 0.9 | 1.0 | 1.0 | 1.2 | 1.3 | 1.0 | 1.1 | 0.7 | 0.7 | 1.4 | 0.9 | 1.3 | 1.0 | 0.9 | 0.9 | 1.5 | 1.1 |
| Serpina3k | 1.3 | 0.3 | 1.0 | 0.1 | 0.7 | 1.0 | 2.9 | 1.0 | 1.1 | 0.7 | 1.4 | 1.0 | 0.6 | 1.0 | 1.3 | 1.0 | 1.0 | 1.0 | 1.2 | 1.0 | 1.0 | 1.0 | 0.9 | 1.0 |
| Serpina4-ps1 | 1.0 | 1.0 | 1.0 | 0.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Serpinb11 | 1.0 | 1.0 | 1.0 | 1.0 | 1.0 | 1.0 | 1.0 | 1.0 | 1.0 | 1.0 | 1.1 | 1.3 | 1.1 | 0.8 | 1.0 | 1.0 | 1.0 | 1.0 | 1.0 | 1.0 | 1.0 | 1.0 | 0.2 | 1.0 |
| Serpinb3a | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 5.8 | 1.0 |
| Serpinb6d | 1.0 | 1.0 | 1.0 | 1.0 | 1.0 | 1.0 | 1.0 | 1.0 | 1.0 | 1.0 | 1.0 | 1.0 | 0.3 | 0.7 | 1.0 | 1.0 | 1.0 | 1.0 | 1.0 | 1.0 | 1.0 | 1.0 | 1.0 | 1.0 |
| Serpinb6e | 1.0 | 1.0 | 1.0 | 1.0 | 1.0 | 1.0 | 1.0 | 1.0 | 1.0 | 1.0 | 1.0 | 1.0 | 4.7 | 9.3 | 1.0 | 1.0 | 1.0 | 1.0 | 1.0 | 1.0 | 1.0 | 1.0 | 1.0 | 1.0 |
| Serpinc1 | 1.0 | 1.0 | 1.0 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Serpind2 | 1.0 | 1.0 | 1.0 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sfrp5 | 0.8 | 1.4 | 1.3 | 1.2 | 0.8 | 1.2 | 1.0 | 1.0 | 1.0 | 1.0 | 1.3 | 1.2 | 1.9 | 1.5 | 0.8 | 0.7 | 1.0 | 1.3 | 1.0 | 1.0 | 1.0 | 1.0 | 0.7 | 0.8 |
| Sgca | 1.0 | 1.0 | 0.9 | 0.8 | 1.0 | 1.0 | 1.0 | 1.0 | 1.0 | 1.0 | 1.0 | 1.0 | 2.4 | 1.0 | 2.6 | 0.5 | 1.0 | 1.1 | 1.0 | 1.0 | 1.2 | 0.8 | 1.2 | 7.7 |
| Sgcg | 1.0 | 1.0 | 1.2 | 0.8 | 1.0 | 1.0 | 0.7 | 0.8 | 1.0 | 1.0 | 1.0 | 1.0 | 2.2 | 1.0 | 4.0 | 0.3 | 1.0 | 1.1 | 1.0 | 1.0 | 1.0 | 1.0 | 1.1 | 9.1 |
| Sh3bp2 | 0.8 | 1.1 | 1.2 | 1.0 | 1.0 | 1.0 | 1.0 | 0.9 | 1.0 | 1.0 | 1.0 | 0.9 | 0.2 | 1.1 | 1.0 | 1.1 | 0.6 | 0.5 | 0.9 | 1.0 | 0.9 | 1.0 | 0.8 | 1.2 |
| Sh3gl2 | 1.0 | 0.9 | 1.0 | 1.0 | 1.0 | 1.0 | 0.7 | 0.8 | 1.0 | 1.0 | 1.0 | 1.0 | 1.4 | 1.0 | 0.7 | 1.0 | 1.0 | 1.0 | 1.0 | 1.0 | 1.1 | 1.3 | 1.3 | 0.8 |
| Shd | 1.0 | 0.2 | 1.0 | 1.0 | 0.9 | 0.9 | 1.0 | 1.0 | 1.0 | 1.0 | 1.0 | 0.8 | 1.1 | 1.0 | 1.0 | 1.0 | 1.0 | 1.0 | 1.0 | 1.0 | 0.9 | 1.1 | 1.0 | 1.0 |
| Shh | 0.5 | 0.6 | 1.0 | 1.0 | 1.0 | 1.0 | 1.2 | 1.0 | 1.0 | 1.0 | 1.0 | 0.3 | 0.6 | 1.0 | 1.0 | 1.0 | 1.0 | 1.0 | 1.0 | 1.0 | 1.0 | 1.0 | 1.0 | 1.0 |
| Foxn3 | 0.3 | 0.7 | 0.3 | 1.2 | 0.7 | 0.9 | 0.6 | 1.1 | 1.0 | 1.0 | 0.6 | 0.9 | 0.3 | 1.2 | 0.2 | 1.5 | 0.3 | 0.7 | 1.0 | 1.0 | 1.0 | 0.2 | 1.0 | |
| Slc16a3 | 1.0 | 1.0 | 1.3 | 1.1 | 0.8 | 1.0 | 1.3 | 1.1 | 1.0 | 1.0 | 1.5 | 1.2 | 1.2 | 0.9 | 1.0 | 0.7 | 1.0 | 1.0 | 1.0 | 1.2 | 1.1 | 0.9 | 5.0 | |
| Slc16a9 | 0.8 | 0.8 | 0.7 | 0.8 | 1.1 | 0.5 | 1.3 | 1.4 | 1.0 | 1.0 | 1.0 | 1.4 | 0.8 | 1.0 | 0.8 | 1.0 | 0.9 | 0.4 | 1.1 | 1.2 | 1.1 | 0.9 | 1.1 | 1.2 |
| Slc17a9 | 1.0 | 0.9 | 1.0 | 1.1 | 1.0 | 1.0 | 0.9 | 1.2 | 1.5 | 1.3 | 0.6 | 0.7 | 0.7 | 0.6 | 1.0 | 1.0 | 1.0 | 1.1 | 1.0 | 1.2 | 0.8 | 0.5 | 1.8 | |
| Slc1a1 | 1.0 | 1.0 | 1.6 | 0.8 | 1.1 | 1.1 | 0.9 | 1.0 | 1.0 | 1.0 | 1.6 | 1.5 | 1.4 | 1.3 | 1.0 | 1.1 | 1.2 | 1.0 | 1.0 | 1.0 | 1.0 | 1.7 | 1.7 | |
| Slc22a26 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc22a27 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc22a28 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc22a30 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc22a7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc25a30 | 0.5 | 0.5 | 1.2 | 0.9 | 0.8 | 0.9 | 1.1 | 2.1 | 1.0 | 1.0 | 1.3 | 0.9 | 0.3 | 1.1 | 1.7 | 0.7 | 0.6 | 0.5 | 1.0 | 0.9 | 1.0 | 0.8 | 0.6 | 0.6 |
| Slc25a47 | 1.0 | 0.9 | 1.8 | 1.1 | 0.8 | 1.3 | 1.4 | 1.3 | 1.1 | 1.0 | 1.0 | 1.3 | 1.0 | 0.9 | 1.0 | 0.9 | 0.9 | 0.5 | 1.1 | 0.9 | 0.8 | 1.3 | 1.3 | |
| Slc30a10 | 1.0 | 1.0 | 1.0 | 1.0 | 0.8 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | |
| | AG | | Aorta | | Brain | | Lung | | Pancreas | | PG | | Skin | | Skull | | SM | | Spleen | | Testis | | TG | |
| | E | M | E | M | E | M | E | M | E | M | E | M | E | M | E | M | E | M | E | M | E | M | E | M |
| Slc34a2 | 1.0 | 1.0 | 1.0 | 1.0 | 1.0 | 1.0 | 1.0 | 1.2 | 1.0 | 1.0 | 1.0 | 1.0 | 1.0 | 0.8 | 1.0 | 1.0 | 1.0 | 1.0 | 1.0 | 0.9 | 1.0 | 1.0 | 1.0 | |
| Slc35f2 | 0.5 | 0.6 | 1.0 | 1.0 | 1.5 | 1.2 | 1.0 | 1.0 | 1.0 | 1.0 | 0.8 | 1.0 | 2.0 | 1.6 | 1.1 | 1.0 | 0.9 | 1.3 | 1.3 | 0.9 | 0.8 | | | |
| Slc38a3 | 1.0 | 1.0 | 1.0 | 0.4 | 0.9 | 1.0 | 1.0 | 1.0 | 0.6 | 0.9 | 1.1 | 1.5 | 2.4 | 0.8 | 2.6 | 0.9 | 1.0 | 1.5 | 1.0 | 1.0 | 1.1 | 0.9 | | |
| Slc38a5 | 1.0 | 1.0 | 1.0 | 1.0 | 1.0 | 1.0 | 0.5 | 0.6 | 0.5 | 0.6 | 1.0 | 1.0 | 1.3 | 1.3 | 1.6 | 1.0 | 1.0 | 4.7 | 0.3 | 1.1 | 1.0 | 1.0 | | |
| Slc45a3 | 2.2 | 1.7 | 1.8 | 3.0 | 1.0 | 1.0 | 0.8 | 1.2 | 1.0 | 1.0 | 1.4 | 1.2 | 1.9 | 1.8 | 1.5 | 1.6 | 2.1 | 2.1 | 3.7 | 0.5 | 1.0 | 1.0 | 1.2 | 1.8 |
| Slc4a3 | 1.0 | 1.0 | 1.0 | 1.0 | 1.0 | 1.0 | 1.2 | 1.4 | 1.0 | 1.0 | 1.4 | 0.7 | 1.7 | 1.8 | 1.0 | 1.6 | 6.1 | 0.4 | 1.0 | 1.0 | 1.0 | | | |
| Slc5b | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | |
| Slc7a12 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | | |
| Slc7a5 | 1.0 | 0.9 | 1.2 | 1.0 | 1.0 | 1.1 | 1.2 | 1.4 | 1.6 | 2.1 | 0.4 | 0.8 | 0.8 | 0.6 | 1.4 | 1.5 | 1.2 | 1.0 | 1.8 | 0.9 | 0.9 | 0.8 | 1.1 | |
| Slc7a8 | 1.0 | 1.0 | 3.1 | 6.9 | 1.0 | 1.0 | 1.3 | 1.2 | 1.2 | 1.2 | 1.1 | 1.1 | 0.7 | 1.2 | 1.3 | 0.7 | 1.1 | 1.3 | 0.9 | 1.0 | 2.2 | 1.4 | | |
| Slc9a8 | 1.0 | 1.2 | 1.0 | 0.9 | 1.0 | 1.0 | 1.0 | 1.2 | 1.2 | 1.1 | 1.1 | 1.1 | 0.9 | 1.2 | 1.0 | 1.2 | 0.9 | 1.0 | 1.0 | 1.0 | 1.0 | 1.0 | | |
| Slco1a1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slco1a4 | 1.0 | 1.0 | 1.0 | 1.0 | 1.1 | 1.0 | 1.0 | 1.0 | 1.0 | 1.0 | 1.0 | 1.0 | 1.0 | 1.0 | 1.0 | 1.0 | 1.0 | 1.0 | 0.9 | 1.1 | 1.0 | 1.0 | | |
| Slitrk4 | 1.0 | 1.0 | 1.0 | 1.0 | 1.0 | 1.0 | 1.8 | 1.8 | 1.0 | 1.0 | 1.0 | 1.0 | 0.3 | 0.5 | 0.7 | 0.7 | 1.0 | 1.0 | 1.2 | 1.4 | 1.0 | 1.0 | | |
| Slpi | 1.4 | 1.0 | 1.5 | 1.3 | 1.0 | 1.0 | 1.5 | 1.3 | 1.0 | 1.6 | 1.0 | 1.0 | 1.7 | 3.4 | 0.9 | 1.1 | 1.0 | 1.2 | 0.6 | 1.0 | 1.0 | 22.6 | 1.0 | |
| Smcp1 | 1.0 | 1.0 | 1.0 | 1.0 | 1.0 | 1.0 | 1.0 | 1.0 | 1.0 | 1.0 | 1.0 | 1.0 | 1.6 | 0.9 | 5.1 | 0.3 | 0.7 | 0.8 | 1.0 | 1.0 | 1.0 | 0.9 | 5.3 | |

[Fig. 23-13]

Table content too dense and low-resolution to transcribe reliably.

| | | | | | | | | | | | | | | | | | | | | | | | |
|---|---|---|---|---|---|---|---|---|---|---|---|---|---|---|---|---|---|---|---|---|---|---|---|
| Yip7 | 1.0 | 1.0 | 1.0 | 1.0 | 1.0 | 1.0 | 1.0 | 1.0 | 1.0 | 1.0 | 1.0 | 1.0 | 1.7 | 1.2 | 2.8 | 0.4 | 0.7 | 0.7 | 1.0 | 1.0 | 0.7 | 0.8 | 0.9 | 5.4 |
| Ypel4 | 0.8 | 0.9 | 0.9 | 0.9 | 1.0 | 0.8 | 1.0 | 1.0 | 1.0 | 1.0 | 1.1 | 0.9 | 1.6 | 1.5 | 1.2 | 1.2 | 1.0 | 1.0 | 5.5 | 0.4 | 1.6 | 0.7 | 1.0 | 0.7 |
| Zbed6 | 1.0 | 0.7 | 1.3 | 1.0 | 0.8 | 0.6 | 0.7 | 2.7 | 1.0 | 1.0 | 1.1 | 1.1 | 0.5 | 1.1 | 1.1 | 0.6 | 1.1 | 1.5 | 1.0 | 0.8 | 0.8 | 1.0 | 1.4 | 0.7 |
| Zfp369 | 1.0 | 1.0 | 1.0 | 1.0 | 0.9 | 0.7 | 0.6 | 1.0 | 1.0 | 1.0 | 1.0 | 1.0 | 0.7 | 1.0 | 1.7 | 0.6 | 1.7 | 1.0 | 1.1 | 0.9 | 1.0 | 0.9 | 1.0 | 1.0 |
| Zfp648 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Zfp750 | 1.0 | 1.0 | 1.0 | 1.0 | 1.0 | 1.0 | 0.9 | 1.3 | 0.6 | 1.0 | 1.2 | 1.1 | 1.0 | 1.0 | 1.0 | 1.0 | 1.0 | 1.0 | 1.0 | 1.0 | 1.0 | 1.0 | 0.7 | 0.8 |
| Zg16 | 0.9 | 0.8 | 1.0 | 1.0 | 2.5 | 0.9 | 0.9 | 1.0 | 1.0 | 1.2 | 0.6 | 0.9 | 1.0 | 1.7 | 1.5 | 0.9 | 1.7 | 2.5 | 1.1 | 0.6 | 1.0 | 2.6 | 1.5 | 1.0 |

[Fig. 23-16]

| | Kidney | | Colon | | Eyeball | | Heart | | Liver | | SG | | Thyroid | | Adipose | | Stomach | | Jejunum | | Ileum | |
|---|---|---|---|---|---|---|---|---|---|---|---|---|---|---|---|---|---|---|---|---|---|---|
| | E | M | E | M | E | M | E | M | E | M | E | M | E | M | E | M | E | M | E | M | E | M |
| Abcb1b | 7.8 | 5.3 | 1.2 | 2.4 | 1.0 | 1.0 | 1.2 | 1.4 | 1.0 | 1.0 | 1.0 | 1.0 | 1.2 | 1.3 | 0.7 | 1.0 | 1.0 | 1.0 | 1.0 | 1.2 | 1.2 | 1.9 |
| Abce4 | 1.0 | 1.0 | 1.0 | 1.0 | 1.0 | 1.0 | 1.0 | 1.0 | 1.0 | 1.0 | 1.0 | 1.0 | 1.0 | 1.0 | 0.6 | 0.7 | 1.0 | 1.0 | 1.0 | 1.0 | 1.0 | 1.0 |
| Abra | 1.0 | 1.0 | 1.0 | 1.0 | 0.6 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Acbd7 | 1.0 | 1.0 | 1.0 | 1.0 | 1.0 | 2.7 | 1.0 | 1.6 | 1.0 | 1.0 | 1.0 | 1.0 | 1.0 | 1.0 | 5.6 | 1.1 | 1.0 | 1.0 | 1.0 | 1.0 | 1.0 | 1.0 |
| Acmsd | 1.7 | 1.5 | 1.0 | 1.0 | 1.0 | 1.0 | 1.0 | 1.0 | 13.8 | 4.1 | 1.0 | 1.0 | 1.0 | 1.0 | 1.0 | 1.0 | 1.3 | 1.0 | 1.0 | 0.6 | 0.8 | 1.0 |
| Acot3 | 2.8 | 3.3 | 1.0 | 1.0 | 1.0 | 1.0 | 1.1 | 1.2 | 2.8 | 19.7 | 1.0 | 1.0 | 1.0 | 1.0 | 4.8 | 3.3 | 1.0 | 1.0 | 1.0 | 1.0 | 1.0 | 1.0 |
| Acsm3 | 0.4 | 0.2 | 1.1 | 0.9 | 1.0 | 1.0 | 1.0 | 1.0 | 0.8 | 0.7 | 1.1 | 1.5 | 1.3 | 1.2 | 2.9 | 6.4 | 1.5 | 1.1 | 0.9 | 0.8 | 1.1 | 1.5 |
| Acka1 | 1.0 | 1.0 | 0.8 | 0.8 | 0.6 | 0.5 | 0.9 | 0.7 | 1.0 | 1.0 | 2.2 | 1.8 | 0.4 | 0.8 | 0.7 | 1.4 | 0.5 | 1.2 | 2.1 | 1.3 | 2.6 | 0.9 |
| Ackc1 | 1.0 | 1.0 | 0.8 | 0.6 | 0.4 | 0.5 | 0.9 | 0.8 | 1.0 | 1.0 | 1.0 | 1.0 | 1.0 | 1.4 | 1.0 | 1.4 | 1.1 | 1.1 | 1.0 | 0.6 | 0.7 | 1.7 |
| Acrg2 | 1.0 | 1.0 | 1.2 | 0.9 | 1.1 | 1.0 | 1.2 | 0.8 | 1.0 | 1.0 | 0.8 | 0.4 | 1.0 | 1.0 | 28.6 | 4.4 | 2.5 | 1.5 | 1.4 | 1.3 | 0.6 | 0.9 |
| Actn2 | 1.0 | 1.0 | 1.0 | 1.0 | 0.6 | 0.7 | 1.0 | 1.1 | 1.0 | 1.0 | 1.0 | 1.0 | 1.0 | 1.0 | 1.0 | 1.0 | 1.0 | 0.9 | 1.0 | 1.0 | 1.0 | 1.0 |
| Actn3 | 1.0 | 1.0 | 1.0 | 1.0 | 0.6 | 0.4 | 1.0 | 1.0 | 1.0 | 1.0 | 1.0 | 1.2 | 1.4 | 1.4 | 1.0 | 0.7 | 1.0 | 1.0 | 1.0 | 1.0 | 1.0 | 1.0 |
| Adam28 | 1.0 | 1.0 | 1.0 | 1.0 | 1.2 | 1.0 | 1.0 | 1.0 | 1.0 | 1.0 | 1.0 | 1.0 | 2.3 | 2.8 | 67.2 | 1.0 | 1.0 | 0.9 | 1.0 | 1.0 | 1.0 | 1.0 |
| Adam7 | 1.0 | 1.0 | 1.0 | 1.0 | 1.0 | 1.0 | 1.0 | 1.0 | 1.0 | 1.0 | 1.0 | 1.0 | 1.0 | 1.0 | 37.0 | 1.0 | 1.0 | 1.0 | 1.0 | 1.0 | 1.0 | 1.0 |
| Adh1 | 1.0 | 1.0 | 1.0 | 1.0 | 1.1 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Adh1 | 0.9 | 0.7 | 1.5 | 1.4 | 0.9 | 1.1 | 0.9 | 1.1 | 1.3 | 1.2 | 2.1 | 1.5 | 4.0 | 3.6 | 0.8 | 1.6 | 1.4 | 1.1 | 1.1 | 1.1 | 1.2 | 1.0 |
| Adh6-ps1 | 1.0 | 1.0 | 1.0 | 1.0 | 1.0 | 1.0 | 1.0 | 1.0 | 0.0 | 0.1 | 1.0 | 1.0 | 1.0 | 1.0 | 1.0 | 1.0 | 1.0 | 1.0 | 1.0 | 1.0 | 1.0 | 1.0 |
| Adh7 | 1.0 | 1.0 | 1.0 | 1.0 | 1.0 | 1.1 | 1.0 | 1.6 | 3.3 | 0.9 | 1.0 | 1.0 | 1.0 | 1.0 | 1.0 | 0.9 | 0.9 | 1.0 | 0.8 | 1.0 | 1.0 |
| Adig | 1.0 | 1.0 | 0.7 | 1.7 | 0.7 | 0.4 | 3.8 | 0.9 | 1.0 | 1.0 | 1.0 | 1.0 | 1.6 | 8.4 | 1.1 | 1.9 | 1.0 | 1.0 | 0.5 | 1.0 | 1.2 | 2.0 |
| Adipoq | 1.0 | 1.0 | 0.6 | 1.5 | 0.3 | 0.8 | 3.8 | 1.6 | 1.0 | 1.0 | 0.7 | 4.2 | 1.8 | 5.3 | 0.7 | 1.3 | 0.5 | 1.2 | 0.9 | 0.8 | 0.5 | 1.4 |
| Agps | 0.3 | 0.3 | 1.0 | 1.1 | 1.0 | 1.2 | 0.9 | 1.6 | 1.3 | 1.2 | 1.0 | 1.1 | 0.7 | 0.8 | 0.9 | 0.9 | 1.0 | 1.0 | 1.2 | 1.1 | 1.1 | 1.2 |
| Agr2 | 1.0 | 1.0 | 0.9 | 0.3 | 1.0 | 1.0 | 1.0 | 1.0 | 1.0 | 1.0 | 1.3 | 1.0 | 1.0 | 1.0 | 3.7 | 1.0 | 1.5 | 1.1 | 1.2 | 1.8 | 1.0 | 0.9 |
| Ahsg | 0.5 | 1.0 | 0.1 | 1.0 | 1.0 | 1.0 | 1.7 | 1.7 | 0.9 | 0.9 | 1.4 | 1.0 | 1.0 | 0.8 | 0.2 | 0.5 | 15.5 | 0.2 | 1.0 | 1.0 | 1.0 | 1.0 |
| Aicda | 1.0 | 1.0 | 0.7 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.9 | 1.0 |
| Aim | 0.3 | 0.4 | 0.6 | 0.9 | 1.8 | 1.8 | 1.2 | 0.6 | 1.5 | 1.3 | 1.0 | 1.8 | 0.8 | 0.8 | 0.9 | 1.1 | 0.9 | 0.7 | 0.6 | 0.9 | 0.7 | 0.9 |
| Akp3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 11.9 | 1.2 | 1.0 | 1.0 |
| Akr1b3 | 1.6 | 6.1 | 1.3 | 2.2 | 0.9 | 3.2 | 1.0 | 3.3 | 1.0 | 0.7 | 2.5 | 1.2 | 0.3 | 1.0 | 1.0 | 0.8 | 0.5 | 1.8 | 2.6 | 1.2 | 1.4 | 1.0 |
| Akr1b7 | 1.3 | 1.6 | 1.2 | 1.3 | 0.8 | 1.0 | 1.0 | 1.0 | 2.0 | 5.1 | 1.0 | 1.0 | 1.0 | 1.0 | 1.1 | 157.1 | 1.0 | 1.0 | 2.4 | 3.6 | 1.0 | 0.6 |
| Akr1b8 | 2.7 | 2.9 | 1.6 | 1.3 | 1.2 | 3.2 | 1.5 | 1.1 | 1.0 | 1.6 | 0.8 | 1.1 | 1.0 | 1.0 | 0.7 | 0.8 | 0.9 | 0.7 | 2.2 | 6.0 | 2.2 | 1.9 |
| Akr1c14 | 0.3 | 0.2 | 1.2 | 1.1 | 0.6 | 1.4 | 0.6 | 0.6 | 0.8 | 1.1 | 1.0 | 1.0 | 1.0 | 1.0 | 0.3 | 0.6 | 1.2 | 1.1 | 0.5 | 0.6 | 1.2 | 1.1 |
| Akr1c18 | 0.2 | 0.2 | 1.8 | 1.6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Alas2 | 1.6 | 1.2 | 1.0 | 1.0 | 4.1 | 0.7 | 0.9 | 2.3 | 0.0 | 0.1 | 1.7 | 0.9 | 2.5 | 1.7 | 1.4 | 1.9 | 1.5 | 1.2 | 1.0 | 1.4 | 1.0 | 1.0 |
| Alb | 1.3 | 1.3 | 0.2 | 1.0 | 1.0 | 0.8 | 1.0 | 1.0 | 1.3 | 1.4 | 0.7 | 1.0 | 1.0 | 6.2 | 0.2 | 1.2 | 146.2 | 0.6 | 1.0 | 0.8 | 1.0 | 1.0 |
| Aldh1a1 | 6.3 | 12.8 | 1.5 | 1.7 | 1.0 | 1.2 | 0.3 | 1.1 | 0.8 | 1.0 | 0.9 | 0.8 | 2.0 | 1.0 | 1.7 | 1.7 | 1.2 | 0.9 | 1.1 | 1.4 | 1.5 | 1.0 |
| Aldh1a3 | 1.6 | 1.3 | 1.9 | 0.9 | 1.1 | 1.3 | 1.0 | 1.0 | 1.0 | 1.0 | 1.2 | 1.1 | 1.7 | 2.5 | 0.7 | 0.7 | 1.0 | 1.8 | 1.1 | 1.1 | 1.0 | 1.1 |
| Aldh3a1 | 1.0 | 1.0 | 1.0 | 1.0 | 1.0 | 1.2 | 1.1 | 1.1 | 1.0 | 1.0 | 1.2 | 1.0 | 1.0 | 1.0 | 1.5 | 1.0 | 1.5 | 1.4 | 1.0 | 1.0 | 1.0 | 1.0 |
| Aldob | 1.1 | 1.2 | 1.0 | 1.1 | 1.0 | 1.0 | 1.3 | 1.6 | 1.4 | 0.9 | 1.0 | 3.0 | 1.0 | 0.4 | 2.5 | 2.9 | 7.3 | 0.2 | 1.1 | 0.9 | 1.0 | 1.0 |
| Aldoc | 1.2 | 1.4 | 0.9 | 1.0 | 1.1 | 1.1 | 1.0 | 1.0 | 1.1 | 1.1 | 1.6 | 1.2 | 1.3 | 1.9 | 6.4 | 1.4 | 1.3 | 0.9 | 2.6 | 0.9 | 1.8 | 1.2 |
| Alpk3 | 1.0 | 1.0 | 1.0 | 1.0 | 0.6 | 0.6 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Alpi | 1.5 | 1.4 | 1.4 | 0.8 | 1.0 | 1.0 | 1.0 | 1.0 | 1.6 | 2.3 | 0.6 | 0.6 | 1.0 | 1.0 | 5.8 | 0.8 | 1.4 | 1.2 | 1.1 | 0.8 | 1.0 | 0.2 |
| Ambp | 1.0 | 1.0 | 0.9 | 1.0 | 1.0 | 1.0 | 1.0 | 1.0 | 1.0 | 1.0 | 1.0 | 1.1 | 1.0 | 1.0 | 1.0 | 1.0 | 2.6 | 0.2 | 1.2 | 1.2 | 1.0 | 1.0 |
| Amd1 | 1.0 | 0.3 | 1.0 | 0.7 | 1.0 | 1.0 | 1.0 | 1.0 | 1.0 | 1.0 | 0.1 | 1.0 | 1.0 | 1.0 | 1.0 | 1.0 | 1.0 | 0.1 | 1.0 | 0.1 | 1.0 | 1.0 |
| Ampd1 | 1.0 | 1.0 | 1.0 | 1.0 | 0.9 | 0.4 | 1.0 | 1.0 | 1.0 | 1.0 | 1.0 | 1.0 | 1.2 | 1.2 | 1.0 | 1.0 | 1.3 | 1.0 | 1.0 | 1.0 | 1.0 | 1.0 |
| Amy1 | 1.2 | 0.9 | 1.3 | 1.5 | 1.2 | 1.1 | 2.0 | 1.2 | 0.5 | 1.7 | 3.0 | 12.9 | 1.6 | 7.9 | 0.7 | 1.8 | 1.8 | 1.0 | 0.6 | 1.0 | 0.9 | 1.1 |
| Amy2a2 | 1.0 | 1.0 | 1.5 | 3.4 | 1.0 | 1.0 | 1.0 | 1.0 | 1.0 | 1.0 | 1.0 | 1.0 | 1.0 | 1.0 | 1.0 | 1.0 | 2.4 | 0.1 | 0.7 | 1.0 | 1.0 | 1.0 |
| Prell | 0.9 | 1.0 | 1.5 | 468.7 | 1.4 | 1.0 | 1.0 | 1.0 | 0.6 | 0.8 | 0.9 | 1.3 | 1.0 | 0.0 | 1.0 | 1.0 | 16.3 | 0.5 | 0.0 | 0.2 | 0.9 | 1.0 |
| Amy2b | 1.0 | 0.9 | 1.6 | 29.9 | 1.0 | 1.0 | 1.0 | 1.0 | 1.0 | 1.5 | 2.8 | 14.5 | 1.0 | 1.0 | 1.0 | 1.0 | 13.6 | 0.5 | 0.0 | 1.0 | 1.0 | 1.0 |
| Ang4 | 1.0 | 1.0 | 0.0 | 0.0 | 1.0 | 1.0 | 1.0 | 1.0 | 1.0 | 1.0 | 1.0 | 1.0 | 0.6 | 0.5 | 1.0 | 1.0 | 1.0 | 1.0 | 0.5 | 0.2 | 0.6 | 0.6 |
| Angptl7 | 0.2 | 0.1 | 2.1 | 1.9 | 1.2 | 1.2 | 1.3 | 1.5 | 1.0 | 1.0 | 1.0 | 1.0 | 1.4 | 1.6 | 1.5 | 0.9 | 2.0 | 1.3 | 1.0 | 1.0 | 1.0 | 1.0 |
| Ank1 | 1.0 | 1.0 | 1.3 | 0.9 | 1.0 | 0.8 | 1.5 | 1.1 | 1.0 | 1.0 | 1.0 | 1.0 | 1.0 | 1.0 | 1.0 | 1.3 | 0.9 | 1.0 | 1.0 | 1.0 | 1.0 | 1.0 |
| Ankrd1 | 1.1 | 2.6 | 1.0 | 1.0 | 1.0 | 1.2 | 1.0 | 1.1 | 1.0 | 1.0 | 1.0 | 1.0 | 1.0 | 1.0 | 1.0 | 1.0 | 1.6 | 1.0 | 1.0 | 1.0 | 1.0 | 1.0 |
| Ankrd2 | 1.0 | 1.0 | 1.0 | 1.0 | 1.1 | 1.1 | 1.0 | 1.0 | 1.0 | 1.0 | 1.0 | 1.0 | 1.0 | 1.0 | 1.0 | 1.0 | 1.6 | 1.0 | 1.0 | 1.0 | 1.6 | 1.0 |
| Ansrd23 | 0.8 | 0.7 | 1.0 | 1.1 | 0.6 | 0.3 | 0.7 | 0.7 | 1.1 | 1.0 | 1.0 | 0.8 | 1.0 | 0.9 | 1.2 | 0.7 | 1.1 | 1.1 | 0.8 | 1.1 | 1.3 | 0.6 |
| Ansrd66 | 1.0 | 1.0 | 1.0 | 1.0 | 1.0 | 1.0 | 1.0 | 1.0 | 1.0 | 1.0 | 1.0 | 1.0 | 1.0 | 1.0 | 1.8 | 1.0 | 1.0 | 1.0 | 1.0 | 1.0 | 1.0 | 1.0 |
| Anpep | 0.8 | 0.7 | 1.8 | 1.7 | 0.7 | 0.8 | 1.0 | 1.0 | 1.1 | 0.9 | 1.3 | 1.1 | 2.0 | 1.2 | 0.8 | 0.6 | 1.1 | 1.2 | 1.7 | 1.7 | 1.2 | 1.6 |
| Aplnr2 | 1.3 | 1.2 | 1.0 | 0.9 | 1.1 | 1.4 | 1.0 | 1.0 | 1.0 | 0.9 | 0.9 | 1.0 | 1.2 | 1.1 | 7.5 | 1.4 | 1.1 | 1.0 | 1.1 | 1.1 | 1.0 | 0.9 |
| Aplc2 | 0.9 | 1.7 | 0.9 | 0.7 | 1.0 | 1.1 | 0.8 | 0.8 | 1.1 | 1.6 | 0.7 | 0.7 | 0.7 | 0.9 | 35.3 | 1.0 | 1.0 | 1.2 | 1.0 | 1.3 | 0.8 | 0.9 |
| Aplc3 | 1.1 | 1.0 | 1.0 | 1.3 | 1.2 | 1.5 | 1.0 | 1.0 | 1.0 | 1.0 | 1.5 | 0.9 | 1.0 | 1.0 | 6.2 | 1.2 | 1.1 | 1.1 | 0.8 | 1.0 | 0.9 | 1.2 |
| Aptn | 0.4 | 0.6 | 0.8 | 0.7 | 0.7 | 0.9 | 0.5 | 0.5 | 1.0 | 1.0 | 1.0 | 1.0 | 1.0 | 1.6 | 0.3 | 0.5 | 1.6 | 1.4 | 0.8 | 1.4 | 1.0 | 0.7 |
| Aptnr | 0.5 | 0.7 | 0.8 | 0.7 | 1.0 | 0.6 | 0.3 | 0.3 | 1.0 | 1.0 | 1.0 | 1.0 | 1.0 | 0.8 | 0.2 | 0.4 | 0.4 | 0.7 | 0.6 | 0.5 | 0.5 | 0.6 |
| Apoa1 | 1.5 | 1.4 | 0.1 | 3.3 | 1.0 | 0.9 | 1.0 | 1.0 | 0.6 | 0.9 | 0.8 | 1.0 | 2.2 | 0.3 | 0.1 | 0.4 | 0.9 | 1.0 | 1.5 | 1.5 | 1.3 | 0.9 |
| Apoa2 | 0.8 | 1.0 | 0.2 | 0.8 | 1.0 | 0.8 | 1.0 | 1.1 | 0.7 | 0.9 | 0.7 | 1.0 | 1.0 | 0.6 | 0.2 | 0.8 | 29.7 | 0.0 | 1.3 | 0.7 | 1.0 | 1.0 |
| Apoa4 | 0.7 | 0.5 | 0.4 | 3.3 | 1.0 | 1.0 | 1.0 | 1.6 | 0.7 | 0.7 | 1.0 | 1.0 | 2.2 | 0.5 | 1.0 | 1.0 | 0.8 | 0.8 | 0.7 | 1.0 | 2.5 | 1.8 |
| Apoa5 | 1.0 | 1.0 | 1.0 | 1.0 | 1.0 | 1.0 | 1.0 | 1.0 | 0.9 | 1.0 | 1.0 | 1.0 | 1.0 | 1.0 | 1.0 | 1.0 | 5.0 | 0.2 | 1.0 | 1.0 | 1.0 | 1.0 |
| Apobec2 | 0.8 | 0.4 | 0.5 | 0.6 | 0.8 | 0.6 | 1.0 | 1.0 | 1.0 | 1.0 | 1.4 | 1.2 | 0.6 | 1.1 | 1.0 | 1.0 | 0.5 | 0.8 | 1.5 | 0.6 | 1.3 | 1.0 |
| Apoc3 | 1.4 | 1.5 | 0.6 | 1.6 | 1.0 | 1.0 | 1.0 | 1.0 | 0.7 | 0.9 | 1.0 | 1.0 | 1.4 | 1.0 | 1.5 | 3.5 | 12.3 | 0.5 | 0.9 | 1.3 | 1.3 | 0.9 |
| Apoc4 | 1.7 | 2.0 | 1.0 | 1.0 | 1.0 | 1.0 | 1.0 | 1.0 | 0.8 | 0.8 | 1.0 | 1.0 | 1.0 | 1.7 | 0.8 | 5.0 | 0.2 | 1.0 | 1.0 | 1.0 | 1.0 |
| Apoe | 4.5 | 5.8 | 1.2 | 0.7 | 1.0 | 0.8 | 1.1 | 1.2 | 0.7 | 0.8 | 0.9 | 0.8 | 2.5 | 1.3 | 0.6 | 0.6 | 1.2 | 1.6 | 1.1 | 0.9 | 0.3 | 0.7 |
| Apoh | 1.1 | 0.9 | 1.0 | 1.0 | 1.0 | 1.0 | 1.0 | 1.0 | 0.9 | 1.2 | 1.0 | 1.0 | 1.0 | 1.0 | 3.9 | 0.3 | 1.0 | 1.0 | 1.0 | 1.0 |
| Apol10a | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.5 | 0.3 | 0.8 | 0.6 |
| Apol11b | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 0.8 | 0.8 |
| Apol6 | 1.0 | 1.0 | 1.2 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.6 | 1.0 |
| Arg2 | 8.4 | 11.3 | 2.2 | 3.0 | 1.1 | 1.3 | 1.0 | 1.0 | 1.0 | 1.0 | 1.0 | 1.0 | 1.0 | 1.0 | 2.8 | 2.9 | 1.2 | 2.0 | 1.1 | 1.3 | 0.9 | 1.2 |
| Armcx6 | 0.9 | 1.4 | 0.8 | 1.2 | 1.1 | 1.1 | 1.0 | 1.0 | 1.0 | 1.0 | 1.0 | 0.9 | 1.0 | 1.1 | 8.5 | 0.7 | 0.5 | 0.9 | 1.0 | 1.0 | 1.0 | 1.0 |
| Arnt2 | 1.4 | 1.3 | 0.9 | 1.0 | 1.2 | 0.9 | 1.0 | 1.0 | 1.0 | 1.0 | 1.0 | 1.0 | 1.6 | 1.0 | 9.1 | 1.0 | 0.6 | 1.1 | 1.2 | 1.3 | 1.0 | 1.0 |
| Art1 | 1.0 | 1.0 | 1.0 | 1.0 | 1.0 | 1.0 | 1.0 | 1.0 | 1.0 | 1.0 | 1.0 | 1.0 | 0.9 | 0.3 | 1.0 | 1.0 | 1.0 | 1.0 | 1.0 | 1.0 | 1.0 | 1.0 |
| Asb11 | 0.8 | 0.9 | 1.2 | 0.9 | 0.6 | 0.8 | 1.5 | 1.2 | 1.0 | 1.0 | 1.0 | 1.0 | 1.0 | 1.0 | 7.7 | 1.0 | 1.5 | 1.6 | 1.0 | 1.0 | 1.0 | 1.0 |
| Asb16 | 1.0 | 1.0 | 1.0 | 1.0 | 0.5 | 0.5 | 1.0 | 1.0 | 1.0 | 0.8 | 1.4 | 1.0 | 1.0 | 1.0 | 1.0 | 1.0 | 1.0 | 1.0 | 1.0 | 1.0 | 1.0 | 1.0 |
| Asb2 | 0.8 | 1.0 | 0.8 | 0.8 | 0.8 | 0.5 | 1.0 | 0.9 | 1.0 | 1.0 | 0.9 | 0.6 | 1.7 | 1.0 | 1.8 | 1.1 | 1.0 | 1.0 | 1.2 | 0.8 | 0.9 | 0.7 |
| Asb5 | 1.0 | 1.0 | 1.0 | 1.0 | 1.0 | 0.6 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ascl4 | 1.0 | 1.0 | 1.0 | 1.0 | 1.2 | 1.0 | 1.0 | 1.0 | 1.0 | 1.0 | 1.0 | 1.0 | 1.0 | 1.0 | 9.8 | 1.0 | 1.0 | 1.0 | 1.0 | 1.0 | 1.0 | 1.0 |
| Asprv1 | 1.0 | 1.0 | 0.8 | 0.9 | 1.0 | 1.1 | 1.0 | 1.0 | 1.0 | 1.0 | 1.0 | 0.9 | 1.8 | 0.5 | 1.0 | 1.1 | 1.0 | 0.9 | 1.1 | 1.1 | 0.8 | 0.5 |

[Fig. 23-17]

| | | | | | | | | | | | | | | | | | | | | | |
|---|---|---|---|---|---|---|---|---|---|---|---|---|---|---|---|---|---|---|---|---|---|
| Atcayos | 1.0 | 1.0 | 0.8 | 1.0 | 0.8 | 0.6 | 1.2 | 0.7 | 1.0 | 1.0 | 1.2 | 1.0 | 1.0 | 1.0 | 1.0 | 1.0 | 1.0 | 0.8 | 1.0 | 1.0 | 1.4 | 0.8 |
| Atp10b | 1.3 | 0.8 | 1.0 | 1.0 | 1.0 | 1.0 | 1.0 | 1.6 | 1.0 | 1.0 | 1.1 | 1.0 | 1.0 | 1.0 | 15.3 | 1.0 | 0.8 | 0.6 | 1.4 | 1.0 | 1.6 | 1.3 |
| Atp2a1 | 1.0 | 1.0 | 1.0 | 1.2 | 0.8 | 0.6 | 0.8 | 1.3 | 1.0 | 1.0 | 3.1 | 4.1 | 0.9 | 1.0 | 1.0 | 0.6 | 0.4 | 1.5 | 1.6 | 1.0 | 1.0 | 0.9 |
| Atp2b3 | 1.0 | 1.0 | 1.0 | 1.0 | 0.3 | 1.0 | 1.0 | 1.0 | 1.0 | 1.0 | 1.0 | 1.0 | 1.0 | 1.0 | 8.5 | 1.0 | 1.0 | 1.0 | 1.0 | 1.0 | 1.0 | 1.0 |
| Atp6v0c-ps2 | 1.0 | 0.2 | 1.0 | 0.8 | 1.0 | 2.6 | 1.0 | 0.6 | 1.0 | 1.0 | 1.0 | 1.0 | 1.0 | 2.0 | 1.0 | 1.0 | 1.0 | 1.9 | 1.0 | 1.0 | 1.0 | 1.0 |
| Atp6v0n2 | 1.0 | 1.5 | 1.0 | 1.0 | 1.0 | 1.2 | 1.0 | 1.0 | 1.5 | 1.9 | 1.1 | 1.1 | 1.5 | 3.3 | 11.6 | 0.5 | 2.0 | 2.9 | 1.0 | 1.0 | 1.0 | 1.0 |
| BC100530 | 1.0 | 1.0 | 1.0 | 1.0 | 1.0 | 1.8 | 1.0 | 1.0 | 1.0 | 1.0 | 1.0 | 1.0 | 1.0 | 1.0 | 1.9 | 1.0 | 0.4 | 5.5 | 1.0 | 1.0 | 1.0 | 1.0 |
| Basp1 | 1.0 | 7.1 | 0.8 | 0.5 | 1.0 | 1.0 | 0.8 | 0.8 | 0.9 | 0.7 | 0.7 | 0.8 | 1.2 | 0.8 | 8.0 | 1.2 | 1.2 | 1.3 | 1.3 | 1.1 | 0.7 | 0.7 |
| Bcl2a1b | 2.2 | 8.2 | 0.8 | 0.6 | 0.6 | 1.8 | 1.8 | 1.6 | 0.5 | 1.4 | 0.7 | 0.9 | 1.4 | 0.9 | 0.5 | 0.7 | 1.9 | 2.7 | 1.0 | 1.2 | 0.7 | 0.7 |
| Bcl2l15 | 1.0 | 1.0 | 1.0 | 1.0 | 1.0 | 1.0 | 1.0 | 1.0 | 1.0 | 1.0 | 1.0 | 1.0 | 2.4 | 1.2 | 26.4 | 1.0 | 1.0 | 1.0 | 1.2 | 1.1 | 1.0 | 0.8 |
| Bcl6 | 0.4 | 0.5 | 0.9 | 0.7 | 1.1 | 1.0 | 0.6 | 0.8 | 0.1 | 0.3 | 1.2 | 1.1 | 0.6 | 0.9 | 0.5 | 0.4 | 0.9 | 1.2 | 1.2 | 0.8 | 0.5 | 0.8 |
| Bcmo1 | 1.1 | 1.6 | 1.0 | 0.7 | 1.0 | 1.0 | 1.0 | 1.0 | 0.6 | 1.0 | 1.0 | 1.0 | 1.0 | 1.0 | 1.0 | 1.0 | 1.6 | 1.0 | 0.1 | 0.1 | 1.4 | 1.4 |
| Bex1 | 3.5 | 5.1 | 0.5 | 1.4 | 1.0 | 1.1 | 1.7 | 1.1 | 1.0 | 1.0 | 1.0 | 1.0 | 0.7 | 0.8 | 1.0 | 1.6 | 2.4 | 0.4 | 1.0 | 1.0 | 0.5 | 0.6 |
| Bex2 | 1.0 | 0.7 | 1.0 | 0.9 | 1.0 | 1.2 | 1.0 | 1.0 | 1.0 | 1.0 | 1.1 | 1.2 | 0.7 | 0.6 | 6.3 | 2.4 | 1.2 | 0.8 | 0.8 | 1.6 | 0.7 | 1.0 |
| Bex4 | 2.7 | 3.7 | 0.7 | 0.8 | 1.0 | 1.3 | 1.0 | 1.4 | 1.0 | 1.0 | 1.0 | 1.0 | 1.0 | 1.0 | 6.8 | 3.0 | 0.8 | 0.9 | 1.0 | 1.0 | 0.5 | 0.5 |
| | Kidney | | Colon | | Eyeball | | Heart | | Liver | | SG | | Thymus | | Adipose | | Stomach | | Jejunum | | Ileum | |
| | E | M | E | M | E | M | E | M | E | M | E | M | E | M | E | M | E | M | E | M | E | M |
| Bgtap3 | 1.0 | 1.0 | 1.9 | 1.4 | 1.0 | 1.0 | 1.0 | 1.0 | 1.0 | 1.0 | 0.8 | 0.5 | 1.9 | 1.0 | 26.0 | 2.0 | 1.1 | 1.0 | 5.5 | 2.0 | 2.0 | 1.2 |
| Bhrm | 3.0 | 6.0 | 0.8 | 1.0 | 1.0 | 1.0 | 1.0 | 1.0 | 0.0 | 0.1 | 1.0 | 1.0 | 1.0 | 1.0 | 1.0 | 1.0 | 1.0 | 0.2 | 1.0 | 1.0 | 0.9 | 0.9 |
| Bmyc | 1.2 | 1.1 | 0.9 | 0.8 | 0.9 | 0.8 | 1.0 | 1.0 | 0.4 | 0.2 | 0.9 | 0.8 | 1.5 | 1.0 | 4.3 | 1.3 | 1.4 | 1.5 | 0.8 | 1.2 | 0.7 | 1.0 |
| Bpi | 1.0 | 1.0 | 1.0 | 1.0 | 1.0 | 1.0 | 1.0 | 1.0 | 1.0 | 1.0 | 1.0 | 1.0 | 1.0 | 1.0 | 8.4 | 1.0 | 1.0 | 1.0 | 1.0 | 1.0 | 1.0 | 1.0 |
| Bpifb1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.5 | 0.9 | 1.0 | 1.0 | 1.0 | 1.0 |
| Bsph1 | 1.0 | 1.0 | 1.0 | 1.0 | 1.0 | 1.0 | 1.0 | 1.0 | 1.0 | 1.0 | 1.0 | 1.0 | 1.0 | 1.0 | 39.8 | 1.0 | 1.0 | 1.0 | 1.0 | 1.0 | 1.0 | 1.0 |
| Bspry | 1.1 | 1.0 | 0.9 | 1.1 | 0.9 | 1.0 | 1.0 | 1.0 | 1.0 | 1.0 | 0.8 | 0.9 | 1.4 | 1.3 | 6.2 | 2.3 | 1.0 | 1.0 | 1.3 | 1.3 | 1.2 | 1.1 |
| Btg3 | 5.2 | 1.0 | 0.3 | 1.0 | 0.8 | 1.0 | 0.2 | 1.0 | 0.5 | 1.0 | 0.5 | 0.2 | 1.3 | 1.0 | 7.2 | 1.0 | 0.4 | 2.0 | 1.0 | 1.0 | 2.3 | 1.0 |
| Btnl10 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| C1qtnf3 | 0.5 | 0.5 | 1.1 | 1.0 | 0.7 | 1.0 | 1.0 | 1.0 | 1.0 | 1.0 | 1.0 | 1.0 | 1.0 | 0.8 | 1.1 | 0.7 | 3.2 | 2.3 | 1.0 | 1.0 | 1.4 | 1.2 |
| C1qtnf6 | 1.1 | 1.8 | 1.1 | 1.0 | 1.0 | 0.9 | 0.8 | 0.9 | 0.9 | 1.0 | 0.3 | 0.7 | 1.0 | 0.8 | 0.4 | 0.5 | 1.2 | 1.4 | 1.1 | 0.9 | 0.8 | 1.1 |
| C2cd4b | 1.0 | 1.0 | 2.2 | 1.1 | 1.0 | 1.0 | 1.0 | 1.6 | 1.0 | 1.0 | 1.0 | 1.0 | 1.0 | 1.0 | 1.3 | 1.8 | 1.0 | 1.0 | 1.0 | 1.0 | 2.3 | 0.7 |
| C3 | 18.6 | 25.9 | 1.0 | 0.9 | 1.2 | 0.5 | 1.2 | 1.1 | 1.8 | 1.6 | 0.3 | 1.9 | 1.9 | 1.5 | 1.7 | 1.2 | 1.0 | 0.8 | 1.4 | 0.7 | 1.2 | 1.5 |
| C4bp | 1.0 | 1.0 | 0.8 | 0.6 | 1.0 | 1.0 | 1.0 | 1.0 | 0.9 | 0.8 | 1.0 | 1.0 | 1.0 | 1.0 | 85.3 | 1.0 | 1.2 | 0.8 | 1.0 | 1.0 | 0.9 | 1.0 |
| C6 | 1.0 | 1.0 | 1.0 | 1.0 | 1.0 | 1.0 | 1.0 | 1.0 | 0.0 | 0.1 | 1.0 | 1.0 | 1.1 | 1.0 | 0.4 | 0.6 | 1.0 | 1.0 | 0.9 | 0.8 | 0.7 | 0.7 |
| C8b | 1.0 | 1.0 | 1.0 | 1.0 | 1.0 | 1.0 | 1.0 | 1.0 | 0.0 | 0.2 | 1.0 | 1.0 | 1.0 | 1.0 | 1.0 | 1.0 | 1.0 | 1.0 | 1.0 | 1.0 | 1.0 | 1.0 |
| Cacna1s | 1.0 | 1.0 | 1.0 | 1.0 | 0.6 | 0.3 | 1.4 | 1.1 | 1.0 | 1.0 | 1.0 | 1.0 | 1.0 | 1.0 | 1.0 | 1.0 | 1.6 | 1.0 | 1.0 | 1.0 | 1.0 | 1.0 |
| Cacng1 | 1.0 | 1.0 | 1.0 | 1.0 | 1.0 | 0.6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cacng6 | 1.0 | 1.0 | 1.0 | 1.0 | 0.4 | 0.7 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Calon4 | 1.0 | 1.0 | 1.0 | 0.6 | 1.0 | 1.0 | 1.0 | 1.0 | 1.0 | 1.0 | 1.0 | 1.0 | 2.1 | 0.5 | 1.0 | 1.0 | 1.3 | 0.9 | 1.0 | 1.0 | 1.0 | 1.0 |
| Calol2 | 2.5 | 3.0 | 1.0 | 1.0 | 1.0 | 1.1 | 1.0 | 1.0 | 1.0 | 1.0 | 1.1 | 1.2 | 2.3 | 1.8 | 2.1 | 6.5 | 1.9 | 1.1 | 1.0 | 1.0 | 1.0 | 1.0 |
| Camk1g | 1.0 | 1.0 | 1.0 | 1.0 | 1.1 | 1.0 | 1.0 | 1.1 | 1.0 | 1.0 | 1.0 | 1.0 | 0.7 | 1.1 | 1.0 | 1.0 | 1.0 | 1.0 | 1.0 | 1.0 | 1.0 | 1.0 |
| Camk2a | 1.0 | 1.0 | 1.0 | 1.0 | 0.9 | 0.7 | 1.1 | 1.0 | 1.0 | 1.0 | 1.0 | 1.0 | 0.8 | 1.3 | 1.0 | 1.0 | 1.0 | 1.0 | 1.0 | 1.0 | 1.0 | 1.3 |
| Camk2b | 1.3 | 1.7 | 1.3 | 1.2 | 1.0 | 0.9 | 0.7 | 1.0 | 0.8 | 0.6 | 1.0 | 1.4 | 1.8 | 1.7 | 6.6 | 3.7 | 1.1 | 1.0 | 1.1 | 1.4 | 1.0 | 0.2 |
| Cap2 | 1.0 | 1.0 | 1.2 | 1.0 | 0.9 | 0.9 | 1.1 | 1.1 | 1.0 | 1.0 | 1.0 | 1.0 | 1.0 | 1.0 | 1.1 | 1.0 | 1.1 | 0.7 | 1.4 | 1.4 | 0.8 | 0.2 |
| Capn6 | 1.5 | 1.4 | 1.1 | 1.1 | 1.0 | 1.1 | 0.9 | 0.8 | 1.3 | 1.0 | 1.1 | 1.1 | 1.3 | 1.4 | 6.3 | 0.3 | 0.9 | 0.8 | 1.6 | 1.1 | 1.3 | 1.5 |
| Car1 | 1.0 | 1.0 | 1.0 | 1.6 | 1.0 | 1.0 | 1.0 | 1.0 | 0.0 | 0.2 | 1.0 | 1.0 | 1.0 | 1.0 | 0.8 | 1.4 | 1.0 | 1.0 | 1.0 | 1.0 | 1.0 | 1.0 |
| Car2 | 1.1 | 1.4 | 1.6 | 1.3 | 1.0 | 1.1 | 1.2 | 1.2 | 1.4 | 1.7 | 1.4 | 1.2 | 1.0 | 0.7 | 3.0 | 2.1 | 1.7 | 1.0 | 1.1 | 1.1 | 0.9 | 0.9 |
| Car3 | 0.2 | 0.1 | 0.8 | 1.9 | 0.8 | 0.9 | 2.2 | 1.0 | 0.0 | 0.1 | 1.4 | 4.1 | 1.7 | 5.1 | 0.9 | 1.1 | 0.8 | 1.1 | 1.2 | 1.0 | 0.8 | 2.2 |
| Car4 | 0.2 | 0.2 | 1.3 | 1.8 | 0.6 | 0.9 | 1.6 | 1.3 | 1.0 | 1.0 | 1.9 | 1.0 | 1.8 | 2.8 | 1.0 | 1.7 | 1.2 | 1.7 | 2.1 | 1.2 | 1.5 | 1.5 |
| Car5b | 1.2 | 1.3 | 1.5 | 1.3 | 0.9 | 1.0 | 1.6 | 1.3 | 1.4 | 1.4 | 1.0 | 1.2 | 2.5 | 5.8 | 1.3 | 1.7 | 1.1 | 1.4 | 0.9 | 1.0 | 0.9 | 1.9 |
| Car6 | 1.0 | 1.0 | 1.0 | 1.0 | 1.1 | 0.8 | 1.0 | 0.6 | 1.7 | 1.0 | 1.3 | 1.9 | 1.0 | 0.6 | 1.9 | 1.7 | 1.0 | 0.9 | 1.0 | 1.0 | 1.0 | 1.0 |
| Casc5 | 1.0 | 1.0 | 0.7 | 0.9 | 1.0 | 1.0 | 1.0 | 1.0 | 1.0 | 1.0 | 1.0 | 1.0 | 0.2 | 0.4 | 1.0 | 1.0 | 1.0 | 1.0 | 0.8 | 0.5 | 1.2 | 1.4 |
| Casq1 | 1.0 | 1.0 | 1.0 | 1.0 | 0.7 | 0.5 | 0.8 | 0.8 | 1.0 | 1.0 | 1.0 | 1.0 | 1.0 | 1.0 | 1.0 | 0.9 | 1.0 | 1.0 | 1.0 | 1.0 | 1.0 | 1.0 |
| Cav3 | 1.0 | 1.0 | 1.3 | 1.0 | 0.6 | 0.7 | 1.0 | 1.0 | 1.0 | 1.0 | 1.0 | 1.0 | 1.0 | 1.0 | 1.0 | 1.0 | 1.5 | 1.3 | 1.0 | 1.1 | 0.7 | 0.8 |
| Cbl | 1.7 | 0.8 | 0.9 | 1.2 | 1.5 | 1.0 | 0.9 | 0.7 | 1.7 | 1.0 | 0.8 | 2.3 | 0.1 | 0.4 | 0.7 | 0.4 | 0.6 | 0.8 | 0.6 | 0.3 | 1.6 | 2.7 |
| Cbr1 | 4.8 | 4.6 | 1.5 | 1.4 | 1.0 | 1.0 | 0.8 | 0.9 | 3.9 | 6.4 | 1.1 | 1.0 | 1.1 | 1.1 | 1.3 | 1.7 | 1.6 | 0.9 | 1.0 | 1.1 | 1.2 | 0.9 |
| Cbr3 | 5.9 | 5.7 | 2.2 | 1.5 | 0.6 | 0.7 | 1.1 | 0.6 | 4.7 | 11.8 | 1.0 | 0.8 | 1.3 | 3.3 | 1.5 | 1.5 | 1.0 | 1.5 | 2.4 | 2.1 | 1.4 | 1.4 |
| Ccl17 | 0.5 | 1.0 | 1.0 | 1.0 | 1.0 | 1.3 | 1.1 | 1.0 | 1.0 | 1.0 | 1.0 | 1.0 | 1.0 | 1.2 | 1.5 | 0.9 | 1.0 | 0.7 | 1.1 | 1.3 | 0.5 | 0.7 |
| Ccl2 | 1.0 | 5.9 | 0.8 | 0.6 | 1.0 | 1.7 | 1.3 | 1.3 | 1.0 | 1.7 | 1.0 | 0.7 | 0.8 | 1.3 | 0.5 | 0.7 | 2.1 | 1.8 | 1.0 | 0.8 | 1.0 | 0.9 |
| Ccl20 | 1.0 | 1.0 | 0.5 | 0.7 | 1.0 | 1.0 | 1.0 | 1.0 | 1.0 | 1.0 | 1.0 | 1.0 | 2.1 | 0.9 | 1.0 | 1.0 | 1.0 | 1.0 | 10.6 | 5.3 | 2.6 | 2.4 |
| Ccl21c | 3.6 | 0.3 | 6.3 | 7.4 | 0.5 | 1.6 | 4.2 | 2.0 | 0.8 | 0.9 | 0.4 | 2.1 | 1.0 | 1.0 | 0.5 | 3.5 | 0.4 | 0.3 | 2.8 | 1.5 | 4.9 | 0.1 |
| Ccl6 | 1.7 | 5.8 | 0.9 | 1.0 | 1.1 | 1.1 | 1.5 | 1.9 | 1.2 | 2.0 | 0.9 | 1.1 | 2.0 | 1.5 | 0.6 | 0.9 | 1.4 | 1.6 | 0.7 | 1.0 | 0.8 | 0.2 |
| Ccl7 | 1.0 | 1.0 | 0.5 | 0.3 | 1.0 | 1.0 | 1.5 | 0.5 | 1.0 | 1.0 | 1.0 | 1.0 | 1.1 | 0.9 | 6.3 | 0.2 | 1.2 | 1.1 | 1.6 | 1.0 | 0.8 | 0.7 |
| Ccl8 | 1.0 | 1.0 | 0.9 | 0.3 | 1.0 | 0.5 | 1.0 | 2.7 | 1.0 | 1.0 | 0.6 | 1.0 | 1.5 | 1.2 | 6.3 | 0.4 | 1.6 | 1.7 | 0.8 | 0.6 | 1.5 | 0.7 |
| Ccnb1 | 1.0 | 1.0 | 0.8 | 0.9 | 1.0 | 1.0 | 1.0 | 1.0 | 1.0 | 1.0 | 1.0 | 1.0 | 0.4 | 0.7 | 1.0 | 1.0 | 1.0 | 0.8 | 1.2 | 1.0 | 1.1 | 1.1 |
| Ccne2 | 1.0 | 1.0 | 0.8 | 0.7 | 1.0 | 1.4 | 1.0 | 1.0 | 1.0 | 1.0 | 1.0 | 1.0 | 0.3 | 0.5 | 1.0 | 1.0 | 0.9 | 1.9 | 1.0 | 0.7 | 0.7 | 0.4 |
| Ccno | 1.0 | 1.0 | 1.0 | 1.0 | 1.0 | 1.0 | 1.0 | 1.0 | 0.8 | 1.0 | 1.0 | 1.0 | 1.9 | 1.0 | 21.2 | 1.0 | 1.0 | 1.0 | 1.0 | 1.0 | 1.0 | 1.0 |
| Cd19 | 1.0 | 1.0 | 0.4 | 0.3 | 1.0 | 1.0 | 1.0 | 1.6 | 1.0 | 1.0 | 0.6 | 1.3 | 1.5 | 0.9 | 1.0 | 1.0 | 1.0 | 1.0 | 0.8 | 0.7 | 0.8 | 0.8 |
| Cd22 | 1.0 | 1.0 | 0.4 | 0.2 | 1.0 | 1.0 | 1.0 | 1.0 | 1.0 | 1.0 | 0.6 | 2.0 | 1.7 | 1.1 | 1.0 | 1.0 | 1.0 | 1.2 | 0.6 | 0.6 | 0.7 | 1.0 |
| Cd27 | 1.0 | 1.0 | 0.8 | 0.6 | 1.0 | 1.0 | 1.0 | 1.0 | 1.0 | 1.0 | 0.9 | 1.0 | 0.8 | 0.9 | 0.9 | 0.9 | 1.0 | 1.0 | 1.3 | 0.8 | 0.9 | 0.6 |
| Cd300ln | 0.7 | 1.0 | 0.5 | 0.5 | 1.0 | 1.0 | 1.2 | 0.3 | 1.0 | 1.0 | 0.6 | 1.6 | 0.6 | 0.5 | 0.4 | 0.4 | 0.6 | 0.8 | 1.0 | 1.0 | 1.0 | 1.0 |
| Cd3e | 1.0 | 1.0 | 0.8 | 0.7 | 1.0 | 1.0 | 1.0 | 1.4 | 1.0 | 1.0 | 0.6 | 0.8 | 1.0 | 1.0 | 1.0 | 1.0 | 0.9 | 0.8 | 0.8 | 0.5 | 0.5 | 0.5 |
| Cd4 | 1.0 | 1.0 | 1.0 | 0.4 | 1.0 | 0.8 | 1.0 | 1.0 | 0.9 | 0.8 | 0.9 | 1.4 | 0.7 | 0.8 | 0.9 | 0.7 | 1.0 | 0.9 | 1.0 | 0.9 | 0.5 | 0.5 |
| Cd52 | 1.0 | 2.4 | 0.6 | 0.3 | 1.0 | 0.9 | 1.4 | 1.2 | 0.8 | 1.4 | 0.5 | 0.8 | 1.2 | 0.9 | 3.8 | 2.0 | 1.1 | 2.3 | 1.0 | 1.1 | 1.0 | 0.5 |
| Cd5l | 1.0 | 1.0 | 1.0 | 1.0 | 1.0 | 1.7 | 1.0 | 1.0 | 1.1 | 1.2 | 1.0 | 1.0 | 2.0 | 1.1 | 1.0 | 0.6 | 1.0 | 1.0 | 1.0 | 1.0 | 1.0 | 1.0 |
| Cd79a | 1.0 | 1.0 | 0.5 | 0.3 | 1.0 | 1.0 | 1.0 | 1.0 | 1.0 | 1.0 | 0.7 | 2.1 | 2.3 | 1.0 | 0.8 | 0.8 | 1.0 | 1.2 | 1.0 | 0.8 | 0.8 | 1.0 |
| Cd79b | 0.8 | 0.8 | 0.5 | 0.3 | 1.0 | 1.0 | 1.0 | 0.8 | 0.6 | 0.6 | 0.5 | 2.5 | 1.2 | 1.0 | 0.4 | 1.2 | 1.0 | 1.4 | 0.9 | 0.8 | 0.7 | 0.6 |
| Cd8a | 1.0 | 1.0 | 0.9 | 0.8 | 1.0 | 1.0 | 1.0 | 1.0 | 1.0 | 1.0 | 1.0 | 1.1 | 0.6 | 0.7 | 1.0 | 1.0 | 1.0 | 1.0 | 1.0 | 0.8 | 0.6 | 0.6 |
| Cd8b1 | 1.0 | 1.0 | 0.6 | 0.4 | 1.0 | 1.0 | 1.0 | 1.0 | 1.0 | 1.0 | 1.0 | 1.5 | 0.6 | 0.8 | 1.0 | 1.0 | 1.0 | 1.0 | 1.0 | 0.8 | 1.2 | 0.4 |
| Cdrp1 | 1.1 | 1.0 | 1.0 | 1.0 | 1.2 | 0.8 | 1.0 | 1.0 | 1.1 | 0.7 | 0.9 | 1.3 | 1.5 | 5.9 | 1.0 | 0.8 | 1.3 | 1.3 | 1.0 | 0.6 | 1.1 | 1.4 |
| Cdh3 | 1.5 | 2.2 | 1.0 | 1.0 | 1.2 | 1.0 | 1.0 | 1.0 | 1.0 | 0.9 | 0.9 | 0.7 | 1.9 | 1.7 | 5.4 | 1.0 | 0.9 | 1.3 | 1.0 | 1.0 | 1.5 | 1.3 |
| Cdx6 | 1.0 | 0.8 | 0.9 | 1.2 | 1.0 | 0.9 | 0.5 | 0.6 | 2.5 | 0.8 | 1.0 | 1.0 | 0.2 | 0.3 | 1.0 | 1.0 | 0.9 | 1.5 | 0.5 | 0.4 | 1.1 | 1.2 |
| Ceacam10 | 1.0 | 1.0 | 1.2 | 0.7 | 0.9 | 1.0 | 1.0 | 1.0 | 1.0 | 1.0 | 1.3 | 1.4 | 1.0 | 1.0 | 11.0 | 1.9 | 1.0 | 0.7 | 2.5 | 1.9 | 1.5 | 1.1 |
| Cel | 0.9 | 1.1 | 1.0 | 73.9 | 1.0 | 1.0 | 1.0 | 1.0 | 1.0 | 0.9 | 1.0 | 1.0 | 1.0 | 0.4 | 1.0 | 1.0 | 13.2 | 0.1 | 0.6 | 1.0 | 1.0 | 1.0 |
| Cela1 | 0.5 | 0.9 | 1.0 | 2.3 | 1.1 | 1.3 | 1.0 | 1.6 | 0.0 | 0.3 | 0.7 | 1.0 | 1.1 | 0.3 | 1.0 | 0.8 | 5.5 | 0.2 | 0.1 | 1.4 | 1.0 | 1.1 |
| Cela2a | 3.3 | 0.8 | 1.3 | 98.2 | 1.0 | 1.0 | 1.0 | 1.6 | 1.0 | 0.8 | 1.3 | 1.0 | 1.0 | 0.3 | 1.0 | 1.0 | 220.7 | 0.0 | 0.6 | 1.0 | 0.7 | 1.0 |

[Fig. 23-18]

The image shows a large data table with gene expression values. Due to the density and low resolution of the table, values are approximate.

| | | | | | | | | | | | | | | | | | | | | | | |
|---|---|---|---|---|---|---|---|---|---|---|---|---|---|---|---|---|---|---|---|---|---|---|
| Cela3b | 1.0 | 0.9 | 2.2 | 89.5 | 1.0 | 1.0 | 1.0 | 1.0 | 1.0 | 0.8 | 1.1 | 1.0 | 1.0 | 0.4 | 1.0 | 1.0 | 154.8 | 0.1 | 0.0 | 1.0 | 1.0 | 1.0 |
| Ces1c | 1.0 | 1.0 | 1.0 | 1.0 | 1.0 | 1.0 | 1.0 | 1.0 | 1.4 | 1.9 | 1.0 | 1.0 | 1.0 | 1.0 | 1.0 | 1.0 | 5.9 | 0.5 | 1.0 | 1.0 | 0.9 | 1.1 |
| Ces1g | 0.3 | 0.3 | 1.3 | 1.3 | 1.0 | 1.0 | 1.0 | 1.0 | 1.4 | 2.4 | 1.0 | 1.0 | 1.0 | 1.0 | 1.0 | 1.0 | 1.3 | 0.9 | 2.2 | 2.7 | 1.6 | 0.8 |
| Ces2g | 1.3 | 1.1 | 0.8 | 1.1 | 1.0 | 1.3 | 1.0 | 1.5 | 1.0 | 0.8 | 1.0 | 1.0 | 1.5 | 1.3 | 0.7 | 0.7 | 1.0 | 0.9 | 1.0 | 1.1 | 1.0 | 1.3 |
| Ces3a | 1.0 | 1.0 | 1.0 | 1.0 | 1.0 | 1.0 | 1.0 | 1.0 | 0.0 | 0.1 | 1.0 | 1.0 | 1.0 | 1.0 | 1.0 | 1.0 | 1.0 | 0.3 | 1.0 | 1.0 | 1.0 | 1.0 |
| Ces3b | 1.0 | 1.0 | 1.0 | 1.0 | 1.0 | 1.0 | 1.0 | 1.0 | 0.0 | 0.3 | 1.0 | 1.0 | 1.0 | 1.0 | 1.0 | 1.0 | 1.0 | 1.0 | 1.0 | 1.0 | 1.0 | 1.0 |
| Ces5a | 1.0 | 1.0 | 1.0 | 1.0 | 0.9 | 1.2 | 1.0 | 1.0 | 1.0 | 1.0 | 1.0 | 1.0 | 1.0 | 1.0 | 7.7 | 1.0 | 1.0 | 1.0 | 1.0 | 1.0 | 1.0 | 1.0 |
| Cfd | 2.1 | 0.8 | 1.1 | 2.0 | 0.3 | 0.5 | 1.4 | 1.3 | 1.0 | 0.7 | 1.7 | 3.0 | 3.4 | 4.9 | 1.1 | 1.8 | 0.9 | 1.1 | 2.1 | 1.9 | 1.7 | 1.7 |
| Cgref1 | 0.9 | 1.0 | 0.9 | 0.8 | 0.8 | 1.2 | 1.0 | 0.7 | 1.4 | 1.1 | 0.8 | 1.0 | 1.0 | 1.0 | 0.4 | 1.5 | 1.4 | 1.0 | 0.8 | 1.2 | 1.1 | 0.9 |
| Chac1 | 0.7 | 0.8 | 0.5 | 0.4 | 0.8 | 0.9 | 0.5 | 1.3 | 0.4 | 0.6 | 0.3 | 1.4 | 1.0 | 1.0 | 0.7 | 1.5 | 0.9 | 1.3 | 0.5 | 0.7 | 0.7 | 0.4 |
| Chga | 1.0 | 1.0 | 0.8 | 1.0 | 1.0 | 1.0 | 1.0 | 0.7 | 1.0 | 1.0 | 1.0 | 1.0 | 5.6 | 4.8 | 1.0 | 1.0 | 1.9 | 1.3 | 0.8 | 1.1 | 0.8 | 0.9 |
| Chrna4 | 0.8 | 0.9 | 1.0 | 1.0 | 1.1 | 1.0 | 1.0 | 1.0 | 2.1 | 0.2 | 1.0 | 1.0 | 1.0 | 1.0 | 1.0 | 1.0 | 1.0 | 1.0 | 1.0 | 1.0 | 1.6 | 1.0 |
| Chst11 | 0.5 | 0.2 | 1.4 | 1.5 | 0.6 | 0.3 | 1.2 | 1.1 | 1.0 | 1.0 | 0.8 | 1.0 | 1.2 | 1.3 | 1.0 | 1.1 | 1.1 | 1.4 | 0.7 | 0.8 | 0.9 | 1.1 |
| Cib3 | 1.0 | 1.0 | 1.0 | 1.0 | 1.0 | 1.0 | 1.0 | 0.9 | 0.8 | 0.3 | 1.0 | 1.0 | 1.0 | 1.0 | 1.0 | 1.0 | 1.0 | 1.0 | 1.0 | 1.0 | 1.0 | 1.0 |
| Cited4 | 1.0 | 1.0 | 1.0 | 1.0 | 0.3 | 0.7 | 1.6 | 1.0 | 1.0 | 1.0 | 1.0 | 2.8 | 0.9 | 3.0 | 0.4 | 0.5 | 0.9 | 0.9 | 1.0 | 1.0 | 1.0 | 1.0 |
| Ckb | 1.0 | 1.0 | 1.1 | 0.7 | 0.8 | 0.8 | 0.7 | 1.0 | 1.0 | 1.0 | 0.4 | 0.3 | 1.3 | 1.3 | 0.7 | 0.5 | 2.2 | 3.4 | 0.9 | 0.8 | 0.9 | 1.1 |
| Ckb2 | 1.0 | 1.0 | 1.0 | 1.0 | 0.7 | 0.5 | 0.7 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ckmed1 | 1.0 | 1.0 | 1.0 | 1.0 | 0.8 | 0.9 | 1.6 | 1.1 | 1.0 | 1.0 | 1.0 | 1.0 | 1.0 | 1.0 | 12.8 | 8.5 | 1.0 | 1.0 | 1.0 | 1.0 | 1.0 | 1.0 |
| Ckmed4 | 1.7 | 0.9 | 1.1 | 0.9 | 0.9 | 0.9 | 1.2 | 0.6 | 1.0 | 1.0 | 1.1 | 1.0 | 1.2 | 1.4 | 5.4 | 4.2 | 1.3 | 1.1 | 1.0 | 1.0 | 0.7 | 0.7 |
| Ckm | 1.0 | 1.0 | 1.0 | 1.0 | 0.7 | 0.5 | 0.9 | 1.1 | 1.0 | 1.0 | 6.0 | 7.3 | 0.4 | 0.8 | 1.8 | 1.5 | 0.7 | 1.0 | 1.5 | 1.5 | 0.6 | 1.0 |
| Ckmt2 | 1.0 | 1.0 | 2.0 | 2.7 | 0.7 | 0.8 | 0.9 | 1.1 | 1.0 | 1.0 | 1.0 | 3.0 | 1.0 | 1.0 | 1.0 | 1.0 | 1.0 | 1.0 | 1.0 | 1.0 | 1.0 | 1.0 |
| Clca5 | 1.0 | 1.0 | 0.2 | 0.3 | 0.9 | 0.7 | 1.0 | 1.0 | 1.0 | 1.0 | 1.0 | 1.0 | 1.1 | 1.0 | 1.0 | 1.0 | 0.6 | 0.5 | 1.1 | 1.2 | 0.8 | 1.1 |
| Cldn3 | 1.2 | 1.7 | 1.3 | 1.0 | 1.4 | 1.4 | 1.0 | 1.0 | 1.1 | 0.6 | 1.0 | 0.7 | 1.7 | 1.4 | 7.1 | 1.6 | 1.0 | 1.0 | 1.0 | 1.0 | 1.0 | 1.0 |
| Cldn13 | 1.0 | 1.0 | 1.0 | 1.0 | 1.0 | 1.0 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 |
| Cldn14 | 1.0 | 1.0 | 1.1 | 1.2 | 1.0 | 1.0 | 1.0 | 1.0 | 0.8 | 0.6 | 1.0 | 1.0 | 1.0 | 1.0 | 17.9 | 1.0 | 1.0 | 1.0 | 1.0 | 1.0 | 1.0 | 1.0 |
| Cldn2 | 0.9 | 0.9 | 2.1 | 1.7 | 1.2 | 1.5 | 1.0 | 1.0 | 1.1 | 0.6 | 1.0 | 1.0 | 1.0 | 1.0 | 5.7 | 6.3 | 2.1 | 1.6 | 1.4 | 1.2 | 1.3 | 1.4 |
| Cldn22 | 1.0 | 0.9 | 1.0 | 1.0 | 0.8 | 1.2 | 1.0 | 1.0 | 1.0 | 1.0 | 2.6 | 8.7 | 1.0 | 1.0 | 1.7 | 2.8 | 1.3 | 0.9 | 1.0 | 1.0 | 1.0 | 1.0 |
| Cldn34 | 1.0 | 1.0 | 1.0 | 1.0 | 1.0 | 1.0 | 1.0 | 1.0 | 1.0 | 1.0 | 3.4 | 12.9 | 1.0 | 1.0 | 1.6 | 2.4 | 1.0 | 1.0 | 1.0 | 1.0 | 1.0 | 1.0 |
| Cldn3 | 1.2 | 1.2 | 1.0 | 1.1 | 1.1 | 0.9 | 1.0 | 1.0 | 0.7 | 0.7 | 1.2 | 0.8 | 3.2 | 3.4 | 11.1 | 4.1 | 2.5 | 0.8 | 1.5 | 1.3 | 1.1 | 1.3 |
| Cldn4 | 1.7 | 1.8 | 0.9 | 1.9 | 1.1 | 1.0 | 1.0 | 1.0 | 1.0 | 1.0 | 0.3 | 0.9 | 1.0 | 0.8 | 40.9 | 2.7 | 1.1 | 1.3 | 0.7 | 2.7 | 1.7 | 1.3 |

| | Kidney | | Colon | | Eyeball | | Heart | | Liver | | SG | | Thymus | | Adipose | | Stomach | | Jejunum | | Ileum | |
|---|---|---|---|---|---|---|---|---|---|---|---|---|---|---|---|---|---|---|---|---|---|---|
| | E | M | E | M | E | M | E | M | E | M | E | M | E | M | E | M | E | M | E | M | E | M |
| Cldn7 | 1.4 | 1.6 | 1.0 | 1.0 | 1.0 | 1.0 | 1.0 | 1.0 | 1.1 | 1.1 | 1.0 | 0.8 | 1.7 | 0.7 | 5.4 | 5.8 | 1.5 | 0.9 | 1.3 | 1.5 | 1.1 | 0.9 |
| Cldn8 | 1.1 | 1.1 | 1.4 | 1.0 | 1.0 | 1.0 | 1.0 | 1.0 | 1.0 | 1.0 | 1.0 | 1.2 | 1.0 | 1.0 | 24.2 | 3.3 | 1.0 | 1.1 | 1.0 | 1.0 | 0.5 | 0.6 |
| Clec11a | 0.7 | 0.9 | 0.8 | 0.9 | 0.6 | 0.7 | 1.0 | 0.6 | 1.0 | 0.8 | 0.6 | 0.9 | 1.4 | 1.9 | 2.0 | 1.2 | 1.2 | 0.9 | 1.0 | 1.0 | 1.0 | 1.0 |
| Clec2h | 0.7 | 0.6 | 1.0 | 1.0 | 1.0 | 1.0 | 1.0 | 1.0 | 0.9 | 0.2 | 1.0 | 1.0 | 1.0 | 1.0 | 1.0 | 1.0 | 1.0 | 1.0 | 1.3 | 2.1 | 1.2 | 8.9 |
| Clec2i | 1.0 | 1.0 | 1.0 | 1.0 | 1.0 | 1.2 | 0.8 | 1.0 | 1.0 | 1.0 | 1.0 | 1.0 | 1.0 | 1.0 | 5.3 | 1.0 | 1.0 | 1.0 | 1.0 | 1.0 | 1.0 | 1.0 |
| Clec7a | 1.0 | 6.5 | 1.2 | 0.9 | 1.1 | 1.3 | 1.0 | 1.9 | 0.5 | 1.1 | 0.7 | 0.7 | 1.1 | 0.9 | 0.8 | 0.7 | 1.9 | 5.9 | 0.9 | 0.9 | 0.9 | 0.9 |
| Clhc1 | 1.0 | 1.0 | 0.6 | 0.8 | 1.0 | 1.0 | 1.0 | 1.0 | 1.0 | 1.0 | 1.0 | 0.5 | 0.6 | 1.0 | 1.8 | 1.0 | 1.4 | 0.7 | 1.6 | 1.0 | 1.0 | 0.8 |
| Clps | 0.9 | 1.2 | 1.0 | 1.9 | 1.0 | 1.3 | 1.0 | 0.6 | 0.7 | 0.9 | 0.9 | 0.8 | 1.0 | 2.4 | 1.0 | 7.0 | 0.9 | 0.9 | 0.3 | 0.8 | 0.7 | 0.6 |
| Clpsl2 | 1.0 | 1.0 | 1.0 | 1.0 | 1.0 | 1.0 | 1.0 | 1.0 | 1.0 | 1.0 | 1.0 | 1.0 | 1.0 | 1.0 | 183.5 | 1.0 | 1.0 | 1.0 | 1.0 | 3.0 | 1.0 | 1.0 |
| Clu | 1.9 | 2.7 | 0.6 | 0.4 | 1.0 | 1.1 | 1.2 | 1.2 | 0.6 | 0.8 | 0.4 | 0.7 | 2.1 | 1.3 | 25.9 | 0.9 | 0.9 | 1.1 | 0.6 | 0.7 | 0.7 | 0.7 |
| Cmah | 0.7 | 0.8 | 1.6 | 1.7 | 0.8 | 1.1 | 1.0 | 1.6 | 0.5 | 0.3 | 1.0 | 1.0 | 0.5 | 0.7 | 0.6 | 0.6 | 1.0 | 1.0 | 0.9 | 0.8 | 0.7 | 1.1 |
| Cml5 | 1.0 | 0.6 | 1.7 | 1.5 | 1.0 | 1.0 | 1.0 | 1.0 | 0.0 | 0.0 | 1.0 | 1.0 | 1.0 | 1.0 | 1.0 | 1.0 | 1.0 | 1.0 | 1.3 | 1.4 | 2.4 | 1.7 |
| Cmya5 | 1.0 | 1.0 | 1.0 | 1.0 | 1.0 | 0.6 | 0.9 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cnfn | 1.0 | 1.0 | 1.0 | 1.0 | 1.0 | 1.6 | 1.0 | 1.0 | 1.0 | 1.0 | 1.0 | 1.0 | 1.0 | 1.0 | 1.0 | 1.0 | 1.0 | 1.0 | 1.0 | 1.2 | 1.0 | 1.0 |
| Cnn1 | 0.8 | 1.2 | 1.0 | 0.9 | 0.7 | 0.8 | 2.9 | 1.0 | 1.0 | 1.0 | 0.7 | 0.6 | 1.0 | 1.0 | 2.2 | 8.0 | 1.4 | 1.1 | 1.2 | 0.7 | 0.9 | 0.8 |
| Col15a1 | 0.6 | 1.3 | 0.9 | 0.6 | 0.8 | 0.6 | 0.5 | 0.5 | 1.1 | 0.7 | 0.4 | 0.5 | 1.1 | 1.2 | 0.4 | 0.4 | 1.0 | 1.2 | 0.8 | 0.7 | 0.6 | 1.0 |
| Col1a1 | 0.8 | 1.9 | 1.0 | 0.6 | 0.8 | 0.6 | 0.7 | 0.5 | 0.8 | 0.5 | 0.0 | 0.3 | 0.7 | 1.2 | 0.5 | 0.5 | 1.4 | 1.4 | 1.5 | 1.0 | 0.9 | 1.0 |
| Col1a2 | 0.8 | 1.8 | 1.0 | 0.7 | 0.7 | 0.8 | 0.7 | 0.7 | 0.6 | 0.7 | 0.3 | 0.4 | 0.8 | 1.3 | 0.5 | 0.5 | 1.1 | 1.3 | 1.1 | 0.9 | 0.8 | 0.9 |
| Col3a1 | 0.8 | 2.7 | 0.9 | 0.5 | 0.4 | 0.4 | 0.5 | 0.4 | 0.5 | 0.5 | 0.1 | 0.2 | 0.5 | 0.7 | 0.3 | 0.4 | 1.2 | 1.3 | 1.0 | 0.9 | 0.8 | 0.7 |
| Col5a1 | 1.1 | 1.6 | 1.2 | 0.7 | 0.8 | 0.6 | 0.6 | 0.8 | 1.0 | 1.0 | 0.8 | 0.7 | 1.1 | 1.3 | 0.4 | 0.5 | 1.4 | 1.4 | 1.3 | 0.9 | 1.0 | 1.0 |
| Col5a2 | 1.0 | 1.8 | 1.2 | 0.6 | 0.8 | 0.8 | 0.7 | 0.6 | 1.0 | 1.0 | 0.7 | 0.9 | 1.1 | 1.1 | 0.3 | 0.5 | 1.2 | 1.4 | 0.8 | 0.9 | 0.8 | 1.2 |
| Col6a2 | 0.8 | 1.5 | 1.1 | 0.7 | 0.7 | 0.7 | 0.6 | 0.6 | 0.8 | 0.7 | 0.3 | 0.4 | 1.3 | 1.2 | 0.4 | 0.4 | 1.2 | 1.3 | 1.2 | 1.0 | 0.6 | 1.0 |
| Col6a3 | 1.0 | 1.1 | 0.3 | 0.6 | 0.8 | 0.7 | 0.5 | 0.4 | 1.0 | 0.8 | 0.4 | 0.6 | 1.2 | 1.3 | 0.4 | 0.3 | 1.0 | 1.3 | 1.0 | 0.7 | 0.8 | 1.2 |
| Col6a4 | 1.0 | 1.0 | 1.0 | 1.0 | 0.7 | 1.0 | 1.0 | 1.0 | 1.0 | 1.0 | 1.0 | 1.0 | 1.1 | 1.0 | 6.7 | 1.0 | 0.9 | 1.9 | 0.9 | 0.9 | 1.0 | 1.3 |
| Col6a6 | 1.0 | 1.0 | 1.0 | 1.0 | 1.0 | 1.0 | 0.6 | 0.7 | 1.0 | 1.0 | 1.0 | 1.0 | 1.0 | 1.2 | 0.8 | 0.3 | 1.0 | 1.0 | 1.0 | 1.0 | 1.0 | 1.0 |
| Cox6a2 | 0.5 | 1.0 | 1.0 | 0.7 | 0.8 | 1.2 | 1.2 | 1.0 | 1.0 | 1.0 | 1.2 | 0.8 | 1.0 | 1.0 | 1.0 | 1.0 | 1.0 | 1.0 | 1.0 | 1.0 | 1.0 | 1.0 |
| Cox7a1 | 0.8 | 0.8 | 0.4 | 1.3 | 0.6 | 0.6 | 0.9 | 0.8 | 1.0 | 1.0 | 1.4 | 1.2 | 1.0 | 1.0 | 0.7 | 1.7 | 1.2 | 1.6 | 1.8 | 0.8 | 0.7 | 1.0 |
| Cpa1 | 1.0 | 0.5 | 1.5 | 74.3 | 1.0 | 1.0 | 1.0 | 1.0 | 1.0 | 0.6 | 0.9 | 1.0 | 1.0 | 0.6 | 1.0 | 1.0 | 127.2 | 0.1 | 0.0 | 1.0 | 1.0 | 1.0 |
| Cpa2 | 1.0 | 1.0 | 1.5 | 32.4 | 1.2 | 1.4 | 1.0 | 1.0 | 1.0 | 1.0 | 1.0 | 1.0 | 1.0 | 1.0 | 1.0 | 1.0 | 32.5 | 0.0 | 0.1 | 1.0 | 1.0 | 1.0 |
| Cpb1 | 0.8 | 1.2 | 1.4 | 55.5 | 1.0 | 1.0 | 1.0 | 1.0 | 1.0 | 1.0 | 1.2 | 0.7 | 0.8 | 1.0 | 1.0 | 0.6 | 1.0 | 1.0 | 95.1 | 0.0 | 0.0 | 1.0 | 0.9 | 1.0 |
| Cpz | 1.0 | 1.0 | 1.0 | 1.0 | 1.0 | 0.8 | 1.0 | 1.0 | 1.0 | 1.0 | 1.0 | 1.0 | 1.0 | 1.0 | 1.1 | 1.1 | 1.0 | 1.0 | 1.0 | 1.0 | 1.0 | 1.0 |
| Crb3 | 1.1 | 1.0 | 1.1 | 1.2 | 0.7 | 1.0 | 1.0 | 1.0 | 0.9 | 1.5 | 0.6 | 0.8 | 2.0 | 1.0 | 5.4 | 2.2 | 1.0 | 0.9 | 1.1 | 1.3 | 1.1 | 1.0 |
| Cre1 | 1.0 | 1.0 | 1.0 | 1.0 | 3.2 | 1.8 | 1.0 | 1.0 | 1.0 | 1.0 | 1.0 | 1.0 | 2.3 | 0.8 | 1.0 | 1.0 | 1.0 | 0.9 | 1.0 | 1.0 | 1.0 | 1.0 |
| Crisp1 | 1.0 | 1.0 | 1.0 | 1.0 | 1.0 | 1.0 | 1.0 | 1.0 | 1.0 | 1.0 | 0.2 | 0.3 | 1.0 | 1.0 | 4.5 | 82.0 | 1.0 | 1.0 | 1.0 | 1.0 | 1.0 | 1.0 |
| Crisp4 | 1.0 | 1.0 | 1.0 | 1.0 | 1.0 | 1.0 | 1.0 | 1.0 | 1.0 | 1.0 | 1.0 | 1.0 | 1.0 | 1.0 | 19.3 | 1.0 | 1.0 | 1.0 | 1.0 | 1.0 | 1.0 | 1.0 |
| Cryaa | 0.4 | 0.7 | 3.2 | 1.0 | 1.0 | 1.1 | 1.1 | 1.4 | 1.0 | 1.0 | 1.0 | 1.0 | 0.7 | 4.1 | 0.9 | 5.6 | 1.0 | 0.4 | 1.0 | 1.0 | 1.0 | 1.0 |
| Cryba2 | 1.0 | 1.0 | 1.0 | 1.0 | 1.0 | 0.9 | 1.0 | 1.0 | 1.0 | 1.0 | 1.0 | 1.0 | 0.9 | 1.7 | 1.0 | 1.0 | 1.0 | 1.0 | 1.0 | 1.0 | 1.0 | 1.0 |
| Cryba4 | 1.0 | 1.0 | 1.4 | 1.0 | 1.0 | 1.1 | 0.6 | 1.0 | 1.0 | 1.0 | 1.0 | 1.0 | 1.0 | 1.0 | 67.6 | 1.0 | 1.0 | 1.0 | 1.0 | 0.7 | 1.0 | 1.0 |
| Crybb3 | 1.0 | 1.0 | 1.2 | 1.0 | 0.9 | 1.0 | 1.0 | 1.0 | 1.0 | 1.0 | 1.0 | 1.0 | 1.0 | 1.0 | 1.0 | 0.7 | 1.0 | 0.7 | 1.5 | 0.3 | 0.2 | |
| Crygc | 1.0 | 1.0 | 1.6 | 1.0 | 1.0 | 1.1 | 1.0 | 0.7 | 1.0 | 1.0 | 1.0 | 1.0 | 1.0 | 1.0 | 1.0 | 5.8 | 1.0 | 0.9 | 1.0 | 1.0 | 1.0 | 1.0 |
| Csad | 0.7 | 0.6 | 1.0 | 1.4 | 1.0 | 1.1 | 1.2 | 0.8 | 11.0 | 16.0 | 1.1 | 0.8 | 1.4 | 1.2 | 0.8 | 1.2 | 1.2 | 1.0 | 0.9 | 1.0 | 1.0 | 0.9 |
| Csrp3 | 1.0 | 1.0 | 1.0 | 1.0 | 0.6 | 1.0 | 0.9 | 1.1 | 0.5 | 1.4 | 1.0 | 1.0 | 1.0 | 1.0 | 1.0 | 1.0 | 1.3 | 1.0 | 1.0 | 1.6 | 1.0 | 1.0 |
| Cst11 | 1.0 | 1.0 | 1.0 | 1.0 | 1.0 | 1.0 | 1.0 | 1.0 | 1.0 | 1.0 | 1.0 | 1.0 | 1.0 | 1.0 | 650.5 | 1.0 | 0.7 | 1.0 | 1.0 | 1.0 | 1.0 | 1.0 |
| Cst12 | 1.0 | 1.0 | 1.0 | 1.0 | 1.0 | 1.0 | 1.0 | 1.0 | 1.0 | 1.0 | 1.0 | 1.0 | 1.0 | 1.0 | 337.0 | 1.0 | 1.0 | 1.0 | 1.0 | 1.0 | 1.0 | 1.0 |
| Cst6 | 1.0 | 1.0 | 1.0 | 1.0 | 1.0 | 0.9 | 1.0 | 1.0 | 1.0 | 1.0 | 0.8 | 0.3 | 2.3 | 0.8 | 1.0 | 1.0 | 0.9 | 1.0 | 1.0 | 1.2 | 1.1 | 0.9 |
| Cst8 | 1.0 | 1.0 | 1.0 | 1.0 | 1.0 | 1.0 | 1.0 | 1.0 | 1.0 | 1.0 | 1.0 | 1.0 | 1.0 | 1.0 | 415.6 | 1.0 | 2.7 | 1.0 | 1.0 | 1.0 | 1.0 | 1.0 |
| Cthrc1 | 1.0 | 1.0 | 1.0 | 1.0 | 0.7 | 0.8 | 1.5 | 1.0 | 1.0 | 1.0 | 0.9 | 1.4 | 1.0 | 1.0 | 0.9 | 1.2 | 2.1 | 1.1 | 1.0 | 1.0 | 1.0 | 1.0 |
| Cogb1a1 | 0.9 | 1.2 | 1.9 | 553.0 | 1.0 | 1.0 | 1.0 | 0.9 | 0.7 | 0.5 | 1.0 | 1.0 | 0.1 | 1.0 | 1.0 | 203.6 | 0.1 | 0.0 | 0.3 | 1.1 | 1.0 |
| Ctrl | 1.0 | 0.7 | 1.0 | 34.8 | 1.0 | 1.0 | 1.0 | 1.0 | 0.5 | 0.9 | 1.0 | 1.0 | 0.4 | 1.0 | 1.0 | 77.6 | 0.0 | 0.0 | 1.0 | 1.1 | 1.0 |
| Ctxn3 | 0.6 | 0.2 | 1.0 | 1.0 | 0.8 | 1.2 | 1.0 | 1.0 | 1.0 | 1.0 | 1.0 | 1.0 | 1.0 | 1.0 | 0.6 | 1.0 | 1.3 | 1.1 | 1.3 | 1.1 | 0.9 | 1.1 |
| Cux2 | 1.0 | 1.0 | 1.0 | 1.0 | 1.1 | 0.8 | 0.8 | 0.9 | 15.2 | 8.3 | 1.0 | 1.0 | 1.0 | 1.0 | 1.0 | 1.0 | 1.0 | 1.0 | 1.0 | 1.0 | 1.0 | 1.0 |
| Cuzd1 | 1.0 | 1.0 | 1.5 | 1.7 | 1.0 | 1.0 | 1.0 | 1.0 | 1.0 | 1.0 | 1.0 | 1.0 | 1.0 | 1.0 | 7.3 | 6.0 | 5.1 | 0.2 | 0.5 | 1.0 | 1.0 | 1.0 |

[Fig. 23-19]

| | | | | | | | | | | | | | | | | | | | | | | | |
|---|---|---|---|---|---|---|---|---|---|---|---|---|---|---|---|---|---|---|---|---|---|---|---|
| Cxcl1 | 4.5 | 7.1 | 1.0 | 1.0 | 1.0 | 1.0 | 2.3 | 1.0 | 0.5 | 1.1 | 1.0 | 1.0 | 1.0 | 1.0 | 0.4 | 0.3 | 1.0 | 1.0 | 1.0 | 1.0 | 1.0 | 1.0 |
| Cxcl13 | 1.0 | 1.0 | 1.2 | 0.5 | 1.1 | 1.0 | 3.8 | 2.2 | 4.5 | 1.8 | 0.8 | 2.5 | 1.8 | 1.6 | 1.1 | 1.6 | 1.6 | 0.7 | 0.9 | 0.9 | 0.8 | 0.6 |
| Cxcr5 | 1.0 | 1.0 | 0.4 | 0.2 | 1.0 | 1.0 | 1.9 | 1.6 | 1.0 | 1.0 | 0.9 | 3.3 | 1.5 | 1.0 | 1.0 | 1.0 | 1.0 | 1.0 | 1.0 | 0.9 | 0.7 | 0.9 |
| Cyb561 | 0.9 | 1.0 | 1.7 | 1.0 | 1.0 | 1.0 | 1.3 | 1.0 | 0.7 | 1.2 | 1.1 | 0.9 | 1.5 | 1.3 | 5.8 | 1.2 | 1.1 | 1.0 | 1.1 | 1.3 | 1.1 | 1.0 |
| Cym | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 7.5 | 0.6 | 0.7 | 1.0 | 1.0 | 1.0 |
| Cyp1a1 | 1.0 | 1.0 | 1.2 | 1.5 | 1.0 | 1.0 | 4.3 | 3.1 | 1.6 | 1.5 | 1.0 | 1.0 | 1.0 | 1.0 | 2.9 | 3.4 | 0.8 | 0.8 | 2.4 | 1.4 | 0.3 | 1.8 |
| Cyp26b1 | 3.4 | 2.3 | 1.9 | 1.8 | 1.1 | 1.1 | 2.7 | 2.1 | 1.9 | 5.4 | 1.0 | 1.0 | 0.9 | 1.0 | 1.4 | 1.9 | 1.1 | 1.7 | 1.4 | 2.0 | 1.7 | 2.1 |
| Cyp27b1 | 10.8 | 27.2 | 1.0 | 1.0 | 1.0 | 1.0 | 1.0 | 1.0 | 1.0 | 1.0 | 1.0 | 1.0 | 1.0 | 1.0 | 1.9 | 1.0 | 0.9 | 1.1 | 1.0 | 1.0 | 1.0 | 1.0 |
| Cyp2a4 | 1.0 | 0.8 | 1.0 | 1.0 | 1.0 | 1.1 | 1.0 | 1.0 | 8.5 | 26.0 | 1.0 | 1.0 | 1.2 | 1.0 | 1.0 | 1.0 | 1.0 | 1.0 | 1.0 | 1.0 | 1.0 | 1.0 |
| Cyp2b6 | 2.2 | 2.0 | 1.0 | 1.0 | 0.8 | 1.5 | 1.0 | 1.0 | 2.5 | 4.1 | 1.9 | 1.4 | 2.5 | 1.4 | 1.0 | 1.0 | 7.5 | 0.5 | 1.0 | 1.0 | 1.0 | 1.0 |
| Cyp2b9 | 1.0 | 1.2 | 1.0 | 1.0 | 1.0 | 1.0 | 1.0 | 1.0 | 26.8 | 106.3 | 1.0 | 1.0 | 1.0 | 1.0 | 1.0 | 1.0 | 1.0 | 1.0 | 1.0 | 1.0 | 1.0 | 1.0 |
| Cyp2c38 | 1.0 | 1.0 | 1.0 | 1.0 | 1.0 | 1.0 | 1.0 | 1.0 | 4.0 | 7.2 | 1.0 | 1.0 | 1.0 | 1.0 | 1.0 | 1.0 | 1.0 | 1.0 | 1.0 | 1.0 | 1.0 | 1.0 |
| Cyp2c54 | 1.0 | 1.0 | 1.0 | 1.0 | 1.0 | 1.0 | 1.0 | 1.0 | 0.0 | 0.3 | 1.0 | 1.0 | 1.0 | 1.0 | 1.0 | 1.0 | 1.0 | 1.0 | 1.0 | 1.0 | 1.0 | 1.0 |
| Cyp2d12 | 0.3 | 0.2 | 1.9 | 2.1 | 1.0 | 1.0 | 1.0 | 1.0 | 0.9 | 0.1 | 1.0 | 1.0 | 1.0 | 1.0 | 1.0 | 1.0 | 1.0 | 1.0 | 1.0 | 1.0 | 1.0 | 1.0 |
| Cyp2d40 | 1.0 | 1.0 | 1.0 | 1.6 | 1.0 | 1.0 | 1.0 | 1.0 | 0.4 | 0.2 | 1.0 | 1.0 | 1.0 | 1.0 | 1.0 | 1.0 | 1.0 | 1.0 | 1.0 | 1.0 | 1.0 | 1.0 |
| Cyp2d9 | 1.9 | 1.1 | 1.4 | 1.0 | 1.0 | 1.0 | 1.0 | 1.0 | 0.0 | 0.1 | 1.0 | 1.0 | 1.2 | 1.0 | 0.9 | 1.0 | 1.2 | 0.2 | 1.0 | 1.0 | 1.0 | 1.0 |
| Cyp2e1 | 0.7 | 0.6 | 1.0 | 2.7 | 0.1 | 0.2 | 3.3 | 1.6 | 0.4 | 0.5 | 1.7 | 4.1 | 2.3 | 7.5 | 1.1 | 2.0 | 2.6 | 0.3 | 1.2 | 1.2 | 1.2 | 3.0 |
| Cyp2f2 | 0.8 | 0.6 | 3.4 | 2.3 | 0.8 | 0.9 | 1.0 | 1.0 | 0.3 | 0.6 | 1.6 | 1.5 | 3.1 | 1.5 | 1.4 | 3.0 | 1.0 | 0.9 | 1.0 | 3.0 | 1.0 | 1.0 |
| Cyp2u1 | 1.4 | 0.7 | 1.0 | 1.5 | 1.2 | 0.8 | 1.2 | 0.6 | 0.1 | 0.1 | 1.0 | 1.0 | 1.0 | 1.0 | 1.0 | 0.9 | 1.0 | 1.1 | 0.4 | 0.4 | 0.4 | 0.2 |
| Cyp39a1 | 0.9 | 1.3 | 1.1 | 1.0 | 1.0 | 1.2 | 1.0 | 0.9 | 2.5 | 6.5 | 1.2 | 0.9 | 1.0 | 1.5 | 1.1 | 1.3 | 0.9 | 0.9 | 1.2 | 0.7 | 1.0 | 1.3 |
| Cyp3a13 | 1.0 | 1.0 | 1.0 | 1.0 | 1.0 | 1.0 | 1.0 | 1.0 | 2.5 | 7.7 | 1.0 | 1.0 | 1.0 | 1.0 | 1.0 | 1.0 | 3.2 | 1.0 | 2.6 | 6.4 | 1.1 | 1.5 |
| Cyp3a44 | 1.0 | 1.0 | 1.0 | 1.0 | 1.0 | 1.0 | 1.0 | 1.0 | 3.6 | 5.6 | 1.0 | 1.0 | 1.0 | 1.0 | 1.0 | 1.0 | 1.0 | 1.0 | 1.3 | 2.0 | 1.0 | 1.2 |
| Cyp3a59 | 1.0 | 1.0 | 1.0 | 1.0 | 1.0 | 1.0 | 1.0 | 1.0 | 2.7 | 5.6 | 1.0 | 1.0 | 1.0 | 1.0 | 1.0 | 1.0 | 1.0 | 0.3 | 1.6 | 1.0 | 0.9 |
| Cyp4a12a | 0.1 | 0.1 | 1.0 | 1.0 | 1.0 | 1.0 | 1.0 | 1.0 | 0.0 | 0.0 | 1.0 | 1.0 | 1.0 | 1.0 | 1.0 | 1.0 | 1.0 | 1.0 | 1.0 | 1.0 | 1.0 | 1.0 |
| Cyp4a12b | 0.6 | 0.3 | 1.0 | 1.0 | 0.9 | 1.2 | 1.0 | 1.0 | 0.0 | 0.0 | 1.0 | 1.0 | 1.0 | 1.0 | 1.0 | 1.0 | 1.0 | 1.0 | 1.0 | 1.0 | 1.0 | 1.0 |
| Cyp4a14 | 29.9 | 42.1 | 1.0 | 1.0 | 1.0 | 1.0 | 1.0 | 1.0 | 7.8 | 51.2 | 1.0 | 1.0 | 1.0 | 1.0 | 1.0 | 1.0 | 4.1 | 1.0 | 1.0 | 1.0 | 1.0 | 1.0 |
| Cyp4b1-ps2 | 0.7 | 0.3 | 1.0 | 1.0 | 1.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Cyp7b1 | 1.0 | 0.5 | 1.0 | 1.0 | 1.2 | 1.4 | 1.0 | 1.0 | 0.1 | 0.3 | 1.0 | 1.0 | 1.4 | 1.6 | 1.0 | 1.0 | 1.4 | 0.7 | 0.7 | 0.9 | 1.1 | 1.5 |
| Cyp8b1 | 1.0 | 1.0 | 1.0 | 1.0 | 1.0 | 1.0 | 1.0 | 1.0 | 0.3 | 0.2 | 1.0 | 1.0 | 1.0 | 1.0 | 1.0 | 1.0 | 2.0 | 0.8 | 1.0 | 1.0 | 1.0 | 1.0 |
| Cysrn1 | 1.0 | 0.8 | 1.1 | 1.0 | 0.9 | 0.6 | 1.0 | 1.0 | 2.0 | 1.9 | 1.0 | 0.8 | 2.6 | 0.5 | 2.4 | 1.4 | 1.1 | 1.0 | 1.2 | 1.3 | 1.6 | 1.0 |
| Dbi15 | 0.7 | 1.0 | 1.0 | 0.8 | 0.6 | 1.2 | 0.7 | 1.0 | 1.0 | 1.0 | 1.0 | 1.0 | 1.0 | 0.9 | 12.1 | 3.5 | 0.6 | 1.0 | 1.0 | 1.0 | 1.3 | 0.9 |
| Dcpp2 | 0.7 | 1.0 | 1.0 | 1.0 | 1.0 | 0.6 | 1.0 | 0.8 | 0.9 | 1.0 | 1.0 | 1.0 | 1.2 | 1.0 | 1.5 | 1.0 | 1.6 | 1.3 | 1.0 | 1.0 | 1.0 | 1.0 |
| Dcpp3 | 1.1 | 1.0 | 1.0 | 1.0 | 1.0 | 0.5 | 1.0 | 0.6 | 0.7 | 1.0 | 1.0 | 1.1 | 1.0 | 2.1 | 1.0 | 2.1 | 1.0 | 0.5 | 1.0 | 1.0 | 1.0 | 1.0 |
| Dcstamp | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.6 | 1.0 | 1.0 | 1.0 | 1.0 | 1.0 |
| Dct | 1.0 | 1.0 | 1.0 | 1.0 | 0.9 | 1.0 | 8.7 | 0.9 | 0.3 | 0.3 | 1.0 | 1.0 | 1.0 | 1.0 | 0.7 | 1.2 | 1.0 | 1.0 | 1.0 | 1.0 | 1.0 | 1.0 |
| Scgb1b27 | 1.3 | 0.5 | 1.1 | 0.9 | 1.1 | 0.5 | 0.8 | 0.9 | 1.8 | 0.5 | 1.0 | 2.4 | 1.0 | 0.7 | 1.3 | 0.9 | 0.7 | 0.9 | 0.7 | 0.5 | 1.0 | 2.4 |
| Ddit4l | 1.7 | 1.2 | 1.0 | 1.0 | 0.7 | 0.7 | 0.9 | 0.8 | 1.0 | 1.0 | 1.1 | 1.0 | 1.6 | 1.6 | 11.7 | 1.6 | 0.9 | 0.9 | 1.0 | 1.0 | 1.0 | 1.0 |
| Defa24 | 1.0 | 1.0 | 1.0 | 1.1 | 1.0 | 1.0 | 1.0 | 1.0 | 1.0 | 1.0 | 1.0 | 1.0 | 1.0 | 1.0 | 1.0 | 0.1 | 2.5 | 1.0 | 0.5 | 1.0 | 1.0 | 0.7 |
| Defb1 | 0.8 | 1.0 | 1.0 | 1.0 | 1.3 | 1.3 | 1.0 | 1.0 | 1.3 | 3.2 | 1.0 | 1.0 | 2.7 | 1.9 | 35.2 | 1.0 | 1.1 | 1.5 | 1.0 | 1.0 | 0.7 | 1.3 |
| Defb10 | 1.0 | 1.0 | 1.0 | 1.0 | 1.0 | 1.0 | 1.0 | 1.0 | 1.0 | 1.0 | 1.0 | 1.0 | 1.0 | 1.0 | 9.3 | 1.0 | 1.0 | 1.0 | 1.0 | 1.0 | 1.0 | 1.0 |
| Defb12 | 1.0 | 1.0 | 1.0 | 1.0 | 1.0 | 1.0 | 1.0 | 1.0 | 1.0 | 1.0 | 1.0 | 1.0 | 1.0 | 1.0 | 136.1 | 1.0 | 1.0 | 1.0 | 1.0 | 1.0 | 1.0 | 1.0 |
| Defb14 | 1.0 | 1.0 | 1.0 | 1.0 | 1.0 | 1.0 | 1.0 | 1.0 | 1.0 | 1.0 | 1.0 | 1.0 | 1.0 | 1.0 | 4.6 | 1.0 | 1.3 | 1.0 | 1.0 | 1.0 | 1.0 | 1.0 |
| Defb15 | 1.0 | 1.0 | 1.0 | 1.0 | 1.0 | 0.9 | 1.0 | 1.0 | 1.0 | 1.0 | 1.0 | 1.0 | 1.0 | 1.0 | 468.1 | 1.0 | 1.0 | 1.0 | 1.0 | 1.0 | 1.0 | 1.0 |
| Defb18 | 1.0 | 1.0 | 1.0 | 1.0 | 1.0 | 1.0 | 1.0 | 1.0 | 1.0 | 1.0 | 1.0 | 1.0 | 1.0 | 1.0 | 172.1 | 1.0 | 1.0 | 1.0 | 1.0 | 1.0 | 1.0 | 1.0 |
| Defb19 | 0.2 | 0.3 | 1.0 | 1.0 | 1.0 | 1.0 | 1.0 | 1.0 | 1.0 | 1.0 | 1.0 | 1.0 | 1.0 | 1.0 | 18.1 | 1.0 | 1.0 | 1.0 | 1.0 | 1.0 | 1.0 | 1.0 |
| | Kidney | | Colon | | Eyeball | | Heart | | Liver | | SG | | Thymus | | Adipose | | Stomach | | Jejunum | | Ileum | |
| | E | M | E | M | E | M | E | M | E | M | E | M | E | M | E | M | E | M | E | M | E | M |
| Defb2 | 1.1 | 2.0 | 1.0 | 1.0 | 1.5 | 0.4 | 1.0 | 1.0 | 1.0 | 1.0 | 1.0 | 1.0 | 1.0 | 1.0 | 7.2 | 1.4 | 1.0 | 1.0 | 1.0 | 1.0 | 1.0 | 1.0 |
| Defb20 | 1.0 | 1.0 | 1.0 | 1.0 | 1.0 | 1.0 | 1.0 | 1.0 | 1.0 | 1.0 | 1.0 | 1.0 | 1.0 | 1.0 | 131.9 | 1.0 | 1.0 | 1.0 | 1.0 | 1.0 | 1.0 | 1.0 |
| Defb21 | 1.0 | 1.0 | 1.0 | 1.0 | 1.0 | 1.0 | 1.0 | 1.0 | 1.0 | 1.0 | 1.0 | 1.0 | 1.0 | 1.0 | 136.6 | 1.0 | 1.0 | 1.0 | 1.0 | 1.0 | 1.0 | 1.0 |
| Defb22 | 1.0 | 1.0 | 1.0 | 1.0 | 1.0 | 1.0 | 1.0 | 1.0 | 1.0 | 1.0 | 1.0 | 1.0 | 1.0 | 1.0 | 6.4 | 1.0 | 1.0 | 1.0 | 1.0 | 1.0 | 1.0 | 1.0 |
| Defb23 | 1.0 | 1.0 | 1.0 | 1.0 | 1.0 | 1.0 | 1.0 | 1.0 | 1.0 | 1.0 | 1.0 | 1.0 | 1.0 | 1.0 | 75.7 | 1.0 | 1.0 | 1.0 | 1.0 | 1.0 | 1.0 | 1.0 |
| Defb25 | 1.0 | 1.0 | 1.0 | 1.0 | 1.0 | 1.0 | 1.0 | 1.0 | 1.0 | 1.0 | 1.0 | 1.0 | 1.0 | 1.4 | 849.2 | 1.0 | 1.0 | 1.0 | 1.0 | 1.0 | 1.0 | 1.0 |
| Defb26 | 1.0 | 1.0 | 1.0 | 1.0 | 1.0 | 1.0 | 1.0 | 1.0 | 1.0 | 1.0 | 1.0 | 1.0 | 1.0 | 1.0 | 7.2 | 1.0 | 1.6 | 1.0 | 1.0 | 1.0 | 1.0 | 1.0 |
| Defb28 | 1.0 | 1.0 | 1.0 | 1.0 | 1.0 | 1.0 | 1.0 | 1.0 | 1.0 | 1.0 | 1.0 | 1.0 | 1.0 | 1.0 | 5.4 | 1.0 | 1.0 | 1.0 | 1.0 | 1.0 | 1.0 | 1.0 |
| Defb29 | 0.3 | 0.2 | 1.0 | 1.0 | 1.0 | 1.0 | 1.0 | 1.0 | 1.0 | 1.0 | 1.0 | 1.0 | 1.0 | 1.0 | 77.5 | 2.0 | 1.0 | 1.0 | 1.0 | 1.0 | 1.0 | 1.0 |
| Defb30 | 1.0 | 1.0 | 1.0 | 1.0 | 1.0 | 1.0 | 1.0 | 1.0 | 1.0 | 1.0 | 1.0 | 1.0 | 1.0 | 1.0 | 239.9 | 1.0 | 1.0 | 1.0 | 1.0 | 1.0 | 1.0 | 1.0 |
| Defb35 | 1.0 | 1.0 | 1.0 | 1.0 | 1.2 | 1.0 | 1.0 | 1.0 | 1.0 | 1.0 | 1.0 | 1.0 | 1.0 | 1.0 | 6.8 | 1.0 | 1.0 | 1.0 | 1.0 | 1.0 | 1.0 | 1.0 |
| Defb37 | 1.0 | 1.0 | 1.0 | 0.8 | 0.6 | 1.0 | 1.0 | 1.0 | 1.0 | 1.0 | 1.0 | 1.0 | 1.0 | 1.0 | 7.0 | 1.0 | 1.0 | 1.0 | 1.0 | 1.0 | 0.4 | 0.2 |
| Defb36 | 1.0 | 1.0 | 1.0 | 1.0 | 1.0 | 1.0 | 1.0 | 1.0 | 1.0 | 1.0 | 1.0 | 1.0 | 1.0 | 1.0 | 28.2 | 1.0 | 1.0 | 1.0 | 1.0 | 1.0 | 1.0 | 1.0 |
| Defb4 | 1.0 | 1.0 | 1.0 | 1.0 | 1.0 | 1.0 | 1.0 | 1.0 | 1.0 | 1.0 | 1.0 | 1.0 | 1.0 | 1.0 | 1.6 | 1.0 | 0.7 | 1.8 | 1.0 | 1.0 | 1.0 | 1.9 |
| Defb41 | 1.0 | 1.0 | 1.0 | 1.0 | 1.0 | 1.0 | 1.0 | 1.0 | 1.0 | 1.0 | 1.0 | 1.0 | 1.0 | 1.0 | 102.0 | 1.0 | 1.0 | 1.0 | 1.0 | 1.0 | 1.0 | 1.0 |
| Defb42 | 1.1 | 2.4 | 1.0 | 1.0 | 1.0 | 1.0 | 1.0 | 1.0 | 1.0 | 1.0 | 1.0 | 1.0 | 0.9 | 1.0 | 97.7 | 22.9 | 1.0 | 1.0 | 1.0 | 1.0 | 1.0 | 1.0 |
| Defb43 | 1.0 | 1.0 | 1.0 | 1.0 | 1.0 | 1.1 | 1.0 | 1.0 | 1.0 | 1.0 | 1.0 | 1.0 | 1.0 | 1.0 | 4.1 | 5.8 | 1.0 | 1.0 | 1.0 | 1.0 | 1.0 | 1.0 |
| Defb45 | 1.0 | 1.0 | 1.0 | 1.0 | 1.0 | 1.1 | 1.0 | 1.0 | 1.0 | 1.0 | 1.0 | 1.0 | 1.0 | 1.0 | 26.0 | 1.0 | 1.0 | 1.0 | 1.0 | 1.0 | 1.0 | 1.0 |
| Defb47 | 1.0 | 1.0 | 1.0 | 1.0 | 1.0 | 1.0 | 1.0 | 1.0 | 1.0 | 1.0 | 1.0 | 1.0 | 1.0 | 1.0 | 454.2 | 1.0 | 1.0 | 1.0 | 1.0 | 1.0 | 1.0 | 1.0 |
| Defb48 | 1.0 | 1.0 | 1.0 | 1.0 | 1.0 | 1.0 | 1.0 | 1.0 | 1.0 | 1.0 | 1.0 | 1.0 | 1.0 | 1.0 | 1265 | 1.0 | 1.0 | 1.0 | 1.0 | 1.0 | 1.0 | 1.0 |
| Defb8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Depdc7 | 0.8 | 0.7 | 1.0 | 1.0 | 1.0 | 1.1 | 1.0 | 1.0 | 0.9 | 1.2 | 1.0 | 1.0 | 1.0 | 1.0 | 5.5 | 1.0 | 1.3 | 1.0 | 0.9 | 1.0 | 1.0 | 1.0 |
| Der3 | 0.8 | 1.2 | 1.3 | 0.6 | 1.0 | 1.1 | 1.0 | 1.0 | 0.6 | 0.8 | 1.1 | 1.1 | 2.1 | 1.3 | 32.1 | 1.1 | 1.1 | 1.5 | 1.3 | 1.0 | 1.0 | 1.2 |
| Des | 0.9 | 1.1 | 1.1 | 0.9 | 0.7 | 0.8 | 1.2 | 1.3 | 1.0 | 1.4 | 1.7 | 2.2 | 1.2 | 1.2 | 1.0 | 1.6 | 1.7 | 1.2 | 1.4 | 1.1 | 0.9 | 0.9 |
| Dhrs7c | 1.0 | 1.0 | 1.0 | 1.0 | 0.5 | 0.5 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 | 3.0 |
| Dio1 | 0.3 | 0.4 | 0.7 | 0.8 | 1.0 | 1.0 | 1.0 | 1.0 | 0.0 | 0.1 | 1.1 | 1.2 | 1.3 | 0.5 | 0.7 | 1.0 | 0.5 | 0.6 | 0.6 | 0.6 | 0.7 | 0.8 |
| Dmbt1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 2.2 | 1.1 | 1.8 | 0.8 | 1.4 | 1.2 |
| Dmkn | 1.0 | 1.0 | 1.0 | 1.0 | 1.0 | 1.1 | 1.0 | 1.0 | 1.0 | 1.0 | 1.0 | 1.0 | 1.9 | 1.0 | 1.3 | 1.6 | 1.0 | 1.0 | 1.0 | 1.0 | 1.0 | 0.8 |
| Dmrtc1a | 1.0 | 1.0 | 1.0 | 1.0 | 1.0 | 1.2 | 1.0 | 1.0 | 1.0 | 1.0 | 1.0 | 1.0 | 2.1 | 1.7 | 7.3 | 1.0 | 1.0 | 1.0 | 1.0 | 1.0 | 1.0 | 1.0 |
| Dmrtn | 0.9 | 0.8 | 0.8 | 1.0 | 1.0 | 1.0 | 0.3 | 0.9 | 1.0 | 1.0 | 1.0 | 1.0 | 1.4 | 2.2 | 0.6 | 0.8 | 1.0 | 1.0 | 1.0 | 1.0 | 1.0 | 1.0 |
| Dnajb8 | 1.0 | 1.0 | 1.0 | 1.0 | 1.0 | 1.0 | 1.0 | 1.0 | 1.0 | 1.0 | 1.0 | 1.0 | 1.0 | 1.0 | 5.8 | 1.0 | 1.0 | 1.0 | 1.0 | 1.0 | 1.0 | 1.0 |
| Dnase1 | 0.1 | 0.1 | 1.0 | 1.0 | 1.0 | 1.0 | 1.0 | 1.0 | 1.0 | 1.0 | 2.4 | 5.4 | 1.0 | 1.3 | 1.0 | 1.0 | 1.0 | 1.0 | 0.7 | 0.5 | 0.6 | 0.7 |
| Dnase1l3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Dnd1 | 1.0 | 1.0 | 1.0 | 1.0 | 1.0 | 1.0 | 1.0 | 1.0 | 0.9 | 0.9 | 1.0 | 1.0 | 0.6 | 0.7 | 1.0 | 1.0 | 1.0 | 1.0 | 1.0 | 1.0 | 1.0 | 1.0 |
| Dnpep2 | 1.6 | 1.0 | 1.0 | 1.2 | 1.1 | 0.8 | 1.0 | 0.9 | 1.4 | 1.0 | 3.3 | 1.1 | 1.1 | 0.7 | 0.8 | 0.9 | 0.9 | 0.8 | 1.1 | 1.4 |
| Drd4 | 1.0 | 1.0 | 1.0 | 1.0 | 1.0 | 1.0 | 1.0 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |
| Duoxa2 | 1.0 | 1.0 | 1.3 | 0.3 | 1.0 | 1.0 | 1.0 | 1.0 | 1.0 | 1.0 | 1.0 | 0.8 | 1.0 | 1.0 | 1.0 | 1.0 | 1.9 | 1.4 | 7.4 | 5.3 | 0.5 | 0.7 |

[Fig. 23-20]

| | Kidney | | Colon | | Eyeball | | Heart | | Liver | | SG | | Thymus | | Adipose | | Stomach | | Jejunum | | Ileum | |
|---|---|---|---|---|---|---|---|---|---|---|---|---|---|---|---|---|---|---|---|---|---|---|
| | F | M | F | M | F | M | F | M | F | M | F | M | F | M | F | M | F | M | F | M | F | M |
| Dupd1 | 1.0 | 1.0 | 1.0 | 1.0 | 0.5 | 0.4 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Dusp10 | 1.0 | 1.0 | 1.0 | 1.1 | 0.8 | 0.9 | 1.2 | 0.6 | 1.2 | 1.2 | 0.9 | 1.0 | 0.8 | 1.0 | 0.5 | 0.2 | 0.8 | 1.0 | 1.1 | 1.3 | 1.0 | 1.0 |
| Dusp13 | 1.0 | 1.0 | 1.0 | 1.0 | 0.5 | 0.7 | 1.0 | 1.0 | 1.0 | 1.0 | 1.0 | 1.0 | 1.0 | 1.0 | 1.0 | 1.0 | 1.0 | 0.9 | 1.0 | 1.0 | 1.0 | 1.0 |
| Dusp15 | 1.5 | 0.7 | 1.0 | 1.0 | 0.3 | 0.8 | 1.0 | 1.0 | 1.0 | 1.0 | 1.0 | 1.0 | 1.8 | 1.6 | 8.2 | 1.0 | 1.0 | 1.0 | 1.0 | 1.0 | 1.0 | 1.0 |
| Dusp2 | 0.8 | 1.0 | 0.6 | 0.2 | 1.0 | 1.0 | 1.0 | 1.0 | 1.0 | 1.0 | 0.9 | 1.0 | 1.7 | 1.3 | 1.5 | 1.0 | 1.0 | 1.0 | 1.7 | 0.9 | 1.1 | 0.8 | 9.8 |
| Dusp6 | 2.3 | 1.9 | 1.1 | 1.1 | 1.1 | 0.7 | 2.2 | 0.7 | 1.0 | 1.0 | 2.1 | 1.4 | 1.4 | 1.0 | 5.9 | 1.2 | 1.0 | 0.8 | 1.2 | 0.8 | 1.3 | 1.9 |
| Ear3 | 1.0 | 2.2 | 1.0 | 1.0 | 1.0 | 1.0 | 0.8 | 3.5 | 2.9 | 1.0 | 1.0 | 1.0 | 1.0 | 1.6 | 1.3 | 0.2 | 1.3 | 2.3 | 1.0 | 1.0 | 1.0 | 1.0 |
| Eddm3b | 0.7 | 1.0 | 1.0 | 1.0 | 1.0 | 1.0 | 1.0 | 1.0 | 1.0 | 1.0 | 1.0 | 1.0 | 1.0 | 1.0 | 19.5 | 2.9 | 1.0 | 1.0 | 1.0 | 1.0 | 1.0 | 1.0 |
| Eef1a2 | 1.0 | 1.0 | 0.8 | 1.1 | 0.9 | 0.7 | 1.0 | 1.1 | 1.0 | 1.0 | 1.0 | 1.0 | 1.0 | 1.0 | 1.0 | 1.0 | 0.5 | 0.9 | 1.1 | 1.0 | 1.1 | 1.1 |
| Egf1 | 1.0 | 0.9 | 1.2 | 0.9 | 1.0 | 1.1 | 0.7 | 0.8 | 0.4 | 0.7 | 1.3 | 1.3 | 1.4 | 1.5 | 0.8 | 0.6 | 0.7 | 0.8 | 0.9 | 0.8 | 1.0 | 1.3 |
| Egr2 | 1.0 | 2.1 | 0.8 | 1.0 | 1.0 | 1.0 | 1.0 | 1.0 | 1.0 | 1.0 | 1.0 | 1.0 | 1.2 | 0.7 | 15.4 | 0.4 | 1.1 | 2.3 | 1.0 | 1.0 | 1.0 | 0.9 |
| Eif3j1 | 1.0 | 0.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.0 |
| Eif3j2 | 0.9 | 2.3 | 1.0 | 0.9 | 1.2 | 1.1 | 1.0 | 1.0 | 1.0 | 1.2 | 0.9 | 0.9 | 0.7 | 0.9 | 0.9 | 1.0 | 1.0 | 1.0 | 0.9 | 1.1 | 1.0 | 17.1 |
| Elk4 | 1.7 | 0.9 | 0.9 | 1.1 | 1.2 | 0.7 | 0.8 | 0.7 | 3.0 | 0.5 | 0.8 | 1.0 | 0.2 | 0.7 | 0.5 | 0.4 | 0.7 | 1.0 | 0.7 | 0.4 | 1.1 | 2.4 |
| Eln | 0.5 | 0.5 | 1.0 | 0.7 | 0.6 | 1.2 | 1.0 | 1.0 | 0.9 | 1.5 | 1.0 | 1.1 | 1.0 | 1.0 | 5.0 | 1.0 | 1.1 | 0.9 | 0.7 | 1.0 | 1.0 | 0.7 |
| Elovl2 | 1.8 | 2.5 | 1.0 | 1.0 | 1.1 | 1.2 | 1.0 | 1.0 | 0.8 | 0.6 | 1.0 | 1.0 | 1.0 | 1.0 | 8.1 | 1.0 | 1.5 | 0.8 | 1.0 | 1.0 | 1.0 | 1.0 |
| Elovl3 | 1.0 | 1.0 | 1.0 | 1.0 | 1.0 | 1.0 | 1.0 | 1.0 | 0.1 | 0.0 | 1.0 | 1.0 | 1.0 | 1.0 | 1.0 | 1.0 | 1.0 | 1.0 | 1.0 | 1.0 | 1.0 | 1.0 |
| Elovl4 | 1.0 | 1.0 | 1.0 | 1.0 | 1.0 | 1.0 | 1.0 | 1.0 | 1.0 | 1.0 | 1.0 | 1.0 | 2.1 | 1.0 | 5.5 | 1.0 | 0.9 | 1.0 | 1.0 | 1.0 | 1.0 | 1.0 |
| Emid1 | 0.5 | 0.9 | 1.1 | 0.7 | 0.7 | 0.9 | 1.0 | 0.8 | 1.0 | 1.0 | 1.0 | 0.8 | 0.9 | 1.1 | 14.2 | 1.0 | 1.4 | 1.4 | 1.1 | 1.2 | 1.1 | 0.6 |
| Emp1 | 1.0 | 1.7 | 1.2 | 1.3 | 1.1 | 1.3 | 0.8 | 0.8 | 0.9 | 0.4 | 0.6 | 0.7 | 0.9 | 0.1 | 0.2 | 1.1 | 1.0 | 1.2 | 1.4 | 1.6 | 1.6 |
| Emp2 | 1.0 | 1.2 | 1.0 | 1.0 | 0.9 | 1.1 | 0.8 | 0.9 | 2.5 | 5.2 | 0.9 | 0.9 | 1.6 | 1.5 | 0.8 | 1.0 | 0.9 | 0.8 | 1.2 | 0.6 | 1.0 | 1.0 |
| Emx2 | 1.2 | 0.9 | 1.0 | 1.0 | 1.0 | 1.1 | 1.0 | 1.0 | 1.0 | 1.0 | 1.0 | 1.0 | 1.0 | 1.0 | 5.3 | 2.6 | 1.0 | 1.0 | 1.0 | 1.0 | 1.0 | 1.0 |
| Eno3 | 0.8 | 1.3 | 1.3 | 1.2 | 0.7 | 0.7 | 1.0 | 1.0 | 1.2 | 0.8 | 1.6 | 1.5 | 1.3 | 1.2 | 1.1 | 1.7 | 0.7 | 0.9 | 0.6 | 1.1 | 0.7 | 1.0 |
| Enpp1 | 0.9 | 1.0 | 1.0 | 1.0 | 1.0 | 1.0 | 1.0 | 0.8 | 1.8 | 2.1 | 1.0 | 0.9 | 1.2 | 1.0 | 13.7 | 1.0 | 1.0 | 1.1 | 1.6 | 1.8 | 0.8 | 1.3 |
| Epb4.1l4b | 1.0 | 1.0 | 1.0 | 1.0 | 1.2 | 1.3 | 1.0 | 1.0 | 0.8 | 1.1 | 1.2 | 1.1 | 1.3 | 1.3 | 5.3 | 1.7 | 1.0 | 0.8 | 1.0 | 1.2 | 1.0 | 1.0 |
| Epb4.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Epcam | 1.1 | 1.2 | 1.0 | 1.0 | 0.9 | 1.1 | 1.0 | 1.0 | 0.7 | 1.0 | 1.0 | 0.9 | 1.8 | 1.4 | 4.6 | 7.1 | 1.1 | 1.1 | 1.1 | 1.3 | 1.0 | 0.9 |
| Epn | 1.0 | 1.0 | 1.0 | 1.0 | 1.0 | 1.0 | 1.0 | 1.0 | 1.0 | 1.0 | 1.0 | 1.0 | 1.0 | 1.0 | 17.3 | 1.0 | 1.0 | 1.0 | 1.0 | 1.0 | 1.0 | 1.0 |
| Ermap | 1.0 | 1.0 | 1.0 | 1.0 | 0.7 | 0.8 | 1.0 | 1.0 | 1.0 | 1.0 | 1.0 | 1.0 | 1.2 | 1.0 | 1.0 | 1.0 | 1.0 | 1.0 | 1.0 | 1.0 | 1.0 | 1.0 |
| Esco2 | 1.0 | 1.0 | 0.7 | 0.7 | 1.0 | 1.0 | 1.0 | 1.0 | 1.0 | 1.0 | 1.0 | 1.0 | 0.4 | 0.7 | 1.0 | 1.0 | 1.1 | 0.9 | 1.1 | 1.1 | 0.8 | 0.8 |
| Esrp1 | 1.2 | 1.4 | 1.1 | 1.1 | 1.1 | 1.3 | 1.0 | 1.0 | 1.0 | 1.0 | 1.1 | 1.0 | 1.5 | 1.4 | 7.6 | 1.3 | 1.0 | 1.0 | 1.1 | 1.2 | 1.2 | 1.1 |
| Esrp2 | 1.0 | 0.7 | 1.1 | 1.0 | 0.9 | 0.9 | 1.0 | 1.0 | 1.3 | 0.8 | 1.0 | 1.2 | 1.2 | 1.4 | 9.4 | 1.0 | 0.9 | 1.0 | 1.1 | 0.7 | 0.9 | 1.3 |
| Etv4 | 3.0 | 3.2 | 1.8 | 0.9 | 0.8 | 0.9 | 1.0 | 1.0 | 1.0 | 1.0 | 1.0 | 1.0 | 1.0 | 1.0 | 8.9 | 1.0 | 1.2 | 1.1 | 1.0 | 1.7 | 1.0 | 1.0 |
| Etv5 | 1.4 | 1.5 | 1.2 | 1.2 | 1.0 | 0.9 | 1.7 | 1.3 | 0.7 | 0.6 | 0.7 | 0.9 | 1.2 | 1.5 | 8.8 | 1.4 | 1.1 | 1.1 | 1.0 | 1.4 | 1.2 | 1.5 |
| F11 | 1.0 | 1.0 | 1.0 | 1.0 | 1.0 | 1.0 | 1.0 | 1.0 | 0.3 | 0.3 | 1.0 | 1.0 | 1.0 | 1.0 | 1.0 | 1.0 | 1.0 | 1.0 | 1.0 | 1.0 | 1.0 | 1.0 |
| Faah | 1.1 | 0.9 | 1.2 | 1.0 | 0.9 | 1.0 | 1.0 | 1.0 | 0.9 | 1.1 | 1.1 | 0.9 | 1.1 | 0.9 | 5.6 | 1.4 | 1.0 | 1.1 | 0.9 | 1.0 | 1.0 | 1.0 |
| Fabp1 | 3.4 | 6.6 | 0.1 | 2.6 | 1.0 | 1.0 | 1.0 | 1.0 | 0.5 | 0.6 | 1.0 | 1.0 | 1.0 | 0.5 | 0.3 | 1.0 | 6.2 | 0.2 | 0.6 | 0.7 | 0.5 | 0.8 |
| Fabp4 | 0.7 | 1.2 | 0.8 | 1.3 | 0.3 | 0.7 | 0.9 | 1.2 | 0.8 | 0.9 | 0.9 | 2.6 | 1.4 | 3.1 | 0.8 | 1.6 | 0.9 | 1.0 | 0.7 | 1.3 | 0.5 | 1.4 |
| Fabp5 | 0.9 | 1.4 | 1.0 | 0.6 | 1.1 | 1.2 | 0.7 | 0.6 | 0.5 | 0.3 | 1.1 | 0.7 | 1.0 | 0.9 | 3.3 | 1.1 | 1.2 | 1.0 | 0.7 | 0.9 | 0.8 |
| Fads2 | 1.2 | 0.9 | 1.0 | 1.0 | 0.9 | 0.8 | 1.4 | 0.7 | 0.7 | 0.2 | 1.0 | 1.5 | 0.7 | 0.7 | 3.7 | 2.1 | 1.0 | 0.6 | 1.2 | 0.6 | 1.0 | 1.1 |
| Faim2 | 1.0 | 1.0 | 0.9 | 1.2 | 1.0 | 1.0 | 1.0 | 1.0 | 1.0 | 1.0 | 0.6 | 0.4 | 1.0 | 1.0 | 5.6 | 1.0 | 1.0 | 1.0 | 1.0 | 1.0 | 1.0 | 1.0 |
| Faim3 | 1.0 | 1.0 | 0.1 | 0.3 | 1.0 | 1.0 | 1.0 | 1.0 | 1.0 | 1.0 | 0.6 | 3.1 | 2.0 | 1.7 | 1.0 | 1.0 | 1.0 | 1.0 | 0.9 | 0.6 | 0.7 | 0.2 |
| Fam150b | 1.0 | 1.0 | 1.0 | 1.0 | 1.0 | 1.0 | 1.0 | 1.0 | 1.0 | 1.0 | 1.0 | 1.0 | 1.0 | 1.0 | 0.3 | 0.7 | 1.0 | 1.0 | 1.0 | 1.0 | 1.0 | 1.0 |
| Fam198a | 1.0 | 1.0 | 1.0 | 1.0 | 1.1 | 0.7 | 0.8 | 1.0 | 0.9 | 0.3 | 1.0 | 1.0 | 1.0 | 1.0 | 1.1 | 1.0 | 1.1 | 1.0 | 1.0 | 1.0 | 1.0 | 1.0 |
| Fam20a | 2.0 | 2.9 | 1.0 | 0.8 | 0.9 | 0.7 | 1.5 | 1.0 | 0.7 | 1.0 | 0.8 | 0.7 | 1.7 | 1.5 | 0.8 | 1.2 | 0.9 | 0.9 | 1.2 | 1.2 | 1.1 | 1.1 |
| Fam20c | 1.0 | 0.7 | 0.6 | 0.7 | 0.3 | 0.8 | 0.9 | 0.9 | 0.5 | 0.5 | 0.8 | 1.4 | 2.2 | 1.1 | 0.4 | 0.2 | 0.9 | 1.7 | 1.0 | 0.9 | 0.7 | 0.8 |
| Fam25c | 4.1 | 3.9 | 1.0 | 1.0 | 1.3 | 1.0 | 1.0 | 1.1 | 2.1 | 2.5 | 0.3 | 1.5 | 0.9 | 1.0 | 1.0 | 1.0 | 0.9 | 1.0 | 1.0 | 1.0 | 1.0 |
| Fam57b | 1.0 | 0.8 | 0.9 | 1.3 | 0.9 | 1.0 | 1.0 | 0.7 | 1.0 | 1.0 | 1.0 | 1.0 | 1.0 | 1.1 | 1.2 | 1.0 | 1.2 | 1.2 | 1.0 | 0.7 | 1.1 |
| Fam64a | 1.0 | 1.0 | 0.6 | 0.6 | 1.0 | 1.0 | 1.0 | 1.0 | 1.0 | 1.0 | 0.5 | 0.7 | 0.6 | 1.0 | 1.3 | 1.0 | 1.0 | 1.0 | 0.9 | 0.7 |
| Fam84a | 1.1 | 1.0 | 0.6 | 0.7 | 1.0 | 1.1 | 1.1 | 1.0 | 1.0 | 1.0 | 1.0 | 1.0 | 2.0 | 1.2 | 11.3 | 0.5 | 0.5 | 0.8 | 1.3 | 1.5 | 1.0 | 1.4 |
| Bxxo40 | 0.5 | 0.3 | 1.0 | 1.0 | 0.7 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Fcamr | 0.4 | 0.7 | 1.0 | 0.7 | 1.0 | 1.0 | 1.0 | 1.0 | 1.0 | 1.0 | 1.0 | 0.9 | 1.0 | 1.0 | 0.7 | 1.3 | 1.0 | 1.0 | 1.3 | 0.7 | 1.2 | 1.9 |
| Fcer2a | 1.0 | 1.0 | 0.3 | 0.3 | 1.0 | 1.0 | 1.0 | 1.0 | 1.0 | 1.0 | 0.6 | 2.3 | 1.2 | 1.3 | 1.0 | 1.0 | 1.0 | 1.0 | 0.9 | 0.8 | 0.5 | 0.7 |
| Fcgbp | 0.7 | 0.6 | 0.5 | 0.5 | 1.1 | 0.8 | 1.0 | 1.0 | 1.0 | 1.0 | 1.0 | 1.0 | 2.0 | 1.2 | 1.0 | 1.0 | 0.4 | 0.2 | 1.1 | 1.0 | 1.1 | 1.3 |
| Fcna | 1.0 | 1.0 | 1.0 | 0.9 | 1.0 | 1.3 | 1.7 | 1.2 | 0.9 | 1.2 | 1.0 | 1.0 | 1.3 | 1.2 | 0.9 | 1.1 | 2.0 | 1.8 | 1.0 | 1.0 | 0.9 | 1.0 |
| Fcrla | 1.0 | 1.0 | 0.4 | 0.2 | 1.0 | 1.0 | 1.0 | 1.0 | 1.0 | 1.0 | 1.0 | 1.2 | 1.1 | 0.7 | 0.8 | 1.0 | 1.0 | 1.0 | 1.0 | 0.9 | 0.6 | 0.6 |
| Fga | 5.5 | 8.4 | 0.3 | 1.0 | 1.0 | 1.0 | 1.0 | 1.0 | 0.9 | 0.3 | 1.0 | 1.0 | 1.0 | 1.0 | 2.7 | 1.0 | 5.4 | 0.2 | 1.0 | 1.0 | 1.0 | 1.0 |
| Fgb | 8.4 | 14.2 | 0.3 | 1.0 | 1.0 | 1.0 | 1.0 | 1.0 | 0.8 | 0.8 | 1.0 | 1.0 | 1.0 | 1.0 | 1.0 | 1.0 | 7.2 | 0.1 | 1.0 | 1.0 | 1.0 | 1.0 |
| Fgf15 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.0 |
| Fgf23 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Fgfbp1 | 3.6 | 1.6 | 1.1 | 1.1 | 1.1 | 1.0 | 1.0 | 1.0 | 1.0 | 1.0 | 1.7 | 1.4 | 1.0 | 1.3 | 1.0 | 1.0 | 1.1 | 1.0 | 1.0 | 1.1 | 1.2 | 0.9 |
| Fgg | 13.0 | 12.3 | 0.5 | 1.0 | 1.0 | 1.0 | 1.0 | 1.0 | 0.7 | 0.8 | 1.0 | 1.0 | 1.0 | 1.0 | 4.4 | 0.2 | 1.0 | 1.0 | 1.0 | 1.0 | 1.0 |
| Fhl2 | 1.1 | 1.0 | 0.9 | 0.7 | 0.6 | 0.6 | 1.1 | 0.9 | 1.0 | 1.0 | 1.0 | 0.9 | 1.0 | 1.1 | 0.6 | 1.8 | 0.8 | 1.0 | 1.0 | 0.9 | 1.2 | 1.2 |
| Fhl4 | 1.0 | 1.0 | 1.0 | 1.0 | 1.0 | 1.0 | 1.0 | 1.0 | 1.0 | 1.0 | 1.0 | 1.0 | 1.0 | 1.0 | 6.6 | 1.1 | 1.0 | 1.0 | 1.0 | 1.0 | 1.0 | 1.0 |
| Fitm1 | 0.7 | 0.8 | 1.0 | 1.0 | 0.8 | 0.4 | 0.9 | 1.0 | 0.3 | 0.2 | 1.0 | 1.0 | 1.0 | 1.0 | 1.0 | 1.0 | 1.0 | 1.0 | 1.0 | 1.0 | 1.0 | 1.0 |
| Flnc | 1.0 | 1.0 | 1.2 | 1.0 | 0.7 | 0.6 | 0.8 | 0.9 | 1.0 | 1.0 | 1.0 | 1.0 | 1.0 | 1.0 | 1.3 | 0.9 | 1.4 | 1.4 | 1.1 | 0.7 | 0.8 | 1.5 |
| Flrt2 | 1.3 | 1.0 | 0.9 | 1.0 | 1.1 | 1.1 | 1.0 | 0.8 | 1.0 | 1.0 | 1.0 | 1.0 | 1.1 | 0.9 | 0.8 | 0.6 | 0.8 | 1.2 | 1.0 | 1.0 | 1.0 | 1.0 |
| Fmo2 | 1.2 | 1.1 | 1.7 | 1.9 | 1.1 | 1.1 | 1.5 | 1.5 | 7.8 | 8.1 | 1.0 | 1.5 | 2.3 | 3.2 | 1.1 | 1.0 | 1.2 | 1.3 | 1.3 | 1.4 | 2.3 |
| Fmo3 | 1.2 | 1.0 | 1.0 | 1.0 | 1.0 | 1.0 | 1.7 | 1.0 | 12.4 | 74.0 | 1.0 | 1.0 | 1.0 | 1.2 | 1.4 | 1.0 | 1.0 | 1.0 | 1.0 | 1.0 | 1.0 |
| Fn3k | 0.6 | 0.7 | 1.0 | 1.1 | 1.1 | 1.0 | 1.7 | 1.2 | 0.6 | 1.0 | 1.7 | 0.7 | 0.9 | 0.5 | 0.9 | 2.8 | 0.6 | 0.4 | 1.0 | 1.0 | 1.0 | 1.1 |
| Foxd3 | 1.4 | 1.0 | 1.0 | 1.0 | 1.0 | 1.0 | 1.0 | 1.0 | 1.0 | 1.0 | 1.2 | 1.2 | 1.0 | 13.7 | 1.0 | 1.0 | 1.0 | 1.0 | 1.0 | 1.0 | 1.0 |
| Foxj1 | 1.0 | 1.4 | 1.0 | 0.8 | 0.7 | 1.0 | 1.0 | 1.0 | 1.0 | 1.0 | 1.0 | 2.2 | 1.0 | 1.1 | 8.3 | 1.0 | 1.0 | 1.0 | 1.0 | 1.0 | 1.0 |
| Snora78 | 1.4 | 0.9 | 0.9 | 1.0 | 1.4 | 0.5 | 1.0 | 0.8 | 2.9 | 0.4 | 0.9 | 1.9 | 0.6 | 1.0 | 0.6 | 0.3 | 0.8 | 1.0 | 0.7 | 0.5 | 1.1 | 3.0 |
| Foxo3 | 1.7 | 1.0 | 0.8 | 1.3 | 1.1 | 0.5 | 0.9 | 1.0 | 1.2 | 0.3 | 0.9 | 1.7 | 1.0 | 0.9 | 1.1 | 0.5 | 0.3 | 1.0 | 0.9 | 0.5 | 1.2 | 1.0 |
| Foxo6 | 1.0 | 1.0 | 1.2 | 1.3 | 0.6 | 0.7 | 0.8 | 0.6 | 1.0 | 1.0 | 1.3 | 1.2 | 1.0 | 1.0 | 1.5 | 1.0 | 0.6 | 0.9 | 1.4 | 1.5 | 0.7 | 0.9 |
| Foxq1 | 1.5 | 1.4 | 1.3 | 1.1 | 0.4 | 0.6 | 1.0 | 1.0 | 0.5 | 0.3 | 1.3 | 1.1 | 1.3 | 1.2 | 1.7 | 1.0 | 0.7 | 1.2 | 1.2 | 2.4 |
| Frzd2 | 1.0 | 1.0 | 1.0 | 1.0 | 0.5 | 0.5 | 0.3 | 0.9 | 1.0 | 1.0 | 1.0 | 1.0 | 0.8 | 0.8 | 0.4 | 0.6 | 1.0 | 1.0 | 1.0 | 1.0 | 1.0 | 1.0 |
| Fst | 1.0 | 2.6 | 1.6 | 1.2 | 0.8 | 1.2 | 1.0 | 0.9 | 0.7 | 0.2 | 0.7 | 0.7 | 1.3 | 1.1 | 0.8 | 0.7 | 2.6 | 1.3 | 1.9 | 1.8 | 1.7 | 1.3 |
| Fut1 | 1.0 | 1.0 | 0.6 | 0.8 | 1.0 | 1.0 | 1.0 | 1.0 | 1.0 | 1.0 | 1.0 | 1.0 | 1.1 | 1.0 | 5.4 | 1.0 | 1.2 | 0.8 | 0.8 | 1.0 | 1.1 | 0.4 |
| Fut4 | 1.0 | 1.0 | 1.0 | 1.0 | 1.2 | 1.0 | 1.6 | 2.3 | 1.0 | 1.0 | 0.8 | 1.1 | 1.2 | 1.4 | 7.4 | 1.0 | 1.1 | 1.1 | 1.3 | 1.3 | 1.0 | 1.0 |
| Fxyd3 | 1.0 | 1.0 | 1.0 | 0.5 | 1.0 | 1.0 | 1.0 | 1.0 | 1.0 | 1.0 | 2.0 | 0.9 | 1.0 | 0.8 | 1.0 | 1.0 | 1.1 | 1.2 | 1.0 | 1.0 | 1.0 | 0.7 |
| Fxyd4 | 0.6 | 1.0 | 1.1 | 5.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |

[Fig. 23-21]

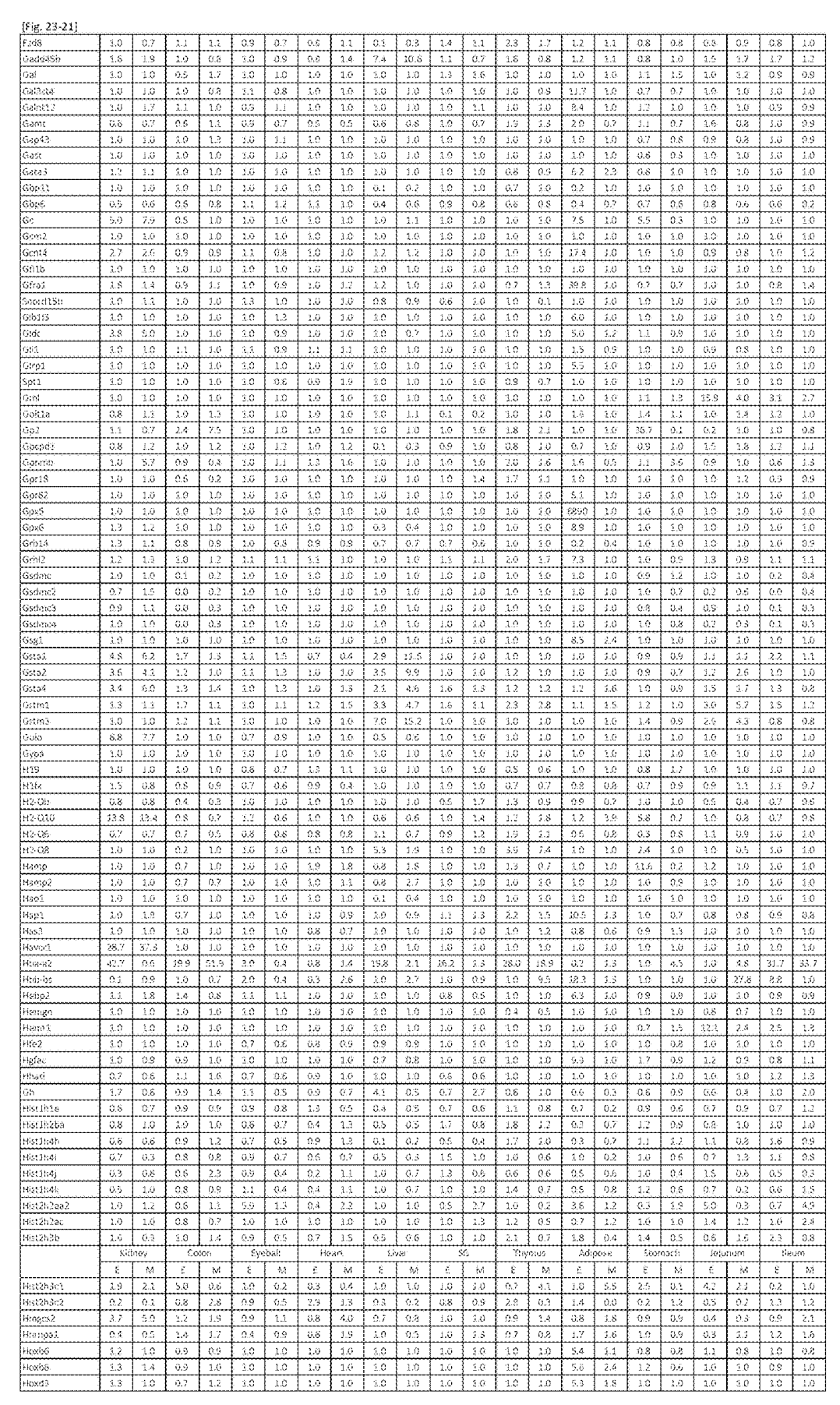

This figure is a large data table that is too dense and low-resolution to transcribe reliably.

[Fig. 23-22]

| | | | | | | | | | | | | | | | | | | | | | |
|---|---|---|---|---|---|---|---|---|---|---|---|---|---|---|---|---|---|---|---|---|---|
| Hod1 | 1.5 | 2.0 | 1.1 | 1.2 | 1.0 | 0.8 | 0.7 | 0.7 | 1.0 | 1.0 | 1.0 | 1.0 | 1.0 | 1.0 | 9.6 | 1.0 | 1.7 | 1.3 | 1.1 | 1.4 | 1.0 | 1.4 |
| Hpx | 1.0 | 1.0 | 0.6 | 1.0 | 1.0 | 1.0 | 1.0 | 1.0 | 0.9 | 1.0 | 1.0 | 1.0 | 1.0 | 1.0 | 1.0 | 1.0 | 7.2 | 0.2 | 1.0 | 1.0 | 1.0 | 1.0 |
| Hr | 1.0 | 1.1 | 0.9 | 0.8 | 0.9 | 0.8 | 0.8 | 1.0 | 1.0 | 1.0 | 0.6 | 0.6 | 1.4 | 1.1 | 6.3 | 0.3 | 1.0 | 0.9 | 0.6 | 0.2 | 1.0 | 1.0 |
| Hrc | 1.0 | 1.0 | 0.8 | 1.2 | 0.7 | 0.7 | 1.0 | 1.1 | 1.0 | 1.0 | 1.0 | 1.0 | 1.0 | 1.0 | 1.0 | 1.0 | 0.8 | 0.9 | 0.6 | 0.6 | 0.9 | 1.4 |
| Hrg | 0.3 | 0.1 | 1.0 | 0.9 | 1.0 | 1.0 | 1.0 | 1.0 | 0.7 | 0.8 | 1.0 | 1.0 | 1.0 | 1.0 | 1.0 | 1.0 | 3.5 | 0.3 | 1.0 | 1.0 | 1.0 | 1.0 |
| Hs3st3b1 | 1.3 | 0.9 | 0.9 | 0.2 | 1.1 | 1.1 | 1.0 | 1.0 | 0.9 | 0.7 | 1.4 | 1.2 | 1.4 | 1.1 | 5.9 | 3.1 | 0.7 | 0.7 | 0.9 | 0.7 | 0.9 | 0.9 |
| Hsd17b11 | 0.3 | 0.3 | 1.1 | 1.3 | 1.1 | 1.0 | 1.0 | 1.5 | 0.8 | 1.5 | 1.0 | 0.2 | 1.1 | 1.1 | 0.9 | 1.8 | 0.9 | 0.9 | 0.9 | 1.4 | 1.2 | 1.0 |
| Hsd17b6 | 1.0 | 1.0 | 1.0 | 1.0 | 1.0 | 1.0 | 1.0 | 1.0 | 1.5 | 1.6 | 1.0 | 1.0 | 1.0 | 1.0 | 1.0 | 1.0 | 0.9 | 0.8 | 1.0 | 1.7 | 0.6 | 1.3 |
| Hsd3b2 | 0.2 | 0.2 | 1.0 | 1.2 | 1.0 | 1.0 | 1.0 | 1.0 | 0.4 | 0.4 | 1.0 | 1.0 | 1.0 | 1.0 | 1.0 | 1.0 | 1.0 | 1.0 | 0.7 | 1.2 | 1.5 | 1.8 |
| Hsd3b6 | 1.0 | 1.3 | 1.0 | 1.0 | 1.0 | 1.0 | 1.0 | 1.0 | 0.1 | 0.0 | 1.0 | 1.0 | 1.0 | 1.0 | 1.0 | 1.0 | 1.0 | 1.0 | 1.0 | 1.0 | 1.0 | 1.0 |
| Hspb3 | 1.0 | 1.0 | 1.0 | 1.0 | 0.8 | 0.5 | 0.9 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 |
| Hspb6 | 0.7 | 0.8 | 0.8 | 0.9 | 0.7 | 0.8 | 1.0 | 1.0 | 1.0 | 1.0 | 1.2 | 0.9 | 0.8 | 0.7 | 1.0 | 0.8 | 1.2 | 1.1 | 0.8 | 1.3 | 0.9 | 1.1 |
| Hspb7 | 1.1 | 1.2 | 1.0 | 1.3 | 0.6 | 1.1 | 1.2 | 1.2 | 1.0 | 1.0 | 2.2 | 1.5 | 1.0 | 1.0 | 0.7 | 0.7 | 1.3 | 1.5 | 1.2 | 1.4 | 0.6 | 0.8 |
| Hspb9 | 0.8 | 1.0 | 1.0 | 1.0 | 1.0 | 1.0 | 1.0 | 1.0 | 1.0 | 1.0 | 1.0 | 1.0 | 1.1 | 1.2 | 6.5 | 1.4 | 1.0 | 1.2 | 0.6 | 1.3 | 0.9 | 1.0 |
| Icam4 | 1.0 | 1.0 | 1.0 | 1.0 | 1.0 | 1.0 | 0.6 | 1.1 | 1.2 | 1.0 | 1.0 | 1.0 | 1.0 | 1.0 | 1.0 | 1.0 | 1.0 | 1.0 | 1.0 | 1.0 | 1.0 | 1.0 |
| Id4 | 1.0 | 1.0 | 0.6 | 0.6 | 1.0 | 1.0 | 1.0 | 1.0 | 1.0 | 1.0 | 1.0 | 1.0 | 1.0 | 1.0 | 52.5 | 1.0 | 1.0 | 1.0 | 1.1 | 1.5 | 0.7 | 0.7 |
| Igfbp3 | 2.1 | 5.3 | 1.0 | 1.0 | 1.0 | 1.0 | 1.0 | 1.7 | 1.5 | 1.0 | 1.0 | 1.0 | 1.0 | 1.0 | 1.0 | 1.0 | 1.0 | 1.0 | 1.0 | 1.0 | 1.0 | 1.0 |
| Igj | 0.7 | 1.1 | 1.1 | 0.5 | 1.0 | 1.2 | 1.0 | 1.0 | 1.0 | 1.0 | 0.4 | 2.2 | 1.3 | 1.5 | 0.6 | 0.5 | 1.6 | 0.8 | 1.0 | 1.2 | 1.0 | 0.9 |
| Ibzf3 | 1.0 | 1.0 | 0.6 | 0.2 | 1.0 | 1.0 | 1.0 | 1.0 | 1.0 | 1.0 | 1.0 | 1.8 | 0.7 | 0.2 | 1.0 | 0.8 | 1.0 | 1.0 | 0.9 | 0.6 | 0.8 | 1.1 |
| Il21 | 1.0 | 1.2 | 0.5 | 0.3 | 1.0 | 1.0 | 1.0 | 1.0 | 1.0 | 1.0 | 0.8 | 3.4 | 0.9 | 0.8 | 1.0 | 0.8 | 1.0 | 1.0 | 1.0 | 0.8 | 0.9 | 0.6 |
| Il22ra1 | 0.5 | 0.4 | 1.1 | 1.2 | 1.0 | 1.0 | 1.0 | 1.0 | 6.0 | 4.5 | 1.0 | 1.0 | 1.0 | 1.0 | 1.0 | 1.0 | 1.4 | 0.8 | 1.5 | 1.4 | 0.8 | 1.2 |
| Ildr1 | 1.2 | 1.3 | 1.2 | 1.2 | 1.0 | 1.2 | 1.0 | 1.0 | 1.0 | 1.0 | 0.9 | 0.5 | 1.8 | 1.7 | 7.3 | 1.0 | 0.8 | 0.8 | 0.8 | 0.7 | 1.0 | 1.0 |
| Ildr2 | 1.0 | 1.1 | 1.0 | 1.0 | 1.1 | 1.1 | 1.0 | 1.0 | 4.0 | 5.6 | 1.0 | 1.0 | 1.0 | 1.0 | 1.2 | 0.8 | 1.0 | 1.0 | 1.0 | 1.0 | 1.0 | 1.0 |
| Inha | 0.9 | 0.7 | 0.6 | 1.3 | 0.9 | 0.7 | 1.2 | 1.0 | 1.0 | 1.0 | 1.2 | 1.1 | 2.7 | 2.4 | 6.6 | 1.7 | 0.8 | 0.9 | 1.0 | 1.0 | 0.6 | 0.8 |
| Insc | 1.0 | 1.0 | 1.4 | 0.9 | 1.0 | 0.8 | 1.0 | 1.0 | 0.5 | 0.3 | 1.0 | 1.0 | 1.0 | 1.0 | 1.0 | 1.0 | 1.0 | 1.0 | 0.6 | 1.3 | 1.2 | 0.7 |
| Iqck3 | 1.0 | 1.0 | 1.0 | 1.0 | 0.3 | 0.8 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Isyna1 | 1.0 | 0.9 | 1.0 | 0.9 | 0.3 | 0.9 | 1.1 | 1.2 | 2.0 | 2.8 | 1.0 | 0.9 | 1.2 | 1.0 | 7.6 | 1.5 | 1.2 | 1.1 | 1.5 | 1.1 | 1.0 | 1.0 |
| Itga2 | 1.0 | 2.3 | 0.8 | 0.6 | 1.0 | 1.0 | 1.0 | 1.0 | 1.0 | 1.0 | 1.0 | 1.2 | 1.2 | 0.5 | 0.4 | 1.6 | 5.1 | 1.0 | 0.8 | 0.7 | 0.6 | |
| Itgb1bp2 | 1.0 | 1.0 | 1.0 | 1.0 | 0.7 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ivgb6 | 0.3 | 0.3 | 1.0 | 0.9 | 0.7 | 0.8 | 1.0 | 0.5 | 1.0 | 1.0 | 0.3 | 0.8 | 1.0 | 1.0 | 1.0 | 1.0 | 0.6 | 0.8 | 1.2 | 1.3 | 1.5 | 0.9 |
| Jph1 | 1.0 | 1.0 | 0.1 | 0.0 | 1.0 | 1.0 | 1.0 | 1.0 | 1.0 | 1.0 | 1.0 | 1.0 | 1.0 | 1.0 | 1.0 | 1.0 | 1.5 | 1.0 | 0.8 | 0.8 | 0.7 | 1.0 |
| Jph1 | 1.0 | 1.0 | 1.0 | 1.0 | 0.9 | 0.6 | 0.9 | 1.1 | 1.8 | 1.0 | 1.0 | 1.0 | 1.0 | 1.4 | 1.4 | 0.9 | 0.9 | 0.7 | 0.9 | 1.0 | 1.0 | 1.0 |
| Jph2 | 1.0 | 1.0 | 0.9 | 1.0 | 0.7 | 0.5 | 1.0 | 1.1 | 1.0 | 1.0 | 0.7 | 0.7 | 1.0 | 1.0 | 1.0 | 2.0 | 1.1 | 0.9 | 1.3 | 1.1 | 0.5 | 1.1 |
| Jsrp1 | 1.0 | 1.0 | 1.0 | 1.0 | 0.6 | 0.7 | 1.0 | 1.0 | 1.0 | 1.0 | 1.0 | 1.0 | 1.0 | 1.0 | 1.0 | 1.0 | 0.9 | 1.2 | 1.0 | 1.0 | 1.0 | 1.0 |
| Kcna7 | 1.0 | 1.0 | 1.0 | 1.0 | 0.5 | 0.4 | 0.3 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |
| Kcnc1 | 1.0 | 1.0 | 1.0 | 1.0 | 1.0 | 0.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Kcnc4 | 1.0 | 1.0 | 1.0 | 1.0 | 1.0 | 0.7 | 1.0 | 1.0 | 1.0 | 1.0 | 1.0 | 1.0 | 1.0 | 1.0 | 6.0 | 1.0 | 1.0 | 1.0 | 1.0 | 1.0 | 1.0 | 1.0 |
| Kcne3 | 0.6 | 0.7 | 0.9 | 0.9 | 1.0 | 1.0 | 1.0 | 1.0 | 1.5 | 2.6 | 0.9 | 1.3 | 1.0 | 1.0 | 1.0 | 1.1 | 1.9 | 0.7 | 1.1 | 0.9 | 0.7 | 0.7 |
| Kcng4 | 1.0 | 1.0 | 1.0 | 1.0 | 1.0 | 0.8 | 1.0 | 1.0 | 1.0 | 1.0 | 1.0 | 1.0 | 1.0 | 1.0 | 1.0 | 1.0 | 2.1 | 1.2 | 1.0 | 1.0 | 1.0 | 1.0 |
| Kcnh3 | 1.0 | 1.0 | 0.7 | 1.1 | 1.0 | 1.0 | 1.0 | 1.0 | 1.0 | 1.0 | 1.0 | 1.0 | 0.9 | 0.7 | 11.9 | 1.0 | 1.0 | 1.0 | 1.0 | 1.0 | 0.9 | 1.3 |
| Kcnj11 | 1.0 | 1.0 | 1.0 | 0.9 | 0.7 | 0.7 | 1.1 | 1.1 | 1.0 | 1.0 | 1.0 | 1.0 | 1.0 | 1.0 | 5.2 | 1.0 | 0.9 | 1.0 | 1.0 | 1.0 | 1.0 | 1.0 |
| Kcnj12 | 0.7 | 0.7 | 1.0 | 1.0 | 1.0 | 0.8 | 1.4 | 1.2 | 1.0 | 1.0 | 1.0 | 1.0 | 1.0 | 1.0 | 1.7 | 1.0 | 1.0 | 0.9 | 1.0 | 1.0 | 1.0 | 1.0 |
| Kcnj15 | 1.1 | 1.0 | 1.0 | 1.0 | 1.0 | 1.0 | 1.0 | 1.0 | 1.0 | 1.0 | 1.3 | 1.8 | 1.8 | 1.1 | 1.0 | 0.9 | 1.0 | 1.0 | 1.0 | 1.0 | 1.0 | 1.0 |
| Kcnk1 | 1.7 | 1.8 | 1.0 | 0.9 | 1.0 | 0.9 | 1.0 | 1.0 | 1.0 | 1.0 | 0.3 | 0.6 | 2.2 | 1.8 | 3.4 | 4.9 | 1.1 | 1.1 | 1.4 | 1.2 | 1.3 | 1.1 |
| Kcnk16 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.7 | 1.2 | 1.0 | 1.0 | 1.0 | 1.0 |
| Cfrb1 | 1.0 | 1.0 | 1.0 | 1.0 | 1.6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Kcld1 | 1.3 | 1.4 | 1.0 | 1.3 | 1.1 | 1.0 | 1.1 | 0.8 | 1.0 | 1.0 | 1.4 | 1.1 | 1.2 | 1.3 | 5.4 | 1.0 | 1.0 | 0.9 | 1.0 | 1.0 | 1.0 | 1.0 |
| Ktelc2 | 0.5 | 1.2 | 0.8 | 0.2 | 0.8 | 0.9 | 0.7 | 0.8 | 1.0 | 1.0 | 0.8 | 0.9 | 1.0 | 0.9 | 0.6 | 0.8 | 1.2 | 1.3 | 0.8 | 1.2 | 0.8 | 0.8 |
| Ksl | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Kena | 1.0 | 1.0 | 1.0 | 1.0 | 0.5 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.3 |
| Kif26b | 0.2 | 0.2 | 0.8 | 0.9 | 1.0 | 1.0 | 1.0 | 1.0 | 1.0 | 1.0 | 1.0 | 1.0 | 0.4 | 0.6 | 1.0 | 1.0 | 0.6 | 1.1 | 0.7 | 1.1 | 1.0 |
| Kiss1 | 1.0 | 0.7 | 1.5 | 2.0 | 1.0 | 1.0 | 1.0 | 1.0 | 1.0 | 0.5 | 0.1 | 0.3 | 1.0 | 1.0 | 1.0 | 1.0 | 1.0 | 1.5 | 1.0 | 1.0 | 1.0 | 0.8 |
| Kit1 | 1.4 | 1.0 | 1.0 | 1.0 | 1.0 | 1.0 | 1.0 | 1.0 | 0.5 | 0.6 | 1.0 | 1.0 | 1.0 | 1.0 | 1.0 | 1.0 | 1.0 | 1.0 | 1.0 | 1.0 | 1.0 | 1.0 |
| Klhl30 | 1.0 | 1.0 | 0.9 | 0.7 | 0.8 | 0.6 | 0.8 | 0.8 | 1.0 | 1.0 | 1.0 | 1.0 | 1.0 | 1.0 | 1.0 | 1.0 | 1.0 | 1.6 | 1.0 | 1.0 | 1.0 | 1.0 |
| Klhl31 | 1.0 | 1.0 | 1.0 | 1.0 | 0.6 | 0.6 | 0.9 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 |
| Klhl34 | 1.0 | 1.0 | 1.0 | 1.0 | 1.1 | 0.6 | 0.9 | 0.7 | 1.0 | 1.0 | 1.0 | 1.0 | 1.0 | 1.0 | 5.4 | 1.0 | 1.0 | 1.0 | 1.0 | 1.0 | 1.0 | 1.0 |
| Klhl40 | 1.0 | 1.0 | 1.0 | 1.0 | 0.6 | 0.5 | 1.0 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |
| Klhl41 | 1.0 | 1.0 | 1.0 | 1.0 | 0.7 | 0.7 | 0.9 | 0.9 | 1.0 | 1.0 | 1.0 | 1.0 | 1.0 | 1.0 | 1.0 | 1.0 | 0.7 | 1.3 | 1.0 | 1.0 | 1.0 | 1.0 |
| Klf5 | 1.2 | 1.3 | 0.7 | 0.5 | 1.0 | 0.9 | 1.0 | 0.9 | 1.3 | 0.2 | 0.8 | 1.6 | 0.9 | 1.1 | 0.7 | 0.9 | 1.2 | 1.8 | 1.0 | 0.7 | 0.9 | 0.9 |
| Klk10 | 1.0 | 1.0 | 1.0 | 1.0 | 1.1 | 1.7 | 1.0 | 1.0 | 1.0 | 1.0 | 1.0 | 1.0 | 1.0 | 1.3 | 1.0 | 1.0 | 0.9 | 1.1 | 1.0 | 1.0 | 1.0 | 1.0 |
| Klk14 | 1.0 | 1.0 | 1.0 | 1.0 | 1.0 | 1.0 | 1.0 | 1.0 | 1.0 | 1.0 | 1.0 | 1.1 | 1.0 | 1.0 | 1.0 | 0.9 | 1.4 | 1.0 | 1.0 | 1.0 | 1.0 | |
| Klk1b3 | 1.0 | 1.0 | 1.0 | 1.0 | 1.0 | 1.0 | 1.0 | 1.0 | 1.0 | 0.3 | 0.3 | 1.0 | 1.0 | 1.0 | 1.0 | 1.0 | 1.0 | 1.0 | 1.0 | 1.0 | 1.0 | 1.0 |
| Klk1b21 | 1.5 | 0.9 | 1.0 | 1.0 | 1.0 | 1.0 | 1.0 | 1.0 | 1.0 | 0.4 | 0.4 | 1.0 | 1.0 | 1.0 | 1.0 | 1.0 | 1.0 | 1.0 | 1.0 | 1.0 | 1.0 | 1.0 |
| Klk1b24 | 1.0 | 1.1 | 1.0 | 1.0 | 1.0 | 1.0 | 1.0 | 1.0 | 1.0 | 0.4 | 0.3 | 1.0 | 1.0 | 1.0 | 1.0 | 1.0 | 1.0 | 1.0 | 1.0 | 1.0 | 1.0 | 1.0 |
| Klk1b26 | 2.5 | 1.0 | 1.0 | 1.0 | 1.0 | 0.8 | 1.0 | 1.1 | 2.2 | 1.0 | 0.5 | 0.5 | 2.1 | 7.2 | 1.0 | 5.4 | 1.0 | 5.5 | 1.0 | 1.0 | 1.0 | 1.0 |
| Klk1b27 | 2.1 | 1.0 | 1.0 | 1.0 | 1.0 | 1.0 | 1.0 | 1.0 | 1.0 | 0.2 | 0.2 | 1.3 | 1.0 | 1.0 | 1.0 | 1.0 | 1.0 | 1.0 | 1.0 | 1.0 | 1.0 | 1.0 |
| Klk1b7-ps | 1.0 | 1.0 | 1.0 | 1.0 | 1.0 | 1.0 | 1.0 | 1.0 | 1.0 | 0.4 | 0.2 | 1.0 | 1.0 | 1.0 | 1.0 | 1.0 | 1.0 | 1.0 | 1.0 | 1.0 | 1.0 | 1.0 |
| Klk1b8 | 1.0 | 1.0 | 1.0 | 1.0 | 1.0 | 1.0 | 1.0 | 0.6 | 1.0 | 1.0 | 0.2 | 0.2 | 1.0 | 1.1 | 1.0 | 1.0 | 1.0 | 1.7 | 1.0 | 1.0 | 1.0 | 1.0 |
| Klk1b9 | 1.4 | 1.0 | 1.0 | 1.0 | 1.0 | 0.7 | 1.0 | 1.0 | 1.0 | 1.0 | 0.2 | 0.3 | 1.0 | 2.8 | 1.0 | 1.0 | 1.0 | 1.4 | 1.0 | 1.0 | 1.0 | 1.0 |
| Klrb1a | 1.0 | 1.0 | 1.0 | 1.0 | 1.0 | 1.0 | 1.0 | 1.0 | 1.0 | 1.0 | 1.0 | 1.0 | 1.0 | 1.0 | 7.6 | 1.0 | 1.0 | 1.0 | 1.0 | 1.0 | 1.0 | 1.0 |
| Klrb1c | 1.0 | 1.0 | 1.0 | 1.0 | 1.0 | 1.0 | 1.0 | 1.0 | 1.0 | 1.0 | 1.0 | 1.0 | 1.8 | 3.4 | 30.0 | 1.0 | 1.0 | 1.0 | 1.0 | 1.0 | 1.0 | 1.0 |
| Kng1 | 1.3 | 1.5 | 1.0 | 1.0 | 1.0 | 1.0 | 1.0 | 1.0 | 1.1 | 1.0 | 1.0 | 1.0 | 1.0 | 1.0 | 5.1 | 0.3 | 1.0 | 1.0 | 1.0 | 1.0 | 1.0 | 1.0 |
| Krt13 | 1.0 | 1.0 | 1.0 | 1.0 | 1.1 | 1.0 | 1.0 | 1.0 | 1.0 | 1.0 | 1.0 | 1.0 | 1.0 | 1.0 | 1.0 | 1.1 | 1.0 | 1.0 | 1.0 | 1.0 | 1.0 | 1.0 |
| Krt14 | 1.0 | 1.0 | 1.0 | 1.0 | 2.3 | 1.0 | 1.0 | 1.0 | 1.0 | 1.0 | 0.9 | 0.8 | 1.7 | 1.0 | 7.5 | 1.0 | 1.0 | 1.0 | 1.0 | 1.0 | 1.0 | 1.0 |
| Krt16 | 1.0 | 1.0 | 1.0 | 1.0 | 2.0 | 13.9 | 1.0 | 1.0 | 1.0 | 1.0 | 1.0 | 1.0 | 1.6 | 0.6 | 1.0 | 1.0 | 1.3 | 8.1 | 1.0 | 1.0 | 1.0 | 1.0 |
| Krt18 | 1.2 | 1.9 | 0.8 | 0.8 | 1.0 | 1.1 | 1.7 | 1.0 | 1.1 | 1.1 | 1.0 | 0.8 | 1.2 | 1.7 | 6.2 | 5.4 | 1.0 | 1.0 | 1.0 | 1.2 | 0.9 | 0.9 |
| Krt23 | 1.0 | 1.4 | 1.5 | 1.2 | 1.2 | 1.7 | 1.0 | 1.0 | 0.8 | 0.5 | 1.0 | 1.0 | 2.1 | 1.0 | 13.9 | 1.0 | 0.9 | 1.0 | 1.0 | 1.2 | 1.2 | 0.5 |
| Krt4 | 1.0 | 1.0 | 1.0 | 1.0 | 1.2 | 1.3 | 1.0 | 1.0 | 1.0 | 1.0 | 1.0 | 1.0 | 1.0 | 1.0 | 1.0 | 1.0 | 1.1 | 1.0 | 1.0 | 1.0 | 1.0 | 1.0 |
| Krt5 | 1.0 | 0.7 | 1.0 | 1.0 | 1.0 | 1.0 | 1.0 | 1.0 | 1.0 | 1.0 | 0.7 | 0.8 | 1.7 | 1.7 | 5.4 | 1.0 | 1.0 | 1.2 | 1.0 | 1.0 | 1.0 | 1.0 |
| Krt6a | 1.0 | 1.0 | 1.0 | 1.0 | 1.4 | 1.0 | 1.0 | 1.0 | 1.0 | 1.0 | 1.0 | 1.4 | 1.0 | 1.0 | 1.0 | 1.0 | 1.2 | 6.0 | 1.0 | 1.0 | 1.0 | 1.0 |
| Krt78 | 1.0 | 1.0 | 1.0 | 1.0 | 1.1 | 0.9 | 1.0 | 1.0 | 1.0 | 1.0 | 1.0 | 2.0 | 1.0 | 1.0 | 1.0 | 1.0 | 0.9 | 1.0 | 1.0 | 1.0 | 1.0 | 1.0 |
| Krtap16-1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Krtap19-1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Krtap19-4 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |

[Fig. 23-23]

| | | | | | | | | | | | | | | | | | | | | | |
|---|---|---|---|---|---|---|---|---|---|---|---|---|---|---|---|---|---|---|---|---|---|
| Krtap5-2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Krtdap | 1.0 | 1.0 | 1.0 | 1.0 | 1.0 | 1.0 | 1.0 | 1.0 | 1.0 | 1.0 | 1.0 | 1.0 | 2.1 | 1.0 | 1.0 | 1.0 | 0.9 | 1.1 | 1.0 | 1.0 | 1.0 |
| Kv | 1.0 | 1.0 | 1.0 | 1.0 | 0.5 | 0.4 | 1.0 | 0.7 | 1.0 | 1.0 | 1.0 | 1.0 | 1.0 | 1.0 | 1.0 | 1.0 | 1.0 | 1.0 | 1.1 | 1.5 | 1.2 | 2.6 |
| Kynu | 4.6 | 9.3 | 1.0 | 1.0 | 1.0 | 1.0 | 1.0 | 1.0 | 0.7 | 0.7 | 1.0 | 1.0 | 1.2 | 0.5 | 1.0 | 1.0 | 1.0 | 1.0 | 0.7 | 0.9 | 1.0 | 1.0 |
| Lart1 | 1.5 | 1.0 | 1.1 | 1.3 | 1.0 | 1.0 | 0.9 | 0.8 | 0.4 | 0.4 | 1.0 | 1.0 | 1.0 | 1.0 | 5.5 | 1.0 | 1.1 | 1.0 | 1.0 | 1.0 | 0.5 | 1.0 |
| Lars2 | 0.9 | 1.6 | 1.0 | 0.3 | 1.0 | 0.6 | 0.8 | 1.1 | 0.8 | 0.4 | 0.8 | 0.7 | 0.8 | 0.7 | 2.1 | 1.2 | 1.1 | 1.0 | 1.0 | 1.4 | 1.0 | 0.7 |
| | Kidney | | Colon | | Eyeball | | Heart | | Liver | | SG | | Thymus | | Adipose | | Stomach | | Jejunum | | Ileum | |
| | E | M | E | M | E | M | E | M | E | M | E | M | E | M | E | M | E | M | E | M | E | M |
| Lbx1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Lce3a | 1.0 | 1.0 | 1.0 | 1.0 | 1.8 | 1.9 | 1.0 | 1.0 | 1.0 | 1.0 | 1.0 | 1.0 | 1.0 | 1.0 | 1.0 | 1.0 | 1.1 | 1.3 | 1.0 | 1.0 | 1.0 | 1.0 |
| Lce3b | 1.0 | 1.0 | 3.3 | 1.0 | 1.0 | 1.0 | 1.0 | 1.0 | 1.0 | 1.0 | 1.0 | 1.0 | 1.0 | 1.0 | 1.0 | 1.0 | 0.9 | 1.3 | 1.0 | 1.0 | 1.0 | 1.0 |
| Lce3c | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.1 | 1.0 | 1.0 | 1.0 | 1.0 |
| Lce3e | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.1 | 1.0 | 1.0 | 1.0 | 1.0 |
| Lce3f | 1.0 | 1.0 | 1.0 | 1.0 | 1.1 | 1.5 | 1.0 | 1.0 | 1.0 | 1.0 | 1.0 | 1.0 | 1.0 | 1.0 | 1.0 | 1.0 | 1.1 | 1.3 | 1.0 | 1.0 | 1.0 | 1.0 |
| Lck | 1.0 | 1.0 | 0.8 | 0.6 | 1.0 | 1.0 | 1.0 | 1.0 | 1.0 | 1.0 | 0.7 | 1.3 | 0.8 | 0.8 | 1.1 | 1.0 | 1.0 | 1.0 | 0.5 | 0.7 | 0.7 | 0.6 |
| Lcn10 | 1.0 | 1.0 | 1.0 | 1.0 | 1.0 | 1.0 | 1.0 | 1.0 | 1.0 | 1.0 | 1.0 | 1.0 | 1.0 | 1.0 | 173.3 | 1.0 | 1.0 | 1.0 | 1.0 | 1.0 | 1.0 | 1.0 |
| Lcn12 | 1.0 | 1.0 | 1.0 | 1.0 | 1.0 | 1.0 | 1.0 | 1.0 | 1.0 | 1.0 | 1.0 | 1.0 | 1.0 | 1.0 | 22.2 | 1.0 | 1.0 | 1.0 | 1.0 | 1.0 | 1.0 | 1.0 |
| Lcn2 | 14.5 | 18.7 | 1.7 | 0.8 | 1.6 | 1.6 | 6.5 | 4.5 | 2.2 | 1.2 | 0.2 | 0.1 | 3.0 | 1.1 | 15.3 | 4.6 | 1.0 | 1.9 | 2.5 | 0.8 | 1.5 | 0.2 |
| Lcn5 | 1.0 | 1.0 | 1.0 | 1.0 | 1.0 | 1.0 | 1.0 | 1.0 | 1.0 | 1.0 | 1.0 | 1.0 | 1.0 | 1.0 | 635.9 | 1.0 | 1.0 | 1.0 | 1.0 | 1.0 | 1.0 | 1.0 |
| Lcn6 | 1.0 | 1.0 | 1.0 | 1.0 | 1.0 | 1.0 | 1.0 | 1.0 | 1.0 | 1.0 | 1.0 | 1.0 | 1.0 | 1.0 | 35.2 | 1.0 | 1.0 | 1.0 | 1.0 | 1.0 | 1.0 | 1.0 |
| Lcn8 | 1.0 | 1.0 | 1.0 | 1.0 | 1.0 | 1.0 | 1.0 | 1.0 | 1.0 | 1.0 | 1.0 | 1.0 | 1.0 | 1.0 | 599.2 | 1.0 | 1.0 | 1.0 | 1.0 | 1.0 | 1.0 | 1.0 |
| Lcn9 | 1.0 | 1.0 | 1.0 | 1.0 | 1.0 | 1.0 | 1.0 | 1.0 | 1.0 | 1.0 | 1.0 | 1.0 | 1.0 | 1.0 | 460.9 | 1.0 | 1.0 | 1.0 | 1.0 | 1.0 | 1.0 | 1.0 |
| Lct | 1.0 | 1.0 | 1.0 | 1.0 | 1.0 | 1.1 | 1.0 | 1.0 | 1.0 | 1.0 | 1.0 | 1.0 | 1.0 | 1.0 | 0.2 | 1.2 | 1.0 | 1.0 | 1.0 | 1.0 | 1.0 | 1.0 |
| Ldb3 | 1.0 | 1.0 | 1.0 | 1.1 | 0.7 | 0.7 | 1.0 | 1.0 | 1.0 | 1.0 | 1.0 | 1.0 | 1.0 | 1.0 | 1.0 | 1.0 | 0.7 | 0.9 | 0.3 | 1.0 | 1.0 | 1.1 |
| Lect1 | 1.0 | 1.0 | 1.0 | 1.0 | 1.0 | 1.0 | 1.4 | 1.2 | 0.1 | 0.2 | 1.0 | 1.0 | 1.2 | 1.0 | 1.0 | 1.0 | 1.0 | 1.0 | 1.0 | 1.0 | 1.0 | 1.0 |
| Lef1 | 1.0 | 1.0 | 0.6 | 1.0 | 0.3 | 1.0 | 1.0 | 1.0 | 1.0 | 1.0 | 1.0 | 1.0 | 0.8 | 0.9 | 5.0 | 1.0 | 1.0 | 1.0 | 1.0 | 1.0 | 1.0 | 1.0 |
| Lelp1 | 1.0 | 1.0 | 1.0 | 1.0 | 1.0 | 1.0 | 1.0 | 1.0 | 1.0 | 1.0 | 1.0 | 1.0 | 1.0 | 1.0 | 6.5 | 1.0 | 1.0 | 1.0 | 1.0 | 1.0 | 1.0 | 1.0 |
| Lgals7 | 1.0 | 1.0 | 1.0 | 1.0 | 1.0 | 0.8 | 1.0 | 1.0 | 1.0 | 1.0 | 1.0 | 1.1 | 1.3 | 1.7 | 1.3 | 1.7 | 1.0 | 1.0 | 1.0 | 1.0 | 1.0 | 1.0 |
| Lhfpl2 | 1.6 | 2.4 | 1.5 | 1.5 | 1.0 | 0.9 | 1.3 | 0.9 | 1.1 | 1.1 | 0.9 | 0.7 | 1.3 | 1.1 | 0.4 | 0.3 | 0.5 | 1.8 | 1.1 | 1.1 | 1.3 | 1.1 |
| Lingo1 | 1.0 | 1.0 | 1.0 | 1.0 | 1.0 | 0.9 | 1.1 | 0.8 | 1.0 | 1.0 | 1.0 | 1.0 | 1.4 | 1.0 | 33.4 | 1.0 | 1.0 | 1.0 | 1.0 | 1.0 | 1.0 | 1.0 |
| Lipf | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Lipg | 1.0 | 1.0 | 1.2 | 1.0 | 1.0 | 0.7 | 1.0 | 1.0 | 1.7 | 1.2 | 1.0 | 1.0 | 1.0 | 1.9 | 14.6 | 1.4 | 0.5 | 0.6 | 1.5 | 0.7 | 1.5 | 1.5 |
| Lipi | 1.0 | 1.0 | 1.0 | 1.0 | 1.0 | 1.0 | 1.0 | 1.0 | 1.0 | 1.0 | 1.0 | 1.0 | 1.0 | 1.0 | 6.7 | 1.0 | 1.0 | 1.0 | 1.0 | 1.0 | 1.0 | 1.0 |
| Lmod2 | 1.0 | 1.0 | 1.0 | 1.0 | 0.7 | 0.7 | 0.9 | 1.1 | 1.0 | 0.5 | 1.3 | 0.9 | 1.0 | 1.0 | 1.0 | 1.0 | 1.0 | 1.0 | 1.0 | 1.0 | 1.0 | 1.0 |
| Lmod3 | 1.0 | 1.0 | 1.0 | 1.0 | 0.7 | 0.6 | 0.7 | 0.8 | 1.0 | 1.0 | 1.2 | 0.8 | 1.0 | 6.9 | 1.0 | 1.0 | 1.0 | 1.0 | 1.0 | 1.0 | 1.0 | 1.0 |
| Lor | 1.0 | 1.0 | 1.0 | 0.7 | 1.0 | 0.6 | 1.0 | 1.0 | 1.6 | 1.2 | 1.0 | 1.0 | 3.3 | 0.9 | 1.8 | 0.5 | 1.1 | 1.0 | 1.0 | 1.9 | 1.0 | 0.6 |
| Loxl2 | 1.4 | 2.4 | 1.3 | 0.8 | 0.9 | 0.9 | 0.7 | 0.6 | 0.9 | 0.9 | 0.6 | 0.8 | 0.9 | 0.9 | 0.4 | 0.5 | 1.7 | 1.8 | 1.7 | 1.0 | 1.0 | 1.5 |
| Lpl | 0.5 | 0.3 | 0.6 | 1.1 | 0.7 | 0.9 | 1.1 | 1.3 | 0.7 | 1.0 | 0.7 | 1.3 | 1.3 | 2.2 | 0.5 | 0.8 | 0.7 | 1.3 | 0.6 | 0.7 | 0.4 | 0.9 |
| Lrp11 | 1.0 | 1.0 | 1.0 | 1.0 | 1.0 | 1.0 | 1.0 | 1.0 | 1.0 | 1.0 | 1.0 | 1.0 | 1.0 | 1.0 | 42.3 | 1.0 | 1.0 | 1.0 | 1.0 | 1.0 | 1.0 | 1.0 |
| Lrrc16a | 0.9 | 1.4 | 0.9 | 1.0 | 1.0 | 1.2 | 0.9 | 1.0 | 0.1 | 0.2 | 1.0 | 1.0 | 1.2 | 1.4 | 2.1 | 1.1 | 1.1 | 1.1 | 1.1 | 1.1 | 1.1 | 1.1 |
| Lrrc26 | 1.5 | 0.9 | 1.0 | 1.1 | 0.9 | 0.9 | 1.0 | 1.0 | 1.0 | 1.0 | 1.3 | 1.1 | 1.7 | 1.0 | 2.0 | 1.0 | 1.0 | 0.9 | 1.2 | 1.1 | 1.0 | 1.0 |
| Lrrc30 | 1.0 | 1.0 | 1.0 | 1.0 | 1.1 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Lst1 | 1.0 | 2.3 | 1.0 | 0.4 | 0.3 | 1.1 | 1.0 | 1.2 | 0.6 | 1.1 | 0.4 | 1.1 | 0.7 | 0.5 | 1.6 | 0.8 | 0.4 | 0.5 | 1.3 | 0.3 | 0.4 | 0.6 | 0.7 | 1.0 |
| Ltb | 1.0 | 0.6 | 0.5 | 0.3 | 1.0 | 1.0 | 1.0 | 0.8 | 0.7 | 0.5 | 0.3 | 1.0 | 1.2 | 0.8 | 0.5 | 1.3 | 1.2 | 0.8 | 1.0 | 0.9 | 0.8 | 0.5 |
| Ltf | 1.0 | 1.0 | 1.0 | 1.0 | 1.2 | 1.1 | 1.0 | 1.0 | 1.0 | 1.0 | 1.0 | 1.0 | 2.8 | 0.8 | 2.2 | 1.0 | 0.8 | 1.9 | 1.0 | 1.0 | 1.0 | 1.0 |
| Ly6d | 1.2 | 0.7 | 0.4 | 0.3 | 1.0 | 1.0 | 0.9 | 1.1 | 4.0 | 1.9 | 0.7 | 0.7 | 1.0 | 1.1 | 1.2 | 1.5 | 1.1 | 1.1 | 0.9 | 1.0 | 1.2 | 0.8 |
| Ly6g5b | 1.0 | 1.0 | 1.0 | 1.1 | 1.3 | 1.7 | 1.1 | 1.0 | 1.0 | 1.0 | 1.0 | 1.0 | 1.0 | 1.0 | 567.5 | 1.0 | 1.0 | 1.0 | 1.1 | 1.0 | 1.4 | 9.9 |
| Ly6g5c | 1.0 | 1.0 | 1.0 | 1.0 | 1.0 | 1.0 | 1.0 | 1.0 | 1.0 | 1.0 | 1.0 | 1.0 | 1.0 | 1.0 | 179.6 | 1.0 | 1.0 | 1.0 | 1.0 | 1.0 | 1.0 | 1.0 |
| Lypd8 | 1.0 | 1.0 | 1.0 | 1.0 | 1.5 | 1.0 | 0.7 | 1.0 | 1.0 | 1.0 | 1.0 | 1.0 | 1.1 | 0.6 | 286.6 | 0.2 | 0.7 | 1.1 | 1.5 | 1.1 | 1.1 | 0.9 |
| Lya1 | 1.0 | 2.8 | 0.8 | 0.6 | 0.5 | 0.9 | 1.1 | 1.3 | 1.0 | 1.0 | 0.5 | 0.8 | 1.9 | 1.2 | 0.5 | 0.6 | 1.1 | 1.5 | 0.8 | 1.1 | 1.2 | 1.0 |
| Lya2 | 1.3 | 6.0 | 1.1 | 0.5 | 0.9 | 0.9 | 0.9 | 1.1 | 0.9 | 1.7 | 0.9 | 1.3 | 1.0 | 0.5 | 0.7 | 1.1 | 1.3 | 0.9 | 0.7 | 0.5 | 0.7 |
| Mafa | 1.0 | 1.0 | 1.0 | 1.0 | 0.9 | 0.3 | 1.0 | 1.0 | 1.0 | 1.0 | 1.0 | 1.0 | 1.1 | 1.0 | 1.0 | 1.0 | 1.0 | 1.0 | 1.0 | 1.0 | 1.0 | 1.0 |
| Mafb | 1.2 | 1.5 | 1.4 | 1.0 | 0.9 | 0.8 | 1.1 | 1.2 | 0.7 | 0.8 | 0.6 | 0.7 | 1.9 | 1.3 | 0.7 | 0.7 | 1.6 | 1.8 | 1.1 | 1.0 | 1.6 | 1.4 |
| Mal | 1.1 | 1.0 | 1.9 | 2.0 | 1.0 | 1.3 | 0.8 | 0.9 | 1.0 | 1.0 | 1.0 | 1.0 | 1.0 | 1.0 | 15.9 | 3.7 | 0.5 | 0.8 | 1.2 | 1.2 | 0.5 | 0.5 |
| Malat1 | 1.6 | 1.3 | 0.8 | 0.8 | 1.2 | 0.8 | 1.0 | 1.3 | 1.7 | 0.3 | 0.8 | 1.0 | 0.6 | 0.7 | 0.9 | 0.8 | 0.8 | 1.0 | 0.7 | 0.9 | 0.9 | 1.2 |
| Map3k7cl | 0.6 | 0.6 | 1.0 | 1.0 | 0.5 | 0.5 | 1.0 | 0.7 | 1.0 | 1.0 | 1.0 | 1.0 | 0.9 | 1.1 | 0.9 | 0.5 | 1.0 | 1.1 | 1.0 | 1.0 | 1.0 | 1.0 |
| Marss | 1.0 | 1.0 | 0.7 | 1.0 | 1.0 | 1.0 | 1.0 | 1.0 | 1.2 | 0.9 | 1.0 | 1.0 | 1.0 | 1.0 | 1.0 | 1.0 | 8.9 | 0.2 | 1.0 | 1.0 | 1.0 | 1.0 |
| Mb | 1.0 | 1.0 | 0.4 | 1.0 | 0.8 | 0.2 | 1.0 | 1.1 | 1.0 | 1.0 | 1.0 | 1.0 | 0.4 | 2.2 | 2.0 | 3.0 | 0.4 | 1.2 | 1.0 | 1.0 | 1.0 | 1.0 |
| Mbnl3 | 1.0 | 1.0 | 1.0 | 0.9 | 1.2 | 1.3 | 1.0 | 1.0 | 1.0 | 1.0 | 1.4 | 1.4 | 0.6 | 0.8 | 7.7 | 1.0 | 1.1 | 0.9 | 1.3 | 0.8 | 1.1 | 1.0 |
| Mboat1 | 1.0 | 1.4 | 0.9 | 0.9 | 1.1 | 1.2 | 1.0 | 1.0 | 1.0 | 1.0 | 0.7 | 0.7 | 1.1 | 1.0 | 5.5 | 1.2 | 1.0 | 1.0 | 1.5 | 1.0 | 1.0 | 1.0 |
| Mcm10 | 0.7 | 0.9 | 1.0 | 0.6 | 1.0 | 1.1 | 1.0 | 1.0 | 0.1 | 0.2 | 1.0 | 1.0 | 0.5 | 0.2 | 1.0 | 1.0 | 1.1 | 1.2 | 1.0 | 1.0 | 1.0 | 0.2 |
| Mcpt3 | 1.0 | 1.0 | 1.0 | 0.2 | 1.0 | 1.0 | 1.0 | 1.0 | 1.0 | 1.0 | 1.0 | 1.0 | 1.0 | 1.0 | 1.0 | 1.0 | 2.8 | 1.1 | 0.9 | 3.2 | 0.5 | 0.2 |
| Mcpt2 | 1.0 | 1.0 | 0.2 | 0.4 | 1.0 | 1.0 | 1.0 | 1.0 | 1.0 | 1.0 | 1.0 | 1.0 | 1.0 | 1.0 | 1.0 | 1.0 | 2.2 | 1.1 | 1.0 | 0.3 | 0.4 |
| Mdk | 0.4 | 0.8 | 1.1 | 1.1 | 0.9 | 1.0 | 0.7 | 1.0 | 1.0 | 1.0 | 0.4 | 0.5 | 1.8 | 1.5 | 1.2 | 5.0 | 0.9 | 1.4 | 1.5 | 0.5 | 0.8 | 0.7 |
| Mef2b | 1.0 | 1.0 | 1.0 | 0.5 | 1.0 | 0.9 | 1.0 | 1.0 | 1.0 | 1.0 | 1.0 | 1.0 | 1.0 | 1.4 | 1.0 | 1.0 | 1.0 | 1.0 | 1.0 | 1.0 | 0.8 | 0.9 |
| Megf6 | 1.7 | 1.4 | 1.0 | 0.9 | 1.3 | 1.1 | 0.6 | 0.7 | 2.1 | 1.0 | 0.9 | 1.1 | 0.8 | 0.9 | 0.6 | 0.3 | 0.7 | 1.1 | 1.0 | 0.5 | 1.0 | 3.7 |
| Meox1 | 0.9 | 1.3 | 0.8 | 0.9 | 0.8 | 1.1 | 0.5 | 0.6 | 1.0 | 1.0 | 0.8 | 0.7 | 1.7 | 1.2 | 0.3 | 0.4 | 0.8 | 1.0 | 0.9 | 0.7 | 0.7 | 1.0 |
| Mesp1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mesp2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 0.9 | 0.5 | 1.0 | 1.0 | 1.0 | 1.0 |
| Mesi | 1.0 | 0.9 | 0.8 | 1.8 | 0.9 | 1.0 | 0.4 | 0.4 | 1.0 | 0.9 | 1.0 | 1.0 | 1.0 | 1.0 | 0.3 | 0.5 | 0.6 | 0.8 | 1.0 | 1.0 | 1.0 | 1.0 |
| Mettl21c | 1.0 | 1.0 | 1.0 | 1.0 | 1.0 | 1.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Mfrp | 1.3 | 1.0 | 1.0 | 1.0 | 8.0 | 0.5 | 1.0 | 1.0 | 1.0 | 1.0 | 1.0 | 1.0 | 1.0 | 1.0 | 11.7 | 1.0 | 1.0 | 1.0 | 1.0 | 1.0 | 1.0 | 1.0 |
| Mfsd2a | 0.5 | 0.6 | 0.9 | 0.7 | 1.1 | 1.0 | 1.0 | 1.0 | 1.9 | 2.5 | 1.0 | 1.0 | 1.0 | 1.0 | 11.0 | 1.0 | 1.1 | 0.9 | 0.7 | 0.6 | 2.0 | 1.9 |
| Mid1 | 0.2 | 0.6 | 0.8 | 0.6 | 0.6 | 0.3 | 0.8 | 0.1 | 0.7 | 0.2 | 0.8 | 6.3 | 1.0 | 0.5 | 0.5 | 0.8 | 0.5 | 1.0 | 0.7 | 0.4 | 0.8 |
| Amy2a5 | 1.8 | 2.0 | 3.8 | 0.3 | 1.0 | 0.2 | 1.0 | 1.2 | 0.3 | 0.6 | 1.1 | 0.7 | 0.6 | 0.3 | 4.4 | 2.1 | 0.4 | 1.2 | 67.1 | 2.1 | 0.5 | 1.0 |
| Kcnk5 | 1.0 | 1.0 | 1.0 | 1.0 | 0.9 | 1.0 | 1.0 | 1.0 | 1.0 | 1.0 | 1.0 | 1.0 | 1.0 | 1.0 | 1.0 | 5.5 | 1.0 | 1.0 | 1.0 | 7.4 | 1.0 | 1.0 |
| Mlf1 | 1.0 | 1.0 | 1.0 | 1.0 | 0.7 | 0.9 | 1.0 | 1.0 | 1.0 | 1.0 | 1.0 | 1.0 | 1.0 | 1.0 | 1.3 | 1.6 | 1.0 | 1.0 | 1.0 | 1.0 | 1.0 | 1.0 |
| Mmp12 | 1.0 | 6.6 | 1.0 | 1.0 | 1.0 | 1.0 | 1.0 | 1.0 | 1.0 | 1.0 | 1.0 | 1.0 | 1.0 | 1.0 | 0.3 | 1.0 | 8.4 | 14.6 | 1.0 | 1.0 | 1.0 | 1.0 |
| Mmp7 | 1.0 | 1.0 | 1.0 | 1.8 | 1.2 | 1.0 | 1.0 | 1.0 | 1.0 | 1.0 | 1.0 | 1.0 | 1.5 | 1.0 | 1.0 | 5.0 | 1.0 | 0.8 | 0.6 | 1.0 | 1.0 | 0.8 |
| Motx1 | 1.0 | 1.0 | 0.0 | 0.1 | 1.0 | 1.0 | 1.0 | 1.0 | 1.0 | 1.0 | 1.0 | 1.0 | 1.0 | 1.0 | 1.0 | 0.7 | 1.0 | 1.0 | 1.2 | 1.1 | 0.7 | 0.7 |
| Motx2 | 1.0 | 1.0 | 0.1 | 0.1 | 1.0 | 1.0 | 1.0 | 1.0 | 1.0 | 1.0 | 1.0 | 1.0 | 1.0 | 1.0 | 567.5 | 1.0 | 1.0 | 1.0 | 1.2 | 1.2 | 1.2 | 1.0 |
| Mpz | 1.0 | 1.0 | 1.0 | 1.0 | 0.3 | 0.5 | 1.0 | 1.0 | 0.5 | 0.8 | 1.0 | 1.0 | 1.0 | 1.0 | 1.0 | 1.0 | 1.1 | 1.0 | 1.0 | 1.0 | 1.0 | 1.0 |
| Mrgp | 1.0 | 1.0 | 1.0 | 1.6 | 0.9 | 0.3 | 1.3 | 1.6 | 0.8 | 0.7 | 1.0 | 2.6 | 2.2 | 3.3 | 0.6 | 1.2 | 0.6 | 0.6 | 0.8 | 1.4 | 0.7 | 1.4 |
| Ms4a3 | 1.0 | 1.0 | 0.4 | 0.2 | 1.0 | 1.0 | 1.0 | 1.0 | 1.0 | 1.0 | 0.5 | 2.5 | 1.2 | 1.0 | 1.0 | 1.0 | 1.0 | 1.0 | 0.5 | 0.6 | 0.7 | 0.2 |

[Fig. 23-24]

[Fig. 23-25]

Due to the extreme density and low resolution of this tabular data (a gene expression table with ~80 rows and 24 numeric columns), reliable OCR of individual cell values cannot be performed without fabrication.

| | | | | | | | | | | | | | | | | | | | | | |
|---|---|---|---|---|---|---|---|---|---|---|---|---|---|---|---|---|---|---|---|---|---|
| Saa1 | 1.2 | 1.3 | 1.2 | 1.3 | 1.0 | 1.0 | 1.0 | 1.0 | 0.3 | 0.2 | 1.0 | 1.0 | 1.2 | 0.3 | 1.0 | 1.0 | 1.0 | 0.7 | 6.6 | 4.5 | 2.0 | 1.3 |
| Saa2 | 1.0 | 1.0 | 1.4 | 1.1 | 1.0 | 1.0 | 1.0 | 1.0 | 0.3 | 0.2 | 1.0 | 1.0 | 1.2 | 1.0 | 1.0 | 1.0 | 1.0 | 1.0 | 1.0 | 1.0 | 1.7 | 0.8 |
| Saa3 | 1.0 | 1.0 | 0.7 | 0.3 | 1.0 | 1.0 | 1.9 | 1.9 | 1.1 | 3.3 | 1.0 | 1.0 | 1.8 | 0.4 | 0.3 | 0.7 | 5.0 | 2.7 | 3.0 | 1.0 | 0.7 | 0.2 |
| Sash3 | 1.0 | 1.3 | 0.6 | 0.8 | 1.0 | 1.0 | 0.7 | 1.0 | 1.0 | 1.0 | 0.9 | 1.1 | 0.7 | 0.8 | 0.6 | 0.6 | 1.0 | 1.7 | 0.8 | 0.7 | 0.7 | 0.7 |
| Sbk2 | 1.0 | 1.0 | 1.0 | 1.0 | 0.8 | 0.7 | 0.8 | 0.8 | 1.0 | 1.0 | 1.0 | 1.0 | 1.0 | 1.0 | 0.6 | 1.7 | 1.0 | 1.0 | 1.0 | 1.0 | 1.0 | 1.0 |
| Sbp | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sbpl | 1.0 | 1.0 | 1.0 | 1.0 | 1.0 | 1.0 | 1.0 | 1.0 | 1.0 | 1.0 | 1.0 | 1.0 | 1.7 | 0.9 | 1.0 | 1.0 | 1.0 | 1.0 | 1.0 | 1.0 | 1.0 | 1.0 |
| Scara5 | 1.3 | 0.8 | 1.4 | 1.2 | 0.8 | 0.7 | 1.1 | 1.0 | 0.4 | 0.2 | 0.7 | 0.2 | 1.5 | 2.0 | 0.7 | 0.6 | 0.8 | 0.9 | 1.0 | 1.0 | 1.2 | 1.0 |
| Scarna3b | 1.0 | 1.0 | 1.0 | 1.0 | 1.0 | 1.0 | 1.0 | 1.0 | 1.0 | 1.0 | 1.0 | 1.0 | 0.6 | 1.0 | 1.0 | 1.0 | 1.0 | 1.0 | 1.0 | 1.0 | 1.0 | 1.0 |
| Scarna8 | 1.0 | 1.0 | 1.0 | 1.0 | 1.0 | 1.0 | 1.0 | 1.0 | 1.0 | 1.0 | 1.0 | 1.0 | 1.0 | 0.0 | 1.0 | 1.0 | 1.0 | 1.0 | 1.0 | 1.0 | 1.0 | 1.0 |
| Scd1 | 3.1 | 2.9 | 0.4 | 1.1 | 0.6 | 0.7 | 2.5 | 0.6 | 1.5 | 0.5 | 0.8 | 2.3 | 0.7 | 2.8 | 0.5 | 1.1 | 0.4 | 0.6 | 0.5 | 0.8 | 0.4 | 1.6 |
| Scd2 | 1.5 | 2.0 | 1.0 | 0.8 | 1.0 | 1.0 | 1.3 | 0.8 | 2.1 | 0.6 | 0.9 | 0.9 | 0.6 | 0.8 | 1.8 | 0.5 | 1.0 | 0.9 | 1.9 | 1.0 | 1.2 | 0.7 |
| Slc15a2 | 2.0 | 2.6 | 0.5 | 1.0 | 1.1 | 0.9 | 1.0 | 0.8 | 2.5 | 0.3 | 1.0 | 1.6 | 0.6 | 2.2 | 0.7 | 0.7 | 0.3 | 0.7 | 0.7 | 1.0 | 0.5 | 2.0 |
| Scd4 | 1.0 | 1.0 | 1.0 | 1.0 | 1.0 | 1.0 | 0.4 | 1.2 | 2.6 | 0.1 | 1.0 | 1.0 | 1.1 | 1.7 | 0.8 | 0.7 | 1.0 | 1.0 | 1.0 | 1.0 | 0.9 | 1.0 |
| Scnm64 | 1.2 | 1.0 | 1.0 | 8.4 | 1.0 | 0.8 | 1.0 | 0.9 | 1.4 | 1.0 | 1.3 | 1.0 | 0.8 | 10.1 | 1.0 | 12.7 | 0.7 | 0.9 | 1.0 | 0.6 | 1.0 | 1.0 |
| Aco1 | 1.7 | 1.0 | 1.0 | 1.0 | 1.0 | 0.9 | 1.0 | 0.7 | 0.5 | 1.0 | 1.0 | 0.8 | 1.0 | 2.8 | 1.0 | 12.5 | 1.0 | 1.3 | 1.0 | 1.0 | 1.0 | 1.0 |
| Scgb2b12 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Scgb2b15 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 2.0 | 0.8 | 0.3 |
| Scgb2b17 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 2.0 | 1.0 | 0.2 |
| Scgb2b20 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Scgb2b27 | 1.2 | 1.0 | 1.0 | 1.0 | 1.0 | 0.6 | 1.0 | 0.6 | 0.7 | 1.0 | 1.0 | 0.8 | 1.0 | 2.0 | 1.0 | 6.2 | 1.0 | 1.5 | 1.0 | 1.0 | 1.0 | 1.0 |
| Scgb3a1 | 1.0 | 1.0 | 1.0 | 1.0 | 1.0 | 1.0 | 2.0 | 1.2 | 1.0 | 1.0 | 1.0 | 1.0 | 1.0 | 1.0 | 1.0 | 1.0 | 0.9 | 1.0 | 0.6 | 0.6 | 0.5 | 0.4 |
| Scgb3a2 | 1.0 | 1.0 | 1.0 | 1.0 | 1.0 | 1.0 | 1.0 | 1.3 | 1.0 | 1.0 | 1.0 | 1.0 | 1.0 | 1.0 | 1.0 | 1.0 | 1.0 | 1.0 | 1.0 | 1.0 | 1.0 | 1.0 |
| Scn8b | 1.2 | 1.3 | 1.0 | 1.0 | 0.7 | 0.6 | 0.6 | 0.7 | 1.0 | 1.0 | 1.0 | 0.7 | 0.9 | 1.1 | 0.8 | 0.9 | 0.8 | 1.6 | 1.0 | 1.0 | 1.0 | 1.0 |
| Scx | 1.1 | 1.3 | 2.3 | 1.0 | 1.3 | 0.8 | 0.7 | 1.7 | 1.0 | 1.0 | 1.1 | 0.6 | 2.5 | 2.7 | 5.9 | 1.0 | 1.4 | 1.1 | 1.0 | 1.0 | 1.0 | 1.0 |
| Sec14l3 | 0.3 | 0.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Selenbp2 | 0.7 | 0.7 | 1.2 | 1.2 | 0.8 | 1.2 | 1.2 | 1.1 | 0.3 | 0.2 | 1.3 | 1.3 | 1.5 | 1.0 | 0.8 | 1.6 | 1.3 | 0.8 | 1.1 | 1.0 | 1.0 | 1.1 |
| Selt | 1.0 | 1.0 | 0.2 | 0.3 | 1.0 | 1.0 | 1.0 | 1.0 | 1.0 | 0.5 | 2.3 | 0.9 | 1.0 | 1.0 | 0.2 | 1.1 | 1.0 | 1.0 | 1.0 | 0.7 | 0.6 | 0.5 |
| Serinc2 | 0.8 | 0.8 | 1.1 | 1.0 | 0.7 | 0.5 | 1.0 | 1.0 | 1.2 | 1.6 | 1.0 | 0.8 | 2.6 | 0.9 | 23.4 | 1.0 | 1.1 | 1.0 | 1.2 | 1.3 | 1.1 | 1.0 |
| Serpina10 | 4.0 | 11.1 | 0.6 | 1.0 | 1.0 | 1.0 | 1.0 | 1.0 | 0.9 | 1.0 | 1.0 | 1.0 | 1.0 | 1.0 | 1.0 | 1.0 | 1.0 | 1.0 | 1.0 | 1.0 | 1.2 | 1.0 |
| Serpina12 | 1.0 | 1.0 | 1.0 | 1.0 | 1.0 | 1.0 | 1.0 | 1.0 | 0.3 | 0.2 | 1.0 | 1.0 | 1.0 | 1.0 | 1.0 | 0.9 | 0.9 | 1.0 | 1.0 | 1.0 | 1.6 | 1.0 |
| Serpina1a | 4.6 | 4.6 | 0.2 | 1.0 | 1.0 | 1.0 | 1.0 | 1.0 | 0.5 | 0.5 | 1.0 | 1.0 | 1.0 | 1.0 | 0.3 | 0.4 | 14.5 | 0.1 | 0.9 | 0.7 | 0.9 | 1.2 |
| Serpina1b | 4.4 | 3.3 | 0.2 | 1.0 | 1.0 | 1.0 | 1.0 | 1.0 | 0.5 | 0.6 | 0.8 | 1.0 | 1.0 | 1.0 | 0.3 | 0.8 | 20.2 | 0.0 | 1.0 | 1.3 | 0.9 | 1.0 |
| Serpina1c | 3.9 | 3.1 | 0.2 | 1.0 | 1.0 | 1.0 | 1.0 | 1.0 | 0.4 | 0.4 | 0.9 | 1.0 | 1.0 | 1.0 | 0.3 | 0.5 | 21.7 | 0.0 | 0.7 | 1.0 | 0.8 | 0.7 |
| Serpina1d | 2.1 | 1.5 | 0.2 | 1.0 | 1.0 | 1.0 | 1.0 | 1.0 | 0.5 | 0.5 | 1.2 | 1.0 | 1.0 | 1.0 | 0.3 | 0.6 | 13.0 | 0.1 | 1.0 | 1.0 | 1.1 | 1.0 |
| Serpina1e | 3.2 | 3.1 | 0.2 | 1.0 | 1.0 | 1.0 | 1.0 | 1.0 | 0.3 | 0.1 | 1.0 | 1.0 | 1.0 | 1.0 | 0.3 | 0.7 | 8.5 | 0.0 | 1.0 | 2.5 | 1.1 | 0.9 |
| Serpina3f | 1.2 | 1.2 | 1.0 | 1.0 | 1.0 | 1.0 | 1.0 | 1.0 | 1.0 | 1.0 | 1.0 | 1.0 | 1.0 | 1.0 | 18.2 | 11.1 | 1.0 | 1.0 | 1.0 | 1.0 | 1.0 | 1.0 |
| Serpina3c | 1.0 | 1.0 | 0.9 | 1.6 | 1.0 | 1.0 | 1.3 | 1.0 | 0.3 | 0.5 | 1.0 | 1.0 | 2.0 | 2.1 | 0.7 | 0.9 | 1.9 | 1.0 | 1.0 | 1.0 | 0.8 | 1.0 |
| Serpina3k | 2.9 | 1.0 | 0.2 | 1.0 | 1.0 | 1.0 | 1.0 | 1.0 | 0.3 | 0.3 | 0.8 | 1.0 | 1.0 | 1.0 | 0.3 | 0.9 | 13.3 | 0.0 | 1.0 | 1.0 | 1.0 | 1.0 |
| Serpina4-ps1 | 1.0 | 1.0 | 1.0 | 1.0 | 1.0 | 1.0 | 1.0 | 1.0 | 0.3 | 0.1 | 1.0 | 1.0 | 1.0 | 1.0 | 1.0 | 1.0 | 1.0 | 0.6 | 1.0 | 1.0 | 1.0 | 1.0 |
| Serpina11 | 1.0 | 1.0 | 1.0 | 1.0 | 1.2 | 1.6 | 1.0 | 1.0 | 1.0 | 1.0 | 1.1 | 1.0 | 2.4 | 1.4 | 1.0 | 1.0 | 0.9 | 1.2 | 1.0 | 1.0 | 1.0 | 1.0 |
| Serpinb3a | 1.0 | 1.0 | 1.0 | 1.0 | 0.7 | 1.2 | 1.0 | 1.0 | 1.0 | 1.0 | 1.0 | 1.0 | 0.2 | 0.4 | 1.0 | 1.0 | 1.1 | 1.0 | 1.0 | 1.0 | 1.0 | 1.0 |
| Serpinb6d | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Serpinb6e | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Serpinc1 | 1.0 | 2.2 | 0.7 | 1.0 | 1.0 | 1.0 | 1.0 | 1.0 | 1.1 | 1.2 | 1.0 | 1.0 | 1.0 | 0.7 | 1.0 | 1.0 | 6.0 | 0.3 | 1.0 | 1.0 | 1.0 | 1.0 |
| Serpinf2 | 0.4 | 0.4 | 1.0 | 1.0 | 1.0 | 1.0 | 1.0 | 1.0 | 0.7 | 0.8 | 1.0 | 1.0 | 1.0 | 1.0 | 11.5 | 1.0 | 2.0 | 0.7 | 0.8 | 1.8 | 1.0 | 1.0 |
| Sfrp5 | 1.0 | 1.0 | 1.0 | 0.9 | 0.7 | 0.8 | 1.0 | 1.0 | 1.0 | 1.0 | 1.2 | 0.9 | 1.0 | 1.0 | 0.2 | 0.2 | 0.8 | 0.8 | 0.4 | 0.5 | 0.5 | 9.6 |
| Sgca | 1.0 | 1.0 | 1.0 | 1.0 | 0.8 | 0.8 | 1.2 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sgcg | 1.0 | 1.0 | 1.0 | 1.0 | 0.8 | 0.8 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Sh3bp2 | 0.3 | 0.4 | 1.0 | 0.7 | 0.5 | 0.9 | 0.9 | 1.0 | 1.0 | 1.0 | 0.8 | 1.0 | 1.2 | 0.9 | 1.1 | 0.6 | 0.5 | 1.1 | 1.0 | 1.0 | 1.4 | 1.1 |
| Sh3gl2 | 0.8 | 0.8 | 1.1 | 1.1 | 1.0 | 0.7 | 1.0 | 1.0 | 1.0 | 1.0 | 1.0 | 1.0 | 1.0 | 1.6 | 7.3 | 1.0 | 0.6 | 0.9 | 1.1 | 1.0 | 1.1 | 1.3 |
| Sh2d4 | 1.0 | 1.0 | 1.0 | 1.0 | 0.9 | 0.8 | 1.0 | 1.0 | 1.0 | 1.0 | 1.0 | 1.0 | 1.0 | 1.0 | 5.2 | 1.0 | 1.0 | 1.0 | 1.0 | 1.0 | 1.0 | 1.0 |
| Shh | 1.0 | 1.0 | 1.0 | 1.0 | 1.0 | 0.8 | 1.0 | 1.0 | 1.0 | 1.0 | 1.0 | 1.0 | 1.0 | 1.0 | 3.2 | 1.0 | 0.8 | 0.9 | 1.0 | 1.0 | 1.0 | 1.0 |
| Foxn3 | 0.7 | 1.0 | 0.2 | 0.7 | 0.4 | 1.0 | 0.3 | 0.8 | 0.5 | 1.4 | 0.7 | 1.0 | 0.2 | 0.5 | 0.7 | 1.3 | 0.5 | 0.9 | 0.3 | 0.9 | 0.2 | 1.2 |
| Slc16a3 | 1.0 | 1.1 | 0.3 | 0.8 | 0.9 | 0.8 | 1.3 | 1.2 | 1.0 | 1.0 | 0.6 | 0.4 | 1.9 | 0.7 | 1.3 | 1.4 | 1.0 | 1.7 | 1.5 | 1.0 | 1.3 | 1.1 |
| Slc16a9 | 1.1 | 1.0 | 1.3 | 1.3 | 1.0 | 0.9 | 0.9 | 0.7 | 1.1 | 1.1 | 1.0 | 1.0 | 1.3 | 0.8 | 0.7 | 0.6 | 1.0 | 1.3 | 5.4 | 2.3 | 1.0 | 1.0 |
| Slc17a9 | 1.0 | 1.0 | 1.0 | 1.1 | 1.1 | 1.1 | 1.0 | 1.0 | 1.0 | 0.6 | 1.1 | 1.1 | 1.6 | 1.3 | 12.0 | 1.1 | 1.2 | 1.1 | 0.5 | 0.9 | 0.9 | 0.9 |
| Slc1a1 | 0.7 | 0.8 | 1.0 | 1.0 | 1.0 | 0.6 | 1.0 | 1.0 | 1.0 | 1.0 | 1.0 | 1.0 | 1.0 | 1.0 | 8.1 | 0.5 | 1.0 | 1.0 | 1.1 | 1.0 | 0.6 | 0.9 |
| Slc22a26 | 0.8 | 0.5 | 1.0 | 1.0 | 1.0 | 1.0 | 1.0 | 1.0 | 2.5 | 9.6 | 1.0 | 1.0 | 1.0 | 1.0 | 1.0 | 1.0 | 1.0 | 1.0 | 1.0 | 1.0 | 1.0 | 1.0 |
| Slc22a27 | 0.7 | 1.0 | 1.0 | 1.0 | 1.0 | 1.0 | 1.0 | 1.0 | 3.2 | 2.7 | 1.0 | 1.0 | 1.0 | 1.0 | 1.0 | 1.0 | 1.0 | 1.0 | 1.0 | 1.0 | 1.0 | 1.0 |
| Slc22a28 | 0.3 | 0.2 | 1.0 | 1.0 | 1.0 | 1.0 | 1.0 | 1.0 | 0.5 | 0.4 | 1.0 | 1.0 | 1.0 | 1.0 | 1.0 | 1.0 | 1.0 | 1.0 | 1.0 | 1.0 | 1.0 | 1.0 |
| Slc22a30 | 0.3 | 0.2 | 1.0 | 1.0 | 1.0 | 1.0 | 1.0 | 1.0 | 0.5 | 0.5 | 1.0 | 1.0 | 1.0 | 1.0 | 1.0 | 1.0 | 1.0 | 1.0 | 1.0 | 1.0 | 1.0 | 1.0 |
| Slc22a7 | 0.2 | 0.1 | 1.0 | 1.0 | 1.0 | 1.0 | 1.0 | 1.0 | 0.3 | 0.1 | 1.0 | 1.0 | 0.6 | 1.6 | 1.0 | 1.0 | 1.0 | 1.0 | 1.0 | 1.0 | 1.0 | 1.0 |
| Slc25a30 | 1.4 | 1.0 | 1.2 | 1.0 | 0.8 | 0.8 | 0.6 | 0.8 | 0.3 | 0.4 | 0.6 | 1.0 | 0.8 | 1.0 | 1.0 | 0.7 | 0.9 | 1.6 | 1.0 | 0.7 | 1.2 | 1.0 |
| Slc25a47 | 1.2 | 0.9 | 0.7 | 1.3 | 0.9 | 0.9 | 1.1 | 1.4 | 1.1 | 1.1 | 1.0 | 1.1 | 1.2 | 1.3 | 5.4 | 1.9 | 2.7 | 0.7 | 1.4 | 0.8 | 0.8 | 1.2 |
| Slc30a10 | 1.0 | 1.0 | 4.7 | 28.6 | 1.3 | 1.0 | 1.0 | 1.0 | 1.0 | 1.0 | 1.0 | 1.0 | 1.0 | 1.0 | 1.0 | 1.0 | 1.0 | 1.0 | 2.0 | 1.7 | 5.3 | 14.7 |

| | Kidney | | Colon | | Eyeball | | Heart | | Liver | | SG | | Thymus | | Adipose | | Stomach | | Jejunum | | Ileum | |
|---|---|---|---|---|---|---|---|---|---|---|---|---|---|---|---|---|---|---|---|---|---|---|
| | F | M | F | M | F | M | F | M | F | M | F | M | F | M | F | M | F | M | F | M | F | M |
| Slc34a3 | 1.9 | 2.3 | 1.1 | 1.8 | 1.0 | 1.3 | 1.0 | 1.0 | 1.0 | 1.0 | 1.0 | 1.0 | 1.0 | 1.0 | 7.0 | 1.0 | 0.8 | 0.9 | 1.0 | 0.4 | 0.9 | 0.8 |
| Slc35f2 | 1.0 | 0.9 | 1.8 | 1.2 | 1.2 | 1.1 | 1.0 | 1.0 | 1.0 | 1.0 | 1.0 | 1.0 | 0.9 | 0.9 | 6.8 | 1.1 | 1.3 | 1.0 | 1.6 | 1.3 | 1.3 | 1.3 |
| Slc38a3 | 4.3 | 5.2 | 1.0 | 1.0 | 1.0 | 1.1 | 1.0 | 1.3 | 0.5 | 0.6 | 1.0 | 1.0 | 1.0 | 1.0 | 0.7 | 1.4 | 3.2 | 0.9 | 1.0 | 1.0 | 1.0 | 1.0 |
| Slc38a5 | 1.0 | 1.0 | 1.0 | 1.0 | 1.0 | 1.0 | 1.0 | 1.0 | 1.0 | 1.0 | 1.0 | 1.0 | 1.0 | 1.0 | 97.0 | 1.0 | 0.7 | 0.6 | 1.0 | 1.0 | 1.0 | 1.0 |
| Slc43a1 | 1.2 | 1.1 | 1.0 | 1.0 | 1.1 | 0.9 | 1.6 | 1.5 | 0.3 | 0.2 | 1.5 | 1.2 | 0.7 | 1.1 | 1.4 | 3.0 | 1.0 | 0.8 | 1.0 | 1.0 | 1.0 | 1.3 |
| Slc4a1 | 1.2 | 1.2 | 1.0 | 1.0 | 1.4 | 1.6 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc6lb | 0.9 | 1.3 | 1.0 | 1.6 | 1.0 | 1.0 | 1.0 | 1.0 | 1.0 | 5.9 | 1.0 | 1.0 | 1.0 | 1.0 | 1.0 | 1.0 | 1.0 | 1.0 | 1.7 | 3.6 | 0.9 | 0.7 |
| Slc7a12 | 1.9 | 7.2 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Slc7a5 | 1.3 | 1.3 | 1.0 | 1.1 | 1.2 | 1.1 | 1.0 | 1.3 | 1.4 | 1.1 | 1.0 | 1.6 | 0.9 | 1.0 | 24.0 | 1.2 | 1.0 | 1.2 | 1.1 | 1.0 | 1.0 | 0.9 |
| Slc7a8 | 1.3 | 1.0 | 1.0 | 1.4 | 1.0 | 1.0 | 1.1 | 0.8 | 0.9 | 0.9 | 1.0 | 1.1 | 1.0 | 2.0 | 0.6 | 1.3 | 0.9 | 1.0 | 0.7 | 1.0 | 0.7 | 1.2 |
| Slc9a8 | 0.8 | 0.2 | 1.0 | 1.0 | 0.9 | 0.9 | 1.1 | 1.0 | 1.1 | 1.1 | 0.8 | 1.0 | 0.9 | 1.2 | 1.2 | 1.1 | 1.1 | 1.2 | 1.0 | 0.9 | 0.9 | 1.0 |
| Slc16a1 | 0.1 | 0.0 | 1.0 | 1.0 | 1.0 | 1.0 | 1.0 | 1.0 | 0.3 | 0.6 | 1.0 | 1.0 | 1.0 | 1.0 | 1.0 | 1.0 | 1.0 | 1.0 | 1.0 | 1.0 | 1.0 | 1.0 |
| Slc16a4 | 1.0 | 1.0 | 1.0 | 1.0 | 1.1 | 1.0 | 1.0 | 1.0 | 5.4 | 9.6 | 1.0 | 1.0 | 1.0 | 1.0 | 1.0 | 1.0 | 1.0 | 1.0 | 1.0 | 1.0 | 1.0 | 1.0 |
| Slfn4 | 1.0 | 1.0 | 0.9 | 0.7 | 1.0 | 1.0 | 1.0 | 1.0 | 1.0 | 1.0 | 1.1 | 1.0 | 1.0 | 1.0 | 0.3 | 1.8 | 1.2 | 1.1 | 1.2 | 0.8 | | |
| Slpi | 1.0 | 1.0 | 0.9 | 0.4 | 1.0 | 1.0 | 1.1 | 1.6 | 1.8 | 1.9 | 0.4 | 1.0 | 3.4 | 1.4 | 1.2 | 1.5 | 1.2 | 0.9 | 1.1 | 0.7 | 0.7 | 0.8 |
| Smco3 | 1.0 | 1.0 | 1.0 | 1.0 | 0.7 | 0.7 | 1.0 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |

[Fig. 23-28]

Due to the extremely dense numerical table with hundreds of cells at low resolution, reliable transcription is not feasible.

[Fig. 23-29]

| | | | | | | | | | | | | | | | | | | | | | |
|---|---|---|---|---|---|---|---|---|---|---|---|---|---|---|---|---|---|---|---|---|---|
| Thrsp | 1.3 | 1.4 | 0.8 | 1.0 | 0.7 | 0.8 | 1.4 | 1.1 | 0.6 | 0.5 | 1.4 | 3.7 | 1.9 | 3.3 | 1.1 | 1.8 | 0.6 | 0.6 | 1.0 | 1.3 | 0.9 | 1.5 |
| Tigd4 | 1.0 | 1.0 | 1.0 | 1.0 | 0.9 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Timp1 | 2.8 | 6.2 | 0.9 | 0.5 | 1.0 | 1.1 | 2.1 | 1.7 | 1.0 | 1.0 | 1.0 | 1.0 | 1.2 | 0.6 | 1.3 | 1.0 | 2.3 | 3.2 | 1.0 | 1.0 | 1.0 | 1.0 |
| Tmem102 | 0.9 | 0.9 | 1.2 | 1.1 | 0.8 | 0.9 | 1.0 | 1.0 | 1.0 | 0.9 | 0.9 | 0.8 | 1.2 | 1.6 | 5.0 | 1.0 | 1.0 | 1.0 | 1.2 | 1.3 | 1.0 | 1.1 |
| Tmem139 | 0.9 | 0.8 | 1.2 | 1.4 | 1.2 | 1.2 | 1.0 | 1.0 | 1.0 | 0.7 | 0.7 | 1.0 | 1.0 | 1.0 | 5.6 | 1.0 | 0.9 | 1.0 | 1.1 | 1.5 | 1.4 | 1.1 |
| Tmem150c | 1.3 | 0.9 | 1.0 | 1.0 | 1.1 | 1.1 | 0.8 | 0.5 | 1.0 | 1.0 | 1.0 | 1.0 | 1.1 | 1.4 | 1.3 | 27.8 | 1.9 | 1.0 | 1.0 | 1.0 | 1.0 | 1.0 |
| Tmem182 | 1.0 | 1.0 | 0.8 | 0.9 | 0.6 | 0.6 | 1.0 | 1.0 | 1.0 | 1.0 | 1.0 | 1.0 | 1.0 | 1.0 | 0.7 | 0.8 | 1.0 | 1.0 | 1.0 | 1.0 | 1.0 | 1.0 |
| Tmem212 | 1.0 | 1.0 | 1.0 | 1.0 | 1.0 | 1.0 | 1.0 | 1.0 | 1.0 | 1.0 | 1.0 | 1.0 | 1.0 | 1.0 | 0.8 | 6.7 | 1.0 | 1.0 | 1.0 | 1.0 | 1.0 | 1.0 |
| Tmem253 | 1.0 | 1.0 | 1.0 | 1.0 | 0.6 | 0.3 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Tmem252 | 3.9 | 5.1 | 1.2 | 0.9 | 1.2 | 1.3 | 1.6 | 0.9 | 1.0 | 1.0 | 1.0 | 1.0 | 1.7 | 2.2 | 1.1 | 2.1 | 1.6 | 1.7 | 1.5 | 0.8 | 1.1 | 0.7 |
| Tmem254c | 0.9 | 0.6 | 2.4 | 0.7 | 0.3 | 0.7 | 1.0 | 1.0 | 0.3 | 0.0 | 0.8 | 0.8 | 3.0 | 0.2 | 1.8 | 1.1 | 1.1 | 0.7 | 0.8 | 0.5 | 0.5 | 2.7 |
| Tmem30b | 1.2 | 1.2 | 1.1 | 1.3 | 0.9 | 1.1 | 1.0 | 1.0 | 1.0 | 1.1 | 1.0 | 1.0 | 2.2 | 2.0 | 7.3 | 2.3 | 1.0 | 1.0 | 1.0 | 1.0 | 1.6 | 1.1 |
| Tmem37 | 2.3 | 2.0 | 1.3 | 1.3 | 1.0 | 1.0 | 1.4 | 1.0 | 1.0 | 1.5 | 0.5 | 0.3 | 2.0 | 1.5 | 1.1 | 1.2 | 1.3 | 1.4 | 1.4 | 1.9 | 2.3 | 1.1 |
| Tmem38a | 1.1 | 1.1 | 1.1 | 1.1 | 0.8 | 0.8 | 1.0 | 1.1 | 1.1 | 0.9 | 1.3 | 1.3 | 0.9 | 0.9 | 1.1 | 1.3 | 0.9 | 0.9 | 0.9 | 1.1 | 0.8 | 1.1 |
| Tmem45b | 0.8 | 0.8 | 1.1 | 1.3 | 1.0 | 0.6 | 2.1 | 0.5 | 1.0 | 1.0 | 1.0 | 1.0 | 1.4 | 3.0 | 0.3 | 0.6 | 0.9 | 0.9 | 1.0 | 1.1 | 1.0 | 1.0 |
| Tmem51 | 1.0 | 0.9 | 1.0 | 1.0 | 1.0 | 1.0 | 1.1 | 0.9 | 1.5 | 2.1 | 0.7 | 0.8 | 1.6 | 1.4 | 7.6 | 1.8 | 1.0 | 1.1 | 1.1 | 1.2 | 1.2 | 0.9 |
| Tmem52 | 1.9 | 2.2 | 1.0 | 1.1 | 0.8 | 0.8 | 0.8 | 1.1 | 1.0 | 1.0 | 1.1 | 0.8 | 1.0 | 1.0 | 0.8 | 2.4 | 1.0 | 1.0 | 1.0 | 1.0 | 1.0 | 1.0 |
| Tnie | 1.3 | 0.8 | 1.0 | 1.3 | 1.1 | 0.9 | 1.6 | 1.0 | 1.3 | 0.5 | 1.6 | 1.5 | 1.2 | 0.7 | 1.4 | 1.5 | 0.9 | 1.1 | 0.8 | 0.5 | 1.0 | 1.0 |
| Tmod1 | 0.9 | 1.0 | 0.8 | 1.6 | 0.8 | 0.8 | 1.0 | 1.0 | 1.0 | 1.0 | 1.0 | 1.0 | 1.0 | 1.0 | 1.7 | 2.0 | 1.0 | 0.8 | 1.0 | 1.5 | 1.6 | 1.0 |
| Tmod4 | 3.0 | 1.0 | 1.0 | 1.0 | 0.7 | 0.6 | 1.0 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 |
| Tmprss15 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 10.2 | 2.7 | 1.0 | 1.0 |
| Tnfrsf13c | 1.0 | 1.0 | 0.6 | 0.2 | 1.0 | 1.0 | 1.0 | 1.0 | 1.0 | 1.0 | 1.8 | 1.8 | 0.8 | 1.0 | 1.0 | 1.0 | 1.0 | 1.5 | 0.8 | 0.7 | 0.9 |
| Tnmd | 1.0 | 1.0 | 1.0 | 1.0 | 0.8 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Tnnc2 | 1.0 | 1.0 | 1.0 | 1.0 | 0.7 | 0.6 | 1.0 | 1.0 | 1.0 | 1.0 | 1.8 | 1.0 | 1.4 | 0.6 | 1.2 | 0.3 | 1.1 | 1.0 | 1.3 | 1.0 | 1.0 |
| Tnni1 | 1.0 | 1.0 | 1.6 | 1.3 | 0.7 | 1.4 | 1.2 | 1.2 | 1.0 | 1.0 | 1.0 | 1.0 | 1.0 | 1.0 | 1.0 | 1.0 | 1.0 | 1.0 | 1.0 | 1.0 | 1.0 | 1.1 |
| Tnni2 | 1.0 | 1.0 | 1.1 | 0.8 | 0.7 | 0.8 | 0.9 | 1.5 | 1.0 | 1.0 | 1.9 | 2.2 | 0.8 | 0.6 | 1.0 | 1.1 | 0.9 | 0.7 | 1.0 | 0.7 | 1.0 | 9.8 |
| Tnnt3 | 1.0 | 1.0 | 1.0 | 1.0 | 0.7 | 0.7 | 1.0 | 0.6 | 1.0 | 1.0 | 1.0 | 2.6 | 0.8 | 1.5 | 1.0 | 1.0 | 1.2 | 1.2 | 1.0 | 1.0 | 1.0 | 1.0 |
| Tnp1 | 1.0 | 1.0 | 1.0 | 1.1 | 1.0 | 1.0 | 1.1 | 1.0 | 1.0 | 1.0 | 1.0 | 1.0 | 1.0 | 1.0 | 7.7 | 13.2 | 0.5 | 1.0 | 1.0 | 1.0 | 1.0 | 1.0 |
| Tnp2 | 1.0 | 1.0 | 1.0 | 0.5 | 1.0 | 1.0 | 1.0 | 1.0 | 1.0 | 1.0 | 1.0 | 1.0 | 1.2 | 1.1 | 15.6 | 11.9 | 1.0 | 1.0 | 1.0 | 2.1 | 1.1 | 0.6 |
| Tox3 | 0.8 | 0.7 | 0.9 | 1.0 | 1.2 | 1.1 | 1.5 | 1.1 | 1.0 | 1.0 | 1.0 | 1.0 | 1.1 | 0.9 | 11.1 | 1.0 | 1.2 | 1.0 | 1.0 | 0.7 | 0.8 | 1.1 |
| Tpd52l1 | 1.0 | 1.0 | 1.0 | 1.2 | 0.7 | 0.7 | 1.1 | 1.3 | 0.9 | 0.9 | 1.0 | 0.8 | 1.4 | 1.1 | 17.1 | 2.8 | 1.2 | 1.3 | 1.0 | 1.1 | 0.8 | 0.9 |
| Tpm2 | 1.0 | 0.6 | 1.1 | 0.9 | 0.7 | 0.7 | 1.0 | 1.0 | 1.4 | 0.8 | 0.7 | 1.5 | 1.1 | 1.0 | 2.4 | 1.4 | 1.0 | 1.3 | 1.1 | 1.0 | 0.9 |
| Tppp2 | 1.0 | 1.0 | 1.0 | 1.0 | 1.0 | 1.0 | 1.0 | 1.0 | 1.0 | 1.0 | 1.0 | 1.0 | 1.0 | 1.0 | 6.2 | 1.0 | 1.0 | 1.0 | 1.0 | 1.0 | 1.0 | 1.0 |
| Tpx2 | 1.0 | 1.0 | 0.9 | 0.8 | 1.0 | 1.0 | 1.0 | 1.0 | 1.0 | 1.0 | 1.0 | 1.0 | 0.5 | 0.7 | 1.0 | 1.0 | 1.1 | 0.9 | 1.4 | 0.9 | 1.0 | 0.9 |
| Trank1 | 1.0 | 1.0 | 1.0 | 1.0 | 1.1 | 0.8 | 1.0 | 1.0 | 1.0 | 1.0 | 1.0 | 1.0 | 1.0 | 1.0 | 7.4 | 1.0 | 1.0 | 1.0 | 1.0 | 1.0 | 1.0 | 1.0 |
| Trdn | 1.0 | 1.0 | 1.0 | 1.0 | 0.9 | 0.7 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Trem2 | 1.0 | 2.4 | 2.1 | 0.5 | 0.9 | 0.9 | 1.3 | 1.2 | 1.0 | 1.0 | 1.5 | 0.7 | 1.7 | 1.9 | 0.8 | 0.4 | 2.1 | 7.8 | 1.0 | 1.0 | 1.0 | 1.0 |
| Trim54 | 1.0 | 1.0 | 1.0 | 1.0 | 0.8 | 0.6 | 1.1 | 1.5 | 1.0 | 1.0 | 1.0 | 1.0 | 1.0 | 1.0 | 1.0 | 1.9 | 1.0 | 1.0 | 1.0 | 1.0 | 1.0 |
| Trim56 | 1.5 | 0.7 | 0.8 | 1.0 | 1.2 | 1.0 | 1.0 | 0.7 | 3.0 | 0.6 | 0.8 | 2.5 | 0.5 | 0.2 | 0.6 | 0.2 | 0.5 | 1.1 | 0.8 | 0.4 | 1.0 | 2.5 |
| Trim63 | 0.7 | 1.4 | 1.0 | 1.0 | 0.8 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Trim72 | 1.0 | 1.0 | 0.9 | 1.1 | 0.6 | 0.7 | 0.9 | 0.5 | 1.0 | 1.0 | 1.4 | 3.4 | 1.0 | 1.0 | 1.0 | 1.0 | 0.9 | 1.0 | 1.0 | 1.3 | 0.7 | 1.3 | 1.2 |
| Trnp1 | 1.0 | 1.3 | 1.1 | 1.3 | 1.0 | 1.0 | 1.2 | 1.9 | 1.0 | 1.0 | 1.0 | 0.8 | 3.0 | 2.7 | 1.7 | 1.1 | 1.1 | 1.2 | 1.6 | 1.7 | 1.2 | 1.3 |
| Trp53inp2 | 0.9 | 1.0 | 1.0 | 1.0 | 0.9 | 0.9 | 0.9 | 1.6 | 0.9 | 0.8 | 0.9 | 1.0 | 0.9 | 0.9 | 0.3 | 0.3 | 1.2 | 1.3 | 1.0 | 0.9 | 0.9 | 1.1 |
| Trpv6 | 1.0 | 1.2 | 4.2 | 4.4 | 1.0 | 1.0 | 1.0 | 1.0 | 1.0 | 0.3 | 0.6 | 0.6 | 0.7 | 7.8 | 1.0 | 1.0 | 1.0 | 1.0 | 1.0 | 1.0 | 1.0 |
| Try4 | 0.9 | 1.8 | 3.4 | 279.5 | 1.0 | 1.0 | 1.0 | 1.0 | 0.8 | 0.7 | 0.8 | 1.0 | 1.0 | 0.2 | 1.0 | 1.0 | 13.6 | 0.1 | 0.0 | 0.5 | 1.7 | 1.0 |
| Try5 | 1.3 | 1.2 | 3.9 | 278.6 | 1.0 | 1.0 | 1.0 | 1.0 | 0.5 | 0.8 | 0.6 | 1.0 | 1.0 | 0.2 | 1.0 | 1.0 | 28.5 | 0.1 | 0.0 | 0.9 | 1.5 | 1.0 |
| Tsc22d1 | 2.4 | 3.0 | 1.2 | 1.1 | 1.0 | 1.0 | 1.0 | 1.1 | 0.3 | 0.2 | 0.8 | 0.8 | 1.7 | 1.5 | 0.8 | 0.9 | 0.9 | 0.9 | 0.7 | 0.8 | 0.6 | 9.7 |
| Tspan1 | 1.2 | 1.1 | 1.2 | 1.0 | 0.7 | 0.9 | 1.0 | 1.0 | 1.0 | 1.0 | 0.8 | 0.7 | 2.4 | 1.0 | 5.3 | 1.0 | 1.1 | 1.3 | 1.8 | 1.5 | 1.4 | 1.0 |
| Tssk6 | 1.8 | 0.7 | 0.9 | 1.4 | 0.9 | 0.8 | 1.0 | 1.0 | 1.0 | 1.0 | 1.0 | 1.0 | 0.8 | 1.0 | 7.3 | 2.2 | 1.0 | 1.0 | 1.1 | 1.0 | 1.5 | 1.3 |
| Ttc36 | 0.6 | 0.6 | 0.9 | 1.5 | 0.5 | 1.1 | 1.0 | 1.0 | 0.8 | 1.0 | 1.5 | 0.8 | 2.3 | 1.2 | 1.3 | 6.1 | 3.6 | 0.5 | 1.4 | 0.7 | 1.7 | 0.6 |
| Ttc39c | 0.6 | 0.5 | 1.0 | 1.1 | 1.0 | 1.1 | 0.8 | 1.0 | 0.3 | 0.2 | 0.9 | 0.7 | 1.6 | 1.5 | 0.9 | 1.2 | 1.1 | 0.9 | 1.0 | 1.0 | 5.1 | 0.8 |
| Tth | 1.0 | 1.0 | 1.0 | 1.0 | 0.9 | 0.6 | 0.8 | 0.8 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ttr | 2.3 | 1.4 | 0.7 | 1.0 | 1.0 | 1.0 | 1.0 | 1.0 | 0.7 | 0.8 | 3.0 | 2.2 | 1.0 | 1.0 | 0.4 | 0.9 | 1.3 | 0.8 | 1.7 | 1.4 | 1.2 | 0.9 |
| Tuba1a | 1.0 | 1.2 | 1.0 | 0.9 | 1.0 | 0.9 | 0.8 | 1.1 | 1.3 | 0.7 | 0.6 | 6.6 | 0.7 | 0.4 | 0.2 | 1.2 | 1.0 | 1.2 | 1.2 | 0.9 | 0.8 |
| Tuba8 | 1.0 | 0.9 | 1.0 | 1.0 | 0.7 | 0.9 | 1.4 | 1.0 | 5.0 | 3.1 | 1.2 | 2.3 | 1.1 | 1.7 | 2.8 | 2.0 | 1.0 | 1.0 | 1.0 | 1.0 | 1.0 | 1.0 |
| Tubb2a-ps2 | 2.3 | 1.9 | 0.7 | 1.5 | 1.0 | 1.0 | 0.7 | 1.0 | 2.4 | 0.8 | 0.4 | 0.5 | 0.6 | 0.9 | 1.5 | 0.5 | 1.0 | 1.3 | 1.7 | 0.9 | 1.6 | 2.6 |
| Txhb | 1.0 | 1.0 | 1.0 | 1.0 | 0.7 | 0.7 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Tyr | 1.0 | 1.0 | 1.0 | 1.0 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Tyrp1 | 1.0 | 1.0 | 1.0 | 1.0 | 1.0 | 1.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ucp1 | 1.0 | 1.0 | 1.0 | 1.0 | 1.0 | 1.0 | 8.0 | 0.6 | 1.0 | 1.0 | 1.0 | 1.2 | 1.6 | 2.0 | 1.0 | 0.4 | 1.0 | 1.0 | 1.0 | 1.0 | 1.0 |
| Ugt1a1 | 27.4 | 33.0 | 1.2 | 2.0 | 1.0 | 1.0 | 1.0 | 1.0 | 1.0 | 1.2 | 1.7 | 1.0 | 1.0 | 1.0 | 1.0 | 1.0 | 0.9 | 0.7 | 0.7 | 0.8 | 1.0 | 1.2 |
| Ugt1a10 | 16.7 | 55.9 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ugt1a2 | 114.4 | 339.1 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Uox | 1.0 | 1.0 | 0.5 | 0.8 | 1.0 | 1.0 | 1.0 | 1.0 | 0.9 | 0.9 | 1.0 | 1.4 | 1.0 | 1.0 | 1.0 | 1.0 | 6.4 | 0.2 | 1.0 | 1.0 | 1.0 | 1.0 |
| Upp2 | 0.7 | 1.3 | 1.0 | 1.0 | 1.6 | 0.9 | 1.0 | 1.0 | 0.3 | 0.5 | 0.5 | 0.3 | 1.0 | 1.0 | 1.0 | 1.0 | 1.0 | 0.8 | 1.0 | 1.0 | 1.0 | 1.0 |
| Usp13 | 1.0 | 1.0 | 1.0 | 1.0 | 1.0 | 0.6 | 1.0 | 0.9 | 1.0 | 1.0 | 1.0 | 1.0 | 1.0 | 1.0 | 1.0 | 1.0 | 1.0 | 1.0 | 1.0 | 1.0 | 1.0 | 1.0 |
| Vash2 | 1.0 | 1.0 | 1.0 | 1.0 | 1.2 | 0.8 | 1.0 | 1.0 | 1.0 | 1.0 | 1.0 | 1.0 | 1.5 | 1.5 | 5.2 | 1.9 | 1.0 | 1.0 | 1.0 | 1.0 | 1.0 | 1.0 |
| Vcan | 1.0 | 1.0 | 0.9 | 0.6 | 1.0 | 1.1 | 0.9 | 0.7 | 1.0 | 1.0 | 0.8 | 1.0 | 1.0 | 1.0 | 0.5 | 0.5 | 1.0 | 1.2 | 1.0 | 1.0 | 1.0 | 1.0 |
| Vgll2 | 1.0 | 1.0 | 1.0 | 1.0 | 0.5 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Vnn1 | 1.1 | 1.3 | 2.3 | 3.8 | 1.0 | 1.0 | 1.0 | 1.0 | 0.4 | 0.5 | 1.0 | 1.0 | 0.3 | 1.6 | 1.3 | 0.7 | 0.8 | 1.6 | 0.9 | 0.9 |
| Vpreb3 | 1.0 | 1.0 | 0.5 | 0.2 | 1.7 | 1.0 | 1.0 | 1.0 | 0.6 | 1.3 | 1.1 | 2.3 | 0.7 | 1.0 | 1.0 | 1.0 | 1.7 | 1.7 | 0.8 | 1.0 |
| Wbscr25 | 1.0 | 1.0 | 1.0 | 1.0 | 1.0 | 1.0 | 1.0 | 1.0 | 1.0 | 1.0 | 1.0 | 1.0 | 1.0 | 1.0 | 11.1 | 1.0 | 1.0 | 1.0 | 1.0 | 1.0 | 1.0 |
| Wfdc10 | 1.0 | 1.0 | 1.0 | 1.0 | 0.6 | 1.4 | 1.0 | 1.0 | 1.0 | 1.0 | 1.0 | 1.0 | 1.0 | 1.0 | 19.9 | 1.6 | 1.0 | 1.0 | 1.0 | 1.0 | 1.0 |
| Wfdc11 | 1.0 | 1.0 | 1.0 | 1.0 | 1.0 | 1.0 | 1.0 | 1.0 | 1.0 | 1.0 | 1.0 | 1.0 | 1.0 | 1.0 | 5.4 | 1.0 | 1.0 | 1.0 | 1.0 | 1.0 | 1.0 |
| Wfdc13 | 1.0 | 1.0 | 1.0 | 1.0 | 1.0 | 1.0 | 1.0 | 1.0 | 1.0 | 1.0 | 1.0 | 1.0 | 1.0 | 1.0 | 7.0 | 1.0 | 1.0 | 1.0 | 1.0 | 1.0 | 1.0 |
| Wfdc15b | 1.0 | 1.0 | 1.0 | 1.0 | 1.0 | 1.0 | 1.0 | 1.0 | 1.0 | 1.0 | 1.0 | 1.0 | 1.0 | 1.0 | 5.0 | 6.3 | 1.4 | 1.0 | 1.0 | 1.0 | 1.0 |
| Wfdc18 | 1.0 | 1.0 | 1.7 | 0.6 | 1.0 | 0.8 | 1.0 | 1.0 | 1.0 | 1.0 | 0.8 | 0.8 | 1.6 | 0.8 | 1.0 | 1.0 | 1.0 | 1.0 | 1.0 | 1.0 | 1.0 |
| Wfdc6a | 1.0 | 1.0 | 1.0 | 1.0 | 1.0 | 1.0 | 1.0 | 1.0 | 1.0 | 1.0 | 1.0 | 1.0 | 1.0 | 1.0 | 12.4 | 1.0 | 1.0 | 1.0 | 1.0 | 1.0 | 1.0 |
| Wfdc6b | 1.0 | 1.0 | 1.0 | 1.0 | 1.0 | 1.0 | 1.0 | 1.0 | 1.5 | 1.0 | 1.0 | 1.0 | 1.0 | 1.0 | 21.2 | 1.0 | 1.0 | 1.0 | 1.0 | 1.0 | 1.0 |
| Wfdc8 | 1.0 | 1.0 | 1.0 | 1.0 | 1.0 | 1.0 | 1.0 | 1.0 | 1.0 | 1.0 | 1.0 | 1.0 | 1.0 | 1.0 | 20.7 | 1.0 | 1.0 | 1.0 | 1.0 | 1.0 | 1.0 |
| Wfdc9 | 1.0 | 1.0 | 1.0 | 1.0 | 1.0 | 1.0 | 1.0 | 1.0 | 1.0 | 1.0 | 1.0 | 1.0 | 1.0 | 1.0 | 29.4 | 1.0 | 1.0 | 1.0 | 1.0 | 1.0 | 1.0 |
| Xkr1 | 1.0 | 1.0 | 1.0 | 1.0 | 0.7 | 0.7 | 1.3 | 1.1 | 1.0 | 0.9 | 1.0 | 1.0 | 1.0 | 1.0 | 1.0 | 1.0 | 1.0 | 1.0 | 1.0 | 1.0 | 1.0 |
| Xkr2 | 1.0 | 1.0 | 1.0 | 1.0 | 0.8 | 0.6 | 0.9 | 0.8 | 1.0 | 1.0 | 1.0 | 1.0 | 1.0 | 1.0 | 1.0 | 1.0 | 1.0 | 1.0 | 1.0 | 1.0 | 1.0 |
| Xkrx | 1.0 | 1.0 | 0.8 | 0.7 | 1.3 | 1.2 | 0.7 | 0.9 | 1.0 | 1.0 | 1.0 | 0.8 | 1.0 | 7.8 | 1.0 | 0.9 | 0.9 | 1.0 | 1.0 | 1.0 | 1.0 |

[Fig. 23-30]

| | | | | | | | | | | | | | | | | | | | | | |
|---|---|---|---|---|---|---|---|---|---|---|---|---|---|---|---|---|---|---|---|---|---|
| Yipf7 | 1.0 | 1.0 | 1.0 | 1.0 | 0.6 | 0.5 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| Ypel4 | 1.0 | 1.0 | 1.2 | 1.5 | 1.1 | 0.7 | 1.1 | 1.0 | 1.0 | 1.0 | 1.0 | 1.0 | 1.0 | 1.0 | 0.8 | 1.0 | 1.0 | 1.0 | 1.0 | 1.0 | 1.0 |
| Zbed6 | 1.8 | 1.2 | 0.8 | 1.2 | 1.0 | 1.0 | 0.4 | 0.4 | 4.1 | 0.4 | 0.7 | 2.7 | 0.1 | 0.2 | 1.0 | 0.8 | 0.7 | 0.8 | 0.6 | 0.4 | 1.0 | 3.0 |
| Zfp369 | 1.5 | 0.7 | 0.8 | 1.1 | 1.0 | 1.0 | 0.7 | 0.6 | 2.7 | 1.0 | 0.8 | 1.3 | 0.1 | 0.4 | 1.0 | 1.0 | 0.7 | 1.0 | 0.7 | 0.4 | 0.9 | 1.3 |
| Zfp648 | 2.4 | 2.0 | 1.0 | 1.0 | 1.0 | 1.0 | 1.0 | 1.0 | 1.0 | 1.0 | 1.0 | 1.0 | 1.0 | 1.0 | 20.8 | 1.0 | 1.0 | 1.0 | 1.0 | 1.0 | 1.0 | 1.0 |
| Zfp750 | 0.9 | 0.7 | 0.9 | 0.9 | 1.0 | 1.1 | 1.0 | 1.0 | 1.5 | 0.9 | 0.8 | 0.9 | 2.8 | 1.6 | 6.1 | 1.0 | 0.8 | 1.1 | 1.0 | 1.0 | 1.0 | 1.0 |
| Zg16 | 0.7 | 0.6 | 1.2 | 1.2 | 1.0 | 1.0 | 1.0 | 1.0 | 0.9 | 1.1 | 1.7 | 1.0 | 0.9 | 0.3 | 1.0 | 0.3 | 1.4 | 0.2 | 1.1 | 1.6 | 1.1 | 1.0 |

SEQUENCE LISTING

<160> NUMBER OF SEQ ID NOS: 36

<210> SEQ ID NO 1
<211> LENGTH: 286
<212> TYPE: PRT
<213> ORGANISM: Homo sapiens

<400> SEQUENCE: 1

Met Ala Leu Val Leu Ile Leu Gln Leu Leu Thr Leu Trp Pro Leu Cys
1               5                   10                  15

His Thr Asp Ile Thr Pro Ser Val Ala Ile Ile Val Pro Pro Ala Ser
            20                  25                  30

Tyr His Pro Lys Pro Trp Leu Gly Ala Gln Pro Ala Thr Val Val Thr
        35                  40                  45

Pro Gly Val Asn Val Thr Leu Arg Cys Arg Ala Pro Gln Pro Ala Trp
    50                  55                  60

Arg Phe Gly Leu Phe Lys Pro Gly Glu Ile Ala Pro Leu Leu Phe Arg
65                  70                  75                  80

Asp Val Ser Ser Glu Leu Ala Glu Phe Phe Leu Glu Glu Val Thr Pro
                85                  90                  95

Ala Gln Gly Gly Ser Tyr Arg Cys Cys Tyr Arg Arg Pro Asp Trp Gly
            100                 105                 110

Pro Gly Val Trp Ser Gln Pro Ser Asp Val Leu Glu Leu Leu Val Thr
        115                 120                 125

Glu Glu Leu Pro Arg Pro Ser Leu Val Ala Leu Pro Gly Pro Val Val
    130                 135                 140

Gly Pro Gly Ala Asn Val Ser Leu Arg Cys Ala Gly Arg Leu Arg Asn
145                 150                 155                 160

Met Ser Phe Val Leu Tyr Arg Glu Gly Val Ala Ala Pro Leu Gln Tyr
                165                 170                 175

Arg His Ser Ala Gln Pro Trp Ala Asp Phe Thr Leu Leu Gly Ala Arg
            180                 185                 190

Ala Pro Gly Thr Tyr Ser Cys Tyr Tyr His Thr Pro Ser Ala Pro Tyr
        195                 200                 205

Val Leu Ser Gln Arg Ser Glu Val Leu Val Ile Ser Trp Glu Gly Glu
    210                 215                 220

Gly Pro Glu Ala Arg Pro Ala Ser Ser Ala Pro Gly Met Gln Ala Pro
225                 230                 235                 240

Gly Pro Pro Pro Ser Asp Pro Gly Ala Gln Ala Pro Ser Leu Ser Ser
                245                 250                 255

Phe Arg Pro Arg Gly Leu Val Leu Gln Pro Leu Leu Pro Gln Thr Gln
            260                 265                 270

Asp Ser Trp Asp Pro Ala Pro Pro Pro Ser Asp Pro Gly Val

-continued

```
                275                 280                 285

<210> SEQ ID NO 2
<211> LENGTH: 459
<212> TYPE: PRT
<213> ORGANISM: Artificial Sequence
<220> FEATURE:
<223> OTHER INFORMATION: Oscar-Fc fusion

<400> SEQUENCE: 2

Met Ala Leu Val Leu Ile Leu Gln Leu Leu Thr Leu Trp Pro Leu Cys
1               5                   10                  15

His Thr Asp Ile Thr Pro Ser Val Ala Ile Ile Val Pro Pro Ala Ser
            20                  25                  30

Tyr His Pro Lys Pro Trp Leu Gly Ala Gln Pro Ala Thr Val Val Thr
        35                  40                  45

Pro Gly Val Asn Val Thr Leu Arg Cys Arg Ala Pro Gln Pro Ala Trp
    50                  55                  60

Arg Phe Gly Leu Phe Lys Pro Gly Glu Ile Ala Pro Leu Leu Phe Arg
65                  70                  75                  80

Asp Val Ser Ser Glu Leu Ala Glu Phe Phe Leu Glu Glu Val Thr Pro
                85                  90                  95

Ala Gln Gly Gly Ser Tyr Arg Cys Cys Tyr Arg Arg Pro Asp Trp Gly
            100                 105                 110

Pro Gly Val Trp Ser Gln Pro Ser Asp Val Leu Glu Leu Leu Val Thr
        115                 120                 125

Glu Glu Leu Pro Arg Pro Ser Leu Val Ala Leu Pro Gly Pro Val Val
    130                 135                 140

Gly Pro Gly Ala Asn Val Ser Leu Arg Cys Ala Gly Arg Leu Arg Asn
145                 150                 155                 160

Met Ser Phe Val Leu Tyr Arg Glu Gly Val Ala Ala Pro Leu Gln Tyr
                165                 170                 175

Arg His Ser Ala Gln Pro Trp Ala Asp Phe Thr Leu Leu Gly Ala Arg
            180                 185                 190

Ala Pro Gly Thr Tyr Ser Cys Tyr Tyr His Thr Pro Ser Ala Pro Tyr
        195                 200                 205

Val Leu Ser Gln Arg Ser Glu Val Leu Val Ile Ser Trp Glu Gly Glu
    210                 215                 220

Gly Pro Glu Ala Arg Pro Ala Ser Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
```

```
                355                 360                 365
Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 3
<211> LENGTH: 271
<212> TYPE: PRT
<213> ORGANISM: Mus musculus

<400> SEQUENCE: 3

Met Val Leu Ser Leu Ile Leu Gln Leu Ser Thr Leu Cys Glu Leu Ser
1               5                   10                  15

Leu Pro Trp Pro Ala Cys Arg Ala Asp Phe Thr Pro Thr Ala Pro Leu
            20                  25                  30

Ala Ser Tyr Pro Gln Pro Trp Leu Gly Ala His Pro Ala Ala Val Val
        35                  40                  45

Thr Pro Gly Ile Asn Val Thr Leu Thr Cys Arg Ala Pro Gln Ser Ala
    50                  55                  60

Trp Arg Phe Ala Leu Phe Lys Ser Gly Leu Val Thr Pro Leu Leu Leu
65                  70                  75                  80

Arg Asp Val Ser Val Glu Leu Ala Glu Phe Phe Leu Glu Glu Val Thr
                85                  90                  95

Pro Ala Gln Gly Gly Ser Tyr His Cys Arg Tyr Arg Lys Thr Asp Trp
            100                 105                 110

Gly Pro Gly Val Trp Ser Gln Pro Ser Asn Val Leu Glu Leu Leu Val
        115                 120                 125

Thr Asp Gln Leu Pro Arg Pro Ser Leu Val Ala Leu Pro Gly Pro Val
    130                 135                 140

Val Ala Pro Gly Ala Asn Val Ser Leu Arg Cys Ala Gly Arg Ile Pro
145                 150                 155                 160

Gly Met Ser Phe Ala Leu Tyr Arg Val Gly Val Ala Thr Pro Leu Gln
                165                 170                 175

Tyr Ile Asp Ser Val Gln Pro Trp Ala Asp Phe Leu Leu Ile Gly Thr
            180                 185                 190

His Thr Pro Gly Thr Tyr Cys Cys Tyr Tyr His Thr Pro Ser Ala Pro
        195                 200                 205

Tyr Val Leu Ser Gln Arg Ser Gln Pro Leu Val Ile Ser Phe Glu Gly
    210                 215                 220

Ser Gly Ser Leu Asp Tyr Thr Gln Gly Asn Leu Ile Arg Leu Gly Leu
225                 230                 235                 240

Ala Gly Met Val Leu Ile Cys Leu Gly Ile Ile Val Thr Cys Asp Trp
                245                 250                 255

His Ser Arg Ser Ser Ala Phe Asp Gly Leu Leu Pro Gln Gln Asn
            260                 265                 270
```

```
<210> SEQ ID NO 4
<211> LENGTH: 462
<212> TYPE: PRT
<213> ORGANISM: Artificial Sequence
<220> FEATURE:
<223> OTHER INFORMATION: Oscar-Fc fusion

<400> SEQUENCE: 4

Met Val Leu Ser Leu Ile Leu Gln Leu Ser Thr Leu Cys Glu Leu Ser
1               5                   10                  15

Leu Pro Trp Pro Ala Cys Arg Ala Asp Phe Thr Pro Thr Ala Pro Leu
            20                  25                  30

Ala Ser Tyr Pro Gln Pro Trp Leu Gly Ala His Pro Ala Ala Val Val
        35                  40                  45

Thr Pro Gly Ile Asn Val Thr Leu Thr Cys Arg Ala Pro Gln Ser Ala
    50                  55                  60

Trp Arg Phe Ala Leu Phe Lys Ser Gly Leu Val Thr Pro Leu Leu Leu
65                  70                  75                  80

Arg Asp Val Ser Val Glu Leu Ala Glu Phe Phe Leu Glu Glu Val Thr
                85                  90                  95

Pro Ala Gln Gly Gly Ser Tyr His Cys Arg Tyr Arg Lys Thr Asp Trp
            100                 105                 110

Gly Pro Gly Val Trp Ser Gln Pro Ser Asn Val Leu Glu Leu Leu Val
        115                 120                 125

Thr Asp Gln Leu Pro Arg Pro Ser Leu Val Ala Leu Pro Gly Pro Val
    130                 135                 140

Val Ala Pro Gly Ala Asn Val Ser Leu Arg Cys Ala Gly Arg Ile Pro
145                 150                 155                 160

Gly Met Ser Phe Ala Leu Tyr Arg Val Gly Val Ala Thr Pro Leu Gln
                165                 170                 175

Tyr Ile Asp Ser Val Gln Pro Trp Ala Asp Phe Leu Leu Ile Gly Thr
            180                 185                 190

His Thr Pro Gly Thr Tyr Cys Cys Tyr Tyr His Thr Pro Ser Ala Pro
        195                 200                 205

Tyr Val Leu Ser Gln Arg Ser Gln Pro Leu Val Ile Ser Phe Glu Gly
    210                 215                 220

Ser Gly Ser Leu Asp Tyr Thr Gln Gly Asn Leu Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365
```

```
Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
    450                 455                 460

<210> SEQ ID NO 5
<211> LENGTH: 20
<212> TYPE: DNA
<213> ORGANISM: Mus musculus

<400> SEQUENCE: 5
acagctggag tatcagcgac                                                      20

<210> SEQ ID NO 6
<211> LENGTH: 20
<212> TYPE: DNA
<213> ORGANISM: Mus musculus

<400> SEQUENCE: 6
gctcacagag agtcgacagc                                                      20

<210> SEQ ID NO 7
<211> LENGTH: 146
<212> TYPE: DNA
<213> ORGANISM: Artificial Sequence
<220> FEATURE:
<223> OTHER INFORMATION: ssODN

<400> SEQUENCE: 7
gccaaggatc cacacacagg ggagggacag ctcacagaga gtcgacagct ggagtatcag          60
cctcagaaga actcgtcaag aagtcacgac aggaccatgg tgggcactct ccgtggagct         120
gaggaaaagg ttgaccctgc cttttt                                              146

<210> SEQ ID NO 8
<211> LENGTH: 146
<212> TYPE: DNA
<213> ORGANISM: Artificial Sequence
<220> FEATURE:
<223> OTHER INFORMATION: ssODN

<400> SEQUENCE: 8
atagccctca gcccagccaa ggatccacac acaggggagg gacagctcac agagagtcga          60
cctcagaaga actcgtcaag aagtcacagc tggagtatca gcgacaggac catggtgggc         120
actctccgtg gagctgagga aaaggt                                              146

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
```
ctacttagcg acaacgtcct                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gccttggggt ttgaaggttt                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cagaggctat gactgttcca                                          20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ggcagggtca acctttttcct                                         20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
agggacagct cacagagagt                                          20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gctcggtgac cctggtcttt                                          20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aatgtgaggc gggtggaact                                          20

<210> SEQ ID NO 16
<211> LENGTH: 20
<212> TYPE: DNA

-continued

```
<213> ORGANISM: Artificial Sequence
<220> FEATURE:
<223> OTHER INFORMATION: primer

<400> SEQUENCE: 16
cgggcatgag ttttgcactg                                             20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tgggtatagt ccaaggagcc a                                           21

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
aggagccatg actcgaaggt                                             20

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gctcaccagg tagtgatgct t                                           21

<210> SEQ ID NO 20
<211> LENGTH: 1601
<212> TYPE: DNA
<213> ORGANISM: Artificial Sequence
<220> FEATURE:
<223> OTHER INFORMATION: Oscar-Fc

<400> SEQUENCE: 20
aagcttgcca ccatggccct cgtgcttatc ctccaacttc tcacgctttg gcctctgtgc    60
cacaccgaca ttactccgtc tgttgcgata attgtccctc cgcctcttat tcaccctaaa   120
ccttggctgg gcgcacagcc agctactgtg gttactcctg gggtgaacgt aacactgcgc   180
tgccgtgctc ctcagcccgc ctggagattt gggttgttta gcccggaga gatagcacca   240 ctgctgtttc gggatgtgtc ctcagagctg gctgagttct tcctggaaga ggtcactcct   300
gcccaaggag gcagctatcg gtgctgttat aggcggccgg attggggacc cggcgtttgg   360
tcccaaccat ctgatgtgct cgaactgctt gtgacagaag agctgccag acctagcttg   420 gtagccttgc ccgtcctgt cgtcggacct ggtgccaatg tttctcttcg atgtgccgga   480
aggctgcgca atatgtcctt tgtactgtat agggagggga tagccgcacc tctgcagtat   540
aggcatagcg ctcagccctg gcggattttt actctgcttg gtgccagagc acccgggacc   600
tattcctgct actaccacac tccttccgca ccctacgtcc tgtcacagag atcagaagtg   660
ctcgtgatct cctgggaggg agaaggccca gaagccgaca aaactcacac atgcccaccg   720
tgcccaggta agccagccca ggcctcgccc tccagctcaa ggcgggacag gtgccctaga   780
```

```
gtagcctgca tccagggaca ggccccagcc gggtgctgac acgtccacct ccatctcttc    840
ctcagcacct gaactcctgg ggggaccgtc agtcttcctc ttcccccaa aacccaagga     900 caccctcatg atctcccgga cccctgaggt cacatgcgtg gtggtggacg tgagccacga    960
agaccctgag gtcaagttca actggtacgt ggacggcgtg gaggtgcata atgccaagac    1020
aaagccgcgg gaggagcagt acaacagcac gtaccgtgtg gtcagcgtcc tcaccgtcct    1080
gcaccaggac tggctgaatg gcaaggagta caagtgcaag gtctccaaca aagccctccc    1140
agcccccatc gagaaaacca tctccaaagc caaaggtggg acccgtgggg tgcgagggcc    1200
acatggacag aggccggctc ggcccaccct ctgcccgag agtgactgct gtaccaacct    1260
ctgtccctac agggcagccc cgagaaccac aggtgtacac cctgccccca tcccgggatg    1320
agctgaccaa gaaccaggtc agcctgacct gcctggtcaa aggcttctat cccagcgaca    1380
tcgccgtgga gtgggagagc aatgggcagc cggagaacaa ctacaagacc acgcctcccg    1440
tgctggactc cgacggctcc ttcttcctct acagcaagct caccgtggac aagagcaggt    1500
ggcagcaggg gaacgtcttc tcatgctccg tgatgcatga ggctctgcac aaccactaca    1560
cgcagaagag cctctccctg tctccgggta aatgatctag a                        1601
```

```
<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
aagaccttga gtagttgccc a                                              21

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
tgctcgatcc tacgtttgca g                                              21

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
aggagccatg actcgaaggt                                                20

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gctcaccagg tagtgatgct t                                              21

<210> SEQ ID NO 25
```

```
<211> LENGTH: 20
<212> TYPE: DNA
<213> ORGANISM: Artificial Sequence
<220> FEATURE:
<223> OTHER INFORMATION: primer

<400> SEQUENCE: 25
accccagcat ggaaacaaag                                              20

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
aagaatggta ttgaagtcat ctgtc                                        25

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
accccgtgaa gaaaatcaga a                                            21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
taacaggcgg tcttggttgg                                              20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
tggtggtcct gtttacagtg g                                            21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ttctgaagtt cttcacgggg t                                            21

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
```

```
cctacgaaga ctcaaattct cagc                                          24

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gaggaccatg gtggtgtcc                                                19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gctcggtgac cctggtctttt                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
aatgtgaggc gggtggaact                                               20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
ctccatcgga gaaggacagc                                               20

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
aggtcctgaa agtccattgt cc                                            22
```

SCREENING METHOD FOR CANDIDATE SUBSTANCES FOR ACTIVE COMPONENT TO PREVENT OR TREAT AT LEAST ONE DISEASE SELECTED FROM THE GROUP CONSISTING OF RENAL HYPOFUNCTION, CHRONIC KIDNEY DISEASE AND KIDNEY FAILURE

TECHNICAL FIELD

The present invention relates to a method and device for screening a candidate substance for an active ingredient to prevent or treat at least one disease selected from the group consisting of declined kidney function, chronic kidney disease, and renal failure. The present invention also relates to a program that causes a computer to perform a function for screening a candidate substance for an active ingredient to prevent or treat at least one disease selected from the group consisting of declined kidney function, chronic kidney disease, and renal failure.

Furthermore, the present invention relates to a device and program for predicting the presence of at least one disease selected from the group consisting of declined kidney function, chronic kidney disease, and renal failure, and/or the stage of the disease in a subject. The present invention also relates to a device and program for predicting the presence of a disease and/or the stage of the disease in each of one or more organs other than the kidneys in a subject affected with at least one disease selected from the group consisting of declined kidney function, chronic kidney disease, and renal failure.

BACKGROUND ART

Diseases include those in a state that can be reversibly treated, and those in a state that cannot, i.e., those in an irreversible state. Early detection and treatment of abnormalities during a reversible state, or preventing such a state from occurring, is essential for health maintenance. Even in a reversible state, early detection of disease directly leads to milder treatment, a shorter treatment period, and better prognostic health. As in heart disease, brain disease, cancer, and diabetes, it is well known that abnormalities in one organ or tissue lead to a disease state in other organs (commonly called a "complication"). In such diseases, it is essential to prevent, at the earliest possible time, abnormalities in one organ or tissue from causing disease in other organs or tissue.

In all animals, including humans, each organ and tissue form a functional network, rather than serving as separate parts, and quality control at the individual level is achieved. Transport of endocrine factors, such as hormones, by the vascular network throughout the entire body and coordinated adjustment of organ functions by the neural network are typical examples of an "inter-organ cross talk system," and systematized as physiology or endocrinology.

Meanwhile, the number of end-stage kidney disease (ESKD) patients in need of dialysis or kidney transplant has been increasing worldwide. The number of ESKD patients increased from 430,000 to 1,065,000 over the decade from 1990 to 2000, and further increased to at least about 1,650,000 in 2008 (Non-patent Literature 1). Chronic kidney disease (CKD) progresses to ESKD. However, in the kidneys, called the "silent organ," even if kidney damage occurs, its condition is less likely to appear in clinical data etc. Thus, early detection of declined kidney function before onset of chronic kidney disease is difficult.

CITATION LIST

Non-Patent Literature

NPL 1: Lysaght M J: J Am Soc Nephrol. 2002 January; 13 Suppl 1; S37-40.

SUMMARY OF INVENTION

Technical Problem

CKD develops due to various diseases such as diabetes, hypertension, and like lifestyle-related diseases; and urinary tract infection, urinary tract obstruction, glomerulonephritis, vascular disease in the kidneys (blood flow disorder), drug-induced nephropathy caused by an analgesic, and like urinary system diseases. Thus, after kidney function has declined, treatment of such a primary disease is first performed in order to slow progression of the declined kidney function. In addition, treatment such as blood-pressure control or dietary restriction is conducted to slow progression of CKD. Further, for example, a drug therapy using a phosphate-binding agent etc. is performed for abnormal bone metabolism associated with chronic kidney disease when CKD progresses.

However, there is currently no fundamental therapeutic agent that halts progression of declined kidney function.

An objective of the present invention is to provide a method and device for screening a candidate substance for an active ingredient to prevent or treat at least one disease selected from the group consisting of declined kidney function, chronic kidney disease, and renal failure. Another object of the present invention is to provide a pharmaceutical composition for suppressing progression of declined kidney function or improving declined kidney function, and preventing or treating at least one disease selected from the group consisting of declined kidney function, chronic kidney disease, and renal failure.

A further object of the present invention is to provide a device and program for detecting, from cells or tissue of one organ other than the kidneys, at least one disease selected from the group consisting of declined kidney function, chronic kidney disease, and renal failure at the earliest possible time. More specifically, a further object of the present invention is to predict the presence of at least one disease selected from the group consisting of declined kidney function, chronic kidney disease, and renal failure, and/or the stage of the disease, from an inter-organ cross talk indicator derived from one or more organs other than the kidneys. A still further object of the present invention is to predict the presence of a disease and/or the stage of the disease in each of one or more organs other than the kidneys from the state of at least one disease selected from the group consisting of declined kidney function, chronic kidney disease, and renal failure.

Solution to Problem

The inventor conducted extensive research, and found that the expression of certain kidney function prediction marker proteins increases in an animal model of kidney disease. The inventor found that progression of declined kidney function can be suppressed, or that declined kidney function can be improved, by suppressing function of such a kidney function prediction marker protein. The inventor further found that whether a test substance can be a candidate substance for an active ingredient to prevent or treat at least one disease selected from the group consisting of declined kidney function, chronic kidney disease, and renal failure can be screened by observing changes in expression or function of such a kidney function prediction marker protein in a subject to which the test subject has been administered.

The present inventor also focused on an inter-organ cross talk system to achieve the above objects. The inventor conducted extensive research, and found that it is possible to provide a device and program for diagnosing the state of at least one disease selected from the group consisting of declined kidney function, chronic kidney disease, and renal failure from the state of an organ other than the kidneys; and for predicting a future state by using the inter-organ cross talk system.

The present invention has been accomplished based on these findings, and includes the following embodiments.

Item 1.

A device for screening a candidate substance for an active ingredient to prevent or treat at least one disease selected from the group consisting of declined kidney function, chronic kidney disease, and renal failure, the device comprising the following computation means:

first measurement value obtaining means for obtaining a measurement value of a kidney function prediction marker protein and/or a measurement value of mRNA of the protein in a specimen collected from a subject (excluding humans), test tissue, or test cell treated with a test substance (a test-substance-treated specimen); and means for determining that the test substance is a candidate substance for the active ingredient based on the measurement value(s) obtained by the first measurement value obtaining means.

Item 2.

The device according to Item 1, further comprising:

second measurement value obtaining means for obtaining a measurement value of the kidney function prediction marker protein and/or a measurement value of mRNA of the protein in a specimen collected from a subject (excluding humans), test tissue, or test cell that is not treated with the test substance (an untreated specimen); and means for comparing the measurement value(s) of the test-substance-treated specimen with the measurement value(s) of the untreated specimen, wherein the determination means determines that the test substance is a candidate substance for the active ingredient based on the comparison result obtained by the measurement value comparison means.

Item 3.

The device according to Item 1 or 2, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 4.

A screening program that, when executed by a computer, causes the computer to carry out the following processing to screen a candidate substance for an active ingredient to prevent or treat at least one disease selected from the group consisting of declined kidney function, chronic kidney disease, and renal failure:

first measurement value obtaining processing of obtaining a measurement value of a kidney function prediction marker protein and/or a measurement value of mRNA of the protein in a specimen collected from a subject (excluding humans), test tissue, or test cell treated with a test substance (a test-substance-treated specimen); and processing of determining that the test substance is a candidate substance for the active ingredient based on the measurement value(s) obtained by the first measurement value obtaining processing.

Item 5.

The screening program according to Item 4, wherein the program further causes the computer to carry out second measurement value obtaining processing of obtaining a measurement value of the kidney function prediction marker protein and/or a measurement value of mRNA of the protein in a specimen collected from a subject (excluding humans), test tissue, or test cell that is not treated with the test substance (an untreated specimen); and processing of comparing the measurement value(s) of the test-substance-treated specimen with the measurement value(s) of the untreated specimen, and in the determination processing, it is determined that the test substance is a candidate substance for the active ingredient based on the comparison result obtained by the measurement value comparison processing.

Item 6.

The screening program according to Item 4 or 5, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 7.

A method for screening a candidate substance for an active ingredient to prevent or treat at least one disease selected from the group consisting of declined kidney function, chronic kidney disease, and renal failure, the method comprising the steps of:

(I) obtaining a measurement value of a kidney function prediction marker protein and/or a measurement value of mRNA of the protein in a specimen collected from a subject (excluding humans), test tissue, or test cell treated with a test substance (a test-substance-treated specimen); and (II) determining that the test substance is a candidate substance for the active ingredient based on the measurement value(s) obtained in step (I).

Item 8.

The method according to Item 7, further comprising, between steps (I) and (II), the step of comparing the measurement value(s) of the test-substance-treated specimen obtained in step (I) with a measurement value of a corresponding kidney function prediction marker protein and/or a measurement value of mRNA of the protein in a specimen collected from a subject (excluding humans), test tissue, or test cell that is not treated with the test substance (an untreated specimen).

Item 9.

The method according to Item 7 or 8, comprising, before step (I), the steps of:

(i) treating the subject (excluding humans), test tissue, or test cell with the test substance;

(ii) collecting the specimen from the subject, test tissue, or test cell treated with the test substance in step (i); and (iii) collecting the protein and/or the mRNA from the specimen obtained in step (ii).

Item 10.

The method according to any one of Items 7 to 9, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 11.

A method for screening a candidate substance for an active ingredient to prevent or treat at least one disease selected from the group consisting of declined kidney function, chronic kidney disease, and renal failure, the method comprising the steps of:
- (A) detecting a kidney function prediction marker protein and/or mRNA of the protein in a specimen collected from a subject (excluding humans), test tissue, or test cell treated with a test substance (a test-substance-treated specimen); and
- (B) determining that the test substance is a candidate substance for the active ingredient based on the result obtained in step (A).

Item 12.

The method according to Item 11, further comprising, between steps (A) and (B), the step of comparing the detection result of the test-substance-treated specimen obtained in step (A) with a detection result of a corresponding kidney function prediction marker protein and/or mRNA of the protein in a specimen collected from a subject (excluding humans), test tissue, or test cell that is not treated with the test substance (an untreated specimen).

Item 13.

The method according to Item 11 or 12, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 14.

A device for screening a candidate substance for an active ingredient to prevent or treat at least one disease selected from the group consisting of declined kidney function, chronic kidney disease, and renal failure, the device comprising the following computation means:
- first evaluation result obtaining means for obtaining an evaluation result of function of a kidney function prediction marker protein in a specimen collected from a subject (excluding humans), test tissue, or test cell treated with a test substance (a test-substance-treated specimen); and
- means for determining that the test substance is a candidate substance for the active ingredient based on the evaluation result obtained by the first evaluation result obtaining means.

Item 15.

The device according to Item 14, further comprising:
- second evaluation result obtaining means for obtaining an evaluation result of function of the kidney function prediction marker protein in a specimen collected from a subject (excluding humans), test tissue, or test cell that is not treated with the test substance (an untreated specimen); and
- means for comparing the evaluation result of the test-substance-treated specimen with the evaluation result of the untreated specimen,
- wherein the determination means determines that the test substance is a candidate substance for the active ingredient based on the comparison result obtained by the evaluation result comparison means.

Item 16.

The device according to Item 14 or 15, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 17.

A screening program that, when executed by a computer, causes the computer to carry out the following processing to screen a candidate substance for an active ingredient to prevent or treat at least one disease selected from the group consisting of declined kidney function, chronic kidney disease, and renal failure:
- first evaluation result obtaining processing of obtaining an evaluation result of function of a kidney function prediction marker protein in a specimen collected from a subject (excluding humans), test tissue, or test cell treated with a test substance (a test-substance-treated specimen); and
- processing of determining that the test substance is a candidate substance for the active ingredient based on the evaluation result obtained by the first evaluation result obtaining processing.

Item 18.

The screening program according to Item 17, wherein the program further causes the computer to carry out second evaluation result obtaining processing of obtaining an evaluation result of function of the kidney function prediction marker protein in a specimen collected from a subject (excluding humans), test tissue, or test cell that is not treated with the test substance (an untreated specimen); and processing of comparing the evaluation result of the test-substance-treated specimen with the evaluation result of the untreated specimen, and
in the determination processing, it is determined that the test substance is a candidate substance for the active ingredient based on the comparison result obtained by the evaluation result comparison processing.

Item 19.

The screening program according to Item 17 or 18, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 20.

A method for screening a candidate substance for an active ingredient to prevent or treat at least one disease selected from the group consisting of declined kidney function, chronic kidney disease, and renal failure, the method comprising the steps of:
- (I) evaluating function of a kidney function prediction marker protein in a specimen collected from a subject (excluding humans), test tissue, or test cell treated with a test substance (a test-substance-treated specimen); and
- (II) determining that the test substance is a candidate substance for the active ingredient based on the evaluation result obtained in step (I).

Item 21.

The method according to Item 20, further comprising, between steps (I) and (II), the step of comparing the evaluation result of the test-substance-treated specimen obtained in step (I) with an evaluation result of function of a corresponding kidney function prediction marker protein in a specimen collected from a subject (excluding humans), test tissue, or test cell that is not treated with the test substance (an untreated specimen).

Item 22.
The method according to Item 20 or 21, comprising, before step (I), the steps of:
(i) treating the subject (excluding humans), test tissue, or test cell with the test substance; and
(ii) collecting the specimen from the subject, test tissue, or test cell treated with the test substance in step (i).

Item 23.
The method according to any one of Items 20 to 22, wherein the kidney function prediction marker protein is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 24.
A device for predicting the presence of at least one disease selected from the group consisting of declined kidney function, chronic kidney disease, and renal failure, and/or the stage of the disease in a subject, the device comprising the following computation means:
means for obtaining data of the subject regarding an inter-organ cross talk indicator in each of one or more organs other than the kidneys in the subject, the inter-organ cross talk indicator being derived from cells or tissue originating from each of the one or more organs;
means for calculating, by comparing the data of the subject obtained by the subject data obtaining means with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and
means for predicting the presence of the at least one disease selected from the group consisting of declined kidney function, chronic kidney disease, and renal failure, and/or the stage of the disease, by using, as a measure, the similarity of patterns of the inter-organ cross talk indicators calculated by the pattern similarity calculation means;
wherein the data of the subject is a pattern of the inter-organ cross talk indicator representing a relationship between an amount of the inter-organ cross talk indicator in the organ other than the kidneys of the subject and an amount of the corresponding inter-organ cross talk indicator in the same organ as the organ other than the kidneys in negative control(s) with no disease in the kidneys, and
the standard data 1 includes patterns of the inter-organ cross talk indicators, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure.

Item 24-1.
The device according to Item 24, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 25.
A prediction program that, when executed by a computer, causes the computer to carry out the following processing to predict the presence of at least one disease selected from the group consisting of declined kidney function, chronic kidney disease, and renal failure, and/or the stage of the disease in a subject:
processing of obtaining data of the subject regarding an inter-organ cross talk indicator in each of one or more organs other than the kidneys in the subject, the inter-organ cross talk indicator being derived from cells or tissue originating from each of the one or more organs;
processing of calculating, by comparing the data of the subject obtained by the subject data obtaining processing with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and
processing of predicting the presence of the at least one disease selected from the group consisting of declined kidney function, chronic kidney disease, and renal failure, and/or the stage of the disease, by using, as a measure, the similarity of patterns of the inter-organ cross talk indicators calculated by the pattern similarity calculation processing;
wherein the data of the subject is a pattern of the inter-organ cross talk indicator representing a relationship between an amount of the inter-organ cross talk indicator in the organ other than the kidneys of the subject and an amount of the corresponding inter-organ cross talk indicator in the same organ as the organ other than the kidneys in negative control(s) without the at least one disease selected from the group consisting of declined kidney function, chronic kidney disease, and renal failure, and
the standard data 1 includes patterns of the inter-organ cross talk indicators, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) with no disease in the kidneys.

Item 25-1.
The prediction program according to Item 25, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 26.
A method for predicting the presence of at least one disease selected from the group consisting of declined kidney function, chronic kidney disease, and renal failure and/or the stage of the disease in a subject, the method comprising the steps of:

(1) obtaining data of the subject regarding an inter-organ cross talk indicator in each of one or more organs other than the kidneys in the subject, the inter-organ cross talk indicator being derived from cells or tissue originating from each of the one or more organs;

(2) calculating, by comparing the data of the subject obtained in step (1) with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and (3) determining that the subject has a disease corresponding to the standard data 1 and/or that the subject is in a stage of a disease corresponding to the standard data 1 when it is determined from the similarity of patterns of the inter-organ cross talk indicators calculated in step (2) that both patterns are similar;

wherein the data of the subject is a pattern of the inter-organ cross talk indicator representing a relationship between an amount of the inter-organ cross talk indicator in the organ other than the kidneys of the subject and an amount of the corresponding inter-organ cross talk indicator in the same organ as the organ other than the kidneys in negative control(s) without the at least one disease selected from the group consisting of declined kidney function, chronic kidney disease, and renal failure, and the standard data 1 includes patterns of the inter-organ cross talk indicators, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure.

Item 26-1.

The method according to Item 26, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 27.

A method for obtaining information regarding similarity of patterns of inter-organ cross talk indicators to predict the presence of at least one disease selected from the group consisting of declined kidney function, chronic kidney disease, and renal failure and/or the stage of the disease in a subject, the method comprising the steps of:

(1) obtaining data of the subject regarding an inter-organ cross talk indicator in each of one or more organs other than the kidneys in the subject, the inter-organ cross talk indicator being derived from cells or tissue originating from each of the one or more organs; and (2) calculating, by comparing the data of the subject obtained in step (1) with predetermined standard data 1 of the corresponding inter-organ cross talk indicator, similarity of patterns of the inter-organ cross talk indicators between the data of the subject and the standard data 1, and obtaining information regarding the similarity;

wherein the data of the subject is a pattern of the inter-organ cross talk indicator representing a relationship between an amount of the inter-organ cross talk indicator in the organ other than the kidneys of the subject and an amount of the corresponding inter-organ cross talk indicator in the same organ as the organ other than the kidneys in negative control(s) without the at least one disease selected from the group consisting of declined kidney function, chronic kidney disease, and renal failure, and the standard data 1 includes patterns of the inter-organ cross talk indicators, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure.

Item 27-1.

The method according to Item 27, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 28.

A device for predicting the presence of a disease and/or the stage of the disease in each of one or more organs other than the kidneys in a subject affected with at least one disease selected from the group consisting of declined kidney function, chronic kidney disease, and renal failure, the device comprising the following computation means:

means for obtaining information about a stage of the at least one disease selected from the group consisting of declined kidney function, chronic kidney disease, and renal failure in the subject;

means for checking the information about the stage obtained by the stage information obtaining means against standard data 2;

means for extracting a pattern of an inter-organ cross talk indicator in each of one or more organs other than the kidneys in the subject based on the result obtained by the stage information checking means; and means for predicting the presence of a disease and/or the stage of the disease in each of the one or more organs other than the kidneys by using, as a measure, the pattern of the inter-organ cross talk indicator obtained by the pattern extraction means;

wherein the standard data 2 includes patterns of the inter-organ cross talk indicators predetermined for each stage of the at least one disease selected from the group consisting of declined kidney function, chronic kidney disease, and renal failure, each of the patterns being derived from a predetermined relationship between an amount of the inter-organ cross talk indicator in the organ other than the kidneys in positive control(s)

affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure.

Item 28-1.

The device according to Item 28, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 29.

A prediction program that, when executed by a computer, causes the computer to carry out the following processing to predict the presence of a disease and/or the stage of the disease in each of one or more organs other than the kidneys in a subject affected with at least one disease selected from the group consisting of declined kidney function, chronic kidney disease, and renal failure:

processing of obtaining information about a stage of the at least one disease selected from the group consisting of declined kidney function, chronic kidney disease, and renal failure in the subject;

stage information comparison processing of checking the information about the stage obtained by the stage information obtaining processing against standard data 2;

processing of extracting a pattern of an inter-organ cross talk indicator in each of one or more organs other than the kidneys in the subject based on the result obtained by the stage information comparison processing; and processing of predicting the presence of a disease and/or the stage of the disease in each of the one or more organs other than the kidneys by using, as a measure, the pattern of the inter-organ cross talk indicator obtained by the pattern extraction processing, wherein the standard data 2 includes patterns of the inter-organ cross talk indicators predetermined for each stage of the at least one disease selected from the group consisting of declined kidney function, chronic kidney disease, and renal failure, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure.

Item 29-1.

The prediction program according to Item 29, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 30.

A method for predicting the presence of a disease and/or the stage of the disease in each of one or more organs other than the kidneys in a subject affected with at least one disease selected from the group consisting of declined kidney function, chronic kidney disease, and renal failure, the method comprising the steps of:

(i) obtaining information about a stage of the at least one disease selected from the group consisting of declined kidney function, chronic kidney disease, and renal failure in the subject from a diagnostic result of the subject;

(ii) checking the information about the stage obtained in step (i) against standard data 2;

(iii) determining, from the standard data 2, standard data a at a stage of the at least one disease selected from the group consisting of declined kidney function, chronic kidney disease, and renal failure corresponding to the information about the stage, based on the checking result obtained in step (ii), and extracting, from the standard data a, a pattern of an inter-organ cross talk indicator corresponding to the stage in the subject in each of one or more organs other than the kidneys in the subject;

(iv) checking the pattern of the inter-organ cross talk indicator extracted in step (iii) against known information about inter-organ cross talk indicators in diseases and/or stages of the diseases, and determining the presence of a disease and/or the stage of the disease in each of the one or more organs other than the kidneys corresponding to the pattern of the inter-organ cross talk indicator in each of the one or more organs other than the kidneys in the subject; and (v) further determining that the disease in each of the one or more organs other than the kidneys determined in step (iv) is a disease from which the subject may be suffering, and/or determining that the stage of the disease in each of the one or more organs other than the kidneys determined in step (iv) is a stage of a disease from which the subject is suffering, wherein the standard data 2 includes patterns of the inter-organ cross talk indicators predetermined for each stage of the at least one disease selected from the group consisting of declined kidney function, chronic kidney disease, and renal failure, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) with no disease in the kidneys.

Item 30-1.

The method according to Item 30, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 31.

A method for obtaining information to predict the presence of a disease and/or the stage of the disease in each of one or more organs other than the kidneys in a subject affected with at least one disease selected from the group consisting of declined kidney function, chronic kidney disease, and renal failure, the method comprising the steps of:

(i) obtaining information about a stage of the at least one disease selected from the group consisting of declined kidney function, chronic kidney disease, and renal failure in the subject from a diagnostic result of the subject;

(ii) checking the information about the stage obtained in step (i) against standard data 2

(iii) determining, from the standard data 2, standard data a at a stage of the at least one disease selected from the group consisting of declined kidney function, chronic kidney disease, and renal failure corresponding to the information about the stage, based on the checking result obtained in step (ii), and extracting, from the standard data a, a pattern of an inter-organ cross talk indicator corresponding to the stage in the subject in each of one or more organs other than the kidneys in the subject; and (iv') checking the pattern of the inter-organ cross talk indicator extracted in step (iii) against known information regarding inter-organ cross talk indicators in diseases and/or the stages of the diseases, and obtaining information regarding the presence of a disease and/or the stage of the disease in each of the one or more organs other than the kidneys corresponding to the pattern of the inter-organ cross talk indicator in each of the one or more organs other than the kidneys in the subject, wherein the standard data 2 includes patterns of the inter-organ cross talk indicators predetermined for each stage of the at least one disease selected from the group consisting of declined kidney function, chronic kidney disease, and renal failure, each of the patterns being derived from a predetermined relationship between an amount of the inter-organ cross talk indicator in the organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) with no disease in the kidneys.

Item 31-1.

The method according to Item 31, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 32.

A method for generating standard data of patterns of inter-organ cross talk indicators for use in prediction of the presence of at least one disease selected from the group consisting of declined kidney function, chronic kidney disease, and renal failure and/or the stage of the disease in a subject, the method comprising the steps of:

extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;

extracting the inter-organ cross talk indicator from cells or tissue collected from each of the one or more organs other than the kidneys of negative control(s) of a gold standard;

identifying and quantifying the inter-organ cross talk indicators;

determining patterns of the inter-organ cross talk indicators, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure; and associating the patterns of the inter-organ cross talk indicators with the corresponding stages of the at least one disease selected from the group consisting of declined kidney function, chronic kidney disease, and renal failure.

Item 32-1.

The method according to Item 32, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Item 33.

A method for generating standard data of patterns of inter-organ cross talk indicators for use in prediction of the presence of a disease and/or the stage of the disease in each of one or more organs other than the kidneys in a subject affected with at least one disease selected from the group consisting of declined kidney function, chronic kidney disease, and renal failure, the method comprising the steps of:

extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;

extracting the inter-organ cross talk indicator from cells or tissue collected from each of the one or more organs other than the kidneys of negative control(s) of a gold standard;

identifying and quantifying the inter-organ cross talk indicators; and determining patterns of the inter-organ cross talk indicators for each stage of the at least one disease selected from the group consisting of declined kidney function, chronic kidney disease, and renal failure, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure.

Item 33-1.

The method according to Item 33, wherein the inter-organ cross talk indicator is at least one member selected from the group consisting of Aplnr, Spp1, Dnase1, Slco1a1, Anpep, Slc7a8, Oscar, proline-rich proteins, defensins, fibrinogens, and Hamp/Hepcidin.

Advantageous Effects of Invention

According to an embodiment of the present invention, a method for screening a candidate substance for an active ingredient to prevent or treat at least one disease selected from the group consisting of declined kidney function, chronic kidney disease, and renal failure can be provided.

Moreover, according to an embodiment of the present invention (Reverse iOrgans), subtle changes in the state of an organ other than the kidneys are correlated with subtle changes in the kidneys to capture subtle changes in the whole kidneys or kidney tissue, and thus the present invention can detect at least one disease selected from the group consisting of declined kidney function, chronic kidney disease, and renal failure earlier than usual diagnostic methods. Furthermore, the use of a device or program for evaluating such a correlation in multiple organs or tissues makes it possible to diagnose the multiple organs or tissues by diagnosing one organ or tissue, dramatically improving diagnostic efficiency. According to an embodiment of the present invention (Forward iOrgans), the state of an organ that cannot yet be diagnosed as having an abnormality by using a usual test is inferred from the state of the kidneys already confirmed to have at least one disease selected from the group consisting of declined kidney function, chronic kidney disease, and renal failure by using a usual diagnostic method; therefore, an abnormality in other organs or tissues caused by at least one disease selected from the group consisting of declined kidney function, chronic kidney disease, and renal failure can be detected early, and secondary and tertiary diseases (such as renal failure, hepatopathy, and cancer metastasis) can be prevented or treated.

BRIEF DESCRIPTION OF DRAWINGS

FIG. 12 schematically illustrates an outline of Forward iOrgans according to the present invention.

FIG. 21 is a list of genes in mice that can be detected by, for example, RNA-Seq. In FIG. 21, "Line No" indicates a line number in the list, "Gene Name" indicates a gene name registered with the U.S. National Center for Biotechnology Information (NCBI), and "Reference Seq. ID" indicates a reference sequence ID number registered with NCBI. "Chromosome Location" indicates a chromosome locus registered in mm10.

FIG. 22: Genes examined for their expression levels were classified as follows. Genes in which CKD/Sham is more than 1 or less than 1 were classified as group 2, genes in which CKD/Sham is more than 1.5 or less than 0.67 were classified as group 3, genes in which CKD/Sham is more than 2 or less than 0.5 were classified as group 4, and genes in which CKD/Sham is more than 5 or less than 0.2 were classified as group 5. In FIG. 22, "Line No." indicates a line number in the list, "Groups" indicates a group number of each of the groups classified based on the CKD/Sham values, "Gene Name" indicates a gene name registered with NCBI, "Human Gene ID" indicates a human gene number registered with NCBI that corresponds to the gene name, and "Updated" indicates the date of update to the Human Gene ID in NCBI. In "Sub-Group," "V-1" indicates genes, among the genes of group 5, in which CKD/Sham is more than 5; and "V-2" indicates genes, among the genes of group 5, in which CKD/Sham is less than 0.2. "IV-1" indicates genes, among the genes of group 4, in which CKD/Sham is more than 2 and that are not included in group 5; and "IV-2" indicates genes, among the genes of group 4, in which CKD/Sham is less than 0.5 and that are not included in group 5. "III-1" indicates genes, among the genes of group 3, in which CKD/Sham is more than 1.5 and that are not included in group 4 or group 5; and "III-2" indicates genes, among the genes of group 3, in which CKD/Sham is less than 0.67 and that are not included in group 4 or group 5. "II-1" indicates genes, among the genes of group 2, in which CKD/Sham is more than 1 and that are not included in any of groups 3 to 5; and "II-2" indicates genes, among the genes of group 2, in which CKD/Sham is less than 1 and that are not included in any of groups 3 to 5. Genes with no group number are a group in which CKD/Sham is 1.

FIG. 23 shows the expression levels of genes in which Sham>1 and CKD/Sham>5, genes in which Sham<1 and CKD/Sham>10, and genes in which Sham>10 and CKD/Sham<0.3 at the early and middle stages.

FIG. 24A shows a mutation site of Oscar-gRNA1 and an ssODN sequence. FIG. 24B shows a mutation site of Oscar-gRNA2 and an ssODN sequence. FIG. 24C indicates phenotypes of Oscar in obtained mice.

DESCRIPTION OF EMBODIMENTS

I. Screening

1. Explanation of Terms

Figure 1:
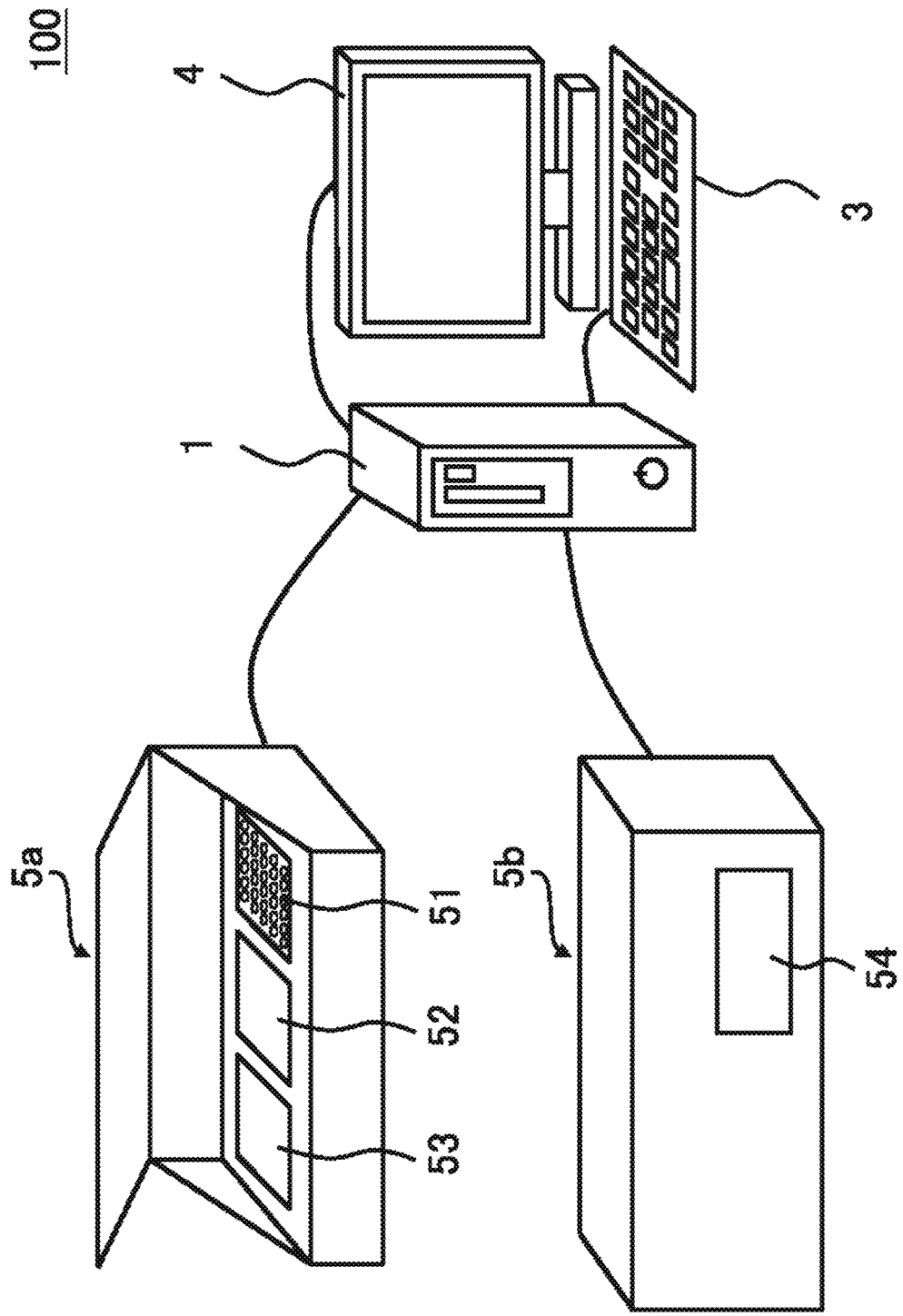
FIG. 1 is an overview of a system 100 according to a first embodiment of the present invention.

First, terms used in the present specification, claims, and abstract regarding inventions relating to a method and device for screening a candidate substance for an active ingredient to prevent or treat at least one disease selected from the group consisting of declined kidney function, chronic kidney disease, and renal failure; and a program that causes a computer to carry out functions for screening a candidate substance for an active ingredient to prevent or treat at least one disease selected from the group consisting of declined kidney function, chronic kidney disease, and renal failure, are explained. The same terms as some of the terms used in this section "I. Screening" are used in the section "II. iOrgans" described later; however, terms relating to the inventions described in "I. Screening" used in the specification, claims, and abstract are in accordance with the definitions in this section, unless otherwise stated. The definitions of the terms used in this section "I. Screening" and the definitions of the terms used in the section "II. iOrgans" described later are independent of each other, unless individual sections are referred to.

"Declined kidney function" as used herein refers to, in the case of humans, a condition in which, for example, at least one kidney disease marker shown in Tables 1-1 to 1-3 below falls outside a threshold range.

TABLE 1-1

| | Item | Threshold | Unit | Measurement method |
|---|---|---|---|---|
| Serum | Total protein | 6.7 to 7.8 | g/dl | Biuret method |
| | Albumin | 3.8 to 5.3 | mg/dl | BCG method |
| | Urea nitrogen | 8 to 20 | mg/dl | Urease-GLDH method |
| | Creatinine | Male: 0.6 to 1.0 Female: 0.4 to 0.8 | mg/dl | Enzymatic method |
| | Uric acid | Male: 3 to 7.7 Female: 2 to 7.7 | mg/dl | Uricase-POD method |
| | Ammonia | 12 to 66 | μg/dl | GLDH method |
| | Sodium | 136 to 145 | mEq/l | ISE |
| | Potassium | 3.4 to 4.5 | mEq/l | ISE |
| | Chlorine | 100 to 108 | mEq/l | ISE |
| | Total calcium | 8.6 to 10.1 | mg/dl | OCPC method |
| | Magnesium | 1.8 to 23 | mg/dl | Enzymatic method |

TABLE 1-1-continued

| | Item | Threshold | Unit | Measurement method |
|---|---|---|---|---|
| | Inorganic phosphorus | Adult: 2.2 to 4.1 Child: 4.0 to 7.0 | mg/dl | Enzymatic method |
| | Copper | 71 to 132 | μg/dl | Chelate colorimetric method |
| | Amylase | 40 to 126 | IU/l | JSCC standardization corresponding method |
| | FGF23 | Full-length assay threshold: 10 to 50 C-terminal assay threshold: 150 | pg/ml RU/ml | ELISA |
| Whole blood | Red blood cell count | Male: 414 to 563 Female: 373 to 495 | $\times 10^4/\mu l$ | Electrical resistance-type automatic blood cell counter |
| | Hemoglobin | Male: 12.9 to 17.4 Female: 10.7 to 15.3 | g/dl | Oxyhemoglobin method |
| | Pyruvic acid | 0.30 to 094 | mg/dl | Enzymatic method |

TABLE 1-2

| | Item | Threshold | Unit | Measurement method |
|---|---|---|---|---|
| Arterial blood gas analysis/acid-base equilibrium | $O_2$ saturation $S_aO_2$ | 94 to 99 | % | |
| | $O_2$ partial pressure $P_aO_2$ | 80 to 100 | Torr | |
| | $CO_2$ partial pressure $P_aCO_2$ | 35 to 45 | Torr | |
| | pH | 7.35 to 7.45 | | |
| | $HCO_3$ | 22 to 26 | mEq/l | |
| | Base excess (BE) | −2.2 to +2.2 | mEq/l | |
| | Buffer base (BB) | 46 to 52 | mEq/l | |
| | Standard bicarbonate (SB) | 21 to 25 | mEq/l | |
| Urine | Urinary output | 600 to 1,600 | ml/day | |
| | Specific gravity (spot urine) | 1.006 to 1.030 | | |
| | pH | 4.5 to 7.5 | | |
| | Urinary protein | 20 to 120 | mg/day | Pyrogallol red-Mo coloring method |
| | Albumin | 5.7 ± 2.6 | mg/day | |
| | Glucose | 2 to 20 | mg/dl | |
| Urinary sediment | Red blood cell count | <5 | /400x field | |
| | Leukocyte count | <5 | | |
| | Epithelial cell count | Less than 1 (excluding squamous epithelium) | | |
| | Cast count | <1 | | |

TABLE 1-3

| | Item | Threshold | Unit | Measurement method |
|---|---|---|---|---|
| Kidney function | Creatinine clearance (Ccr) | 70 to 130 | ml/min | |
| | 24-Hour creatinine clearance | Male: 62 to 108 Female: 57 to 78 | ml/min | |
| | Glomerular filtration rate (GFR) | Male: 129 ± 26 Female: 97 ± 13 | ml/min | |
| | Urea clearance | Maximum clearance: 62 to 77 Standard clearance: 45 to 55 | ml/min | |
| | Inulin clearance (GFR) | Male: 72 to 176 | ml/min/ 1.73 $m^2$ | |
| | | Female: 81 to 137 | ml/min/ 1.73 $m^2$ | |

TABLE 1-3-continued

| Item | Threshold | Unit | Measurement method |
|---|---|---|---|
| Sodium thiosulfate clearance | Male: 90 to 138 Female: 86 to 120 | ml/min | |
| Renal plasma flow (RPF) | 350 to 650 | ml/min | $C_{PAH}$ |
| Filtration fraction (FF) | 0.18 to 0.22 | | GRF/RPF |
| Fractional excretion of sodium | 1≤ | % | |
| Fractional excretion of lithium | 20 to 30 | % | |
| Phenolsulfonphthalein (PSP) test | ≤100 15 min value: ≥25 120 min value: ≥55 | mOsm/kg % % | |
| Concentration test | ≥1.025 | (Specific gravity) | Fishberg |
| Dilution test | ≤1.006 | (Specific gravity) | Fishberg |
| Free water clearance | At the time of water diuresis: 13 to 15 | ml/min | |
| Free water reabsorption | At the time of concentration: 1.5 to 2.0 | ml/min | |
| Maximal tubular excretory capacity | 81 ± 11 | mg/min/ 1.48 m² | $T_{mPAH}$ |
| Maximal tubular reabsorption capacity | 340 ± 18 | mg/min/ 1.48 m² | $T_{mPAH}$ |
| Rate of phosphate reabsorption | 80 to 96 | % | % TRP |
| $\beta_2$- Microglobulin | Serum: 0.8 to 0.2 Urine: 11 to 253 (30 to 340) | mg/l μg/day (μg/l) | LPIA LPIA |
| $\alpha_1$- Microglobulin | Serum: 10 to 30 Urine: 1.8 ± 0.9 | mg/l mg/l | EIA EIA |

"Chronic kidney disease" as used herein refers to, when the subject is a human, a condition in which kidney damage (for example, urine abnormalities such as proteinuria including microalbuminuria, abnormal urinary sediment, imaging abnormalities such as a single kidney and polycystic kidney disease, declined kidney function such as increased serum creatinine, electrolyte abnormalities such as hypokalemia due to tubular damage, abnormalities in histopathological examination such as renal biopsy), or declined kidney function, i.e., an estimated GFR (glomerular filtration rate) of less than 60 mL/min/1.73 m², persists for 3 months or more, according to the Clinical Practice Guidebook for Diagnosis and Treatment of Chronic Kidney Disease 2012 (edited by the Japanese Society of Nephrology).

Here, the estimated GFR (eGFR) can be calculated using the estimation formulas (eGFRcreat) from a serum creatinine value shown in Table 2 below. The estimation formulas (eGFRcys) based on serum cystatin C can be applied to those who have extremely low muscle mass, such as lower-extremity amputees.

For example, in the case in which protein is used as an index, when the results of a urine test 3 months or more prior and a recent urine test show that the subject has a persistent urinary protein level of 0.15 g/gCr or more, such a condition can be diagnosed as chronic kidney disease. When the subject has diabetes and the results of an albuminuria test 3 months or more prior and a recent albuminuria test show that the subject has a persistent urinary albumin level of 30 mg/gCr or more, such a condition can be diagnosed as chronic kidney disease.

For children, a threshold of serum creatinine (Cr) can be determined by using an enzymatic method for Japanese children, and used to evaluate children with kidney function abnormalities. For example, the eGFR in % for children aged 2 or older but 11 or younger can be represented by equation 1 below.

$$\text{eGFR (\%)} \times (0.3 \times \text{body height (m)/serum Cr value in subject}) \times 100 \quad \text{Equation 1}$$

In the case of non-human mammals, such as cats and dogs, it can be predicted whether a non-human mammal has chronic kidney disease from, for example, average daily water intake or urine specific gravity.

The severity of chronic kidney disease can be determined based on, for example, Table 3 below in the case of humans

TABLE 2

| | |
|---|---|
| Male | eGFRcreat (mL/min/1.73 m²) = 194 × Cr$^{-1.094}$ × age$^{-0.287}$ |
| | eGFRcys (mL/min/1.73 m²) = (104 × Cys-C $^{-1.094}$ × 0.996 $^{age}$)-8 |
| Female | eGFRcreat (mL/min/1.73 m²) = 194 × Cr$^{-1.094}$ × age$^{-0.287}$ × 0.739 |
| | eGFRcys (mL/min/1.73 m²) = (104 × Cys-C $^{-1.094}$ × 0.996 $^{age}$ × 0.929)-8 |

*This evaluation of kidney function is performed for persons aged 18 or older.

(Table 3 is Table 2 in the Clinical Practice Guidebook for Diagnosis and Treatment of Chronic Kidney Disease, 2012).

TABLE 3

| Primary disease | proteinuria category | | A1 | A2 | A3 |
|---|---|---|---|---|---|
| Diabetes | Urinary albumin quantification (mg/day) | | Normal | Micro-albuminuria | Macro-albuminuria |
| | Urinary albumin/Cr ratio (mg/gCr) | | Less than 30 | 30~299 | 300 or more |
| High blood pressure | Urinary protein quantification (g/day) | | Normal | Mild proteinuria | High proteinuria |
| Nephritis | | | | | |
| Polycystic kidney | Urinary protein/Cr ratio (g/gCr) | | Less than 0.15 | 0.15~0.49 | 0.50 or more |
| Renal graft | | | | | |
| Unknown | | | | | |
| Others | | | | | |
| GFR Category (Ml/MIN/1.73M2) | G1 | Normal or elevated value | ≥90 | A | B | C |
| | G2 | Normal or mild reduction | 60~89 | A | B | C |
| | G3a | Mild to moderate reduction | 45~59 | B | C | D |
| | G3b | Moderate to severe reduction | 30~44 | C | D | D |
| | G4 | Severe reduction | 15~29 | D | D | D |
| | G5 | End-stage kidney disease (ESKD) | <15 | D | D | D |

The severity is evaluated by a stage in which the primary disease, the GFR category, and the proteinuria category are combined.
Regarding the severity of CKD, the risks of mortality, end-stage kidney disease, and cardiovascular mortality increase as the stage increases in the order of B, C, and D with reference to the stage A.

"Renal failure" as used herein is included in the "chronic kidney disease" described above. For example, in the case of humans, "renal failure" refers to a condition in which eGFR is less than 45 ml/min/1.73 m$^2$, preferably less than 30 ml/min/1.73 m$^2$, and more preferably less than 15 ml/min/1.73 m$^2$ in chronic kidney disease.

"Individual" as used herein is not particularly limited, and includes humans and non-human mammals. Examples of non-human mammals include bovines, horses, sheep, goats, pigs, dogs, cats, rabbits, monkeys, and the like. Humans, cats, and dogs are preferable. There is no limitation on the age or sex of the individual.

"Subject" is an individual to which a test substance is to be administered, and preferably excludes humans. The subject is preferably an individual with a history of declined kidney function or other kidney disease. Individuals that may be the subject preferably have symptoms, such as polyuria, thirst, increased water intake, excessive gastric juice, vomiting, bloody urine, and general malaise. Further, individuals that may be the subject include individuals suspected of having kidney damage or chronic kidney disease according to a known diagnostic method, such as a medical interview, a urine test, a biochemical test of blood, kidney diagnostic imaging, or a renal biopsy, disease animal models, and the like.

"Test tissue" as used herein refers to tissue to which a test substance is to be administered. For example, the test tissue is living tissue in vitro, for example, collected from an individual that may be the subject, and cultured in vitro. The tissue may be an entire organ, or a portion of an organ.

"Test cell" as used herein refers to a cell to which a test substance is to be administered. For example, the test cell is a living cell in vitro, for example, collected from an individual that may be the subject, and cultured in vitro. The cell may be a cell whose passage capability is limited, such as a primary cultured cell; or may be a so-called cultured cell whose passage capability is maintained. Such cells may be cells prepared by genetic engineering.

"Specimen" as used herein includes cells, tissue (the adrenal glands, aorta, brain, lungs, pancreas, pituitary glands, skin, skull, skeletal muscle, spleen, testes, thyroid gland, kidneys, colon, eyeballs, heart, liver, submandibular glands, thymus, adipose tissue, stomach, jejunum, ileum, and the like), body fluids (sweat, secretions from skin, lacrimal fluid, saliva, spinal fluid, ascites fluid, and pleural effusion), urine, blood samples, and the like, derived from a subject described above. As specimens, adipose tissue, skin, hair roots, salivary glands (the parotid glands, submandibular glands, and sublingual glands, and preferably submandibular glands), sweat, secretions from skin, lacrimal fluid, saliva, urine, and blood samples are preferable; and urine, saliva, the parotid glands, blood samples, adipose tissue, hair roots, skin, secretions from skin, and sweat are more preferable.

Moreover, "specimen" may include test tissue itself, a portion of test tissue, a test cell itself, a portion of a test cell, and a culture supernatant of test tissue or a test cell.

In the section "2. Method for obtaining each measurement value" described later, when the measurement value of a kidney function prediction marker protein is obtained, the specimen is preferably a blood sample or a body fluid. In the same section, when the measurement value of mRNA of a kidney function prediction marker protein is obtained, the specimen is preferably tissue, a blood sample, or a body fluid.

"Blood sample" as used herein includes blood (whole blood) collected from a subject, or serum, plasma, or the like prepared from the blood. When the measurement value of a kidney function prediction marker protein is obtained, the blood sample is more preferably serum or plasma, and even more preferably serum. When the measurement value of mRNA of a kidney function prediction marker protein is obtained, it is preferable to use whole blood. The type of anticoagulant used for collecting plasma is not particularly limited. The type of blood sample of a subject used for measurement and the type of blood sample used for determining a predetermined threshold may be the same or different, and are preferably the same. When plasma is used as a blood sample, it is preferable that plasma for determining a predetermined threshold is prepared frao blood collected using the same anticoagulant as used for plasma of the subject.

Further, the specimen may be a fresh specimen, or may be a preserved specimen. When the specimen is preserved, it can be preserved in a room-temperature environment, a refrigerated environment, or a frozen environment; and cryopreservation is preferable.

"Test substance" as used herein refers to a substance to be evaluated as to whether it is a candidate substance for an active ingredient, and is not particularly limited. Examples include compounds, proteins, peptides, nucleic acids, lipids, carbohydrates, glycolipids, glycoproteins, metals, and the like. The method for administering a test substance is not particularly limited. When a test substance is administered to a test cell or test tissue, for example, the test substance can be administered to a culture medium of the cell or tissue in an amount of 1 pg/ml to 1 mg/ml. In the case of a subject, a test substance can be administered to the subject in an amount of 1 ng/kg to 1 g/kg per day. The period from administration of a test substance to collection of a specimen is not particularly limited, as long as an effect of the test substance is obtained.

Further, a specimen collected from a subject, test tissue, or test cell treated with a test substance may be referred to "test-substance-treated specimen" in the present specification. In addition, a specimen collected from a subject, test tissue, or test cell that is not treated with a test substance may be referred to as "untreated specimen" in the present specification.

"Healthy individual" is not particularly limited. Preferably, the healthy individual is a human or non-human mammal that is described in the explanation of the term "individual" and that does not show abnormal data in biochemical tests, blood tests, urine tests, serum tests, physiological tests, etc. The age and sex of the healthy individual are not particularly limited.

"Kidney function prediction marker" as used herein includes at least one member selected from the group consisting of the genes shown in FIG. 21 ("group 1"). More specifically, the kidney function prediction marker includes at least one member selected from the group consisting of the genes selected from group 2 shown in FIG. 22, preferably at least one member selected from the group consisting of the genes of group 3 shown in FIG. 22, more preferably at least one member selected from the group consisting of the genes of group 4 shown in FIG. 22, and even more preferably at least one member selected from the group consisting of the genes of group 5 shown in FIG. 22. Most preferably, the kidney function prediction marker is at least one member selected from the group consisting of the genes of group 6 shown in FIG. 23, in particular, at least one member selected from the group consisting of proline-rich proteins (Prh1, Prp2, Prb1, Prpmp5), defensins (Defa and Defb), Aplnr, Spp1, Dnase1, Slco1a1, Anpep, Slc7a8, Oscar, fibrinogens (Fga, Fgb, and Fgg), and Hamp/Hepcidin. Moreover, these groups may also include splicing variants of the individual genes.

As specific examples of combinations of a kidney function prediction marker protein and a specimen, it is preferable to use saliva and/or salivary glands (preferably the parotid glands) as a specimen in the case of PRPs, and it is preferable to use adipose tissue, hair roots, skin, secretions from skin, and/or sweat as a specimen when kidney function prediction markers are defensins and/or Hamp2.

In particular, skin is preferable as a specimen for obtaining the measurement value of Defb8; the stomach, skeletal muscle, and/or testes are preferable as a specimen for obtaining the measurement value of Defa24; adipose tissue is preferable as a specimen for obtaining the measurement values of Defb1, Defb10, Defb12, Defb14, Defb15, Defb18, Defb19, Defb2, Defb20, Defb21, Defb22, Defb23, Defb25, Defb26, Defb28, Defb29, Defb30, Defb35, Defb37, Defb39, Defb41, Defb42, Defb43, Defb45, Defb47, and/or Defb48; the skull is preferable as a specimen for obtaining the measurement value of Oscar; saliva, the salivary glands, or parotid glands are preferable as a specimen for obtaining the measurement values of Prb1, Prh1, Prp2, and/or Prpmp5; the skull, kidneys, and/or heart is preferable as a specimen for obtaining the measurement value of Spp1; the kidneys, salivary glands, preferably parotid glands, are preferable as a specimen for obtaining the measurement value of Dnase1; the aorta is preferable as a specimen for obtaining the measurement value of Slc7a8; the thyroid gland is preferable as a specimen for obtaining the measurement value of Anpep; the kidneys and/or liver is preferable as a specimen for obtaining the measurement value of Slco1a1; the adrenal glands, aorta, lungs, pituitary glands, skin, skin, skull, skeletal muscle, spleen, thyroid gland, kidneys, heart, and/or adipose tissue is preferable as a specimen for obtaining the measurement value of Aplnr; and the kidneys, a blood sample, and/or urine is preferable when the measurement values of Fga, Fgb, and Fgg are obtained.

"Measurement value of at least one protein selected from the group consisting of kidney function prediction markers" refers to a value reflecting the amount or concentration of at least one protein selected from the group consisting of kidney function prediction markers. When the measurement value is indicated by "amount," it may be expressed on either a mole basis or a mass basis; however, it is preferable to indicate the amount on a mass basis. When the value is expressed in terms of "concentration," it may be a molar concentration or a ratio of a mass per constant volume of a specimen (mass/volume), preferably a mass/volume ratio. The value reflecting the amount or concentration may be the above or the intensity of a signal such as fluorescence or luminescence.

"Measurement value of at least one mRNA selected from the group consisting of kidney function prediction markers" may be represented by the number of copies (absolute amount) of the kidney function prediction marker mRNA present in a certain amount of a specimen; or may be a value reflecting the relative expression level to that of a housekeeping gene, such as β2-microglobulin mRNA, GAPDH mRNA, Maea mRNA, or β-actin mRNA. The measurement value may also be represented by the intensity of a signal such as fluorescence or luminescence.

"Antibody against a kidney function prediction marker" is not limited, as long as the antibody specifically binds to at least one protein selected from the group consisting of the above-described kidney function prediction markers; and any of polyclonal antibodies, monoclonal antibodies, and fragments thereof (for example, Fab, F(ab)$_2$, etc.) obtained by immunizing a non-human animal with at least one protein selected from the group consisting of the kidney function prediction markers or a part thereof as an antigen can be used. Additionally, immunoglobulin classes and subclasses are not particularly limited. Moreover, the antibody against a kidney function prediction marker may be a chimeric antibody. Further, the antibody against a kidney function prediction marker may be scFv or the like.

Examples of a kidney function prediction marker protein used as an antigen for preparing an antibody against a kidney function prediction marker include the entirety or a part of at least one protein selected from the group consisting of the above-described kidney function prediction markers.

"Nucleic acid for kidney function prediction marker mRNA detection" as used herein is not limited, as long as it contains a sequence that specifically hybridizes to at least one mRNA selected from the group consisting of the above-described kidney function prediction markers, or to a reverse transcription product of the mRNA. The nucleic acid for detection may be DNA or RNA, and the nucleotides contained in the nucleic acid for detection may be naturally occurring nucleotides or artificially synthesized nucleotides.

The length of the nucleic acid for detection is not particularly limited. When the nucleic acid for detection is used as a capture probe in, for example, a microarray, the length of sequence that hybridizes to a target nucleic acid is preferably about 100 mer, more preferably about 60 mer, and even more preferably about 20 to 30 mer. The capture probe can be produced with, for example, a known oligonucleotide synthesizer. The capture probe may contain a sequence that does not hybridize to the target nucleic acid.

When the nucleic acid for detection is a primer used for PCR reactions, the length of sequence that hybridizes to a target nucleic acid is preferably about 50 mer, more preferably about 30 mer, and even more preferably about 15 to 25 mer. The primer can be produced with, for example, a known oligonucleotide synthesizer. The primer may contain a sequence that does not hybridize to the target nucleic acid. The primer may be labeled with a fluorescent dye or the like.

A probe for quantification that is decomposed during a PCR reaction may also be used for real-time quantification of a PCR product in RT-PCR, in addition to primers. The probe for quantification is not limited as long as it hybridizes to a target nucleic acid. The probe for quantification is preferably a nucleic acid with a length of about 5 to 20 mer that contains a sequence that hybridizes to a target nucleic acid. Further, it is preferred that the probe for quantification is labeled at one end with a fluorescent dye, and at the other end with a quencher of the fluorescent dye.

2. Method for Obtaining Each Measurement Value

The methods for obtaining the measurement value of at least one protein selected from the group consisting of kidney function prediction markers and the measurement value of at least one mRNA selected from the group consisting of kidney function prediction markers in the present specification are not limited, as long as the measurement values can be obtained. For example, they can be obtained according to the methods described below.

2-1. Method for Measuring Kidney Function Prediction Marker Protein

When the measurement value of at least one protein selected from the group consisting of kidney function prediction markers (hereinafter may be abbreviated as "measurement value of a kidney function prediction marker protein" in the present specification) is measured, a measurement method using an antibody against a kidney function prediction marker described in the section "1. Explanation of terms" can be used in the process in order to obtain the measurement value. The known ELISA method or the like can be used as the measurement method for obtaining the measurement value of a kidney function prediction marker protein.

In this embodiment, an antibody against a kidney function prediction marker for antigen capture can be immobilized on a solid phase such as a microplate, fluorescent beads, or magnetic beads in advance, and a complex between the immobilized antibody against a kidney function prediction marker and a kidney function prediction marker protein in a specimen can be formed. The amount or concentration of the kidney function prediction marker protein contained in the specimen can be measured by detecting the complex immobilized on the solid phase or the complex formed on the solid phase by a method known in the art. In this embodiment, a complex between an antibody against a kidney function prediction marker for antigen capture and a kidney function prediction marker protein in a specimen may be formed in advance, and then immobilized on a solid phase.

The method for immobilizing an antibody against a kidney function prediction marker for antigen capture on a solid phase is not particularly limited. An antibody against a kidney function prediction marker may be directly immobilized or indirectly immobilized with another substance interposed therebetween by using a known method. Examples of direct binding include physical adsorption and the like. Preferably, for example, an immunoplate may be used to directly physically bind an antibody against a kidney function prediction marker to the microplate.

The shape of the solid phase is not particularly limited. Examples include microplates, microtubes, test tubes, beads, and the like. The material of the solid phase is not particularly limited. For example, polystyrene, polypropylene, and the like can be used for microplates, microtubes, test tubes, etc. In the case of beads, Polystyrene xMAP (registered trademark) Beads (Luminex), MagPlex (registered trademark) Microspheres (Luminex), and the like can be used.

This method may comprise, following the formation of the complex, an operation of washing the solid phase. In washing, for example, PBS containing a surfactant or the like may be used.

In this method, the complex can be detected by using an antibody against a kidney function prediction marker for detection labeled with a labeling substance, or using an unlabeled antibody against a kidney function prediction marker, an anti-immunoglobulin antibody labeled with a labeling substance and capable of binding to the unlabeled antibody against a kidney function prediction marker, etc. It is preferable to use a labeled antibody against a kidney function prediction marker for detection. It is also preferable that the epitope in the kidney function prediction marker protein of the antibody against a kidney function prediction marker for detection is different from the epitope in the kidney function prediction marker protein of the antibody against a kidney function prediction marker for antigen capture.

The labeling substance used for the antibody against a kidney function prediction marker for detection or the labeled anti-immunoglobulin antibody is not particularly limited as long as the labeling substance generates a detectable signal. Examples include fluorescent substances, radioactive isotopes, enzymes, and the like. Examples of enzymes include alkaline phosphatase, peroxidase, and the like. Examples of fluorescent substances include fluorescent dyes such as fluorescein isothiocyanate (FITC), rhodamine, and Alexa Fluor (registered trademark), fluorescent proteins such as GFP, and the like. Examples of radioactive isotopes include $^{125}$I, $^{14}$C, $^{32}$P, and the like. Among them, alkaline phosphatase or peroxidase is preferable as the labeling substance.

The antibody against a kidney function prediction marker for detection is obtained by labeling an antibody against a kidney function prediction marker with the above-mentioned labeling substance by a labeling method known in the art. Alternatively, such labeling may be performed using a commercially available labeling kit or the like. For the labeled immunoglobulin antibody, the same method as the labeling of the antibody against a kidney function prediction marker may be used, or a commercially available product may be used.

In this method, the measurement value of the kidney function prediction marker contained in the specimen can be obtained by detecting a signal generated by the labeling substance of the labeled antibody against a kidney function prediction marker contained in the complex. Here, "detecting a signal" includes qualitatively detecting the presence or absence of a signal, quantifying the signal intensity, and semi-quantitatively detecting the signal intensity. Such semi-quantitative detection means to indicate the signal intensity in stages such as "no signal generation," "weak," "medium," and "strong." In this step, it is preferable to detect the signal intensity quantitatively or semi-quantitatively.

As the method for detecting a signal, a known method may be used. In this method, a measurement method according to the type of signal derived from the above-mentioned labeling substance may be appropriately selected. For example, when the labeling substance is an enzyme, detection of a signal may be performed by measuring a signal such as light or color generated by the reaction of the enzyme with a substrate using a known device such as a luminometer or a spectrophotometer.

The substrate of an enzyme can be appropriately selected from known substrates depending on the type of enzyme. For example, when alkaline phosphatase is used as an enzyme, examples of substrates include chemiluminescent substrates such as CDP-Star (registered trademark) (disodium 4-chloro-3-(methoxyspiro [1,2-dioxetane-3,2'-(5'-chloro)tricyclo [3.3.1.1$^{3,7}$]decan]-4-yl)phenyl phosphate), and chromogenic substrates such as 5-bromo-4-chloro-3-indolyl phosphate (BCIP), disodium 5-bromo-6-chloro-3-indolyl phosphate, and p-nitrophenyl phosphate. When the labeling substance is peroxidase, examples of substrates include tetramethylbenzidine (TMB) and the like.

When the labeling substance is a radioactive isotope, a signal, i.e., radiation, can be measured using a known device such as a scintillation counter. When the labeling substance is a fluorescent substance, a signal, i.e., fluorescence, can be measured using a known device such as a fluorescence microplate reader or Luminex (registered trademark) system (Luminex). The excitation wavelength and the fluorescence wavelength can be appropriately determined according to the type of fluorescent substance used.

The detection results of the signal can be used as the measurement value of the kidney function prediction marker protein. For example, when the signal intensity is quantitatively detected, the measurement value itself of the signal intensity or a value calculated from the measurement value of the signal intensity can be used as the measurement value of the kidney function prediction marker protein.

2-2. Method for Measuring Kidney Function Prediction Marker mRNA

A known measurement method, such as a microarray method, an RNA-Seq analysis method, or a quantitative RT-PCR method, can be used to obtain the measurement value of at least one mRNA selected from the group consisting of kidney function prediction markes (hereinafter may be abbreviated as "measurement value of a kidney function prediction marker mRNA" in the present specification). As probes used for the microarray method, probes of one's choosing, or known probes, may be synthesized and used; or a commercially available microarray chip may be used.

In this method, any of total RNA and mRNA extracted from a specimen may be used. It is preferred that the specimen used for total RNA and mRNA extraction is subjected to RNA extraction immediately after being collected from an individual; or is frozen (preferably under an atmosphere at −196° C. or less (rapidly cooled in liquid nitrogen)) immediately after being collected from an individual, and stored at −80° C. or less until RNA extraction.

The method for extracting total RNA and mRNA from a specimen is not particularly limited, and a known extraction method may be used.

Quantification by the microarray method may be performed according to a known method. The expression level of a kidney function prediction marker mRNA may be expressed as the relative expression level to that of a housekeeping gene; or expressed as the measurement value of the signal intensity of, for example, a fluorescent dye.

Quantification by RT-PCR may be performed by conducting a reverse transcription reaction using total RNA or mRNA extracted from a specimen as a template, and performing analysis by a real-time PCR method or the like with the obtained cDNA as a template by using specific primers for a kidney function prediction marker mRNA. In this case, the expression level of the kidney function prediction marker mRNA may be expressed as the relative expression level to that of a housekeeping gene or expressed as the measurement value of the signal intensity of, for example, a fluorescent dye.

In the RNA-Seq analysis method, mRNA extracted from a specimen is fragmented, cDNA is synthesized by reverse transcription reaction using these fragments as a temperate, and libraries are prepared. The nucleotide sequence of each fragment contained in each library is determined by using a next-generation sequencer, the obtained information is mapped to a reference gene sequence, and the expression level of mRNA is represented as RPKM (Reads Per Kilobase per Million). RPKM may be represented as the intensity of a signal in, for example, a heat map.

The detection results of the signal can be used as the expression level of the kidney function prediction marker mRNA. For example, when the signal intensity is quantitatively detected, the measurement value itself of the signal intensity or a value calculated from the measurement value of the signal intensity can be used as the expression level of the kidney function prediction marker mRNA.

Examples of the value calculated from the measurement value of the signal intensity include a value obtained by subtracting, from the measurement value of the signal intensity, the measurement value of the signal intensity of a negative control sample; a value obtained by dividing the measurement value of the signal intensity by the measurement value of the signal intensity of a positive control sample; a combination thereof; and the like. Examples of negative control samples include specimens of healthy subjects and the like. Examples of positive control samples include specimens containing the kidney function prediction marker mRNA at a predetermined expression level.

3. Evaluation of Function of Kidney Function Prediction Marker Protein

In the present invention, the method for evaluating function of a kidney function prediction marker protein is not particularly limited, as long as the function of the kidney function prediction marker protein can be evaluated. "Function of a kidney function prediction marker protein" as used herein is the original function of a kidney function prediction marker protein. For example, when the kidney function prediction marker protein is a receptor, the function is a function to activate when its ligand binds to the kidney function prediction marker protein, transmit a signal of the activation to a protein or a chemical mediator downstream in the signaling pathway to which the protein belongs, and act on cells etc. through the signaling pathway under the control of the receptor. When the kidney function prediction marker protein is a ligand, the function is a function to activate a receptor to which the ligand binds.

An example of the method for evaluating function of a kidney function prediction marker protein is a method in which the presence or absence of, for example, phosphorylation or dephosphorylation of a protein downstream in the signaling pathway to which a kidney function prediction marker protein belongs; an increase or decrease in the expression level of a protein located downstream; activation or inactivation of the transcriptional regulatory region of a protein located downstream; or the like, is detected. For example, the presence or absence of phosphorylation of a protein can be detected by a known method, such as the Western blotting method. For example, an increase or decrease in the expression level of a protein can be detected by a known method, such as the ELISA method, Western blotting method, quantitative RT-PCR method, or RNA-Seq method. Further, activation or inactivation of the transcriptional regulatory region can be detected by a reporter assay. Examples of reporters include firefly luciferase, Renilla luciferase, GFP (Green Fluorescent Protein), β-galactosidase, and the like. The reporter assay can be performed according to a known method.

As another method for evaluating function of a kidney function prediction marker protein, the function of a kidney function prediction marker protein can be evaluated by measuring the amount of a chemical mediator (e.g., inositol trisphosphate, cAMP, cGMP, $Ca^{2+}$) downstream in the signaling pathway to which the kidney function prediction marker protein belongs. Such a chemical mediator can be measured according to a known method.

The detection results obtained by using the ELISA method, Western blotting method, quantitative RT-PCR method, RNA-Seq method, and reporter assay, and the measurement results of a chemical mediator, can be used as evaluation results of function of the kidney function prediction marker protein. The evaluation results may be quantitative data, semi-quantitative information such as "high" and "low," or qualitative data such as "present" and "not present."

4. System Configuration for Screening

In the present invention, "I. 5. Screening 1" described later is performed using a measurement value obtained in the above "I. 2. Method for obtaining each measurement value." Moreover, in the present invention, "I. 6. Screening 2" described later is performed using an evaluation result obtained in the above "I. 3. Evaluation of function of kidney function prediction marker protein." First, system configurations for performing these processes are described.

Figure 2:
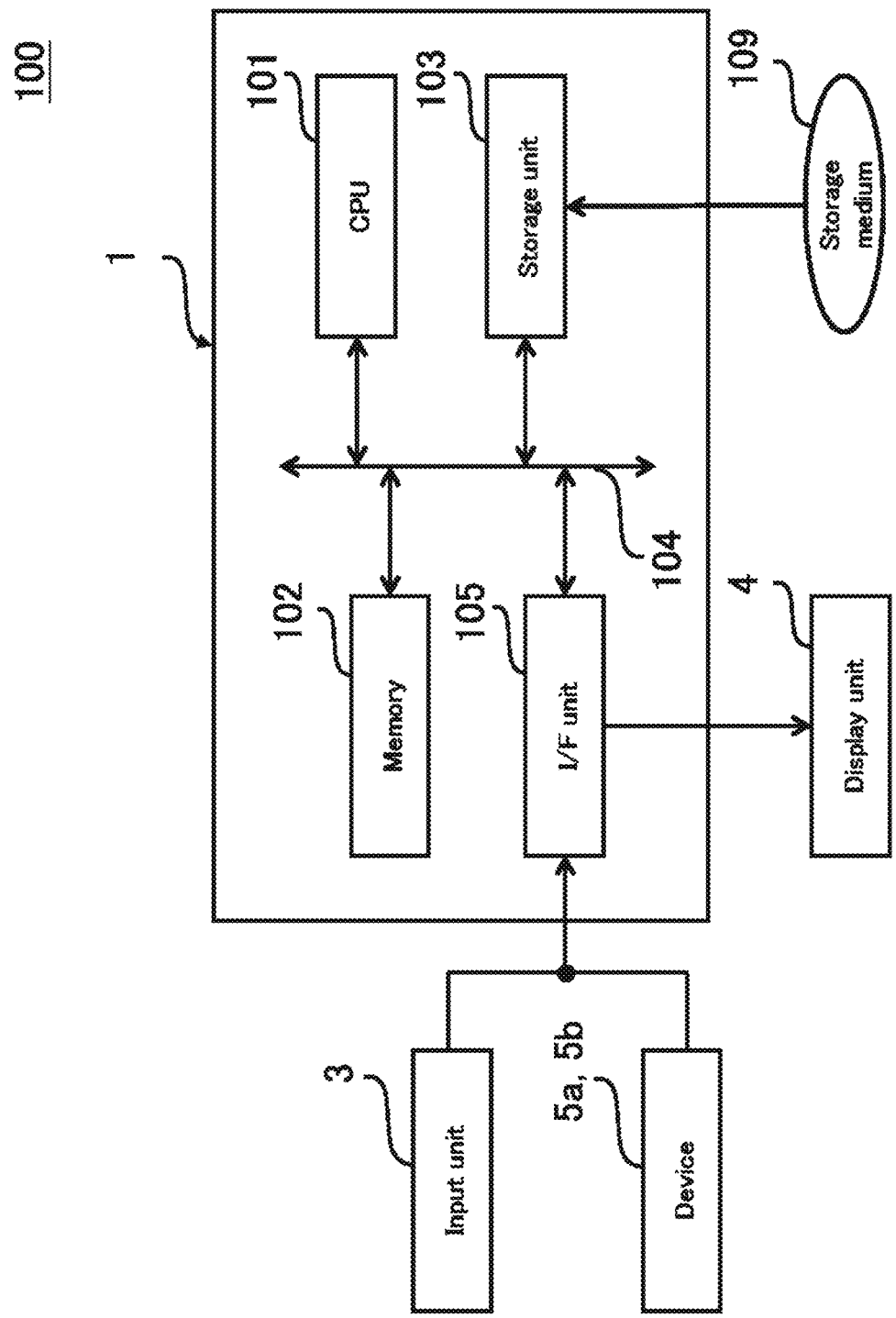
FIG. 2 is a block diagram illustrating a hardware configuration of the system 100 according to the first embodiment of the present invention.

FIG. 1 is an overview of a system 100 for performing screening 1 according to a first embodiment of the present invention. FIG. 2 is a block diagram illustrating a hardware configuration of the system 100. As an embodiment, the system 100 comprises a screening device 1, an input unit 3, a display unit 4, and a device 5a or a device 5b.

The screening device 1 includes, for example, a general-purpose personal computer, and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the screening device and external devices. The input unit 3 and the display unit 4 are connected to the screening device 1. The input unit 3 includes, for example, a keyboard; and the display unit 4 includes, for example, a liquid crystal display. The input unit 3 and the display unit 4 may be integrated and implemented as a display with a touch panel. The screening device 1 need not be a single device; and the CPU 101, the memory 102, the storage unit 103, and the like may be located in separate places, and connected via a network. The screening device may also be a device that omits the input unit 3 and the display unit 4, and that does not require an operator.

The screening device 1 and the device 5a or the device 5b are also not necessarily located in one place, and may be configured such that the devices located in separate places are communicatively connected to each other via a network.

In the explanation below, a process performed by the screening device 1 means a process performed by the CPU 101 of the screening device 1 based on a screening program stored in the storage unit 103 or the memory 102 shown in FIG. 2, unless otherwise specified. The CPU 101 temporarily stores necessary data (such as intermediate data being processed) in the memory 102 that serves as a work area, and suitably stores data that is stored for a long period of time, such as computation results, in the storage unit 103.

The device 5a is a device for measuring the amount or concentration of a protein, and comprises a sample placement area 51, a reaction unit 52, and a detection unit 53. A specimen, collected from a subject, set in the sample placement area 51 is dispensed into and incubated in a microplate that is placed in the reaction unit 52 and on which an antibody against a kidney function prediction marker for antigen capture is immobilized. The unreacted antigen is removed, if necessary. Thereafter, a detection antibody is dispensed into the microplate, followed by incubation. The unreacted antigen is removed if necessary, and a substrate for detecting the detection antibody is dispensed into the microplate. The microplate is transferred to the detection unit 53, and a signal generated by reaction with the substrate is measured. Another embodiment of the device 5a is a device for measuring the expression level of mRNA by microarray analysis. A reverse transcription reaction product set in the sample placement area 51 is dispensed into a microarray chip set in the reaction unit 52, followed by hybridization. After the microarray chip is washed, it is transferred to the detection unit 53, and a signal is measured.

Further, another embodiment of the device 5a is a device for measuring the expression level of mRNA by RT-PCR. A reverse transcription reaction product set in the sample placement area 51 is dispensed into a microtube set in the reaction unit 52, and a reagent for quantitative PCR is subsequently dispensed into the microtube. A signal in the tube is detected by the detection unit 53 while performing a PCR reaction in the reaction unit 52.

The device 5b is a device for measuring the expression level of mRNA by the RNA-Seq method, and comprises a sequence analysis unit 54. A sample subjected to a reaction for RNA-Seq is set in the sequence analysis unit 54, and analysis of nucleotide sequences is performed in the sequence analysis unit 54.

The devices 5a or 5b are connected to the screening device 1 by a wired or wireless connection. The device 5a A/D converts the measurement value of a protein or the measurement value of mRNA, and transmits it as digital data to the screening device 1. Similarly, the device 5b A/D converts the measurement value of mRNA, and transmits it as digital data to the screening device 1. Therefore, the screening device 1 can obtain, as digital data that can be computed, the measurement value of a protein or the measurement value of mRNA.

Figure 5:
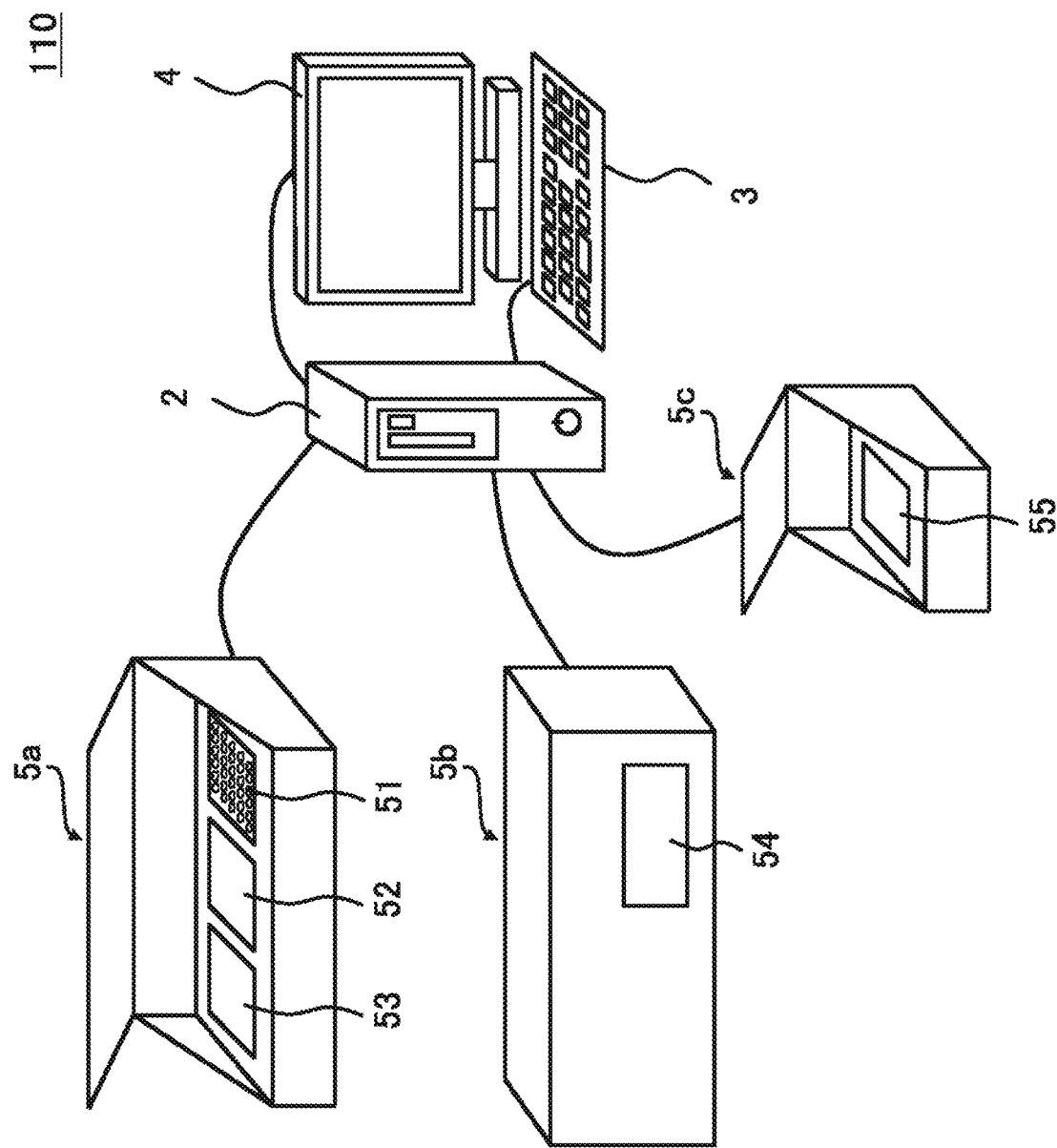
FIG. 5 is an overview of a system 110 according to a second embodiment of the present invention.
Figure 6:
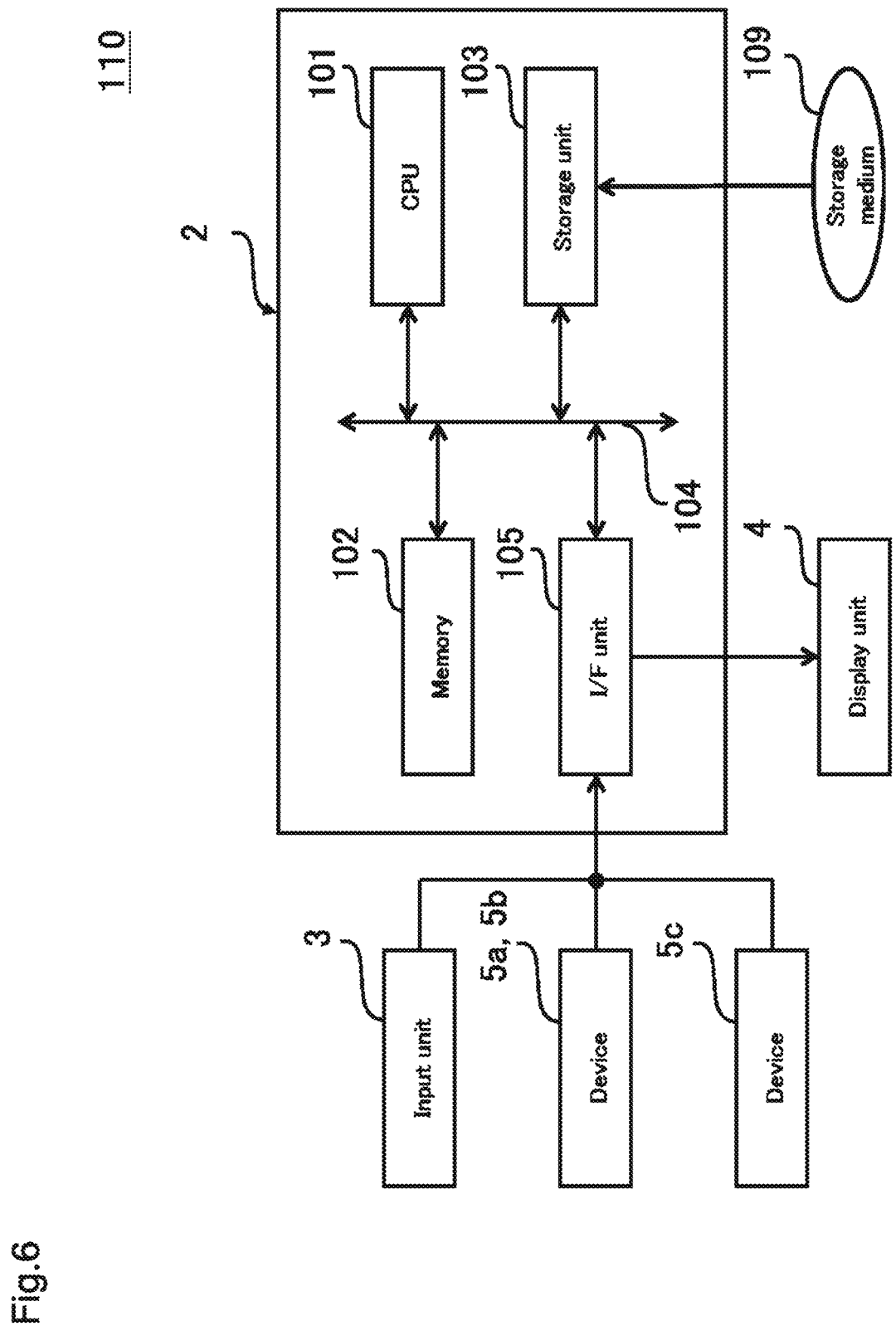
FIG. 6 is a block diagram illustrating a hardware configuration of the system 110 according to the second embodiment of the present invention.

FIG. 5 is an overview of a system 110 for performing screening 2 according to a second embodiment of the present invention. FIG. 6 is a block diagram illustrating a hardware configuration of the system 110. As an embodiment, the system 110 comprises a screening device 2, an input unit 3, a display unit 4, and a device 5a, a device 5b, or a device 5c.

The screening device 2 includes, for example, a general-purpose personal computer, and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the screening device and external devices. The input unit 3 and the display unit 4 are connected to screening device 2. The input unit 3 includes, for example, a keyboard; and the display unit 4 includes, for example, a liquid crystal display. The input unit 3 and the display unit 4 may be integrated and implemented as a display with a touch panel. The screening device 2 need not be a single device; and the CPU 101, the memory 102, the storage unit 103, and the like may be located in separate places, and connected via a network. The screening device may also be a device that omits the input unit 3 and the display unit 4, and that does not require an operator.

The screening device 2 and the device 5a, the device 5b, or the device 5c are also not necessarily located in one place, and may be configured such that the devices located in separate places are communicatively connected to each other via a network.

In the explanation below, a process performed by the screening device 2 means a process performed by the CPU 101 of the screening device 2 based on a screening program stored in the storage unit 103 or the memory 102 shown in FIG. 6, unless otherwise specified. The CPU 101 temporarily stores necessary data (such as intermediate data being processed) in the memory 102 that serves as a work area, and suitably stores data that is stored for a long period of time, such as computation results, in the storage unit 103.

The device 5a is a device for measuring the amount or concentration of a protein, and comprises a sample placement area 51, a reaction unit 52, and a detection unit 53. A specimen, collected from a subject, set in the sample placement area 51 is dispensed into and incubated in a microplate that is placed in the reaction unit 52, and on which an antibody against a kidney function prediction marker for antigen capture is immobilized. The unreacted antigen is removed, if necessary. Thereafter, a detection antibody is dispensed into the microplate, followed by incubation. The unreacted antigen is removed if necessary, and a substrate for detecting the detection antibody is dispensed into the microplate. The microplate is transferred to the detection unit 53, and a signal generated by reaction with the substrate is measured. Another embodiment of the device 5a is a device for measuring the expression level of mRNA by microarray analysis. A reverse transcription reaction product set in the sample placement area 51 is dispensed into a microarray chip set in the reaction unit 52, followed by hybridization. After the microarray chip is washed, it is transferred to the detection unit 53, and a signal is measured.

Further, another embodiment of the device 5a is a device for measuring the expression level of mRNA by RT-PCR. A reverse transcription reaction product set in the sample placement area 51 is dispensed into a microtube set in the reaction unit 52, and a reagent for quantitative PCR is subsequently dispensed into the microtube. A signal in the tube is detected by the detection unit 53 while performing a PCR reaction in the reaction unit 52. Further, another embodiment of the device 5a is a device for measuring a chemical mediator. A cell lysate set in the sample placement area 51 is dispensed into a microtube set in the reaction unit 52, and a reagent for measuring a chemical mediator is subsequently dispensed into the microtube. A signal in the tube is detected by the detection unit 53.

The device 5b is a device for measuring the expression level of mRNA by the RNA-Seq method, and comprises a sequence analysis unit 54. A sample subjected to a reaction for RNA-Seq is set in the sequence analysis unit 54, and analysis of nucleotide sequences is performed in the sequence analysis unit 54.

An embodiment of the device 5c is a device for detecting a signal in, for example, Western blotting. For example, when the function of a kidney function prediction marker protein is evaluated by using the Western blotting method or the like, a membrane for detection is set in the detection unit 55 of the device 5c, and chemiluminescence intensity or fluorescence intensity is measured. Another embodiment of the device 5c is a device for detecting the expression intensity of a reporter gene in a reporter assay. A cell lysate for a reporter assay is set in the detection unit 55 of the device 5c, and a liquid of a substrate is dispensed thereinto. Thereafter, chemiluminescence intensity is measured.

The devices 5a, 5b, or 5c are connected to the screening device 2 by a wired or wireless connection. The device 5a A/D converts the detection result of a protein, the detection result of mRNA, or the measurement result of a chemical mediator, and transmits it as digital data to the screening device 2. The device 5b A/D converts the detection result of mRNA, and transmits it as digital data to the screening device 2. The device 5c A/D converts the measurement result of a signal in Western blotting or the like or the measurement result of a reporter assay or the like, and transmits it as digital data to the screening device 2. Therefore, the screening device 2 can obtain, as digital data regarding the evaluation result of function of a kidney function prediction marker protein that can be computed, the detection result of a protein, the detection result of mRNA, the measurement result of a chemical mediator, the measurement result of a signal in Western blotting, or the measurement result of a reporter assay.

5. Screening 1

5-1. Outline

In this embodiment, it is determined that a test substance is a candidate substance for an active ingredient to prevent or treat at least one disease selected from the group consisting of declined kidney function, chronic kidney disease, and renal failure, by using the measurement value of a kidney function prediction marker protein and/or the measurement value of mRNA of the protein in a specimen collected from a subject, test tissue, or test cell treated with the test substance (a test-substance-treated specimen). The measurement value(s) of the test-substance-treated specimen are obtained by performing the above "I. 2. Method for obtaining each measurement value."

More specifically, this embodiment comprises the steps of:
(I) obtaining a measurement value of a kidney function prediction marker protein and/or a measurement value of mRNA of the protein in a specimen collected from a subject, test tissue, or test cell treated with a test substance (a test-substance-treated specimen); and
(II) determining that the test substance is a candidate substance for the active ingredient based on the measurement value(s) obtained in step (I).

In this case, when the measurement value of a kidney function prediction marker protein and/or the measurement value of mRNA of the protein in the test-substance-treated specimen is close to the measurement value of a corresponding kidney function prediction marker protein and/or the measurement value of mRNA of the protein in a healthy individual, it can be determined that the test substance is a candidate substance for the active ingredient.

Here, step (I) may be performed in such a manner that a measurement value is obtained by actually performing the "I. 2. Method for obtaining each measurement value," or in such a manner that the prediction device described later or the like is allowed to obtain a measurement value already obtained. In addition, step (I) and step (II) are not necessarily performed consecutively in the same organization. For example, the measurement value(s) obtained in step (I) may be sent to a third-party organization to perform step (II) and the subsequent process.

Further, in this embodiment, it may be determined that the test substance is a candidate substance for an active ingredient to prevent or treat at least one disease selected from the group consisting of declined kidney function, chronic kidney disease, and renal failure, by comparing the measurement value(s) of the test-substance-treated specimen with the measurement value of the kidney function prediction marker protein and/or the measurement value of mRNA of the protein in a specimen collected from a subject, test tissue, or test cell that is not treated with the test substance (an untreated specimen). The measurement value(s) of the untreated specimen are obtained by performing the above "I. 2. Method for obtaining each measurement value." More specifically, this embodiment may comprise, between steps (I) and (II), the step of comparing the measurement value(s) of the test-substance-treated specimen obtained in step (I) with a measurement value of a corresponding kidney function prediction marker protein and/or a measurement value of mRNA of the protein in a specimen collected from a subject, test tissue, or test cell that is not treated with the test substance (an untreated specimen). In this case, when the measurement value of the kidney function prediction marker protein and/or the measurement value of mRNA of the protein in the test-substance-treated specimen indicates a more improved result than the measurement value of the corresponding kidney function prediction marker protein and/or the measurement value of mRNA of the protein in the untreated specimen, it can be determined that the test substance is a candidate substance for the active ingredient.

Here, for example, in the case where the specimen is collected from a subject with at least one disease selected from the group consisting of declined kidney function, chronic kidney disease, and renal failure, and where the measurement value of the kidney function prediction marker protein and/or the measurement value of mRNA of the protein increases with a decline in kidney function, if the measurement value of the kidney function prediction marker protein and/or the measurement value of mRNA of the protein in the test-substance-treated specimen is lower than the measurement value of the corresponding kidney function prediction marker protein and/or the measurement value of mRNA of the protein in the untreated specimen when compared with each other, it can be determined that the at least one disease selected from the group consisting of declined kidney function, chronic kidney disease, and renal failure has been improved by the test substance. In this case, there is no particular limitation on how much lower the measurement value(s) are. When the measurement value(s) of the test-substance-treated specimen are, for example, 85% or less, preferably 70% or less, more preferably 50% or less of the measurement value(s) of the untreated specimen, it can be determined that the at least one disease selected from the group consisting of declined kidney function, chronic kidney disease, and renal failure has been improved by the test substance.

In the case where the specimen is collected from a subject with at least one disease selected from the group consisting of declined kidney function, chronic kidney disease, and renal failure, and where the measurement value of the kidney function prediction marker protein and/or the measurement value of mRNA of the protein decreases with a decline in kidney function, if the measurement value of the kidney function prediction marker protein and/or the measurement value of mRNA of the protein in the test-substance-treated specimen is higher than the measurement value of the corresponding kidney function prediction marker protein and/or the measurement value of mRNA of the protein in the untreated specimen when compared with each other, it can be determined that the at least one disease selected from the group consisting of declined kidney function, chronic kidney disease, and renal failure has been improved by the test substance. In this case, there is no particular limitation on how much higher the measurement value(s) are. When the measurement value(s) of the test-substance-treated specimen are, for example, 115% or more, preferably 130% or more, more preferably 150% or more of the measurement value(s) of the untreated specimen, it can be determined that the at least one disease selected from the group consisting of declined kidney function, chronic kidney disease, and renal failure has been improved by the test substance.

Further, the screening 1 may comprise, before step (I), the steps of (i) treating the test substance to the subject, test tissue, or test cell, (ii) collecting the specimen from the subject, test tissue, or test cell to which the test substance has been treated in step (i), and (iii) collecting the protein and/or the mRNA from the specimen obtained in step (ii). In this case, step (ii) and step (iii) are not necessarily performed consecutively in the same organization. For example, the specimen collected in step (ii) may be sent to a third-party organization to perform step (iii) and the subsequent steps. In addition, step (iii) and step (I) are also not necessarily performed consecutively in the same organization. For example, the protein and/or the mRNA collected in step (iii) may be sent to a third-party organization to perform the steps after step (iii).

5-2. Screening Device

The present invention includes, as the first embodiment, a device for screening a candidate substance for an active ingredient to prevent or treat at least one disease selected from the group consisting of declined kidney function, chronic kidney disease, and renal failure, the device comprising the following computation means:
   first measurement value obtaining means for obtaining a measurement value of a kidney function prediction marker protein and/or a measurement value of mRNA of the protein in a specimen collected from a subject, test tissue, or test cell treated with a test substance (a test-substance-treated specimen); and
   means for determining that the test substance is a candidate substance for the active ingredient based on the measurement value(s) obtained by the first measurement value obtaining means.

Preferably, the above screening device further comprises:
   second measurement value obtaining means for obtaining a measurement value of the kidney function prediction marker protein and/or a measurement value of mRNA of the protein in a specimen collected from a subject, test tissue, or test cell that is not treated with the test substance (an untreated specimen); and
   means for comparing the measurement value(s) of the test-substance-treated specimen with the measurement value(s) of the untreated specimen,
   wherein the determination means determines that the test substance is a candidate substance for the active ingredient based on the comparison result obtained by the measurement value comparison means. The determination method is in accordance with the description in the section "I. 5-4. Screening method" described later.

In this embodiment, a candidate substance for an active ingredient to prevent or treat at least one disease selected from the group consisting of declined kidney function, chronic kidney disease, and renal failure can be screened by the system 100 (FIGS. 1 and 2) comprising the screening device 1 as the screening device described above.

Figure 3:
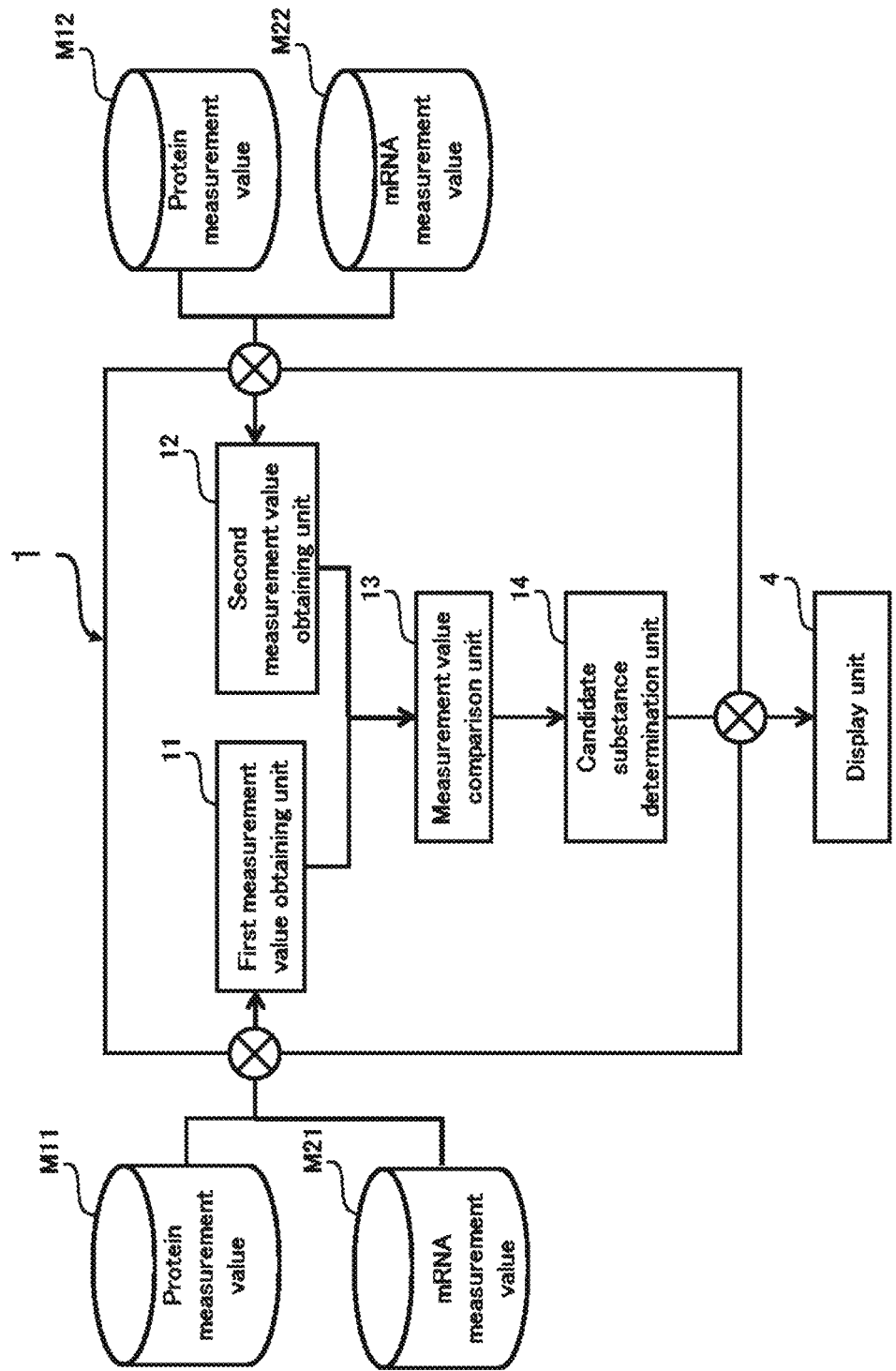
FIG. 3 is a block diagram illustrating functions of a screening device 1 according to the first embodiment of the present invention.

FIG. 3 is a block diagram illustrating functions of the screening device 1 according to this embodiment. The screening device 1 comprises a first measurement value obtaining unit 11, a second measurement value obtaining unit 12, a measurement value comparison unit 13, and a candidate substance determination unit 14. The second measurement value obtaining unit 12 may be optional. These functional blocks are implemented by installing the screening program according to the present invention in the storage unit 103 or the memory 102 of the screening device 1 shown in FIG. 2, and causing the CPU 101 to execute the screening program. Thereby, the screening device 1 carries out the screening method described in the section "I. 5-4. Screening method" described later. The first measurement value obtaining means, second measurement value obtaining means, measurement value comparison means, and determination means recited in the claims correspond to the first measurement value obtaining unit 11, second measurement value obtaining unit 12, measurement value comparison unit 13, and candidate substance determination unit 14 shown in FIG. 3, respectively.

In other words, the screening device 1 is a device for screening a candidate substance for an active ingredient to prevent or treat at least one disease selected from the group consisting of declined kidney function, chronic kidney disease, and renal failure, the device executing the following computation functions by the CPU 101:
   a first measurement value obtaining function for obtaining a measurement value of a kidney function prediction marker protein and/or a measurement value of mRNA of the protein in a specimen collected from a subject, test tissue, or test cell treated with a test substance (a test-substance-treated specimen); and
   a function for determining that the test substance is a candidate substance for the active ingredient based on the measurement value(s) obtained by the first measurement value obtaining function.

Preferably, the screening device 1 further executes the following functions by the CPU 101:
   a second measurement value obtaining function for obtaining a measurement value of the kidney function prediction marker protein and/or a measurement value of mRNA of the protein in a specimen collected from a subject, test tissue, or test cell that is not treated with the test substance (an untreated specimen); and
   a function for comparing the measurement value(s) of the test-substance-treated specimen with the measurement value(s) of the untreated specimen,
   wherein the determination function determines that the test substance is a candidate substance for the active ingredient based on the comparison result obtained by the measurement value comparison function.

In this embodiment, a measurement value M11 of a kidney function prediction marker protein in a test-substance-treated specimen is put into the screening device 1 from the device 5a, and a measurement value M21 of mRNA of the protein is put into the screening device 1 from the device 5a or 5b. Similarly, a measurement value M12 of the kidney function prediction marker protein in an untreated specimen is also put into the screening device 1 from the device 5a, and a measurement value M22 of mRNA of the protein is also put into the screening device 1 from the device 5a or 5b.

The measurement values M11 and M12 of the kidney function prediction marker protein and the measurement values M21 and M22 of mRNA of the protein in the test-substance-treated specimen and the untreated specimen may also be put into the screening device 1 from a third-party organization (not shown) via a network.

Moreover, the functional blocks, i.e., the first measurement value obtaining unit 11, the second measurement value obtaining unit 12, the measurement value comparison unit 13, and the candidate substance determination unit 14, are not necessarily executed by a single CPU, and may be processed by multiple CPUs in a distributed manner. For example, these functional blocks may be configured such that the functions of the first measurement value obtaining unit 11 and the second measurement value obtaining unit 12 are executed by a CPU of a first computer, and such that the functions of the measurement value comparison unit 13 and the candidate substance determination unit 14 are executed by a CPU of a second computer, i.e., another computer.

5-3. Screening Program

In order to carry out the processing for steps S11 to S17 in FIG. 4 below, the screening device 1 according to the first embodiment of the present invention stores the screening program according to this embodiment in the storage unit 103 beforehand, for example, in an executable format (for example, a form in which the program can be produced by conversion from a programming language using a compiler). The screening device 1 carries out the processing using the screening program stored in the storage unit 103.

Specifically, the screening program according to the first embodiment of the present invention is a screening program that, when executed by a computer, causes the computer to carry out the following processing to screen a candidate substance for an active ingredient to prevent or treat at least one disease selected from the group consisting of declined kidney function, chronic kidney disease, and renal failure:

first measurement value obtaining processing of obtaining a measurement value of a kidney function prediction marker protein and/or a measurement value of mRNA of the protein in a specimen collected from a subject, test tissue, or test cell treated with a test substance (a test-substance-treated specimen); and processing of determining that the test substance is a candidate substance for the active ingredient based on the measurement value(s) obtained by the first measurement value obtaining processing.

Preferably, the screening program further causes the computer to carry out second measurement value obtaining processing of obtaining a measurement value of the kidney function prediction marker protein and/or a measurement value of mRNA of the protein in a specimen collected from a subject, test tissue, or test cell that is not treated with the test substance (an untreated specimen); and, in the determination processing, it is determined that the test substance is a candidate substance for the active ingredient, by comparing the measurement value(s) obtained by the first measurement value obtaining processing with the measurement value(s) obtained by the second measurement value obtaining processing. The determination method is in accordance with the description in the section "I. 5-4. Screening method" described later.

In this embodiment, as shown in FIG. 2, the screening program is stored in a computer-readable non-transitory tangible storage medium 109, such as a CD-ROM, and is installed in the screening device 1 from the storage medium 109; alternatively, the screening device 1 may be connected to the internet (not shown) to download the program code of the screening program via the internet.

5-4. Screening Method

The screening device 1 according to the first embodiment of the present invention carries out the screening method according to the first embodiment of the present invention. The screening method according to the first embodiment of the present invention includes a method for screening a candidate substance for an active ingredient to prevent or treat at least one disease selected from the group consisting of declined kidney function, chronic kidney disease, and renal failure, the method comprising the steps of:

(I) obtaining a measurement value of a kidney function prediction marker protein and/or a measurement value of mRNA of the protein in a specimen collected from a subject, test tissue, or test cell treated with a test substance (a test-substance-treated specimen); and (II) determining that the test substance is a candidate substance for the active ingredient based on the measurement value(s) obtained in step (I).

Preferably, the above screen method further comprises, between steps (I) and (II), the step of comparing the measurement value(s) of the test-substance-treated specimen obtained in step (I) with a measurement value of a corresponding kidney function prediction marker protein and/or a measurement value of mRNA of the protein in a specimen collected from a subject, test tissue, or test cell that is not treated with the test substance (an untreated specimen).

Figure 4:
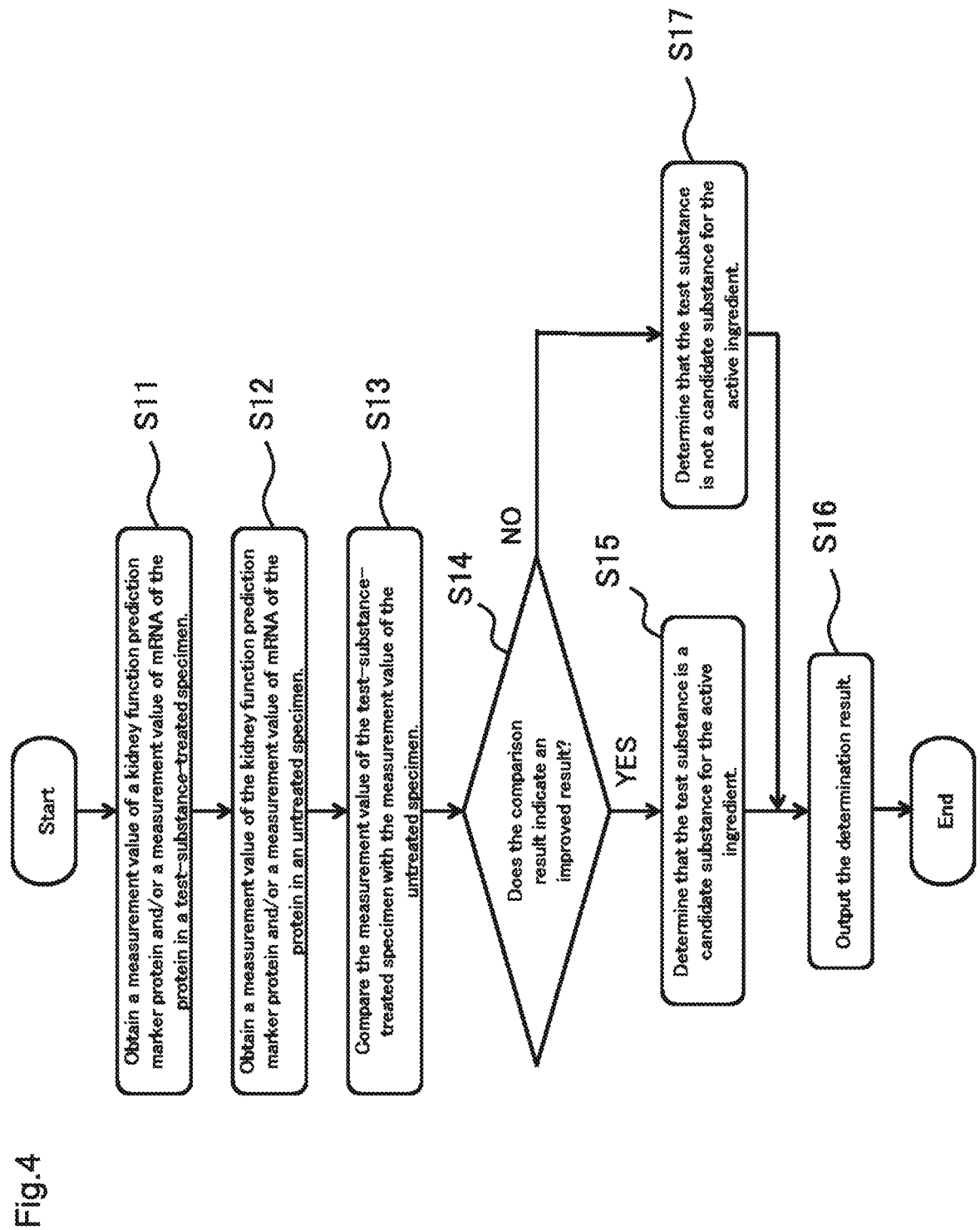
FIG. 4 is a flow chart illustrating a flow of data processing performed by the screening device 1 according to the first embodiment of the present invention to carry out a screening method.

FIG. 4 is a flow chart illustrating a flow of data processing performed by the screening device 1 according to the first embodiment of the present invention to carry out the screening method. Steps S11, S12, and S13 are performed by the first measurement value obtaining unit 11, second measurement value obtaining unit 12, and measurement value comparison unit 13 shown in FIG. 3, respectively. Steps S14 to S17 are performed by the candidate substance determination unit 14 shown in FIG. 3.

In step S11, the first measurement value obtaining unit 11 obtains a measurement value M11 of a protein and/or a measurement value M21 of mRNA in a test-substance-treated specimen.

In step S12, the second measurement value obtaining unit 12 obtains a measurement value M12 of the protein and/or a measurement value M22 of the mRNA in an untreated specimen.

In step S13, the measurement value comparison unit 13 compares the measurement value(s) of the test-substance-treated specimen obtained in step S11 with the measurement value(s) of the untreated specimen obtained in step S12. The comparison result is output to the candidate substance determination unit 14.

The candidate substance determination unit 14 determines that the test substance is a candidate substance for the active ingredient based on the comparison result obtained by the measurement value comparison unit 13. More specifically, when the comparison result indicates an improved result (YES in step S14), the candidate substance determination unit 14 determines, in step S15, that the test substance is a candidate substance for the active ingredient.

More specifically, in the case where the test-substance-treated specimen is collected from a subject with at least one disease selected from the group consisting of declined kidney function, chronic kidney disease, and renal failure, and where the measurement value of the kidney function prediction marker protein and/or the measurement value of mRNA of the protein increases with a decline in kidney function, when a value obtained by dividing M11 by M12 or a value obtained by dividing M21 by M22 is, for example, 0.85 or less, preferably 0.7, and more preferably 0.5 or less, the measurement value comparison unit 13 determines that the at least one disease selected from the group consisting of declined kidney function, chronic kidney disease, and renal failure has been improved by the test substance, and outputs a comparison result such that the disease has been improved. When the comparison result indicates that the disease has been improved, the candidate substance determination unit 14 determines that the test substance is a candidate substance for the active ingredient. In the case where the test-substance-treated specimen is collected from a subject with at least one disease selected from the group consisting of declined kidney function, chronic kidney disease, and renal failure, and where the measurement value of the kidney function prediction marker protein and/or the measurement value of mRNA of the protein decreases with a decline in kidney function, when a value obtained by dividing M11 by M12 or a value obtained by dividing M21 by M22 is, for example, 1.15 or more, preferably 1.3 or more, and more preferably 1.5 or more, the measurement value comparison unit 13 determines that the at least one disease selected from the group consisting of declined kidney function, chronic kidney disease, and renal failure has been improved by the test substance, and outputs a comparison result such that the disease has been improved. When determining that the at least one disease selected from the group consisting of declined kidney function, chronic kidney disease, and renal failure has not been improved by the test substance, the measurement value comparison unit 13 outputs a comparison result such that the disease has not been improved. When the comparison result indicates that the disease has been improved, the candidate substance determination unit 14 determines that the test substance is a candidate substance for the active ingredient.

In step S16, the candidate substance determination unit 14 outputs the result determined in step S15. In this embodiment, the candidate substance for the active ingredient is displayed on the display unit 4, and the determination result is stored in the storage unit 103 in the screening device 1. The determination result may be displayed on a display unit of an external computer terminal connected to the screening device 1 via the internet, for example, a display unit of a computer terminal in a third-party organization (not shown), instead of displaying the determination result on the display unit 4.

In step S14, when the comparison result indicates that the disease has not been improved, the processing proceeds to step S17, and the candidate substance determination unit 14 determines that the test substance is not the active ingredient. In this case, the result such that the test substance is not the active ingredient may be displayed on the display unit 4.

6. Screening 2
6-1. Outline

In this embodiment, it is determined that a test substance is a candidate substance for an active ingredient to prevent or treat at least one disease selected from the group consisting of declined kidney function, chronic kidney disease, and renal failure, using an evaluation result of function of a kidney function prediction marker protein in a test-substance-treated specimen obtained by performing a method described in the above section "I.3. Evaluation of function of kidney function prediction marker protein." More specifically, this embodiment comprises the following steps: (I) evaluating function of a kidney function prediction marker protein in a specimen collected from a subject, test tissue, or test cell treated with a test substance (a test-substance-treated specimen); and (II) determining that the test substance is a candidate substance for the active ingredient based on the evaluation result obtained in step (I). In this case, when the evaluation result of function of the kidney function prediction marker protein in the test-substance-treated specimen is closed to an evaluation result of function of a corresponding kidney function prediction marker protein in a healthy individual, it can be determined that the test substance is a candidate substance for the active ingredient.

Here, step (I) may be performed in such a manner that an evaluation result is obtained by actually performing "I. 3. Evaluation of function of kidney function prediction marker protein," or in such a manner that the prediction device described later or the like is allowed to obtain an evaluation result already obtained. In addition, step (I) and determination step (II) are not necessarily performed consecutively in the same organization. For example, the evaluation result obtained in step (I) may be sent to a third-party organization to perform step (II) and the subsequent process.

Further, in this embodiment, the above evaluation result can be compared with an evaluation result of function of the kidney function prediction marker protein in an untreated specimen obtained by the method described in the above section "I. 3. Evaluation of function of kidney function prediction marker protein," and it can be determined that the test substance is a candidate substance for an active ingredient to prevent or treat at least one disease selected from the group consisting of declined kidney function, chronic kidney disease, and renal failure. More specifically, this embodiment further comprises, between steps (I) and (II), the step of comparing the evaluation result of the test-substance-treated specimen obtained in step (I) with an evaluation result of function of a corresponding kidney function prediction marker protein in an untreated specimen. In this case, when the evaluation result of function of the kidney function prediction marker protein of the test-substance-treated specimen indicates a more improved result than the evaluation result of function of the corresponding kidney function prediction marker protein of the untreated specimen, it can be determined that the test substance is a candidate substance for the active ingredient.

For example, in the case where the specimen is collected from a subject with at least one disease selected from the group consisting of declined kidney function, chronic kidney disease, and renal failure, and where the function of the kidney function prediction marker protein is activated as kidney function declines, when the evaluation result of function of the kidney function prediction marker protein in the test-substance-treated specimen shows a lower result than the evaluation result of function of the corresponding kidney function prediction marker protein in the untreated specimen when compared with each other, it can be determined that the at least one disease selected from the group consisting of declined kidney function, chronic kidney disease, and renal failure has been improved by the test substance. In this case, there is no particular limitation on how much lower the evaluation result is. When the measurement value of the test-substance-treated specimen is, for example, 85% or less, preferably 70% or less, more preferably 50% or less of the evaluation result of the untreated specimen, it can be determined that the at least one disease selected from the group consisting of declined kidney function, chronic kidney disease, and renal failure has been improved by the test substance.

In the case where the specimen is collected from a subject with at least one disease selected from the group consisting of declined kidney function, chronic kidney disease, and renal failure, and where the function of the kidney function prediction marker protein is suppressed as kidney function declines, when the evaluation result of function of the kidney function prediction marker protein in the test-substance-treated specimen shows a higher result than the evaluation result of function of the corresponding kidney function prediction marker protein in the untreated specimen when compared with each other, it can be determined that the at least one disease selected from the group consisting of declined kidney function, chronic kidney disease, and renal failure has been improved by the test substance. In this case, there is no particular limitation on how much higher the evaluation result is. When the measurement value of the test-substance-treated specimen is, for example, 115% or more, preferably 130% or more, more preferably 150% or more of the evaluation result of the untreated specimen, it can be determined that the at least one disease selected from the group consisting of declined kidney function, chronic kidney disease, and renal failure has been improved by the test substance.

Further, the screening 2 may comprises, before step (I), the steps of (i) treating the test substance to the subject, test tissue, or test cell; and (ii) collecting the specimen from the subject, test tissue, or test cell after step (i). In this case, step (i) and step (I) are not necessarily performed consecutively in the same organization. For example, the specimen collected in step (ii) may be sent to a third-party organization to perform step (I) and the subsequent process.

6-2. Screening Device

The present invention includes, as the second embodiment, a device for screening a candidate substance for an active ingredient to prevent or treat at least one disease selected from the group consisting of declined kidney function, chronic kidney disease, and renal failure, the device comprising the following computation means:

first evaluation result obtaining means for obtaining an evaluation result of function of a kidney function prediction marker protein in a specimen collected from a subject, test tissue, or test cell treated with a test substance (a test-substance-treated specimen); and means for determining that the test substance is a candidate substance for the active ingredient based on the evaluation result obtained by the first evaluation result obtaining means.

Preferably, the screening device further comprising:

second evaluation result obtaining means for obtaining an evaluation result of function of the kidney function prediction marker protein in a specimen collected from a subject, test tissue, or test cell that is not treated with the test substance (an untreated specimen); and means for comparing the evaluation result of the test-substance-treated specimen with the evaluation result of the untreated specimen, wherein the determination means determines that the test substance is a candidate substance for the active ingredient based on the comparison result obtained by the evaluation result comparison means. The determination method is in accordance with the description in the section "I. 6-4. Screening method" described later.

In this embodiment, a candidate substance for an active ingredient to prevent or treat at least one disease selected from the group consisting of declined kidney function, chronic kidney disease, and renal failure can be screened by the system 110 (FIGS. 5 and 6) comprising the screening device 2 described above.

Figure 7:
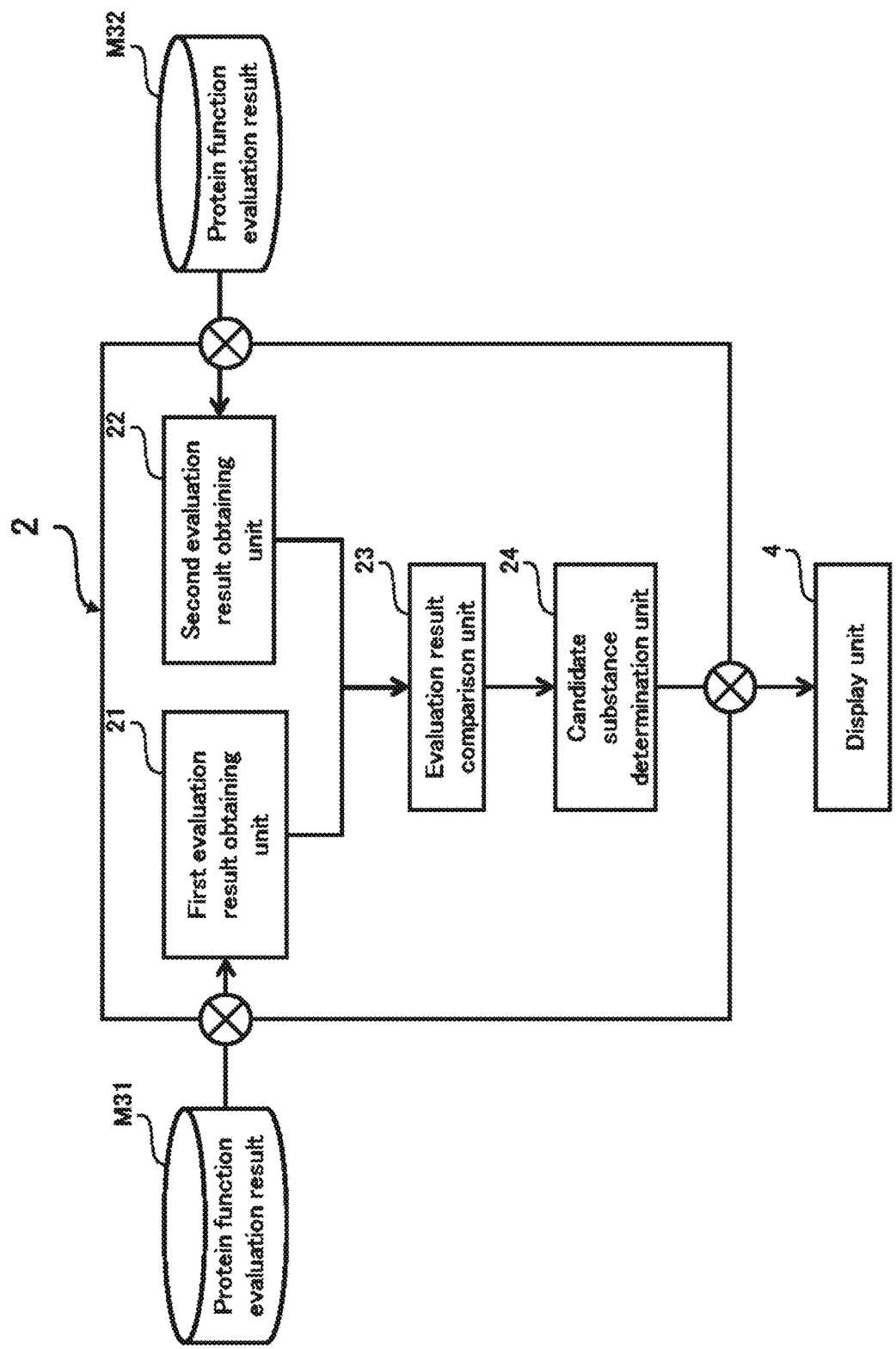
FIG. 7 is a block diagram illustrating functions of a screening device 2 according to the second embodiment of the present invention.

FIG. 7 is a block diagram illustrating functions of the screening device 2 according to the second embodiment of the present invention. The screening device 2 comprises a first evaluation result obtaining unit 21, a second evaluation result obtaining unit 22, an evaluation result comparison unit 23, and a candidate substance determination unit 24. The second evaluation result obtaining unit 22 may be optional. These functional blocks are implemented by installing the screening program according to the present invention in the storage unit 103 or the memory 102 of the screening device 2 shown in FIG. 6, and causing the CPU 101 to execute the screening program. Thereby, the screening device 2 carries out the screening method described in the "I. 6-4. Screening method" described later. The first evaluation result obtaining means, second evaluation result obtaining means, evaluation result comparison means, and determination means recited in the claims correspond to the first evaluation result obtaining unit 21, second evaluation result obtaining unit 22, evaluation result comparison unit 23, and candidate substance determination unit 24 shown in FIG. 7, respectively.

In other words, the screening device 2 is a device for screening a candidate substance for an active ingredient to prevent or treat at least one disease selected from the group consisting of declined kidney function, chronic kidney disease, and renal failure, the device executing the following computation functions by the CPU 101:

a first evaluation result obtaining function for obtaining an evaluation result of function of a kidney function prediction marker protein in a specimen collected from a subject, test tissue, or test cell treated with a test substance (a test-substance-treated specimen); and a function for determining that the test substance is a candidate substance for the active ingredient based on the evaluation result obtained by the first evaluation result obtaining function.

Preferably, the screening device 2 further executing the following functions by the CPU 101:

a second evaluation result obtaining function for obtaining an evaluation result of function of the kidney function prediction marker protein in a specimen collected from a subject, test tissue, or test cell that is not treated with the test substance (an untreated specimen); and a function for comparing the evaluation result of the test-substance-treated specimen with the evaluation result of the untreated specimen, wherein the determination function determines that the test substance is a candidate substance for the active ingredient based on the comparison result obtained by the evaluation result comparison function. The determination method is in accordance with the description in the section "I. 6-4. Screening method" described later.

In this embodiment, an evaluation result M31 of function of a kidney function prediction marker protein in a test-substance-treated specimen is put into the screening device 2 from the device 5a, 5b, or 5c. Similarly, an evaluation result M32 of the kidney function prediction marker protein in an untreated specimen is also put into the screening device 2 from the device 5a, 5b, or 5c.

The evaluation results M31 and M32 of function of the kidney function prediction marker protein in the test-substance-treated specimen and the untreated specimen may also be put into the screening device from a third-party organization (not shown) via a network.

Moreover, the functional blocks, i.e., the first evaluation result obtaining unit 21, the second evaluation result obtaining unit 22, the evaluation result comparison unit 23, and the candidate substance determination unit 24, are not necessarily executed by a single CPU, and may be processed by multiple CPUs in a distributed manner. For example, these functional blocks may be configured such that the functions of the first evaluation result obtaining unit 21 and the second evaluation result obtaining unit 22 are executed by a CPU of a first computer, and such that the functions of the evaluation result comparison unit 23 and the candidate substance determination unit 24 are executed by a CPU of a second computer, i.e., another computer.

6-3. Screening Program

In order to carry out the processing for steps S21 to S27 in FIG. 8 below, the screening device 2 according to the second embodiment of the present invention stores the screening program according to this embodiment in the storage unit 103 beforehand, for example, in an executable format (for example, a form in which the program can be produced by conversion from a programming language using a compiler). The screening device 2 carries out the processing using the screening program stored in the storage unit 103.

Specifically, the screening program according to the second embodiment of the present invention is a screening program that, when executed by a computer, causes the computer to carry out the following processing to screen a candidate substance for an active ingredient to prevent or treat at least one disease selected from the group consisting of declined kidney function, chronic kidney disease, and renal failure:

first evaluation result obtaining processing of obtaining an evaluation result of function of a kidney function prediction marker protein in a specimen collected from a subject, test tissue, or test cell treated with a test substance (a test-substance-treated specimen); and processing of determining that the test substance is a candidate substance for the active ingredient based on the evaluation result obtained by the first evaluation result obtaining processing.

Preferably, the screening program further causes the computer to carry out second evaluation result obtaining processing of obtaining an evaluation result of function of the kidney function prediction marker protein in a specimen collected from a subject, test tissue, or test cell that is not treated with the test substance (an untreated specimen); and processing of comparing the evaluation result of the test-substance-treated specimen with the evaluation result of the untreated specimen, and in the determination processing, it is determined that the test substance is a candidate substance for the active ingredient based on the comparison result obtained by the evaluation result comparison processing. The determination method is in accordance with the description in the section "I. 6-4. Screening method" described later.

In this embodiment, as shown in FIG. 6, the screening program is stored in a computer-readable non-transitory tangible storage medium 109, such as a CD-ROM, and is installed in the screening device 2 from the storage medium 109; alternatively, the screening device 2 may be connected to the internet (not shown) to download the program code of the screening program via the internet.

6-4. Screening Method

The screening device 2 according to the second embodiment of the present invention carries out the screening method according to the second embodiment of the present invention. The screening method according to the second embodiment of the present invention includes a method for screening a candidate substance for an active ingredient to prevent or treat at least one disease selected from the group consisting of declined kidney function, chronic kidney disease, and renal failure, the method comprising the steps of:

(I) evaluating function of a kidney function prediction marker protein in a specimen collected from a subject, test tissue, or test cell treated with a test substance (a test-substance-treated specimen); and (II) determining that the test substance is a candidate substance for the active ingredient based on the evaluation result obtained in step (I).

Preferably, the screening method further comprises, between steps (I) and (II), the step of comparing the evaluation result of the test-substance-treated specimen obtained in step (I) with an evaluation result of function of a corresponding kidney function prediction marker protein in a specimen collected from a subject, test tissue, or test cell that is not treated with the test substance (an untreated specimen).

Figure 8:
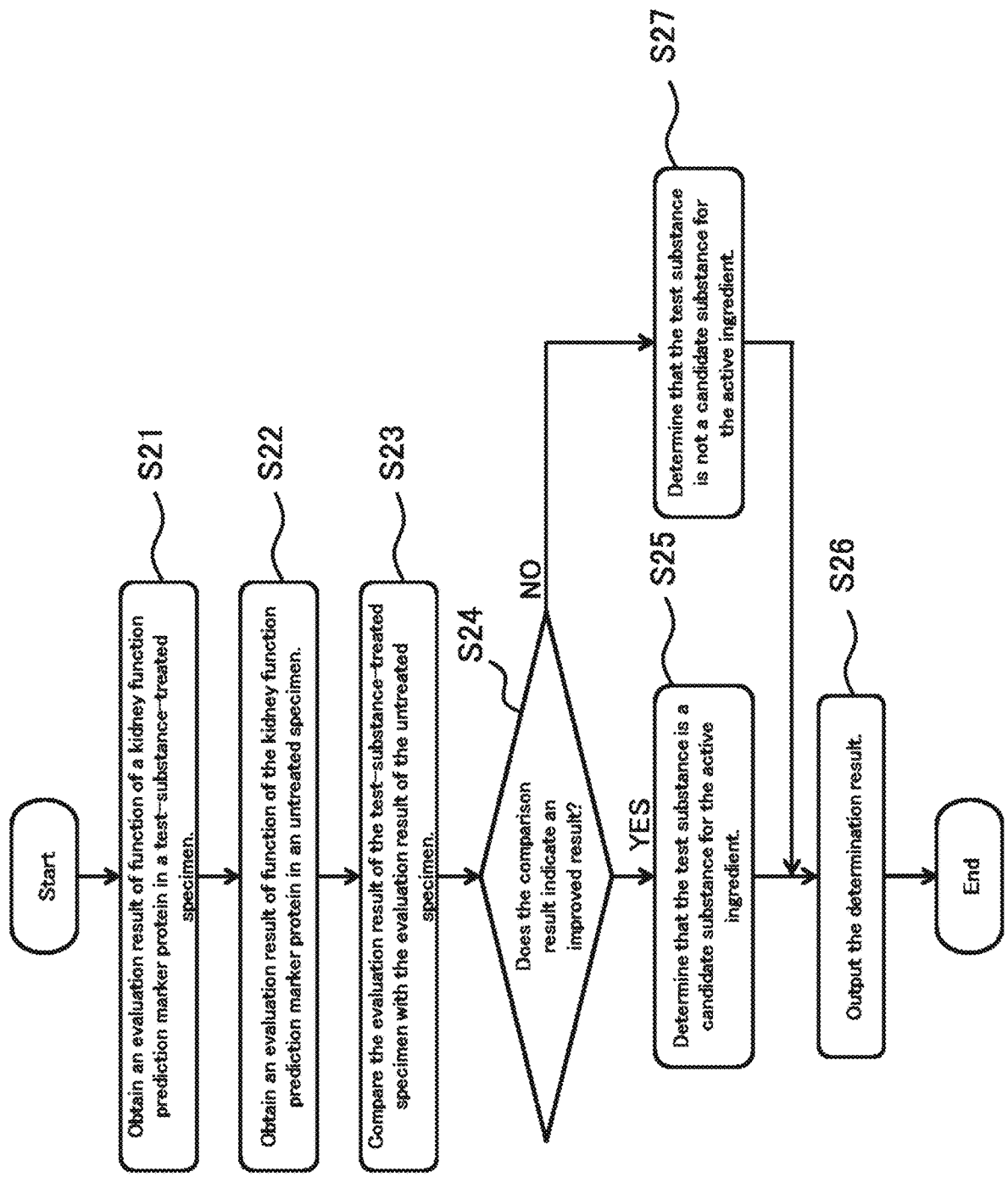
FIG. 8 is a flow chart illustrating a flow of data processing performed by the screening device 2 according to the second embodiment of the present invention to carry out a screening method.

FIG. 8 is a flow chart illustrating a flow of data processing performed by the screening device 2 according to the second embodiment of the present invention to carry out the method described above. Steps S21, S22, and S23 are performed by the first evaluation result obtaining unit 21, second evaluation result obtaining unit 22, and evaluation result comparison unit 23 shown in FIG. 7, respectively. Steps S24 to S27 are performed by the candidate substance determination unit 24 shown in FIG. 7.

In step S21, the first evaluation result obtaining unit 21 obtains an evaluation result M31 of function of a protein in a test-substance-treated specimen.

In step S22, the second evaluation result obtaining unit 22 obtains an evaluation result M32 of function of the protein in an untreated specimen.

In step S23, the evaluation result comparison unit 23 compares the evaluation result of the test-substance-treated specimen obtained in step S21 with the evaluation result of the untreated specimen obtained in step S22. The comparison result is output to the candidate substance determination unit 24.

The candidate substance determination unit 24 determines a candidate substance for the active ingredient based on the comparison result obtained by the evaluation result comparison unit 23. Specifically, when the comparison result indicates an improved result (YES in step S24), the candidate substance determination unit 24 determines, in step S25, that the test substance is a candidate substance for the active ingredient.

More specifically, in the case where the test-substance-treated specimen is collected from a subject with at least one disease selected from the group consisting of declined kidney function, chronic kidney disease, and renal failure, and where the function of the kidney function prediction marker protein is activated as kidney function declines, when a value obtained by dividing M31 by M32 is, for example, 0.85 or less, preferably 0.7 or less, more preferably 0.5 or less, the evaluation result comparison unit 23 determines that the at least one disease selected from the group consisting of declined kidney function, chronic kidney disease, and renal failure has been improved by the test substance, and outputs a comparison result such that the disease has been improved. When the comparison result indicates that the disease has been improved, the candidate substance determination unit 24 determines that the test substance is a candidate substance for the active ingredient. In the case where the test-substance-treated specimen is collected from a subject with at least one disease selected from the group consisting of declined kidney function, chronic kidney disease, and renal failure, and where the function of the kidney function prediction marker protein is suppressed as kidney function declines, when a value obtained by dividing M31 by M32 is, for example, 1.15 or more, preferably 1.3 or more, more preferably 1.5 or more, the evaluation result comparison unit 23 determines that the at least one disease selected from the group consisting of declined kidney function, chronic kidney disease, and renal failure has been improved by the test substance, and outputs a comparison result such that the disease has been improved. When determining that the at least one disease selected from the group consisting of declined kidney function, chronic kidney disease, and renal failure has not been improved by the test substance, the evaluation result comparison unit 23 outputs a comparison result such that the disease has not been improved. When the comparison result indicates an improved result, the candidate substance determination unit 24 determines that the test substance is a candidate substance for the active ingredient.

In step S26, the candidate substance determination unit 24 outputs the result determined in step S25. In this embodiment, the determination result is displayed on the display unit 4, and stored in the storage unit 103 in the screening device 2. The determination result may be displayed on a display unit of an external computer terminal connected to the screening device 2 via the internet, for example, a display unit of a computer terminal in a third-party organization, instead of displaying the determination result on the display unit 4.

In step S24, when the comparison result indicates that the disease has not been improved, the processing proceeds to step S27, and the candidate substance determination unit 24 determines that the test substance is not the active ingredient. In this case, the result such that the test substance is not the active ingredient may be displayed on the display unit 4.

7. Screening 3

The present invention further includes a third screening method. This embodiment is a method for screening a candidate substance for an active ingredient to prevent or treat at least one disease selected from the group consisting of declined kidney function, chronic kidney disease, and renal failure, the method comprising step (A) of detecting a kidney function prediction marker protein and/or mRNA of the protein in a test-substance-treated specimen. The detection of the kidney function prediction marker protein can be performed, for example, by a known detection method of proteins, such as the Western blotting method or ELISA method, using an "antibody against a kidney function prediction marker" described in the above section "I. 1. Explanation of terms." The detection of the kidney function prediction marker mRNA can be performed, for example, by a known method, such as the microarray method or RT-PCR, using a "nucleic acid for kidney function prediction marker mRNA detection" described in the above section "I. 1. Explanation of terms."

The detection result may be obtained through visual observation, or may be obtained as absorbance, fluorescence intensity, or luminescence intensity.

This embodiment may comprise step (B) of determining that the test substance is a candidate substance for the active ingredient based on the result obtained in the detection step. In this step, for example, in the case where the specimen is collected from a subject with at least one disease selected from the group consisting of declined kidney function, chronic kidney disease, and renal failure, and where the kidney function prediction marker protein is a protein whose expression increases with a decline in kidney function, when the kidney function prediction marker protein and/or mRNA of the protein is not detected, or even if detected, is significantly small, in the test-substance-treated specimen, it can be determined that the test substance is a candidate substance for the active ingredient. In the case where the specimen is collected from a subject with at least one disease selected from the group consisting of declined kidney function, chronic kidney disease, and renal failure, and where the kidney function prediction marker protein is a protein whose expression decrease with a decline in kidney function, when the kidney function prediction marker protein and/or mRNA of the protein in the test-substance-treated specimen is detected in a larger amount than a corresponding kidney function prediction marker protein and/or mRNA of the protein in an untreated specimen, it can be determined that the test substance is a candidate substance for the active ingredient.

Further, in this embodiment, the detection result of the kidney function prediction marker protein and/or mRNA of the protein in the test-substance-treated specimen may be compared with a detection result of a corresponding protein and/or mRNA in an untreated specimen, and it may be determined that the test substance is a candidate substance for the active ingredient. More specifically, this embodiment may comprise, between step (A) and step (B), a step of comparing the detection result of the test-substance-treated specimen obtained in step (A) with a detection result of a corresponding kidney function prediction marker protein and/or mRNA of the protein in an untreated specimen. For example, in the case where the specimen is collected from a subject with at least one disease selected from the group consisting of declined kidney function, chronic kidney disease, and renal failure, and where the expression of the kidney function prediction marker protein and/or mRNA of the protein increases with a decline in kidney function, when the protein and/or mRNA is detected in the untreated specimen, and when the corresponding protein and/or mRNA is not detected in the test-substance-treated specimen or the expression thereof is decreased in the test-substance-treated specimen, it can be determined that the test substance is a candidate substance for the active ingredient. In the case where the specimen is collected from a subject with at least one disease selected from the group consisting of declined kidney function, chronic kidney disease, and renal failure, and where the expression of the kidney function prediction marker protein and/or mRNA of the protein decreases with a decline in kidney function, when the protein and/or mRNA in the test-substance-treated specimen is detected in a larger amount than the kidney function prediction marker protein and/or mRNA of the protein in the untreated specimen, it can be determined that the test substance is a candidate substance for the active ingredient. In a comparison between the detection result of the kidney function prediction marker protein and/or mRNA of the protein in the test-substance-treated specimen and the detection result of the corresponding protein and/or mRNA in the untreated specimen, a difference between them may be a difference that can be visually detected.

This embodiment may comprise, before step (A), the following steps: (a) treating the test substance to the subject, test tissue, or test cell; (b) collecting the specimen from the subject, test tissue, or test cell to which the test substance has been administered in step (a); and (c) collecting the protein or mRNA from the specimen obtained in step (b).

8. Screening 4

When the functional expression of Oscar, which is a kidney function prediction marker protein, is suppressed, induction of expression of FGF23 is suppressed under ingestion of a diet with high phosphorus content. Thus, in the screening 1 to the screening 3 described above, when the kidney function prediction marker protein is Oscar, "screening a candidate substance for an active ingredient to prevent or treat at least one disease selected from the group consisting of declined kidney function, chronic kidney disease, and renal failure" can also be read as "screening a candidate substance capable of suppressing the functional expression of FGF23."

9. Biomarker

The present invention relates to a method for using a kidney function prediction marker protein and/or mRNA of the kidney function prediction marker protein as a biomarker for screening a candidate substance for an active ingredient to prevent or treat at least one disease selected from the group consisting of declined kidney function, chronic kidney disease, and renal failure. Here, the definition of "kidney function prediction marker" is in accordance with the description in the "1. Explanation of terms."

Any one protein selected from proteins encoded by the genes shown in FIG. 22 or any one mRNA selected from mRNAs encoded by the genes shown in FIG. 23 can be used as a biomarker for screening a candidate substance for an active ingredient to prevent or treat at least one disease selected from the group consisting of declined kidney function, chronic kidney disease, and renal failure.

Moreover, as another embodiment, a combination of at least two proteins selected from proteins encoded by the genes shown in FIG. 22, or a combination of at least two mRNAs of proteins selected from mRNAs encoded by the genes shown in FIG. 23 can be used as a biomarker for screening a candidate substance for an active ingredient to prevent or treat at least one disease selected from the group consisting of declined kidney function, chronic kidney disease, and renal failure.

These biomarkers are contained in each specimen.

II. iOrgans

This embodiment relates to two novel disease determination methods called "Reverse iOrgans" and "Forward iOrgans," based on a new methodology called "iOrgans (Inter-Organ Cross Talks) technology." In the methodology, a comprehensive database of changes in the amounts of gene expression, metabolites, etc., derived from organs other than a specific organ is constructed, and the changes are associated with functional and histological changes of the specific organ in a subject. The disease determination is achieved by using the comprehensive database. "iOrgans" is a technology to diagnose, prevent, and/or treat disease by using the interrelationship between the state of one organ and that of one or more other organs as a measure.

Figure 9:
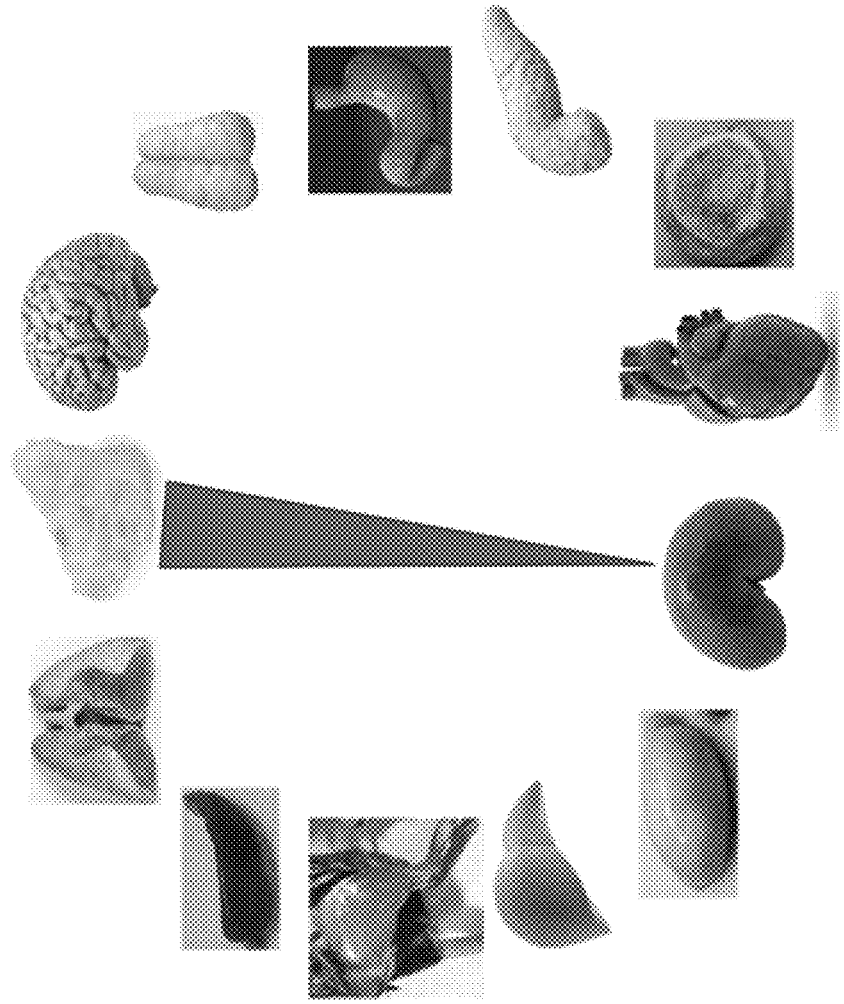
FIG. 9 schematically illustrates an outline of Reverse iOrgans according to the present invention.
Figure 10:
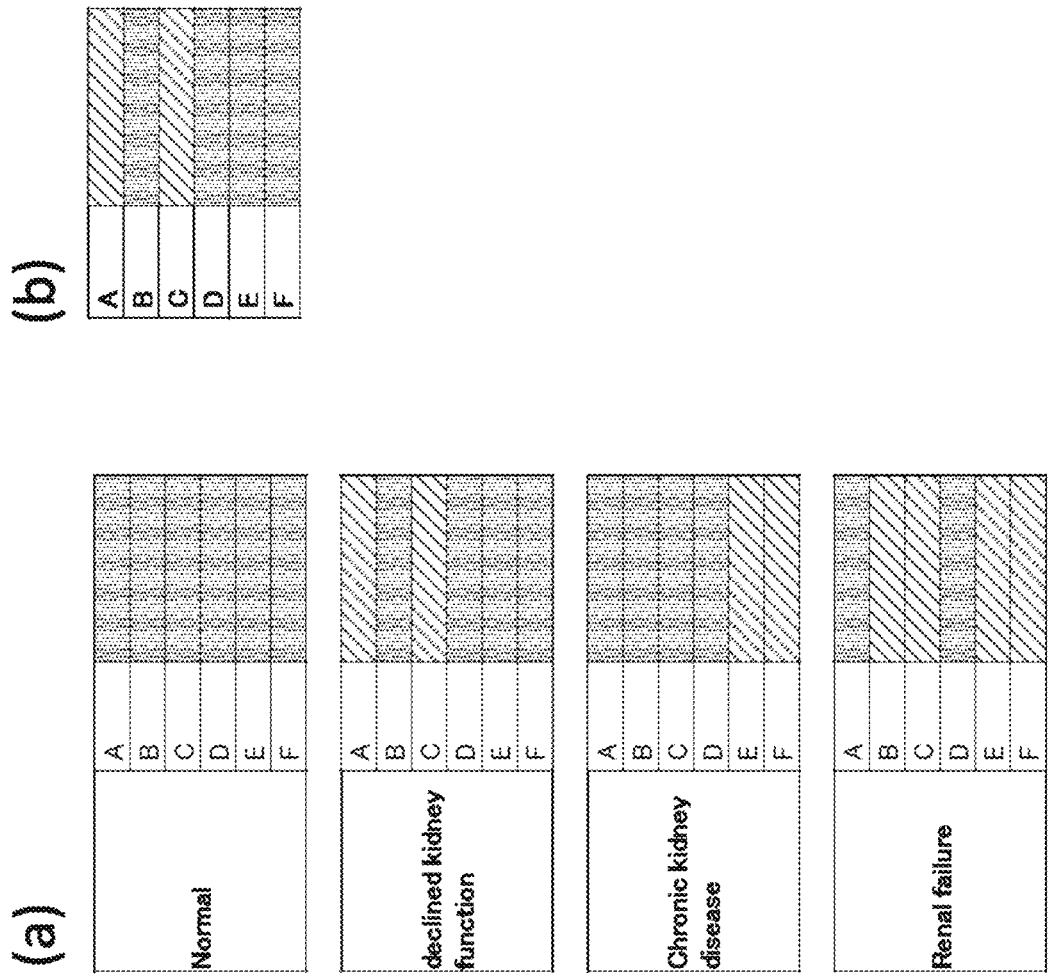
FIG. 10 schematically illustrates an outline of Reverse iOrgans according to the present invention.

FIGS. 9 and 10 schematically illustrate an outline of Reverse iOrgans according to the present invention.

Reverse iOrgans is a method for predicting a specific disease in a subject from information regarding, for example, the pattern of gene expression in each organ other than a specific organ collected from the same subject at the same time point. It is possible to predict the presence of a specific latent disease or the state of a specific organ by this method. In the example shown in FIG. 9, a disease (e.g., at least one disease selected from the group consisting of declined kidney function, chronic kidney disease, and renal failure) in a specific organ (e.g., kidneys) is predicted from information regarding, for example, the pattern of gene expression in another organ (e.g., adipose tissue or cells). An outline of the prediction method of Reverse iOrgans is described with reference to FIG. 10, assuming, as an example, that the other organ is adipose tissue, and that the disease in the specific organ is at least one disease selected from the group consisting of declined kidney function, chronic kidney disease, and renal failure. A to F shown in FIG. 10 represent an inter-organ cross talk indicator.

First, a pattern of gene expression (i.e., a pattern of an inter-organ cross talk indicator) in adipose tissue is collected beforehand for each stage of at least one disease selected from the group consisting of declined kidney function, chronic kidney disease, and renal failure, as standard data for each stage; and a group of standard data is prepared. FIG. 10(a) shows an example of standard data. The standard data of FIG. 10(a) shows a pattern of the inter-organ cross talk indicator, i.e., A to F in adipose tissue at each stage of the state of the kidneys (selected from normal state, declined kidney function, chronic kidney disease, and renal failure). In the pattern of the inter-organ cross talk indicator in declined kidney function, chronic kidney disease, or renal failure, items in the inter-organ cross talk indicator shown in gray represent items in the inter-organ cross talk indicator showing no changes relative to normal, and items in the inter-organ cross talk indicator shown with diagonal hatching represent items in the inter-organ cross talk indicator showing changes relative to normal.

Next, adipose tissue is collected from a subject, and the pattern of the inter-organ cross talk indicator in the adipose tissue is determined and used as data of the subject (e.g., FIG. 10(b)). Subsequently, the standard data and the data of the subject derived from adipose tissue are compared with each other, and similarity between patterns is calculated. When a pattern similar to the data of the subject is present in the standard data, it can be predicted that the state of the kidneys linked with the similar pattern in the standard data is the state of the kidneys (a disease stage selected from declined kidney function, chronic kidney disease, and renal failure) from which the subject is suffering. In the example shown in FIG. 10, the pattern of the data of the subject shown in (b) is similar to the second pattern from the top in the standard data. The second pattern from the top is a pattern obtained when the kidneys are in the state of declined kidney function. It can thus be predicted that the kidneys of the subject are in the state of declined kidney function.

Figure 11:
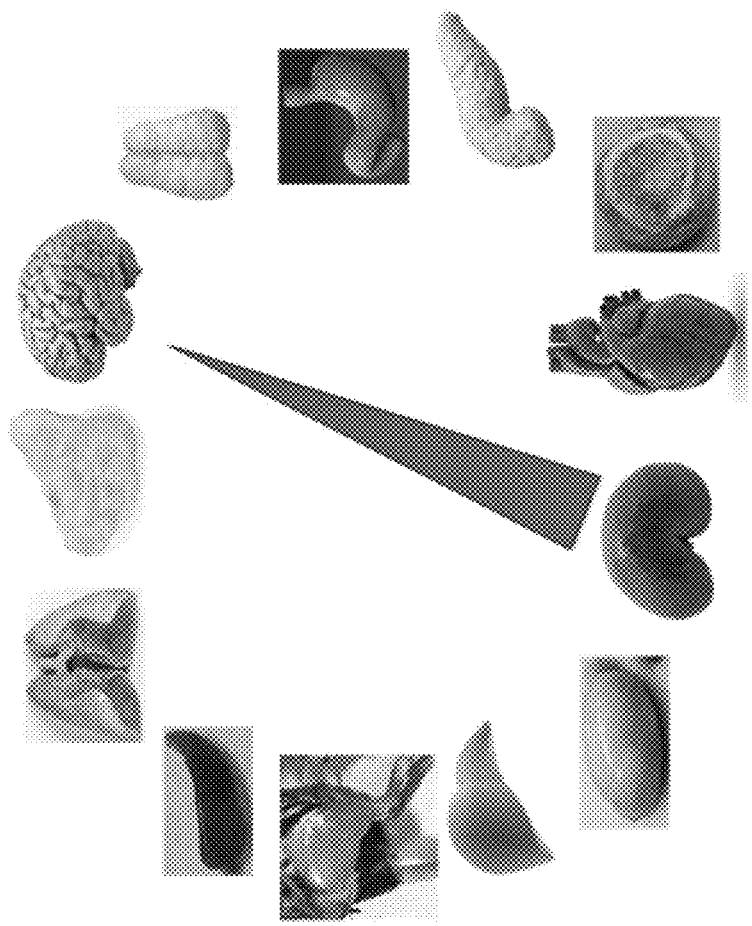
FIG. 11 schematically illustrates an outline of Forward iOrgans according to the present invention.

FIGS. 11 and 12 schematically illustrate an outline of Forward iOrgans according to the present invention.

Forward iOrgans is a method in which, after one disease stage selected from declined kidney function, chronic kidney disease, and renal failure in the kidneys of a subject is determined by using a usual test etc., the one disease stage selected from declined kidney function, chronic kidney disease, and renal failure is compared with predetermined data regarding inter-organ cross talk indicators in other organs to determine the pattern of gene expression etc. derived from each organ other than the kidneys of the subject; and, on the basis of this, the presence of a disease or the stage of the disease, including complications, in each of the organs other than the kidneys is predicted. The presence of a disease or the stage of the disease, including complications, in each organ other than the kidneys can be predicted by checking the pattern of gene expression etc. derived from each of the organs other than the kidneys of the subject against previously reported information regarding gene expression in the disease in each of the organs other than the kidneys. In the example of FIG. 11, one disease stage selected from declined kidney function, chronic kidney disease, and renal failure is identified beforehand by using a usual test etc., and the state of an organ (e.g., brain) other than the kidneys is predicted from the one disease stage selected from declined kidney function, chronic kidney disease, and renal failure. Taking this case as an example, an outline of the prediction method of Forward iOrgans is described with reference to FIG. 12.

First, information that the state of the kidneys in a subject is one disease stage selected from declined kidney function, chronic kidney disease, and renal failure is determined from the results of, for example, a biochemical test of serum or the like. Next, the stage of the subject is checked against patterns of gene expression etc. in organs including the kidneys stored for the one disease stage selected from declined kidney function, chronic kidney disease, and renal failure (patterns of inter-organ cross talk indicators) (e.g., FIG. 12(a)), thereby extracting patterns of the inter-organ cross talk indicators corresponding to the stage in the subject (e.g., the state of declined kidney function) (FIG. 12(b)) from the data of FIG. 12(a). Furthermore, the pattern of the inter-organ cross talk indicator derived from the brain (FIG. 12(c)) is extracted from the patterns of FIG. 12(b). By this procedure, the pattern of the inter-organ cross talk indicator derived from the brain (FIG. 12(c)) can be inferred to be the pattern of the inter-organ cross talk indicator derived from the brain at the stage in the subject. Based on the inter-organ cross talk indicator shown in the pattern inferred, the state of the brain can be predicted from previously reported information regarding diseases and complications.

1. Explanation of Terms

First, terms used in the present specification, claims, and abstract regarding inventions relating to iOrgans are explained. Unless otherwise stated, terms used in the present specification, claims, and abstract are in accordance with the definitions in this section. The same terms as some of the terms used in the above section "I. Screening" are used in this section "II. iOrgans"; however, terms relating to the inventions described in "II. iOrgans" used in the specification, claims, and abstract are in accordance with the definitions in this section, unless otherwise stated. The definitions of the terms used in the above section "I. Screening" and the definitions of the terms used in this section "II. iOrgans" are independent of each other, unless individual sections are referred to.

"Individual" as used herein is not particularly limited. Examples include mammals, such as humans, mice, rats, dogs, cats, rabbits, bovines, horses, goats, sheep, and pigs, birds, such as chickens, and the like. The individual is preferably a mammal such as a human, a mouse, a dog, a cat, a bovine, a horse, or a pig, more preferably a human, a mouse, a dog, a cat, or the like, even more preferably a human or a mouse, and most preferably a human. In addition, the term "individual" includes both individuals having disease and individuals having no disease. There is no limitation on the age or sex (male or female) of the individual; however, the individual is preferably the same species, the same age, and/or the same sex as the subject described later.

Moreover, the term "individual" also includes individuals that gestate.

The ages of the individuals in the present invention may be classified into the following age groups in humans: under 7 years of age, 7 years of age or older but under 15 years of age, 15 years of age or older but under 30 years of age, 30 years of age or older but under 60 years of age, and 60 years of age or older. The age in the present invention is not particularly limited and is preferably 15 years of age or older but under 30 years of age, 30 years of age or older but under 60 years of age, or 60 years of age or older, and more preferably 30 years of age or older but under 60 years of age, or 60 years of age or older. In mice, the ages may be classified into the following age groups: under 6 weeks of age, 6 weeks of age or older but under 24 weeks of age, 24 weeks of age or older but under 48 weeks of age, and 48 weeks of age or older.

Here, an individual with at least one disease selected from the group consisting of declined kidney function, chronic kidney disease, and renal failure described later is referred to as a "positive control," and an individual without at least one disease selected from the group consisting of declined kidney function, chronic kidney disease, and renal failure described later is referred to as a "negative control."

In the present invention, "tissue" refers to a collection of cells that have a similar function and a similar shape.

"Organ" as used herein means a collection of tissue, in a subject, that has a certain independent form and a specific function. Specific examples include organs of the circulatory system (such as the heart, arteries, veins, and lymphatic vessels), organs of the respiratory system (such as the nasal cavity, paranasal sinus, larynx, trachea, bronchus, and lungs), organs of the digestive system (such as the lips, buccal region, palate, teeth, gums, tongue, salivary glands, pharynx, esophagus, stomach, duodenum, jejunum, ileum, cecum, appendix, ascending colon, transverse colon, sigmoid colon, rectum, anus, liver, gallbladder, bile duct, biliary tract, pancreas, and pancreatic duct), organs of the urinary system (such as the urethra, urinary bladder, ureter, and kidneys), organs of the nervous system (such as the cerebrum, cerebellum, midbrain, brainstem, spinal cord, peripheral nerves, and autonomic nerves), organs of the female reproductive system (such as the ovaries, Fallopian tubes, uterus, and vagina), the breasts, organs of the male reproductive system (such as the penis, prostate gland, testes, epididymis, and vas deferens), organs of the endocrine system (such as the hypothalamus, pituitary glands, pineal body, thyroid gland, parathyroid glands, and adrenal glands), organs of the integumentary system (such as the skin, hair, and nails), organs of the hematopoietic system (such as peripheral blood, bone marrow, and spleen), organs of the immune system (such as the lymph nodes, tonsils, and thymus), bones and soft-tissue organs (such as the bones, cartilage, skeletal muscles, connective tissue, ligaments, tendons, diaphragm, peritoneum, pleura, and adipose tissue), and organs of the sensory organ system (such as the eyeballs, eyelids, lacrimal glands, outer ear, middle ear, inner ear, and cochlea). Preferable examples of tissue in the present invention include tissue of the heart, cerebrum, lungs, kidneys, adipose tissue, liver, skeletal muscle, testes, spleen, thymus, bone marrow, pancreas, and the like. More preferred examples of tissue include tissue of the heart, cerebrum, lungs, kidneys, adipose tissue, liver, skeletal muscle, spleen, bone marrow, pancreas, and the like.

Furthermore, in the case of using an individual that gestates (preferably an individual other than humans) as a subject, the term "organ" in the present invention may include the whole body of an embryo or the organs described above of an embryo.

In the present invention, body fluids, such as serum, plasma, urine, spinal fluid, ascites fluid, pleural effusion, saliva, gastric fluid, pancreatic fluid, bile, and milk, particularly preferably plasma, may be used instead of the organs described above.

"Inter-organ cross talk indicator" as used herein is at least one in vivo factor (or molecule) that is present in a living organism and acts as a measure representing the states of organs through organ-to-organ communication (i.e., inter-organ cross talk) in a living organism. In other words, the inter-organ cross talk indicator is an in vivo substance or substances that can undergo changes in cells or tissue originating from each organ, and/or a body fluid in an individual having at least one disease selected from the group consisting of declined kidney function, chronic kidney disease, and renal failure, depending on whether the disease is present. Examples of in vivo substances that can act as an inter-organ cross talk indicator include nucleic acids; carbohydrates; lipids; glycoproteins; glycolipids; lipoproteins; amino acids, peptides; proteins; polyphenols; chemokines; at least one metabolite selected from the group consisting of metabolic end products of the above substances, intermediate metabolites of the above substances, and starting substances for one or more metabolic pathways of the above substance; metal ions; and the like. Preferable examples are nucleic acids.

In the present invention, the nucleic acid is preferably RNA, such as mRNA, non-coding RNA, or microRNA, and more preferably mRNA. The RNA is preferably at least one RNA selected from the group consisting of mRNAs, non-coding RNAs, and microRNAs that can be expressed in cells or tissue originating from organs described above, more preferably RNAs expressed from genes listed in FIG. 21 in which the RNAs can be detected by RNA-Seq etc. (also referred to herein as "group 1"). Among these, the RNAs having polyA sequences are preferable. More specifically, the RNA is at least one RNA selected from the group consisting of RNAs expressed from the genes of group 2 listed in FIG. 22, or at least one RNA selected from the group consisting of RNAs expressed from the orthologs of group 2 that are present in the individual described above. More preferably, the RNA is at least one RNA selected from the group consisting of RNAs expressed from the genes of group 3 listed in FIG. 22, or at least one RNA selected from the group consisting of RNAs expressed from the orthologs of group 3 that are present in the individual described above.

More preferably, the RNA is at least one RNA selected from the group consisting of RNAs expressed from the genes of group 4 listed in FIG. 22, or at least one RNA selected from the group consisting of RNAs expressed from the orthologs of group 4 that are present in the individual described above. More preferably, the RNA is at least one RNA selected from the group consisting of RNAs expressed from the genes of group 5 listed in FIG. 22, or at least one RNA selected from the group consisting of RNAs expressed from the orthologs of group 5 that are present in the individual described above. More preferably, the RNA is at least one RNA selected from the group consisting of RNAs expressed from the genes of group 6 listed in FIG. 23, or at least one RNA selected from the group consisting of RNAs expressed from the orthologs of group 6 that are present in the individual described above. Particularly preferably, the RNA is mRNA expressed from at least one gene selected from the group consisting of proline-rich proteins (Prh1, Prp2, Prb1, Prpmp5), defensins (Defa and Defb), Aplnr, Spp1, Dnase1, Slco1a1, Anpep, Slc7a8, Oscar, fibrinogens, and Hamp/Hepcidin; or at least one RNAs expressed from the orthologs of these genes that are present in the individual described above. In an individual in which an ortholog corresponding to a gene described in FIG. 22 or 23 is not present, the ortholog is excluded from the analysis. It is more preferred that non-coding RNAs and microRNAs (their NCBI Reference Seq IDs start with "NR") be excluded from the analysis in individuals other than mice. Human orthologs corresponding to groups 2 to 6 are RNAs expressed from genes indicated by the Human Gene ID listed in FIG. 22.

"An amount of an inter-organ cross talk indicator" or "amounts of inter-organ cross talk indicators" as used herein may be expressed as a quantitative value (or a quantitative level), or expressed semi-quantitatively as follows: for example, "increase," "no change," and "decrease." "An amount of an inter-organ cross talk indicator" or "amounts of inter-organ cross talk indicators" may be the measurement value of the inter-organ cross talk indicator.

In the present invention, the definitions of the terms "declined kidney function," "chronic kidney disease," and "renal failure" are in accordance with the definitions in the above section "I. Screening, 1. Explanation of terms."

"Standard data 1" as used herein is data of inter-organ cross talk indicators in each organ that serve as a measure for predicting the presence of at least one disease selected from the group consisting of declined kidney function, chronic kidney disease, and renal failure, and/or the stage of the disease in a subject. More specifically, standard data 1 is a group of patterns of inter-organ cross talk indicators, each of the patterns being derived from a predetermined relationship between an amount of an inter-organ cross talk indicator in an organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure; and preferably a group of patterns of inter-organ cross talk indicators, each of the patterns being derived from a predetermined ratio between an amount of an inter-organ cross talk indicator in an organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure. More preferably, the amount of the inter-organ cross talk indicator is the expression level of at least one gene, and the patterns of the inter-organ cross talk indicators are a group of patterns of expression of at least one gene. Moreover, instead of a group of standard data 1, correlation maps (standard data 1-Maps) may be used. The correlation maps (standard data 1-Maps) are generated using a group of standard data 1 derived from multiple organs by determining, for each disease or each stage, the correlation of the patterns of inter-organ cross talk indicators between the organs. The method for generating the correlation maps is described below.

"Standard data 2" as used herein is data of inter-organ cross talk indicators in each organ that serve as a measure for predicting the presence of a disease and/or the stage of the disease in each of one or more organs other than the kidneys in a subject affected with at least one disease selected from the group consisting of declined kidney function, chronic kidney disease, and renal failure. More specifically, standard data 2 is a group of patterns of inter-organ cross talk indicators predetermined for each stage of the at least one disease selected from the group consisting of declined kidney function, chronic kidney disease, and renal failure, each of the patterns being derived from a predetermined relationship between an amount of an inter-organ cross talk indicator in an organ other than the kidneys in positive control(s) affected with the at least one disease selected from the group consisting of declined kidney function, chronic kidney disease, and renal failure, and an amount of the corresponding inter-organ cross talk indicator in the same organ as the organ other than the kidneys in negative control(s) without the at least one disease selected from the group consisting of declined kidney function, chronic kidney disease, and renal failure. Preferably, standard data 2 is a group of patterns of inter-organ cross talk indicators predetermined for each stage of at least one disease selected from the group consisting of declined kidney function, chronic kidney disease, and renal failure, each of the patterns being derived from a value obtained by dividing an amount of an inter-organ cross talk indicator in an organ other than the kidneys in the positive control(s) by an amount of the corresponding inter-organ cross talk indicator in the same organ as the organ other than the kidneys in the negative control(s). More preferably, the amount of the inter-organ cross talk indicator is the expression level of at least one gene, and the patterns of the inter-organ cross talk indicators are a group of patterns of expression of at least one gene.

Standard data 1 or 2 is obtained for each stage of at least one disease selected from the group consisting of declined kidney function, chronic kidney disease, and renal failure; each organ or body fluid; and, if necessary, each sex and/or each age group. A database of a group of standard data 1 or a group of standard data 2 may be established. Each of the patterns of the inter-organ cross talk indicators is linked with information regarding the corresponding stage of at least one disease selected from the group consisting of declined kidney function, chronic kidney disease, and renal failure, and the corresponding organ or body fluid. The database may be stored in a storage medium or a storage device.

The term "pattern" includes, for example, the presence or absence of an inter-organ cross talk indicator, the amounts of inter-organ cross talk indicators, or changes in the amounts of inter-organ cross talk indicators over time; and a combination of the amounts of inter-organ cross talk indicators, and changes in the amounts of inter-organ cross talk indicators over time. Preferably, the pattern includes the presence or absence of an inter-organ cross talk indicator, the amounts of inter-organ cross talk indicators, or changes in the amounts of inter-organ cross talk indicators over time; and a combination of the amounts of inter-organ cross talk indicators and changes in the amounts of inter-organ cross talk indicators over time, for each stage. Preferably, the pattern includes the presence or absence of expression of RNA from at least one gene, the expression level of RNA from at least one gene, or changes in the expression level of RNA from at least one gene over time; and a combination of the expression level of RNA from at least one gene, and changes in the expression level of RNA from at least one gene over time.

The amassment of standard data 1, standard data 2, a group of standard data 1, or a group of standard data 2 above is called a "database." The corresponding pattern of an inter-organ cross talk indicator in standard data 1, standard data 2, a group of standard data 1, or a group of standard data 2 can be retrieved and extracted from the database based on, for example, information regarding one disease stage selected from the group consisting of chronic kidney disease and renal failure, and/or the name of each organ or body fluid.

"Subject" is a subject to which the prediction methods according to the present invention are applied, and is preferably of a species corresponding to those of individuals used for obtaining standard data 1 or 2 above. For example, if individuals used for obtaining the standard data are mice, then a mouse, a rat, a human, or the like may be selected as the subject. The age and sex of the subject are not particularly limited, and the subject may be in the same age group and/or of the same sex as individuals used for obtaining standard data 1 or 2.

"Data of a subject" or "subject data" as used herein is data of an inter-organ cross talk indicator derived from all or part of an organ collected from a subject, and the pattern is linked with the corresponding information about the subject and the organ. More specifically, data of a subject or subject data is a pattern of an inter-organ cross talk indicator indicating the relationship between the amount of the inter-organ cross talk indicator in an organ other than the kidneys of the subject, and the amount of the corresponding inter-organ cross talk indicator in the same organ as the organ other than the kidneys in negative control(s) without at least one disease selected from the group consisting of declined kidney function, chronic kidney disease, and renal failure. Data of a subject or subject data is preferably a pattern of an inter-organ cross talk indicator indicating the ratio between the amount of the inter-organ cross talk indicator in an organ other than the kidneys of the subject, and the amount of the corresponding inter-organ cross talk indicator in the same organ as the organ other than the kidneys in negative control(s) without at least one disease selected from the group consisting of declined kidney function, chronic kidney disease, and renal failure. More preferably, the amount of the inter-organ cross talk indicator is the expression level of RNA from at least one gene, and the pattern of the inter-organ cross talk indicator is a pattern of expression of least one gene.

"Gold standard" as used herein is an individual or individuals that have already been determined to have or not have at least one disease selected from the group consisting of declined kidney function, chronic kidney disease, and renal failure by a known test method and/or diagnostic method. The term "gold standard" also includes healthy individuals.

"Similarity" as used herein indicates the degree to which patterns of inter-organ cross talk indicators are similar when data of a subject is compared with standard data or when subject data X is compared with standard data Y. More specifically, the similarity can be determined visually, or by statistical analysis or the like. Examples of statistical analysis for calculating the similarity include Z-score, Spearman's pairwise correlation, Kullback-Leibler divergence, principal component analysis (PCA), and the like.

For example, when a ρ-value is calculated using Spearman pairwise correlation, it can be determined as follows: when the ρ-value is 1, it can be determined that the data of the subject is identical to the standard data 1; when the ρ-value is more than 0.4 and less than 1, preferably more than 0.65 and less than 1, more preferably more than 0.75 and less than 1, and even more preferably more than 0.85 and less than 1, it can be determined that the data of the subject is similar to the standard data 1; on the other hand, when the ρ-value is 0.8 or less, preferably 0.65 or less, and more preferably 0.40 or less, it can be determined that the data of the subject is not similar to the standard data 1.

For example, when a z-value is calculated using a Z-score, it can be determined as follows: when the z-value is 0, it can be determined that the data of the subject is identical to the standard data 1; when the z-value falls within the range of 0±0.5 (excluding 0), preferably within the range of 0±0.4 (excluding 0), more preferably within the range of 0±0.3 (excluding 0), and even more preferably within the range of 0±0.15 (excluding 0), it can be determined that the data of the subject is similar to the standard data 1; on the other hand, when the z-value falls outside the range of 0±0.15, preferably outside the range of 0±0.3, more preferably outside the range of 0±0.4, and even more preferably outside the range of 0±0.5, it can be determined that the data of the subject is not similar to the standard data 1.

Further, when at least 50%, preferably at least 70%, more preferably at least 80%, and even more preferably at least 90% of items in examined inter-organ cross talk indicators are identical or similar between standard data 1 and data of a subject, it can be determined that the pattern in the standard data 1 is similar to the pattern in the data of the subject. On the other hand, when at least 50%, preferably at least 70%, more preferably at least 80%, and even more preferably at least 90% of items in examined inter-organ cross talk indicators are not identical or similar between standard data 1 and data of a subject, it can be determined that the pattern in the standard data 1 is not similar to the pattern in the data of the subject.

Standard data 1-Maps are determined as follows. When standard data 1-Maps are determined, multiple organs are collected for each stage of at least one disease selected from the group consisting of declined kidney function, chronic kidney disease, and renal failure; and patterns of inter-organ cross talk indicators derived from the organs are determined (for example, when the inter-organ cross talk indicator is RNA, the genes expressing RNAs are listed in a certain order that is consistent among organs). Correlation coefficients are calculated between the patterns of the organs using, for example, Spearman's rank correlation, and maps between the organs are generated.

More specifically, for example, the correlation coefficient of patterns of inter-organ cross talk indicators j between organ m and organ l in disease model i is represented by $r_{ijml}$.

The number of individuals of disease model i is represented by n.

In this case, the correlation coefficient between organ m and organ l of disease model i can be represented by probability model p (the following equation).

$$p(r \mid i, m, l) = \frac{1}{\sqrt{2\pi}\,\sigma_{iml}} \exp\left(-\frac{(r - r_{iml})^2}{2\sigma_{iml}^2}\right) \quad \text{Equation 1}$$

wherein $r_{iml}$ is the mean of n correlation coefficients $r_{ijml}$, and $\sigma_{iml}^2$ is the sample variance of the correlation coefficients $r_{ijml}$.

Comparisons between data of a subject and standard data 1-Maps, comparisons between subject data X and standard data Y2-Maps, and comparisons between subject data X and standard data Y3-Maps can be performed using Bayesian inference, machine-learning methods, etc.

For example, patterns of inter-organ cross talk indicators of multiple organs in a subject are obtained, and correlation coefficient(s) of the patterns of inter-organ cross talk indicators are determined between the organs in the subject from which the data of the subject or the subject data X is obtained, in the same manner as described above. The obtained value(s) are represented by the following:
$\{r'_{ml}\}_{m,l \in (collected\ organs)}$
In this case, the likelihood $L_i$ of correlation
$\{r'_{ml}\}_{m,l \in (collected\ organs)}$
with respect to each model i can be calculated using the following equation.

$$L_i = \prod_{m,l} p(r'_{ml} \mid i, m, l) \quad \text{Equation 2}$$

The likelihood is calculated for each model i, and a model i with the highest likelihood can be inferred to be the state of the subject.

When the number of organs to be compared is three or more, the likelihood between a disease model and a subject is determined between two of each of the organs, and the product of the calculated likelihoods is determined. A model i with the highest product may be inferred to be the state of the subject.

Which inter-organ cross talk indicator is used is not particularly limited when comparisons between data of a subject and standard data 1-Maps are performed. For example, it is preferable to use an inter-organ cross talk indicator in which the difference between positive control(s) and negative control(s) is large. More specifically, for example, when the inter-organ cross talk indicator is RNA, it is RNA in which the ratio between positive control(s) and negative control(s) is more than 1.5 or less than 0.65, preferably more than 2 or less than 0.5, and more preferably more than 5 or less than 0.2.

The statistical analysis described above can be performed, for example, with a computer using a calculation program. In this case, the prediction program according to the present invention described later may comprise program code of a statistical analysis program for performing statistical analysis, or commercially available statistical analysis software may be used as a statistical analysis program. For example, the analysis can be performed using commercially available statistical analysis software, such as StatFlex Ver. 6 (Artech Co., Ltd., Osaka, Japan) or IBM SPSS Statistics (IBM Japan Ltd.).

"One or more" as used herein includes cases of one kind, and cases of multiple kinds. The term "multiple" is not particularly limited as long as it means two or more, and preferably refers to three or more, more preferably five or more, and even more preferably ten or more. Further, in the present specification, the use of a singular noun may include the plural.

2. Methods for Collecting and Storing Cells or Tissue for Extraction of an Inter-Organ Cross Talk Indicator, and Methods for Extracting and Measuring an Inter-Organ Cross Talk Indicator The method for collecting cells or tissue for extraction of an inter-organ cross talk indicator used in the present invention and the method for their storage are not particularly limited, and cells or tissue can be collected and stored according to known methods depending on the type of inter-organ cross talk indicator. The method for extracting an inter-organ cross talk indicator used in the present invention is also not particularly limited, and the inter-organ cross talk indicator can be extracted according to a known method depending on the type of inter-organ cross talk indicator. The method for measuring an inter-organ cross talk indicator in the present invention is not particularly limited as long as the amount of an inter-organ cross talk indicator can be measured.

Cells or tissue used for extraction of an inter-organ cross talk indicator is not particularly limited. Examples include cells, tissue, etc., collected from a subject by, for example, puncture, biopsy, or surgery. (The collected cells or tissue is also called a "specimen.") The cells or tissue may be, for example, fresh material after collection or cryopreserved material.

In this embodiment, an inter-organ cross talk indicator may be obtained from cells or tissue originating from the kidneys suspected of having a disease and from one or more organs other than the kidneys, for each stage of at least one disease selected from the group consisting of declined kidney function, chronic kidney disease, and renal failure. In addition, an inter-organ cross talk indicator may be derived from the corresponding cells or tissue in an individual without the at least one disease selected from the group consisting of declined kidney function, chronic kidney disease, and renal failure.

The time at which cells, tissue, or body fluids are collected can suitably be selected according to the disease stage from, for example, the following: before the onset of at least one disease selected from the group consisting of declined kidney function, chronic kidney disease, and renal failure (in the normal state); at the onset of at least one disease selected from the group consisting of declined kidney function, chronic kidney disease, and renal failure; 1 month, 6 months, 1 year, 2 years, 3 years, 5 years, or 10 years after the onset of at least one disease selected from the group consisting of declined kidney function, chronic kidney disease, and renal failure; and the like.

When RNA is used as an inter-organ cross talk indicator, it is preferable that RNA extraction from cells or tissue is performed immediately after the cells or tissue is collected; or is performed after freezing the cells or tissue with liquid nitrogen or the like immediately after the cells or tissue is collected, and then transporting and storing the cells or tissue.

The method for extracting RNA is not particularly limited, and RNA can be extracted using a known method. RNA may be purified using, for example, an oligo dT probe, as necessary. If necessary, cDNA may be synthesized from extracted or purified RNA by a reverse transcription reaction, and used for measurement. Qualitative or quantitative measurement (including semi-quantitative measurement) of RNA may be performed by a known method, such as a method using a microarray, which can comprehensively analyze gene expression; or a method in which analysis is conducted by RNA-Seq, which determines the absolute amounts of RNAs in cells. As comprehensive and quantitative analysis, RNA-Seq is preferable.

Data obtained by RNA-Seq or the like can be analyzed using a known method. For example, when the data is analyzed with Illumina HiSeq (Illumina, Inc.) or the like, the output data can be processed by the following method: (1) text data of nucleotide sequences are obtained from the output raw data of analysis (image data) (base calling); (2) the data is selected using predetermined filtering such as removing low fluorescence purity clusters caused by overlapping clusters from the data by using a calculation formula, such as chastity (filtering); and (3) the sample data is sorted based on index sequence information provided for each sample (specific nucleotide sequence information).

A data file (Fastq format or the like) obtained from the RNA-Seq sequencer is uploaded on, for example, Galaxy (https://usegalaxy.org/). Thereafter, analysis is carried out using, for example, Bowtie2 (http://bowtie-bio.sourceforge.net/bowtie2/index.shtml) to map each sequence to mouse genome map information mm9 or mm10. A BAM file obtained using Bowtie2 or the like is analyzed using, for example, Cufflinks (http://cole-trapnell-lab.github.io/cufflinks/) to calculate FPKM (RPKM) for each gene. In the obtained FPKM data, all FPKM values less than 1 are regarded as 0; pairwise correlation ($\rho=1-(6\Sigma D^2)/(n^3-n)$) is calculated using Python, and a heat map is generated using MeV. The FPKM values may also be visually analyzed.

If necessary, expression can also be confirmed by real-time PCR or the like. In addition, the mRNA expression level can be normalized by the expression level of a housekeeping gene, such as GAPDH, $\beta$2-microglobulin ($\beta$2M), or Maea, as necessary, and expressed as a relative expression level.

The expression level obtained by the method described above can be stored in the storage unit of a device, or a device having a storage unit that is different from the device, as a pattern of the inter-organ cross talk indicator for each stage of at least one disease selected from the group consisting of declined kidney function, chronic kidney disease, and renal failure; each organ or body fluid; each type of individual; each age group of individuals; and/or each sex of individuals.

3. Reverse iOrgans
3-1. Outline

In this embodiment, the presence of at least one disease selected from the group consisting of declined kidney function, chronic kidney disease, and renal failure, and/or the stage of the disease in a subject is predicted from the pattern of an inter-organ cross talk indicator derived from each of one or more organs other than the kidneys of the subject. Specifically, data of the subject regarding an inter-organ cross talk indicator in each of one or more organs other than the kidneys is obtained by performing a measurement method described in section II. 2. above, wherein the inter-organ cross talk indicator is derived from cells or tissue originating from each of the one or more organs; the data of the subject is compared with standard data 1 in one or more organs corresponding to the one or more organs from which the data of the subject originates, and similarity of patterns of the inter-organ cross talk indicators between the data of the subject and the standard data 1 is calculated, wherein the standard data 1 is extracted from a group of standard data 1 predetermined for each of the at least one disease selected from the group consisting of declined kidney function, chronic kidney disease, and renal failure, or for each stage of the disease; and the presence of the at least one disease selected from the group consisting of declined kidney function, chronic kidney disease, and renal failure, and/or the stage of the disease is predicted by using, as a measure, the similarity. Specifically, this embodiment comprises the steps of: (1) obtaining data of the subject regarding an inter-organ cross talk indicator in each of one or more organs other than the kidneys in the subject, the inter-organ cross talk indicator being derived from cells or tissue originating from each of the one or more organs; (2) calculating, by comparing the data of the subject obtained in step (1) with standard data 1 in one or more organs corresponding to the one or more organs from which the data of the subject originates, similarity of patterns of the inter-organ cross talk indicators between the data of the subject and the standard data 1, more specifically calculating, by checking the name of the one or more organs from which the data of the subject obtained in step (1) originates against the name of one or more organs stored in predetermined standard data 1, and comparing the pattern of the inter-organ cross talk indicator in the data of the subject with the pattern of the corresponding inter-organ cross talk indicator in the standard data 1 derived from the same organ as each of the one or more organs from which the data of the subject originates, similarity of the patterns of the inter-organ cross talk indicators, wherein the standard data 1 is extracted from a group of standard data 1 predetermined for each of the at least one disease selected from the group consisting of declined kidney function, chronic kidney disease, and renal failure, or for each stage of the disease; and (3) determining that the subject has a disease corresponding to the standard data 1 and/or is in a stage of a disease corresponding to the standard data 1 when it is determined from the similarity of the patterns of the inter-organ cross talk indicators calculated in step (2) that both patterns are similar.

Step (1) may be performed in such a manner that the data of the subject is obtained by actually performing a measurement method described in the section II. 2., or in such a manner that the data of the subject already obtained is further put into the prediction device described later or the like. The method for calculating the similarity between the standard data 1 and the data of the subject in step (2), and the method for determining whether the standard data 1 and the data of the subject are similar in step (3), can be performed according to a method described in the above section "II. 1. Explanation of terms." Here, step (1) and step (2) are not necessarily performed consecutively in the same organization. For example, the data of the subject obtained in step (1) may be sent to a third-party organization to perform step (2) and the subsequent step.

Moreover, this embodiment may further comprise, before step (1), the following steps: (i) extracting the inter-organ cross talk indicator from the cells or tissue originating from each of the one or more organs other than the kidneys of the subject; and (ii) measuring the amount of the inter-organ cross talk indicator extracted in step (i). In this case, step (i) and step (ii) are not necessarily performed consecutively. For example, the inter-organ cross talk indicator obtained in step (i) may be sent to a third-party organization to perform step (ii). Step (ii) and step (1) are also not necessarily performed consecutively. The measurement result of the inter-organ cross talk indicator obtained in step (ii) may be sent to a third-party organization to perform step (1) and the subsequent steps.

Here, the method for calculating the similarity between the standard data 1 and the data of the subject, and the method for determining whether the standard data 1 and the data of the subject are similar are as described in the above section "II. iOrgans, 1. Explanation of terms."

As another embodiment, this embodiment also includes a method for obtaining information regarding the similarity of patterns of inter-organ cross talk indicators to predict the presence of at least one disease selected from the group consisting of declined kidney function, chronic kidney disease, and renal failure, and/or the stage of the disease in a subject, the method comprising steps (1) and (2) mentioned above, and a step of obtaining the information from step (2).

The prediction method may also comprise a step of obtaining a group of standard data 1 from a storage device 8 (FIG. 13) storing the group of standard data 1, or a step of obtaining one or more sets of standard data 1 from the storage device 8 storing the group of standard data 1.

3-2. System Configuration

Figure 13:
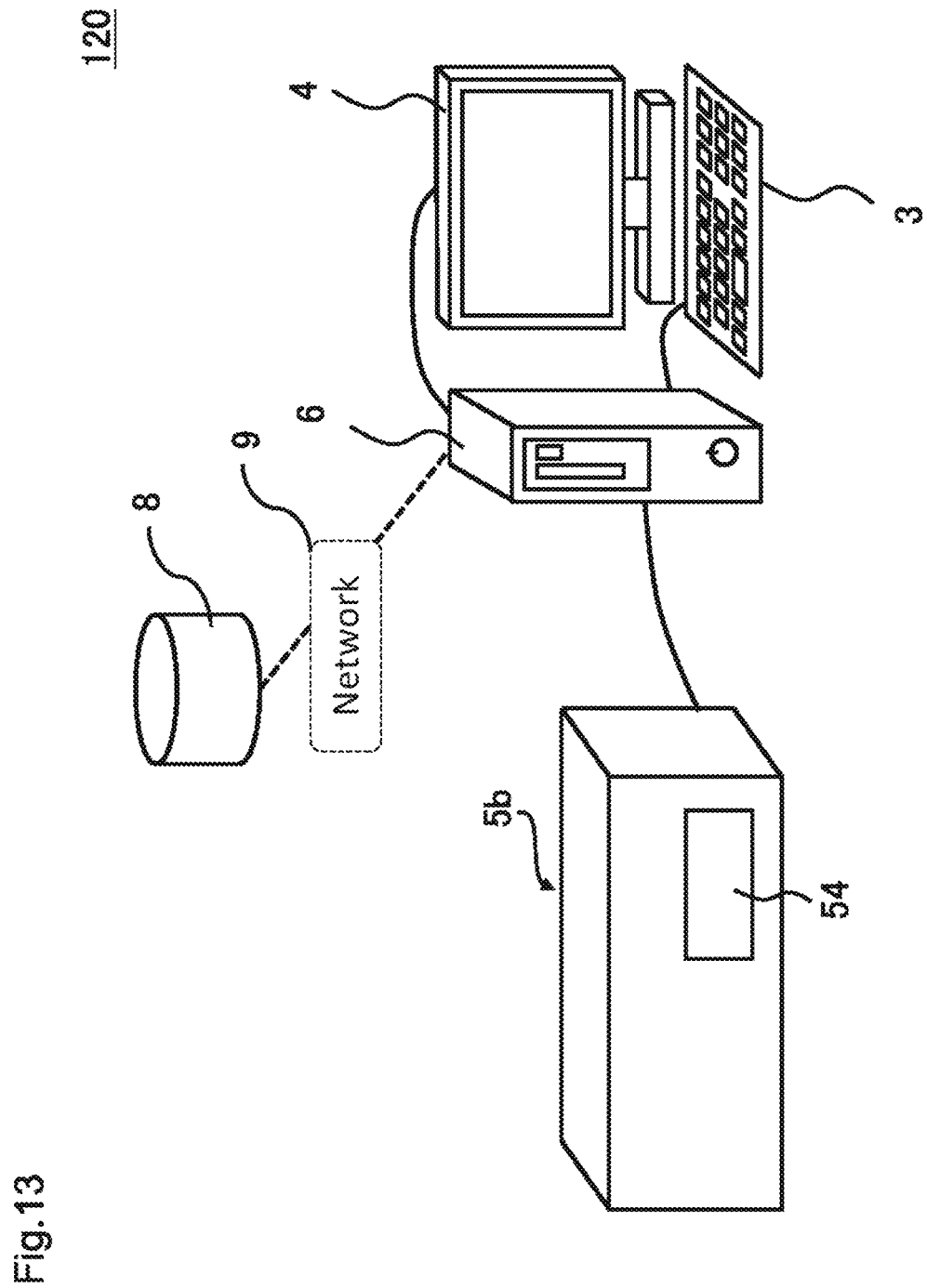
FIG. 13 is an overview of a system 120 according to a third embodiment of the present invention.
Figure 14:
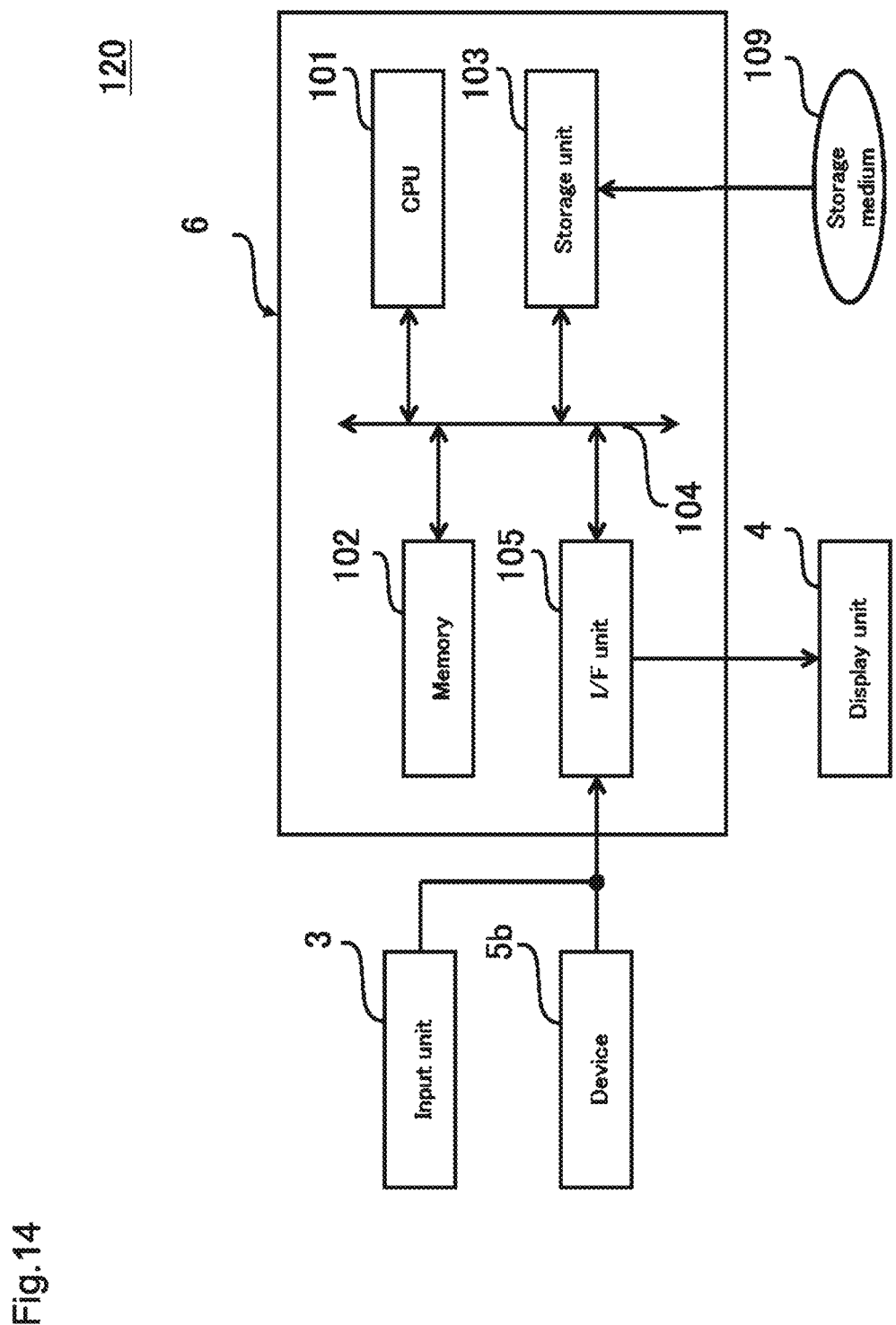
FIG. 14 is a block diagram illustrating a hardware configuration of the system 120 according to the third embodiment of the present invention.

FIG. 13 is an overview of a system 120 according to a third embodiment of the present invention. FIG. 14 is a block diagram illustrating a hardware configuration of the system 120. The system 120 comprises an input unit 3, a display unit 4, a device 5b, and a prediction device 6.

The prediction device 6 includes, for example, a general-purpose personal computer; and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the prediction device and external devices. The input unit 3 and the display unit 4 are connected to the prediction device 6. The input unit 3 includes, for example, a keyboard; and the display unit 4 includes, for example, a liquid crystal display. The input unit 3 and the display unit 4 may be integrated and implemented as a display with a touch panel. The prediction device 6 need not be a single device; and the CPU 101, the memory 102, the storage unit 103, and the like may be located in separate places, and connected via a network. The prediction device may also be a device that omits the input unit 3 and the display unit 4, and that does not require an operator.

The prediction device 6 and the device 5b are also not necessarily located in one place, and may be configured such that the devices located in separate places are communicatively connected to each other via a network.

In the explanation below, a process performed by the prediction device 6 means a process performed by the CPU 101 of the prediction device 6 based on a prediction program unless otherwise specified. The CPU 101 temporarily stores necessary data (such as intermediate data being processed) in the memory 102 that serves as a work area, and suitably stores data that is stored for a long period of time, such as computation results, in the storage unit 103.

The device 5b is a device for measuring the expression level of mRNA by the RNA-Seq method, and comprises a sequence analysis unit 54. A sample subjected to a reaction for RNA-Seq is set in the sequence analysis unit 54, and analysis of nucleotide sequences is performed in the sequence analysis unit 54.

The device 5b is connected to the prediction device 6 by a wired or wireless connection. The device 5b A/D converts the measurement value of mRNA and transmits it as digital data to the prediction device 6. Therefore, the prediction device 6 can obtain, as digital data that can be computed, the measurement value of mRNA. In this embodiment, digital data from the device 5b is referred to as "data of a subject regarding an inter-organ cross talk indicator," or simply referred to as "data of a subject."

As described above, the hardware configuration of each of the input unit 3, display unit 4, device 5b, and prediction device 6 of the system 120 may be the same as that of each of the input unit 3, display unit 4, device 5b, and screening device 1 of the system 100 shown in FIG. 1; or that of each of the input unit 3, display unit 4, device 5b, and screening device 2 of the system 110 shown in FIG. 5.

The system 120 may also comprise a storage device 8 storing standard data 1 or a group of standard data 1, the storage device 8 being connected to the prediction device via a network. A network 9 is, for example, a communication medium, such as the internet, virtual private network (VPN), wide area network (WAN), or public switched telephone network (PSTN), and is not limited as long as it enables communication between the storage device 8 and the prediction device 6. Specifically, the system 120 may be a prediction system for predicting the presence of a disease and/or the stage of the disease in each of one or more organs other than the kidneys in a subject affected with at least one disease selected from the group consisting of declined kidney function, chronic kidney disease, and renal failure, the system comprising the storage device 8 storing standard data 1 or a group of standard data 1 and the prediction device 6 described later.

3-3. Prediction Device

The present invention includes, as the third embodiment, a device for predicting the presence of at least one disease selected from the group consisting of declined kidney function, chronic kidney disease, and renal failure, and/or the stage of the disease in a subject, the device comprising the following computation means:

means for obtaining data of the subject regarding an inter-organ cross talk indicator in each of one or more organs other than the kidneys in the subject, the inter-organ cross talk indicator being derived from cells or tissue originating from each of the one or more organs;

means for calculating, by comparing the data of the subject with standard data in one or more organs corresponding to the one or more organs from which the data of the subject originates, similarity of patterns of the inter-organ cross talk indicators between the data of the subject and the standard data 1, wherein the standard data is extracted from a group of standard data 1 predetermined for each of the at least one disease selected from the group consisting of declined kidney function, chronic kidney disease, and renal failure, or for each stage of the disease; and means for predicting the presence of the at least one disease selected from the group consisting of declined kidney function, chronic kidney disease, and renal failure, and/or the stage of the disease, by using, as a measure, the similarity of patterns of the inter-organ cross talk indicators calculated by the comparison means.

Here, the method for calculating the similarity between the standard data 1 and the data of the subject, and the method for determining whether the standard data 1 and the data of the subject are similar are as described in the above section "II. iOrgans, 1. Explanation of terms."

In this embodiment, the presence of at least one disease selected from the group consisting of declined kidney function, chronic kidney disease, and renal failure, and/or the stage of the disease in a subject, can be predicted by the system 120 (FIGS. 13 and 14) comprising the prediction device 6 as the prediction device described above.

Figure 15:
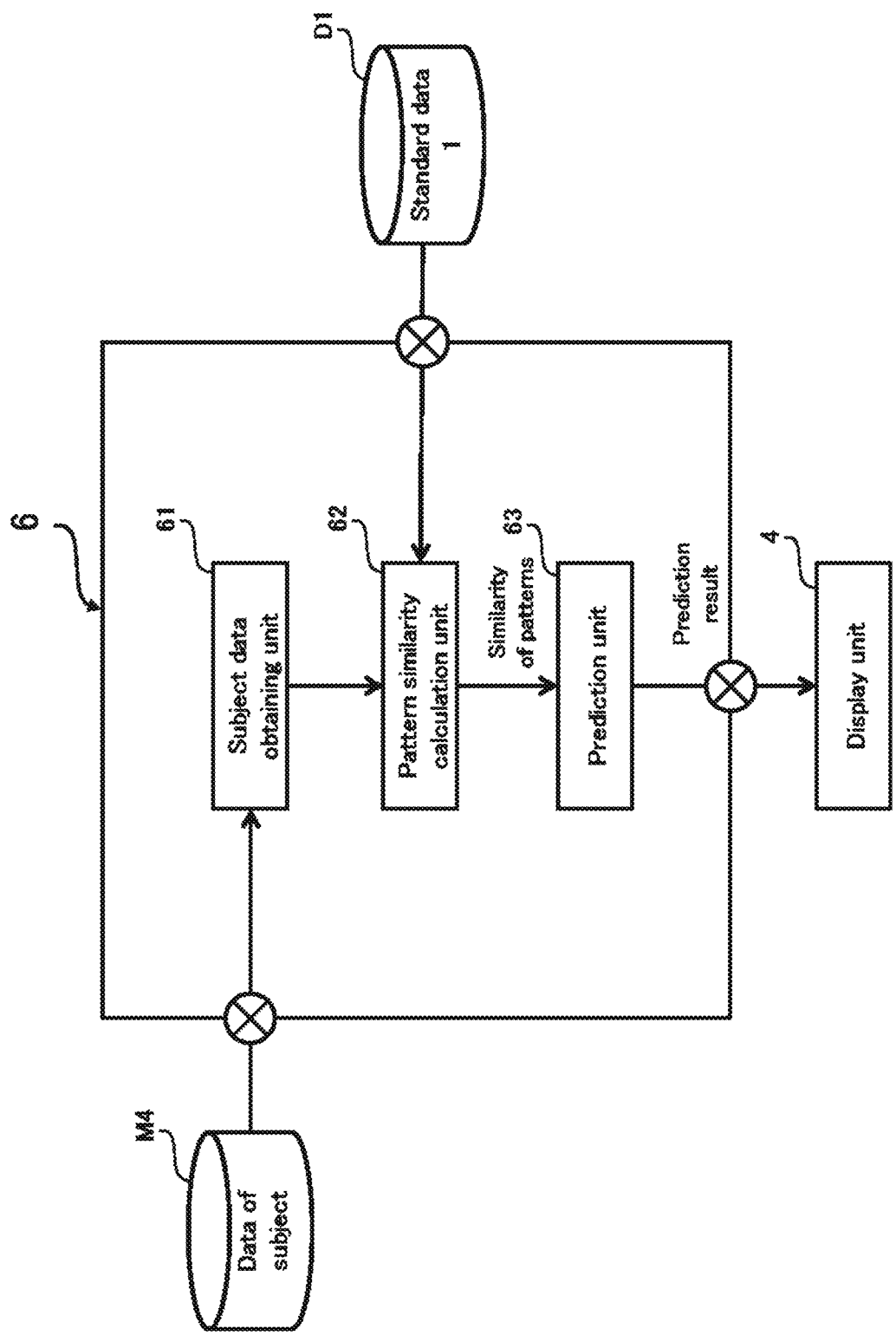
FIG. 15 is a block diagram illustrating functions of a prediction device 6 according to the third embodiment of the present invention.

FIG. 15 is a block diagram illustrating functions of the prediction device 6 according to the third embodiment of the present invention. The prediction device 6 comprises a subject data obtaining unit 61, a pattern similarity calculation unit 62, and a prediction unit 63. These functional blocks are implemented by installing the prediction program according to the present invention in the storage unit 103 or the memory 102 of the prediction device 6, and causing the CPU 101 to execute the program. With this structure, the prediction device 6 carries out the prediction method described later in the section "II. iOrgans, 3-5. Prediction method." The subject data obtaining means, pattern similarity calculation means, and prediction means recited in the claims correspond to the subject data obtaining unit 61, pattern similarity calculation unit 62, and prediction unit 63 shown in FIG. 15, respectively.

In other words, the prediction device 6 is a prediction device for predicting the presence of at least one disease selected from the group consisting of declined kidney function, chronic kidney disease, and renal failure, and/or the stage of the disease in a subject, the device executing the following computation functions by the CPU 101:

a function for obtaining data of the subject regarding an inter-organ cross talk indicator in each of one or more organs other than the kidneys, the inter-organ cross talk indicator being derived from cells or tissue originating from each of the one or more organs;

a function for calculating, by comparing the data of the subject obtained by the subject data obtaining function with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and a function for predicting the presence of the at least one disease selected from the group consisting of declined kidney function, chronic kidney disease, and renal failure, and/or the stage of the disease, by using, as a measure, the similarity of patterns of the inter-organ cross talk indicators calculated by the pattern similarity calculation function.

The prediction device may also comprise a function for obtaining a group of standard data 1 from the storage device 8 storing the group of standard data 1, or a function for obtaining one or more sets of standard data 1 from the storage device 8 storing the group of standard data 1.

In this embodiment, subject data M4 of an inter-organ cross talk indicator measured in device 5b is put into the prediction device 6 from the device 5b. Standard data 1 (D1) is stored outside the prediction device 6, and put into the prediction device 6 via, for example, the internet.

The subject data M4 may be put into the prediction device 6 from a third-party organization (not shown) via a network. The subject data M4 and the standard data D1 may be stored in the storage unit 103 or the memory 102 of the prediction device 6 beforehand.

Moreover, the functional blocks, i.e., the subject data obtaining unit 61, the pattern similarity calculation unit 62, and the prediction unit 63, are not necessarily executed by a single CPU, and may be processed by multiple CPUs in a distributed manner. For example, these functional blocks may be configured such that the function of the subject data obtaining unit 61 is executed by a CPU of a first computer, and such that the functions of the pattern similarity calculation unit 62 and the prediction unit 63 are executed by a CPU of a second computer, i.e., another computer.

3-4. Prediction Program

In order to carry out the processing for steps S31 to S36 in FIG. 16 below, the prediction device 6 stores the prediction program according to the present invention in the storage unit 103 beforehand, for example, in an executable format (for example, a form in which the program can be produced by conversion from a programming language using a compiler). The prediction device 6 carries out the processing using the prediction program stored in the storage unit 103.

Specifically, the prediction program according to the third embodiment of the present invention is a prediction program that, when executed by a computer, causes the computer to carry out the following processing to predict the presence of at least one disease selected from the group consisting of declined kidney function, chronic kidney disease, and renal failure, and/or the stage of the disease in a subject:

processing of obtaining data of the subject regarding an inter-organ cross talk indicator in each of one or more organs other than the kidneys in the subject, the inter-organ cross talk indicator being derived from cells or tissue originating from each of the one or more organs;

processing of calculating, by comparing the data of the subject obtained by the subject data obtaining processing with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and processing of predicting the presence of the at least one disease selected from the group consisting of declined kidney function, chronic kidney disease, and renal failure, and/or the stage of the disease, by using, as a measure, the similarity of patterns of the inter-organ cross talk indicators calculated by the pattern comparison processing.

The prediction program may also comprise processing of obtaining a group of standard data 1 from the storage device 8 storing the group of standard data 1, or processing of obtaining one or more sets of standard data 1 from the storage device 8 storing the group of standard data 1.

In this embodiment, as shown in FIG. 14, the prediction program is stored in a computer-readable non-transitory tangible storage medium 109, such as a CD-ROM, and installed to the prediction device 6 from the storage medium 109; alternatively, the prediction device 6 may be connected to the internet (not shown) to download the program code of the prediction program via the internet. To cause a computer to carry out the computation processing described above, the prediction program according to the present invention may be linked to another program stored in the storage unit 103 or the memory 102. For example, the prediction program may be linked to statistical analysis software mentioned in the above section "II. iOrgans, 1. Explanation of terms," and the pattern similarity calculation processing may be carried out using the statistical analysis software.

3-5. Prediction Method

The prediction device 6 according to the third embodiment of the present invention carries out the prediction method according to the third embodiment of the present invention. The prediction method according to the third embodiment of the present invention is a method for predicting the presence of at least one disease selected from the group consisting of declined kidney function, chronic kidney disease, and renal failure, and/or the stage of the disease in a subject, the method comprising the steps of:

calculating, by comparing data of the subject regarding an inter-organ cross talk indicator in each of one or more organs other than the kidneys in the subject, the inter-organ cross talk indicator being derived from cells or tissue originating from each of the one or more organs, with standard data 1 in one or more organs corresponding to the one or more organs from which the data of the subject originates, similarity of patterns of the inter-organ cross talk indicators between the data of the subject and the standard data 1, wherein the standard data 1 is extracted from a group of standard data 1 predetermined for each of the at least one disease selected from the group consisting of declined kidney function, chronic kidney disease, and renal failure, or for each stage of the disease; and predicting the presence of the at least one disease selected from the group consisting of declined kidney function, chronic kidney disease, and renal failure, and/or the stage of the disease by using, as a measure, the similarity of patterns of the inter-organ cross talk indicators calculated in the similarity calculation step.

The prediction method may also comprise a step of obtaining a group of standard data 1 from the storage device 8 storing the group of standard data 1, or a step of obtaining one or more sets of standard data 1 from the storage device 8 storing the group of standard data 1.

Figure 16:
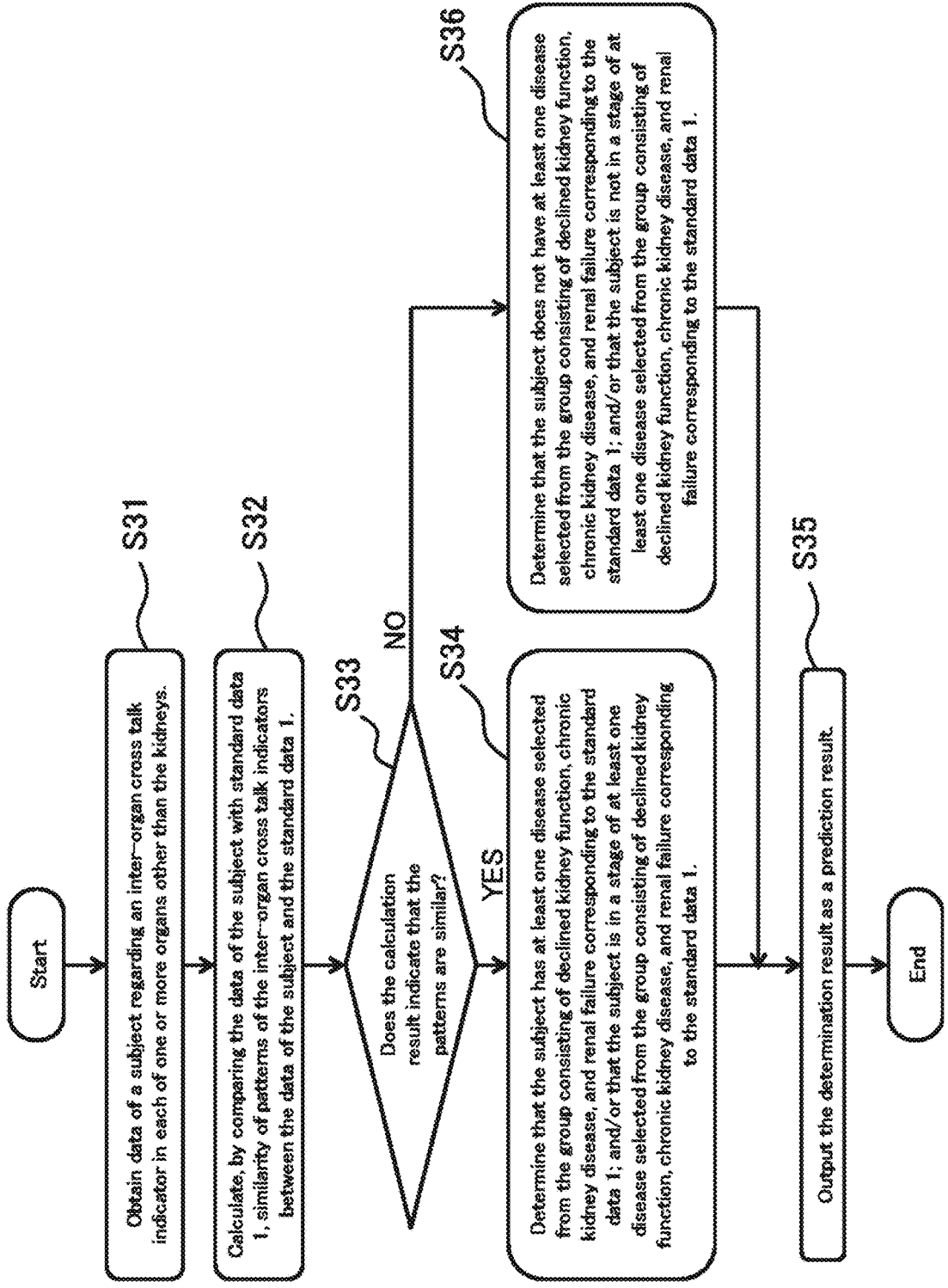
FIG. 16 is a flow chart illustrating a flow of data processing performed by the prediction device 6 according to the third embodiment of the present invention to carry out a prediction method.

FIG. 16 is a flow chart illustrating a flow of data processing performed by the prediction device 6 according to the third embodiment of the present invention to carry out the prediction method described above. The processing for steps S31 to S36 shown in FIG. 16 is performed by the subject data obtaining unit 61, pattern similarity calculation unit 62, and prediction unit 63 shown in FIG. 15.

In step S31, the subject data obtaining unit 61 obtains subject data M4. The subject data M4 is a pattern of an inter-organ cross talk indicator in each of one or more organs other than the kidneys of a subject, the inter-organ cross talk indicator being derived from cells or tissue originating from each of the one or more organs, and transmitted from the device 5b to the prediction device 6.

In step S32, the pattern similarity calculation unit 62 compares the obtained subject data M4 with standard data 1 (D1), and calculates similarity of patterns of the inter-organ cross talk indicators. Specifically, the pattern similarity calculation unit 62 selects standard data 1 (D1) corresponding to the name of each of the one or more organs from which the subject data M4 originates, compares the pattern of the selected standard data 1 (D1) with the pattern of the subject data M4, and calculates the similarity between them. The method for calculating the similarity and the method for determining whether patterns are similar are as described in the above section "II. iOrgans, 1. Explanation of terms." The prediction program described in the above section "II. iOrgans, 3-4. Prediction program" may comprise program code of a program for causing the CPU 101 of the prediction device 6 to perform computation processing by the pattern similarity calculation unit 62; or, for example, may be linked to statistical analysis software mentioned in the above section "II. iOrgans, 1. Explanation of terms," to cause the CPU 101 to perform computation processing by the pattern similarity calculation unit 62 using the statistical analysis software.

In step S34, the prediction unit 63 predicts the presence of at least one disease selected from the group consisting of declined kidney function, chronic kidney disease, and renal failure, and/or the stage of the disease by using, as a measure, the similarity obtained in step S32. Specifically, when it is determined from the similarity that patterns are similar ("YES" in step 33), the prediction unit 63 determines in step S34 that the subject has at least one disease selected from the group consisting of declined kidney function, chronic kidney disease, and renal failure corresponding to a pattern in the standard data 1 (D1) that is similar to the subject data M4, and/or that the subject is in a stage of at least one disease selected from the group consisting of declined kidney function, chronic kidney disease, and renal failure corresponding to the standard data 1.

When it is determined from the similarity obtained in step S32 that patterns are not similar ("NO" in step 33), the prediction unit 63 determines in step S36 that the subject does not have at least one disease selected from the group consisting of declined kidney function, chronic kidney disease, and renal failure corresponding to the standard data 1, and/or that the subject is not in a stage of at least one disease selected from the group consisting of declined kidney function, chronic kidney disease, and renal failure corresponding to the standard data 1.

In step S35, the prediction unit 63 outputs the result determined in step S34 as prediction result data. In this embodiment, the prediction result is displayed on the display unit 4, and the prediction result data is stored in the storage unit 103 in the prediction device 6. The prediction result may be displayed on a display unit of an external computer terminal connected to the prediction device 6 via the internet, for example, a display unit of a computer terminal in a third-party organization, instead of displaying the prediction result on the display unit 4.

4. Forward iOrgans 4-1. Outline

In this embodiment, the presence of a disease and/or the stage of the disease in each of one or more organs other than the kidneys in a subject affected with at least one disease selected from the group consisting of declined kidney function, chronic kidney disease, and renal failure is predicted. Specifically, the presence of a disease and/or the stage of the disease in each of one or more organs other than the kidneys in a subject affected with at least one disease selected from the group consisting of declined kidney function, chronic kidney disease, and renal failure is predicted based on information regarding the stage of the at least one disease selected from the group consisting of declined kidney function, chronic kidney disease, and renal failure in the subject obtained from diagnostic result of the subject. This embodiment comprises the steps of (i) obtaining information regarding a stage of at least one disease selected from the group consisting of declined kidney function, chronic kidney disease, and renal failure in a subject from a diagnostic result of the subject; (ii) checking the information about the stage obtained in step (i) against standard data 2; (iii) determining, from the standard data 2, standard data a at a stage of the at least one disease selected from the group consisting of declined kidney function, chronic kidney disease, and renal failure corresponding to the information about the stage, based on the checking result obtained in step (ii), and extracting, from the standard data a, a pattern of an inter-organ cross talk indicator corresponding to the stage in the subject in each of one or more organs other than the kidneys in the subject; (iv) checking the pattern of the inter-organ cross talk indicator extracted in step (iii) against known information about inter-organ cross talk indicators in diseases and/or stages of the diseases, and determining the presence of a disease and/or the stage of the disease in each of the one or more organs other than the kidneys corresponding to the pattern of the inter-organ cross talk indicator in each of the one or more organs other than the kidneys in the subject; and (v) further determining that the disease in each of the one or more organs other than the kidneys determined in step (iv) is a disease from which the subject may be suffering, and/or determining that the stage of the disease in each of the one or more organs other than the kidneys determined in step (iv) is a stage of a disease from which the subject is suffering.

In step (i), the diagnostic result of the subject is not limited as long as it is derived by, for example, a physician based on, for example, test results or a medical interview. The diagnostic result may be information obtained from, for example, a paper chart; or may be electronic data extracted from, for example, an electronic chart. In step (i), information about the stage of at least one disease selected from the group consisting of declined kidney function, chronic kidney disease, and renal failure in a subject is obtained as, for example, oral, written, or digital information, based on the diagnostic result of the subject. That is, the information about the stage of at least one disease selected from the group consisting of declined kidney function, chronic kidney disease, and renal failure in a subject is information regarding in what stage of at least one disease selected from the group consisting of declined kidney function, chronic kidney disease, and renal failure the subject is.

In checking the information regarding the stage obtained in step (i) against the standard data 2 in step (ii), for example, it is checked whether the name of the stage matches the name of the stage of the at least one disease selected from the group consisting of declined kidney function, chronic kidney disease, and renal failure assigned to each pattern of an inter-organ cross talk indicator in the standard data 2. The checking may be carried out visually; or may be carried out, for example, on database software, such as Microsoft (registered trademark) Excel (Microsoft Corporation) or Microsoft (registered trademark) Access (Microsoft Corporation), using the search function, the filtering function, or the like of the software.

In step (iii), patterns of inter-organ cross talk indicators linked with the name of the stage of the at least one disease selected from the group consisting of declined kidney function, chronic kidney disease, and renal failure in the subject are extracted based on the result of the checking in step (ii). The group of the extracted patterns of inter-organ cross talk indicators is determined to be standard data a. Further, at least one organ other than the kidneys is selected from the names of organs linked with the corresponding patterns of inter-organ cross talk indicators contained in standard data a, and the pattern of the inter-organ cross talk indicator in the at least one selected organ is extracted. Selection of at least one organ other than the kidneys, and extraction of the pattern of the inter-organ cross talk indicator in the at least one selected organ may be carried out visually; or may be carried out on the database software described above using the search function, the filtering function, or the like of the software.

In step (iv), the similarity between the extracted pattern of the inter-organ cross talk indicator in the at least one selected organ and the information regarding inter-organ cross talk indicators in diseases and/or stages of the diseases stored in a database of known information regarding diseases (e.g., DPC database (provided by Japanese Ministry of Health, Labour and Welfare), PubMed (provided by National Center for Biotechnology Information), Embase (provided by Elsevier), or Cochrane Library (Cochrane); hereinafter also referred to as "disease information database") is calculated and determined. Subsequently, the name of a disease, or the name of a stage of a disease, whose pattern of the inter-organ cross talk indicator stored in the disease information database is determined to be wholly or partially similar to the pattern of the inter-organ cross talk indicator in the at least one selected organ, is extracted. Whether the pattern of the inter-organ cross talk indicator in the at least one selected organ is similar to the known information can be determined according to a method for determining similarity described in the above section "II. iOrgans, 1. Explanation of terms." It can then be determined that the extracted disease is present in the selected organ other than the kidneys, or that the selected organ other than the kidneys is in the extracted stage of the disease. In this determination process, the pattern of the inter-organ cross talk indicator in the at least one selected organ can be compared with known information regarding the inter-organ cross talk indicator in healthy individuals to determine that the organ is normal.

In step (v), it is further determined that the disease in the selected organ other than the kidneys determined in step (iv) is a disease from which the subject may be suffering, and/or that the stage of the disease determined in step (iv) is a stage of a disease from which the subject is suffering. When multiple diseases are determined in step (iv), it can be determined that a disease showing high similarity to the pattern of the inter-organ cross talk indicator in the selected organ is a disease from which the subject may be suffering. When multiple stages of diseases are determined in step (iv), it can be determined that a stage of a disease showing high similarity to the pattern of the inter-organ cross talk indicator in the selected organ is the stage of the disease from which the subject may be suffering.

Further, this embodiment may also be a method for obtaining information to predict the presence of a disease and/or the stage of the disease in each of one or more organs other than the kidneys in a subject affected with at least one disease selected from the group consisting of declined kidney function, chronic kidney disease, and renal failure, the method comprising steps (i) to (iii) above; and further comprising, instead of step (iv) above, step (iv') of checking the pattern of the inter-organ cross talk indicator extracted in step (iii) against known information regarding inter-organ cross talk indicators in diseases and/or the stages of the diseases, and obtaining information regarding the presence of a disease and/or the stage of the disease in each of the one or more organs other than the kidneys corresponding to the pattern of the inter-organ cross talk indicator in each of the one or more organs other than the kidneys in the subject. Checking the extracted pattern of the inter-organ cross talk indicator against known information regarding inter-organ cross talk indicators in diseases and/or stages of the diseases is in accordance with step (iv) above.

The prediction method above may also comprise a step of obtaining a group of standard data 2 from a storage device

10 (FIG. 17) storing the group of standard data 2, or a step of obtaining one or more sets of standard data 2 from the storage device 10 storing the group of standard data 2.

4-2. System Configuration

Figure 17:
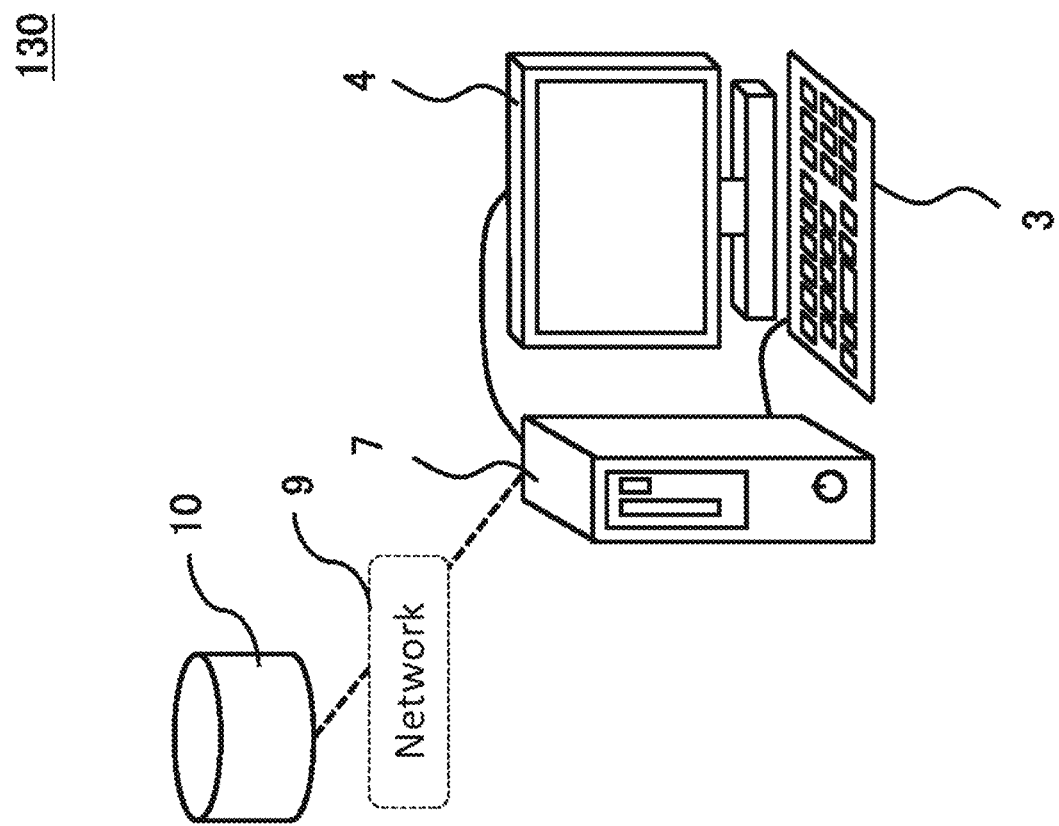
FIG. 17 is an overview of a system 130 according to a fourth embodiment of the present invention.
Figure 18:
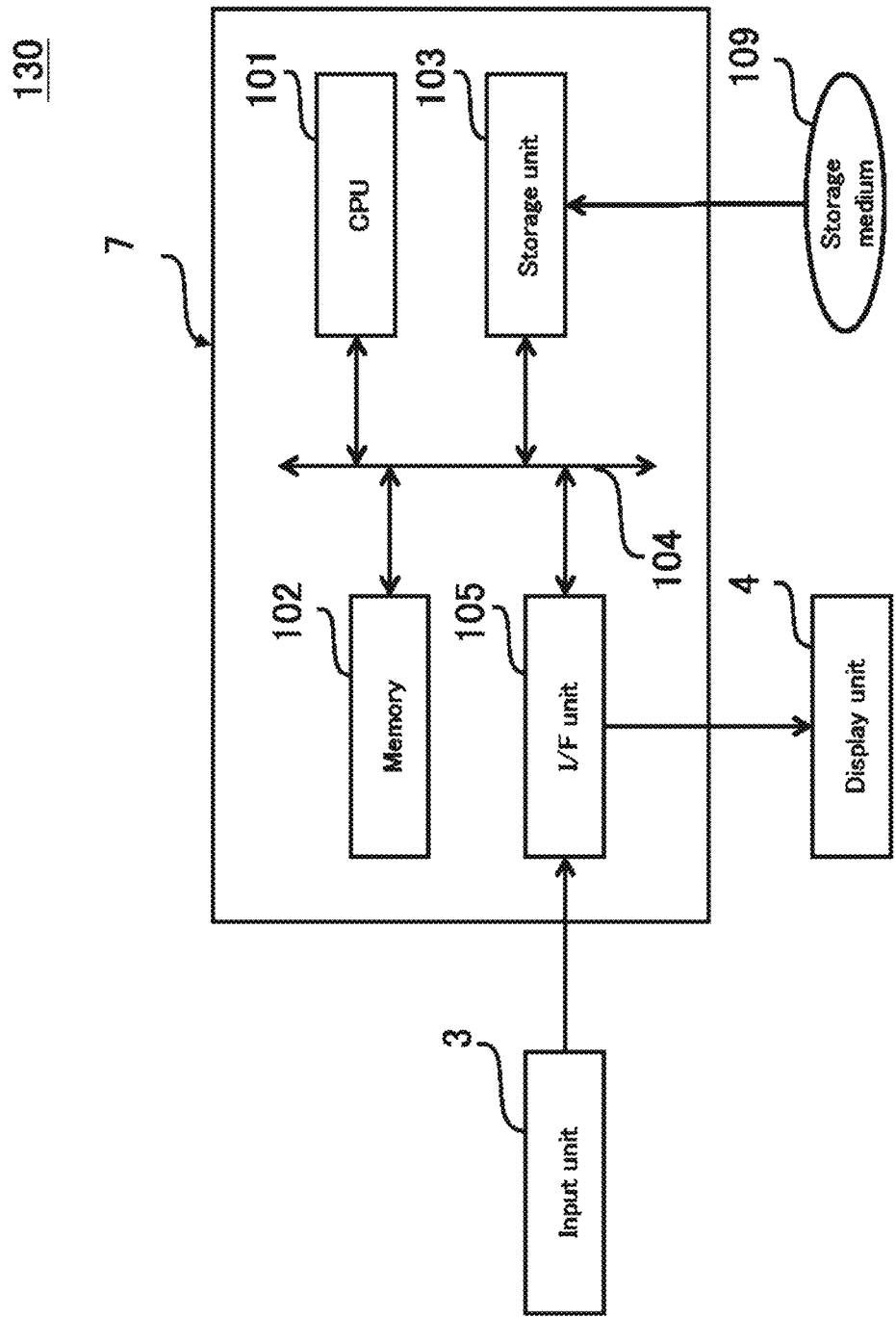
FIG. 18 is a block diagram illustrating a hardware configuration of the system 130 according to the fourth embodiment of the present invention.

FIG. 17 is an overview of a system 130 according to a fourth embodiment of the present invention, and FIG. 18 is a block diagram illustrating a hardware configuration of the system 130. The system 130 comprises an input unit 3, a display unit 4, and a prediction device 7.

The prediction device 7 includes, for example, a general-purpose personal computer; and comprises a CPU 101 for performing data processing described later, a memory 102 serving as a work area for data processing, a storage unit 103 for storing processed data, a bus 104 for transmitting data between the units, and an interface unit 105 (hereinafter referred to as an "I/F unit") for performing data input and output between the prediction device and external devices. The input unit 3 and the display unit 4 are connected to the prediction device 7. The input unit 3 includes, for example, a keyboard, and the display unit 4 includes, for example, a liquid crystal display. The input unit 3 and the display unit 4 may be integrated and implemented as a display with a touch panel. The prediction device 7 need not be a single apparatus; and the CPU 101, the memory 102, the storage unit 103, and the like may be located in separate places, and connected via a network. The prediction device 7 may also be a device that omits the input unit 3 and the display unit 4 and that does not require an operator.

In the explanation below, a process performed by the prediction device 7 means a process performed by the CPU 101 of the prediction device 7 based on a prediction program unless otherwise specified. The CPU 101 temporarily stores necessary data (such as intermediate data being processed) in the memory 102 that serves as a work area, and suitably stores data that is stored for a long period of time, such as computation results, in the storage unit 103.

As described above, the hardware configuration of each of the input unit 3, display unit 4, and prediction device 7 of the system 130 may be the same as that of each of the input unit 3, display unit 4, and screening device 1 of the system 100 shown in FIG. 1; or that of each of the input unit 3, display unit 4, and screening device 2 of the system 110 shown in FIG. 5.

The system 130 may also comprise a storage device 10 storing standard data 2 or a group of standard data 2, the storage device 10 being connected to the prediction device via a network. A network 9 is, for example, a communication medium, such as the internet, virtual private network (VPN), wide area network (WAN), or public switched telephone network (PSTN), and is not limited as long as it enables communication between the storage device 10 and the prediction device 7. Specifically, the system 130 may be a prediction system for predicting the presence of a disease and/or the stage of the disease in each of one or more organs other than the kidneys in a subject affected with at least one disease selected from the group consisting of declined kidney function, chronic kidney disease, and renal failure, the system comprising the storage device 10 storing standard data 2 or a group of standard data 2 and the prediction device 7 described later.

4-3. Prediction Device

The present invention includes, as the fourth embodiment, a device for predicting the presence of a disease and/or the stage of the disease in each of one or more organs other than the kidneys in a subject affected with at least one disease selected from the group consisting of declined kidney function, chronic kidney disease, and renal failure, the device comprising the following computation means:

means for obtaining information about a stage of the at least one disease selected from the group consisting of declined kidney function, chronic kidney disease, and renal failure in the subject;

means for checking the information about the stage obtained by the stage information obtaining means against standard data 2;

means for extracting a pattern of an inter-organ cross talk indicator in each of one or more organs other than the kidneys in the subject based on the result obtained by the stage information checking means; and means for predicting the presence of a disease and/or the stage of the disease in each of the one or more organs other than the kidneys by using, as a measure, the pattern of the inter-organ cross talk indicator obtained by the pattern extraction means.

The prediction device may also comprise a function for obtaining a group of standard data 2 from the storage device 10 storing the group of standard data 2, or a function for obtaining one or more sets of standard data 2 from the storage device 10 storing the group of standard data 2.

In this embodiment, the presence of at least one disease selected from the group consisting of declined kidney function, chronic kidney disease, and renal failure and/or stage of the disease in a subject can be predicted by the system 130 (FIGS. 17 and 18) comprising the prediction device 7 as the prediction device above.

Figure 19:
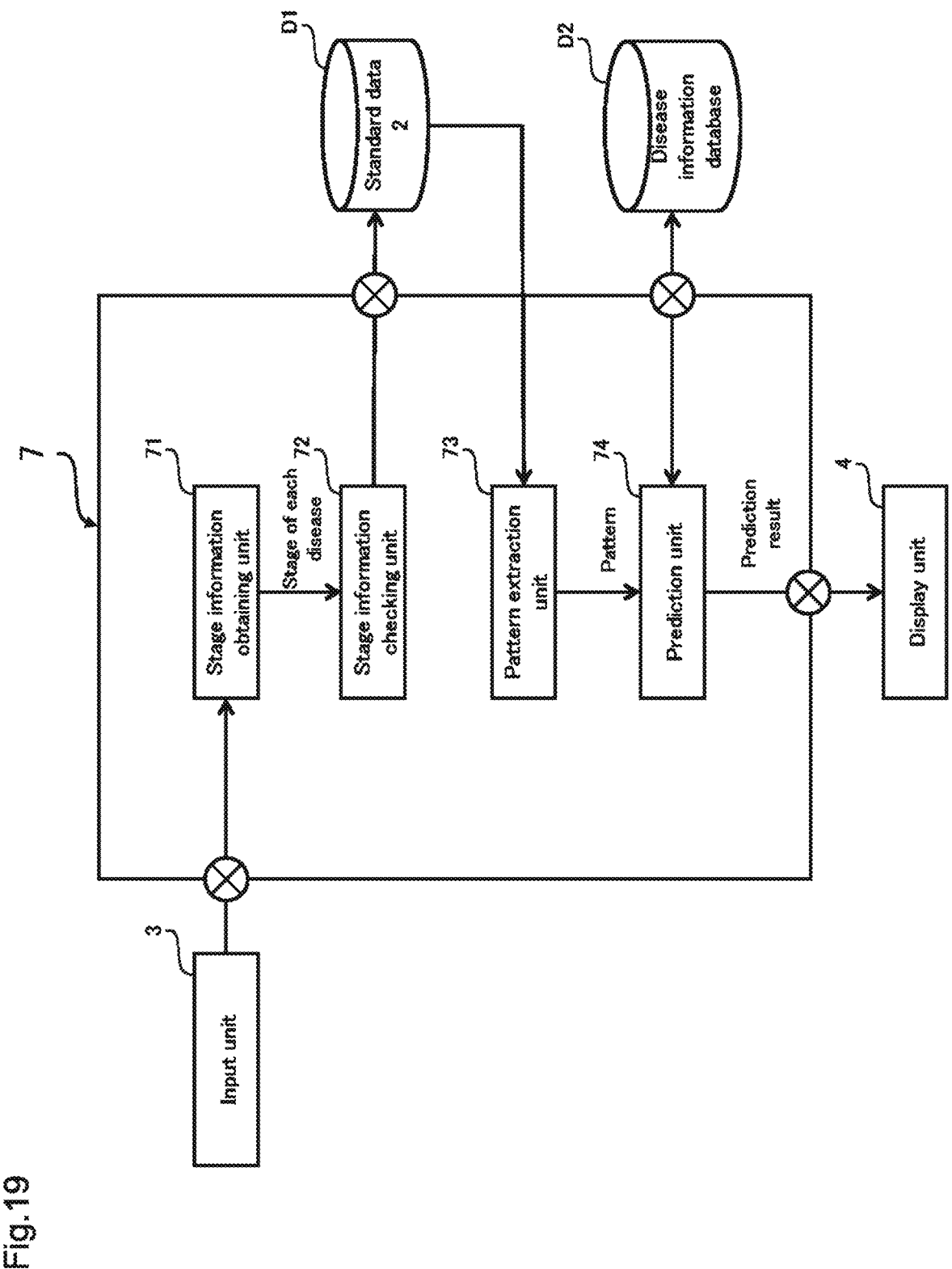
FIG. 19 is a block diagram illustrating functions of a prediction device 7 according to the fourth embodiment of the present invention.

FIG. 19 is a block diagram illustrating functions of the prediction device 7 according to the fourth embodiment of the present invention. The prediction device 7 comprises a stage information obtaining unit 71, a stage information checking unit 72, a pattern extraction unit 73, and a prediction unit 74. These functional blocks are implemented by installing the prediction program according to the present invention in the storage unit 103 or the memory 102 of the prediction device 7, and causing the CPU 101 to execute the program. With this structure, the prediction device 7 carries out the prediction method described later in the section "II. iOrgans, 4-5. Prediction method." The stage information obtaining means, stage information checking means, pattern extraction means, and prediction means recited in the claims correspond to the stage information obtaining unit 71, stage information checking unit 72, pattern extraction unit 73, and prediction unit 74 shown in FIG. 19, respectively.

In other words, the prediction device 7 is a device for predicting the presence of a disease and/or the stage of the disease in each of one or more organs other than the kidneys in a subject affected with at least one disease selected from the group consisting of declined kidney function, chronic kidney disease, and renal failure, the device executing the following computation functions by the CPU 101:

a function for obtaining information about a stage of the at least one disease selected from the group consisting of declined kidney function, chronic kidney disease, and renal failure in the subject;

a function for checking the information about the stage obtained by the stage information obtaining function against standard data 2;

a function for extracting a pattern of an inter-organ cross talk indicator in each of one or more organs other than the kidneys in the subject based on the result obtained by the stage information checking function; and a function for predicting the presence of a disease and/or the stage of the disease in each of the one or more organs other than the kidneys by using, as a measure, the pattern of the inter-organ cross talk indicator obtained by the pattern extraction function.

In this embodiment, standard data 2 (D1) and disease information database D2 are stored outside the prediction device 7, and put into the prediction device 7 via, for example, the internet.

The standard data 2 (D1) and the disease information database D2 may be stored in the storage unit 103 or the memory 102 of the prediction device 7 beforehand.

Moreover, the functional blocks, i.e., the stage information obtaining unit 71, the stage information checking unit 72, the pattern extraction unit 73, and the prediction unit 74, are not necessarily executed by a single CPU, and may be processed by multiple CPUs in a distributed manner. For example, these functional blocks may be configured such that the function of the stage information obtaining unit 71 is executed by a CPU of a first computer; and such that the functions of the stage information checking unit 72, the pattern extraction unit 73, and the prediction unit 74 are executed by a CPU of a second computer, i.e., another computer.

4-4. Prediction Program

Moreover, in order to carry out steps S41 to S49 in FIG. 20 described below, the prediction device 7 stores the prediction program according to the present invention beforehand in the storage unit 103, for example, in an executable format. The prediction device 7 carries out processing using the prediction program stored in the storage unit 103.

Specifically, the prediction program according to the fourth embodiment of the present invention is a prediction program that, when executed by a computer, causes the computer to carry out the following processing to predict the presence of a disease and/or the stage of the disease in each of one or more organs other than the kidneys in a subject affected with at least one disease selected from the group consisting of declined kidney function, chronic kidney disease, and renal failure:

processing of obtaining information about a stage of the at least one disease selected from the group consisting of declined kidney function, chronic kidney disease, and renal failure in the subject;

processing of checking the information about the stage obtained by the stage information obtaining processing against standard data 2;

processing of extracting a pattern of an inter-organ cross talk indicator in each of one or more organs other than the kidneys in the subject based on the result obtained by the stage information checking processing; and processing of predicting the presence of a disease and/or the stage of the disease in each of the one or more organs other than the kidneys by using, as a measure, the pattern of the inter-organ cross talk indicator obtained by the pattern extraction processing.

The prediction program may also comprise processing of obtaining a group of standard data 2 from the storage device 10 storing the group of standard data 2, or processing of obtaining two or more sets of standard data 2 from the storage device 10 storing the group of standard data 2.

In this embodiment, as shown in FIG. 18, the prediction program is stored in a computer-readable non-transitory tangible storage medium 109, such as a CD-ROM, and installed to the prediction device 7 from the storage medium 109; alternatively, the prediction device 7 may be connected to the internet (not shown) to download the program code of the prediction program via the internet. To cause a computer to carry out the computation processing described above, the prediction program according to the present invention may be linked to another program stored in the storage unit 103 or the memory 102. For example, the prediction program may be linked to the commercially available database software mentioned in the above section "II. iOrgans, 4-1. Outline," and the stage information checking processing and the pattern extraction processing may be carried out using the database software.

4-5. Prediction Method

The prediction device 7 according to the fourth embodiment of the present invention carries out the prediction method according to the fourth embodiment of the present invention. The prediction method according to the fourth embodiment of the present invention is a method for predicting the presence of a disease and/or the stage of the disease in each of one or more organs other than the kidneys in a subject affected with at least one disease selected from the group consisting of declined kidney function, chronic kidney disease, and renal failure, the method comprising the steps of:

obtaining information about a stage of the at least one disease selected from the group consisting of declined kidney function, chronic kidney disease, and renal failure in the subject;

checking the information about the stage obtained in the stage information obtaining processing against standard data 2;

extracting a pattern of an inter-organ cross talk indicator in each of one or more organs other than the kidneys in the subject, based on the checking result obtained in the stage information checking step; and predicting the presence of a disease and/or the stage of the disease in each of the one or more organs other than the kidneys, by using, as a measure, the pattern of the inter-organ cross talk indicator obtained in the pattern extraction processing.

The prediction method may also comprise a step of obtaining a group of standard data 2 from the storage device 10 storing the group of standard data 2, or a step of obtaining one or more sets of standard data 2 from the storage device 10 storing the group of standard data 2.

Figure 20:
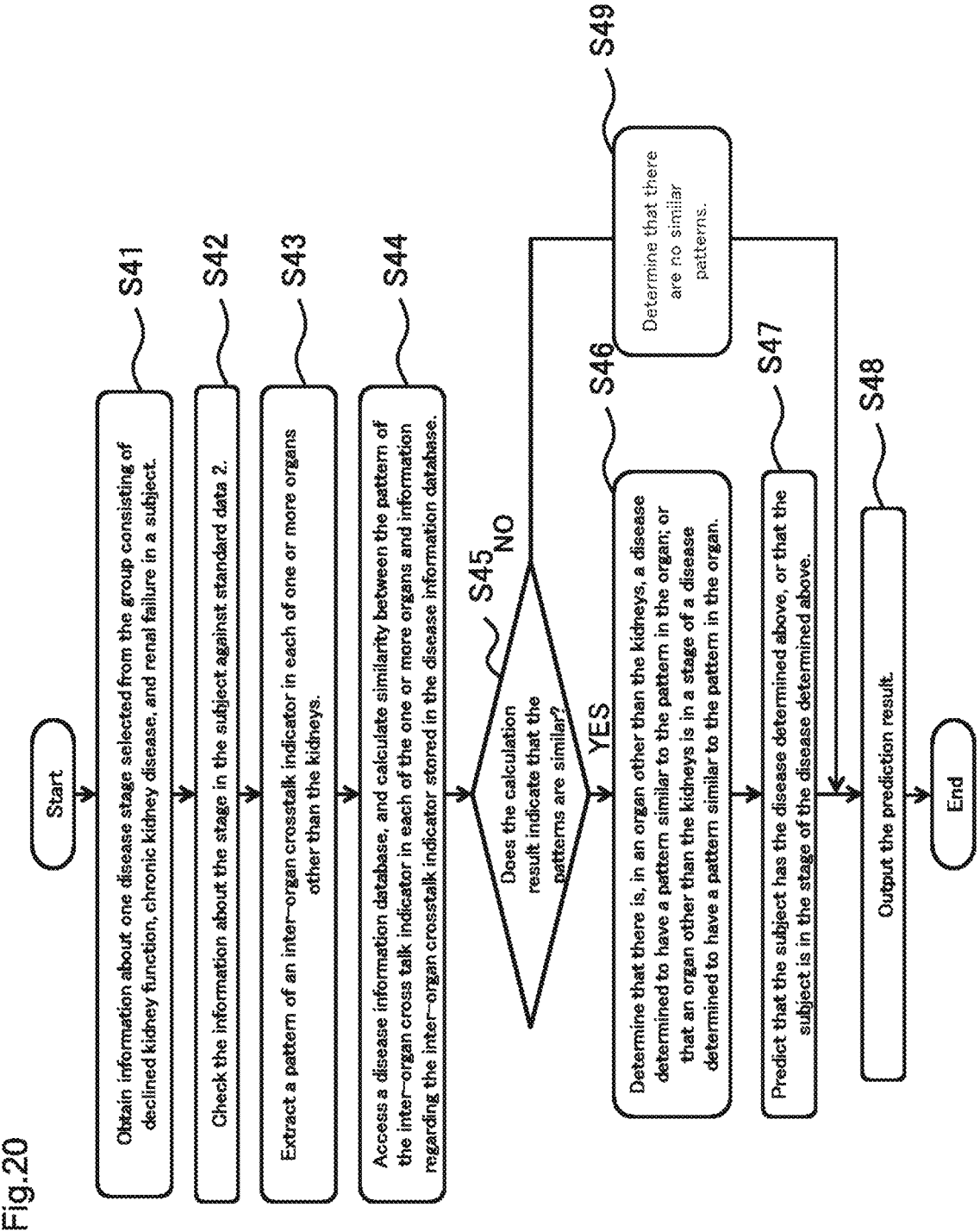
FIG. 20 is a flow chart illustrating a flow of data processing performed by the prediction device 7 according to the fourth embodiment of the present invention to carry out a prediction method.

FIG. 20 is a flow chart illustrating a flow of data processing performed by the prediction device 7 according to the fourth embodiment of the present invention to carry out the prediction method described above. The processing of steps S41 to S49 shown in FIG. 20 is performed by the stage information obtaining unit 71, stage information checking unit 72, pattern extraction unit 73, and prediction unit 74 shown in FIG. 19.

In step S41, the stage information obtaining unit 71 obtains stage information. The stage information is information regarding in what stage of at least one disease selected from the group consisting of declined kidney function, chronic kidney disease, and renal failure the subject is. The stage information obtaining unit 71 obtains the stage information by, for example, operation of the input unit 3. The manner in which the stage information is obtained is not limited to this, and the stage information may be stored in the storage unit 103 of the prediction device 7 from an electronic chart or by any method, such as external data communication.

In step S42, the stage information checking unit 72 checks the stage information against standard data 2 (D1). Subsequently, in step S43, the pattern extraction unit 73 determines, from the standard data 2, standard data a at a stage of the at least one disease selected from the group consisting of declined kidney function, chronic kidney disease, and renal failure corresponding to the stage information, based on the checking result obtained in step S42; and extracts, from the standard data a, a pattern of an inter-organ cross talk indicator corresponding to the stage in the subject in each of the one or more organs other than the kidneys in the subject. The name of one or more organs other than the kidneys to be extracted may be input from the input unit 3. The specific procedure for extraction is in accordance with the description in the above section "II. iOrgans, 4-1. Outline." The prediction program described in the above section "II. iOrgans, 4-4. Prediction program" may comprise program code of a program for causing the CPU 101 of the prediction device 7 to perform computation processing by the stage information checking unit 72 and the pattern extraction unit 73; or, for example, may be linked to commercially available database software mentioned above to cause the CPU 101 to perform the computation processing by the stage information checking unit 72 and the pattern extraction unit 73, using the database software.

In step S44, the prediction unit 74 suitably accesses a disease information database D2 downloaded outside of the prediction device 7 or downloaded in the memory 102 or the storage unit 103; and calculates and determines similarity between the pattern of the inter-organ cross talk indicator in each of the one or more organs extracted in step S43, and information regarding the inter-organ cross talk indicator stored in the disease information database. In step S46, it is determined that there is, in an organ other than the kidneys, a disease determined to have a pattern that is wholly or partially similar to the pattern of the inter-organ cross talk indicator in the organ ("YES" in step S45); or it is determined that an organ other than the kidneys is in a stage of a disease determined to have a pattern that is wholly or partially similar to the pattern of the inter-organ cross talk indicator in the organ ("YES" in step S45). In step S47, it is predicted that the subject is suffering from the disease determined in step S46, or that the subject is in the stage of the disease determined in step S46. The prediction program described in the above section "II. iOrgans, 4-4. Prediction program" may comprise program code of a program for causing the CPU 101 of the prediction device 7 to perform computation processing by the prediction unit 74; or, for example, may be linked to statistical analysis software mentioned in the above section "II. iOrgans, 1. Explanation of terms" to cause the CPU 101 to perform the computation processing by the prediction unit 74, using the statistical analysis software.

In step S48, the prediction unit 74 outputs the result predicted in step S47. In this embodiment, the prediction result is displayed on the display unit 4, and the prediction result is stored in the storage unit 103 in the prediction device 7. The prediction result may be displayed on a display unit of an external computer terminal connected to the prediction device 7 via the internet, for example, a display unit of a computer terminal in a third-party organization, instead of displaying the prediction result on the display unit 4.

When it is determined in step S45 from the result in step S44 that patterns are not similar ("NO" in step S45), the prediction unit 74 determines in step S49 that there are no similar patterns.

The specific procedure of each step is in accordance with the description in the above section "II. iOrgans, 4-1. Outline."

5. Generation of Standard Data, and Standard Data 5-1. Generation of Standard Data The present invention relates to a method for generating standard data 1 for use in "3. Reverse iOrgans" above, and a method for generating standard data 2 for use in "4. Forward iOrgans" above.

The method for generating standard data is a method for generating standard data of patterns of inter-organ cross talk indicators for use in prediction of the presence of at least one disease selected from the group consisting of declined kidney function, chronic kidney disease, and renal failure, and/or the stage of the disease in a subject, the method comprising the steps of:

extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;

extracting the inter-organ cross talk indicator from cells or tissue collected from each of the one or more organs other than the kidneys of negative control(s) of a gold standard;

identifying and quantifying the inter-organ cross talk indicators;

determining patterns of the inter-organ cross talk indicators, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure; and associating the patterns of the inter-organ cross talk indicators with the corresponding stages of the one disease selected from the group consisting of declined kidney function, chronic kidney disease, and renal failure.

Specifically, the procedure for generating standard data 1 is a procedure as described later in the Examples.

First, cells or tissue is collected from one or more organs (e.g., adipose) other than the kidneys of negative control(s) and positive control(s) in each stage of at least one disease selected from the group consisting of declined kidney function, chronic kidney disease, and renal failure; and an inter-organ cross talk indicator is extracted. The extracted inter-organ cross talk indicator is then identified and quantified.

Next, patterns of inter-organ cross talk indicators are determined, each of the patterns being determined from the relationship (ratio) between the amount of an inter-organ cross talk indicator in an organ other than the kidneys of the positive control(s) affected with the at least one disease selected from the group consisting of declined kidney function, chronic kidney disease, and renal failure, and the amount of the corresponding inter-organ cross talk indicator in the organ other than the kidneys of the negative control(s) without the at least one disease selected from the group consisting of declined kidney function, chronic kidney disease, and renal failure. The determined patterns of inter-organ cross talk indicators are linked to the at least one disease selected from the group consisting of declined kidney function, chronic kidney disease, and renal failure; and stored in, for example, a storage device as standard data 1 or a group of standard data 1. Further, the standard data 1 or the group of standard data 1 can be stored in an external server.

Furthermore, the present invention includes a method for generating standard data 2.

The method for generating standard data is a method for generating standard data 2 of patterns of inter-organ cross talk indicators for use in prediction of the presence of a disease and/or the stage of the disease in each of one or more organs other than the kidneys in a subject affected with at least one disease selected from the group consisting of declined kidney function, chronic kidney disease, and renal failure, the method comprising the steps of:
- extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;
- extracting the inter-organ cross talk indicator from cells or tissue collected from each of the one or more organs other than the kidneys of negative control(s) of a gold standard;
- identifying and quantifying the inter-organ cross talk indicators; and
- determining patterns of the inter-organ cross talk indicators for each stage of the at least one disease selected from the group consisting of declined kidney function, chronic kidney disease, and renal failure, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure.

Specifically, the procedure for generating standard data 2 is a procedure as described later in the Examples.

First, cells or tissue are collected from one or more organs other than the kidneys collected from negative control(s) and positive control(s) affected with at least one disease selected from the group consisting of declined kidney function, chronic kidney disease, and renal failure, and an inter-organ cross talk indicator is extracted. The extracted inter-organ cross talk indicator is then identified and quantified.

Next, patterns of inter-organ cross talk indicators are determined for each stage of the at least one disease selected from the group consisting of declined kidney function, chronic kidney disease, and renal failure, each of the patterns being determined from the relationship (ratio) between the amount of an inter-organ cross talk indicator in an organ other than the kidneys collected from the positive control(s) affected with the at least one disease selected from the group consisting of declined kidney function, chronic kidney disease, and renal failure, and the amount of the corresponding inter-organ cross talk indicator in the organ other than the kidneys collected from the negative control(s) without the at least one disease selected from the group consisting of declined kidney function, chronic kidney disease, and renal failure. Such patterns of inter-organ cross talk indicators determined for each stage of the at least one disease selected from the group consisting of declined kidney function, chronic kidney disease, and renal failure are stored in, for example, a storage device as standard data 2 or a group of standard data 2. Further, the standard data 2 or the group of standard data 2 can be stored in an external server.

5-2. Standard Data

The present invention includes standard data 1 or a group of standard data 1 generated by the method described above.

The standard data 1 is standard data of patterns of inter-organ cross talk indicators for use in prediction of the presence of at least one disease selected from the group consisting of declined kidney function, chronic kidney disease, and renal failure and/or the stage of the disease in a subject, the standard data being generated by the steps of:
- extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;
- extracting the inter-organ cross talk indicator from cells or tissue collected from each of the one or more organs other than the kidneys of negative control(s) of a gold standard;
- identifying and quantifying the inter-organ cross talk indicators;
- determining patterns of the inter-organ cross talk indicators, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure; and
- associating the patterns of the inter-organ cross talk indicators with the corresponding stages of the at least one disease selected from the group consisting of declined kidney function, chronic kidney disease, and renal failure.

Generated standard data 1 or group of standard data 1 may be stored in the storage unit 103 or the memory 102 of the prediction device 6. Alternatively, generated standard data 1 may be stored in a storage device connected locally to the prediction device 6 or in an external storage device, for example, a storage device of a server, accessible via a network by the prediction device 6.

Furthermore, the present invention includes standard data 2 or a group of standard data 2 generated by the method described above.

The standard data 2 is standard data of patterns of inter-organ cross talk indicators for use in prediction of the presence of a disease and/or the stage of the disease in each of one or more organs other than the kidneys in a subject affected with at least one disease selected from the group consisting of declined kidney function, chronic kidney disease, and renal failure, the standard data being generated by the steps of:
- extracting an inter-organ cross talk indicator from cells or tissue collected from each of one or more organs other than the kidneys of positive control(s) of a gold standard for each stage of the at least one disease selected from the group consisting of declined kidney function, chronic kidney disease, and renal failure;

extracting the inter-organ cross talk indicator from cells or tissue collected from each of the one or more organs other than the kidneys of negative control(s) of a gold standard;

identifying and quantifying the inter-organ cross talk indicators; and determining patterns of the inter-organ cross talk indicators for each stage of the at least one disease selected from the group consisting of declined kidney function, chronic kidney disease, and renal failure, each of the patterns being determined from a relationship between an amount of the inter-organ cross talk indicator in the organ other than the kidneys in the positive control(s) affected with the at least one disease selected from the group consisting of declined kidney function, chronic kidney disease, and renal failure, and an amount of the corresponding inter-organ cross talk indicator in the same organ as the organ other than the kidneys in the negative control(s) without the at least one disease selected from the group consisting of declined kidney function, chronic kidney disease, and renal failure.

Generated standard data 2 or group of standard data 2 may be stored in the storage unit 103 or the memory 102 of the prediction device 7. Alternatively, generated standard data 2 or group of standard data 2 may be stored in a storage device connected locally to the prediction device 7 or in an external storage device, for example, a storage device of a server, accessible via a network by the prediction device 7.

6. Treatment Method

R-iOrgans and F-iOrgans may further comprise a process for treating at least one disease selected from the group consisting of declined kidney function, chronic kidney disease, and renal failure. The process for treating the disease can be performed according to a known method. When it is determined that a subject has declined kidney function, first, a clinical state causing declined kidney function may be treated in order to slow progression of declined kidney function. Examples of such clinical states include lifestyle-related diseases, such as diabetes and hypertension; urinary diseases, such as urinary tract infection, urinary tract obstruction, glomerulonephritis, vascular disease in the kidneys (blood flow disorder), and drug-induced nephropathy due to an analgesic; and the like. Moreover, treatment such as blood-pressure control or dietary restriction may be performed in order to slow progression of chronic kidney disease. Further, a drug therapy etc. may be performed for abnormal bone metabolism associated with chronic kidney disease using, for example, a phosphate-binding agent when chronic kidney disease progresses. Further, if necessary, dialysis etc. may be performed.

Moreover, in the treatment of at least one disease selected from the group consisting of declined kidney function, chronic kidney disease, and renal failure, an antagonist of an Oscar protein can be used as an active ingredient in the treatment. Examples of the antagonist include soluble receptors of an Oscar protein. The soluble receptors comprise an amino acid sequence of a ligand-binding region in an Oscar protein. The soluble receptors may also comprise, for example, the Fc portion of an immunoglobulin or synthetic polymer polyethylene glycol (PEG) as a molecule other than an amino acid sequence of a ligand-binding region in the Oscar protein. In the case of humans, an example of such a soluble receptor is the soluble receptor set forth in NP_996554.2 (SEQ ID NO: 1), which is capable of inhibiting activation of the Oscar protein. In the case of humans, the soluble receptor comprises, among the sequence of the 1st to 228th amino acids of the amino acid sequence set forth in SEQ ID NO: 1, at least the sequence of the 1st to 220th amino acids, preferably the sequence of the 1st to 228th amino acids. The soluble receptor may comprise an amino acid sequence with at least 70%, preferably at least 80%, more preferably at least 85%, even more preferably at least 90%, still even more preferably 95% homology to the sequence of the 1st to 228th amino acids of the amino acid sequence set forth in SEQ ID NO: 1, in place of the amino acid sequence set forth in SEQ ID NO: 1. The soluble receptor is preferably, for example, a soluble receptor comprising a peptide comprising the amino acid sequence set forth in SEQ ID NO: 2; or a peptide having the same amino acid sequence as the amino acid sequence of the peptide, except that one to three amino acids are substituted, deleted, or inserted, the amino acid sequence being capable of inhibiting activation of human Oscar. In the case of mice, an example of such a soluble receptor is a soluble receptor set forth in NP_783440.1 (SEQ ID NO: 3), which is capable of inhibiting activation of Oscar. The soluble receptor comprises, among the sequence of the 1st to 235th amino acids of the amino acid sequence set forth in SEQ ID NO: 3, at least the sequence of the 1st to 225th amino acids, and preferably the sequence of the 1st to 235th amino acids. The soluble receptor may comprise an amino acid sequence with at least 70%, preferably at least 80%, more preferably at least 85%, even more preferably at least 90%, still even more preferably 95% homology to the sequence of the 1st to 235th amino acids of the amino acid sequence set forth in SEQ ID NO: 3, in place of the amino acid sequence set forth in SEQ ID NO: 3. The soluble receptor is preferably a soluble receptor comprising a peptide comprising the amino acid sequence set forth in SEQ ID NO: 4; or a peptide having the same amino acid sequence as the amino acid sequence of the peptide, except that one to three amino acids are substituted, deleted, or inserted, the amino acid sequence being capable of inhibiting activation of mouse Oscar.

When systemically administered, the antagonist can be administered in an amount of 0.01 to 1,000 mg/day per kg of body weight of an adult.

When locally administered, the antagonist can be administered in an amount of 0.01 to 100 mg per $cm^2$ of target tissue.

The antagonist can be prepared by combining it with pharmaceutically acceptable carriers or additives.

EXAMPLES

The present invention is described in more detail below with reference to examples. The present invention, however, should not be construed as limited to the examples.

Experimental Example 1: Establishment of Model Mice of Chronic Kidney Disease

Model mice of chronic kidney disease were obtained by feeding mice a diet with high phosphorus content after unilateral nephrectomy. As a control, mice were obtained by feeding them a normal diet after a sham operation.

1. Unilateral Nephrectomy

After mice (C57BL/6, 8 weeks old, male) were anesthetized by intraperitoneal administration of Avertin (250 mg/kg), the skin was incised from the back. The right renal artery and vein, and ureter were ligated. After cutting on the distal side of the ligation, the right kidney was removed, and the incision was closed. The control mice were subjected to a sham operation. In the sham operation, the right renal artery and vein, and ureter were exposed, and the incision was closed without ligation. In order to wait for the mice to completely recover from operative stress, the mice were fed a normal diet (containing 0.35% inorganic phosphorus) for 4 weeks.

2. Phosphorus Overload

From 4 weeks after the completion of the operation (12 weeks old), the unilaterally nephrectomized mice were given a diet with high phosphorus content (containing 2.0% inorganic phosphorus) (hereinafter also referred to as the "kidney disease group"). The sham-operated mice were given a normal diet (containing 0.35% inorganic phosphorus) (hereinafter also referred to as the "Sham group").

The model mice of chronic kidney disease were obtained by a modification of the method described in Hu M. C. et al. (J Am Soc Nephrol 22, 124-136, 2011). In Hu M. C. et al., the remaining kidney (left kidney) is subjected to ischemia-reperfusion injury at the time of unilateral nephrectomy in Item 1 above. However, in this modification, ischemia-reperfusion was not performed.

Experimental Example 2: CKD Evaluation 1. 4 Weeks after Start of Diet with High Phosphorus Content (16 Weeks Old)

In histological observation of the kidneys, a decrease in the stainability of proximal tubule cells to an acidophilic dye (Eosin) was observed in Hematoxylin-Eosin (HE) staining, suggesting that some change occurred in mitochondria. There was no finding of evident fibrosis in the renal interstitium; however, a mild degree of inflammatory cell infiltration was observed.

In physiological observation, an increase in urinary proteins was observed; however, an increase in blood creatinine or phosphorus, or a decrease in creatinine clearance, was not observed.

In gene expression observation by the RNA-Seq analysis described later, it was observed that expression of fibrosis markers (Collagen-1, TGF-1) and inflammatory markers (IL-1, MCP-1) was enhanced.

2. 8 Weeks after Start of Diet with High Phosphorus Content (20 Weeks Old)

In histological observation of the kidneys, fibrosis and cell infiltration in the renal interstitium, i.e., kidney fibrosis, was observed. In physiological observation, an increase in urinary proteins and an increase in blood creatinine, phosphorus, and FGF23 were observed; however, creatinine clearance rather increased, indicating the state of so-called hyperfiltration.

3. 12 Weeks after Start of Diet with High Phosphorus Content (24 Weeks Old)

12 weeks after the start of the diet with high phosphorus content, the above-mentioned findings observed 8 weeks after the start of the diet with high phosphorus content further progressed. In some cases, calcification was observed at and around the cortico-medullary junction of the kidney. However, none of the mice died.

Example 1: Observation of Inter-Organ Cross Talk by R-iOrgans

1. Collection of Each Organ

Organs or tissue (the pancreas, skull, brain, pituitary gland (PG), kidney, adrenal glands (AG), liver, spleen, thymus, heart, lungs, submandibular gland (SG), thyroid gland (TG), aorta, skeletal muscle (muscle, SM), skin, testis, adipose, eyes, stomach, jejunum, ileum, and colon) was collected 1 week (early stage: E) and 4 weeks (middle stage: M) after the start of the diet with high phosphorus content (the normal diet in the Sham group).

The animals from which the organs and tissue were to be collected were fasted overnight from the day before dissection and euthanized by cervical dislocation without anesthesia, and the organs and tissue were collected. After the wet weights of the collected organs and tissue were measured, the organs and tissue were rapidly frozen in liquid nitrogen and stored at −80° C.

2. Analysis of RNA (1) Extraction of RNA from Each Tissue

Each cryopreserved tissue was individually homogenized in TRIzol Reagent (Life Technologies) with a Cell Destroyer PS1000 (Pro Sense, Inc.) or PT 10-35 6T Polytron homogenizer (KINEATICA). After incubation at roan temperature for 5 minutes to separate proteins, 0.2 mL of chloroform was added per mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy Mini column (Qiagen), and purified RNAs were collected according to the RNeasy Mini kit (Qiagen) standard protocol. The quality and concentration of each of the collected RNAs was evaluated by 1% agarose electrophoresis and NanoDrop.

(2) Obtaining RNA-Seq Data

RNA-Seq data was obtained using the samples described above by the following procedure in Macrogen Japan Corp.

i. Quality Check

Quality testing of the samples was performed based on the following item.

Concentration measurement and quality check using an Agilent 2200 TapeStation System ii. Preparation of Sample A library for sequencing was prepared using 500 to 1000 ng of each total RNA sample that passed the quality testing as a template with Illumina's TruSeq RNA Sample Prep Kit according to the standard protocol in the following manner.

(a) Purification of poly(A)+RNA using Oligo-dT beads
(b) Poly(A)+RNA fragmentation
(c) Reverse transcription 2nd strand cDNA synthesis
(d) Terminus repair and 3'A addition
(e) Adapter ligation Note: The adapters contain index tags for identification of specimens.

(f) PCR amplification
(g) Purification and removal of low-molecular-weight substances (<200 bp) using AMPure XP beads iii. Obtaining Data Using Next-Generation Sequencer Nucleotide sequence data was obtained using an Illumina HiSeq 4000 next-generation sequencer by reading 100 bases according to the paired-end method.

(3) Analysis of RNA-Seq Data (3-1) Analysis of Output Data Obtained Using Next-Generation Sequencer The following information processing was carried out for the output data.

i. Base calling: text data of nucleotide sequences was obtained from the output raw data of analysis (image data).

ii. Filtering: selection of read data by predetermined filtering was performed.

iii. Sorting based on index sequences: sample data was sorted based on index information.

(3-2) Secondary Analysis of Output Data

The data file (Fastq format) obtained using Illumina HiSeq was uploaded on Galaxy (https://usegalaxy.org/) downloaded to a local server. Thereafter, analysis was carried out using Bowtie2 (http://bowtie-bio.sourceforge.net/bowtie2/index.shtml) to map each sequence to mouse genome map information mm10. The BAM file obtained using Bowtie2 was analyzed using Cufflinks (http://cole-trapnell-lab.github.io/cufflinks/) to calculate FPKM (RPKM) for each gene.

(3-3) Results

Values were calculated by dividing the RNA expression level of each gene (FPKM value) by the expression level of the corresponding RNA (FPKM value) in the mice of the sham group (hereinafter also referred to as "CKD/sham"). Genes in which CKD/sham is more than 1 or less than 1 were classified as group 2, genes in which CKD/sham is more than 1.5 or less than 0.67 were classified as group 3, genes in which CKD/sham is more than 2 or less than 0.5 were classified as group 4, and genes in which CKD/sham is more than 5 or less than 0.2 were classified as group 5 (FIG. 22). All FPKM values of less than 1 were treated as "1." FIG. 23 lists genes in which Sham>1 and CKD/Sham>5, genes in which Sham<1 and CKD/Sham>10, and genes in which Sham>10 and CKD/Sham<0.3. In particular, the genes of FIG. 23 were considered to best reflect the state of kidney function.

From the above results, proteins or mRNAs expressed from the genes listed in FIGS. 22 and 23 were considered to be preferably used as markers for predicting kidney function. Moreover, proteins or mRNAs expressed from the genes listed in FIGS. 22 and 23 were considered to be preferably used as an inter-organ cross talk indicator in the iOrgans technology.

Example 2: Comparison of Pattern Similarities of Inter-Organ Cross Talk Indicators in Each Disease To demonstrate that the presence of chronic kidney disease and a stage can be predicted from the pattern of an inter-organ cross talk indicator obtained from cells or tissue of each organ collected at each stage in the model mice of chronic kidney disease according to the theory of R-iOrgans, correlation coefficients between patterns of expression of RNAs of group 5 shown in FIG. 22 in individual organs were determined for each stage of diseases such as myocardial infarction. The correlation coefficients were determined by modifying Spearman's rank correlation method and Z-score method.

The similarity was calculated based on correlation coefficients of the patterns of inter-organ cross talk indicators between two organs.

1. Spearman's Rank Correlation

Calculation was performed by using function cor (method="spearman") of analysis software R. Tables 4-1 to 4-8 show the results.

TABLE 4-1

| | | | Model mice of chronic kidney disease | | | | | | | | | | | | | | | | | | | |
|---|---|---|---|---|---|---|---|---|---|---|---|---|---|---|---|---|---|---|---|---|---|---|
| | | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
| Model mice of chronic kidney disease | Brain | Early stage | 1.00 | 0.27 | 0.07 | 0.08 | 0.15 | 0.06 | -0.06 | 0.05 | -0.04 | -0.09 | 0.10 | 0.00 | 0.12 | -0.05 | 0.07 | 0.01 | 0.10 | 0.03 |
| | Brain | Middle stage | 0.27 | 1.00 | 0.00 | 0.06 | 0.26 | 0.06 | -0.15 | 0.03 | -0.04 | -0.18 | 0.19 | 0.01 | 0.13 | -0.21 | 0.04 | -0.01 | 0.20 | 0.06 |
| | Brain | Late stage | 0.07 | 0.00 | 1.00 | 0.06 | 0.01 | 0.06 | -0.06 | 0.05 | 0.00 | 0.08 | 0.01 | 0.04 | 0.02 | 0.12 | 0.10 | 0.03 | -0.03 | 0.01 |
| | Heart | Early stage | 0.08 | 0.06 | 0.06 | 1.00 | 0.24 | 0.36 | 0.07 | 0.02 | 0.06 | 0.00 | 0.04 | 0.05 | 0.12 | 0.08 | 0.12 | 0.04 | 0.04 | 0.07 |
| | Heart | Middle stage | 0.15 | 0.26 | 0.01 | 0.24 | 1.00 | 0.32 | -0.06 | 0.03 | -0.04 | -0.12 | 0.14 | 0.02 | 0.14 | -0.05 | 0.08 | 0.03 | 0.20 | 0.09 |
| | Heart | Late stage | 0.06 | 0.06 | 0.06 | 0.36 | 0.32 | 1.00 | 0.09 | 0.02 | 0.12 | 0.01 | 0.06 | 0.09 | 0.12 | 0.08 | 0.13 | 0.04 | 0.08 | 0.10 |
| | Kidney | Early stage | -0.06 | -0.15 | 0.05 | 0.07 | -0.06 | 0.09 | 1.00 | 0.42 | 0.49 | 0.21 | -0.01 | 0.13 | 0.04 | 0.17 | 0.05 | 0.05 | -0.08 | 0.03 |
| | Kidney | Middle stage | 0.05 | 0.03 | 0.03 | 0.02 | 0.03 | 0.02 | 0.42 | 1.00 | 0.57 | 0.07 | 0.16 | 0.10 | 0.01 | -0.04 | 0.05 | -0.01 | 0.04 | 0.04 |
| | Kidney | Late stage | -0.04 | -0.04 | 0.00 | 0.06 | -0.04 | 0.12 | 0.49 | 0.57 | 1.00 | 0.11 | 0.07 | 0.17 | -0.03 | 0.00 | -0.04 | -0.01 | -0.01 | 0.04 |
| | Liver | Early stage | -0.09 | -0.18 | 0.08 | 0.00 | -0.12 | 0.01 | 0.21 | 0.07 | 0.11 | 1.00 | 0.33 | 0.45 | 0.02 | 0.24 | 0.07 | 0.08 | -0.11 | 0.02 |
| | Liver | Middle stage | 0.10 | 0.19 | 0.01 | 0.04 | 0.14 | 0.06 | -0.01 | 0.16 | 0.07 | 0.33 | 1.00 | 0.50 | 0.09 | -0.04 | 0.10 | -0.01 | 0.12 | 0.06 |
| | Liver | Late stage | 0.00 | 0.01 | 0.04 | 0.05 | 0.02 | 0.09 | 0.13 | 0.10 | 0.17 | 0.45 | 0.50 | 1.00 | 0.04 | 0.10 | 0.08 | 0.06 | 0.01 | 0.08 |
| | Lung | Early stage | 0.12 | 0.13 | 0.02 | 0.12 | 0.14 | 0.12 | 0.04 | 0.01 | -0.03 | 0.02 | 0.09 | 0.04 | 1.00 | 0.23 | 0.36 | 0.06 | 0.08 | 0.05 |
| | Lung | Middle stage | -0.05 | -0.21 | 0.12 | 0.08 | -0.05 | 0.08 | 0.17 | -0.04 | 0.00 | 0.24 | -0.04 | 0.10 | 0.23 | 1.00 | 0.29 | 0.09 | -0.07 | 0.02 |
| | Lung | Late stage | 0.07 | 0.04 | 0.10 | 0.12 | 0.08 | 0.13 | 0.05 | 0.05 | -0.04 | 0.07 | 0.10 | 0.08 | 0.36 | 0.29 | 1.00 | 0.04 | 0.01 | 0.05 |
| | Pancreas | Early stage | 0.01 | -0.01 | 0.03 | 0.12 | 0.03 | 0.04 | 0.05 | -0.01 | -0.01 | 0.08 | -0.01 | 0.06 | 0.06 | 0.09 | 0.04 | 1.00 | 0.17 | 0.15 |
| | Pancreas | Middle stage | 0.10 | 0.20 | -0.03 | 0.04 | 0.20 | 0.08 | -0.08 | 0.04 | -0.01 | -0.11 | 0.12 | 0.01 | 0.08 | -0.07 | 0.01 | 0.17 | 1.00 | 0.17 |
| | Pancreas | Late stage | 0.03 | 0.06 | 0.01 | 0.07 | 0.09 | 0.10 | 0.03 | 0.04 | 0.04 | -0.02 | 0.06 | 0.08 | 0.05 | 0.02 | 0.05 | 0.15 | 0.17 | 1.00 |
| | Muscle | Early stage | 0.12 | 0.11 | 0.06 | 0.14 | 0.21 | 0.15 | 0.03 | -0.01 | -0.05 | 0.03 | 0.08 | 0.06 | 0.14 | 0.09 | 0.11 | 0.04 | 0.09 | 0.07 |
| | Muscle | Middle stage | 0.02 | -0.06 | 0.09 | 0.16 | 0.18 | 0.16 | 0.11 | -0.06 | -0.02 | 0.15 | 0.02 | 0.07 | 0.08 | 0.30 | 0.08 | 0.08 | 0.04 | 0.06 |
| | Muscle | Late stage | 0.03 | -0.11 | 0.11 | 0.18 | 0.12 | 0.23 | 0.18 | 0.04 | 0.08 | 0.18 | 0.01 | 0.09 | 0.10 | 0.25 | 0.13 | 0.09 | -0.02 | 0.07 |
| | Skin | Early stage | 0.12 | 0.11 | -0.01 | 0.07 | 0.16 | 0.10 | 0.01 | -0.05 | -0.07 | -0.02 | 0.08 | 0.02 | 0.15 | 0.06 | 0.10 | 0.00 | 0.06 | 0.04 |
| | Skin | Middle stage | 0.00 | -0.04 | 0.06 | 0.06 | 0.01 | 0.07 | 0.07 | 0.10 | 0.02 | 0.05 | 0.05 | 0.04 | 0.04 | 0.11 | 0.09 | 0.00 | -0.06 | 0.01 |
| | Skin | Late stage | 0.11 | 0.14 | -0.02 | 0.08 | 0.20 | 0.11 | -0.09 | -0.04 | -0.07 | -0.10 | 0.09 | 0.01 | 0.10 | -0.05 | 0.08 | -0.03 | 0.09 | 0.07 |
| | Spleen | Early stage | 0.05 | 0.01 | 0.04 | 0.06 | 0.08 | 0.07 | 0.07 | 0.01 | 0.00 | 0.06 | 0.04 | 0.04 | 0.16 | 0.10 | 0.11 | 0.05 | -0.01 | 0.01 |
| | Spleen | Middle stage | 0.01 | 0.00 | 0.07 | 0.11 | 0.05 | 0.10 | 0.09 | 0.00 | 0.08 | 0.05 | -0.01 | 0.08 | 0.05 | 0.17 | 0.07 | -0.01 | 0.00 | 0.05 |
| | Spleen | Late stage | 0.01 | 0.04 | 0.03 | 0.13 | 0.04 | 0.11 | 0.07 | 0.02 | 0.11 | 0.00 | -0.01 | 0.07 | 0.08 | 0.10 | 0.10 | 0.02 | 0.04 | 0.07 |
| | Testis | Early stage | 0.05 | 0.11 | -0.06 | 0.05 | 0.09 | 0.03 | -0.04 | -0.05 | -0.01 | -0.08 | 0.03 | -0.03 | 0.01 | -0.09 | -0.02 | -0.02 | 0.07 | 0.04 |
| | Testis | Middle stage | 0.06 | 0.04 | 0.07 | -0.03 | -0.02 | -0.05 | -0.04 | 0.18 | -0.06 | 0.02 | 0.14 | 0.01 | 0.02 | -0.03 | 0.10 | 0.00 | 0.00 | -0.02 |
| | Testis | Late stage | 0.05 | 0.14 | -0.11 | 0.03 | 0.10 | 0.03 | -0.06 | 0.02 | 0.07 | -0.10 | 0.08 | 0.03 | 0.01 | -0.10 | -0.02 | -0.03 | 0.07 | 0.03 |
| | Adipose | Early stage | 0.04 | 0.03 | 0.03 | 0.10 | 0.08 | 0.08 | 0.08 | -0.05 | 0.01 | 0.04 | 0.00 | 0.04 | 0.08 | 0.11 | 0.04 | 0.07 | 0.08 | 0.04 |
| | Adipose | Middle stage | 0.18 | 0.29 | -0.03 | 0.11 | 0.30 | 0.07 | -0.15 | -0.05 | -0.14 | -0.19 | 0.13 | -0.03 | 0.15 | -0.12 | 0.08 | -0.02 | 0.22 | 0.05 |
| | Adipose | Late stage | 0.18 | 0.24 | 0.01 | 0.15 | 0.28 | 0.15 | -0.10 | -0.05 | -0.14 | -0.13 | 0.12 | 0.00 | 0.16 | -0.04 | 0.14 | 0.01 | 0.19 | 0.08 |

TABLE 4-2

| | | Model mice of chronic kidney disease | | | | | | | | | | | | | | |
|---|---|---|---|---|---|---|---|---|---|---|---|---|---|---|---|---|
| | | Muscle Early stage | Muscle Middle stage | Muscle Late stage | Skin Early stage | Skin Middle stage | Skin Late stage | Spleen Early stage | Spleen Middle stage | Spleen Late stage | Testis Early stage | Testis Middle stage | Testis Late stage | Adipose Early stage | Adipose Middle stage | Adipose Late stage |
| Model mice of chronic kidney disease | Brain Early stage | 0.12 | 0.02 | 0.03 | 0.12 | 0.00 | 0.11 | 0.05 | 0.01 | 0.01 | 0.05 | 0.06 | 0.05 | 0.04 | 0.18 | 0.18 |
| | Brain Middle stage | 0.11 | -0.06 | -0.11 | 0.11 | -0.04 | 0.14 | 0.01 | 0.00 | 0.04 | 0.11 | 0.04 | 0.14 | 0.03 | 0.29 | 0.24 |
| | Brain Late stage | 0.06 | 0.09 | 0.11 | -0.01 | 0.06 | -0.02 | 0.04 | 0.07 | 0.03 | -0.06 | 0.07 | -0.11 | 0.03 | -0.03 | 0.01 |
| | Heart Early stage | 0.14 | 0.16 | 0.18 | 0.07 | 0.06 | 0.08 | 0.06 | 0.11 | 0.13 | 0.05 | -0.03 | 0.03 | 0.10 | 0.11 | 0.15 |
| | Heart Middle stage | 0.21 | 0.18 | 0.12 | 0.16 | 0.01 | 0.20 | 0.08 | 0.05 | 0.04 | 0.09 | -0.02 | 0.10 | 0.08 | 0.30 | 0.28 |
| | Heart Late stage | 0.15 | 0.16 | 0.23 | 0.10 | 0.07 | 0.11 | 0.07 | 0.10 | 0.11 | 0.03 | -0.05 | 0.03 | 0.08 | 0.07 | 0.15 |
| | Kidney Early stage | 0.03 | 0.11 | 0.18 | 0.01 | 0.07 | -0.09 | 0.07 | 0.09 | 0.07 | -0.04 | -0.04 | -0.06 | 0.08 | -0.15 | -0.10 |
| | Kidney Middle stage | -0.01 | -0.06 | 0.04 | -0.05 | 0.10 | -0.04 | 0.01 | 0.00 | 0.02 | -0.05 | 0.18 | 0.02 | -0.05 | -0.05 | -0.05 |
| | Kidney Late stage | -0.05 | -0.02 | 0.08 | -0.07 | 0.02 | -0.07 | 0.00 | 0.08 | 0.11 | -0.01 | -0.06 | 0.07 | 0.01 | -0.14 | -0.14 |
| | Liver Early stage | 0.03 | 0.15 | 0.18 | -0.02 | 0.05 | -0.10 | 0.06 | 0.05 | 0.00 | -0.08 | 0.02 | -0.10 | 0.04 | -0.19 | -0.13 |
| | Liver Middle stage | 0.08 | 0.02 | 0.01 | 0.08 | 0.05 | 0.09 | 0.04 | -0.01 | -0.01 | 0.03 | 0.14 | 0.08 | 0.00 | 0.13 | 0.12 |
| | Liver Late stage | 0.06 | 0.07 | 0.09 | 0.02 | 0.04 | 0.01 | 0.04 | 0.08 | 0.08 | -0.03 | 0.01 | 0.03 | 0.04 | -0.03 | 0.00 |
| | Lung Early stage | 0.14 | 0.08 | 0.10 | 0.15 | 0.04 | 0.10 | 0.16 | 0.05 | 0.08 | 0.01 | 0.02 | 0.01 | 0.08 | 0.15 | 0.16 |
| | Lung Middle stage | 0.09 | 0.30 | 0.25 | 0.06 | 0.11 | -0.05 | 0.10 | 0.17 | 0.10 | -0.09 | -0.03 | -0.10 | 0.11 | -0.12 | -0.04 |
| | Lung Late stage | 0.11 | 0.08 | 0.13 | 0.10 | 0.09 | 0.08 | 0.11 | 0.07 | 0.10 | -0.02 | 0.10 | -0.02 | 0.04 | 0.08 | 0.14 |
| | Pancreas Early stage | 0.04 | 0.08 | 0.09 | 0.00 | 0.00 | -0.03 | 0.05 | -0.01 | 0.02 | -0.02 | 0.00 | -0.03 | 0.07 | -0.02 | 0.01 |
| | Pancreas Middle stage | 0.09 | 0.04 | -0.02 | 0.06 | -0.06 | 0.09 | -0.01 | 0.00 | 0.04 | 0.07 | 0.00 | 0.07 | 0.08 | 0.22 | 0.19 |
| | Pancreas Late stage | 0.07 | 0.06 | 0.07 | 0.04 | 0.01 | 0.07 | 0.01 | 0.05 | 0.07 | 0.04 | -0.02 | 0.03 | 0.04 | 0.05 | 0.08 |
| | Muscle Early stage | 1.00 | 0.39 | 0.34 | 0.17 | 0.03 | 0.12 | 0.09 | 0.00 | -0.02 | 0.06 | 0.02 | 0.00 | 0.13 | 0.18 | 0.21 |
| | Muscle Middle stage | 0.39 | 1.00 | 0.47 | 0.18 | 0.03 | 0.09 | -0.02 | 0.06 | 0.01 | 0.00 | -0.04 | -0.04 | 0.18 | 0.05 | 0.14 |
| | Muscle Late stage | 0.34 | 0.47 | 1.00 | 0.09 | 0.08 | 0.02 | 0.04 | 0.10 | 0.05 | 0.11 | 0.01 | -0.08 | 0.17 | 0.00 | 0.12 |
| | Skin Early stage | 0.17 | 0.18 | 0.09 | 1.00 | 0.18 | 0.46 | -0.02 | 0.13 | 0.09 | -0.03 | -0.02 | 0.02 | 0.10 | 0.19 | 0.23 |
| | Skin Middle stage | 0.03 | 0.03 | 0.08 | 0.18 | 1.00 | 0.21 | 0.04 | 0.19 | 0.11 | 0.10 | 0.05 | -0.02 | -0.09 | 0.00 | 0.03 |
| | Skin Late stage | 0.12 | 0.09 | 0.02 | 0.46 | 0.21 | 1.00 | 0.04 | 0.12 | 0.11 | 0.10 | -0.04 | 0.08 | -0.01 | 0.22 | 0.25 |
| | Spleen Early stage | 0.09 | 0.09 | 0.10 | 0.04 | -0.02 | 0.04 | 1.00 | 0.09 | 0.06 | 0.10 | 0.00 | 0.00 | 0.03 | 0.07 | 0.09 |
| | Spleen Middle stage | 0.00 | 0.06 | 0.10 | 0.13 | 0.19 | 0.12 | 0.09 | 1.00 | 0.45 | -0.01 | -0.10 | -0.01 | 0.01 | 0.03 | 0.06 |
| | Spleen Late stage | -0.02 | 0.01 | 0.05 | 0.09 | 0.11 | 0.11 | 0.06 | 0.45 | 1.00 | -0.02 | -0.08 | 0.02 | 0.03 | 0.05 | 0.07 |
| | Testis Early stage | 0.06 | 0.00 | -0.03 | 0.11 | -0.03 | 0.10 | -0.01 | -0.02 | 0.01 | 1.00 | -0.05 | 0.17 | 0.08 | 0.13 | 0.12 |
| | Testis Middle stage | 0.02 | -0.04 | 0.01 | -0.02 | 0.05 | -0.04 | 0.00 | -0.10 | -0.08 | -0.05 | 1.00 | 0.00 | -0.04 | 0.00 | 0.01 |
| | Testis Late stage | 0.00 | -0.08 | -0.08 | 0.02 | -0.02 | 0.08 | 0.00 | 0.01 | 0.02 | 0.17 | 0.00 | 1.00 | -0.04 | 0.00 | 0.05 |
| | Adipose Early stage | 0.13 | 0.18 | 0.17 | 0.10 | -0.09 | -0.01 | 0.03 | 0.01 | 0.03 | 0.08 | -0.04 | 0.03 | 1.00 | 0.30 | 0.30 |
| | Adipose Middle stage | 0.18 | 0.05 | 0.00 | 0.19 | 0.00 | 0.22 | 0.07 | 0.03 | 0.05 | 0.13 | 0.00 | 0.08 | 0.30 | 1.00 | 0.59 |
| | Adipose Late stage | 0.21 | 0.14 | 0.12 | 0.23 | 0.03 | 0.25 | 0.09 | 0.06 | 0.07 | 0.12 | 0.01 | 0.05 | 0.30 | 0.59 | 1.00 |

TABLE 4-3

| | | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|---|---|---|---|---|---|---|---|---|
| Modeled mice of myo-cardial infarction | Brain | Early stage | 0.10 | -0.01 | 0.18 | 0.08 | 0.02 | 0.07 | 0.10 | 0.08 | 0.06 | 0.11 | 0.03 | 0.05 | 0.07 | 0.14 | 0.08 | 0.06 | -0.03 | 0.03 |
| | Brain | Middle stage | 0.07 | 0.02 | 0.06 | 0.02 | 0.00 | 0.03 | 0.06 | 0.04 | 0.09 | 0.02 | 0.00 | 0.04 | -0.05 | 0.00 | -0.06 | 0.00 | 0.00 | 0.02 |
| | Brain | Late stage | -0.08 | -0.10 | -0.06 | -0.04 | -0.05 | -0.03 | 0.01 | 0.00 | 0.00 | 0.02 | -0.03 | -0.05 | -0.01 | -0.04 | -0.01 | -0.03 | -0.06 | 0.02 |
| | Heart | Early stage | -0.04 | -0.03 | 0.02 | 0.04 | -0.04 | 0.10 | 0.14 | 0.13 | 0.25 | 0.11 | 0.06 | 0.12 | 0.06 | 0.09 | 0.04 | 0.06 | -0.01 | 0.04 |
| | Heart | Middle stage | -0.04 | -0.09 | 0.00 | 0.00 | -0.14 | 0.03 | 0.12 | 0.19 | 0.29 | 0.06 | -0.01 | 0.07 | -0.08 | -0.01 | -0.10 | 0.03 | -0.04 | 0.01 |
| | Heart | Late stage | -0.07 | -0.11 | 0.00 | -0.01 | -0.18 | 0.01 | 0.16 | 0.15 | 0.26 | 0.08 | -0.02 | 0.07 | -0.06 | -0.01 | -0.06 | 0.02 | -0.10 | -0.01 |
| | Kidney | Early stage | 0.03 | -0.07 | 0.11 | 0.02 | -0.01 | 0.02 | 0.21 | 0.11 | 0.07 | 0.16 | 0.03 | 0.08 | 0.06 | 0.18 | 0.07 | 0.05 | -0.06 | 0.03 |
| | Kidney | Middle stage | -0.03 | -0.06 | 0.04 | -0.04 | -0.05 | 0.02 | 0.23 | 0.25 | 0.37 | 0.13 | -0.01 | 0.13 | -0.04 | 0.08 | -0.03 | 0.05 | -0.03 | 0.03 |
| | Kidney | Late stage | 0.01 | 0.00 | -0.05 | -0.01 | 0.00 | 0.00 | -0.13 | -0.07 | -0.10 | -0.05 | 0.20 | -0.05 | 0.01 | -0.06 | -0.02 | -0.01 | 0.03 | -0.03 |
| | Liver | Early stage | 0.01 | -0.03 | 0.05 | 0.04 | 0.03 | 0.06 | 0.10 | 0.02 | 0.03 | 0.26 | 0.09 | 0.23 | -0.10 | 0.12 | 0.08 | 0.03 | -0.03 | 0.03 |
| | Liver | Middle stage | -0.04 | -0.05 | 0.00 | 0.00 | -0.07 | 0.02 | 0.10 | 0.17 | 0.26 | 0.16 | -0.08 | 0.17 | 0.03 | -0.04 | -0.07 | 0.00 | -0.02 | 0.01 |
| | Liver | Late stage | 0.00 | -0.02 | -0.01 | 0.01 | -0.03 | 0.01 | -0.01 | -0.02 | -0.02 | -0.09 | 0.10 | -0.11 | 0.26 | -0.03 | -0.01 | 0.01 | 0.04 | 0.00 |
| | Lung | Early stage | 0.04 | 0.02 | 0.06 | 0.04 | 0.06 | 0.09 | 0.05 | 0.04 | 0.04 | 0.08 | 0.09 | 0.10 | -0.04 | 0.16 | 0.21 | 0.08 | 0.07 | 0.04 |
| | Lung | Middle stage | 0.06 | 0.12 | -0.01 | 0.02 | 0.06 | 0.03 | -0.06 | 0.08 | 0.07 | -0.07 | 0.00 | 0.02 | 0.00 | -0.22 | -0.04 | 0.01 | 0.11 | 0.01 |
| | Lung | Late stage | -0.02 | -0.11 | 0.03 | 0.00 | -0.11 | 0.01 | 0.10 | 0.08 | 0.06 | 0.08 | 0.03 | -0.01 | 0.05 | 0.04 | 0.03 | 0.03 | -0.06 | -0.03 |
| | Pancreas | Early stage | 0.01 | 0.08 | 0.01 | 0.01 | 0.08 | 0.05 | -0.05 | -0.06 | -0.04 | -0.02 | 0.01 | 0.00 | 0.03 | 0.00 | 0.01 | 0.04 | 0.04 | -0.02 |
| | Pancreas | Middle stage | 0.02 | -0.03 | 0.05 | 0.02 | -0.03 | 0.04 | 0.01 | -0.03 | -0.05 | 0.06 | 0.00 | 0.04 | 0.10 | 0.07 | 0.05 | 0.03 | 0.03 | 0.00 |
| | Muscle | Early stage | 0.02 | -0.04 | 0.01 | 0.04 | 0.07 | 0.05 | 0.01 | -0.10 | -0.06 | 0.01 | 0.00 | 0.01 | 0.13 | 0.07 | 0.05 | 0.06 | 0.05 | 0.02 |
| | Muscle | Middle stage | 0.03 | -0.02 | 0.11 | 0.04 | 0.09 | 0.12 | 0.13 | 0.03 | 0.01 | 0.16 | 0.07 | 0.08 | 0.01 | 0.22 | 0.12 | 0.07 | 0.00 | 0.03 |
| | Muscle | Late stage | 0.01 | -0.04 | 0.05 | 0.02 | 0.03 | 0.01 | 0.06 | 0.02 | 0.00 | 0.03 | -0.03 | -0.03 | -0.02 | 0.04 | 0.02 | 0.00 | -0.03 | 0.00 |
| | Skin | Early stage | -0.04 | -0.04 | -0.03 | -0.04 | -0.07 | -0.04 | -0.01 | -0.02 | 0.00 | 0.00 | 0.01 | -0.01 | 0.01 | -0.05 | -0.04 | 0.01 | -0.01 | -0.01 |
| | Skin | Middle stage | -0.03 | -0.17 | 0.07 | 0.02 | -0.04 | 0.07 | 0.10 | 0.12 | 0.00 | 0.17 | -0.03 | 0.06 | -0.06 | 0.26 | 0.09 | 0.04 | -0.11 | -0.01 |
| | Skin | Late stage | 0.00 | -0.01 | -0.03 | -0.04 | -0.08 | -0.06 | -0.04 | 0.04 | 0.00 | 0.02 | 0.08 | -0.01 | 0.01 | -0.10 | 0.01 | -0.04 | -0.02 | -0.04 |
| | Spleen | Early stage | -0.03 | -0.03 | 0.00 | -0.02 | -0.06 | -0.01 | 0.01 | 0.04 | 0.02 | 0.04 | 0.01 | -0.02 | 0.07 | 0.06 | 0.07 | 0.02 | 0.00 | -0.01 |
| | Spleen | Middle stage | -0.03 | -0.11 | 0.09 | 0.02 | -0.04 | 0.06 | 0.17 | 0.04 | 0.04 | 0.14 | -0.05 | 0.07 | 0.04 | 0.18 | 0.03 | 0.04 | -0.08 | 0.04 |
| | Spleen | Late stage | 0.08 | 0.09 | -0.03 | 0.00 | 0.10 | -0.01 | -0.09 | -0.01 | -0.07 | -0.01 | 0.11 | 0.01 | 0.07 | -0.07 | 0.03 | 0.03 | 0.09 | 0.00 |
| | Testis | Early stage | 0.05 | 0.09 | 0.00 | 0.01 | 0.07 | -0.01 | -0.10 | -0.09 | -0.17 | -0.03 | 0.05 | -0.04 | 0.10 | -0.03 | 0.07 | 0.00 | 0.04 | -0.03 |
| | Testis | Middle stage | 0.04 | 0.06 | -0.02 | -0.01 | 0.06 | 0.00 | -0.03 | -0.07 | -0.03 | -0.03 | 0.02 | 0.00 | 0.06 | 0.00 | -0.01 | 0.02 | 0.04 | -0.02 |
| | Testis | Late stage | 0.00 | 0.01 | -0.03 | 0.00 | -0.02 | -0.01 | -0.04 | -0.05 | -0.04 | -0.01 | 0.00 | 0.00 | 0.00 | -0.01 | -0.01 | 0.00 | -0.01 | 0.03 |
| | Adipose | Early stage | 0.03 | 0.06 | -0.02 | 0.01 | 0.05 | 0.02 | -0.04 | -0.04 | -0.05 | -0.06 | 0.00 | -0.02 | 0.04 | -0.04 | -0.02 | -0.03 | 0.06 | 0.02 |
| | Adipose | Middle stage | 0.02 | -0.02 | 0.07 | 0.04 | 0.06 | 0.10 | 0.09 | 0.11 | 0.09 | 0.12 | 0.11 | 0.13 | 0.13 | 0.10 | 0.10 | 0.05 | 0.04 | 0.03 |
| | Adipose | Middle stage | 0.02 | 0.06 | 0.00 | 0.03 | 0.07 | 0.03 | 0.03 | 0.05 | 0.05 | -0.02 | 0.04 | 0.03 | 0.04 | -0.01 | 0.01 | 0.07 | 0.13 | 0.04 |
| | Adipose | Late stage | 0.02 | 0.06 | -0.01 | -0.01 | 0.05 | -0.01 | -0.11 | -0.16 | -0.21 | -0.10 | -0.03 | -0.10 | 0.07 | -0.06 | 0.06 | 0.01 | 0.08 | -0.01 |

TABLE 4-4

|  |  |  | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of myocardial infarction | Brain | Early stage | 0.06 | 0.10 | 0.14 | 0.05 | 0.09 | −0.01 | 0.06 | 0.04 |
| | Brain | Middle stage | −0.01 | 0.01 | 0.03 | −0.01 | 0.04 | −0.04 | −0.02 | 0.04 |
| | Brain | Late stage | −0.04 | −0.06 | −0.03 | −0.03 | −0.04 | −0.05 | −0.02 | −0.10 |
| | Heart | Early stage | −0.02 | 0.01 | 0.13 | −0.14 | −0.02 | −0.19 | −0.02 | −0.02 |
| | Heart | Middle stage | −0.09 | −0.08 | 0.06 | −0.25 | 0.02 | −0.27 | −0.08 | −0.01 |
| | Heart | Late stage | −0.14 | −0.15 | 0.02 | −0.20 | 0.05 | −0.24 | −0.06 | −0.02 |
| | Kidney | Early stage | 0.08 | 0.15 | 0.15 | 0.05 | 0.10 | 0.00 | 0.09 | 0.09 |
| | Kidney | Middle stage | −0.01 | 0.06 | 0.07 | −0.03 | 0.06 | −0.05 | −0.02 | 0.03 |
| | Kidney | Late stage | −0.02 | −0.04 | −0.02 | −0.05 | −0.06 | −0.07 | −0.01 | −0.08 |
| | Liver | Early stage | 0.08 | 0.10 | 0.10 | 0.08 | 0.05 | 0.02 | 0.06 | 0.09 |
| | Liver | Middle stage | −0.03 | −0.03 | 0.05 | −0.12 | 0.01 | −0.10 | −0.05 | −0.08 |
| | Liver | Late stage | −0.01 | −0.02 | −0.01 | −0.06 | −0.11 | −0.08 | −0.04 | −0.07 |
| | Lung | Early stage | 0.06 | 0.06 | 0.08 | −0.02 | −0.09 | −0.07 | 0.09 | −0.06 |
| | Lung | Middle stage | 0.05 | −0.06 | −0.03 | −0.13 | −0.13 | −0.06 | −0.02 | −0.21 |
| | Lung | Late stage | −0.04 | 0.00 | 0.05 | −0.08 | −0.07 | −0.14 | 0.00 | −0.09 |
| | Pancreas | Early stage | 0.07 | 0.01 | 0.02 | 0.04 | −0.06 | 0.02 | 0.04 | 0.02 |
| | Pancreas | Middle stage | 0.10 | 0.11 | 0.08 | 0.01 | 0.00 | −0.04 | 0.03 | 0.01 |
| | Pancreas | Late stage | 0.07 | 0.12 | 0.07 | 0.06 | −0.02 | 0.05 | 0.07 | 0.00 |
| | Muscle | Early stage | 0.22 | 0.27 | 0.29 | 0.10 | 0.08 | 0.00 | 0.09 | 0.09 |
| | Musde | Middle stage | 0.17 | 0.09 | 0.12 | 0.04 | 0.10 | 0.02 | 0.02 | 0.11 |
| | Muscle | Late stage | −0.10 | −0.18 | −0.09 | −0.12 | −0.04 | −0.09 | −0.04 | 0.00 |
| | Skin | Early stage | 0.04 | 0.18 | 0.15 | 0.10 | 0.18 | 0.10 | 0.02 | 0.10 |
| | Skin | Middle stage | −0.06 | −0.09 | −0.06 | −0.15 | 0.04 | −0.04 | 0.01 | −0.12 |
| | Skin | Late stage | −0.05 | 0.02 | −0.01 | −0.03 | −0.01 | −0.07 | 0.00 | −0.07 |
| | Spleen | Early stage | 0.03 | 0.11 | 0.16 | 0.10 | 0.12 | 0.00 | 0.13 | 0.21 |
| | Spleen | Middle stage | 0.10 | 0.04 | 0.02 | −0.05 | −0.15 | −0.01 | 0.16 | −0.30 |
| | Spleen | Late stage | 0.05 | 0.01 | −0.02 | −0.04 | −0.19 | −0.01 | 0.26 | −0.24 |
| | Testis | Early stage | 0.06 | 0.06 | 0.00 | 0.04 | −0.07 | 0.02 | 0.04 | −0.02 |
| | Testis | Middle stage | 0.03 | 0.03 | 0.00 | −0.01 | −0.04 | 0.00 | −0.01 | −0.04 |
| | Testis | Late stage | 0.03 | 0.00 | −0.22 | 0.00 | −0.05 | 0.03 | 0.00 | 0.00 |
| | Adipose | Early stage | 0.10 | 0.09 | 0.09 | 0.04 | 0.08 | 0.02 | 0.05 | 0.05 |
| | Adipose | Middle stage | 0.07 | 0.07 | 0.06 | 0.00 | −0.07 | −0.04 | −0.03 | −0.05 |
| | Adipose | Late stage | 0.02 | −0.04 | −0.06 | 0.01 | −0.08 | 0.02 | 0.04 | −0.04 |

|  |  |  | Spleen Late stage | Testis Early stage | Testis Middle stage | Testis Late stage | Adipose Early stage | Adipose Middle stage | Adipose Late stage |
|---|---|---|---|---|---|---|---|---|---|
| Model mice of myocardial infarction | Brain | Early stage | 0.02 | −0.04 | 0.05 | −0.04 | −0.02 | −0.07 | −0.01 |
| | Brain | Middle stage | 0.02 | 0.01 | −0.03 | 0.01 | −0.03 | −0.03 | −0.04 |
| | Brain | Late stage | −0.06 | −0.02 | 0.03 | −0.04 | −0.02 | −0.04 | −0.05 |
| | Heart | Early stage | 0.01 | −0.05 | 0.00 | −0.02 | −0.04 | −0.17 | −0.17 |
| | Heart | Middle stage | 0.00 | −0.08 | 0.01 | 0.00 | −0.09 | −0.24 | −0.25 |
| | Heart | Late stage | 0.04 | −0.07 | −0.02 | 0.00 | −0.10 | −0.26 | −0.27 |
| | Kidney | Early stage | 0.06 | −0.06 | 0.03 | −0.08 | 0.02 | −0.01 | 0.00 |
| | Kidney | Middle stage | 0.02 | −0.05 | −0.01 | 0.00 | −0.01 | −0.16 | −0.12 |
| | Kidney | Late stage | −0.03 | 0.00 | 0.03 | 0.03 | −0.02 | −0.02 | −0.05 |
| | Liver | Early stage | 0.05 | −0.01 | 0.01 | −0.02 | 0.03 | −0.02 | 0.03 |
| | Liver | Middle stage | −0.06 | −0.05 | 0.01 | −0.01 | −0.08 | −0.18 | −0.16 |
| | Liver | Late stage | −0.05 | 0.01 | 0.02 | −0.01 | 0.01 | −0.05 | −0.04 |
| | Lung | Early stage | −0.03 | −0.03 | 0.02 | −0.01 | 0.02 | −0.02 | 0.01 |
| | Lung | Middle stage | −0.20 | 0.01 | 0.05 | 0.04 | −0.05 | 0.03 | 0.04 |
| | Lung | Late stage | −0.04 | −0.09 | 0.08 | −0.05 | −0.04 | −0.19 | −0.15 |
| | Pancreas | Early stage | −0.01 | 0.04 | −0.04 | 0.02 | 0.03 | 0.07 | 0.08 |
| | Pancreas | Middle stage | −0.03 | −0.01 | 0.04 | −0.02 | 0.07 | 0.02 | 0.04 |
| | Pancreas | Late stage | 0.01 | 0.02 | −0.08 | −0.02 | 0.09 | 0.07 | 0.08 |
| | Muscle | Early stage | 0.03 | −0.07 | 0.00 | −0.06 | 0.02 | −0.04 | 0.03 |
| | Musde | Middle stage | 0.03 | −0.03 | 0.00 | −0.03 | 0.01 | 0.04 | 0.05 |
| | Muscle | Late stage | −0.03 | −0.02 | 0.00 | 0.02 | −0.09 | −0.09 | −0.11 |
| | Skin | Early stage | 0.04 | −0.06 | 0.01 | −0.09 | −0.05 | −0.14 | −0.12 |
| | Skin | Middle stage | −0.09 | −0.08 | 0.19 | 0.00 | −0.11 | −0.07 | −0.07 |
| | Skin | Late stage | −0.03 | −0.04 | 0.08 | −0.03 | −0.01 | −0.07 | −0.02 |
| | Spleen | Early stage | 0.13 | −0.06 | −0.01 | −0.07 | 0.03 | −0.07 | −0.02 |
| | Spleen | Middle stage | −0.32 | 0.02 | 0.03 | 0.04 | 0.03 | 0.10 | 0.11 |
| | Spleen | Late stage | −0.21 | 0.02 | 0.04 | 0.01 | 0.03 | 0.10 | 0.09 |
| | Testis | Early stage | −0.04 | 0.10 | −0.07 | −0.01 | 0.08 | 0.11 | 0.06 |
| | Testis | Middle stage | −0.05 | 0.07 | −0.04 | 0.00 | 0.03 | 0.04 | 0.02 |
| | Testis | Late stage | −0.02 | 0.09 | −0.12 | −0.01 | 0.04 | 0.10 | 0.08 |
| | Adipose | Early stage | 0.03 | −0.02 | 0.04 | −0.03 | −0.13 | −0.11 | −0.04 |
| | Adipose | Middle stage | −0.05 | 0.03 | 0.05 | 0.02 | 0.44 | 0.08 | 0.12 |
| | Adipose | Late stage | 0.00 | 0.05 | −0.02 | 0.02 | 0.04 | 0.14 | 0.17 |

TABLE 4-5

|  |  |  | Brain Early stage | Brain Middle stage | Brain Late stage | Heart Early stage | Heart Middle stage | Heart Late stage | Kidney Early stage | Kidney Middle stage | Kidney Late stage |
|---|---|---|---|---|---|---|---|---|---|---|---|
| Model mice of glioma | Left brain | Early stage | 0.06 | 0.02 | −0.08 | 0.00 | 0.00 | 0.02 | 0.01 | 0.10 | 0.03 |
|  | Left brain | Middle stage | −0.24 | −0.52 | 0.15 | −0.05 | −0.27 | −0.04 | 0.23 | −0.02 | 0.06 |
|  | Right brain | Early stage | −0.12 | −0.26 | 0.04 | −0.01 | −0.14 | −0.02 | 0.12 | 0.05 | 0.05 |
|  | Right brain | Middle stage | 0.04 | 0.06 | −0.07 | −0.02 | 0.02 | −0.02 | −0.05 | 0.05 | 0.08 |
|  | Heart | Early stage | −0.11 | −0.17 | 0.05 | −0.05 | −0.21 | −0.09 | 0.11 | −0.03 | 0.00 |
|  | Heart | Middle stage | −0.10 | −0.28 | 0.04 | −0.04 | −0.30 | −0.06 | 0.15 | −0.01 | 0.07 |
|  | Kidney | Early stage | 0.14 | 0.29 | −0.10 | 0.00 | 0.14 | 0.00 | −0.23 | −0.04 | −0.09 |
|  | Kidney | Middle stage | −0.07 | −0.08 | −0.01 | 0.00 | −0.08 | 0.00 | −0.03 | −0.16 | 0.01 |
|  | Liver | Early stage | −0.10 | −0.24 | 0.10 | −0.01 | −0.17 | −0.02 | 0.17 | 0.02 | 0.05 |
|  | Liver | Middle stage | 0.12 | 0.28 | −0.08 | 0.04 | 0.16 | 0.02 | −0.20 | −0.05 | −0.04 |
|  | Lung | Early stage | −0.11 | −0.27 | 0.06 | −0.06 | −0.22 | −0.04 | 0.10 | 0.02 | 0.04 |
|  | Lung | Middle stage | −0.03 | −0.01 | −0.03 | 0.00 | −0.02 | 0.00 | −0.02 | −0.09 | 0.03 |
|  | Pancreas | Early stage | −0.06 | −0.17 | 0.02 | −0.02 | −0.12 | −0.02 | 0.08 | −0.04 | −0.01 |
|  | Pancreas | Middle stage | 0.09 | 0.18 | −0.07 | −0.01 | 0.09 | 0.01 | −0.13 | 0.04 | 0.02 |
|  | Muscle | Early stage | 0.07 | 0.18 | −0.07 | 0.01 | 0.08 | 0.01 | −0.10 | −0.03 | −0.01 |
|  | Muscle | Middle stage | 0.00 | −0.04 | −0.03 | −0.04 | −0.15 | −0.10 | −0.04 | 0.09 | 0.02 |
|  | Skin | Early stage | 0.09 | 0.21 | −0.05 | 0.03 | 0.10 | 0.02 | −0.13 | 0.02 | −0.01 |
|  | Skin | Middle stage | −0.13 | −0.21 | 0.04 | −0.05 | −0.20 | −0.06 | 0.07 | 0.04 | 0.04 |
|  | Spleen | Early stage | 0.02 | 0.05 | −0.01 | 0.01 | 0.00 | 0.05 | −0.02 | −0.02 | −0.01 |
|  | Spleen | Middle stage | −0.01 | 0.00 | −0.01 | 0.01 | −0.02 | 0.01 | −0.03 | −0.06 | −0.03 |
|  | Testis | Early stage | 0.12 | 0.34 | −0.13 | 0.04 | 0.23 | 0.02 | −0.20 | −0.07 | −0.06 |
|  | Testis | Middle stage | −0.05 | −0.15 | 0.08 | −0.03 | −0.12 | −0.05 | 0.07 | 0.11 | 0.00 |
|  | Adipose | Early stage | 0.02 | 0.10 | −0.01 | 0.03 | 0.07 | −0.02 | −0.01 | −0.07 | 0.02 |
|  | Adipose | Middle stage | −0.05 | −0.01 | −0.03 | −0.01 | −0.06 | −0.04 | 0.05 | −0.03 | 0.06 |

|  |  |  | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|
| Model mice of glioma | Left brain | Early stage | 0.02 | 0.05 | 0.03 | 0.05 | −0.04 | 0.01 | 0.00 | −0.02 | −0.01 |
|  | Left brain | Middle stage | 0.27 | −0.23 | 0.00 | −0.10 | 0.33 | −0.01 | 0.66 | −0.26 | −0.05 |
|  | Right brain | Early stage | 0.12 | −0.09 | 0.04 | −0.07 | 0.12 | −0.03 | 0.02 | −0.12 | −0.01 |
|  | Right brain | Middle stage | −0.10 | 0.06 | 0.03 | −0.01 | −0.13 | −0.05 | −0.04 | 0.05 | −0.02 |
|  | Heart | Early stage | 0.14 | −0.11 | −0.03 | −0.02 | 0.14 | 0.02 | 0.03 | −0.15 | −0.13 |
|  | Heart | Middle stage | 0.14 | −0.16 | −0.01 | −0.09 | 0.14 | −0.03 | 0.03 | −0.18 | −0.03 |
|  | Kidney | Early stage | −0.28 | 0.12 | −0.05 | 0.08 | −0.29 | −0.02 | −0.07 | 0.17 | 0.02 |
|  | Kidney | Middle stage | 0.01 | −0.13 | 0.00 | −0.04 | 0.01 | −0.04 | 0.04 | −0.05 | −0.01 |
|  | Liver | Early stage | 0.23 | −0.13 | 0.02 | −0.04 | 0.20 | 0.02 | 0.03 | −0.16 | −0.01 |
|  | Liver | Middle stage | −0.35 | 0.03 | −0.08 | 0.05 | −0.28 | −0.04 | −0.04 | 0.19 | 0.00 |
|  | Lung | Early stage | 0.18 | −0.09 | 0.01 | −0.04 | 0.17 | 0.02 | 0.05 | −0.18 | −0.04 |
|  | Lung | Middle stage | −0.05 | −0.09 | −0.03 | −0.12 | −0.14 | −0.08 | 0.01 | −0.02 | −0.01 |
|  | Pancreas | Early stage | 0.15 | −0.06 | 0.02 | −0.02 | 0.13 | 0.01 | 0.09 | −0.14 | −0.06 |
|  | Pancreas | Middle stage | −0.18 | 0.10 | 0.00 | 0.01 | −0.22 | −0.02 | −0.07 | 0.14 | 0.01 |
|  | Muscle | Early stage | −0.17 | 0.05 | −0.03 | 0.07 | −0.22 | −0.03 | −0.04 | 0.10 | 0.03 |
|  | Muscle | Middle stage | 0.00 | 0.00 | −0.02 | −0.06 | −0.04 | −0.02 | 0.00 | −0.05 | −0.04 |
|  | Skin | Early stage | −0.15 | 0.12 | 0.00 | 0.04 | −0.20 | −0.04 | −0.05 | 0.11 | 0.03 |
|  | Skin | Middle stage | 0.13 | −0.10 | 0.00 | −0.15 | 0.05 | −0.03 | 0.00 | −0.16 | −0.05 |
|  | Spleen | Early stage | −0.05 | 0.00 | 0.00 | 0.03 | −0.04 | 0.02 | −0.02 | 0.01 | 0.01 |
|  | Spleen | Middle stage | 0.03 | 0.01 | 0.01 | −0.01 | −0.03 | 0.03 | 0.04 | −0.02 | −0.02 |
|  | Testis | Early stage | −0.23 | 0.12 | 0.00 | 0.08 | −0.26 | −0.04 | −0.03 | 0.20 | 0.05 |
|  | Testis | Middle stage | 0.13 | 0.01 | 0.02 | −0.03 | 0.09 | 0.06 | 0.03 | −0.09 | −0.03 |
|  | Adipose | Early stage | −0.03 | −0.01 | 0.01 | 0.03 | −0.02 | −0.06 | 0.01 | 0.07 | −0.02 |
|  | Adipose | Middle stage | −0.04 | −0.11 | −0.02 | −0.03 | −0.01 | −0.07 | −0.02 | 0.00 | −0.02 |

TABLE 4-6

|  |  |  | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of glioma | Left brain | Early stage | 0.01 | −0.05 | 0.02 | −0.02 | 0.04 | −0.02 | 0.03 | −0.02 |
|  | Left brain | Middle stage | −0.06 | 0.14 | 0.20 | −0.10 | 0.11 | −0.20 | 0.01 | 0.06 |
|  | Right brain | Early stage | −0.03 | 0.05 | 0.07 | −0.08 | 0.05 | −0.09 | 0.02 | 0.00 |
|  | Right brain | Middle stage | −0.05 | −0.12 | −0.09 | −0.02 | −0.01 | 0.02 | −0.03 | −0.01 |
|  | Heart | Early stage | −0.04 | 0.00 | 0.08 | −0.05 | 0.03 | −0.11 | 0.00 | 0.00 |
|  | Heart | Middle stage | −0.16 | −0.06 | 0.07 | −0.11 | 0.06 | −0.16 | −0.02 | 0.01 |
|  | Kidney | Early stage | 0.03 | −0.16 | −0.19 | 0.05 | −0.09 | 0.12 | −0.03 | −0.08 |
|  | Kidney | Middle stage | −0.08 | −0.02 | 0.01 | −0.06 | −0.06 | −0.06 | −0.03 | 0.00 |
|  | Liver | Early stage | −0.02 | 0.11 | 0.14 | −0.07 | 0.03 | −0.16 | 0.00 | 0.04 |
|  | Liver | Middle stage | 0.03 | −0.15 | −0.19 | 0.05 | −0.08 | 0.13 | −0.01 | −0.06 |
|  | Lung | Early stage | −0.06 | 0.04 | 0.11 | −0.12 | 0.05 | −0.20 | 0.00 | −0.08 |
|  | Lung | Middle stage | −0.04 | −0.06 | −0.05 | −0.05 | −0.05 | −0.03 | −0.04 | −0.02 |
|  | Pancreas | Early stage | −0.04 | 0.06 | 0.09 | −0.06 | 0.02 | −0.09 | −0.01 | −0.02 |

TABLE 4-6-continued

|   |   |   |   |   |   |   |   |   |   |   |
|---|---|---|---|---|---|---|---|---|---|---|
|   | Pancreas | Middle stage | −0.03 | −0.15 | −0.15 | 0.02 | −0.06 | 0.06 | −0.05 | −0.09 |
|   | Muscle | Early stage | 0.00 | −0.15 | −0.13 | 0.06 | −0.05 | 0.13 | 0.02 | 0.00 |
|   | Muscle | Middle stage | −0.16 | −0.17 | −0.12 | −0.12 | −0.03 | −0.09 | −0.06 | −0.07 |
|   | Skin | Early stage | 0.01 | −011 | −0.12 | 0.02 | −0.04 | 0.09 | 0.07 | −0.03 |
|   | Skin | Middle stage | −0.09 | −0.04 | 0.02 | −0.18 | 0.04 | −0.15 | −0.07 | −0.05 |
|   | Spleen | Early stage | 0.03 | 0.00 | 0.01 | 0.00 | 0.00 | 0.01 | −0.08 | −0.03 |
|   | Spleen | Middle stage | 0.03 | 0.00 | 0.02 | −0.08 | −0.11 | −0.08 | 0.02 | −0.19 |
|   | Testis | Early stage | 0.06 | −0.08 | −0.18 | 0.09 | −0.13 | 0.16 | −0.01 | −0.03 |
|   | Testis | Middle stage | −0.04 | 0.00 | 0.05 | −0.10 | 0.06 | −0.13 | −0.01 | −0.04 |
|   | Adipose | Early stage | 0.03 | 0.04 | 0.00 | 0.02 | −0.13 | −0.05 | 0.01 | 0.00 |
|   | Adipose | Middle stage | −0.08 | −0.05 | −0.02 | −0.07 | −0.09 | −0.09 | −0.06 | 0.00 |

|   |   |   | Spleen Late stage | Testis Early stage | Testis Middle stage | Testis Late stage | Adipose Early stage | Adipose Middle stage | Adipose Late stage |
|---|---|---|---|---|---|---|---|---|---|
| Model mice of glioma | Left brain | Early stage | 0.01 | −0.01 | 0.13 | 0.00 | −0.04 | −0.04 | 0.00 |
|   | Left brain | Middle stage | 0.00 | −0.14 | −0.05 | −0.19 | 0.00 | −0.36 | −0.29 |
|   | Right brain | Early stage | −0.01 | −0.09 | −0.01 | −0.08 | −0.08 | −0.22 | −0.17 |
|   | Right brain | Middle stage | 0.01 | 0.03 | −0.01 | 0.07 | −0.05 | 0.04 | 0.01 |
|   | Heart | Early stage | −0.03 | −0.03 | 0.00 | −0.08 | 0.00 | −0.18 | −0.16 |
|   | Heart | Middle stage | 0.01 | −0.11 | −0.01 | −0.11 | 0.02 | −0.25 | −0.21 |
|   | Kidney | Early stage | −0.02 | 0.10 | 0.04 | 0.14 | −0.02 | 0.25 | 0.19 |
|   | Kidney | Middle stage | −0.01 | 0.00 | −0.09 | −0.03 | 0.02 | −0.11 | −0.08 |
|   | Liver | Early stage | −0.02 | −0.10 | 0.04 | −0.10 | −0.02 | −0.27 | −0.19 |
|   | Liver | Middle stage | 0.02 | 0.11 | −0.05 | 0.12 | −0.01 | 0.25 | 0.17 |
|   | Lung | Early stage | −0.05 | −0.11 | 0.06 | −0.12 | −0.07 | −0.30 | −0.22 |
|   | Lung | Middle stage | 0.03 | 0.04 | −0.10 | 0.00 | 0.00 | −0.04 | −0.05 |
|   | Pancreas | Early stage | −0.06 | −0.09 | 0.03 | −0.07 | 0.01 | −0.16 | −0.11 |
|   | Pancreas | Middle stage | 0.01 | 0.10 | 0.01 | 0.09 | 0.01 | 0.15 | 0.11 |
|   | Muscle | Early stage | 0.05 | 0.08 | −0.03 | 0.11 | 0.01 | 0.16 | 0.14 |
|   | Muscle | Middle stage | −0.04 | −0.07 | 0.11 | −0.02 | −0.02 | −0.09 | −0.09 |
|   | Skin | Early stage | 0.02 | 0.09 | 0.02 | 0.09 | 0.02 | 0.18 | 0.14 |
|   | Skin | Middle stage | −0.06 | −0.10 | 0.07 | −0.09 | −0.13 | −0.25 | −0.23 |
|   | Spleen | Early stage | 0.06 | −0.01 | 0.01 | −0.01 | 0.04 | 0.03 | 0.06 |
|   | Spleen | Middle stage | −0.14 | 0.01 | 0.02 | −0.02 | 0.05 | −0.01 | 0.02 |
|   | Testis | Early stage | 0.00 | 0.22 | −0.10 | 0.21 | 0.08 | 0.34 | 0.24 |
|   | Testis | Middle stage | −0.05 | −0.19 | 0.22 | −0.15 | −0.09 | −0.18 | −0.12 |
|   | Adipose | Early stage | 0.02 | 0.11 | −0.09 | 0.06 | 0.44 | 0.26 | 0.09 |
|   | Adipose | Middle stage | 0.01 | 0.03 | −0.06 | 0.01 | 0.23 | 0.05 | −0.09 |

TABLE 4-7

| | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|---|---|---|---|---|---|---|---|
| Model mice of early onset dementia | Brain Early stage | 0.15 | 0.29 | -0.06 | 0.05 | 0.16 | 0.05 | -0.12 | -0.04 | -0.03 | -0.13 | 0.08 | 0.00 | 0.07 | -0.11 | 0.02 | 0.00 | 0.12 | 0.03 |
| | Brain Middle stage | 0.02 | 0.03 | 0.02 | 0.00 | 0.02 | 0.01 | 0.02 | 0.03 | 0.02 | 0.01 | -0.01 | -0.02 | 0.00 | 0.00 | 0.00 | 0.01 | 0.02 | 0.01 |
| | Brain Late stage | 0.11 | 0.20 | -0.03 | 0.03 | 0.12 | 0.06 | -0.04 | -0.01 | 0.03 | -0.11 | 0.05 | -0.02 | 0.06 | -0.09 | 0.03 | 0.01 | 0.10 | 0.02 |
| | Heart Early stage | -0.01 | -0.09 | 0.05 | 0.02 | 0.01 | 0.05 | 0.05 | -0.04 | 0.00 | 0.03 | -0.07 | -0.01 | 0.07 | 0.14 | 0.06 | 0.04 | -0.05 | 0.01 |
| | Heart Middle stage | -0.06 | -0.22 | 0.07 | 0.01 | -0.08 | 0.02 | 0.13 | 0.02 | 0.01 | 0.19 | -0.05 | 0.02 | 0.05 | 0.26 | 0.10 | 0.06 | -0.13 | -0.01 |
| | Heart Late stage | -0.08 | -0.22 | 0.06 | 0.07 | -0.11 | 0.06 | 0.18 | 0.05 | 0.13 | 0.15 | -0.10 | 0.04 | 0.00 | 0.19 | 0.04 | 0.06 | -0.13 | 0.00 |
| | Kidney Early stage | -0.03 | -0.13 | 0.05 | -0.01 | -0.06 | 0.00 | 0.09 | -0.03 | -0.03 | 0.13 | -0.07 | 0.02 | 0.02 | 0.19 | 0.07 | 0.01 | -0.08 | -0.02 |
| | Kidney Middle stage | -0.02 | -0.15 | 0.07 | -0.03 | 0.09 | 0.00 | 0.08 | 0.05 | -0.02 | 0.12 | -0.04 | -0.02 | 0.00 | 0.16 | 0.07 | 0.06 | -0.11 | -0.01 |
| | Kidney Late stage | -0.06 | -0.15 | 0.05 | -0.01 | -0.04 | 0.03 | 0.09 | -0.08 | -0.02 | 0.10 | -0.10 | 0.01 | -0.01 | 0.15 | 0.03 | 0.04 | -0.07 | 0.00 |
| | Liver Early stage | 0.03 | 0.02 | -0.01 | 0.02 | 0.03 | 0.04 | 0.01 | 0.05 | 0.05 | -0.03 | -0.03 | -0.05 | 0.06 | 0.02 | 0.05 | 0.04 | 0.05 | 0.03 |
| | Liver Middle stage | 0.03 | 0.13 | -0.01 | 0.06 | 0.14 | 0.06 | -0.06 | -0.05 | 0.02 | -0.08 | 0.05 | 0.02 | 0.07 | -0.05 | 0.05 | 0.02 | 0.09 | 0.03 |
| | Liver Late stage | -0.02 | -0.06 | 0.00 | 0.00 | 0.00 | 0.06 | 0.09 | 0.04 | 0.10 | 0.07 | -0.07 | -0.01 | 0.03 | 0.09 | 0.01 | 0.05 | -0.01 | 0.03 |
| | Lung Early stage | 0.05 | 0.22 | -0.06 | 0.08 | 0.19 | 0.06 | -0.11 | -0.08 | -0.04 | -0.14 | 0.08 | 0.03 | 0.10 | -0.11 | 0.07 | 0.01 | 0.14 | 0.03 |
| | Lung Middle stage | 0.10 | 0.31 | -0.07 | 0.08 | 0.23 | 0.06 | -0.14 | -0.06 | -0.04 | -0.22 | 0.12 | 0.01 | 0.13 | -0.19 | 0.07 | -0.02 | 0.19 | 0.04 |
| | Lung Late stage | 0.01 | -0.06 | 0.03 | 0.05 | 0.02 | 0.04 | 0.09 | -0.01 | -0.01 | 0.06 | -0.02 | 0.01 | 0.20 | 0.20 | 0.18 | 0.08 | -0.01 | 0.01 |
| | Pancreas Early stage | -0.04 | -0.05 | 0.02 | 0.00 | 0.00 | 0.01 | 0.05 | -0.03 | 0.01 | 0.11 | 0.02 | 0.06 | 0.05 | 0.12 | 0.08 | 0.11 | 0.03 | 0.04 |
| | Pancreas Middle stage | -0.01 | -0.02 | 0.03 | 0.04 | -0.01 | 0.05 | 0.06 | 0.04 | 0.07 | 0.10 | 0.02 | 0.06 | 0.04 | 0.08 | 0.06 | 0.09 | 0.03 | 0.05 |
| | Pancreas Late stage | -0.02 | -0.09 | 0.07 | 0.02 | -0.01 | 0.04 | 0.09 | 0.04 | 0.06 | 0.15 | 0.03 | 0.09 | 0.01 | 0.14 | 0.06 | 0.08 | -0.03 | 0.05 |
| | Muscle Early stage | 0.10 | 0.15 | -0.08 | 0.06 | 0.17 | 0.11 | -0.05 | 0.01 | 0.02 | -0.12 | 0.11 | 0.01 | 0.12 | -0.10 | 0.05 | -0.01 | 0.13 | 0.03 |
| | Muscle Middle stage | -0.03 | -0.21 | 0.06 | 0.01 | -0.11 | 0.03 | 0.16 | 0.10 | 0.04 | 0.16 | -0.07 | -0.02 | 0.05 | 0.21 | 0.11 | 0.05 | -0.13 | -0.01 |
| | Muscle Late stage | -0.02 | -0.09 | 0.03 | 0.07 | -0.01 | 0.11 | 0.12 | 0.04 | 0.09 | 0.08 | -0.02 | 0.05 | 0.04 | 0.11 | 0.06 | 0.04 | -0.05 | 0.01 |
| | Skin Early stage | 0.07 | 0.20 | -0.08 | 0.05 | 0.21 | 0.09 | -0.07 | -0.05 | -0.03 | -0.14 | 0.04 | -0.02 | 0.09 | -0.10 | 0.00 | -0.02 | 0.11 | 0.04 |
| | Skin Middle stage | 0.09 | 0.32 | -0.08 | 0.04 | 0.22 | 0.04 | -0.18 | -0.06 | -0.05 | -0.25 | 0.11 | 0.00 | 0.04 | -0.26 | 0.00 | -0.04 | 0.18 | 0.02 |
| | Skin Late stage | -0.01 | -0.06 | 0.04 | 0.03 | 0.01 | 0.06 | 0.04 | 0.02 | -0.02 | 0.07 | -0.02 | 0.01 | -0.02 | 0.10 | 0.03 | 0.01 | -0.06 | 0.00 |
| | Spleen Early stage | 0.10 | 0.13 | 0.03 | 0.07 | 0.10 | 0.04 | -0.04 | 0.04 | -0.05 | -0.06 | 0.11 | 0.01 | 0.10 | -0.02 | 0.09 | 0.03 | 0.09 | 0.02 |
| | Spleen Middle stage | 0.09 | 0.26 | -0.07 | 0.07 | 0.16 | 0.04 | -0.09 | -0.02 | -0.03 | -0.17 | 0.10 | -0.02 | 0.08 | -0.13 | 0.03 | -0.02 | 0.15 | 0.04 |
| | Spleen Late stage | 0.01 | -0.08 | 0.05 | 0.04 | -0.01 | 0.02 | 0.07 | -0.01 | -0.03 | 0.10 | -0.01 | -0.01 | 0.03 | 0.13 | 0.04 | 0.05 | -0.04 | 0.02 |
| | Testis Early stage | -0.06 | -0.13 | 0.05 | -0.02 | -0.09 | -0.02 | 0.10 | 0.00 | 0.03 | 0.13 | -0.06 | -0.01 | -0.04 | 0.14 | 0.01 | 0.03 | -0.10 | -0.03 |
| | Testis Middle stage | 0.02 | 0.14 | -0.05 | 0.05 | 0.12 | 0.02 | -0.08 | -0.10 | -0.03 | -0.12 | 0.03 | 0.02 | 0.03 | -0.09 | 0.00 | -0.01 | 0.09 | 0.02 |
| | Testis Late stage | -0.03 | -0.07 | -0.01 | 0.00 | -0.04 | -0.03 | 0.06 | -0.06 | 0.04 | 0.06 | -0.06 | 0.02 | -0.04 | 0.09 | -0.03 | 0.03 | -0.06 | 0.01 |
| | Adipose Early stage | 0.02 | -0.04 | -0.01 | 0.04 | 0.03 | 0.05 | 0.07 | 0.00 | 0.02 | 0.10 | 0.00 | 0.03 | -0.04 | 0.15 | 0.09 | 0.08 | 0.02 | 0.04 |
| | Adipose Middle stage | 0.14 | 0.32 | -0.09 | 0.05 | 0.24 | 0.05 | -0.17 | -0.03 | -0.04 | -0.23 | 0.15 | 0.00 | 0.08 | -0.21 | 0.02 | -0.02 | 0.21 | 0.02 |
| | Adipose Late stage | 0.09 | 0.11 | -0.04 | 0.08 | 0.13 | 0.07 | 0.00 | -0.01 | 0.01 | -0.03 | 0.06 | 0.02 | 0.11 | 0.03 | 0.06 | 0.04 | 0.08 | 0.04 | p-values of 1.00; and 0.5 or more, less than 1.0 are shown in the tables above

TABLE 4-8

|  |  |  | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of early onset dementia | Brain | Early stage | 0.05 | −0.04 | −0.09 | 0.11 | −0.04 | 0.13 | 0.01 | −0.01 |
| | Brain | Middle stage | 0.01 | 0.01 | 0.03 | 0.01 | −0.01 | 0.00 | 0.01 | 0.00 |
| | Brain | Late stage | 0.05 | −0.04 | −0.04 | 0.08 | −0.02 | 0.12 | 0.00 | 0.03 |
| | Heart | Early stage | 0.09 | 0.10 | 0.12 | 0.06 | 0.02 | 0.01 | 0.03 | 0.05 |
| | Heart | Middle stage | 0.06 | 0.19 | 0.19 | 0.00 | 0.07 | −0.10 | 0.04 | 0.01 |
| | Heart | Late stage | −0.01 | 0.08 | 0.17 | −0.06 | 0.08 | −0.12 | 0.00 | 0.05 |
| | Kidney | Early stage | 0.04 | 0.12 | 0.12 | 0.04 | 0.08 | −0.06 | 0.00 | 0.07 |
| | Kidney | Middle stage | −0.03 | 0.07 | 0.13 | −0.01 | 0.08 | −0.07 | 0.00 | 0.03 |
| | Kidney | Late stage | 0.01 | 0.11 | 0.12 | 0.05 | 0.06 | −0.03 | 0.01 | 0.09 |
| | Liver | Early stage | 0.03 | 0.01 | 0.03 | 0.01 | 0.00 | −0.01 | −0.01 | 0.00 |
| | Liver | Middle stage | 0.08 | 0.04 | −0.03 | 0.06 | −0.05 | 0.08 | 0.00 | 0.01 |
| | Liver | Late stage | 0.03 | 0.06 | 0.10 | 0.00 | 0.03 | −0.03 | −0.02 | 0.03 |
| | Lung | Early stage | 0.11 | 0.01 | −0.08 | 0.09 | −0.07 | 0.13 | 0.04 | −0.02 |
| | Lung | Middle stage | 0.10 | −0.05 | −0.13 | 0.09 | −0.08 | 0.17 | 0.02 | −0.03 |
| | Lung | Late stage | 0.07 | 0.11 | 0.09 | 0.08 | 0.04 | 0.01 | 0.06 | 0.01 |
| | Pancreas | Early stage | 0.02 | 0.05 | 0.07 | 0.02 | 0.01 | −0.06 | 0.01 | 0.02 |
| | Pancreas | Middle stage | 0.01 | 0.04 | 0.04 | 0.00 | 0.00 | −0.06 | −0.01 | 0.02 |
| | Pancreas | Late stage | 0.03 | 0.11 | 0.10 | 0.01 | 0.05 | −0.04 | 0.02 | 0.04 |
| | Muscle | Early stage | 0.13 | −0.01 | 0.01 | 0.11 | 0.00 | 0.13 | 0.01 | −0.02 |
| | Muscle | Middle stage | 0.00 | 0.10 | 0.21 | 0.00 | 0.12 | −0.08 | 0.04 | 0.02 |
| | Muscle | Late stage | 0.05 | 0.05 | 0.17 | 0.01 | 0.12 | −0.04 | 0.02 | 0.06 |
| | Skin | Early stage | 0.07 | 0.01 | −0.03 | 0.24 | 0.03 | 0.26 | 0.01 | 0.11 |
| | Skin | Middle stage | 0.08 | −0.09 | −0.17 | 0.12 | −0.07 | 0.21 | −0.01 | −0.01 |
| | Skin | Late stage | 0.03 | 0.08 | 0.09 | 0.11 | 0.16 | 0.20 | 0.03 | 0.13 |
| | Spleen | Early stage | 0.10 | 0.04 | 0.03 | 0.10 | 0.06 | 0.11 | −0.04 | 0.09 |
| | Spleen | Middle stage | 0.07 | −0.06 | −0.08 | 0.12 | −0.03 | 0.18 | 0.00 | 0.10 |
| | Spleen | Late stage | 0.07 | 0.12 | 0.14 | 0.06 | 0.08 | 0.04 | −0.02 | 0.16 |
| | Testis | Early stage | −0.01 | 0.09 | 0.10 | −0.04 | 0.03 | −0.10 | 0.03 | −0.02 |
| | Testis | Middle stage | 0.07 | −0.01 | −0.06 | 0.08 | −0.05 | 0.09 | −0.02 | 0.02 |
| | Testis | Late stage | 0.02 | 0.07 | 0.06 | −0.01 | −0.03 | −0.05 | −0.02 | −0.01 |
| | Adipose | Early stage | 0.09 | 0.15 | 0.16 | 0.08 | −0.01 | −0.02 | 0.04 | 0.01 |
| | Adipose | Middle stage | 0.11 | −0.04 | −0.10 | 0.12 | −0.09 | 0.16 | 0.03 | −0.04 |
| | Adipose | Late stage | 0.13 | 0.13 | 0.11 | 0.14 | 0.00 | 0.09 | 0.05 | 0.02 |

|  |  |  | Spleen Late stage | Testis Early stage | Testis Middle stage | Testis Late stage | Adipose Early stage | Adipose Middle stage | Adipose Late stage |
|---|---|---|---|---|---|---|---|---|---|
| Model mice of early onset dementia | Brain | Early stage | 0.04 | 0.08 | −0.06 | 0.11 | 0.03 | 0.16 | 0.13 |
| | Brain | Middle stage | −0.01 | 0.00 | 0.02 | 0.01 | 0.02 | 0.02 | 0.00 |
| | Brain | Late stage | 0.02 | 0.05 | −0.04 | 0.12 | 0.00 | 0.10 | 0.08 |
| | Heart | Early stage | 0.02 | 0.00 | −0.11 | −0.03 | −0.01 | −0.05 | −0.05 |
| | Heart | Middle stage | −0.02 | −0.10 | 0.01 | −0.10 | 0.00 | −0.18 | −0.15 |
| | Heart | Late stage | 0.02 | −0.10 | −0.04 | −0.09 | −0.05 | −0.25 | −0.20 |
| | Kidney | Early stage | 0.01 | −0.07 | −0.02 | −0.08 | −0.04 | −0.16 | −0.13 |
| | Kidney | Middle stage | 0.00 | −0.11 | 0.07 | −0.07 | −0.05 | −0.17 | −0.16 |
| | Kidney | Late stage | 0.01 | −0.03 | −0.09 | −0.08 | −0.02 | −0.12 | −0.12 |
| | Liver | Early stage | −0.02 | −0.02 | −0.01 | −0.01 | −0.03 | −0.04 | −0.03 |
| | Liver | Middle stage | 0.03 | 0.10 | −0.11 | 0.07 | 0.04 | 0.13 | 0.14 |
| | Liver | Late stage | −0.02 | −0.03 | −0.03 | −0.02 | −0.02 | −0.12 | −0.11 |
| | Lung | Early stage | 0.00 | 0.15 | −0.10 | 0.10 | 0.10 | 0.27 | 0.21 |
| | Lung | Middle stage | 0.00 | 0.16 | −0.09 | 0.14 | 0.06 | 0.32 | 0.25 |
| | Lung | Late stage | 0.02 | −0.01 | −0.04 | −0.03 | 0.04 | −0.01 | 0.01 |
| | Pancreas | Early stage | 0.02 | −0.03 | 0.00 | −0.02 | 0.01 | −0.10 | −0.07 |
| | Pancreas | Middle stage | 0.03 | −0.04 | 0.01 | −0.01 | −0.04 | −0.10 | −0.09 |
| | Pancreas | Late stage | 0.02 | −0.06 | 0.02 | −0.04 | −0.01 | −0.14 | −0.10 |
| | Muscle | Early stage | 0.00 | 0.08 | −0.03 | 0.10 | −0.02 | 0.13 | 0.10 |
| | Muscle | Middle stage | 0.01 | −0.13 | 0.09 | −0.10 | −0.06 | −0.23 | −0.16 |
| | Muscle | Late stage | 0.04 | −0.04 | −0.02 | −0.03 | −0.05 | −0.12 | −0.09 |
| | Skin | Early stage | 0.08 | 0.15 | −0.12 | 0.11 | 0.04 | 0.26 | 0.18 |
| | Skin | Middle stage | 0.02 | 0.17 | −0.07 | 0.14 | 0.03 | 0.32 | 0.24 |
| | Skin | Late stage | 0.07 | −0.03 | −0.01 | −0.04 | −0.11 | −0.06 | −0.02 |
| | Spleen | Early stage | 0.13 | 0.01 | 0.07 | 0.02 | 0.00 | 0.14 | 0.16 |
| | Spleen | Middle stage | 0.18 | 0.10 | −0.08 | 0.08 | 0.04 | 0.27 | 0.22 |
| | Spleen | Late stage | 0.15 | −0.03 | 0.01 | −0.06 | 0.03 | −0.04 | 0.02 |
| | Testis | Early stage | −0.06 | −0.09 | 0.05 | −0.11 | −0.02 | −0.19 | −0.12 |
| | Testis | Middle stage | 0.03 | 0.13 | −0.11 | 0.09 | 0.05 | 0.16 | 0.15 |
| | Testis | Late stage | −0.04 | 0.00 | −0.06 | 0.03 | 0.02 | −0.09 | −0.06 |
| | Adipose | Early stage | 0.00 | 0.01 | −0.03 | 0.00 | 0.16 | 0.04 | 0.01 |
| | Adipose | Middle stage | −0.02 | 0.18 | −0.04 | 0.13 | 0.12 | 0.37 | 0.29 |
| | Adipose | Late stage | 0.01 | 0.03 | −0.03 | 0.06 | 0.17 | 0.25 | 0.25 |

ρ-values of 1.00; and 0.5 or more, less than 1.0 are shown in the tables above

Tables 4-1 to 4-8 show that, in the same organ, when diseases are different, the ρ-value is less than 0.55. In the case of the same organ and the same disease, when the stages are different, the ρ-value is less than 0.75. In other words, it was believed that when the ρ-value obtained between standard data 1 and the data of a subject is 0.55 or more, it can be determined that the data of the subject indicates the same disease as the disease corresponding to the standard data 1; when the ρ-value obtained between standard data 1 and the data of a subject is 0.75 or more, it can be determined that the data of the subject indicates the same stage as the stage corresponding to the standard data 1.

2. Application of Z-Score Method

The amount of expression of each gene in data of a subject was divided by the amount of expression of the corresponding gene in standard data, and the obtained value was scaled by log 2. The scaled value was represented by $x_i$ (i=1, . . . , the number of genes). Regarding the value $x_i$, the mean p and variance a of all of the analyzed genes were determined.

Here, Z-score $z_i$ for a gene i is represented by the following equation.

$$z_i = \frac{x_i - \mu}{\sigma} \qquad \text{Equation 3}$$

This is a quantification value indicating how far the scaled value $x_i$ of the gene i is from the mean of all of the analyzed genes. Here, this value indicates how much the gene i exhibits specific changes in expression compared to all of the analyzed genes. The closer this value is to 0, the less the gene exhibits specific changes in expression. The farther this value is from 0, the more the gene exhibits specific changes in expression. How much a gene exhibits specific changes in expression can be quantified by taking the median (Z') of the scaled value $z_i$.

For the analysis, a script for calculating Equation 1 was described using R. Tables 5-1 to 5-8 show the results.

TABLE 5-1

| | | | Model mice of chronic kidney disease | | | | | | | | | | | | | | | | |
|---|---|---|---|---|---|---|---|---|---|---|---|---|---|---|---|---|---|---|---|
| | | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
| Model mice of chronic kidney disease | Brain | Early stage | 0.00 | -0.92 | -0.17 | -0.64 | 1.10 | -0.13 | 0.74 | 1.32 | 6.51 | -0.85 | -1.36 | -1.83 | -2.98 | -5.19 | -0.93 | 3.35 | 10.44 | 1.80 |
| | Brain | Middle stage | 0.92 | 0.00 | 0.67 | 0.16 | 1.89 | 0.59 | 1.33 | 1.83 | 6.77 | -0.30 | -0.86 | -1.33 | -2.07 | -4.06 | -0.11 | 3.99 | 10.98 | 2.46 |
| | Brain | Late stage | 0.17 | -0.67 | 0.00 | -0.49 | 1.14 | 0.01 | 0.85 | 1.38 | 6.68 | -0.77 | -1.26 | -1.73 | -2.62 | -5.42 | 0.77 | 3.32 | 9.86 | 1.75 |
| | Heart | Early stage | 0.64 | -0.16 | 0.49 | 0.00 | 1.62 | 0.50 | 1.15 | 1.64 | 6.80 | -0.41 | -0.94 | -1.41 | -1.99 | -4.49 | -0.27 | 3.50 | 9.52 | 2.08 |
| | Heart | Middle stage | -1.10 | -1.89 | -1.14 | -1.62 | 0.00 | -1.19 | -0.07 | 0.52 | 5.58 | -1.47 | -1.96 | -2.35 | -3.81 | -5.46 | -1.80 | 2.09 | 8.55 | 0.59 |
| | Heart | Late stage | 0.13 | -0.59 | -0.01 | -0.50 | 1.19 | 0.00 | 0.79 | 1.33 | 6.55 | -0.72 | -1.21 | -1.70 | -2.43 | -4.74 | 0.71 | 3.04 | 9.06 | 1.70 |
| | Kidney | Early stage | -0.74 | -1.33 | -0.85 | -1.15 | 0.07 | -0.79 | 0.00 | 0.77 | 7.46 | -1.41 | -1.70 | -2.20 | 2.89 | -4.80 | -1.36 | 1.88 | 6.56 | 0.54 |
| | Kidney | Middle stage | -1.32 | -1.83 | -1.38 | -1.64 | -0.52 | -1.33 | -0.77 | 0.00 | 7.90 | -1.75 | -2.19 | -2.56 | -3.16 | -4.74 | -1.86 | 1.09 | 5.59 | 0.09 |
| | Kidney | Late stage | -6.51 | -6.77 | -6.68 | -6.80 | -5.58 | -6.55 | -7.46 | -7.90 | 0.00 | -6.34 | -6.44 | -6.84 | -7.70 | -9.12 | -6.71 | -4.31 | -0.87 | -5.33 |
| | Liver | Early stage | 0.85 | 0.30 | 0.77 | 0.41 | 1.47 | 0.72 | 1.41 | 1.75 | 6.34 | 0.00 | -0.68 | -1.30 | -1.06 | -3.10 | 0.23 | 3.15 | 7.28 | 1.97 |
| | Liver | Middle stage | 1.36 | 0.86 | 1.26 | 0.94 | 1.96 | 1.21 | 1.70 | 2.19 | 6.44 | 0.68 | 0.00 | -0.75 | -0.39 | -2.09 | 0.76 | 3.25 | 7.31 | 2.26 |
| | Liver | Late stage | 1.83 | 1.33 | 1.73 | 1.41 | 2.35 | 1.70 | 2.20 | 2.56 | 6.84 | 1.30 | 0.75 | 0.00 | 0.11 | -1.60 | 1.26 | 3.77 | 7.55 | 2.81 |
| | Lung | Early stage | 2.98 | 2.07 | 2.62 | 1.99 | 3.81 | 2.43 | 2.89 | 3.16 | 7.70 | 1.06 | 0.39 | -0.11 | 0.00 | -2.78 | 2.14 | 5.79 | 12.19 | 4.18 |
| | Lung | Middle stage | 5.19 | 4.06 | 5.42 | 4.49 | 5.46 | 4.74 | 4.80 | 4.74 | 9.12 | 3.10 | 2.09 | 1.60 | 2.78 | 0.00 | 4.78 | 7.46 | 12.80 | 6.19 |
| | Lung | Late stage | 0.93 | 0.11 | 0.77 | 0.27 | 1.80 | 0.71 | 1.36 | 1.86 | 6.71 | -0.23 | -0.76 | -1.26 | -2.14 | -4.78 | 0.00 | 3.83 | 9.95 | 2.43 |
| | Pancreas | Early stage | -3.35 | -3.99 | -3.32 | -3.50 | -2.09 | -3.04 | -1.88 | -1.09 | 4.31 | -3.15 | -3.25 | -3.77 | -5.79 | -7.46 | -3.83 | 0.00 | 6.80 | -1.79 |
| | Pancreas | Middle stage | -10.44 | -10.98 | -9.86 | -9.52 | -8.55 | -9.06 | -6.56 | -5.59 | 0.87 | -7.28 | -7.31 | -7.55 | -12.19 | -12.80 | -9.95 | -6.80 | 0.00 | -8.85 |
| | Pancreas | Late stage | -1.80 | -2.46 | -1.75 | -2.08 | -0.59 | -1.70 | -0.54 | 0.09 | 5.33 | -1.97 | -2.26 | -2.81 | -4.18 | -6.19 | -2.43 | 1.79 | 8.85 | 0.00 |
| | Muscle | Early stage | 3.44 | 2.55 | 3.30 | 2.80 | 4.30 | 3.06 | 3.25 | 3.50 | 7.87 | 1.54 | 0.87 | 0.35 | 0.70 | -1.80 | 2.37 | 5.90 | 11.82 | 4.44 |
| | Muscle | Middle stage | 4.19 | 3.33 | 3.88 | 3.32 | 5.11 | 3.84 | 4.04 | 4.06 | 8.11 | 2.35 | 1.49 | 1.04 | 1.70 | -0.72 | 3.20 | 6.66 | 11.90 | 5.53 |
| | Muscle | Late stage | 0.20 | -0.44 | 0.08 | -0.31 | 1.08 | 0.09 | 0.84 | 1.30 | 6.11 | -0.64 | -1.07 | -1.56 | -2.15 | -4.42 | -0.54 | 2.95 | 8.00 | 1.56 |
| | Skin | Early stage | 0.40 | -0.21 | 0.27 | -0.07 | 1.16 | 0.27 | 0.91 | 1.32 | 5.66 | -0.41 | -0.89 | -1.33 | -1.72 | -3.57 | -0.28 | 2.76 | 7.49 | 1.59 |
| | Skin | Middle stage | 0.16 | -0.47 | 0.04 | -0.31 | 0.95 | 0.05 | 0.77 | 1.28 | 5.89 | -0.63 | -1.06 | -1.54 | -2.02 | -3.88 | -0.54 | 2.71 | 7.53 | 1.49 |
| | Skin | Late stage | -4.21 | -4.63 | -4.20 | -4.41 | -3.47 | -4.13 | -3.00 | -2.43 | 2.25 | -3.90 | -4.22 | -4.51 | -5.87 | -7.19 | -4.59 | -1.82 | 2.17 | -3.00 |
| | Spleen | Early stage | -8.31 | -8.56 | -7.98 | -7.96 | -6.93 | -7.39 | -5.71 | -4.56 | 1.31 | -6.53 | -6.37 | -6.66 | -10.39 | -11.40 | -8.31 | -4.53 | 0.76 | -6.20 |
| | Spleen | Middle stage | 2.54 | 1.69 | 2.34 | 1.81 | 3.25 | 2.18 | 2.62 | 2.91 | 7.75 | 0.94 | 0.29 | -0.19 | -0.13 | -2.56 | 1.55 | 4.98 | 10.90 | 3.85 |
| | Spleen | Late stage | -5.32 | -5.74 | -5.27 | -5.47 | -4.13 | -5.05 | -3.68 | -2.86 | 2.61 | -4.56 | -4.63 | -5.16 | -7.25 | -8.89 | -5.93 | -2.32 | 2.63 | -3.84 |
| | Testis | Early stage | -2.52 | -3.27 | -2.54 | -2.81 | -1.21 | -2.27 | -1.06 | -0.36 | 5.08 | -2.43 | -2.71 | -3.17 | -4.83 | -6.92 | -3.01 | 1.01 | 7.44 | -0.67 |
| | Testis | Middle stage | -0.95 | -1.60 | -1.06 | -1.34 | 0.07 | -0.92 | -0.02 | 0.57 | 5.56 | -1.44 | -1.87 | -2.26 | -1.65 | -5.29 | -1.65 | 2.01 | 7.81 | 0.62 |
| | Testis | Late stage | -0.55 | -1.34 | -0.67 | -1.04 | 0.52 | -0.60 | 0.33 | 0.91 | 6.20 | -1.17 | -1.62 | -2.11 | -3.20 | -5.20 | -1.32 | 2.69 | 9.29 | 1.16 |
| | Adipose | Early stage | -13.87 | -14.04 | -13.85 | -13.95 | -13.18 | -13.69 | -12.58 | -11.59 | -7.26 | -13.00 | -12.83 | -13.26 | -14.77 | -16.00 | -13.98 | -12.07 | -9.40 | -13.06 |
| | Adipose | Middle stage | -1.87 | -2.47 | -1.87 | -2.24 | -1.13 | -1.80 | -0.97 | -0.47 | 3.96 | -2.00 | -2.49 | -2.82 | -3.67 | -4.93 | -2.40 | 0.48 | 4.97 | -0.66 |
| | Adipose | Late stage | -2.50 | -3.06 | -2.55 | -2.96 | -1.80 | -2.47 | -1.51 | 0.96 | 3.51 | -2.52 | -2.98 | -3.24 | -4.35 | -5.80 | -3.00 | -0.13 | 4.22 | -1.25 |

TABLE 5-2

| | | | Model mice of chronic kidney disease | | | | | | | |
|---|---|---|---|---|---|---|---|---|---|---|
| | | | Muscle Early stage | Muscle Middle stage | Muscle Late stage | Skin Early stage | Skin Middle stage | Skin Late stage | Spleen Early stage | Spleen Middle stage |
| Model mice of chronic kidney disease | Brain | Early stage | −3.44 | −4.19 | −0.20 | −0.40 | −0.16 | 4.21 | 8.31 | −2.54 |
| | Brain | Middle stage | −2.55 | −3.33 | 0.44 | 0.21 | 0.47 | 4.63 | 8.56 | −1.69 |
| | Brain | Late stage | −3.30 | −3.88 | −0.08 | −0.27 | −0.04 | 4.20 | 7.98 | −2.34 |
| | Heart | Early stage | −2.80 | −3.32 | 0.31 | 0.07 | 0.31 | 4.41 | 7.96 | −1.81 |
| | Heart | Middle stage | −4.30 | −5.11 | −1.08 | −1.16 | −0.95 | 3.47 | 6.93 | −3.25 |
| | Heart | Late stage | −3.06 | −3.84 | −0.09 | −0.27 | −0.05 | 4.13 | 7.39 | −2.18 |
| | Kidney | Early stage | −3.25 | −4.04 | −0.84 | −0.91 | −0.77 | 3.00 | 5.71 | −2.62 |
| | Kidney | Middle stage | −3.50 | −4.06 | −1.30 | −1.32 | −1.28 | 2.43 | 4.56 | −2.91 |
| | Kidney | Late stage | −7.87 | −8.11 | −6.11 | −5.66 | −5.89 | −2.25 | −1.31 | −7.75 |
| | Liver | Early stage | −1.54 | −2.35 | 0.64 | 0.41 | 0.63 | 3.90 | 6.53 | −0.94 |
| | Liver | Middle stage | −0.87 | −1.49 | 1.07 | 0.89 | 1.06 | 4.22 | 6.37 | −0.29 |
| | Liver | Late stage | −0.35 | −1.04 | 1.56 | 1.33 | 1.54 | 4.51 | 6.66 | 0.19 |
| | Lung | Early stage | −0.70 | −1.70 | 2.15 | 1.72 | 2.02 | 5.87 | 10.39 | 0.13 |
| | Lung | Middle stage | 1.80 | 0.72 | 4.42 | 3.57 | 3.88 | 7.19 | 11.40 | 2.56 |
| | Lung | Late stage | −2.37 | −3.20 | 0.54 | 0.28 | 0.54 | 4.59 | 8.31 | −1.55 |
| | Pancreas | Early stage | −5.90 | −6.66 | −2.95 | −2.76 | −2.71 | 1.82 | 4.53 | −4.98 |
| | Pancreas | Middle stage | −11.82 | −11.90 | −8.00 | −7.49 | −7.53 | −2.17 | −0.76 | −10.90 |
| | Pancreas | Late stage | −4.44 | −5.53 | −1.56 | −1.59 | −1.49 | 3.00 | 6.20 | −3.85 |
| | Muscle | Early stage | 0.00 | −1.16 | 3.34 | 2.32 | 2.46 | 6.27 | 10.05 | 0.75 |
| | Muscle | Middle stage | 1.16 | 0.00 | 4.56 | 3.11 | 3.32 | 6.91 | 10.46 | 1.70 |
| | Muscle | Late stage | −3.34 | −4.56 | 0.00 | −0.19 | 0.03 | 4.02 | 6.96 | −1.88 |
| | Skin | Early stage | −2.32 | −3.11 | 0.19 | 0.00 | 0.22 | 5.31 | 6.41 | −1.59 |
| | Skin | Middle stage | −2.46 | −3.32 | −0.03 | −0.22 | 0.00 | 4.06 | 6.43 | −1.92 |
| | Skin | Late stage | −6.27 | −6.91 | −4.02 | −5.31 | −4.06 | 0.00 | 1.49 | −5.77 |
| | Spleen | Early stage | −10.05 | −10.46 | −6.96 | −6.41 | −6.43 | −1.49 | 0.00 | −8.73 |
| | Spleen | Middle stage | −0.75 | −1.70 | 1.88 | 1.59 | 1.92 | 5.77 | 8.73 | 0.00 |
| | Spleen | Late stage | −7.06 | −7.66 | −4.56 | −4.60 | −4.59 | −0.03 | 1.61 | −8.77 |
| | Testis | Early stage | −5.33 | −5.90 | −2.13 | −2.13 | −2.00 | 2.58 | 5.85 | −4.46 |
| | Testis | Middle stage | −3.77 | −4.42 | −0.92 | −1.01 | −0.86 | 3.27 | 6.39 | −2.93 |
| | Testis | Late stage | −3.58 | −4.40 | −0.61 | −0.75 | −0.56 | 3.76 | 7.32 | −2.86 |
| | Adipose | Early stage | −15.22 | −15.55 | −13.58 | −13.22 | −12.70 | −9.54 | −9.50 | −14.42 |
| | Adipose | Middle stage | −4.20 | −4.51 | −1.78 | −1.97 | −1.71 | 2.07 | 3.91 | −3.36 |
| | Adipose | Late stage | −5.05 | −6.27 | −2.47 | −2.54 | −2.23 | 1.59 | 3.39 | −3.97 |

| | | | Model mice of chronic kidney disease | | | | | | |
|---|---|---|---|---|---|---|---|---|---|
| | | | Spleen Late stage | Testis Early stage | Tests Middle stage | Testis Late stage | Adipose Early stage | Adipose Middle stage | Adipose Late stage |
| Model mice of chronic kidney disease | Brain | Early stage | 5.32 | 2.52 | 0.95 | 0.55 | 13.87 | 1.87 | 2.52 |
| | Brain | Middle stage | 5.74 | 3.27 | 1.60 | 1.34 | 14.04 | 2.47 | 3.06 |
| | Brain | Late stage | 5.27 | 2.54 | 1.06 | 0.67 | 13.85 | 1.87 | 2.55 |
| | Heart | Early stage | 5.47 | 2.81 | 1.34 | 1.04 | 13.95 | 2.24 | 2.96 |
| | Heart | Middle stage | 4.13 | 1.21 | −0.07 | −0.52 | 13.18 | 1.13 | 1.80 |
| | Heart | Late stage | 5.05 | 2.27 | 0.92 | 0.60 | 13.69 | 1.80 | 2.47 |
| | Kidney | Early stage | 3.68 | 1.06 | 0.02 | −0.33 | 12.58 | 0.97 | 1.51 |
| | Kidney | Middle stage | 2.86 | 0.36 | −0.57 | −0.91 | 11.59 | 0.47 | 0.96 |
| | Kidney | Late stage | −2.61 | −5.08 | −5.56 | −6.20 | 7.26 | −3.96 | −3.51 |
| | Liver | Early stage | 4.56 | 2.43 | 1.44 | 1.17 | 13.00 | 2.00 | 2.52 |
| | Liver | Middle stage | 4.63 | 2.71 | 1.87 | 1.62 | 12.83 | 2.49 | 2.98 |
| | Liver | Late stage | 5.16 | 3.17 | 2.26 | 2.11 | 13.26 | 2.82 | 3.24 |
| | Lung | Early stage | 7.25 | 4.83 | 3.25 | 3.20 | 14.77 | 3.67 | 4.35 |
| | Lung | Middle stage | 8.89 | 6.92 | 5.29 | 5.20 | 16.00 | 4.93 | 5.80 |
| | Lung | Late stage | 5.93 | 3.01 | 1.65 | 1.32 | 13.98 | 2.40 | 3.00 |
| | Pancreas | Early stage | 2.32 | −1.01 | −2.01 | −2.69 | 12.07 | −0.48 | 0.13 |
| | Pancreas | Middle stage | −2.63 | −7.44 | −7.81 | −9.29 | 9.40 | −4.97 | −4.22 |
| | Pancreas | Late stage | 3.84 | 0.67 | −0.62 | −1.16 | 13.06 | 0.66 | 1.25 |
| | Muscle | Early stage | 7.06 | 5.33 | 3.77 | 3.58 | 15.22 | 4.20 | 5.05 |
| | Muscle | Middle stage | 7.66 | 5.90 | 4.42 | 4.40 | 15.55 | 4.51 | 5.27 |
| | Muscle | Late stage | 4.56 | 2.13 | 0.92 | 0.61 | 13.58 | 1.78 | 2.47 |
| | Skin | Early stage | 4.60 | 2.13 | 1.01 | 0.75 | 13.22 | 1.97 | 2.54 |
| | Skin | Middle stage | 4.59 | 2.00 | 0.86 | 0.56 | 12.70 | 1.71 | 2.23 |
| | Skin | Late stage | 0.03 | −2.58 | −3.27 | −3.76 | 9.54 | −2.07 | −1.59 |
| | Spleen | Early stage | −1.61 | −5.85 | −6.39 | −7.32 | 9.50 | −3.91 | −3.39 |
| | Spleen | Middle stage | 8.77 | 4.46 | 2.93 | 2.86 | 14.42 | 3.36 | 3.97 |
| | Spleen | Late stage | 0.00 | −3.23 | −3.96 | −4.71 | 10.20 | −2.23 | −1.67 |
| | Testis | Early stage | 3.23 | 0.00 | −1.25 | −2.00 | 12.78 | 0.23 | 0.85 |
| | Testis | Middle stage | 3.96 | 1.25 | 0.00 | −0.44 | 13.01 | 1.06 | 1.65 |
| | Testis | Late stage | 4.71 | 2.00 | 0.44 | 0.00 | 13.36 | 1.45 | 2.03 |
| | Adipose | Early stage | −10.20 | −12.78 | −13.01 | −13.36 | 0.00 | −12.68 | −11.87 |
| | Adipose | Middle stage | 2.23 | −0.23 | −1.06 | −1.45 | 12.68 | 0.00 | 0.74 |
| | Adipose | Late stage | 1.67 | −0.85 | −1.65 | −2.03 | 11.87 | −0.74 | 0.00 |

TABLE 5-3

| | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|---|---|---|---|---|---|---|---|
| Model mice of myocardial infarction | Brain Early stage | −2.34 | −2.91 | −2.41 | −2.60 | −1.04 | −2.14 | −0.95 | −0.27 | 5.19 | −2.36 | −2.60 | −3.06 | −4.68 | −6.93 | −2.90 | 1.13 | 7.24 | −0.49 |
| | Brain Middle stage | −7.91 | −8.12 | −7.68 | −7.48 | −6.08 | −7.07 | −5.25 | −4.23 | 1.95 | −6.08 | −5.94 | −6.36 | −9.39 | −10.98 | −7.65 | −3.97 | 1.71 | −5.79 |
| | Brain Late stage | −0.83 | −1.58 | −0.93 | −1.31 | 0.28 | −0.82 | 0.15 | 0.74 | 5.96 | −1.39 | −1.78 | −2.24 | −3.51 | −5.69 | −1.60 | 2.54 | 9.07 | 0.94 |
| | Heart Early stage | −8.21 | −8.57 | −8.14 | −8.31 | −7.04 | −8.12 | −6.66 | −5.87 | −0.22 | −7.34 | −7.20 | −7.64 | −9.95 | −11.09 | −8.67 | −5.62 | −1.34 | −6.85 |
| | Heart Middle stage | −8.85 | −9.12 | −8.76 | −8.80 | −7.54 | −8.52 | −7.44 | −6.98 | −1.44 | −7.96 | −7.76 | −8.26 | −9.87 | −11.14 | −8.72 | −6.43 | −2.58 | −7.57 |
| | Heart Late stage | −9.80 | −10.27 | −9.91 | −10.00 | −8.45 | −9.66 | −8.33 | −7.61 | −1.99 | −8.76 | −8.45 | −9.00 | −11.04 | −12.09 | −9.84 | −7.32 | −3.30 | −8.64 |
| | Kidney Early stage | −3.39 | −3.95 | −3.44 | −3.54 | −2.15 | −3.05 | −1.98 | −1.18 | 4.28 | −3.18 | −3.32 | −3.76 | −5.66 | −7.83 | −3.87 | −0.11 | 5.56 | −1.67 |
| | Kidney Middle stage | −0.59 | −1.24 | −0.70 | −1.01 | 0.33 | −0.63 | 0.22 | 0.81 | 6.43 | −1.23 | −1.62 | −2.11 | −2.88 | −4.99 | −1.26 | 2.28 | 7.81 | 0.87 |
| | Kidney Late stage | 0.63 | −0.14 | 0.47 | 0.02 | 1.47 | 0.45 | 1.11 | 1.59 | 6.40 | −0.39 | −0.90 | −1.36 | −1.94 | −4.08 | −0.23 | 3.52 | 9.55 | 2.12 |
| | Liver Early stage | −0.81 | −1.47 | −0.90 | −1.23 | 0.13 | −0.82 | 0.04 | 0.59 | 5.58 | −1.52 | −1.91 | −2.37 | −3.08 | −5.15 | −1.46 | 2.04 | 7.32 | 0.66 |
| | Liver Middle stage | −12.34 | −12.39 | −12.17 | −11.99 | −10.77 | −11.83 | −10.14 | −9.44 | −3.17 | −10.96 | −10.42 | −10.97 | −13.16 | −14.16 | −12.04 | −9.27 | −5.12 | −10.74 |
| | Liver Late stage | 2.24 | 1.47 | 2.07 | 1.52 | 2.90 | 1.94 | 2.35 | 2.71 | 7.31 | 0.73 | 0.15 | −0.31 | −0.33 | −2.55 | 1.28 | 4.89 | 10.69 | 3.57 |
| | Lung Early stage | 1.50 | 0.76 | 1.30 | 0.86 | 2.21 | 1.25 | 1.82 | 2.24 | 6.97 | 0.28 | −0.28 | −0.75 | −1.03 | −3.28 | 0.69 | 4.16 | 9.70 | 2.79 |
| | Lung Middle stage | −16.95 | −17.11 | −16.31 | −16.20 | −15.33 | −15.78 | −14.03 | −13.40 | −7.49 | −14.22 | −14.07 | −14.13 | −16.94 | −17.03 | −16.10 | −13.92 | −10.56 | −15.20 |
| | Lung Late stage | −0.04 | −0.73 | −0.17 | −0.56 | 0.85 | −0.15 | 0.66 | 1.20 | 6.29 | −0.85 | −1.29 | −1.75 | −2.52 | −4.64 | −0.82 | 2.91 | 8.66 | 1.45 |
| | Pancreas Early stage | −4.08 | −4.62 | −3.96 | −4.11 | −2.51 | −3.46 | −2.00 | −1.18 | 4.44 | −3.32 | −3.50 | −3.93 | −6.50 | −8.30 | −4.35 | −0.08 | 6.81 | −1.97 |
| | Pancreas Middle stage | −3.93 | −4.31 | −3.84 | −3.90 | −2.40 | −3.38 | −2.04 | −1.25 | 4.20 | −3.34 | −3.50 | −3.93 | −6.13 | −7.92 | −4.25 | −0.22 | 5.95 | −1.92 |
| | Pancreas Late stage | −5.66 | −6.12 | −5.72 | −5.55 | −3.93 | −4.98 | −3.32 | −2.34 | 3.48 | −4.46 | −4.45 | −4.90 | −7.90 | −9.83 | −5.90 | −1.68 | 4.68 | −3.53 |
| | Muscle Early stage | −3.93 | −4.29 | −3.95 | −4.11 | −2.84 | −3.75 | −2.47 | −1.69 | 3.62 | −3.72 | −3.95 | −4.38 | −6.07 | −8.10 | −4.42 | −0.86 | 4.39 | −2.31 |
| | Muscle Middle stage | −2.13 | −2.72 | −2.18 | −2.43 | −1.02 | −1.98 | −0.96 | −0.31 | 4.82 | −2.27 | −2.50 | −2.92 | −4.34 | −6.18 | −2.61 | 0.95 | 6.48 | −0.53 |
| | Muscle Late stage | −1.67 | −2.34 | −1.74 | −2.01 | −0.59 | −1.56 | −0.58 | 0.04 | 5.24 | −1.96 | −2.27 | −2.69 | −4.05 | −5.88 | −2.23 | 1.44 | 7.25 | −0.06 |
| | Skin Early stage | 1.53 | 0.68 | 1.42 | 0.87 | 2.32 | 1.24 | 1.83 | 2.24 | 7.18 | 0.20 | −0.38 | −0.86 | −1.17 | −3.82 | 0.58 | 4.35 | 10.18 | 2.83 |
| | Skin Middle stage | −0.54 | −1.32 | −0.64 | −1.03 | 0.51 | −0.55 | 0.32 | 0.91 | 6.03 | −1.20 | −1.69 | −2.11 | −3.12 | −5.13 | −1.30 | 2.62 | 9.01 | 1.14 |
| | Skin Late stage | −0.90 | −1.58 | −0.93 | −1.30 | 0.25 | −0.86 | 0.13 | 0.73 | 5.86 | −1.40 | −1.76 | −2.27 | −3.45 | −5.62 | −1.69 | 2.53 | 8.98 | 0.96 |
| | Spleen Early stage | −1.59 | −2.10 | −1.68 | −1.92 | −0.55 | −1.52 | −0.56 | 0.05 | 5.15 | −1.91 | −2.19 | −2.66 | −3.78 | −5.91 | −2.12 | 1.38 | 6.70 | −0.04 |
| | Spleen Middle stage | −1.04 | −1.60 | −1.11 | −1.40 | −0.19 | −1.02 | −0.22 | 0.30 | 5.02 | −1.51 | −1.89 | −2.28 | −3.09 | −4.89 | −1.65 | 1.54 | 6.43 | 0.28 |
| | Spleen Late stage | −6.76 | −7.11 | −6.65 | −6.79 | −5.90 | −6.43 | −5.41 | −4.72 | −0.06 | −6.28 | −6.32 | −6.52 | −8.22 | −9.30 | −7.01 | 4.48 | −0.97 | −5.56 |
| | Testis Early stage | 4.23 | 3.30 | 3.95 | 3.16 | 4.68 | 3.50 | 3.79 | 4.05 | 8.50 | 2.00 | 1.22 | 0.71 | 1.26 | −1.29 | 3.00 | 6.76 | 12.89 | 5.45 |
| | Testis Middle stage | 1.85 | 1.04 | 1.67 | 1.12 | 2.58 | 1.51 | 2.10 | 2.48 | 7.22 | 0.43 | −0.16 | −0.65 | −0.84 | −3.17 | 0.88 | 4.66 | 10.63 | 3.32 |
| | Testis Late stage | 0.62 | −0.18 | 0.45 | −0.01 | 1.52 | 0.42 | 1.16 | 1.65 | 6.57 | −0.42 | −0.92 | −1.41 | −2.07 | −4.23 | −0.27 | 3.61 | 9.93 | 2.18 |
| | Adipose Early stage | 1.10 | 0.43 | 0.97 | 0.55 | 1.83 | 0.93 | 1.54 | 1.98 | 6.68 | 0.06 | −0.46 | −0.92 | −1.17 | −3.27 | 0.35 | 3.59 | 8.67 | 2.33 |
| | Adipose Middle stage | −11.96 | −12.18 | −11.88 | −11.87 | −11.23 | −11.66 | −10.57 | −9.95 | −5.43 | −11.05 | −10.90 | −11.20 | −12.94 | −13.87 | −11.99 | −10.09 | −7.26 | −10.98 |
| | Adipose Late stage | 8.40 | 7.37 | 7.97 | 7.16 | 8.44 | 7.25 | 7.06 | 6.88 | 10.31 | 5.15 | 4.19 | 3.62 | 5.69 | 2.93 | 7.08 | 10.32 | 15.89 | 9.28 |

TABLE 5-4

| | | | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of myocardial infarction | Brain | Early stage | −5.08 | −5.85 | −2.01 | −1.96 | −1.86 | 2.67 | 5.71 | −4.31 |
| | Brain | Middle stage | −9.44 | −9.86 | −6.35 | −5.84 | −6.13 | −0.94 | 0.79 | −8.82 |
| | Brain | Late stage | −3.90 | −4.72 | −0.82 | −0.94 | −0.76 | 3.60 | 7.20 | −3.11 |
| | Heart | Early stage | −9.68 | −10.08 | −7.58 | −6.72 | −7.08 | −2.65 | −1.82 | −9.16 |
| | Heart | Middle stage | −9.83 | −10.16 | −8.03 | −6.98 | −8.03 | −3.39 | −2.92 | −9.74 |
| | Heart | Late stage | −10.77 | −10.92 | −8.84 | −8.08 | −9.05 | −4.07 | −3.71 | −10.87 |
| | Kidney | Early stage | −5.94 | −6.66 | −2.97 | −2.85 | −2.78 | 1.76 | 4.42 | −5.21 |
| | Kidney | Middle stage | −3.30 | −4.21 | −0.66 | −0.77 | −0.60 | 3.38 | 6.39 | −2.63 |
| | Kidney | Late stage | −2.43 | −3.27 | 0.31 | 0.09 | 0.32 | 4.23 | 7.72 | −1.69 |
| | Liver | Early stage | −3.56 | −4.39 | −0.85 | −0.95 | −0.78 | 3.22 | 6.14 | −2.81 |
| | Liver | Middle stage | −13.33 | −13.51 | −10.96 | −9.84 | −10.68 | −5.58 | −5.30 | −12.66 |
| | Liver | Late stage | −0.94 | −1.83 | 1.64 | 1.29 | 1.55 | 5.15 | 8.71 | −0.19 |
| | Lung | Early stage | −1.49 | −2.34 | 1.06 | 0.75 | 1.01 | 4.60 | 8.11 | −0.74 |
| | Lung | Middle stage | −17.49 | −17.37 | −14.92 | −13.22 | −14.17 | −9.53 | −10.62 | −15.45 |
| | Lung | Late stage | −2.93 | −3.77 | −0.21 | −0.37 | −0.17 | 3.77 | 7.05 | −2.17 |
| | Pancreas | Early stage | −6.61 | −7.24 | −3.18 | −3.05 | −2.94 | 1.90 | 4.92 | −5.85 |
| | Pancreas | Middle stage | −6.41 | −7.07 | −3.15 | −3.00 | −2.93 | 1.72 | 4.39 | −5.60 |
| | Pancreas | Late stage | −7.94 | −8.57 | −4.58 | 4.26 | −4.23 | 0.80 | 3.28 | −7.05 |
| | Muscle | Early stage | −6.94 | −7.55 | −3.83 | −3.40 | −3.34 | 1.14 | 3.40 | −5.50 |
| | Muscle | Middle stage | −5.04 | −5.65 | −1.99 | −1.93 | −1.83 | 2.46 | 5.32 | −4.13 |
| | Muscle | Late stage | −4.26 | −4.85 | −1.47 | −1.53 | −1.44 | 2.75 | 5.77 | −3.70 |
| | Skin | Early stage | −1.84 | −2.62 | 1.05 | 0.73 | 1.05 | 5.14 | 8.51 | −1.02 |
| | Skin | Middle stage | −3.52 | −4.28 | −0.58 | −0.69 | −0.55 | 3.67 | 7.29 | −2.71 |
| | Skin | Late stage | −3.75 | −4.87 | −0.83 | −0.96 | −0.80 | 3.56 | 7.07 | −3.03 |
| | Spleen | Early stage | −4.22 | −4.98 | −1.50 | −1.55 | −1.39 | 2.81 | 5.82 | −3.79 |
| | Spleen | Middle stage | −3.52 | −4.19 | −1.04 | −1.09 | −0.95 | 2.79 | 5.56 | −2.59 |
| | Spleen | Late stage | −8.25 | −8.82 | −6.22 | −5.81 | −5.82 | −2.37 | −1.61 | −7.14 |
| | Testis | Early stage | 0.53 | −0.52 | 3.16 | 2.64 | 3.01 | 6.46 | 10.85 | 1.31 |
| | Testis | Middle stage | −1.45 | −2.36 | 1.29 | 0.97 | 1.27 | 5.05 | 8.83 | −0.66 |
| | Testis | Late stage | −2.59 | −3.41 | 0.29 | 0.07 | 0.31 | 4.36 | 7.88 | −1.81 |
| | Adipose | Early stage | −1.71 | −2.52 | 0.78 | 0.53 | 0.78 | 4.44 | 7.28 | −0.99 |
| | Adipose | Middle stage | −13.11 | −13.37 | −11.35 | −10.97 | −11.01 | −7.55 | −7.34 | −12.52 |
| | Adipose | Late stage | 4.63 | 3.48 | 6.71 | 6.03 | 6.33 | 9.26 | 13.83 | 5.28 |
| | | | Spleen Late stage | Testis Early stage | Testis Middle stage | Testis Late stage | Adipose Early stage | Adipose Middle stage | Adipose Late stage | |
| Model mice of myocardial infarction | Brain | Early stage | 3.31 | 0.15 | −1.06 | −1.64 | 12.59 | 0.31 | 0.93 | |
| | Brain | Middle stage | −1.12 | −5.27 | −5.91 | −6.88 | 9.93 | −3.40 | −2.71 | |
| | Brain | Late stage | 4.54 | 1.65 | 0.20 | −0.26 | 13.42 | 1.28 | 1.89 | |
| | Heart | Early stage | −3.28 | −6.38 | −6.87 | −7.73 | 7.60 | −4.68 | −4.11 | |
| | Heart | Middle stage | −4.24 | −7.19 | −7.69 | −8.50 | 6.35 | −5.29 | −4.75 | |
| | Heart | Late stage | −5.10 | −8.30 | −8.63 | −9.70 | 6.13 | −6.11 | −5.47 | |
| | Kidney | Early stage | 2.15 | −1.09 | −2.15 | −2.73 | 11.96 | −0.55 | 0.05 | |
| | Kidney | Middle stage | 4.15 | 1.45 | 0.26 | −0.12 | 12.90 | 1.19 | 1.76 | |
| | Kidney | Late stage | 5.27 | 2.78 | 1.38 | 1.08 | 13.65 | 2.09 | 2.64 | |
| | Liver | Early stage | 3.91 | 1.22 | 0.06 | −0.33 | 12.86 | 1.08 | 1.68 | |
| | Liver | Middle stage | −6.48 | −10.42 | −10.76 | −11.76 | 5.45 | −7.56 | −6.97 | |
| | Liver | Late stage | 6.38 | 4.23 | 2.76 | 2.59 | 14.36 | 3.16 | 3.65 | |
| | Lung | Early stage | 5.56 | 3.33 | 2.04 | 1.84 | 13.79 | 2.62 | 3.18 | |
| | Lung | Middle stage | −10.49 | −14.88 | −15.28 | −15.85 | 1.29 | −12.20 | −11.50 | |
| | Lung | Late stage | 4.74 | 2.09 | 0.79 | 0.43 | 13.26 | 1.60 | 2.15 | |
| | Pancreas | Early stage | 2.44 | −1.26 | −2.38 | −3.16 | 12.26 | −0.58 | 0.08 | |
| | Pancreas | Middle stage | 2.20 | −1.31 | −2.43 | −3.06 | 12.13 | −0.65 | −0.02 | |
| | Pancreas | Late stage | 1.06 | −2.93 | −3.73 | −4.82 | 11.52 | −1.70 | −1.04 | |
| | Muscle | Early stage | 1.39 | −1.76 | −2.67 | −3.27 | 11.26 | −1.10 | −0.52 | |
| | Muscle | Middle stage | 2.98 | 0.05 | −1.05 | −1.56 | 12.34 | 0.25 | 0.84 | |
| | Muscle | Late stage | 3.49 | 0.55 | −0.65 | −1.16 | 12.47 | 0.58 | 1.14 | |
| | Skin | Early stage | 6.03 | 3.59 | 2.10 | 1.88 | 13.93 | 2.63 | 3.29 | |
| | Skin | Middle stage | 4.46 | 1.81 | 0.45 | 0.01 | 13.30 | 1.43 | 2.01 | |
| | Skin | Late stage | 4.64 | 1.59 | 0.18 | −0.29 | 13.36 | 1.26 | 1.82 | |
| | Spleen | Early stage | 3.51 | 0.52 | −0.59 | −1.03 | 12.53 | 0.57 | 1.17 | |
| | Spleen | Middle stage | 2.89 | 0.79 | −0.24 | −0.61 | 12.30 | 0.80 | 1.34 | |
| | Spleen | Late stage | −2.23 | −5.23 | −5.80 | −6.32 | 7.29 | −4.35 | −3.82 | |
| | Testis | Early stage | 7.82 | 6.43 | 4.44 | 4.53 | 15.42 | 4.52 | 4.97 | |
| | Testis | Middle stage | 6.15 | 4.11 | 2.48 | 2.27 | 14.26 | 2.97 | 3.50 | |
| | Testis | Late stage | 5.39 | 2.91 | 1.39 | 1.10 | 13.87 | 2.18 | 2.74 | |
| | Adipose | Early stage | 5.29 | 2.84 | 1.71 | 1.43 | 13.00 | 2.22 | 2.85 | |
| | Adipose | Middle stage | −8.17 | −10.71 | −11.16 | −11.48 | 3.20 | −9.39 | −9.10 | |
| | Adipose | Late stage | 10.96 | 10.02 | 8.20 | 8.46 | 17.19 | 7.85 | 8.45 | |

TABLE 5-5

|  |  |  | Brain Early stage | Brain Middle stage | Brain Late stage | Heart Early stage | Heart Middle stage | Heart Late stage | Kidney Early stage | Kidney Middle stage | Kidney Late stage |
|---|---|---|---|---|---|---|---|---|---|---|---|
| Model mice of glioma | Left Brain | Early stage | −1.00 | −1.78 | −1.07 | −1.43 | 0.19 | −0.94 | 0.07 | 0.69 | 6.05 |
|  | Left Brain | Middle stage | −3.10 | −3.31 | −3.60 | −3.55 | −2.22 | −3.13 | −2.40 | −1.54 | 3.38 |
|  | Right Brain | Early stage | −4.28 | −4.59 | −4.47 | −4.46 | −2.69 | −3.85 | −2.46 | −1.57 | 4.26 |
|  | Right Brain | Middle stage | −8.37 | −8.38 | −7.61 | −7.52 | −6.12 | −7.10 | −4.91 | −4.05 | 2.33 |
|  | Heart | Early stage | −1.09 | −1.76 | −1.26 | −1.53 | 0.04 | −1.06 | −0.04 | 0.55 | 5.84 |
|  | Heart | Middle stage | 0.66 | −0.18 | 0.48 | −0.01 | 1.45 | 0.43 | 1.20 | 1.65 | 6.77 |
|  | Kidney | Early stage | 0.64 | −0.25 | 0.42 | −0.05 | 1.60 | 0.40 | 1.10 | 1.66 | 6.55 |
|  | Kidney | Middle stage | −0.58 | −1.37 | −0.79 | −1.19 | 0.49 | −0.63 | 0.33 | 0.87 | 6.25 |
|  | Liver | Early stage | −3.87 | −4.29 | −4.08 | −4.04 | −2.35 | −3.51 | −2.20 | −1.29 | 4.30 |
|  | Liver | Middle stage | −0.16 | −0.92 | −0.28 | −0.70 | 0.77 | −0.24 | 0.53 | 1.07 | 6.18 |
|  | Lung | Early stage | −0.53 | −1.20 | −0.68 | −1.03 | 0.49 | −0.57 | 0.35 | 0.89 | 6.19 |
|  | Lung | Middle stage | −4.76 | −5.30 | −4.92 | −5.03 | −3.00 | −4.08 | −2.55 | −1.64 | 4.21 |
|  | Pancreas | Early stage | −1.53 | −2.19 | −1.68 | −1.94 | −0.37 | −1.45 | −0.39 | 0.24 | 5.45 |
|  | Pancreas | Middle stage | −4.47 | −5.10 | −4.43 | −4.73 | −3.06 | −3.94 | −2.51 | −1.84 | 3.81 |
|  | Muscle | Early stage | −2.97 | −3.63 | −3.01 | −3.28 | −1.65 | −2.73 | −1.41 | −0.71 | 4.74 |
|  | Muscle | Middle stage | −0.42 | −1.13 | −0.50 | −0.86 | 0.56 | −0.46 | 0.41 | 0.98 | 5.99 |
|  | Skin | Early stage | −1.02 | −1.80 | −1.11 | −1.58 | 0.13 | −0.95 | 0.02 | 0.62 | 5.90 |
|  | Skin | Middle stage | −4.24 | −4.59 | −4.37 | −4.23 | −2.89 | −3.77 | −2.60 | −1.86 | 3.71 |
|  | Spleen | Early stage | −4.46 | −4.92 | −4.48 | −4.50 | −3.26 | −4.14 | −2.90 | −2.13 | 3.21 |
|  | Spleen | Middle stage | 2.21 | 1.46 | 2.11 | 1.61 | 2.80 | 1.91 | 2.37 | 2.74 | 7.35 |
|  | Testis | Early stage | −1.53 | −2.27 | −1.45 | −1.76 | −0.60 | −1.43 | −0.53 | 0.01 | 4.83 |
|  | Testis | Middle stage | −0.12 | −0.86 | −0.27 | −0.67 | 0.86 | −0.22 | 0.63 | 1.18 | 6.24 |
|  | Adipose | Early stage | −11.86 | −12.17 | −11.85 | −11.77 | −10.91 | −11.46 | −10.12 | −9.20 | −4.16 |
|  | Adipose | Middle stage | −13.65 | −13.59 | −13.35 | −13.19 | −11.89 | −12.72 | −11.11 | −9.99 | −4.14 |

|  |  |  | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|
| Model mice of glioma | Left Brain | Early stage | −1.45 | −1.87 | −2.32 | −3.74 | −5.89 | −1.72 | 2.40 | 8.97 | 0.84 |
|  | Left Brain | Middle stage | −3.69 | −3.32 | −3.88 | −4.91 | −7.86 | −3.69 | −0.81 | 3.43 | −1.97 |
|  | Right Brain | Early stage | −3.73 | −3.68 | −4.19 | −6.39 | −9.09 | 4.68 | −0.57 | 5.61 | −2.36 |
|  | Right Brain | Middle stage | −5.85 | −5.90 | −6.25 | −9.73 | −11.10 | −7.82 | −3.67 | 2.36 | −5.73 |
|  | Heart | Early stage | −1.61 | −1.90 | −2.37 | −3.72 | −6.20 | −1.85 | 2.28 | 8.60 | 0.69 |
|  | Heart | Middle stage | −0.45 | −0.94 | −1.43 | −2.12 | −4.63 | −0.28 | 3.74 | 9.81 | 2.28 |
|  | Kidney | Early stage | −0.43 | −1.00 | −1.46 | −2.23 | −4.13 | −0.32 | 3.68 | 10.75 | 2.26 |
|  | Kidney | Middle stage | −1.23 | −1.64 | −2.12 | −3.28 | −5.83 | −1.37 | 2.85 | 9.40 | 1.15 |
|  | Liver | Early stage | −3.70 | −3.41 | −3.97 | −6.05 | −8.77 | −4.34 | −0.27 | 5.75 | −2.04 |
|  | Liver | Middle stage | −0.80 | −1.33 | −1.74 | −2.52 | −4.40 | −0.87 | 2.67 | 8.86 | 1.29 |
|  | Lung | Early stage | −1.25 | −1.58 | −2.06 | −3.18 | −5.66 | −1.35 | 2.71 | 8.69 | 1.14 |
|  | Lung | Middle stage | −3.74 | −3.87 | −4.33 | 6.81 | −8.84 | −4.96 | −0.75 | 5.74 | −2.49 |
|  | Pancreas | Early stage | −1.90 | −2.14 | −2.66 | −4.02 | −6.49 | −2.24 | 1.86 | 7.79 | 0.22 |
|  | Pancreas | Middle stage | −3.54 | −4.06 | −4.28 | −6.27 | −7.84 | −4.65 | −0.95 | 4.86 | −2.46 |
|  | Muscle | Early stage | −2.65 | −2.98 | −3.39 | −5.33 | −6.96 | −3.40 | 0.48 | 6.72 | −1.17 |
|  | Muscle | Middle stage | −1.09 | −1.49 | −1.97 | −2.98 | −4.94 | −1.15 | 2.74 | 8.86 | 1.27 |
|  | Skin | Early stage | −1.42 | −1.96 | −2.33 | −3.67 | −5.71 | −1.68 | 2.29 | 8.83 | 0.70 |
|  | Skin | Middle stage | −3.90 | −3.98 | −4.40 | −6.01 | −7.94 | −4.53 | −1.00 | 4.43 | −2.50 |
|  | Spleen | Early stage | −3.90 | −4.07 | −4.49 | −6.36 | −7.89 | −4.78 | −1.42 | 3.71 | −2.91 |
|  | Spleen | Middle stage | 0.82 | 0.21 | −0.26 | −0.23 | −2.52 | 1.34 | 4.73 | 9.90 | 3.31 |
|  | Testis | Early stage | −1.70 | −2.18 | −2.59 | −3.62 | −4.89 | −2.01 | 1.22 | 6.69 | −0.09 |
|  | Testis | Middle stage | −0.94 | −1.37 | −1.83 | −2.76 | −5.11 | −0.95 | 2.96 | 9.29 | 1.51 |
|  | Adipose | Early stage | −10.52 | −10.18 | −10.59 | −12.96 | −14.00 | −11.86 | −9.54 | −6.18 | −10.66 |
|  | Adipose | Middle stage | −11.14 | −10.46 | −10.75 | −14.67 | −15.81 | −13.19 | −10.48 | −6.52 | −11.92 |

TABLE 5-6

|  |  |  | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of glioma | Left Brain | Early stage | −4.00 | −4.80 | −0.90 | −1.01 | −0.83 | 3.57 | 7.17 | −3.26 |
|  | Left Brain | Middle stage | −5.47 | −6.20 | −3.31 | −2.88 | −2.98 | 0.92 | 2.86 | −4.97 |
|  | Right Brain | Early stage | −6.67 | −7.39 | −3.51 | −3.25 | −3.33 | 1.51 | 4.27 | −6.09 |
|  | Right Brain | Middle stage | −9.54 | −9.64 | −6.09 | −5.71 | −6.13 | −0.65 | 1.27 | −9.19 |
|  | Heart | Early stage | −4.11 | −4.92 | −1.06 | −1.11 | −0.95 | 3.38 | 7.13 | −3.38 |
|  | Heart | Middle stage | −2.54 | −3.44 | 0.29 | 0.06 | 0.31 | 4.38 | 8.20 | −1.88 |
|  | Kidney | Early stage | −2.73 | −3.39 | 0.26 | 0.04 | 0.29 | 4.50 | 8.42 | −1.84 |
|  | Kidney | Middle stage | −3.88 | −4.37 | −0.66 | −0.76 | −0.55 | 3.72 | 7.52 | −2.95 |
|  | Liver | Early stage | −6.47 | −7.39 | −3.38 | −3.05 | −3.06 | 1.66 | 4.52 | −5.85 |
|  | Liver | Middle stage | −3.12 | −3.49 | −0.28 | −0.46 | −0.25 | 3.84 | 6.87 | −2.23 |
|  | Lung | Early stage | −3.57 | −4.49 | −0.61 | −0.71 | −0.55 | 3.51 | 7.37 | −2.76 |
|  | Lung | Middle stage | −7.24 | −7.19 | −3.65 | −3.42 | −3.40 | 1.40 | 4.22 | −6.36 |
|  | Pancreas | Early stage | −4.47 | −5.28 | −1.44 | −1.43 | −1.26 | 3.07 | 6.38 | −3.65 |

TABLE 5-6-continued

| | | | | | | | | | |
|---|---|---|---|---|---|---|---|---|---|
| Pancreas | Middle stage | −6.73 | −6.54 | −3.47 | −3.48 | −3.30 | 1.13 | 3.46 | −5.77 |
| Muscle | Early stage | −5.44 | −5.85 | −2.41 | −2.41 | −2.31 | 2.26 | 5.21 | −4.90 |
| Muscle | Middle stage | −3.07 | −4.06 | −0.47 | −0.62 | −0.46 | 3.71 | 7.04 | −2.61 |
| Skin | Early stage | −4.13 | −4.51 | −0.90 | −1.05 | −0.81 | 3.52 | 6.77 | −3.17 |
| Skin | Middle stage | −6.39 | −7.11 | −3.62 | −3.27 | −3.56 | 1.06 | 3.38 | −5.67 |
| Spleen | Early stage | −6.60 | −7.07 | −3.82 | −3.74 | −3.65 | 0.68 | 2.65 | −5.86 |
| Spleen | Middle stage | −0.84 | −1.63 | 1.71 | 1.30 | 1.58 | 5.02 | 8.46 | −0.10 |
| Testis | Early stage | −3.84 | −4.56 | −1.32 | −1.51 | −1.31 | 2.75 | 5.09 | −3.27 |
| Testis | Middle stage | −3.20 | −4.02 | −0.28 | −0.44 | −0.24 | 3.89 | 7.54 | −2.46 |
| Adipose | Early stage | −13.10 | −13.49 | −11.03 | −10.59 | −10.60 | −6.54 | −6.35 | −12.58 |
| Adipose | Middle stage | −14.17 | −14.66 | −11.88 | −11.20 | −11.59 | −6.74 | −6.71 | −13.85 |

| | | | Spleen Late stage | Testis Early stage | Testis Middle stage | Testis Late stage | Adipose Early stage | Adipose Middle stage | Adipose Late stage |
|---|---|---|---|---|---|---|---|---|---|
| Model mice of glioma | Left Brain | Early stage | 4.54 | 1.55 | 0.12 | −0.37 | 13.38 | 1.19 | 1.83 |
| | Left Brain | Middle stage | 1.16 | −1.58 | −2.35 | −2.77 | 10.69 | −0.95 | −0.49 |
| | Right Brain | Early stage | 1.93 | −1.76 | −2.76 | −3.44 | 11.82 | −0.86 | −0.26 |
| | Right Brain | Middle stage | −0.80 | −5.28 | −6.03 | −7.17 | 10.27 | −3.18 | −2.50 |
| | Heart | Early stage | 4.33 | 1.40 | −0.03 | −0.51 | 13.34 | 1.07 | 1.69 |
| | Heart | Middle stage | 5.62 | 2.90 | 1.43 | 1.08 | 13.94 | 2.06 | 2.68 |
| | Kidney | Early stage | 5.52 | 3.09 | 1.42 | 1.16 | 13.83 | 2.32 | 2.87 |
| | Kidney | Middle stage | 4.73 | 2.00 | 0.41 | −0.02 | 13.64 | 1.43 | 2.09 |
| | Liver | Early stage | 2.15 | −1.40 | −2.44 | −3.11 | 12.02 | −0.65 | −0.05 |
| | Liver | Middle stage | 4.74 | 2.00 | 0.66 | 0.32 | 13.27 | 1.71 | 2.30 |
| | Lung | Early stage | 4.71 | 1.82 | 0.44 | 0.01 | 13.20 | 1.33 | 1.95 |
| | Lung | Middle stage | 1.88 | −1.99 | −2.92 | −3.92 | 11.92 | −1.02 | −0.38 |
| | Pancreas | Early stage | 3.86 | 0.87 | −0.44 | −0.94 | 13.19 | 0.77 | 1.39 |
| | Pancreas | Middle stage | 1.40 | −2.09 | −2.98 | −3.76 | 11.44 | −1.28 | −0.63 |
| | Muscle | Early stage | 2.83 | −0.55 | −1.72 | −2.40 | 12.33 | −0.14 | 0.50 |
| | Muscle | Middle stage | 4.63 | 1.82 | 0.52 | 0.11 | 13.29 | 1.46 | 2.01 |
| | Skin | Early stage | 4.31 | 1.43 | 0.05 | −0.42 | 13.18 | 1.20 | 1.87 |
| | Skin | Middle stage | 1.33 | −2.02 | −3.04 | −3.68 | 11.18 | −1.14 | −0.58 |
| | Spleen | Early stage | 1.02 | −2.38 | −3.25 | −3.76 | 10.89 | −1.54 | −0.96 |
| | Spleen | Middle stage | 5.61 | 4.13 | 2.70 | 2.62 | 14.23 | 3.17 | 3.73 |
| | Testis | Early stage | 3.16 | 0.46 | −0.59 | −1.07 | 12.37 | 0.58 | 1.11 |
| | Testis | Middle stage | 4.84 | 2.06 | 0.81 | 0.37 | 13.41 | 1.63 | 2.29 |
| | Adipose | Early stage | −7.47 | −10.58 | −10.66 | −11.45 | 5.96 | −9.72 | −8.23 |
| | Adipose | Middle stage | −7.95 | −11.55 | −11.78 | −12.66 | 5.86 | −9.72 | −8.41 |

TABLE 5-7

| | | Brain Early stage | Brain Middle stage | Brain Late stage | Heart Early stage | Heart Middle stage | Heart Late stage | Kidney Early stage | Kidney Middle stage | Kidney Late stage | Liver Early stage | Liver Middle stage | Liver Late stage | Lung Early stage | Lung Middle stage | Lung Late stage | Pancreas Early stage | Pancreas Middle stage | Pancreas Late stage |
|---|---|---|---|---|---|---|---|---|---|---|---|---|---|---|---|---|---|---|---|
| Model mice of early onset dementia | Brain Early stage | −0.03 | −0.86 | −0.16 | −0.59 | 0.96 | −0.15 | 0.65 | 1.20 | 6.21 | −0.81 | −1.34 | −1.79 | −2.65 | −4.65 | −0.84 | 2.99 | 9.41 | 1.57 |
| | Brain Middle stage | −5.21 | −5.55 | −5.26 | −5.40 | −4.59 | −5.08 | −4.35 | −3.87 | 0.09 | −5.06 | −5.31 | −5.48 | −6.35 | −7.53 | −5.44 | −3.50 | −0.61 | −4.29 |
| | Brain Late stage | 1.22 | 0.32 | 0.96 | 0.46 | 2.06 | 0.89 | 1.52 | 2.00 | 6.92 | −0.09 | −0.64 | −1.12 | −1.64 | −3.85 | 0.18 | 4.11 | 10.56 | 2.72 |
| | Heart Early stage | −6.67 | −6.82 | −6.58 | −6.77 | −5.50 | −6.33 | −5.07 | −4.12 | 1.17 | −5.81 | −5.52 | −6.06 | −8.34 | −9.98 | −6.91 | −3.93 | 0.55 | −5.21 |
| | Heart Middle stage | −2.45 | −2.78 | −2.56 | −2.74 | −1.61 | −2.43 | −1.57 | −0.95 | 3.71 | −2.81 | −2.84 | −3.32 | −4.23 | −6.48 | −2.99 | −0.09 | 4.06 | −1.26 |
| | Heart Late stage | −1.77 | −2.20 | −1.86 | −2.18 | −0.86 | −1.80 | −0.88 | −0.27 | 4.87 | −2.15 | −2.30 | −2.80 | −3.74 | −5.80 | −2.34 | 0.87 | 5.50 | −0.43 |
| | Kidney Early stage | −4.61 | −4.86 | −4.62 | −4.69 | −3.38 | −4.24 | −3.12 | −2.30 | 2.77 | −4.29 | −4.16 | −4.64 | −6.48 | −8.66 | −4.98 | −1.74 | 2.96 | −3.12 |
| | Kidney Middle stage | −2.45 | −2.80 | −2.51 | −2.68 | −1.70 | −2.36 | −1.60 | −1.10 | 3.24 | −2.66 | −2.90 | −3.24 | −4.00 | −5.65 | −2.90 | −0.33 | 3.43 | −1.36 |
| | Kidney Late stage | −1.58 | −2.09 | −1.70 | −1.95 | 0.62 | −1.55 | −0.62 | 0.03 | 4.88 | −1.97 | −2.19 | −2.66 | −3.69 | −5.90 | −2.19 | 1.20 | 6.28 | −0.15 |
| | Liver Early stage | −1.11 | −1.61 | −1.22 | −1.45 | −0.41 | −1.15 | −0.43 | 0.06 | 4.65 | −1.55 | −1.82 | −2.21 | −2.88 | −4.58 | −1.64 | 1.08 | 5.25 | −0.02 |
| | Liver Middle stage | −1.73 | −2.08 | −1.76 | −1.97 | −1.21 | −1.76 | −1.18 | −0.76 | 3.08 | −2.05 | −2.25 | −2.61 | −3.03 | −4.25 | −2.11 | −0.09 | 2.96 | −0.93 |
| | Liver Late stage | −0.96 | −1.49 | −1.06 | −1.33 | −0.17 | −1.00 | −0.22 | 0.29 | 5.16 | −1.47 | −1.72 | −2.14 | −2.91 | −4.77 | −1.53 | 1.48 | 6.02 | 0.27 |
| | Lung Early stage | −1.41 | −1.77 | −1.46 | −1.65 | −0.95 | −1.45 | −0.91 | −0.55 | 2.94 | −1.74 | −2.08 | −2.38 | −2.65 | −3.77 | −1.80 | 0.08 | 2.90 | −0.67 |
| | Lung Middle stage | −6.07 | −6.55 | −6.02 | −6.22 | −5.74 | −6.05 | −5.22 | −4.85 | −1.35 | −5.73 | −6.21 | −6.32 | −7.25 | −7.79 | −6.42 | −4.60 | −2.25 | −5.32 |
| | Lung Late stage | −3.64 | −4.04 | −3.65 | −3.89 | −2.62 | −3.51 | −2.29 | −1.57 | 3.65 | −3.44 | −3.55 | −3.95 | −6.10 | −7.79 | −4.43 | −0.71 | 4.44 | −2.13 |
| | Pancreas Early stage | −4.78 | −5.23 | −4.87 | −4.85 | −3.54 | −4.46 | −3.16 | −2.32 | 3.14 | −4.38 | −4.34 | −4.75 | −6.87 | −8.81 | −5.27 | −1.77 | 3.72 | −3.26 |
| | Pancreas Middle stage | −3.06 | −3.54 | −3.23 | −3.42 | −2.09 | −2.97 | −1.93 | −1.28 | 3.96 | −3.14 | −3.35 | −3.72 | −5.02 | −7.04 | −3.55 | −0.39 | 4.64 | −1.69 |
| | Pancreas Late stage | 1.86 | 1.09 | 1.79 | 1.25 | 2.60 | 1.60 | 2.16 | 2.52 | 7.38 | 0.56 | −0.06 | −0.54 | −0.64 | −3.08 | 0.98 | 4.66 | 10.10 | 3.14 |
| | Muscle Early stage | −7.71 | −8.10 | −7.45 | −7.74 | 6.87 | −7.48 | −5.82 | −5.18 | 0.22 | −6.42 | −6.61 | −6.84 | −9.30 | −10.13 | −7.86 | −4.93 | −0.77 | −6.24 |
| | Muscle Middle stage | −5.11 | −5.27 | −5.12 | −5.28 | −4.29 | −5.01 | −4.11 | −3.47 | 1.21 | −4.97 | −4.86 | −5.24 | −6.58 | −8.16 | −5.54 | −2.98 | 0.65 | −3.97 |
| | Muscle Late stage | −4.47 | −4.81 | −4.39 | −4.60 | −3.47 | −4.46 | −3.20 | −2.53 | 2.72 | −4.20 | −4.18 | −4.72 | 6.24 | −7.78 | −4.90 | −1.83 | 2.63 | −3.22 |
| | Skin Early stage | −8.74 | −9.28 | −8.26 | −8.53 | −7.91 | −8.33 | −6.95 | −6.14 | −1.11 | −7.49 | −7.49 | −7.91 | −10.13 | −10.86 | −8.74 | −6.17 | −2.49 | −7.66 |
| | Skin Middle stage | −2.67 | −2.91 | −2.67 | −2.79 | −2.44 | −2.68 | −2.33 | −2.15 | 0.01 | −2.74 | −3.07 | −3.19 | −3.31 | −3.83 | −2.84 | −1.83 | −0.37 | −2.26 |
| | Skin Late stage | −2.41 | −2.87 | −2.51 | −2.69 | −1.58 | −2.38 | −1.42 | 0.86 | 4.00 | −2.58 | −2.82 | −3.22 | −4.30 | −6.14 | −2.92 | 0.10 | 4.64 | −1.14 |
| | Spleen Early stage | 0.20 | −0.35 | 0.10 | −0.23 | 0.91 | 0.10 | 0.72 | 1.17 | 5.71 | −0.52 | −0.99 | −1.36 | −1.76 | −3.63 | −0.43 | 2.41 | 7.03 | 1.29 |
| | Spleen Middle stage | −13.45 | −14.09 | −13.17 | −13.35 | −12.72 | −13.03 | −11.71 | −11.13 | −6.55 | −11.85 | −12.05 | −12.11 | −14.49 | −14.94 | −13.47 | −11.35 | −8.76 | −12.42 |
| | Spleen Late stage | 2.86 | 2.14 | 2.79 | 2.33 | 3.35 | 2.55 | 2.91 | 3.21 | 7.49 | 1.53 | 0.90 | 0.44 | 0.72 | −1.34 | 2.08 | 4.86 | 9.39 | 3.79 |
| | Testis Early stage | 1.79 | 1.06 | 1.77 | 1.21 | 2.45 | 1.56 | 2.11 | 2.46 | 7.13 | 0.57 | −0.02 | −0.48 | −0.55 | −2.87 | 0.97 | 4.31 | 9.37 | 2.92 |
| | Testis Middle stage | −5.39 | −5.72 | −5.44 | −5.60 | −4.87 | −5.37 | −4.67 | −4.16 | −0.47 | −5.32 | −5.43 | −5.73 | −6.48 | −7.52 | −5.64 | −3.86 | −1.21 | −4.64 |
| | Testis Late stage | 4.60 | 3.71 | 4.29 | 3.67 | 5.06 | 4.01 | 4.31 | 4.47 | 8.74 | 2.56 | 1.70 | 1.21 | 1.93 | −0.46 | 3.46 | 6.96 | 12.18 | 5.74 |
| | Adipose Early stage | −3.29 | −3.65 | −3.34 | −3.48 | −2.62 | −3.28 | −2.43 | −1.86 | 2.57 | −3.44 | −3.57 | −3.93 | 4.90 | −6.53 | −3.73 | −1.24 | 2.44 | −2.25 |
| | Adipose Middle stage | −9.44 | −9.95 | −9.16 | −9.32 | −9.12 | −9.35 | −8.32 | −8.12 | −4.67 | −8.60 | −9.33 | −9.28 | −10.31 | −10.52 | −9.46 | −7.94 | −6.08 | −8.74 |
| | Adipose Late stage | 2.69 | 2.20 | 2.48 | 2.21 | 3.24 | 2.50 | 2.83 | 3.10 | 6.79 | 1.57 | 1.08 | 0.68 | 0.98 | −0.69 | 2.05 | 4.46 | 8.30 | 3.62 |

TABLE 5-8

| | | | Muscle Early stage | Muscle Middle stage | Muscle Late stage | Skin Early stage | Skin Middle stage | Skin Late stage | Spleen Early stage | Spleen Middle stage |
|---|---|---|---|---|---|---|---|---|---|---|
| Model mice of early onset dementia | Brain | Early stage | −3.11 | −3.87 | −0.20 | −0.40 | −0.17 | 4.04 | 7.42 | −2.30 |
| | Brain | Middle stage | −6.65 | −6.91 | −4.96 | −4.94 | −4.82 | −1.90 | −0.99 | −6.14 |
| | Brain | Late stage | −2.20 | −3.05 | 0.68 | 0.42 | 0.70 | 4.76 | 8.60 | −1.42 |
| | Heart | Early stage | −8.77 | −9.20 | −6.22 | −5.83 | −5.86 | −1.40 | −0.07 | −8.05 |
| | Heart | Middle stage | −4.76 | −5.57 | −2.50 | −2.34 | −2.27 | 1.47 | 3.37 | −4.01 |
| | Heart | Late stage | −4.16 | −4.92 | −1.75 | −1.68 | −1.64 | 2.26 | 4.57 | −3.60 |
| | Kidney | Early stage | −6.64 | −7.31 | −4.12 | −3.89 | −3.94 | 0.34 | 2.14 | −6.12 |
| | Kidney | Middle stage | −4.34 | −4.96 | −2.35 | −2.37 | −2.26 | 1.17 | 2.79 | −3.81 |
| | Kidney | Late stage | −4.11 | −4.91 | −1.52 | −1.55 | −1.41 | 2.63 | 5.21 | −3.57 |
| | Liver | Early stage | −3.25 | −3.89 | −1.16 | −1.21 | −1.08 | 2.34 | 4.28 | −2.68 |
| | Liver | Middle stage | −3.30 | −3.93 | −1.74 | −1.78 | −1.68 | 1.14 | 2.42 | −2.91 |
| | Liver | Late stage | −3.29 | −4.08 | −1.02 | −1.07 | −0.94 | 2.70 | 5.02 | −2.72 |
| | Lung | Early stage | −2.95 | −3.42 | −1.43 | −1.53 | −1.38 | 1.25 | 2.41 | −2.48 |
| | Lung | Middle stage | −7.41 | −7.56 | −5.77 | −5.96 | −5.72 | −3.27 | −2.48 | −6.81 |
| | Lung | Late stage | −5.98 | −6.67 | −3.29 | −3.17 | −3.07 | 1.21 | 3.37 | −5.29 |
| | Pancreas | Early stage | −7.00 | −7.77 | −4.24 | −3.98 | −3.92 | 0.52 | 2.55 | −6.34 |
| | Pancreas | Middle stage | −5.43 | −5.82 | −2.82 | −2.74 | −2.59 | 1.36 | 3.46 | −4.69 |
| | Pancreas | Late stage | −1.26 | −2.10 | 1.40 | 1.04 | 1.30 | 4.96 | 8.44 | −0.50 |
| | Muscle | Early stage | −9.56 | −9.61 | −6.94 | −6.71 | −6.63 | −2.43 | −1.29 | −8.53 |
| | Muscle | Middle stage | −6.87 | −7.49 | −5.06 | −4.73 | −4.71 | −1.05 | 0.14 | −6.21 |
| | Muscle | Late stage | −6.48 | −7.14 | −4.31 | −3.94 | −4.12 | 0.19 | 1.89 | −5.93 |
| | Skin | Early stage | −10.00 | −10.86 | −7.87 | −8.45 | −7.86 | −4.02 | −2.86 | −9.98 |
| | Skin | Middle stage | −3.50 | −3.68 | −2.61 | −2.77 | −2.63 | −1.16 | −0.57 | −3.25 |
| | Skin | Late stage | −4.64 | −5.41 | −2.32 | −2.41 | −2.25 | 1.95 | 3.78 | −4.22 |
| | Spleen | Early stage | −2.27 | −2.82 | 0.03 | −0.14 | 0.05 | 3.63 | 5.58 | −1.65 |
| | Spleen | Middle stage | −14.43 | −14.48 | −12.42 | −12.77 | −12.52 | −9.23 | −8.64 | −14.51 |
| | Spleen | Late stage | 0.19 | −0.63 | 2.35 | 2.01 | 2.20 | 5.51 | 7.75 | 0.89 |
| | Testis | Early stage | −1.16 | −1.95 | 1.39 | 1.03 | 1.27 | 4.81 | 8.19 | 0.41 |
| | Testis | Middle stage | −6.77 | −7.11 | −5.23 | −5.26 | −5.13 | −2.38 | −1.55 | −6.40 |
| | Testis | Late stage | 1.22 | 0.24 | 3.66 | 3.08 | 3.53 | 6.66 | 10.63 | 1.94 |
| | Adipose | Early stage | −5.22 | −5.90 | −3.27 | −3.16 | −2.97 | 0.38 | 1.83 | −4.59 |
| | Adipose | Middle stage | −10.45 | −10.66 | 8.93 | −9.22 | −8.96 | −6.69 | −6.09 | −9.93 |
| | Adipose | Late stage | 0.50 | −0.21 | 2.34 | 2.13 | 2.28 | 5.28 | 7.42 | 1.01 |

| | | | Spleen Late stage | Testis Early stage | Tests Middle stage | Testis Late stage | Adipose Early stage | Adipose Middle stage | Adipose Late stage |
|---|---|---|---|---|---|---|---|---|---|
| Model mice of early onset dementia | Brain | Early stage | 4.99 | 2.24 | 0.82 | 0.47 | 13.61 | 1.79 | 2.35 |
| | Brain | Middle stage | −2.00 | −4.04 | −4.56 | −4.89 | 6.74 | −3.52 | −3.14 |
| | Brain | Late stage | 5.86 | 3.45 | 1.85 | 1.63 | 14.01 | 2.54 | 3.11 |
| | Heart | Early stage | −1.58 | −4.84 | −5.23 | −6.06 | 8.87 | −3.53 | −2.94 |
| | Heart | Middle stage | 1.72 | −0.82 | −1.66 | −1.98 | 10.96 | −0.45 | 0.03 |
| | Heart | Late stage | 2.82 | 0.07 | −0.89 | −1.31 | 11.71 | 0.23 | 0.74 |
| | Kidney | Early stage | 0.44 | −2.62 | −3.41 | −3.90 | 10.34 | −1.73 | −1.21 |
| | Kidney | Middle stage | 1.34 | −0.98 | −1.74 | −2.07 | 10.25 | −0.64 | −0.18 |
| | Kidney | Late stage | 3.23 | 0.38 | −0.67 | −1.10 | 12.34 | 0.47 | 1.01 |
| | Liver | Early stage | 2.69 | 0.40 | −0.45 | −0.77 | 11.37 | 0.49 | 0.97 |
| | Liver | Middle stage | 1.28 | −0.61 | −1.19 | −1.47 | 9.47 | −0.40 | 0.00 |
| | Liver | Late stage | 3.22 | 0.74 | −0.22 | −0.58 | 12.01 | 0.73 | 1.23 |
| | Lung | Early stage | 1.32 | −0.39 | −0.93 | −1.19 | 9.41 | −0.23 | 0.16 |
| | Lung | Middle stage | −3.32 | −5.15 | −5.40 | −5.88 | 4.90 | −4.94 | −4.48 |
| | Lung | Late stage | 1.49 | −1.61 | −2.48 | −3.08 | 11.25 | −1.00 | −0.42 |
| | Pancreas | Early stage | 0.67 | −2.67 | −3.52 | −4.22 | 10.83 | −1.69 | −1.13 |
| | Pancreas | Middle stage | 1.69 | −1.19 | −2.10 | −2.59 | 11.12 | −0.69 | −0.16 |
| | Pancreas | Late stage | 6.08 | 3.80 | 2.43 | 2.24 | 13.99 | 2.82 | 3.46 |
| | Muscle | Early stage | −2.66 | −5.85 | −6.32 | −7.18 | 7.93 | −4.56 | −3.96 |
| | Muscle | Middle stage | −1.15 | −3.58 | 4.33 | −4.61 | 8.29 | −2.77 | −2.35 |
| | Muscle | Late stage | 0.26 | −2.63 | −3.35 | −3.94 | 10.05 | −1.85 | −1.31 |
| | Skin | Early stage | −4.16 | −7.22 | −7.30 | −8.14 | 6.79 | −6.26 | −5.28 |
| | Skin | Middle stage | −1.13 | −2.13 | −2.38 | −2.56 | 4.21 | −2.08 | −1.82 |
| | Skin | Late stage | 2.04 | −0.67 | −1.55 | −1.97 | 11.00 | −0.33 | 0.19 |
| | Spleen | Early stage | 4.52 | 1.80 | 0.85 | 0.54 | 12.48 | 1.64 | 2.23 |
| | Spleen | Middle stage | −10.44 | −12.20 | −12.24 | −13.04 | 0.95 | −11.34 | −10.65 |
| | Spleen | Late stage | 7.07 | 4.37 | 3.26 | 3.00 | 14.06 | 3.56 | 4.23 |
| | Testis | Early stage | 5.73 | 3.57 | 2.42 | 2.14 | 13.85 | 2.73 | 3.42 |
| | Testis | Middle stage | −2.53 | 4.45 | −4.75 | −5.20 | 5.99 | −3.89 | −3.50 |
| | Testis | Late stage | 8.08 | 6.33 | 4.80 | 4.84 | 15.21 | 4.65 | 5.22 |
| | Adipose | Early stage | 0.46 | −1.88 | −2.54 | −2.97 | 9.86 | −1.43 | −0.97 |
| | Adipose | Middle stage | −6.74 | −8.61 | −8.79 | −9.22 | 1.36 | −8.60 | −8.03 |
| | Adipose | Late stage | 5.75 | 3.94 | 2.93 | 2.92 | 13.66 | 3.85 | 4.45 |

$z_i$ values of 0.00; and more than 0.00, 0.15 or less are shown in the tables above.

Tables 5-1 to 5-8 show that, in the same organ, when diseases are different, the absolute value of the zi value is large.

Reference Example 1

Experimental Example I. Establishment of Oscar Gene Mutant Mice

Figure 24:
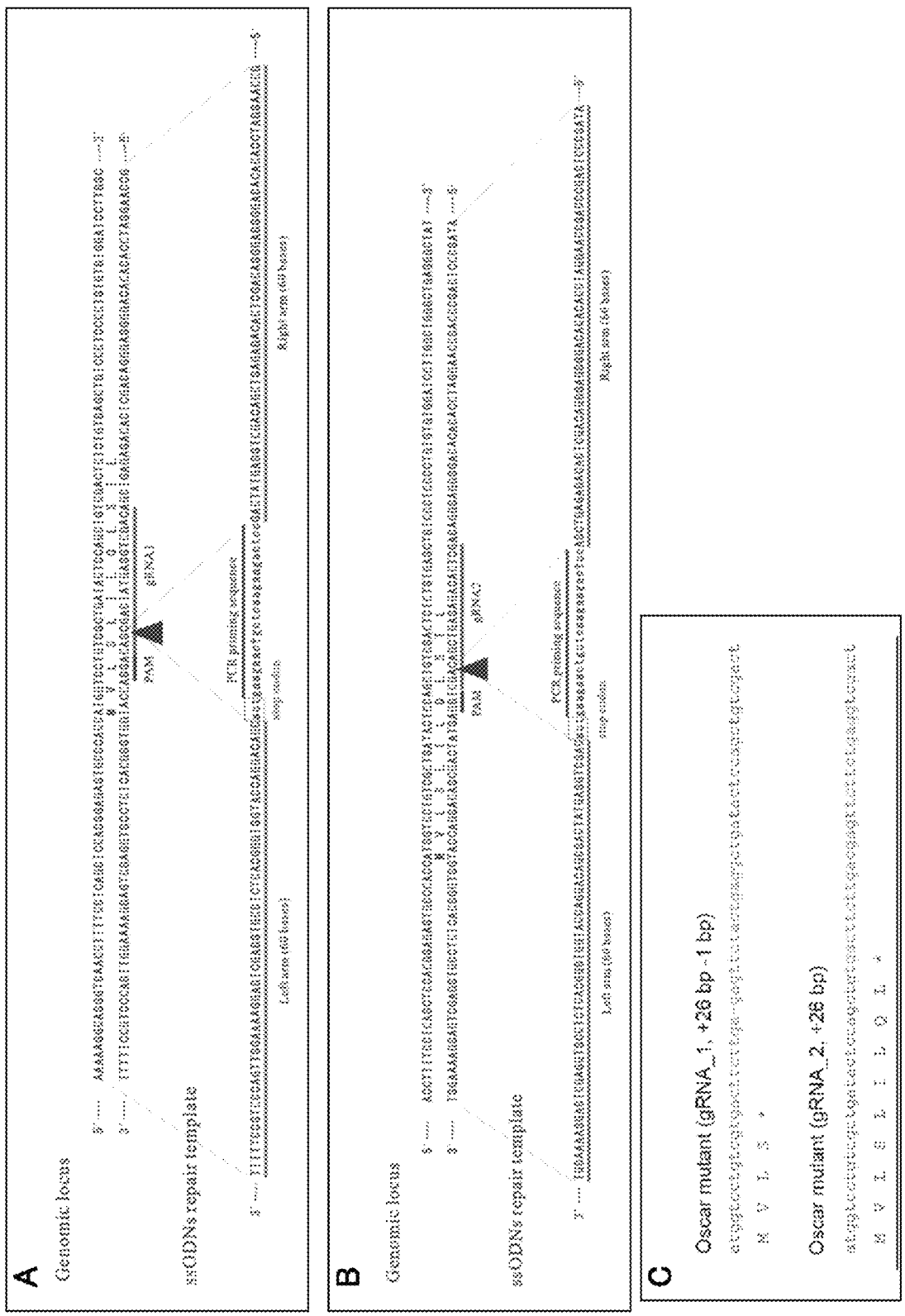
FIG. 24 shows mutation sites by CRISPR/Cas9 and sequences of ssODNs for obtaining Oscar gene mutant mice.

1. Construction of gRNA and Cas9 Expression Vector gRNA sequences (Oscar-gRNA1 and Oscar-gRNA2) were designed, and oligo DNA encoding the gRNA sequences was synthesized using an Optimized CRISPR design tool (publicly available on the website of Massachusetts Institute of Technology, Zhang Lab (http://crispr.mit.edu/)). The Oscar gene target sequences contained in these sequences are the following sequences: ACAGCTGGAGTATCAGCGAC (SEQ ID NO: 5) in Oscar-gRNA1 and GCTCACAGAGAGTCGACAGC (SEQ ID NO: 6) in Oscar-gRNA2, which are present in exon 1 of the Oscar gene. These were individually inserted into pX330-U6-Chimeric_BB-CBh-hSpCas9, which is a Cas9 expression vector (pX330-Oscar-gRNA1 and pX330-Oscar-gRNA2). The nucleotide sequences of the gRNA insertion sites in the obtained vectors were determined to confirm that gRNA was inserted as designed. In addition, single-stranded oligodeoxynucleotides (ssODNs) were individually synthesized so as to include the respective Oscar gene target sequences. The donor oligo DNA region was designed so that a stop codon is placed immediately downstream of the Serine coding sequence of the predetermined Oscar-gRNA1 cleavage site, and immediately downstream of the Leucine coding sequence of the predetermined Oscar-gRNA2 cleavage site (FIG. 24A and FIG. 24B).

```
ssODN for Oscar-gRNA1:
                                            (SEQ ID NO: 7)
GCCAAGGATCCACACACAGGGGAGGGACAGCTCACAGAGAGTCGACAGCT GGAGTATCAGcctcagaagaactcgtcaagaagtcaCGACAGGACCATGG

TGGGCACTCTCCGTGGAGCTGAGGAAAAGGTTGACCCTGCCTTTTT ssODN for Oscar-gRNA2:
                                            (SEQ ID NO: 8)
ATAGCCCTCAGCCCAGCCAAGGATCCACACACAGGGGAGGGACAGCTCAC AGAGAGTCGAcctcagaagaactcgtcaagaagtcaCAGCTGGAGTATCA

GCGACAGGACCATGGTGGGCACTCTCCGTGGAGCTGAGGAAAAGGT
```

2. Establishment of Oscar Gene Mutant Mice pX330-Oscar-gRNA1 and pX330-Oscar-gRNA2 were individually injected into C57BL/6N Slc fertilized eggs together with the corresponding ssODN. The fertilized eggs after the injection were injected into the oviducts of pseudopregnant ICR female mice. The genotype of the F0 mice was confirmed by PCR (for the primers, see Table 6) and direct sequencing. F1 mice were obtained by mating the F0 mice.

The genotype of each mouse was determined by direct sequencing and high-resolution melting (HRM) analyses using the primers shown in Table 6.

FIG. 24C shows the sequences of the genotypes of the obtained mutant mice.

Experimental Example II. Establishment of Disease Model Mice

1. Establishment of UNx/HPi Model Mice

UNx/HPi mice (unilateral nephrectomy—a diet with high phosphorus content-ingested mice) were obtained by feeding mice a diet with high phosphorus content after unilateral nephrectomy. As a control, mice were obtained by feeding them a diet with low phosphorus content after a sham operation.

1-1. Unilateral Nephrectomy

After mice (C57BL/6J, 8 weeks old, male) were anesthetized by intraperitoneal administration of Avertin (250 mg/kg), the skin was incised from the back. The right renal artery and vein, and ureter were ligated. After cutting on the distal side of the ligation, the right kidney was removed, and the incision was closed. The control mice were subjected to a sham operation. In the sham operation, the right renal artery and vein, and ureter were exposed, and the incision was closed without ligation. In order to wait for the mice to completely recover from operative stress, the mice were fed a 0.54% inorganic phosphorus-containing normal diet (CE-2, CLEA Japan, Inc.) for 4 weeks.

1-2. Phosphorus Overload and Collection of Tissue

From 4 weeks after the completion of the operation (12 weeks old), the unilaterally nephrectomized mice were given a diet with high phosphorus content in which contains (TD.10662, OrientalBioService, Inc.) (hereinafter also referred to as the "kidney disease group"). The sham-operated mice were given a diet with low phosphorus content in which contains (TD.10662 modified type, OrientalBioService, Inc.) (hereinafter also referred to as the "Sham group").

The model mice of chronic kidney disease were obtained by a modification of the method described in Hu M. C. et al. (J Am Soc Nephrol 22, 124-136, 2011). In Hu M. C. et al., the remaining kidney (left kidney) is subjected to ischemia-reperfusion injury at the time of unilateral nephrectomy in Item 1 above. However, in this modification, ischemia-reperfusion was not performed. Tissue was collected 1 week (E), 4 weeks (M), and 8 weeks (L) after the start of the diet with high phosphorus content (the diet with low phosphorus content in which contains in the Sham group).

The animals from which the tissue was to be collected were euthanized by cervical dislocation after blood was collected from the orbit under anesthesia, and the organs and tissue (bone marrow, brain, skin, heart, kidney, liver, lung, pancreas, skeletal muscle, spleen, testis, thymus, adipose, colon, stomach, adrenal glands, aorta, eyes, ileum, jejunum, pituitary gland, skull, salivary glands, and thyroid gland) were collected. After the wet weights of the collected organs and tissue were measured, the organs and tissue were rapidly frozen in liquid nitrogen and stored at −80° C.

2. Establishment of Model of Phosphorus-Overloaded Mice 2-1. Phosphorus Overload WT mice (C57BL/6N, 7 weeks old, male) or Oscar gene mutant mice (7-16 weeks old, male/female) were fed a 0.54% inorganic phosphorus-containing normal diet (CE-2, CLEA Japan, Inc.) for 1 week. Thereafter, the mice were given a diet with high phosphorus content in which contains 2% inorganic phosphorus (TD.10662, OrientalBioService, Inc.) or a diet with high phosphorus content in which contains 0.35% inorganic phosphorus (TD.10662 modified type, OrientalBioService, Inc.) as a special phosphorus diet.

2-2. Collection of Tissue

The skull was collected at the time of the start of the special phosphorus diet fed to the WT mice (8 weeks old), 1 day, 3 days, 1 week (9 weeks old), and 4 weeks (12 weeks old) after the start. In the Oscar gene mutant mice, the skull was collected 1 week after the start of the special phosphorus diet. The animals from which the tissue was to be collected were euthanized by cervical dislocation after being anesthetized by intraperitoneal administration of Avertin (250 mg/kg), and the tissue was collected. After the weight of the collected tissue was measured, the tissue was rapidly frozen in liquid nitrogen, and stored at −80° C.

Experimental Example III. Analysis of Gene Expression in Each Tissue

1. Extraction of RNA from Each Tissue

Each cryopreserved tissue was individually homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes; or ground with a mortar and pestle in liquid nitrogen, dried, and then homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes; or homogenized using zirconia beads of different sizes (1.5 nm diameter×50, 3 mm diameter×5, 5 mm diameter×2) with Cell Destroyer PS1000 or PS2000 (Bio Medical Science Inc., Tokyo, Japan) at 4,260 r.p.m. for 45 seconds at 4° C. After incubation at room temperature for 5 minutes to separate proteins, 0.2 mL of chloroform was added per mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy Mini column (Qiagen), and purified RNAs were collected according to the RNeasy Mini kit (Qiagen) standard protocol. The quality and concentration of each of the collected RNAs was evaluated by using NanoDrop (Thermo Fisher Scientific, MA, USA).

2. Analysis of RNA Expression (RNA-Seq)

(1) Obtaining RNA-Seq Data

RNA-Seq data was obtained using the samples described above by the following procedure.

a. Quality Check

Quality testing of the samples was performed based on the following items.
   Concentration measurement using NanoDrop (spectrophotometer)
   Concentration measurement and quality check using Agilent 2100 Bioanalyzer b. Preparation of Sample A library for a HiSeq next-generation sequencer was prepared with SureSelect Strand-Specific RNA library preparation kit in the following manner.
   i. Collection of poly (A)+RNA (mRNA) from total RNA using Oligo (dT) magnetic beads
   ii. Fragmentation of RNA
   iii. cDNA synthesis
   iv. Double-stranded cDNA synthesis
   v. Terminus repair, phosphorylation, A tail addition
   vi. Ligation of adapters with indices
   vii. 13-cycle PCR
   viii. Purification with magnetic beads c. Obtaining Data Using Next-Generation Sequencer Sequencing was performed using a HiSeq 2500 or 4000 next-generation sequencer (Illumina) in the following manner.
   i. Addition of sequencing reagent
      Reagent: TruSeq PE Cluster Kit v3-cBot-HS (1 flowcell) <PE-401-3001> (Illumina)
      Reagent: TruSeq SBS Kit v3-HS (200 cycle)<FC-401-3001> (Illumina)
   ii. Single-base extension reaction
   iii. Removal of unreacted bases
   iv. Incorporation of fluorescent signal
   v. Removal of protecting groups and fluorescence
The cycle was repeated (e.g., cycle 2, cycle 3 . . . ) and these steps were carried out to 100 cycles.
   vi. For the opposite strand (Read 2), i to v were carried out to 100 cycles.

(2) Analysis of RNA-Seq Data (2)-1. Analysis of Output Data Obtained Using Next-Generation Sequencer The following information processing was carried out for the output data.
   i. Base calling: text data of nucleotide sequences was obtained from the output raw data of analysis (image data).
   ii. Filtering: selection of read data by predetermined filtering was performed.
   iii. Sorting based on index sequences: sample data was sorted based on index information.

(2)-2. Secondary Analysis of Output Data

The data file (Fastq format) obtained using Illumina HiSeq 2500 or 4000 was uploaded on Galaxy (https://usegalaxy.org/) downloaded to a local server. Thereafter, analysis was carried out using Bowtie2 (http://bowtie-bio-.sourceforge.net/bowtie2/index.shtml) to map each sequence to mouse genome map information mm10. The BAM file obtained using Bowtie2 was analyzed using Cufflinks (http://cole-trapnell-lab.github.io/cufflinks/) to calculate FPKM (RPKM) of genes. That is, in this analysis, all RNAs expressed in each tissue were analyzed.

3. qRT-PcR

1 μg of total RNA obtained from each tissue was used as a template for cDNA synthesis, and cDNA was synthesized using Oligo dT20 primer according to the standard protocol of SuperScript III First-Strand Synthesis SuperMix (Life Technologies). After the synthesized cDNA was diluted 20-fold with TE buffer (10 mM Tris-HCl, pH 8.0, 0.1 mM EDTA), real-time PCR was performed with a LightCycler 480 II (Roche) according to the standard protocol of LightCycler 480 SYBR Green I Master (Roche, Basel, Switzerland), and Cp values were measured. The relative expression level of each gene to a reference gene was quantified by comparing the Cp value obtained for each gene with the Cp value for β2-microglobulin (B2m) as the reference gene. The primer pairs used in the real-time PCR are as shown in Table 6. All of the primers were designed by using Primer-BLAST (NCBI).

TABLE 6

| Target | Sequence | SEQ ID NO. |
|---|---|---|
| Forward primer for direct-sequence analysis | CTACTTAGCGACAACGTCCT | 9 |

TABLE 6-continued

| Target | Sequence | SEQ ID NO. |
|---|---|---|
| Reverse primer for direct-sequence analysis | GCCTTGGGGTTTGAAGGTTT | 10 |
| Sequence primer for direct-sequence analysis | CAGAGGCTATGACTGTTCCA | 11 |
| Forward primer for HRM analysis | GGCAGGGTCAACCTTTTCCT | 12 |
| Reverse primer for HRM analysis | AGGGACAGCTCACAGAGAGT | 13 |
| Forward primer: B2m | GCTCGGTGACCCTGGTCTTT | 14 |
| Reverse primer: B2m | AATGTGAGGCGGGTGGAACT | 15 |
| Forward primer: Oscar | CGGGCATGAGTTTTGCACTG | 16 |
| Reverse primer: Oscar | TGGGTATAGTCCAAGGAGCCA | 17 |
| Forward primer: Fgf23 | AGGAGCCATGACTCGAAGGT | 18 |
| Reverse primer: Fgf23 | GCTCACCAGGTAGTGATGCTT | 19 |

4. Analysis of Differentially Expressed Genes

To extract differentially expressed genes, the number of annotation reads of each transcript in sequence data mapped by Bowtie2 was counted by using HTSeq-count (parameter: −r was pos, and −s was no). The obtained results were analyzed by DESeq2 (Love, M. I., Huber, W. & Anders, S.; Genome biology 15, 550, doi:10.1186/s13059-014-0550-8 (2014)) with default settings. Expression differences were compared in E-UNx/HPi vs. E-/M-/L-Sham (n=3), M-UNx/HPi vs. E-/M-/L-Sham (n=3), and L-UNx/HPi vs. E-/M-/L-Sham (n=3). Gene ontology (GO) enrichment analysis was performed using R package "topGO." In the gene ontology (GO) enrichment analysis, the case in which the result of the DESeq2 analysis is 1 or more and the ρ-value is less than 0.05 was defined as "$\log_2$ (fold-change)."

5. Statistical Analysis

In statistical analysis, Student's t-test or one-way analysis of variance was performed, and then significant differences were determined by the Tukey-Kramer test. The case in which the ρ-value is less than 0.05 was defined as being significant (* $p<0.05$,  $p<0.01$, and * $p<0.001$). In the scatter plots, the average is indicated by a horizontal line.

6. Results

Figure 25:
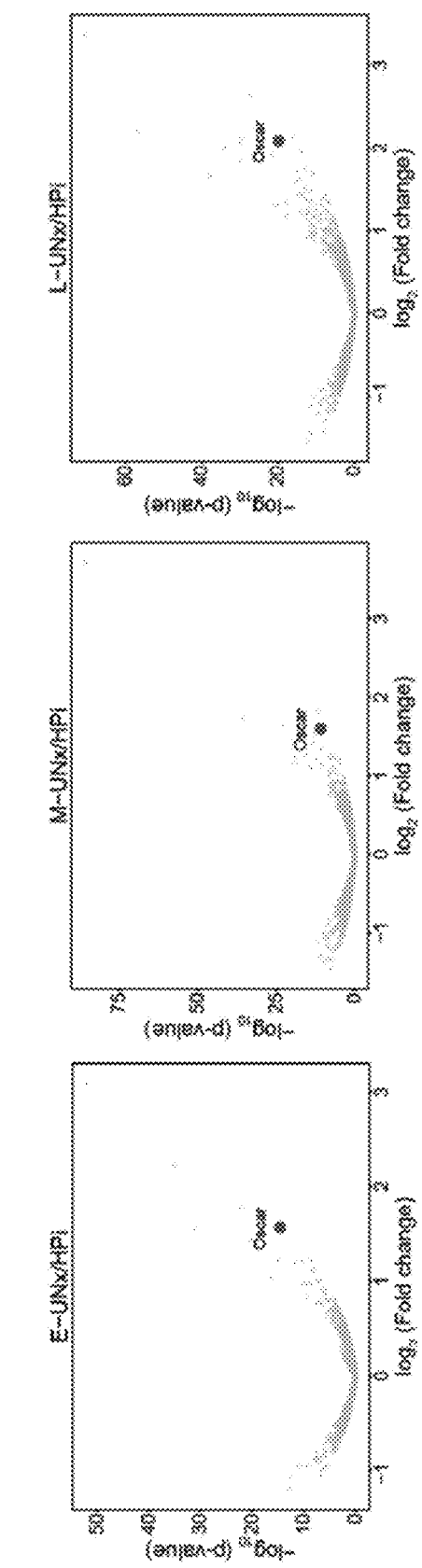
FIG. 25 shows volcano plots in the skull 1 week (E), 4 weeks (M), and 8 weeks (L) after the start of a diet with high phosphorus content in UNx/HPi model mice (a diet with low phosphorus content in a Sham group).
Figure 26:
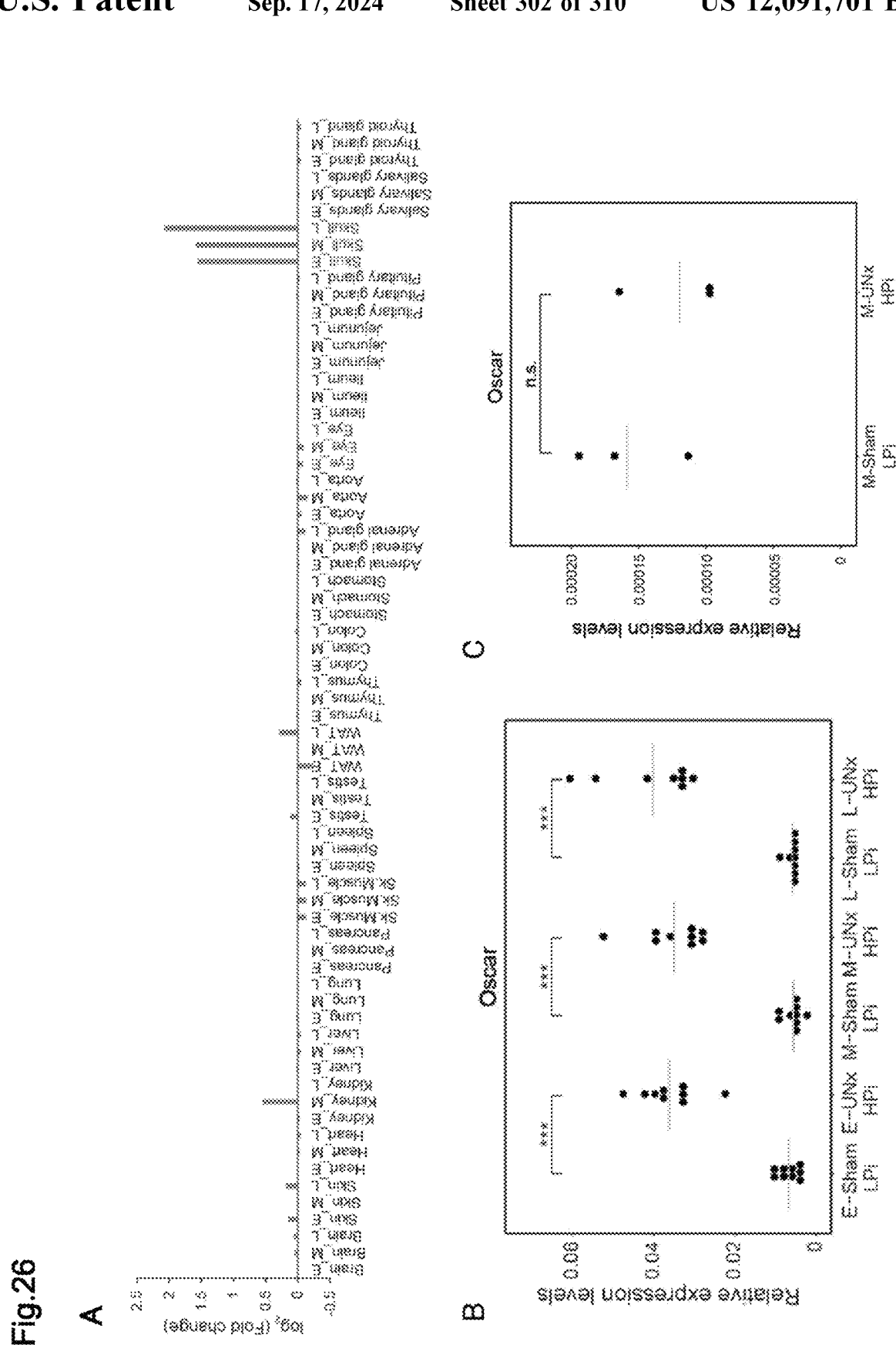
FIG. 26A shows DESeq analysis results of expression of Oscar gene in each tissue.
FIG. 26B shows results of expression of Oscar mRNA in the UNx/HPi model mice and sham mice at E, M, and L examined by qRT-PCR.
FIG. 26C shows results of the expression of Oscar gene in the kidneys confirmed by qRT-PCR. In the graphs, *** indicates p<0.001, and n.s. indicates no significant difference.

FIG. 25 shows volcano plots of the skull 1 week (E-UNx/HPi), 4 weeks (M-UNx/HPi), and 8 weeks (L-UNx/HPi) after the start of the diet with high phosphorus content. Each mRNA after DESeq analysis was plotted as a small dot, and Oscar was indicated by a large dot. The expression of the Oscar gene increased in the UNx/HPi model mice (HPi) at E-UNx/HPi, M-UNx/HPi, L-UNx/HPi compared with that in the sham-operated mice (LPi). FIG. 26A shows DESeq analysis results of expression of the Oscar gene in each tissue. The Oscar gene showed high expression in the skull of the UNx/HPi model at E-, M-, L-. This result was confirmed by qRT-PCR (n=8 to 9). As a result, it was revealed that the expression of the Oscar gene increased in the skull in the UNx/HPi model mice (HPi) at E-UNx/HPi, M-UNx/HPi, and L-UNx/HPi compared with that in the sham-operated mice (LPi) (FIG. 26B). The expression of the Oscar gene slightly increased in the kidney in the DESeq analysis; however, no significant difference was observed in confirmation by qRT-PCR (FIG. 26C).

Figure 27:
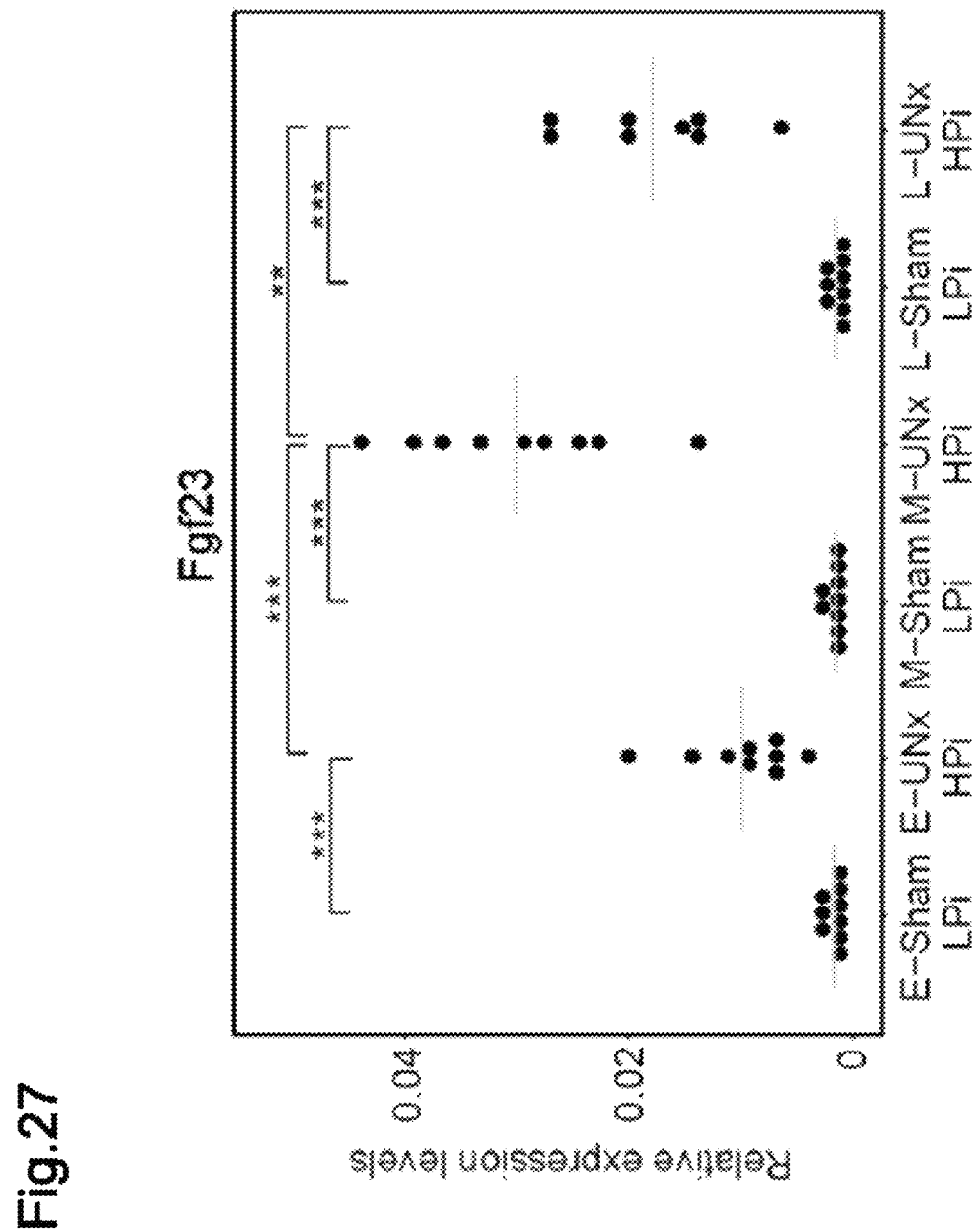
FIG. 27 shows results of expression of FGF23 gene in the skull confirmed by qRT-PCR. In the graph,  indicates p<0.01, and * indicates p<0.001.

FGF23 is a master regulator of inter-organ cross talk between the parathyroid glands, bones, and kidneys in kidney disease. The expression of the FGF23 gene in the skull increased in the UNx/HPi model mice (HPi) at E-UNx/HPi, M-UNx/HPi, L-UNx/HPi compared with that in the sham-operated mice (LPi) (FIG. 27).

Figure 28:
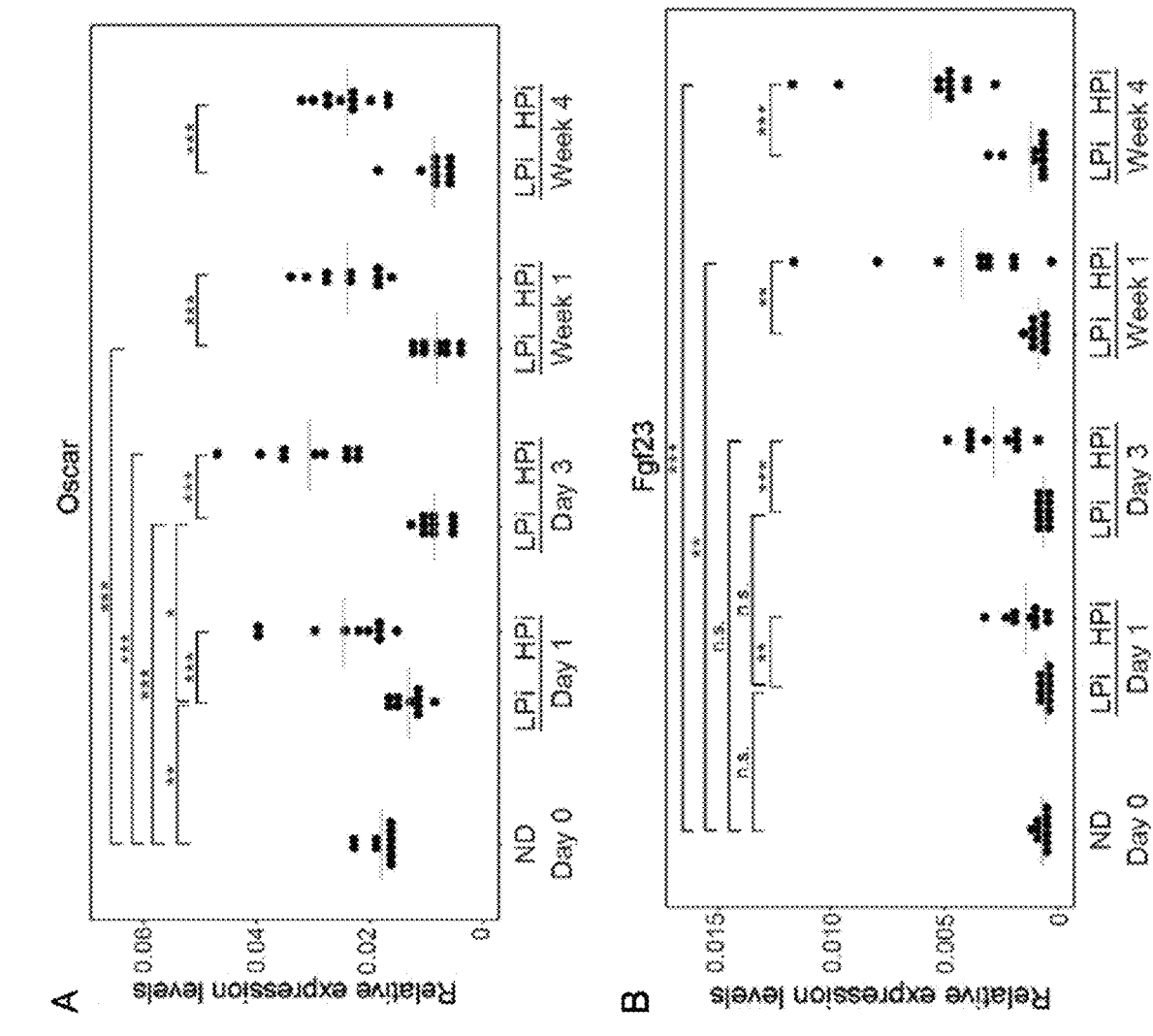
FIG. 28A shows the expression of Oscar gene in the skull 1 day, 3 days, 1 week, and 4 weeks after switching from a normal diet to a diet with low phosphorus content or a diet with high phosphorus content.
FIG. 28B shows the expression of FGF23 gene in the skull 1 day, 3 days, 1 week, and 4 weeks after switching from a normal diet to a diet with low phosphorus content or a diet with high phosphorus content. In the graphs, * indicates p<0.05,  indicates p<0.01, * indicates p<0.001, and n.s. indicates no significant difference.

Next, the expression of the Oscar gene and the FGF23 gene over time after the feed of the mice was switched from the normal diet to the diet with low phosphorus content or the diet with high phosphorus content was examined in the skull. FIG. 28A shows the expression of the Oscar gene in the skull 1 day, 3 days, 1 week, and 4 weeks after switching to the diet with low phosphorus content or the diet with high phosphorus content. FIG. 28B shows the expression of the FGF23 gene in the skull 1 day, 3 days, 1 week, and 4 weeks after switching to the diet with low phosphorus content or the diet with high phosphorus content. The expression of the Oscar gene and the FGF23 gene already increased in the skull on day 1 after switching to the diet with high phosphorus content. Because the ρ-value was lower in Student's t-test, the expression of the Oscar gene increased more robustly than the expression of the FGF23 gene. After the feed was switched from the normal diet to the diet with low phosphorus content, the expression level of the Oscar gene significantly decreased, whereas the expression level of the FGF23 gene was unchanged. After peaking 3 days following the switch to the diet with high phosphorus content, the expression of the Oscar gene showed a tendency to gradually cease to increase. In contrast, the expression of the FGF23 gene gradually increased as the period of the diet with high phosphorus content lengthened. These results showed that the expression of the Oscar gene reflects phosphorus intake more strongly and more sensitively than the expression of FGF23.

Figure 29:
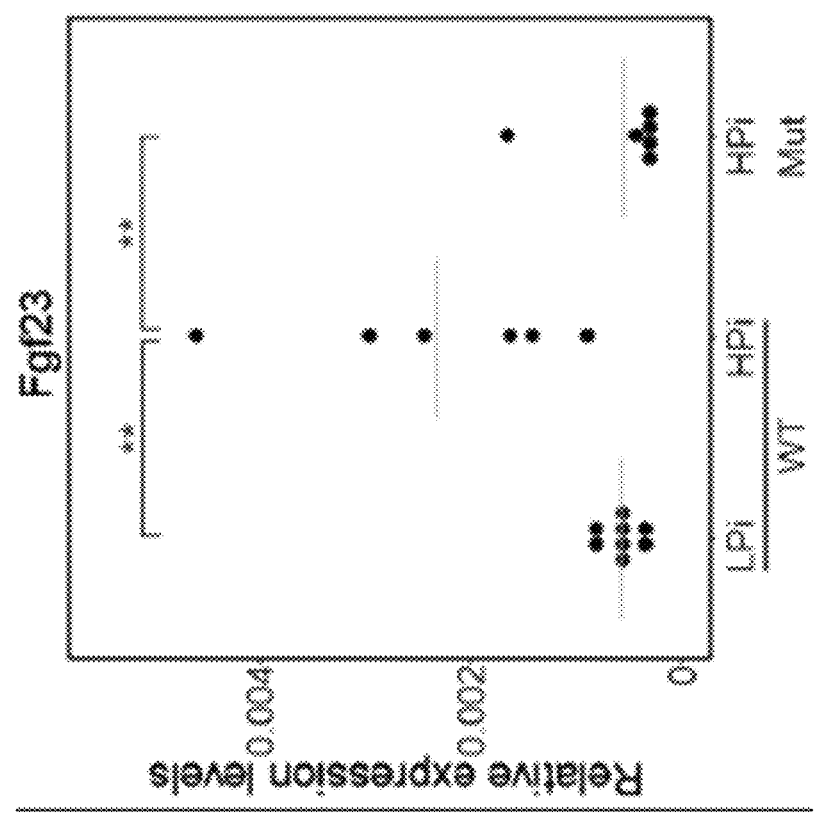
FIG. 29 shows the expression of FGF23 in the bones of normal mice and Oscar gene mutant mice fed a diet with high phosphorus content. ** indicates p<0.01.

Further, what effect an increase in the expression of Oscar in the bones has on the expression of FGF23 in the bones was examined. The Oscar gene mutant mice obtained in Item 1 above were fed a diet with high phosphorus content, and the expression of FGF23 in the bones was examined by qRT-PCR. The results revealed that the expression of FGF23 did not increase in the bones of the Oscar gene mutant mice even if they were fed the diet with high phosphorus content, as shown in FIG. 29.

The above results showed that Oscar up-regulates the expression pathway of FGF23. This indicated that suppressing the functional expression of Oscar enables suppression of the functional expression of FGF23, and further that suppressing the functional expression of Oscar enables control of disease involving FGF23.

Reference Example 2: Preparation of Soluble Human Oscar-Fc Fusion Protein

An expression plasmid containing a nucleotide sequence encoding a soluble human Oscar-Fc fusion protein was expressed in animal cells, thereby preparing the soluble human Oscar-Fc fusion protein shown in SEQ ID NO: 2. The preparation of the protein was outsourced to Protein-Express Co., Ltd. (Chiba, Japan).

<Amino acid sequence of humanOscar-humanIgG1>
(SEQ ID NO: 2)
MALVLILQLLTLWPLCHTDITPSVAIIVPPASYHPKPWLGAQPATVVTPG

VNVTLRCRAPQPAWRFGLFKPGEIAPLLFRDVSSELAEFFLEEVTPAQGG

```
SYRCCYRRPDWGPGVWSQPSDVLELLVTEELPRPSLVALPGPVVGPGANV

SLRCAGRLRNMSFVLYREGVAAPLQYRHSAQPWADFTLLGARAPGTYSCY

YHTPSAPYVLSQRSEVLVISWEGEGPEARPASDKTHTCPPCPAPELLGGP

SVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPE

NNYKTTPPVLDSDGSFELYSKLTVDKSRWQQGNVESCSVMHEALHNHYTQ

KSLSLSPGK*
```

(The underline indicates a hinge region. The upstream from the hinge region indicates the sequence of human Oscar, and the downstream from the hinge region indicates the human IgG1 sequence.)

1. Preparation of Cells

FreeStyle 293-F cells were subcultured in FreeStyle 293 Expression Medium (Invitrogen). The subculture was performed using a 500 ml-flask at the following conditions: a shaking speed of 120 r.p.m., a carbon dioxide concentration of 8%, and a temperature of 37° C. (170 mL of medium). The cells were diluted to 6×10$^5$ cells/mL to a total amount of 1 L the day before transfection and cultured for 24 hours. After the culture, the number of cells was adjusted to 1×10$^6$ cells/mL, and the cells were used for transfection.

2. Expression Test 2.1 mL of 293fectin Transfection Reagent (Invitrogen) was added to 30 mL of OptiPRO SFM (Invitrogen) pre-warmed to 37° C., thereby preparing a reagent solution. Similarly, 1 mg of pcDNA3 (Invitrogen) containing kozak-hOscar-hIgG1-intronXbaI having the following sequence was added to 30 mL of OptiPRO SFM, thereby preparing a DNA solution. The prepared reagent solution and DNA solution were incubated at room temperature for 5 minutes. The reagent solution and DNA solution after the 5 minutes were mixed to prepare a transfection solution. The transfection solution was incubated at room temperature for 20 minutes and added to a culture medium adjusted for transfection, followed by sampling on day 1, day 2, and day 3 after the start of the transfection. The culture was then terminated on day 4. The obtained samples were centrifuged to separate into a supernatant and a precipitate. The protein expression was confirmed by SDS-PAGE and Western blotting.

```
<kozak-hOscar-hIgG1-intronXbaI>
                                    (SEQ ID NO: 20)
aagcttgccaccATGGCCCTCGTGCTTATCCTCCAACTTCTCACGCTTTG

GCCTCTGTGCCACACCGACATTACTCCGTCTGTTGCGATAATTGTCCCTC

CCGCCTCTTATCACCCTAAACCTTGGCTGGGCGCACAGCCAGCTACTGTG

GTTACTCCTGGGGTGAACGTAACACTGCGCTGCCGTGCTCCTCAGCCCGC

CTGGAGATTTGGGTTGTTTAAGCCCGGAGAGATAGCACCACTGCTGTTTC

GGGATGTGTCCTCAGAGCTGGCTGAGTTCTTCCTGGAAGAGGTCACTCCT

GCCCAAGGAGGCAGCTATCGGTGCTGTTATAGGCGGCCGGATTGGGGACC

CGGCGTTTGGTCCCAACCATCTGATGTGCTCGAACTGCTTGTGACAGAAG

AGCTGCCCAGACCTAGCTTGGTAGCCTTGCCCGGTCCTGTCGTCGGACCT

GGTGCCAATGTTTCTCTTCGATGTGCCGGAAGGCTGCGCAATATGTCCTT

TGTACTGTATAGGGAGGGAGTAGCCGCACCTCTGCAGTATAGGCATAGCG

CTCAGCCCTGGGCGGATTTTACTCTGCTTGGTGCCAGAGCACCCGGGACC

TATTCCTGCTACTACCACACTCCTTCCGCACCCTACGTCCTGTCACAGAG

ATCAGAAGTGCTCGTGATCTCCTGGGAGGGAGAAGGCCCAGAAGCCGACA

AAACTCACACATGCCCACCGTGCCCAGgtaagccagcccaggcctcgccc tccagctcaaggcgggacaggtgccctagagtagcctgcatccagggaca ggccccagccgggtgctgacacgtccacctccatctcttcctcagCACCT

GAACTCCTGGGGGGACCGTCAGTCTTCCTCTTCCCCCCAAAACCCAAGGA

CACCCTCATGATCTCCCGGACCCCTGAGGTCACATGCGTGGTGGTGGACG

TGAGCCACGAAGACCCTGAGGTCAAGTTCAACTGGTACGTGGACGGCGTG

GAGGTGCATAATGCCAAGACAAAGCCGCGGGAGGAGCAGTACAACAGCAC

GTACCGTGTGGTCAGCGTCCTCACCGTCCTGCACCAGGACTGGCTGAATG

GCAAGGAGTACAAGTGCAAGGTCTCCAACAAAGCCCTCCCAGCCCCCATC

GAGAAAACCATCTCCAAAGCCAAAGgtgggacccgtggggtgcgagggcc acatggacagaggccggctcggcccaccctctgccctgagagtgactgct gtaccaacctctgtccctacagGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTAAATGAtctag a
```

3. Purification Using Bipo Resin Protein A (10 mL)

The culture supernatant (1 L) was loaded on Bipo Resin Protein A (10 mL) to purify a target protein. After washing with PBS, elution of the target protein was performed using 100 mM citric acid buffer (pH 2.5) (5 mL×5). The eluate was neutralized with 1M Tris-HCl (pH 9.0). After the purification, purity of protein was confirmed in each fraction by SDS-PAGE and Western blotting. The results confirmed a band of the target protein in the elution fraction. The fraction containing the target protein was collected, followed by a buffer exchange into PBS (total amount: 50 mL). Thereby, 1 mg/mL of a soluble human Oscar-Fc fusion protein was obtained.

Example 2: Experiment of Administration of Soluble Human Oscar-Fc Fusion Protein to HP Model Mice HP mice (mice of diet with high phosphorus content intake) were obtained by feeding mice a diet with high phosphorus content. The soluble human Oscar-Fc fusion protein was administered to this model every week.

1. Phosphorus Overload

Mice ingested a diet with high phosphorus content (HP) were obtained by feeding mice (C57BL/6N, 8 weeks old, male) a diet containing 2% inorganic phosphorus (TD.10662, OrientalBioService, Inc.) as a special phosphorus diet. Mice ingested a diet with low phosphorus content (LP) were fed a diet containing 0.35% inorganic phosphorus (TD.10662 modified type, OrientalBioService, Inc.).

2. Administration of Soluble Human Oscar-Fc Fusion Protein and Collection of Tissue The soluble human Oscar-Fc fusion protein (10 mg/kg) was intraperitoneally administered weekly from the start date of the diet with high phosphorus content (week 0) to week 4, i.e., a total of five times. In this experiment, physiological saline was administered to a control group. Tissue was collected the day after completion of the intraperitoneal administration on week 4, i.e., the fifth intraperitoneal administration. The animals from which the tissue was to be collected were euthanized by cervical dislocation after blood was collected in an EDTA-supplemented tube from the orbit under tribromoethanol anesthesia (250 mg/kg), and the organs and tissue (the skull, brain, pituitary gland, parotid glands, thyroid gland, heart, lung, pancreas, kidney, adrenal glands, liver, spleen, thymus, aorta, femoral muscle, skin, testis, adipose tissue, stomach, jejunum, ileum, colon, and bone marrow cells) were collected. After the wet weights of the collected organs and tissue were measured, the organs and tissue were rapidly frozen in liquid nitrogen and stored at −80° C. The collected blood was centrifuged at 1200 g for 10 minutes at room temperature. After the centrifugation, the supernatant plasma was collected and stored at −80° C.

3. Analysis of Gene Expression in Each Tissue and Measurement of Blood Components 3-1. RNA Extraction from Each Tissue Each cryopreserved tissue was individually homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes, or homogenized using zirconia beads of different sizes (1.5 mm diameter×50, 3 mm diameter×5, 5 mm diameter×2) with a Cell Destroyer PS1000 or PS2000 (Bio Medical Science Inc., Tokyo, Japan) at 4,260 r.p.m. for 45 seconds at 4° C. After incubation at room temperature for 5 minutes to separate proteins, 0.2 ml of chloroform was added per mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy Mini column (Qiagen), and purified RNAs were collected according to the RNeasy Mini kit (Qiagen) standard protocol. The quality and concentration of each of the collected RNAs was evaluated by using NanoDrop (Thermo Fisher Scientific, MA, USA).

3-2. qRT-PCR 0.5 to 1 μg of total RNA obtained from each tissue was used as a template for cDNA synthesis, and cDNA was synthesized using Oligo dT20 primer according to the standard protocol of SuperScript III First-Strand Synthesis SuperMix (Life Technologies). After the synthesized cDNA was diluted 20-fold with TE buffer (10 mM Tris-HCl, pH 8.0, 0.1 mM EDTA), real-time PCR was performed with a LightCycler 480 II (Roche) according to the standard protocol of LightCycler 480 SYBR Green I Master (Roche, Basel, Switzerland), and Cp values were measured. The relative expression level of each gene to a reference gene was quantified by comparing the Cp value obtained for each gene with the Cp value for Maea as the reference gene. The primer pairs used in the real-time PCR are as shown in Table 7. All of the primers were designed by using Primer-BLAST (NCBI).

TABLE 7

|   | Gene | Forward | SEQ ID NO. | Reverse | SEQ ID NO. |
|---|------|---------|------------|---------|------------|
| 1 | Maea | AAGACCTTGAGTAGTTGCCCA | (21) | TGCTCGATCCTACGTTTGCAG | (22) |
| 2 | Fgf23 | AGGAGCCATGACTCGAAGGT | (23) | GCTCACCAGGTAGTGATGCTT | (24) |
| 3 | Prb1 | ACCCCAGCATGGAAACAAAG | (25) | AAGAATGGTATTGAAGTCATCTGTC | (26) |
| 4 | Prh1 | ACCCCGTGAAGAAAATCAGAA | (27) | TAACAGGCGGTCTTGGTTGG | (28) |
| 5 | Prp2 | TGGTGGTCCTGTTTACAGTGG | (29) | TTCTGAAGTTCTTCACGGGGT | (39) |
| 6 | Prpmp5 | CCTACGAAGACTCAAATTCTCAGC | (31) | GAGGACCATGGTGGTGTCC | (32) |
| 7 | B2m | GCTCGGTGACCCTGGTCTTT | (33) | AATGTGAGGCGGGTGGAACT | (34) |
| 8 | Fgg | CTCCATCGGAGAAGGACAGC | (35) | AGGTCCTGAAAGTCCATTGTCC | (36) |

4. Measurement of Concentration of FGF23 in Plasma by ELISA Method

The concentration of FGF23 in plasma was measured using an ELISA kit sold by KAINOS Laboratories, Inc. (TCY4000). A plasma sample cryopreserved in a freezer was thawed on ice, and the sample undiluted or the sample diluted 5-fold with standard solution 1 (FGF-23 concentration, 0 pg/ml) supplied with the kit was used for measurement.

50 μl of the diluted sample or a sample for a calibration curve was added to each well of an ELISA plate supplied with the kit. The plate was sealed, followed by stirring and incubating at room temperature for 2 hours. After the two hours, the sample in each well was aspirated and discarded. 300 μl of a wash solution supplied with the kit was then added to each well, and the wash solution was removed. This operation was performed four times. After the wash solution was thoroughly removed, 100 μl of an enzyme-labeled antibody solution (FGF-23 Conjugate) supplied with the kit was added to each well, and the plate was sealed, followed by stirring and incubating at room temperature for 1 hour. After the 1 hour, the sample in each well was aspirated and discarded. 300 μl of the wash solution supplied with the kit was then added to each well, and the wash solution was removed. This operation was performed four times. After the wash solution was thoroughly removed, 100 µl of a substrate solution (Substrate) supplied with the kit was added to each well, and the plate was allowed to stand at room temperature for 30 minutes in the shade. Thereafter, 100 µl of a reaction stop solution (Stop Solution) supplied with the kit was added to each well, followed by gentle shaking. Absorbance at 450 nm was then measured with an absorbance microplate reader (Multiskan GO, Thermo Fisher Scientific Inc.). The concentration of FGF23 in plasma was calculated by making a calibration curve from the measurement result of recombinant FGF23 supplied with the kit.

5. Statistical Analysis

In statistical analysis, Student's t-test or one-way analysis of variance was performed, and then significant differences were determined by the Tukey-Kramer test. The case in which the p-value is less than 0.05 was defined as being significant.

6. Results

Hereinafter, in the drawings, HP4W indicates mice 4 weeks after the start of the diet with high phosphorus content, and LP4W indicates mice 4 weeks after the start of the diet with low phosphorus content (control group). sOscar indicates mice to which the soluble human Oscar-Fc fusion protein was administered, and NS indicates mice to which physiological saline was administered in place of the soluble human Oscar-Fc fusion protein. WT (12W) indicates 12-week-old male wild-type mice fed a normal diet.

Figure 30:
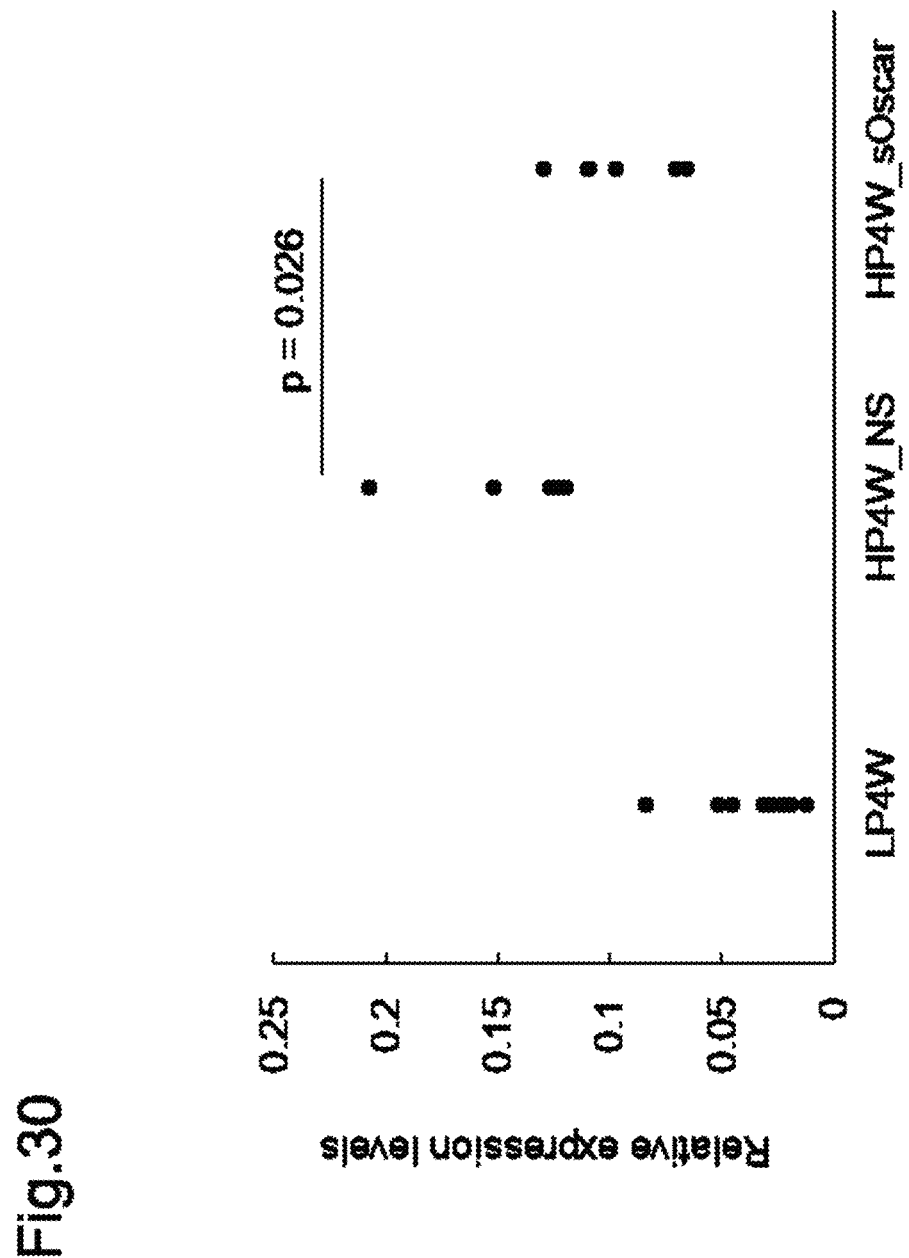
FIG. 30 shows qRT-PCR results of FGF23 in the skull. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.
Figure 31:
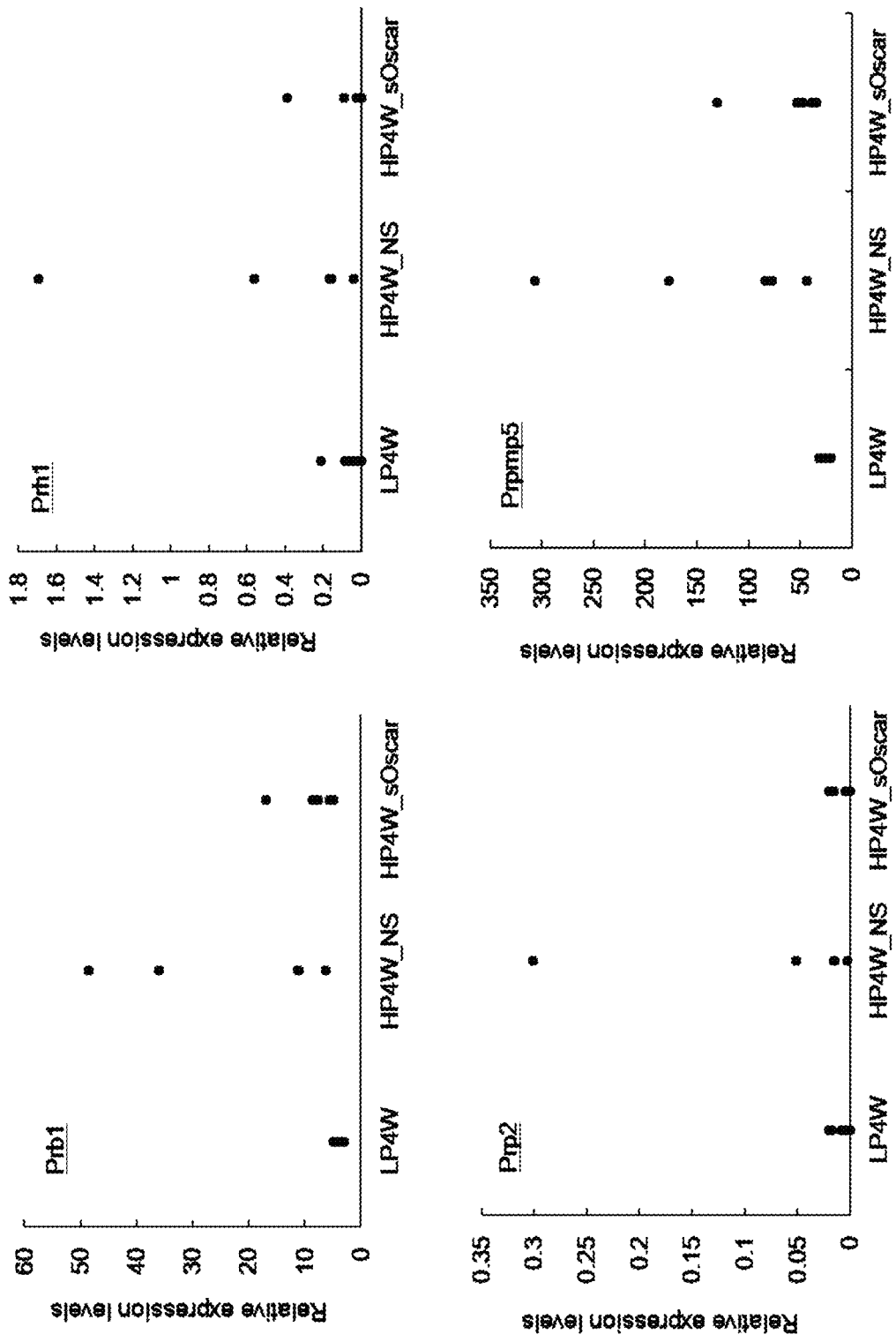
FIG. 31 shows qRT-PCR results of PRP genes in the parotid glands. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.

FIG. 30 shows qRT-PCR results of FGF23 in the skull. FIG. 31 shows qRT-PCR results of PRP genes in the parotid glands. FGF23 is a master regulator of inter-organ cross talk between the parathyroid glands, bones, and kidneys in kidney disease. The expression of FGF23 was induced by the diet with high phosphorus content in the skulls. However, the expression of FGF23 was suppressed by administration of the soluble human Oscar-Fc fusion protein (FIG. 30) (n=5 to 6). The expression of the Maea gene was normalized, and a significance test was performed. The results showed a significant difference (p=0.026) between HP to which sOscar was administered, and HP to which sOscar was not administered. The expression of PRP genes (Prb1, Prh1, Prp2, and Prpmp5) whose expression is induced by the diet with high phosphorus content was suppressed by administration of the soluble human Oscar-Fc fusion protein in the parotid glands (FIG. 31) (n=5 to 6). From the above, it was indicated that the expression of renal failure early markers FGF23 gene (the skull) and PRP genes (the parotid glands) were suppressed by administration of the soluble human Oscar-Fc fusion protein to the model mouse of phosphorus overload for 4 weeks.

Figure 32:
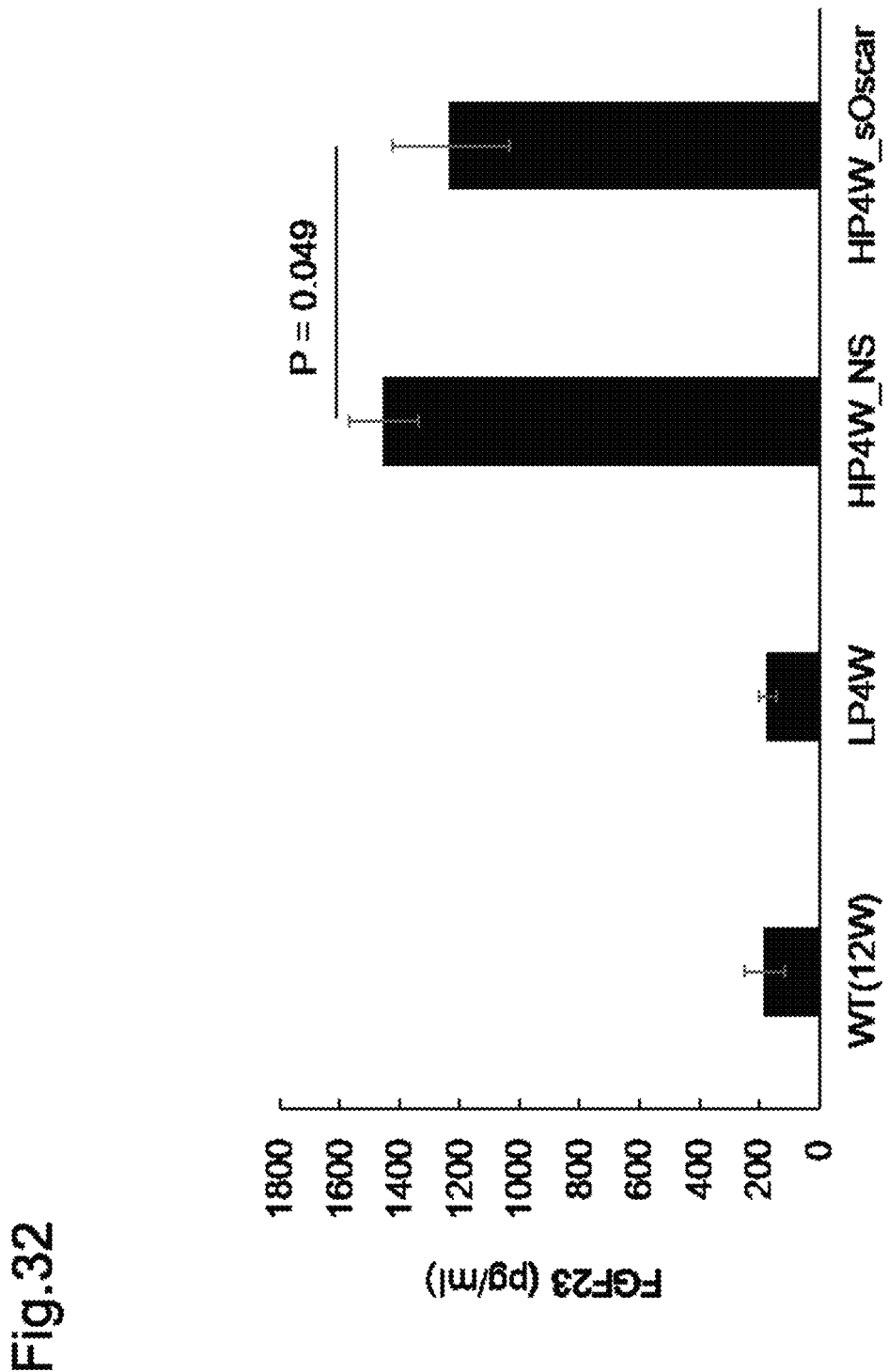
FIG. 32 shows ELISA measurement results of FGF23 in plasma. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein. WT (12W) indicates 12-week-old male wild-type mice fed a normal diet.

FIG. 32 shows ELISA measurement results of FGF23 in plasma. In HP, the concentration of FGF23 in plasma was higher than that in LP4W and WT (12W). The increase in the concentration of FGF23, which is a renal failure early marker in blood, was statistically significantly suppressed by administration of the soluble human Oscar-Fc fusion protein to HP (p=0.049).

As described later, qRT-PCR analysis in the bones of the 1-week model of Oscar gene mutant mice fed the diet with high phosphorus content showed that the increase in the expression of renal failure early marker FGF23 gene was significantly suppressed. In this experiment, administering the soluble human Oscar-Fc fusion protein, which has an effect of inhibiting ligand binding to Oscar, from the early stage of phosphorus overload suppressed the expression of the FGF23 gene, which is deeply involved in clinical states such as chronic kidney disease, in the bones; and further suppressed the increase in the concentration of FGF23 in plasma. This showed the potential of administering the soluble human Oscar-Fc fusion protein as a novel treatment method for improving a clinical state caused by an excess phosphorus state, such as kidney damage.

Reference Example 3: Measurement of Creatinine in Plasma

Mice (C57BL/6N, 8 weeks old, male) were fed a diet with high phosphorus content in which contains 2% inorganic phosphorus (TD.10662, OrientalBioService, Inc.) or a diet with low phosphorus content in which contains 0.35% inorganic phosphorus (TD.10662 modified type, OrientalBioService, Inc.) as a special phosphorus diet for 4 weeks. Thereafter, plasma samples (LP4W, HP4W) were collected and cryopreserved. A plasma sample (WT (12W)) was collected from 12-week-old male mice (C57BL/6N) and cryopreserved. 8-week-old male mice (C57BL/6N) were subjected to unilateral nephrectomy, and after being adapted for 4 weeks, the mice were fed a diet with high phosphorus content for 4 weeks. Thereafter, a plasma sample (UNx/HP4W) was collected and cryopreserved. Creatinine values in plasma were measured using 100 µl of each sample by an enzymatic method.

Figure 33:
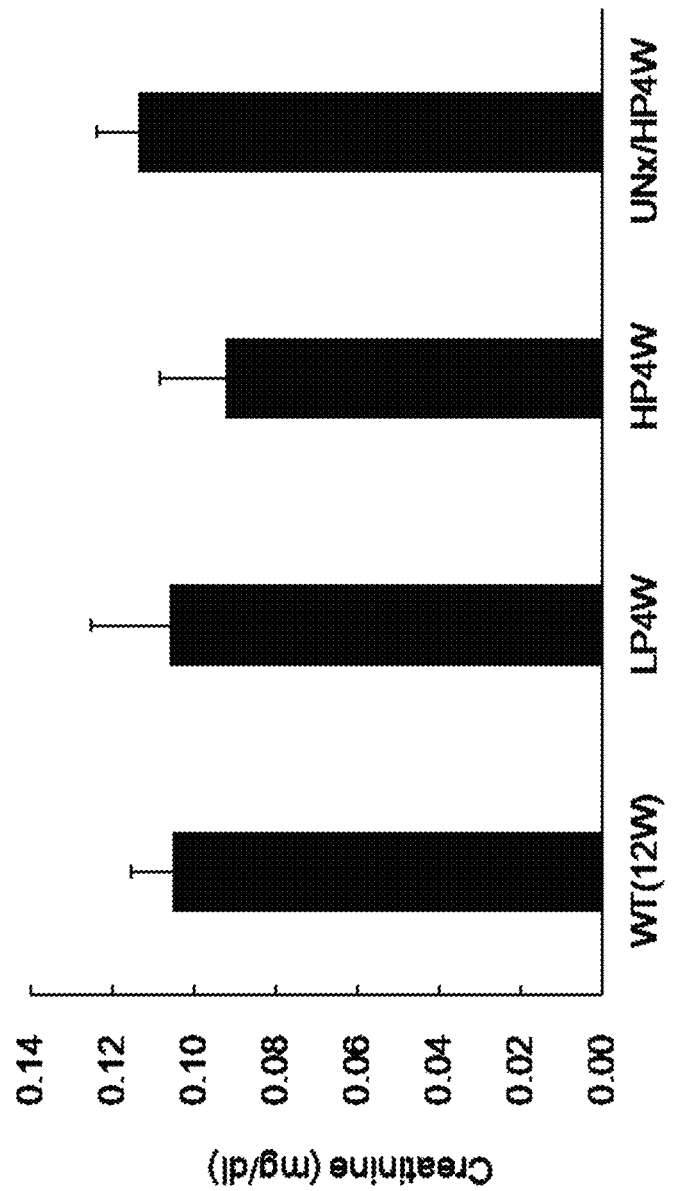
FIG. 33 shows the concentration of creatinine in plasma. HP4W indicates mice 4 weeks after the start of a diet with high phosphorus content, and LP4W indicates mice 4 weeks after the start of a diet with low phosphorus content (a control group). WT (12W) indicates 12-week-old male wild-type mice.

FIG. 33 shows a creatinine value in plasma in each model of phosphorus overload. In the HP4W model and the UNx/HP4W model, the amount of creatinine, which is a blood marker of renal failure, did not increase. Thus, it was believed that the soluble human Oscar-Fc fusion protein can be used for suppressing a decline in kidney function. It was also believed that the kidney function prediction markers shown in FIGS. 22 and 23 can detect a decline in kidney function earlier than the amount of creatinine in blood increases. Therefore, it was believed that a decline in kidney function can be suppressed in an early stage by administering the soluble human Oscar-Fc fusion protein at a stage when the amount of creatinine has not yet increased, and when the kidney function prediction markers shown in FIGS. 22 and 23 are increased or decreased.

Reference Example 4: Expression of Fibrinogen in Kidneys

To evaluate the effect of the soluble Oscar-Fc fusion protein on kidney function, the expression of a kidney function marker was confirmed in the kidneys of HP4W_NS, HP4W_sOscar, and LP4W of Reference Example 2.

Figure 34:
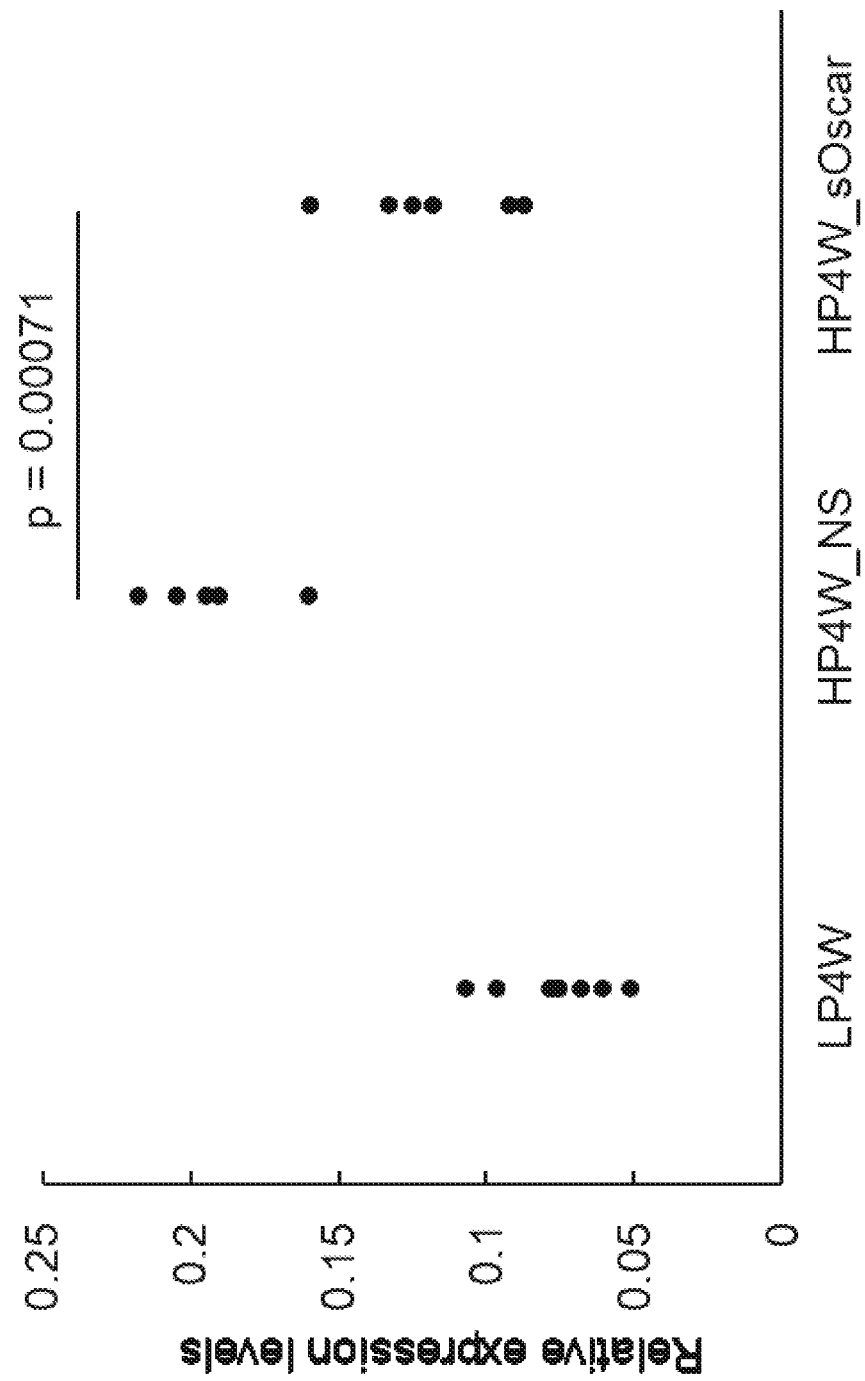
FIG. 34 shows qRT-PCR results of Fgg gene in the kidneys. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.

In the kidneys, the expression of the Fgg gene, which is a fibrinogen gene whose expression is induced by a diet with high phosphorus content, was significantly suppressed by administration of the soluble Oscar-Fc fusion protein. (FIG. 34) (p=0.00071; n=5 to 6). Fibrinogen genes have been reported as kidney function markers and therapeutic targets. This suggested that at least one disease selected from the group consisting of declined kidney function, chronic kidney disease, and renal failure, which are associated with a high-phosphorus state, can be prevented or treated by administering the soluble Oscar-Fc fusion protein.

DESCRIPTION OF REFERENCE NUMERALS 1,2 Screening device
3 Input unit
4 Display unit
5a Device
5b Device 5c Device
6,7 Prediction device
11 First measurement value obtaining unit
12 Second measurement value obtaining unit
13 Measurement value comparison unit
14 Candidate substance determination unit
21 First evaluation result obtaining unit
22 Second evaluation result obtaining unit
23 Evaluation result comparison unit
24 Candidate substance determination unit
52 Reaction/electrophoresis unit
53 Detection unit
61 Subject data obtaining unit
62 Pattern similarity calculation unit
63 Prediction unit
71 Stage information obtaining unit
72 Stage information checking unit
73 Pattern extraction unit
74 Prediction unit
100,110,120,130 System
101 CPU
102 Memory
103 Storage unit
104 Bus
105 Interface unit
109 Storage medium

The invention claimed is:

1. A device for screening a candidate substance for an active ingredient, the device comprising:
   a memory for storing a program;
   an interface; and
   a processor, during execution of the program, configured to:
   obtain, through the interface, a first measurement value of a kidney function prediction marker protein and/or a measurement value of mRNA of the protein in a specimen collected from a subject (excluding humans), test tissue, or test cell treated with a test substance (a test-substance-treated specimen); and
   determine that the test substance is a candidate substance for the active ingredient based on the first measurement value(s),
   wherein the active ingredient prevents or treats at least one disease selected from the group consisting of declined kidney function, chronic kidney disease, and renal failure,
   the kidney function prediction marker protein is at least one member selected from the group consisting of Defb8, and Hamp2,
   the specimen for obtaining the measurement value of Defb8 is skin, and the specimen for obtaining the measurement value of Hamp2 is skin, hair roots, or secretions from skin.

2. The device according to claim 1, the processor, during execution of the program, further configured to:
obtain, through the interface, a second measurement value of the kidney function prediction marker protein and/or a measurement value of mRNA of the protein in a specimen collected from a subject (excluding humans), test tissue, or test cell that is not treated with the test substance (an untreated specimen);
compare the first measurement value(s) of the test-substance-treated specimen with the second measurement value(s) of the untreated specimen, and
determine that the test substance is a candidate substance for the active ingredient based on the comparison result between the first measurement value(s) and second measurement value(s).

3. A method for screening a candidate substance for an active ingredient to prevent or treat at least one disease selected from the group consisting of declined kidney function, chronic kidney disease, and renal failure, the method comprising the steps of:
(I) obtaining a first measurement value of a kidney function prediction marker protein and/or a measurement value of mRNA of the protein in a specimen collected from a subject (excluding humans), test tissue, or test cell treated with a test substance (a test-substance-treated specimen); and
(II) determining that the test substance is a candidate substance for the active ingredient based on the first measurement value(s) obtained in step (I),
wherein the active ingredient prevents or treats at least one disease selected from the group consisting of declined kidney function, chronic kidney disease, and renal failure,
the kidney function prediction marker protein is at least one member selected from the group consisting of Defb8, and Hamp2,
the specimen for obtaining the measurement value of Defb8 is skin, and
the specimen for obtaining the measurement value of Hamp2 is skin, hair roots, or secretions from skin.

4. The method according to claim 3, further comprising, between steps (I) and (II), the step of comparing the first measurement value(s) of the test-substance-treated specimen obtained in step (I) with a second measurement value of a corresponding kidney function prediction marker protein and/or a measurement value of mRNA of the protein in a specimen collected from a subject (excluding humans), test tissue, or test cell that is not treated with the test substance (an untreated specimen), and
determining that the test substance is a candidate substance for the active ingredient based on the comparison result between the first measurement value(s) and second measurement value(s) in step (II).

5. The method according to claim 3, comprising, before step (I), the steps of:
(i) treating the subject (excluding humans), test tissue, or test cell with the test substance;
(ii) collecting the specimen from the subject, test tissue, or test cell treated with the test substance in step (i); and
(iii) collecting the protein and/or the mRNA from the specimen obtained in step (ii).

6. A device for screening a candidate substance for an active ingredient, the device comprising:
a memory for storing a program;
an interface; and
a processor, during execution of the program, configured to:
obtain, through the interface, a first evaluation result of function of a kidney function prediction marker protein in a specimen collected from a subject (excluding humans), test tissue, or test cell treated with a test substance (a test-substance-treated specimen); and
determine that the test substance is a candidate substance for the active ingredient based on the first evaluation result obtained by the first evaluation result obtaining means,
wherein the active ingredient prevents or treats at least one disease selected from the group consisting of declined kidney function, chronic kidney disease, and renal failure,
the kidney function prediction marker protein is at least one member selected from the group consisting of Defb8, and Hamp2,
the specimen for obtaining the measurement value of Defb8 is skin, and
the specimen for obtaining the measurement value of Hamp2 is skin, hair roots, or secretions from skin.

7. The device according to claim 6, the processor, during execution of the program, further configured to:
obtain, through the interface, a second evaluation result of function of the kidney function prediction marker protein in a specimen collected from a subject (excluding humans), test tissue, or test cell that is not treated with the test substance (an untreated specimen); and
compare the first evaluation result of the test-substance-treated specimen with the second evaluation result of the untreated specimen, and
determine that the test substance is a candidate substance for the active ingredient based on the comparison result obtained by the evaluation result comparison means between the first evaluation result and second evaluation result.

8. A method for screening a candidate substance for an active ingredient to prevent or treat at least one disease selected from the group consisting of declined kidney function, chronic kidney disease, and renal failure, the method comprising the steps of:
(I) obtaining a first evaluation result of function of a kidney function prediction marker protein in a specimen collected from a subject (excluding humans), test tissue, or test cell treated with a test substance (a test-substance-treated specimen); and
(II) determining that the test substance is a candidate substance for the active ingredient based on the first evaluation result obtained in step (I),
wherein the kidney function prediction marker protein is at least one member selected from the group consisting of Defb8, and Hamp2,
the specimen for obtaining the measurement value of Defb8 is skin, and
the specimen for obtaining the measurement value of Hamp2 is skin, hair roots, or secretions from skin.

9. The method according to claim 8, further comprising, between steps (I) and (II), the step of comparing the first evaluation result of the test-substance-treated specimen obtained in step (I) with a second evaluation result of function of a corresponding kidney function prediction marker protein in a specimen collected from a subject (excluding humans), test tissue, or test cell that is not treated with the test substance (an untreated specimen), and
determining that the test substance is a candidate substance for the active ingredient based on the comparison result between the first evaluation result and second evaluation result in step (II).

10. The method according to claim 8, comprising, before step (I), the steps of:
   (i) treating the subject (excluding humans), test tissue, or test cell with the test substance; and
   (ii) collecting the specimen from the subject, test tissue, or test cell treated with the test substance in step (i).

\* \* \* \* \*